United States Patent
Chan et al.

US011566003B2

(10) Patent No.: US 11,566,003 B2
(45) Date of Patent: Jan. 31, 2023

(54) ISOQUINOLINES AS INHIBITORS OF HPK1

(71) Applicant: Genentech, Inc., South San Francisco, CA (US)

(72) Inventors: Bryan Chan, Foster City, CA (US); Joy Drobnick, Daly City, CA (US); Lewis Gazzard, Belmont, CA (US); Timothy Heffron, Burlingame, CA (US); Jun Liang, Los Altos Hills, CA (US); Sushant Malhotra, Burlingame, CA (US); Rohan Mendonca, Pleasanton, CA (US); Naomi Rajapaksa, San Mateo, CA (US); Craig Stivala, San Mateo, CA (US); John Tellis, San Mateo, CA (US); Weiru Wang, Lafayette, CA (US); BinQing Wei, Belmont, CA (US); Aihe Zhou, San Jose, CA (US); Matthew W. Cartwright, Harlow (GB); Michael Lainchbury, Harlow (GB); Emanuela Gancia, Harlow (GB); Eileen Seward, Harlow (GB); Andrew Madin, Harlow (GB); David Favor, Shanghai (CN); Kin Chiu Fong, Shanghai (CN); Yonghan Hu, Shanghai (CN); Andrew Good, Shanghai (CN)

(73) Assignee: Genentech, Inc., South San Francisco, CA (US)

( * ) Notice: Subject to any disclaimer, the term of this patent is extended or adjusted under 35 U.S.C. 154(b) by 30 days.

(21) Appl. No.: 16/921,297

(22) Filed: Jul. 6, 2020

(65) Prior Publication Data

US 2021/0163417 A1  Jun. 3, 2021

Related U.S. Application Data

(62) Division of application No. 15/942,333, filed on Mar. 30, 2018, now abandoned.

(30) Foreign Application Priority Data

Mar. 30, 2017 (WO) ............... PCT/CN2017/078790
Feb. 15, 2018 (WO) ............... PCT/CN2018/076908

(51) Int. Cl.
| | | |
|---|---|---|
| C07D 217/22 | (2006.01) |
| A61K 31/549 | (2006.01) |
| A61P 35/00 | (2006.01) |
| A61K 45/06 | (2006.01) |
| C07D 401/04 | (2006.01) |
| A61K 31/4725 | (2006.01) |
| A61K 31/506 | (2006.01) |
| A61K 31/501 | (2006.01) |
| C07D 471/04 | (2006.01) |
| C07D 413/04 | (2006.01) |
| C07D 413/14 | (2006.01) |
| A61K 31/5377 | (2006.01) |
| C07D 417/04 | (2006.01) |
| A61K 31/4985 | (2006.01) |
| C07D 401/14 | (2006.01) |
| C07D 487/04 | (2006.01) |
| A61K 31/551 | (2006.01) |

(Continued)

(52) U.S. Cl.
CPC .......... *C07D 217/22* (2013.01); *A61K 31/472* (2013.01); *A61K 31/4725* (2013.01); *A61K 31/4985* (2013.01); *A61K 31/501* (2013.01); *A61K 31/506* (2013.01); *A61K 31/5377* (2013.01); *A61K 31/5383* (2013.01); *A61K 31/549* (2013.01); *A61K 31/55* (2013.01); *A61K 31/551* (2013.01); *A61K 31/554* (2013.01); *A61K 45/06* (2013.01); *A61P 35/00* (2018.01); *C07D 401/04* (2013.01); *C07D 401/14* (2013.01); *C07D 405/14* (2013.01); *C07D 409/14* (2013.01); *C07D 413/04* (2013.01); *C07D 413/14* (2013.01); *C07D 417/04* (2013.01); *C07D 471/04* (2013.01); *C07D 487/04* (2013.01); *C07D 487/14* (2013.01); *C07D 491/04* (2013.01); *C07D 498/04* (2013.01); *C07D 498/14* (2013.01); *C07D 513/04* (2013.01); *C07D 519/00* (2013.01)

(58) Field of Classification Search
CPC .................................................... C07D 217/22
See application file for complete search history.

(56) References Cited

U.S. PATENT DOCUMENTS

| | | | |
|---|---|---|---|
| 4,590,273 A | 5/1986 | Konz et al. |
| 7,863,291 B2 | 1/2011 | Cook, II et al. |

(Continued)

FOREIGN PATENT DOCUMENTS

| | | |
|---|---|---|
| CN | 107266421 A | 10/2017 |
| EA | 018163 B1 | 5/2013 |

(Continued)

OTHER PUBLICATIONS

Bur et al. CAS: 155:509957, 2011.*

(Continued)

*Primary Examiner* — Rei Tsang Shiao

(57) ABSTRACT

Isoquinoline compounds and their use as inhibitors of HPK1 (hematopoietic kinase 1) are described. The compounds are useful in treating HPK1-dependent disorders and enhancing an immune response. Also described are methods of inhibiting HPK1, methods of treating HPK1-dependent disorders, methods for enhancing an immune response, and methods for preparing the isoquinoline compounds.

31 Claims, No Drawings

Specification includes a Sequence Listing.

(51) Int. Cl.
  C07D 498/04      (2006.01)
  A61K 31/5383     (2006.01)
  C07D 405/14      (2006.01)
  C07D 519/00      (2006.01)
  C07D 498/14      (2006.01)
  C07D 513/04      (2006.01)
  A61K 31/554      (2006.01)
  A61K 31/55       (2006.01)
  A61K 31/472      (2006.01)
  C07D 409/14      (2006.01)
  C07D 491/04      (2006.01)
  C07D 487/14      (2006.01)

(56) References Cited

U.S. PATENT DOCUMENTS

| | | |
|---|---|---|
| 8,309,577 B2 | 11/2012 | Cook, II et al. |
| 8,461,339 B2 | 6/2013 | Boyle et al. |
| 8,530,468 B2 | 9/2013 | Collins et al. |
| 2006/0156485 A1 | 7/2006 | Lim et al. |
| 2009/0143399 A1 | 6/2009 | Hurley et al. |
| 2010/0081671 A1 | 4/2010 | Plettenburg et al. |
| 2010/0113467 A1 | 5/2010 | Manley et al. |
| 2010/0331328 A1 | 12/2010 | Collins et al. |
| 2011/0245248 A1 | 10/2011 | Plettenburg et al. |
| 2013/0096119 A1 | 4/2013 | Bur et al. |
| 2013/0302303 A1 | 11/2013 | Hurley et al. |
| 2014/0066453 A1 | 3/2014 | Blake et al. |
| 2016/0060262 A1 | 3/2016 | Lyssikatos et al. |
| 2018/0072719 A1 | 3/2018 | Ye et al. |
| 2018/0072720 A1 | 3/2018 | Vechorkin et al. |
| 2020/0108075 A1 | 4/2020 | Liang et al. |
| 2021/0253580 A1 | 8/2021 | Liang et al. |
| 2021/0332064 A1 | 10/2021 | Liang et al. |

FOREIGN PATENT DOCUMENTS

| | | |
|---|---|---|
| EP | 2937345 A2 | 10/2015 |
| PL | 176081 B1 | 4/1999 |
| WO | 2000/071508 A2 | 11/2000 |
| WO | 2000/071508 A3 | 11/2000 |
| WO | 2000/071510 A2 | 11/2000 |
| WO | 2000/071510 A3 | 11/2000 |
| WO | 2005/032468 A2 | 4/2005 |
| WO | 2005/032468 A3 | 4/2005 |
| WO | 2005/035503 A1 | 4/2005 |
| WO | 2006/048248 A2 | 5/2006 |
| WO | 2006/048248 A3 | 5/2006 |
| WO | 2006/048251 A1 | 5/2006 |
| WO | 2007/000240 A1 | 1/2007 |
| WO | 2007/041511 A2 | 4/2007 |
| WO | 2007/053346 A1 | 5/2007 |
| WO | 2007/071348 A1 | 6/2007 |
| WO | 2007/084391 A2 | 7/2007 |
| WO | 2007/125405 A2 | 11/2007 |
| WO | 2007/125405 A3 | 11/2007 |
| WO | 2008/077554 A1 | 7/2008 |
| WO | 2008/119569 A1 | 10/2008 |
| WO | 2009/000558 A1 | 12/2008 |
| WO | 2009/023193 A1 | 2/2009 |
| WO | 2009/103966 A1 | 8/2009 |
| WO | 2009/131926 A1 | 10/2009 |
| WO | 2010/007374 A1 | 1/2010 |
| WO | 2010/042699 A1 | 4/2010 |
| WO | 2011/073845 A1 | 6/2011 |
| WO | 2011/075607 A1 | 6/2011 |
| WO | 2011/121555 A1 | 10/2011 |
| WO | 2012/056372 A1 | 5/2012 |
| WO | 2012/080284 A2 | 6/2012 |
| WO | 2012/080284 A3 | 6/2012 |
| WO | 2012/137099 A1 | 10/2012 |
| WO | 2012/177725 A1 | 12/2012 |
| WO | 2012/177728 A1 | 12/2012 |
| WO | 2013/003315 A2 | 1/2013 |
| WO | 2013/169793 A2 | 11/2013 |
| WO | 2013/169793 A3 | 11/2013 |
| WO | 2014/036015 A1 | 3/2014 |
| WO | 2014/037751 A1 | 3/2014 |
| WO | 2014/043296 A1 | 3/2014 |
| WO | 2014/123900 A1 | 8/2014 |
| WO | 2015/003166 A1 | 1/2015 |
| WO | 2016/014674 A1 | 1/2016 |
| WO | 2016/0436530 A1 | 3/2016 |
| WO | 2016/090300 A1 | 6/2016 |
| WO | 2016/205942 A1 | 12/2016 |
| WO | 2017/069980 A1 | 4/2017 |
| WO | 2017/106556 A1 | 6/2017 |
| WO | 2017/152821 A1 | 9/2017 |
| WO | 2017/155765 A1 | 9/2017 |
| WO | 2017/158388 A1 | 9/2017 |
| WO | 2017/189823 A2 | 11/2017 |
| WO | 2017/189829 A1 | 11/2017 |
| WO | 2018/065768 A1 | 4/2018 |
| WO | 2018/102366 A1 | 6/2018 |
| WO | 2018/119263 A1 | 6/2018 |
| WO | 2018/136700 A1 | 7/2018 |
| WO | 2018/182051 A1 | 10/2018 |
| WO | 2018/183418 A1 | 10/2018 |
| WO | 2018/183964 A1 | 10/2018 |
| WO | 2018/231745 A1 | 12/2018 |
| WO | 2019/079626 A1 | 4/2019 |
| WO | 2019/084497 A1 | 5/2019 |
| WO | 2019/155066 A1 | 8/2019 |
| WO | 2020/023560 A1 | 1/2020 |
| WO | 2020/072627 A1 | 4/2020 |
| WO | 2020/072695 A1 | 4/2020 |

OTHER PUBLICATIONS

Bartmann, W. et al., "Synthesis of di- and tetraalkyl-3-piperazinoisoquinolines and related compounds as potential antidepressant agents" Journal of Heterocyclic Chemistry 24(3):677-82 (1987).

Collins, I., et al., CAS Registry Database, 1184844-45-8, CAPLUS Accession No. 2009:1042183Document No. 151:289187, Entitled: Bicyclylaryl-aryl-amine compounds, their preparation, and their use as CHKI kinase inhibitors for treating proliferative diseases, pp. 1-3 (2009).

Dibartolo, V., et al., "A novel pathway down-modulating T cell activation involves HPK-1-dependent recruitment of 14-3-3 proteins on SLP-76" J Exp Med 204(3):681-691 (Mar. 19, 2007).

Dong, X. et al., "QSAR study of Akt/protein kinase B (PKB) inhibitors using support vector machine" European Journal of Medicinal Chemistry 44(10):4090-4097 (2009).

"International Search Report—PCT/US2018/025573" (w/Written Opinion), pp. 1-26 (Jun. 22, 2018).

Johnson, C.N. et al., "Structure-Based Design of Type II Inhibitors Applied to Maternal Embryonic Leucine Zipper Kinase" ACS Medicinal Chemistry Letters 6(1):31-36 (2015).

Lasserre, R., et al., "Release of serine/threonine-phosphorylated adaptors from signaling microclusters down-regulates T cell activation" J Cell Biol 195(5):839-853 (Nov. 28, 2011).

Liang, J. et al., "Identification of an imidazopyridine scaffold to generate potent and selective TYK2 inhibitors that demonstrate activity in an in vivo psoriasis model" Bioorganic & Medicinal Chemistry Letters 27(18):4370-4376 (2017).

Lu, B. et al., "Discovery of EBI-907: A highly potent and orally active B-RafV600E inhibitor for the treatment of melanoma and associated cancers" Bioorganic & Medicinal Chemistry Letters 26(3):819-823 (2016).

Ma, X. et al., "Identification of New FLT3 Inhibitors That Potently Inhibit AML Cell Lines via an Azo Click-It/Staple-It Approach" ACS Medicinal Chemistry Letters 8(5):492-497 (2017).

Panchaud, P. et al., "Discovery and Optimization of Isoquinoline Ethyl Ureas as Antibacteiial Agents" Journal of Medicinal Chemistry 60(9):3755-3775 (2017).

Yule, I.A. et al., "Pyridine-3-carboxamide-6-yl-ureas as novel inhibitors of bacterial DNA gyrase: Structure based design, synthesis, SAR and antimicrobial activity" European Journal of Medicinal Chemistry 86:31-38 (2014).

(56) References Cited

OTHER PUBLICATIONS

Zdrojewski, T. et al., "A general approach to 3-aminoisoquinoline, its N-mono- and N,N-disubstituted derivatives" Tetrahedron 51(45):12439-44 (1995).
Zeng, Q. et al., "Azole-based inhibitors of AKT/PKB for the treatment of cancer" Bioorganic & Medicinal Chemistry Letters 20(5):1559-1564 (2010).
Zhu, G. et al., "Isoquinoline-pyridine-based protein kinase B/Akt antagonists: SAR and in Vivo antitumor activity" Bioorganic & Medicinal Chemistry Letters 16(12):3150-3155 (2006).
Belikov et al., Pharmaceutical Chemistry (Text in Russian with English translation attached), Moscow, MEDpress-inforrn, pp. 27-29 (2007).
Dyson et al., Chemistry of Synthetic Medicinal Substances (Text in Russian with English translation attached), Moscow, pp. 12-19 (1964).
International Preliminary Report on Patentability, PCT/US2018/025573, 7 pages (dated Oct. 1, 2019).
Kharkevich, Pharmacology (Text in Russian with English translation attached), 10th edition, Moscow, GEOTAR-Media, pp. 73-74 (2010).
Linney et al., "Inhibitors of Immuno-oncology Target HPK1—A Patent Review (2016 to 2020)," Expert Opin. Ther. Pat., 31(10):893-910 (2021).
Mashkovsky, "Medicines" (Text in Russian with English translation attached), Moscow (Part 1), p. 8 (1993).
U.S. Appl. No. 15/942,333, filed Mar. 30, 2018, Bryan Chan et al., Abandoned.
U.S. Appl. No. 16/592,502, filed Oct. 3, 2019, Jun Liang et al., Pending.
U.S. Appl. No. 16/806,654, filed Mar. 2, 2020, Bryan Chan et al., Abandoned.
U.S. Appl. No. 17/156,387, filed Jan. 22, 2021, Jun Liang et al., Pending.
U.S. Appl. No. 17/220,307, filed Apr. 1, 2021, Jun Liang et al., Pending.

\* cited by examiner

SEQUENCE LISTING

<160> NUMBER OF SEQ ID NOS: 4

<210> SEQ ID NO 1

```
<211> LENGTH: 2502
<212> TYPE: DNA
<213> ORGANISM: Homo sapiens

<400> SEQUENCE: 1
atggacgtcg tggaccctga cattttcaat agagaccccc gggaccacta tgacctgcta      60
cagcggctgg gtggcggcac gtatggggaa gtctttaagg ctcgagacaa ggtgtcaggg     120
gacctggtgg cactgaagat ggtgaagatg gagcctgatg atgatgtctc caccccttcag    180 aaggaaatcc tcatattgaa aacttgccgg cacgccaaca tcgtggccta ccatgggagt     240
tatctctggt tgcagaaact ctggatctgc atggaattct gtggggctgg ttctctccag     300
gacatctacc aagtgacagg ctccctgtca gagctccaga ttagctatgt ctgccgggaa     360
gtgctccagg actggccta tttgcactca cagaagaaga tacacaggga catcaaggga      420
gctaacatcc tcatcaatga tgctggggag gtcagattgg ctgactttgg catctcggcc    480
cagattgggg ctacactggc cagacgcctc tctttcattg gacaccccta ctggatggct    540
ccggaagtgg cagctgtggc cctgaaggga ggatacaatg agctgtgtga catctggtcc    600
ctgggcatca cggccatcga actggccgag ctacagccac cgctctttga tgtgcaccct    660
ctcagagttc tcttcctcat gaccaagagt ggctaccagc tcccccgact gaaggaaaaa    720
ggcaaatggt cggctgcctt ccacaacttc atcaaagtca ctctgactaa gagtcccaag    780
aaacgaccca cgccaccaa gatgctcagt catcaactgg tatcccagcc tgggctgaat     840
cgaggcctga tcctggatct tcttgacaaa ctgaagaatc ccgggaaagg accctccatt    900
ggggacattg aggatgagga gcccgagcta ccccctgcta ccctcggcg gatcagatcc    960 acccaccgct ccagctctct ggggatccca gatgcagact gctgtcggcg gcacatggag   1020
ttcaggaagc tccgaggaat ggagaccaga cccccagcca caccgctcg cctacagcct    1080 cctcgagacc tcaggagcag cagccccagg aagcaactgt cagagtcgtc tgacgatgac   1140
tatgacgacg tggacatccc cacccctgca gaggacacac tcctccact tcccccccaag   1200 cccaagttcc gttctccatc agacgagggt cctgggagca tggggatga tgggcagctg   1260 agcccggggg tgctggtccg tgtgccagt gggccccac caaacagccc ccgtcctggg     1320
cctcccccat ccaccagcag cccccacctc accgcccatt cagaaccctc actctggaac   1380
ccaccctccc gggagcttga caagccccca cttctgcccc caagaagga aaagatgaag   1440 agaaagggat gtgcccttct cgtaaagttg ttcaatggct gcccctccg gatccacagc   1500 acggccgcct ggacacatcc ctccaccaag gaccagcacc tgctcctggg ggcagaggaa   1560
ggcatcttca tcctgaaccg gaatgaccag gaggccacgc tggaaatgct ctttcctagc   1620
cggactacgt gggtgtactc catcaacaac gttctcatgt ctctctcagg aaagaccccc    1680
cacctgtatt ctcatagcat ccttggcctg ctggaacgga aagagaccag agcaggaaac   1740
cccatcgctc acattagccc ccaccgccta ctggcaagga gaacatggt ttccaccaag    1800 atccaggaca ccaaaggctg ccgggcgtgc tgtgtggcgg agggtgcgag ctctgggggc   1860
ccgttcctgt gcggtgcatt ggagacgtcc gttgtcctgc ttcagtggta ccagcccatg   1920
aacaaattcc tgcttgtccg gcaggtgctg ttcccactgc cgacgcctct gtccgtgttc   1980
gcgctgctga ccgggccagg ctctgagctg cccgctgtgt gcatcggcgt gagccccggg   2040
cggccgggga agtcggtgct cttccacacg gtgcgctttg gcgcgctctc ttgctggctg   2100
ggcgagatga gcaccgagca cagggggaccc gtgcaggtga cccaggtaga ggaagatatg   2160
gtgatggtgt tgatggatgg ctctgtgaag ctggtgaccc cggaggggtc cccagtccgg   2220
```

```
ggacttcgca cacctgagat ccccatgacc gaagcggtgg aggccgtggc tatggttgga  2280
ggtcagcttc aggccttctg gaagcatgga gtgcaggtgt gggctctagg ctcggatcag  2340
ctgctacagg agctgagaga ccctacccctc actttccgtc tgcttggctc ccccaggctg  2400
gagtgcagtg gcacgatctc gcctcactgc aacctcctcc tcccaggttc aagcaattct  2460
cctgcctcag cctcccgagt agctgggatt acaggcctgt ag                    2502
```

<210> SEQ ID NO 2
<211> LENGTH: 833
<212> TYPE: PRT
<213> ORGANISM: Homo sapiens

<400> SEQUENCE: 2

```
Met Asp Val Val Asp Pro Asp Ile Phe Asn Arg Asp Pro Arg Asp His
1               5                   10                  15

Tyr Asp Leu Leu Gln Arg Leu Gly Gly Gly Thr Tyr Gly Glu Val Phe
            20                  25                  30

Lys Ala Arg Asp Lys Val Ser Gly Asp Leu Val Ala Leu Lys Met Val
        35                  40                  45

Lys Met Glu Pro Asp Asp Asp Val Ser Thr Leu Gln Lys Glu Ile Leu
    50                  55                  60

Ile Leu Lys Thr Cys Arg His Ala Asn Ile Val Ala Tyr His Gly Ser
65                  70                  75                  80

Tyr Leu Trp Leu Gln Lys Leu Trp Ile Cys Met Glu Phe Cys Gly Ala
                85                  90                  95

Gly Ser Leu Gln Asp Ile Tyr Gln Val Thr Gly Ser Leu Ser Glu Leu
            100                 105                 110

Gln Ile Ser Tyr Val Cys Arg Glu Val Leu Gln Gly Leu Ala Tyr Leu
        115                 120                 125

His Ser Gln Lys Lys Ile His Arg Asp Ile Lys Gly Ala Asn Ile Leu
    130                 135                 140

Ile Asn Asp Ala Gly Glu Val Arg Leu Ala Asp Phe Gly Ile Ser Ala
145                 150                 155                 160

Gln Ile Gly Ala Thr Leu Ala Arg Arg Leu Ser Phe Ile Gly Thr Pro
                165                 170                 175

Tyr Trp Met Ala Pro Glu Val Ala Ala Val Ala Leu Lys Gly Gly Tyr
            180                 185                 190

Asn Glu Leu Cys Asp Ile Trp Ser Leu Gly Ile Thr Ala Ile Glu Leu
        195                 200                 205

Ala Glu Leu Gln Pro Pro Leu Phe Asp Val His Pro Leu Arg Val Leu
    210                 215                 220

Phe Leu Met Thr Lys Ser Gly Tyr Gln Pro Pro Arg Leu Lys Glu Lys
225                 230                 235                 240

Gly Lys Trp Ser Ala Ala Phe His Asn Phe Ile Lys Val Thr Leu Thr
                245                 250                 255

Lys Ser Pro Lys Lys Arg Pro Ser Ala Thr Lys Met Leu Ser His Gln
            260                 265                 270

Leu Val Ser Gln Pro Gly Leu Asn Arg Gly Leu Ile Leu Asp Leu Leu
        275                 280                 285

Asp Lys Leu Lys Asn Pro Gly Lys Gly Pro Ser Ile Gly Asp Ile Glu
    290                 295                 300

Asp Glu Glu Pro Glu Leu Pro Pro Ala Ile Pro Arg Arg Ile Arg Ser
305                 310                 315                 320
```

```
Thr His Arg Ser Ser Ser Leu Gly Ile Pro Asp Ala Asp Cys Cys Arg
            325                 330                 335

Arg His Met Glu Phe Arg Lys Leu Arg Gly Met Glu Thr Arg Pro Pro
        340                 345                 350

Ala Asn Thr Ala Arg Leu Gln Pro Pro Arg Asp Leu Arg Ser Ser Ser
        355                 360                 365

Pro Arg Lys Gln Leu Ser Glu Ser Ser Asp Asp Tyr Asp Asp Val
    370                 375                 380

Asp Ile Pro Thr Pro Ala Glu Asp Thr Pro Pro Leu Pro Pro Lys
385                 390                 395                 400

Pro Lys Phe Arg Ser Pro Ser Asp Glu Gly Pro Gly Ser Met Gly Asp
            405                 410                 415

Asp Gly Gln Leu Ser Pro Gly Val Leu Val Arg Cys Ala Ser Gly Pro
            420                 425                 430

Pro Pro Asn Ser Pro Arg Pro Gly Pro Pro Ser Thr Ser Ser Pro
        435                 440                 445

His Leu Thr Ala His Ser Glu Pro Ser Leu Trp Asn Pro Pro Ser Arg
            450                 455                 460

Glu Leu Asp Lys Pro Pro Leu Leu Pro Pro Lys Lys Glu Lys Met Lys
465                 470                 475                 480

Arg Lys Gly Cys Ala Leu Leu Val Lys Leu Phe Asn Gly Cys Pro Leu
            485                 490                 495

Arg Ile His Ser Thr Ala Ala Trp Thr His Pro Ser Thr Lys Asp Gln
            500                 505                 510

His Leu Leu Leu Gly Ala Glu Glu Gly Ile Phe Ile Leu Asn Arg Asn
            515                 520                 525

Asp Gln Glu Ala Thr Leu Glu Met Leu Phe Pro Ser Arg Thr Thr Trp
    530                 535                 540

Val Tyr Ser Ile Asn Asn Val Leu Met Ser Leu Ser Gly Lys Thr Pro
545                 550                 555                 560

His Leu Tyr Ser His Ser Ile Leu Gly Leu Leu Glu Arg Lys Glu Thr
            565                 570                 575

Arg Ala Gly Asn Pro Ile Ala His Ile Ser Pro His Arg Leu Leu Ala
            580                 585                 590

Arg Lys Asn Met Val Ser Thr Lys Ile Gln Asp Thr Lys Gly Cys Arg
            595                 600                 605

Ala Cys Cys Val Ala Glu Gly Ala Ser Ser Gly Pro Phe Leu Cys
        610                 615                 620

Gly Ala Leu Glu Thr Ser Val Val Leu Leu Gln Trp Tyr Gln Pro Met
625                 630                 635                 640

Asn Lys Phe Leu Leu Val Arg Gln Val Leu Phe Pro Leu Pro Thr Pro
            645                 650                 655

Leu Ser Val Phe Ala Leu Leu Thr Gly Pro Gly Ser Glu Leu Pro Ala
            660                 665                 670

Val Cys Ile Gly Val Ser Pro Gly Arg Pro Gly Lys Ser Val Leu Phe
            675                 680                 685

His Thr Val Arg Phe Gly Ala Leu Ser Cys Trp Leu Gly Glu Met Ser
            690                 695                 700

Thr Glu His Arg Gly Pro Val Gln Val Thr Gln Val Glu Glu Asp Met
705                 710                 715                 720

Val Met Val Leu Met Asp Gly Ser Val Lys Leu Val Thr Pro Glu Gly
                725                 730                 735

Ser Pro Val Arg Gly Leu Arg Thr Pro Glu Ile Pro Met Thr Glu Ala
```

|  |  |  | 740 |  |  |  | 745 |  |  |  | 750 |  |
|---|---|---|---|---|---|---|---|---|---|---|---|---|

Val Glu Ala Val Ala Met Val Gly Gly Gln Leu Gln Ala Phe Trp Lys
            755                 760                 765

His Gly Val Gln Val Trp Ala Leu Gly Ser Asp Gln Leu Leu Gln Glu
        770                 775                 780

Leu Arg Asp Pro Thr Leu Thr Phe Arg Leu Leu Gly Ser Pro Arg Leu
785                 790                 795                 800

Glu Cys Ser Gly Thr Ile Ser Pro His Cys Asn Leu Leu Leu Pro Gly
                805                 810                 815

Ser Ser Asn Ser Pro Ala Ser Ala Ser Arg Val Ala Gly Ile Thr Gly
                820                 825                 830

Leu

<210> SEQ ID NO 3
<211> LENGTH: 2466
<212> TYPE: DNA
<213> ORGANISM: Homo sapiens

<400> SEQUENCE: 3

| atggacgtcg tggaccctga cattttcaat agagaccccc gggaccacta tgacctgcta | 60 |
|---|---|
| cagcggctgg gtggcggcac gtatggggaa gtctttaagg ctcgagacaa ggtgtcaggg | 120 |
| gacctggtgg cactgaagat ggtgaagatg gagcctgatg atgatgtctc cacccttcag | 180 |
| aaggaaatcc tcatattgaa aacttgccgg cacgccaaca tcgtggccta ccatgggagt | 240 |
| tatctctggt tgcagaaact ctggatctgc atggaattct gtggggctgg ttctctccag | 300 |
| gacatctacc aagtgacagg ctccctgtca gagctccaga ttagctatgt ctgccgggaa | 360 |
| gtgctccagg gactggccta tttgcactca cagaagaaga tacacaggga catcaaggga | 420 |
| gctaacatcc tcatcaatga tgctggggag gtcagattgg ctgactttgg catctcggcc | 480 |
| cagattgggg ctacactggc cagacgcctc tctttcattg gacacccta ctggatggct | 540 |
| ccggaagtgg cagctgtggc cctgaaggga ggatacaatg agctgtgtga catctggtcc | 600 |
| ctgggcatca cggccatcga actggccgag ctacagccac cgctctttga tgtgcaccct | 660 |
| ctcagagttc tcttcctcat gaccaagagt ggctaccagc ctcccgact gaaggaaaaa | 720 |
| ggcaaatggt cggctgcctt ccacaacttc atcaaagtca ctctgactaa gagtcccaag | 780 |
| aaacgaccca cgccaccaa gatgctcagt catcaactgg tatcccagcc tgggctgaat | 840 |
| cgaggcctga tcctggatct tcttgacaaa ctgaagaatc ccgggaaagg accctccatt | 900 |
| ggggacattg aggatgagga gcccgagcta cccctgcta tccctcggcg atcagatcc | 960 |
| acccaccgct ccagctctct ggggatccca gatgcagact gctgtcggcg gcacatggag | 1020 |
| ttcaggaagc tccgaggaat ggagaccaga ccccagcca acaccgctcg cctacagcct | 1080 |
| cctcgagacc tcaggagcag cagccccagg aagcaactgt cagagtcgtc tgacgatgac | 1140 |
| tatgacgacg tggacatccc cacccctgca gaggacacac ctcctccact tccccccaag | 1200 |
| cccaagttcc gttctccatc agacgagggt cctgggagca tggggatga tgggcagctg | 1260 |
| agcccggggg tgctggtccg gtgtgccagt gggcccccac caaacagccc ccgtcctggg | 1320 |
| cctcccccat ccaccagcag ccccaccctc accgccatt cagaaccctc actctggaac | 1380 |
| ccacccctccc gggagcttga caagccccca cttctgcccc caagaaggga aagatgaag | 1440 |
| agaaagggat gtgcccttct cgtaaagttg ttcaatggct gccccctccg gatccacagc | 1500 |
| acggccgcct ggacacatcc ctccaccaag gaccagcacc tgctcctggg ggcagaggaa | 1560 |

-continued

```
ggcatcttca tcctgaaccg gaatgaccag gaggccacgc tggaaatgct ctttcctagc   1620
cggactacgt gggtgtactc catcaacaac gttctcatgt ctctctcagg aaagaccccc   1680
cacctgtatt ctcatagcat ccttggcctg ctggaacgga aagagaccag agcaggaaac   1740
cccatcgctc acattagccc ccaccgccta ctggcaagga agaacatggt ttccaccaag   1800
atccaggaca ccaaaggctg ccgggcgtgc tgtgtggcgg agggtgcgag ctctgggggc   1860
ccgttcctgt gcggtgcatt ggagacgtcc gttgtcctgc ttcagtggta ccagcccatg   1920
aacaaattcc tgcttgtccg gcaggtgctg ttcccactgc cgacgcctct gtccgtgttc   1980
gcgctgctga ccgggccagg ctctgagctg cccgctgtgt gcatcggcgt gagcccggg    2040 cggccgggga agtcggtgct cttccacacg gtgcgctttg gcgcgctctc ttgctggctg   2100
ggcgagatga gcaccgagca caggggaccc gtgcaggtga cccaggtaga ggaagatatg   2160
gtgatggtgt tgatggatgg ctctgtgaag ctggtgaccc cggagggggtc cccagtccgg   2220 ggacttcgca cacctgagat ccccatgacc gaagcggtgg aggccgtggc tatggttgga   2280
ggtcagcttc aggccttctg gaagcatgga gtgcaggtgt gggctctagg ctcggatcag   2340
ctgctacagg agctgagaga ccctacccte actttccgtc tgcttggctc ccccaggcct   2400
gtagtggtgg agacacgccc agtggatgat cctactgctc ccagcaacct ctacatccag   2460
gaatga                                                              2466
```

<210> SEQ ID NO 4
<211> LENGTH: 821
<212> TYPE: PRT
<213> ORGANISM: Homo sapiens

<400> SEQUENCE: 4

```
Met Asp Val Val Asp Pro Asp Ile Phe Asn Arg Asp Pro Arg Asp His
1               5                   10                  15

Tyr Asp Leu Leu Gln Arg Leu Gly Gly Gly Thr Tyr Gly Glu Val Phe
            20                  25                  30

Lys Ala Arg Asp Lys Val Ser Gly Asp Leu Val Ala Leu Lys Met Val
        35                  40                  45

Lys Met Glu Pro Asp Asp Asp Val Ser Thr Leu Gln Lys Glu Ile Leu
    50                  55                  60

Ile Leu Lys Thr Cys Arg His Ala Asn Ile Val Ala Tyr His Gly Ser
65                  70                  75                  80

Tyr Leu Trp Leu Gln Lys Leu Trp Ile Cys Met Glu Phe Cys Gly Ala
                85                  90                  95

Gly Ser Leu Gln Asp Ile Tyr Gln Val Thr Gly Ser Leu Ser Glu Leu
            100                 105                 110

Gln Ile Ser Tyr Val Cys Arg Glu Val Leu Gln Gly Leu Ala Tyr Leu
        115                 120                 125

His Ser Gln Lys Lys Ile His Arg Asp Ile Lys Gly Ala Asn Ile Leu
    130                 135                 140

Ile Asn Asp Ala Gly Glu Val Arg Leu Ala Asp Phe Gly Ile Ser Ala
145                 150                 155                 160

Gln Ile Gly Ala Thr Leu Ala Arg Arg Leu Ser Phe Ile Gly Thr Pro
                165                 170                 175

Tyr Trp Met Ala Pro Glu Val Ala Ala Val Ala Leu Lys Gly Gly Tyr
            180                 185                 190

Asn Glu Leu Cys Asp Ile Trp Ser Leu Gly Ile Thr Ala Ile Glu Leu
        195                 200                 205
```

-continued

```
Ala Glu Leu Gln Pro Pro Leu Phe Asp Val His Pro Leu Arg Val Leu
    210                 215                 220

Phe Leu Met Thr Lys Ser Gly Tyr Gln Pro Pro Arg Leu Lys Glu Lys
225                 230                 235                 240

Gly Lys Trp Ser Ala Ala Phe His Asn Phe Ile Lys Val Thr Leu Thr
                245                 250                 255

Lys Ser Pro Lys Lys Arg Pro Ser Ala Thr Lys Met Leu Ser His Gln
                260                 265                 270

Leu Val Ser Gln Pro Gly Leu Asn Arg Gly Leu Ile Leu Asp Leu Leu
            275                 280                 285

Asp Lys Leu Lys Asn Pro Gly Lys Gly Pro Ser Ile Gly Asp Ile Glu
    290                 295                 300

Asp Glu Glu Pro Glu Leu Pro Pro Ala Ile Pro Arg Arg Ile Arg Ser
305                 310                 315                 320

Thr His Arg Ser Ser Ser Leu Gly Ile Pro Asp Ala Asp Cys Cys Arg
                325                 330                 335

Arg His Met Glu Phe Arg Lys Leu Arg Gly Met Glu Thr Arg Pro Pro
                340                 345                 350

Ala Asn Thr Ala Arg Leu Gln Pro Pro Arg Asp Leu Arg Ser Ser Ser
            355                 360                 365

Pro Arg Lys Gln Leu Ser Glu Ser Ser Asp Asp Tyr Asp Asp Val
    370                 375                 380

Asp Ile Pro Thr Pro Ala Glu Asp Thr Pro Pro Pro Leu Pro Pro Lys
385                 390                 395                 400

Pro Lys Phe Arg Ser Pro Ser Asp Glu Gly Pro Gly Ser Met Gly Asp
                405                 410                 415

Asp Gly Gln Leu Ser Pro Gly Val Leu Val Arg Cys Ala Ser Gly Pro
            420                 425                 430

Pro Pro Asn Ser Pro Arg Pro Gly Pro Pro Ser Thr Ser Ser Pro
    435                 440                 445

His Leu Thr Ala His Ser Glu Pro Ser Leu Trp Asn Pro Pro Ser Arg
            450                 455                 460

Glu Leu Asp Lys Pro Pro Leu Leu Pro Pro Lys Lys Glu Lys Met Lys
465                 470                 475                 480

Arg Lys Gly Cys Ala Leu Leu Val Lys Leu Phe Asn Gly Cys Pro Leu
                485                 490                 495

Arg Ile His Ser Thr Ala Ala Trp Thr His Pro Ser Thr Lys Asp Gln
                500                 505                 510

His Leu Leu Leu Gly Ala Glu Glu Gly Ile Phe Ile Leu Asn Arg Asn
            515                 520                 525

Asp Gln Glu Ala Thr Leu Glu Met Leu Phe Pro Ser Arg Thr Thr Trp
    530                 535                 540

Val Tyr Ser Ile Asn Asn Val Leu Met Ser Leu Ser Gly Lys Thr Pro
545                 550                 555                 560

His Leu Tyr Ser His Ser Ile Leu Gly Leu Leu Glu Arg Lys Glu Thr
                565                 570                 575

Arg Ala Gly Asn Pro Ile Ala His Ile Ser Pro His Arg Leu Leu Ala
            580                 585                 590

Arg Lys Asn Met Val Ser Thr Lys Ile Gln Asp Thr Lys Gly Cys Arg
            595                 600                 605

Ala Cys Cys Val Ala Glu Gly Ala Ser Ser Gly Gly Pro Phe Leu Cys
            610                 615                 620

Gly Ala Leu Glu Thr Ser Val Val Leu Leu Gln Trp Tyr Gln Pro Met
```

```
625              630              635              640
Asn Lys Phe Leu Leu Val Arg Gln Val Leu Phe Pro Leu Pro Thr Pro
                645              650              655

Leu Ser Val Phe Ala Leu Leu Thr Gly Pro Gly Ser Glu Leu Pro Ala
                660              665              670

Val Cys Ile Gly Val Ser Pro Gly Arg Pro Gly Lys Ser Val Leu Phe
            675              680              685

His Thr Val Arg Phe Gly Ala Leu Ser Cys Trp Leu Gly Glu Met Ser
        690              695              700

Thr Glu His Arg Gly Pro Val Gln Val Thr Gln Val Glu Glu Asp Met
705              710              715              720

Val Met Val Leu Met Asp Gly Ser Val Lys Leu Val Thr Pro Glu Gly
                725              730              735

Ser Pro Val Arg Gly Leu Arg Thr Pro Glu Ile Pro Met Thr Glu Ala
                740              745              750

Val Glu Ala Val Ala Met Val Gly Gly Gln Leu Gln Ala Phe Trp Lys
                755              760              765

His Gly Val Gln Val Trp Ala Leu Gly Ser Asp Gln Leu Leu Gln Glu
        770              775              780

Leu Arg Asp Pro Thr Leu Thr Phe Arg Leu Leu Gly Ser Pro Arg Pro
785              790              795              800

Val Val Val Glu Thr Arg Pro Val Asp Asp Pro Thr Ala Pro Ser Asn
                805              810              815

Leu Tyr Ile Gln Glu
                820
```

ISOQUINOLINES AS INHIBITORS OF HPK1

CROSS-REFERENCE TO RELATED APPLICATIONS

This application is a divisional of U.S. Ser. No. 15/942,333 filed 30 Mar. 2018, which claims the benefit of priority to International Patent Application No. PCT/CN2017/078790 filed 30 Mar. 2017 and International Patent Application No. PCT/CN2018/076908 filed 15 Feb. 2018, the contents of which applications are hereby incorporated by reference in their entireties.

SEQUENCE LISTING

The instant application contains a Sequence Listing which has been submitted electronically in ASCII format and is hereby incorporated by reference in its entirety. Said ASCII copy, created 25 Jun. 2020, is named P34138-US-2SL.TXT and is 21,229 bytes in size.

FIELD OF THE INVENTION

This invention pertains to compounds that modulate the function of HPK1 and are useful for treatment of HPK1 mediated diseases and conditions such as cancer.

BACKGROUND

The major treatment modalities used by oncologists to treat cancer are surgical resection, radiation therapy, and classical chemotherapeutic drugs. Unfortunately, surgical resection is not a viable option for many tumors or forms of cancers. Further, radiation therapy and chemotherapeutic drugs do not target only diseased cells and therefore, end up damaging healthy cells. Therapeutics that more specifically target tumor cells are being developed by taking advantage of tumor-specific expression of antigens or inappropriate overexpression or activation of specific proteins within tumor cells, but tumor cells are prone to mutation and can become resistant to drugs that specifically target tumor cells.

A new cancer treatment paradigm has emerged that harnesses the patient's own immune system to overcome immunoevasive strategies utilized by many cancers and to enhance anti-tumor immunity. One such strategy is to inhibit negative regulators of immune responses that normally function to maintain peripheral tolerance, allowing tumor antigens to be recognized as non-self entities.

The hematopoietic progenitor kinase 1 (HPK1) is an example of a negative regulator of dendritic cell activation, and T and B cell responses that can be targeted to enhance anti-tumor immunity. HPK1 is expressed predominantly by hematopoietic cells, including early progenitors. In T cells, it is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters (Lasserre et al. (2011) *J Cell Biol* 195(5):839-853). HPK1 can also become activated in response to prostaglandin E2, which is often secreted by tumors, contributing to the escape of tumor cells from the immune system.

BRIEF SUMMARY

Antagonists of the enzyme HPK1 are provided herein. The compounds have a structure set forth in Formula I or Ia or are pharmaceutically acceptable salts, metabolites, prodrugs, or derivatives thereof. Further provided are methods of preparing the compounds of Formula I or Ia.

The compounds find use in inhibiting HPK1 kinase activity, enhancing an immune response, and in the treatment of HPK1-dependent disorders. Accordingly, pharmaceutical compositions comprising a compound of Formula I or Ia or a pharmaceutically acceptable salt, prodrug, metabolite, or derivative thereof and a pharmaceutically acceptable carrier are also provided. Methods of inhibiting HPK1 comprise contacting HPK1 with an effective amount of a compound of Formula I or Ia or a pharmaceutically acceptable salt, prodrug, metabolite, or derivative thereof are provided. Methods of treating a HPK1-dependent disorder comprise administering to a subject in need thereof a compound of Formula I or Ia or a pharmaceutical formulation thereof are provided. Also provided is a kit for treating a HPK1-dependent disorder, the kit comprising a pharmaceutical composition comprising a compound of Formula I or Ia; and instructions for use.

DETAILED DESCRIPTION

Disclosed herein, are compounds of Formula I or Ia and pharmaceutical compositions thereof that are inhibitors or modulators of HPK1 (hematopoietic progenitor kinase 1). As such, the compounds and compositions are useful in treating diseases and disorders mediated by HPK1. An example of a method of treating is in the case of a subject who is suffering from cancer. The compounds can be used not only to combat cancer, but can also advantageously be used to enhance an immune response in a subject in need thereof.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

Definitions

The term "substituent" refers to an atom or a group of atoms that replaces a hydrogen atom on a molecule. The term "substituted" denotes that a specified molecule bears one or more substituents. The term "a compound of the formula" or "a compound of formula" or "compounds of the formula" or "compounds of formula" refers to any compound selected from the genus of compounds as defined by Formula I or Ia.

As used herein, the term "alkyl" refers to a straight-chained or branched hydrocarbon group containing 1 to 12 carbon atoms. The term "lower alkyl" refers to a $C_1$-$C_6$ alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to linear or branched-chain monovalent hydrocarbon radical of two to eight carbon atoms ($C_2$-$C_8$), preferably ($C_{2-6}$), with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (CH=$CH_2$), allyl ($CH_2$CH=$CH_2$), and the like.

The term "alkenylene" refers to linear or branched-chain divalent hydrocarbon radical of two to eight carbon atoms ($C_2$-$C_8$), preferably ($C_{2-6}$), with at least one site of unsaturation, i.e., a carbon-carbon, $sp^2$ double bond, wherein the alkenylene radical may be optionally substituted substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkoxy" refers to an —O-alkyl group. Alkoxy groups may be optionally substituted with one or more substituents.

The term "haloalkyl" refers to an alkyl radical that is substituted by one or more halo substituents. Examples of haloalkyl groups include difluoromethyl ($CHF_2$), trifluoromethyl ($CF_3$), and 2,2,2-trifluoroethyl.

As used herein, the term "halogen", "hal" or "halo" means —F, —Cl, —Br or —I.

As used herein, the designations "(CO)" and "C(O)" are used to indicate a carbonyl moiety. Examples of suitable carbonyl moieties include, but are not limited to, ketone and aldehyde moieties.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-10 membered mono- or bi-cyclic where the heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" or "heterocyclyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolanyl, tetrahydrofuranyl, tetrahydrothienyl, thienyl, and the like.

The term "hydroxyalkyl" refers to an alkyl substituent which is further substituted with one or more hydroxyl groups. The alkyl portion may be further optionally substituted with one or more substituents.

Combinations of substituents and/or variables are permissible only if such combinations result in correct valences. Unless otherwise indicated by context, a hyphen (-) designates the point of attachment of the pendant group or radical.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not minor images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

With respect to the nomenclature of a chiral center, the terms "d" and "l" (or plus and minus) configuration are as defined by the IUPAC Recommendations.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

A "metabolite" is a product produced through metabolism in the body of a specified compound or salt thereof. Metabolites of a compound may be identified using routine techniques known in the art and their activities determined using tests such as those described herein. Such products may result, for example, from the oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The phrase "pharmaceutically acceptable" indicates that the substance or composition is compatible, chemically and/or toxicologically, with the other ingredients comprising a formulation and/or the subject being treated therewithours.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt, the salt can have multiple counter ions. Hence, a pharmaceutically acceptable salt can have one or more charged atoms and/or one or more counter ion.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Non-limiting examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™ In certain embodiments, the pharmaceutically acceptable carrier is a non-naturally occurring pharmaceutically acceptable carrier.

Use of the word "inhibitor" herein is meant to mean a molecule that inhibits activity of HPK1. By "inhibit" herein is meant to decrease the activity of the target enzyme, as compared to the activity of that enzyme in the absence of the inhibitor. In some embodiments, the term "inhibit" means a decrease in HPK1 activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in HPK1 activity of about 5% to about 25%, about 25% to about 50%, about 50% to about 75%, or about 75% to 100%. In some embodiments, inhibit means a decrease in HPK1 activity of about 95% to 100%, e.g., a decrease in activity of 95%, 96%, 97%, 98%, 99%, or 100%. Such decreases can be measured using a variety of techniques that would be recognizable by one of skill in the art, including in vitro kinase assays.

As used herein, a "HPK1 antagonist" or a "HPK1 inhibitor" is a molecule that reduces, inhibits, or otherwise diminishes one or more of the biological activities of HPK1 (e.g., serine/threonine kinase activity, recruitment to the TCR complex upon TCR activation, interaction with a protein binding partner, such as SLP76). Antagonism using the HPK1 antagonist does not necessarily indicate a total elimination of the HPK1 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of HPK1 compared to an appropriate control. In some embodiments, the HPK1 antagonist reduces, inhibits, or otherwise diminishes the serine/threonine kinase activity of HPK1. In some of these embodiments, the HPK1 antagonist reduces, inhibits, or otherwise diminishes the HPK1-mediated phosphorylation of SLP76 and/or Gads. The presently disclosed compounds bind directly to HPK1 and inhibit its kinase activity.

By "specific antagonist" is intended an agent that reduces, inhibits, or otherwise diminishes the activity of a defined target greater than that of an unrelated target. For example, a HPK1 specific antagonist reduces at least one biological activity of HPK1 by an amount that is statistically greater than the inhibitory effect of the antagonist on any other protein (e.g., other serine/threonine kinases). In some embodiments, the $IC_{50}$ of the antagonist for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the HPK1 antagonist specifically inhibits the serine/threonine kinase activity of HPK1. In some of these embodiments, the $IC_{50}$ of the HIPK1 antagonist for HIPK1 is about 90%, 80%, 70%, 60%, 50%, 40%, 30%, 20%, 10%, 0.1%, 0.01%, 0.001%, or less of the $IC_{50}$ of the HIPK1 antagonist for another serine/threonine kinase or other type of kinase (e.g., tyrosine kinase).

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount can also be one in which any toxic or detrimental effects (e.g., side effects) of the inhibitor compound are not outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "abnormal cell growth," "unregulated cell growth," and "hyperproliferative disorder" are used interchangeably in this application. "Abnormal cell growth", as used herein, unless otherwise indicated, refers to cell growth that is independent of normal regulatory mechanisms (e.g., loss of contact inhibition).

The term "cancer" refers to the condition in a subject that is characterized by unregulated cell growth, wherein the cancerous cells are capable of local invasion and/or metastasis to noncontiguous sites. As used herein, "cancer cells," "cancerous cells," or "tumor cells" refer to the cells that are characterized by this unregulated cell growth and invasive property. The term "cancer" encompasses all types of cancers, including, but not limited to, all forms of carcinomas, melanomas, blastomas, sarcomas, lymphomas and leukemias, including without limitation, bladder cancer, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer, acute lymphocytic leukemia, acute myeloid leukemia, ependymoma, Ewing's sarcoma, glioblastoma, medulloblastoma, neuroblastoma, osteosarcoma, rhabdomyosarcoma, rhabdoid cancer, and nephroblastoma (Wilm's tumor).

A "chemotherapeutic agent" is a chemical compound or biologic useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., *Angew. Chem Intl. Ed. Engl.,* 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, and floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"- trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; EGFR inhibitor such as erlotinib or cetuximab; an anti-VEGF inhibitor such as bevacizumab; arinotecan; rmRH (e.g., ABARELIX®); 17AAG (geldanamycin derivative that is a heat shock protein (Hsp) 90 poison), and pharmaceutically acceptable salts, acids or derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN, Genentech); and (x) pharmaceutically acceptable salts, acids and derivatives of any of the above.

In some embodiments, the chemotherapeutic agent is an immunotherapeutic agent. As used herein, an "immunotherapeutic agent" is a compound that enhances the immune system to help fight cancer, specifically or non-specifically. Immunotherapeutics include monoclonal antibodies and non-specific immunotherapies that boost the immune system, such as cytokines, interleukins (e.g., IL-2, IL-7, IL-12, IL-15, IL-21), interferons (e.g., IFN-$\alpha$, IFN-$\beta$, IFN-$\gamma$), GM-CSF, thalidomide, (THALOMID®, Celgene), lenalidomide (REVLIMID®, Celgene), pomalidomide (POMALYST®, Celgene), imiquimod (ZYCLARA®, Valeant). Non-limiting examples of monoclonal antibodies that are useful as a chemotherapeutic agent include trastuzumab (HERCEPTIN®, Genentech), bevacizumab (AVASTIN®, Genentech), cetuximab (ERBITUX®, Bristol-Myers Squibb), panitumumab (VECTIBIX®, Amgen), ipilimumab (YERVOY®, Bristol-Myers Squibb), rituximab (RITUXAN®, Genentech), alemtuzumab (CAMPATH®, Genzyme), ofatumumab (ARZERRA®, Genmab), gemtuzumab ozogamicin (MYLOTARG®, Wyeth), brentuximab vedotin (ADCETRIS®, Seattle Genetics), $^{90}$Y-labelled ibritumomab tiuxetan (ZEVALIN®, Biogen Idec), $^{131}$I-labelled tositumomab (BEXXAR®, GlaxoSmithKline), ado-trastuzumab emtansine (KADCYLA®, Genentech) blinatumomab (BLINCYTO®, Amgen), pertuzumab (PERJETA®, Genentech), obinutuzumab (GAZYVA®, Genentech), nivolumab (OPDIVO®, ) Bristol-Myers Squibb), pembrolizumab (KEYTRUDA®, Merck), pidilizumab (CureTech), MPDL3280A (described in WO2010/077634, herein incorporated by reference in its entirety), MDX-1105 (described in WO2007/005874, herein incorporated by reference in its entirety), and MEDI4736 (described in WO2011/066389 and US2013/034559, each of which is herein incorporated by reference in its entirety). Another useful immunotherapeutic agent is AMP-224 (described in WO2010/027827 and WO2011/066342, each of which is incorporated herein in its entirety).

Compounds

The compounds disclosed herein are compounds of Formula I or Ia, or salts (e.g., pharmaceutically acceptable salts), solvates (e.g., hydrates), prodrugs, metabolites, or derivatives thereof. These compounds are useful inhibitors of HPK1.

In one aspect, provided is a compound of Formula I:

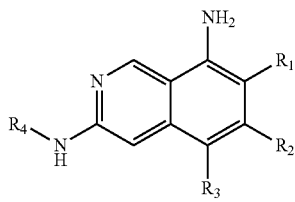

(I)

or salt (e.g., a pharmaceutically acceptable salt), solvate (e.g., hydrate), prodrug, metabolites or derivative thereof, wherein:

$R_1$ is hydrogen, halogen, cyano, $C_6$ alkyl, $C_{3-7}$ cycloalkyl, $C_{1-6}$ haloalkyl, $C_{1-6}$ hydroxyalkyl, hydroxyl, $C_{1-6}$ alkoxyl, optionally substituted amino or optionally substituted acylamino;

$R_2$ is (a), (b), (c), (d), (e), (f), (g) or (h):
(a) a 5-10 membered heteroaryl or 5-10 membered heterocyclyl, having 1-4 heteroatoms selected from O, S, and N; and optionally substituted with one, two, three, four or five substituents; or
(b) a $C_{6-10}$ aryl optionally substituted with one, two, three, four or five substituents; or
(c) hydrogen, halogen, cyano, $-NR^bC(O)R^a$, $-NR^bSO_2R^a$, $-SO_2NR^aR^b$; or $-SO_2R^a$; wherein each $R^a$ is independently $C_{1-6}$ alkyl, and $R^b$ is independently hydrogen or $C_{1-6}$ alkyl; or $R^a$ and $R^b$ are taken together with the atom(s) to which they are attached to form an optionally substituted 5-10 membered heterocyclyl; or
(d) $-OR^{a1}$ or $-(C_{1-6}$ alkylene$)-OR^{a1}$; wherein each $R^{a1}$ is independently $C_{1-6}$ alkyl optionally substituted with $C_{6-10}$ aryl; 5-10 membered heteroaryl; or 5-10 membered heterocyclyl; wherein the $C_{6-10}$ aryl, 5-10 membered heteroaryl, and 5-10 membered heterocyclyl are optionally substituted; or
(e) a $C_{1-6}$ alkyl, $C_{2-6}$ alkenyl, or $C_{2-6}$ alkynyl, each optionally substituted with one to five substituents; or
(f) a $C_{3-8}$ cycloalkyl optionally substituted with one to five substituents;
(g) $-C(O)NR^{a2}R^{b2}$ or $-NR^{a2}(CO)R^{b2}$, wherein each $R^{a2}$ is independently hydrogen or $C_{1-6}$ alkyl, and $R^{b2}$ is hydrogen, $C_{1-6}$ alkyl, $C_{6-10}$ aryl, 5-10 membered heteroaryl or 5-10 membered heterocyclyl; or $R^{a2}$ and $R^{b2}$ are taken together with the atom(s) to which they are attached to form an optionally substituted 5-10 membered heterocyclyl; wherein the $C_{1-6}$ alkyl, $C_{6-10}$ aryl, 5-10 membered heteroaryl and 5-10 membered heterocyclyl are optionally substituted; or
(h) 5-10 membered heteroaryl fused with a ring selected from the group consisting of 5 or 6 membered heteroaryl, 5-10 membered heterocyclyl, $C_{6-10}$ aryl and $C_{3-7}$ cycloalkyl, wherein the 5-10 membered heteroaryl of $R_2$ and the fused ring are optionally substituted with one to four substituents;

$R_3$ is hydrogen, cyano, halogen, optionally substituted $C_{1-6}$ alkyl, optionally substituted $C_{2-9}$ heterocyclyl, or optionally substituted $C_{1-6}$ alkoxy; and $R_4$ is A-C(O)— or D;

A is $C_{1-6}$ alkyl, $C_{3-7}$ cycloalkyl, $C_{2-9}$ heteroaryl, $C_{2-9}$ heterocyclyl, $-NHR^g$ or $-OR^h$; wherein the $C_{1-6}$ alkyl, $C_{3-7}$ cycloalkyl, 7 $C_{2-9}$ heteroaryl and $C_{2-9}$ heterocyclyl of A are optionally substituted independently with one, two, three, four or five substituents;

$R^g$ and $R^h$ are independently $C_{1-6}$ alkyl, $C_{2-6}$ alkenyl, $C_{3-7}$ cycloalkyl, $C_{6-10}$ aryl, $C_{2-9}$ heteroaryl, or $C_{2-9}$ heterocyclyl; wherein the $C_{1-6}$ alkyl, $C_{2-6}$ alkenyl, $C_{3-7}$ cycloalkyl, $C_{6-10}$ aryl, $C_{2-9}$ heteroaryl and $C_{2-9}$ heterocyclyl of $R^g$ and $R^h$ are optionally substituted independently with one, two, three, four or five substituents; and D is hydrogen, a $C_{6-10}$ aryl, or a 5-10 membered heteroaryl having 1-4 heteroatoms selected from O, S, and N; or a 5-10 membered heteroaryl fused with a ring selected from the group consisting of 5- or 6-membered heteroaryl, 5-10 membered heterocyclyl, $C_6$ aryl and $C_{3-8}$ cycloalkyl; wherein the 5-10 membered heteroaryl of D and the fused ring are optionally substituted with one, two, three, four or five substituents.

In one aspect of the general structure of Formula (I):

$R_1$ is hydrogen, halogen, cyano, $C_6$ alkyl, $C_{3-7}$ cycloalkyl, $C_{1-6}$ haloalkyl, $C_{1-6}$ hydroxyalkyl, hydroxyl, $C_{1-6}$ alkoxyl, optionally substituted amino or optionally substituted acylamino;

$R_2$ is (a), (b), (c), (d), (e), (f), (g) or (h):
(a) a 5-10 membered heteroaryl or 5-10 membered heterocyclyl, having 1-4 heteroatoms selected from O, S, and N; and optionally substituted with one, two, three, four or five substituents; or
(b) a $C_{6-10}$ aryl optionally substituted with one, two, three, four or five substituents; or
(c) hydrogen, $-NHSO_2R^a$, $-SO_2NR^aR^b$; or $-SO_2NH_2$; wherein each $R^a$ is independently $C_{1-6}$ alkyl, and $R^b$ is hydrogen or $C_{1-6}$ alkyl; or
(d) $-OR^{a1}$ or $-(C_{1-6}$ alkylene$)-OR^{a1}$; wherein each $R^{a1}$ is independently $C_{1-6}$ alkyl optionally substituted with $C_{6-10}$ aryl; 5-10 membered heteroaryl; or 5-10 membered heterocyclyl; wherein the 5-10 membered heteroaryl, and 5-10 membered heterocyclyl are optionally substituted; or
(e) a $C_{1-6}$ alkyl optionally substituted with one to five substituents; or
(f) a $C_{3-8}$ cycloalkyl optionally substituted with one to five substituents;
(g) $-C(O)NR^{a2}R^{b2}$, wherein each $R^{a2}$ is independently hydrogen or $C_{1-6}$ alkyl, and $R^{b2}$ is hydrogen, $C_{1-6}$ alkyl, 5-10 membered heteroaryl or 5-10 membered heterocyclyl, wherein the 5-10 membered heteroaryl and 5-10 membered heterocyclyl are optionally substituted; or
(h) 5-10 membered heteroaryl fused with a ring selected from the group consisting of 5 or 6 membered heteroaryl, 5-10 membered heterocyclyl, $C_6$ aryl and $C_{3-7}$ cycloalkyl, wherein the 5-10 membered heteroaryl of $R_2$ and the fused ring are optionally substituted with one to four substituents;

$R_3$ is hydrogen, cyano, halogen, optionally substituted $C_{1-6}$ alkyl, optionally substituted $C_{2-9}$ heterocyclyl, or optionally substituted $C_{1-6}$ alkoxy; and $R_4$ is A-C(O)— or D;

A is $C_{1-6}$ alkyl, $C_{3-7}$ cycloalkyl, $C_{2-9}$ heteroaryl, $C_{2-9}$ heterocyclyl, $NHR^g$ or —$OR^h$; wherein the $C_{1-6}$ alkyl, $C_{3-7}$ cycloalkyl, $C_{2-9}$ heteroaryl and $C_{2-9}$ heterocyclyl of A are optionally substituted independently with one, two, three, four or five substituents;

$R^g$ and $R^h$ are independently $C_{1-6}$ alkyl, $C_{2-6}$ alkenyl, $C_{3-7}$ cycloalkyl, $C_{6-10}$ aryl, $C_{2-9}$ heteroaryl, or $C_{2-9}$ heterocyclyl; wherein the $C_{1-6}$ alkyl, $C_{2-6}$ alkenyl, $C_{3-7}$ cycloalkyl, $C_{6-10}$ aryl, $C_{2-9}$ heteroaryl and $C_{2-9}$ heterocyclyl of $R^g$ and $R^h$ are optionally substituted independently with one, two, three, four or five substituents; and D is hydrogen, or a 5-10 membered heteroaryl, having 1-4 heteroatoms selected from O, S, and N; or a 5-10 membered heteroaryl fused with a ring selected from the group consisting of 5- or 6-membered heteroaryl, 5-10 membered heterocyclyl, $C_6$ aryl and $C_{3-8}$ cycloalkyl; wherein the 5-10 membered heteroaryl of D and the fused ring are optionally substituted with one, two, three, four or five substituents.

In one aspect of the general structure of Formula (I):

$R_1$ is hydrogen, halogen, methyl, $CF_3$, $CHF_2$, $CH_2OH$, or cyano;

$R_2$ is:
  a 5-10 member heteroaryl or 5-10 member heterocyclyl, having 1-4 heteroatoms selected from O, S, and N; and optionally substituted with one, two, three or four substituents, $R_6$, $R_7$, $R_8$ and $R_{8'}$, each of which is independently selected from the group consisting of:
  i. branched or linear $C_{1-6}$ alkyl, $C_{1-6}$ alkenyl, or $C_{1-6}$ alkenylene, wherein said alkyl, alkenyl and alkenylene can be optionally substituted with one to four hydroxyl, halogen, nitrile, amino, mono($C_{1-6}$)alkylamino-, di($C_{1-6}$)alkylamino-, —$SO_2R^y$, $SONR^y$, —(CO)$NR^yR^z$ or —$NR^y$(CO)$R^z$, wherein $R^y$ and $R^z$, in each instance, is independently hydrogen or $C_{1-6}$ alkyl, wherein said alkyl can optionally be substituted with one to four hydroxyl or halogen;
  ii. $NR^yR^z$—C(O)—, wherein $R^y$ and $R^z$ are each independently hydrogen or $C_{1-6}$ alkyl, wherein said alkyl can optionally be substituted with one to four hydroxyl or halogen;
  iii. hydroxy($C_{1-6}$)alkyl;
  iv. $C_{1-6}$ alkoxy, wherein said alkoxy can be optionally substituted with one to four hydroxyl or halogen;
  v. $C_{3-9}$ cycloalkyl, substituted or unsubstituted $C_6$ aryl, substituted or unsubstituted 5-member heteroaryl, or $C_{2-9}$ heterocyclyl;
  vi. halogen;
  vii. amino;
  viii. cyano;
  ix. —$NR^y$(CO)$R^z$, wherein $R^y$ and $R^z$ are each independently hydrogen or $C_{1-6}$ alkyl, wherein said alkyl can optionally be substituted with one to four hydroxyl or halogen;
  x. —$SO_2R'$, wherein $R'$ is H or $C_{1-6}$ alkyl;
  xi. —$SO_2NR'R''$, wherein $R'$ and $R''$ are independently H or $C_{1-6}$ alkyl; and
  xii. wherein a carbon embedded in said heterocyclyl taken together with an oxygen to which it is bound can form a carbonyl; or $R_2$ is $C_{6-10}$ aryl having one, two, three or four substituents selected from the group consisting of branched or linear $C_{1-6}$ alkyl, $C_{1-6}$ alkenyl, $C_{1-6}$ alkenylene, $C_{3-4}$ cycloalkyl, wherein said alkyl, alkenyl, alkenylene and cycloalkyl can be substituted with amino, hydroxyl, nitrile, halogen and amide; cyano, hydroxyl, halogen, nitrile, amino, mono ($C_{1-6}$)alkylamino-, di($C_{1-6}$)alkylamino-, —$SO_2R^c$, $SONR^d$, —(CO)$NR^cR^d$ or —$NR^c$(CO)$R^d$, wherein $R^c$ and $R^d$ are each independently selected from the group consisting of hydrogen and $C_{1-6}$ alkyl, wherein said alkyl can be optionally substituted with one to four hydroxyl or halogen; or $R_2$ is hydrogen or —$SO_2NH_2$;

$R_3$ is hydrogen, cyano, or halogen; and $R_4$ is A-C(O)—, wherein, A is:
  i. $C_{3-7}$ cycloalkyl, $C_{2-9}$ heteroaryl, or $C_{2-9}$ heterocyclyl, wherein said cycloalkyl, heteroaryl, or heterocyclyl can be optionally substituted with one, two, three or four of $R_5$, wherein $R_5$ is selected from the group consisting of hydrogen, branched or linear $C_{1-6}$ alkyl, $C_{1-6}$ alkenyl, $C_{1-6}$ alkenylene, wherein said alkyl, alkenyl and alkenylene can be substituted with amino, $C_{1-6}$ alkoxy, hydroxyl, nitrile, halogen, —$SO_2R^e$ and amide; halogen, hydroxy($C_{1-6}$)alkyl, halo($C_{1-6}$)alkyl, cyano, cyano ($C_{1-6}$)alkyl, hydroxyl, $C_1$-6 alkoxy, amino, $C_{2-9}$ heteroaryl, —$SO_2R^e$, and $NR^eR^f$—C(O)—, wherein $R^e$ and $R^f$ are independently selected from the group consisting of hydrogen and branched or linear $C_{1-6}$ alkyl; or, said cycloalkyl or heterocyclyl together with two of $R_5$ form a bicyclic or spiro ring, wherein two of $R_5$ attached to different carbons are taken together with the carbon to which each is attached to form a bicyclic, or two of $R_5$ attached to the same carbon are taken together with the carbon to which each is attached to form a spiro ring; and
  ii. —$NHR^g$, wherein $R^9$ is selected from the group consisting of:
    a. branched or linear $C_{1-6}$ alkyl, $C_{1-6}$ alkenyl, $C_{1-6}$ alkenylene, $C_{2-9}$ heterocyclyl, and $C_{3-7}$ cycloalkyl, wherein said alkyl, alkenyl, alkenylene, heterocyclyl and cycloalkyl can be optionally substituted with hydroxyl, halogen, —$CF_2$, —$CF_3$, amino, di($C_{1-6}$)alkylamino, mono($C_{1-6}$)alkylamino, cyano, $C_{3-7}$ cycloalkyl, $C_{1-6}$ alkoxy, —$SO_2R'$, —$SO_2NR'R''$, —(CO)$NR'R''$, or —$NR'$(CO)$R''$, wherein $R'$ and $R''$ are independently H or $C_{1-6}$ alkyl; and
    b. $C_{2-9}$ heteroaryl or $C_{6-10}$ aryl, wherein said heteroaryl has 1-4 heteroatoms selected from O, S and N; and wherein said aryl and heteroaryl can be optionally substituted with one, two, three or four substituents selected from the group consisting of branched or linear $C_{1-6}$ alkyl, $C_{1-6}$ alkenyl, $C_{1-6}$ alkenylene, $C_{2-9}$ heterocyclyl, $C_{3-7}$ cycloalkyl, hydroxyl, halogen, —$CF_2$, —$CF_3$, amino, di($C_{1-6}$)alkylamino, mono ($C_{1-6}$)alkylamino, cyano, $C_{3-7}$ cycloalkyl, $C_{1-6}$ alkoxy, —$SO_2R'$, —$SO_2NR'R''$, —(CO)$NR'R''$, and —$NR'$(CO)$R''$, wherein $R'$ and $R''$ are independently H or $C_{1-6}$ alkyl;

or, $R_4$ is D, wherein D is:
  a 5-10 member heteroaryl, having 1-4 heteroatoms selected from O, S, and N; and optionally substituted with one, two, three or four substituents.

In one aspect, provided is a compound of Formula Ia:

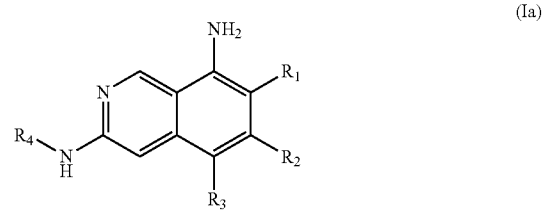

(Ia)

or salt (e.g., a pharmaceutically acceptable salt), solvate (e.g., hydrate), prodrug, metabolites or derivative thereof, wherein:

$R_1$ is hydrogen, halogen, methyl, $CF_3$, $CHF_2$, $CH_2OH$, or cyano;

$R_2$ is (a), (b), (c), (d), (e), (f), (g) or (h):

(a) a 5-10 membered heteroaryl or 5-10 membered heterocyclyl, having 1-4 heteroatoms selected from O, S, and N; and optionally substituted with one, two, three or four substituents, $R_6$, $R_7$, $R_8$ and $R_{8'}$, each of which is independently selected from the group consisting of:
  i. branched or linear $C_{1-6}$ alkyl, $C_{1-6}$ alkenyl, or $C_{1-6}$ alkenylene, wherein said alkyl, alkenyl and alkenylene can be optionally substituted with one to four substituents independently selected from the group consisting of hydroxyl, halogen, nitrile, amino, mono($C_{1-6}$alkyl)amino-, di($C_{1-6}$alkyl)amino-, —$SO_2R^y$, —$S(O)NR^y$, —$(CO)NR^yR^z$ and —$NR^y(CO)R^z$, wherein $R^y$ and $R^z$, in each instance, is independently hydrogen or $C_{1-6}$ alkyl, wherein said alkyl can optionally be substituted with one to four substituents independently selected from the group consisting of hydroxyl and halogen;
  ii. $NR^yR^z$—C(O)—, wherein $R^y$ and $R^z$ are each independently hydrogen or $C_{1-6}$ alkyl, wherein said alkyl can optionally be substituted with one to four substituents independently selected from the group consisting of hydroxyl and halogen;
  iii. hydroxy($C_{1-6}$ alkyl);
  iv. $C_{1-6}$ alkoxy, wherein said alkoxy can be optionally substituted with one to four substituents independently selected from the group consisting of hydroxyl and halogen;
  v. $C_{3-9}$ cycloalkyl, substituted or unsubstituted $C_6$ aryl, substituted or unsubstituted 5-membered heteroaryl, or $C_{2-9}$ heterocyclyl;
  vi. halogen;
  vii. amino;
  viii. cyano;
  ix. —$NR^yC(O)R^z$, wherein $R^y$ and $R^z$ are each independently hydrogen or $C_{1-6}$ alkyl, wherein said alkyl can optionally be substituted with one to four substituents independently selected from the group consisting of hydroxyl and halogen;
  x. —$SO_2R'$, wherein R' is H or $C_{1-6}$ alkyl;
  xi. —$SO_2NR'R''$, wherein R' and R'' are independently H or $C_{1-6}$ alkyl;
  xii. —NR'C(O)OR'', —$NR'SO_2NR''$ or —NR'S(O)R'', wherein R' is independently H or $C_{1-6}$ alkyl and R'' is independently $C_{1-6}$ alkyl, halo($C_{1-6}$ alkyl) or $C_{6-10}$ aryl optionally substituted with $C_{1-6}$ alkyl; and
  xiii. wherein a carbon embedded in said heterocyclyl taken together with an oxygen to which it is bound can form a carbonyl; or (b) a $C_{6-10}$ aryl having one, two, three or four substituents selected from the group consisting of branched or linear $C_{1-6}$ alkyl, $C_{1-6}$ alkenyl, $C_{1-6}$ alkenylene, $C_{3-4}$ cycloalkyl, wherein said alkyl, alkenyl, alkenylene and cycloalkyl can be substituted with amino, hydroxyl, cyano, halogen, amide, mono($C_{1-6}$ alkyl)amino-di($C_{1-6}$ alkyl)amino-, —$SO_2R^c$, —$S(O)NR^d$, —$C(O)NR^cR^d$ and —$NR^cC(O)R^d$, wherein $R^c$ and $R^d$ are each independently selected from the group consisting of hydrogen and $C_{1-6}$ alkyl, wherein said alkyl can be optionally substituted with one to four hydroxyl or halogen; or (c) hydrogen, —$NHSO_2R^a$, —$SO_2NR^aR^b$; or —$SO_2NH_2$; wherein each $R^a$ is independently $C_{1-6}$ alkyl, and $R^b$ is hydrogen or $C_{1-6}$ alkyl; or (d) —$OR^{a1}$ or —($C_{1-6}$ alkyl)-$OR^{a1}$; wherein each $R^{a1}$ is independently $C_{1-6}$ alkyl optionally substituted with $C_{6-10}$ aryl; 5-10 membered heteroaryl; or 5-10 membered heterocyclyl; wherein the 5-10 membered heteroaryl, and 5-10 membered heterocyclyl are optionally substituted with one to four substituents independently selected from the group consisting of hydroxyl, oxo, $C_{1-6}$ alkyl or $C_{1-6}$ alkoxy; or (e) a $C_{1-6}$ alkyl optionally substituted with one to four substituents independently selected from the group consisting of hydroxyl, halogen, cyano, amino, mono($C_{1-6}$ alkyl)amino, di($C_{1-6}$ alkyl)amino, $C_{3-8}$ cycloalkyl, $C_{6-10}$ aryl, 5-10 membered heteroaryl, and 5-10 membered heterocyclyl; wherein the $C_{3-8}$ cycloalkyl, $C_{6-10}$ aryl, 5-10 membered heteroaryl, and 5-10 membered heterocyclyl are optionally substituted with one to four substituents independently selected from the group consisting of hydroxyl, oxo, $C_{1-6}$ alkyl or $C_{1-6}$ alkoxy; or (f) $C_{3-8}$ cycloalkyl optionally substituted with one to four substituents independently selected from the group consisting of $C_{1-6}$ alkyl, hydroxyl, halogen, cyano, amino, mono($C_{1-6}$alkyl)amino, di($C_{1-6}$alkyl)amino, 5-10 membered heteroaryl, and 5-10 membered heterocyclyl; wherein the 5-10 membered heteroaryl, and 5-10 membered heterocyclyl are optionally substituted with one to four substituents independently selected from the group consisting of hydroxyl, oxo, $C_{1-6}$ alkyl or $C_{1-6}$ alkoxy;

(g) —$C(O)NR^{a2}R^{b2}$, wherein each $R^{a2}$ is independently hydrogen or $C_{1-6}$ alkyl, and $R^{b2}$ is hydrogen, $C_{1-6}$ alkyl, 5-10 membered heteroaryl or 5-10 membered heterocyclyl, wherein the 5-10 membered heteroaryl and 5-10 membered heterocyclyl are optionally substituted with one to four substituents independently selected from the group consisting of $C_{1-6}$ alkyl, $C_{3-7}$ cycloalkyl, oxo, hydroxyl, halo and cyano; or (h) 5-10 membered heteroaryl fused with a ring selected from the group consisting of 5 or 6 membered heteroaryl, 5-10 membered heterocyclyl, $C_6$ aryl and $C_{3-7}$ cycloalkyl, wherein the 5-10 membered heteroaryl of $R_2$ and the fused ring are optionally substituted with one to four substituents independently selected from the group consisting of hydroxyl, oxo, $C_{1-6}$ alkyl or $C_{1-6}$ alkoxy;

$R_3$ is $C_{1-6}$ alkyl, hydrogen, cyano, or halogen; and $R_4$ is A-C(O)— or D, wherein A is:
  i. $C_{3-7}$ cycloalkyl, $C_{2-9}$ heteroaryl, or $C_{2-9}$ heterocyclyl, wherein said cycloalkyl, heteroaryl, or heterocyclyl can be optionally substituted with one, two, three or four of $R_5$, wherein $R_5$ is selected from the group consisting of hydrogen, $C_{1-6}$ alkyl, $C_{3-7}$ cycloalkyl, $C_{2-6}$ alkenyl, $C_{2-6}$ alkenylene, halogen, cyano, hydroxyl, $C_{1-6}$ alkoxy, optionally substituted $C_{2-9}$ heteroaryl, —$SO_2R^e$, —$NR^eR^f$—$NR'C(O)R^f$ and $NR'R^f$—C(O)—; wherein the $C_{1-6}$ alkyl, $C_{3-7}$ cycloalkyl, $C_{2-6}$ alkenyl, $C_{2-6}$ alkenylene of $R_5$ can be optionally substituted with one to four substituents independently selected from the group consisting of $C_{1-6}$ alkoxy, hydroxyl, halogen, cyano, —$SO_2R^e$, —$NR^eR^f$ and —$C(O)NR^eR^f$, wherein $R^e$ and $R^f$ in each occurrence are independently selected from the group consisting of hydrogen and branched or linear $C_{1-6}$ alkyl;

or, said cycloalkyl or heterocyclyl together with two of $R_5$ form a bicyclic or spiro ring, wherein two of $R_5$ attached to different atoms are taken together with the carbon to which each is attached to form a bicyclic, or two of $R_5$ attached to the same carbon are taken together with the carbon to which each is attached to form a spiro ring;

ii. —$NHR^g$ or —$OR^h$, wherein $R^g$ and $R^h$ are independently selected from the group consisting of:
   a. branched or linear $C_{1-6}$ alkyl, $C_{3-5}$ cycloalkyl, $C_{1-6}$ alkenyl, $C_{1-6}$ alkenylene, $C_{2-9}$ heterocyclyl, and $C_{3-7}$ cycloalkyl, wherein said alkyl, alkenyl, alkenylene, heterocyclyl and cycloalkyl can be optionally substituted with one to four substituents independently selected from the group consisting of hydroxyl, halogen, —$CHF_2$, —$CF_3$, amino, di($C_{1-6}$ alkyl)amino, mono($C_{1-6}$ alkyl)amino, cyano, $C_{3-7}$ cycloalkyl, $C_{1-6}$ alkoxy, —$SO_2R'$, —$SO_2NR'R''$, —$C(O)NR'R''$, and —$NR'C(O)R''$, wherein $R'$ and $R''$ are independently H or $C_{1-6}$ alkyl; and
   b. $C_{2-9}$ heteroaryl or $C_{6-10}$ aryl, wherein said heteroaryl has 1-4 heteroatoms selected from O, S and N; and wherein said aryl and heteroaryl can be optionally substituted with one, two, three or four substituents selected from the group consisting of branched or linear $C_{1-6}$ alkyl, $C_{1-6}$ alkenyl, $C_{1-6}$ alkenylene, $C_{2-9}$ heterocyclyl, $C_{3-7}$ cycloalkyl, hydroxyl, halogen, —$CHF_2$, —$CF_3$, amino, di($C_{1-6}$ alkyl)amino, mono($C_{1-6}$ alkyl)amino, cyano, $C_{3-7}$ cycloalkyl, $C_{1-6}$ alkoxy, —$SO_2R'$, —$SO_2NR'R''$, —$C(O)NR'R''$, and —$NR'C(O)R''$, wherein $R'$ and $R''$ are independently H or $C_{1-6}$ alkyl; or iii. $C_{1-6}$ alkyl optionally substituted with one to four substituents independently selected from the group consisting of hydroxyl, halogen, cyano, $C_{1-6}$ alkoxy, amino, mono($C_{1-6}$ alkyl)amino, di($C_{1-6}$ alkyl)amino, $C_{3-7}$ cycloalkyl, $C_{6-10}$ aryl, 5-10 membered heteroaryl, and 5-10 membered heterocyclyl; wherein the $C_{3-7}$ cycloalkyl, $C_{6-10}$ aryl, 5-10 membered heteroaryl, and 5-10 membered heterocyclyl are optionally substituted with one to four substituents independently selected from the group consisting of hydroxyl, oxo, $C_{1-6}$ alkyl or $C_{1-6}$ alkoxy; and D is hydrogen or a 5-10 membered heteroaryl, having 1-4 heteroatoms selected from O, S, and N; and optionally substituted with one, two, three or four substituents independently selected from the group consisting of hydroxyl, oxo, $C_{1-6}$ alkyl or $C_{1-6}$ alkoxy; or 5-10 membered heteroaryl fused with a ring selected from the group consisting of 5 or 6 membered heteroaryl, 5-10 membered heterocyclyl, $C_6$ aryl and $C_{3-8}$ cycloalkyl, wherein the 5-10 membered heteroaryl of D and the fused ring are optionally substituted with one to four substituents independently selected from the group consisting of hydroxyl, oxo, $C_{1-6}$ alkyl or $C_{1-6}$ alkoxy.

In some embodiments, the compound is Formula I or Ia is other than one or more compounds selected from the group consisting of N-(8-amino-3-isoquinolinyl)-N'-ethylurea, 5-[(8-amino-3-isoquinolinyl)amino]-2-pyrazinecarbonitrile, and 5-[(8-amino-3-isoquinolinyl)amino]-3-[(1R)-2-(dimethylamino)-1-methylethoxy]-2-pyrazinecarbonitrile, and salts thereof. In some embodiments of the compound of Formula I or Ia, at least one of $R_2$ and $R_3$ is other than hydrogen. In some embodiments of the compound of Formula I or Ia, $R_2$ is other than hydrogen.

In various embodiments of the compounds of Formula I or Ia, the alkyl, alkenyl, alkynyl, cycloalkyl, aryl, heteroaryl and heterocyclyl are optionally substituted with one to five substituents. In some embodiments, $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl, 5-10 membered heteroaryl, 5-10 membered heterocyclyl or $C_{2-9}$ heterocyclyl may be independently optionally substituted with one to five $R^{30}$.

In some embodiments, $R^{30}$, in each instance, is independently $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl, $C_{2-9}$ heterocyclyl, halogen, cyano, oxo, —$C(O)NR^{31}R^{32}$, —$C(O)OR^{33}$, —$C(=NR^{36})R^{34}$, —$C(=NR^{36})NR^{31}R^{32}$, —$C(=NOR^{36})R^{34}$, cyano, hydrogen, halogen, —$R^{31}R^{32}$, —$NR^{35}C(O)R^{34}$, —$NR^{35}C(O)NR^{31}R^{32}$, —$NR^{35}C(O)OR^{33}$, —$NR^{35}S(O)R^{36}$, —$NR^{35}SO_2R^{36}$, —$NR^{35}SO_2NR^{31}R^{32}$, —$OR^{33}$, —$OC(O)R^{34}$, —$OC(O)NR^{31}R^{32}$, —$S(O)R^{36}$, —$SO_2R^{36}$, or —$SO_2NR^{31}R^{32}$; wherein the $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl, $C_{2-9}$ heterocyclyl of $R^{30}$ are optionally substituted with one to four $R^{40}$; or two $R^{30}$ groups are taken together with the parent moiety to which they are attached to form a ring which is optionally substituted with one to four $R^{40}$;

each $R^{31}$ and $R^{32}$ is independently hydrogen, $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl or $C_{2-9}$ heterocyclyl, each is independently optionally substituted with one to four $R^{40}$; or $R^{31}$ and $R^{32}$ are taken together with the nitrogen atom to which they are attached to form a $C_{3-7}$ heterocyclyl optionally substituted with one to four $R^{40}$;

each $R^{33}$, $R^{34}$ and $R^{35}$ are independently hydrogen, $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl or $C_{2-9}$ heterocyclyl, each is independently optionally substituted with one to four $R^{40}$;

$R^{36}$ is $C_{1-6}$ alkyl optionally substituted with one to four $R^{40}$.

$R^{40}$ in each instance is independently selected from the group consisting of halogen, cyano, oxo, —$NR^{41}R^{42}$, —$SO_2NR^{41}R^{42}$, —$C(O)NR^{41}R^{42}$, —$C(O)OR^{43}$, —$OR^{43}$, —$NR^{43}C(O)R^{44}$, —$NR^{43}C(O)OR^{43}$, —$NR^{43}C(O)NR^{41}R^{42}$, $NR^{43}SO_2R^{45}$, —$SO_2R^{45}$, $C_{1-6}$ alkyl, $C_{3-7}$ cycloalkyl, $C_{6-10}$ aryl, $C_{2-9}$ heteroaryl, or $C_{2-9}$ heterocyclyl; or two $R^{40}$ groups are taken together with the parent moiety to which they are attached to form a ring which is optionally substituted with one to three substituents selected from $C_{1-6}$ alkyl, $C_{1-6}$ haloalkyl, hydroxyl and oxo; the $C_{1-6}$ alkyl, $C_{3-7}$ cycloalkyl, $C_{6-10}$ aryl, $C_{2-9}$ heteroaryl, or $C_{2-9}$ heterocyclyl of $R^{40}$ are independently optionally substituted with one to three substituents selected from $C_{1-6}$ alkyl, $C_{1-6}$ haloalkyl, hydroxyl and oxo.

each $R^{41}$ and $R^{42}$ is independently hydrogen or $C_{1-6}$ alkyl; or $R^{41}$ and $R^{42}$ are taken together with the nitrogen atom to which they are attached to form a $C_{3-7}$ heterocyclyl optionally substituted with one to three substituents selected from $C_{1-6}$ alkyl, $C_{1-6}$ haloalkyl, hydroxyl and oxo;

each $R^{43}$ and $R^{44}$ are independently hydrogen or $C_{1-6}$ alkyl; and $R^{45}$ is $C_{1-6}$ alkyl.

In some embodiments of the compound of Formula I or Ia, the optionally substituted $C_{2-9}$ heteroaryl of $R_5$ is optionally substituted with $C_{1-6}$ alkyl optionally substituted with one to four substituents independently selected from the group consisting of hydroxyl, halogen, cyano, $C_{1-6}$ alkoxy, amino-($C_{1-6}$ alkoxy)- and $C_{2-9}$ heterocyclyl optionally substituted with one to four substituents independently selected from the group consisting of hydroxyl, oxo, $C_{1-6}$ alkyl or $C_{1-6}$ alkoxy.

Useful values of $R_1$ are described above. In an embodiment, $R_1$ is hydrogen and all other variables are as described in Formula I or Ia. In an embodiment, $R_1$ is halogen and all other variables are as described in Formula I or Ia. In an aspect of this embodiment, $R_1$ is fluoro and all other variables are as described in Formula I or Ia. In an embodiment, $R_1$ is cyano and all other variables are as described in Formula I or Ia.

Useful values of $R_3$ are described above. In an embodiment, $R_3$ is hydrogen and all other variables are as described in Formula I or Ia or are as described in any of the embodiments described herein. In an embodiment, $R_3$ is halogen and all other variables are as described in Formula I or Ia or are as described in any of the embodiments described herein. In certain aspects of this embodiment, $R_3$ is fluoro, chloro, or bromo, and all other variables are as described in Formula I or Ia or are as described in any of the embodiments described herein. In a particular aspect, $R_3$ is fluoro, and all other variables are as described in Formula I or Ia or are as described in any of the embodiments described herein.

Useful values of $R_4$ are described above. In certain aspects, $R_4$ is A-C(O)—, wherein A is a $C_{3-6}$ cycloalkyl, which can be optionally substituted with one or two of $R_5$, and all other variables are as described in Formula I or Ia or are as described in any of the embodiments described herein. In certain aspects, A is a $C_{3-5}$ cycloalkyl, which can be optionally substituted with one or two of $R_5$, and all other variables are as described in Formula I or Ia or are as described in any of the embodiments described herein. In a particular aspect, A is cyclopropyl, which can be optionally substituted with one or two of $R_5$, and all other variables are as described in Formula I or Ia or are as described in any of the embodiments described herein.

In embodiments where all other variables are as defined in any embodiment above, $R_2$ is -A-C(O)—. In some embodiments, A is optionally substituted $C_{1-6}$ alkyl, optionally substituted $C_{3-7}$ cycloalkyl, optionally substituted $C_{2-9}$ heteroaryl, optionally substituted $C_{2-9}$ heterocyclyl, —NHR$^g$ or —OR$^h$.

In some embodiments, A is:
  i. $C_{3-7}$ cycloalkyl, $C_{2-9}$ heteroaryl, or $C_{2-9}$ heterocyclyl, wherein said cycloalkyl, heteroaryl, or heterocyclyl can be optionally substituted with one, two, three or four of $R_5$, wherein $R_5$ is selected from the group consisting of hydrogen, $C_{1-6}$ alkyl, $C_{3-7}$ cycloalkyl, $C_{2-6}$ alkenyl, $C_{2-6}$ alkenylene, halogen, cyano, hydroxyl, $C_{1-6}$ alkoxy, optionally substituted $C_{2-9}$ heteroaryl, —SO$_2$R$^e$, —NR$^e$R$^f$, —NR$^e$C(O)R$^f$, —NR$^e$SO$_2$R$^f$ and NR$^e$R$^f$—C(O)—; wherein the $C_{1-6}$ alkyl, $C_{3-7}$ cycloalkyl, $C_{2-6}$ alkenyl, $C_{2-6}$ alkenylene of $R_5$ can be optionally substituted with one to four substituents independently selected from the group consisting of $C_{1-6}$ alkoxy, hydroxyl, halogen, cyano, —SO$_2$R$^e$, —NR$^e$R$^f$— NR'C(O)R$^f$ and —C(O)NR$^e$R$^f$, wherein R$^e$ and R$^f$ in each occurrence are independently selected from the group consisting of hydrogen, branched or linear $C_{1-6}$ alkyl and $C_{3-7}$ cycloalkyl;
    or, said cycloalkyl or heterocyclyl together with two of $R_5$ form a bicyclic or spiro ring, wherein two of $R_5$ attached to different atoms are taken together with the carbon to which each is attached to form a bicyclic, or two of $R_5$ attached to the same carbon are taken together with the carbon to which each is attached to form a spiro ring;
  ii. —NHR$^g$ or —OR$^h$, wherein R$^g$ and R$^h$ are independently selected from the group consisting of:
    a. branched or linear $C_{1-6}$ alkyl, $C_{1-6}$ alkenyl, $C_{1-6}$ alkenylene, $C_{2-9}$ heterocyclyl, and $C_{3-7}$ cycloalkyl, wherein said alkyl, alkenyl, alkenylene, heterocyclyl and cycloalkyl can be optionally substituted with one to four substituents independently selected from the group consisting of hydroxyl, halogen, —CHF$_2$, —CF$_3$, amino, di($C_{1-6}$ alkyl)amino, mono($C_{1-6}$ alkyl)amino, cyano, $C_{3-7}$ cycloalkyl, $C_{1-6}$ alkoxy, —SO$_2$R', —SO$_2$NR'R''', —C(O)NR'R''', —NR'C(O)R''', —NR'C(O)OR''', —NR'C(O)NR''R''', —NR'SO$_2$NR''R''' or —NR'S(O)R''', wherein R' and R''' are independently H or $C_{1-6}$ alkyl and R'' is independently $C_{1-6}$ alkyl, halo($C_{1-6}$ alkyl) or $C_{6-10}$ aryl optionally substituted with $C_{1-6}$ alkyl; or R'' and R''' are taken together with the nitrogen to which they are attached to form a substituted or unsubstituted heterocyclyl; and
    b. $C_{2-9}$ heteroaryl or $C_{6-10}$ aryl, wherein said heteroaryl has 1-4 heteroatoms selected from O, S and N; and wherein said aryl and heteroaryl can be optionally substituted with one, two, three or four substituents selected from the group consisting of branched or linear $C_{1-6}$ alkyl, $C_{1-6}$ alkenyl, $C_{1-6}$ alkenylene, $C_{2-9}$ heterocyclyl, $C_{3-7}$ cycloalkyl, hydroxyl, halogen, —CHF$_2$, —CF$_3$, amino, di($C_{1-6}$ alkyl)amino, mono($C_{1-6}$ alkyl)amino, cyano, $C_{3-7}$ cycloalkyl, $C_{1-6}$ alkoxy, —SO$_2$R', —SO$_2$NR'R''', —C(O)NR'R''', and —NR'C(O)R''', wherein R' and R'' are independently H or $C_{1-6}$ alkyl; or
  iii. $C_{1-6}$ alkyl optionally substituted with one to four substituents independently selected from the group consisting of hydroxyl, halogen, cyano, $C_{1-6}$ alkoxy, amino, mono($C_{1-6}$ alkyl)amino, di($C_{1-6}$ alkyl)amino, $C_{3-7}$ cycloalkyl, $C_{6-10}$ aryl, 5-10 membered heteroaryl, 5-10 membered heterocyclyl, —SO$_2$R', —SO$_2$NR'R''', —C(O)NR'R''', —NR'C(O)R''', —NR'C(O)OR''', —NR'C(O)NR''R''', —NR'SO$_2$NR''R''' and —NR'S(O)R''';
    wherein R' and R''' are independently H or $C_{1-6}$ alkyl and R'' is independently $C_{1-6}$ alkyl, halo($C_{1-6}$ alkyl) or $C_{6-10}$ aryl optionally substituted with $C_{1-6}$ alkyl; or R'' and R''' are taken together with the nitrogen to which they are attached to form an optionally substituted $C_{3-7}$ heterocyclyl.

In some embodiments, A is $C_{3-7}$ cycloalkyl, $C_{2-9}$ heteroaryl, or $C_{2-9}$ heterocyclyl, wherein said cycloalkyl, heteroaryl, or heterocyclyl can be optionally substituted with one, two, three or four of $R_5$, wherein $R_5$ is selected from the group consisting of hydrogen, $C_{1-6}$ alkyl, $C_{3-7}$ cycloalkyl, $C_{2-6}$ alkenyl, $C_{2-6}$ alkenylene, halogen, cyano, hydroxyl, $C_{1-6}$ alkoxy, optionally substituted $C_{2-9}$ heteroaryl, —SO$_2$R$^e$, —NR$^e$R$^f$, —NR$^e$C(O)R$^f$, —NR$^e$SO$_2$R$^f$ and NR$^e$R$^f$—C(O)—; wherein the $C_{1-6}$ alkyl, $C_{3-7}$ cycloalkyl, $C_{2-6}$ alkenyl, $C_{2-6}$ alkenylene of $R_5$ can be optionally substituted with one to four substituents independently selected from the group consisting of $C_{1-6}$ alkoxy, hydroxyl, halogen, cyano, —SO$_2$R$^e$, —NR$^e$R$^f$, —NR$^e$C(O)R$^f$ and —C(O)NR$^e$R$^f$, wherein R$^e$ and R$^f$ in each occurrence are independently selected from the group consisting of hydrogen, branched or linear $C_{1-6}$ alkyl and $C_{3-7}$ cycloalkyl; or, said cycloalkyl or heterocyclyl together with two of $R_5$ form a bicyclic or spiro ring, wherein two of $R_5$ attached to different atoms are taken together with the carbon to which each is attached to form a bicyclic, or two of $R_5$ attached to the same carbon are taken together with the carbon to which each is attached to form a spiro ring.

In some embodiments, A is optionally substituted $C_{3-7}$ cycloalkyl.

In some embodiments, A is $C_{1-6}$ alkyl optionally substituted with one to four substituents independently selected from the group consisting of hydroxyl, halogen, cyano, $C_{1-6}$ alkoxy, amino, mono($C_{1-6}$ alkyl)amino, di($C_{1-6}$ alkyl)amino, $C_{3-7}$ cycloalkyl, $C_{6-10}$ aryl, 5-10 membered heteroaryl, and 5-10 membered heterocyclyl, —SO$_2$R', —SO$_2$NR'R", —C(O)NR'R", —NR'C(O)R", —NR'C(O)OR", —NR'C(O)NR"R'", —NR'SO$_2$NR"R'" or —NR'S(O)R", wherein R' and R'" are independently H or C$_{1-6}$ alkyl and R" is independently C$_{1-6}$ alkyl, halo(C$_{1-6}$ alkyl) or C$_{6-10}$ aryl optionally substituted with C$_{1-6}$ alkyl; or R" and R'" are taken together with the nitrogen to which they are attached to form a substituted or unsubstituted heterocyclyl; wherein the C$_{3-7}$ cycloalkyl, C$_{6-10}$ aryl, 5-10 membered heteroaryl, and 5-10 membered heterocyclyl are optionally substituted (e.g., with one to four substituents independently selected from the group consisting of hydroxyl, oxo, C$_{1-6}$ alkyl or C$_{1-6}$ alkoxy).

Useful values of R$_5$ are described above. In an embodiment, R$_5$ is selected from the group consisting of hydrogen, fluoro, cyano, NH$_2$—C(O)—, C$_{2-9}$ heteroaryl, cyano(C$_{1-6}$) alkyl, and hydroxyl(C$_{1-6}$)alkyl, and all other variables are as described in Formula I or Ia or are as described in any of the embodiments described herein. In particular aspects of this embodiment, R$_5$ is fluoro or cyano and all other variables are as described in Formula I or Ia or are as described in any of the embodiments described herein.

In an embodiment, R$_5$ is C$_{2-9}$ heteroaryl. In particular aspects of this embodiment, the C$_{2-9}$ heteroaryl is an optionally substituted heteroaryl containing at least one nitrogen. In particular aspects of this embodiment, the heteroaryl is an optionally substituted 5-member heteroaryl containing 1 or 2 nitrogen atoms. In particular aspects of this embodiment, the 5-member heteroaryl is an optionally substituted pyrazole.

In an embodiment, at least one R$_5$ is cyano(C$_{1-6}$)alkyl. In particular aspects of this embodiment, at least one R$_5$ is cyano-CH$_2$—.

In an embodiment, R$_5$ is hydrogen.

In an embodiment, R$_5$ is a group described above other than hydrogen, and all other variables are as described in Formula I or Ia or are as described in any of the embodiments described herein.

In an embodiment where R$_5$ is other than hydrogen, R$_4$ is A-C(O)—, wherein, A is:

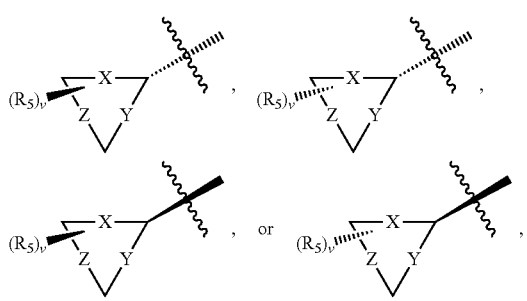

where, v is zero, one, two, three or four; X, Y and Z are each independently absent or —CH$_2$—, and wherein, if present, zero, one or two of H on each of X, Y and Z can be R$_5$; and all other variables are as described in Formula I or Ia or are as described in any of the embodiments described herein.

In an embodiment, A is

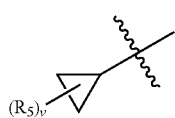

where, v is zero, one or two, and all other variables are as defined in Formula I or Ia or are as described in any of the embodiments described herein.

In an embodiment, A is

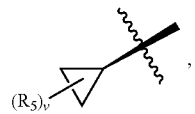

and all other variables are as defined in Formula I or Ia or are as defined in any of the embodiments described above.

In an embodiment, R$_5$ is other than hydrogen and R$_4$ is A-C(O)—, wherein, A is

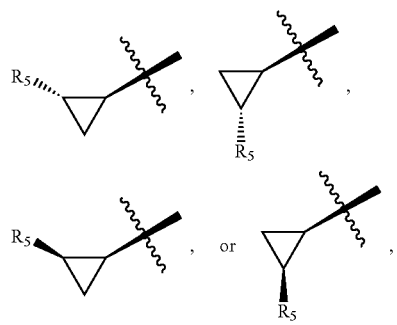

and all other variables are as defined in Formula I or Ia or are as defined in any of the embodiments described above.

In an embodiment, A is

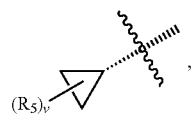

where, v is zero, one or two, and all other variables are as defined in Formula I or Ia or are as defined in any of the embodiments described above.

In an embodiment, R$_5$ is other than hydrogen and R$_4$ is A-C(O)—, wherein, A is

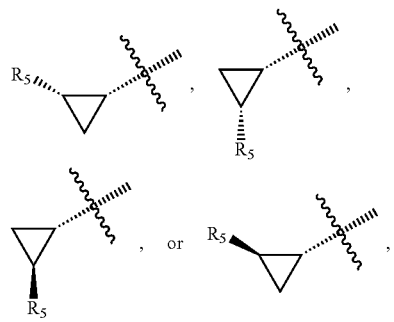

and all other variables are as defined in Formula I or Ia or are as defined in any of the embodiments described above.

In some embodiments, $R_4$ is

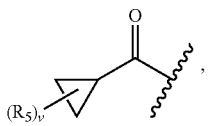

wherein, v is 0, 1, 2 or 3; and $R_5$ is selected from the group consisting of $C_{1-6}$ alkyl, $C_{3-7}$ cycloalkyl, $C_{2-6}$ alkenyl, $C_{2-6}$ alkenylene, halogen, cyano, hydroxyl, $C_{1-6}$ alkoxy, optionally substituted $C_{2-9}$ heteroaryl, $-SO_2R^e$, $-NR^eR^f$, $-NR^eC(O)R^f$, $-NR^eSO_2R^f$ and $NR'R^f-C(O)-$; wherein the $C_{1-6}$ alkyl, $C_{3-7}$ cycloalkyl, $C_{2-6}$ alkenyl, $C_{2-6}$ alkenylene of $R_5$ can be optionally substituted with one to four substituents independently selected from the group consisting of $C_{1-6}$ alkoxy, hydroxyl, halogen, cyano, $-SO_2R^e$, $-NR^eR^f$, $-NR^eC(O)R^f$ and $-C(O)NR^eR^f$, wherein $R^e$ and $R^f$ in each occurrence are independently selected from the group consisting of hydrogen, branched or linear $C_{1-6}$ alkyl and $C_{3-7}$ cycloalkyl.

In embodiments where all other variables areas defined in any embodiment above, $R_5$ is selected from the group consisting of hydrogen, fluorine, cyano, $NH_2-C(O)-$, alkyl-$(C_{1-6})$alkoxy-, optionally substituted $C_{2-9}$ heteroaryl, and cyano$(C_{1-6})$alkyl. In these embodiments, $R_5$ is fluoro or cyano. In these embodiments, $R_5$ is hydrogen. In these embodiments, $R_5$ is optionally substituted $C_{2-9}$ heteroaryl or cyano$(C_{1-6})$alkyl. In these embodiments, $R_5$ is cyano-$CH_2-$. In some embodiments, at least one $R_5$ is $C_{1-6}$ alkyl (e.g., methyl).

In embodiments where all other variables are as defined in any embodiment above, the compound wherein at least one $R_5$ is optionally substituted $C_{2-9}$ heteroaryl.

In embodiments where all other variables are as defined in any embodiment above, the compound wherein the at least one $R_5$ is optionally substituted $C_{2-9}$ heteroaryl is an optionally substituted 5-member heteroaryl containing 1 or 2 nitrogen atoms.

In embodiments where all other variables are as defined in any embodiment above, the compound wherein the optionally substituted 5-member heteroaryl is an optionally substituted pyrazole.

In embodiments where all other variables are as defined in any embodiment above, the compound wherein the optionally substituted pyrazole is

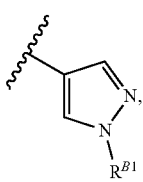

wherein the wavy line denotes the point of attachment to the cyclopropyl ring; and wherein $R^{B1}$ is branched or linear $C_{1-6}$ alkyl, wherein the alkyl can be optionally substituted with one to four hydroxyl, halogen, nitrile, amino, $-O-(C_{1-6})$ alkyl, $-O-(C_{1-6})$alkylamino-, di$(C_{1-6})$alkylamino-, or $-NR^y(CO)R^z$, wherein R and $R^z$, in each instance, is independently hydrogen or $C_{1-6}$ alkyl; or $-SO_2R'$, wherein R' is $C_{1-6}$ alkyl.

In embodiments where all other variables are as defined in any embodiment above, the compound wherein $R^{B1}$ is optionally substituted linear $C_{1-6}$ alkyl.

In embodiments where all other variables are as defined in any embodiment above, the compound wherein the optionally substituted linear $C_{1-6}$ alkyl is methyl.

In some embodiments, $R_4$ is

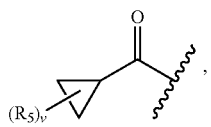

wherein v is 2, one $R_5$ is methyl and the second $R_5$ is 1-methylpyrazol-4-yl.

In some embodiments, $R_4$ is

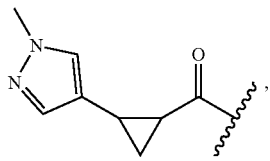

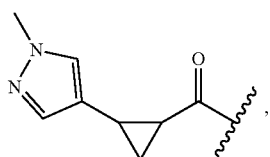

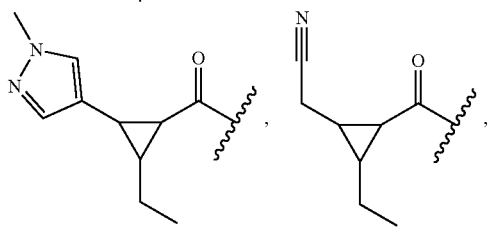

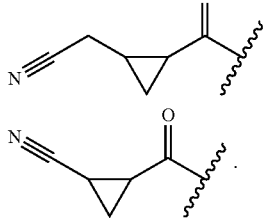

In some embodiments, $R_4$ is

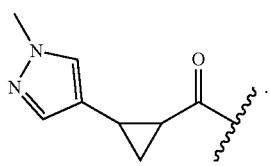 [SMILES: *C(=O)C1CC1c1cnn(C)c1]

In some embodiments, R$_4$ is

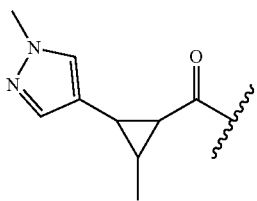

In some embodiments, R$_4$ is

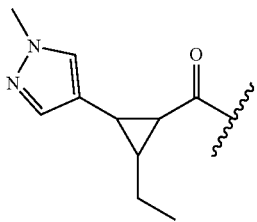

In some embodiments, R$_4$ is

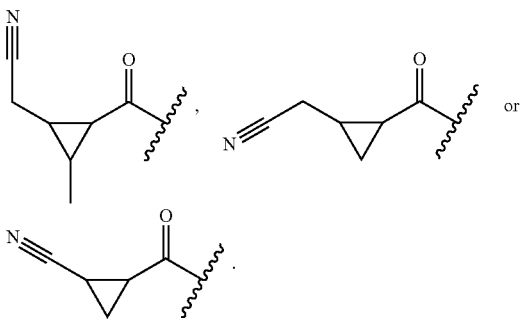

In some embodiments, the compound of Formula I or Ia is selected from Compound Nos. 195, 196, 197, 198, 279, 280, 281, 282 and 358, or a pharmaceutically acceptable salt thereof.

In some embodiments, R$_4$ is A-C(O)—, wherein A is —NHR$^g$ or —OR$^h$, wherein R$^g$ and R$^h$ are independently C$_{1-6}$ alkyl, C$_{1-6}$ alkenyl, C$_{1-6}$ alkenylene, C$_{2-9}$ heterocyclyl, C$_{3-7}$ cycloalkyl, C$_{2-9}$ heteroaryl or C$_{6-10}$ aryl; each of which can be optionally substituted as detailed herein. In some embodiments, R$^g$ and R$^h$ are independently selected from the group consisting of:

a. branched or linear C$_{1-6}$ alkyl, C$_{1-6}$ alkenyl, C$_{1-6}$ alkenylene, C$_{2-9}$ heterocyclyl, and C$_{3-7}$ cycloalkyl, wherein said alkyl, alkenyl, alkenylene, heterocyclyl and cycloalkyl can be optionally substituted with one to four substituents independently selected from the group consisting of hydroxyl, halogen, —CHF$_2$, —CF$_3$, amino, di(C$_{1-6}$ alkyl)amino, mono (C$_{1-6}$ alkyl)amino, cyano, C$_{3-7}$ cycloalkyl, C$_{1-6}$ alkoxy, —SO$_2$R', —SO$_2$NR'R'', —C(O)NR'R'', —NR'C(O)R'', —NR'C(O)OR'', —NR'C(O)NR''R''', —NR'SO$_2$NR''R''' or —NR'S(O)R'', wherein R' and R''' are independently H or C$_{1-6}$ alkyl and R'' is independently C$_{1-6}$ alkyl, halo(C$_{1-6}$ alkyl) or C$_{6-10}$ aryl optionally substituted with C$_{1-6}$ alkyl; or R'' and R''' are taken together with the nitrogen to which they are attached to form a substituted or unsubstituted heterocyclyl; and b. C$_{2-9}$ heteroaryl or C$_{6-10}$ aryl, wherein said heteroaryl has 1-4 heteroatoms selected from O, S and N; and wherein said aryl and heteroaryl can be optionally substituted with one, two, three or four substituents selected from the group consisting of branched or linear C$_{1-6}$ alkyl, C$_{1-6}$ alkenyl, C$_{1-6}$ alkenylene, C$_{2-9}$ heterocyclyl, C$_{3-7}$ cycloalkyl, hydroxyl, halogen, —CHF$_2$, —CF$_3$, amino, di(C$_{1-6}$ alkyl)amino, mono (C$_{1-6}$ alkyl)amino, cyano, C$_{3-7}$ cycloalkyl, C$_{1-6}$ alkoxy, —SO$_2$R', —SO$_2$NR'R'', —C(O)NR'R'', and —NR'C(O)R'', wherein R' and R'' are independently H or C$_{1-6}$ alkyl.

In embodiments, R$_4$ is A-C(O)—, wherein, A is: ii. —NHR$^g$, wherein R$^g$ is selected from the group consisting of: a. branched or linear C$_{1-6}$ alkyl, C$_{1-6}$ alkenyl, C$_{1-6}$ alkenylene, C$_{2-9}$ heterocyclyl, and C$_{3-7}$ cycloalkyl, wherein said alkyl, alkenyl, alkenylene, heterocyclyl and cycloalkyl can be optionally substituted with hydroxyl, halogen, —CF$_2$, —CF$_3$, amino, di(C$_{1-6}$)alkylamino, mono(C$_{1-6}$)alkylamino, cyano, C$_{3-7}$ cycloalkyl, C$_{1-6}$ alkoxy, —SO$_2$R', —SO$_2$NR'R'', —(CO)NR'R'', or —NR'(CO)R'', wherein R' and R'' are independently H or C$_{1-6}$ alkyl; and b. C$_{2-9}$ heteroaryl or C$_{6-10}$ aryl, wherein said heteroaryl has 1-4 heteroatoms selected from O, S and N; and wherein said aryl and heteroaryl can be optionally substituted with one, two, three or four substituents selected from the group consisting of branched or linear C$_{1-6}$ alkyl, C$_{1-6}$ alkenyl, C$_{1-6}$ alkenylene, C$_{2-9}$ heterocyclyl, C$_{3-7}$ cycloalkyl, hydroxyl, halogen, —CF$_2$, —CF$_3$, amino, di(C$_{1-6}$)alkylamino, mono(C$_{1-6}$)alkylamino, cyano, C$_{3-7}$ cycloalkyl, C$_{1-6}$ alkoxy, —SO$_2$R', —SO$_2$NR'R'', —(CO)NR'R'', and —NR'(CO)R'', wherein R' and R'' are independently H or C$_{1-6}$ alkyl, and all other variables are as described in Formula I or Ia or are as described in any of the embodiments herein.

In embodiments where all other variables are as defined in any embodiment above, R$_2$ is D. In some embodiments, D is a 5-10 membered heteroaryl, having 1-4 heteroatoms selected from O, S, and N; and optionally substituted with one, two, three or four substituents, wherein two of the substituents attached to different atoms are taken together with the atom to which each is attached to form a bicyclic or tricyclic, wherein said bicyclic or tricyclic is optionally substituted; or the 5-10 membered heteroaryl is fused with a ring selected from the group consisting of 5 or 6 membered heteroaryl, 5-10 membered heterocyclyl, C$_6$ aryl and C$_{3-8}$ cycloalkyl, wherein the 5-10 membered heteroaryl of D and the fused ring are optionally substituted, wherein said fused ring forms an optionally substituted bicyclic or tricyclic ring system.

In some embodiments, D is hydrogen or a 5-10 membered heteroaryl, having 1-4 heteroatoms selected from O, S, and N; and optionally substituted (e.g., with one, two, three or four substituents independently selected from the group consisting of hydroxyl, oxo, C$_{1-6}$ alkyl and C$_{1-6}$ alkoxy); or 5-10 membered heteroaryl fused with a ring selected from the group consisting of 5 or 6 membered heteroaryl, 5-10 membered heterocyclyl, C$_6$ aryl and C$_{3-8}$ cycloalkyl, wherein the 5-10 membered heteroaryl of D and the fused ring are optionally substituted (e.g., with one to four substituents independently selected from the group consisting of hydroxyl, oxo, C$_{1-6}$ alkyl and C$_{1-6}$ alkoxy).

In an embodiment, R$_4$ is D, wherein, D is an optionally substituted heteroaryl containing at least one nitrogen. In embodiments, the heterocyclyl is an optionally substituted 5-member heterocyclyl containing 1 or 2 nitrogen atoms. In embodiments, the 5-member heterocyclyl is an optionally substituted pyrazole.

In an embodiment, the optionally substituted pyrazole is

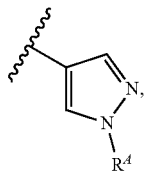

wherein the wavy line denotes the point of attachment to the N; and wherein $R^4$ is branched or linear $C_{1-6}$ alkyl, wherein said alkyl can be optionally substituted with one to four hydroxyl, halogen, nitrile, amino, mono($C_{1-6}$)alkylamino-, di($C_{1-6}$)alkylamino-, or —$NR^y(CO)R^z$, wherein $R^y$ and $R^z$, in each instance, is independently hydrogen or $C_{1-6}$ alkyl.

In an embodiment, $R^4$ is linear $C_{1-6}$ alkyl substituted with hydroxyl, halogen, nitrile, or amino.

In an embodiment, the linear $C_{1-6}$ alkyl is ethyl substituted with nitrile.

In an embodiment, $R^4$ is

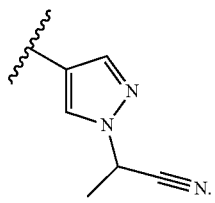 [SMILES: *c1cnn(C(C)C#N)c1]

In an embodiment, $R^4$ is

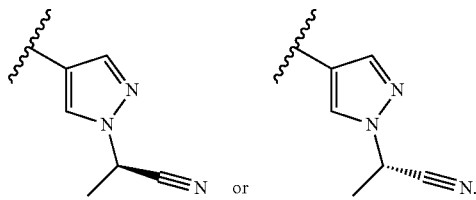

In some embodiments, the optionally substituted pyrazole is fused with another cyclic moiety to form an optionally substituted bicyclic or tricyclic, e.g., a 3-pyrozolyl having another cyclic moiety fused to the 1,5 bond. In some embodiments, D is a bicyclic (or tricyclic where further ring fusion is present) which is

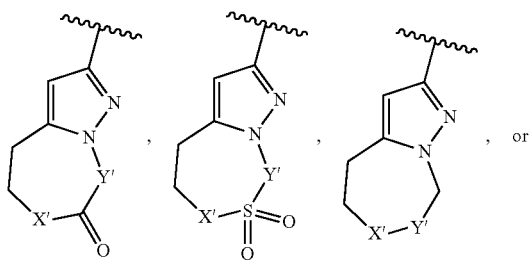

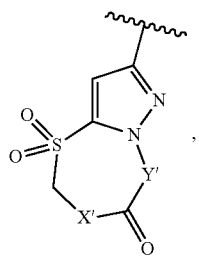

wherein X' and Y' are each independently C, N, S, or O; and wherein said bicyclic is optionally substituted with one, two, three or four substituents independently selected from the group consisting of hydrogen, hydroxyl, amino and $C_{1-6}$ alkyl; and wherein two of the substituents taken together with the atoms to which they are attached can form a $C_3$-$C_5$ spiro or a $C_{2-9}$ heteroaryl ring; wherein said $C_{2-9}$ heteroaryl ring may be fused to said bicyclic to form a tricyclic. In some of these embodiments, at least one of X' or Y' are N.

In some embodiments, D is

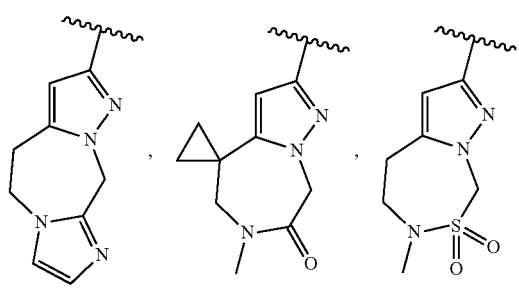

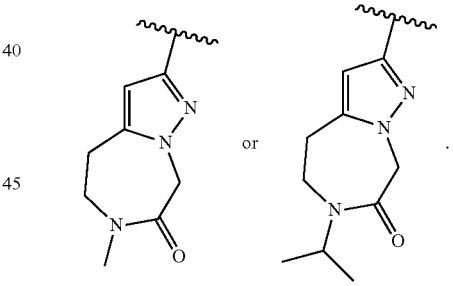

In some embodiments, the compound of Formula I or Ia is selected from Compound Nos. 228, 229, 230, 247, 276, 315 and 316, or a pharmaceutically acceptable salt thereof.

In embodiments where all other variables are as defined in any embodiment detailed herein, the compound wherein D is is a 5-membered heteroaryl having the formula

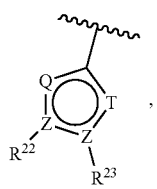

or a 6-membered heteroaryl having the formula

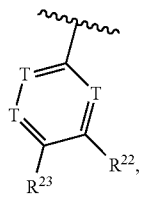

wherein:

Q is $NR^{20}$, $R^{20}$, O or s;

each T is independently N or $CR^{21}$;

each Z is independently N or C, provided that only one Z is N;

each $R^{20}$ and $R^{21}$ is independently hydrogen, alkyl, haloalkyl, alkoxy, halogen, hydroxy, or cyano; and $R^{22}$ and $R^{23}$ are taken together with the atoms to which they are attached to form a bicyclic; wherein the bicyclic may contain one or more heteroatoms selected from N, S and O; and wherein the bicyclic is optionally substituted with one, two, three, four or five $R^{30}$;

wherein each $R^{30}$ is independently $C_{1-6}$ alkyl, $C_{2-6}$ alkenyl, $C_{3-7}$ cycloalkyl, $C_{3-7}$ heterocyclyl, halogen, cyano, oxo, $-NR^{31}R^{32}$, $-SO_2NR^{31}R^{32}$, $-C(O)NR^{31}R^{32}$, $-C(O)OR^{33}$, $-OR^{33}$, $-NR^{33}C(O)R^{34}$, $-NR^{33}SO_2R^{35}$ or $-SO_2R^{35}$; wherein the $C_{1-6}$ alkyl, $C_{2-6}$ alkenyl, $C_{3-7}$ cycloalkyl and $C_{3-7}$ heterocyclyl of $R^{30}$ are optionally substituted with one to four $R^{40}$; or two $R^{30}$ groups are taken together with the parent moiety to which they are attached to form a ring which is optionally substituted with one to four $R^{40}$;

each $R^{31}$ and $R^{32}$ is independently hydrogen or $C_{1-6}$ alkyl; or $R^{31}$ and $R^{32}$ are taken together with the nitrogen atom to which they are attached to form a $C_{3-7}$ heterocyclyl optionally substituted with one to four $R^{40}$;

each $R^{33}$ and $R^{34}$ are independently hydrogen or $C_{1-6}$ alkyl;

$R^{35}$ is $C_{1-6}$ alkyl;

each $R^{40}$ is independently selected from the group consisting of halogen, cyano, oxo, $-NR^{41}R^{42}$, $-SO_2NR^{41}R^{42}$, $-C(O)NR^{41}R^{42}$, $-C(O)OR^{43}$, $-OR^{43}$, $-NR^{43}C(O)R^{44}$, $-NR^{43}SO_2R^{45}$ or $-SO_2R^{45}$; $C_{1-6}$ alkyl, $C_{1-6}$ haloalkyl [e.g., $-CHF_2$, or $-CF_3$], $C_{2-9}$ heteroaryl, $C_{6-10}$ aryl, oxo; or two $R^{40}$ groups are taken together with the parent moiety to which they are attached to form a ring which is optionally substituted with one to three substituents selected from $C_{1-6}$ alkyl, $C_{1-6}$ haloalkyl, hydroxyl and oxo;

each $R^{41}$ and $R^{42}$ is independently hydrogen or $C_{1-6}$ alkyl; or $R^{41}$ and $R^{42}$ are taken together with the nitrogen atom to which they are attached to form a $C_{3-7}$ heterocyclyl optionally substituted with one to three substituents selected from $C_{1-6}$ alkyl, $C_{1-6}$ haloalkyl, hydroxyl and oxo;

each $R^{43}$ and $R^{44}$ are independently hydrogen or $C_{1-6}$ alkyl; and $R^{45}$ is $C_{1-6}$ alkyl.

In some embodiments, D is:

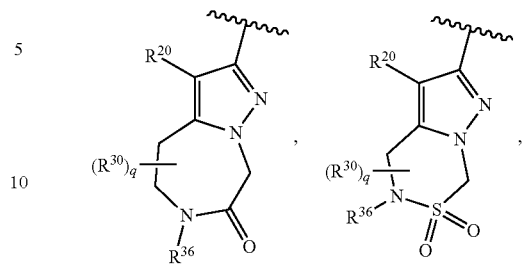

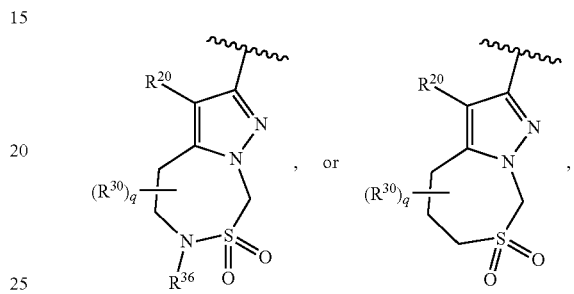

wherein q is 0, 1, 2, 3, 4, 5 or 6; $R^{36}$ is independently hydrogen or $R^{30}$; and $R^{20}$ and $R^{30}$ are as detailed herein. In some of these embodiments, $R^{20}$ is hydrogen, $C_{1-6}$ alkyl (e.g., methyl), halogen (e.g., fluoro), hydroxyl, or $C_{1-6}$ alkoxy (e.g., methoxy). In some embodiments, $R^{20}$ is H, Me, F or OH. In some of these embodiments, $R^{36}$ is hydrogen or $C_{1-6}$ alkyl (e.g., methyl). In some of these embodiments, q is 0.

In some embodiments, D is:

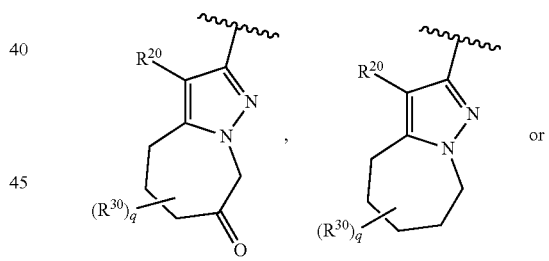

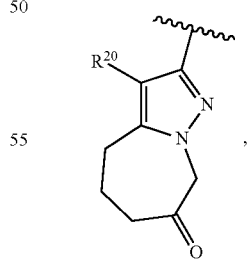

wherein q is 0, 1, 2, 3, 4, 5 or 6; and $R^{20}$ and $R^{30}$ are as detailed herein. In some of these embodiments, q is 0. In some of these embodiments, $R^{20}$ is hydrogen, $C_6$ alkyl (e.g., methyl), halogen (e.g., fluoro), hydroxyl, or $C_{1-6}$ alkoxy (e.g., methoxy). In some embodiments, $R^{20}$ is H, Me, F or OH.

In some embodiments, D is:

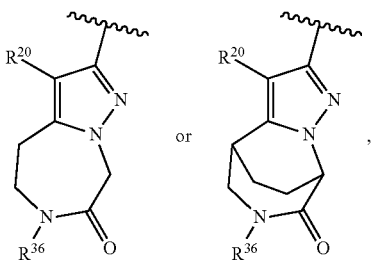

wherein $R^{36}$ is independently hydrogen or $R^{30}$; and $R^{20}$ and $R^{30}$ are as detailed herein. In some embodiments, $R^{36}$ is hydrogen or $C_{1-6}$ alkyl (e.g., methyl); and $R^{20}$ is hydrogen.

In some embodiments, wherein D is

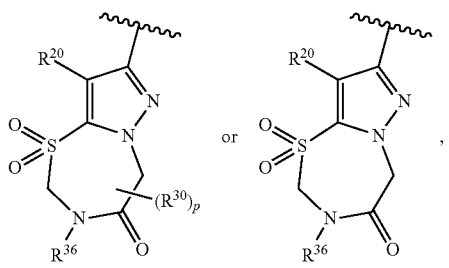

wherein p is 0, 1, 2, 3 or 4; $R^{36}$ is independently hydrogen or $R^{30}$; and $R^{20}$ and $R^{30}$ are as detailed herein. In some embodiments, p is 0. In some embodiments, $R^{36}$ is hydrogen or $C_{1-6}$ alkyl (e.g., methyl); and $R^{20}$ is hydrogen.

In some embodiments, wherein D is

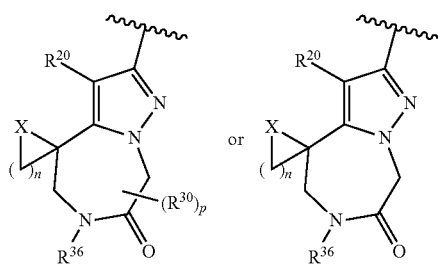

wherein X is $CH_2$, N, O or S; n is 1, 2, 3 or 4; p is 0, 1, 2, 3 or 4; $R^{36}$ is hydrogen or $R^3$; and $R^{20}$ and $R^{30}$ are as detailed herein. In some of these embodiments, X is $CH_2$ and n is 1. In some embodiments, $R^{36}$ is hydrogen or $C_{1-6}$ alkyl (e.g., methyl); and $R^{20}$ is hydrogen.

In some embodiments, wherein D is

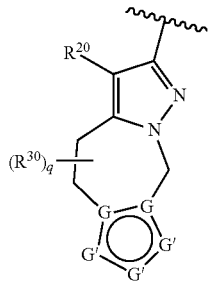

wherein q is 0, 1, 2, 3, 4, 5 or 6; G is independently C or N; G' is independently N, $NR^{46}$, $CR^{47}$, S or O; $R^{46}$ and $R^{47}$ are independently hydrogen or $R^{40}$, and $R^{20}$ and $R^{40}$ are as detailed herein. In some embodiments, two groups $R^{46}$ and $R^{47}$ are taken together to form a ring. In some of these embodiments, one of G is C and the other one of G is N. In some embodiments, each G is C. In some embodiments, at least one of G' is N. In some embodiments, at least one of G' is $CR^{47}$. In some embodiments, $R^{47}$ is H. In some embodiments, $R^{20}$ is hydrogen.

In some embodiments, wherein D is

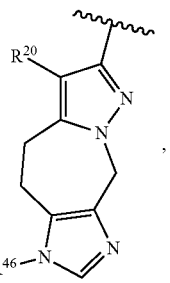

wherein $R^{20}$ and $R^{46}$ areas detailed herein. In some embodiments, $R^{46}$ is hydrogen or $C_{1-6}$ alkyl (e.g., methyl); and $R^{20}$ is hydrogen.

In some embodiments, wherein D is

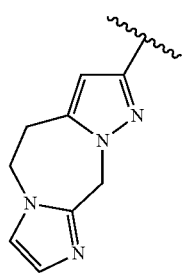

In some embodiments, wherein D is

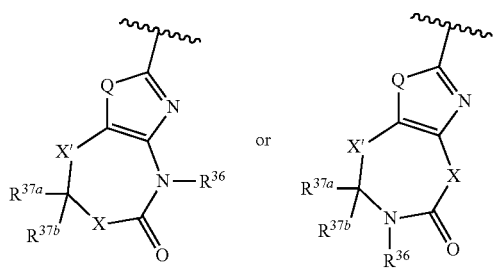

wherein Q is $NR^{20}$, O or S; X is $CR^{38a}R^{38b}$, $NR^{36}$, S or O; X' is $CR^{39a}R^{39b}$, $NR^{36}$, S, $SO_2$ or O; $R^{36}$, $R^{37a}$, $R^{37b}$, $R^{39a}$ and $R^{38b}$ are independently hydrogen or $R^{30}$; $R^{39a}$ and $R^{39b}$ are independently hydrogen or $R^{30}$, or $R^{39a}$ and $R^{39b}$ are taken together with the carbon atom to which they are attached to form a $C_{3-7}$ cycloalkyl or $C_{3-7}$ heterocyclyl; and $R^{20}$ and $R^{30}$ are as detailed herein. In some of these embodiments, Q is $NR^{20}$. In some of these embodiments, Q is S. In some embodiments, X is $CH_2$ or $NR^{36}$. In some embodiments, X' is $CH_2$. In some embodiments, X' is $SO_2$. In some embodiments, X' is CR^{39a}R^{39b} where R^{39a} and R^{39b} are taken together with the carbon atom to which they are attached to form a cyclopropyl. In some embodiments, R^{36} is hydrogen or C_{1-6} alkyl (e.g., methyl); and R^{20} is hydrogen.

In some embodiments, wherein D is

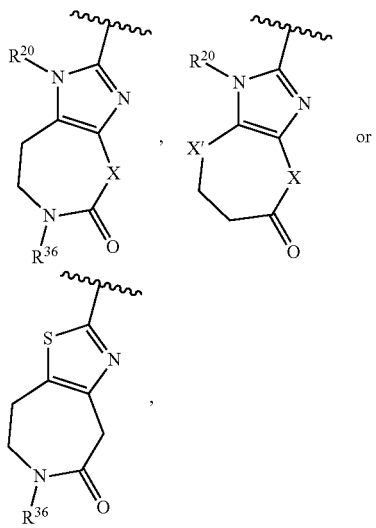

wherein X, X', R^{20} and R^{36} are as detailed herein. In some of these embodiments, X is CH_2 or NR^{36}. In some embodiments, X' is CH_2. In some embodiments, X' is SO_2. In some embodiments, X' is CR^{39a}R^{39b} where R^{39a} and R^{39b} are taken together with the carbon atom to which they are attached to form a cyclopropyl. In some embodiments, R^{36} is hydrogen or C_{1-6} alkyl (e.g., methyl). In some embodiments, R^{20} is hydrogen.

In some aspects in the compound of Formula I or Ia, R_2 is:

(a) a C_{6-10} aryl, 5-10 membered heteroaryl or 5-10 membered heterocyclyl, having 1-4 heteroatoms selected from O, S, and N; and optionally substituted with one, two, three or four substituents, R_6, R_7, R_8 and R_{8'}, each of which is independently selected from the group consisting of:
  i. branched or linear C_{1-6} alkyl, C_{1-6} alkenyl, or C_{1-6} alkenylene, wherein said alkyl, alkenyl and alkenylene can be optionally substituted with one to four substituents independently selected from the group consisting of hydroxyl, halogen, nitrile, amino, mono(C_{1-6}alkyl)amino-, di(C_{1-6}alkyl)amino-, —SO_2R^y, —S(O)NR^y, —(CO)NR^yR^z, —NR^zSO_2R^y, —NR^y(CO)OR^z, —NR^y(CO)NR^yR^z, and —NR^y(CO)R^z, wherein R^y and R^z, in each instance, is independently hydrogen or optionally substituted C_{1-6} alkyl (e.g., an alkyl optionally substituted with one to four substituents independently selected from the group consisting of hydroxyl and halogen);
  ii. NR^yR^z—C(O)—, wherein R^y and R^z are each independently hydrogen or optionally substituted C_{1-6} alkyl (e.g., an alkyl optionally substituted with one to four substituents independently selected from the group consisting of hydroxyl and halogen);
  iii. hydroxy(C_{1-6} alkyl);
  iv. hydroxyl or optionally substituted C_{1-6} alkoxy (e.g., an alkoxy optionally substituted with one to four substituents independently selected from the group consisting of hydroxyl and halogen);
  v. substituted or unsubstituted C_{3-9} cycloalkyl, substituted or unsubstituted C_6 aryl, substituted or unsubstituted 5-membered heteroaryl, or substituted or unsubstituted C_{2-9} heterocyclyl;
  vi. halogen;
  vii. substituted or unsubstituted amino;
  viii. cyano;
  ix. —NR^yC(O)R^z, wherein R^y and R^z are each independently hydrogen or optionally substituted C_{1-6} alkyl (e.g., an alkyl optionally substituted with one to four substituents independently selected from the group consisting of hydroxyl and halogen);
  x. —SO_2R', wherein R' is H or C_{1-6} alkyl;
  xi. —SO_2NR'R'', wherein R' and R'' are independently H or C_{1-6} alkyl; or R' and R'' are taken together with the nitrogen to which they are attached to form a substituted or unsubstituted heterocyclyl;
  xii. —NR'C(O)OR'', —NR'C(O)NR''R''', —NR'SO_2NR''R''' or —NR'S(O)R'', wherein R' and R''' are independently H or C_{1-6} alkyl and R'' is independently C_{1-6} alkyl, halo(C_{1-6} alkyl) or C_{6-10} aryl optionally substituted with C_{1-6} alkyl; or R'' and R''' are taken together with the nitrogen to which they are attached to form a substituted or unsubstituted heterocyclyl; and
  xiii. wherein a carbon embedded in said heterocyclyl taken together with an oxygen to which it is bound can form a carbonyl; or (b) a C_{6-10} aryl having one, two, three or five substituents selected from the group consisting of branched or linear C_{1-6} alkyl, C_{1-6} alkenyl, C_{1-6} alkenylene, C_{3-4} cycloalkyl, wherein said alkyl, alkenyl, alkenylene and cycloalkyl can be substituted with amino, hydroxyl, cyano, halogen, amide, mono(C_{1-6} alkyl)amino-, di(C_{1-6} alkyl)amino-, —SO_2R^c, —S(O)NR^d, —C(O)NR^cR^d and —NR^cC(O)R^d, wherein R^c and R^d are each independently selected from the group consisting of hydrogen and C_{1-6} alkyl, wherein said alkyl can be optionally substituted with one to four hydroxyl or halogen; or (c) hydrogen, —NHSO_2R^a, —SO_2NR^aR^b; or —SO_2NH_2; wherein each R^a is independently C_{1-6} alkyl, and R^b is hydrogen or C_{1-6} alkyl; or (d) —OR^{a1} or —(C_{1-6} alkyl)-OR^{a1}; wherein each R^{a1} is independently C_{1-6} alkyl optionally substituted with C_{6-10} aryl; 5-10 membered heteroaryl; or 5-10 membered heterocyclyl; wherein the 5-10 membered heteroaryl, and 5-10 membered heterocyclyl are optionally substituted with one to four substituents independently selected from the group consisting of hydroxyl, oxo, C_{1-6} alkyl or C_{1-6} alkoxy; or (e) a C_{1-6} alkyl optionally substituted with one to five substituents independently selected from the group consisting of hydroxyl, halogen, cyano, amino, mono(C_{1-6} alkyl)amino, di(C_{1-6} alkyl)amino, amido, sulfonyl, sulfonamide, C_{3-8} cycloalkyl, C_{6-10} aryl, 5-10 membered heteroaryl, and 5-10 membered heterocyclyl; wherein the C_{3-8} cycloalkyl, C_{6-10} aryl, 5-10 membered heteroaryl, and 5-10 membered heterocyclyl are optionally substituted (e.g., with one to four substituents independently selected from the group consisting of hydroxyl, oxo, C_{1-6} alkyl or C_{1-6} alkoxy); or (f) C_{3-8} cycloalkyl optionally substituted with one to four substituents independently selected from the group consisting of C_{1-6} alkyl, hydroxyl, halogen, cyano, amino, mono(C_{1-6}alkyl)amino, di(C_{1-6}alkyl)amino, amido, sulfonyl, sulfonamide, 5-10 membered heteroaryl, and 5-10 membered heterocyclyl; wherein the 5-10 membered heteroaryl, and 5-10 membered heterocyclyl are optionally substituted (e.g., with one to four substituents independently selected from the group consisting of hydroxyl, oxo, $C_{1-6}$ alkyl or $C_{1-6}$ alkoxy);

(g) —C(O)NR$^{a2}$R$^{b2}$ or —SO$_2$NR$^{a2}$R$^{b2}$, wherein each R$^{a2}$ is independently hydrogen or $C_{1-6}$ alkyl, and R$^{b2}$ is hydrogen, $C_{1-6}$ alkyl, 5-10 membered heteroaryl or 5-10 membered heterocyclyl, wherein the 5-10 membered heteroaryl and 5-10 membered heterocyclyl are optionally substituted (e.g., with one to four substituents independently selected from the group consisting of $C_{1-6}$ alkyl, $C_{3-7}$ cycloalkyl, oxo, hydroxyl, halo and cyano); or R$^{a2}$ and R$^{b2}$ are taken together with the nitrogen to which they are attached to form a substituted or unsubstituted heterocyclyl (e.g., piperidine, piperazine, pyrrolidine); or (h) 5-10 membered heteroaryl fused with a ring selected from the group consisting of 5 or 6 membered heteroaryl, 5-10 membered heterocyclyl, $C_6$ aryl and $C_{3-7}$ cycloalkyl, wherein the 5-10 membered heteroaryl of R$_2$ and the fused ring are optionally substituted (e.g., with one to four substituents independently selected from the group consisting of hydroxyl, oxo, $C_{1-6}$ alkyl or $C_{1-6}$ alkoxy).

In embodiments where all other variables are as defined above, useful values of R$_2$ are an optionally substituted $C_{2-9}$ heteroaryl, or an optionally substituted $C_{2-9}$ heterocyclyl (e.g., $C_{3-7}$ heterocyclyl). In an embodiment, R$_2$ is an optionally substituted 5-10 member heteroaryl or an optionally substituted 5-10 member heterocyclyl; and all other variables are as defined in Formula I or Ia or are as defined in any of the embodiments described herein. In an aspect of this embodiment, R$_2$ is a 5 member heteroaryl. In an aspect of this embodiment, R$_2$ is a 5 member heterocyclyl. In an aspect of this embodiment, R$_2$ is a 6 member heteroaryl. In an aspect of this embodiment, R$_2$ is a 6 member heterocyclyl. In an aspect of this embodiment, R$_2$ is a 7 member heteroaryl. In an aspect of this embodiment, R$_2$ is a 7 member heterocyclyl. In an aspect of this embodiment, R$_2$ is an 8 member heteroaryl. In an aspect of this embodiment, R$_2$ is an 8 member heterocyclyl. In an aspect of this embodiment, R$_2$ is a 9 member heteroaryl. In an aspect of this embodiment, R$_2$ is a 9 member heterocyclyl. In an aspect of this embodiment, R$_2$ is a 10 member heteroaryl. In an aspect of this embodiment, R$_2$ is a 10 member heterocyclyl. In each instance, the heteroaryl or heterocyclyl can be optionally substituted at with one, two or three substituents, R$_6$, R$_7$ and R$_8$.

In some embodiments, R$_6$, R$_7$, and R$_8$ are each independently selected from the group consisting of:
i. branched or linear $C_{1-6}$ alkyl, $C_{1-6}$ alkenyl, or $C_{1-6}$ alkenylene, wherein said alkyl, alkenyl and alkenylene can be optionally substituted with one to four substituents independently selected from the group consisting of hydroxyl, halogen, nitrile, amino, mono($C_{1-6}$alkyl)amino-, di($C_{1-6}$alkyl)amino-, —SO$_2$R$^y$, —S(O)NR$^y$, —(CO)NR$^y$R$^z$ and —NR$^y$(CO)R$^z$, wherein R$^y$ and R$^z$, in each instance, is independently hydrogen or $C_{1-6}$ alkyl, wherein said alkyl can optionally be substituted with one to four substituents independently selected from the group consisting of hydroxyl and halogen;
ii. NR$^y$R$^z$—C(O)—, wherein R$^y$ and R$^z$ are each independently hydrogen or $C_{1-6}$ alkyl, wherein said alkyl can optionally be substituted with one to four substituents independently selected from the group consisting of hydroxyl and halogen;
iii. hydroxy($C_{1-6}$ alkyl);
iv. $C_{1-6}$ alkoxy, wherein said alkoxy can be optionally substituted with one to four substituents independently selected from the group consisting of hydroxyl and halogen;
v. $C_{3-9}$ cycloalkyl, substituted or unsubstituted $C_6$ aryl, substituted or unsubstituted 5-membered heteroaryl, or $C_{2-9}$ heterocyclyl;
vi. halogen;
vii. amino;
viii. cyano;
ix. —NR$^y$C(O)R$^z$, wherein R$^y$ and R$^z$ are each independently hydrogen or $C_{1-6}$ alkyl, wherein said alkyl can optionally be substituted with one to four substituents independently selected from the group consisting of hydroxyl and halogen;
x. —SO$_2$R', wherein R' is H or $C_{1-6}$ alkyl;
xi. —SO$_2$NR'R", wherein R' and R" are independently H or $C_{1-6}$ alkyl;
xii. —NR'C(O)OR", —NR'SO$_2$NR" or —NR'S(O)R", wherein R' is independently H or $C_{1-6}$ alkyl and R" is independently $C_{1-6}$ alkyl, halo($C_{1-6}$ alkyl) or $C_{6-10}$ aryl optionally substituted with $C_{1-6}$ alkyl; and
xiii. wherein a carbon embedded in said heterocyclyl taken together with an oxygen to which it is bound can form a carbonyl.

In an embodiment, R$_2$ is selected from the group consisting of:

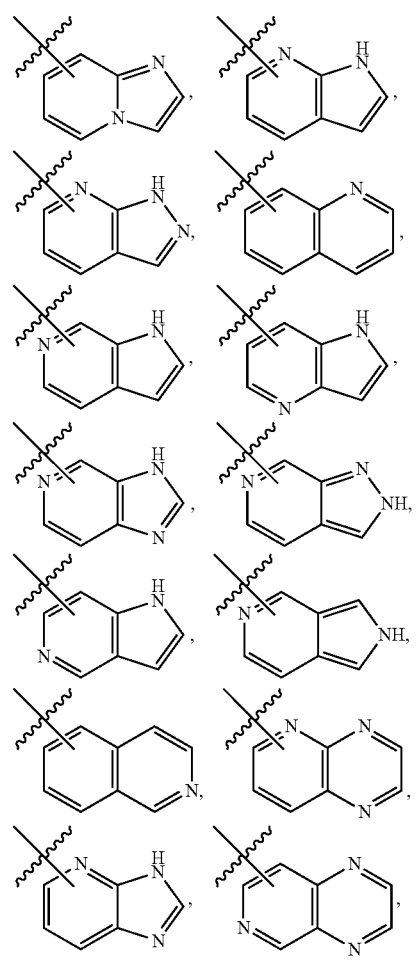

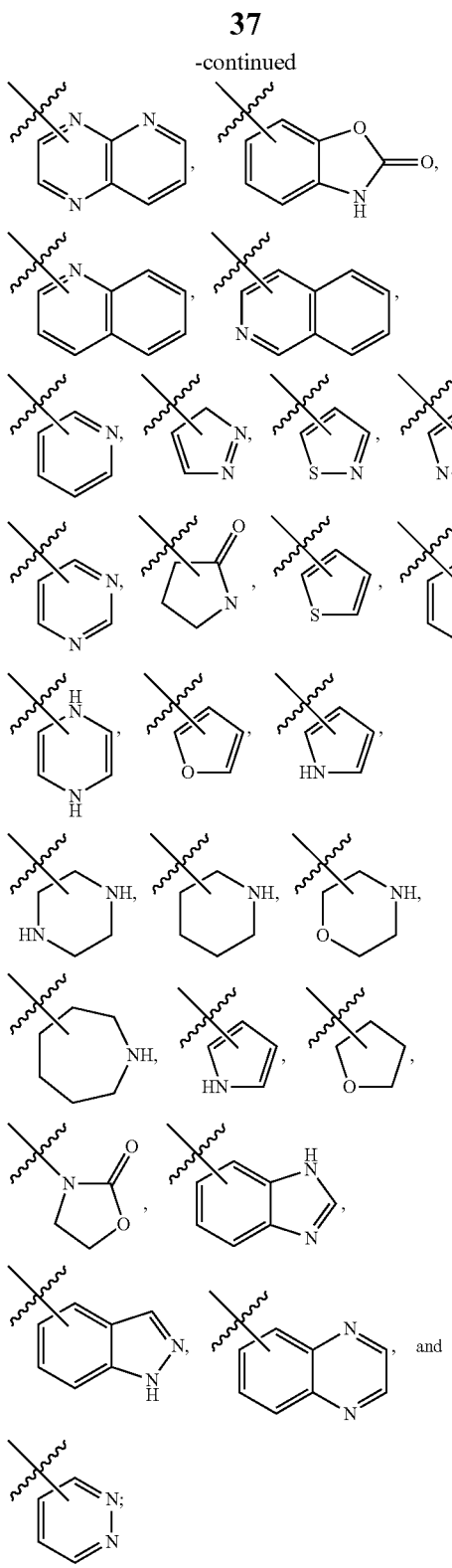

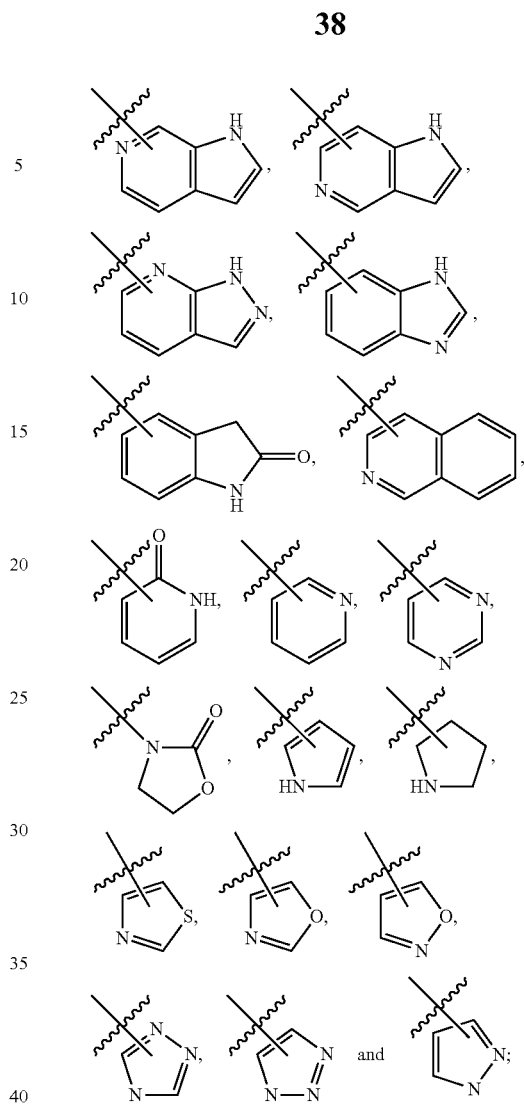

each of which is optionally substituted. In some embodiments, each of the above moieties can be optionally substituted with one, two or three substituents, $R_6$, $R_7$ and $R_8$; and all other variables are as defined in Formula I or Ia or are as defined in any of the embodiments described herein.

In some embodiments, $R_2$ is selected from the group consisting of:

each of which is optionally substituted. In some embodiments, each of the above moieties can be optionally substituted with one, two or three substituents, $R_6$, $R_7$ and $R_8$; and all other variables are as defined in Formula I or Ia or are as defined in any of the embodiments described herein.

In embodiments where all other variables areas defined in any embodiment above, useful values of $R_2$ are

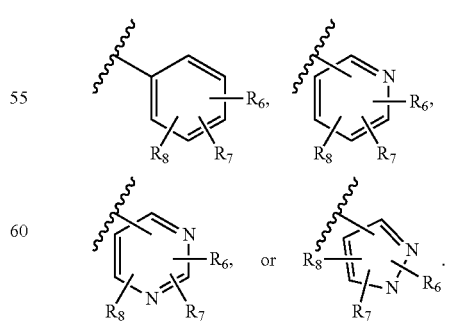

In embodiments where all other variables areas defined in any embodiment above, $R_2$ is

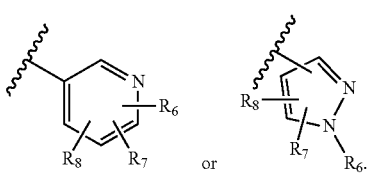

In embodiments where all other variables areas defined in any embodiment above, wherein $R_2$ is

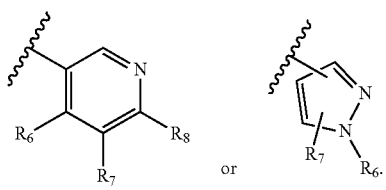

In embodiments where all other variables are as defined in any embodiment above, wherein $R_2$ is

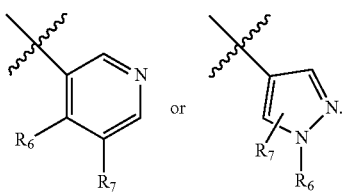

In an embodiment, $R_2$ is

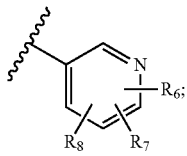

and all other variables are as defined in Formula I or Ia or are as defined in any of the embodiments described herein.

In some embodiments, $R_2$ is

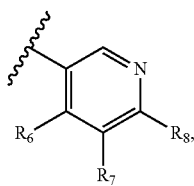

wherein $R_6$, $R_7$, and $R_8$ are each independently selected from the group consisting of hydrogen, hydroxyl, amino, $C_{1-6}$ alkyl, $C_{1-6}$ alkoxy, and mono($C_{1-6}$ alkyl)amino; or two of $R_6$, $R_7$, and $R_8$ can form a bicyclic.

In an embodiment, $R_2$ is

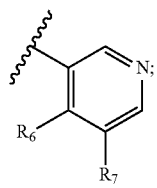

and all other variables are as defined in Formula I or Ia or are as defined in any of the embodiments described herein. In some of these embodiments, $R_6$ and $R_7$ are selected from the group consisting of hydrogen, amino, and $C_{1-6}$ alkyl. In some embodiments, $R_6$ is $C_{1-6}$ alkyl (e.g., methyl). In some embodiments, $R_7$ is hydrogen or amino. In some embodiments, $R_7$ is hydrogen. In some embodiments, $R_7$ is amino. In some embodiments, $R_6$ is $C_{1-6}$ alkyl (e.g., methyl) and $R_7$ is hydrogen or amino.

In an embodiment, $R_2$ is

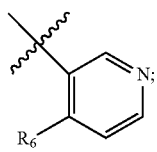

and all other variables are as defined in Formula I or Ia or are as defined in any of the embodiments described herein. In this embodiment, $R_6$ can be hydrogen, optionally substituted $C_{1-6}$ alkyl or hydroxy($C_{1-6}$)alkyl, and all other variables are as defined in Formula I or Ia or are as defined in any of the embodiments described herein. In an aspect of this embodiment, $R_6$ can be $C_{1-6}$ alkyl, such as methyl, ethyl, propyl, isopropyl, n-butyl, t-butyl, pentyl, and hexyl, and all other variables are as defined in Formula I or Ia or are as defined in any of the embodiments described herein. In a particular aspect of this embodiment, $R_6$ is methyl and all other variables are as defined in Formula I or Ia or are as defined in any of the embodiments described herein. In some of these embodiments, $R_6$ is $C_{1-6}$ alkyl, optionally substituted with hydroxyl, —$CF_2$, —$CF_3$, or halogen.

In some embodiments, $R_2$ is

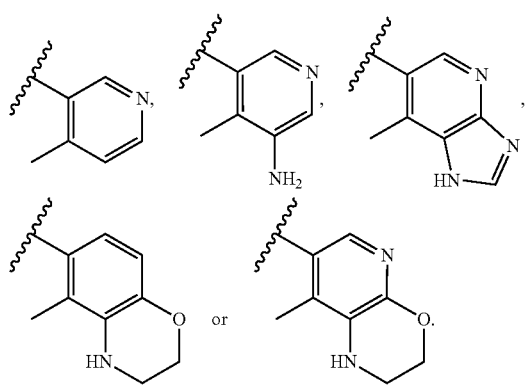

In some embodiments, $R_2$ is

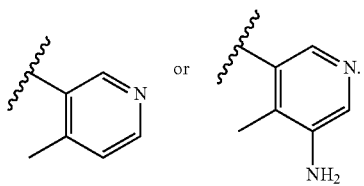

In some embodiments, $R_2$ is

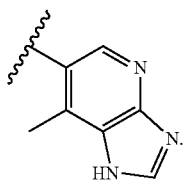 [SMILES: *c1cnc2nc[nH]c2c1C]

In some embodiments, $R_2$ is

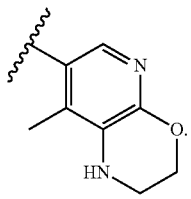 [SMILES: *c1cnc2c(c1C)NCCO2]

In some embodiments, $R_2$ is

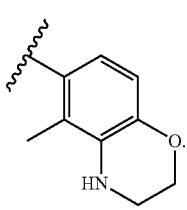 [SMILES: *c1ccc2c(c1C)NCCO2]

In an embodiment, $R_2$ is

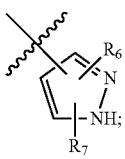

and all other variables are as defined in Formula I or Ia or are as defined in any of the embodiments described herein.

In an embodiment, $R_2$ is

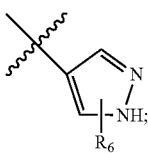

and all other variables are as defined in Formula I or Ia or are as defined in any of the embodiments described herein.

In an embodiment, $R_2$ is

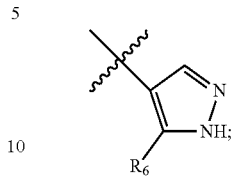

and all other variables are as defined in Formula I or Ia or are as defined in any of the embodiments described above. In this embodiment, $R_6$ can be optionally substituted branched or linear $C_{1-6}$ alkyl, which can be substituted with one to four hydroxyl or halogen; and all other variables are as defined in Formula I or Ia or are as defined in any of the embodiments described herein.

In an embodiment, $R_2$ is

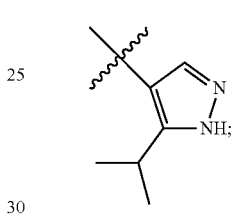

and all other variables are as defined in Formula I or Ia or are as defined in any of the embodiments described herein.

In an embodiment, $R_2$ is

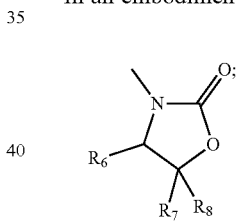

and all other variables are as defined in Formula I or Ia or are as defined in any of the embodiments described herein.

In an embodiment, $R_2$ is

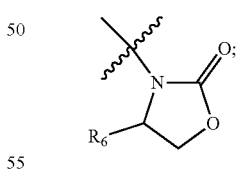

and all other variables are as defined in Formula I or Ia or are as defined in any of the embodiments described herein. In this embodiment, $R_6$ can be optionally substituted branched or linear $C_{1-6}$ alkyl; and all other variables are as defined in Formula I or Ia or are as defined in any of the embodiments described herein. In an aspect of this embodiment, $R_6$ can be $C_{1-6}$ alkyl, such as methyl, ethyl, propyl, isopropyl, n-butyl, t-butyl, pentyl, and hexyl, and all other variables are as defined in Formula I or Ia or are as defined in any of the embodiments described herein. In a particular aspect of this embodiment, $R_6$ is methyl and all other variables are as defined in Formula I or Ia or are as defined in any of the embodiments described herein.

In an embodiment, $R_2$ is

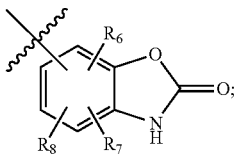

and all other variables are as defined in Formula I or Ia or are as defined in any of the embodiments described herein.

In an embodiment, $R_2$ is

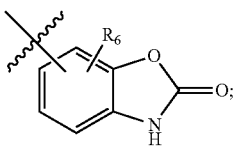

and all other variables are as defined in Formula I or Ia or are as defined in any of the embodiments described herein.

In an embodiment, $R_2$ is

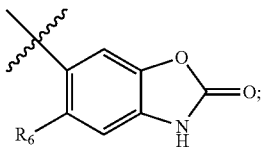

and all other variables are as defined in Formula I or Ia or are as defined in any of the embodiments described herein. In a particular aspect of this embodiment, $R_6$ can be optionally substituted branched or linear $C_{1-6}$ alkyl; and all other variables are as defined in Formula I or Ia or are as defined in any of the embodiments described herein. In an aspect of this embodiment, $R_6$ can be $C_{1-6}$ alkyl, such as methyl, ethyl, propyl, isopropyl, n-butyl, t-butyl, pentyl, and hexyl, and all other variables are as defined in Formula I or Ia or are as defined in any of the embodiments described herein. In a particular aspect of this embodiment, $R_6$ is methyl and all other variables are as defined in Formula I or Ia or are as defined in any of the embodiments described herein.

In an embodiment, $R_2$ is

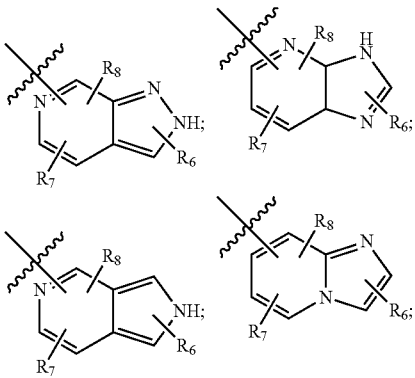

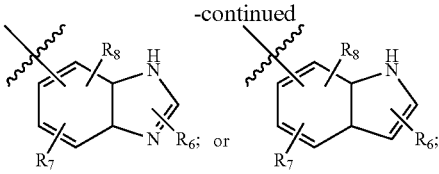

and all other variables are as defined in Formula I or Ia or are as defined in any of the embodiments described herein. In a particular aspect of this embodiment, $R_6$ can be hydrogen or optionally substituted branched or linear $C_{1-6}$ alkyl, $R_7$ can be hydrogen or optionally substituted branched or linear $C_{1-6}$ alkyl, and all other variables are as defined in Formula I or Ia or are as defined in any of the embodiments described herein. In an aspect of this embodiment, $R_6$ can be $C_{1-6}$ alkyl, such as methyl, ethyl, propyl, isopropyl, n-butyl, t-butyl, pentyl, and hexyl, and all other variables are as defined in Formula I or Ia or are as defined in any of the embodiments described herein. In a particular aspect of this embodiment, $R_6$ is methyl and all other variables are as described in Formula I or Ia or are as defined in any of the embodiments described herein. In a particular aspect of this embodiment, $R_6$ and $R_7$ are each hydrogen and all other variables are as defined in Formula I or Ia or are as defined in any of the embodiments described herein. In a particular aspect of this embodiment, $R_5$ is hydrogen, and all other variables are as defined in Formula I or Ia or are as defined in any of the embodiments described herein.

In an embodiment, $R_2$ is

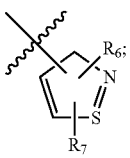

and all other variables are as defined in Formula I or Ia or are as defined in any of the embodiments described herein.

In an embodiment, $R_2$ is

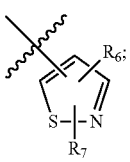

and all other variables are as defined in Formula I or Ia or are as defined in any of the embodiments described herein.

In an embodiment, $R_2$ is

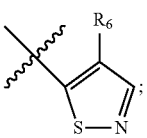

and all other variables are as defined in Formula I or Ia or are as defined in any of the embodiments described above. In this embodiment, $R_6$ can be optionally substituted branched or linear $C_{1-6}$ alkyl, which can be substituted with one to four hydroxyl or halogen; and all other variables are as defined in Formula I or Ia or are as defined in any of the embodiments described herein. In an aspect of this embodiment, $R_6$ can be $C_{1-6}$ alkyl, such as methyl, ethyl, propyl, isopropyl, n-butyl, t-butyl, pentyl, and hexyl, and all other variables are as defined in Formula I or Ia or are as defined in any of the embodiments described herein. In a particular aspect, $R_6$ is methyl.

In an embodiment, in a 5-10 member heterocyclyl, one of $R_6$, $R_7$ and $R_8$ is O and together with the carbon to which it is attached forms a carbonyl; and all other variables are as defined in Formula I or Ia or are as defined in any of the embodiments described herein. In a particular aspect of this embodiment, $R_2$ is

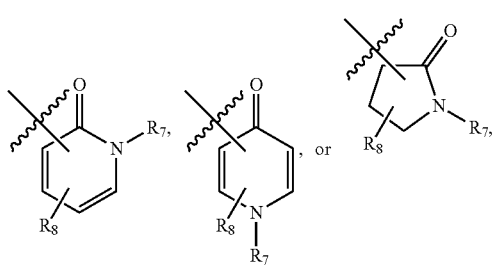

wherein, $R_7$ is hydrogen or $C_{1-5}$ alkyl; and all other variables are as defined in Formula I or Ia or are as defined in any of the embodiments described herein.

In an embodiment, in a 5-10 member heterocyclyl, one of $R_6$, $R_7$ and $R_8$ is O and together with the carbon to which it is attached forms a carbonyl; and all other variables are as defined in Formula I or Ia or are as defined in any of the embodiments described herein. In a particular aspect of this embodiment, $R_2$ is

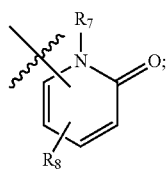

and all other variables are as defined in Formula I or Ia or are as defined in any of the embodiments described herein. In this embodiment, $R_7$ and $R_8$ are independently selected from hydrogen or branched or linear $C_{1-6}$ alkyl, which can be substituted with one to four hydroxyl or halogen; and all other variables are as defined in Formula I or Ia or are as defined in any of the embodiments described herein.

In embodiments, the subject matter described herein is directed to a compound having one of the following structures:

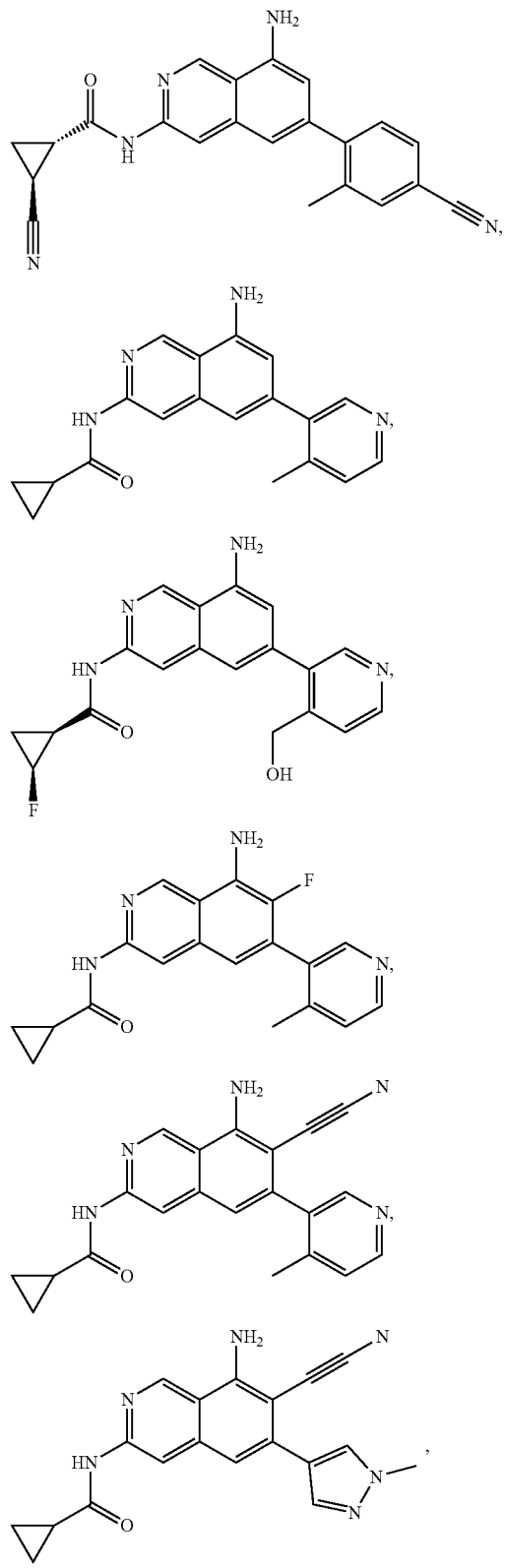

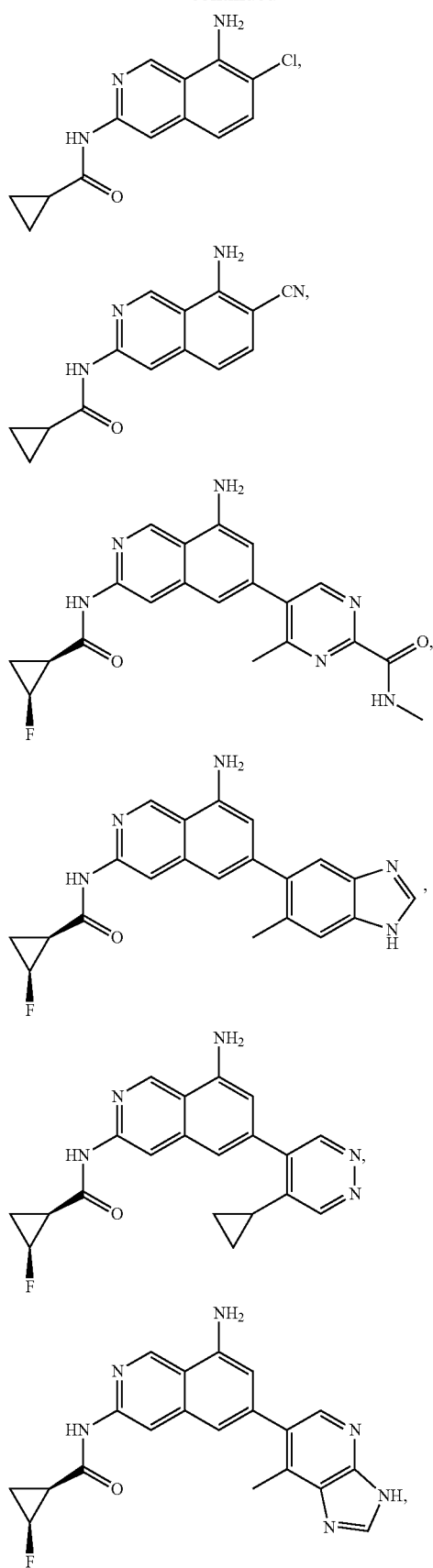
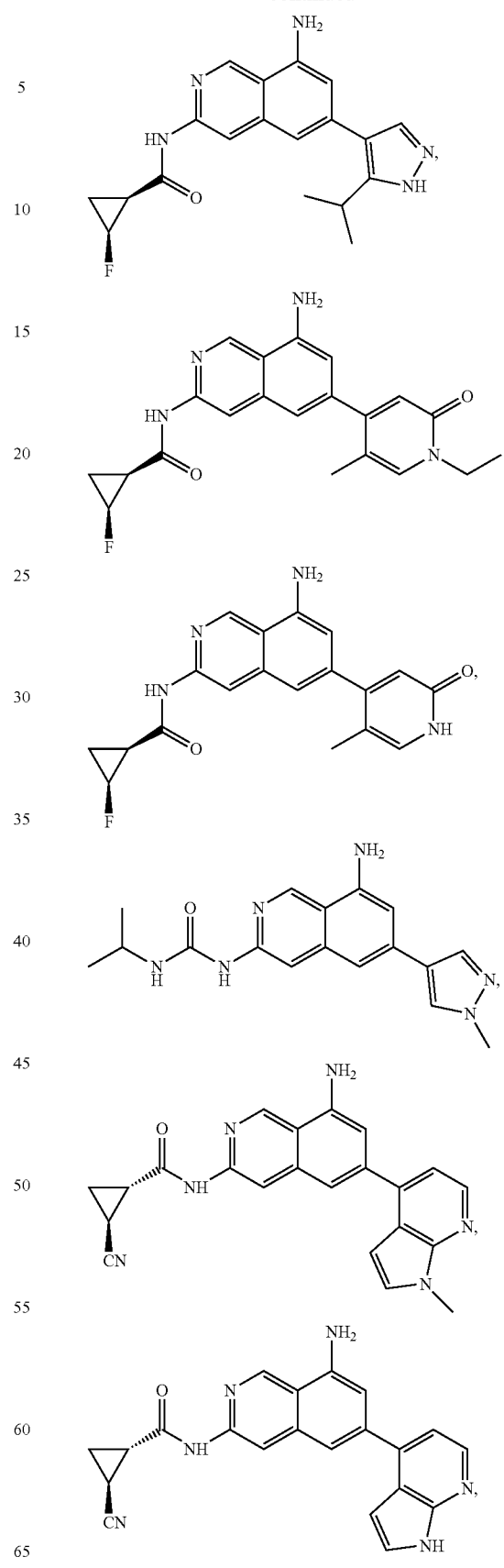

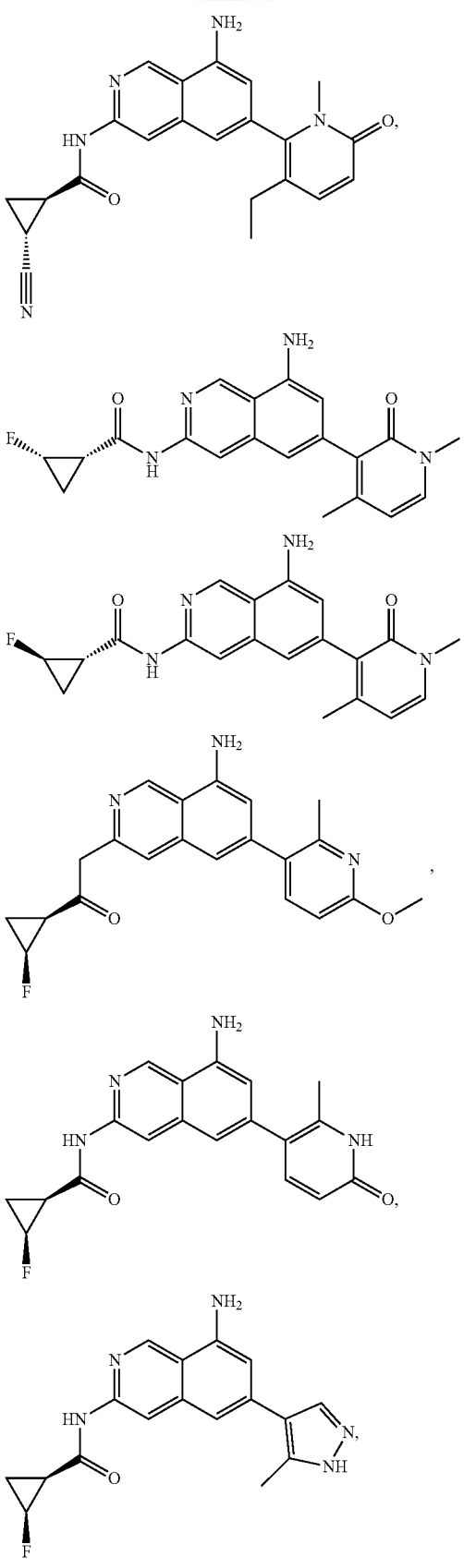
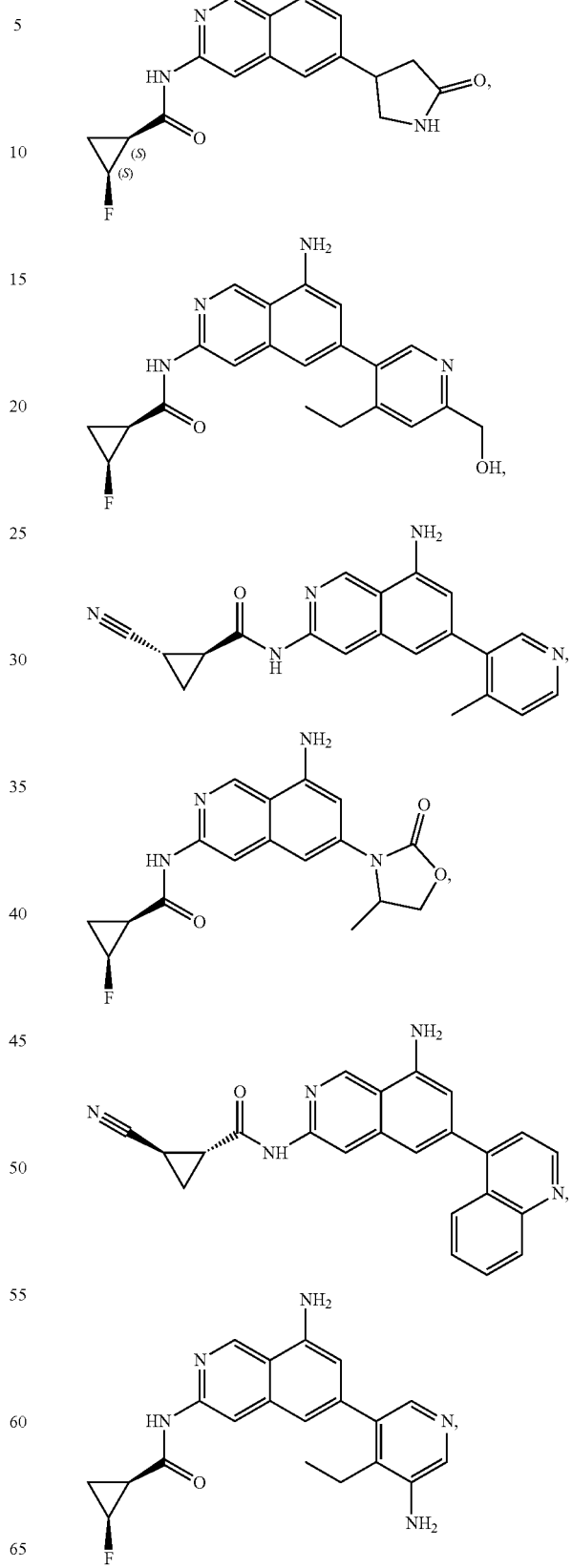

51
-continued
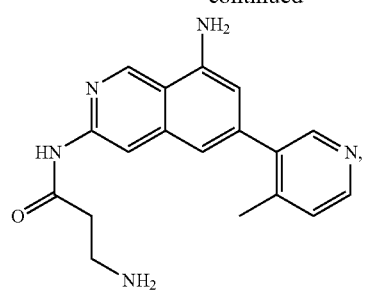
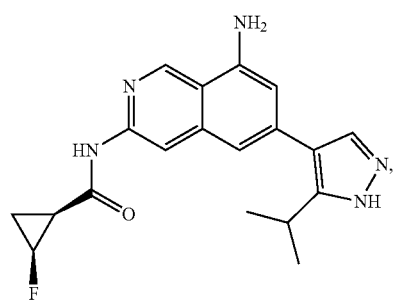
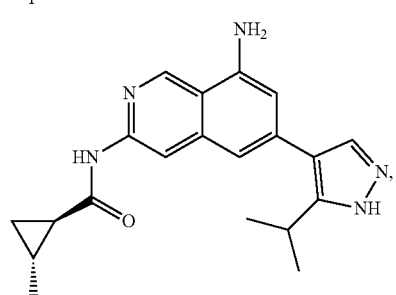
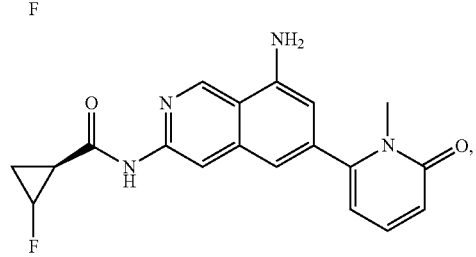
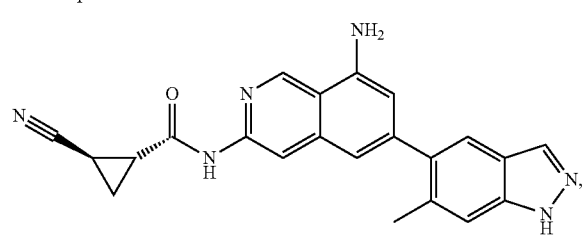
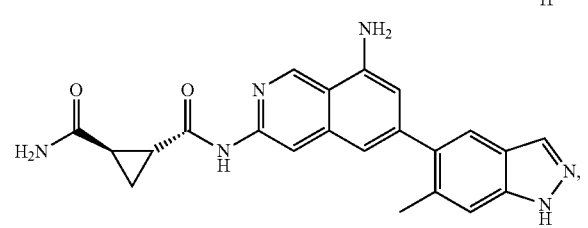
52
-continued
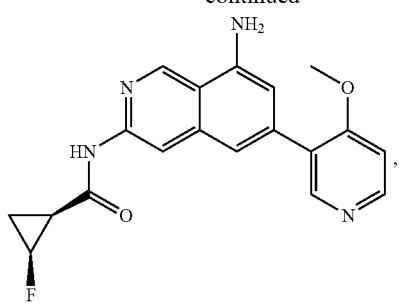
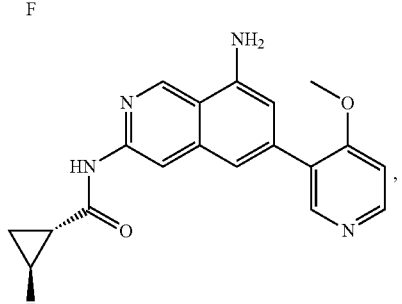
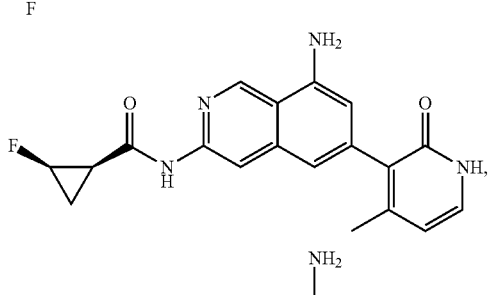
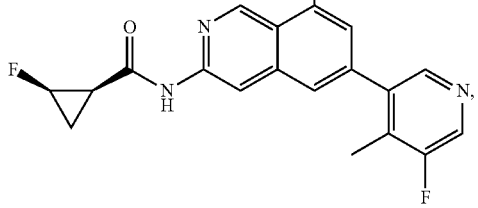
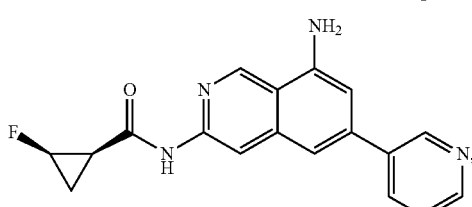
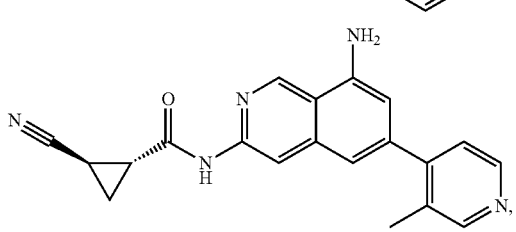

53
-continued
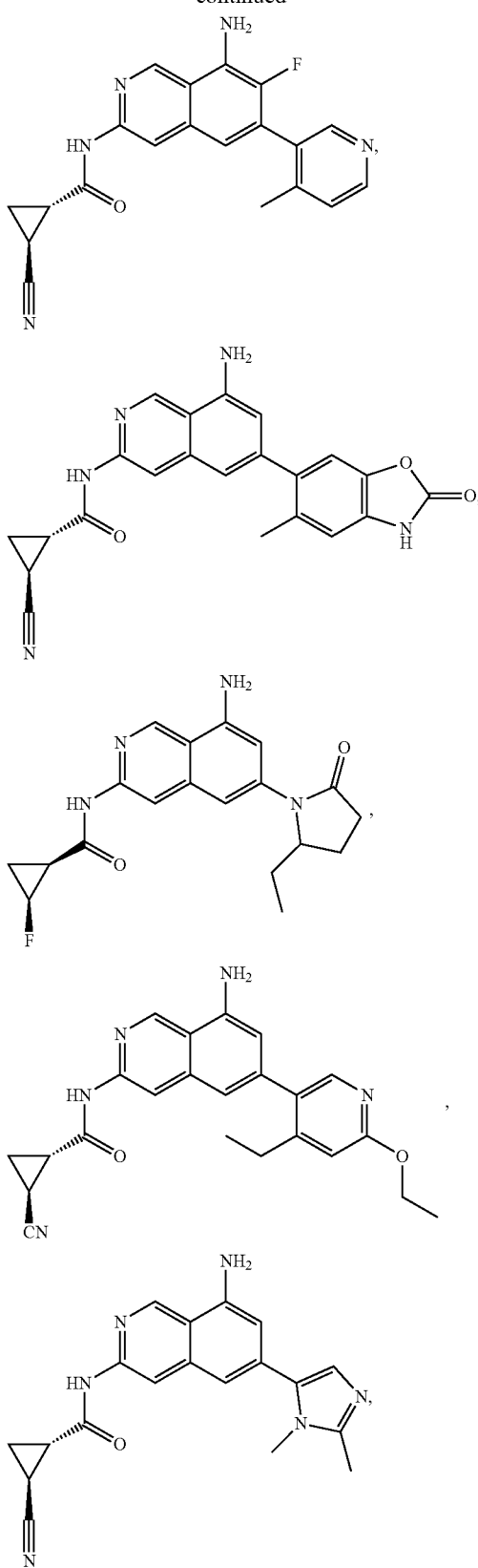
54
-continued
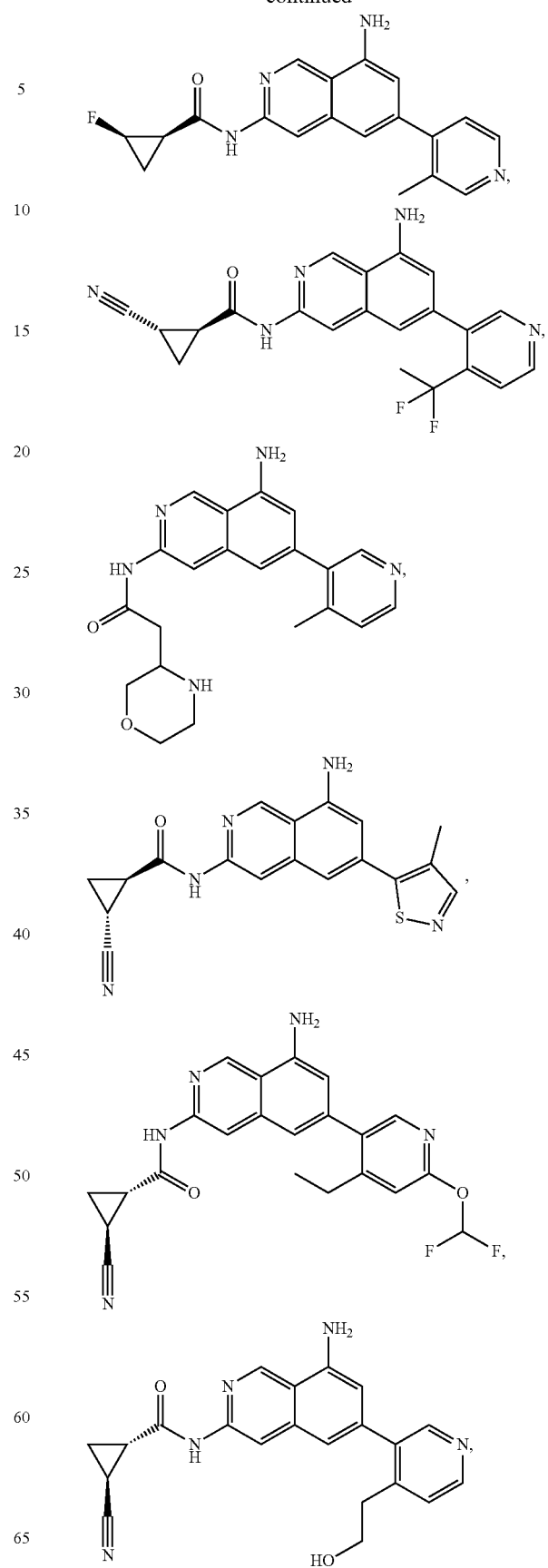

55
-continued
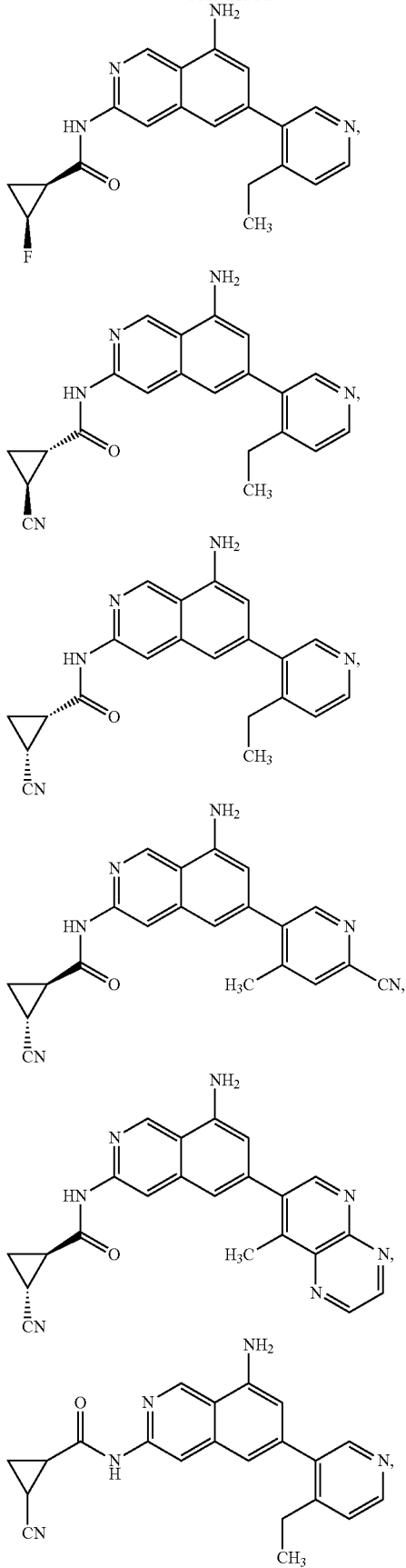
56
-continued
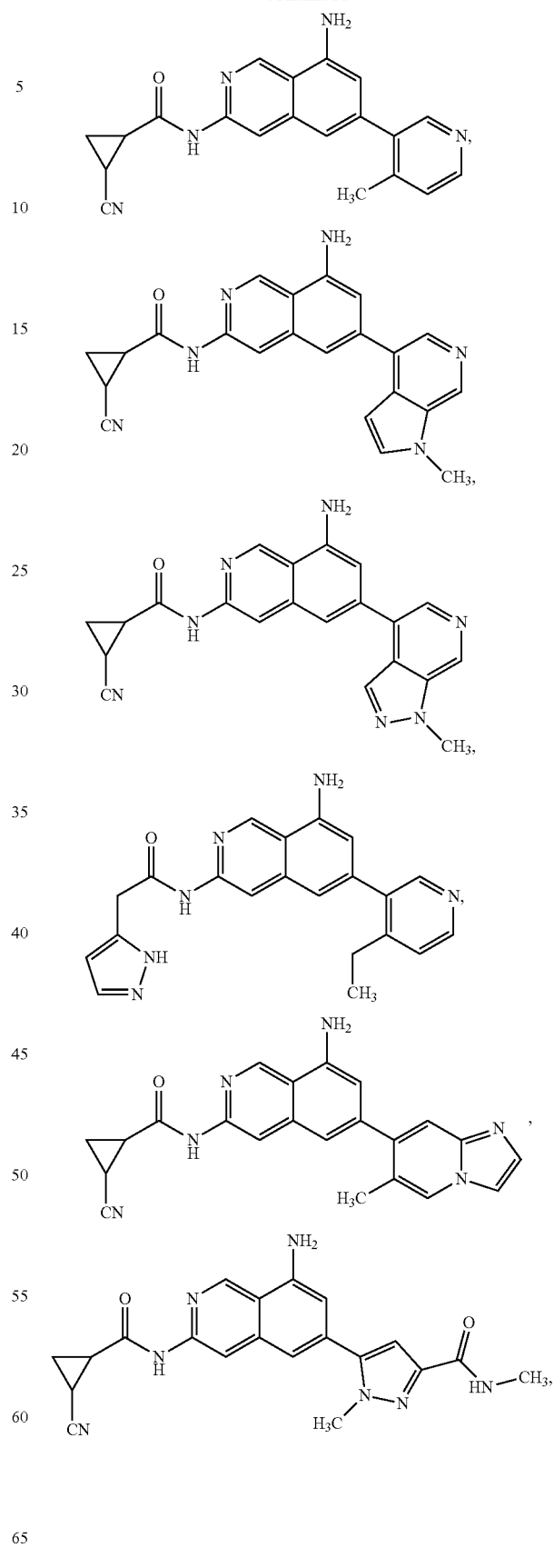

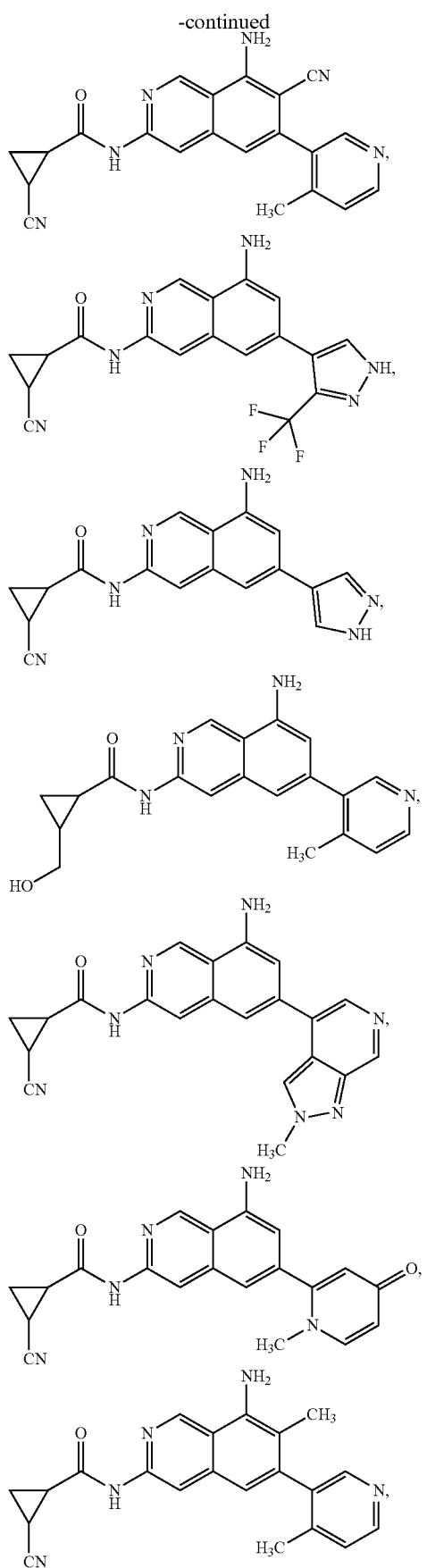
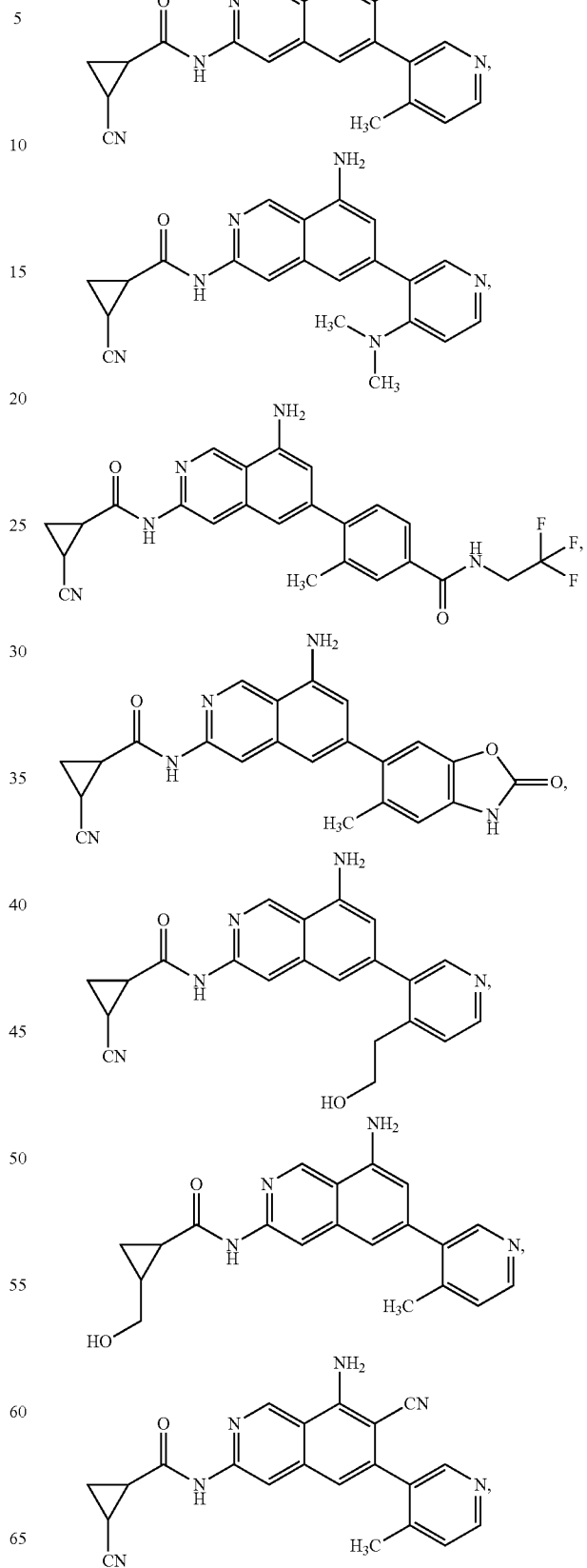

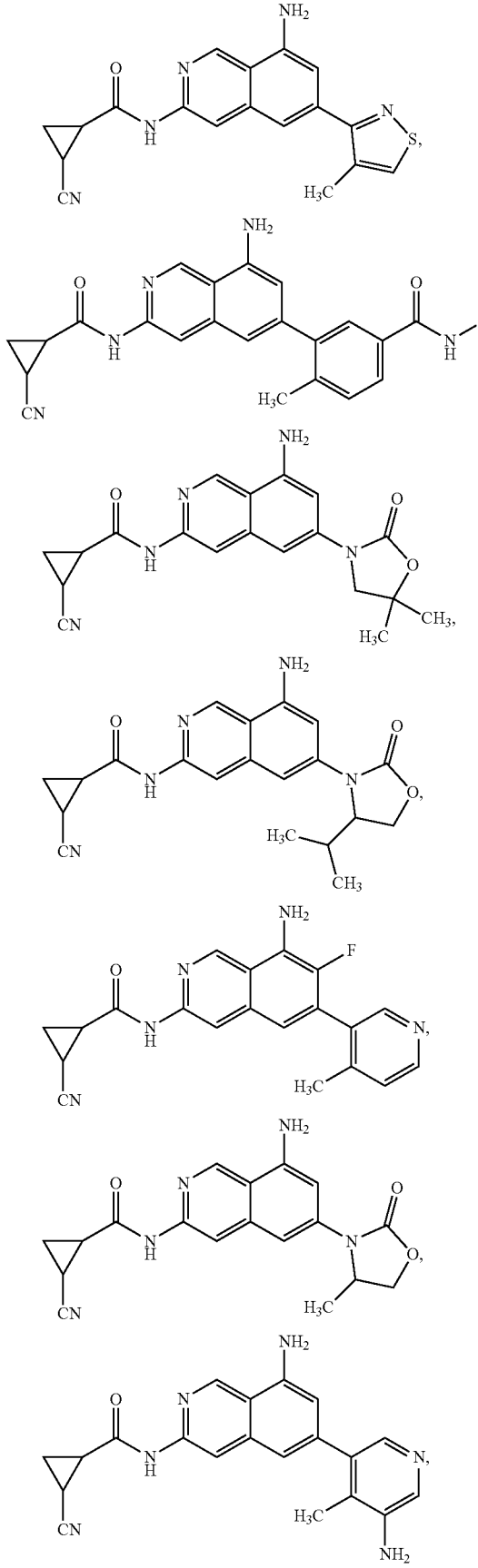
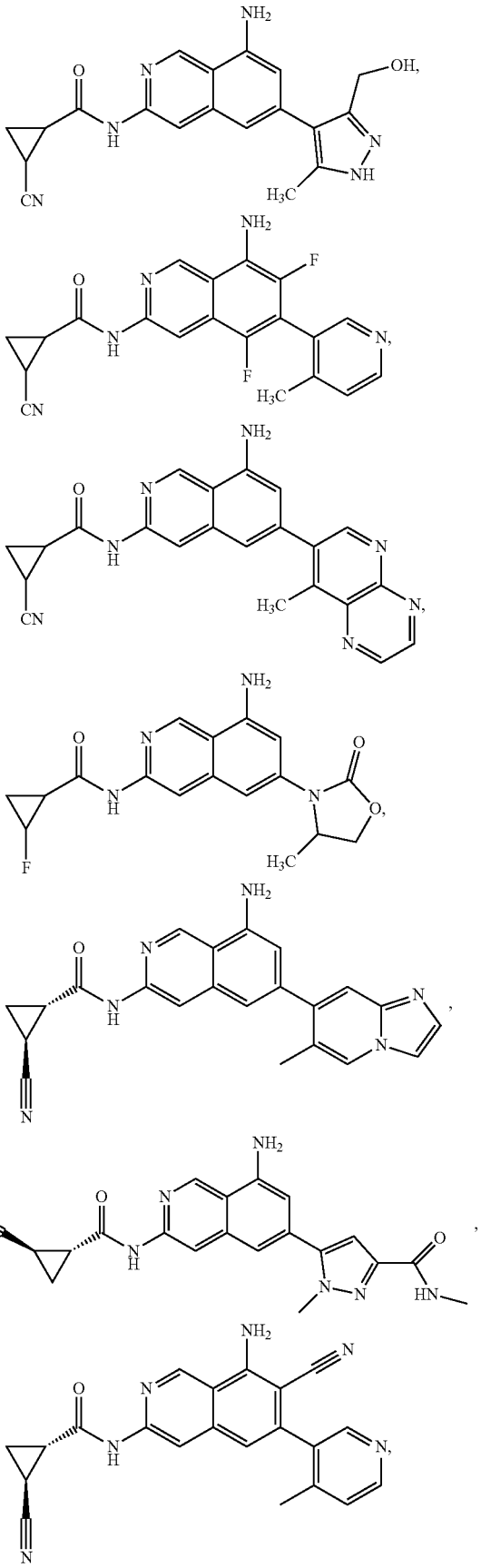

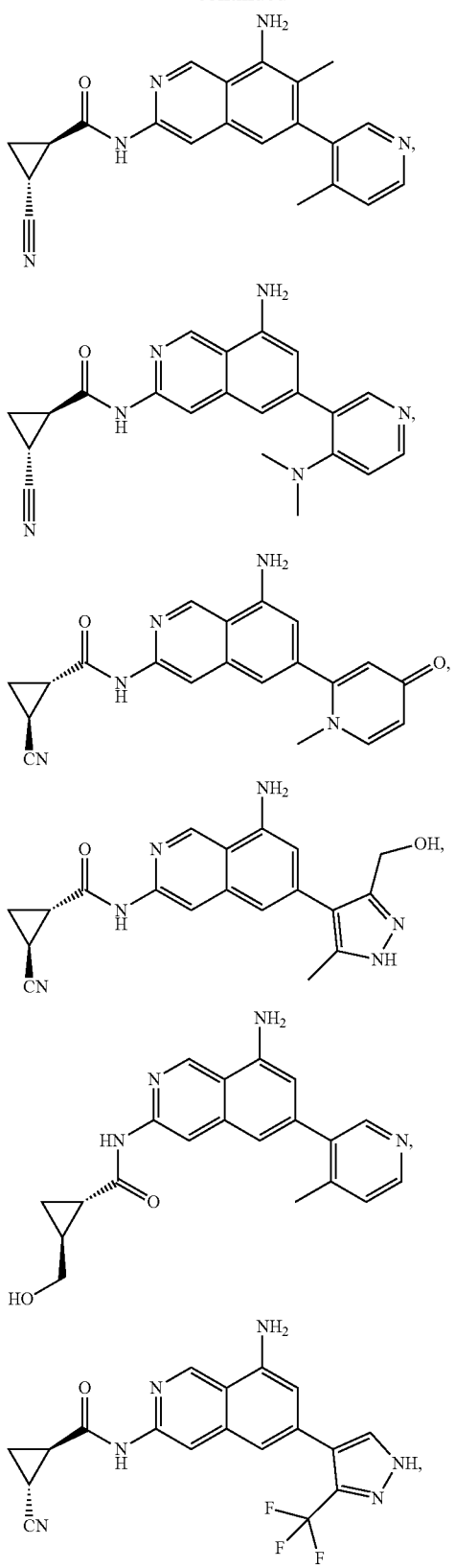
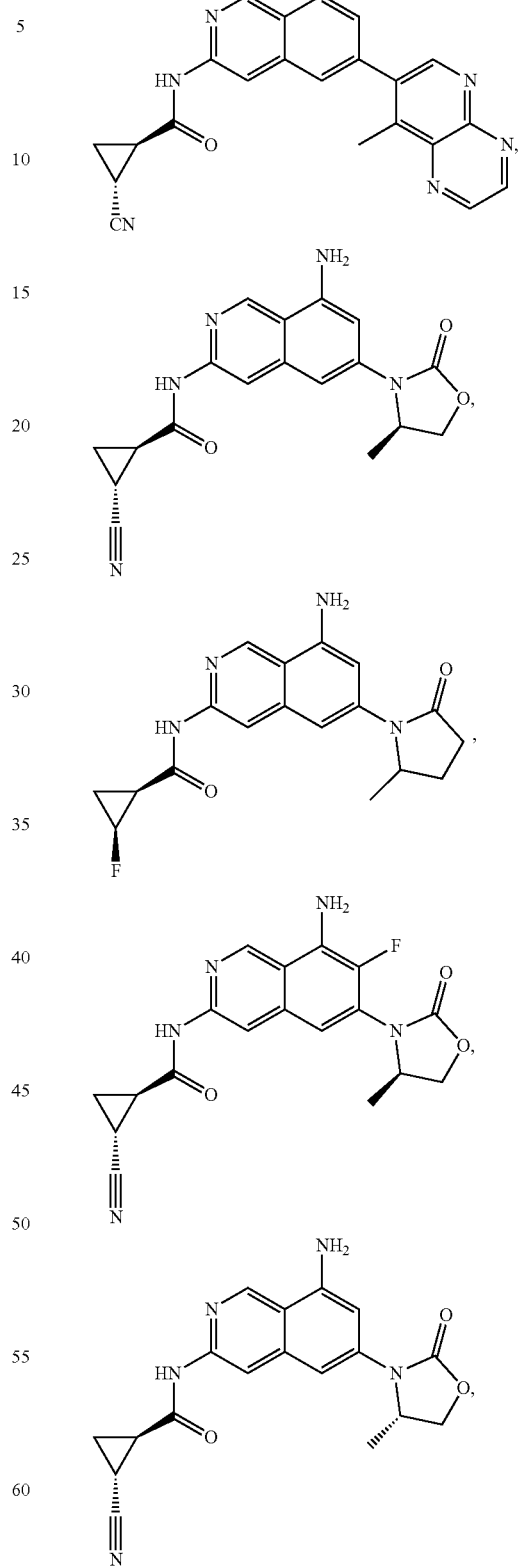

63
-continued
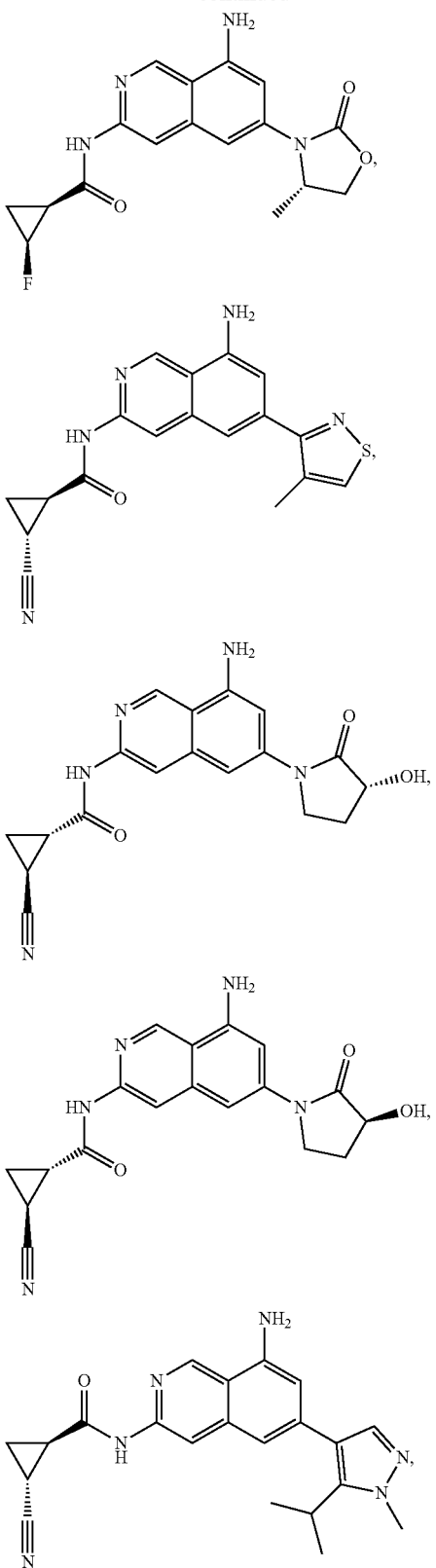
64
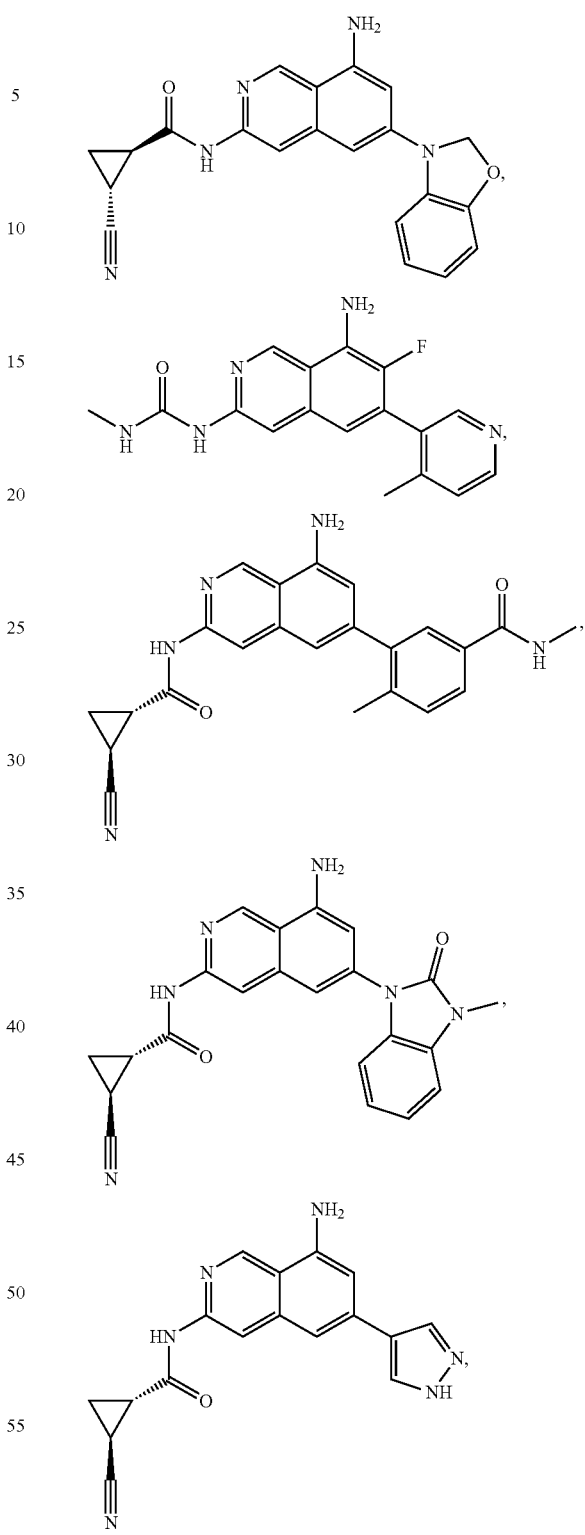

65
-continued
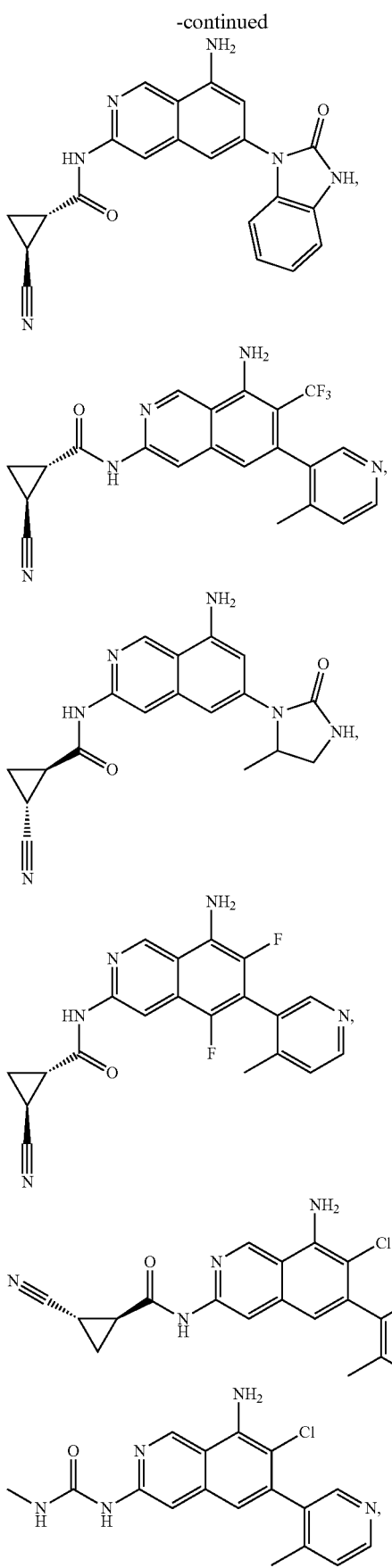
66
-continued
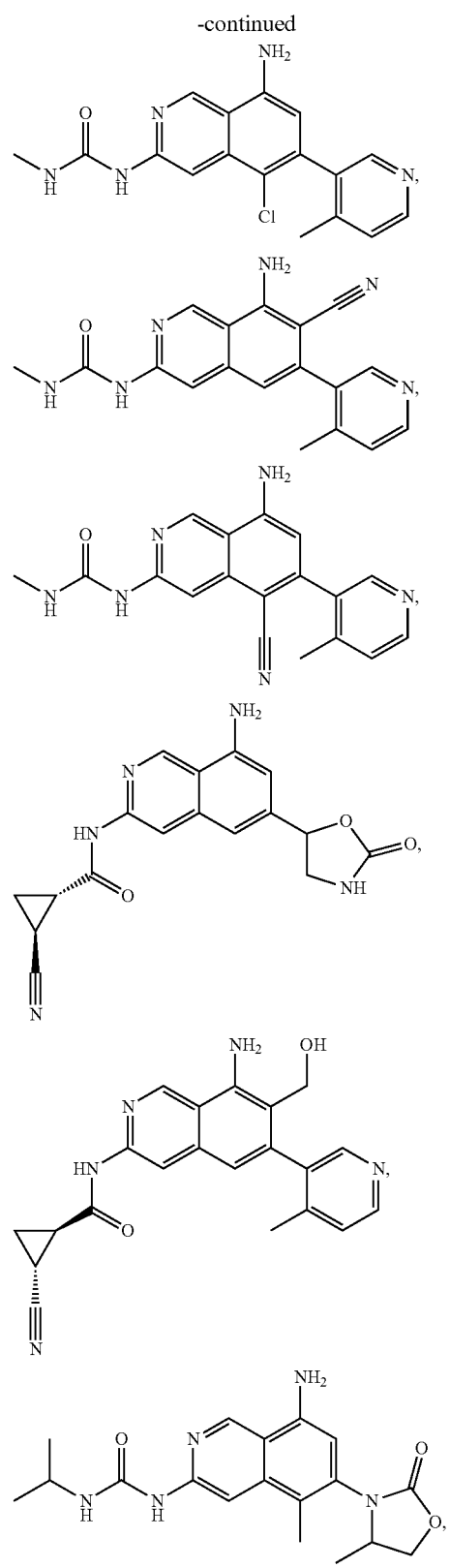

67
-continued
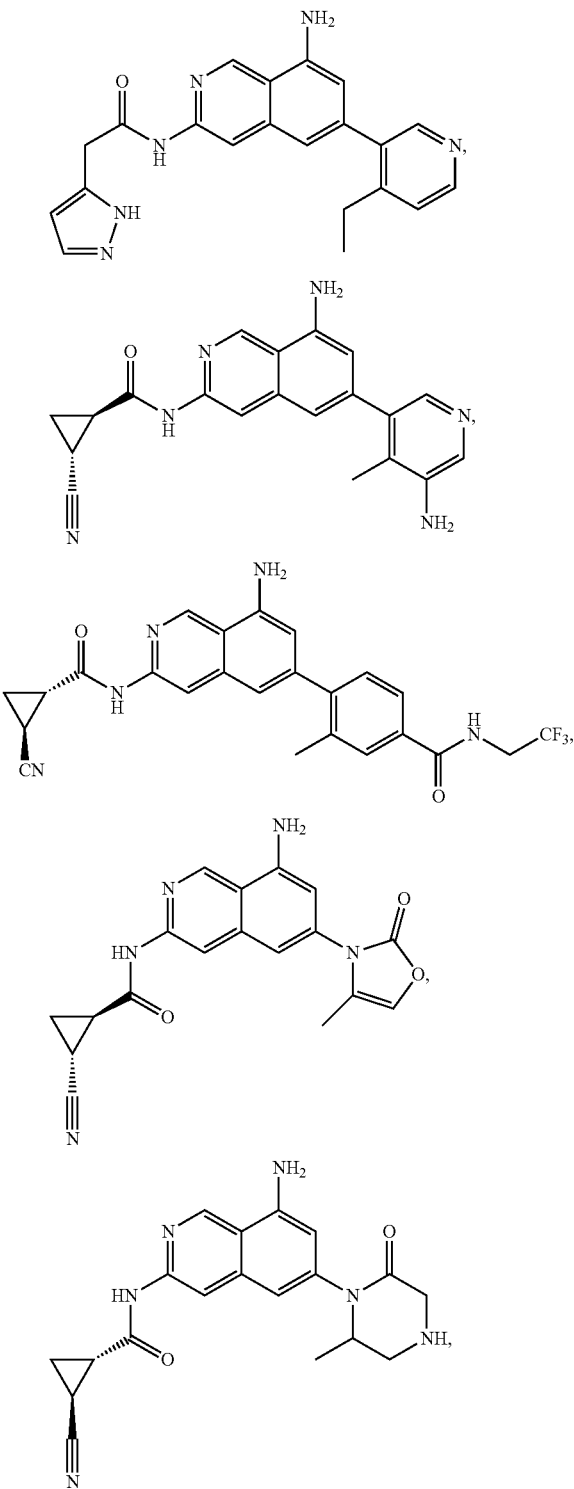
68
-continued
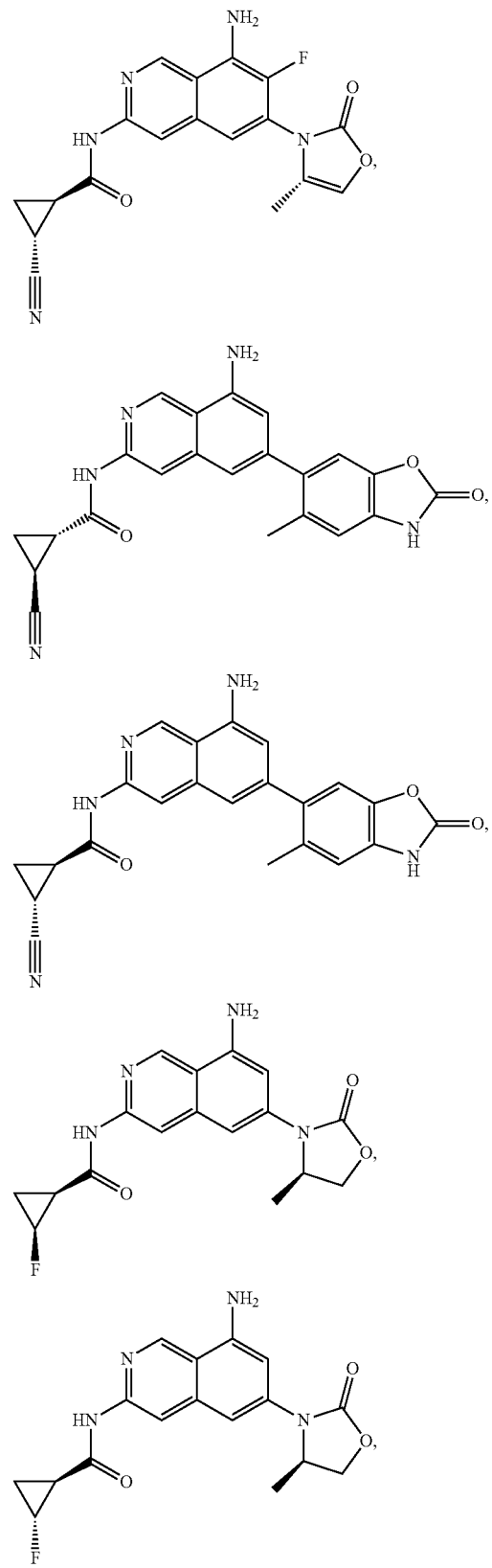

-continued
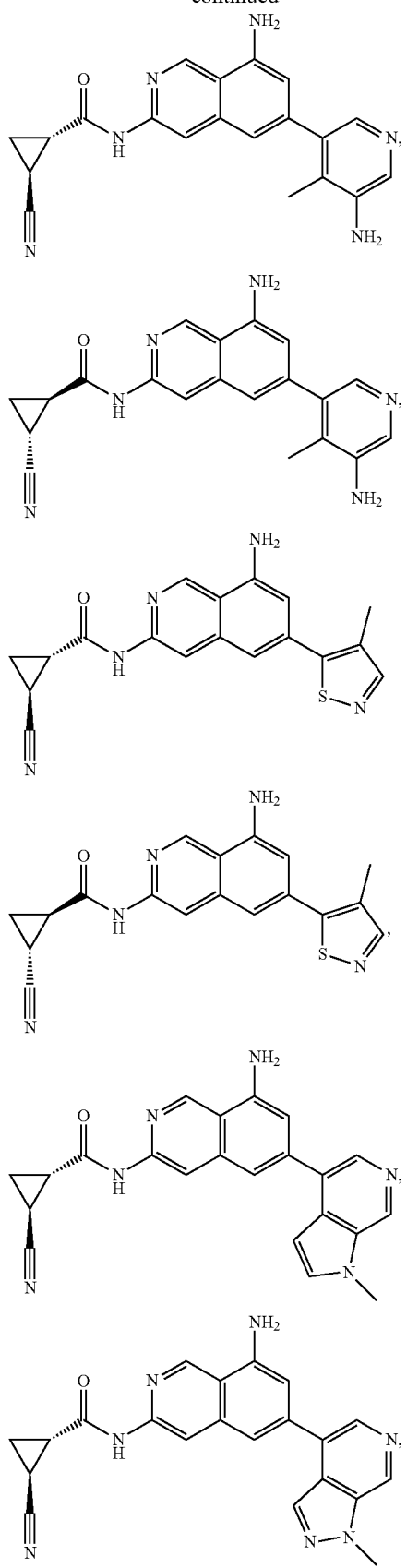
-continued
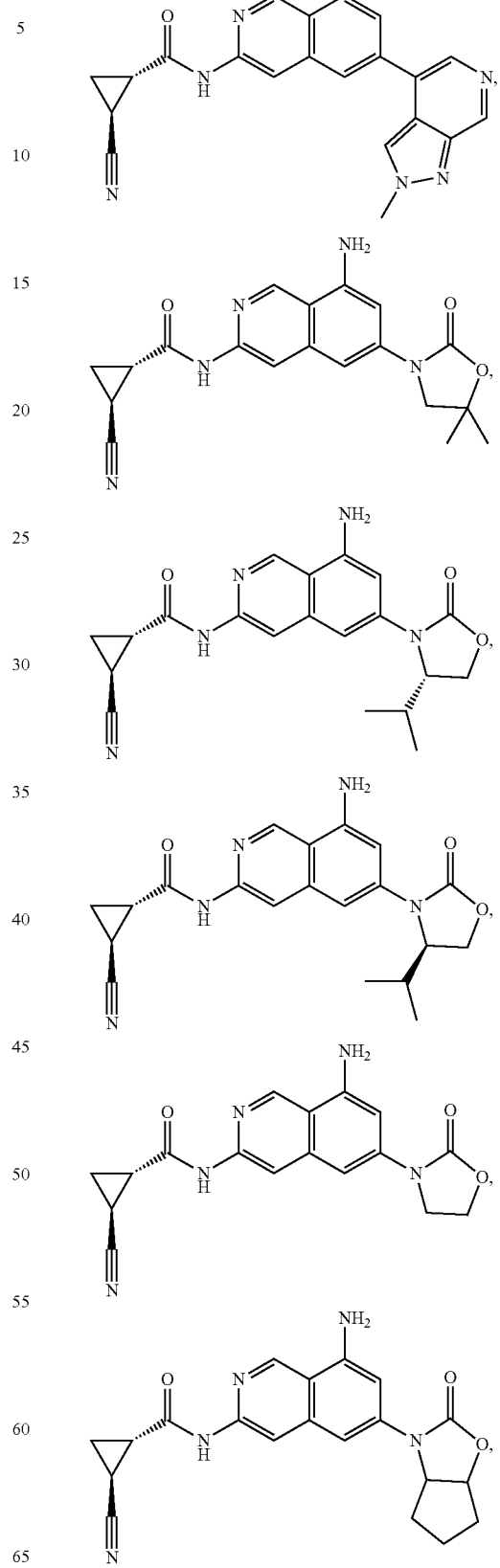

71
-continued
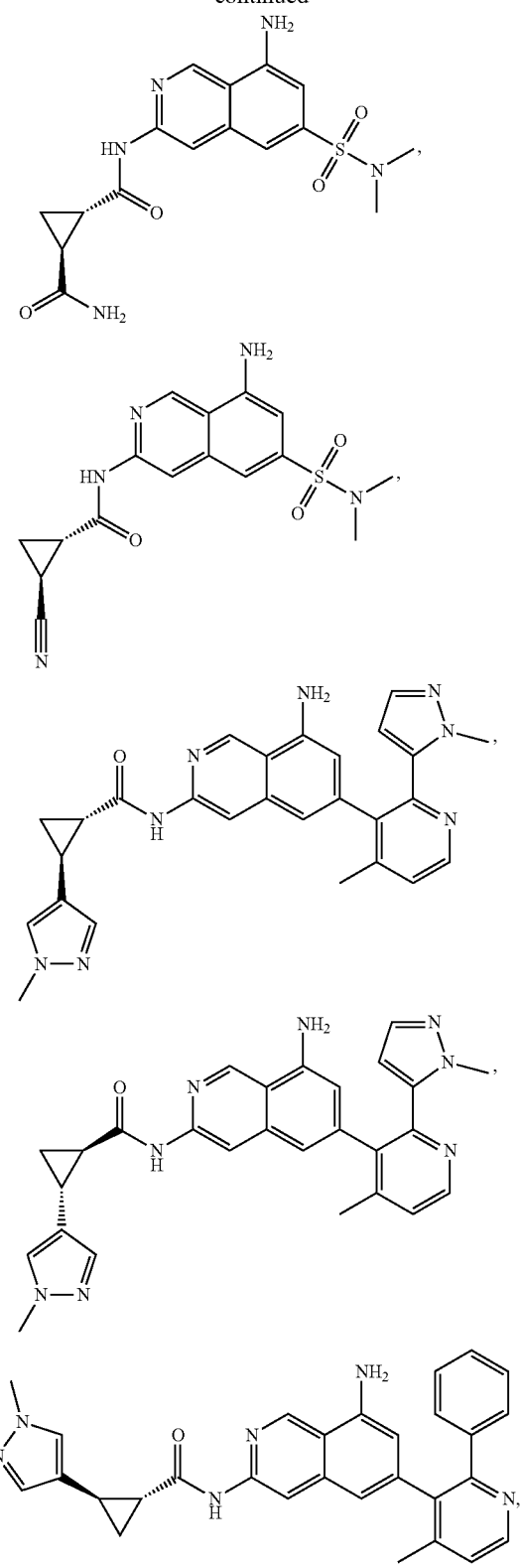
72
-continued
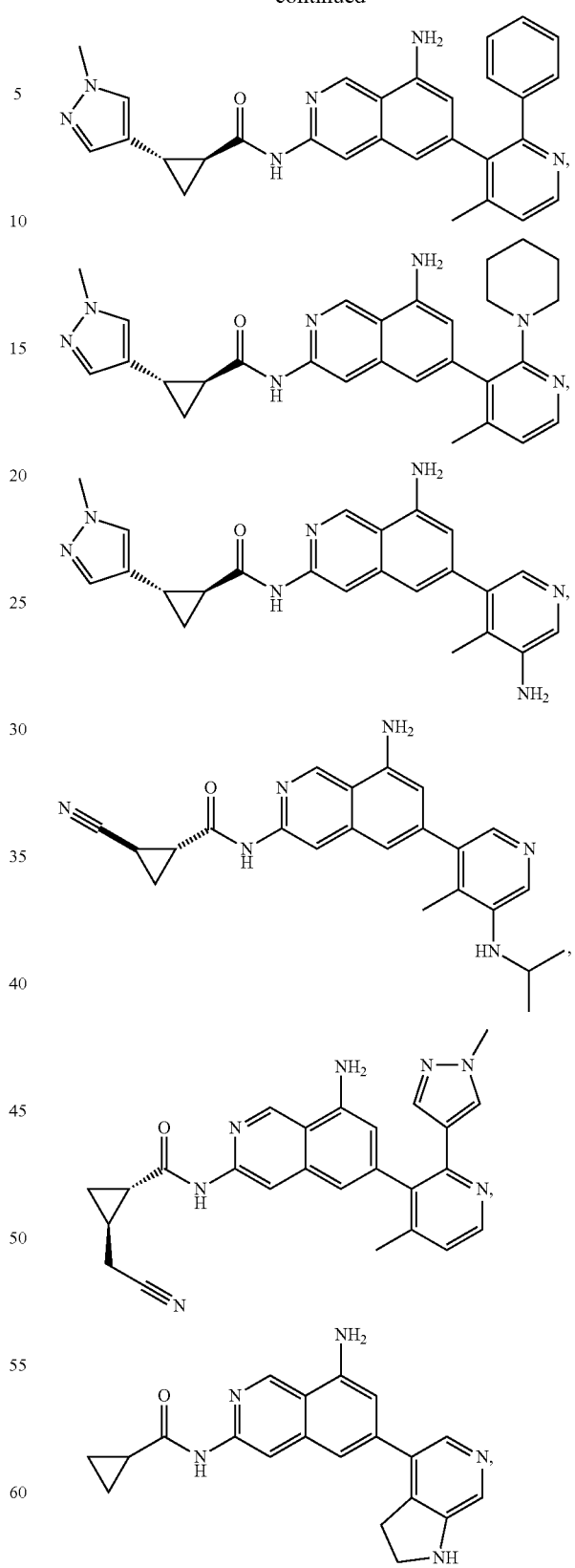

73
-continued
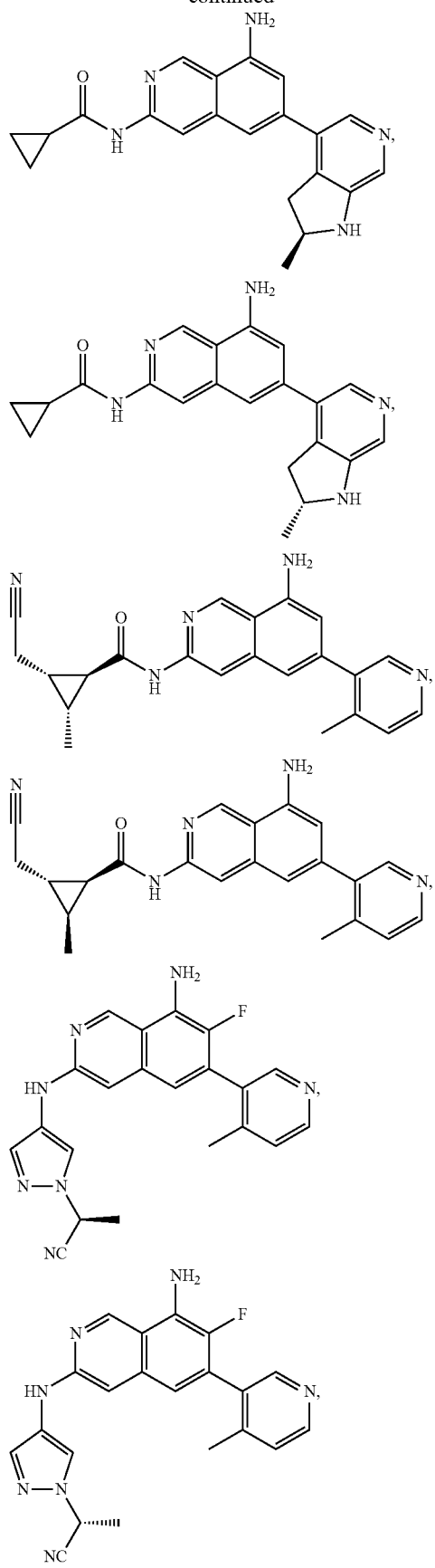
74
-continued
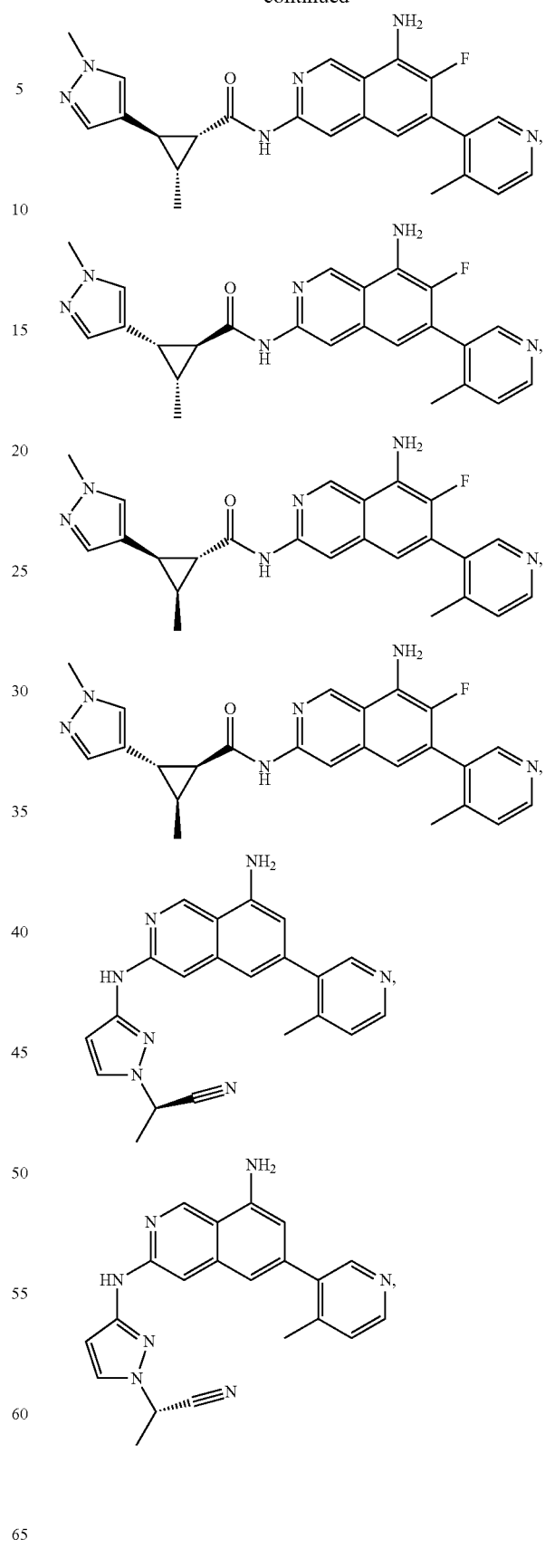

75
-continued
76
-continued
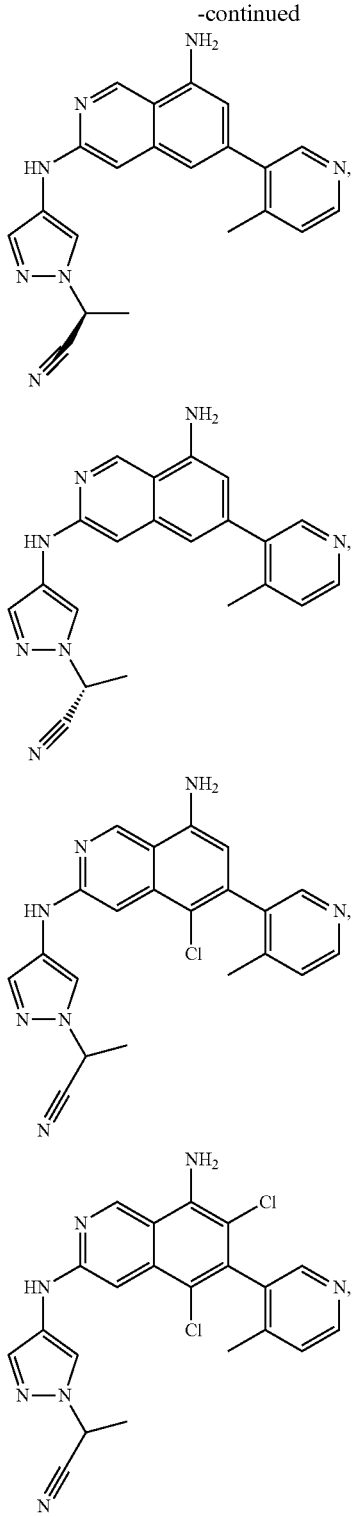
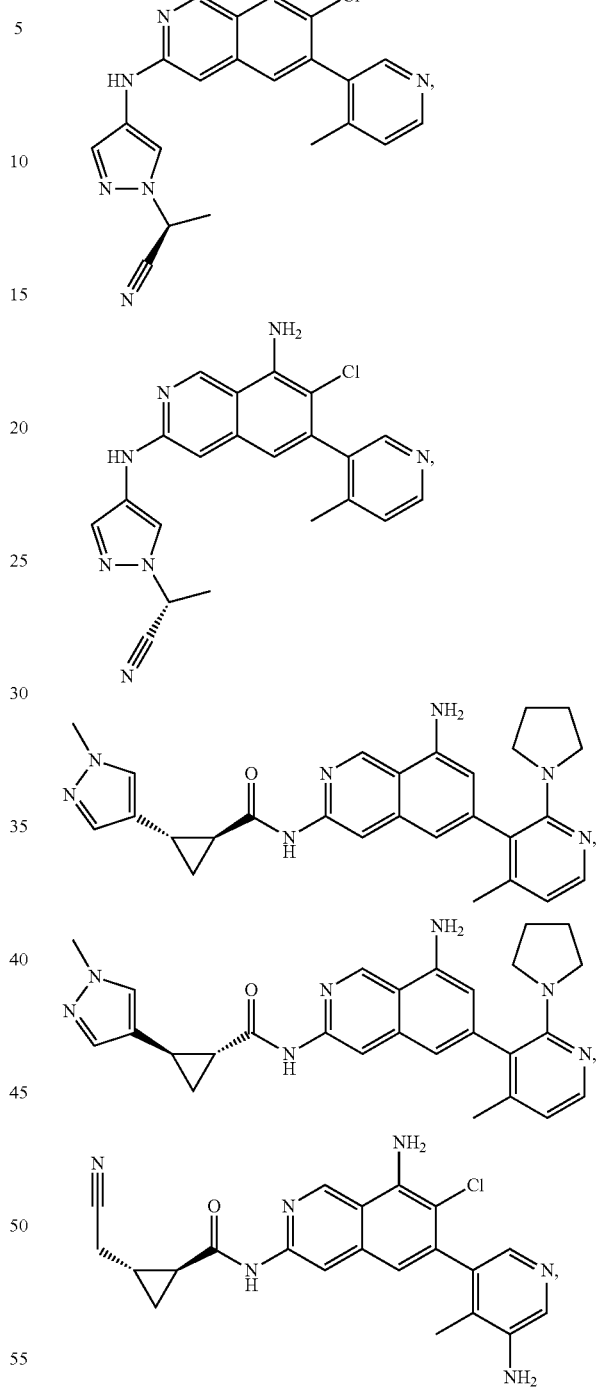

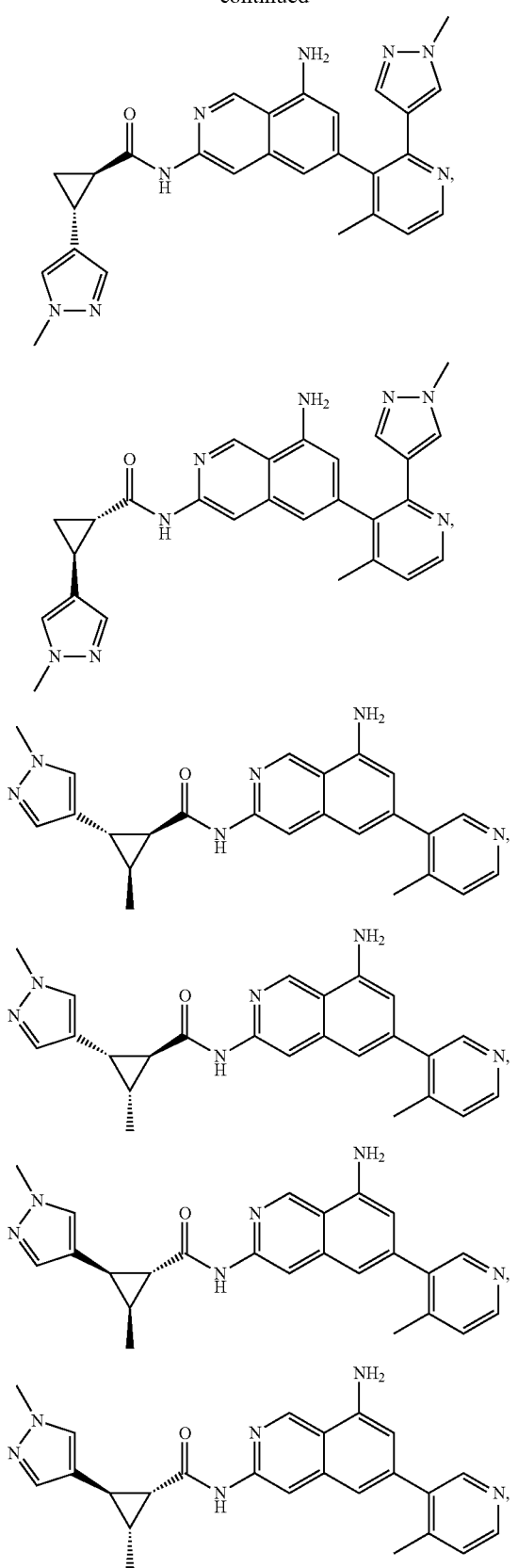
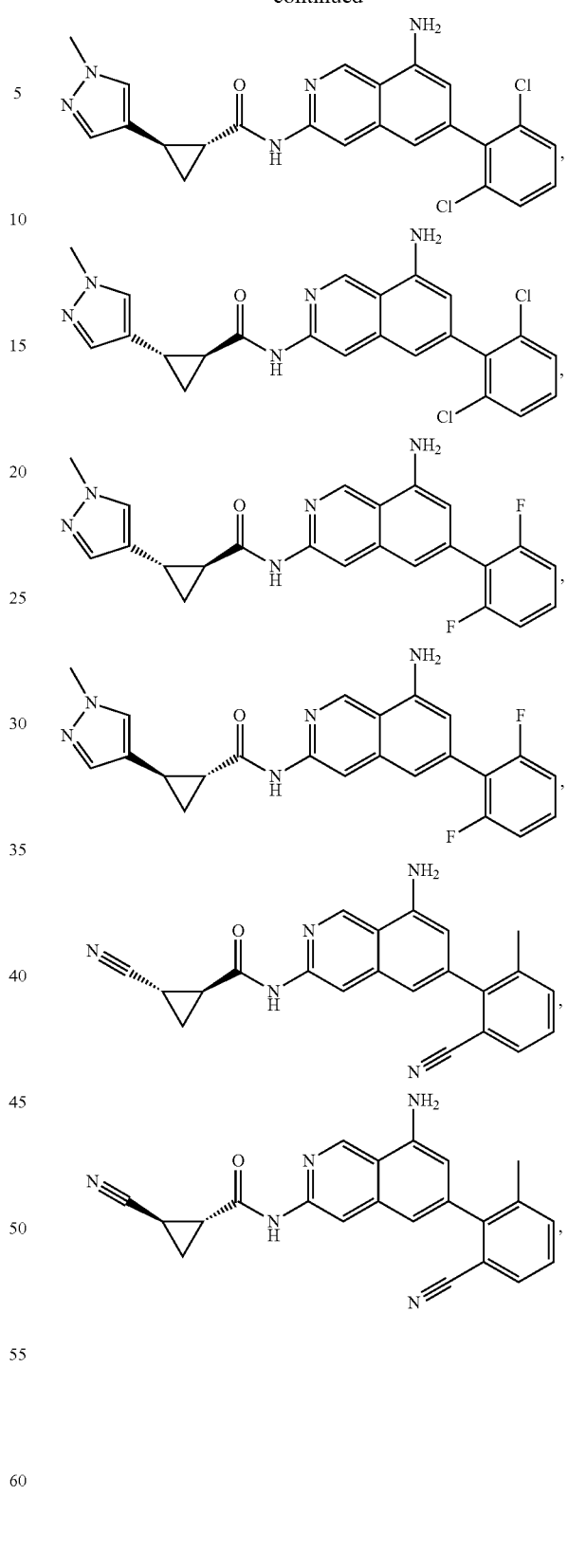

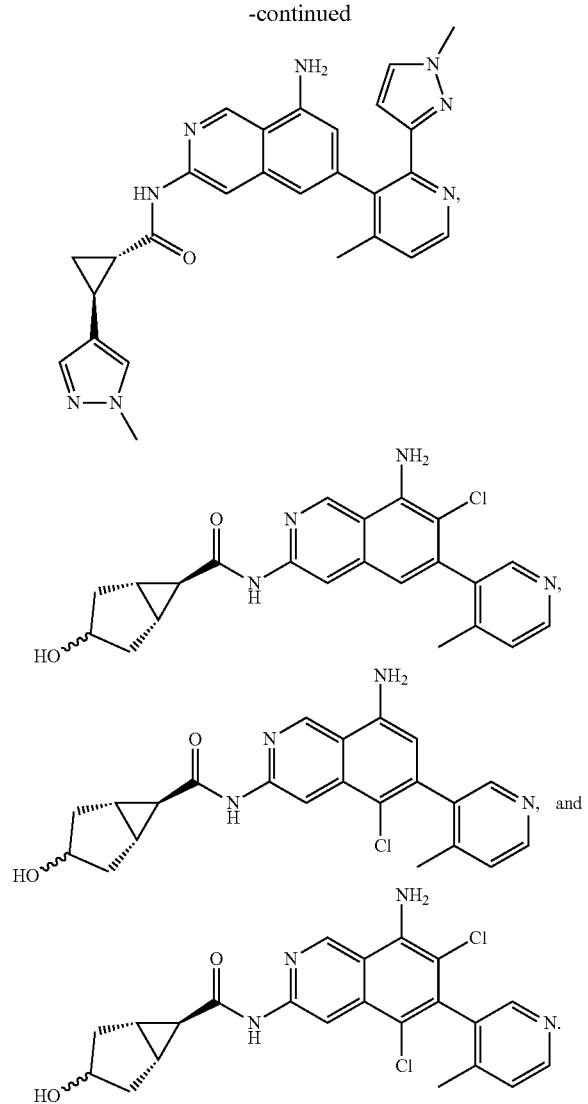

In an embodiment, where all other variables are as defined in any embodiment above, provided are compounds including any of compound numbers 1, 2, 3, 4, 5, 6, 7, 8, 13, 14, 15, 16, 17, 18, 19, 20, 21, 22, 23, 24, 25, 26, 27, 28, 30, 31, 32, 37, 38, 39, 40, 41, 42, 43, 44, 45, 46, 47, 48, 49, 50, 51, 52, 54, 55, 56, 57, 59, 60, 61, 62, 63, 65, 66, 67, 68, 69, 70, 71, 72, 73, 74, 75, 76, 77, 78, 79, 80, 81, 82, 85, 86, 87, 88, 89, 90, 91, 92, 93, 94, 95, 96, 97, 98, 99, 100, 101, 102, 103, 104, 105, 106, 107, 108, 109, 110, 113, 115, 116, 117, 118, 119, 122, 123, 124, 125, 126, 127, 128, 130, 131, 132, 133, 134, 135, 136, 137, 138, 139, 140, 143, 144, 145, 146, 147, 148, 149, 150, 151, 153, 154, 155, 156, 157, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, and 226.

In some embodiments, the disclosure provides a compound of formula I or Ia, or a pharmaceutically acceptable salt thereof, wherein the compound is selected from the group consisting of one or more compounds in Table 1, Table 2 and/or Table 3. In some embodiments, the compound is selected from Compound Nos. 9-12, 29, 33-36, 53, 58, 64, 83, 84, 96, 97, 111, 112, 114, 120, 121, 129, 137, 141, 142, 152 and 158 in Table 1, or a pharmaceutically acceptable salt thereof. In some embodiments, the compound is selected from Compound Nos. 231-390 in Table 2, or a pharmaceutically acceptable salt thereof. In some embodiments, the compound is selected from Compound Nos. 391-528 in Table 3, or a pharmaceutically acceptable salt thereof.

TABLE 1

| Compound No. | Structure | Name |
|---|---|---|
| 1 | 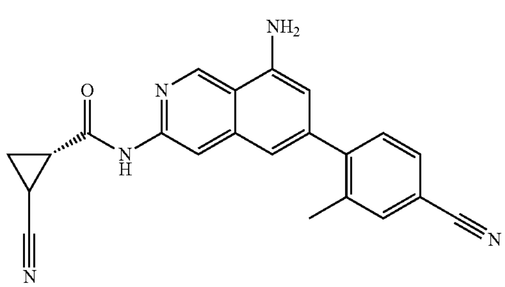 [SMILES: Cc1cc(C#N)ccc1-c1cc(N)c2cnc(NC(=O)[C@H]3CC3C#N)cc2c1] | trans-N-[8-amino-6-(4-cyano-2-methyl-phenyl)-3-isoquinolyl]-2-cyano-cyclopropane-1-carboxamide |

TABLE 1-continued

| Compound No. | Structure | Name |
|---|---|---|
| 2 | 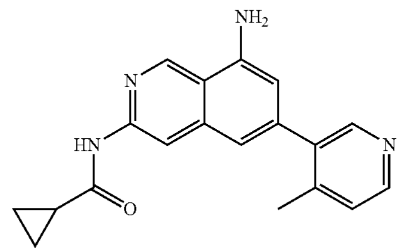 [SMILES: Cc1ccncc1-c1cc(N)c2cnc(NC(=O)C3CC3)cc2c1] | N-(8-amino-6-(4-methylpyridin-3-yl)isoquinolin-3-yl)cyclopropanecarboxamide |
| 3 | 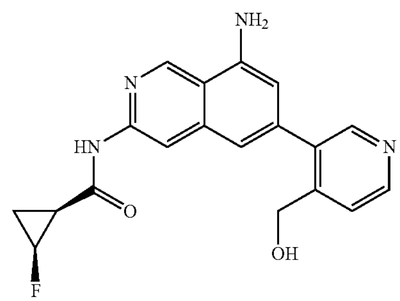 [SMILES: Nc1cc(-c2cnccc2CO)cc2cc(NC(=O)[C@@H]3C[C@@H]3F)ncc12] | cis-N-[8-amino-6-[4-(hydroxymethyl)-3-pyridyl]-3-isoquinolyl]-2-fluoro-cyclopropane-1-carboxamide |
|  | | |
| 4 | 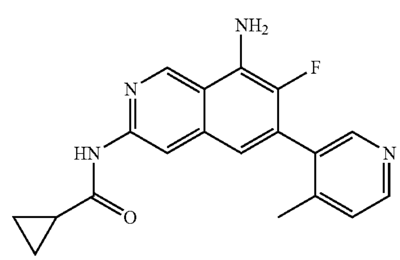 [SMILES: Cc1ccncc1-c1cc2cc(NC(=O)C3CC3)ncc2c(N)c1F] | N-(8-amino-7-fluoro-6-(4-methylpyridin-3-yl)isoquinolin-3-yl)cyclopropanecarboxamide |
| 5 | 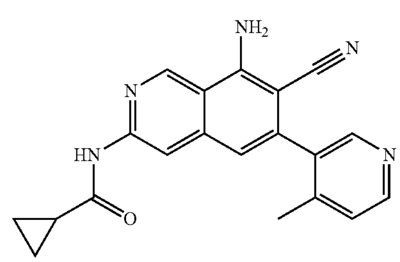 [SMILES: Cc1ccncc1-c1cc2cc(NC(=O)C3CC3)ncc2c(N)c1C#N] | N-(8-amino-7-cyano-6-(4-methylpyridin-3-yl)isoquinolin-3-yl)cyclopropanecarboxamide |

TABLE 1-continued
| Compound No. | Structure | Name |
|---|---|---|
| 6 | 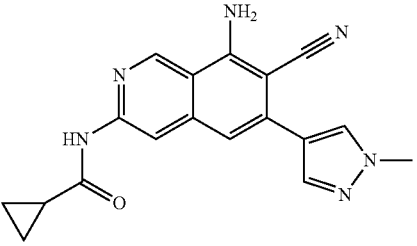 [SMILES: Cn1cc(-c2cc3cc(NC(=O)C4CC4)ncc3c(N)c2C#N)cn1] | N-(8-amino-7-cyano-6-(1-methyl-1H-pyrazol-4-yl)isoquinolin-3-yl)cyclopropanecarboxamide |
| 7 | 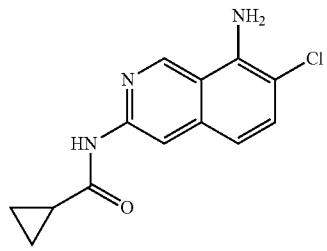 [SMILES: Nc1c(Cl)ccc2cc(NC(=O)C3CC3)ncc12] | N-(8-amino-7-chloroisoquinolin-3-yl)cyclopropanecarboxamide |
| 8 | 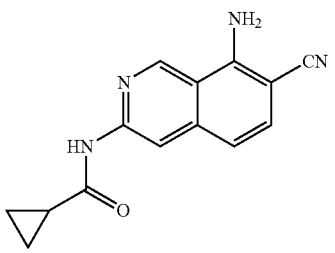 [SMILES: N#Cc1ccc2cc(NC(=O)C3CC3)ncc2c1N] | N-(8-amino-7-cyanoisoquinolin-3-yl)cyclopropanecarboxamide |
| 13 | 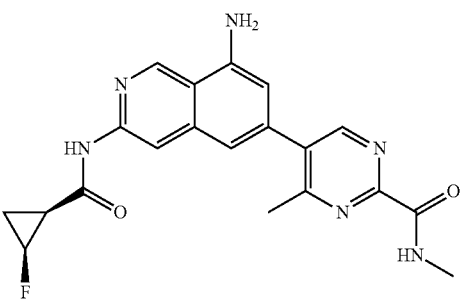 [SMILES: CNC(=O)c1ncc(-c2cc(N)c3cnc(NC(=O)[C@@H]4C[C@@H]4F)cc3c2)c(C)n1]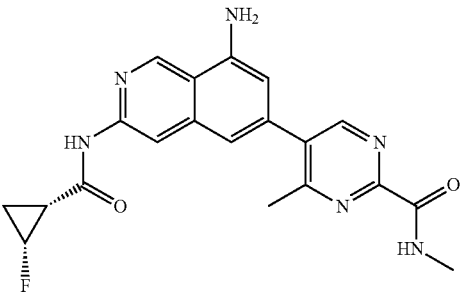 [SMILES: CNC(=O)c1ncc(-c2cc(N)c3cnc(NC(=O)[C@H]4C[C@H]4F)cc3c2)c(C)n1] | 5-[8-amino-3-[(cis-2-fluorocyclopropanecarbonyl)amino]-6-isoquinolyl]-N,4-dimethyl-pyrimidine-2-carboxamide |

TABLE 1-continued

| Compound No. | Structure | Name |
|---|---|---|
| 14 | 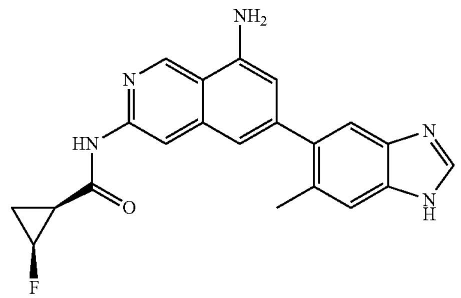 [SMILES: Cc1cc2[nH]cnc2cc1-c1cc(N)c2cnc(NC(=O)[C@@H]3C[C@@H]3F)cc2c1] | cis-N-(8-amino-6-(6-methyl-1H-benzo[d]imidazol-5-yl)isoquinolin-3-yl)-2-fluorocyclopropane-1-carboxamide |
| | | |
| 15 | 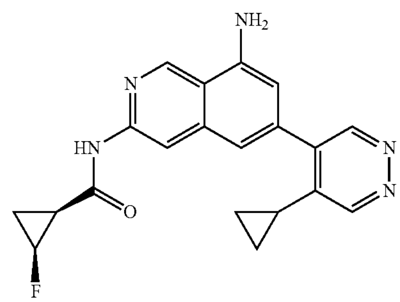 | cis-N-(8-amino-6-(5-cyclopropylpyridazin-4-yl)isoquinolin-3-yl)-2-fluorocyclopropane-1-carboxamide |
| | | |
| 16 | 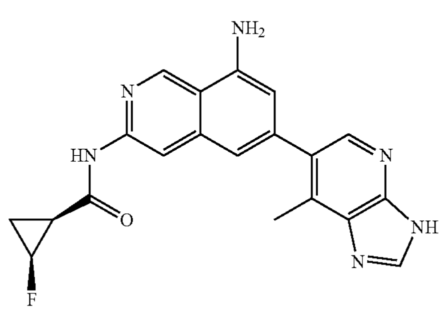 [SMILES: Cc1c(-c2cc(N)c3cnc(NC(=O)[C@@H]4C[C@@H]4F)cc3c2)cnc2[nH]cnc12] | cis-N-(8-amino-6-(7-methyl-3H-imidazo[4,5-b]pyridin-6-yl)isoquinolin-3-yl)-2-fluorocyclopropane-1-carboxamide |

TABLE 1-continued

| Compound No. | Structure | Name |
|---|---|---|
| 17 | 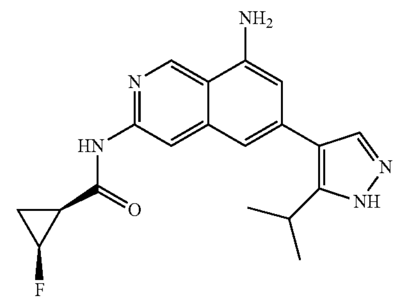 [SMILES: CC(C)c1[nH]ncc1-c1cc(N)c2cnc(NC(=O)[C@@H]3C[C@@H]3F)cc2c1] | cis-N-(8-amino-6-(5-isopropyl-1H-pyrazol-4-yl)isoquinolin-3-yl)-2-fluorocyclopropane-1-carboxamide |
| 18 | 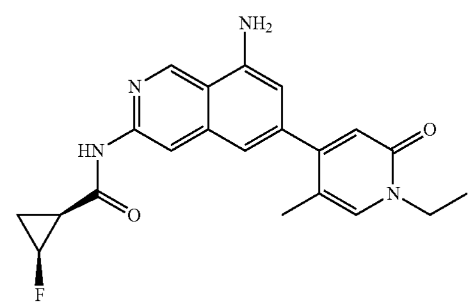 [SMILES: CCn1cc(C)c(-c2cc(N)c3cnc(NC(=O)[C@@H]4C[C@@H]4F)cc3c2)cc1=O] | cis-N-(8-amino-6-(1-ethyl-5-methyl-2-oxo-1,2-dihydropyridin-4-yl)isoquinolin-3-yl)-2-fluorocyclopropane-1-carboxamide |

TABLE 1-continued
| Compound No. | Structure | Name |
|---|---|---|
| 19 | 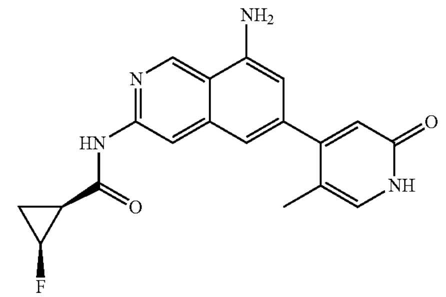 [SMILES: Cc1c[nH]c(=O)cc1-c1cc(N)c2cnc(NC(=O)[C@@H]3C[C@@H]3F)cc2c1]  | cis-N-(8-amino-6-(5-methyl-2-oxo-1,2-dihydropyridin-4-yl)isoquinolin-3-yl)-2-fluorocyclopropane-1-carboxamide |
| 20 | 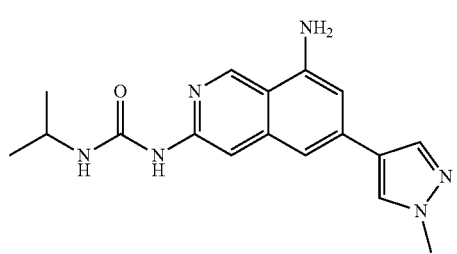 [SMILES: CC(C)NC(=O)Nc1cc2cc(-c3cnn(C)c3)cc(N)c2cn1] | 1-(8-amino-6-(1-methyl-1H-pyrazol-4-yl)isoquinolin-3-yl)-3-isopropylurea |
| 21 | 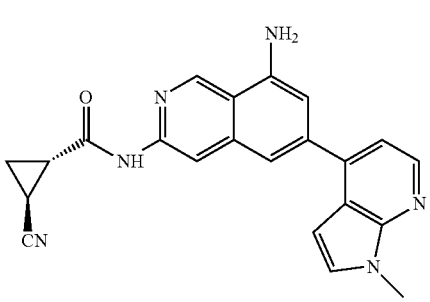 [SMILES: Cn1ccc2c(-c3cc(N)c4cnc(NC(=O)[C@H]5C[C@@H]5C#N)cc4c3)ccnc21] 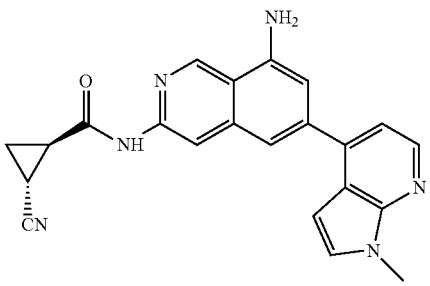 [SMILES: Cn1ccc2c(-c3cc(N)c4cnc(NC(=O)[C@@H]5C[C@H]5C#N)cc4c3)ccnc21] | trans--N-[8-amino-6-[1-methylpyrrolo[2,3-b]pyridin-4-yl)-3-isoquinolyl]-2-cyano-cyclopropane-1-carboxamide |

TABLE 1-continued

| Compound No. | Structure | Name |
|---|---|---|
| 22 | 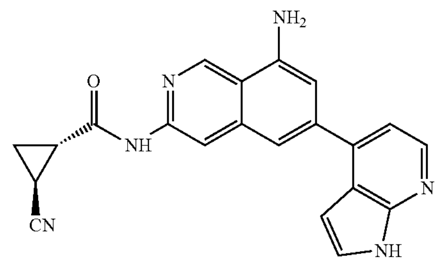 [SMILES: N#C[C@H]1C[C@@H]1C(=O)Nc1cc2cc(-c3ccnc4[nH]ccc34)cc(N)c2cn1] | trans-N-[8-amino-6-(1H-pyrrolo[2,3-b]pyridin-4-yl)-3-isoquinolyl]-2-cyano-cyclopropane-1-carboxamide |
| | | trans-N-[8-amino-6-(1H-pyrrolo[2,3-b]pyridin-4-yl)-3-isoquinolyl]-2-cyano-cyclopropane-1-carboxamide |
| 23 | 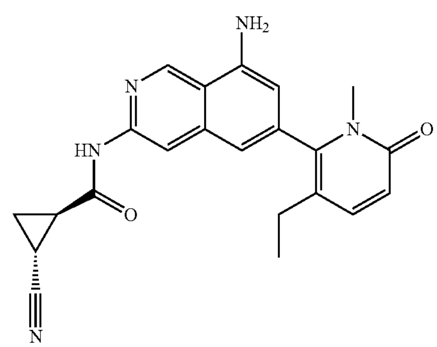 [SMILES: CCc1ccc(=O)n(C)c1-c1cc(N)c2cnc(NC(=O)[C@@H]3C[C@H]3C#N)cc2c1] | trans-N-[8-amino-6-(3-ethyl-1-methyl-6-oxo-2-pyridyl)-3-isoquinolyl]-2-cyano-cyclopropane-1-carboxamide |
| | | |
| 24 | 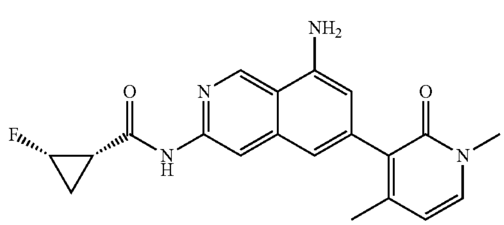 [SMILES: Cc1ccn(C)c(=O)c1-c1cc(N)c2cnc(NC(=O)[C@@H]3C[C@@H]3F)cc2c1] | cis-N-[8-amino-6-(1,4-dimethyl-2-oxo-3-pyridyl)-3-isoquinolyl]-2-fluoro-cyclopropane-1-carboxamide |

TABLE 1-continued

| Compound No. | Structure | Name |
|---|---|---|
| | | |
| 25 | 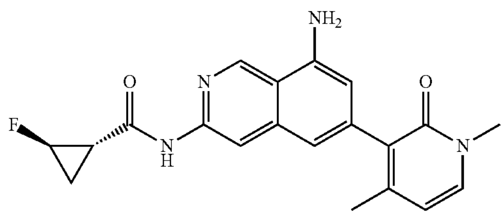 [SMILES: Cc1ccn(C)c(=O)c1-c1cc(N)c2cnc(NC(=O)[C@@H]3C[C@H]3F)cc2c1] | trans-N-[8-amino-6-(1,4-dimethyl-2-oxo-3-pyridyl)-3-isoquinolyl]-2-fluoro-cyclopropane-1-carboxamide |
| 26 | 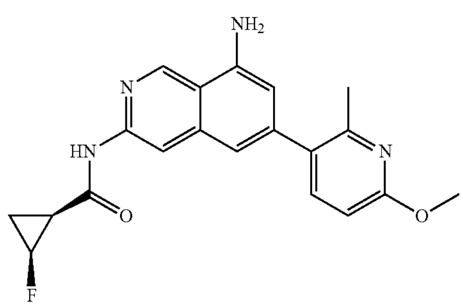 [SMILES: COc1ccc(-c2cc(N)c3cnc(NC(=O)[C@@H]4C[C@@H]4F)cc3c2)c(C)n1] | cis-N-(8-amino-6-(6-methoxy-2-methylpyridin-3-yl)isoquinolin-3-yl)-2-fluorocyclopropane-1-carboxamide |
| 27 | 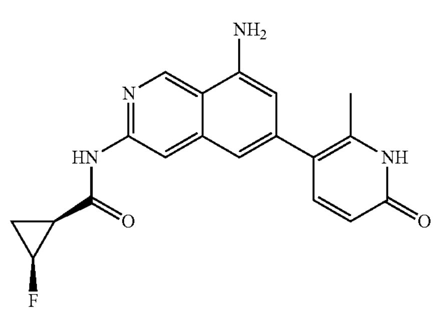 [SMILES: Cc1[nH]c(=O)ccc1-c1cc(N)c2cnc(NC(=O)[C@@H]3C[C@@H]3F)cc2c1] | cis-N-(8-amino-6-(2-methyl-6-oxo-1,6-dihydropyridin-3-yl)isoquinolin-3-yl)-2-fluorocyclopropane-1-carboxamide |

TABLE 1-continued

| Compound No. | Structure | Name |
|---|---|---|
| | (structure) | |
| 28 | (structure) | cis-N-(8-amino-6-(5-methyl-1H-pyrazol-4-yl)isoquinolin-3-yl)-2-fluorocyclopropane-1-carboxamide |
| | (structure) | |
| 30 | (structure) | (1S,2S)-N-(8-amino-6-(5-oxopyrrolidin-3-yl)isoquinolin-3-yl)-2-fluorocyclopropane-1-carboxamide |
| 31 | (structure) | cis-N-(8-amino-6-(4-ethyl-6-(hydroxymethyl)pyridin-3-yl)isoquinolin-3-yl)-2-fluorocyclopropane-1-carboxamide |

TABLE 1-continued

| Compound No. | Structure | Name |
|---|---|---|
| | (structure) | |
| 32 | (structure) | trans-N-(8-amino-6-(4-methylpyridin-3-yl)isoquinolin-3-yl)-2-cyanocyclopropane-1-carboxamide |
| | (structure) | |
| 37, 108 | (structure) | (1S,2S)-N-(8-amino-6-(4-methyl-2-oxooxazolidin-3-yl)isoquinolin-3-yl)-2-fluorocyclopropane-1-carboxamide |
| 38 | (structure) | trans-N-(8-amino-6-(quinolin-4-yl)isoquinolin-3-yl)-2-cyanocyclopropane-1-carboxamide |
| | (structure) | |

TABLE 1-continued
| Compound No. | Structure | Name |
|---|---|---|
| 39 | 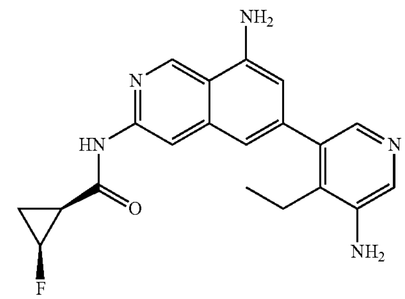 [SMILES: CCc1c(N)cncc1-c1cc(N)c2cnc(NC(=O)[C@@H]3C[C@@H]3F)cc2c1] | cis-N-(8-amino-6-(5-amino-4-ethylpyridin-3-yl)isoquinolin-3-yl)-2-fluorocyclopropane-1-carboxamide |
| 40 | 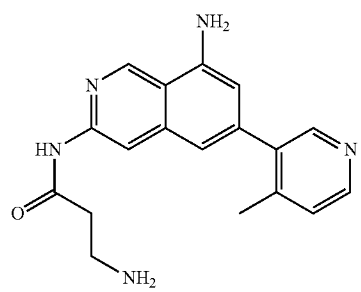 [SMILES: Cc1ccncc1-c1cc(N)c2cnc(NC(=O)CCN)cc2c1] | 3-amino-N-(8-amino-6-(4-methylpyridin-3-yl)isoquinolin-3-yl)propanamide |
| 41 | 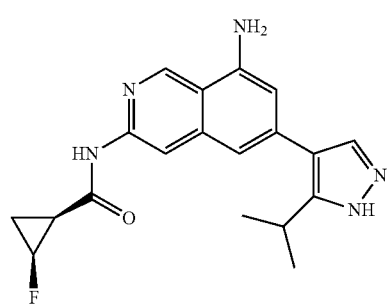 [SMILES: CC(C)c1[nH]ncc1-c1cc(N)c2cnc(NC(=O)[C@@H]3C[C@@H]3F)cc2c1] | cis-N-(8-amino-6-(5-isopropyl-1H-pyrazol-4-yl)isoquinolin-3-yl)-2-fluorocyclopropane-1-carboxamide |

TABLE 1-continued

| Compound No. | Structure | Name |
|---|---|---|
| 42 | 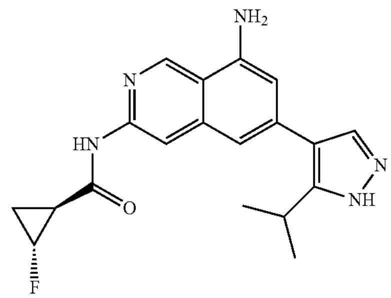 [SMILES: CC(C)c1[nH]ncc1-c1cc(N)c2cnc(NC(=O)[C@@H]3C[C@H]3F)cc2c1] | trans-N-(8-amino-6-(5-isopropyl-1H-pyrazol-4-yl)isoquinolin-3-yl)-2-fluorocyclopropane-1-carboxamide |
| 43 | 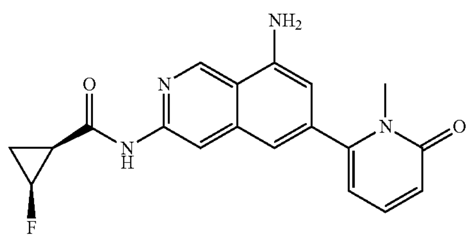 [SMILES: Cn1c(-c2cc(N)c3cnc(NC(=O)[C@@H]4C[C@@H]4F)cc3c2)cccc1=O] | cis-N-(8-amino-6-(1-methyl-6-oxo-1,6-dihydropyridin-2-yl)isoquinolin-3-yl)-2-fluorocyclopropane-1-carboxamide |
| 44 | 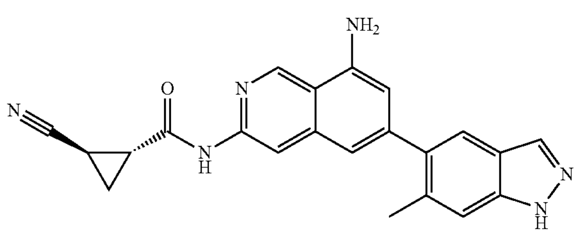 | trans-N-[8-amino-6-(6-methyl-1H-indazol-5-yl)-3-isoquinolyl]-2-cyano-cyclopropane-1-carboxamide |

TABLE 1-continued

| Compound No. | Structure | Name |
|---|---|---|
| 45 | 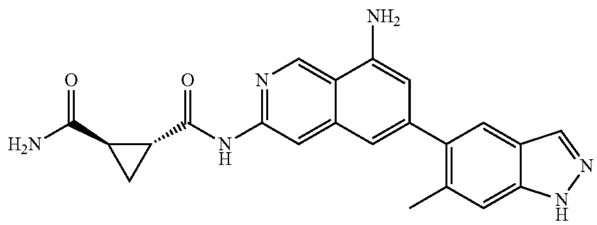 [SMILES: Cc1cc2[nH]ncc2cc1-c1cc(N)c2cnc(NC(=O)[C@@H]3C[C@H]3C(N)=O)cc2c1] | trans-N1-[8-amino-6-(6-methyl-1H-indazol-5-yl)-3-isoquinolyl]cyclopropane-1,2-dicarboxamide |
| 46 | 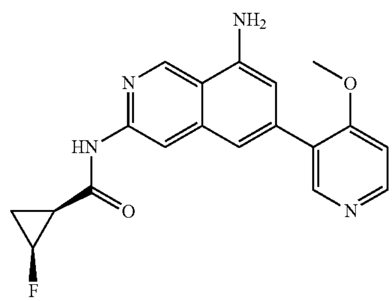 [SMILES: COc1ccncc1-c1cc(N)c2cnc(NC(=O)[C@@H]3C[C@@H]3F)cc2c1] | cis-N-(8-amino-6-(4-methoxypyridin-3-yl)isoquinolin-3-yl)-2-fluorocyclopropane-1-carboxamide |
| 47 | 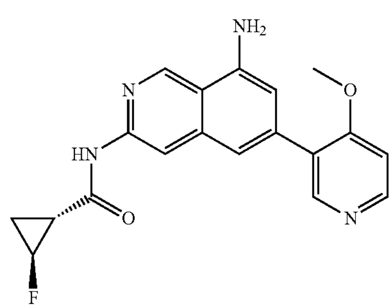 [SMILES: COc1ccncc1-c1cc(N)c2cnc(NC(=O)[C@H]3C[C@@H]3F)cc2c1] | trans-N-(8-amino-6-(4-methoxypyridin-3-yl)isoquinolin-3-yl)-2-fluorocyclopropane-1-carboxamide |

TABLE 1-continued

| Compound No. | Structure | Name |
|---|---|---|
| | (structure) | |
| 48 | (structure) | cis-N-[8-amino-6-(2-hydroxy-4-methyl-3-pyridyl)-3-isoquinolyl]-2-fluoro-cyclopropane-1-carboxamide |
| | (structure) | |
| 49 | (structure) | cis-N-[8-amino-6-(5-fluoro-4-methyl-3-pyridyl)-3-isoquinolyl]-2-fluoro-cyclopropane-1-carboxamide |
| | (structure) | |
| 50 | (structure) | cis-N-[8-amino-6-(3-pyridyl)-3-isoquinolyl]-2-fluoro-cyclopropane-1-carboxamide |

TABLE 1-continued
| Compound No. | Structure | Name |
|---|---|---|
| 51 | 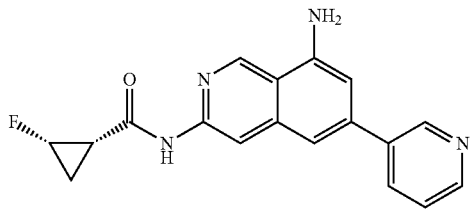 [SMILES: Nc1cc(-c2cccnc2)cc2cc(NC(=O)[C@@H]3C[C@@H]3F)ncc12]<br>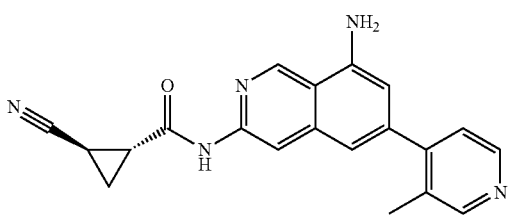 [SMILES: Cc1cnccc1-c1cc(N)c2cnc(NC(=O)[C@@H]3C[C@H]3C#N)cc2c1] | trans-N-[8-amino-6-(3-methyl-4-pyridyl)-3-isoquinolyl]-2-cyano-cyclopropane-1-carboxamide |
| 52, 102 | 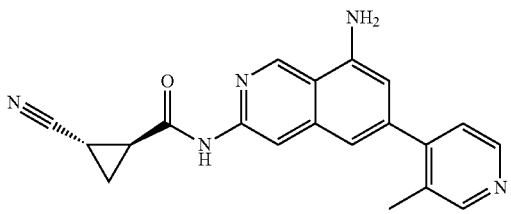 [SMILES: Cc1cnccc1-c1cc(N)c2cnc(NC(=O)[C@H]3C[C@@H]3C#N)cc2c1]<br>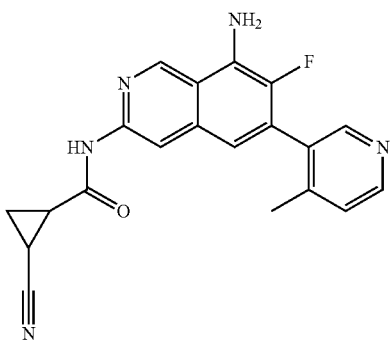 [SMILES: Cc1ccncc1-c1cc2cc(NC(=O)C3CC3C#N)ncc2c(N)c1F]<br>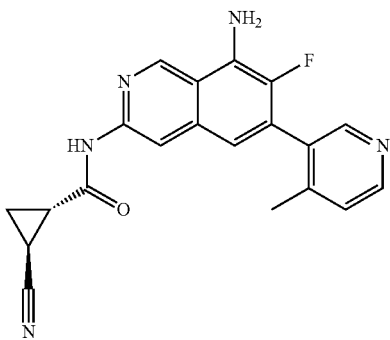 [SMILES: Cc1ccncc1-c1cc2cc(NC(=O)[C@H]3C[C@@H]3C#N)ncc2c(N)c1F] | trans-N-[8-amino-7-fluoro-6-(4-methyl-3-pyridyl)-3-isoquinolyl]-2-cyano-cyclopropane-1-carboxamide |

TABLE 1-continued

| Compound No. | Structure | Name |
|---|---|---|
| 54, 92, 93 | 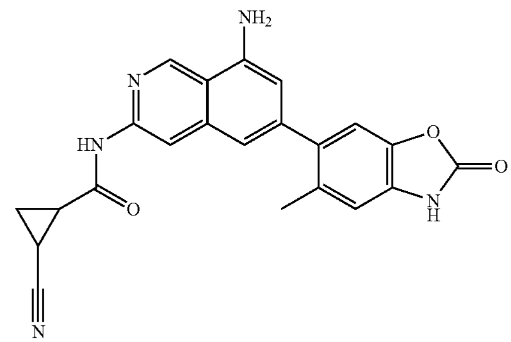 [SMILES: Cc1cc2[nH]c(=O)oc2cc1-c1cc(N)c2cnc(NC(=O)C3CC3C#N)cc2c1] | trans-N-(8-amino-6-(5-methyl-2-oxo-2,3-dihydrobenzo[d]oxazol-6-yl)isoquinolin-3-yl)-2-cyanocyclopropane-1-carboxamide |

TABLE 1-continued
| Compound No. | Structure | Name |
|---|---|---|
| 55 | 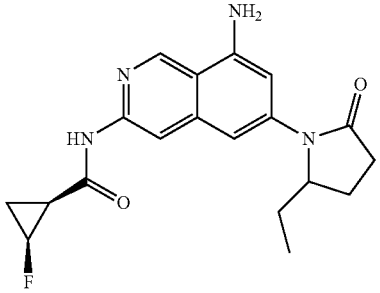 [SMILES: CCC1CCC(=O)N1c1cc(N)c2cnc(NC(=O)[C@@H]3C[C@@H]3F)cc2c1] | cis-N-(8-amino-6-(2-ethyl-5-oxopyrrolidin-1-yl)isoquinolin-3-yl)-2-fluorocyclopropane-1-carboxamide |
| | 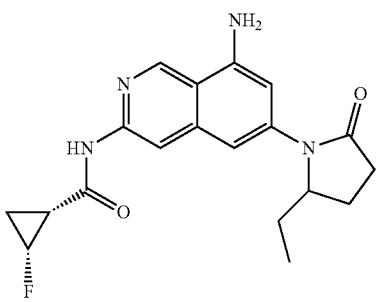 [SMILES: CCC1CCC(=O)N1c1cc(N)c2cnc(NC(=O)[C@H]3C[C@H]3F)cc2c1] | |
| 56 | 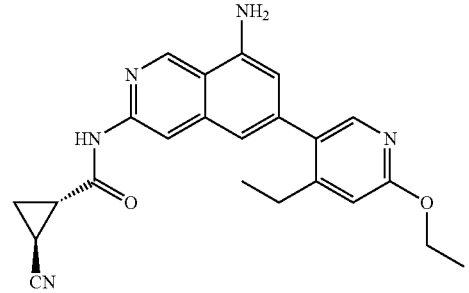 [SMILES: CCOc1cc(CC)c(-c2cc(N)c3cnc(NC(=O)[C@H]4C[C@@H]4C#N)cc3c2)cn1] | trans-N-(8-amino-6-(4-ethylpyridin-3-yl)-2,7-naphthyridin-3-yl)-2-cyanocyclopropane-1-carboxamide |
| | 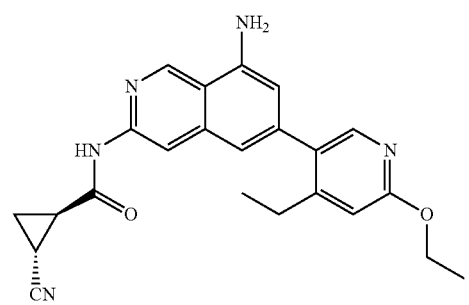 [SMILES: CCOc1cc(CC)c(-c2cc(N)c3cnc(NC(=O)[C@@H]4C[C@H]4C#N)cc3c2)cn1] | |
| 57 | 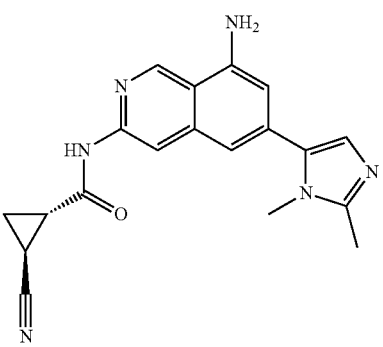 [SMILES: Cc1ncc(-c2cc(N)c3cnc(NC(=O)[C@H]4C[C@@H]4C#N)cc3c2)n1C] | trans-N-(8-amino-6-(1,2-dimethyl-1H-imidazol-5-yl)isoquinolin-3-yl)-2-cyanocyclopropane-1-carboxamide |

TABLE 1-continued

| Compound No. | Structure | Name |
|---|---|---|
| 59 | | cis-N-[8-amino-6-(3-methyl-4-pyridyl)-3-isoquinolyl]-2-fluoro-cyclopropane-1-carboxamide |
| 60 | | trans-N-(8-amino-6-(4-(1,1-difluoroethyl)pyridin-3-yl)isoquinolin-3-yl)-2-cyanocyclopropane-1-carboxamide |

TABLE 1-continued

| Compound No. | Structure | Name |
|---|---|---|
| 61 | 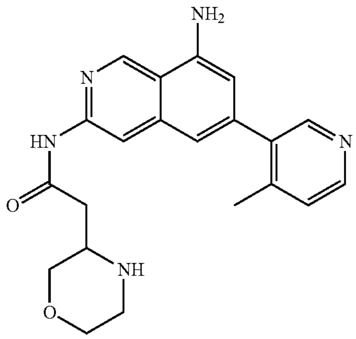 [SMILES: Cc1ccncc1-c1cc(N)c2cnc(NC(=O)CC3COCCN3)cc2c1] | N-(8-amino-6-(4-methylpyridin-3-yl)isoquinolin-3-yl)-2-(morpholin-3-yl)acetamide |
| 62 | 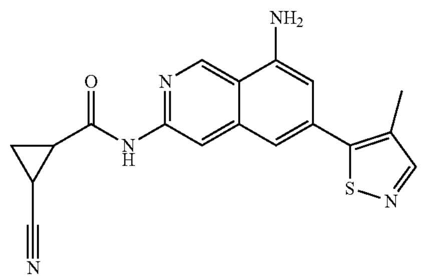 [SMILES: Cc1cnsc1-c1cc(N)c2cnc(NC(=O)C3CC3C#N)cc2c1] | trans-N-(8-amino-6-(4-methylisothiazol-5-yl)isoquinolin-3-yl)-2-cyanocyclopropanec-1-arboxamide |
| | | |
| | | |
| 63 | 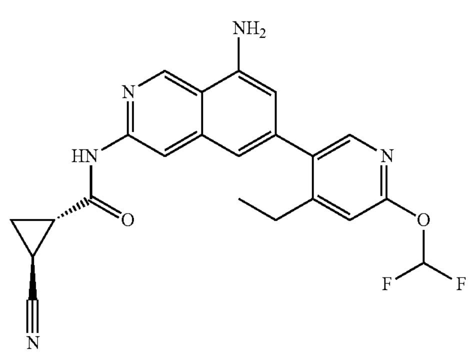 | trans-N-[8-amino-6-[6-(difluoromethoxy)-4-ethyl-3-pyridyl]-3-isoquinolyl]-2-cyanocyclopropane-1-carboxamide |

TABLE 1-continued

| Compound No. | Structure | Name |
|---|---|---|
| | | |
| 65, 94, 95 | 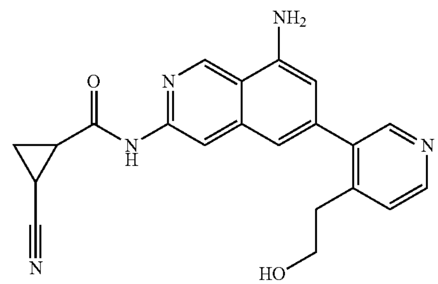 [SMILES: N#CC1CC1C(=O)Nc1cc2cc(-c3cnccc3CCO)cc(N)c2cn1] | trans-N-[8-amino-6-[4-(2-hydroxyethyl)-3-pyridyl]-3-isoquinolyl]-2-cyanocyclopropane-1-carboxamide |
| 66 | 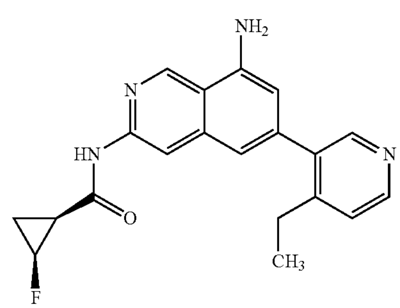 | (1S,2S)-N-(8-amino-6-(4-ethylpyridin-3-yl)isoquinolin-3-yl)-2-fluorocyclopropane-1-carboxamide |

TABLE 1-continued

| Compound No. | Structure | Name |
|---|---|---|
| 67, 71, 72 | 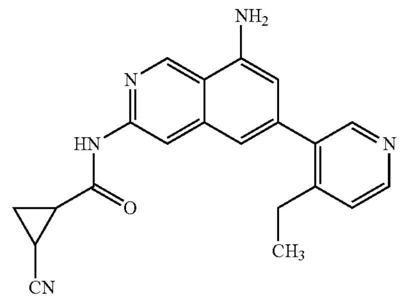 [SMILES: CCc1ccncc1-c1cc(N)c2cnc(NC(=O)C3CC3C#N)cc2c1] | trans-N-(8-amino-6-(4-ethylpyridin-3-yl)isoquinolin-3-yl)-2-cyanocyclopropane-1-carboxamide |
| | | |
| | | |
| 68 | 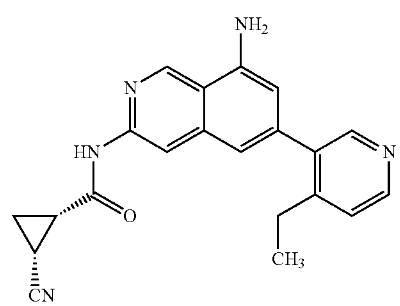 [SMILES: CCc1ccncc1-c1cc(N)c2cnc(NC(=O)[C@H]3C[C@H]3C#N)cc2c1] | cis-N-(8-amino-6-(4-ethylpyridin-3-yl)isoquinolin-3-yl)-2-cyanocyclopropane-1-carboxamide |
| | | |

TABLE 1-continued
| Compound No. | Structure | Name |
|---|---|---|
| 69 | 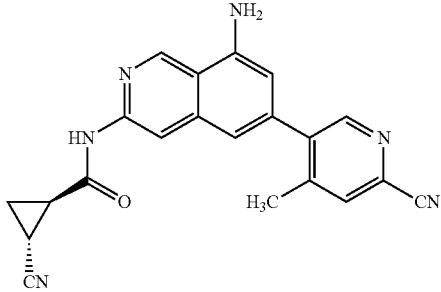 [SMILES: Cc1cc(C#N)ncc1-c1cc(N)c2cnc(NC(=O)[C@@H]3C[C@H]3C#N)cc2c1] | trans-N-(8-amino-6-(6-cyano-4-methylpyridin-3-yl)isoquinolin-3-yl)-2-cyanocyclopropane-1-carboxamide |
|  | 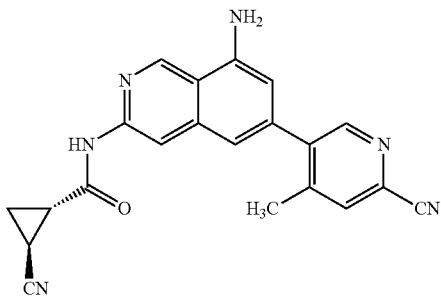 [SMILES: Cc1cc(C#N)ncc1-c1cc(N)c2cnc(NC(=O)[C@H]3C[C@@H]3C#N)cc2c1] |  |
| 70, 107, 123 | 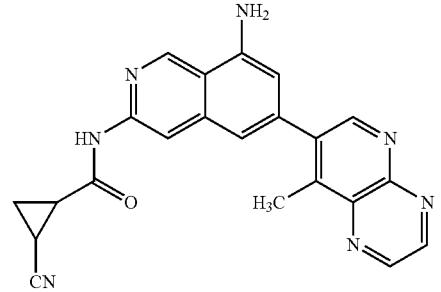 [SMILES: Cc1c(-c2cc(N)c3cnc(NC(=O)C4CC4C#N)cc3c2)cnc2nccnc12] | trans-N-(8-amino-6-(8-methylpyrido[2,3-b]pyrazin-7-yl)isoquinolin-3-yl)-2-cyanocyclopropane-1-carboxamide |
|  | 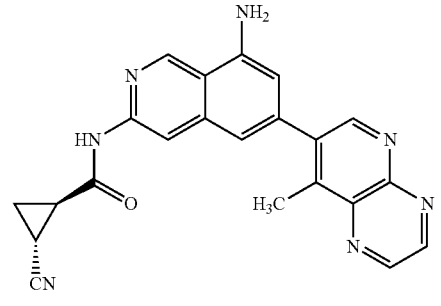 [SMILES: Cc1c(-c2cc(N)c3cnc(NC(=O)[C@@H]4C[C@H]4C#N)cc3c2)cnc2nccnc12] |  |
|  | 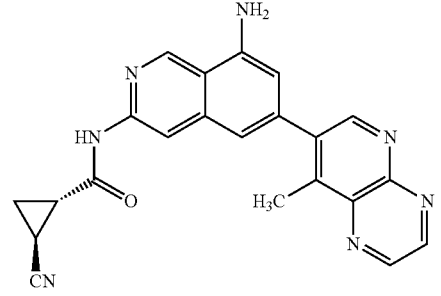 |  |

TABLE 1-continued
| Compound No. | Structure | Name |
|---|---|---|
| 73, 74 | 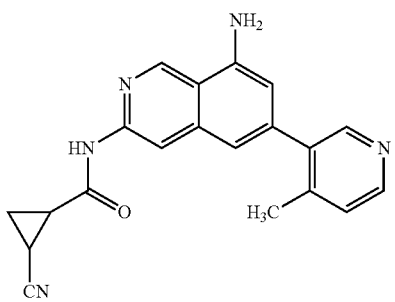 [SMILES: Cc1ccncc1-c1cc(N)c2cnc(NC(=O)C3CC3C#N)cc2c1] 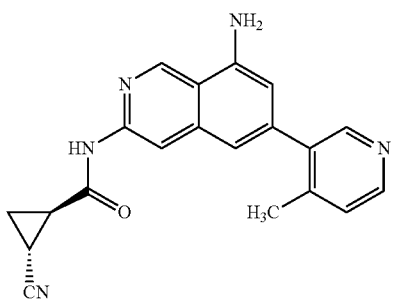 [SMILES: Cc1ccncc1-c1cc(N)c2cnc(NC(=O)[C@@H]3C[C@H]3C#N)cc2c1] 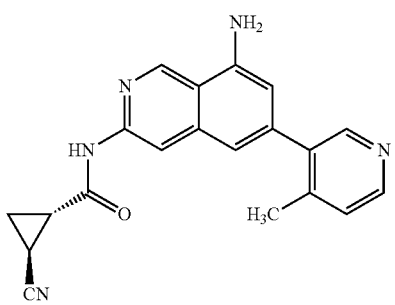 [SMILES: Cc1ccncc1-c1cc(N)c2cnc(NC(=O)[C@H]3C[C@@H]3C#N)cc2c1] | trans-N-(8-amino-6-(4-methylpyridin-3-yl)isoquinolin-3-yl)-2-cyanocyclopropane-1-carboxamide |
| 75, 170 | 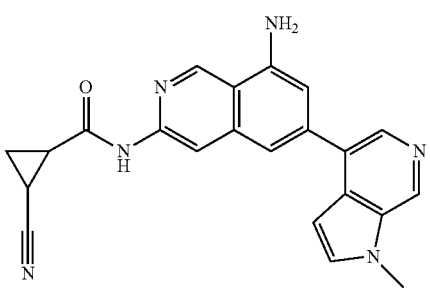 [SMILES: Cn1ccc2c(-c3cc(N)c4cnc(NC(=O)C5CC5C#N)cc4c3)cncc21] 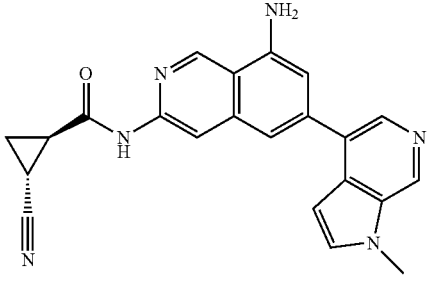 [SMILES: Cn1ccc2c(-c3cc(N)c4cnc(NC(=O)[C@@H]5C[C@H]5C#N)cc4c3)cncc21] | trans-N-(8-amino-6-(1-methyl-1H-pyrrolo[2,3-c]pyridin-4-yl)isoquinolin-3-yl)-2-cyanocyclopropane-1-carboxamide |

125 126
TABLE 1-continued
| Compound No. | Structure | Name |
|---|---|---|
| | 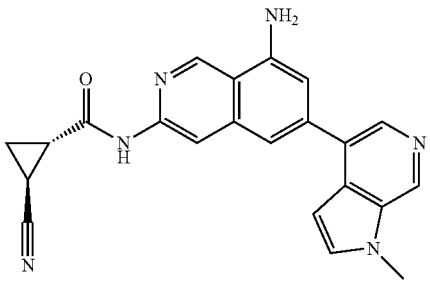 [SMILES: Cn1ccc2c(-c3cc(N)c4cnc(NC(=O)[C@H]5C[C@@H]5C#N)cc4c3)cncc21] | |
| 76, 171 | 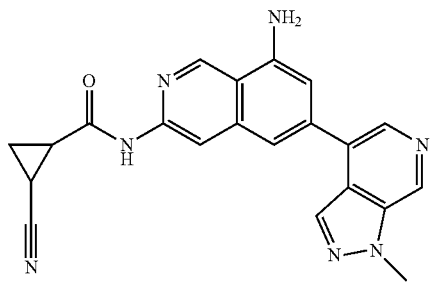 [SMILES: Cn1ncc2c(-c3cc(N)c4cnc(NC(=O)C5CC5C#N)cc4c3)cncc21] | trans-N-(8-amino-6-(1-methyl-1H-pyrazolo[3,4-c]pyridin-4-yl)isoquinolin-3-yl)-2-cyanocyclopropane-1-carboxamide |
| | 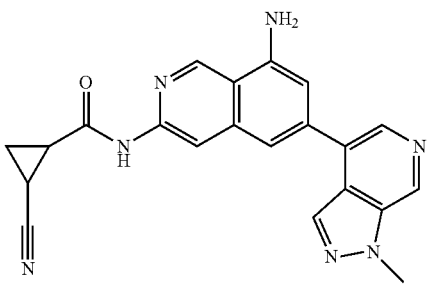 | |
| 77 | 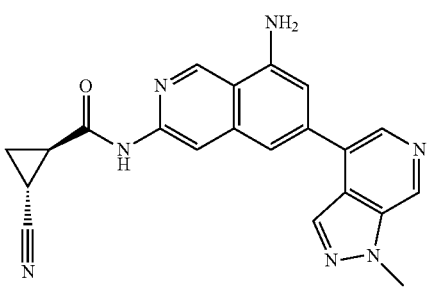 [SMILES: Cn1ncc2c(-c3cc(N)c4cnc(NC(=O)[C@@H]5C[C@H]5C#N)cc4c3)cncc21] | N-(8-amino-6-(4-ethylpyridin-3-yl)isoquinolin-3-yl)-2-(1H-pyrazol-5-yl)acetamide |

TABLE 1-continued

| Compound No. | Structure | Name |
|---|---|---|
| 78, 109 | 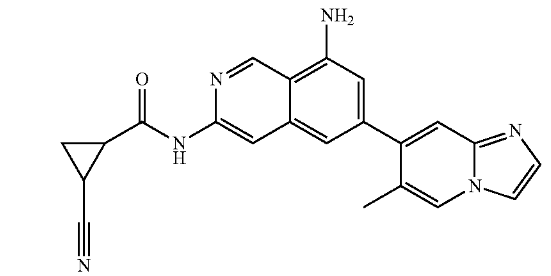 [SMILES: Cc1cn2ccnc2cc1-c1cc(N)c2cnc(NC(=O)C3CC3C#N)cc2c1] | trans-N-(8-amino-6-(6-methylimidazo[1,2-a]pyridin-7-yl)isoquinolin-3-yl)-2-cyanocyclopropane-1-carboxamide |
| 79, 110 | 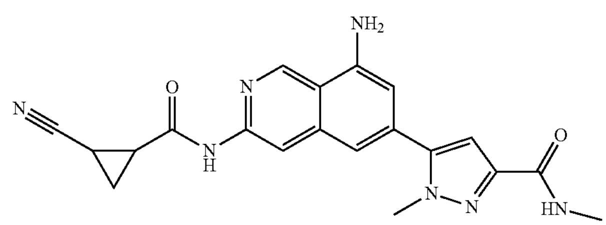 [SMILES: CNC(=O)c1cc(-c2cc(N)c3cnc(NC(=O)C4CC4C#N)cc3c2)n(C)n1] | 5-(8-amino-3-(trans-2-cyanocyclopropane-1-carboxamido)isoquinolin-6-yl)-N,1-dimethyl-1H-pyrazole-3-carboxamide |

TABLE 1-continued

| Compound No. | Structure | Name |
|---|---|---|
| 80, 113 | 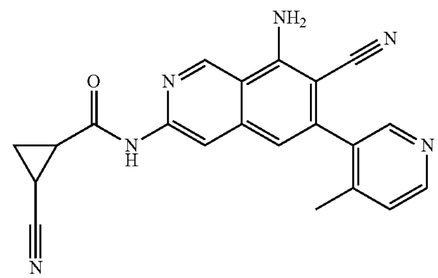 [SMILES: Cc1ccncc1-c1cc2cc(NC(=O)C3CC3C#N)ncc2c(N)c1C#N] | trans-N-[8-amino-7-cyano-6-(4-methyl-3-pyridyl)-3-isoquinolyl]-2-cyanocyclopropane-1-carboxamide |
| 81, 122 | 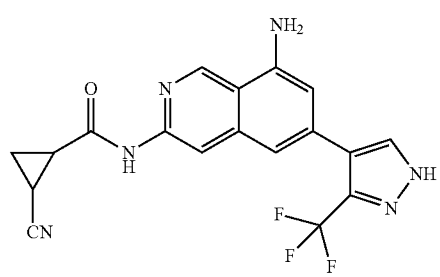 [SMILES: N#CC1CC1C(=O)Nc1cc2cc(-c3c[nH]nc3C(F)(F)F)cc(N)c2cn1] | trans-N-(8-amino-6-(3-(trifluoromethyl)-1H-pyrazol-4-yl)isoquinolin-3-yl)-2-cyanocyclopropane-1-carboxamide |

TABLE 1-continued
| Compound No. | Structure | Name |
|---|---|---|
| 82, 139 | 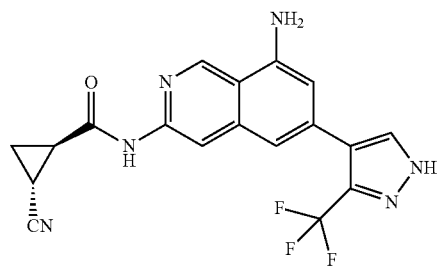 [SMILES: N#C[C@@H]1C[C@H]1C(=O)Nc1cc2cc(-c3c[nH]nc3C(F)(F)F)cc(N)c2cn1] | trans-N-(8-amino-6-(1H-pyrazol-4-yl)isoquinolin-3-yl)-2-cyanocyclopropane-1-carboxamide |
| | 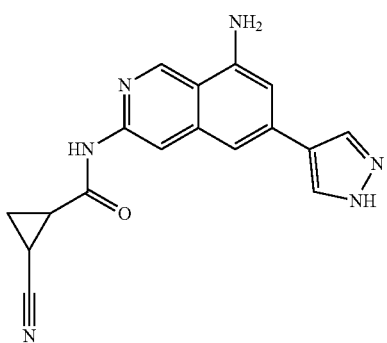 [SMILES: N#CC1CC1C(=O)Nc1cc2cc(-c3cn[nH]c3)cc(N)c2cn1] | |
| | 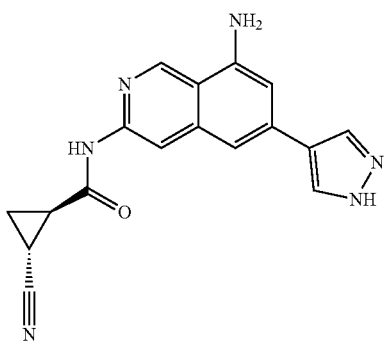 [SMILES: N#C[C@@H]1C[C@H]1C(=O)Nc1cc2cc(-c3cn[nH]c3)cc(N)c2cn1] | |
| | 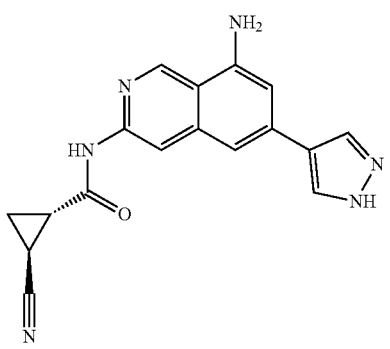 [SMILES: N#C[C@H]1C[C@@H]1C(=O)Nc1cc2cc(-c3cn[nH]c3)cc(N)c2cn1] | |

TABLE 1-continued

| Compound No. | Structure | Name |
|---|---|---|
| 85, 119 | 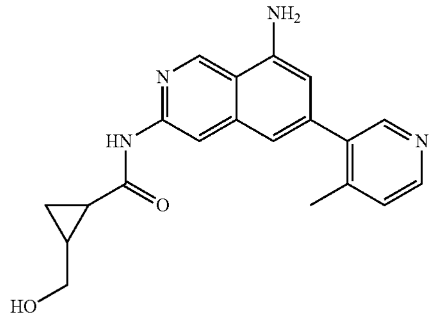 [SMILES: Cc1ccncc1-c1cc(N)c2cnc(NC(=O)C3CC3CO)cc2c1] | trans-N-(8-amino-6-(4-methylpyridin-3-yl)isoquinolin-3-yl)-2-(hydroxymethyl)cyclopropane-1-carboxamide |
| 86, 172 | 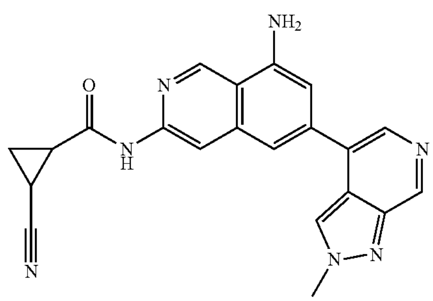 [SMILES: Cn1cc2c(-c3cc(N)c4cnc(NC(=O)C5CC5C#N)cc4c3)cncc2n1] | trans-N-(8-amino-6-(2-methyl-2H-pyrazolo[3,4-c]pyridin-4-yl)isoquinolin-3-yl)-2-cyanocyclopropane-1-carboxamide |

TABLE 1-continued

| Compound No. | Structure | Name |
|---|---|---|
| | (structure) | |
| 87, 117 | (structure) | trans-N-(8-amino-6-(1-methyl-4-oxo-1,4-dihydropyridin-2-yl)isoquinolin-3-yl)-2-cyanocyclopropane-1-carboxamide |
| | (structure) | |
| | (structure) | |
| 88, 115 | (structure) | trans-N-(8-amino-7-methyl-6-(4-methylpyridin-3-yl)isoquinolin-3-yl)-2-cyanocyclopropane-1-carboxamide |
| | (structure) | |

TABLE 1-continued

| Compound No. | Structure | Name |
|---|---|---|
| | | |
| 89, 146 | 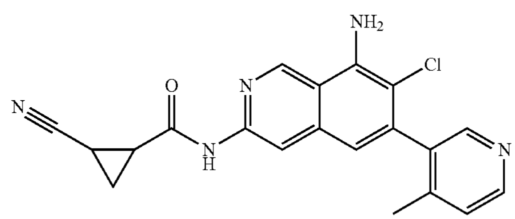 [SMILES: Cc1ccncc1-c1cc2cc(NC(=O)C3CC3C#N)ncc2c(N)c1Cl] | trans-N-(8-amino-7-chloro-6-(4-methylpyridin-3-yl)isoquinolin-3-yl)-2-cyanocyclopropane-1-carboxamide |
| 90, 116 | 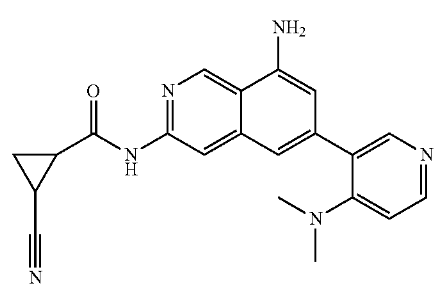 [SMILES: CN(C)c1ccncc1-c1cc(N)c2cnc(NC(=O)C3CC3C#N)cc2c1] | trans-N-(8-amino-6-(4-(dimethylamino)pyridin-3-yl)isoquinolin-3-yl)-2-cyanocyclopropane-1-carboxamide |

TABLE 1-continued

| Compound No. | Structure | Name |
|---|---|---|
| 91, 157 | 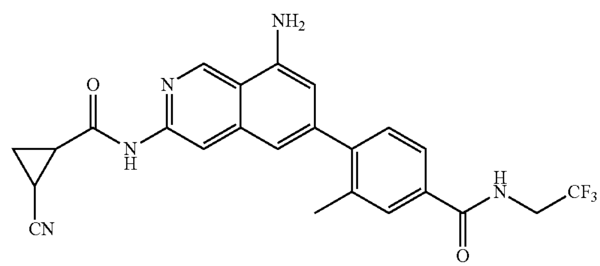 [SMILES: Cc1cc(C(=O)NCC(F)(F)F)ccc1-c1cc(N)c2cnc(NC(=O)C3CC3C#N)cc2c1] | 4-(8-amino-3-(trans-2-cyanocyclopropane-1-carboxamido)isoquinolin-6-yl)-3-methyl-N-(2,2,2-trifluoroethyl)benzamide |
| 98 | 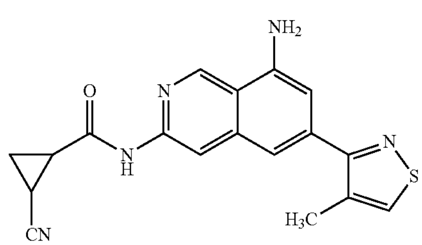 [SMILES: Cc1csnc1-c1cc(N)c2cnc(NC(=O)C3CC3C#N)cc2c1] | N-(8-amino-6-(4-methylisothiazol-3-yl)isoquinolin-3-yl)-2-cyanocyclopropane-1-carboxamide |

TABLE 1-continued

| Compound No. | Structure | Name |
|---|---|---|
| 99, 136 | 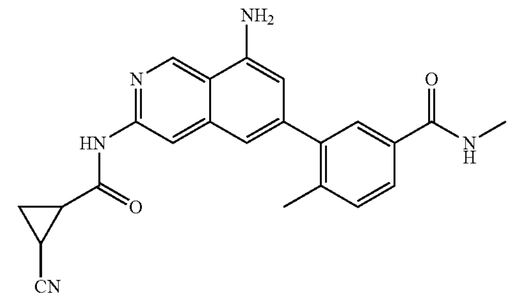 [SMILES: CNC(=O)c1ccc(C)c(-c2cc(N)c3cnc(NC(=O)C4CC4C#N)cc3c2)c1] | 3-(8-amino-3-(trans-2-cyanocyclopropane-1-carboxamido)isoquinolin-6-yl)-N,4-dimethylbenzamide |
| 100, 173 | 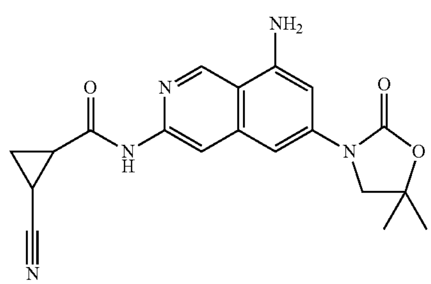 [SMILES: CC1(C)CN(c2cc(N)c3cnc(NC(=O)C4CC4C#N)cc3c2)C(=O)O1] | trans-N-(8-amino-6-(5,5-dimethyl-2-oxooxazolidin-3-yl)isoquinolin-3-yl)-2-cyanocyclopropane-1-carboxamide |

TABLE 1-continued

| Compound No. | Structure | Name |
|---|---|---|
| | (structure) | |
| 101, 174 | (structure) | trans-N-(8-amino-6-((S)-4-isopropyl-2-oxooxazolidin-3-yl)isoquinolin-3-yl)-2-cyanocyclopropane-1-carboxamide |
| | (structure) | |
| | (structure) | |
| 103, 124 | (structure) | trans-N-(8-amino-6-((R)-4-methyl-2-oxooxazolidin-3-yl)isoquinolin-3-yl)-2-cyanocyclopropane-1-carboxamide |

TABLE 1-continued
| Compound No. | Structure | Name |
|---|---|---|
|  | 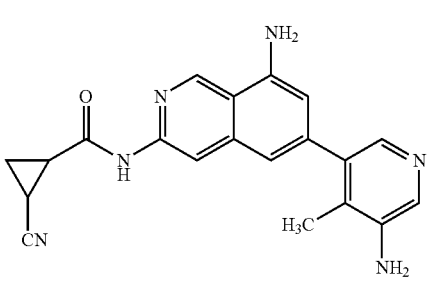 [SMILES: Cc1c(N)cncc1-c1cc(N)c2cnc(NC(=O)C3CC3C#N)cc2c1] |  |
|  | 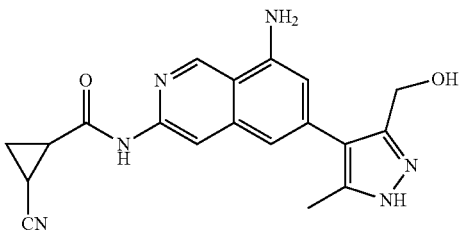 [SMILES: Cc1[nH]nc(CO)c1-c1cc(N)c2cnc(NC(=O)C3CC3C#N)cc2c1] |  |
| 104 | 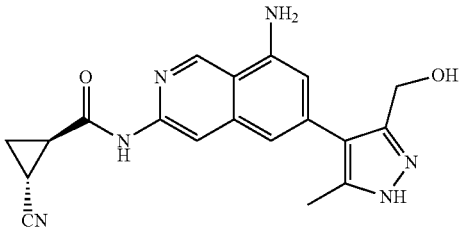 [SMILES: Cc1[nH]nc(CO)c1-c1cc(N)c2cnc(NC(=O)[C@@H]3C[C@H]3C#N)cc2c1] |  |
| 105, 118 | 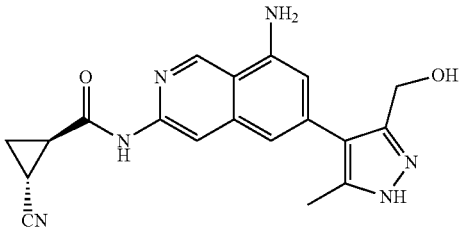 [SMILES: Cc1[nH]nc(CO)c1-c1cc(N)c2cnc(NC(=O)[C@@H]3C[C@H]3C#N)cc2c1] | trans-N-(8-amino-6-(3-(hydroxymethyl)-5-methyl-1H-pyrazol-4-yl)isoquinolin-3-yl)-2-cyanocyclopropane-1-carboxamide |

TABLE 1-continued

| Compound No. | Structure | Name |
|---|---|---|
| | [Structure: 8-amino isoquinoline with cyanocyclopropanecarboxamide and hydroxymethyl-methylpyrazole substituents] | |
| 106, 145 | [Structure: trans-cyanocyclopropane carboxamide with 8-amino-5,7-difluoro-6-(4-methylpyridin-3-yl)isoquinolin-3-yl] | trans-N-(8-amino-5,7-difluoro-6-(4-methylpyridin-3-yl)isoquinolin-3-yl)-2-cyanocyclopropane-1-carboxamide |
| | [Structure: (1S,2S) isomer of the above] | |
| | [Structure: (1R,2R) isomer] | |
| 125 | [Structure: (1S,2S)-2-fluorocyclopropanecarboxamide with 8-amino-6-(2-methyl-5-oxopyrrolidin-1-yl)isoquinolin-3-yl] | (1S,2S)-N-(8-amino-6-(2-methyl-5-oxopyrrolidin-1-yl)isoquinolin-3-yl)-2-fluorocyclopropanecarboxamide |

TABLE 1-continued

| Compound No. | Structure | Name |
|---|---|---|
| 126 | | trans-N-(8-amino-7-fluoro-6-((R)-4-methyl-2-oxooxazolidin-3-yl)isoquinolin-3-yl)-2-cyanocyclopropane-1-carboxamide |
| 127 | | trans-N-(8-amino-6-((S)-4-methyl-2-oxooxazolidin-3-yl)isoquinolin-3-yl)-2-cyanocyclopropane-1-carboxamide |

TABLE 1-continued

| Compound No. | Structure | Name |
|---|---|---|
| 128 | 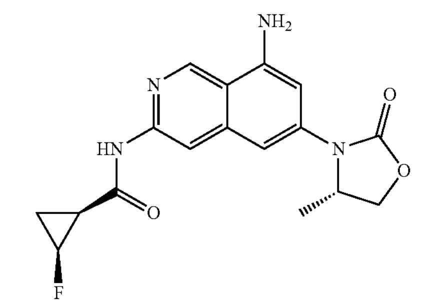 [SMILES: C[C@H]1COC(=O)N1c1cc(N)c2cnc(NC(=O)[C@@H]3C[C@@H]3F)cc2c1] | (1S,2S)-N-(8-amino-6-((S)-4-methyl-2-oxooxazolidin-3-yl)isoquinolin-3-yl)-2-fluorocyclopropane-1-carboxamide |
| 130 | | trans-N-(8-amino-6-(4-methylisothiazol-3-yl)isoquinolin-3-yl)-2-cyanocyclopropane-1-carboxamide |
| | | |
| 131 | 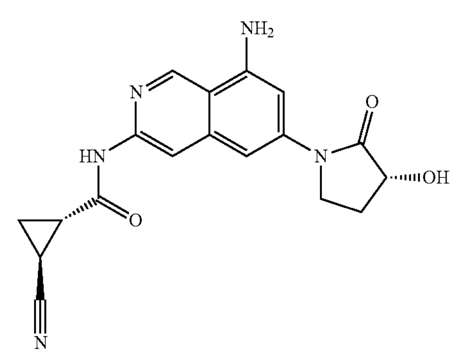 [SMILES: N#C[C@H]1C[C@@H]1C(=O)Nc1cc2cc(N3CC[C@@H](O)C3=O)cc(N)c2cn1] | trans-N-(8-amino-6-((R)-3-hydroxy-2-oxopyrrolidin-1-yl)isoquinolin-3-yl)-2-cyanocyclopropane-1-carboxamide |

TABLE 1-continued

| Compound No. | Structure | Name |
|---|---|---|
| | (structure) | |
| 132 | (structure) | trans-N-(8-amino-6-((S)-3-hydroxy-2-oxopyrrolidin-1-yl)isoquinolin-3-yl)-2-cyanocyclopropane-1-carboxamide |
| | (structure) | |
| 133 | (structure) | trans-N-[8-amino-6-(5-isopropyl-1-methyl-pyrazol-4-yl)-3-isoquinolyl]-2-cyano-cyclopropane-1-carboxamide |
| | (structure) | |

TABLE 1-continued

| Compound No. | Structure | Name |
|---|---|---|
| 134 | 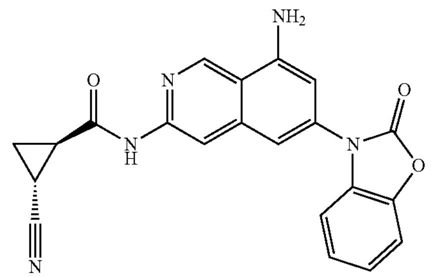 [SMILES: N#C[C@@H]1C[C@H]1C(=O)Nc1cc2cc(-n3c(=O)oc4ccccc43)cc(N)c2cn1] | trans-N-[8-amino-6-(2-oxo-1,3-benzoxazol-3-yl)-3-isoquinolyl]-2-cyano-cyclopropane-1-carboxamide |
| | | |
| 135 | 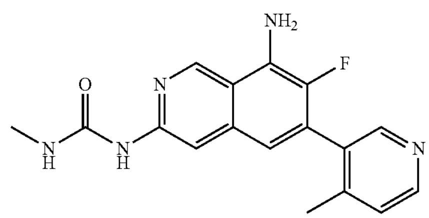 | 1-[8-amino-7-fluoro-6-(4-methyl-3-pyridyl)-3-isoquinolyl]-3-methylurea |
| 138 | 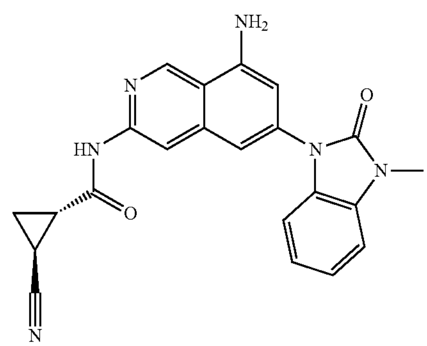 [SMILES: Cn1c(=O)n(-c2cc(N)c3cnc(NC(=O)[C@H]4C[C@@H]4C#N)cc3c2)c2ccccc21] | trans-N-(8-amino-6-(3-methyl-2-oxo-2,3-dihydro-1H-benzo[d]imidazol-1-yl)isoquinolin-3-yl)-2-cyanocyclopropane-1-carboxamide |

TABLE 1-continued

| Compound No. | Structure | Name |
|---|---|---|
| 140 | 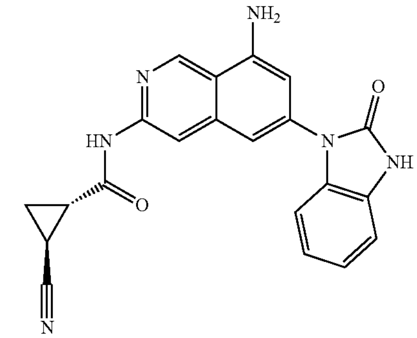 [SMILES: N#C[C@H]1C[C@@H]1C(=O)Nc1cc2cc(-n3c(=O)[nH]c4ccccc43)cc(N)c2cn1] | trans-N-(8-amino-6-(2-oxo-2,3-dihydro-1H-benzo[d]imidazol-1-yl)isoquinolin-3-yl)-2-cyanocyclopropane-1-carboxamide |
| | | |
| 143 | 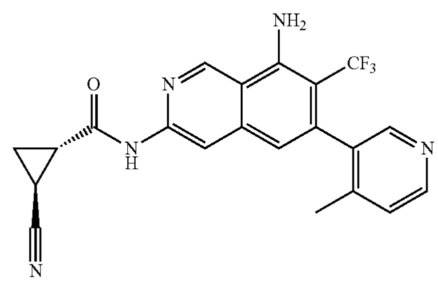 | trans-N-(8-amino-6-(4-methylpyridin-3-yl)-7-(trifluoromethyl)isoquinolin-3-yl)-2-cyanocyclopropane-1-carboxamide |
| | | |
| 144 | 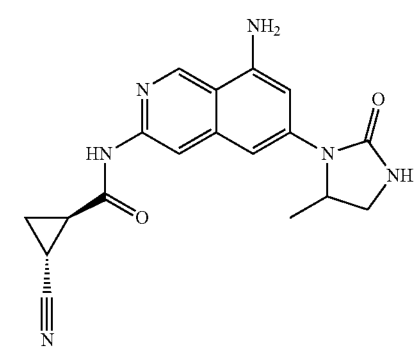 [SMILES: CC1CNC(=O)N1c1cc(N)c2cnc(NC(=O)[C@@H]3C[C@H]3C#N)cc2c1] | trans-N-(8-amino-6-(5-methyl-2-oxoimidazolidin-1-yl)isoquinolin-3-yl)-2-cyanocyclopropane-1-carboxamide |

TABLE 1-continued

| Compound No. | Structure | Name |
|---|---|---|
| | | |
| 145 | 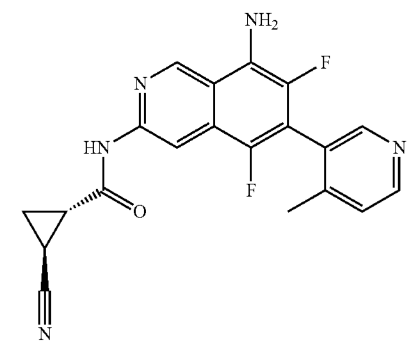 [SMILES: Cc1ccncc1-c1c(F)c(N)c2cnc(NC(=O)[C@H]3C[C@@H]3C#N)cc2c1F] | trans-N-(8-amino-5,7-difluoro-6-(4-methylpyridin-3-yl)isoquinolin-3-yl)-2-cyanocyclopropane-1-carboxamide |
| 147 | 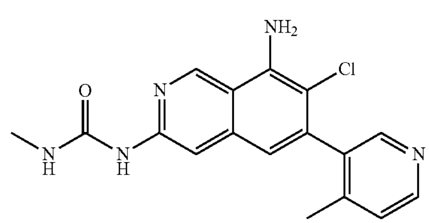 [SMILES: CNC(=O)Nc1cc2cc(-c3cnccc3C)c(Cl)c(N)c2cn1] | 1-(8-amino-7-chloro-6-(4-methylpyridin-3-yl)isoquinolin-3-yl)-3-methylurea |
| 148 | 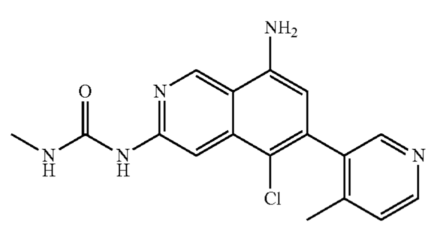 [SMILES: CNC(=O)Nc1cc2c(Cl)c(-c3cnccc3C)cc(N)c2cn1] | 1-(8-amino-5-chloro-6-(4-methylpyridin-3-yl)isoquinolin-3-yl)-3-methylurea |

TABLE 1-continued

| Compound No. | Structure | Name |
|---|---|---|
| 149 | 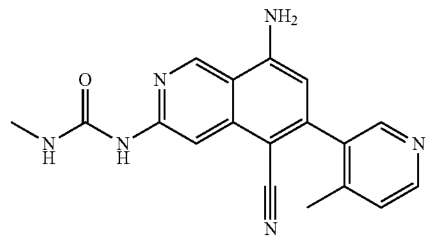 [SMILES: CNC(=O)Nc1cc2c(C#N)c(-c3cnccc3C)cc(N)c2cn1] | 1-(8-amino-5-cyano-6-(4-methylpyridin-3-yl)isoquinolin-3-yl)-3-methylurea |
| 150 | 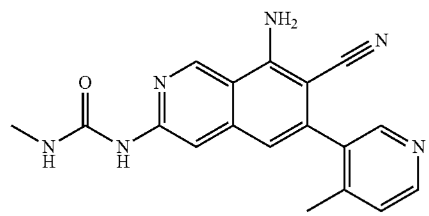 [SMILES: CNC(=O)Nc1cc2cc(-c3cnccc3C)c(C#N)c(N)c2cn1] | 1-(8-amino-7-cyano-6-(4-methylpyridin-3-yl)isoquinolin-3-yl)-3-methylurea |
| 151 | 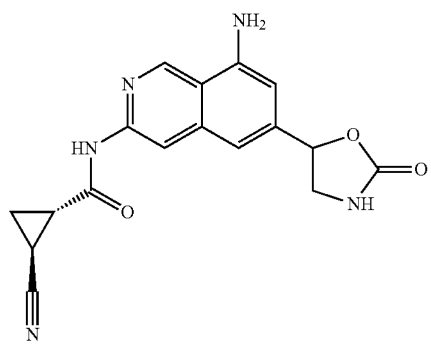 [SMILES: N#C[C@H]1C[C@@H]1C(=O)Nc1cc2cc(C3CNC(=O)O3)cc(N)c2cn1] | trans-N-[8-amino-6-(2-oxooxazolidin-5-yl)-3-isoquinolyl]-2-cyano-cyclopropane-1-carboxamide |
| | | |
| 153 | 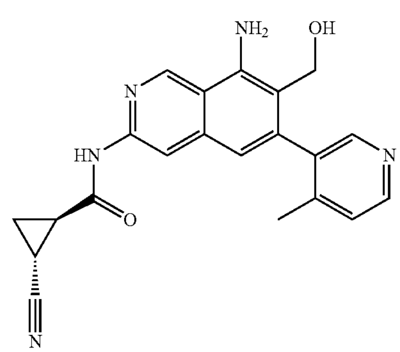 [SMILES: Cc1ccncc1-c1cc2cc(NC(=O)[C@@H]3C[C@H]3C#N)ncc2c(N)c1CO] | trans-N-[8-amino-7-(hydroxymethyl)-6-(4-methyl-3-pyridyl)-3-isoquinolyl]-2-cyano-cyclopropane-1-carboxamide |

TABLE 1-continued

| Compound No. | Structure | Name |
|---|---|---|
| | | |
| 154 | 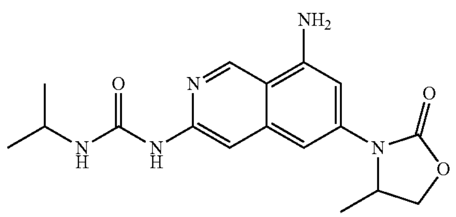 [SMILES: CC(C)NC(=O)Nc1cc2cc(N3C(=O)OCC3C)cc(N)c2cn1] | 1-[8-amino-6-(4-methyl-2-oxo-oxazolidin-3-yl)-3-isoquinolyl]-3-isopropylurea |
| 155 | 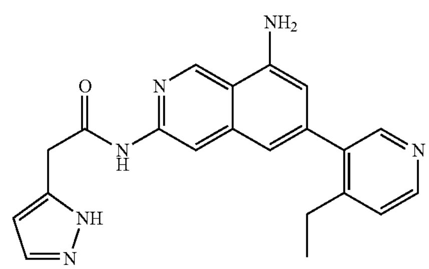 [SMILES: CCc1ccncc1-c1cc(N)c2cnc(NC(=O)Cc3ccn[nH]3)cc2c1] | N-(8-amino-6-(4-ethylpyridin-3-yl)isoquinolin-3-yl)-2-(1H-pyrazol-5-yl)acetamide |
| 156 | 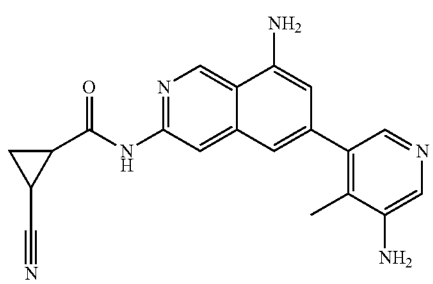 [SMILES: Cc1c(N)cncc1-c1cc(N)c2cnc(NC(=O)C3CC3C#N)cc2c1] | trans-N-(8-amino-6-(5-amino-4-methylpyridin-3-yl)isoquinolin-3-yl)-2-cyanocyclopropane-1-carboxamide |
| 159 | 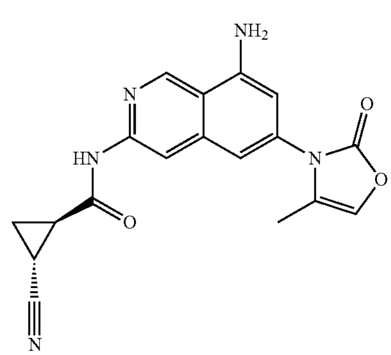 [SMILES: Cc1coc(=O)n1-c1cc(N)c2cnc(NC(=O)[C@@H]3C[C@H]3C#N)cc2c1] | trans-N-(8-amino-6-(4-methyl-2-oxooxazol-3(2H)-yl)isoquinolin-3-yl)-2-cyanocyclopropane-1-carboxamide |

| Compound No. | Structure | Name |
|---|---|---|
| | 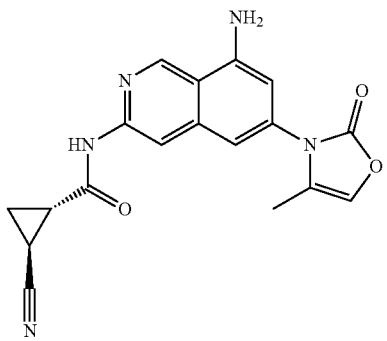 [SMILES: Cc1coc(=O)n1-c1cc(N)c2cnc(NC(=O)[C@H]3C[C@@H]3C#N)cc2c1] | |
| 160 | 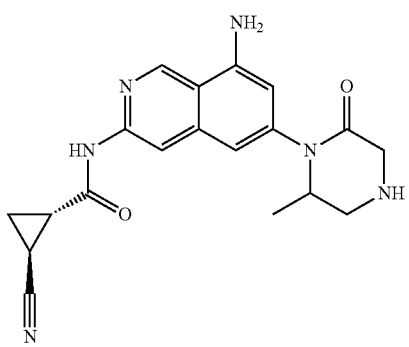 [SMILES: CC1CNCC(=O)N1c1cc(N)c2cnc(NC(=O)[C@H]3C[C@@H]3C#N)cc2c1] | trans-N-(8-amino-6-(2-methyl-6-oxopiperazin-1-yl)isoquinolin-3-yl)-2-cyanocyclopropane-1-carboxamide |
| | 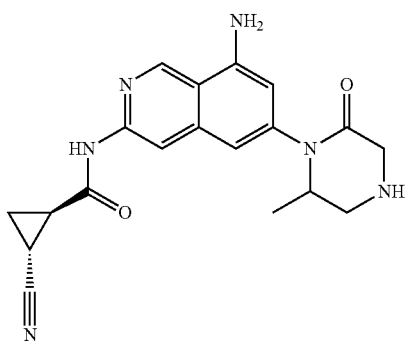 [SMILES: CC1CNCC(=O)N1c1cc(N)c2cnc(NC(=O)[C@@H]3C[C@H]3C#N)cc2c1] | |
| 161 | 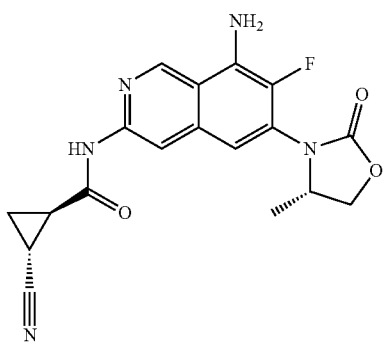 [SMILES: C[C@H]1COC(=O)N1c1cc2cc(NC(=O)[C@@H]3C[C@H]3C#N)ncc2c(N)c1F] | trans-N-(8-amino-7-fluoro-6-((S)-4-methyl-2-oxooxazolidin-3-yl)isoquinolin-3-yl)-2-cyanocyclopropane-1-carboxamide |

TABLE 1-continued

| Compound No. | Structure | Name |
|---|---|---|
| 162 | 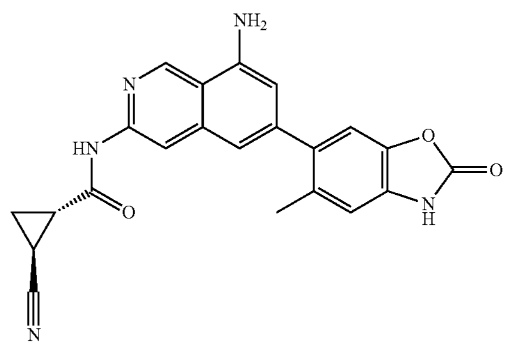 [SMILES: Cc1cc2[nH]c(=O)oc2cc1-c1cc(N)c2cnc(NC(=O)[C@H]3C[C@@H]3C#N)cc2c1] | (1S,2S)-N-(8-amino-6-(5-methyl-2-oxo-2,3-dihydrobenzo[d]oxazol-6-yl)isoquinolin-3-yl)-2-cyanocyclopropane-1-carboxamide |
| 163 | 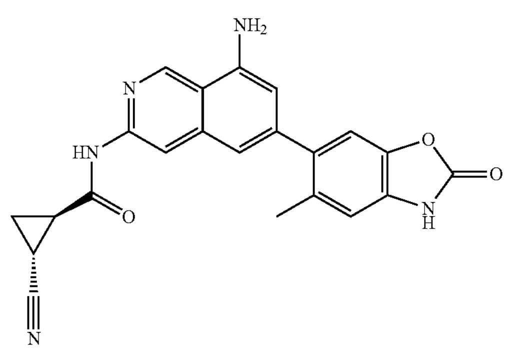 [SMILES: Cc1cc2[nH]c(=O)oc2cc1-c1cc(N)c2cnc(NC(=O)[C@@H]3C[C@H]3C#N)cc2c1] | (1R,2R)-N-(8-amino-6-(5-methyl-2-oxo-2,3-dihydrobenzo[d]oxazol-6-yl)isoquinolin-3-yl)-2-cyanocyclopropane-1-carboxamide |
| 164 | 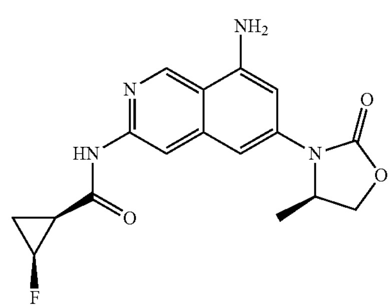 [SMILES: C[C@@H]1COC(=O)N1c1cc(N)c2cnc(NC(=O)[C@@H]3C[C@@H]3F)cc2c1] | (1S,2S)-N-(8-amino-6-((R)-4-methyl-2-oxooxazolidin-3-yl)isoquinolin-3-yl)-2-fluorocyclopropane-1-carboxamide |

TABLE 1-continued

| Compound No. | Structure | Name |
|---|---|---|
| 165 | 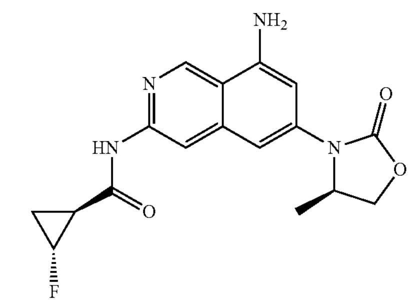 [SMILES: C[C@@H]1COC(=O)N1c1cc(N)c2cnc(NC(=O)[C@@H]3C[C@H]3F)cc2c1] | (1S,2R)-N-(8-amino-6-((R)-4-methyl-2-oxooxazolidin-3-yl)isoquinolin-3-yl)-2-fluorocyclopropane-1-carboxamide |
| 166 | 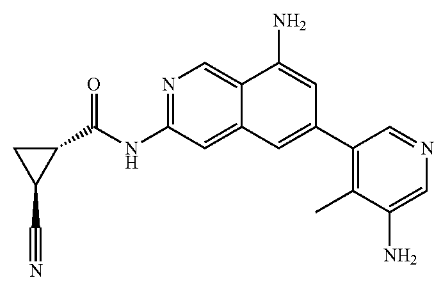 [SMILES: Cc1c(N)cncc1-c1cc(N)c2cnc(NC(=O)[C@H]3C[C@@H]3C#N)cc2c1] | (1S,2S)-N-(8-amino-6-(5-amino-4-methylpyridin-3-yl)isoquinolin-3-yl)-2-cyanocyclopropane-1-carboxamide |
| 167 | 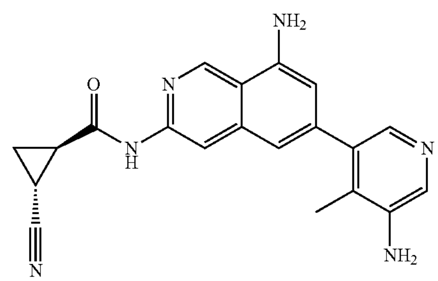 [SMILES: Cc1c(N)cncc1-c1cc(N)c2cnc(NC(=O)[C@@H]3C[C@H]3C#N)cc2c1] | (1R,2R)-N-(8-amino-6-(5-amino-4-methylpyridin-3-yl)isoquinolin-3-yl)-2-cyanocyclopropane-1-carboxamide |
| 168, 169 | | trans-N-(8-amino-6-(4-methylisothiazol-5-yl)isoquinolin-3-yl)-2-cyanocyclopropane-1-carboxamide |

TABLE 1-continued

| Compound No. | Structure | Name |
|---|---|---|
| 175 | 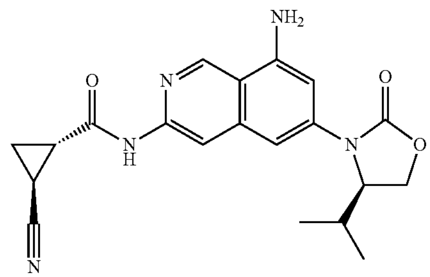 [SMILES: CC(C)[C@@H]1COC(=O)N1c1cc(N)c2cnc(NC(=O)[C@H]3C[C@@H]3C#N)cc2c1] | trans-N-(8-amino-6-((R)-4-isopropyl-2-oxooxazolidin-3-yl)isoquinolin-3-yl)-2-cyanocyclopropane-1-carboxamide |
| | | |
| 176 | 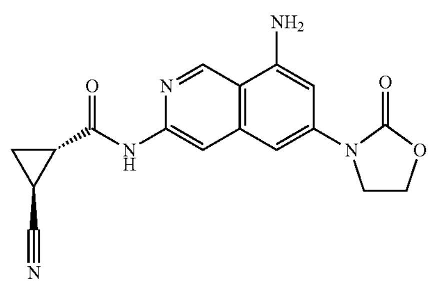 [SMILES: N#C[C@H]1C[C@@H]1C(=O)Nc1cc2cc(N3CCOC3=O)cc(N)c2cn1] | trans-N-(8-amino-6-(2-oxooxazolidin-3-yl)isoquinolin-3-yl)-2-cyanocyclopropane-1-carboxamide |
| | | |
| 177 | 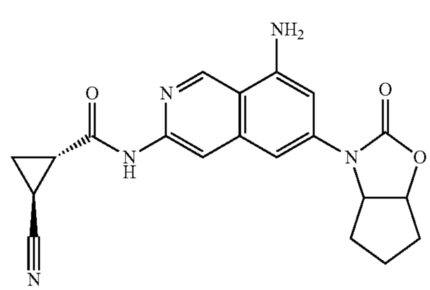 [SMILES: N#C[C@H]1C[C@@H]1C(=O)Nc1cc2cc(N3C(=O)OC4CCCC43)cc(N)c2cn1] | trans-N-(8-amino-6-(2-oxotetrahydro-2H-cyclopenta[d]oxazol-3(3aH)-yl)isoquinolin-3-yl)-2-cyanocyclopropane-1-carboxamide |

| Compound No. | Structure | Name |
|---|---|---|
| 178 | 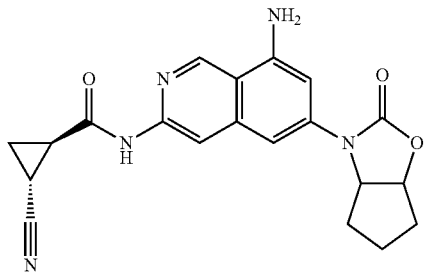 [SMILES: N#C[C@@H]1C[C@H]1C(=O)Nc1cc2cc(N3C(=O)OC4CCCC43)cc(N)c2cn1] | trans-N-(8-amino-6-(N,N-dimethylsulfamoyl)isoquinolin-3-yl)cyclopropane-1,2-dicarboxamide |
| | 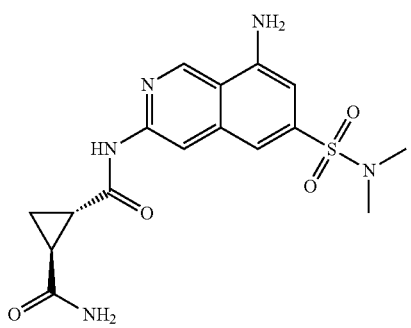 [SMILES: CN(C)S(=O)(=O)c1cc(N)c2cnc(NC(=O)[C@H]3C[C@@H]3C(N)=O)cc2c1] | |
| 179 | 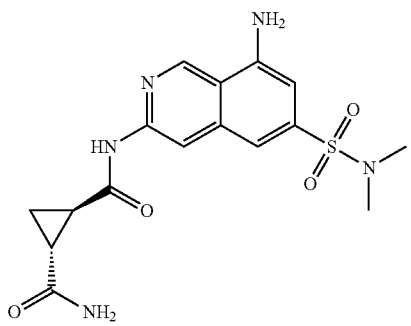 [SMILES: CN(C)S(=O)(=O)c1cc(N)c2cnc(NC(=O)[C@@H]3C[C@H]3C(N)=O)cc2c1] | trans-N-(8-amino-6-(N,N-dimethylsulfamoyl)isoquinolin-3-yl)-2-cyanocyclopropane-1-carboxamide |
| | 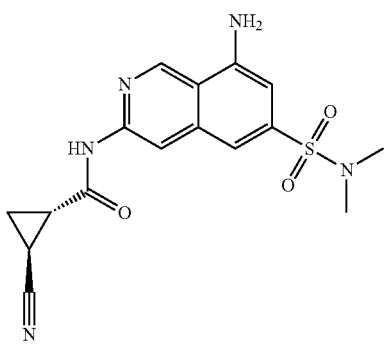 [SMILES: CN(C)S(=O)(=O)c1cc(N)c2cnc(NC(=O)[C@H]3C[C@@H]3C#N)cc2c1] | |

| Compound No. | Structure | Name |
|---|---|---|
| | (structure) | |
| 180 | (structure) | (1S,2S)-N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropane-1-carboxamide |
| 181 | (structure) | (1R,2R)-N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropane-1-carboxamide |
| 182 | (structure) | (1R,2R)-N-(8-amino-6-(4-methyl-2-phenylpyridin-3-yl)isoquinolin-3-yl)-2-(1-methyl-1H-pyrazol-4-yl)cyclopropane-1-carboxamide |
| 183 | (structure) | (1S,2S)-N-(8-amino-6-(4-methyl-2-phenylpyridin-3-yl)isoquinolin-3-yl)-2-(1-methyl-1H-pyrazol-4-yl)cyclopropane-1-carboxamide |

TABLE 1-continued

| Compound No. | Structure | Name |
|---|---|---|
| 184 | 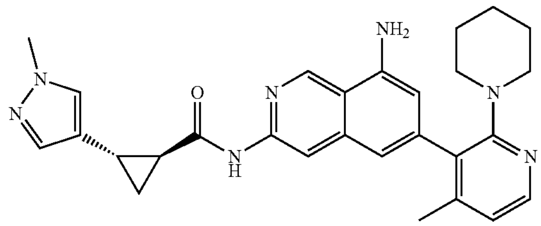 [SMILES: Cc1ccnc(N2CCCCC2)c1-c1cc(N)c2cnc(NC(=O)[C@H]3C[C@@H]3c3cnn(C)c3)cc2c1] | trans-N-(8-amino-6-(4-methyl-2-(piperidin-1-yl)pyridin-3-yl)isoquinolin-3-yl)-2-(1-methyl-1H-pyrazol-4-yl)cyclopropane-1-carboxamide |
| 185 | 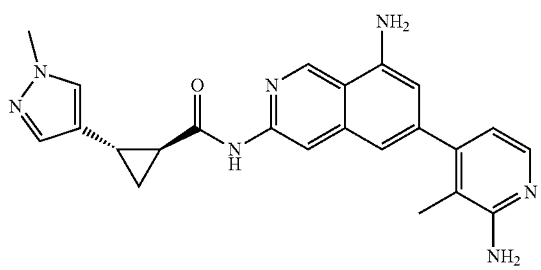 [SMILES: Cc1c(-c2cc(N)c3cnc(NC(=O)[C@H]4C[C@@H]4c4cnn(C)c4)cc3c2)ccnc1N] | trans-N-(8-amino-6-(2-amino-3-methylpyridin-4-yl)isoquinolin-3-yl)-2-(1-methyl-1H-pyrazol-4-yl)cyclopropane-1-carboxamide |
| 186 | 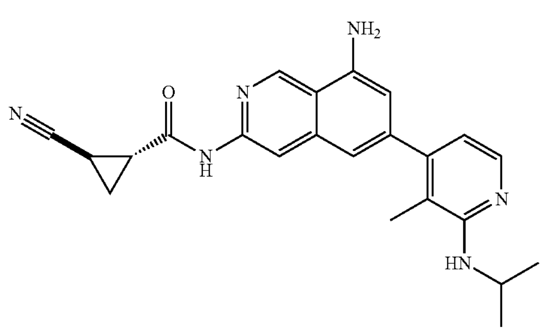 [SMILES: Cc1c(-c2cc(N)c3cnc(NC(=O)[C@@H]4C[C@H]4C#N)cc3c2)ccnc1NC(C)C] | trans-N-(8-amino-6-[4-methyl-5-[(propan-2-yl)amino]pyridin-3-yl]isoquinolin-3-yl)-2-cyanocyclopropane-1-carboxamide |

TABLE 1-continued

| Compound No. | Structure | Name |
|---|---|---|
| | (structure) | |
| 187 | (structure) | trans-N-(8-amino-6-(4-methyl-2-(1-methyl-1H-pyrazol-4-yl)pyridin-3-yl)isoquinolin-3-yl)-2-(cyanomethyl)cyclopropane-1-carboxamide |
| | (structure) | |
| 188 | (structure) | N-(8-amino-6-(2,3-dihydro-1H-pyrrolo[2,3-c]pyridin-4-yl)isoquinolin-3-yl)cyclopropanecarboxamide |
| 189, 190 | (structure) | N-(8-amino-6-(2-methyl-2,3-dihydro-1H-pyrrolo[2,3-c]pyridin-4-yl)isoquinolin-3-yl)cyclopropanecarboxamide |

TABLE 1-continued

| Compound No. | Structure | Name |
|---|---|---|
| | [structure] | |
| 191, 192 | [structure] | (1,2)trans-N-(8-amino-6-(4-methylpyridin-3-yl)isoquinolin-3-yl)-2-(cyanomethyl)-3-methylcyclopropane-1-carboxamide |
| | [structure] | |
| | [structure] | |
| | [structure] | |
| 193, 194 | [structure] | 2-(4-(8-amino-7-fluoro-6-(4-methylpyridin-3-yl)isoquinolin-3-ylamino)-1H-pyrazol-1-yl)propanenitrile |

TABLE 1-continued

| Compound No. | Structure | Name |
|---|---|---|
| 195, 196, 197, 198 | | (1,3)trans-N-(8-amino-7-fluoro-6-(4-methylpyridin-3-yl)isoquinolin-3-yl)-2-methyl-3-(1-methyl-1H-pyrazol-4-yl)cyclopropane-1-carboxamide |

TABLE 1-continued

| Compound No. | Structure | Name |
|---|---|---|
| 199, 200 | | 2-(3-(8-amino-6-(4-methylpyridin-3-yl)isoquinolin-3-ylamino)-1H-pyrazol-1-yl)propanenitrile |
| 201, 202 | | 2-(4-(8-amino-6-(4-methylpyridin-3-yl)isoquinolin-3-ylamino)-1H-pyrazol-1-yl)propanenitrile |

TABLE 1-continued

| Compound No. | Structure | Name |
|---|---|---|
| 203 | 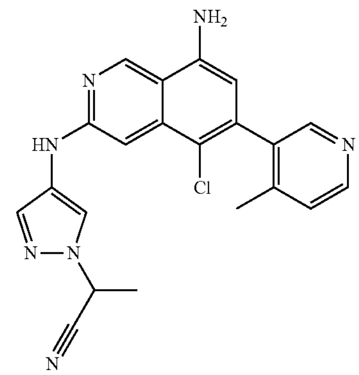 [SMILES: Cc1ccncc1-c1cc(N)c2cnc(Nc3cnn(C(C)C#N)c3)cc2c1Cl] | 2-(4-(8-amino-5-chloro-6-(4-methylpyridin-3-yl)isoquinolin-3-ylamino)-1H-pyrazol-1-yl)propanenitrile |
| 204 | 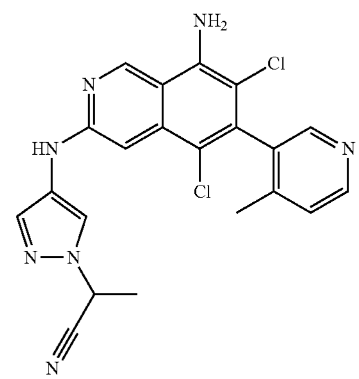 [SMILES: Cc1ccncc1-c1c(Cl)c(N)c2cnc(Nc3cnn(C(C)C#N)c3)cc2c1Cl] | 2-(4-(8-amino-5,7-dichloro-6-(4-methylpyridin-3-yl)isoquinolin-3-ylamino)-1H-pyrazol-1-yl)propanenitrile |
| 205, 206 | 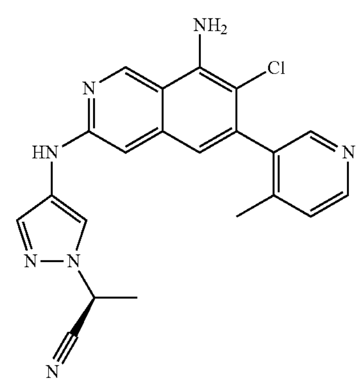 [SMILES: Cc1ccncc1-c1cc2cc(Nc3cnn([C@@H](C)C#N)c3)ncc2c(N)c1Cl] | 2-(4-(8-amino-7-chloro-6-(4-methylpyridin-3-yl)isoquinolin-3-ylamino)-1H-pyrazol-1-yl)propanenitrile |

TABLE 1-continued

| Compound No. | Structure | Name |
|---|---|---|
| 207, 208 | 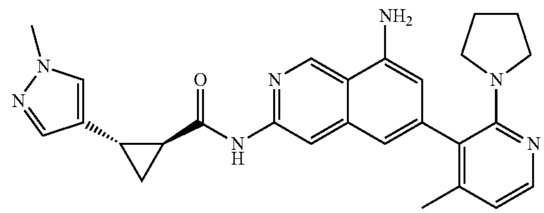 [SMILES: Cc1ccnc(N2CCCC2)c1-c1cc(N)c2cnc(NC(=O)[C@H]3C[C@@H]3c3cnn(C)c3)cc2c1] | trans-N-(8-amino-6-(4-methyl-2-(pyrrolidin-1-yl)pyridin-3-yl)isoquinolin-3-yl)-2-(1-methyl-1H-pyrazol-4-yl)cyclopropane-1-carboxamide |
| 209 | 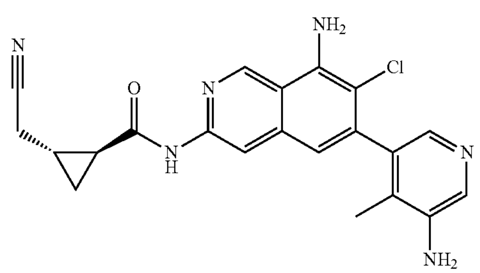 | trans-N-(8-amino-6-(5-amino-4-methylpyridin-3-yl)-7-chloroisoquinolin-3-yl)-2-(cyanomethyl)cyclopropane-1-carboxamide |
| 210, 211 | 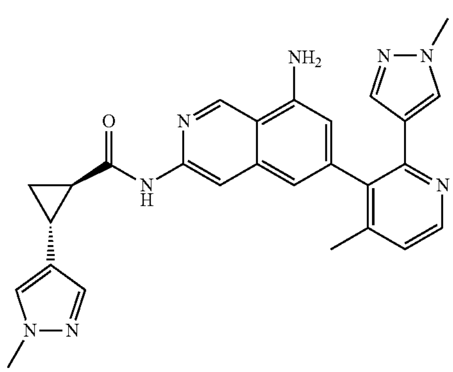 | trans-N-(8-amino-6-(4-methyl-2-(1-methyl-1H-pyrazol-4-yl)pyridin-3-yl)isoquinolin-3-yl)-2-(1-methyl-1H-pyrazol-4-yl)cyclopropane-1-carboxamide |

TABLE 1-continued

| Compound No. | Structure | Name |
|---|---|---|
| | | |
| 212, 213, 214, 215 | 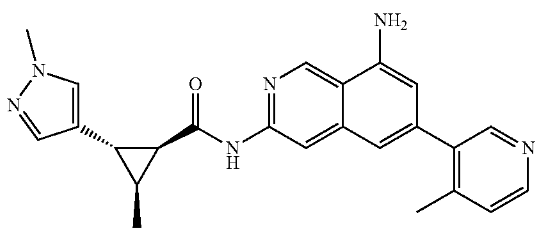 [SMILES: Cc1ccncc1-c1cc(N)c2cnc(NC(=O)[C@H]3[C@@H](C)[C@@H]3c3cnn(C)c3)cc2c1] | (1,3)trans-N-(8-amino-6-(4-methylpyridin-3-yl)isoquinolin-3-yl)-2-methyl-3-(1-methyl-1H-pyrazol-4-yl)cyclopropane-1-carboxamide |
| 216, 217 | 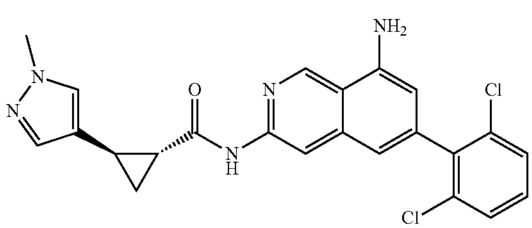 [SMILES: Cn1cc([C@@H]2C[C@H]2C(=O)Nc2cc3cc(-c4c(Cl)cccc4Cl)cc(N)c3cn2)cn1] | trans-N-(8-amino-6-(2,6-dichlorophenyl)isoquinolin-3-yl)-2-(1-methyl-1H-pyrazol-4-yl)cyclopropane-1-carboxamide |

TABLE 1-continued

| Compound No. | Structure | Name |
|---|---|---|
| 218, 219 | 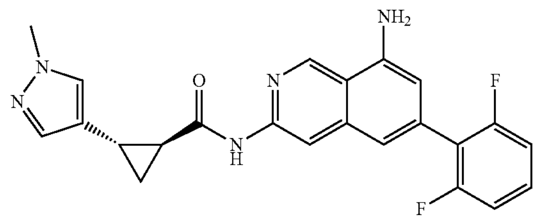 [SMILES: Cn1cc([C@H]2C[C@@H]2C(=O)Nc2cc3cc(-c4c(F)cccc4F)cc(N)c3cn2)cn1] | trans-N-(8-amino-6-(2,6-difluorophenyl)isoquinolin-3-yl)-2-(1-methyl-1H-pyrazol-4-yl)cyclopropane-1-carboxamide |
| 220, 221 | 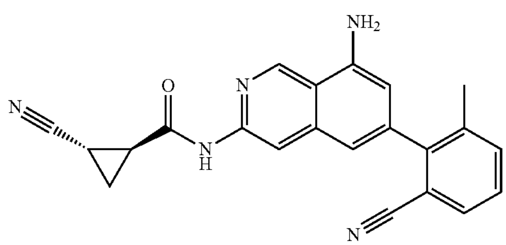 [SMILES: Cc1cccc(C#N)c1-c1cc(N)c2cnc(NC(=O)[C@H]3C[C@@H]3C#N)cc2c1] | trans-N-(8-amino-6-(2-cyano-6-methylphenyl)isoquinolin-3-yl)-2-cyanocyclopropane-1-carboxamide |
| 222, 223 | 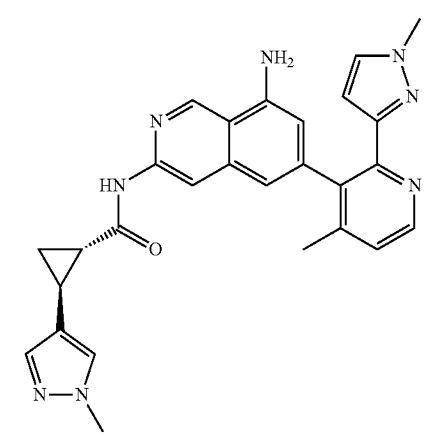 [SMILES: Cc1ccnc(-c2ccn(C)n2)c1-c1cc(N)c2cnc(NC(=O)[C@H]3C[C@@H]3c3cnn(C)c3)cc2c1] | trans-N-(8-amino-6-(4-methyl-2-(1-methyl-1H-pyrazol-3-yl)pyridin-3-yl)isoquinolin-3-yl)-2-(1-methyl-1H-pyrazol-4-yl)cyclopropane-1-carboxamide |

TABLE 1-continued

| Compound No. | Structure | Name |
|---|---|---|
| 224 | 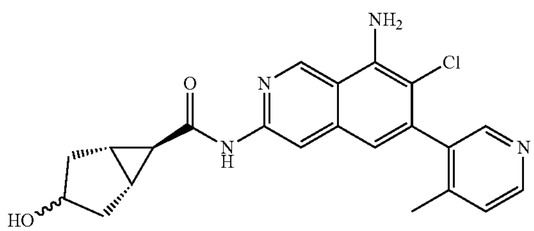 | (1R,5S,6r)-N-(8-amino-7-chloro-6-(4-methylpyridin-3-yl)isoquinolin-3-yl)-3-hydroxybicyclo[3.1.0]hexane-6-carboxamide |
| 225 | 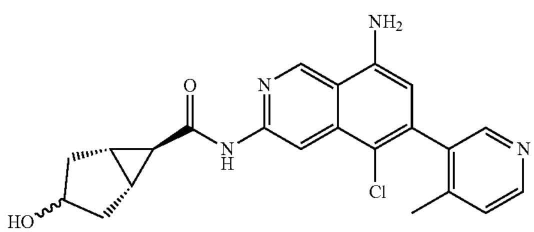 | (1R,5S,6r)-N-(8-amino-5-chloro-6-(4-methylpyridin-3-yl)isoquinolin-3-yl)-3-hydroxybicyclo[3.1.0]hexane-6-carboxamide |
| 226 | 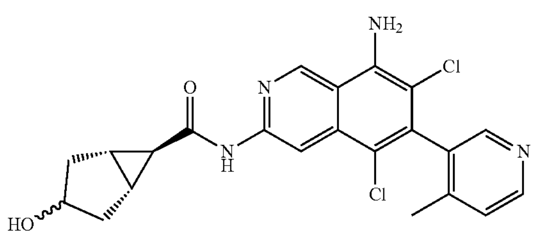 | (1R,5S,6r)-N-(8-amino-5,7-dichloro-6-(4-methylpyridin-3-yl)isoquinolin-3-yl)-3-hydroxybicyclo[3.1.0]hexane-6-carboxamide |
| 227 | 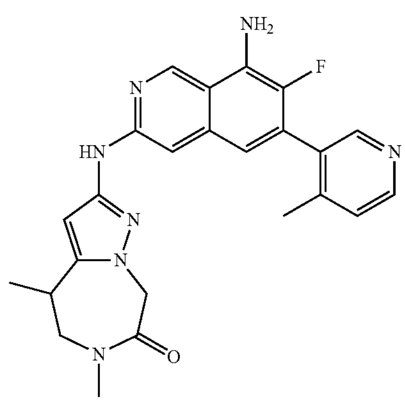 [SMILES: Cc1ccncc1-c1cc2cc(Nc3cc4n(n3)CC(=O)N(C)CC4C)ncc2c(N)c1F] | 2-((8-amino-7-fluoro-6-(4-methylpyridin-3-yl)isoquinolin-3-yl)amino)-4,6-dimethyl-5,6-dihydro-4H-pyrazolo[1,5-d][1,4]diazepin-7(8H)-one |

TABLE 1-continued

| Compound No. | Structure | Name |
|---|---|---|
| 228 | 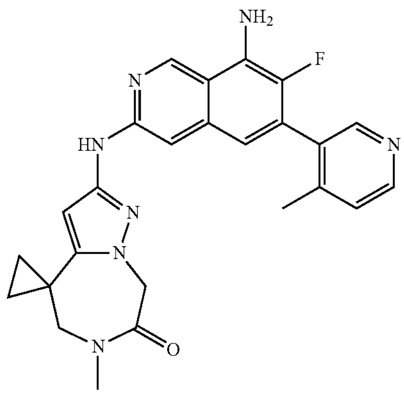 [SMILES: Cc1ccncc1-c1cc2cc(Nc3cc4n(n3)CC(=O)N(C)CC43CC3)ncc2c(N)c1F] | 2'-((8-amino-7-fluoro-6-(4-methylpyridin-3-yl)isoquinolin-3-yl)amino)-6'-methyl-5',6'-dihydrospiro[cyclopropane-1,4'-pyrazolo[1,5-d][1,4]diazepin]-7'(8'H)-one |
| 229 | 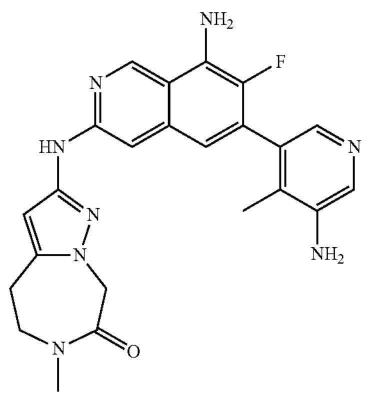 [SMILES: Cc1c(N)cncc1-c1cc2cc(Nc3cc4n(n3)CC(=O)N(C)CC4)ncc2c(N)c1F] | 2-((8-amino-6-(5-amino-4-methylpyridin-3-yl)-7-fluoroisoquinolin-3-yl)amino)-6-methyl-5,6-dihydro-4H-pyrazolo[1,5-d][1,4]diazepin-7(8H)-one |
| 230 | 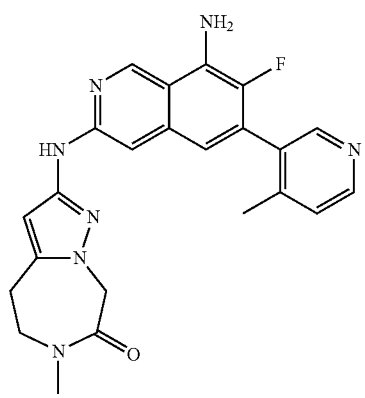 [SMILES: Cc1ccncc1-c1cc2cc(Nc3cc4n(n3)CC(=O)N(C)CC4)ncc2c(N)c1F] | 2-((8-amino-7-fluoro-6-(4-methylpyridin-3-yl)isoquinolin-3-yl)amino)-6-methyl-5,6-dihydro-4H-pyrazolo[1,5-d][1,4]diazepin-7(8H)-one |
| 9, 10, 11, 12 | 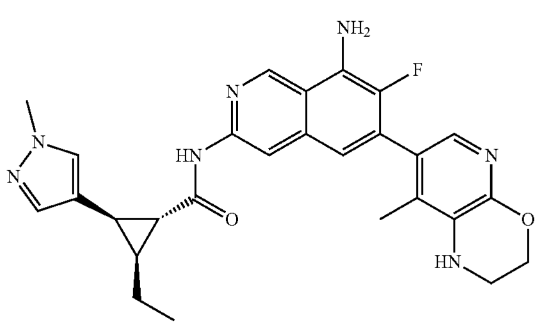 [SMILES: CC[C@@H]1[C@@H](C(=O)Nc2cc3cc(-c4cnc5c(c4C)NCCO5)c(F)c(N)c3cn2)[C@@H]1c1cnn(C)c1] | (1,3)trans-N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide |

TABLE 1-continued

| Compound No. | Structure | Name |
|---|---|---|
| 29 | 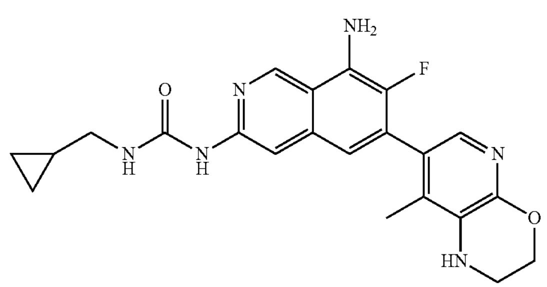 [SMILES: Cc1c(-c2cc3cc(NC(=O)NCC4CC4)ncc3c(N)c2F)cnc2c1NCCO2] | 1-(8-amino-7-fluoro-6-(8-methyl-2,3-dihydro-1H-pyrido[2,3-b][1,4]oxazin-7-yl)isoquinolin-3-yl)-3-(cyclopropylmethyl)urea |
| 33, 34, 35, 36 | 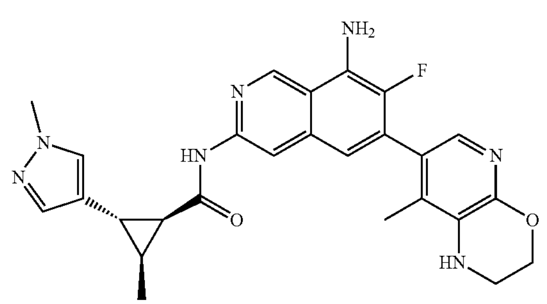 [SMILES: Cc1c(-c2cc3cc(NC(=O)[C@H]4[C@@H](C)[C@@H]4c4cnn(C)c4)ncc3c(N)c2F)cnc2c1NCCO2] | (1,3)trans-N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide |

| Compound No. | Structure | Name |
|---|---|---|
| | | |
| | | |
| | | |
| 53 | 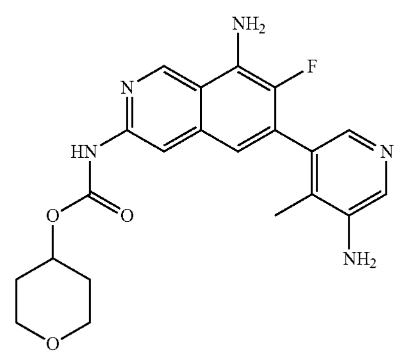 [SMILES: Cc1c(N)cncc1-c1cc2cc(NC(=O)OC3CCOCC3)ncc2c(N)c1F] | tetrahydro-2H-pyran-4-yl (8-amino-6-(5-amino-4-methylpyridin-3-yl)-7-fluoroisoquinolin-3-carbamate-yl)carbamate |
| 58 | 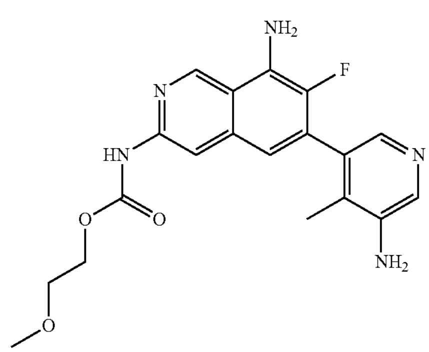 [SMILES: COCCOC(=O)Nc1cc2cc(-c3cncc(N)c3C)c(F)c(N)c2cn1] | 2-methoxyethyl (8-amino-6-(5-amino-4-methylpyridin-3-yl)-7-fluoroisoquinolin-3-yl)carbamate |

TABLE 1-continued

| Compound No. | Structure | Name |
|---|---|---|
| 64 | 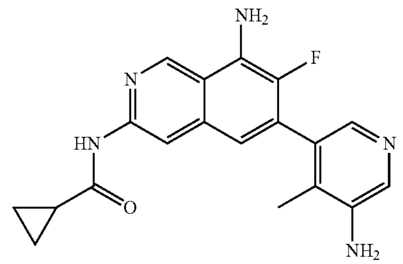 [SMILES: Cc1c(N)cncc1-c1cc2cc(NC(=O)C3CC3)ncc2c(N)c1F] | N-(8-amino-6-(5-amino-4-methylpyridin-3-yl)-7-fluoroisoquinolin-3-yl)cyclopropanecarboxamide |
| 83, 84 | 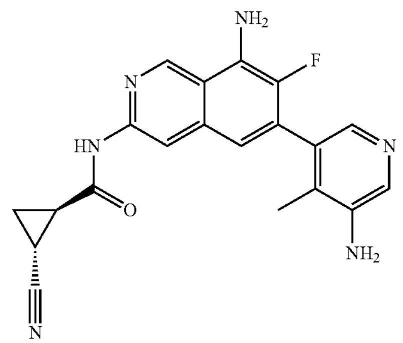 [SMILES: Cc1c(N)cncc1-c1cc2cc(NC(=O)[C@@H]3C[C@H]3C#N)ncc2c(N)c1F] | trans-N-(8-amino-6-(5-amino-4-methylpyridin-3-yl)-7-fluoroisoquinolin-3-yl)-2-cyanocyclopropane-1-carboxamide |
| | | |
| 96 | 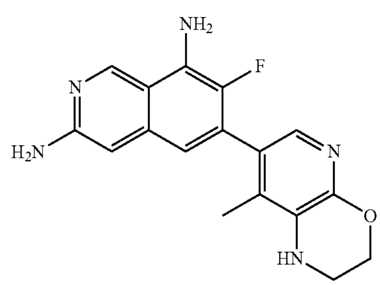 [SMILES: Cc1c(-c2cc3cc(N)ncc3c(N)c2F)cnc2c1NCCO2] | 7-fluoro-6-(8-methyl-2,3-dihydro-1H-pyrido[2,3-b][1,4]oxazin-7-yl)isoquinoline-3,8-diamine |
| 97 | 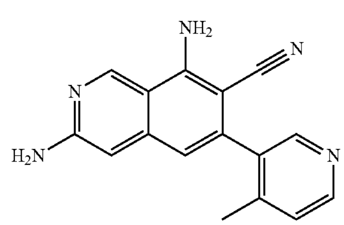 [SMILES: Cc1ccncc1-c1cc2cc(N)ncc2c(N)c1C#N] | 3,8-diamino-6-(4-methylpyridin-3-yl)isoquinoline-7-carbonitrile |

TABLE 1-continued

| Compound No. | Structure | Name |
|---|---|---|
| 111, 112 | | 1-(8-amino-7-fluoro-6-(8-methyl-2,3-dihydro-1H-pyrido[2,3-b][1,4]oxazin-7-yl)isoquinolin-3-yl)-3-(1-(1-methyl-1H-pyrazol-4-yl)ethyl)urea |
| 114 | 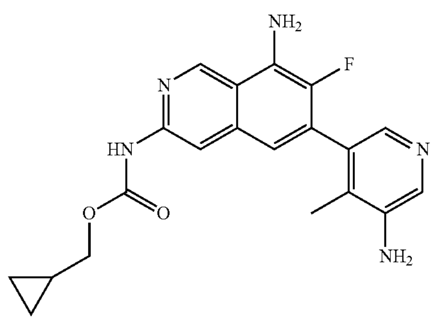 [SMILES: Cc1c(N)cncc1-c1cc2cc(NC(=O)OCC3CC3)ncc2c(N)c1F] | cyclopropylmethyl (8-amino-6-(5-amino-4-methylpyridin-3-yl)-7-fluoroisoquinolin-3-yl)carbamate |
| 120, 121 | | trans-N-(8-amino-6-(5-amino-4-methylpyridin-3-yl)-7-fluoroisoquinolin-3-yl)-2,2-dimethyl-3-(1-methyl-1H-pyrazol-4-yl)cyclopropane-1-carboxamide |

TABLE 1-continued

| Compound No. | Structure | Name |
|---|---|---|
| 129 | 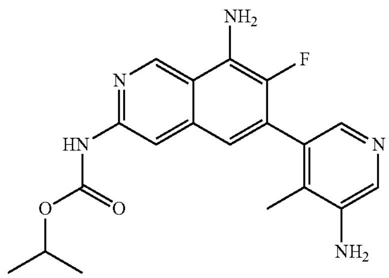 [SMILES: Cc1c(N)cncc1-c1cc2cc(NC(=O)OC(C)C)ncc2c(N)c1F] | isopropyl (8-amino-6-(5-amino-4-methylpyridin-3-yl)-7-fluoroisoquinolin-3-yl)carbamate |
| 137 | 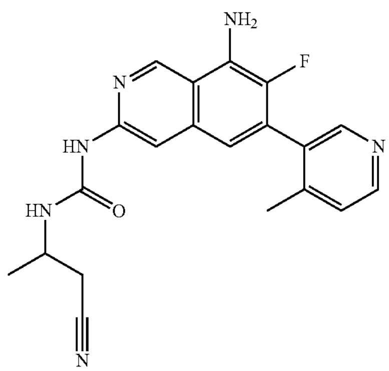 [SMILES: Cc1ccncc1-c1cc2cc(NC(=O)NC(C)CC#N)ncc2c(N)c1F] | 1-(8-amino-7-fluoro-6-(4-methylpyridin-3-yl)isoquinolin-3-yl)-3-(1-cyanopropan-2-yl)urea |
| 141 | 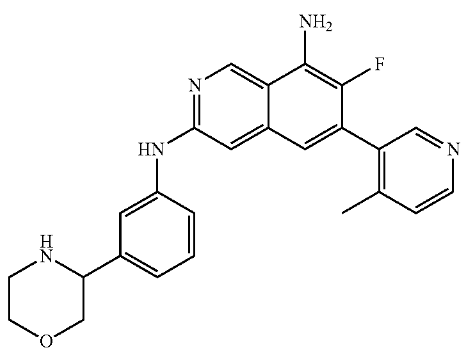 [SMILES: Cc1ccncc1-c1cc2cc(Nc3cccc(C4COCCN4)c3)ncc2c(N)c1F] | 7-fluoro-6-(4-methylpyridin-3-yl)-N3-(3-(morpholin-3-yl)phenyl)isoquinoline-3,8-diamine |
| 142 | 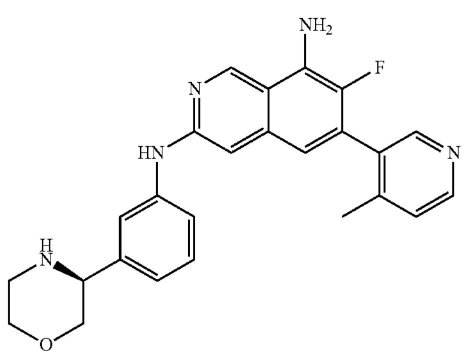 [SMILES: Cc1ccncc1-c1cc2cc(Nc3cccc([C@H]4COCCN4)c3)ncc2c(N)c1F] | (S)-7-fluoro-6-(4-methylpyridin-3-yl)-N3-(3-(morpholin-3-yl)phenyl)isoquinoline-3,8-diamine |
| 152 | 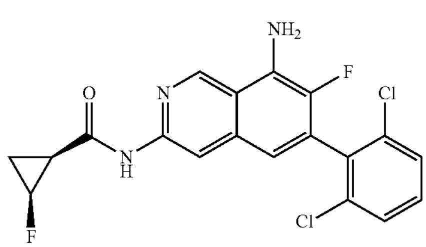 [SMILES: Nc1c(F)c(-c2c(Cl)cccc2Cl)cc2cc(NC(=O)[C@@H]3C[C@@H]3F)ncc12] | cis-N-(8-amino-6-(2,6-dichlorophenyl)-7-fluoroisoquinolin-3-yl)-2-fluorocyclopropane-1-carboxamide |

TABLE 1-continued

| Compound No. | Structure | Name |
|---|---|---|
| 158 | 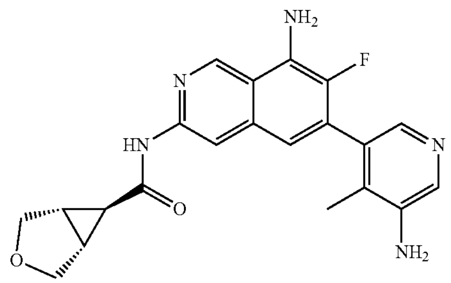 [SMILES: Cc1c(N)cncc1-c1cc2cc(NC(=O)[C@H]3[C@@H]4COC[C@@H]43)ncc2c(N)c1F] | (1R,5S,6r)-N-(8-amino-6-(5-amino-4-methylpyridin-3-yl)-7-fluoroisoquinolin-3-yl)-3-oxabicyclo[3.1.0]hexane-6-carboxamide |

TABLE 2

| Compound No. | Structure | Name |
|---|---|---|
| 231 | 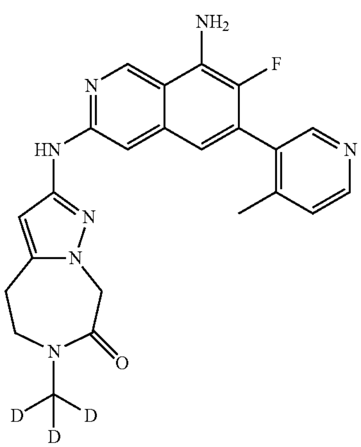 [SMILES: [2H]C([2H])([2H])N1CCc2cc(Nc3cc4cc(-c5cnccc5C)c(F)c(N)c4cn3)nn2CC1=O] | 2-((8-amino-7-fluoro-6-(4-methylpyridin-3-yl)isoquinolin-3-yl)amino)-6-(methyl-d3)-5,6-dihydro-4H-pyrazolo[1,5-d][1,4]diazepin-7(8H)-one |
| 232 | 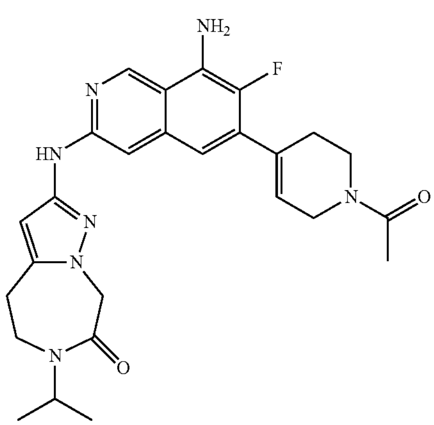 [SMILES: CC(=O)N1CC=C(c2cc3cc(Nc4cc5n(n4)CC(=O)N(C(C)C)CC5)ncc3c(N)c2F)CC1] | 2-((6-(1-acetyl-1,2,3,6-tetrahydropyridin-4-yl)-8-amino-7-fluoroisoquinolin-3-yl)amino)-6-isopropyl-5,6-dihydro-4H-pyrazolo[1,5-d][1,4]diazepin-7(8H)-one |

TABLE 2-continued

| Compound No. | Structure | Name |
|---|---|---|
| 233 | 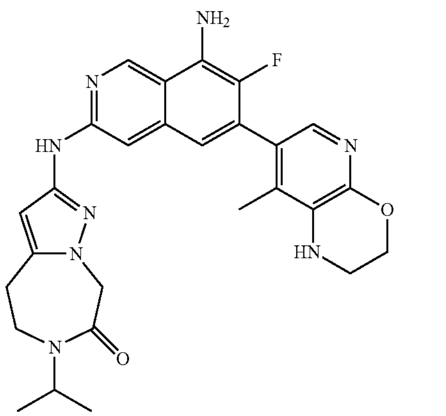 [SMILES: Cc1c(-c2cc3cc(Nc4cc5n(n4)CC(=O)N(C(C)C)CC5)ncc3c(N)c2F)cnc2c1NCCO2] | 2-((8-amino-7-fluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one |
| 234 | 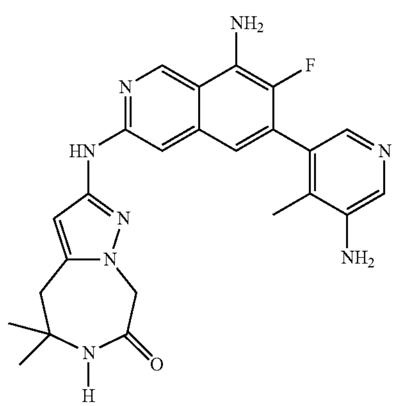 [SMILES: Cc1c(N)cncc1-c1cc2cc(Nc3cc4n(n3)CC(=O)NC(C)(C)C4)ncc2c(N)c1F] | 2-((8-amino-6-(5-amino-4-methylpyridin-3-yl)-7-fluoroisoquinolin-3-yl)amino)-5,5-dimethyl-5,6-dihydro-4H-pyrazolo[1,5-d][1,4]diazepin-7(8H)-one |
| 235 | 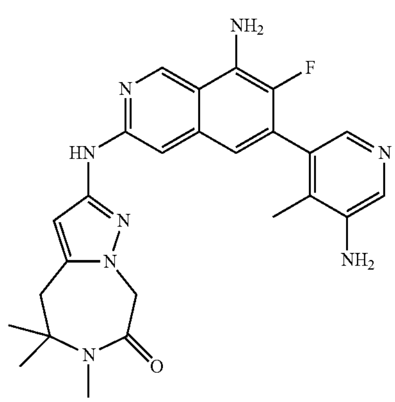 [SMILES: Cc1c(N)cncc1-c1cc2cc(Nc3cc4n(n3)CC(=O)N(C)C(C)(C)C4)ncc2c(N)c1F] | 2-((8-amino-6-(5-amino-4-methylpyridin-3-yl)-7-fluoroisoquinolin-3-yl)amino)-5,5,6-trimethyl-5,6-dihydro-4H-pyrazolo[1,5-d][1,4]diazepin-7(8H)-one |
| 236, 237, 238, 239 | 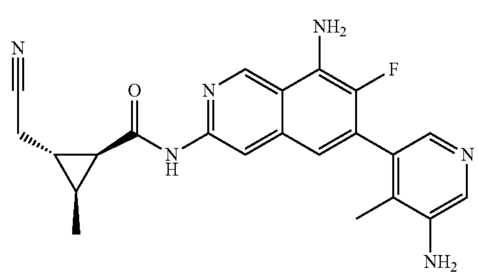 | (1,2)trans-N-(8-amino-6-(5-amino-4-methylpyridin-3-yl)-7-fluoroisoquinolin-3-yl)-2-(cyanomethyl)-3-methylcyclopropane-1-carboxamide |

| Compound No. | Structure | Name |
|---|---|---|
| | 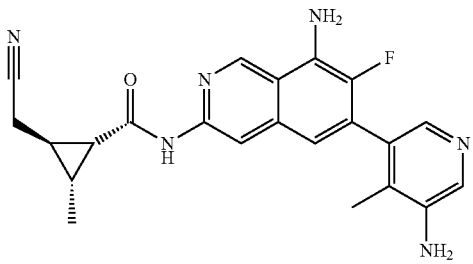 | |
| | 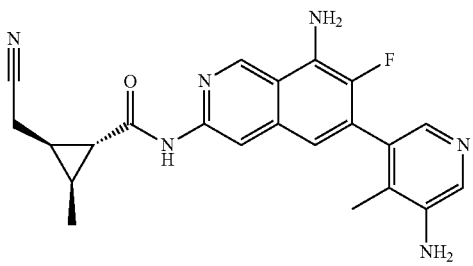 [SMILES: Cc1c(N)cncc1-c1cc2cc(NC(=O)[C@@H]3[C@@H](C)[C@H]3CC#N)ncc2c(N)c1F] | |
| | 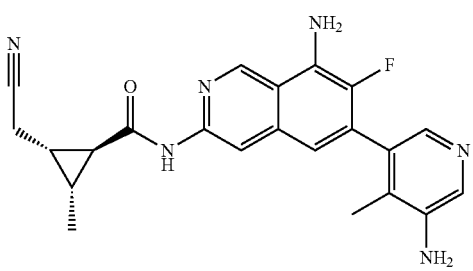 [SMILES: Cc1c(N)cncc1-c1cc2cc(NC(=O)[C@H]3[C@H](C)[C@@H]3CC#N)ncc2c(N)c1F] | |
| 240 | 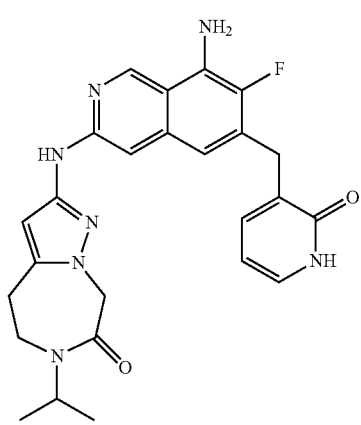 [SMILES: CC(C)N1CCc2cc(Nc3cc4cc(Cc5ccc[nH]c5=O)c(F)c(N)c4cn3)nn2CC1=O] | 2-((8-amino-7-fluoro-6-((2-oxo-1,2-dihydropyridin-3-yl)methyl)isoquinolin-3-yl)amino)-6-isopropyl-5,6-dihydro-4H-pyrazolo[1,5-d][1,4]diazepin-7(8H)-one |

TABLE 2-continued

| Compound No. | Structure | Name |
|---|---|---|
| 241 | 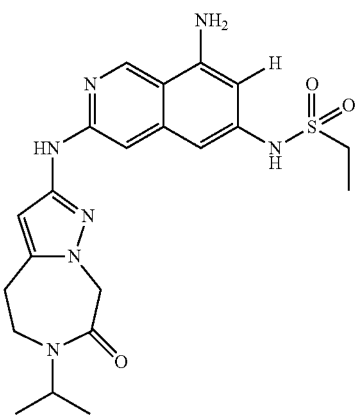 [SMILES: CCS(=O)(=O)Nc1cc(N)c2cnc(Nc3cc4n(n3)CC(=O)N(C(C)C)CC4)cc2c1] | N-(8-amino-3-((6-isopropyl-7-oxo-5,6,7,8-tetrahydro-4H-pyrazolo[1,5-d][1,4]diazepin-2-yl)amino)isoquinolin-6-yl)ethanesulfonamide |
| 242 | 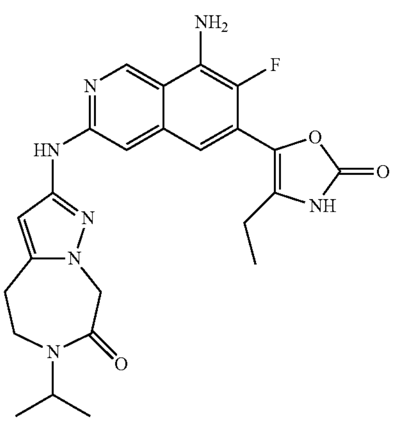 [SMILES: CCc1[nH]c(=O)oc1-c1cc2cc(Nc3cc4n(n3)CC(=O)N(C(C)C)CC4)ncc2c(N)c1F] | 5-(8-amino-7-fluoro-3-((6-isopropyl-7-oxo-5,6,7,8-tetrahydro-4H-pyrazolo[1,5-d][1,4]diazepin-2-yl)amino)isoquinolin-6-yl)-4-ethyloxazol-2(3H)-one |
| 243 | 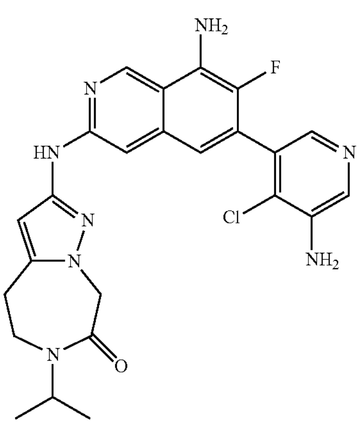 [SMILES: CC(C)N1CCc2cc(Nc3cc4cc(-c5cncc(N)c5Cl)c(F)c(N)c4cn3)nn2CC1=O] | 2-((8-amino-6-(5-amino-4-chloropyridin-3-yl)-7-fluoroisoquinolin-3-yl)amino)-6-isopropyl-5,6-dihydro-4H-pyrazolo[1,5-d][1,4]diazepin-7(8H)-one |

TABLE 2-continued

| Compound No. | Structure | Name |
|---|---|---|
| 244 | 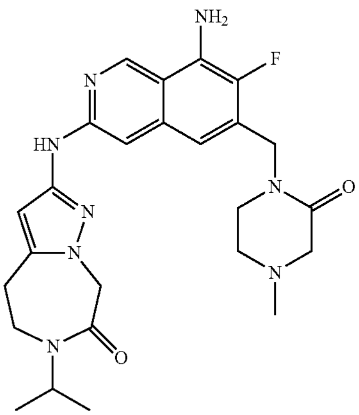 [SMILES: CC(C)N1CCc2cc(Nc3cc4cc(CN5CCN(C)CC5=O)c(F)c(N)c4cn3)nn2CC1=O] | 2-((8-amino-7-fluoro-6-((4-methyl-2-oxopiperazin-1-yl)methyl)isoquinolin-3-yl)amino)-6-isopropyl-5,6-dihydro-4H-pyrazolo[1,5-d][1,4]diazepin-7(8H)-one |
| 245 | 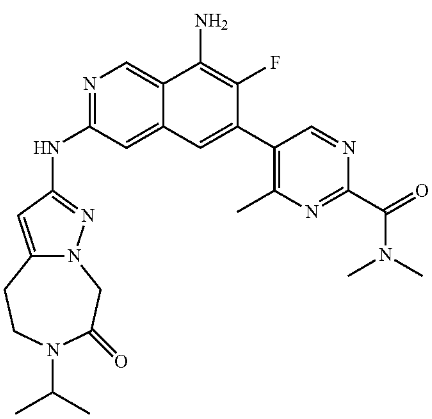 [SMILES: Cc1nc(C(=O)N(C)C)ncc1-c1cc2cc(Nc3cc4n(n3)CC(=O)N(C(C)C)CC4)ncc2c(N)c1F] | 5-(8-amino-7-fluoro-3-((6-isopropyl-7-oxo-5,6,7,8-tetrahydro-4H-pyrazolo[1,5-d][1,4]diazepin-2-yl)amino)isoquinolin-6-yl)-N,N,4-trimethylpyrimidine-2-carboxamide |
| 246 | 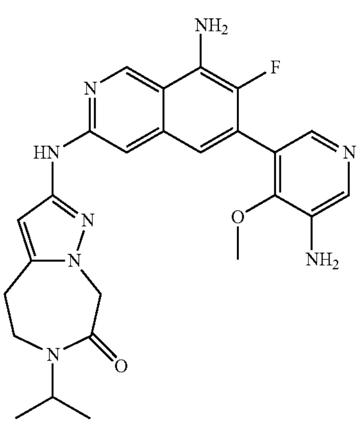 [SMILES: COc1c(N)cncc1-c1cc2cc(Nc3cc4n(n3)CC(=O)N(C(C)C)CC4)ncc2c(N)c1F] | 2-((8-amino-6-(5-amino-4-methoxypyridin-3-yl)-7-fluoroisoquinolin-3-yl)amino)-6-isopropyl-5,6-dihydro-4H-pyrazolo[1,5-d][1,4]diazepin-7(8H)-one |

| Compound No. | Structure | Name |
|---|---|---|
| 247 | 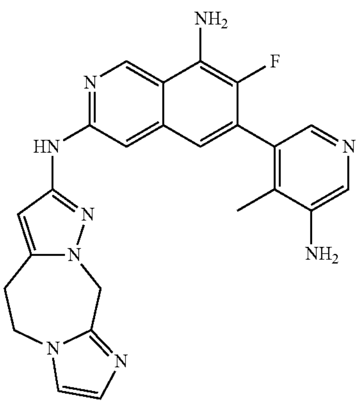 [SMILES: Cc1c(N)cncc1-c1cc2cc(Nc3cc4n(n3)Cc3nccn3CC4)ncc2c(N)c1F] | 6-(5-amino-4-methylpyridin-3-yl)-N3-(5,6-dihydro-11H-imidazo[1,2-a]pyrazolo[1,5-d][1,4]diazepin-8-yl)-7-fluoroisoquinoline-3,8-diamine |
| 248 | 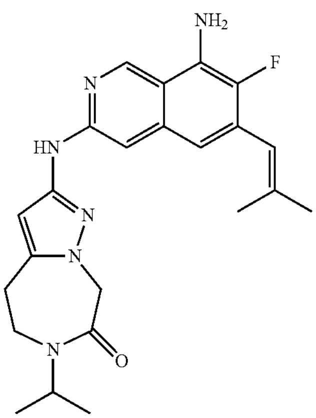 [SMILES: CC(C)=Cc1cc2cc(Nc3cc4n(n3)CC(=O)N(C(C)C)CC4)ncc2c(N)c1F] | 2-((8-amino-7-fluoro-6-(2-methylprop-1-en-1-yl)isoquinolin-3-yl)amino)-6-isopropyl-5,6-dihydro-4H-pyrazolo[1,5-d][1,4]diazepin-7(8H)-one |
| 249 | 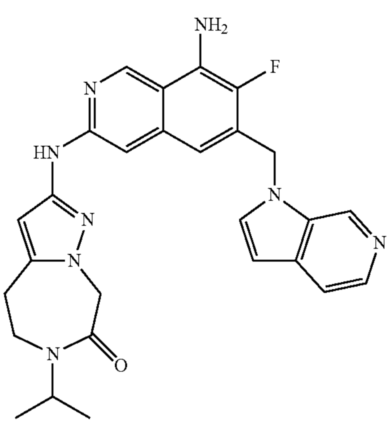 [SMILES: CC(C)N1CCc2cc(Nc3cc4cc(Cn5ccc6ccncc65)c(F)c(N)c4cn3)nn2CC1=O] | 2-((6-((1H-pyrrolo[2,3-c]pyridin-1-yl)methyl)-8-amino-7-fluoroisoquinolin-3-yl)amino)-6-isopropyl-5,6-dihydro-4H-pyrazolo[1,5-d][1,4]diazepin-7(8H)one |

TABLE 2-continued

| Compound No. | Structure | Name |
|---|---|---|
| 250 | 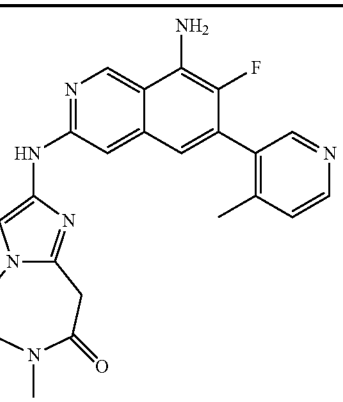 | 2-((8-amino-7-fluoro-6-(4-methylpyridin-3-yl)isoquinolin-3-yl)amino)-7-methyl-6,7-dihydro-5H-imidazo[1,2-d][1,4]diazepin-8(9H)-one |
| 251 | 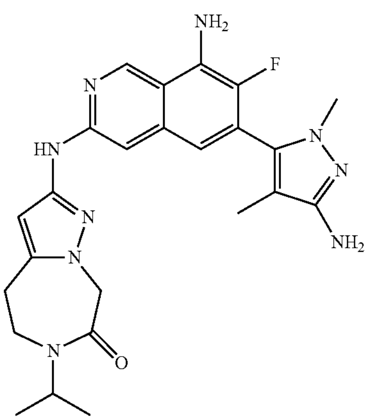 [SMILES: Cc1c(N)nn(C)c1-c1cc2cc(Nc3cc4n(n3)CC(=O)N(C(C)C)CC4)ncc2c(N)c1F] | 2-((8-amino-6-(3-amino-1,4-dimethyl-1H-pyrazol-5-yl)-7-fluoroisoquinolin-3-yl)amino)-6-isopropyl-5,6-dihydro-4H-pyrazolo[1,5-d][1,4]diazepin-7(8H)-one |
| 252 | 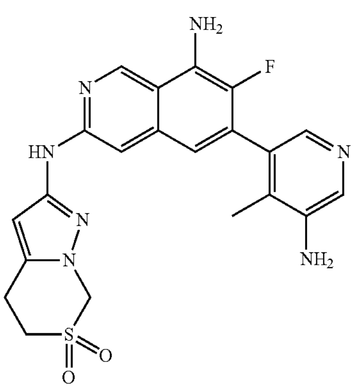 [SMILES: Cc1c(N)cncc1-c1cc2cc(Nc3cc4n(n3)CS(=O)(=O)CC4)ncc2c(N)c1F] | 2-((8-amino-6-(5-amino-4-methylpyridin-3-yl)-7-fluoroisoquinolin-3-yl)amino)-4,5-dihydro-7H-pyrazolo[1,5-c][1,3]thiazine 6,6-dioxide |
| 253 | 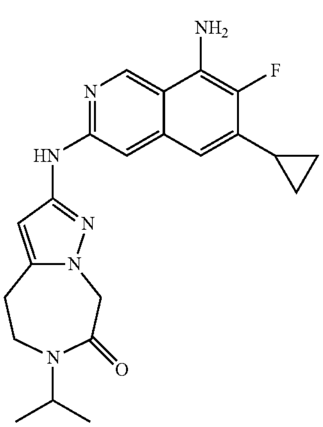 [SMILES: CC(C)N1CCc2cc(Nc3cc4cc(C5CC5)c(F)c(N)c4cn3)nn2CC1=O] | 2-((8-amino-6-cyclopropyl-7-fluoroisoquinolin-3-yl)amino)-6-isopropyl-5,6-dihydro-4H-pyrazolo[1,5-d][1,4]diazepin-7(8H)-one |

TABLE 2-continued

| Compound No. | Structure | Name |
|---|---|---|
| 254 | 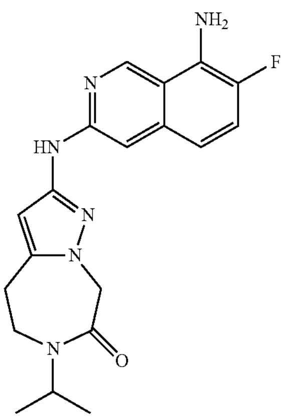 [SMILES: CC(C)N1CCc2cc(Nc3cc4ccc(F)c(N)c4cn3)nn2CC1=O] | 2-((8-amino-7-fluoroisoquinolin-3-yl)amino)-6-isopropyl-5,6-dihydro-4H-pyrazolo[1,5-d][1,4]diazepin-7(8H)-one |
| 255 | 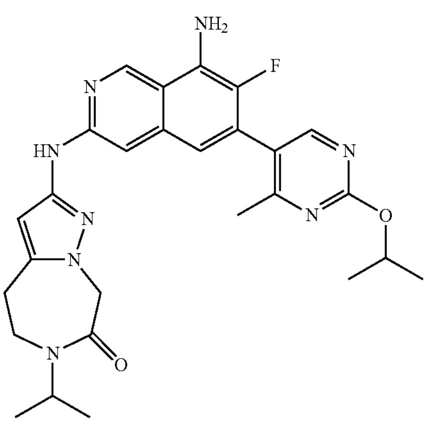 [SMILES: Cc1nc(OC(C)C)ncc1-c1cc2cc(Nc3cc4n(n3)CC(=O)N(C(C)C)CC4)ncc2c(N)c1F] | 2-((8-amino-7-fluoro-6-(2-isopropoxy-4-methylpyrimidin-5-yl)isoquinolin-3-yl)amino)-6-isopropyl-5,6-dihydro-4H-pyrazolo[1,5-d][1,4]diazepin-7(8H)-one |
| 256 | 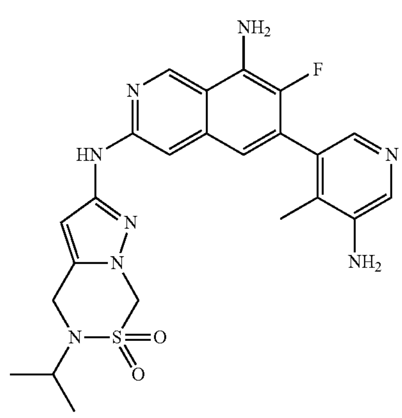 [SMILES: Cc1c(N)cncc1-c1cc2cc(Nc3cc4n(n3)CS(=O)(=O)N(C(C)C)C4)ncc2c(N)c1F] | 2-((8-amino-6-(5-amino-4-methylpyridin-3-yl)-7-fluoroisoquinolin-3-yl)amino)-5-isopropyl-4,5-dihydro-7H-pyrazolo[5,1-d][1,2,5]thiadiazine 6,6-dioxide |

TABLE 2-continued

| Compound No. | Structure | Name |
|---|---|---|
| 257 | 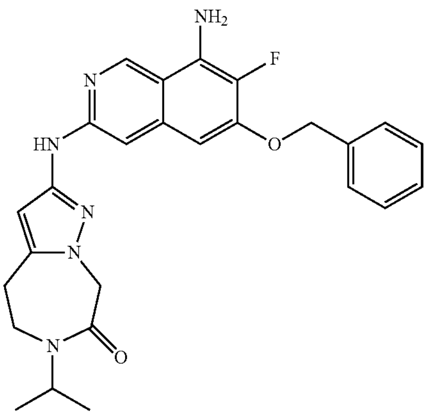 [SMILES: CC(C)N1CCc2cc(Nc3cc4cc(OCc5ccccc5)c(F)c(N)c4cn3)nn2CC1=O] | 2-((8-amino-6-(benzyloxy)-7-fluoroisoquinolin-3-yl)amino)-6-isopropyl-5,6-dihydro-4H-pyrazolo[1,5-d][1,4]diazepin-7(8H)-one |
| 258 | 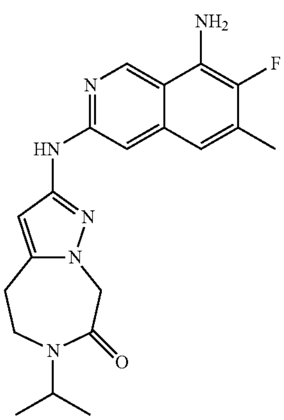 [SMILES: Cc1cc2cc(Nc3cc4n(n3)CC(=O)N(C(C)C)CC4)ncc2c(N)c1F] | 2-((8-amino-7-fluoro-6-methylisoquinolin-3-yl)amino)-6-isopropyl-5,6-dihydro-4H-pyrazolo[1,5-d][1,4]diazepin-7(8H)-one |
| 259 | 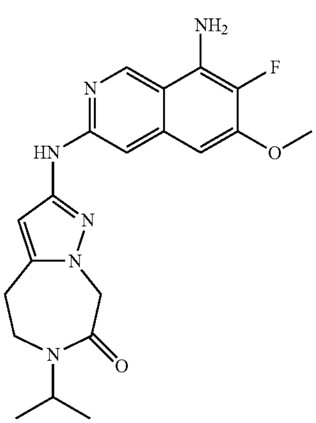 [SMILES: COc1cc2cc(Nc3cc4n(n3)CC(=O)N(C(C)C)CC4)ncc2c(N)c1F] | 2-((8-amino-7-fluoro-6-methoxyisoquinolin-3-yl)amino)-6-isopropyl-5,6-dihydro-4H-pyrazolo[1,5-d][1,4]diazepin-7(8H)-one |

TABLE 2-continued

| Compound No. | Structure | Name |
|---|---|---|
| 260 | 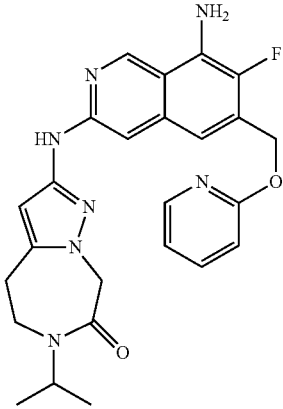 [SMILES: CC(C)N1CCc2cc(Nc3cc4cc(COc5ccccn5)c(F)c(N)c4cn3)nn2CC1=O] | 2-((8-amino-7-fluoro-6-((pyridin-2-yloxy)methyl)isoquinolin-3-yl)amino)-6-isopropyl-5,6-dihydro-4H-pyrazolo[1,5-d][1,4]diazepin-7(8H)-one |
| 261 | 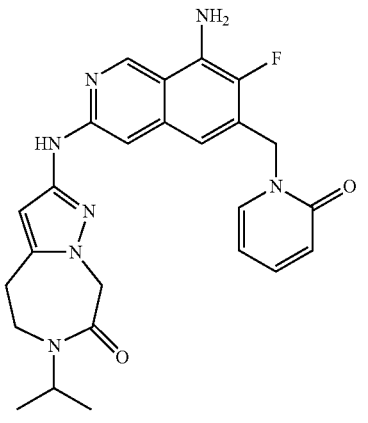 [SMILES: CC(C)N1CCc2cc(Nc3cc4cc(Cn5ccccc5=O)c(F)c(N)c4cn3)nn2CC1=O] | 2-((8-amino-7-fluoro-6-((2-oxopyridin-1(2H)-yl)methyl)isoquinolin-3-yl)amino)-6-isopropyl-5,6-dihydro-4H-pyrazolo[1,5-d][1,4]diazepin-7(8H)-one |
| 262 | 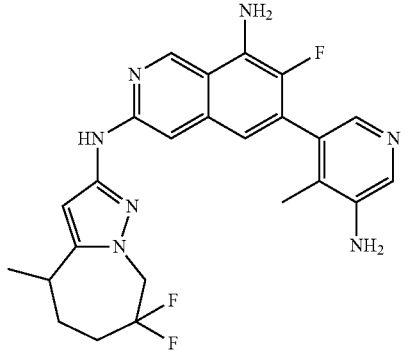 [SMILES: Cc1c(N)cncc1-c1cc2cc(Nc3cc4n(n3)CC(F)(F)CCC4C)ncc2c(N)c1F] | (±)-6-(5-amino-4-methylpyridin-3-yl)-N3-(7,7-difluoro-4-methyl-5,6,7,8-tetrahydro-4H-pyrazolo[1,5-a]azepin-2-yl)-7-fluoroisoquinoline-3,8-diamine |
| 263 | 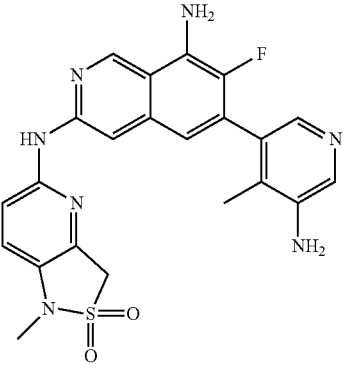 [SMILES: Cc1c(N)cncc1-c1cc2cc(Nc3ccc4c(n3)CS(=O)(=O)N4C)ncc2c(N)c1F] | 5-((8-amino-6-(5-amino-4-methylpyridin-3-yl)-7-fluoroisoquinolin-3-yl)amino)-1-methyl-1,3-dihydroisothiazolo[4,3-b]pyridine 2,2-dioxide |

TABLE 2-continued

| Compound No. | Structure | Name |
|---|---|---|
| 264 | 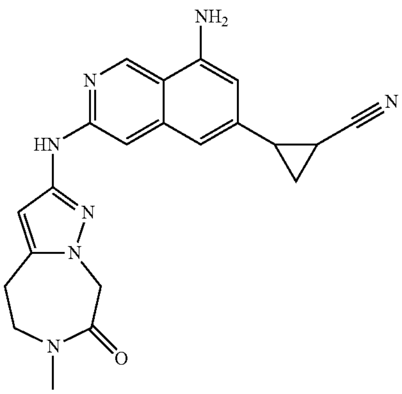 [SMILES: CN1CCc2cc(Nc3cc4cc(C5CC5C#N)cc(N)c4cn3)nn2CC1=O] | 2-(8-amino-3-((6-methyl-7-oxo-5,6,7,8-tetrahydro-4H-pyrazolo[1,5-d][1,4]diazepin-2-yl)amino)isoquinolin-6-yl)cyclopropane-1-carbonitrile |
| 265 | 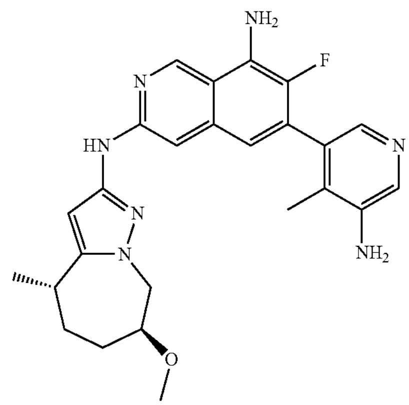 [SMILES: CO[C@H]1CC[C@H](C)c2cc(Nc3cc4cc(-c5cncc(N)c5C)c(F)c(N)c4cn3)nn2C1] | 6-(5-amino-4-methylpyridin-3-yl)-7-fluoro-N3-((4S,7S)-7-methoxy-4-methyl-5,6,7,8-tetrahydro-4H-pyrazolo[1,5-a]azepin-2-yl)isoquinoline-3,8-diamine |
| 266 | 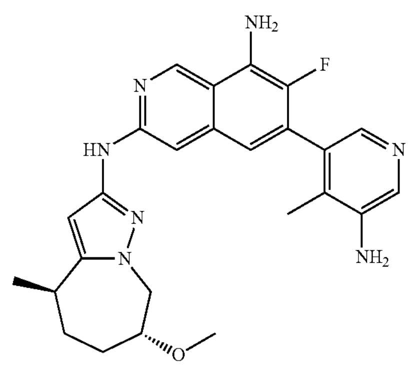 [SMILES: CO[C@@H]1CC[C@@H](C)c2cc(Nc3cc4cc(-c5cncc(N)c5C)c(F)c(N)c4cn3)nn2C1] | 6-(5-amino-4-methylpyridin-3-yl)-7-fluoro-N3-((4R,7R)-7-methoxy-4-methyl-5,6,7,8-tetrahydro-4H-pyrazolo[1,5-a]azepin-2-yl)isoquinoline-3,8-diamine<br>(Stereochemistry arbitrarily assigned) |
| 267 | 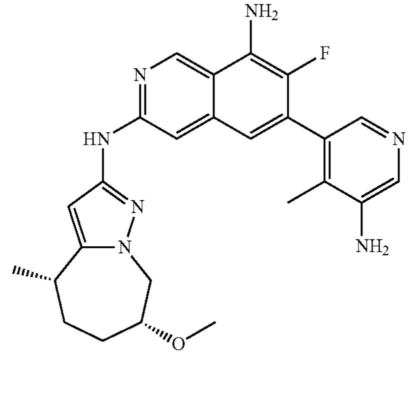 [SMILES: CO[C@@H]1CC[C@H](C)c2cc(Nc3cc4cc(-c5cncc(N)c5C)c(F)c(N)c4cn3)nn2C1] | 6-(5-amino-4-methylpyridin-3-yl)-7-fluoro-N3-((4S,7R)-7-methoxy-4-methyl-5,6,7,8-tetrahydro-4H-pyrazolo[1,5-a]azepin-2-yl)isoquinoline-3,8-diamine<br>(Stereochemistry arbitrarily assigned) |

TABLE 2-continued

| Compound No. | Structure | Name |
|---|---|---|
| 268 | 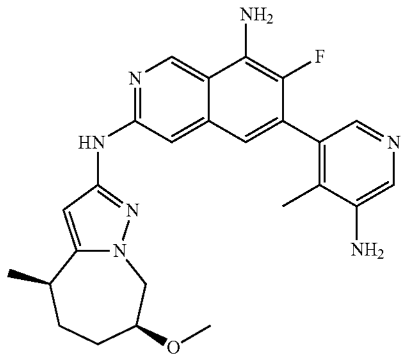 [SMILES: CO[C@H]1CC[C@@H](C)c2cc(Nc3cc4cc(-c5cncc(N)c5C)c(F)c(N)c4cn3)nn2C1] | 6-(5-amino-4-methylpyridin-3-yl)-7-fluoro-N3-((4R,7S)-7-methoxy-4-methyl-5,6,7,8-tetrahydro-4H-pyrazolo[1,5-a]azepin-2-yl)isoquinoline-3,8-diamine (Stereochemistry arbitrarily assigned) |
| 269 | 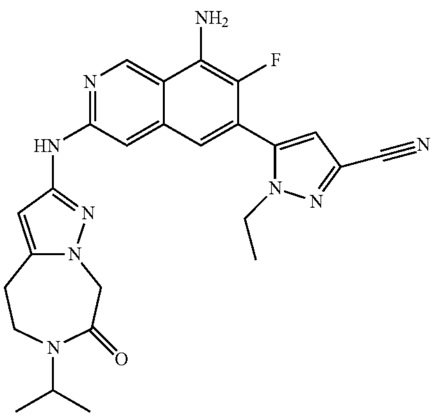 [SMILES: CCn1nc(C#N)cc1-c1cc2cc(Nc3cc4n(n3)CC(=O)N(C(C)C)CC4)ncc2c(N)c1F] | 5-(8-amino-7-fluoro-3-((6-isopropyl-7-oxo-5,6,7,8-tetrahydro-4H-pyrazolo[1,5-d][1,4]diazepin-2-yl)amino)isoquinolin-6-yl)-1-ethyl-1H-pyrazole-3-carbonitrile |
| 270 | 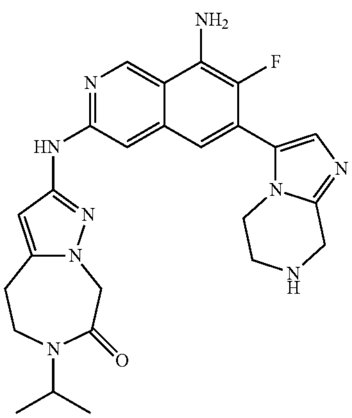 [SMILES: CC(C)N1CCc2cc(Nc3cc4cc(-c5cnc6n5CCNC6)c(F)c(N)c4cn3)nn2CC1=O] | 2-((8-amino-7-fluoro-6-(5,6,7,8-tetrahydroimidazo[1,2-a]pyrazin-3-yl)isoquinolin-3-yl)amino)-6-isopropyl-5,6-dihydro-4H-pyrazolo[1,5-d][1,4]diazepin-7(8H)-one |
| 271 | 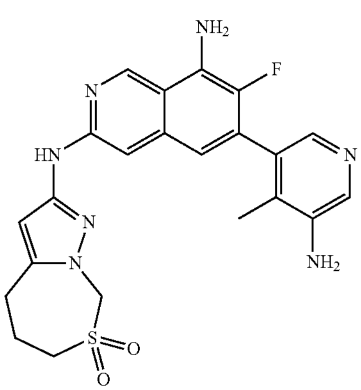 [SMILES: Cc1c(N)cncc1-c1cc2cc(Nc3cc4n(n3)CS(=O)(=O)CCC4)ncc2c(N)c1F] | 2-((8-amino-6-(5-amino-4-methylpyridin-3-yl)-7-fluoroisoquinolin-3-yl)amino)-5,6-dihydro-4H,8H-pyrazolo[1,5-c][1,3]thiazepine 7,7-dioxide |

TABLE 2-continued

| Compound No. | Structure | Name |
|---|---|---|
| 272 | 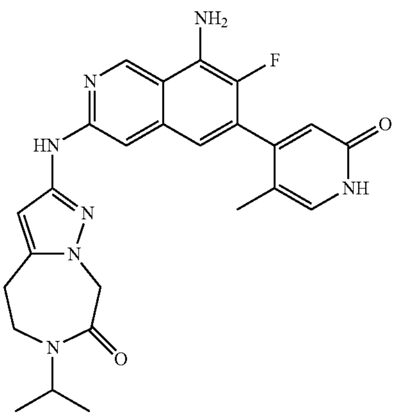 [SMILES: Cc1c[nH]c(=O)cc1-c1cc2cc(Nc3cc4n(n3)CC(=O)N(C(C)C)CC4)ncc2c(N)c1F] | 2-((8-amino-7-fluoro-6-(5-methyl-2-oxo-1,2-dihydropyridin-4-yl)isoquinolin-3-yl)amino)-6-isopropyl-5,6-dihydro-4H-pyrazolo[1,5-d][1,4]diazepin-7(8H)-one |
| 273 | 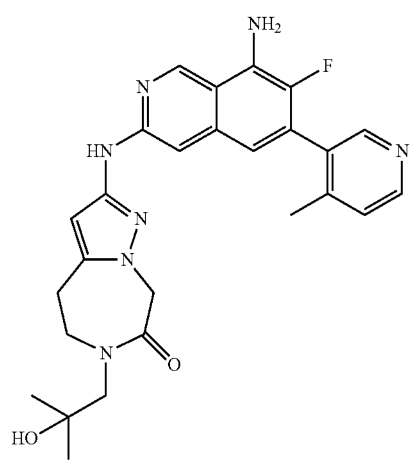 [SMILES: Cc1ccncc1-c1cc2cc(Nc3cc4n(n3)CC(=O)N(CC(C)(C)O)CC4)ncc2c(N)c1F] | .2-((8-amino-7-fluoro-6-(4-methylpyridin-3-yl)isoquinolin-3-yl)amino)-6-(2-hydroxy-2-methylpropyl)-5,6-dihydro-4H-pyrazolo[1,5-d][1,4]diazepin-7(8H)-one |
| 274 | 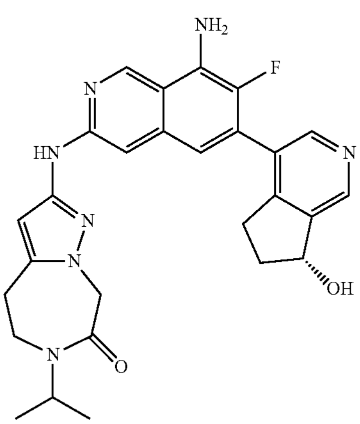 [SMILES: CC(C)N1CCc2cc(Nc3cc4cc(-c5cncc6c5CC[C@H]6O)c(F)c(N)c4cn3)nn2CC1=O] | (R)-2-((8-amino-7-fluoro-6-(7-hydroxy-6,7-dihydro-5H-cyclopenta[c]pyridin-4-yl)isoquinolin-3-yl)amino)-6-isopropyl-5,6-dihydro-4H-pyrazolo[1,5-d][1,4]diazepin-7(8H)-one |

TABLE 2-continued

| Compound No. | Structure | Name |
|---|---|---|
| 275 | 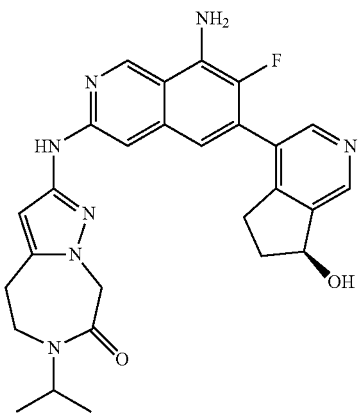 [SMILES: CC(C)N1CCc2cc(Nc3cc4cc(-c5cncc6c5CC[C@@H]6O)c(F)c(N)c4cn3)nn2CC1=O] | (S)-2-((8-amino-7-fluoro-6-(7-hydroxy-6,7-dihydro-5H-cyclopenta[c]pyridin-4-yl)isoquinolin-3-yl)amino)-6-isopropyl-5,6-dihydro-4H-pyrazolo[1,5-d][1,4]diazepin-7(8H)-one (Absolute stereochemistry arbitrarily assigned) |
| 276 | 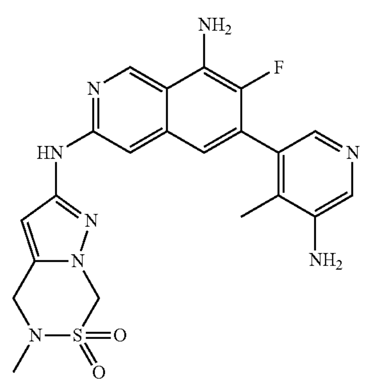 [SMILES: Cc1c(N)cncc1-c1cc2cc(Nc3cc4n(n3)CS(=O)(=O)N(C)C4)ncc2c(N)c1F] | 2-((8-amino-6-(5-amino-4-methylpyridin-3-yl)-7-fluoroisoquinolin-3-yl)amino)-5-methyl-4,5-dihydro-7H-pyrazolo[5,1-d][1,2,5]thiadiazine 6,6-dioxide |
| 277 | 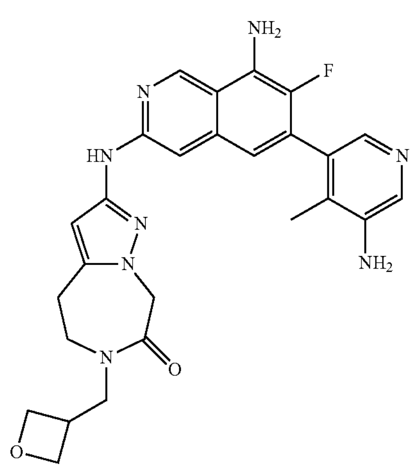 [SMILES: Cc1c(N)cncc1-c1cc2cc(Nc3cc4n(n3)CC(=O)N(CC3COC3)CC4)ncc2c(N)c1F] | 2-((8-amino-6-(5-amino-4-methylpyridin-3-yl)-7-fluoroisoquinolin-3-yl)amino)-6-(oxetan-3-ylmethyl)-5,6-dihydro-4H-pyrazolo[1,5-d][1,4]diazepin-7(8H)-one |

TABLE 2-continued

| Compound No. | Structure | Name |
|---|---|---|
| 278 | 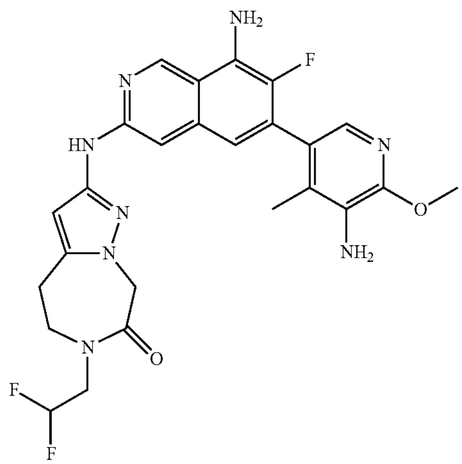 [SMILES: COc1ncc(-c2cc3cc(Nc4cc5n(n4)CC(=O)N(CC(F)F)CC5)ncc3c(N)c2F)c(C)c1N] | 2-((8-amino-6-(5-amino-6-methoxy-4-methylpyridin-3-yl)-7-fluoroisoquinolin-3-yl)amino)-6-(2,2-difluoroethyl)-5,6-dihydro-4H-pyrazolo [1,5-d][1,4]diazepin-7(8H)-one |
| 279, 280, 281, 282 | 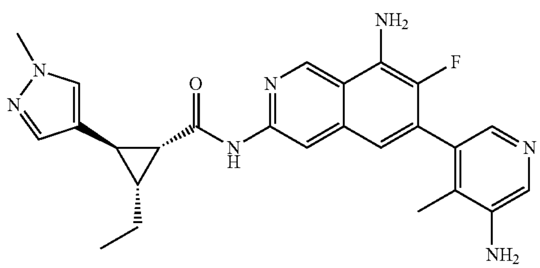 [SMILES: CC[C@H]1[C@@H](C(=O)Nc2cc3cc(-c4cncc(N)c4C)c(F)c(N)c3cn2)[C@@H]1c1cnn(C)c1] | (1,3)trans-N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide |

TABLE 2-continued

| Compound No. | Structure | Name |
|---|---|---|
| 283 | 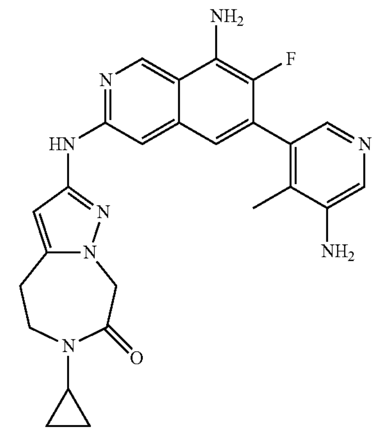 [SMILES: Cc1c(N)cncc1-c1cc2cc(Nc3cc4n(n3)CC(=O)N(C3CC3)CC4)ncc2c(N)c1F] | 2-((8-amino-6-(5-amino-4-methylpyridin-3-yl)-7-fluoroisoquinolin-3-yl)amino)-6-cyclopropyl-5,6-dihydro-4H-pyrazolo[1,5-d][1,4]diazepin-7(8H)-one |
| 284 | 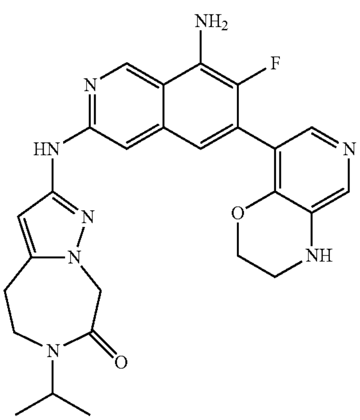 [SMILES: CC(C)N1CCc2cc(Nc3cc4cc(-c5cncc6c5OCCN6)c(F)c(N)c4cn3)nn2CC1=O] | 2-((8-amino-6-(3,4-dihydro-2H-pyrido[4,3-b][1,4]oxazin-8-yl)-7-fluoroisoquinolin-3-yl)amino)-6-isopropyl-5,6-dihydro-4H-pyrazolo[1,5-d][1,4]diazepin-7(8H)-one |
| 285 | 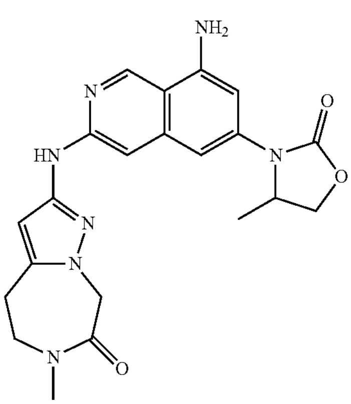 [SMILES: CC1COC(=O)N1c1cc(N)c2cnc(Nc3cc4n(n3)CC(=O)N(C)CC4)cc2c1] | 3-(8-amino-3-((6-methyl-7-oxo-5,6,7,8-tetrahydro-4H-pyrazolo[1,5-d][1,4]diazepin-2-yl)amino)isoquinolin-6-yl)-4-methyloxazolidin-2-one |

TABLE 2-continued

| Compound No. | Structure | Name |
| --- | --- | --- |
| 286 | 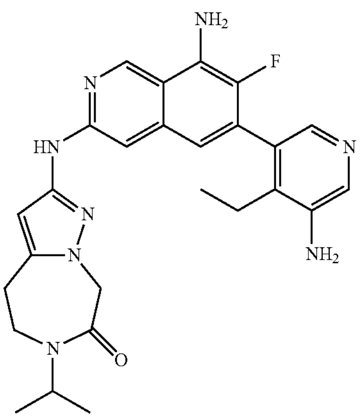 [SMILES: CCc1c(N)cncc1-c1cc2cc(Nc3cc4n(n3)CC(=O)N(C(C)C)CC4)ncc2c(N)c1F] | 2-((8-amino-6-(5-amino-4-ethylpyridin-3-yl)-7-fluoroisoquinolin-3-yl)amino)-6-isopropyl-5,6-dihydro-4H-pyrazolo[1,5-d][1,4]diazepin-7(8H)-one |
| 287 | 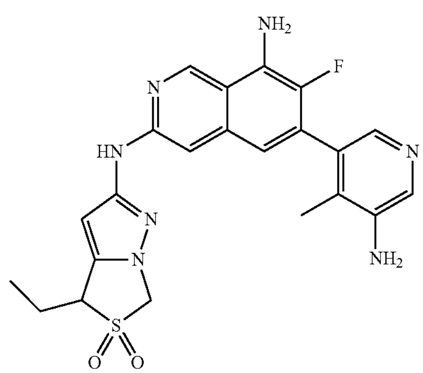 [SMILES: CCC1c2cc(Nc3cc4cc(-c5cncc(N)c5C)c(F)c(N)c4cn3)nn2CS1(=O)=O] | 2-((8-amino-6-(5-amino-4-methylpyridin-3-yl)-7-fluoroisoquinolin-3-yl)amino)-4-ethyl-4H,6H-pyrazolo[1,5-c]thiazole 5,5-dioxide |
| 288 | 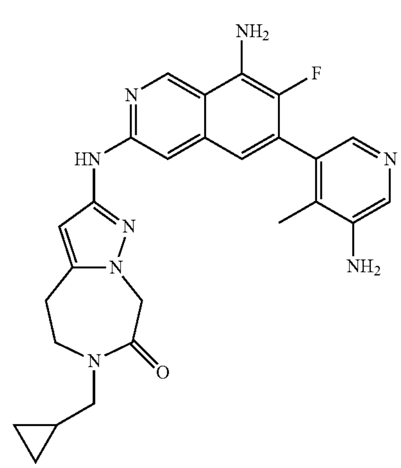 [SMILES: Cc1c(N)cncc1-c1cc2cc(Nc3cc4n(n3)CC(=O)N(CC3CC3)CC4)ncc2c(N)c1F] | 2-((8-amino-6-(5-amino-4-methylpyridin-3-yl)-7-fluoroisoquinolin-3-yl)amino)-6-(cyclopropylmethyl)-5,6-dihydro-4H-pyrazolo[1,5-d][1,4]diazepin-7(8H)-one |

TABLE 2-continued

| Compound No. | Structure | Name |
|---|---|---|
| 289 | 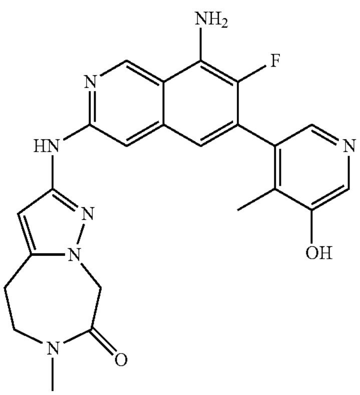 [SMILES: Cc1c(O)cncc1-c1cc2cc(Nc3cc4n(n3)CC(=O)N(C)CC4)ncc2c(N)c1F] | 2-((8-amino-7-fluoro-6-(5-hydroxy-4-methylpyridin-3-yl)isoquinolin-3-yl)amino)-6-methyl-5,6-dihydro-4H-pyrazolo[1,5-d][1,4]diazepin-7(8H)-one |
| 290 | 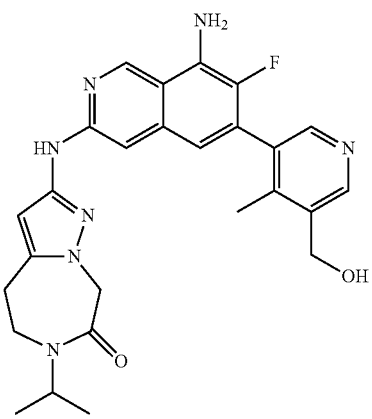 [SMILES: Cc1c(CO)cncc1-c1cc2cc(Nc3cc4n(n3)CC(=O)N(C(C)C)CC4)ncc2c(N)c1F] | 2-((8-amino-7-fluoro-6-(5-(hydroxymethyl)-4-methylpyridin-3-yl)isoquinolin-3-yl)amino)-6-isopropyl-5,6-dihydro-4H-pyrazolo[1,5-d][1,4]diazepin-7(8H)-one |
| 291 | 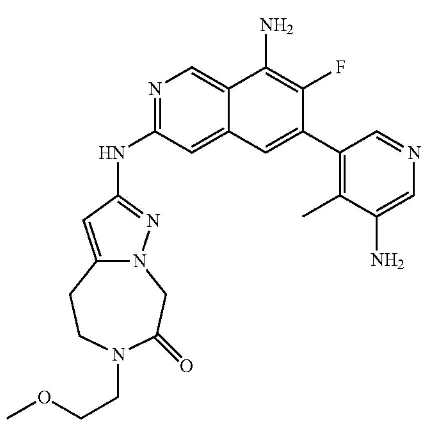 [SMILES: COCCN1CCc2cc(Nc3cc4cc(-c5cncc(N)c5C)c(F)c(N)c4cn3)nn2CC1=O] | 2-((8-amino-6-(5-amino-4-methylpyridin-3-yl)-7-fluoroisoquinolin-3-yl)amino)-6-(2-methoxyethyl)-5,6-dihydro-4H-pyrazolo[1,5-d][1,4]diazepin-7(8H)-one |

TABLE 2-continued

| Compound No. | Structure | Name |
|---|---|---|
| 292 | 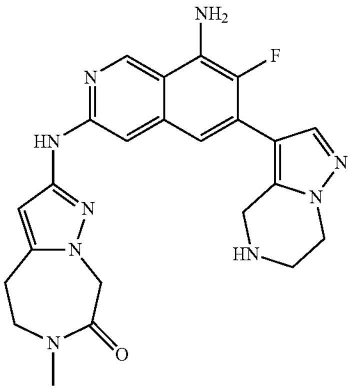 [SMILES: CN1CCc2cc(Nc3cc4cc(-c5cnn6c5CNCC6)c(F)c(N)c4cn3)nn2CC1=O] | 2-((8-amino-7-fluoro-6-(4,5,6,7-tetrahydropyrazolo[1,5-a]pyrazin-3-yl)isoquinolin-3-yl)amino)-6-methyl-5,6-dihydro-4H-pyrazolo [1,5-d][1,4]diazepin-7(8H)-one |
| 293 | 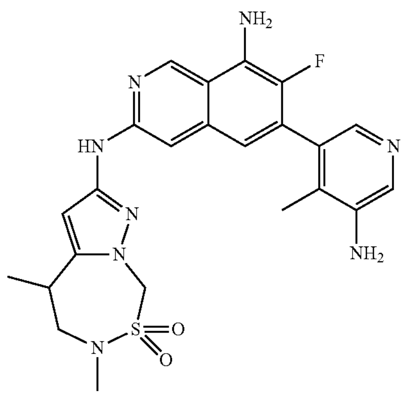 [SMILES: Cc1c(N)cncc1-c1cc2cc(Nc3cc4n(n3)CS(=O)(=O)N(C)CC4C)ncc2c(N)c1F] | 2-((8-amino-6-(5-amino-4-methylpyridin-3-yl)-7-fluoroisoquinolin-3-yl)amino)-4,6-dimethyl-5,6-dihydro-4H,8H-pyrazolo[5,1-e][1,2,6]thiadiazepine 7,7-dioxide |
| 294, 295, 296, 297 | | (1,3)trans-N-(8-amino-6-(5-amino-6-methoxy-4-methylpyridin-3-yl)-7-fluoroisoquinolin-3-yl)-2-methyl-3-(1-methyl-1H-pyrazol-4-yl)cyclopropane-1-carboxamide |
| | | |

| Compound No. | Structure | Name |
|---|---|---|
| | (structure) | |
| | (structure) | |
| 298 | (structure) | 2-((8-amino-6-(5-amino-4-methylpyridin-3-yl)-7-fluoroisoquinolin-3-yl)amino)-6-ethyl-5,6-dihydro-4H-pyrazolo [1,5-d][1,4]diazepin-7(8H)-one |
| 299 | (structure) | 2-((8-amino-6-(5-amino-4,6-dimethylpyridin-3-yl)-7-fluoroisoquinolin-3-yl)amino)-6-methyl-5,6-dihydro-4H-pyrazolo[1,5-d][1,4]diazepin-7(8H)-one |

TABLE 2-continued

| Compound No. | Structure | Name |
|---|---|---|
| 300 | 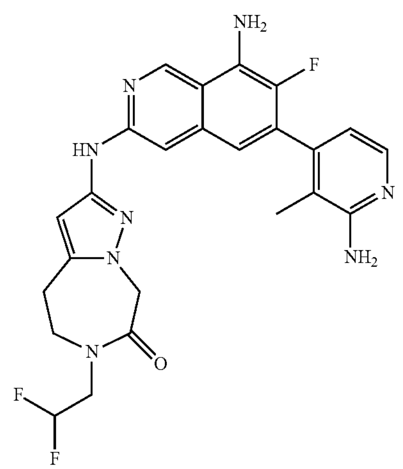 | 2-((8-amino-6-(2-amino-3-methylpyridin-4-yl)-7-fluoroisoquinolin-3-yl)amino)-6-(2,2-difluoroethyl)-5,6-dihydro-4H-pyrazolo[1,5-d][1,4]diazepin-7(8H)-one |
| 301 | 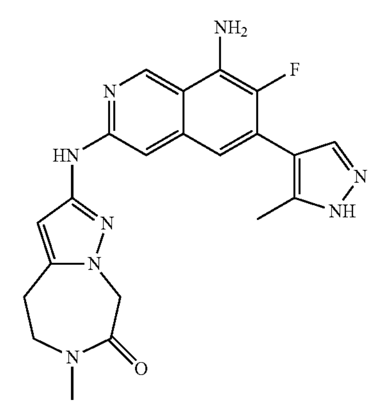 [SMILES: Cc1[nH]ncc1-c1cc2cc(Nc3cc4n(n3)CC(=O)N(C)CC4)ncc2c(N)c1F] | 2-((8-amino-7-fluoro-6-(5-methyl-1H-pyrazol-4-yl)isoquinolin-3-yl)amino)-6-methyl-5,6-dihydro-4H-pyrazolo[1,5-d][1,4]diazepin-7(8H)-one |
| 302 | 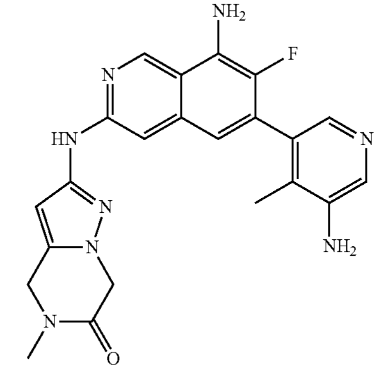 [SMILES: Cc1c(N)cncc1-c1cc2cc(Nc3cc4n(n3)CC(=O)N(C)C4)ncc2c(N)c1F] | 2-((8-amino-6-(5-amino-4-methylpyridin-3-yl)-7-fluoroisoquinolin-3-yl)amino)-5-methyl-4,5-dihydropyrazolo[1,5-a]pyrazin-6(7H)-one |

TABLE 2-continued

| Compound No. | Structure | Name |
|---|---|---|
| 303 | 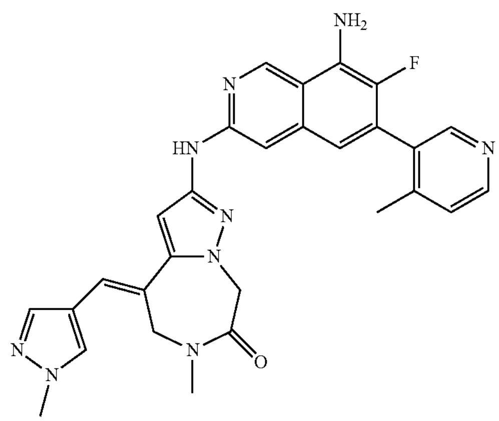 [SMILES: Cc1ccncc1-c1cc2cc(Nc3cc4n(n3)CC(=O)N(C)C/C4=C\c3cnn(C)c3)ncc2c(N)c1F] | (E)-2-((8-amino-7-fluoro-6-(4-methylpyridin-3-yl)isoquinolin-3-yl)amino)-6-methyl-4-((1-methyl-1H-pyrazol-4-yl)methylene)-5,6-dihydro-4H-pyrazolo[1,5-d][1,4]diazepin-7(8H)-one |
| 304 | 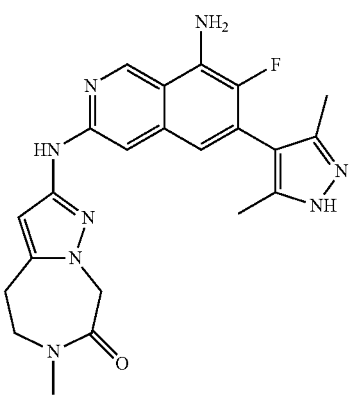 [SMILES: Cc1n[nH]c(C)c1-c1cc2cc(Nc3cc4n(n3)CC(=O)N(C)CC4)ncc2c(N)c1F] | 2-((8-amino-6-(3,5-dimethyl-1H-pyrazol-4-yl)-7-fluoroisoquinolin-3-yl)amino)-6-methyl-5,6-dihydro-4H-pyrazolo[1,5-d][1,4]diazepin-7(8H)-one |
| 305 | 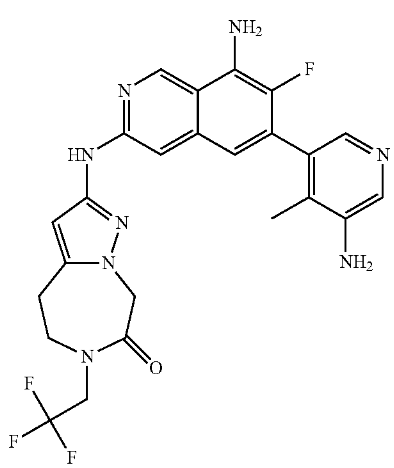 [SMILES: Cc1c(N)cncc1-c1cc2cc(Nc3cc4n(n3)CC(=O)N(CC(F)(F)F)CC4)ncc2c(N)c1F] | 2-((8-amino-6-(5-amino-4-methylpyridin-3-yl)-7-fluoroisoquinolin-3-yl)amino)-6-(2,2,2-trifluoroethyl)-5,6-dihydro-4H-pyrazolo[1,5-d][1,4]diazepin-7(8H)-one |

TABLE 2-continued

| Compound No. | Structure | Name |
|---|---|---|
| 306 | 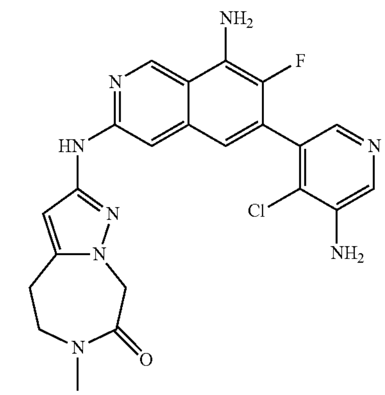 [SMILES: CN1CCc2cc(Nc3cc4cc(-c5cncc(N)c5Cl)c(F)c(N)c4cn3)nn2CC1=O] | 2-((8-amino-6-(5-amino-4-chloropyridin-3-yl)-7-fluoroisoquinolin-3-yl)amino)-6-methyl-5,6-dihydro-4H-pyrazolo[1,5-d][1,4]diazepin-7(8H)-one |
| 307 | 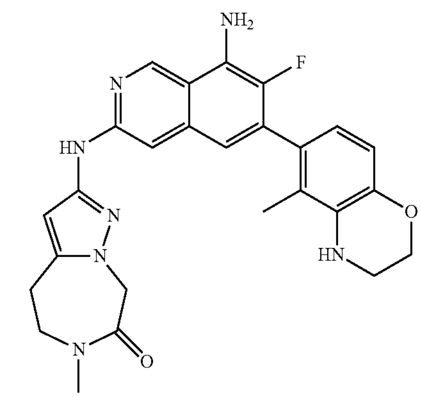 [SMILES: Cc1c(-c2cc3cc(Nc4cc5n(n4)CC(=O)N(C)CC5)ncc3c(N)c2F)ccc2c1NCCO2] | 2-((8-amino-7-fluoro-6-(5-methyl-3,4-dihydro-2H-benzo[b][1,4]oxazin-6-yl)isoquinolin-3-yl)amino)-6-methyl-5,6-dihydro-4H-pyrazolo[1,5-d][1,4]diazepin-7(8H)-one |
| 308 | 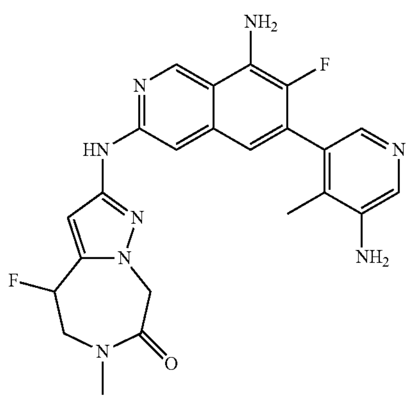 [SMILES: Cc1c(N)cncc1-c1cc2cc(Nc3cc4n(n3)CC(=O)N(C)CC4F)ncc2c(N)c1F] | 2-((8-amino-6-(5-amino-4-methylpyridin-3-yl)-7-fluoroisoquinolin-3-yl)amino)-4-fluoro-6-methyl-5,6-dihydro-4H-pyrazolo[1,5-d][1,4]diazepin-7(8H)-one |
| 309 | 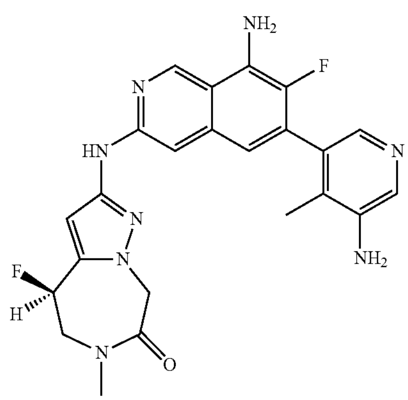 [SMILES: Cc1c(N)cncc1-c1cc2cc(Nc3cc4n(n3)CC(=O)N(C)C[C@H]4F)ncc2c(N)c1F] | (R)-2-((8-amino-6-(5-amino-4-methylpyridin-3-yl)-7-fluoroisoquinolin-3-yl)amino)-4-fluoro-6-methyl-5,6-dihydro-4H-pyrazolo[1,5-d][1,4]diazepin-7(8H)-one (Absolute stereochemistry arbitrarily assigned) |

TABLE 2-continued

| Compound No. | Structure | Name |
|---|---|---|
| 310 | 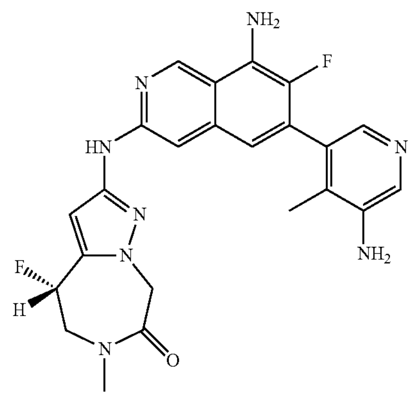 [SMILES: Cc1c(N)cncc1-c1cc2cc(Nc3cc4n(n3)CC(=O)N(C)C[C@@H]4F)ncc2c(N)c1F] | (S)-2-((8-amino-6-(5-amino-4-methylpyridin-3-yl)-7-fluoroisoquinolin-3-yl)amino)-4-fluoro-6-methyl-5,6-dihydro-4H-pyrazolo[1,5-d][1,4]diazepin-7(8H)-one (Absolute stereochemistry arbitrarily assigned) |
| 311 | 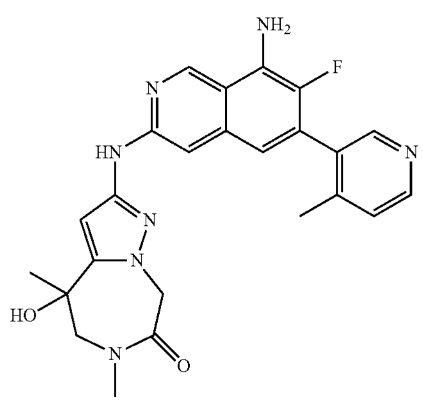 [SMILES: Cc1ccncc1-c1cc2cc(Nc3cc4n(n3)CC(=O)N(C)CC4(C)O)ncc2c(N)c1F] | 2-((8-amino-7-fluoro-6-(4-methylpyridin-3-yl)isoquinolin-3-yl)amino)-4-hydroxy-4,6-dimethyl-5,6-dihydro-4H-pyrazolo[1,5-d][1,4]diazepin-7(8H)-one |
| 312 | 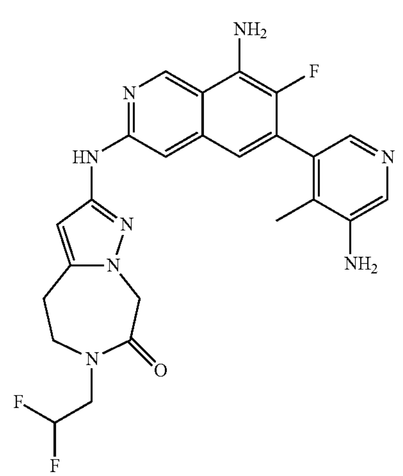 [SMILES: Cc1c(N)cncc1-c1cc2cc(Nc3cc4n(n3)CC(=O)N(CC(F)F)CC4)ncc2c(N)c1F] | 2-((8-amino-6-(5-amino-4-methylpyridin-3-yl)-7-fluoroisoquinolin-3-yl)amino)-6-(2,2-difluoroethyl)-5,6-dihydro-4H-pyrazolo[1,5-d][1,4]diazepin-7(8H)-one |

TABLE 2-continued

| Compound No. | Structure | Name |
|---|---|---|
| 313 | 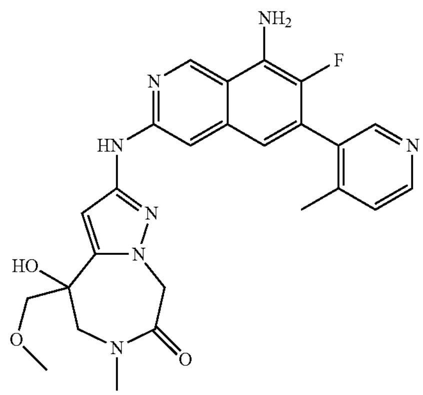 [SMILES: COCC1(O)CN(C)C(=O)Cn2nc(Nc3cc4cc(-c5cnccc5C)c(F)c(N)c4cn3)cc21] | 2-((8-amino-7-fluoro-6-(4-methylpyridin-3-yl)isoquinolin-3-yl)amino)-4-hydroxy-4-(methoxymethyl)-6-methyl-5,6-dihydro-4H-pyrazolo[1,5-d][1,4]diazepin-7(8H)-one |
| 314 | 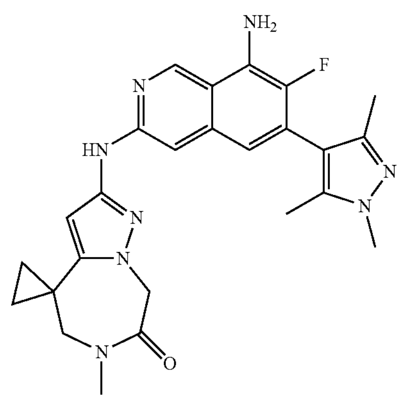 [SMILES: Cc1nn(C)c(C)c1-c1cc2cc(Nc3cc4n(n3)CC(=O)N(C)CC43CC3)ncc2c(N)c1F] | 2'-((8-amino-7-fluoro-6-(1,3,5-trimethyl-1H-pyrazol-4-yl)isoquinolin-3-yl)amino)-6'-methyl-5',6'-dihydrospiro[cyclopropane-1,4'-pyrazolo[1,5-d][1,4]diazepin]-7'(8'H)-one |
| 315 | 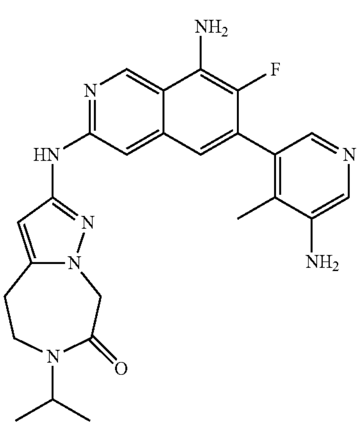 | 2-((8-amino-6-(5-amino-4-methylpyridin-3-yl)-7-fluoroisoquinolin-3-yl)amino)-6-isopropyl-5,6-dihydro-4H-pyrazolo[1,5-d][1,4]diazepin-7(8H)-one |
| 316 | 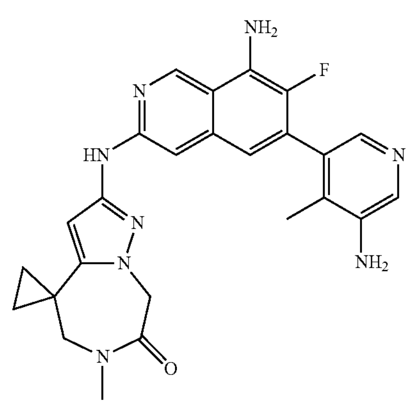 [SMILES: Cc1c(N)cncc1-c1cc2cc(Nc3cc4n(n3)CC(=O)N(C)CC43CC3)ncc2c(N)c1F] | 2'-((8-amino-6-(5-amino-4-methylpyridin-3-yl)-7-fluoroisoquinolin-3-yl)amino)-6'-methyl-5',6'-dihydrospiro[cyclopropane-1,4'-pyrazolo[1,5-d][1,4]diazepin]-7'(8'H)-one |

TABLE 2-continued

| Compound No. | Structure | Name |
|---|---|---|
| 317 | 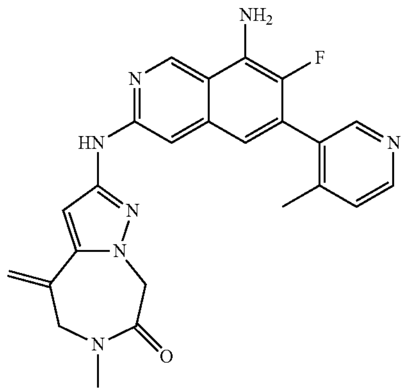 [SMILES: C=C1CN(C)C(=O)Cn2nc(Nc3cc4cc(-c5cnccc5C)c(F)c(N)c4cn3)cc21] | 2-((8-amino-7-fluoro-6-(4-methylpyridin-3-yl)isoquinolin-3-yl)amino)-6-methyl-4-methylene-5,6-dihydro-4H-pyrazolo[1,5-d][1,4]diazepin-7(8H)-one |
| 318 | 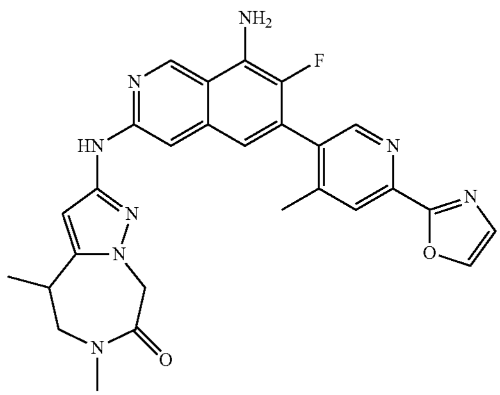 [SMILES: Cc1cc(-c2ncco2)ncc1-c1cc2cc(Nc3cc4n(n3)CC(=O)N(C)CC4C)ncc2c(N)c1F] | 2-((8-amino-7-fluoro-6-(4-methyl-6-(oxazol-2-yl)pyridin-3-yl)isoquinolin-3-yl)amino)-4,6-dimethyl-5,6-dihydro-4H-pyrazolo[1,5-d][1,4]diazepin-7(8H)-one |
| 319, 320, 321, 322 | | (1,2)trans-N-(8-amino-7-fluoro-6-(4-methylpyridin-3-yl)isoquinolin-3-yl)-2-(1H-imidazol-5-yl)-3-methylcyclopropane-1-carboxamide |

TABLE 2-continued

| Compound No. | Structure | Name |
|---|---|---|
| 323, 324 | | N-(8-amino-7-fluoro-6-(4-methylpyridin-3-yl)isoquinolin-3-yl)-2-(cyanomethyl)-3-(1H-imidazol-4-yl)cyclopropane-1-carboxamide |
| 325 | 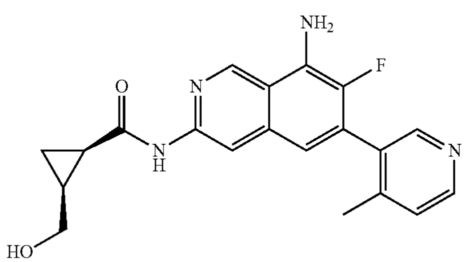 [SMILES: Cc1ccncc1-c1cc2cc(NC(=O)[C@@H]3C[C@@H]3CO)ncc2c(N)c1F] | cis-N-(8-amino-7-fluoro-6-(4-methylpyridin-3-yl)isoquinolin-3-yl)-2-(hydroxymethyl)cyclopropane-1-carboxamide |
| 326 | 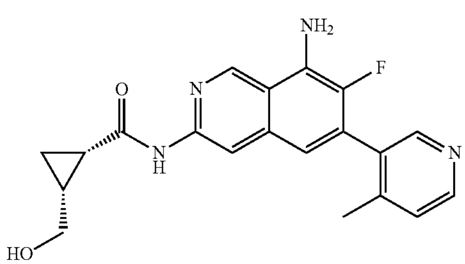 [SMILES: Cc1ccncc1-c1cc2cc(NC(=O)[C@H]3C[C@H]3CO)ncc2c(N)c1F] | (1S,2R)-N-(8-amino-7-fluoro-6-(4-methylpyridin-3-yl)isoquinolin-3-yl)-2-(hydroxymethyl)cyclopropane-1-carboxamide (Hydroxymethyl trans to amide; Absolute stereochemistry arbitrarily assigned) |

TABLE 2-continued

| Compound No. | Structure | Name |
|---|---|---|
| 327 | 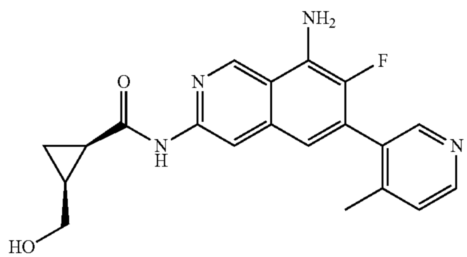 [SMILES: Cc1ccncc1-c1cc2cc(NC(=O)[C@@H]3C[C@@H]3CO)ncc2c(N)c1F] | (1R,2S)-N-(8-amino-7-fluoro-6-(4-methylpyridin-3-yl)isoquinolin-3-yl)-2-(hydroxymethyl)cyclopropane-1-carboxamide (Hydroxymethyl trans to amide; Absolute stereochemistry arbitrarily assigned) |
| 328 | 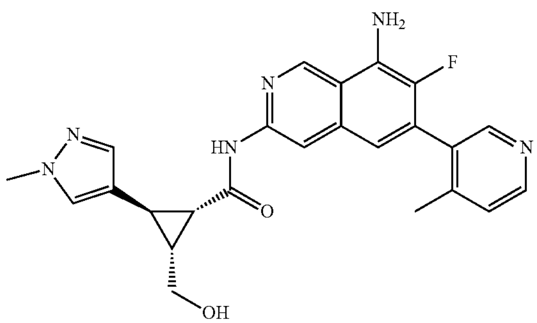 [SMILES: Cc1ccncc1-c1cc2cc(NC(=O)[C@@H]3[C@H](CO)[C@H]3c3cnn(C)c3)ncc2c(N)c1F] | N-(8-amino-7-fluoro-6-(4-methylpyridin-3-yl)isoquinolin-3-yl)-2-(hydroxymethyl)-3-(1-methyl-1H-pyrazol-4-yl)cyclopropane-1-carboxamide |
| 329, 330, 331, 332 | 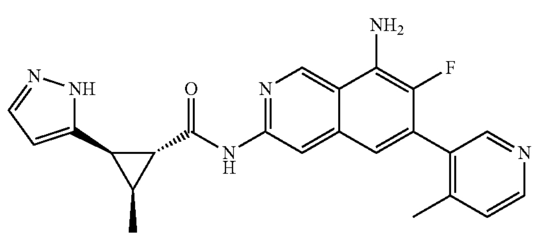 [SMILES: Cc1ccncc1-c1cc2cc(NC(=O)[C@@H]3[C@@H](C)[C@H]3c3ccn[nH]3)ncc2c(N)c1F] | (1,3) trans-N-(8-amino-7-fluoro-6-(4-methylpyridin-3-yl)isoquinolin-3-yl)-2-methyl-3-(1H-pyrazol-5-yl)cyclopropane-1-carboxamide |

TABLE 2-continued

| Compound No. | Structure | Name |
|---|---|---|
| | | |
| | | |
| 333 | 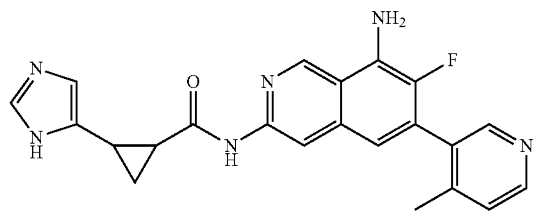 [SMILES: Cc1ccncc1-c1cc2cc(NC(=O)C3CC3c3cnc[nH]3)ncc2c(N)c1F] | trans-N-(8-amino-7-fluoro-6-(4-methylpyridin-3-yl)isoquinolin-3-yl)-2-(1H-imidazol-5-yl)cyclopropane-1-carboxamide |
| 334 | 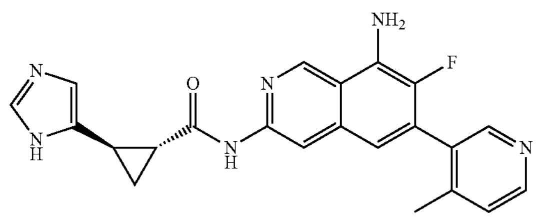 [SMILES: Cc1ccncc1-c1cc2cc(NC(=O)[C@@H]3C[C@H]3c3cnc[nH]3)ncc2c(N)c1F] | (1R,2R)-N-(8-amino-7-fluoro-6-(4-methylpyridin-3-yl)isoquinolin-3-yl)-2-(1H-imidazol-5-yl)cyclopropane-1-carboxamide |
| 335 | 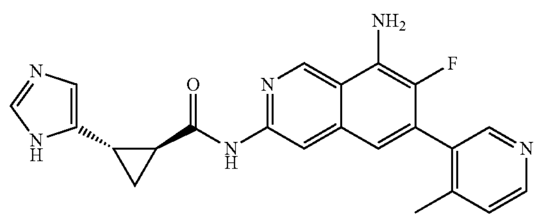 [SMILES: Cc1ccncc1-c1cc2cc(NC(=O)[C@H]3C[C@@H]3c3cnc[nH]3)ncc2c(N)c1F] | (1S,2S)-N-(8-amino-7-fluoro-6-(4-methylpyridin-3-yl)isoquinolin-3-yl)-2-(1H-imidazol-5-yl)cyclopropane-1-carboxamide |
| 336 | 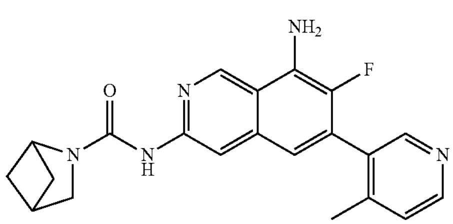 [SMILES: Cc1ccncc1-c1cc2cc(NC(=O)N3CC4CC3C4)ncc2c(N)c1F] | N-(8-amino-7-fluoro-6-(4-methylpyridin-3-yl)isoquinolin-3-yl)-2-azabicyclo[2.1.1]hexane-2-carboxamide |
| 337, 338, 339, 340 | 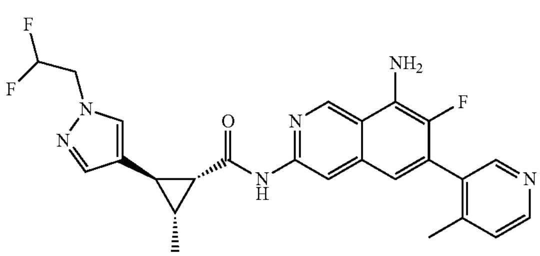 [SMILES: Cc1ccncc1-c1cc2cc(NC(=O)[C@@H]3[C@H](C)[C@H]3c3cnn(CC(F)F)c3)ncc2c(N)c1F] | (1,2)trans-N-(8-amino-7-fluoro-6-(4-methylpyridin-3-yl)isoquinolin-3-yl)-2-(1-(2,2-difluoroethyl)-1H-pyrazol-4-yl)-3-methylcyclopropane-1-carboxamide |

| Compound No. | Structure | Name |
|---|---|---|
| | 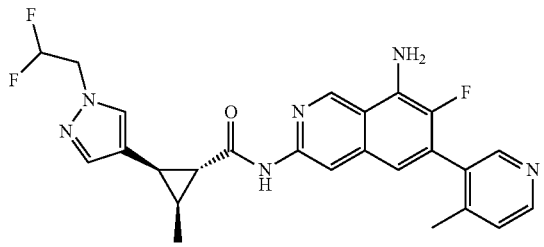 [SMILES: Cc1ccncc1-c1cc2cc(NC(=O)[C@@H]3[C@@H](C)[C@H]3c3cnn(CC(F)F)c3)ncc2c(N)c1F] | |
| | 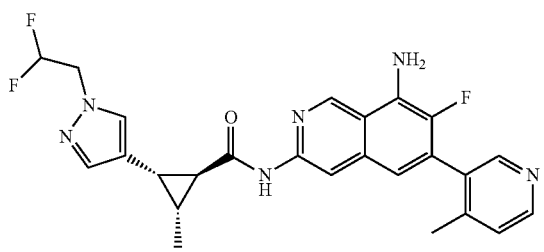 [SMILES: Cc1ccncc1-c1cc2cc(NC(=O)[C@H]3[C@H](C)[C@@H]3c3cnn(CC(F)F)c3)ncc2c(N)c1F] | |
| | 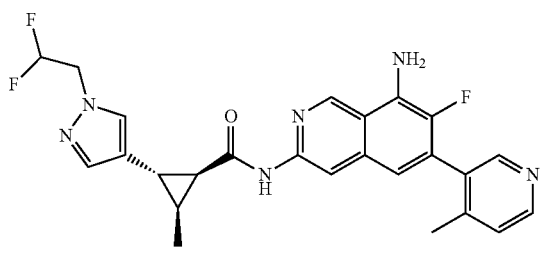 [SMILES: Cc1ccncc1-c1cc2cc(NC(=O)[C@H]3[C@@H](C)[C@@H]3c3cnn(CC(F)F)c3)ncc2c(N)c1F] | |
| 341, 342 | 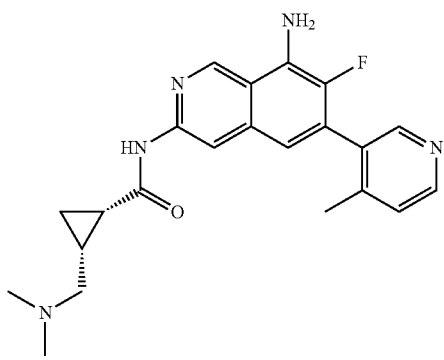 [SMILES: Cc1ccncc1-c1cc2cc(NC(=O)[C@H]3C[C@H]3CN(C)C)ncc2c(N)c1F] | cis-N-(8-amino-7-fluoro-6-(4-methylpyridin-3-yl)isoquinolin-3-yl)-2-((dimethylamino)methyl)cyclopropane-1-carboxamide |
| | 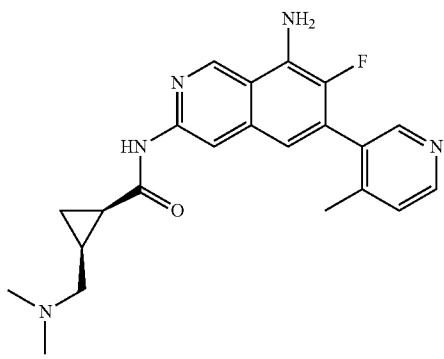 [SMILES: Cc1ccncc1-c1cc2cc(NC(=O)[C@@H]3C[C@@H]3CN(C)C)ncc2c(N)c1F] | |

TABLE 2-continued

| Compound No. | Structure | Name |
|---|---|---|
| 343, 344, 345 | | N-(8-amino-7-fluoro-6-(4-methylpyridin-3-yl)isoquinolin-3-yl)-2-(cyanomethyl)-3-((dimethylamino)methyl)cyclopropane-1-carboxamide |
| 346, 347, 348, 349 | 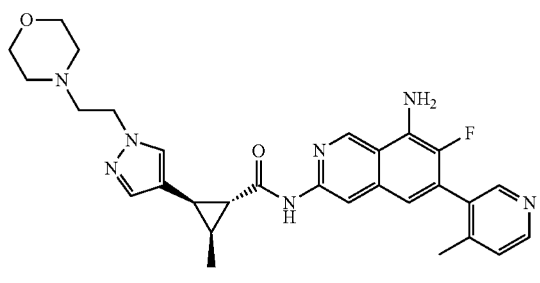 [SMILES: Cc1ccncc1-c1cc2cc(NC(=O)[C@@H]3[C@@H](C)[C@H]3c3cnn(CCN4CCOCC4)c3)ncc2c(N)c1F] | (1,3)trans-N-(8-amino-7-fluoro-6-(4-methylpyridin-3-yl)isoquinolin-3-yl)-2-methyl-3-(1-(2-morpholinoethyl)-1H-pyrazol-4-yl)cyclopropane-1-carboxamide |

TABLE 2-continued

| Compound No. | Structure | Name |
|---|---|---|
| 350, 351, 352, 353 | 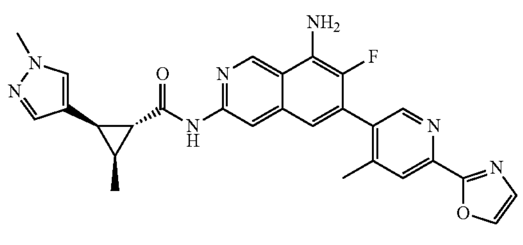 [SMILES: Cc1cc(-c2ncco2)ncc1-c1cc2cc(NC(=O)[C@@H]3[C@@H](C)[C@H]3c3cnn(C)c3)ncc2c(N)c1F] | (1,3)trans-N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide |

TABLE 2-continued

| Compound No. | Structure | Name |
|---|---|---|
| | (structure) | |
| 354 | (structure) | N-(8-amino-7-fluoro-6-(4-methylpyridin-3-yl)isoquinolin3-yl)-2-(1-methyl-1H-1,2,3-triazol-4-yl)cyclopropane-1-carboxamide |
| 355 | (structure) | (1S,2S)-N-(8-amino-7-fluoro-6-(4-methylpyridin-3-yl)isoquinolin-3-yl)-2-(1-methyl-1H-1,2,3-triazol-4-yl)cyclopropane-1-carboxamide (Relative stereochemistry as drawn; Absolute stereochemistry arbitrarily assigned) |
| 356 | (structure) | (1R,2R)-N-(8-amino-7-fluoro-6-(4-methylpyridin-3-yl)isoquinolin-3-yl)-2-(1-methyl-1H-1,2,3-triazol-4-yl)cyclopropane-1-carboxamide (Relative stereochemistry as drawn; Absolute stereochemistry arbitrarily assigned) |
| 357, 358, 359, 360 | (structure) | (1,3)trans-N-(8-amino-6-(5-amino-4-methylpyridin-3-yl)-7-fluoroisoquinolin-3-yl)-2-methyl-3-(1-methyl-1H-pyrazol-4-yl)cyclopropane-1-carboxamide |

TABLE 2-continued
| Compound No. | Structure | Name |
|---|---|---|
| | 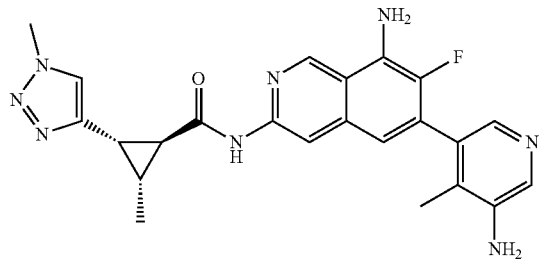 [SMILES: Cc1c(N)cncc1-c1cc2cc(NC(=O)[C@H]3[C@H](C)[C@@H]3c3cn(C)nn3)ncc2c(N)c1F] | |
| | | |
| 361 | 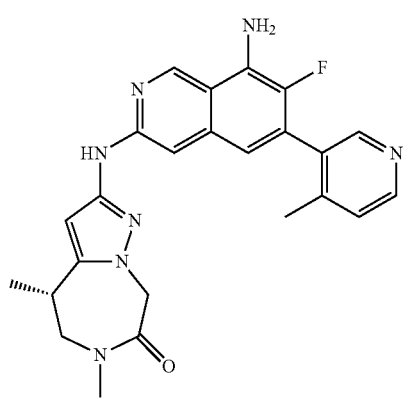 [SMILES: Cc1ccncc1-c1cc2cc(Nc3cc4n(n3)CC(=O)N(C)C[C@@H]4C)ncc2c(N)c1F] | (S)-2-((8-amino-7-fluoro-6-(4-methylpyridin-3-yl)isoquinolin-3-yl)amino)-4,6-dimethyl-5,6-dihydro-4H-pyrazolo[1,5-d][1,4]diazepin-7(8H)-one (Absolute stereochemistry arbitrarily assigned) |
| 362 | 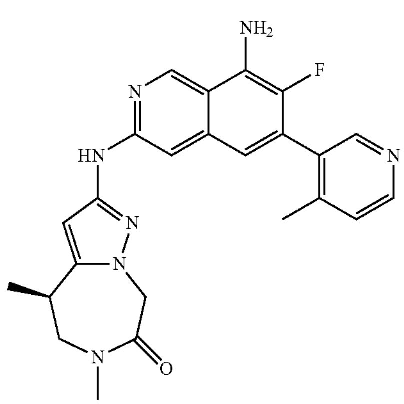 [SMILES: Cc1ccncc1-c1cc2cc(Nc3cc4n(n3)CC(=O)N(C)C[C@H]4C)ncc2c(N)c1F] | (R)-2-((8-amino-7-fluoro-6-(4-methylpyridin-3-yl)isoquinolin-3-yl)amino)-4,6-dimethyl-5,6-dihydro-4H-pyrazolo[1,5-d][1,4]diazepin-7(8H)-one (Absolute stereochemistry arbitrarily assigned |

TABLE 2-continued

| Compound No. | Structure | Name |
|---|---|---|
| 363, 364 | | trans-N-(8-amino-7-fluoro-6-(4-methylpyridin-3-yl)isoquinolin-3-yl)-2-(1H-pyrazol-5-yl)cyclopropane-1-carboxamide |
| 365, 366, 367, 368 | | (1,2)trans-N-(8-amino-7-fluoro-6-(4-methylpyridin-3-yl)isoquinolin-3-yl)-2-(1-(2-hydroxyethyl)-1H-pyrazol-4-yl)-3-methylcyclopropane-1-carboxamide |

TABLE 2-continued

| Compound No. | Structure | Name |
|---|---|---|
| | [Structure] | |
| 369, 370 | [Structure] | (1,3)trans-N-(8-amino-7-fluoro-6-(4-methylpyridin-3-yl)isoquinolin-3-yl)-2-(1H-imidazol-4-yl)-3-(1-methyl-1H-pyrazol-4-yl)cyclopropane-1-carboxamide |
| | [Structure] | |
| 371, 372, 373, 374 | [Structure] | exo-N-(8-amino-7-fluoro-6-(4-methylpyridin-3-yl)isoquinolin-3-yl)-2-hydroxybicyclo[4.1.0]heptane-7-carboxamide |
| | [Structure] | |

TABLE 2-continued

| Compound No. | Structure | Name |
|---|---|---|
| 375, 376, 377, 378 | 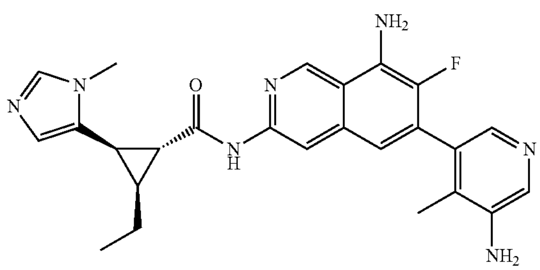 [SMILES: CC[C@@H]1[C@@H](C(=O)Nc2cc3cc(-c4cncc(N)c4C)c(F)c(N)c3cn2)[C@@H]1c1cncn1C] | (1,3)trans-N-(8-amino-6-(5-amino-4-methylpyridin-3-yl)-7-fluoroisoquinolin-3-yl)-2-ethyl-3-(1-methyl-1H-imidazol-5-yl)cyclopropane-1-carboxamide |

| Compound No. | Structure | Name |
|---|---|---|
| 379, 380, 381, 382 | 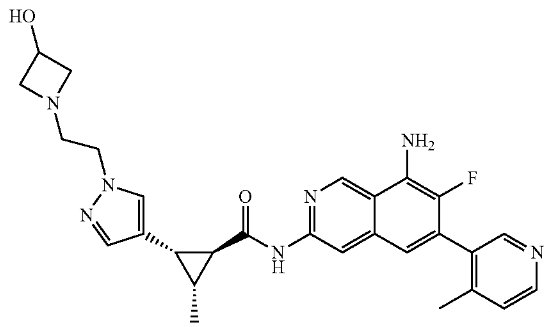 [SMILES: Cc1ccncc1-c1cc2cc(NC(=O)[C@H]3[C@H](C)[C@@H]3c3cnn(CCN4CC(O)C4)c3)ncc2c(N)c1F] | (1,2)trans-N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropane-1-carboxamide |

TABLE 2-continued

| Compound No. | Structure | Name |
|---|---|---|
| 383, 384, 385, 386 | | (1,2)trans-N-(8-amino-7-fluoro-6-(4-methylpyridin-3-yl)isoquinolin-3-yl)-2-(cyanomethyl)-3-methylcyclopropane-1-carboxamide |
| 387 | 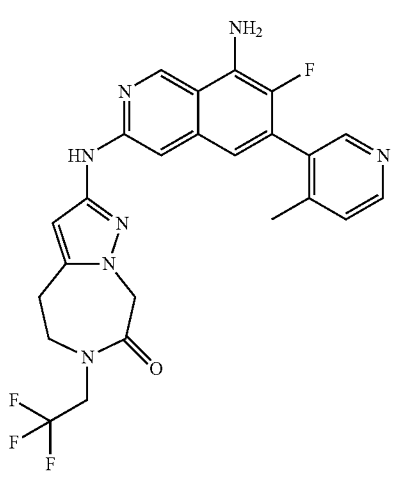 [SMILES: Cc1ccncc1-c1cc2cc(Nc3cc4n(n3)CC(=O)N(CC(F)(F)F)CC4)ncc2c(N)c1F] | 2-((8-amino-7-fluoro-6-(4-methylpyridin-3-yl)isoquinolin-3-yl)amino)-6-(2,2,2-trifluoroethyl)-5,6-dihydro-4H-pyrazolo[1,5-d][1,4]diazepin-7(8H)-one |

TABLE 2-continued

| Compound No. | Structure | Name |
| --- | --- | --- |
| 388 | 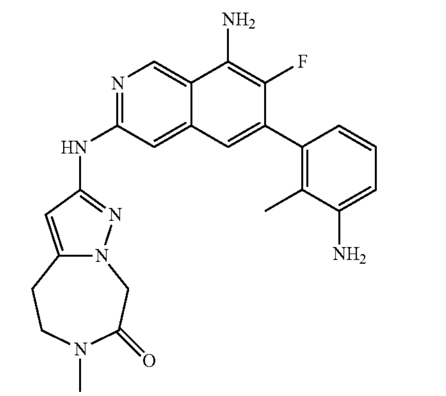 [SMILES: Cc1c(N)cccc1-c1cc2cc(Nc3cc4n(n3)CC(=O)N(C)CC4)ncc2c(N)c1F] | 2-((8-amino-6-(3-amino-2-methylphenyl)-7-fluoroisoquinolin-3-yl)amino)-6-methyl-5,6-dihydro-4H-pyrazolo[1,5-d][1,4]diazepin-7(8H)-one |
| 389 | 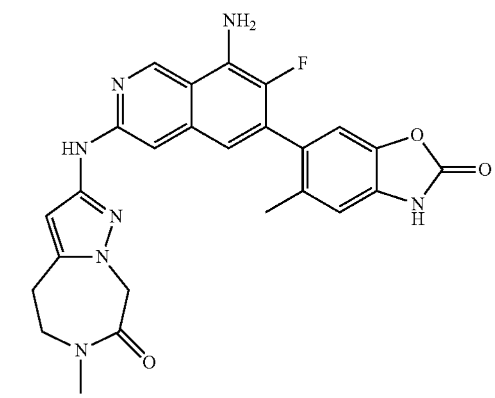 [SMILES: Cc1cc2[nH]c(=O)oc2cc1-c1cc2cc(Nc3cc4n(n3)CC(=O)N(C)CC4)ncc2c(N)c1F] | 6-(8-amino-7-fluoro-3-((6-methyl-7-oxo-5,6,7,8-tetrahydro-4H-pyrazolo[1,5-d][1,4]diazepin-2-yl)amino)isoquinolin-6-yl)-5-methylbenzo[d]oxazol-2(3H)-one |
| 390 | 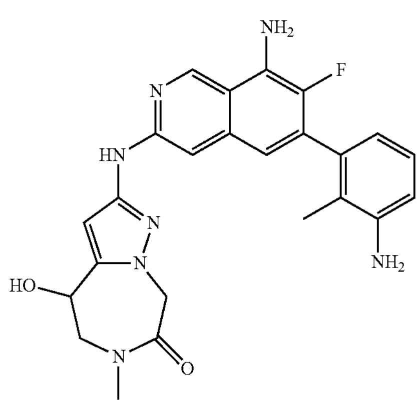 [SMILES: Cc1c(N)cccc1-c1cc2cc(Nc3cc4n(n3)CC(=O)N(C)CC4O)ncc2c(N)c1F] | 2-((8-amino-6-(3-amino-2-methylphenyl)-7-fluoroisoquinolin-3-yl)amino)-4-hydroxy-6-methyl-5,6-dihydro-4H-pyrazolo[1,5-d][1,4]diazepin-7(8H)-one |

TABLE 3

| Compound No. | Structure | Name |
|---|---|---|
| 391 | 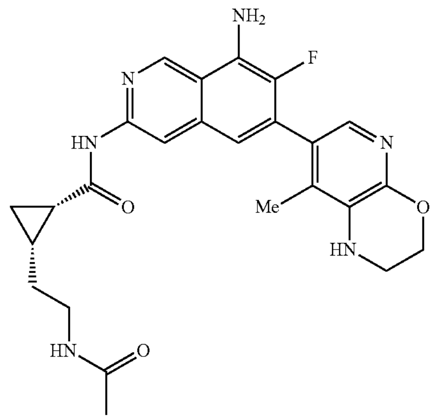 [SMILES: CC(=O)NCC[C@@H]1C[C@@H]1C(=O)Nc1cc2cc(-c3cnc4c(c3C)NCCO4)c(F)c(N)c2cn1] | cis-2-(2-acetamidoethyl)-N-(8-amino-7-fluoro-6-(8-methyl-2,3-dihydro-1H-pyrido[2,3-b][1,4]oxazin-7-yl)isoquinolin-3-yl)cyclopropane-1-carboxamide |
| 392 | 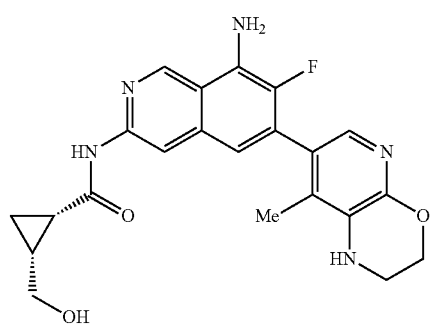 [SMILES: Cc1c(-c2cc3cc(NC(=O)[C@H]4C[C@H]4CO)ncc3c(N)c2F)cnc2c1NCCO2] | cis-N-(8-amino-7-fluoro-6-(8-methyl-2,3-dihydro-1H-pyrido[2,3-b][1,4]oxazin-7-yl)isoquinolin-3-yl)-2-(hydroxymethyl)cyclopropane-1-carboxamide |

| Compound No. | Structure | Name |
|---|---|---|
| 393 | 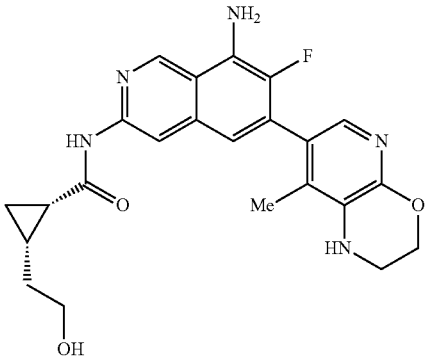 [SMILES: Cc1c(-c2cc3cc(NC(=O)[C@H]4C[C@H]4CCO)ncc3c(N)c2F)cnc2c1NCCO2] | cis-N-(8-amino-7-fluoro-6-(8-methyl-2,3-dihydro-1H-pyrido[2,3-b][1,4]oxazin-7-yl)isoquinolin-3-yl)-2-(2-hydroxyethyl)cyclopropane-1-carboxamide |
| 394 | 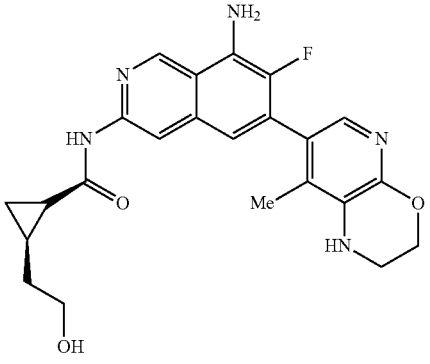 | 3-methyltetrahydrofuran-3-yl (8-amino-6-(5-amino-4-methylpyridin-3-yl)-7-fluoroisoquinolin-3-yl)carbamate |
| 395 | 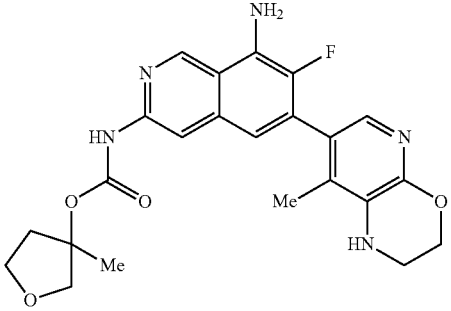 [SMILES: Cc1c(-c2cc3cc(NC(=O)OC4(C)CCOC4)ncc3c(N)c2F)cnc2c1NCCO2] | 3-methyltetrahydrofuran-3-yl (8-amino-7-fluoro-6-(8-methyl-2,3-dihydro-1H-pyrido[2,3-b][1,4]oxazin-7-yl)isoquinolin-3-yl)carbamate |

TABLE 3-continued

| Compound No. | Structure | Name |
|---|---|---|
| 396 | 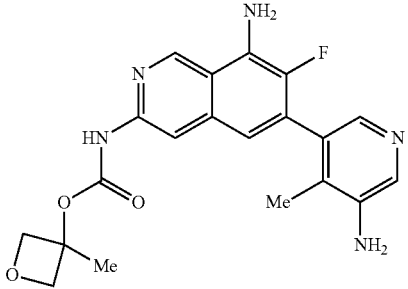 [SMILES: Cc1c(N)cncc1-c1cc2cc(NC(=O)OC3(C)COC3)ncc2c(N)c1F] | 3-methyloxetan-3-yl (8-amino-6-(5-amino-4-methylpyridin-3-yl)-7-fluoroisoquinolin-3-yl)carbamate |
| 397 | 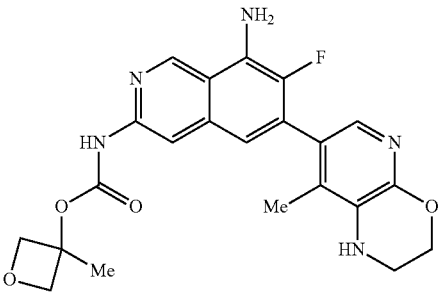 [SMILES: Cc1c(-c2cc3cc(NC(=O)OC4(C)COC4)ncc3c(N)c2F)cnc2c1NCCO2] | 3-methyloxetan-3-yl (8-amino-7-fluoro-6-(8-methyl-2,3-dihydro-1H-pyrido[2,3-b][1,4]oxazin-7-yl)isoquinolin-3-yl)carbamate |
| 398 | 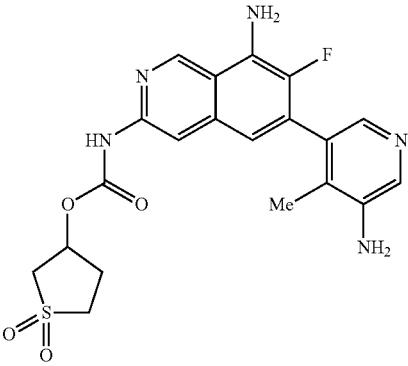 [SMILES: Cc1c(N)cncc1-c1cc2cc(NC(=O)OC3CCS(=O)(=O)C3)ncc2c(N)c1F] | 1,1-dioxidotetrahydrothiophen-3-yl (8-amino-6-(5-amino-4-methylpyridin-3-yl)-7-fluoroisoquinolin-3-yl)carbamate |
| 399 | 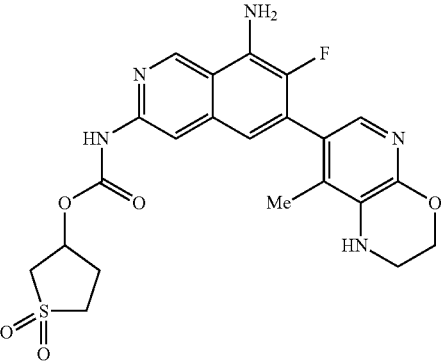 [SMILES: Cc1c(-c2cc3cc(NC(=O)OC4CCS(=O)(=O)C4)ncc3c(N)c2F)cnc2c1NCCO2] | 1,1-dioxidotetrahydrothiophen-3-yl (8-amino-7-fluoro-6-(8-methyl-2,3-dihydro-1H-pyrido[2,3-b][1,4]oxazin-7-yl)isoquinolin-3-yl)carbamate |

TABLE 3-continued

| Compound No. | Structure | Name |
|---|---|---|
| 400 | 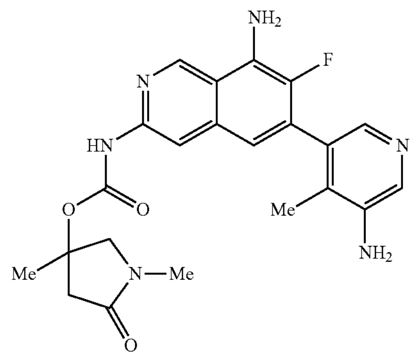 [SMILES: Cc1c(N)cncc1-c1cc2cc(NC(=O)OC3(C)CC(=O)N(C)C3)ncc2c(N)c1F] | 1,3-dimethyl-5-oxopyrrolidin-3-yl (8-amino-6-(5-amino-4-methylpyridin-3-yl)-7-fluoroisoquinolin-3-yl)carbamate |
| 401 | 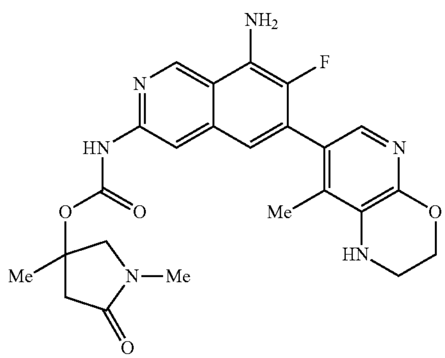 [SMILES: Cc1c(-c2cc3cc(NC(=O)OC4(C)CC(=O)N(C)C4)ncc3c(N)c2F)cnc2c1NCCO2] | 1,3-dimethyl-5-oxopyrrolidin-3-yl (8-amino-7-fluoro-6-(8-methyl-2,3-dihydro-1H-pyrido[2,3-b][1,4]oxazin-7-yl)isoquinolin-3-yl)carbamate |
| 402 | 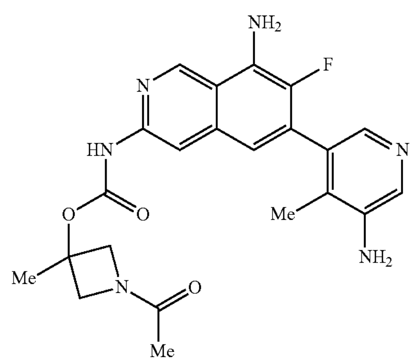 [SMILES: CC(=O)N1CC(C)(OC(=O)Nc2cc3cc(-c4cncc(N)c4C)c(F)c(N)c3cn2)C1] | 1-acetyl-3-methylazetidin-3-yl (8-amino-6-(5-amino-4-methylpyridin-3-yl)-7-fluoroisoquinolin-3-yl)carbamate |
| 403 | 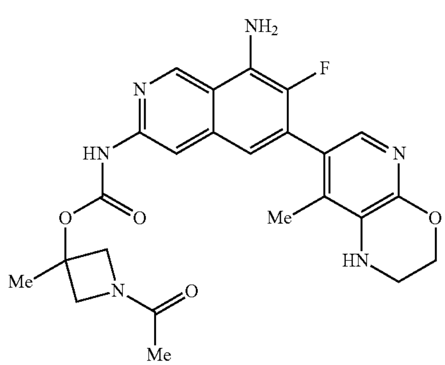 [SMILES: CC(=O)N1CC(C)(OC(=O)Nc2cc3cc(-c4cnc5c(c4C)NCCO5)c(F)c(N)c3cn2)C1] | 1-acetyl-3-methylazetidin-3-yl (8-amino-7-fluoro-6-(8-methyl-2,3-dihydro-1H-pyrido[2,3-b][1,4]oxazin-7-yl)isoquinolin-3-yl)carbamate |

TABLE 3-continued

| Compound No. | Structure | Name |
|---|---|---|
| 404 | 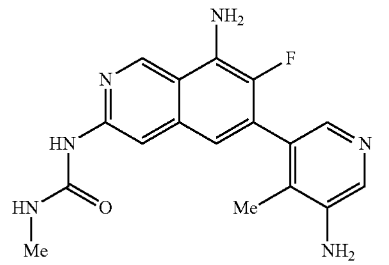 [SMILES: CNC(=O)Nc1cc2cc(-c3cncc(N)c3C)c(F)c(N)c2cn1] | 1-(8-amino-6-(5-amino-4-methylpyridin-3-yl)-7-fluoroisoquinolin-3-yl)-3-methylurea |
| 405 | 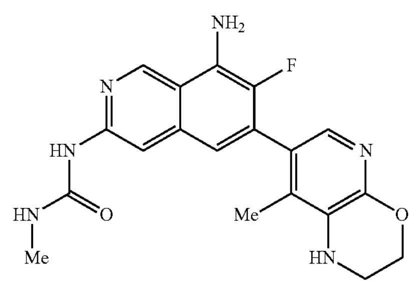 [SMILES: CNC(=O)Nc1cc2cc(-c3cnc4c(c3C)NCCO4)c(F)c(N)c2cn1] | 1-(8-amino-7-fluoro-6-(8-methyl-2,3-dihydro-1H-pyrido[2,3-b][1,4]oxazin-7-yl)isoquinolin-3-yl)-3-methylurea |
| 406 | 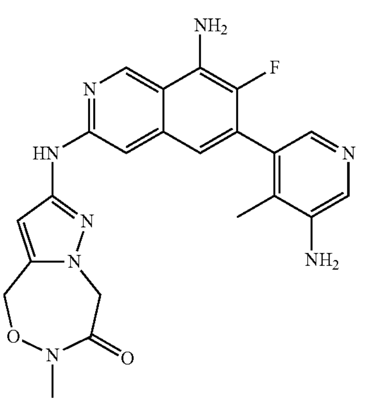 [SMILES: Cc1c(N)cncc1-c1cc2cc(Nc3cc4n(n3)CC(=O)N(C)OC4)ncc2c(N)c1F] | 2-((8-amino-6-(5-amino-4-methylpyridin-3-yl)-7-fluoroisoquinolin-3-yl)amino)-6-methyl-4H,6H-pyrazolo[1,5-e][1,2,5]oxadiazepin-7(8H)-one |
| 407 | 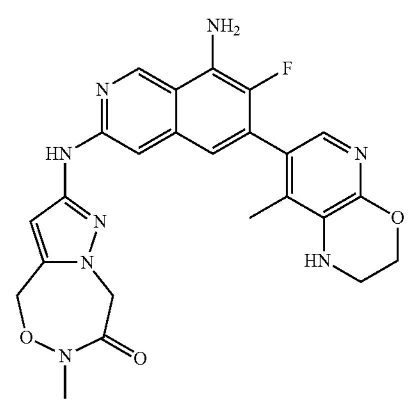 [SMILES: Cc1c(-c2cc3cc(Nc4cc5n(n4)CC(=O)N(C)OC5)ncc3c(N)c2F)cnc2c1NCCO2] | 2-((8-amino-7-fluoro-6-(8-methyl-2,3-dihydro-1H-pyrido[2,3-b][1,4]oxazin-7-yl)isoquinolin-3-yl)amino)-6-methyl-4H,6H-pyrazolo[1,5-e][1,2,5]oxadiazepin-7(8H)-one |

TABLE 3-continued

| Compound No. | Structure | Name |
|---|---|---|
| 408 | 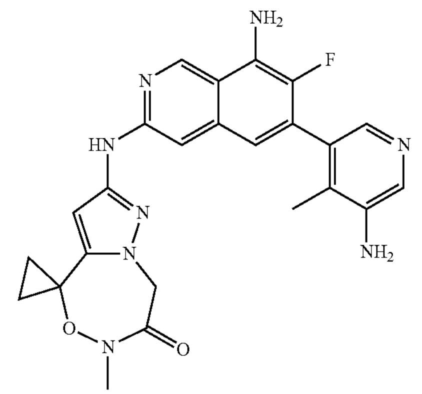 [SMILES: Cc1c(N)cncc1-c1cc2cc(Nc3cc4n(n3)CC(=O)N(C)OC43CC3)ncc2c(N)c1F] | 2'-((8-amino-6-(5-amino-4-methylpyridin-3-yl)-7-fluoroisoquinolin-3-yl)amino)-6'-methyl-6'H-spiro[cyclopropane-1,4'-pyrazolo[1,5-e][1,2,5]oxadiazepin]-7'(8'H)-one |
| 409 | 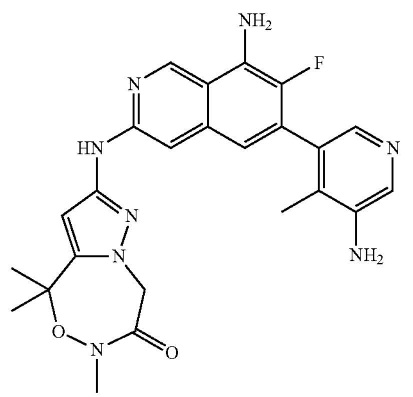 [SMILES: Cc1c(N)cncc1-c1cc2cc(Nc3cc4n(n3)CC(=O)N(C)OC4(C)C)ncc2c(N)c1F] | 2-((8-amino-6-(5-amino-4-methylpyridin-3-yl)-7-fluoroisoquinolin-3-yl)amino)-4,4,6-trimethyl-4H,6H-pyrazolo[1,5-e][1,2,5]oxadiazepin-7(8H)-one |
| 410 | 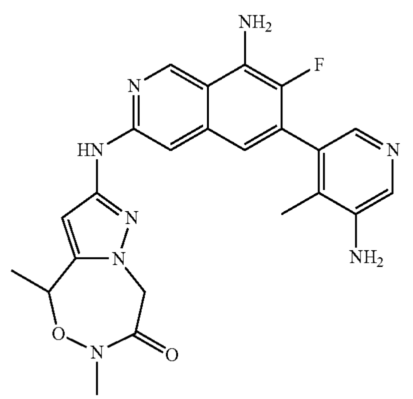 [SMILES: Cc1c(N)cncc1-c1cc2cc(Nc3cc4n(n3)CC(=O)N(C)OC4C)ncc2c(N)c1F] | (+/−)-2-((8-amino-6-(5-amino-4-methylpyridin-3-yl)-7-fluoroisoquinolin-3-yl)amino)-4,6-dimethyl-4H,6H-pyrazolo[1,5-e][1,2,5]oxadiazepin-7(8H)-one |
| 411 | 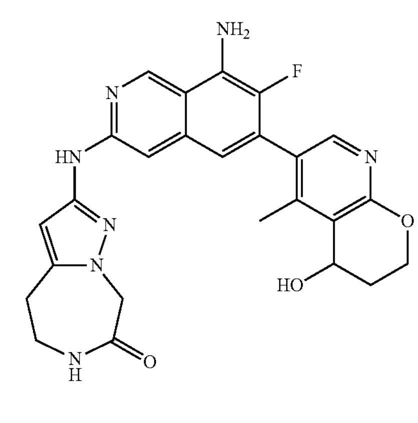 | (+/−)-2-((8-amino-7-fluoro-6-(4-hydroxy-5-methyl-3,4-dihydro-2H-pyrano[2,3-b]pyridin-6-yl)isoquinolin-3-yl)amino)-5,6-dihydro-4H-pyrazolo[1,5-d][1,4]diazepin-7(8H)-one |

TABLE 3-continued

| Compound No. | Structure | Name |
|---|---|---|
| 412 | 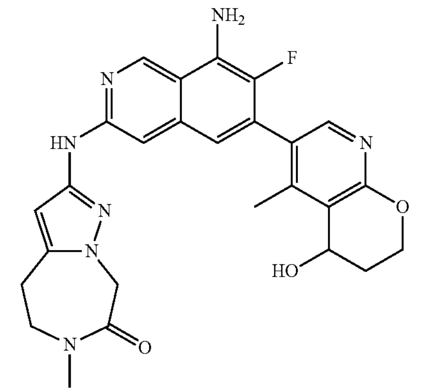 [SMILES: Cc1c(-c2cc3cc(Nc4cc5n(n4)CC(=O)N(C)CC5)ncc3c(N)c2F)cnc2c1C(O)CCO2] | (+/−)-2-((8-amino-7-fluoro-6-(4-hydroxy-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one |
| 413 | 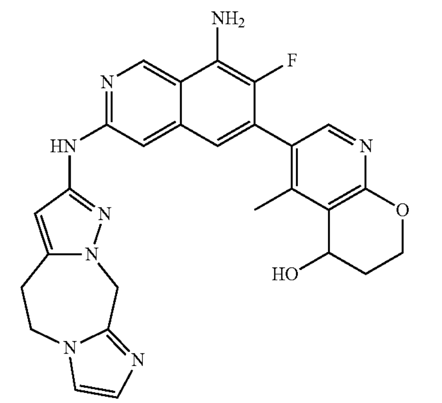 [SMILES: Cc1c(-c2cc3cc(Nc4cc5n(n4)Cc4nccn4CC5)ncc3c(N)c2F)cnc2c1C(O)CCO2] | (+/−)-6-(8-amino-3-((5,6-dihydro-11H-imidazo[1,2-a]pyrazolo[1,5-d][1,4]diazepin-8-yl)amino)-7-fluoroisoquinolin-6-yl)-5-methyl-3,4-dihydro-2H-pyrano[2,3-b]pyridin-4-ol |
| 414 | 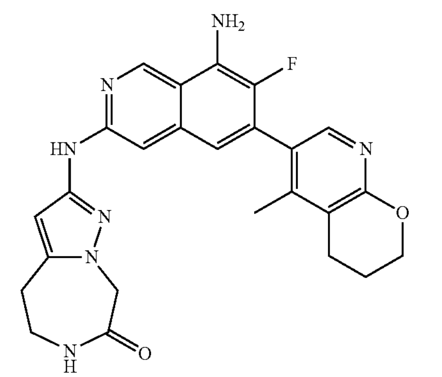 [SMILES: Cc1c(-c2cc3cc(Nc4cc5n(n4)CC(=O)NCC5)ncc3c(N)c2F)cnc2c1CCCO2] | 2-((8-amino-7-fluoro-6-(5-methyl-3,4-dihydro-2H-pyrano[2,3-b]pyridin-6-yl)isoquinolin-3-yl)amino)-5,6-dihydro-4H-pyrazolo[1,5-d][1,4]diazepin-7(8H)-one |
| 415 | 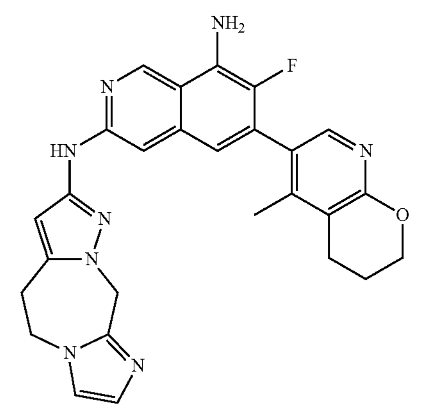 [SMILES: Cc1c(-c2cc3cc(Nc4cc5n(n4)Cc4nccn4CC5)ncc3c(N)c2F)cnc2c1CCCO2] | N3-(5,6-dihydro-11H-imidazo[1,2-a]pyrazolo[1,5-d][1,4]diazepin-8-yl)-7-fluoro-6-(5-methyl-3,4-dihydro-2H-pyrano[2,3-b]pyridin-6-yl)isoquinoline-3,8-diamine |

TABLE 3-continued

| Compound No. | Structure | Name |
|---|---|---|
| 416 | 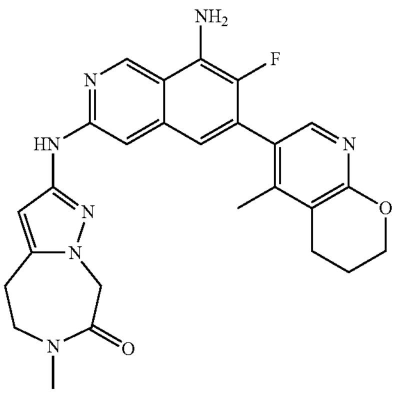 [SMILES: Cc1c(-c2cc3cc(Nc4cc5n(n4)CC(=O)N(C)CC5)ncc3c(N)c2F)cnc2c1CCCO2] | 2-((8-amino-7-fluoro-6-(5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one |
| 417 | 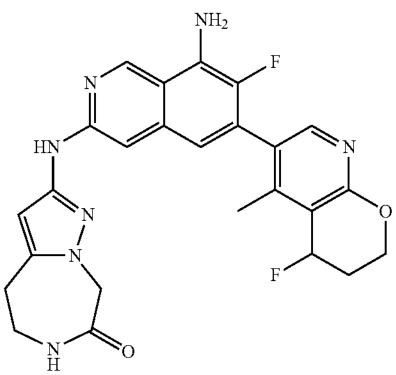 [SMILES: Cc1c(-c2cc3cc(Nc4cc5n(n4)CC(=O)NCC5)ncc3c(N)c2F)cnc2c1C(F)CCO2] | (+/−)-2-((8-amino-7-fluoro-6-(4-fluoro-5-methyl-3,4-dihydro-2H-pyrano[2,3-b]pyridin-6-yl)isoquinolin-3-yl)amino)-5,6-dihydro-4H-pyrazolo[1,5-d][1,4]diazepin-7(8H)-one |
| 418 | 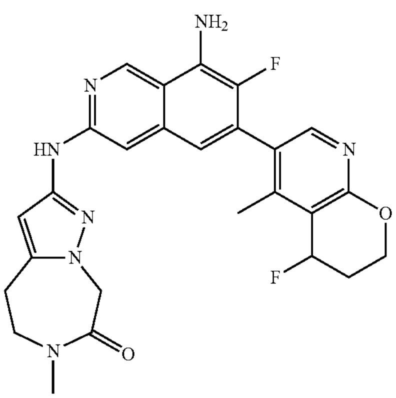 [SMILES: Cc1c(-c2cc3cc(Nc4cc5n(n4)CC(=O)N(C)CC5)ncc3c(N)c2F)cnc2c1C(F)CCO2] | (+/−)-2-((8-amino-7-fluoro-6-(4-fluoro-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one |
| 419 | 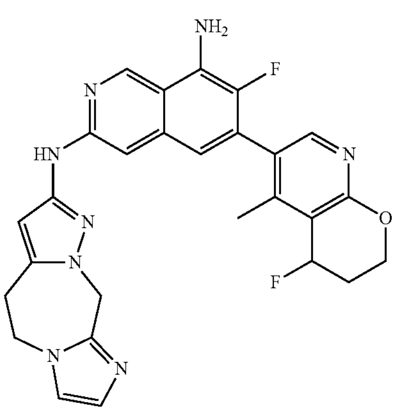 [SMILES: Cc1c(-c2cc3cc(Nc4cc5n(n4)Cc4nccn4CC5)ncc3c(N)c2F)cnc2c1C(F)CCO2] | (+/−)-N3-(5,6-dihydro-11H-imidazo[1,2-a]pyrazolo[1,5-d][1,4]diazepin-8-yl)-7-fluoro-6-(4-fluoro-5-methyl-3,4-dihydro-2H-pyrano[2,3-b]pyridin-6-yl)isoquinoline-3,8-diamine |

TABLE 3-continued

| Compound No. | Structure | Name |
|---|---|---|
| 420 | 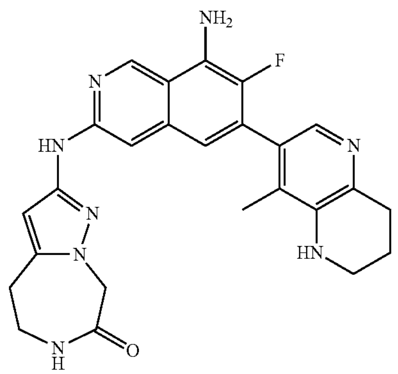 [SMILES: Cc1c(-c2cc3cc(Nc4cc5n(n4)CC(=O)NCC5)ncc3c(N)c2F)cnc2c1NCCC2] | 2-((8-amino-7-fluoro-6-(4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one |
| 421 | 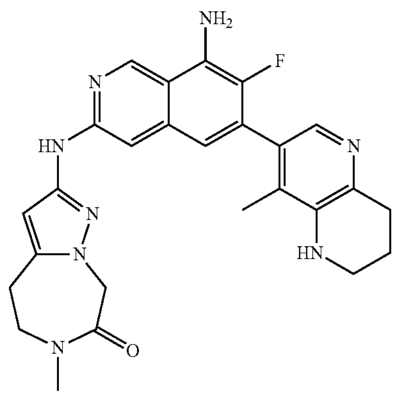 [SMILES: Cc1c(-c2cc3cc(Nc4cc5n(n4)CC(=O)N(C)CC5)ncc3c(N)c2F)cnc2c1NCCC2] | 2-((8-amino-7-fluoro-6-(4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |
| 422 | 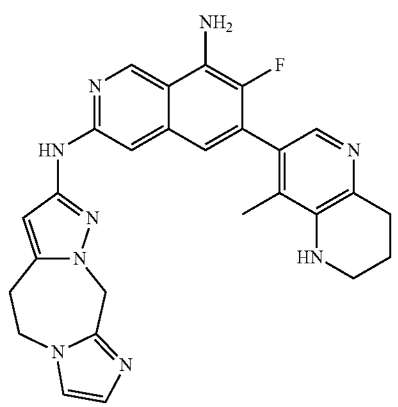 [SMILES: Cc1c(-c2cc3cc(Nc4cc5n(n4)Cc4nccn4CC5)ncc3c(N)c2F)cnc2c1NCCC2] | N3-(5,6-dihydro-11H-imidazo[1,2-a]pyrazolo[1,5-d][1,4]diazepin-8-yl)-7-fluoro-6-(4-methyl-5,6,7,8-tetrahydro-1,5-naphthyridin-3-yl)isoquinoline-3,8-diamine |
| 423 | 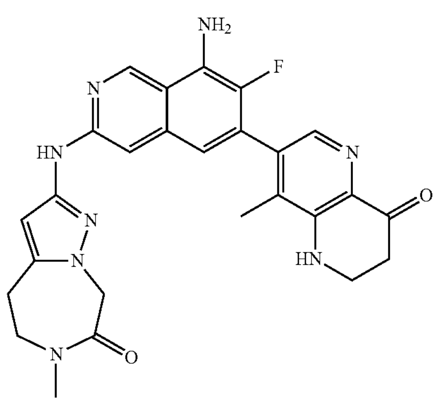 [SMILES: Cc1c(-c2cc3cc(Nc4cc5n(n4)CC(=O)N(C)CC5)ncc3c(N)c2F)cnc2c1NCCC2=O] | 2-((8-amino-7-fluoro-6-(4-methyl-8-oxo-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |

TABLE 3-continued

| Compound No. | Structure | Name |
|---|---|---|
| 424 | 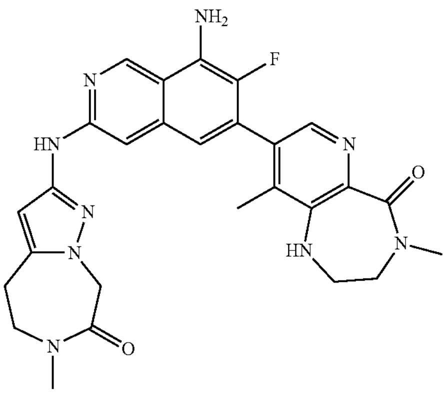 [SMILES: Cc1c(-c2cc3cc(Nc4cc5n(n4)CC(=O)N(C)CC5)ncc3c(N)c2F)cnc2c1NCCN(C)C2=O] | 8-(8-amino-7-fluoro-3-((6-methyl-7-oxo-5,6,7,8-tetrahydro-4H-pyrazolo[1,5-d][1,4]diazepin-2-yl)amino)isoquinolin-6-yl)-4,9-dimethyl-1,2,3,4-tetrahydro-5H-pyrido[3,2-e][1,4]diazepin-5-one |
| 425 | 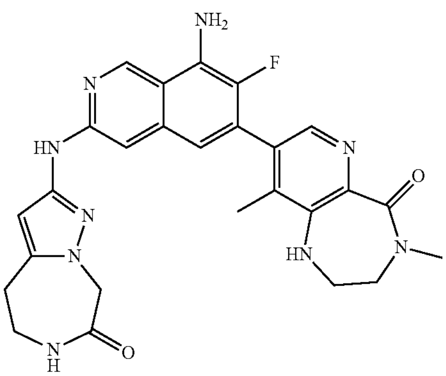 [SMILES: Cc1c(-c2cc3cc(Nc4cc5n(n4)CC(=O)NCC5)ncc3c(N)c2F)cnc2c1NCCN(C)C2=O] | 8-(8-amino-7-fluoro-3-((7-oxo-5,6,7,8-tetrahydro-4H-pyrazolo[1,5-d][1,4]diazepin-2-yl)amino)isoquinolin-6-yl)-4,9-dimethyl-1,2,3,4-tetrahydro-5H-pyrido[3,2-e][1,4]diazepin-5-one |
| 426 | 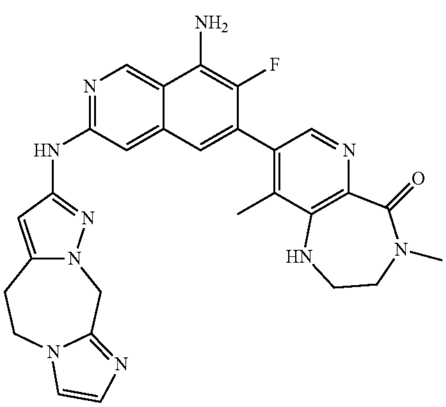 [SMILES: Cc1c(-c2cc3cc(Nc4cc5n(n4)Cc4nccn4CC5)ncc3c(N)c2F)cnc2c1NCCN(C)C2=O] | 8-(8-amino-3-((5,6-dihydro-11H-imidazo[1,2-a]pyrazolo[1,5-d][1,4]diazepin-8-yl)amino)-7-fluoroisoquinolin-6-yl)-4,9-dimethyl-1,2,3,4-tetrahydro-5H-pyrido[3,2-e][1,4]diazepin-5-one |
| 427 | 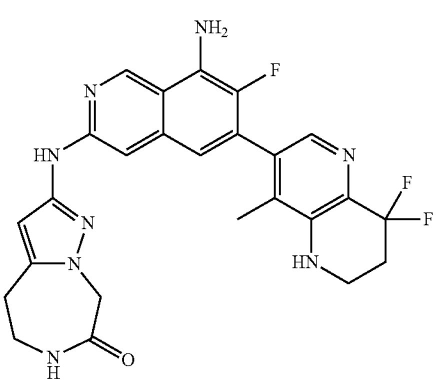 [SMILES: Cc1c(-c2cc3cc(Nc4cc5n(n4)CC(=O)NCC5)ncc3c(N)c2F)cnc2c1NCCC2(F)F] | 2-((8-amino-6-(8,8-difluoro-4-methyl-5,6,7,8-tetrahydro-1,5-naphthyridin-3-yl)-7-fluoroisoquinolin-3-yl)amino)-5,6-dihydro-4H-pyrazolo[1,5-d][1,4]diazepin-7(8H)-one |

TABLE 3-continued

| Compound No. | Structure | Name |
|---|---|---|
| 428 | 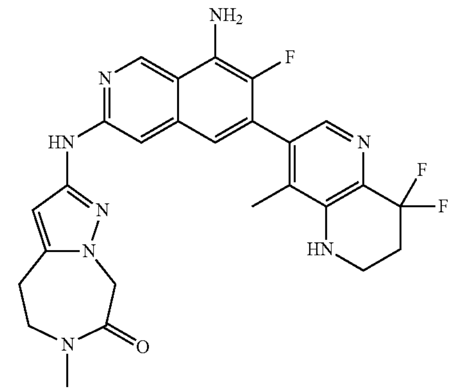 [SMILES: Cc1c(-c2cc3cc(Nc4cc5n(n4)CC(=O)N(C)CC5)ncc3c(N)c2F)cnc2c1NCCC2(F)F] | 2-((8-amino-6-(8,8-difluoro-4-methyl-5,6,7,8-tetrahydro-1,5-naphthyridin-3-yl)-7-fluoroisoquinolin-3-yl)amino)-6-methyl-5,6-dihydro-4H-pyrazol[1,5-d][1,4]diazepin-7(8H)-one |
| 429 | 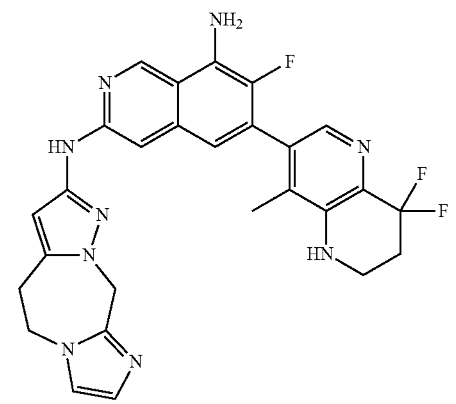 [SMILES: Cc1c(-c2cc3cc(Nc4cc5n(n4)Cc4nccn4CC5)ncc3c(N)c2F)cnc2c1NCCC2(F)F] | 6-(8,8-difluoro-4-methyl-5,6,7,8-tetrahydro-1,5-naphthyridin-3-yl)-N3-(5,6-dihydro-11H-imidazo[1,2-a]pyrazolo[1,5-d][1,4]diazepin-8-yl)-7-fluoroisoquinoline-3,8-diamine |
| 430 | 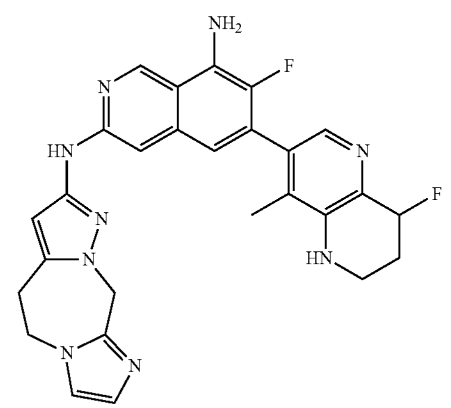 [SMILES: Cc1c(-c2cc3cc(Nc4cc5n(n4)Cc4nccn4CC5)ncc3c(N)c2F)cnc2c1NCCC2F] | (+/−)-N3-(5,6-dihydro-11H-imidazo[1,2-a]pyrazolo[1,5-d][1,4]diazepin-8-yl)-7-fluoro-6-(8-fluoro-4-methyl-5,6,7,8-tetrahydro-1,5-naphthyridin-3-yl)isoquinoline-3,8-diamine |
| 431 | 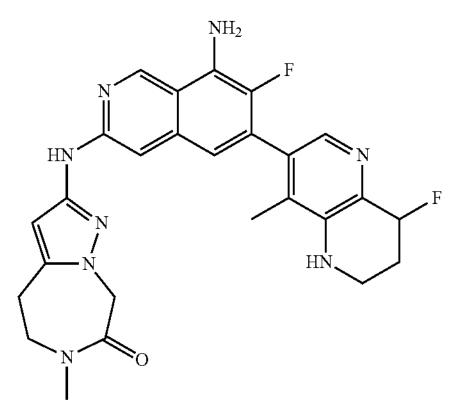 [SMILES: Cc1c(-c2cc3cc(Nc4cc5n(n4)CC(=O)N(C)CC5)ncc3c(N)c2F)cnc2c1NCCC2F] | (+/−)-2-((8-amino-7-fluoro-6-(8-fluoro-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |

TABLE 3-continued

| Compound No. | Structure | Name |
|---|---|---|
| 432 | 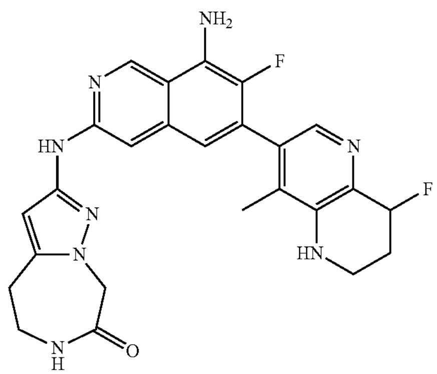 [SMILES: Cc1c(-c2cc3cc(Nc4cc5n(n4)CC(=O)NCC5)ncc3c(N)c2F)cnc2c1NCCC2F] | (+/−)-2-((8-amino-7-fluoro-6-(8-fluoro-4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one |
| 433 | 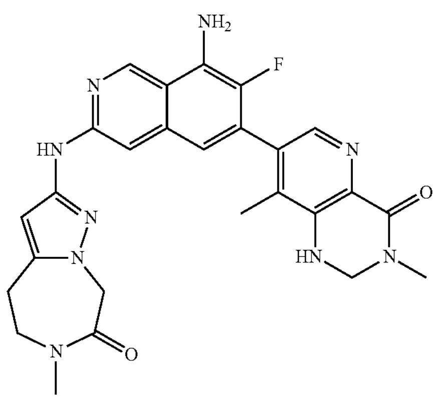 [SMILES: Cc1c(-c2cc3cc(Nc4cc5n(n4)CC(=O)N(C)CC5)ncc3c(N)c2F)cnc2c1NCN(C)C2=O] | 7-(8-amino-7-fluoro-3-((6-methyl-7-oxo-5,6,7,8-tetrahydro-4H-pyrazolo[1,5-d][1,4]diazepin-2-yl)amino)isoquinolin-6-yl)-3,8-dimethyl-2,3-dihydropyrido[3,2-d]pyrimidin-4(1H)-one |
| 434 | 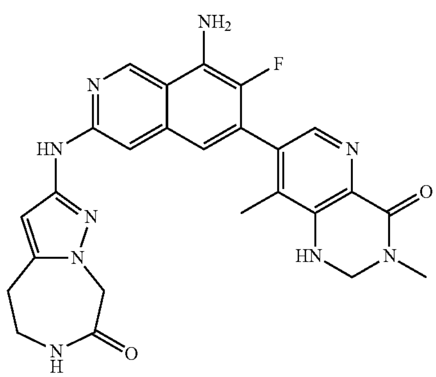 [SMILES: Cc1c(-c2cc3cc(Nc4cc5n(n4)CC(=O)NCC5)ncc3c(N)c2F)cnc2c1NCN(C)C2=O] | 7-(8-amino-7-fluoro-3-((7-oxo-5,6,7,8-tetrahydro-4H-pyrazolo[1,5-d][1,4]diazepin-2-yl)amino)isoquinolin-6-yl)-3,8-dimethyl-2,3-dihydropyrido[3,2-d]pyrimidin-4(1H)-one |
| 435 | 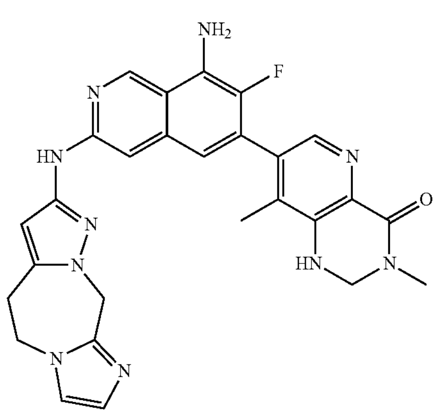 [SMILES: Cc1c(-c2cc3cc(Nc4cc5n(n4)Cc4nccn4CC5)ncc3c(N)c2F)cnc2c1NCN(C)C2=O] | 7-(8-amino-3-((5,6-dihydro-11H-imidazo[1,2-a]pyrazolo[1,5-d][1,4]diazepin-8-yl)amino)-7-fluoroisoquinolin-6-yl)-3,8-dimethyl-2,3-dihydropyrido[3,2-d]pyrimidin-4(1H)-one |

TABLE 3-continued

| Compound No. | Structure | Name |
|---|---|---|
| 436 | 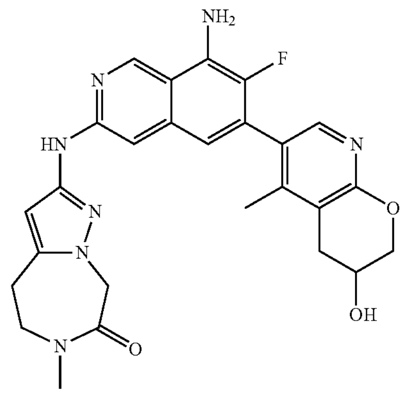 [SMILES: Cc1c(-c2cc3cc(Nc4cc5n(n4)CC(=O)N(C)CC5)ncc3c(N)c2F)cnc2c1CC(O)CO2] | (+/−)-2-((8-amino-7-fluoro-6-(3-hydroxy-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one |
| 437 | 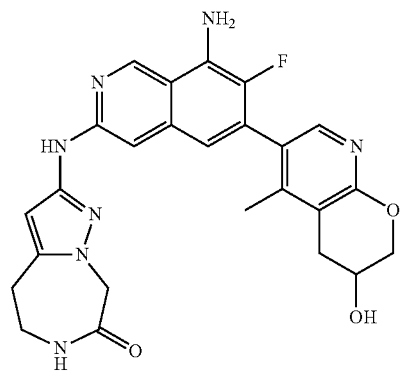 [SMILES: Cc1c(-c2cc3cc(Nc4cc5n(n4)CC(=O)NCC5)ncc3c(N)c2F)cnc2c1CC(O)CO2] | (+/−)-2-((8-amino-7-fluoro-6-(3-hydroxy-5-methyl-3,4-dihydro-2H-pyrano[2,3-b]pyridin-6-yl)isoquinolin-3-yl)amino)-5,6-dihydro-4H-pyrazolo[1,5-d][1,4]diazepin-7(8H)-one |
| 438 | 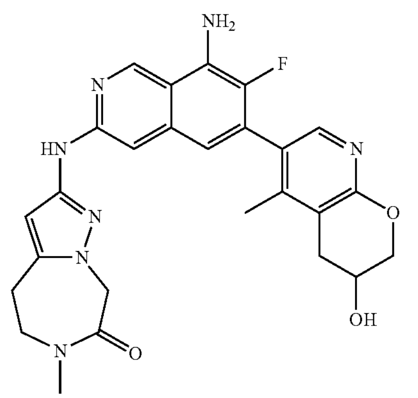 [SMILES: Cc1c(-c2cc3cc(Nc4cc5n(n4)CC(=O)N(C)CC5)ncc3c(N)c2F)cnc2c1CC(O)CO2] | (+/−)-2-((8-amino-7-fluoro-6-(3-hydroxy-5-methyl-3,4-dihydro-2H-pyrano[2,3-b]pyridin-6-yl)isoquinolin-3-yl)amino)-6-methyl-5,6-dihydro-4H-pyrazolo[1,5-d][1,4]diazepin-7(8H)-one |
| 439 | 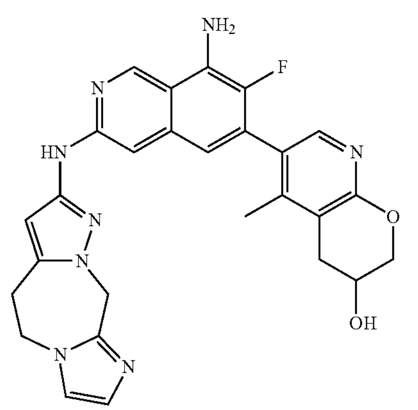 [SMILES: Cc1c(-c2cc3cc(Nc4cc5n(n4)Cc4nccn4CC5)ncc3c(N)c2F)cnc2c1CC(O)CO2] | (+/−)-6-(8-amino-3-((5,6-dihydro-11H-imidazo[1,2-a]pyrazolo[1,5-d][1,4]diazepin-8-yl)amino)-7-fluoroisoquinolin-6-yl)-5-methyl-3,4-dihydro-2H-pyrano[2,3-b]pyridin-3-ol |

TABLE 3-continued

| Compound No. | Structure | Name |
|---|---|---|
| 440 | 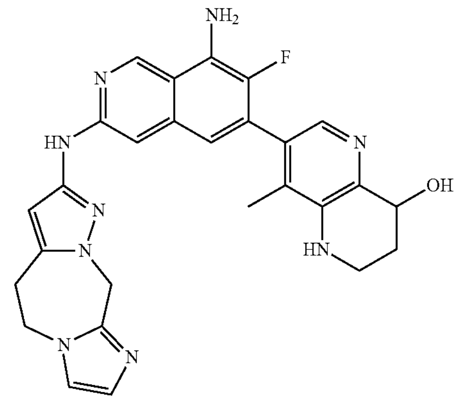 [SMILES: Cc1c(-c2cc3cc(Nc4cc5n(n4)Cc4nccn4CC5)ncc3c(N)c2F)cnc2c1NCCC2O] | (+/−)-7-(8-amino-3-((5,6-dihydro-11H-imidazo[1,2-a]pyrazolo[1,5-d][1,4]diazepin-8-yl)amino)-7-fluoroisoquinolin-6-yl)-8-methyl-1,2,3,4-tetrahydro-1,5-naphthyridin-4-ol |
| 441 | 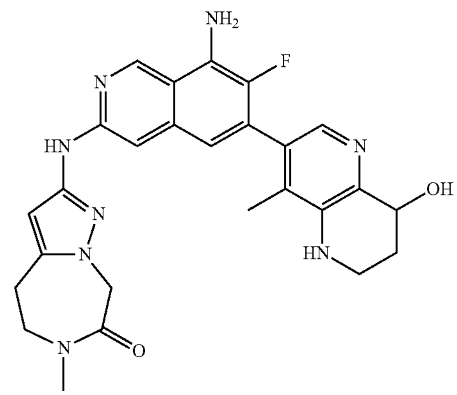 [SMILES: Cc1c(-c2cc3cc(Nc4cc5n(n4)CC(=O)N(C)CC5)ncc3c(N)c2F)cnc2c1NCCC2O] | (+/−)-2-((8-amino-7-fluoro-6-(8-hydroxy-4-methyl-5,6,7,8-tetrahydro-1,5-naphthyridin-3-yl)isoquinolin-3-yl)amino)-6-methyl-5,6-dihydro-4H-pyrazolo[1,5-d][1,4]diazepin-7(8H)-one |
| 442 | 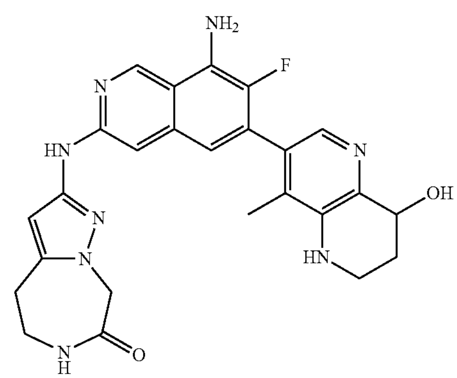 [SMILES: Cc1c(-c2cc3cc(Nc4cc5n(n4)CC(=O)NCC5)ncc3c(N)c2F)cnc2c1NCCC2O] | (+/−)-2-((8-amino-7-fluoro-6-(8-hydroxy-4-methyl-5,6,7,8-tetrahydro-1,5-naphthyridin-3-yl)isoquinolin-3-yl)amino)-5,6-dihydro-4H-pyrazolo[1,5-d][1,4]diazepin-7(8H)-one |
| 443 | 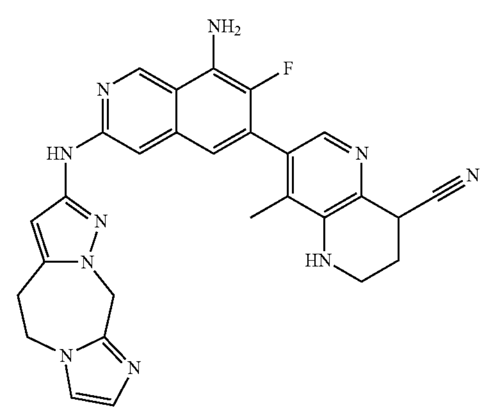 [SMILES: Cc1c(-c2cc3cc(Nc4cc5n(n4)Cc4nccn4CC5)ncc3c(N)c2F)cnc2c1NCCC2C#N] | (+/−)-7-(8-amino-3-((5,6-dihydro-11H-imidazo[1,2-a]pyrazolo[1,5-d][1,4]diazepin-8-yl)amino)-7-fluoroisoquinolin-6-yl)-8-methyl-1,2,3,4-tetrahydro-1,5-naphthyridine-4-carbonitrile |

TABLE 3-continued

| Compound No. | Structure | Name |
|---|---|---|
| 444 | 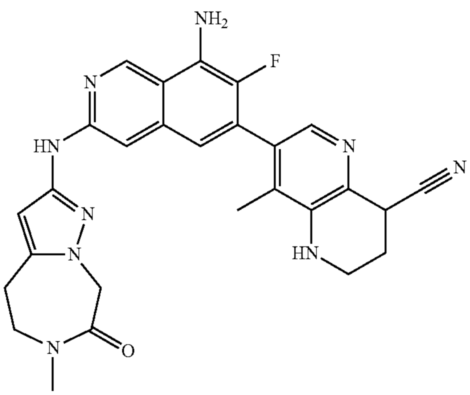 [SMILES: Cc1c(-c2cc3cc(Nc4cc5n(n4)CC(=O)N(C)CC5)ncc3c(N)c2F)cnc2c1NCCC2C#N] | (+/−)-7-(8-amino-7-fluoro-3-((6-methyl-7-oxo-5,6,7,8-tetrahydro-4H-pyrazolo[1,5-d][1,4]diazepin-2-yl)amino)isoquinolin-6-yl)-8-methyl-1,2,3,4-tetrahydro-1,5-naphthyridine-4-carbonitrile |
| 445 | 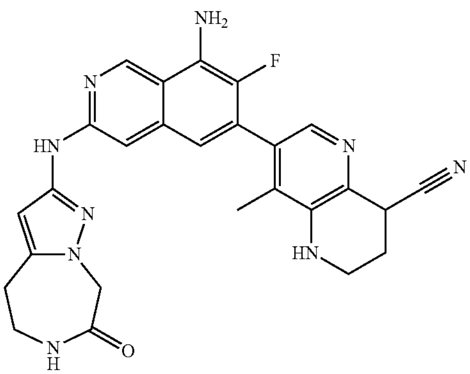 [SMILES: Cc1c(-c2cc3cc(Nc4cc5n(n4)CC(=O)NCC5)ncc3c(N)c2F)cnc2c1NCCC2C#N] | (+/−)-7-(8-amino-7-fluoro-3-((7-oxo-5,6,7,8-tetrahydro-4H-pyrazolo[1,5-d][1,4]diazepin-2-yl)amino)isoquinolin-6-yl)-8-methyl-1,2,3,4-tetrahydro-1,5-naphthyridine-4-carbonitrile |
| 446 | 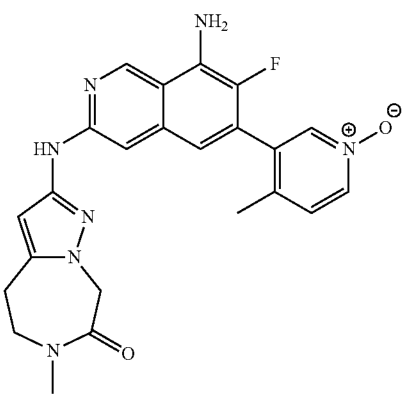 [SMILES: Cc1cc[n+]([O-])cc1-c1cc2cc(Nc3cc4n(n3)CC(=O)N(C)CC4)ncc2c(N)c1F] | 3-(8-amino-7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridine-1-oxide |
| 447 | 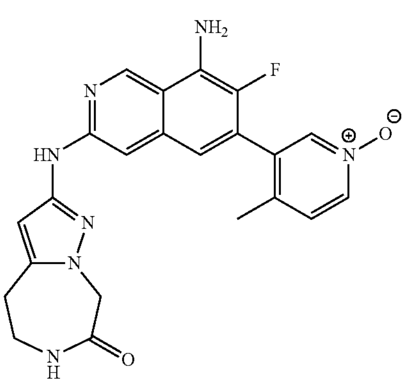 [SMILES: Cc1cc[n+]([O-])cc1-c1cc2cc(Nc3cc4n(n3)CC(=O)NCC4)ncc2c(N)c1F] | 3-(8-amino-7-fluoro-3-((7-oxo-5,6,7,8-tetrahydro-4H-pyrazolo[1,5-d][1,4]diazepin-2-yl)amino)isoquinolin-6-yl)-4-methylpyridine 1-oxide |

TABLE 3-continued

| Compound No. | Structure | Name |
|---|---|---|
| 448 | 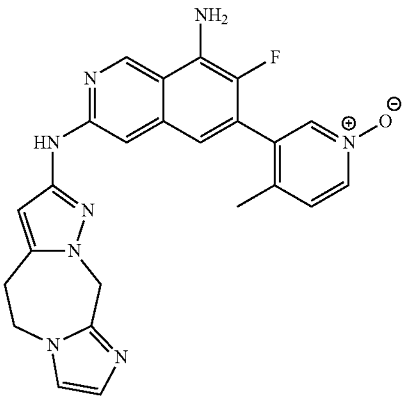 [SMILES: Cc1cc[n+]([O-])cc1-c1cc2cc(Nc3cc4n(n3)Cc3nccn3CC4)ncc2c(N)c1F] | 3-(8-amino-3-((5,6-dihydro-11H-imidazo[1,2-a]pyrazolo[1,5-d][1,4]diazepin-8-yl)amino)-7-fluoroisoquinolin-6-yl)-4-methylpyridine 1-oxide |
| 449 | 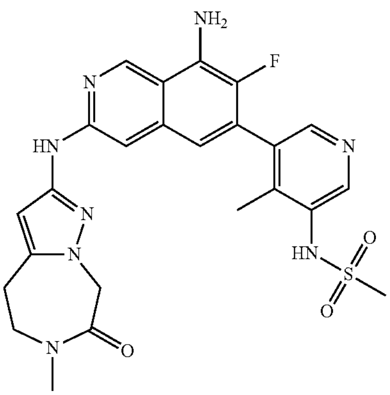 [SMILES: Cc1c(NS(C)(=O)=O)cncc1-c1cc2cc(Nc3cc4n(n3)CC(=O)N(C)CC4)ncc2c(N)c1F] | N-(5-(8-amino-7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)methanesulfonamide |
| 450 | 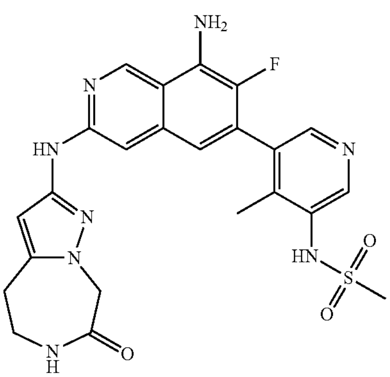 [SMILES: Cc1c(NS(C)(=O)=O)cncc1-c1cc2cc(Nc3cc4n(n3)CC(=O)NCC4)ncc2c(N)c1F] | N-(5-(8-amino-7-fluoro-3-((7-oxo-5,6,7,8-tetrahydro-4H-pyrazolo[1,5-d][1,4]diazepin-2-yl)amino)isoquinolin-6-yl)-4-methylpyridin-3-yl)methanesulfonamide |
| 451 | 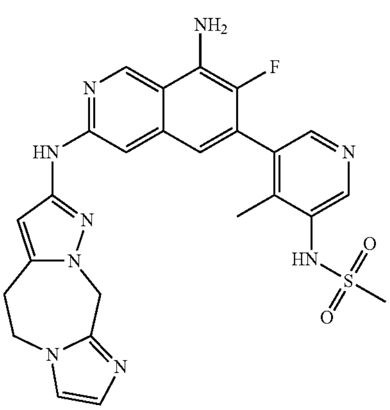 [SMILES: Cc1c(NS(C)(=O)=O)cncc1-c1cc2cc(Nc3cc4n(n3)Cc3nccn3CC4)ncc2c(N)c1F] | N-(5-(8-amino-3-((5,6-dihydro-11H-imidazo[1,2-a]pyrazolo[1,5-d][1,4]diazepin-8-yl)amino)-7-fluoroisoquinolin-6-yl)-4-methylpyridin-3-yl)methanesulfonamide |

TABLE 3-continued

| Compound No. | Structure | Name |
|---|---|---|
| 452 | 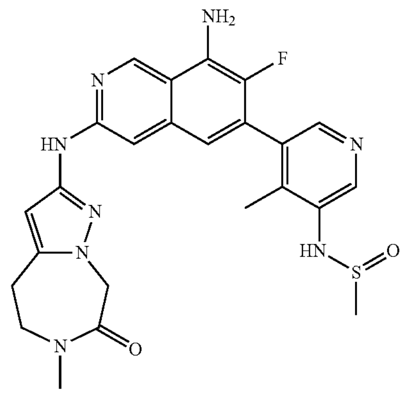 [SMILES: Cc1c(NS(C)=O)cncc1-c1cc2cc(Nc3cc4n(n3)CC(=O)N(C)CC4)ncc2c(N)c1F] | N-(5-(8-amino-7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)methanesulfinamide |
| 453 | 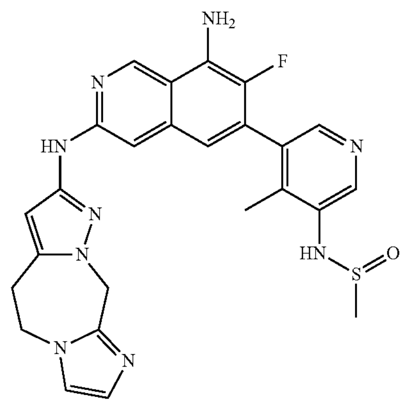 [SMILES: Cc1c(NS(C)=O)cncc1-c1cc2cc(Nc3cc4n(n3)Cc3nccn3CC4)ncc2c(N)c1F] | N-(5-(8-amino-3-((5,6-dihydro-11H-imidazo[1,2-a]pyrazolo[1,5-d][1,4]diazepin-8-yl)amino)-7-fluoroisoquinolin-6-yl)-4-methylpyridin-3-yl)methane sulfinamide |
| 454 | 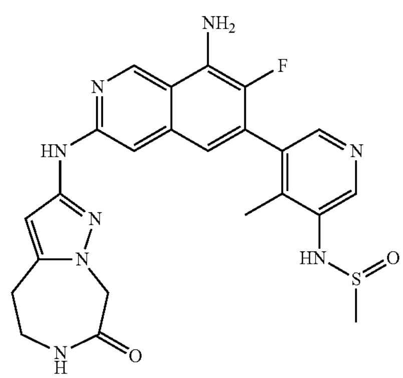 [SMILES: Cc1c(NS(C)=O)cncc1-c1cc2cc(Nc3cc4n(n3)CC(=O)NCC4)ncc2c(N)c1F] | N-(5-(8-amino-7-fluoro-3-((7-oxo-5,6,7,8-tetrahydro-4H-pyrazolo[1,5-d][1,4]diazepin-2-yl)amino)isoquinolin-6-yl)-4-methylpyridin-3-yl)methanesulfinamide |
| 455 | 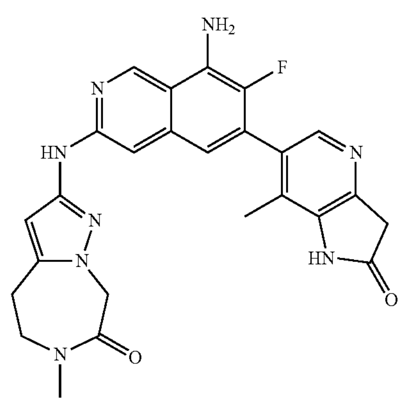 [SMILES: Cc1c(-c2cc3cc(Nc4cc5n(n4)CC(=O)N(C)CC5)ncc3c(N)c2F)cnc2c1NC(=O)C2] | 2-((8-amino-7-fluoro-6-(7-methyl-2-oxo-2,3-dihydro-1H-pyrrolo[3,2-b]pyridin-6-yl)isoquinolin-3-yl)amino)-6-methyl-5,6-dihydro-4H-pyrazolo[1,5-d][1,4]diazepin-7(8H)-one |

TABLE 3-continued

| Compound No. | Structure | Name |
|---|---|---|
| 456 | 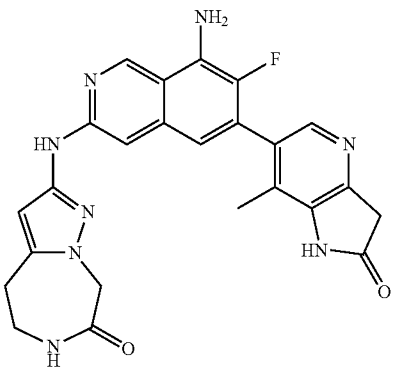 [SMILES: Cc1c(-c2cc3cc(Nc4cc5n(n4)CC(=O)NCC5)ncc3c(N)c2F)cnc2c1NC(=O)C2] | 2-((8-amino-7-fluoro-6-(7-methyl-2-oxo-2,3-dihydro-1H-pyrrolo[3,2-b]pyridin-6-yl)isoquinolin-3-yl)amino)-5,6-dihydro-4H-pyrazolo[1,5-d][1,4]diazepin-7(8H)-one |
| 457 | 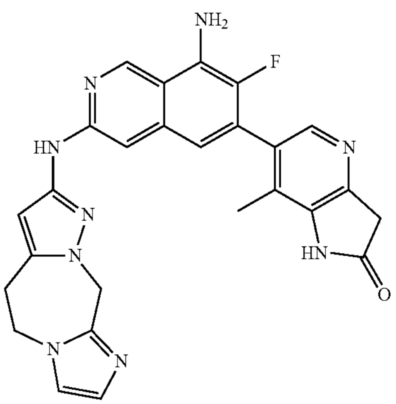 [SMILES: Cc1c(-c2cc3cc(Nc4cc5n(n4)Cc4nccn4CC5)ncc3c(N)c2F)cnc2c1NC(=O)C2] | 6-(8-amino-3-((5,6-dihydro-11H-imidazo[1,2-a]pyrazolo[1,5-d][1,4]diazepin-8-yl)amino)-7-fluoroisoquinolin-6-yl)-7-methyl-1,3-dihydro-2H-pyrrolo[3,2-b]pyridin-2-one |
| 458 | 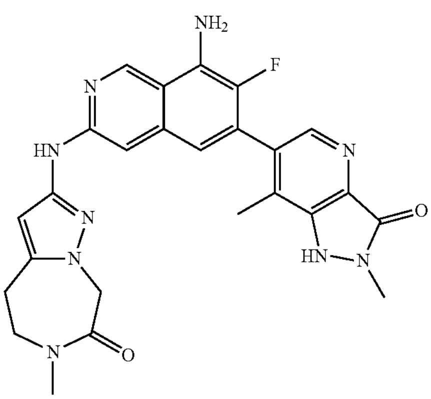 [SMILES: Cc1c(-c2cc3cc(Nc4cc5n(n4)CC(=O)N(C)CC5)ncc3c(N)c2F)cnc2c(=O)n(C)[nH]c12] | 2-((8-amino-6-(2,7-dimethyl-3-oxo-2,3-dihydro-1H-pyrazolo[4,3-b]pyridin-6-yl)-7-fluoroisoquinolin-3-yl)amino)-6-methyl-5,6-dihydro-4H-pyrazolo[1,5-d][1,4]diazepin-7(8H)-one |
| 459 | 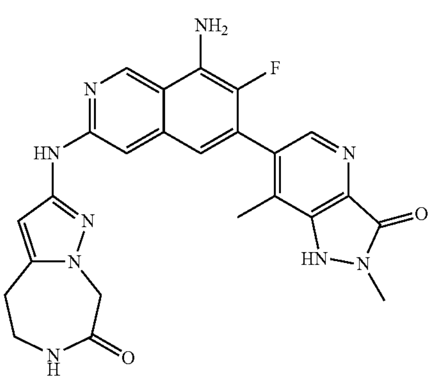 [SMILES: Cc1c(-c2cc3cc(Nc4cc5n(n4)CC(=O)NCC5)ncc3c(N)c2F)cnc2c(=O)n(C)[nH]c12] | 2-((8-amino-6-(2,7-dimethyl-3-oxo-2,3-dihydro-1H-pyrazolo[4,3-b]pyridin-6-yl)-7-fluoroisoquinolin-3-yl)amino)-5,6-dihydro-4H-pyrazolo[1,5-d][1,4]diazepin-7(8H)-one |

TABLE 3-continued

| Compound No. | Structure | Name |
|---|---|---|
| 460 | 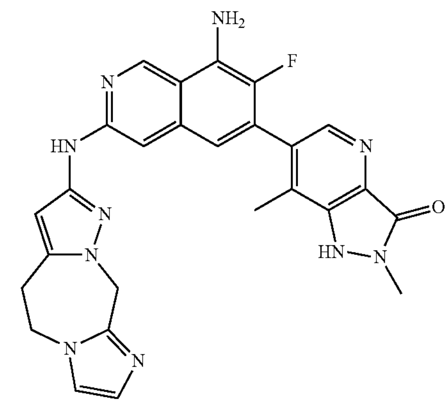 [SMILES: Cc1c(-c2cc3cc(Nc4cc5n(n4)Cc4nccn4CC5)ncc3c(N)c2F)cnc2c(=O)n(C)[nH]c12] | 6-(8-amino-3-((5,6-dihydro-11H-imidazo[1,2-a]pyrazolo[1,5-d][1,4]diazepin-8-yl)amino)-7-fluoroisoquinolin-6-yl)-2,7-dimethyl-1,2-dihydro-3H-pyrazolo[4,3-b]pyridin-3-one |
| 461 | 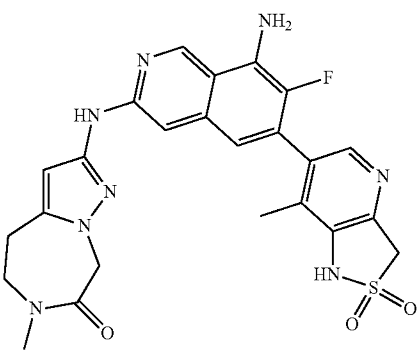 [SMILES: Cc1c(-c2cc3cc(Nc4cc5n(n4)CC(=O)N(C)CC5)ncc3c(N)c2F)cnc2c1NS(=O)(=O)C2] | 2-((8-amino-7-fluoro-6-(7-methyl-2,2-dioxido-1,3-dihydroisothiazolo[4,3-b]pyridin-6-yl)isoquinolin-3-yl)amino)-6-methyl-5,6-dihydro-4H-pyrazolo[1,5-d][1,4]diazepin-7(8H)-one |
| 462 | 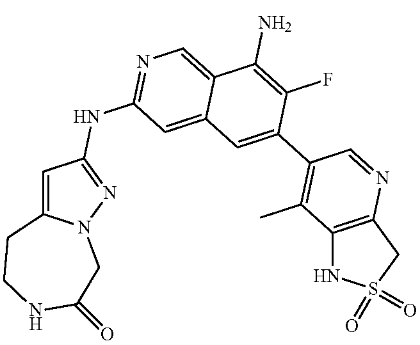 [SMILES: Cc1c(-c2cc3cc(Nc4cc5n(n4)CC(=O)NCC5)ncc3c(N)c2F)cnc2c1NS(=O)(=O)C2] | 2-((8-amino-7-fluoro-6-(7-methyl-2,2-dioxido-1,3-dihydroisothiazolo[4,3-b]pyridin-6-yl)isoquinolin-3-yl)amino)-5,6-dihydro-4H-pyrazolo[1,5-d][1,4]diazepin-7(8H)-one |
| 463 | 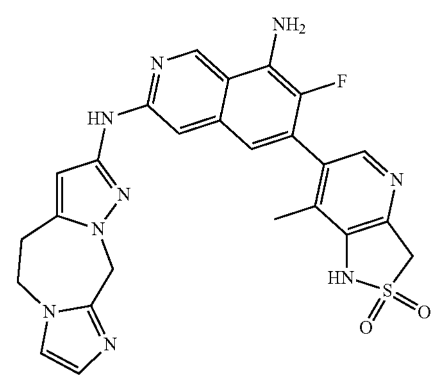 [SMILES: Cc1c(-c2cc3cc(Nc4cc5n(n4)Cc4nccn4CC5)ncc3c(N)c2F)cnc2c1NS(=O)(=O)C2] | 6-(8-amino-3-((5,6-dihydro-11H-imidazo[1,2-a]pyrazolo[1,5-d][1,4]diazepin-8-yl)amino)-7-fluoroisoquinolin-6-yl)-7-methyl-1,3-dihydroisothiazolo[4,3-b]pyridine 2,2-dioxide |

TABLE 3-continued

| Compound No. | Structure | Name |
|---|---|---|
| 464 | 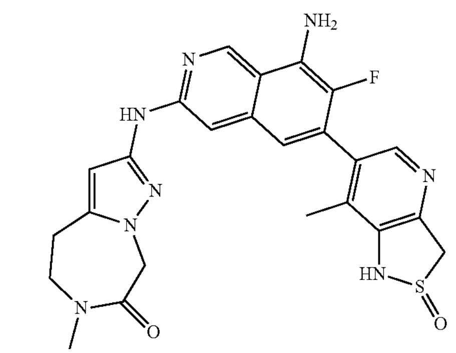 [SMILES: Cc1c(-c2cc3cc(Nc4cc5n(n4)CC(=O)N(C)CC5)ncc3c(N)c2F)cnc2c1NS(=O)C2] | 2-((8-amino-7-fluoro-6-(7-methyl-2-oxido-1,3-dihydroisothiazolo[4,3-b]pyridin-6-yl)isoquinolin-3-yl)amino)-6-methyl-5,6-dihydro-4H-pyrazolo[1,5-d][1,4]diazepin-7(8H)-one |
| 465 | 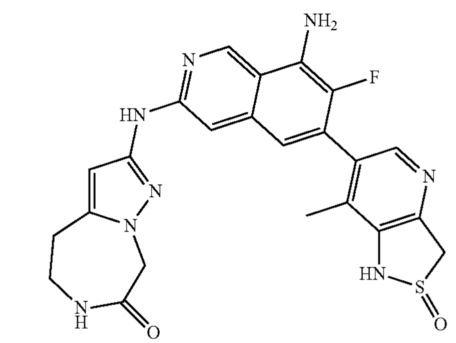 [SMILES: Cc1c(-c2cc3cc(Nc4cc5n(n4)CC(=O)NCC5)ncc3c(N)c2F)cnc2c1NS(=O)C2] | 2-((8-amino-7-fluoro-6-(7-methyl-2-oxido-1,3-dihydroisothiazolo[4,3-b]pyridin-6-yl)isoquinolin-3-yl)amino)-5,6-dihydro-4H-pyrazolo[1,5-d][1,4]diazepin-7(8H)-one |
| 466 | 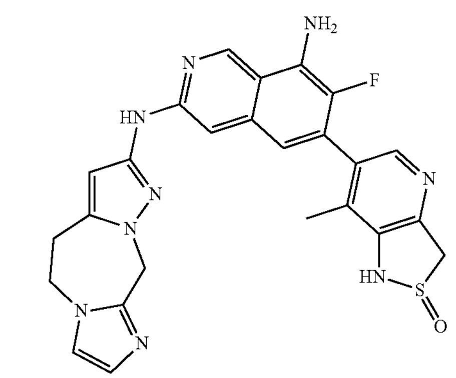 [SMILES: Cc1c(-c2cc3cc(Nc4cc5n(n4)Cc4nccn4CC5)ncc3c(N)c2F)cnc2c1NS(=O)C2] | 6-(8-amino-3-((5,6-dihydro-11H-imidazo[1,2-a]pyrazolo[1,5-d][1,4]diazepin-8-yl)amino)-7-fluoroisoquinolin-6-yl)-7-methyl-1,3-dihydroisothiazolo[4,3-b]pyridine 2-oxide |
| 467 | 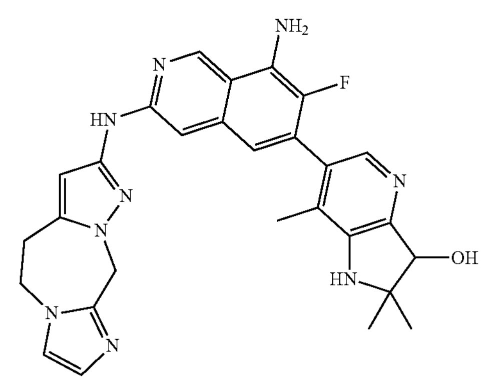 [SMILES: Cc1c(-c2cc3cc(Nc4cc5n(n4)Cc4nccn4CC5)ncc3c(N)c2F)cnc2c1NC(C)(C)C2O] | (+/−)-6-(8-amino-3-((5,6-dihydro-11H-imidazo[1,2-a]pyrazolo[1,5-d][1,4]diazepin-8-yl)amino)-7-fluoroisoquinolin-6-yl)-2,2,7-trimethyl-2,3-dihydro-1H-pyrrolo[3,2-b]pyridin-3-ol |

TABLE 3-continued

| Compound No. | Structure | Name |
|---|---|---|
| 468 | 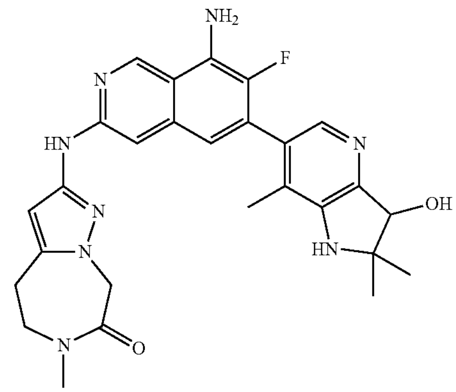 [SMILES: Cc1c(-c2cc3cc(Nc4cc5n(n4)CC(=O)N(C)CC5)ncc3c(N)c2F)cnc2c1NC(C)(C)C2O] | (+/−)-2-((8-amino-7-fluoro-6-(3-hydroxy-2,2,7-trimethyl-2,3-dihydro-1H-pyrrolo[3,2-b]pyridin-6-yl)isoquinolin-3-yl)amino)-6-methyl-5,6-dihydro-4H-pyrazolo[1,5-d][1,4]diazepin-7(8H)-one |
| 469 | 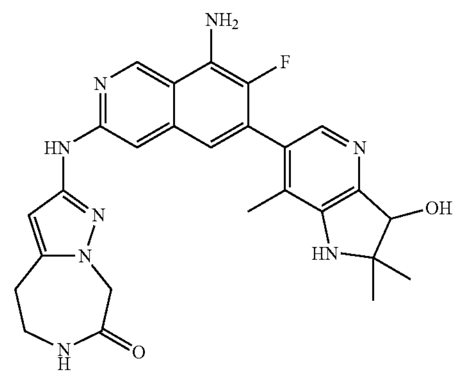 [SMILES: Cc1c(-c2cc3cc(Nc4cc5n(n4)CC(=O)NCC5)ncc3c(N)c2F)cnc2c1NC(C)(C)C2O] | (+/−)-2-((8-amino-7-fluoro-6-(3-hydroxy-2,2,7-trimethyl-2,3-dihydro-1H-pyrrolo[3,2-b]pyridin-6-yl)isoquinolin-3-yl)amino)-5,6-dihydro-4H-pyrazolo[1,5-d][1,4]diazepin-7(8H)-one |
| 470 | 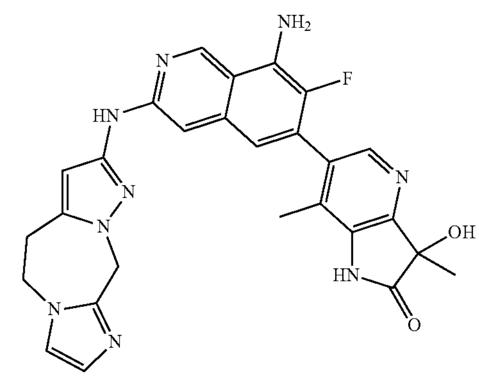 [SMILES: Cc1c(-c2cc3cc(Nc4cc5n(n4)Cc4nccn4CC5)ncc3c(N)c2F)cnc2c1NC(=O)C2(C)O] | (+/−)-6-(8-amino-3-((5,6-dihydro-11H-imidazo[1,2-a]pyrazolo[1,5-d][1,4]diazepin-8-yl)amino)-7-fluoroisoquinolin-6-yl)-3-hydroxy-3,7-dimethyl-1,3-dihydro-2H-pyrazolo[3,2-b]pyridin-2-one |
| 471 | 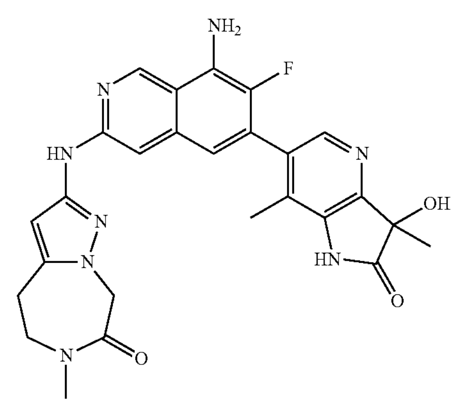 [SMILES: Cc1c(-c2cc3cc(Nc4cc5n(n4)CC(=O)N(C)CC5)ncc3c(N)c2F)cnc2c1NC(=O)C2(C)O] | (+/−)-2-((8-amino-7-fluoro-6-(3-hydroxy-3,7-dimethyl-2-oxo-2,3-dihydro-1H-pyrrolo[3,2-b]pyridin-6-yl)isoquinolin-3-yl)amino)-6-methyl-5,6-dihydro-4H-pyrazolo[1,5-d][1,4]diazepin-7(8H)-one |

TABLE 3-continued

| Compound No. | Structure | Name |
| --- | --- | --- |
| 472 | 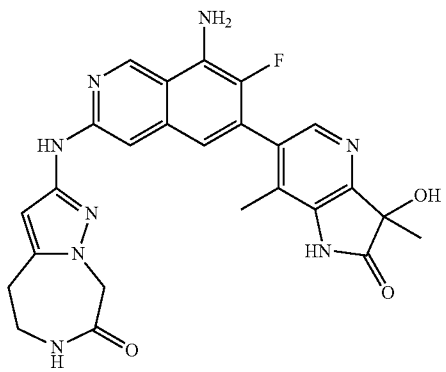 [SMILES: Cc1c(-c2cc3cc(Nc4cc5n(n4)CC(=O)NCC5)ncc3c(N)c2F)cnc2c1NC(=O)C2(C)O] | (+/−)-2-((8-amino-7-fluoro-6-(3-hydroxy-3,7-dimethyl-2-oxo-2,3-dihydro-1H-pyrrolo[3,2-b]pyridin-6-yl)isoquinolin-3-yl)amino)-5,6-dihydro-4H-pyrazolo[1,5-d][1,4]diazepin-7(8H)-one |
| 473 | 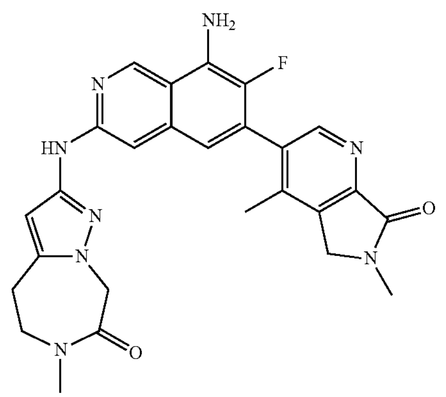 [SMILES: Cc1c(-c2cc3cc(Nc4cc5n(n4)CC(=O)N(C)CC5)ncc3c(N)c2F)cnc2c1CN(C)C2=O] | 2-((8-amino-6-(4,6-dimethyl-7-oxo-6,7-dihydro-5H-pyrrolo[3,4-b]pyridin-3-yl)-7-fluoroisoquinolin-3-yl)amino)-6-methyl-5,6-dihydro-4H-pyrazolo[1,5-d][1,4]diazepin-7(8H)-one |
| 474 | 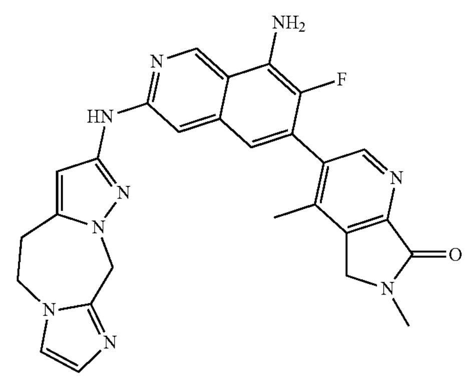 [SMILES: Cc1c(-c2cc3cc(Nc4cc5n(n4)Cc4nccn4CC5)ncc3c(N)c2F)cnc2c1CN(C)C2=O] | 3-(8-amino-3-((5,6-dihydro-11H-imidazo[1,2-a]pyrazolo[1,5-d][1,4]diazepin-8-yl)amino)-7-fluoroisoquinolin-6-yl)-4,6-dimethyl-5,6-dihydro-7H-pyrrolo[3,4-b]pyridin-7-one |
| 475 | 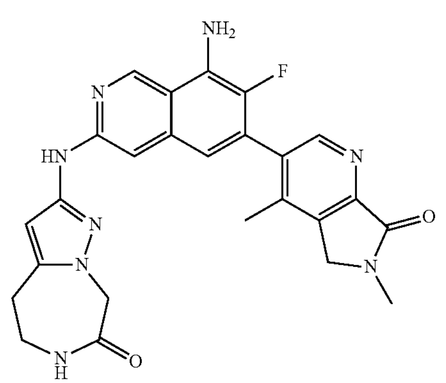 [SMILES: Cc1c(-c2cc3cc(Nc4cc5n(n4)CC(=O)NCC5)ncc3c(N)c2F)cnc2c1CN(C)C2=O] | 2-((8-amino-6-(4,6-dimethyl-7-oxo-6,7-dihydro-5H-pyrrolo[3,4-b]pyridin-3-yl)-7-fluoroisoquinolin-3-yl)amino)-5,6-dihydro-4H-pyrazolo[1,5-d][1,4]diazepin-7(8H)-one |

TABLE 3-continued

| Compound No. | Structure | Name |
|---|---|---|
| 476 | 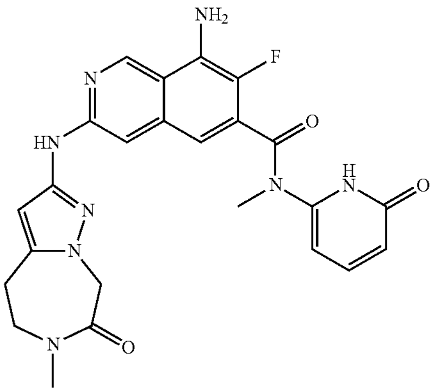 [SMILES: CN1CCc2cc(Nc3cc4cc(C(=O)N(C)c5cccc(=O)[nH]5)c(F)c(N)c4cn3)nn2CC1=O] | 8-amino-7-fluoro-N-methyl-3-((6-methyl-7-oxo-5,6,7,8-tetrahydro-4H-pyrazolo[1,5-d][1,4]diazepin-2-yl)amino)-N-(6-oxo-1,6-dihydropyridin-2-yl)isoquinoline-6-carboxamide |
| 477 | 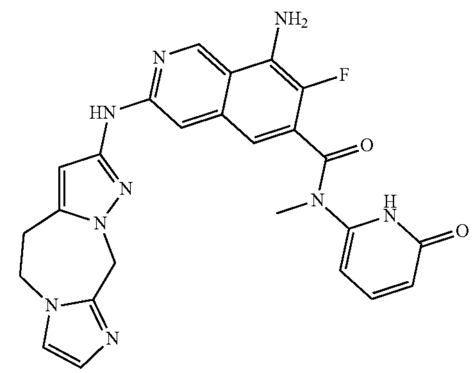 [SMILES: CN(C(=O)c1cc2cc(Nc3cc4n(n3)Cc3nccn3CC4)ncc2c(N)c1F)c1cccc(=O)[nH]1] | 8-amino-3-((5,6-dihydro-11H-imidazo[1,2-a]pyrazolo[1,5-d][1,4]diazepin-8-yl)amino)-7-fluoro-N-methyl-N-(6-oxo-1,6-dihydropyridin-2-yl)isoquinoline-6-carboxamide |
| 478 | 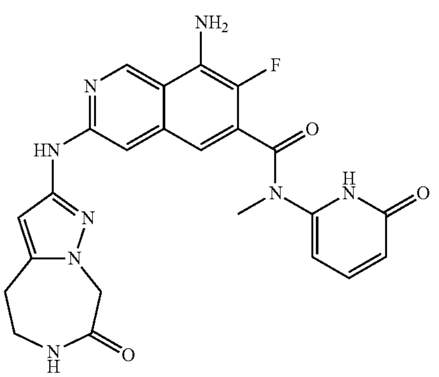 [SMILES: CN(C(=O)c1cc2cc(Nc3cc4n(n3)CC(=O)NCC4)ncc2c(N)c1F)c1cccc(=O)[nH]1] | 8-amino-7-fluoro-N-methyl-N-(6-oxo-1,6-dihydropyridin-2-yl)-3-((7-oxo-5,6,7,8-tetrahydro-4H-pyrazolo[1,5-d][1,4]diazepin-2-yl)amino)isoquinoline-6-carboxamide |
| 479 | 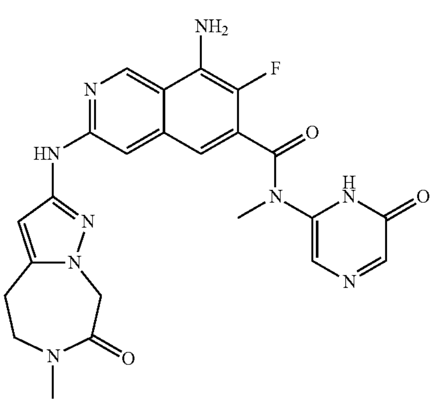 [SMILES: CN1CCc2cc(Nc3cc4cc(C(=O)N(C)c5cncc(=O)[nH]5)c(F)c(N)c4cn3)nn2CC1=O] | 8-amino-7-fluoro-N-methyl-3-((6-methyl-7-oxo-5,6,7,8-tetrahydro-4H-pyrazolo[1,5-d][1,4]diazepin-2-yl)amino)-N-(6-oxo-1,6-dihydropyrazin-2-yl)isoquinoline-6-carboxamide |

TABLE 3-continued

| Compound No. | Structure | Name |
|---|---|---|
| 480 | 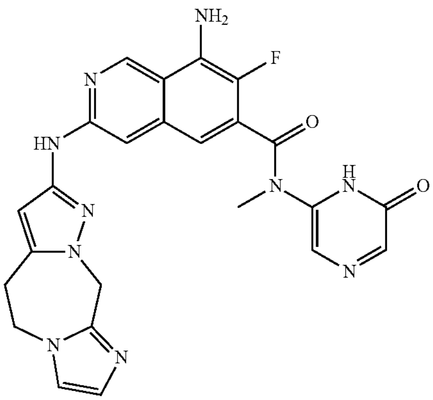 [SMILES: CN(C(=O)c1cc2cc(Nc3cc4n(n3)Cc3nccn3CC4)ncc2c(N)c1F)c1cncc(=O)[nH]1] | 8-amino-3-((5,6-dihydro-11H-imidazo[1,2-a]pyrazolo[1,5-d][1,4]diazepin-8-yl)amino)-7-fluoro-N-methyl-N-(6-oxo-1,6-dihydropyrazin-2-yl)isoquinoline-6-carboxamide |
| 481 | 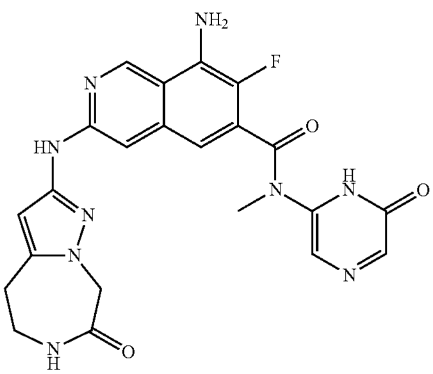 [SMILES: CN(C(=O)c1cc2cc(Nc3cc4n(n3)CC(=O)NCC4)ncc2c(N)c1F)c1cncc(=O)[nH]1] | 8-amino-7-fluoro-N-methyl-N-(6-oxo-1,6-dihydropyrazin-2-yl)-3-((7-oxo-5,6,7,8-tetrahydro-4H-pyrazolo[1,5-d][1,4]diazepin-2-yl)amino)isoquinoline-6-carboxamide |
| 482 | 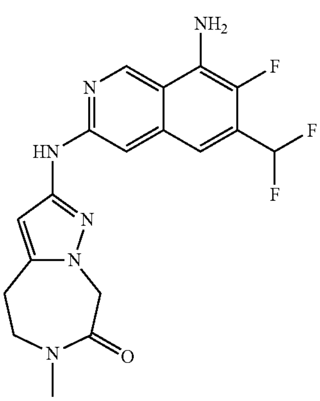 [SMILES: CN1CCc2cc(Nc3cc4cc(C(F)F)c(F)c(N)c4cn3)nn2CC1=O] | 2-((8-amino-6-(difluoromethyl)-7-fluoroisoquinolin-3-yl)amino)-6-methyl-5,6-dihydro-4H-pyrazolo[1,5-d][1,4]diazepin-7(8H)-one |
| 483 | 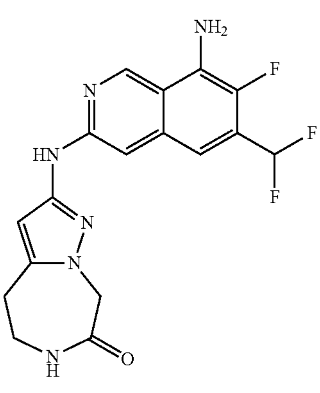 [SMILES: Nc1c(F)c(C(F)F)cc2cc(Nc3cc4n(n3)CC(=O)NCC4)ncc12] | 2-((8-amino-6-(difluoromethyl)-7-fluoroisoquinolin-3-yl)amino)-5,6-dihydro-4H-pyrazolo[1,5-d][1,4]diazepin-7(8H)-one |

TABLE 3-continued

| Compound No. | Structure | Name |
|---|---|---|
| 484 | 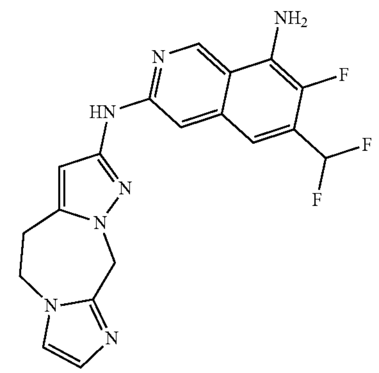 [SMILES: Nc1c(F)c(C(F)F)cc2cc(Nc3cc4n(n3)Cc3nccn3CC4)ncc12] | 6-(difluoromethyl)-N3-(5,6-dihydro-11H-imidazo[1,2-a]pyrazolo[1,5-d][1,4]diazepin-8-yl)-7-fluoroisoquinoline-3,8-diamine |
| 485 | 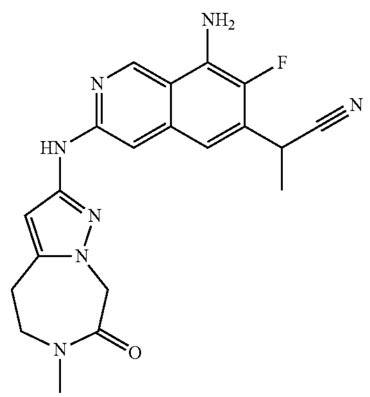 [SMILES: CC(C#N)c1cc2cc(Nc3cc4n(n3)CC(=O)N(C)CC4)ncc2c(N)c1F] | (+/−)-2-(8-amino-7-fluoro-3-((6-methyl-7-oxo-5,6,7,8-tetrahydro-4H-pyrazolo[1,5-d][1,4]diazepin-2-yl)amino)isoquinolin-6-yl)propanenitrile |
| 486 | 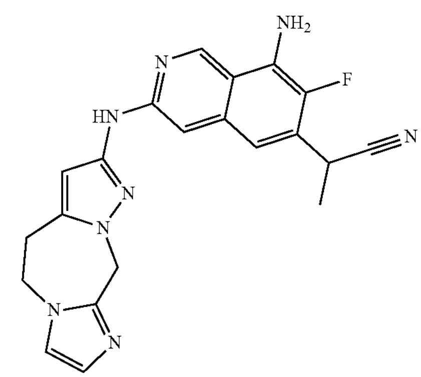 [SMILES: CC(C#N)c1cc2cc(Nc3cc4n(n3)Cc3nccn3CC4)ncc2c(N)c1F] | (+/−)-2-(8-amino-3-((5,6-dihydro-11H-imidazo[1,2-a]pyrazolo[1,5-d][1,4]diazepin-8-yl)amino)-7-fluoroisoquinolin-6-yl)propanenitrile |
| 487 | 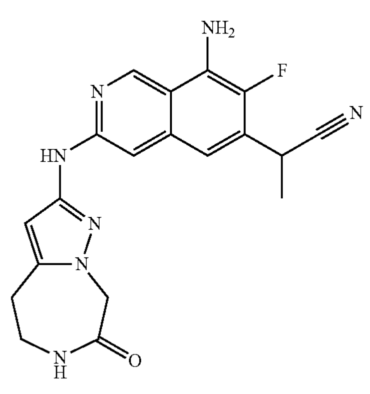 [SMILES: CC(C#N)c1cc2cc(Nc3cc4n(n3)CC(=O)NCC4)ncc2c(N)c1F] | (+/−)-2-(8-amino-7-fluoro-3-((7-oxo-5,6,7,8-tetrahydro-4H-pyrazolo[1,5-d][1,4]diazepin-2-yl)amino)isoquinolin-6-yl)propanenitrile |

TABLE 3-continued

| Compound No. | Structure | Name |
|---|---|---|
| 488 | 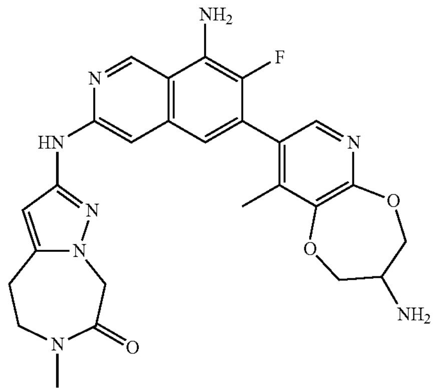 [SMILES: Cc1c(-c2cc3cc(Nc4cc5n(n4)CC(=O)N(C)CC5)ncc3c(N)c2F)cnc2c1OCC(N)CO2] | (+/−)-2-((8-amino-6-(3-amino-9-methyl-3,4-dihydro-2H-[1,4]dioxepino[2,3-b]pyridin-8-yl)-7-fluoroisoquinolin-3-yl)amino)-6-methyl-5,6-dihydro-4H-pyrazolo[1,5-d][1,4]diazepin-7(8H)-one |
| 489 | 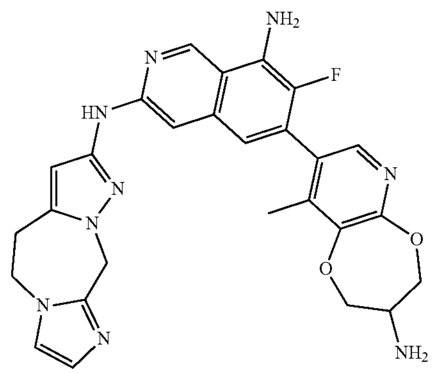 [SMILES: Cc1c(-c2cc3cc(Nc4cc5n(n4)Cc4nccn4CC5)ncc3c(N)c2F)cnc2c1OCC(N)CO2] | (+/−)-6-(3-amino-9-methyl-3,4-dihydro-2H-[1,4]dioxepino[2,3-b]pyridin-8-yl)-N3-(5,6-dihydro-11H-imidazo[1,2-a]pyrazolo[1,5-d][1,4]diazepin-8-yl)-7-fluoroisoquinoline-3,8-diamine |
| 490 | 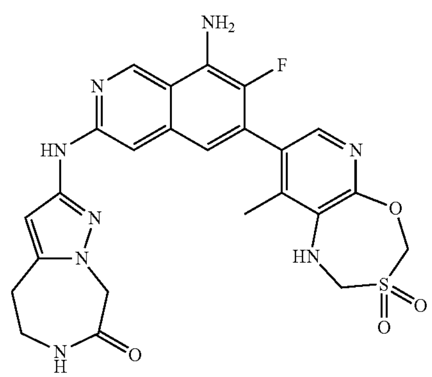 [SMILES: Cc1c(-c2cc3cc(Nc4cc5n(n4)CC(=O)NCC5)ncc3c(N)c2F)cnc2c1NCS(=O)(=O)CO2] | 2-((8-amino-7-fluoro-6-(9-methyl-3,3-dioxido-1,2-dihydro-4H-pyrido[3,2-f][1,3,5]oxathiazepin-8-yl)isoquinolin-3-yl)amino)-5,6-dihydro-4H-pyrazolo[1,5-d][1,4]diazepin-7(8H)-one |
| 491 | 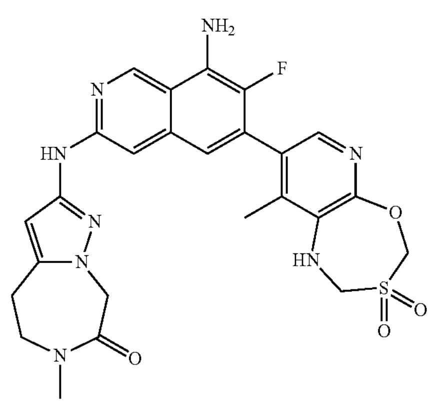 [SMILES: Cc1c(-c2cc3cc(Nc4cc5n(n4)CC(=O)N(C)CC5)ncc3c(N)c2F)cnc2c1NCS(=O)(=O)CO2] | 2-((8-amino-7-fluoro-6-(9-methyl-3,3-dioxido-1,2-dihydro-4H-pyrido[3,2-f][1,3,5]oxathiazepin-8-yl)isoquinolin-3-yl)amino)-6-methyl-5,6-dihydro-4H-pyrazolo[1,5-d][1,4]diazepin-7(8H)-one |

TABLE 3-continued

| Compound No. | Structure | Name |
|---|---|---|
| 492 | 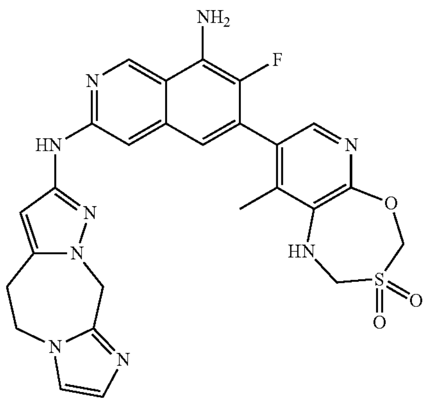 [SMILES: Cc1c(-c2cc3cc(Nc4cc5n(n4)Cc4nccn4CC5)ncc3c(N)c2F)cnc2c1NCS(=O)(=O)CO2] | 8-(8-amino-3-((5,6-dihydro-11H-imidazo[1,2-a]pyrazolo[1,5-d][1,4]diazepin-8-yl)amino)-7-fluoroisoquinolin-6-yl)-9-methyl-1,2-dihydro-4H-pyrido[3,2-f][1,3,5]oxathiazepine 3,3-dioxide |
| 493 | 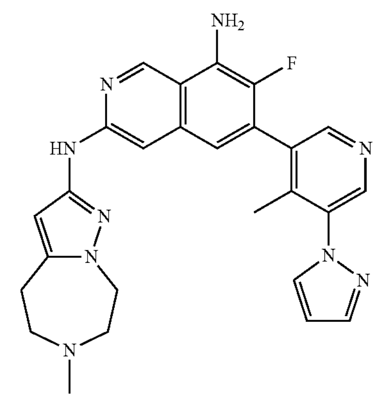 [SMILES: Cc1c(-c2cc3cc(Nc4cc5n(n4)CCN(C)CC5)ncc3c(N)c2F)cncc1-n1cccn1] | 2-((8-amino-7-fluoro-6-(4-methyl-5-(1H-pyrazol-1-yl)pyridin-3-yl)isoquinolin-3-yl)amino)-6-methyl-5,6-dihydro-4H-pyrazolo[1,5-d][1,4]diazepin-7(8H)-one |
| 494 | 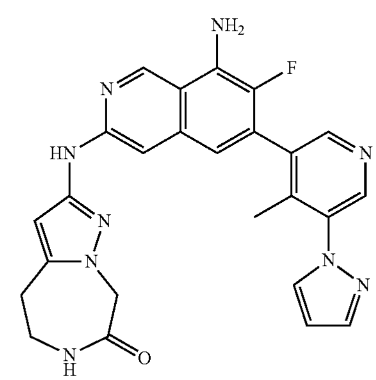 [SMILES: Cc1c(-c2cc3cc(Nc4cc5n(n4)CC(=O)NCC5)ncc3c(N)c2F)cncc1-n1cccn1] | 2-((8-amino-7-fluoro-6-(4-methyl-5-(1H-pyrazol-1-yl)pyridin-3-yl)isoquinolin-3-yl)amino)-5,6-dihydro-4H-pyrazolo[1,5-d][1,4]diazepin-7(8H)-one |
| 495 | 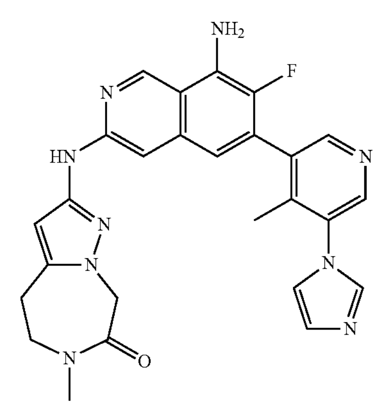 [SMILES: Cc1c(-c2cc3cc(Nc4cc5n(n4)CC(=O)N(C)CC5)ncc3c(N)c2F)cncc1-n1ccnc1] | 2-((6-(5-(1H-imidazol-1-yl)-4-methylpyridin-3-yl)-8-amino-7-fluoroisoquinolin-3-yl)amino)-6-methyl-5,6-dihydro-4H-pyrazolo[1,5-d][1,4]diazepin-7(8H)-one |

TABLE 3-continued

| Compound No. | Structure | Name |
|---|---|---|
| 496 | 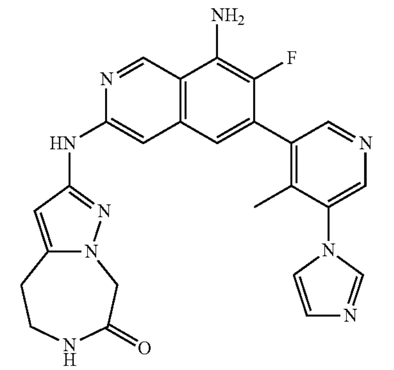 [SMILES: Cc1c(-c2cc3cc(Nc4cc5n(n4)CC(=O)NCC5)ncc3c(N)c2F)cncc1-n1ccnc1] | 2-((6-(5-(1H-imidazol-1-yl)-4-methylpyridin-3-yl)-8-amino-7-fluoroisoquinolin-3-yl)amino)-5,6-dihydro-4H-pyrazolo[1,5-d][1,4]diazepin-7(8H)-one |
| 497 | 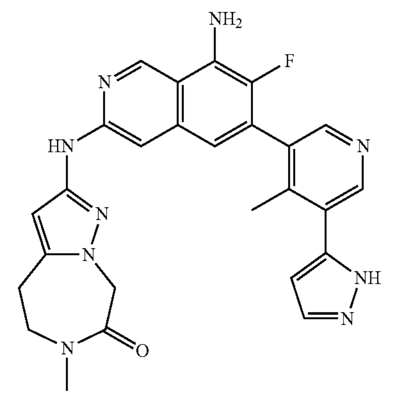 [SMILES: Cc1c(-c2ccn[nH]2)cncc1-c1cc2cc(Nc3cc4n(n3)CC(=O)N(C)CC4)ncc2c(N)c1F] | 2-((8-amino-7-fluoro-6-(4-methyl-5-(1H-pyrazol-5-yl)pyridin-3-yl)isoquinolin-3-yl)amino)-6-methyl-5,6-dihydro-4H-pyrazolo[1,5-d][1,4]diazepin-7(8H)-one |
| 498 | 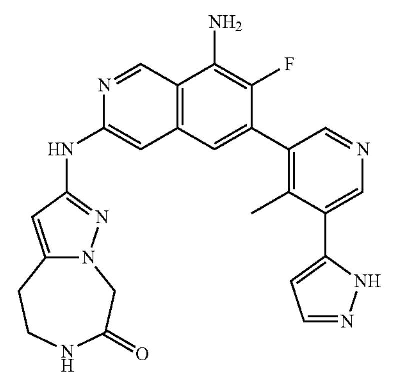 [SMILES: Cc1c(-c2ccn[nH]2)cncc1-c1cc2cc(Nc3cc4n(n3)CC(=O)NCC4)ncc2c(N)c1F] | 2-((8-amino-7-fluoro-6-(4-methyl-5-(1H-pyrazol-5-yl)pyridin-3-yl)isoquinolin-3-yl)amino)-5,6-dihydro-4H-pyrazolo[1,5-d][1,4]diazepin-7(8H)-one |
| 499 | 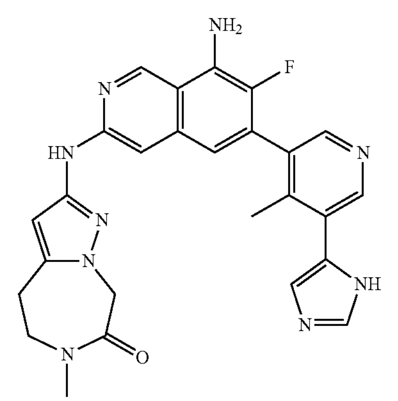 [SMILES: Cc1c(-c2cnc[nH]2)cncc1-c1cc2cc(Nc3cc4n(n3)CC(=O)N(C)CC4)ncc2c(N)c1F] | 2-((6-(5-(1H-imidazol-5-yl)-4-methylpyridin-3-yl)-8-amino-7-fluoroisoquinolin-3-yl)amino)-6-methyl-5,6-dihydro-4H-pyrazolo[1,5-d][1,4]diazepin-7(8H)-one |

TABLE 3-continued

| Compound No. | Structure | Name |
|---|---|---|
| 500 | 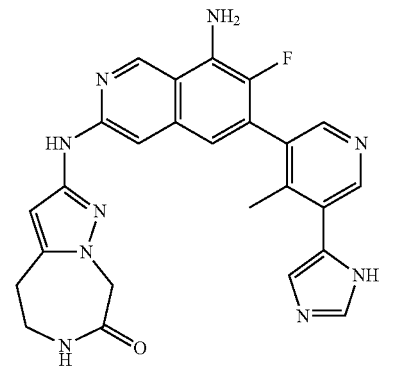 [SMILES: Cc1c(-c2cnc[nH]2)cncc1-c1cc2cc(Nc3cc4n(n3)CC(=O)NCC4)ncc2c(N)c1F] | 2-((6-(5-(1H-imidazol-5-yl)-4-methylpyridin-3-yl)-8-amino-7-fluoroisoquinolin-3-yl)amino)-5,6-dihydro-4H-pyrazolo[1,5-d][1,4]diazepin-7(8H)-one |
| 501 | 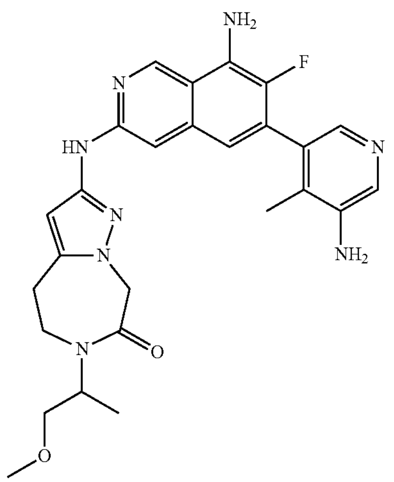 [SMILES: COCC(C)N1CCc2cc(Nc3cc4cc(-c5cncc(N)c5C)c(F)c(N)c4cn3)nn2CC1=O] | (+/−)-2-((8-amino-6-(5-amino-4-methylpyridin-3-yl)-7-fluoroisoquinolin-3-yl)amino)-6-(1-methoxypropan-2-yl)-5,6-dihydro-4H-pyrazolo[1,5-d][1,4]diazepin-7(8H)-one |
| 502 | 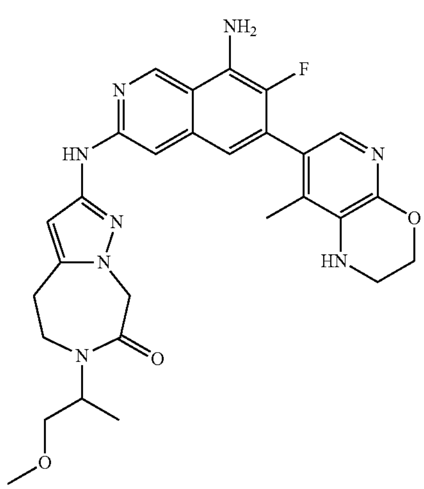 [SMILES: COCC(C)N1CCc2cc(Nc3cc4cc(-c5cnc6c(c5C)NCCO6)c(F)c(N)c4cn3)nn2CC1=O] | (+/−)-2-((8-amino-7-fluoro-6-(8-methyl-2,3-dihydro-1H-pyrido[2,3-b][1,4]oxazin-7-yl)isoquinolin-3-yl)amino)-6-(1-methoxypropan-2-yl)-5,6-dihydro-4H-pyrazolo[1,5-d][1,4]diazepin-7(8H)-one |

TABLE 3-continued

| Compound No. | Structure | Name |
|---|---|---|
| 503 | 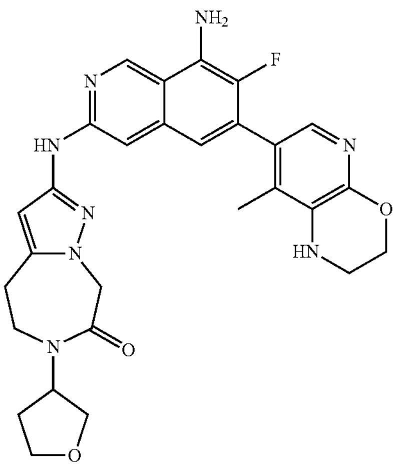 [SMILES: Cc1c(-c2cc3cc(Nc4cc5n(n4)CC(=O)N(C4CCOC4)CC5)ncc3c(N)c2F)cnc2c1NCCO2] | (+/−)-2-((8-amino-7-fluoro-6-(8-methyl-2,3-dihydro-1H-pyrido[2,3-b][1,4]oxazin-7-yl)isoquinolin-3-yl)amino)-6-(tetrahydrofuran-3-yl)-5,6-dihydro-4H-pyrazolo[1,5-d][1,4]diazepin-7(8H)-one |
| 504 | 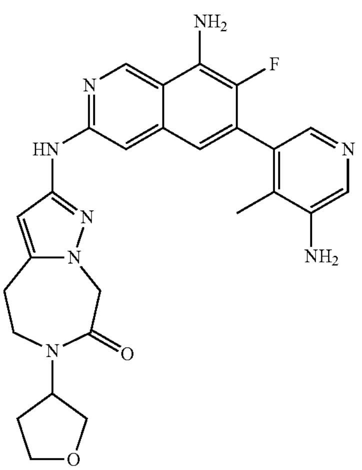 [SMILES: Cc1c(N)cncc1-c1cc2cc(Nc3cc4n(n3)CC(=O)N(C3CCOC3)CC4)ncc2c(N)c1F] | (+/−)-2-((8-amino-6-(5-amino-4-methylpyridin-3-yl)-7-fluoroisoquinolin-3-yl)amino)-6-(tetrahydrofuran-3-yl)-5,6-dihydro-4H-pyrazolo[1,5-d][1,4]diazepin-7(8H)-one |
| 505 | 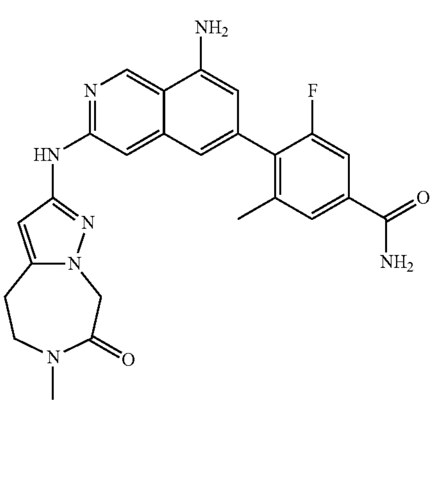 [SMILES: Cc1cc(C(N)=O)cc(F)c1-c1cc(N)c2cnc(Nc3cc4n(n3)CC(=O)N(C)CC4)cc2c1] | 4-(8-amino-3-((6-methyl-7-oxo-5,6,7,8-tetrahydro-4H-pyrazolo[1,5-d][1,4]diazepin-2-yl)amino)isoquinolin-6-yl)-3-fluoro-5-methylbenzamide |

TABLE 3-continued

| Compound No. | Structure | Name |
|---|---|---|
| 506 | 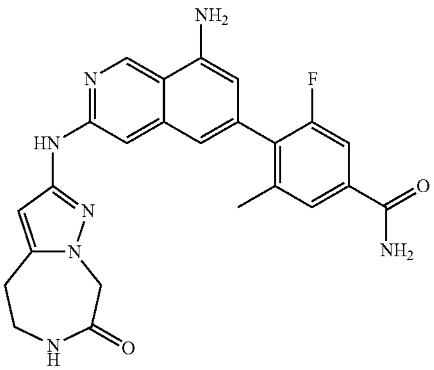 [SMILES: Cc1cc(C(N)=O)cc(F)c1-c1cc(N)c2cnc(Nc3cc4n(n3)CC(=O)NCC4)cc2c1] | 4-(8-amino-3-((7-oxo-5,6,7,8-tetrahydro-4H-pyrazolo[1,5-d][1,4]diazepin-2-yl)amino)isoquinolin-6-yl)-3-fluoro-5-methylbenzamide |
| 507 | 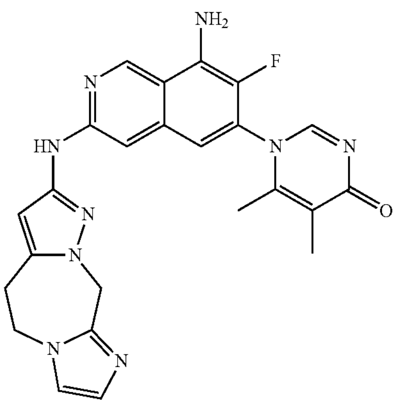 [SMILES: Cc1c(C)n(-c2cc3cc(Nc4cc5n(n4)Cc4nccn4CC5)ncc3c(N)c2F)cnc1=O] | 1-(8-amino-3-((5,6-dihydro-11H-imidazo[1,2-a]pyrazolo[1,5-d][1,4]diazepin-8-yl)amino)-7-fluoroisoquinolin-6-yl)-5,6-dimethylpyrimidin-4(1H)-one |
| 508 | 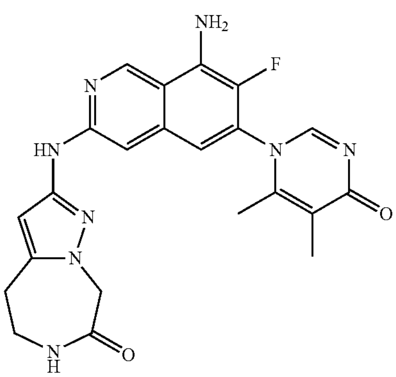 [SMILES: Cc1c(C)n(-c2cc3cc(Nc4cc5n(n4)CC(=O)NCC5)ncc3c(N)c2F)cnc1=O] | 2-((8-amino-6-(5,6-dimethyl-4-oxopyrimidin-1(4H)-yl)-7-fluoroisoquinolin-3-yl)amino)-5,6-dihydro-4H-pyrazolo[1,5-d][1,4]diazepin-7(8H)-one |
| 509 | 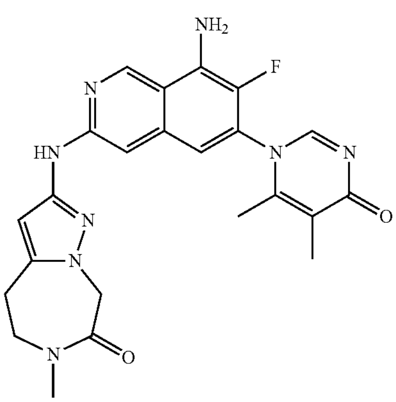 [SMILES: Cc1c(C)n(-c2cc3cc(Nc4cc5n(n4)CC(=O)N(C)CC5)ncc3c(N)c2F)cnc1=O] | 2-((8-amino-6-(5,6-dimethyl-4-oxopyrimidin-1(4H)-yl)-7-fluoroisoquinolin-3-yl)amino)-6-methyl-5,6-dihydro-4H-pyrazolo[1,5-d][1,4]diazepin-7(8H)-one |

TABLE 3-continued

| Compound No. | Structure | Name |
|---|---|---|
| 510 | 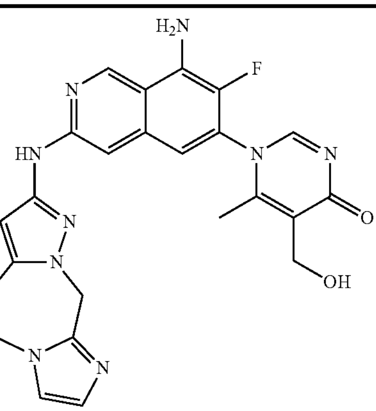 | 1-(8-amino-3-((5,6-dihydro-11H-imidazo[1,2-a]pyrazolo[1,5-d][1,4]diazepin-8-yl)amino)-7-fluoroisoquinolin-6-yl)-5-(hydroxymethyl)-6-methylpyrimidin-4(1H)-one |
| 511 | 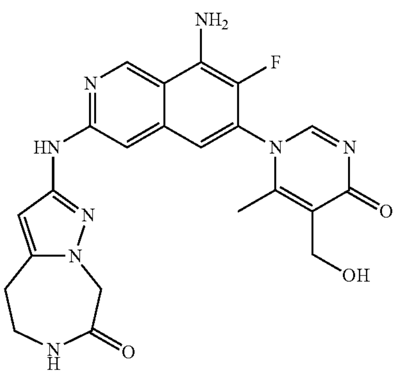 [SMILES: Cc1c(CO)c(=O)ncn1-c1cc2cc(Nc3cc4n(n3)CC(=O)NCC4)ncc2c(N)c1F] | 2-((8-amino-7-fluoro-6-(5-(hydroxymethyl)-6-methyl-4-oxopyrimidin-1(4H)-yl)isoquinolin-3-yl)amino)-5,6-dihydro-4H-pyrazolo[1,5-d][1,4]diazepin-7(8H)-one |
| 512 | 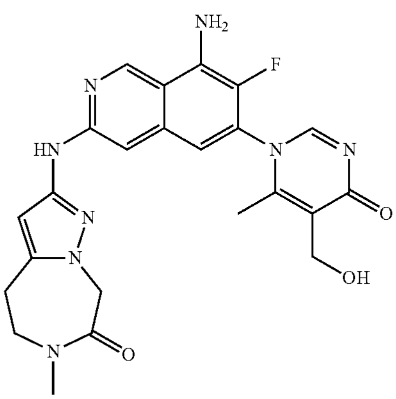 [SMILES: Cc1c(CO)c(=O)ncn1-c1cc2cc(Nc3cc4n(n3)CC(=O)N(C)CC4)ncc2c(N)c1F] | 2-((8-amino-7-fluoro-6-(5-(hydroxymethyl)-6-methyl-4-oxopyrimidin-1(4H)-yl)isoquinolin-3-yl)amino)-6-methyl-5,6-dihydro-4H-pyrazolo[1,5-d][1,4]diazepin-7(8H)-one |
| 513 | 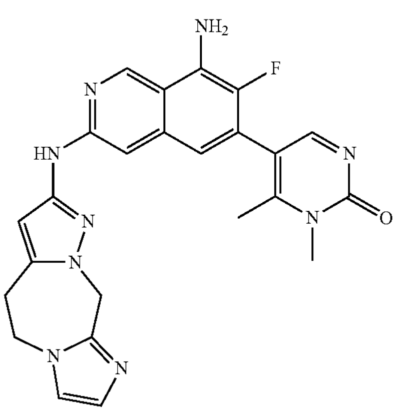 [SMILES: Cc1c(-c2cc3cc(Nc4cc5n(n4)Cc4nccn4CC5)ncc3c(N)c2F)cnc(=O)n1C] | 5-(8-amino-3-((5,6-dihydro-11H-imidazo[1,2-a]pyrazolo[1,5-d][1,4]diazepin-8-yl)amino)-7-fluoroisoquinolin-6-yl)-1,6-dimethylpyrimidin-2(1H)-one |

TABLE 3-continued

| Compound No. | Structure | Name |
|---|---|---|
| 514 | 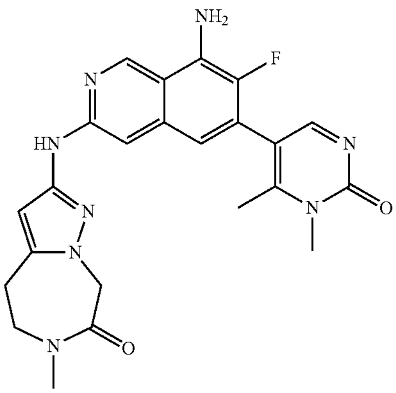 [SMILES: Cc1c(-c2cc3cc(Nc4cc5n(n4)CC(=O)N(C)CC5)ncc3c(N)c2F)cnc(=O)n1C] | 2-((8-amino-6-(1,6-dimethyl-2-oxo-1,2-dihydropyrimidin-5-yl)-7-fluoroisoquinolin-3-yl)amino)-6-methyl-5,6-dihydro-4H-pyrazolo[1,5-d][1,4]diazepin-7(8H)-one |
| 515 | 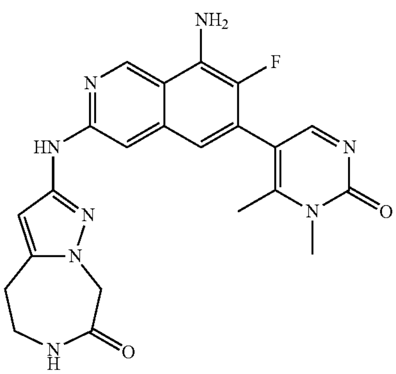 [SMILES: Cc1c(-c2cc3cc(Nc4cc5n(n4)CC(=O)NCC5)ncc3c(N)c2F)cnc(=O)n1C] | 2-((8-amino-6-(1,6-dimethyl-2-oxo-1,2-dihydropyrimidin-5-yl)-7-fluoroisoquinolin-3-yl)amino)-5,6-dihydro-4H-pyrazolo[1,5-d][1,4]diazepin-7(8H)-one |
| 516 | 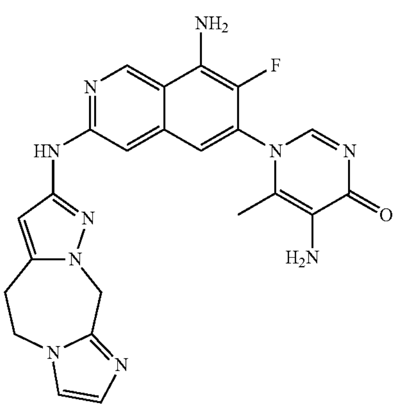 [SMILES: Cc1c(N)c(=O)ncn1-c1cc2cc(Nc3cc4n(n3)Cc3nccn3CC4)ncc2c(N)c1F] | 5-amino-1-(8-amino-3-((5,6-dihydro-11H-imidazo[1,2-a]pyrazolo[1,5-d][1,4]diazepin-8-yl)amino)-7-fluoroisoquinolin-6-yl)-6-methylpyrimidin-4(1H)-one |
| 517 | 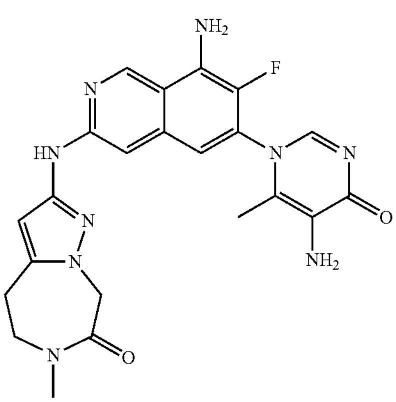 [SMILES: Cc1c(N)c(=O)ncn1-c1cc2cc(Nc3cc4n(n3)CC(=O)N(C)CC4)ncc2c(N)c1F] | 2-((8-amino-6-(5-amino-6-methyl-4-oxopyrimidin-1(4H)-yl)-7-fluoroisoquinolin-3-yl)amino)-6-methyl-5,6-dihydro-4H-pyrazolo[1,5-d][1,4]diazepin-7(8H)-one |

TABLE 3-continued

| Compound No. | Structure | Name |
|---|---|---|
| 518 | 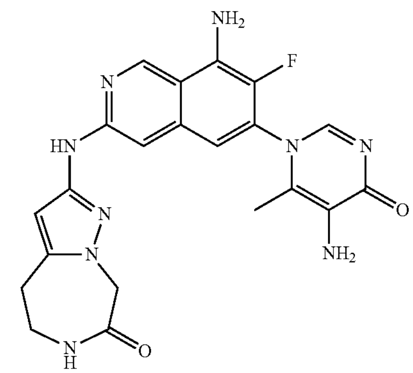 [SMILES: Cc1c(N)c(=O)ncn1-c1cc2cc(Nc3cc4n(n3)CC(=O)NCC4)ncc2c(N)c1F] | 2-((8-amino-6-(5-amino-6-methyl-4-oxopyrimidin-1(4H)-yl)-7-fluoroisoquinolin-3-yl)amino)-5,6-dihydro-4H-pyrazolo[1,5-d][1,4]diazepin-7(8H)-one |
| 519 | 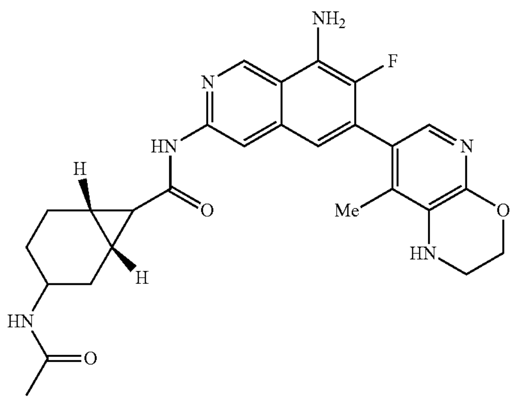 [SMILES: CC(=O)NC1CC[C@@H]2C(C(=O)Nc3cc4cc(-c5cnc6c(c5C)NCCO6)c(F)c(N)c4cn3)[C@@H]2C1] | (1R,6S)-3-acetamido-N-(8-amino-7-fluoro-6-(8-methyl-2,3-dihydro-1H-pyrido[2,3-b][1,4]oxazin-7-yl)isoquinolin-3-yl)bicyclo[4.1.0]heptane-7-carboxamide (1R,3R,6S,7S)-3-acetamido-N-(8-amino-7-fluoro-6-(8-methyl-2,3-dihydro-1H-pyrido[2,3-b][1,4]oxazin-7-yl)isoquinolin-3-yl)bicyclo[4.1.0]heptane-7-carboxamide |
| | | |
| 520 | 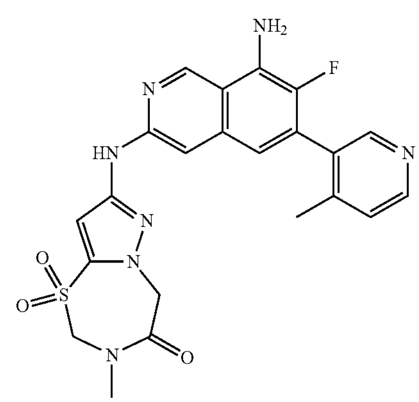 [SMILES: Cc1ccncc1-c1cc2cc(Nc3cc4n(n3)CC(=O)N(C)CS4(=O)=O)ncc2c(N)c1F] | 8-((8-amino-7-fluoro-6-(4-methylpyridin-3-yl)isoquinolin-3-yl)amino)-3-methyl-2,3-dihydropyrazolo[5,1-b][1,3,6]thiadiazepin-4(5H)-one 1,1-dioxide |

TABLE 3-continued

| Compound No. | Structure | Name |
|---|---|---|
| 521 | 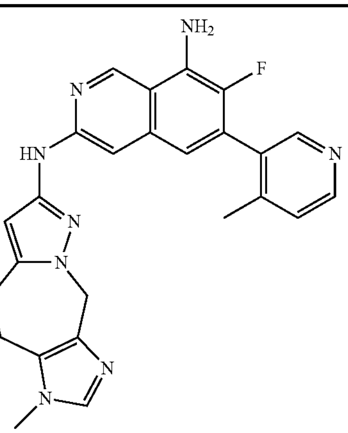 | 7-fluoro-N³-(1-methyl-1,4,9,10-tetrahydroimidazo[4,5-e]pyrazolo[1,5-a]azepin-7-yl)-6-(4-methylpyridin-3-yl)isoquinoline-3,8-diamine |
| 522 | 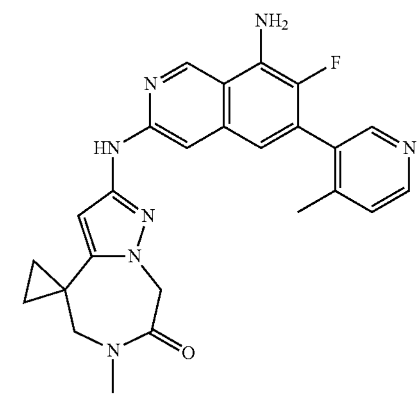 [SMILES: Cc1ccncc1-c1cc2cc(Nc3cc4n(n3)CC(=O)N(C)CC43CC3)ncc2c(N)c1F] | 2'-((8-amino-7-fluoro-6-(4-methylpyridin-3-yl)isoquinolin-3-yl)amino)-6'-methyl-5',6'-dihydrospiro[cyclopropane-1,4'-pyrazolo[1,5-d][1,4]diazepin]-7'(8'H)-one |
| 523 | 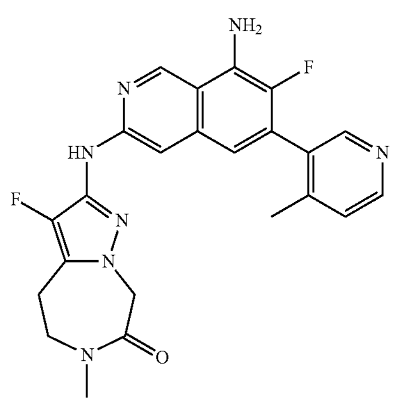 [SMILES: Cc1ccncc1-c1cc2cc(Nc3nn4c(c3F)CCN(C)C(=O)C4)ncc2c(N)c1F] | 2-((8-amino-7-fluoro-6-(4-methylpyridin-3-yl)isoquinolin-3-yl)amino)-3-fluoro-6-methyl-5,6-dihydro-4H-pyrazolo[1,5-d][1,4]diazepin-7(8H)-one |
| 524 | 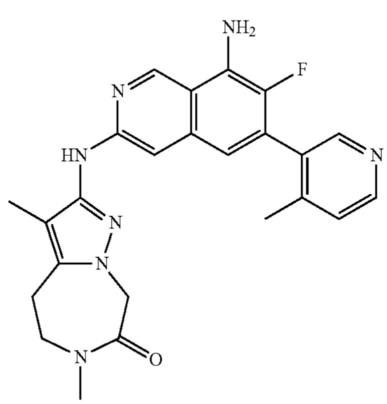 [SMILES: Cc1ccncc1-c1cc2cc(Nc3nn4c(c3C)CCN(C)C(=O)C4)ncc2c(N)c1F] | 2-((8-amino-7-fluoro-6-(4-methylpyridin-3-yl)isoquinolin-3-yl)amino)-3,6-dimethyl-5,6-dihydro-4H-pyrazolo[1,5-d][1,4]diazepin-7(8H)-one |

TABLE 3-continued

| Compound No. | Structure | Name |
|---|---|---|
| 525 | 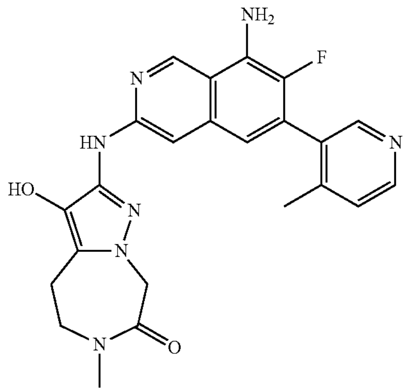 [SMILES: Cc1ccncc1-c1cc2cc(Nc3nn4c(c3O)CCN(C)C(=O)C4)ncc2c(N)c1F] | 2-((8-amino-7-fluoro-6-(4-methylpyridin-3-yl)isoquinolin-3-yl)amino)-3-hydroxy-6-methyl-5,6-dihydro-4H-pyrazolo[1,5-d][1,4]diazepin-7(8H)-one |
| 526 | 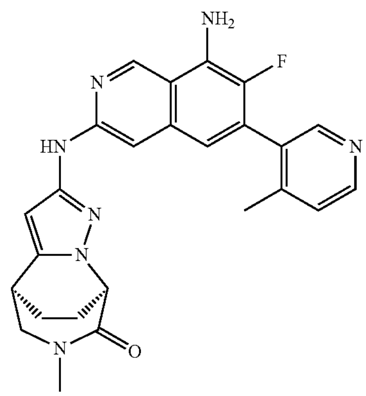 [SMILES: Cc1ccncc1-c1cc2cc(Nc3cc4n(n3)[C@@H]3CC[C@H]4CN(C)C3=O)ncc2c(N)c1F] | (4S,8R)-2-((8-amino-7-fluoro-6-(4-methylpyridin-3-yl)isoquinolin-3-yl)amino)-6-methyl-5,6-dihydro-4H-4,8-ethanopyrazolo[1,5-d][1,4]diazepin-7(8H)-one |
| 527 | 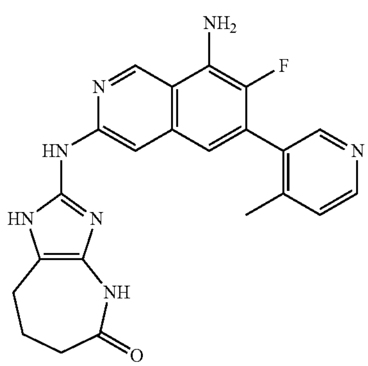 [SMILES: Cc1ccncc1-c1cc2cc(Nc3nc4c([nH]3)CCCC(=O)N4)ncc2c(N)c1F] | 2-((8-amino-7-fluoro-6-(4-methylpyridin-3-yl)isoquinolin-3-yl)amino)-4,6,7,8-tetrahydroimidazo[4,5-b]azepin-5(1H)-one |
| 528 | | 2-((8-amino-7-fluoro-6-(4-methylpyridin-3-yl)isoquinolin-3-yl)amino)-5,6-dihydro-4H-pyrazolo[1,5-a]azepin-7(8H)-one |

In some embodiments, the compound is selected from the group consisting of Compound Nos. 1-230 in Table 1, or a pharmaceutically acceptable salt thereof. In some embodiments, the compound is selected from the group consisting of Compound Nos. 1, 2, 3, 4, 5, 6, 7, 8, 13, 14, 15, 16, 17, 18, 19, 20, 21, 22, 23, 24, 25, 26, 27, 28, 30, 31, 32, 37, 38, 39, 40, 41, 42, 43, 44, 45, 46, 47, 48, 49, 50, 51, 52, 54, 55, 56, 57, 59, 60, 61, 62, 63, 65, 66, 67, 68, 69, 70, 71, 72, 73, 74, 75, 76, 77, 78, 79, 80, 81, 82, 85, 86, 87, 88, 89, 90, 91, 92, 93, 94, 95, 98, 99, 100, 101, 102, 103, 104, 105, 106, 107, 108, 109, 110, 113, 115, 116, 117, 118, 119, 122, 123, 124, 125, 126, 127, 128, 130, 131, 132, 133, 134, 135, 136, 138, 139, 140, 143, 144, 145, 146, 147, 148, 149, 150, 151, 153, 154, 155, 156, 157, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229 and 230, or a pharmaceutically acceptable salt thereof. In some embodiments, the compound is selected from the group consisting of Compound Nos. 9-12, 29, 33-36, 53, 58, 64, 83, 84, 96, 97, 111, 112, 114, 120, 121, 129, 137, 141, 142, 152 and 158, or a pharmaceutically acceptable salt thereof. In some embodiments, the compound is selected from the group consisting of Compound Nos. 231-390 in Table 2, or a pharmaceutically acceptable salt thereof. In some embodiments, the compound is selected from the group consisting of Compound Nos. 391-528 in Table 3, or a pharmaceutically acceptable salt thereof.

Compounds of Formula I or Ia described herein or a salt thereof may exist in stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound or salt of Formulas I or Ia may exist in tautomeric forms other than that shown in the formula and these are also included within the scope of the subject matter disclosed herein. It is to be understood that the subject matter disclosed herein includes combinations and subsets of the particular groups described herein. The scope of the subject matter disclosed herein includes mixtures of stereoisomers as well as purified enantiomers or enantiomerically/diastereomerically enriched mixtures. It is to be understood that the subject matter disclosed herein includes combinations and subsets of the particular groups defined herein.

The subject matter disclosed herein also includes isotopically-labelled forms of the compounds described herein, but for the fact that one or more atoms are replaced by an atom having an atomic mass or mass number different from the atomic mass or mass number usually found in nature. Examples of isotopes that can be incorporated into compounds described herein and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

The subject matter disclosed herein includes prodrugs, metabolites, derivatives, and pharmaceutically acceptable salts of compounds of Formula I or Ia. Metabolites of the compounds of Formula I or Ia include compounds produced by a process comprising contacting a compound of Formula I or Ia with a mammal for a period of time sufficient to yield a metabolic product thereof.

If the compound of Formula I or Ia is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of Formula I or Ia is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of Formula I or Ia can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

General Synthetic Schemes

Compounds of Formula I or Ia can be prepared by procedures in the Examples and generally by Schemes 1 and 2, where R groups are as described in Formula I or Ia, or precursors thereof.

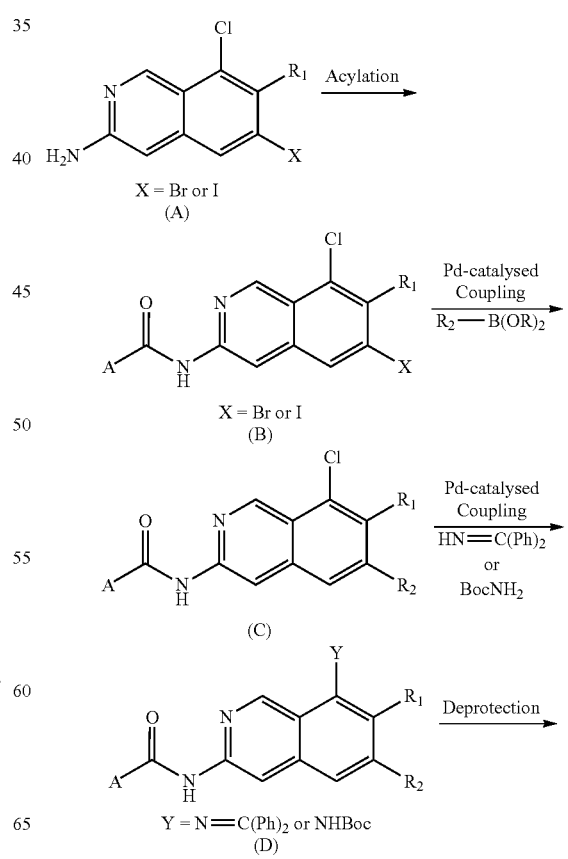

Scheme 1

-continued

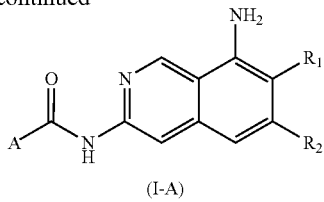

(I-A)

-continued

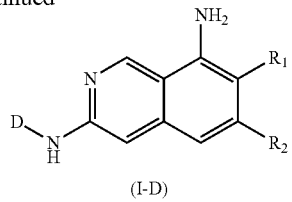

(I-D)

Scheme 1 shows a general synthetic method for preparing a compound of Formula I or Ia wherein $R_2$ is A-C(O)—. Reaction of compound A with an activated acyl compound A-C(O)—X' results in acylation of the 3-amino group giving compound B. Pd-catalysed coupling of compound B with a boronic ester $R_2$—B(OR)$_2$ gives compound C. Pd-catalysed coupling of compound C with a protected amine gives compound D. Deprotection of compound D yields the product of Formula (I-A), where A, $R_1$ and $R_2$ are as defined for Formula I or Ia.

Provided is a method for making a compound of Formula (I-A) comprising reacting a compound C with a protected amine (e.g., HN=C(Ph)$_2$ or Boc-NH$_2$) to form compound D, and subjecting compound D to a condition for amine deprotection to form compound (I-A), where A, $R_1$ and $R_2$ are as defined for Formula I or Ia. The method may further comprise acylating a compound A (comprising reacting compound A with A-C(O)—X, where X is halogen such as Br or I) to form compound B; reacting compound B with with a boronic ester $R_2$—B(OR)$_2$ (where R is an alkyl or aryl, or the two OR groups together with the boron atom to form a ring) and a Pd catalyst to form a compound C.

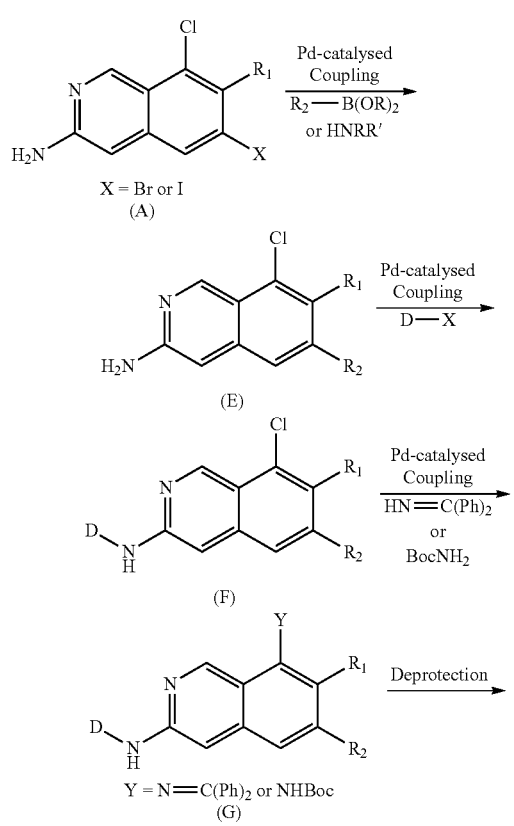

Scheme 2 shows a general synthetic method for preparing a compound of Formula I or Ia wherein $R_2$ is D. Pd-catalysed coupling of compound A with a boronic ester $R_2$—B(OR)$_2$, or a protected amine when the desired $R_2$ group is an amino group, gives compound E. Pd-catalysed coupling of compound E with a compound D-X gives compound F. Pd-catalysed coupling of compound C with a protected amine gives compound G. Deprotection of compound G yields the product of Formula (I-D), where D, $R_1$ and $R_2$ are as defined for Formula I or Ia.

Provided is a method for making a compound of Formula (I-D) comprising reacting a compound F with a protected amine (e.g., HN=C(Ph)$_2$ or Boc-NH$_2$) to form compound D, and subjecting compound D to a condition for amine deprotection to form compound (I-A), where A, $R_1$ and $R_2$ are as defined for Formula I or Ia. The method may further comprise reacting compound A with a boronic ester $R_2$—B(OR)$_2$ (where R is an alkyl or aryl, or the two OR groups together with the boron atom to form a ring) and a Pd catalyst to form a compound E; and reacting a compound E with a compound D-X (where X is a leaving group such as Cl, Br or I) and a Pd catalyst to form a compound F. Where the desired $R_2$ is an optionally substituted amino group, the method may further comprise reacting compound A with a protected amine (e.g., HNRR' where R and R's are amine protecting groups) and a Pd catalyst to form a compound E; and reacting a compound E with a compound D-X (where X is a leaving group such as Cl, Br or I) and a Pd catalyst to form a compound F.

Compositions

The presently disclosed compounds can be formulated into pharmaceutical compositions along with a pharmaceutically acceptable carrier.

Compounds of Formula I or Ia can be formulated in accordance with standard pharmaceutical practice as a pharmaceutical composition. According to this aspect, there is provided a pharmaceutical composition comprising a compound of Formula I or Ia in association with a pharmaceutically acceptable diluent or carrier.

A typical formulation is prepared by mixing a Formula I or Ia compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of Formula I or Ia is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of Formula I or Ia or pharmaceutical composition thereof) or aid in the manufacturing of the pharmaceutical product (i.e., medicament).

The formulations may be prepared using conventional dissolution and mixing procedures. For example, the bulk drug substance (i.e., compound of Formula I or Ia or stabilized form of the Formula I or Ia compound (e.g., complex with a cyclodextrin derivative or other known complexation agent) is dissolved in a suitable solvent in the presence of one or more of the excipients described above. The compound of Formula I or Ia is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations may be prepared for various routes and types of administration. For example, a compound of Formula I or Ia having the desired degree of purity may optionally be mixed with pharmaceutically acceptable diluents, carriers, excipients or stabilizers (Remington's Pharmaceutical Sciences (1980) $16^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compounds of Formula I or Ia can be sterile. In particular, formulations to be used for in vivo administration should be sterile. Such sterilization is readily accomplished by filtration through sterile filtration membranes.

The compound ordinarily can be stored as a solid composition, a lyophilized formulation or as an aqueous solution.

The pharmaceutical compositions comprising a compound of Formula I or Ia can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. In some embodiments, the amount is below the amount that is toxic to the host or renders the host more susceptible to bleeding.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences $16^{th}$ edition, Osol, A. Ed. (1980).

Sustained-release preparations of Formula I or Ia compounds may be prepared. Suitable examples of sustained-release preparations include semipermeable matrices of solid hydrophobic polymers containing a compound of Formula I or Ia, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I or Ia suitable for oral administration may be prepared as discrete units such as pills, capsules, cachets or tablets each containing a predetermined amount of a compound of Formula I or Ia.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I or Ia intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient (s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400), and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise solely an emulsifier, it may also comprise a mixture of at least one emulsifier and a fat or oil, or both a fat and an oil. A hydrophilic emulsifier included together with a lipophilic emulsifier may act as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation include Tween® 60, Span® 80, cetostearyl alcohol, benzyl alcohol, myristyl alcohol, glyceryl mono-stearate and sodium lauryl sulfate.

Aqueous suspensions of Formula I or Ia compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I or Ia may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

In particular embodiments the pharmaceutical composition comprising the presently disclosed compounds further comprise a chemotherapeutic agent. In some of these embodiments, the chemotherapeutic agent is an immunotherapeutic agent.

Methods

The presently disclosed compounds find use in inhibiting the activity of the enzyme HPK1. HPK1, also referred to as mitogen activated protein kinase kinase kinase kinase 1 or MAP4K1, is a member of the germinal center kinase subfamily of Ste20-related serine/threnonine kinases. HPK1 functions as a MAP4K by phosphorylating and activating MAP3K proteins, including MEKK1, MLK3 and TAK1, leading to the activation of the MAPK Jnk.

In an embodiment, the subject matter disclosed herein is directed to a method of inhibiting HPK1, the method comprising contacting HPK1 with an effective amount of a compound of Formula I or Ia or a pharmaceutical composition described herein.

In an embodiment, the subject matter disclosed herein is directed to a method for enhancing an immune response in a subject in need thereof, wherein the method comprises administering to said subject an effective amount of a compound of Formula I or Ia or a pharmaceutical composition described herein. In certain aspects of this embodiment, the T cells in the subject have at least one of enhanced priming, enhanced activation, enhanced migration, enhanced proliferation, enhanced survival, and enhanced cytolytic activity relative to prior to the administration of the compound or pharmaceutical composition. In certain aspects of this embodiment, the T cell activation is characterized by an elevated frequency of γ-IFN+ CD8 T cells or enhanced levels of IL-2 or granzyme B production by T cells relative to prior to administration of the compound or pharmaceutical composition. In certain aspects of this embodiment, the number of T cells is elevated relative to prior to administration of the compound or pharmaceutical composition. In certain aspects of this embodiment, the T cell is an antigen-specific CD8 T cell. In certain aspects of this embodiment, the antigen presenting cells in the subject have enhanced maturation and activation relative prior to the administration of the compound or pharmaceutical composition. In certain aspects of this embodiment, the antigen presenting cells are dendritic cells. In certain aspects of this embodiment, the maturation of the antigen presenting cells is characterized by increased frequency of CD83+ dendritic cells. In certain aspects of this embodiment, the activation of the antigen presenting cells is characterized by elevated expression of CD80 and CD86 on dendritic cells.

In the methods described herein, a compound of Formula I or Ia or a pharmaceutical composition thereof is administered to a subject that has cancer as described elsewhere herein.

In an embodiment, the subject matter disclosed herein is directed to a method for treating a HPK1-dependent disorder, the method comprising administering to a subject in need thereof an effective amount of a compound of Formula I or Ia or a pharmaceutical composition described herein. In certain aspects of this embodiment, the HPK1-dependent disorder is a cancer. In certain aspects of this embodiment, the cancer comprises at least one cancer selected from the group consisting of colorectal cancer, melanoma, non-small cell lung cancer, ovarian cancer, breast cancer, pancreatic cancer, a hematological malignancy, and a renal cell carcinoma. In certain aspects of this embodiment, the cancer has elevated levels of T-cell infiltration. In certain aspects of this embodiment, the cancer cells in the subject selectively have elevated expression of MHC class I antigen expression relative to prior to the administration of the compound or composition.

In the methods described herein, the method can further comprise administering a chemotherapeutic agent to said subject. In certain aspects of this embodiment, the chemotherapeutic agent is administered to the subject simultaneously with the compound or the composition. In certain aspects of this embodiment, the chemotherapeutic agent is administered to the subject prior to administration of the compound or the composition. In certain aspects of this embodiment, the chemotherapeutic agent is administered to the subject after administration of the compound or said composition.

HPK1 polynucleotides and polypeptides are known in the art (Hu et al. (1996) *Genes Dev.* 10: 2251-2264, which is herein incorporated by reference in its entirety). Non-limiting examples of HPK1 polynucleotides and polypeptides comprise the human HPK1 polynucleotide as set forth in SEQ ID NO: 1 (nucleotides 141-2642 of GenBank Accession No. NM_007181.5) and the encoded human HPK1 polypeptide (Accession No. NP_009112.1) as set forth in SEQ ID NO: 2. A shorter 821 amino acid isoform of HPK1 exists in humans, the coding sequence and amino acid sequence of which is set forth in SEQ ID NOs: 3 and 1, respectively (nucleotides 141-2606 of GenBank Accession No. NM_001042600.2 and GenBank Accession No. NP_001036065.1, respectively).

HPK1 polypeptides comprise a variety of conserved structural motifs. For ease of reference, such motifs will be discussed as they relate to the longer human HPK1 isoform, which is set forth in SEQ ID NO:2, comprises 833 amino acid residues. HPK1 polypeptides comprise an amino-terminal Ste20-like kinase domain that spans amino acid residues 17-293, which includes the ATP-binding site from amino acid residues 23-46. The kinase domain is followed by four proline-rich (PR) motifs that serve as binding sites for SH3-containing proteins, such as CrkL, Grb2, HIP-55, Gads, Nck, and Crk. The four PR motifs span amino acid residues 308-407, 394-402, 432-443, and 468-477, respectively. HPK1 becomes phosphorylated and activated in response to TCR or BCR stimulation. TCR- and BCR-induced phosphorylation of the tyrosine at position 381, located between PR1 and PR2, mediates binding to SLP-76 in T cells or BLNK in B cells via a SLP-76 or BLNK SH2 domain, and is required for activation of the kinase. A citron homology domain found in the C-terminus of HPK1, approximately spanning residues 495-800, may act as a regulatory domain and may be involved in macromolecular interactions.

The presently disclosed compounds bind directly to HPK1 and inhibit its kinase activity. In some embodiments, the presently disclosed compounds reduce, inhibit, or otherwise diminish the HPK1-mediated phosphorylation of SLP76 and/or Gads.

The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the presently disclosed compounds specifically inhibit the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

The presently disclosed compounds can be used in a method for inhibiting HPK1. Such methods comprise contacting HPK1 with an effective amount of a presently disclosed compound. By "contact" is intended bringing the compound within close enough proximity to an isolated HPK1 enzyme or a cell expressing HPK1 (e.g., T cell, B cell, dendritic cell) such that the compound is able to bind to and inhibit the activity of HPK1. The compound can be contacted with HPK1 in vitro or in vivo via administration of the compound to a subject.

Any method known in the art to measure the kinase activity of HPK1 may be used to determine if HPK1 has been inhibited, including in vitro kinase assays, immunoblots with antibodies specific for phosphorylated targets of HPK1, such as SLP76 and Gads, or the measurement of a downstream biological effect of HPK1 kinase activity, such as the recruitment of 14-3-3 proteins to phosphorylated SLP7 and Gads, release of the SLP76-Gads-14-3-3 complex from LAT-containing microclusters, or T or B cell activation.

The presently disclosed compounds can be used to treat a HPK1-dependent disorder. As used herein, a "HPK1-dependent disorder" is a pathological condition in which HPK1 activity is necessary for the genesis or maintenance of the pathological condition. In some embodiments, the HPK1-dependent disorder is cancer.

The presently disclosed compounds also find use in enhancing an immune response in a subject in need thereof. Such methods comprise administering an effective amount of a presently disclosed compound (i.e., compound of Formula I or Ia or a pharmaceutically acceptable salt, prodrug, metabolite, or derivative thereof).

As used herein, "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CD8 T cells), enhanced T cell (e.g., CD4 T cell, CD8 T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2-induced immune suppression, and enhanced priming and/or cytolytic activity of CD8 T cells.

In some embodiments, the CD8 T cells in the subject have enhanced priming, activation, proliferation and/or cytolytic activity relative to prior to the administration of the compound of Formula I or Ia or a pharmaceutically acceptable salt, prodrug, metabolite, or derivative thereof. In some embodiments, the CD8 T cell priming is characterized by elevated CD44 expression and/or enhanced cytolytic activity in CD8 T cells. In some embodiments, the CD8 T cell activation is characterized by an elevated frequency of γ-IFN$^+$ CD8 T cells. In some embodiments, the CD8 T cell is an antigen-specific T-cell.

In some embodiments, the antigen presenting cells in the subject have enhanced maturation and activation relative to prior to the administration of the compound of Formula I or Ia or a pharmaceutically acceptable salt, prodrug, metabolite, or derivative thereof. In some embodiments, the antigen presenting cells are dendritic cells. In some embodiments, the maturation of the antigen presenting cells is characterized by an increased frequency of CD83$^+$ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the subject are reduced relative to prior to the administration of the compound of Formula I or Ia or a pharmaceutically acceptable salt, prodrug, metabolite, or derivative thereof.

Engagement of the TCR leads to HPK1 activation, which functions as a negative regulator of TCR-induced AP-1 response pathway. It is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters, which leads to T cell dysfunction, including anergy and exhaustion (Lasserre et al. (2011) *J Cell Biol* 195(5):839-853).

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growthours.

The term "dysfunctional", as used herein, also includes refractory or unresponsive to antigen recognition, specifically, impaired capacity to translate antigen recognition into down-stream T-cell effector functions, such as proliferation, cytokine production (e.g., IL-2, γ-IFN) and/or target cell killing.

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells.

Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

In some embodiments, administration of a compound of Formula I or Ia or a pharmaceutically acceptable salt, prodrug, metabolite, or derivative thereof to a subject results in an enhancement of T cell function.

"Enhancing T cell function" means to induce, cause or stimulate a T cell to have a sustained or amplified biological function, or renew or reactivate exhausted or inactive T cells.

Examples of enhancing T cell function include: increased secretion of cytokines (e.g., γ-interferon, IL-2, IL-12, and TNFα), increased proliferation, increased antigen responsiveness (e.g., viral, pathogen, or tumor clearance) relative to such levels before the intervention, and increased effector granule production by CD8 T cells, such as granzyme B. In one embodiment, the level of enhancement is as least 50%, alternatively 60%, 70%, 80%, 90%, 100%, 120%, 150%, 200%. The manner of measuring this enhancement is known to one of ordinary skill in the art.

Accordingly, the presently disclosed compounds of Formula I or Ia or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation. In a particular embodiment, a T cell dysfunctional disorder is a disorder that is specifically associated with increased kinase activity of HPK1. In another embodiment, a T cell dysfunctional disorder is one in which T cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

Thus, the presently disclosed compounds can be used in treating conditions where enhanced immunogenicity is desired, such as increasing tumor immunogenicity for the treatment of cancer.

"Immunogenecity" refers to the ability of a particular substance to provoke an immune response. Tumors are immunogenic and enhancing tumor immunogenicity aids in the clearance of the tumor cells by the immune response.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

In one aspect, provided herein is a method for treating of cancer in a subject in need thereof comprising administering to the subject an effective amount of a compound of Formula I or Ia or a pharmaceutically acceptable salt, prodrug, metabolite, or derivative thereof. In some embodiments, the subject has melanoma. The melanoma may be at early stage or at late stage.

In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or late state. In some embodiments, the subject has a hematological malignancy. The hematological malignancy may beat early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

The presently disclosed compounds may be administered in any suitable manner known in the art. In some embodiments, the compound of Formula I or Ia or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the HPK1 antagonist is administered continuously. In other embodiments, the HPK1 antagonist is administered intermittently. Moreover, treatment of a subject with an effective amount of a HPK1 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of Formula I or Ia or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the HPK1 antagonist is administered to the subject at a dose of between about 0.001 µg/kg and about 1000 mg/kg, including but not limited to about 0.001 µg/kg, about 0.01 µg/kg, about 0.05 µg/kg, about 0.1 µg/kg, about 0.5 µg/kg, about 1 µg/kg, about 10 µg/kg, about 25 µg/kg, about 50 µg/kg, about 100 µg/kg, about 250 µg/kg, about 500 µg/kg, about 1 mg/kg, about 5 mg/kg, about 10 mg/kg, about 25 mg/kg, about 50 mg/kg, about 100 mg/kg, and about 200 mg/kg.

In some embodiments, provided is a method for treating a cancer in a subject in need thereof comprising administering to the subject an effective amount of a compound of Formula I or Ia or a pharmaceutically acceptable salt, prodrug, metabolite, or derivative thereof, further comprising administering an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of an anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting the PI3K/AKT/mTOR pathway, HSP90 inhibitor, tubulin inhibitor, apoptosis inhibitor, and/or chemopreventative agent.

The additional therapy may be one or more of a chemotherapeutic agent. Thus, the method of treating cancer can comprise administering the presently disclosed HPK1 antagonists in conjunction with at least one chemotherapeutic agent.

As used herein, "in conjunction with" refers to administration of one treatment modality in addition to another treatment modality. As such, "in conjunction with" refers to administration of one treatment modality before, during, or after administration of the other treatment modality to the subject.

For example, the HPK1 antagonist and chemotherapeutic agent may be administered sequentially (at different times) or concurrently (at the same time). The HPK1 antagonist and chemotherapeutic agent may be administered by the same route of administration or by different routes of administration.

In certain embodiments, the HPK1 antagonist is administered in conjunction with another immunotherapy. For example, the HPK1 antagonist can be combined with a chemotherapeutic agent or biologic that targets the PDL1/PD1 pathway. A known inhibitory checkpoint pathway involves signaling through PD-1 receptors. The programmed-death 1 (PD-1) receptor and its ligands PD-L1 and PD-L2 are part of the same family of coregulatory molecules as CTLA-4.—See more at: http://www.onclive.com/web-exclusives/the-role-of-anti-pd-11-immunotherapy-in-cancer/2 #sthash.cGfYaT.dpuf Chemotherapeutic agents or biologics that block PD-L1 binding to PD-1 and CD80 can prevent PD-L1-mediated inhibition/suppression of T-cell activation. Programmed cell death ligand-1 (PD-L1) is widely expressed on antigen-presenting cells (APC) and other immune cells. It is upregulated on tumor cells from a broad range of human cancers, and has been implicated with inhibition of antitumor T-cell immunity. PD-L1 is a cell surface protein that binds to the receptors PD-1 and CD80 on activated T cells, B cells, and other myeloid cells. PD-L1 binding to PD-1 on activated T-cells has been found to interfere with T-cell proliferation and inhibit immune responses. Overexpression of PD-L1 on cancer cells may allow these cells to avoid immune detection and elimination. High levels of PD-L1 expression on tumor cells have been associated with increased tumor aggressiveness and a poor prognosis. Chemotherapeutic agents or biologics that block PD-L1 binding to PD-1 include anti-PD-L1 antibodies, such as durvalumab, nivolumab, pidlizumab, MPDL3280A, MK-3475 and BMS-936559, among others.

In another example, the HPK1 antagonist can be combined with a chemotherapeutic agent or biologic that targets OX40 and its ligand, OX40L, are members of the TNF superfamily. OX40 is expressed on activated CD4(+) and CD8(+) T cells as well as on a number of other lymphoid and non-lymphoid cells. Costimulatory signals from OX40 to a conventional T cell promote division and survival, augmenting the clonal expansion of effector and memory populations as they are being generated to antigen. OX40 additionally suppresses the differentiation and activity of T-regulatory cells, further amplifying this process. OX40 and OX40L also regulate cytokine production from T cells, antigen-presenting cells, natural killer cells, and natural killer T cells, and modulate cytokine receptor signaling. As one of the most prominent costimulatory molecules known to control T cells, stimulating OX40 has been shown be a target for therapeutic immunization strategies for cancer. Certain OX40 agonists include GBR 830, and those disclosed in Linch, et al., Frontiers in Oncology, v. 5, pp. 1-10 (2015), herein incorporated by reference in its entirety.

In some embodiments, the invention also provides compounds of Formula I or Ia described herein or pharmaceutical compositions described herein for use in a method for inhibiting HPK1 as described herein, in a method for enhancing an immune response in a subject in need thereof as described herein and/or in a method for treating a HPK1-dependent disorder as described herein.

In some embodiments, the invention also provides compounds of Formula I or Ia described herein or pharmaceutical compositions described herein for use in a method for inhibiting HPK1 as described herein.

In some embodiments, the invention also provides compounds of Formula I or Ia described herein or pharmaceutical compositions described herein for use in a method for enhancing an immune response in a subject in need thereof as described herein.

In some embodiments, the invention also provides compounds of Formula I or Ia described herein or pharmaceutical compositions described herein for use in a method for treating a HPK1-dependent disorder as described herein.

In some embodiments, the invention also provides the use of a compound of Formula I or Ia described herein or a pharmaceutical composition described herein for the manufacture of a medicament for inhibiting HPK1, a medicament for enhancing an immune response in a subject in need thereof and/or a medicament for treating a HPK1-dependent disorder.

In some embodiments, the invention also provides the use of a compound of Formula I or Ia described herein or a pharmaceutical composition described herein for the manufacture of a medicament for inhibiting HPK1.

In some embodiments, the invention also provides the use of a compound of Formula I or Ia described herein or a pharmaceutical composition described herein for the manufacture of a medicament for enhancing an immune response in a subject in need thereof.

In some embodiments, the invention also provides the use of a compound of Formula I or Ia described herein or a pharmaceutical composition described herein for the manufacture of a medicament treating a HPK1-dependent disorder.

In some embodiments, the invention also provides the use of compounds of Formula I or Ia described herein or pharmaceutical compositions described herein in a method for inhibiting HPK1 as described herein, in a method for enhancing an immune response in a subject in need thereof as described herein and/or in a method for treating a HPK1-dependent disorder as described herein.

In some embodiments, the invention also provides the use of compounds of Formula I or Ia described herein or pharmaceutical compositions described herein in a method for inhibiting HPK1 as described herein.

In some embodiments, the invention also provides the use of compounds of Formula I or Ia described herein or pharmaceutical compositions described herein in a method for enhancing an immune response in a subject in need thereof as described herein.

In some embodiments, the invention also provides the use of compounds of Formula I or Ia described herein or pharmaceutical compositions described herein in a method for treating a HPK1-dependent disorder as described herein.

In some embodiments, the treatment results in a sustained response in the subject after cessation of the treatment. "Sustained response" refers to the sustained effect on reducing tumor growth after cessation of a treatment. For example, the tumor size may remain the same or smaller as compared to the size at the beginning of the administration phase. In some embodiments, the sustained response has a duration at least the same as the treatment duration, at least 1.5×, 2.0×, 2.5×, or 3.0× length of the treatment duration.

The treatment methods disclosed herein may result in a partial or complete response. As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started. As used herein, "overall response rate" (ORR) refers to the sum of complete response (CR) rate and partial response (PR) rate.

The treatment methods disclosed herein can lead to an increase in progression free survival and overall survival of the subject administered the HPK1 antagonist. As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" refers to the percentage of subjects in a group who are likely to be alive after a particular duration of time.

In some embodiments, the subject that is administered a HPK1 antagonist is a mammal, such as domesticated animals (e.g., cows, sheep, cats, dogs, and horses), primates (e.g., humans and non-human primates such as monkeys), rabbits, and rodents (e.g., mice and rats). In some embodiments, the subject treated is a human.

The subject in need of treatment for cancer may be a person demonstrating symptoms of cancer, one that has been diagnosed with cancer, a subject that is in remission from cancer, or a subject having an increased risk for developing cancer (e.g., a genetic predisposition, certain dietary or environmental exposures).

The following examples are offered by way of illustration and not by way of limitation.

EXAMPLES

Materials and Methods

Method A: Experiments performed on an Agilent 1100 HPLC with Agilent MSD mass spectrometer using ESI as ionization source using an Agilent SunFire-C18 3.5 µm, 4.6×50 column and a 2.0 ml/minute flow rate. The solvent system was a gradient starting with 95% water with 0.05% TFA (solvent A) and 5% acetonitrile with 0.05% TFA (solvent B), ramping up to 100% solvent B over 1.3 minutes. The final solvent system was held constant for a further 1.2 minutes.

Method B: Experiments performed on an Agilent 1200 HPLC with Agilent MSD mass spectrometer using ESI as ionization source using an Agilent SunFire-C18 3.5 µm, 4.6×50 column and a 2.0 ml/minute flow rate. The solvent system was a gradient starting with 95% water with 0.01% TFA (solvent A) and 5% acetonitrile with 0.01% TFA (solvent B), ramping up to 5% solvent A and 95% solvent B over 1.4 minutes. The final solvent system was held constant for a further 1.0 minute.

Method C: Experiments performed on an Agilent 1200 HPLC with Agilent MSD mass spectrometer using ESI as ionization source using an Agilent Xbridge-C18, 3.5 µm, 4.6×50 mm column and a 1.8 ml/minute flow rate. The solvent system was a gradient starting with 95% water with 10 mM $NH_4HCO_3$ (solvent A) and 5% acetonitrile (solvent B), ramping up to 5% solvent A and 95% solvent B over 1.3 minutes. The final solvent system was held constant for a further 1.2 minutes.

Method D: Experiments performed on an Agilent 1200 HPLC with Agilent MSD mass spectrometer using ESI as ionization source using an Agilent Xbridge-C18, 3.5 µm, 4.6×50 mm column and a 1.8 ml/minute flow rate. The solvent system was a gradient starting with 95% water with 10 mM $NH_4HCO_3$ (solvent A) and 5% acetonitrile (solvent B), ramping up to 5% solvent A and 95% solvent B over 1.6 minutes. The final solvent system was held constant for a further 1.0 minute.

Method E: Experiments performed on an Agilent 1200 HPLC with Agilent MSD mass spectrometer using ESI as ionization source using an Agilent SunFire-C18 3.5 µm, 4.6×50 column and a 2.0 ml/minute flow rate. The solvent system was a gradient starting with 95% water with 0.01% TFA (solvent A) and 5% acetonitrile with 0.01% TFA (solvent B), ramping up to 5% solvent A and 95% solvent B over 1.5 minutes. The final solvent system was held constant for a further 1.0 minute.

Method F: Experiments performed on an Agilent 1200 HPLC with Agilent MSD mass spectrometer using ESI as ionization source using an Agilent Xbridge-C18, 3.5 μm, 4.6×50 mm column and a 1.8 ml/minute flow rate. The solvent system was a gradient starting with 90% water with 10 mM $NH_4HCO_3$ (solvent A) and 10% acetonitrile (solvent B), ramping up to 5% solvent A and 95% solvent B over 1.5 minutes. The final solvent system was held constant for a further 1.0 minute.

Method G: Experiments performed on an Agilent 1200 HPLC with Agilent MSD mass spectrometer using ESI as ionization source using an Agilent Xbridge-C18, 3.5 μm, 4.6×50 mm column and a 1.8 ml/minute flow rate. The solvent system was a gradient starting with 95% water with 10 mM $NH_4HCO_3$ (solvent A) and 5% acetonitrile (solvent B), ramping up to 5% solvent A and 95% solvent B over 1.4 minutes. The final solvent system was held constant for a further 1.0 minute.

Method H: Experiments performed on an Agilent 1200 HPLC with Agilent MSD mass spectrometer using ESI as ionization source using Gemini-Nx 3u, C18, 3 μm, 4.6×50 mm column and a 1.8 ml/minute flow rate. The solvent system was a gradient starting with 90% water with 10 mM $NH_4HCO_3$ (solvent A) and 10% acetonitrile (solvent B), ramping up to 5% solvent A and 95% solvent B over 1.5 minutes. The final solvent system was held constant for a further 1.0 minute.

Method I: Experiments performed on an Agilent 1200 HPLC with Agilent MSD mass spectrometer using ESI as ionization source using XBridge-C18, 3.5 μm, 4.6×50 mm column and a 1.8 ml/minute flow rate. The solvent system was a gradient starting with 95% water with 10 mM $NH_4HCO_3$ (solvent A) and 5% acetonitrile (solvent B), ramping up to 5% solvent A and 95% solvent B over 1.6 minutes. The final solvent system was held constant for a further 1.0 minute.

Method J: Experiments performed on an Agilent 1290 UHPLC coupled with Agilent MSD (6140) mass spectrometer using ESI as ionization source. The LC separation was using a Phenomenex XB-C18, 1.7 μm, 50×2.1 mm column with a 0.4 ml/minute flow rate. Solvent A is water with 0.1% FA and solvent B is acetonitrile with 0.1% FA. The gradient consisted with 2-98% solvent B over 7 min and hold 98% B for 1.5 min following equilibration for 1.5 min. LC column temperature is 40° C. UV absorbance was collected at 220 nm and 254 nm and mass spec full scan was applied to all experiments.

Method J*: Experiments were performed on a Shimadzu 20AD HPLC with Shimadzu LCMS2020 mass spectrometer using ESI as ionization source, a Shim-Pack XR-ODS C18 2.2 μm, 3.0×50 column, and a 1.2 ml/minute flow rate. The solvent system was a gradient starting with 95% water with 0.05% TFA (solvent A) and 5% acetonitrile with 0.05% TFA (solvent B), ramping up to 95% solvent B over 2.0 minutes. The final solvent system was held constant for a further 0.7 minutes.

Method K: Experiments performed on a Shimadzu LC-20AD with LCMS-2020 mass spectrometer using ESI as ionization source using a Shim-Pack XR-ODS 2.2 m, 3.0×50 column and a 1.2 ml/minute flow rate. The solvent system was a gradient starting with 95% water with 0.05% TFA (solvent A) and 5% acetonitrile with 0.05% TFA (solvent B), ramping up to 5% solvent A and 95% solvent B over 2.0 minutes. The final solvent system was held constant for a further 0.7 minute.

Method K*: Experiments performed on a Shimadzu 20AD HPLC with Shimadzu LCMS-2020 mass spectrometer using ESI as ionization source using a Shim-Pack XR-ODS 2.2 m, 3.0×50 column and a 1.2 ml/minute flow rate. The solvent system was a gradient starting with 95% water with 0.05% TFA (solvent A) and 5% acetonitrile with 0.05% TFA (solvent B), ramping up to 95% solvent B over 2.0 minutes. The final solvent system was held constant for a further 0.7 minute.

Method L: Experiments performed on a Shimadzu LC-30AD with LCMS-2020 mass spectrometer using ESI as ionization source using an Ascentis Express C18 2.7 μm, 3.0×50 mm column and a 1.0 ml/minute flow rate. The solvent system was a gradient starting with 95% water with 0.05% TFA (solvent A) and 5% acetonitrile with 0.05% TFA (solvent B), ramping up to 5% solvent A and 95% solvent B over 2.0 minutes. The final solvent system was held constant for a further 0.7 minute.

Method L*: Experiments performed on a Shimadzu 30AD HPLC with Shimadzu LCMS-2020 mass spectrometer using ESI as ionization source using an Ascentis Express C18 2.7 μm, 2.1×50 column and a 1.0 ml/minute flow rate. The solvent system was a gradient starting with 95% water with 0.05% TFA (solvent A) and 5% acetonitrile with 0.05% TFA (solvent B), ramping up to 95% solvent B over 2.0 minutes. The final solvent system was held constant for a further 0.7 minute.

Method M: Experiments performed on a Shimadzu LC-20ADXR with LCMS-2020 mass spectrometer using ESI as ionization source using a poroshell HPH-C18, 2.7 μm, 3.0×50 column and a 1.2 ml/minute flow rate. The solvent system was a gradient starting with 95% water with 5 mM $NH_4HCO_3$ (solvent A) and 5% acetonitrile (solvent B), ramping up to 95% solvent B over 2.0 minutes. The final solvent system was held constant for a further 0.7 minutes.

Method M*: Experiments performed on a Shimadzu 20AD XR HPLC with Shimadzu LCMS2020 mass spectrometer using ESI as ionization source using a poroshell HPH-C18, 2.7 μm, 3.0×50 column and a 1.2 ml/minute flow rate. The solvent system was a gradient starting with 95% water with 5 mM Ammonium bicarbonate (solvent A) and 5% acetonitrile (solvent B), ramping up to 95% solvent B over 2.0 minutes. The final solvent system was held constant for a further 0.7 minutes.

Method N: Experiments performed on a Shimadzu LC-30AD with LCMS-2020 mass spectrometer using ESI as ionization source using a CAPCELL CORE C18, 2.7 μm, 2.1×50 mm column and a 1.0 ml/minute flow rate. The solvent system was a gradient starting with 95% water with 0.1% FA (solvent A) and 5% acetonitrile with 0.1% FA (solvent B), ramping up to 5% solvent A and 95% solvent B over 2.0 minutes. The final solvent system was held constant for a further 0.7 minute.

Method N*: Experiments performed on an Agilent 1290 UHPLC coupled with Agilent MSD (6140) mass spectrometer using ESI as ionization source. The LC separation used a Phenomenex XB-C18, 1.7 μm, 50×2.1 mm column with a 0.4 ml/minute flow rate. Solvent A was water with 0.1% FA and solvent B was acetonitrile with 0.1% FA. The gradient consisted with 2-98% solvent B over 7 min and hold 98% B for 1.5 min following equilibration for 1.5 min. LC column temperature is 40° C. UV absorbance was collected at 220 nm and 254 nm and mass spec full scan was applied to all experiment.

Method O: Experiments performed on a Shimadzu LC-30AD with LCMS-2020 mass spectrometer using ESI as ionization source using a kinetex EVO C18, 2.7 μm, 2.1×50 column and a 1.2 ml/minute flow rate. The solvent system was a gradient starting with 95% water with 6.5 mM NH$_4$HCO$_3$ (solvent A) and 5% acetonitrile (solvent B), ramping up to 95% solvent B over 2.0 minutes. The final solvent system was held constant for a further 0.7 minutes.

Method O*: Experiment was performed on a Waters Acquity UPLC with Waters LCT Premier XE mass spectrometer using ESI ionization. The LC separation was using an Acquity UPLC BEH C18, 1.7 μm, 2.1×50 mm column and a 0.6 ml/min flow rate. MPA (mobile phase A) was water with 0.05% TFA and MPB (mobile phase B) was acetonitrile with 0.05% TFA. The gradient consisted with 2-98% MPB over 5 min and hold 98% B for 0.5 min following equilibration for 0.5 min. LC column temperature is 40° C. UV data was collected at 220 nm and 254 nm and mass spec full scan was applied to all experiments.

Method P: Experiments performed on a Shimadzu LC-20AD with LCMS-2010 mass spectrometer using ESI as ionization source using a Shim-Pack XR-ODS 2.2 m, 3.0×50 column and a 1.2 ml/minute flow rate. The solvent system was a gradient starting with 95% water with 0.05% TFA (solvent A) and 5% acetonitrile with 0.05% TFA (solvent B), ramping up to 5% solvent A and 95% solvent B over 2.0 minutes. The final solvent system was held constant for a further 0.7 minute. LC column temperature is 40° C. UV absorbance was collected at 220 nm and 254 nm and mass spec full scan was applied to all experiments.

Compound Syntheses

SYNTHETIC INTERMEDIATES

Example I.1

Intermediate 1: 6-bromo-8-chloro-isoquinolin-3-amine

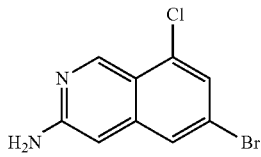 [SMILES: Nc1cc2cc(Br)cc(Cl)c2cn1]

Step 1: methyl 2,2-diethoxyethanimidate

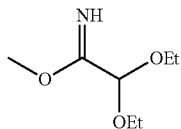

To a stirred solution of diethoxyacetonitrile (7.0 g, 54.2 mmol) in dry methanol (50 mL) was added a solution of sodium methoxide in methanol (4.2 mL, 20%, 8.4 mmol). After the addition, the reaction mixture was stirred at room temperature for 48 hours. The reaction was concentrated to dryness and the residue was taken up in chloroform and the organic layer washed with water, dried and concentrated to give methyl 2,2-diethoxyethanimidate (8.37 g, 95% yield) as a colorless oil, which was used in the next step without further purification. $^1$H NMR (400 MHz, DMSO-d$_6$) δ 7.95 (s, 1H), 4.82 (s, 1H), 3.65 (s, 3H), 3.51 (q, J=7.2 Hz, 4H), 1.14 (t, J=7.2 Hz, 6H).

Step 2: 4-bromo-2-chloro-phenyl)methanamine

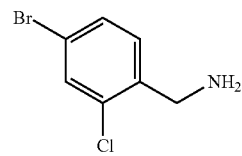

To a 50 mL round bottom flask was added BH$_3$-THF (1.0 Min THF, 32.5 mL, 32.5 mmol) and 4-bromo-2-chlorobenzonitrile (1.76 g, 8.13 mmol) in THF (10 mL). The mixture was heated to reflux for 2 hours. The reaction mixture was quenched by the addition of an aqueous HCl solution (10 wt % yield). The pH was adjusted to 8 by adding an aqueous solution of NaOH (5 wt % yield) and extracted with dichloromethane. The organic layer was dried, filtered and concentrated to afford (4-bromo-2-chloro-phenyl)methanamine (1.62 g, 90% yield), which was used in the next step without further purification. LCMS (ESI) [M+H]$^+$=220.0.

Step 3: N-[(4-bromo-2-chloro-phenyl)methyl]-2,2-diethoxy-acetamidine

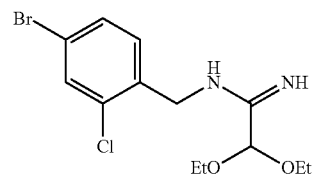 [SMILES: CCOC(OCC)C(=N)NCc1ccc(Br)cc1Cl]

Methyl 2,2-diethoxyethanimidate (2.7 g, 16.8 mmol) was added drop-wise to a stirred solution of (4-bromo-2-chloro-phenyl)methanamine (2.47 g, 11.2 mmol) in methanol (100 mL). The mixture was stirred for 2 hours at room temperature. The reaction was concentrated to dryness and the residue was taken up in dichloromethane. The organic layer washed with brine, dried (Na$_2$SO$_4$) and concentrated to crude N-[(4-bromo-2-chloro-phenyl)methyl]-2,2-diethoxy-acetamidine (3.76 g, 89% yield) as a white solid, which was used in the next step without further purification. LCMS (ESI) [M+H]+=349.0

Step 4: 6-bromo-8-chloro-isoquinolin-3-amine

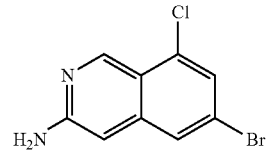 [SMILES: Nc1cc2cc(Br)cc(Cl)c2cn1]

To the crude N-[(4-bromo-2-chloro-phenyl)methyl]-2,2-diethoxy-acetamidine (1.9 g, 5.05 mmol) was added conc.

H₂SO₄ (14.9 g, 152 mmol) at 0° C. under N₂. The reaction mixture was stirred at room temperature for 16 hours. The reaction mixture was cooled to 0° C. and a 1 M NaOH solution added to adjust the pH to 7. The residue was extracted with dichloromethane. The combined organic layers were washed with brine and dried (Na₂SO₄) before concentration to dryness. The crude was purified by flash column chromatography (ethyl acetate:petroleum ether=1:3) to give 6-bromo-8-chloro-isoquinolin-3-amine (410 mg, 33% yield) as a yellow solid. LCMS (ESI) [M+H]⁺=256.9

Example I.2

Intermediate 2: N-(6-bromo-8-chloro-3-isoquinolyl)cyclopropanecarboxamide

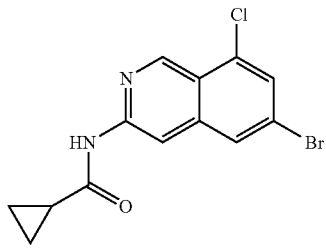 [SMILES: O=C(Nc1cc2cc(Br)cc(Cl)c2cn1)C1CC1]

To a cooled (0° C.) mixture of 6-bromo-8-chloro-isoquinolin-3-amine (900 mg, 2.1 mmol) and pyridine (166 mg, 2.1 mmol) in dichloromethane (10 mL) was added cyclopropanecarbonyl chloride (263 mg, 2.52 mmol). The reaction was stirred at 0° C. for 1 hour. The reaction mixture was quenched by the addition of a saturated aqueous solution of NH₄Cl and extracted with dichloromethane. The organic was dried, filtered and concentrated. The crude was purified by flash column chromatography (40% dichloromethane in petroleum ether) to give (N-(6-bromo-8-chloro-3-isoquinolyl)cyclopropanecarboxamide (550 mg, 74% yield) as a yellow solid. LCMS (ESI) [M+H]⁺=324.9

Example I.3

Intermediate 3: 8-chloro-7-fluoro-6-iodoisoquinolin-3-amine

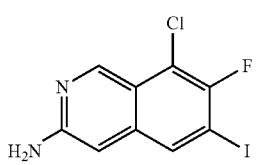

Step 1: 4-amino-2-chloro-3-fluorobenzonitrile

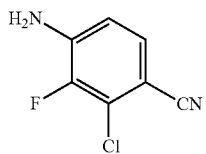

To a sealed tube were added copper (I) cyanide (1.2 g, 13.37 mmol), 4-bromo-3-chloro-2-fluoroaniline (1 g, 4.46 mmol) and 1-methyl-2-pyrrolidinone (8 mL). The mixture was heated at 170° C. for 1 hour in a microwave reactor. The reaction mixture was quenched by addition of a saturated solution of NH₄Cl (20 mL) and filtered. The filtrate was extracted with ethyl acetate (3×100 mL). The combined organic layers were washed with brine (3×10 mL), dried with Na₂SO₄, filtered through a pad of silica gel, and concentrated to dryness to give 4-amino-2-chloro-3-fluorobenzonitrile (700 mg, 92% yield) as a yellow solid. LCMS (ESI) [M+H]⁺=171.1.

Step 2: 2-chloro-3-fluoro-4-iodobenzonitrile

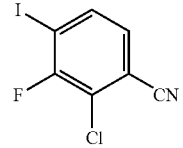

To a suspension of CuI (3341 mg, 17.59 mmol) in acetonitrile (50 mL) was added tert-butyl nitrite (1811 mg, 17.59 mmol) at 65° C. under N₂. The mixture was stirred at 65° C. for 10 minutes. Then 4-amino-2-chloro-3-fluorobenzonitrile (2 g, 11.73 mmol) was added to the reaction mixture. The mixture was stirred at 65° C. for 12 hours. The mixture was quenched with saturated aqueous Na₂S2O4 (30 mL) and aqueous NH₄Cl (30 mL) and extracted with ethyl acetate (3×300 mL). The combined organic layers were washed with brine (2×10 mL), dried over Na₂SO₄ and filtered. The filtrate was concentrated to give crude product, which was purified by flash chromatography (petroleum ether/ethyl acetate=5/1) to give 2-chloro-3-fluoro-4-iodobenzonitrile (1 g, 30% yield) as a yellow solid. ¹H NMR (400 MHz, CDCl₃) δ 7.80 (dd, J=5.6, 8.2 Hz, 1H), 7.22 (dd, J=1.4, 8.2 Hz, 1H).

Step 3: (2-chloro-3-fluoro-4-iodophenyl)methanamine

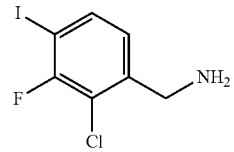

2-Chloro-3-fluoro-4-iodobenzonitrile (1 g, 3.55 mmol) was added to a solution of borane-THF (35.53 mL, 1 M in THF, 35.53 mmol) in THF (30 mL) at 0° C. The mixture was then warmed to room temperature and stirred overnight. The reaction solution was quenched by the dropwise addition of a solution of HCl (6 M, 2 mL). The mixture was neutralized with an aqueous solution of NaHCO₃ to pH=8 and extracted with dichloromethane (2×200 mL). The combined organic layer was washed with water (2×10 mL) and brine (1×10 mL), dried (Na₂SO₄), filtered and concentrated to give (2-chloro-3-fluoro-4-iodophenyl)methanamine (400 mg, crude), which was used directly in the next step without further purification. LCMS (ESI) [M+H]⁺=285.9.

Step 4: N-(2-chloro-3-fluoro-4-iodobenzyl)-2,2-diethoxyacetimidamide

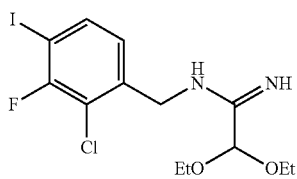 [SMILES: CCOC(OCC)C(=N)NCc1ccc(I)c(F)c1Cl]

To a solution of methyl 2,2-diethoxyacetimidate (0.3 g, 1.88 mmol) in methanol (5 mL) was added (2-chloro-3-fluoro-4-iodophenyl)methanamine (250 mg, 0.88 mmol). The reaction mixture was stirred at 25° C. for 12 hours, and then concentrated to dryness. The residue was taken up in dichloromethane (20 mL), washed with water (2×10 mL) then brine, dried (MgSO$_4$), filtered and concentrated to give N-(2-chloro-3-fluoro-4-iodobenzyl)-2,2-diethoxyacetimidamide (360 mg, crude) as a yellow solid. It was directly used to the next step without purification. LCMS (ESI) [M+H]$^+$ =415.0.

Step 5: 8-chloro-7-fluoro-6-iodoisoquinolin-3-amine

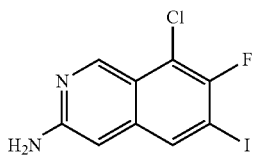

A solution of N-(2-chloro-3-fluoro-4-iodobenzyl)-2,2-diethoxyacetimidamide (0.36 g, 0.87 mmol) and conc. H$_2$SO$_4$ (10 mL, 26.05 mmol) was stirred at 60° C. for 12 hours. The mixture was cooled to 0° C. and NaOH was added to adjust to pH 9. The residue was extracted with dichloromethane (5×100 mL). The combined organic layers were washed with brine, dried (Na$_2$SO$_4$), filtered and concentrated to give 8-chloro-7-fluoro-6-iodoisoquinolin-3-amine (0.25 g, crude) as a yellow solid, which was directly used to the next step. LCMS (ESI) [M+H]$^+$=322.9. $^1$H NMR (400 MHz, CD$_3$OD) δ 9.00 (s, 1H), 8.08 (d, J=5.6 Hz, 1H), 6.70 (s, 1H).

Example I.4

Intermediate 4: 7-bromo-8-chloro-6-iodoisoquinolin-3-amine

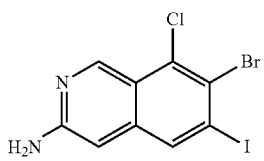 [SMILES: Nc1cc2cc(I)c(Br)c(Cl)c2cn1]

Step 1: 4-amino-3-bromo-2-chlorobenzonitrile

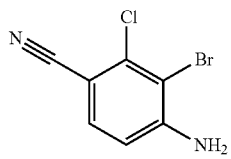

To a solution of 4-amino-2-chlorobenzonitrile (1.5 g, 9.83 mmol) in acetonitrile (30 mL) was added 1,3-dibromo-5,5-dimethyl-2,4-imidazolidinedione (1.5 g, 5.25 mmol). The solution was stirred at 25° C. for 2 hours. The reaction was quenched by addition with a saturated solution of NaHSO$_3$ (30 mL) and extracted with ethyl acetate (50 mL×2). The organic layer was concentrated. The crude product was purified by flash chromatography (10% ethyl acetate in petroleum ether) to give a mixture of 4-amino-3-bromo-2-chlorobenzonitrile and 4-amino-5-bromo-2-chlorobenzonitrile (850 mg, 5/2 ratio of regio-isomers, 26% yield) as a yellow solid. The mixture would be used directly at next step. $^1$H NMR (400 MHz, CDCl$_3$) δ 7.67 (s, 1H), 7.38 (d, J=8.4 Hz, 2.6H), 6.80 (s, 1H), 6.65 (d, J=8.4 Hz, 2.6H), 4.81 (bs, 5H), 4.71 (bs, 2H).

Step 2: 3-bromo-2-chloro-4-iodobenzonitrile

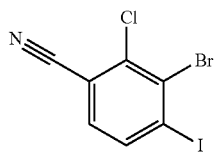 [SMILES: N#Cc1ccc(I)c(Br)c1Cl]

To a suspension of CuI (51.63 g, 271.74 mmol) in acetonitrile (300 mL) was added tert-butyl nitrite (33.59 g, 326.09 mmol). The mixture was stirred at 65° C. for 10 minutes. A mixture of 4-amino-3-bromo-2-chlorobenzonitrile and 4-amino-5-bromo-2-chlorobenzonitrile (3/4 ratio, 25 g, 108.7 mmol) was added to the reaction mixture. The mixture was stirred at 65° C. for 12 hours. The mixture was quenched with saturated Na$_2$S204 solution (30 mL) and extracted with ethyl acetate (3×50 mL). The combined organic layers were washed with brine (10 mL), dried over by Na$_2$SO$_4$ and filtered. The filtrate was concentrated and purified by flash column chromatography (5% ethyl acetate in petroleum ether) to give 3-bromo-2-chloro-4-iodobenzonitrile (5 g, 31% yield) as a yellow solid. $^1$H NMR (400 MHz, CDCl$_3$) 7.91 (d, J=8.0 Hz, 1H), 7.30 (d, J=8.0 Hz, 1H).

Step 3: (3-bromo-2-chloro-4-iodophenyl)methanamine

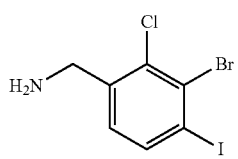

To a solution of 3-bromo-2-chloro-4-iodobenzonitrile (3 g, 8.76 mmol) in THF (30 mL) was added borane-THF (30 mL, 1 M in THF, 30 mmol). The mixture was stirred at 65° C. for 3 h under N₂. The mixture was quenched by addition of methanol (10 mL) and HCl (12 N, 10 mL). The reaction was concentrated to dryness. The residue was taken up in ethyl acetate (100 mL) and extracted with water (50 mL×2). The organic layer was discarded and the pH of the aqueous layer was adjusted to pH 9 by adding a saturated NaHCO₃ solution. The mixture was extracted with ethyl acetate (50 mL×3). The combined organic layers were washed with water (10 mL×2) then brine (10 mL), dried (Na₂SO₄), filtered and concentrated to give (3-bromo-2-chloro-4-iodophenyl)methanamine (3 g, 99% yield) as a yellow oil. It was be used directly at next step. LCMS (ESI) [M+H]⁺=345.9.

Step 4: N-(3-bromo-2-chloro-4-iodobenzyl)-2,2-diethoxyacetimidamide

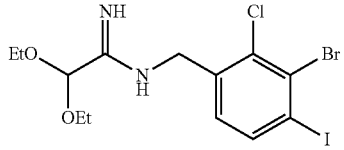 [SMILES: CCOC(OCC)C(=N)NCc1ccc(I)c(Br)c1Cl]

To a solution of (3-bromo-2-chloro-4-iodophenyl)methanamine (2.5 g, 7.22 mmol) in methanol (20 mL) was added methyl 2,2-diethoxyacetimidate (3.75 g, 23.26 mmol). The solution was stirred at 25° C. for 12 hours. The reaction was concentrated to dryness. The residue was dissolved in dichloromethane (20 mL), washed with water and brine, dried over MgSO₄, filtered and concentrated to give N-(3-bromo-2-chloro-4-iodobenzyl)-2,2-diethoxyacetimidamide (3 g, 87% yield) as a yellow solid. It was used directly at next step. LCMS (ESI) [M+H]⁺=474.9.

Step 5:
7-bromo-8-chloro-6-iodoisoquinolin-3-amine

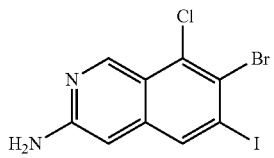 [SMILES: Nc1cc2cc(I)c(Br)c(Cl)c2cn1]

A mixture of sulfuric acid (10 mL) and N-(3-bromo-2-chloro-4-iodobenzyl)-2,2-diethoxyacetimidamide (3 g, 6.31 mmol) was stirred at 60° C. for 12 hours. The reaction mixture was cooled to 0° C. and then NaOH solution was added to adjust the pH to 9. The residue was extracted with dichloromethane (100 mL×3). The combined organic layer was washed with brine, dried over Na₂SO₄, filtered and concentrated to give 7-bromo-8-chloro-6-iodoisoquinolin-3-amine (2.4 g, 99% yield) as a yellow solid. LCMS (ESI) [M+H]⁺=382.8. ¹H NMR (400 MHz, DMSO-d₆): δ 8.99 (s, 1H), 8.32 (s, 1H), 6.56 (s, 1H), 6.49 (s, 2H).

Example I.5

Intermediate 5:
7-bromo-8-chloroisoquinolin-3-amine

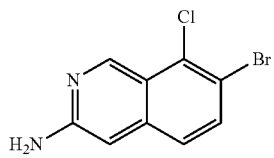 [SMILES: Nc1cc2ccc(Br)c(Cl)c2cn1]

Step 1: (3-bromo-2-chlorophenyl)methanamine

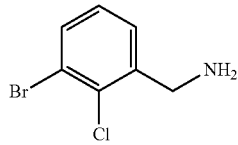

A mixture of 1-bromo-2-chloro-3-methylbenzene (1.0 g, 4.87 mmol), NBS (1.3 g, 7.3 mmol), and benzoyl peroxide (11 mg, 0.05 mmol) in carbon tetrachloride (10 mL) was heated at 80° C. for 18 hours. The mixture was concentrated, then dichloromethane (10 mL) and water (10 mL) were added. The organic layer was dried over Na₂SO₄, filtered and concentrated. The residue was re-dissolved in ethanol (10 mL) and NH₄OH (10 mL, 4.87 mmol) was added. Then the mixture was stirred at room temperature for 2 hours. The mixture was concentrated and purified by prep-TLC (normal phase, silica gel, dichloromethane\Methanol=20:1) to give (3-bromo-2-chlorophenyl)methanamine (500 mg, 46% yield) as a yellow solid. LCMS (ESI) [M+H]⁺=220.0.

Step 2: N-(3-bromo-2-chlorobenzyl)-2,2-diethoxyacetimidamide

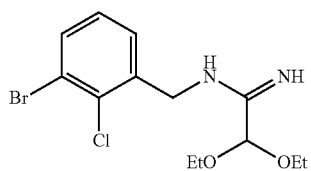 [SMILES: CCOC(OCC)C(=N)NCc1cccc(Br)c1Cl]

Methyl 2,2-diethoxyethanimidate (548 mg, 3.4 mmol) was added dropwise to a stirred solution of (3-bromo-2-chlorophenyl) methanamine (500 mg, 2.27 mmol) in methanol (100 mL). The mixture was stirred at room temperature for 16 hours. The reaction was concentrated to dryness. The residue was taken up in dichloromethane and the organic solution was washed with brine. The organic extract was dried (Na₂SO₄) and concentrated to give the crude product N-(3-bromo-2-chlorobenzyl)-2,2-diethoxyacetimidamide (500 mg, 1.43 mmol, 63% yield) as a yellow oil, which was used in the next step without further purification. LCMS (ESI) [M+H]⁺=351.0.

Step 3: 7-bromo-8-chloroisoquinolin-3-amine

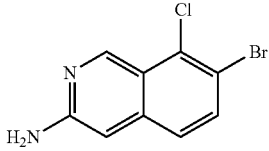 [SMILES: Nc1cc2ccc(Br)c(Cl)c2cn1]

The crude N-(3-bromo-2-chlorobenzyl)-2,2-diethoxyacetimidamide (500 mg, 1.43 mmol) was placed in a round-bottomed flask at 0° C. under inert atmosphere (N$_2$) and conc. H$_2$SO$_4$ (4207 mg, 42.9 mmol) was added. The reaction mixture is stirred overnight at room temperature. The reaction mixture was poured into ice water. NH$_4$OH was added to adjust the pH to 8. The solid was collected by filtration to give 7-bromo-8-chloroisoquinolin-3-amine (300 mg, 81% yield) as a yellow solid. LCMS (ESI) [M+H]$^+$=257.0.

Example I.6

Intermediate 6: 8-bromo-7-chloroisoquinolin-3-yl trifluoromethanesulfonate

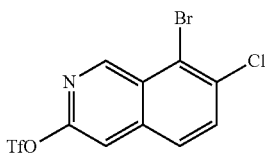 [SMILES: O=S(=O)(Oc1cc2ccc(Cl)c(Br)c2cn1)C(F)(F)F]

Step 1: (2-bromo-3-chlorophenyl)methanamine

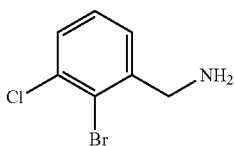

A mixture of 2-bromo-1-chloro-3-methylbenzene (500 mg, 2.43 mmol), NBS (649 mg, 3.65 mmol), benzoyl peroxide (5 mg, 0.02 mmol) and carbon tetrachloride (10 mL) was heated at 80° C. for 18 hours. The mixture was then concentrated. Dichloromethane (10 mL) and water (10 mL) were then added. The organic layer was dried over Na$_2$SO$_4$, filtered and concentrated. The residue was dissolved in ethanol (10 mL) and NH$_4$OH (5 mL, 2.43 mmol) was added. The mixture was stirred at room temperature for 2 hours. The mixture was concentrated and purified by prep-TLC (normal phase, silica gel, dichloromethane\methanol=20:1) to give (2-bromo-3-chlorophenyl)methanamine (300 mg, 1.36 mmol, 55% yield) as a yellow solid. LCMS (ESI) [M+H]$^+$=220.0.

Step 2: N-(2-bromo-3-chlorobenzyl)-2,2-diethoxyacetamide

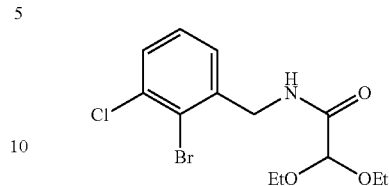

To a mixture of (2,2-diethoxyacetyl)oxysodium (270 mg, 1.59 mmol), (2-bromo-3-chlorophenyl) methanamine (350 mg, 1.59 mmol), HOBT (321 mg, 2.38 mmol), EDCI (454 mg, 2.38 mmol) and DMF (50 mL) was added DIPEA (819 mg, 6.35 mmol). The mixture was stirred at room temperature for 18 hours. Water (50 mL) was then added. The mixture was extracted with ethyl acetate (30 mL×2). The combined organic extracts were washed with water (50 mL×3) then brine (20 mL), dried over Na$_2$SO$_4$, filtered and concentrated to give N-(2-bromo-3-chlorobenzyl)-2,2-diethoxyacetamide (500 mg, 89% yield) as a yellow solid. LCMS (ESI) [M+H]$^+$=351.0.

Step 3: 8-bromo-7-chloroisoquinolin-3-ol

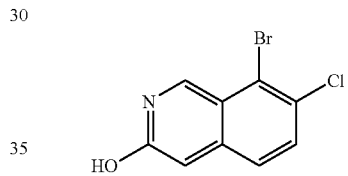

A mixture of N-(2-bromo-3-chlorobenzyl)-2,2-diethoxyacetamide (500 mg, 1.43 mmol) and conc H$_2$SO$_4$ (10 mL, 14.26 mmol) was stirred at room temperature for 3 hours. The mixture was poured into ice water. Ammonium hydroxide was added to adjust the mixture to pH 8. The mixture was extracted with ethyl acetate (30 mL×2). The organic layer was washed with water (20 mL×3), brine (20 ml), dried over Na$_2$SO$_4$, filtered and concentrated to give the 8-bromo-7-chloroisoquinolin-3-ol (270 mg, 73% yield) as a yellow solid, which was used in next step without further purification. LCMS (ESI) [M+H]$^+$=258.0.

Step 4: 8-bromo-7-chloroisoquinolin-3-yl trifluoromethanesulfonate

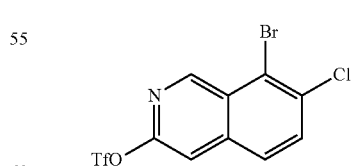

A mixture of 8-bromo-7-chloroisoquinolin-3-ol (270 mg, 1.04 mmol), dichloromethane (10 mL) and DIPEA (404 mg, 3.13 mmol) was cooled to 0° C. Triflic anhydride (383.1 mg, 1.36 mmol) was added slowly. Then the mixture was stirred at room temperature for 16 hours. A saturated aqueous solution of NH$_4$Cl (10 mL) was added. The mixture was extracted with dichloromethane (10 mL×2). The organic layer was dried over Na₂SO₄, filtered and concentrated. The residue was purified by prep-TLC (normal phase, silica gel, petroleum ether/ethyl acetate=10/1) to give 8-bromo-7-chloroisoquinolin-3-yl trifluoromethanesulfonate (290 mg, 71% yield) as a yellow solid. LCMS (ESI) [M+H]⁺=391.0.

Example I.7

Intermediate 7: 8-bromo-7-fluoroisoquinolin-3-yl trifluoromethanesulfonate

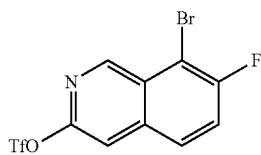 [SMILES: O=S(=O)(Oc1cc2ccc(F)c(Br)c2cn1)C(F)(F)F]

Step 1: (2-bromo-3-fluorophenyl)methanamine

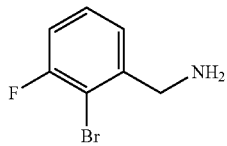

To a solution of 2-bromo-3-fluorobenzonitrile (1.5 g, 7.5 mmol) in THF (10 mL) was added BH₃-THF (2 M in THF, 11.2 mL, 22.4 mmol). The resulting solution was heated at 60° C. for 2 hours. The mixture was cooled to 0° C. A 1N HCl solution was added to quench the reaction. A 1N NaOH solution was added to adjust the pH of the mixture to 8. The mixture was extracted with dichloromethane (20 mL×2). The organic extracts were washed with water (20 mL×3), brine (20 ml), dried over Na₂SO₄, filtered and concentrated to give (2-bromo-3-fluorophenyl)methanamine (850 mg, 56% yield) as a yellow solid. LCMS (ESI) [M+H]⁺=206.0.

Step 2: N-(2-bromo-3-fluorobenzyl)-2,2-diethoxyacetamide

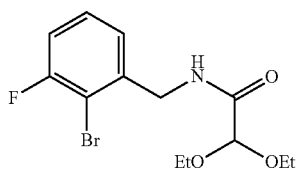 [SMILES: CCOC(OCC)C(=O)NCc1cccc(F)c1Br]

A mixture of (2,2-diethoxyacetyl)oxysodium (667 mg, 3.92 mmol), (2-bromo-3-fluorophenyl)methanamine (800 mg, 3.92 mmol), HOBT (793 mg, 5.88 mmol) and DIPEA (2.0 g, 15.68 mmol) in DMF (5 mL) was stirred at room temperature for 18 hours. Water (50 mL) was then added. The mixture was extracted with ethyl acetate (30 mL×2). The organic layer was washed with water (50 mL×3), brine (20 ml), dried over Na₂SO₄, filtered and concentrated. The crude product was purified by flash chromatography (petroleum ether/ethyl acetate=5/1) to give N-(2-bromo-3-fluorobenzyl)-2,2-diethoxyacetamide (820 mg, 62% yield) as a colorless oil. LCMS (ESI) [M+H]⁺=336.0.

Step 3: 8-bromo-7-fluoroisoquinolin-3-ol

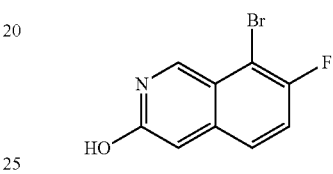

A mixture of N-(2-bromo-3-fluorobenzyl)-2,2-diethoxyacetamide (953 mg, 2.85 mmol) and conc H₂SO₄ (10 mL, 28 mmol) was stirred at room temperature for 3 hours. The mixture was poured into ice water. Ammonium hydroxide was added to adjust the pH to 8. The mixture was extracted with ethyl acetate (30 mL×2). The organic layer was washed with water (20 mL×3), brine (20 mL), dried over Na₂SO₄, filtered and concentrated to get crude 8-bromo-7-fluoroisoquinolin-3-ol (500 mg, 72% yield) as a yellow solid, which was used in next step without further purification. LCMS (ESI) [M+H]⁺=243.9.

Step 4: 8-bromo-7-fluoroisoquinolin-3-yl trifluoromethanesulfonate

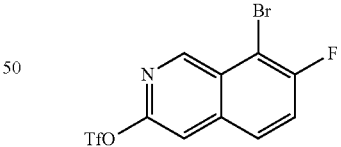

A mixture of 8-bromo-7-fluoroisoquinolin-3-ol (500 mg, 2.07 mmol), dichloromethane (10 mL) and DIPEA (799 mg, 6.2 mmol) was cooled to 0° C. Triflic anhydride (757 mg, 2.69 mmol) was added slowly. The mixture was stirred at room temperature for 3 hours. Aqueous saturated NH₄Cl (10 mL) was added. The mixture was extracted with dichloromethane (10 mL×2). The combined organic extracts were dried over Na₂SO₄, filtered and concentrated. The residue was purified by prep-TLC (normal phase silica gel, petroleum ether/ethyl acetate=10/1) to give 8-bromo-7-fluoroisoquinolin-3-yl trifluoromethanesulfonate (600 mg, 77% yield) as a yellow solid. LCMS (ESI) [M+H]⁺=373.9.

Example I.8

Intermediate 8: (±)-trans-N-[7-bromo-8-chloro-6-(4-methyl-3-pyridyl)-3-isoquinolyl]-2-cyano-cyclopropanecarboxamide

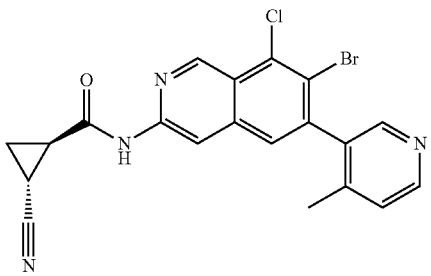 [SMILES: Cc1ccncc1-c1cc2cc(NC(=O)[C@@H]3C[C@H]3C#N)ncc2c(Cl)c1Br]

Step 1: 7-bromo-8-chloro-6-(4-methyl-3-pyridyl)isoquinolin-3-amine

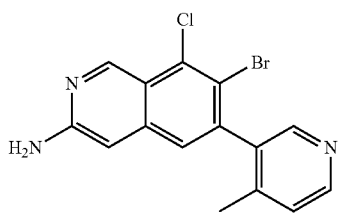 [SMILES: Cc1ccncc1-c1cc2cc(N)ncc2c(Cl)c1Br]

A mixture of 7-bromo-8-chloro-6-iodo-isoquinolin-3-amine (3.6 g, 9.39 mmol), 4-methyl-3-(4,4,5,5-tetramethyl-1,3,2-dioxaborolan-2-yl)pyridine (2.5 g, 11.41 mmol), Pd(PPh$_3$)$_4$ (750 mg, 0.65 mmol), K$_2$CO$_3$ (3.8 g, 27.54 mmol) in 1,4-dioxane (160 mL) and water (40 mL) was stirred at 70° C. under Ar for 23 hours. The reaction mixture was cooled to room temperature. Ethyl acetate was added and the mixture was washed with brine (100 mL). The organic layer was separated, dried over Na$_2$SO$_4$, filtered and evaporated. The residue was purified with silica-gel column chromatography (petroleum ether/ethyl acetate=1:2 to ethyl acetate) to give 7-bromo-8-chloro-6-(4-methyl-3-pyridyl)isoquinolin-3-amine (2.9 g, 89% yield) as a yellow solid. LCMS (ESI) [M+H]$^+$=348.0.

Step 2: (±)-trans-N-[7-bromo-8-chloro-6-(4-methyl-3-pyridyl)-3-isoquinolyl]-2-cyano-cyclopropanecarboxamide

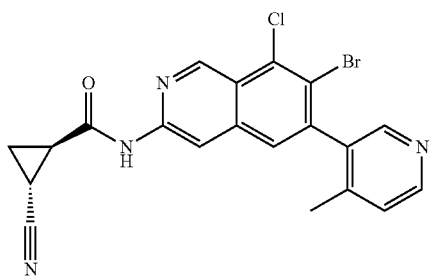 [SMILES: Cc1ccncc1-c1cc2cc(NC(=O)[C@@H]3C[C@H]3C#N)ncc2c(Cl)c1Br]

Oxalyl chloride (3.0 g, 23.62 mmol) was added dropwise to a suspension of (±)-trans-2-cyanocyclopropanecarboxylic acid (1.2 g, 10.8 mmol) at 0° C. The mixture was stirred at 0° C. for 1 hour. The mixture was evaporated at room temperature to remove the dichloromethane and excess oxalyl chloride. The residue was re-suspended in dichloromethane (5 mL) and was added dropwise to a mixture of 7-bromo-8-chloro-6-(4-methyl-3-pyridyl)isoquinolin-3-amine (2.9 g, 8.32 mmol), and pyridine (10 mL, 123.64 mmol) in dichloromethane (50 mL) at 0° C. Then the reaction mixture was stirred at 0° C. for 0.5 hours. The reaction mixture was diluted with dichloromethane (100 mL) and washed with H$_2$O (50 mL). The organic layer was separated, dried over Na$_2$SO$_4$, filtered and evaporated. The residue was purified with silica-gel column chromatography (petroleum ether/ethyl acetate=1:1 to 1:2) to give (±)-trans-N-[7-bromo-8-chloro-6-(4-methyl-3-pyridyl)-3-isoquinolyl]-2-cyano-cyclopropanecarboxamide (2.85 g, 78% yield) as a light brown solid. LCMS (ESI) [M+H]$^+$=441.0.

Example I.9

Intermediate 9: (3-amino-8-chloro-6-isoquinolyl)boronic Acid

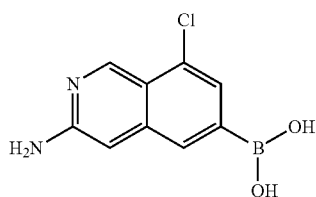 [SMILES: Nc1cc2cc(B(O)O)cc(Cl)c2cn1]

A mixture of bis(pinacolato)diboron (976 mg, 3.84 mmol), 6-bromo-8-chloro-isoquinolin-3-amine (900 mg, 3.5 mmol), Pd(dppf)Cl$_2$ (127 mg, 0.17 mmol) and potassium acetate (1370 mg, 13.98 mmol) in 1,4-dioxane (20 mL) was stirred at 100° C. for 3 hours under nitrogen. Ethyl acetate (50 mL) was added. The mixture was filtered and concentrated to give crude (3-amino-8-chloro-6-isoquinolyl)boronic acid (830 mg, 78% yield) as a yellow oil, which was used directly without further purification. LCMS (ESI): [M+H]$^+$=223.1.

Example I.10

Intermediate 10: (±)-trans-N-(6-bromo-8-chloroisoquinolin-3-yl)-2-cyanocyclopropanecarboxamide

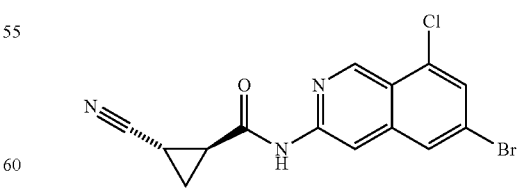

A mixture of ethanedioyl dichloride (1330 mg, 10.49 mmol), (±)-trans-2-cyanocyclopropanecarboxylic acid (582 mg, 5.24 mmol) and one drop of DMF in dichloromethane (5 mL) was stirred at room temperature for 0.5 hours. The reaction was concentrated to dryness. To a solution of 6-bromo-8-chloro-isoquinolin-3-amine (450 mg, 1.75 mmol) in dichloromethane (5 mL) and pyridine (1 mL) was added the residue in portions at 0° C. The mixture was stirred for 1 hour at room temperature. The reaction was concentrated to dryness. The residue was purified by silica-gel column chromatography (petroleum ether/ethyl acetate=4:1 to petroleum ether:ethyl acetate=2:1) to give the title compound as a yellow solid (200 mg, 32.6% yield). LCMS (ESI) [M+H]⁺=352.0.

Example I.11

Intermediate 11: (±)-cis-N-(6-bromo-8-chloro-3-isoquinolyl)-2-fluoro-cyclopropanecarboxamide

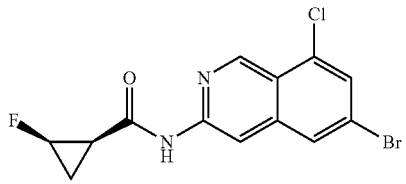 [SMILES: O=C(Nc1cc2cc(Br)cc(Cl)c2cn1)[C@H]1C[C@H]1F]

Step 1: (±)-cis-2-fluorocyclopropanecarbonyl Chloride

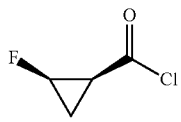

To a solution of (±)-cis-2-fluorocyclopropanecarboxylic acid (2.1 g, 20.18 mmol) in dichloromethane (10 mL) and DMF (0.10 mL) was added dropwise ethanedioyl dichloride (3.33 g, 26.23 mmol). The mixture was stirred at 25° C. for 2 hours. The reaction mixture was concentrated in vacuum to give a yellow residue, which was then used directly in the next step.

Step 2: (±)-cis-N-(6-bromo-8-chloro-3-isoquinolyl)-2-fluoro-cyclopropanecarboxamide

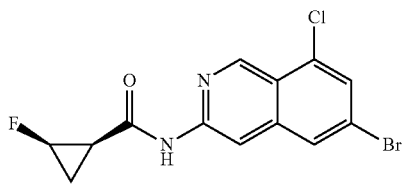 [SMILES: O=C(Nc1cc2cc(Br)cc(Cl)c2cn1)[C@H]1C[C@H]1F]

To a solution of 6-bromo-8-chloro-isoquinolin-3-amine (2.0 g, 7.77 mmol) in dichloromethane (10 mL) and pyridine (1.88 mL, 23.3 mmol) was added a solution of (±)-cis-2-fluorocyclopropanecarbonyl chloride (2.38 g, 19.42 mmol) dissolved in dichloromethane (2 mL). The mixture was stirred at 25° C. for 2 hours and then concentrated. Water (10 mL) was added and then a 1 N HCl solution was added to adjust the pH of the mixture to 6. The mixture was extracted with dichloromethane (10 mL×3). The organic layer was washed with brine (20 ml), dried over Na₂SO₄, filtered and concentrated. The residue was purified by flash chromatography (petroleum ether/ethyl acetate=4:1) to give (±)-cis-N-(6-bromo-8-chloro-3-isoquinolyl)-2-fluoro-cyclopropanecarboxamide (2.3 g, 86% yield) as a yellow solid. LCMS (ESI): [M+H]⁺=343.0.

Example I.12

Intermediate 12: (±)-trans-8-chloro-3-((trans)-2-cyanocyclopropanecarboxamido)isoquinolin-6-ylboronic Acid

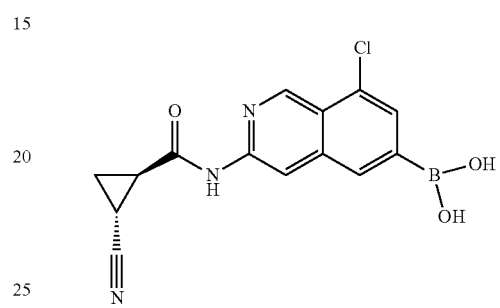

A mixture of (±)-trans-N-(6-bromo-8-chloro-3-isoquinolyl)-2-cyano-cyclopropanecarboxamide (300 mg, 0.86 mmol), bis(pinacolato)diboron (261 mg, 1.03 mmol), potassium acetate (210 mg, 2.14 mmol) and Pd(dppf)Cl₂ (31 mg, 0.04 mmol) in 1,4-dioxane (4 mL) was stirred in a sealed tube at 80° C. for 3 hours. The mixture was concentrated to give (±)-[8-chloro-3-[[(trans)-2-cyanocyclopropane carbonyl] amino]-6-isoquinolyl]boronic acid (240 mg, 59% yield) as a black solid. LCMS (ESI): [M+H]⁺=316.0.

Examples I.13

Intermediate 13: tert-butyl N-[5-(3-amino-8-chloro-7-fluoro-6-isoquinolyl)-4-methyl-3-pyridyl]-N-tert-butoxycarbonyl-carbamate

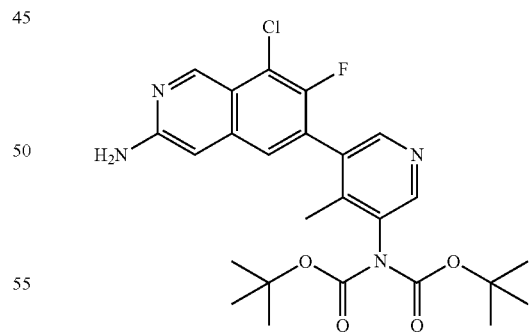

A mixture of 8-chloro-7-fluoro-6-iodo-isoquinolin-3-amine (3.6 g, 11.2 mmol), tert-butyl N-tert-butoxycarbonyl-N-[4-methyl-5-(4,4,5,5-tetramethyl-1,3,2-dioxaborolan-2-yl)-3-pyridyl]carbamate (10 g, 23 mmol), Pd(dppf)Cl₂ (0.82 g, 1.1 mmol), potassium carbonate (3.4 g, 25 mmol) in 1,4-dioxane (100 mL) and water (10 mL) was stirred at 90° C. for 2 h. The reaction was filtered. The product was extracted with ethyl acetate. The combined organic extracts were combined and concentrated under vacuum. The residue was purified by flash chromatrography (40% ethyl acetate in pet. ether) to give the title compound as a yellow oil (3.4 g, 61%).

Examples I.14

Intermediate 14: tert-butyl 8-methyl-7-(4,4,5,5-tetramethyl-1,3,2-dioxaborolan-2-yl)-2,3-dihydropyrido[2,3-b][1,4]oxazine-1-carboxylate

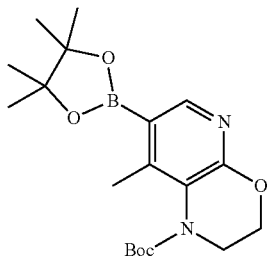 [SMILES: Cc1c(B2OC(C)(C)C(C)(C)O2)cnc2c1N(C(=O)OC(C)(C)C)CCO2]

Step 1: tert-butyl 7-bromo-8-methyl-2,3-dihydropyrido[2,3-b][1,4]oxazine-1-carboxylate

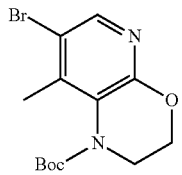

To a solution of 7-bromo-8-methyl-2,3-dihydro-1H-pyrido[2,3-b][1,4]oxazine (1 g, 4.37 mmol) in tetrahydrofuran (2 mL) was added dropwise LiHMDS (8.73 mL, 8.73 mmol, 1 mol/L) at 0° C. The resulting solution was stirred under nitrogen for 0.5 h at 0° C. Then di-tert-butyl dicarbonate (2.85 g, 13.07 mmol) was added and the reaction was stirred at room temperature for 2 h. The reaction was quenched by methanol (50 mL). The solvent was concentrated under vacuum. The residue was purified by silica gel flash chromatography (ethyl acetate/petroleum ether, 1/4) to afford tert-butyl 7-bromo-8-methyl-2,3-dihydropyrido[2,3-b][1,4]oxazine-1-carboxylate (800 mg, 2.43 mmol) as a yellow oil. LCMS (ESI) [M+H]⁺=329.2.

Step 2: tert-butyl 8-methyl-7-(4,4,5,5-tetramethyl-1,3,2-dioxaborolan-2-yl)-2,3-dihydropyrido[2,3-b][1,4]oxazine-1-carboxylate

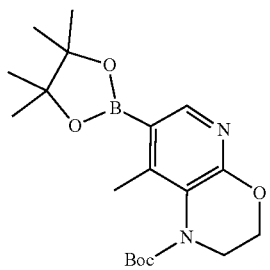 [SMILES: Cc1c(B2OC(C)(C)C(C)(C)O2)cnc2c1N(C(=O)OC(C)(C)C)CCO2]

A mixture of tert-butyl 7-bromo-8-methyl-2,3-dihydropyrido[2,3-b][1,4]oxazine-1-carboxylate (6.2 g, 18.83 mmol), dipinacoldiboron (23.93 g, 94.22 mmol), [1,1'-bis(diphenylphosphino)ferrocene]dichloropalladium(II) (2.76 g, 3.77 mmol) and potassium acetate (5.55 g, 56.62 mmol) in 1,4-dioxane (2 mL) was stirred under nitrogen for 2.5 h at 90° C. The solvent was concentrated under vacuum. The residue was purified by flash chromatography on silica gel eluting with ethyl acetate/petroleum ether (30%) to afford tert-butyl 8-methyl-7-(4,4,5,5-tetramethyl-1,3,2-dioxaborolan-2-yl)-2,3-dihydropyrido[2,3-b][1,4]oxazine-1-carboxylate (5 g, 13.29 mmol) as a yellow oil. LCMS (ESI) [M+H]⁺=376.3.

Examples I.15

Intermediate 15: 2-ethyl-3-(1-methylpyrazol-4-yl)cyclopropanecarboxylic Acid

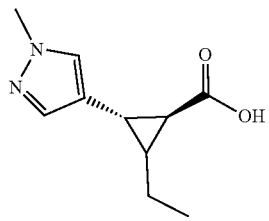

Step 1: Diphenyl(propyl)sulfonium Tetrafluoroborate

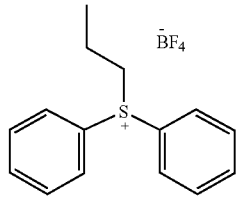

To a solution of silver tetrafluoroborate (2 g, 10.31 mmol) in dichloromethane (20 mL) was added 1-iodopropane (1.75 g, 10.31 mmol) and diphenyl sulfide (5.76 g, 30.93 mmol) at 0° C. The reaction was stirred at 35° C. for 15 hours. The mixture was filtered and the filtrate was concentrated under vacuum. The residue was washed with dichloromethane-ether to afford diphenyl(propyl)sulfonium tetrafluoroborate (2 g, 6.32 mmol) as a white solid. LCMS (ESI) [M+H]⁺=229.

Step 2: tert-butyl 2-ethyl-3-(1-methylpyrazol-4-yl)cyclopropanecarboxylate

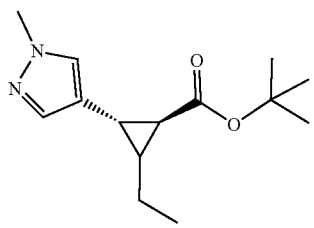 [SMILES: CCC1[C@H](C(=O)OC(C)(C)C)[C@H]1c1cnn(C)c1]

To a solution of diphenyl(propyl)sulfonium tetrafluoroborate (1.50 g, 4.75 mmol) in 1,2-dimethoxyethane (30 mL) and dichloromethane (3 mL) was added lithium diisopropylamide (5.54 ml, 11.09 mmol) at −78° C. The resulting mixture was stirred for 1 hour at −78° C. Then tert-butyl (Z)-3-(1-methylpyrazol-4-yl)prop-2-enoate (330 mg, 1.58 mmol) was added and stirred at −78° C. to 25° C. for 15 hours. The reaction was quenched with water. The resulting mixture was extracted with dichloromethane and dried with anhydrous sodium sulfate. After filtration, the filtrate was concentrated under vacuum to afford tert-butyl 2-ethyl-3-(1-methylpyrazol-4-yl)cyclopropanecarboxylate (350 mg, 1.40 mmol) as a brown oil. LCMS (ESI) [M+H]$^+$=251.

Step 3: 2-ethyl-3-(1-methylpyrazol-4-yl)cyclopropanecarboxylic Acid

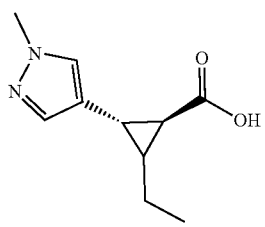

A solution of trans-tert-butyl 2-ethyl-3-(1-methylpyrazol-4-yl)cyclopropanecarboxyate (350 mg, 1.4 mmol) and 2,2,2-trifluoroacetic acid (8 mL) in dichloromethane (3 mL) was stirred at 25° C. for 1 hour. The mixture was concentrated under vacuum. The resulting residue was purified by reverse phase chromatography (acetonitrile 0-40/0.1% HCl in water) to afford 2-ethyl-3-(1-methylpyrazol-4-yl)cyclopropanecarboxylic acid (260 mg, 1.34 mmol) as a brown oil. Product mixture consists of 4 stereoisomers where pyrazole is trans to carboxylic acid and (+/−)-2,2-dimethyl-3-(1-methyl-1H-pyrazol-4-yl)cyclopropane-1-carboxylic acid as a contaminant. LCMS (ESI) [M+H]$^+$=195.

Examples I.16

Intermediate 16: 2-bromo-5,5,6-trimethyl-4,8-dihydropyrazolo[1,5-d][1,4]diazepin-7-one

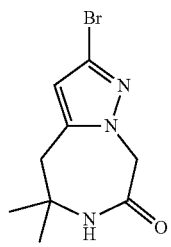

Step 1: 2-(3,5-dibromopyrazol-1-yl)acetonitrile

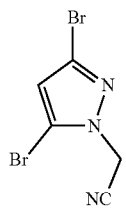

A mixture of 3,5-dibromo-1H-pyrazole (1.0 g, 4.43 mmol) and potassium carbonate (1.22 g, 8.85 mmol) in N,N-dimethylformamide (20 mL) was stirred at 25° C. for 10 min. Bromoacetonitrile (796.59 mg, 6.64 mmol) was added and the reaction was stirred at 25° C. for 2 h. After filtration, the filtrate was diluted with ethyl acetate (30 mL). The reaction was washed with water. The organic phase was dried with anhydrous sodium sulfate. After filtration, the filtrate was concentrated under vacuum. The residue was purified by flash chromatography on silica gel eluting with petroleum ether/dichloromethanol (1/1) to afford 2-(3,5-dibromopyrazol-1-yl)acetonitrile (950 mg, 3.59 mmol) as a white solid. LCMS (ESI) [M+H]$^+$=264.

Step 2: 2-[3-bromo-5-(2-methylprop-1-enyl)pyrazol-1-yl]acetonitrile

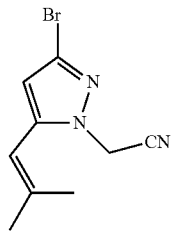

A mixture of 2-(3,5-dibromopyrazol-1-yl)acetonitrile (1.0 g, 3.77 mmol), 4,4,5,5-tetramethyl-2-(2-methylprop-1-en-1-yl)-1,3,2-dioxaborolane (687.29 mg, 3.77 mmol), Pd(dppf)Cl$_2$ (552.64 mg, 0.75 mmol), and potassium carbonate (1.56 g, 11.32 mmol) in 1,4-dioxane (20 mL) and water (2 mL) was stirred under nitrogen for 1 h at 100° C. After filtration, the filtrate was concentrated under vacuum. The residue was purified by silica gel flash chromatography eluting with ethyl acetate/petroleum ether (1/3) to afford 2-[3-bromo-5-(2-methylprop-1-enyl)pyrazol-1-yl]acetonitrile (700 mg, 2.92 mmol) as a white solid. LCMS (ESI) [M+H]$^+$=240.

Step 3: 2-bromo-5,5-dimethyl-6,8-dihydro-4H-pyrazolo[1,5-d][1,4]diazepin-7-one

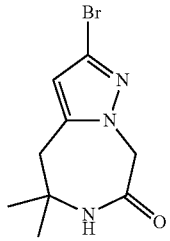

A mixture of 2-[3-bromo-5-(2-methylprop-1-enyl)pyrazol-1-yl]acetonitrile (700 mg, 2.92 mmol) in methylsulfonic acid (15 mL) was stirred at 65° C. for 3 d. The reaction was quenched with ice water. The reaction mixture was adjusted to pH 9-10 with an aqueous sodium hydroxide solution. The resulting solution was extracted with dichloromethane and dried with anhydrous sodium sulfate. After filtration, the filtrate was concentrated under vacuum. The residue was purified by reverse phase chromatography (acetonitrile 0-40/0.1% NH$_4$HCO$_3$ in water) to afford 2-bromo-5,5-dimethyl-6,8-dihydro-4H-pyrazolo[1,5-d][1,4]diazepin-7-one (300 mg, 1.16 mmol) as a white solid. LCMS (ESI) [M+H]$^+$=258.

Step 4: 2-bromo-5,5,6-trimethyl-4,8-dihydropyrazolo[1,5-d][1,4]diazepin-7-one

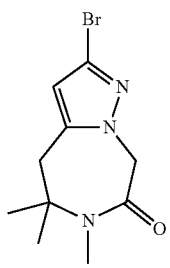

A mixture of 2-bromo-5,5-dimethyl-6,8-dihydro-4H-pyrazolo[1,5-d][1,4]diazepin-7-one (100 mg, 0.39 mmol) and potassium tert-butoxide (52.07 mg, 0.46 mmol) in tetrahydrofuran (10 mL) was stirred at 25° C. for 10 min. Iodomethane (82.52 mg, 0.58 mmol) was added. The reaction was stirred at 25° C. for 1 h. The reaction was concentrated under vacuum and purified by flash chromatography on silica gel eluting with dichloromethane/methanol (95/5) to afford 2-bromo-5,5,6-trimethyl-4,8-dihydropyrazolo[1,5-d][1,4]diazepin-7-one (80 mg, 0.29 mmol) as a white solid. LCMS (ESI) [M+H]$^+$=272.

Examples I.17

Intermediate 17: 2-bromo-4-methylene-5,6-dihydro-4H-pyrazolo[1,5-d][1,4]diazepin-7(8H)-one

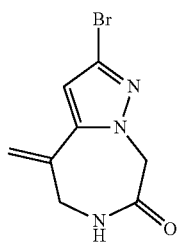

Step 1: 3,5-dibromo-1H-pyrazole

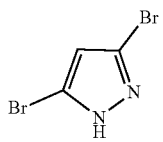

To a 3 L 3-necked round-bottom flask was added compound 1 (200 g, 656 mmol, 1.0 eq) in dimethyl tetrahydrofuran (1000 mL) under N$_2$ and then the solution was cooled to −78° C. n-BuLi (2.5 M, 525 mL, 2.0 eq) was added dropwise to the above solution for 1 hour at −78° C. and the mixture was stirred at −78° C. for 3 hours. TLC (Petroleum ether/Ethyl acetate=3/1, R$_f$=0.51) showed the reaction was completed and one main new spot formed. The two reactions were combined and the reaction mixture was poured into water (1000 mL) at 0° C. and the pH value of the solution was acidified to 4-5 with 2N HCl. The resulting solution was extracted with ethyl acetate (1000 mL, 800 mL, 400 mL). The combined organic phase was washed with brine (800 mL), dried with anhydrous Na$_2$SO$_4$ and concentrated under vacuum to give the title compound (284 g, 1.26 mol, 95.8% yield) as a yellow solid. The crude product was directly used to the next step without further purification.

Step 2: tert-butyl 2-(3,5-dibromo-1H-pyrazol-1-yl)acetate

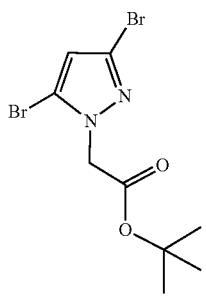

To the solution of 3,5-dibromo-1H-pyrazole (137 g, 607 mmol, 1.0 eq) in MeCN (959 mL) was added tert-butyl 2-chloroacetate (137 g, 910 mmol, 131 mL, 1.5 eq), K$_2$CO$_3$ (137 g, 989 mmol, 1.63 eq) and TBAI (11.0 g, 29.7 mmol, 0.049 eq). The resulting solution was stirred at 25° C. for 12 hours. TLC (Petroleum ether/Ethyl acetate=5/1, $R_f$=0.74) showed the reaction was complete and one main new spot formed. The reaction mixture was filtered, the filter cake was washed with EtOAc (500 mL×3, 300 mL, 200 mL). The combined filtrate was concentrated to give a residue. The residue was dissolved in EtOAc (2.0 L), washed with water (1.0 L), brine (1.0 L). The organic phase was dried with anhydrous $Na_2SO_4$, filtered and concentrated in vacuum to give the title compound (744 g, crude) as a brown oil. $^1$H NMR: (400 MHz, $CDCl_3$): δ 6.35 (s, 1H), 4.80 (s, 2H), 1.46 (s, 9H).

Step 3: 2-(3,5-dibromo-1H-pyrazol-1-yl)acetic Acid

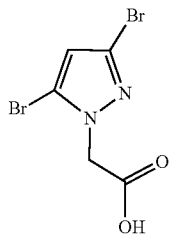

To the solution of compound tert-butyl 2-(3,5-dibromo-1H-pyrazol-1-yl)acetate (248 g, 729 mmol, 1.0 eq) in DCM (140 mL) was added TFA (2.08 kg, 18.2 mol, 1.35 L, 25 eq) and the resulting solution was heated to 80° C. and stirred for 2 hours. TLC (Petroleum ether/Ethyl acetate=5/1, $R_f$=0.03) showed the reaction was complete and one main new spot formed. The reaction was repeated twice. The combined reaction mixtures were concentrated under reduced pressure to give a crude product. The crude product was diluted with petroleum ether/ethyl acetate (4/1, 1.0 L) and the resulting suspension was stirred at 25° C. for 1 hour, then filtered. The filter cake was collected and dried in vacuum to give the title compound (471 g, 1.66 mol, 75.8% yield) as a creamy white solid. 1H NMR: (400 MHz, DMSO) δ 13.3 (br s, 1H), 6.70 (s, 1H), 4.96 (s, 2H).

Step 4:
N-allyl-2-(3,5-dibromo-1H-pyrazol-1-yl)acetamide

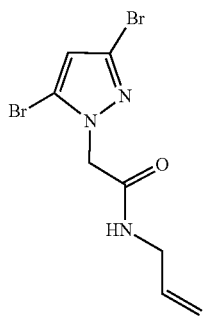

To the solution of 2-(3,5-dibromo-1H-pyrazol-1-yl)acetic acid (157 g, 553 mmol, 1.0 eq) in DMF (1.10 L) was added DIPEA (357 g, 2.77 mol, 482 mL, 5.0 eq) and EDCI (138 g, 719 mmol, 1.3 eq) at 0° C., the resulting solution was stirred at 0° C. for 30 min. Then HOBt (97.1 g, 719 mmol, 1.3 eq) was added and the mixture was stirred at 0° C. for another 30 min. Then prop-2-en-1-amine (47.4 g, 830 mmol, 62.2 mL, 1.5 eq) was added at 0° C. and the mixture was warmed to 25° C. and stirred for 16 hours. TLC (Petroleum ether/ Ethyl acetate=1/1, $R_f$=0.60) showed the reaction was completed and one main new spot formed. The reaction was repeated two more times. The three batches of reactions were combined and the reaction mixture was poured into ice water (12.0 L), extracted with ethyl acetate (2.00 L, 2.00 L, 1.00 L). The combined organic phase was washed with brine (2.0 L), and then concentrated in vacuum to give a crude product. The crude product was purified by column chromatography on silica gel (Petroleum ether/Ethyl acetate=3/1) to afford the title compound (340 g, 1.05 mol, 63.5% yield) as a white solid. H NMR: (400 MHz, $CDCl_3$) δ 6.41 (s, 1H), 5.89 (br s, 1H), 5.79 (m, 1H), 5.08-5.17 (m, 2H), 4.85 (s, 2H), 3.86-3.93 (m, 2H).

Step 5: N-allyl-2-(3,5-dibromo-1H-pyrazol-1-yl)-N-(4-methoxybenzyl)acetamide

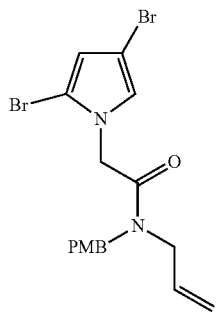

To a solution of N-allyl-2-(3,5-dibromo-1H-pyrazol-1-yl)acetamide (103 g, 319 mmol, 1.0 eq) in THF (721 mL) was added KOH (32.2 g, 574 mmol, 1.8 eq), 18-Crown-6 (3.37 g, 12.8 mmol, 0.04 eq) and 1-(chloromethyl)-4-methoxybenzene (64.9 g, 415 mmol, 56.5 mL, 1.3 eq), then the mixture was stirred at 25° C. for 64 h. TLC (Petroleum ether/Ethyl acetate=2/1, $R_f$=0.50) showed one main new spot formed. The reaction was repeated two more times. The three batches reactions were combined and the reaction mixture was added water (1.00 L), and the pH value was adjusted to 7-8 with 1M HCl, then extracted with EtOAc (1.00 L, 800 mL×3). The combined organic phase was washed with brine (800 mL), dried with anhydrous $Na_2SO_4$, filtered and concentrated in vacuum to give a crude product. The crude product was purified by column chromatography on silica gel (Petroleum ether/Ethyl acetate=2/1) to afford the title compound (320 g, 722 mmol, 75.5% yield) as a yellow oil.

Step 6: 2-bromo-6-(4-methoxybenzyl)-4-methylene-5,6-dihydro-4H-pyrazolo[1,5-d][1,4]diazepin-7(8H)-one

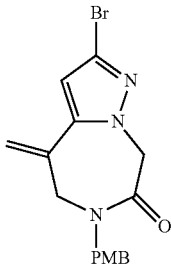

To a solution of N-allyl-2-(3,5-dibromo-1H-pyrazol-1-yl)-N-(4-methoxybenzyl)acetamide (50.0 g, 113 mmol, 1.0 eq) in DMF (1.0 L) was added K$_2$CO$_3$ (31.2 g, 226 mmol, 2.0 eq), Pd(PPh$_3$)$_4$ (17.0 g, 14.7 mmol, 0.13 eq) under Ar, then the mixture was stirred at 120° C. for 16 hours. The reaction was repeated six more times. The seven batches of reactions were combined and the reaction mixture was concentrated in vacuum to remove the solvent to give a residue. Then the residue was added water (2.0 L), extracted with ethyl acetate (2.0 L, 1.0 L, 1.0 L). The combined organic phase was washed with brine (1.0 L) and concentrated to give a crude product. The crude product was purified by column chromatography on silica gel (Petroleum ether/Ethyl acetate=2/1) to afford the title compound compound (74.1 g, 204 mmol, 25.9% yield, 98.7% purity) as a white solid. $^1$H NMR: (400 MHz, CDCl$_3$) δ 7.21 (d, J=8.8 Hz, 2H), 6.86-6.92 (m, 2H), 6.52 (s, 1H), 5.50 (s, 1H), 5.20 (s, 2H), 5.02 (s, 1H), 4.58 (s, 2H), 4.13 (s, 2H), 3.83 (s, 3H).

Step 7: 2-bromo-4-methylene-5,6-dihydro-4H-pyrazolo[1,5-d][1,4]diazepin-7(8H)-one

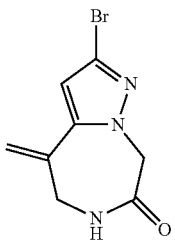

A solution of 2-bromo-6-(4-methoxybenzyl)-4-methylene-5,6-dihydro-4H-pyrazolo[1,5-d][1,4]diazepin-7(8H)-one (3.90 g, 10.8 mmol, 1.0 eq), TFA (38.4 g, 336 mmol, 24.9 mL, 31.3 eq) and trifluoromethanesulfonic acid (16.2 g, 108 mmol, 9.5 mL, 10 eq) in DCM (28 mL) was stirred at 25° C. for 12 hours. The reaction mixture was concentrated to give a residue. To the residue was added water (100 mL), then the pH value was adjusted to 6-7 with saturated aqueous NaHCO$_3$ solution, extracted with EtOAc (100 mL×3, 60 mL×3). The combined organic phase was dried with anhydrous Na$_2$SO$_4$, filtered and concentrated in vacuum to give a crude product. The crude product was purified by column chromatography on silica gel (Petroleum ether/Ethyl acetate=1/1) to afford the title compound (1.90 g, 7.85 mmol, 72.9% yield) as a gray solid. $^1$H NMR: (400 MHz, CDCl$_3$) δ 6.88 (s, 1H), 6.54 (s, 1H), 5.55 (s, 1H), 5.21 (s, 1H), 5.08 (s, 2H), 4.15 (d, J=6.0 Hz, 2H).

Examples I.18

Intermediate 18: 2-Bromo-6-methyl-4-methylidene-4H,5H,6H,7H,8H-pyrazolo[1,5-d][1,4]diazepin-7-one

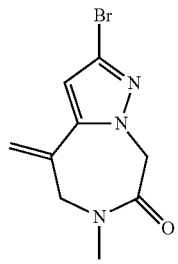

Step 1: 2-(3,5-Dibromo-1H-pyrazol-1-yl)-N-methyl-N-(prop-2-en-1-yl)acetamide

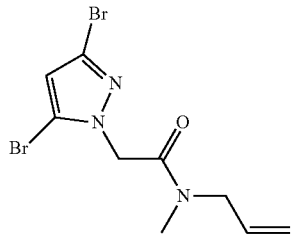

A solution of 2-(3,5-dibromo-1H-pyrazol-1-yl)acetic acid (15 g, 52.84 mmol), methyl(prop-2-en-1-yl)amine (5.7 g, 80.15 mmol), N,N-diisopropylethylamine (27 g, 208.9 mmol) and HATU (30 g, 78.9 mmol) in N,N-dimethylformamide (500 mL) was stirred for 16 hours at room temperature. The resulting mixture was diluted with ethyl acetate and then washed with sodium chloride solution. The organic phase was dried with anhydrous sodium sulfate. After filtration, the filtrate was concentrated under vacuum. The residue was purified by flash chromatography on silica gel eluting with ethyl acetate/petroleum ether (2/3) to afford 2-(3,5-dibromo-1H-pyrazol-1-yl)-N-methyl-N-(prop-2-en-1-yl)acetamide (16.3 g, 92%) as a yellow oil. LCMS (ESI) [M+H]$^+$=338.0.

Step 2: 2-Bromo-6-methyl-4-methylidene-4H,5H,6H,7H,8H-pyrazolo[1,5-d][1,4]diazepin-7-one

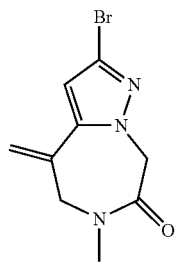

A mixture of 2-(3,5-dibromo-1H-pyrazol-1-yl)-N-methyl-N-(prop-2-en-1-yl)acetamide (5 g, 14.84 mmol), palladium acetate (166 mg, 0.74 mmol), triphenylphosphine (388 mg, 1.48 mmol), TBAB (4.8 g, 14.890 mmol) and potassium acetate (4.2 g, 42.80 mmol) in N,N-dimethylformamide (100 mL) was stirred for 10 h at 80° C. After filtration, the filtrate was concentrated under vacuum. The residue was purified on a silica gel column eluted with ethyl acetate/petroleum ether (2/1) to afford 2-bromo-6-methyl-4-methylidene-4H,5H,6H,7H,8H-pyrazolo[1,5-d][1,4]diazepin-7-one (3.2 g, 84%) as a brown oil. LCMS (ESI) [M+H]$^+$=258.1.

Examples I.19

Intermediate 19: 2-bromo-6-isopropyl-4-methylene-5,6-dihydro-4H-pyrazolo[1,5-d][1,4]diazepin-7(8H)-one

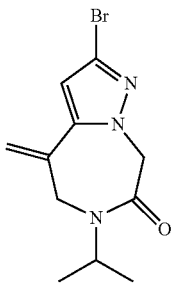 [SMILES: C=C1CN(C(C)C)C(=O)Cn2nc(Br)cc21]

To a mixture of N-allyl-2-(3,5-dibromopyrazol-1-yl)-N-isopropyl-acetamide (6.3 g, 17.26 mmol), palladium diacetate (386.5 mg, 1.73 mmol), triphenylphosphine (904.29 mg, 3.45 mmol) and tetrabutylammonium bromide (5.56 g, 17.26 mmol) in N,N-dimethylformamide (150 mL) was added potassium acetate (4.87 g, 51.77 mmol) at 25° C. The resulting mixture was stirred for 12 hours at 90° C. The reaction mixture was diluted with ethyl acetate and then washed with water. The organic layer was dried over anhydrous sodium sulfate, filtered and concentrated under vacuum. The residue was purified by flash chromatography on silica gel eluting with ethyl acetate/petroleum ether (2/3) to afford 2-bromo-6-isopropyl-4-methylene-5,8-dihydropyrazolo[1,5-d][1,4]diazepin-7-one (2.34 g, 8.23 mmol, 47.7% yield) as a yellow solid. LCMS (ESI) [M+H]$^+$=284.

Examples I.20

Intermediate 20: 2'-bromo-6'-methyl-5',6'-dihydrospiro[cyclopropane-1,4'-pyrazolo[1,5-d][1,4]diazepin]-7'(8'H)-one

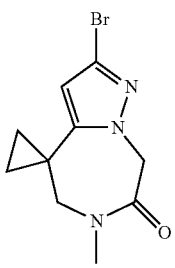

A mixture of trimethylsulfoxonium iodide (1.29 g, 5.86 mmol) and potassium tert-butoxide (656 mg, 5.85 mmol) in dimethyl sulfoxide (30 mL) was stirred for 30 min at room temperature. Then a solution of 2-bromo-6-methyl-4-methylidene-4H,5H,6H,7H,8H-pyrazolo[1,5-d][1,4]diazepin-7-one (500 mg, 1.95 mmol) in dimethyl sulfoxide (3 mL) was added. The mixture was then stirred for 12 h at 50° C. The reaction mixture was diluted with ethyl acetate and then washed with water. The organic layer was dried over anhydrous sodium sulfate, filtered and concentrated under vacuum. The residue was purified by silica gel column with dichloromethane/methanol (10/1) to afford 2'-bromo-6'-methyl-5',6'-dihydrospiro[cyclopropane-1,4'-pyrazolo[1,5-d][1,4]diazepin]-7'(8'H)-one (120 mg, 23%) as a white solid. LCMS (ESI) [M+H]$^+$=270.

Examples I.21

Intermediate 21: 2-bromo-6-methyl-5,6-dihydro-4H-pyrazolo[1,5-d][1,4]diazepin-7(8H)-one

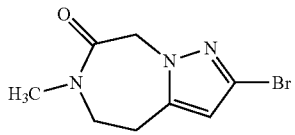

Step 1: Methyl 2-(3-bromo-5-methyl-pyrazol-1-yl)acetate

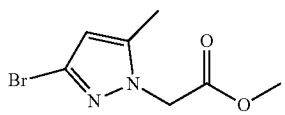

A solution of 3-bromo-5-methyl-1H-pyrazole (100 g, 621.12 mmol), methyl 2-chloroacetate (101.11 g, 931.68 mmol) and K$_2$CO$_3$ (154.29 g, 1118 mmol) in N,N-dimethylformamide (1 L) was added TBAI (11.46 g, 31.06 mmol). The resulting solution was stirred for 12 h at 20° C. The reaction mixture was diluted with EA (5000 mL). The solution was washed with water (300 mL×3) and the organic layers were combined. The organic layer was dried over anhydrous sodium sulfate and concentrated under vacuum. The residue was purified by flash chromatography on silica gel eluting with PE/DCM (60/40) to afford methyl 2-(3-bromo-5-methyl-pyrazol-1-yl)acetate (120 g, 82.9% yield) as a white solid.

Step 2: Methyl 2-[3-bromo-5-(bromomethyl)pyrazol-1-yl]acetate

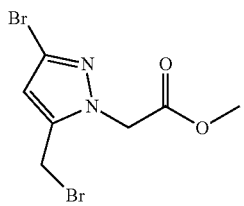

A solution of methyl 2-(3-bromo-5-methyl-pyrazol-1-yl)acetate (50.0 g, 214.54 mmol) and AIBN (3.52 g, 21.45 mmol) in carbon tetrachloride (1500 mL) was stirred at RT for 5 mins. 1-Bromo-2,5-pyrrolidinedione (40.09 g, 225.26 mmol) was added. The mixture was stirred at 80° C. for 1 hour. The reaction mixture was concentrated under vacuum. The residue was purified by flash chromatography on silica gel eluting with PE/EA (92/8) to afford methyl 2-[3-bromo-5-(bromomethyl)pyrazol-1-yl]acetate (35.5 g, 53% yield) as a white solid.

Step 3: Methyl 2-(3-bromo-5-(cyanomethyl)-1H-pyrazol-1-yl)acetate

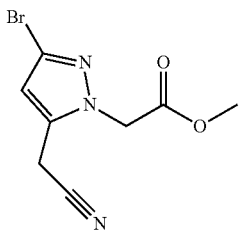

A solution of methyl 2-[3-bromo-5-(bromomethyl)pyrazol-1-yl]acetate (35.4 g, 113.48 mmol) and sodium cyanide (8.87 g, 181.02 mmol) in dimethyl sulfoxide (550 mL) was stirred at RT for 1 hour. The reaction solution was diluted with EA (2.5 L). The solution was washed with water (200 mL×5) and the organic layers were combined. The organic layer was dried over anhydrous sodium sulfate, filtered and concentrated under vacuum. The residue was purified by flash chromatography on silica gel eluting with DCM/MeOH (99/1) to afford methyl 2-(3-bromo-5-(cyanomethyl)-1H-pyrazol-1-yl)acetate (17.6 g, 60% yield) as a white solid.

Step 4: Methyl 2-(5-(2-aminoethyl)-3-bromo-1H-pyrazol-1-yl)acetate

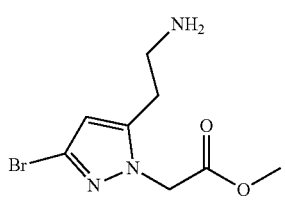

To a solution of methyl 2-[3-bromo-5-(cyanomethyl)pyrazol-1-yl]acetate (3.0 g, 11.62 mmol) in methanol (600 mL) was added PtO$_2$ (600 mg, 2.64 mmol). The mixture was stirred under 10 atm of hydrogen gas at 25° C. for 15 hours. The mixture was filtered. The filtrate would be directly used in the next step without purification.

Step 5: 2-bromo-4,5,6,8-tetrahydropyrazolo[1,5-d][1,4]diazepin-7-one

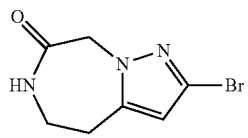 [SMILES: O=C1Cn2nc(Br)cc2CCN1]

To a solution (600 mL) of methyl 2-[5-(2-aminoethyl)-3-bromo-pyrazol-1-yl]acetate was added TEA (70 mL). The mixture was stirred at 25° C. for 15 hours. The resulting solution was concentrated under vacuum. The residue was purified by flash chromatography on silica gel eluting with DCM/MeOH (98/2) to afford 2-bromo-4,5,6,8-tetrahydro-pyrazolo[1,5-d][1,4]diazepin-7-one (1.12 g, 41.9% yield in two steps) as a white solid.

Step 6: 2-bromo-6-methyl-5,6-dihydro-4H-pyrazolo[1,5-d][1,4]diazepin-7(8H)-one

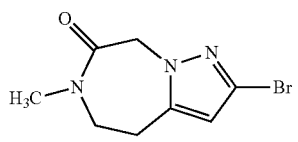

To a mixture of 2-bromo-5,6,7,8-tetrahydro-4H-pyrazolo[1,5-d][1,4]diazepine (469.53 mg, 2.17 mmol) and potassium tert-butoxide (365.74 mg, 3.26 mmol) in tetrahydrofuran (20 mL) was added iodomethane (616.86 mg, 4.35 mmol) at 20° C. The resulting solution was stirred at 20° C. for 1 h. The mixture was concentrated under vacuum. The residue was purified by flash chromatography on silica gel eluting with dichloromethane/methanol (20/1) to afford 2-bromo-6-methyl-4,5,7,8-tetrahydropyrazolo[1,5-d][1,4]diazepine (400 mg, 1.74 mmol, 80% yield). LCMS (ESI) [M+H]$^+$=244

Examples I.22

Intermediate 22: 2-bromo-6-isopropyl-5,6-dihydro-4H-pyrazolo[1,5-d][1,4]diazepin-7(8H)-one

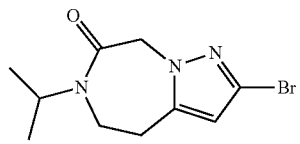

A solution of 2-bromo-4,5,6,8-tetrahydropyrazolo[1,5-d][1,4]diazepin-7-one (3.0 g, 13.04 mmol) and NaH (1.56 g, 39.12 mmol) in N,N-dimethylformamide (75 mL) was stirred at 0° C. for 10 min. Then 2-iodopropane (11.08 g, 65.2 mmol) was added. The mixture was stirred at 25° C. for 1 hour. The reaction was quenched with water. The mixture was concentrated under vacuum. The resulting residue was purified by reverse phase chromatography (acetonitrile 0-40/ 0.1% NH$_4$HCO$_3$ in water) to afford 2-bromo-6-isopropyl-5, 8-dihydro-4H-pyrazolo[1,5-d][1,4]diazepin-7-one (2.1 g, 7.7166 mmol, 59.2% yield) as a white solid. LCMS (ESI) [M+H]$^+$=272.

Examples I.23

Intermediate 23: 8-bromo-5,6-dihydro-11H-imidazo [1,2-a]pyrazolo[1,5-d][1,4]diazepine

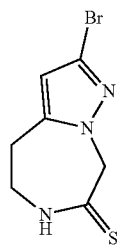

Step 1: 2-bromo-4,5,6,8-tetrahydropyrazolo[1,5-d] [1,4]diazepine-7-thione

A mixture of 2-bromo-4,5,6,8-tetrahydropyrazolo[1,5-d] [1,4]diazepin-7-one (314 mg, 1.36 mmol) and Lawsson reagent (551.4 mg, 1.36 mmol) in 1,4-dioxane (10 mL) was stirred at 90° C. for 1 h. The reaction was concentrated under vacuum. The residue was purified by flash chromatography on silica gel eluting with dichloromethane/methanol (96/4) to afford 2-bromo-4,5,6,8-tetrahydropyrazolo[1,5-d][1,4]diazepine-7-thione (265 mg, 78.9%) as a white solid. LCMS (ESI) [M+H]$^+$=246.0.

Step 2: 2-bromo-N-(2,2-diethoxyethyl)-5,8-dihydro-4H-pyrazolo[1,5-d][1,4]diazepin-7-amine

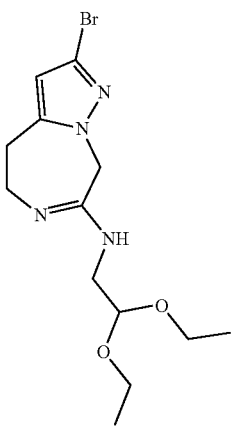 [SMILES: CCOC(CNC1=NCCc2cc(Br)nn2C1)OCC]

A mixture of 2-bromo-5,6-dihydro-4H-pyrazolo[1,5-d][1, 4]diazepine-7(8H)-thione (265.0 mg, 1.07 mmol), 2,2-diethoxyethan-1-amine (1.42 g, 10.7 mmol) and silver carbonate (590 mg, 2.14 mmol) in tetrahydrofuran (10 mL) was stirred at 80° C. for 1 h. The solvent was concentrated under vacuum. The residue was purified by reverse-phase column eluting with water (0.05% TFA)/CH$_3$CN (85/15) to afford 2-bromo-N-(2,2-diethoxyethyl)-5,8-dihydro-4H-pyrazolo [1,5-d][1,4]diazepin-7-amine (295 mg, 80%) as a brown oil. LCMS (ESI) [M+H]$^+$=345.0.

Step 3: 8-bromo-5,6-dihydro-11H-imidazo[1,2-a] pyrazolo[1,5-d][1,4]diazepine

A solution of 2-bromo-N-(2,2-diethoxyethyl)-5,8-dihydro-4H-pyrazolo[1,5-d][1,4]diazepin-7-amine (228 mg, 0.66 mmol) and concentrated hydrochloric acid (0.17 mL, 0.66 mmol) in acetic acid (5 mL) was stirred at 80° C. for 1 h. The reaction was concentrated under vacuum. The residue was purified by reverse-phase column eluting with water (0.05% TFA)/ACN (85/15) to afford 8-bromo-5,6-dihydro-11H-imidazo[1,2-a]pyrazolo[1,5-d][1,4]diazepine (150 mg, 89.7%) as a brown oil. LCMS (ESI) [M+H]$^+$=253.0.

EXEMPLARY COMPOUNDS

Example 1

(±)-trans-N-[8-amino-6-(4-cyano-2-methyl-phenyl)-3-isoquinolyl]-2-cyano-cyclopropanecarboxamide (Compound 1)

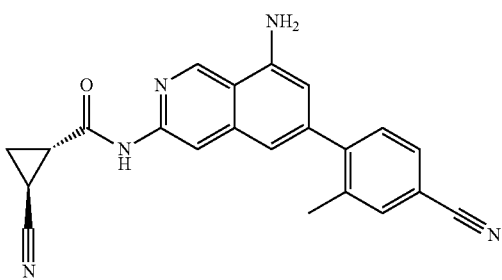

Step 1: (±)-trans-N-[8-chloro-6-(4-cyano-2-methyl-phenyl)-3-isoquinolyl]-2-cyano-cyclopropanecarboxamide

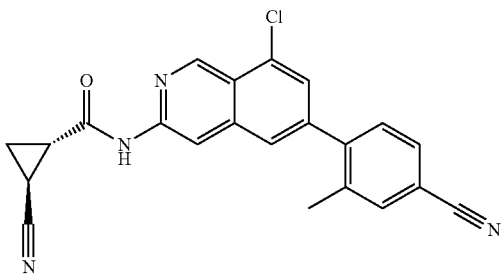 [SMILES: Cc1cc(C#N)ccc1-c1cc(Cl)c2cnc(NC(=O)[C@H]3C[C@@H]3C#N)cc2c1]

A mixture of (±)-trans-N-(6-bromo-8-chloro-3-isoquinolyl)-2-cyano-cyclopropanecarboxamide (350 mg, 1.0 mmol), 2-methyl-4-cyanophenylboronic acid (193 mg, 1.2 mmol), Pd(PPh$_3$)$_4$ (115 mg, 0.1 mmol) and Na$_2$CO$_3$ (212 mg, 2 mmol) in 1,4-dioxane (15 mL) and water (1 mL) under Ar was stirred at 90° C. for 3 hours. The mixture was concentrated and purified by column chromatography (ethyl acetate/hexane=1:3) to afford (±)-trans-N-[8-chloro-6-(4-cyano-2-methyl-phenyl)-3-isoquinolyl]-2-cyano-cyclopropanecarboxamide (380 mg, 86% yield) as a white solid. LCMS (ESI) [M+H]$^+$=387.1.

Step 2: (±)-trans-N-[8-(benzhydrylideneamino)-6-(4-cyano-2-methyl-phenyl)-3-isoquinolyl]-2-cyano-cyclopropanecarboxamide

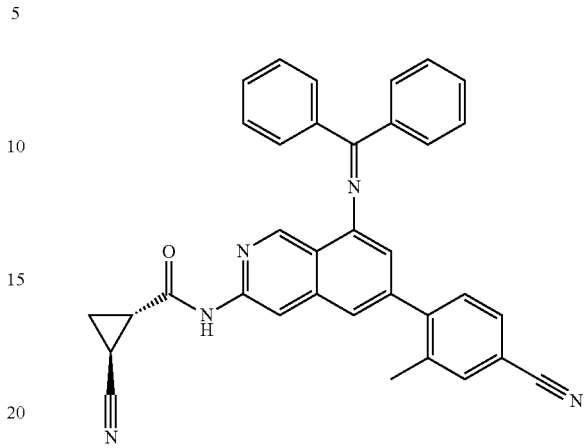

A mixture of (±)-trans-N-[8-chloro-6-(4-cyano-2-methyl-phenyl)-3-isoquinolyl]-2-cyano-cyclopropanecarboxamide (100 mg, 0.26 mmol), benzophenone imine (94 mg, 0.52 mmol), Pd(OAc)$_2$ (12 mg, 0.05 mmol), Xantphos (60 mg, 0.1 mmol) and Cs$_2$CO$_3$ (168 mg, 0.52 mmol) in DMF (6 mL) and toluene (6 mL) was stirred under Ar at 130° C. for 2.5 hours. Ethyl acetate (20 mL) was added. The mixture was washed with brine (3×50 mL), dried with Na$_2$SO$_4$, filtered and evaporated under reduced pressure. The residue was purified by column chromatography (ethyl acetate/hexane=1:3) to afford (±)-trans-N-[8-(benzhydrylideneamino)-6-(4-cyano-2-methyl-phenyl)-3-isoquinolyl]-2-cyano-cyclopropanecarboxamide (130 mg, 74% yield) as a yellow solid. LCMS (ESI) [M+H]$^+$=532.1.

Step 3: (±)-trans-N-[8-amino-6-(4-cyano-2-methyl-phenyl)-3-isoquinolyl]-2-cyano-cyclopropanecarboxamide

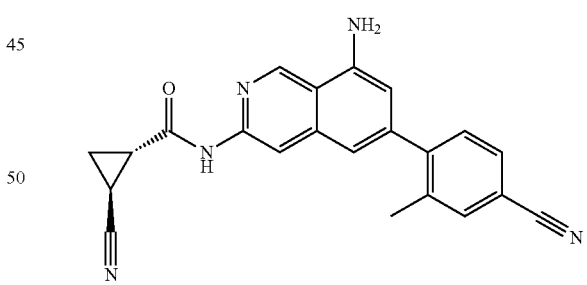

A mixture of (±)-trans-N-[8-(benzhydrylideneamino)-6-(4-cyano-2-methyl-phenyl)-3-isoquinolyl]-2-cyano-cyclopropanecarboxamide (130 mg, 0.19 mmol) in dichloromethane (10 mL), water (1 mL) and 2,2,2-trifluoroacetic acid (2 mL) was stirred at 25° C. for 1 hour. The reaction mixture was neutralized with NH$_4$OH (37% yield) to pH=7-8. The mixture was concentrated and purified by column chromatography (ethyl acetate/hexane=1:2) to afford (±)-trans-N-[8-amino-6-(4-cyano-2-methyl-phenyl)-3-isoquinolyl]-2-cyano-cyclopropanecarboxamide (65 mg, 93% yield) as a yellow solid. LCMS (ESI) R$_T$ (min)=1.842, [M+H]$^+$=368.1, method=C. $^1$H NMR (400 MHz, DMSO-d$_6$) δ 11.12 (s, 1H), 9.35 (s, 1H), 8.24 (s, 1H), 7.81 (s, 1H), 7.73 (d, J=8.0 Hz, 1H), 7.44 (d, J=8.0 Hz, 1H), 6.88 (s, 1H), 6.54 (d, J=1.2 Hz, 1H), 6.39 (s, 2H), 2.78-2.73 (m, 1H), 2.29 (s, 3H), 2.16-2.11 (m, 1H), 1.62-1.57 (m, 1H), 1.45-1.44 (m, 1H).

Example 2

N-(8-amino-6-(4-methylpyridin-3-yl)isoquinolin-3-yl)cyclopropanecarboxamide (Compound 2)

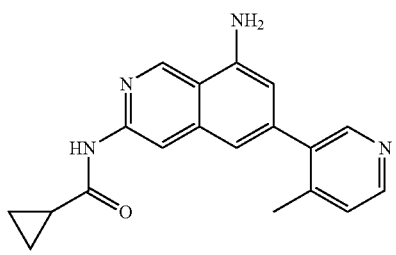 [SMILES: Cc1ccncc1-c1cc(N)c2cnc(NC(=O)C3CC3)cc2c1]

Step 1: N-[8-chloro-6-(4-methyl-3-pyridyl)-3-isoquinolyl]cyclopropanecarboxamide

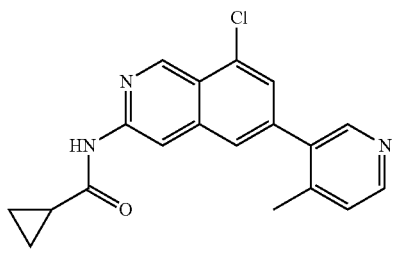 [SMILES: Cc1ccncc1-c1cc(Cl)c2cnc(NC(=O)C3CC3)cc2c1]

A mixture of N-(6-bromo-8-chloro-3-isoquinolyl)cyclopropanecarboxamide (270 mg, 0.83 mmol), 4-methyl-3-(4,4,5,5-tetramethyl-1,3,2-dioxaborolan-2-yl)pyridine (500 mg, 0.91 mmol), Pd(dppf)Cl₂ (121 mg, 0.17 mmol) and Na₂CO₃ (175 mg, 1.66 mmol) in 1,4-dioxane (5 mL) was heated in a glove box at 90° C. for 18 hours. The reaction was concentrated and purified by prep-TLC (petroleum ether:ethyl acetate=2:1) to give N-[8-chloro-6-(4-methyl-3-pyridyl)-3-isoquinolyl]cyclopropanecarboxamide (240 mg, 72% yield) as a white solid. LCMS (ESI) [M+H]⁺=338.0

Step 2: N-(8-amino-6-(4-methylpyridin-3-yl)isoquinolin-3-yl)cyclopropanecarboxamide

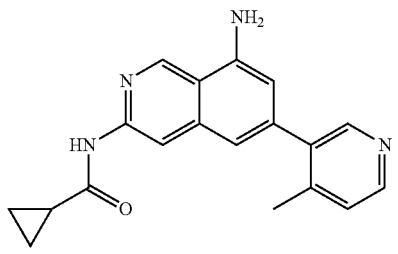 [SMILES: Cc1ccncc1-c1cc(N)c2cnc(NC(=O)C3CC3)cc2c1]

A mixture of N-[8-chloro-6-(4-methyl-3-pyridyl)-3-isoquinolyl]cyclopropanecarboxamide (120 mg, 0.36 mmol), benzophenone imine (77 mg, 0.43 mmol), Cs₂CO₃ (347 mg, 1.07 mmol), Pd(OAc)₂ (16 mg, 0.07 mmol) and XantPhos (41 mg, 0.07 mmol) in DMF (3 mL) and toluene (3 mL) was heated in a microwave at 150° C. for 3 hours. The mixture was filtered and concentrated. THF (5 mL) and HCl in 1,4-dioxane (4 M, 3 mL, 12 mmol) was added, followed by stirring at room temperature for 30 minutes. The mixture was filtered and concentrated. The crude product was purified by prep-HPLC to afford N-[8-amino-6-(4-methyl-3-pyridyl)-3-isoquinolyl]cyclopropane-carboxamide (21 mg, 18.6% yield) as a white solid. LCMS (ESI): R_T(min)=1.781, [M+H]⁺=319.2, method=C; ¹H NMR (400 MHz, DMSO-d₆) δ 10.78 (s, 1H), 9.31 (s, 1H), 8.44 (d, J=4.8 Hz, 1H), 8.40 (s, 1H), 8.26 (s, 1H), 7.34 (d, J=4.8 Hz, 1H), 6.88 (s, 1H), 6.54 (s, 1H), 6.33 (s, 2H), 2.29 (s, 3H), 2.07-2.04 (m, 1H), 0.83-0.80 (m, 4H).

Example 3

(±)-cis-N-[8-amino-6-[4-(hydroxymethyl)-3-pyridyl]-3-isoquinolyl]-2-fluoro-cyclopropanecarboxamide (Compound 3)

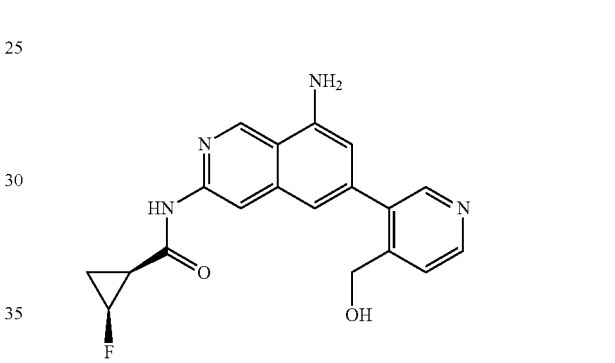

Step 1: (1)-cis-N-[8-chloro-6-[4-(hydroxymethyl)-3-pyridyl]-3-isoquinolyl]-2-fluoro-cyclopropanecarboxamide

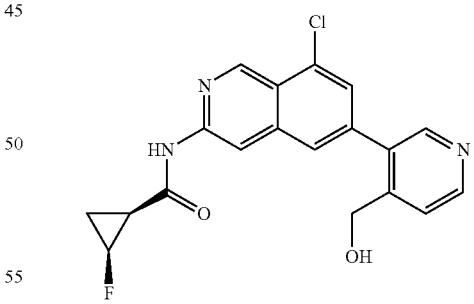

A mixture of (±)-cis-N-(6-bromo-8-chloro-3-isoquinolyl)-2-fluoro-cyclopropanecarboxamide (170 mg, 0.49 mmol), 1-hydroxy-3H-oxaborolo[3,4-c]pyridine (1 g, 7.41 mmol), PdCl₂dppf (150 mg, 0.21 mmol), K₂CO₃ (200 mg, 1.45 mmol) in 1,4-dioxane (16 mL) and water (4 mL) was stirred under Ar at 80° C. for 1 hour. The reaction mixture was cooled to room temperature, diluted with ethyl acetate (100 mL), and washed with brine (20 mL). The organic layer was separated, dried over Na₂SO₄, filtered and evaporated. The residue was purified by silica-gel column chromatography (petroleum ether/ethyl acetate=1:2) to afford (±)-cis-N-[8-chloro-6-[4-(hydroxymethyl)-3-pyridyl]-3-isoquinolyl]-2-fluoro-cyclopropanecarboxamide (140 mg, 77% yield) as a light brown solid. LCMS (ESI) [M+H]⁺=372.0.

Step 2: (±)-cis-N-[6-[4-[[tert-butyl(dimethyl)silyl]oxymethyl]-3-pyridyl]-8-chloro-3-isoquinolyl]-2-fluoro-cyclopropanecarboxamide

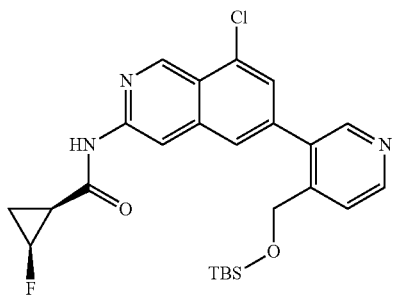

A mixture of (±)-cis-N-[8-chloro-6-[4-(hydroxymethyl)-3-pyridyl]-3-isoquinolyl]-2-fluoro-cyclopropanecarboxamide (140 mg, 0.38 mmol), tert-butyldimethylchlorosilane (500 mg, 3.32 mmol), triethylamine (600 mg, 5.94 mmol) in dichloromethane (15 mL) was refluxed overnight. The reaction mixture was concentrated and the resulting residue was purified with silica-gel column chromatography (petroleum ether/EA=2:1 to 1:1) to afford (±)-cis-N-[6-[4-[[tert-butyl(dimethyl)silyl] oxymethyl]-3-pyridyl]-8-chloro-3-isoquinolyl]-2-fluoro-cyclopropanecarboxamide (110 mg, 59% yield) as a light brown solid. LCMS (ESI) [M+H]⁺=486.2.

Step 3: (±)-tert-butyl N-[6-[4-[[tert-butyl(dimethyl)silyl]oxymethyl]-3-pyridyl]-3-[(cis-2-fluorocyclopropanecarbonyl)amino]-8-isoquinolyl]carbamate

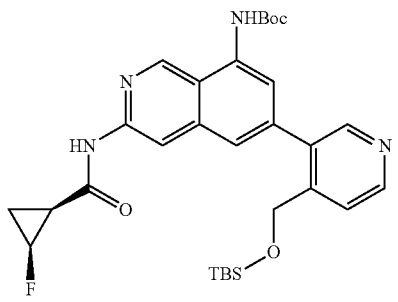

A mixture of (±)-cis-N-[6-[4-[[tert-butyl(dimethyl)silyl] oxymethyl]-3-pyridyl]-8-chloro-3-isoquinolyl]-2-fluoro-cyclopropanecarboxamide (95 mg, 0.20 mmol), BocNH₂ (300 mg, 2.56 mmol), Pd₂dba₃ (40 mg, 0.04 mmol), BrettPhos (40 mg, 0.07 mmol), t-BuONa (40 mg, 0.42 mmol) in 1,4-dioxane (10 mL) was stirred under Ar at 90° C. for 1 hour. The reaction mixture was cooled to room temperature, diluted with ethyl acetate (100 mL), and washed with sat. NH₄Cl (20 mL). Organic layer was separated, dried over Na₂SO₄, filtered and evaporated. The residue was purified by silica-gel column chromatography (petroleum ether/ethyl acetate=1:1 to 1:2) to afford (±)-tert-butyl N-[6-[4-[[tert-butyl(dimethyl)silyl]oxymethyl]-3-pyridyl]-3-[(cis-2-fluorocyclopropanecarbonyl) amino]-8-isoquinolyl]carbamate (35 mg, 31% yield) as a light yellow solid. LCMS (ESI) [M+H]⁺=567.3.

Step 4: (±)-cis-N-[8-amino-6-[4-(hydroxymethyl)-3-pyridyl]-3-isoquinolyl]-2-fluoro-cyclopropanecarboxamide

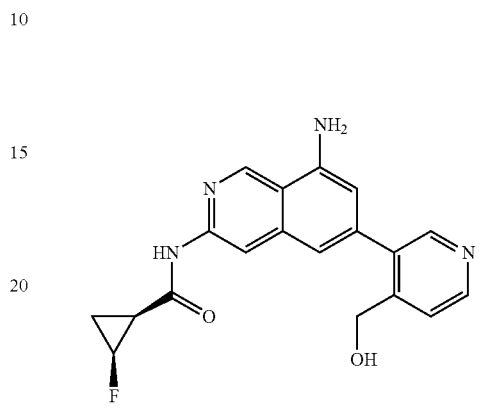

A mixture of (±)-tert-butyl N-[6-[4-[[tert-butyl(dimethyl)silyl]oxymethyl]-3-pyridyl]-3-[(cis-2-fluorocyclopropanecarbonyl)amino]-8-isoquinolyl]carbamate (35 mg, 0.062 mmol) in methanol (2 mL) and 4N HCl-dioxane (2 mL, 8 mmol) was stirred at 30° C. for 2 hours. The reaction mixture was concentrated. The residue was dissolved in methanol (1 mL), the pH adjusted by adding 7N NH₃/methanol until pH=9-10 was obtained, and concentrated. The crude product was purified by flash chromatography (Cis, NH₄HCO₃/methanol/water) to afford (±)-cis-N-[8-amino-6-[4-(hydroxymethyl)-3-pyridyl]-3-isoquinolyl]-2-fluoro-cyclopropanecarboxamide (11 mg, 50% yield) was as a light brown solid. LCMS (ESI): R$_T$ (min)=1.216, [M+H]⁺=353.1, method=A; ¹H NMR (400 MHz, CD₃OD) δ 9.25 (s, 1H), 8.57 (d, J=5.2 Hz, 1H), 8.43 (s, 1H), 8.33 (s, 1H), 7.74 (d, J=5.2 Hz, 1H), 7.02 (s, 1H), 6.67 (d, J=1.6 Hz, 1H), 4.99-4.95 (m, 0.5H), 4.83-4.79 (m, 0.5H), 4.67 (s, 2H), 2.18-2.13 (m, 1H), 1.88-1.77 (m, 1H), 1.27-1.18 (m, 1H).

Example 4

N-(8-amino-7-fluoro-6-(4-methylpyridin-3-yl)isoquinolin-3-yl)cyclopropanecarboxamide (Compound 4)

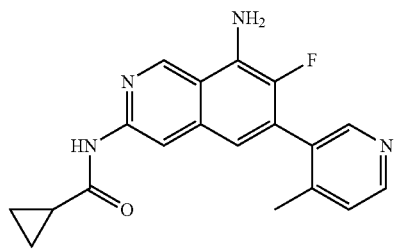

Step 1: N-(8-chloro-7-fluoro-6-iodoisoquinolin-3-yl)cyclopropanecarboxamide

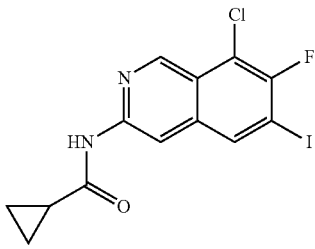 [SMILES: O=C(Nc1cc2cc(I)c(F)c(Cl)c2cn1)C1CC1]

To a solution of 8-chloro-7-fluoro-6-iodoisoquinolin-3-amine (0.25 g, 0.78 mmol) in dichloromethane (25 mL) was added pyridine (3 mL) and cyclopropanecarbonyl chloride (0.3 g, 2.84 mmol). The mixture was stirred at 25° C. for 3 hours. The solution was concentrated. The residue was purified by flash column chromatography (30% ethyl acetate in petroleum ether) to give N-(8-chloro-7-fluoro-6-iodoisoquinolin-3-yl)cyclopropanecarboxamide (35 mg) as a yellow solid. LCMS (ESI) [M+H]$^+$=390.9.

Step 2: N-(8-chloro-7-fluoro-6-(4-methylpyridin-3-yl)isoquinolin-3-yl)cyclopropanecarboxamide

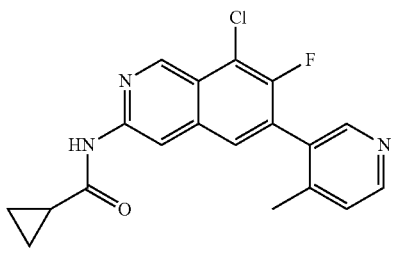

To a solution of N-(8-chloro-7-fluoro-6-iodoisoquinolin-3-yl)cyclopropanecarboxamide (35 mg, 0.09 mmol) and 4-methylpyridine-3-boronic acid (13 mg, 0.1 mmol) in water (2 mL) and THF (5 mL) was added Na$_2$CO$_3$ (27 mg, 0.25 mmol) and Pd(dppf)Cl$_2$ (7 mg, 0.01 mmol). The solution was stirred at 65° C. for 3 hours. After cooling, the organic layer was concentrated. The crude was then purified by flash column chromatography (50% ethyl acetate in petroleum ether) to give N-(8-chloro-7-fluoro-6-(4-methylpyridin-3-yl)isoquinolin-3-yl)cyclopropanecarboxamide (20 mg, 63% yield) as a yellow solid. LCMS (ESI) [M+H]$^+$=356.1.

Step 3: N-(8-amino-7-fluoro-6-(4-methylpyridin-3-yl)isoquinolin-3-yl)cyclopropanecarboxamide

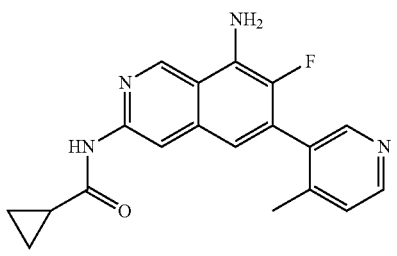 [SMILES: Cc1ccncc1-c1cc2cc(NC(=O)C3CC3)ncc2c(N)c1F]

A mixture of N-(8-chloro-7-fluoro-6-(4-methylpyridin-3-yl)isoquinolin-3-yl)cyclopropanecarboxamide (20 mg, 0.06 mmol), benzophenone imine (15 mg, 0.08 mmol), Pd(OAc)$_2$ (3 mg, 0.01 mmol), Xantphos (5 mg, 0.01 mmol), Cs$_2$CO$_3$ (51 mg, 0.16 mmol), DMF (3 mL) and toluene (1 mL) was heated in a microwave reactor at 145° C. for 1 hour. Water (10 mL) was added. The mixture was extracted with ethyl acetate (10 mL×3). The organic layer was washed with water (30 mL×3), dried over Na$_2$SO$_4$, filtered and concentrated. The residue was re-dissolved in a solution of HCl in 1,4-dioxane (0.73 mL, 4 M, 2.93 mmol) and the mixture was stirred at room temperature for 12 hours. The solution was concentrated. The residue was washed with a mixture of 10 mL petroleum ether and 5 mL of ethyl acetate. The crude was purified by reverse phase prep-HPLC to give N-(8-amino-7-fluoro-6-(4-methylpyridin-3-yl)isoquinolin-3-yl)cyclopropanecarboxamide (3 mg, 16% yield) as a yellow solid. LCMS (ESI): R$_T$ (min)=1.819, [M+H]$^+$=337.0, method=C; $^1$H NMR (400 MHz, CDCl$_3$) δ 9.05 (s, 1H), 8.54 (d, J=4.8 Hz, 1H), 8.48 (s, 2H), 8.26 (s, 1H), 7.26 (d, J=7.2 Hz, 1H), 7.06 (d, J=6.4 Hz, 1H), 4.45 (bs, 2H), 2.26 (s, 3H), 1.63-1.60 (m, 1H), 1.16-1.14 (m, 2H), 0.94-0.92 (m, 2H).

Example 5

N-(8-amino-7-cyano-6-(4-methylpyridin-3-yl)isoquinolin-3-yl)cyclopropanecarboxamide (Compound 5)

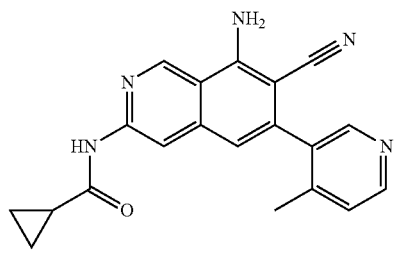 [SMILES: Cc1ccncc1-c1cc2cc(NC(=O)C3CC3)ncc2c(N)c1C#N]

Step 1: N-(7-bromo-8-chloro-6-iodoisoquinolin-3-yl)cyclopropanecarboxamide

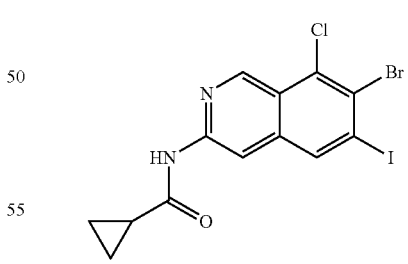

To a solution of 7-bromo-8-chloro-6-iodoisoquinolin-3-amine (3 g, 7.82 mmol) in dichloromethane (25 mL) was added pyridine (3 mL) and cyclopropanecarbonyl chloride (3 g, 28.7 mmol). The solution was stirred at 25° C. for 3 hours. The solution was concentrated. The residue was purified by flash column chromatography (5% methanol in dichloromethane) to give N-(7-bromo-8-chloro-6-iodoisoquinolin-3-yl)cyclopropanecarboxamide (1.2 g, 34% yield) as a yellow solid. LCMS (ESI) [M+H]$^+$=450.9.

Step 2: N-(7-bromo-8-chloro-6-(4-methylpyridin-3-yl)isoquinolin-3-yl)cyclopropanecarboxamide

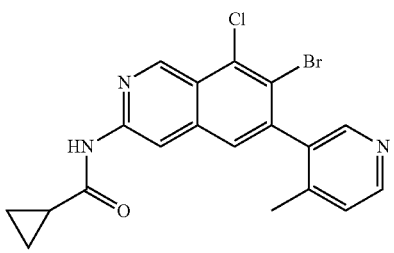 [SMILES: Cc1ccncc1-c1cc2cc(NC(=O)C3CC3)ncc2c(Cl)c1Br]

To a mixture of N-(7-bromo-8-chloro-6-iodoisoquinolin-3-yl)cyclopropanecarboxamide (300 mg, 0.66 mmol) and 4-methylpyridine-3-boronic acid (100 mg, 0.73 mmol) in water (2 mL) and THF (5 mL) was added Na$_2$CO$_3$ (200 mg, 1.89 mmol) and Pd(dppf)Cl$_2$ (50 mg, 0.06 mmol). The mixture was stirred at 65° C. for 3 hours. After cooling, the organic layer was concentrated. The crude material was then purified by flash column chromatography (50% ethyl acetate in petroleum ether) to give N-(7-bromo-8-chloro-6-(4-methylpyridin-3-yl)isoquinolin-3yl)cyclopropanecarboxamide (110 mg, 40% yield) as a brown solid. LCMS (ESI) [M+H]$^+$=416.0. $^1$H NMR (400 MHz, DMSO-d$_6$): δ 11.21 (s, 1H), 9.43 (s, 1H), 8.55-8.53 (m, 2H), 8.37 (s, 1H), 7.94 (s, 1H), 7.42 (d, J=5.2 Hz, 1H), 2.10-2.07 (m, 4H), 0.86-0.85 (m, 4H).

Step 3: N-(8-chloro-7-cyano-6-(4-methylpyridin-3-yl)isoquinolin-3-yl)cyclopropanecarboxamide

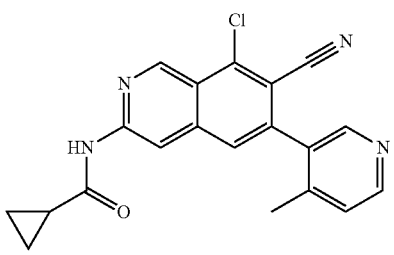 [SMILES: Cc1ccncc1-c1cc2cc(NC(=O)C3CC3)ncc2c(Cl)c1C#N]

A mixture of N-(7-bromo-8-chloro-6-(4-methylpyridin-3-yl)isoquinolin-3yl)cyclopropanecarboxamide (300 mg, 0.72 mmol) and CuCN (300 mg, 3.33 mmol) in 1-methyl-2-pyrrolidinone (3 mL) was heated in a microwave reactor at 200° C. for 1 hour. The mixture was diluted with ethyl acetate (10 mL) to give a brown precipitate. The mixture was filtered and concentrated. The residue was diluted with ammonium hydroxide (5 mL) and stirred at room temperature for 1 hour. The mixture was extracted with dichloromethane (30 mL×2) and washed with water (20 mL×2). The organic layer was concentrated and purified by prep-HPLC to give N-(8-chloro-7-cyano-6-(4-methylpyridin-3-yl)isoquinolin-3-yl)cyclopropanecarboxamide (120 mg, 46% yield) as a yellow solid. LCMS (ESI) [M+H]$^+$=363.1. $^1$H NMR (400 MHz, CDCl$_3$): δ 9.48 (s, 1H), 8.62-8.61 (m, 2H), 8.47 (s, 1H), 8.40 (s, 1H), 7.64 (s, 1H), 7.31 (d, J=4.8 Hz, 1H), 2.27 (s, 3H), 1.68-1.62 (m, 1H), 1.19-1.15 (m, 2H), 1.01-0.98 (m, 2H).

Step 4: N-(8-amino-7-cyano-6-(4-methylpyridin-3-yl)isoquinolin-3-yl)cyclopropanecarboxamide

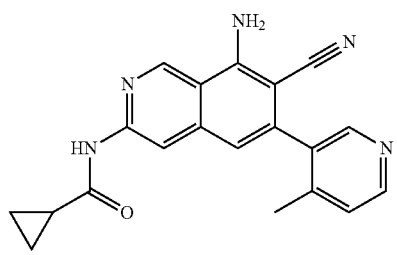 [SMILES: Cc1ccncc1-c1cc2cc(NC(=O)C3CC3)ncc2c(N)c1C#N]

A mixture of N-(8-chloro-7-cyano-6-(4-methylpyridin-3-yl)isoquinolin-3-yl)cyclopropanecarboxamide (20 mg, 0.06 mmol), benzophenoneimine (15 mg, 0.08 mmol), Pd(OAc)$_2$ (3 mg, 0.01 mmol), Xantphos (5 mg, 0.01 mmol), Cs$_2$CO$_3$ (50 mg, 0.15 mmol), DMF (3 mL) and toluene (1 mL) were added to a reaction tube in a glove box. The reaction was then sealed and heated in a microwave reactor at 145° C. for 1 hour. Water (10 mL) was added. The mixture was extracted with ethyl acetate (10 mL×3). The organic layer was washed with water (30 mL×3), dried over Na$_2$SO$_4$, filtered and concentrated. The residue was re-dissolved in a solution of HCl in 1,4-dioxane (0.72 mL, 4 M, 2.87 mmol). The mixture was stirred at room temperature for 12 hours. The solution was concentrated, washed with a mixture of 10 mL petroleum ether and 5 mL of ethyl acetate. The residue was purified by prep-HPLC to give N-(8-amino-7-cyano-6-(4-methylpyridin-3-yl)isoquinolin-3-yl)cyclopropanecarboxamide (4 mg, 21% yield) as a white solid. LCMS (ESI): R$_T$ (min)=1.688, [M+H]$^+$=344.1, method=F; $^1$H NMR (400 MHz, CDCl$_3$) δ 9.04 (s, 1H), 8.55 (d, J=5.2 Hz, 1H), 8.47 (s, 1H), 8.46 (s, 1H), 8.25 (s, 1H), 7.27 (d, J=5.2 Hz, 1H), 6.99 (s, 1H), 5.43 (bs, 2H), 2.28 (s, 3H), 1.60-1.57 (m, 1H), 1.17-1.15 (m, 2H), 0.97-0.96 (m, 2H).

Example 6

N-(8-amino-7-cyano-6-(1-methyl-1H-pyrazol-4-yl)isoquinolin-3-yl) cyclopropanecarboxamide (Compound 6)

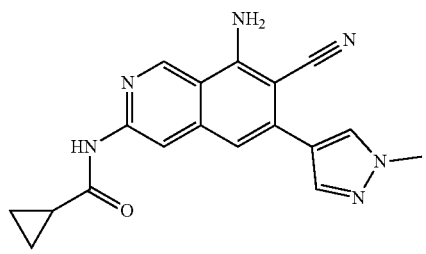 [SMILES: Cn1cc(-c2cc3cc(NC(=O)C4CC4)ncc3c(N)c2C#N)cn1]

Step 1: N-(7-bromo-8-chloro-6-(1-methyl-1H-pyrazol-4-yl)isoquinolin-3-yl)cyclopropanecarboxamide

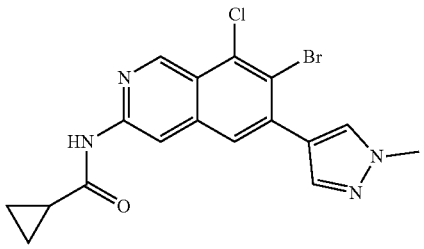 [SMILES: Cn1cc(-c2cc3cc(NC(=O)C4CC4)ncc3c(Cl)c2Br)cn1]

To a solution of N-(7-bromo-8-chloro-6-iodoisoquinolin-3-yl)cyclopropanecarboxamide (250 mg, 0.55 mmol), 1-methyl-4-(4,4,5,5-tetramethyl-1,3,2-dioxaborolan-2-yl)-1H-pyrazole (126 mg, 0.61 mmol) in water (3 mL) and THF (10 mL) was added Na$_2$CO$_3$ (166 mg, 1.57 mmol) and Pd(dppf)Cl$_2$ (41 mg, 0.05 mmol). The reaction solution was stirred under N$_2$ at 85° C. for 12 hours before being concentrated to dryness. The residue was taken up in ethyl acetate (10 mL), washed with water and brine, dried over MgSO$_4$ and concentrated. The crude was purified by flash column chromatography (50% ethyl acetate in petroleum ether) to give N-(7-bromo-8-chloro-6-(1-methyl-H-pyrazol-4-yl)isoquinolin-3-yl)cyclopropanecarboxamide (150 mg, 67% yield) as a yellow solid. LCMS (ESI): [M+H]$^+$=405.0.

Step 2: N-(8-chloro-7-cyano-6-(1-methyl-1H-pyrazol-4-yl)isoquinolin-3-yl)cyclopropanecarboxamide

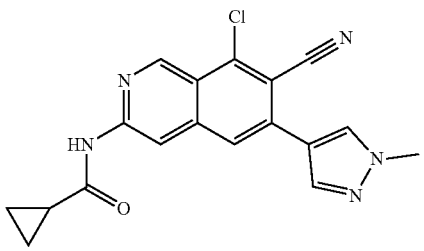 [SMILES: Cn1cc(-c2cc3cc(NC(=O)C4CC4)ncc3c(Cl)c2C#N)cn1]

A mixture of N-(7-bromo-8-chloro-6-(1-methyl-1H-pyrazol-4-yl)isoquinolin-3-yl)cyclopropanecarboxamide (150 mg, 0.37 mmol) and CuCN (154 mg, 1.71 mmol) in 1-methyl-2-pyrrolidinone (3 mL) was heated in a microwave reactor at 200° C. for 1 hour. The reaction mixture was diluted with ammonium hydroxide (5 mL) and stirred at room temperature for 1 hour. The mixture was extracted with dichloromethane (30 mL×2). The combined organic layers were washed with water (20 mL×2), dried and concentrated. The residue was purified by flash column chromatography (50% ethyl acetate in petroleum ether) to give N-(8-chloro-7-cyano-6-(1-methyl-1H-pyrazol-4-yl)isoquinolin-3-yl)cyclopropanecarboxamide (50 mg, 38% yield) as a yellow solid. LCMS (ESI): [M+H]$^+$=352.1.

Step 3: N-(8-amino-7-cyano-6-(1-methyl-1H-pyrazol-4-yl)isoquinolin-3-yl)cyclopropanecarboxamide

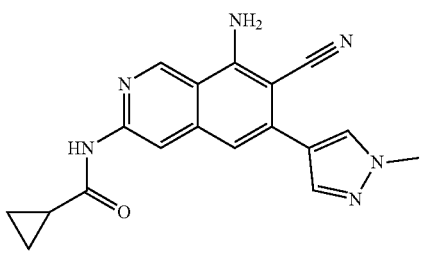

A mixture of N-(8-chloro-7-cyano-6-(1-methyl-1H-pyrazol-4-yl)isoquinolin-3-yl)cyclopropanecarboxamide (50 mg, 0.14 mmol), benzophenone (39 mg, 0.21 mmol), Pd(OAc)$_2$ (8 mg, 0.03 mmol), Xantphos (13 mg, 0.02 mmol), Cs$_2$CO$_3$ (129 mg, 0.4 mmol), DMF (3 mL) and toluene (1 mL) was added to a sealed tube in glove box. The resulting mixture was heated at 145° C. in microwave reactor for 1 hour. Water (10 mL) was added. The mixture was extracted with ethyl acetate (10 mL×3). The combined organic layer was washed with water (30 mL×3), dried over Na$_2$SO$_4$, filtered and concentrated. The residue was dissolved in a solution of HCl in 1,4-dioxane (1.85 mL, 4M, 7.41 mmol). The mixture was stirred at room temperature for 13 hours. The reaction solution was concentrated, washed with a mixture of 10 mL petroleum ether and 5 mL of ethyl acetate. The residue was purified by prep-HPLC to give N-(8-amino-7-cyano-6-(1-methyl-1H-pyrazol-4-yl)isoquinolin-3-yl)cyclopropanecarboxamide (5 mg, 11% yield) as a yellow solid. LCMS (ESI): R$_T$(min)=1.724, [M+H]$^+$=333.1, method=H; $^1$H NMR (400 MHz, CD$_3$OD) δ 9.27 (s, 1H), 8.28 (s, 1H), 8.18 (s, 1H), 8.00 (s, 1H), 7.12 (s, 1H), 4.00 (s, 3H), 1.33-1.32 (m, 1H), 1.04-1.03 (m, 2H), 0.95-0.92 (m, 2H).

Example 7

(±)-[8-amino-3-[(cis-2-fluorocyclopropanecarbonyl)amino]-6-isoquinolyl]-N,4-dimethyl-pyrimidine-2-carboxamide (Compound 13)

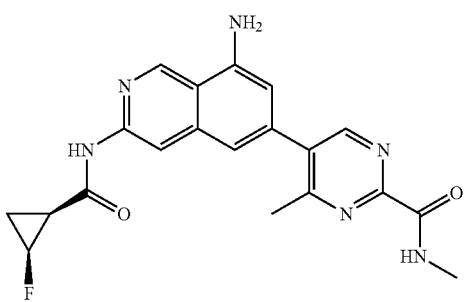 [SMILES: CNC(=O)c1ncc(-c2cc(N)c3cnc(NC(=O)[C@@H]4C[C@@H]4F)cc3c2)c(C)n1]

Step 1: 5-bromo-2-chloro-4-methyl-pyrimidine

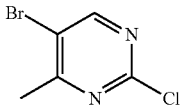

Tert-butyl nitrite (16 g, 155 mmol) was added dropwise to a mixture of 5-bromo-4-methyl-2-pyrimidinylamine (5 g, 26.59 mmol), and benzyltriethylammoniumchloride (27 g, 118.54 mmol) in dichloromethane (200 mL). The reaction mixture was stirred at 25° C. for 2 hours. The reaction mixture was diluted with $H_2O$ (50 mL), neutralized with sat. $NaHCO_3$ and extracted with dichloromethane (300 mL×3). All of the dichloromethane layers were combined, dried over $Na_2SO_4$, filtered and evaporated. The residue was purified by silica-gel column chromatography (petroleum ether/ethyl acetate=10:1) to give 5-bromo-2-chloro-4-methyl-pyrimidine (2.5 g, 45% yield) as a white solid. LCMS (ESI) $[M+H]^+=208.9$.

Step 2: 5-bromo-4-methyl-pyrimidine-2-carbonitrile

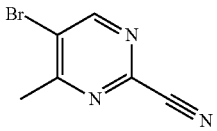

A mixture of 5-bromo-2-chloro-4-methylpyrimidine (2.5 g, 12.08 mmol), sodium cyanide (600 mg, 12.24 mmol), and DABCO (500 mg, 4.46 mmol) in dimethyl sulfoxide (40 mL) and water (40 mL) was stirred overnight. The reaction mixture was diluted with $H_2O$ (100 mL) and extracted with ethyl acetate (80 mL×3). The ethyl acetate layers were combined, washed with brine (50 mL×2), dried over $Na_2SO_4$, filtered and concentrated. The residue was purified with silica-gel column chromatography (petroleum ether/ethyl acetate=10:1) to give 5-bromo-4-methyl-pyrimidine-2-carbonitrile (1.75 g, 73% yield) as a light yellow solid. LCMS (ESI) $[M+H]^+=199.9$.

Step 3: Methyl 5-bromo-4-methyl-pyrimidine-2-carboxylate

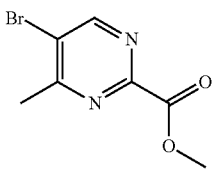

A mixture of 5-bromo-4-methyl-pyrimidine-2-carbonitrile (1.35 g, 6.82 mmol) in conc. HCl (20 mL) and methanol (20 mL) was refluxed for 2 hours. The reaction mixture was concentrated. The residue was diluted with water (20 mL), adjusted to pH 7 by adding sat. $NaHCO_3$ and extracted with ethyl acetate (30 mL×3). All of ethyl acetate layers were combined, dried over $Na_2SO_4$, filtered and concentrated. The residue was purified by silica-gel column chromatography (petroleum ether/ethyl acetate=1:1) to give methyl 5-bromo-4-methyl-pyrimidine-2-carboxylate (940 mg, 60% yield) as a white solid. LCMS (ESI) $[M+H]^+=233.0$.

Step 4: 5-bromo-4-methyl-pyrimidine-2-carboxylic Acid

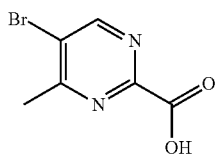

A mixture of methyl 5-bromo-4-methyl-pyrimidine-2-carboxylate (300 mg, 1.3 mmol) and LiOH monohydrate (160 mg, 3.81 mmol) in THF (5 mL) and water (5 mL) was stirred at 25° C. for 2 hours. The reaction mixture was concentrated to remove THF. The residue aqueous layer was diluted with water (20 mL) and washed with ethyl acetate (20 mL×2). The aqueous layer was acidified to pH 4-5 by adding conc. HCl. Sodium chloride was added until saturation and the product was then extracted with ethyl acetate (40 mL×5). The combined extracts were combined, dried over $Na_2SO_4$, filtered and evaporated. 5-bromo-4-methyl-pyrimidine-2-carboxylic acid (230 mg, 81% yield) as a white solid. LCMS (ESI) $[M+H]^+=219.0$.

Step 5: 5-bromo-N,4-dimethyl-pyrimidine-2-carboxamide

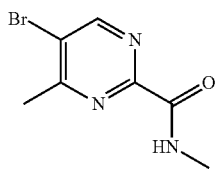

Oxalyl chloride (200 mg, 1.57 mmol) was added dropwise to a mixture of 5-bromo-4-methyl-pyrimidine-2-carboxylic acid (230 mg, 1.06 mmol) in DMF (0.1 mL) and dichloromethane (5 mL) at 0° C. The reaction mixture was stirred at 25° C. for 0.5 hours and concentrated. The residue was re-dissolved in dichloromethane (2 mL) and added dropwise to a solution of $CH_3NH_2$ (2M in THF, 2 mL, 4 mmol) and pyridine (0.51 mL, 6.33 mmol) in dichloromethane (5 mL) at 0° C. The reaction mixture was stirred at 25° C. for 1 hour and evaporated. The residue was purified with silica-gel column chromatography (dichloromethane/ethyl acetate=1:4) to give 5-bromo-N,4-dimethyl-pyrimidine-2-carboxamide (240 mg, 98% yield) as a white solid. LCMS (ESI) $[M+H]^+=230.0$.

427

Step 6: [4-methyl-2-(methylcarbamoyl)pyrimidin-5-yl]boronic Acid

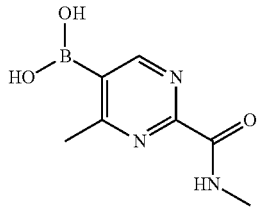

A mixture of bis(pinacolato)diboron (200 mg, 0.79 mmol), 5-bromo-N,4-dimethyl-pyrimidine-2-carboxamide (100 mg, 0.43 mmol), PdCl₂dppf (20 mg, 0.03 mmol), potassium acetate (120 mg, 1.22 mmol) in 1,4-dioxane (8 mL) was stirred under Ar at 80° C. overnight. The reaction mixture of [4-methyl-2-(methylcarbamoyl)pyrimidin-5-yl] boronic acid was used directly in next step. LCMS (ESI) [M+H]⁺=196.1.

Step 7: (±)-5-[8-chloro-3-[(cis-2-fluorocyclopropanecarbonyl)amino]-6-isoquinolyl]-N,4-dimethyl-pyrimidine-2-carboxamide

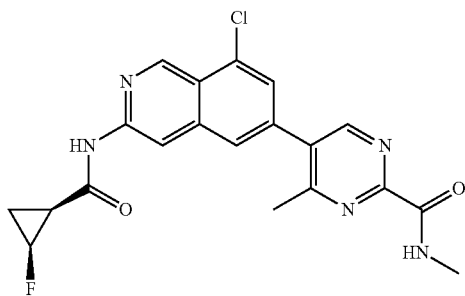 [SMILES: CNC(=O)c1ncc(-c2cc(Cl)c3cnc(NC(=O)[C@@H]4C[C@@H]4F)cc3c2)c(C)n1]

A mixture of (±)-cis-N-(6-bromo-8-chloro-3-isoquinolyl)-2-fluoro-cyclopropanecarboxamide (100 mg, 0.29 mmol), [4-methyl-2-(methylcarbamoyl)pyrimidin-5-yl]boronic acid (reaction mixture, about 8 mL, about 0.43 mmol), PdCl₂dppf (20 mg, 0.03 mmol), K₂CO₃ (120 mg, 0.87 mmol) and water (2 mL) was stirred under Ar at 80° C. for 2 hours. The reaction mixture was cooled to room temperature, diluted with ethyl acetate (100 mL) and washed with brine (30 mL). The organic layer was separated, dried over Na₂SO₄, filtered and concentrated. The residue was purified with silica gel column chromatography (petroleum ether/ethyl acetate=1:2) to give (±)-5-[8-chloro-3-[(cis-2-fluorocyclopropanecarbonyl)amino]-6-isoquinolyl]-N,4-dimethyl-pyrimidine-2-carboxamide (20 mg, 17% yield) as a light brown solid. LCMS (ESI) [M+H]⁺=414.0.

428

Step 8: (±)-5-[8-(benzhydrylideneamino)-3-[(cis-2-fluorocyclopropanecarbonyl)amino]-6-isoquinolyl]-N,4-dimethyl-pyrimidine-2-carboxamide

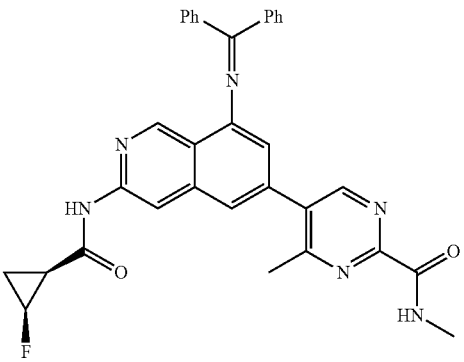 [SMILES: CNC(=O)c1ncc(-c2cc(N=C(c3ccccc3)c3ccccc3)c3cnc(NC(=O)[C@@H]4C[C@@H]4F)cc3c2)c(C)n1]

A mixture of (±)-5-[8-chloro-3-[(cis-2-fluorocyclopropanecarbonyl)amino]-6-isoquinolyl]-N,4-dimethyl-pyrimidine-2-carboxamide (20 mg, 0.048 mmol), benzophenone imine (80 mg, 0.44 mmol), Pd₂dba₃ (10 mg, 0.01 mmol), Xantphos (10 mg, 0.02 mmol), Cs₂CO₃ (40 mg, 0.12 mmol) in DMF (1 mL) and toluene (1 mL) was stirred under Ar at 130° C. for 1.5 hours. The reaction mixture was cooled to room temperature. The residue was diluted with ethyl acetate (80 mL) and washed with water (20 mL). The organic layer was separated, dried over Na₂SO₄, filtered and evaporated. The residue was purified with silica-gel column chromatography (petroleum ether/ethyl acetate=1:2 to dichloromethane/ethyl acetate=1:3) to give (±)-5-[8-(benzhydrylideneamino)-3-[(cis-2-fluorocyclopropanecarbonyl) amino]-6-isoquinolyl]-N,4-dimethyl-pyrimidine-2-carboxamide (12 mg, 44% yield) as a yellow solid. LCMS (ESI) [M+H]⁺=559.2.

Step 9: (±)-5-[8-amino-3-[(cis-2-fluorocyclopropanecarbonyl)amino]-6-isoquinolyl]-N,4-dimethyl-pyrimidine-2-carboxamide

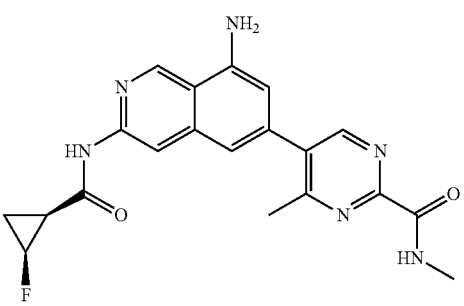 [SMILES: CNC(=O)c1ncc(-c2cc(N)c3cnc(NC(=O)[C@@H]4C[C@@H]4F)cc3c2)c(C)n1]

A mixture of (±)-5-[8-(benzhydrylideneamino)-3-[(cis-2-fluorocyclopropanecarbonyl)amino]-6-isoquinolyl]-N,4-dimethyl-pyrimidine-2-carboxamide (12 mg, 0.021 mmol) in water (0.1 ml), 2,2,2-trifluoroacetic acid (0.5 ml) and dichloromethane (3 ml) was stirred at 30° C. for 1 hour. The reaction mixture was evaporated. The residue was dissolved in methanol (1 mL), neutralized with 7N NH₃ in methanol until pH 9-10, and purified by flash chromatography (Cis, methanol/water to formic acid/methanol/water) to give the formic acid salt of (±)-5-[8-amino-3-[(cis-2-fluorocyclopropanecarbonyl)amino]-6-isoquinolyl]-N,4-dimethyl-pyrimidine-2-carboxamide (3.4 mg, 37% yield) as a yellow solid. LCMS (ESI): $R_T$ (min)=1.493, [M+H]$^+$=395.1, method=E; $^1$H NMR (400 MHz, CD$_3$OD) δ 9.27 (s, 1H), 8.77 (s, 1H), 8.52 (brs, 1H), 8.36 (s, 1H), 7.09 (s, 1H), 6.72 (s, 1H), 4.99-4.79 (m, 1H), 3.04 (s, 3H), 2.65 (s, 3H), 2.18-2.13 (m, 1H), 1.88-1.78 (m, 1H), 1.27-1.19 (m, 1H).

Example 8

(±)-cis-N-(8-amino-6-(6-methyl-1H-benzo[d]imidazol-5-yl)isoquinolin-3-yl)-2-fluorocyclopropanecarboxamide (Compound 14)

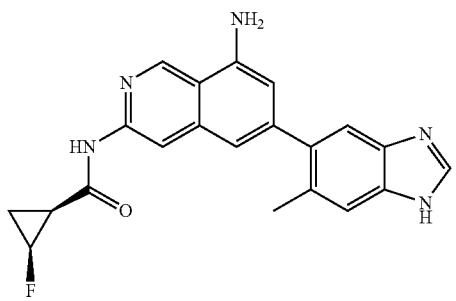 [SMILES: Cc1cc2[nH]cnc2cc1-c1cc(N)c2cnc(NC(=O)[C@@H]3C[C@@H]3F)cc2c1]

Step 1: (±)-tert-butyl 5-(8-chloro-3-(cis-2-fluorocyclopropanecarboxamido)isoquinolin-6-yl)-6-methyl-1H-benzo[d]imidazole-1-carboxylate

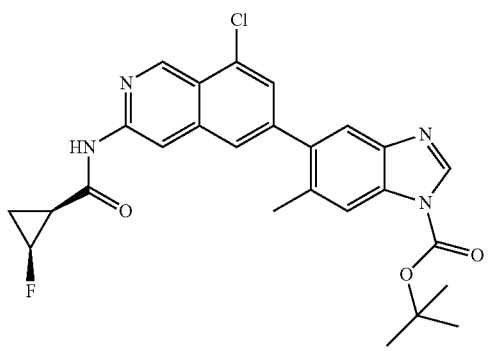 [SMILES: Cc1cc2c(cc1-c1cc(Cl)c3cnc(NC(=O)[C@@H]4C[C@@H]4F)cc3c1)ncn2C(=O)OC(C)(C)C]

A mixture of (±)-cis-N-(6-bromo-8-chloro-3-isoquinolyl)-2-fluoro-cyclopropanecarboxamide (80 mg, 0.23 mmol), tert-butyl 6-methyl-5-(4,4,5,5-tetramethyl-1,3,2-dioxaborolan-2-yl)benzimidazole-1-carboxylate (83 mg, 0.23 mmol), Pd(dppf)Cl$_2$ (17 mg, 0.02 mmol) and K$_2$CO$_3$ (96 mg, 0.70 mmol) in 1,4-dioxane (6 mL) and water (1 mL) was stirred at 90° C. for 4 hours. The reaction mixture was concentrated. The residue was purified by prep-TLC (normal phase silica gel, uv 254 nm, dichloromethane/methanol=30/1) to give (±)-tert-butyl 5-[8-chloro-3-[[cis-2-fluorocyclopropanecarbonyl]amino]-6-isoquinolyl]-6-methyl-benzimidazole-1-carboxylate (70 mg, 60% yield) as a yellow oil.

Step 2: (±)-cis-N-(8-amino-6-(6-methyl-1H-benzo[d]imidazol-5-yl)isoquinolin-3-yl)-2-fluorocyclopropanecarboxamide

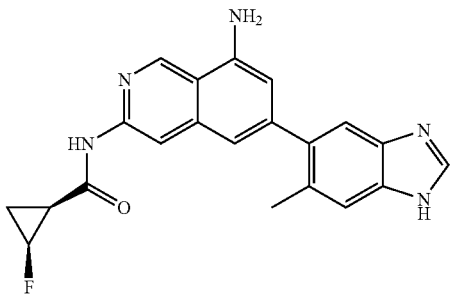 [SMILES: Cc1cc2[nH]cnc2cc1-c1cc(N)c2cnc(NC(=O)[C@@H]3C[C@@H]3F)cc2c1]

To a sealed tube was added (±)-tert-butyl 5-[8-chloro-3-[[cis-2-fluorocyclopropanecarbonyl]amino]-6-isoquinolyl]-6-methyl-benzimidazole-1-carboxylate (60 mg, 0.12 mmol), tert-butyl carbamate (142 mg, 1.21 mmol), Pd$_2$(dba)$_3$ (23 mg, 0.03 mmol), NaOtBu (34 mg, 0.36 mmol), tBuBrettPhos (13 mg, 0.03 mmol) and 1-methyl-2-pyrrolidinone (4 mL). The mixture was stirred at 110° C. for 2 hours. The reaction mixture was concentrated in vacuum. The residue was purified by reverse phase prep-HPLC to give (±)-cis-N-[8-amino-6-(6-methyl-1H-benzimidazol-5-yl)-3-isoquinolyl]-2-fluoro-cyclopropanecarboxamide (5 mg, 11% yield) as a white solid. LCMS (ESI): $R_T$ (min)=1.335, [M+H]$^+$=376.1, method=C; $^1$H NMR (400 MHz, CD$_3$OD) δ 9.23 (s, 1H), 8.30 (s, 1H), 8.16 (s, 1H), 7.59-7.47 (m, 2H), 7.03 (s, 1H), 6.76 (s, 1H), 4.99-4.78 (m, 1H), 2.40 (s, 3H), 2.20-2.12 (m, 1H), 1.87-1.76 (m, 1H), 1.27-1.17 (m, 1H).

Example 9

(±)-cis-N-(8-amino-6-(5-cyclopropylpyridazin-4-yl)isoquinolin-3-yl)-2-fluorocyclopropanecarboxamide (Compound 15)

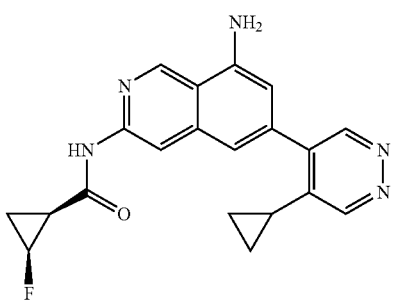 [SMILES: Nc1cc(-c2cnncc2C2CC2)cc2cc(NC(=O)[C@@H]3C[C@@H]3F)ncc12]

Step 1:
8-chloro-6-(cyclopropylethynyl)isoquinolin-3-amine

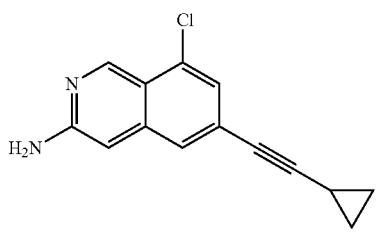 [SMILES: Nc1cc2cc(C#CC3CC3)cc(Cl)c2cn1]

A mixture of ethynylcyclopropane (500 mg, 7.56 mmol), CuI (50 mg, 0.26 mmol), 6-bromo-8-chloro-isoquinolin-3-amine (200 mg, 0.78 mmol), Et$_3$N (785 mg, 7.77 mmol) and Pd(PPh$_3$)$_2$C$_2$ (62 mg, 0.08 mmol) in DMF (2 mL) was heated at 110° C. for 16 hours. The reaction solution was diluted with ethyl acetate, washed with saturated aqueous NH$_4$Cl (20 mL×3), dried over Na$_2$SO$_4$, filtered and concentrated. The residue was purified by prep-TLC (normal phase silica gel, dichloromethane/methanol=25/1) to give 8-chloro-6-(2-cyclopropylethynyl) isoquinolin-3-amine (170 mg, 81% yield) as a yellow solid.

Step 2: 8-chloro-6-(5-cyclopropylpyridazin-4-yl) isoquinolin-3-amine

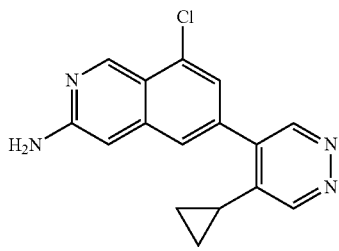 [SMILES: Nc1cc2cc(-c3cnncc3C3CC3)cc(Cl)c2cn1]

A solution of 1,2,4,5-tetrazine (80 mg, 0.97 mmol) and 8-chloro-6-(2-cyclopropylethynyl)isoquinolin-3-amine (60 mg, 0.25 mmol) in p-xylene (3 mL) was stirred at 140° C. for 18 hours. The reaction solution was concentrated. The residue was purified by prep-TLC (normal phase silica gel, dichloromethane/methanol=30/1) to give 8-chloro-6-(5-cyclopropylpyridazin-4-yl)isoquinolin-3-amine (40 mg, 55% yield) as a yellow oil.

Step 3: (±)-cis-N-(8-chloro-6-(5-cyclopropylpyridazin-4-yl)isoquinolin-3-yl)-2-fluorocyclopropanecarboxamide

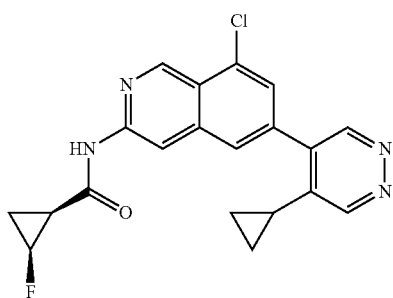 [SMILES: O=C(Nc1cc2cc(-c3cnncc3C3CC3)cc(Cl)c2cn1)[C@@H]1C[C@@H]1F]

To a solution of (±)-8-chloro-6-(5-cyclopropylpyridazin-4-yl)isoquinolin-3-amine (100 mg, 0.34 mmol) in dichloromethane (10 mL) and pyridine (0.08 mL, 1.01 mmol) was added a solution of cis-2-fluorocyclopropanecarbonyl chloride (0.13 g, 1.08 mmol) in dichloromethane (2 mL) at 0° C. The mixture was stirred at 20° C. for 1 hour before concentrated under vacuum. The residue was purified by prep-TLC (normal phase, silica gel, petroleum ether/ethyl acetate=4:1) to give (±)-cis-N-[8-chloro-6-(5-cyclopropylpyridazin-4-yl)-3-isoquinolyl]-2-fluoro-cyclopropanecarboxamide (100 mg, 77% yield) as a yellow solid.

Step 4: (±)-cis-N-(8-amino-6-(5-cyclopropylpyridazin-4-yl)isoquinolin-3-yl)-2-fluorocyclopropanecarboxamide

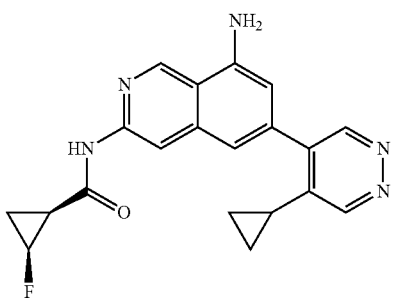

To a sealed tube was added (±)-cis-N-[8-chloro-6-(5-cyclopropylpyridazin-4-yl)-3-isoquinolyl]-2-fluoro-cyclopropanecarboxamide (80 mg, 0.21 mmol), tert-butyl carbamate (244 mg, 2.09 mmol), Pd$_2$(dba)$_3$ (19 mg, 0.02 mmol), NaOtBu (59 mg, 0.62 mmol), tBuBrettPhos (10 mg, 0.02 mmol) and 1-methyl-2-pyrrolidinone (3 mL). The mixture was stirred at 110° C. for 2 hours. The reaction mixture was concentrated in vacuum. The residue was purified by reverse phase prep-HPLC to give (±)-cis-N-[8-amino-6-(5-cyclopropylpyridazin-4-yl)-3-isoquinolyl]-2-fluoro-cyclopropanecarboxamide (8 mg, 10% yield) as a yellow solid. LCMS (ESI): R$_T$(min)=1.566, [M+H]$^+$=364.1, method=C; $^1$H NMR (400 MHz, CD$_3$OD) δ 9.28 (s, 1H), 9.00 (s, 1H), 8.78 (s, 1H), 8.37 (s, 1H), 7.18 (s, 1H), 6.80 (s, 1H), 4.99-4.78 (m, 1H), 2.21-2.08 (m, 2H), 1.88-1.76 (m, 1H), 1.27-1.17 (m, 3H), 1.12-1.06 (m, 2H).

Example 10

(±)-cis-N-(8-amino-6-(7-methyl-3H-imidazo [4,5-b] pyridin-6-yl) isoquinolin-3-yl)-2-fluorocyclopropanecarboxamide (Compound 16)

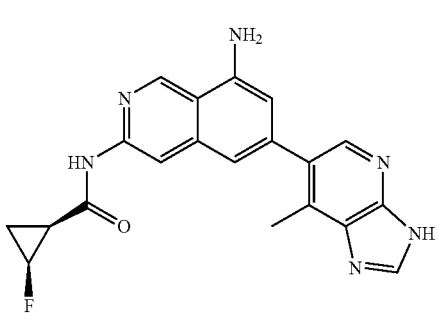 [SMILES: Cc1c(-c2cc(N)c3cnc(NC(=O)[C@@H]4C[C@@H]4F)cc3c2)cnc2[nH]cnc12]

Step 1: (±)-cis-N-(8-chloro-6-(7-methyl-3H-imidazo [4, 5-b] pyridin-6-yl) isoquinolin-3-yl)-2-fluorocyclopropanecarboxamide

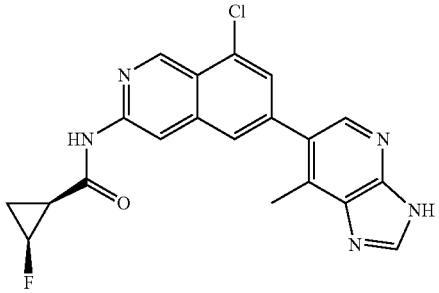 [SMILES: Cc1c(-c2cc(Cl)c3cnc(NC(=O)[C@@H]4C[C@@H]4F)cc3c2)cnc2[nH]cnc12]

A mixture of (±)-cis-N-(6-bromo-8-chloro-3-isoquinolyl)-2-fluoro-cyclopropanecarboxamide (300 mg, 0.87 mmol), 7-methyl-6-(4,4,5,5-tetramethyl-1,3,2-dioxaborolan-2-yl)-3H-imidazo[4,5-b]pyridine (280 mg, 1.08 mmol), Pd(dppf)Cl$_2$ (60 mg, 0.08 mmol), K$_2$CO$_3$ (350 mg, 2.54 mmol) in 1,4-dioxane (6 mL) and water (1 mL) was stirred under an Ar atmosphere at 110° C. for 3 hours. The reaction was concentrated to dryness. The crude product was then purified by column chromatography (ethyl acetate/petroleum ether=1:1) to afford (1)-cis-N-[8-chloro-6-(7-methyl-1H-imidazo[4,5-b]pyridin-6-yl)-3-isoquinolyl]-2-fluoro-cyclopropanecarboxamide (280 mg, 64% yield) as a yellow solid. LCMS (ESI): [M+H]$^+$=396.1.

Step 2: (±)-cis-N-(8-chloro-6-(7-methyl-3-(tetrahydro-2H-pyran-2-yl)-3H-imidazo[4,5-b]pyridin-6-yl)isoquinolin-3-yl)-2-fluorocyclopropanecarboxamide

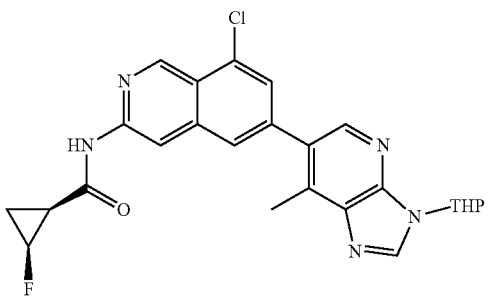

A solution of (±)-cis-N-[8-chloro-6-(7-methyl-3H-imidazo[4,5-b]pyridin-6-yl)-3-isoquinolyl]-2-fluoro-cyclopropanecarboxamide (280 mg, 0.71 mmol), 3,4-dihydro-2H-pyran (1.0 mL, 10.96 mmol), and trifluoroacetic acid (0.1 mL, 1.34 mmol) in dichloromethane (15 mL) was heated overnight at reflux. The reaction was then diluted with 5 mL of a saturated NaHCO$_3$ solution was added. The organic layer was then separated, dried (Na$_2$SO$_4$) and concentrated. The crude was then purified by column chromatography on silica gel (ethyl acetate/petroleum ether=1:10) to afford (±)-cis-N-[8-chloro-6-(7-methyl-3-tetrahydropyran-2-yl-imidazo[4,5-b]pyridin-6-yl)-3-isoquinolyl]-2-fluoro-cyclopropanecarboxamide (160 mg, 46% yield) as a yellow solid. LCMS (ESI): [M+H]$^+$=480.2.

Step 3: (±)-tert-butyl 3-(cis-2-fluorocyclopropanecarboxamido)-6-(7-methyl-3-(tetrahydro-2H-pyran-2-yl)-3H-imidazo [4, 5-b] pyridin-6-yl) isoquinolin-8-ylcarbamate

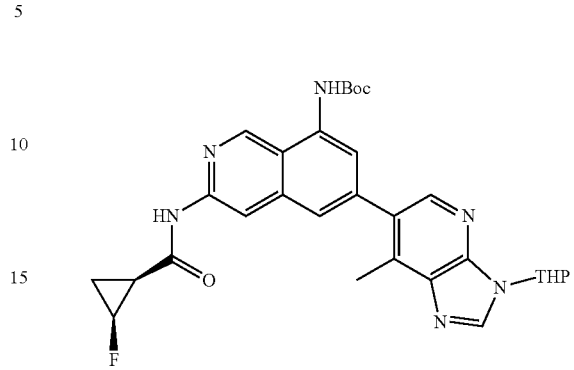

A mixture of (±)-cis-N-[8-chloro-6-(7-methyl-3-tetrahydropyran-2-yl-imidazo[4,5-b]pyridin-6-yl)-3-isoquinolyl]-2-fluoro-cyclopropanecarboxamide (50 mg, 0.10 mmol), tert-butyl carbamate (120 mg, 1.02 mmol), Xantphos (25 mg, 0.04 mmol), Pd$_2$(dba)$_3$ (20 mg, 0.02 mmol), sodium tert-butoxide (50 mg, 0.52 mmol) in dry DMF (2.0 mL) and dry toluene (2.0 mL) was stirred overnight at 115° C. The reaction was concentrated. The residue was taken up in ethyl acetate (15 ml). The mixture was washed with 20 mL of saturated brine solution. The organic layer was then separated, dried (Na$_2$SO$_4$) and concentrated. The crude was purified by column chromatography on silica gel (ethyl acetate/petroleum ether, 1/5 to 1/1) to afford (±)-tert-butyl N-[3-[[cis-2-fluorocyclopropanecarbonyl]amino]-6-(7-methyl-3-tetrahydropyran-2-yl-imidazo[4,5-b]pyridin-6-yl)-8-isoquinolyl]carbamate (60 mg, 60% yield) as a yellow solid. LCMS (ESI): [M+H]$^+$=477.1.

Step 4: (±)-cis-N-(8-amino-6-(7-methyl-3H-imidazo [4, 5-b] pyridin-6-yl) isoquinolin-3-yl)-2-fluorocyclopropanecarboxamide

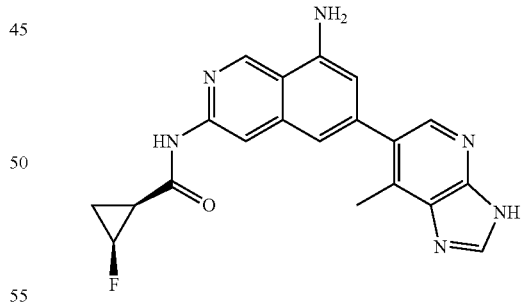

A solution of (±)-tert-butyl N-[3-[[cis-2-fluorocyclopropanecarbonyl]amino]-6-(7-methyl-3-tetrahydropyran-2-yl-imidazo[4,5-b]pyridin-6-yl)-8-isoquinolyl]carbamate (60 mg, 0.06 mmol) in methanol (1 mL) and HCl (4M in dioxane, 1.0 mL, 4 mmol) was stirred at room temperature for 1 hour. The reaction was purified by reverse phase prep-HPLC to afford (±)-cis-N-[8-amino-6-(7-methyl-3H-imidazo[4,5-b]pyridin-6-yl)-3-isoquinolyl]-2-fluoro-cyclopropanecarboxamide (9 mg, 38% yield) as a yellow solid. LCMS (ESI): [M+H]$^+$=377.2, Rt (min)=1.42, Method=E; $^1$HNMR (400 MHz, CD$_3$OD) δ 9.25 (s, 1H), 8.43 (s, 1H), 8.33 (s, 2H), 7.06 (s, 1H), 6.76 (d, J=1.6 Hz, 1H), 4.99-4.79 (m, 1H), 2.65 (s, 3H), 2.18-2.13 (m, 1H), 1.88-1.77 (m, 1H), 1.27-1.18 (m, 1H).

Example 11

(±)-cis-N-(8-amino-6-(5-isopropyl-1H-pyrazol-4-yl) isoquinolin-3-yl)-2-fluoro cyclopropanecarboxamide (Compound 17)

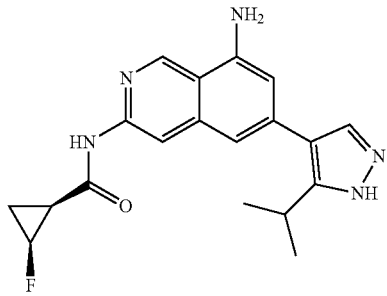 [SMILES: CC(C)c1[nH]ncc1-c1cc(N)c2cnc(NC(=O)[C@@H]3C[C@@H]3F)cc2c1]

Step 1: 5-isopropyl-4-(4,4,5,5-tetramethyl-1,3,2-dioxaborolan-2-yl)-1H-pyrazole

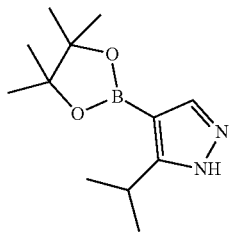 [SMILES: CC(C)c1[nH]ncc1B1OC(C)(C)C(C)(C)O1]

A mixture of 4-bromo-3-isopropyl-1H-pyrazole (380 mg, 2.01 mmol), Pd(dppf)Cl₂ (140 mg, 0.19 mmol), potassium acetate (800 mg, 8.16 mmol), bis(pinacolato)diboron (4750 mg, 18.71 mmol) in 1,4-dioxane (20 mL) was stirred under an inert atmosphere at 110° C. for 5 hours. The reaction was concentrated to dryness. The crude was then purified by column chromatography on silica gel (ethyl acetate/petroleum ether=1:1) to afford 5-isopropyl-4-(4,4,5,5-tetramethyl-1,3,2-dioxaborolan-2-yl)-1H-pyrazole (400 mg, 28% yield) as a red liquid. LCMS (ESI): [M+H]⁺=237.2.

Step 2: (±)-cis-N-(8-chloro-6-(5-isopropyl-1H-pyrazol-4-yl) isoquinolin-3-yl)-2-fluorocyclopropanecarboxamide

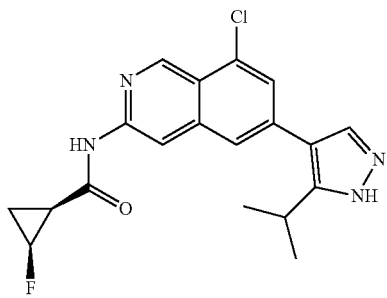 [SMILES: CC(C)c1[nH]ncc1-c1cc(Cl)c2cnc(NC(=O)[C@@H]3C[C@@H]3F)cc2c1]

To a sealed tube containing the reaction mixture of 5-isopropyl-4-(4,4,5,5-tetramethyl-1,3,2-dioxaborolan-2-yl)-1H-pyrazole (400 mg, 0.56 mmol), Pd(dppf)Cl₂ (35 mg, 0.05 mmol), K₂CO₃ (200 mg, 1.45 mmol), and (±)-cis-N-(6-bromo-8-chloro-3-isoquinolyl)-2-fluoro-cyclopropanecarboxamide (150 mg, 0.44 mmol) in 1,4-dioxane (6 mL) and water (1 mL). The reaction mixture was heated at 130° C. in a microwave for 1 hour. The reaction was concentrated to dryness. The crude was then purified by column chromatography on silica gel (ethyl acetate) to afford crude (±)-cis-N-[8-chloro-6-(5-isopropyl-1H-pyrazol-4-yl)-3-isoquinolyl]-2-fluoro-cyclopropanecarboxamide (200 mg, 50% yield) as a yellow liquid. LCMS (ESI): [M+H]+=373.1.

Step 3: (±)-cis-N-(8-chloro-6-(5-isopropyl-1-(tetrahydro-2H-pyran-2-yl)-1H-pyrazol-4-yl) isoquinolin-3-yl)-2-fluorocyclopropanecarboxamide

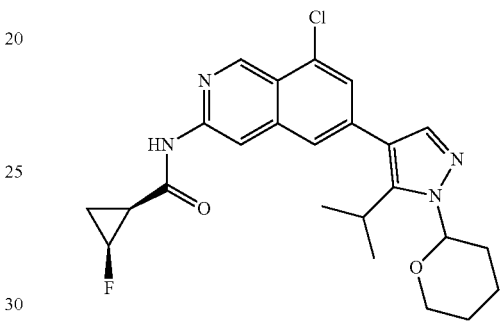

A solution of (±)-cis-N-[8-chloro-6-(5-isopropyl-1H-pyrazol-4-yl)-3-isoquinolyl]-2-fluoro-cyclopropanecarboxamide (200 mg, 0.22 mmol), 3,4-dihydro-2H-pyran (1.0 mL, 10.96 mmol), and trifluoroacetic acid (0.1 mL, 1.34 mmol) in dichloromethane (15 mL) was refluxed overnight. The reaction was then concentrated to dryness. The crude was then purified by column chromatography on silica gel (petroleum ether/ethyl acetate=10/1) to afford (±)-cis-N-[8-chloro-6-(5-isopropyl-1-tetrahydropyran-2-yl-pyrazol-4-yl)-3-isoquinolyl]-2-fluoro-cyclopropanecarboxamide (80 mg, 70% yield) as a yellow solid. LCMS (ESI): [M+H]⁺=457.2.

Step 4: (±)-cis-N-(8-amino-6-(5-isopropyl-1-(tetrahydro-2H-pyran-2-yl)-1H-pyrazol-4-yl) isoquinolin-3-yl)-2-fluorocyclopropanecarboxamide

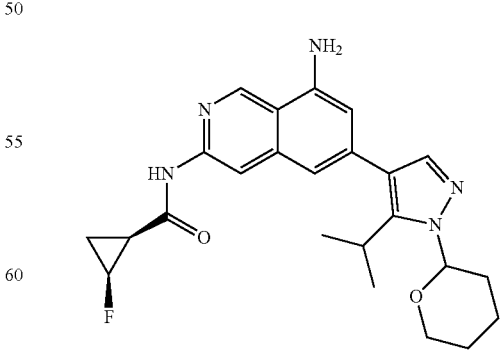

A mixture of (±)-cis-N-[8-chloro-6-(5-isopropyl-1-tetrahydropyran-2-yl-pyrazol-4-yl)-3-isoquinolyl]-2-fluoro-cyclopropanecarboxamide (70 mg, 0.15 mmol), tert-butyl carbamate (100 mg, 0.85 mmol), Xantphos (35 mg, 0.06 mmol), Pd$_2$(dba)$_3$ (25 mg, 0.03 mmol), and Cs$_2$CO$_3$ (200 mg, 0.62 mmol) in dry DMF (1 mL) and dry toluene (1 mL) was stirred at 130° C. under an inert atmosphere for 4 hours. The reaction was then concentrated and purified by reverse phase chromatography (methanol 40-60/0.05% ammonia in water) to afford (±)-cis-N-[8-amino-6-(5-isopropyl-1-tetrahydropyran-2-yl-pyrazol-4-yl)-3-isoquinolyl]-2-fluoro-cyclopropane carboxamide (25 mg, 37% yield) as a white solid. LCMS (ESI): [M+H]=438.2.

Step 5: (±)-cis-N-(8-amino-6-(5-isopropyl-1H-pyrazol-4-yl) isoquinolin-3-yl)-2-fluorocyclopropanecarboxamide

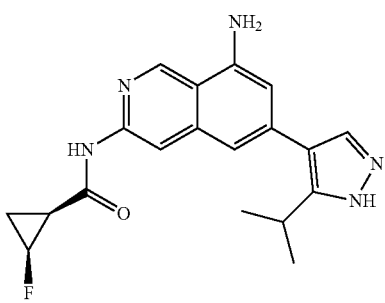 [SMILES: CC(C)c1[nH]ncc1-c1cc(N)c2cnc(NC(=O)[C@@H]3C[C@@H]3F)cc2c1]

A solution of (±)-cis-N-[8-amino-6-(5-isopropyl-1-tetrahydropyran-2-yl-pyrazol-4-yl)-3-isoquinolyl]-2-fluoro-cyclopropanecarboxamide (25 mg, 0.06 mmol) in HCl in 1,4-dioxane (4M, 1.0 mL, 4.0 mmol) was stirred at room temperature for 30 minutes. The resulting mixture was purified by reverse phase chromatography (methanol 60%/0.05% ammonia in water) to afford (1)-cis-N-[8-amino-6-(5-isopropyl-1H-pyrazol-4-yl)-3-isoquinolyl]-2-fluoro-cyclopropanecarboxamide (9 mg, 43% yield) as a yellow solid. LCMS (ESI): R$_T$ (min)=1.57, [M+H]$^+$=354.1, method=E; $^1$H NMR (400 MHz, CD$_3$OD) δ 9.17 (s, 1H), 8.26 (s, 1H), 7.69 (s, 1H), 7.07 (s, 1H), 6.83 (d, J=0.9 Hz, 1H), 4.99-4.92 (m, 0.5H), 4.83-4.79 (m, 0.5H), 3.45-3.44 (m, 1H), 2.17-2.13 (m, 1H), 1.87-1.79 (m, 1H), 1.37-1.35 (d, J=6.8 Hz, 6H), 1.27-1.18 (m, 1H).

Example 12

(±)-cis-N-(8-amino-6-(1-ethyl-5-methyl-2-oxo-1,2-dihydropyridin-4-yl)isoquinolin-3-yl)-2-fluorocyclopropanecarboxamide (Compound 18)

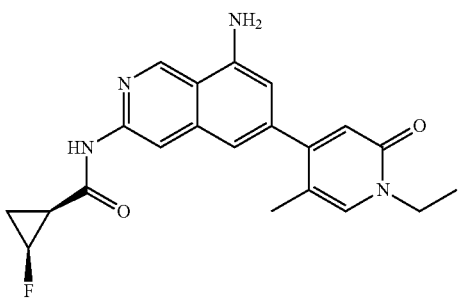 [SMILES: CCn1cc(C)c(-c2cc(N)c3cnc(NC(=O)[C@@H]4C[C@@H]4F)cc3c2)cc1=O]

Step 1: 4-iodo-5-methylpyridin-2-ol

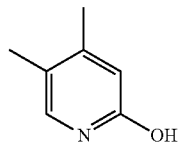

A mixture of 4-iodo-2-methoxy-5-methyl-pyridine (700 mg, 2.81 mmol), iodide trimethylsilane (752 mg, 3.76 mmol) in acetonitrile (10 mL) was heated to reflux for 2 hours. The reaction was then concentrated to dryness. The crude product was then purified by column chromatography on silica gel (ethyl acetate) to afford 4-iodo-5-methyl-pyridin-2-ol (500 mg, 71% yield) as a white solid. LCMS (ESI): [M+H]$^+$=235.9.

Step 2: 1-ethyl-4-iodo-5-methylpyridin-2(1H)-one

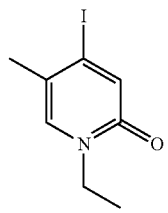

A mixture of 4-iodo-5-methyl-pyridin-2-ol (480 mg, 2.04 mmol) and sodium hydride (60% in mineral oil, 200 mg, 5 mmol) in DMF (5 mL) was stirred at room temperature for 20 minutes. Iodoethane (0.5 mL, 6.25 mmol) was then added. The mixture was stirred at room temperature for 1 hour. The mixture was purified by reverse phase chromatography (methanol 60%/0.1% ammonia in water) to afford 1-ethyl-4-iodo-5-methyl-pyridin-2-one (250 mg, 47% yield) as a white solid. LCMS (ESI): [M+H]$^+$=264.0.

Step 3: (±)-cis-N-(8-chloro-6-(1-ethyl-5-methyl-2-oxo-1,2-dihydropyridin-4-yl)isoquinolin-3-yl)-2-fluorocyclopropanecarboxamide

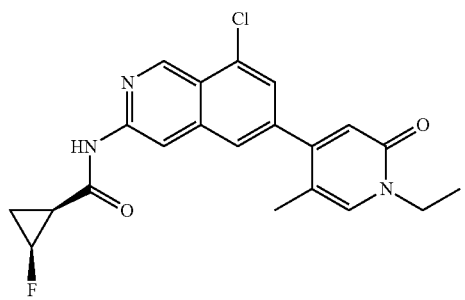 [SMILES: CCn1cc(C)c(-c2cc(Cl)c3cnc(NC(=O)[C@@H]4C[C@@H]4F)cc3c2)cc1=O]

A mixture of 1-ethyl-4-iodo-5-methyl-pyridin-2-one (120 mg, 0.46 mmol), Pd(dppf)Cl$_2$ (30 mg, 0.04 mmol), potassium phosphate (400 mg, 1.89 mmol), and (±)-[8-chloro-3-[[cis-2-fluorocyclopropanecarbonyl]amino]-6-isoquinolyl] boronic acid (140 mg, 0.45 mmol) in 1,4-dioxane (6 mL)

and water (1 mL) was stirred at 100° C. for 1 hour. The reaction was concentrated to dryness. The crude was then purified by column chromatography on silica gel (ethyl acetate) to afford (±)-cis-N-[8-chloro-6-(1-ethyl-5-methyl-2-oxo-4-pyridyl)-3-isoquinolyl]-2-fluoro-cyclopropanecarboxamide (70 mg, 37% yield) as a white solid. LCMS (ESI): [M+H]=400.1.

Step 4: (±)-cis-N-(8-amino-6-(1-ethyl-5-methyl-2-oxo-1,2-dihydropyridin-4-yl)isoquinolin-3-yl)-2-fluorocyclopropanecarboxamide

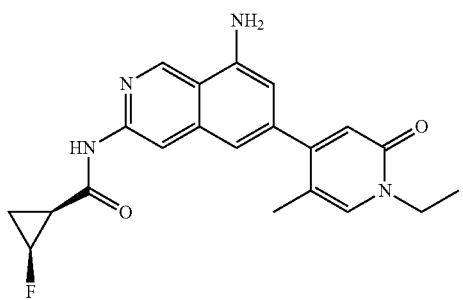 [SMILES: CCn1cc(C)c(-c2cc(N)c3cnc(NC(=O)[C@@H]4C[C@@H]4F)cc3c2)cc1=O]

A mixture of (±)-cis-N-[8-chloro-6-(1-ethyl-5-methyl-2-oxo-4-pyridyl)-3-isoquinolyl]-2-fluoro-cyclopropanecarboxamide (50 mg, 0.13 mmol), tert-butyl carbamate (155 mg, 1.32 mmol), Xantphos (30 mg, 0.05 mmol), $Pd_2(dba)_3$ (25 mg, 0.03 mmol), and $Cs_2CO_3$ (200 mg, 0.62 mmol) in dry DMF (2 mL) and dry toluene (2 mL) was stirred overnight under inert atmosphere at 112° C. The reaction was then concentrated and purified by reverse phase chromatography (acetonitrile 0-40/0.1% HCl in water) to afford (±)-cis-N-[8-amino-6-(1-ethyl-5-methyl-2-oxo-4-pyridyl)-3-isoquinolyl]-2-fluoro-cyclopropanecarboxamide (8.1 mg, 17% yield) as a formate salt (yellow solid). LCMS(ESI): $R_T$ (min)=1.44, [M+H]$^+$=381.1, method=A; $^1$H NMR (400 MHz, $CD_3OD$) δ 9.24 (s, 1H), 8.32 (s, 1H), 7.58 (s, 1H), 6.96 (s, 1H), 6.63 (d, J=0.8 Hz, 1H), 6.49 (s, 1H), 4.97-4.80 (m, 1H), 4.108 (q, J=7.2 Hz, 2H), 2.17-2.14 (m, 1H), 2.05 (s, 3H), 1.86-1.79 (m, 1H), 1.39 (t, J=7.2 Hz, 3H), 1.25-1.20 (m, 1H).

Example 13

(±)-cis-N-(8-amino-6-(5-methyl-2-oxo-1, 2-dihydropyridin-4-yl) isoquinolin-3-yl)-2-fluorocyclopropanecarboxamide (Compound 19)

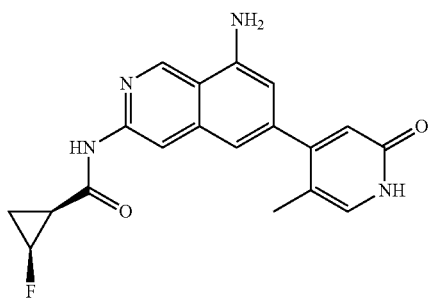 [SMILES: Cc1c[nH]c(=O)cc1-c1cc(N)c2cnc(NC(=O)[C@@H]3C[C@@H]3F)cc2c1]

Step 1: (±)-cis-N-(8-chloro-6-(2-methoxy-5-methylpyridin-4-yl) isoquinolin-3-yl)-2-fluorocyclopropanecarboxamide

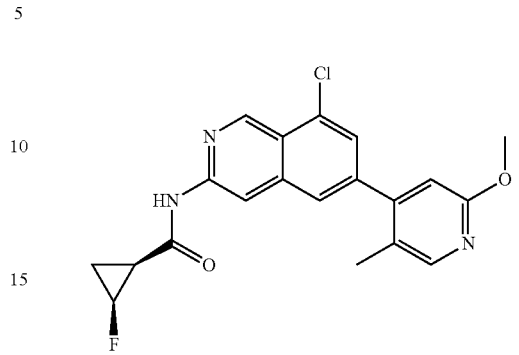

A mixture of 4-iodo-2-methoxy-5-methyl-pyridine (255 mg, 1.02 mmol), Pd(dppf)Cl$_2$ (40 mg, 0.05 mmol), K$_3$PO$_4$ (350 mg, 1.65 mmol), [8-chloro-3-[[cis-2-fluorocyclopropanecarbonyl] amino]-6-isoquinolyl]boronic acid (220 mg, 0.71 mmol) in 1,4-dioxane (6 mL) and water (1 mL) was stirred at 100° C. for 1 hour. The reaction mixture was concentrated to dryness. The crude was then purified by column chromatography on silica gel (petroleum ether/ethyl acetate=5/1) to afford (±)-cis-N-[8-chloro-6-(2-methoxy-5-methyl-4-pyridyl)-3-isoquinolyl]-2-fluoro-cyclopropanecarboxamide (100 mg, 35% yield) as a white solid. LCMS (ESI): [M+H]$^+$=386.1.

Step 2: (±)-cis-N-(8-amino-6-(2-methoxy-5-methylpyridin-4-yl) isoquinolin-3-yl)-2-fluorocyclopropanecarboxamide

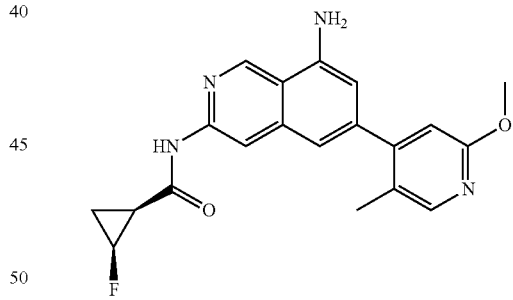

A mixture of (±)-cis-N-[8-chloro-6-(2-methoxy-5-methyl-4-pyridyl)-3-isoquinolyl]-2-fluoro-cyclopropanecarboxamide (100 mg, 0.26 mmol), tert-butyl carbamate (200 mg, 1.71 mmol), Xantphos (60 mg, 0.10 mmol), Pd$_2$(dba)$_3$ (50 mg, 0.05 mmol), Cs$_2$CO$_3$ (420 mg, 1.29 mmol) in dry DMF (2 mL) and dry toluene (2 mL) was stirred at 115° C. under Ar for 4 hours. The reaction was concentrated to dryness. The crude was then purified by column chromatography on silica gel eluted ethyl acetate/petroleum ether (1:1) to afford crude (±)-cis-N-[8-amino-6-(2-methoxy-5-methyl-4-pyridyl)-3-isoquinolyl]-2-fluoro-cyclopropane carboxamide (25 mg) as a yellow solid. LCMS (ESI): [M+H]$^+$=367.2.

Step 3: (±)-cis-N-(8-amino-6-(5-methyl-2-oxo-1,2-dihydropyridin-4-yl) isoquinolin-3-yl)-2-fluorocyclopropanecarboxamide

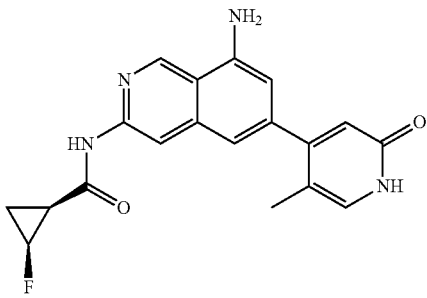 [SMILES: Cc1c[nH]c(=O)cc1-c1cc(N)c2cnc(NC(=O)[C@@H]3C[C@@H]3F)cc2c1]

A mixture of (±)-cis-N-[8-amino-6-(2-methoxy-5-methyl-4-pyridyl)-3-isoquinolyl]-2-fluoro-cyclopropanecarboxamide (35 mg, 0.05 mmol) and iodotrimethylsilane (30 mg, 0.15 mmol) in acetonitrile (10 mL) was heated to reflux for 2 hours. Then 0.5 mL of saturated Na₂S2O3 solution was added and the reaction was concentrated. The resulting residue was purified by reverse phase chromatography (methanol 40-50/0.05% ammonia in water) to afford (1)-cis-N-[8-amino-6-(5-methyl-2-oxo-1H-pyridin-4-yl)-3-isoquinolyl]-2-fluoro-cyclopropanecarboxamide (9 mg, 53% yield) as a yellow solid. LCMS(ESI):$R_T$ (min)=1.45, [M+H]⁺=353.1, method=B; ¹H NMR (400 MHz, DMSO-d₆) δ 11.53-11.49 (m, 1H), 10.81 (s, 1H), 9.32 (s, 1H), 8.27 (s, 1H), 7.28 (s, 1H), 6.85 (s, 1H), 6.49 (s, 1H), 6.34 (s, 2H), 6.19 (s, 1H), 5.0-4.83 (m, 1H), 2.28-2.22 (m, 1H), 1.91 (s, 3H), 1.71-1.63 (m, 1H), 1.21-1.14 (m, 1H).

Example 14

1-(8-amino-6-(1-methyl-1H-pyrazol-4-yl)isoquinolin-3-yl)-3-isopropylurea (Compound 20)

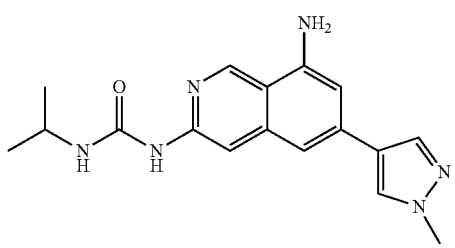

Step 1: 8-chloro-6-(1-methyl-1H-pyrazol-4-yl)isoquinolin-3-amine

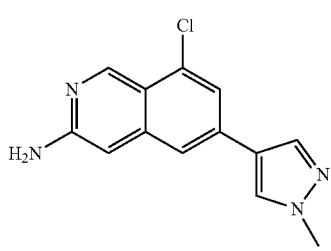 [SMILES: Cn1cc(-c2cc(Cl)c3cnc(N)cc3c2)cn1]

To a sealed tube was added 6-bromo-8-chloro-isoquinolin-3-amine (300 mg, 1.17 mmol), 1-methyl-4-(4,4,5,5-tetramethyl-1,3,2-dioxaborolan-2-yl)-1h-pyrazole (364 mg, 1.75 mmol), Pd(dppf)Cl₂ (105 mg, 0.14 mmol), Na₂CO₃ (375 mg, 3.54 mmol), 1,4-dioxane (15 mL) and water (1.5 mL). The mixture was bubbled through with N₂ for 2 min, and stirred at 100° C. for 2.5 hours. The mixture was concentrated in vacuo and then purified by column chromatography (silica-gel column, petroleum ether/ethyl acetate from 1:1 to 0:100, uv 254 nm) to get 8-chloro-6-(1-methylpyrazol-4-yl)isoquinolin-3-amine (290 mg, 94% yield) as a yellow solid. LCMS (ESI) [M+H]⁺=259.1.

Step 2: 1-(8-chloro-6-(1-methyl-1H-pyrazol-4-yl)isoquinolin-3-yl)-3-isopropylurea

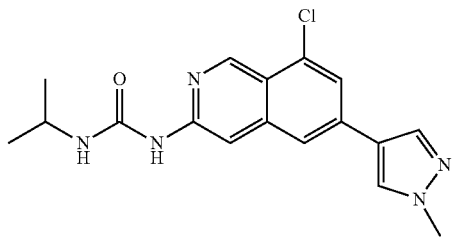 [SMILES: CC(C)NC(=O)Nc1cc2cc(-c3cnn(C)c3)cc(Cl)c2cn1]

To a pressure tube was added 8-chloro-6-(1-methylpyrazol-4-yl)isoquinolin-3-amine (280 mg, 1.08 mmol), isopropyl isocyanate (1 mL, 10.18 mmol), and DBU (494 mg, 3.25 mmol). The mixture was stirred at 100° C. for 4 hours. The mixture was concentrated and purified by column chromatography (20 g silica-gel column, eluted with petroleum ether/ethyl acetate from 1:1 to 0:100) to give 1-[8-chloro-6-(1-methylpyrazol-4-yl)-3-isoquinolyl]-3-isopropyl-urea (200 mg, 52% yield) as yellow solid. LCMS (ESI) [M+H]⁺=344.1.

Step 3: 1-(8-amino-6-(1-methyl-1H-pyrazol-4-yl)isoquinolin-3-yl)-3-isopropylurea

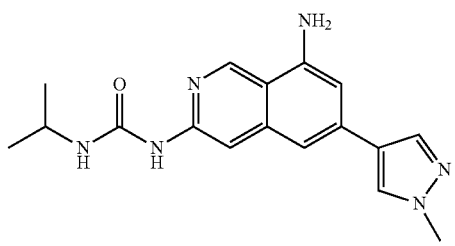 [SMILES: CC(C)NC(=O)Nc1cc2cc(-c3cnn(C)c3)cc(N)c2cn1]

To a sealed tube was added 1-[8-chloro-6-(1-methylpyrazol-4-yl)-3-isoquinolyl]-3-isopropyl-urea (180 mg, 0.52 mmol), tert-butyl carbamate (500 mg, 4.27 mmol), Pd₂(dba)₃ (100 mg, 0.11 mmol), NaOtBu (150 mg, 1.56 mmol), tBuBrettPhos (60 mg, 0.12 mmol) and 1-methyl-2-pyrrolidinone (15 mL). The mixture was stirred at 110° C. for 2 hours. The reaction mixture was concentrated under vacuum. The residue was purified by column chromatography (10 mmol/L NH₄HCO₃ aq./acetonitrile from 100:0 to 1:5) to give 1-[8-amino-6-(1-methylpyrazol-4-yl)-3-isoquinolyl]-3-isopropyl-urea (31 mg, 18% yield) as a pale-brown solid. LCMS (ESI): $R_T$ (min)=1.167, [M+H]⁺=325.2, method=B; $^1$H NMR (400 MHz, CD$_3$OD) δ: 8.94 (s, 1H), 7.92 (s, 1H), 7.78 (s, 1H), 7.35 (s, 1H), 7.06 (s, 1H), 6.76 (d, J=1.6 Hz, 1H), 3.92-3.85 (m, 1H), 3.85 (s, 3H), 1.15 (d, J=6.4 Hz, 6H).

Example 15

(±)-trans-N-[8-amino-6-(1-methylpyrrolo[2,3-b]pyridin-4-yl)-3-isoquinolyl]-2-cyano-cyclopropanecarboxamide (Compound 21)

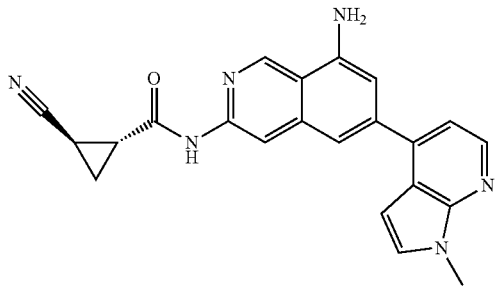 [SMILES: Cn1ccc2c(-c3cc(N)c4cnc(NC(=O)[C@@H]5C[C@H]5C#N)cc4c3)ccnc21]

Step 1: 4-(4,4,5,5-tetramethyl-1,3,2-dioxaborolan-2-yl)-1H-pyrrolo[2,3-b]pyridine

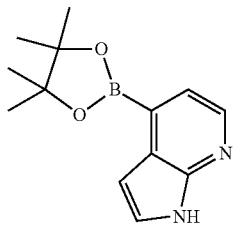

A mixture of 4-bromo-1H-pyrrolo[2,3-b]pyridine (500 mg, 2.54 mmol), bis(pinacolato)diboron (1289 mg, 5.08 mmol), Pd(dppf)Cl$_2$ (186 mg, 0.25 mmol) and potassium acetate (497 mg, 5.08 mmol) in 1,4-dioxane (18 mL) was stirred under Ar at 90° C. for 3 hours. The mixture was concentrated and purified by column chromatography (ethyl acetate/hexane=1:1) to afford 4-(4,4,5,5-tetramethyl-1,3,2-dioxaborolan-2-yl)-1H-pyrrolo[2,3-b]pyridine (480 mg, 78% yield) as a white solid. LCMS (ESI) [M+H]$^+$=245.1.

Step 2: (±)-trans-N-[8-chloro-6-(1H-pyrrolo[2,3-b]pyridin-4-yl)-3-isoquinolyl]-2-cyano-cyclopropanecarboxamide

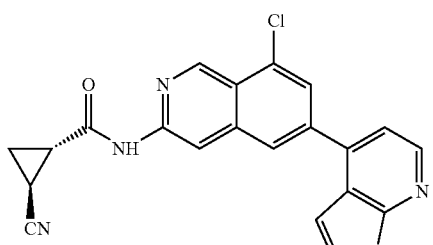

A mixture of (±)-trans-N-(6-bromo-8-chloro-3-isoquinolyl)-2-cyano-cyclopropanecarboxamide (180 mg, 0.51 mmol), 4-(4,4,5,5-tetramethyl-1,3,2-dioxaborolan-2-yl)-1h-pyrrolo[2,3-b]pyridine (150 mg, 0.62 mmol), Pd(PPh$_3$)$_4$ (59 mg, 0.05 mmol) and Na$_2$CO$_3$ (109 mg, 1.03 mmol) in 1,4-dioxane (2 mL) and water (0.1 mL) was stirred under Ar at 90° C. for 3 hours. The mixture was concentrated and purified by column chromatography (ethyl acetate/hexane=2:1) to afford (±)-trans-N-[8-chloro-6-(1H-pyrrolo[2,3-b]pyridin-4-yl)-3-isoquinolyl]-2-cyano-cyclopropanecarboxamide (210 mg, 65% yield) as a yellow solid. LCMS (ESI) [M+H]$^+$=388.1.

Step 3: (±)-trans-N-[8-chloro-6-(1-methylpyrrolo[2,3-b]pyridin-4-yl)-3-isoquinolyl]-2-cyano-cyclopropanecarboxamide

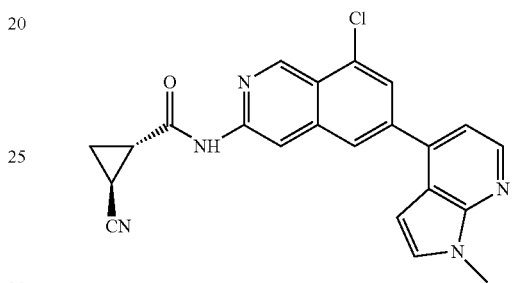

To a solution of (±)-trans-N-[8-chloro-6-(1H-pyrrolo[2,3-b]pyridin-4-yl)-3-isoquinolyl]-2-cyano-cyclopropanecarboxamide (100 mg, 0.16 mmol) in DMF (3 mL) was added NaH (13 mg, 0.32 mmol) at 0° C. The mixture was stirred at 0° C. for 0.5 hours. Methyl 4-methylbenzenesulfonate (30 mg, 0.16 mmol) was then added. The reaction was stirred at 0° C. for 2 hours. The crude mixture was purified by preparative reverse phase HPLC (C-18, acetonitrile/water+ 0.05% NH$_4$HCO$_3$) to give (±)-trans-N-[8-chloro-6-(1-methylpyrrolo[2,3-b]pyridin-4-yl)-3-isoquinolyl]-2-cyano-cyclopropanecarboxamide (110 mg, 53% yield) as a yellow solid. LCMS (ESI) [M+H]$^+$=402.1.

Step 4: (±)-trans-N-[8-(benzhydrylideneamino)-6-(1-methylpyrrolo[2,3-b]pyridin-4-yl)-3-isoquinolyl]-2-cyano-cyclopropanecarboxamide

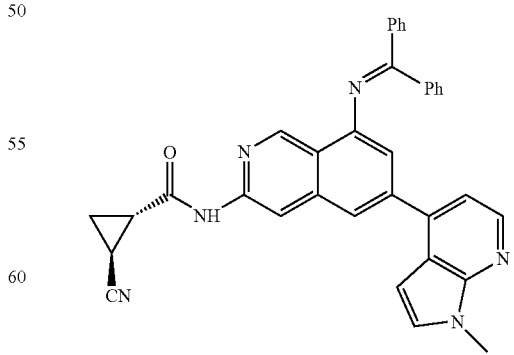

A mixture of (±)-trans-N-[8-chloro-6-(1-methylpyrrolo[2,3-b]pyridin-4-yl)-3-isoquinolyl]-2-cyano-cyclopropanecarboxamide (110 mg, 0.09 mmol), Pd$_2$(dba)$_3$ (16 mg, 0.02 mmol), Xantphos (20 mg, 0.04 mmol), Cs₂CO₃ (57 mg, 0.18 mmol) and benzophenone imine (48 mg, 0.26 mmol) in DMF (3 ml) and toluene (3 mL) was stirred under Ar at 130° C. for 2.5 hours. Ethyl acetate (80 mL) was added. The mixture was washed with brine (3×50 mL), dried with Na₂SO₄, filtered and evaporated under reduced pressure. The residue was purified by column chromatography (ethyl acetate/hexane, 1:1) to afford (±)-trans-N-[8-(benzhydrylideneamino)-6-(1-methylpyrrolo[2,3-b]pyridin-4-yl)-3-isoquinolyl]-2-cyano-cyclopropanecarboxamide (31 mg, 59% yield) as a yellow solid. LCMS (ESI) [M+H]⁺=547.3.

Step 5: (±)-trans-N-[8-amino-6-(1-methylpyrrolo[2,3-b]pyridin-4-yl)-3-isoquinolyl]-2-cyano-cyclopropanecarboxamide

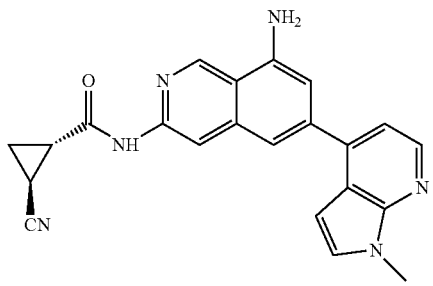 [SMILES: Cn1ccc2c(-c3cc(N)c4cnc(NC(=O)[C@H]5C[C@@H]5C#N)cc4c3)ccnc21]

A mixture of (±)-trans-N-[8-(benzhydrylideneamino)-6-(1-methylpyrrolo[2,3-b]pyridin-4-yl)-3-isoquinolyl]-2-cyano-cyclopropanecarboxamide (31 mg, 0.06 mmol) and 2,2,2-trifluoroacetic acid (1 mL) in dichloromethane (10 mL) and water (2 mL) was stirred at 25° C. for 2 hours. The reaction mixture was neutralized with NH₄OH to pH=7-8. The mixture was concentrated and purified by reverse phase prep-HPLC (Cis, acetonitrile/water+0.05% NH₄HCO₃) to give (±)-trans-N-[8-amino-6-(1-methylpyrrolo[2,3-b]pyridin-4-yl)-3-isoquinolyl]-2-cyano-cyclopropanecarboxamide (16 mg, 69% yield) as a yellow solid. LCMS (ESI) $R_T$ (min)=1.479, [M+H]⁺=383.1, method=A; ¹H NMR (400 MHz, DMSO-d₆) δ 11.13 (s, 1H), 9.37 (s, 1H), 8.36 (d, J=4.8 Hz, 1H), 8.32 (s, 1H), 7.62 (d, J=3.2 Hz, 1H), 7.28 (s, 1H), 7.27 (d, J=4.8 Hz, 1H), 7.04 (d, J=1.2 Hz, 1H), 6.69 (d, J=3.2 Hz, 1H), 6.44 (s, 2H), 3.88 (s, 3H), 2.80-2.75 (m, 1H), 2.18-2.13 (m, 1H), 1.63-1.58 (m, 1H), 1.47-1.42 (m, 1H).

Example 16

(±)-trans-N-[8-amino-6-(1H-pyrrolo[2,3-b]pyridin-4-yl)-3-isoquinolyl]-2-cyano-cyclopropanecarboxamide (Compound 22)

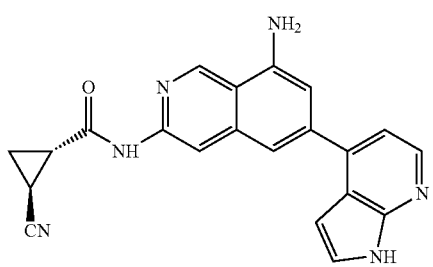 [SMILES: N#C[C@H]1C[C@@H]1C(=O)Nc1cc2cc(-c3ccnc4[nH]ccc34)cc(N)c2cn1]

Step 1: (±)-trans-N-[8-chloro-6-[1-(p-tolylsulfonyl)pyrrolo[2,3-b]pyridin-4-yl]-3-isoquinolyl]-2-cyano-cyclopropanecarboxamide

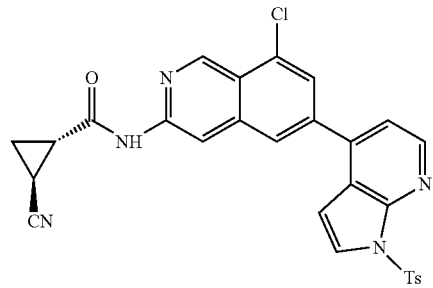 [SMILES: Cc1ccc(S(=O)(=O)n2ccc3c(-c4cc(Cl)c5cnc(NC(=O)[C@H]6C[C@@H]6C#N)cc5c4)ccnc32)cc1]

To a solution of (±)-trans-N-[8-chloro-6-(1H-pyrrolo[2,3-b]pyridin-4-yl)-3-isoquinolyl]-2-cyano-cyclopropanecarboxamide (170 mg, 0.27 mmol) in DMF (10 mL) was added NaH (22 mg, 0.54 mmol) at 0° C. The mixture was stirred at 0° C. for 0.5 hours. Tosyl chloride (104 mg, 0.54 mmol) was added and the reaction mixture was stirred at 0° C. for 2 hours. The mixture was purified by reverse phase prep-HPLC (C-18; acetonitrile/water+0.05% NH₄HCO₃) to give (±)-trans-N-[8-chloro-6-[1-(p-tolylsulfonyl)pyrrolo[2,3-b]pyridin-4-yl]-3-isoquinolyl]-2-cyano-cyclopropanecarboxamide (169 mg, 79% yield) as a yellow solid. LCMS (ESI) [M+H]⁺=542.1.

Step 2: (±)-trans-N-[8-(benzhydrylideneamino)-6-[1-(p-tolylsulfonyl)pyrrolo[2,3-b]pyridin-4-yl]-3-isoquinolyl]-2-cyano-cyclopropanecarboxamide

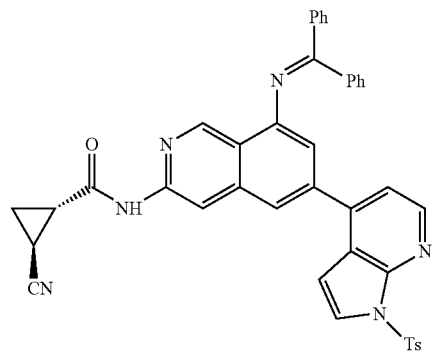 [SMILES: Cc1ccc(S(=O)(=O)n2ccc3c(-c4cc(N=C(c5ccccc5)c5ccccc5)c5cnc(NC(=O)[C@H]6C[C@@H]6C#N)cc5c4)ccnc32)cc1]

A mixture of (±)-trans-N-[8-chloro-6-[1-(p-tolylsulfonyl)pyrrolo[2,3-b]pyridin-4-yl]-3-isoquinolyl]-2-cyano-cyclopropanecarboxamide (170 mg, 0.22 mmol), Pd₂(dba)₃ (40 mg, 0.04 mmol), Xantphos (50 mg, 0.09 mmol), Cs₂CO₃ (140 mg, 0.43 mmol) and benzophenone imine (118 mg, 0.65 mmol) in DMF (6 mL) and toluene (6 mL) was stirred under Ar at 130° C. for 2.5 hours. Ethyl acetate (180 mL) was added. The mixture was washed with brine (3×50 mL), dried with Na₂SO₄, filtered and evaporated under reduced pressure. The residue was purified by column chromatography (ethyl acetate/hexane=1:1) to afford (±)-trans-N-[8-(benzhydrylideneamino)-6-[1-(p-tolylsulfonyl)pyrrolo[2,3-b]pyridin-4-yl]-3-isoquinolyl]-2-cyano-cyclopropanecarboxamide (100 mg, 67% yield) as a yellow solid. LCMS (ESI) [M+H]⁺=687.2.

Step 3: (±)-trans-N-[8-(benzhydrylideneamino)-6-(1H-pyrrolo[2,3-b]pyridin-4-yl)-3-isoquinolyl]-2-cyano-cyclopropanecarboxamide

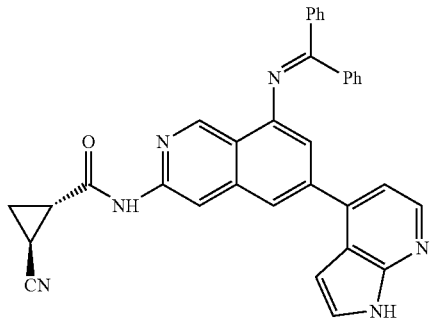 [SMILES: N#C[C@H]1C[C@@H]1C(=O)Nc1cc2cc(-c3ccnc4[nH]ccc34)cc(N=C(c3ccccc3)c3ccccc3)c2cn1]

A mixture of (±)-trans-N-[8-(benzhydrylideneamino)-6-[1-(p-tolylsulfonyl)pyrrolo[2,3-b]pyridin-4-yl]-3-isoquinolyl]-2-cyano-cyclopropanecarboxamide (100 mg, 0.15 mmol) and TBAF (152 mg, 0.58 mmol) in THF (15 mL) was stirred at 50° C. for 24 hours. The mixture was concentrated and purified by reverse phase prep-HPLC (Cis; acetonitrile/water+0.05% NH$_4$HCO$_3$) to give (±)-trans-N-[8-(benzhydrylideneamino)-6-(1H-pyrrolo[2,3-b]pyridin-4-yl)-3-isoquinolyl]-2-cyano-cyclopropanecarboxamide (68 mg, 88% yield) as a yellow solid. LCMS (ESI) [M+H]$^+$=533.2.

Step 4: (±)-trans-N-[8-amino-6-(1H-pyrrolo[2,3-b]pyridin-4-yl)-3-isoquinolyl]-2-cyano-cyclopropanecarboxamide

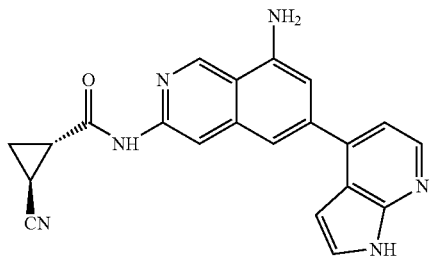 [SMILES: N#C[C@H]1C[C@@H]1C(=O)Nc1cc2cc(-c3ccnc4[nH]ccc34)cc(N)c2cn1]

A mixture of (±)-trans-N-[8-(benzhydrylideneamino)-6-(1H-pyrrolo[2,3-b]pyridin-4-yl)-3-isoquinolyl]-2-cyano-cyclopropanecarboxamide (68 mg, 0.13 mmol) in acetonitrile (10 mL), 2,2,2-trifluoroacetic acid (1 mL) and water (10 mL) was stirred at 25° C. for 20 minutes. The reaction mixture was neutralized with NH$_4$OH to pH=7-8. The mixture was concentrated and purified by reverse phase prep-HPLC (Cis, acetonitrile/water+0.05% NH$_4$HCO$_3$) to give (1)-trans-N-[8-amino-6-(1H-pyrrolo[2,3-b]pyridin-4-yl)-3-isoquinolyl]-2-cyano-cyclopropanecarboxamide (35 mg, 74% yield) as a yellow solid. LCMS (ESI) R$_T$ (min)=1.392, [M+H]$^+$=369.1, method=A. $^1$H NMR (400 MHz, DMSO-d$_6$) δ 11.80 (s, 1H), 11.11 (s, 1H), 9.36 (s, 1H), 8.31 (s, 1H), 8.30 (d, J=5.2 Hz, 1H), 7.56 (t, J=2.8 Hz, 1H), 7.28 (s, 1H), 7.23 (d, J=4.8 Hz, 1H), 7.04 (d, J=1.2 Hz, 1H), 6.67 (q, J=1.7 Hz, 1H), 6.42 (s, 2H), 2.79-2.75 (m, 1H), 2.17-2.12 (m, 1H), 1.62-1.57 (m, 1H), 1.47-1.42 (m, 1H).

Example 17

(±)-trans-N-[8-amino-6-(3-ethyl-1-methyl-6-oxo-2-pyridyl)-3-isoquinolyl]-2-cyano-cyclopropanecarboxamide (Compound 23)

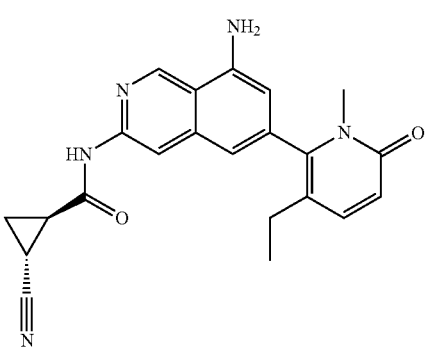 [SMILES: CCc1ccc(=O)n(C)c1-c1cc(N)c2cnc(NC(=O)[C@@H]3C[C@H]3C#N)cc2c1]

Step 1: 6-bromo-1-methyl-pyridin-2-one

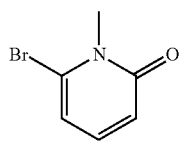

To a mixture of 6-bromo-1H-pyridin-2-one (5.0 g, 28.74 mmol) and K$_2$CO$_3$ (7.93 g, 57.47 mmol) in acetonitrile (100 mL) was added iodomethane (8.16 g, 57.47 mmol). The mixture was stirred overnight. The mixture was then filtered. The filtrate was concentrated and purified by flash column chromatography (50% ethyl acetate in petroleum ether) to afford 6-bromo-1-methyl-pyridin-2-one (4.5 g, 83% yield) as a white solid. LCMS (ESI): [M+H]$^+$=189.9.

Step 2: 6-bromo-5-iodo-1-methyl-pyridin-2-one

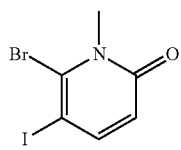

A mixture of 6-bromo-1-methyl-pyridin-2-one (3.7 g, 19.68 mmol) and NIS (4.43 g, 25.58 mmol) in DMF (15 mL) was stirred for 2 days at room temperature. The mixture was purified by prep-TLC (petroleum ether/ethyl acetate=2/1) to give 6-bromo-5-iodo-1-methyl-pyridin-2-one (1.1 g, 18% yield) as a yellow solid. LCMS (ESI): [M+H]$^+$=313.9; $^1$H NMR (400 MHz, CD$_3$OD) δ 7.68 (d, J=9.6 Hz, 1H), 6.27 (d, J=9.6 Hz, 1H), 3.77 (s, 3H).

Step 3: 6-bromo-1-methyl-5-vinyl-pyridin-2-one

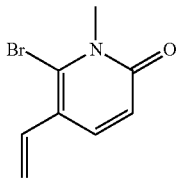

A mixture of 6-bromo-5-iodo-1-methyl-pyridin-2-one (1000 mg, 3.19 mmol), 4,4,5,5-tetramethyl-2-vinyl-1,3,2-dioxaborolane (1471 mg, 9.56 mmol), Pd(PPh$_3$)$_4$ (367 mg, 0.32 mmol), and K$_2$CO$_3$ (879 mg, 6.37 mmol) in 1,4-dioxane (50 mL) and water (2 mL) was stirred under N$_2$ at 60° C. for 18 hours. The mixture was concentrated and purified by prep-TLC (petroleum ether/ethyl acetate=4/1) to give 6-bromo-1-methyl-5-vinyl-pyridin-2-one (600 mg, 68% yield) as white solid. LCMS (ESI): [M+H]$^+$=216.0.

Step 4: 6-bromo-5-ethyl-1-methyl-pyridin-2-one

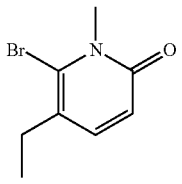

To a 25 mL flask was added 6-bromo-1-methyl-5-vinyl-pyridin-2-one (500 mg, 2.34 mmol), Pt/C (80 mg, 2.34 mmol) and ethyl acetate (15 mL), the mixture was stirred at room temperature under a H$_2$ atmosphere for 10 minutes. The mixture was filtered and the filtrate was concentrated. The crude product was purified by prep-TLC eluting with petroleum ether/ethyl acetate (2:1) to afford 6-bromo-5-ethyl-1-methyl-pyridin-2-one (470 mg, 89% yield) as a white solid. LCMS (ESI): [M+H]$^+$=218.0.

Step 5: 6-(3-amino-8-chloro-6-isoquinolyl)-5-ethyl-1-methyl-pyridin-2-one

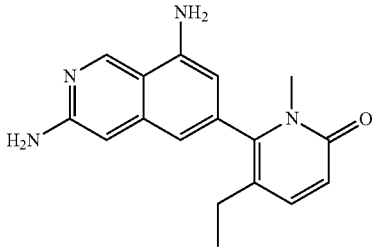 [SMILES: CCc1ccc(=O)n(C)c1-c1cc(N)c2cnc(N)cc2c1]

To a sealed tube was added (3-amino-8-chloro-6-isoquinolyl)boronic acid (494 mg, 2.22 mmol), 6-bromo-5-ethyl-1-methyl-pyridin-2-one (400 mg, 1.85 mmol), Pd(dppf) Cl$_2$ (151 mg, 0.21 mmol), K$_3$PO$_4$ (355 mg, 1.68 mmol), sodium acetate (414 mg, 5.05 mmol), acetonitrile (20 mL) and water (2 mL). The mixture was bubbled through with N$_2$ for 2 minutes, and stirred at 90° C. for 3 hours. The mixture was concentrated and purified by prep-TLC (petroleum ether/ethyl acetate, 1/4) to give 6-(3-amino-8-chloro-6-isoquinolyl)-5-ethyl-1-methyl-pyridin-2-one (210 mg, 26% yield) as a yellow solid. LCMS (ESI): [M+H]$^+$=314.1.

Step 6: (±)-trans-N-(8-chloro-6-(3-ethyl-1-methyl-6-oxo-1,6-dihydropyridin-2-yl)isoquinolin-3-yl)-2-cyanocyclopropanecarboxamide

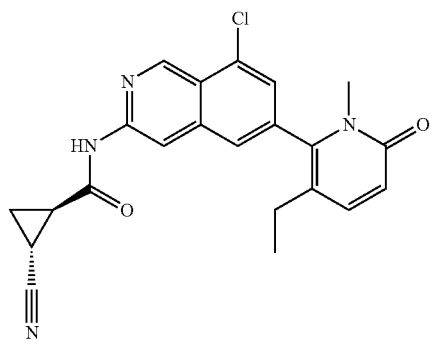

To a solution of 6-(3-amino-8-chloro-6-isoquinolyl)-5-ethyl-1-methyl-pyridin-2-one (180 mg, 0.57 mmol) and pyridine (0.14 mL, 1.72 mmol) in dichloromethane (15 mL) was added (±)-trans-2-cyanocyclopropanecarbonyl chloride (111 mg, 0.86 mmol). The mixture was stirred at 25° C. for 30 minutes. The mixture was concentrated and purified by prep-TLC to give (±)-trans-N-[8-chloro-6-(3-ethyl-1-methyl-6-oxo-2-pyridyl)-3-isoquinolyl]-2-cyano-cyclopropanecarboxamide (120 mg, 45% yield) as a yellow solid. LCMS (ESI): [M+H]$^+$=407.1.

Step 7: (±)-trans-N-[8-amino-6-(3-ethyl-1-methyl-6-oxo-2-pyridyl)-3-isoquinolyl]-2-cyano-cyclopropanecarboxamide

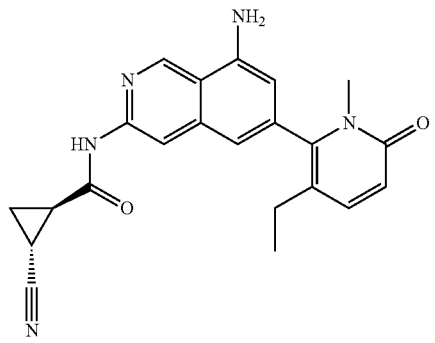 [SMILES: CCc1ccc(=O)n(C)c1-c1cc(N)c2cnc(NC(=O)[C@@H]3C[C@H]3C#N)cc2c1]

To a sealed tube was added tert-butyl carbamate (345 mg, 2.95 mmol), Pd$_2$(dba)$_3$ (54 mg, 0.06 mmol), Cs$_2$CO$_3$ (288 mg, 0.88 mmol), Xantphos (57 mg, 0.12 mmol), (±)-trans-N-[8-chloro-6-(3-ethyl-1-methyl-6-oxo-2-pyridyl)-3-isoquinolyl]-2-cyano-cyclopropanecarboxamide (120 mg, 0.29 mmol), DMF (3 mL) and toluene (3 mL) in a glove box. The mixture was stirred at 110° C. for 18 hours. The mixture was taken up in ethyl acetate (50 ml) and washed with brine. The organic layer was then separated, dried (Na$_2$SO$_4$) and concentrated to dryness. The crude was then purified by reverse phase prep-HPLC to give (±)-trans-N-[8-amino-6-(3-ethyl- 1-methyl-6-oxo-2-pyridyl)-3-isoquinolyl]-2-cyano-cyclopropanecarboxamide (25.5 mg, 22% yield) as a white solid. LCMS (ESI): $R_T$ (min)=1.528, [M+H]$^+$=388.1, method=A; $^1$H NMR (400 MHz, CD$_3$OD) δ 9.30 (s, 1H), 8.32 (s, 1H), 7.58 (d, J=9.2 Hz, 1H), 6.96 (s, 1H), 6.64 (d, J=9.2 Hz, 1H), 6.56 (s, 1H), 3.30 (s, 3H), 2.67-2.62 (m, 1H), 2.22-2.10 (m, 3H), 1.62-1.53 (m, 2H), 1.3 (t, J=7.6 Hz, 3H).

Example 18

(1)-cis-N-[8-amino-6-(1,4-dimethyl-2-oxo-3-pyridyl)-3-isoquinolyl]-2-fluoro-cyclopropanecarboxamide (Compound 24)

(±)-trans-N-[8-amino-6-(1,4-dimethyl-2-oxo-3-pyridyl)-3-isoquinolyl]-2-fluoro-cyclopropanecarboxamide (Compound 25)

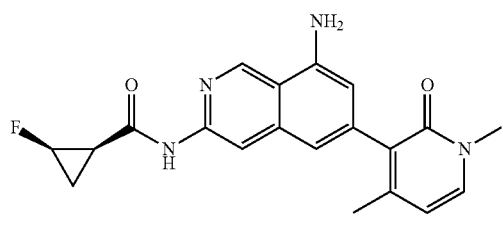

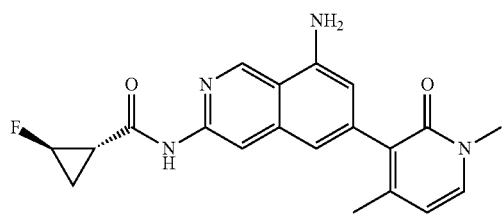

Step 1: 3-bromo-1,4-dimethyl-pyridin-2-one

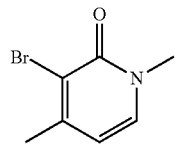

To a mixture of 3-bromo-4-methyl-1H-pyridin-2-one (600 mg, 3.19 mmol) and K$_2$CO$_3$ (880 mg, 6.38 mmol) in acetonitrile (100 mL) was added iodomethane (905 mg, 6.38 mmol). The mixture was stirred overnight at room temperature. The mixture was then filtered, concentrated and purified by flash column chromatography (50% ethyl acetate in petroleum ether) to afford 3-bromo-1,4-dimethyl-pyridin-2-one (570 mg, 88% yield) as a white solid. LCMS (ESI): [M+H]$^+$=202.0.

Step 2: 3-(3-amino-8-chloroisoquinolin-6-yl)-1,4-dimethylpyridin-2(1H)-one

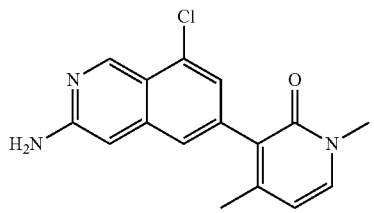 [SMILES: Cc1ccn(C)c(=O)c1-c1cc(Cl)c2cnc(N)cc2c1]

To a sealed tube was added 3-bromo-1,4-dimethyl-pyridin-2-one (350 mg, 1.73 mmol), (3-amino-8-chloro-6-isoquinolyl)boronic acid (462 mg, 2.08 mmol), Pd(dppf)Cl$_2$ (141 mg, 0.19 mmol), K$_3$PO$_4$ (332 mg, 1.57 mmol), sodium acetate (387 mg, 4.72 mmol), acetonitrile (20 mL) and water (2 mL). The mixture was bubbled through with N$_2$ for 2 minutes and stirred at 90° C. for 3 hours. The mixture was concentrated and purified by flash column chromatography (100% ethyl acetate) to give 3-(3-amino-8-chloro-6-isoquinolyl)-1,4-dimethyl-pyridin-2-one (240 mg, 43% yield) as a yellow solid. LCMS (ESI): [M+H]$^+$=300.1.

Step 3: (±)-cis-N-[8-chloro-6-(1,4-dimethyl-2-oxo-3-pyridyl)-3-isoquinolyl]-2-fluoro-cyclopropanecarboxamide

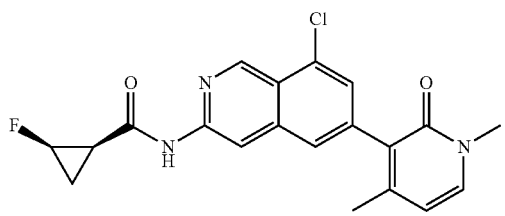 [SMILES: Cc1ccn(C)c(=O)c1-c1cc(Cl)c2cnc(NC(=O)[C@H]3C[C@H]3F)cc2c1]

To a cooled (0° C.) mixture of (±)-cis-2-fluorocyclopropanecarboxylic acid (83 mg, 0.80 mmol), 3-(3-amino-8-chloro-6-isoquinolyl)-1,4-dimethyl-pyridin-2-one (200 mg, 0.67 mmol) and pyridine (0.54 mL, 6.67 mmol) in dichloromethane (10 mL) was added POCl$_3$ (102 mg, 0.67 mmol). The mixture was stirred at room temperature for 1 hour. The mixture was concentrated and purified by prep-TLC (petroleum ether/ethyl acetate=1/2) to give (±)-cis-N-[8-chloro-6-(1,4-dimethyl-2-oxo-3-pyridyl)-3-isoquinolyl]-2-fluoro-cyclopropanecarboxamide (239 mg, 92% yield) as a gray solid. LCMS (ESI): [M+H]$^+$=386.1.

453

Step 4: (±)-cis-N-[8-amino-6-(1,4-dimethyl-2-oxo-3-pyridyl)-3-isoquinolyl]-2-fluoro-cyclopropanecarboxamide and trans-N-[8-amino-6-(1,4-dimethyl-2-oxo-3-pyridyl)-3-isoquinolyl]-2-fluoro-cyclopropanecarboxamide

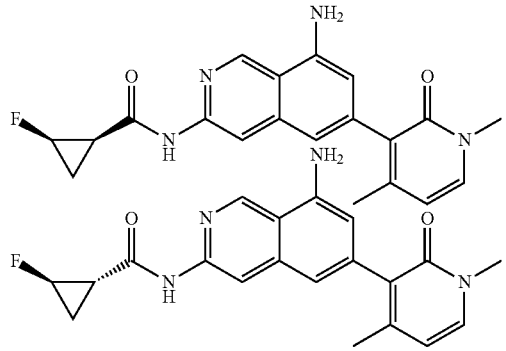

To a sealed tube was added tert-butyl carbamate (668 mg, 5.7 mmol), Pd$_2$(dba)$_3$ (104 mg, 0.11 mmol), Cs$_2$CO$_3$ (557 mg, 1.71 mmol), Xantphos (110 mg, 0.23 mmol), (±)-cis-N-[8-chloro-6-(1,4-dimethyl-2-oxo-3-pyridyl)-3-isoquinolyl]-2-fluoro-cyclopropanecarboxamide (220 mg, 0.57 mmol), DMF (3 mL), and toluene (3 mL) in a glove box. The mixture was stirred at 110° C. for 18 hours. The mixture was taken up in ethyl acetate (50 ml) and washed with brine. The organics were then separated, dried (Na$_2$SO$_4$), and concentrated to dryness. The crude product was then purified by reverse phase prep-HPLC to give (±)-cis-N-[8-amino-6-(1,4-dimethyl-2-oxo-3-pyridyl)-3-isoquinolyl]-2-fluoro-cyclopropanecarboxamide (29.6 mg, 14% yield) as a yellow solid and trans-N-[8-amino-6-(1,4-dimethyl-2-oxo-3-pyridyl)-3-isoquinolyl]-2-fluoro-cyclopropanecarboxamide (13 mg, 6% yield) as a yellow solid. (1)-cis-N-[8-amino-6-(1,4-dimethyl-2-oxo-3-pyridyl)-3-isoquinolyl]-2-fluoro-cyclopropanecarboxamide: LCMS (ESI): R$_T$ (min)=1.543, [M+H]$^+$=367.1, method=C; $^1$H NMR (400 MHz, CD$_3$OD) δ 9.21 (s, 1H), 8.28 (s, 1H), 7.58 (d, J=6.8 Hz, 1H), 6.91 (s, 1H), 6.58 (s, 1H), 6.40 (d, J=6.8 Hz, 1H), 4.98-4.78 (m, 1H), 3.59 (s, 3H), 2.17-2.13 (m, 1H), 2.01 (s, 3H), 1.87-1.76 (m, 1H), 1.26-1.17 (m, 1H). (±)-trans-N-[8-amino-6-(1,4-dimethyl-2-oxo-3-pyridyl)-3-isoquinolyl]-2-fluoro-cyclopropanecarboxamide: LCMS (ESI): R$_T$ (min)=1.524, [M+H]$^+$=367.1, method=B; $^1$H NMR (400 MHz, CD$_3$OD) δ 9.21 (s, 1H), 8.21 (s, 1H), 7.58 (d, J=6.8 Hz, 1H), 6.89 (s, 1H), 6.58 (s, 1H), 6.40 (d, J=6.8 Hz, 1H), 4.97-4.78 (m, 1H), 3.59 (s, 3H), 2.49-2.39 (m, 1H), 2.01 (s, 3H), 1.55-1.47 (m, 1H), 1.41-1.36 (m, 1H).

Example 19

(±)-cis-N-(8-amino-6-(6-methoxy-2-methylpyridin-3-yl)isoquinolin-3-yl)-2-fluorocyclopropanecarboxamide (Compound 26)

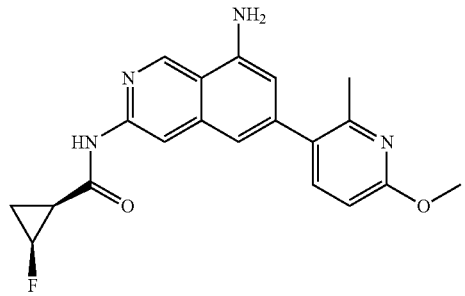 [SMILES: COc1ccc(-c2cc(N)c3cnc(NC(=O)[C@@H]4C[C@@H]4F)cc3c2)c(C)n1]

454

Step 1: 6-methoxy-2-methyl-3-(4,4,5,5-tetramethyl-1,3,2-dioxaborolan-2-yl)pyridine

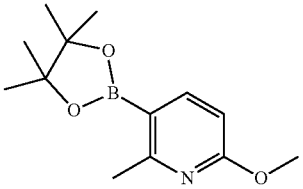

To a sealed tube was added 3-bromo-6-methoxy-2-methyl-pyridine (1.2 g, 5.94 mmol), bis(pinacolato)diboron (1.81 g, 7.13 mmol), Pd(dppf)Cl$_2$ (434 mg, 0.59 mmol), potassium acetate (1164 mg, 11.88 mmol) and 1,4-dioxane (10 mL). The mixture was stirred at 95° C. for 16 hours. The mixture was then concentrated and purified by prep-TLC (silica gel, petroleum ether/ethyl acetate=15/1) to give 2-methoxy-4-methyl-5-(4,4,5,5-tetramethyl-1,3,2-dioxaborolan-2-yl)pyridine (1.4 g, 94% yield) as a yellow oil. LCMS (ESI) [M+H]$^+$=250.0.

Step 2: (±)-cis-N-(8-chloro-6-(6-methoxy-2-methylpyridin-3-yl)isoquinolin-3-yl)-2-fluorocyclopropanecarboxamide

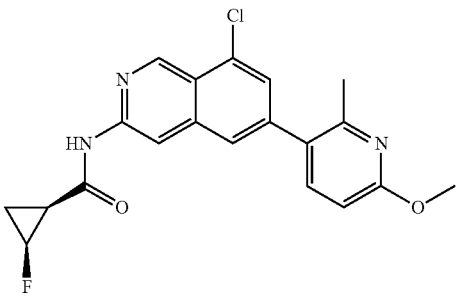 [SMILES: COc1ccc(-c2cc(Cl)c3cnc(NC(=O)[C@@H]4C[C@@H]4F)cc3c2)c(C)n1]

A mixture of 6-methoxy-2-methyl-3-(4,4,5,5-tetramethyl-1,3,2-dioxaborolan-2-yl)pyridine (725 mg, 2.91 mmol), (±)-cis-N-(6-bromo-8-chloro-3-isoquinolyl)-2-fluoro-cyclopropanecarboxamide (500 mg, 1.46 mmol), PdCl$_2$(dppf) (106 mg, 0.15 mmol), and K$_2$CO$_3$ (602 mg, 4.37 mmol) in 1,4-dioxane (3 mL) and water (0.5 mL) was purged 3 times with N$_2$. The mixture was stirred at 90° C. for 3 hours. Water (10 mL) was added. The mixture was extracted with ethyl acetate (10 mL×2). The organic layer was washed with water (20 mL×3) then brine (20 mL), dried over Na$_2$SO$_4$, filtered and concentrated. The residue was purified by prep-TLC (silica gel, petroleum ether/ethyl acetate=3/1) to give (±)-cis-N-[8-chloro-6-(6-methoxy-2-methyl-3-pyridyl)-3-isoquinolyl]-2-fluoro-cyclopropanecarboxamide (370 mg, 66% yield) as white solid. LCMS (ESI) [M+H]$^+$=386.0.

Step 3: (±)-cis-N-(8-amino-6-(6-methoxy-2-methylpyridin-3-yl)isoquinolin-3-yl)-2-fluorocyclopropanecarboxamide

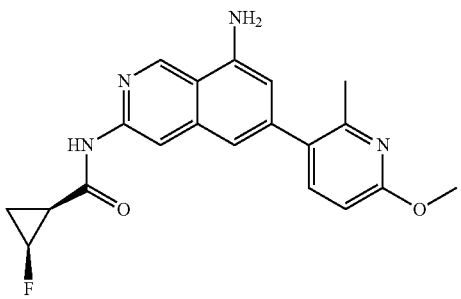 [SMILES: COc1ccc(-c2cc(N)c3cnc(NC(=O)[C@@H]4C[C@@H]4F)cc3c2)c(C)n1]

To a sealed tube was added tert-butyl carbamate (151 mg, 1.3 mmol), $Pd_2(dba)_3$ (23 mg, 0.03 mmol), $Cs_2CO_3$ (126 mg, 0.39 mmol), Xantphos (25 mg, 0.05 mmol), (±)-cis-N-[8-chloro-6-(6-methoxy-2-methyl-3-pyridyl)-3-isoquinolyl]-2-fluoro-cyclopropanecarboxamide (50 mg, 0.13 mmol) and toluene (1 mL) in a glove box. The mixture was stirred at 130° C. for 2 hours. Water (10 mL) was added. The mixture was extracted with ethyl acetate (10 mL×2). The organic layer was washed with water (20 mL×3), brine (20 mL), dried over $Na_2SO_4$, filtered and concentrated. The residue was purified by prep-TLC (silica gel, dichloromethane/methanol=20/1) to give (±)-cis-N-[8-amino-6-(6-methoxy-2-methyl-3-pyridyl)-3-isoquinolyl]-2-fluoro-cyclopropanecarboxamide (13 mg, 27% yield) as a yellow solid. LCMS (ESI) $R_T$ (min)=1.738, $[M+H]^+$=367.0. Method=G; $^1$H NMR (400 MHz, $CD_3OD$) δ 9.22 (s, 1H), 8.29 (s, 1H), 7.59 (d, J=8.4 Hz, 1H), 6.98 (s, 1H), 6.71 (d, J=8.0 Hz, 1H), 6.69 (d, J=1.6 Hz, 1H), 4.99-4.80 (m, 1H), 3.96 (s, 3H), 2.44 (s, 3H), 2.18-2.14 (m, 1H), 1.86-1.79 (m, 1H), 1.25-1.22 (m, 1H).

Example 20

(±)-cis-N-(8-amino-6-(2-methyl-6-oxo-1,6-dihydropyridin-3-yl)isoquinolin-3-yl)-2-fluorocyclopropanecarboxamide (Compound 27)

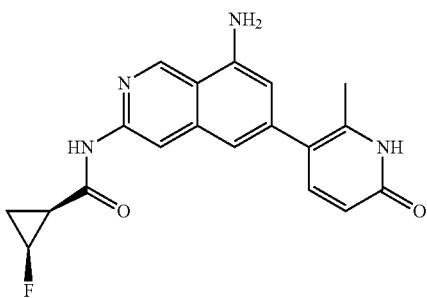 [SMILES: Cc1[nH]c(=O)ccc1-c1cc(N)c2cnc(NC(=O)[C@@H]3C[C@@H]3F)cc2c1]

A mixture of (±)-cis-N-[8-amino-6-(6-methoxy-2-methyl-3-pyridyl)-3-isoquinolyl]-2-fluoro-cyclopropanecarboxamide (100 mg, 0.27 mmol) in acetonitrile (4 mL) was added iodotrimethylsilane (0.04 mL, 0.27 mmol). The mixture was stirred at 90° C. for 1 hour. Water (10 mL) was added. The mixture was extracted with ethyl acetate (10 mL×2). The organic layer was washed with water (20 mL×3) then brine (20 mL), dried over $Na_2SO_4$, filtered and concentrated. The mixture was purified with reverse phase prep-HPLC to give (±)-cis-N-[8-amino-6-(6-hydroxy-2-methyl-3-pyridyl)-3-isoquinolyl]-2-fluoro-cyclopropanecarboxamide (50 mg, 52% yield) as a yellow solid. LCMS (ESI) $R_T$ (min)=1.348, $[M+H]^+$=353.0. Method=G; H NMR (400 MHz, $CD_3OD$) δ 9.20 (s, 1H), 8.29 (s, 1H), 7.62 (d, J=9.2 Hz, 1H), 6.97 (s, 1H), 6.65 (d, J=1.2 Hz, 1H), 6.48 (d, J=9.2 Hz, 1H), 4.98-4.80 (m, 1H), 2.35 (s, 3H), 2.18-2.13 (m, 1H), 1.86-1.79 (m, 1H), 1.24-1.20 (m, 1H).

Example 21

(±)-cis-N-(8-amino-6-(5-methyl-1H-pyrazol-4-yl)isoquinolin-3-yl)-2-fluorocyclopropanecarboxamide (Compound 28)

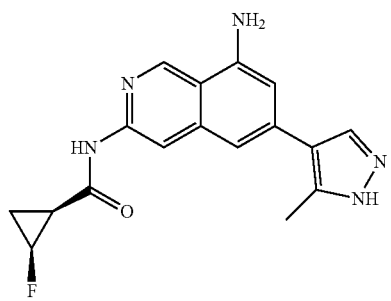 [SMILES: Cc1[nH]ncc1-c1cc(N)c2cnc(NC(=O)[C@@H]3C[C@@H]3F)cc2c1]

Step 1: (±)-cis-N-(8-chloro-6-(5-methyl-1-(tetrahydro-2H-pyran-2-yl)-1H-pyrazol-4-yl)isoquinolin-3-yl)-2-fluorocyclopropanecarboxamide

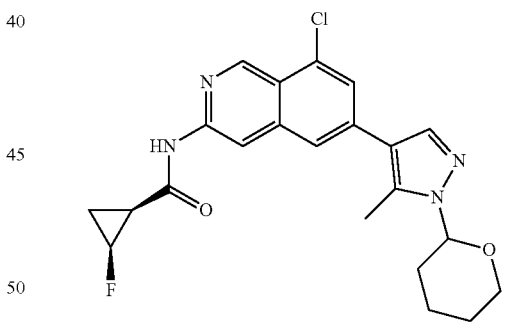

To a sealed tube was added (±)-cis-N-(6-bromo-8-chloro-3-isoquinolyl)-2-fluoro-cyclopropanecarboxamide (350 mg, 1.02 mmol), 5-methyl-1-tetrahydropyran-2-yl-4-(4,4,5,5-tetramethyl-1,3,2-dioxaborolan-2-yl)pyrazole (386 mg, 1.32 mmol), $Pd(dppf)Cl_2$ (92 mg, 0.13 mmol), $K_3PO_4$ (214 mg, 1.02 mmol) and sodium acetate (253 mg, 3.09 mmol), acetonitrile (20 mL) and water (2 mL). The mixture was bubbled through with $N_2$ for 2 min and stirred at 90° C. for 3 hours. Water (10 mL) was added. The mixture was extracted with ethyl acetate (10 mL×2). The organic layer was washed with brine (20 mL), dried over $Na_2SO_4$, filtered and concentrated. The residue was purified by prep-TLC (silica gel, petroleum ether/ethyl acetate=2/1) to give (±)-cis-N-[8-chloro-6-(5-methyl-1-tetrahydropyran-2-yl-pyrazol-4-yl)-3-isoquinolyl]-2-fluoro-cyclopropanecarboxamide (350 mg, 80% yield) as a yellow solid. LCMS (ESI) [M+H]⁺=429.7.

Step 2: (±)-cis-N-(8-amino-6-(5-methyl-1-(tetrahydro-2H-pyran-2-yl)-1H-pyrazol-4-yl)isoquinolin-3-yl)-2-fluorocyclopropanecarboxamide

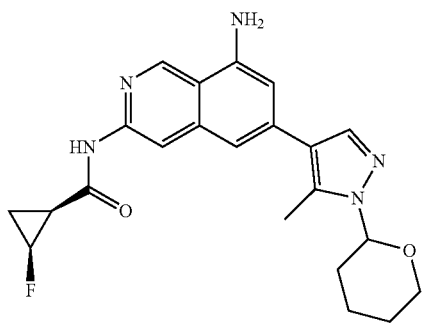 [SMILES: Cc1c(-c2cc(N)c3cnc(NC(=O)[C@@H]4C[C@@H]4F)cc3c2)cnn1C1CCCCO1]

To a sealed tube was added tert-butyl carbamate (956 mg, 8.16 mmol), Pd₂(dba)₃ (149 mg, 0.16 mmol), Cs₂CO₃ (1.33 g, 4.08 mmol), Xantphos (158 mg, 0.33 mmol), (±)-cis-N-[8-chloro-6-(5-methyl-1-tetrahydropyran-2-yl-pyrazol-4-yl)-3-isoquinolyl]-2-fluoro-cyclopropanecarboxamide (350 mg, 0.82 mmol) and toluene (5 mL) in a glove box. The mixture was stirred at 110° C. for 2 hours. Water (10 mL) was added. The mixture was extracted with ethyl acetate (10 mL×2). The organic layer was washed with water (20 mL×3) then brine (20 mL), dried over Na₂SO₄, filtered and concentrated to give crude product (±)-cis-N-[8-amino-6-(5-methyl-1-tetrahydropyran-2-yl-pyrazol-4-yl)-3-isoquinolyl]-2-fluoro-cyclopropanecarboxamide (0.3 g, 90% yield) as a yellow solid. LCMS (ESI) [M+H]⁺=410.7.

Step 3: (±)-cis-N-(8-amino-6-(5-methyl-H-pyrazol-4-yl)isoquinolin-3-yl)-2-fluorocyclopropanecarboxamide

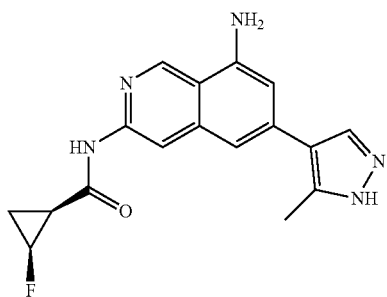 [SMILES: Cc1[nH]ncc1-c1cc(N)c2cnc(NC(=O)[C@@H]3C[C@@H]3F)cc2c1]

To a mixture of (±)-cis-N-[8-amino-6-(5-methyl-1-tetrahydropyran-2-yl-pyrazol-4-yl)-3-isoquinolyl]-2-fluoro-cyclopropanecarboxamide (200 mg, 0.49 mmol) in THF (3 mL) was added HCl in 1,4-dioxane (4 M in 1,4-dioxane, 8 mL, 32 mmol). The mixture was stirred at room temperature for 16 hours. The mixture was concentrated. A 7 M of NH₃ in methanol solution was added to adjust the pH of the mixture to 8. The mixture was concentrated and purified by reverse phase prep-HPLC to give (±)-cis-N-[8-amino-6-(5-methyl-H-pyrazol-4-yl)-3-isoquinolyl]-2-fluoro-cyclopropanecarboxamide (20 mg, 12.6% yield) as a yellow solid. LCMS (ESI) R_T (min)=1.417, [M+H]⁺=326.7. Method=G; ¹H NMR (400 MHz, CD₃OD) δ 9.14 (s, 1H), 8.27 (s, 1H), 7.81 (s, 1H), 7.14 (s, 1H), 6.90 (d, J=1.6 Hz, 1H), 4.99-4.79 (m, 1H), 2.52 (s, 3H), 2.19-2.12 (m, 1H), 1.87-1.79 (m, 1H), 1.25-1.20 (m, 1H).

Example 22

(1S,2S)—N-(8-amino-6-(5-oxopyrrolidin-3-yl)isoquinolin-3-yl)-2-fluorocyclopropanecarboxamide (Compound 30)

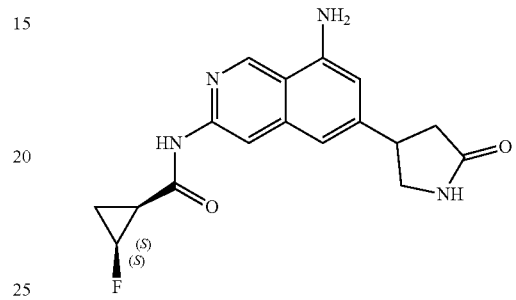

To a sealed tube was added tert-butyl carbamate (202 mg, 1.73 mmol), Pd₂(dba)₃ (31 mg, 0.03 mmol), Cs₂CO₃ (168 mg, 0.52 mmol), xantphos (33 mg, 0.07 mmol), (1S,2S)—N-[8-chloro-6-(6-methoxy-2-methyl-3-pyridyl)-3-isoquinolyl]-2-fluoro-cyclopropanecarboxamide (10 mg, 0.03 mmol), DMF (0.5 mL) and toluene (0.5 mL) in glove box. The mixture was stirred at 110° C. for 16 hours. Water (10 mL) was added. The mixture was extracted with ethyl acetate (10 mL×2). The organic extracts were washed with water (20 mL×3) then brine (20 mL), dried over Na₂SO₄, filtered and concentrated. The mixture was purified by reverse phase prep-HPLC to give (1S,2S)—N-[8-amino-6-(5-oxopyrrolidin-3-yl)-3-isoquinolyl]-2-fluoro-cyclopropanecarboxamide (10 mg, 17% yield) as a yellow solid. LCMS (ESI) R_T (min)=1.401, [M+H]⁺=329.7. Method=C; ¹H NMR (400 MHz, CD₃OD) δ 9.14 (s, 1H), 8.24 (s, 1H), 6.99 (s, 1H), 6.69 (s, 1H), 4.99-4.78 (m, 1H), 3.86-3.76 (m, 2H), 3.51-3.47 (m, 1H), 2.81-2.74 (m, 1H), 2.59-2.53 (m, 1H), 2.14-2.11 (m, 1H), 1.79-1.73 (m, 1H), 1.22-1.20 (m, 1H).

Example 23

(±)-cis-N-(8-amino-6-(4-ethyl-6-(hydroxymethyl)pyridin-3-yl)isoquinolin-3-yl)-2-fluorocyclopropanecarboxamide (Compound 31)

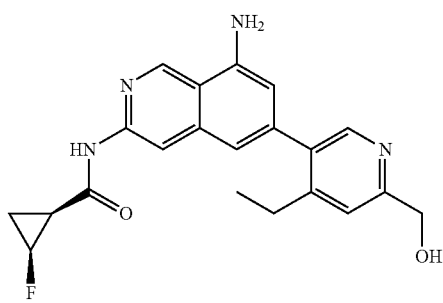 [SMILES: CCc1cc(CO)ncc1-c1cc(N)c2cnc(NC(=O)[C@@H]3C[C@@H]3F)cc2c1]

Step 1: (±)-methyl 5-(8-chloro-3-(cis-2-fluorocyclopropanecarboxamido)isoquinolin-6-yl)-4-ethylpicolinate

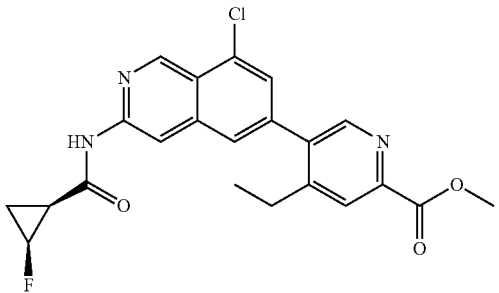 [SMILES: CCc1cc(C(=O)OC)ncc1-c1cc(Cl)c2cnc(NC(=O)[C@@H]3C[C@@H]3F)cc2c1]

A mixture of (±)-cis-N-(6-bromo-8-chloro-3-isoquinolyl)-2-fluoro-cyclopropanecarboxamide (130 mg, 0.38 mmol), methyl 4-ethyl-5-(4,4,5,5-tetramethyl-1,3,2-dioxaborolan-2-yl)pyridine-2-carboxylate (227 mg, 0.78 mmol), Pd(dppf)Cl$_2$ (26 mg, 0.04 mmol), K$_2$CO$_3$ (156 mg, 1.14 mmol) in 1,4-dioxane (1 mL) and water (0.2 mL) was purged 3 times with N$_2$. The mixture was stirred at 90° C. for 2 hours. Water (10 mL) was added. The mixture was extracted with ethyl acetate (10 mL×2). The combined extracts were washed with water and then brine, dried over Na$_2$SO$_4$, filtered and concentrated. The residue was purified by prep-TLC (silica gel, petroleum ether/ethyl acetate=2/1) to give (±)-methyl 5-[8-chloro-3-[[cis-2-fluorocyclopropanecarbonyl]amino]-6-isoquinolyl]-4-ethyl-pyridine-2-carboxylate (150 mg, 92% yield) as a yellow oil. LCMS (ESI) [M+H]$^+$=428.7.

Step 2: (±)-methyl 5-(8-amino-3-(cis-2-fluorocyclopropanecarboxamido)isoquinolin-6-yl)-4-ethylpicolinate

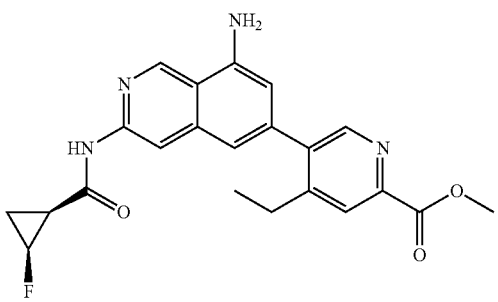 [SMILES: CCc1cc(C(=O)OC)ncc1-c1cc(N)c2cnc(NC(=O)[C@@H]3C[C@@H]3F)cc2c1]

To a sealed tube was added tert-butyl carbamate (410 mg, 3.51 mmol), Pd$_2$(dba)$_3$ (64 mg, 0.07 mmol), Cs$_2$CO$_3$ (342 mg, 1.05 mmol), Xantphos (67 mg, 0.1400 mmol), (±)-methyl 5-[8-chloro-3-[[cis-2-fluorocyclopropanecarbonyl]amino]-6-isoquinolyl]-4-ethyl-pyridine-2-carboxylate (150 mg, 0.35 mmol) toluene (1 mL) and DMF (1 mL) in glove box. The mixture was stirred at 130° C. for 2 hours. Water (10 mL) was added. The mixture was extracted with ethyl acetate (10 mL×2). The organic layer was washed with water (20 mL×3), brine (20 mL), dried over Na$_2$SO$_4$, filtered and concentrated. The residue was purified by prep-TLC (silica gel, dichloromethane/methanol, 20/1) to give (±)-methyl 5-[8-amino-3-[[cis-2-fluorocyclopropanecarbonyl]amino]-6-isoquinolyl]-4-ethyl-pyridine-2-carboxylate (60 mg, 42% yield) as a yellow solid. LCMS (ESI) [M+H]$^+$=409.7.

Step 3: (±)-cis-N-(8-amino-6-(4-ethyl-6-(hydroxymethyl)pyridin-3-yl)isoquinolin-3-yl)-2-fluorocyclopropanecarboxamide

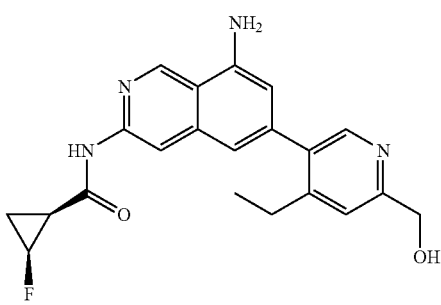 [SMILES: CCc1cc(CO)ncc1-c1cc(N)c2cnc(NC(=O)[C@@H]3C[C@@H]3F)cc2c1]

To a mixture of (±)-methyl 5-[8-amino-3-[[cis-2-fluorocyclopropanecarbonyl]amino]-6-isoquinolyl]-4-ethyl-pyridine-2-carboxylate (60 mg, 0.15 mmol) in methyl alcohol (5 mL) was added NaBH$_4$ (111 mg, 2.94 mmol) at 0° C. The mixture was stirred at room temperature for 5 hours. Water (2 mL) was added to quench the reaction. The mixture was concentrated and re-suspended in a solution of dichloromethane and methanol (10:1, 10 mL). The mixture was filtered and washed with a solution of dichloromethane and methanol (10:1). The filtrated was concentrated and purified by reverse phase rep-HPLC to give (±)-cis-N-[8-amino-6-[4-ethyl-6-(hydroxymethyl)-3-pyridyl]-3-isoquinolyl]-2-fluoro-cyclopropanecarboxamide (12 mg, 21% yield) as a yellow solid. LCMS (ESI) RT (min)=1.565, [M+H]$^+$=381.7. Method=C; $^1$HNMR (400 MHz, CD$_3$OD) δ 9.25 (s, 1H), 8.31 (s, 1H), 8.30 (s, 1H) 7.56 (s, 1H), 6.99 (s, 1H), 6.67 (d, J=1.6 Hz, 1H), 4.98-4.75 (m, 1H), 4.75 (s, 2H), 2.74 (q, J=7.2 Hz, 2H), 2.18-2.15 (m, 1H), 1.88-1.85 (m, 1H), 1.23-1.20 (m, 1H), 1.18 (t, J=7.2 Hz, 3H).

Example 24

(±)-trans-N-(8-amino-6-(4-methylpyridin-3-yl)isoquinolin-3-yl)-2-cyanocyclopropanecarboxamide (Compound 32)

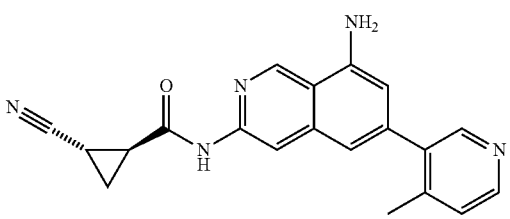 [SMILES: Cc1ccncc1-c1cc(N)c2cnc(NC(=O)[C@H]3C[C@@H]3C#N)cc2c1]

The compound was synthesized using a method similar to those described herein. The LC/MS and NMR data are shown in Table A-1.

Example 25

(1S,2S)—N-(8-amino-6-(4-methyl-2-oxooxazolidin-3-yl)isoquinolin-3-yl)-2-fluorocyclopropane carboxamide (Compound 37)

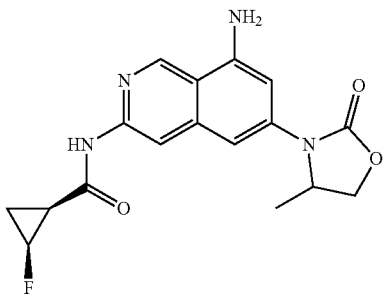 [SMILES: CC1COC(=O)N1c1cc(N)c2cnc(NC(=O)[C@@H]3C[C@@H]3F)cc2c1]

Step 1: 3-methyl-4-(4,4,5,5-tetramethyl-1,3,2-dioxaborolan-2-yl)pyridine

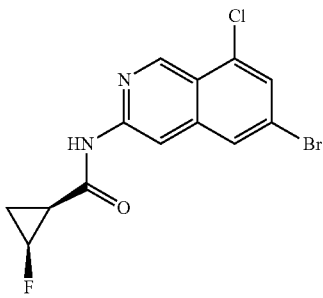 [SMILES: O=C(Nc1cc2cc(Br)cc(Cl)c2cn1)[C@@H]1C[C@@H]1F]

A mixture of 6-bromo-8-chloro-isoquinolin-3-amine (1 g, 3.88 mmol) and (1S,2S)-2-fluorocyclopropanecarboxylic acid (0.49 g, 4.66 mmol) in dichloromethane (10 mL) and pyridine (0.5 mL) was stirred at 0° C. for 0.5 hours before the addition of POCl₃ (0.4 mL, 4.29 mmol). The reaction was then stirred at room temperature for 1 hour. The reaction mixture was diluted with ethyl acetate (10 mL) and pH adjusted to 7-8 with saturated NaHCO₃. The organic layer was then separated, dried (NaSO₄) and concentrated to dryness. The residue was purified with silica-gel column chromatography (petroleum ether:ethyl acetate, 1:1) to give the title compound (1 g, 62.5% yield). LCMS (ESI) [M+H]⁺=345.0.

Step 2: (1S,2S)—N-(8-chloro-6-(4-methyl-2-oxooxazolidin-3-yl)isoquinolin-3-yl)-2-fluorocyclopropanecarboxamide

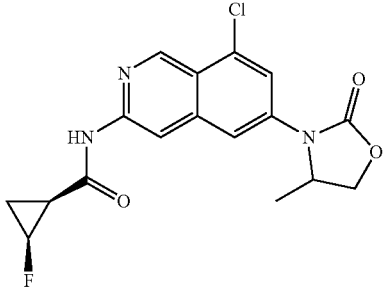 [SMILES: CC1COC(=O)N1c1cc(Cl)c2cnc(NC(=O)[C@@H]3C[C@@H]3F)cc2c1]

A mixture of (1S,2S)—N-(6-bromo-8-chloro-3-isoquinolyl)-2-fluoro-cyclopropanecarboxamide (150 mg, 0.44 mmol), 4-methyloxazolidin-2-one (53 mg, 0.52 mmol), Xanphos (25 mg, 0.04 mmol), Pd₂(dba)₃ (40 mg, 0.04 mmol) and K₃PO₄ (277 mg, 1.31 mmol) in 1,4-dioxane (4 mL) was stirred at 90° C. for 3 hours. The reaction was concentrated to dryness. The residue was purified with silica-gel column chromatography (petroleum ether/ethyl acetate=1:1 to petroleum ether/ethyl acetate=1:2) to give the title compound as a yellow solid (140 mg, 61% yield). LCMS (ESI) [M+H]⁺=364.1.

Step 3: tert-butyl 3-((1S,2S)-2-fluorocyclopropanecarboxamido)-6-(4-methyl-2-oxooxazolidin-3-yl)isoquinolin-8-ylcarbamate

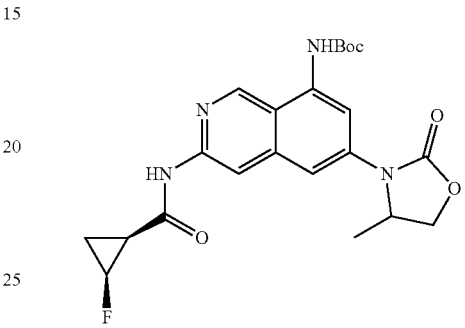

A mixture of tert-butyl carbamate (241 mg, 2.06 mmol), (1S,2S)—N-[8-chloro-6-(4-methyl-2-oxo-oxazolidin-3-yl)-3-isoquinolyl]-2-fluoro-cyclopropanecarboxamide (150 mg, 0.41 mmol), Pd₂(dba)₃ (74 mg, 0.08 mmol), Brettphos (44 mg, 0.08 mmol), and tBuONa (118 mg, 1.23 mmol) in 1,4-dioxane (3 mL) was stirred under Ar at 90° C. for 6 hours. The reaction was concentrated to dryness. The residue was purified by silica-gel column chromatography (petroleum ether:ethyl acetate=2:1 to petroleum ether:ethyl acetate=1:1) to give the title compound as a yellow solid (70 mg, 14.8% yield). LCMS (ESI) [M+H]⁺=445.2.

Step 4: (1S,2S)—N-(8-amino-6-(4-methyl-2-oxooxazolidin-3-yl)isoquinolin-3-yl)-2-fluorocyclopropanecarboxamide

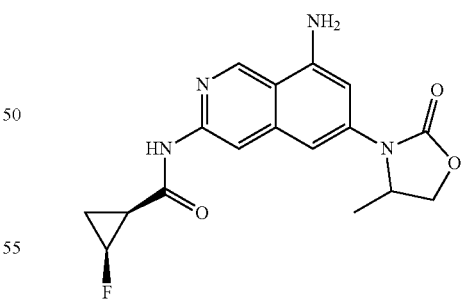

A mixture of tert-butyl N-[3-[[(1S,2S)-2-fluorocyclopropanecarbonyl]amino]-6-(4-methyl-2-oxo-oxazolidin-3-yl)-8-isoquinolyl]carbamate (70 mg, 0.16 mmol) in HCl in 1,4-dioxane (1 mL, 4 M) was stirred at room temperature for 1 hour. The reaction was concentrated to dryness. The residue was taken up in methanol (2 mL) and adjusted pH to 7-8 with sat NaHCO₃. The mixture was purified by reverse phase prep-HPLC to give the title compound as a brown solid. LCMS (ESI): RT (min)=1.54, [M+H]⁺=345.1, method=C. $^1$H NMR (400 MHz, DMSO-$d_6$) δ 10.74 (s, 1H), 9.19 (s, 1H), 8.19 (s, 1H), 7.00 (d, J=2.0 Hz, 1H), 6.92 (d, J=1.6 Hz, 1H), 6.32 (s, 2H), 5.01-4.83 (m, 1H), 4.71-4.68 (m, 1H), 4.58-4.54 (m, 1H), 4.06-4.03 (m, 1H), 2.28-2.21 (m, 1H), 1.71-1.61 (m, 1H), 1.29 (d, J=6.0 Hz, 3H), 1.19-1.12 (m, 1H).

Example 26

(±)-trans-N-(8-amino-6-(quinolin-4-yl)isoquinolin-3-yl)-2-cyanocyclopropanecarboxamide (Compound 38)

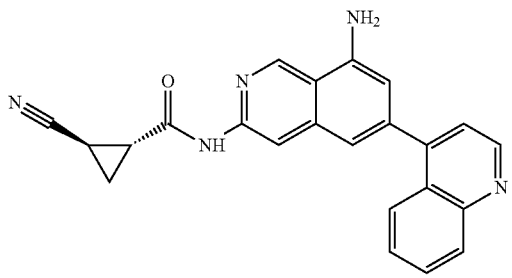 [SMILES: N#C[C@@H]1C[C@H]1C(=O)Nc1cc2cc(-c3ccnc4ccccc34)cc(N)c2cn1]

Step 1: quinolin-4-ylboronic Acid

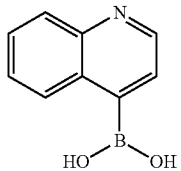 [SMILES: OB(O)c1ccnc2ccccc12]

A mixture of 4-bromoquinoline (1.0 g, 4.81 mmol), bis(pinacolato)diboron (12.0 g, 47.26 mmol), PdCl$_2$dppf (0.7 g, 0.96 mmol), potassium acetate (1.4 g, 14.29 mmol) in 1,4-dioxane (100 mL) was stirred under Ar at 80° C. for 2 hours. The reaction was concentrated to dryness. The residue was purified by silica-gel column chromatography (petroleum ether/ethyl acetate=1:1 to dichloromethane: methanol=1:1) to give the title compound as a yellow solid (2 g, crude). LCMS (ESI) [M+H]$^+$=256.1.

Step 2: (±)-trans-N-(8-chloro-6-(quinolin-4-yl)isoquinolin-3-yl)-2-cyanocyclopropanecarboxamide

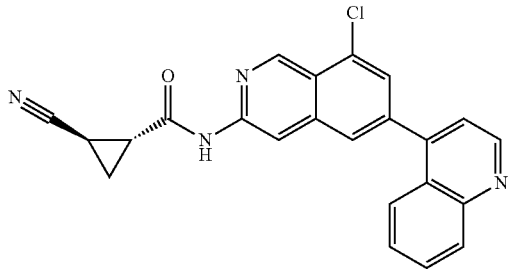

A mixture of trans-N-(6-bromo-8-chloro-3-isoquinolyl)-2-cyano-cyclopropanecarboxamide (800 mg, 2.28 mmol), quinoline-4-boronic acid (100 mg, 0.58 mmol), Pd(PPh$_3$)$_4$ (67 mg, 0.06 mmol), and K$_2$CO$_3$ (239 mg, 1.73 mmol) in 1,4-dioxane (4 mL) and water (1 mL) was stirred under Ar at 90° C. for 3 hours. The reaction was concentrated to dryness. The residue was purified by silica gel column chromatography (petroleum ether/ethyl acetate=4:1 to petroleum ether/acetate=2:1) to give the title compound as a yellow solid (100 mg, 25.3% yield). LCMS (ESI) [M+H]$^+$=399.1.

Step 3: (±)-trans-2-cyano-N-(8-(diphenylmethyleneamino)-6-(quinolin-4-yl)isoquinolin-3-yl)cyclopropanecarboxamide

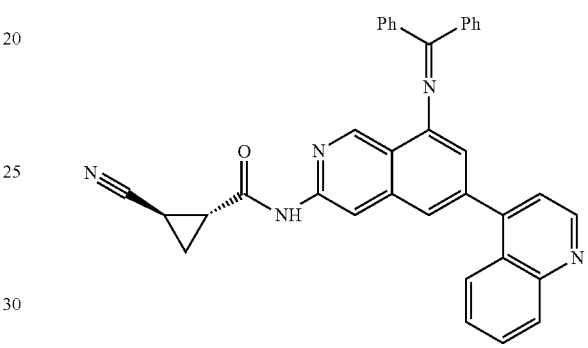

A mixture of trans-N-[8-chloro-6-(4-quinolyl)-3-isoquinolyl]-2-cyano-cyclopropanecarboxamide (90 mg, 0.23 mmol), benzophenone imine (123 mg, 0.68 mmol), Pd$_2$(dba)$_3$ (41 mg, 0.04 mmol), Xantphos (13 mg, 0.02 mmol), and Cs$_2$CO$_3$ (220 mg, 0.67 mmol) in DMF (3 mL) and toluene (1 mL) was heated in a microwave reactor at 150° C. for 1 hour. The reaction was diluted with ethyl acetate and washed with brine. The organic extract was then separated, dried (Na$_2$SO$_4$) and concentrated to dryness. The residue was purified by silica gel column chromatography (petroleum ether/ethyl acetate=4:1) to give the title compound as a yellow solid (40 mg, 33% yield). LCMS (ESI) [M+H]$^+$=544.2.

Step 4: (±)-trans-N-(8-amino-6-(quinolin-4-yl)isoquinolin-3-yl)-2-cyanocyclopropanecarboxamide

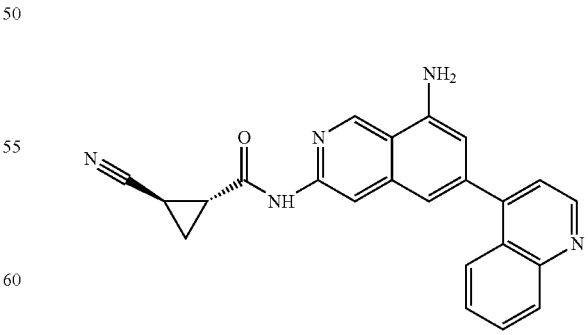

A mixture of (±)-trans-N-[8-(benzhydrylideneamino)-6-(4-quinolyl)-3-isoquinolyl]-2-cyano-cyclopropanecarboxamide (40 mg, 0.07 mmol), and TFA (0.5 mL, 6.71 mmol) in dichloromethane (2 mL) and two drops of water was stirred at room temperature for 3 hours. The reaction was concentrated to dryness. The residue was taken up in ethyl acetate (10 mL) and adjusted pH to 7-8 with saturated aqueous NaHCO$_3$. The mixture was concentrated to dryness and purified by silica gel column chromatography (ethyl acetate/petroleum ether=2:1 to ethyl acetate) to give the title compound as a yellow solid (18.5 mg, 64% yield). LCMS (ESI) R$_T$(min)=1.573, [M+H]$^+$=380.1, method=B. $^1$H NMR (400 MHz, DMSO-d$_6$) δ 11.15 (s, 1H), 9.41 (s, 1H), 8.96 (d, J=4.4 Hz, 1H), 8.28 (s, 1H), 8.12 (d, J=8.0 Hz, 1H), 7.95 (d, J=8.4 Hz, 1H), 7.82-7.78 (m, 1H), 7.62-7.58 (m, 1H), 7.51 (d, J=4.4 Hz, 1H), 7.07 (s, 1H), 6.73 (d, J=1.6 Hz, 1H), 6.49 (s, 2H), 2.77-2.72 (m, 1H), 2.15-2.11 (m, 1H), 1.60-1.58 (m, 1H), 1.45-1.40 (m, 1H).

Example 27

(±)-cis-N-(8-amino-6-(5-amino-4-ethylpyridin-3-yl)isoquinolin-3-yl)-2-fluorocyclopropanecarboxamide (Compound 39)

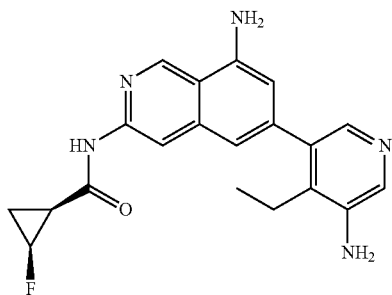 [SMILES: CCc1c(N)cncc1-c1cc(N)c2cnc(NC(=O)[C@@H]3C[C@@H]3F)cc2c1]

Step 1: 3,5-dibromo-4-ethylpyridine

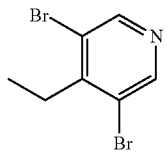

To a solution of diisopropylamine (3.5 mL, 24.8 mmol) in THF (50 mL) was added n-BuLi (2.5 M in hexane, 10.5 mL, 26.25 mmol) in portions at −78° C. The mixture was stirred at room temperature for 15 minutes. To the reaction mixture was then added 3,5-dibromopyridine (5.0 g, 21.11 mmol) at −78° C. under N$_2$. After 1 h of stirring at −78° C., iodoethane (3.29 g, 21.11 mmol) was added at −78° C. The mixture was then stirred at room temperature for 16 hours. The reaction was then washed with a saturated solution of NH$_4$Cl (100 mL). The organics were then separated, dried (Na$_2$SO$_4$) and concentrated to dryness. The residue was purified by silica-gel column chromatography (petroleum ether/ethyl acetate=20:1) to give the title compound as a yellow solid. LCMS (ESI) [M+H]$^+$=265.9.

Step 2: tert-butyl 5-bromo-4-ethylpyridin-3-ylcarbamate

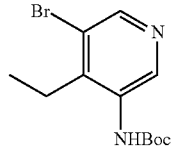 [SMILES: CCc1c(Br)cncc1NC(=O)OC(C)(C)C]

A mixture of 3,5-dibromo-4-ethyl-pyridine (2.4 g, 9.06 mmol), tert-butyl carbamate (1.0 g, 8.54 mmol), K$_2$CO$_3$ (2.5 g, 18.12 mmol), CuI (0.86 g, 4.53 mmol), and N1,N2-dimethylethane-1,2-diamine (0.4 g, 4.55 mmol) in 1,4-dioxane (60 mL) was stirred under Ar at 100° C. for 4 hours. The reaction was filtered and concentrated to dryness. The residue was purified by silica-gel column chromatography (petroleum ether/ethyl acetate=10:1 to petroleum ether/ethyl acetate=4:1) to give the title compound as a white solid (1.01 g, 37% yield). LCMS (ESI) [M+H]$^+$=301.0.

Step 3: tert-butyl 4-ethyl-5-(4,4,5,5-tetramethyl-1,3,2-dioxaborolan-2-yl)pyridin-3-ylcarbamate

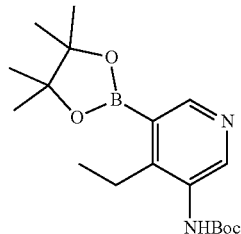 [SMILES: CCc1c(NC(=O)OC(C)(C)C)cncc1B1OC(C)(C)C(C)(C)O1]

A mixture of bis(pinacolato)diboron (1.26 g, 4.98 mmol), tert-butyl N-(5-bromo-4-ethyl-3-pyridyl)carbamate (1.0 g, 3.32 mmol), PdCl$_2$dppf (0.24 g, 0.33 mmol), and potassium acetate (0.98 g, 9.96 mmol) in 1,4-dioxane (20 mL) was stirred under Ar at 90° C. for 3 hours. The reaction was concentrated to dryness and purified by silica-gel column chromatography (ethyl acetate) to give the title compound as a black oil (490 mg, 25% yield). LCMS (ESI) [M+H]$^+$=349.3.

Step 4: (±)-tert-butyl 5-(8-chloro-3-((cis)-2-fluorocyclopropanecarboxamido)isoquinolin-6-yl)-4-ethylpyridin-3-ylcarbamate

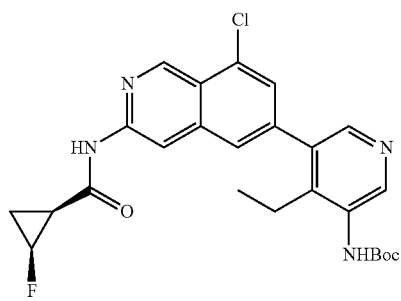 [SMILES: CCc1c(NC(=O)OC(C)(C)C)cncc1-c1cc(Cl)c2cnc(NC(=O)[C@@H]3C[C@@H]3F)cc2c1]

A mixture of (±)-tert-butyl N-[4-ethyl-5-(4,4,5,5-tetramethyl-1,3,2-dioxaborolan-2-yl)-3-pyridyl]carbamate (250 mg, 0.72 mmol), cis-N-(6-bromo-8-chloro-3-isoquinolyl)-2-fluoro-cyclopropanecarboxamide (150 mg, 0.44 mmol), PdCl$_2$dppf (52 mg, 0.07 mmol), K$_3$PO$_4$ (304 mg, 1.43 mmol) and sodium acetate (117 mg, 1.43 mmol) in acetonitrile (4 mL) and water (1 mL) was stirred under Ar at 90° C. for 3 hours. The reaction was concentrated to dryness. The residue was then purified by silica gel column chromatography (petroleum ether/ethyl acetate=4:1 to petroleum ether/ethyl acetate=1:1) to give the title compound as a yellow solid (70 mg, 20.1% yield). LCMS (ESI) [M+H]$^+$=485.2.

Step 5: (±)-tert-butyl N-[6-[5-(tert-butoxycarbonylamino)-4-ethyl-3-pyridyl]-3-[[cis-2-fluorocyclopropanecarbonyl] amino]-8-isoquinolyl]carbamate

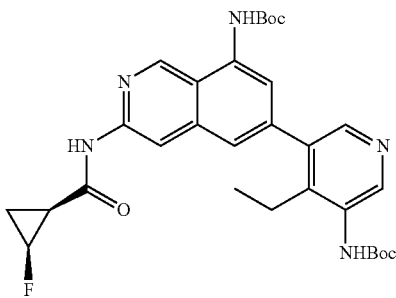 [SMILES: CCc1c(NC(=O)OC(C)(C)C)cncc1-c1cc(NC(=O)OC(C)(C)C)c2cnc(NC(=O)[C@@H]3C[C@@H]3F)cc2c1]

A mixture of tert-butyl N-[5-[8-chloro-3-[[cis-2-fluorocyclopropanecarbonyl]amino]-6-isoquinolyl]-4-ethyl-3-pyridyl]carbamate (40 mg, 0.08 mmol), tert-butyl carbamate (96 mg, 0.82 mmol), Pd$_2$(dba)$_3$ (8 mg, 0.01 mmol), Brettphos (5 mg, 0.01 mmol), and tBuONa (23 mg, 0.24 mmol) in 1,4-dioxane (2 mL) was heated under Ar at 90° C. for 1 hour. The reaction was concentrated to dryness. The residue was purified by silica-gel column chromatography (petroleum ether/ethyl acetate=1:1 to ethyl acetate/petroleum ether=2:1) to give the title compound as a yellow solid (20 mg, 34.7% yield). LCMS (ESI) [M+H]$^+$=566.3.

Step 6: (±)-cis-N-(8-amino-6-(5-amino-4-ethylpyridin-3-yl)isoquinolin-3-yl)-2-fluorocyclopropanecarboxamide

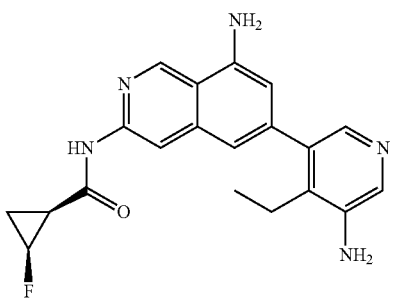 [SMILES: CCc1c(N)cncc1-c1cc(N)c2cnc(NC(=O)[C@@H]3C[C@@H]3F)cc2c1]

A mixture of (±)-tert-butyl N-[6-[5-(tert-butoxycarbonylamino)-4-ethyl-3-pyridyl]-3-[[(cis)-2-fluorocyclopropanecarbonyl]amino]-8-isoquinolyl]carbamate (20 mg, 0.04 mmol) in a solution of HCl in 1,4-dioxane (1 mL, 4 M) was stirred at room temperature for 1 hour. The reaction was concentrated to dryness. The residue was taken up in methanol (2 ml) and adjusted pH to 7-8 with saturated NaHCO$_3$. The mixture was purified by reverse phase prep-HPLC (5-95% methanol and 1% NH$_4$HCO$_3$ in water) to give the title compound as a yellow solid (11.6 mg, 83.5% yield). LCMS (ESI): R$_T$(min)=1.54, [M+H]$^+$=366.2, method=F. $^1$H NMR (400 MHz, DMSO-d$_6$) δ 10.80 (s, 1H), 9.30 (s, 1H), 8.24 (s, 1H), 7.94 (s, 1H), 7.57 (s, 1H), 6.79 (s, 1H), 6.48 (s, 1H), 6.31 (s, 2H), 5.21 (s, 2H), 5.02-4.84 (m, 1H), 2.46-2.41 (m, 2H), 2.27-2.24 (m, 1H), 1.69-1.62 (m, 1H), 1.18-1.14 (m, 1H), 0.98 (t, J=7.6 Hz, 3H).

Example 28

3-amino-N-(8-amino-6-(4-methylpyridin-3-yl)isoquinolin-3-yl)propanamide (Compound 40)

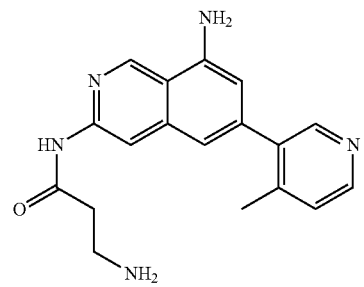 [SMILES: Cc1ccncc1-c1cc(N)c2cnc(NC(=O)CCN)cc2c1]

Step 1: tert-butyl 3-(6-bromo-8-chloroisoquinolin-3-ylamino)-3-oxopropylcarbamate

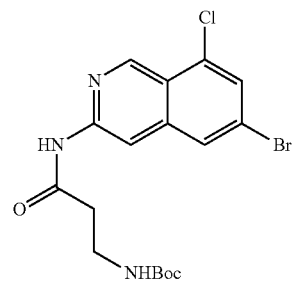 [SMILES: CC(C)(C)OC(=O)NCCC(=O)Nc1cc2cc(Br)cc(Cl)c2cn1]

A mixture of 6-bromo-8-chloro-isoquinolin-3-amine (150 mg, 0.58 mmol), 3-(tert-butoxycarbonylamino)propanoic acid (165 mg, 0.87 mmol) in dichloromethane (2 mL) and pyridine (0.5 mL) was stirred at 0° C. for 0.5 hours. POCl$_3$ (89 mg, 0.58 mmol) was added to the reaction mixture, then the mixture was stirred at room temperature for 1 hour. The reaction mixture was washed with 10 mL water and pH adjusted to 7-8 with saturated aqueous NaHCO$_3$. The organic layer was then separated and dried (NaSO$_4$) before concentration to dryness. The residue was purified with silica-gel column chromatography (petroleum ether/ethyl acetate=4:1 to petroleum ether/ethyl acetate=2:1) to give the title compound as a yellow solid (200 mg, 70% yield). LCMS (ESI) [M+H]$^+$=430.0.

469

Step 2: tert-butyl 3-(8-chloro-6-(4-methylpyridin-3-yl)isoquinolin-3-ylamino)-3-oxopropylcarbamate

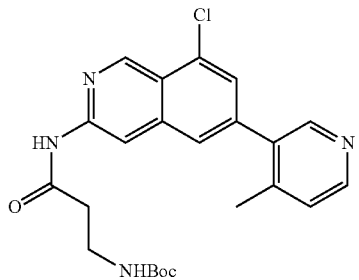 [SMILES: Cc1ccncc1-c1cc(Cl)c2cnc(NC(=O)CCNC(=O)OC(C)(C)C)cc2c1]

A mixture of tert-butyl N-[3-[(6-bromo-8-chloro-3-isoquinolyl)amino]-3-oxo-propyl]carbamate (195 mg, 0.45 mmol), 4-methyl-3-(4,4,5,5-tetramethyl-1,3,2-dioxaborolan-2-yl)pyridine (120 mg, 0.55 mmol), Pd(PPh$_3$)$_4$ (53 mg, 0.05 mmol), and K$_2$CO$_3$ (188 mg, 1.36 mmol) in 1,4-dioxane (8 mL) and water (2 mL) was heated under Ar at 90° C. for 3 hours. The reaction was concentrated to dryness. The residue was purified with silica-gel column chromatography (petroleum ether/ethyl acetate=1:1 to 100% ethyl acetate) to give the title compound as a yellow solid (190 mg, 59% yield). LCMS (ESI) [M+H]$^+$=441.2.

Step 3: tert-butyl 3-(3-aminopropanamido)-6-(4-methylpyridin-3-yl)isoquinolin-8-ylcarbamate

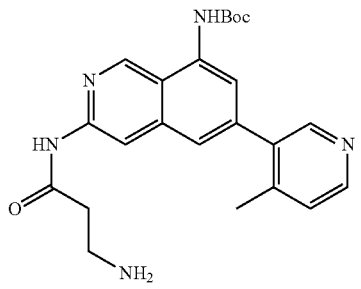 [SMILES: Cc1ccncc1-c1cc(NC(=O)OC(C)(C)C)c2cnc(NC(=O)CCN)cc2c1]

A mixture of tert-butyl carbamate (470 mg, 4.01 mmol), tert-butyl N-[3-[[8-chloro-6-(4-methyl-3-pyridyl)-3-isoquinolyl]amino]-3-oxo-propyl]carbamate (180 mg, 0.41 mmol), Cs$_2$CO$_3$ (398 mg, 1.22 mmol), Pd$_2$(dba)$_3$ (37 mg, 0.04 mmol), and Brettphos (21 mg, 0.04 mmol) in 1,4-dioxane (5 mL) was heated under Ar at 90° C. for 3 hours. The reaction was concentrated to dryness. The residue was purified with silica-gel column chromatography (petroleum ether/ethyl acetate=1:1 to ethyl acetate/petroleum ether=2:1) to give the title compound as a yellow solid (150 mg, 38% yield). LCMS (ESI) [M+H]$^+$=522.3.

Step 4: 3-amino-N-(8-amino-6-(4-methylpyridin-3-yl)isoquinolin-3-yl)propanamide

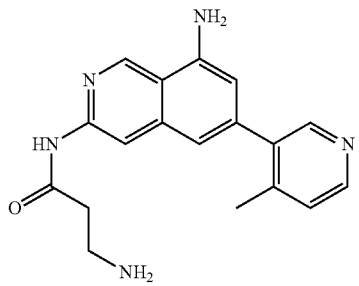

470

A mixture of tert-butyl N-[3-[[8-(tert-butoxycarbonylamino)-6-(4-methyl-3-pyridyl)-3-isoquinolyl]amino]-3-oxo-propyl]carbamate (150 mg, 0.29 mmol) in HCl in 1,4-dioxane (4.0 M, 2 mL, 8 mmol) was stirred at room temperature for 1 hour. The reaction was concentrated to dryness and the residue was taken up in methanol (2 mL) and adjusted pH to 7-8 with sat NaHCO$_3$. The mixture was purified directly with reverse phase prep-HPLC (5-95% methanol and 1% NH$_4$HCO$_3$) to give the title compound as a yellow solid (39.5 mg). LCMS (ESI): R$_T$ (min)=1.45, [M+H]$^+$=322.2, method=F. $^1$H NMR (400 MHz, CD$_3$OD) δ 9.23 (s, 1H), 8.40 (d, J=5.2 Hz, 1H), 8.39 (s, 1H), 8.33 (s, 1H), 7.39 (d, J=5.2 Hz, 1H), 6.99 (s, 1H), 6.68 (d, J=1.2 Hz, 1H), 3.05 (t, J=6.8 Hz, 2H), 2.66 (t, J=6.8 Hz, 2H), 2.37 (s, 3H).

Example 29

(±)-cis-N-(8-amino-6-(5-isopropyl-1H-pyrazol-4-yl)isoquinolin-3-yl)-2-fluoro cyclopropanecarboxamide (Compound 41)

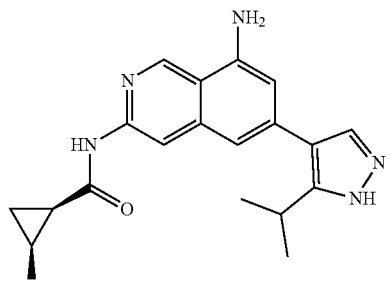

Step 1: 5-isopropyl-4-(4,4,5,5-tetramethyl-1,3,2-dioxaborolan-2-yl)-1H-pyrazole

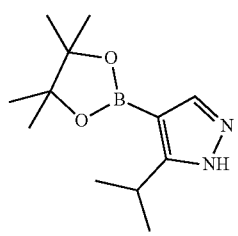 [SMILES: CC(C)c1[nH]ncc1B1OC(C)(C)C(C)(C)O1]

A mixture of 4-bromo-3-isopropyl-1H-pyrazole (2.0 g, 10.58 mmol), Pd(dppf)Cl$_2$ (1.0 g, 1.37 mmol), potassium acetate (4.8 g, 48.98 mmol), bis(pinacolato)diboron (25.0 g, 98.45 mmol) in 1,4-dioxane (100 mL) was stirred overnight under Ar at 100° C. The reaction was concentrated to dryness and the crude was then purified by silica gel column chromatography (ethyl acetate/petroleum ether, 1/10 to 1/1) to afford 3-isopropyl-4-(4,4,5,5-tetramethyl-1,3,2-dioxaborolan-2-yl)-1H-pyrazole (1.28 g, 39% yield) as a yellow liquid. LCMS(ESI):[M+H]$^+$=237.2.

Step 2: (±)-cis-N-(8-chloro-6-(5-isopropyl-1H-pyrazol-4-yl) isoquinolin-3-yl)-2-fluorocyclopropanecarboxamide Step 4: (±)-cis-N-[8-(benzhydrylideneamino)-6-(3-isopropyl-1-tetrahydropyran-2-yl-pyrazol-4-yl)-3-isoquinolyl]-2-fluoro-cyclopropanecarboxamide and (±)-trans-N-[8-(benzhydrylideneamino)-6-(3-isopropyl-1-tetrahydropyran-2-yl-pyrazol-4-yl)-3-isoquinolyl]-2-fluoro-cyclopropanecarboxamide

A pressure tube containing the reaction mixture of 3-isopropyl-4-(4,4,5,5-tetramethyl-1,3,2-dioxaborolan-2-yl)-1H-pyrazole (600 mg, 1.91 mmol), Pd(dppf)Cl$_2$ (100 mg, 0.14 mmol), K$_2$CO$_3$ (560 mg, 4.06 mmol), (±)-cis-N-(6-bromo-8-chloro-3-isoquinolyl)-2-fluoro-cyclopropanecarboxamide (520 mg, 1.51 mmol), 1,4-dioxane (10 mL) and water (1.5 mL) was heated in a microwave reactor at 130° C. for 80 minutes. The reaction was concentrated to dryness and the crude was then purified by silica gel column chromatography (ethyl acetate) to afford (±)-cis-N-[8-chloro-6-(3-isopropyl-1H-pyrazol-4-yl)-3-isoquinolyl]-2-fluoro-cyclopropanecarboxamide (220 mg, 37% yield) as a yellow solid. LCMS(ESI):[M+H]$^+$=373.1.

Step 3: (±)-cis-N-(8-chloro-6-(5-isopropyl-1-(tetrahydro-2H-pyran-2-yl)-1H-pyrazol-4-yl) isoquinolin-3-yl)-2-fluorocyclopropanecarboxamide

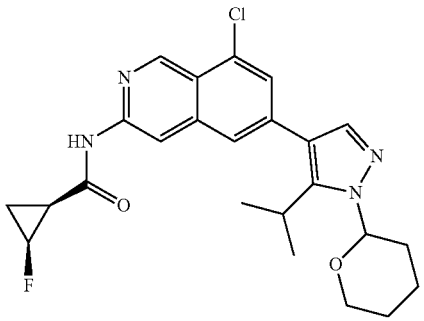 [SMILES: CC(C)c1c(-c2cc(Cl)c3cnc(NC(=O)[C@@H]4C[C@@H]4F)cc3c2)cnn1C1CCCCO1]

A solution of (±)-cis-N-[8-chloro-6-(5-isopropyl-1H-pyrazol-4-yl)-3-isoquinolyl]-2-fluoro-cyclopropanecarboxamide (220 mg, 0.59 mmol), 3,4-dihydro-2h-pyran (2.0 mL, 21.92 mmol), TFA (0.5 mL, 6.71 mmol) in dichloromethane (15 mL) was heated overnight at reflux. The reaction was concentrated to dryness and the crude was then purified by silica gel column chromatography (ethyl acetate/petroleum ether, 1/4 to 1/1) to afford (±)-cis-N-[8-chloro-6-(5-isopropyl-1-tetrahydropyran-2-yl-pyrazol-4-yl)-3-isoquinolyl]-2-fluoro-cyclopropanecarboxamide (230 mg, 84% yield) as a yellow solid. LCMS(ESI):[M+H]$^+$=457.2.

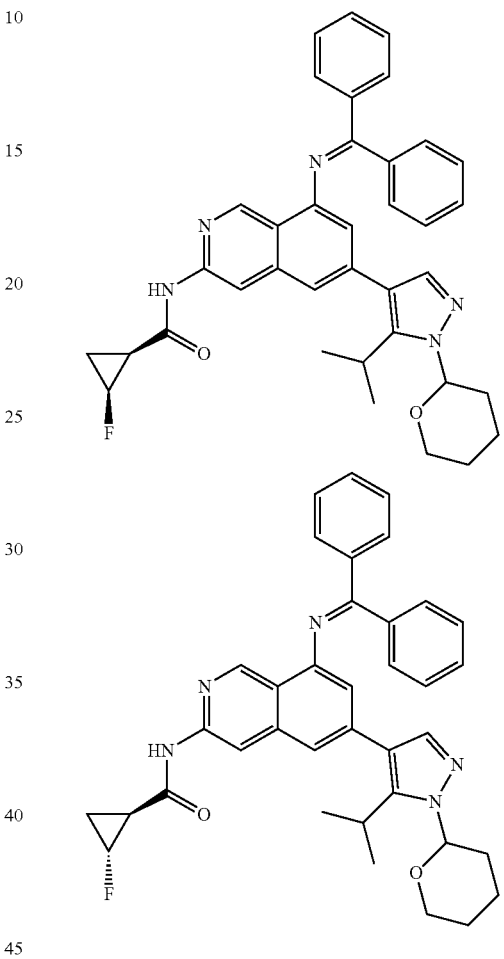

A mixture of (±)-cis-N-[8-chloro-6-[1-tetrahydropyran-2-yl-3-(trifluoromethyl)pyrazol-4-yl]-3-isoquinolyl]-2-cyano-cyclopropanecarboxamide (100 mg, 0.2 mmol), benzophenone imine (182 mg, 1.0 mmol), Xantphos (58 mg, 0.1 mmol), Pd$_2$(dba)$_3$ (46 mg, 0.05 mmol), and Cs$_2$CO$_3$ (170 mg, 0.52 mmol) in dry DMF (3.0 mL) and dry toluene (3.0 mL) was stirred at 130° C. under an Ar atmosphere for 4 hours. The reaction was concentrated. The residue was taken up in ethyl acetate (15 ml) and washed with 20 mL of brine. The organic layer was then separated, dried (Na$_2$SO$_4$) and concentrated to dryness. The crude was then purified by silica gel column chromatography (ethyl acetate/petroleum ether, 1:3 to 1:1) to afford (±)-cis-N-[8-(benzhydrylideneamino)-6-(3-isopropyl-1-tetrahydropyran-2-yl-pyrazol-4-yl)-3-isoquinolyl]-2-fluoro-cyclopropanecarboxamide (77 mg, 61% yield) as a yellow liquid (LCMS(ESI): [M+H]$^+$=602.3) and (±)-trans-N-[8-(benzhydrylideneamino)-6-(3-isopropyl-1-tetrahydropyran-2-yl-pyrazol-4-yl)-3-isoquinolyl]-2-fluoro-cyclopropanecarboxamide (43 mg, 32% yield) as yellow solid (LCMS (ESI): [M+H]$^+$=602.3).

Step 5: (±)-cis-N-(8-amino-6-(5-isopropyl-1H-pyrazol-4-yl) isoquinolin-3-yl)-2-fluorocyclopropanecarboxamide

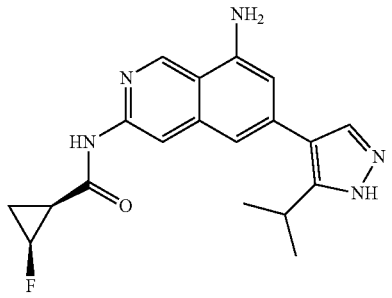

A solution of (±)-cis-N-[8-(benzhydrylideneamino)-6-(3-isopropyl-1-tetrahydropyran-2-yl-pyrazol-4-yl)-3-isoquinolyl]-2-fluoro-cyclopropanecarboxamide (120.0 mg, 0.20 mmol) in HCl in 1,4-dioxane (2.0 mL, 4 M, 8 mmol) was stirred at room temperature for 1 hour. The reaction was concentrated and the resulting residue was purified by reverse phase prep-HPLC (methanol 0-40/0.1% HCl in water) to afford (±)-cis-N-[8-amino-6-(3-isopropyl-1H-pyrazol-4-yl)-3-isoquinolyl]-2-fluoro-cyclopropanecarboxamide (30 mg, 43% yield) as a red solid (HCl salt). LCMS (ESI): [M+H]$^+$=354.2, R$_T$ (min)=1.53, method=B; $^1$HNMR (400 MHz, CD$_3$OD) δ 9.43 (s, 1H), 8.39 (s, 1H), 7.70 (s, 1H), 7.29 (s, 1H), 7.03 (s, 1H), 5.10-5.06 (m, 1H), 3.62-3.57 (m, 1H), 2.20-2.17 (m, 1H), 1.99-1.89 (m, 1H), 1.42 (d, J=6.8 Hz, 6H), 1.39-1.30 (m, 1H).

Example 30

(±)-trans-N-(8-amino-6-(5-isopropyl-1H-pyrazol-4-yl) isoquinolin-3-yl)-2-fluoro cyclopropanecarboxamide (Compound 42)

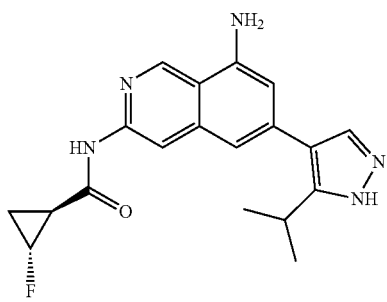 [SMILES: CC(C)c1[nH]ncc1-c1cc(N)c2cnc(NC(=O)[C@@H]3C[C@H]3F)cc2c1]

A solution of (±)-trans-N-[8-(benzhydrylideneamino)-6-(3-isopropyl-1-tetrahydropyran-2-yl-pyrazol-4-yl)-3-isoquinolyl]-2-fluoro-cyclopropanecarboxamide (115 mg, 0.19 mmol) in a HCl in 1,4-dioxane solution (2.0 mL, 4 M, 8 mmol) was stirred at room temperature for 1 hour. The reaction was concentrated and the resulting residue was purified by reverse phase prep-HPLC (methanol 0-50/0.1% HCl in water) to afford (±)-trans-N-[8-amino-6-(3-isopropyl-1H-pyrazol-4-yl)-3-isoquinolyl]-2-fluoro-cyclopropanecarboxamide (45 mg, 65% yield) as a red solid (HCl salt). LCMS(ESI): [M+H]$^+$=354.2, R$_T$(min)=1.59, method=B; $^1$H NMR (400 MHz, CD$_3$OD) δ 9.41 (s, 1H), 8.37 (s, 1H), 7.68 (s, 1H), 7.30 (s, 1H), 7.03 (s, 1H), 5.08-5.05 (m, 1H), 3.62-3.58 (m, 1H), 2.46-2.38 (m, 1H), 1.75-1.65 (m, 1H), 1.58-1.50 (m, 1H), 1.42 (d, J=6.8 Hz, 6H).

Example 31

(+)-cis-N-(8-amino-6-(1-methyl-6-oxo-1,6-dihydropyridin-2-yl)isoquinolin-3-yl)-2-fluorocyclopropanecarboxamide (Compound 43)

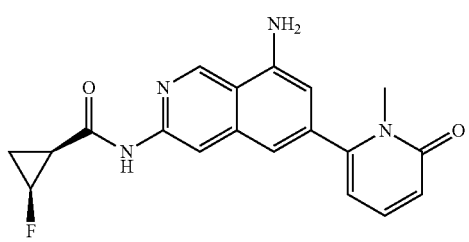 [SMILES: Cn1c(-c2cc(N)c3cnc(NC(=O)[C@@H]4C[C@@H]4F)cc3c2)cccc1=O]

Step 1: methyl-5-(4,4,5,5-tetramethyl-1,3,2-dioxaborolan-2-yl)-1H-indazole

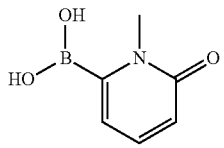

A mixture of 6-bromo-1-methyl-pyridin-2-one (500 mg, 2.66 mmol), bis(pinacolato)diboron (675 mg, 2.66 mmol), Pd(dppf)Cl$_2$ (97 mg, 0.13 mmol) and potassium acetate (781 mg, 7.98 mmol) in 1,4-dioxane (20 mL) was heated at 100° C. for 12 hours. The mixture was diluted with ethyl acetate (50 mL), filtered and concentrated to give crude product 1-methyl-6-oxo-1,6-dihydropyridin-2-ylboronic acid (320 mg) as a grey solid, which was used in the next step without further purification. LCMS (ESI): [M+H]$^+$=154.1.

Step 2: (±)-cis-N-(8-chloro-6-(1-methyl-6-oxo-1,6-dihydropyridin-2-yl)isoquinolin-3-yl)-2-fluorocyclopropanecarboxamide

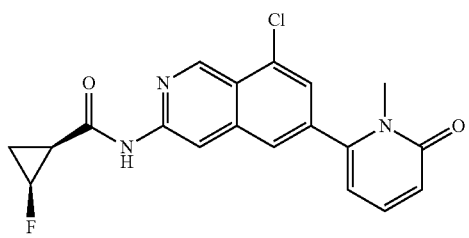 [SMILES: Cn1c(-c2cc(Cl)c3cnc(NC(=O)[C@@H]4C[C@@H]4F)cc3c2)cccc1=O]

To a sealed tube was added (1-methyl-6-oxo-2-pyridyl) boronic acid (106 mg, 0.70 mmol), (±)-cis-N-(6-bromo-8-chloroisoquinolin-3-yl)-2-fluorocyclopropanecarboxamide (160 mg, 0.47 mmol), Pd(dppf)$_2$Cl$_2$ (42 mg, 0.06 mmol), K$_3$PO$_4$ (98 mg, 0.47 mmol), sodium acetate (116 mg, 1.41 mmol), acetonitrile (20 mL) and water (2 mL). The mixture was bubbled through with nitrogen for 2 min and then stirred at 90° C. for 3 hours. The mixture was concentrated and purified by prep-TLC (petroleum ether/ethyl acetate, 1/2) to give (±)-cis-N-(8-chloro-6-(1-methyl-6-oxo-1,6-dihydropyridin-2-yl)isoquinolin-3-yl)-2-fluorocyclopropanecarboxamide (50 mg, 28% yield) as a white solid. LCMS (ESI): [M+H]$^+$=372.0.

Step 3: (±)-cis-N-(8-amino-6-(1-methyl-6-oxo-1,6-dihydropyridin-2-yl)isoquinolin-3-yl)-2-fluorocyclopropanecarboxamide

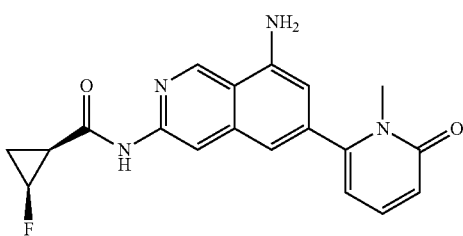 [SMILES: Cn1c(-c2cc(N)c3cnc(NC(=O)[C@@H]4C[C@@H]4F)cc3c2)cccc1=O]

To a sealed tube was added tert-butyl carbamate (157 mg, 1.34 mmol), Pd$_2$(dba)$_3$ (24 mg, 0.03 mmol), Cs$_2$CO$_3$ (131 mg, 0.40 mmol), Xantphos (26 mg, 0.05 mmol), (±)-cis-N-(8-chloro-6-(1-methyl-6-oxo-1,6-dihydropyridin-2-yl)isoquinolin-3-yl)-2-fluorocyclopropanecarboxamide (50 mg, 0.13 mmol), DMF (2 mL), and toluene (2 mL) in a glove box. The mixture was stirred at 110° C. for 18 hours. The mixture was concentrated and purified by reverse phase prep-HPLC to give (±)-cis-N-(8-amino-6-(1-methyl-6-oxo-1,6-dihydropyridin-2-yl)isoquinolin-3-yl)-2-fluorocyclopropanecarboxamide (7 mg, 15% yield) as a yellow solid. LCMS (ESI): R$_T$ (min)=1.385, [M+H]$^+$=353.1, method=A; 1H NMR (400 MHz, CD$_3$OD) δ 9.27 (s, 1H), 8.36 (s, 1H), 7.59 (dd, J=6.8, 9.2 Hz, 1H), 7.09 (s, 1H), 6.67 (d, J=1.6 Hz, 1H), 6.62 (dd, J=1.2, 9.2 Hz, 1H), 6.42 (dd, J=1.2, 6.8 Hz, 1H), 4.99-4.79 (m, 1H), 3.46 (s, 3H), 2.19-2.13 (m, 1H), 1.87-1.78 (m, 1H), 1.27-1.18 (m, 1H).

Example 32

(±)-trans-N-[8-amino-6-(6-methyl-1H-indazol-5-yl)-3-isoquinolyl]-2-cyano-cyclopropanecarboxamide (Compound 44)

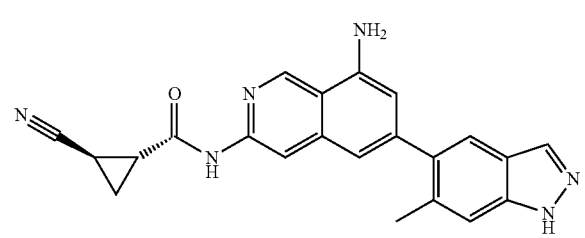

Step 1: methyl-5-(4,4,5,5-tetramethyl-1,3,2-dioxaborolan-2-yl)-1H-indazole

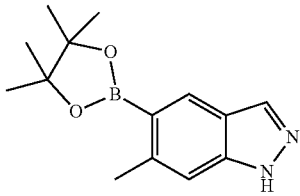 [SMILES: Cc1cc2[nH]ncc2cc1B1OC(C)(C)C(C)(C)O1]

A mixture of 5-bromo-6-methyl-1h-indazole (400 mg, 1.9 mmol), bis(pinacolato)diboron (2.41 g, 9.48 mmol), Pd(dppf)Cl$_2$ (277 mg, 0.38 mmol), and potassium acetate (557 mg, 5.69 mmol) in DMF (10 mL) was heated to 90° C. for 3 hours under nitrogen. The mixture was concentrated and purified by prep-TLC (petroleum ether) to give 6-methyl-5-(4,4,5,5-tetramethyl-1,3,2-dioxaborolan-2-yl)-1H-indazole (370 mg, 37% yield) as yellow oil. LCMS (ESI): [M+H]$^+$=259.1.

Step 2: (±)-trans-N-(8-chloro-6-(6-methyl-1H-indazol-5-yl)isoquinolin-3-yl)-2-cyanocyclopropanecarboxamide

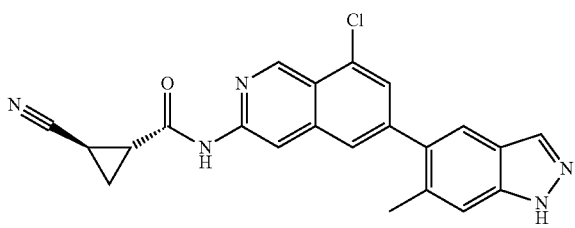

To a sealed tube was added trans-N-(6-bromo-8-chloro-3-isoquinolyl)-2-cyano-cyclopropanecarboxamide (160 mg, 0.46 mmol), 6-methyl-5-(4,4,5,5-tetramethyl-1,3,2-dioxaborolan-2-yl)-1H-indazole (141 mg, 0.55 mmol), Pd(dppf)$_2$Cl$_2$ (41 mg, 0.06 mmol), sodium acetate (113 mg, 1.39 mmol), acetonitrile (2 mL) and water (0.2 mL). The mixture was bubbled through with nitrogen for 2 min and then stirred at 100° C. for 3 hours. The mixture was concentrated and purified by prep-TLC (petroleum ether/ethyl acetate=2/1) to give (±)-trans-N-[8-chloro-6-(6-methyl-1H-indazol-5-yl)-3-isoquinolyl]-2-cyano-cyclopropanecarboxamide (160 mg, 82% yield) as a yellow oil. LCMS (ESI): [M+H]$^+$=402.1.

Step 3: (±)-trans-N-[8-chloro-6-(6-methyl-1-tetrahydropyran-2-yl-indazol-5-yl)-3-isoquinolyl]-2-cyano-cyclopropanecarboxamide

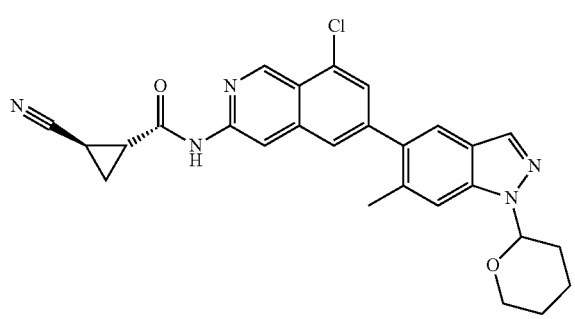

To a cooled (0° C.) suspension of trans-N-[8-chloro-6-(6-methyl-1H-indazol-5-yl)-3-isoquinolyl]-2-cyano-cyclopropanecarboxamide (190 mg, 0.47 mmol) and p-toluenesulfonic acid (8 mg, 0.05 mmol) in dichloromethane (5 mL) was added 3,4-dihydro-2h-pyran (47 mg, 0.57 mmol). The reaction mixture was stirred at room temperature for 16 hours. The mixture was concentrated and purified by prep-TLC (petroleum ether/ethyl acetate, 4:1) to afford trans-N-[8-chloro-6-(6-methyl-1-tetrahydropyran-2-yl-indazol-5-yl)-3-isoquinolyl]-2-cyano-cyclopropanecarboxamide (190 mg, 75% yield) as a yellow oil. LCMS (ESI): [M+H]⁺=486.2.

Step 4: (±)-trans-2-cyano-N-(8-(diphenylmethyleneamino)-6-(6-methyl-1-(tetrahydro-2H-pyran-2-yl)-1H-indazol-5-yl)isoquinolin-3-yl)cyclopropanecarboxamide

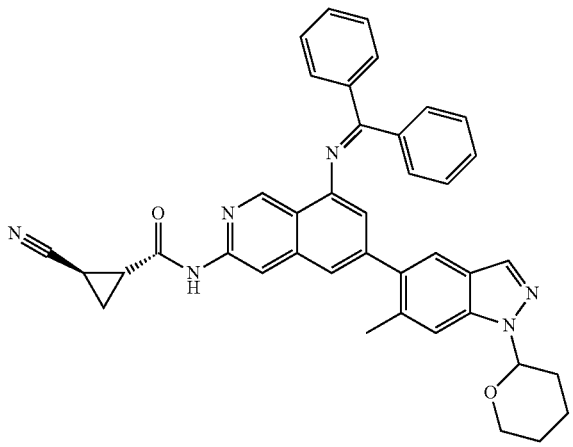

To a sealed tube was added benzophenone imine (61 mg, 0.34 mmol), trans-N-[8-chloro-6-(6-methyl-1-tetrahydropyran-2-yl-indazol-5-yl)-3-isoquinolyl]-2-cyano-cyclopropanecarboxamide (150 mg, 0.31 mmol), Pd(OAc)₂ (7 mg, 0.03 mmol), Cs₂CO₃ (201 mg, 0.62 mmol), xantphos (15 mg, 0.03 mmol) and toluene (5 mL). The mixture was stirred at 145° C. for 16 hours. The reaction mixture was concentrated and purified by prep-TLC (petroleum ether/ethyl acetate, 1/2) to give (±)-trans-2-cyano-N-(8-(diphenylmethyleneamino)-6-(6-methyl-1-(tetrahydro-2H-pyran-2-yl)-1H-indazol-5-yl)isoquinolin-3-yl)cyclopropanecarboxamide (90 mg, 46% yield) as a yellow solid. LCMS (ESI): [M+H]⁺=631.1.

Step 5: (±)-trans-N-[8-amino-6-(6-methyl-1H-indazol-5-yl)-3-isoquinolyl]-2-cyano-cyclopropanecarboxamide

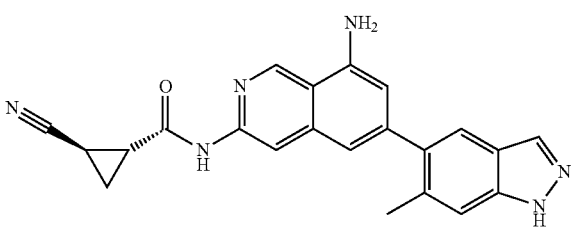

To a mixture of (±)-trans-N-[8-(benzhydrylideneamino)-6-(6-methyl-1-tetrahydropyran-2-yl-indazol-5-yl)-3-isoquinolyl]-2-cyano-cyclopropanecarboxamide (80 mg, 0.13 mmol) in THF (3 mL) was added a HCl in 1,4-dioxane solution (2 mL, 4 M, 8 mmol). The mixture was stirred at room temperature for 1 hour. The mixture was concentrated and purified by reverse phase prep-HPLC to give (±)-trans-N-[8-amino-6-(6-methyl-1H-indazol-5-yl)-3-isoquinolyl]-2-cyano-cyclopropanecarboxamide (6.3 mg, 12.9% yield) as a yellow solid. LCMS (ESI): $R_T$ (min)=1.513, [M+H]⁺=383.1, method=A; ¹H NMR (400 MHz, CD₃OD) δ 9.24 (s, 1H), 8.27 (s, 1H), 8.03 (s, 1H), 7.65 (s, 1H), 7.45 (s, 1H), 7.00 (s, 1H), 6.76 (d, J=1.2 Hz, 1H), 2.65-2.64 (m, 1H), 2.39 (s, 3H), 2.14-2.09 (m, 1H), 1.62-1.55 (m, 2H).

Example 33

(±)-trans-N1-[8-amino-6-(6-methyl-1H-indazol-5-yl)-3-isoquinolyl]cyclopropane-1,2-dicarboxamide (Compound 45)

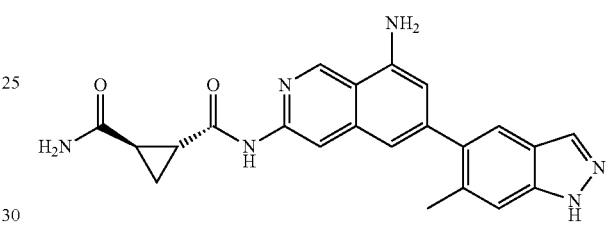

To a mixture of (±)-trans-N-[8-(benzhydrylideneamino)-6-(6-methyl-1-tetrahydropyran-2-yl-indazol-5-yl)-3-isoquinolyl]-2-cyano-cyclopropanecarboxamide (80 mg, 0.13 mmol) in THF (3 mL) was added a HCl in 1,4-dioxane solution (2 mL, 4 M, 8 mmol). The mixture was stirred at room temperature for 1 hour. The mixture was concentrated and purified by reverse phase prep-HPLC to give (±)-trans-N1-[8-amino-6-(6-methyl-1H-indazol-5-yl)-3-isoquinolyl]cyclopropane-1,2-dicarboxamide (8.3 mg, 16% yield) as a yellow solid. LCMS (ESI): $R_T$(min)=1.372, [M+H]⁺=401.1, method=A; ¹H NMR (400 MHz, CD₃OD) δ 9.23 (s, 1H), 8.25 (s, 1H), 8.03 (s, 1H), 7.65 (s, 1H), 7.45 (s, 1H), 7.00 (s, 1H), 6.75 (s, 1H), 2.42-2.38 (m, 4H), 2.25-2.20 (m, 1H), 1.44-1.40 (m, 2H).

Example 34

(±)-cis-N-(8-amino-6-(4-methoxypyridin-3-yl)isoquinolin-3-yl)-2-fluorocyclopropane carboxamide (Compound 46)

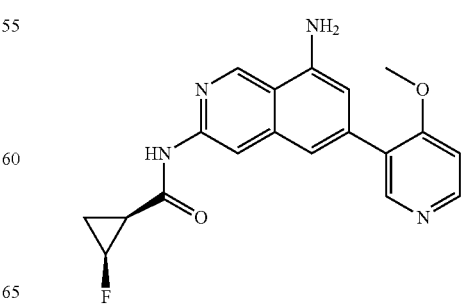

(±)-trans-N-(8-amino-6-(4-methoxypyridin-3-yl)
isoquinolin-3-yl)-2-fluorocyclopropanecarboxamide
(Compound 47)

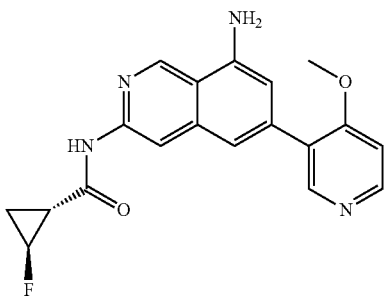 [SMILES: COc1ccncc1-c1cc(N)c2cnc(NC(=O)[C@H]3C[C@@H]3F)cc2c1]

Step 1: (±)-8-chloro-3-(cis-2-fluorocyclopropanecarboxamido)isoquinolin-6-ylboronic Acid

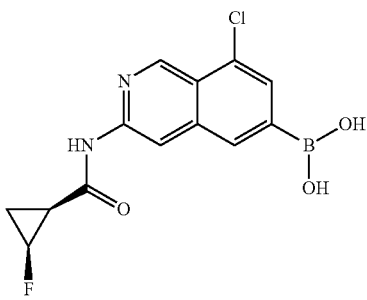 [SMILES: O=C(Nc1cc2cc(B(O)O)cc(Cl)c2cn1)[C@@H]1C[C@@H]1F]

A mixture of (±)-cis-N-(6-bromo-8-chloro-3-isoquinolyl)-2-fluoro-cyclopropanecarboxamide (1.0 g, 2.91 mmol), bis(pinacolato)diboron (960 mg, 3.78 mmol), Pd(dppf)Cl₂ (424 mg, 0.58 mmol), and potassium acetate (855 mg, 8.73 mmol) in DMF (4 mL) was purged three times with N₂. The mixture was stirred at 100° C. for 1 hour. The mixture was extracted with ethyl acetate. The organic layer was washed with water and brine, dried over Na₂SO₄, filtered and concentrated. The crude product was purified by silica gel flash chromatography (petroleum ether/ethyl acetate, 3:1) to give 8-chloro-3-(cis-2-fluorocyclopropanecarboxamido)isoquinolin-6-ylboronic acid (600 mg, 66% yield) as a yellow solid. LCMS (ESI): [M+H]⁺=309.0.

Step 2: (±)-cis-N-(8-chloro-6-(4-methoxypyridin-3-yl)isoquinolin-3-yl)-2-fluorocyclopropanecarboxamide

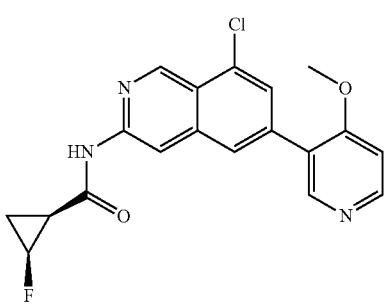 [SMILES: COc1ccncc1-c1cc(Cl)c2cnc(NC(=O)[C@@H]3C[C@@H]3F)cc2c1]

To a sealed tube was added (±)-[8-chloro-3-[[cis-2-fluorocyclopropanecarbonyl]amino]-6-isoquinolyl]boronic acid (200 mg, 0.57 mmol), 3-bromo-4-methoxy-pyridine (128 mg, 0.68 mmol), Pd(dppf)₂Cl₂ (51 mg, 0.07 mmol), K₃PO₄ (120 mg, 0.57 mmol), sodium acetate (142 mg, 1.73 mmol), 1,4-dioxane (2 mL) and water (0.2 mL). The mixture was bubbled through with N₂ for 2 minutes and stirred at 100° C. for 3 hours. The mixture was concentrated and purified by prep-TLC (petroleum ether/ethyl acetate, 2/1) to give (±)-cis-N-(8-chloro-6-(4-methoxypyridin-3-yl)isoquinolin-3-yl)-2-fluorocyclopropanecarboxamide (80 mg, 36% yield) as a yellow oil. LCMS (ESI): [M+H]⁺=372.1.

Step 3: (±)-cis-N-(8-(diphenylmethyleneamino)-6-(4-methoxypyridin-3-yl)isoquinolin-3-yl)-2-fluorocyclopropanecarboxamide

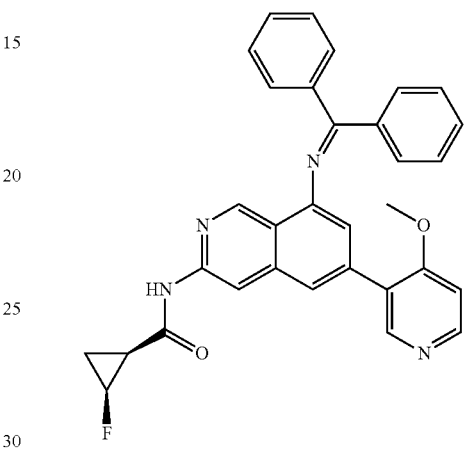

To a sealed tube was added (±)-cis-N-[8-chloro-6-(4-methoxy-3-pyridyl)-3-isoquinolyl]-2-fluoro-cyclopropanecarboxamide (60 mg, 0.16 mmol), benzophenone imine (32 mg, 0.18 mmol), Pd(OAc)₂ (4 mg, 0.02 mmol), Cs₂CO₃ (105 mg, 0.32 mmol), Xantphos (8 mg, 0.02 mmol), DMF (1 mL) and toluene (3 mL). The mixture was heated in a microwave reactor at 145° C. for 30 minutes. The reaction was diluted with ethyl acetate (50 mL), washed with brine, dried (Na₂SO₄) and concentrated. The crude product was then purified by flash silica gel column chromatography (80% ethyl acetate in hexane) to give a mixture of (±)-cis-N-(8-(diphenylmethyleneamino)-6-(4-methoxypyridin-3-yl)isoquinolin-3-yl)-2-fluorocyclopropanecarboxamide and (±)-trans-N-(8-(diphenylmethyleneamino)-6-(4-methoxypyridin-3-yl)isoquinolin-3-yl)-2-fluorocyclopropanecarboxamide (20 mg, 24% yield) as a yellow solid. LCMS (ESI): [M+H]⁺=517.2.

Step 4: (±)-cis-N-(8-amino-6-(4-methoxypyridin-3-yl)isoquinolin-3-yl)-2-fluorocyclopropanecarboxamide

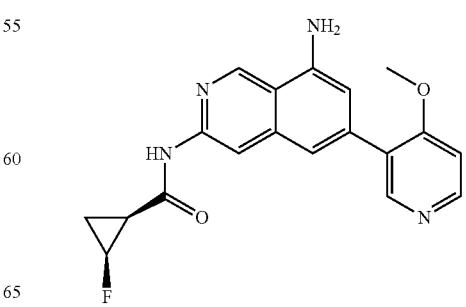

To a solution of mixture of (±)-cis-N-(8-(diphenylmethyleneamino)-6-(4-methoxypyridin-3-yl)isoquinolin-3-yl)-2-fluorocyclopropanecarboxamide and trans-N-(8-(diphenylmethyleneamino)-6-(4-methoxypyridin-3-yl)isoquinolin-3-yl)-2-fluorocyclopropanecarboxamide (20 mg, 0.04 mmol) in THF (3 mL) was added a solution of HCl in 1,4-dioxane (2 mL, 4 M, 8 mmol). The mixture was stirred at room temperature for 1 hour. The mixture was concentrated and purified by reverse phase prep-HPLC to give the two desired isomers: (±)-cis-N-[8-amino-6-(4-methoxy-3-pyridyl)-3-isoquinolyl]-2-fluoro-cyclopropanecarboxamide (4.9 mg, 36%, yellow solid). LCMS (ESI): $R_T$ (min)=1.253, [M+H]$^+$=353.1, method=A; $^1$H NMR (400 MHz, CD$_3$OD): δ 9.22 (s, 1H), 8.44 (d, J=6.0 Hz, 1H), 8.41 (s, 1H), 8.31 (s, 1H), 7.21 (d, J=6.0 Hz, 1H), 7.19 (s, 1H), 6.88 (d, J=1.6 Hz, 1H), 4.98-4.80 (m, 1H), 3.96 (s, 3H), 2.19-2.14 (m, 1H), 1.88-1.78 (m, 1H), 1.27-1.18 (m, 1H). (±)-trans-N-[8-amino-6-(4-methoxy-3-pyridyl)-3-isoquinolyl]-2-fluoro-cyclopropanecarboxamide (6 mg, 44%, yellow solid). LCMS (ESI): $R_T$ (min)=1.295, [M+H]$^+$=353.1, method=A; $^1$H NMR (400 MHz, CD$_3$OD): δ 9.22 (s, 1H), 8.44 (d, J=6.0 Hz, 1H), 8.40 (s, 1H), 8.25 (s, 1H), 7.21 (d, J=6.0 Hz, 1H), 7.17 (s, 1H), 6.88 (d, J=0.8 Hz, 1H), 4.99-4.78 (m, 1H), 3.96 (s, 3H), 2.50-2.40 (m, 1H), 1.55-1.49 (m, 1H), 1.42-1.37 (m, 1H).

Example 35

(1)-cis-N-[8-amino-6-(2-hydroxy-4-methyl-3-pyridyl)-3-isoquinolyl]-2-fluoro-cyclopropanecarboxamide (Compound 48)

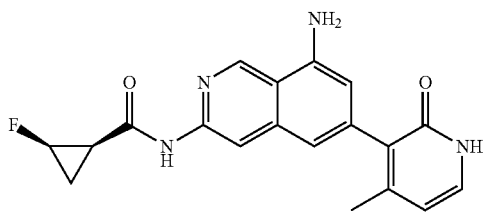 [SMILES: Cc1cc[nH]c(=O)c1-c1cc(N)c2cnc(NC(=O)[C@H]3C[C@H]3F)cc2c1]

Step 1: 2-methoxy-4-methyl-3-(4,4,5,5-tetramethyl-1,3,2-dioxaborolan-2-yl)pyridine

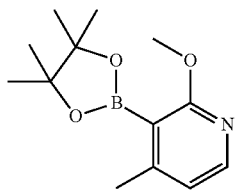 [SMILES: COc1nccc(C)c1B1OC(C)(C)C(C)(C)O1]

To a pressure tube was added 3-bromo-2-methoxy-4-methylpyridine (396 mg, 1.96 mmol), bis(pinacolato)diboron (597 mg, 2.35 mmol), Pd(dppf)$_2$Cl$_2$ (143 mg, 0.20 mmol), potassium acetate (384 mg, 3.92 mmol) and 1,4-dioxane (15 mL). The mixture was stirred at 95° C. for 4 hours. The residue was purified by silica gel flash chromatography (petroleum ether/ethyl acetate, 4:1) to give 2-methoxy-4-methyl-3-(4,4,5,5-tetramethyl-1,3,2-dioxaborolan-2-yl)pyridine (250 mg, 51% yield) as a colourless oil. LCMS (ESI): [M+H]$^+$=249.3.

Step 2: (±)-cis-N-[8-chloro-6-(2-methoxy-4-methyl-3-pyridyl)-3-isoquinolyl]-2-fluoro-cyclopropanecarboxamide

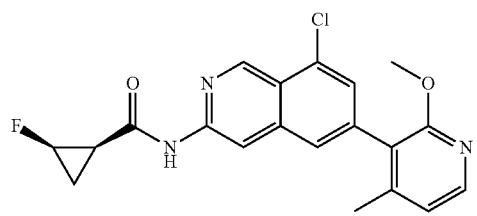 [SMILES: COc1nccc(C)c1-c1cc(Cl)c2cnc(NC(=O)[C@H]3C[C@H]3F)cc2c1]

To a pressure tube was added (±)-cis-N-(6-bromo-8-chloro-3-isoquinolyl)-2-fluoro-cyclopropanecarboxamide (260 mg, 0.76 mmol), 2-methoxy-4-methyl-3-(4,4,5,5-tetramethyl-1,3,2-dioxaborolan-2-yl)pyridine (226 mg, 0.91 mmol), Pd(dppf)$_2$Cl$_2$ (68 mg, 0.09 mmol), sodium acetate (244 mg, 2.3 mmol), K$_3$PO$_4$ (160 mg, 0.76 mmol), acetonitrile (10 mL) and water (1 mL). The mixture was bubbled through with N$_2$ for 2 minutes and stirred at 90° C. for 2 hours. The residue was purified by silica gel flash chromatography (petroleum ether/ethyl acetate, 4:1) to afford (±)-cis-N-[8-chloro-6-(2-methoxy-4-methyl-3-pyridyl)-3-isoquinolyl]-2-fluoro-cyclopropanecarboxamide (145 mg, 50% yield) as a white solid. LCMS (ESI): [M+H]$^+$=386.1.

Step 3: (±)-cis-N-[8-amino-6-(2-methoxy-4-methyl-3-pyridyl)-3-isoquinolyl]-2-fluoro-cyclopropanecarboxamide

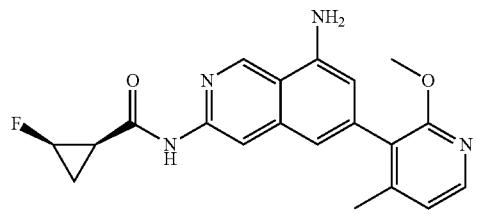 [SMILES: COc1nccc(C)c1-c1cc(N)c2cnc(NC(=O)[C@H]3C[C@H]3F)cc2c1]

A mixture of Pd$_2$dba$_3$ (32 mg, 0.03 mmol), Cs$_2$CO$_3$ (253 mg, 0.78 mmol), (±)-cis-N-[8-chloro-6-(2-methoxy-4-methyl-3-pyridyl)-3-isoquinolyl]-2-fluoro-cyclopropanecarboxamide (100 mg, 0.26 mmol) and tert-butyl carbamate (304 mg, 2.59 mmol), and Xantphos (40 mg, 0.07 mmol) in toluene (1 mL) and DMF (1 mL) was heated at 110° C. for 2 hours. The mixture diluted with ethyl acetate, washed with water (30 mL), brine (30 mL), dried over Na$_2$SO$_4$, filtered and concentrated. The residue was purified by reverse phase prep-HPLC to give (±)-cis-N-[8-amino-6-(2-methoxy-4-methyl-3-pyridyl)-3-isoquinolyl]-2-fluoro-cyclopropanecarboxamide (12 mg, 13% yield) as a yellow solid. LCMS (ESI): [M+H]$^+$=367.1.

Step 4: (±)-cis-N-[8-amino-6-(2-hydroxy-4-methyl-3-pyridyl)-3-isoquinolyl]-2-fluoro-cyclopropanecarboxamide

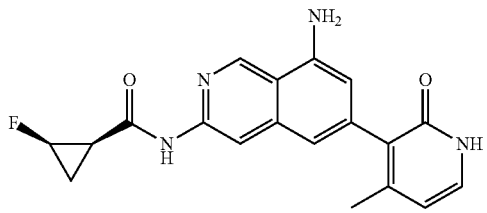 [SMILES: Cc1cc[nH]c(=O)c1-c1cc(N)c2cnc(NC(=O)[C@H]3C[C@H]3F)cc2c1]

To a mixture of (±)-cis-N-[8-amino-6-(2-methoxy-4-methyl-3-pyridyl)-3-isoquinolyl]-2-fluoro-cyclopropanecarboxamide (12 mg, 0.03 mmol) in acetonitrile (4 mL) was added iodotrimethylsilane (0.02 mL, 0.14 mmol). The mixture was stirred at 90° C. for 1 hour. The mixture was diluted with ethyl acetate, washed with water (30 mL), brine (30 mL), dried over $Na_2SO_4$, filtered and concentrated. The residue was purified by reverse phase prep-HPLC to give (±)-cis-N-[8-amino-6-(2-hydroxy-4-methyl-3-pyridyl)-3-isoquinolyl]-2-fluoro-cyclopropanecarboxamide (9 mg, 78% yield) as a yellow solid. LCMS (ESI): $R_T$ (min)=1.625, $[M+H]^+$=353.1, method=I; $^1H$ NMR (400 MHz, DMSO-$d_6$) δ 11.26 (s, 1H), 10.47 (s, 1H), 9.25 (s, 1H), 8.17 (s, 1H), 7.23 (d, J=8.8 Hz, 1H), 6.74 (s, 1H), 6.47 (s, 1H), 6.13 (d, J=8.8 Hz, 1H), 5.91 (s, 2H), 5.00-4.76 (m, 1H), 2.27-2.23 (m, 1H), 2.00 (s, 3H), 1.74-1.61 (m, 1H), 1.18-1.12 (m, 1H).

Example 36

(±)-cis-N-[8-amino-6-(5-fluoro-4-methyl-3-pyridyl)-3-isoquinolyl]-2-fluoro-cyclopropanecarboxamide (Compound 49)

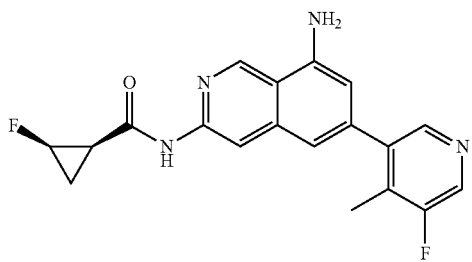 [SMILES: Cc1c(F)cncc1-c1cc(N)c2cnc(NC(=O)[C@H]3C[C@H]3F)cc2c1]

Step 1: (±)-cis-N-[8-chloro-6-(5-fluoro-4-methyl-3-pyridyl)-3-isoquinolyl]-2-fluoro-cyclopropanecarboxamide

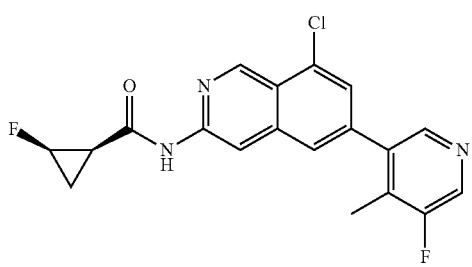

To a sealed tube was added (±)-cis-N-(6-bromo-8-chloro-3-isoquinolyl)-2-fluoro-cyclopropanecarboxamide (200 mg, 0.58 mmol), 3-fluoro-4-methyl-5-(4,4,5,5-tetramethyl-1,3,2-dioxaborolan-2-yl)pyridine (179 mg, 0.76 mmol), $Pd(dppf)_2Cl_2$ (52 mg, 0.07 mmol), $K_3PO_4$ (123 mg, 0.58 mmol) and sodium acetate (145 mg, 1.77 mmol), acetonitrile (20 mL) and water (2 mL). The mixture was bubbled through with $N_2$ for 2 min, and stirred at 90° C. for 3 hours. The mixture was concentrated and purified by silica gel flash chromatography (petroleum ether/ethyl acetate, 2:1) to afford (±)-cis-N-[8-chloro-6-(5-fluoro-4-methyl-3-pyridyl)-3-isoquinolyl]-2-fluoro-cyclopropanecarboxamide (100 mg, 46% yield) as a white solid. LCMS (ESI): $[M+H]^+$=374.1.

Step 2: (±)-cis-N-[8-amino-6-(5-fluoro-4-methyl-3-pyridyl)-3-isoquinolyl]-2-fluoro-cyclopropanecarboxamide

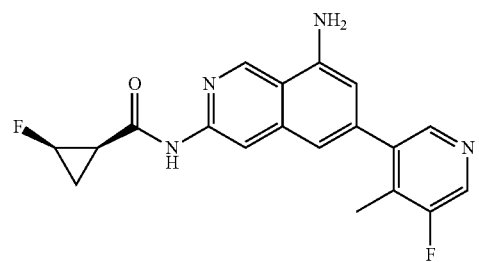 [SMILES: Cc1c(F)cncc1-c1cc(N)c2cnc(NC(=O)[C@H]3C[C@H]3F)cc2c1]

A mixture of $Pd_2dba_3$ (33 mg, 0.04 mmol), $Cs_2CO_3$ (262 mg, 0.80 mmol), (±)-cis-N-[8-chloro-6-(5-fluoro-4-methyl-3-pyridyl)-3-isoquinolyl]-2-fluoro-cyclopropanecarboxamide (100 mg, 0.27 mmol) and tert-butyl carbamate (313 mg, 2.68 mmol), and Xantphos (41 mg, 0.07 mmol) in toluene (1 mL) and DMF (1 mL) was heated at 110° C. for 2 hours. The mixture was diluted with ethyl acetate, washed with water (30 mL), brine (30 mL), dried over $Na_2SO_4$, filtered and concentrated. The residue was purified by reverse phase prep-HPLC to give (±)-cis-N-[8-amino-6-(5-fluoro-4-methyl-3-pyridyl)-3-isoquinolyl]-2-fluoro-cyclopropanecarboxamide (18 mg, 19% yield) as a yellow solid. LCMS (ESI): $R_T$ (min)=1.422, $[M+H]^+$=355.1, method=D; $^1H$ NMR (400 MHz, $CD_3OD$) δ 9.25 (s, 1H), 8.39 (d, J=1.2 Hz, 1H), 8.34 (s, 1H), 8.30 (s, 1H), 7.01 (s, 1H), 6.68 (d, J=1.6 Hz, 1H), 4.99-4.78 (m, 1H), 2.31 (d, J=2.0 Hz, 3H), 2.18-2.13 (m, 1H), 1.87-1.77 (m, 1H), 1.26-1.21 (m, 1H).

Example 37

(±)-cis-N-[8-amino-6-(3-pyridyl)-3-isoquinolyl]-2-fluoro-cyclopropanecarboxamide (Compound 50)

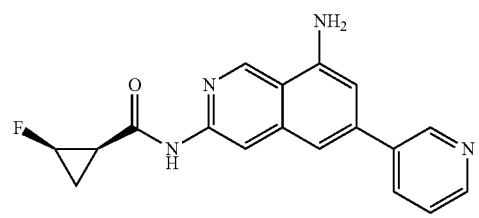 [SMILES: Nc1cc(-c2cccnc2)cc2cc(NC(=O)[C@H]3C[C@H]3F)ncc12]

Step 1: (±)-cis-N-[8-chloro-6-(3-pyridyl)-3-isoquinolyl]-2-fluoro-cyclopropanecarboxamide

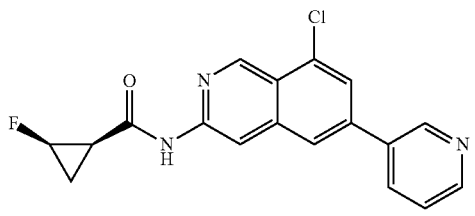 [SMILES: O=C(Nc1cc2cc(-c3cccnc3)cc(Cl)c2cn1)[C@H]1C[C@H]1F]

To a sealed tube was added cis-N-(6-bromo-8-chloro-3-isoquinolyl)-2-fluoro-cyclopropanecarboxamide (300 mg, 0.87 mmol), 3-(4,4,5,5-tetramethyl-1,3,2-dioxaborolan-2-yl)pyridine (214 mg, 1.05 mmol), Pd(dppf)$_2$Cl$_2$ (78 mg, 0.11 mmol), sodium acetate (281 mg, 2.65 mmol), K$_3$PO$_4$ (184 mg, 0.87 mmol), acetonitrile (10 mL) and water (1 mL). The mixture was bubbled through with N$_2$ for 2 minutes, and stirred at 90° C. for 2 hours. The mixture was concentrated and purified by silica gel flash chromatography (petroleum ether/ethyl acetate, 1:1) to afford cis-N-[8-chloro-6-(3-pyridyl)-3-isoquinolyl]-2-fluoro-cyclopropanecarboxamide (200 mg, 67% yield) as a white solid. LCMS (ESI): [M+H]$^+$=342.1.

Step 2: (±)-cis-N-[8-amino-6-(3-pyridyl)-3-isoquinolyl]-2-fluoro-cyclopropanecarboxamide

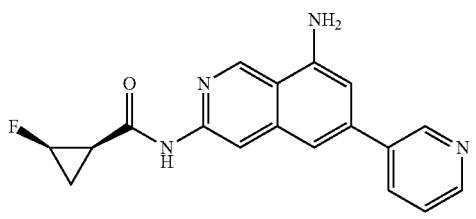 [SMILES: Nc1cc(-c2cccnc2)cc2cc(NC(=O)[C@H]3C[C@H]3F)ncc12]

A mixture of Pd$_2$dba$_3$ (66 mg, 0.07 mmol), Cs$_2$CO$_3$ (529 mg, 1.62 mmol), cis-N-[8-chloro-6-(3-pyridyl)-3-isoquinolyl]-2-fluoro-cyclopropanecarboxamide (185 mg, 0.54 mmol), and tert-butyl carbamate (634 mg, 5.41 mmol), Xantphos (83 mg, 0.14 mmol) in toluene (1 mL) and DMF (1 mL) was heated at 110° C. for 2 hours. The mixture was diluted with ethyl acetate, washed with water (30 mL), brine (30 mL), dried over Na$_2$SO$_4$, filtered and concentrated. The residue was purified by reverse phase prep-HPLC to give cis-N-[8-amino-6-(3-pyridyl)-3-isoquinolyl]-2-fluoro-cyclopropanecarboxamide (20 mg, 11% yield) as a yellow solid. LCMS (ESI): R$_T$ (min)=1.273, [M+H]$^+$=323.0, method=A; $^1$H NMR (400 MHz, CD$_3$OD) δ 9.23 (s, 1H), 8.89 (d, J=1.6 Hz, 1H), 8.56 (dd, J=1.6, 4.8 Hz, 1H), 8.37 (s, 1H), 8.21-8.18 (m, 1H), 7.56 (dd, J=4.8, 8.0 Hz, 1H), 7.34 (s, 1H), 7.01 (d, J=1.2 Hz, 1H), 4.99-4.79 (m, 1H), 2.20-2.13 (m, 1H), 1.88-1.78 (m, 1H), 1.27-1.19 (m, 1H).

Example 38

(±)-trans-N-[8-amino-6-(3-methyl-4-pyridyl)-3-isoquinolyl]-2-cyano-cyclopropanecarboxamide (Compound 51)

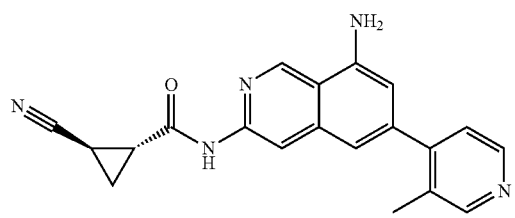 [SMILES: Cc1cnccc1-c1cc(N)c2cnc(NC(=O)[C@@H]3C[C@H]3C#N)cc2c1]

Step 1: (±)-trans-N-[8-chloro-6-(3-methyl-4-pyridyl)-3-isoquinolyl]-2-cyano-cyclopropanecarboxamide

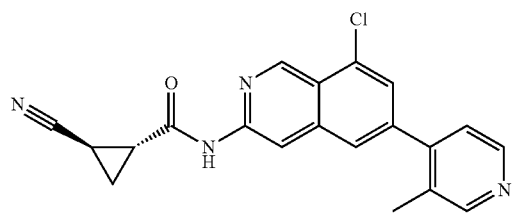 [SMILES: Cc1cnccc1-c1cc(Cl)c2cnc(NC(=O)[C@@H]3C[C@H]3C#N)cc2c1]

To a sealed tube was added (±)-trans-N-(6-bromo-8-chloro-3-isoquinolyl)-2-cyano-cyclopropanecarboxamide (150 mg, 0.43 mmol), 3-methylpyridine-4-boronicacid (70 mg, 0.51 mmol), Pd(dppf)$_2$Cl$_2$ (39 mg, 0.05 mmol) and Na$_2$CO$_3$ (138 mg, 1.3 mmol), 1,4-dioxane (10 mL) and water (1 mL). The mixture was bubbled through with N$_2$ for 2 min, and then heated in microwave reactor at 120° C. for 1 hour. The mixture was concentrated and purified by prep-TLC (ethyl acetate/petroleum ether, 1:1) to afford trans-N-[8-chloro-6-(3-methyl-4-pyridyl)-3-isoquinolyl]-2-cyano-cyclopropanecarboxamide (70 mg, 45% yield) as a yellow solid. LCMS (ESI): [M+H]$^+$=363.1.

Step 2: (±)-trans-N-[8-amino-6-(3-methyl-4-pyridyl)-3-isoquinolyl]-2-cyano-cyclopropanecarboxamide

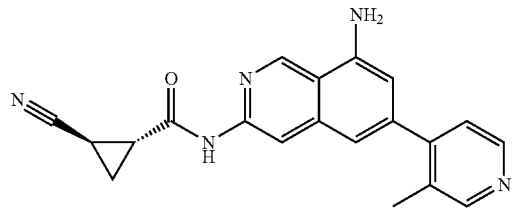 [SMILES: Cc1cnccc1-c1cc(N)c2cnc(NC(=O)[C@@H]3C[C@H]3C#N)cc2c1]

To a sealed tube was added (±)-trans-N-[8-chloro-6-(3-methyl-4-pyridyl)-3-isoquinolyl]-2-cyano-cyclopropanecarboxamide (60 mg, 0.17 mmol), tert-butyl carbamate (157 mg, 1.35 mmol), Pd$_2$(dba)$_3$ (31 mg, 0.03 mmol), NaOtBu (47 mg, 0.49 mmol), tBuBrettPhos (19 mg, 0.04 mmol) and 1-methyl-2-pyrrolidinone (5 mL). The mixture was stirred at 110° C. for 2 hours. The mixture was diluted with ethyl acetate, washed with water (30 mL), brine (30 mL), dried over Na$_2$SO$_4$, filtered and concentrated. The crude product was purified by prep-TLC (ethyl acetate) and reverse phase prep-HPLC to give (±)-trans-N-[8-amino-6-(3-methyl-4-pyridyl)-3-isoquinolyl]-2-cyano-cyclopropanecarboxamide (3 mg, 5% yield) as a yellow solid. LCMS (ESI): R$_T$ (min)=1.338, [M+H]$^+$=344.2, method=D; $^1$H NMR (400 MHz, CD$_3$OD) δ 9.26 (s, 1H), 8.47 (s, 1H), 8.41 (d, J=5.2 Hz, 1H), 8.30 (s, 1H), 7.35 (d, J=5.2 Hz, 1H), 7.00 (s, 1H), 6.69 (d, J=1.2 Hz, 1H), 2.64-2.63 (m, 1H), 2.34 (s, 3H), 2.12-2.10 (m, 1H), 1.60-1.53 (m, 2H).

Example 39

(±)-trans-N-[8-amino-7-fluoro-6-(4-methyl-3-pyridyl)-3-isoquinolyl]-2-cyano-cyclopropanecarboxamide (Compound 52)

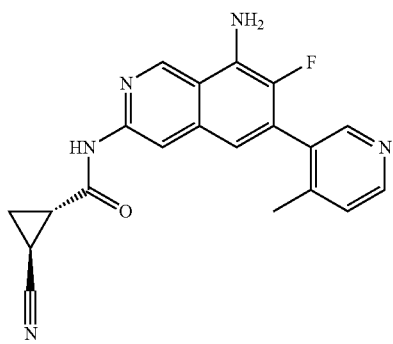 [SMILES: Cc1ccncc1-c1cc2cc(NC(=O)[C@H]3C[C@@H]3C#N)ncc2c(N)c1F]

Step 1: (±)-trans-N-(8-chloro-7-fluoro-6-iodo-3-isoquinolyl)-2-cyano-cyclopropanecarboxamide

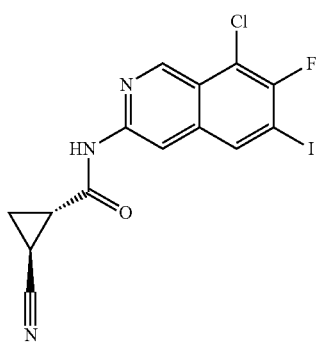 [SMILES: N#C[C@H]1C[C@@H]1C(=O)Nc1cc2cc(I)c(F)c(Cl)c2cn1]

To a solution of 8-chloro-7-fluoro-6-iodo-isoquinolin-3-amine (800 mg, 2.48 mmol) in dichloromethane (10 mL) and pyridine (0.6 mL, 7.44 mmol) was added (±)-trans-2-cyanocyclopropanecarbonyl chloride (830 mg, 6.41 mmol). The mixture was stirred at 25° C. for 2 hours. The mixture was concentrated and re-suspended in water (10 mL). The mixture was extracted with ethyl acetate (50 mL×3). The organic layer was washed with brine (50 mL), dried over Na$_2$SO$_4$, filtered and concentrated. The crude product was suspended in 100 ml of petroleum ether and 10 ml of ethyl acetate and then filtered to give (±)-trans-N-(8-chloro-7-fluoro-6-iodo-3-isoquinolyl)-2-cyano-cyclopropanecarboxamide (800 mg, 78% yield) as a yellow solid. LCMS (ESI): [M+H]$^+$=416.0.

Step 2: (±)-trans-N-[8-chloro-7-fluoro-6-(4-methyl-3-pyridyl)-3-isoquinolyl]-2-cyano-cyclopropanecarboxamide

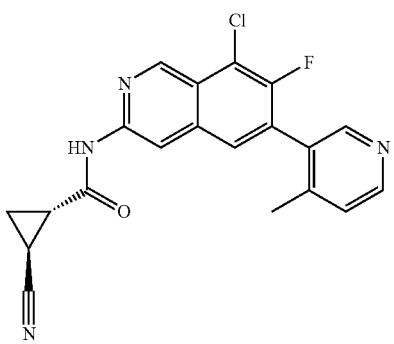 [SMILES: Cc1ccncc1-c1cc2cc(NC(=O)[C@H]3C[C@@H]3C#N)ncc2c(N)c1F]

To a sealed tube was added (±)-trans-N-(8-chloro-7-fluoro-6-iodo-3-isoquinolyl)-2-cyano-cyclopropanecarboxamide (400 mg, 0.96 mmol), 4-methyl-3-(4,4,5,5-tetramethyl-1,3,2-dioxaborolan-2-yl)pyridine (253 mg, 1.15 mmol), Pd(dppf)$_2$Cl$_2$ (84 mg, 0.12 mmol) and Na$_2$CO$_3$ (255 mg, 2.41 mmol), tetrahydrofuran (20 mL) and water (8 mL). The mixture was bubbled through with N$_2$ for 2 minutes, and stirred at 65° C. for 3 hours. Water (50 mL) was then added. The mixture was extracted with ethyl acetate (50 mL×3). The combined organic extracts were washed with brine (50 mL), dried over Na$_2$SO$_4$, filtered and concentrated. The residue was purified by silica gel flash chromatography (petroleum ether/ethyl acetate, 1:1) to afford (±)-trans-N-[8-chloro-7-fluoro-6-(4-methyl-3-pyridyl)-3-isoquinolyl]-2-cyano-cyclopropanecarboxamide (220 mg, 60% yield) as a white solid. LCMS (ESI): [M+H]$^+$=381.1.

Step 3: (±)-trans-N-[8-amino-7-fluoro-6-(4-methyl-3-pyridyl)-3-isoquinolyl]-2-cyano-cyclopropanecarboxamide

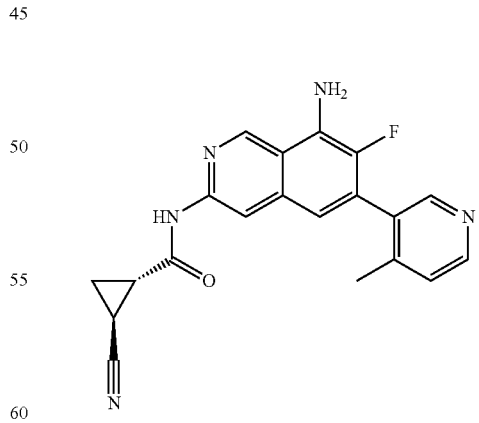

A mixture of Pd$_2$dba$_3$ (96 mg, 0.11 mmol), Cs$_2$CO$_3$ (513 mg, 1.58 mmol), trans-N-[8-chloro-7-fluoro-6-(4-methyl-3-pyridyl)-3-isoquinolyl]-2-cyano-cyclopropanecarboxamide (200 mg, 0.53 mmol), tert-butyl carbamate (615 mg, 5.25 mmol), and Xantphos (121 mg, 0.21 mmol) in toluene (6 mL) and DMF (6 mL) was heated overnight at 130° C. The mixture was diluted with ethyl acetate, washed with water (30 mL), brine (30 mL), dried over Na$_2$SO$_4$, filtered and concentrated. The residue was purified by reverse phase prep-HPLC to give (±)-trans-N-[8-amino-7-fluoro-6-(4-methyl-3-pyridyl)-3-isoquinolyl]-2-cyano-cyclopropanecarboxamide (20 mg, 10.5% yield). LCMS (ESI): R$_T$ (min)=1.330, [M+H]$^+$=362.1, method=A; $^1$H NMR (400 MHz, CD$_3$OD) δ 9.32 (s, 1H), 8.47 (d, J=5.2 Hz, 1H), 8.41 (s, 1H), 8.33 (s, 1H), 7.42 (d, J=5.2 Hz, 1H), 6.99 (d, J=6.4 Hz, 1H), 2.65-2.61 (m, 1H), 2.30 (s, 3H), 2.14-2.09 (m, 1H), 1.61-1.52 (m, 2H).

Example 40

(±)-trans-N-(8-amino-6-(5-methyl-2-oxo-2,3-dihydrobenzo[d]oxazol-6-yl)isoquinolin-3-yl)-2-cyanocyclopropanecarboxamide (Compound 54)

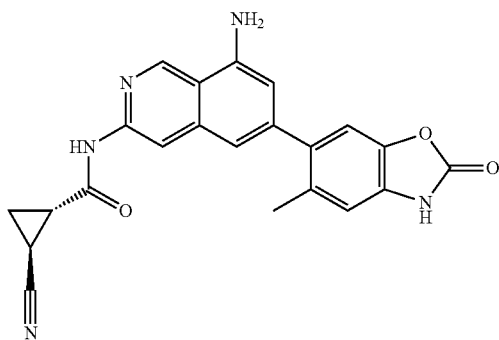

Step 1: (±)-trans-N-(8-chloro-6-(3-(4-methoxybenzyl)-5-methyl-2-oxo-2,3-dihydrobenzo[d]oxazol-6-yl)isoquinolin-3-yl)-2-cyanocyclopropanecarboxamide

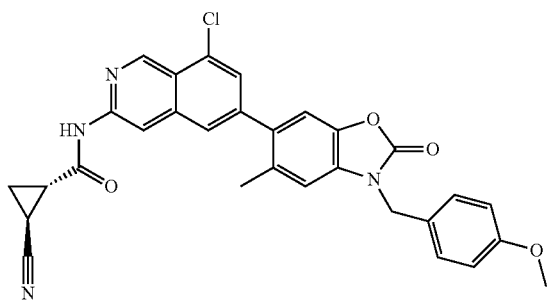 [SMILES: COc1ccc(Cn2c(=O)oc3cc(-c4cc(Cl)c5cnc(NC(=O)[C@H]6C[C@@H]6C#N)cc5c4)c(C)cc32)cc1]

A mixture of (±)-trans-N-(6-bromo-8-chloro-3-isoquinolyl)-2-cyano-cyclopropanecarboxamide (90 mg, 0.26 mmol), Pd(dppf)Cl$_2$ (18 mg, 0.03 mmol), K$_2$CO$_3$ (70 mg, 0.51 mmol), 3-[(4-methoxyphenyl)methyl]-5-methyl-6-(4,4,5,5-tetramethyl-1,3,2-dioxaborolan-2-yl)-1,3-benzoxazol-2-one (101 mg, 0.26 mmol), water (0.2 mL) and 1,4-dioxane (10 mL) was stirred at 100° C. under N$_2$ for 4 hours. The mixture was concentrated and purified by silica gel column chromatography (30% ethyl acetate in petroleum ether) to give (±)-trans-N-[8-chloro-6-[3-[(4-methoxyphenyl)methyl]-5-methyl-2-oxo-1,3-benzoxazol-6-yl]-3-isoquinolyl]-2-cyano-cyclopropanecarboxamide (90 mg, 62% yield) as a white solid. LCMS (ESI): [M+H]$^+$=539.2

Step 2: (±)-tert-butyl 3-(trans-2-cyanocyclopropanecarboxamido)-6-(3-(4-methoxybenzyl)-5-methyl-2-oxo-2,3-dihydrobenzo[d]oxazol-6-yl)isoquinolin-8-ylcarbamate

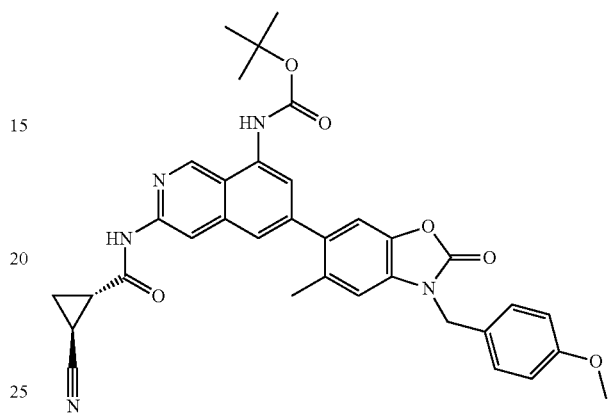

To a sealed tube was added trans-N-[8-chloro-6-[3-[(4-methoxyphenyl)methyl]-5-methyl-2-oxo-1,3-benzoxazol-6-yl]-3-isoquinolyl]-2-cyano-cyclopropanecarboxamide (75 mg, 0.14 mmol), Pd$_2$(dba)$_3$ (25 mg, 0.03 mmol), t-BuONa (27 mg, 0.28 mmol), tert-butyl carbamate (326 mg, 2.78 mmol) and 1,4-dioxane (4 mL). The mixture was stirred at 90° C. for 1 hour. The mixture was concentrated and the residue was purified by silica gel column chromatography (0-50% ethyl acetate in petroleum ether) to give (±)-tert-butyl N-[3-[[trans-2-cyanocyclopropanecarbonyl]amino]-6-[3-[(4-methoxyphenyl)methyl]-5-methyl-2-oxo-1,3-benzoxazol-6-yl]-8-isoquinolyl]carbamate (60 mg, 70% yield) as a brown solid. LCMS (ESI): [M+H]$^+$=620.3.

Step 3: (±)-trans-N-(8-amino-6-(5-methyl-2-oxo-2,3-dihydrobenzo[d]oxazol-6-yl)isoquinolin-3-yl)-2-cyanocyclopropanecarboxamide

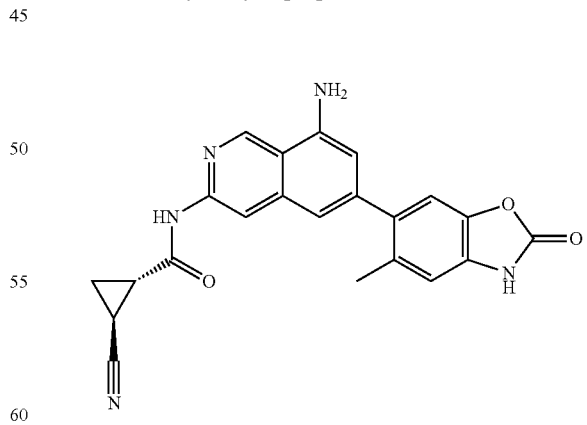

A mixture of (±)-tert-butyl N-[3-[[trans-2-cyanocyclopropanecarbonyl]amino]-6-[3-[(4-methoxyphenyl)methyl]-5-methyl-2-oxo-1,3-benzoxazol-6-yl]-8-isoquinolyl]carbamate (20 mg), TFA (0.5 mL), and trifluoromethanesulfonic acid (1 mL) was stirred at 25° C. for 2 hours. The mixture was concentrated and basified with NH$_3$ in methanol (7M).

491

The resulting residue was purified by reverse phase prep-HPLC (acetonitrile 0-50/0.1% formic acid in water) to afford (±)-trans-N-[8-amino-6-(5-methyl-2-oxo-3H-1,3-benzoxazol-6-yl)-3-isoquinolyl]-2-cyano-cyclopropanecarboxamide (4 mg, 31% yield) as a yellow solid. LCMS (ESI): R$_T$ (min)=1.669, [M+H]$^+$=400.1, method=B; $^1$H NMR (400 MHz, DMSO-d$_6$) δ 11.14 (s, 1H), 9.36 (s, 1H), 8.26 (s, 1H), 7.18 (s, 1H), 7.06 (s, 1H), 6.89 (s, 1H), 6.61 (s, 1H), 6.35 (s, 2H), 2.83-2.78 (m, 1H), 2.30 (s, 3H), 2.21-2.16 (m, 1H), 1.66-1.62 (m, 1H), 1.51-1.46 (m, 1H).

Example 41

(±)-cis-N-(8-amino-6-(2-ethyl-5-oxopyrrolidin-1-yl)isoquinolin-3-yl)-2-fluorocyclopropanecarboxamide (Compound 55)

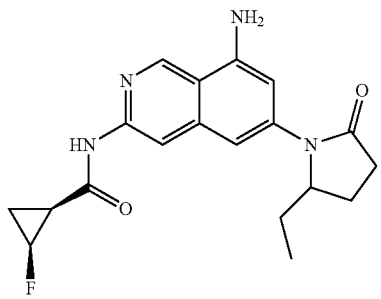 [SMILES: CCC1CCC(=O)N1c1cc(N)c2cnc(NC(=O)[C@@H]3C[C@@H]3F)cc2c1]

Step 1: (±)-cis-N-(8-chloro-6-(2-ethyl-5-oxopyrrolidin-1-yl)isoquinolin-3-yl)-2-fluorocyclopropanecarboxamide

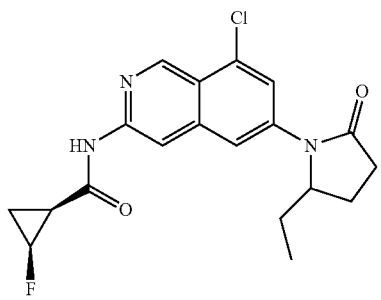

A mixture of (±)-cis-N-(6-bromo-8-chloro-3-isoquinolyl)-2-fluoro-cyclopropanecarboxamide (150 mg, 0.5 mmol), 5-ethylpyrrolidin-2-one (56 mg, 0.5 mmol), Pd$_2$(dba)$_3$ (45 mg, 0.05 mmol), Cs$_2$CO$_3$ (324 mg, 1.0 mmol), Xantphos (58 mg, 0.1 mmol) in 1,4-dioxane (10 mL) was stirred at 100° C. under N$_2$ for 16 hours. The mixture was concentrated and the residue was purified by silica gel column chromatography (0-100% ethyl acetate in petroleum ether) to give (±)-cis-N-[8-chloro-6-[2-ethyl-5-oxo-pyrrolidin-1-yl]-3-isoquinolyl]-2-fluoro-cyclopropanecarboxamide (120 mg, 64% yield) as a white solid. LCMS (ESI): [M+H]=376.1.

492

Step 2: (±)-cis-N-(8-amino-6-(2-ethyl-5-oxopyrrolidin-1-yl)isoquinolin-3-yl)-2-fluorocyclopropane Carboxamide


A mixture of (±)-cis-N-[8-chloro-6-(2-ethyl-5-oxo-pyrrolidin-1-yl)-3-isoquinolyl]-2-fluoro-cyclopropanecarboxamide (100 mg, 0.27 mmol), tert-butyl carbamate (311 mg, 2.66 mmol), tert-BuBrettphos (51 mg, 0.108 mmol), Pd$_2$(dba)$_3$ (47 mg, 0.054 mmol), and t-BuONa (51 mg, 0.53 mmol) in 1-methyl-2-pyrrolidinone (1 mL) was stirred at 110° C. under N$_2$ for 2 hours. The mixture was concentrated and purified by silica gel column chromatography (0-100% ethyl acetate in petroleum ether) to give (±)-cis-N-[8-amino-6-(2-ethyl-5-oxo-pyrrolidin-1-yl)-3-isoquinolyl]-2-fluoro-cyclopropanecarboxamide (6 mg, 6.3% yield) as a yellow solid. LCMS (ESI): R$_T$ (min)=1.625, [M+H]$^+$=356.7, method=C; $^1$H NMR (400 MHz, CD$_3$OD) δ 9.15 (s, 1H), 8.26 (s, 1H), 7.07-7.04 (m, 1H), 6.85-6.84 (m, 1H), 5.00-4.78 (m, 1H), 4.43-4.35 (m, 1H), 2.67-2.54 (m, 2H), 2.43-2.34 (m, 1H), 2.20-2.10 (m, 1H), 1.97-1.69 (m, 3H), 1.55-1.47 (m, 1H), 1.26-1.17 (m, 1H), 0.91 (t, J=7.2 Hz, 3H).

Example 42

(±)-trans-N-(8-amino-6-(6-ethoxy-4-ethylpyridin-3-yl)isoquinolin-3-yl)-2-cyanocyclopropanecarboxamide (Compound 56)

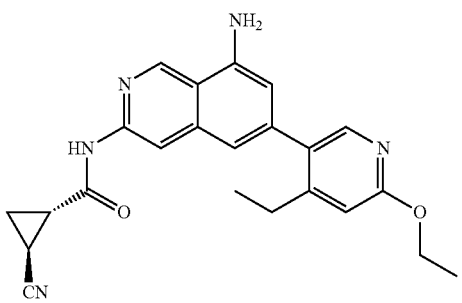 [SMILES: CCOc1cc(CC)c(-c2cc(N)c3cnc(NC(=O)[C@H]4C[C@@H]4C#N)cc3c2)cn1]

493

Step 1: (±)-trans-N-(8-amino-6-(4-ethylpyridin-3-yl)-2,7-naphthyridin-3-yl)-2-cyanocyclopropane carboxamide

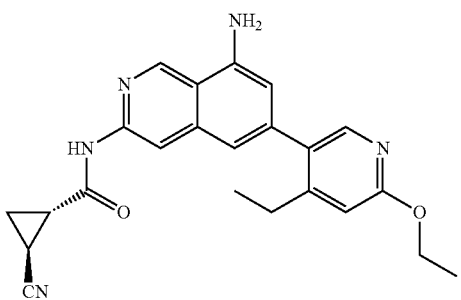 [SMILES: CCOc1cc(CC)c(-c2cc(N)c3cnc(NC(=O)[C@H]4C[C@@H]4C#N)cc3c2)cn1]

A mixture of (±)-trans-N-[8-chloro-6-(6-ethoxy-4-ethyl-3-pyridyl)-3-isoquinolyl]-2-cyano-cyclopropanecarboxamide (100 mg, 0.24 mmol), tert-butyl carbamate (555 mg, 4.74 mmol), t-BuBrettphos (46 mg, 0.1 mmol), Pd$_2$(dba)$_3$ (43 mg, 0.05 mmol), and t-BuONa (45 mg, 0.48 mmol) in 1-methyl-2-pyrrolidinone (4 mL) was stirred at 110° C. for 2 hours. The mixture was concentrated and purified by silica gel column chromatography (0-100% ethyl acetate in petroleum ether) to give (±)-trans-N-[8-amino-6-(6-ethoxy-4-ethyl-3-pyridyl)-3-isoquinolyl]-2-cyano-cyclopropanecarboxamide (6 mg, 6.3% yield) as a yellow solid. LCMS (ESI): R$_T$ (min)=1.956, [M+H]$^+$=402.2, method=C; $^1$H NMR (400 MHz, CD$_3$OD) δ 9.24 (s, 1H), 8.26 (s, 1H), 7.94 (s, 1H), 6.95 (s, 1H), 6.76 (s, 1H), 6.67 (d, J=1.6 Hz, 1H), 4.35 (q, J=6.8 Hz, 2H), 2.69-2.63 (m, 3H), 2.14-2.09 (m, 1H), 1.61-1.53 (m, 2H), 1.42 (t, J=7.2 Hz, 3H), 1.12 (t, J=7.6 Hz, 3H).

Example 43

(±)-trans-N-(8-amino-6-(1,2-dimethyl-1H-imidazol-5-yl)isoquinolin-3-yl)-2-cyanocyclopropanecarboxamide (Compound 57)

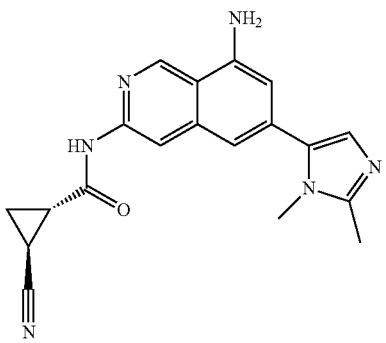 [SMILES: Cc1ncc(-c2cc(N)c3cnc(NC(=O)[C@H]4C[C@@H]4C#N)cc3c2)n1C]

494

Step 1: 1,2-dimethyl-5-(4,4,5,5-tetramethyl-1,32-dioxaborolan-2-yl)-1H-imidazole

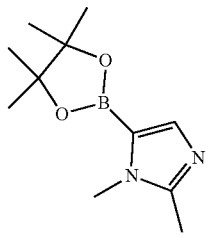 [SMILES: Cc1ncc(B2OC(C)(C)C(C)(C)O2)n1C]

In a glove box, a pressure tube was charged with [Ir(OMe)(COD)]$_2$ (105 mg, 0.16 mmol), THF (5 mL), and pinacolborane (1.1 mL, 7.8 mmol). The reaction mixture was stirred at room temperature for 10 minutes and to this 4,4-di-tert-butyl bipyridine (42 mg, 0.16 mmol) was added. The reaction was stirred at room temperature for an additional 10 minutes. A solution of 1,2-dimethylimidazole (500 mg, 5.2 mmol) in THF (5 mL) was added. The mixture was stirred at room temperature for 16 hours. The mixture was then concentrated in vacuo. The residue was washed with hexane (10 mL×4) and concentrated to give 1,2-dimethyl-5-(4,4,5,5-tetramethyl-1,3,2-dioxaborolan-2-yl)imidazole (1 g, 52% yield) as a brown solid. LCMS (ESI) [M+H]$^+$=223.2.

Step 2: (±)-trans-N-(8-amino-6-chloro-2,7-naphthyridin-3-yl)-2-methylcyclopropanecarboxamide

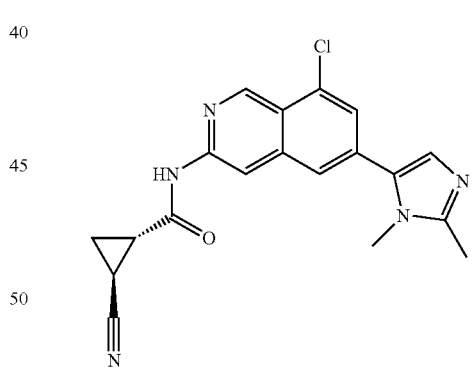

To a sealed tube was added (±)-trans-N-(6-bromo-8-chloro-3-isoquinolyl)-2-cyano-cyclopropanecarboxamide (220 mg, 0.63 mmol), 1,2-dimethyl-5-(4,4,5,5-tetramethyl-1,3,2-dioxaborolan-2-yl)imidazole (385 mg, 1.73 mmol), Pd(dppf)Cl$_2$ (101 mg, 0.14 mmol) and Na$_2$CO$_3$ (202 mg, 1.91 mmol), 1,4-dioxane (10 mL) and water (1 mL). The mixture was bubbled through with N$_2$ for 2 minutes and stirred at 100° C. for 2.5 hours. The mixture was concentrated and purified by silica gel flash chromatography (petroleum ether/ethyl acetate, 1:1 to 0:100) to give (±)-trans-N-[8-chloro-6-(2,3-dimethylimidazol-4-yl)-3-isoquinolyl]-2-cyano-cyclopropanecarboxamide (250 mg, 97% yield) as a yellow solid. LCMS (ESI): [M+H]$^+$=366.1.

Step 3: (±)-trans-N-(8-amino-6-(1,2-dimethyl-1H-imidazol-5-yl)isoquinolin-3-yl)-2-cyanocyclopropanecarboxamide

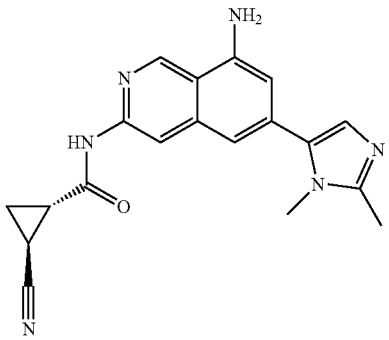 [SMILES: Cc1ncc(-c2cc(N)c3cnc(NC(=O)[C@H]4C[C@@H]4C#N)cc3c2)n1C]

To a sealed tube was added tert-butyl carbamate (768 mg, 6.56 mmol), (±)-trans-N-[8-chloro-6-(2,3-dimethylimidazol-4-yl)-3-isoquinolyl]-2-cyano-cyclopropanecarboxamide (240 mg, 0.66 mmol), Pd$_2$(dba)$_3$ (150 mg, 0.16 mmol), Cs$_2$CO$_3$ (700 mg, 2.15 mmol), Xantphos (100 mg, 17 mmol) and 1-methyl-2-pyrrolidinone (15 mL). The mixture was stirred at 130° C. for 2 hours. The reaction mixture was concentrated in vacuum and purified by column chromatography (BOSTOM ODS 40 g column, eluted with 10 mM NH$_4$HCO$_3$ in acetonitrile from 100:0 to 1:5) to give the crude product (100 mg). The crude product was purified again by prep-TLC (silica-gel, dichloromethane/methanol, 10:1) to give (±)-trans-N-[8-amino-6-(2,3-dimethylimidazol-4-yl)-3-isoquinolyl]-2-cyano-cyclopropanecarboxamide (10 mg, 4% yield) as a pale-yellow solid. LCMS (ESI): R$_T$ (min)=1.532, [M+H]$^+$=346.8, method=H; $^1$H NMR (400 MHz, CD$_3$OD) δ: 9.19 (s, 1H), 8.27 (s, 1H), 7.06 (s, 1H), 6.98 (s, 1H), 7.76 (d, J=1.6 Hz, 1H), 3.66 (s, 3H), 2.67-2.60 (m, 1H), 2.45 (s, 3H), 2.13-2.04 (m, 1H), 1.63-1.50 (m, 2H).

Example 44

(±)-cis-N-[8-amino-6-(3-methyl-4-pyridyl)-3-isoquinolyl]-2-fluoro-cyclopropanecarboxamide (Compound 59)

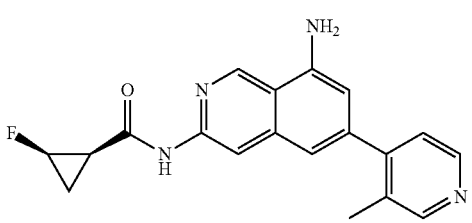

Step 1: (±)-cis-N-(8-chloro-6-(3-methylpyridin-4-yl)isoquinolin-3-yl)-2-fluorocyclopropanecarboxamide

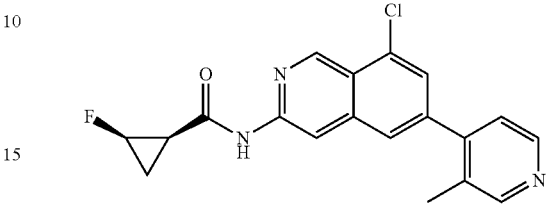

To a sealed tube was added (±)-cis-N-(6-bromo-8-chloro-3-isoquinolyl)-2-fluoro-cyclopropanecarboxamide (200 mg, 0.58 mmol), 3-methylpyridine-4-boronic acid (95 mg, 0.70 mmol), Pd(dppf)Cl$_2$ (52 mg, 0.07 mmol), K$_3$PO$_4$ (122 mg, 0.58 mmol), sodium acetate (185 mg, 1.75 mmol), acetonitrile (20 mL) and water (2 mL). The mixture was stirred at 90° C. for 3 hours under N$_2$. The mixture was concentrated and purified by silica gel flash chromatography (petroleum ether/ethyl acetate, 2:3) to afford (±)-cis-N-[8-chloro-6-(3-methyl-4-pyridyl)-3-isoquinolyl]-2-fluoro-cyclopropanecarboxamide (140 mg, 67% yield) as a white solid. LCMS (ESI): [M+H]$^+$=356.1.

Step 2: (±)-cis-N-[8-amino-6-(3-methyl-4-pyridyl)-3-isoquinolyl]-2-fluoro-cyclopropanecarboxamide

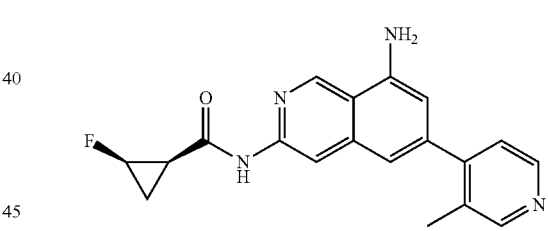

A mixture of (±)-cis-N-[8-chloro-6-(3-methyl-4-pyridyl)-3-isoquinolyl]-2-fluoro-cyclopropanecarboxamide (130 mg, 0.37 mmol), tert-butyl carbamate (428 mg, 3.65 mmol), Pd$_2$dba$_3$ (66 mg, 0.07 mmol), Xantphos (84 mg, 0.15 mmol), and Cs$_2$CO$_3$ (357 mg, 1.1 mmol) in toluene (3 mL) and DMF (3 mL) was heated in a sealed tube at 110° C. for 16 hours. The reaction mixture was cooled to room temperature, diluted with ethyl acetate, washed with brine, dried over Na$_2$SO$_4$, filtered and concentrated. The residue was washed with petroleum ether and ethyl acetate to give the crude product, which was purified by reverse phase prep-HPLC to give (±)-cis-N-[8-amino-6-(3-methyl-4-pyridyl)-3-isoquinolyl]-2-fluoro-cyclopropanecarboxamide (25 mg, 20% yield) as a yellow solid. LCMS (ESI): R$_T$ (min)=1.605, [M+H]$^+$=337.1, method=C; $^1$H NMR (400 MHz, CD$_3$OD) δ 9.25 (s, 1H), 8.48 (s, 1H), 8.43 (d, J=4.8 Hz, 1H), 8.33 (s, 1H), 7.36 (d, J=4.8 Hz, 1H), 7.02 (s, 1H), 6.69 (d, J=1.2 Hz, 1H), 4.99-4.79 (m, 1H), 2.35 (s, 3H), 2.20-2.12 (m, 1H), 1.87-1.77 (m, 1H), 1.27-1.18 (m, 1H).

Example 45

(±)-((trans)-N-(8-amino-6-(4-(1,1-difluoroethyl)
pyridin-3-yl)isoquinolin-3-yl)-2-cyanocyclopropan-
ecarboxamide (Compound 60)

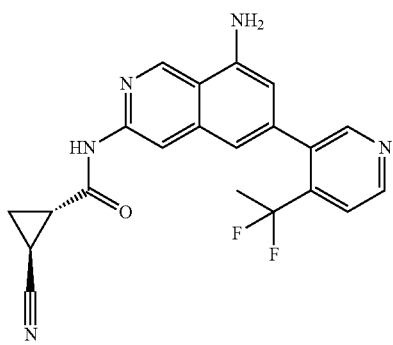 [SMILES: CC(F)(F)c1ccncc1-c1cc(N)c2cnc(NC(=O)[C@H]3C[C@@H]3C#N)cc2c1]

Step 1: 4-(1,1-difluoroethyl)-3-(4,4,5,5-tetramethyl-
1,3,2-dioxaborolan-2-yl)pyridine

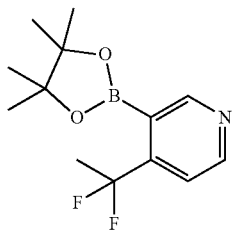 [SMILES: CC(F)(F)c1ccncc1B1OC(C)(C)C(C)(C)O1]

A mixture of 3-bromo-4-(1,1-difluoroethyl)pyridine (500 mg, 2.25 mmol), bis(pinacolato)diboron (857 mg, 3.37 mmol), PdCl$_2$dppf (164 mg, 0.22 mmol), and potassium acetate (662 mg, 6.76 mmol) in 1,4-dioxane (10 mL) was heated at 100° C. for 16 hours under Ar. The reaction was concentrated to dryness. The residue was purified by silica gel column chromatography (petroleum ether:ethyl acetate=10:1 to petroleum ether/ethyl acetate=2:1) to give the title compound as a yellow oil (105 mg, 17% yield). LCMS (ESI) [M+H]$^+$=270.2.

Step 2: (±)-(trans)-N-(8-chloro-6-(4-(1,1-difluoro-
ethyl)pyridin-3-yl)isoquinolin-3-yl)-2-cyanocyclo-
propanecarboxamide

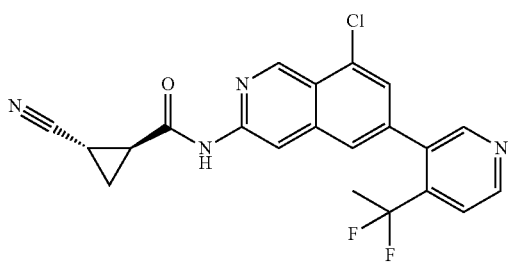 [SMILES: CC(F)(F)c1ccncc1-c1cc(N)c2cnc(NC(=O)[C@H]3C[C@@H]3C#N)cc2c1]

A mixture of trans-N-(6-bromo-8-chloro-3-isoquinolyl)-2-cyano-cyclopropanecarboxamide (108 mg, 0.31 mmol), 4-(1,1-difluoroethyl)-3-(4,4,5,5-tetramethyl-1,3,2-dioxa-borolan-2-yl)pyridine (100 mg, 0.37 mmol), Pd(PPh$_3$)$_4$ (36 mg, 0.03 mmol), potassium acetate (90 mg, 0.92 mmol) in 1,4-dioxane (4 mL) and water (1 mL) was heated at 90° C. for 4 hours under Ar. The reaction was concentrated to dryness. The residue was purified by silica gel column chromatography (petroleum ether/ethyl acetate=4:1 to petroleum ether/ethyl acetate=2:1) to give the title compound as a white solid (80 mg, 61% yield). LCMS (ESI) [M+H]$^+$=413.1.

Step 3: (±)-trans-2-cyano-N-(6-(4-(1,1-difluoro-
ethyl)pyridin-3-yl)-8-(diphenylmethyleneamino)
isoquinolin-3-yl)cyclopropanecarboxamide

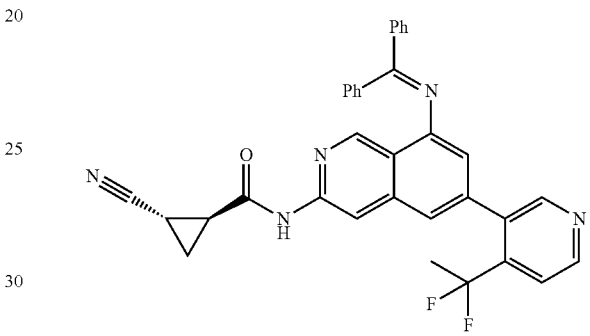

A mixture of (±)-trans-N-[8-chloro-6-[4-(1,1-difluoro-ethyl)-3-pyridyl]-3-isoquinolyl]-2-cyano-cyclopropanecar-boxamide (70 mg, 0.17 mmol), benzophenone imine (92 mg, 0.51 mmol), Pd$_2$(dba)$_3$ (31 mg, 0.03 mmol), Xantphos (10 mg, 0.02 mmol), Cs$_2$CO$_3$ (165 mg, 0.51 mmol) in DMF (0.5 mL) and toluene (0.5 mL) was heated at 130° C. for 3 hours under Ar. The reaction was diluted with ethyl acetate and washed with brine. The organic layer was separated, dried (NaSO$_4$) and concentrated to dryness. The residue was purified by silica gel column chromatography (petroleum ether/ethyl acetate=4:1 to petroleum ether/ethyl acetate=2:1) to give the title compound as a yellow solid (25 mg, 23.6% yield). LCMS (ESI) [M+H]$^+$=558.2.

Step 4: (±)-trans-N-(8-amino-6-(4-(1,1-difluoro-
ethyl)pyridin-3-yl)isoquinolin-3-yl)-2-cyanocyclo-
propanecarboxamide

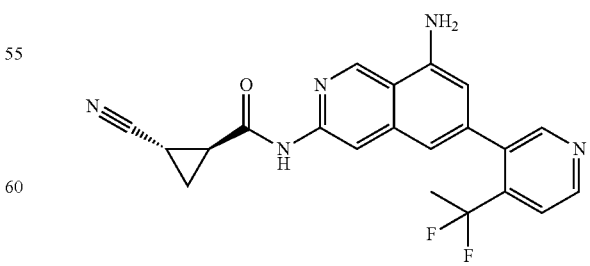

A mixture of (±)-(trans)-N-[8-(benzhydrylideneamino)-6-[4-(1,1-difluoroethyl)-3-pyridyl]-3-isoquinolyl]-2-cyano-cyclopropanecarboxamide (25 mg, 0.04 mmol) and TFA (0.5 mL, 6.71 mmol) in dichloromethane (2 mL) and two drops of water was stirred at room temperature for 2 hours under N$_2$. The reaction was concentrated to dryness. The residue was taken up in methanol (0.5 mL) and adjusted pH to 7-8 with sat NaHCO$_3$. The mixture was purified directly by reverse phase prep-HPLC (eluent: 5%-95% methanol and water) to give the title compound as a yellow solid (14.2 mg, 81% yield). LCMS (ESI): R$_T$ (min)=1.75, [M+H]$^+$=394.2, method=B. $^1$H NMR (400 MHz, DMSO-d$_6$) δ 11.13 (s, 1H), 9.35 (s, 1H), 8.75 (d, J=5.2 Hz, 1H), 8.51 (s, 1H), 8.21 (s, 1H), 7.64 (d, J=5.6 Hz, 1H), 6.87 (s, 1H), 6.53 (s, 1H), 6.41 (s, 2H), 2.77-2.50 (m, 1H), 2.14-2.10 (m, 1H), 1.77 (t, J=19.2 Hz, 1H), 1.61-1.58 (m, 1H), 1.44-1.43 (m, 1H).

Example 46

(±)-N-(8-amino-6-(4-methylpyridin-3-yl)isoquinolin-3-yl)-2-(morpholin-3-yl)acetamide (Compound 61)

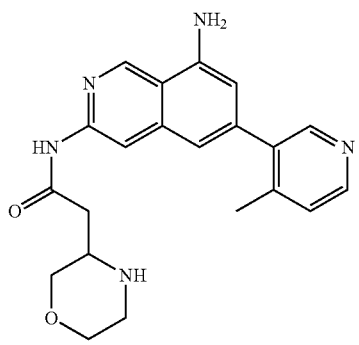 [SMILES: Cc1ccncc1-c1cc(N)c2cnc(NC(=O)CC3COCCN3)cc2c1]

Step 1: 8-chloro-6-(4-methylpyridin-3-yl)isoquinolin-3-amine

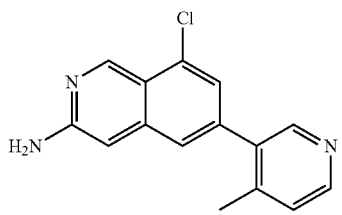 [SMILES: Cc1ccncc1-c1cc(Cl)c2cnc(N)cc2c1]

A mixture of 6-bromo-8-chloro-isoquinolin-3-amine (2000 mg, 7.77 mmol), 4-methyl-3-(4,4,5,5-tetramethyl-1,3,2-dioxaborolan-2-yl)pyridine (2042 mg, 9.32 mmol), Pd(dppf)Cl$_2$ (284 mg, 0.39 mmol), and Na$_2$CO$_3$ (2058 mg, 19.42 mmol) in 1,4-dioxane (20 mL) and water (2 mL) was stirred at 90° C. for 2 hours. The reaction was concentrated. The residue was purified by silica gel flash column chromatography (petroleum ether/ethyl acetate, 2:1 to 1:4) to give 8-chloro-6-(4-methyl-3-pyridyl)isoquinolin-3-amine (1.3 g, 52% yield) as a yellow solid. LCMS (ESI): [M+H]$^+$=270.1.

Step 2: (±)-tert-butyl 3-(2-(8-chloro-6-(4-methylpyridin-3-yl)isoquinolin-3-ylamino)-2-oxoethyl)morpholine-4-carboxylate

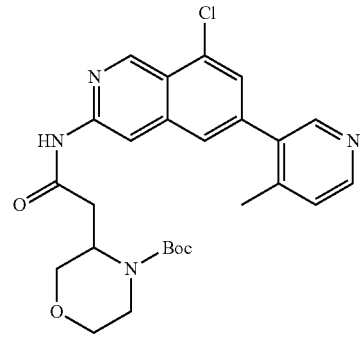 [SMILES: Cc1ccncc1-c1cc(Cl)c2cnc(NC(=O)CC3COCCN3C(=O)OC(C)(C)C)cc2c1]

To a solution of 8-chloro-6-(4-methyl-3-pyridyl)isoquinolin-3-amine (130 mg, 0.48 mmol) and 2-(4-tert-butoxycarbonylmorpholin-3-yl)acetic acid (142 mg, 0.58 mmol) in pyridine (2 mL) was added phosphorus oxychloride (369 mg, 2.4 mmol). The resulting mixture was stirred at 25° C. for 1 hour. The mixture was concentrated and purified by silica gel flash column chromatography (petroleum ether/ethyl acetate, 3:1 to 1:2) to give (±)-tert-butyl 3-[2-[[8-chloro-6-(4-methyl-3-pyridyl)-3-isoquinolyl]amino]-2-oxoethyl]morpholine-4-carboxylate (130 mg, 48% yield) as a yellow solid. LCMS (ESI): [M+H]$^+$=497.2.

Step 3: (±)-tert-butyl 3-(2-(8-(tert-butoxycarbonylamino)-6-(4-methylpyridin-3-yl)isoquinolin-3-ylamino)-2-oxoethyl)morpholine-4-carboxylate

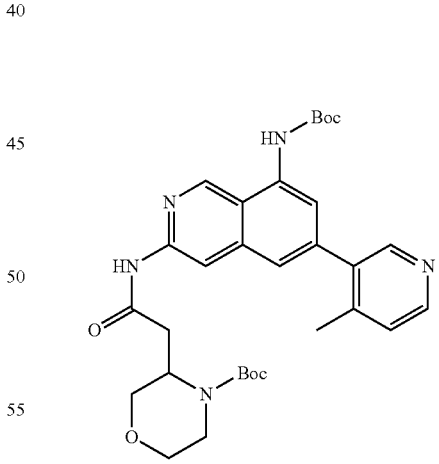

A mixture of (±)-tert-butyl carbamate (259 mg, 2.21 mmol), tert-butoxysodium (234 mg, 2.43 mmol), tert-butyl 3-[2-[[8-chloro-6-(4-methyl-3-pyridyl)-3-isoquinolyl]amino]-2-oxo-ethyl]morpholine-4-carboxylate (110 mg, 0.22 mmol), Pd$_2$(dba)$_3$ (20 mg, 0.02 mmol) and Brettphos (24 mg, 0.04 mmol) in 1,4-dioxane (4 mL) was stirred at 90° C. for 1 hour. The reaction was concentrated and purified by silica gel flash column chromatography (petroleum ether: ethyl acetate, 3:1 to 1:3) to give (±)-tert-butyl 3-[2-[[8-(tert-butoxycarbonylamino)-6-(4-methyl-3-pyridyl)-3-isoquinolyl]amino]-2-oxo-ethyl]morpholine-4-carboxylate (36 mg, 23% yield) as a yellow solid. LCMS (ESI): [M+H]⁺=578.3.

Step 4: (±)-N-(8-amino-6-(4-methylpyridin-3-yl)isoquinolin-3-yl)-2-(morpholin-3-yl)acetamide

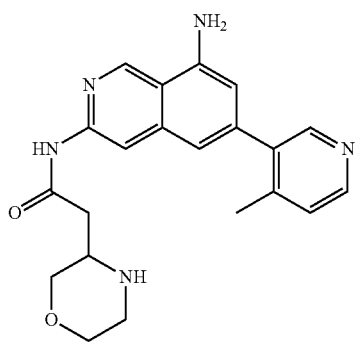 [SMILES: Cc1ccncc1-c1cc(N)c2cnc(NC(=O)CC3COCCN3)cc2c1]

A mixture of (±)-tert-butyl 3-[2-[[8-(tert-butoxycarbonylamino)-6-(4-methyl-3-pyridyl)-3-isoquinolyl]amino]-2-oxo-ethyl]morpholine-4-carboxylate (36 mg, 0.06 mmol) in 0.5 mL of 4 M HCl in 1,4-dioxane was stirred for 1 hour. The reaction was concentrated and purified by reverse phase HPLC (acetonitrile 10-47/0.05% ammonia in water) to give (±)-N-[8-amino-6-(4-methyl-3-pyridyl)-3-isoquinolyl]-2-morpholin-3-yl-acetamide (7.1 mg, 30.2% yield) as a yellow solid. LCMS (ESI): R$_T$ (min)=1.490, [M+H]⁺=378.2, method=C; ¹H NMR (400 MHz, DMSO-d$_6$): 10.62 (s, 1H), 9.30 (s, 1H), 8.45 (d, J=4.8 Hz, 1H), 8.41 (s, 1H), 8.29 (s, 1H), 7.35 (d, J=4.8 Hz, 1H), 6.92 (s, 1H), 6.56 (s, 1H), 6.33 (s, 2H), 3.71-3.63 (m, 2H), 3.22-3.20 (m, 1H), 3.12-3.10 (m, 2H), 2.78-2.75 (m, 2H), 2.41-2.40 (m, 2H), 2.30 (s, 3H).

Example 47

(±)-trans-N-(8-amino-6-(4-methylisothiazol-5-yl)isoquinolin-3-yl)-2-cyanocyclopropanecarboxamide
(Compound 62)

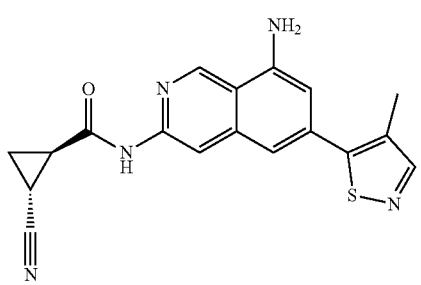 [SMILES: Cc1cnsc1-c1cc(N)c2cnc(NC(=O)[C@@H]3C[C@H]3C#N)cc2c1]

Step 1: (±)-trans-N-(8-chloro-6-(4-methylisothiazol-5-yl)isoquinolin-3-yl)-2-cyanocyclopropanecarboxamide

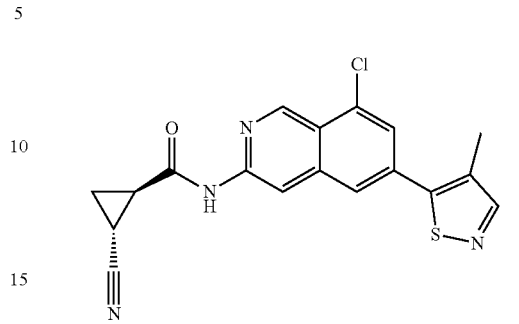

A mixture of (±)-trans-8-chloro-3-(2-cyanocyclopropanecarboxamido)isoquinolin-6-ylboronic acid (240 mg, 0.76 mmol), 5-bromo-4-methyl-isothiazole (162 mg, 0.91 mmol), Pd(dppf)Cl$_2$ (28 mg, 0.04 mmol), and Na$_2$CO$_3$ (161 mg, 1.52 mmol) in 1,4-dioxane (4 mL) and water (0.4 mL) was stirred at 90° C. for 3 hours. The mixture was concentrated. The residue was purified by silica gel flash column chromatography (petroleum ether/ethyl acetate, 5:1 to 1:5) to give (±)-trans-N-[8-chloro-6-(4-methylisothiazol-5-yl)-3-isoquinolyl]-2-cyano-cyclopropanecarboxamide (190 mg, 48% yield) as a yellow solid. LCMS (ESI): [M+H]⁺=369.0.

Step 2: (±)-trans-2-cyano-N-(8-(diphenylmethyleneamino)-6-(4-methylisothiazol-5-yl)isoquinolin-3-yl)cyclopropanecarboxamide

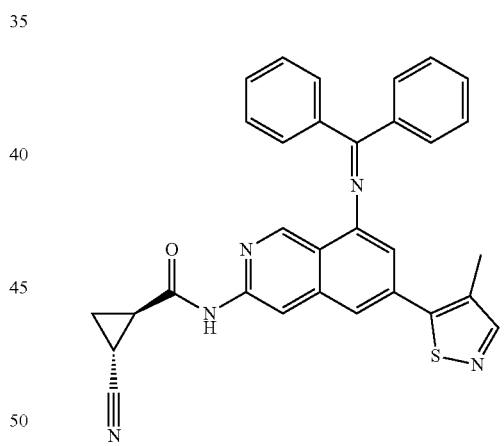

A mixture of (±)-trans-N-[8-chloro-6-(4-methylisothiazol-5-yl)-3-isoquinolyl]-2-cyano-cyclopropanecarboxamide (90 mg, 0.24 mmol), benzophenone imine (88 mg, 0.49 mmol), Pd$_2$(dba)$_3$ (45 mg, 0.05 mmol), Xantphos (56 mg, 0.10 mmol), and Cs$_2$CO$_3$ (161 mg, 0.49 mmol) in DMF (2 mL) and toluene (2 mL) was stirred at 130° C. for 3 hours. The reaction was then cooled to room temperature and diluted with water (10 mL). The mixture was extracted with ethyl acetate (20 mL×2). The combined organic extracts were concentrated in vacuo. The residue was purified by silica gel column chromatography (petroleum ether/ethyl acetate, 3:1 to 1:2) to give (±)-trans-N-[8-(benzhydrylideneamino)-6-(4-methylisothiazol-5-yl)-3-isoquinolyl]-2-cyano-cyclopropanecarboxamide (36 mg, 20% yield) as a yellow solid. LCMS (ESI): [M+H]⁺=514.2.

Step 3: (±)-trans-N-(8-amino-6-(4-methylisothiazol-5-yl)isoquinolin-3-yl)-2-cyanocyclopropanecarboxamide

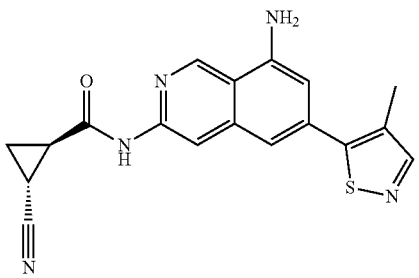 [SMILES: Cc1cnsc1-c1cc(N)c2cnc(NC(=O)[C@@H]3C[C@H]3C#N)cc2c1]

To a solution of (±)-trans-N-[8-(benzhydrylideneamino)-6-(4-methylisothiazol-5-yl)-3-isoquinolyl]-2-cyano-cyclopropanecarboxamide (36 mg, 0.05 mmol) in acetonitrile (3 mL) was added 1 drop of TFA and 1 drop of water. The resulting solution was stirred for 20 minutes. The reaction solution was concentrated and purified by reverse phase prep-HPLC (acetonitrile 10-47/0.05% ammonia in water) to give (±)-trans-N-[8-amino-6-(4-methylisothiazol-5-yl)-3-isoquinolyl]-2-cyano-cyclopropanecarboxamide (8 mg, 47% yield) as a yellow solid. LCMS (ESI): $R_T$ (min)=1.759, $[M+H]^+$=350.1, method=C; $^1$H NMR (400 MHz, DMSO-$d_6$): 9.34 (s, 1H), 8.47 (s, 1H), 8.28 (s, 1H), 7.09 (s, 1H), 6.74 (d, J=1.6 Hz, 1H), 6.52 (s, 2H), 6.08 (d, J=1.6 Hz, 1H), 2.78-2.74 (m, 1H), 2.40 (s, 3H), 2.17-2.12 (m, 1H), 1.62-1.60 (m, 1H), 1.46-1.42 (m, 1H).

Example 48

(±)-trans-N-[8-amino-6-[6-(difluoromethoxy)-4-ethyl-3-pyridyl]-3-isoquinolyl]-2-cyano-cyclopropanecarboxamide (Compound 63)

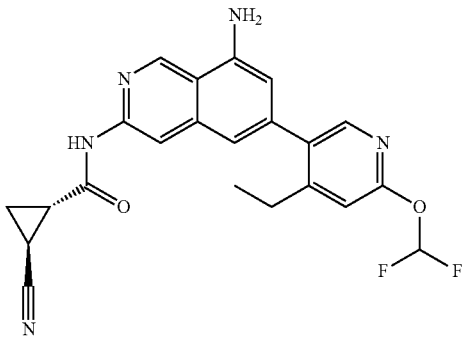 [SMILES: CCc1cc(OC(F)F)ncc1-c1cc(N)c2cnc(NC(=O)[C@H]3C[C@@H]3C#N)cc2c1]

Step 1: 5-bromo-2-(difluoromethoxy)-4-ethyl-pyridine

A mixture of 5-bromo-4-ethyl-pyridin-2-ol (1.0 g, 4.9 mmol), cesium carbonate (2.4 g, 7.4 mmol) and sodium chlorodifluoroacetate (760 mg, 5.0 mmol) in DMF (20 mL) was stirred at 100° C. for 3 hours. The cooled mixture was diluted with water (30 mL) and extracted with ether (25 mL). The organic phase was washed with water then brine, dried (Na$_2$SO$_4$), and concentrated. The major isomer, the O-alkylated product, was isolated by silica gel flash chromatography (0-10% ethyl acetate in hexane) to give the title compound (130 mg, 8.5% yield) as a colorless liquid. LCMS (ESI): $[M+H]^+$=253.1.

Step 2: 2-(difluoromethoxy)-4-ethyl-5-(4,4,5,5-tetramethyl-1,3,2-dioxaborolan-2-yl)pyridine

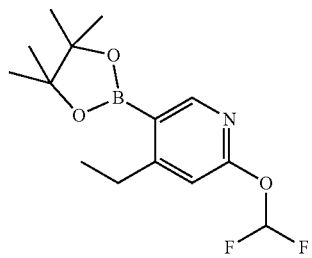 [SMILES: CCc1cc(OC(F)F)ncc1B1OC(C)(C)C(C)(C)O1]

Bis(pinacolato)diborane (220 mg, 0.9 mmol), potassium acetate (100.0 mg, 1.0 mmol) and Pd(dppf)Cl$_2$ (40 mg, 0.05 mmol) were added sequentially to a solution of 5-bromo-2-(difluoromethoxy)-4-ethyl-pyridine (110 mg, 0.4 mmol) in 1,4-dioxane (10 mL) under an Ar atmosphere. The reaction mixture was stirred overnight at 100° C. The reaction mixture was concentrated in vacuo. The residue was purified by silica gel column chromatography (ethyl acetate/petroleum ether, 0-100% yield) to afford 2-(difluoromethoxy)-4-ethyl-5-(4,4,5,5-tetramethyl-1,3,2-dioxaborolan-2-yl)pyridine (150 mg, 63% yield) as a light yellow oil. LCMS (ESI): $[M+H]^+$=300.1.

Step 3: (±)-trans-N-[8-chloro-6-[6-(difluoromethoxy)-4-ethyl-3-pyridyl]-3-isoquinolyl]-2-cyano-cyclopropanecarboxamide

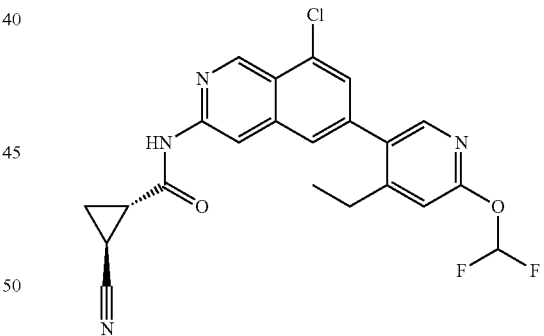

A mixture of (±)-trans-N-(6-bromo-8-chloro-3-isoquinolyl)-2-cyano-cyclopropanecarboxamide (100 mg, 0.3 mmol), Pd(PPh$_3$)$_4$ (35 mg, 0.03 mmol) and K$_3$PO$_4$ (120 mg, 0.6 mmol) were added sequentially to a solution of 2-(difluoromethoxy)-4-ethyl-5-(4,4,5,5-tetramethyl-1,3,2-dioxaborolan-2-yl)pyridine (105 mg, 0.4 mmol) in 1,4-dioxane (6 mL) and water (0.6 mL). The reaction mixture was stirred at 100° C. for 2 hours. The reaction mixture was concentrated in vacuo. The residue was purified on silica gel column chromatography (methanol/dichloromethane, 1:3) to afford (±)-trans-N-[8-chloro-6-[6-(difluoromethoxy)-4-ethyl-3-pyridyl]-3-isoquinolyl]-2-cyano-cyclopropanecarboxamide (100 mg, 53% yield) as a white solid. LCMS (ESI): $[M+H]^+$=443.1.

Step 4: (±)-trans-N-[8-amino-6-[6-(difluoromethoxy)-4-ethyl-3-pyridyl]-3-isoquinolyl]-2-cyano-cyclopropanecarboxamide

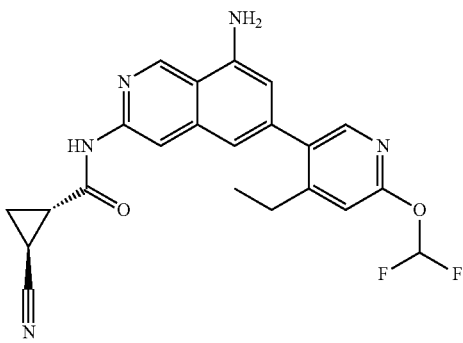 [SMILES: CCc1cc(OC(F)F)ncc1-c1cc(N)c2cnc(NC(=O)[C@H]3C[C@@H]3C#N)cc2c1]

A mixture of tert-butyl carbamate (265.0 mg, 2.3 mmol), (±)-trans-N-[8-chloro-6-[6-(difluoromethoxy)-4-ethyl-3-pyridyl]-3-isoquinolyl]-2-cyano-cyclopropanecarboxamide (100 mg, 0.23 mmol), Pd$_2$(dba)$_3$ (40 mg, 0.04 mmol), NaOtBu (55.0 mg, 0.6 mmol) and tBu-Brettphos (49.0 mg, 0.09 mmol) in dichloromethane (5 mL) was stirred at 120° C. for 1 h under N$_2$. The reaction mixture was concentrated in vacuum and the residue was purified by silica gel flash chromatography (ethyl acetate/petroleum ether, 0 to 50% yield) and reverse phase prep-HPLC to give (±)-trans-N-[8-amino-6-[6-(difluoromethoxy)-4-ethyl-3-pyridyl]-3-isoquinolyl]-2-cyano-cyclopropanecarboxamide (3 mg, 3.1% yield) as a yellow solid. LCMS (ESI): R$_T$ (min)=1.950, [M+H]$^+$=424.2, method=F; $^1$H NMR (400 MHz, CD$_3$OD) δ: 9.26 (s, 1H), 8.28 (s, 1H), 8.06 (s, 1H), 7.58 (t, J=73.2 Hz, 1H), 6.97 (s, 2H), 6.67 (s, 1H), 2.71 (q, J=7.6 Hz, 2H), 2.68-2.65 (m, 1H), 2.14-2.09 (m, 1H), 1.63-1.52 (m, 2H), 1.15 (t, J=7.6 Hz, 3H).

Example 49

(±)-trans-N-[8-amino-6-[4-(2-hydroxyethyl)-3-pyridyl]-3-isoquinolyl]-2-cyano-cyclopropanecarboxamide (Compound 65)

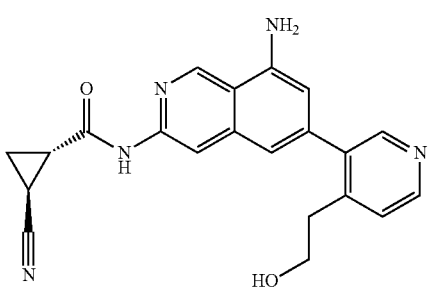 [SMILES: N#C[C@H]1C[C@@H]1C(=O)Nc1cc2cc(-c3cnccc3CCO)cc(N)c2cn1]

Step 1: methyl 2-(3-bromo-4-pyridyl)acetate

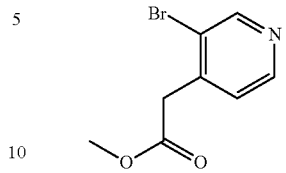

To an ice-cooled solution of 3-bromo-4-methylpyridine (1.0 g, 5.8 mmol) and dimethyl carbonate (950.0 mg, 10.6 mmol) in tetrahydrofuran (10 mL) was added LiHMDS (1.0 M in THF, 9 mL, 9 mmol). After stirring at 0° C. for 5 hours, additional LiHMDS (1.0 M in THF, 6 mL, 6 mmol) was added. The mixture was stirred at room temperature for 2 hours. The reaction mixture was quenched by the addition of a saturated aqueous NH$_4$Cl solution and extracted with ethyl acetate. The organic layer was dried, filtered and concentrated. The crude product was purified by silica gel column chromatography (petroleum ether/ethyl acetate=1:3) to give methyl 2-(3-bromo-4-pyridyl)acetate (1.2 g, 85% yield) as a colorless oil. LCMS (ESI): [M+H]$^+$=231.1.

Step 2: 2-(3-bromo-4-pyridyl)ethanol

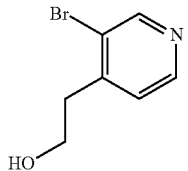

To an ice-cooled solution of methyl 2-(3-bromo-4-pyridyl)acetate (800 mg, 3.5 mmol) in methyl alcohol (10 mL) was added NaBH$_4$ (264.0 mg, 6.9 mmol) in portions. The mixture was stirred at room temperature for 2 hours. The mixture was concentrated and purified by silica gel column chromatography (petroleum ether/ethyl acetate, 1:1) to give 2-(3-bromo-4-pyridyl)ethanol (550 mg, 78% yield) as a colorless oil. LCMS (ESI): [M+H]$^+$=203.1.

Step 3: 2-[3-(3-amino-8-chloro-6-isoquinolyl)-4-pyridyl]ethanol

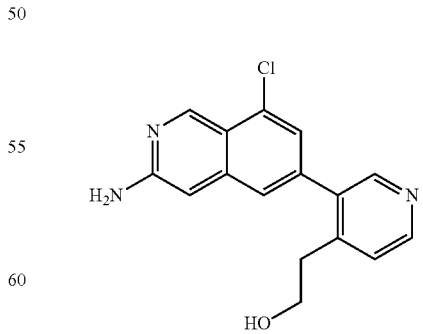

2-(3-bromo-4-pyridyl)ethanol (300 mg, 1.5 mmol), Pd(dppf)Cl$_2$ (120 mg, 0.16 mmol), sodium acetate (300 mg, 3.7 mmol), and K$_3$PO$_4$ (600 mg, 2.8 mmol) were added sequentially to a solution 8-chloro-6-(4,4,5,5-tetramethyl-1, 3,2-dioxaborolan-2-yl)isoquinolin-3-amine (800 mg, 2.6 mmol) in acetonitrile (15 mL) and water (2 mL). The reaction mixture was stirred at 90° C. for 4 hours. The reaction was concentrated to dryness. The residue was purified by silica gel flash column chromatography (30% methanol in dichloromethane) to give 2-[3-(3-amino-8-chloro-6-isoquinolyl)-4-pyridyl]ethanol (400 mg, 84% yield) as a yellow solid. LCMS (ESI): [M+H]$^+$=300.1.

Step 4: 6-[4-[2-[tert-butyl(dimethyl)silyl]oxyethyl]-3-pyridyl]-8-chloro-isoquinolin-3-amine

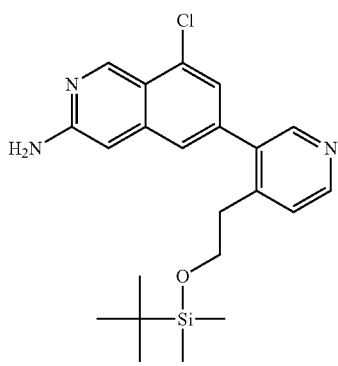 [SMILES: CC(C)(C)[Si](C)(C)OCCc1ccncc1-c1cc(Cl)c2cnc(N)cc2c1]

A mixture of 2-[3-(3-amino-8-chloro-6-isoquinolyl)-4-pyridyl] ethanol (400.0 mg, 1.3 mmol), tert-butyldimethylchlorosilane (2.0 g, 13.3 mmol) and triethylamine (3.0 g, 29.7 mmol) in dichloromethane (50 mL) was refluxed overnight. The reaction mixture was concentrated The residue was purified with silica-gel column chromatography (petroleum ether/ethyl acetate, 2:1 to 1:1) to give 6-[4-[2-[tert-butyl(dimethyl)silyl]oxyethyl]-3-pyridyl]-8-chloro-isoquinolin-3-amine (350 mg, 62% yield) as a light brown solid. LCMS (ESI): [M+H]$^+$=415.2.

Step 5: (±)-trans-N-[6-[4-[2-[tert-butyl(dimethyl)silyl]oxyethyl]-3-pyridyl]-8-chloro-3-isoquinolyl]-2-cyano-cyclopropanecarboxamide

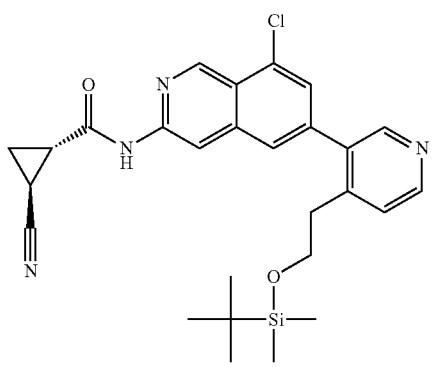 [SMILES: CC(C)(C)[Si](C)(C)OCCc1ccncc1-c1cc(Cl)c2cnc(NC(=O)[C@H]3C[C@@H]3C#N)cc2c1]

Oxalyl chloride (350 mg, 2.8 mmol) was added dropwise to a suspension of trans-2-cyanocyclopropane carboxylic acid (200 mg, 1.8 mmol) in dichloromethane (1 mL) at 0° C. and the mixture was stirred at 0° C. for 1 hour. The mixture was concentrated at room temperature to remove dichloromethane and the excess oxalyl chloride. The residue was suspended in dichloromethane (1 mL) and was added dropwise to a mixture of 6-[4-[2-[tert-butyl(dimethyl)silyl]oxyethyl]-3-pyridyl]-8-chloro-isoquinolin-3-amine (360 mg, 0.87 mmol), pyridine (5.1 mL, 63.2 mmol) in dichloromethane (2 mL) at 0° C. The reaction mixture was stirred at 0° C. for an additional 0.5 hours. The reaction mixture was diluted with dichloromethane (100 mL) and washed with H$_2$O (50 mL). The organic layer was separated, dried over Na$_2$SO$_4$, filtered and evaporated. The residue was purified by silica gel column chromatography (petroleum ether/ethyl acetate, 1:1 to 1:2) to give (±)-trans-N-[6-[4-[2-[tert-butyl(dimethyl)silyl]oxyethyl]-3-pyridyl]-8-chloro-3-isoquinolyl]-2-cyano-cyclopropanecarboxamide (350 mg, 63% yield) as a light brown solid. LCMS (ESI): [M+H]$^+$=508.1.

Step 6: (±)-tert-butyl N-[6-[4-[2-[tert-butyl(dimethyl)silyl]oxyethyl]-3-pyridyl]-3-[[trans-2-cyano cyclopropanecarbonyl]amino]-8-isoquinolyl]carbamate

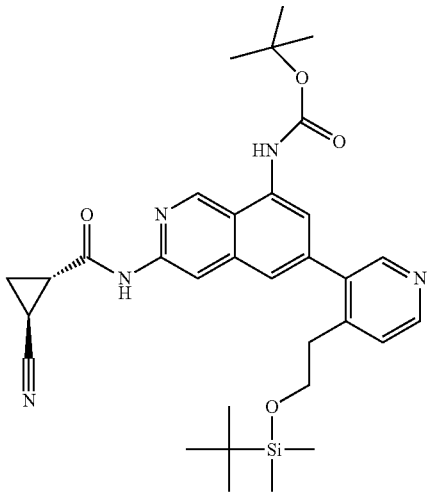 [SMILES: CC(C)(C)OC(=O)Nc1cc(-c2cnccc2CCO[Si](C)(C)C(C)(C)C)cc2cc(NC(=O)[C@H]3C[C@@H]3C#N)ncc12]

A mixture of (±)-trans-N-[6-[4-[2-[tert-butyl(dimethyl)silyl]oxyethyl]-3-pyridyl]-8-chloro-3-isoquinolyl]-2-cyano-cyclopropanecarboxamide (330 mg, 0.65 mmol), tert-butyl carbamate (1.5 g, 12.8 mmol), Pd$_2$(dba)$_3$ (120 mg, 0.1300 mmol), Brettphos (130 mg, 0.24 mmol), and t-BuONa (170 mg, 1.7 mmol) in 1,4-dioxane (10 mL) was stirred at 90° C. under N$_2$ for 1 hour. The reaction mixture was concentrated in vacuo. The residue was purified by silica gel column chromatography (ethyl acetate/petroleum ether, 1:1) to afford (±)-tert-butyl N-[6-[4-[2-[tert-butyl(dimethyl)silyl]oxyethyl]-3-pyridyl]-3-[[trans-2-cyanocyclopropanecarbonyl]amino]-8-isoquinolyl]carbamate (220 mg, 52% yield) as a light yellow oil. LCMS (ESI): [M+H]$^+$=588.1.

Step 7: (±)-trans-N-[8-amino-6-[4-(2-hydroxyethyl)-3-pyridyl]-3-isoquinolyl]-2-cyano-cyclopropane carboxamide

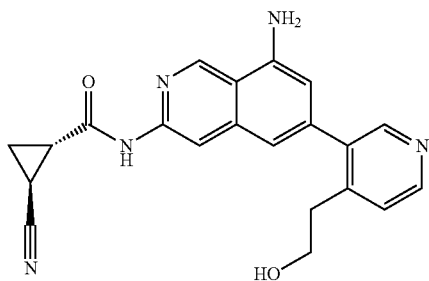 [SMILES: N#C[C@H]1C[C@@H]1C(=O)Nc1cc2cc(-c3cnccc3CCO)cc(N)c2cn1]

A mixture of (±)-tert-butyl N-[6-[4-[2-[tert-butyl(dimethyl)silyl]oxyethyl]-3-pyridyl]-3-[[trans-2-cyanocyclopropanecarbonyl]amino]-8-isoquinolyl]carbamate (200 mg, 0.34 mmol) and TFA (10 mL, 134.6 mmol) in dichloromethane (10 mL) was stirred at room temperature for 2 hours. The reaction was concentrated and purified by reverse phase prep-HPLC to give (1)-trans-N-[8-amino-6-[4-(2-hydroxyethyl)-3-pyridyl]-3-isoquinolyl]-2-cyano-cyclopropane carboxamide (82 mg, 65% yield) as a yellow solid. LCMS (ESI): RT (min)=1.409, [M+H]$^+$=374.2, method=G; 1H NMR (400 MHz, CD$_3$OD) δ 9.26 (s, 1H), 8.47 (d, J=5.2 Hz, 1H), 8.40 (s, 1H), 8.30 (s, 1H), 7.49 (d, J=5.2 Hz, 1H), 7.01 (s, 1H), 6.70 (d, J=1.2 Hz, 1H), 3.70 (t, J=6.8 Hz, 2H), 2.94 (t, J=6.8 Hz, 2H), 2.70-2.61 (m, 1H), 2.17-2.06 (m, 1H), 1.66-1.49 (m, 2H).

Example 50

(1S,2S)—N-(8-amino-6-(4-ethylpyridin-3-yl)isoquinolin-3-yl)-2-fluorocyclopropane-1-carboxamide (Compound 66)

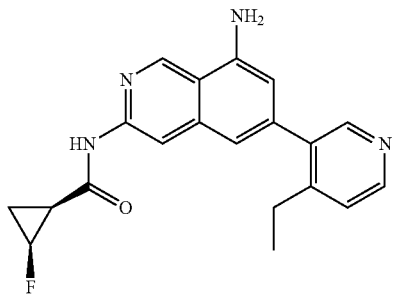 [SMILES: CCc1ccncc1-c1cc(Cl)c2cnc(NC(=O)[C@@H]3C[C@@H]3F)cc2c1]

Step 1: (1S,2S)—N-(8-chloro-6-(4-ethylpyridin-3-yl)isoquinolin-3-yl)-2-fluorocyclopropane-1-carboxamide

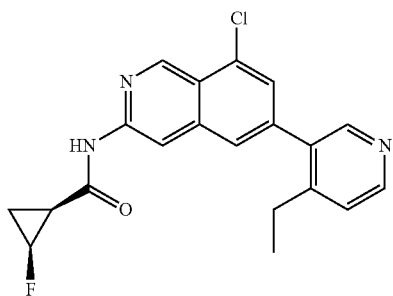

A mixture of (1S,2S)—N-(6-bromo-8-chloroisoquinolin-3-yl)-2-fluorocyclopropane-1-carboxamide (130 mg, 0.381 mmol), bis(pinacolato)diboron (148 mg, 0.572 mmol), potassium acetate (112 mg, 1.14 mmol) and Pd(dppf)Cl$_2$ (28.2 mg, 0.038 mmol) in 1,4-dioxane (3 mL) was heated in a microwave at 130° C. for 20 minutes to give (8-chloro-3-((1S,2S)-2-fluorocyclopropane-1-carboxamido)isoquinolin-6-yl)boronic acid. LCMS (ESI): [M+H]$^+$=309.0.

3-Bromo-4-ethylpyridine (106 mg, 0.574 mmol) and water (0.5 ml, 30 mmol) were added to the reaction mixture. The reaction was heated in a microwave at 140° C. for 2 hours. The organic layer was purified with silica-gel column chromatography (0 to 7% methanol in dichloromethane) to give (1S,2S)—N-(8-chloro-6-(4-ethylpyridin-3-yl)isoquinolin-3-yl)-2-fluorocyclopropane-1-carboxamide (120 mg, 84.8% yield). LCMS (ESI) [M+H]$^+$=370.0.

Step 2: tert-butyl (6-(4-ethylpyridin-3-yl)-3-((1S,2S)-2-fluorocyclopropane-1-carboxamido)isoquinolin-8-yl)carbamate

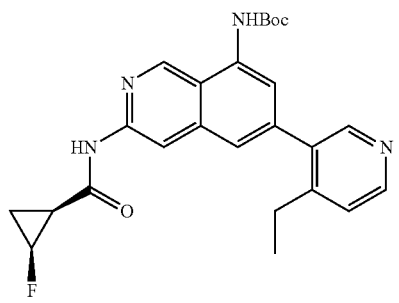 [SMILES: CCc1ccncc1-c1cc(NC(=O)OC(C)(C)C)c2cnc(NC(=O)[C@@H]3C[C@@H]3F)cc2c1]

A mixture of (1S,2S)—N-(8-chloro-6-(4-ethylpyridin-3-yl)isoquinolin-3-yl)-2-fluorocyclopropane-1-carboxamide (120 mg, 0.325 mmol), tert-butyl carbamate (194 mg, 1.622 mmol), Pd$_2$(dba)$_3$ (15 mg, 0.016 mmol), Brettphos (9.168 mg, 0.016 mmol), and tBuONa (47 mg, 0.0.487 mmol) in 1,4-dioxane (5 mL) was stirred under Ar at 70° C. for 5 hours. The reaction was concentrated to dryness. The residue was purified by silica gel column chromatography (0 to 8% methanol in dichloromethane) to give the title compound (74 mg, 50.6% yield). LCMS (ESI) [M+H]$^+$=451.0.

Step 3: (1S,2S)—N-(8-amino-6-(4-ethylpyridin-3-yl)isoquinolin-3-yl)-2-fluorocyclopropane-1-carboxamide

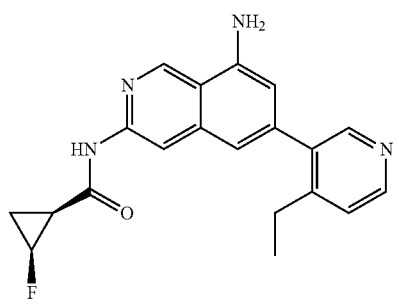 [SMILES: CCc1ccncc1-c1cc(N)c2cnc(NC(=O)[C@@H]3C[C@@H]3F)cc2c1]

A mixture of tert-butyl-(6-(4-ethylpyridin-3-yl)-3-((1S,2S)-2-fluorocyclopropane-1-carboxamido)isoquinolin-8-yl)

carbamate (74 mg, 0.164 mmol) in dichloromethane (4 mL) and 2,2,2-trifluoroacetic acid (0.5 mL) was stirred at 25° C. for 2 hours. The mixture was concentrated and purified by reverse phase prep-HPLC to afford (1S,2S)—N-(8-amino-6-(4-ethylpyridin-3-yl)isoquinolin-3-yl)-2-fluorocyclopropane-1-carboxamide (9.3 mg, 15.8% yield) as a solid. LCMS (ESI) $R_T$ (min)=2.808, $[M+H]^+$=351.1, method=T. $^1$H NMR (400 MHz, DMSO) δ 10.80 (s, 1H), 9.32 (s, 1H), 8.49 (d, J=5.1 Hz, 1H), 8.39-8.35 (m, 1H), 8.27 (s, 1H), 7.38 (d, J=5.2 Hz, 1H), 6.88 (s, 1H), 6.53 (d, J=1.5 Hz, 1H), 6.34 (s, 2H), 5.04-4.81 (m, 1H), 2.62 (q, J=7.6 Hz, 2H), 2.26 (dq, J=14.1, 7.1 Hz, 1H), 1.73-1.59 (m, 1H), 1.17 (ddt, J=13.1, 9.8, 6.7 Hz, 1H), 1.13-1.06 (m, 3H).

Example 51

(±)-trans-N-(8-amino-6-(4-ethylpyridin-3-yl)isoquinolin-3-yl)-2-cyanocyclopropane-1-carboxamide (Compound 67)

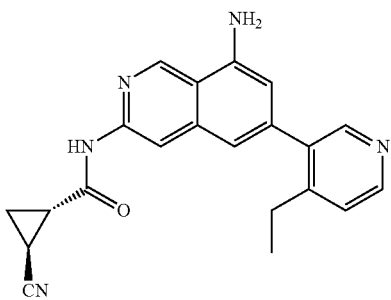 [SMILES: CCc1ccncc1-c1cc(N)c2cnc(NC(=O)[C@H]3C[C@@H]3C#N)cc2c1]

Step 1: (±)-trans-N-(8-chloro-6-(4-ethylpyridin-3-yl)isoquinolin-3-yl)-2-cyanocyclopropane-1-carboxamide

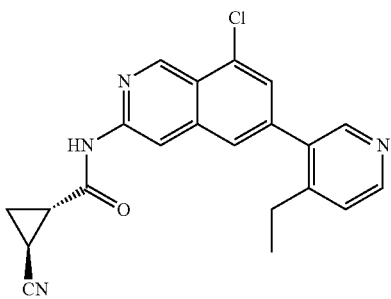 [SMILES: CCc1ccncc1-c1cc(Cl)c2cnc(NC(=O)[C@H]3C[C@@H]3C#N)cc2c1]

A mixture of (±)-trans-N-(6-bromo-8-chloroisoquinolin-3-yl)-2-cyanocyclopropane-1-carboxamide (150 mg, 0.428 mmol), bis(pinacolato)diboron (166 mg, 0.642 mmol), potassium acetate (126 mg, 1.28 mmol), and Pd(dppf)Cl$_2$ (31.6 mg, 0.043 mmol) in 1,4-dioxane (4 mL) was heated in a microwave at 130° C. for 45 minutes to give (8-chloro-3-((trans-2-cyanocyclopropane-1-carboxamido)isoquinolin-6-yl)boronic acid. LCMS (ESI): $[M+H]^+$=316.0.

3-Bromo-4-ethylpyridine (143 mg, 0.77 mmol) and sodium carbonate (1 mol/L) in water (2.14 ml, 2.139 mmol) were then added. The reaction mixture was heated in a microwave at 80° C. for 70 minutes. The organic layer was purified with silica gel column chromatography (0 to 7% methanol in dichloromethane) to give (±)-trans-N-(8-chloro-6-(4-ethylpyridin-3-yl)isoquinolin-3-yl)-2-cyanocyclopropane-1-carboxamide (141 mg, 87.4% yield). LCMS (ESI) $[M+H]^+$=377.0.

Step 2: (±)-tert-butyl (3-((trans-2-cyanocyclopropane-1-carboxamido)-6-(4-ethylpyridin-3-yl)isoquinolin-8-yl)carbamate

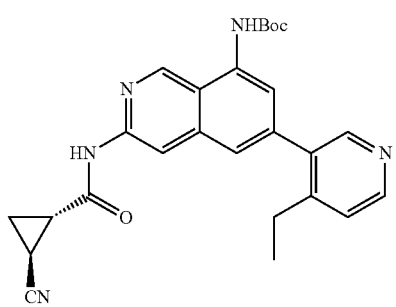 [SMILES: CCc1ccncc1-c1cc(NC(=O)OC(C)(C)C)c2cnc(NC(=O)[C@H]3C[C@@H]3C#N)cc2c1]

A mixture of (±)-trans-N-(8-chloro-6-(4-ethylpyridin-3-yl)isoquinolin-3-yl)-2-cyanocyclopropane-1-carboxamide (141 mg, 0.374 mmol), tert-butyl carbamate (224 mg, 1.871 mmol), Pd$_2$(dba)$_3$ (34.2 mg, 0.037 mmol), Brettphos (21.14 mg, 0.037 mmol), and tBuONa (71.9 mg, 0.748 mmol) in 1,4-dioxane (5 mL) was stirred under Ar at 120° C. for 2 hours. The reaction was concentrated to dryness. The residue was purified by silica-gel column chromatography (0 to 8% methanol in dichloromethane) to give the title compound (150 mg, 88% yield). LCMS (ESI) $[M+H]^+$=458.0.

Step 3: (±)-trans-N-(8-amino-6-(4-ethylpyridin-3-yl)isoquinolin-3-yl)-2-cyanocyclopropane-1-carboxamide

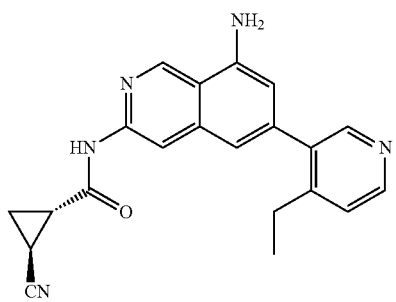 [SMILES: CCc1ccncc1-c1cc(N)c2cnc(NC(=O)[C@H]3C[C@@H]3C#N)cc2c1]

A mixture of (±)-tert-butyl (3-((trans-2-cyanocyclopropane-1-carboxamido)-6-(4-ethylpyridin-3-yl)isoquinolin-8-yl)carbamate (150 mg, 0.327 mmol) in dichloromethane (3 mL) and 2,2,2-trifluoroacetic acid (0.3 mL) was stirred at 25° C. for 1.5 hours. The mixture was concentrated and purified by reverse phase prep-HPLC to afford trans-N-(8-amino-6-(4-ethylpyridin-3-yl)isoquinolin-3-yl)-2-cyanocyclopropane-1-carboxamide (16.8 mg, 14.3% yield) as solid. LCMS (ESI) $R_T$ (min)=2.999, $[M+H]^+$=358.1, method=T. $^1$H NMR (400 MHz, DMSO) δ 11.10 (s, 1H), 9.34 (s, 1H), 8.49 (d, J=5.1 Hz, 1H), 8.40-8.34 (m, 1H), 8.23 (s, 1H), 7.41-7.35 (m, 1H), 6.88 (s, 1H), 6.55 (d, J=1.5 Hz, 1H), 6.38 (s, 2H), 2.80-2.72 (m, 1H), 2.61 (q, J=7.5 Hz, 2H), 2.13

(ddd, J=9.3, 6.1, 4.3 Hz, 1H), 1.59 (ddd, J=8.6, 6.0, 4.4 Hz, 1H), 1.43 (ddd, J=9.3, 5.9, 4.4 Hz, 1H), 1.09 (t, J=7.6 Hz, 3H).

Example 52

(±)-cis-N-(8-amino-6-(4-ethylpyridin-3-yl)isoquinolin-3-yl)-2-cyanocyclopropane-1-carboxamide (Compound 68)

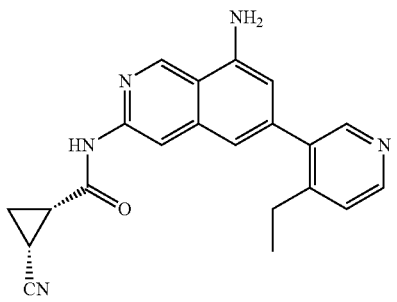 [SMILES: CCc1ccncc1-c1cc(N)c2cnc(NC(=O)[C@H]3C[C@H]3C#N)cc2c1]

Step 1: (±)-cis-N-(8-chloro-6-(4-ethylpyridin-3-yl)isoquinolin-3-yl)-2-cyanocyclopropane-1-carboxamide

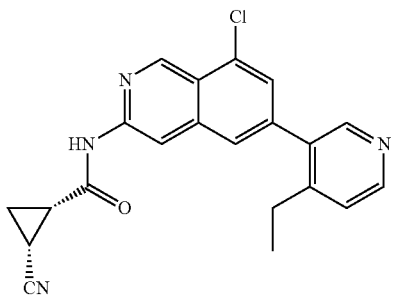 [SMILES: CCc1ccncc1-c1cc(Cl)c2cnc(NC(=O)[C@H]3C[C@H]3C#N)cc2c1]

A mixture of (±)-cis-N-(6-bromo-8-chloroisoquinolin-3-yl)-2-cyanocyclopropane-1-carboxamide (125 mg, 0.357 mmol), bis(pinacolato)diboron (139 mg, 0.535 mmol), potassium acetate (105 mg, 1.07 mmol), and Pd(dppf)Cl$_2$ (26.4 mg, 0.0357 mmol) in 1,4-dioxane (2 mL) was heated in a microwave at 130° C. for 45 minutes to give (8-chloro-3-((cis-2-cyanocyclopropane-1-carboxamido)isoquinolin-6-yl)boronic acid. LCMS (ESI): [M+H]$^+$=316.0.

3-Bromo-4-ethylpyridine (127 mg, 0.685 mmol) and sodium carbonate (1 M) in water (1.71 ml, 1.71 mmol) were then added. The reaction mixture was heated in a microwave at 80° C. for 2 hours. The organic layer was purified with silica gel column chromatography (0 to 10% methanol in dichloromethane) to give (±)-cis-N-(8-chloro-6-(4-ethylpyridin-3-yl)isoquinolin-3-yl)-2-cyanocyclopropane-1-carboxamide (81.5 mg, 63.2% yield). LCMS (ESI) [M+H]$^+$=377.0.

Step 2: (±)-tert-butyl (3-((cis-2-cyanocyclopropane-1-carboxamido)-6-(4-ethylpyridin-3-yl)isoquinolin-8-yl)carbamate

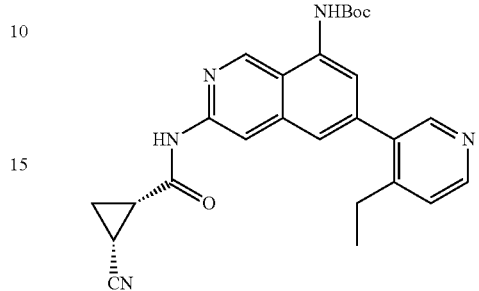

A mixture of (±)-(cis-N-(8-chloro-6-(4-ethylpyridin-3-yl)isoquinolin-3-yl)-2-cyanocyclopropane-1-carboxamide (81.5 mg, 0.216 mmol), tert-butyl carbamate (129 mg, 1.08 mmol), Pd$_2$(dba)$_3$ (9.90 mg, 0.0108 mmol), Brettphos (6.11 mg, 0.0108 mmol), and tBuONa (31.2 mg, 0.324 mmol) in 1,4-dioxane (4.5 mL) was stirred under Ar at 90° C. for 2.5 hours. The mixture was extracted with dichloromethane (30 mL×2). The organic extracts were washed with water (20 mL), brine (20 ml), dried over Na$_2$SO$_4$, filtered and concentrated to give the title compound (96 mg, 97.0% yield). LCMS (ESI) [M+H]$^+$=458.0.

Step 3: (±)-cis-N-(8-amino-6-(4-ethylpyridin-3-yl)isoquinolin-3-yl)-2-cyanocyclopropane-1-carboxamide A mixture of (±)-tert-butyl (3-((cis-2-cyanocyclopropane-1-carboxamido)-6-(4-ethylpyridin-3-yl)isoquinolin-8-yl)carbamate (96 mg, 0.210 mmol) in dichloromethane (3 mL) and 2,2,2-trifluoroacetic acid (0.3 mL) was stirred at 25° C. for 50 minutes. The mixture was concentrated and purified by reverse phase prep-HPLC to afford (±)-(cis-N-(8-amino-6-(4-ethylpyridin-3-yl)isoquinolin-3-yl)-2-cyanocyclopropane-1-carboxamide (3.6 mg, 4.5% yield) as a solid. LCMS (ESI) RT (min)=2.745, [M+H]$^+$=358.2, method=T. $^1$H NMR (400 MHz, DMSO) δ 11.06 (d, J=20.0 Hz, 1H), 9.34 (s, 1H), 8.49 (d, J=5.1 Hz, 1H), 8.37 (d, J=0.5 Hz, 1H), 8.30 (s, 1H), 7.38 (dt, J=9.0, 4.5 Hz, 1H), 6.92 (s, 1H), 6.55 (d, J=1.5 Hz, 1H), 6.37 (s, 2H), 2.62 (dt, J=15.0, 7.5 Hz, 3H), 2.30-2.22 (m, 1H), 1.51-1.40 (m, 2H), 1.09 (t, J=7.6 Hz, 3H).

Example 53

(±)-trans-N-(8-amino-6-(6-cyano-4-methylpyridin-3-yl)isoquinolin-3-yl)-2-cyanocyclopropane-1-carboxamide (Compound 69)

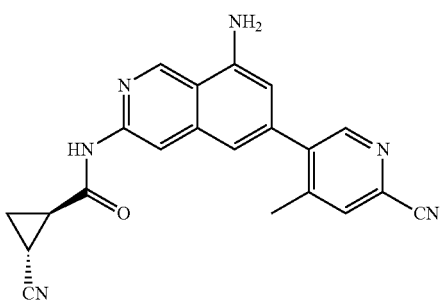 [SMILES: Cc1cc(C#N)ncc1-c1cc(N)c2cnc(NC(=O)[C@@H]3C[C@H]3C#N)cc2c1]

Step 1: (±)-trans-N-(8-chloro-6-(6-cyano-4-methylpyridin-3-yl)isoquinolin-3-yl)-2-cyanocyclopropane-1-carboxamide

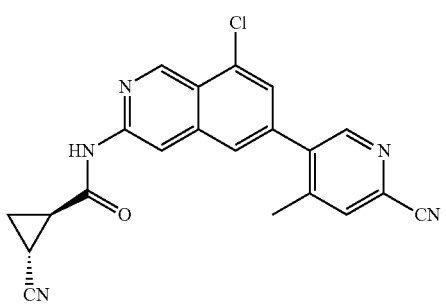 [SMILES: Cc1cc(C#N)ncc1-c1cc(Cl)c2cnc(NC(=O)[C@@H]3C[C@H]3C#N)cc2c1]

A mixture of (±)-trans-N-(6-bromo-8-chloroisoquinolin-3-yl)-2-cyanocyclopropane-1-carboxamide (125 mg, 0.571 mmol), bis(pinacolato)diboron (222 mg, 0.856 mmol), potassium acetate (168 mg, 1.711 mmol), and Pd(dppf)Cl$_2$ (42.2 mg, 0.0571 mmol) in 1,4-dioxane (3 mL) was heated in a microwave at 130° C. for 45 minutes to give (±)-(8-chloro-3-((trans-2-cyanocyclopropane-1-carboxamido)isoquinolin-6-yl)boronic acid. LCMS (ESI): [M+H]$^+$=316.0.

5-Bromo-4-methylpicolinonitrile (168 mg, 0.856 mmol) and sodium carbonate (1 mol/L) in water (2.85 ml, 2.852 mmol) were then added. The reaction mixture was heated in a microwave at 90° C. for 55 minutes. The organic layer was purified with silica gel column chromatography (0.5 to 9% methanol in dichloromethane) to give (±)-(trans-N-(8-chloro-6-(6-cyano-4-methylpyridin-3-yl)isoquinolin-3-yl)-2-cyanocyclopropane-1-carboxamide (187 mg, 86.5% yield). LCMS (ESI) [M+H]$^+$=388.0.

Step 2: (±)-tert-butyl (6-(6-cyano-4-methylpyridin-3-yl)-3-((trans-2-cyanocyclopropane-1-carboxamido)isoquinolin-8-yl)carbamate

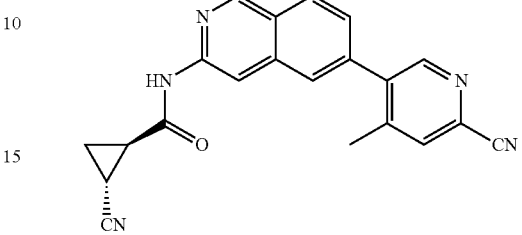

A mixture of (±)-(trans-N-(8-chloro-6-(6-cyano-4-methylpyridin-3-yl)isoquinolin-3-yl)-2-cyanocyclopropane-1-carboxamide (160 mg, 0.413 mmol), tert-butyl carbamate (247 mg, 2.063 mmol), Pd$_2$(dba)$_3$ (37.8 mg, 0.041 mmol), Brettphos (23.3 mg, 0.041 mmol), and tBuONa (59.5 mg, 0.619 mmol) in 1,4-dioxane (10 mL) was stirred under Ar at 80° C. for 1.5 hours. The reaction was concentrated to dryness. The residue was purified by silica gel column chromatography (0.5 to 8% methanol in dichloromethane) to give the title compound (45 mg, 23.3% yield). LCMS (ESI) [M+H]$^+$=469.0.

Step 3: (±)-trans-N-(8-amino-6-(6-cyano-4-methylpyridin-3-yl)isoquinolin-3-yl)-2-cyanocyclopropane-1-carboxamide

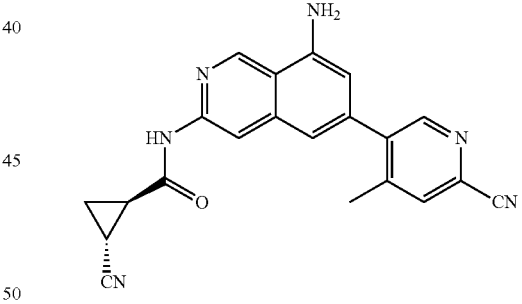

A mixture of (±)-tert-butyl (6-(6-cyano-4-methylpyridin-3-yl)-3-((trans-2-cyanocyclopropane-1-carboxamido)isoquinolin-8-yl)carbamate (45 mg, 0.096 mmol) and TFA (0.3 mL) in dichloromethane (4 mL) was stirred at 25° C. for 1.5 hours. The mixture was concentrated and purified by reverse phase prep-HPLC to afford (±)-trans-N-(8-amino-6-(6-cyano-4-methylpyridin-3-yl)isoquinolin-3-yl)-2-cyanocyclopropane-1-carboxamide (16.5 mg, 45.2% yield) as solid. LCMS (ESI) R$_T$ (min)=4.401, [M+H]$^+$=369.1, method=T. $^1$H NMR (400 MHz, DMSO) δ 11.06 (d, J=20.0 Hz, 1H), 9.34 (s, 1H), 8.49 (d, J=5.1 Hz, 1H), 8.37 (d, J=0.5 Hz, 1H), 8.30 (s, 1H), 7.38 (dt, J=9.0, 4.5 Hz, 1H), 6.92 (s, 1H), 6.55 (d, J=1.5 Hz, 1H), 6.37 (s, 2H), 2.62 (dt, J=15.0, 7.5 Hz, 3H), 2.30-2.22 (m, 1H), 1.51-1.40 (m, 2H), 1.09 (t, J=7.6 Hz, 3H).

Example 54

(±)-trans-N-(8-amino-6-(6-cyano-4-methylpyridin-3-yl)isoquinolin-3-yl)-2-cyanocyclopropane-1-carboxamide (Compound 70)

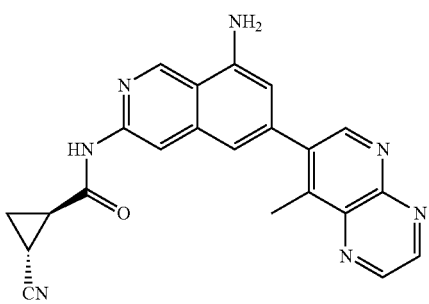 [SMILES: Cc1c(-c2cc(N)c3cnc(NC(=O)[C@@H]4C[C@H]4C#N)cc3c2)cnc2nccnc12]

Step 1: (±)-trans-N-(8-chloro-6-(8-methylpyrido[2,3-b]pyrazin-7-yl)isoquinolin-3-yl)-2-cyanocyclopropane-1-carboxamide

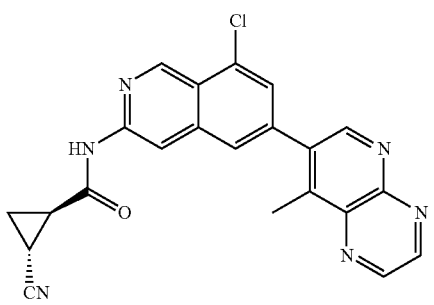 [SMILES: Cc1c(-c2cc(Cl)c3cnc(NC(=O)[C@@H]4C[C@H]4C#N)cc3c2)cnc2nccnc12]

A mixture of (±)-trans-N-(6-bromo-8-chloroisoquinolin-3-yl)-2-cyanocyclopropane-1-carboxamide (98 mg, 0.279 mmol), bis(pinacolato)diboron (109 mg, 0.419 mmol), potassium acetate (82.3 mg, 0.839 mmol), and Pd(dppf)Cl$_2$ (20.7 mg, 0.028 mmol) in 1,4-dioxane (3 mL) was heated in a microwave at 130° C. for 45 minutes to give (±)-(8-chloro-3-(trans-2-cyanocyclopropane-1-carboxamido)isoquinolin-6-yl)boronic acid. LCMS (ESI): [M+H]$^+$=316.0.

7-Bromo-8-methylpyrido[2,3-b]pyrazine (93.9 mg, 0.419 mmol) and sodium carbonate (1 M) in water (1.398 ml, 1.398 mmol) were then added. The reaction mixture was heated in a microwave at 90° C. for 55 minutes. The organic layer was purified with silica gel column chromatography (0.5 to 9% methanol in dichloromethane) to give (±)-trans-N-(8-chloro-6-(8-methylpyrido[2,3-b]pyrazin-7-yl)isoquinolin-3-yl)-2-cyanocyclopropane-1-carboxamide (73 mg, 55.3% yield). LCMS (ESI) [M+H]$^+$=415.0.

Step 2: (±)-tert-butyl (3-(trans-2-cyanocyclopropane-1-carboxamido)-6-(8-methylpyrido[2,3-b]pyrazin-7-yl)isoquinolin-8-yl)carbamate

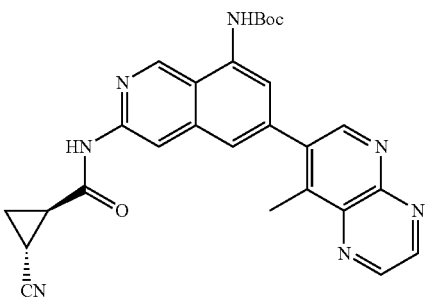 [SMILES: Cc1c(-c2cc(NC(=O)OC(C)(C)C)c3cnc(NC(=O)[C@@H]4C[C@H]4C#N)cc3c2)cnc2nccnc12]

A mixture of (±)-trans-N-(8-chloro-6-(8-methylpyrido[2,3-b]pyrazin-7-yl)isoquinolin-3-yl)-2-cyanocyclopropane-1-carboxamide (67 mg, 0.0.1615 mmol), tert-butyl carbamate (96.5 mg, 0.807 mmol), Pd$_2$(dba)$_3$ (14.8 mg, 0.016 mmol), Brettphos (9.12 mg, 0.016 mmol), and tBuONa (23.3 mg, 0.242 mmol) in 1,4-dioxane (4 mL) was stirred under Ar at 80° C. for 1.5 hours. The reaction was concentrated to dryness. The residue was purified by silica gel column chromatography (0.5 to 8% methanol in dichloromethane) to give the title compound (19 mg, 23.7% yield). LCMS (ESI) [M+H]$^+$=496.0.

Step 3: (±)-trans-N-(8-amino-6-(8-methylpyrido[2,3-b]pyrazin-7-yl)isoquinolin-3-yl)-2-cyanocyclopropane-1-carboxamide

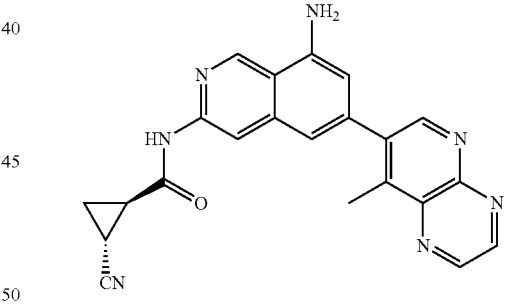

A mixture of (±)-tert-butyl (3-(trans-2-cyanocyclopropane-1-carboxamido)-6-(8-methylpyrido[2,3-b]pyrazin-7-yl)isoquinolin-8-yl)carbamate (19 mg, 0.038 mmol) in dichloromethane (4 mL) and TFA (0.3 mL) was stirred at 25° C. for 1 hour. The mixture was concentrated and purified by reverse phase prep-HPLC to afford (±)-trans-N-(8-amino-6-(8-methylpyrido[2,3-b]pyrazin-7-yl)isoquinolin-3-yl)-2-cyanocyclopropane-1-carboxamide (4.2 mg, 28% yield) as solid. LCMS (ESI) R$_T$ (min)=3.847, [M+H]$^+$=396.1, method=T. $^1$H NMR (400 MHz, DMSO) δ 11.14 (s, 1H), 9.40 (s, 1H), 9.17 (t, J=1.5 Hz, 1H), 9.14 (d, J=1.8 Hz, 1H), 9.07 (s, 1H), 8.29 (s, 1H), 7.08 (s, 1H), 6.71 (d, J=1.5 Hz, 1H), 6.47 (s, 2H), 2.82-2.73 (m, 4H), 2.14 (ddd, J=9.3, 6.1, 4.3 Hz, 1H), 1.59 (ddd, J=8.6, 6.0, 4.5 Hz, 1H), 1.43 (ddd, J=9.2, 5.9, 4.4 Hz, 1H).

Example 55

(±)-trans-N-(8-amino-6-(6-methylimidazo[1,2-a]pyridin-7-yl)isoquinolin-3-yl)-2-cyanocyclopropanecarboxamide (Compound 109)

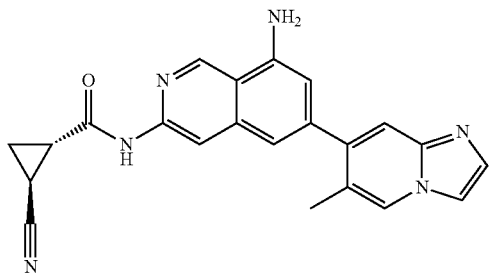 [SMILES: Cc1cn2ccnc2cc1-c1cc(N)c2cnc(NC(=O)[C@H]3C[C@@H]3C#N)cc2c1]

Step 1: N-(2,4-dimethoxybenzyl)-4-iodo-5-methylpyridin-2-amine

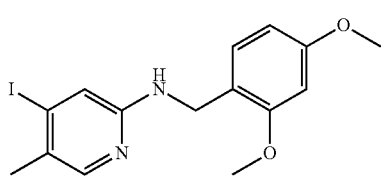 [SMILES: COc1ccc(CNc2cc(I)c(C)cn2)c(OC)c1]

A mixture of 2-fluoro-4-iodo-5-methylpyridine (1.0 g, 4.2 mmol), 2,4-dimethoxybenzylamine (2.0 g, 12.6 mmol), and DIEA (1.6 g, 12.6 mmol) in 1,4-dioxane (5 mL) was heated at 110° C. for 16 h under Ar gas. The reaction was concentrated to dryness. The crude product was purified by flash chromatography (Biotage, 20 g column, PE/EA=5:1) to give N-[(2,4-dimethoxyphenyl)methyl]-4-iodo-5-methyl-pyridin-2-amine (1.0 g, 61% yield) as a yellow solid. LCMS (ESI) [M+H]⁺=250.0.

Step 2: 4-iodo-5-methylpyridin-2-amine

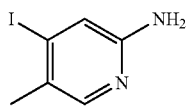

To a mixture of N-[(2,4-dimethoxyphenyl)methyl]-4-iodo-5-methyl-pyridin-2-amine (1.0 g, 2.6 mmol) in dichloromethane (10 mL) was added 2,2,2-trifluoroacetic acid (5 mL). Then the mixture was stirred overnight. The mixture was then concentrated. A 7N NH₃ solution in MeOH was added to adjust the mixture to pH 8 and the mixture was concentrated. The crude product was purified by flash chromatography (PE/EA=2:1) to give 4-iodo-5-methyl-pyridin-2-amine (590 mg, 97% yield) as a yellow solid. LCMS (ESI) [M+H]⁺=235.7.

Step 3: 7-iodo-6-methylimidazo[1,2-a]pyridine

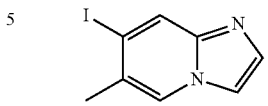

A mixture of 4-iodo-5-methyl-pyridin-2-amine (1.0 g, 4.3 mmol), chloroacetaldehyde (0.42 mL, 6.41 mmol), and NaHCO₃ (430 mg, 5.13 mmol) in ethanol (4 mL) and water (1 mL) was heated to 100° C. and stirred overnight. The mixture was concentrated. The residue was purified by flash column chromatography (DCM/MeOH=20/1) to give the product 7-iodo-6-methyl-imidazo[1,2-a]pyridine (1.0 g, 90% yield) as yellow solid. LCMS (ESI) [M+H]⁺=259.7.

Step 4: 8-chloro-6-(6-methylimidazo[1,2-a]pyridin-7-yl)isoquinolin-3-amine

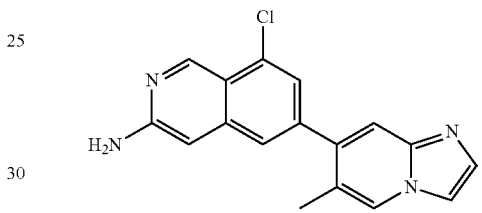

A solution of 7-iodo-6-methyl-imidazo[1,2-a]pyridine (150 mg, 0.58 mmol), 8-chloro-6-(4,4,5,5-tetramethyl-1,3,2-dioxaborolan-2-yl)isoquinolin-3-amine (442 mg, 1.45 mmol), Pd(dppf)Cl₂ (42 mg, 0.06 mmol), Na₂CO₃ (183 mg, 1.74 mmol), and water (1 mL) in tetrahydrofuran (10 mL) was heated to 65° C. for 3 h under N₂. Water (10 mL) was added. The mixture was extracted with ethyl acetate (10 mL×2). The organic layer was washed with water (20 mL×3), brine (20 mL), dried over Na₂SO₄, filtered and concentrated. The crude product was purified by flash chromatography (DCM/MeOH=15:1) to give 8-chloro-6-(6-methylimidazo[1,2-a]pyridin-7-yl)isoquinolin-3-amine (180 mg, 77% yield) as a yellow solid. LCMS (ESI) [M+H]+=309.7.

Step 5: (±)-trans-N-(8-chloro-6-(6-methylimidazo[1,2-a]pyridin-7-yl)isoquinolin-3-yl)-2-cyanocyclopropanecarboxamide

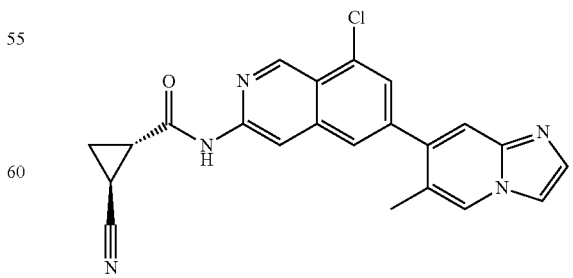

To a solution of (±)-trans-2-cyanocyclopropanecarboxylic acid (120 mg, 1.08 mmol) in dichloromethane (5 mL) and N,N-dimethylformamide (0.02 mL) was added ethanedioyl dichloride (274 mg, 2.16 mmol) at 0° C. The reaction was stirred at 25° C. for 2 h. The mixture was concentrated to give crude product (±)-trans-2-cyanocyclopropanecarbonyl chloride (130 mg, 1 mmol, 93% yield) as a yellow oil. To a solution of 8-chloro-6-(6-methylimidazo[1,2-a]pyridin-7-yl)isoquinolin-3-amine (180 mg, 0.58 mmol) in dichloromethane (15 mL) and pyridine (0.14 mL, 1.75 mmol) was added (±)-trans-2-cyanocyclo propanecarbonyl chloride (113 mg, 0.87 mmol). The mixture was stirred at 25° C. for 30 min. The mixture was concentrated and water (10 mL) was added. 1 N HCl was then added to adjust the mixture to a pH of 6. The mixture was extracted with DCM (10 mL×3). The organic layer was washed with brine (20 mL×1), dried over Na$_2$SO$_4$, filtered and concentrated. The crude product was purified by flash chromatography (PE/EA=2:1) to give the product trans-N-[8-chloro-6-(6-methylimidazo[1,2-a]pyridin-7-yl)-3-isoquinolyl]-2-cyano-cyclopropanecarboxamide (200 mg, 85% yield) as a yellow solid. LCMS (ESI) [M+H]$^+$=402.7.

Step 6: (±)-trans-N-(8-amino-6-(6-methylimidazo[1,2-a]pyridin-7-yl)isoquinolin-3-yl)-2-cyanocyclopropanecarboxamide

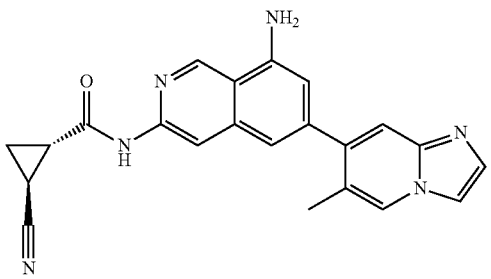 [SMILES: Cc1cn2ccnc2cc1-c1cc(N)c2cnc(NC(=O)[C@H]3C[C@@H]3C#N)cc2c1]

A mixture of Pd$_2$(dba)$_3$ (45 mg, 0.05 mmol), xantphos (57 mg, 0.1 mmol), Cs$_2$CO$_3$ (243 mg, 0.75 mmol), (±)-trans-N-[8-chloro-6-(6-methylimidazo[1,2-a]pyridin-7-yl)-3-isoquinolyl]-2-cyano-cyclopropane carboxamide (100 mg, 0.25 mmol) and tert-butyl carbamate (291 mg, 2.49 mmol) in toluene (0.5 mL) and N,N-dimethylformamide (0.5 mL) was heated to 130° C. for 16 h in a sealed tube. The reaction mixture was cooled to rt, diluted with ethyl acetate, washed with brine, dried over Na$_2$SO$_4$, filtered and concentrated. The residue was washed with PE and ethyl acetate to give the crude product. The crude product was purified by prep-HPLC (Column Xbridge 21.2*250 mm c18, 10 μm, Mobile Phase A:water (10 mMol/LNH$_4$HCO$_3$) B:ACN) to give the product (±)-trans-N-[8-amino-6-(6-methylimidazo[1,2-a]pyridin-7-yl)-3-isoquinolyl]-2-cyano-cyclopropanecarboxamide (5 mg, 5.3% yield) as a yellow solid. LCMS (ESI) R$_T$ (min)=1.646, [M+H]$^+$=383.7. Method=C; $^1$H NMR (400 MHz, CD$_3$OD) δ 9.26 (s, 1H), 8.37 (s, 1H), 8.30 (s, 1H), 7.82 (s, 1H), 7.59 (s, 1H), 7.45 (s, 1H), 7.04 (s, 1H), 6.74 (s, 1H), 2.66-2.64 (m, 1H), 2.27 (s, 3H), 2.15-2.10 (m, 1H), 1.61-1.57 (m, 2H).

Example 56

5-(8-amino-3-(trans-2-cyanocyclopropanecarboxamido)isoquinolin-6-yl)-N,1-dimethyl-1H-pyrazole-3-carboxamide (Compound 110)

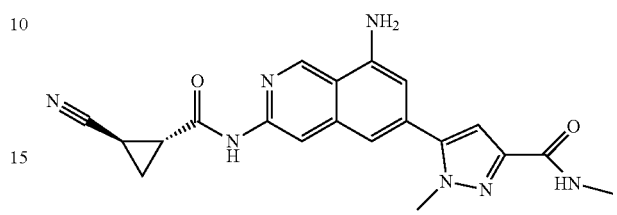

Step 1:
5-bromo-N,1-dimethyl-1H-pyrazole-3-carboxamide

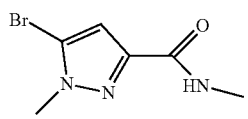

A mixture of ethyl 5-bromo-1-methyl-pyrazole-3-carboxylate (300 mg, 1.29 mmol) and methanamine in MeOH (10 mL, 12.87 mmol) was heated to 80° C. and stirred overnight. The reaction solution was concentrated to give the product 5-bromo-N,1-dimethyl-pyrazole-3-carboxamide (280 mg, 99% yield) as a colorless oil. LCMS (ESI) [M+H]$^+$=218.2

Step 2: 5-(3-amino-8-chloroisoquinolin-6-yl)-N,1-dimethyl-1H-pyrazole-3-carboxamide

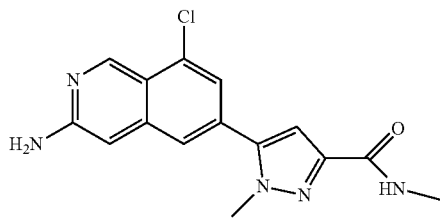 [SMILES: CNC(=O)c1cc(-c2cc(Cl)c3cnc(N)cc3c2)n(C)n1]

To a sealed tube was added 5-bromo-N,1-dimethyl-pyrazole-3-carboxamide (200 mg, 0.92 mmol), 8-chloro-6-(4,4,5,5-tetramethyl-1,3,2-dioxaborolan-2-yl)isoquinolin-3-amine (698 mg, 2.29 mmol), Pd(dppf)Cl$_2$ (67 mg, 0.09 mmol), K$_3$PO$_4$ (193 mg, 0.92 mmol) and NaOAc (225 mg, 2.75 mmol), acetonitrile (5 mL), water (1 mL). The mixture was bubbled with N$_2$ for 2 min, and stirred at 90° C. for 3 h. The mixture was concentrated. The crude product was purified by flash chromatography (DCM/MeOH=15:1) to give 5-(3-amino-8-chloro-6-isoquinolyl)-N,1-dimethyl-pyrazole-3-carboxamide (290 mg, 81% yield) as a yellow solid. LCMS (ESI) [M+H]$^+$=316.7.

Step 3: (±)-5-(8-chloro-3-(trans-2-cyanocyclopropanecarboxamido)isoquinolin-6-yl)-N,1-dimethyl-1H-pyrazole-3-carboxamide

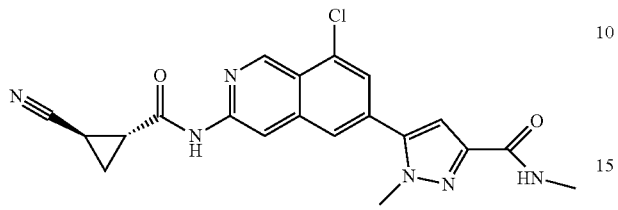

To a solution of trans-2-cyanocyclopropanecarboxylic acid (250 mg, 2.25 mmol) in dichloromethane (5 mL) and N,N-dimethylformamide (0.02 mL) was added ethanedioyl dichloride (571 mg, 4.5 mmol) at 0° C. The reaction was stirred at 25° C. for 2 h. The mixture was concentrated by rotavap to give crude (±)-trans-2-cyanocyclopropanecarbonyl chloride (290 mg, 99% yield) as a yellow oil. To a solution of 5-(3-amino-8-chloro-6-isoquinolyl)-N,1-dimethyl-pyrazole-3-carboxamide (230 mg, 0.73 mmol) in dichloromethane (15 mL) and pyridine (0.18 mL, 2.19 mmol) was added the (±)-trans-2-cyanocyclopropane carbonyl chloride (141 mg, 1.09 mmol). The mixture was stirred at 25° C. for 30 min. The mixture was concentrated and water (10 mL) was added. 1 N HCl was added to adjust the mixture to pH 6. The mixture was extracted with DCM (10 mL×3). The organic layer was washed with brine (20 mL×1), dried over $Na_2SO_4$, filtered and concentrated. The crude product was purified by flash chromatography (DCM/MeOH=15:1) to give the product (±)-5-[8-chloro-3-[[trans-2-cyanocyclopropanecarbonyl]amino]-6-isoquinolyl]-N,1-dimethyl-pyrazole-3-carboxamide (280 mg, 94% yield) as a yellow solid. LCMS (ESI) $[M+H]^+=409.7$.

Step 4: 5-(8-amino-3-(trans-2-cyanocyclopropanecarboxamido)isoquinolin-6-yl)-N,1-dimethyl-1H-pyrazole-3-carboxamide

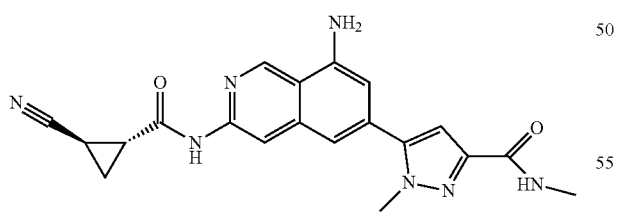

A mixture of $Pd_2dba_3$ (44 mg, 0.05 mmol), xantphos (56 mg, 0.1 mmol), $Cs_2CO_3$ (239 mg, 0.73 mmol), 5-[8-chloro-3-[[trans-2-cyanocyclopropanecarbonyl]amino]-6-isoquinolyl]-N,1-dimethyl-pyrazole-3-carboxamide (100 mg, 0.24 mmol) and tert-butyl carbamate (286 mg, 2.45 mmol) in toluene (0.5 mL) and N,N-dimethylformamide (0.5 mL) was heated to 130° C. for 16 h in a sealed tube. The reaction mixture was cooled to rt, diluted with EA, washed with brine, dried over $Na_2SO_4$, filtered and concentrated. The residue was washed with PE and ethyl acetate to give the crude product, which was purified by prep-HPLC (Column Xbridge 21.2*250 mm c18, 10 μm, Mobile Phase A:water (10 mMol/L $NH_4HCO_3$) B:CAN, to give the product (±)-5-[8-amino-3-[[trans-2-cyanocyclopropanecarbonyl]amino]-6-isoquinolyl]-N,1-dimethyl-pyrazole-3-carboxamide (17 mg, 17.8% yield) as a yellow solid. LCMS (ESI) $R_T$ (min)=1.543, $[M+H]^+=390.7$. Method=C; $^1H$ NMR (400 MHz, $CD_3OD$) δ 9.25 (s, 1H), 8.32 (s, 1H), 7.15 (s, 1H), 6.84 (s, 1H), 6.80 (d, J=1.2 Hz, 1H), 3.99 (s, 3H), 2.93 (s, 3H), 2.65-2.62 (m, 1H), 2.15-2.10 (m, 1H), 1.62-1.48 (m, 2H).

Example 57

(±)-trans-N-[8-amino-7-cyano-6-(4-methyl-3-pyridyl)-3-isoquinolyl]-2-cyano-cyclopropanecarboxamide (Compound 113)

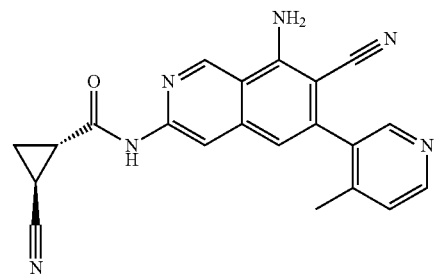 [SMILES: Cc1ccncc1-c1cc2cc(NC(=O)[C@H]3C[C@@H]3C#N)ncc2c(N)c1C#N]

Step 1: (±)-trans-N-(8-chloro-7-cyano-6-(4-methylpyridin-3-yl)isoquinolin-3-yl)-2-cyanocyclopropanecarboxamide

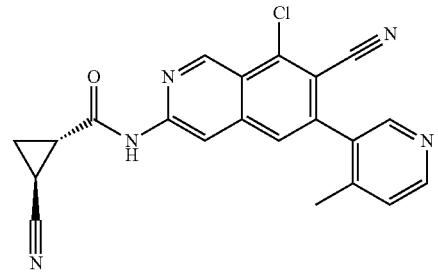 [SMILES: Cc1ccncc1-c1cc2cc(NC(=O)[C@H]3C[C@@H]3C#N)ncc2c(Cl)c1C#N]

A mixture of (±)-trans-N-[7-bromo-8-chloro-6-(4-methyl-3-pyridyl)-3-isoquinolyl]-2-cyano-cyclopropanecarboxamide (300 mg, 0.68 mmol), $Pd(PPh_3)_4$ (75 mg, 0.06 mmol) and $Zn(CN)_2$ (44 mg, 0.38 mmol) in N,N-dimethylformamide (14 mL) was stirred at 130° C. for 3 h. The mixture was purified by preparative reverse phase HPLC (C-18, acetonitrile/water+0.05% $NH_4HCO_3$), to give (±)-trans-N-[8-chloro-7-cyano-6-(4-methyl-3-pyridyl)-3-isoquinolyl]-2-cyano-cyclopropanecarboxamide (190 mg, 24% yield) as a white solid. LCMS (ESI) $[M+H]^+=388.1$.

Step 2: (±)-trans-N-[8-(benzhydrylideneamino)-7-cyano-6-(4-methyl-3-pyridyl)-3-isoquinolyl]-2-cyano-cyclopropane carboxamide

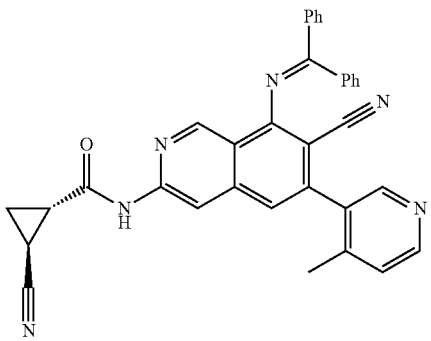 [SMILES: Cc1ccncc1-c1cc2cc(NC(=O)[C@H]3C[C@@H]3C#N)ncc2c(N=C(c2ccccc2)c2ccccc2)c1C#N]

A mixture of (±)-trans-N-[8-chloro-7-cyano-6-(4-methyl-3-pyridyl)-3-isoquinolyl]-2-cyano-cyclopropanecarboxamide (190 mg, 0.16 mmol), Pd$_2$(dba)$_3$ (28 mg, 0.03 mmol), Xantphos (37 mg, 0.06 mmol), Cs$_2$CO$_3$ (107 mg, 0.33 mmol) and benzophenone imine (100 mg, 0.55 mmol) in N,N-dimethylformamide (7 mL) and toluene (7 mL) under Ar was stirred at 130° C. for 2.5 h. EtOAc (200 mL) was added. The mixture was washed with H$_2$O (3×50 mL), brine (50 mL), dried with Na$_2$SO$_4$, filtered and evaporated under reduced pressure. The residue was purified by preparative reverse phase HPLC (C-18, acetonitrile/water+0.05% NH$_4$HCO$_3$) to give (±)-trans-N-[8-(benzhydrylideneamino)-7-cyano-6-(4-methyl-3-pyridyl)-3-isoquinolyl]-2-cyano-cyclopropanecarboxamide (36 mg, 17% yield) as a white solid. LCMS (ESI) [M+H]$^+$=533.3.

Step 3: (±)-trans-N-[8-amino-7-cyano-6-(4-methyl-3-pyridyl)-3-isoquinolyl]-2-cyano-cyclopropanecarboxamide

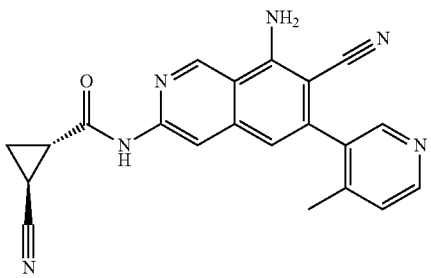 [SMILES: Cc1ccncc1-c1cc2cc(NC(=O)[C@H]3C[C@@H]3C#N)ncc2c(N)c1C#N]

A mixture of (±)-trans-N-[8-(benzhydrylideneamino)-7-cyano-6-(4-methyl-3-pyridyl)-3-isoquinolyl]-2-cyano-cyclopropanecarboxamide (36 mg, 0.04 mmol) and 2,2,2-trifluoroacetic acid (1 mL) in acetonitrile (10 mL) and water (10 mL) was stirred at 25° C. for 2 h. The reaction mixture was neutralized with NH$_4$OH (aq., 37%) to pH=7-8. The mixture was concentrated and purified by preparative reverse phase HPLC (C-18, acetonitrile/water+0.05% NH$_4$HCO$_3$) to give (±)-trans-N-[8-amino-7-cyano-6-(4-methyl-3-pyridyl)-3-isoquinolyl]-2-cyano-cyclopropanecarboxamide (11 mg, 72% yield) as a white solid. LCMS (ESI) R$_T$(min)=1.593, [M+H]$^+$=369.1, Method=G. 1H NMR (400 MHz, DMSO-d$_6$) δ 11.33 (s, 1H), 9.57 (s, 1H), 8.52 (d, J=5.2 Hz, 1H), 8.40 (s, 1H), 8.27 (s, 1H), 7.44 (s, 2H), 7.40 (d, J=5.2 Hz, 1H), 6.93 (s, 1H), 2.78-2.75 (m, 1H), 2.21 (s, 3H), 2.19-2.14 (m, 1H), 1.64-1.60 (m, 1H), 1.46-1.42 (m, 1H).

Example 58 trans-N-[8-amino-7-methyl-6-(4-methyl-3-pyridyl)-3-isoquinolyl]-2-cyano-cyclopropanecarboxamide (Compound 115)

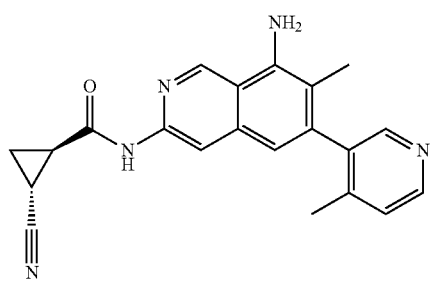 [SMILES: Cc1ccncc1-c1cc2cc(NC(=O)[C@@H]3C[C@H]3C#N)ncc2c(N)c1C]

Step 1: 7-bromo-8-chloro-6-(4-methyl-3-pyridyl)isoquinolin-3-amine

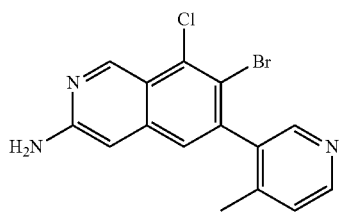 [SMILES: Cc1ccncc1-c1cc2cc(N)ncc2c(Cl)c1Br]

A mixture of 7-bromo-8-chloro-6-iodo-isoquinolin-3-amine (3.6 g, 9.39 mmol), 4-methyl-3-(4,4,5,5-tetramethyl-1,3,2-dioxaborolan-2-yl)pyridine (2.5 g, 11.41 mmol), Pd(PPh$_3$)$_4$ (750 mg, 0.65 mmol), K$_2$CO$_3$ (3.8 g, 27.54 mmol) in 1,4-dioxane (160 mL), water (40 mL) was stirred at 70° C. under Ar for 23 h. The reaction mixture was cooled to room temperature, ethyl acetate was added (500 mL), and the mixture washed with brine (100 mL). The organic layer was separated, dried over Na$_2$SO$_4$, filtered and evaporated. The residue was purified with silica-gel column chromatography (PE:EA=1:2 to EA, R$_f$=0.5 at PE/EA 1/2) to afford 7-bromo-8-chloro-6-(4-methyl-3-pyridyl)isoquinolin-3-amine (2.9 g, 89% yield) as a yellow solid. LCMS (ESI) [M+H]$^+$=348.0.

Step 2: (±)-trans-N-[7-bromo-8-chloro-6-(4-methyl-3-pyridyl)-3-isoquinolyl]-2-cyano-cyclopropanecarboxamide

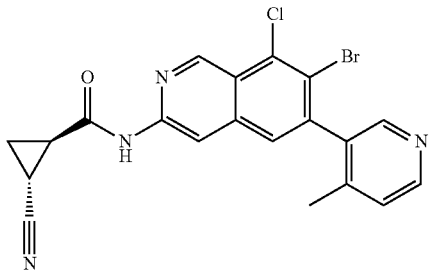 [SMILES: Cc1ccncc1-c1cc2cc(NC(=O)[C@@H]3C[C@H]3C#N)ncc2c(Cl)c1Br]

(COCl)₂ (3.0 g, 23.62 mmol) was added dropwise to a suspension of (±)-trans-2-cyanocyclopropane carboxylic acid (1.2 g, 10.8 mmol) at 0° C. and the mixture was stirred at 0° C. for another 1 h. The mixture was evaporated at room temperature to remove the unreacted (COCl)₂. The residue was suspended in DCM (5 mL) and was added dropwise to a mixture of 7-bromo-8-chloro-6-(4-methyl-3-pyridyl)isoquinolin-3-amine (2.9 g, 8.32 mmol) and pyridine (10 mL, 123.64 mmol) in dichloromethane (50 mL) at 0° C. The reaction mixture was stirred at 0° C. for another 0.5 h. To the reaction mixture was added DCM (100 mL) and it was washed with H₂O (50 mL). The organic layer was separated, dried over Na₂SO₄, filtered and evaporated. The residue was purified with silica-gel column chromatography (PE:EA=1:1 to 1:2, R$_f$=0.4 at PE/EA 1/1) to afford (±)-trans-N-[7-bromo-8-chloro-6-(4-methyl-3-pyridyl)-3-isoquinolyl]-2-cyano-cyclopropanecarboxamide (2.85 g, 78% yield) as a light brown solid. LCMS (ESI) [M+H]⁺=441.0.

Step 3: (±)-trans-N-[8-chloro-7-methyl-6-(4-methyl-3-pyridyl)-3-isoquinolyl]-2-cyano-cyclopropanecarboxamide

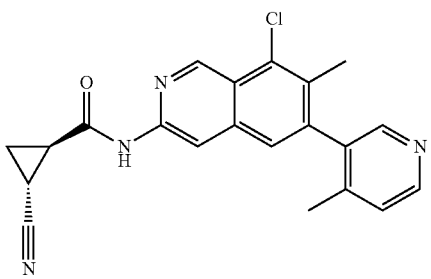 [SMILES: Cc1ccncc1-c1cc2cc(NC(=O)[C@@H]3C[C@H]3C#N)ncc2c(Cl)c1C]

A mixture of (±)-trans-N-[7-bromo-8-chloro-6-(4-methyl-3-pyridyl)-3-isoquinolyl]-2-cyano-cyclopropanecarboxamide (200 mg, 0.45 mmol), trimethylboroxine (250 mg, 1.99 mmol), PdCl₂dppf (60 mg, 0.08 mmol), and K₂CO₃ (200 mg, 1.45 mmol) in 1,4-dioxane (10 mL) and water (2.5 mL) was stirred at 80° C. under Ar in sealed tube for 18 h. The reaction mixture was cooled to room temperature, ethyl acetate added (100 mL) and washed with brine (30 mL). The organic layer was separated, dried over Na₂SO₄, filtered and evaporated. The residue was purified with silica-gel column chromatography (PE:EA=2:1 to 3:2 to 1:1) to afford (±)-trans-N-[8-chloro-7-methyl-6-(4-methyl-3-pyridyl)-3-isoquinolyl]-2-cyano-cyclopropanecarboxamide (50 mg, 29% yield) as a white solid. LCMS (ESI) [M+H]⁺=377.1.

Step 4: (±)-tert-butyl N-[3-[(trans-2-cyanocyclopropanecarbonyl)amino]-7-methyl-6-(4-methyl-3-pyridyl)-8-isoquinolyl]carbamate

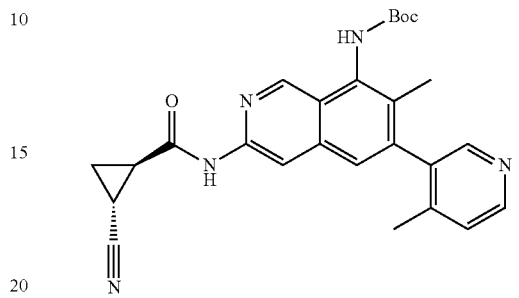

A mixture of (±)-trans-N-[8-chloro-7-methyl-6-(4-methyl-3-pyridyl)-3-isoquinolyl]-2-cyano-cyclopropanecarboxamide (25 mg, 0.07 mmol), tert-butyl carbamate (75 mg, 0.64 mmol), Pd₂dba₃ (20 mg, 0.02 mmol), Brettphos (20 mg, 0.04 mmol), and t-BuONa (2M in THF, 0.08 mL, 0.16 mmol) in 1,4-dioxane (2 mL) was stirred at 90° C. under Ar for 2 h. The reaction mixture was cooled to room temperature. To the residue was added ethyl acetate (30 mL) and washed with sat. NH₄Cl (10 mL). The ethyl acetate layer was separated, dried over Na₂SO₄, filtered and evaporated. The residue was purified with prep-TLC (EA:PE=3:2) to afford (±)-tert-butyl N-[3-[(trans-2-cyanocyclopropanecarbonyl)amino]-7-methyl-6-(4-methyl-3-pyridyl)-8-isoquinolyl]carbamate (7 mg, 23.1% yield) as white solid. LCMS (ESI) [M+H]⁺=458.2.

Step 5: (±)-trans-N-[8-amino-7-methyl-6-(4-methyl-3-pyridyl)-3-isoquinolyl]-2-cyano-cyclopropanecarboxamide

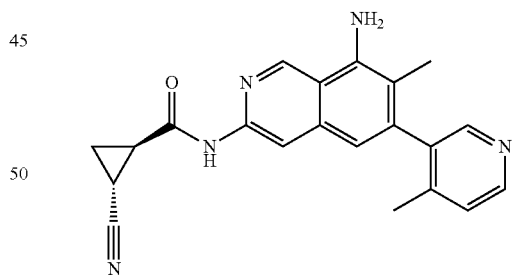

A mixture of (±)-tert-butyl N-[3-[(trans-2-cyanocyclopropanecarbonyl)amino]-7-methyl-6-(4-methyl-3-pyridyl)-8-isoquinolyl]carbamate (7 mg, 0.02 mmol) in 2,2,2-trifluoroacetic acid (0.5 mL) and dichloromethane (2 mL) was stirred at 25° C. for 2 h. The reaction mixture was evaporated. The residue was dissolved in MeOH (1 mL), 7N NH₃/MeOH added until pH 9-10, and then purified by flash column chromatography (C₁₈, NH₄HCO₃/MeOH/H₂O) to give (±)-trans-N-[8-Amino-7-methyl-6-(4-methyl-3-pyridyl)-3-isoquinolyl]-2-cyano-cyclopropanecarboxamide (3 mg, 54.9% yield) as a light brown solid. LCMS (ESI):R$_T$ (min)=1.70, [M+H]⁺=358.1, Method=C; ¹H NMR (400 MHz, CD₃OD) δ 9.31 (s, 1H), 8.45 (d, J=5.2 Hz, 1H), 8.28 (s, 1H), 8.22 (s, 1H), 7.42 (d, J=5.2 Hz, 1H), 6.90 (s, 1H), 2.66-2.62 (m, 1H), 2.16 (s, 3H), 2.13-2.08 (m, 1H), 1.98 (s, 3H), 1.61-1.52 (m, 2H).

Example 59

(±)-trans-N-[8-amino-6-[4-(dimethylamino)-3-pyridyl]-3-isoquinolyl]-2-cyano-cyclopropanecarboxamide (Compound 116)

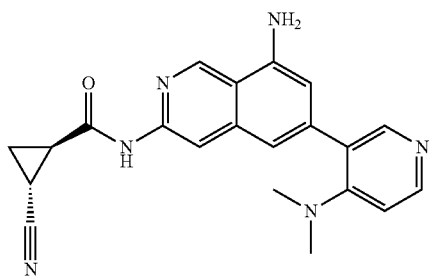 [SMILES: CN(C)c1ccncc1-c1cc(N)c2cnc(NC(=O)[C@@H]3C[C@H]3C#N)cc2c1]

Step 1: (±)-trans-N-[8-chloro-6-[4-(dimethylamino)-3-pyridyl]-3-isoquinolyl]-2-cyano-cyclopropanecarboxamide

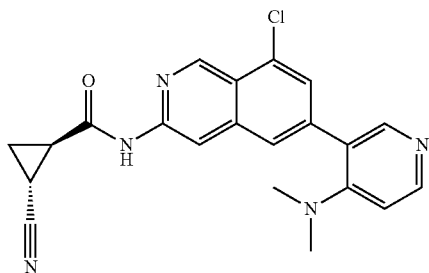 [SMILES: CN(C)c1ccncc1-c1cc(Cl)c2cnc(NC(=O)[C@@H]3C[C@H]3C#N)cc2c1]

The reaction mixture of [8-chloro-3-[(trans-2-cyanocyclopropanecarbonyl)amino]-6-isoquinolyl]boronic acid and (±)-trans-N-[8-chloro-6-(4,4,5,5-tetramethyl-1,3,2-dioxaborolan-2-yl)-3-isoquinolyl]-2-cyano-cyclopropanecarboxamide (5 mL, about 0.43 mmol) was added 3-bromo-N,N-dimethyl-pyridin-4-amine (150 mg, 0.75 mmol), PdCl₂dppf (50 mg, 0.07 mmol), K₂CO₃ (150 mg, 1.09 mmol) and water (1.5 mL). The reaction was then stirred at 80° C. under Ar for 1 h. The reaction mixture was cooled to room temperature, ethyl acetate added (40 mL) and washed with brine (15 mL). The organic layer was separated, dried over Na₂SO₄, filtered and evaporated. The residue was purified with silica-gel column chromatography (PE:DCM:EA=1:1:1 to 1:1:0) to give (±)-trans-N-[8-chloro-6-[4-(dimethylamino)-3-pyridyl]-3-isoquinolyl]-2-cyano-cyclopropanecarboxamide (80 mg, 48% yield) as a brown solid. LCMS (ESI) [M+H]⁺=392.1.

Step 2: (±)-trans-N-[8-(benzhydrylideneamino)-6-[4-(dimethylamino)-3-pyridyl]-3-isoquinolyl]-2-cyano-cyclopropanecarboxamide

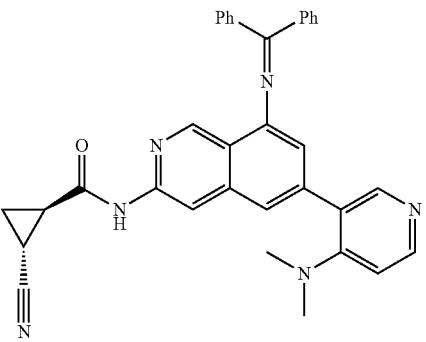 [SMILES: CN(C)c1ccncc1-c1cc(N=C(c2ccccc2)c2ccccc2)c2cnc(NC(=O)[C@@H]3C[C@H]3C#N)cc2c1]

A mixture of (±)-trans-N-[8-chloro-6-[4-(dimethylamino)-3-pyridyl]-3-isoquinolyl]-2-cyano-cyclopropanecarboxamide (80 mg, 0.20 mmol), benzophenone imine (210 mg, 1.16 mmol), Pd₂dba₃ (40 mg, 0.04 mmol), Xantphos (50 mg, 0.09 mmol), and Cs₂CO₃ (120 mg, 0.37 mmol) in N,N-dimethylformamide (2 mL) and toluene (2 mL) was stirred at 130° C. under Ar for 4 h. The reaction mixture was cooled to room temperature and ethyl acetate (50 mL) was added. The mixture washed with brine (15 mL). The ethyl acetate layer was separated, dried over Na₂SO₄, filtered and evaporated. The residue was purified with silica chromatography (PE:EA=1:1 to 1:3) to give (±)-trans-N-[8-(benzhydrylideneamino)-6-[4-(dimethylamino)-3-pyridyl]-3-isoquinolyl]-2-cyano-cyclopropanecarboxamide (45 mg, 41% yield) as a brown solid. LCMS (ESI) [M+H]⁺=537.2.

Step 3: (±)-trans-N-[8-amino-6-[4-(dimethylamino)-3-pyridyl]-3-isoquinolyl]-2-cyano-cyclopropanecarboxamide

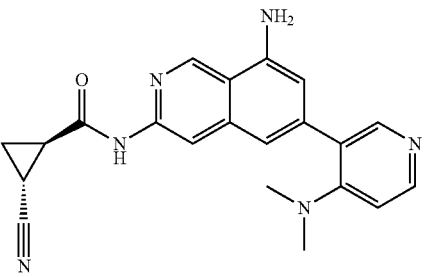 [SMILES: CN(C)c1ccncc1-c1cc(N)c2cnc(NC(=O)[C@@H]3C[C@H]3C#N)cc2c1]

A mixture of (±)-trans-N-[8-(benzhydrylideneamino)-6-[4-(dimethylamino)-3-pyridyl]-3-isoquinolyl]-2-cyano-cyclopropanecarboxamide (45 mg, 0.08 mmol) in 2,2,2-trifluoroacetic acid (1 mL), dichloromethane (2 mL) and water (0.5 mL) was stirred at 25° C. for 20 min. The residue was dissolved in MeOH (1 mL). To the mixture was added 7N NH₃/MeOH until pH 9-10. The mixture was then concentrated. The residue was purified with prep-TLC (EA: MeOH=20:1) to give (±)-trans-N-[8-amino-6-[4-(dimethylamino)-3-pyridyl]-3-isoquinolyl]-2-cyano-cyclopropanecarboxamide (18.8 mg, 60% yield) as a yellow solid. LCMS (ESI): R_T (min)=1.64, [M+H]⁺=373.2, method=C; ¹H NMR (400 MHz, CD₃OD) δ 9.21 (s, 1H), 8.26 (s, 1H), 8.17 (d, J=6.0 Hz, 1H), 8.11 (s, 1H), 7.07 (s, 1H), 6.93 (d, J=6.0 Hz, 1H), 6.80 (d, J=1.2 Hz, 1H), 2.77 (s, 6H), 2.65-2.62 (m, 1H), 2.14-2.09 (m, 1H), 1.62-1.52 (m, 2H).

Example 60

(±)-trans-N-(8-amino-6-(1-methyl-4-oxo-1,4-dihydropyridin-2-yl)isoquinolin-3-yl)-2-cyanocyclopropanecarboxamide (Compound 117)

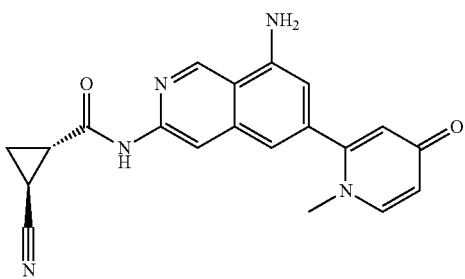 [SMILES: Cn1ccc(=O)cc1-c1cc(N)c2cnc(NC(=O)[C@H]3C[C@@H]3C#N)cc2c1]

Step 1: 2-(3-amino-8-chloroisoquinolin-6-yl)-1-methylpyridin-4(1H)-one

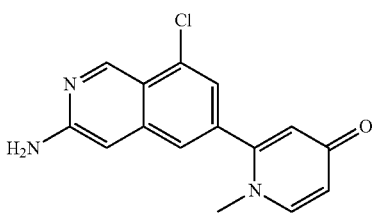 [SMILES: Cn1ccc(=O)cc1-c1cc(Cl)c2cnc(N)cc2c1]

To a sealed tube was added (3-amino-8-chloro-6-isoquinolyl)boronic acid (371 mg, 1.67 mmol), 2-chloro-1-methylpyridin-4-one (200 mg, 1.39 mmol), Pd(dppf)Cl₂ (101 mg, 0.14 mmol), K₃PO₄ (293 mg, 1.39 mmol), NaOAc (342 mg, 4.18 mmol), acetonitrile (20 mL) and water (2 mL). The mixture was bubbled with N₂ for 2 min and stirred at 90° C. for 3 h. The mixture was concentrated and purified by prep-TLC (DCM/MeOH=20/1) to give 2-(3-amino-8-chloro-6-isoquinolyl)-1-methyl-pyridin-4-one (220 mg, 55% yield) as a yellow solid. LCMS (ESI): [M-56]⁺=286.0.

Step 2: (±)-trans-N-(8-chloro-6-(1-methyl-4-oxo-1,4-dihydropyridin-2-yl)isoquinolin-3-yl)-2-cyanocyclopropanecarboxamide

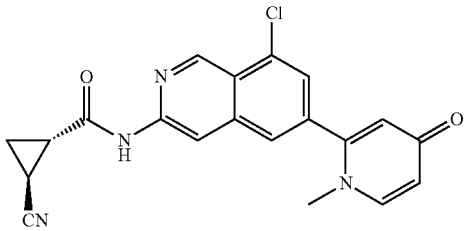 [SMILES: Cn1ccc(=O)cc1-c1cc(Cl)c2cnc(NC(=O)[C@H]3C[C@@H]3C#N)cc2c1]

To a solution of 2-(3-amino-8-chloro-6-isoquinolyl)-1-methyl-pyridin-4-one (210 mg, 0.74 mmol) and pyridine (0.18 mL, 2.2 mmol) in dichloromethane (15 mL) was added (±)-trans-2-cyanocyclopropanecarbonyl chloride (238 mg, 1.84 mmol). The mixture was stirred at 25° C. for 30 min. The mixture was then concentrated and purified by flash chromatography (PE/EA=2:1) to give the (±)-trans-N-[8-chloro-6-(1-methyl-4-oxo-2-pyridyl)-3-isoquinolyl]-2-cyano-cyclopropanecarboxamide (160 mg, 40% yield) as a yellow solid. LCMS (ESI): [M-56]⁺=379.1.

Step 3: (±)-trans-N-(8-amino-6-(1-methyl-4-oxo-1,4-dihydropyridin-2-yl)isoquinolin-3-yl)-2-cyanocyclopropanecarboxamide

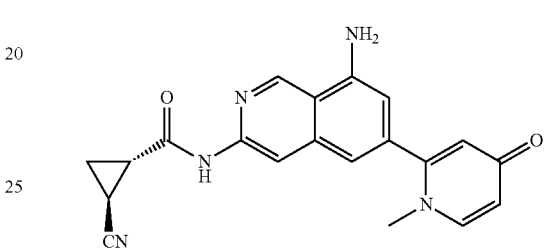

A mixture of (±)-trans-N-[8-chloro-6-(1-methyl-4-oxo-2-pyridyl)-3-isoquinolyl]-2-cyano-cyclopropanecarboxamide (70 mg, 0.18 mmol), xantphos (42 mg, 0.07 mmol), Pd₂dba₃ (33 mg, 0.04 mmol), and Cs₂CO₃ (180 mg, 0.55 mmol) in DMF (3 mL) and toluene (3 mL) was heated to 130° C. for 2 h. The mixture was concentrated and purified by prep-HPLC to give (±)-trans-N-[8-amino-6-(1-methyl-4-oxo-2-pyridyl)-3-isoquinolyl]-2-cyano-cyclopropanecarboxamide (11.4 mg, 17% yield) as a yellow solid. LCMS (ESI): R$_T$ (min)=1.310, [M+H]⁺=360.1, Method=G; ¹H NMR (400 MHz, DMSO-d₆) δ 11.15 (s, 1H), 9.37 (s, 1H), 8.27 (s, 1H), 7.74 (d, J=7.6 Hz, 1H), 6.99 (s, 1H), 6.54-6.51 (m, 3H), 6.14 (dd, J=2.8, 7.6 Hz, 1H), 6.02 (d, J=2.8 Hz, 1H), 3.41 (s, 3H), 2.77-2.73 (m, 1H), 2.17-2.12 (m, 1H), 1.62-1.57 (m, 1H), 1.45-1.41 (m, 1H).

Example 61

(±)-trans-N-(8-amino-6-(3-(hydroxymethyl)-5-methyl-1H-pyrazol-4-yl)isoquinolin-3-yl)-2-cyanocyclopropanecarboxamide (Compound 118)

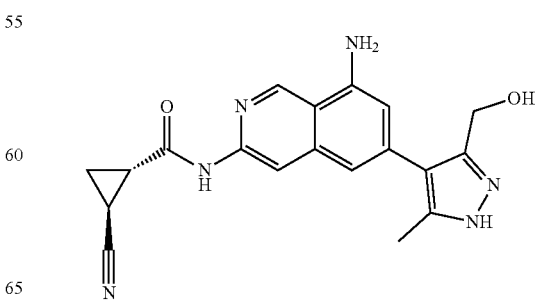

Step 1: 4-bromo-3-(ethoxymethyl)-5-methyl-1H-pyrazole

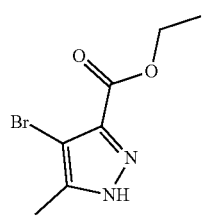

A mixture of ethyl 5-methyl-1H-pyrazole-3-carboxylate (4.0 g, 25.95 mmol) and NBS (5.08 g, 28.54 mmol) in N,N-dimethylformamide (15 mL) was stirred at room temperature for 16 h. The mixture was taken up in EtOAc (200 mL) and the organics were washed with saturated brine solution. The organics were then separated and dried ($Na_2SO_4$) before concentrated to dryness. The crude was then purified by flash column chromatography (PE/EA=3/2) to give ethyl 4-bromo-5-methyl-1H-pyrazole-3-carboxylate (4.8 g, 79% yield) as a white solid. LCMS (ESI): $[M+H]^+=234.9$.

Step 2: 4-bromo-3-(ethoxymethyl)-5-methyl-1-(tetrahydro-2H-pyran-2-yl)-1H-pyrazole

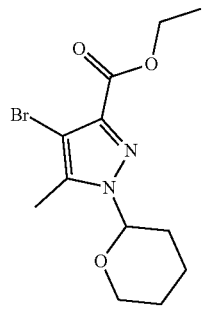 [SMILES: CCOC(=O)c1nn(C2CCCCO2)c(C)c1Br]

To a stirred solution of TsOH-$H_2O$ (490 mg, 2.57 mmol) and ethyl 4-bromo-5-methyl-1H-pyrazole-3-carboxylate (3.0 g, 12.87 mmol) in dichloromethane (50 mL) was added 3,4-dihydro-2h-pyran (2.17 g, 25.74 mmol). The mixture was stirred at room temperature for 4 h. The mixture was concentrated and purified by flash column chromatography (PE/EA=4/1) to give the product ethyl 4-bromo-5-methyl-1-tetrahydropyran-2-yl-pyrazole-3-carboxylate (3.4 g, 83% yield) as a yellow oil. $^1$HNMR (400 MHz, $CD_3OD$) δ 5.52 (dd, J=2.8, 9.6 Hz, 1H), 4.38 (q, J=7.2 Hz, 2H), 4.01-3.96 (m, 1H), 3.77-3.71 (m, 1H), 2.42-2.35 (m, 4H), 2.14-2.10 (m, 1H), 1.99-1.94 (m, 1H), 1.82-1.62 (m, 3H), 1.40 (t, J=7.2 Hz, 3H).

Step 3: 8-chloro-6-(3-(ethoxymethyl)-5-methyl-1-(tetrahydro-2H-pyran-2-yl)-1H-pyrazol-4-yl)isoquinolin-3-amine

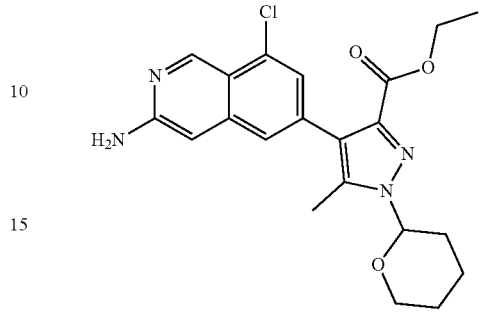

To a sealed tube was added (3-amino-8-chloro-6-isoquinolyl)boronic acid (252 mg, 1.14 mmol), ethyl 4-bromo-5-methyl-1-tetrahydropyran-2-yl-pyrazole-3-carboxylate (300 mg, 0.95 mmol), $Pd(dppf)_2Cl_2$ (69 mg, 0.09 mmol), $K_3PO_4$ (199 mg, 0.95 mmol), NaOAc (232 mg, 2.84 mmol), acetonitrile (5 mL) and water (0.5 mL). The mixture was bubbled with $N_2$ for 20 min and stirred at 90° C. for 3 h. The reaction was concentrated and purified by prep-TLC (PE/EA=1:1) to give ethyl 4-(3-amino-8-chloro-6-isoquinolyl)-5-methyl-1-tetrahydropyran-2-yl-pyrazole-3-carboxylate (320 mg, 75% yield) as a yellow solid. LCMS (ESI): $[M+H]^+=415.1$.

Step 4: (4-(3-amino-8-chloroisoquinolin-6-yl)-5-methyl-1-(tetrahydro-2H-pyran-2-yl)-1H-pyrazol-3-yl)methanol

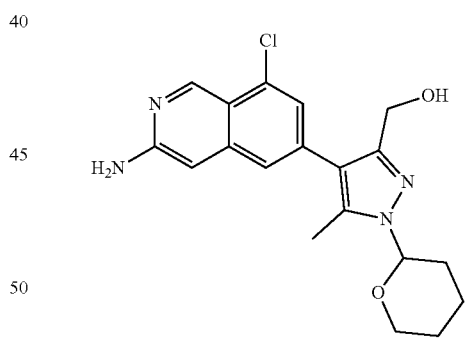

A mixture of ethyl 4-(3-amino-8-chloro-6-isoquinolyl)-5-methyl-1-tetrahydropyran-2-yl-pyrazole-3-carboxylate (310 mg, 0.75 mmol) in methyl alcohol (15 mL) was added $NaBH_4$ (282 mg, 7.47 mmol) at 0° C. The mixture was stirred at rt for 5 h and water (2 mL) was added to quench the reaction. The mixture was concentrated and a solution of DCM:MeOH (10:1, 10 mL) was added. The mixture was filtered and the filtrate was concentrated and purified by prep-TLC (100% EA) to give [4-(3-amino-8-chloro-6-isoquinolyl)-5-methyl-1-tetrahydropyran-2-yl-pyrazol-3-yl]methanol (300 mg, 75% yield) as a yellow solid. LCMS (ESI): $[M+H]^+=373.1$.

Step 5: 6-(3-((tert-butyldimethylsilyloxy)methyl)-5-methyl-1-(tetrahydro-2H-pyran-2-yl)-1H-pyrazol-4-yl)-8-chloroisoquinolin-3-amine

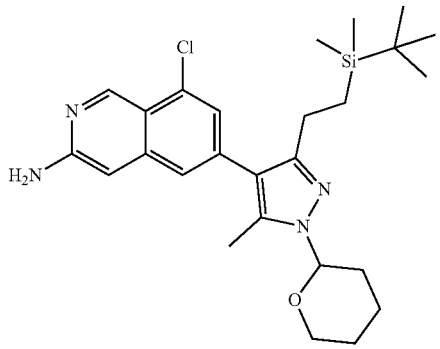 [SMILES: Cc1c(-c2cc(Cl)c3cnc(N)cc3c2)c(CC[Si](C)(C)C(C)(C)C)nn1C1CCCCO1]

A mixture of [4-(3-amino-8-chloro-6-isoquinolyl)-5-methyl-1-tetrahydropyran-2-yl-pyrazol-3-yl]methanol (300 mg, 0.56 mmol), tert-butyldimethylchlorosilane (849 mg, 5.64 mmol), and TEA (1267 mg, 12.55 mmol) in dichloromethane (50 mL) was refluxed overnight. The mixture was concentrated and purified by prep-TLC (PE/EA=2/1) to give 6-[3-[[tert-butyl(dimethyl)silyl]oxymethyl]-5-methyl-1-tetrahydropyran-2-yl-pyrazol-4-yl]-8-chloro-isoquinolin-3-amine (210 mg, 72% yield) as a yellow oil. LCMS (ESI): [M+H]$^+$=488.2.

Step 6: trans-N-(6-(3-((tert-butyldimethylsilyloxy)methyl)-5-methyl-1-(tetrahydro-2H-pyran-2-yl)-1H-pyrazol-4-yl)-8-chloroisoquinolin-3-yl)-2-cyanocyclopropanecarboxamide

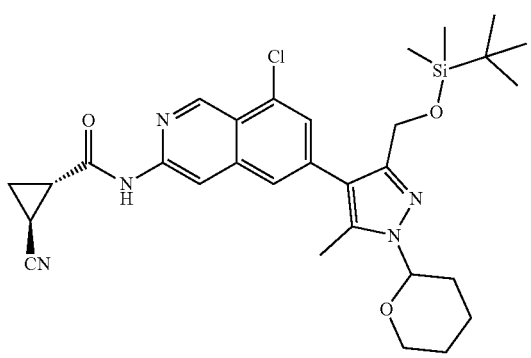 [SMILES: Cc1c(-c2cc(Cl)c3cnc(NC(=O)[C@H]4C[C@@H]4C#N)cc3c2)c(CO[Si](C)(C)C(C)(C)C)nn1C1CCCCO1]

To a solution of 6-[3-[[tert-butyl(dimethyl)silyl]oxymethyl]-5-methyl-1-tetrahydropyran-2-yl-pyrazol-4-yl]-8-chloro-isoquinolin-3-amine (200 mg, 0.41 mmol) in dichloromethane (15 mL) and pyridine (0.3 mL) was added (±)-trans-2-cyanocyclopropanecarbonyl chloride (132 mg, 1.03 mmol). The mixture was stirred at 25° C. for 30 min. The mixture was concentrated and purified by prep-TLC (PE/EA=3:1) to give (±)-trans-N-[6-[3-[[tert-butyl(dimethyl)silyl]oxymethyl]-5-methyl-1-tetrahydropyran-2-yl-pyrazol-4-yl]-8-chloro-3-isoquinolyl]-2-cyano-cyclopropanecarboxamide (150 mg, 60% yield) as a yellow solid. LCMS (ESI): [M+H]$^+$=580.3.

Step 7: (±)-trans-N-(8-amino-6-(3-((tert-butyldimethylsilyloxy)methyl)-5-methyl-1-(tetrahydro-2H-pyran-2-yl)-1H-pyrazol-4-yl)isoquinolin-3-yl)-2-cyanocyclopropanecarboxamide

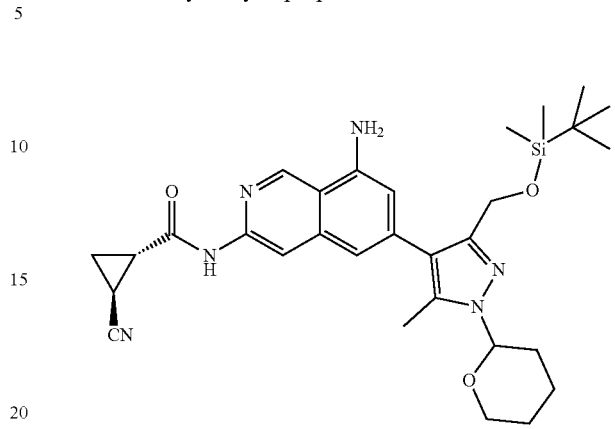

A mixture of (±)-trans-N-[6-[3-[[tert-butyl(dimethyl)silyl]oxymethyl]-5-methyl-1-tetrahydropyran-2-yl-pyrazol-4-yl]-8-chloro-3-isoquinolyl]-2-cyano-cyclopropanecarboxamide (140 mg, 0.24 mmol), xantphos (55 mg, 0.10 mmol), Pd$_2$dba$_3$ (44 mg, 0.05 mmol), and Cs$_2$CO$_3$ (235 mg, 0.72 mmol) in N,N-dimethylformamide (1.5 mL)/toluene (1.5 mL) was heated at 145° C. for 3 h. The mixture was concentrated and used in the next step without further purification. LCMS (ESI): [M+H]$^+$=561.3.

Step 8: (±)-trans-N-(8-amino-6-(3-(hydroxymethyl)-5-methyl-H-pyrazol-4-yl)isoquinolin-3-yl)-2-cyano-cyclopropanecarboxamide

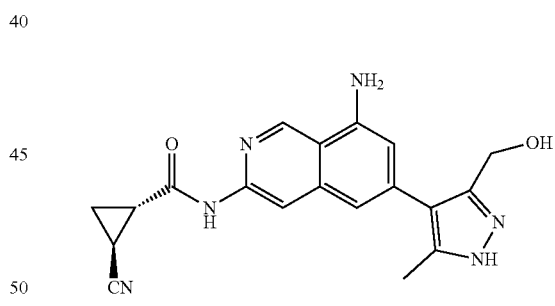

To a sealed tube was added (±)-trans-N-[8-amino-6-[3-[[tert-butyl(dimethyl)silyl]oxymethyl]-5-methyl-1-tetrahydropyran-2-yl-pyrazol-4-yl]-3-isoquinolyl]-2-cyano-cyclopropanecarboxamide (60 mg, 0.11 mmol), dichloromethane (5 mL) and 2,2,2-trifluoroacetic acid (1 mL) and the mixture was stirred at rt for 2 h. The mixture was concentrated and purified by prep-HPLC to give (±)-trans-N-[8-amino-6-[3-(hydroxymethyl)-5-methyl-1H-pyrazol-4-yl]-3-isoquinolyl]-2-cyano-cyclopropanecarboxamide (9 mg, 23% yield) as a yellow solid. LCMS (ESI): R$_T$ (min)=1.268, [M+H]$^+$=363.1, method=A; $^1$HNMR (400 MHz, CD$_3$OD) δ 9.19 (s, 1H), 8.26 (s, 1H), 7.12 (s, 1H), 6.85 (s, 1H), 4.63 (s, 2H), 2.67-2.62 (m, 1H), 2.38 (s, 3H), 2.14-2.09 (m, 1H), 1.61-1.53 (m, 2H).

Example 62

(±)-trans-N-(8-amino-6-(4-methylpyridin-3-yl)isoquinolin-3-yl)-2-(hydroxymethyl)cyclopropanecarboxamide (Compound 119)

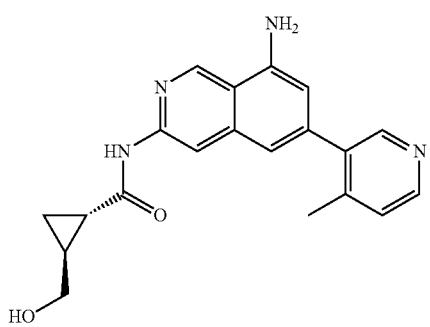 [SMILES: Cc1ccncc1-c1cc(N)c2cnc(NC(=O)[C@H]3C[C@@H]3CO)cc2c1]

Step 1: (±)-trans-2-(hydroxymethyl)cyclopropanecarboxylic Acid

To a vial was added methyl (±)-trans-2-(hydroxymethyl)cyclopropanecarboxylate (500 mg, 3.84 mmol), water (5 mL), tetrahydrofuran (5 mL), methyl alcohol (5 mL) and NaOH (700 mg, 17.5 mmol) and the mixture stirred at 40° C. for 2 hours. The mixture was concentrated and acidified to pH=34 with 2 N HCl. The product was extracted with ethyl acetate (50 mL×2), washed with brine (20 mL), dried over Na$_2$SO$_4$, filtered and concentrated in vacuo to give (±)-trans-2-(hydroxymethyl)cyclopropanecarboxylic acid (390 mg, 87% yield) as a pale-yellow oil. $^1$H NMR (400 MHz, DMSO-d$_6$) δ: 3.40 (dd, J=5.2, 11.6 Hz, 1H), 3.22 (dd, J=5.6, 11.6 Hz, 1H), 1.41-1.35 (m, 2H), 0.91-0.85 (m, 1H), 0.75-0.70 (m, 1H).

Step 2: (±)-trans-2-(acetoxymethyl)cyclopropanecarboxylic Acid

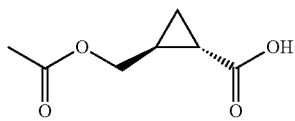

To a vial was added (±)-trans-2-(hydroxymethyl)cyclopropanecarboxylic acid (390 mg, 3.36 mmol), dichloromethane (10 mL) and acetyl chloride (1 mL, 14.14 mmol) and the mixture was stirred at 40° C. for 2 hours. The mixture was concentrated in vacuo to get (±)-trans-2-(acetoxymethyl)cyclopropanecarboxylic acid (530 mg, 90% yield) as a pale-yellow oil. $^1$H NMR (400 MHz, DMSO-d$_6$) δ: 12.20 (s, 1H), 3.99 (dd, J=6.0, 11.6 Hz, 1H), 3.83 (dd, J=7.2, 11.6 Hz, 1H), 2.02 (s, 3H), 1.59-1.50 (m, 2H), 1.04-0.99 (m, 1H), 0.92-0.87 (m, 1H).

Step 3: (±)-trans-2-(chlorocarbonyl)cyclopropyl)methyl Acetate

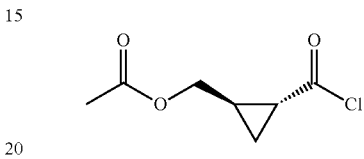

To a vial was added (±)-trans-2-(acetoxymethyl)cyclopropanecarboxylic acid (530 mg, 3.02 mmol) and DCM (30 mL) and cooled to 0° C. Oxalyl dichloride (0.5 mL, 6.03 mmol) was added dropwise and then N,N-dimethylformamide (0.01 mL, 0.13 mmol). The mixture was stirred at 20° C. for 2 hours. The reaction mixture was concentrated in vacuo to afford a crude product that was used directly in the next step.

Step 4: (±)-trans-2-(8-chloro-6-(4-methylpyridin-3-yl)isoquinolin-3-ylcarbamoyl)cyclopropyl)methyl Acetate

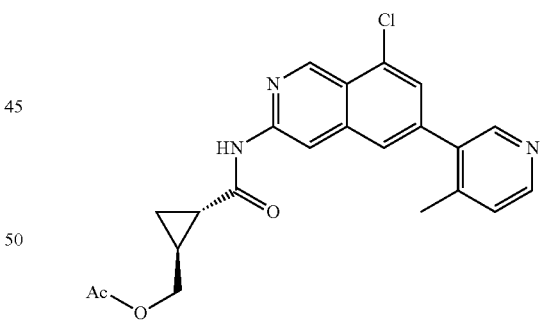

To a vial was added 8-chloro-6-(4-methyl-3-pyridyl)isoquinolin-3-amine (200 mg, 0.74 mmol), TEA (0.8 mL, 5.69 mmol) and DCM (5 mL) and then a solution of (±)-trans-2-chlorocarbonylcyclopropyl)methyl acetate (650 mg, 2.94 mmol) in DCM (5 mL) was added dropwise. The mixture was stirred at rt for 2 hours. The mixture was concentrated and purified by flash column chromatography (PE/EA from 1:1 to 0:100) to get (±)-trans-[2-[[8-chloro-6-(4-methyl-3-pyridyl)-3-isoquinolyl]carbamoyl]cyclopropyl]methyl acetate (220 mg, 72% yield) as white solid. LCMS (ESI): [M+H]$^+$=410.1.

Step 5: (±)-trans-N-(8-(diphenylmethyleneamino)-6-(4-methylpyridin-3-yl)isoquinolin-3-yl)-2-(hydroxymethyl)cyclopropanecarboxamide

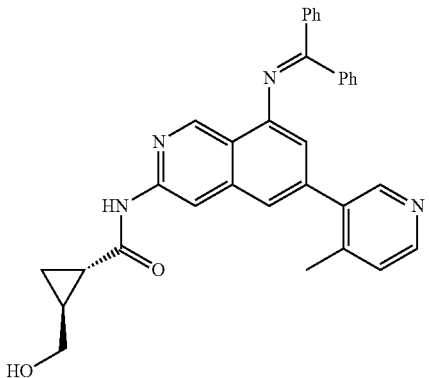 [SMILES: Cc1ccncc1-c1cc(N=C(c2ccccc2)c2ccccc2)c2cnc(NC(=O)[C@H]3C[C@@H]3CO)cc2c1]

To a sealed tube was added (±)-[trans-2-[[8-chloro-6-(4-methyl-3-pyridyl)-3-isoquinolyl]carbamoyl] cyclopropyl] methyl acetate (210 mg, 0.51 mmol), Xantphos (150 mg, 0.2600 mmol), Pd$_2$(dba)$_3$ (150 mg, 0.16 mmol), Cs$_2$CO$_3$ (500 mg, 1.54 mmol), benzophenone imine (600 mg, 3.31 mmol) and N,N-dimethylformamide (10 mL). The mixture was bubbled with N$_2$ for 2 min and then stirred at 130° C. for 4 hours. The mixture was concentrated at 100° C. to remove all organic solvents. Methyl alcohol (20 mL) was added and the reaction was stirred at 50° C. for 1 hour. The mixture was then filtered and concentrated in vacuo. The residue was purified by column chromatography (PE/EA from 1:1 to 0:100) to give (±)-trans-N-[8-benzhydrylideneamino)-6-(4-methyl-3-pyridyl)-3-isoquinolyl]-2-(hydroxymethyl) cyclopropanecarboxamide (151 mg, 50% yield) as a yellow solid. LCMS (ESI): [M+H]$^+$=513.3.

Step 6: (±)-trans-N-(8-amino-6-(4-methylpyridin-3-yl)isoquinolin-3-yl)-2-(hydroxymethyl)cyclopropanecarboxamide

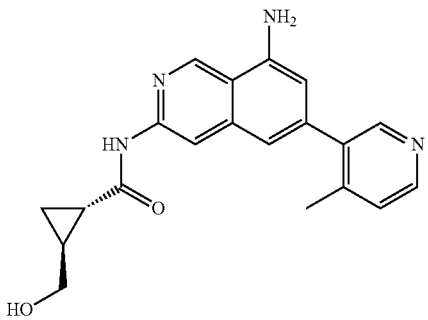 [SMILES: Cc1ccncc1-c1cc(N)c2cnc(NC(=O)[C@H]3C[C@@H]3CO)cc2c1]

To a vial was added (±)-trans-N-[8-(benzhydrylideneamino)-6-(4-methyl-3-pyridyl)-3-isoquinolyl]-2-(hydroxymethyl)cyclopropanecarboxamide (150 mg, 0.25 mmol) and 2 N HCl (5 mL, 10 mmol). The mixture was stirred at rt for 2 h. The pH of the mixture was then adjusted to pH 7 with aq. NaHCO$_3$. The product was then extracted with DCM/MeOH=10:1 (100 mL×2). The organic extracts were concentrated in vacuo and purified by combiflash (DCM/MEOH from 30:1 to 15:1) to get (±)-trans-N-[8-amino-6-(4-methyl-3-pyridyl)-3-isoquinolyl]-2-(hydroxymethyl)cyclopropanecarboxamide (74 mg, 82% yield) as a yellow solid. The single enantiomers were further isolated by chiral SFC. LCMS (ESI) of racemate: R$_T$ (min)=1.302, [M+H]$^+$=349.2, method=B; $^1$H NMR of racemate (400 MHz, CD$_3$OD) δ 9.24 (s, 1H), 8.40 (d, J=5.6 Hz, 1H), 8.39 (s, 1H), 8.28 (s, 1H), 7.39 (d, J=5.2 Hz, 1H), 6.98 (s, 1H), 6.67 (d, J=1.6 Hz, 1H), 3.64 (dd, J=6.0, 11.2 Hz, 1H), 3.48 (dd, J=6.8, 11.2 Hz, 1H), 2.37 (s, 3H), 1.92-1.85 (m, 1H), 1.77-1.66 (m, 1H), 1.28-1.21 (m, 1H), 0.97-0.90 (m, 1H).

Example 63

(±)-trans-N-[8-amino-6-[3-(trifluoromethyl)-1H-pyrazol-4-yl]-3-isoquinolyl]-2-cyano-cyclopropane Carboxamide (Compound 122)

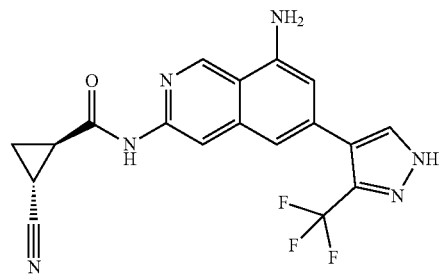 [SMILES: N#C[C@@H]1C[C@H]1C(=O)Nc1cc2cc(-c3c[nH]nc3C(F)(F)F)cc(N)c2cn1]

Step 1: (±)-trans-N-[8-chloro-6-[3-(trifluoromethyl)-1H-pyrazol-4-yl]-3-isoquinolyl]-2-cyano-cyclopropanecarboxamide

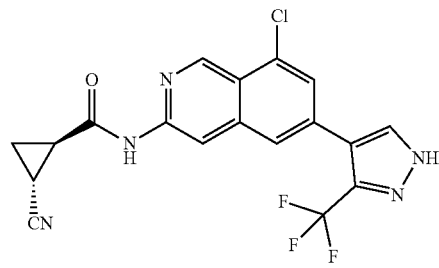

A mixture of (±)-trans-N-(6-bromo-8-chloro-3-isoquinolyl)-2-cyano-cyclopropanecarboxamide (350 mg, 1 mmol), 4-(4,4,5,5-tetramethyl-1,3,2-dioxaborolan-2-yl)-3-(trifluoromethyl)-1H-pyrazole (300 mg, 1.14 mmol), Pd(dppf)Cl$_2$ (70 mg, 0.1 mmol), potassium phosphate (3H$_2$O) (660 mg, 2.48 mmol) in 1,4-dioxane (9 mL) and water (1.5 mL) was stirred at 100° C. for 3 h. The reaction was concentrated to dryness. The crude residue was then purified by silica gel column chromatography (ethyl acetate/ petroleum ether1/13-1/1) to afford (±)-trans-N-[8-chloro-6-[3-(trifluoromethyl)-1H-pyrazol-4-yl]-3-isoquinolyl]-2-cyano-cyclopropanecarboxamide (230 mg, 51% yield) as a white solid. LCMS (ESI): [M+H]$^+$=406.1.

Step 2: (±)-trans-N-[8-chloro-6-[1-tetrahydropyran-2-yl-3-(trifluoromethyl)pyrazol-4-yl]-3-isoquinolyl]-2-cyano-cyclopropanecarboxamide

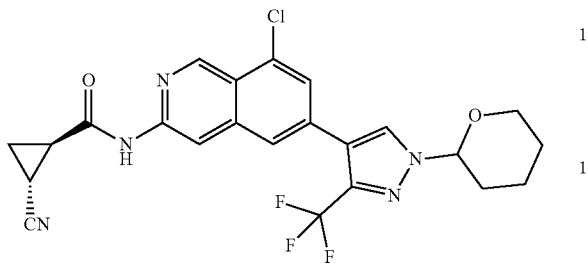

A solution of (±)-trans-N-[8-chloro-6-[3-(trifluoromethyl)-1H-pyrazol-4-yl]-3-isoquinolyl]-2-cyano-cyclopropanecarboxamide (200 mg, 0.49 mmol) and 3,4-dihydro-2h-pyran (2.0 mL) in trifluoroacetic acid (0.5 mL) and dichloromethane (15 mL) was heated to reflux for overnight. The reaction was concentrated to dryness and the crude residue was then purified by column chromatography (ethyl acetate/petroleum ether 1/5-1/3) to afford (±)-trans-N-[8-chloro-6-[1-tetrahydropyran-2-yl-3-(trifluoromethyl)pyrazol-4-yl]-3-isoquinolyl]-2-cyano-cyclopropanecarboxamide (230 mg, 95% yield) as a yellow solid. LCMS (ESI): [M+H]⁺=490.1.

Step 3: (±)-trans-N-[8-(benzhydrylideneamino)-6-[1-tetrahydropyran-2-yl-3-(trifluoromethyl)pyrazol-4-yl]-3-isoquinolyl]-2-cyano-cyclopropanecarboxamide

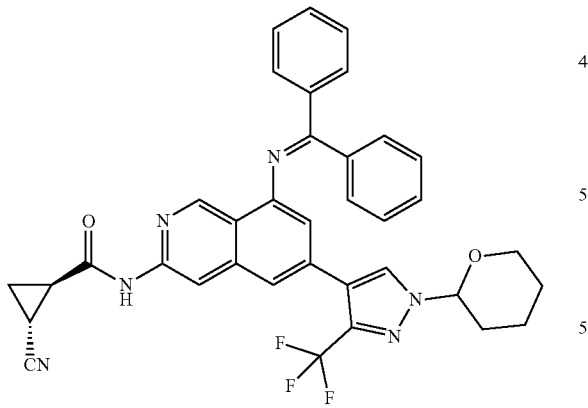

A mixture of (±)-trans-N-[8-chloro-6-[1-tetrahydropyran-2-yl-3-(trifluoromethyl)pyrazol-4-yl]-3-isoquinolyl]-2-cyano-cyclopropanecarboxamide (100 mg, 0.2 mmol), benzophenone imine (182 mg, 1.0 mmol), Xantphos (58 mg, 0.1 mmol), Pd₂(dba)₃ (46.0 mg, 0.05 mmol) and Cs₂CO₃ (170.0 mg, 0.52 mmol) in dry N,N-dimethylformamide (3.0 mL) and dry toluene (3.0 mL) was stirred at 130° C. under inert atmosphere for 4 h. The reaction was concentrated to remove toluene and the residue was taken up in ethyl acetate (15 ml). The organic mixture was washed with 20 mL of brine. The organics were then separated, dried (Na₂SO₄) and concentrated to dryness. The crude product was then purified by column chromatography (ethyl acetate/petroleum ether, 1/3-1/1) to afford (±)-trans-N-[8-(benzhydrylideneamino)-6-[1-tetrahydropyran-2-yl-3-(trifluoromethyl)pyrazol-4-yl]-3-isoquinolyl]-2-cyano-cyclopropanecarboxamide (100 mg, 57% yield) as a yellow liquid. LCMS (ESI): [M+H]⁺=635.2.

Step 4: (±)-trans-N-[8-amino-6-[3-(trifluoromethyl)-1H-pyrazol-4-yl]-3-isoquinolyl]-2-cyano-cyclopropanecarboxamide

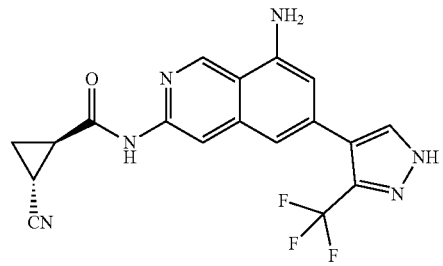 [SMILES: N#C[C@@H]1C[C@H]1C(=O)Nc1cc2cc(-c3c[nH]nc3C(F)(F)F)cc(N)c2cn1]

A solution of (±)-trans-N-[8-(benzhydrylideneamino)-6-[1-tetrahydropyran-2-yl-3-(trifluoromethyl) pyrazol-4-yl]-3-isoquinolyl]-2-cyano-cyclopropanecarboxamide (100 mg, 0.11 mmol) in methyl alcohol (2 mL) and 4M HCl (2 mL, 8 mmol) was stirred at room temperature for 1 h. Excess sodium bicarbonate was added. The mixture was then filtered. The filtrate was concentrated and purified by reverse phase chromatography (methanol 60%/0.1% HCl in water) to afford (±)-trans-N-[8-amino-6-[3-(trifluoromethyl)-1H-pyrazol-4-yl]-3-isoquinolyl]-2-cyano-cyclopropane carboxamide (8 mg, 18.2% yield) as a red solid (HCl salt). LCMS (ESI): [M+H]⁺=387.1, R_T(min)=1.69, Method=B; ¹H NMR (400 MHz, CD₃OD) δ 9.27 (s, 1H), 8.07 (s, 1H), 8.04 (s, 1H), 7.19 (s, 1H), 6.92 (s, 1H), 2.63-2.61 (m, 1H), 2.20-2.15 (m, 1H), 1.65-1.59 (m, 2H).

Example 64

(±)-trans-N-(8-amino-6-(8-methylpyrido[3,2-b]pyrazin-7-yl)isoquinolin-3-yl)-2-cyanocyclopropanecarboxamide (Compound 123)

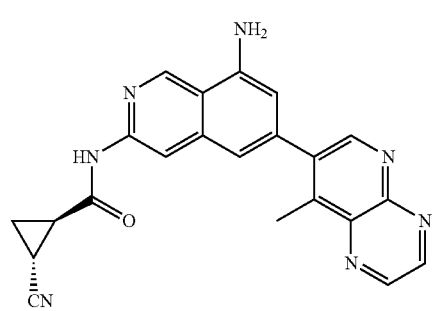

Step 1: (±)-trans-N-(8-chloro-6-(8-methylpyrido[3,2-b]pyrazin-7-yl)isoquinolin-3-yl)-2-cyanocyclopropane Carboxamide

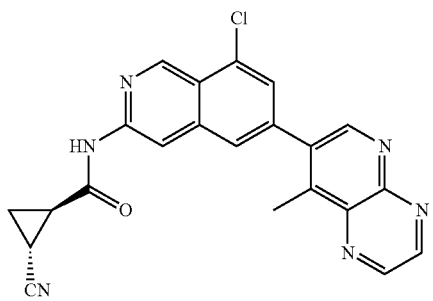 [SMILES: Cc1c(-c2cc(Cl)c3cnc(NC(=O)[C@@H]4C[C@H]4C#N)cc3c2)cnc2nccnc12]

A mixture of (±)-[8-chloro-3-[[(trans)-2-cyanocyclopropanecarbonyl]amino]-6-isoquinolyl]boronic acid (400 mg, 1.27 mmol), 7-bromo-8-methyl-pyrido[2,3-b]pyrazine (285 mg, 1.27 mmol), PdCl$_2$dppf (93 mg, 0.13 mmol), and K$_2$CO$_3$ (525 mg, 3.8 mmol) in 1,4-dioxane (8 mL) and water (2 mL) was heated at 100° C. for 3 h under Ar. The reaction was concentrated to dryness. The residue was purified by silica gel column chromatography (PE:EA=2:1 to PE:EA=1:1) to give the title compound as a yellow solid (300 mg, 38% yield). LCMS (ESI) [M+H]$^+$=415.2.

Step 2: (±)-tert-butyl 3-((trans)-2-cyanocyclopropanecarboxamido)-6-(8-methylpyrido[3,2-b]pyrazin-7-yl)isoquinolin-8-ylcarbamate

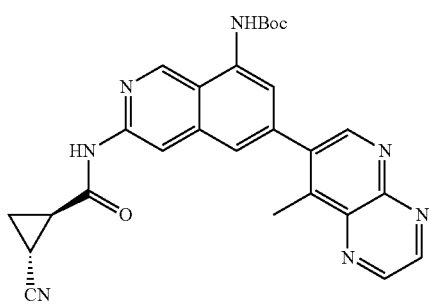 [SMILES: Cc1c(-c2cc(NC(=O)OC(C)(C)C)c3cnc(NC(=O)[C@@H]4C[C@H]4C#N)cc3c2)cnc2nccnc12]

A mixture of (±)-trans-N-[8-chloro-6-(8-methylpyrido[2,3-b]pyrazin-7-yl)-3-isoquinolyl]-2-cyano-cyclopropanecarboxamide (290 mg, 0.7 mmol), tert-butyl carbamate (245 mg, 2.09 mmol), Pd$_3$(dba)$_2$ (64 mg, 0.07 mmol), Brettphos (38 mg, 0.07 mmol), and Cs$_2$CO$_3$ (684 mg, 2.1 mmol) in 1,4-dioxane (10 mL) was heated at 90° C. for 2 h under Ar gas. The reaction was concentrated to dryness. The residue was purified by silica column chromatography (PE:EA=1:1 to PE:EA=1:2) to give the title compound as a yellow solid (190 mg, 49% yield). LCMS (ESI) [M+H]$^+$=496.3.

Step 3: (±)-trans-N-(8-amino-6-(8-methylpyrido[3,2-b]pyrazin-7-yl)isoquinolin-3-yl)-2-cyanocyclopropane Carboxamide A mixture of (±)-tert-butyl N-[3-[[(trans)-2-cyanocyclopropanecarbonyl]amino]-6-(8-methylpyrido[2,3-b]pyrazin-7-yl)-8-isoquinolyl]carbamate (190 mg, 0.38 mmol) and TFA (1 mL, 0.38 mmol) in dichloromethane (2 mL) was stirred at room temperature under N$_2$ gas. The reaction was concentrated to dryness and the residue was taken up in EtOAc (10 mL) and pH adjusted 7-8 with sat NaHCO$_3$. The organics were then separated, dried (NaSO$_4$) and concentrated to dryness. The residue was purified with silica column chromatography (EA:PE=1:1 to EA:DCM=2:1) to give the title compound as a yellow solid (49.5 mg, 32% yield). LCMS (ESI): RT (min)=1.65, [M+H]$^+$=396.2, Method=B. $^1$H NMR (400 MHz, DMSO-d$_6$) δ 11.15 (s, 1H), 9.40 (s, 1H), 9.17 (d, J=1.6 Hz, 1H), 9.13 (d, J=1.6 Hz, 1H), 9.06 (s, 1H), 8.29 (s, 1H), 7.08 (s, 1H), 6.71 (s, 1H), 6.48 (s, 2H), 2.79-2.75 (m, 3H), 2.15-2.11 (m, 1H), 1.61-1.59 (m, 1H), 1.44-1.42 (m, 1H).

Example 65

(trans)-N-(8-amino-6-((R)-4-methyl-2-oxooxazolidin-3-yl)isoquinolin-3-yl)-2-cyanocyclopropanecarboxamide (Compound 124)

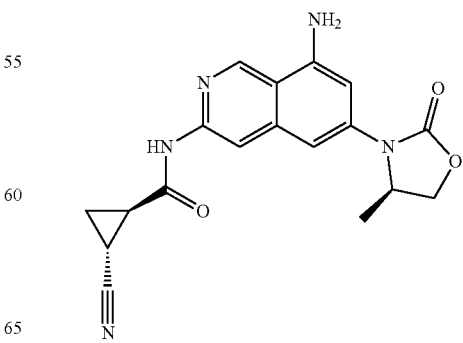

Step 1: (±)-trans-N-(8-chloro-6-((R)-4-methyl-2-oxooxazolidin-3-yl)isoquinolin-3-yl)-2-cyanocyclopropane Carboxamide

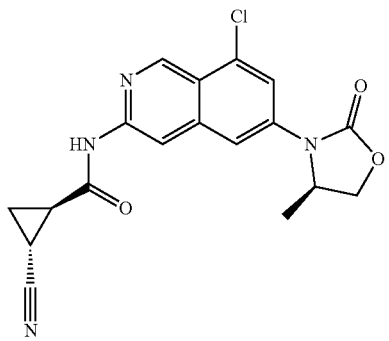 [SMILES: C[C@@H]1COC(=O)N1c1cc(N)c2cnc(NC(=O)[C@@H]3C[C@H]3C#N)cc2c1]

A mixture of trans-N-(6-bromo-8-chloro-3-isoquinolyl)-2-cyano-cyclopropanecarboxamide (400 mg, 1.14 mmol), (4R)-4-methyloxazolidin-2-one (140 mg, 1.38 mmol), Pd$_2$(dba)$_3$ (105 mg, 0.11 mmol), Xantphos (66 mg, 0.11 mmol), and K$_3$PO$_4$ (726 mg, 3.42 mmol) in 1,4-dioxane (5 mL) was heated at 90° C. for 3 h under Ar. The reaction was concentrated to dryness. The residue was purified by silica gel column chromatography (PE:EA=2:1 to PE:EA=1:1) to give the title compound as a yellow solid (350 mg, 83% yield) in the end. LCMS (ESI) [M+H]$^+$=371.1.

Step 2: tert-butyl 3-(trans-2-cyanocyclopropanecarboxamido)-6-((R)-4-methyl-2-oxooxazolidin-3-yl)isoquinolin-8-ylcarbamate

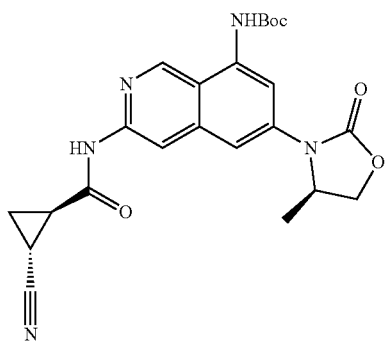 [SMILES: C[C@@H]1COC(=O)N1c1cc(NC(=O)OC(C)(C)C)c2cnc(NC(=O)[C@@H]3C[C@H]3C#N)cc2c1]

A mixture of trans-N-[8-chloro-6-[(4R)-4-methyl-2-oxo-oxazolidin-3-yl]-3-isoquinolyl]-2-cyano-cyclopropanecarboxamide (340 mg, 0.92 mmol), tert-butyl carbamate (500 mg, 4.27 mmol), Pd$_2$(dba)$_3$ (84 mg, 0.09 mmol), Brettphos (50 mg, 0.09 mmol) and Cs$_2$CO$_3$ (897 mg, 2.75 mmol) in 1,4-dioxane (10 mL) was heated at 90° C. for 3 h under Ar. The reaction was concentrated to dryness. The residue was purified with silica gel column chromatography (PE:EA=2:1 to PE:EA=1:1) to give the title compound as a yellow solid (240 mg, 58% yield) in the end. LCMS (ESI) [M+H]+=452.2.

Step 3: (trans)-N-(8-amino-6-((R)-4-methyl-2-oxooxazolidin-3-yl)isoquinolin-3-yl)-2-cyanocyclopropanecarboxamide

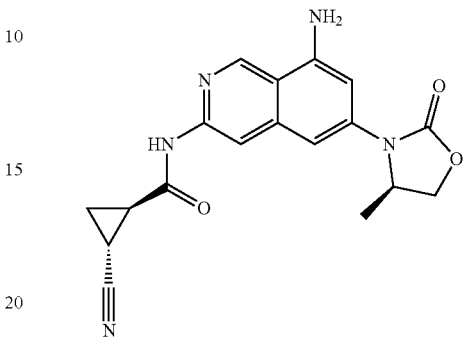

A mixture of tert-butyl N-[3-[[(trans)-2-cyanocyclopropanecarbonyl]amino]-6-[(4R)-4-methyl-2-oxo-oxazolidin-3-yl]-8-isoquinolyl]carbamate (240 mg, 0.53 mmol) and TFA (1 mL, 0.53 mmol) in dichloromethane (4 mL) was stirred for 2 h at room temperature under Ar gas. The reaction was concentrated to dryness and the residue was taken up in EtOAc (10 ml) and adjusted pH to 7-8 with sat NaHCO$_3$. The organics were then separated, dried (Na$_2$SO$_4$) and concentrated to dryness. The residue was purified by silica gel column chromatography (EA:PE=1:1 to EA:DCM=2:1) to give the title product as a yellow solid. LCMS (ESI): RT (min)=1.56, [M+H]+=352.2, Method=B. $^1$H NMR (400 MHz, DMSO-d$_6$) δ 11.04 (s, 1H), 9.21 (s, 1H), 8.15 (s, 1H), 7.00 (d, J=1.6 Hz, 1H), 6.94 (d, J=1.6 Hz, 1H), 6.35 (s, 2H), 4.70-4.67 (m, 1H), 4.57-4.53 (m, 1H), 4.06-4.03 (m, 1H), 2.75-2.73 (m, 1H), 2.14-2.10 (m, 1H), 1.60-1.58 (m, 1H), 1.42-1.38 (m, 1H), 1.28 (d, J=6.0 Hz, 3H).

Example 66

(1S,2S)—N-(8-amino-6-(2-methyl-5-oxopyrrolidin-1-yl)isoquinolin-3-yl)-2-fluorocyclopropanecarboxamide (Compound 125)

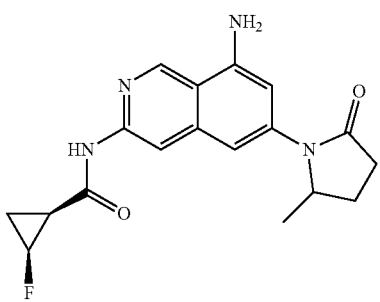 [SMILES: CC1CCC(=O)N1c1cc(N)c2cnc(NC(=O)[C@@H]3C[C@@H]3F)cc2c1]

Step 1: (1S,2S)—N-(8-chloro-6-(2-methyl-5-oxopyrrolidin-1-yl)isoquinolin-3-yl)-2-fluorocyclopropanecarboxamide

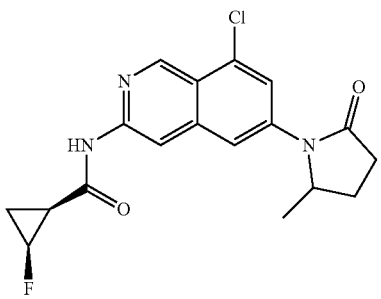 [SMILES: CC1CCC(=O)N1c1cc(Cl)c2cnc(NC(=O)[C@@H]3C[C@@H]3F)cc2c1]

A mixture of 5-methyl-2-pyrrolidinone (87 mg, 0.88 mmol), (1S,2S)—N-(6-bromo-8-chloro-3-isoquinolyl)-2-fluoro-cyclopropanecarboxamide (250 mg, 0.73 mmol), Xantphos (43 mg, 0.07 mmol), Pd₂(dba)₃ (67 mg, 0.07 mmol), and K₃PO₄ (462 mg, 2.18 mmol) in 1,4-dioxane (10 mL) was heated at 90° C. for 3 h under Ar. The reaction was concentrated to dryness. The residue was purified by silica gel column chromatography (EA:PE=1:1 to EA:DCM=2:1) to give the title compound as a yellow solid (200 mg, 76% yield). LCMS (ESI) [M+H]⁺=362.1.

Step 2: tert-butyl 3-((1S,2S)-2-fluorocyclopropanecarboxamido)-6-(2-methyl-5-oxopyrrolidin-1-yl) isoquinolin-8-ylcarbamate

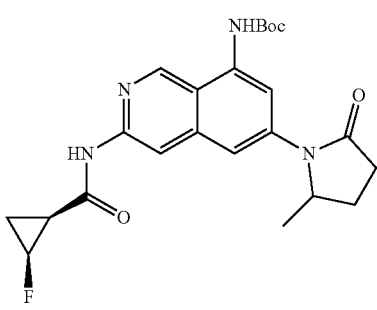 [SMILES: CC1CCC(=O)N1c1cc(NC(=O)OC(C)(C)C)c2cnc(NC(=O)[C@@H]3C[C@@H]3F)cc2c1]

A mixture of (1S,2S)—N-[8-chloro-6-(2-methyl-5-oxo-pyrrolidin-1-yl)-3-isoquinolyl]-2-fluoro-cyclopropanecarboxamide (170 mg, 0.47 mmol), tert-butyl carbamate (550 mg, 4.69 mmol), Brettphos (53 mg, 0.1 mmol), Pd₂(dba)₃ (86 mg, 0.09 mmol) and Cs₂CO₃ (460 mg, 1.41 mmol) in 1,4-dioxane (10 mL) was heated at 90° C. for 3 h under Ar. The reaction was concentrated to dryness. The residue was purified with silica gel column chromatography (PE:EA=1:1 to PE:EA=1:2) to give the title compound as is yellow solid (140 mg, 59% yield). LCMS (ESI) [M+H]+=443.2

Step 3: (1S,2S)—N-(8-amino-6-(2-methyl-5-oxopyrrolidin-1-yl)isoquinolin-3-yl)-2-fluorocyclopropanecarboxamide

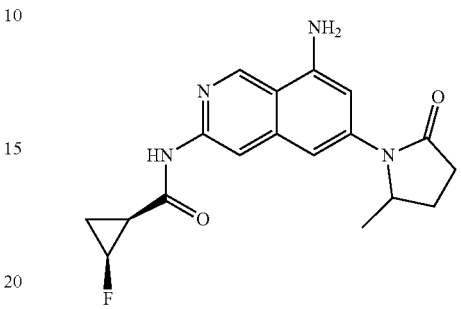

A mixture of tert-butyl N-[3-[[(1S,2S)-2-fluorocyclopropanecarbonyl]amino]-6-(2-methyl-5-oxo-pyrrolidin-1-yl)-8-isoquinolyl]carbamate (140 mg, 0.32 mmol) and TFA (0.5 mL, 0.32 mmol) in dichloromethane (2 mL) was stirred at room temperature for 1 h. The reaction was concentrated to dryness. The residue was taken up in EtOAc (10 mL) and the pH adjusted to 7-8 with sat NaHCO₃. The solution was concentrated and purified by silica gel chromatography (PE:EA=1:1 to EA) to give the title compound as a yellow solid (78.2 mg, 72% yield). LCMS (ESI): RT (min)=1.52, [M+H]+=343.1, Method=B. ¹HNMR (400 MHz, CD₃OD) δ 9.14 (s, 1H), 8.11 (s, 1H), 7.09 (s, 1H), 6.92 (s, 1H), 4.98 (d, J=3.6 Hz, 0.5H), 4.82-4.81 (m, 0.5H), 4.51 (d, J=6.4 Hz, 1H), 2.72-2.61 (m, 1H), 2.59-2.53 (m, 1H), 2.48-2.41 (m, 1H), 2.16-2.14 (m, 1H), 1.88-1.78 (m, 2H), 1.28-1.21 (m, 4H).

Example 67

(±)-trans-N-(8-amino-7-fluoro-6-((R)-4-methyl-2-oxooxazolidin-3-yl)isoquinolin-3-yl)-2-cyanocyclopropanecarboxamide (Compound 126)

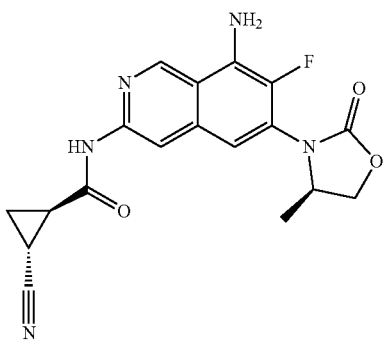 [SMILES: C[C@@H]1COC(=O)N1c1cc2cc(NC(=O)[C@@H]3C[C@H]3C#N)ncc2c(N)c1F]

Step 1: trans-N-(8-chloro-7-fluoro-6-((R)-4-methyl-2-oxooxazolidin-3-yl)isoquinolin-3-yl)-2-cyanocyclopropanecarboxamide

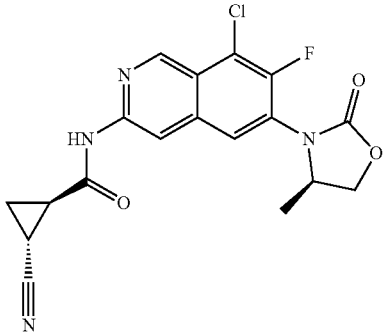 [SMILES: C[C@@H]1COC(=O)N1c1cc2cc(NC(=O)[C@@H]3C[C@H]3C#N)ncc2c(Cl)c1F]

A mixture of trans-N-(8-chloro-7-fluoro-6-iodo-3-isoquinolyl)-2-cyano-cyclopropanecarboxamide (330 mg, 0.79 mmol), (4R)-4-methyloxazolidin-2-one (160 mg, 1.58 mmol), CuI (151 mg, 0.79 mmol) and N1,N2-dimethylethane-1,2-diamine (71 mg, 0.81 mmol) in 1,4-dioxane (15 mL) was heated at 90° C. for 3 h under Ar. The reaction was concentrated to dryness and purified by silica gel column chromatography (PE:EA=2:1 to PE:EA=2:1) to give the title compound as a white solid (290 mg, 77% yield). LCMS (ESI) [M+H]+=345.0.

Step 2: tert-butyl 3-((trans)-2-cyanocyclopropanecarboxamido)-7-fluoro-6-((R)-4-methyl-2-oxooxazolidin-3-yl)isoquinolin-8-ylcarbamate

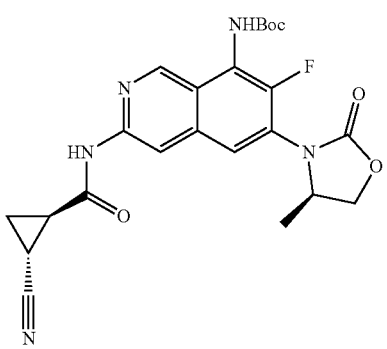 [SMILES: C[C@@H]1COC(=O)N1c1cc2cc(NC(=O)[C@@H]3C[C@H]3C#N)ncc2c(NC(=O)OC(C)(C)C)c1F]

A mixture of tert-butyl carbamate (693 mg, 5.92 mmol), trans-N-[8-chloro-7-fluoro-6-[(4R)-4-methyl-2-oxo-oxazolidin-3-yl]-3-isoquinolyl]-2-cyano-cyclopropanecarboxamide (230 mg, 0.59 mmol), Pd$_2$(dba)$_3$ (270 mg, 0.3 mmol), Brettphos (158 mg, 0.29 mmol) and Cs$_2$CO$_3$ (576 mg, 1.77 mmol) in 1,4-dioxane (8 mL) was heated at 90° C. for 3 h under Ar. The reaction was concentrated to dryness and purified by silica gel column chromatography (PE:EA=2:1 to PE:EA=1:2) followed by prep-HPLC (eluent: 5%-95% methanol and 0.8 g/L NH$_4$HCO$_3$ in water) to give the title compound as a white solid (55 mg, 14% yield). LCMS (ESI) [M+H]+=470.2.

Step 3: (trans)-N-(8-amino-7-fluoro-6-((R)-4-methyl-2-oxooxazolidin-3-yl)isoquinolin-3-yl)-2-cyanocyclopropanecarboxamide

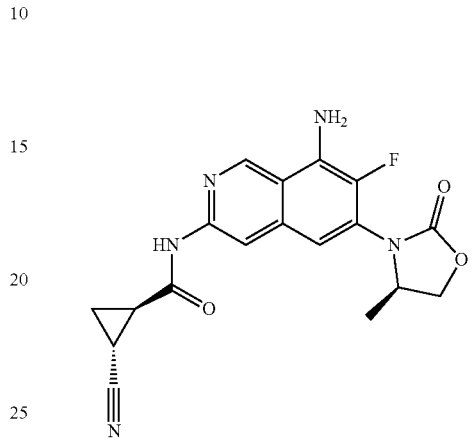

A mixture of tert-butyl N-[3-[[(trans)-2-cyanocyclopropanecarbonyl]amino]-7-fluoro-6-[(4R)-4-methyl-2-oxo-oxazolidin-3-yl]-8-isoquinolyl]carbamate (55 mg, 0.12 mmol) and TFA (0.5 mL, 0.12 mmol) in dichloromethane (2 mL) was stirred at room temperature for 1 h. The reaction mixture was purified with prep-HPLC (5-95% methanol and 0.8 g/L NH$_4$HCO$_3$ in water) to give the title compound (30.6 mg, 13.7% yield). LCMS (ESI): RT (min)=1.65, [M+H]+=370.2, Method=B. $^1$HNMR (400 MHz, DMSO-d$_6$) δ 11.14 (s, 1H), 9.39 (s, 1H), 8.22 (s, 1H), 7.05 (d, J=6.4 Hz, 1H), 6.37 (s, 2H), 4.67 (t, J=8.4 Hz, 1H), 4.54-4.52 (m, 1H), 4.06 (t, J=8.0 Hz, 1H), 2.77-2.76 (m, 1H), 2.14-2.12 (m, 1H), 1.60-1.56 (m, 1H), 1.44-1.42 (m, 1H), 1.15 (d, J=6.0 Hz, 3H).

Example 68

(±)-trans-N-(8-amino-6-((S)-4-methyl-2-oxooxazolidin-3-yl)isoquinolin-3-yl)-2-cyanocyclopropanecarboxamide (Compound 127)

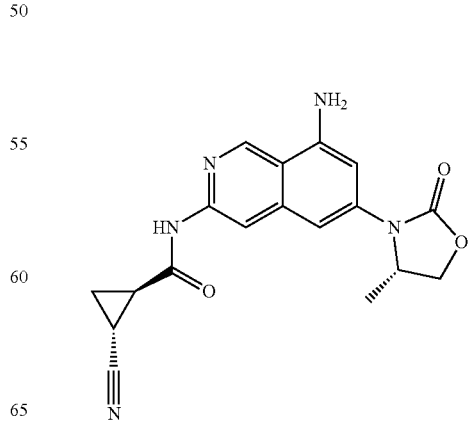

Step 1: trans-N-(8-chloro-6-((S)-4-methyl-2-oxooxazolidin-3-yl)isoquinolin-3-yl)-2-cyanocyclopropanecarboxamide

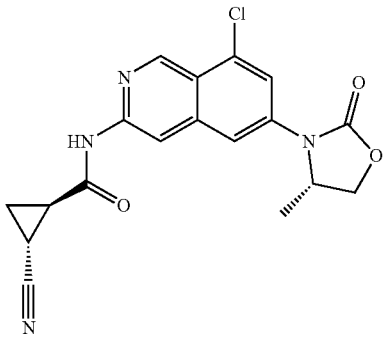 [SMILES: C[C@H]1COC(=O)N1c1cc(Cl)c2cnc(NC(=O)[C@@H]3C[C@H]3C#N)cc2c1]

A mixture of trans-N-(6-bromo-8-chloro-3-isoquinolyl)-2-cyano-cyclopropanecarboxamide (250 mg, 0.71 mmol), (4S)-4-methyloxazolidin-2-one (86 mg, 0.85 mmol), $K_3PO_4$ (453 mg, 2.14 mmol), Xanphos (42 mg, 0.07 mmol), and $Pd_2(dba)_3$ (66 mg, 0.07 mmol) in 1,4-dioxane (10 mL) was heated at 90° C. for 3 h under Ar. The reaction was concentrated to dryness and purified by silica gel column chromatography (PE:EA=4:1 to PE:EA=1:1) to give the title compound as a yellow solid (180 mg, 37% yield). LCMS (ESI) [M+H]+=371.1.

Step 2: tert-butyl 3-((trans)-2-cyanocyclopropanecarboxamido)-6-((S)-4-methyl-2-oxooxazolidin-3-yl)isoquinolin-8-ylcarbamate

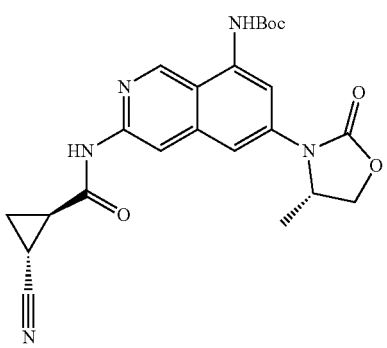 [SMILES: C[C@H]1COC(=O)N1c1cc(NC(=O)OC(C)(C)C)c2cnc(NC(=O)[C@@H]3C[C@H]3C#N)cc2c1]

A mixture of (trans)-N-[8-chloro-6-[(4S)-4-methyl-2-oxo-oxazolidin-3-yl]-3-isoquinolyl]-2-cyano-cyclopropane carboxamide (330 mg, 0.89 mmol), tert-butyl carbamate (520 mg, 4.44 mmol), Brettphos (96 mg, 0.18 mmol), $Pd_2(dba)_3$ (162 mg, 0.18 mmol), and $Cs_2CO_3$ (870 mg, 2.67 mmol) in 1,4-dioxane (10 mL) was heated at 90° C. for 3 h under Ar gas. The reaction was concentrated to dryness. The residue was purified with silica column chromatography (PE:EA=2:1 to PE:EA=1:1, $R_f$=0.4 at PE/EA 1/1). The product is yellow solid (220 mg, 51% yield) in the end. LCMS (ESI) [M+H]+=452.2

Step 3: trans-N-(8-amino-6-((S)-4-methyl-2-oxooxazolidin-3-yl)isoquinolin-3-yl)-2-cyanocyclopropanecarboxamide

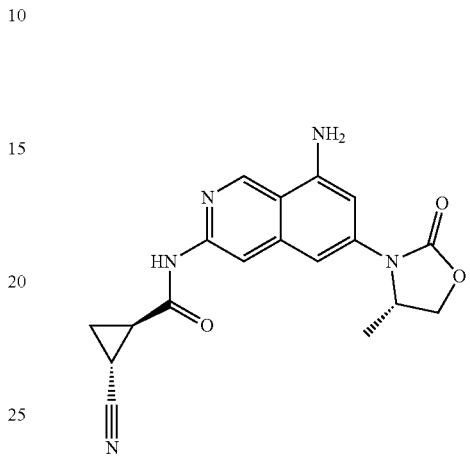

A mixture of tert-butyl N-[3-[[(trans)-2-cyanocyclopropanecarbonyl]amino]-6-[(4S)-4-methyl-2-oxo-oxazolidin-3-yl]-8-isoquinolyl]carbamate (220 mg, 0.49 mmol) and TFA (0.5 mL, 0.49 mmol) in dichloromethane (2 mL) was stirred at room temperature for 1 h. The reaction mixture was purified by prep-HPLC (5%-95% methanol and 0.08 g/L $NH_4HCO_3$ in water) to give the title compound as a yellow solid (64.7 mg, 37.4% yield). LCMS (ESI): RT (min)=1.52, [M+H]+=352.1, Method=B. $^1$HNMR (400 MHz, DMSO-$d_6$) δ 11.03 (s, 1H), 9.20 (s, 1H), 8.15 (s, 1H), 7.00 (d, J=1.6 Hz, 1H), 6.94 (d, J=1.6 Hz, 1H), 6.35 (s, 2H), 4.70-4.67 (m, 1H), 4.57-5.54 (m, 1H), 4.06-4.03 (m, 1H), 2.75-2.72 (m, 1H), 2.14-2.10 (m, 1H), 1.60-1.55 (m, 1H), 1.44-1.40 (m, 1H), 1.28 (d, J=6.4 Hz, 3H).

Example 69

((1S,2S)—N-(8-amino-6-((S)-4-methyl-2-oxooxazolidin-3-yl)isoquinolin-3-yl)-2-fluorocyclopropanecarboxamide (Compound 128)

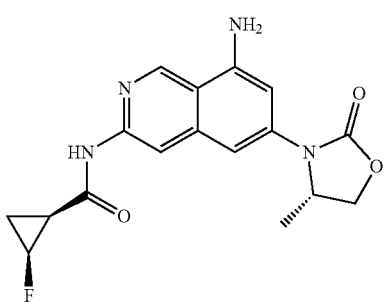

Step 1: (1S,2S)—N-(8-chloro-6-((S)-4-methyl-2-oxooxazolidin-3-yl)isoquinolin-3-yl)-2-fluorocyclopropane Carboxamide Step 3: (1S,2S)—N-(8-amino-6-((S)-4-methyl-2-oxooxazolidin-3-yl)isoquinolin-3-yl)-2-fluorocyclopropanecarboxamide

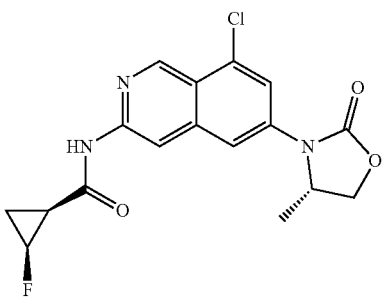 [SMILES: C[C@H]1COC(=O)N1c1cc(Cl)c2cnc(NC(=O)[C@@H]3C[C@@H]3F)cc2c1]

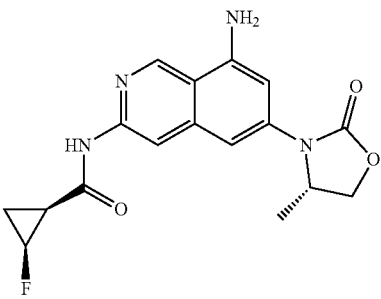

A mixture of (1S,2S)—N-(6-bromo-8-chloro-3-isoquinolyl)-2-fluoro-cyclopropanecarboxamide (200 mg, 0.58 mmol), (4S)-4-methyloxazolidin-2-one (71 mg, 0.7 mmol), Xantphos (34 mg, 0.06 mmol), Pd$_2$(dba)$_3$ (54 mg, 0.06 mmol) and K$_3$PO$_4$ (369 mg, 1.74 mmol) in 1,4-dioxane (8 mL) was heated at 90° C. for 3 h under Ar. The reaction was concentrated to dryness and purified with silica gel column chromatography (PE:EA=4:1 to PE:EA=1:1) to give the title compound as a yellow solid (140 mg, 58% yield). LCMS (ESI) [M+H]$^+$=364.1.

Step 2: tert-butyl 3-((1S,2S)-2-fluorocyclopropanecarboxamido)-6-((S)-4-methyl-2-oxooxazolidin-3-yl)isoquinolin-8-ylcarbamate A mixture of tert-butyl N-[3-[[(1S,2S)-2-fluorocyclopropanecarbonyl]amino]-6-[(4S)-4-methyl-2-oxo-oxazolidin-3-yl]-8-isoquinolyl]carbamate (110 mg, 0.25 mmol) and TFA (0.5 mL, 0.25 mmol) in dichloromethane (2 mL) was stirred at room temperature for 1 h. The reaction was adjusted pH to 7-8 with sat NaHCO$_3$. The mixture was purified with prep-HPLC (5%-95% methanol and 0.8 g/L NH$_4$HCO$_3$ in water) to give the title compound as a brown solid (56.3 mg, 48.2% yield). LCMS (ESI): RT (min)=1.47, [M+H]$^+$=345.1, method=B. $^1$HNMR (400 MHz, DMSO-d$_6$) δ 10.75 (s, 1H), 9.19 (s, 1H), 8.19 (s, 1H), 7.00 (d, J=2.0 Hz, 1H), 6.93 (s, 1H), 6.32 (s, 2H), 5.02-5.00 (m, 0.5H), 4.84-4.83 (m, 0.5H), 4.72-4.67 (m, 1H), 4.58-4.54 (m, 1H), 4.06-4.03 (m, 1H), 2.26-2.23 (m, 1H), 1.69-1.63 (m, 1H), 1.28 (d, J=6.4 Hz, 3H), 1.17-1.13 (m, 1H).

Example 70

(±)-trans-N-(8-amino-6-(4-methylisothiazol-3-yl)isoquinolin-3-yl)-2-cyanocyclopropanecarboxamide (Compound 130)

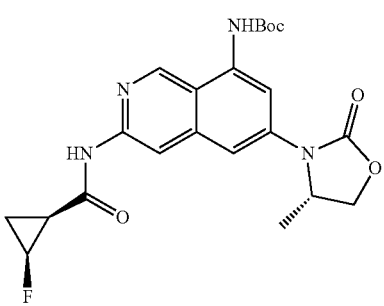 [SMILES: C[C@H]1COC(=O)N1c1cc(NC(=O)OC(C)(C)C)c2cnc(NC(=O)[C@@H]3C[C@@H]3F)cc2c1]

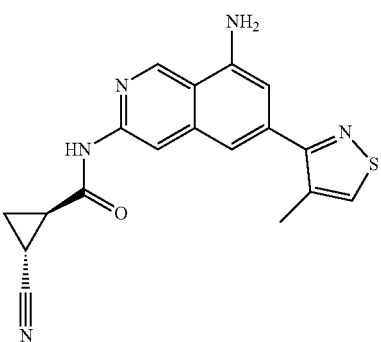 [SMILES: Cc1csnc1-c1cc(N)c2cnc(NC(=O)[C@@H]3C[C@H]3C#N)cc2c1]

A mixture of (1S,2S)—N-[8-chloro-6-[(4S)-4-methyl-2-oxo-oxazolidin-3-yl]-3-isoquinolyl]-2-fluoro-cyclopropane carboxamide (140 mg, 0.38 mmol), tert-butyl carbamate (225 mg, 1.92 mmol), Pd$_2$(dba)$_3$ (70 mg, 0.08 mmol), Brettphos (40 mg, 0.07 mmol) and Cs$_2$CO$_3$ (375 mg, 1.15 mmol) in 1,4-dioxane (4 mL) was heated at 90° C. for 3 h under Ar. The reaction was concentrated to dryness and purified by silica column chromatography (PE:EA=2:1 to PE:EA=1:1) to give the title compound as a white solid (110 mg, 58% yield). LCMS (ESI) [M+H]$^+$=445.2

Step 1: (±)-trans-N-(8-chloro-6-(4-methylisothiazol-3-yl)isoquinolin-3-yl)-2-cyanocyclopropane Carboxamide

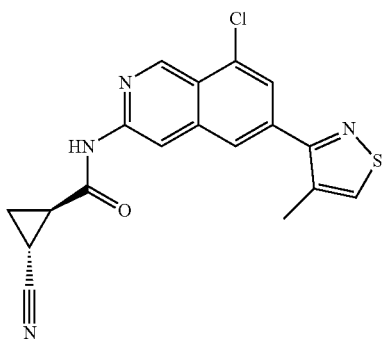 [SMILES: Cc1csnc1-c1cc(Cl)c2cnc(NC(=O)[C@@H]3C[C@H]3C#N)cc2c1]

A mixture of (±)-trans-N-[8-chloro-6-(4,4,5,5-tetramethyl-1,3,2-dioxaborolan-2-yl)-3-isoquinolyl]-2-cyano-cyclopropanecarboxamide (200 mg, 0.5 mmol), 3-bromo-4-methyl-isothiazole (107 mg, 0.6 mmol), Pd(dppf)Cl₂ (73 mg, 0.1 mmol) and K₂CO₃ (138 mg, 1.0 mmol) in 1,4-dioxane (10 mL) and water (1 mL) was stirred at 100° C. under N₂ for 16 h. The mixture was concentrated and purified by flash column chromatography eluting with 0-100% ethyl acetate in PE to give (±)-trans-N-[8-chloro-6-(4-methylisothiazol-3-yl)-3-isoquinolyl]-2-cyano-cyclopropanecarboxamide (100 mg, 54% yield) as a white solid. LCMS (ESI): [M+H]=369.2.

Step 2: (±)-tert-butyl 3-((trans-)-2-cyanocyclopropanecarboxamido)-6-(4-methylisothiazol-3-yl)isoquinolin-8-ylcarbamate

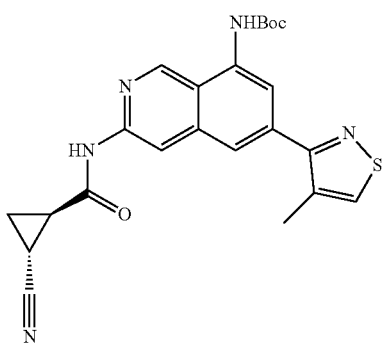 [SMILES: Cc1csnc1-c1cc(NC(=O)OC(C)(C)C)c2cnc(NC(=O)[C@@H]3C[C@H]3C#N)cc2c1]

A mixture of (±)-trans-N-[8-chloro-6-(4-methylisothiazol-3-yl)-3-isoquinolyl]-2-cyano-cyclopropanecarboxamide (80 mg, 0.22 mmol), tert-butyl carbamate (508 mg, 4.34 mmol), Pd₂(dba)₃ (39 mg, 0.04 mmol) and brettphos (46 mg, 0.09 mmol) in 1,4-dioxane (10 mL) was stirred at 90° C. under N₂ for 1 hour. The mixture was concentrated and the residue was purified by flash column chromatography eluting with 0-50% EA in PE to give (±)-tert-butyl N-[3-[[(trans-)-2-cyanocyclopropanecarbonyl]amino]-6-(4-methylisothiazol-3-yl)-8-isoquinolyl]carbamate (60 mg, 62% yield) as a white solid. LCMS (ESI): [M+H]⁺=450.1.

Step 3: (±)-trans-N-(8-amino-6-(4-methylisothiazol-3-yl)isoquinolin-3-yl)-2-cyanocyclopropane Carboxamide

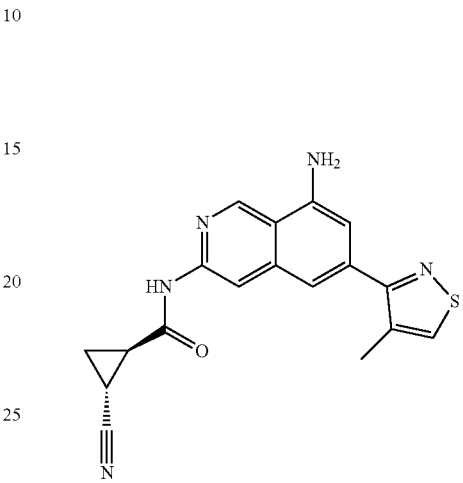

To a solution of (±)-tert-butyl N-[3-[[(trans-)-2-cyanocyclopropanecarbonyl]amino]-6-(4-methylisothiazol-3-yl)-8-isoquinolyl]carbamate (80 mg, 0.18 mmol) in dichloromethane (2 mL) was added TFA (2 mL). The mixture was stirred at 25° C. for 2 hours. The mixture was concentrated and basified with NH₃ in methanol (7M). The mixture was purified by reverse phase chromatography (acetonitrile 0-50/ 0.05% NH₄HCO₃ in water) to afford (±)-(trans-)-N-[8-amino-6-(4-methylisothiazol-3-yl)-3-isoquinolyl]-2-cyano-cyclopropanecarboxamide (36 mg, 58% yield) as alight yellow solid. LCMS (ESI): R_T(min)=1.698, [M+H]⁺=350.1, method=C; ¹H NMR (400 MHz, DMSO-d₆) δ 11.12 (s, 1H), 9.33 (s, 1H), 8.81 (d, J=0.4 Hz, 1H), 8.29 (s, 1H), 7.20 (s, 1H), 6.97 (d, J=1.2 Hz, 1H), 6.37 (s, 2H), 2.78-2.73 (m, 1H), 2.42 (s, 3H), 2.16-2.12 (m, 1H), 1.62-1.57 (m, 1H), 1.46-1.41 (m, 1H).

Example 71

(±)-trans-N-(8-amino-6-((R)-3-hydroxy-2-oxopyrrolidin-1-yl)isoquinolin-3-yl)-2-cyanocyclopropanecarboxamide (Compound 131)

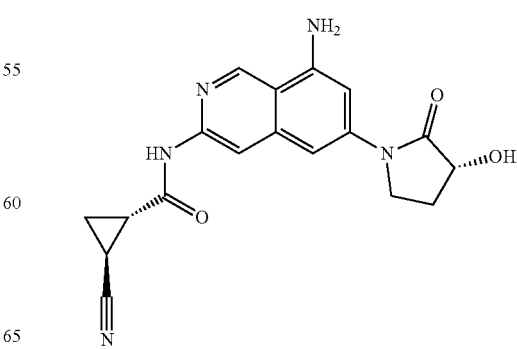

Step 1: trans-N-(8-chloro-6-((R)-3-hydroxy-2-oxopyrrolidin-1-yl)isoquinolin-3-yl)-2-cyanocyclopropanecarboxamide

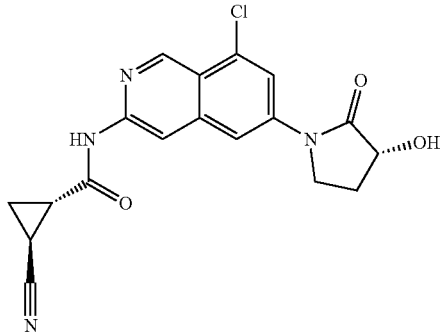 [SMILES: N#C[C@H]1C[C@@H]1C(=O)Nc1cc2cc(N3CC[C@@H](O)C3=O)cc(Cl)c2cn1]

A mixture of (3R)-3-hydroxypyrrolidin-2-one (129 mg, 1.28 mmol), (trans-)-N-(6-bromo-8-chloro-3-isoquinolyl)-2-cyano-cyclopropanecarboxamide (300 mg, 0.86 mmol), Pd$_2$(dba)$_3$ (83 mg, 0.09 mmol), xantphos (98 mg, 0.17 mmol), and Cs$_2$CO$_3$ (556 mg, 1.71 mmol) in 1,4-dioxane (10 mL) was stirred at 100° C. for 2 h. The mixture was concentrated and purified by flash column chromatography eluting with 0-20% MeOH in DCM to give trans-N-[8-chloro-6-[(3R)-3-hydroxy-2-oxo-pyrrolidin-1-yl]-3-isoquinolyl]-2-cyano-cyclopropanecarboxamide (200 mg, 47% yield) as a brown solid. LCMS (ESI): [M+H]$^+$=371.1.

Step 2: trans-N-(8-amino-6-((R)-3-hydroxy-2-oxopyrrolidin-1-yl)isoquinolin-3-yl)-2-cyanocyclopropanecarboxamide

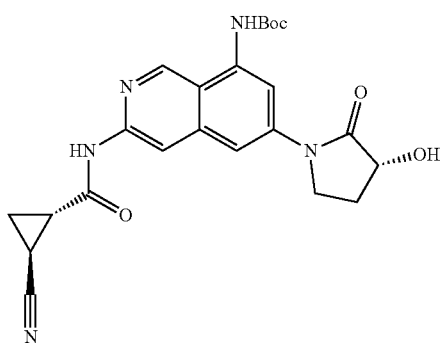 [SMILES: CC(C)(C)OC(=O)Nc1cc(N2CC[C@@H](O)C2=O)cc2cc(NC(=O)[C@H]3C[C@@H]3C#N)ncc12]

A mixture of trans-N-[8-chloro-6-[(3R)-3-hydroxy-2-oxo-pyrrolidin-1-yl]-3-isoquinolyl]-2-cyano-cyclopropanecarboxamide (110 mg, 0.3 mmol), Pd$_2$(dba)$_3$ (28 mg, 0.03 mmol), brettphos (31 mg, 0.06 mmol), t-BuONa (192 mg, 0.59 mmol) and tert-butyl carbamate (695 mg, 5.93 mmol) in 1,4-dioxane (10 mL) was stirred at 90° C. for 2 h. The mixture was concentrated and purified by flash column chromatography eluting with 0-20% MeOH in DCM to give tert-butyl N-[3-[[(trans-)-2-cyanocyclopropanecarbonyl]amino]-6-[(3R)-3-hydroxy-2-oxo-pyrrolidin-1-yl]-8-isoquinolyl]carbamate (62 mg, 28% yield) as a brown solid. LCMS (ESI): [M+H]$^+$=452.0.

Step 3: trans-N-(8-amino-6-((R)-3-hydroxy-2-oxopyrrolidin-1-yl)isoquinolin-3-yl)-2-cyanocyclopropanecarboxamide

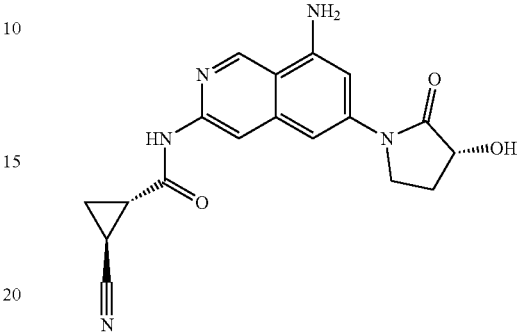

To a solution of tert-butyl N-[3-[[(trans-)-2-cyanocyclopropanecarbonyl]amino]-6-[(3R)-3-hydroxy-2-oxo-pyrrolidin-1-yl]-8-isoquinolyl]carbamate (50 mg, 0.11 mmol) in dichloromethane (3 mL) was added TFA (3 mL) and the mixture was stirred at 25° C. for 2 hours. The mixture was concentrated and basified with NH$_3$ in methanol (7M), concentrated and the resulting residue was purified by reverse phase chromatography (acetonitrile 0-70/0.1% NH$_4$HCO$_3$ in water) to afford trans-N-[8-amino-6-[(3R)-3-hydroxy-2-oxo-pyrrolidin-1-yl]-3-isoquinolyl]-2-cyano-cyclopropanecarboxamide (2 mg, 5.1% yield) as a brown solid. LCMS (ESI): R$_T$ (min)=1.396, [M+H]$^+$=352.1, Method=C; $^1$H NMR (400 MHz, DMSO-d$_6$) δ 11.02 (s, 1H), 9.20 (s, 1H), 8.14 (s, 1H), 7.28 (d, J=1.6 Hz, 1H), 7.05 (d, J=1.6 Hz, 1H), 6.315 (s, 2H), 5.78-5.77 (m, 1H), 4.34-4.28 (m, 1H), 3.82-3.71 (m, 1H), 2.77-2.72 (m, 1H), 2.44-2.33 (m, 1H), 2.15-2.10 (m, 1H), 1.87-1.82 (m, 1H), 1.60-1.56 (m, 1H), 1.44-1.40 (m, 1H).

Example 72

(±)-trans-N-(8-amino-6-((S)-3-hydroxy-2-oxopyrrolidin-1-yl)isoquinolin-3-yl)-2-cyanocyclopropanecarboxamide (Compound 132)

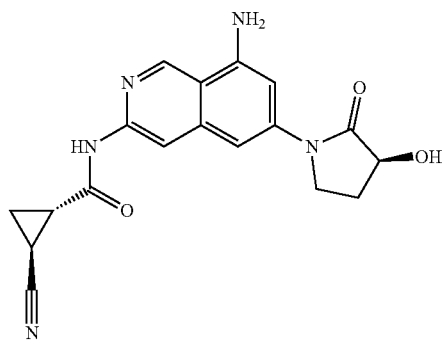 [SMILES: N#C[C@H]1C[C@@H]1C(=O)Nc1cc2cc(N3CC[C@H](O)C3=O)cc(N)c2cn1]

Step 1: trans-N-(8-chloro-6-((S)-3-hydroxy-2-oxopyrrolidin-1-yl)isoquinolin-3-yl)-2-cyanocyclopropanecarboxamide

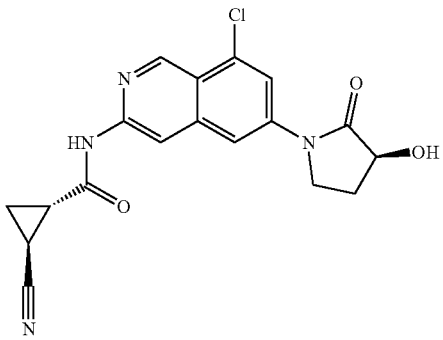 [SMILES: N#C[C@H]1C[C@@H]1C(=O)Nc1cc2cc(N3CC[C@H](O)C3=O)cc(Cl)c2cn1]

A mixture of (3S)-3-hydroxypyrrolidin-2-one (216 mg, 2.14 mmol), trans-N-(6-bromo-8-chloro-3-isoquinolyl)-2-cyano-cyclopropanecarboxamide (500 mg, 1.43 mmol), Pd$_2$(dba)$_3$ (128 mg, 0.14 mmol), xantphos (163 mg, 0.28 mmol), and Cs$_2$CO$_3$ (929 mg, 2.86 mmol) in 1,4-dioxane (15 mL) was stirred at 100° C. for 2 hours. The mixture was concentrated and the residue was purified by flash column chromatography eluting with 0-20% MeOH in DCM to give trans-N-[8-chloro-6-[(3S)-3-hydroxy-2-oxo-pyrrolidin-1-yl]-3-isoquinolyl]-2-cyano-cyclopropanecarboxamide (90 mg, 17% yield) as a brown solid. LCMS (ESI): [M+H]$^+$=371.1

Step 2: trans-N-(8-amino-6-((S)-3-hydroxy-2-oxopyrrolidin-1-yl)isoquinolin-3-yl)-2-cyanocyclopropanecarboxamide

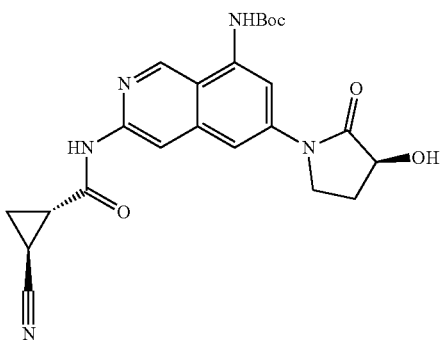 [SMILES: CC(C)(C)OC(=O)Nc1cc(N2CC[C@H](O)C2=O)cc2cc(NC(=O)[C@H]3C[C@@H]3C#N)ncc12]

A mixture of Pd$_2$(dba)$_3$ (23 mg, 0.02 mmol), brettphos (26 mg, 0.05 mmol), t-BuONa (46 mg, 0.49 mmol), tert-butyl carbamate (284 mg, 2.43 mmol), and (trans-)-N-[8-chloro-6-[(3S)-3-hydroxy-2-oxo-pyrrolidin-1-yl]-3-isoquinolyl]-2-cyano-cyclopropanecarboxamide (90 mg, 0.24 mmol) in 1,4-dioxane (8 mL) was stirred at 90° C. for 2 hours. The mixture was concentrated and the residue was purified by flash column chromatography eluting with 0-100% ethyl acetate in PE to give tert-butyl N-[3-[[(trans-)-2-cyanocyclopropanecarbonyl]amino]-6-[(3S)-3-hydroxy-2-oxo-pyrrolidin-1-yl]-8-isoquinolyl]carbamate (52 mg, 47% yield) as a brown solid. LCMS (ESI): [M+H]$^+$=452.0.

Step 3: trans-N-(8-amino-6-((S)-3-hydroxy-2-oxopyrrolidin-1-yl)isoquinolin-3-yl)-2-cyanocyclopropanecarboxamide

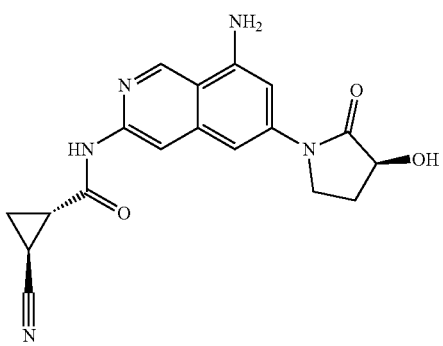 [SMILES: N#C[C@H]1C[C@@H]1C(=O)Nc1cc2cc(N3CC[C@H](O)C3=O)cc(N)c2cn1]

To a solution of tert-butyl N-[3-[[(trans-)-2-cyanocyclopropanecarbonyl]amino]-6-[(3S)-3-hydroxy-2-oxo-pyrrolidin-1-yl]-8-isoquinolyl]carbamate (60 mg, 0.13 mmol) in dichloromethane (3 mL) was added TFA (3 mL) and the mixture was stirred at 25° C. for 2 hours. The mixture was concentrated and basified with NH$_3$ in methanol (7M), concentrated and purified by reverse phase chromatography (acetonitrile 0-70/0.1% NH$_4$HCO$_3$ in water) to afford trans-N-[8-amino-6-[(3S)-3-hydroxy-2-oxo-pyrrolidin-1-yl]-3-isoquinolyl]-2-cyano-cyclopropanecarboxamide (3 mg, 6.4% yield) as a brown solid. LCMS (ESI): R$_T$(min)=1.394, [M+H]$^+$=352.1, method=C; $^1$H NMR (400 MHz, DMSO-d$_6$) δ 11.04 (s, 1H), 9.20 (s, 1H), 8.14 (s, 1H), 7.28 (d, J=1.6 Hz, 1H), 7.05 (d, J=1.6 Hz, 1H), 6.33 (s, 2H), 5.79-5.78 (m, 1H), 4.34-4.28 (m, 1H), 3.79-3.71 (m, 1H), 2.75-2.73 (m, 1H), 2.42-2.39 (m, 1H), 2.13-2.10 (m, 1H), 1.87-1.82 (m, 1H), 1.61-1.56 (m, 1H), 1.44-1.41 (m, 1H).

Example 73

(±)-trans-N-[8-amino-6-(5-isopropyl-1-methyl-pyrazol-4-yl)-3-isoquinolyl]-2-cyano-cyclopropane Carboxamide (Compound 133)

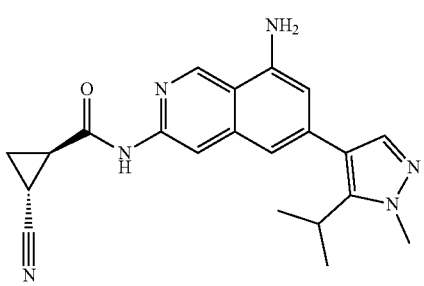 [SMILES: CC(C)c1c(-c2cc(N)c3cnc(NC(=O)[C@@H]4C[C@H]4C#N)cc3c2)cnn1C]

Step 1: 4-bromo-5-isopropyl-1-methyl-pyrazole

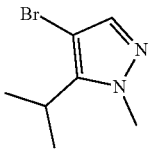

To a solution of 4-bromo-5-isopropyl-1H-pyrazole (950 mg, 5.03 mmol) in DMF (10 mL) was added sodium hydride (300 mg, 7.5 mmol) at 0° C. After 10 min, iodomethane (0.5 mL, 7.4 mmol) was added. The reaction mixture was stirred at 0° C. for 1 h, followed by the addition of 40 ml of saturated brine. The mixture was extracted with ethyl acetate (30 mL×3). The organics were washed with saturated brine (2×20 mL), then separated and dried ($Na_2SO_4$). The organics were concentrated to afford crude 4-bromo-5-isopropyl-1-methyl-pyrazole (900 mg) as a yellow liquid. LCMS (ESI): $[M+H]^+$=203.1.

Step 2: 8-chloro-6-(4,4,5,5-tetramethyl-1,3,2-dioxaborolan-2-yl)isoquinolin-3-amine

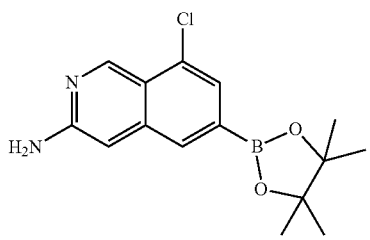 [SMILES: CC1(C)OB(c2cc(Cl)c3cnc(N)cc3c2)OC1(C)C]

A mixture of 6-bromo-8-chloro-isoquinolin-3-amine (517 mg, 2.01 mmol), bis(pinacolato)diboron (600 mg, 2.36 mmol), Pd(dppf)Cl$_2$ (130 mg, 0.18 mmol) and potassium acetate (500 mg, 5.09 mmol) in 1,4-dioxane (10 mL) was stirred under an Ar atmosphere at 90° C. for 2 h. The reaction was concentrated to dryness and purified by column chromatography (ethyl acetate/petroleum ether 1/4 to 1/1) to afford 8-chloro-6-(4,4,5,5-tetramethyl-1,3,2-dioxaborolan-2-yl)isoquinolin-3-amine (600 mg, 89% yield) as a yellow solid. LCMS(ESI):$[M+H]^+$=305.2.

Step 3: 8-chloro-6-(5-isopropyl-1-methyl-pyrazol-4-yl)isoquinolin-3-amine

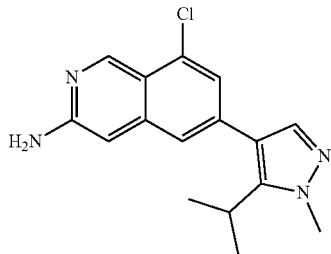 [SMILES: CC(C)c1c(-c2cc(Cl)c3cnc(N)cc3c2)cnn1C]

A mixture of 4-bromo-5-isopropyl-1-methyl-pyrazole (500 mg, 2.46 mmol), (3-amino-8-chloro-6-isoquinolyl) boronic acid (600 mg, 2.7 mmol), Pd(dppf)Cl$_2$ (140 mg, 0.19 mmol) and potassium carbonate (700 mg, 5.07 mmol) was heated to 130° C. in a microwave reactor for 1 h. The reaction was concentrated to dryness and purified by column chromatography (ethyl acetate/petroleum ether1/3-1/2), followed by prep-HPLC to afford 8-chloro-6-(5-isopropyl-1-methyl-pyrazol-4-yl) isoquinolin-3-amine (90 mg, 12% yield) as a yellow solid. LCMS (ESI): $[M+H]^+$4=301.1.

Step 4: (±)-trans-N-[8-chloro-6-(5-isopropyl-1-methyl-pyrazol-4-yl)-3-isoquinolyl]-2-cyano-cyclopropanecarboxamide

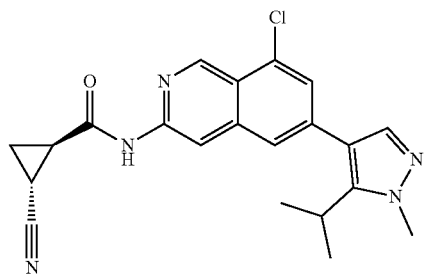

To a mixture of (±)-trans-2-cyanocyclopropanecarboxylic acid (113 mg, 1.02 mmol) and one drop of DMF in dichloromethane (10 mL) was added oxalyl dichloride (0.3 mL, 3.52 mmol). The mixture was stirred at room temperature for 20 min. The mixture was concentrated to remove excess oxalyl dichloride and dichloromethane (5 mL) was then added. The solution was then added dropwise to a mixture of 8-chloro-6-(5-isopropyl-1-methyl-pyrazol-4-yl)isoquinolin-3-amine (85 mg, 0.28 mmol) and pyridine (0.5 mL, 6.18 mmol) in dichloromethane (5 mL). The mixture was stirred at room temperature for 1 h. The reaction was concentrated and purified by column chromatography (ethyl acetate/dichloromethane=1/1) to afford (±)-trans-N-[8-chloro-6-(5-isopropyl-1-methyl-pyrazol-4-yl)-3-isoquinolyl]-2-cyano-cyclopropanecarboxamide (110 mg, 97% yield) as a yellow solid. LCMS(ESI):$[M+H]^+$=394.2.

Step 5: (±)-trans-N-[8-(benzhydrylideneamino)-6-(5-isopropyl-1-methyl-pyrazol-4-yl)-3-isoquinolyl]-2-cyano-cyclopropanecarboxamide

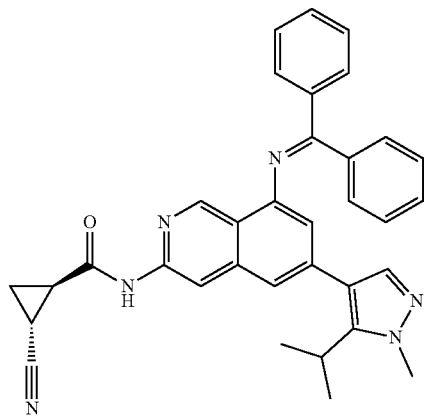 [SMILES: CC(C)c1c(-c2cc(N=C(c3ccccc3)c3ccccc3)c3cnc(NC(=O)[C@@H]4C[C@H]4C#N)cc3c2)cnn1C]

A sealed tube containing (±)-trans-N-[8-chloro-6-(5-isopropyl-1-methyl-pyrazol-4-yl)-3-isoquinolyl]-2-cyano-cyclopropanecarboxamide (110 mg, 0.28 mmol), benzophenone imine (225 mg, 1.24 mmol), Xantphos (70 mg, 0.12 mmol), Pd$_2$(dba)$_3$ (57 mg, 0.06 mmol) and Cs$_2$CO$_3$ (200 mg, 0.62 mmol) in N,N-dimethylformamide (3 mL) and toluene (4 mL) was stirred under an Ar atmosphere at 130° C. for 3 h. The reaction was then quenched by the addition of 40 ml of brine and the mixture extracted with ethyl acetate (30 mL×3). The organics were washed with brine (2×20 mL) and concentrated. The residue was then purified by column chromatography (ethyl acetate/petroleum ether 1/3-1/1) to afford trans-N-[8-(benzhydrylideneamino)-6-(5-isopropyl-1-methyl-pyrazol-4-yl)-3-isoquinolyl]-2-cyano-cyclopropanecarboxamide (64 mg, 27% yield) as a yellow solid. LCMS(ESI):[M+H]$^+$=539.3.

Step 6: (±)-trans-N-[8-amino-6-(5-isopropyl-1-methyl-pyrazol-4-yl)-3-isoquinolyl]-2-cyano-cyclopropanecarboxamide

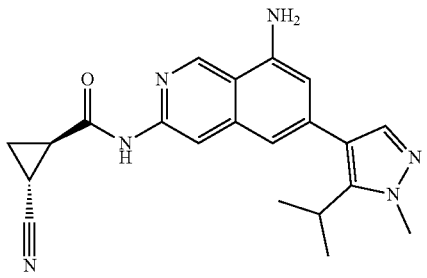 [SMILES: CC(C)c1c(-c2cc(N)c3cnc(NC(=O)[C@@H]4C[C@H]4C#N)cc3c2)cnn1C]

A solution of (±)-trans-N-[8-(benzhydrylideneamino)-6-(5-isopropyl-1-methyl-pyrazol-4-yl)-3-isoquinolyl]-2-cyano-cyclopropanecarboxamide (64 mg, 0.08 mmol) and concentrated aqueous HCl (0.1 mL, 1.2 mmol) in methyl alcohol (5 mL) was stirred at room temperature for 30 min. Triethylamine (0.2 mL, 1.43 mmol) was then added. The reaction mixture was then concentrated and purified by reverse phase chromatography (methanol 0-60/0.1% NH$_4$HCO$_3$ in water) to afford (±)-trans-N-[8-amino-6-(5-isopropyl-1-methyl-pyrazol-4-yl)-3-isoquinolyl]-2-cyano-cyclopropanecarboxamide (18 mg, 63% yield) as a yellow solid. LCMS (ESI): [M+H]$^+$=375.2, R$_T$ (min)=1.72, Method=F; $^1$NMR (400 MHz, CD$_3$OD) δ 9.19 (s, 1H), 8.23 (s, 1H), 7.45 (s, 1H), 6.96 (s, 1H), 6.73 (d, J=1.6 Hz, 1H), 3.95 (s, 3H), 3.47-3.40 (m, 1H), 2.67-2.62 (m, 1H), 2.15-2.10 (m, 1H), 1.62-1.52 (m, 2H), 1.36 (d, J=6.8 Hz, 6H).

Example 74

(±)-trans-N-[8-amino-6-(2-oxo-1,3-benzoxazol-3-yl)-3-isoquinolyl]-2-cyano-cyclopropanecarboxamide (Compound 134)

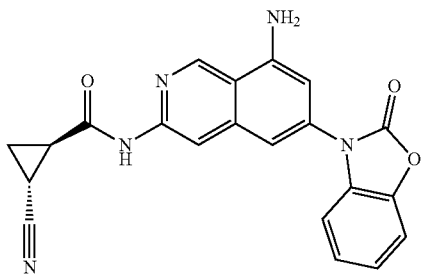 [SMILES: N#C[C@@H]1C[C@H]1C(=O)Nc1cc2cc(-n3c(=O)oc4ccccc43)cc(N)c2cn1]

Step 1: (±)-trans-N-[8-chloro-6-(2-hydroxyanilino)-3-isoquinolyl]-2-cyano-cyclopropanecarboxamide

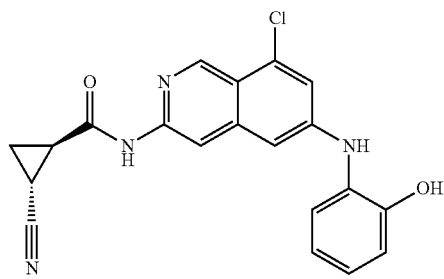 [SMILES: N#C[C@@H]1C[C@H]1C(=O)Nc1cc2cc(Nc3ccccc3O)cc(Cl)c2cn1]

A mixture of (±)-trans-N-(6-bromo-8-chloro-3-isoquinolyl)-2-cyano-cyclopropanecarboxamide (400 mg, 1.14 mmol), 2-aminophenol (150 mg, 1.37 mmol), Pd$_2$(dba)$_3$ (48 mg, 0.05 mmol), Cs$_2$CO$_3$ (650 mg, 2 mmol), and Xantphos (60 mg, 0.1 mmol) in 1,4-dioxane (10 mL) was stirred under inert atmosphere at 100° C. for 2 h. The reaction was concentrated under reduced pressure. The residue was then purified by column chromatography on silica gel eluting with ethyl acetate/petroleum ether 1/5-1/1 to afford trans-N-[8-chloro-6-(2-hydroxyanilino)-3-isoquinolyl]-2-cyano-cyclopropanecarboxamide (420 mg, 78% yield) as yellow solid. LCMS(ESI):[M+H]$^+$=379.1.

Step 2: (±)-trans-N-[8-chloro-6-(2-oxo-1,3-benzoxazol-3-yl)-3-isoquinolyl]-2-cyano-cyclopropanecarboxamide

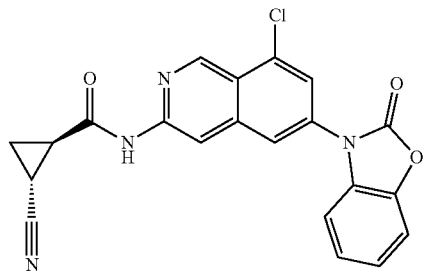

A solution of (±)-trans-N-[8-chloro-6-(2-hydroxyanilino)-3-isoquinolyl]-2-cyano-cyclopropanecarboxamide (400 mg, 1.06 mmol), 1,1'-carbonyldiimidazole (400 mg, 2.47 mmol), triethylamine (2.0 mL, 14.35 mmol) in dichloromethane (20 mL) was stirred at room temperature for 2 h. The reaction was concentrated to dryness and purified by silica gel column chromatography (ethyl acetate/petroleum ether 1/3-1/1) to afford (±)-trans-N-[8-chloro-6-(2-oxo-1,3-benzoxazol-3-yl)-3-isoquinolyl]-2-cyano-cyclopropanecarboxamide (260 mg, 52% yield) as a yellow solid. LCMS (ESI):[M+H]$^+$=405.1.

Step 3: (±)-tert-butyl N-[3-[[(trans)-2-cyanocyclopropanecarbonyl]amino]-6-(2-oxo-1,3-benzoxazol-3-yl)-8-isoquinolyl]carbamate

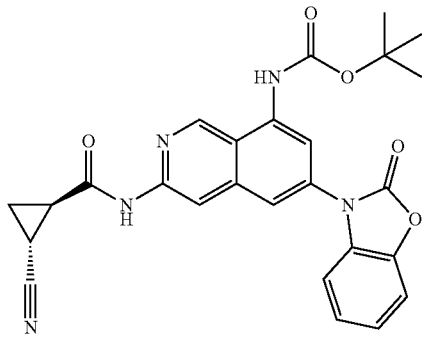 [SMILES: CC(C)(C)OC(=O)Nc1cc(-n2c(=O)oc3ccccc32)cc2cc(NC(=O)[C@@H]3C[C@H]3C#N)ncc12]

A mixture of (±)-trans-N-[8-chloro-6-(2-oxo-1,3-benzoxazol-3-yl)-3-isoquinolyl]-2-cyano-cyclopropanecarboxamide (200 mg, 0.49 mmol), tert-butyl carbamate (600 mg, 5.12 mmol), Brettphos (120 mg, 0.22 mmol), Pd$_2$(dba)$_3$ (100 mg, 0.11 mmol) and Cs$_2$CO$_3$ (325 mg, 1 mmol) in 1,4-dioxane (10 mL) was stirred under an Ar atmosphere at 90° C. for 2 h. The reaction was concentrated to dryness and purified by silica gel column chromatography eluting with ethyl acetate/petroleum ether (1/1) to afford (±)-tert-butyl N-[3-[[(trans)-2-cyanocyclopropane carbonyl]amino]-6-(2-oxo-1,3-benzoxazol-3-yl)-8-isoquinolyl]carbamate (62 mg, 21% yield) as a yellow solid. LCMS(ESI):[M+H]$^+$=486.1.

Step 4: (±)-trans-N-[8-amino-6-(2-oxo-1,3-benzoxazol-3-yl)-3-isoquinolyl]-2-cyano-cyclopropane Carboxamide

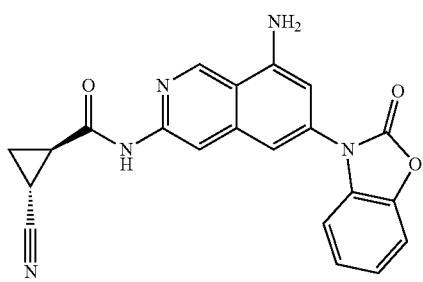 [SMILES: N#C[C@@H]1C[C@H]1C(=O)Nc1cc2cc(-n3c(=O)oc4ccccc43)cc(N)c2cn1]

A solution of (±)-tert-butyl N-[3-[[(trans)-2-cyanocyclopropanecarbonyl]amino]-6-(2-oxo-1,3-benzoxazol-3-yl)-8-isoquinolyl]carbamate (62 mg, 0.13 mmol) in methyl alcohol (2 mL) and HCl (4 M in dioxane, 2 mL, 8 mmol) was stirred at room temperature for 1 h. The reaction was quenched by adding NaHCO$_3$ powder and purified by prep-HPLC to afford (±)-trans-N-[8-amino-6-(2-oxo-1,3-benzoxazol-3-yl)-3-isoquinolyl]-2-cyano-cyclopropane carboxamide (6 mg, 11.8% yield) as a red solid. LCMS(ESI):[M+H]$^+$=386.1, RT (min)=1.83 method=B; 1H NMR (400 MHz, DMSO-d$_6$) δ 11.18 (s, 1H), 9.38 (s, 1H), 8.28 (s, 1H), 7.46 (s, 1H), 7.25-7.22 (m, 3H), 7.16 (s, 1H), 6.82 (d, J=1.2 Hz, 1H), 6.65-6.64 (m, 2H), 2.78-2.76 (m, 1H), 2.17-2.12 (m, 1H), 1.62-1.58 (m, 1H), 1.46-1.41 (m, 1H).

Example 75

1-[8-amino-7-fluoro-6-(4-methyl-3-pyridyl)-3-isoquinolyl]-3-methyl-urea (Compound 135)

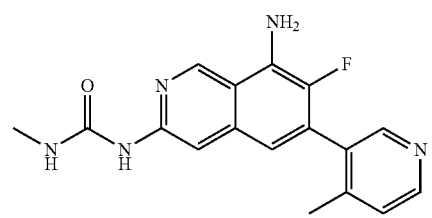 [SMILES: CNC(=O)Nc1cc2cc(-c3cnccc3C)c(F)c(N)c2cn1]

Step 1: 1-(8-chloro-7-fluoro-6-iodo-3-isoquinolyl)-3-methyl-urea

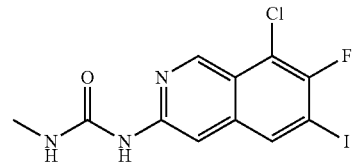 [SMILES: CNC(=O)Nc1cc2cc(I)c(F)c(Cl)c2cn1]

A mixture of 8-chloro-7-fluoro-6-iodo-isoquinolin-3-amine (400 mg, 1.24 mmol) in tetrahydrofuran (5 mL) was added in triethylamine (4 mL, 28.7 mmol) and triphosgene (400 mg, 1.35 mmol). The mixture was stirred at room temperature for 10 min prior to the addition of methanamine hydrochloride (940 mg, 13.92 mmol). The reaction mixture was stirred at room temperature for 1 h. The mixture was concentrated to dryness and purified by column chromatography eluting ethyl acetate/petroleum ether (1/3-1/1) to afford 1-(8-chloro-7-fluoro-6-iodo-3-isoquinolyl)-3-methyl-urea (190 mg, 33% yield) as a yellow solid. LCMS (ESI): [M+H]$^+$=379.9.

Step 2: 1-[8-chloro-7-fluoro-6-(4-methyl-3-pyridyl)-3-isoquinolyl]-3-methyl-urea

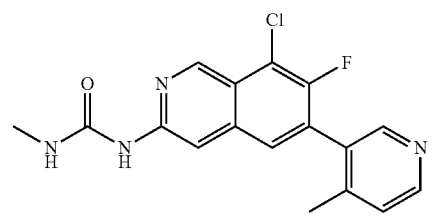 [SMILES: CNC(=O)Nc1cc2cc(-c3cnccc3C)c(F)c(Cl)c2cn1]

A mixture of 1-(8-chloro-7-fluoro-6-iodo-3-isoquinolyl)-3-methyl-urea (190 mg, 0.50 mmol), 4-methyl-3-(4,4,5,5-tetramethyl-1,3,2-dioxaborolan-2-yl)pyridine (120 mg, 0.55 mmol), Pd(dppf)Cl$_2$ (40 mg, 0.05 mmol), and K$_2$CO$_3$ (180 mg, 1.3 mmol) in 1,4-dioxane (6 mL) and water (1 mL) was stirred under an Ar atmosphere at 80° C. for 3 h. The reaction mixture was concentrated to dryness and the crude was then purified by column chromatography eluting methanol/dichloromethane (1:12) to afford 1-[8-chloro-7-fluoro-6-(4- methyl-3-pyridyl)-3-isoquinolyl]-3-methyl-urea (145 mg, 74% yield) as a yellow solid. LCMS(ESI):[M+H]⁺=345.0.

Step 3: tert-butyl N-[7-fluoro-3-(methylcarbamoylamino)-6-(4-methyl-3-pyridyl)-8-isoquinolyl]carbamate

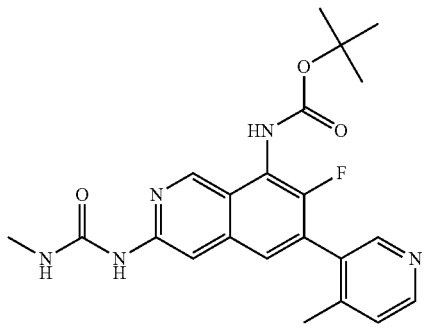 [SMILES: CNC(=O)Nc1cc2cc(-c3cnccc3C)c(F)c(NC(=O)OC(C)(C)C)c2cn1]

A mixture of 1-[8-chloro-7-fluoro-6-(4-methyl-3-pyridyl)-3-isoquinolyl]-3-methyl-urea (120 mg, 0.35 mmol), tert-butyl carbamate (515 mg, 4.4 mmol), Pd$_2$(dba)$_3$ (70 mg, 0.08 mmol), Brettphos (90 mg, 0.17 mmol) and Cs$_2$CO$_3$ (260 mg, 0.80 mmol) in 1,4-dioxane (6 mL) was stirred under an Ar atmosphere at 90° C. for 1 h. The reaction was purified by reverse phase chromatography (methanol 0-50/0.1% ammonia in water) to afford tert-butyl N-[7-fluoro-3-(methylcarbamoylamino)-6-(4-methyl-3-pyridyl)-8-isoquinolyl] carbamate (30 mg, 18% yield) as a yellow solid. LCMS(ESI):[M+H]⁺=426.2.

Step 4: 1-[8-amino-7-fluoro-6-(4-methyl-3-pyridyl)-3-isoquinolyl]-3-methyl-urea

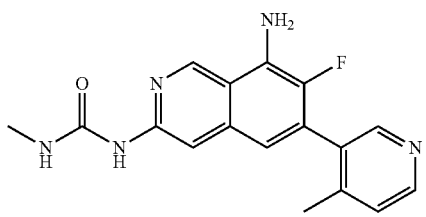

A solution of tert-butyl N-[7-fluoro-3-(methylcarbamoylamino)-6-(4-methyl-3-pyridyl)-8-isoquinolyl] carbamate (30 mg, 0.07 mmol) in a HCl in dioxane solution (4 M, 2 mL, 8 mmol) was stirred at room temperature for 2 h. The solution was concentrated and purified by reverse phase chromatography (methanol 5-50/0.05% ammonia in water) to afford 1-[8-amino-7-fluoro-6-(4-methyl-3-pyridyl)-3-isoquinolyl]-3-methyl-urea (15.4 mg, 67% yield) as a yellow solid. LCMS(ESI):[M+H]⁺=326.1, R$_T$ (min)=1.40, Method=E; ¹H NMR (400 MHz, CD$_3$OD) δ 9.25 (s, 1H), 8.47 (d, J=5.6 Hz, 1H), 8.41 (s, 1H), 7.53 (s, 1H), 7.40 (d, J=5.2 Hz, 1H), 6.91 (d, J=6.0 Hz, 1H), 2.91 (s, 3H), 2.31 (s, 3H).

Example 76

(±)-trans-3-(8-amino-3-(2-cyanocyclopropanecarboxamido)isoquinolin-6-yl)-N,4-dimethylbenzamide (Compound 136)

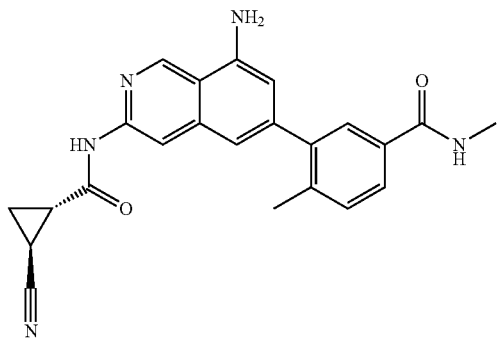 [SMILES: CNC(=O)c1ccc(C)c(-c2cc(N)c3cnc(NC(=O)[C@H]4C[C@@H]4C#N)cc3c2)c1]

Step 1: 3-bromo-N,4-dimethylbenzamide

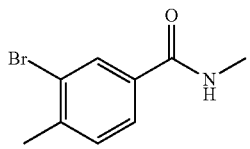

To a vial was added 4-bromo-3-methylbenzoic acid (1 g, 4. mmol), dichloromethane (10 mL), DMF (0.1 mL, 4. mmol) and oxalyl chloride (1.2 mL, 14.18 mmol). The mixture was stirred at rt for 2 h. The mixture was then concentrated in vacuo. The mixture was re-dissolved in dichloromethane (10 mL) and methanamine (30% in EtOH, 10 mL) was added. The mixture was stirred at rt. for 30 min. The mixture was concentrated in vacuo and purified by column chromatography (PE/EA from 1:1 to 0:100) to get 4-bromo-N,3-dimethyl-benzamide (820 mg, 77% yield) as a white solid. LCMS (ESI) [M+H]⁺=228.1.

Step 2: N,4-dimethyl-3-(4,4,5,5-tetramethyl-1,3,2-dioxaborolan-2-yl)benzamide

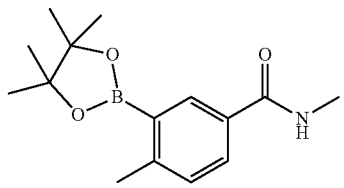

To a sealed tube was added 3-bromo-N,4-dimethyl-benzamide (800 mg, 3.51 mmol), bis(pinacolato)diboron (1.1 g, 4.33 mmol), acetoxypotassium (1.1 g, 11.21 mmol) and Pd(dppf)Cl$_2$ (256 mg, 0.35 mmol) and 1,4-dioxane (100 mL). The mixture was bubbled with N$_2$ for 2 min, and then stirred at 100° C. for 3 h. The mixture was purified directly by silica-gel column chromatography (EA:PE=1:3 to 1:2) to give N,4-dimethyl-3-(4,4,5,5-tetramethyl-1,3,2-dioxaborolan-2-yl)benzamide (800 mg, 41% yield) as a white solid. LCMS (ESI) [M+H]$^+$=276.1.

Step 3: (±)-trans-3-(8-chloro-3-(2-cyanocyclopropanecarboxamido)isoquinolin-6-yl)-N,4-dimethyl-benzamide

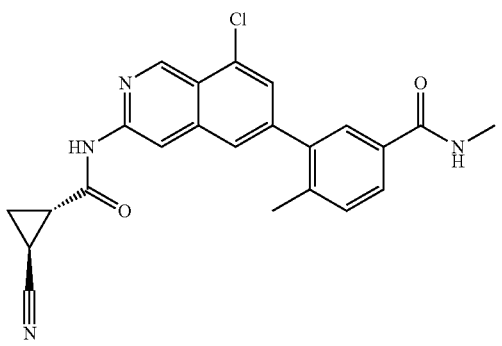 [SMILES: CNC(=O)c1ccc(C)c(-c2cc(Cl)c3cnc(NC(=O)[C@H]4C[C@@H]4C#N)cc3c2)c1]

A solution of (±)-trans-N-(6-bromo-8-chloro-3-isoquinolyl)-2-cyano-cyclopropanecarboxamide (200 mg, 0.57 mmol), N,4-dimethyl-3-(4,4,5,5-tetramethyl-1,3,2-dioxaborolan-2-yl)benzamide (500 mg, 0.91 mmol), Pd(dppf)Cl$_2$ (50 mg, 0.07 mmol), and Na$_2$CO$_3$ (130 mg, 1.24 mmol) in 1,4-dioxane (15 mL) and water (3 mL) was heated at 90° C. for 2 h under Ar. The mixture was purified directly by silica-gel column chromatography (EA:PE=1:2 to 1:1) to give (±)-trans-3-[8-chloro-3-[(2-cyanocyclopropane carbonyl) amino]-6-isoquinolyl]-N,4-dimethyl-benzamide (200 mg, 84% yield) as a white solid. LCMS (ESI) [M+H]$^+$=419.1.

Step 4: (±)-trans-3-(8-amino-3-(2-cyanocyclopropanecarboxamido)isoquinolin-6-yl)-N,4-dimethyl-benzamide

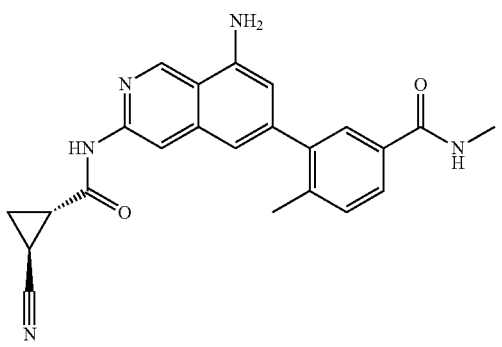 [SMILES: CNC(=O)c1ccc(C)c(-c2cc(N)c3cnc(NC(=O)[C@H]4C[C@@H]4C#N)cc3c2)c1]

A mixture of (±)-trans-3-[8-chloro-3-[(2-cyanocyclopropanecarbonyl)amino]-6-isoquinolyl]-N,4-dimethyl-benzamide (100 mg, 0.24 mmol), tert-butyl carbamate (265 mg, 2.26 mmol), Xantphos (55 mg, 0.10 mmol), Pd$_2$(dba)$_3$ (44 mg, 0.05 mmol) and Cs$_2$CO$_3$ (350 mg, 1.08 mmol) in dry N,N-dimethylformamide (5 mL) and dry toluene (5 mL) was stirred at 130° C. under Ar for 16 h. The reaction was concentrated to remove toluene and then 20 mL saturated brine solution was added. The mixture was extracted with ethyl acetate (20 mL×2). The organics were then separated and dried (Na$_2$SO$_4$). The resulting residue was purified by silica-gel column chromatography (EA:PE=1:1 to EA to DCM:MeOH=20:1) followed by reverse phase chromatography (acetonitrile 0-50/0.1% NH$_4$HCO$_3$ in water) to afford (+)-trans-3-[8-amino-3-[(2-cyanocyclopropanecarbonyl) amino]-6-isoquinolyl]-N,4-dimethyl-benzamide (29 mg, 31% yield) as a yellow solid. LCMS (ESI): R$_T$ (min)=1.67, [M+H]$^+$=400.1, method=C; $^1$H NMR (400 MHz, CD$_3$OD): δ 9.24 (s, 1H), 8.27 (s, 1H), 7.75-7.73 (m, 2H), 7.40-7.38 (m, 1H), 6.97 (s, 1H), 6.71 (s, 1H), 2.92 (s, 3H), 2.67-2.62 (m, 1H), 2.34 (s, 3H), 2.14-2.09 (m, 1H), 1.62-1.52 (m, 2H).

Example 77

(±)-trans-N-(8-amino-6-(3-methyl-2-oxo-2,3-dihydro-1H-benzo[d]imidazol-1-yl)isoquinolin-3-yl)-2-cyanocyclopropanecarboxamide (Compound 138)

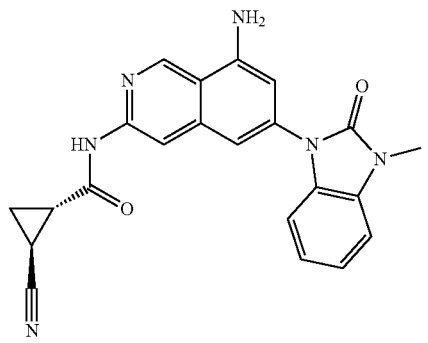 [SMILES: Cn1c(=O)n(-c2cc(N)c3cnc(NC(=O)[C@H]4C[C@@H]4C#N)cc3c2)c2ccccc21]

Step 1: (±)-trans-N-(8-chloro-6-(3-methyl-2-oxo-2,3-dihydro-1H-benzo[d]imidazol-1-yl)isoquinolin-3-yl)-2-cyanocyclopropanecarboxamide

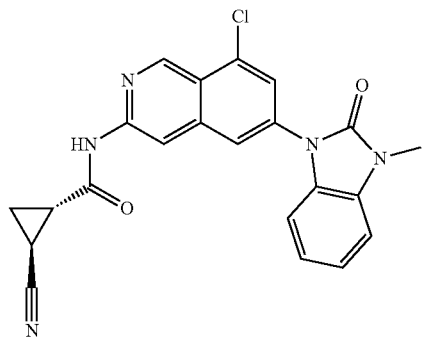

A mixture of (±)-trans-N-(6-bromo-8-chloro-3-isoquinolyl)-2-cyano-cyclopropanecarboxamide (200 mg, 0.57 mmol), 1-methyl-2-benzimidazolinone (120 mg, 0.81 mmol), Pd$_3$(dba)$_2$ (100 mg, 0.11 mmol), Xantphos (130 mg, 0.22 mmol) and K$_3$PO$_4$ (360 mg, 1.7 mmol) in 1,4-dioxane (15 mL) was heated at 90° C. for 3 h under Ar. The mixture was concentrated and purified by silica-gel column chromatography (EA:PE=1:3 to 1:2) to give (±)-trans-N-[8-chloro-6-(3-methyl-2-oxo-benzimidazol-1-yl)-3-isoquinolyl]-2-cyano-cyclopropanecarboxamide (120 mg, 50% yield) as a yellow solid. LCMS (ESI) [M+H]$^+$=418.1.

Step 2: (±)-tert-butyl 3-(trans-2-cyanocyclopropanecarboxamido)-6-(3-methyl-2-oxo-2,3-dihydro-1H-benzo[d]imidazol-1-yl)isoquinolin-8-ylcarbamate

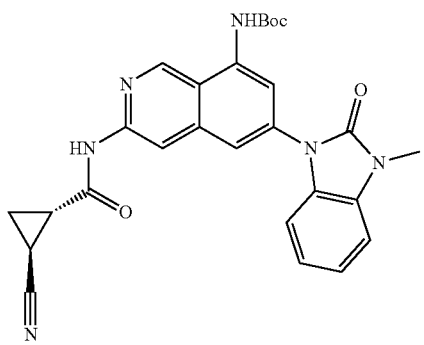 [SMILES: Cn1c(=O)n(-c2cc(NC(=O)OC(C)(C)C)c3cnc(NC(=O)[C@H]4C[C@@H]4C#N)cc3c2)c2ccccc21]

A mixture of (±)-trans-N-[8-chloro-6-(3-methyl-2-oxo-benzimidazol-1-yl)-3-isoquinolyl]-2-cyano-cyclopropanecarboxamide (100 mg, 0.24 mmol), tert-butyl carbamate (280 mg, 2.39 mmol), Pd$_3$(dba)$_2$ (40 mg, 0.04 mmol), Brettphos (20 mg, 0.04 mmol), Cs$_2$CO$_3$ (230 mg, 0.71 mmol) in 1,4-dioxane (1 mL) was heated at 90° C. for 3 h under Ar. The mixture was directly purified by silica gel column chromatography (EA:PE=1:2) to give (±)-tert-butyl N-[3-[(trans-2-cyanocyclopropanecarbonyl)amino]-6-(3-methyl-2-oxo-benzimidazol-1-yl)-8-isoquinolyl]carbamate (70 mg, 59% yield) as a yellow solid. LCMS (ESI) [M+H]$^+$=499.1.

Step 3: (±)-trans-N-(8-amino-6-(3-methyl-2-oxo-2,3-dihydro-1H-benzo[d]imidazol-1-yl)isoquinolin-3-yl)-2-cyanocyclopropanecarboxamide

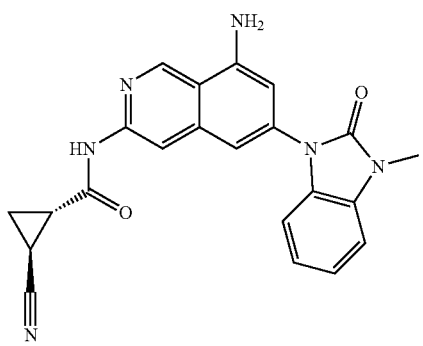 [SMILES: Cn1c(=O)n(-c2cc(N)c3cnc(NC(=O)[C@H]4C[C@@H]4C#N)cc3c2)c2ccccc21]

To the (±)-tert-butyl N-[3-[(trans-2-cyanocyclopropanecarbonyl)amino]-6-(3-methyl-2-oxo-benzimidazol-1-yl)-8-isoquinolyl]carbamate (60 mg, 0.12 mmol) dissolved in dichloromethane (4 mL) was added TFA (0.2 mL, 0.24 mmol) and stirred at room temperature for 2 h. The mixture was directly purified by reverse phase chromatography (acetonitrile 0-50/0.1% NH$_4$HCO$_3$ in water) to afford (±)-trans-N-[8-amino-6-(3-methyl-2-oxo-benzimidazol-1-yl)-3-isoquinolyl]-2-cyano-cyclopropanecarboxamide (13 mg, 27% yield) as a white solid. LCMS (ESI): R$_T$ (min)=1.77, [M+H]$^+$=399.1, method=C; $^1$H NMR (400 MHz, DMSO-d$_6$): δ 11.15 (s, 1H), 9.35 (s, 1H), 8.26 (s, 1H), 7.27-7.08 (m, 5H), 6.78 (s, 1H), 6.54 (s, 2H), 3.17 (s, 3H), 2.77-2.74 (m, 1H), 2.17-2.12 (m, 1H), 1.62-1.57 (m, 1H), 1.46-1.41 (m, 1H).

Example 78

(±)-trans-N-(8-amino-6-(1H-pyrazol-4-yl)isoquinolin-3-yl)-2-cyanocyclopropanecarboxamide (Compound 139)

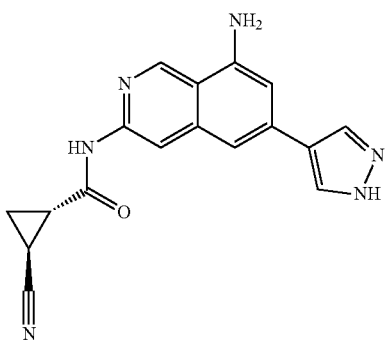 [SMILES: N#C[C@H]1C[C@@H]1C(=O)Nc1cc2cc(-c3cn[nH]c3)cc(N)c2cn1]

Step 1: (±)-trans-N-(8-chloro-6-(1-(tetrahydro-2H-pyran-2-yl)-1H-pyrazol-4-yl)isoquinolin-3-yl)-2-cyanocyclopropanecarboxamide

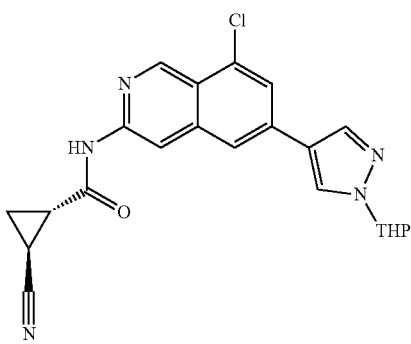

A solution of (±)-trans-N-(6-bromo-8-chloro-3-isoquinolyl)-2-cyano-cyclopropanecarboxamide (200 mg, 0.57 mmol), 1-(tetrahydro-2H-pyran-2-yl)-4-(4,4,5,5-tetramethyl-1,3,2-dioxaborolan-2-yl)-1H-pyrazole (320 mg, 1.15 mmol), Pd(dppf)Cl$_2$ (50 mg, 0.07 mmol) and Na$_2$CO$_3$ (130 mg, 1.24 mmol) in 1,4-dioxane (15 mL) and water (3 mL) was heated at 90° C. for 2 h under Ar. The mixture was directly purified by silica gel column chromatography (EA:PE=1:2) to give (±)-trans-N-[8-chloro-6-(1-tetrahydropyran-2-ylpyrazol-4-yl)-3-isoquinolyl]-2-cyano-cyclopropanecarboxamide (220 mg, 91% yield) as a white solid. LCMS (ESI) [M+H]$^+$=422.7.

Step 2: (±)-trans-N-(8-amino-6-(1-(tetrahydro-2H-pyran-2-yl)-1H-pyrazol-4-yl)isoquinolin-3-yl)-2-cyanocyclopropanecarboxamide

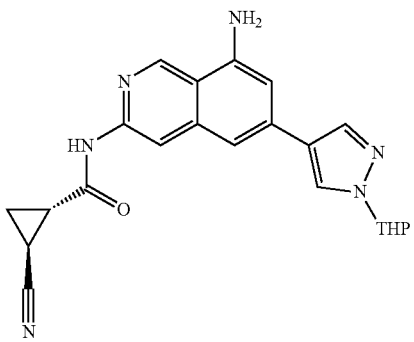

A mixture of (±)-trans-N-[8-chloro-6-(1-tetrahydropyran-2-ylpyrazol-4-yl)-3-isoquinolyl]-2-cyano-cyclopropanecarboxamide (200 mg, 0.47 mmol), tert-butyl carbamate (555 mg, 4.74 mmol), Xantphos (110 mg, 0.19 mmol), Pd$_2$(dba)$_3$ (90 mg, 0.10 mmol) and Cs$_2$CO$_3$ (690 mg, 2.12 mmol) in dry N,N-dimethylformamide (5 mL) and toluene (5 mL) was stirred at 130° C. under Ar atmosphere for 4 h. The reaction was concentrated to remove toluene and then a 10 mL saturated brine solution was added. The mixture was extracted with ethyl acetate (10 mL×2). The organics were then separated and dried (Na$_2$SO$_4$). The resulting residue was purified by silica gel column chromatography (EA: PE=1:1 to 2:1) to give (±)-trans-N-[8-amino-6-(1-tetrahydropyran-2-ylpyrazol-4-yl)-3-isoquinolyl]-2-cyano-cyclopropanecarboxamide (100 mg, 52% yield) as a yellow solid. LCMS (ESI) [M+H]$^+$=403.7.

Step 3: (±)-trans-N-(8-amino-6-(1H-pyrazol-4-yl)isoquinolin-3-yl)-2-cyanocyclopropanecarboxamide

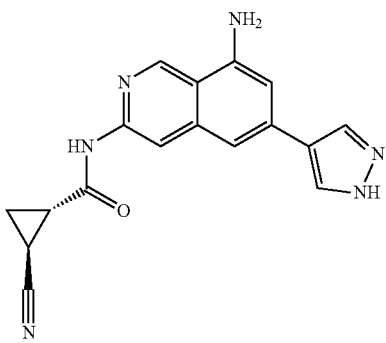 [SMILES: N#C[C@H]1C[C@@H]1C(=O)Nc1cc2cc(-c3cn[nH]c3)cc(N)c2cn1]

The (±)-trans-N-[8-amino-6-(1-tetrahydropyran-2-ylpyrazol-4-yl)-3-isoquinolyl]-2-cyano-cyclopropanecarboxamide (80 mg, 0.20 mmol) was dissolved in dichloromethane (10 mL), and added the TFA (1.5 mL, 0.20 mmol) stirred at room temperature for 2 h. The mixture was evaporated and neutralized by adding a solution of NH$_3$ in MeOH. The resulting mixture was purified by reverse phase chromatography (acetonitrile 0-50/0.1% NH$_4$HCO$_3$ in water) to afford (±)-trans-N-[8-amino-6-(1H-pyrazol-4-yl)-3-isoquinolyl]-2-cyano-cyclopropanecarboxamide (26 mg, 42% yield) as a white solid. LCMS (ESI): R$_T$ (min)=1.47, [M+H]$^+$=319.7, Method=C; $^1$HNMR (400 MHz, DMSO-d$_6$): δ 13.01 (s, 1H), 11.02 (s, 1H), 9.21 (s, 1H), 8.21 (s, 1H), 8.17 (s, 1H), 7.94 (s, 1H), 7.19 (s, 1H), 6.86 (s, 1H), 6.17 (s, 2H), 2.77-2.74 (m, 1H), 2.15-2.11 (m, 1H), 1.61-1.56 (m, 1H), 1.46-1.41 (m, 1H).

Example 79

(±)-trans-N-(8-amino-6-(2-oxo-2,3-dihydro-1H-benzo[d]imidazol-1-yl)isoquinolin-3-yl)-2-cyanocyclopropanecarboxamide (Compound 140)

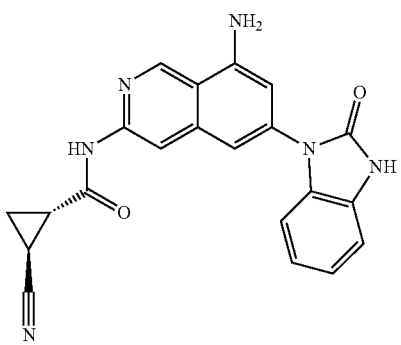 [SMILES: N#C[C@H]1C[C@@H]1C(=O)Nc1cc2cc(-n3c(=O)[nH]c4ccccc43)cc(N)c2cn1]

Step 1: (±)-trans-N-(8-chloro-6-(2-oxo-2,3-dihydro-1H-benzo[d]imidazol-1-yl)isoquinolin-3-yl)-2-cyanocyclopropanecarboxamide

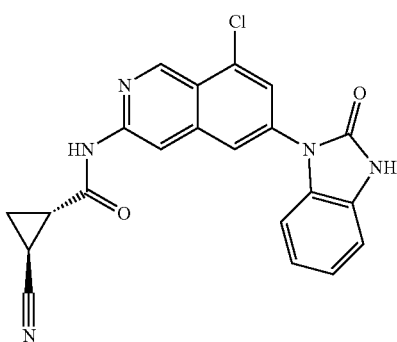 [SMILES: N#C[C@H]1C[C@@H]1C(=O)Nc1cc2cc(-n3c(=O)[nH]c4ccccc43)cc(Cl)c2cn1]

A mixture of (±)-trans-N-(6-bromo-8-chloro-3-isoquinolyl)-2-cyano-cyclopropanecarboxamide (200 mg, 0.57 mmol), 2-hydroxybenzimidazole (110 mg, 0.82 mmol), Pd$_2$(dba)$_3$ (100 mg, 0.11 mmol), Xanphos (130 mg, 0.22 mmol), K$_3$PO$_4$ (360 mg, 1.70 mmol) in 1,4-dioxane (15 mL) was heated at 90° C. for 3 h under Ar gas. The mixture was directly purified by silica gel column chromatography (EA: PE=1:1) to give (±)-trans-N-[8-chloro-6-(2-oxo-3H-benzimidazol-1-yl)-3-isoquinolyl]-2-cyano-cyclopropanecarboxamide (180 mg, 78% yield) as a yellow solid. LCMS (ESI) [M+H]$^+$=404.1.

Step 2: (±)-tert-butyl 3-(trans-2-cyanocyclopropanecarboxamido)-6-(2-oxo-2,3-dihydro-1H-benzo[d]imidazol-1-yl)isoquinolin-8-ylcarbamate

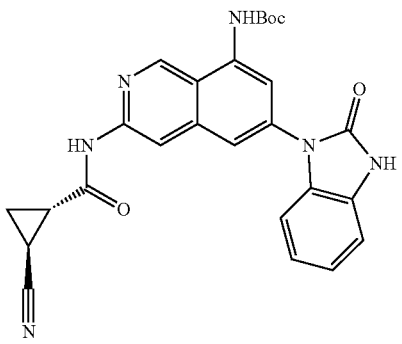 [SMILES: CC(C)(C)OC(=O)Nc1cc(-n2c(=O)[nH]c3ccccc32)cc2cc(NC(=O)[C@H]3C[C@@H]3C#N)ncc12]

A mixture of (±)-trans-N-[8-chloro-6-(2-oxo-3H-benzimidazol-1-yl)-3-isoquinolyl]-2-cyano-cyclopropanecarboxamide (160 mg, 0.40 mmol), tert-butyl carbamate (696 mg, 5.94 mmol), Pd$_2$(dba)$_3$ (72 mg, 0.08 mmol), Brettphos (40 mg, 0.07 mmol) and Cs$_2$CO$_3$ (387 mg, 1.19 mmol) in 1,4-dioxane (10 mL) was heated at 90° C. for 3 h under Ar. The reaction was concentrated to dryness. The residue was purified with silica chromatography (PE:EA=2:1 to PE:EA=1:1) to give (±)-tert-butyl N-[3-[(trans-2-cyanocyclopropanecarbonyl)amino]-6-(2-oxo-3H-benzimidazol-1-yl)-8-isoquinolyl]carbamate (60 mg, 31% yield) as a white solid. LCMS (ESI) [M+H]$^+$=485.1.

Step 3: (±)-trans-N-(8-amino-6-(2-oxo-2,3-dihydro-1H-benzo[d]imidazol-1-yl)isoquinolin-3-yl)-2-cyanocyclopropanecarboxamide

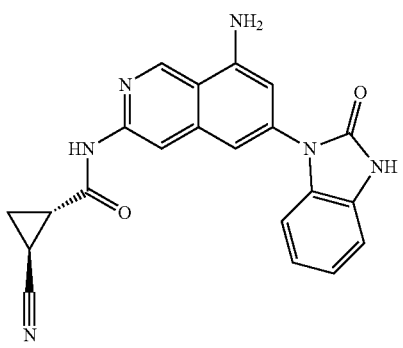 [SMILES: N#C[C@H]1C[C@@H]1C(=O)Nc1cc2cc(-n3c(=O)[nH]c4ccccc43)cc(N)c2cn1]

To a solution of (±)-tert-Butyl N-[3-[(trans-2-cyanocyclopropanecarbonyl)amino]-6-(2-oxo-3H-benzimidazol-1-yl)-8-isoquinolyl]carbamate (55 mg, 0.11 mmol) dissolved in dichloromethane (2 mL) was added TFA (1.0 mL, 0.11 mmol). The reaction was stirred at room temperature for 2 h. The mixture was directly purified by silica gel column chromatography (EA:PE=1:1 to EA), followed by reverse phase chromatography (acetonitrile 0-50/0.1% NH$_4$HCO$_3$ in water) to afford (±)-trans-N-[8-amino-6-(2-oxo-3H-benzimidazol-1-yl)-3-isoquinolyl]-2-cyano-cyclopropanecarboxamide (2.6 mg, 6% yield) as a white solid. LCMS (ESI): R$_T$ (min)=1.64, [M+H]$^+$=385.1, method=C; $^1$HNMR (400 MHz, DMSO-d$_6$): δ 11.13 (s, 1H), 9.34 (s, 1H), 8.25 (s, 1H), 7.15-7.00 (m, 6H), 6.79 (s, 1H), 6.51 (s, 2H), 2.78-2.74 (m, 1H), 2.17-2.12 (m, 1H), 1.61-1.57 (m, 1H), 1.46-1.41 (m, 1H).

Example 80

(±)-trans-N-(8-amino-6-(4-methylpyridin-3-yl)-7-(trifluoromethyl)isoquinolin-3-yl)-2-cyanocyclopropanecarboxamide (Compound 143)

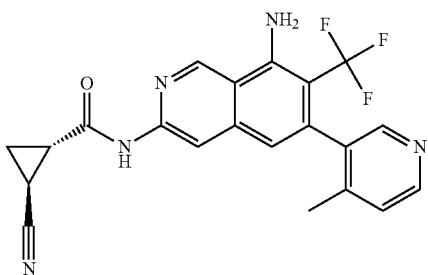 [SMILES: Cc1ccncc1-c1cc2cc(NC(=O)[C@H]3C[C@@H]3C#N)ncc2c(N)c1C(F)(F)F]

Step 1: (±)-trans-N-(8-chloro-7-iodo-6-(4-methylpyridin-3-yl)isoquinolin-3-yl)-2-cyanocyclopropane Carboxamide

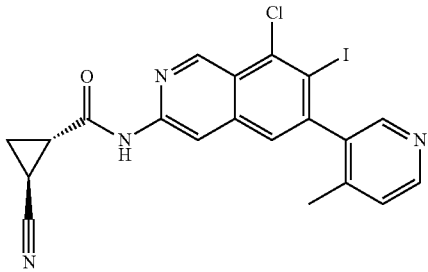 [SMILES: Cc1ccncc1-c1cc2cc(NC(=O)[C@H]3C[C@@H]3C#N)ncc2c(Cl)c1I]

A solution of (±)-trans-N-[7-bromo-8-chloro-6-(4-methyl-3-pyridyl)-3-isoquinolyl]-2-cyano-cyclopropanecarboxamide (500 mg, 1.13 mmol), iodosodium (750 mg, 5 mmol), CuI (50 mg, 0.26 mmol) and dimethylethane-1,2-diamine (1.5 mL, 13.69 mmol) in 1,4-dioxane (20 mL) was heated to 110° C. for 2 days. The mixture was diluted with ethyl acetate (100 mL), washed with water (30 mL×3) and brine (30 mL). The organic layer was dried over sodium sulfate, filtered and concentrated in vacuo. The residue was purified by silica gel column (EA:PE=1:1) to give (±)-trans-N-[8-chloro-7-iodo-6-(4-methyl-3-pyridyl)-3-isoquinolyl]-2-cyano-cyclopropanecarboxamide (430 mg, 78% yield) as a yellow solid. LCMS (ESI) [M+H]$^+$=489.0.

Step 2: (±)-(trans)-N-(8-chloro-6-(4-methylpyridin-3-yl)-7-(trifluoromethyl)isoquinolin-3-yl)-2-cyano-cyclopropanecarboxamide

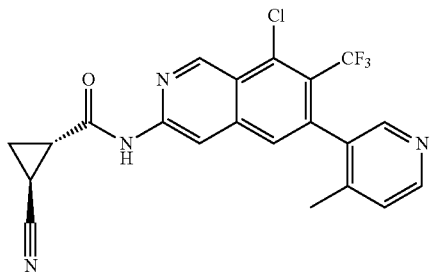 [SMILES: Cc1ccncc1-c1cc2cc(NC(=O)[C@H]3C[C@@H]3C#N)ncc2c(Cl)c1C(F)(F)F]

To a solution of (±)-(trans)-N-[8-chloro-7-iodo-6-(4-methyl-3-pyridyl)-3-isoquinolyl]-2-cyano-cyclopropanecarboxamide (370 mg, 0.76 mmol) and diphenyl(trifluoromethyl)sulfonium trifluoromethanesulfonate (620 mg, 1.53 mmol) in N,N-dimethylformamide (11 mL) was added Cu (150 mg, 2.34 mmol) at room temperature. The mixture was heated to 67° C. for 16 h. After cooling, the reaction mixture was dissolved in EtOAc (30 mL), washed with saturated aqueous sodium chloride (10 mL×3). The organic layer was dried over $Na_2SO_4$, filtered and concentrated in vacuo. The residue was purified by silica gel column chromatography (EA:PE=2:3) followed by reverse phase chromatography (acetonitrile 0-40/0.1% HCOOH in water) to afford (±)-(trans)-N-[8-chloro-6-(4-methyl-3-pyridyl)-7-(trifluoromethyl)-3-isoquinolyl]-2-cyano-cyclopropanecarboxamide (35 mg, 11% yield). LCMS (ESI) [M+H]⁺=431.1.

Step 3: (±)-(trans)-2-cyano-N-(8-(diphenylmethyleneamino)-6-(4-methylpyridin-3-yl)-7-(trifluoromethyl)isoquinolin-3-yl)cyclopropanecarboxamide

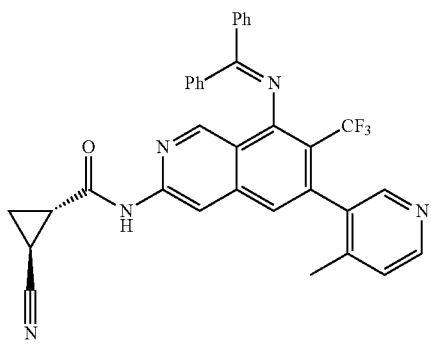 [SMILES: Cc1ccncc1-c1cc2cc(NC(=O)[C@H]3C[C@@H]3C#N)ncc2c(N=C(c2ccccc2)c2ccccc2)c1C(F)(F)F]

A mixture of (±)-(trans)-N-[8-chloro-6-(4-methyl-3-pyridyl)-7-(trifluoromethyl)-3-isoquinolyl]-2-cyano-cyclopropanecarboxamide (30 mg, 0.07 mmol), $Pd_2(dba)_3$ (12 mg, 0.01 mmol), Xantphos (15 mg, 0.03 mmol), $Cs_2CO_3$ (48 mg, 0.15 mmol), and benzophenone imine (300 mg, 1.66 mmol) in 1,4-dioxane (5 mL) was stirred at 115° C. under Ar for 6 h. The reaction was directly purified by silica gel column (EA:PE=1:5 to 1:1) to give (±)-(trans)-N-[8-(benzhydrylideneamino)-6-(4-methyl-3-pyridyl)-7-(trifluoromethyl)-3-isoquinolyl]-2-cyano-cyclopropanecarboxamide (20 mg, 50% yield) as a yellow oil. LCMS (ESI) [M+H]⁺=576.2.

Step 4: (±)-(trans)-N-(8-amino-6-(4-methylpyridin-3-yl)-7-(trifluoromethyl)isoquinolin-3-yl)-2-cyano-cyclopropanecarboxamide

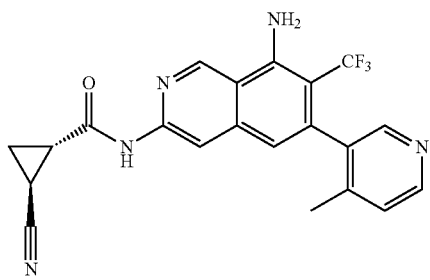 [SMILES: Cc1ccncc1-c1cc2cc(NC(=O)[C@H]3C[C@@H]3C#N)ncc2c(N)c1C(F)(F)F]

A solution of (±)-(trans)-N-[8-(benzhydrylideneamino)-6-(4-methyl-3-pyridyl)-7-(trifluoromethyl)-3-isoquinolyl]-2-cyano-cyclopropanecarboxamide (20 mg, 0.02 mmol) in acetonitrile (1 mL), water (1 mL) and 2,2,2-trifluoroacetic acid (0.5 mL) was stirred for 2 h. Then 0.2 mL concentrated HCl was added and the mixture stirred for 16 h. The mixture was evaporated, dissolved in $CH_3CN$ (1 mL), and neutralized with sat. sodium bicarbonate. The resulting mixture was purified by reverse phase chromatography (acetonitrile 17-47/0.05% ammonia in water) to give (±)-(trans)-N-[8-amino-6-(4-methyl-3-pyridyl)-7-(trifluoromethyl)-3-isoquinolyl]-2-cyano-cyclopropanecarboxamide (4 mg, 40% yield) as a white solid. LCMS (ESI) $R_T$ (min)=1.864, [M+H]⁺=421.1, Method=C; ¹HNMR (400 MHz, $CD_3OD$): δ 9.41 (s, 1H), 8.39 (s, 1H), 8.25-8.23 (m, 2H), 7.35 (s, 1H), 6.74 (s, 1H), 2.64-2.26 (m, 1H), 2.16 (s, 3H), 2.09-2.05 (m, 1H), 1.57-1.47 (m, 2H).

Example 81

(±)-(trans)-N-(8-amino-6-(5-methyl-2-oxoimidazolidin-1-yl)isoquinolin-3-yl)-2-cyanocyclopropanecarboxamide (Compound 144)

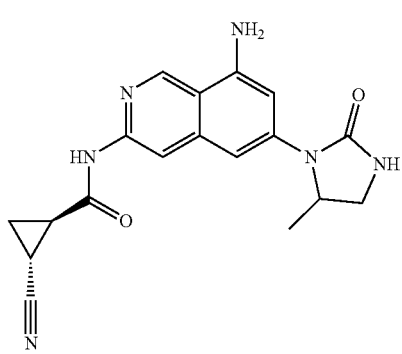 [SMILES: CC1CNC(=O)N1c1cc(N)c2cnc(NC(=O)[C@@H]3C[C@H]3C#N)cc2c1]

579

Step 1: tert-butyl 8-chloro-3-((trans)-2-cyanocyclo-propanecarboxamido)isoquinolin-6-ylcarbamate

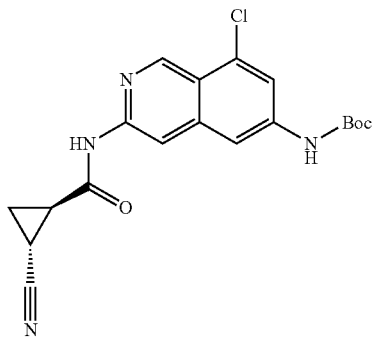 [SMILES: CC(C)(C)OC(=O)Nc1cc(Cl)c2cnc(NC(=O)[C@@H]3C[C@H]3C#N)cc2c1]

A mixture of (trans)-N-(6-bromo-8-chloro-3-isoquinolyl)-2-cyano-cyclopropanecarboxamide (600 mg, 1.71 mmol), Pd$_2$(dba)$_3$ (240 mg, 0.26 mmol), Xantphos (300 mg, 0.52 mmol), K$_2$CO$_3$ (510 mg, 3.7 mmol) and tert-butyl carbamate (400 mg, 3.41 mmol) in 1,4-dioxane (20 mL) under Ar was stirred at 90° C. for 7 h. The mixture was directly purified by silica gel column (EA:PE=1:5 to 1:3) to give tert-butyl N-[8-chloro-3-[[(trans)-2-cyanocyclopropanecarbonyl]amino]-6-isoquinolyl]carbamate (500 mg, 76% yield) as a yellow solid. LCMS (ESI) [M+H]$^+$=387.1.

Step 2: (trans)-N-(8-chloro-6-(5-methyl-2-oxoimidazolidin-1-yl)isoquinolin-3-yl)-2-cyanocyclopropanecarboxamide

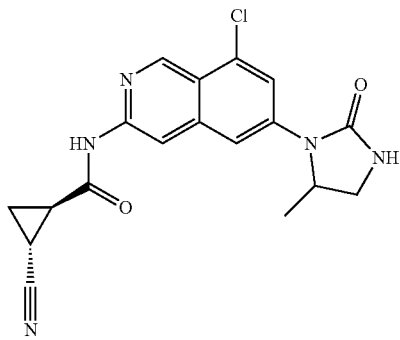 [SMILES: CC1CNC(=O)N1c1cc(Cl)c2cnc(NC(=O)[C@@H]3C[C@H]3C#N)cc2c1]

To a stirred solution of tert-butyl N-[8-chloro-3-[[(trans)-2-cyanocyclopropanecarbonyl]amino]-6-isoquinolyl]carbamate (450 mg, 1.16 mmol) in N,N-dimethylformamide (20 mL) was added NaH (450 mg, 11.25 mmol) at 0° C. The resulting mixture was stirred for 30 min at 0° C. Then tert-butyl N-(2-bromopropyl)carbamate (500 mg, 2.1 mmol) was added. The resulting mixture was stirred overnight at 80° C. After cooling to room temperature, the mixture was quenched with sat. NH$_4$Cl, and diluted with ethyl acetate. The organic layer was washed with water and brine, dried over sodium sulfate, filtered and concentrated in vacuo. The residue was purified by silica gel column (EA:PE=1:1) to give tert-butyl N-[2-[[8-chloro-3-[[(trans)-2-cyanocyclopropanecarbonyl]amino]-6-isoquinolyl]amino]propyl]carbamate (25 mg, 5% yield) as a light yellow solid. LCMS (ESI) [M+H]$^+$=370.1.

580

Step 3: tert-butyl 3-((trans)-2-cyanocyclopropanecarboxamido)-6-(5-methyl-2-oxoimidazolidin-1-yl)isoquinolin-8-ylcarbamate

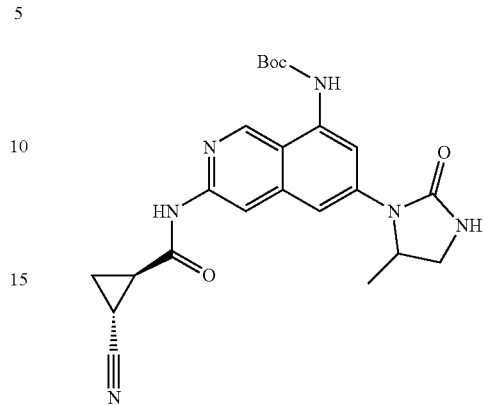

A mixture of (trans)-N-[8-chloro-6-(5-methyl-2-oxo-imidazolidin-1-yl)-3-isoquinolyl]-2-cyano-cyclopropanecarboxamide (25 mg, 0.07 mmol), tert-butyl carbamate (80 mg, 0.68 mmol), Pd$_2$(dba)$_3$ (12 mg, 0.01 mmol), Brettphos (12 mg, 0.02 mmol) and Cs$_2$CO$_3$ (65 mg, 0.20 mmol) in 1,4-dioxane (2 mL) was heated at 90° C. for 3 h under Ar. The mixture was directly purified by silica gel column (EA:PE=1:1 to 100% EA) to give tert-butyl N-[3-[[(trans)-2-cyanocyclopropanecarbonyl]amino]-6-(5-methyl-2-oxo-imidazolidin-1-yl)-8-isoquinolyl]carbamate (15 mg, 49% yield) as a yellow solid. LCMS (ESI) [M+H]$^+$=451.1.

Step 4: (trans)-N-(8-amino-6-(5-methyl-2-oxoimidazolidin-1-yl)isoquinolin-3-yl)-2-cyanocyclopropanecarboxamide

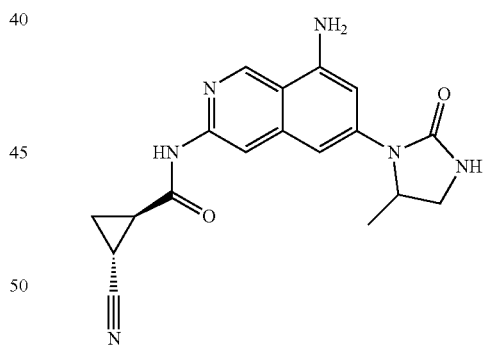

A solution of tert-butyl N-[3-[[(trans)-2-cyanocyclopropanecarbonyl]amino]-6-(5-methyl-2-oxo-imidazolidin-1-yl)-8-isoquinolyl]carbamate (15 mg, 0.03 mmol) in dichloromethane (4 mL) and 2,2,2-trifluoroacetic acid (1 mL) was stirred for 30 min at room temperature. The mixture was evaporated and purified by reverse phase chromatography (acetonitrile 17-47/0.05% HCOOH in water) to give (trans)-N-[8-amino-6-(5-methyl-2-oxo-imidazolidin-1-yl)-3-isoquinolyl]-2-cyano-cyclopropanecarboxamide (3 mg, 26% yield) as a yellow solid. LCMS (ESI): R$_T$ (min)=1.332, [M+H]$^+$=351.2, Method=A; $^1$HNMR (400 MHz, DMSO-d$_6$): δ 10.96 (s, 1H), 9.11 (s, 1H), 8.08 (s, 1H), 7.36 (s, 1H), 7.25 (s, 1H), 6.71 (s, 1H), 6.18 (s, 2H), 4.12-3.97 (m, 2H), 3.81-3.75 (m, 1H), 2.76-2.67 (m, 1H), 2.14-2.08 (m, 1H), 1.58-1.50 (m, 1H), 1.42-1.40 (m, 1H), 1.20 (d, J=6.0 Hz, 3H).

Example 82

(±)-trans-N-(8-amino-5,7-difluoro-6-(4-methylpyridin-3-yl)isoquinolin-3-yl)-2-cyanocyclopropanecarboxamide (Compound 145)

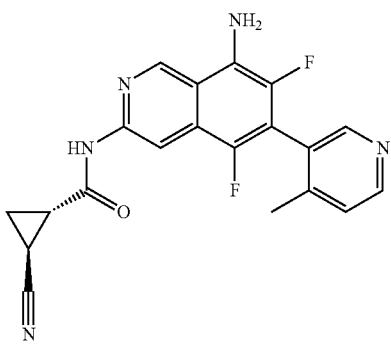 [SMILES: Cc1ccncc1-c1c(F)c(N)c2cnc(NC(=O)[C@H]3C[C@@H]3C#N)cc2c1F]

To a solution of (±)-trans-N-[8-amino-6-(4-methyl-3-pyridyl)-3-isoquinolyl]-2-cyano-cyclopropane carboxamide (100 mg, 0.29 mmol) in acetonitrile (5 mL) was added 1-fluoro-4-hydroxy-1,4-diazabicyclo[2.2.2]octane bis(tetrafluoroborate) (220 mg, 0.69 mmol). The mixture was stirred at 90° C. for 2 h in a microwave reactor. The crude was purified by prep-HPLC (Column Xbridge 21.2×250 mm c18, 10 um Mobile Phase A: water (10 mMol/LNH$_4$HCO$_3$) B: ACN) to give (±)-trans-N-[8-amino-5,7-difluoro-6-(4-methyl-3-pyridyl)-3-isoquinolyl]-2-cyano-cyclopropanecarboxamide (5 mg, 4.5% yield). (ESI): R$_T$ (min)=1.625, [M+H]$^+$=380.2, method=G; 1H NMR (400 MHz, DMSO-d6) δ 11.32 (s, 1H), 9.53 (s, 1H), 8.55 (d, J=5.2 Hz, 1H), 8.48 (s, 1H), 8.42 (s, 1H), 7.48 (d, J=5.2 Hz, 1H), 6.20 (s, 2H), 2.62-2.75 (m, 1H), 2.11-2.25 (m, 4H), 1.60-1.68 (m, 1H), 1.40-1.48 (m, 1H).

Example 83

(±)-trans-N-(8-amino-7-chloro-6-(4-methylpyridin-3-yl)isoquinolin-3-yl)-2-cyanocyclopropanecarboxamide (Compound 146)

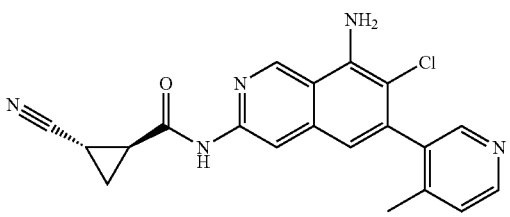 [SMILES: Cc1ccncc1-c1cc2cc(NC(=O)[C@H]3C[C@@H]3C#N)ncc2c(N)c1Cl]

Step 1: trans-2-cyano-N-(8-(diphenylmethyleneamino)-6-(4-methylpyridin-3-yl)isoquinolin-3-yl)cyclopropanecarboxamide

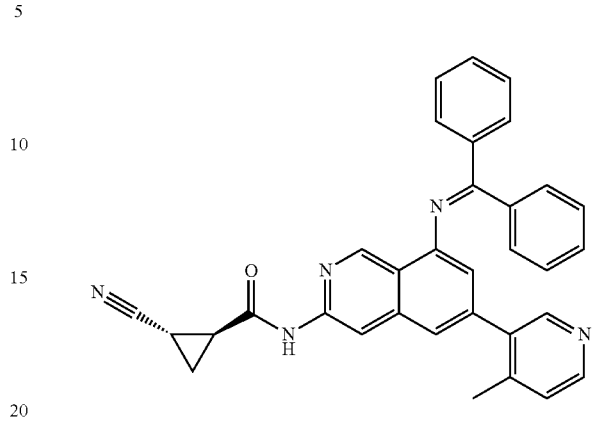

To a sealed tube was added (±)-trans-N-[8-chloro-6-(4-methyl-3-pyridyl)-3-isoquinolyl]-2-cyano-cyclopropanecarboxamide (450 mg, 1.24 mmol), Xantphos (300 mg, 0.52 mmol), Pd$_2$(dba)$_3$ (225 mg, 0.25 mmol), Cs$_2$CO$_3$ (1.0 g, 3.08 mmol), benzophenone imine (1.2 g, 6.62 mmol), and N,N-dimethylformamide (15 mL). The mixture was bubbled with N$_2$ for 2 min, stirred at 130° C. for 4 hours. The mixture was concentrated and purified by silica-gel column chromatography (eluted with PE/EA from 10:1 to 1:1) to get (±)-trans-N-[8-(benzhydrylideneamino)-6-(4-methyl-3-pyridyl)-3-isoquinolyl]-2-cyano-cyclopropanecarboxamide (250 mg, 31% yield) as yellow solid. LCMS (ESI) [M+H]$^+$=508.3.

Step 2: (±)-trans-N-(8-amino-7-chloro-6-(4-methylpyridin-3-yl)isoquinolin-3-yl)-2-cyanocyclopropanecarboxamide

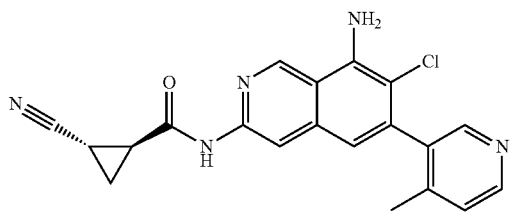 [SMILES: Cc1ccncc1-c1cc2cc(NC(=O)[C@H]3C[C@@H]3C#N)ncc2c(N)c1Cl]

To a vial was added (±)-trans-N-[8-(benzhydrylideneamino)-6-(4-methyl-3-pyridyl)-3-isoquinolyl]-2-cyano-cyclopropanecarboxamide (500 mg, 0.39 mmol), tetrahydrofuran (5 mL), and 2 N HCl (4.81 mL, 9.63 mmol). The mixture was stirred at rt for 2 hours. The mixture was concentrated and purified by silica-gel column chromatography (with DCM/MeOH from 20:1 to 10:1) followed by prep-HPLC (Mobile Phase: A: Water (10 mmol NH$_4$HCO$_3$) B: Acetonitrile) to give (±)-trans-N-[8-amino-7-chloro-6-(4-methyl-3-pyridyl)-3-isoquinolyl]-2-cyano-cyclopropanecarboxamide (11 mg, 8% yield) as a pale-brown solid. LCMS (ESI): R$_T$ (min)=1.667, [M+H]$^+$=378.1, Method=G; $^1$H NMR (400 MHz, DMSO-d$_6$) δ 9.49 (s, 1H), 8.48 (d, J=5.2 Hz, 1H), 8.32 (s, 1H), 8.24 (s, 1H), 7.36 (d, J=5.2 Hz, 1H), 6.96 (s, 1H), 6.61 (s, 1H), 6.03 (br, 2H), 2.79-2.71 (m, 1H), 2.17-2.10 (m, 1H), 2.11 (s, 3H), 1.63-1.55 (m, 1H), 1.46-1.40 (m, 1H).

Example 84

1-(8-amino-7-chloro-6-(4-methylpyridin-3-yl)isoquinolin-3-yl)-3-methylurea (Compound 147) and 1-(8-amino-5-chloro-6-(4-methylpyridin-3-yl)isoquinolin-3-yl)-3-methylurea (Compound 148)

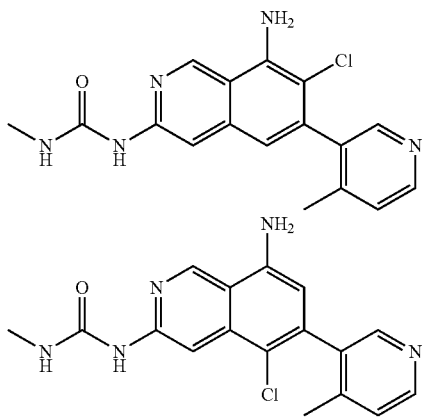

Step 1: 1-(8-chloro-6-(4-methylpyridin-3-yl)isoquinolin-3-yl)-3-methylurea

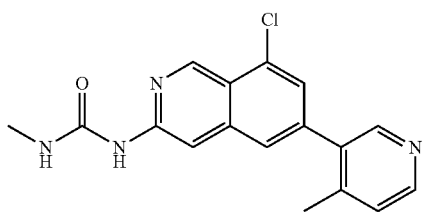 [SMILES: CNC(=O)Nc1cc2cc(-c3cnccc3C)cc(Cl)c2cn1]

To a sealed tube was added 8-chloro-6-(4-methyl-3-pyridyl)isoquinolin-3-amine (700 mg, 2.6 mmol), methylaminoformylchloride (1.2 g, 13 mmol), DBU (1 mL, 6.69 mmol) and 1,4-dioxane (10 mL). The reaction was stirred at 120° C. for 16 h. The mixture was concentrated and purified by silica-gel column chromatography (eluted with DCM/MeOH from 100:1 to 30:1) to give 1-[8-chloro-6-(4-methyl-3-pyridyl)-3-isoquinolyl]-3-methyl-urea (820 mg, 84% yield) as a brown solid. LCMS (ESI): [M+H]⁺=327.1.

Step 2: tert-butyl 6-(4-methylpyridin-3-yl)-3-(3-methylureido)isoquinolin-8-ylcarbamate

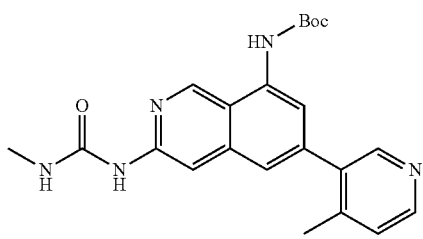 [SMILES: CNC(=O)Nc1cc2cc(-c3cnccc3C)cc(NC(=O)OC(C)(C)C)c2cn1]

To a reaction vial was added 1-[8-chloro-6-(4-methyl-3-pyridyl)-3-isoquinolyl]-3-methyl-urea (800 mg, 2.45 mmol), Brettphos (200 mg, 0.37 mmol), Pd₂(dba)₃ (300 mg, 0.33 mmol), Cs₂CO₃ (2.0 g, 6.15 mmol), tert-butyl carbamate (1.6 g, 13.7 mmol) and 1,4-dioxane (50 mL), bubbled with N₂ for 2 min. The reaction was stirred at 95° C. for 3 hours. The mixture was concentrated and purified by silica-gel column chromatography (eluted with DCM/MeOH from 100:1 to 30:1) to get tert-butyl N-[3-(methylcarbamoylamino)-6-(4-methyl-3-pyridyl)-8-isoquinolyl]carbamate (430 mg, 41% yield) as a brown solid. LCMS (ESI): [M+H]⁺=408.1.

Step 3: 1-(8-amino-6-(4-methylpyridin-3-yl)isoquinolin-3-yl)-3-methylurea

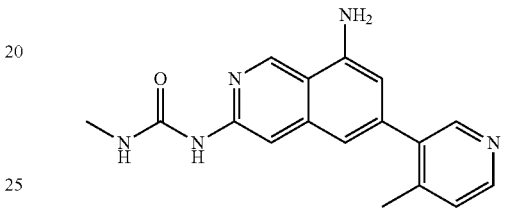

To a reaction vial was added tert-butyl N-[3-(methylcarbamoylamino)-6-(4-methyl-3-pyridyl)-8-isoquinolyl]carbamate (420 mg, 0.98 mmol) and HCl (4 N in dioxane, 5 mL). The reaction was stirred at rt for 4 hours. The mixture was concentrated and re-dissolved in a solution of NH₃ in MeOH (7 N, 20 mL) The mixture was concentrated and purified by silica-gel column chromatography (eluted with DCM/MeOH from 30:1 to 10:1) to get 1-[8-amino-6-(4-methyl-3-pyridyl)-3-isoquinolyl]-3-methyl-urea (230 mg, 75% yield) as yellow solid. LCMS (ESI): [M+H]⁺=308.2.

Step 4: 1-(8-amino-7-chloro-6-(4-methylpyridin-3-yl)isoquinolin-3-yl)-3-methylurea and 1-(8-amino-5-chloro-6-(4-methylpyridin-3-yl)isoquinolin-3-yl)-3-methylurea

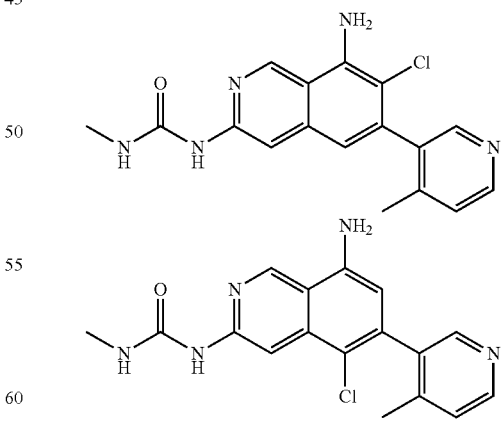

To a vial was added 1-[8-amino-6-(4-methyl-3-pyridyl)-3-isoquinolyl]-3-methyl-urea (100 mg, 0.33 mmol), acetonitrile (10 mL) and N-chlorosuccinimide (45 mg, 0.34 mmol). The mixture was stirred at 50° C. for 16 hours. The mixture was concentrated and purified by prep-HPLC (acetonitrile 30-70%/0.1% NH₄OH in water) to provide the following: 1-[8-amino-7-chloro-6-(4-methyl-3-pyridyl)-3-isoquinolyl]-3-methyl-urea (Compound 147) as a yellow solid (38 mg, 34% yield). LCMS (ESI): R$_T$ (min)=1.533, [M+H]⁺=342.2, method=G; ¹H NMR (400 MHz, DMSO-d₆) δ 9.35 (s, 1H), 9.12 (s, 1H), 8.48 (d, J=5.2 Hz, 1H), 8.31 (s, 1H), 7.82 (s, 1H), 7.36 (d, J=5.2 Hz, 1H), 7.04 (q, J=4.8 Hz, 1H), 6.85 (s, 1H), 6.52 (s, 2H), 2.71 (d, J=4.8 Hz, 3H), 2.12 (s, 3H). 1-[8-amino-5-chloro-6-(4-methyl-3-pyridyl)-3-isoquinolyl]-3-methyl-urea (Compound 148) as a yellow solid (21 mg, 19% yield). LCMS (ESI): R$_T$ (min)=1.499, [M+H]+=342.1, method=G; ¹H NMR (400 MHz, DMSO-d6) δ 9.28 (s, 1H), 9.23 (s, 1H), 8.48 (d, J=5.2 Hz, 1H), 8.32 (s, 1H), 8.22 (s, 1H), 7.37 (d, J=5.2 Hz, 1H), 7.06 (q, J=4.8 Hz, 1H), 6.49 (s, 2H), 6.36 (s, 1H), 2.72 (d, J=4.8 Hz, 3H), 2.12 (s, 3H).

Example 85

1-(8-amino-5-cyano-6-(4-methylpyridin-3-yl)isoquinolin-3-yl)-3-methylurea (Compound 149) 1-(8-amino-7-cyano-6-(4-methylpyridin-3-yl)isoquinolin-3-yl)-3-methylurea (Compound 150)

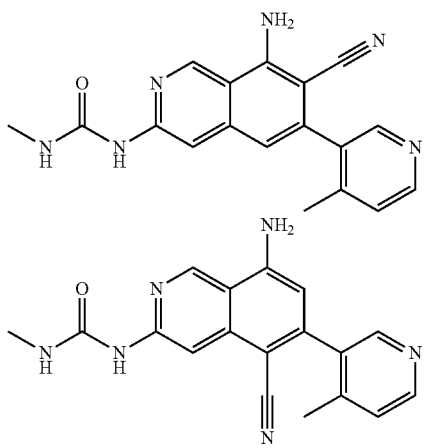

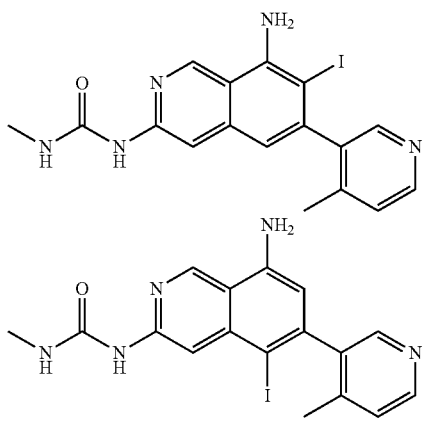

Step 1: 1-(8-amino-5-iodo-6-(4-methylpyridin-3-yl)isoquinolin-3-yl)-3-methylurea and 1-(8-amino-7-iodo-6-(4-methylpyridin-3-yl)isoquinolin-3-yl)-3-methylurea To a reaction vial was added 1-[8-amino-6-(4-methyl-3-pyridyl)-3-isoquinolyl]-3-methyl-urea (100 mg, 0.33 mmol), acetic acid (5 mL) and N-iodosuccinimide (75 mg, 0.33 mmol). The mixture was stirred at 20° C. for 3 days. The mixture was concentrated and pH adjusted to 7 with sat. NaHCO₃. The product extracted with ethyl acetate (50 mL×2), dried over Na₂SO₄, filtered and concentrated to give a crude mixture of 1-(8-amino-5-iodo-6-(4-methylpyridin-3-yl)isoquinolin-3-yl)-3-methylurea and 1-(8-amino-7-iodo-6-(4-methylpyridin-3-yl)isoquinolin-3-yl)-3-methylurea. The crude mixture was used in the next step without further purification. LCMS (ESI): [M+H]⁺=434.1

Step 2: 1-(8-amino-5-cyano-6-(4-methylpyridin-3-yl)isoquinolin-3-yl)-3-methylurea & 1-(8-amino-7-cyano-6-(4-methylpyridin-3-yl)isoquinolin-3-yl)-3-methylurea

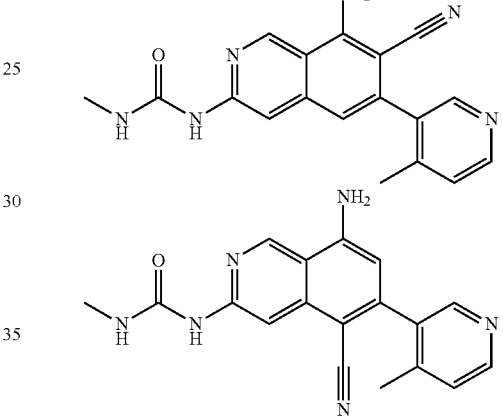

To a vial was added a mixture of 1-(8-amino-5-iodo-6-(4-methylpyridin-3-yl)isoquinolin-3-yl)-3-methylurea & 1-(8-amino-7-iodo-6-(4-methylpyridin-3-yl)isoquinolin-3-yl)-3-methylurea (100 mg, 0.23 mmol), Pd(t-Bu₃P)₂ (15 mg, 0.03 mmol), Zn (5 mg, 0.08 mmol), Zn(CN)₂ (50 mg, 0.43 mmol) and N,N-dimethylformamide (5 mL). The reaction mixture was bubbled for 2 min with N₂ and stirred at 90° C. for 4 hours. The mixture was concentrated and purified by silica-gel column chromatography (eluted with DCM/MeOH from 100:1 to30:1) to give: Compound 149: 1-[8-amino-7-cyano-6-(4-methyl-3-pyridyl)-3-isoquinolyl]-3-methyl-urea (14 mg, 18% yield) as a white solid. LCMS (ESI): RT (min)=1.512, [M+H]⁺=333.1, method=C; ¹H NMR (400 MHz, DMSO-d₆) δ 9.41 (s, 1H), 9.32 (s, 1H), 8.51 (d, J=5.2 Hz, 1H), 8.39 (s, 1H), 7.86 (s, 1H), 7.39 (d, J=5.2 Hz, 1H), 7.35 (s, 2H), 7.07 (q, J=4.4 Hz, 1H), 6.80 (s, 1H), 2.71 (d, J=4.4 Hz, 3H), 2.22 (s, 3H). Compound 150: 1-[8-amino-5-cyano-6-(4-methyl-3-pyridyl)-3-isoquinolyl]-3-methyl-urea (23 mg, 30% yield) was isolated as a white solid. LCMS (ESI): RT (min)=1.428, [M+H]⁺=333.2, method=G; ¹H NMR (400 MHz, DMSO-d₆) δ 9.37 (s, 1H), 9.34 (s, 1H), 8.54 (d, J=5.2 Hz, 1H), 8.43 (s, 1H), 8.18 (s, 1H), 7.50 (s, 2H), 7.43 (d, J=5.2 Hz, 1H), 7.00 (q, J=4.4 Hz, 1H), 6.41 (s, 1H), 2.73 (d, J=4.4 Hz, 3H), 2.22 (s, 3H).

Example 86

(±)-trans-N-[8-amino-6-(2-oxooxazolidin-5-yl)-3-isoquinolyl]-2-cyano-cyclopropanecarboxamide (Compound 151)

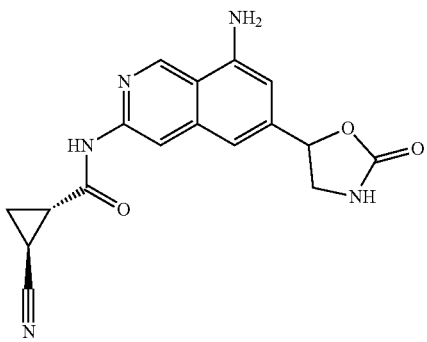 [SMILES: N#C[C@H]1C[C@@H]1C(=O)Nc1cc2cc(C3CNC(=O)O3)cc(N)c2cn1]

Step 1: tert-butyl N-[2-(3-amino-8-chloro-6-isoquinolyl)-2-oxo-ethyl]carbamate

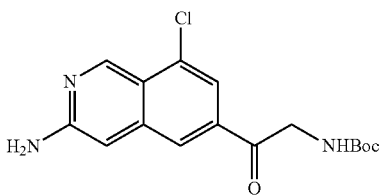 [SMILES: CC(C)(C)OC(=O)NCC(=O)c1cc(Cl)c2cnc(N)cc2c1]

To a solution of 6-bromo-8-chloro-isoquinolin-3-amine (500 mg, 1.94 mmol) in dry tetrahydrofuran (20 mL) was added iPrMgCl.LiCl complex (1.3 M in THF) (20 mL, 26 mmol) at 0° C. under $N_2$. After addition completed, the reaction solution was stirred at rt for 1 h. The mixture was cooled to 0° C. and added (±)-tert-butyl 2-(methoxy(methyl)amino)-2-oxoethylcarbamate (1.27 g, 5.83 mmol). The reaction solution was stirred at rt for 1 h. The reaction mixture was quenched by the addition of the saturated aqueous NaCl and extracted with ethyl acetate (30 mL×3). The organic extract was dried with anhydrous $Na_2SO_4$, filtered and concentrated. The crude product was purified by flash column chromatography eluting with 40% ethyl acetate in PE to give tert-butyl N-[2-(3-amino-8-chloro-6-isoquinolyl)-2-oxo-ethyl]carbamate (330 mg, 48% yield) as a yellow oil. LCMS (ESI): [M+H]$^+$=336.1.

Step 2: tert-butyl N-[2-(3-amino-8-chloro-6-isoquinolyl)-2-hydroxy-ethyl]carbamate

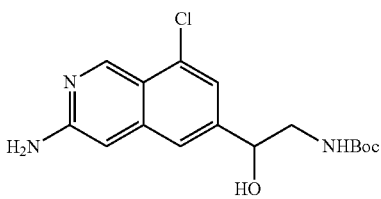 [SMILES: CC(C)(C)OC(=O)NCC(O)c1cc(Cl)c2cnc(N)cc2c1]

To a solution of tert-butyl N-[2-(3-amino-8-chloro-6-isoquinolyl)-2-oxo-ethyl]carbamate (150 mg, 0.45 mmol) in MeOH (3 mL) was added $NaBH_4$ (42 mg, 1.12 mmol) at 0° C. The resulting solution was stirred at 0° C. for 1 h. The water (5 mL) was added to quenched the reaction. The mixture was extracted by EA (10 mL×2). The organic layers were washed with water (5 mL), dried with anhydrous $Na_2SO_4$, filtered and concentrated in vacuo. The crude product tert-butyl N-[2-(3-amino-8-chloro-6-isoquinolyl)-2-hydroxy-ethyl]carbamate (140 mg, 93% yield) was used in the next step without purification. LCMS (ESI): [M+H-100]$^+$=338.1.

Step 3:
5-(3-amino-8-chloro-6-isoquinolyl)oxazolidin-2-one

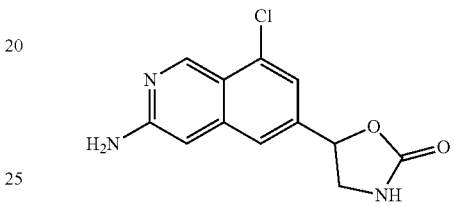

The tert-butyl N-[2-(3-amino-8-chloro-6-isoquinolyl)-2-hydroxy-ethyl]carbamate (140 mg, 0.41 mmol) was dissolved in N,N-dimethylformamide (3 mL). NaH (15 mg, 0.62 mmol) was added at 0° C. The resulting solution was stirred at room temperature for 3 h. Water (5 mL) was added to quench the reaction and the mixture was extracted with ethyl acetate (10 mL×2). The organic layers were washed with brine (10 mL×3), dried over anhydrous $Na_2SO_4$, filtered and concentrated. The crude product was purified by prep-TLC (DCM:MeOH=20:1) to obtained the title product 5-(3-amino-8-chloro-6-isoquinolyl)oxazolidin-2-one (60 mg, 51% yield) as a yellow oil. LCMS (ESI): [M+H]$^+$=264.0.

Step 4: trans-N-[8-chloro-6-(2-oxooxazolidin-5-yl)-3-isoquinolyl]-2-cyano-cyclopropane Carboxamide

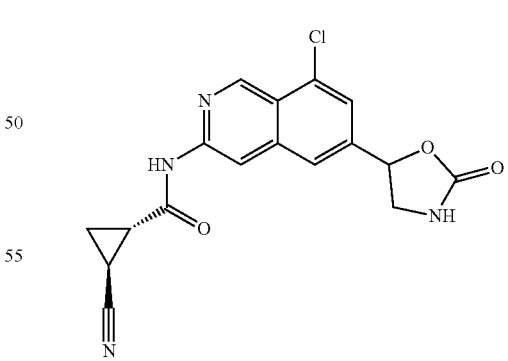

A mixture of (±)-trans-2-cyanocyclopropanecarboxylic acid (250 mg, 2.25 mmol) in dichloromethane (5 mL) was stirred at 0° C. for 10 min. Then ethanedioyl dichloride (572 mg, 4.51 mmol) was added dropwise. The reaction mixture was stirred at 25° C. for 1 h, and concentrated. The crude product was then added to a solution of 5-(3-amino-8-chloro-6-isoquinolyl)oxazolidin-2-one (60 mg, 0.23 mmol)

and pyridine (0.06 mL, 0.68 mmol) in dichloromethane (5 mL) at 0° C. The reaction mixture was stirred at 25° C. for 1 h. The reaction mixture was filtered and concentrated. The residue was purified by flash column chromatography (DCM/MeOH=10/1) to give trans-N-[8-chloro-6-(2-oxooxazolidin-5-yl)-3-isoquinolyl]-2-cyano-cyclopropanecarboxamide (70 mg, 86% yield) as a white solid. LCMS (ESI): [M+H]$^+$=357.0.

Step 5: trans-N-[8-amino-6-(2-oxooxazolidin-5-yl)-3-isoquinolyl]-2-cyano-cyclopropane Carboxamide

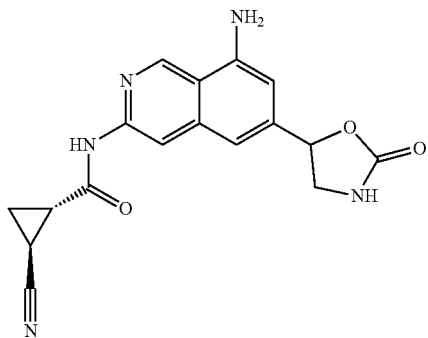 [SMILES: N#C[C@H]1C[C@@H]1C(=O)Nc1cc2cc(C3CNC(=O)O3)cc(N)c2cn1]

To a sealed tube was added tert-butyl carbamate (229 mg, 1.96 mmol), Pd$_2$(dba)$_3$ (36 mg, 0.04 mmol), Cs$_2$CO$_3$ (192 mg, 0.59 mmol), xantphos (38 mg, 0.08 mmol), trans-N-[8-chloro-6-(2-oxooxazolidin-5-yl)-3-isoquinolyl]-2-cyano-cyclopropanecarboxamide (70 mg, 0.20 mmol), N,N-dimethylformamide (1 mL) and toluene (1 mL) in glove box. The mixture was stirred at 130° C. for 2 d. The reaction was concentrated and diluted with water (20 mL). The mixture was extracted with ethyl acetate (30 mL×3) and the combined organic layers was washed with water (20 mL), saturated NaCl solution (30 mL×3), dried over sodium sulfate, filtered and concentrated. The crude product was purified by prep-HPLC (mobile phase:A water (0.01% NH$_3$)+10 mm (NH$_4$HCO$_3$), B Acetonitrile) to give trans-N-[8-amino-6-(2-oxooxazolidin-5-yl)-3-isoquinolyl]-2-cyano-cyclopropanecarboxamide (4.8 mg, 7.3% yield) as yellow solid. LCMS (ESI): R$_T$ (min)=1.398, [M+H]$^+$=338.0, method=C; $^1$H NMR (400 MHz, CD$_3$OD) δ 9.20 (s, 1H), 8.27 (s, 1H), 7.06 (s, 1H), 6.74 (s, 1H), 5.72-5.68 (m, 1H), 4.07-4.02 (m, 1H), 3.53-3.49 (m, 1H), 2.65-2.62 (m, 1H), 2.13-2.11 (m, 1H), 1.61-1.53 (m, 1H).

Example 87

(±)-trans-N-[8-amino-7-(hydroxymethyl)-6-(4-methyl-3-pyridyl)-3-isoquinolyl]-2-cyano-cyclopropanecarboxamide (Compound 153)

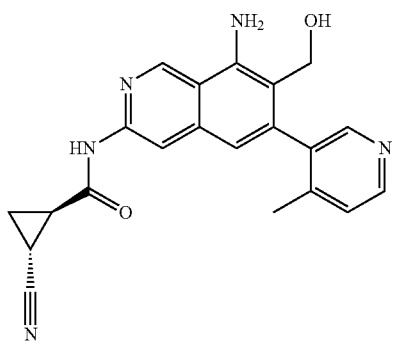 [SMILES: Cc1ccncc1-c1cc2cc(NC(=O)[C@@H]3C[C@H]3C#N)ncc2c(N)c1CO]

Step 1: (±)-trans-N-[8-amino-7-formyl-6-(4-methyl-3-pyridyl)-3-isoquinolyl]-2-cyano-cyclopropanecarboxamide

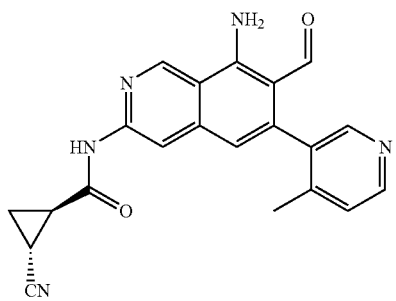 [SMILES: Cc1ccncc1-c1cc2cc(NC(=O)[C@@H]3C[C@H]3C#N)ncc2c(N)c1C=O]

A mixture of (±)-trans-N-[8-(benzhydrylideneamino)-7-(difluoromethyl)-6-(4-methyl-3-pyridyl)-3-isoquinolyl]-2-cyano-cyclopropanecarboxamide (140 mg, 0.25 mmol) and 2,2,2-trifluoroacetic acid (8 mL) in water (20 mL) and acetonitrile (20 mL) was stirred at 25° C. for 3 h. The reaction mixture was concentrated and neutralized with sat NaHCO$_3$(aq.) to pH=7-8. The mixture was concentrated and purified by preparative HPLC Reverse phase (C-18, acetonitrile/Water+0.05% NH$_4$HCO$_3$) to give (±)-trans-N-[8-amino-7-formyl-6-(4-methyl-3-pyridyl)-3-isoquinolyl]-2-cyano-cyclopropanecarboxamide (120 mg, 68% yield) as a yellow solid. LCMS (ESI) [M+H]$^+$=372.7.

Step 2: (±)-trans-N-[8-amino-7-(hydroxymethyl)-6-(4-methyl-3-pyridyl)-3-isoquinolyl]-2-cyano-cyclopropanecarboxamide

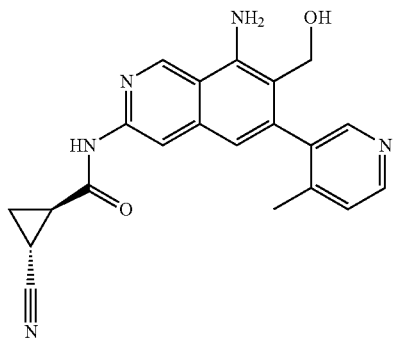 [SMILES: Cc1ccncc1-c1cc2cc(NC(=O)[C@@H]3C[C@H]3C#N)ncc2c(N)c1CO]

To a solution of (±)-trans-N-[8-amino-7-formyl-6-(4-methyl-3-pyridyl)-3-isoquinolyl]-2-cyano-cyclopropanecarboxamide (100 mg, 0.16 mmol) in acetonitrile (20 mL) and methyl alcohol (20 mL) at 0° C. was added NaBH$_4$ (24 mg, 0.63 mmol). The mixture was stirred at 0° C. for 10 min. The mixture was concentrated and purified by preparative reverse phase HPLC (C-18, acetonitrile/Water+0.05% NH$_4$HCO$_3$) to give (±)-trans-N-[8-amino-7-(hydroxymethyl)-6-(4-methyl-3-pyridyl)-3-isoquinolyl]-2-cyano-cyclopropanecarboxamide (25 mg, 41% yield) as a yellow solid. LCMS (ESI) R$_T$ (min)=1.852, [M+H]$^+$=374.1, method=C. $^1$H NMR (400 MHz, DMSO-d$_6$) δ 11.12 (s, 1H), 9.46 (s, 1H), 8.46 (d, J=4.8 Hz, 1H), 8.32 (d, J=1.2 Hz, 1H), 8.19 (s, 1H), 7.34 (d, J=4.8 Hz, 1H), 6.75 (s, 1H), 6.32 (s, 2H), 4.95 (s, 1H), 4.29 (d, J=12.4 Hz, 1H), 4.18 (d, J=12.0 Hz, 1H), 2.78-2.75 (m, 1H), 2.17-2.11 (m, 1H), 2.08 (s, 3H), 1.61-1.56 (m, 1H), 1.46-1.40 (m, 1H).

Example 88

(1)-1-[8-amino-6-(4-methyl-2-oxo-oxazolidin-3-yl)-3-isoquinolyl]-3-isopropyl-urea (Compound 154)

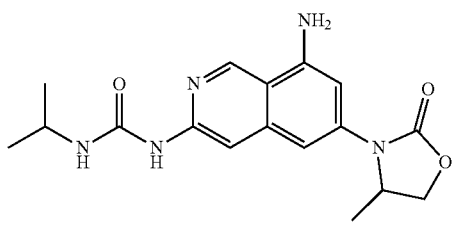

Step 1: 1-(6-bromo-8-chloro-3-isoquinolyl)-3-isopropyl-urea

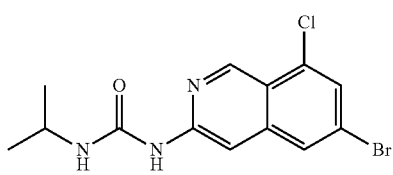 [SMILES: CC(C)NC(=O)Nc1cc2cc(Br)cc(Cl)c2cn1]

A mixture of 6-bromo-8-chloro-isoquinolin-3-amine (400 mg, 1.55 mmol), isopropyl isocyanate (1.19 g, 13.98 mmol) and DBU (1.18 g, 7.76 mmol) in 1,4-dioxane (15 mL) was stirred at 100° C. for 5 h. The mixture was concentrated and purified by column chromatography eluting with EtOAc/hexane=1:2 to afford 1-(6-bromo-8-chloro-3-isoquinolyl)-3-isopropyl-urea (570 mg, 1.03 mmol, 66% yield) as a yellow solid. LCMS (ESI) [M+H]$^+$=342.0.

Step 2: 1-[8-chloro-6-(4-methyl-2-oxo-oxazolidin-3-yl)-3-isoquinolyl]-3-isopropyl-urea

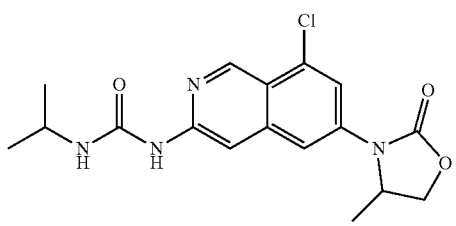 [SMILES: CC(C)NC(=O)Nc1cc2cc(N3C(=O)OCC3C)cc(Cl)c2cn1]

A mixture of 1-(6-bromo-8-chloro-3-isoquinolyl)-3-isopropyl-urea (570 mg, 1.03 mmol), 4-methyloxazolidin-2-one (125 mg, 1.24 mmol), Pd$_2$(dba)$_3$ (95 mg, 0.1 mmol), Xantphos (119 mg, 0.21 mmol) and K$_3$PO$_4$ (437 mg, 2.06 mmol) in 1,4-dioxane (18 mL) was stirred under Ar at 90° C. for 2 h. The mixture was concentrated and purified by column chromatography eluting with EtOAc/hexane=2:1 to afford 1-[8-chloro-6-(4-methyl-2-oxo-oxazolidin-3-yl)-3-isoquinolyl]-3-isopropyl-urea (306 mg, 81% yield) as a white solid. LCMS (ESI) [M+H]$^+$=363.1.

Step 3: (±)-tert-butyl N-[3-(isopropylcarbonylamino)-6-(4-methyl-2-oxo-oxazolidin-3-yl)-8-isoquinolyl]carbamate

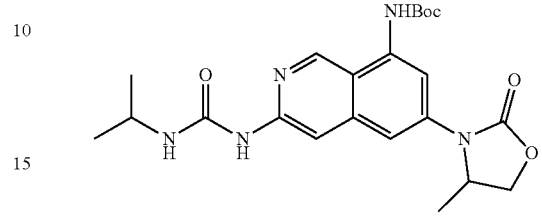

A mixture of 1-[8-chloro-6-(4-methyl-2-oxo-oxazolidin-3-yl)-3-isoquinolyl]-3-isopropyl-urea (286 mg, 0.79 mmol), BocNH$_2$ (922 mg, 7.88 mmol), Pd$_2$(dba)$_3$ (108 mg, 0.12 mmol), Brettphos (127 mg, 0.24 mmol) and Cs$_2$CO$_3$ (512 mg, 1.58 mmol) in 1,4-dioxane (20 mL) was stirred at 90° C. under Ar for 2 h. The mixture was concentrated and purified by column chromatography eluting with EtOAc/DCM=3:1 to afford tert-butyl N-[3-(isopropylcarbonylamino)-6-(4-methyl-2-oxo-oxazolidin-3-yl)-8-isoquinolyl]carbamate (285 mg, 66% yield) as a yellow solid. LCMS (ESI) [M+H]$^+$=444.4.

Step 4: (±)-1-[8-amino-6-(4-methyl-2-oxo-oxazolidin-3-yl)-3-isoquinolyl]-3-isopropyl-urea

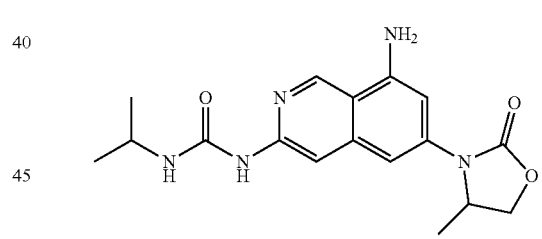

A mixture of (±)-tert-butyl N-[3-(isopropylcarbonylamino)-6-(4-methyl-2-oxo-oxazolidin-3-yl)-8-isoquinolyl]carbamate (280 mg, 0.52 mmol) and 2,2,2-trifluoroacetic acid (2 mL) in dichloromethane (10 mL) was stirred at 25° C. for 2 h. The reaction mixture was concentrated and neutralized with sat NaHCO$_3$ (aq.) to pH=7-8. The mixture was concentrated and purified by preparative reverse phase HPLC (C-18, acetonitrile/water+0.05% NH$_4$HCO$_3$) to give (±)-1-[8-amino-6-(4-methyl-2-oxo-oxazolidin-3-yl)-3-isoquinolyl]-3-isopropyl-urea (140 mg, 78% yield) as a yellow solid. LCMS (ESI) R$_T$ (min)=1.399, [M+H]$^+$=344.2, method=A. $^1$H NMR (400 MHz, DMSO-d$_6$) δ 9.09 (s, 1H), 8.80 (s, 1H), 7.67 (s, 1H), 7.21 (d, J=6.8 Hz, 1H), 6.87 (d, J=1.2 Hz, 1H), 6.84 (s, 1H), 6.25 (s, 2H), 4.71-4.68 (m, 1H), 4.55 (t, J=8.2 Hz, 1H), 4.04 (q, J=4.4 Hz, 1H), 3.84-3.78 (m, 1H), 1.28 (d, J=6.4 Hz, 3H), 1.13 (d, J=6.8 Hz, 6H).

Example 89

N-(8-amino-6-(4-ethylpyridin-3-yl)isoquinolin-3-yl)-2-(1H-pyrazol-5-yl)acetamide (Compound 155)

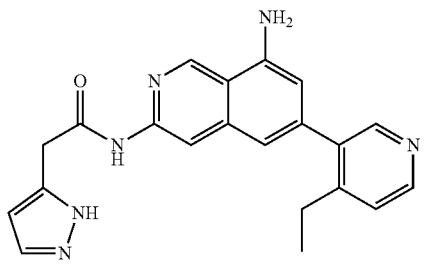 [SMILES: CCc1ccncc1-c1cc(N)c2cnc(NC(=O)Cc3ccn[nH]3)cc2c1]

Step 1: 2-(1-(tetrahydro-2H-pyran-2-yl)-1H-pyrazol-5-yl)acetonitrile

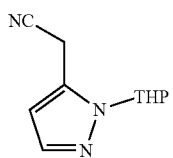

A mixture of 2-(1H-pyrazol-5-yl)acetonitrile (250 mg, 2.33 mmol), p-toluenesulfonicacid (40 mg, 0.23 mmol) and 3,4-dihydro-2h-pyran (295 mg, 3.5 mmol) in ethyl acetate (5 mL) was stirred for 18 hs at 25° C. 5 mL saturated aqueous NaHCO₃ was added to reaction mixture and stirred for 10 min. The EA was dried over Na₂SO₄ and concentrated in vacuo to give 2-(2-tetrahydropyran-2-ylpyrazol-3-yl)acetonitrile (430 mg, 74.6% yield) as colorless oil. LCMS (ESI): $[M+23]^+=214.2$.

Step 2: 2-(1-(tetrahydro-2H-pyran-2-yl)-1H-pyrazol-5-yl)acetic Acid

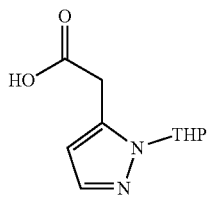

A mixture of 2-(2-tetrahydropyran-2-ylpyrazol-3-yl)acetonitrile (430 mg, 2.25 mmol) and KOH (378. mg, 6.75 mmol) in ethanol (5 mL), water (5 mL) was stirred for 5 hs at 80° C.

The EtOH was removed and the resulting mixture diluted with water (10 mL) and extracted with ethyl acetate (10 mL). The aqueous phase was adjusted pH=5 with 1N HCl and extracted with ethyl acetate (20 mL×2). The combined ethyl acetate layers were dried over Na₂SO₄ and concentrated in vacuo to give 2-(2-tetrahydropyran-2-ylpyrazol-3-yl)acetic acid (480 mg, 83.7% yield) as colorless oil. LCMS (ESI): $[M+H]^+=233.1$.

Step 3: 8-chloro-6-(4-ethylpyridin-3-yl)isoquinolin-3-amine

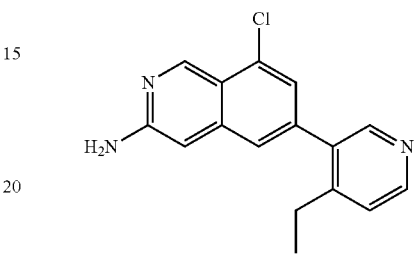

A mixture of 6-bromo-8-chloro-isoquinolin-3-amine (300 mg, 1.17 mmol), 4-ethyl-3-(4,4,5,5-tetramethyl-1,3,2-dioxaborolan-2-yl)pyridine (326 mg, 1.4 mmol), Na₂CO₃ (309 mg, 2.91 mmol) and Pd(dppf)Cl₂ (43 mg, 0.06 mmol) in 1,4-dioxane (3 mL), H₂O (0.3 mL) was stirred for 3 hrs at 90° C. The solvent was removed and the residue was purified by flash column chromatography (PE:EA=2:1-1:4) to give 8-chloro-6-(4-ethyl-3-pyridyl)isoquinolin-3-amine (260 mg, 78.6% yield) as yellow solid. LCMS (ESI): $[M+H]^+=284.1$.

Step 4: N-(8-chloro-6-(4-ethylpyridin-3-yl)isoquinolin-3-yl)-2-(1-(tetrahydro-2H-pyran-2-yl)-1H-pyrazol-5-yl)acetamide

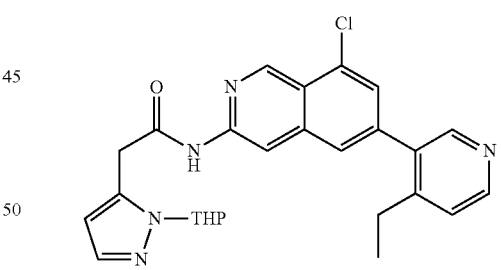

To a mixture of 8-chloro-6-(4-ethyl-3-pyridyl)isoquinolin-3-amine (130 mg, 0.46 mmol) and 2-(2-tetrahydropyran-2-ylpyrazol-3-yl)acetic acid (130 mg, 0.62 mmol) in pyridine (2 mL) was added phosphorus oxychloride (281 mg, 1.83 mmol) at 0° C. The resulting mixture was stirred for 1 h at 0° C. Quenched with saturated aq.NaHCO₃ and extracted with ethyl acetate (20 mL×2). The combined ethyl acetate layers were concentrated in vacuo and the residue was purified by flash column chromatography (PE:EA=3:1-1:3) to give N-[8-chloro-6-(4-ethyl-3-pyridyl)-3-isoquinolyl]-2-(2-tetrahydropyran-2-ylpyrazol-3-yl)acetamide (90 mg, 38.5% yield) as yellow solid. LCMS (ESI): $[M+H]^+=476.2$.

Step 5: N-(8-(diphenylmethyleneamino)-6-(4-ethylpyridin-3-yl)isoquinolin-3-yl)-2-(1-(tetrahydro-2H-pyran-2-yl)-1H-pyrazol-5-yl)acetamide

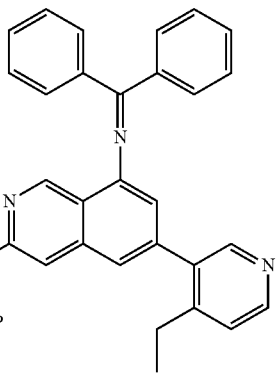

A mixture of N-[8-chloro-6-(4-ethyl-3-pyridyl)-3-isoquinolyl]-2-(2-tetrahydropyran-2-ylpyrazol-3-yl)acetamide (80 mg, 0.17 mmol), benzophenone imine (61 mg, 0.34 mmol), Pd2(dba)3 (31 mg, 0.03 mmol), Xantphos (39 mg, 0.07 mmol) and Cs₂CO₃ (110 mg, 0.34 mmol) in N,N-dimethylformamide (2 mL), toluene (2 mL) was stirred for 3 hrs at 130° C. The reaction was cooled to rt, diluted with water, and extracted with ethyl acetate (20 mL×2). The combined ethyl acetate layers were concentrated in vacuo to give N-[8-(benzhydrylideneamino)-6-(4-ethyl-3-pyridyl)-3-isoquinolyl]-2-(2-tetrahydropyran-2-ylpyrazol-3-yl)acetamide (170 mg, 50.5% yield, crude) as brown solid. This crude was used to next step without purification. LCMS (ESI): [M+H]⁺=611.2.

Step 6: N-(8-amino-6-(4-ethylpyridin-3-yl)isoquinolin-3-yl)-2-(1H-pyrazol-5-yl)acetamide

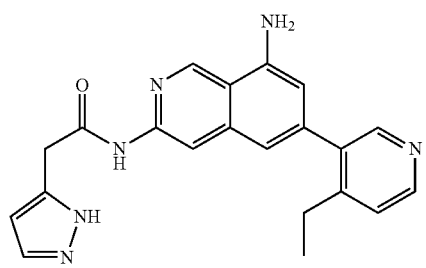 [SMILES: CCc1ccncc1-c1cc(N)c2cnc(NC(=O)Cc3ccn[nH]3)cc2c1]

A mixture of N-[8-(benzhydrylideneamino)-6-(4-ethyl-3-pyridyl)-3-isoquinolyl]-2-(2-tetrahydropyran-2-ylpyrazol-3-yl)acetamide (160 mg, 0.26 mmol) in 1 mL 4 M HCl/dioxane was stirred for 0.5 h at 25° C. The solvent was removed and the residue was purified by reverse phase chromatography (acetonitrile 10-45/0.05% NH₄HCO₃ in water) to give N-[8-amino-6-(4-ethyl-3-pyridyl)-3-isoquinolyl]-2-(1H-pyrazol-5-yl)acetamide (5.3 mg, 5.5% yield) as yellow solid. LCMS (ESI): R$_T$ (min)=1.59, [M+H]⁺=373.1, method=C. ¹H NMR (400 MHz, DMSO-d₆): 12.62 (s, 1H), 10.52 (s, 1H), 9.31 (s, 1H), 8.49 (d, J=5.2 Hz, 1H), 8.37 (s, 1H), 8.25 (s, 1H), 7.65 (s, 1H), 7.39 (d, J=5.2 Hz, 1H), 6.88 (s, 1H), 6.35 (d, J=6.8 Hz, 1H), 6.34 (s, 2H), 6.22 (d, J=6.8 Hz, 1H), 3.83 (s, 2H), 2.64 (q, J=7.6 Hz, 2H), 1.11 (t, J=7.6 Hz, 3H).

Example 90

(±)-trans-N-(8-amino-6-(5-amino-4-methylpyridin-3-yl)isoquinolin-3-yl)-2-cyanocyclopropanecarboxamide (Compound 156)

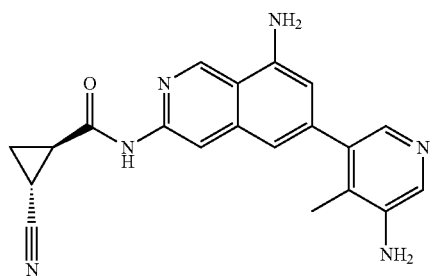 [SMILES: Cc1c(N)cncc1-c1cc(N)c2cnc(NC(=O)[C@@H]3C[C@H]3C#N)cc2c1]

Step 1: (±)-tert-butyl 5-(8-chloro-3-(trans-2-cyanocyclopropanecarboxamido)isoquinolin-6-yl)-4-methylpyridin-3-ylcarbamate

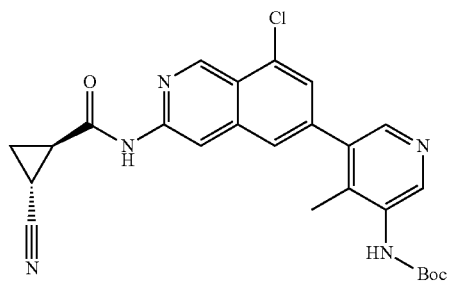 [SMILES: Cc1c(NC(=O)OC(C)(C)C)cncc1-c1cc(Cl)c2cnc(NC(=O)[C@@H]3C[C@H]3C#N)cc2c1]

A mixture of tert-butyl N-(5-bromo-4-methyl-3-pyridyl)carbamate (250 mg, 0.87 mmol), [8-chloro-3-[[(trans)-2-cyanocyclopropanecarbonyl]amino]-6-isoquinolyl]boronic acid (350 mg, 1.11 mmol), Na₂CO₃ (185 mg, 1.75 mmol) and Pd(dppf)Cl₂ (35 mg, 0.05 mmol) in 1,4-dioxane (10 mL) and H₂O (0.4 mL) was stirred for 4 h at 90° C. The reaction was concentrated and purified by flash column chromotography (PE/EA=20%-60%) to give tert-butyl N-[5-[8-chloro-3-[[(trans)-2-cyanocyclopropanecarbonyl]amino]-6-isoquinolyl]-4-methyl-3-pyridyl]carbamate (160 mg, 36.2% yield) as a white solid. LCMS (ESI): [M+H]⁺=478.1.

Step 2: (±)-tert-butyl N-[5-[8-(tert-butoxycarbonylamino)-3-[[(trans)-2-cyanocyclopropanecarbonyl]amino]-6-isoquinolyl]-4-methyl-3-pyridyl]carbamate

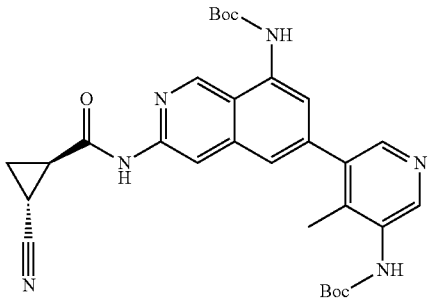 [SMILES: Cc1c(NC(=O)OC(C)(C)C)cncc1-c1cc(NC(=O)OC(C)(C)C)c2cnc(NC(=O)[C@@H]3C[C@H]3C#N)cc2c1]

A mixture of tert-butyl carbamate (178 mg, 1.52 mmol), tert-butyl N-[5-[8-chloro-3-[[(trans)-2-cyanocyclopropanecarbonyl]amino]-6-isoquinolyl]-4-methyl-3-pyridyl]carbamate (160 mg, 0.33 mmol), Pd$_3$(dba)$_2$ (30 mg, 0.03 mmol), Brettphos (20 mg, 0.04 mmol) and Cs$_2$CO$_3$ (320 mg, 0.98 mmol) in 1,4-dioxane (4 mL) was stirred for 2 h at 90° C. The reaction was then cooled to rt and diluted with water (20 mL). The product was extracted with ethyl acetate (50 mL×2). The combined ethyl acetate layers were dried over Na$_2$SO$_4$ and concentrated in vacuo. The residue was purified by flash column chromatography (PE/EA=40%-70%) to give (±)-tert-butyl N-[5-[8-(tert-butoxycarbonylamino)-3-[[(trans)-2-cyanocyclopropanecarbonyl]amino]-6-isoquinolyl]-4-methyl-3-pyridyl]carbamate (80 mg, 42.78% yield) as yellow solid. LCMS (ESI): [M+H]$^+$=559.2.

Step 3: (±)-trans-N-(8-amino-6-(5-amino-4-methylpyridin-3-yl)isoquinolin-3-yl)-2-cyanocyclopropanecarboxamide

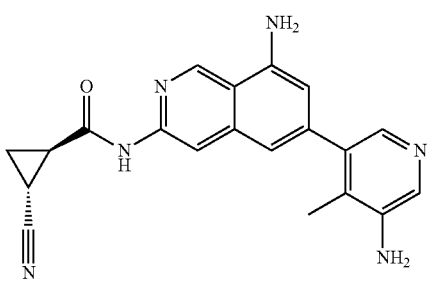 [SMILES: Cc1c(N)cncc1-c1cc(N)c2cnc(NC(=O)[C@@H]3C[C@H]3C#N)cc2c1]

A mixture of (±)-tert-butyl N-[5-[8-(tert-butoxycarbonylamino)-3-[[trans-2-cyanocyclopropane carbonyl]amino]-6-isoquinolyl]-4-methyl-3-pyridyl]carbamate (90 mg, 0.15 mmol) in dichloromethane (2 mL) and 2,2,2-trifluoroacetic acid (1 mL) was stirred for 4 h. The reaction was concentrated and purified by prep-HPLC (acetonitrile 5-40%/0.1% NH$_4$HCO$_3$ in water) to give (±)-(trans)-N-[8-amino-6-(5-amino-4-methyl-3-pyridyl)-3-isoquinolyl]-2-cyano-cyclopropanecarboxamide (31.4 mg, 60.1% yield) as a yellow solid. LCMS (ESI): R$_T$ (min)=1.49, [M+H]$^+$=359.1, method=C. $^1$H NMR (400 MHz, CD$_3$OD): 9.25 (s, 1H), 8.28 (s, 2H), 7.97 (s, 1H), 7.74 (s, 1H), 6.96 (s, 1H), 6.68 (s, 1H), 2.66-2.64 (m, 1H), 2.14 (s, 3H), 2.14-2.11 (m, 1H), 1.62-1.54 (m, 2H).

Example 91

(±)-4-(8-amino-3-((trans)-2-cyanocyclopropanecarboxamido)isoquinolin-6-yl)-3-methyl-N-(2,2,2-trifluoroethyl)benzamide (Compound 157)

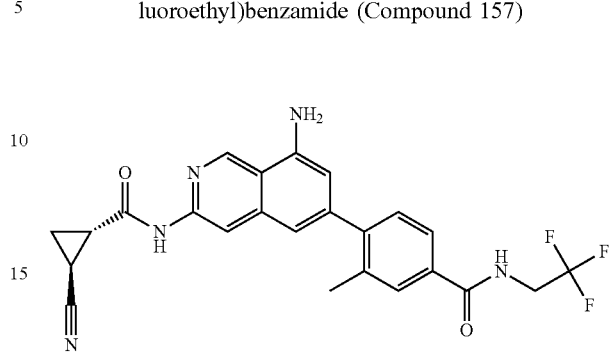

Step 1: 8-chloro-3-((trans)-2-cyanocyclopropanecarboxamido)isoquinolin-6-ylboronic Acid

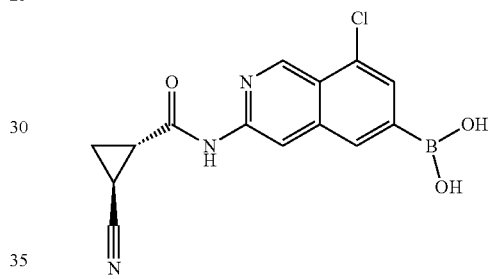

A mixture of (±)-trans-N-(6-bromo-8-chloro-3-isoquinolyl)-2-cyano-cyclopropanecarboxamide (200 mg, 0.57 mmol), bis(pinacolato)diboron (174 mg, 0.68 mmol), acetoxypotassium (140 mg, 1.43 mmol) and Pd(dppf)Cl$_2$ (21 mg, 0.03 mmol) in 1,4-dioxane (4 mL) was stirred in a sealed tube at 80° C. for 3 h. The mixture was concentrated to give (±)-[8-chloro-3-[[(trans)-2-cyanocyclopropanecarbonyl] amino]-6-isoquinolyl]boronic acid (150 mg, crude) as a black solid. This material was use in the next step without purification. LCMS (ESI): [M+H]$^+$=316.1.

Step 2: (±)-4-(8-chloro-3-((trans)-2-cyanocyclopropanecarboxamido)isoquinolin-6-yl)-3-methyl-N-(2,2,2-trifluoroethyl)benzamide

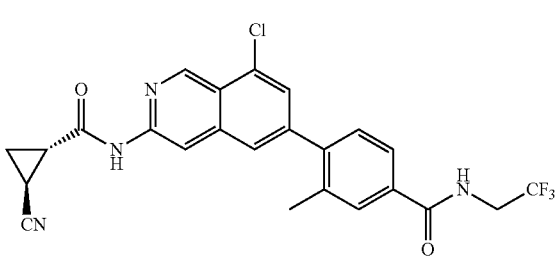 [SMILES: Cc1cc(C(=O)NCC(F)(F)F)ccc1-c1cc(Cl)c2cnc(NC(=O)[C@H]3C[C@@H]3C#N)cc2c1]

A mixture of crude (±)-[8-chloro-3-[[trans-2-cyanocyclopropanecarbonyl]amino]-6-isoquinolyl]boronic acid (150 mg, 0.48 mmol), 4-bromo-3-methyl-N-(2,2,2-trifluoroethyl)

benzamide (140 mg, 0.47 mmol), Pd(dppf)Cl$_2$ (35 mg, 0.05 mmol) and Na$_2$CO$_3$ (101 mg, 0.95 mmol) in 1,4-dioxane (4 mL), H$_2$O (0.4 mL) was heated for 3 h. The reaction was concentrated and purified by flash column chromatography (PE/EA=40%-70%) to give 4-[8-chloro-3-[[(trans)-2-cyano-cyclopropanecarbonyl] amino]-6-isoquinolyl]-3-methyl-N-(2,2,2-trifluoroethyl)benzamide (120 mg, 51.8% yield) as a yellow solid. LCMS (ESI): [M+H]$^+$=487.1.

Step 3: (±)-4-(3-(trans-2-cyanocyclopropanecarbox-amido)-8-(diphenylmethyleneamino)isoquinolin-6-yl)-3-methyl-N-(2,2,2-trifluoroethyl)benzamide

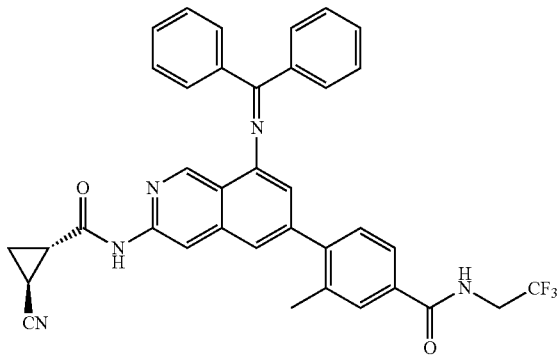 [SMILES: Cc1cc(C(=O)NCC(F)(F)F)ccc1-c1cc(N=C(c2ccccc2)c2ccccc2)c2cnc(NC(=O)[C@H]3C[C@@H]3C#N)cc2c1]

A mixture of 4-[8-chloro-3-[[(trans)-2-cyanocyclopropanecarbonyl]amino]-6-isoquinolyl]-3-methyl-N-(2,2,2-trifluoroethyl)benzamide (100 mg, 0.21 mmol), benzophenone imine (75 mg, 0.41 mmol), Cs$_2$CO$_3$ (134 mg, 0.41 mmol), Pd$_2$(dba)$_3$ (38 mg, 0.04 mmol) and Xantphos (48 mg, 0.08 mmol) in N,N-dimethylformamide (3 mL) and toluene (1 mL) was stirred at 140° C. for 3 h. The reaction was cooled to rt, diluted with water (10 mL) and extracted with EA (20 mL×2). The combined EA extracts were concentrated in vacuo to give crude 4-[8-(benzhydrylideneamino)-3-[[(1R,2R)-2-cyanocyclopropanecarbonyl]amino]-6-isoquinolyl]-3-methyl-N-(2,2,2-trifluoroethyl)benzamide (240 mg, 65.8% yield) as a brown oil. This crude material was used in the next step without purification. LCMS (ESI): [M+H]$^+$=632.2.

Step 4: (±)-4-(8-amino-3-((trans)-2-cyanocyclopropanecarboxamido)isoquinolin-6-yl)-3-methyl-N-(2,2,2-trifluoroethyl)benzamide

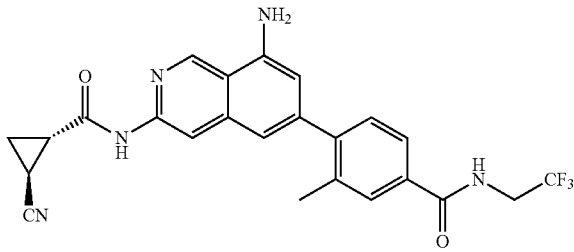 [SMILES: Cc1cc(C(=O)NCC(F)(F)F)ccc1-c1cc(N)c2cnc(NC(=O)[C@H]3C[C@@H]3C#N)cc2c1]

To a solution of (±)-4-[8-(benzhydrylideneamino)-3-[[(trans)-2-cyanocyclopropanecarbonyl]amino]-6-isoquinolyl]-3-methyl-N-(2,2,2-trifluoroethyl)benzamide (240 mg, 0.14 mmol) in N,N-dimethylformamide (2 mL) and H$_2$O (0.5 mL) was added 2 drops of TFA. The resulting mixture was stirred for 1 h. This reaction mixture was purified by prep-HPLC (acetonitrile 20-50%/0.1% NH$_4$HCO$_3$ in water) to give (±)-4-[8-amino-3-[[(trans)-2-cyanocyclopropanecarbonyl]amino]-6-isoquinolyl]-3-methyl-N-(2,2,2-trifluoroethyl)benzamide (16.4 mg, 26% yield) as yellow solid.

LCMS (ESI): R$_T$(min)=1.80, [M+H]$^+$=468.1, method=C. $^1$H NMR (400 MHz, CD$_3$OD): 9.25 (s, 1H), 8.28 (s, 1H), 7.82 (s, 1H), 7.76 (d, J=7.6 Hz, 1H), 7.40 (d, J=7.6 Hz, 1H), 6.97 (s, 1H), 4.17-4.10 (m, 2H), 2.67-2.62 (m, 1H), 2.36 (s, 3H), 2.14-2.09 (m, 1H), 1.62-1.52 (m, 2H).

Example 92

(±)-trans-N-(8-amino-6-(4-methyl-2-oxooxazol-3(2H)-yl)isoquinolin-3-yl)-2-cyanocyclopropanecarboxamide (Compound 159)

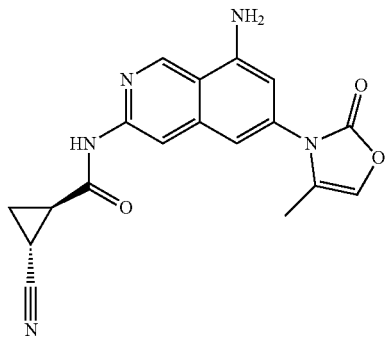 [SMILES: Cc1coc(=O)n1-c1cc(N)c2cnc(NC(=O)[C@@H]3C[C@H]3C#N)cc2c1]

Step 1: 6-bromo-8-chloro-N,N-bis(4-methoxybenzyl)isoquinolin-3-amine

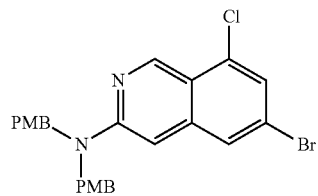

To a solution of NaH (1.25 g, 31 mmol) in N,N-Dimethylformamide (50 mL) was added 6-bromo-8-chloro-isoquinolin-3-amine (2.0 g, 7.77 mmol) and the resulting mixture was stirred for 30 min at 0° C. 4-Methoxybenzyl chloride (2.2 mL, 16 mmol) was added. The mixture was stirred overnight at room temperature. The mixture was quenched with sat. NH$_4$Cl and diluted with ethyl acetate (200 mL). The resulting mixture was washed with water and brine. The organic layer was dried over sodium sulfate, filtered and concentrated in vacuo. The residue was purified by silica gel column chromatography (EA:PE=1:10) to give 6-bromo-8-chloro-N,N-bis[(4-methoxyphenyl)methyl]isoquinolin-3-amine (2.8 g, 72% yield) as a yellow solid. LCMS (ESI) [M+H]$^+$=497.1.

Step 2: tert-butyl 3-(bis(4-methoxybenzyl)amino)-8-chloroisoquinolin-6-ylcarbamate

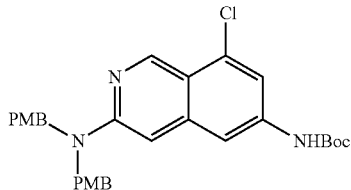

A mixture of Pd$_2$(dba)$_3$ (0.94 g, 1.03 mmol), Xantphos (1.12 g, 1.94 mmol), K$_2$CO$_3$ (1.87 g, 13.55 mmol), tert-butyl carbamate (1.4 g, 11.95 mmol) and 6-bromo-8-chloro-N,N-bis[(4-methoxyphenyl) methyl]isoquinolin-3-amine (2.8 g, 5.62 mmol) in 1,4-dioxane (100 mL) was stirred overnight at 90° C. under Ar. The mixture was directly purified by silica gel column chromatography (EA:PE=1:10 to 1:8) to give tert-butyl N-[3-[bis[(4-methoxyphenyl)methyl]amino]-8-chloro-6-isoquinolyl]carbamate (2.4 g, 80% yield) as a yellow solid. LCMS (ESI) [M+H]$^+$=534.2.

Step 3: 8-chloro-N3,N3-bis(4-methoxybenzyl)isoquinoline-3,6-diamine

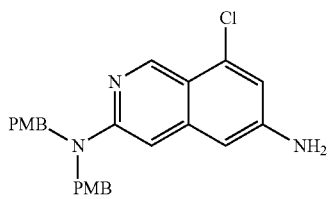

A solution of tert-butyl N-[3-[bis[(4-methoxyphenyl)methyl]amino]-8-chloro-6-isoquinolyl]carbamate (2.4 g, 4.49 mmol) and Cs$_2$CO$_3$ (4.8 g, 14.72 mmol) in 1,4-dioxane (40 mL) and N,N-dimethylformamide (40 mL) was stirred overnight at 130° C. The mixture was diluted with ethyl acetate (100 mL) and washed with water and brine. The organic layer was dried over sodium sulfate, filtered and concentrated in vacuo. The residue was purified by silica gel chromatography (EA:PE=1:2) to give 8-chloro-N3,N3-bis[(4-methoxyphenyl)methyl]isoquinoline-3,6-diamine (900 mg, 46% yield) as a red solid. LCMS (ESI) [M+H]$^+$=434.2.

Step 4: 2-oxopropyl 3-(bis(4-methoxybenzyl)amino)-8-chloroisoquinolin-6-ylcarbamate

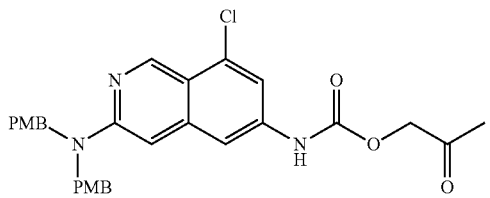

To a stirred solution of triphosgene (1.2 g, 4.04 mmol) in tetrahydrofuran (20 mL) was added a solution of triethylamine (3 mL, 21.52 mmol) and 8-chloro-N3,N3-bis[(4-methoxyphenyl)methyl]isoquinoline-3,6-diamine (900 mg, 2.07 mmol) in tetrahydrofuran (20 mL) at 0° C. The mixture was stirred at 0° C. for 1 h followed by the addition of hydroxyacetone (2.0 g, 27 mmol). The reaction mixture was stirred at room temperature overnight. The mixture was diluted with ethyl acetate (100 mL) and washed with brine. The organic layer was dried over sodium sulfate, filtered and concentrated in vacuo. The residue was purified by silica gel column (EA:PE=1:2) to give acetonyl N-[3-[bis[(4-methoxyphenyl)methyl]amino]-8-chloro-6-isoquinolyl]carbamate (650 mg, 59% yield) as a brown solid. LCMS (ESI) [M+H]$^+$=534.2.

Step 5: 3-(8-chloro-3-(4-methoxybenzylamino)isoquinolin-6-yl)-4-methyloxazol-2(3H)-one

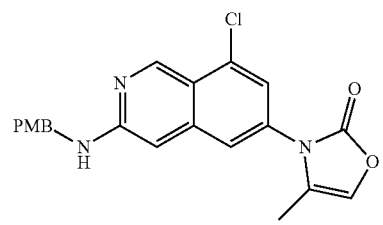

A solution of acetonyl N-[3-[bis[(4-methoxyphenyl)methyl]amino]-8-chloro-6-isoquinolyl]carbamate (640 mg, 1.2 mmol) in acetic acid (40 mL) was heated to 120° C. for 2 h.

After the solvent was evaporated, the residue was dissolved in dichloromethane (10 mL) and 2,2,2-trifluoroacetic acid (2 mL) and continued to stir for 1 h at room temperature. The reaction was concentrated to give crude 3-[8-chloro-3-[(4-methoxyphenyl)methylamino]-6-isoquinolyl]-4-methyl-oxazol-2-one (430 mg, 91% yield) as a red oil, which was directly used in the next reaction. LCMS (ESI) [M+H]$^+$=396.1.

Step 6: 3-(3-amino-8-chloroisoquinolin-6-yl)-4-methyloxazol-2(3H)-one

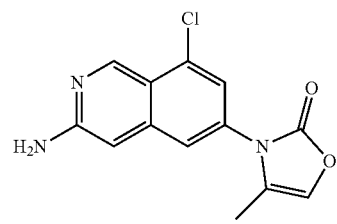 [SMILES: Cc1coc(=O)n1-c1cc(Cl)c2cnc(N)cc2c1]

A solution of 3-[8-chloro-3-[(4-methoxyphenyl)methylamino]-6-isoquinolyl]-4-methyl-oxazol-2-one (430 mg, 1.09 mmol) in 2,2,2-trifluoroacetic acid (8 mL) was heated at 45° C. for 1 h. The reaction was concentrated and the residue was re-dissolved in DCM (50 mL) and washed with sat. sodium bicarbonate and brine. The organic layer was dried over sodium sulfate, filtered and concentrated in vacuo. The residue was purified by silica gel column chromatography (EA:PE=1:2 to EA:DCM=1:1) to give 3-(3-amino-8-chloro-6-isoquinolyl)-4-methyl-oxazol-2-one (160 mg, 53% yield) as a red solid. LCMS (ESI) [M+H]$^+$=276.0.

Step 7: (±)-trans-N-(8-chloro-6-(4-methyl-2-oxooxazol-3(2H)-yl)isoquinolin-3-yl)-2-cyanocyclopropanecarboxamide

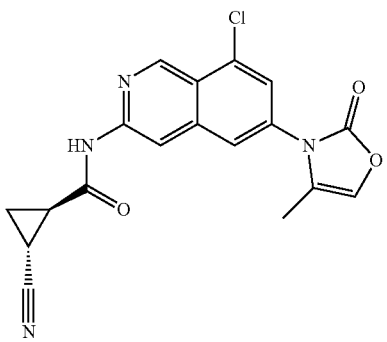 [SMILES: Cc1coc(=O)n1-c1cc(Cl)c2cnc(NC(=O)[C@@H]3C[C@H]3C#N)cc2c1]

(COCl)₂ (0.09 mL, 1.06 mmol) was added dropwise to a suspension of (±)-trans-2-cyanocyclopropanecarboxylic acid (50 mg, 0.45 mmol) and DMF (3 mg, 0.04 mmol) in dichloromethane (5 mL) at 0° C. The mixture was stirred at room temperature for another 1 h. The mixture was evaporated at room temperature to remove most of the DCM and (COCl)₂. The residue was suspended in DCM (5 mL) and was added dropwise to a mixture of 3-(3-amino-8-chloro-6-isoquinolyl)-4-methyl-oxazol-2-one (80 mg, 0.29 mmol) and pyridine (0.5 mL, 6.18 mmol) in dichloromethane (5 mL) at 0° C. The reaction mixture was stirred at 0° C. for another 0.5 h. The reaction mixture was diluted with DCM (50 mL), washed with H₂O (20 mL). The organic layer was separated, dried over Na₂SO₄, filtered and evaporated. The residue was purified by silica gel chromatography (EA: PE=1:2) to give (±)-(trans)-N-[8-chloro-6-(4-methyl-2-oxo-oxazol-3-yl)-3-isoquinolyl]-2-cyano-cyclopropanecarboxamide (40 mg, 37% yield) as a light yellow solid. LCMS (ESI) [M+H]⁺=369.1.

Step 8: tert-butyl 3-(trans-2-cyanocyclopropanecarboxamido)-6-(4-methyl-2-oxooxazol-3(2H)-yl)isoquinolin-8-ylcarbamate

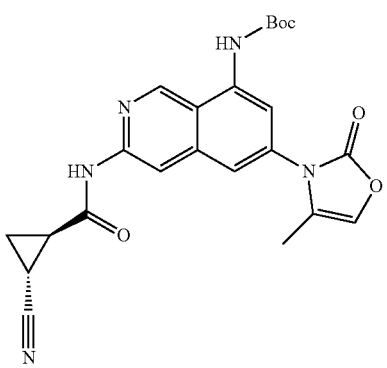 [SMILES: Cc1coc(=O)n1-c1cc(NC(=O)OC(C)(C)C)c2cnc(NC(=O)[C@@H]3C[C@H]3C#N)cc2c1]

A mixture of tert-butyl carbamate (230 mg, 1.96 mmol), Pd₂(dba)₃ (35 mg, 0.04 mmol), Brettphos (35 mg, 0.07 mmol), Cs₂CO₃ (210 mg, 0.64 mmol) and trans-N-[8-chloro-6-(4-methyl-2-oxo-oxazol-3-yl)-3-isoquinolyl]-2-cyano-cyclopropanecarboxamide (70 mg, 0.19 mmol) in 1,4-dioxane (10 mL) was heated at 90° C. for 2 days under Ar. The mixture was directly purified by silica gel column (EA:PE=1:1 to 100% EA) to give (±)-tert-butyl N-[3-[[(trans)-2-cyanocyclopropanecarbonyl]amino]-6-(4-methyl-2-oxo-oxazol-3-yl)-8-isoquinolyl]carbamate (35 mg, 41% yield) as a yellow solid. LCMS (ESI) [M+H]⁺=450.1.

Step 9: trans-N-(8-amino-6-(4-methyl-2-oxooxazol-3(2H)-yl)isoquinolin-3-yl)-2-cyanocyclopropanecarboxamide

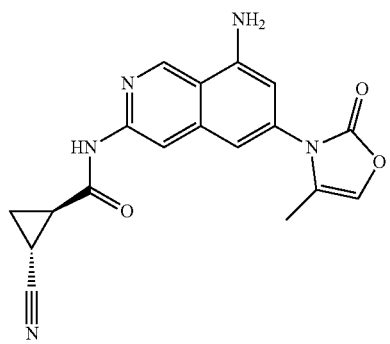

A solution of tert-butyl N-[3-[[trans-2-cyanocyclopropanecarbonyl]amino]-6-(4-methyl-2-oxo-oxazol-3-yl)-8-isoquinolyl]carbamate (30 mg, 0.07 mmol) in dichloromethane (4 mL) and 2,2,2-trifluoroacetic acid (1 mL) was stirred for 1 h at room temperature. After the reaction was concentrated, the residue was neutralized by ammonium in MeOH. The resulting mixture was purified by reverse phase chromatography (acetonitrile 17-47/0.05% sodium bicarbonate in water) to give (±)-(trans)-N-[8-amino-6-(4-methyl-2-oxo-oxazol-3-yl)-3-isoquinolyl]-2-cyano-cyclopropanecarboxamide (2.7 mg, 12% yield) as a white solid. LCMS (ESI): R$_T$ (min)=1.572, [M+H]⁺=350.1, method=C; ¹H-NMR (400 MHz, CD₃OD): δ 9.26 (s, 1H), 8.33 (s, 1H), 7.02 (s, 1H), 6.65 (s, 1H), 4.65 (s, 1H), 2.67-2.62 (m, 1H), 2.15-2.09 (m, 1H), 2.01 (s, 3H), 1.62-1.52 (m, 2H).

Example 93

(±)-trans-N-(8-amino-6-(2-methyl-6-oxopiperazin-1-yl)isoquinolin-3-yl)-2-cyanocyclopropanecarboxamide (Compound 160)

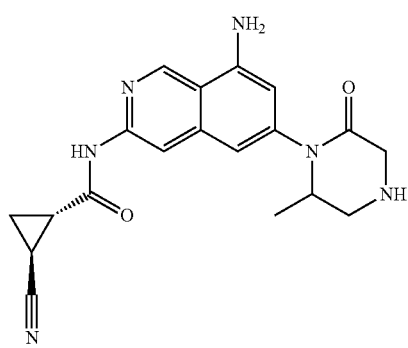 [SMILES: CC1CNCC(=O)N1c1cc(N)c2cnc(NC(=O)[C@H]3C[C@@H]3C#N)cc2c1]

Step 1: tert-butyl 3-methyl-5-oxopiperazine-1-carboxylate

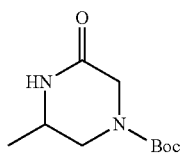

A mixture of 6-methylpiperazin-2-one (200 mg, 1.75 mmol), (Boc)$_2$O (420 mg, 1.93 mmol) and Na$_2$CO$_3$ (370 mg, 3.49 mmol) in 1,4-dioxane (8 mL) and water (2 mL) was stirred at 25° C. for 4 h. The reaction was diluted with water (10 ml) and EtOAc (20 ml). The organics were then separated and dried (Na$_2$SO$_4$). The residue was concentrated to give tert-butyl 3-methyl-5-oxo-piperazine-1-carboxylate (350 mg, 93.2% yield) as a white solid. LCMS (ESI) [M+H]$^+$=215.1.

Step 2: tert-butyl 4-(8-chloro-3-(trans-2-cyanocyclopropanecarboxamido)isoquinolin-6-yl)-3-methyl-5-oxopiperazine-1-carboxylate

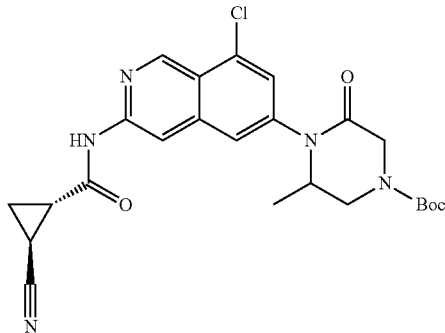 [SMILES: CC1CN(C(=O)OC(C)(C)C)CC(=O)N1c1cc(Cl)c2cnc(NC(=O)[C@H]3C[C@@H]3C#N)cc2c1]

A mixture of trans-N-(6-bromo-8-chloro-3-isoquinolyl)-2-cyano-cyclopropanecarboxamide (200 mg, 0.57 mmol), Pd$_2$(dba)$_3$ (100 mg, 0.11 mmol), Xantphos (130 mg, 0.22 mmol), K$_3$PO$_4$ (360 mg, 1.7 mmol) and tert-butyl-3-methyl-5-oxo-piperazine-1-carboxylate (170 mg, 0.79 mmol) in 1,4-dioxane (15 mL) was stirred at 90° C. for 3 h under Ar. The mixture was directly purified by silica gel column (EA:PE=1:2 to 1:1) to give tert-butyl 4-[8-chloro-3-[(trans-2-cyanocyclopropanecarbonyl)amino]-6-isoquinolyl]-3-methyl-5-oxo-piperazine-1-carboxylate (100 mg, 36.2% yield) as a white solid. LCMS (ESI) [M+H]$^+$=484.1.

Step 3: tert-butyl 4-(8-(tert-butoxycarbonylamino)-3-(trans-2-cyanocyclopropanecarboxamido)isoquinolin-6-yl)-3-methyl-5-oxopiperazine-1-carboxylate

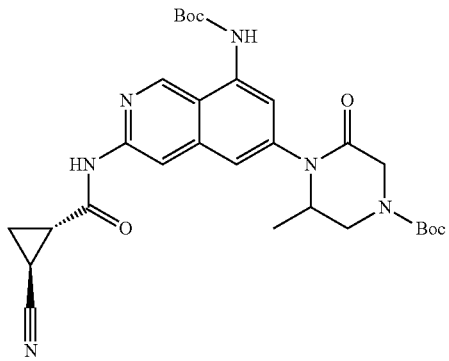 [SMILES: CC1CN(C(=O)OC(C)(C)C)CC(=O)N1c1cc(NC(=O)OC(C)(C)C)c2cnc(NC(=O)[C@H]3C[C@@H]3C#N)cc2c1]

A mixture of tert-butyl carbamate (200 mg, 1.71 mmol), Pd$_2$(dba)$_3$ (32 mg, 0.03 mmol), Brettphos (20 mg, 0.04 mmol), Cs$_2$CO$_3$ (160 mg, 0.49 mmol) and tert-butyl 4-[8-chloro-3-[(trans-2-cyanocyclopropanecarbonyl)amino]-6-isoquinolyl]-3-methyl-5-oxo-piperazine-1-carboxylate (80 mg, 0.17 mmol) in 1,4-dioxane (10 mL) was stirred at 90° C. for 3 h under Ar. The mixture was directly purified by silica gel column (EA:PE=2:1 to 4:1) to give tert-butyl 4-[8-(tert-butoxycarbonylamino)-3-[(trans-2-cyanocyclopropanecarbonyl)amino]-6-isoquinolyl]-3-methyl-5-oxo-piperazine-1-carboxylate (50 mg, 0.09 mmol, 53.6% yield) as a yellow solid. LCMS (ESI) [M+H]$^+$=565.1.

Step 4: trans-N-(8-amino-6-(2-methyl-6-oxopiperazin-1-yl)isoquinolin-3-yl)-2-cyanocyclopropanecarboxamide

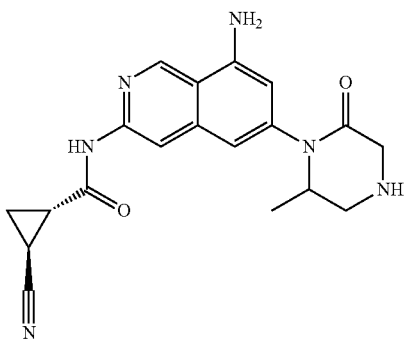 [SMILES: CC1CNCC(=O)N1c1cc(N)c2cnc(NC(=O)[C@H]3C[C@@H]3C#N)cc2c1]

To a solution of tert-butyl 4-[8-(tert-butoxycarbonylamino)-3-[(trans-2-cyanocyclopropanecarbonyl)amino]-6-isoquinolyl]-3-methyl-5-oxo-piperazine-1-carboxylate (40 mg, 0.07 mmol) dissolved in dichloromethane (4 mL) was added TFA (2 mL, 0.14 mmol). The mixture was stirred at room temperature for 2 h. The reaction was concentrated to dryness. The residue was purified by reverse phase chromatography (acetonitrile 0-50/0.1% NH$_4$HCO$_3$ in water) to afford trans-N-[8-amino-6-(2-methyl-6-oxo-piperazin-1-yl)-3-isoquinolyl]-2-cyano-cyclopropanecarboxamide (9.7 mg, 37.6% yield) as a white solid. LCMS (ESI): R$_T$ (min)=1.35, [M+H]$^+$=365.1, method=C; $^1$NMR (400 MHz, DMSO-d$_6$): δ 11.09 (s, 1H), 9.27 (s, 1H), 8.16 (s, 1H), 6.79 (s, 1H), 6.44 (s, 1H), 6.30 (s, 2H), 4.05-3.92 (m, 2H), 3.17-3.12 (m, 2H), 2.78-2.74 (m, 3H), 2.17-2.11 (m, 1H), 1.61-1.56 (m, 1H), 1.45-1.42 (m, 1H), 1.01 (d, J=6.4 Hz, 3H).

Example 94

(±)-trans-N-(8-amino-7-fluoro-6-((S)-4-methyl-2-oxooxazolidin-3-yl)isoquinolin-3-yl)-2-cyanocyclopropanecarboxamide (Compound 161)

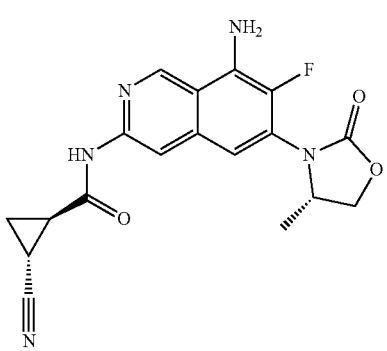

Step 1: trans-N-(8-chloro-7-fluoro-6-iodoisoquinolin-3-yl)-2-cyanocyclopropanecarboxamide

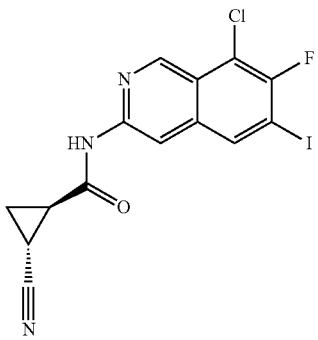 [SMILES: N#C[C@@H]1C[C@H]1C(=O)Nc1cc2cc(I)c(F)c(Cl)c2cn1]

A mixture of (±)-trans-2-cyanocyclopropanecarboxylic acid (290 mg, 2.61 mmol), oxalyl dichloride (0.2 mL, 2.36 mmol) in DCM (3 mL) and one drop DMF was stirred for 0.5 h. The reaction mixture was concentrated. To a solution of 8-chloro-7-fluoro-6-iodo-isoquinolin-3-amine (700 mg, 2.17 mmol) in DCM (7 mL) and pyridine (0.5 mL) was added the concentrated acid chloride mixture in portions at room temperature. The mixture was stirred for 1 h. The reaction was concentrated to dryness and the residue was taken up in EtOAc (50 mL) and adjusted pH to 7-8 with sat NaHCO$_3$. The organic layer was washed with 100 mL saturated brine solution. The organics were then separated and dried (NaSO$_4$) before concentration to dryness. The residue was purified with silica chromatography (PE:EA=2:1 to PE:EA=1:1) to give the title compound as a yellow solid (730 mg, 40.2% yield). LCMS (ESI) [M+H]$^+$=416.0.

Step 2: trans-N-(8-chloro-7-fluoro-6-((S)-4-methyl-2-oxooxazolidin-3-yl)isoquinolin-3-yl)-2-cyanocyclopropanecarboxamide

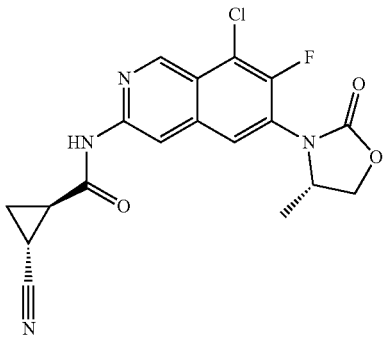 [SMILES: C[C@H]1COC(=O)N1c1cc2cc(NC(=O)[C@@H]3C[C@H]3C#N)ncc2c(Cl)c1F]

A mixture of trans-N-(8-chloro-7-fluoro-6-iodo-3-isoquinolyl)-2-cyano-cyclopropanecarboxamide (730 mg, 1.76 mmol), (4S)-4-methyloxazolidin-2-one (270 mg, 2.67 mmol), CuI (667 mg, 3.51 mmol), N1,N2-dimethylethane-1,2-diamine (616 mg, 7 mmol) in 1,4-dioxane (10 mL) was heated at 90° C. for 3 h under Ar. The reaction was concentrated to dryness. The residue was purified with silica gel chromatography (PE:EA=4:1 to PE:EA=1:1) to give the title compound as a yellow solid (460 mg, 40.9% yield) in the end. LCMS (ESI) [M+H]$^+$=389.1.

Step 3: tert-butyl 3-(trans-2-cyanocyclopropanecarboxamido)-7-fluoro-6-((S)-4-methyl-2-oxooxazolidin-3-yl)isoquinolin-8-ylcarbamate

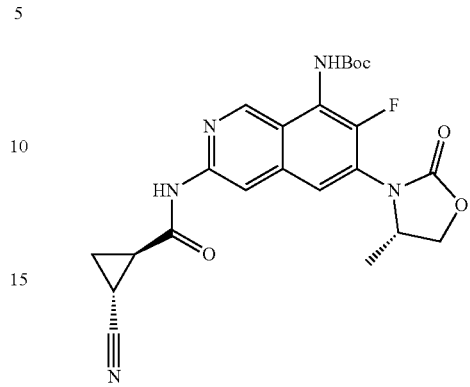

A mixture of trans-N-[8-chloro-7-fluoro-6-[(4S)-4-methyl-2-oxo-oxazolidin-3-yl]-3-isoquinolyl]-2-cyano-cyclopropanecarboxamide (450 mg, 1.16 mmol), tert-butyl carbamate (1.3 g, 11.1 mmol), Brettphos (120 mg, 0.22 mmol), Pd$_2$(dba)$_3$ (210 mg, 0.23 mmol), and Cs$_2$CO$_3$ (1.1 g, 3.37 mmol) in 1,4-dioxane (10 mL) was heated at 90° C. for 3 h under Ar. The reaction was concentrated to dryness. The residue was purified by silica gel chromatography (PE:EA=4:1 to PE:EA=1:1) to give the title compound as a white solid (55 mg, 6.2% yield). LCMS (ESI) [M+H]$^+$=470.2

Step 4: trans-N-(8-amino-7-fluoro-6-((S)-4-methyl-2-oxooxazolidin-3-yl)isoquinolin-3-yl)-2-cyanocyclopropanecarboxamide

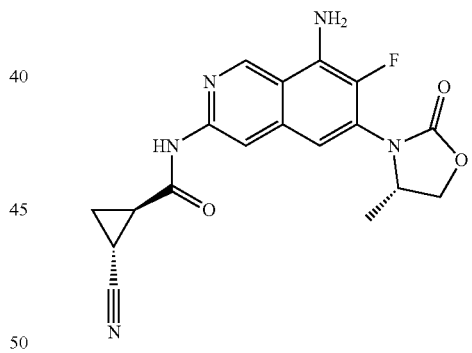

A mixture of tert-butyl N-[3-[[trans-2-cyanocyclopropanecarbonyl]amino]-7-fluoro-6-[(4S)-4-methyl-2-oxo-oxazolidin-3-yl]-8-isoquinolyl]carbamate (55 mg, 0.12 mmol), TFA (0.5 mL, 0.12 mmol) in dichloromethane (2 mL) was stirred at room temperature for 1 h. The reaction was concentrated to dryness and the residue was taken up in MeOH (2 mL) and adjusted pH to 7-8 with sat NaHCO$_3$. The mixture was purified by prep-HPLC (5%-95% methanol and 0.8 g/L NH$_4$HCO$_3$ in water) to give the title compound as a yellow solid (16.7 mg, 37.8% yield.) LCMS (ESI): RT (min)=1.65, [M+H]$^+$=370.1, Method=B. $^1$NMR (400 MHz, DMSO-d6) δ 11.14 (s, 1H), 9.39 (s, 1H), 8.22 (s, 1H), 7.06 (d, J=6.4 Hz, 1H), 6.39 (s, 2H), 4.67 (t, J=8.0 Hz, 1H), 4.53 (d, J=7.2 Hz, 1H), 4.06 (t, J=8.0 Hz, 1H), 2.75-2.71 (m, 1H), 2.15-2.12 (m, 1H), 1.61-1.57 (m, 1H), 1.42-1.40 (m, 1H), 1.15 (d, J=6.0 Hz, 3H).

Example 95

(1S,2S)—N-(8-amino-6-(5-methyl-2-oxo-2,3-dihydrobenzo[d]oxazol-6-yl)isoquinolin-3-yl)-2-cyanocyclopropane-1-carboxamide (Compound 162) and (1R,2R)—N-(8-amino-6-(5-methyl-2-oxo-2,3-dihydrobenzo[d]oxazol-6-yl)isoquinolin-3-yl)-2-cyanocyclopropane-1-carboxamide (Compound 163)

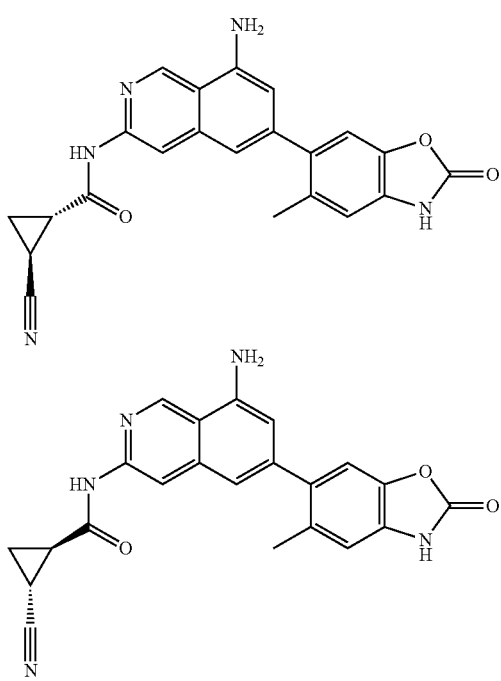

The title compounds were prepared using procedures as described for (±)-trans-N-(8-amino-6-(5-methyl-2-oxo-2,3-dihydrobenzo[d]oxazol-6-yl)isoquinolin-3-yl)-2-cyanocyclopropanecarboxamide. The single enantiomers were isolated by chiral SFC. Compound 162: LCMS (ESI): RT (min)=3.83, [M+H]$^+$=400.1, Method=J. Compound 163: LCMS (ESI): RT (min)=3.83, [M+H]$^+$=400.1, Method=J.

Example 96

(1S,2S)—N-(8-amino-6-((R)-4-methyl-2-oxooxazolidin-3-yl)isoquinolin-3-yl)-2-fluorocyclopropane-1-carboxamide (Compound 164)

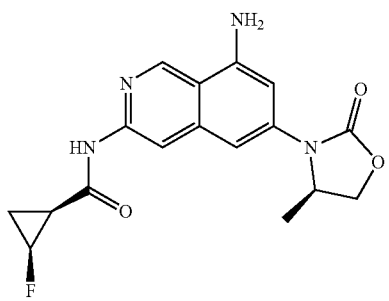 [SMILES: C[C@@H]1COC(=O)N1c1cc(N)c2cnc(NC(=O)[C@@H]3C[C@@H]3F)cc2c1]

The title compound was prepared using a procedure as described for (1S,2S)—N-(8-amino-6-((S)-4-methyl-2-oxooxazolidin-3-yl)isoquinolin-3-yl)-2-fluorocyclopropanecarboxamide (Compound 128). $^1$HNMR (400 MHz, DMSO-d6) δ 10.7 (s, 1H), 9.19 (s, 1H), 8.19 (s, 1H), 7.0 (s, 1H), 6.93 (s, 1H), 4.84-5.02 (m, 1H), 4.58-4.72 (m, 1H), 4.56 (t, 1H), 4.04-4.07 (m, 1H), 2.23-2.51 (m, 1H), 1.63-1.70 (m, 1H), 1.14-1.3 (m, 4H)

Example 97

(1S,2R)—N-(8-amino-6-((R)-4-methyl-2-oxooxazolidin-3-yl)isoquinolin-3-yl)-2-fluorocyclopropane-1-carboxamide (Compound 165)

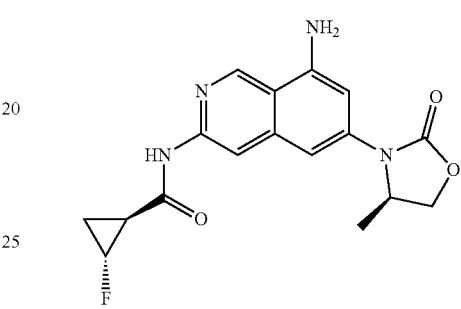

The title compound was prepared using a procedure as described for (1S,2S)—N-(8-amino-6-((S)-4-methyl-2-oxooxazolidin-3-yl)isoquinolin-3-yl)-2-fluorocyclopropanecarboxamide (Compound 128). LCMS (ESI): RT (min)=1.52, [M+H]+=345.2, Method=B.

Example 98

(1S,2S)—N-(8-amino-6-(5-amino-4-methylpyridin-3-yl)isoquinolin-3-yl)-2-cyanocyclopropane-1-carboxamide (Compound 166) and (1R,2R)—N-(8-amino-6-(5-amino-4-methylpyridin-3-yl)isoquinolin-3-yl)-2-cyanocyclopropane-1-carboxamide (Compound 167)

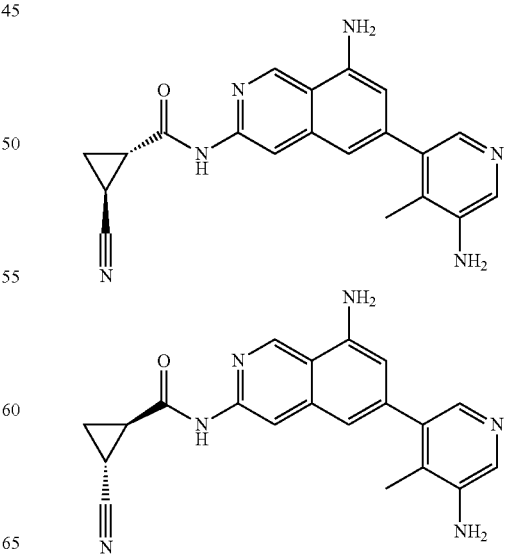

The title compound was prepared using a procedure as described for (±)-trans-N-(8-amino-6-(5-amino-4-methylpyridin-3-yl)isoquinolin-3-yl)-2-cyanocyclopropanecarboxamide (Compound 156). The single isomers were isolated by chiral SFC. Compound 166: ¹H NMR (400 MHz, DMSO-d6) δ 11.08 (s, 1H), 9.32 (s, 1H), 8.21 (s, 1H), 7.94 (s, 1H), 7.64 (s, 1H), 6.82 (s, 1H), 6.53 (s, 1H), 6.31 (s, 2H), 5.18 (s, 1H), 2.73-2.77 (m, 1H), 2.12-2.14 (m, 1H), 1.59-1.61 (m, 1H), 1.40-1.57 (m, 1H). LCMS (ESI): RT (min)=2.48, [M+H]+=359.1, method=J. Compound 167: ¹H NMR (400 MHz, DMSO-d6) δ 11.08 (s, 1H), 9.31 (s, 1H), 8.21 (s, 1H), 7.93 (s, 1H), 7.64 (s, 1H), 6.82 (s, 1H), 6.53 (s, 1H), 6.31 (s, 2H), 5.18 (s, 1H), 2.73-2.77 (m, 1H), 2.12-2.14 (m, 1H), 1.59-1.61 (m, 1H), 1.40-1.57 (m, 1H). LCMS (ESI): RT (min)=2.48, [M+H]+=359.1, Method=J.

Example 99

(1S,2S)—N-(8-amino-6-(4-methylisothiazol-5-yl)isoquinolin-3-yl)-2-cyanocyclopropane-1-carboxamide (Compound 168) and (1R,2R)—N-(8-amino-6-(4-methylisothiazol-5-yl)isoquinolin-3-yl)-2-cyanocyclopropane-1-carboxamide (Compound 169)

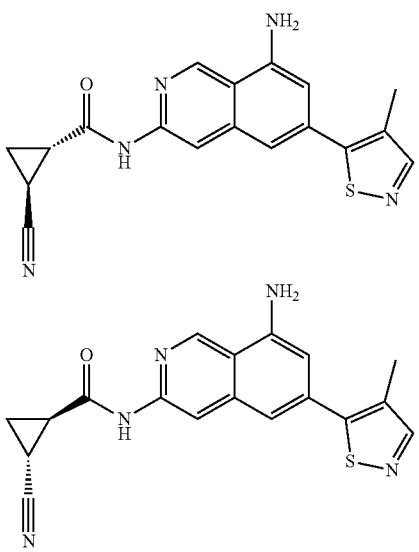

The title compound was prepared using a procedure as described for (±)-trans-N-(8-amino-6-(4-methylisothiazol-5-yl)isoquinolin-3-yl)-2-cyanocyclopropanecarboxamide (Compound 62). The single isomers were separated by chiral SFC. Compound 168: ¹H NMR (400 MHz, DMSO-d6) δ 11.18 (s, 1H), 3.34 (s, 1H), 8.48 (s, 1H), 8.29 (s, 1H), 7.09 (s, 1H), 6.73 (s, 1H), 6.55 (s, 2H), 2.74-2.76 (m, 1H), 2.40 (s, 3H), 2.08-2.17 (m, 1H), 1.62-1.63 (m, 1H), 1.40-1.45 (m, 1H). LCMS (ESI): RT (min)=4.66, [M+H]+=350.1, Method=J. Compound 169: ¹H NMR (400 MHz, DMSO-d6) δ 11.18 (s, 1H), 3.34 (s, 1H), 8.48 (s, 1H), 8.29 (s, 1H), 7.09 (s, 1H), 6.73 (s, 1H), 6.55 (s, 2H), 2.74-2.76 (m, 1H), 2.40 (s, 3H), 2.08-2.17 (m, 1H), 1.62-1.58 (m, 1H), 1.40-1.45 (m, 1H).). LCMS (ESI): RT (min)=4.66, [M+H]+=350.1, Method=J.

Example 100

(±)-trans-N-(8-amino-6-(1-methyl-1H-pyrrolo[2,3-c]pyridin-4-yl)isoquinolin-3-yl)-2-cyanocyclopropane-1-carboxamide (Compound 170)

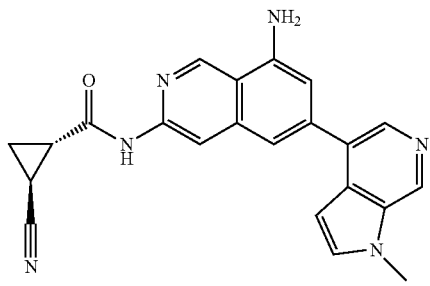 [SMILES: Cn1ccc2c(-c3cc(N)c4cnc(NC(=O)[C@H]5C[C@@H]5C#N)cc4c3)cncc21]

The title compound was prepared using procedures that are analogous to the one described for (±)-trans-N-(8-amino-6-(8-methylpyrido[3,2-b]pyrazin-7-yl)isoquinolin-3-yl)-2-cyanocyclopropane carboxamide (Compound 123). 1H NMR (400 MHz, DMSO) δ 11.09 (s, 1H), 9.34 (s, 1H), 8.86 (s, 1H), 8.29 (d, J=9.8 Hz, 2H), 7.66 (d, J=3.1 Hz, 1H), 7.22 (s, 1H), 7.00 (d, J=1.5 Hz, 1H), 6.68 (dd, J=3.0, 0.8 Hz, 1H), 6.37 (s, 2H), 3.97 (s, 3H), 2.80-2.73 (m, 1H), 2.17-2.11 (m, 1H), 1.63-1.55 (m, 1H), 1.48-1.40 (m, 1H). LCMS (ESI): RT (min)=2.76, [M+H]+=383.1, Method=J.

Example 101

(±)-trans-N-(8-amino-6-(1-methyl-1H-pyrazolo[3,4-c]pyridin-4-yl)isoquinolin-3-yl)-2-cyanocyclopropane-1-carboxamide (Compound 171)

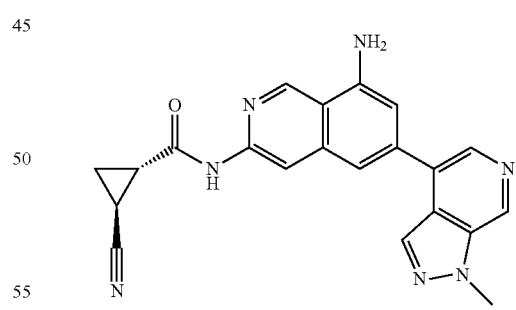

The title compound was prepared using procedures that are analogous to the one described for (±)-trans-N-(8-amino-6-(8-methylpyrido[3,2-b]pyrazin-7-yl)isoquinolin-3-yl)-2-cyanocyclopropane carboxamide (Compound 123). 1H NMR (400 MHz, DMSO) δ 11.11 (s, 1H), 9.36 (s, 1H), 9.20 (s, 1H), 8.47 (s, 1H), 8.40-8.29 (m, 2H), 7.34 (s, 1H), 7.06 (d, J=1.5 Hz, 1H), 6.44 (s, 2H), 4.24 (s, 3H), 2.77 (dd, J=10.8, 8.0 Hz, 1H), 2.19-2.09 (m, 1H), 1.65-1.56 (m, 1H), 1.49-1.39 (m, 1H). LCMS (ESI): RT (min)=3.09, [M+H]+=384.1, Method=J.

Example 102

(±)-trans-N-(8-amino-6-(2-methyl-2H-pyrazolo[3,4-c]pyridin-4-yl)isoquinolin-3-yl)-2-cyanocyclopropane-1-carboxamide (Compound 172)

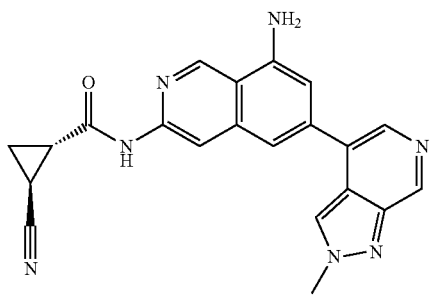 [SMILES: Cn1cc2c(-c3cc(N)c4cnc(NC(=O)[C@H]5C[C@@H]5C#N)cc4c3)cncc2n1]

The title compound was prepared using procedures that are analogous to the one described for (±)-trans-N-(8-amino-6-(8-methylpyrido[3,2-b]pyrazin-7-yl)isoquinolin-3-yl)-2-cyanocyclopropane carboxamide (Compound 123). 1H NMR (400 MHz, DMSO) δ 11.11 (s, 1H), 9.35 (s, 1H), 9.15 (s, 1H), 8.76 (s, 1H), 8.32 (d, J=14.3 Hz, 2H), 7.33 (s, 1H), 7.02 (d, J=1.5 Hz, 1H), 6.39 (s, 2H), 4.30 (s, 3H), 2.75 (d, J=5.9 Hz, 1H), 2.19-2.09 (m, 1H), 1.64-1.55 (m, 1H), 1.49-1.39 (m, 1H). LCMS (ESI): RT (min)=2.70, [M+H]+=384.1, Method=J.

Example 103

(±)-trans-N-(8-amino-6-(5,5-dimethyl-2-oxooxazolidin-3-yl)isoquinolin-3-yl)-2-cyanocyclopropane-1-carboxamide (Compound 173)

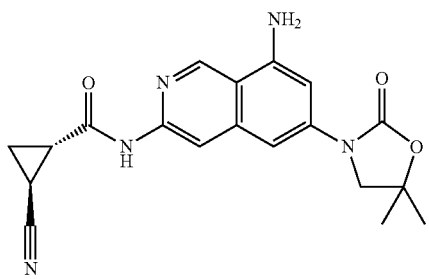 [SMILES: CC1(C)CN(c2cc(N)c3cnc(NC(=O)[C@H]4C[C@@H]4C#N)cc3c2)C(=O)O1]

The title compound was prepared using procedures that are analogous to the one described for (1S,2S)—N-(8-amino-6-((S)-4-methyl-2-oxooxazolidin-3-yl)isoquinolin-3-yl)-2-fluorocyclopropanecarboxamide (Compound 128). 1H NMR (400 MHz, DMSO) δ 11.01 (s, 1H), 9.19 (s, 1H), 8.12 (s, 1H), 7.21 (d, J=2.1 Hz, 1H), 6.81 (d, J=1.8 Hz, 1H), 6.34 (s, 2H), 3.89 (s, 2H), 2.74 (dd, J=11.4, 7.2 Hz, 1H), 2.18-2.09 (m, 1H), 1.60-1.55 (m, 1H), 1.48 (s, 6H), 1.42 (dt, J=10.2, 5.1 Hz, 1H). LCMS (ESI): RT (min)=3.58, [M+H]+=366.1, Method=J.

Example 104 trans-N-(8-amino-6-((S)-4-isopropyl-2-oxooxazolidin-3-yl)isoquinolin-3-yl)-2-cyanocyclopropane-1-carboxamide (Compound 174)

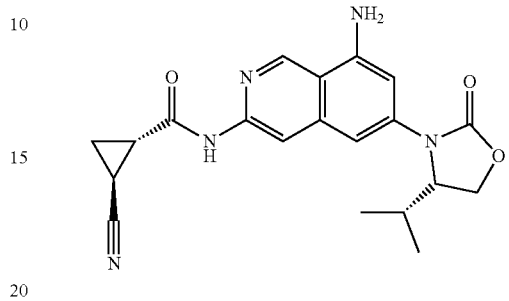

The title compound was prepared using procedures that are analogous to the one described for (1S,2S)—N-(8-amino-6-((S)-4-methyl-2-oxooxazolidin-3-yl)isoquinolin-3-yl)-2-fluorocyclopropanecarboxamide (Compound 128). 1H NMR (400 MHz, DMSO) δ 11.03 (s, 1H), 9.21 (s, 1H), 8.15 (s, 1H), 7.00 (s, 2H), 6.35 (s, 2H), 4.63 (dd, J=8.4, 4.1 Hz, 1H), 4.42 (t, J=8.9 Hz, 1H), 4.29 (dd, J=9.0, 4.0 Hz, 1H), 2.73 (d, J=12.9 Hz, 1H), 2.16-2.07 (m, 2H), 1.61-1.55 (m, 1H), 1.42 (dt, J=9.3, 4.7 Hz, 1H), 0.88 (d, J=7.0 Hz, 3H), 0.75 (d, J=6.8 Hz, 3H). LCMS (ESI): RT (min)=3.89, [M+H]+=380.1, Method=J.

Example 105 trans-N-(8-amino-6-((R)-4-isopropyl-2-oxooxazolidin-3-yl)isoquinolin-3-yl)-2-cyanocyclopropane-1-carboxamide (Compound 175)

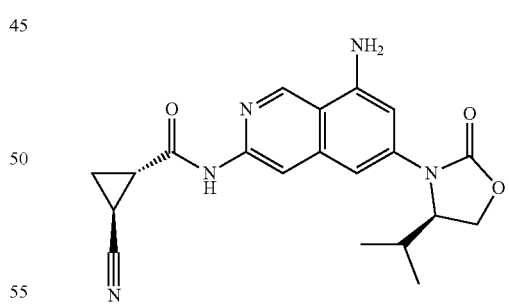

The title compound was prepared using procedures that are analogous to the one described for (1S,2S)—N-(8-amino-6-((S)-4-methyl-2-oxooxazolidin-3-yl)isoquinolin-3-yl)-2-fluorocyclopropanecarboxamide (Compound 128). 1H NMR (400 MHz, DMSO) δ 11.03 (s, 1H), 9.21 (s, 1H), 8.15 (s, 1H), 7.00 (s, 2H), 6.35 (s, 2H), 4.69-4.59 (m, 1H), 4.42 (t, J=8.9 Hz, 1H), 4.30 (dd, J=8.9, 4.0 Hz, 1H), 2.79-2.69 (m, 1H), 2.18-2.06 (m, 2H), 1.64-1.54 (m, 1H), 1.46-1.37 (m, 1H), 0.88 (d, J=7.0 Hz, 3H), 0.75 (d, J=6.8 Hz, 3H). LCMS (ESI): RT (min)=3.98, [M+H]+=380.2, method=J.

Example 106

(±)-trans-N-(8-amino-6-(2-oxooxazolidin-3-yl)iso-quinolin-3-yl)-2-cyanocyclopropane-1-carboxamide (Compound 176)

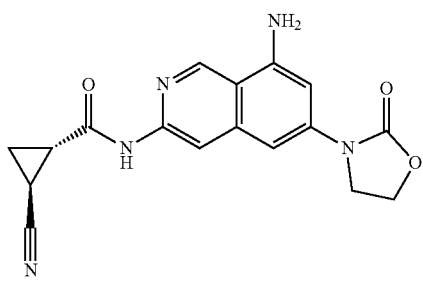 [SMILES: N#C[C@H]1C[C@@H]1C(=O)Nc1cc2cc(N3CCOC3=O)cc(N)c2cn1]

The title compound was prepared using procedures that are analogous to the one described for (1S,2S)—N-(8-amino-6-((S)-4-methyl-2-oxooxazolidin-3-yl)isoquinolin-3-yl)-2-fluorocyclopropanecarboxamide (Compound 128). 1H NMR (400 MHz, DMSO) δ 11.01 (s, 1H), 9.19 (s, 1H), 8.14 (s, 1H), 7.20 (d, J=2.0 Hz, 1H), 6.86 (d, J=1.8 Hz, 1H), 6.35 (s, 2H), 4.47-4.40 (m, 2H), 4.13-4.06 (m, 2H), 2.78-2.71 (m, 1H), 2.17-2.08 (m, 1H), 1.61-1.54 (m, 1H), 1.46-1.38 (m, 1H). LCMS (ESI): RT (min)=3.02, [M+H]+=338.1, Method=J.

Example 107

(±)-trans-N-(8-amino-6-(2-oxotetrahydro-2H-cyclopenta[d]oxazol-3(3aH)-yl)isoquinolin-3-yl)-2-cyano-cyclopropane-1-carboxamide (Compound 177)

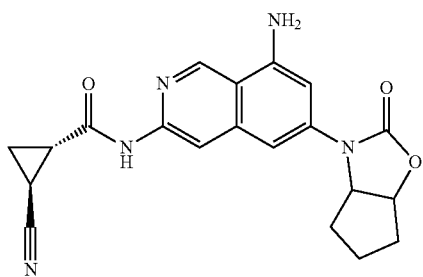 [SMILES: N#C[C@H]1C[C@@H]1C(=O)Nc1cc2cc(N3C(=O)OC4CCCC43)cc(N)c2cn1]

The title compound was prepared using procedures that are analogous to the one described for (1S,2S)—N-(8-amino-6-((S)-4-methyl-2-oxooxazolidin-3-yl)isoquinolin-3-yl)-2-fluorocyclopropanecarboxamide (Compound 128). 1H NMR (400 MHz, DMSO) δ 11.02 (s, 1H), 9.19 (s, 1H), 8.14 (s, 1H), 7.16 (d, J=2.0 Hz, 1H), 6.93 (d, J=1.8 Hz, 1H), 6.35 (s, 2H), 5.14-5.04 (m, 1H), 4.89 (s, 1H), 2.73 (m, J=5.3 Hz, 1H), 2.16-2.08 (m, 1H), 2.01-1.93 (m, 1H), 1.86-1.76 (m, 3H), 1.68 (s, 1H), 1.63-1.52 (m, 2H), 1.42 (d, J=4.3 Hz, 1H). LCMS (ESI): RT (min)=3.73, [M+H]+=378.1, Method=J.

Example 108

(±)-trans-N-(8-amino-6-(N,N-dimethylsulfamoyl)isoquinolin-3-yl)cyclopropane-1,2-dicarboxamide (Compound 178)

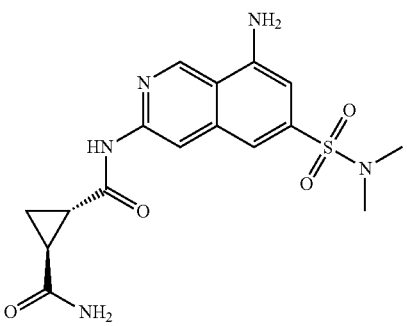 [SMILES: CN(C)S(=O)(=O)c1cc(N)c2cnc(NC(=O)[C@H]3C[C@@H]3C(N)=O)cc2c1]

LCMS (ESI): RT (min)=3.32, [M+H]+=378.1, Method=N*.

Example 109

(±)-trans-N-(8-amino-6-(N,N-dimethylsulfamoyl)isoquinolin-3-yl)-2-cyanocyclopropane-1-carboxamide (Compound 179)

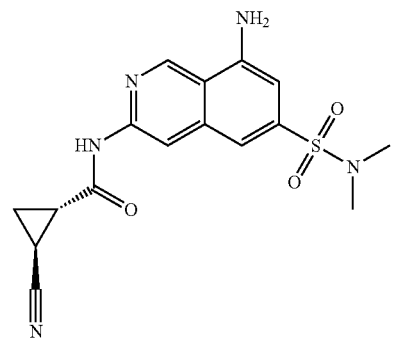 [SMILES: CN(C)S(=O)(=O)c1cc(N)c2cnc(NC(=O)[C@H]3C[C@@H]3C#N)cc2c1]

LCMS (ESI): RT (min)=3.39, [M+H]+=369.1, Method=N*.

Example 110

(1S,2S)—N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropanecarboxamide (Compound 180) and (1R,2R)—N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropanecarboxamide (Compound 181)

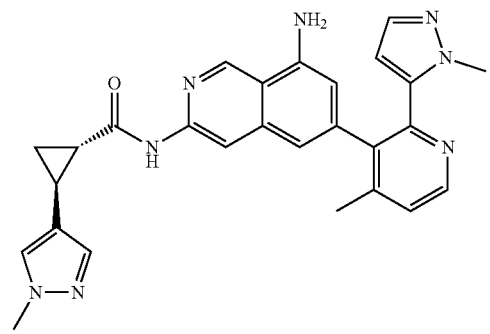

-continued

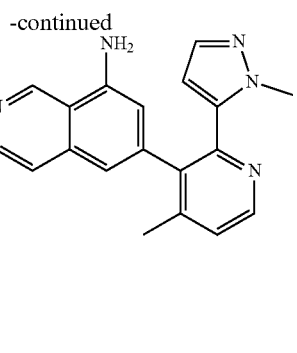

Step 1: 4-methyl-2-(1-methyl-1H-pyrazol-5-yl)pyridin-3-amine

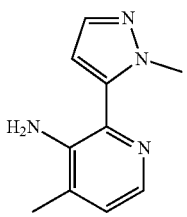

A mixture of 2-chloro-4-methylpyridin-3-amine (5.0 g, 35 mmol), (1-methyl-1H-pyrazol-5-yl)boronic acid (13.25 g, 105.2 mmol), K$_3$PO$_4$ (22.33 g, 105.20 mmol), and Pd(dppf)Cl$_2$ (2.57 g, 3.51 mmol) in 10:1 dioxane/water (110 mL) was heated at 100° C. After 3 h, the solids were filtered, and the filtrate was concentrated in vacuo. Purification of the resulting residue by flash column chromatography (3:2 petroleum ether/ethyl acetate) afforded 4-methyl-2-(1-methyl-1H-pyrazol-5-yl)pyridin-3-amine (2.0 g, 30% yield) as a brown solid. LCMS (ESI) [M+H]$^+$=189.

Step 2: 3-iodo-4-methyl-2-(1-methyl-1H-pyrazol-5-yl)pyridine

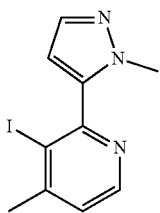

To an ice-cooled solution of 4-methyl-2-(1-methyl-H-pyrazol-5-yl)pyridin-3-amine (0.50 g, 2.7 mmol), t-BuNO$_2$ (1.09 g, 10.6 mmol) in CH$_3$CN (10 mL) was added CuI (2.02 g, 10.6 mmol). The resulting mixture was warmed to room temperature. After 16 h, the reaction was sequentially diluted with ammonium hydroxide (10 mL) and water (10 mL). The resulting solution was extracted with dichloromethane (20 mL). The organic layer was dried over Na$_2$SO$_4$, filtered, and concentrated in vacuo. Purification by flash column chromatography (3:1 ethyl acetate/petroleum ether) provided 3-iodo-4-methyl-2-(1-methyl-H-pyrazol-5-yl)pyridine (0.30 g, 38%) as a yellow solid. LCMS (ESI) [M+H]$^+$=300.

Step 3: 8-chloro-6-[4-methyl-2-(1-methyl-1H-pyrazol-5-yl)pyridin-3-yl]isoquinolin-3-amine

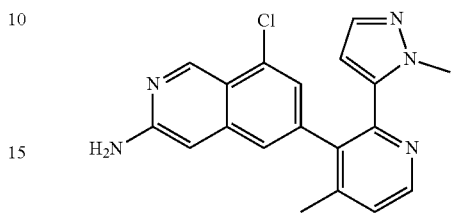

A mixture of (3-amino-8-chloroisoquinolin-6-yl)boronic acid (892 mg, 4.01 mmol), 3-iodo-4-methyl-2-(1-methyl-1H-pyrazol-5-yl)pyridine (0.60 g, 2.0 mmol), Pd(dppf)Cl$_2$ (147 mg, 0.20 mmol), AcONa (164 mg, 2.01 mmol), and K$_3$PO$_4$ (1.28 g, 6.02 mmol) in 10:1 1,4-dioxane/water (22 mL) was heated at 100° C. After 2 h, the solids were filtered, and the filtrate was concentrated in vacuo. Purification by flash column chromatography (ethyl acetate) gave 8-chloro-6-[4-methyl-2-(1-methyl-1H-pyrazol-5-yl)pyridin-3-yl]isoquinolin-3-amine (0.70 g, 74% yield) as a dark red solid. LCMS (ESI) [M+H]$^+$=350.

Step 4: trans-N-[8-Chloro-6-[4-methyl-2-(1-methyl-H-pyrazol-5-yl)pyridin-3-yl]isoquinolin-3-yl]-2-(1-methyl-1H-pyrazol-4-yl)cyclopropane-1-carboxamide

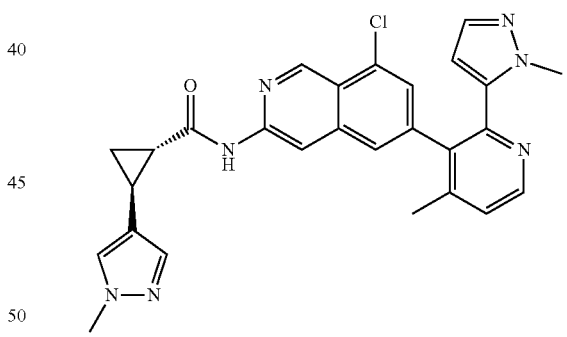

To an ice-cooled solution of 8-chloro-6-[4-methyl-2-(1-methyl-1H-pyrazol-5-yl)pyridin-3-yl]isoquinolin-3-amine (632 mg, 1.81 mmol), trans-2-(1-methyl-1H-pyrazol-4-yl)cyclopropane-1-carboxylic acid (0.20 g, 1.2 mmol) and pyridine (6.00 mL) in dichloromethane (40.00 mL) was added POCl$_3$ (277 mg, 1.81 mmol) dropwise. The mixture was warmed to room temperature. After 30 min, excess POCl$_3$ was quenched with water (30 mL). The resulting solution was extracted with dichloromethane (100 mL). The collected organic was dried over anhydrous sodium sulfate, filtered, and concentrated in vacuo to afford crude trans-N-[8-chloro-6-[4-methyl-2-(1-methyl-1H-pyrazol-5-yl)pyridin-3-yl]isoquinolin-3-yl]-2-(1-methyl-1H-pyrazol-4-yl)cyclopropane-1-carboxamide (0.60 g) as a dark red solid. LCMS (ESI) [M+H]$^+$=498.

Step 4: Trans-tert-butyl N-(3-[[2-(1-methyl-1H-pyrazol-4-yl)cyclopropane]amido]-6-[4-methyl-2-(1-methyl-1H-pyrazol-5-yl)pyridin-3-yl]isoquinolin-8-yl)carbamate

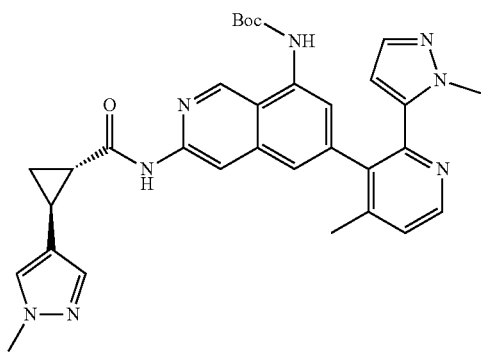

A suspension of trans-N-[8-chloro-6-[4-methyl-2-(1-methyl-H-pyrazol-5-yl)pyridin-3-yl]isoquinolin-3-yl]-2-(1-methyl-1H-pyrazol-4-yl)cyclopropane-1-carboxamide (0.80 g, 1.61 mmol), tert-butyl carbamate (3.76 g, 32.1 mmol), Pd$_2$(dba)$_3$ (294 mg, 3.21 mmol), BrettPhos (302 mg, 0.56 mmol), and t-BuONa (386 mg, 4.03 mmol) in dioxane (20 mL) was heated at 90° C. After 16 h, the solids were filtered, and the filtrate was concentrated in vacuo. Purification by flash column chromatography (ethyl acetate) afforded trans-tert-butyl N-(3-[[2-(1-methyl-1H-pyrazol-4-yl)cyclopropane]amido]-6-[4-methyl-2-(1-methyl-1H-pyrazol-5-yl)pyridin-3-yl]isoquinolin-8-yl)carbamate (350 mg, 38% yield) as a yellow solid. LCMS (ESI) [M+H]$^+$=579.

Step 5: (1S,2S)—N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropanecarboxamide and (1R,2R)—N-(8-amino-6-(4-methyl-2-(1-methyl-1H-pyrazol-5-yl)pyridin-3-yl)isoquinolin-3-yl)-2-(1-methyl-H-pyrazol-4-yl)cyclopropanecarboxamide

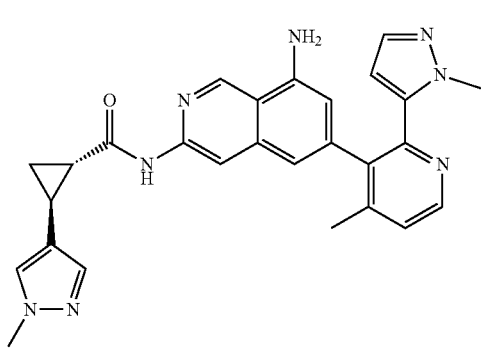

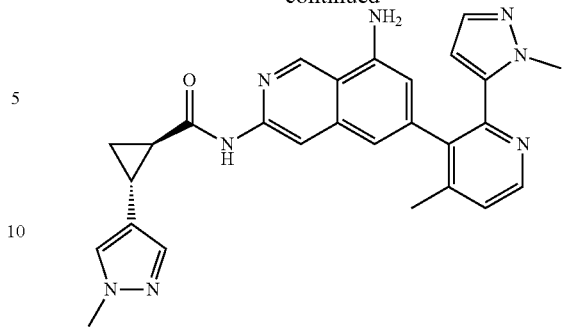

To a solution of trans-tert-butyl N-(3-[[2-(1-methyl-H-pyrazol-4-yl)cyclopropane]amido]-6-[4-methyl-2-(1-methyl-1H-pyrazol-5-yl)pyridin-3-yl]isoquinolin-8-yl)carbamate (0.30 g, 0.52 mmoL) in N,N-dimethylformamide (2.0 mL) was added HCl (5 mL, 4M in dioxane) at room temperature. After 1 h, the reaction was concentrated in vacuo. Purification of crude material by Prep-HPLC afforded the racemic product (60 mg, 24%) as a light yellow solid. The enantiomers were separated by chiral SFC. Compound 180: $^1$HNMR (400 MHz, CD$_3$OD) δ 9.17 (s, 1H), 8.56 (d, J=5.1 Hz, 1H), 8.20 (s, 1H), 7.49 (d, J=5.7 Hz, 2H), 7.37 (s, 1H), 7.20 (d, J=2.0 Hz, 1H), 6.82 (s, 1H), 6.47 (d, J=1.3 Hz, 1H), 5.99 (d, J=2.0 Hz, 1H), 3.86 (s, 3H), 3.81 (s, 3H), 2.38-2.33 (m, 1H), 2.29 (s, 3H), 2.12-2.04 (m, 1H), 1.57-1.53 (m, 1H), 1.30-1.18 (m, 1H). LCMS (ESI): RT (min)=1.23, [M+H]$^+$=479, Method=K. Compound 181: $^1$H NMR (400 MHz, CD$_3$OD) δ 9.17 (s, 1H), 8.56 (d, J=5.1 Hz, 1H), 8.20 (s, 1H), 7.49 (d, J=5.7 Hz, 2H), 7.37 (s, 1H), 7.20 (d, J=2.0 Hz, 1H), 6.82 (s, 1H), 6.47 (d, J=1.3 Hz, 1H), 5.99 (d, J=2.0 Hz, 1H), 3.86 (s, 3H), 3.81 (s, 3H), 2.38-2.33 (m, 1H), 2.29 (s, 3H), 2.12-2.04 (m, 1H), 1.57-1.53 (m, 1H), 1.30-1.18 (m, 1H). LCMS (ESI): RT (min)=1.22, [M+H]$^+$=479, Method=K.

Example 111

(1R,2R)—N-(8-amino-6-(4-methyl-2-phenylpyridin-3-yl)isoquinolin-3-yl)-2-(1-methyl-H-pyrazol-4-yl)cyclopropanecarboxamide (Compound 182) and (1S,2S)—N-(8-amino-6-(4-methyl-2-phenylpyridin-3-yl)isoquinolin-3-yl)-2-(1-methyl-1H-pyrazol-4-yl)cyclopropanecarboxamide (Compound 183)

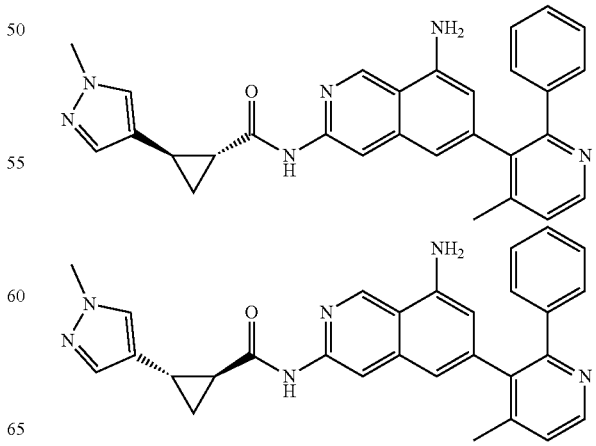

The title compound was prepared by following the procedure as described for (1S,2S)—N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropanecarboxamide (Compound 180) and making slight variations. The enantiomers were isolated by chiral SFC. Compound 182: ¹HNMR (300 MHz, CD₃OD) δ 9.14 (s, 1H), 8.47 (s, 1H), 8.13 (s, 1H), 7.50 (s, 1H), 7.44-7.26 (m, 4H), 7.22-7.11 (m, 3H), 6.78 (s, 1H), 6.50 (d, J=1.3 Hz, 1H), 3.85 (d, J=0.6 Hz, 3H), 2.41-2.31 (m, 1H), 2.27 (s, 3H), 2.13-2.04 (m, 1H), 1.56-1.53 (m, 1H), 1.32-1.17 (m, 1H). LCMS (ESI): RT (min)=1.13, [M+H]⁺=474, Method=K. Compound 183; T¹HNMR (300 MHz, CD₃OD) δ 9.14 (s, 1H), 8.47 (s, 1H), 8.13 (s, 1H), 7.50 (s, 1H), 7.44-7.26 (m, 4H), 7.22-7.11 (m, 3H), 6.78 (s, 1H), 6.50 (d, J=1.3 Hz, 1H), 3.85 (s, 3H), 2.41-2.31 (m, 1H), 2.27 (s, 3H), 2.13-2.04 (m, 1H), 1.56-1.53 (m, 1H), 1.32-1.17 (m, 1H). LCMS (ESI): RT (min)=1.13, [M+H]+=474, Method=K.

Example 112

(±)-trans-N-(8-amino-6-(4-methyl-2-(piperidin-1-yl)pyridin-3-yl)isoquinolin-3-yl)-2-(1-methyl-1H-pyrazol-4-yl)cyclopropanecarboxamide (Compound 184)

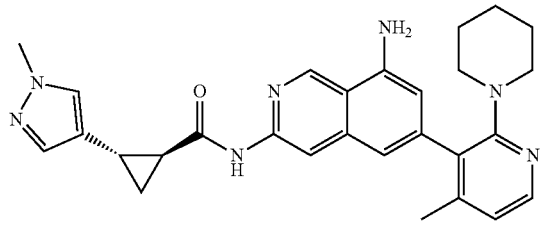 [SMILES: Cc1ccnc(N2CCCCC2)c1-c1cc(N)c2cnc(NC(=O)[C@H]3C[C@@H]3c3cnn(C)c3)cc2c1]

The title compound was prepared by following the procedure as described for (1S,2S)—N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropanecarboxamide (Compound 180) but substituting 3-bromo-4-methyl-2-(piperidin-1-yl)pyridine and making slight variations. ¹HNMR (400 MHz, DMSO-d₆) δ 10.75 (s, 1H), 9.27 (s, 1H), 8.24 (s, 1H), 8.06 (d, J=5.0 Hz, 1H), 7.56 (s, 1H), 7.29 (d, J=0.8 Hz, 1H), 6.94-6.80 (m, 2H), 6.53 (d, J=1.4 Hz, 1H), 6.20 (s, 2H), 3.78 (s, 3H), 2.96 (s, 4H), 2.19 (t, J=7.1 Hz, 2H), 2.07 (s, 3H), 1.36 (qd, J=7.0, 6.2, 4.3 Hz, 3H), 1.25 (d, J=8.3 Hz, 4H), 1.20-1.10 (m, 1H). LCMS (ESI): RT (min)=2.02, [M+H]+=482.3, Method=K.

Example 113

(±)-trans-N-(8-amino-6-(2-amino-3-methylpyridin-4-yl)isoquinolin-3-yl)-2-(1-methyl-1H-pyrazol-4-yl)cyclopropanecarboxamide (Compound 185)

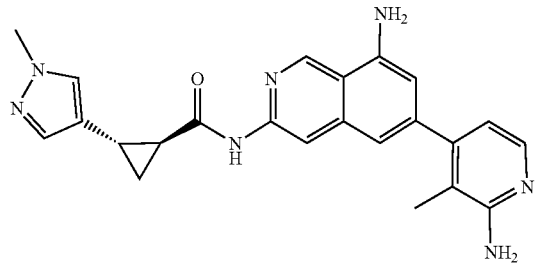 [SMILES: Cc1c(-c2cc(N)c3cnc(NC(=O)[C@H]4C[C@@H]4c4cnn(C)c4)cc3c2)ccnc1N]

The title compound was prepared by following the procedure as described for (±)-trans-N-(8-amino-6-(5-amino-4-methylpyridin-3-yl)isoquinolin-3-yl)-2-cyanocyclopropanecarboxamide (Compound 156) and making slight variations. ¹HNMR (300 MHz, DMSO-d₆) δ 10.75 (s, 1H), 9.30 (s, 1H), 8.27 (s, 1H), 7.83 (d, J=5.1 Hz, 1H), 7.57 (d, J=0.9 Hz, 1H), 7.30 (d, J=0.8 Hz, 1H), 6.81 (d, J=1.3 Hz, 1H), 6.53-6.41 (m, 2H), 6.31 (s, 2H), 5.78 (s, 2H), 3.78 (s, 3H), 2.20-2.16 (m, 2H), 1.98 (s, 3H), 1.44-1.32 (m, 1H), 1.17-1.14 (m, 1H).

LCMS (ESI): RT (min)=1.05, [M+H]+=414.1, Method=K.

Example 114

(±)-trans-N-(8-amino-6-[4-methyl-5-[(propan-2-yl)amino]pyridin-3-yl]isoquinolin-3-yl)-2-cyanocyclopropane-1-carboxamide (Compound 186)

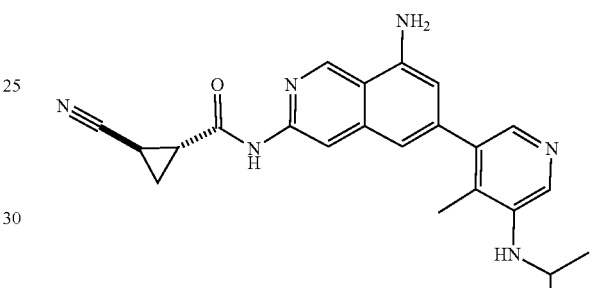

The title compound was prepared by following the procedure as described for (±)-trans-N-(8-amino-6-(5-amino-4-methylpyridin-3-yl)isoquinolin-3-yl)-2-cyanocyclopropanecarboxamide (Compound 156) and making slight variations. ¹HNMR (300 MHz, CD₃OD) δ 9.26 (s, 1H), 8.29 (s, 1H), 7.91 (s, 1H), 7.76 (s, 1H), 6.97 (s, 1H), 6.68 (d, J=1.4 Hz, 1H), 3.83-3.80 (m, 1H), 2.71-2.60 (m, 1H), 2.18-2.03 (m, 4H), 1.58-1.54 (m, 2H), 1.33 (d, J=12 Hz, 6H). LCMS (ESI): RT (min)=1.03, [M+H]+=401.1, Method=K.

Example 115

(±)-trans-(1S,2R)—N-(8-amino-6-(4-methyl-2-(1-methyl-1H-pyrazol-4-yl)pyridin-3-yl)isoquinolin-3-yl)-2-(cyanomethyl)cyclopropanecarboxamide (Compound 187)

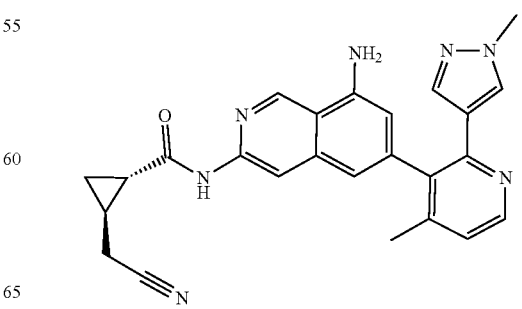

The title compound was prepared by following the procedure as described for (1S,2S)—N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropanecarboxamide (Compound 180) and making slight variations. $^1$H NMR (300 MHz, CD$_3$OD) δ 9.28 (s, 1H), 8.41 (d, J=5.1 Hz, 1H), 8.23 (s, 1H), 7.35 (s, 1H), 7.26 (d, J=5.1 Hz, 1H), 7.15 (s, 1H), 6.88 (s, 1H), 6.53 (s, 1H), 3.71 (s, 3H), 2.83-2.59 (m, 2H), 2.18 (t, J=0.7 Hz, 3H), 2.01 (dt, J=8.7, 4.5 Hz, 1H), 1.85-1.58 (m, 1H), 1.33 (dt, J=9.0, 4.7 Hz, 1H), 1.07-1.00 (m, 1H). LCMS (ESI): RT (min)=1.207, [M+H]$^+$=438.2, Method=K.

Example 116

N-(8-Amino-6-(2,3-dihydro-1H-pyrrolo[2,3-c]pyridin-4-yl)isoquinolin-3-yl)cyclopropanecarboxamide (Compound 188)

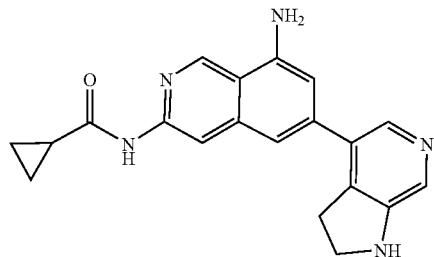 [SMILES: Nc1cc(-c2cncc3c2CCN3)cc2cc(NC(=O)C3CC3)ncc12]

Step 1: tert-Butyl 4-(3-amino-8-chloroisoquinolin-6-yl)-1H,2H,3H-pyrrolo[2,3-c]pyridine-1-carboxylate

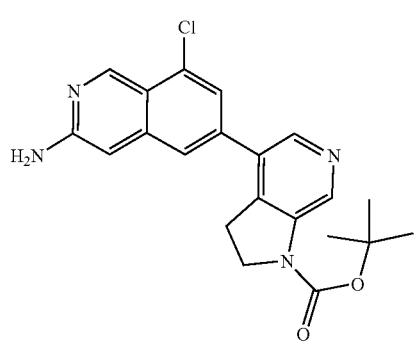 [SMILES: CC(C)(C)OC(=O)N1CCc2c(-c3cc(Cl)c4cnc(N)cc4c3)cncc21]

To a mixture of tert-butyl 4-[(trifluoromethane)sulfonyloxy]-1H,2H,3H-pyrrolo[2,3-c]pyridine-1-carboxylate (0.50 g, 1.36 mmol, (J. Med. Chem. 2014, 57, 2462), (3-amino-8-chloroisoquinolin-6-yl)boronic acid (602 mg, 2.71 mmol), Pd(dppf)Cl$_2$ (198 mg, 0.27 mmol) in 5:1 dioxane/water (12 mL) was added K$_3$PO$_4$ (288 mg, 1.36 mmol) and NaOAc (167 mg, 2.04 mmol). The suspension was heated at 100° C. for 1 h. The reaction was concentrated in vacuo, and the resulting residue was purified by flash column chromatography (10:1 dichloromethane/methanol) to afford tert-butyl 4-(3-amino-8-chloroisoquinolin-6-yl)-1H,2H,3H-pyrrolo[2,3-c]pyridine-1-carboxylate (0.30 g, 56% yield) as a yellow solid. LCMS (ESI) [M+H]$^+$=397.1.

Step 2: tert-Butyl 4-(8-chloro-3-cyclopropaneamidoisoquinolin-6-yl)-1H,2H,3H-pyrrolo[2,3-c]pyridine-1-carboxylate

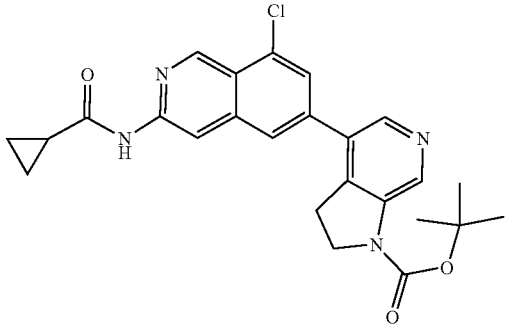 [SMILES: CC(C)(C)OC(=O)N1CCc2c(-c3cc(Cl)c4cnc(NC(=O)C5CC5)cc4c3)cncc21]

To a solution of tert-butyl 4-(3-amino-8-chloroisoquinolin-6-yl)-1H,2H,3H-pyrrolo[2,3-c]pyridine-1-carboxylate (0.40 g, 1.0 mmol) in tetrahydrofuran (20 mL) was added cyclopropanecarbonyl chloride (0.120 g, 1.15 mmol) and pyridine (0.20 g, 2.5 mmol) at 25° C. After 3 h, the reaction was concentrated under vacuum to afford crude tert-butyl 4-(8-chloro-3-cyclopropaneamidoisoquinolin-6-yl)-1H,2H,3H-pyrrolo[2,3-c]pyridine-1-carboxylate (0.50 g) as a yellow solid. LCMS (ESI) [M+H]$^+$=465.1.

Step 3: tert-Butyl 4-(8-[[(tert-butoxy)carbonyl]amino]-3-cyclopropaneamidoisoquinolin-6-yl)-1H,2H,3H-pyrrolo[2,3-c]pyridine-1-carboxylate A suspension of tert-butyl 4-(8-chloro-3-cyclopropaneamidoisoquinolin-6-yl)-1H,2H,3H-pyrrolo[2,3-c]pyridine-1-carboxylate (0.50 g, 1.08 mmol), tert-butyl N-[(tert-butoxy)carbonyl]carbamate (2.50 g, 11.5 mmol), Pd$_2$(dba)$_3$ (0.20 g, 0.22 mmol), BrettPhos (0.20 g, 0.37 mmol), and t-BuONa (0.260 g, 2.71 mmol) in dioxane (50 mL) was heated at 90° C. After 1 h, the reaction was concentrated in vacuo, and the resulting residue was purified by flash column chromatography (10:1 dichloromethane/methanol) to afford tert-butyl 4-(8-[[(tert-butoxy)carbonyl]amino]-3-cyclopropaneamidoisoquinolin-6-yl)-1H,2H,3H-pyrrolo[2,3-c]pyridine-1-carboxylate (0.40 g, 68% yield) as a yellow solid. LCMS (ESI) [M+H]$^+$=546.1.

Step 4: N-(8-Amino-6-[1H,2H,3H-pyrrolo[2,3-c]pyridin-4-yl]isoquinolin-3-yl)cyclopropanecarboxamide

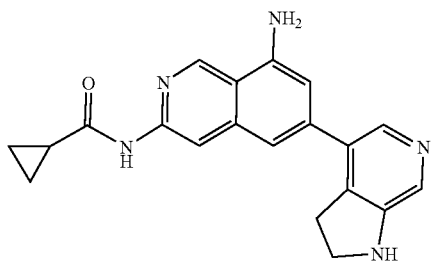 [SMILES: Nc1cc(-c2cncc3c2CCN3)cc2cc(NC(=O)C3CC3)ncc12]

To a solution of tert-butyl 4-(8-[[(tert-butoxy)carbonyl]amino]-3-cyclopropaneamidoisoquinolin-6-yl)-1H,2H,3H-pyrrolo[2,3-c]pyridine-1-carboxylate (250 mg, 0.46 mmol) in dioxane (10 mL) was added concentrated hydrochloric acid (10 mL) at 25° C. After 30 min, the reaction was concentrated in vacuo, and the resulting residue was purified by Prep-HPLC to afford N-(8-amino-6-[1H,2H,3H-pyrrolo[2,3-c]pyridin-4-yl]isoquinolin-3-yl)cyclopropanecarboxamide (4.7 mg, 3%) as a yellow solid. $^1$HNMR (300 MHz, DMSO-$d_6$) δ 10.80 (s, 1H), 9.32 (s, 1H), 8.31 (s, 1H), 7.99 (s, 1H), 7.83 (s, 1H), 7.11-7.02 (m, 1H), 6.73 (d, J=1.5 Hz, 1H), 6.36 (s, 2H), 6.18 (s, 1H), 3.55-3.50 (m, 2H), 3.20-3.15 (m, 2H), 2.06-2.01 (m, 1H), 0.84-0.80 (m, 4H). LCMS (ESI): RT (min)=1.193, [M+H]+=346.1, Method=K.

Example 117

(S)—N-(8-amino-6-(2-methyl-2,3-dihydro-1H-pyrrolo[2,3-c]pyridin-4-yl)isoquinolin-3-yl)cyclopropanecarboxamide (Compound 189) and (R)—N-(8-amino-6-(2-methyl-2,3-dihydro-1H-pyrrolo[2,3-c]pyridin-4-yl)isoquinolin-3-yl)cyclopropanecarboxamide (Compound 190)

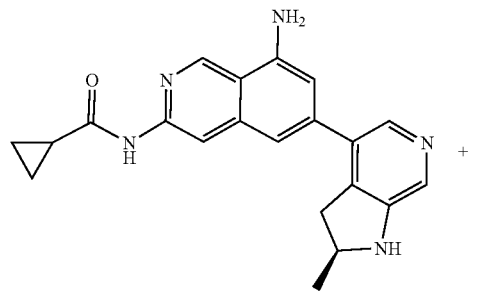

+

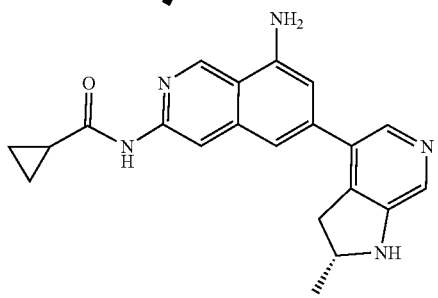

The title compound was prepared by following the procedure as described for N-(8-amino-6-[1H,2H,3H-pyrrolo[2,3-c]pyridin-4-yl]isoquinolin-3-yl)cyclopropanecarboxamide (Compound 188) and making slight variations. The single isomers were purified by chiral SFC. Compound 189: $^1$H NMR (300 MHz, CD$_3$OD) δ 9.21 (s, 1H), 8.28 (s, 1H), 7.94 (s, 1H), 7.78 (s, 1H), 7.11 (s, 1H), 6.83 (s, 1H), 4.18-3.91 (m, 1H), 3.34-3.31 (m, 1H), 2.81 (dd, J=16.8 Hz, 7.7 Hz, 1H), 1.98-1.90 (m, 1H), 1.29 (d, J=6.2 Hz, 3H), 1.05-0.99 (m, 2H), 0.98-0.85 (m, 2H). LCMS (ESI): RT (min)=1.09, [M+H]+=360.3, method=K. Compound 190: $^1$HNMR (300 MHz, CD$_3$OD) δ 9.21 (s, 1H), 8.28 (s, 1H), 7.94 (s, 1H), 7.78 (s, 1H), 7.11 (s, 1H), 6.83 (s, 1H), 4.18-3.91 (m, 1H), 3.34-3.31 (m, 1H), 2.81 (dd, J=16.8, 7.7 Hz, 1H), 1.98-1.90 (m, 1H), 1.29 (d, J=6.2 Hz, 3H), 1.05-0.99 (m, 2H), 0.98-0.85 (m, 2H). LCMS (ESI): RT (min)=1.09, [M+H]+=360.3, Method=K.

Example 118

(±)-(1S*,2S*,3R*)—N-(8-Amino-6-(4-methylpyridin-3-yl)isoquinolin-3-yl)-2-(cyanomethyl)-3-methylcyclopropanecarboxamide (Compound 191) and (±)-(1S*,2S*,3S*)—N-(8-Amino-6-(4-methylpyridin-3-yl)isoquinolin-3-yl)-2-(cyanomethyl)-3-methylcyclopropanecarboxamide (Compound 192)

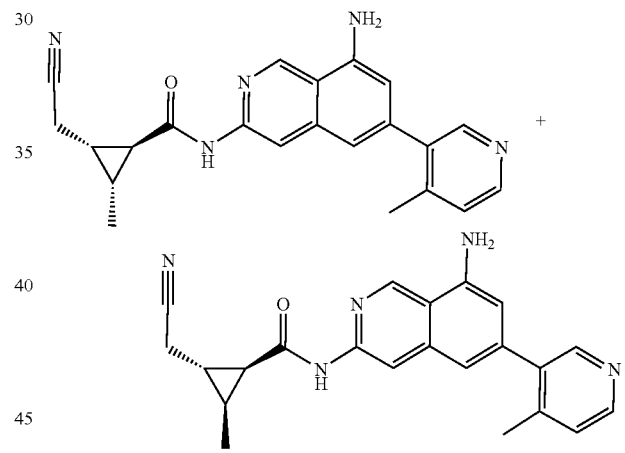

Step 1: 2-[(Benzyloxy)methyl]-N-[8-chloro-6-(4-methylpyridin-3-yl)isoquinolin-2-yl]-3-methylcyclopropane-1-carboxamide

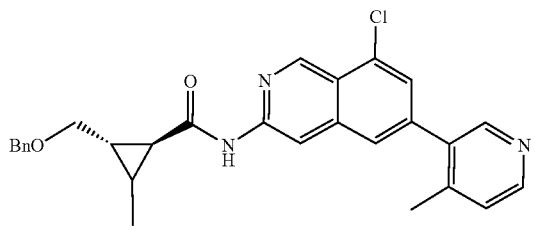 [SMILES: Cc1ccncc1-c1cc(Cl)c2cnc(NC(=O)[C@H]3C(C)[C@@H]3COCc3ccccc3)cc2c1]

To an ice-cooled solution of 8-chloro-6-(4-methylpyridin-3-yl)isoquinolin-3-amine (282 mg, 1.05 mmol) in dichloromethane (30 mL) was sequentially added pyridine (6.0 mL, 74 mmol), trans-2-[(benzyloxy)methyl]-3-methylcyclopropane-1-carboxylic acid (0.30 g, 1.4 mmol), and POCl₃ (321 mg, 2.09 mmol). The reaction mixture was warmed to 25° C. for 30 min before the addition of water (20 mL). The resulting solution was extracted with dichloromethane (3×30 mL). The combined organic was dried over anhydrous sodium sulfate, filtered, and concentrated in vacuo to afford 2-[(benzyloxy)methyl]-N-[8-chloro-6-(4-methylpyridin-3-yl)isoquinolin-3-yl]-3-methylcyclopropane-1-carboxamide (210 mg, 43%) as a yellow solid. LCMS (ESI) [M+H]⁺=472.0

Step 2: tert-Butyl N-(3-[[2-[(benzyloxy)methyl]-3-methylcyclopropane]amido]-6-(4-methylpyridin-3-yl)isoquinolin-8-yl)carbamate

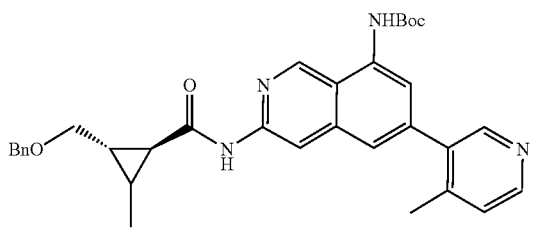 [SMILES: Cc1ccncc1-c1cc(NC(=O)OC(C)(C)C)c2cnc(NC(=O)[C@H]3C(C)[C@@H]3COCc3ccccc3)cc2c1]

A suspension of trans-2-[(benzyloxy)methyl]-N-[8-chloro-6-(4-methylpyridin-3-yl)isoquinolin-3-yl]-3-methylcyclopropane-1-carboxamide (420 mg, 0.89 mmol), NH₂Boc (2.61 g, 22 mmol), Pd₂(dba)₃·CHCl₃ (184 mg, 0.18 mmol), Brettphos (191 mg, 0.36 mmol), and Cs₂CO₃ (1.16 g, 3.57 mmol) in dioxane (10 mL) was heated at 120° C. After 1.5 h, the reaction was concentrated in vacuo, and the resulting residue was purified by flash column chromatography (4:1 ethyl acetate/petroleum ether) to afford tert-butyl N-(3-[[2-[(benzyloxy)methyl]-3-methylcyclopropane]amido]-6-(4-methylpyridin-3-yl)isoquinolin-8-yl)carbamate (450 mg, 92%) as a yellow solid. LCMS (ESI) [M+H]⁺=472.2.

Step 3: tert-Butyl 3-(2-(hydroxymethyl)-3-methylcyclopropanecarboxamido)-6-(4-methylpyridin-3-yl)isoquinolin-8-ylcarbamate

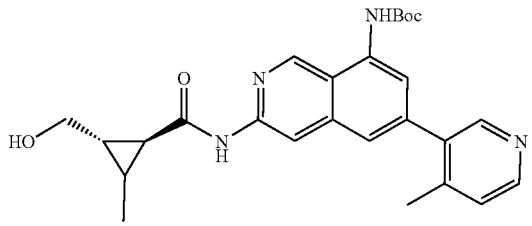 [SMILES: Cc1ccncc1-c1cc(NC(=O)OC(C)(C)C)c2cnc(NC(=O)[C@H]3C(C)[C@@H]3CC#N)cc2c1]

A suspension of tert-butyl N-(3-[[(1S,2S)-2-[(benzyloxy)methyl]-3-methylcyclopropane]amido]-6-(4-methylpyridin-3-yl)isoquinolin-8-yl)carbamate (350 mg, 0.63 mmol) and Pd(OH)₂ on carbon (2.5 g) in methanol (30 mL) was stirred for 30 min at 25° C. under H₂ (1 atm). The solids were filtered, and the filtrated was concentrated in vacuo to afford crude tert-butyl N-(3-[[(2-(hydroxymethyl)-3-methylcyclopropane]amido]-6-(4-methylpyridin-3-yl)isoquinolin-8-yl)carbamate (0.20 g, 68%) as a light green solid. LCMS (ESI) [M+H]⁺=463.3.

Step 4: 2-(8-(tert-Butoxycarbonylamino)-6-(4-methylpyridin-3-yl)isoquinolin-3-ylcarbamoyl)-3-methylcyclopropyl)methyl methanesulfonate

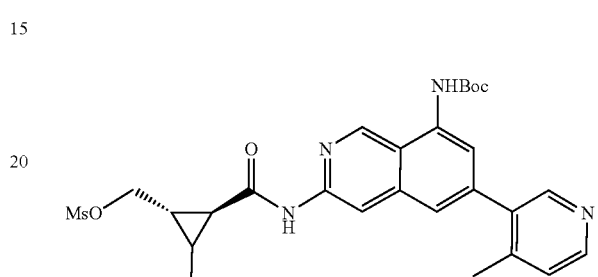

To an ice-cooled solution of tert-butyl N-(3-[[(1S,2S)-2-(hydroxymethyl)-3-methylcyclopropane]amido]-6-(4-methylpyridin-3-yl)isoquinolin-8-yl)carbamate (140 mg, 0.30 mmol) and triethylamine (183 mg, 1.81 mmol) in dichloromethane (3 mL) was added MsCl (138 mg, 1.21 mmol) dropwise. The reaction mixture warmed to 25° C. for 30 min before the addition of water (10 mL). The resulting solution was extracted with dichloromethane (50 mL). The organic extract was dried over anhydrous sodium sulfate, filtered, and concentrated in vacuo to afford crude 2-(8-(tert-butoxycarbonylamino)-6-(4-methylpyridin-3-yl)isoquinolin-3-ylcarbamoyl)-3-methylcyclopropyl)methyl methanesulfonate (150 mg) as a yellow oil. LCMS (ESI) [M+H]⁺=541.3.

Step 5: tert-butyl N-(3-[[2-(Cyanomethyl)-3-methylcyclopropane]amido]-6-(4-methylpyridin-3-yl)isoquinolin-8-yl)carbamate

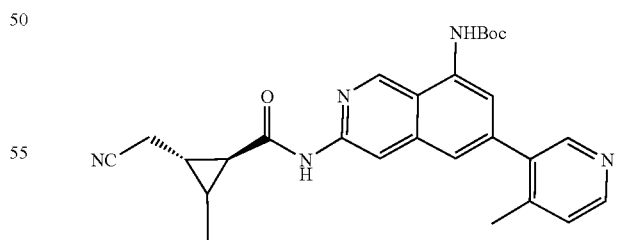

A solution of tert-butyl N-(3-[[2-(methanesulfonylmethyl)-3-methylcyclopropane]amido]-6-(4-methylpyridin-3-yl)isoquinolin-8-yl)carbamate (0.10 g) and KCN (99 mg, 1.5 mmol) in DMSO (3 mL) was heated at 50° C. After 2 h, the reaction was diluted with water (20 mL). The resulting solution was extracted with dichloromethane (50 mL). The collected organic was dried over anhydrous sodium sulfate, filtered, and concentrated in vacuo. Purification by flash column chromatography (10:1 dichloromethane/methanol) afforded tert-butyl N-(3-[[2-(cyanomethyl)-3-methylcyclopropane]amido]-6-(4-methylpyridin-3-yl)isoquinolin-8-yl)carbamate (0.070 g, 78%) as a brown solid. LCMS (ESI) [M+H]⁺=472.3.

Step 6: (±)-(1S*,2S*,3R*)—N-(8-Amino-6-(4-methylpyridin-3-yl)isoquinolin-3-yl)-2-(cyanomethyl)-3-methylcyclopropanecarboxamide and (±)-(1S*,2S*,3S*)—N-(8-Amino-6-(4-methylpyridin-3-yl)isoquinolin-3-yl)-2-(cyanomethyl)-3-methylcyclopropanecarboxamide

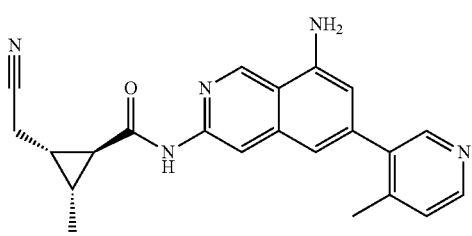

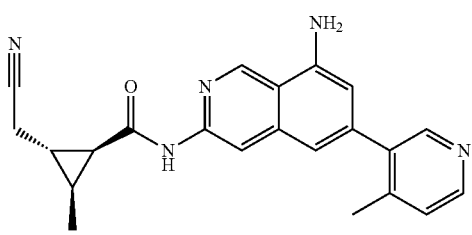

To a solution of tert-butyl N-(3-[[2-(cyanomethyl)-3-methylcyclopropane]amido]-6-(4-methylpyridin-3-yl)isoquinolin-8-yl)carbamate (0.070 g, 0.15 mmol) in dichloromethane (1 mL) was added trifluoroacetic acid (1.0 mL, 13 mmol) at 25° C. After 25 min, the reaction mixture was adjusted to pH=8 with 2M aqueous sodium bicarbonate. The resulting solution was extracted with dichloromethane (50 mL). The collected organic was dried over anhydrous sodium sulfate, filtered, and concentrated in vacuo. Purification by Prep-HPLC afforded two diastereoisomers. Compound 191: ¹HNMR (400 MHz, DMSO-d₆) 10.80 (s, 1H), 9.32 (s, 1H), 8.67-8.39 (m, 2H), 8.26 (s, 1H), 7.45 (d, J=5.1 Hz, 1H), 6.97-6.81 (m, 1H), 6.55 (d, J=1.5 Hz, 1H), 6.37 (s, 2H), 2.81 (dd, J=17.6, 7.3 Hz, 1H), 2.69 (dd, J=17.7, 7.7 Hz, 1H), 2.33 (s, 3H), 1.79 (t, J=4.5 Hz, 1H), 1.71-1.57 (m, 1H), 1.52-1.37 (m, 1H), 1.17 (d, J=6.3 Hz, 3H). LCMS (ESI) RT (min)=1.153, [M+H]+=372.2, Method=C. Compound 192: ¹HNMR (400 MHz, DMSO-d₆) 10.79 (s, 1H), 9.32 (s, 1H), 8.48-8.36 (m, 2H), 8.28 (s, 1H), 7.35 (d, J=5.0 Hz, 1H), 6.99-6.86 (m, 1H), 6.55 (d, J=1.5 Hz, 1H), 6.34 (s, 2H), 2.83-2.61 (m, 2H), 2.30 (s, 3H), 2.15-2.03 (m, 1H), 1.58-1.45 (m, 1H), 1.36 (dt, J=9.1, 6.1 Hz, 1H), 1.17 (d, J=6.1 Hz, 3H). LCMS (ESI) RT (min)=1.924, [M+H]⁺=372.2 Method=C.

Example 119

(2S)-2-(4-(8-amino-7-fluoro-6-(4-methylpyridin-3-yl)isoquinolin-3-ylamino)-1H-pyrazol-1-yl)propanenitrile (Compound 193) and (2R)-2-(4-(8-amino-7-fluoro-6-(4-methylpyridin-3-yl)isoquinolin-3-ylamino)-1H-pyrazol-1-yl)propanenitrile (Compound 194)

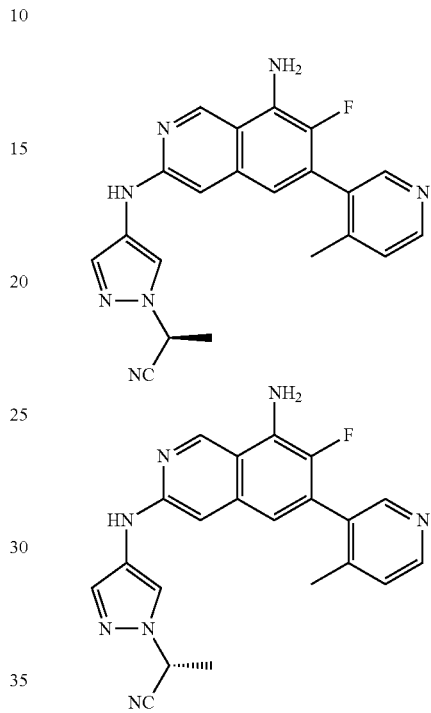

Step 1: 2-(4-[[8-Chloro-7-fluoro-6-(4-methylpyridin-3-yl)isoquinolin-3-yl]amino]-1H-pyrazol-1-yl)propanenitrile

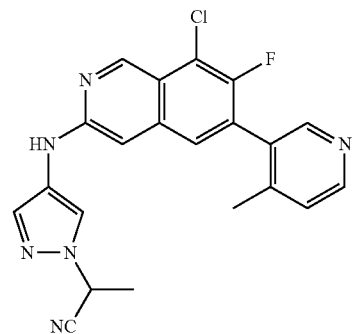 [SMILES: Cc1ccncc1-c1cc2cc(Nc3cnn(C(C)C#N)c3)ncc2c(Cl)c1F]

A suspension of 8-chloro-7-fluoro-6-(4-methylpyridin-3-yl)isoquinolin-3-amine (250 mg, 0.86 mmol), 2-(4-bromo-1H-pyrazol-1-yl)propanenitrile (1.04 g, 5.21 mmol), 3rd generation t-BuBrettPhos precatalyst (370 mg, 0.43 mmol), t-BuBrettPhos (210 mg, 0.43 mmol) and potassium carbonate (720 mg, 5.2 mmol) in 1,4-dioxane (15 mL) was heated at 120° C. After 16 h, the reaction was concentrated in vacuo. Purification by flash column chromatography (100% ethyl acetate) afforded 2-(4-[[8-chloro-7-fluoro-6-(4-methylpyridin-3-yl)isoquinolin-3-yl]amino]-1H-pyrazol-1-yl)propanenitrile (240 mg, 68%) as a yellow oil. LCMS (ESI) [M+H]⁺=407.1.

Step 2: tert-Butyl N-(3-[[1-(1-cyanoethyl)-1H-pyrazol-4-yl]amino]-7-fluoro-6-(4-methylpyridin-3-yl)isoquinolin-8-yl)carbamate

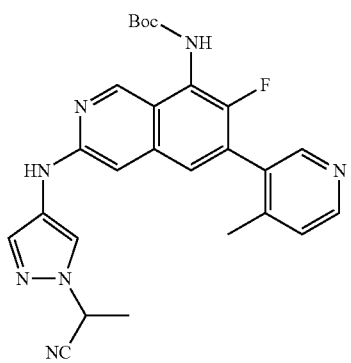 [SMILES: Cc1ccncc1-c1cc2cc(Nc3cnn(C(C)C#N)c3)ncc2c(NC(=O)OC(C)(C)C)c1F]

A suspension of 2-(4-[[8-chloro-7-fluoro-6-(4-methylpyridin-3-yl)isoquinolin-3-yl]amino]-1H-pyrazol-1-yl)propanenitrile (0.420 g, 1.03 mmol), tert-butyl carbamate (3.63 g, 31.0 mmol), Pd₂(dba)₃·CHCl₃ (160 mg, 0.15 mmol), BrettPhos (110 mg, 0.20 mmol), and Cs₂CO₃ (1.35 g, 4.12 mmol) in 1,4-dioxane (50 mL) was heated at 90° C. After 3 h, the reaction was concentrated in vacuo, and the resulting residue was purified by flash column chromatography (95:5 dichloromethane/methanol) to afford tert-butyl N-(3-[[1-(1-cyanoethyl)-1H-pyrazol-4-yl]amino]-7-fluoro-6-(4-methylpyridin-3-yl)isoquinolin-8-yl)carbamate (0.40 g, 79%) as a brown oil. LCMS (ESI) [M+H]⁺=488.3.

Step 3: (2S)-2-(4-(8-Amino-7-fluoro-6-(4-methylpyridin-3-yl)isoquinolin-3-ylamino)-1H-pyrazol-1-yl)propanenitrile and (2R)-2-(4-(8-Amino-7-fluoro-6-(4-methylpyridin-3-yl)isoquinolin-3-ylamino)-1H-pyrazol-1-yl)propanenitrile

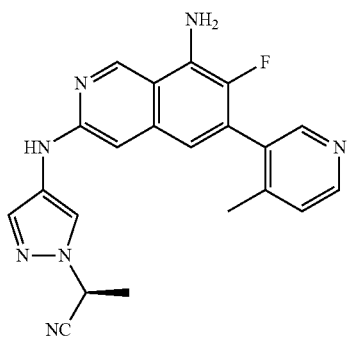

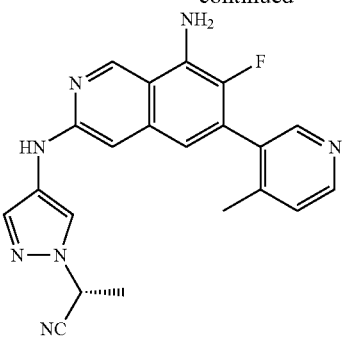

To a solution of tert-butyl N-(3-[[1-(1-cyanoethyl)-1H-pyrazol-4-yl]amino]-7-fluoro-6-(4-methylpyridin-3-yl)isoquinolin-8-yl)carbamate (350 mg, 0.71 mmol) in dichloromethane (10.0 mL) was added trifluoroacetic acid (10.0 mL, 134 mmol) at 25° C. After 1 h, the reaction was concentrated in vacuo. The residue was purified by Prep-HPLC followed by Chiral SFC to afford two enantiomers. Compound 193: ¹HNMR (300 MHz, CD₃OD) δ 9.29 (s, 1H), 8.76 (s, 1H), 8.49 (d, J=5.0 Hz, 1H), 8.41 (s, 1H), 8.09 (d, J=0.8 Hz, 1H), 7.62 (d, J=0.8 Hz, 1H), 7.39-7.34 (m, 1H), 6.83 (s, 1H), 6.76 (d, J=6.1 Hz, 1H), 6.13 (s, 2H), 5.82 (q, J=7.1 Hz, 1H), 2.22 (s, 3H), 1.80 (d, J=7.1 Hz, 3H). LCMS (ESI) RT (min)=1.08, [M+H]+=388.2. Method=K. Compound 194: ¹HNMR (300 MHz, CD₃OD) δ 9.29 (s, 1H), 8.76 (s, 1H), 8.49 (d, J=5.0 Hz, 1H), 8.41 (s, 1H), 8.09 (d, J=0.8 Hz, 1H), 7.62 (d, J=0.8 Hz, 1H), 7.39-7.34 (m, 1H), 6.83 (s, 1H), 6.76 (d, J=6.1 Hz, 1H), 6.13 (s, 2H), 5.82 (q, J=7.1 Hz, 1H), 2.22 (s, 3H), 1.80 (d, J=7.1 Hz, 3H). LCMS (ESI) RT (min)=1.08, [M+H]+=388.2. Method=K.

Example 120

(1R,2R,3R)—N-(8-Amino-7-fluoro-6-(4-methylpyridin-3-yl)isoquinolin-3-yl)-2-methyl-3-(1-methyl-1H-pyrazol-4-yl)cyclopropanecarboxamide (Compound 195), (1S,2R,3S)—N-(8-amino-7-fluoro-6-(4-methylpyridin-3-yl)isoquinolin-3-yl)-2-methyl-3-(1-methyl-1H-pyrazol-4-yl)cyclopropanecarboxamide (Compound 196), (1R,2S,3R)—N-(8-amino-7-fluoro-6-(4-methylpyridin-3-yl)isoquinolin-3-yl)-2-methyl-3-(1-methyl-1H-pyrazol-4-yl)cyclopropanecarboxamide (Compound 197) and (1S,2S,3S)—N-(8-amino-7-fluoro-6-(4-methylpyridin-3-yl)isoquinolin-3-yl)-2-methyl-3-(1-methyl-1H-pyrazol-4-yl)cyclopropanecarboxamide (Compound 198)

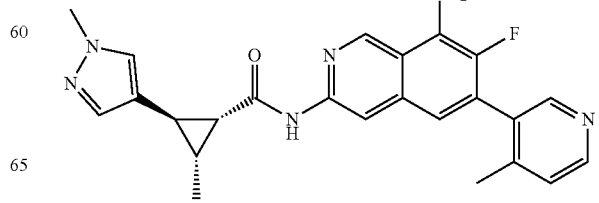

-continued

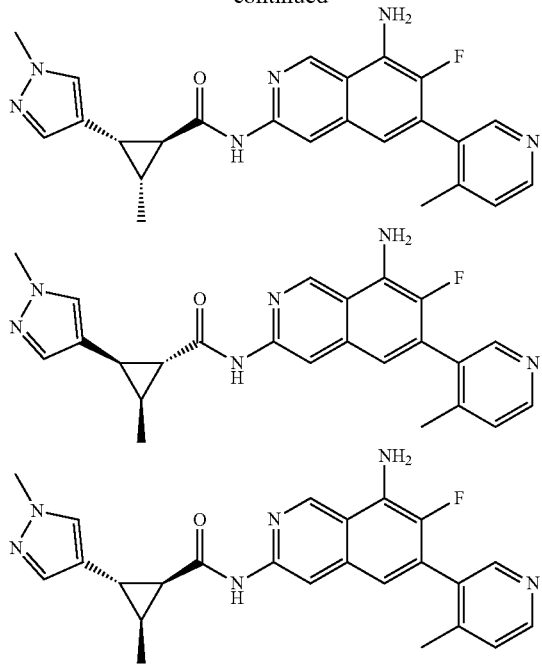

Step 1: Ethyldiphenylsulfonium tetrafluoroborate

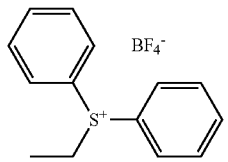

To a solution of AgBF₄ (37.48 g, 192.5 mmol) in dichloromethane (450 mL) was added iodoethane (30.0 g, 192 mmol) under N₂ at room temperature. After 30 min, diphenylsulfide (107 g, 574 mmol) was added, and the reaction mixture was warmed to 35° C. After 16 h, the solids were filtered out, and the filtrate was concentrated under vacuum. The resulting residue was rinsed with dichloromethane/ether (3×500 mL) to afford ethyldiphenylsulfanium tetrafluoroboranuide (25 g, 39%) as an off-white solid.

Step 2: tert-Butyl (2E)-3-(1-methyl-H-pyrazol-4-yl)prop-2-enoate

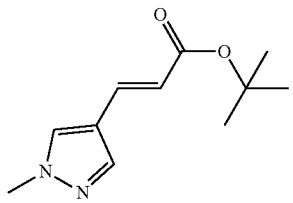

A solution of 4-iodo-1-methyl-1H-pyrazole (5.0 g, 24 mmol), tert-butyl prop-2-enoate (9.23 g, 72.0 mmol), triethylamine (2.91 g, 28.8 mmol), Pd(OAc)₂ (538 mg, 2.40 mmol) and P(o-Tol)₃ (1.46 g, 4.80 mmol) in N,N-dimethylformamide (20 mL) was heated at 110° C. After 16 h, the reaction was concentrated under vacuum, and the resulting residue was purified by flash column chromatography (3:1 petroleum ether/ethyl acetate) to afford tert-butyl (2E)-3-(1-methyl-1H-pyrazol-4-yl)prop-2-enoate as a light yellow oil (3.9 g, 74%). LCMS (ESI): M+H⁺=209.0.

Step 3: tert-Butyl-2-methyl-3-(1-methyl-H-pyrazol-4-yl)cyclopropane-1-carboxylate

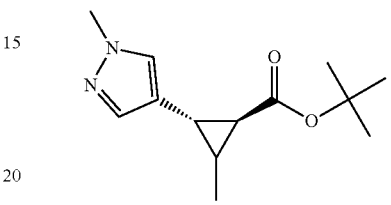

To a solution of ethyldiphenylsulfonium tetrafluoroborate (6.53 g, 21.6 mmol) in 1,2-dimethoxyethane (100 mL) and dichloromethane (15 mL) was added a solution of LDA (12.6 mL, 235.24 mmol, 2M in THF) dropwise at −78° C. After 30 min tert-butyl (2E)-3-(1-methyl-1H-pyrazol-4-yl)prop-2-enoate (1.50 g, 7.20 mmol) in 1,2-diemethoxyethane (10 mL) was added dropwise to the ylide solution at −78° C. After the addition, the reaction was warmed to room temperature. After 16 h, the reaction was diluted with water (100 mL), and the resulting mixture was extracted with chloroform (3×150 mL). The collected organic layers were dried over anhydrous sodium sulfate, filtered, and concentrated under vacuum to afford crude tert-butyl-2-methyl-3-(1-methyl-1H-pyrazol-4-yl)cyclopropane-1-carboxylate (1.5 g) as a light yellow oil.

Step 4: 2-Methyl-3-(1-methyl-1H-pyrazol-4-yl)cyclopropane-1-carboxylic Acid

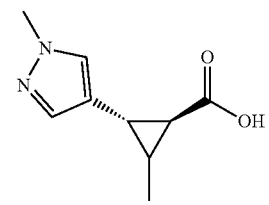

To a solution of tert-butyl-2-methyl-3-(1-methyl-H-pyrazol-4-yl)cyclopropane-1-carboxylate (0.60 g, 2.5 mmol) in dichloromethane (10 mL) was added trifluoroacetic acid (10 mL) at room temperature. After 5 h, the reaction was concentrated under vacuum, and the resulting residue was diluted with water (45 mL). The aqueous solution was basified to pH=9-10 with 10 M sodium hydroxide. The aqueous solution was then washed with ether (30 mL), and the resulting aqueous was acidified to pH=3-4 with 1M aqueous hydrochloric acid. The acidic aqueous solution was extracted with ethyl acetate (3×70 mL). The combined organic extracts were concentrated under vacuum to afford crude 2-methyl-3-(1-methyl-1H-pyrazol-4-yl)cyclopropane-1-carboxylic acid as off-white solid (450 mg, 70% purity, contains 30% TFA). LCMS (ESI): M+H⁺=181.0;

Step 5: N-[8-Chloro-7-fluoro-6-(4-methylpyridin-3-yl)isoquinolin-3-yl]-2-methyl-3-(1-methyl-1H-pyrazol-4-yl)cyclopropane-1-carboxamide

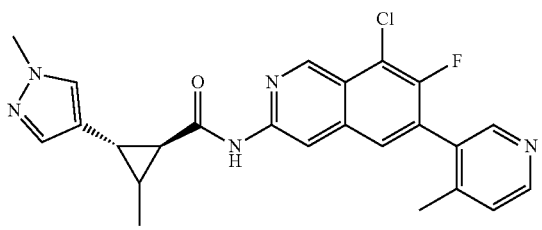 [SMILES: Cc1ccncc1-c1cc2cc(NC(=O)[C@H]3C(C)[C@@H]3c3cnn(C)c3)ncc2c(Cl)c1F]

A mixture of 8-chloro-7-fluoro-6-(4-methylpyridin-3-yl)isoquinolin-3-amine (1.0 g, 3.5 mmol), 2-methyl-3-(1-methyl-1H-pyrazol-4-yl)cyclopropane-1-carboxylic acid (690 mg, 3.8 mmol), pyridine (7 mL), and propargyl alcohol (953 mg, 6.22 mmol) in dichloromethane (50 mL) was stirred for 30 min at room temperature. The reaction mixture was diluted with water, and the resulting solution was extracted with dichloromethane. The organic layers were combined and concentrated under vacuum. Purification by flash column chromatography (30:1 dichloromethane/methanol) afforded N-[8-chloro-7-fluoro-6-(4-methylpyridin-3-yl)isoquinolin-3-yl]-2-methyl-3-(1-methyl-1H-pyrazol-4-yl)cyclopropane-1-carboxamide (750 mg, 48%) as a yellow solid. LCMS (ESI): M+H$^+$=450.2

Step 6: tert-Butyl N-(7-fluoro-3-[[2-methyl-3-(1-methyl-H-pyrazol-4-yl)cyclopropane]amido]-6-(4-methylpyridin-3-yl)isoquinolin-8-yl)carbamate

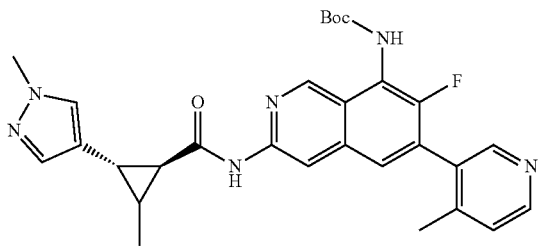 [SMILES: Cc1ccncc1-c1cc2cc(NC(=O)[C@H]3C(C)[C@@H]3c3cnn(C)c3)ncc2c(NC(=O)OC(C)(C)C)c1F]

To a solution of N-[8-chloro-7-fluoro-6-(4-methylpyridin-3-yl)isoquinolin-3-yl]-2-methyl-3-(1-methyl-1H-pyrazol-4-yl)cyclopropane-1-carboxamide (2.0 g, 4.45 mmol) in 1,4-dioxane (260 mL) was added tert-butyl carbamate (11.5 g, 98.2 mmol), tris(dibenylideneacetone)dipalladium-chloroform (691 mg, 0.67 mmol), dicyclohexyl[3,6-dimethoxy-2',4',6'-tris(1-methylethyl)[1,1'-biphenyl]-2-yl]phosphine (477 mg, 0.89 mmol) and cesium carbonate (7.3 g, 22.41 mmol). The resulting suspension was stirred heated at 90° C. After 2.5 h, the solids were filtered, and the filtrate was concentrated under vacuum. The resulting residue was purified by flash column chromatography (15:1 dichloromethane/methanol) to afford tert-butyl N-(7-fluoro-3-[[2-methyl-3-(1-methyl-H-pyrazol-4-yl)cyclopropane]amido]-6-(4-methylpyridin-3-yl)isoquinolin-8-yl)carbamate (1.2 g, 51%) as a yellow solid. LCMS (ESI): M+H$^+$=531.1.

Step 7: (1R,2R,3R)—N-(8-amino-7-fluoro-6-(4-methylpyridin-3-yl)isoquinolin-3-yl)-2-methyl-3-(1-methyl-1H-pyrazol-4-yl)cyclopropanecarboxamide, (1S,2R,3S)—N-(8-amino-7-fluoro-6-(4-methylpyridin-3-yl)isoquinolin-3-yl)-2-methyl-3-(1-methyl-1H-pyrazol-4-yl)cyclopropanecarboxamide, (1R,2S,3R)—N-(8-amino-7-fluoro-6-(4-methylpyridin-3-yl)isoquinolin-3-yl)-2-methyl-3-(1-methyl-1H-pyrazol-4-yl)cyclopropanecarboxamide and (1S,2S,3S)—N-(8-amino-7-fluoro-6-(4-methylpyridin-3-yl)isoquinolin-3-yl)-2-methyl-3-(1-methyl-1H-pyrazol-4-yl)cyclopropanecarboxamide

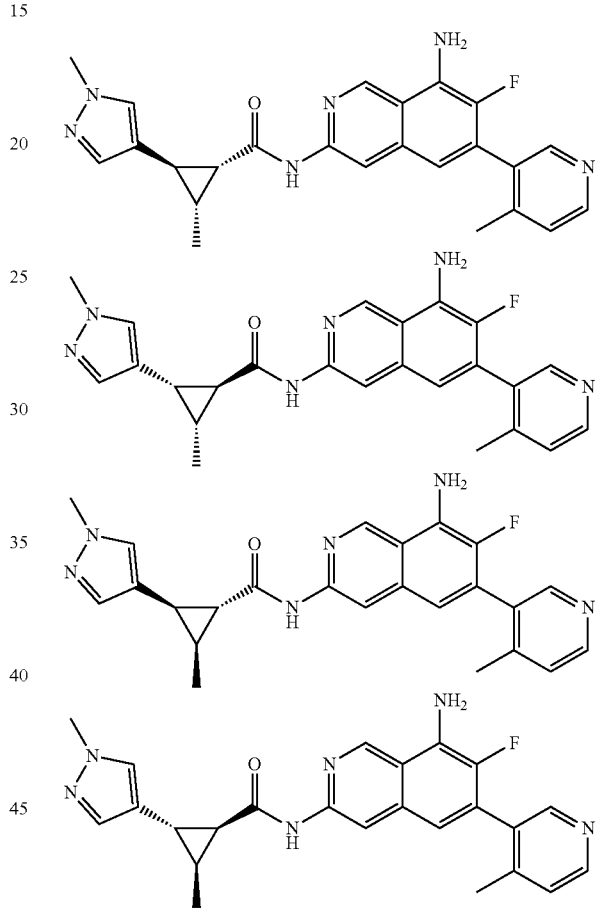

A solution of N-(7-fluoro-3-[[2-methyl-3-(1-methyl-1H-pyrazol-4-yl)cyclopropane]amido]-6-(4-methylpyridin-3-yl)isoquinolin-8-yl)carbamate (1.0 g, 1.88 mmol) in dichloromethane (25 mL) and trifluoroacetic acid (25 mL) was stirred for 1.5 h at room temperature. The reaction was concentrated under vacuum. Purification by Prep-HPLC and chiral SFC afforded four isomers. Compound 195: $^1$HNMR (400 MHz, CD$_3$OD) δ 9.30 (s, 1H), 8.47 (d, J=5.2 Hz, 1H), 8.42 (s, 1H), 8.36 (s, 1H), 7.45 (t, J=6.2 Hz, 2H), 7.34 (s, 1H), 7.00 (d, J=8.0 Hz, 1H), 3.85 (s, 3H), 2.34-2.32 (m, 4H), 2.17-2.14 (m, 1H), 1.62-1.48 (m, 1H), 1.35 (d, J=6.4 Hz, 3H). LCMS (ESI): RT (min)=1.14, [M+H]$^+$=461.3, Method=K. Compound 196: $^1$HNMR (400 MHz, CD$_3$OD) δ 9.31 (s, 1H), 8.46 (d, J=5.2 Hz, 1H), 8.41 (s, 1H), 8.34 (s, 1H), 7.51 (s, 1H), 7.42 (d, J=5.2 Hz, 1H), 7.39 (s, 1H), 6.98 (d, J=6.0 Hz, 1H), 3.88 (s, 3H), 2.52-2.49 (m, 1H), 2.30 (s, 3H), 1.99-1.97 (m, 1H), 1.79-1.72 (m, 1H), 1.17 (d, J=6.4

Hz, 3H). LCMS (ESI): RT (min)=1.15, [M+H]⁺=461.3, Method=K. Compound 197: ¹HNMR (400 MHz, CD₃OD) δ 9.31 (s, 1H), 8.46 (d, J=5.2 Hz, 1H), 8.41 (s, 1H), 8.34 (s, 1H), 7.51 (s, 1H), 7.43 (d, J=5.2 Hz, 1H), 7.39 (s, 1H), 6.98 (d, J=6.0 Hz, 1H), 3.88 (s, 3H), 2.53-2.49 (m, 1H), 2.31 (s, 3H), 1.99-1.97 (m, 1H), 1.77-1.72 (m, 1H), 1.17 (d, J=6.4 Hz, 3H). LCMS (ESI): RT (min)=1.15, [M+H]⁺=461.3, Method=K. Compound 198: ¹H NMR (400 MHz, CD₃OD) δ 9.30 (s, 1H), 8.47 (d, J=5.2 Hz, 1H), 8.42 (s, 1H), 8.36 (s, 1H), 7.45 (t, J=6.2 Hz, 2H), 7.34 (s, 1H), 7.00 (d, J=8.0 Hz, 1H), 3.85 (s, 3H), 2.34-2.32 (m, 4H), 2.17-2.14 (m, 1H), 1.67-1.61 (m, 1H), 1.35 (d, J=6.4 Hz, 3H). LCMS (ESI): RT (min)=1.14, [M+H]⁺=461.3, Method=K.

Example 121

(R)-2-(3-(8-amino-6-(4-methylpyridin-3-yl)isoquinolin-3-ylamino)-1H-pyrazol-1-yl)propanenitrile (Compound 199 and (S)-2-(3-(8-amino-6-(4-methylpyridin-3-yl)isoquinolin-3-ylamino)-1H-pyrazol-1-yl)propanenitrile (Compound 200)

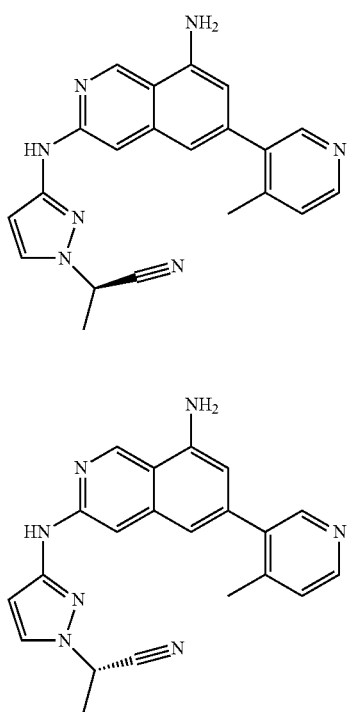

The title compound was prepared using a procedure as described for (2S)-2-(4-(8-amino-7-fluoro-6-(4-methylpyridin-3-yl)isoquinolin-3-ylamino)-1H-pyrazol-1-yl)propanenitrile (Compound 193). The single isomers were isolated by chiral HPLC. Compound 199: ¹H NMR (400 MHz, CD₃OD) δ 9.14 (s, 1H), 8.39 (d, J=4.4 Hz, 2H), 7.80 (s, 1H), 7.67 (d, J=2.4 Hz, 1H), 7.40 (d, J=5.2 Hz, 1H), 6.89 (s, 1H), 6.52 (s, 1H), 6.25 (d, J=2.4 Hz, 1H), 5.59-5.54 (m, 1H), 2.39 (s, 3H), 1.91 (d, J=6.8 Hz, 3H). LCMS (ESI): RT (min)=0.99, [M+H]⁺=461.3, Method=K. Compound 200: ¹HNMR (400 MHz, CD₃OD) δ 9.14 (s, 1H), 8.39 (d, J=4.4 Hz, 2H), 7.80 (s, 1H), 7.67 (d, J=2.4 Hz, 1H), 7.40 (d, J=5.2 Hz, 1H), 6.89 (s, 1H), 6.52 (s, 1H), 6.25 (d, J=2.4 Hz, 1H), 5.59-5.54 (m, 1H), 2.39 (s, 3H), 1.91 (d, J=6.8 Hz, 3H). LCMS (ESI): RT (min)=0.99, [M+H]+=461.3, Method=K.

Example 122

(S)-2-(4-(8-amino-6-(4-methylpyridin-3-yl)isoquinolin-3-ylamino)-1H-pyrazol-1-yl)propanenitrile (Compound 201) and (R)-2-(4-(8-amino-6-(4-methylpyridin-3-yl)isoquinolin-3-ylamino)-1H-pyrazol-1-yl)propanenitrile (Compound 202)

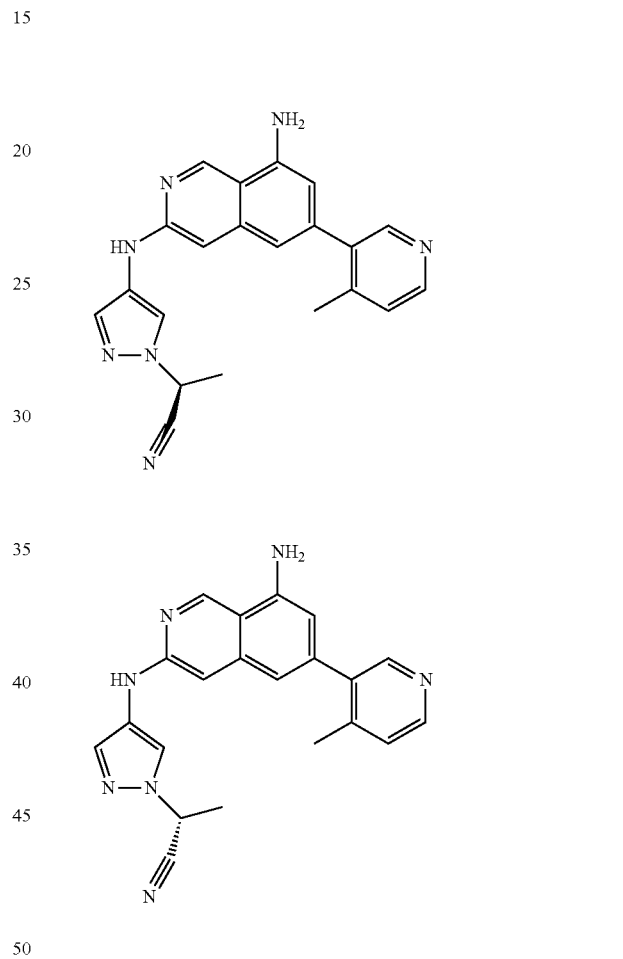

The title compound was prepared by following the procedure as described for (2S)-2-(4-(8-amino-7-fluoro-6-(4-methylpyridin-3-yl)isoquinolin-3-ylamino)-1H-pyrazol-1-yl)propanenitrile (Compound 193) and making slight variations. The enantiomers were isolated by chiral HPLC. Compound 201: ¹HNMR (300 MHz, CD₃OD) δ 9.12 (s, 1H), 8.39-8.37 (m, 2H), 8.06 (s, 1H), 7.67 (s, 1H), 7.37 (d, J=5.1 Hz, 1H), 6.82 (d, J=5.1 Hz, 2H), 6.45 (s, 1H), 5.62 (q, J=7.2 Hz, 1H), 2.37 (s, 3H), 1.90 (d, J=7.2 Hz, 3H). LCMS (ESI): RT (min)=1.585, [M+H]⁺=370.2, method=K. Compound 202: ¹HNMR (300 MHz, CD₃OD) δ 9.12 (s, 1H), 8.39-8.37 (m, 2H), 8.06 (s, 1H), 7.67 (s, 1H), 7.37 (d, J=5.1 Hz, 1H), 6.82 (d, J=5.1 Hz, 2H), 6.45 (s, 1H), 5.62 (q, J=7.2 Hz, 1H), 2.37 (s, 3H), 1.90 (d, J=7.2 Hz, 3H). LCMS (ESI): RT (min)=0.946, [M+H]+=370.2, Method=K.

Example 123

2-(4-(8-amino-5-chloro-6-(4-methylpyridin-3-yl)
isoquinolin-3-ylamino)-1H-pyrazol-1-yl)propaneni-
trile (Compound 203), 2-(4-(8-amino-5,7-dichloro-
6-(4-methylpyridin-3-yl)isoquinolin-3-ylamino)-1H-
pyrazol-1-yl)propanenitrile (Compound 204), (2S)-
2-(4-(8-amino-7-chloro-6-(4-methylpyridin-3-yl)
isoquinolin-3-ylamino)-1H-pyrazol-1-yl)
propanenitrile (Compound 205), and (2R)-2-(4-(8-
amino-7-chloro-6-(4-methylpyridin-3-yl)isoquinolin-
3-ylamino)-1H-pyrazol-1-yl)propanenitrile
(Compound 206)

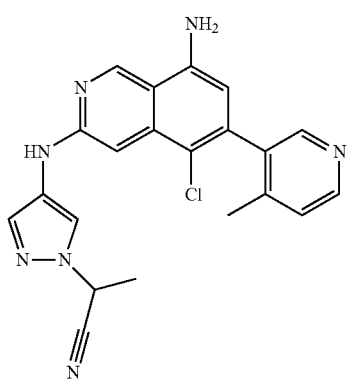

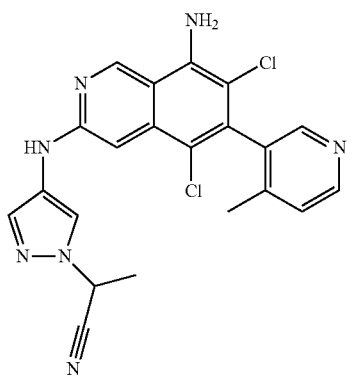

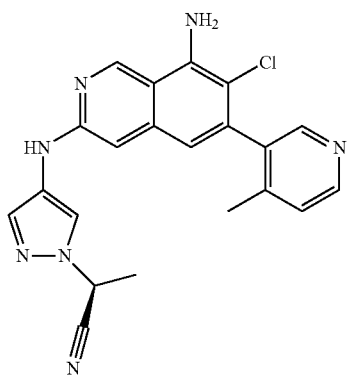

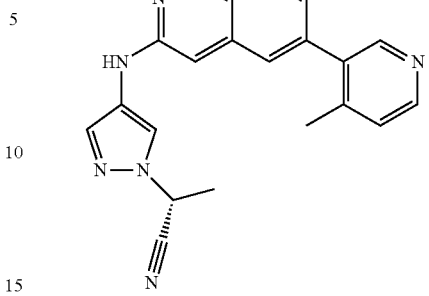

A solution of 2-(4-[[8-amino-6-(4-methylpyridin-3-yl) isoquinolin-3-yl]amino]-1H-pyrazol-1-yl)propanenitrile (0.20 g, 0.54 mmol) and NCS (72 mg, 0.54 mmol) in CH₃CN (10 mL) was heated at 50° C. After 2 h, the reaction was concentrated in vacuo, and the resulting residue was sequentially purified by Prep-HPLC and Chiral SFC to afford four isomers. Compound 203: ¹NMR (300 MHz, CD₃OD) δ 9.17 (s, 1H), 8.42 (d, J=5.1 Hz, 1H), 8.27 (s, 1H), 8.10 (s, 1H), 7.69 (s, 1H), 7.40 (d, J=5.1 Hz, 1H), 7.15 (s, 1H), 6.32 (s, 1H), 5.63 (q, J=7.2, 1H), 2.22 (s, 3H), 1.89 (d, J=7.2, 3H). LCMS (ESI): RT (min)=1.12, [M+H]+=404.2, Method=K. Compound 204: ¹HNMR (300 MHz, CD₃OD) δ 9.26 (s, 1H), 8.48 (d, J=5.1 Hz, 1H), 8.29 (s, 1H), 8.14 (1H, s), 7.70 (s, 1H), 7.46 (d, J=5.1 Hz, 1H), 7.16 (s, 1H), 5.65 (q, J=7.2 Hz, 1H), 2.17 (s, 3H), 1.90 (d, J=7.2 Hz, 3H). LCMS (ESI): RT (min)=2.20, [M+H]+=438.1, Method=K. Compound 205: ¹HNMR (300 MHz, CD₃OD) δ 9.17 (s, 1H), 8.42 (d, J=5.1 Hz, 1H), 8.27 (s, 1H), 8.07 (s, 1H), 7.66 (s, 1H), 7.39 (d, J=5.1 Hz, 1H), 6.80 (s, 2H), 5.61 (q, J=7.2 Hz, 1H), 2.22 (s, 3H), 1.89 (d, J=7.2 Hz, 3H). LCMS (ESI): RT (min)=1.78, [M+H]+=404.2, Method=K. Compound 206: ¹HNMR (300 MHz, CD₃OD) δ 9.17 (s, 1H), 8.42 (d, J=5.1 Hz, 1H), 8.27 (s, 1H), 8.07 (s, 1H), 7.66 (s, 1H), 7.39 (d, J=5.1 Hz, 1H), 6.80 (s, 2H), 5.61 (q, J=7.2 Hz, 1H), 2.22 (s, 3H), 1.89 (d, J=7.2 Hz, 3H). LCMS (ESI): RT (min)=1.78, [M+H]+=404.2, Method=K.

Example 124

(1S,2S)—N-(8-amino-6-(4-methyl-2-(pyrrolidin-1-
yl)pyridin-3-yl)isoquinolin-3-yl)-2-(1-methyl-1H-
pyrazol-4-yl)cyclopropanecarboxamide (Compound
207) and (1R,2R)—N-(8-amino-6-(4-methyl-2-(pyr-
rolidin-1-yl)pyridin-3-yl)isoquinolin-3-yl)-2-(1-
methyl-1H-pyrazol-4-yl)cyclopropanecarboxamide
(Compound 208)

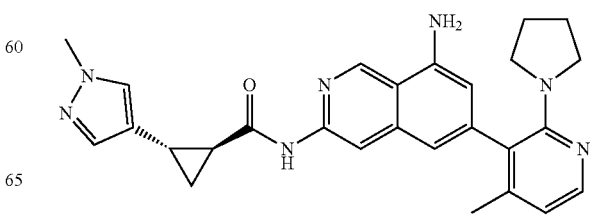

-continued

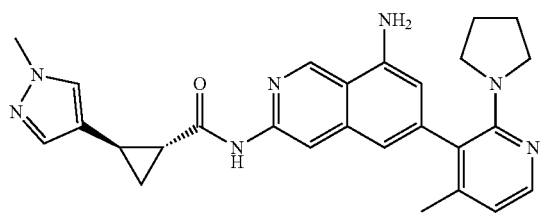

Step 1: 3-iodo-4-methyl-2-(pyrrolidin-1-yl)pyridine

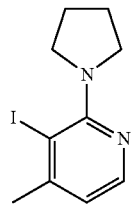

A solution of 2-chloro-3-iodo-4-methylpyridine (600 mg, 2.367 mmol), pyrrolidine (336.71 mg, 4.73 mmol) and DIEA (611.88 mg, 4.73 mmol) in DMA (10.00 mL) was heated at 120° C. After 2 h, the reaction was diluted with water (50 mL). The resulting solution was extracted with ethyl acetate (2×50 mL). The collected organic was dried over anhydrous sodium sulfate, filtered, and concentrated in vacuo to afford crude 3-iodo-4-methyl-2-(pyrrolidin-1-yl)pyridine (630 mg, 92%) as a dark red oil. LCMS (ESI): M+H$^+$=289.0.

Step 2: 8-chloro-6-[4-methyl-2-(pyrrolidin-1-yl)pyridin-3-yl]isoquinolin-3-amine

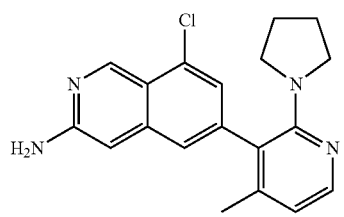 [SMILES: Cc1ccnc(N2CCCC2)c1-c1cc(Cl)c2cnc(N)cc2c1]

A suspension of (3-amino-8-chloroisoquinolin-6-yl)boronic acid (926.4 mg, 4.17 mmol), 3-iodo-4-methyl-2-(pyrrolidin-1-yl)pyridine (600 mg, 2.08 mmol), XPhos palladium(II) biphenyl-2-amine chloride (328 mg, 0.42 mmol), X-Phos (397 mg, 0.83 mmol), and potassium carbonate (576 mg, 4.16 mmol) in 1,4-dioxane (10 mL) and water (2.5 mL) was heated at 100° C. After 2 h, the solids were filtered, and the filtrate was concentrated in vacuo. Purification by flash column chromatography (1:1 ethyl acetate/petroleum ether) afforded 8-chloro-6-[4-methyl-2-(pyrrolidin-1-yl)pyridin-3-yl]isoquinolin-3-amine (0.40 g, 57%) as a light yellow solid. LCMS (ESI): M+H$^+$=339.1

Step 3: (±)-trans-N-[8-chloro-6-[4-methyl-2-(pyrrolidin-1-yl)pyridin-3-yl]isoquinolin-3-yl]-2-(1-methyl-1H-pyrazol-4-yl)cyclopropane-1-carboxamide

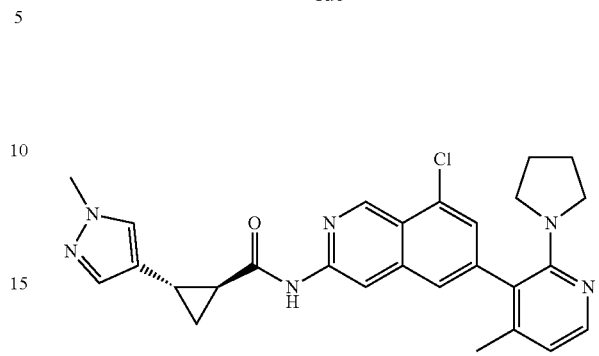

To an ice-cooled solution of 8-chloro-6-[4-methyl-2-(pyrrolidin-1-yl)pyridin-3-yl]isoquinolin-3-amine (440 mg, 1.3 mmol), trans-2-(1-methyl-1H-pyrazol-4-yl)cyclopropane-1-carboxylic acid (180 mg, 1.08 mmol), and pyridine (6.00 mL, 74.54 mmol) in dichloromethane (40 mL) was added POCl$_3$ (249 mg, 1.63 mmol) dropwise. The reaction mixture was warmed to room temperature for 30 min and diluted with water (50 mL). The resulting solution was extracted with dichloromethane (100 mL). The organic layer was dried over anhydrous sodium sulfate, filtered, and concentrated in vacuo to afford crude (±)-trans-N-[8-chloro-6-[4-methyl-2-(pyrrolidin-1-yl)pyridin-3-yl]isoquinolin-3-yl]-2-(1-methyl-1H-pyrazol-4-yl)cyclopropane-1-carboxamide (0.40 g, 76%) as a orange solid. LCMS (ESI): M+H$^+$=487.0

Step 4: (±)-trans-tert-butyl N-(3-[[2-(1-methyl-H-pyrazol-4-yl)cyclopropane]amido]-6-[4-methyl-2-(pyrrolidin-1-yl)pyridin-3-yl]isoquinolin-8-yl)carbamate

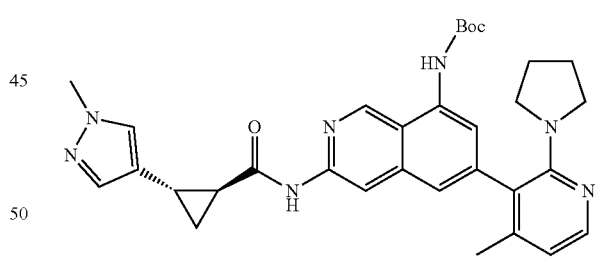

A mixture of (±)-trans-N-[8-chloro-6-[4-methyl-2-(pyrrolidin-1-yl)pyridin-3-yl]isoquinolin-3-yl]-2-(1-methyl-1H-pyrazol-4-yl)cyclopropane-1-carboxamide (0.30 g, 0.62 mmol), tert-butyl carbamate (1.50 g, 12.8 mmol), Pd$_2$(dba)$_3$CHCl$_3$ (148 mg, 0.14 mmol), BrettPhos (120 mg, 0.22 mmol), and t-BuONa (152 mg, 1.58 mmol) in 1,4-dioxane (10 mL) was heated at 100° C. After 4 h, the reaction was concentrated in vacuo, and the resulting residue was purified by flash column chromatography (10% ethyl acetate in petroleum ether→100% ethyl acetate) to afford crude (±)-trans-tert-butyl N-(3-[[2-(1-methyl-H-pyrazol-4-yl)cyclopropane]amido]-6-[4-methyl-2-(pyrrolidin-1-yl)pyridin-3-yl]isoquinolin-8-yl)carbamate (0.20 g, 57%) as a light yellow solid. LCMS (ESI): M+H$^+$=568.0.

643

Step 5: (1S,2S)—N-(8-amino-6-(4-methyl-2-(pyrrolidin-1-yl)pyridin-3-yl)isoquinolin-3-yl)-2-(1-methyl-1H-pyrazol-4-yl)cyclopropanecarboxamide and (1R,2R)—N-(8-amino-6-(4-methyl-2-(pyrrolidin-1-yl)pyridin-3-yl)isoquinolin-3-yl)-2-(1-methyl-1H-pyrazol-4-yl)cyclopropanecarboxamide

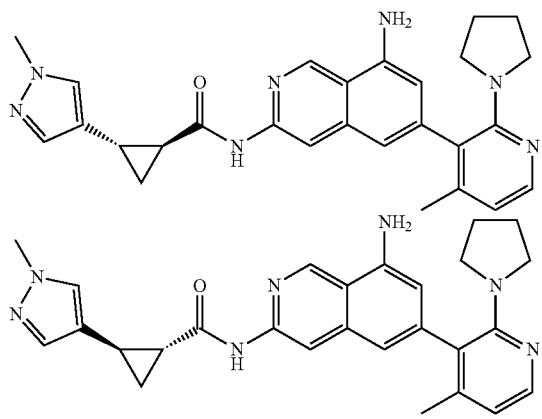

A solution of (±)-trans-tert-butyl N-(3-[[2-(1-methyl-1H-pyrazol-4-yl)cyclopropane]amido]-6-[4-methyl-2-(pyrrolidin-1-yl)pyridin-3-yl]isoquinolin-8-yl)carbamate (0.050 g, 0.088 mmol) in 4 NHCl/1,4-dioxane (5 mL) was stirred for 24 h at room temperature.

The reaction was concentrated in vacuo and the resulting residue was purified by chiral SFC to afford two enantiomers. Compound 207: $^1$HNMR (400 MHz, CD$_3$OD) δ 9.22 (s, 1H), 8.24 (s, 1H), 7.93 (d, J=5.2 Hz, 1H), 7.51 (s, 1H), 7.38 (s, 1H), 6.91 (s, 1H), 6.67-6.60 (m, 2H), 3.86 (s, 3H), 3.15-3.07 (m, 4H), 2.42-2.32 (m, 1H), 2.15-2.04 (m, 4H), 1.75-1.67 (m, 4H), 1.57 (dt, J=9.1, 4.5 Hz, 1H), 1.33-1.20 (m, 1H). LCMS (ESI): RT (min)=1.14, [M+H]+=467.0, Method=K. Compound 208: $^1$HNMR (400 MHz, CD$_3$OD) δ 9.22 (s, 1H), 8.24 (s, 1H), 7.93 (d, J=5.3 Hz, 1H), 7.51 (s, 1H), 7.38 (s, 1H), 6.91 (s, 1H), 6.67-6.60 (m, 2H), 3.86 (s, 3H), 3.15-3.07 (m, 4H), 2.37 (dt, J=9.7, 4.4 Hz, 1H), 2.14-2.04 (m, 4H), 1.75-1.67 (m, 4H), 1.57 (dt, J=9.3, 4.6 Hz, 1H), 1.33-1.20 (m, 1H). LCMS (ESI): RT (min)=1.38, [M+H]+=467.0, Method=K.

Example 125

(±)-trans-N-(8-amino-6-(5-amino-4-methylpyridin-3-yl)-7-chloroisoquinolin-3-yl)-2-(cyanomethyl)cyclopropanecarboxamide (Compound 209)

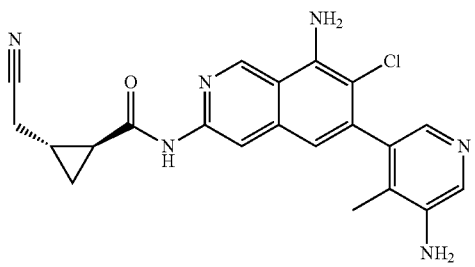 [SMILES: Cc1c(N)cncc1-c1cc2cc(NC(=O)[C@H]3C[C@@H]3CC#N)ncc2c(N)c1Cl]

644

Step 1: tert-Butyl N-[5-(3-amino-8-chloroisoquinolin-6-yl)-4-methylpyridin-3-yl]-N-[(tert-butoxy)carbonyl]carbamate

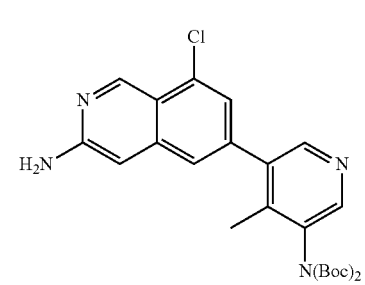

A suspension of 6-bromo-8-chloroisoquinolin-3-amine (5.8 g, 22 mmol), (5-[bis[(tert-butoxy)carbonyl]amino]-4-methylpyridin-3-yl)boronic acid (16.0 g, 45.4 mmol), Pd(dppf)Cl$_2$·CH$_2$Cl$_2$ (3.3 g, 4.0 mmol), and sodium carbonate (4.81 g, 45.38 mmol) in dioxane (100 mL) and water (10 mL) was heated at 85° C. After 16 h, the reaction was filtered, and the filtrate was concentrated in vacuo. Purification by flash column chromatography (1%→50% ethyl acetate/petroleum ether) afforded tert-butyl N-[5-(3-amino-8-chloroisoquinolin-6-yl)-4-methylpyridin-3-yl]-N-[(tert-butoxy)carbonyl]carbamate (4.5 g, 41%) as a light yellow solid. LCMS (ESI): M+H+=485, 487.

Step 2: tert-butyl N-[3-amino-6-(5-[bis[(tert-butoxy)carbonyl]amino]-4-methylpyridin-3-yl)isoquinolin-8-yl]carbamate

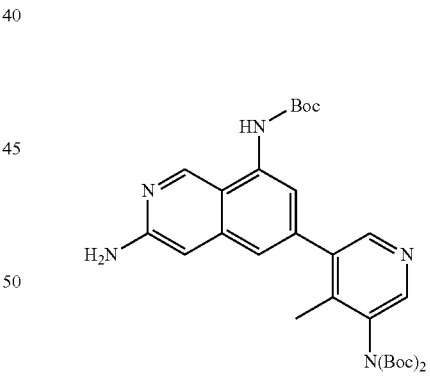

A suspension of tert-butyl N-[5-(3-amino-8-chloroisoquinolin-6-yl)-4-methylpyridin-3-yl]-N-[(tert-butoxy)carbonyl]carbamate (5.0 g, 10.3 mmol), tert-butyl carbamate (24 g, 205 mmol), BrettPhos (1.1 g, 2.05 mmol), Pd$_2$(dba)$_3$·CHCl$_3$ (2.13 g, 2.06 mmol), and Cs$_2$CO$_3$ (6.7 g, 20.6 mmol) in 1,4-dioxane (120 mL) was heated at 85° C. After 3 h, the reaction was concentrated in vacuo, and the resulting residue was purified by flash column chromatography (1%→10% dichloromethane/methanol) to afford tert-butyl N-[3-amino-6-(5-[bis[(tert-butoxy)carbonyl]amino]-4-methylpyridin-3-yl)isoquinolin-8-yl]carbamate (1.5 g, 26%) as a light yellow solid. LCMS (ESI): M+H+=566.0

Step 3: (±)-trans-tert-butyl N-[6-(5-[bis[(tert-butoxy)carbonyl]amino]-4-methylpyridin-3-yl)-3-[[2-(cyanomethyl)cyclopropane]amido]isoquinolin-8-yl]carbamate

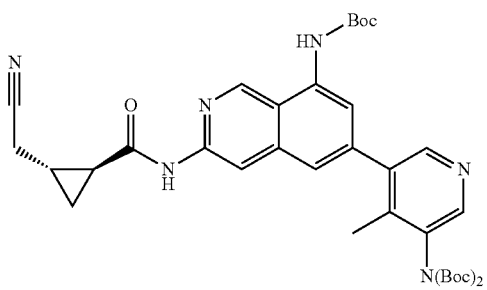

To an ice-cooled of solution of trans-2-(cyanomethyl)cyclopropane-1-carboxylic acid (0.50 g, 3.40 mmol), tert-butyl N-[3-amino-6-(5-[bis[(tert-butoxy)carbonyl]amino]-4-methylpyridin-3-yl)isoquinolin-8-yl]carbamate (132 mg, 0.23 mmol) and pyridine (4 mL, 50 mmol) in dichloromethane (20 mL) was added $POCl_3$ (401 mg, 2.62 mmol) dropwise. The reaction was warmed to room temperature for 1 h and then diluted with water (20 mL). The resulting solution was extracted with ethyl acetate (3×50 mL). The combine organics were dried over anhydrous sodium sulfate, filtered, and concentrated in vacuo. Purification by flash column chromatography (1%→10% dichloromethane/methanol) afforded (±)-trans-tert-butyl N-[6-(5-[bis[(tert-butoxy)carbonyl]amino]-4-methylpyridin-3-yl)-3-[[2-(cyanomethyl)cyclopropane]amido]isoquinolin-8-yl]carbamate (330 mg, 12%) as a light yellow solid. LCMS (ESI): $M+H^+$=673.1

Step 4: (±)-trans-N-[8-amino-6-(5-amino-4-methylpyridin-3-yl)isoquinolin-3-yl]-2-(cyanomethyl)cyclopropane-1-carboxamide

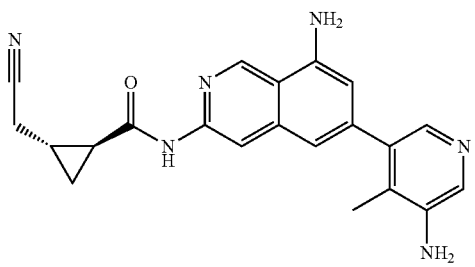 [SMILES: Cc1c(N)cncc1-c1cc(N)c2cnc(NC(=O)[C@H]3C[C@@H]3CC#N)cc2c1]

To a solution of trans-tert-butyl N-[6-(5-[bis[(tert-butoxy)carbonyl]amino]-4-methylpyridin-3-yl)-3-[[2-(cyanomethyl)cyclopropane]amido]isoquinolin-8-yl]carbamate (0.060 g, 0.089 mmol) in dichloromethane (5 mL) was added trifluoroacetic acid (5 mL) at room temperature. After 2 h, the reaction mixture was concentrated in vacuo to afford crude trans-N-[8-amino-6-(5-amino-4-methylpyridin-3-yl)isoquinolin-3-yl]-2-(cyanomethyl)cyclopropane-1-carboxamide (20.4 mg, 31%) as a light yellow solid. LCMS (ESI): $M+H^+$=473.1

Step 5: (±)-trans-N-[8-amino-6-(5-amino-4-methylpyridin-3-yl)-7-chloroisoquinolin-3-yl]-2-(cyanomethyl)cyclopropane-1-carboxamide

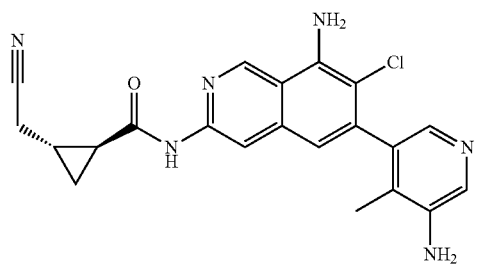 [SMILES: Cc1c(N)cncc1-c1cc2cc(NC(=O)[C@H]3C[C@@H]3CC#N)ncc2c(N)c1Cl]

A solution of (±)-trans-N-[8-amino-6-(5-amino-4-methylpyridin-3-yl)isoquinolin-3-yl]-2-(cyanomethyl)cyclopropane-1-carboxamide (110 mg, 0.30 mmol) and NCS (39.5 mg, 0.30 mmol) in $CH_3CN$ (10 mL) was heated at 60° C. After 6 h, the reaction mixture was concentrated in vacuo, and the resulting residue was purified by Prep-HPLC to afford (±)-trans-N-[8-amino-6-(5-amino-4-methylpyridin-3-yl)-7-chloroisoquinolin-3-yl]-2-(cyanomethyl)cyclopropane-1-carboxamide (20.4 mg, 17%) as a light yellow solid. $^1$HNMR (400 MHz, DMSO-$d_6$) δ 10.95 (s, 1H), 9.45 (s, 1H), 8.24 (s, 1H), 7.97 (s, 1H), 7.56 (s, 1H), 6.88 (s, 1H), 6.54 (s, 2H), 5.22 (s, 2H), 2.77-2.70 (m, 2H), 2.11-2.07 (m, 1H), 1.82 (s, 3H), 1.58-1.55 (m, 1H), 1.15-1.08 (m, 1H), 0.99-0.92 (m, 1H). LCMS (ESI): RT (min)=1.21, [M+H]+=407.0, method=M.

Example 126

(1R,2R)—N-(8-amino-6-(4-methyl-2-(1-methyl-1H-pyrazol-4-yl)pyridin-3-yl)isoquinolin-3-yl)-2-(1-methyl-1H-pyrazol-4-yl)cyclopropanecarboxamide (Compound 210) and (1S,2S)—N-(8-amino-6-(4-methyl-2-(1-methyl-1H-pyrazol-4-yl)pyridin-3-yl)isoquinolin-3-yl)-2-(1-methyl-1H-pyrazol-4-yl)cyclopropanecarboxamide (Compound 211)

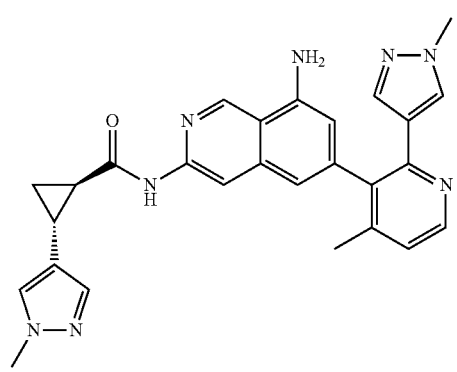

-continued

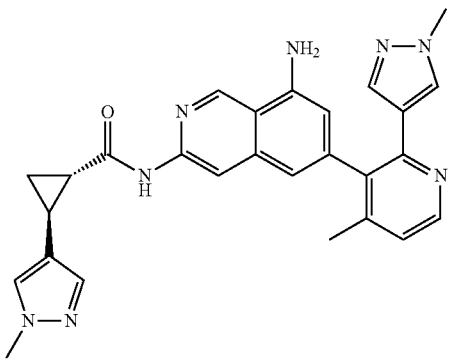

The title compound was prepared by following the procedure as described for (1S,2S)—N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropanecarboxamide (Compound 180) and making slight variations. The enantiomers were isolated by chiral SFC. Compound 210: $^1$HNMR (400 MHz, CD$_3$OD) δ 9.28 (s, 1H), 8.41 (d, J=5.1 Hz, 1H), 8.26 (s, 1H), 7.51 (s, 1H), 7.37 (d, J=8.0 Hz, 2H), 7.27 (d, J=5.1 Hz, 1H), 7.16 (s, 1H), 6.89 (s, 1H), 6.53 (d, J=1.4 Hz, 1H), 3.86 (s, 3H), 3.71 (s, 3H), 2.36 (ddd, J=9.6, 6.3, 4.0 Hz, 1H), 2.18 (s, 3H), 2.14-2.05 (m, 1H), 1.56 (dt, J=9.1, 4.6 Hz, 1H), 1.27-1.20 (m, 1H). LCMS (ESI): RT (min)=1.09, [M+H]$^+$=479.3, Method=K. Compound 211: $^1$HNMR (400 MHz, CD$_3$OD) δ 9.28 (s, 1H), 8.41 (d, J=5.1 Hz, 1H), 8.26 (s, 1H), 7.51 (s, 1H), 7.37 (d, J=8.0 Hz, 2H), 7.27 (d, J=5.1 Hz, 1H), 7.16 (s, 1H), 6.89 (s, 1H), 6.53 (d, J=1.4 Hz, 1H), 3.86 (s, 3H), 3.71 (s, 3H), 2.36 (ddd, J=9.8, 6.4, 4.0 Hz, 1H), 2.18 (s, 3H), 2.14-2.07 (m, 1H), 1.56 (dt, J=9.2, 4.6 Hz, 1H), 1.28-1.19 (m, 1H) LCMS (ESI): RT (min)=1.09, [M+H]$^+$=479.3, Method=K.

Example 127

(1S,2S,3S)—N-(8-amino-6-(4-methylpyridin-3-yl)isoquinolin-3-yl)-2-methyl-3-(1-methyl-1H-pyrazol-4-yl)cyclopropanecarboxamide (Compound 212), (1S,2R,3S)—N-(8-amino-6-(4-methylpyridin-3-yl)isoquinolin-3-yl)-2-methyl-3-(1-methyl-1H-pyrazol-4-yl)cyclopropanecarboxamide (Compound 213), (1R,2S,3R)—N-(8-amino-6-(4-methylpyridin-3-yl)isoquinolin-3-yl)-2-methyl-3-(1-methyl-1H-pyrazol-4-yl)cyclopropanecarboxamide (Compound 214), and (1R,2R,3R)—N-(8-amino-6-(4-methylpyridin-3-yl)isoquinolin-3-yl)-2-methyl-3-(1-methyl-1H-pyrazol-4-yl)cyclopropanecarboxamide (Compound 215)

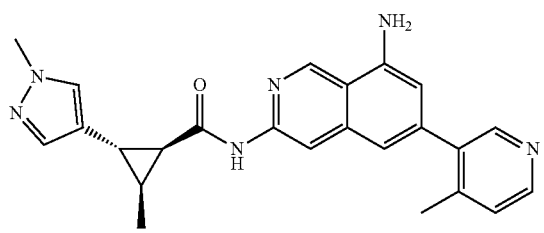

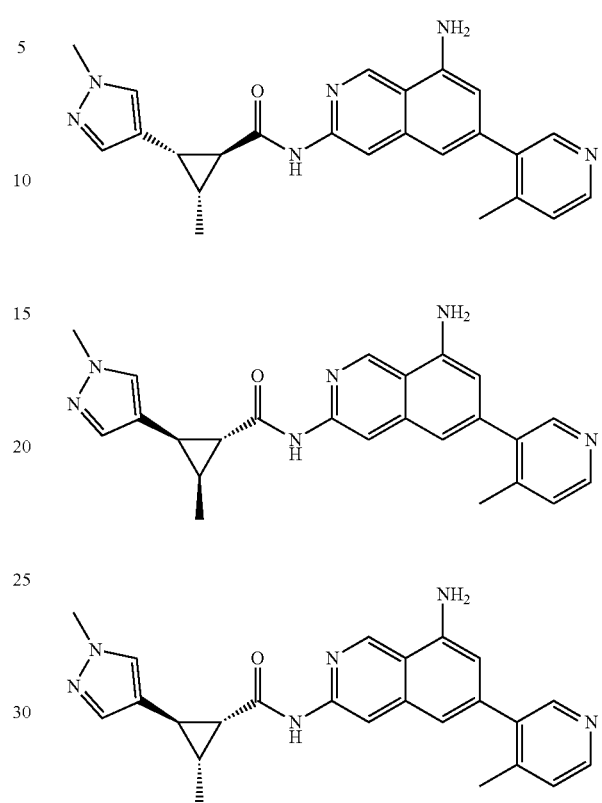

The title compound was prepared by following the procedure as described for (1R,2R,3R)—N-(8-amino-7-fluoro-6-(4-methylpyridin-3-yl)isoquinolin-3-yl)-2-methyl-3-(1-methyl-1H-pyrazol-4-yl)cyclopropanecarboxamide (Compound 195) and making slight variations. The isomers were isolated by chiral SFC. Compound 212: $^1$HNMR (300 MHz, CD$_3$OD) δ 9.26 (s, 1H), 8.45-8.43 (m, 2H), 8.34 (s, 1H), 7.48 (s, 1H), 7.45 (d, J=6.0 Hz 1H), 7.35 (s, 1H), 7.03 (s, 1H), 6.70 (d, J=3.0 Hz, 1H), 3.86 (s, 3H), 2.41 (s, 3H), 2.34 (dd, J=6.5, 4.8 Hz, 1H), 2.17 (dd, J=9.1, 4.9 Hz, 1H), 1.66 (dt, J=8.9, 6.2 Hz, 1H), 1.37 (d, J=6.2 Hz, 3H). LCMS (ESI): RT (min)=0.95, [M+H]$^+$=413.4, Method=N. Compound 213: $^1$HNMR (400 MHz, CD$_3$OD) δ 9.26 (s, 1H), 8.46-8.37 (m, 2H), 8.32 (s, 1H), 7.52 (s, 1H), 7.41 (d, J=4.8 Hz, 2H), 7.04 (s, 1H), 6.69 (d, J=3.0 Hz, 1H), 3.89 (s, 3H), 2.52 (dd, J=9.3, 4.7 Hz, 1H), 2.39 (s, 3H), 1.99 (t, J=4.7 Hz, 1H), 1.82-1.72 (m, 1H), 1.07 (d, J=6.3 Hz, 3H). LCMS (ESI): RT (min)=0.75, [M+H]$^+$=413.2, Method=K. Compound 214: $^1$HNMR (300 MHz, CD$_3$OD) δ 9.24 (s, 1H), 8.42 (d, J=5.4 Hz, 2H), 8.33 (s, 1H), 7.53 (s, 1H), 7.41 (t, J=2.6 Hz, 2H), 7.01 (s, 1H), 6.70 (d, J=3.0 Hz, 1H), 3.90 (s, 3H), 2.53 (dd, J=9.2, 4.7 Hz, 1H), 2.39 (s, 3H), 2.00 (t, J=4.7 Hz, 1H), 1.77 (ddd, J=9.4, 6.1, 4.7 Hz, 1H), 1.07 (d, J=6.2 Hz, 3H). LCMS (ESI): RT (min)=0.74, [M+H]+=413.3, Method=K. Compound 215: $^1$HNMR (300 MHz, CD$_3$OD) δ 9.31 (s, 1H), 8.49-8.39 (m, 2H), 8.34 (s, 1H), 7.55-7.41 (m, 2H), 7.35 (s, 1H), 7.03 (s, 1H), 6.70 (d, J=3.0 Hz, 1H), 3.86 (s, 3H), 2.41 (s, 3H), 2.34 (dd, J=6.5, 4.9 Hz, 1H), 2.17 (dd, J=9.1, 4.9 Hz, 1H), 1.66 (dt, J=9.0, 6.3 Hz, 1H), 1.37 (d, J=6.2 Hz, 3H). LCMS (ESI): RT (min)=0.95, [M+H]+=413.3, Method=N.

Example 128

(1R,2R)—N-(8-amino-6-(2,6-dichlorophenyl)isoquinolin-3-yl)-2-(1-methyl-1H-pyrazol-4-yl)cyclopropanecarboxamide (Compound 216) and (1S,2S)—N-(8-amino-6-(2,6-dichlorophenyl)isoquinolin-3-yl)-2-(1-methyl-1H-pyrazol-4-yl)cyclopropanecarboxamide (Compound 217)

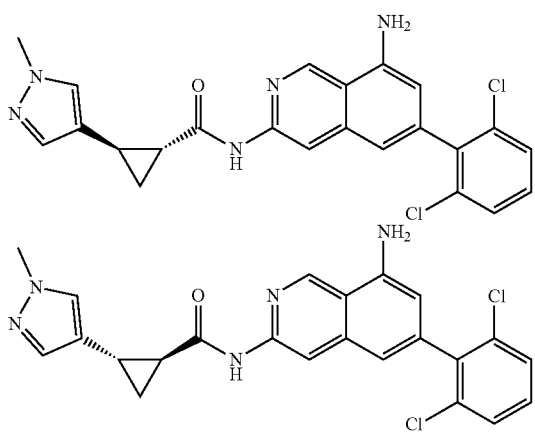

The title compound was prepared by following the procedure as described for (±)-trans-N-(8-amino-6-(8-methylpyrido[3,2-b]pyrazin-7-yl)isoquinolin-3-yl)-2-cyanocyclopropanecarboxamide (Compound 123) and making slight variations. The enantiomers were isolated by chiral SFC. Compound 216: $^1$HNMR (400 MHz, DMSO-$d_6$) δ 10.78 (s, 1H), 9.32 (s, 1H), 8.26 (s, 1H), 7.63-7.55 (m, 3H), 7.48-7.41 (m, 1H), 7.29 (s, 1H), 6.79 (s, 1H), 6.40 (s, 1H), 6.35 (s, 2H), 3.77 (s, 3H), 2.21-2.16 (m, 2H), 1.39-1.35 (m, 1H), 1.19-1.14 (m, 1H). LCMS (ESI): RT (min)=1.30, [M+H]+=452.1, Method=K. Compound 217: $^1$HNMR (400 MHz, DMSO-$d_6$) δ 10.78 (s, 1H), 9.32 (s, 1H), 8.26 (s, 1H), 7.65-7.51 (m, 3H), 7.46 (dd, J=8.7, 7.5 Hz, 1H), 7.30 (s, 1H), 6.79 (s, 1H), 6.40 (s, 1H), 6.35 (s, 2H), 3.78 (s, 3H), 2.23-2.13 (m, 2H), 1.42-1.33 (m, 1H), 1.21-1.12 (m, 1H). LCMS (ESI): RT (min)=1.31, [M+H]$^+$=452.2, Method=K.

Example 129

(1S,2S)—N-(8-amino-6-(2,6-difluorophenyl)isoquinolin-3-yl)-2-(1-methyl-1H-pyrazol-4-yl)cyclopropanecarboxamide (Compound 218) and (1R,2R)—N-(8-amino-6-(2,6-difluorophenyl)isoquinolin-3-yl)-2-(1-methyl-1H-pyrazol-4-yl)cyclopropanecarboxamide

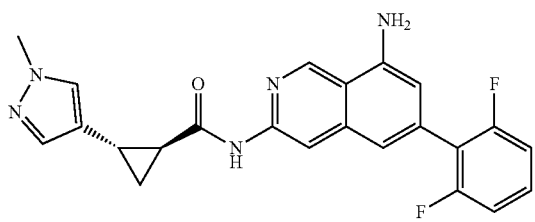

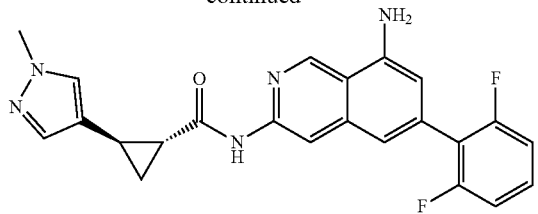

The title compound was prepared by following the procedure as described for (±)-trans-N-(8-amino-6-(8-methylpyrido[3,2-b]pyrazin-7-yl)isoquinolin-3-yl)-2-cyanocyclopropanecarboxamide (Compound 123) and making slight variations. The single isomers were isolated by chiral SFC. Compound 218: $^1$HNMR (400 MHz, CD$_3$OD) δ 9.24 (s, 1H), 8.30 (s, 1H), 7.51 (s, 1H), 7.44 (ddd, J=8.5, 6.3, 2.1 Hz, 1H), 7.38 (s, 1H), 7.10 (t, J=8.0 Hz, 3H), 6.78 (s, 1H), 3.86 (s, 3H), 2.37 (td, J=6.1, 3.2 Hz, 1H), 2.11 (dt, J=8.7, 4.7 Hz, 1H), 1.57 (ddd, J=9.2, 5.1, 4.1 Hz, 1H), 1.26 (ddd, J=8.2, 6.4, 4.1 Hz, 1H). LCMS (ESI): RT (min)=1.49, [M+H]$^+$=420.2, Method=K. Compound 219: $^1$HNMR (400 MHz, CD$_3$OD) δ 9.24 (s, 1H), 8.30 (s, 1H), 7.51 (s, 1H), 7.44 (ddd, J=8.5, 6.3, 2.1 Hz, 1H), 7.38 (s, 1H), 7.10 (t, J=8.0 Hz, 3H), 6.78 (s, 1H), 3.86 (s, 3H), 2.37 (td, J=6.1, 3.2 Hz, 1H), 2.11 (dt, J=8.7, 4.7 Hz, 1H), 1.57 (ddd, J=9.2, 5.1, 4.1 Hz, 1H), 1.26 (ddd, J=8.2, 6.4, 4.1 Hz, 1H). LCMS (ESI): RT (min)=1.49, [M+H]$^+$=420.2, Method=K.

Example 130

(1S,2S)—N-(8-amino-6-(2-cyano-6-methylphenyl)isoquinolin-3-yl)-2-cyanocyclopropanecarboxamide (Compound 220) and (1R,2R)—N-(8-amino-6-(2-cyano-6-methylphenyl)isoquinolin-3-yl)-2-cyanocyclopropanecarboxamide (Compound 221)

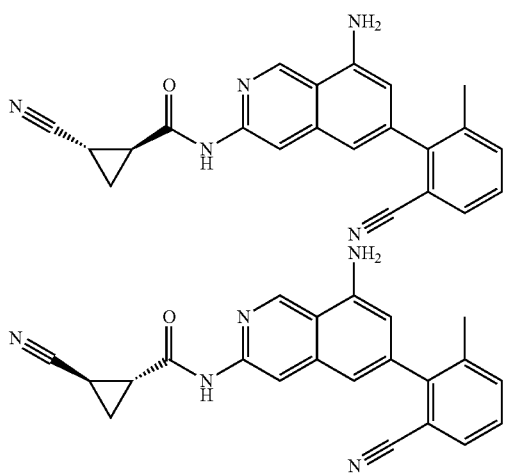

The title compound was prepared by following the procedure as described for (±)-trans-N-(8-amino-6-(8-methylpyrido[3,2-b]pyrazin-7-yl)isoquinolin-3-yl)-2-cyanocyclopropanecarboxamide (Compound 123) and making slight variations. The enantiomers were isolated by chiral SFC. Compound 220: $^1$H NMR (300 MHz, DMSO-$d_6$) δ 11.14 (s, 1H), 9.37 (s, 1H), 8.24 (s, 1H), 7.76 (d, J=5.5 Hz, 1H), 7.66 (d, J=5.5 Hz, 1H), 7.50 (t, J=5.8 Hz, 1H), 6.86 (s, 1H), 6.46

(d, J=7.2 Hz, 3H), 2.78-2.72 (m, 1H), 2.16-2.10 (m, 4H), 1.62-1.57 (m, 1H), 1.45-1.43 (m, 1H). LCMS (ESI): RT (min)=1.55, [M+H]$^+$=368.2, Method=M. Compound 221: $^1$H NMR (300 MHz, DMSO-d$_6$) δ 11.14 (s, 1H), 9.37 (s, 1H), 8.24 (s, 1H), 7.76 (d, J=5.5 Hz, 1H), 7.66 (d, J=5.5 Hz, 1H), 7.50 (t, J=5.8 Hz, 1H), 6.86 (s, 1H), 6.46 (d, J=7.2 Hz, 3H), 2.78-2.72 (m, 1H), 2.16-2.10 (m, 4H), 1.62-1.57 (m, 1H), 1.45-1.43 (m, 1H). LCMS (ESI): RT (min)=1.55, [M+H]$^+$=368.2, Method=M.

Example 131

(1S,2S)—N-(8-amino-6-(4-methyl-2-(1-methyl-1H-pyrazol-3-yl)pyridin-3-yl)isoquinolin-3-yl)-2-(1-methyl-1H-pyrazol-4-yl)cyclopropanecarboxamide (Compound 222) and (1R,2R)—N-(8-amino-6-(4-methyl-2-(1-methyl-1H-pyrazol-3-yl)pyridin-3-yl)isoquinolin-3-yl)-2-(1-methyl-1H-pyrazol-4-yl)cyclopropanecarboxamide (Compound 223)

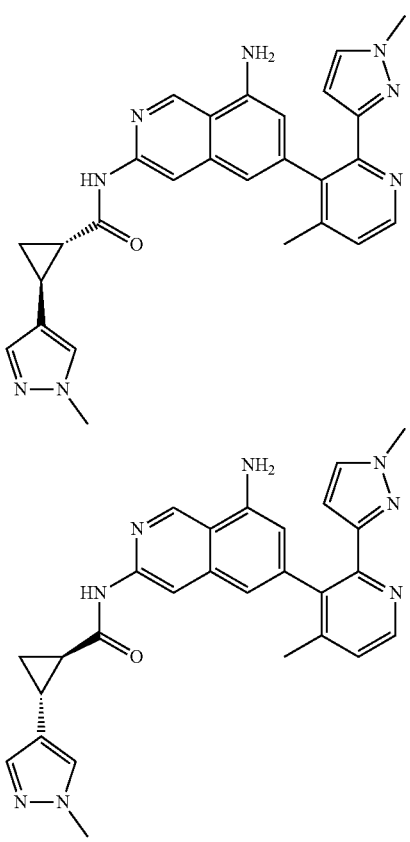

The title compound was prepared by following the procedure as described for (1S,2S)—N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropanecarboxamide (Compound 180) and making slight variations. The enantiomers were isolated by chiral SFC. Compound 222: $^1$HNMR (400 MHz, DMSO-d$_6$) 10.74 (s, 1H), 9.27 (s, 1H), 8.48 (d, J=6.0 Hz, 1H), 8.19 (s, 1H), 7.56 (s, 1H), 7.38-7.29 (m, 3H), 6.71 (s, 1H), 6.33 (s, 1H), 6.20 (s, 2H), 5.77 (s, 1H), 3.77 (s, 3H), 3.68 (s, 3H), 2.18 (t, J=6.0 Hz, 2H), 2.09 (s, 3H), 1.35-1.34 (m, 1H), 1.17-1.15 (m, 1H). LCMS (ESI): RT (min)=1.10, [M+H]$^+$=479.3, Method=K. Compound 223: $^1$HNMR (400 MHz, DMSO-d$_6$) 10.74 (s, 1H), 9.27 (s, 1H), 8.48 (d, J=6.0 Hz, 1H), 8.19 (s, 1H), 7.56 (s, 1H), 7.38-7.29 (m, 3H), 6.71 (s, 1H), 6.33 (s, 1H), 6.20 (s, 2H), 5.77 (s, 1H), 3.77 (s, 3H), 3.68 (s, 3H), 2.18 (t, J=6.0 Hz, 2H), 2.09 (s, 3H), 1.35-1.34 (m, 1H), 1.17-1.15 (m, 1H). LCMS (ESI): RT (min)=1.10, [M+H]$^+$=479.3, Method=K.

Example 132 exo-N-(8-amino-7-chloro-6-(4-methylpyridin-3-yl)isoquinolin-3-yl)-3-hydroxybicyclo[3.1.0]hexane-6-carboxamide (Compound 224), exo-N-(8-amino-5-chloro-6-(4-methylpyridin-3-yl)isoquinolin-3-yl)-3-hydroxybicyclo[3.1.0]hexane-6-carboxamide (Compound 225) and exo-N-(8-amino-5,7-dichloro-6-(4-methylpyridin-3-yl)isoquinolin-3-yl)-3-hydroxybicyclo[3.1.0]hexane-6-carboxamide (Compound 226)

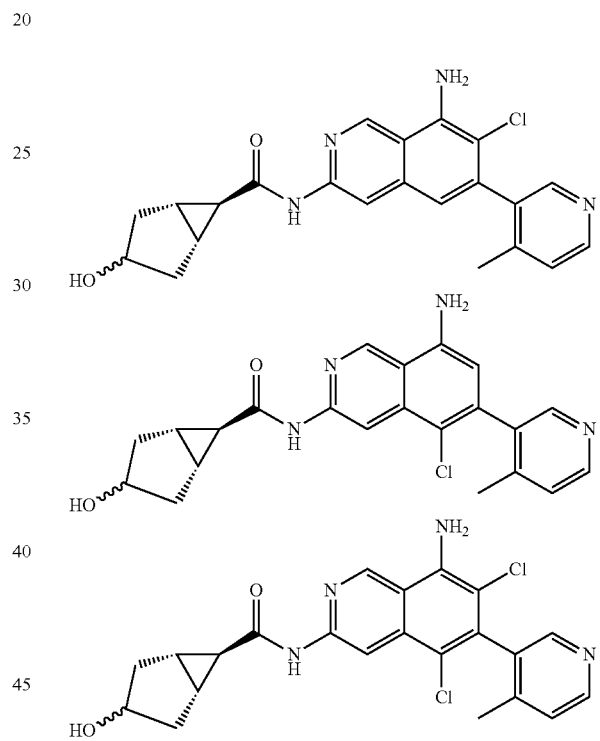

Step 1: (exo)-3-[(tert-butyldiphenylsilyl)oxy]-N-[8-chloro-6-(4-methylpyridin-3-yl)isoquinolin-3-yl]-1-methylbicyclo[3.1.0]hexane-6-carboxamide

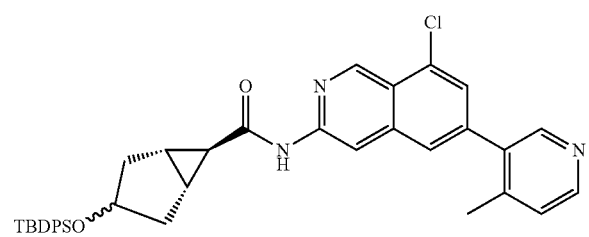

To an ice-cooled solution of (exo)-3-[(tert-butyldiphenylsilyl)oxy]bicyclo[3.1.0]hexane-6-carboxylic acid (289 mg, 0.75 mmol) (WO2015091889), 8-chloro-6-(4-methylpyridin-3-yl)isoquinolin-3-amine (488 mg, 1.80 mmol) and pyridine (1 mL) in dichloromethane (5 mL) was added POCl$_3$ (491 mg, 3.20 mmol) dropwise. The reaction was warmed to room temperature for 30 min and then diluted with water (10 mL). The solution was extracted with ethyl acetate (3×50 mL). The combined organic layers were dried over anhydrous sodium sulfate, filtered, and concentrated in vacuo. Purification by flash column chromatography (1:1ethyl acetate/petroleum ether) afforded (exo)-3-[(tert-butyldiphenylsilyl)oxy]-N-[8-chloro-6-(4-methylpyridin-3-yl)isoquinolin-3-yl]-1-methylbicyclo[3.1.0]hexane-6-carboxamide (0.30 g, 61%) as light yellow oil. LCMS (ESI): M+H$^+$=632.2

Step 2: Tert-butyl N-[6-(4-methylpyridin-3-yl)-3-[(exo)-3-[(tert-butyldiphenylsilyl)oxy]bicyclo[3.1.0]hexane-6-amido]isoquinolin-8-yl]carbamate

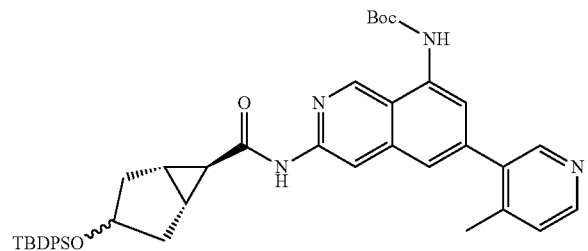

A suspension of (exo)-3-[(tert-butyldiphenylsilyl)oxy]-N-[8-chloro-6-(4-methylpyridin-3-yl)isoquinolin-3-yl]bicyclo[3.1.0]hexane-6-carboxamide (0.40 g, 0.63 mmol), tert-butyl carbamate (1.85 mg, 0.02 mmol), Pd$_2$(dba)$_3$ (130 mg, 0.14 mmol), Cs$_2$CO$_3$ (819 mg, 2.51 mmol), and BrettPhos (135 mg, 0.25 mmol) in dioxane (10 mL) was heated at 120° C. After 2 h, the reaction was filtered, and the filtrate was concentrated in vacuo. Purification by flash column chromatography (1:1 ethyl acetate/petroleum ether) afforded tert-butyl N-[6-(4-methylpyridin-3-yl)-3-[(exo)-3-[(tert-butyldiphenylsilyl)oxy]bicyclo[3.1.0]hexane-6-amido]isoquinolin-8-yl]carbamate (315 mg, 70%) as a yellow solid. LCMS (ESI): M+H$^+$=713.3

Step 3: (exo)-N-[8-amino-6-(4-methylpyridin-3-yl)isoquinolin-3-yl]-3-[(tert-butyldiphenylsilyl)methyl]bicyclo[3.1.0]hexane-6-carboxamide

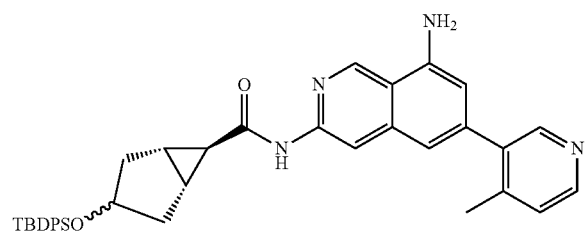

A solution of tert-butyl N-[6-(4-methylpyridin-3-yl)-3-[(exo)-3-[(tert-butyldiphenylsilyl)methyl]bicyclo[3.1.0]hexane-6-amido]isoquinolin-8-yl]carbamate (630 mg, 0.88 mmol) in trifluoroacetic acid (6 mL) and dichloromethane (30 mL) was stirred for 1 h at room temperature. The reaction was concentrated in vacuo, and the residue was diluted with DCM (20 mL). The mixture was basified to pH=8 with a solution of NH$_3$ in methanol (7 M) and concentrated. Purification by flash column chromatography provided (exo)-N-[8-amino-6-(4-methylpyridin-3-yl)isoquinolin-3-yl]-3-[(tert-butyldiphenylsilyl)methyl]bicyclo[3.1.0]hexane-6-carboxamide (480 mg, 89%) as a yellow solid. LCMS (ESI): M+H$^+$=613.3

Step 4: (exo)-N-(8-amino-7-chloro-6-(4-methylpyridin-3-yl)isoquinolin-3-yl)-3-(tert-butyldiphenylsilyloxy)bicyclo[3.1.0]hexane-6-carboxamide, (exo)-N-(8-amino-5-chloro-6-(4-methylpyridin-3-yl)isoquinolin-3-yl)-3-(tert-butyldiphenylsilyoxy)bicycle[3.1.0]hexane-6-carboxamide and (exo)-N-(8-amino-5,7-dichloro-6-(4-methylpyridin-3-yl)isoquinolin-3-yl)-3-(tert-butyldiphenylsilyloxy)bicyclo[3.1.0]hexane-6-carboxamide

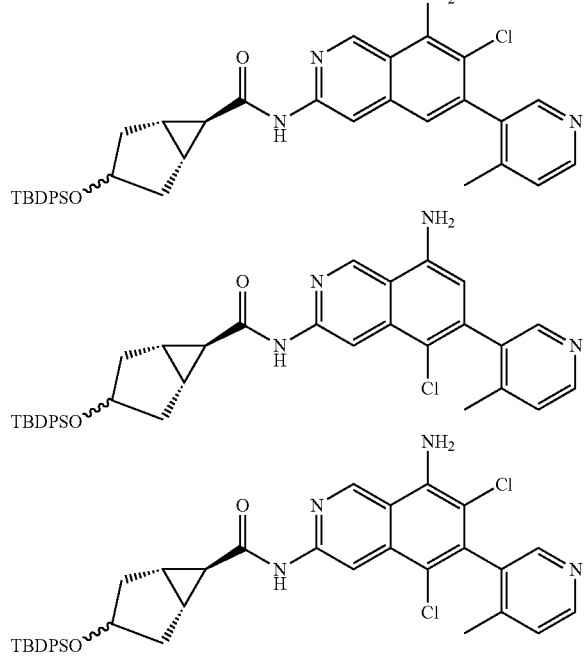

A solution of (exo)-N-[8-amino-6-(4-methylpyridin-3-yl)isoquinolin-3-yl]-3-[(tert-butyldiphenylsilyl)methyl]bicyclo[3.1.0]hexane-6-carboxamide (320 mg, 0.52 mmol) and NCS (35 mg, 0.52 mmol) in CH$_3$CN (10 mL) was heated at 50° C. After 1 h, additional NCS (35 mg, 0.52 mmol) was added, and the solution was maintained at 50° C. for another 2 h. The reaction was concentrated under vacuum, and the resulting residue was purified by flash column chromatography (10:1 dichloromethane/methanol) to provide a mixture of (exo)-N-(8-amino-7-chloro-6-(4-methylpyridin-3-yl)isoquinolin-3-yl)-3-(tert-butyldiphenylsilyloxy)bicyclo[3.1.0]hexane-6-carboxamide, (exo)-N-(8-amino-5-chloro-6-(4-methylpyridin-3-yl)isoquinolin-3-yl)-3-(tert-butydiphenylsilyoxy)bicycle[3.1.0]hexane-6-carboxamide and (exo)-N-(8-amino-5,7-dichloro-6-(4-methylpyridin-3-yl)isoquinolin-3-yl)-3-(tert-butyldiphenylsilyloxy)bicyclo[3.1.0]hexane-6-carboxamide (0.30 g, 89%) as a solid. LCMS (ESI): M+H$^+$=647.3, 681.2;

Step 5: (exo)-N-(8-amino-7-chloro-6-(4-methylpyridin-3-yl)isoquinolin-3-yl)-3-hydroxybicyclo[3.1.0]hexane-6-carboxamide and (exo)-N-(8-amino-5-chloro-6-(4-methylpyridin-3-yl)isoquinolin-3-yl)-3-hydroxybicyclo[3.1.0]hexane-6-carboxamide and (exo)-N-(8-amino-5,7-dichloro-6-(4-methylpyridin-3-yl)isoquinolin-3-yl)-3-hydroxybicyclo[3.1.0]hexane-6-carboxamide

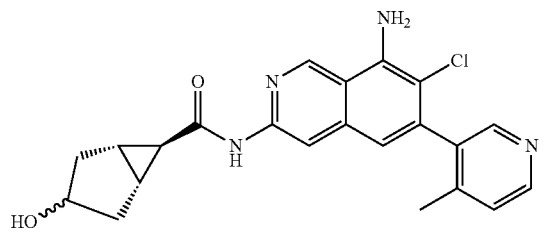

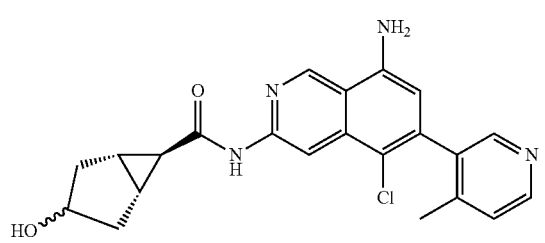

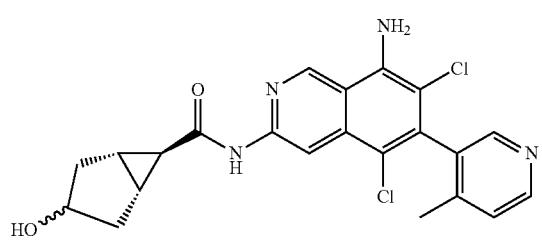

To a mixture of (exo)-N-(8-amino-7-chloro-6-(4-methylpyridin-3-yl)isoquinolin-3-yl)-3-(tert-butyldiphenylsilyloxy)bicyclo[3.1.0]hexane-6-carboxamide, (exo)-N-(8-amino-5-chloro-6-(4-methylpyridin-3-yl)isoquinolin-3-yl)-3-(tert-butydiphenylsilyoxy)bicycle[3.1.0]hexane-6-carboxamide and (exo)-N-(8-amino-5,7-dichloro-6-(4-methylpyridin-3-yl)isoquinolin-3-yl)-3-(tert-butyldiphenylsilyloxy)bicyclo[3.1.0]hexane-6-carboxamide (0.30 g) in tetrahydrofuran (10 mL) was added TBAF (1.03 g, 3.93 mmol) at room temperature. After 30 min the reaction was concentrated in vacuo, and the crude product was purified by Prep-HPLC to afford three products. Compound 224: ¹HNMR (300 MHz, DMSO-d₆) 10.59 (s, 1H), 9.44 (s, 1H), 8.49 (d, J=6.0 Hz, 1H), 8.32 (s, 1H), 8.23 (s, 1H), 7.37 (d, J=6.0 Hz, 1H), 6.91 (s, 1H), 6.57 (s, 2H), 4.70 (d, J=6.0 Hz, 1H), 3.85-3.78 (m, 1H), 2.11 (s, 3H), 2.09-2.04 (m, 2H), 1.89-1.87 (m, 1H), 1.73-1.71 (m, 2H), 1.69-1.61 (m, 2H). LCMS (ESI): RT (min)=2.236, [M+H]+=409.1, Method=K. Compound 225: ¹HNMR (300 MHz, DMSO-d₆) 10.70 (s, 1H), 9.37 (s, 1H), 8.62 (s, 1H), 8.49 (d, J=6.0 Hz, 1H), 8.32 (s, 1H), 7.38 (d, J=6.0 Hz, 1H), 6.54 (s, 2H), 6.44 (s, 1H), 4.71 (d, J=6.0 Hz, 1H), 3.83-3.78 (m, 1H), 2.12 (s, 3H), 2.09-2.05 (m, 2H), 1.92-1.90 (m, 1H), 1.76-1.74 (m, 2H), 1.69-1.62 (m, 2H). LCMS (ESI): RT (min)=1.029, [M+H]+=409.2, Method=K. Compound 226: ¹HNMR (300 MHz, DMSO-d₆) 10.79 (s, 1H), 9.53 (s, 1H), 8.64 (s, 1H), 8.53 (d, J=6.0 Hz, 1H), 8.29 (s, 1H), 7.43 (d, J=6.0 Hz, 1H), 6.77 (s, 2H), 4.71 (d, J=6.0 Hz, 1H), 3.85-3.79 (m, 1H), 2.12-2.08 (m, 2H), 2.05 (s, 3H), 1.92-1.90 (m, 1H), 1.75-1.74 (m, 2H), 1.69-1.62 (m, 2H). LCMS (ESI): RT (min)=1.205, [M+H]+=443.1, Method=L.

Example 133

1-(8-amino-7-fluoro-6-(8-methyl-2,3-dihydro-1H-pyrido[2,3-b][1,4]oxazin-7-yl)isoquinolin-3-yl)-3-(cyclopropylmethyl)urea (Compound 29)

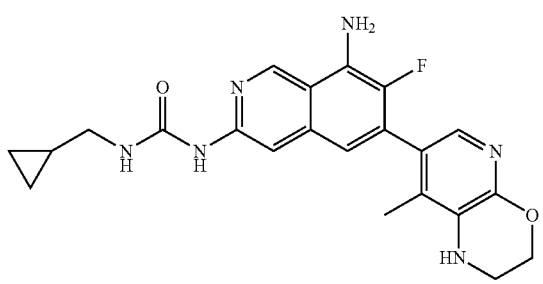 [SMILES: Cc1c(-c2cc3cc(NC(=O)NCC4CC4)ncc3c(N)c2F)cnc2c1NCCO2]

Step 1: tert-butyl 7-(3-amino-8-chloro-7-fluoro-6-isoquinolyl)-8-methyl-2,3-dihydropyrido[2,3-b][1,4]oxazine-1-carboxylate

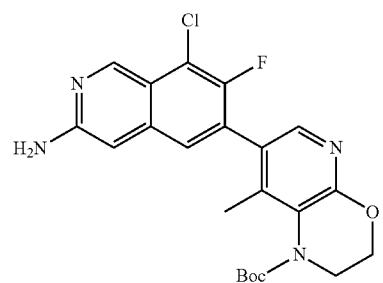 [SMILES: Cc1c(-c2cc3cc(N)ncc3c(Cl)c2F)cnc2c1N(C(=O)OC(C)(C)C)CCO2]

A solution of 8-chloro-7-fluoro-6-iodo-isoquinolin-3-amine (1.14 g, 3.54 mmol), [1,1'-bis(diphenylphosphino)ferrocene]dichloropalladium(II) (518.19 mg, 0.71 mmol), potassium carbonate (1.47 g, 10.62 mmol) and tert-butyl 8-methyl-7-(4,4,5,5-tetramethyl-1,3,2-dioxaborolan-2-yl)-2,3-dihydropyrido[2,3-b][1,4]oxazine-1-carboxylate (2.0 g, 5.32 mmol) in 1,4-dioxane (20 mL)/water (4 mL) was stirred for 1 hour at 90° C. After filtration, the filtrate was concentrated under vacuum. The residue was purified by flash chromatography on silica gel eluting with petroleum ether/ethyl acetate (3/1) to afford tert-butyl 7-(3-amino-8-chloro-7-fluoro-6-isoquinolyl)-8-methyl-2,3-dihydropyrido[2,3-b][1,4]oxazine-1-carboxylate (1.5 g, 3.37 mmol) as a yellow solid. LCMS (ESI) [M+H]⁺=445.1.

Step 2: tert-butyl 7-(8-chloro-7-fluoro-3-(((4-nitrophenoxy)carbonyl)amino)isoquinolin-6-yl)-8-methyl-2,3-dihydro-1H-pyrido[2,3-b][1,4]oxazine-1-carboxylate

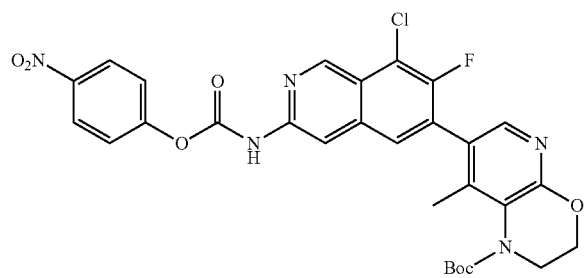 [SMILES: Cc1c(-c2cc3cc(NC(=O)Oc4ccc([N+](=O)[O-])cc4)ncc3c(Cl)c2F)cnc2c1N(C(=O)OC(C)(C)C)CCO2]

A solution of tert-butyl 7-(3-amino-8-chloro-7-fluoro-6-isoquinolyl)-8-methyl-2,3-dihydropyrido[2,3-b][1,4]oxazine-1-carboxylate (200 mg, 0.45 mmol), pyridine (106.68 mg, 1.35 mmol) and 4-nitrophenylchloroformate (135.92 mg, 0.67 mmol) in dichloromethane (4 mL) was stirred at room temperature for 2 hours. The resulting solution was directly used in the next step without work up. LCMS (ESI) [M+H]⁺=610.

Step 3: tert-butyl 7-[8-chloro-3-(cyclopropylmethylcarbamoylamino)-7-fluoro-6-isoquinolyl]-8-methyl-2,3-dihydropyrido[2,3-b][1,4]oxazine-1-carboxylate

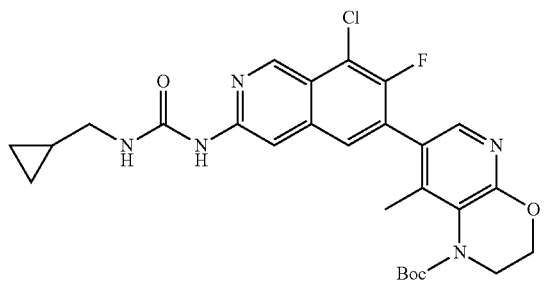 [SMILES: Cc1c(-c2cc3cc(NC(=O)NCC4CC4)ncc3c(Cl)c2F)cnc2c1N(C(=O)OC(C)(C)C)CCO2]

To a solution of tert-butyl 7-[8-chloro-7-fluoro-3-[(4-nitrophenoxy)carbonylamino]-6-isoquinolyl]-8-methyl-2,3-dihydropyrido[2,3-b][1,4]oxazine-1-carboxylate was added cyclopropanemethylamine (34.98 mg, 0.49 mmol) and pyridine (77.8 mg, 0.98 mmol). The reaction was stirred at 25° C. for 2 hours. The solvent was concentrated under vacuum. The residue was purified by reverse phase flash (C18 column, CH₃CN/H₂O=0-80% in 40 mins) to afford tert-butyl 7-[8-chloro-3-(cyclopropylmethylcarbamoylamino)-7-fluoro-6-isoquinolyl]-8-methyl-2,3-dihydropyrido[2,3-b][1,4]oxazine-1-carboxylate (150 mg, 0.28 mmol) as a yellow solid. LCMS (ESI) [M+H]⁺=542.

Step 4: tert-butyl 7-[8-(tert-butoxycarbonylamino)-3-(cyclopropylmethylcarbamoylamino)-7-fluoro-6-isoquinolyl]-8-methyl-2,3-dihydropyrido[2,3-b][1,4]oxazine-1-carboxylate

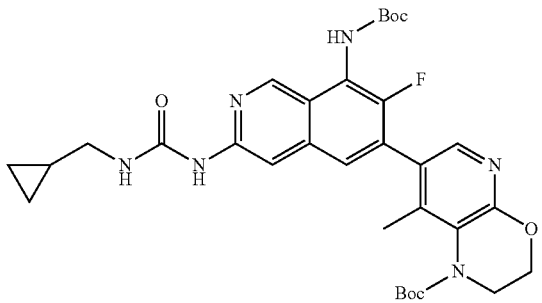 [SMILES: Cc1c(-c2cc3cc(NC(=O)NCC4CC4)ncc3c(NC(=O)OC(C)(C)C)c2F)cnc2c1N(C(=O)OC(C)(C)C)CCO2]

A solution of 1-[8-chloro-7-fluoro-6-(8-methyl-2,3-dihydro-1H-pyrido[2,3-b][1,4]oxazin-7-yl)-3-isoquinolyl]-3-(cyclopropylmethyl)urea (150 mg, 0.28 mmol) and cesium carbonate (353.92 mg, 1.09 mmol), tris(dibenzylideneacetone)dipalladium-chloroform adduct (74.96 mg, 0.07 mmol), 2-(dicyclohexylphosphino)3,6-dimethoxy-2',4',6'-triisopropyl-1,1'-biphenyl (77.74 mg, 0.14 mmol) in 1,4-dioxane (10 mL) was stirred at 90° C. for 3 hours. After filtration, the solvent was concentrated under vacuum. The residue was purified by flash chromatography on silica gel eluting with dichloromethane/methanol (20/1) to afford tert-butyl 7-[8-(tert-butoxycarbonylamino)-3-(cyclopropylmethylcarbamoylamino)-7-fluoro-6-isoquinolyl]-8-methyl-2,3-dihydropyrido[2,3-b][1,4]oxazine-1-carboxylate (130 mg, 0.21 mmol) as a yellow solid. LCMS (ESI) [M+H]⁺=623.

Step 5: 1-[8-amino-7-fluoro-6-(8-methyl-2,3-dihydro-1H-pyrido[2,3-b][1,4]oxazin-7-yl)-3-isoquinolyl]-3-(cyclopropylmethyl)urea

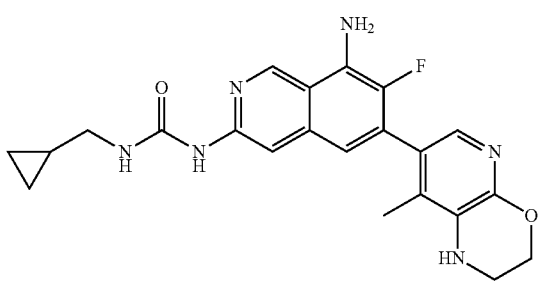 [SMILES: Cc1c(-c2cc3cc(NC(=O)NCC4CC4)ncc3c(N)c2F)cnc2c1NCCO2]

A solution of tert-butyl 7-[8-(tert-butoxycarbonylamino)-3-(cyclopropylmethylcarbamoylamino)-7-fluoro-6-isoquinolyl]-8-methyl-2,3-dihydropyrido[2,3-b][1,4]oxazine-1-carboxylate (130 mg, 0.21 mmol) and trifluoroacetic acid (2 mL) in dichloromethane (4 mL) was stirred at 25° C. for 1 hour. The solvent was concentrated under vacuum. The residue was purified by prep-HPLC (XBridge Prep C18 OBD Column 19×150 mm 5 um; Water (10 mmol/L sodium bicarbonate): CH₃CN=30% B to 50% B in 7 min; 25 mL/min) to afford 1-[8-amino-7-fluoro-6-(8-methyl-2,3-dihydro-1H-pyrido[2,3-b][1,4]oxazin-7-yl)-3-isoquinolyl]-3-(cyclopropylmethyl)urea (49.8 mg, 0.12 mmol) as a yellow solid. LCMS (ESI) [M+H]⁺=423. ¹H NMR (300 MHz, Methanol-d₄) δ 9.21 (s, 1H), 7.53 (s, 1H), 7.35 (s, 1H), 6.86

(d, J=6.2 Hz, 1H), 4.42-4.35 (m, 2H), 3.48 (t, J=4.4 Hz, 2H), 3.18 (d, J=6.9 Hz, 2H), 2.00 (d, J=1.7 Hz, 3H), 1.11-1.08 (m, 1H), 0.58-0.50 (m, 2H), 0.29-0.27 (m, 2H).

Example 134

(1R,2S,3R)—N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide (Compound 9); (1S,2R,3S)—N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide (Compound 10); (1S,2S,3S)—N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide (Compound 11) and (1R,2R,3R)—N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide (Compound 12)

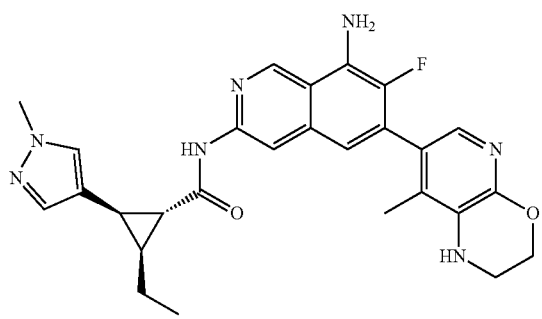

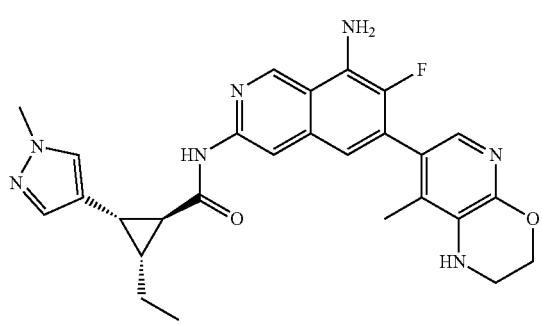

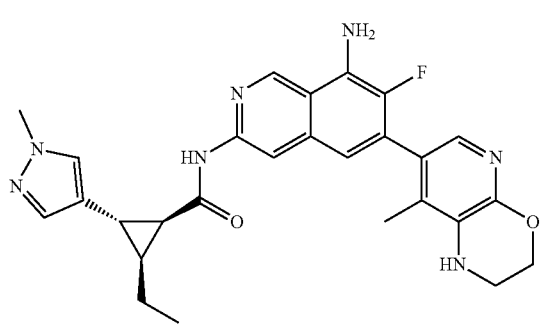

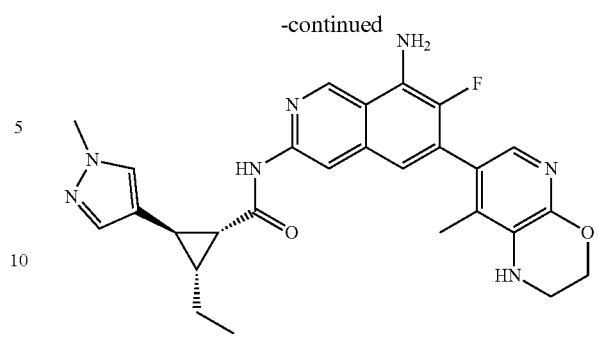

Step 1: tert-butyl 7-(8-chloro-3-((1S,3S)-2-ethyl-3-(1-methyl-1H-pyrazol-4-yl)cyclopropane-1-carboxamido)-7-fluoroisoquinolin-6-yl)-8-methyl-2,3-dihydro-1H-pyrido[2,3-b][1,4]oxazine-1-carboxylate

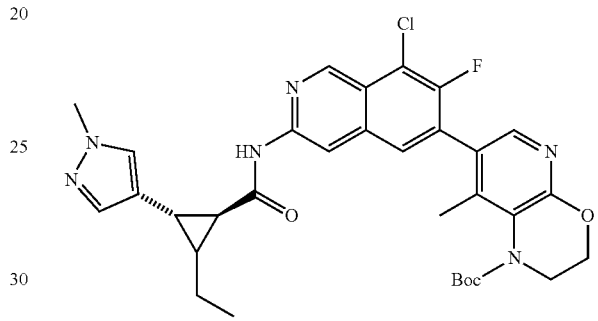

A solution of tert-butyl 7-(3-amino-8-chloro-7-fluoro-6-isoquinolyl)-8-methyl-2,3-dihydropyrido[2,3-b][1,4]oxazine-1-carboxylate (1.6 g, 3.6 mmol) and 2-ethyl-3-(1-methylpyrazol-4-yl)cyclopropanecarboxylic acid (908.09 mg, 4.68 mmol) in dichloromethane (30 mL) and pyridine (6 mL) was stirred at 0° C. for 3 minutes. Phosphorus oxychloride (1.1 g, 7.19 mmol) was added at 0° C. and the mixture was stirred at 25° C. for 30 minutes. The resulting solution was extracted with dichloromethane. The organic layers were combined and concentrated to afford tert-butyl 7-[8-chloro-3-[[(1S,2S)-2-ethyl-3-(1-methylpyrazol-4-yl)cyclopropanecarbonyl]amino]-7-fluoro-6-isoquinolyl]-8-methyl-2,3-dihydropyrido[2,3-b][1,4]oxazine-1-carboxylate (1.4 g, 2.25 mmol) as a brown solid. LCMS (ESI) [M+H]$^+$=621.

Step 2: tert-butyl 7-(8-((tert-butoxycarbonyl)amino)-3-(2-ethyl-3-(1-methyl-1H-pyrazol-4-yl)cyclopropane-1-carboxamido)-7-fluoroisoquinolin-6-yl)-8-methyl-2,3-dihydro-1H-pyrido[2,3-b][1,4]oxazine-1-carboxylate

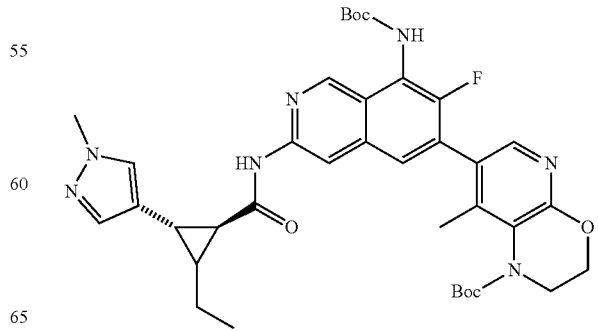

A mixture of tert-butyl 7-[8-chloro-3-[[2-ethyl-3-(1-methylpyrazol-4-yl)cyclopropanecarbonyl]amino]-7-fluoro-6-isoquinolyl]-8-methyl-2,3-dihydropyrido[2,3-b][1,4]oxazine-1-carboxylate (1.4 g, 2.25 mmol), tert-butyl carbamate (6.6 g, 56.35 mmol), tris(dibenzylideneacetone)dipalladium(0) chloroform adduct (466.59 mg, 0.45 mmol), 2-(dicyclohexylphosphino)3,6-dimethoxy-2',4',6'-triisopropyl-1,1'-biphenyl (483.27 mg, 0.90 mmol) and cesium carbonate (3.67 g, 11.27 mmol) in 1,4-dioxane (80 mL) was stirred at 90° C. for 2 hours. The mixture was concentrated under vacuum. The residue was purified by flash chromatography on silica gel eluting with dichloromethane/methanol (95/5) to afford tert-butyl 7-[8-(tert-butoxycarbonylamino)-3-[[2-ethyl-3-(1-methylpyrazol-4-yl)cyclopropanecarbonyl]amino]-7-fluoro-6-isoquinolyl]-8-methyl-2,3-dihydropyrido[2,3-b][1,4]oxazine-1-carboxylate (1 g, 1.42 mmol) as a yellow solid. LCMS (ESI) [M+H]$^+$=702.

Step 3: (1R,2S,3R)—N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide; (1S,2R,3S)—N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide; (1S,2S,3S)—N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide and (1R,2R,3R)—N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide

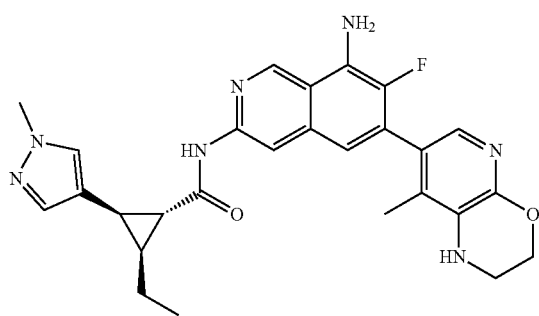

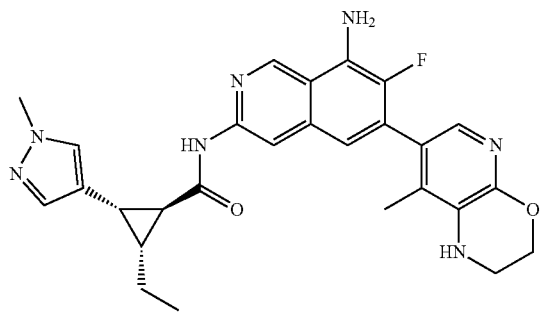

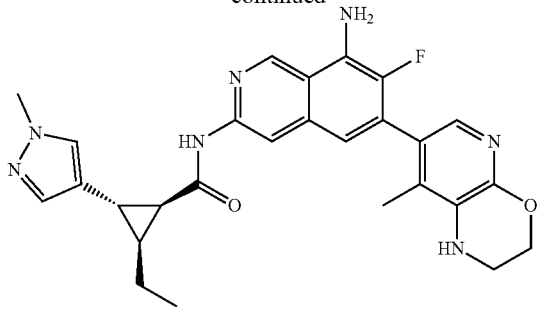

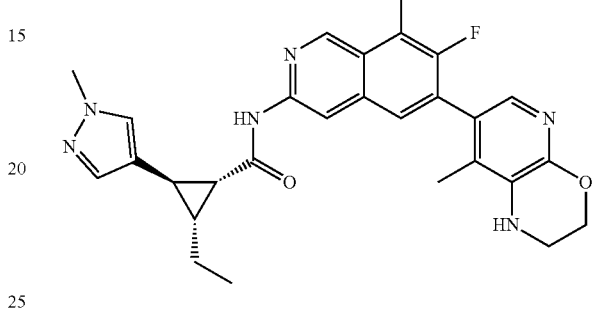

A solution of tert-butyl 7-[8-(tert-butoxycarbonylamino)-3-[[2-ethyl-3-(1-methylpyrazol-4-yl)cyclopropanecarbonyl]amino]-7-fluoro-6-isoquinolyl]-8-methyl-2,3-dihydropyrido[2,3-b][1,4]oxazine-1-carboxylate (1.0 g, 1.42 mmol) and 2,2,2-trifluoroacetic acid (10 mL) in dichloromethane (50 mL) was stirred at 25° C. for 1 hour. The mixture was concentrated under vacuum. The reaction mixture was adjusted to pH 10 with NH$_3$.H$_2$O. The crude product was purified by Prep-HPLC with the following conditions:Column: XBridge Prep OBD C18 Column 30×150 mm 5 um; Mobile Phase A:Water (10 mmol/L sodium bicarbonate), Mobile Phase B: ACN; Flow rate: 60 mL/min; Gradient: 25% B to 47% B in 7 min; 254/220 nm; Rt: 6.13 min to afford a mixture of isomers of N-[8-amino-7-fluoro-6-(8-methyl-2,3-dihydro-1H-pyrido[2,3-b][1,4]oxazin-7-yl)-3-isoquinolyl]-2-ethyl-3-(1-methylpyrazol-4-yl)cyclopropanecarboxamide (400 mg, 0.80 mmol) as a yellow solid. LCMS (ESI) [M+H]$^+$=502. The mixture was separated into 4 isomers by chiral SFC (Cyclopropane stereochemistry for isomers: pyrazole trans to amide; methyl relative stereochemistry arbitrarily assigned; All absolute stereochemistry arbitrarily assigned): Compound 9: (28.7 mg, 0.057 mmol) as a yellow solid. Retention time:2.401 min (CHIRALPAK IE-3, 0.46*10 cm; 3 μm; MtBE (0.1% DEA):MeOH=70:30; 1.0 ml/min); LCMS (ESI) [M+H]$^+$=502; $^1$H NMR (300 MHz, DMSO-d$_6$) δ 10.68 (s, 1H), 9.38 (s, 1H), 8.30 (s, 1H), 7.52 (s, 1H), 7.33 (s, 1H), 7.25 (d, J=0.8 Hz, 1H), 6.85 (d, J=6.2 Hz, 1H), 6.20 (s, 2H), 5.67 (s, 1H), 4.30 (s, 2H), 3.77 (s, 3H), 3.37 (s, 2H), 2.26-2.17 (m, 2H), 1.93 (d, J=1.6 Hz, 3H), 1.86-1.43 (m, 3H), 0.92 (t, J=7.3 Hz, 1H). Compound 10: (22.5 mg, 0.045 mmol) as a yellow solid. Retention time: 2.090 min (Repaired Chiral IA, 0.46*10 cm; 5 μm; MtBE (0.1% DEA):MeOH=70:30; 1.0 ml/min); LCMS (ESI) [M+H]$^+$=502; $^1$H NMR (300 MHz, DMSO-d$_6$) δ 10.68 (s, 1H), 9.38 (s, 1H), 8.30 (s, 1H), 7.52 (s, 1H), 7.33 (s, 1H), 7.25 (d, J=0.8 Hz, 1H), 6.85 (d, J=6.2 Hz, 1H), 6.20 (s, 2H), 5.67 (s, 1H), 4.30 (s, 2H), 3.77 (s, 3H), 3.38 (s, 2H), 2.35-2.12 (m, 2H), 1.93 (d, J=1.6 Hz, 3H), 1.84-1.38 (m, 3H), 0.92 (t, J=7.3 Hz, 1H). Compound 12: (89.3 mg, 0.18 mmol) as a yellow solid. Retention time: 4.15 min (Repaired Chiral IA, 0.46*10 cm; 5 μm;

MtBE (0.1% DEA):MeOH=70:30; 1.0 ml/min); LCMS (ESI) [M+H]⁺=502; ¹H NMR (300 MHz, DMSO-d₆) δ 10.72 (s, 1H), 9.40 (s, 1H), 8.28 (s, 1H), 7.53 (s, 1H), 7.33 (s, 1H), 7.29 (s, 1H), 6.84 (d, J=6.2 Hz, 1H), 6.21 (s, 2H), 5.67 (s, 1H), 4.29 (s, 2H), 3.80 (s, 3H), 3.37 (s, 2H), 2.37-2.29 (m, 1H), 2.17 (t, J=4.7 Hz, 1H), 1.93 (d, J=1.6 Hz, 3H), 1.58-1.44 (m, 1H), 1.30-1.16 (m, 2H), 0.89 (t, J=7.3 Hz, 3H). Compound 11: (113.1 mg, 0.23 mmol) as a yellow solid. Retention time: 2.66 min (CHIRALPAK IE-3, 0.46*10 cm; 3 μm;

MtBE (0.1% DEA):MeOH=70:30; 1.0 ml/min); LCMS (ESI) [M+H]⁺=502; ¹H NMR (300 MHz, DMSO-d₆) δ 10.72 (s, 1H), 9.40 (s, 1H), 8.29 (s, 1H), 7.53 (s, 1H), 7.33 (s, 1H), 7.29 (s, 1H) 6.84 (d, J=6.2 Hz, 1H), 6.21 (s, 2H), 5.67 (s, 1H), 4.29 (s, 2H), 3.80 (s, 3H), 3.37 (s, 2H), 2.38-2.29 (m, 1H), 2.17 (t, J=4.7 Hz, 1H), 1.93 (d, J=1.6 Hz, 3H), 1.58-1.44 (m, 1H), 1.30-1.16 (m, 2H), 0.89 (t, J=7.3 Hz, 3H).

Example 135

(1R,2S,3R)—N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide (assumed) (Compound 36), (1S,2R,3S)—N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide (assumed) (Compound 35), (1R,2R,3R)—N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide (assumed) (Compound 34) and (1S,2S,3S)—N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide (assumed) (Compound 33)

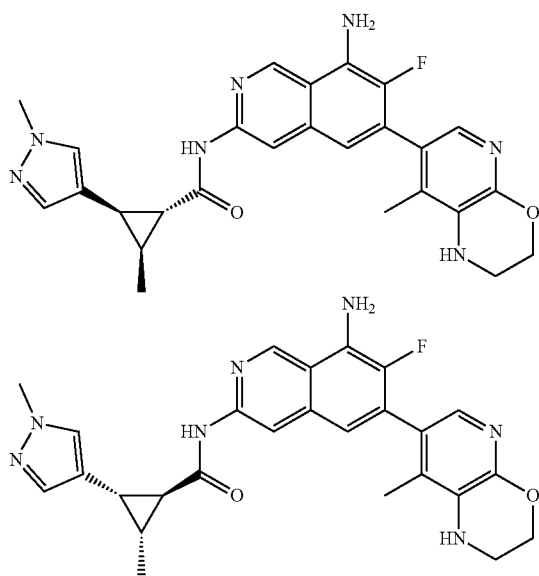

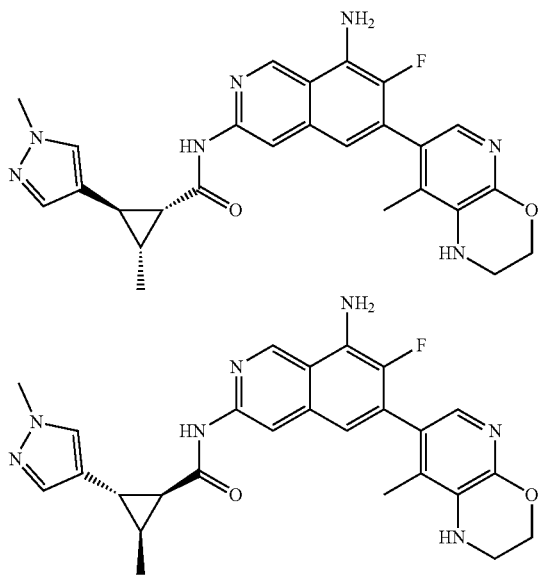

Step 1: ethyldiphenylsulfanium tetrafluoroboranuide

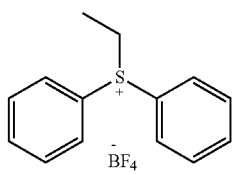

To a solution of AgBF₄ (37.48 g, 192.53 mmol) in dichloromethane (450 mL) was added iodoethane (30 g, 192.35 mmol) under nitrogen. The solution was stirred for 30 minutes at room temperature. Phenylsulfanyl)benzene (106.92 g, 573.99 mmol) was added and then stirred for 16 hours at 35° C. The mixture was filtered and the filtrate was concentrated under vacuum. The residue was washed with dichloromethane/ether (1/1) to afford ethyldiphenylsulfanium tetrafluoroboranuide (25 g, 116.28 mmol) as off-white solid. LCMS (ESI) [M+H]⁺=215.

Step 2: trans-tert-butyl 2-methyl-3-(1-methylpyrazol-4-yl)cyclopropanecarboxylate

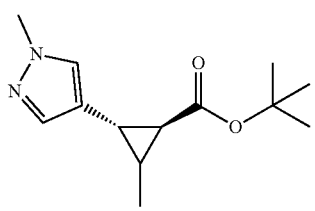 [SMILES: CC1[C@H](C(=O)OC(C)(C)C)[C@H]1c1cnn(C)c1]

To a solution of ethyl(diphenyl)sulfonium (1.55 g, 7.2 mmol) in dichloromethane (2 mL) and 1,2-dimethoxyethane (20 mL) was added lithium diisopropylamide (4.2 mL, 8.4 mmol) at −78° C. The resulting solution was stirred for 1 hour at −78° C. tert-Butyl (E)-3-(1-methylpyrazol-4-yl)prop-2-enoate (500 mg, 2.4 mmol) was added at −78° C. The mixture was stirred at 25° C. for 6 hours. The reaction was quenched with water and then extracted with dichloromethane. The organic layers were combined, dried over anhydrous sodium sulfate and concentrated under vacuum to afford trans-tert-butyl 2-methyl-3-(1-methylpyrazol-4-yl)cyclopropanecarboxylate (550 mg, crude) as a yellow oil. LCMS (ESI) [M+H]$^+$=237.

Step 3: (+/−)-trans-tert-butyl 2-methyl-3-(1-methylpyrazol-4-yl)cyclopropanecarboxylate

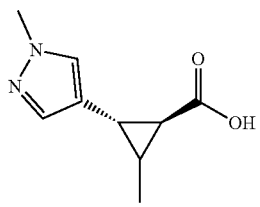

A solution of trans-tert-butyl 2-methyl-3-(1-methylpyrazol-4-yl)cyclopropanecarboxylate (500 mg, crude) in dichloromethane (3 mL) and 2,2,2-trifluoroacetic acid (4 mL) was stirred at 25° C. for 2 hours. The solvent was concentrated under vacuum. The reaction mixture was adjusted to pH 7 with ammonia in methanol (7 mol/L). The residue was purified by reverse phase chromatography (acetonitrile 0-40/0.1% HCl in water) to afford a mixture of 4 stereoisomers of 2-methyl-3-(1-methylpyrazol-4-yl)cyclopropanecarboxylic acid where pyrazole is trans to carboxylic acid (180 mg, 0.99 mmol) as a yellow oil. LCMS (ESI) [M+H]$^+$=181.

Step 4: tert-butyl 7-[8-chloro-7-fluoro-3-[[(1S)-2-methyl-3-(1-methylpyrazol-4-yl)cyclopropanecarbonyl]amino]-6-isoquinolyl]-8-methyl-2,3-dihydropyrido[2,3-b][1,4]oxazine-1-carboxylate

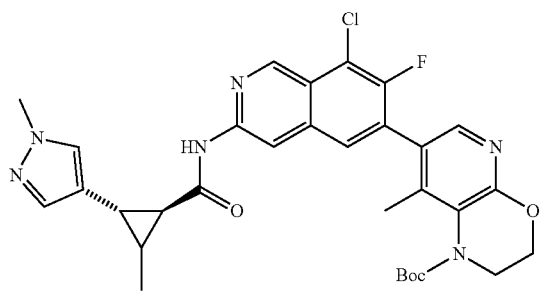 [SMILES: Cc1c(-c2cc3cc(NC(=O)[C@H]4C(C)[C@@H]4c4cnn(C)c4)ncc3c(Cl)c2F)cnc2c1N(C(=O)OC(C)(C)C)CCO2]

To a solution of trans-2-methyl-3-(1-methylpyrazol-4-yl)cyclopropanecarboxylic acid (182.27 mg, 1.01 mmol) in dichloromethane (15 mL) and pyridine (3 mL) was added tert-butyl 7-(3-amino-8-chloro-7-fluoro-6-isoquinolyl)-8-methyl-2,3-dihydropyrido[2,3-b][1,4]oxazine-1-carboxylate (450 mg, 1.01 mmol) at 25° C. The resulting solution was stirred for 20 minutes at 25° C. Phosphorus oxychloride (309.51 mg, 2.02 mmol) was added and stirred at 25° C. for 30 minutes. The reaction was quenched with water and then extracted with dichloromethane. The organic layers were combined, dried over anhydrous sodium sulfate and concentrated under vacuum. The residue was purified by flash chromatography on silica gel eluting with petroleum ether/ethyl acetate (9:1) to afford tert-butyl 7-[8-chloro-7-fluoro-3-[[(1S)-2-methyl-3-(1-methylpyrazol-4-yl)cyclopropanecarbonyl]amino]-6-isoquinolyl]-8-methyl-2,3-dihydropyrido[2,3-b][1,4]oxazine-1-carboxylate (320 mg, 0.53 mmol) as a yellow solid. LCMS (ESI) [M+H]$^+$=607.

Step 5: tert-butyl 7-[8-(tert-butoxycarbonylamino)-7-fluoro-3-[[(1S)-2-methyl-3-(1-methylpyrazol-4-yl)cyclopropanecarbonyl]amino]-6-isoquinolyl]-8-methyl-2,3-dihydropyrido[2,3-b][1,4]oxazine-1-carboxylate

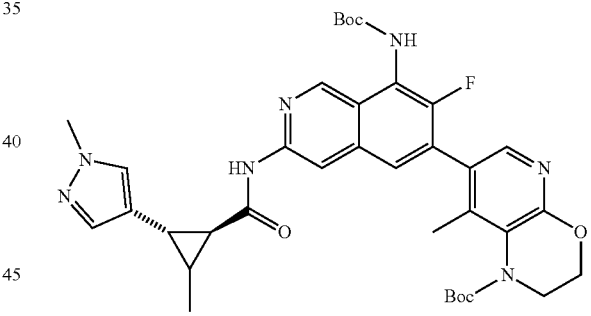

To a solution of tert-butyl 7-[8-chloro-7-fluoro-3-[[(1S)-2-methyl-3-(1-methylpyrazol-4-yl)cyclopropanecarbonyl]amino]-6-isoquinolyl]-8-methyl-2,3-dihydropyrido[2,3-b][1,4]oxazine-1-carboxylate (420 mg, 0.69 mmol), tert-butyl carbamate (2.43 g, 20.76 mmol), tris(dibenzylideneacetone)dipalladium (143.21 mg, 0.14 mmol) and Brettphos (148.61 mg, 0.28 mmol) in 1,4-dioxane (15 mL) was added cesium carbonate (902.15 mg, 2.77 mmol) at 25° C. The resulting solution was stirred at 90° C. for 3 hours. After filtration, the filtrate was concentrated under reduced pressure. The residue was purified by flash chromatography on silica gel eluting with dichloromethane/methanol (9/1) to afford tert-butyl 7-[8-(tert-butoxycarbonylamino)-7-fluoro-3-[[(1S)-2-methyl-3-(1-methylpyrazol-4-yl)cyclopropanecarbonyl]amino]-6-isoquinolyl]-8-methyl-2,3-dihydropyrido[2,3-b][1,4]oxazine-1-carboxylate (450 mg, 0.65 mmol) as a yellow solid. LCMS (ESI) [M+H]$^+$=688.

Step 6: (1R,2S,3R)—N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide, (1S,2R,3S)—N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide, (1R,2R,3R)—N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide and (1S,2S,3S)—N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide

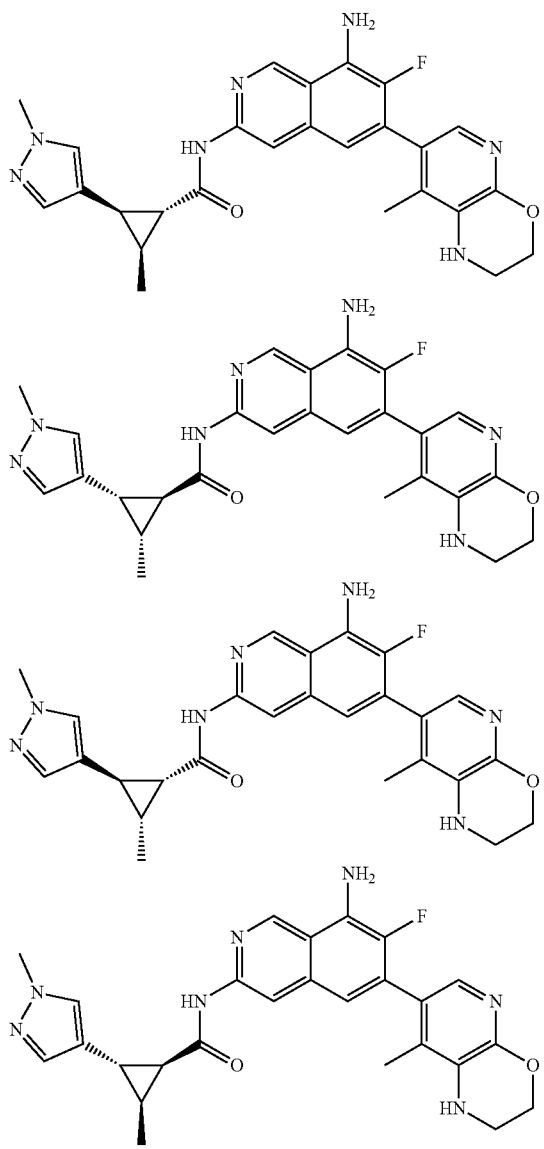

A solution of tert-butyl 7-[8-(tert-butoxycarbonylamino)-7-fluoro-3-[[(1S)-2-methyl-3-(1-methylpyrazol-4-yl)cyclopropanecarbonyl]amino]-6-isoquinolyl]-8-methyl-2,3-dihydropyrido[2,3-b][1,4]oxazine-1-carboxylate (800 mg, 1.16 mmol) in dichloromethane (10 mL) and 2,2,2-trifluoroacetic acid (10 mL) was stirred at 25° C. for 2 hours. The solvent was concentrated under vacuum. The crude product was purified by prep-HPLC (C18 silica gel; 0.5% sodium bicarbonate in water:ACN=20%-50% in 7 min) to afford the mixture (260 mg, 0.44 mmol) as a yellow solid. The mixture was separated by chiral-HPLC to afford four isomers (Cyclopropane stereochemistry for each isomer: pyrazole trans to amide; methyl relative stereochemistry arbitrarily assigned; All absolute stereochemistry arbitrarily assigned): Compound 33: (27.3 mg, 0.056 mmol) as a yellow solid. Retention time: 3.92 min (CHIRALPAK IE-3. 0.46*10 cm; 3 µm; MtBE (0.3% IPAmine):EtOH=70:30; 1.0 ml/min); LCMS (ESI) [M+H]⁺=488.2; ¹HNMR (300 MHz, DMSO-d₆) δ 10.68 (s, 1H), 9.39 (s, 1H), 8.32 (s, 1H), 7.53 (s, 1H), 7.34 (s, 1H), 7.26 (s, 1H), 6.86 (d, J=6.2 Hz, 1H), 6.21 (s, 2H), 5.68 (s, 1H), 4.30-4.29 (m, 2H), 3.77 (s, 3H), 3.38-3.37 (m, 2H), 2.28-2.12 (m, 2H), 1.94 (s, 3H), 1.64-1.50 (m, 1H), 1.28 (d, J=6.1 Hz, 3H). Compound 34: (26.6 mg, 0.055 mmol) as a yellow solid. Retention time: 5.736 min (CHIRALPAK IE-3. 0.46*10 cm; 3 µm; MtBE (0.3% IPAmine):EtOH=70:30; 1.0 ml/min); LCMS (ESI) [M+H]⁺=488.2; ¹HNMR (300 MHz, DMSO-d₆) δ 10.68 (s, 1H), 9.39 (s, 1H), 8.32 (s, 1H), 7.53 (s, 1H), 7.34 (s, 1H), 7.26 (s, 1H), 6.86 (d, J=6.2 Hz, 1H), 6.21 (s, 2H), 5.68 (s, 1H), 4.30-4.29 (m, 2H), 3.77 (s, 3H), 3.38-3.37 (m, 2H), 2.28-2.12 (m, 2H), 1.94 (s, 3H), 1.64-1.50 (m, 1H), 1.28 (d, J=6.1 Hz, 3H). Compound 35: (72.6 mg, 0.15 mmol) as a yellow solid. Retention time: 7.063 min (CHIRALPAK IE-3. 0.46*10 cm; 3 µm; MtBE (0.3% IPAmine):EtOH=70:30; 1.0 ml/min); LCMS (ESI) [M+H]⁺=488.2; ¹HNMR (300 MHz, DMSO-d₆) δ 10.72 (s, 1H), 9.41 (s, 1H), 8.29 (s, 1H), 7.55 (s, 1H), 7.32 (s 1H), 7.29 (s, 1H), 6.84 (d, J=6.2 Hz, 1H), 6.22 (s, 2H), 5.68 (s, 1H), 4.30-4.29 (m, 2H), 3.81 (s, 3H), 3.38-3.37 (m, 2H), 2.31 (dd, J=9.1, 4.5 Hz, 1H), 2.12 (t, J=4.6 Hz, 1H), 1.93 (d, J=1.6 Hz, 3H), 1.67-1.54 (m, 1H), 0.97 (d, J=6.3 Hz, 3H). Compound 36: (80.2 mg, 0.16 mmol) as a yellow solid. Retention time: 9.167 min (CHIRALPAK IE-3. 0.46*10 cm; 3 µm; MtBE (0.3% IPAmine):EtOH=70:30; 1.0 ml/min); LCMS (ESI) [M+H]⁺=488.2; ¹HNMR (300 MHz, DMSO-d₆) δ 10.72 (s, 1H), 9.41 (s, 1H), 8.29 (s, 1H), 7.55 (s, 1H), 7.32 (s 1H), 7.29 (s, 1H), 6.84 (d, J=6.2 Hz, 1H), 6.22 (s, 2H), 5.68 (s, 1H), 4.30-4.29 (m, 2H), 3.81 (s, 3H), 3.38-3.37 (m, 2H), 2.31 (dd, J=9.1, 4.5 Hz, 1H), 2.12 (t, J=4.6 Hz, 1H), 1.93 (d, J=1.6 Hz, 3H), 1.67-1.54 (m, 1H), 0.97 (d, J=6.3 Hz, 3H).

Example 136

2-((8-amino-7-fluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one (Compound 233)

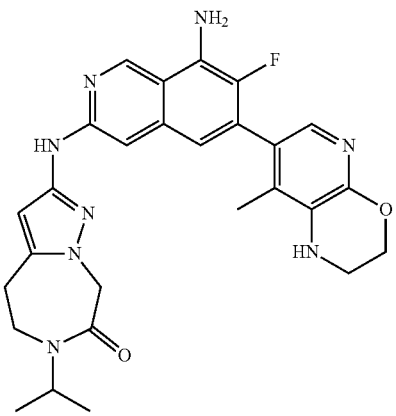 [SMILES: Cc1c(-c2cc3cc(Nc4cc5n(n4)CC(=O)N(C(C)C)CC5)ncc3c(N)c2F)cnc2c1NCCO2]

Step 1: tert-butyl 7-(3-amino-8-chloro-7-fluoro-6-isoquinolyl)-8-methyl-2,3-dihydropyrido[2,3-b][1,4]oxazine-1-carboxylate

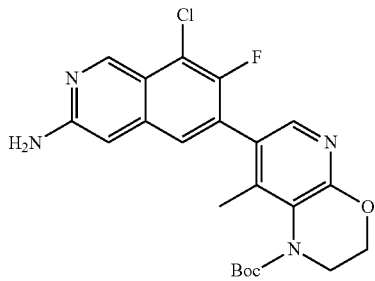 [SMILES: Cc1c(-c2cc3cc(N)ncc3c(Cl)c2F)cnc2c1N(C(=O)OC(C)(C)C)CCO2]

A solution of 8-chloro-7-fluoro-6-iodo-isoquinolin-3-amine (1.14 g, 3.54 mmol), [1,1'-bis(diphenylphosphino)ferrocene]dichloropalladium(II) (518.19 mg, 0.71 mmol), potassium carbonate (1.47 g, 10.62 mmol) and tert-butyl 8-methyl-7-(4,4,5,5-tetramethyl-1,3,2-dioxaborolan-2-yl)-2,3-dihydropyrido[2,3-b][1,4]oxazine-1-carboxylate (2.0 g, 5.32 mmol) in 1,4-dioxane (20 ml) and water (4 mL) was stirred at 90° C. for 1 hour. The reaction was cooled to room temperature and then filtered. The filtrate was concentrated under vacuum. The residue was purified by flash chromatography on silica gel eluting with petroleum ether/ethyl acetate (3/1) to afford tert-butyl 7-(3-amino-8-chloro-7-fluoro-6-isoquinolyl)-8-methyl-2,3-dihydropyrido[2,3-b][1,4]oxazine-1-carboxylate (1.5 g, 3.37 mmol) as a yellow solid.

Step 2: tert-butyl 7-[8-chloro-7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate

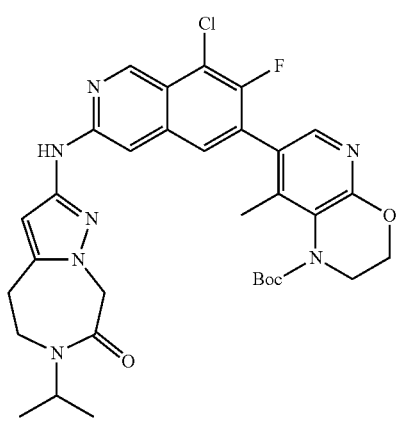 [SMILES: Cc1c(-c2cc3cc(Nc4cc5n(n4)CC(=O)N(C(C)C)CC5)ncc3c(Cl)c2F)cnc2c1N(C(=O)OC(C)(C)C)CCO2]

A solution of tert-butyl 7-(3-amino-8-chloro-7-fluoro-6-isoquinolyl)-8-methyl-2,3-dihydropyrido[2,3-b][1,4]oxazine-1-carboxylate (200 mg, 0.44 mmol) and 2-bromo-6-isopropyl-5,8-dihydro-4H-pyrazolo[1,5-d][1,4]diazepin-7-one (147 mg, 0.52 mmol), t-BuBrettphos Pd G3 (77 mg, 0.08 mmol), t-BuBrettphos (104 mg, 0.16 mmol), cesium carbonate (439 mg, 1.36 mmol) in 1,4-dioxane (40 mL) was stirred at 120° C. for 1 hour. After filtration, the filtrate was concentrated under vacuum. The residue was purified by flash chromatography on silica gel eluting with dichloromethane/methanol (20/1) to afford tert-butyl 7-[8-chloro-7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (150 mg, 0.024 mmol) as a yellow solid. LCMS (ESI) [M+H]$^+$=517.24.

Step 3: tert-butyl 7-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate

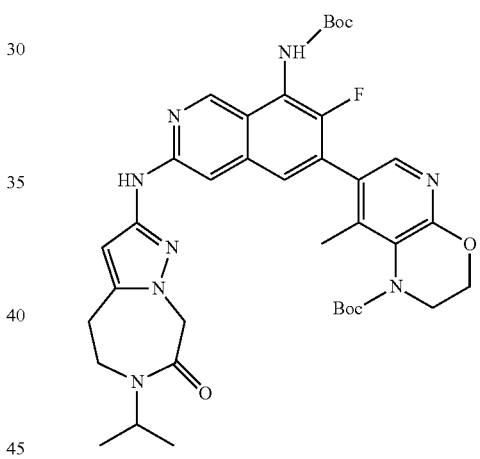

A solution of tert-butyl 7-[8-chloro-7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (150 mg, 0.24 mmol), tert-butyl carbamate (552.4 mg, 4.8 mmol), tris(dibenzylideneacetone)dipalladium-chloroform adduct (48.82 mg, 0.048 mmol), 2-(dicyclohexylphosphino)3,6-dimethoxy-2',4',6'-triisopropyl-1,1'-biphenyl (50.63 mg, 0.096 mmol) and cesium carbonate (230.49 mg, 0.71 mmol) in 1,4-dioxane (10 mL) was stirred at 90° C. for 2 hours. After filtration, the solvent was concentrated under vacuum. The residue was purified by flash chromatography on silica gel eluting with dichloromethane/methanol (10/1) to afford tert-butyl 7-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (100 mg, 0.14 mmol) as a yellow solid. LCMS (ESI) [M+H]$^+$=717.8.

Step 4: 2-[[8-amino-7-fluoro-6-(8-methyl-2,3-dihydro-1H-pyrido[2,3-b][1,4]oxazin-7-yl)-3-isoquinolyl]amino]-6-isopropyl-5,8-dihydro-4H-pyrazolo[1,5-d][1,4]diazepin-7-one

A solution of tert-butyl 7-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-8-methyl-2,3-dihydropyrido[2,3-b][1,4]oxazine-1-carboxylate (100 mg, 0.07 mmol) and trifluoroacetic acid (2 mL, 0.07 mmol) in dichloromethane (4 mL) was stirred at 25° C. for 1 hour. The solvent was concentrated under vacuum and then adjusted to pH 9 with ammonia in methanol (7 mol/L). The residue was purified by prep-HPLC (SunFire Prep C18 OBD Column 19×150 mm 5 um 10 nm; Water (0.1% FA): CAN=9% B to 30% B in 7 min; 25 mL/min) to afford 2-[[8-amino-7-fluoro-6-(8-methyl-2,3-dihydro-1H-pyrido[2,3-b][1,4]oxazin-7-yl)-3-isoquinolyl]amino]-6-isopropyl-5,8-dihydro-4H-pyrazolo[1,5-d][1,4]diazepin-7-one (10 mg, 0.019 mmol) as a yellow solid. LCMS (ESI) [M+H]$^+$=517.24. $^1$HNMR (300 MHz, Methanol-d$_4$) δ 9.11 (s, 1H), 7.59 (s, 1H), 7.36 (s, 1H), 6.81 (d, J=6.2 Hz, 1H), 6.03 (s, 1H), 5.03 (s, 2H), 4.77-4.68 (m, 1H), 4.39 (t, J=4.4 Hz, 2H), 3.89-3.79 (m, 2H), 3.48 (t, J=4.4 Hz, 2H), 3.10 (t, J=6.1 Hz, 2H), 2.02 (s, 3H), 1.21 (d, J=6.8 Hz, 6H).

Example 137

1-[8-amino-7-fluoro-6-(8-methyl-2,3-dihydro-1H-pyrido[2,3-b][1,4]oxazin-7-yl)-3-isoquinolyl]-3-[(1R)-1-(1-methylpyrazol-4-yl)ethyl]urea (Compound 111) and 1-[8-amino-7-fluoro-6-(8-methyl-2,3-dihydro-1H-pyrido[2,3-b][1,4]oxazin-7-yl)-3-isoquinolyl]-3-[(1S)-1-(1-methylpyrazol-4-yl)ethyl]urea (Compound 112)

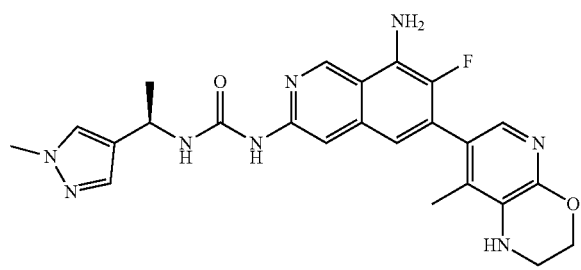

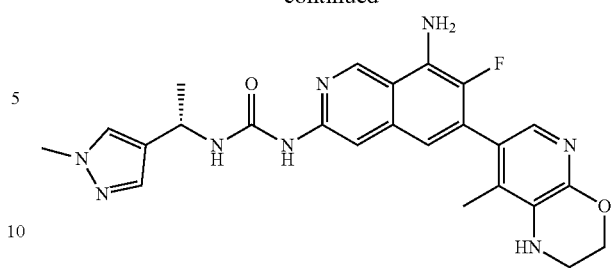

Step 1: tert-butyl 7-[8-chloro-7-fluoro-3-[1-(1-methylpyrazol-4-yl)ethylcarbamoylamino]-6-isoquinolyl]-8-methyl-2,3-dihydropyrido[2,3-b][1,4]oxazine-1-carboxylate

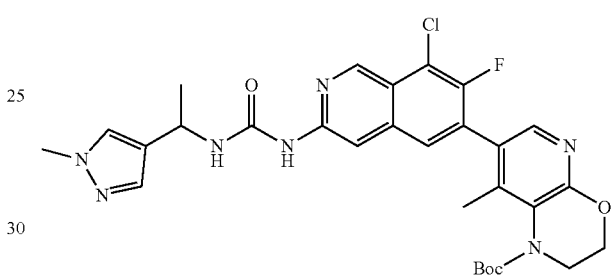

The title compound was prepared in a fashion analogous to that described for Example 133 (Compound 29) using tert-butyl 7-(8-chloro-7-fluoro-3-(((4-nitrophenoxy)carbonyl)amino)isoquinolin-6-yl)-8-methyl-2,3-dihydro-1H-pyrido[2,3-b][1,4]oxazine-1-carboxylate. LCMS (ESI) [M+H]$^+$=596.1.

Step 3: tert-butyl 7-[8-(tert-butoxycarbonylamino)-7-fluoro-3-[1-(1-methylpyrazol-4-yl)ethylcarbamoylamino]-6-isoquinolyl]-8-methyl-2,3-dihydropyrido[2,3-b][1,4]oxazine-1-carboxylate

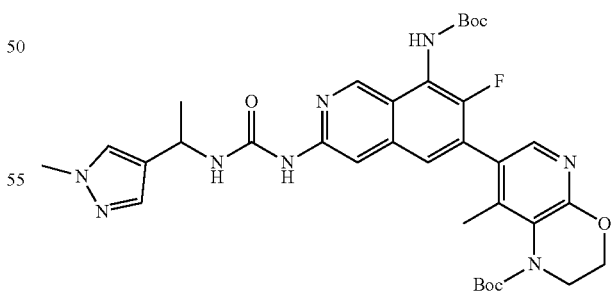

The title compound was prepared in a fashion analogous to that described for Example 133 (Compound 29) using tert-butyl 7-[8-chloro-7-fluoro-3-[1-(1-methylpyrazol-4-yl)ethylcarbamoylamino]-6-isoquinolyl]-8-methyl-2,3-dihydropyrido[2,3-b][1,4]oxazine-1-carboxylate LCMS (ESI) [M+H]$^+$=677.3.

Step 4: 1-[8-amino-7-fluoro-6-(8-methyl-2,3-di-hydro-1H-pyrido[2,3-b][1,4]oxazin-7-yl)-3-isoqui-nolyl]-3-[(1R)-1-(1-methylpyrazol-4-yl)ethyl]urea (Compound 111) and 1-[8-amino-7-fluoro-6-(8-methyl-2,3-dihydro-1H-pyrido[2,3-b][1,4]oxazin-7-yl)-3-isoquinolyl]-3-[(1S)-1-(1-methylpyrazol-4-yl)ethyl]urea (Compound 112)

Example 138

2-[[8-amino-6-(5-amino-4-methyl-3-pyridyl)-7-fluoro-3-isoquinolyl]amino]-5,5,6-trimethyl-4,8-dihydropyrazolo[1,5-d][1,4]diazepin-7-one (Compound 234)

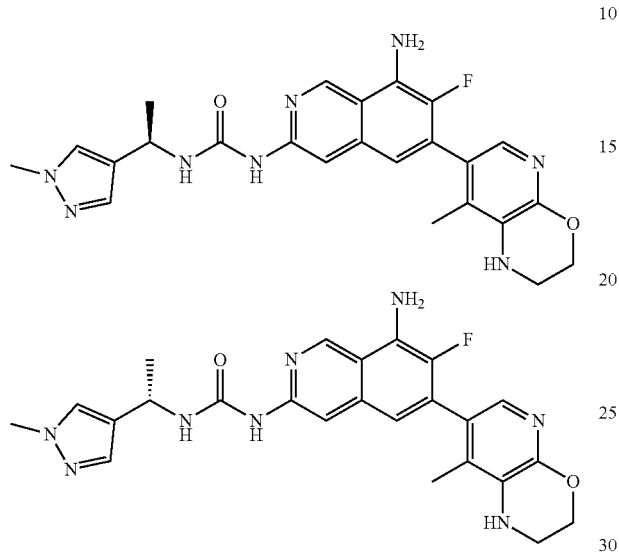

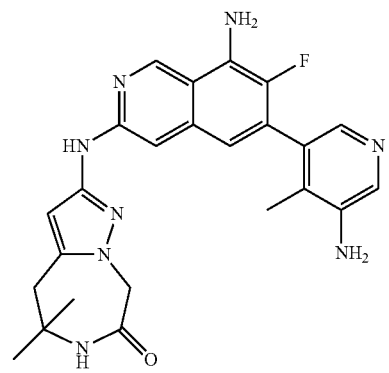

Step 1: tert-butyl(tert-butoxycarbonyl)(5-(8-((tert-butoxycarbonyl)amino)-3-((5,5-dimethyl-7-oxo-5,6,7,8-tetrahydro-4H-pyrazolo[1,5-d][1,4]diazepin-2-yl)amino)-7-fluoroisoquinolin-6-yl)-4-methylpyridin-3-yl)carbamate

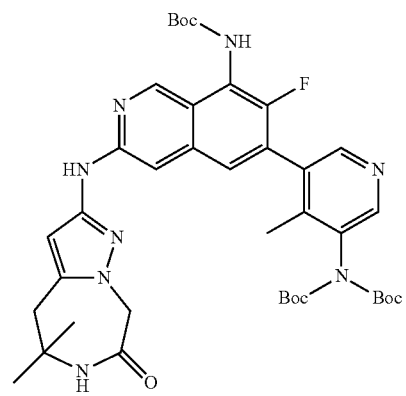

A solution of tert-butyl 7-[8-(tert-butoxycarbonylamino)-7-fluoro-3-[1-(1-methylpyrazol-4-yl)ethylcarbamoy-lamino]-6-isoquinolyl]-8-methyl-2,3-dihydropyrido[2,3-b][1,4]oxazine-1-carboxylate (80 mg, 0.12 mmol) and trifluoroacetic acid (2 mL, 25.96 mmol) in dichloromethane (5 mL) was stirred at 25° C. for 1 hour. The reaction solution was concentrated under vacuum and then adjusted to pH 8 with ammonia in methanol (7 mol/L). The residue was purified by Prep-HPLC (X-Bridge Prep C18 OBD 5 μm, 19*150 mm; water (10 mmol/L sodium bicarbonate): ACN=5% B to 45% B in 9 min) and chiral-HPLC to afford two enantiomers: Compound 111: 1-[8-amino-7-fluoro-6-(8-methyl-2,3-dihydro-1H-pyrido[2,3-b][1,4]oxazin-7-yl)-3-isoquinolyl]-3-[(1R)-(1-methylpyrazol-4-yl)ethyl]urea (assumed) (20.6 mg, 0.043 mmol) as a yellow solid. Rt=2.634 min (Lux Cellulose-4, 0.46*15 cm; 3 m, MtBE (0.1% DEA): EtOH=50:50, 1.0 ml/min). LCMS (ESI) [M+H]$^+$=477.2; $^1$HNMR (300 MHz, Methanol-d$_4$) δ 9.21 (s, 1H), 7.61 (s, 1H), 7.58 (s, 1H), 7.51 (s, 1H), 7.38 (s, 1H), 6.89 (d, J=6.2 Hz, 1H), 5.08-5.02 (m, 1H), 4.42 (t, J=4.2 Hz, 2H), 3.89 (s, 3H), 3.51 (t, J=4.2 Hz, 2H), 2.03 (s, 3H), 1.57 (d, J=6.8 Hz, 3H). Compound 112: 1-[8-amino-7-fluoro-6-(8-methyl-2,3-dihydro-1H-pyrido[2,3-b][1,4]oxazin-7-yl)-3-isoquinolyl]-3-[1(S)-(1-methylpyrazol-4-yl)ethyl]urea (20.7 mg, 0.043 mmol) as a yellow solid. Rt=3.544 (Lux Cellulose-4, 0.46*15 cm, 3 m; MtBE (0.1% DEA): EtOH=50:50, 1.0 ml/min). LCMS (ESI) [M+H]$^+$=477.2; $^1$HNMR (300 MHz, Methanol-d$_4$) δ 9.21 (s, 1H), 7.61 (s, 1H), 7.58 (s, 1H), 7.51 (s, 1H), 7.38 (s, 1H), 6.89 (d, J=6.2 Hz, 1H), 5.08-5.02 (m, 1H), 4.42 (t, J=4.2 Hz, 2H), 3.89 (s, 3H), 3.51 (t, J=4.2 Hz, 2H), 2.03 (s, 3H), 1.57 (d, J=6.8 Hz, 3H).

A mixture of 2-bromo-5,5-dimethyl-6,8-dihydro-4H-pyrazolo[1,5-d][1,4]diazepin-7-one (66.34 mg, 0.26 mmol), tert-butyl N-[5-[3-amino-8-(tert-butoxycarbonylamino)-7-fluoro-6-isoquinolyl]-4-methyl-3-pyridyl]-N-tert-butoxy-carbonyl-carbamate (100.0 mg, 0.17 mmol), t-BuBrettphos-PdG3 (58.53 mg, 0.07 mmol), t-BuBrettphos (41.55 mg, 0.09 mmol) and cesium carbonate (167.57 mg, 0.51 mmol) in 1,4-dioxane (15 mL) was stirred for 1 hour at 120° C. under nitrogen. After filtration, the filtrate was concentrated under reduced pressure. The residue was purified by flash chromatography on silica gel eluting with dichloromethane/methanol (98/2) to afford tert-butyl N-tert-butoxycarbonyl-N-[5-[8-(tert-butoxycarbonylamino)-3-[(5,5-dimethyl-7-oxo-6,8-dihydro-4H-pyrazolo[1,5-d][1,4]diazepin-2-yl) amino]-7-fluoro-6-isoquinolyl]-4-methyl-3-pyridyl] carbamate (60 mg, 0.08 mmol) as a brown solid. LCMS (ESI) [M+H]$^+$=761.

Step 2: 2-[[8-amino-6-(5-amino-4-methyl-3-pyridyl)-7-fluoro-3-isoquinolyl]amino]-5,5,6-trimethyl-4,8-dihydropyrazolo[1,5-d][1,4]diazepin-7-one

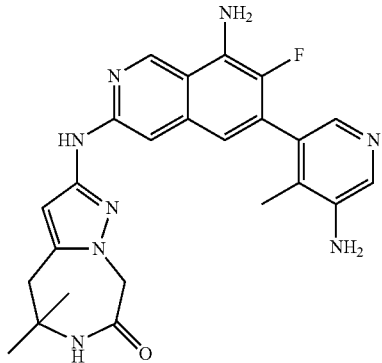

A solution of tert-butyl N-tert-butoxycarbonyl-N-[5-[8-(tert-butoxycarbonylamino)-7-fluoro-3-[(5,5,6-trimethyl-7-oxo-4,8-dihydropyrazolo[1,5-d][1,4]diazepin-2-yl)amino]-6-isoquinolyl]-4-methyl-3-pyridyl]carbamate (80.0 mg, 0.10 mmol) and 2,2,2-trifluoroacetic acid (2 mL) in dichloromethane (6 mL) was stirred at 25° C. for 2 hours. The solvent was concentrated under vacuum. The reaction mixture was adjusted to pH 9 with ammonia in methanol (7 mol/L). The resulting residue was purified by reverse phase chromatography (acetonitrile 0-40/0.1% FA in water) to afford 2-[[8-amino-6-(5-amino-4-methyl-3-pyridyl)-7-fluoro-3-isoquinolyl]amino]-5,5,6-trimethyl-4,8-dihydropyrazolo[1,5-d][1,4]diazepin-7-one (30.5 mg, 0.06 mmol) as an orange solid. LCMS (ESI) [M+H]$^+$=461.2; $^1$H NMR (400 MHz, DMSO-d$_6$) δ 9.26 (s, 1H), 9.10 (s, 1H), 7.99 (s, 1H), 7.76-7.65 (m, 3H), 6.73 (d, J=6.0 Hz, 1H), 6.07 (s, 2H), 6.04 (s, 1H, 5.41 (s, 2H), 4.83 (s, 2H), 3.05 (s, 2H), 1.96 (d, J=1.5 Hz, 3H), 1.18 (s, 6H).

Example 139

2-((8-amino-6-(5-amino-4-methylpyridin-3-yl)-7-fluoroisoquinolin-3-yl)amino)-5,5,6-trimethyl-5,6-dihydro-4H-pyrazolo[1,5-d][1,4]diazepin-7(8H)-one (Compound 235)

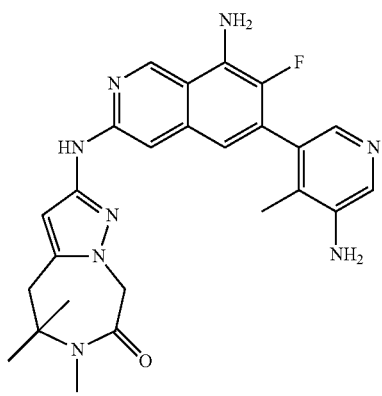

Step 1: tert-butyl N-tert-butoxycarbonyl-N-[5-[8-(tert-butoxycarbonylamino)-7-fluoro-3-[(5,5,6-trimethyl-7-oxo-4,8-dihydropyrazolo[1,5-d][1,4]diazepin-2-yl)amino]-6-isoquinolyl]-4-methyl-3-pyridyl]carbamate

A mixture of 2-bromo-5,5,6-trimethyl-4,8-dihydropyrazolo[1,5-d][1,4]diazepin-7-one (65.28 mg, 0.24 mmol), tert-butyl N-[5-[3-amino-8-(tert-butoxycarbonylamino)-7-fluoro-6-isoquinolyl]-4-methyl-3-pyridyl]-N-tert-butoxycarbonyl-carbamate (100 mg, 0.17 mmol), t-BuBrettphosPdG3 (58.53 mg, 0.07 mmol), t-BuBrettphos (41.55 mg, 0.09 mmol) and cesium carbonate (167.57 mg, 0.51 mmol) in 1,4-dioxane (10 mL) was stirred for 1 hour at 120° C. After filtration, the filtrate was concentrated under reduced pressure. The residue was purified by flash chromatography on silica gel eluting with dichloromethane/methanol (100/3) to afford tert-butyl N-tert-butoxycarbonyl-N-[5-[8-(tert-butoxycarbonylamino)-7-fluoro-3-[(5,5,6-trimethyl-7-oxo-4,8-dihydropyrazolo[1,5-d][1,4]diazepin-2-yl)amino]-6-isoquinolyl]-4-methyl-3-pyridyl]carbamate (80 mg, 0.10 mmol) as a brown solid. LCMS (ESI) [M+H]$^+$=775.

Step 2: 2-[[8-amino-6-(5-amino-4-methyl-3-pyridyl)-7-fluoro-3-isoquinolyl]amino]-5,5,6-trimethyl-4,8-dihydropyrazolo[1,5-d][1,4]diazepin-7-one; Formic Acid

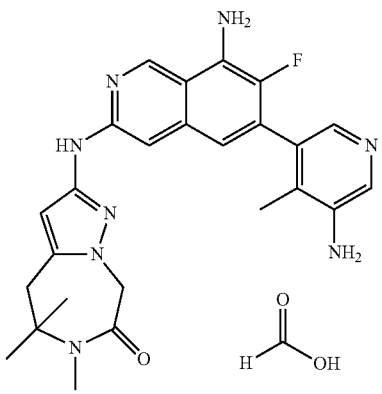

A mixture of tert-butyl N-tert-butoxycarbonyl-N-[5-[8-(tert-butoxycarbonylamino)-7-fluoro-3-[(5,5,6-trimethyl-7-oxo-4,8-dihydropyrazolo[1,5-d][1,4]diazepin-2-yl)amino]-6-isoquinolyl]-4-methyl-3-pyridyl]carbamate (80 mg, 0.10 mmol) and 2,2,2-trifluoroacetic acid (2 mL) in dichloromethane (6 mL) was stirred at 25° C. for 2 hours. The solvent was concentrated under vacuum. The reaction mixture was adjusted to pH 9 with ammonia in methanol (7 mol/L). The mixture was concentrated under vacuum. The resulting residue was purified by reverse phase chromatography (acetonitrile 0-40/0.1% FA in water) to afford 2-[[8-amino-6-(5-amino-4-methyl-3-pyridyl)-7-fluoro-3-isoquinolyl]amino]-5,5,6-trimethyl-4,8-dihydropyrazolo[1,5-d][1,4]diazepin-7-one; formic acid (30.5 mg, 0.059 mmol) as an orange solid. LCMS (ESI) [M+H]$^+$=475; $^1$HNMR (400 MHz, DMSO-d$_6$) δ 9.25 (s, 1H), 9.11 (s, 1H), 7.98 (s, 1H), 7.69-7.67 (d, J=7.2 Hz, 2H), 6.70-6.69 (d, J=7.2 Hz, 1H), 6.05 (s, 3H), 5.26 (s, 2H), 4.94 (s, 2H), 3.20 (s, 2H), 2.76 (s, 3H), 1.93 (s, 3H), 1.28 (s, 6H).

Example 140

(1S,2S,3R)—N-(8-amino-6-(5-amino-4-methylpyridin-3-yl)-7-fluoroisoquinolin-3-yl)-2-(cyanomethyl)-3-methylcyclopropane-1-carboxamide (Compound 239), (1R,2R,3R)—N-(8-amino-6-(5-amino-4-methylpyridin-3-yl)-7-fluoroisoquinolin-3-yl)-2-(cyanomethyl)-3-methylcyclopropane-1-carboxamide (Compound 237), (1R,2R,3S)—N-(8-amino-6-(5-amino-4-methylpyridin-3-yl)-7-fluoroisoquinolin-3-yl)-2-(cyanomethyl)-3-methylcyclopropane-1-carboxamide (Compound 238), and (1S,2S,3S)—N-(8-amino-6-(5-amino-4-methylpyridin-3-yl)-7-fluoroisoquinolin-3-yl)-2-(cyanomethyl)-3-methylcyclopropane-1-carboxamide (Compound 236)

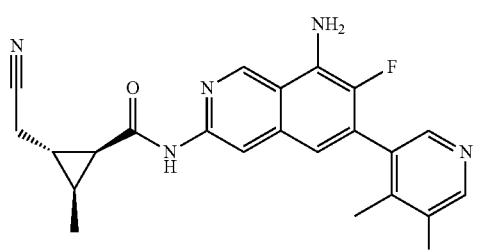

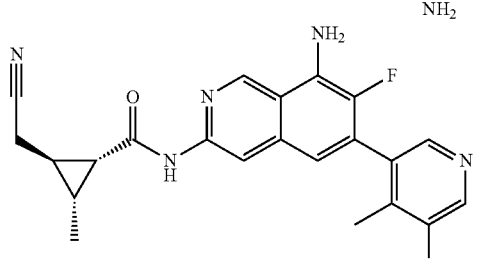

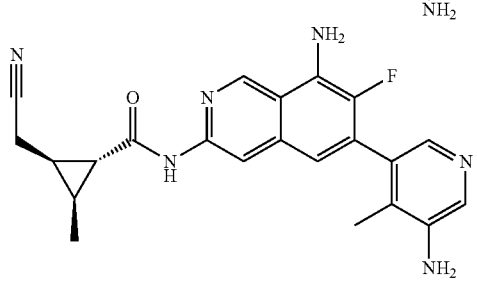

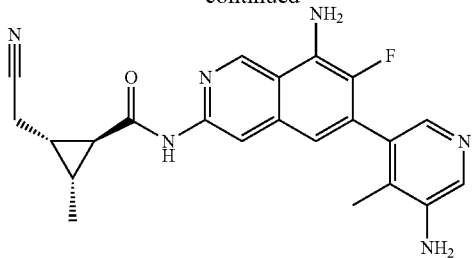

Step 1: trans-tert-butyl 2-(benzyloxymethyl)-3-methylcyclopropanecarboxylate

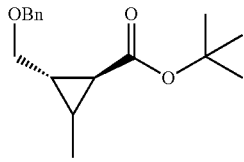 [SMILES: CC1[C@H](COCc2ccccc2)[C@H]1C(=O)OC(C)(C)C]

The title compound was prepared in a fashion analogous to that described for Example 135 (Compound 36) using (E)-tert-butyl 4-(benzyloxy)but-2-enoate. LCMS (ESI) [M+H]$^+$=277.

Step 2: trans-2-(benzyloxymethyl)-3-methylcyclopropanecarboxylic Acid

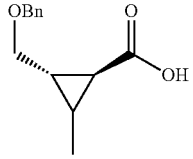 [SMILES: CC1[C@H](COCc2ccccc2)[C@H]1C(=O)O]

The title compound was prepared in a fashion analogous to that described for Example 135 (Compound 36) using trans-tert-butyl 2-(benzyloxymethyl)-3-methylcyclopropanecarboxylate. LCMS (ESI) [M+H]$^+$=221.

Step 3: trans-tert-butyl N-[5-[3-[[2-(benzyloxymethyl)-3-methyl-cyclopropanecarbonyl]amino]-8-chloro-7-fluoro-6-isoquinolyl]-4-methyl-3-pyridyl]-N-tert-butoxycarbonyl-carbamate

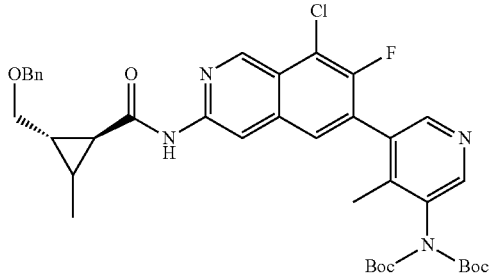 [SMILES: Cc1c(-c2cc3cc(NC(=O)[C@H]4C(C)[C@@H]4COCc4ccccc4)ncc3c(Cl)c2F)cncc1N(C(=O)OC(C)(C)C)C(=O)OC(C)(C)C]

The title compound was prepared in a fashion analogous to that described for Example 135 (Compound 36) using trans-2-(benzyloxymethyl)-3-methyl-cyclopropanecarboxylic acid. LCMS (ESI) [M+H]$^+$=705.

Step 4:tert-butyl N-[5-[3-[[trans-2-(benzyloxymethyl)-3-methyl-cyclopropanecarbonyl]amino]-8-(tert-butoxycarbonylamino)-7-fluoro-6-isoquinolyl]-4-methyl-3-pyridyl]-N-tert-butoxycarbonyl-carbamate

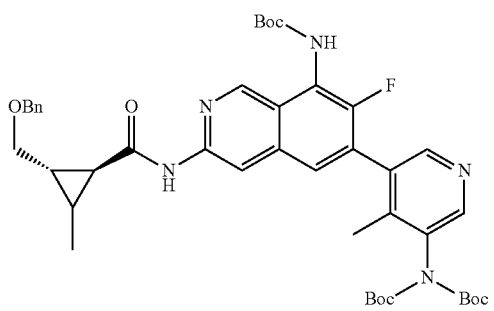 [SMILES: Cc1c(-c2cc3cc(NC(=O)[C@H]4C(C)[C@@H]4COCc4ccccc4)ncc3c(NC(=O)OC(C)(C)C)c2F)cncc1N(C(=O)OC(C)(C)C)C(=O)OC(C)(C)C]

The title compound was prepared in a fashion analogous to that described for Example 135 (Compound 36) using trans-tert-butyl N-[5-[3-[[2-(benzyloxymethyl)-3-methyl-cyclopropanecarbonyl]amino]-8-chloro-7-fluoro-6-isoquinolyl]-4-methyl-3-pyridyl]-N-tert-butoxycarbonyl-carbamate. LCMS (ESI) [M+H]$^+$=786.

Step 5:trans-tert-butyl N-tert-butoxycarbonyl-N-[5-[8-(tert-butoxycarbonylamino)-7-fluoro-3-[[2-(hydroxymethyl)-3-methyl-cyclopropanecarbonyl]amino]-6-isoquinolyl]-4-methyl-3-pyridyl]carbamate

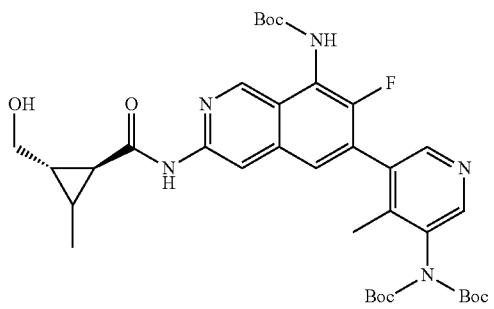 [SMILES: Cc1c(-c2cc3cc(NC(=O)[C@H]4C(C)[C@@H]4CC#N)ncc3c(NC(=O)OC(C)(C)C)c2F)cncc1N(C(=O)OC(C)(C)C)C(=O)OC(C)(C)C]

A solution of trans-tert-butyl N-[5-[3-[[2-(benzyloxymethyl)-3-methyl-cyclopropanecarbonyl]amino]-8-(tert-butoxycarbonylamino)-7-fluoro-6-isoquinolyl]-4-methyl-3-pyridyl]-N-tert-butoxycarbonyl-carbamate (1.1 g, 1.4 mmol) and Pd(OH)$_2$/C (979.77 mg, 1.4 mmol) in methanol (30 mL) was stirred for 36 hours at 25° C. under a hydrogen atmosphere. After filtration, the filtrate was concentrated under vacuum to afford trans-tert-butyl N-tert-butoxycarbonyl-N-[5-[8-(tert-butoxycarbonylamino)-7-fluoro-3-[[2-(hydroxymethyl)-3-methyl-cyclopropanecarbonyl]amino]-6-isoquinolyl]-4-methyl-3-pyridyl]carbamate (450 mg, 0.65 mmol) as a color solid. LCMS (ESI) [M+H]$^+$=696.

Step 6:trans-[2-[[6-[5-[bis(tert-butoxycarbonyl)amino]-4-methyl-3-pyridyl]-8-(tert-butoxycarbonylamino)-7-fluoro-3-isoquinolyl]carbamoyl]-3-methyl-cyclopropyl]methyl methanesulfonate

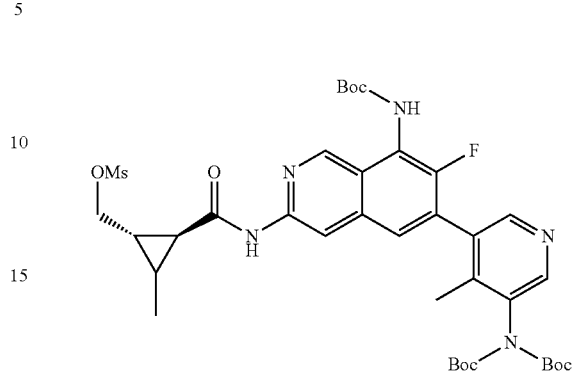

To a solution of trans-tert-butyl N-tert-butoxycarbonyl-N-[5-[8-(tert-butoxycarbonylamino)-7-fluoro-3-[[2-(hydroxymethyl)-3-methyl-cyclopropanecarbonyl]amino]-6-isoquinolyl]-4-methyl-3-pyridyl]carbamate (450 mg, 0.65 mmol) and triethylamine (195.97 mg, 1.94 mmol) in dichloromethane (15 mL) was added methanesulfonyl chloride (187.56 mg, 1.29 mmol) at 0° C. The resulting solution was stirred for 1 hour at 25° C. The reaction was quenched with water, extracted with dichloromethane and dried over anhydrous sodium sulfate.

After filtration, the filtrate was concentrated under vacuum to afford trans-[2-[[6-[5-[bis(tert-butoxycarbonyl)amino]-4-methyl-3-pyridyl]-8-(tert-butoxycarbonylamino)-7-fluoro-3-isoquinolyl]carbamoyl]-3-methyl-cyclopropyl]methyl methanesulfonate (450 mg, 0.58 mmol) as a yellow solid. LCMS (ESI) [M+H]$^+$=774.

Step 7: trans-tert-butyl N-tert-butoxycarbonyl-N-[5-[8-(tert-butoxycarbonylamino)-3-[[2-(cyanomethyl)-3-methyl-cyclopropanecarbonyl]amino]-7-fluoro-6-isoquinolyl]-4-methyl-3-pyridyl]carbamate

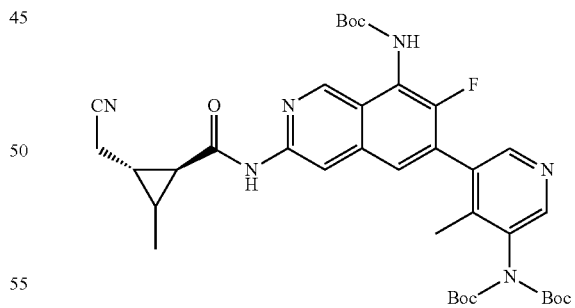

A solution of trans-[2-[[6-[5-[bis(tert-butoxycarbonyl)amino]-4-methyl-3-pyridyl]-8-(tert-butoxycarbonylamino)-7-fluoro-3-isoquinolyl]carbamoyl]-3-methyl-cyclopropyl]methyl methanesulfonate (450 mg, 0.58 mmol) and potassium cyanide (113.39 mg, 1.74 mmol) in dimethyl sulfoxide (10 mL) was stirred at 60° C. for 12 hours. The reaction was quenched with a solution of ferrous sulfate and then extracted with acetic ether. The organic layer was dried over anhydrous sodium sulfate, filtrated and concentrated under vacuum to afford trans-tert-butyl N-tert-butoxycarbonyl-N-[5-[8-(tert-butoxycarbonylamino)-3-[[2-(cyanomethyl)-3-methyl-cyclopropanecarbonyl]amino]-7-fluoro-6-isoquinolyl]-4-methyl-3-pyridyl]carbamate (400 mg, 0.57 mmol) as a brown solid. LCMS (ESI) [M+H]$^+$=705.

Step 8: (1S,2S,3R)—N-(8-amino-6-(5-amino-4-methylpyridin-3-yl)-7-fluoroisoquinolin-3-yl)-2-(cyanomethyl)-3-methylcyclopropane-1-carboxamide, (1R,2R,3R)—N-(8-amino-6-(5-amino-4-methylpyridin-3-yl)-7-fluoroisoquinolin-3-yl)-2-(cyanomethyl)-3-methylcyclopropane-1-carboxamide, (1R,2R,3S)—N-(8-amino-6-(5-amino-4-methylpyridin-3-yl)-7-fluoroisoquinolin-3-yl)-2-(cyanomethyl)-3-methylcyclopropane-1-carboxamide, (1S,2S,3S)—N-(8-amino-6-(5-amino-4-methylpyridin-3-yl)-7-fluoroisoquinolin-3-yl)-2-(cyanomethyl)-3-methylcyclopropane-1-carboxamide The title compound was prepared in a fashion analogous to that described for Example 135 (Compound 36) using trans-tert-butyl N-tert-butoxycarbonyl-N-[5-[8-(tert-butoxycarbonylamino)-3-[[2-(cyanomethyl)-3-methyl-cyclopropanecarbonyl]amino]-7-fluoro-6-isoquinolyl]-4-methyl-3-pyridyl]carbamate (400 mg, 0.57 mmol). The mixture was purified by chiral SFC separation to afford four isomers (Cyclopropane stereochemistry for each isomer: cyanomethyl trans to amide; methyl relative stereochemistry arbitrarily assigned; All absolute stereochemistry arbitrarily assigned): Compound 236: (14.5 mg, 0.036 mmol) as a yellow solid. Retention time: 8.931 min (CHIRALPAK IE-3. 0.46*10 cm; 3 m;

MtBE (0.1% DEA):MeOH=95:5; 1.0 ml/min); LCMS (ESI) [M+H]$^+$=405.2; $^1$HNMR (300 MHz, DMSO-d$_6$) δ 10.76 (s, 1H), 9.38 (s, 1H), 8.27 (s, 1H), 7.97 (s, 1H), 7.63 (s, 1H), 6.85 (d, J=6.2 Hz, 1H), 6.22 (s, 2H), 5.22 (s, 2H), 2.82-2.59 (m, 2H), 2.06 (dd, J=9.1, 4.7 Hz, 1H), 1.89 (d, J=1.4 Hz, 3H), 1.54-1.48 (m, 1H), 1.34 (dt, J=8.9, 6.1 Hz, 1H), 1.14 (d, J=6.1 Hz, 3H). Compound 237: (14.7 mg, 0.036 mmol) as a yellow solid. Retention time: 10.678 min (CHIRALPAK IE-3. 0.46*10 cm; 3 m; MtBE (0.1% DEA): MeOH=95:5; 1.0 ml/min); LCMS (ESI) [M+H]$^+$=405.2; $^1$HNMR (300 MHz, DMSO-d$_6$) δ 10.76 (s, 1H), 9.38 (s, 1H), 8.27 (s, 1H), 7.97 (s, 1H), 7.63 (s, 1H), 6.85 (d, J=6.2 Hz, 1H), 6.22 (s, 2H), 5.22 (s, 2H), 2.82-2.59 (m, 2H), 2.06 (dd, J=9.1, 4.7 Hz, 1H), 1.89 (d, J=1.4 Hz, 3H), 1.54-1.48 (m, 1H), 1.34 (dt, J=8.9, 6.1 Hz, 1H), 1.14 (d, J=6.1 Hz, 3H). Compound 238: (15.3 mg, 0.038 mmol) as a yellow solid. Retention time: 4.185 min (CHIRALPAK IE-3. 0.46*10 cm; 3 m;

MtBE (0.1% DEA):EtOH=80:20; 1.0 ml/min); LCMS (ESI) [M+H]$^+$=405.2; $^1$HNMR (300 MHz, DMSO-d$_6$) δ 10.76 (s, 1H), 9.38 (s, 1H), 8.23 (s, 1H), 7.97 (s, 1H), 7.64 (s, 1H), 6.83 (d, J=6.2 Hz, 1H), 6.23 (s, 2H), 5.24 (s, 2H), 2.86-2.58 (m, 2H), 1.89 (d, J=1.5 Hz, 3H), 1.76 (t, J=4.5 Hz, 1H), 1.70-1.53 (m, 1H), 1.52-1.38 (m, 1H), 1.15 (d, J=6.4 Hz, 3H). Compound 239: (15.5 mg, 0.038 mmol) as a yellow solid. Retention time: 6.037 min (CHIRALPAK IE-3. 0.46*10 cm; 3 m; MtBE (0.1% DEA):EtOH=80:20; 1.0 ml/min); LCMS (ESI) [M+H]$^+$=405.2; $^1$HNMR (300 MHz, DMSO-d$_6$) δ 10.76 (s, 1H), 9.38 (s, 1H), 8.23 (s, 1H), 7.97 (s, 1H), 7.64 (s, 1H), 6.83 (d, J=6.2 Hz, 1H), 6.23 (s, 2H), 5.24 (s, 2H), 2.86-2.58 (m, 2H), 1.89 (d, J=1.5H.

Example 141

2-((8-amino-7-fluoro-6-((2-oxo-1,2-dihydropyridin-3-yl)methyl)isoquinolin-3-yl)amino)-6-isopropyl-5,6-dihydro-4H-pyrazolo[1,5-d][1,4]diazepin-7(8H)-one (Compound 240)

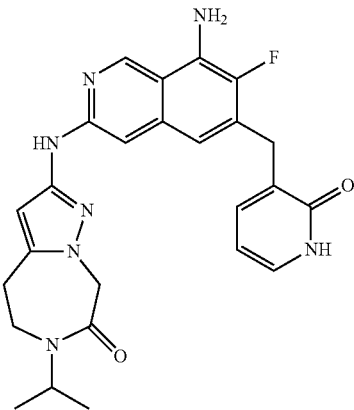 [SMILES: CC(C)N1CCc2cc(Nc3cc4cc(Cc5ccc[nH]c5=O)c(F)c(N)c4cn3)nn2CC1=O]

Step 1: 2-methoxy-3-pyridyl)methanol

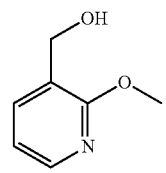

A solution of 2-methoxynicotinic acid (200.0 mg, 1.31 mmol) and borane tetrahydrofuran complex solution (1 mol/L) (4 mL, 3.92 mmol) was stirred under nitrogen in tetrahydrofuran (5 mL) at 0° C. The resulting solution was stirred for 1 hour at 25° C. The reaction was quenched by methanol (2 mL). The solvent was concentrated under vacuum to afford 2-methoxy-3-pyridyl)methanol (150 mg, 1.08 mmol) as a yellow oil. LCMS (ESI) [M+H]+=139.2.

Step 2: 3-(chloromethyl)-2-methoxypyridine

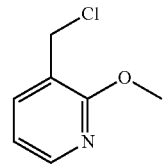

A solution of (2-methoxy-3-pyridyl)methanol (1.0 g, 7.19 mmol) and SOCl$_2$ (2.56 g, 21.55 mmol) in dichloromethane (5 mL) was stirred at 25° C. for 3 hours. The solvent was concentrated under vacuum. The residue was purified by flash chromatography on silica gel eluting with methanol/dichloromethane (5 95) to afford 3-(chloromethyl)-2-methoxypyridine (500 mg, 3.17 mmol) as a yellow oil. LC/MS (ESI) [M+H]+=157.6.

Step 3: tert-butyl (7-fluoro-3-((6-isopropyl-7-oxo-5, 6,7,8-tetrahydro-4H-pyrazolo[1,5-d][1,4]diazepin-2-yl)amino)-6-((2-methoxypyridin-3-yl)methyl)isoquinolin-8-yl)carbamate

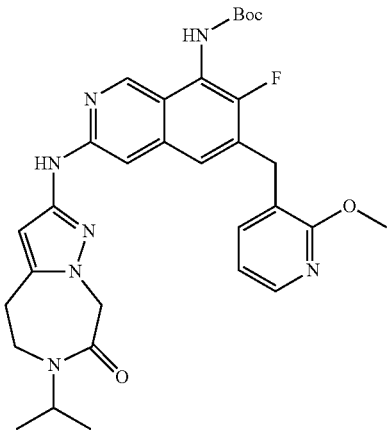 [SMILES: COc1ncccc1Cc1cc2cc(Nc3cc4n(n3)CC(=O)N(C(C)C)CC4)ncc2c(NC(=O)OC(C)(C)C)c1F]

A mixture of (8-((tert-butoxycarbonyl)amino)-7-fluoro-3-((6-isopropyl-7-oxo-5,6,7,8-tetrahydro-4H-pyrazolo[1,5-d][1,4]diazepin-2-yl)amino)isoquinolin-6-yl)boronic acid (86.96 mg, 0.17 mmol), 3-(chloromethyl)-2-methoxy-pyridine (40.0 mg, 0.25 mmol), [1,1'-bis(diphenylphosphino)ferrocene]dichloropalladium(II) (24.35 mg, 0.03 mmol) and cesium carbonate (165.22 mg, 0.51 mmol) in tetrahydrofuran (1 mL) and water (0.10 mL) was stirred for 1 hour at 100° C. The solvent was concentrated under vacuum. The residue was purified by flash chromatography on silica gel eluting with methanol/dichloromethane (1/5) to afford tert-butyl (7-fluoro-3-((6-isopropyl-7-oxo-5,6,7,8-tetrahydro-4H-pyrazolo[1,5-d][1,4]diazepin-2-yl)amino)-6-((2-methoxypyridin-3-yl)methyl)isoquinolin-8-yl)carbamate (76 mg, 0.13 mmol) as a brown solid. LCMS (ESI) [M+H]$^+$=589.7.

Step 4: 2-((8-amino-7-fluoro-6-((2-oxo-1,2-dihydro-pyridin-3-yl)methyl)isoquinolin-3-yl)amino)-6-isopropyl-5,6-dihydro-4H-pyrazolo[1,5-d][1,4]diaz-epin-7(8H)-one

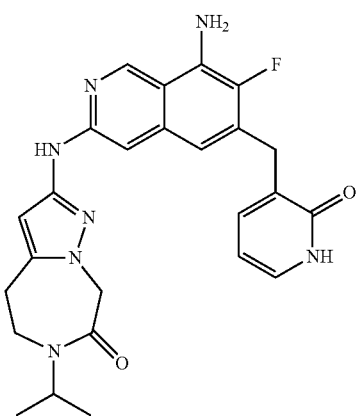 [SMILES: CC(C)N1CCc2cc(Nc3cc4cc(Cc5ccc[nH]c5=O)c(F)c(N)c4cn3)nn2CC1=O]

A mixture of tert-butyl (7-fluoro-3-((6-isopropyl-7-oxo-5,6,7,8-tetrahydro-4H-pyrazolo[1,5-d][1,4]diazepin-2-yl) amino)-6-((2-methoxypyridin-3-yl)methyl)isoquinolin-8-yl)carbamate (60 mg, 0.10 mmol), lithium chloride (54 mg, 1.29 mmol) and p-toluenesulfonic acid (240 mg, 1.26 mmol) in N,N-dimethylformamide (5 mL) was stirred at 120° C. for 0.5 h. The residue was purified by flash chromatography on C18 (acetonitrile-0.1% sodium bicarbonate in water) to afford 2-((8-amino-7-fluoro-6-((2-oxo-1,2-dihydropyridin-3-yl)methyl)isoquinolin-3-yl)amino)-6-isopropyl-5,6-dihydro-4H-pyrazolo[1,5-d][1,4]diazepin-7(8H)-one (5.1 mg, 0.01 mmol) as a yellow solid. LCMS (ESI) [M+H]$^+$=476.2; $^1$H NMR (300 MHz, DMSO-d$_6$) δ 11.59 (s, 1H), 9.17 (s, 1H), 9.00 (s, 1H), 7.57 (s, 1H), 7.27-7.25 (m, 1H), 7.12 (d, J=6.7 Hz, 1H), 6.69 (d, J=6.6 Hz, 1H), 6.14-6.09 (m, 1H), 5.95-5.88 (m, 3H), 4.96 (s, 2H), 4.61-4.57 (m, 1H) 3.78 (s, 4H), 2.99 (s, 2H), 1.13 (d, J=6.8 Hz, 6H).

Example 142

N-(8-amino-3-((6-isopropyl-7-oxo-5,6,7,8-tetra-hydro-4H-pyrazolo[1,5-d][1,4]diazepin-2-yl)amino)isoquinolin-6-yl)ethanesulfonamide (Compound 241)

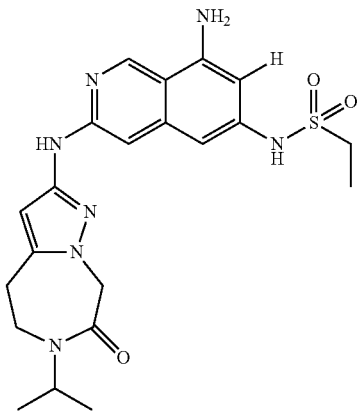 [SMILES: CCS(=O)(=O)Nc1cc(N)c2cnc(Nc3cc4n(n3)CC(=O)N(C(C)C)CC4)cc2c1]

Step 1:tert-butyl(3-amino-8-chloroisoquinolin-6-yl)carbamate

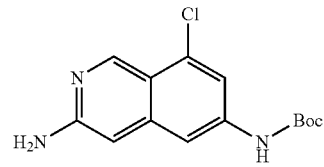 [SMILES: CC(C)(C)OC(=O)Nc1cc(Cl)c2cnc(N)cc2c1]

A mixture of 6-bromo-8-chloro-isoquinolin-3-amine (1.0 g, 3.88 mmol), tert-butyl carbamate (13.65 g, 116.5 mmol), tris(dibenzylideneacetone)dipalladium-chloroform adduct (803.85 mg, 0.78 mmol), 4,5-bis(diphenylphosphino)-9,9-dimethylxanthene (897.83 mg, 1.55 mmol) and cesium carbonate (6.33 g, 19.42 mmol) in 1,4-dioxane (30 mL) was stirred at 90° C. for 2 hours. The solvent was concentrated under vacuum. The residue was purified by flash chromatography on silica gel eluting with petroleum ether/ethyl acetate (1/2) to afford tert-butyl N-(3-amino-8-chloro-6-isoquinolyl)carbamate (500 mg, 1.70 mmol) as a yellow solid. LCMS (ESI) [M+H]$^+$=294.

Step 2: tert-butyl (8-chloro-3-((6-isopropyl-7-oxo-5,6,7,8-tetrahydro-4H-pyrazolo[1,5-d][1,4]diazepin-2-yl)amino)isoquinolin-6-yl)carbamate

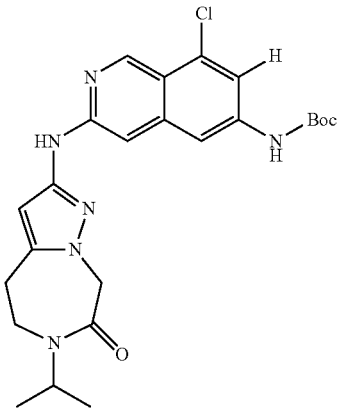 [SMILES: CC(C)N1CCc2cc(Nc3cc4cc(NC(=O)OC(C)(C)C)cc(Cl)c4cn3)nn2CC1=O]

A solution of tert-butyl N-(3-amino-8-chloro-6-isoquinolyl)carbamate (300 mg, 1.02 mmol), tert-butyl N-(3-amino-8-chloro-6-isoquinolyl)carbamate (300 mg, 1.02 mmol), t-BuBrettphosPdG3 (348.87 mg, 0.41 mmol), t-Bu-Brettphos (247.15 mg, 0.51 mmol) and cesium carbonate (1.66 g, 5.11 mmol) in 1,4-dioxane (50 mL) was stirred at 120° C. for 1 hour. The solvent was concentrated under vacuum. The residue was purified by flash chromatography on silica gel eluting with dichloromethane/methanol (97/3) to afford tert-butyl N-[8-chloro-3-[(6-isopropyl-7-oxo-5,8-dihydro-4H-pyrazolo[1,5-d][1,4]diazepin-2-yl)amino]-6-isoquinolyl]carbamate (279 mg, 0.58 mmol) as a brown solid. LCMS (ESI) [M+H]$^+$=485.

Step 3: 2-((6-amino-8-chloroisoquinolin-3-yl)amino)-6-isopropyl-5,6-dihydro-4H-pyrazolo[1,5-d][1,4]diazepin-7(8H)-one

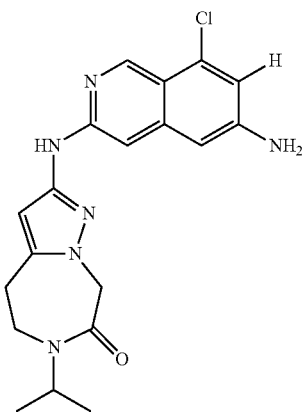 [SMILES: CC(C)N1CCc2cc(Nc3cc4cc(N)cc(Cl)c4cn3)nn2CC1=O]

A solution of tert-butyl N-[8-chloro-3-[(6-isopropyl-7-oxo-5,8-dihydro-4H-pyrazolo[1,5-d][1,4]diazepin-2-yl)amino]-6-isoquinolyl]carbamate (270 mg, 0.56 mmol) in 2,2,2-trifluoroacetic acid (10 mL) was stirred at 25° C. for 1 hour. The solvent was concentrated under vacuum. The reaction mixture was adjusted to pH 10 with ammonia in methanol (7 mol/L). The resulting residue was purified by reverse phase chromatography (acetonitrile 0-40/0.1% NH$_4$CO$_3$ in water) to afford 2-[(6-amino-8-chloro-3-isoquinolyl)amino]-6-isopropyl-5,8-dihydro-4H-pyrazolo[1,5-d][1,4]diazepin-7-one (200 mg, 0.52 mmol) as a gray solid. LCMS (ESI) [M+H]$^+$=385.

Step 4: N-(8-chloro-3-((6-isopropyl-7-oxo-5,6,7,8-tetrahydro-4H-pyrazolo[1,5-d][1,4]diazepin-2-yl)amino)isoquinolin-6-yl)ethanesulfonamide

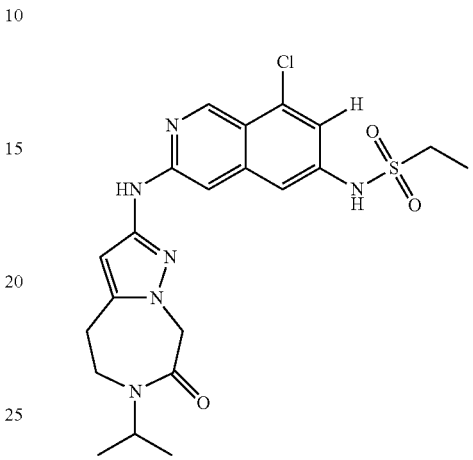

To a solution of 2-[(6-amino-8-chloro-3-isoquinolyl)amino]-6-isopropyl-5,8-dihydro-4H-pyrazolo[1,5-d][1,4]diazepin-7-one (200 mg, 0.52 mmol) and triethylamine (262.43 mg, 2.60 mmol) in dichloromethane (2 mL) was added ethanesulfonyl chloride (200.46 mg, 1.56 mmol) at 0° C. The resulting solution was stirred for 1 hour at 0° C. The organic layer was concentrated under vacuum. Then sodium hydroxide (500 mg, 20.83 mmol) in water (10 mL) was added and stirred at 25° C. for 1 hour. The resulting solution was extracted with ethyl acetate, dried with anhydrous sodium sulfate. After filtration, the filtrate was concentrated under vacuum. The resulting residue was purified by reverse phase chromatography (acetonitrile 0-40/0.1% NH$_4$CO$_3$ in water) to afford N-[8-chloro-3-[(6-isopropyl-7-oxo-5,8-dihydro-4H-pyrazolo[1,5-d][1,4]diazepin-2-yl)amino]-6-isoquinolyl]ethanesulfonamide (85 mg, 0.18 mmol) as a brown solid. LCMS (ESI) [M+H]$^+$=477.

Step 5: tert-butyl (6-(ethylsulfonamido)-3-((6-isopropyl-7-oxo-5,6,7,8-tetrahydro-4H-pyrazolo[1,5-d][1,4]diazepin-2-yl)amino)isoquinolin-8-yl)carbamate

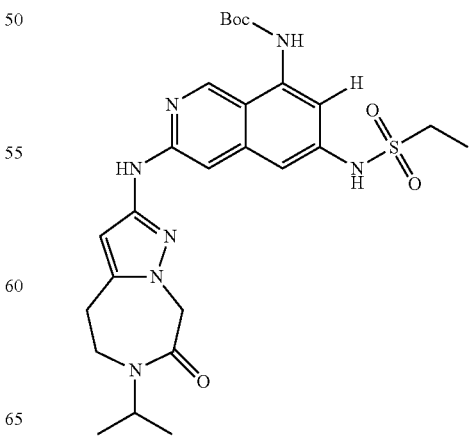

A mixture of N-[8-chloro-3-[(6-isopropyl-7-oxo-5,8-dihydro-4H-pyrazolo[1,5-d][1,4]diazepin-2-yl)amino]-6-isoquinolyl]ethanesulfonamide (80 mg, 0.17 mmol), tert-butyl carbamate (491.22 mg, 4.19 mmol), tris(dibenzylideneacetone)dipalladium-chloroformadduct (69.44 mg, 0.07 mmol), Brettphos (71.92 mg, 0.13 mmol) and cesium carbonate (164.03 mg, 0.50 mmol) in 1,4-dioxane (8 mL) was stirred at 120° C. for 1 hour. The solvent was concentrated under vacuum. The residue was purified by flash chromatography on silica gel eluting with dichloromethane/methanol (96/4) to afford tert-butyl N-[6-(ethylsulfonylamino)-3-[(6-isopropyl-7-oxo-5,8-dihydro-4H-pyrazolo[1,5-d][1,4]diazepin-2-yl)amino]-8-isoquinolyl]carbamate (35 mg, 0.063 mmol) as a yellow solid. LCMS (ESI) [M+H]$^+$=558.

Step 6N-(8-amino-3-((6-isopropyl-7-oxo-5,6,7,8-tetrahydro-4H-pyrazolo[1,5-d][1,4]diazepin-2-yl)amino)isoquinolin-6-yl)ethanesulfonamide

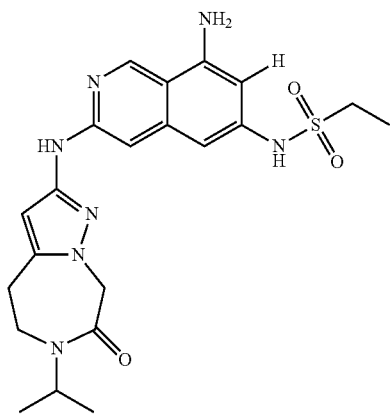 [SMILES: CCS(=O)(=O)Nc1cc(N)c2cnc(Nc3cc4n(n3)CC(=O)N(C(C)C)CC4)cc2c1]

A solution of tert-butyl N-[6-(ethylsulfonylamino)-3-[(6-isopropyl-7-oxo-5,8-dihydro-4H-pyrazolo[1,5-d][1,4]diazepin-2-yl)amino]-8-isoquinolyl]carbamate (30 mg, 0.05 mmol) and 2,2,2-trifluoroacetic acid (3 mL) was stirred at 25° C. for 1 hour. The reaction solution was concentrated under vacuum. The residue was adjusted to pH 10 with ammonia in methanol (7 mol/L). The crude product was purified by prep-HPLC with (XSelect CSH Prep C18 OBD Column, 19*250 mm, 5 um; Water (0.1% FA). ACN (5%-70%) in 7 min; 25 mL/min) to afford N-[8-amino-3-[(6-isopropyl-7-oxo-5,8-dihydro-4H-pyrazolo[1,5-d][1,4]diazepin-2-yl)amino]-6-isoquinolyl]ethanesulfonamide; formic acid (14 mg, 0.028 mmol) as a yellow solid. LCMS (ESI) [M+H]$^+$=458; $^1$HNMR (300 MHz, DMSO-d$_6$) δ 9.84 (s, 1H), 9.00 (s, 2H), 7.40 (s, 1H), 6.57 (d, J=1.8 Hz, 1H), 6.33 (d, J=1.9 Hz, 1H), 6.19 (s, 2H), 6.00 (s, 1H), 4.97 (s, 2H), 4.61 (m, 1H), 3.90-3.71 (m, 2H), 3.19 (m, 2H), 3.00 (d, J=6.1 Hz, 2H), 1.22 (m, 3H), 1.14 (d, J=6.8 Hz, 6H).

Example 143

5-(8-amino-7-fluoro-3-((6-isopropyl-7-oxo-5,6,7,8-tetrahydro-4H-pyrazolo[1,5-d][1,4]diazepin-2-yl)amino)isoquinolin-6-yl)-4-ethyloxazol-2(3H)-one (Compound 242)

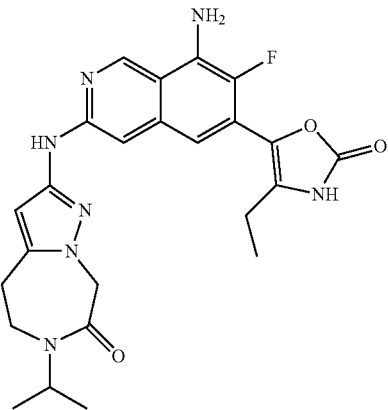 [SMILES: CCc1[nH]c(=O)oc1-c1cc2cc(Nc3cc4n(n3)CC(=O)N(C(C)C)CC4)ncc2c(N)c1F]

Step 1: 4-ethyl-3H-oxazol-2-one

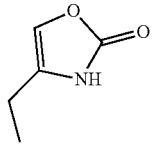

A solution of potassium cyanate (6.0 g, 74.07 mmol), 1-hydroxybutan-2-one (3.0 g, 34.05 mmol) in diethyl ether (100 mL) was added acetic acid (3.0 mL, 34.05 mmol) was stirred at 20° C. for 12 h. After filtration, the filtrate was concentrated under reduced pressure to afford 4-ethyl-3H-oxazol-2-one (1.0 g, 8.84 mmol) as yellow oil. LCMS (ESI) [M+H]$^+$=114.

Step 2: 4-ethyl-3-[(4-methoxyphenyl)methyl]oxazol-2-one

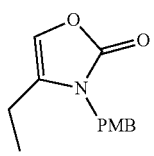

Sodium hydride (579.52 mg, 60% purity, 25.2 mmol) was added to a solution of 4-ethyl-3H-oxazol-2-one (1.9 g, 16.8 mmol) in N,N-dimethylformamide (30 mL) at 0° C. The solution was stirred at 0° C. for 10 minutes. 4-Methoxybenzylchloride (3.14 g, 20.16 mmol) was added and stirred at 25° C. for 2 hours. The reaction solution was diluted with ethyl acetate and washed with water. The organic extract was dried with anhydrous sodium sulfate. After filtration, the filtrate was concentrated under vacuum. The residue was purified by reverse phase flash water (10 mmol/1 sodium bicarbonate)/ACN (60/40) to afford 4-ethyl-3-[(4-methoxyphenyl)methyl]oxazol-2-one (2.1 g, 9.00 mmol) as a light yellow solid. LCMS (ESI) [M+H]$^+$=234.

Step 3: 5-(3-amino-8-chloro-7-fluoro-6-isoquinolyl)-4-ethyl-3-[(4-methoxyphenyl)methyl]oxazol-2-one

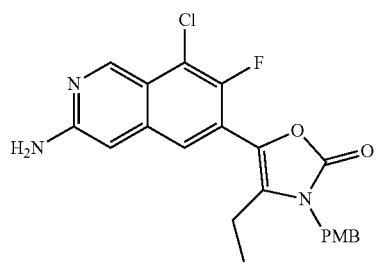

A solution of 8-chloro-7-fluoro-6-iodo-isoquinolin-3-amine (287 mg, 0.89 mmol), 4-ethyl-3-[(4-methoxyphenyl)methyl]oxazol-2-one (207.58 mg, 0.89 mmol), tricyclohexyl phosphine (49.83 mg, 0.18 mmol), palladium acetate (29.01 mg, 0.09 mmol), pivalic acid (22.69 mg, 0.22 mmol) and potassium carbonate (245.61 mg, 1.78 mmol) in N,N-dimethylacetamide (4 mL) was stirred at 100° C. for 3 hours and then concentrated The residue was purified by reverse column eluting with water (sodium bicarbonate 10 mmol/L)/ACN (30/70) to afford 5-(3-amino-8-chloro-7-fluoro-6-isoquinolyl)-4-ethyl-3-[(4-methoxyphenyl)methyl]oxazol-2-one (225 mg, 0.53 mmol) as a yellow solid. LCMS (ESI) [M+H]$^+$=428.

Step 4: 5-[8-chloro-7-fluoro-3-[(6-isopropyl-7-oxo-5,8-dihydro-4H-pyrazolo[1,5-d][1,4]diazepin-2-yl)amino]-6-isoquinolyl]-4-ethyl-3-[(4-methoxyphenyl)methyl]oxazol-2-one

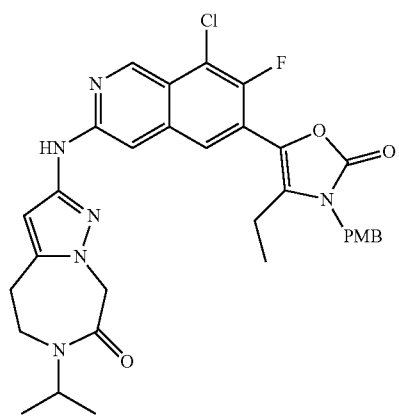

A solution of 5-(3-amino-8-chloro-7-fluoro-6-isoquinolyl)-4-ethyl-3-[(4-methoxyphenyl)methyl]oxazol-2-one (225 mg, 0.53 mmol), 2-bromo-6-isopropyl-5,8-dihydro-4H-pyrazolo[1,5-d][1,4]diazepin-7-one (171.73 mg, 0.63 mmol), tris(dibenzylideneacetone)dipalladium-chloroformadduct (108.86 mg, 0.11 mmol), 4,5-bis(diphenylphosphino)-9,9-dimethylxanthene (121.58 mg, 0.21 mmol) and cesium carbonate (514.3 mg, 1.58 mmol) in 1,4-dioxane (20 mL) was stirred at 100° C. for 12 hours. The mixture was concentrated under vacuum. The residue was purified by flash chromatography on silica gel eluting with dichloromethane/methanol (96/4) to afford 5-[8-chloro-7-fluoro-3-[(6-isopropyl-7-oxo-5,8-dihydro-4H-pyrazolo[1,5-d][1,4]diazepin-2-yl)amino]-6-isoquinolyl]-4-ethyl-3-[(4-methoxyphenyl)methyl]oxazol-2-one (158 mg, 0.26 mmol) as a yellow solid. LCMS (ESI) [M+H]$^+$=619.

Step 5: tert-butyl N-[6-[4-ethyl-3-[(4-methoxyphenyl)methyl]-2-oxo-oxazol-5-yl]-7-fluoro-3-[(6-isopropyl-7-oxo-5,8-dihydro-4H-pyrazolo[1,5-d][1,4]diazepin-2-yl)amino]-8-isoquinolyl]carbamate

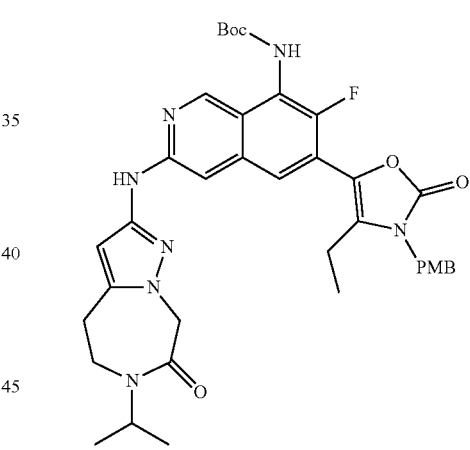

A mixture of 5-[8-chloro-7-fluoro-3-[(6-isopropyl-7-oxo-5,8-dihydro-4H-pyrazolo[1,5-d][1,4]diazepin-2-yl)amino]-6-isoquinolyl]-4-ethyl-3-[(4-methoxyphenyl)methyl]oxazol-2-one (155 mg, 0.25 mmol), tert-butyl carbamate (732.32 mg, 6.26 mmol), tris(dibenzylideneacetone)dipalladium-chloroformadduct (51.83 mg, 0.05 mmol), Brettphos (40.26 mg, 0.08 mmol), and cesium carbonate (244.86 mg, 0.75 mmol) in 1,4-dioxane (12 mL) was stirred at 90° C. for 2 hours. The mixture was concentrated under vacuum. The residue was purified by flash chromatography on silica gel eluting with dichloromethane/methanol (96/4) to afford tert-butyl N-[6-[4-ethyl-3-[(4-methoxyphenyl)methyl]-2-oxo-oxazol-5-yl]-7-fluoro-3-[(6-isopropyl-7-oxo-5,8-dihydro-4H-pyrazolo[1,5-d][1,4]diazepin-2-yl)amino]-8-isoquinolyl]carbamate (80 mg, 0.11 mmol) as a light yellow solid. LCMS (ESI) [M+H]$^+$=700.

Step 6: 5-[8-amino-7-fluoro-3-[(6-isopropyl-7-oxo-5,8-dihydro-4H-pyrazolo[1,5-d][1,4]diazepin-2-yl)amino]-6-isoquinolyl]-4-ethyl-3H-oxazol-2-one

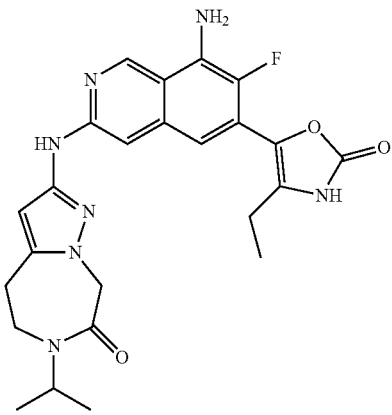 [SMILES: CCc1[nH]c(=O)oc1-c1cc2cc(Nc3cc4n(n3)CC(=O)N(C(C)C)CC4)ncc2c(N)c1F]

A solution of tert-butyl N-[6-[4-ethyl-3-[(4-methoxyphenyl)methyl]-2-oxo-oxazol-5-yl]-7-fluoro-3-[(6-isopropyl-7-oxo-5,8-dihydro-4H-pyrazolo[1,5-d][1,4]diazepin-2-yl)amino]-8-isoquinolyl]carbamate (140 mg, 0.20 mmol) in 2,2,2-trifluoroacetic acid (5.0 mL) and trifluoromethanesulfonic acid (1.0 mL) was stirred at 25° C. for 48 hours. The crude product was purified by prep-HPLC [XBridge Prep C18 5 um×30 mm×150 mm; water (sodium bicarbonate 10 mmol/L):ACN (15%-50%) in 6.03 min] to afford 5-[8-amino-7-fluoro-3-[(6-isopropyl-7-oxo-5,8-dihydro-4H-pyrazolo[1,5-d][1,4]diazepin-2-yl)amino]-6-isoquinolyl]-4-ethyl-3H-oxazol-2-one (33 mg, 0.069 mmol) as a brown solid. LCMS (ESI) [M+H]⁺=480; ¹HNMR (400 MHz, DMSO-d₆) δ 11.04 (s, 1H), 9.21 (s, 1H), 9.09 (s, 1H), 7.66 (s, 1H), 6.86 (d, J=6.0 Hz, 1H), 6.13 (s, 2H), 5.98 (s, 1H), 4.98 (s, 2H), 4.65-4.56 (m, 1H), 3.78 (t, J=6.0 Hz, 2H), 2.98 (t, J=6.0 Hz, 2H), 2.51-2.47 (m, 2H), 1.21-1.12 (m, 9H).

Example 144

2-((8-amino-6-(5-amino-4-chloropyridin-3-yl)-7-fluoroisoquinolin-3-yl)amino)-6-isopropyl-5,6-dihydro-4H-pyrazolo[1,5-d][1,4]diazepin-7(8H)-one (Compound 243)

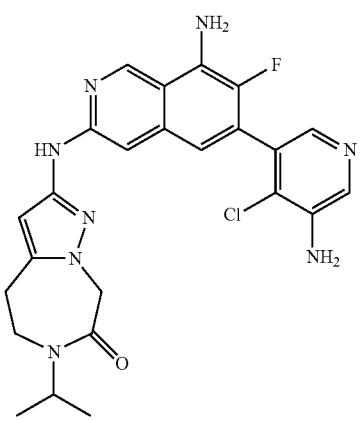 [SMILES: CC(C)N1CCc2cc(Nc3cc4cc(-c5cncc(N)c5Cl)c(F)c(N)c4cn3)nn2CC1=O]

Step 1: 4-chloro-5-iodo-pyridin-3-amine

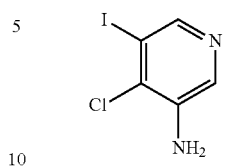

To a solution of 4-chloro-3-iodo-5-nitro-pyridine (1.0 g, 3.52 mmol) in diethyl ether (10 mL) was added hydrochloric acid (7.4 mL, 3.52 mmol) and stannous chloride (8.0 g, 35.4 mmol) at 25° C. The mixture was stirred at rt for 2 hours. The reaction was quenched with ammonia in methanol (7 mol/L). The resulting solution was extracted with ethyl acetate, dried with anhydrous sodium sulfate. After filtration, the filtrate was concentrated under vacuum to afford 4-chloro-5-iodo-pyridin-3-amine (800 mg, 3.14 mmol) as a yellow solid. LCMS (ESI) [M+H]⁺=254.5.

Step 2:tert-butyl N-[6-(5-amino-4-chloro-3-pyridyl)-7-fluoro-3-[(6-isopropyl-7-oxo-5,8-dihydro-4H-pyrazolo[1,5-d][1,4]diazepin-2-yl)amino]-8-isoquinolyl]carbamate

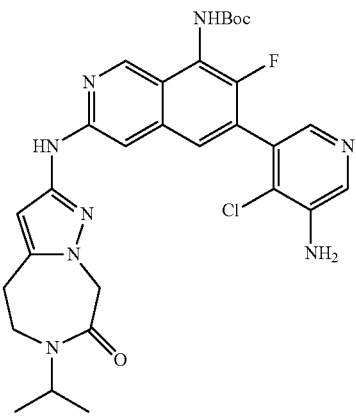 [SMILES: CC(C)N1CCc2cc(Nc3cc4cc(-c5cncc(N)c5Cl)c(F)c(NC(=O)OC(C)(C)C)c4cn3)nn2CC1=O]

Under nitrogen, a solution of 4-chloro-5-iodo-pyridin-3-amine (74.0 mg, 0.29 mmol), [8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl] boronic acid (50.0 mg, 0.10 mmol), potassium phosphate (20.0 mg, 0.09 mmol), sodium acetate (23.85 mg, 0.29 mmol) and [1,1'-bis(diphenylphosphino)ferrocene]dichloropalladium(II) (15.0 mg, 0.02 mmol) in acetonitrile (1 mL) and water (0.10 mL). The resulting solution was stirred for 1 hour at 90° C. The solvent was concentrated under vacuum. The residue was purified by flash chromatography on silica gel eluting with methanol/dichloromethane (5/95) to afford tert-butyl N-[6-(5-amino-4-chloro-3-pyridyl)-7-fluoro-3-[(6-isopropyl-7-oxo-5,8-dihydro-4H-pyrazolo[1,5-d][1,4]diazepin-2-yl)amino]-8-isoquinolyl]carbamate (50 mg, 0.084 mmol) as a yellow solid. LC/MS (ESI) [M+H]⁺=595.1.

Step 3: 2-((8-amino-6-(5-amino-4-chloropyridin-3-yl)-7-fluoroisoquinolin-3-yl)amino)-6-isopropyl-5,6-dihydro-4H-pyrazolo[1,5-d][1,4]diazepin-7(8H)-one

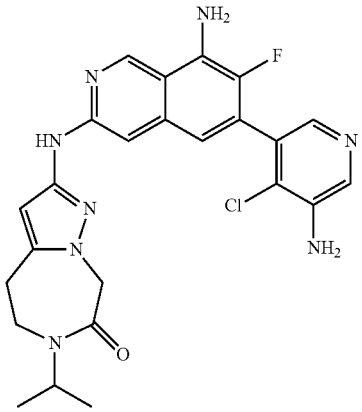 [SMILES: CC(C)N1CCc2cc(Nc3cc4cc(-c5cncc(N)c5Cl)c(F)c(N)c4cn3)nn2CC1=O]

A solution of tert-butyl N-[6-(5-amino-4-chloro-3-pyridyl)-7-fluoro-3-[(6-isopropyl-7-oxo-5,8-dihydro-4H-pyrazolo[1,5-d][1,4]diazepin-2-yl)amino]-8-isoquinolyl]carbamate (50.0 mg, 0.08 mmol) and TFA (1 mL, 0.08 mmol) in dichloromethane (5 mL) was stirred at 25° C. for 2 hours. The reaction mixture was adjusted to pH 7 with ammonia in methanol (7 mol/L). The residue was purified by flash chromatography on C18 (acetonitrile-0.1% sodium bicarbonate in water) to afford 2-((8-amino-6-(5-amino-4-chloropyridin-3-yl)-7-fluoroisoquinolin-3-yl)amino)-6-isopropyl-5,6-dihydro-4H-pyrazolo[1,5-d][1,4]diazepin-7(8H)-one (12.9 mg, 0.026 mmol) as a red solid. LCMS (ESI) $[M+H]^+=495.2$. $^1$HNMR (300 MHz, DMSO-$d_6$) δ 9.24 (s, 1H), 9.08 (s, 1H), 8.13 (s, 1H), 7.73 (s, 1H), 7.70 (s, 1H), 6.77 (d, J=5.9 Hz, 1H), 6.09 (s, 2H), 5.94 (s, 1H), 5.77 (s, 2H), 4.94 (s, 2H), 4.63-4.51 (m, 1H), 3.81-3.70 (m, 2H), 2.99-2.91 (m, 2H), 1.10 (d, J=6.8 Hz, 6H).

Example 145

2-((8-amino-7-fluoro-6-((4-methyl-2-oxopiperazin-1-yl)methyl)isoquinolin-3-yl)amino)-6-isopropyl-5,6-dihydro-4H-pyrazolo[1,5-d][1,4]diazepin-7(8H)-one (Compound 244)

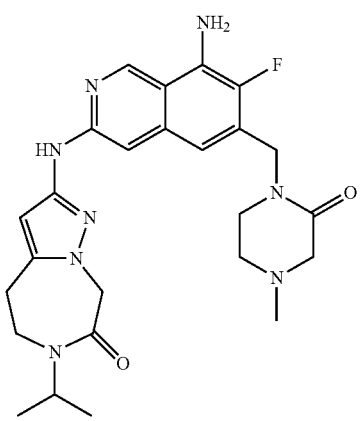 [SMILES: CC(C)N1CCc2cc(Nc3cc4cc(CN5CCN(C)CC5=O)c(F)c(N)c4cn3)nn2CC1=O]

Step 1: (3-amino-8-chloro-7-fluoro-6-isoquinolyl)methanol

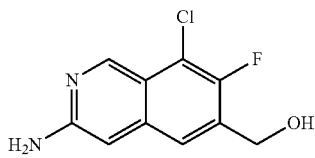 [SMILES: Nc1cc2cc(CO)c(F)c(Cl)c2cn1]

A solution of tributylstannylmethanol (3.98 g, 12.4 mmol), 8-chloro-7-fluoro-6-iodo-isoquinolin-3-amine (2.0 g, 6.2 mmol) and tetrakis(triphenylphosphine)palladium (1.43 g, 1.24 mmol) in 1,4-dioxane (20 mL) was stirred for 60 hours at 90° C. After filtration, the filtrate was concentrated under vacuum. The residue was purified by flash chromatography on silica gel eluting with dichloromethane/methanol (10/1) to afford (3-amino-8-chloro-7-fluoro-6-isoquinolyl)methanol (550 mg, 2.43 mmol) as a yellow solid. LCMS (ESI) $[M+H]^+=227$.

Step 2: 2-[[8-chloro-7-fluoro-6-(hydroxymethyl)-3-isoquinolyl]amino]-6-isopropyl-5,8-dihydro-4H-pyrazolo[1,5-d][1,4]diazepin-7-one

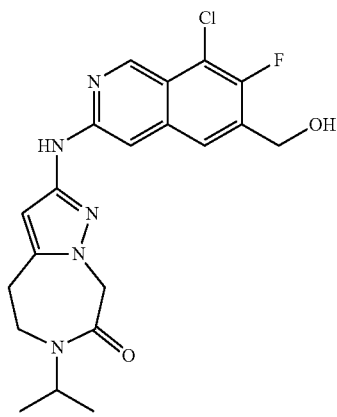 [SMILES: CC(C)N1CCc2cc(Nc3cc4cc(CO)c(F)c(Cl)c4cn3)nn2CC1=O]

To a solution of 3-amino-8-chloro-7-fluoro-6-isoquinolyl)methanol (200 mg, 0.88 mmol), 2-bromo-6-isopropyl-5,8-dihydro-4H-pyrazolo[1,5-d][1,4]diazepin-7-one (264.18 mg, 0.97 mmol), t-BuBrettphos (213.56 mg, 0.44 mmol) and t-BuBrettphos PdG3 (301.46 mg, 0.35 mmol) in 1,4-dioxane (40 mL) was added cesium carbonate (1.44 g, 4.41 mmol) at 25° C. The resulting solution was stirred for 1 hour at 120° C. After filtration, the filtrate was concentrated under vacuum. The residue was purified by flash chromatography on silica gel eluting with dichloromethane/methanol (9/1) to afford 2-[[8-chloro-7-fluoro-6-(hydroxymethyl)-3-isoquinolyl]amino]-6-isopropyl-5,8-dihydro-4H-pyrazolo[1,5-d][1,4]diazepin-7-one (120 mg, 0.29 mmol) as a yellow solid. LCMS (ESI) $[M+H]^+=418$.

Step 3: 2-[[8-chloro-6-(chloromethyl)-7-fluoro-3-isoquinolyl]amino]-6-isopropyl-5,8-dihydro-4H-pyrazolo[1,5-d][1,4]diazepin-7-one

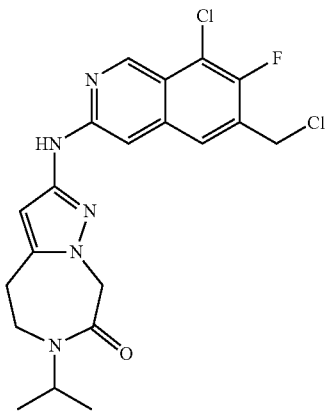 [SMILES: CC(C)N1CCc2cc(Nc3cc4cc(CCl)c(F)c(Cl)c4cn3)nn2CC1=O]

A solution of 2-[[8-chloro-7-fluoro-6-(hydroxymethyl)-3-isoquinolyl]amino]-6-isopropyl-5,8-dihydro-4H-pyrazolo[1,5-d][1,4]diazepin-7-one (50 mg, 0.12 mmol) and thionyl chloride (70.6 mg, 0.60 mmol) in dichloromethane (5 mL) was stirred at 25° C. for 1 hour. The solvent was concentrated under vacuum to afford 2-[[8-chloro-6-(chloromethyl)-7-fluoro-3-isoquinolyl]amino]-6-isopropyl-5,8-dihydro-4H-pyrazolo[1,5-d][1,4]diazepin-7-one (50 mg, 0.11 mmol) as a color solid. LCMS (ESI) [M+H]$^+$=436.

Step 4: 2-[[8-chloro-7-fluoro-6-[(4-methyl-2-oxo-piperazin-1-yl)methyl]-3-isoquinolyl]amino]-6-isopropyl-5,8-dihydro-4H-pyrazolo[1,5-d][1,4]diazepin-7-one

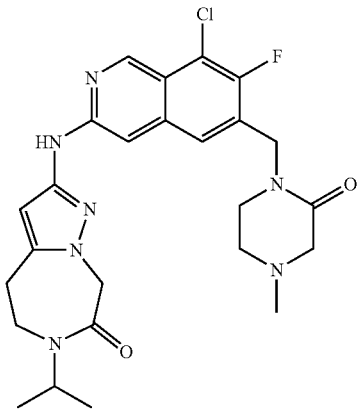 [SMILES: CC(C)N1CCc2cc(Nc3cc4cc(CN5CCN(C)CC5=O)c(F)c(Cl)c4cn3)nn2CC1=O]

To a solution of 4-methyl-2-piperazinone (26.16 mg, 0.23 mmol) in N,N-dimethylformamide (3 mL) was added sodium hydride (18.34 mg, 60% purity, 0.46 mmol) at 0° C. The reaction was stirred for 20 minutes at 0° C. 2-[[8-Chloro-6-(chloromethyl)-7-fluoro-3-isoquinolyl]amino]-6-isopropyl-5,8-dihydro-4H-pyrazolo[1,5-d][1,4]diazepin-7-one (50 mg, 0.11 mmol) was added and stirred at 25° C. for 1 hour. The reaction was quenched with water, extracted with ethyl acetate, dried with anhydrous sodium sulfate. After filtration, the filtrate was concentrated under vacuum. The residue was purified by reverse phase chromatography (acetonitrile 0-40/0.1% sodium bicarbonate in water) to afford 2-[[8-chloro-7-fluoro-6-[(4-methyl-2-oxo-piperazin-1-yl)methyl]-3-isoquinolyl]amino]-6-isopropyl-5,8-dihydro-4H-pyrazolo[1,5-d][1,4]diazepin-7-one (9 mg, 0.018 mmol) as a yellow solid. LCMS (ESI) [M+H]$^+$=514.

Step 5: tert-butyl N-[7-fluoro-3-[(6-isopropyl-7-oxo-5,8-dihydro-4H-pyrazolo[1,5-d][1,4]diazepin-2-yl)amino]-6-[(4-methyl-2-oxo-piperazin-1-yl)methyl]-8-isoquinolyl]carbamate

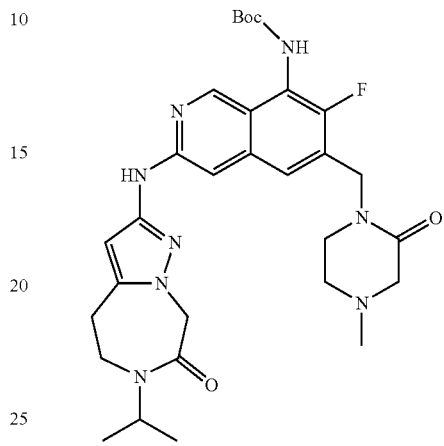

To a mixture of 2-[[8-chloro-7-fluoro-6-[(4-methyl-2-oxo-piperazin-1-yl)methyl]-3-isoquinolyl]amino]-6-isopropyl-5,8-dihydro-4H-pyrazolo[1,5-d][1,4]diazepin-7-one (46 mg, 0.09 mmol), tert-Butyl carbamate (314.53 mg, 2.68 mmol), tris(dibenzylideneacetone)dipalladium (18.53 mg, 0.02 mmol) and Brettphos (19.22 mg, 0.04 mmol) in 1,4-dioxane (5 mL) was added cesium carbonate (116.7 mg, 0.36 mmol) at 25° C. The reaction was stirred for 3 hours at 90° C. After filtration, the filtrate was concentrated under vacuum. The residue was purified by flash chromatography on silica gel eluting with dichloromethane/methanol (9/1) to afford tert-butyl N-[7-fluoro-3-[(6-isopropyl-7-oxo-5,8-dihydro-4H-pyrazolo[1,5-d][1,4]diazepin-2-yl)amino]-6-[(4-methyl-2-oxo-piperazin-1-yl)methyl]-8-isoquinolyl]carbamate (45 mg, 0.076 mmol) as a yellow solid. LCMS (ESI) [M+H]$^+$=595.

Step 6: 2-[[8-amino-7-fluoro-6-[(4-methyl-2-oxo-piperazin-1-yl)methyl]-3-isoquinolyl]amino]-6-isopropyl-5,8-dihydro-4H-pyrazolo[1,5-d][1,4]diazepin-7-one

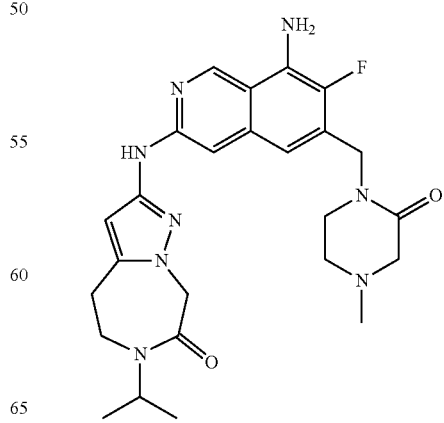

A solution of tert-butyl N-[7-fluoro-3-[(6-isopropyl-7-oxo-5,8-dihydro-4H-pyrazolo[1,5-d][1,4]diazepin-2-yl)amino]-6-[(4-methyl-2-oxo-piperazin-1-yl)methyl]-8-isoquinolyl]carbamate (43 mg, 0.07 mmol) in 2,2,2-trifluoroacetic acid (2 mL) and dichloromethane (4 mL) was stirred at 25° C. for 2 hours. The mixture was concentrated under vacuum. The residue was purified by prep-HPLC (Atlantis HILIC OBD, 19×150 mm 5 um; water (0.1% FA):CH3CN=7%-15% B in 7 min) to afford 2-[[8-amino-7-fluoro-6-[(4-methyl-2-oxo-piperazin-1-yl)methyl]-3-isoquinolyl]amino]-6-isopropyl-5,8-dihydro-4H-pyrazolo[1,5-d][1,4]diazepin-7-one (15.5 mg, 0.029 mmol) as a red solid. LCMS (ESI) [M+H]$^+$=495.3; $^1$HNMR (300 MHz, DMSO-d$_6$) δ 9.16 (s, 1H), 9.04 (s, 1H), 8.12 (s, 1H), 7.57 (s, 1H), 6.63 (d, J=6.0 Hz, 1H), 5.99 (s, 1H), 5.94 (s, 1H), 4.95 (s, 2H), 4.66-4.50 (m, 3H), 3.76 (t, J=5.9 Hz, 2H), 3.3-3.2 (m, 2H), 3.19 (s, 2H), 2.96 (t, J=5.5 Hz, 2H), 2.88-2.64 (m, 2H), 2.32 (s, 3H), 1.10 (d, J=6.8 Hz, 6H).

Example 146

5-(8-amino-7-fluoro-3-((6-isopropyl-7-oxo-5,6,7,8-tetrahydro-4H-pyrazolo[1,5-d][1,4]diazepin-2-yl)amino)isoquinolin-6-yl)-N,N,4-trimethylpyrimidine-2-carboxamide (Compound 245)

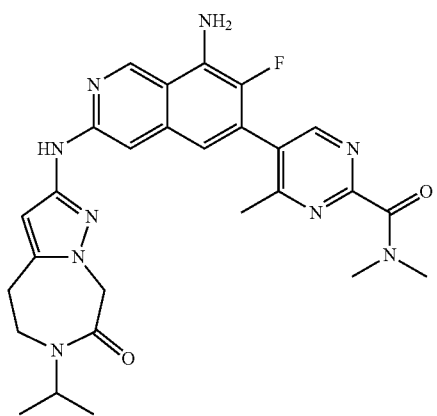 [SMILES: Cc1nc(C(=O)N(C)C)ncc1-c1cc2cc(Nc3cc4n(n3)CC(=O)N(C(C)C)CC4)ncc2c(N)c1F]

Step 1: 5-bromo-4-methyl-pyrimidine-2-carbonitrile

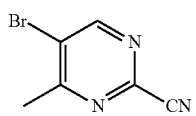

A solution of sodium cyanide (1062.86 mg, 21.69 mmol) and 1,4-diazabicyclooctane triethylenediamine (323.92 mg, 2.89 mmol) in dimethyl sulfoxide (2 mL) and water (2 mL) was stirred at 25° C. for 1 hour. A solution of 5-bromo-2-chloro-4-methylpyrimidine (3.0 g, 14.46 mmol) in dimethyl sulfoxide was added and stirred for 12 hours. The reaction was quenched with ferrous sulfate in water. The resulting solution was extracted with ethyl acetate, dried with anhydrous sodium sulfate. After filtration, the filtrate was concentrated under vacuum. The residue was purified by flash chromatography on silica gel eluting with methanol/dichloromethane (5/95) to afford 5-bromo-4-methyl-pyrimidine-2-carbonitrile (700 mg, 3.54 mmol) as a yellow solid. LCMS (ESI) [M+H]$^+$=198.0.

Step 2: 5-bromo-4-methyl-pyrimidine-2-carboxylic Acid

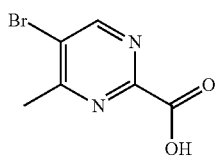

A solution of 5-bromo-4-methyl-pyrimidine-2-carbonitrile (1.0 g, 5.05 mmol) and NaOH (606 mg, 15.15 mmol) in water (40 mL) was stirred at 60° C. for 2 hours. The reaction mixture was adjusted to pH 2 with hydrochloric acid (2 mol/L). The resulting solution was extracted with ethyl acetate, dried with anhydrous sodium sulfate. After filtration, the filtrate was concentrated under vacuum to afford 5-bromo-4-methyl-pyrimidine-2-carboxylic acid (800 mg, 3.69 mmol) as light yellow oil. LC0MS (ESI) [M+H]$^+$=217.0.

Step 3: 5-bromo-N,N,4-trimethyl-pyrimidine-2-carboxamide

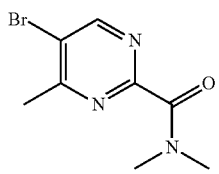

To a solution of 5-bromo-4-methyl-pyrimidine-2-carboxylic acid (1.0 g, 4.61 mmol), N,N-dimethylamine (311.58 mg, 6.91 mmol) and N,N-diisopropylethylamine (2377.66 mg, 18.43 mmol) in N,N-dimethylformamide (30 mL) was added 2-(7-azabenzotriazol-1-yl)-N,N,N',N'-tetramethyluronium hexafluorophosphate (2628.08 mg, 6.91 mmol). The mixture was stirred at 25° C. for 12 hours and then quenched by water. The resulting solution was extracted with ethyl acetate, dried with anhydrous sodium sulfate. After filtration, the filtrate was concentrated under vacuum. The residue was purified by flash chromatography on silica gel eluting with methanol/dichloromethane (5/95) to afford 5-bromo-N,N,4-trimethyl-pyrimidine-2-carboxamide (600 mg, 2.46 mmol) as a yellow oil. LC/MS (ESI) [M+H]$^+$=244.1.

Step 4:tert-butyl N-[6-[2-(dimethylcarbamoyl)-4-methyl-pyrimidin-5-yl]-7-fluoro-3-[(6-isopropyl-7-oxo-5,8-dihydro-4H-pyrazolo[1,5-d][1,4]diazepin-2-yl)amino]-8-isoquinolyl]carbamate

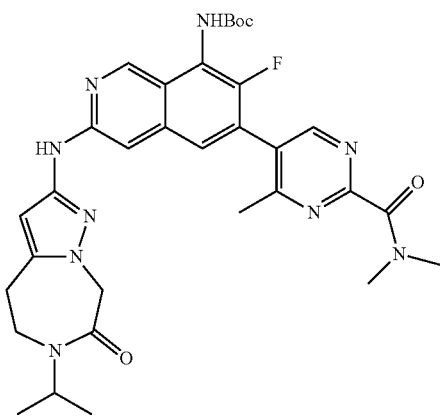 [SMILES: Cc1nc(C(=O)N(C)C)ncc1-c1cc2cc(Nc3cc4n(n3)CC(=O)N(C(C)C)CC4)ncc2c(NC(=O)OC(C)(C)C)c1F]

A mixture of [8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]boronic acid (50.0 mg, 0.10 mmol), 5-bromo-N,N,4-trimethyl-pyrimidine-2-carboxamide (47.64 mg, 0.20 mmol), terakis(triphenylphosphine)palladium (22.56 mg, 0.02 mmol) and potassium carbonate (40 mg, 0.29 mmol) in 1,4-dioxane (5 mL) and water (1 mL) was stirred at 90° C. for 1 hour. The solvent was concentrated under vacuum. The residue was purified by reverse column eluting with sodium bicarbonate (10 mmol/L)/ACN (70/30) to afford tert-butyl N-[6-[2-(dimethylcarbamoyl)-4-methyl-pyrimidin-5-yl]-7-fluoro-3-[(6-isopropyl-7-oxo-5,8-dihydro-4H-pyrazolo[1,5-d][1,4]diazepin-2-yl)amino]-8-isoquinolyl]carbamate (40 mg, 0.063 mmol) as a light yellow solid. LCMS (ESI) [M+H]$^+$=631.7.

Step 5: tert-butyl N-[6-[2-(dimethylcarbamoyl)-4-methyl-pyrimidin-5-yl]-7-fluoro-3-[(6-isopropyl-7-oxo-5,8-dihydro-4H-pyrazolo[1,5-d][1,4]diazepin-2-yl)amino]-8-isoquinolyl]carbamate

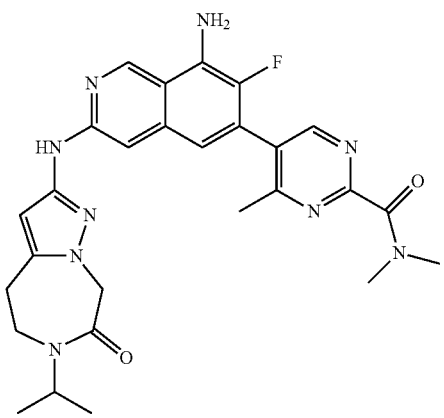 [SMILES: Cc1nc(C(=O)N(C)C)ncc1-c1cc2cc(Nc3cc4n(n3)CC(=O)N(C(C)C)CC4)ncc2c(N)c1F]

A mixture of tert-butyl N-[6-[2-(dimethylcarbamoyl)-4-methyl-pyrimidin-5-yl]-7-fluoro-3-[(6-isopropyl-7-oxo-5,8-dihydro-4H-pyrazolo[1,5-d][1,4]diazepin-2-yl)amino]-8-isoquinolyl]carbamate (5.0 mg, 0.010 mmol) and 2,2,2-trifluoroacetic acid (0.2 mL) in dichloromethane (2 mL) was stirred at 25° C. for 3 hours. The reaction mixture was adjusted to pH 7 with ammonia in methanol (7 mol/L). The mixture was concentrated under vacuum. The residue was purified by flash chromatography on C18 (acetonitrile-0.1% sodium bicarbonate in water) to afford 5-(8-amino-7-fluoro-3-((6-isopropyl-7-oxo-5,6,7,8-tetrahydro-4H-pyrazolo[1,5-d][1,4]diazepin-2-yl)amino)isoquinolin-6-yl)-N,N,4-trimethylpyrimidine-2-carboxamide (9.1 mg, 0.017 mmol) as an orange solid. LCMS (ESI) [M+H]$^+$=532.2. $^1$H NMR (400 MHz, DMSO-d$_6$) δ 9.30 (s, 1H), 9.16 (s, 1H), 8.77 (s, 1H), 7.78 (s, 1H), 6.92 (d, J=6.1 Hz, 1H), 6.23 (s, 2H), 5.96 (s, 1H), 4.96 (s, 2H), 4.56-4.58 (m, 1H), 3.80-3.77 (m, 2H), 3.05 (s, 3H), 2.98-2.90 (m, 2H), 2.86 (s, 3H), 2.45 (d, J=1.2 Hz, 3H), 1.12 (d, J=6.8 Hz, 6H).

Example 147

2-((8-amino-6-(5-amino-4-methoxypyridin-3-yl)-7-fluoroisoquinolin-3-yl)amino)-6-isopropyl-5,6-dihydro-4H-pyrazolo[1,5-d][1,4]diazepin-7(8H)-one
(Compound 246)

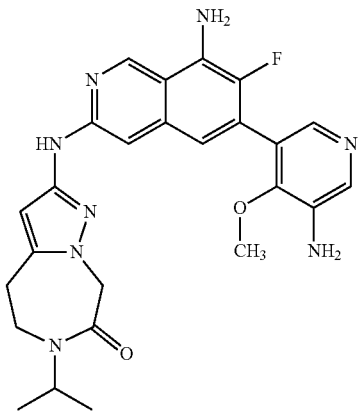 [SMILES: COc1c(N)cncc1-c1cc2cc(Nc3cc4n(n3)CC(=O)N(C(C)C)CC4)ncc2c(N)c1F]

Step 1: 3-bromo-4-methoxy-5-nitro-pyridine

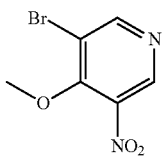

A solution of 3-bromo-4-chloro-5-nitropyridine (3.0 g, 12.63 mmol), methanol (4.68 mL) and potassium carbonate (3.49 g, 25.27 mmol) in N,N-dimethylformamide (3 mL) was stirred at 25° C. for 1 hour. The solvent was concentrated under vacuum. The residue was purified by flash chromatography on silica gel eluting with methanol/dichloromethane (2/98) to afford 3-bromo-4-methoxy-5-nitropyridine (600 mg, 2.57 mmol) as a colorless oil. LCMS (ESI) [M+H]$^+$=233.0.

Step 2: [tert-butyl N-[7-fluoro-3-[(6-isopropyl-7-oxo-5,8-dihydro-4H-pyrazolo[1,5-d][1,4]diazepin-2-yl)amino]-6-(4-methoxy-5-nitro-3-pyridyl)-8-isoquinolyl]carbamate

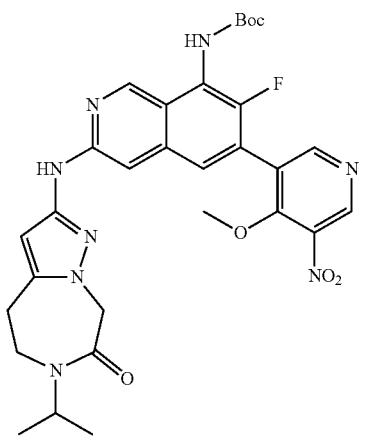 [SMILES: COc1c(-c2cc3cc(Nc4cc5n(n4)CC(=O)N(C(C)C)CC5)ncc3c(NC(=O)OC(C)(C)C)c2F)cncc1[N+](=O)[O-]]

A mixture of [8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl boronic acid (102.94 mg, 0.20 mmol), 3-bromo-4-methoxy-5-nitro-pyridine (70.0 mg, 0.30 mmol), tetrakis(triphenylphosphine)palladium (47.35 mg, 0.04 mmol) and potassium carbonate (82.35 mg, 0.60 mmol) in 1,4-dioxane (1 mL) and water (0.10 mL) was stirred at 90° C. for 1 hour. The mixture was concentrated under vacuum. The residue was purified by flash chromatography on C18 eluting with ACN/water (70%) to afford tert-butyl N-[7-fluoro-3-[(6-isopropyl-7-oxo-5,8-dihydro-4H-pyrazolo[1,5-d][1,4]diazepin-2-yl)amino]-6-(4-methoxy-5-nitro-3-pyridyl)-8-isoquinolyl]carbamate (60 mg, 0.097 mmol) as a brown oil. LCMS (ESI) [M+H]⁺=620.6.

Step 3: [tert-butyl N-[6-(5-amino-4-methoxy-3-pyridyl)-7-fluoro-3-[(6-isopropyl-7-oxo-5,8-dihydro-4H-pyrazolo[1,5-d][1,4]diazepin-2-yl)amino]-8-isoquinolyl]carbamate

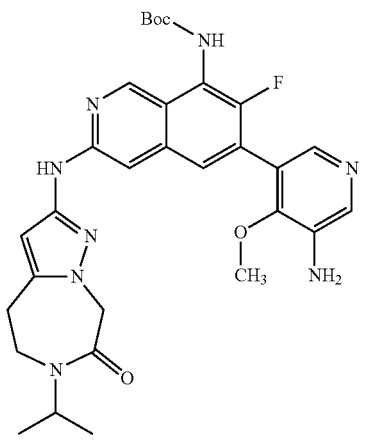 [SMILES: COc1c(N)cncc1-c1cc2cc(Nc3cc4n(n3)CC(=O)N(C(C)C)CC4)ncc2c(NC(=O)OC(C)(C)C)c1F]

A mixture of tert-butyl N-[7-fluoro-3-[(6-isopropyl-7-oxo-5,8-dihydro-4H-pyrazolo[1,5-d][1,4]diazepin-2-yl)amino]-6-(4-methoxy-5-nitro-3-pyridyl)-8-isoquinolyl]carbamate (70 mg, 0.11 mmol) and raney nickel (10 mg, 0.11 mmol)] in methanol (5 mL) was stirred at 25° C. After filtration, the filtrate was concentrated under vacuum. The residue was purified by flash chromatography on C18 eluting with ACN/water (60%) to afford [tert-butyl N-[6-(5-amino-4-methoxy-3-pyridyl)-7-fluoro-3-[(6-isopropyl-7-oxo-5,8-dihydro-4H-pyrazolo[1,5-d][1,4]diazepin-2-yl)amino]-8-isoquinolyl]carbamate (40 mg, 0.07 mmol) as a yellow oil. LCMS (ESI) [M+H]⁺=590.6.

Step 4: 2-((8-amino-6-(5-amino-4-methoxypyridin-3-yl)-7-fluoroisoquinolin-3-yl)amino)-6-isopropyl-5,6-dihydro-4H-pyrazolo[1,5-d][1,4]diazepin-7(8H)-one

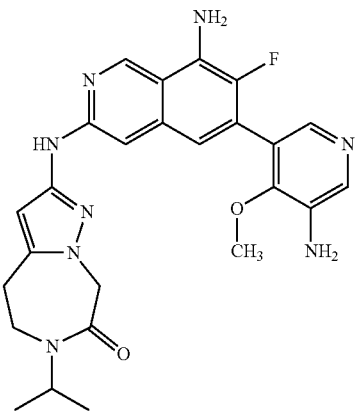 [SMILES: COc1c(N)cncc1-c1cc2cc(Nc3cc4n(n3)CC(=O)N(C(C)C)CC4)ncc2c(N)c1F]

A mixture of tert-butyl N-[6-(5-amino-4-methoxy-3-pyridyl)-7-fluoro-3-[(6-isopropyl-7-oxo-5,8-dihydro-4H-pyrazolo[1,5-d][1,4]diazepin-2-yl)amino]-8-isoquinolyl]carbamate (40.0 mg, 0.07 mmol) and 2,2,2-trifluoroacetic acid (1 mL) in dichloromethane (5 mL) was stirred at 25° C. for 3 hours. The mixture was concentrated under vacuum. The reaction mixture was adjusted to pH 7 with ammonia in methanol (7 mol/L). The residue was purified by flash chromatography on C18 (acetonitrile-0.1% sodium bicarbonate in water) to afford 2-((8-amino-6-(5-amino-4-methoxypyridin-3-yl)-7-fluoroisoquinolin-3-yl)amino)-6-isopropyl-5,6-dihydro-4H-pyrazolo[1,5-d][1,4]diazepin-7(8H)-one (6.1 mg, 0.012 mmol) as a yellow solid. LCMS (ESI) [M+H]⁺=491.3. ¹H NMR (400 MHz, DMSO-d₆) δ 9.24 (s, 1H), 9.06 (s, 1H), 8.05 (s, 1H), 7.72 (s, 1H), 7.68 (s, 1H), 6.83 (d, J=6.0 Hz, 1H), 6.04 (s, 2H), 5.96 (s, 1H), 5.22 (s, 2H), 4.96 (s, 2H), 4.62-4.55 (m, 1H), 3.81-3.73 (m, 2H), 3.45 (s, 3H), 3.02-2.94 (m, 2H), 1.12 (d, J=6.8 Hz, 6H).

Example 148

6-(5-amino-4-methylpyridin-3-yl)-N3-(5,6-dihydro-11H-imidazo[1,2-a]pyrazolo[1,5-d][1,4]diazepin-8-yl)-7-fluoroisoquinoline-3,8-diamine (Compound 247)

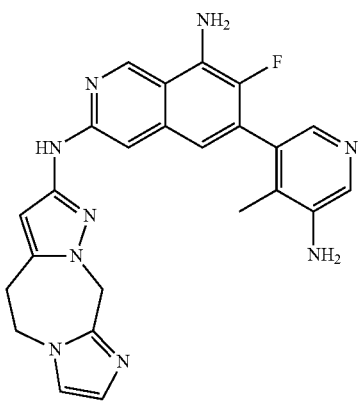 [SMILES: Cc1c(N)cncc1-c1cc2cc(Nc3cc4n(n3)Cc3nccn3CC4)ncc2c(N)c1F]

Step 1: 2-bromo-4,5,6,8-tetrahydropyrazolo[1,5-d][1,4]diazepine-7-thione

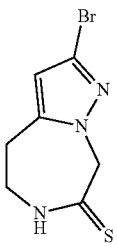

A solution of 2-bromo-4,5,6,8-tetrahydropyrazolo[1,5-d][1,4]diazepin-7-one (1.0 g, 4.35 mmol) and Lawesson's reagent (1.8 g, 4.45 mmol) in 1,4-dioxane (30 mL) was stirred at 90° C. for 1 hour. The solvent was concentrated under vacuum. The residue was purified by flash chromatography on silica gel eluting with dichloromethane/methanol (20/1) to afford 2-bromo-4,5,6,8-tetrahydropyrazolo[1,5-d][1,4]diazepine-7-thione (530 mg, 2.15 mmol) as a light yellow solid. LCMS (ESI) [M+H]$^+$=246.1.

Step 2: 2-bromo-N-(2,2-diethoxyethyl)-5,8-dihydro-4H-pyrazolo[1,5-d][1,4]diazepin-7-amine

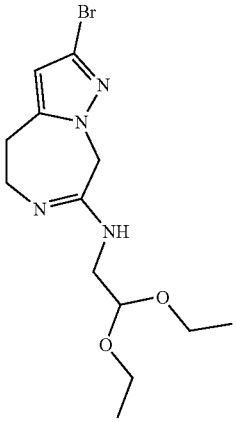 [SMILES: CCOC(CNC1=NCCc2cc(Br)nn2C1)OCC]

A solution of 2-bromo-4,5,6,8-tetrahydropyrazolo[1,5-d][1,4]diazepine-7-thione (1.2 g, 4.88 mmol), aminoacetaldehyde diethyl acetal (3.25 g, 24.38 mmol) and Ag$_2$CO$_3$ (2.69 g, 9.75 mmol) in tetrahydrofuran (100 mL) was stirred at 85° C. for 1 hour. After filtration, the filtrate was concentrated under reduced pressure. The resulting residue was purified by reverse phase chromatography (acetonitrile 0.05% TFA in water) to afford 2-bromo-N-(2,2-diethoxyethyl)-5,8-dihydro-4H-pyrazolo[1,5-d][1,4]diazepin-7-amine (900 mg, 2.6 mmol) as yellow solid. LC/MS (ESI) [M+H]$^+$=245.2.

Step 3: 8-bromo-5,6-dihydro-11H-imidazo[1,2-a]pyrazolo[1,5-d][1,4]diazepine

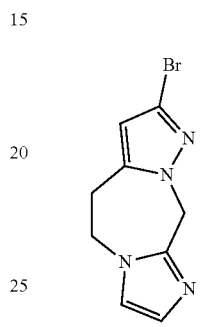

A solution of 2-bromo-N-(2,2-diethoxyethyl)-5,8-dihydro-4H-pyrazolo[1,5-d][1,4]diazepin-7-amine (425 mg, 1.23 mmol) and hydrochloric acid (0.31 mL, 1.23 mmol) in acetic acid (10 mL) was stirred at 80° C. for 1 hour. The solvent was concentrated under vacuum.

The residue was purified by reverse-phase column eluting with water (0.05% 2,2,2-trifluoroacetic acid)/acetonitrile (85/15) to afford 8-bromo-5,6-dihydro-11H-imidazo[1,2-a]pyrazolo[1,5-d][1,4]diazepine (200 mg, 0.79 mmol) as a brown oil. LCMS (ESI) [M+H]$^+$=253.1.

Step 4: tert-butyl N-[5-[3-amino-8-(tert-butoxycarbonylamino)-7-fluoro-6-isoquinolyl]-4-methyl-3-pyridyl]-N-tert-butoxycarbonyl-carbamate

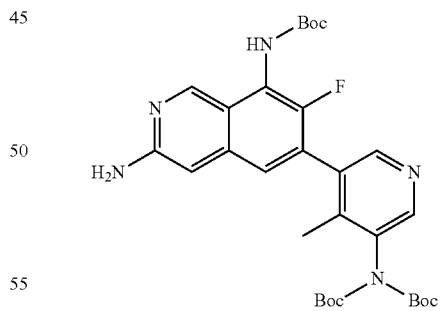

A mixture of tert-butyl N-[5-(3-amino-8-chloro-7-fluoro-6-isoquinolyl)-4-methyl-3-pyridyl]-N-tert-butoxycarbonyl-carbamate (500 mg, 0.99 mmol), tert-butyl carbamate (3489.27 mg, 29.82 mmol), tris(dibenzylideneacetone)dipalladium-chloroformadduct (205.78 mg, 0.20 mmol), Brettphos (159.85 mg, 0.30 mmol) and cesium carbonate (972.22 mg, 2.98 mmol) in 1,4-dioxane (50 mL) was stirred at 90° C. for 1 hour. The solvent was concentrated under vacuum. The residue was purified by reverse column eluting with sodium bicarbonate (10 mmol/L) in water/acetonitrile (40/60) to afford tert-butyl N-[5-[3-amino-8-(tert-butoxycarbonylamino)-7-fluoro-6-isoquinolyl]-4-methyl-3-pyridyl]-N-tert-butoxycarbonyl-carbamate (100 mg, 0.17 mmol) as a light yellow solid. LCMS (ESI) [M+H]$^+$=583.7.

Step 5: tert-butyl (tert-butoxycarbonyl)(5-(8-((tert-butoxycarbonyl)amino)-3-((5,6-dihydro-11H-imidazo[1,2-a]pyrazolo[1,5-d][1,4]diazepin-8-yl)amino)-7-fluoroisoquinolin-6-yl)-4-methylpyridin-3-yl)carbamate

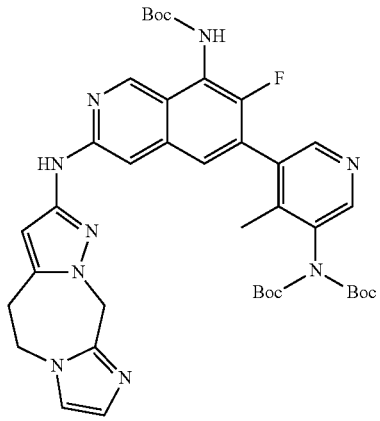 [SMILES: Cc1c(-c2cc3cc(Nc4cc5n(n4)Cc4nccn4CC5)ncc3c(NC(=O)OC(C)(C)C)c2F)cncc1N(C(=O)OC(C)(C)C)C(=O)OC(C)(C)C]

A solution of tert-butyl N-[5-[3-amino-8-(tert-butoxycarbonylamino)-7-fluoro-6-isoquinolyl]-4-methyl-3-pyridyl]-N-tert-butoxycarbonyl-carbamate (130 mg, 0.20 mmol), 8-bromo-5,6-dihydro-11H-imidazo[1,2-a]pyrazolo[1,5-d][1,4]diazepine (249.6 mg, 1.0 mmol), t-BuBretphosG3 (145.6 mg, 0.20 mmol), t-BuBretophos (108 mg, 0.20 mmol) and cesium carbonate (421.2 mg, 1.30 mmol)] in 1,4-dioxane (10 mL) at 120° C. for 1 hour. The mixture was concentrated under vacuum. The residue was purified by flash chromatography on silica gel eluting with ethyl acetate/petroleum ether (1/1) to afford tert-butyl (tert-butoxycarbonyl)(5-(8-((tert-butoxycarbonyl)amino)-3-((5,6-dihydro-11H-imidazo[1,2-a]pyrazolo[1,5-d][1,4]diazepin-8-yl)amino)-7-fluoroisoquinolin-6-yl)-4-methylpyridin-3-yl)carbamate (70 mg, 0.10 mmol) as a yellow oil. LCMS (ESI) [M+H]$^+$=755.8.

Step 6: 6-(5-amino-4-methylpyridin-3-yl)-N3-(5,6-dihydro-11H-imidazo[1,2-a]pyrazolo[1,5-d][1,4]diazepin-8-yl)-7-fluoroisoquinoline-3,8-diamine

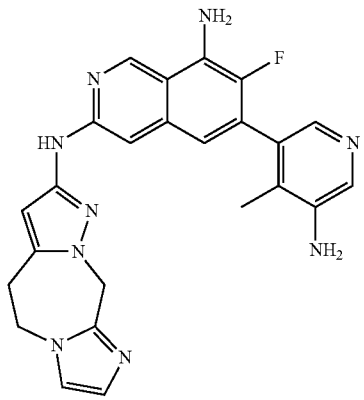 [SMILES: Cc1c(N)cncc1-c1cc2cc(Nc3cc4n(n3)Cc3nccn3CC4)ncc2c(N)c1F]

A mixture of tert-butyl (tert-butoxycarbonyl)(5-(8-((tert-butoxycarbonyl)amino)-3-((5,6-dihydro-11H-imidazo[1,2-a]pyrazolo[1,5-d][1,4]diazepin-8-yl)amino)-7-fluoroisoquinolin-6-yl)-4-methylpyridin-3-yl)carbamate (70 mg, 0.09 mmol) and 2,2,2-trifluoroacetic acid (1 mL) in dichloromethane (5 mL) was stirred at 25° C. for 3 hours. The mixture was concentrated under vacuum. The reaction mixture was adjusted to pH 7 with ammonia in methanol (7 mol/L). The residue was purified by reverse phase column eluting with water (0.05% TFA)/ACN (85/15) to afford 6-(5-amino-4-methylpyridin-3-yl)-N3-(5,6-dihydro-11H-imidazo[1,2-a]pyrazolo[1,5-d][1,4]diazepin-8-yl)-7-fluoroisoquinoline-3,8-diamine (19.2 mg, 0.038 mmol) as an orange solid. LCMS (ESI) [M+H]$^+$=456.2. $^1$HNMR (400 MHz, DMSO-d$_6$) δ 9.25 (s, 1H), 9.10 (s, 1H), 7.99 (s, 1H), 7.70 (s, 1H), 7.67 (s, 1H), 7.21 (d, J=1.2 Hz, 1H), 6.84 (d, J=1.2 Hz, 1H), 6.72 (d, J=6.1 Hz, 1H), 6.05 (s, 3H), 5.40 (s, 2H), 5.22 (s, 2H), 4.39-4.31 (m, 2H), 3.27-3.19 (m, 2H), 1.93 (s, 3H).

Example 149

2-((6-((1H-pyrrolo[2,3-c]pyridin-1-yl)methyl)-8-amino-7-fluoroisoquinolin-3-yl)amino)-6-isopropyl-5,6-dihydro-4H-pyrazolo[1,5-d][1,4]diazepin-7(8H)-one (Compound 249)

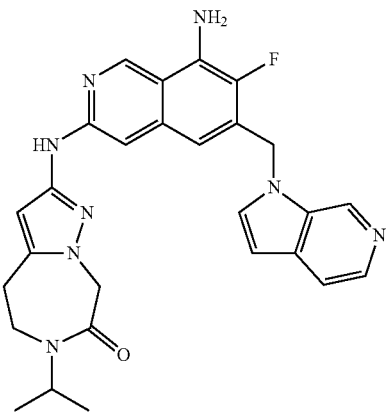 [SMILES: CC(C)N1CCc2cc(Nc3cc4cc(Cn5ccc6ccncc65)c(F)c(N)c4cn3)nn2CC1=O]

Step 1: 2-[[8-chloro-6-(chloromethyl)-7-fluoro-3-isoquinolyl]amino]-6-isopropyl-5,8-dihydro-4H-pyrazolo[1,5-d][1,4]diazepin-7-one

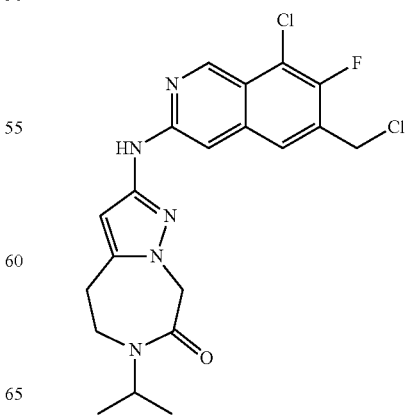

A solution of 2-[[8-chloro-7-fluoro-6-(hydroxymethyl)-3-isoquinolyl]amino]-6-isopropyl-5,8-dihydro-4H-pyrazolo[1,5-d][1,4]diazepin-7-one (50 mg, 0.12 mmol) and thionyl chloride (70.6 mg, 0.60 mmol) in dichloromethane (5 mL) was stirred at 25° C. for 1 hour. The mixture was concentrated under vacuum to afford 2-[[8-chloro-6-(chloromethyl)-7-fluoro-3-isoquinolyl]amino]-6-isopropyl-5,8-dihydro-4H-pyrazolo[1,5-d][1,4]diazepin-7-one (50 mg, 0.11 mmol) as a brown solid. LCMS (ESI) [M+H]⁺=436.

Step 2: 2-[[8-chloro-7-fluoro-6-(pyrrolo[2,3-c]pyridin-1-ylmethyl)-3-isoquinolyl]amino]-6-isopropyl-5,8-dihydro-4H-pyrazolo[1,5-d][1,4]diazepin-7-one

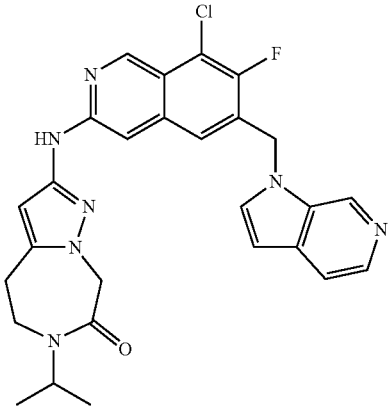

A mixture of 2-[[8-chloro-6-(chloromethyl)-7-fluoro-3-isoquinolyl]amino]-6-isopropyl-5,8-dihydro-4H-pyrazolo[1,5-d][1,4]diazepin-7-one (50 mg, 0.11 mmol), 1H-pyrrolo[2,3-c]pyridine (40.62 mg, 0.34 mmol) and cesium carbonate (186.79 mg, 0.57 mmol) in N,N-dimethylformamide (6 mL) was stirred at 25° C. for 2 hours. After filtration, the filtrate was concentrated under vacuum. The residue was purified by flash chromatography on silica gel eluting with dichloromethane/methanol (9/1) to afford 2-[[8-chloro-7-fluoro-6-(pyrrolo[2,3-c]pyridin-1-ylmethyl)-3-isoquinolyl]amino]-6-isopropyl-5,8-dihydro-4H-pyrazolo[1,5-d][1,4]diazepin-7-one (15 mg, 0.029 mmol) as a yellow solid. LCMS (ESI) [M+H]⁺=518.

Step 3: tert-butyl N-[7-fluoro-3-[(6-isopropyl-7-oxo-5,8-dihydro-4H-pyrazolo[1,5-d][1,4]diazepin-2-yl)amino]-6-(pyrrolo[2,3-c]pyridin-1-ylmethyl)-8-isoquinolyl]carbamate

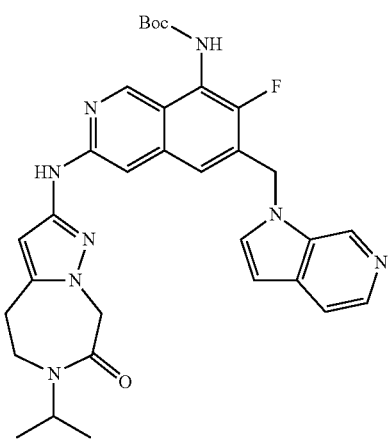 [SMILES: CC(C)N1CCc2cc(Nc3cc4cc(Cn5ccc6ccncc65)c(F)c(NC(=O)OC(C)(C)C)c4cn3)nn2CC1=O]

A mixture of 2-[[8-chloro-7-fluoro-6-(pyrrolo[2,3-c]pyridin-1-ylmethyl)-3-isoquinolyl]amino]-6-isopropyl-5,8-dihydro-4H-pyrazolo[1,5-d][1,4]diazepin-7-one (70 mg, 0.14 mmol), tert-Butyl carbamate (474.33 mg, 4.05 mmol), tris(dibenzylideneacetone)dipalladium (27.97 mg, 0.03 mmol) and Brettphos (29.03 mg, 0.05 mmol) in 1,4-dioxane (10 mL) was added cesium carbonate (176.22 mg, 0.54 mmol) at 25° C.

The resulting solution was stirred for 2 hours at 90° C. After filtration, the filtrate was concentrated under vacuum. The residue was purified by flash chromatography on silica gel eluting with dichloromethane/methanol (9/1) to afford tert-butyl N-[7-fluoro-3-[(6-isopropyl-7-oxo-5,8-dihydro-4H-pyrazolo[1,5-d][1,4]diazepin-2-yl)amino]-6-(pyrrolo[2,3-c]pyridin-1-ylmethyl)-8-isoquinolyl]carbamate (45 mg, 0.075 mmol) as a yellow solid. LCMS (ESI) [M+H]⁺=599.

Step 4: 2-((6-((1H-pyrrolo[2,3-c]pyridin-1-yl)methyl)-8-amino-7-fluoroisoquinolin-3-yl)amino)-6-isopropyl-5,6-dihydro-4H-pyrazolo[1,5-d][1,4]diazepin-7(8H)-one

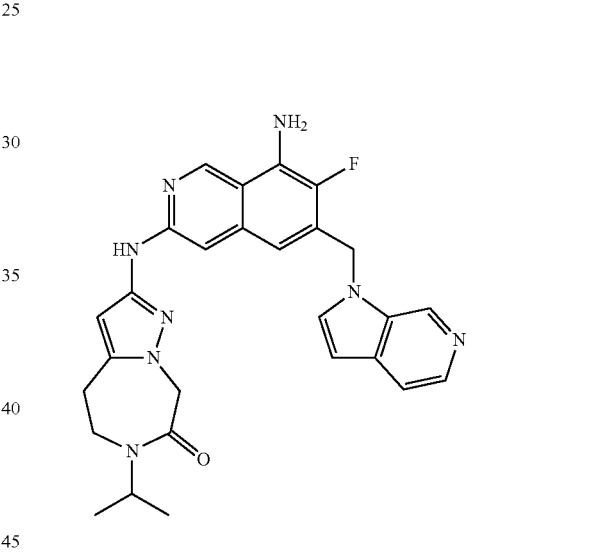

A mixture of tert-butyl N-[7-fluoro-3-[(6-isopropyl-7-oxo-5,8-dihydro-4H-pyrazolo[1,5-d][1,4]diazepin-2-yl)amino]-6-(pyrrolo[2,3-c]pyridin-1-ylmethyl)-8-isoquinolyl]carbamate (80 mg, 0.13 mmol) in dichloromethane (4 mL) and 2,2,2-trifluoroacetic acid (4 mL) was stirred at 25° C. for 2 hours. The mixture was concentrated under vacuum. The residue was purified by prep-HPLC (Atlantis HILIC OBD, 19×150 mm 5 um; water (0.1% FA): CH₃CN=5%-6% B in 7 min) to afford 2-[[8-amino-7-fluoro-6-(pyrrolo[2,3-c]pyridin-1-ylmethyl)-3-isoquinolyl]amino]-6-isopropyl-5,8-dihydro-4H-pyrazolo[1,5-d][1,4]diazepin-7-one (9.4 mg, 0.017 mmol) as a yellow solid. LCMS (ESI) [M+H]⁺=499.3; ¹HNMR (300 MHz, DMSO-d₆) δ 9.17 (s, 1H), 9.08 (s, 1H), 8.96 (s, 1H), 8.12 (d, J=5.4 Hz, 1H), 7.72 (d, J=3.0 Hz, 1H), 7.56 (s, 1H), 7.54 (d, J=1.0 Hz, 1H), 6.74 (d, J=6.1 Hz, 1H), 6.57 (d, J=3.1 Hz, 1H), 6.06 (s, 2H), 5.95 (s, 1H), 5.64 (s, 2H), 4.96 (s, 2H), 4.60 (t, J=6.8 Hz, 1H), 3.78 (s, 2H), 2.98 (s, 2H), 1.13 (d, J=6.8 Hz, 6H).

Example 150

2-((8-amino-7-fluoro-6-(4-methylpyridin-3-yl)isoquinolin-3-yl)amino)-7-methyl-6,7-dihydro-5H-imidazo[1,2-d][1,4]diazepin-8(9H)-one (Compound 250)

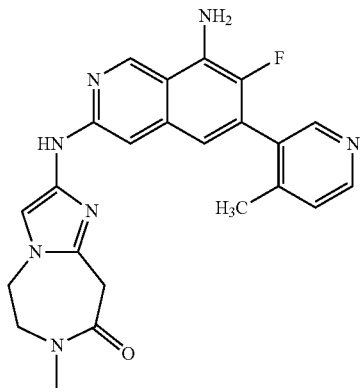 [SMILES: Cc1ccncc1-c1cc2cc(Nc3cn4c(n3)CC(=O)N(C)CC4)ncc2c(N)c1F]

Step 1: 2-[tert-butoxycarbonyl(methyl)amino]ethyl methanesulfonate

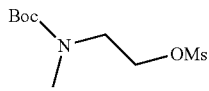

To a solution of tert-butyl (2-hydroxyethyl)(methyl)carbamate (1.0 g, 5.71 mmol) and triethylamine (1.15 g, 11.41 mmol) in dichloromethane (20 mL) was added dropwise methanesulfonyl chloride (975.86 mg, 8.56 mmol). The mixture was stirred at 0° C. for 1 hour. The resulting solution was washed with water and the organic phase was dried with anhydrous sodium sulfate. After filtration, the filtrate was concentrated under vacuum to afford 2-[tert-butoxycarbonyl(methyl)amino]ethyl methanesulfonate (1.29 g, 5.08 mmol) as a colorless oil. LCMS (ESI) [M+H]$^+$=254.

Step 2: tert-butyl N-[2-(4-bromo-2-methyl-imidazol-1-yl)ethyl]-N-methyl-carbamate

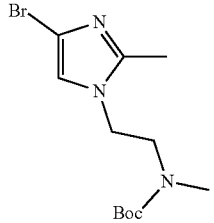 [SMILES: Cc1nc(Br)cn1CCN(C)C(=O)OC(C)(C)C]

A solution of 5-bromo-2-methyl-1H-imidazole (5.0 g, 31.06 mmol) and sodium hydride (1.86 g, 60% purity, 46.58 mmol) in N,N-dimethylformamide (100 mL) was stirred for 30 minutes at 0° C. 2-[tert-Butoxycarbonyl(methyl)amino]ethyl methanesulfonate (8.0 g, 31.58 mmol) was added and stirred at room temperature for 12 hours. The reaction was quenched with water, extracted with ethyl acetate and dried with anhydrous sodium sulfate. After filtration, the filtrate was concentrated under vacuum. The residue was purified by reverse phase chromatography (acetonitrile 0-40/0.1% NH$_3$H$_2$O in water) to afford tert-butyl N-[2-(4-bromo-2-methyl-imidazol-1-yl)ethyl]-N-methyl-carbamate (6 g, 18.85 mmol) as a colorless oil. LCMS (ESI) [M+H]$^+$=318.

Step 3: methyl 2-[4-bromo-1-[2-[tert-butoxycarbonyl(methyl)amino]ethyl]imidazol-2-yl]acetate

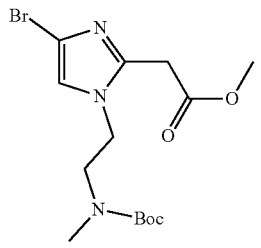 [SMILES: COC(=O)Cc1nc(Br)cn1CCN(C)C(=O)OC(C)(C)C]

To a solution of tert-butyl N-[2-(4-bromo-2-methyl-imidazol-1-yl)ethyl]-N-methyl-carbamate (2.0 g, 6.29 mmol) and dimethyl carbonate (2.83 g, 31.43 mmol) in tetrahydrofuran (100 mL) was added lithium diisopropylamide (7.54 mL, 15.08 mmol, 2 mol/L) at −70° C. The resulting solution was stirred for 2 hours at −70° C. to −30° C. The reaction was quenched with water. The resulting mixture was concentrated under vacuum. The resulting residue was purified by reverse phase chromatography (acetonitrile 0-40/0.1% NH3 in water) to afford methyl 2-[4-bromo-1-[2-[tert-butoxycarbonyl(methyl)amino]ethyl]imidazol-2-yl]acetate (400 mg, 1.06 mmol) as a colorless solid. LCMS (ESI) [M+H]$^+$=376.

Step 4: methyl 2-[4-bromo-1-[2-(methylamino)ethyl]imidazol-2-yl]acetate

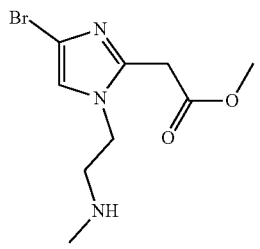

A solution of methyl 2-[4-bromo-1-[2-[tert-butoxycarbonyl(methyl)amino]ethyl]imidazol-2-yl]acetate (400 mg, 1.06 mmol) and 2,2,2-trifluoroacetic acid (1 mL) in dichloromethane (3 mL) was stirred at 25° C. for 2 hours. The solvent was concentrated under vacuum to afford methyl 2-[4-bromo-1-[2-(methylamino)ethyl]imidazol-2-yl]acetate (250 mg, 0.91 mmol) as a colorless solid. LCMS (ESI) [M+H]$^+$=276.

Step 5: 2-bromo-7-methyl-6,9-dihydro-5H-imidazo[1,2-d][1,4]diazepin-8-one

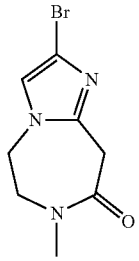

A solution of methyl 2-[4-bromo-1-[2-(methylamino)ethyl]imidazol-2-yl]acetate (250 mg, 0.91 mmol) and triethylamine (914.42 mg, 9.05 mmol) in methanol (10 mL) was stirred at 25° C. for 12 hours. The solvent was concentrated under vacuum. The residue was purified by reverse phase chromatography (acetonitrile 0-40/0.1% NH3 in water) to afford 2-bromo-7-methyl-6,9-dihydro-5H-imidazo[1,2-d][1,4]diazepin-8-one (160 mg, 0.65 mmol) as a colorless oil. LCMS (ESI) [M+H]$^+$=244.

Step 6: 2-[[8-chloro-7-fluoro-6-(4-methyl-3-pyridyl)-3-isoquinolyl]amino]-7-methyl-6,9-dihydro-5H-imidazo[1,2-d][1,4]diazepin-8-one

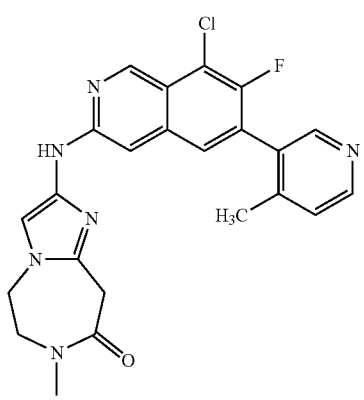 [SMILES: Cc1ccncc1-c1cc2cc(Nc3cn4c(n3)CC(=O)N(C)CC4)ncc2c(Cl)c1F]

A mixture of 2-bromo-7-methyl-6,9-dihydro-5H-imidazo[1,2-d][1,4]diazepin-8-one (50 mg, 0.20 mmol), 8-chloro-7-fluoro-6-(4-methyl-3-pyridyl)isoquinolin-3-amine (47.15 mg, 0.16 mmol), t-BuBrettPhosG3 (69.97 mg, 0.08 mmol), t-BuBrettPhos (49.67 mg, 0.10 mmol) and cesium carbonate (200.34 mg, 0.61 mmol) in 1,4-dioxane (6 mL) was stirred at 120° C. for 3 hours. After filtration, the filtrate was concentrated under vacuum. The residue was purified by reverse phase chromatography (acetonitrile 0-40/0.1% NH4CO3 in water) to afford 2-[[8-chloro-7-fluoro-6-(4-methyl-3-pyridyl)-3-isoquinolyl]amino]-7-methyl-6,9-dihydro-5H-imidazo[1,2-d][1,4]diazepin-8-one (5.7 mg, 0.013 mmol) as a yellow solid. LCMS (ESI) [M+H]$^+$=451.

Step 7: tert-butyl(7-fluoro-3-((7-methyl-8-oxo-6,7,8,9-tetrahydro-5H-imidazo[1,2-d][1,4]diazepin-2-yl)amino)-6-(4-methylpyridin-3-yl)isoquinolin-8-yl)carbamate

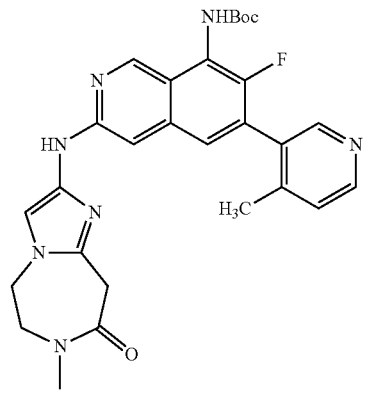 [SMILES: Cc1ccncc1-c1cc2cc(Nc3cn4c(n3)CC(=O)N(C)CC4)ncc2c(NC(=O)OC(C)(C)C)c1F]

To a mixture of 2-[[8-chloro-7-fluoro-6-(4-methyl-3-pyridyl)-3-isoquinolyl]amino]-7-methyl-6,9-dihydro-5H-imidazo[1,2-d][1,4]diazepin-8-one (230 mg, 0.51 mmol), tert-butyl carbamate (1.79 g, 15.3 mmol), tris(dibenzylideneacetone)dipalladium (105.59 mg, 0.10 mmol) and Brettphos (109.57 mg, 0.20 mmol) in 1,4-dioxane (15 mL) was added cesium carbonate (665.16 mg, 2.04 mmol) at 25° C. The reaction was stirred for 1 hour at 90° C. After filtration, the filtrate was concentrated under vacuum. The residue was purified by flash chromatography on silica gel eluting with dichloromethane/methanol (9/1) to afford tert-butyl N-[7-fluoro-3-[(7-methyl-8-oxo-6,9-dihydro-5H-imidazo[1,2-d][1,4]diazepin-2-yl)amino]-6-(4-methyl-3-pyridyl)-8-isoquinolyl]carbamate (70 mg, 0.13 mmol) as a yellow solid. LCMS (ESI) [M+H]$^+$=532.

Step 8: 2-[[8-amino-7-fluoro-6-(4-methyl-3-pyridyl)-3-isoquinolyl]amino]-7-methyl-6,9-dihydro-5H-imidazo[1,2-d][1,4]diazepin-8-one

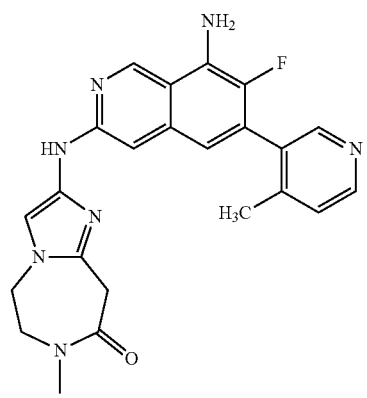 [SMILES: Cc1ccncc1-c1cc2cc(Nc3cn4c(n3)CC(=O)N(C)CC4)ncc2c(N)c1F]

A solution of tert-butyl N-[7-fluoro-3-[(7-methyl-8-oxo-6,9-dihydro-5H-imidazo[1,2-d][1,4]diazepin-2-yl)amino]-6-(4-methyl-3-pyridyl)-8-isoquinolyl]carbamate (65 mg, 0.12 mmol) in dichloromethane (5 mL) and 2,2,2-trifluoroacetic acid (5 mL) was stirred at 25° C. for 2 hours. The solvent was concentrated under vacuum. The residue was purified by prep-HPLC (Atlantis HILIC OBD, 19×150 mm 5um; water (0.1% FA): CH₃CN=7%-10% B in 7 min) to afford 2-[[8-amino-7-fluoro-6-(4-methyl-3-pyridyl)-3-isoquinolyl]amino]-7-methyl-6,9-dihydro-5H-imidazo[1,2-d][1,4]diazepin-8-one (2 mg, 0.0042 mmol) as a red solid. LCMS (ESI) [M+H]⁺=432.2; ¹H NMR (400 MHz, DMSO-d₆) δ 9.26 (s, 1H), 8.87 (s, 1H), 8.49 (d, J=5.0 Hz, 1H), 8.41 (s, 1H), 7.38 (d, J=5.1 Hz, 1H), 7.07 (d, J=19.2 Hz, 2H), 6.70 (d, J=6.1 Hz, 1H), 6.10 (s, 2H), 4.11 (d, J=5.8 Hz, 2H), 3.99 (d, J=5.4 Hz, 2H), 3.89 (s, 2H), 2.96 (s, 3H), 2.21 (s, 3H).

Example 151

2-((8-amino-6-(5-amino-4-methylpyridin-3-yl)-7-fluoroisoquinolin-3-yl)amino)-4,5-dihydro-7H-pyrazolo[1,5-c][1,3]thiazine 6,6-dioxide (Compound 252)

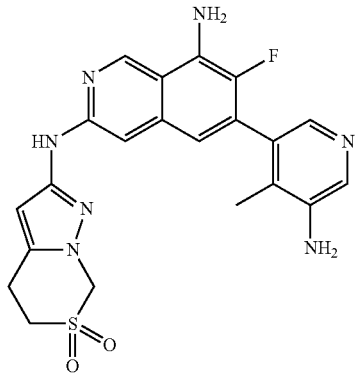 [SMILES: Cc1c(N)cncc1-c1cc2cc(Nc3cc4n(n3)CS(=O)(=O)CC4)ncc2c(N)c1F]

Step 1: ethyl 2-(chloromethylsulfanyl)acetate

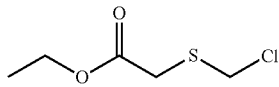

To a solution of sodium hydride (5.83 g, 60% purity, 145.63 mmol) in tetrahydrofuran (200 mL) was added ethyl 2-mercaptoacetate (17.5 g, 145.63 mmol) at 0° C. The resulting solution was stirred for 30 minutes at 0° C. Bromochloromethane (94.21 g, 728.14 mmol) was added and stirred at 0° C. for 2 hours. After filtration, the filtrate was concentrated under vacuum. The crude product was distilled in vacuo to afford ethyl 2-(chloromethylsulfanyl)acetate (14 g, 83.02 mmol) as a colorless oil. GCMS=168.

Step 2: methyl 5-bromo-2-[(2-ethoxy-2-oxo-ethyl)sulfanylmethyl]pyrazole-3-carboxylate

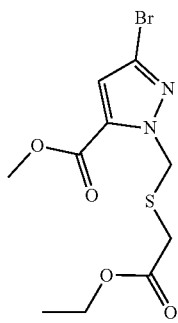 [SMILES: CCOC(=O)CSCn1nc(Br)cc1C(=O)OC]

To a mixture of methyl 5-bromo-1H-pyrazole-3-carboxylate (1.5 g, 7.32 mmol), ethyl 2-(chloromethylsulfanyl)acetate (1.36 g, 8.05 mmol) and potassium carbonate (2.02 g, 14.63 mmol) in N,N-dimethylformamide (30 mL) was added tetrabutylammonium iodide (134.99 mg, 0.37 mmol) at 25° C. The resulting solution was stirred for 4 hours at 25° C. After filtration, the filtrate was concentrated under vacuum. The residue was purified by flash chromatography on silica gel eluting with petroleum ether/ethyl acetate (5/1) to afford methyl 5-bromo-2-[(2-ethoxy-2-oxo-ethyl)sulfanylmethyl]pyrazole-3-carboxylate (1.8 g, 5.34 mmol) as a yellow oil. LCMS (ESI) [M+H]⁺=337.

Step 3: methyl 2-bromo-4-oxo-7H-pyrazolo[1,5-c][1,3]thiazine-5-carboxylate

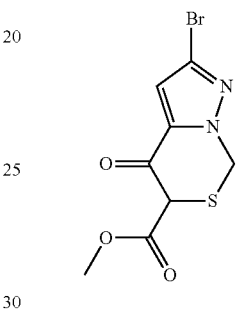

A solution of methyl 5-bromo-2-[(2-ethoxy-2-oxo-ethyl)sulfanylmethyl]pyrazole-3-carboxylate (500 mg, 1.48 mmol) and sodium methylate (0.55 mL, 2.97 mmol) in methanol (10 mL) was stirred at 25° C. for 4 hours. The reaction mixture was adjusted to pH 8 with acetic acid. The solvent was concentrated under vacuum. The residue was purified by flash chromatography on silica gel eluting with petroleum ether/ethyl acetate (5/1) to afford methyl 2-bromo-4-oxo-7H-pyrazolo[1,5-c][1,3]thiazine-5-carboxylate (270 mg, 0.93 mmol) as a yellow solid. LCMS (ESI) [M+H]⁺=291.

Step 4: 2-bromo-7H-pyrazolo[1,5-c][1,3]thiazin-4-one

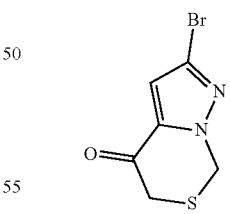

A solution of methyl 2-bromo-4-oxo-7H-pyrazolo[1,5-c][1,3]thiazine-5-carboxylate (1.1 g, 3.78 mmol) and concentrated sulfuric acid (49.37 g, 75.57 mmol) in 1,4-dioxane (15 mL) was stirred at 100° C. for 12 hours. The reaction mixture was adjusted to pH 6 with sodium hydroxide (10%). The resulting solution was extracted with ethyl acetate, dried with anhydrous sodium sulfate. After filtration, the filtrate was concentrated under vacuum to afford 2-bromo-7H-pyrazolo[1,5-c][1,3]thiazin-4-one (900 mg, 2.90 mmol) as a yellow solid. LCMS (ESI) [M+H]⁺=233.

Step 5: N—[(Z)-(2-bromo-7H-pyrazolo[1,5-c][1,3]thiazin-4-ylidene)amino]-4-methyl-benzenesulfonamide

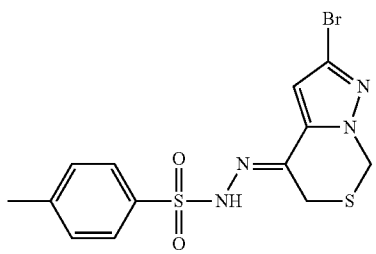 [SMILES: Cc1ccc(S(=O)(=O)N/N=C2\CSCn3nc(Br)cc32)cc1]

A solution of 2-bromo-7H-pyrazolo[1,5-c][1,3]thiazin-4-one (50 mg, 0.21 mmol) and 4-methylbenzenesulfonohydrazide (39.95 mg, 0.21 mmol) in methanol (3 mL) was stirred at 25° C. for 12 hours. The solvent was concentrated under vacuum. The solid was washed with petroleum ether (10 mL) to afford N—[(Z)-(2-bromo-7H-pyrazolo[1,5-c][1,3]thiazin-4-ylidene)amino]-4-methyl-benzenesulfonamide (80 mg, 0.20 mmol) as a yellow solid. LCMS (ESI) $[M+H]^+$=401.

Step 6: 2-bromo-5,7-dihydro-4H-pyrazolo[1,5-c][1,3]thiazine

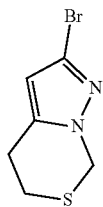

To a solution of N—[(Z)-(2-bromo-7H-pyrazolo[1,5-c][1,3]thiazin-4-ylidene)amino]-4-methyl-benzenesulfonamide (80 mg, 0.20 mmol) in dichloromethane (10 mL) was added diisobutylaluminium hydride (1 mL, 1.0 mmol, 1 mol/L) at 0° C. The resulting solution was stirred 1 hour at 0° C. The reaction was quenched with water and then extracted with ethyl acetate. The organic layers were combined, dried over anhydrous sodium sulfate. After filtration, the filtrate was concentrated under vacuum. The residue was purified by reverse phase chromatography (acetonitrile 0-40/0.1% sodium bicarbonate in water) to afford 2-bromo-5,7-dihydro-4H-pyrazolo[1,5-c][1,3]thiazine (20 mg, 0.091 mmol) as a white solid. LCMS (ESI) $[M+H]^+$=219.

Step 7: 2-bromo-5,7-dihydro-4H-pyrazolo[1,5-c][1,3]thiazine 6,6-dioxide

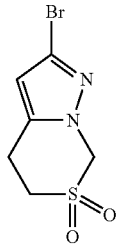

A solution of 2-bromo-5,7-dihydro-4H-pyrazolo[1,5-c][1,3]thiazine (130 mg, 0.59 mmol) and 3-chloroperoxybenzoic acid (612.32 mg, 3.56 mmol) in dichloromethane (10 mL) was stirred at 25° C. for 3 hours. The reaction was quenched with sodium sulfite and sodium bicarbonate solution. The resulting solution was extracted with ethyl acetate, dried with anhydrous sodium sulfate. After filtration, the filtrate was concentrated under vacuum. The resulting residue was purified by reverse phase chromatography (acetonitrile 0-40/0.1% HCl in water) to afford 2-bromo-5,7-dihydro-4H-pyrazolo[1,5-c][1,3]thiazine 6,6-dioxide (70 mg, 0.28 mmol) as a white solid. LCMS (ESI) $[M+H]^+$=251.

Step 8: tert-butyl N-tert-butoxycarbonyl-N-[5-[8-chloro-3-[(6,6-dioxo-5,7-dihydro-4H-pyrazolo[1,5-c][1,3]thiazin-2-yl)amino]-7-fluoro-6-isoquinolyl]-4-methyl-3-pyridyl]carbamate

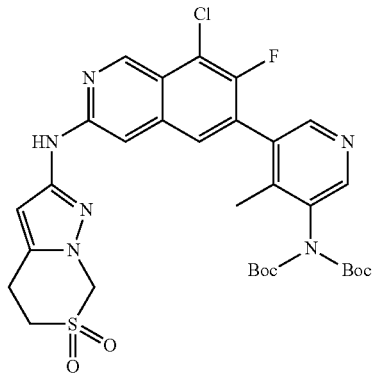 [SMILES: Cc1c(-c2cc3cc(Nc4cc5n(n4)CS(=O)(=O)CC5)ncc3c(Cl)c2F)cncc1N(C(=O)OC(C)(C)C)C(=O)OC(C)(C)C]

To a mixture of tert-butyl N-[5-(3-amino-8-chloro-7-fluoro-6-isoquinolyl)-4-methyl-3-pyridyl]-N-tert-butoxycarbonyl-carbamate (250 mg, 0.50 mmol), 2-bromo-5,7-dihydro-4H-pyrazolo[1,5-c][1,3]thiazine 6,6-dioxide (149.77 mg, 0.60 mmol), tris(dibenzylideneacetone)dipalladium-chloroformadduct (102.89 mg, 0.10 mmol) and 4,5-bis(diphenylphosphino)-9,9-dimethylxanthene (115.12 mg, 0.20 mmol) in 1,4-dioxane (10 mL) was added cesium carbonate (486.11 mg, 1.49 mmol) at 25° C. The resulting solution was stirred for 2 hours at 100° C. After filtration, the filtrate was concentrated under vacuum. The residue was purified by flash chromatography on silica gel eluting with petroleum ether/ethyl acetate (2/3) to afford tert-butyl N-tert-butoxycarbonyl-N-[5-[8-chloro-3-[(6,6-dioxo-5,7-dihydro-4H-pyrazolo[1,5-c][1,3]thiazin-2-yl)amino]-7-fluoro-6-isoquinolyl]-4-methyl-3-pyridyl]carbamate (70 mg, 0.10 mmol) as a yellow solid. LCMS (ESI) $[M+H]^+$=673.

Step 9: tert-butyl N-tert-butoxycarbonyl-N-[5-[8-(tert-butoxycarbonylamino)-3-[(6,6-dioxo-5,7-dihydro-4H-pyrazolo[1,5-c][1,3]thiazin-2-yl)amino]-7-fluoro-6-isoquinolyl]-4-methyl-3-pyridyl]carbamate

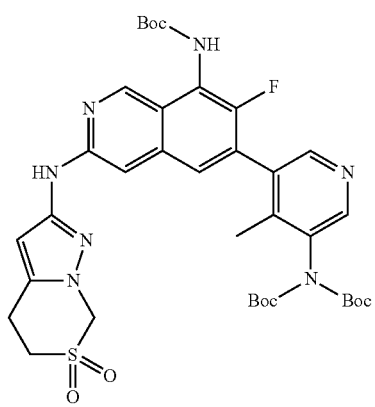 [SMILES: Cc1c(-c2cc3cc(Nc4cc5n(n4)CS(=O)(=O)CC5)ncc3c(NC(=O)OC(C)(C)C)c2F)cncc1N(C(=O)OC(C)(C)C)C(=O)OC(C)(C)C]

To a mixture of tert-butyl N-tert-butoxycarbonyl-N-[5-[8-chloro-3-[(6,6-dioxo-5,7-dihydro-4H-pyrazolo[1,5-c][1,3]thiazin-2-yl)amino]-7-fluoro-6-isoquinolyl]-4-methyl-3-pyridyl]carbamate (65 mg, 0.10 mmol), tert-Butyl carbamate (339.36 mg, 2.90 mmol), tris(dibenzylideneacetone)dipalladium-chloroformadduct (19.99 mg, 0.020 mmol) and Brettphos (20.74 mg, 0.040 mmol) in 1,4-dioxane (10 mL) was added cesium carbonate (125.92 mg, 0.39 mmol) at 25° C. The resulting solution was stirred for 4 hours at 90° C. After filtration, the filtrate was concentrated under vacuum. The residue was purified by flash chromatography on silica gel eluting with dichloromethane/methanol (10/1) to afford tert-butyl N-tert-butoxycarbonyl-N-[5-[8-(tert-butoxycarbonylamino)-3-[(6,6-dioxo-5,7-dihydro-4H-pyrazolo[1,5-c][1,3]thiazin-2-yl)amino]-7-fluoro-6-isoquinolyl]-4-methyl-3-pyridyl]carbamate (60 mg, 0.080 mmol) as a yellow solid. LCMS (ESI) [M+H]⁺=754.

Step 10: 6-(5-amino-4-methyl-3-pyridyl)-N3-(6,6-dioxo-5,7-dihydro-4H-pyrazolo[1,5-c][1,3]thiazin-2-yl)-7-fluoro-isoquinoline-3,8-diamine

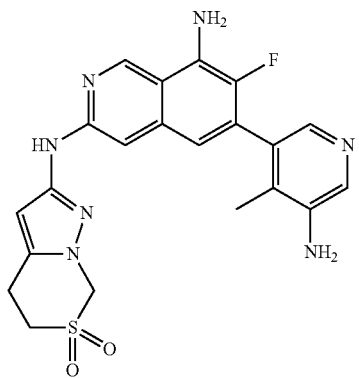 [SMILES: Cc1c(N)cncc1-c1cc2cc(Nc3cc4n(n3)CS(=O)(=O)CC4)ncc2c(N)c1F]

A solution of tert-butyl N-tert-butoxycarbonyl-N-[5-[8-(tert-butoxymethylamino)-3-[(6,6-dioxo-5,7-dihydro-4H-pyrazolo[1,5-c][1,3]thiazin-2-yl)amino]-7-fluoro-6-isoquinolyl]-4-methyl-3-pyridyl]carbamate (53.98 mg, 0.070 mmol) in dichloromethane (2 mL) and 2,2,2-trifluoroacetic acid (2 mL) was stirred at 25° C. for 2 hours. The solvent was concentrated under vacuum. The crude product was purified by prep-HPLC (Atlantis HILIC OBD, 19×150 mm Sum; water (0.1% FA): CH₃CN=3%-15% B in 7 min) to afford 6-(5-amino-4-methyl-3-pyridyl)-N3-(6,6-dioxo-5,7-dihydro-4H-pyrazolo[1,5-c][1,3]thiazin-2-yl)-7-fluoro-isoquinoline-3,8-diamine (5.5 mg, 0.011 mmol) as a yellow solid. LCMS (ESI) [M+H]⁺=454.2; ¹HNMR (300 MHz, DMSO-d₆) δ 9.33 (s, 1H), 9.30 (s, 1H), 8.00 (s, 1H), 7.87 (s, 1H), 7.71 (s, 1H), 6.70 (d, J=6.0 Hz, 1H), 6.18 (s, 2H), 6.08 (s, 1H), 5.82 (s, 2H), 5.43 (s, 2H), 3.58 (t, J=6.6 Hz, 2H), 3.27 (t, J=6.6 Hz, 2H), 2.00 (d, J=1.5 Hz, 3H).

Example 152

2-((8-amino-6-cyclopropyl-7-fluoroisoquinolin-3-yl)amino)-6-isopropyl-5,6-dihydro-4H-pyrazolo[1,5-d][1,4]diazepin-7(8H)-one (Compound 253)

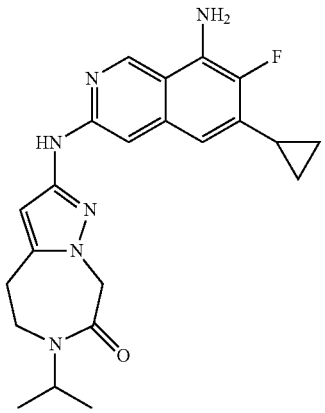 [SMILES: CC(C)N1CCc2cc(Nc3cc4cc(C5CC5)c(F)c(N)c4cn3)nn2CC1=O]

Step 1: tert-butyl 6-cyclopropyl-7-fluoro-3-(6-isopropyl-7-oxo-5,6,7,8-tetrahydro-4H-pyrazolo[1,5-g][1,4]diazepin-2-ylamino)isoquinolin-8-ylcarbamate

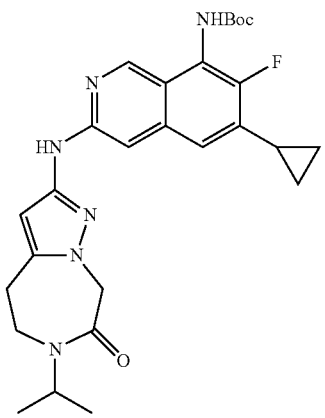 [SMILES: CC(C)N1CCc2cc(Nc3cc4cc(C5CC5)c(F)c(NC(=O)OC(C)(C)C)c4cn3)nn2CC1=O]

To a mixture of 8-(tert-butoxycarbonylamino)-7-fluoro-3-(6-isopropyl-7-oxo-5,6,7,8-tetrahydro-4H-pyrazolo[1,5-g][1,4]diazepin-2-ylamino)isoquinolin-6-yl trifluoromethanesulfonate (150 mg, 0.24 mmol), cyclopropylboronic acid (41.88 mg, 0.49 mmol) and tetrakis(triphenylphosphine)palladium (56.20 mg, 0.049 mmol) in 1,4-dioxane (5 mL) was added potassium carbonate (84.01 mg, 0.61 mmol) at 25° C. The resulting solution was stirred for 3 hours at 100° C. After filtration, the filtrate was concentrated under reduced pressure. The residue was purified by flash chromatography on silica gel eluting with dichloromethane/methanol (9/1) to afford tert-butyl 6-cyclopropyl-7-fluoro-3-(6-isopropyl-7-oxo-5,6,7,8-tetrahydro-4H-pyrazolo[1,5-g][1,4]diazepin-2-ylamino)isoquinolin-8-ylcarbamate (100 mg, 0.20 mmol) as a yellow solid. LCMS (ESI) [M+H]⁺=509.

Step 2: 2-[(8-amino-6-cyclopropyl-7-fluoro-3-isoquinolyl)amino]-6-isopropyl-5,8-dihydro-4H-pyrazolo[1,5-d][1,4]diazepin-7-one

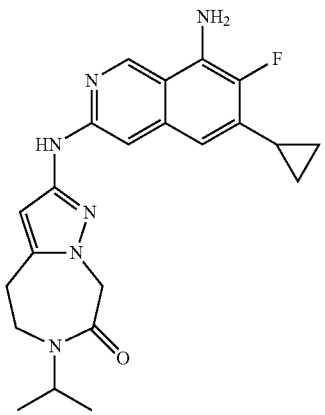 [SMILES: CC(C)N1CCc2cc(Nc3cc4cc(C5CC5)c(F)c(N)c4cn3)nn2CC1=O]

A solution of tert-butyl N-[6-cyclopropyl-7-fluoro-3-[(6-isopropyl-7-oxo-5,8-dihydro-4H-pyrazolo[1,5-d][1,4]diazepin-2-yl)amino]-8-isoquinolyl]carbamate (70 mg, 0.14 mmol) in 2,2,2-trifluoroacetic acid (4 mL) was stirred at 25° C. for 2 hours. The solvent was concentrated under vacuum. The crude product was purified by prep-HPLC (Atlantis HILIC OBD, 19×150 mm 5 um; water (10 mmol/L sodium bicarbonate): $CH_3CN$=33%-50% B in 10 min) to afford 2-[(8-amino-6-cyclopropyl-7-fluoro-3-isoquinolyl)amino]-6-isopropyl-5,8-dihydro-4H-pyrazolo[1,5-d][1,4]diazepin-7-one (8.4 mg, 0.021 mmol) as ared solid. LCMS (ESI) [M+H]$^+$=409.2; $^1$HNMR (300 MHz, DMSO-$d_6$) δ 9.12 (s, 1H), 7.47 (s, 1H), 6.48 (d, J=6.3 Hz, 1H), 5.97 (s, 1H), 4.95 (s, 2H), 4.64-4.53 (m, 1H), 3.76 (t, J=6.0 Hz, 2H), 3.00 (t, J=6.0 Hz, 2H), 2.13-2.09 (m, 1H), 1.14 (d, J=6.9 Hz, 6H), 1.06-0.96 (m, 2H), 0.84-0.82 (m, 2H).

Example 153 and Example 154

2-((8-amino-7-fluoroisoquinolin-3-yl)amino)-6-isopropyl-5,6-dihydro-4H-pyrazolo[1,5-d][1,4]diazepin-7(8H)-one (Compound 254) and 2-((8-amino-7-fluoro-6-(2-isopropoxy-4-methylpyrimidin-5-yl)isoquinolin-3-yl)amino)-6-isopropyl-5,6-dihydro-4H-pyrazolo[1,5-d][1,4]diazepin-7(8H)-one (Compound 255)

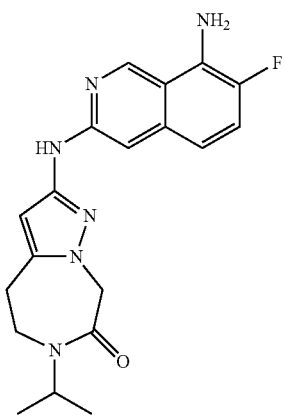

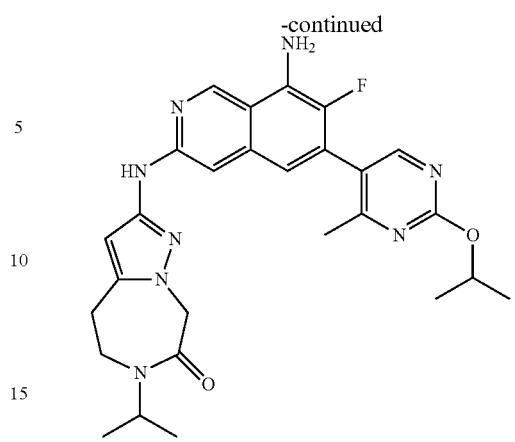

Step 1: 5-bromo-2-isopropoxy-4-methylpyrimidine

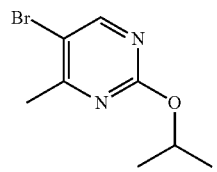

Sodium hydride (550 mg, 60% purity, 13.75 mmol) was added batchwise into a solution of 2-propanol (1.75 g, 29.12 mmol) in tetrahydrofuran (50 mL) at 0° C. The resulting solution was stirred for 30 minutes at room temperature. 5-Bromo-2-chloro-4-methylpyrimidine (1.0 g, 4.82 mmol) was added at 0° C. The resulting solution was stirred for 16 hours at room temperature. The mixture was diluted with brine. The resulting solution was extracted with ethyl acetate, dried with anhydrous sodium sulfate. After filtration, the filtrate was concentrated under vacuum. The residue was purified by flash chromatography on silica gel eluting with petroleum ether/dichloromethane (2/1) to afford 5-bromo-2-isopropoxy-4-methyl-pyrimidine (350 mg, 1.51 mmol) as light yellow oil. LCMS (ESI) [M+H]$^+$=231.

Step 2: 2-isopropoxy-4-methyl-5-(4,4,5,5-tetramethyl-1,3,2-dioxaborolan-2-yl)pyrimidine

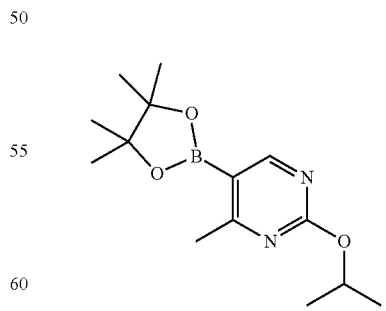

A mixture of bis(pinacolato)diboron (2.043 g, 8.05 mmol), 5-bromo-2-isopropoxy-4-methyl-pyrimidine (310 mg, 1.34 mmol), potassium acetate (394.39 mg, 4.02 mmol) and [1,1'-bis(diphenylphosphino)ferrocene]dichloropalladium(II) (98.2 mg, 0.13 mmol) in 1,4-dioxane (50 mL) was stirred at 80° C. for 15 hours. The mixture was concentrated under vacuum. The residue was purified by flash chromatography on silica gel eluting with petroleum ether/dichloromethane (3/7) to afford 2-isopropoxy-4-methyl-5-(4,4,5,5-tetramethyl-1,3,2-dioxaborolan-2-yl)pyrimidine (350 mg, 1.26 mmol) as a colorless oil. LCMS (ESI) [M+H]⁺=279.

Step 3: tert-butyl (7-fluoro-6-(2-isopropoxy-4-methylpyrimidin-5-yl)-3-((6-isopropyl-7-oxo-5,6,7,8-tetrahydro-4H-pyrazolo[1,5-d][1,4]diazepin-2-yl)amino)isoquinolin-8-yl)carbamate and tert-butyl (7-fluoro-3-((6-isopropyl-7-oxo-5,6,7,8-tetrahydro-4H-pyrazolo[1,5-d][1,4]diazepin-2-yl)amino)isoquinolin-8-yl)carbamate

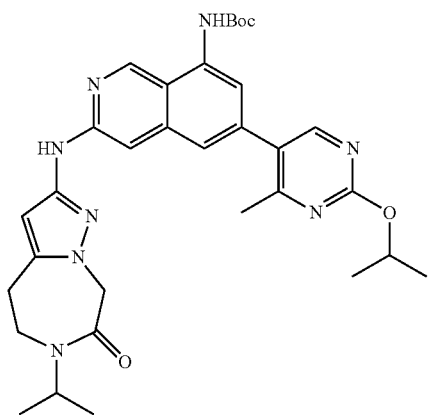

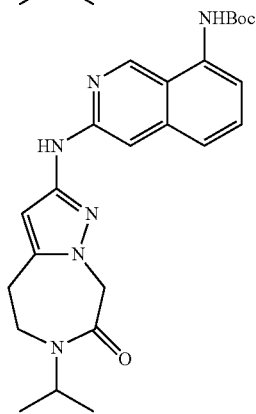

A solution of [8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]trifluoromethanesulfonate (150 mg, 0.24 mmol), 2-isopropoxy-4-methyl-5-(4,4,5,5-tetramethyl-1,3,2-dioxaborolan-2-yl)pyrimidine (101.5 mg, 0.36 mmol), terakis(triphenylphosphine)palladium (56.2 mg, 0.05 mmol) and potassium carbonate (100.72 mg, 0.73 mmol) in 1,4-dioxane (10 mL) and water (1 mL) was stirred at 90° C. for 2 hours. The residue was purified by flash chromatography on silica gel eluting with dichloromethane/methanol (20/1) to afford tert-butyl N-[7-fluoro-6-(2-isopropoxy-4-methyl-pyrimidin-5-yl)-3-[(6-isopropyl-7-oxo-5,8-dihydro-4H-pyrazolo[1,5-d][1,4]diazepin-2-yl)amino]-8-isoquinolyl]carbamate (35 mg, 0.057 mmol) as a yellow solid. LCMS (ESI) [M+H]⁺=619. And tert-butyl (7-fluoro-3-((6-isopropyl-7-oxo-5,6,7,8-tetrahydro-4H-pyrazolo[1,5-d][1,4]diazepin-2-yl)amino)isoquinolin-8-yl)carbamate (20 mg, 0.042 mmol) as a yellow solid. LCMS (ESI) [M+H]⁺=469.

Step 4: 2-((8-amino-7-fluoro-6-(2-isopropoxy-4-methylpyrimidin-5-yl)isoquinolin-3-yl)amino)-6-isopropyl-5,6-dihydro-4H-pyrazolo[1,5-d][1,4]diazepin-7(8H)-one (Compound 255)

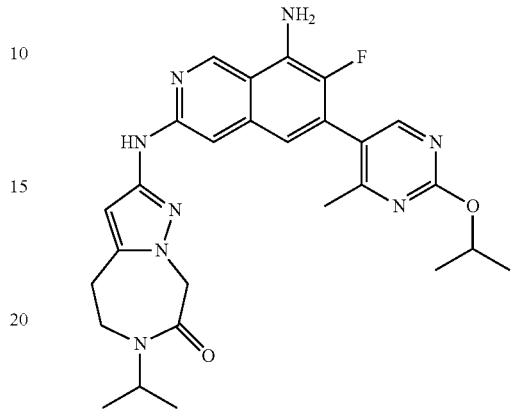

A solution of tert-butyl N-[7-fluoro-6-(2-isopropoxy-4-methyl-pyrimidin-5-yl)-3-[(6-isopropyl-7-oxo-5,8-dihydro-4H-pyrazolo[1,5-d][1,4]diazepin-2-yl)amino]-8-isoquinolyl]carbamate (30 mg, 0.05 mmol) and TFA (5 mL) in dichloromethane (1 mL) was stirred at 25° C. for 1 hour. The mixture was concentrated under vacuum. The reaction was adjusted to pH 10 with ammonia in methanol (7 mol/L). The crude product was purified by Prep-HPLC (XBridge Shield RP18 OBD Column 30*150 mm, 5 um; Water (10 mmol/L sodium bicarbonate): ACN (32%-60%) in 8 min; 60 mL/min) to afford 2-[[8-amino-7-fluoro-6-(2-isopropoxy-4-methyl-pyrimidin-5-yl)-3-isoquinolyl]amino]-6-isopropyl-5,8-dihydro-4H-pyrazolo[1,5-d][1,4]diazepin-7-one (7.7 mg, 0.015 mmol) as a yellow solid. LCMS (ESI) [M+H]⁺=519.3; ¹HNMR (300 MHz, Methanol-d₄) δ 9.15 (s, 1H), 8.41 (s, 1H), 7.66 (s, 1H), 6.89 (d, J=6.0 Hz, 1H), 6.05 (s, 1H), 5.49-5.34 (m, 1H), 5.06 (s, 2H), 4.89-4.71 (m, 1H), 3.97-3.80 (m, 2H), 3.24-3.06 (m, 2H), 2.41 (s, 3H), 1.44 (d, J=6.2 Hz, 6H), 1.24 (d, J=6.8 Hz, 6H).

Step 5: 2-((8-amino-7-fluoroisoquinolin-3-yl)amino)-6-isopropyl-5,6-dihydro-4H-pyrazolo[1,5-d][1,4]diazepin-7(8H)-one (Compound 254)

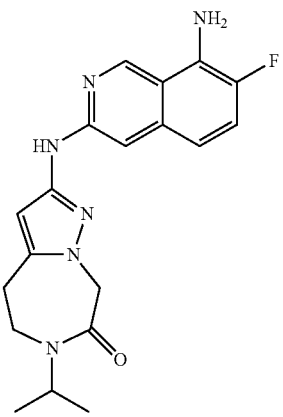 [SMILES: CC(C)N1CCc2cc(Nc3cc4ccc(F)c(N)c4cn3)nn2CC1=O]

A solution of tert-butyl N-[7-fluoro-3-[(6-isopropyl-7-oxo-5,8-dihydro-4H-pyrazolo[1,5-d][1,4]diazepin-2-yl)amino]-8-isoquinolyl]carbamate (20 mg, 0.04 mmol) and 2,2,2-trifluoroacetic acid (4 mL) was stirred at 25° C. for 1 hour. The mixture was concentrated under vacuum. The reaction mixture was adjusted to pH 10 with ammonia in methanol (7 mol/L). The crude product was purified by Prep-HPLC (SunFire Prep C18 OBD Column 19×150 mm Sum; Water (0.1% FA): ACN (25%-52%) in 7 min; 25 mL/min) to afford 2-[(8-amino-7-fluoro-3-isoquinolyl)amino]-6-isopropyl-5,8-dihydro-4H-pyrazolo[1,5-d][1,4]diazepin-7-one (2.5 mg, 0.0068 mmol) as a orange solid. LCMS (ESI) [M+H]$^+$=369.2; $^1$HNMR (300 MHz, Methanol-d$_4$) δ 9.23 (s, 1H), 7.55 (s, 1H), 7.51-7.42 (m, 1H), 7.06-7.02 (m, 1H), 5.99 (s, 1H), 5.14 (s, 2H), 4.83-4.72 (m, 1H), 3.96-3.85 (m, 2H), 3.18-3.05 (m, 2H), 1.25 (d, J=6.8 Hz, 6H).

Example 155

2-((8-amino-6-(5-amino-4-methylpyridin-3-yl)-7-fluoroisoquinolin-3-yl)amino)-5-isopropyl-4,5-dihydro-7H-pyrazolo[5,1-d][1,2,5]thiadiazine 6,6-dioxide (Compound 256)

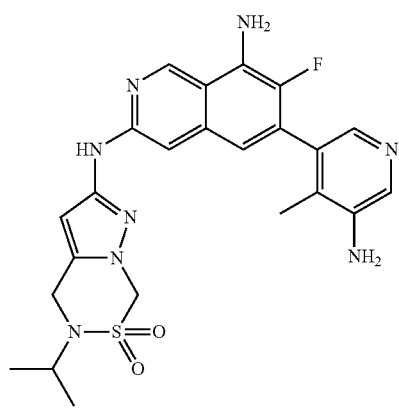 [SMILES: Cc1c(N)cncc1-c1cc2cc(Nc3cc4n(n3)CS(=O)(=O)N(C(C)C)C4)ncc2c(N)c1F]

Step 1: 1-chloro-N-isopropyl-methanesulfonamide

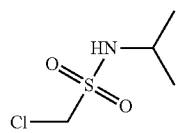

A mixture of isopropylamine (1.19 g, 20.13 mmol) and triethylamine (2.03 g, 20.13 mmol) in dichloromethane (100 mL) was added chloromethane sulfonylchloride (1.5 g, 10.07 mmol) at 0° C. The reaction was stirred for 2 hours at 0° C. The resulting solution was washed with water. The organic layer was dried over anhydrous sodium sulfate. After filtration, the filtrate was concentrated under vacuum to afford 1-chloro-N-isopropyl-methanesulfonamide (1.1 g, 6.40 mmol) as colorless oil. GCMS=171.

Step 2: methyl 5-bromo-2-(isopropylsulfamoylmethyl)pyrazole-3-carboxylate

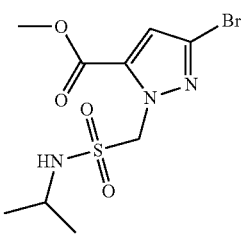 [SMILES: COC(=O)c1cc(Br)nn1CS(=O)(=O)NC(C)C]

A mixture of 1-chloro-N-isopropyl-methanesulfonamide (1381.51 mg, 8.05 mmol) methyl 3-bromo-1H-pyrazole-5-carboxylate (1.1 g, 5.37 mmol) and potassium carbonate (2.22 g, 16.1 mmol) in 1-methyl-2-pyrrolidinone (20 mL) was stirred at 60° C. for 5 hours. After filtration, the filtrate was concentrated under reduced pressure. The residue was purified by reverse phase chromatography (acetonitrile 0-40/0.1% NH$_3$H$_2$O in water) to afford methyl 5-bromo-2-(isopropylsulfamoylmethyl) pyrazole-3-carboxylate (600 mg, 1.76 mmol) as a white solid. LCMS (ESI) [M+H]$^+$=340.

Step 3: 1-[3-bromo-5-(hydroxymethyl)pyrazol-1-yl]-N-isopropyl-methanesulfonamide

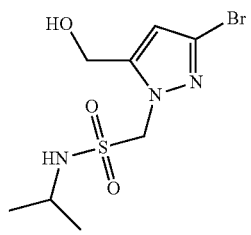 [SMILES: CC(C)NS(=O)(=O)Cn1nc(Br)cc1CO]

To a solution of methyl 5-bromo-2-(isopropylsulfamoylmethyl)pyrazole-3-carboxylate (600 mg, 1.76 mmol) in dichloromethane (20 mL) was added diisobutylaluminium hydride (3.53 mL, 3.53 mmol, 1 mol/L) at 0° C. The resulting solution was stirred for 2 hours at 0° C. The reaction was quenched with methanol. After filtration, the filtrate was concentrated under reduced pressure. The resulting residue was purified by reverse phase chromatography (acetonitrile 0-40/0.1% sodium bicarbonate in water) to afford 1-[3-bromo-5-(hydroxymethyl)pyrazol-1-yl]-N-isopropyl-methanesulfonamide (400 mg, 1.28 mmol) as a colorless oil. LCMS (ESI) [M+H]$^+$=312.

Step 4: 2-bromo-5-isopropyl-4,7-dihydropyrazolo[5,1-d][1,2,5]thiadiazine 6,6-dioxide

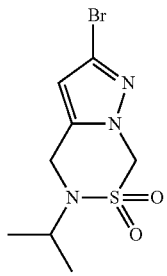

A solution of 1-[3-bromo-5-(hydroxymethyl)pyrazol-1-yl]-N-isopropyl-methanesulfonamide (400 mg, 1.28 mmol) and triphenylphosphine (671 mg, 2.56 mmol) in tetrahydrofuran (10 mL) was added diisopropyl azodicarboxylate (517 mg, 2.56 mmol) at 0° C. under nitrogen. The resulting solution was stirred for 2 hours at room temperature. The organic layer was concentrated under vacuum. The residue was purified by flash chromatography on silica gel eluting with petroleum ether/ethyl acetate (7/3) to afford 2-bromo-5-isopropyl-4,7-dihydropyrazolo[5,1-d][1,2,5]thiadiazine 6,6-dioxide (300 mg, 1.02 mmol) as a white solid. LCMS (ESI) [M+H]$^+$=294.

Step 5: tert-butyl N-tert-butoxycarbonyl-N-[5-[8-chloro-7-fluoro-3-[(5-isopropyl-6,6-dioxo-4,7-dihydropyrazolo[5,1-d][1,2,5]thiadiazin-2-yl)amino]-6-isoquinolyl]-4-methyl-3-pyridyl]carbamate

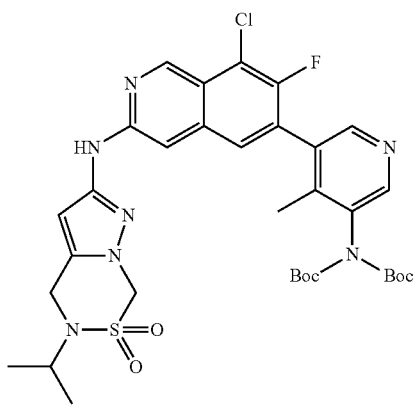 [SMILES: Cc1c(-c2cc3cc(Nc4cc5n(n4)CS(=O)(=O)N(C(C)C)C5)ncc3c(Cl)c2F)cncc1N(C(=O)OC(C)(C)C)C(=O)OC(C)(C)C]

A mixture of tert-butyl N-[5-(3-amino-8-chloro-7-fluoro-6-isoquinolyl)-4-methyl-3-pyridyl]-N-tert-butoxycarbonyl-carbamate (342 mg, 0.68 mmol), 2-bromo-5-isopropyl-4,7-dihydropyrazolo[5,1-d][1,2,5]thiadiazine 6,6-dioxide (200 mg, 0.68 mmol) tris(dibenzylideneacetone)dipalladium-chloroformadduct (140 mg, 0.14 mmol), 4,5-bis(diphenylphosphino)-9,9-dimethylxanthene (157.19 mg, 0.27 mmol), cesium carbonate (665 mg, 2.04 mmol) in 1,4-dioxane (20 mL) was stirred under nitrogen for 6 hours at 100° C. After filtration, the filtrate was concentrated under reduced pressure. The residue was purified by flash chromatography on silica gel eluting with petroleum ether/ethyl acetate (2/3) to afford tert-butyl N-tert-butoxycarbonyl-N-[5-[8-chloro-7-fluoro-3-[(5-isopropyl-6,6-dioxo-4,7-dihydropyrazolo[5,1-d][1,2,5]thiadiazin-2-yl)amino]-6-isoquinolyl]-4-methyl-3-pyridyl]carbamate (105 mg, 0.15 mmol) as a yellow solid. LCMS (ESI) [M+H]$^+$=716.

Step 6: tert-butyl N-tert-butoxycarbonyl-N-[5-[8-(tert-butoxycarbonylamino)-7-fluoro-3-[(5-isopropyl-6,6-dioxo-4,7-dihydropyrazolo[5,1-d][1,2,5]thiadiazin-2-yl)amino]-6-isoquinolyl]-4-methyl-3-pyridyl]carbamate

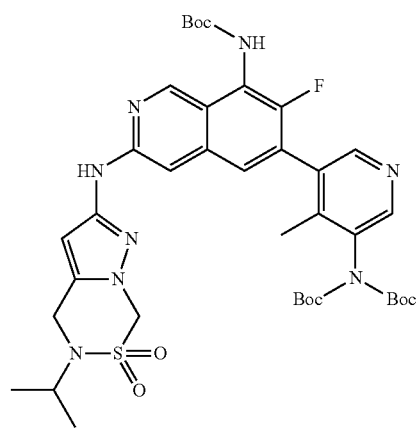 [SMILES: Cc1c(-c2cc3cc(Nc4cc5n(n4)CS(=O)(=O)N(C(C)C)C5)ncc3c(NC(=O)OC(C)(C)C)c2F)cncc1N(C(=O)OC(C)(C)C)C(=O)OC(C)(C)C]

A mixture of tert-butyl N-tert-butoxycarbonyl-N-[5-[8-chloro-7-fluoro-3-[(5-isopropyl-6,6-dioxo-4,7-dihydropyrazolo[5,1-d][1,2,5]thiadiazin-2-yl)amino]-6-isoquinolyl]-4-methyl-3-pyridyl]carbamate (90 mg, 0.13 mmol), tert-butyl carbamate (294.42 mg, 2.51 mmol), tris(dibenzylideneacetone)dipalladium-chloroformadduct (26 mg, 0.03 mmol), Brettphos (27 mg, 0.05 mmol) and cesium carbonate (122 mg, 0.38 mmol) in 1,4-dioxane (10 mL) was stirred for 2 hours at 90° C. After filtration, the filtrate was concentrated under reduced pressure. The residue was purified by flash chromatography on silica gel eluting with petroleum ether/ethyl acetate (2/3) to afford tert-butyl N-tert-butoxycarbonyl-N-[5-[8-(tert-butoxycarbonylamino)-7-fluoro-3-[(5-isopropyl-6,6-dioxo-4,7-dihydropyrazolo[5,1-d][1,2,5]thiadiazin-2-yl)amino]-6-isoquinolyl]-4-methyl-3-pyridyl]carbamate (60 mg, 0.075 mmol) as a yellow solid. LCMS (ESI) [M+H]$^+$=797.

Step 7: 6-(5-amino-4-methyl-3-pyridyl)-7-fluoro-N3-(5-isopropyl-6,6-dioxo-4,7-dihydropyrazolo[5,1-d][1,2,5]thiadiazin-2-yl)isoquinoline-3,8-diamine; Formic Acid

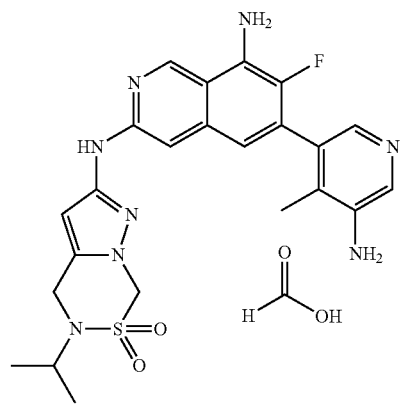

A solution of tert-butyl N-tert-butoxycarbonyl-N-[5-[8-(tert-butoxycarbonylamino)-7-fluoro-3-[(5-isopropyl-6,6-dioxo-4,7-dihydropyrazolo[5,1-d][1,2,5]thiadiazin-2-yl)amino]-6-isoquinolyl]-4-methyl-3-pyridyl]carbamate (60 mg, 0.08 mmol) and 2,2,2-trifluoroacetic acid (2 mL) in dichloromethane (4 mL) was stirred at 25° C. for 2 hours. The solvent was concentrated under vacuum. The resulting residue was purified by reverse phase chromatography (acetonitrile 0-40/0.1% FA in water) to afford 6-(5-amino-4-methyl-3-pyridyl)-7-fluoro-N 3-(5-isopropyl-6,6-dioxo-4,7-dihydropyrazolo[5,1-d][1,2,5]thiadiazin-2-yl)isoquinoline-3,8-diamine; formic acid (18.6 mg, 0.034 mmol) as a orange solid. LCMS (ESI) [M+H]$^+$=497; $^1$HNMR (400 MHz, CD$_3$OD) δ 9.17 (s, 1H), 8.01 (s, 1H), 7.78 (s, 1H), 7.77 (s, 1H), 6.85 (d, J=6.4 Hz, 1H), 6.13 (s, 1H), 5.28 (s, 2H), 4.63 (s, 2H), 4.34-4.27 (m, 1H), 2.08 (s, 3H), 1.20 (d, J=6.4 Hz, 6H).

Example 156

2-((8-amino-6-(benzyloxy)-7-fluoroisoquinolin-3-yl)amino)-6-isopropyl-5,6-dihydro-4H-pyrazolo[1,5-d][1,4]diazepin-7(8H)-one (Compound 257)

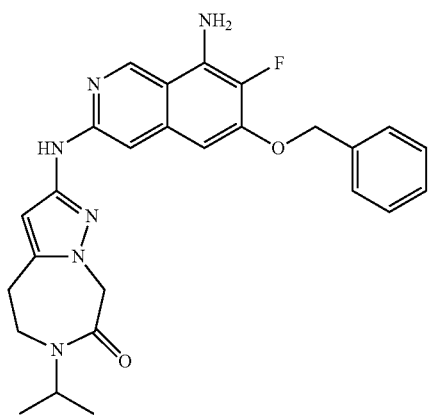 [SMILES: CC(C)N1CCc2cc(Nc3cc4cc(OCc5ccccc5)c(F)c(N)c4cn3)nn2CC1=O]

A solution of tert-butyl N-[6-benzyloxy-7-fluoro-3-[(6-isopropyl-7-oxo-5,8-dihydro-4H-pyrazolo[1,5-d][1,4]diazepin-2-yl)amino]-8-isoquinolyl]carbamate (50 mg, 0.086 mmol) and 2,2,2-trifluoroacetic acid (1 mL) in dichloromethane (5 mL) was stirred at 25° C. for 3 hours. The mixture was concentrated under vacuum. The reaction mixture was adjusted to pH 7 with ammonia in methanol (7 mol/L). The residue was purified by flash chromatography on C18 (acetonitrile-0.1% sodium bicarbonate in water) to afford 2-((8-amino-6-(benzyloxy)-7-fluoroisoquinolin-3-yl)amino)-6-isopropyl-5,6-dihydro-4H-pyrazolo[1,5-d][1,4]diazepin-7(8H)-one (12.2 mg, 0.026 mmol) as a brown solid. LCMS (ESI) [M+H]$^+$=475.2. $^1$H NMR (300 MHz, DMSO-d$_6$) δ 9.02 (d, J=14.0 Hz, 2H), 7.60 (s, 1H), 7.56-7.46 (m, 2H), 7.50-7.31 (m, 3H), 6.62-6.59 (m, 1H), 5.94 (d, J=6.4 Hz, 3H), 5.25 (s, 2H), 4.98 (s, 2H), 4.63-4.58 (m, 1H), 3.79-3.77 (m, 2H), 3.00-2.98 (m, 2H), 1.13 (d, J=6.8 Hz, 6H).

Example 157

2-((8-amino-7-fluoro-6-methylisoquinolin-3-yl)amino)-6-isopropyl-5,6-dihydro-4H-pyrazolo[1,5-d][1,4]diazepin-7(8H)-one (Compound 258)

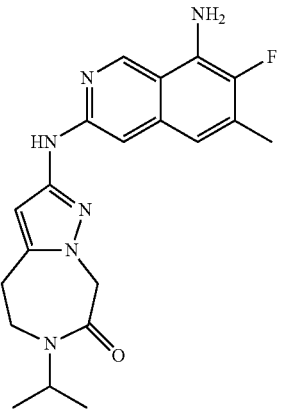 [SMILES: Cc1cc2cc(Nc3cc4n(n3)CC(=O)N(C(C)C)CC4)ncc2c(N)c1F]

Step 1: tert-butyl (7-fluoro-3-((6-isopropyl-7-oxo-5,6,7,8-tetrahydro-4H-pyrazolo[1,5-d][1,4]diazepin-2-yl)amino)-6-methylisoquinolin-8-yl)carbamate

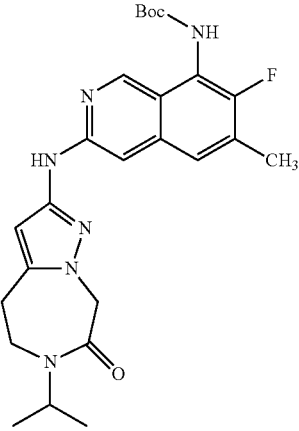 [SMILES: Cc1cc2cc(Nc3cc4n(n3)CC(=O)N(C(C)C)CC4)ncc2c(NC(=O)OC(C)(C)C)c1F]

A solution of [8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl] trifluoromethanesulfonate (100 mg, 0.16 mmol), trimethylboroxine (101.79 mg, 0.81 mmol), tetrakis(triphenylphosphine)palladium (37.46 mg, 0.03 mmol) and potassium carbonate (67.14 mg, 0.49 mmol) was stirred at 90° C. for 2 hours. The solvent was concentrated under vacuum. The residue was purified by flash chromatography on silica gel eluting with dichloromethane/methanol (20/1) to afford tert-butyl N-[7-fluoro-3-[(6-isopropyl-7-oxo-5,8-dihydro-4H-pyrazolo[1,5-d][1,4]diazepin-2-yl)amino]-6-methyl-8-isoquinolyl]carbamate (35 mg, 0.073 mmol) as a yellow solid. LCMS (ESI) [M+H]$^+$=483.

729

Step 2: 2-((8-amino-7-fluoro-6-methylisoquinolin-3-yl)amino)-6-isopropyl-5,6-dihydro-4H-pyrazolo[1,5-d][1,4]diazepin-7(8H)-one

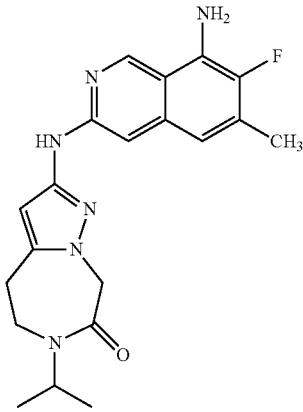 [SMILES: Cc1cc2cc(Nc3cc4n(n3)CC(=O)N(C(C)C)CC4)ncc2c(N)c1F]

A solution of tert-butyl N-[7-fluoro-3-[(6-isopropyl-7-oxo-5,8-dihydro-4H-pyrazolo[1,5-d][1,4]diazepin-2-yl)amino]-6-methyl-8-isoquinolyl]carbamate (25 mg, 0.05 mmol) and 2,2,2-trifluoroacetic acid (5 mL) was stirred at 25° C. for 1 hour. The reaction was concentrated under vacuum. The residue was adjusted to pH 10 with ammonia in methanol (7 mol/L). The crude product was purified by Prep-HPLC (SunFire Prep C18 OBD Column 19×150 mm 5 um 10 nm; Water (0.1% FA): ACN (10%-27%) in 12 min: 25 mL/min) to afford 2-[(8-amino-7-fluoro-6-methyl-3-isoquinolyl)amino]-6-isopropyl-5,8-dihydro-4H-pyrazolo[1,5-d][1,4]diazepin-7-one (5.4 mg, 0.014 mmol) as a orange solid. LCMS (ESI) [M+H]$^+$=383.2; $^1$HNMR (300 MHz, Methanol-d$_4$) δ 9.03 (s, 1H), 7.53 (s, 1H), 6.85 (d, J=6.6 Hz, 1H), 6.03 (s, 1H), 5.07 (s, 2H), 4.83-4.65 (m, 1H), 3.96-3.81 (m, 2H), 3.24-3.08 (m, 2H), 2.39 (d, J=2.3 Hz, 3H), 1.25 (d, J=6.8 Hz, 6H).

Example 158

2-((8-amino-7-fluoro-6-methoxyisoquinolin-3-yl)amino)-6-isopropyl-5,6-dihydro-4H-pyrazolo[1,5-d][1,4]diazepin-7(8H)-one (Compound 259)

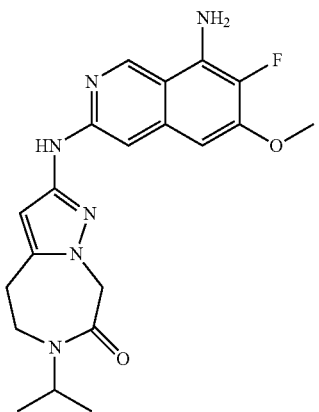 [SMILES: COc1cc2cc(Nc3cc4n(n3)CC(=O)N(C(C)C)CC4)ncc2c(N)c1F]

730

Step 1: tert-butyl (7-fluoro-3-((6-isopropyl-7-oxo-5,6,7,8-tetrahydro-4H-pyrazolo[1,5-d][1,4]diazepin-2-yl)amino)-6-methoxyisoquinolin-8-yl)carbamate

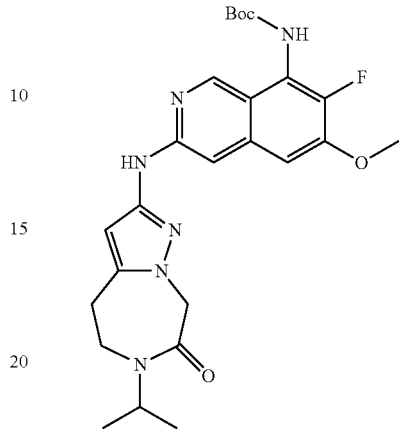

A solution of tert-butyl N-[7-fluoro-6-hydroxy-3-[(6-isopropyl-7-oxo-5,8-dihydro-4H-pyrazolo[1,5-d][1,4]diazepin-2-yl)amino]-8-isoquinolyl]carbamate (100 mg, 0.21 mmol) and potassium carbonate (42.72 mg, 0.31 mmol) in N,N-dimethylformamide (10 mL) was stirred at 0° C. for 15 minutes. Then iodomethane (43.96 mg, 0.31 mmol) was added and then stirred at 0° C. for 2 hours. After filtration, the filtrate was concentrated under vacuum. The residue was purified by flash chromatography on silica gel eluting with dichloromethane/methanol (20/1) to afford tert-butyl N-[7-fluoro-3-[(6-isopropyl-7-oxo-5,8-dihydro-4H-pyrazolo[1,5-d][1,4]diazepin-2-yl)amino]-6-methoxy-8-isoquinolyl]carbamate (58 mg, 0.12 mmol) as a yellow solid. LCMS (ESI) [M+H]$^+$=499

Step 2: 2-((8-amino-7-fluoro-6-methoxyisoquinolin-3-yl)amino)-6-isopropyl-5,6-dihydro-4H-pyrazolo[1,5-d][1,4]diazepin-7(8H)-one

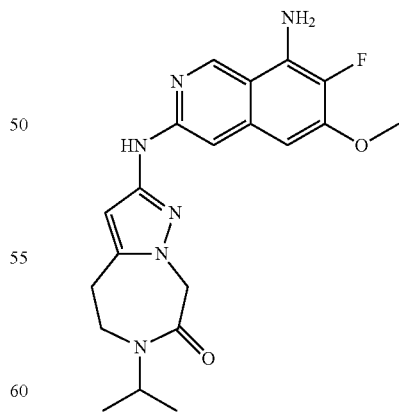

A solution of tert-butyl N-[7-fluoro-3-[(6-isopropyl-7-oxo-5,8-dihydro-4H-pyrazolo[1,5-d][1,4]diazepin-2-yl)amino]-6-methoxy-8-isoquinolyl]carbamate (55 mg, 0.11 mmol) and 2,2,2-trifluoroacetic acid (0.5 mL) in dichloromethane (2 mL) was stirred at 25° C. for 1 hour. The mixture was concentrated under vacuum. The reaction mixture was adjusted to pH 10 with ammonia in methanol (7 mol/L). The crude product was purified by Prep-HPLC (XBridge Shield RP18 OBD Column 30*150 mm, 5 um; Water (10 mmol/L sodium bicarbonate): ACN (20%-46%) in 9 min: 60 mL/min) to afford 2-[(8-amino-7-fluoro-6-methoxy-3-isoquinolyl)amino]-6-isopropyl-5,8-dihydro-4H-pyrazolo[1,5-d][1,4]diazepin-7-one (17.2 mg, 0.043 mmol) as a yellow solid. LCMS (ESI) [M+H]$^+$=399.2; $^1$HNMR (300 MHz, DMSO-d$_6$) δ 9.02 (s, 1H), 8.97 (s, 1H), 7.62 (s, 1H), 6.48 (d, J=7.2 Hz, 1H), 5.95 (s, 2H), 5.89 (s, 1H), 4.98 (s, 2H), 4.62-4.57 (m, 1H), 3.90 (s, 3H), 3.80-3.76 (m, 2H), 2.99-2.96 (m, 2H), 1.13 (d, J=6.8 Hz, 6H).

Example 159

2-((8-amino-7-fluoro-6-((pyridin-2-yloxy)methyl) isoquinolin-3-yl)amino)-6-isopropyl-5,6-dihydro-4H-pyrazolo[1,5-d][1,4]diazepin-7(8H)-one (Compound 260)

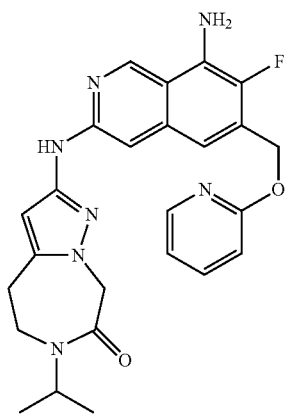 [SMILES: CC(C)N1CCc2cc(Nc3cc4cc(COc5ccccn5)c(F)c(N)c4cn3)nn2CC1=O]

Step 1: 2-[[8-chloro-6-(chloromethyl)-7-fluoro-3-isoquinolyl]amino]-6-isopropyl-5,8-dihydro-4H-pyrazolo[1,5-d][1,4]diazepin-7-one

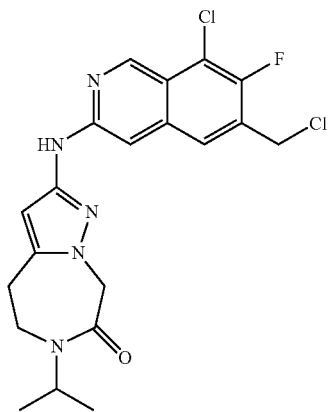 [SMILES: CC(C)N1CCc2cc(Nc3cc4cc(CCl)c(F)c(Cl)c4cn3)nn2CC1=O]

A solution of 2-[[8-chloro-7-fluoro-6-(hydroxymethyl)-3-isoquinolyl]amino]-6-isopropyl-5,8-dihydro-4H-pyrazolo[1,5-d][1,4]diazepin-7-one (145 mg, 0.35 mmol) and thionyl chloride (204.73 mg, 1.74 mmol) in dichloromethane (5 mL) was stirred at 25° C. for 1 hour. The solvent was concentrated under vacuum to afford 2-[[8-chloro-6-(chloromethyl)-7-fluoro-3-isoquinolyl]amino]-6-isopropyl-5,8-dihydro-4H-pyrazolo[1,5-d][1,4]diazepin-7-one (150 mg, 0.34 mmol) as a brown solid. LCMS (ESI) [M+H]$^+$=436.

Step 2: 2-((8-chloro-7-fluoro-6-((pyridin-2-yloxy) methyl)isoquinolin-3-yl)amino)-6-isopropyl-5,6-dihydro-4H-pyrazolo[1,5-d][1,4]diazepin-7(8H)-one and 2-[[8-chloro-7-fluoro-6-[(2-oxo-1-pyridyl) methyl]-3-isoquinolyl]amino]-6-isopropyl-5,8-dihydro-4H-pyrazolo[1,5-d][1,4]diazepin-7-one

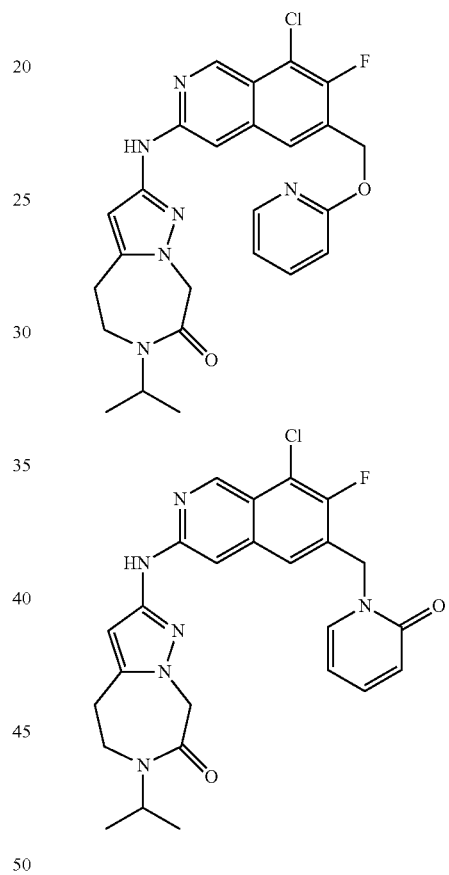

A mixture of 2-[[8-chloro-6-(chloromethyl)-7-fluoro-3-isoquinolyl]amino]-6-isopropyl-5,8-dihydro-4H-pyrazolo [1,5-d][1,4]diazepin-7-one (150 mg, 0.34 mmol), 1H-pyridin-2-one (98.08 mg, 1.03 mmol) and cesium carbonate (560.38 mg, 1.72 mmol) in N,N-dimethylformamide (5 mL) was stirred at 25° C. for 4 hours. After filtration, the filtrate was concentrated under reduced pressure. The resulting residue was purified by reverse phase chromatography (acetonitrile 0-40/0.1% hydrochloric acid in water) to afford 2-((8-chloro-7-fluoro-6-((pyridin-2-yloxy)methyl)isoquinolin-3-yl)amino)-6-isopropyl-5,6-dihydro-4H-pyrazolo[1,5-d][1,4]diazepin-7(8H)-one (15 mg, 0.03 mmol) and 2-[[8-chloro-7-fluoro-6-[(2-oxo-1-pyridyl)methyl]-3-isoquinolyl] amino]-6-isopropyl-5,8-dihydro-4H-pyrazolo[1,5-d][1,4] diazepin-7-one (85 mg, 0.17 mmol) as a yellow solid. LCMS (ESI) [M+H]$^+$=495.

Step 3:tert-butyl 7-fluoro-3-(6-isopropyl-7-oxo-5,6,7,8-tetrahydro-4H-pyrazolo[1,5-g][1,4]diazepin-2-ylamino)-6-((pyridin-2-yloxy)methyl)isoquinolin-8-ylcarbamate

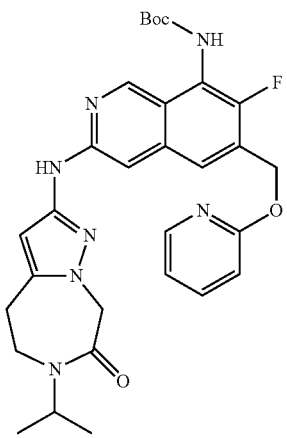 [SMILES: CC(C)N1CCc2cc(Nc3cc4cc(COc5ccccn5)c(F)c(NC(=O)OC(C)(C)C)c4cn3)nn2CC1=O]

To a mixture of 2-(8-chloro-7-fluoro-6-((pyridin-2-yloxy)methyl)isoquinolin-3-ylamino)-6-isopropyl-5,6-dihydro-4H-pyrazolo[1,5-g][1,4]diazepin-7(8H)-one (14 mg, 0.028 mmol), tert-butyl carbamate (99.47 mg, 0.85 mmol), tris(dibenzylideneacetone)dipalladium-chloroformadduct (5.86 mg, 0.0057 mmol) and Brettphos (6.08 mg, 0.011 mmol) in 1,4-dioxane (3 mL) was added cesium carbonate (36.9 mg, 0.11 mmol) at 25° C. The resulting solution was stirred for 3 hours at 90° C. After filtration, the filtrate was concentrated under reduced pressure. The residue was purified by flash chromatography on silica gel eluting with dichloromethane/methanol (9/1) to afford tert-butyl 7-fluoro-3-(6-isopropyl-7-oxo-5,6,7,8-tetrahydro-4H-pyrazolo[1,5-g][1,4]diazepin-2-ylamino)-6-((pyridin-2-yloxy)methyl)isoquinolin-8-ylcarbamate (15 mg, 0.076 mmol) as a yellow solid. LCMS (ESI) [M+H]$^+$=576.

Step 4: 2-[[8-amino-7-fluoro-6-(2-pyridyloxymethyl)-3-isoquinolyl]amino]-6-isopropyl-5,8-dihydro-4H-pyrazolo[1,5-d][1,4]diazepin-7-one

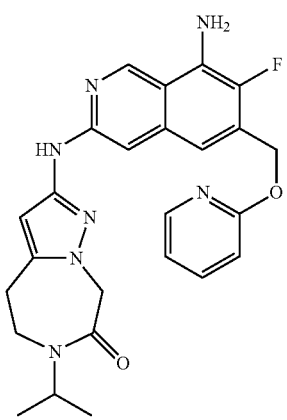 [SMILES: CC(C)N1CCc2cc(Nc3cc4cc(COc5ccccn5)c(F)c(N)c4cn3)nn2CC1=O]

A solution of tert-butyl N-[7-fluoro-3-[(6-isopropyl-7-oxo-5,8-dihydro-4H-pyrazolo[1,5-d][1,4]diazepin-2-yl)amino]-6-(2-pyridyloxymethyl)-8-isoquinolyl]carbamate (18 mg, 0.03 mmol) in dichloromethane (3 mL) and 2,2,2-trifluoroacetic acid (2 mL) was stirred at 25° C. for 2 hours. The solvent was concentrated under vacuum. The crude product was purified by Prep-HPLC (Atlantis HILIC OBD, 19×150 mm 5 um; water (10 mmol/sodium bicarbonate):CH$_3$CN=35%-55% B in 7 min) to afford 2-[[8-amino-7-fluoro-6-(2-pyridyloxymethyl)-3-isoquinolyl]amino]-6-isopropyl-5,8-dihydro-4H-pyrazolo[1,5-d][1,4]diazepin-7-one (3.4 mg, 0.0072 mmol) as a yellow solid. LCMS (ESI) [M+H]$^+$=476.2; $^1$HNMR (400 MHz, DMSO-d$_6$) δ 9.20 (s, 1H), 9.06 (s, 1H), 8.20 (ddd, J=5.1, 2.0, 0.8 Hz, 1H), 7.76 (ddd, J=8.4, 7.1, 2.0 Hz, 1H), 7.64 (s, 1H), 7.02 (ddd, J=7.1, 5.0, 1.0 Hz, 1H), 6.99-6.91 (m, 2H), 6.01 (s, 2H), 5.96 (s, 1H), 5.45 (s, 2H), 4.96 (s, 2H), 4.59 (q, J=6.8 Hz, 1H), 3.78 (t, J=5.9 Hz, 2H), 2.98 (t, J=5.9 Hz, 2H), 1.12 (d, J=6.8 Hz, 6H).

Example 160

2-((8-amino-7-fluoro-6-((2-oxopyridin-1(2H)-yl)methyl)isoquinolin-3-yl)amino)-6-isopropyl-5,6-dihydro-4H-pyrazolo[1,5-d][1,4]diazepin-7(8H)-one (Compound 261)

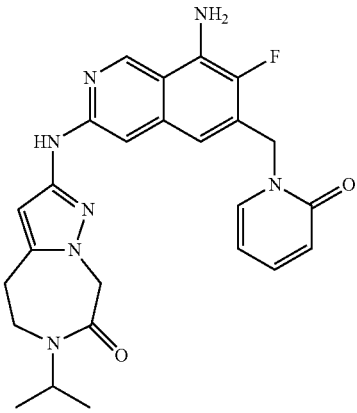 [SMILES: CC(C)N1CCc2cc(Nc3cc4cc(Cn5ccccc5=O)c(F)c(N)c4cn3)nn2CC1=O]

Step 1:tert-butyl N-[7-fluoro-3-[(6-isopropyl-7-oxo-5,8-dihydro-4H-pyrazolo[1,5-d][1,4]diazepin-2-yl)amino]-6-[(2-oxo-1-pyridyl)methyl]-8-isoquinolyl]carbamate

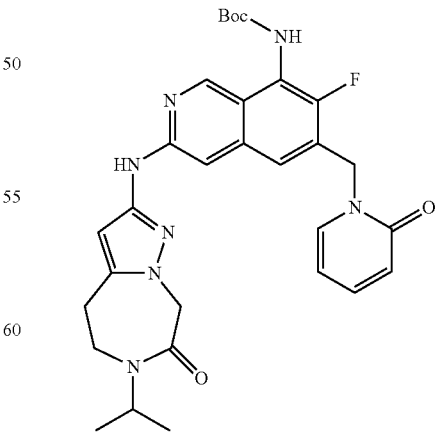

A solution of 2-[[8-chloro-7-fluoro-6-[(2-oxo-1-pyridyl)methyl]-3-isoquinolyl]amino]-6-isopropyl-5,8-dihydro-4H- pyrazolo[1,5-d][1,4]diazepin-7-one (95 mg, 0.19 mmol), tert-butyl carbamate (673.7 mg, 5.76 mmol), tris(dibenzylideneacetone)dipalladium-chloroformadduct (39.73 mg, 0.040 mmol) and Brettphos (41.23 mg, 0.080 mmol) in 1,4-dioxane (10 mL) was added cesium carbonate (250.29 mg, 0.77 mmol) at 25° C. The resulting solution was stirred for 3 hours at 90° C. After filtration, the filtrate was concentrated under reduced pressure. The residue was purified by flash chromatography on silica gel eluting with dichloromethane/methanol (10/1) to afford tert-butyl N-[7-fluoro-3-[(6-isopropyl-7-oxo-5,8-dihydro-4H-pyrazolo[1,5-d][1,4]diazepin-2-yl)amino]-6-[(2-oxo-1-pyridyl)methyl]-8-isoquinolyl]carbamate (75 mg, 0.13 mmol) as a yellow solid. LCMS (ESI) [M+H]$^+$=576

Step 2: 2-[[8-amino-7-fluoro-6-[(2-oxo-1-pyridyl)methyl]-3-isoquinolyl]amino]-6-isopropyl-5,8-dihydro-4H-pyrazolo[1,5-d][1,4]diazepin-7-one

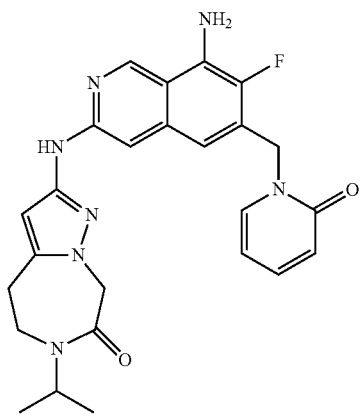 [SMILES: CC(C)N1CCc2cc(Nc3cc4cc(Cn5ccccc5=O)c(F)c(N)c4cn3)nn2CC1=O]

A solution of tert-butyl N-[7-fluoro-3-[(6-isopropyl-7-oxo-5,8-dihydro-4H-pyrazolo[1,5-d][1,4]diazepin-2-yl)amino]-6-[(2-oxo-1-pyridyl)methyl]-8-isoquinolyl]carbamate (70 mg, 0.12 mmol) in 2,2,2-trifluoroacetic acid (3 mL) and dichloromethane (5 mL) was stirred at 25° C. for 2 hours. The solvent was concentrated under vacuum. The crude product was purified by Prep-HPLC (Atlantis HILIC OBD, 19×150 mm 5 um; water (10 mmol/sodium bicarbonate): CH$_3$CN=13%-43% B in 7 min) to afford 2-[[8-amino-7-fluoro-6-[(2-oxo-1-pyridyl)methyl]-3-isoquinolyl]amino]-6-isopropyl-5,8-dihydro-4H-pyrazolo[1,5-d][1,4]diazepin-7-one (23.8 mg, 0.050 mmol) as a yellow solid. LCMS (ESI) [M+H]$^+$=476.2; $^1$HNMR (400 MHz, DMSO-d$_6$) δ 9.18 (s, 1H), 9.06 (s, 1H), 7.72 (dd, J=6.9, 2.0 Hz, 1H), 7.53-7.43 (m, 2H), 6.49-6.39 (m, 2H), 6.29 (td, J=6.7, 1.4 Hz, 1H), 6.05 (s, 2H), 5.96 (s, 1H), 5.20 (s, 2H), 4.94 (s, 2H), 4.59 (m, J=6.8 Hz, 1H), 3.77 (t, J=5.9 Hz, 2H), 2.97 (t, J=5.9 Hz, 2H), 1.11 (d, J=6.8 Hz, 6H).

Example 161

6-(5-amino-4-methylpyridin-3-yl)-N3-(7,7-difluoro-4-methyl-5,6,7,8-tetrahydro-4H-pyrazolo[1,5-a]azepin-2-yl)-7-fluoroisoquinoline-3,8-diamine (Compound 262)

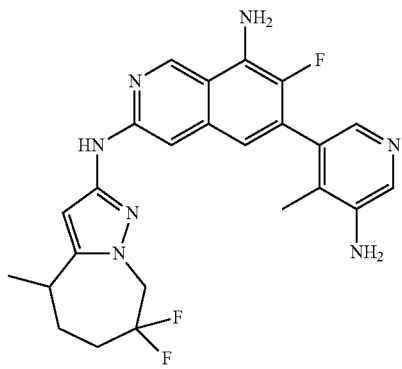 [SMILES: Cc1c(N)cncc1-c1cc2cc(Nc3cc4n(n3)CC(F)(F)CCC4C)ncc2c(N)c1F]

Step 1: 1-(3,5-dibromopyrazol-1-yl)hex-5-en-2-ol

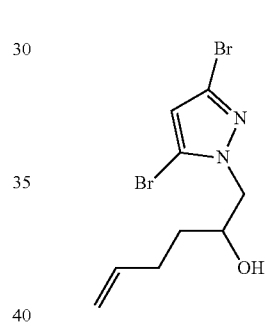

A solution of 3,5-dibromo-1H-pyrazole (5.0 g, 22.14 mmol), 1,2-epoxy-5-hexene (4.35 g, 44.27 mmol) and cesium carbonate (21.78 g, 66.41 mmol) in N,N-dimethylformamide (20 mL) was stirred at 85° C. for 2 hours. The solvent was concentrated under vacuum. The residue was purified by flash chromatography on silica gel eluting with petroleum ether/ethyl acetate (3/1) to afford 1-(3,5-dibromopyrazol-1-yl)hex-5-en-2-ol (4.2 g, 13.0 mmol) as a light yellow oil. LCMS (ESI) [M+H]$^+$=324.0.

Step 2: 2-bromo-4-methylene-5,6,7,8-tetrahydropyrazolo[1,5-a]azepin-7-ol

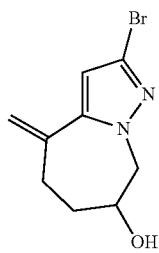

A mixture of [1-(3,5-dibromopyrazol-1-yl)hex-5-en-2-ol (7.2 g, 22.22 mmol), palladium acetate (500 mg, 2.23 mmol), triphenylphosphine (1170.0 mg, 4.47 mmol), potassium acetate (6570.0 mg, 67.04 mmol) and tetrabutylammonium bromide (7155.33 mg, 22.22 mmol)] in N,N-dimethylacetamide (70 mL) at 90° C. for 12 hours under nitrogen. After filtration, filtrate was concentrated under vacuum. The residue was purified by flash chromatography on silica gel eluting with petroleum ether/ethyl acetate (2/1) to afford 2-bromo-4-methylene-5,6,7,8-tetrahydropyrazolo[1,5-a]azepin-7-ol (3.8 g, 15.63 mmol) as a yellow solid. LCMS (ESI) [M+H]=243.1.

Step 3: 2-bromo-4-methylene-6,8-dihydro-5H-pyrazolo[1,5-a]azepin-7-one

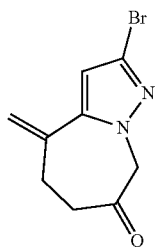

A mixture of 2-bromo-4-methylene-5,6,7,8-tetrahydropyrazolo[1,5-a]azepin-7-ol (1.5 g, 6.17 mmol) and DMP in dichloromethane (20 mL) was stirred at 25° C. for 3 hours. The reaction mixture was adjusted to pH 7 with sodium bicarbonate in water. The resulting solution was extracted with dichloromethane, dried with anhydrous sodium sulfate. After filtration, the filtrate was concentrated under vacuum. The residue was purified by flash chromatography on silica gel eluting with petroleum ether/ethyl acetate (4/1) to afford 2-bromo-4-methylene-6,8-dihydro-5H-pyrazolo[1,5-a]azepin-7-one (600 mg, 2.49 mmol) as a yellow oil. LC/MS (ESI) [M+H]$^+$=241.1.

Step 4: 2-bromo-7,7-difluoro-4-methylene-6,8-dihydro-5H-pyrazolo[1,5-a]azepine

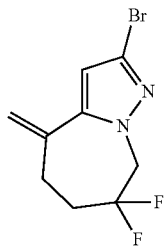

A solution of 2-bromo-4-methylene-6,8-dihydro-5H-pyrazolo[1,5-a]azepin-7-one (400 mg, 1.66 mmol) and diethylaminosulfur trifluoride (801.39 mg, 4.98 mmol) in dichloromethane (10 mL) was stirred at 0° C. for 1 hour. The mixture was quenched by water. The resulting solution was extracted with ethyl acetate, dried with anhydrous sodium sulfate. After filtration, the filtrate was concentrated under vacuum. The residue was purified by flash chromatography on silica gel eluting with petroleum ether/ethyl acetate (5/1) to afford 2-bromo-7,7-difluoro-4-methylene-6,8-dihydro-5H-pyrazolo[1,5-a]azepine (120 mg, 0.46 mmol) as a light yellow oil. LC/MS (ESI): [M+H]$^+$=263.1.

Step 5: tert-butyl N-tert-butoxycarbonyl-N-[5-[8-chloro-3-[(7,7-difluoro-4-methylene-6,8-dihydro-5H-pyrazolo[1,5-a]azepin-2-yl)amino]-7-fluoro-6-isoquinolyl]-4-methyl-3-pyridyl]carbamate

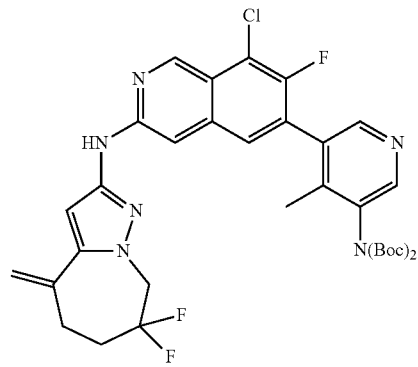

A mixture of 2-bromo-7,7-difluoro-4-methylene-6,8-dihydro-5H-pyrazolo[1,5-a]azepine (21.24 mg, 0.08 mmol), tert-butyl N-[5-(3-amino-8-chloro-7-fluoro-6-isoquinolyl)-4-methyl-3-pyridyl]-N-tert-butoxycarbonyl-carbamate (65.0 mg, 0.13 mmol), t-BuBrettphosPdG3 (44.15 mg, 0.05 mmol), t-BuBrettphos (31.27 mg, 0.06 mmol) and cesium carbonate (126.39 mg, 0.39 mmol) in 1,4-dioxane (6 mL) was stirred at 130° C. for 2 hours. The solvent was concentrated under vacuum. The residue was purified by flash chromatography on silica gel eluting with PE/EA (1/1) to afford tert-butyl N-tert-butoxycarbonyl-N-[5-[8-chloro-3-[(7,7-difluoro-4-methylene-6,8-dihydro-5H-pyrazolo[1,5-a]azepin-2-yl)amino]-7-fluoro-6-isoquinolyl]-4-methyl-3-pyridyl]carbamate (30 mg, 0.044 mmol) as a yellow solid. LCMS (ESI) [M+H]$^+$=685.1.

Step 6: tert-butyl N-tert-butoxycarbonyl-N-[5-[8-chloro-3-[(7,7-difluoro-4-methylene-6,8-dihydro-5H-pyrazolo[1,5-a]azepin-2-yl)amino]-7-fluoro-6-isoquinolyl]-4-methyl-3-pyridyl]carbamate

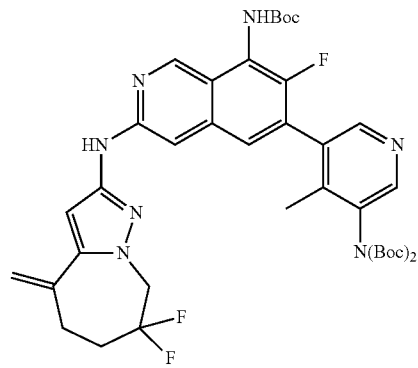

A mixture of tert-butyl N-tert-butoxycarbonyl-N-[5-[8-chloro-3-[(7,7-difluoro-4-methylene-6,8-dihydro-5H-pyrazolo[1,5-a]azepin-2-yl)amino]-7-fluoro-6-isoquinolyl]-4-methyl-3-pyridyl]carbamate (40 mg, 0.06 mmol), tert-butyl carbamate (170.99 mg, 1.46 mmol), tris(dibenzylideneacetone)dipalladium-chloroformadduct (12.09 mg, 0.01 mmol), Brettphos (9.39 mg, 0.02 mmol) and cesium carbonate (57.1 mg, 0.18 mmol) in 1,4-dioxane (4 mL) was stirred at 90° C. for 3 hours. The solvent was concentrated under vacuum. The residue was purified by flash chromatography on silica gel eluting with dichloromethane/methanol (10/1) to afford tert-butyl N-tert-butoxycarbonyl-N-[5-[8-chloro-3-[(7,7-difluoro-4-methylene-6,8-dihydro-5H-pyrazolo[1,5-a]azepin-2-yl)amino]-7-fluoro-6-isoquinolyl]-4-methyl-3-pyridyl]carbamate (40 mg, 0.06 mmol) as a yellow solid. LCMS (ESI) [M+H]$^+$=765.8.

Step 7: tert-butyl N-tert-butoxycarbonyl-N-[5-[8-(tert-butoxycarbonylamino)-3-[(7,7-difluoro-4-methyl-4,5,6,8-tetrahydropyrazolo[1,5-a]azepin-2-yl)amino]-7-fluoro-6-isoquinolyl]-4-methyl-3-pyridyl]carbamate

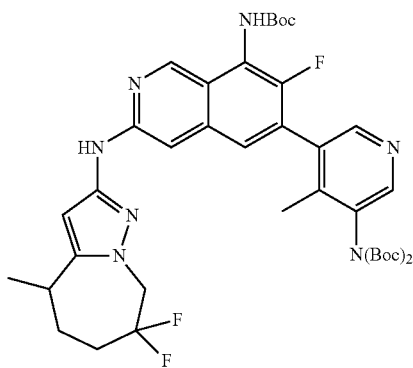

A mixture of tert-butyl N-tert-butoxycarbonyl-N-[5-[8-(tert-butoxycarbonylamino)-3-[(7,7-difluoro-4-methylene-6,8-dihydro-5H-pyrazolo[1,5-a]azepin-2-yl)amino]-7-fluoro-6-isoquinolyl]-4-methyl-3-pyridyl]carbamate (105.0 mg, 0.14 mmol) and palladium carbon (10%) (20 mg, 0.14 mmol) in methanol (5 mL) was stirred at 25° C. for 1 hour. After filtration, the filtrate was concentrated under reduced pressure. The residue was purified by flash chromatography on silica gel eluting with dichloromethane/methanol (10/1) to afford tert-butyl N-tert-butoxycarbonyl-N-[5-[8-(tert-butoxycarbonylamino)-3-[(7,7-difluoro-4-methyl-4,5,6,8-tetrahydropyrazolo[1,5-a]azepin-2-yl)amino]-7-fluoro-6-isoquinolyl]-4-methyl-3-pyridyl]carbamate (70 mg, 0.09 mmol) as a light yellow solid. LC/MS (ESI) [M+H]$^+$=767.8.

Step 8: 6-(5-amino-4-methylpyridin-3-yl)-N3-(7,7-difluoro-4-methyl-5,6,7,8-tetrahydro-4H-pyrazolo[1,5-a]azepin-2-yl)-7-fluoroisoquinoline-3,8-diamine

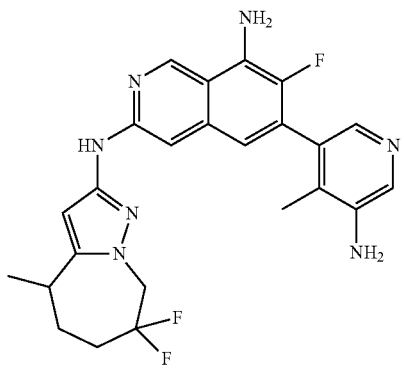 [SMILES: Cc1c(N)cncc1-c1cc2cc(Nc3cc4n(n3)CC(F)(F)CCC4C)ncc2c(N)c1F]

A solution of [tert-butyl N-tert-butoxycarbonyl-N-[5-[8-(tert-butoxycarbonylamino)-3-[(7,7-difluoro-4-methyl-4,5,6,8-tetrahydropyrazolo[1,5-a]azepin-2-yl)amino]-7-fluoro-6-isoquinolyl]-4-methyl-3-pyridyl]carbamate (70 mg, 0.09 mmol) and 2,2,2-trifluoroacetic acid (1 mL) in dichloromethane (5 mL) was stirred at 25° C. for 2 hours. The mixture was concentrated under vacuum. The reaction mixture was adjusted to pH 7 with ammonia in methanol (7 mol/L). The residue was purified by lash chromatography on C18 (acetonitrile-0.1% FA in water) to afford 6-(5-amino-4-methylpyridin-3-yl)-N3-(7,7-difluoro-4-methyl-5,6,7,8-tetrahydro-4H-pyrazolo[1,5-a]azepin-2-yl)-7-fluoroisoquinoline-3,8-diamine (19.9 mg, 0.043 mmol) as a yellow solid. LCMS (ESI) [M+H]$^+$=486.2. $^1$HNMR (300 MHz, DMSO-d$_6$) δ 9.29 (s, 1H), 9.14 (s, 1H), 8.01 (s, 1H), 7.77 (s, 1H), 7.73 (s, 1H), 6.75 (d, J=6.1 Hz, 1H), 6.13 (s, 2H), 5.94 (s, 1H), 5.55 (s, 2H), 4.77-4.65 (m, 1H), 4.48-4.35 (m, 1H), 3.04-2.95 (m, 1H), 2.40-2.20 (m, 2H) 1.99 (s, 3H), 1.82 (d, J=14.4 Hz, 1H), 1.50-1.40 (m, 1H), 1.32 (d, J=6.9 Hz, 3H).

Example 162

5-((8-amino-6-(5-amino-4-methylpyridin-3-yl)-7-fluoroisoquinolin-3-yl)amino)-1-methyl-1,3-dihydroisothiazolo[4,3-b]pyridine 2,2-dioxide (Compound 263)

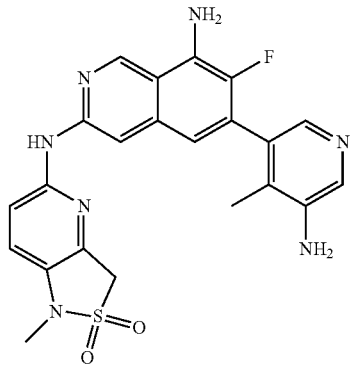 [SMILES: Cc1c(N)cncc1-c1cc2cc(Nc3ccc4c(n3)CS(=O)(=O)N4C)ncc2c(N)c1F]

Step 1:
N-(2,6-dichloro-3-pyridyl)methanesulfonamide

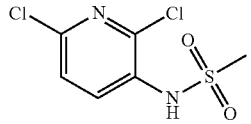

A solution of 2,6-dichloro-3-pyridinylamine (3.0 g, 18.4 mmol), triethylamine (9.29 g, 92.02 mmol) and methanesulfonyl chloride (6.29 g, 55.21 mmol) in dichloromethane (120 mL) was stirred at 0° C. for 2 hours. The reaction mixture was adjusted to pH 10 with 10% sodium hydroxide solution. The resulting mixture was stirred at 20° C. for 1 hour. The resulting mixture was extracted with dichloromethane and aqueous layers were combined. The reaction mixture was adjusted to pH 5 with 12% hydrochloric acid solution. After filtration, the solids were collected and dried to afford N-(2,6-dichloro-3-pyridyl)methanesulfonamide (3 g, 12.44 mmol) as a colorless solid. LCMS (ESI) [M+H]$^+$=241.1.

Step 2: N-(2,6-dichloro-3-pyridyl)-N-methyl-methanesulfonamide

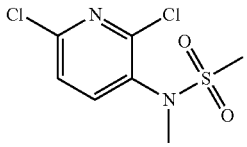

A solution of N-(2,6-dichloro-3-pyridyl)methanesulfonamide (3.5 g, 14.52 mmol), potassium carbonate (5.01 g, 36.29 mmol), tetrabutylammonium bromide (0.93 g, 2.9 mmol) and iodomethane (6.18 g, 43.55 mmol) in N,N-dimethylformamide (170 mL) was stirred at 20° C. for 3 hours. After filtration, the filtrate was concentrated under reduced pressure. The residue was purified by a reversed-phase chromatography (C18 silica gel; 0.5% sodium bicarbonate in water: ACN (5% 70%) in 30 min) to afford N-(2,6-dichloro-3-pyridyl)-N-methyl-methanesulfonamide (3.5 g, 13.72 mmol) as a red oil. LC/MS (ESI): [M+H]+=255.1.

Step 3: 5-chloro-1-methyl-3H-isothiazolo[4,3-b]pyridine 2,2-dioxide

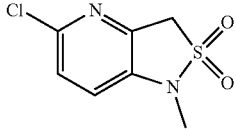

To a solution of N-(2,6-dichloro-3-pyridyl)-N-methyl-methanesulfonamide (2.2 g, 8.62 mmol) and potassium tert-butoxide (2.41 g, 21.56 mmol) in dimethyl sulfoxide (70 mL) was stirred at 20° C. for 2 hours. After filtration, the reaction system was purified by a reversed-phase chromatography (C18 silica gel; 0.5% sodium bicarbonate in water: methanol (5% 45%) in 30 min) to afford 5-chloro-1-methyl-3H-isothiazolo[4,3-b]pyridine 2,2-dioxide (900 mg, 4.12 mmol) as a brown solid. LCMS (ESI) [M+H]+=218.7.

Step 4: tert-butyl N-tert-butoxycarbonyl-N-[5-[8-chloro-7-fluoro-3-[(1-methyl-2,2-dioxo-3H-isothiazolo[4,3-b]pyridin-5-yl)amino]-6-isoquinolyl]-4-methyl-3-pyridyl]carbamate

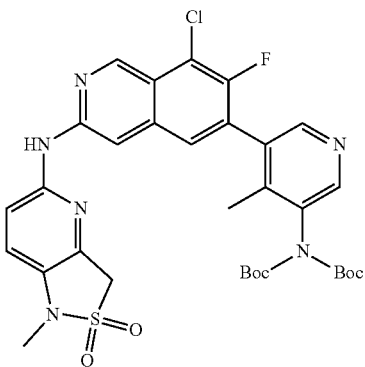 [SMILES: Cc1c(-c2cc3cc(Nc4ccc5c(n4)CS(=O)(=O)N5C)ncc3c(Cl)c2F)cncc1N(C(=O)OC(C)(C)C)C(=O)OC(C)(C)C]

A mixture of tert-butyl N-[5-(3-amino-8-chloro-7-fluoro-6-isoquinolyl)-4-methyl-3-pyridyl]-N-tert-butoxycarbonyl-carbamate (300 mg, 0.60 mmol), 5-chloro-1-methyl-3H-isothiazolo[4,3-b]pyridine 2,2-dioxide (300 mg, 1.37 mmol), tris(dibenzylideneacetone)dipalladium-chloroformadduct (123.47 mg, 0.12 mmol), 4,5-bis(diphenylphosphino)-9,9-dimethylxanthene (103.43 mg, 0.18 mmol) and cesium carbonate (486.11 mg, 1.49 mmol) in 1,4-dioxane (30 mL) was stirred at 95° C. for 2 hours. After filtration, the filtrate was concentrated under reduced pressure. The residue was purified by a reversed-phase chromatography (C18 silica gel; 0.5% sodium bicarbonate in water:methanol (5% 70%) in 30 min) to afford tert-butyl N-tert-butoxycarbonyl-N-[5-[8-chloro-7-fluoro-3-[(1-methyl-2,2-dioxo-3H-isothiazolo[4,3-b]pyridin-5-yl)amino]-6-isoquinolyl]-4-methyl-3-pyridyl]carbamate (150 mg, 0.22 mmol) as a brown solid. LCMS (ESI) [M+H]+=685.2.

Step 5: tert-butyl N-tert-butoxycarbonyl-N-[5-[8-(tert-butoxycarbonylamino)-7-fluoro-3-[(1-methyl-2,2-dioxo-3H-isothiazolo[4,3-b]pyridin-5-yl)amino]-6-isoquinolyl]-4-methyl-3-pyridyl]carbamate

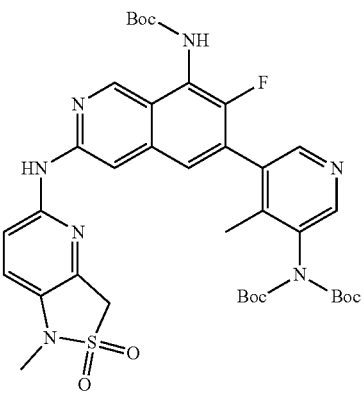 [SMILES: Cc1c(-c2cc3cc(Nc4ccc5c(n4)CS(=O)(=O)N5C)ncc3c(NC(=O)OC(C)(C)C)c2F)cncc1N(C(=O)OC(C)(C)C)C(=O)OC(C)(C)C]

A mixture of [tert-Butyl carbamate (250 mg, 2.13 mmol), tris(dibenzylideneacetone)dipalladium-chloroformadduct (15 mg, 0.01 mmol), Brettphos (8.0 mg, 0.01 mmol), tert-butyl N-tert-butoxycarbonyl-N-[5-[8-chloro-7-fluoro-3-[(1-methyl-2,2-dioxo-3H-isothiazolo[4,3-b]pyridin-5-yl)amino]-6-isoquinolyl]-4-methyl-3-pyridyl]carbamate (50 mg, 0.07 mmol) and cesium carbonate (95.0 mg, 0.29 mmol) in 1,4-dioxane (1 mL) was stirred for 2 hours at 90° C. The mixture was concentrated under vacuum. The residue was purified by flash chromatography on silica gel eluting with methanol/dichloromethane] (5/95) to afford tert-butyl N-tert-butoxycarbonyl-N-[5-[8-(tert-butoxycarbonylamino)-7-fluoro-3-[(1-methyl-2,2-dioxo-3H-isothiazolo[4,3-b]pyridin-5-yl)amino]-6-isoquinolyl]-4-methyl-3-pyridyl]carbamate (50 mg, 0.065 mmol) as a yellow oil. LCMS (ESI) [M+H]+=765.9.

Step 6: [6-(5-amino-4-methyl-3-pyridyl)-7-fluoro-N3-(1-methyl-2,2-dioxo-3H-isothiazolo[4,3-b]pyridin-5-yl)isoquinoline-3,8-diamine

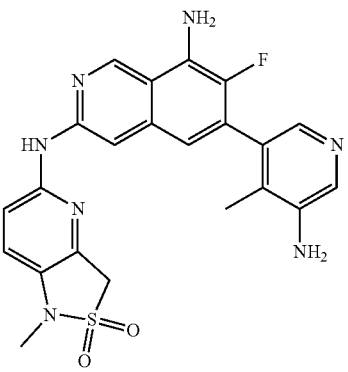 [SMILES: Cc1c(N)cncc1-c1cc2cc(Nc3ccc4c(n3)CS(=O)(=O)N4C)ncc2c(N)c1F]

A solution of [tert-butyl N-tert-butoxycarbonyl-N-[5-[8-(tert-butoxycarbonylamino)-7-fluoro-3-[(1-methyl-2,2-dioxo-3H-isothiazolo[4,3-b]pyridin-5-yl)amino]-6-isoquinolyl]-4-methyl-3-pyridyl]carbamate (300 mg, 0.39 mmol) and 2,2,2-trifluoroacetic acid (0.2 mL, 0.39 mmol) in dichloromethane (1 mL) was stirred at 25° C. for 30 minutes. The reaction was quenched by ammonia in methanol (7 mol/L). The solvent was concentrated under vacuum. The residue was purified by flash chromatography on C18 (acetonitrile-0.1% sodium bicarbonate in water) afford 5-((8-amino-6-(5-amino-4-methylpyridin-3-yl)-7-fluoroisoquinolin-3-yl)amino)-1-methyl-1,3-dihydroisothiazolo[4,3-b]pyridine 2,2-dioxide (17.1 mg, 0.037 mmol) as a yellow solid. LCMS (ESI): [M+H]$^+$=466.2. $^1$H NMR (300 MHz, DMSO-d$_6$) δ 9.69 (s, 1H), 9.35 (s, 1H), 8.23 (s, 1H), 8.00 (s, 1H), 7.68 (s, 1H), 7.45-7.28 (m, 2H), 6.77 (d, J=6.2 Hz, 1H), 6.16 (s, 2H), 5.26 (s, 2H), 4.79 (s, 2H), 3.05 (s, 3H), 1.94 (d, J=1.4 Hz, 3H).

Example 163

6-(5-amino-4-methylpyridin-3-yl)-7-fluoro-N3-((4S,7S)-7-methoxy-4-methyl-5,6,7,8-tetrahydro-4H-pyrazolo[1,5-a]azepin-2-yl)isoquinoline-3,8-diamine (Compound 265)

6-(5-amino-4-methylpyridin-3-yl)-7-fluoro-N3-((4R,7R)-7-methoxy-4-methyl-5,6,7,8-tetrahydro-4H-pyrazolo[1,5-a]azepin-2-yl)isoquinoline-3,8-diamine (Compound 266)

6-(5-amino-4-methylpyridin-3-yl)-7-fluoro-N3-((4S,7R)-7-methoxy-4-methyl-5,6,7,8-tetrahydro-4H-pyrazolo[1,5-a]azepin-2-yl)isoquinoline-3,8-diamine (Compound 267) and 6-(5-amino-4-methylpyridin-3-yl)-7-fluoro-N3-((4R,7S)-7-methoxy-4-methyl-5,6,7,8-tetrahydro-4H-pyrazolo[1,5-a]azepin-2-yl)isoquinoline-3,8-diamine (Compound 268)

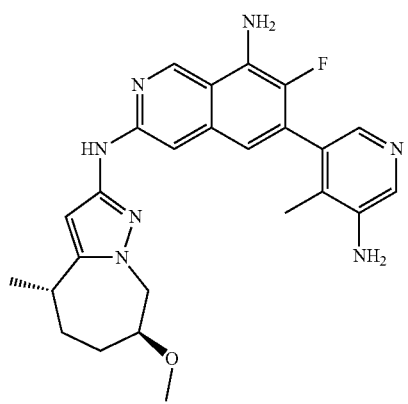

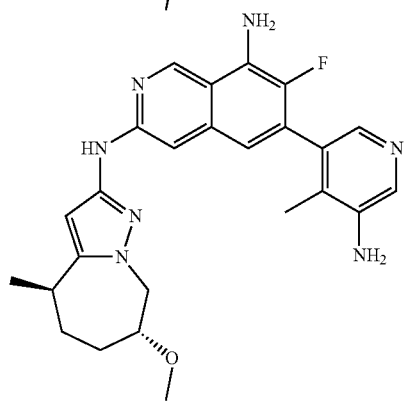

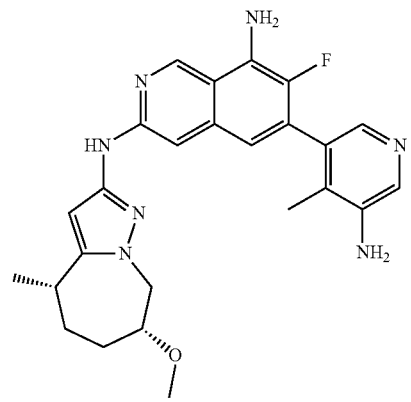

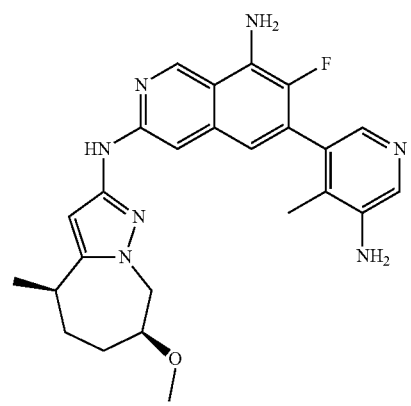

Step 1: 1-(3,5-dibromo-1H-pyrazol-1-yl)hex-5-en-2-ol

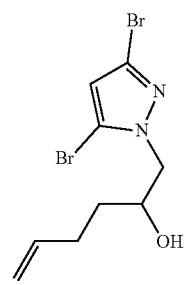

To a solution of 3,5-dibromo-1H-pyrazole (1.5 g, 6.7 mmol) in acetonitrile (20 mL) and 2-(but-3-enyl)oxirane (2 g, 20 mmol) was added potassium carbonate (2.8 g, 20 mmol). The resulting mixture was stirred for 2 hour at 80° C. The reaction was quenched with water and then extracted with ethyl acetate dried with anhydrous sodium sulfate. After filtration, the filtrate was concentrated under vacuum to afford 1-(3,5-dibromo-1H-pyrazol-1-yl)hex-5-en-2-ol (1.4 g, 4.3 mmol) as a yellow oil. LCMS (ESI) [M+H]$^+$=323.

Step 2: 2-bromo-4-methylene-5,6,7,8-tetrahydro-4H-pyrazolo[1,5-a]azepin-7-ol

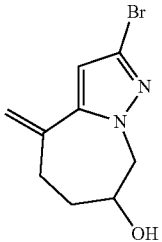

A mixture of 1-(3,5-dibromo-1H-pyrazol-1-yl)hex-5-en-2-ol (5.2 g, 16.15 mmol), palladium acetate (361 mg, 1.62 mmol), triphenylphosphine (846 mg, 3.23 mmol), potassium acetate (4.7 g, 48.45 mmol) and tetrabutylammonium bromide (5.2 g, 16.15 mmol) in N,N-dimethylformamide (50 mL) was stirred overnight at 90° C. After filtration, the filtrate was concentrated under vacuum. The residue was purified by flash chromatography on silica gel eluting with petroleum ether/ethyl acetate (1/1) to afford 2-bromo-4-methylene-5,6,7,8-tetrahydro-4H-pyrazolo[1,5-a]azepin-7-ol (3.6 g, 14.8 mmol) as an off-white solid. LCMS (ESI) [M+H]$^+$=243.

Step 3: 2-bromo-7-methoxy-4-methylene-5,6,7,8-tetrahydro-4H-pyrazolo[1,5-a]azepine

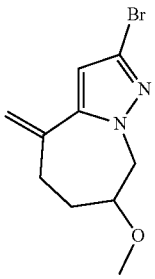

A mixture of 2-bromo-4-methylene-5,6,7,8-tetrahydro-4H-pyrazolo[1,5-a]azepin-7-ol (1 g, 4.12 mmol) and silver oxide in methyl iodide (15 mL) was refluxed overnight. The resulting solution was concentrated under vacuum. The residue was purified by flash chromatography on silica gel eluting with petroleum ether/ethyl acetate (2/1) to afford 2-bromo-7-methoxy-4-methylene-5,6,7,8-tetrahydro-4H-pyrazolo[1,5-a]azepine (1.02 g, 3.98 mmol) as a white solid. LCMS (ESI) [M+H]$^+$=257.

Step 4: tert-butyl N-tert-butoxycarbonyl (5-(8-chloro-7-fluoro-3-((7-methoxy-4-methylene-5,6,7,8-tetrahydro-4H-pyrazolo[1,5-a]azepin-2-yl)amino)isoquinolin-6-yl)-4-methylpyridin-3-yl)carbamate

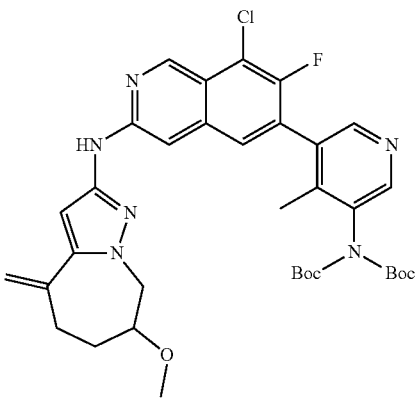 [SMILES: C=C1CCC(OC)Cn2nc(Nc3cc4cc(-c5cncc(N(C(=O)OC(C)(C)C)C(=O)OC(C)(C)C)c5C)c(F)c(Cl)c4cn3)cc21]

To a solution of 2-bromo-7-methoxy-4-methylene-5,6,7,8-tetrahydro-4H-pyrazolo[1,5-a]azepine (1.02 g, 3.97 mmol), tert-butyl N-tert-butoxycarbonyl (5-(3-amino-8-chloro-7-fluoroisoquinolin-6-yl)-4-methylpyridin-3-yl)carbamate (2 g, 3.97 mmol), t-BuBrettPhos Pd G3 (683 mg, 0.8 mmol) and t-BuBrettphos (774 mg, 1.6 mmol) in 1,4-dioxane (20 mL) was added cesium carbonate (3.9 g, 12 mmol). The resulting mixture was stirred for 2 hours at 120° C. After filtration, the filtrate was concentrated under vacuum. The residue was purified by flash chromatography on silica gel eluting with dichloromethane/methanol (9/1) to afford tert-butyl N-tert-butoxycarbonyl (5-(8-chloro-7-fluoro-3-((7-methoxy-4-methylene-5,6,7,8-tetrahydro-4H-pyrazolo[1,5-a]azepin-2-yl)amino)isoquinolin-6-yl)-4-methylpyridin-3-yl)carbamate (1.5 g, 2.21 mmol) as a deep-brown solid. LCMS (ESI) [M+H]$^+$=679.

Step 5: tert-butyl N-tert-butoxycarbonyl-N-(5-(8-((tert-butoxycarbonyl)amino)-7-fluoro-3-((7-methoxy-4-methylene-5,6,7,8-tetrahydro-4H-pyrazolo[1,5-a]azepin-2-yl)amino)isoquinolin-6-yl)-4-methylpyridin-3-yl)carbamate

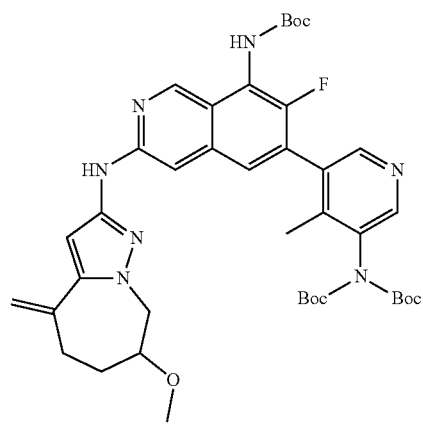

A mixture of the tert-butyl N-tert-butoxycarbonyl (5-(8-chloro-7-fluoro-3-((7-methoxy-4-methylene-5,6,7,8-tetrahydro-4H-pyrazolo[1,5-a]azepin-2-yl)amino)isoquinolin-6-yl)-4-methylpyridin-3-yl)carbamate (1.5 g, 2.2 mmol), tert-Butyl carbamate (7.7 g, 66 mmol), tris(dibenzylideneacetone)dipalladium (455 mg, 0.44 mmol) and Brettphos (236 mg, 0.44 mmol) in 1,4-dioxane (15 mL) was added cesium carbonate (2.9 g, 0.8 mmol). The resulting solution was stirred for 2 hours at 90° C. After filtration, the filtrate was concentrated under vacuum. The residue was purified by flash chromatography on silica gel eluting with dichloromethane/methanol (9/1) to afford tert-butyl N-tert-butoxycarbonyl-N-(5-(8-((tert-butoxycarbonyl)amino)-7-fluoro-3-((7-methoxy-4-methylene-5,6,7,8-tetrahydro-4H-pyrazolo[1,5-a]azepin-2-yl)amino)isoquinolin-6-yl)-4-methylpyridin-3-yl)carbamate (1.10 g, 1.45 mmol) as a deep-brown solid. LCMS (ESI) [M+H]$^+$=760.

747

Step 6: tert-butyl (tert-butoxycarbonyl)(5-(8-((tert-butoxycarbonyl)amino)-7-fluoro-3-((7-methoxy-4-methyl-5,6,7,8-tetrahydro-4H-pyrazolo[1,5-a]azepin-2-yl)amino)isoquinolin-6-yl)-4-methylpyridin-3-yl)carbamate

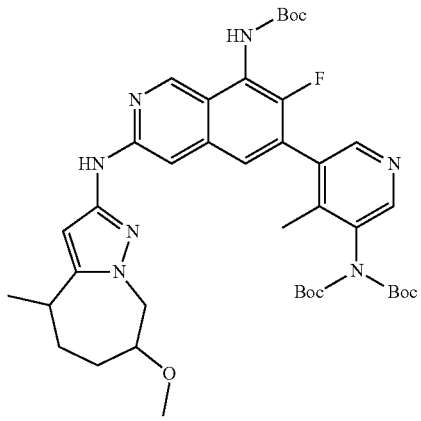 [SMILES: C=C1CCC(OC)Cn2nc(Nc3cc4cc(-c5cncc(N(C(=O)OC(C)(C)C)C(=O)OC(C)(C)C)c5C)c(F)c(NC(=O)OC(C)(C)C)c4cn3)cc21]

A mixture of tert-butyl N-tert-butoxycarbonyl-N-(5-(8-((tert-butoxycarbonyl)amino)-7-fluoro-3-((7-methoxy-4-methylene-5,6,7,8-tetrahydro-4H-pyrazolo[1,5-a]azepin-2-yl)amino)isoquinolin-6-yl)-4-methylpyridin-3-yl)carbamate (1.1 g, 1.45 mmol), platinum oxide (120 mg) in methanol (15 mL) was stirred for 16 hours at the room temperature. After filtration, the filtrate was concentrated under vacuum to afford tert-butyl (tert-butoxycarbonyl)(5-(8-((tert-butoxycarbonyl)amino)-7-fluoro-3-((7-methoxy-4-methyl-5,6,7,8-tetrahydro-4H-pyrazolo[1,5-a]azepin-2-yl)amino)isoquinolin-6-yl)-4-methylpyridin-3-yl)carbamate (800 mg, 1.05 mmol) as a yellow solid. LCMS (ESI) [M+H]⁺=762.

Step 7: 6-(5-amino-4-methylpyridin-3-yl)-7-fluoro-N3-((4S,7S)-7-methoxy-4-methyl-5,6,7,8-tetrahydro-4H-pyrazolo[1,5-a]azepin-2-yl)isoquinoline-3,8-diamine, 6-(5-amino-4-methylpyridin-3-yl)-7-fluoro-N3-((4R,7R)-7-methoxy-4-methyl-5,6,7,8-tetrahydro-4H-pyrazolo[1,5-a]azepin-2-yl)isoquinoline-3,8-diamine, 6-(5-amino-4-methylpyridin-3-yl)-7-fluoro-N3-((4S,7R)-7-methoxy-4-methyl-5,6,7,8-tetrahydro-4H-pyrazolo[1,5-a]azepin-2-yl)isoquinoline-3,8-diamine and 6-(5-amino-4-methylpyridin-3-yl)-7-fluoro-N3-((4R,7S)-7-methoxy-4-methyl-5,6,7,8-tetrahydro-4H-pyrazolo[1,5-a]azepin-2-yl)isoquinoline-3,8-diamine

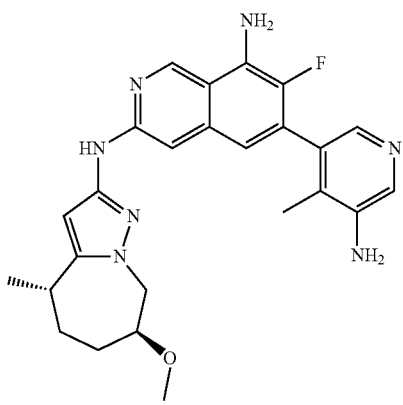

748

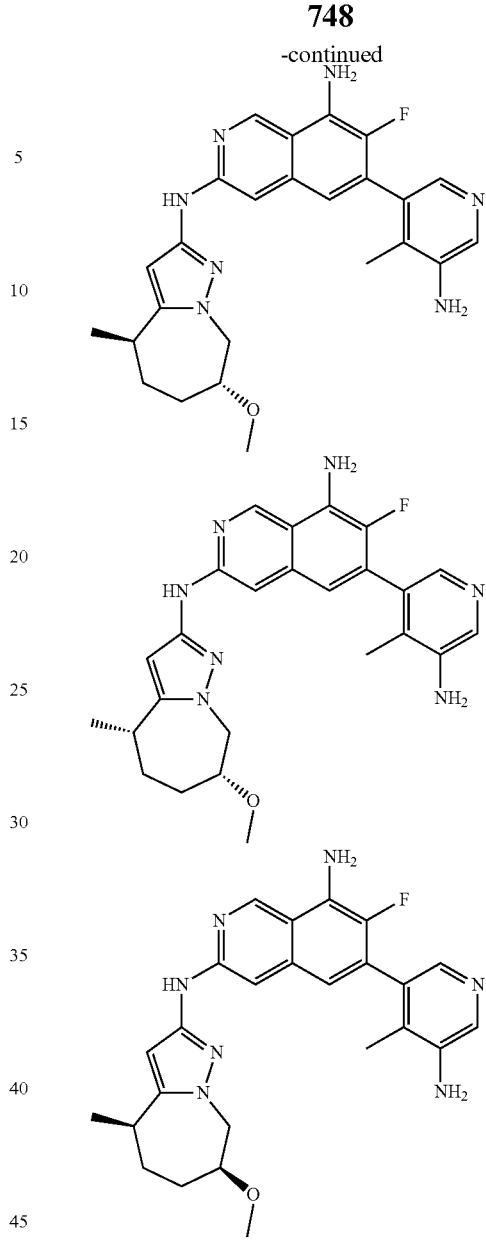

A solution of the tert-butyl (tert-butoxycarbonyl)(5-(8-((tert-butoxycarbonyl)amino)-7-fluoro-3-((7-methoxy-4-methyl-5,6,7,8-tetrahydro-4H-pyrazolo[1,5-a]azepin-2-yl)amino)isoquinolin-6-yl)-4-methylpyridin-3-yl)carbamate (800 mg, 1.05 mmol) in dichloromethane (10 mL) and 2,2,2-trifluoroacetic acid (10 mL) was stirred at 25° C. for 2 hours. The solvent was concentrated under vacuum. The crude product was purified by reverse-HPLC (C18 silica gel; 0.5% sodium bicarbonate in water:ACN=20%-50% in 7 min) to afford the mixture (168 mg, 0.36 mmol) as a yellow solid. The mixture was separated by Chiral-HPLC to afford four isomers. Compound 265: (56.3 mg) yellow solid. Retention time: 6.06 min (CHIRALPAK IE-3. 0.46*10 cm; 3 μm; MtBE (0.3% IPAmine):EtOH=70:30; 1.0 ml/min); LCMS (ESI) [M+H]⁺=462.3; ¹H NMR (300 MHz, DMSO-d6) δ 9.25 (s, 1H), 8.91 (s, 1H), 7.98 (s, 1H), 7.66 (d, J=4.6 Hz, 2H), 6.64 (d, J=6.1 Hz, 1H), 6.04 (s, 2H), 5.85 (s, 1H), 5.22 (s, 2H), 4.51 (dd, J=15.2, 5.3 Hz, 1H), 4.16 (d, J=14.7 Hz, 1H), 3.53 (s, 1H), 3.27 (s, 3H), 2.89-2.72 (m, 1H), 2.16-2.03 (m, 1H), 1.93 (s, 3H), 1.87-1.72 (m, 1H), 1.58-

1.42 (m, 2H), 1.27 (d, J=6.9 Hz, 3H). Compound 266: (48.7 mg) as a yellow solid. Retention time: 4.46 min (CHIRAL-PAK IE-3. 0.46*10 cm; 3 μm; MtBE (0.3% IPAmine):EtOH=70:30; 1.0 ml/min); LCMS (ESI) [M+H]+=462.3. Compound 268: (17.8 mg) as a yellow solid. Retention time: 6.53 min (CHIRALPAK IE-3. 0.46*10 cm; 3 μm; MtBE (0.3% IPAmine):EtOH=70:30; 1.0 ml/min); LCMS (ESI) [M+H]+=462.3; $^1$H NMR (300 MHz, DMSO-d6) δ 9.25 (s, 1H), 8.98 (s, 1H), 7.98 (s, 1H), 7.68 (d, J=6.9 Hz, 2H), 6.69 (d, J=6.1 Hz, 1H), 6.05 (s, 2H), 5.87 (s, 1H), 5.22 (s, 2H), 4.34 (d, J=14.0 Hz, 1H), 4.03 (dd, J=14.0, 9.5 Hz, 1H), 3.33 (s, 3H), 3.16 (s, 1H), 2.86 (s, 1H), 2.13 (s, 1H), 1.93 (s, 3H), 1.86-1.56 (m, 2H), 1.41-1.20 (m, 1H), 1.27 (t, J=6.8 Hz, 3H). Compound 267: (17.8 mg) as a yellow solid. Retention time: 11.8 min (CHIRALPAK IE-3. 0.46*10 cm; 3 μm;

MtBE (0.3% IPAmine):EtOH=70:30; 1.0 ml/min); LCMS (ESI) [M+H]$^+$=462.3.

Example 164

5-[8-amino-7-fluoro-3-[(6-isopropyl-7-oxo-5,8-di-hydro-4H-pyrazolo[1,5-d][1,4]diazepin-2-yl)amino]-6-isoquinolyl]-1-ethyl-pyrazole-3-carbonitrile (Compound 269)

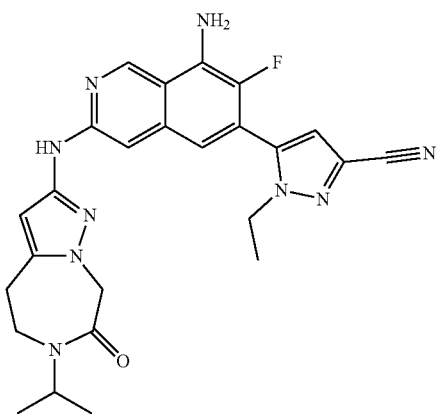 [SMILES: CCn1nc(C#N)cc1-c1cc2cc(Nc3cc4n(n3)CC(=O)N(C(C)C)CC4)ncc2c(N)c1F]

Step 1: methyl 5-bromo-1-ethyl-pyrazole-3-carboxylate

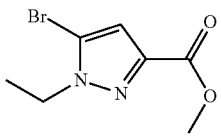

A mixture of methyl 5-bromo-1H-pyrazole-3-carboxylate (2.0 g, 9.76 mmol), iodoethane (4.5 g, 28.85 mmol) and potassium carbonate (3.0 g, 21.74 mmol) in tetrahydrofuran (50 mL) was stirred for 1 hour at 80° C. After filtration, the filtrate was concentrated under vacuum. The residue was purified by flash chromatography on silica gel eluting with petroleum ether/ethyl acetate (3/1) to afford methyl 5-bromo-1-ethyl-pyrazole-3-carboxylate (1.2 g, 5.15 mmol) as light yellow solid. LCMS (ESI) [M+H]$^+$=233.1.

Step 2: 5-bromo-1-ethyl-pyrazole-3-carboxamide

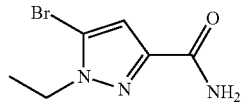

A mixture of methyl 5-bromo-1-ethyl-pyrazole-3-carboxylate (1.2 g, 5.15 mmol) in ammonium hydroxide (10 mL, 30%) was stirred for 1 hour at room temperature. The reaction solution was concentrated under vacuum to afford 5-bromo-1-ethyl-pyrazole-3-carboxamide (1.1 g, 5.05 mmol) as a white solid. LCMS (ESI) [M+H]$^+$=218.1.

Step 3: 5-bromo-1-ethyl-1H-pyrazole-3-carbonitrile

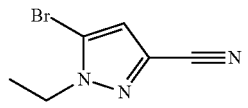

Trifluoroacetic anhydride (1.27 g, 6.05 mmol) was added dropwise into a solution of 5-bromo-1-ethyl-pyrazole-3-carboxamide (1.1 g, 5.05 mmol) and triethylamine (1.53 g, 15.14 mmol) in dichloromethane (30 mL) at 0° C. The resulting solution was stirred for 1 hour at room temperature. The mixture was concentrated under vacuum. The residue was purified by reverse phase chromatography (acetonitrile 0-60/0.05% sodium bicarbonate in water) to afford 5-bromo-1-ethyl-1H-pyrazole-3-carbonitrile (1 g, 5.00 mmol) as a white solid. LCMS (ESI) [M+H]=200.

Step 4: tert-butyl N-[6-(5-cyano-2-ethyl-pyrazol-3-yl)-7-fluoro-3-[(6-isopropyl-7-oxo-5,8-dihydro-4H-pyrazolo[1,5-d][1,4]diazepin-2-yl)amino]-8-isoquinolyl]carbamate

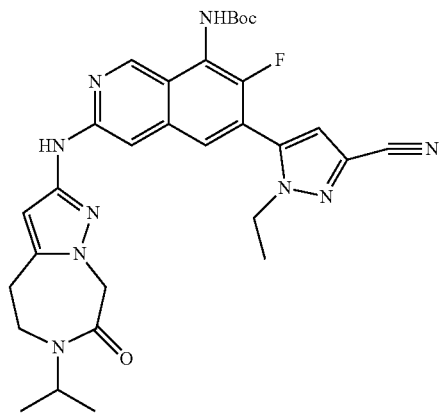 [SMILES: CCn1nc(C#N)cc1-c1cc2cc(Nc3cc4n(n3)CC(=O)N(C(C)C)CC4)ncc2c(NC(=O)OC(C)(C)C)c1F]

A solution of [8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]boronic acid (80 mg, 0.16 mmol) and potassium bifluoride (40 mg, 0.41 mmol) in 2-methyl-2-propanol (0.80 mL) and water (0.20 mL) was stirred at room temperature for 5 hours. 5-Bromo-1-ethyl-pyrazole-3-carbonitrile (80 mg, 0.40 mmol), potassium phosphate (96 mg, 0.45 mmol) and tetrakis(triphenylphosphine)palladium (40 mg, 0.03 mmol) was added. The resulting mixture was stirred at 100° C. for 4.5 hours under the irradiation of microwave. The resulting mixture was concentrated under vacuum. The residue was purified by flash chromatography on silica gel eluting with dichloromethane/methanol (20/1) to afford tert-butyl N-[6-(5-cyano-2-ethyl-pyrazol-3-yl)-7-fluoro-3-[(6-isopropyl-7-oxo-5,8-dihydro-4H-pyrazolo[1,5-d][1,4]diazepin-2-yl)amino]-8-isoquinolyl]carbamate (45 mg, 0.077 mmol) as yellow solid. LCMS (ESI) [M+H]$^+$=588.3.

Step 5: 5-[8-amino-7-fluoro-3-[(6-isopropyl-7-oxo-5,8-dihydro-4H-pyrazolo[1,5-d][1,4]diazepin-2-yl)amino]-6-isoquinolyl]-1-ethyl-pyrazole-3-carbonitrile

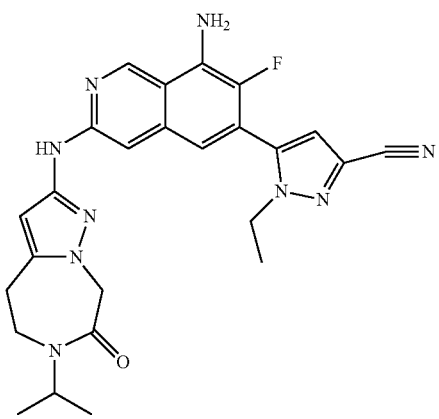 [SMILES: CCn1nc(C#N)cc1-c1cc2cc(Nc3cc4n(n3)CC(=O)N(C(C)C)CC4)ncc2c(N)c1F]

A solution of tert-butyl N-[6-(5-cyano-2-ethyl-pyrazol-3-yl)-7-fluoro-3-[(6-isopropyl-7-oxo-5,8-dihydro-4H-pyrazolo[1,5-d][1,4]diazepin-2-yl)amino]-8-isoquinolyl]carbamate (40 mg, 0.07 mmol) and 2,2,2-trifluoroacetic acid (1 mL) in dichloromethane (4 mL) was stirred for 1 hours at room temperature. The mixture was concentrated under vacuum. The reaction mixture was adjusted to pH 7 with triethylamine. The crude product was purified by Prep-HPLC with the following conditions: Column, Atlantis HILIC OBD Column 19*150*5 μm; mobile phase: Water (10 mmol/L sodium bicarbonate) and ACN (40-50% in 7 min); Detector, UV 254 nm. 5-[8-amino-7-fluoro-3-[(6-isopropyl-7-oxo-5,8-dihydro-4H-pyrazolo[1,5-d][1,4]diazepin-2-yl)amino]-6-isoquinolyl]-1-ethyl-pyrazole-3-carbonitrile (13.8 mg, 0.028 mmol) was obtained as yellow solid. LCMS (ESI) [M+H]$^+$=488.4; $^1$HNMR (400 MHz, DMSO-d$_6$) δ 9.30 (s, 1H), 9.19 (s, 1H), 7.76 (s, 1H), 7.19 (s, 1H), 6.94 (d, J=5.8 Hz, 1H), 6.30 (s, 2H), 5.96 (s, 1H), 4.97 (s, 2H), 4.61-4.57 (m, 1H), 4.16 (q, J=7.3 Hz, 2H), 3.79-3.76 (m, 2H), 2.98 (t, J=5.8 Hz, 2H), 1.33 (t, J=7.2 Hz, 3H), 1.12 (d, J=6.8 Hz, 6H).

Example 165

2-[[8-amino-7-fluoro-6-(5,6,7,8-tetrahydroimidazo[1,2-a]pyrazin-3-yl)-3-isoquinolyl]amino]-6-isopropyl-5,8-dihydro-4H-pyrazolo[1,5-d][1,4]diazepin-7-one (Compound 270)

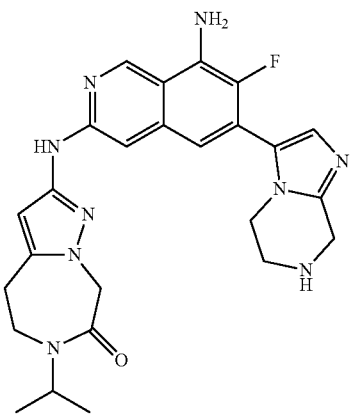 [SMILES: CC(C)N1CCc2cc(Nc3cc4cc(-c5cnc6n5CCNC6)c(F)c(N)c4cn3)nn2CC1=O]

Step 1: tert-butyl 3-(3-amino-8-chloro-7-fluoro-6-isoquinolyl)-6,8-dihydro-5H-imidazo [1,2-a]pyrazine-7-carboxylate

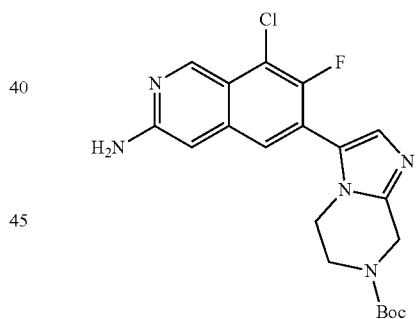

A mixture of tert-butyl 6,8-dihydro-5H-imidazo[1,2-a]pyrazine-7-carboxylate (1.0 g, 4.48 mmol), 8-chloro-7-fluoro-6-iodo-isoquinolin-3-amine (1.5 g, 4.65 mmol), potassium carbonate (1.0 g, 7.25 mmol), palladium acetate (122 mg, 0.37 mmol), tricyclohexyl phosphine (210 mg, 0.75 mmol) and trimethylacetic acid (115 mg, 1.13 mmol) in N,N-dimethylacetamide (20 mL) was stirred for 6 hours at 100° C. The resulting mixture was cooled to room temperature and then filtered. The filtrate was concentrated under vacuum. The residue was purified by reverse phase chromatography (acetonitrile 0-55/0.05% sodium bicarbonate in water) to afford tert-butyl 3-(3-amino-8-chloro-7-fluoro-6-isoquinolyl)-6,8-dihydro-5H-imidazo[1,2-a]pyrazine-7-carboxylate (500 mg, 1.20 mmol) as a yellow solid. LCMS (ESI) [M+H]$^+$=418.1.

Step 2: tert-butyl 3-[8-chloro-7-fluoro-3-[(6-isopropyl-7-oxo-5,8-dihydro-4H-pyrazolo[1,5-d][1,4]diazepin-2-yl)amino]-6-isoquinolyl]-6,8-dihydro-5H-imidazo[1,2-a]pyrazine-7-carboxylate

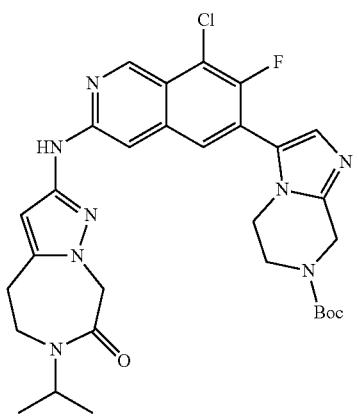 [SMILES: CC(C)N1CCc2cc(Nc3cc4cc(-c5cnc6n5CCN(C(=O)OC(C)(C)C)C6)c(F)c(Cl)c4cn3)nn2CC1=O]

A mixture of tert-butyl 3-(3-amino-8-chloro-7-fluoro-6-isoquinolyl)-6,8-dihydro-5H-imidazo[1,2-a]pyrazine-7-carboxylate (350 mg, 0.84 mmol), 2-bromo-6-isopropyl-5,8-dihydro-4H-pyrazolo[1,5-d][1,4]diazepin-7-one (455 mg, 1.67 mmol), t-BuBrettPhosPdG3 (350 mg, 0.41 mmol), t-BuBrettPhos (420 mg, 0.73 mmol) and cesium carbonate (805 mg, 2.47 mmol) in 1,4-dioxane (35 mL) was stirred at 120° C. for 1.5 hours. After filtration, the filtrate was concentrated under vacuum. The residue was purified by flash chromatography on silica gel eluting with dichloromethane/methanol (20/1) to afford tert-butyl 3-[8-chloro-7-fluoro-3-[(6-isopropyl-7-oxo-5,8-dihydro-4H-pyrazolo[1,5-d][1,4]diazepin-2-yl)amino]-6-isoquinolyl]-6,8-dihydro-5H-imidazo[1,2-a]pyrazine-7-carboxylate (300 mg, 0.49 mmol) as yellow solid. LCMS (ESI) [M+H]$^+$=609.2.

Step 3: tert-butyl 3-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-6,8-dihydro-5H-imidazo[1,2-a]pyrazine-7-carboxylate

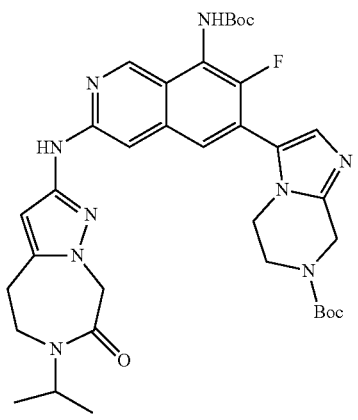 [SMILES: CC(C)N1CCc2cc(Nc3cc4cc(-c5cnc6n5CCN(C(=O)OC(C)(C)C)C6)c(F)c(NC(=O)OC(C)(C)C)c4cn3)nn2CC1=O]

A mixture of tert-butyl 3-[8-chloro-7-fluoro-3-[(6-isopropyl-7-oxo-5,8-dihydro-4H-pyrazolo[1,5-d][1,4]diazepin-2-yl)amino]-6-isoquinolyl]-6,8-dihydro-5H-imidazo[1,2-a]pyrazine-7-carboxylate (260 mg, 0.43 mmol), tris(dibenzylideneacetone)dipalladium (78 mg, 0.08 mmol), Brettphos (91 mg, 0.17 mmol), tert-Butyl carbamate (1.56 g, 13.32 mmol) and cesium carbonate (416 mg, 1.28 mmol) in 1,4-dioxane (26 mL) was stirred for 16 hours at 90° C. After filtration, the filtrate was concentrated under vacuum. The residue was purified by reverse phase chromatography (acetonitrile 0-60/0.05% sodium bicarbonate in water) to afford tert-butyl 3-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-6,8-dihydro-5H-imidazo[1,2-a]pyrazine-7-carboxylate (150 mg, 0.22 mmol) as a brown solid. LCMS (ESI) [M+H]$^+$=690.3.

Step 4: 2-[[8-amino-7-fluoro-6-(5,6,7,8-tetrahydroimidazo[1,2-a]pyrazin-3-yl)-3-isoquinolyl]amino]-6-isopropyl-5,8-dihydro-4H-pyrazolo[1,5-d][1,4]diazepin-7-one

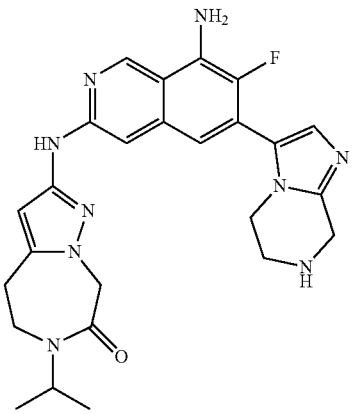 [SMILES: CC(C)N1CCc2cc(Nc3cc4cc(-c5cnc6n5CCNC6)c(F)c(N)c4cn3)nn2CC1=O]

A solution of tert-butyl 3-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-6,8-dihydro-5H-imidazo[1,2-a]pyrazine-7-carboxylate (145 mg, 0.21 mmol) in dichloromethane (6 mL) was added 2,2,2-trifluoroacetic acid (1.5 mL). The resulting solution was stirred for 1 hour at 25° C. and then concentrated under vacuum. The residue was adjusted to pH 7 with triethylamine. The crude product was purified by Prep-HPLC: Atlantis HILIC OBD Column 19*150*5 um; Water (10 mmol/L sodium bicarbonate) and ACN (20-30% in 7 min) to afford 2-[[8-amino-7-fluoro-6-(5,6,7,8-tetrahydroimidazo[1,2-a]pyrazin-3-yl)-3-isoquinolyl]amino]-6-isopropyl-5,8-dihydro-4H-pyrazolo[1,5-d][1,4]diazepin-7-one (17.2 mg, 0.035 mmol) as a yellow solid. LCMS (ESI) [M+H]$^+$=490.3. $^1$HNMR (400 MHz, DMSO-d$_6$) δ 9.22 (s, 1H), 9.06 (s, 1H), 7.67 (s, 1H), 7.07 (d, J=1.5 Hz, 1H), 6.85 (d, J=6.1 Hz, 1H), 6.07 (s, 2H), 5.96 (s, 1H), 4.97 (s, 2H), 4.60 (t, J=6.7 Hz, 1H), 3.97-3.85 (m, 4H), 3.79-3.77 (m, 2H), 3.04-2.98 (m, 4H), 2.75 (s, 1H), 1.12 (d, J=6.8 Hz, 6H).

Example 166

2-((8-amino-6-(5-amino-4-methylpyridin-3-yl)-7-fluoroisoquinolin-3-yl)amino)-5,6-dihydro-4H,8H-pyrazolo[1,5-c][1,3]thiazepine 7,7-dioxide (Compound 271)

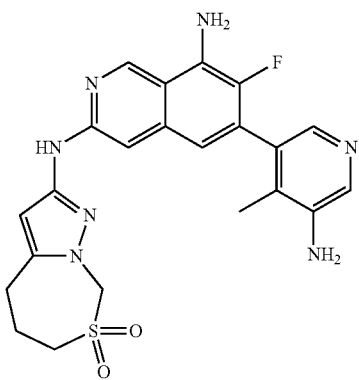 [SMILES: Cc1c(N)cncc1-c1cc2cc(Nc3cc4n(n3)CS(=O)(=O)CCC4)ncc2c(N)c1F]

Step 1: 2-bromo-6,8-dihydropyrazolo[1,5-c][1,3]thiazepine 7,7-dioxide

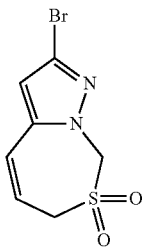 [SMILES: O=S1(=O)CC=Cc2cc(Br)nn2C1]

A mixture of 1-(allylsulfonylmethyl)-3,5-dibromo-pyrazole (2.0 g, 5.81 mmol), triethylamine (4.11 g, 40.7 mmol), palladium acetate (0.2 g, 0.87 mmol) and tri(2-methylphenyl)phosphine (530.2 mg, 1.74 mmol) in N,N-dimethylformamide (120 mL) was stirred at 140° C. for 1 hour. The reaction was cooled to room temperature and then concentrated under vacuum. The residue was purified by flash chromatography on silica gel eluting with petroleum ether/ethyl acetate (6/1) to afford 2-bromo-6,8-dihydropyrazolo[1,5-c][1,3]thiazepine 7,7-dioxide (100 mg, 0.38 mmol) as a light yellow solid. LCMS (ESI) [M+H]$^+$=263.2.

Step 2: 2-bromo-4,5,6,8-tetrahydropyrazolo[1,5-c][1,3]thiazepine 7,7-dioxide

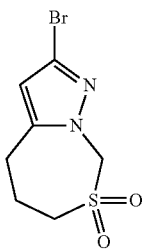 [SMILES: O=S1(=O)CCCc2cc(Br)nn2C1]

A mixture of 2-bromo-6,8-dihydropyrazolo[1,5-c][1,3]thiazepine 7,7-dioxide (200.0 mg, 0.76 mmol), platinum oxide (17.26 mg, 0.08 mmol) and acetic acid (9.12 mg, 0.15 mmol) in methanol (30 mL) was stirred at 20° C. for 1 hour under hydrogen (2 atm). After filtration, the filtrate was concentrated under reduced pressure. The residue was purified by a reversed-phase flash (C18 silica gel; 0.5% sodium bicarbonate in water: MeOH=95% 60% in 20 min) to afford 2-bromo-4,5,6,8-tetrahydropyrazolo[1,5-c][1,3]thiazepine 7,7-dioxide (130 mg, 0.49 mmol) as a white solid. LCMS45 (ESI) [M+H]$^+$=265.3.

Step 3: Tert-butyl N-tert-butoxycarbonyl-N-[5-[8-chloro-3-[(7,7-dioxo-4,5,6,8-tetrahydropyrazolo[1,5-c][1,3]thiazepin-2-yl)amino]-7-fluoro-6-isoquinolyl]-4-methyl-3-pyridyl]carbamate

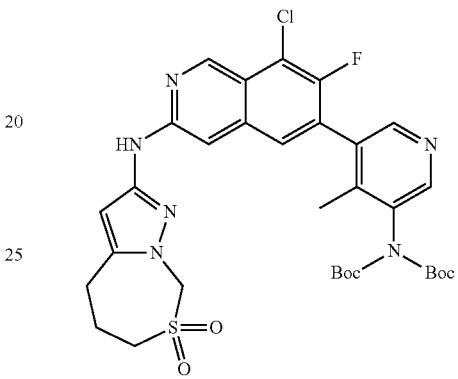

A mixture of tert-butyl N-[5-(3-amino-8-chloro-7-fluoro-6-isoquinolyl)-4-methyl-3-pyridyl]-N-tert-butoxycarbonyl-carbamate (140 mg, 0.28 mmol), 2-bromo-4,5,6,8-tetrahydropyrazolo[1,5-c][1,3]thiazepine 7,7-dioxide (140 mg, 0.53 mmol), t-BuBrettPhos Pd G3 (190.17 mg, 0.22 mmol), t-BuBrettPhos (134.72 mg, 0.28 mmol) and cesium carbonate (453.7 mg, 1.39 mmol) in 1,4-dioxane (28 mL) was stirred for 2 hours at 130° C. After filtration, the filtrate was concentrated under reduced pressure. The residue was purified by a reversed-phase flash (C18 silica gel; 0.5% sodium bicarbonate in water: MeOH=95% 35% in 20 min) to afford tert-butyl N-tert-butoxycarbonyl-N-[5-[8-chloro-3-[(7,7-dioxo-4,5,6,8-tetrahydropyrazolo[1,5-c][1,3]thiazepin-2-yl)amino]-7-fluoro-6-isoquinolyl]-4-methyl-3-pyridyl]carbamate (75 mg, 0.11 mmol) as a yellow solid. LCMS (ESI) [M+H]$^+$=687.3.

Step 4: Tert-butyl N-tert-butoxycarbonyl-N-[5-[8-(tert-butoxycarbonylamino)-3-[(7,7-dioxo-4,5,6,8-tetrahydropyrazolo[1,5-c][1,3]thiazepin-2-yl)amino]-7-fluoro-6-isoquinolyl]-4-methyl-3-pyridyl]carbamate

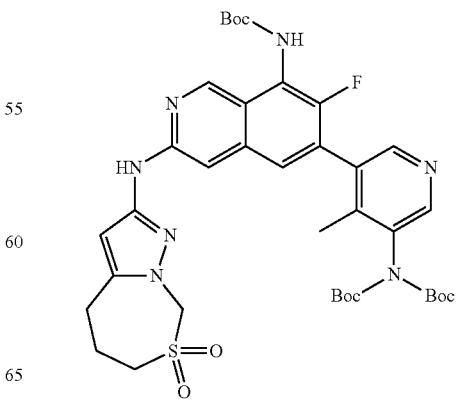

A mixture of tert-butyl N-tert-butoxycarbonyl-N-[5-[8-chloro-3-[(7,7-dioxo-4,5,6,8-tetrahydropyrazolo[1,5-c][1,3]thiazepin-2-yl)amino]-7-fluoro-6-isoquinolyl]-4-methyl-3-pyridyl]carbamate (100 mg, 0.15 mmol), tert-butyl carbamate (425.65 mg, 3.64 mmol), tris(dibenzylideneacetone)dipalladium-chloroformadduct (22.59 mg, 0.02 mmol), BrettPhos (15.6 mg, 0.03 mmol) and cesium carbonate (237.2 mg, 0.73 mmol) in 1,4-dioxane (10 mL) was stirred for 2 hours at 90° C. After filtration, the filtrate was concentrated under reduced pressure to afford tert-butyl N-tert-butoxycarbonyl-N-[5-[8-(tert-butoxycarbonylamino)-3-[(7,7-dioxo-4,5,6,8-tetrahydropyrazolo[1,5-c][1,3]thiazepin-2-yl)amino]-7-fluoro-6-isoquinolyl]-4-methyl-3-pyridyl]carbamate (100 mg, 0.13 mmol) as a brown oil. LCMS (ESI) [M+H]$^+$=768.4.

Step 5: 6-(5-amino-4-methyl-3-pyridyl)-N3-(7,7-dioxo-4,5,6,8-tetrahydropyrazolo[1,5-c][1,3]thiazepin-2-yl)-7-fluoro-isoquinoline-3,8-diamine

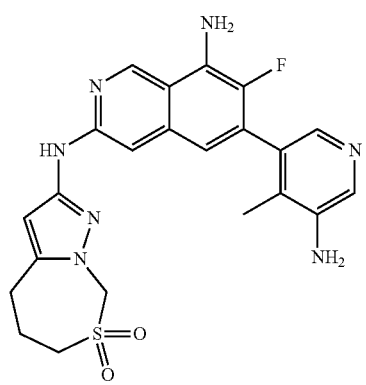 [SMILES: Cc1c(N)cncc1-c1cc2cc(Nc3cc4n(n3)CS(=O)(=O)CCC4)ncc2c(N)c1F]

A solution of tert-butyl N-tert-butoxycarbonyl-N-[5-[8-(tert-butoxycarbonylamino)-3-[(7,7-dioxo-4,5,6,8-tetrahydropyrazolo[1,5-c][1,3]thiazepin-2-yl)amino]-7-fluoro-6-isoquinolyl]-4-methyl-3-pyridyl]carbamate (100 mg, 0.13 mmol) and 2,2,2-trifluoroacetic acid (10.0 mL, 1.3 mmol) in dichloromethane (10 mL) was stirred at 20° C. for 1 hour. The resulting mixture was concentrated under vacuum. The pH value of the solution was adjusted to 10 with ammonia in methanol (7 mol/L). The crude product was purified by Prep-HPLC (C18 silica gel; 0.5% sodium bicarbonate in water: CH$_3$CN=95% 35% in 45 min) to afford 6-(5-amino-4-methyl-3-pyridyl)-N3-(7,7-dioxo-4,5,6,8-tetrahydropyrazolo[1,5-c][1,3]thiazepin-2-yl)-7-fluoro-isoquinoline-3,8-diamine (10.3 mg, 0.02 mmol) as a yellow solid. LCMS (ESI) [M+H]$^+$=468.2; $^1$HNMR (300 MHz, DMSO-d$_6$) δ 9.28 (s, 1H), 9.26 (s, 2H), 8.00 (s, 1H), 7.80 (s, 2H), 6.74-6.72 (m, 1H), 6.13 (s, 2H), 6.04 (s, 1H), 5.73-5.45 (m, 4H), 3.50-3.40 (m, 2H), 2.97-2.94 (m, 2H), 2.03-1.98 (m, 5H).

Example 167

2-[[8-amino-7-fluoro-6-(5-methyl-2-oxo-1H-pyridin-4-yl)-3-isoquinolyl]amino]-6-isopropyl-5,8-dihydro-4H-pyrazolo[1,5-d][1,4]diazepin-7-one; Formic Acid (Compound 272)

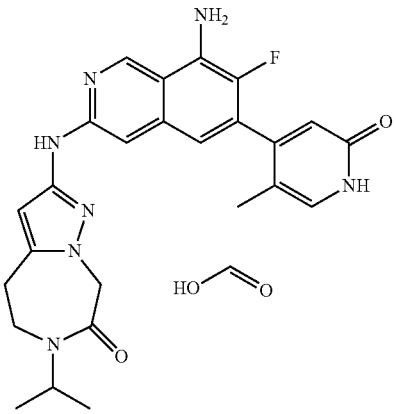 [SMILES: Cc1c[nH]c(=O)cc1-c1cc2cc(Nc3cc4n(n3)CC(=O)N(C(C)C)CC4)ncc2c(N)c1F ; O=CO]

Step 1: 4-iodo-2-methoxy-5-methyl-pyridine

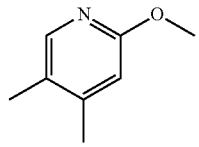

A solution of 2-fluoro-4-iodo-5-methylpyridine (5.0 g, 21.1 mmol) and sodium methanolate in methanol (50 mL, 30%) in methanol (50 mL) was stirred at 80° C. for 2.5 hours. The reaction was quenched by water. The resulting solution was extracted with ethyl acetate, dried with anhydrous sodium sulfate. After filtration, the filtrate was concentrated under vacuum. The residue was purified by flash chromatography on silica gel eluting with petroleum ether/ethyl acetate (5/1) to afford 4-iodo-2-methoxy-5-methyl-pyridine (3.7 g, 14.86 mmol) as a light yellow solid. LCMS (ESI) [M+H]$^+$=250.

Step 2: (2-methoxy-5-methyl-4-pyridyl)boronic Acid

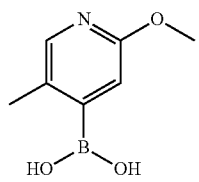

A solution of 4-iodo-2-methoxy-5-methyl-pyridine (200 mg, 0.80 mmol), n-Butyllithium (0.8 mL, 2 mmol) in tetrahydrofuran (5 mL) was stirred for 1 hour at −78° C. Triisopropoxyborane (1 mL, 4.33 mmol) was added and then stirred at 25° C. for 1 hour. The reaction was quenched with water. The resulting solution was extracted with ethyl acetate, dried with anhydrous sodium sulfate. After filtration, the filtrate was concentrated under vacuum to afford (2-methoxy-5-methyl-4-pyridyl)boronic acid (300 mg, 0.72 mmol) as a white solid. LCMS (ESI) [M+H]$^+$=168.

Step 3: tert-butyl N-[7-fluoro-3-[(6-isopropyl-7-oxo-5,8-dihydro-4H-pyrazolo[1,5-d][1,4]diazepin-2-yl)amino]-6-(2-methoxy-5-methyl-4-pyridyl)-8-isoquinolyl]carbamate

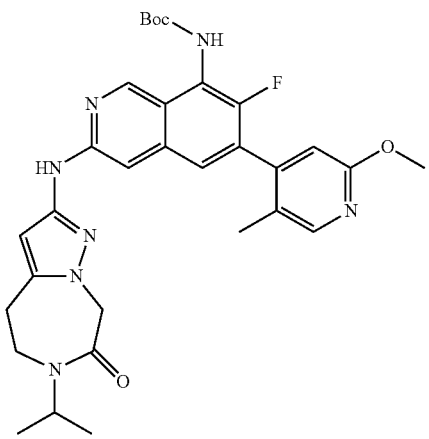 [SMILES: COc1cc(-c2cc3cc(Nc4cc5n(n4)CC(=O)N(C(C)C)CC5)ncc3c(NC(=O)OC(C)(C)C)c2F)c(C)cn1]

A mixture of (2-methoxy-5-methyl-4-pyridyl)boronic acid (54.16 mg, 0.32 mmol), [8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl] trifluoromethanesulfonate (100.0 mg, 0.16 mmol), [1,1'-bis(diphenylphosphino)ferrocene]dichloropalladium(II) (11.87 mg, 0.02 mmol) and potassium carbonate (49.24 mg, 0.36 mmol) in 1,4-dioxane (10 mL) and water (1 mL) was stirred at 90° C. for 3 hours under nitrogen. After filtration, the filtrate was concentrated under reduced pressure. The residue was purified by flash chromatography on silica gel eluting with methanol/dichloromethane (1:9) to afford tert-butyl N-[7-fluoro-3-[(6-isopropyl-7-oxo-5,8-dihydro-4H-pyrazolo[1,5-d][1,4]diazepin-2-yl)amino]-6-(2-methoxy-5-methyl-4-pyridyl)-8-isoquinolyl]carbamate (59 mg, 0.10 mmol) as a yellow solid. LCMS (ESI) [M+H]$^+$=590.

Step 4: 2-[[8-amino-7-fluoro-6-(5-methyl-2-oxo-1H-pyridin-4-yl)-3-isoquinolyl]amino]-6-isopropyl-5,8-dihydro-4H-pyrazolo[1,5-d][1,4]diazepin-7-one; Formic Acid

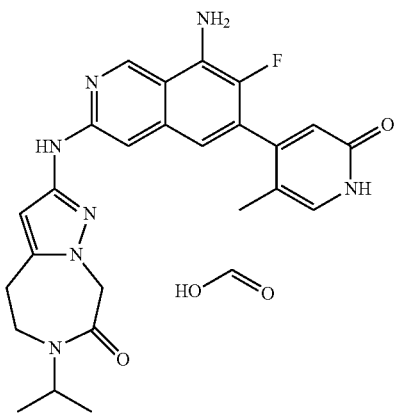 [SMILES: Cc1c[nH]c(=O)cc1-c1cc2cc(Nc3cc4n(n3)CC(=O)N(C(C)C)CC4)ncc2c(N)c1F ; O=CO]

A mixture of tert-butyl N-[7-fluoro-3-[(6-isopropyl-7-oxo-5,8-dihydro-4H-pyrazolo[1,5-d][1,4]diazepin-2-yl)amino]-6-(2-methoxy-5-methyl-4-pyridyl)-8-isoquinolyl]carbamate (60 mg, 0.10 mmol) and iodotrimethylsilane (122.16 mg, 0.61 mmol) in acetonitrile (60 mL) was stirred at 80° C. for 2 hours. The solvent was concentrated under vacuum. The crude product was purified by Prep-HPLC (Atlantis HILIC OBD, 19×150 mm 5 um; water (0.1% FA): CH$_3$CN=13%-24% B in 10 min) to afford 2-[[8-amino-7-fluoro-6-(5-methyl-2-oxo-1H-pyridin-4-yl)-3-isoquinolyl]amino]-6-isopropyl-5,8-dihydro-4H-pyrazolo[1,5-d][1,4]diazepin-7-one; formic acid (11.4 mg, 0.022 mmol) as a yellow solid. LCMS (ESI) [M+H]$^+$=476.2; $^1$H NMR (300 MHz, DMSO-d$_6$) δ 11.89-11.19 (s, 1H), 9.26 (s, 1H), 9.10 (s, 1H), 8.38 (s, 1H), 7.73 (s, 1H), 7.31 (s, 1H), 6.73 (d, J=6.0 Hz, 1H), 6.26 (s, 1H), 6.13 (s, 2H), 5.97 (s, 1H), 4.98 (s, 2H), 4.66-4.55 (m, 1H), 3.84-3.74 (m, 2H), 3.04-2.94 (s, 2H), 1.84 (s, 3H), 1.13 (d, J=6.8 Hz, 6H).

Example 168

2-(8-amino-7-fluoro-6-(4-methylpyridin-3-yl)isoquinolin-3-ylamino)-6-(2-hydroxy-2-methylpropyl)-5,6-dihydro-4H-pyrazolo[1,5-g][1,4]diazepin-7(8H)-one (Compound 273)

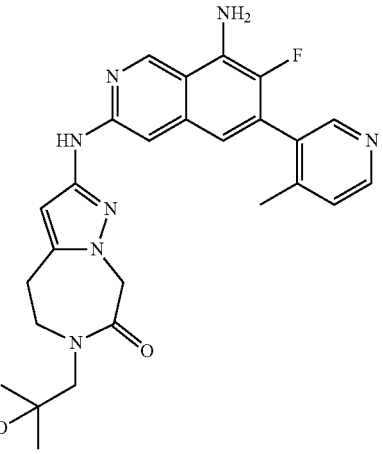

Step 1: methyl 2-(3-bromo-5-(2-(2-hydroxy-2-methylpropylamino)ethyl)-1H-pyrazol-1-yl)acetate

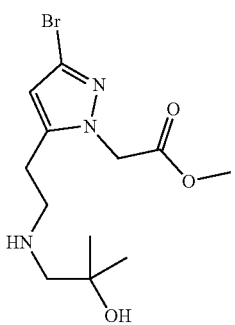 [SMILES: COC(=O)Cn1nc(Br)cc1CCNCC(C)(C)O]

A solution of methyl 2-[5-(2-aminoethyl)-3-bromo-pyrazol-1-yl]acetate (400 mg, 1.53 mmol) and isobutyleneoxide (20 mL, 1.53 mmol) in methanol (10 mL) was stirred at 25° C. for 40 hours. The mixture was concentrated under vacuum. The crude product would be directly used in the next step without purification. LCMS (ESI) [M+H]⁺=334.

Step 2: 2-bromo-6-(2-hydroxy-2-methylpropyl)-5,6-dihydro-4H-pyrazolo[1,5-g][1,4]diazepin-7(8H)-one

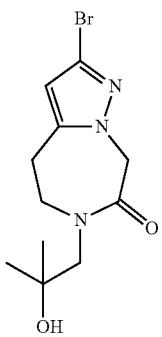 [SMILES: CC(C)(O)CN1CCc2cc(Br)nn2CC1=O]

A solution of methyl 2-[3-bromo-5-[2-[(2-hydroxy-2-methyl-propyl)amino]ethyl]pyrazol-1-yl]acetate (200 mg, 0.60 mmol) and triethylamine (604.41 mg, 5.98 mmol) in methanol (50 mL) was stirred at 25° C. for 12 hours. The mixture was concentrated under vacuum. The residue was purified by flash chromatography on silica gel eluting with methanol/dichloromethane (5/95) to afford 2-bromo-6-(2-hydroxy-2-methyl-propyl)-5,8-dihydro-4H-pyrazolo[1,5-d][1,4]diazepin-7-one (40 mg, 0.13 mmol) as a white solid. LCMS (ESI) [M+H]⁺=302.

Step 3: 2-(8-chloro-7-fluoro-6-(4-methylpyridin-3-yl)isoquinolin-3-ylamino)-6-(2-hydroxy-2-methyl-propyl)-5,6-dihydro-4H-pyrazolo[1,5-g][1,4]diazepin-7(8H)-one

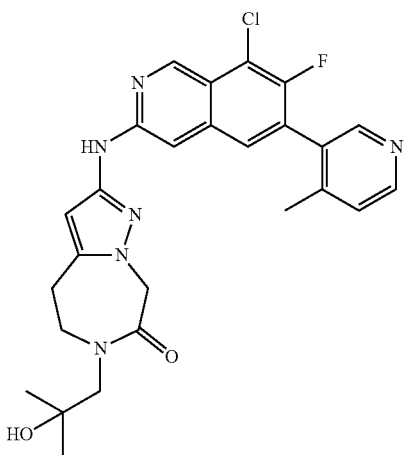 [SMILES: Cc1ccncc1-c1cc2cc(Nc3cc4n(n3)CC(=O)N(CC(C)(C)O)CC4)ncc2c(Cl)c1F]

A mixture of 2-bromo-6-(2-hydroxy-2-methyl-propyl)-5,8-dihydro-4H-pyrazolo[1,5-d][1,4]diazepin-7-one (252.05 mg, 0.83 mmol), 8-chloro-7-fluoro-6-(4-methyl-3-pyridyl)isoquinolin-3-amine (200 mg, 0.70 mmol), tris(dibenzylideneacetone)dipalladium-chloroformadduct (143.89 mg, 0.14 mmol), 4,5-bis(diphenylphosphino)-9,9-dimethylxanthene (160.99 mg, 0.28 mmol) and cesium carbonate (679.83 mg, 2.09 mmol) in 1,4-dioxane (20 mL) was stirred for 3 hours at 100° C. After filtration, the filtrate was concentrated under reduced pressure. The residue was purified by flash chromatography on silica gel eluting with methanol/dichloromethane (1/9) to afford 2-[[8-chloro-7-fluoro-6-(4-methyl-3-pyridyl)-3-isoquinolyl]amino]-6-(2-hydroxy-2-methyl-propyl)-5,8-dihydro-4H-pyrazolo[1,5-d][1,4]diazepin-7-one (150 mg, 0.29 mmol) as a yellow solid. LCMS (ESI) [M+H]⁺=509.

Step 4: tert-butyl 7-fluoro-3-(6-(2-hydroxy-2-methylpropyl)-7-oxo-5,6,7,8-tetrahydro-4H-pyrazolo[1,5-g][1,4]diazepin-2-ylamino)-6-(4-methylpyridin-3-yl)isoquinolin-8-ylcarbamate

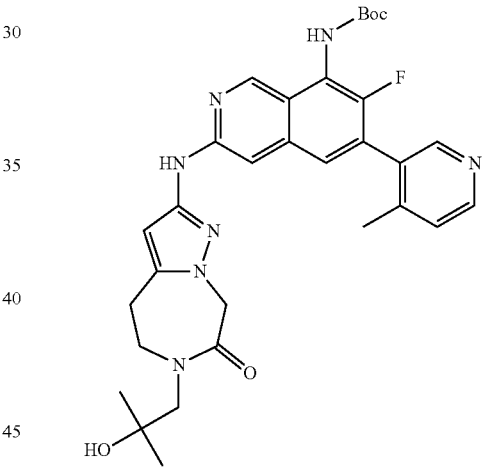

A mixture of tert-Butyl carbamate (1173.85 mg, 10.02 mmol), 2-[[8-chloro-7-fluoro-6-(4-methyl-3-pyridyl)-3-isoquinolyl]amino]-6-(2-hydroxy-2-methyl-propyl)-5,8-dihydro-4H-pyrazolo[1,5-d][1,4]diazepin-7-one (170 mg, 0.33 mmol), tris(dibenzylideneacetone)dipalladium-chloroformadduct (69.14 mg, 0.07 mmol), Brettphos (71.74 mg, 0.13 mmol) and cesium carbonate (435.54 mg, 1.34 mmol) in 1,4-dioxane (15 mL) was stirred for 2 hours at 90° C. After filtration, the filtrate was concentrated under reduced pressure. The residue was purified by flash chromatography on silica gel eluting with methanol/dichloromethane (1/9) to afford tert-butyl N-[7-fluoro-3-[[6-(2-hydroxy-2-methyl-propyl)-7-oxo-5,8-dihydro-4H-pyrazolo[1,5-d][1,4]diazepin-2-yl]amino]-6-(4-methyl-3-pyridyl)-8-isoquinolyl]carbamate (60 mg, 0.10 mmol) as a yellow solid. LCMS (ESI) [M+H]⁺=590.

Step 5: 2-((8-amino-7-fluoro-6-(4-methylpyridin-3-yl)isoquinolin-3-ylamino)-6-(2-hydroxy-2-methyl-propyl)-5,6-dihydro-4H-pyrazolo[1,5-g][1,4]diaz-epin-7(8H)-one

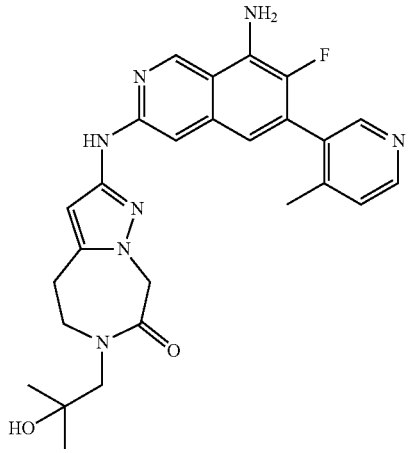 [SMILES: Cc1ccncc1-c1cc2cc(Nc3cc4n(n3)CC(=O)N(CC(C)(C)O)CC4)ncc2c(N)c1F]

A solution of tert-butyl N-[7-fluoro-3-[[6-(2-hydroxy-2-methyl-propyl)-7-oxo-5,8-dihydro-4H-pyrazolo[1,5-d][1,4]diazepin-2-yl]amino]-6-(4-methyl-3-pyridyl)-8-isoquinolyl]carbamate (60 mg, 0.10 mmol) in 2,2,2-trifluoroacetic acid (6 mL) was stirred at 25° C. for 2 hours. The mixture was concentrated under vacuum. The crude product was purified by Prep-HPLC (Atlantis HILIC OBD, 19×150 mm Sum; water (10 mmol/L sodium bicarbonate): $CH_3CN=20\%-45\%$ B in 7 min) to afford 2-[[8-amino-7-fluoro-6-(4-methyl-3-pyridyl)-3-isoquinolyl]amino]-6-(2-hydroxy-2-methyl-propyl)-5,8-dihydro-4H-pyrazolo[1,5-d][1,4]diazepin-7-one (14.1 mg, 0.029 mmol) as a yellow solid. LCMS (ESI) $[M+H]^+$=490.2; H NMR (400 MHz, DMSO-$d_6$) δ 9.27 (s, 1H), 9.10 (s, 1H), 8.50 (d, J=5.0 Hz, 1H), 8.43 (s, 1H), 7.75 (s, 1H), 7.39 (d, J=5.1 Hz, 1H), 6.78 (d, J=6.1 Hz, 1H), 6.12 (s, 2H), 5.96 (s, 1H), 5.01 (s, 2H), 4.59 (s, 1H), 4.00-3.93 (m, 2H), 3.82 (s, 2H), 3.15-3.07 (s, 2H), 2.22 (s, 3H), 1.06 (s, 6H).

Example 169

(R)-2-((8-amino-7-fluoro-6-(7-hydroxy-6,7-dihydro-5H-cyclopenta[c]pyridin-4-yl)isoquinolin-3-yl)amino)-6-isopropyl-5,6-dihydro-4H-pyrazolo[1,5-d][1,4]diazepin-7(8H)-one (Compound 274) and (S)-2-((8-amino-7-fluoro-6-(7-hydroxy-6,7-dihydro-5H-cyclopenta[c]pyridin-4-yl)isoquinolin-3-yl)amino)-6-isopropyl-5,6-dihydro-4H-pyrazolo[1,5-d][1,4]diazepin-7(8H)-one (Compound 275)

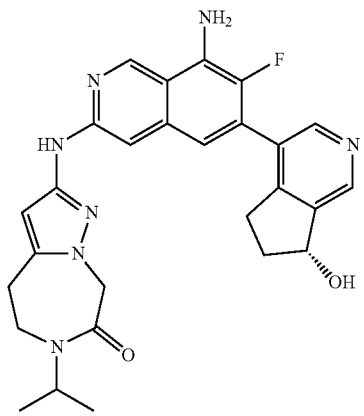

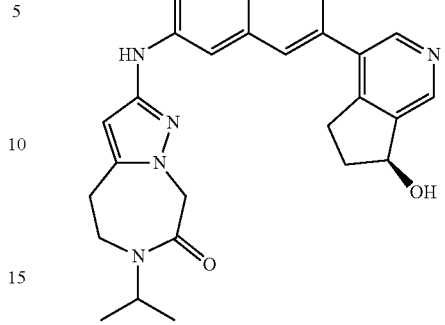

Step 1: methyl 4-bromo-7-hydroxy-5H-cyclopenta[c]pyridine-6-carboxylate

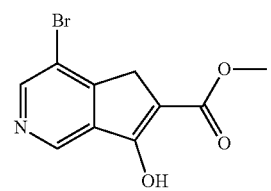

To a solution of ethyl 5-bromonicotinate (5 g, 21.7 mmol) in tetrahydrofuran (22 mL) was added dropwise lithium diisopropylamide (23.9 mmol, 2.5 M in tetrahydrofuran) over 5 minutes at −78° C. The resulting dark red solution was stirred for 30 minutes at −78° C. Methyl acrylate (4.9 mL, 54.3 mmol) in tetrahydrofuran (22 mL) was added over 5 minutes at −78° C. The reaction was stirred an additional 1.5 hours at −78° C. Then aq. 10% acetic acid (43.5 mL, 76.1 mmol) was added (giving a pH of 4-5) and the reaction was allowed to warm to room temperature. The resulting solution was concentrated under vacuum to afford methyl 4-bromo-7-hydroxy-5H-cyclopenta[c]pyridine-6-carboxylate (5.38 g, crude) as dark green amorphous solid. LCMS (ESI) $[M+H^+]$=270, 272

Step 2: 4-bromo-5,6-dihydro-7H-cyclopenta[c]pyridin-7-one

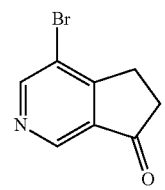 [SMILES: O=C1CCc2c(Br)cncc21]

4-bromo-6-(methoxycarbonyl)-5H-cyclopenta[c]pyridine-7-olate (5.38 g, crude) was dissolved in aq. 6M hydrochloric acid (54 mL) and heated at reflux for 1.5 hours. The reaction was cooled in ice/water and then adjusted to pH 9 with potassium hydroxide (6 mol/L). The resulting solution was extracted with ether dried with anhydrous sodium sulfate. After filtration, the filtrate was concentrated under vacuum. The residue was purified by flash chromatography on silica gel eluting with dichloromethane/methanol (100/1) to afford 4-bromo-5,6-dihydro-7H-cyclopenta[c]pyridin-7-one (0.69 g, 3.25 mmol) as pink solid. LCMS (ESI) [M+H]⁺=212, 214.

Step 3: 4-bromo-6,7-dihydro-5H-cyclopenta[c]pyridin-7-ol

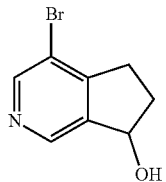 [SMILES: OC1CCc2c(Br)cncc21]

To a solution of 4-bromo-5,6-dihydrocyclopenta[c]pyridin-7-one (0.69 g, 3.3 mmol) in ethanol (10 mL) was added sodium borohydride (188 mg, 5 mmol) at 0° C. The resulting solution was stirred overnight at room temperature. The reaction was quenched with water and then extracted with dichloromethane, dried with anhydrous sodium sulfate. After filtration, the filtrate was concentrated under vacuum to afford 4-bromo-6,7-dihydro-5H-cyclopenta[c]pyridin-7-ol (580 mg, 2.72 mmol) as an off-white solid. LCMS (ESI) [M+H]⁺=214, 216.

Step 4: 4-bromo-7-(tert-butyldiphenylsilyloxy)-6,7-dihydro-5H-cyclopenta[c]pyridine

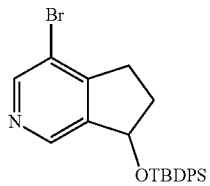

To a solution of 4-bromo-6,7-dihydro-5H-cyclopenta[c]pyridin-7-ol (424 mg, 2 mmol) in N,N-dimethylformamide (10 mL) was added imidazole (408 mg, 6.0 mmol) and tert-butylchlorodiphenylsilane (1.1 g, 4.0 mmol). The reaction mixture was stirred at 25° C. for 2 hours. The reaction mixture was diluted with ethyl acetate and then washed with brine. The organic layers were dried with anhydrous sodium sulfate. After filtration, the filtrate was concentrated under vacuum to afford 4-bromo-7-(tert-butyldiphenylsilyloxy)-6,7-dihydro-5H-cyclopenta[c]pyridine (820 mg, 1.81 mmol) as a light yellow oil. LCMS (ESI) [M+H]⁺=452, 454.

Step 5: 7-(tert-butyldiphenylsilyloxy)-6,7-dihydro-5H-cyclopenta[c]pyridin-4-ylboronic Acid

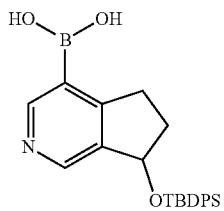

To a pressure tube was added 4-bromo-7-(tert-butyldiphenylsilyloxy)-6,7-dihydro-5H-cyclopenta[c]pyridine (450 mg, 1 mmol), bis(pinacolato)diboron (2.54 g, 10 mmol), [1,1'-bis(diphenylphosphino)ferrocene]dichloropalladium (II) (73 mg, 0.1 mmol) and potassium acetate (290 mg, 0.3 mmol) in 1,4-dioxane. The reaction mixture was stirred at 90° C. for 3 hours. The mixture was concentrated under vacuum. The residue was purified by reverse-HPLC to afford 7-(tert-butyldiphenylsilyloxy)-6,7-dihydro-5H-cyclopenta[c]pyridin-4-ylboronic acid (320 mg, 0.77 mmol) as an off-white solid. LCMS (ESI) [M+H]⁺=418.

Step 6: tert-butyl 6-(7-(tert-butyldiphenylsilyloxy)-6,7-dihydro-5H-cyclopenta[c]pyridin-4-yl)-7-fluoro-3-(6-isopropyl-7-oxo-5,6,7,8-tetrahydro-4H-pyrazolo[1,5-g][1,4]diazepin-2-ylamino)isoquinolin-8-ylcarbamate

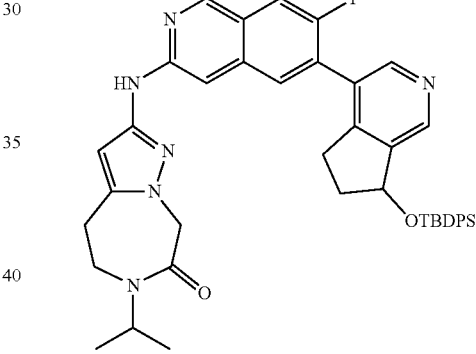

To a pressure tube was added 7-(tert-butyldiphenylsilyloxy)-6,7-dihydro-5H-cyclopenta[c]pyridin-4-ylboronic acid (100 mg, 0.24 mmol), 8-(tert-butoxycarbonylamino)-7-fluoro-3-(6-isopropyl-7-oxo-5,6,7,8-tetrahydro-4H-pyrazolo[1,5-g][1,4]diazepin-2-ylamino)isoquinolin-6-yl trifluoromethanesulfonate (98 mg, 0.16 mmol), [1,1'-bis(diphenylphosphino)ferrocene]dichloropalladium(II) (26 mg, 0.032 mmol) and potassium carbonate (66 mg, 0.48 mmol) in 1,4-dioxane. The reaction mixture was stirred at 90° C. for 3 hours. The reaction was cooled to room temperature and then concentrated under vacuum. The residue was purified by reverse-HPLC to afford tert-butyl 6-(7-(tert-butyldiphenylsilyloxy)-6,7-dihydro-5H-cyclopenta[c]pyridin-4-yl)-7-fluoro-3-(6-isopropyl-7-oxo-5,6,7,8-tetrahydro-4H-pyrazolo[1,5-g][1,4]diazepin-2-ylamino)isoquinolin-8-ylcarbamate (108 mg, 0.13 mmol) as a brown solid. LCMS (ESI) [M+H]⁺=840.

Step 7: 2-(8-amino-6-(7-(tert-butyldiphenylsilyloxy)-6,7-dihydro-5H-cyclopenta[c]pyridin-4-yl)-7-fluoroisoquinolin-3-ylamino)-6-isopropyl-5,6-dihydro-4H-pyrazolo[1,5-g][1,4]diazepin-7(8H)-one

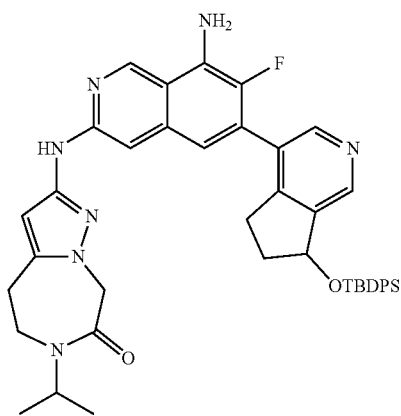

To a solution of tert-butyl 6-(7-(tert-butyldiphenylsilyloxy)-6,7-dihydro-5H-cyclopenta[c]pyridin-4-yl)-7-fluoro-3-(6-isopropyl-7-oxo-5,6,7,8-tetrahydro-4H-pyrazolo[1,5-g][1,4]diazepin-2-ylamino)isoquinolin-8-ylcarbamate (108 mg, 0.13 mmol) in dichloromethane (5 mL) was added 2,2,2-trifluoroacetic acid (2 mL) at 0° C. The reaction was stirred for 30 minutes at room temperature. The resulting solution was concentrated under vacuum to afford 2-(8-amino-6-(7-(tert-butyldiphenylsilyloxy)-6,7-dihydro-5H-cyclopenta[c]pyridin-4-yl)-7-fluoroisoquinolin-3-ylamino)-6-isopropyl-5,6-dihydro-4H-pyrazolo[1,5-g][1,4]diazepin-7(8H)-one (45 mg, 0.061 mmol) as a brown oil. The residue was used directly for next step. LCMS (ESI) [M+H]⁺=740.

Step 8: (R)-2-((8-amino-7-fluoro-6-(7-hydroxy-6,7-dihydro-5H-cyclopenta[c]pyridin-4-yl)isoquinolin-3-yl)amino)-6-isopropyl-5,6-dihydro-4H-pyrazolo[1,5-d][1,4]diazepin-7(8H)-one and (S)-2-((8-amino-7-fluoro-6-(7-hydroxy-6,7-dihydro-5H-cyclopenta[c]pyridin-4-yl)isoquinolin-3-yl)amino)-6-isopropyl-5,6-dihydro-4H-pyrazolo[1,5-d][1,4]diazepin-7(8H)-one

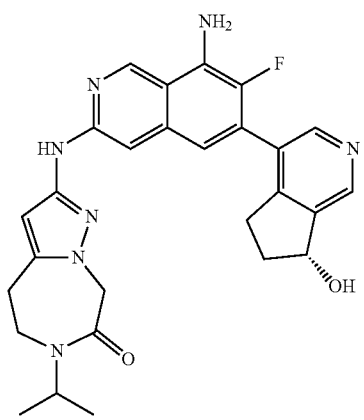

-continued

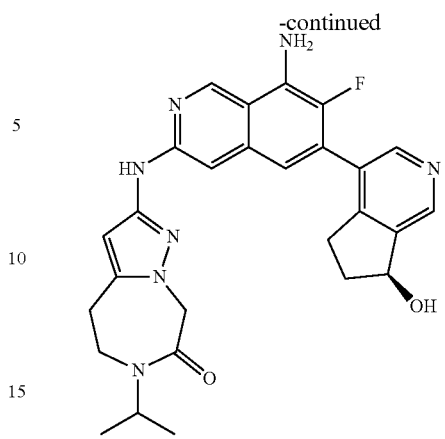

A solution of 2-(8-amino-6-(7-(tert-butyldiphenylsilyloxy)-6,7-dihydro-5H-cyclopenta[c]pyridin-4-yl)-7-fluoroisoquinolin-3-ylamino)-6-isopropyl-5,6-dihydro-4H-pyrazolo[1,5-g][1,4]diazepin-7(8H)-one (45 mg, 0.061 mmol) in dichloromethane (10 mL) and tetrabutylammonium fluoride (0.1 mL) was stirred at 25° C. for 2 hours. The mixture was concentrated under vacuum. The crude product was purified by Prep-HPLC (C18 silica gel; 0.5% sodium bicarbonate in water:ACN=20%-50% in 30 mins) to afford the racemic product (25 mg, 0.049 mmol) as a white solid. The racemic product was separated by Chiral-HPLC to afford two isomers: Compound 275: (7.1 mg, 0.014 mmol) as a white solid. Retention time: 2.68 min (CHIRALPAK IE-3. 0.46*10 cm; 3 μm; MtBE (0.3% IPAmine):EtOH=70:30; 1.0 ml/min); LCMS (ESI) [M+H]⁺=502.2; ¹H NMR (300 MHz, DMSO-d₆) δ 9.26 (s, 1H), 9.09 (s, 1H), 8.58 (s, 1H), 8.45 (s, 1H), 7.72 (s, 1H), 6.85 (d, J=6.2 Hz, 1H), 6.12 (s, 2H), 5.97 (s, 1H), 5.52 (d, J=5.8 Hz, 1H), 5.26 (dd, J=12.6, 6.4 Hz, 1H), 4.97 (s, 2H), 4.64-4.54 (m, 1H), 3.78 (s, 2H), 3.03-2.71 (m, 4H), 2.40-2.31 (m, 1H), 1.88-1.78 (m, 1H), 1.12 (d, J=6.8 Hz, 6H). Compound 274: (7.8 mg, 0.015 mmol) as a white solid. Retention time: 3.73 min (CHIRALPAK IE-3. 0.46*10 cm; 3 μm; MtBE (0.3% IPAmine):EtOH=70:30; 1.0 ml/min).

Example 170

2-((8-amino-6-(5-amino-4-methylpyridin-3-yl)-7-fluoroisoquinolin-3-yl)amino)-5-methyl-4,5-dihydro-7H-pyrazolo[5,1-d][1,2,5]thiadiazine 6,6-dioxide (Compound 276)

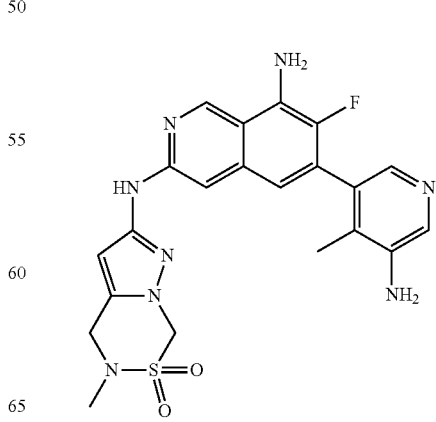

Step 1: methyl 5-bromo-2-(methylsulfamoylmethyl) pyrazole-3-carboxylate

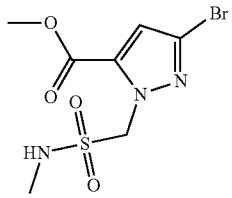 [SMILES: CNS(=O)(=O)Cn1nc(Br)cc1C(=O)OC]

A mixture of methyl 3-bromo-1H-pyrazole-5-carboxylate (100 mg, 0.49 mmol), 1-bromo-N-methyl-methanesulfonamide (91.72 mg, 0.49 mmol) and potassium carbonate (134.63 mg, 0.98 mmol) in 1-methyl-2-pyrrolidinone (10 mL) was stirred at 50° C. for 1 hour. After filtration, the filtrate was concentrated under reduced pressure. The residue was purified by flash chromatography on silica gel eluting with petroleum ether/ethyl acetate (3/1) to afford methyl 5-bromo-2-(methylsulfamoylmethyl)pyrazole-3-carboxylate (100 mg, 0.32 mmol) as a white solid. LCMS (ESI) [M+H]$^+$=312.

Step 2: 1-[3-bromo-5-(hydroxymethyl)pyrazol-1-yl]-N-methyl-methanesulfonamide

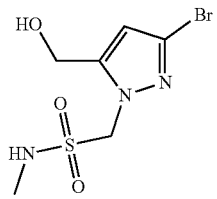

To a solution of methyl 5-bromo-2-(methylsulfamoylmethyl)pyrazole-3-carboxylate (60 mg, 0.19 mmol) in dichloromethane (10 mL) was added diisobutylaluminium hydride (0.19 mL, 0.38 mmol) at 0° C. The resulting solution was stirred for 1 hour at 0° C. The reaction was quenched with methanol. After filtration, the filtrate was concentrated under reduced pressure.

The residue was purified by reverse phase chromatography (acetonitrile 0-50/0.1% ammonium hydroxide in water) to afford 1-[3-bromo-5-(hydroxymethyl)pyrazol-1-yl]-N-methyl-methanesulfonamide (35 mg, 0.12 mmol) as a colorless oil. LCMS (ESI) [M+H]$^+$=284.

Step 3: 2-bromo-5-methyl-4,7-dihydropyrazolo[5,1-d][1,2,5]thiadiazine 6,6-dioxide

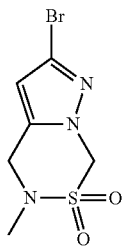

A mixture of 1-[3-bromo-5-(hydroxymethyl)pyrazol-1-yl]-N-methyl-methanesulfonamide (200 mg, 0.70 mmol) and triphenylphosphine (370.25 mg, 1.41 mmol) in tetrahydrofuran (10 mL) was stirred at 25° C. for 5 minutes. Then diisopropyl azodicarboxylate (284.38 mg, 1.41 mmol) was added. The reaction was stirred at 25° C. for 2 hours. The mixture was concentrated under vacuum. The residue was purified by flash chromatography on silica gel eluting with petroleum ether/ethyl acetate (5/1) to afford 2-bromo-5-methyl-4,7-dihydropyrazolo[5,1-d][1,2,5]thiadiazine 6,6-dioxide (170 mg, 0.64 mmol) as a white solid. LCMS (ESI) [M+H]$^+$=266.

Step 4: tert-butyl N-tert-butoxycarbonyl-N-[5-[8-chloro-7-fluoro-3-[(5-methyl-6,6-dioxo-4,7-dihydropyrazolo[5,1-d][1,2,5]thiadiazin-2-yl)amino]-6-isoquinolyl]-4-methyl-3-pyridyl]carbamate

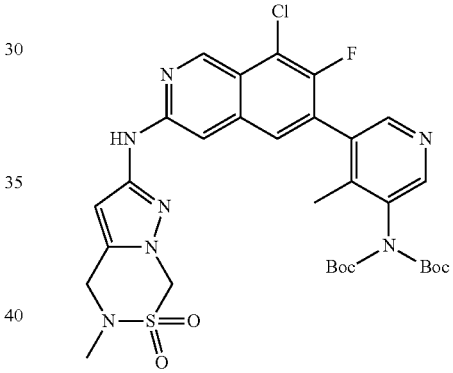

A mixture of tert-butyl N-[5-(3-amino-8-chloro-7-fluoro-6-isoquinolyl)-4-methyl-3-pyridyl]-N-tert-butoxycarbonyl-carbamate (321.3 mg, 0.64 mmol), 2-bromo-5-methyl-4,7-dihydropyrazolo[5,1-d][1,2,5]thiadiazine 6,6-dioxide (170 mg, 0.64 mmol), tris(dibenzylideneacetone)dipalladium-chloroformadduct (132.23 mg, 0.13 mmol), 4,5-bis(diphenylphosphino)-9,9-dimethylxanthene (147.69 mg, 0.26 mmol) and cesium carbonate (624.76 mg, 1.92 mmol) in 1,4-dioxane (20 mL) was stirred for 6 hours at 100° C. After filtration, the filtrate was concentrated under reduced pressure. The residue was purified by flash chromatography on silica gel eluting with petroleum ether/ethyl acetate (3/2) to afford tert-butyl N-tert-butoxycarbonyl-N-[5-[8-chloro-7-fluoro-3-[(5-methyl-6,6-dioxo-4,7-dihydropyrazolo[5,1-d][1,2,5]thiadiazin-2-yl)amino]-6-isoquinolyl]-4-methyl-3-pyridyl]carbamate (110 mg, 0.16 mmol) as a yellow solid. LCMS (ESI) [M+H]$^+$=688.

Step 5: tert-butyl N-tert-butoxycarbonyl-N-[5-[8-(tert-butoxycarbonylamino)-7-fluoro-3-[(5-methyl-6,6-dioxo-4,7-dihydropyrazolo[5,1-d][1,2,5]thiadiazin-2-yl)amino]-6-isoquinolyl]-4-methyl-3-pyridyl]carbamate

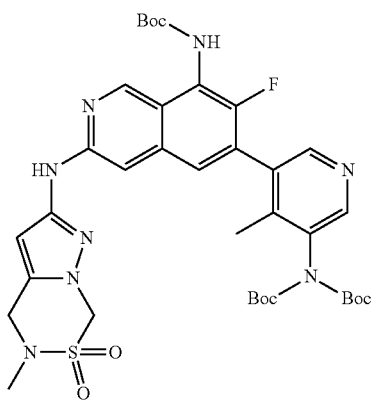 [SMILES: Cc1c(-c2cc3cc(Nc4cc5n(n4)CS(=O)(=O)N(C)C5)ncc3c(NC(=O)OC(C)(C)C)c2F)cncc1N(C(=O)OC(C)(C)C)C(=O)OC(C)(C)C]

A mixture of tert-butyl N-tert-butoxycarbonyl-N-[5-[8-chloro-7-fluoro-3-[(5-methyl-6,6-dioxo-4,7-dihydropyrazolo[5,1-d][1,2,5]thiadiazin-2-yl)amino]-6-isoquinolyl]-4-methyl-3-pyridyl]carbamate (100 mg, 0.15 mmol), tert-butyl carbamate (340.47 mg, 2.91 mmol), tris(dibenzylideneacetone)dipalladium-chloroformadduct (30.08 mg, 0.03 mmol), 4,5-bis(diphenylphosphino)-9,9-dimethylxanthene (33.6 mg, 0.06 mmol) and cesium carbonate (142.12 mg, 0.44 mmol) in 1,4-dioxane (15 mL) was stirred for 6 hours at 100° C. After filtration, the filtrate was concentrated under reduced pressure. The residue was purified by flash chromatography on silica gel eluting with petroleum ether/ethyl acetate (2/1) to afford tert-butyl N-tert-butoxycarbonyl-N-[5-[8-(tert-butoxycarbonylamino)-7-fluoro-3-[(5-methyl-6,6-dioxo-4,7-dihydropyrazolo[5,1-d][1,2,5]thiadiazin-2-yl)amino]-6-isoquinolyl]-4-methyl-3-pyridyl]carbamate (105 mg, 0.14 mmol) as a yellow solid. LCMS (ESI) [M+H]$^+$=769.

Step 6: 6-(5-amino-4-methyl-3-pyridyl)-7-fluoro-N3-(5-methyl-6,6-dioxo-4,7-dihydropyrazolo[5,1-d][1,2,5]thiadiazin-2-yl)isoquinoline-3,8-diamine

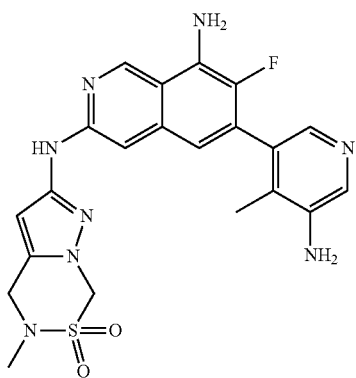 [SMILES: Cc1c(N)cncc1-c1cc2cc(Nc3cc4n(n3)CS(=O)(=O)N(C)C4)ncc2c(N)c1F]

A mixture of tert-butyl N-tert-butoxycarbonyl-N-[5-[8-(tert-butoxycarbonylamino)-7-fluoro-3-[(5-methyl-6,6-dioxo-4,7-dihydropyrazolo[5,1-d][1,2,5]thiadiazin-2-yl)amino]-6-isoquinolyl]-4-methyl-3-pyridyl]carbamate (100 mg, 0.13 mmol) and 2,2,2-trifluoroacetic acid (1 mL) in dichloromethane (3 mL) was stirred at 25° C. for 1 hour. The mixture was concentrated under vacuum. The reaction mixture was adjusted to pH 9 with ammonia in methanol (7 mol/L). The resulting residue was purified by reverse phase chromatography (acetonitrile 0-40/0.1% sodium bicarbonate in water) to afford 6-(5-amino-4-methyl-3-pyridyl)-7-fluoro-N3-(5-methyl-6,6-dioxo-4,7-dihydropyrazolo[5,1-d][1,2,5]thiadiazin-2-yl)isoquinoline-3,8-diamine (55.3 mg, 0.12 mmol) as a yellow solid. LCMS (ESI) [M+H]$^+$=469; $^1$HNMR (400 MHz, DMSO-d$_6$) δ 9.33 (s, 1H), 9.28 (s, 1H), 7.98 (s, 1H), 7.70 (s, 1H), 7.66 (s, 1H), 6.65-6.64 (d, J=4.0 Hz, 1H), 6.16 (s, 1H), 6.09 (s, 2H), 5.57 (s, 2H), 5.22 (s, 2H), 4.59 (s, 2H), 2.86 (s, 3H), 1.92 (s, 3H).

Example 171

2-((8-amino-6-(5-amino-4-methylpyridin-3-yl)-7-fluoroisoquinolin-3-yl)amino)-6-(oxetan-3-ylmethyl)-5,6-dihydro-4H-pyrazolo[1,5-d][1,4]diazepin-7(8H)-one (Compound 277)

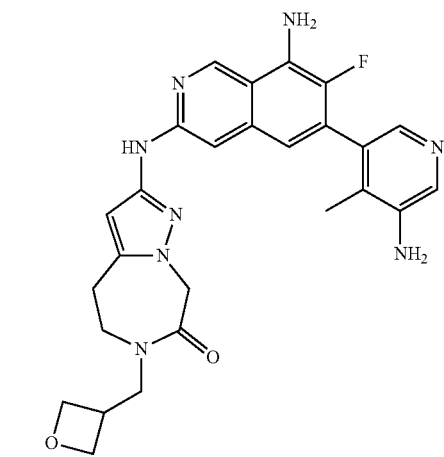 [SMILES: Cc1c(N)cncc1-c1cc2cc(Nc3cc4n(n3)CC(=O)N(CC3COC3)CC4)ncc2c(N)c1F]

Step 1: 2-bromo-6-(oxetan-3-ylmethyl)-5,8-dihydro-4H-pyrazolo[1,5-d][1,4]diazepin-7-one

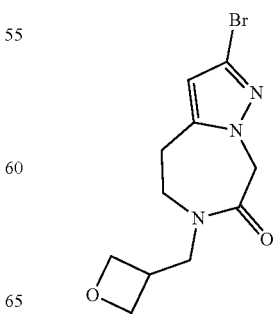

To a solution of 2-bromo-4,5,6,8-tetrahydropyrazolo[1,5-d][1,4]diazepin-7-one (200 mg, 0.87 mmol) in N,N-dimethylformamide (5 mL) was added NaH (79.98 mg, 3.48 mmol) at 0° C. and then stirred for 5 minutes. 3-(iodomethyl) oxetane (344.26 mg, 1.74 mmol) was added and then stirred at 25° C. for 1 hour. The reaction was quenched by water. The resulting solution was extracted with ethyl acetate, dried with anhydrous sodium sulfate. After filtration, the filtrate was concentrated under vacuum. The residue was purified by flash chromatography on silica gel eluting with dichloromethane/methanol (96/4) to afford 2-bromo-6-(oxetan-3-ylmethyl)-5,8-dihydro-4H-pyrazolo[1,5-d][1,4]diazepin-7-one (192 mg, 0.64 mmol) as a orange solid. LCMS (ESI) [M+H]$^+$=300.3.

Step 2: Tert-butyl N-tert-butoxycarbonyl-N-[5-[8-chloro-7-fluoro-3-[[6-(oxetan-3-ylmethyl)-7-oxo-5,8-dihydro-4H-pyrazolo[1,5-d][1,4]diazepin-2-yl]amino]-6-isoquinolyl]-4-methyl-3-pyridyl]carbamate

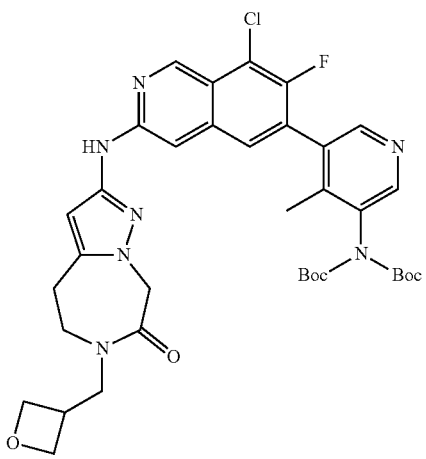 [SMILES: Cc1c(-c2cc3cc(Nc4cc5n(n4)CC(=O)N(CC4COC4)CC5)ncc3c(Cl)c2F)cncc1N(C(=O)OC(C)(C)C)C(=O)OC(C)(C)C]

A mixture of tert-butyl N-[5-(3-amino-8-chloro-7-fluoro-6-isoquinolyl)-4-methyl-3-pyridyl]-N-tert-butoxycarbonyl-carbamate (214.5 mg, 0.43 mmol), 2-bromo-6-(oxetan-3-ylmethyl)-5,8-dihydro-4H-pyrazolo[1,5-d][1,4]diazepin-7-one (192.01 mg, 0.64 mmol), tris(dibenzylideneacetone)dipalladium-chloroformadduct (88.28 mg, 0.09 mmol), 4,5-bis(diphenylphosphino)-9,9-dimethylxanthene (98.6 mg, 0.17 mmol) and cesium carbonate (347.57 mg, 1.07 mmol) in 1,4-dioxane (19 mL) was stirred at 100° C. for 4 hours. The mixture was concentrated under vacuum. The residue was purified by flash chromatography on silica gel eluting with dichloromethane/methanol (96/4) to afford tert-butyl N-tert-butoxycarbonyl-N-[5-[8-chloro-7-fluoro-3-[[6-(oxetan-3-ylmethyl)-7-oxo-5,8-dihydro-4H-pyrazolo[1,5-d][1,4]diazepin-2-yl]amino]-6-isoquinolyl]-4-methyl-3-pyridyl]carbamate (231.3 mg, 0.32 mmol) as orange solid. LCMS15 (ESI) [M+H]$^+$=722.3.

Step 3: Tert-butyl N-[7-fluoro-3-([6-methyl-7-oxo-4H,5H,6H,7H,8H-pyrazolo[1,5-d][1,4]diazepin-2-yl] amino)-6-(4-methylpyridin-3-yl)isoquinolin-8-yl] carbamate

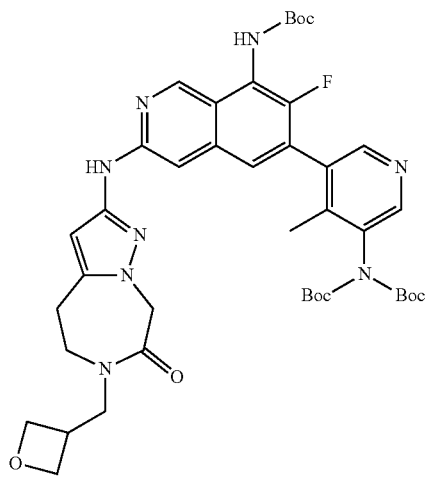 [SMILES: Cc1c(-c2cc3cc(Nc4cc5n(n4)CC(=O)N(CC4COC4)CC5)ncc3c(NC(=O)OC(C)(C)C)c2F)cncc1N(C(=O)OC(C)(C)C)C(=O)OC(C)(C)C]

A mixture of tert-butyl N-tert-butoxycarbonyl-N-[5-[8-chloro-7-fluoro-3-[[6-(oxetan-3-ylmethyl)-7-oxo-5,8-dihydro-4H-pyrazolo[1,5-d][1,4]diazepin-2-yl]amino]-6-isoquinolyl]-4-methyl-3-pyridyl]carbamate (231.3 mg, 0.32 mmol), tert-butyl carbamate (936.78 mg, 8.01 mmol), tris(dibenzylideneacetone)dipalladium-chloroformadduct (66.3 mg, 0.06 mmol) and Brettphos (68.67 mg, 0.13 mmol) in 1,4-dioxane (20 mL) was added cesium carbonate (261.02 mg, 0.80 mmol) at 25° C. The reaction solution was stirred at 90° C. for 1 hour. After filtration, the filtrate was concentrated under vacuum. The residue was purified by flash chromatography on silica gel eluting with petroleum ether/ethyl acetate (1/1) to afford tert-butyl N-tert-butoxycarbonyl-N-[5-[8-(tert-butoxycarbonylamino)-7-fluoro-3-[[6-(oxetan-3-ylmethyl)-7-oxo-5,8-dihydro-4H-pyrazolo[1,5-d][1,4]diazepin-2-yl]amino]-6-isoquinolyl]-4-methyl-3-pyridyl]carbamate (105.4 mg, 0.1313 mmol) as a brown solid. LCMS (ESI) [M+H]$^+$=803.3.

Step 4: 2-[[8-amino-6-(5-amino-4-methyl-3-pyridyl)-7-fluoro-3-isoquinolyl]amino]-6-(oxetan-3-ylmethyl)-5,8-dihydro-4H-pyrazolo[1,5-d][1,4]diazepin-7-one

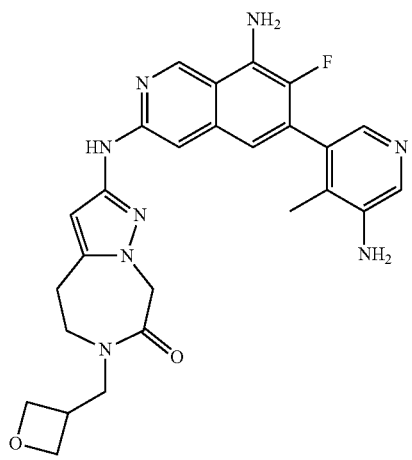 [SMILES: Cc1c(N)cncc1-c1cc2cc(Nc3cc4n(n3)CC(=O)N(CC3COC3)CC4)ncc2c(N)c1F]

A solution of tert-butyl N-tert-butoxycarbonyl-N-[5-[8-(tert-butoxycarbonylamino)-7-fluoro-3-[[6-(oxetan-3-ylmethyl)-7-oxo-5,8-dihydro-4H-pyrazolo[1,5-d][1,4]diazepin-2-yl]amino]-6-isoquinolyl]-4-methyl-3-pyridyl]carbamate (66 mg, 0.08 mmol) in oxydibenzene (2.0 mL) was stirred for 3 hours at 180° C. The reaction was dissolved in N,N-dimethylformamide and then purified by Prep-HPLC (Atlantis HILIC OBD Column 19*150 mm*5 um; Water (10 mmol/L sodium bicarbonate)/ACN=15%-30% in 7 min) to afford 2-[[8-amino-6-(5-amino-4-methyl-3-pyridyl)-7-fluoro-3-isoquinolyl]amino]-6-(oxetan-3-ylmethyl)-5,8-dihydro-4H-pyrazolo[1,5-d][1,4]diazepin-7-one (4.6 mg, 0.0092 mmol) as a yellow solid. LCMS (ESI) [M+H]$^+$=503.3. $^1$HNMR (300 MHz, DMSO-d$_6$) δ 9.24 (s, 1H), 9.06 (s, 1H), 7.98 (s, 1H), 7.69-7.66 (m, 2H), 6.72-6.70 (m, 1H), 6.06 (s, 2H), 5.97 (s, 1H), 5.22 (s, 2H), 4.97 (s, 2H), 4.63-4.59 (m, 2H), 4.34-4.30 (m, 2H), 3.83 (m, 2H), 3.71-3.69 (m, 2H), 3.25-3.21 (m, 1H), 2.99-2.98 (m, 2H), 1.92 (s, 3H).

Example 172

2-((8-amino-6-(5-amino-6-methoxy-4-methylpyridin-3-yl)-7-fluoroisoquinolin-3-yl)amino)-6-(2,2-difluoroethyl)-5,6-dihydro-4H-pyrazolo[1,5-d][1,4]diazepin-7(8H)-one (Compound 278)

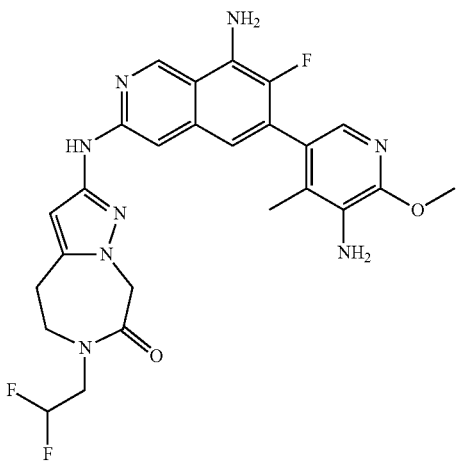 [SMILES: COc1ncc(-c2cc3cc(Nc4cc5n(n4)CC(=O)N(CC(F)F)CC5)ncc3c(N)c2F)c(C)c1N]

Step 1: 2-methoxy-4-methyl-3-nitro-5-(4,4,5,5-tetramethyl-1,3,2-dioxaborolan-2-yl)pyridine

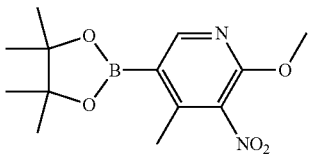

A mixture of 5-bromo-2-methoxy-4-methyl-3-nitro-pyridine (2.0 g, 8.1 mmol), bis(pinacolato)diboron (10.28 g, 40.48 mmol), [1,1'-bis(diphenylphosphino)ferrocene]dichloropalladium(II) (1.19 g, 1.62 mmol) and potassium acetate (2.38 g, 24.29 mmol) in 1,4-dioxane (40 mL) was stirred at 100° C. for 2 hours. The mixture was concentrated under vacuum. The residue was purified by flash chromatography on silica gel eluting with petroleum ether/ethyl acetate (1/1) to afford 2-methoxy-4-methyl-3-nitro-5-(4,4,5,5-tetramethyl-1,3,2-dioxaborolan-2-yl)pyridine (2.1 g, 7.14 mmol) as a yellow solid. LCMS (ESI) [M+H]$^+$=295.

Step 2: 8-chloro-7-fluoro-6-(6-methoxy-4-methyl-5-nitro-3-pyridyl)isoquinolin-3-amine

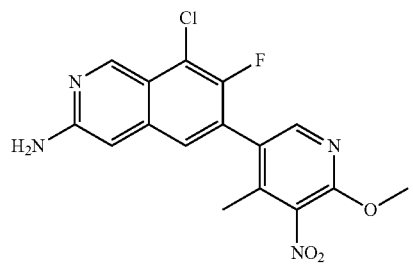 [SMILES: COc1ncc(-c2cc3cc(N)ncc3c(Cl)c2F)c(C)c1[N+](=O)[O-]]

A mixture of 8-chloro-7-fluoro-6-iodo-isoquinolin-3-amine (1.0 g, 3.1 mmol), 2-methoxy-4-methyl-3-nitro-5-(4,4,5,5-tetramethyl-1,3,2-dioxaborolan-2-yl)pyridine (1.37 g, 4.65 mmol), [1,1'-bis(diphenylphosphino)ferrocene]dichloropalladium(II) (226.97 mg, 0.31 mmol) and potassium carbonate (941.37 mg, 6.82 mmol) in 1,4-dioxane (30 mL) and water (3 mL) was stirred at 90° C. for 2 hours. The solvent was concentrated under vacuum. The residue was purified by flash chromatography on silica gel eluting with petroleum ether/ethyl acetate (1/1) to afford 8-chloro-7-fluoro-6-(6-methoxy-4-methyl-5-nitro-3-pyridyl)isoquinolin-3-amine (780 mg, 2.15 mmol) as a yellow solid. LCMS (ESI) [M+H]$^+$=363.

Step 3: 2-bromo-6-(2,2-difluoroethyl)-5,8-dihydro-4H-pyrazolo[1,5-d][1,4]diazepin-7-one

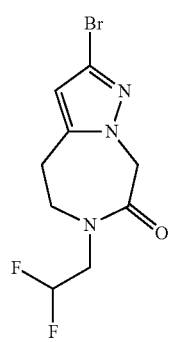

To a solution of 2-bromo-4,5,6,8-tetrahydropyrazolo[1,5-d][1,4]diazepin-7-one (500 mg, 2.17 mmol) in N,N-dimethylformamide (20 mL) was added sodium hydride (156.48 mg, 60% purity, 6.52 mmol) at 0° C. The resulting mixture was stirred for 30 minutes at 0° C. Then 2-iodo-1,1-difluoroethane (2.09 g, 10.87 mmol) was added. The mixture was stirred at 25° C. for 3 hours. The reaction was quenched with water. The resulting solution was extracted with ethyl acetate, dried with anhydrous sodium sulfate. After filtration, the filtrate was concentrated under vacuum. The residue was purified by reverse phase chromatography (acetonitrile 0-40/0.1% sodium bicarbonate in water) to afford 2-bromo-6-(2,2-difluoroethyl)-5,8-dihydro-4H-pyrazolo[1, 5-d][1,4]diazepin-7-one (480 mg, 1.63 mmol) as a white solid. LCMS (ESI) [M+H]$^+$=294.

Step 4: 2-[[8-chloro-7-fluoro-6-(6-methoxy-4-methyl-5-nitro-3-pyridyl)-3-isoquinolyl]amino]-6-(2,2-difluoroethyl)-5,8-dihydro-4H-pyrazolo[1,5-d][1,4]diazepin-7-one

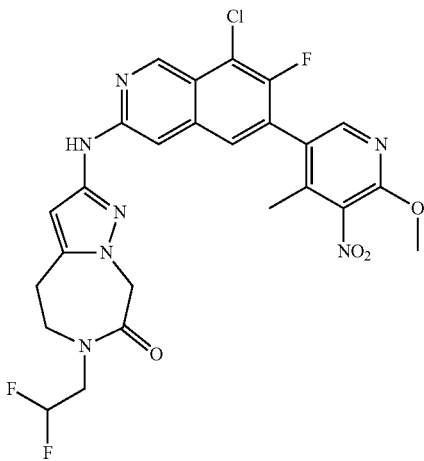 [SMILES: COc1ncc(-c2cc3cc(Nc4cc5n(n4)CC(=O)N(CC(F)F)CC5)ncc3c(Cl)c2F)c(C)c1[N+](=O)[O-]]

A mixture of 8-chloro-7-fluoro-6-(6-methoxy-4-methyl-5-nitro-3-pyridyl)isoquinolin-3-amine (300 mg, 0.83 mmol), 2-bromo-6-(2,2-difluoroethyl)-5,8-dihydro-4H-pyrazolo[1,5-d][1,4]diazepin-7-one (291.88 mg, 0.99 mmol), tris(dibenzylideneacetone)dipalladium-chloroform adduct (171.2 mg, 0.17 mmol), 4,5-bis(diphenylphosphino)-9,9-dimethylxanthene (191.21 mg, 0.33 mmol) and cesium carbonate (674.04 mg, 2.07 mmol) in 1,4-dioxane (45 mL) was stirred at 100° C. for 7 hours. After filtration, the filtrate was concentrated under vacuum. The residue was purified by flash chromatography on silica gel eluting with petroleum ether/ethyl acetate (4/1) to afford 2-[[8-chloro-7-fluoro-6-(6-methoxy-4-methyl-5-nitro-3-pyridyl)-3-isoquinolyl]amino]-6-(2,2-difluoroethyl)-5,8-dihydro-4H-pyrazolo[1,5-d][1,4]diazepin-7-one (175 mg, 0.30 mmol) as a yellow solid. LCMS (ESI) [M+H]$^+$=576.

Step 5: tert-butyl N-[3-[[6-(2,2-difluoroethyl)-7-oxo-5,8-dihydro-4H-pyrazolo[1,5-d][1,4]diazepin-2-yl]amino]-7-fluoro-6-(6-methoxy-4-methyl-5-nitro-3-pyridyl)-8-isoquinolyl]carbamate

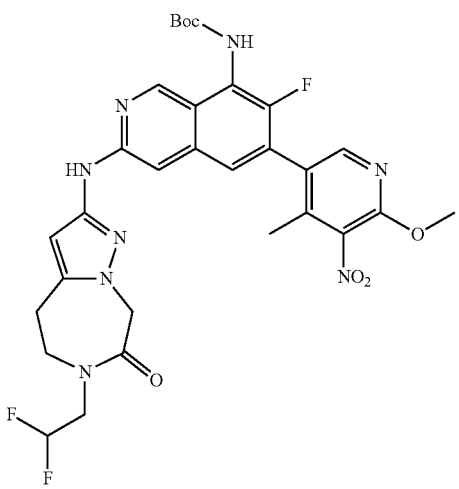 [SMILES: COc1ncc(-c2cc3cc(Nc4cc5n(n4)CC(=O)N(CC(F)F)CC5)ncc3c(NC(=O)OC(C)(C)C)c2F)c(C)c1N]

A mixture of 2-[[8-chloro-7-fluoro-6-(6-methoxy-4-methyl-5-nitro-3-pyridyl)-3-isoquinolyl]amino]-6-(2,2-difluoroethyl)-5,8-dihydro-4H-pyrazolo[1,5-d][1,4]diazepin-7-one (84 mg, 0.15 mmol), tert-butyl carbamate (427.16 mg, 3.65 mmol), tris(dibenzylideneacetone)dipalladium-chloroform adduct (30.19 mg, 0.03 mmol), Brettphos (31.27 mg, 0.06 mmol) and cesium carbonate (237.74 mg, 0.73 mmol) in 1,4-dioxane (8 mL) was stirred at 90° C. for 2 hours. The mixture was concentrated under vacuum. The resulting residue was purified by reverse phase chromatography (acetonitrile 0-50/0.1% sodium bicarbonate in water) to afford tert-butyl N-[3-[[6-(2,2-difluoroethyl)-7-oxo-5,8-dihydro-4H-pyrazolo[1,5-d][1,4]diazepin-2-yl]amino]-7-fluoro-6-(6-methoxy-4-methyl-5-nitro-3-pyridyl)-8-isoquinolyl]carbamate (40 mg, 0.061 mmol) as a yellow solid. LCMS (ESI) [M+H]$^+$=657.

Step 6: tert-butyl (6-(5-amino-6-methoxy-4-methylpyridin-3-yl)-3-((6-(2,2-difluoroethyl)-7-oxo-5,6,7,8-tetrahydro-4H-pyrazolo[1,5-d][1,4]diazepin-2-yl)amino)-7-fluoroisoquinolin-8-yl)carbamate

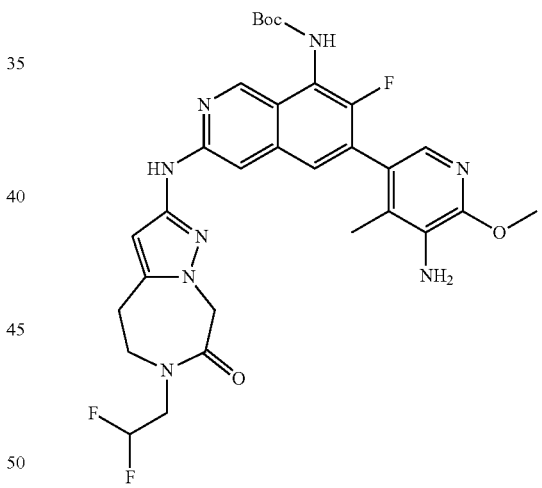

A mixture of tert-butyl N-[3-[[6-(2,2-difluoroethyl)-7-oxo-5,8-dihydro-4H-pyrazolo[1,5-d][1,4]diazepin-2-yl]amino]-7-fluoro-6-(6-methoxy-4-methyl-5-nitro-3-pyridyl)-8-isoquinolyl]carbamate (40 mg, 0.06 mmol) and raney nickel (60 mg, 0.06 mmol) in methanol (7 mL) was stirred at 25° C. for 1 hour under hydrogen (1 atm). After filtration, the filtrate was concentrated under vacuum to afford tert-butyl (6-(5-amino-6-methoxy-4-methylpyridin-3-yl)-3-((6-(2,2-difluoroethyl)-7-oxo-5,6,7,8-tetrahydro-4H-pyrazolo[1,5-d][1,4]diazepin-2-yl)amino)-7-fluoroisoquinolin-8-yl)carbamate (30 mg, 0.048 mmol) as a yellow solid. LCMS (ESI) [M+H]$^+$=627.

779

Step 7: 2-[[8-amino-6-(5-amino-6-methoxy-4-methyl-3-pyridyl)-7-fluoro-3-isoquinolyl]amino]-6-(2,2-difluoroethyl)-5,8-dihydro-4H-pyrazolo[1,5-d][1,4]diazepin-7-one

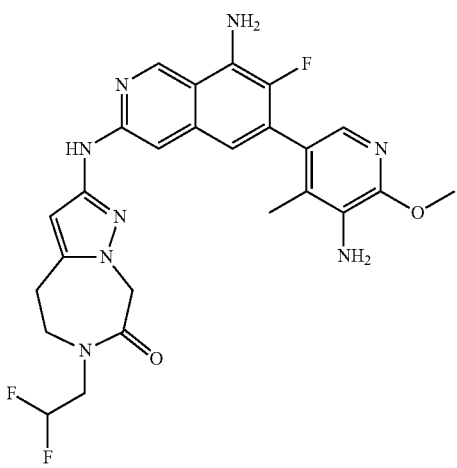 [SMILES: COc1ncc(-c2cc3cc(Nc4cc5n(n4)CC(=O)N(CC(F)F)CC5)ncc3c(N)c2F)c(C)c1N]

A solution of tert-butyl N-[6-(5-amino-6-methoxy-4-methyl-3-pyridyl)-3-[[6-(2,2-difluoroethyl)-7-oxo-5,8-dihydro-4H-pyrazolo[1,5-d][1,4]diazepin-2-yl]amino]-7-fluoro-8-isoquinolyl]carbamate (20 mg, 0.03 mmol) and 2,2,2-trifluoroacetic acid (3 mL) in dichloromethane (3 mL) was stirred at 25° C. for 1 hour. The reaction was concentrated under vacuum. The residue was adjusted to pH 10 with ammonia in methanol (7 mol/L). The crude product was purified by Prep-HPLC (XBridge Shield RP18 OBD Column 30*150 mm, 5 um; Water (10 mmol/L sodium bicarbonate): ACN (30% to 45%) in 7 min) to afford 2-[[8-amino-6-(5-amino-6-methoxy-4-methyl-3-pyridyl)-7-fluoro-3-isoquinolyl]amino]-6-(2,2-difluoroethyl)-5,8-dihydro-4H-pyrazolo[1,5-d][1,4]diazepin-7-one (1.8 mg, 0.0034 mmol) as a dark yellow solid. LCMS (ESI) [M+H]$^+$=527.2; $^1$HNMR (300 MHz, DMSO-d$_6$) δ 9.24 (s, 1H), 9.06 (s, 1H), 7.70 (s, 1H), 7.34 (s, 1H), 6.70 (d, J=6.1 Hz, 1H), 6.29-5.89 (m, 4H), 5.05 (s, 2H), 4.80 (s, 2H), 3.93 (m, 6H), 3.80 (s, 1H), 3.06 (m, 2H), 1.95 (d, J=1.6 Hz, 3H).

Example 173

(1R,2R,3R)—N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide (Compound 279)

(1S,2S,3S)—N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide (Compound 280)

(1R,2S,3R)—N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide (Compound 281)

780

(1S,2R,3S)—N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide (Compound 282)

(1S,3S)—N-(8-amino-6-(5-amino-4-methylpyridin-3-yl)-7-fluoroisoquinolin-3-yl)-2,2-dimethyl-3-(1-methyl-1H-pyrazol-4-yl)cyclopropane-1-carboxamide (Compound 120) and (1R,3R)—N-(8-amino-6-(5-amino-4-methylpyridin-3-yl)-7-fluoroisoquinolin-3-yl)-2,2-dimethyl-3-(1-methyl-1H-pyrazol-4-yl)cyclopropane-1-carboxamide (Compound 121)

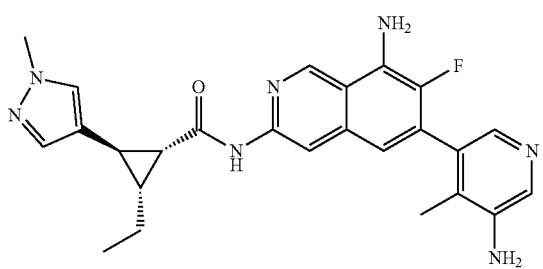

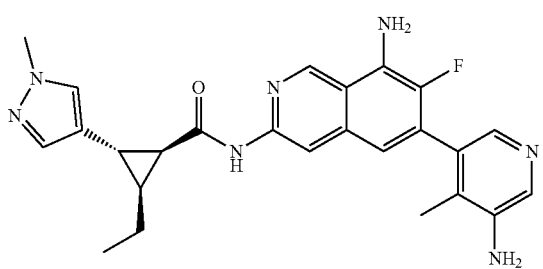

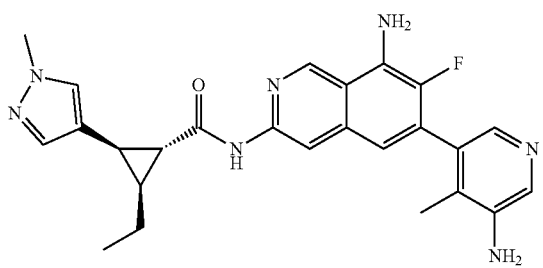

-continued

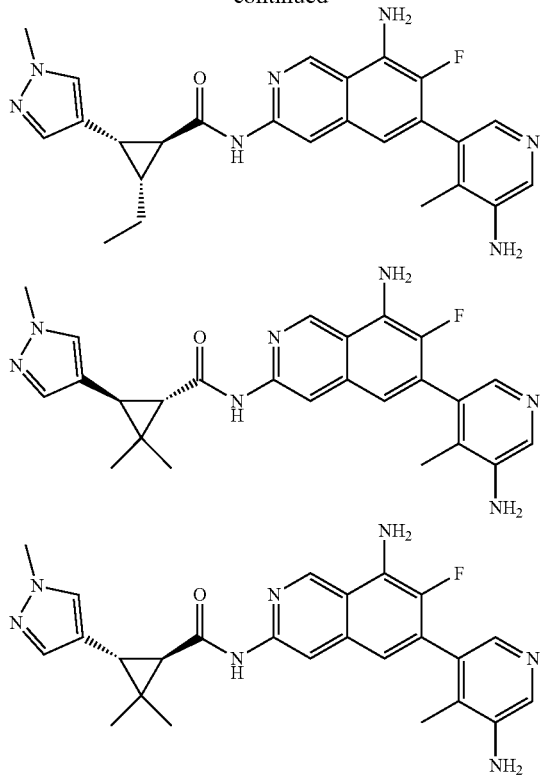

Step 1: Diphenyl(propyl)sulfonium tetrafluoroborate

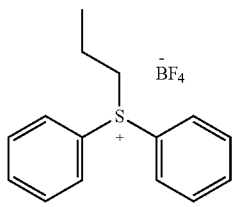

To a solution of silver tetrafluoroborate (2 g, 10.31 mmol) in dichloromethane (20 mL) was added 1-iodopropane (1.75 g, 10.31 mmol) and diphenyl sulfide (5.76 g, 30.93 mmol) at 0° C. The reaction was stirred at 35° C. for 15 hours. The mixture was filtered and the filtrate was concentrated under vacuum. The residue was washed with dichloromethane-ether to afford diphenyl(propyl)sulfonium tetrafluoroborate (2 g, 6.32 mmol) as a white solid. LCMS (ESI) [M+H]$^+$=229.

Step 2: trans-tert-butyl 2-ethyl-3-(1-methylpyrazol-4-yl)cyclopropanecarboxylate

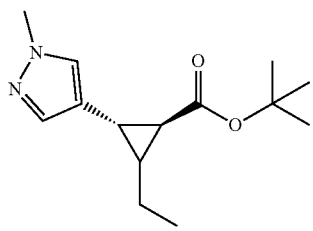 [SMILES: CCC1[C@H](C(=O)OC(C)(C)C)[C@H]1c1cnn(C)c1]

To a solution of diphenyl(propyl)sulfonium tetrafluoroborate (1.50 g, 4.75 mmol) in 1,2-dimethoxyethane (30 mL) and dichloromethane (3 mL) was added lithium diisopropylamide (5.54 ml, 11.09 mmol) at −78° C. The resulting mixture was stirred for 1 hour at −78° C. Then tert-butyl (Z)-3-(1-methylpyrazol-4-yl)prop-2-enoate (330 mg, 1.58 mmol) was added and stirred at −78° C. to 25° C. for 15 hours. The reaction was quenched with water. The resulting mixture was extracted with dichloromethane and dried with anhydrous sodium sulfate. After filtration, the filtrate was concentrated under vacuum to afford trans-tert-butyl 2-ethyl-3-(1-methylpyrazol-4-yl)cyclopropanecarboxylate as a mixture of 4 stereoisomers where pyrazole is trans to ester (350 mg, 1.40 mmol) as a brown oil. LCMS (ESI) [M+H]$^+$=251.

Step 3: trans-2-ethyl-3-(1-methylpyrazol-4-yl)cyclopropanecarboxylic Acid

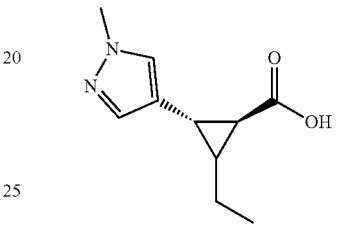

A solution of trans-tert-butyl 2-ethyl-3-(1-methylpyrazol-4-yl)cyclopropanecarboxyate (350 mg, 1.4 mmol) and 2,2,2-trifluoroacetic acid (8 mL) in dichloromethane (3 mL) was stirred at 25° C. for 1 hour. The mixture was concentrated under vacuum. The resulting residue was purified by reverse phase chromatography (acetonitrile 0-40/0.1% HCl in water) to afford trans-2-ethyl-3-(1-methylpyrazol-4-yl)cyclopropanecarboxylic acid (260 mg, 1.34 mmol) as a brown oil. LCMS (ESI) [M+H]$^+$=195.

Step 4: trans-tert-butyl N-tert-butoxycarbonyl-N-[5-[8-chloro-3-[[2-ethyl-3-(1-methylpyrazol-4-yl)cyclopropanecarbonyl]amino]-7-fluoro-6-isoquinolyl]-4-methyl-3-pyridyl]carbamate

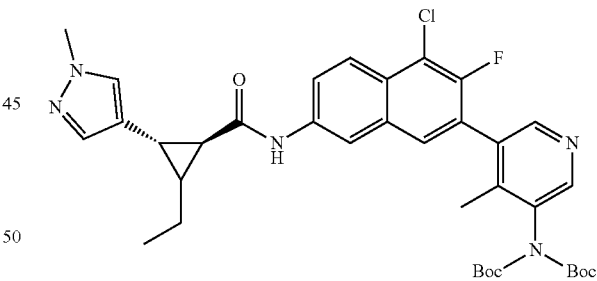

A solution of tert-butyl N-[5-(3-amino-8-chloro-7-fluoro-6-isoquinolyl)-4-methyl-3-pyridyl]-N-tert-butoxycarbonyl-carbamate (675 mg, 1.34 mmol), trans-2-ethyl-3-(1-methylpyrazol-4-yl)cyclopropanecarboxylic acid (338.86 mg, 1.74 mmol) and pyridine (3 mL) in dichloromethane (15 mL) was added phosphorus oxychloride (410.66 mg, 2.68 mmol) at 0° C. The reaction was stirred at 25° C. for 30 minutes and then quenched by water. The resulting mixture was extracted with dichloromethane, dried with anhydrous sodium sulfate. After filtration, the filtrate was concentrated under vacuum to afford trans-tert-butyl N-tert-butoxycarbonyl-N-[5-[8-chloro-3-[[2-ethyl-3-(1-methylpyrazol-4-yl)cyclopropanecarbonyl]amino]-7-fluoro-6-isoquinolyl]-4-methyl-3-pyridyl]carbamate (900 mg, 1.32 mmol) as a brown solid. LCMS (ESI) [M+H]$^+$=679.

Step 5:trans-tert-butyl N-tert-butoxycarbonyl-N-[5-[8-(tert-butoxycarbonylamino)-3-[[2-ethyl-3-(1-methylpyrazol-4-yl)cyclopropanecarbonyl]amino]-7-fluoro-6-isoquinolyl]-4-methyl-3-pyridyl]carbamate

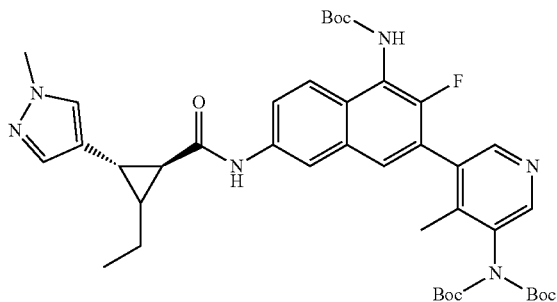 [SMILES: CCC1[C@H](C(=O)Nc2ccc3c(NC(=O)OC(C)(C)C)c(F)c(-c4cncc(N(C(=O)OC(C)(C)C)C(=O)OC(C)(C)C)c4C)cc3c2)[C@H]1c1cnn(C)c1]

A mixture of trans-tert-butyl N-tert-butoxycarbonyl-N-[5-[8-chloro-3-[[2-ethyl-3-(1-methylpyrazol-4-yl)cyclopropanecarbonyl]amino]-7-fluoro-6-isoquinolyl]-4-methyl-3-pyridyl]carbamate (1.3 g, 1.91 mmol), tert-butyl carbamate (5.61 g, 47.85 mmol), tris(dibenzylideneacetone)dipalladium-chloroformadduct (396.21 mg, 0.38 mmol), Brettphos (410.38 mg, 0.77 mmol) and cesium carbonate (3.12 g, 9.57 mmol) in 1,4-dioxane (80 mL) was stirred at 90° C. for 2 hours. The mixture was concentrated under vacuum. The residue was purified by flash chromatography on silica gel eluting with dichloromethane/methanol (95/5) to afford trans-tert-butyl N-tert-butoxycarbonyl-N-[5-[8-(tert-butoxycarbonylamino)-3-[[2-ethyl-3-(1-methylpyrazol-4-yl)cyclopropanecarbonyl]amino]-7-fluoro-6-isoquinolyl]-4-methyl-3-pyridyl]carbamate (1 g, 1.32 mmol) as a yellow solid. LCMS (ESI) [M+H]$^+$=760.

Step 6: (1R,2R,3R)—N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide, (1S,2S,3S)—N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide, (1R,2S,3R)—N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide, (1S,2R,3S)—N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide, (1S,3S)—N-(8-amino-6-(5-amino-4-methylpyridin-3-yl)-7-fluoroisoquinolin-3-yl)-2,2-dimethyl-3-(1-methyl-1H-pyrazol-4-yl)cyclopropane-1-carboxamide and (1R,3R)—N-(8-amino-6-(5-amino-4-methylpyridin-3-yl)-7-fluoroisoquinolin-3-yl)-2,2-dimethyl-3-(1-methyl-1H-pyrazol-4-yl)cyclopropane-1-carboxamide

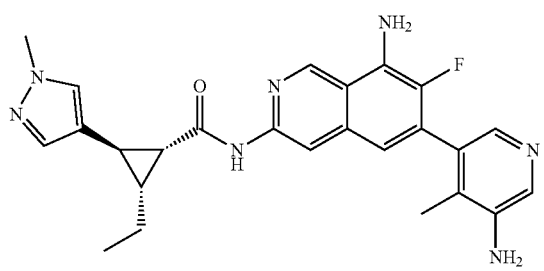

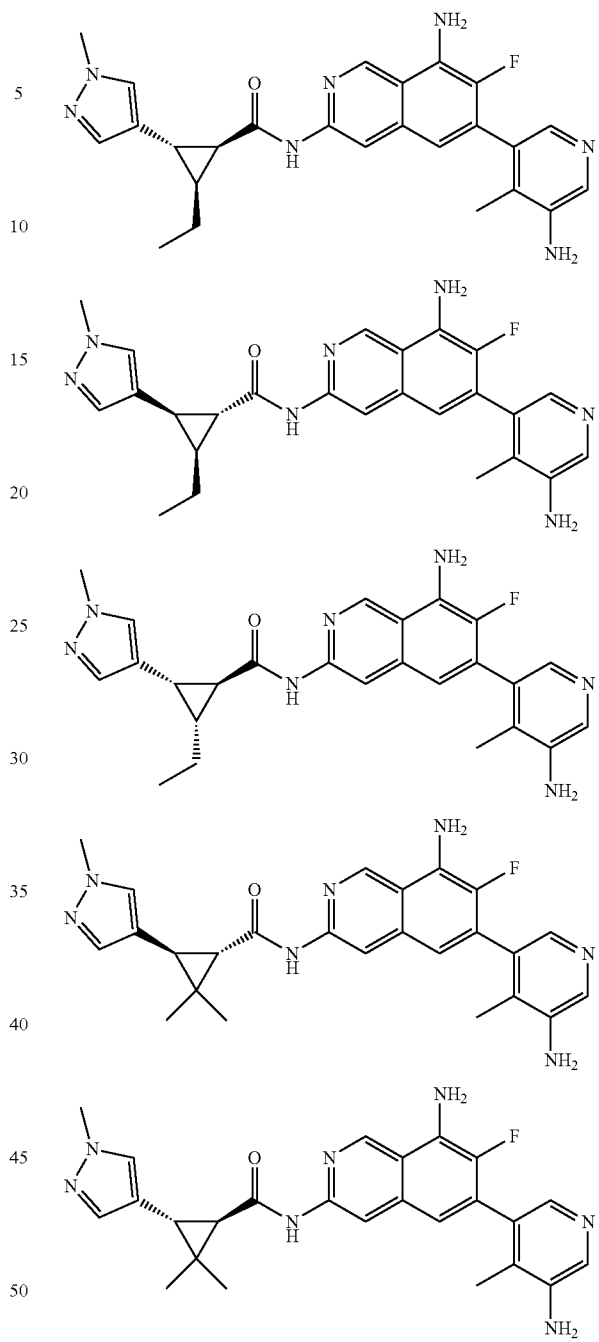

A solution of trans-tert-butyl N-tert-butoxycarbonyl-N-[5-[8-(tert-butoxycarbonylamino)-3-[[2-ethyl-3-(1-methylpyrazol-4-yl)cyclopropanecarbonyl]amino]-7-fluoro-6-isoquinolyl]-4-methyl-3-pyridyl]carbamate (1.0 g, 1.32 mmol) and 2,2,2-trifluoroacetic acid (10 mL) in dichloromethane (10 mL) was stirred at 25° C. for 1 hour. The reaction was concentrated under vacuum. The residue was purified by Prep-HPLC with the following conditions (XBridge Prep OBD C18 Column 30×150 mm 5 um; Water (10 mmol/L sodium bicarbonate): ACN (22% to 40%) in 7 min) to afford the mixture of the six isomeric products (230 mg, 0.50 mmol). The mixture was purified by chiral-HPLC to afford six isomers.

Cyclopropane stereochemistry for ethylcyclopropane-containing isomers (Compounds 279-282) (Pyrazole trans to amide; Ethyl relative stereochemistry arbitrarily assigned; All absolute stereochemistry arbitrarily assigned): Compound 279: (47.7 mg, 0.104 mmol) as a yellow solid. Retention time: 6.036 min (CHIRALPAK ID-3, 0.46*10 cm; 3 m;

MtBE (0.1% DEA):EtOH=70:30; 2 ml/min). LCMS (ESI) [M+H]$^+$=460.2; $^1$HNMR (300 MHz, DMSO-d$_6$) δ 10.73 (s, 1H), 9.41 (s, 1H), 8.29 (s, 1H), 7.99 (s, 1H), 7.66 (s, 1H), 7.53 (s, 1H), 7.29 (s, 1H), 6.86 (d, J=6.1 Hz, 1H), 6.24 (s, 2H), 5.25 (s, 2H), 3.80 (s, 3H), 2.37-2.27 (m, 1H), 2.18 (m, 1H), 1.92 (d, J=1.5 Hz, 3H), 1.62-1.45 (m, 1H), 1.22 (m, 2H), 0.89 (m, 3H). Compound 280: (56 mg, 0.12 mmol) as a yellow solid. Retention time: 7.559 min (CHIRALPAK ID-3, 0.46*10 cm; 3 m; MtBE (0.1% DEA): EtOH=70:30; 2 ml/min). LCMS (ESI) [M+H]$^+$=460.2; $^1$HNMR (300 MHz, DMSO-d$_6$) δ 10.73 (s, 1H), 9.41 (s, 1H), 8.29 (s, 1H), 7.99 (s, 1H), 7.66 (s, 1H), 7.53 (s, 1H), 7.29 (s, 1H), 6.86 (d, J=6.1 Hz, 1H), 6.24 (s, 2H), 5.25 (s, 2H), 3.80 (s, 3H), 2.38-2.15 (m, 2H), 1.92 (d, J=1.5 Hz, 3H), 1.62-1.43 (m, 1H), 1.23 (m, 2H), 0.89 (m, 3H). Compound 281: (13.5 mg, 0.029 mmol) as a yellow solid. Retention time: 4.98 min (CHIRALPAK ID-3, 0.46*10 cm; 3 m; MtBE (0.1% DEA):EtOH=70:30; 2 ml/min). LCMS (ESI) [M+H]$^+$=460.2; $^1$HNMR (300 MHz, DMSO-d$_6$) δ 10.69 (s, 1H), 9.40 (s, 1H), 8.31 (s, 1H), 7.99 (s, 1H), 7.67 (s, 1H), 7.52 (s, 1H), 7.25 (d, J=0.8 Hz, 1H), 6.87 (d, J=6.1 Hz, 1H), 6.24 (s, 2H), 5.25 (s, 2H), 3.77 (s, 3H), 2.29-2.17 (m, 2H), 1.92 (d, J=1.5 Hz, 3H), 1.83-1.42 (m, 3H), 0.92 (t, J=7.3 Hz, 3H). Compound 282: (10.2 mg, 0.022 mmol) as a yellow solid. Retention time: 3.847 min (CHIRALPAK ID-3, 0.46*10 cm; 3 m;

MtBE (0.1% DEA):EtOH=70:30; 2 ml/min). LCMS (ESI) [M+H]$^+$=460.2; HNMR (300 MHz, DMSO-d$_6$) δ 10.69 (s, 1H), 9.40 (s, 1H), 8.31 (s, 1H), 7.99 (s, 1H), 7.67 (s, 1H), 7.52 (s, 1H), 7.25 (d, J=0.8 Hz, 1H), 6.87 (d, J=6.1 Hz, 1H), 6.24 (s, 2H), 5.25 (s, 2H), 3.77 (s, 3H), 2.29-2.17 (m, 2H), 1.92 (d, J=1.5 Hz, 3H), 1.83-1.42 (m, 3H), 0.92 (t, J=7.3 Hz, 3H). Compound 120: N-[8-amino-6-(5-amino-4-methyl-3-pyridyl)-7-fluoro-3-isoquinolyl]-2,2-dimethyl-3-(1-methylpyrazol-4-yl)cyclopropanecarboxamide (16.6 mg, 0.036 mmol) as a yellow solid. Retention time: 6.312 min (CHIRALPAK ID-3, 0.46*10 cm; 3 m;

MtBE (0.1% DEA):EtOH=70:30; 2 ml/min). LCMS (ESI) [M+H]$^+$=460.2; HNMR (300 MHz, DMSO-d$_6$) δ 10.63 (s, 1H), 9.41 (s, 1H), 8.32 (s, 1H), 7.99 (s, 1H), 7.66 (s, 1H), 7.51 (s, 1H), 7.25 (s, 1H), 6.87 (d, J=6.2 Hz, 1H), 6.23 (s, 2H), 5.25 (s, 2H), 3.79 (s, 3H), 2.33-2.19 (m, 2H), 1.92 (d, J=1.4 Hz, 3H), 1.29 (s, 3H), 0.99 (s, 3H). Compound 121: N-[8-amino-6-(5-amino-4-methyl-3-pyridyl)-7-fluoro-3-isoquinolyl]-2,2-dimethyl-3-(1-methylpyrazol-4-yl)cyclopropanecarboxamide (16 mg, 0.035 mmol) as a yellow solid. Retention time: 5.166 min (CHIRALPAK ID-3, 0.46*10 cm; 3 m; MtBE (0.1% DEA):EtOH=70:30; 2 ml/min). LCMS (ESI) [M+H]$^+$=460.2; $^1$HNMR (300 MHz, DMSO-d$_6$) δ 10.63 (s, 1H), 9.41 (s, 1H), 8.32 (s, 1H), 7.99 (s, 1H), 7.66 (s, 1H), 7.51 (s, 1H), 7.26 (s, 1H), 6.87 (d, J=6.1 Hz, 1H), 6.24 (s, 2H), 5.25 (s, 2H), 3.79 (s, 3H), 2.38-2.15 (m, 2H), 1.92 (d, J=1.5 Hz, 3H), 1.28 (s, 3H), 0.99 (s, 3H).

Example 174

2-[[8-amino-6-(5-amino-4-methyl-3-pyridyl)-7-fluoro-3-isoquinolyl]amino]-6-cyclopropyl-5,8-dihydro-4H-pyrazolo[1,5-d][1,4]diazepin-7-one (Compound 283)

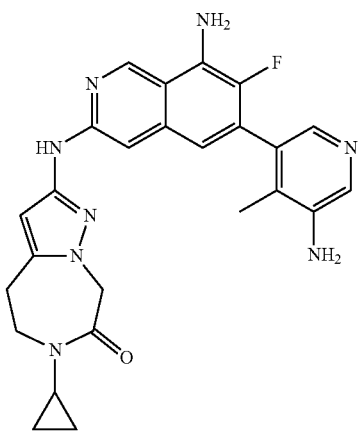 [SMILES: Cc1c(N)cncc1-c1cc2cc(Nc3cc4n(n3)CC(=O)N(C3CC3)CC4)ncc2c(N)c1F]

Step 1: [2-bromo-6-cyclopropyl-5,8-dihydro-4H-pyrazolo[1,5-d][1,4]diazepin-7-one

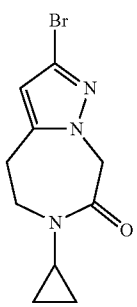 [SMILES: O=C1Cn2nc(Br)cc2CCN1C1CC1]

A mixture of cyclopropylboronic acid (448.06 mg, 5.22 mmol), 2-bromo-4,5,6,8-tetrahydropyrazolo[1,5-d][1,4]diazepin-7-one (400.0 mg, 1.74 mmol), copper(II)acetate (567.97 mg, 1.74 mmol), triethylamine (526.82 mg, 5.22 mmol) and pyridine (206.03 mg, 2.61 mmol) in tetrahydrofuran (5 mL) was stirred for 12 h at 60° C. under oxygen. The reaction mixture was diluted with water (50 mL). The resulting mixture was extracted with dichloromethane, dried over anhydrous sodium sulfate and concentrated under vacuum. The residue was purified by flash chromatography on silica gel eluting with methanol/dichloromethane (2/98) to afford [2-bromo-6-cyclopropyl-5,8-dihydro-4H-pyrazolo[1,5-d][1,4]diazepin-7-one (260 mg, 0.96 mmol) as a yellow oil. LC/MS (ESI) [M+H]$^+$=270.1

Step 2: tert-butyl N-tert-butoxycarbonyl-N-[5-[8-chloro-3-[(6-cyclopropyl-7-oxo-5,8-dihydro-4H-pyrazolo[1,5-d][1,4]diazepin-2-yl)amino]-7-fluoro-6-isoquinolyl]-4-methyl-3-pyridyl]carbamate

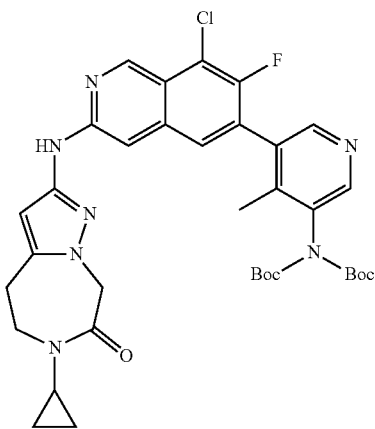 [SMILES: Cc1c(-c2cc3cc(Nc4cc5n(n4)CC(=O)N(C4CC4)CC5)ncc3c(Cl)c2F)cncc1N(C(=O)OC(C)(C)C)C(=O)OC(C)(C)C]

A mixture of 2-bromo-6-cyclopropyl-5,8-dihydro-4H-pyrazolo[1,5-d][1,4]diazepin-7-one (150 mg, 0.56 mmol), tert-butyl N-[5-(3-amino-8-chloro-7-fluoro-6-isoquinolyl)-4-methyl-3-pyridyl]-N-tert-butoxycarbonyl-carbamate (195 mg, 0.39 mmol), tris(dibenzylideneacetone)dipalladium-chloroformadduct (80.25 mg, 0.08 mmol), 4,5-bis(diphenylphosphino)-9,9-dimethylxanthene (175.5 mg, 0.30 mmol) and cesium carbonate (379.88 mg, 1.17 mmol) in 1,4-dioxane (10 mL) was stirred for 3 hours at 100° C. under nitrogen. After filtration, the filtrate was concentrated under reduced pressure. The residue was purified by flash chromatography on silica gel eluting with methanol/dichloromethane (1/10) to afford tert-butyl N-tert-butoxycarbonyl-N-[5-[8-chloro-3-[(6-cyclopropyl-7-oxo-5,8-dihydro-4H-pyrazolo[1,5-d][1,4]diazepin-2-yl)amino]-7-fluoro-6-isoquinolyl]-4-methyl-3-pyridyl]carbamate (160 mg, 0.23 mmol) as a brown oil. LCMS (ESI) [M+H]⁺=692.2.

Step 3: tert-butyl N-tert-butoxycarbonyl-N-[5-[8-(tert-butoxycarbonylamino)-3-[(6-cyclopropyl-7-oxo-5,8-dihydro-4H-pyrazolo[1,5-d][1,4]diazepin-2-yl)amino]-7-fluoro-6-isoquinolyl]-4-methyl-3-pyridyl]carbamate

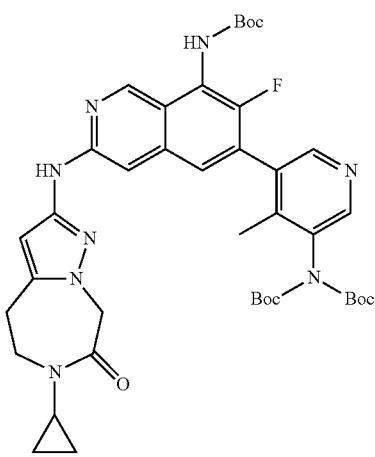 [SMILES: Cc1c(-c2cc3cc(Nc4cc5n(n4)CC(=O)N(C4CC4)CC5)ncc3c(NC(=O)OC(C)(C)C)c2F)cncc1N(C(=O)OC(C)(C)C)C(=O)OC(C)(C)C]

A mixture of tert-butyl carbamate (812.8 mg, 6.94 mmol), tert-butyl N-tert-butoxycarbonyl-N-[5-[8-chloro-3-[(6-cyclopropyl-7-oxo-5,8-dihydro-4H-pyrazolo[1,5-d][1,4]diazepin-2-yl)amino]-7-fluoro-6-isoquinolyl]-4-methyl-3-pyridyl]carbamate (160.0 mg, 0.23 mmol), tris(dibenzylideneacetone)dipalladium-chloroformadduct (48.0 mg, 0.05 mmol), Brettphos (25.6 mg, 0.05 mmol) and cesium carbonate (304 mg, 0.93 mmol) in 1,4-dioxane (2 mL) was stirred for 3 hours at 90° C. under nitrogen. After filtration, the filtrate was concentrated under reduced pressure. The residue was purified by flash chromatography on silica gel eluting with methanol/dichloromethane (1/10) to afford tert-butyl N-tert-butoxycarbonyl-N-[5-[8-(tert-butoxycarbonylamino)-3-[(6-cyclopropyl-7-oxo-5,8-dihydro-4H-pyrazolo[1,5-d][1,4]diazepin-2-yl)amino]-7-fluoro-6-isoquinolyl]-4-methyl-3-pyridyl]carbamate (160.0 mg, 0.21 mmol) as a brown oil. LCMS (ESI) [M+H]⁺=772.9

Step 4: 2-[[8-amino-6-(5-amino-4-methyl-3-pyridyl)-7-fluoro-3-isoquinolyl]amino]-6-cyclopropyl-5,8-dihydro-4H-pyrazolo[1,5-d][1,4]diazepin-7-one

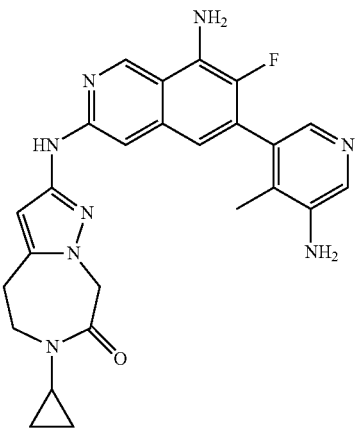 [SMILES: Cc1c(N)cncc1-c1cc2cc(Nc3cc4n(n3)CC(=O)N(C3CC3)CC4)ncc2c(N)c1F]

A solution of tert-butyl N-tert-butoxycarbonyl-N-[5-[8-(tert-butoxycarbonylamino)-3-[(6-cyclopropyl-7-oxo-5,8-dihydro-4H-pyrazolo[1,5-d][1,4]diazepin-2-yl)amino]-7-fluoro-6-isoquinolyl]-4-methyl-3-pyridyl]carbamate (160 mg, 0.21 mmol) and 2,2,2-trifluoroacetic acid (2 mL, 0.21 mmol) in dichloromethane (2 mL) was stirred at 25° C. for 3 hours. The reaction mixture was adjusted to pH 7 with ammonia in methanol (7 mol/L). The mixture was concentrated under vacuum. The residue was purified by flash chromatography by flash chromatography on C18 to afford 2-[[8-amino-6-(5-amino-4-methyl-3-pyridyl)-7-fluoro-3-isoquinolyl]amino]-6-cyclopropyl-5,8-dihydro-4H-pyrazolo[1,5-d][1,4]diazepin-7-one (11.4 mg, 0.02 mmol) as a yellow solid. LCMS (ESI) [M+H]⁺=472.5; ¹H NMR (300 MHz, DMSO-d₆) δ 9.26 (s, 1H), 9.08 (s, 1H), 8.00 (s, 1H), 7.71 (d, J=3.4 Hz, 2H), 6.73 (d, J=6.1 Hz, 1H), 6.08 (s, 2H), 5.97 (s, 1H), 5.30 (s, 2H), 4.95 (s, 2H), 3.87-3.77 (m, 2H), 3.06-2.96 (m, 2H), 2.81-2.70 (m, 1H), 1.95 (s, 3H), 0.75-0.60 (m, 2H), 0.71-0.59 (m, 2H).

Example 175

2-[[8-amino-6-(3,4-dihydro-2H-pyrido[4,3-b][1,4]oxazin-8-yl)-7-fluoro-3-isoquinolyl]amino]-6-isopropyl-5,8-dihydro-4H-pyrazolo[1,5-d][1,4]diazepin-7-one (Compound 284)

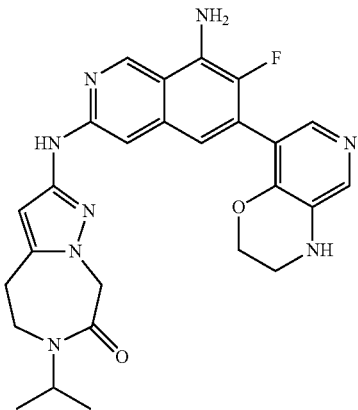 [SMILES: CC(C)N1CCc2cc(Nc3cc4cc(-c5cncc6c5OCCN6)c(F)c(N)c4cn3)nn2CC1=O]

Step 1: 8-bromo-4H-pyrido[4,3-b][1,4]oxazin-3-one

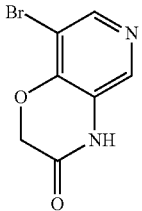

A mixture of 3-amino-5-bromo-4-pyridinol (5 g, 26.45 mmol), chloroacetyl chloride (3.25 g, 28.78 mmol), potassium carbonate (11.0 g, 79.71 mmol) in N,N-dimethylformamide (30 mL) was stirred at 100° C. for 12 hours. After filtration, the filtrate was concentrated under vacuum. The residue was purified by flash chromatography on silica gel eluted with dichloromethane/methanol (10/1) to afford 8-bromo-4H-pyrido[4,3-b][1,4]oxazin-3-one (3.5 g, 15.28 mmol) as a light yellow solid. LCMS (ESI) [M+H]$^+$=229.

Step 2: 8-bromo-3,4-dihydro-2H-pyrido(4,3-b)(1,4)oxazine

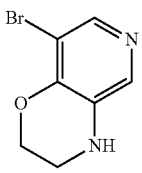

A mixture of 8-bromo-4H-pyrido(4,3-b)(1,4)oxazin-3-one (1.0 g, 4.37 mmol) in tetrahydrofuran (15 mL) was added borane-tetrahydrofuran complex (13.1 mL, 13.1 mmol) at 0° C. The reaction was stirred for 12 hours at 60° C. The resulting mixture was added dropwise to a solution of methanol (5 mL) and hydrochloric acid (5 mL, 12 mol/L) at 60° C. for 5 hours. The reaction mixture was diluted with water (50 mL). The resulting mixture was extracted with ethyl acetate, dried with anhydrous sodium sulfate. After filtration, the filtrate was concentrated under vacuum to afford 8-bromo-3,4-dihydro-2H-pyrido(4,3-b)(1,4) oxazine (1 g, 4.7 mmol) as a yellow oil. LCMS (ESI) [M+H]$^+$=215.0.

Step 3: tert-butyl 8-bromo-2,3-dihydropyrido(4,3-b)(1,4)oxazine-4-carboxylate

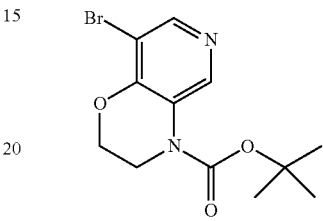

A mixture of di-tert-butyldicarbonate (1.67 g, 7.67 mmol), 8-bromo-3,4-dihydro-2H-pyrido(4,3-b)(1,4)oxazine (1.1 g, 5.12 mmol), triethylamine (1.5 g, 15.3 mmol), in dichloromethane (30 mL) was stirred at 25° C. for 3 hours. After filtration, the filtrate was concentrated under vacuum. The residue was purified by flash chromatography on silica gel eluted with dichloromethane/methanol (10/1) to afford tert-butyl 8-bromo-2,3-dihydropyrido(4,3-b)(1,4)oxazine-4-carboxylate (770 mg, 2.44 mmol) as a light yellow solid. LCMS (ESI) [M+H]$^+$=315.2.

Step 4: tert-butyl 8-(4,4,5,5-tetramethyl-1,3,2-dioxaborolan-2-yl)-2,3-dihydropyrido[4,3-b][1,4]oxazine-4-carboxylate

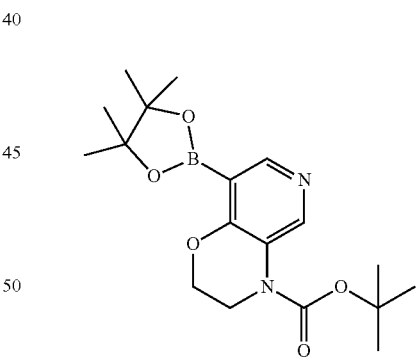

A mixture of tert-butyl 8-bromo-2,3-dihydropyrido(4,3-b)(1,4)oxazine-4-carboxylate (350 mg, 1.11 mmol), bis(pinacolato)diboron (2.8 g, 11.15 mmol), [1,1'-bis(diphenylphosphino)ferrocene]dichloropalladium(II) (161.0 mg, 0.22 mmol) and potassium acetate (327.8 mg, 3.34 mmol) in 1,4-dioxane (5 mL) was stirred at 90° C. for 3 hours. After filtration, the filtrate was concentrated under vacuum. The residue was purified by flash chromatography on silica gel eluted with dichloromethane/methanol (30/1) to afford tert-butyl 8-(4,4,5,5-tetramethyl-1,3,2-dioxaborolan-2-yl)-2,3-dihydropyrido[4,3-b][1,4]oxazine-4-carboxylate (240 mg, 0.66 mmol) as a light yellow solid. LCMS (ESI) [M+H]$^+$=362.2.

Step 5: tert-butyl 8-(4,4,5,5-tetramethyl-1,3,2-dioxaborolan-2-yl)-2,3-dihydropyrido(4,3-b)(1,4)oxazine-4-carboxylate

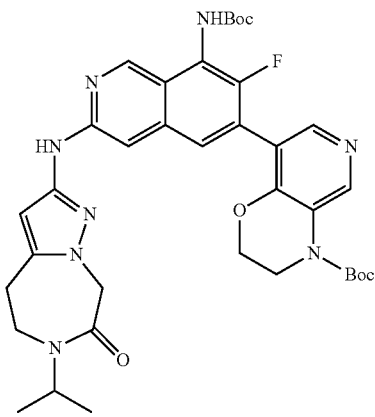 [SMILES: CC(C)N1CCc2cc(Nc3cc4cc(-c5cncc6c5OCCN6C(=O)OC(C)(C)C)c(F)c(NC(=O)OC(C)(C)C)c4cn3)nn2CC1=O]

A mixture of (4-tert-butoxycarbonyl-2,3-dihydropyrido[4,3-b][1,4]oxazin-8-yl)boronic acid (100.0 mg, 0.36 mmol), [8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl] trifluoromethanesulfonate (111.1 mg, 0.18 mmol), [1,1'-bis(diphenylphosphino)ferrocene]dichloropalladium(II) (13.33 mg, 0.02 mmol) and potassium carbonate (75.56 mg, 0.55 mmol) in 1,4-dioxane (2 mL) was stirred under nitrogen at 90° C. for 2 hours. After filtration, the filtrate was concentrated under vacuum. The residue was purified by flash chromatography on silica gel eluting with methanol/dichloromethane (1/10) to afford [tert-butyl 8-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-2,3-dihydropyrido[4,3-b][1,4]oxazine-4-carboxylate (120 mg, 0.17 mmol) as a brown oil.

Step 6: 2-[[8-amino-6-(3,4-dihydro-2H-pyrido[4,3-b][1,4]oxazin-8-yl)-7-fluoro-3-isoquinolyl]amino]-6-isopropyl-5,8-dihydro-4H-pyrazolo[1,5-d][1,4]diazepin-7-one

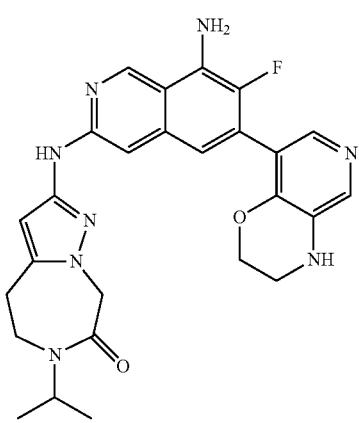

A solution of tert-butyl 8-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-2,3-dihydropyrido[4,3-b][1,4]oxazine-4-carboxylate (140 mg, 0.20 mmol) and 2,2,2-trifluoroacetic acid (2 mL) in dichloromethane (2 mL) was stirred at 25° C. for 3 hours. The reaction mixture was adjusted to pH 7 with ammonia in methanol (7 mol/L). The mixture was concentrated under vacuum. The residue was purified by prep-HPLC to afford 2-[[8-amino-6-(3,4-dihydro-2H-pyrido[4,3-b][1,4]oxazin-8-yl)-7-fluoro-3-isoquinolyl]amino]-6-isopropyl-5,8-dihydro-4H-pyrazolo[1,5-d][1,4]diazepin-7-one (10.3 mg, 0.02 mmol) as a yellow solid. LCMS (ESI) [M+H]$^+$=502.5. $^1$H NMR (300 MHz, DMSO-$d_6$) δ 9.25 (s, 1H), 9.08 (s, 1H), 7.93 (s, 1H), 7.78 (s, 1H), 7.71 (s, 1H), 6.82 (d, J=5.9 Hz, 1H), 6.30 (s, 1H), 6.03 (s, 1H), 5.97 (s, 1H), 4.98 (s, 2H), 4.70-4.55 (m, 1H), 4.28-4.21 (m, 2H), 3.83-3.74 (m, 2H), 3.40 (s, 2H), 3.04-2.95 (m, 2H), 1.13 (d, J=6.8 Hz, 6H).

Example 176

2-[[8-amino-6-(5-amino-4-ethyl-3-pyridyl)-7-fluoro-3-isoquinolyl]amino]-6-isopropyl-5,8-dihydro-4H-pyrazolo[1,5-d][1,4]diazepin-7-one (Compound 286)

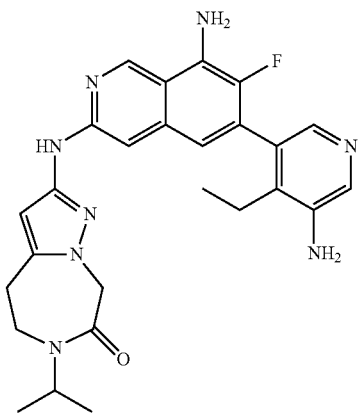 [SMILES: CCc1c(N)cncc1-c1cc2cc(Nc3cc4n(n3)CC(=O)N(C(C)C)CC4)ncc2c(N)c1F]

Step 1: 3-bromo-4-iodo-5-nitro-pyridine

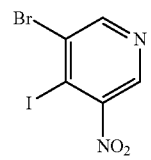 [SMILES: O=[N+]([O-])c1cncc(Br)c1I]

A mixture of 3-bromo-4-chloro-5-nitropyridine (5.0 g, 21.06 mmol) and potassium iodide (70 g, 422.02 mmol) in acetonitrile (300 mL) was stirred for 16 hours at 80° C. The resulting solution was cooled to room temperature and then filtrated. The filtrate was concentrated under vacuum. The residue was purified by flash chromatography on silica gel eluting with petroleum ether/ethyl acetate (10/1) to afford 3-bromo-4-iodo-5-nitro-pyridine (6.5 g, 19.76 mmol) as a red solid. LCMS (ESI) [M+H]$^+$=328.7.

Step 2: 3-bromo-5-nitro-4-vinyl-pyridine

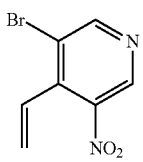

A mixture of 3-bromo-4-iodo-5-nitro-pyridine (5.0 g, 15.2 mmol), potassium trifluoro(vinyl)borate (2.6 g, 19.41 mmol), sodium carbonate (4.8 g, 45.28 mmol) and [1,1'-bis (diphenylphosphino)ferrocene]dichloropalladium(II) (1.1 g, 1.5 mmol) in 1,4-dioxane (300 mL) and water (30 mL) was stirred for 3 days at 50° C. After filtration, the filtrate was concentrated under vacuum. The residue was purified by flash chromatography on silica gel eluting with petroleum ether/ethyl acetate (10/1) to afford 3-bromo-5-nitro-4-vinyl-pyridine (2.8 g, 12.22 mmol). LCMS (ESI) [M+H]$^+$=229.

Step 3: 5-bromo-4-ethyl-pyridin-3-amine

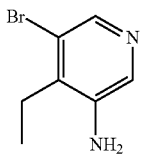

A mixture of 3-bromo-5-nitro-4-vinyl-pyridine (500 mg, 2.18 mmol), platinum dioxide (100 mg, 0.44 mmol) and acetic acid (5 drops) in methanol (20 mL) was stirred for 4 hour at 20° C. under hydrogen. After filtration, the filtrate was concentrated under vacuum. The residue was purified by flash chromatography on silica gel eluting with petroleum ether/ethyl acetate (2/1) to afford 5-bromo-4-ethyl-pyridin-3-amine (220 mg, 1.09 mmol) as light yellow oil. LCMS (ESI) [M+H]$^+$=201.

Step 4: tert-butyl N-(5-bromo-4-ethyl-3-pyridyl)-N-tert-butoxycarbonyl-carbamate

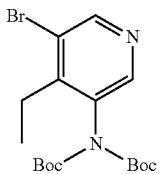

A solution of 5-bromo-4-ethyl-pyridin-3-amine (200 mg, 0.99 mmol) and di-tert-butyldicarbonate (650 g, 2.98 mmol) in tetrahydrofuran (2 mL) was stirred at 90° C. for 2 hours in a seal tube. The organic layer was concentrated under vacuum. The residue was purified by flash chromatography on silica gel eluting with petroleum ether/ethyl acetate (10/1) to afford tert-butyl N-(5-bromo-4-ethyl-3-pyridyl)-N-tert-butoxycarbonyl-carbamate (180 mg, 0.45 mmol). LCMS (ESI) [M+H]$^+$=401.

Step 5: [5-[bis(tert-butoxycarbonyl)amino]-4-ethyl-3-pyridyl]boronic Acid

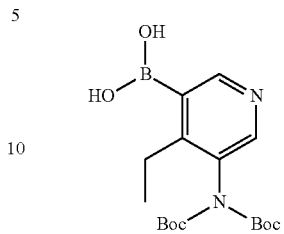

A mixture of tert-butyl N-(5-bromo-4-ethyl-3-pyridyl)-N-tert-butoxycarbonyl-carbamate (200 mg, 0.50 mmol), bis (pinacolato)diboron (600 mg, 2.36 mmol), [1,1'-bis(diphenylphosphino)ferrocene]dichloropalladium(II) (70 mg, 0.10 mmol), potassium acetate (150 mg, 1.53 mmol) in N,N-dimethylacetamide (5 mL) was stirred for 2 hours at 90° C. The resulting mixture was cooled to room temperature and then filtered. The filtrate was concentrated under vacuum. The residue was purified by reverse phase chromatography (acetonitrile 0-70/0.05% sodium bicarbonate in water) to afford [5-[bis(tert-butoxycarbonyl)amino]-4-ethyl-3-pyridyl]boronic acid (100 mg, 0.27 mmol) as a brown solid. LCMS (ESI) [M+H]$^+$=367.3.

Step 6: tert-butyl(tert-butoxycarbonyl)(5-(8-((tert-butoxycarbonyl)amino)-7-fluoro-3-((6-isopropyl-7-oxo-5,6,7,8-tetrahydro-4H-pyrazolo[1,5-d][1,4]diazepin-2-yl)amino)isoquinolin-6-yl)-4-ethylpyridin-3-yl)carbamate

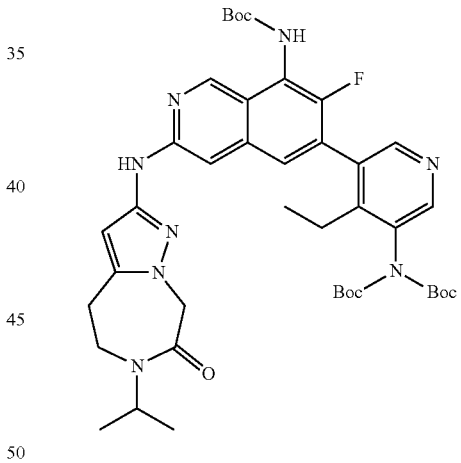

A mixture of [1,1'-bis(diphenylphosphino)ferrocene]dichloropalladium(II) (13 mg, 0.02 mmol), potassium carbonate (65 mg, 0.47 mmol), [8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl] trifluoromethanesulfonate (100 mg, 0.16 mmol), [5-[bis (tert-butoxycarbonyl)amino]-4-ethyl-3-pyridyl]boronic acid (90 mg, 0.25 mmol) in 1,4-dioxane (5 mL) and water (0.05 mL) was stirred for 3 hours at 90° C. The resulting mixture was cooled to room temperature and then filtered. The filtrate was concentrated under vacuum. The residue was purified by flash chromatography on silica gel eluting with ethyl acetate/methanol (40/1) to afford tert-butyl(tert-butoxycarbonyl)(5-(8-((tert-butoxycarbonyl)amino)-7-fluoro-3-((6-isopropyl-7-oxo-5,6,7,8-tetrahydro-4H-pyrazolo[1,5-d][1,4]diazepin-2-yl)amino)isoquinolin-6-yl)-4-ethylpyridin-3-yl)carbamate (46 mg, 0.058 mmol) as a red solid. LCMS (ESI) [M+H]$^+$=789.4.

Step 7: 2-[[8-amino-6-(5-amino-4-ethyl-3-pyridyl)-7-fluoro-3-isoquinolyl]amino]-6-isopropyl-5,8-dihydro-4H-pyrazolo[1,5-d][1,4]diazepin-7-one

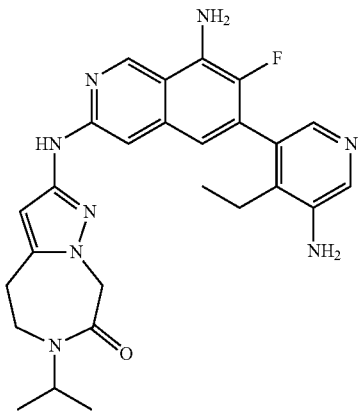 [SMILES: CCc1c(N)cncc1-c1cc2cc(Nc3cc4n(n3)CC(=O)N(C(C)C)CC4)ncc2c(N)c1F]

A solution of tert-butyl N-tert-butoxycarbonyl-N-[5-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-4-ethyl-3-pyridyl]carbamate (41 mg, 0.05 mmol) in dichloromethane (5 mL) and 2,2,2-trifluoroacetic acid (1 mL) was stirred for 1 hour at room temperature. The mixture was concentrated under vacuum. The residue was dissolved in N,N-dimethylformamide and the solution was adjusted pH 7 with triethylamine. The resulting solution was purified by Prep-HPLC with (XBridge prep C18 OBD Column 19*150 mm 5 um; water (10 mmol/L sodium bicarbonate)/CH$_3$CN=25%-45% in 7 min) to afford 2-[[8-amino-6-(5-amino-4-ethyl-3-pyridyl)-7-fluoro-3-isoquinolyl]amino]-6-isopropyl-5,8-dihydro-4H-pyrazolo[1,5-d][1,4]diazepin-7-one (8.1 mg, 0.017 mmol) as a yellow solid. LCMS (ESI) [M+H]$^+$=489.3. $^1$HNMR (400 MHz, DMSO-d$_6$) δ 9.24 (s, 1H), 9.06 (s, 1H), 7.98 (s, 1H), 7.70 (s, 1H), 7.59 (s, 1H), 6.70 (d, J=5.9 Hz, 1H), 6.06 (s, 2H), 5.97 (s, 1H), 5.25 (s, 2H), 4.96 (s, 2H), 4.63-4.55 (m, 1H), 3.77 (s, 2H), 2.98 (s, 2H), 2.35-2.33 (m, 2H), 1.12 (d, J=6.7 Hz, 6H), 0.92 (t, J=7.4 Hz, 3H).

Example 177

2-((8-amino-6-(5-amino-4-methylpyridin-3-yl)-7-fluoroisoquinolin-3-yl)amino)-4-ethyl-4H,6H-pyrazolo[1,5-c]thiazole 5,5-dioxide (Compound 287)

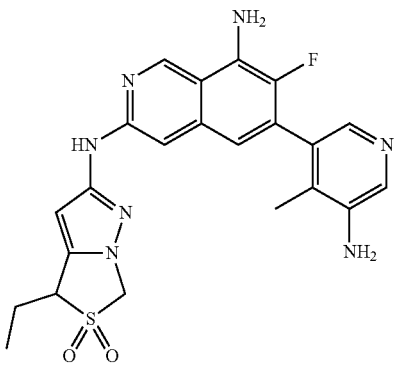 [SMILES: CCC1c2cc(Nc3cc4cc(-c5cncc(N)c5C)c(F)c(N)c4cn3)nn2CS1(=O)=O]

Step 1: 3-(bromomethylsulfanyl)prop-1-ene

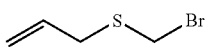

To a solution of polyformaldehyde (16 g, 0.13 mol) in toluene (110 mL) was added 270 mL of hydrogen bromide (aq, 48%) over 5 minutes. The mixture was stirred for 20 minutes at 20° C. The reaction was then warmed to 40° C. and allyl mercaptan (45 g, 606.96 mmol) was added via addition funnel over 20 minutes. The mixture was then heated to 50° C. and then stirred for an additional 2 hours. The reaction was quenched by water. The resulting solution was extracted with ethyl acetate, dried with anhydrous sodium sulfate. After filtration, the filtrate was concentrated under vacuum to afford 3-(bromomethylsulfanyl)prop-1-ene (20 g, crude) as a light yellow oil. GCMS (ESI) M=168.0.

Step 2: 1-(allylsulfanylmethyl)-3,5-dibromo-pyrazole

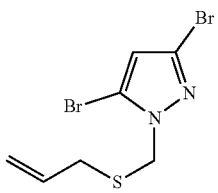

To a solution of 3,5-dibromo-1H-pyrazole (10 g, 44.27 mmol) in N,N-dimethylformamide (100 mL) was added potassium carbonate (12.22 g, 88.55 mmol), tetrabutylammonium iodide (0.82 g, 2.21 mmol) and 3-(bromomethylsulfanyl)prop-1-ene (22.19 g, 132.82 mmol). The reaction was stirred at 20° C. for 3 hours. After filtration, the filtrate was concentrated under reduced pressure. The residue was purified by flash chromatography on silica gel eluting with petroleum ether/ethyl acetate (8/1) to afford 1-(allylsulfanylmethyl)-3,5-dibromo-pyrazole (10 g, 32.05 mmol) as a colorless oil. LCMS (ESI) [M+H]$^+$=310.9.

Step 3: 1-(allylsulfonylmethyl)-3,5-dibromo-pyrazole

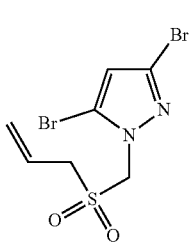

To a solution of 1-(allylsulfanylmethyl)-3,5-dibromo-pyrazole (10 g, 32.05 mmol) in dichloromethane (400 mL) was added 3-chloroperoxybenzoic acid (12.13 g, 70.51 mmol) at 0° C. The resulting solution was stirred at 0° C. for 3 hours. The reaction was quenched by sodium thiosulfate and sodium carbonate aqueous solution. The resulting solution was extracted with dichloromethane, dried with anhydrous sodium sulfate. After filtration, the filtrate was concentrated under vacuum. The residue was purified by flash chromatography on silica gel eluting with petroleum ether/ethyl acetate (4/1) to afford 1-(allylsulfonylmethyl)-3,5-dibromo-pyrazole (1.5 g, 4.36 mmol) as a white solid. LCMS (ESI) [M+H]⁺=345.1.

Step 4: 2-bromo-4-methyl-7H-pyrazolo[1,5-c][1,3]thiazine 6,6-dioxide

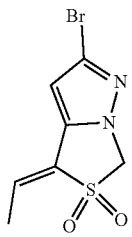

A mixture of triethylamine (1.47 g, 14.53 mmol), tris(2-methylphenyl)phosphine (264.48 mg, 0.87 mmol), palladium acetate (97.66 mg, 0.44 mmol) and 1-(allylsulfonylmethyl)-3,5-dibromo-pyrazole (1 g, 2.91 mmol) in N,N-dimethylformamide (50 mL) was stirred at 90° C. for 1 hour. The mixture was concentrated under vacuum. The residue was purified by flash chromatography on silica gel eluting with petroleum ether/ethyl acetate (9/1) to afford 2-bromo-4-methyl-7H-pyrazolo[1,5-c][1,3]thiazine 6,6-dioxide (500 mg, 1.90 mmol) as a yellow oil. LCMS (ESI) [M+H]⁺=263.2.

Step 5: 2-bromo-4-methyl-5,7-dihydro-4H-pyrazolo[1,5-c][1,3]thiazine 6,6-dioxide

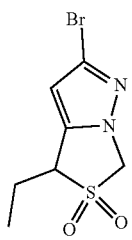

A mixture of 2-bromo-4-methyl-7H-pyrazolo[1,5-c][1,3]thiazine 6,6-dioxide (500 mg, 1.9 mmol) and sodium borohydride (252.75 mg, 6.65 mmol) in methanol (30 mL) was stirred at 20° C. for 1 hour. The reaction was quenched by water. The resulting mixture was extracted with ethyl acetate, dried with anhydrous sodium sulfate. After filtration, the filtrate was concentrated under vacuum. The residue was purified by a reversed-phase flash (C18 silica gel; 0.5% sodium bicarbonate in water: CH₃CN=70% 5% in 30 min) to afford 2-bromo-4-methyl-5,7-dihydro-4H-pyrazolo[1,5-c][1,3]thiazine 6,6-dioxide (280 mg, 1.06 mmol) as a colorless solid. LCMS (ESI) [M+H]⁺=267.3.

Step 6: Tert-butyl N-tert-butoxycarbonyl-N-[5-[8-chloro-7-fluoro-3-[(4-methyl-6,6-dioxo-5,7-dihydro-4H-pyrazolo[1,5-c][1,3]thiazin-2-yl)amino]-6-isoquinolyl]-4-methyl-3-pyridyl]carbamate

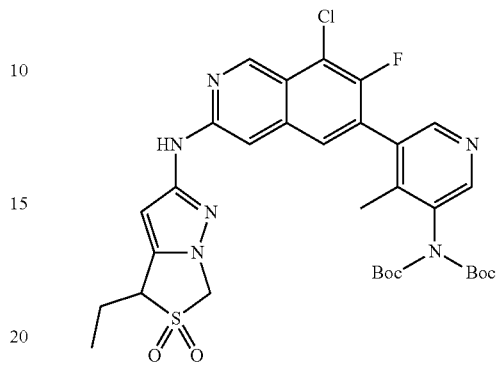

A mixture of tert-butyl N-[5-(3-amino-8-chloro-7-fluoro-6-isoquinolyl)-4-methyl-3-pyridyl]-N-tert-butoxycarbonyl-carbamate (150 mg, 0.30 mmol), 2-bromo-4-methyl-5,7-dihydro-4H-pyrazolo[1,5-c][1,3]thiazine 6,6-dioxide (237.21 mg, 0.89 mmol), tris(dibenzylideneacetone)dipalladium-chloroformadduct (123.47 mg, 0.12 mmol), 4,5-bis(diphenylphosphino)-9,9-dimethylxanthene (103.43 mg, 0.18 mmol) and cesium carbonate (291.67 mg, 0.89 mmol) in 1,4-dioxane (15 mL) was stirred for 2 hours at 120° C. After filtration, the filtrate was concentrated under reduced pressure. The residue was purified by a reversed-phase flash (C18 silica gel; 0.5% sodium bicarbonate in water: CH₃CN=70% 5% in 30 min) to afford tert-butyl N-tert-butoxycarbonyl-N-[5-[8-chloro-7-fluoro-3-[(4-methyl-6,6-dioxo-5,7-dihydro-4H-pyrazolo[1,5-c][1,3]thiazin-2-yl)amino]-6-isoquinolyl]-4-methyl-3-pyridyl]carbamate (50 mg, 0.07 mmol) as a yellow solid. LCMS45 (ESI) [M+H]⁺=687.3.

Step 7: Tert-butyl N-tert-butoxycarbonyl-N-[5-[8-(tert-butoxycarbonylamino)-7-fluoro-3-[(4-methyl-6,6-dioxo-5,7-dihydro-4H-pyrazolo[1,5-c][1,3]thiazin-2-yl)amino]-6-isoquinolyl]-4-methyl-3-pyridyl]carbamate

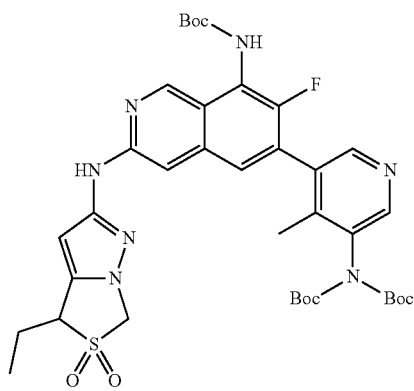 [SMILES: CCC1c2cc(Nc3cc4cc(-c5cncc(N(C(=O)OC(C)(C)C)C(=O)OC(C)(C)C)c5C)c(F)c(NC(=O)OC(C)(C)C)c4cn3)nn2CS1(=O)=O]

A mixture of tert-butyl N-tert-butoxycarbonyl-N-[5-[8-chloro-7-fluoro-3-[(4-methyl-6,6-dioxo-5,7-dihydro-4H-pyrazolo[1,5-c][1,3]thiazin-2-yl)amino]-6-isoquinolyl]-4-methyl-3-pyridyl]carbamate (50 mg, 0.07 mmol), tert-butyl carbamate (213.1 mg, 1.82 mmol), tris(dibenzylideneacetone)dipalladium-chloroformadduct (26.36 mg, 0.03 mmol), BrettPhos (19.5 mg, 0.04 mmol) and cesium carbonate (118.6 mg, 0.36 mmol) in 1,4-dioxane (8 mL) was stirred at 90° C. for 2 hours. After filtration, the filtrate was concentrated under reduced pressure. The residue was purified by flash chromatography on silica gel eluting with methanol/dichloromethane (1/10) to afford tert-butyl N-tert-butoxycarbonyl-N-[5-[8-(tert-butoxycarbonylamino)-7-fluoro-3-[(4-methyl-6,6-dioxo-5,7-dihydro-4H-pyrazolo[1,5-c][1,3]thiazin-2-yl)amino]-6-isoquinolyl]-4-methyl-3-pyridyl]carbamate (50 mg, 0.07 mmol) as a brown oil. LCMS (ESI) [M+H]⁺=768.4.

Step 8: 6-(5-amino-4-methyl-3-pyridyl)-7-fluoro-N3-(4-methyl-6,6-dioxo-5,7-dihydro-4H-pyrazolo[1,5-c][1,3]thiazin-2-yl)isoquinoline-3,8-diamine Formate Salt

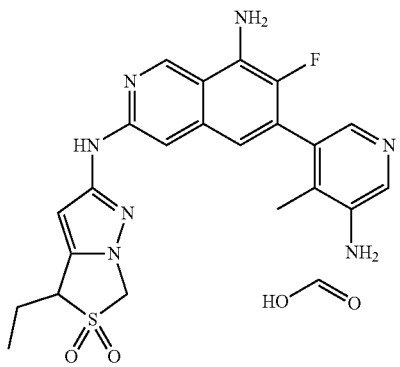

A solution of tert-butyl N-tert-butoxycarbonyl-N-[5-[8-(tert-butoxycarbonylamino)-7-fluoro-3-[(4-methyl-6,6-dioxo-5,7-dihydro-4H-pyrazolo[1,5-c][1,3]thiazin-2-yl)amino]-6-isoquinolyl]-4-methyl-3-pyridyl]carbamate (50 mg, 0.07 mmol) and 2,2,2-trifluoroacetic acid (12 mL) in dichloromethane (3 mL) was stirred at 20° C. for 1 hour. The resulting solution was concentrated under vacuum. The crude product was purified directly by Prep-HPLC (XBridge Prep C18 OBD Column19*15 mm 5 umC-0013; 0.1% HCOOH in water: CH₃CN=93%-60% in 7 min) afford 6-(5-amino-4-methyl-3-pyridyl)-7-fluoro-N3-(4-methyl-6,6-dioxo-5,7-dihydro-4H-pyrazolo[1,5-c][1,3]thiazin-2-yl)isoquinoline-3,8-diamine (1.3 mg, 0.003 mmol) as a yellow solid. LCMS (ESI) [M+H]⁺=468.2; ¹HNMR (400 MHz, DMSO-d₆) δ 9.45 (s, 1H), 9.30 (s, 1H), 8.39 (s, 1H), 7.98 (s, 1H), 7.68-7.66 (m, 2H), 6.69-6.67 (m, 1H), 6.25 (s, 1H), 6.11 (s, 2H), 5.46-5.38 (m, 2H), 5.22 (s, 2H), 4.67-4.63 (m, 1H), 2.03-1.99 (m, 2H), 1.92 (s, 3H), 1.14-1.10 (m, 3H).

Example 178

2-((8-amino-6-(5-amino-4-methylpyridin-3-yl)-7-fluoroisoquinolin-3-yl)amino)-6-(cyclopropylmethyl)-5,6-dihydro-4H-pyrazolo[1,5-d][1,4]diazepin-7(8H)-one formate salt (Compound 288)

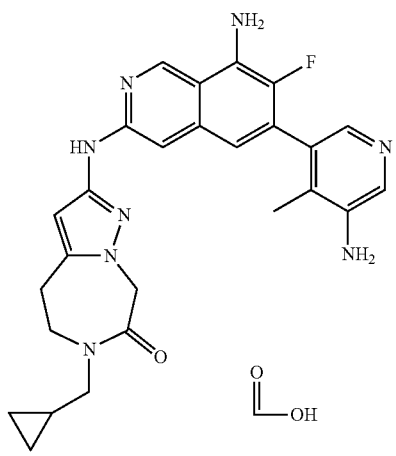 [SMILES: Cc1c(N)cncc1-c1cc2cc(Nc3cc4n(n3)CC(=O)N(CC3CC3)CC4)ncc2c(N)c1F ; O=CO]

Step 1: 2-bromo-6-(cyclopropylmethyl)-5,8-dihydro-4H-pyrazolo[1,5-d][1,4]diazepin-7-one

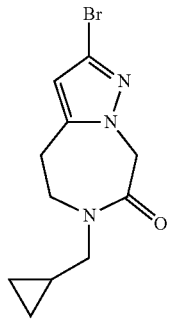 [SMILES: O=C1Cn2nc(Br)cc2CCN1CC1CC1]

A solution of 2-bromo-4,5,6,8-tetrahydropyrazolo[1,5-d][1,4]diazepin-7-one (200 mg, 0.87 mmol) and sodium hydride (79.98 mg, 3.48 mmol) in N,N-dimethylformamide (5 mL) was stirred at 20° C. for 5 minutes. Then (iodomethyl)cyclopropane (316.44 mg, 1.74 mmol) was added. The mixture was stirred at 20° C. for 1 hour. The reaction was quenched with water. The resulting solution was extracted with ethyl acetate, dried with anhydrous sodium sulfate. After filtration, the filtrate was concentrated under vacuum. The residue was purified by flash chromatography on silica gel eluting with dichloromethane/methanol (98/2) to afford 2-bromo-6-(cyclopropylmethyl)-5,8-dihydro-4H-pyrazolo[1,5-d][1,4]diazepin-7-one (191 mg, 0.67 mmol) as a yellow solid. LCMS (ESI) [M+H]⁺=284.1.

801

Step 2: Tert-butyl N-tert-butoxycarbonyl-N-[5-[8-chloro-3-[[6-(cyclopropylmethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate

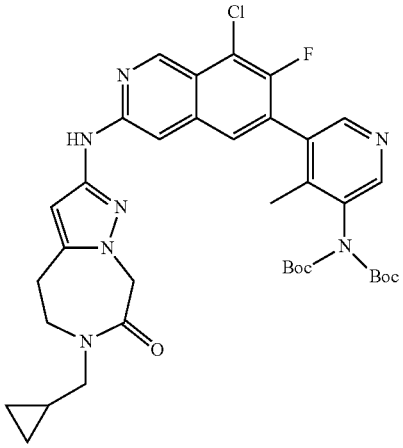 [SMILES: Cc1c(-c2cc3cc(Nc4cc5n(n4)CC(=O)N(CC4CC4)CC5)ncc3c(Cl)c2F)cncc1N(C(=O)OC(C)(C)C)C(=O)OC(C)(C)C]

To a mixture of 2-bromo-6-(cyclopropylmethyl)-5,8-dihydro-4H-pyrazolo[1,5-d][1,4]diazepin-7-one (180.5 mg, 0.64 mmol), tert-butyl N-[5-(3-amino-8-chloro-7-fluoro-6-isoquinolyl)-4-methyl-3-pyridyl]-N-tert-butoxycarbonyl-carbamate (213 mg, 0.42 mmol), tris(dibenzylideneacetone)dipalladium-chloroformadduct (87.66 mg, 0.08 mmol) and 4,5-bis(diphenylphosphino)-9,9-dimethylxanthene (97.91 mg, 0.17 mmol) in 1,4-dioxane (18 mL) was added cesium carbonate (345.14 mg, 1.06 mmol) at 25° C. The resulting solution was stirred at 100° C. for 12 hours. The mixture was concentrated under vacuum. The residue was purified by flash chromatography on silica gel eluting with dichloromethane/methanol (96/4) to afford tert-butyl N-tert-butoxycarbonyl-N-[5-[8-chloro-3-[[6-(cyclopropylmethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate (225 mg, 0.32 mmol) as a yellow solid. LCMS (ESI) [M+H]$^+$=706.4

Step 3: Tert-butyl N-tert-butoxycarbonyl-N-[5-[8-(tert-butoxycarbonylamino)-3-[[6-(cyclopropylmethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate

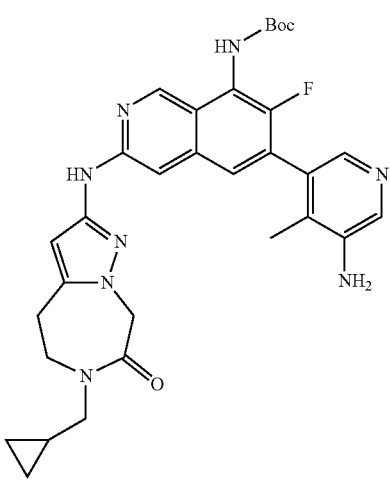 [SMILES: Cc1c(N)cncc1-c1cc2cc(Nc3cc4n(n3)CC(=O)N(CC3CC3)CC4)ncc2c(NC(=O)OC(C)(C)C)c1F]

802

To a mixture of tert-butyl N-tert-butoxycarbonyl-N-[5-[8-chloro-3-[[6-(cyclopropylmethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate (225 mg, 0.32 mmol), tert-butyl carbamate (933.11 mg, 7.97 mmol), tris (dibenzylideneacetone)dipalladium-chloroform adduct (65.95 mg, 0.06 mmol) and Brettphos (68.31 mg, 0.13 mmol) in 1,4-dioxane (10 mL) was added cesium carbonate (259.66 mg, 0.80 mmol) at rt. The resulting solution was stirred at 90° C. for 1 hour. The mixture was concentrated under vacuum. The residue was purified by flash chromatography on silica gel eluting with dichloromethane/methanol (95/5) to afford tert-butyl N-tert-butoxycarbonyl-N-[5-[8-(tert-butoxycarbonylamino)-3-[[6-(cyclopropylmethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate (67 mg, 0.085 mmol) as orange oil. LCMS (ESI) [M+H]$^+$=787.2.

Step 4: 2-((8-amino-6-(5-amino-4-methylpyridin-3-yl)-7-fluoroisoquinolin-3-yl)amino)-6-(cyclopropylmethyl)-5,6-dihydro-4H-pyrazolo[1,5-d][1,4]diazepin-7(8H)-one; Formic Acid

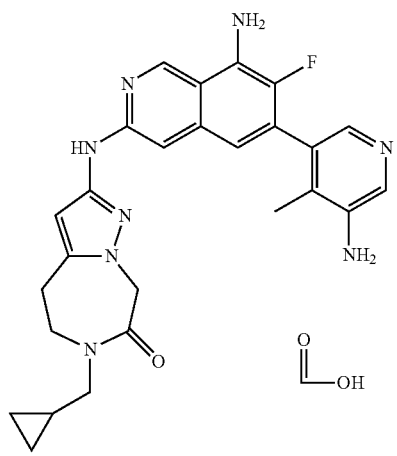 [SMILES: Cc1c(N)cncc1-c1cc2cc(Nc3cc4n(n3)CC(=O)N(CC3CC3)CC4)ncc2c(N)c1F ; O=CO]

A solution of tert-butyl N-tert-butoxycarbonyl-N-[5-[8-(tert-butoxycarbonylamino)-3-[[6-(cyclopropylmethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate (65 mg, 0.08 mmol) and 2,2,2-trifluoroacetic acid (1.0 mL, 0.08 mmol) in dichloromethane (3.0 mL) was stirred at 20° C. for 1 hour. The mixture was concentrated under vacuum. The reaction mixture was adjusted to pH 8 with ammonia in methanol (7 mol/L). The crude product was purified by Prep-HPLC (XBridge Prep C18 OBD Column 19×150 mm 5 um; Water (0.1% FA) and ACN (5%-18%) in 10 min) to afford 2-[[8-amino-6-(5-amino-4-methyl-3-pyridyl)-7-fluoro-3-isoquinolyl]amino]-6-(cyclopropylmethyl)-5,8-dihydro-4H-pyrazolo[1,5-d][1,4]diazepin-7-one; formic acid (13.5 mg, 0.025 mmol) as a yellow solid. LCMS (ESI) [M+H]$^+$=487.3; $^1$HNMR (300 MHz, DMSO-d$_6$) δ 9.25 (s, 1H), 9.07 (s, 1H), 8.24 (s, 1H), 7.98 (s, 1H), 7.70 (s, 1H), 7.66 (s, 1H), 6.72-6.70 (m, 1H), 6.06 (s, 2H), 5.98 (s, 1H), 5.22 (s, 2H), 4.99 (s, 2H), 3.93-3.89 (m, 2H), 3.28-3.26 (m, 2H), 3.09-3.05 (m, 2H), 1.93 (s, 3H), 1.01 (s, 1H), 0.48-0.44 (m, 2H), 0.29 (m, 2H).

Example 179

2-((8-amino-7-fluoro-6-(5-hydroxy-4-methylpyridin-3-yl)isoquinolin-3-yl)amino)-6-methyl-5,6-dihydro-4H-pyrazolo[1,5-d][1,4]diazepin-7(8H)-one; Formic Acid (Compound 289)

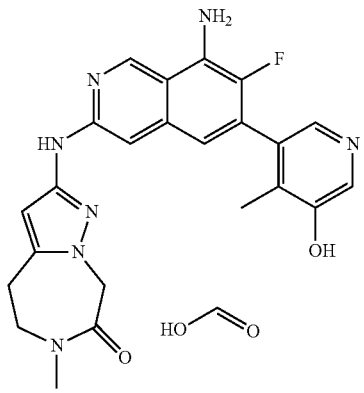 [SMILES: Cc1c(O)cncc1-c1cc2cc(Nc3cc4n(n3)CC(=O)N(C)CC4)ncc2c(N)c1F ; O=CO]

Step 1:
3-bromo-5-(methoxymethoxy)-4-methyl-pyridine

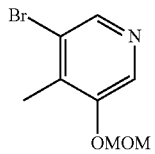

A mixture of 5-bromo-4-methyl-pyridin-3-ol (213 mg, 1.13 mmol) and sodium hydride (52.11 mg, 2.27 mmol, 60% purity) in tetrahydrofuran (5 mL) was stirred at 0° C. for 30 minutes. Bromomethyl methyl ether (169.87 mg, 1.36 mmol) was added. The mixture was stirred at 0° C. for 1 hour. The reaction was quenched with methanol. The mixture was concentrated under vacuum. The residue was purified by flash chromatography on silica gel eluting with petroleum ether/ethyl acetate (4/1) to afford 3-bromo-5-(methoxymethoxy)-4-methyl-pyridine (190 mg, 0.82 mmol) as a white solid. LCMS (ESI) [M+H]$^+$=232

Step 2: [5-(methoxymethoxy)-4-methyl-3-pyridyl]boronic Acid

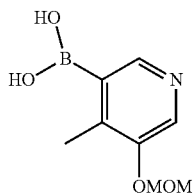

A mixture of 3-bromo-5-(methoxymethoxy)-4-methyl-pyridine (714 mg, 3.08 mmol), bis(pinacolato)diboron (781 mg, 3.08 mmol), [1,1'-bis(diphenylphosphino)ferrocene]dichloropalladium(II) (450 mg, 0.62 mmol) and potassium acetate (904 mg, 9.23 mmol) in 1,4-dioxane (15 mL) was stirred at 90° C. for 2 hours. The mixture was concentrated under vacuum. The residue was purified by flash chromatography on silica gel eluting with dichloromethane/methanol (95/5) to afford [5-(methoxymethoxy)-4-methyl-3-pyridyl]boronic acid (300 mg, 1.52 mmol) as a brown solid. LCMS (ESI) [M+H]$^+$=198.

Step 3: 8-chloro-7-fluoro-6-[5-(methoxymethoxy)-4-methyl-3-pyridyl]isoquinolin-3-amine

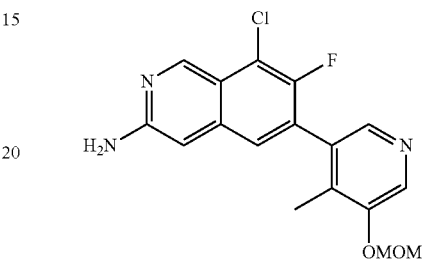

A mixture of 8-chloro-7-fluoro-6-iodo-isoquinolin-3-amine (300 mg, 0.93 mmol), [5-(methoxymethoxy)-4-methyl-3-pyridyl]boronic acid (275 mg, 1.4 mmol), [1,1'-bis(diphenylphosphino)ferrocene]dichloropalladium(II) (68 mg, 0.09 mmol) and potassium carbonate (385 mg, 2.79 mmol) in 1,4-dioxane (10 mL) and water (1 mL) was stirred at 90° C. for 1 hour. The mixture was concentrated under vacuum. The residue was purified by flash chromatography on silica gel eluting with dichloromethane/methanol (10/1) to afford 8-chloro-7-fluoro-6-[5-(methoxymethoxy)-4-methyl-3-pyridyl]isoquinolin-3-amine (145 mg, 0.42 mmol) as a brown solid. LCMS (ESI) [M+H]$^+$=348.

Step 4: 2-[[8-chloro-7-fluoro-6-[5-(methoxymethoxy)-4-methyl-3-pyridyl]-3-isoquinolyl]amino]-6-methyl-5,8-dihydro-4H-pyrazolo[1,5-d][1,4]diazepin-7-one

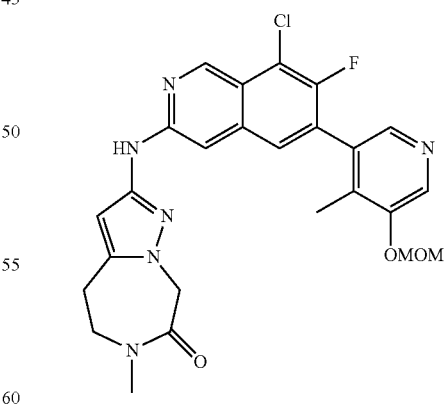

A mixture of 8-chloro-7-fluoro-6-[5-(methoxymethoxy)-4-methyl-3-pyridyl]isoquinolin-3-amine (135 mg, 0.39 mmol), 2-bromo-6-methyl-5,8-dihydro-4H-pyrazolo[1,5-d][1,4]diazepin-7-one (142 mg, 0.58 mmol), tris(dibenzylideneacetone)dipalladium-chloroformadduct (80 mg, 0.08 mmol), 4,5-bis(diphenylphosphino)-9,9-dimethylxanthene (89 mg, 0.16 mmol) and cesium carbonate (381 mg, 1.16 mmol) in 1,4-dioxane (5 mL) was stirred at 100° C. for 12 hours. The mixture was concentrated under vacuum. The residue was purified by flash chromatography on silica gel eluting with dichloromethane/methanol (10/1) to afford 2-[[8-chloro-7-fluoro-6-[5-(methoxymethoxy)-4-methyl-3-pyridyl]-3-isoquinolyl]amino]-6-methyl-5,8-dihydro-4H-pyrazolo[1,5-d][1,4]diazepin-7-one (50 mg, 0.098 mmol) as a light yellow solid. LCMS (ESI) [M+H]⁺=511.

Step 5: tert-butyl N-[7-fluoro-6-[5-(methoxymethoxy)-4-methyl-3-pyridyl]-3-[(6-methyl-7-oxo-5,8-dihydro-4H-pyrazolo[1,5-d][1,4]diazepin-2-yl)amino]-8-isoquinolyl]carbamate

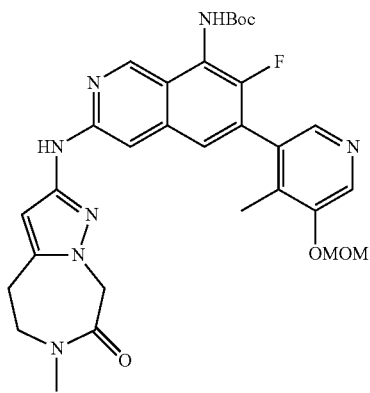

A mixture of 2-[[8-chloro-7-fluoro-6-[5-(methoxymethoxy)-4-methyl-3-pyridyl]-3-isoquinolyl]amino]-6-methyl-5,8-dihydro-4H-pyrazolo[1,5-d][1,4]diazepin-7-one (50 mg, 0.10 mmol), tert-butyl carbamate (286 mg, 2.45 mmol), tris(dibenzylideneacetone)dipalladium-chloroform adduct (20 mg, 0.020 mmol), Brettphos (15.74 mg, 0.03 mmol) and cesium carbonate (95 mg, 0.29 mmol) in 1,4-dioxane (3 mL) was stirred at 90° C. for 2 hours. The mixture was concentrated under vacuum. The residue was purified by flash chromatography on silica gel eluting with dichloromethane/methanol (10/1) to afford tert-butyl N-[7-fluoro-6-[5-(methoxymethoxy)-4-methyl-3-pyridyl]-3-[(6-methyl-7-oxo-5,8-dihydro-4H-pyrazolo[1,5-d][1,4]diazepin-2-yl)amino]-8-isoquinolyl]carbamate (40 mg, 0.067 mmol) as a light yellow solid. LCMS (ESI) [M+H]⁺=592.

Step 6: 2-[[8-amino-7-fluoro-6-(5-hydroxy-4-methyl-3-pyridyl)-3-isoquinolyl]amino]-6-methyl-5,8-dihydro-4H-pyrazolo[1,5-d][1,4]diazepin-7-one; Formic Acid

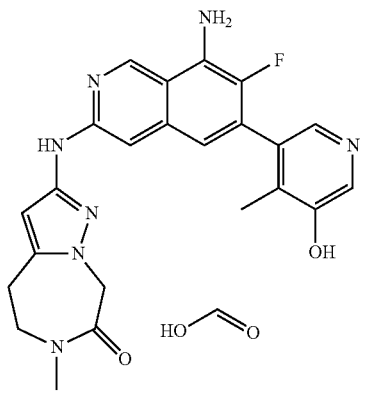 [SMILES: Cc1c(O)cncc1-c1cc2cc(Nc3cc4n(n3)CC(=O)N(C)CC4)ncc2c(N)c1F ; O=CO]

A mixture of tert-butyl N-[7-fluoro-6-[5-(methoxymethoxy)-4-methyl-3-pyridyl]-3-[(6-methyl-7-oxo-5,8-dihydro-4H-pyrazolo[1,5-d][1,4]diazepin-2-yl)amino]-8-isoquinolyl]carbamate (30 mg, 0.05 mmol) and hydrochloric acid (0.17 mL, 0.5 mmol) in dichloromethane (2 mL) was stirred at 20° C. for 1 hour. The reaction mixture was concentrated under vacuum. The reaction mixture was adjusted to pH 8 with ammonia in methanol (7 mol/L). The crude product was purified by Prep-HPLC (XBridge Prep C18 OBD Column 19×150 nm 5 um; water (0.1% FA): CH₃CN=5%-19% in 7 min) to afford 2-[[8-amino-7-fluoro-6-(5-hydroxy-4-methyl-3-pyridyl)-3-isoquinolyl]amino]-6-methyl-5,8-dihydro-4H-pyrazolo[1,5-d][1,4]diazepin-7-one; formic acid (1.4 mg, 0.0028 mmol) as a yellow solid. LCMS (ESI) [M+H]⁺=448. ¹HNMR (400 MHz, CD₃OD) δ 9.16 (s, 1H), 8.07 (s, 1H), 7.94 (s, 1H), 7.64 (s, 1H), 6.86 (d, J=6.0 Hz, 1H), 6.07 (s, 1H), 5.06 (s, 2H), 3.92 (t, J=6.0 Hz, 2H), 3.16 (t, J=6.0 Hz, 2H), 3.10 (s, 3H), 2.15 (s, 3H).

Example 180

2-(8-amino-7-fluoro-6-(5-(hydroxymethyl)-4-methylpyridin-3-yl)isoquinolin-3-ylamino)-6-isopropyl-5,6-dihydro-4H-pyrazolo[1,5-g][1,4]diazepin-7(8H)-one (Compound 290)

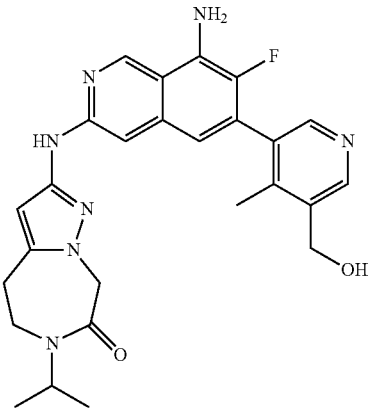 [SMILES: Cc1c(CO)cncc1-c1cc2cc(Nc3cc4n(n3)CC(=O)N(C(C)C)CC4)ncc2c(N)c1F]

Step 1: 3-bromo-5-((tert-butyldimethylsilyloxy)methyl)-4-methylpyridine

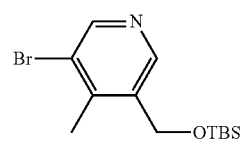

A solution of (5-bromo-4-methyl-3-pyridyl)methanol (500 mg, 2.47 mmol) and imidazole (505.42 mg, 7.42 mmol) in N,N-dimethylformamide (15 mL) was stirred at 25° C. for 10 minutes. TBSCl (742.39 mg, 4.95 mmol) was added and stirred at 25° C. for 2 hours. The mixture was concentrated under vacuum. The residue was purified by flash chromatography on silica gel eluting with ethyl acetate/petroleum ether (16/84) to afford (5-bromo-4-methyl-3-pyridyl)methoxy-tert-butyl-dimethyl-silane (820 mg, 2.07 mmol) as a white oil. LC/MS (ESI) [M+H]⁺=316.

Step 2: 5-((tert-butyldimethylsilyloxy)methyl)-4-methylpyridin-3-ylboronic Acid

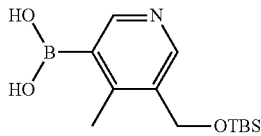 [SMILES: Cc1c(CO[Si](C)(C)C(C)(C)C)cncc1B(O)O]

A mixture of (5-bromo-4-methyl-3-pyridyl)methoxy-tert-butyl-dimethyl-silane (1.65 g, 5.22 mmol), bis(pinacolato)diboron (1.99 g, 7.82 mmol), [1,1'-bis(diphenylphosphino)ferrocene]dichloropalladium(II) (381.84 mg, 0.52 mmol) and potassium acetate (1.28 g, 13.04 mmol) in 1,4-dioxane (18 mL) was stirred for 12 hours at 90° C. After filtration, the filtrate was concentrated under reduced pressure. The resulting residue was purified by reverse phase chromatography (acetonitrile 0-40/0.1% sodium bicarbonate in water) to afford [5-[[tert-butyl(dimethyl)silyl]oxymethyl]-4-methyl-3-pyridyl]boronic acid (480 mg, 1.70 mmol) as a white solid. LC/MS (ESI) [M+H]⁺=282.

Step 3: 6-(5-((tert-butyldimethylsilyloxy)methyl)-4-methylpyridin-3-yl)-8-chloro-7-fluoroisoquinolin-3-amine

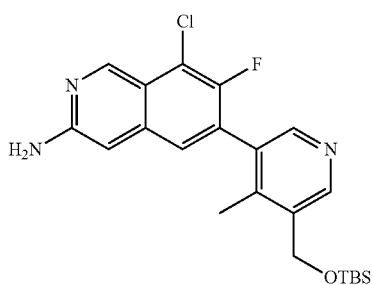 [SMILES: Cc1c(CO[Si](C)(C)C(C)(C)C)cncc1-c1cc2cc(N)ncc2c(Cl)c1F]

A mixture of 8-chloro-7-fluoro-6-iodo-isoquinolin-3-amine (382 mg, 1.18 mmol), [5-[[tert-butyl(dimethyl)silyl]oxymethyl]-4-methyl-3-pyridyl]boronic acid (499.66 mg, 1.78 mmol), [1,1'-bis(diphenylphosphino)ferrocene]dichloropalladium(II) (86.7 mg, 0.12 mmol), potassium carbonate (359.6 mg, 2.61 mmol) in 1,4-dioxane (15 mL) and water (1.5 mL) was stirred for 3 hours at 90° C. After filtration, the filtrate was concentrated under reduced pressure. The residue was purified by flash chromatography on silica gel eluting with ethyl acetate/petroleum ether (7:3) to afford 6-[5-[[tert-butyl(dimethyl)silyl]oxymethyl]-4-methyl-3-pyridyl]-8-chloro-7-fluoro-isoquinolin-3-amine (320 mg, 0.74 mmol) as a yellow solid. LC/MS (ESI) [M+H]=432.

Step 4: 2-(6-(5-((tert-butyldimethylsilyloxy)methyl)-4-methylpyridin-3-yl)-8-chloro-7-fluoroisoquinolin-3-ylamino)-6-isopropyl-5,6-dihydro-4H-pyrazolo[1,5-g][1,4]diazepin-7(8H)-one

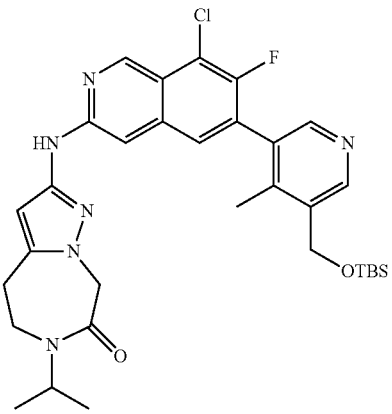 [SMILES: Cc1c(CO[Si](C)(C)C(C)(C)C)cncc1-c1cc2cc(Nc3cc4n(n3)CC(=O)N(C(C)C)CC4)ncc2c(Cl)c1F]

A mixture of 2-bromo-6-isopropyl-5,8-dihydro-4H-pyrazolo[1,5-d][1,4]diazepin-7-one (181.42 mg, 0.67 mmol), 6-[5-[[tert-butyl(dimethyl)silyl]oxymethyl]-4-methyl-3-pyridyl]-8-chloro-7-fluoro-isoquinolin-3-amine (240.0 mg, 0.56 mmol), tris(dibenzylideneacetone)dipalladium-chloroformadduct (115.0 mg, 0.11 mmol), 4,5-bis(diphenylphosphino)-9,9-dimethylxanthene (128.66 mg, 0.22 mmol) and cesium carbonate (543.32 mg, 1.67 mmol) in 1,4-dioxane (20 mL) was stirred for 12 hours at 100° C. After filtration, the filtrate was concentrated under reduced pressure. The residue was purified by flash chromatography on silica gel eluting with ethyl acetate/petroleum ether (10/1) to afford 2-[[6-[5-[[tert-butyl(dimethyl)silyl]oxymethyl]-4-methyl-3-pyridyl]-8-chloro-7-fluoro-3-isoquinolyl]amino]-6-isopropyl-5,8-dihydro-4H-pyrazolo[1,5-d][1,4]diazepin-7-one (56 mg, 0.090 mmol) as a yellow solid. LCMS (ESI) [M+H]⁺=623.

Step 5: tert-butyl 6-(5-((tert-butyldimethylsilyloxy)methyl)-4-methylpyridin-3-yl)-7-fluoro-3-(6-isopropyl-7-oxo-5,6,7,8-tetrahydro-4H-pyrazolo[1,5-g][1,4]diazepin-2-ylamino)isoquinolin-8-ylcarbamate

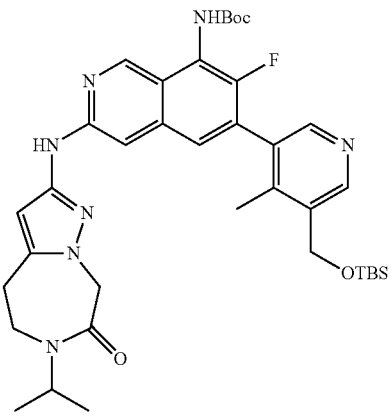 [SMILES: Cc1c(CO[Si](C)(C)C(C)(C)C)cncc1-c1cc2cc(Nc3cc4n(n3)CC(=O)N(C(C)C)CC4)ncc2c(NC(=O)OC(C)(C)C)c1F]

A mixture of 2-[[6-[5-[[tert-butyl(dimethyl)silyl]oxymethyl]-4-methyl-3-pyridyl]-8-chloro-7-fluoro-3-isoquinolyl]amino]-6-isopropyl-5,8-dihydro-4H-pyrazolo[1,5-d][1,4]diazepin-7-one (60.0 mg, 0.10 mmol), tert-butyl carbamate (337.91 mg, 2.89 mmol), tris(dibenzylideneacetone)dipalladium-chloroform adduct (19.93 mg, 0.020 mmol), Brettphos (20.68 mg, 0.040 mmol) and cesium carbonate (125.54 mg, 0.39 mmol) in 1,4-dioxane (5 mL) was stirred for 12 hours at 90° C. After filtration, the filtrate was concentrated under reduced pressure. The residue was purified by flash chromatography on silica gel eluting with methanol/dichloromethane (12:88) to afford tert-butyl N-[6-[5-[[tert-butyl(dimethyl)silyl]oxymethyl]-4-methyl-3-pyridyl]-7-fluoro-3-[(6-isopropyl-7-oxo-5,8-dihydro-4H-pyrazolo[1,5-d][1,4]diazepin-2-yl)amino]-8-isoquinolyl]carbamate (60 mg, 0.085 mmol) as a yellow solid. LCMS (ESI) [M+H]⁺=704.

Step 6: 2-(8-amino-7-fluoro-6-(5-(hydroxymethyl)-4-methylpyridin-3-yl)isoquinolin-3-ylamino)-6-isopropyl-5,6-dihydro-4H-pyrazolo[1,5-g][1,4]diazepin-7(8H)-one

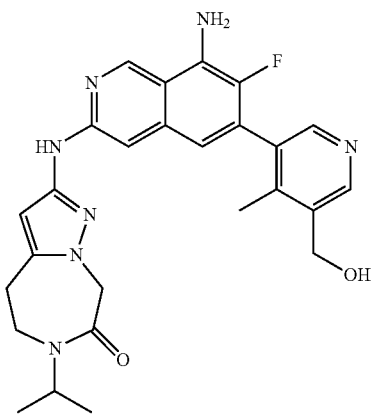 [SMILES: Cc1c(CO)cncc1-c1cc2cc(Nc3cc4n(n3)CC(=O)N(C(C)C)CC4)ncc2c(N)c1F]

A solution of tert-butyl N-[6-[5-[[tert-butyl(dimethyl)silyl]oxymethyl]-4-methyl-3-pyridyl]-7-fluoro-3-[(6-isopropyl-7-oxo-5,8-dihydro-4H-pyrazolo[1,5-d][1,4]diazepin-2-yl)amino]-8-isoquinolyl]carbamate (50.0 mg, 0.070 mmol) in 2,2,2-trifluoroacetic acid (5 mL) was stirred at 25° C. for 12 hours. The mixture was concentrated under vacuum. The crude product was purified by Prep-HPLC (Atlantis HILIC OBD, 19×150 mm 5 um; water (10 mmol/L sodium bicarbonate): CH₃CN=20%-40% B in 7 min) to afford 2-[[8-amino-7-fluoro-6-[5-(hydroxymethyl)-4-methyl-3-pyridyl]-3-isoquinolyl]amino]-6-isopropyl-5,8-dihydro-4H-pyrazolo[1,5-d][1,4]diazepin-7-one (5.1 mg, 0.010 mmol) as a yellow solid. LCMS (ESI) [M+H]⁺=490.2; ¹H NMR (300 MHz, Methanol-d₄) δ 9.17 (s, 1H), 8.56 (s, 1H), 8.37 (s, 1H), 7.66 (s, 1H), 6.87 (d, J=6.2 Hz, 1H), 6.07 (s, 1H), 5.06 (s, 2H), 4.80 (s, 2H), 4.75 (d, J=6.7 Hz, 1H), 3.88 (t, J=6.0 Hz, 2H), 3.14 (d, J=6.1 Hz, 2H), 2.32 (d, J=1.3 Hz, 3H), 1.25 (d, J=6.8 Hz, 6H).

Example 181

2-((8-amino-6-(5-amino-4-methylpyridin-3-yl)-7-fluoroisoquinolin-3-yl)amino)-6-(2-methoxyethyl)-5,6-dihydro-4H-pyrazolo[1,5-d][1,4]diazepin-7(8H)-one (Compound 291)

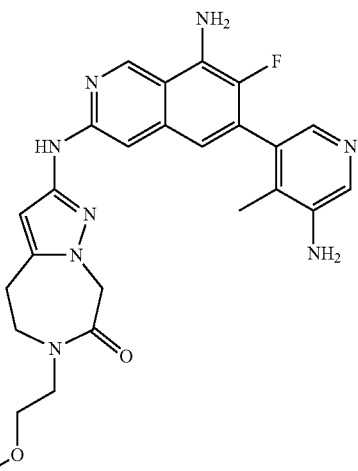

Step 1: 2-bromo-6-(cyclopropylmethyl)-5,8-dihydro-4H-pyrazolo[1,5-d][1,4]diazepin-7-one

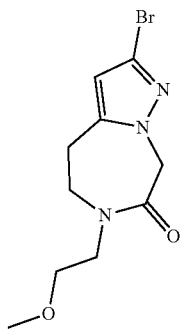 [SMILES: COCCN1CCc2cc(Br)nn2CC1=O]

To a mixture of 2-bromo-4,5,6,8-tetrahydropyrazolo[1,5-d][1,4]diazepin-7-one (200 mg, 0.86 mmol) in N,N-dimethylformamide (6 mL) was added sodium hydride (79.18 mg, 3.48 mmol) at 0° C. The mixture was stirred for 20 mins at 20° C. 1-Iodo-2-methoxy-ethane (485.06 mg, 2.6 mmol) was added. The mixture was then stirred at 20° C. for 1 hour. The reaction was quenched with water. The resulting mixture was extracted with ethyl acetate, dried with anhydrous sodium sulfate. After filtration, the filtrate was concentrated under vacuum. The residue was purified by flash chromatography on silica gel eluting with dichloromethane/methanol (95/5) to afford 2-bromo-6-(2-methoxyethyl)-5,8-dihydro-4H-pyrazolo[1,5-d][1,4]diazepin-7-one (172 mg, 0.31 mmol) as orange oil. LCMS (ESI) [M+H]⁺=288.1.

Step 2: Tert-butyl N-tert-butoxycarbonyl-N-[5-[8-chloro-7-fluoro-3-[[6-(2-methoxyethyl)-7-oxo-5,8-dihydro-4H-pyrazolo[1,5-d][1,4]diazepin-2-yl]amino]-6-isoquinolyl]-4-methyl-3-pyridyl]carbamate

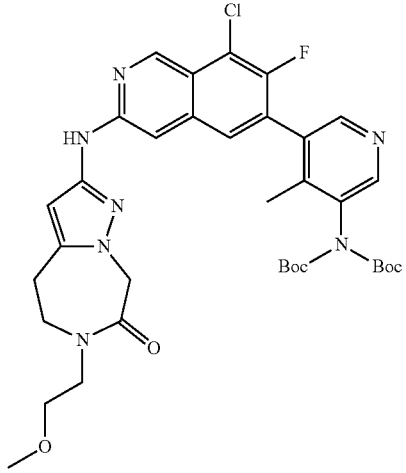 [SMILES: COCCN1CCc2cc(Nc3cc4cc(-c5cncc(N(C(=O)OC(C)(C)C)C(=O)OC(C)(C)C)c5C)c(F)c(Cl)c4cn3)nn2CC1=O]

A mixture of tert-butyl N-[5-(3-amino-8-chloro-7-fluoro-6-isoquinolyl)-4-methyl-3-pyridyl]-N-tert-butoxycarbonyl-carbamate (199 mg, 0.82 mmol), 2-bromo-6-(2-methoxyethyl)-5,8-dihydro-4H-pyrazolo[1,5-d][1,4]diazepin-7-one (172 mg, 1.24 mmol), tris(dibenzylideneacetone)dipalladium-chloroformadduct (82.12 mg, 0.08 mmol), 4,5-bis(diphenylphosphino)-9,9-dimethylxanthene (92.32 mg, 0.16 mmol) and cesium carbonate (389.23 mg, 1.22 mmol) in 1,4-dioxane (16 mL) was stirred at 95° C. for 2 hours. The mixture was concentrated under vacuum. The residue was purified by flash chromatography on silica gel eluting with dichloromethane/methanol (96/4) to afford tert-butyl N-tert-butoxycarbonyl-N-[5-[8-chloro-7-fluoro-3-[[6-(2-methoxyethyl)-7-oxo-5,8-dihydro-4H-pyrazolo[1,5-d][1,4]diazepin-2-yl]amino]-6-isoquinolyl]-4-methyl-3-pyridyl]carbamate (222 mg, 0.17 mmol) as a canary yellow solid. LCMS (ESI) [M+H]$^+$=710.3.

Step 3: Tert-butyl N-tert-butoxycarbonyl-N-[5-[8-(tert-butoxycarbonylamino)-7-fluoro-3-[[6-(2-methoxyethyl)-7-oxo-5,8-dihydro-4H-pyrazolo[1,5-d][1,4]diazepin-2-yl]amino]-6-isoquinolyl]-4-methyl-3-pyridyl]carbamate

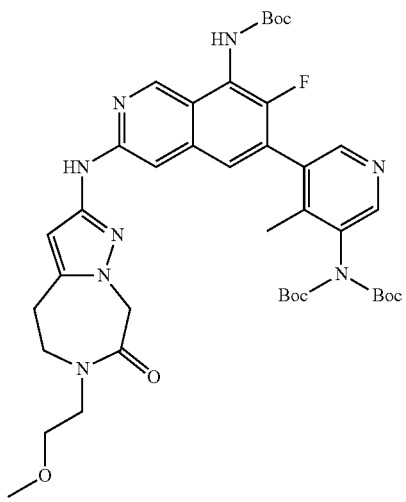 [SMILES: COCCN1CCc2cc(Nc3cc4cc(-c5cncc(N(C(=O)OC(C)(C)C)C(=O)OC(C)(C)C)c5C)c(F)c(NC(=O)OC(C)(C)C)c4cn3)nn2CC1=O]

To a mixture of tert-butyl N-tert-butoxycarbonyl-N-[5-[8-chloro-7-fluoro-3-[[6-(2-methoxyethyl)-7-oxo-5,8-dihydro-4H-pyrazolo[1,5-d][1,4]diazepin-2-yl]amino]-6-isoquinolyl]-4-methyl-3-pyridyl]carbamate (222 mg, 0.31 mmol), tert-butyl carbamate (915.51 mg, 7.81 mmol), Tris(dibenzylideneacetone)dipalladium-chloroform adduct (64.71 mg, 0.06 mmol) and Brettphos (67.02 mg, 0.13 mmol) in 1,4-dioxane (10 mL) was added cesium carbonate (254.76 mg, 0.78 mmol) at 25° C. The resulting solution was stirred at 90° C. for 1 hour. The mixture was concentrated under vacuum. The residue was purified by flash chromatography on silica gel eluting with dichloromethane/methanol (94/6) to afford tert-butyl N-tert-butoxycarbonyl-N-[5-[8-(tert-butoxycarbonylamino)-7-fluoro-3-[[6-(2-methoxyethyl)-7-oxo-5,8-dihydro-4H-pyrazolo[1,5-d][1,4]diazepin-2-yl]amino]-6-isoquinolyl]-4-methyl-3-pyridyl]carbamate (131 mg, 0.17 mmol) as orange solid. LCMS (ESI) [M+H]$^+$=791.4.

Step 4: 2-[[8-amino-6-(5-amino-4-methyl-3-pyridyl)-7-fluoro-3-isoquinolyl]amino]-6-(2-methoxyethyl)-5,8-dihydro-4H-pyrazolo[1,5-d][1,4]diazepin-7-one

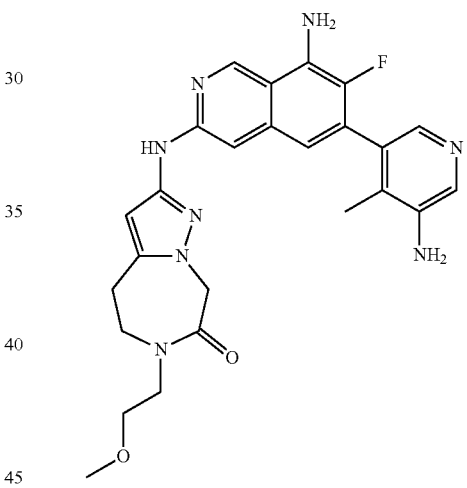

A solution of tert-butyl N-tert-butoxycarbonyl-N-[5-[8-(tert-butoxycarbonylamino)-7-fluoro-3-[[6-(2-methoxyethyl)-7-oxo-5,8-dihydro-4H-pyrazolo[1,5-d][1,4]diazepin-2-yl]amino]-6-isoquinolyl]-4-methyl-3-pyridyl]carbamate (131 mg, 0.17 mmol) and 2,2,2-trifluoroacetic acid (1.0 mL) in dichloromethane (2 mL) was stirred at 20° C. for 1 hour. The mixture was concentrated under vacuum. The reaction mixture was adjusted to pH 8 with a solution of amine in methanol. The crude product was purified by Prep-HPLC (XBridge Prep C18 OBD Column 19×150 mm Sum C-0013; Water (0.1% FA) and ACN (5%-15%) in 7 min) to afford 2-[[8-amino-6-(5-amino-4-methyl-3-pyridyl)-7-fluoro-3-isoquinolyl]amino]-6-(2-methoxyethyl)-5,8-dihydro-4H-pyrazolo[1,5-d][1,4]diazepin-7-one (34.2 mg, 0.064 mol) as light yellow solid. LCMS (ESI) [M+H]$^+$=491.2; $^1$HNMR (300 MHz, DMSO) δ 9.25 (s, 1H), 9.06 (s, 1H), 7.98 (s, 1H), 7.70 (s, 1H), 7.66 (s, 1H), 6.72-6.70 (m, 1H), 6.06 (s, 2H), 5.97 (s, 1H), 5.22 (s, 2H), 4.98 (s, 2H), 3.87-3.85 (m, 2H), 3.57-3.54 (m, 2H), 3.46-3.43 (m, 2H), 3.26 (s, 3H), 3.03-3.01 (m, 2H), 1.93 (s, 3H).

Example 182

2-((8-amino-7-fluoro-6-(4,5,6,7-tetrahydropyrazolo[1,5-a]pyrazin-3-yl)isoquinolin-3-yl)amino)-6-methyl-5,6-dihydro-4H-pyrazolo[1,5-d][1,4]diazepin-7(8H)-one (Compound 292)

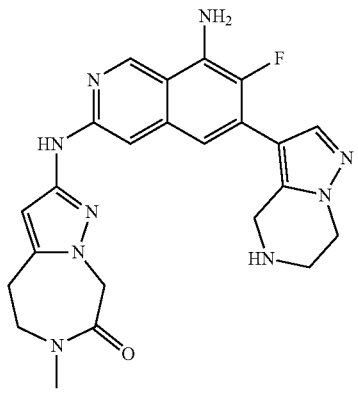 [SMILES: CN1CCc2cc(Nc3cc4cc(-c5cnn6c5CNCC6)c(F)c(N)c4cn3)nn2CC1=O]

Step 1: tert-butyl 3-[8-(tert-butoxycarbonylamino)-7-fluoro-3-[(6-methyl-7-oxo-5,8-dihydro-4H-pyrazolo[1,5-d][1,4]diazepin-2-yl)amino]-6-isoquinolyl]-6,7-dihydro-4H-pyrazolo[1,5-a]pyrazine-5-carboxylate

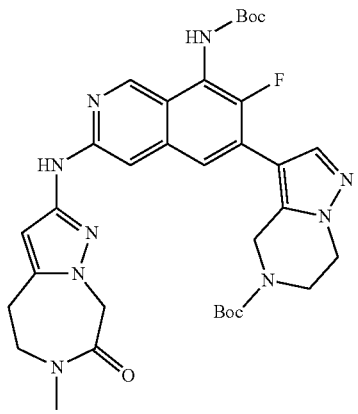 [SMILES: CN1CCc2cc(Nc3cc4cc(-c5cnn6c5CN(C(=O)OC(C)(C)C)CC6)c(F)c(NC(=O)OC(C)(C)C)c4cn3)nn2CC1=O]

A mixture of [7-fluoro-8-(isopropoxycarbonylamino)-3-[(6-methyl-7-oxo-5,8-dihydro-4H-pyrazolo[1,5-d][1,4]diazepin-2-yl)amino]-6-isoquinolyl]boronic acid (100 mg, 0.21 mmol), tert-butyl 3-bromo-6,7-dihydro-4H-pyrazolo[1,5-a]pyrazine-5-carboxylate (120 mg, 0.40 mmol), potassium phosphate (40 mg, 0.19 mmol), sodium acetate (50 mg, 0.61 mmol) and [1,1'-bis(diphenylphosphino)ferrocene]dichloropalladium(II) (40 mg, 0.05 mmol) in acetonitrile (10 mL) and water (1 mL) was stirred at 90° C. for 1 hour. After filtration, the filtrate was concentrated under vacuum. The residue was purified by Prep-TLC with ethyl acetate/methanol (50/1) to afford tert-butyl 3-[8-(tert-butoxycarbonylamino)-7-fluoro-3-[(6-methyl-7-oxo-5,8-dihydro-4H-pyrazolo[1,5-d][1,4]diazepin-2-yl)amino]-6-isoquinolyl]-6,7-dihydro-4H-pyrazolo[1,5-a]pyrazine-5-carboxylate (43 mg, 0.065 mmol) as yellow solid. LCMS (ESI) [M+H]$^+$=662.

Step 2: 2-[[8-amino-7-fluoro-6-(4,5,6,7-tetrahydropyrazolo[1,5-a]pyrazin-3-yl)-3-isoquinolyl]amino]-6-methyl-5,8-dihydro-4H-pyrazolo[1,5-d][1,4]diazepin-7-one

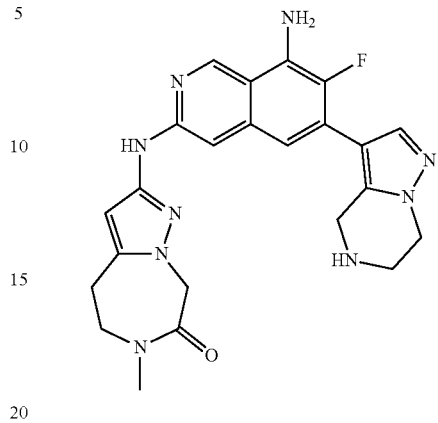

A mixture of tert-butyl 3-[8-(tert-butoxycarbonylamino)-7-fluoro-3-[(6-methyl-7-oxo-5,8-dihydro-4H-pyrazolo[1,5-d][1,4]diazepin-2-yl)amino]-6-isoquinolyl]-6,7-dihydro-4H-pyrazolo[1,5-a]pyrazine-5-carboxylate (40 mg, 0.06 mmol), 2,2,2-trifluoroacetic acid (1 mL) and dichloromethane (5 mL) was stirred for 1 hour at room temperature. The mixture was concentrated under vacuum. The residue was dissolved in dichloromethane and then adjusted to pH 7 with ammonia in methanol (7 mol/L). The mixture was concentrated under vacuum. The residue was purified by Prep-HPLC (XBridge prep C18 OBD, 19*150 mm, 5 um; Water (0.05% NH$_3$H$_2$O): ACN (7-24% in 7 min)) to afford 2-[[8-amino-7-fluoro-6-(4,5,6,7-tetrahydropyrazolo[1,5-a]pyrazin-3-yl)-3-isoquinolyl]amino]-6-methyl-5,8-dihydro-4H-pyrazolo[1,5-d][1,4]diazepin-7-one (4 mg, 0.0087 mmol) as a yellow solid. LCMS (ESI) [M+H]$^+$=462. $^1$HNMR (300 MHz, DMSO-d$_6$) δ 9.17 (s, 1H), 9.01 (s, 1H), 7.73 (d, J=2.9 Hz, 1H), 7.63 (s, 1H), 6.74 (d, J=6.3 Hz, 1H), 5.98 (s, 3H), 4.99 (s, 2H), 4.06-4.05 (m, 4H), 3.83-3.82 (m, 2H), 3.18-3.17 (m, 2H), 3.05-3.03 (m, 2H), 2.96 (s, 3H), 2.69 (s, 1H).

Example 183

2-((8-amino-6-(5-amino-4-methylpyridin-3-yl)-7-fluoroisoquinolin-3-yl)amino)-4,6-dimethyl-5,6-dihydro-4H,8H-pyrazolo[5,1-e][1,2,6]thiadiazepine 7,7-dioxide (Compound 293)

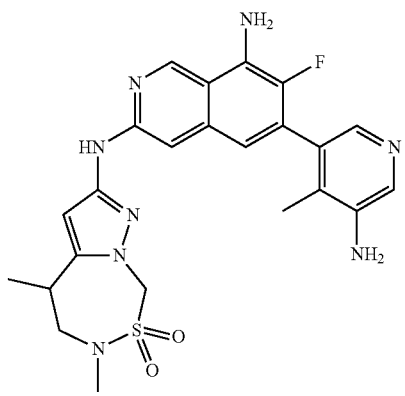 [SMILES: Cc1c(N)cncc1-c1cc2cc(Nc3cc4n(n3)CS(=O)(=O)N(C)CC4C)ncc2c(N)c1F]

Step 1: tert-butyl N-tert-butoxycarbonyl-N-[5-[8-chloro-7-fluoro-3-[(6-methyl-4-methylene-7,7-dioxo-5,8-dihydropyrazolo[5,1-e][1,2,6]thiadiazepin-2-yl)amino]-6-isoquinolyl]-4-methyl-3-pyridyl]carbamate

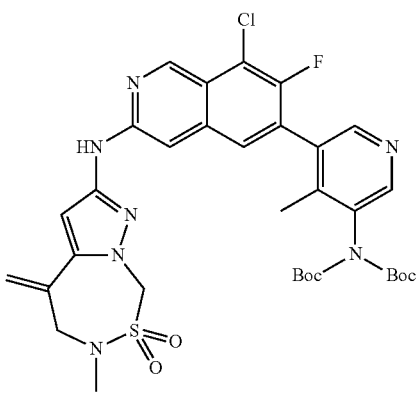 [SMILES: C=C1CN(C)S(=O)(=O)Cn2nc(Nc3cc4cc(-c5cncc(N(C(=O)OC(C)(C)C)C(=O)OC(C)(C)C)c5C)c(F)c(Cl)c4cn3)cc21]

A mixture of 2-bromo-6-methyl-4-methylene-5,8-dihydropyrazolo[5,1-e][1,2,6]thiadiazepine 7,7-dioxide (200 mg, 0.68 mmol), tert-butyl N-[5-(3-amino-8-chloro-7-fluoro-6-isoquinolyl)-4-methyl-3-pyridyl]-N-tert-butoxycarbonyl-carbamate (309.89 mg, 0.62 mmol), t-BuBrettphos (165.67 mg, 0.34 mmol), t-BuBrettphos Pd G3 (233.85 mg, 0.27 mmol) and cesium carbonate (557.93 mg, 1.71 mmol) in 1,4-dioxane (15 mL) was stirred for 1 hour at 120° C. After filtration, the filtrate was concentrated under reduced pressure. The residue was purified by flash chromatography on silica gel eluting with ethyl acetate/petroleum ether (4/1) to afford tert-butyl N-tert-butoxycarbonyl-N-[5-[8-chloro-7-fluoro-3-[(6-methyl-4-methylene-7,7-dioxo-5,8-dihydropyrazolo[5,1-e][1,2,6]thiadiazepin-2-yl)amino]-6-isoquinolyl]-4-methyl-3-pyridyl]carbamate (100 mg, 0.14 mmol) as a brown solid. LCMS (ESI) [M+H]$^+$=714

Step 2: tert-butyl N-tert-butoxycarbonyl-N-[5-[8-(tert-butoxycarbonylamino)-7-fluoro-3-[(6-methyl-4-methylene-7,7-dioxo-5,8-dihydropyrazolo[5,1-e][1,2,6]thiadiazepin-2-yl)amino]-6-isoquinolyl]-4-methyl-3-pyridyl]carbamate

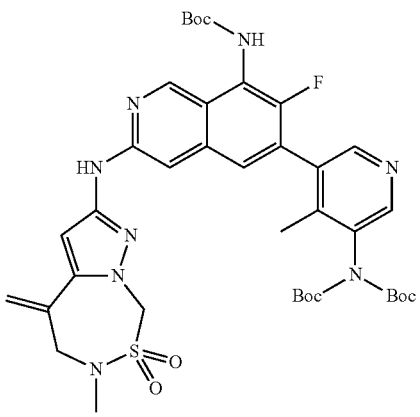 [SMILES: C=C1CN(C)S(=O)(=O)Cn2nc(Nc3cc4cc(-c5cncc(N(C(=O)OC(C)(C)C)C(=O)OC(C)(C)C)c5C)c(F)c(NC(=O)OC(C)(C)C)c4cn3)cc21]

A mixture of tert-butyl carbamate (262.44 mg, 2.24 mmol), tert-butyl N-tert-butoxycarbonyl-N-[5-[8-chloro-7-fluoro-3-[(6-methyl-4-methylene-7,7-dioxo-5,8-dihydropyrazolo[5,1-e][1,2,6]thiadiazepin-2-yl)amino]-6-isoquinolyl]-4-methyl-3-pyridyl]carbamate (80 mg, 0.11 mmol), tris(dibenzylideneacetone)dipalladium-chloroformadduct (23.19 mg, 0.02 mmol), Brettphos (18.05 mg, 0.03 mmol) and cesium carbonate (91.29 mg, 0.28 mmol) in 1,4-dioxane (10 mL) was stirred for 2 hours at 100° C. After filtration, the filtrate was concentrated under reduced pressure. The residue was purified by flash chromatography on silica gel eluting with methanol/dichloromethane (2/98) to afford tert-butyl N-tert-butoxycarbonyl-N-[5-[8-(tert-butoxycarbonylamino)-7-fluoro-3-[(6-methyl-4-methylene-7,7-dioxo-5,8-dihydropyrazolo[5,1-e][1,2,6]thiadiazepin-2-yl)amino]-6-isoquinolyl]-4-methyl-3-pyridyl]carbamate (60 mg, 0.076 mmol) as a yellow solid. LCMS (ESI) [M+H]$^+$=795

Step 3: tert-butyl N-tert-butoxycarbonyl-N-[5-[8-(tert-butoxycarbonylamino)-3-[(4,6-dimethyl-7,7-dioxo-5,8-dihydro-4H-pyrazolo[5,1-e][1,2,6]thiadiazepin-2-yl)amino]-7-fluoro-6-isoquinolyl]-4-methyl-3-pyridyl]carbamate

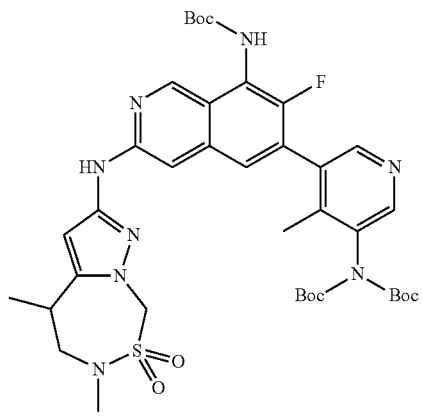 [SMILES: Cc1c(-c2cc3cc(Nc4cc5n(n4)CS(=O)(=O)N(C)CC5C)ncc3c(NC(=O)OC(C)(C)C)c2F)cncc1N(C(=O)OC(C)(C)C)C(=O)OC(C)(C)C]

A mixture of tert-butyl N-tert-butoxycarbonyl-N-[5-[8-(tert-butoxycarbonylamino)-7-fluoro-3-[(6-methyl-4-methylene-7,7-dioxo-5,8-dihydropyrazolo[5,1-e][1,2,6]thiadiazepin-2-yl)amino]-6-isoquinolyl]-4-methyl-3-pyridyl]carbamate (50 mg, 0.06 mmol) and Raney nickel (10 mg) in methanol (10 mL) was stirred at 25° C. for 12 hours. After filtration, the filtrate was concentrated under reduced pressure to afford tert-butyl N-tert-butoxycarbonyl-N-[5-[8-(tert-butoxycarbonylamino)-3-[(4,6-dimethyl-7,7-dioxo-5,8-dihydro-4H-pyrazolo[5,1-e][1,2,6]thiadiazepin-2-yl)amino]-7-fluoro-6-isoquinolyl]-4-methyl-3-pyridyl]carbamate (45 mg, 0.05 mmol) as a yellow solid. LCMS (ESI) [M+H]$^+$=797

Step 4: 6-(5-amino-4-methyl-3-pyridyl)-N3-(4,6-dimethyl-7,7-dioxo-5,8-dihydro-4H-pyrazolo[5,1-e][1,2,6]thiadiazepin-2-yl)-7-fluoro-isoquinoline-3,8-diamine; Formic Acid

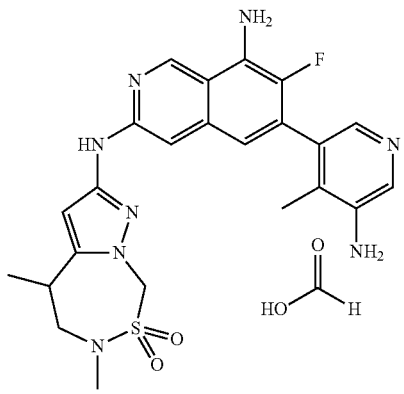

A solution of tert-butyl N-tert-butoxycarbonyl-N-[5-[8-(tert-butoxycarbonylamino)-3-[(4,6-dimethyl-7,7-dioxo-5,8-dihydro-4H-pyrazolo[5,1-e][1,2,6]thiadiazepin-2-yl)amino]-7-fluoro-6-isoquinolyl]-4-methyl-3-pyridyl]carbamate (50 mg, 0.06 mmol) and 2,2,2-trifluoroacetic acid (1 mL) in dichloromethane (2 mL) was stirred at 25° C. for 2 hours. The mixture was concentrated under vacuum. The residue was adjusted to pH 10 with ammonia in methanol (7 mol/L). The resulting residue was purified by reverse phase chromatography (acetonitrile 0-40/0.1% FA in water) to afford 6-(5-amino-4-methyl-3-pyridyl)-N3-(4,6-dimethyl-7,7-dioxo-5,8-dihydro-4H-pyrazolo[5,1-e][1,2,6]thiadiazepin-2-yl)-7-fluoro-isoquinoline-3,8-diamine; formic acid (2.9 mg, 0.0053 mmol) as a brown solid. LCMS (ESI) [M+H]$^+$=497. $^1$HNMR (400 MHz, CD$_3$OD) δ 9.16 (s, 1H), 8.39 (s, 1H), 7.78-7.77 (d, J=4.0 Hz, 2H), 6.90-6.88 (d, J=8.0 Hz, 1H), 6.11 (s, 1H), 5.92-5.88 (d, J=16 Hz, 1H), 5.36-5.32 (d, J=16 Hz, 1H), 3.79-3.55 (m, 3H), 3.13 (s, 3H), 2.09 (s, 3H), 1.39-1.38 (d, J=4.0 Hz, 3H)

Example 184

[2-[[8-amino-6-(5-amino-4-methyl-3-pyridyl)-7-fluoro-3-isoquinolyl]amino]-6-ethyl-5,8-dihydro-4H-pyrazolo[1,5-d][1,4]diazepin-7-one (Compound 298)

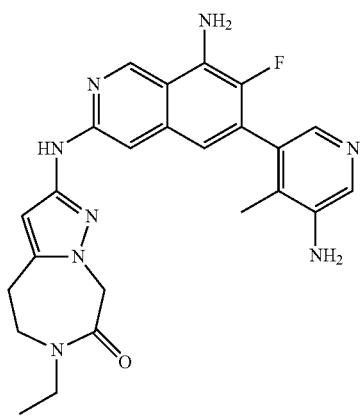 [SMILES: CCN1CCc2cc(Nc3cc4cc(-c5cncc(N)c5C)c(F)c(N)c4cn3)nn2CC1=O]

Step 1: 2-bromo-6-ethyl-5,8-dihydro-4H-pyrazolo[1,5-d][1,4]diazepin-7-one

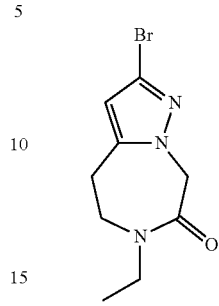

To a solution of 2-bromo-4,5,6,8-tetrahydropyrazolo[1,5-d][1,4]diazepin-7-one (1 g, 4.0 mmol) in N,N-dimethylformamide (2 mL) was added sodium hydride (313 mg, 13.0 mmol) at 0° C. The mixture was stirred for 30 minutes at 0° C. Iodoethane (1.3 g, 9.0 mmol) was added to this reaction solution at 0° C. and then stirred for 4 hours. The reaction was quenched by water. The resulting solution was extracted with ethyl acetate, dried with anhydrous sodium sulfate. After filtration, the filtrate was concentrated under vacuum. The residue was purified by reverse phase chromatography (acetonitrile-0.1% sodium bicarbonate in water) to afford 2-bromo-6-ethyl-5,8-dihydro-4H-pyrazolo[1,5-d][1,4]diazepin-7-one (1 g, 3.89 mmol) as a white solid. LCMS (ESI) [M+H]$^+$=258.1.

Step 2: tert-butyl N-tert-butoxycarbonyl-N-[5-[8-chloro-3-[(6-ethyl-7-oxo-5,8-dihydro-4H-pyrazolo[1,5-d][1,4]diazepin-2-yl)amino]-7-fluoro-6-isoquinolyl]-4-methyl-3-pyridyl]carbamate

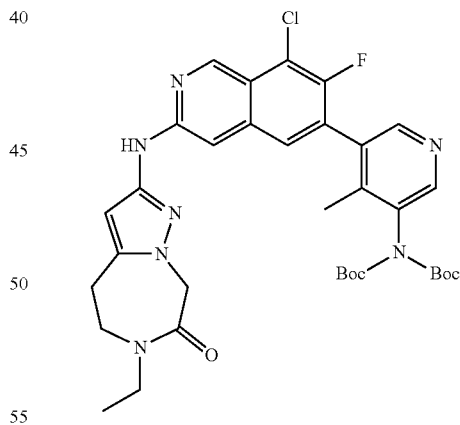

A mixture of 2-bromo-6-ethyl-5,8-dihydro-4H-pyrazolo[1,5-d][1,4]diazepin-7-one (140.0 mg, 0.54 mmol), tert-butyl N-[5-(3-amino-8-chloro-7-fluoro-6-isoquinolyl)-4-methyl-3-pyridyl]-N-tert-butoxycarbonyl-carbamate (272.8 mg, 0.54 mmol), tris(dibenzylideneacetone)dipalladium-chloroformadduct (112.27 mg, 0.11 mmol), 4,5-bis(diphenylphosphino)-9,9-dimethylxanthene (125.4 mg, 0.22 mmol) and cesium carbonate (530.45 mg, 1.63 mmol) in 1,4-dioxane (2 mL) was stirred at 100° C. for 4 hours. After filtration, the filtrate was concentrated under vacuum. The residue was purified by flash chromatography on silica gel eluting with ethyl acetate/petroleum ether (1/1) to afford tert-butyl N-tert-butoxycarbonyl-N—[5-[8-chloro-3-[(6-ethyl-7-oxo-5,8-dihydro-4H-pyrazolo[1,5-d][1,4]diazepin-2-yl)amino]-7-fluoro-6-isoquinolyl]-4-methyl-3-pyridyl]carbamate (70 mg, 0.10 mmol) as a yellow oil. LCMS (ESI) [M+H]$^+$=680.2.

Step 3: tert-butyl N-tert-butoxycarbonyl-N-[5-[8-(tert-butoxycarbonylamino)-3-[(6-ethyl-7-oxo-5,8-dihydro-4H-pyrazolo[1,5-d][1,4]diazepin-2-yl)amino]-7-fluoro-6-isoquinolyl]-4-methyl-3-pyridyl]carbamate

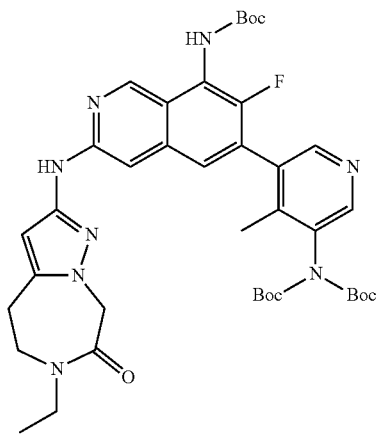 [SMILES: CCN1CCc2cc(Nc3cc4cc(-c5cncc(N(C(=O)OC(C)(C)C)C(=O)OC(C)(C)C)c5C)c(F)c(NC(=O)OC(C)(C)C)c4cn3)nn2CC1=O]

A mixture of tert-butyl N-tert-butoxycarbonyl-N-[5-[8-chloro-3-[(6-ethyl-7-oxo-5,8-dihydro-4H-pyrazolo[1,5-d][1,4]diazepin-2-yl)amino]-7-fluoro-6-isoquinolyl]-4-methyl-3-pyridyl]carbamate (40.0 mg, 0.06 mmol), tert-butyl carbamate (206.76 mg, 1.76 mmol), tris(dibenzylideneacetone)dipalladium-chloroformadduct (12.0 mg, 0.01 mmol), Brettphos (6.32 mg, 0.01 mmol) and cesium carbonate (76.8 mg, 0.24 mmol) in 1,4-dioxane (2 mL) was stirred for 4 hours at 90° C. The mixture was concentrated under vacuum. The residue was purified by flash chromatography on silica gel eluting with methanol/dichloromethane (1/4) to afford tert-butyl N-tert-butoxycarbonyl-N-[5-[8-(tert-butoxycarbonylamino)-3-[(6-ethyl-7-oxo-5,8-dihydro-4H-pyrazolo[1,5-d][1,4]diazepin-2-yl)amino]-7-fluoro-6-isoquinolyl]-4-methyl-3-pyridyl]carbamate (40 mg, 0.053 mmol) as a yellow oil. LCMS (ESI) [M+H]$^+$=706.9.

Step 4: 2-[[8-amino-6-(5-amino-4-methyl-3-pyridyl)-7-fluoro-3-isoquinolyl]amino]-6-ethyl-5,8-dihydro-4H-pyrazolo[1,5-d][1,4]diazepin-7-one

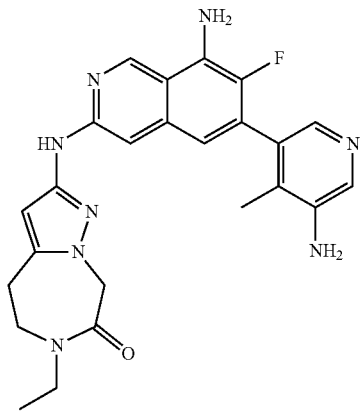 [SMILES: CCN1CCc2cc(Nc3cc4cc(-c5cncc(N)c5C)c(F)c(N)c4cn3)nn2CC1=O]

A mixture of tert-butyl N-tert-butoxycarbonyl-N-[5-[8-(tert-butoxycarbonylamino)-3-[(6-ethyl-7-oxo-5,8-dihydro-4H-pyrazolo[1,5-d][1,4]diazepin-2-yl)amino]-7-fluoro-6-isoquinolyl]-4-methyl-3-pyridyl]carbamate (40.0 mg, 0.05 mmol) and 2,2,2-trifluoroacetic acid (2 mL) in dichloromethane (2 mL) was stirred at 25° C. for 2 hours. The mixture was concentrated under vacuum. The residue was purified by flash chromatography on C18 (acetonitrile-0.1% sodium bicarbonate in water) afford 2-[[8-amino-6-(5-amino-4-methyl-3-pyridyl)-7-fluoro-3-isoquinolyl]amino]-6-ethyl-5,8-dihydro-4H-pyrazolo[1,5-d][1,4]diazepin-7-one (2.4 mg, 0.01 mmol) as a yellow solid. LCMS (ESI) [M+H]$^+$=460.5. $^1$HNMR (300 MHz, DMSO-d$_6$) δ 9.26 (s, 1H), 9.07 (s, 1H), 7.99 (s, 1H), 7.69 (d, J=9.4 Hz, 2H), 6.72 (d, J=6.1 Hz, 1H), 6.07 (s, 2H), 5.99 (s, 1H), 5.24 (s, 2H), 4.97 (s, 2H), 3.90-3.84 (m, 2H), 3.50-3.43 (m, 2H), 3.05-2.90 (m, 2H), 1.94 (s, 3H), 1.09-1.01 (m, 3H).

Example 185

2-((8-amino-6-(5-amino-4,6-dimethylpyridin-3-yl)-7-fluoroisoquinolin-3-yl)amino)-6-methyl-5,6-dihydro-4H-pyrazolo[1,5-d][1,4]diazepin-7(8H)-one (Compound 299)

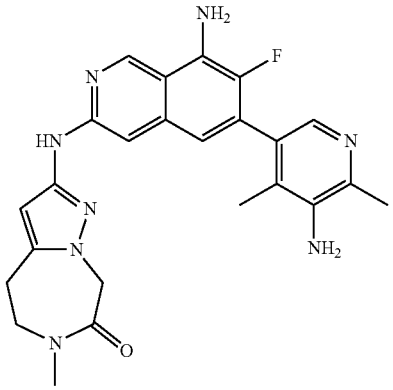 [SMILES: Cc1ncc(-c2cc3cc(Nc4cc5n(n4)CC(=O)N(C)CC5)ncc3c(N)c2F)c(C)c1N]

Step 1: dimethyl 2-(5-bromo-4-methyl-3-nitro-2-pyridyl)propanedioate

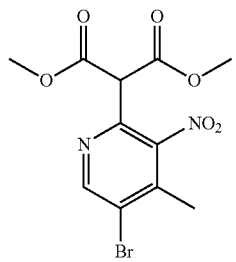

To a solution of dimethyl malonate (3.15 g, 23.86 mmol) in 1-methyl-2-pyrrolidinone (100 mL) was added sodium hydride (0.95 g, 23.86 mmol, 60% purity) at 0° C. The mixture was stirred at 0° C. for 10 mins. 5-Bromo-2-chloro-4-methyl-3-nitropyridine (4.0 g, 15.91 mmol) was added. The mixture was stirred at 40° C. for 12 hours. The reaction was quenched with water. The reaction mixture was diluted with water. The resulting mixture was extracted with ethyl acetate, dried with anhydrous sodium sulfate. After filtration, the filtrate was concentrated under vacuum to afford dimethyl 2-(5-bromo-4-methyl-3-nitro-2-pyridyl)propanedioate (3.5 g, 10.08 mmol) as a brown solid. LCMS (ESI) [M+H]$^+$=347.

Step 2: 5-bromo-2,4-dimethyl-3-nitro-pyridine

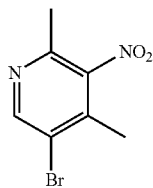

A solution of dimethyl 2-(5-bromo-4-methyl-3-nitro-2-pyridyl)propanedioate (3.5 g, 10.08 mmol) in hydrochloric acid (20 mL, 12 mol/L) was stirred at 100° C. for 12 hours. The mixture was concentrated under vacuum. The reaction mixture was adjusted to pH 10 with sodium hydroxide solution (10%). The resulting solution was extracted with ethyl acetate, dried with anhydrous sodium sulfate. After filtration, the filtrate was concentrated under vacuum. The residue was purified by flash chromatography on silica gel eluting with ethyl acetate/petroleum ether (1/9) to afford 5-bromo-2,4-dimethyl-3-nitro-pyridine (1.5 g, 6.49 mmol) as a yellow solid. LCMS (ESI) [M+H]$^+$=231.

Step 3: (4,6-dimethyl-5-nitropyridin-3-yl)boronic Acid

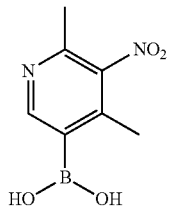

A mixture of 5-bromo-2,4-dimethyl-3-nitro-pyridine (1.5 g, 6.49 mmol), bis(pinacolato)diboron (3.29 g, 12.98 mmol), [1,1'-bis(diphenylphosphino)ferrocene]dichloropalladium (II) (950.44 mg, 1.30 mmol) and potassium acetate (1.91 g, 19.48 mmol) in 1,4-dioxane (30 mL) was stirred for 12 hours at 90° C. After filtration, the filtrate was concentrated under reduced pressure. The reaction mixture was adjusted to pH 10 with sodium hydroxide solution (10%). The water layer was washed with diethyl ether. The solution was adjusted to pH 5 with hydrochloric acid (1 mol/L). The resulting mixture was extracted with ethyl acetate, dried with anhydrous sodium sulfate. After filtration, the filtrate was concentrated under vacuum to afford (4,6-dimethyl-5-nitropyridin-3-yl) boronic acid (1.1 g, 3.95 mmol) as a brown solid. LCMS (ESI) [M+H]$^+$=197.

Step 4: 8-chloro-6-(4,6-dimethyl-5-nitro-3-pyridyl)-7-fluoro-isoquinolin-3-amine

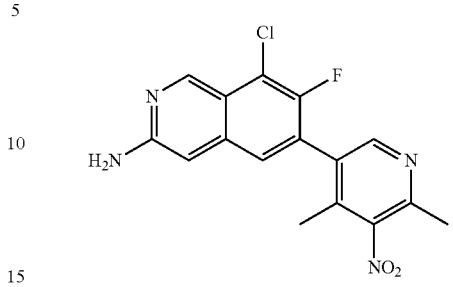

A mixture of (4,6-dimethyl-5-nitro-3-pyridyl)boronic acid (364.58 mg, 1.86 mmol), 8-chloro-7-fluoro-6-iodo-isoquinolin-3-amine (400 mg, 1.24 mmol), [1,1'-bis(diphenylphosphino)ferrocene]dichloropalladium(II) (90.79 mg, 0.12 mmol) and potassium carbonate (342.31 mg, 2.48 mmol) in 1,4-dioxane (15 mL) was stirred for 12 hours at 90° C. After filtration, the filtrate was concentrated under reduced pressure. The residue was purified by flash chromatography on silica gel eluting with dichloromethane/methanol (10/1) to afford 8-chloro-6-(4,6-dimethyl-5-nitro-3-pyridyl)-7-fluoro-isoquinolin-3-amine (220 mg, 0.63 mmol) as a yellow solid. LCMS (ESI) [M+H]$^+$=347.

Step 5: 2-[[8-chloro-6-(4,6-dimethyl-5-nitro-3-pyridyl)-7-fluoro-3-isoquinolyl]amino]-6-methyl-5,8-dihydro-4H-pyrazolo[1,5-d][1,4]diazepin-7-one

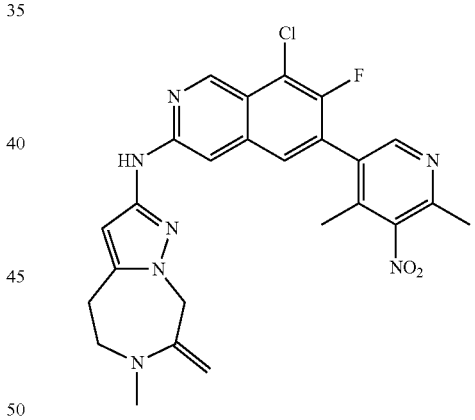

A mixture of 8-chloro-6-(4,6-dimethyl-5-nitro-3-pyridyl)-7-fluoro-isoquinolin-3-amine (220 mg, 0.63 mmol), 2-bromo-6-methyl-5,8-dihydro-4H-pyrazolo[1,5-d] [1,4]diazepin-7-one (154.87 mg, 0.63 mmol), tris(dibenzylideneacetone)dipalladium-chloroformadduct (65.67 mg, 0.06 mmol), 4,5-bis(diphenylphosphino)-9,9-dimethylxanthene (108.37 mg, 0.13 mmol) and cesium carbonate (620.52 mg, 1.9 mmol) in 1,4-dioxane (15 mL) was stirred for 12 hours at 100° C. After filtration, the filtrate was concentrated under reduced pressure. The residue was purified by flash chromatography on silica gel eluting with dichloromethane/methanol (10/1) to afford 2-[[8-chloro-6-(4,6-dimethyl-5-nitro-3-pyridyl)-7-fluoro-3-isoquinolyl] amino]-6-methyl-5,8-dihydro-4H-pyrazolo[1,5-d][1,4]diazepin-7-one (210 mg, 0.41 mmol) as a brown solid. LCMS (ESI) [M+H]$^+$=510

Step 6: tert-butyl N-[6-(4,6-dimethyl-5-nitro-3-pyridyl)-7-fluoro-3-[(6-methyl-7-oxo-5,8-dihydro-4H-pyrazolo[1,5-d][1,4]diazepin-2-yl)amino]-8-isoquinolyl]carbamate

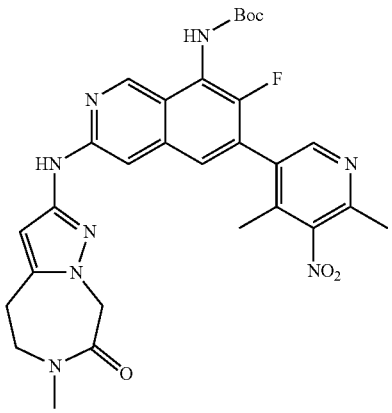 [SMILES: Cc1ncc(-c2cc3cc(Nc4cc5n(n4)CC(=O)N(C)CC5)ncc3c(NC(=O)OC(C)(C)C)c2F)c(C)c1[N+](=O)[O-]]

A mixture of 2-[[8-chloro-6-(4,6-dimethyl-5-nitro-3-pyridyl)-7-fluoro-3-isoquinolyl]amino]-6-methyl-5,8-dihydro-4H-pyrazolo[1,5-d][1,4]diazepin-7-one (260 mg, 0.51 mmol), tert-butyl carbamate (1194.66 mg, 10.2 mmol), tris(dibenzylideneacetone)dipalladium-chloroformadduct (105.55 mg, 0.10 mmol), Brettphos (82.14 mg, 0.15 mmol) and cesium carbonate (415.56 mg, 1.27 mmol) in 1,4-dioxane (20 mL) was stirred at 90° C. for 2 hours. After filtration, the filtrate was concentrated under reduced pressure. The residue was purified by flash chromatography on silica gel eluting with dichloromethane/methanol (10/1) to afford tert-butyl N-[6-(4,6-dimethyl-5-nitro-3-pyridyl)-7-fluoro-3-[(6-methyl-7-oxo-5,8-dihydro-4H-pyrazolo[1,5-d][1,4]diazepin-2-yl)amino]-8-isoquinolyl]carbamate (150 mg, 0.25 mmol) as a brown solid. LCMS (ESI) [M+H]$^+$=591

Step 7: tert-butyl N-[6-(5-amino-4,6-dimethyl-3-pyridyl)-7-fluoro-3-[(6-methyl-7-oxo-5,8-dihydro-4H-pyrazolo[1,5-d][1,4]diazepin-2-yl)amino]-8-isoquinolyl]carbamate

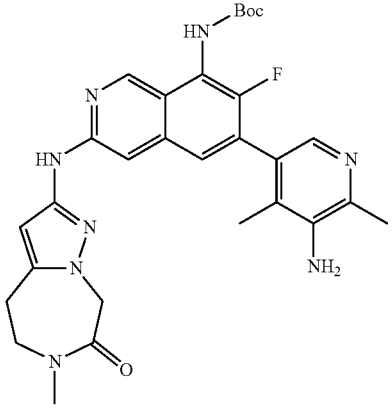

A mixture of tert-butyl N-[6-(4,6-dimethyl-5-nitro-3-pyridyl)-7-fluoro-3-[(6-methyl-7-oxo-5,8-dihydro-4H-pyrazolo[1,5-d][1,4]diazepin-2-yl)amino]-8-isoquinolyl]carbamate (150 mg, 0.25 mmol) and Raney nickel (50 mg) in methanol (10 mL) was stirred for 5 hours at 25° C. under H$_2$. After filtration, the filtrate was concentrated under reduced pressure to afford tert-butyl N-[6-(5-amino-4,6-dimethyl-3-pyridyl)-7-fluoro-3-[(6-methyl-7-oxo-5,8-dihydro-4H-pyrazolo[1,5-d][1,4]diazepin-2-yl)amino]-8-isoquinolyl]carbamate (100 mg, 0.17 mmol) as a brown solid. LCMS (ESI) [M+H]$^+$=561

Step 8: 2-[[8-amino-6-(5-amino-4,6-dimethyl-3-pyridyl)-7-fluoro-3-isoquinolyl]amino]-6-methyl-5,8-dihydro-4H-pyrazolo[1,5-d][1,4]diazepin-7-one

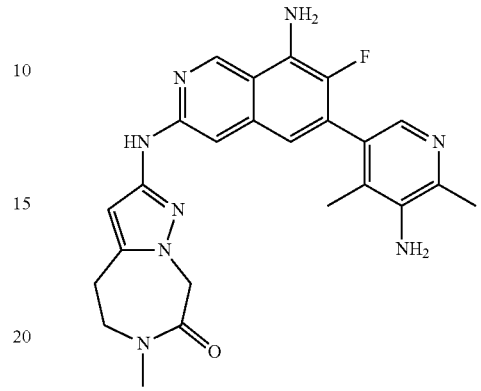

A mixture of tert-butyl N-[6-(5-amino-4,6-dimethyl-3-pyridyl)-7-fluoro-3-[(6-methyl-7-oxo-5,8-dihydro-4H-pyrazolo[1,5-d][1,4]diazepin-2-yl)amino]-8-isoquinolyl]carbamate (100 mg, 0.18 mmol) and 2,2,2-trifluoroacetic acid (2 mL) in dichloromethane (2 mL) was stirred at 25° C. for 2 hours. The mixture was concentrated under vacuum. The reaction mixture was adjusted to pH 10 with ammonia in methanol (7 mol/L). The resulting residue was purified by reverse phase chromatography (acetonitrile 0-40/0.1% ammonia in water) to afford 2-[[8-amino-6-(5-amino-4,6-dimethyl-3-pyridyl)-7-fluoro-3-isoquinolyl]amino]-6-methyl-5,8-dihydro-4H-pyrazolo[1,5-d][1,4]diazepin-7-one (22.2 mg, 0.04 mmol) as a yellow solid. LCMS (ESI) [M+H]$^+$=561. $^1$HNMR (300 MHz, DMSO-d$_6$) δ 9.23 (s, 1H), 9.04 (s, 1H), 7.67 (s, 1H), 7.59 (s, 1H), 6.69 (d, J=6.0 Hz, 1H), 6.03 (s, 2H), 5.97 (s, 1H), 4.96 (s, 2H), 4.90 (s, 2H), 3.89-3.80 (m, 2H), 3.03-3.00 (m, 2H), 2.94 (s, 3H), 2.35 (s, 3H), 1.95 (s, 3H).

Example 186

2-(8-amino-6-(2-amino-3-methylpyridin-4-yl)-7-fluoroisoquinolin-3-ylamino)-6-(2,2-difluoroethyl)-5,6-dihydro-4H-pyrazolo[1,5-g][1,4]diazepin-7(8H)-one (Compound 300)

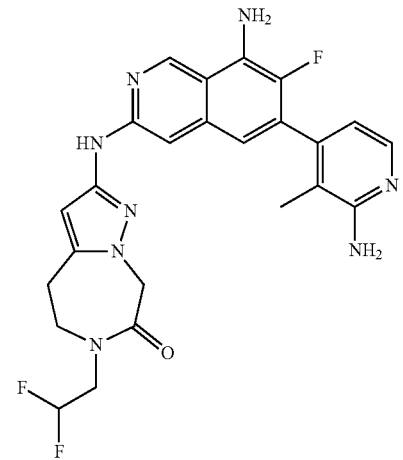 [SMILES: Cc1c(-c2cc3cc(Nc4cc5n(n4)CC(=O)N(CC(F)F)CC5)ncc3c(N)c2F)ccnc1N]

Step 1: 4-bromo-N,N-bis(4-methoxybenzyl)-3-methylpyridin-2-amine

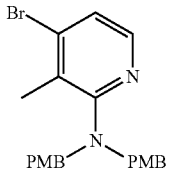

A solution of 4-bromo-3-methyl-pyridin-2-amine (500.0 mg, 2.67 mmol), sodium hydride (427.72 mg, 10.69 mmol) in N,N-dimethylformamide (50 mL) was stirred for 30 minutes at 0° C. 4-methoxybenzyl chloride (2.09 g, 13.37 mmol) was added and stirred at 25° C. for 2 hours. The reaction was quenched with water. The reaction mixture was diluted with ethyl acetate. The resulting mixture was washed with water and the organic layers were combined. The organic layer was dried with anhydrous sodium sulfate. After filtration, the filtrate was concentrated under vacuum. The residue was purified by flash chromatography on silica gel eluting with ethyl acetate/petroleum ether (2/8) to afford 4-bromo-N,N-bis[(4-methoxyphenyl)methyl]-3-methyl-pyridin-2-amine (1.1 g, 2.57 mmol) as a yellow oil. LCMS (ESI) [M+H]$^+$=427.

Step 2: 2-(bis(4-methoxybenzyl)amino)-3-methylpyridin-4-ylboronic Acid

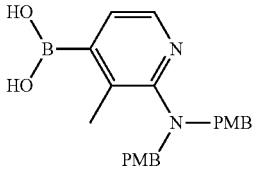

A mixture of 4-bromo-N,N-bis[(4-methoxyphenyl)methyl]-3-methyl-pyridin-2-amine (1.1 g, 2.57 mmol), bis(pinacolato)diboron (980.51 mg, 3.86 mmol) and [1,1'-bis(diphenylphosphino)ferrocene]dichloropalladium(II) (188.43 mg, 0.26 mmol) in 1,4-dioxane (15 mL) was stirred for 3 hours at 90° C. After filtration, the filtrate was concentrated under reduced pressure. The resulting residue was purified by reverse phase chromatography (acetonitrile 5-85/0.1% sodium bicarbonate in water) to afford 2-[bis[(4-methoxyphenyl)methyl]amino]-3-methyl-4-pyridyl]boronic acid (750 mg, 1.91 mmol) as a yellow solid. LCMS (ESI) [M+H]$^+$=393.

Step 3: 6-(2-(bis(4-methoxybenzyl)amino)-3-methylpyridin-4-yl)-8-chloro-7-fluoroisoquinolin-3-amine

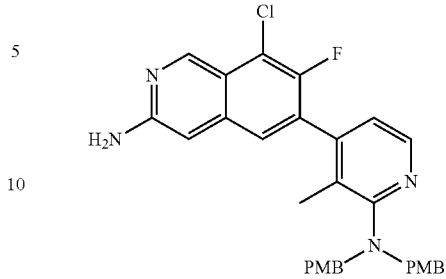

A mixture of 8-chloro-7-fluoro-6-iodo-isoquinolin-3-amine (400 mg, 1.24 mmol), 2-[bis[(4-methoxyphenyl)methyl]amino]-3-methyl-4-pyridyl]boronic acid (729.76 mg, 1.86 mmol), potassium carbonate (376.55 mg, 2.73 mmol), [1,1'-bis(diphenylphosphino)ferrocene]dichloropalladium(II) (90.79 mg, 0.12 mmol) in 1,4-dioxane (10 mL) and water (1 mL) was stirred for 2 hours at 90° C. After filtration, the filtrate was concentrated under reduced pressure. The residue was purified by flash chromatography on silica gel eluting with ethyl acetate/petroleum ether (1/1) to afford 6-[2-[bis[(4-methoxyphenyl)methyl]amino]-3-methyl-4-pyridyl]-8-chloro-7-fluoro-isoquinolin-3-amine (480 mg, 0.88 mmol) as a yellow solid. LCMS (ESI) [M+H]$^+$=543.

Step 4: 2-(6-(2-(bis(4-methoxybenzyl)amino)-3-methylpyridin-4-yl)-8-chloro-7-fluoroisoquinolin-3-ylamino)-6-(2,2-difluoroethyl)-5,6-dihydro-4H-pyrazolo[1,5-g][1,4]diazepin-7(8H)-one

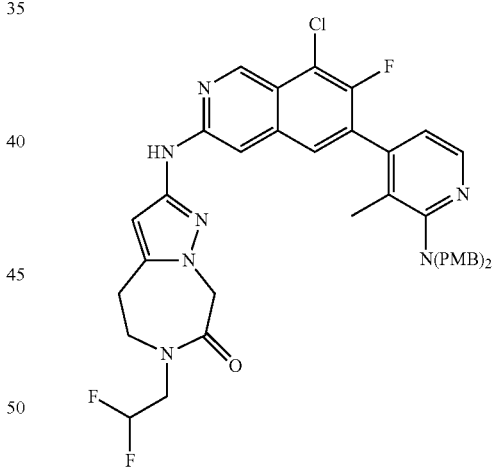

A mixture of 2-bromo-6-(2,2-difluoroethyl)-5,8-dihydro-4H-pyrazolo[1,5-d][1,4]diazepin-7-one (100.19 mg, 0.34 mmol), 6-[2-[bis[(4-methoxyphenyl)methyl]amino]-3-methyl-4-pyridyl]-8-chloro-7-fluoro-isoquinolin-3-amine (185 mg, 0.34 mmol), tris(dibenzylideneacetone)dipalladium-chloroformadduct (70.52 mg, 0.07 mmol), 4,5-bis(diphenylphosphino)-9,9-dimethylxanthene (59.18 mg, 0.10 mmol) and cesium carbonate (222.12 mg, 0.68 mmol) in 1,4-dioxane (10 mL) was stirred for 12 hours at 90° C. After filtration, the filtrate was concentrated under reduced pressure. The residue was purified by flash chromatography on silica gel eluting with ethyl acetate/petroleum ether (7/3) to afford 2-[[6-[2-[bis[(4-methoxyphenyl)methyl]amino]-3-methyl-4-pyridyl]-8-chloro-7-fluoro-3-isoquinolyl]amino]-

6-(2,2-difluoroethyl)-5,8-dihydro-4H-pyrazolo[1,5-d][1,4]diazepin-7-one (90 mg, 0.12 mmol) as a yellow solid. LCMS (ESI) [M+H]⁺=756.

Step 5: tert-butyl 6-(2-(bis(4-methoxybenzyl)amino)-3-methylpyridin-4-yl)-3-(6-(2,2-difluoroethyl)-7-oxo-5,6,7,8-tetrahydro-4H-pyrazolo[1,5-g][1,4]diazepin-2-ylamino)-7-fluoroisoquinolin-8-ylcarbamate

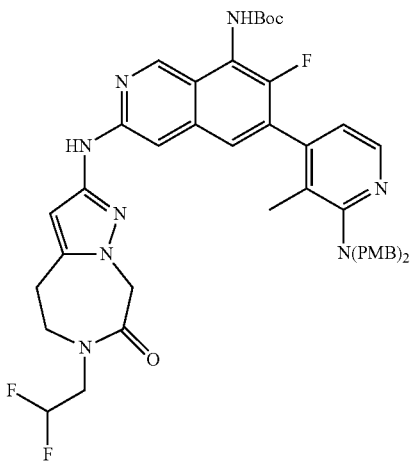

A mixture of 2-[[6-[2-[bis[(4-methoxyphenyl)methyl]amino]-3-methyl-4-pyridyl]-8-chloro-7-fluoro-3-isoquinolyl]amino]-6-(2,2-difluoroethyl)-5,8-dihydro-4H-pyrazolo[1,5-d][1,4]diazepin-7-one (150 mg, 0.20 mmol), tert-butyl carbamate (696.23 mg, 5.95 mmol), tris(dibenzylideneacetone)dipalladium-chloroformadduct (41.06 mg, 0.040 mmol), Brettphos (21.3 mg, 0.040 mmol) and cesium carbonate (258.65 mg, 0.79 mmol) in 1,4-dioxane (15 mL) was stirred for 3 hours at 90° C. After filtration, the filtrate was concentrated under reduced pressure. The residue was purified by flash chromatography on silica gel eluting with ethyl acetate/petroleum ether (9/1) to afford tert-butyl N-[6-[2-[bis[(4-methoxyphenyl)methyl]amino]-3-methyl-4-pyridyl]-3-[[6-(2,2-difluoroethyl)-7-oxo-5,8-dihydro-4H-pyrazolo[1,5-d][1,4]diazepin-2-yl]amino]-7-fluoro-8-isoquinolyl]carbamate (110 mg, 0.13 mmol) as a yellow solid. LCMS (ESI) [M+H]⁺=457.2.

Step 6: 2-(8-amino-6-(2-amino-3-methylpyridin-4-yl)-7-fluoroisoquinolin-3-ylamino)-6-(2,2-difluoroethyl)-5,6-dihydro-4H-pyrazolo[1,5-][1,4]diazepin-7(8H-one

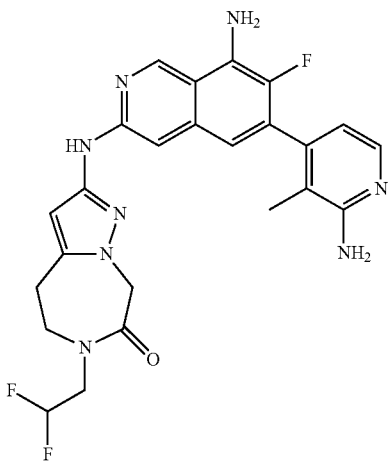 [SMILES: Cc1c(-c2cc3cc(Nc4cc5n(n4)CC(=O)N(CC(F)F)CC5)ncc3c(N)c2F)ccnc1N]

A solution of tert-butyl N-[6-[2-[bis[(4-methoxyphenyl)methyl]amino]-3-methyl-4-pyridyl]-3-[[6-(2,2-difluoroethyl)-7-oxo-5,8-dihydro-4H-pyrazolo[1,5-d][1,4]diazepin-2-yl]amino]-7-fluoro-8-isoquinolyl]carbamate (110.0 mg, 0.13 mmol) in 2,2,2-trifluoroacetic acid (10 mL) was stirred at 25° C. for 5 hours. The mixture was concentrated under vacuum. The crude product was purified by Prep-HPLC (Atlantis HILIC OBD, 19×150 mm 5 um; water (10 mmol/L sodium bicarbonate): CH₃CN=27%-42% B in 7 min) to afford 2-[[8-amino-6-(2-amino-3-methyl-4-pyridyl)-7-fluoro-3-isoquinolyl]amino]-6-(2,2-difluoroethyl)-5,8-dihydro-4H-pyrazolo[1,5-d][1,4]diazepin-7-one (18.3 mg, 0.037 mmol) as a yellow solid. LCMS (ESI) [M+H]⁺=497.2; ¹H NMR (400 MHz, DMSO-d₆) δ 9.25 (s, 1H), 9.09 (s, 1H), 7.85 (d, J=5.1 Hz, 1H), 7.71 (s, 1H), 6.69 (d, J=6.0 Hz, 1H), 6.47 (d, J=5.1 Hz, 1H), 6.34-6.02 (m, 3H), 5.99 (s, 1H), 5.82 (s, 2H), 5.05 (s, 2H), 3.95 (t, J=5.7 Hz, 2H), 3.85 (td, J=15.5, 4.0 Hz, 2H), 3.10-3.02 (m, 2H), 1.90 (d, J=1.3 Hz, 3H).

Example 187

2-(8-amino-6-(5-amino-4-methylpyridin-3-yl)-7-fluoroisoquinolin-3-ylamino)-5-methyl-4,5-dihydropyrazolo[1,5-a]pyrazin-6(7H)-one (Compound 302)

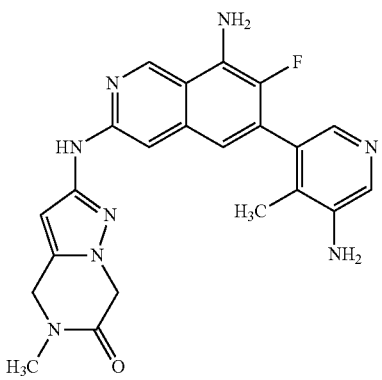 [SMILES: Cc1c(N)cncc1-c1cc2cc(Nc3cc4n(n3)CC(=O)N(C)C4)ncc2c(N)c1F]

Step 1: methyl 2-(3-bromo-5-methyl-1H-pyrazol-1-yl)acetate

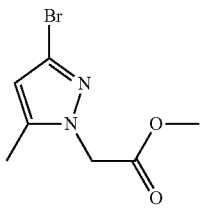

A solution of 3-bromo-5-methyl-1h-pyrazole (500.0 mg, 3.11 mmol), methyl chloroacetate (505.53 mg, 4.66 mmol), tetrabutylammonium iodide (57.3 mg, 0.16 mmol) and potassium carbonate (771.43 mg, 5.59 mmol) in tetrahydrofuran (10 mL) was stirred for 12 h at 20° C. The mixture was concentrated under vacuum. The residue was purified by flash chromatography on silica gel eluting with dichloromethane/methanol (98/2) to afford methyl 2-(3-bromo-5-methyl-pyrazol-1-yl)acetate (671 mg, 2.88 mmol) as a white solid. LC/MS (ESI) [M+H]+=233.

Step 2: methyl 2-(3-bromo-5-(bromomethyl)-1H-pyrazol-1-yl)acetate

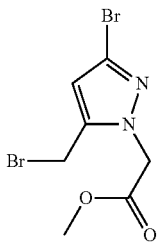

A solution of methyl 2-(3-bromo-5-methyl-pyrazol-1-yl)acetate (20 g, 85.81 mmol), 2,2'-Azobis(2-methylpropionitrile)(1.41 g, 8.58 mmol), 1-bromo-2,5-pyrrolidinedione (16.80 g, 94.4 mmol) in carbon tetrachloride (400 mL) was stirred at 80° C. for 2 hours. The resulting mixture was concentrated under vacuum. The residue was purified by flash chromatography on silica gel eluting with ethyl acetate/petroleum ether (4/1) to afford methyl 2-[3-bromo-5-(bromomethyl)pyrazol-1-yl]acetate (20 g, 64.11 mmol) as a yellow solid. LCMS (ESI) [M+H]+=311.

Step 3: 2-bromo-5-methyl-4,5-dihydropyrazolo[1,5-a]pyrazin-6(7H)-one

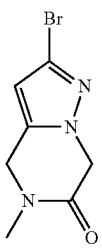

A solution of methyl 2-[3-bromo-5-(bromomethyl)pyrazol-1-yl]acetate (900 mg, 2.88 mmol) and methanamine (896.08 mg, 28.85 mmol) in tetrahydrofuran (10 mL) was stirred at 25° C. for 2 hours. The mixture was concentrated under vacuum. The residue was purified by flash chromatography on silica gel eluting with ethyl acetate/petroleum ether (4/1) to afford 2-bromo-5-methyl-4,7-dihydropyrazolo[1,5-a]pyrazin-6-one (460 mg, 2.00 mmol) as a white solid. LC/MS (ESI) [M+H]+=230.

Step 4: tert-butyl N-tert-butoxycarbonyl-N-[5-[8-chloro-7-fluoro-3-[(5-methyl-6-oxo-4,7-dihydropyrazolo[1,5-a]pyrazin-2-yl)amino]-6-isoquinolyl]-4-methyl-3-pyridyl]carbamate

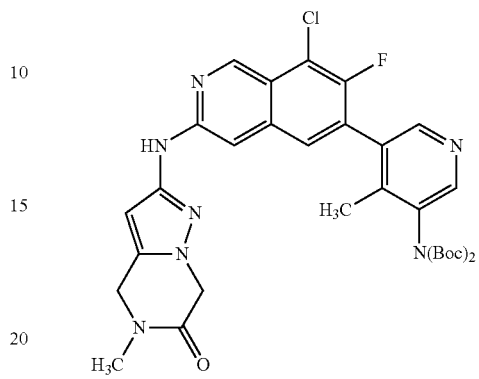

A mixture of 2-bromo-5-methyl-4,7-dihydropyrazolo[1,5-a]pyrazin-6-one (219.55 mg, 0.95 mmol), tert-butyl N-[5-(3-amino-8-chloro-7-fluoro-6-isoquinolyl)-4-methyl-3-pyridyl]-N-tert-butoxycarbonyl-carbamate (400.0 mg, 0.80 mmol), tris(dibenzylideneacetone)dipalladium-chloroform adduct (164.62 mg, 0.16 mmol), 4,5-bis(diphenylphosphino)-9,9-dimethylxanthene (138.14 mg, 0.24 mmol) and cesium carbonate (518.52 mg, 1.59 mmol) in 1,4-dioxane (60 mL) was stirred for 12 hours at 100° C. After filtration, the filtrate was concentrated under reduced pressure. The residue was purified by flash chromatography on silica gel eluting with ethyl acetate/petroleum ether (10:1) to afford tert-butyl N-tert-butoxycarbonyl-N-[5-[8-chloro-7-fluoro-3-[(5-methyl-6-oxo-4,7-dihydropyrazolo[1,5-a]pyrazin-2-yl)amino]-6-isoquinolyl]-4-methyl-3-pyridyl]carbamate (340 mg, 0.52 mmol) as a yellow solid. LCMS (ESI) [M+H]+=652.

Step 5: tert-butyl N-tert-butoxycarbonyl-N-[5-[8-(tert-butoxycarbonylamino)-7-fluoro-3-[(5-methyl-6-oxo-4,7-dihydropyrazolo[1,5-a]pyrazin-2-yl)amino]-6-isoquinolyl]-4-methyl-3-pyridyl]carbamate

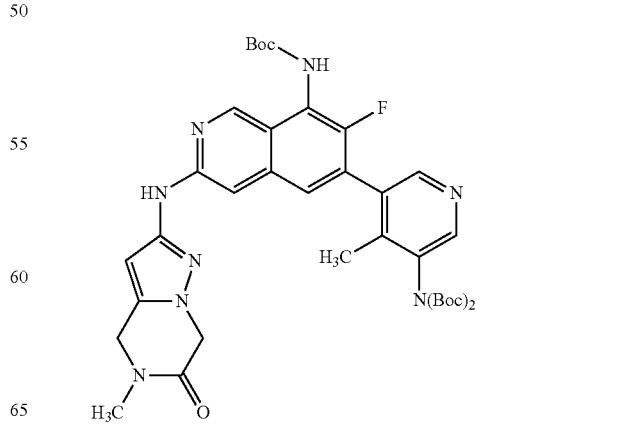

831

A mixture of tert-butyl carbamate (1.83 g, 15.64 mmol), tert-butyl N-tert-butoxycarbonyl-N-[5-[8-chloro-7-fluoro-3-[(5-methyl-6-oxo-4,7-dihydropyrazolo[1,5-a]pyrazin-2-yl)amino]-6-isoquinolyl]-4-methyl-3-pyridyl]carbamate (340.0 mg, 0.52 mmol), tris(dibenzylideneacetone)dipalladium-chloroformadduct (107.92 mg, 0.10 mmol), Bretthpos (56.0 mg, 0.10 mmol) and cesium carbonate (679.87 mg, 2.09 mmol) in 1,4-dioxane (10 mL) was stirred for 3 hours at 90° C. After filtration, the filtrate was concentrated under reduced pressure. The residue was purified by flash chromatography on silica gel eluting with methanol/dichloromethane (12/88) to afford tert-butyl N-tert-butoxycarbonyl-N-[5-[8-(tert-butoxycarbonylamino)-7-fluoro-3-[(5-methyl-6-oxo-4,7-dihydropyrazolo[1,5-a]pyrazin-2-yl)amino]-6-isoquinolyl]-4-methyl-3-pyridyl]carbamate (250 mg, 0.34 mmol) as a yellow solid. LCMS (ESI) [M+H]$^+$=733.

Step 6: 2-(8-amino-6-(5-amino-4-methylpyridin-3-yl)-7-fluoroisoquinolin-3-ylamino)-5-methyl-4,5-dihydropyrazolo[1,5-a]pyrazin-6(7H)-one

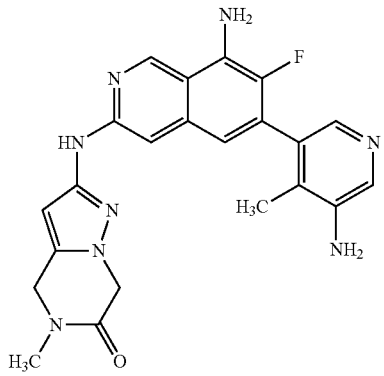 [SMILES: Cc1c(N)cncc1-c1cc2cc(Nc3cc4n(n3)CC(=O)N(C)C4)ncc2c(N)c1F]

A solution of tert-butyl N-tert-butoxycarbonyl-N-[5-[8-(tert-butoxycarbonylamino)-7-fluoro-3-[(5-methyl-6-oxo-4,7-dihydropyrazolo[1,5-a]pyrazin-2-yl)amino]-6-isoquinolyl]-4-methyl-3-pyridyl]carbamate (240.0 mg, 0.33 mmol) in 2,2,2-trifluoroacetic acid (20 mL) was stirred at 25° C. for 2 hours. The mixture was concentrated under vacuum. The crude product was purified by Prep-HPLC (Atlantis HILIC OBD, 19×150 mm Sum; water (10 mmol/L): CH$_3$CN=15%-35% B in 7 min) to afford 2-[[8-amino-6-(5-amino-4-methyl-3-pyridyl)-7-fluoro-3-isoquinolyl]amino]-5-methyl-4,7-dihydropyrazolo[1,5-a]pyrazin-6-one (49 mg, 0.11 mmol) as a yellow solid. LCMS (ESI) [M+H]$^+$=433.3; $^1$H NMR (400 MHz, DMSO-d$_6$) δ 9.27 (s, 1H), 9.20 (s, 1H), 7.99 (s, 1H), 7.68 (d, J=2.5 Hz, 2H), 6.67 (d, J=6.0 Hz, 1H), 6.08 (s, 2H), 6.05 (s, 1H), 5.24 (s, 2H), 4.67 (s, 2H), 4.60 (s, 2H), 3.01 (s, 3H), 1.93 (d, J=1.5 Hz, 3H).

832

Example 188

(E)-2-((8-amino-7-fluoro-6-(4-methylpyridin-3-yl)isoquinolin-3-yl)amino)-6-methyl-4-((1-methyl-1H-pyrazol-4-yl)methylene)-5,6-dihydro-4H-pyrazolo[1,5-d][1,4]diazepin-7(8H)-one (Compound 303)

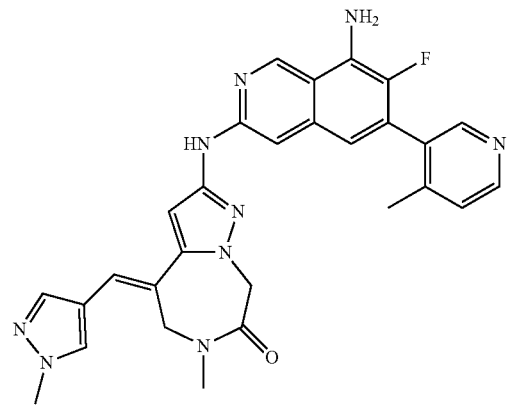 [SMILES: Cc1ccncc1-c1cc2cc(Nc3cc4n(n3)CC(=O)N(C)C/C4=C\c3cnn(C)c3)ncc2c(N)c1F]

Step 1: (E)-3-(1-methylpyrazol-4-yl)prop-2-en-1-ol

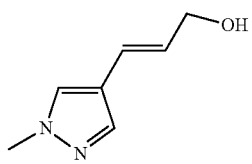

A solution of tert-butyl (E)-3-(1-methylpyrazol-4-yl)prop-2-enoate (3.0 g, 14.41 mmol) and DIBAL-H (43.0 mL, 43.22 mmol) in dichloromethane (100 mL) was stirred at 0° C. for 1 hour. The reaction was quenched by adding methanol. After filtration, the filtrate was concentrated under vacuum. The residue was purified by flash chromatography on silica gel eluting with dichloromethane/methanol (10/1) to afford (E)-3-(1-methylpyrazol-4-yl)prop-2-en-1-ol (800 mg, 5.79 mmol) as a colorless oil. LCMS (ESI) [M+H]$^+$=139.

Step 2: (E)-3-(1-methylpyrazol-4-yl)prop-2-enal

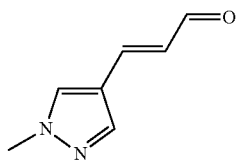

A solution of (E)-3-(1-methylpyrazol-4-yl)prop-2-en-1-ol (897 mg, 6.49 mmol) and Dess-Martin periodinane (2.75 g, 6.49 mmol) in dichloromethane (30 mL) was stirred at 20° C. for 1 hour. The mixture was concentrated under vacuum. The residue was purified by flash chromatography on silica gel eluting with dichloromethane/methanol (95/5) to afford (E)-3-(1-methylpyrazol-4-yl)prop-2-enal (800 mg, 5.87 mmol) as a yellow oil. LCMS (ESI) [M+H]$^+$=137.

Step 3: (E)-N-methyl-3-(1-methylpyrazol-4-yl)prop-2-en-1-amine

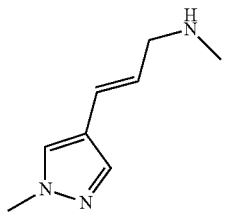

A solution of (E)-3-(1-methylpyrazol-4-yl)prop-2-enal (794.0 mg, 5.83 mmol) and methanamine (543.41 mg, 17.5 mmol) in tetrahydrofuran (20 mL) was stirred at 20° C. for 30 min. Methanol (10 mL) and sodium borohydride (664.83 mg, 17.5 mmol) were added and stirred at 20° C. for 1 hour. The mixture was concentrated under vacuum. The crude product was purified by reverse phase (C18; water (10 mmol/L sodium bicarbonate) and MeOH (5%-25%)) to afford (E)-N-methyl-3-(1-methylpyrazol-4-yl)prop-2-en-1-amine (412 mg, 2.72 mmol) as a colorless oil LCMS (ESI) [M+H]$^+$=152.

Step 4: 2-(3,5-dibromopyrazol-1-yl)-N-methyl-N—[(E)-3-(1-methylpyrazol-4-yl)allyl]acetamide

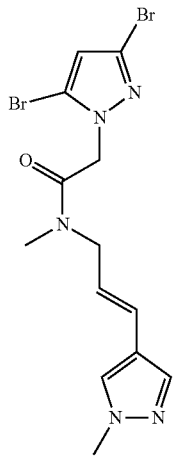 [SMILES: CN(C/C=C/c1cnn(C)c1)C(=O)Cn1nc(Br)cc1Br]

A solution of 2-(3,5-dibromopyrazol-1-yl)acetic acid (770 mg, 2.71 mmol), (E)-N-methyl-3-(1-methylpyrazol-4-yl) prop-2-en-1-amine (410.1 mg, 2.71 mmol) and N,N-diisopropylethylamine (1.05 g, 8.14 mmol) in N,N-dimethylformamide (15 mL) was stirred at 25° C. for 5 min. 2-(7-Azabenzotriazol-1-yl)-N,N,N',N'-tetramethyluronium hexafluorophosphate (1.55 g, 4.07 mmol) was added and stirred at 25° C. for 12 hours. The reaction mixture was diluted with ethyl acetate and then washed with water. The organic phase was dried with anhydrous sodium sulfate. After filtration, the filtrate was concentrated under vacuum. The residue was purified by reverse phase column (C18; Water (10 mmol/L sodium bicarbonate) and MeOH (5%-70%) in 20 mins) to afford 2-(3,5-dibromopyrazol-1-yl)-N-methyl-N—[(E)-3-(1-methylpyrazol-4-yl)allyl]acetamide (852 mg, 2.04 mmol) as a colorless oil. LCMS (ESI) [M+H]$^+$=416.

Step 5: (4E)-2-bromo-6-methyl-4-[(1-methylpyrazol-4-yl)methylene]-5,8-dihydropyrazolo[1,5-d][1,4] diazepin-7-one

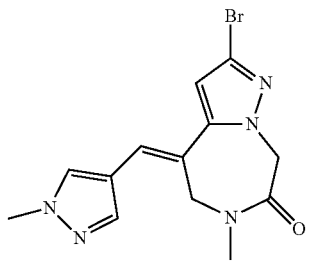 [SMILES: CN1C/C(=C\c2cnn(C)c2)c2cc(Br)nn2CC1=O]

A mixture of 2-(3,5-dibromopyrazol-1-yl)-N-methyl-N—[(E)-3-(1-methylpyrazol-4-yl)allyl]acetamide (817 mg, 1.96 mmol), palladium acetate (43.88 mg, 0.20 mmol), triphenylphosphine (102.64 mg, 0.39 mmol), tetrabutylammonium bromide (630.72 mg, 1.96 mmol) and potassium acetate (575.88 mg, 5.88 mmol) in N,N-dimethylformamide (10 mL) was stirred at 90° C. for 12 hours. After filtration, the filtrate was concentrated under vacuum. The residue was purified by flash chromatography on silica gel eluting with dichloromethane/methanol (10/1) to afford (4E)-2-bromo-6-methyl-4-[(1-methylpyrazol-4-yl)methylene]-5,8-dihydropyrazolo[1,5-d][1,4]diazepin-7-one (540 mg, 1.61 mmol) as a yellow solid. LCMS (ESI) [M+H]$^+$=336.

Step 6: (4Z)-2-[[8-chloro-7-fluoro-6-(4-methyl-3-pyridyl)-3-isoquinolyl]amino]-6-methyl-4-[(1-methylpyrazol-4-yl)methylene]-5,8-dihydropyrazolo[1,5-d][1,4]diazepin-7-one

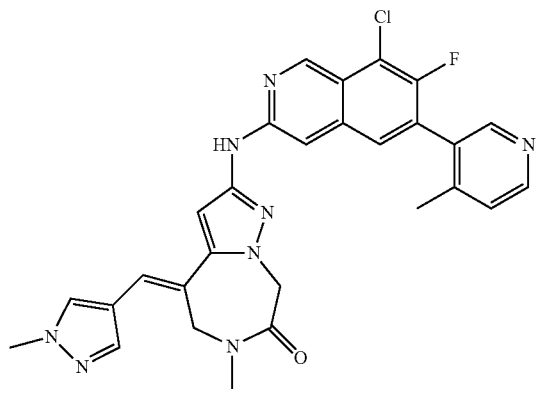 [SMILES: Cc1ccncc1-c1cc2cc(Nc3cc4n(n3)CC(=O)N(C)C/C4=C\c3cnn(C)c3)ncc2c(Cl)c1F]

A mixture of (4E)-2-bromo-6-methyl-4-[(1-methylpyrazol-4-yl)methylene]-5,8-dihydropyrazolo[1,5-d][1,4]diazepin-7-one (520 mg, 1.55 mmol), 8-chloro-7-fluoro-6-(4-methyl-3-pyridyl)isoquinolin-3-amine (445.03 mg, 1.55 mmol), tBuBrettphos Pd G3 (528.37 mg, 0.62 mmol), tBu-Brettphos (374.31 mg, 0.77 mmol) and cesium carbonate (1512.72 mg, 4.64 mmol) in 1,4-dioxane (20 mL) was stirred at 130° C. for 1 hour. The residue was purified by flash chromatography on silica gel eluting with dichloromethane/methanol (10/1) to afford (4Z)-2-[[8-chloro-7-fluoro-6-(4-methyl-3-pyridyl)-3-isoquinolyl]amino]-6-methyl-4-[(1-methylpyrazol-4-yl)methylene]-5,8-dihydropyrazolo[1,5-d][1,4]diazepin-7-one (305 mg, 0.56 mmol) as a yellow solid. LCMS (ESI) [M+H]$^+$=543.

Step 7: tert-butyl N-[7-fluoro-3-[[(4Z)-6-methyl-4-[(1-methylpyrazol-4-yl)methylene]-7-oxo-5,8-dihydropyrazolo[1,5-d][1,4]diazepin-2-yl]amino]-6-(4-methyl-3-pyridyl)-8-isoquinolyl]carbamate

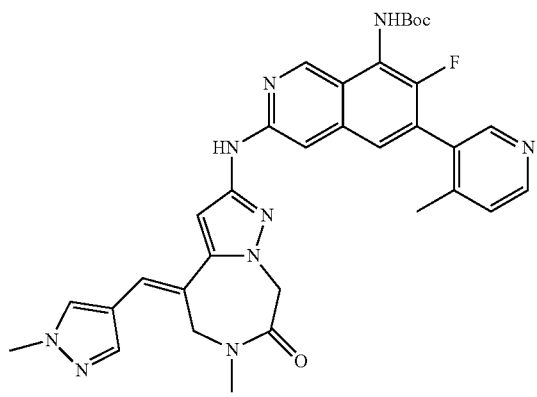 [SMILES: Cc1ccncc1-c1cc2cc(Nc3cc4n(n3)CC(=O)N(C)C/C4=C\c3cnn(C)c3)ncc2c(NC(=O)OC(C)(C)C)c1F]

A mixture of (4Z)-2-[[8-chloro-7-fluoro-6-(4-methyl-3-pyridyl)-3-isoquinolyl]amino]-6-methyl-4-[(1-methylpyrazol-4-yl)methylene]-5,8-dihydropyrazolo[1,5-d][1,4]diazepin-7-one (300 mg, 0.55 mmol), tert-butyl carbamate (1.62 g, 13.81 mmol), tris(dibenzylideneacetone)dipalladium-chloroformadduct (114.37 mg, 0.11 mmol), Brettphos (88.84 mg, 0.17 mmol) and cesium carbonate (540.34 mg, 1.66 mmol) in 1,4-dioxane (15 mL) was stirred at 90° C. for 2 hours. After filtration, the filtrate was concentrated under vacuum. The residue was purified by flash chromatography on silica gel eluting with dichloromethane/methanol (10/1) to afford tert-butyl N-[7-fluoro-3-[[(4Z)-6-methyl-4-[(1-methylpyrazol-4-yl)methylene]-7-oxo-5,8-dihydropyrazolo[1,5-d][1,4]diazepin-2-yl]amino]-6-(4-methyl-3-pyridyl)-8-isoquinolyl]carbamate (100 mg, 0.16 mmol) as a light yellow solid. LCMS (ESI) [M+H]$^+$=624.

Step 8: (4E)-2-[[8-amino-7-fluoro-6-(4-methyl-3-pyridyl)-3-isoquinolyl]amino]-6-methyl-4-[(1-methylpyrazol-4-yl)methylene]-5,8-dihydropyrazolo[1,5-d][1,4]diazepin-7-one

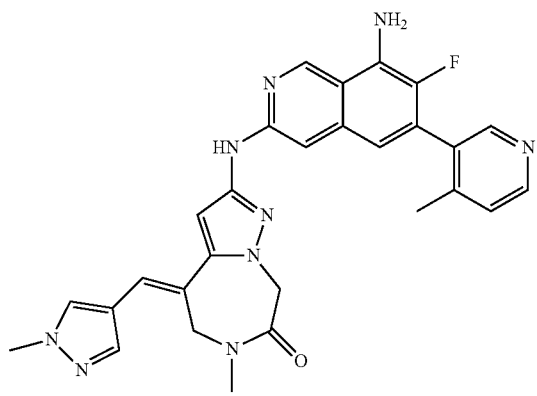

A solution of tert-butyl N-[7-fluoro-3-[[(4E)-6-methyl-4-[(1-methylpyrazol-4-yl)methylene]-7-oxo-5,8-dihydropyrazolo[1,5-d][1,4]diazepin-2-yl]amino]-6-(4-methyl-3-pyridyl)-8-isoquinolyl]carbamate (95 mg, 0.15 mmol) and 2,2,2-trifluoroacetic acid (3 mL) in dichloromethane (3 mL) was stirred at 20° C. for 1 hour. The reaction solution was concentrated under vacuum. The crude product was purified by Prep-HPLC with the following conditions (xBridge Prep C18 OBD Column19×150 nm]; water (10 mmol/L sodium bicarbonate) and ACN (20%-45%) in 7 min) to afford (4E)-2-[[8-amino-7-fluoro-6-(4-methyl-3-pyridyl)-3-isoquinolyl]amino]-6-methyl-4-[(1-methylpyrazol-4-yl)methylene]-5,8-dihydropyrazolo[1,5-d][1,4]diazepin-7-one (13.5 mg, 0.026 mmol) as a yellow solid. LCMS (ESI) [M+H]$^+$=524; $^1$HNMR (400 MHz, DMSO-d$_6$) δ 9.31 (s, 1H), 9.20 (s, 1H), 8.50 (d, J=6.0 Hz, 1H), 8.44 (s, 1H), 8.09 (s, 1H), 7.77 (s, 1H), 7.68 (s, 1H), 7.39 (d, J=6.0 Hz, 1H), 7.00 (s, 1H), 6.80 (d, J=6.0 Hz, 1H), 6.50 (s, 1H), 6.14 (s, 2H), 5.10 (s, 2H), 4.68 (s, 2H), 3.89 (s, 3H), 2.90 (s, 3H), 2.23 (s, 3H).

Example 189

2-((8-amino-6-(5-amino-4-methylpyridin-3-yl)-7-fluoroisoquinolin-3-yl)amino)-6-(2,2,2-trifluoroethyl)-5,6-dihydro-4H-pyrazolo[1,5-d][1,4]diazepin-7(8H)-one (Compound 305)

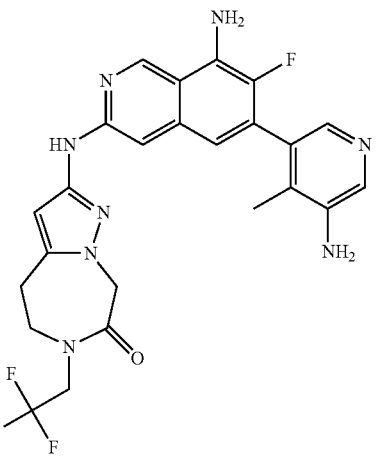

Step 1: 2-bromo-6-(2,2,2-trifluoroethyl)-5,8-dihydro-4H-pyrazolo[1,5-d][1,4]diazepin-7-one

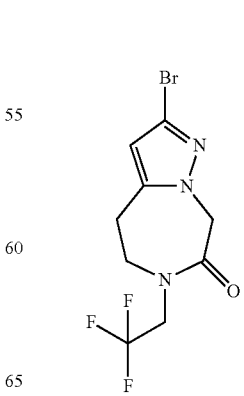

To a mixture of 2-bromo-4,5,6,8-tetrahydropyrazolo[1,5-d][1,4]diazepin-7-one (600 mg, 2.61 mmol) in N,N-dimethylformamide (25 mL) was added sodium hydride (187.78 mg, 60% purity, 4.69 mmol) at 0° C. The reaction was stirred at 0° C. for 30 min before 2,2,2-trifluoroethyl trifluoromethanesulfonate (3.03 g, 13.04 mmol) in tetrahydrofuran was added at 0° C. The reaction was stirred at room temperature for 3 hours before concentrated under vacuum. The residue was purified directly by a reversed phase column with 0.5% sodium bicarbonate solution/methanol (60%) to afford 2-bromo-6-(2,2,2-trifluoroethyl)-5,8-dihydro-4H-pyrazolo[1,5-d][1,4]diazepin-7-one (500 mg, 1.60 mmol) as a light yellow solid. LCMS (ESI) [M+H]$^+$=312.

Step 2: tert-butyl N-tert-butoxycarbonyl-N-[5-[8-chloro-7-fluoro-3-[[7-oxo-6-(2,2,2-trifluoroethyl)-5,8-dihydro-4H-pyrazolo[1,5-d][1,4]diazepin-2-yl]amino]-6-isoquinolyl]-4-methyl-3-pyridyl]carbamate

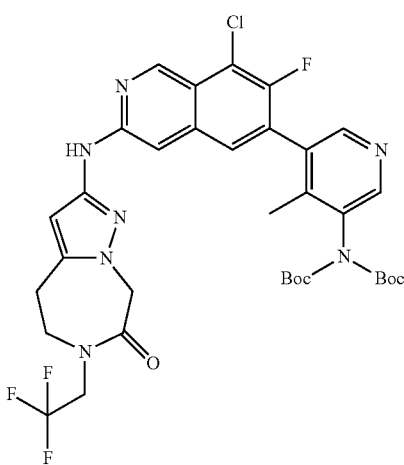 [SMILES: Cc1c(-c2cc3cc(Nc4cc5n(n4)CC(=O)N(CC(F)(F)F)CC5)ncc3c(Cl)c2F)cncc1N(C(=O)OC(C)(C)C)C(=O)OC(C)(C)C]

A mixture of 2-bromo-6-(2,2,2-trifluoroethyl)-5,8-dihydro-4H-pyrazolo[1,5-d][1,4]diazepin-7-one (250 mg, 0.80 mmol), tert-butyl N-[5-(3-amino-8-chloro-7-fluoro-6-isoquinolyl)-4-methyl-3-pyridyl]-N-tert-butoxycarbonyl-carbamate (402.9 mg, 0.80 mmol), tris(dibenzylideneacetone)dipalladium (165.82 mg, 0.16 mmol), 4,5-bis(diphenylphosphino)-9,9-dimethylxanthene (185.2 mg, 0.32 mmol) and cesium carbonate (783.43 mg, 2.40 mmol) in 1,4-dioxane (60 mL) was stirred at 100° C. for 4 hours. The mixture was concentrated under vacuum. The residue was purified by flash chromatography on silica gel eluting with petroleum ether/ethyl acetate (2/3) to afford tert-butyl N-tert-butoxycarbonyl-N-[5-[8-chloro-7-fluoro-3-[[7-oxo-6-(2,2,2-trifluoroethyl)-5,8-dihydro-4H-pyrazolo[1,5-d][1,4]diazepin-2-yl]amino]-6-isoquinolyl]-4-methyl-3-pyridyl]carbamate (200 mg, 0.27 mmol) as a yellow solid. LCMS (ESI) [M+H]$^+$=734.

Step 3: tert-butyl N-tert-butoxycarbonyl-N-[5-[8-(tert-butoxycarbonylamino)-7-fluoro-3-[[7-oxo-6-(2,2,2-trifluoroethyl)-5,8-dihydro-4H-pyrazolo[1,5-d][1,4]diazepin-2-yl]amino]-6-isoquinolyl]-4-methyl-3-pyridyl]carbamate

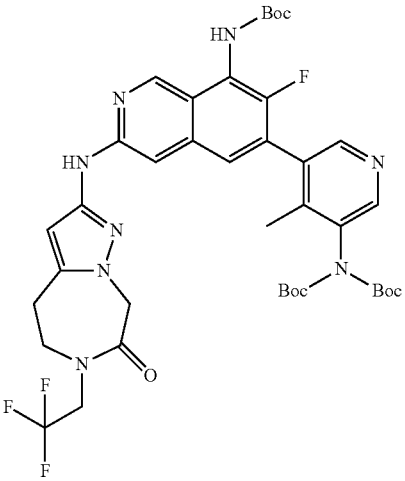 [SMILES: Cc1c(-c2cc3cc(Nc4cc5n(n4)CC(=O)N(CC(F)(F)F)CC5)ncc3c(NC(=O)OC(C)(C)C)c2F)cncc1N(C(=O)OC(C)(C)C)C(=O)OC(C)(C)C]

A mixture of tert-butyl N-tert-butoxycarbonyl-N-[5-[8-chloro-7-fluoro-3-[[7-oxo-6-(2,2,2-trifluoroethyl)-5,8-dihydro-4H-pyrazolo[1,5-d][1,4]diazepin-2-yl]amino]-6-isoquinolyl]-4-methyl-3-pyridyl]carbamate (280 mg, 0.38 mmol), tert-butyl carbamate (1.12 g, 9.53 mmol), tris(dibenzylideneacetone)dipalladium (78.95 mg, 0.080 mmol), Brettphos (81.77 mg, 0.15 mmol) and cesium carbonate (621.68 mg, 1.91 mmol) in 1,4-dioxane (20 mL) was stirred at 90° C. for 2 hours. The mixture was concentrated under vacuum. The residue was purified by flash chromatography on silica gel eluting with dichloromethane/methanol (97/3) to afford tert-butyl N-tert-butoxycarbonyl-N-[5-[8-(tert-butoxycarbonylamino)-7-fluoro-3-[[7-oxo-6-(2,2,2-trifluoroethyl)-5,8-dihydro-4H-pyrazolo[1,5-d][1,4]diazepin-2-yl]amino]-6-isoquinolyl]-4-methyl-3-pyridyl]carbamate (120 mg, 0.15 mmol) as a yellow solid. LCMS (ESI) [M+H]$^+$=815.

Step 4: 2-[[8-amino-6-(5-amino-4-methyl-3-pyridyl)-7-fluoro-3-isoquinolyl]amino]-6-(2,2,2-trifluoroethyl)-5,8-dihydro-4H-pyrazolo[1,5-d][1,4]diazepin-7-one

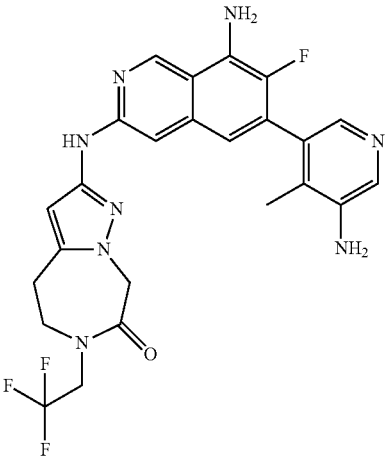 [SMILES: Cc1c(N)cncc1-c1cc2cc(Nc3cc4n(n3)CC(=O)N(CC(F)(F)F)CC4)ncc2c(N)c1F]

A solution of tert-butyl N-tert-butoxycarbonyl-N-[5-[8-(tert-butoxycarbonylamino)-7-fluoro-3-[[7-oxo-6-(2,2,2-trifluoroethyl)-5,8-dihydro-4H-pyrazolo[1,5-d][1,4]diazepin-2-yl]amino]-6-isoquinolyl]-4-methyl-3-pyridyl]carbamate (110 mg, 0.13 mmol) and 2,2,2-trifluoroacetic acid (2 mL) in dichloromethane (2 mL) was stirred at 25° C. for 1 hour. The mixture was concentrated under vacuum. The residue was adjusted to pH 10 with ammonia in methanol (7 mol/L). The residue was purified by Prep-HPLC (SunFire Prep C18 OBD Column 19×150 mm 5 um 10 nm; Water (0.1% FA): CAN=22% B to 36% B in 10 min; 25 mL/min) to afford 2-[[8-amino-6-(5-amino-4-methyl-3-pyridyl)-7-fluoro-3-isoquinolyl]amino]-6-(2,2,2-trifluoroethyl)-5,8-dihydro-4H-pyrazolo[1,5-d][1,4]diazepin-7-one (47.4 mg, 0.092 mmol) as a yellow solid. LCMS (ESI) [M+H]+=515.2; 1HNMR (300 MHz, DMSO-d6) δ 9.26 (s, 1H), 9.11 (s, 1H), 7.99 (s, 1H), 7.73 (s, 1H), 7.68 (s, 1H), 6.73 (d, J=6.1 Hz, 1H), 6.07 (s, 2H), 6.01 (s, 1H), 5.23 (s, 2H), 5.10 (s, 2H), 4.34-4.24 (m, 2H), 4.00-3.98 (m, 2H), 3.07-3.05 (m, 2H), 1.94 (s, 3H).

Example 190

2-((8-amino-6-(5-amino-4-chloropyridin-3-yl)-7-fluoroisoquinolin-3-yl)amino)-6-methyl-5,6-dihydro-4H-pyrazolo[1,5-d][1,4]diazepin-7(8H)-one; Formic Acid (Compound 306)

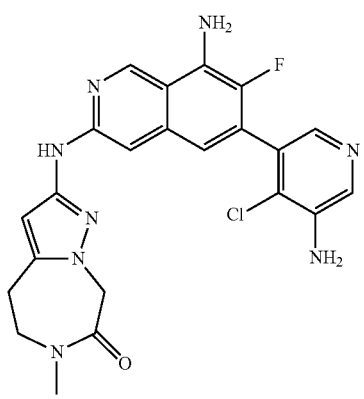

Step 1:
6-benzyloxy-8-chloro-7-fluoro-isoquinolin-3-amine

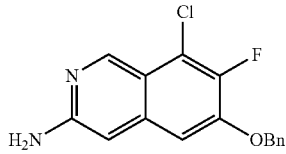 [SMILES: Nc1cc2cc(OCc3ccccc3)c(F)c(Cl)c2cn1]

A mixture of 8-chloro-7-fluoro-6-iodo-isoquinolin-3-amine (100 mg, 0.31 mmol), CuI (23.69 mg, 0.12 mmol), 3,4,7,8-tetramethyl-1,10-phenanthroline (58.62 mg, 0.25 mmol), phenylmethanol (334.87 mg, 3.1 mmol), cesium carbonate (303.25 mg, 0.93 mmol) in N,N-dimethylformamide (2 mL) was stirred for 2 hours at 95° C. The mixture was cooled to ambient temperature. After filtration, the filtrate was concentrated under reduced pressure. The residue was purified by flash chromatography on silica gel eluting with petroleum ether/ethyl acetate (1/2) to afford 6-benzyloxy-8-chloro-7-fluoro-isoquinolin-3-amine (70 mg, 0.23 mmol) as a color solid. LCMS (ESI) [M+H]+=301.1.

Step 2: 2-[(6-benzyloxy-8-chloro-7-fluoro-3-isoquinolyl)amino]-6-methyl-5,8-dihydro-4H-pyrazolo[1,5-d][1,4]diazepin-7-one

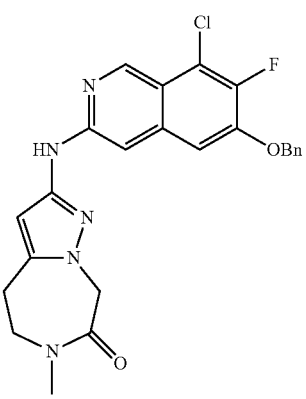 [SMILES: CN1CCc2cc(Nc3cc4cc(OCc5ccccc5)c(F)c(Cl)c4cn3)nn2CC1=O]

A mixture of 2-bromo-6-methyl-5,8-dihydro-4H-pyrazolo[1,5-d][1,4]diazepin-7-one (60 mg, 0.25 mmol), 6-benzyloxy-8-chloro-7-fluoro-isoquinolin-3-amine (74.41 mg, 0.25 mmol), tris(dibenzylideneacetone)dipalladium-chloroformadduct (50.88 mg, 0.05 mmol), 4,5-bis(diphenylphosphino)-9,9-dimethylxanthene (56.83 mg, 0.10 mmol) and cesium carbonate (240.4 mg, 0.74 mmol) in 1,4-dioxane (9.6 mL) was stirred for 12 hours at 100° C. The mixture was cooled to ambient temperature. After filtration, the filtrate was concentrated under reduced pressure. The residue was purified by flash chromatography on silica gel eluting with dichloromethane/methanol (40/1) to afford 2-[(6-benzyloxy-8-chloro-7-fluoro-3-isoquinolyl)amino]-6-methyl-5,8-dihydro-4H-pyrazolo[1,5-d][1,4]diazepin-7-one (65 mg, 0.14 mmol) as a color solid. LCMS (ESI) [M+H]+=466.1.

Step 3: tert-butyl N-[6-benzyloxy-7-fluoro-3-[(6-methyl-7-oxo-5,8-dihydro-4H-pyrazolo[1,5-d][1,4]diazepin-2-yl)amino]-8-isoquinolyl]carbamate

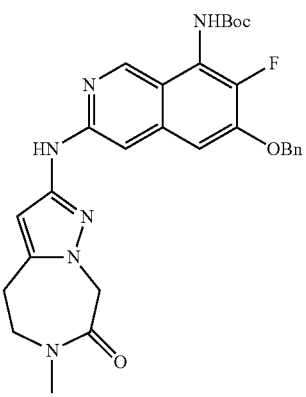 [SMILES: CN1CCc2cc(Nc3cc4cc(OCc5ccccc5)c(F)c(NC(=O)OC(C)(C)C)c4cn3)nn2CC1=O]

A mixture of 2-[(6-benzyloxy-8-chloro-7-fluoro-3-isoquinolyl)amino]-6-methyl-5,8-dihydro-4H-pyrazolo[1,5-d][1, 4]diazepin-7-one (60 mg, 0.13 mmol), tert-butyl carbamate (376.68 mg, 3.22 mmol), tris(dibenzylideneacetone)dipalladium-chloroform adduct (26.66 mg, 0.03 mmol), BrettPhos (20.71 mg, 0.04 mmol) and cesium carbonate (125.95 mg, 0.39 mmol) in 1,4-dioxane (7.5 mL) was stirred at 85° C. for 2 hours under nitrogen. After filtration, the filtrate was concentrated under reduced pressure. The residue was purified by flash chromatography on silica gel eluting with dichloromethane/methanol (20/1) to afford tert-butyl N-[6-benzyloxy-7-fluoro-3-[(6-methyl-7-oxo-5,8-dihydro-4H-pyrazolo[1,5-d][1,4]diazepin-2-yl)amino]-8-isoquinolyl] carbamate (50 mg, 0.092 mmol) as a brown solid. LCMS (ESI) [M+H]$^+$=547.1.

Step 4: tert-butyl N-[7-fluoro-6-hydroxy-3-[(6-methyl-7-oxo-5,8-dihydro-4H-pyrazolo[1,5-d][1,4]diazepin-2-yl)amino]-8-isoquinolyl]carbamate

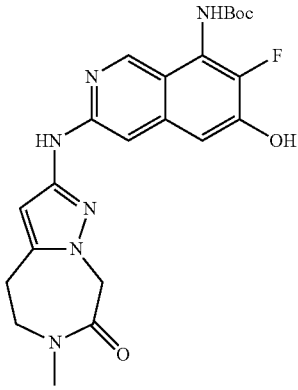 [SMILES: CN1CCc2cc(Nc3cc4cc(O)c(F)c(NC(=O)OC(C)(C)C)c4cn3)nn2CC1=O]

A solution of tert-butyl N-[6-benzyloxy-7-fluoro-3-[(6-methyl-7-oxo-5,8-dihydro-4H-pyrazolo[1,5-d][1,4]diazepin-2-yl)amino]-8-isoquinolyl]carbamate (220 mg, 0.40 mmol) and palladium carbon (40 mg, 0.40 mmol) in methanol (20 mL) was stirred under hydrogen (1 atm) at 25° C. for 4 hours. After filtration, the filtrate was concentrated under vacuum. The residue was purified by flash chromatography on silica gel eluting with dichloromethane/methanol (5/1) to afford tert-butyl N-[7-fluoro-6-hydroxy-3-[(6-methyl-7-oxo-5,8-dihydro-4H-pyrazolo[1,5-d][1,4]diazepin-2-yl)amino]-8-isoquinolyl]carbamate (97.3 mg, 0.21 mmol) as a brown solid. LCMS (ESI) [M+H]$^+$=457.1.

Step 5: [8-(tert-butoxycarbonylamino)-7-fluoro-3-[(6-methyl-7-oxo-5,8-dihydro-4H-pyrazolo[1,5-d][1,4]diazepin-2-yl)amino]-6-isoquinolyl] trifluoromethanesulfonate

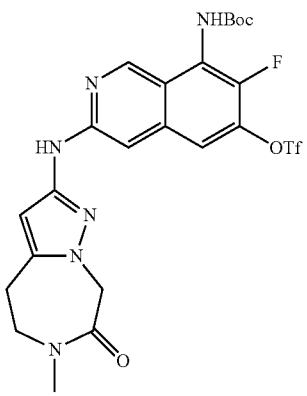 [SMILES: CN1CCc2cc(Nc3cc4cc(OS(=O)(=O)C(F)(F)F)c(F)c(NC(=O)OC(C)(C)C)c4cn3)nn2CC1=O]

To a mixture of [tert-butyl N-[7-fluoro-6-hydroxy-3-[(6-methyl-7-oxo-5,8-dihydro-4H-pyrazolo[1,5-d][1,4]diazepin-2-yl)amino]-8-isoquinolyl]carbamate (550 mg, 1.2 mmol), tert-butyl N-[7-fluoro-6-hydroxy-3-[(6-methyl-7-oxo-5,8-dihydro-4H-pyrazolo[1,5-d][1,4]diazepin-2-yl)amino]-8-isoquinolyl]carbamate (550 mg, 1.2 mmol) in dichloromethane (20 mL) was added triethylamine (243.39 mg, 2.41 mmol) and trifluoromethanesulfonic (509.93 mg, 1.81 mmol) at −60° C. The resulting mixture was stirred for 1 hour at −60° C. The reaction was quenched with water. The resulting mixture was extracted with dichloromethane, dried with anhydrous sodium sulfate. After filtration, the filtrate was concentrated under vacuum to afford[8-(tert-butoxycarbonylamino)-7-fluoro-3-[(6-methyl-7-oxo-5,8-dihydro-4H-pyrazolo[1,5-d][1,4]diazepin-2-yl)amino]-6-isoquinolyl] trifluoromethanesulfonate (670 mg, crude) as a yellow oil. LCMS (ESI) [M+H]$^+$=589.1.

Step 6: [8-(tert-butoxycarbonylamino)-7-fluoro-3-[(6-methyl-7-oxo-5,8-dihydro-4H-pyrazolo[1,5-d][1,4]diazepin-2-yl)amino]-6-isoquinolyl]boronic Acid

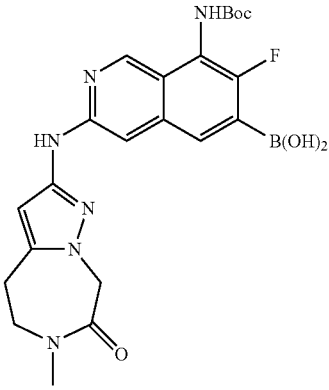 [SMILES: CN1CCc2cc(Nc3cc4cc(B(O)O)c(F)c(NC(=O)OC(C)(C)C)c4cn3)nn2CC1=O]

To a mixture of [8-(tert-butoxycarbonylamino)-7-fluoro-3-[(6-methyl-7-oxo-5,8-dihydro-4H-pyrazolo[1,5-d][1,4]diazepin-2-yl)amino]-6-isoquinolyl] trifluoromethanesulfonate (670 mg, 1.14 mmol) in 1,4-dioxane (20 mL) was added bis(pinacolato)diboron (867.28 mg, 3.42 mmol) and [1,1'-bis(diphenylphosphino)ferrocene]dichloropalladium (II) (83.3 mg, 0.11 mmol) at 90° C. The resulting mixture was stirred for 1 hour at 90° C. The reaction was quenched with water. The resulting mixture was extracted with dichloromethane, dried with anhydrous sodium sulfate. After filtration, the filtrate was concentrated under vacuum to afford [8-(tert-butoxycarbonylamino)-7-fluoro-3-[(6-methyl-7-oxo-5,8-dihydro-4H-pyrazolo[1,5-d][1,4]diazepin-2-yl)amino]-6-isoquinolyl]boronic acid (380 mg, 0.78 mmol) as a yellow oil. LCMS (ESI) [M+H]$^+$=485.1.

Step 7: tert-butyl N-[6-(5-amino-4-chloro-3-pyridyl)-7-fluoro-3-[(6-methyl-7-oxo-5,8-dihydro-4H-pyrazolo[1,5-d][1,4]diazepin-2-yl)amino]-8-isoquinolyl]carbamate

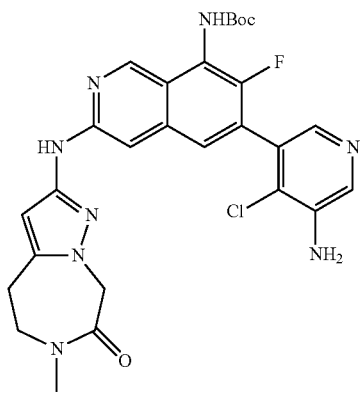 [SMILES: CN1CCc2cc(Nc3cc4cc(-c5cncc(N)c5Cl)c(F)c(NC(=O)OC(C)(C)C)c4cn3)nn2CC1=O]

A mixture of 4-chloro-5-iodo-pyridin-3-amine (189.15 mg, 0.74 mmol) and [8-(tert-butoxycarbonylamino)-7-fluoro-3-[(6-methyl-7-oxo-5,8-dihydro-4H-pyrazolo[1,5-d][1,4]diazepin-2-yl)amino]-6-isoquinolyl]boronic acid (120 mg, 0.25 mmol), [1,1'-bis(diphenylphosphino)ferrocene]dichloropalladium(II) (36.28 mg, 0.05 mmol), potassium phosphate (157.79 mg, 0.74 mmol), sodium acetate (20.32 mg, 0.25 mmol) in acetonitrile (2 mL)/water (0.2 ml) was stirred for 1 h at 90° C. The reaction was concentrated under vacuum. The crude was used in next step directly. LCMS (ESI) [M+H]$^+$=567.1

Step 8: 2-[[8-amino-6-(5-amino-4-chloro-3-pyridyl)-7-fluoro-3-isoquinolyl]amino]-6-methyl-5,8-dihydro-4H-pyrazolo[1,5-d][1,4]diazepin-7-one; Formic Acid

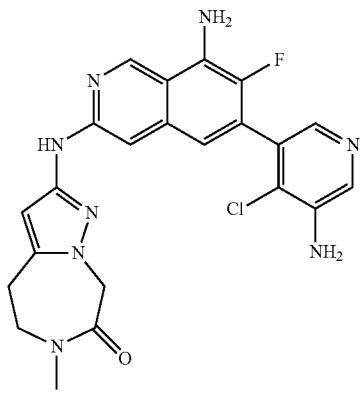 [SMILES: CN1CCc2cc(Nc3cc4cc(-c5cncc(N)c5Cl)c(F)c(N)c4cn3)nn2CC1=O]

A solution of tert-butyl N-[6-(5-amino-4-chloro-3-pyridyl)-7-fluoro-3-[(6-methyl-7-oxo-5,8-dihydro-4H-pyrazolo[1,5-d][1,4]diazepin-2-yl)amino]-8-isoquinolyl]carbamate (120 mg, 0.21 mmol) and 2,2,2-trifluoroacetic acid (3 mL) in dichloromethane (3 mL) was stirred at room temperature for 2 hours. The mixture was concentrated under vacuum. The residue was purified by Prep-HPLC to afford 2-[[8-amino-6-(5-amino-4-chloro-3-pyridyl)-7-fluoro-3-isoquinolyl]amino]-6-methyl-5,8-dihydro-4H-pyrazolo[1,5-d][1,4]diazepin-7-one; formic acid (15.6 mg, 0.030 mmol) as a yellow solid. LCMS (ESI) [M+H]$^+$=467.1; $^1$HNMR (300 MHz, DMSO) δ 9.26 (s, 1H), 9.07 (s, 1H), 8.15 (s, 1H), 7.75 (s, 1H), 7.72 (s, 1H), 6.80 (d, J=6.0 Hz, 1H), 6.10 (s, 2H), 5.98 (s, 1H), 5.79 (s, 2H), 4.97 (s, 2H), 3.83-3.81 (m, 2H), 3.18-3.16 (m, 2H), 2.95 (s, 3H).

Example 191

2-((8-amino-7-fluoro-6-(4-methylpyridin-3-yl)isoquinolin-3-yl)amino)-6-(methyl-d3)-5,6-dihydro-4H-pyrazolo[1,5-d][1,4]diazepin-7(8H)-one (Compound 231)

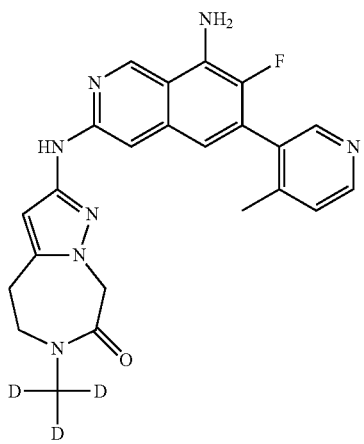 [SMILES: [2H]C([2H])([2H])N1CCc2cc(Nc3cc4cc(-c5cnccc5C)c(F)c(N)c4cn3)nn2CC1=O]

Step 1: 2-bromo-6-(trideuteriomethyl)-5,8-dihydro-4H-pyrazolo[1,5-d][1,4]diazepin-7-one

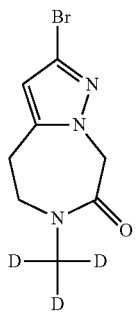 [SMILES: [2H]C([2H])([2H])N1CCc2cc(Br)nn2CC1=O]

To a solution of 2-bromo-4,5,6,8-tetrahydropyrazolo[1,5-d][1,4]diazepin-7-one (250 mg, 1.09 mmol) and potassium tert-butoxide (243.41 mg, 2.17 mmol) in tetrahydrofuran (20 mL) was added iodomethane-D$_3$ (236.29 mg, 1.63 mmol) at 25° C. The reaction was stirred for 1 hour at 25° C. After filtration, the filtrate was concentrated under vacuum. The residue was purified by flash chromatography on silica gel eluting with methanol/dichloromethane (5/95) to afford 2-bromo-6-(trideuteriomethyl)-5,8-dihydro-4H-pyrazolo[1,5-d][1,4]diazepin-7-one (220 mg, 0.89 mmol) as a white solid. LCMS (ESI) [M+H]$^+$=247.

Step 2: 2-[[8-chloro-7-fluoro-6-(4-methyl-3-pyridyl)-3-isoquinolyl]amino]-6-(trideuteriomethyl)-5,8-dihydro-4H-pyrazolo[1,5-d][1,4]diazepin-7-one

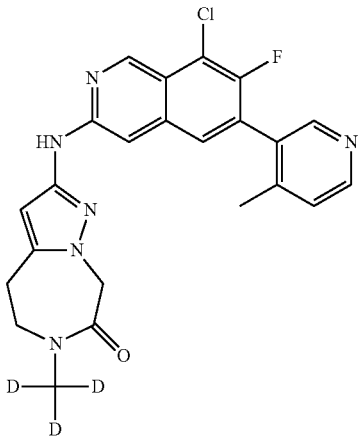 [SMILES: [2H]C([2H])([2H])N1CCc2cc(Nc3cc4cc(-c5cnccc5C)c(F)c(Cl)c4cn3)nn2CC1=O]

A mixture of 2-bromo-6-(trideuteriomethyl)-5,8-dihydro-4H-pyrazolo[1,5-d][1,4]diazepin-7-one (220 mg, 0.89 mmol), 8-chloro-7-fluoro-6-(4-methyl-3-pyridyl)isoquinolin-3-amine (256.15 mg, 0.89 mmol), tris(dibenzylideneacetone)dipalladium-chloroformadduct (138.22 mg, 0.13 mmol), 4,5-bis(diphenylphosphino)-9,9-dimethylxanthene (152.06 mg, 0.18 mmol) and cesium carbonate (870.71 mg, 2.67 mmol) in 1,4-dioxane (20 mL) was stirred for 5 hours at 100° C. After filtration, the filtrate was concentrated under reduced pressure. The residue was purified by flash chromatography on silica gel eluting with methanol/dichloromethane (1/10) to afford 2-[[8-chloro-7-fluoro-6-(4-methyl-3-pyridyl)-3-isoquinolyl]amino]-6-(trideuteriomethyl)-5,8-dihydro-4H-pyrazolo[1,5-d][1,4]diazepin-7-one (280 mg, 0.62 mmol) as a yellow solid. LCMS (ESI) [M+H]$^+$=454.

Step 3: tert-butyl N-[7-fluoro-6-(4-methyl-3-pyridyl)-3-[[7-oxo-6-(trideuteriomethyl)-5,8-dihydro-4H-pyrazolo[1,5-d][1,4]diazepin-2-yl]amino]-8-isoquinolyl]carbamate

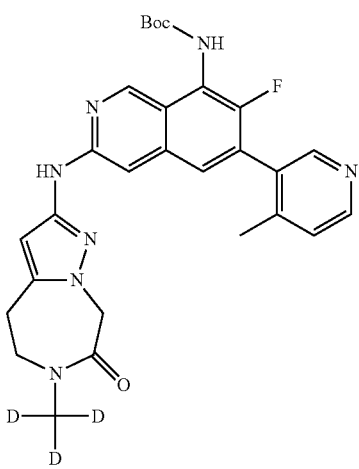 [SMILES: [2H]C([2H])([2H])N1CCc2cc(Nc3cc4cc(-c5cnccc5C)c(F)c(NC(=O)OC(C)(C)C)c4cn3)nn2CC1=O]

A mixture of 2-[[8-chloro-7-fluoro-6-(4-methyl-3-pyridyl)-3-isoquinolyl]amino]-6-(trideuteriomethyl)-5,8-dihydro-4H-pyrazolo[1,5-d][1,4]diazepin-7-one (280 mg, 0.62 mmol), tert-butyl carbamate (1.80 g, 15.42 mmol), tris(dibenzylideneacetone)dipalladium-chloroform adduct (127.69 mg, 0.12 mmol), BrettPhos (99.38 mg, 0.19 mmol) and cesium carbonate (804.39 mg, 2.47 mmol) in 1,4-dioxane (20 mL) was stirred for 2 hours at 90° C. After filtration, the filtrate was concentrated under reduced pressure. The residue was purified by flash chromatography on silica gel eluting with methanol/dichloromethane (1/10) to afford tert-butyl N-[7-fluoro-6-(4-methyl-3-pyridyl)-3-[[7-oxo-6-(trideuteriomethyl)-5,8-dihydro-4H-pyrazolo[1,5-d][1,4]diazepin-2-yl]amino]-8-isoquinolyl]carbamate (150 mg, 0.28 mmol) as a yellow solid. LCMS (ESI) [M+H]$^+$=535

Step 4: 2-[[8-amino-7-fluoro-6-(4-methyl-3-pyridyl)-3-isoquinolyl]amino]-6-(trideuteriomethyl)-5,8-dihydro-4H-pyrazolo[1,5-d][1,4]diazepin-7-one

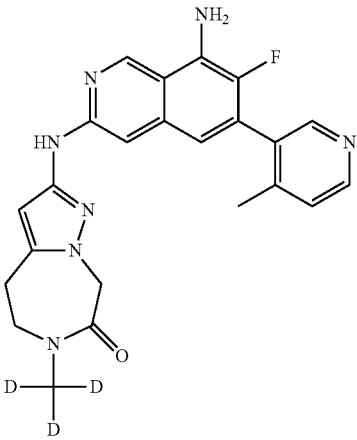 [SMILES: [2H]C([2H])([2H])N1CCc2cc(Nc3cc4cc(-c5cnccc5C)c(F)c(N)c4cn3)nn2CC1=O]

A mixture of tert-butyl N-[7-fluoro-6-(4-methyl-3-pyridyl)-3-[[7-oxo-6-(trideuteriomethyl)-5,8-dihydro-4H-pyrazolo[1,5-d][1,4]diazepin-2-yl]amino]-8-isoquinolyl]carbamate (120 mg, 0.22 mmol) and 2,2,2-trifluoroacetic acid (2 mL) in dichloromethane (2 mL) was stirred at 25° C. for 1 hour. The mixture was concentrated under vacuum. The resulting residue was purified by reverse phase chromatography (acetonitrile 0-40/0.1% ammonia in water) to afford 2-[[8-amino-7-fluoro-6-(4-methyl-3-pyridyl)-3-isoquinolyl]amino]-6-(trideuteriomethyl)-5,8-dihydro-4H-pyrazolo[1,5-d][1,4]diazepin-7-one (40.7 mg, 0.09 mmol) as a yellow solid. LCMS (ESI) [M+H]$^+$=435; $^1$HNMR (400 MHz, DMSO) δ 9.27 (s, 1H), 9.08 (s, 1H), 8.50-8.49 (d, J=4.0 Hz, 1H), 8.43 (s, 1H), 7.72 (s, 1H), 7.39-7.38 (d, J=4.0 Hz, 1H), 6.79-6.77 (d, J=8.0 Hz, 1H), 6.10 (s, 2H), 5.98 (s, 1H), 4.97 (s, 2H), 3.83-3.81 (m, 2H), 3.18-3.16 (m, 2H), 2.22 (s, 3H).

847

Example 192 and Example 193

(±)-2-(8-amino-6-(5-amino-4-methylpyridin-3-yl)-7-fluoroisoquinolin-3-ylamino)-4-fluoro-6-methyl-5,6-dihydro-4H-pyrazolo[1,5-g][1,4]diazepin-7(8H)-one (Compound 308)

(4R)-2-(8-amino-6-(5-amino-4-methylpyridin-3-yl)-7-fluoroisoquinolin-3-ylamino)-4-fluoro-6-methyl-5,6-dihydro-4H-pyrazolo[1,5-g][1,4]diazepin-7(8H)-one (Compound 309) and (4S)-2-(8-amino-6-(5-amino-4-methylpyridin-3-yl)-7-fluoroisoquinolin-3-ylamino)-4-fluoro-6-methyl-5,6-dihydro-4H-pyrazolo[1,5-g][1,4]diazepin-7(8H)-one (Compound 310)

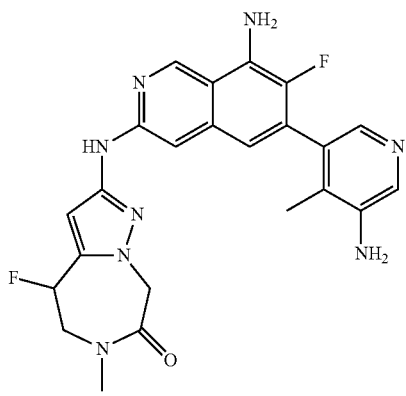

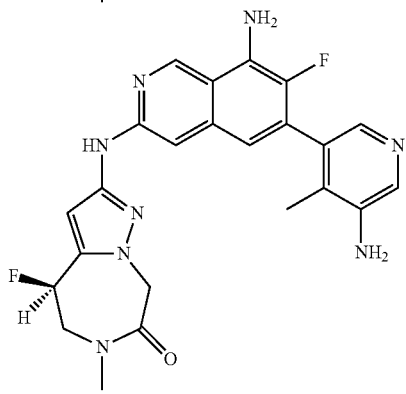

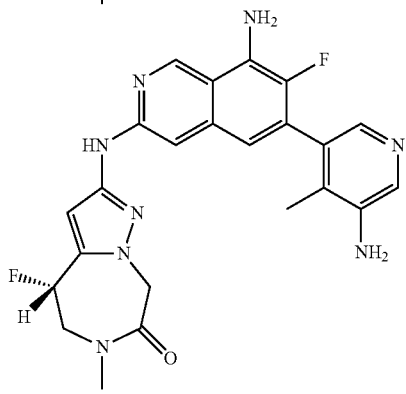

848

Step 1: 2-bromo-4-hydroxy-6-methyl-5,6-dihydro-4H-pyrazolo[1,5-g][1,4]diazepin-7(8H)-one

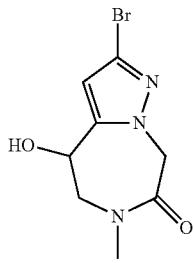

A mixture of 2-bromo-6-methyl-5,8-dihydropyrazolo[1,5-d][1,4]diazepine-4,7-dione (300 mg, 1.16 mmol) and NaBH$_4$ (44.17 mg, 1.16 mmol) in methanol (5 mL) was stirred at room temperature for 3 hours. The mixture was concentrated under vacuum. The residue was purified by flash chromatography on C18 eluting with ACN/water (17%) to afford 2-bromo-4-hydroxy-6-methyl-5,8-dihydro-4H-pyrazolo[1,5-d][1,4]diazepin-7-one (200 mg, 0.77 mmol) as a colorless oil. LC/MS (ESI) [M+H]$^+$=260

Step 2: 2-bromo-4-fluoro-6-methyl-5,6-dihydro-4H-pyrazolo[1,5-g][1,4]diazepin-7(8H)-one

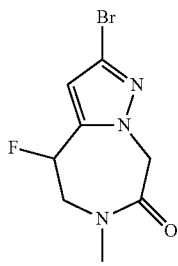

A mixture of 2-bromo-4-hydroxy-6-methyl-5,8-dihydro-4H-pyrazolo[1,5-d][1,4]diazepin-7-one (200 mg, 0.77 mmol) and diethylaminosulfur trifluoride (247.9 mg, 1.54 mmol) in dichloromethane (20 mL) was stirred at 0° C. for 1 hours. The reaction was quenched by NaHCO$_3$ solution. The resulting mixture was extracted with dichloromethane, dried with anhydrous sodium sulfate. After filtration, the filtrate was concentrated under vacuum. The residue was purified by reverse phase chromatography (acetonitrile 0-40/0.5% sodium bicarbonate in water) to afford 2-bromo-4-fluoro-6-methyl-5,8-dihydro-4H-pyrazolo[1,5-d][1,4]diazepin-7-one (150 mg, 0.57 mmol) as a white solid. LCMS (ESI) [M+H]$^+$=262.

Step 3: tert-butyl N-tert-butoxycarbonyl-N-[5-[8-chloro-7-fluoro-3-[(4-fluoro-6-methyl-7-oxo-5,8-dihydro-4H-pyrazolo[1,5-d][1,4]diazepin-2-yl)amino]-6-isoquinolyl]-4-methyl-3-pyridyl]carbamate

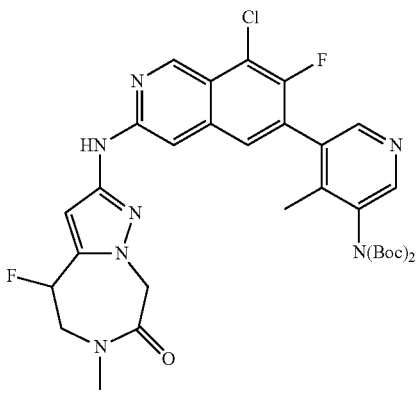

A mixture of 2-bromo-4-fluoro-6-methyl-5,8-dihydro-4H-pyrazolo[1,5-d][1,4]diazepin-7-one (300.0 mg, 1.14 mmol), tert-butyl N-[5-(3-amino-8-chloro-7-fluoro-6-isoquinolyl)-4-methyl-3-pyridyl]-N-tert-butoxycarbonyl-carbamate (575.74 mg, 1.14 mmol), tris(dibenzylideneacetone)dipalladium-chloroformadduct (236.95 mg, 0.23 mmol), 4,5-bis(diphenylphosphino)-9,9-dimethylxanthene (264.65 mg, 0.46 mmol) and potassium carbonate (473.9 mg, 3.43 mmol) in 1,4-dioxane (50 mL) was stirred for 12 hours at 100° C. After filtration, the filtrate was concentrated under reduced pressure. The residue was purified by flash chromatography on silica gel eluting with methanol/dichloromethane (1/10) to afford tert-butyl N-tert-butoxycarbonyl-N-[5-[8-chloro-7-fluoro-3-[(4-fluoro-6-methyl-7-oxo-5,8-dihydro-4H-pyrazolo[1,5-d][1,4]diazepin-2-yl)amino]-6-isoquinolyl]-4-methyl-3-pyridyl]carbamate (400 mg, 0.58 mmol) as a yellow solid. LCMS (ESI) [M+H]$^+$=684.

Step 4: tert-butyl N-tert-butoxycarbonyl-N-[5-[8-(tert-butoxycarbonylamino)-7-fluoro-3-[(4-fluoro-6-methyl-7-oxo-5,8-dihydro-4H-pyrazolo[1,5-d][1,4]diazepin-2-yl)amino]-6-isoquinolyl]-4-methyl-3-pyridyl]carbamate

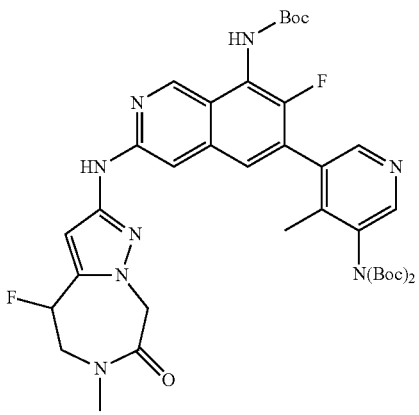

A mixture of tert-butyl N-tert-butoxycarbonyl-N-[5-[8-chloro-7-fluoro-3-[(4-fluoro-6-methyl-7-oxo-5,8-dihydro-4H-pyrazolo[1,5-d][1,4]diazepin-2-yl)amino]-6-isoquinolyl]-4-methyl-3-pyridyl]carbamate (420 mg, 0.61 mmol), Boc-NH$_2$ (2.15 g, 18.42 mmol), tris(dibenzylideneacetone)dipalladium-chloroformadduct (127.08 mg, 0.12 mmol), Brettphos (65.93 mg, 0.12 mmol) and cesium carbonate (800.55 mg, 2.46 mmol) in 1,4-dioxane (10 mL) was stirred for 2 hours at 90° C. After filtration, the filtrate was concentrated under reduced pressure. The residue was purified by flash chromatography on silica gel eluting with methanol/dichloromethane (1/10) to afford tert-butyl N-tert-butoxycarbonyl-N-[5-[8-(tert-butoxycarbonylamino)-7-fluoro-3-[(4-fluoro-6-methyl-7-oxo-5,8-dihydro-4H-pyrazolo[1,5-d][1,4]diazepin-2-yl)amino]-6-isoquinolyl]-4-methyl-3-pyridyl]carbamate (400 mg, 0.52 mmol) as a yellow solid. LCMS (ESI) [M+H]$^+$=765

Step 5: (±)-2-(8-amino-6-(5-amino-4-methylpyridin-3-yl)-7-fluoroisoquinolin-3-ylamino)-4-fluoro-6-methyl-5,6-dihydro-4H-pyrazolo[1,5-g][1,4]diazepin-7(8H)-one (Compound 308)

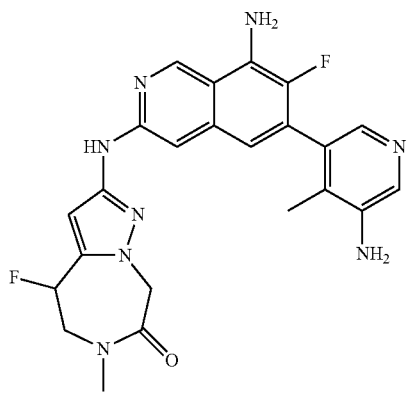 [SMILES: Cc1c(N)cncc1-c1cc2cc(Nc3cc4n(n3)CC(=O)N(C)CC4F)ncc2c(N)c1F]

A solution of tert-butyl N-tert-butoxycarbonyl-N-[5-[8-(tert-butoxycarbonylamino)-7-fluoro-3-[(4-fluoro-6-methyl-7-oxo-5,8-dihydro-4H-pyrazolo[1,5-d][1,4]diazepin-2-yl)amino]-6-isoquinolyl]-4-methyl-3-pyridyl]carbamate (400 mg, 0.52 mmol) and TFA (10 mL, 0.52 mmol)] in dichloromethane (5 mL) was stirred at 25° C. for 1 hour. The mixture was concentrated under vacuum. The crude product was purified by Prep-HPLC (Atlantis HILIC OBD, 19×150 mm 5 um; water (10 mmol/L): CH$_3$CN=17%-27% B in 10 min) to afford [2-[[8-amino-6-(5-amino-4-methyl-3-pyridyl)-7-fluoro-3-isoquinolyl]amino]-4-fluoro-6-methyl-5,8-dihydro-4H-pyrazolo[1,5-d][1,4]diazepin-7-one (150 mg, 0.32 mmol)] as a yellow solid. LCMS (ESI) [M+H]$^+$=465.3; $^1$H NMR (400 MHz, DMSO-d$_6$) δ 9.28 (s, 1H), 9.25 (s, 1H), 7.99 (s, 1H), 7.67 (s, 1H), 6.74 (d, J=6.1 Hz, 1H), 6.42 (d, J=2.5 Hz, 1H), 6.08 (s, 2H), 5.99-5.86 (m, 1H), 5.27-5.18 (m, 3H), 4.81 (d, J=14.9 Hz, 1H), 4.45-4.36 (m, 1H), 4.05-3.93 (m, 1H), 3.00 (s, 3H), 1.93 (d, J=1.5 Hz, 3H).

Step 6: (4R)-2-(8-amino-6-(5-amino-4-methylpyridin-3-yl)-7-fluoroisoquinolin-3-ylamino)-4-fluoro-6-methyl-5,6-dihydro-4H-pyrazolo[1,5-g][1,4]diazepin-7(8H)-one and (4S)-2-(8-amino-6-(5-amino-4-methylpyridin-3-yl)-7-fluoroisoquinolin-3-ylamino)-4-fluoro-6-methyl-5,6-dihydro-4H-pyrazolo[1,5-g][1,4]diazepin-7(8H)-one

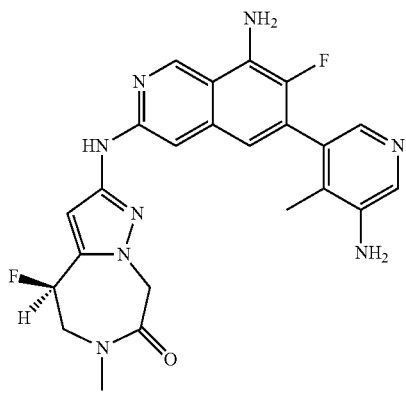

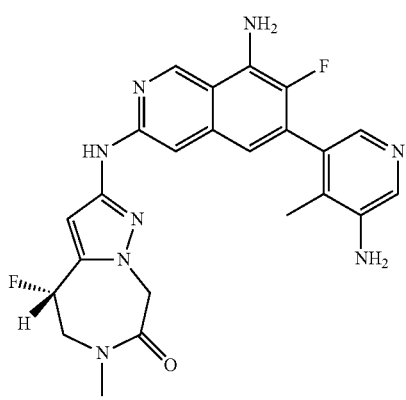

2-(8-amino-6-(5-amino-4-methylpyridin-3-yl)-7-fluoroisoquinolin-3-ylamino)-4-fluoro-6-methyl-5,6-dihydro-4H-pyrazolo[1,5-g][1,4]diazepin-7(8H)-one was separated by Chiral-HPLC to afford two isomers: Compound 309: (18.8 mg, 0.041 mmol) as a yellow solid. Retention time: 4.500 min (CHIRAL Cellulose-SB. 0.46*15 cm; 3 μm MtBE (0.1% DEA):EtOH=70:30; 1.0 ml/min); LCMS (ESI) [M+H]⁺=465.3; ¹H NMR (300 MHz, DMSO-d₆) δ 9.27 (s, 1H), 9.24 (s, 1H), 7.98 (s, 1H), 7.66 (s, 2H), 6.73 (d, J=6.1 Hz, 1H), 6.41 (d, J=2.5 Hz, 1H), 6.07 (s, 2H), 6.00-5.83 (m, 1H), 5.27-5.16 (m, 3H), 4.80 (d, J=15.0 Hz, 1H), 4.39 (dd, J=35.2, 16.1 Hz, 1H), 4.00 (dd, J=14.6, 8.0 Hz, 1H), 2.99 (s, 3H), 1.92 (d, J=1.5 Hz, 3H). Compound 310: (20.9 mg, 0.045 mmol) (assumed) as a yellow solid. Retention time: 5.344 min (CHIRAL Cellulose-SB. 0.46*15 cm; 3 μm; MtBE (0.1% DEA):EtOH=70:30; 1.0 ml/min); LCMS (53) [M+H]⁺=465.3; ¹H NMR (300 MHz, DMSO-d₆) δ 9.27 (s, 1H), 9.24 (s, 1H), 7.98 (s, 1H), 7.66 (s, 2H), 6.73 (d, J=6.1 Hz, 1H), 6.41 (d, J=2.5 Hz, 1H), 6.07 (s, 2H), 5.99-5.83 (m, 1H), 5.27-5.16 (m, 3H), 4.80 (d, J=14.9 Hz, 1H), 4.45-4.34 (m, 1H), 4.07-3.96 (m, 1H), 2.99 (s, 3H), 1.92 (d, J=1.5 Hz, 3H).

Example 194

2-(8-amino-7-fluoro-6-(4-methylpyridin-3-yl)isoquinolin-3-ylamino)-4-hydroxy-4,6-dimethyl-5,6-dihydro-4H-pyrazolo[1,5-g][1,4]diazepin-7(8H)-one (Compound 311)

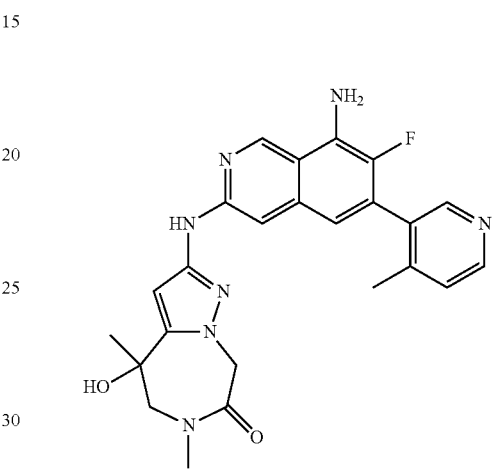

Step 1: 2-bromo-6-methyl-5,6-dihydro-8H-pyrazolo[1,5-g][1,4]diazepine-4,7-dione

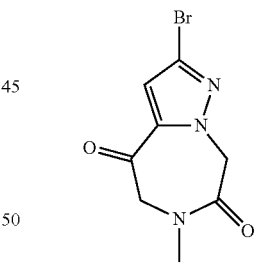

A solution of 2-bromo-6-methyl-4-methylene-5,8-dihydropyrazolo[1,5-d][1,4]diazepin-7-one (1.0 g, 3.9 mmol) in carbon tetrachloride (1 mL), acetonitrile (1 mL) and water (1 mL) was stirred at 25° C. for 10 minutes. RuCl₃ (265.0 mg, 1.18 mmol) and sodium periodate (2520 mg, 11.78 mmol) was added. The mixture was stirred at 25° C. for 2 hours. The reaction was quenched by Na₂S₂O₃/NaHCO₃ solution. The resulting mixture was extracted with ethyl acetate, dried with anhydrous sodium sulfate. After filtration, the filtrate was concentrated under vacuum. The residue was purified by flash chromatography on silica gel eluting with EA/PE (20%) to afford 2-bromo-6-methyl-5,8-dihydropyrazolo[1,5-d][1,4]diazepine-4,7-dione (300 mg, 1.16 mmol) as a yellow oil. LCMS (ESI) [M+H]⁺=258

Step 2: 2-(8-chloro-7-fluoro-6-(4-methylpyridin-3-yl)isoquinolin-3-ylamino)-6-methyl-5,6-dihydro-8H-pyrazolo[1,5-g][1,4]diazepine-4,7-dione

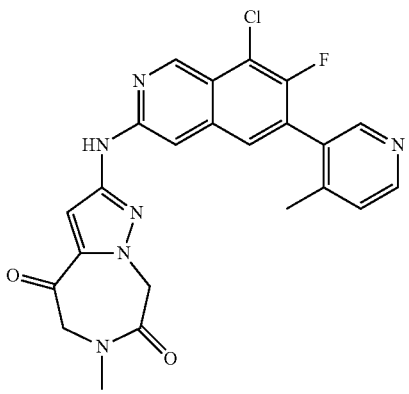 [SMILES: Cc1ccncc1-c1cc2cc(Nc3cc4n(n3)CC(=O)N(C)CC4=O)ncc2c(Cl)c1F]

A mixture of 2-bromo-6-methyl-5,8-dihydropyrazolo[1,5-d][1,4]diazepine-4,7-dione (160.0 mg, 0.62 mmol), 8-chloro-7-fluoro-6-(4-methyl-3-pyridyl)isoquinolin-3-amine (178.38 mg, 0.62 mmol), t-BuBrettphos (150.04 mg, 0.31 mmol), t-BuBrettphos Pd G3 (211.79 mg, 0.25 mmol) and cesium carbonate (606.35 mg, 1.86 mmol) in 1,4-dioxane (10 mL) was stirred for 4 hours at 120° C. After filtration, the filtrate was concentrated under reduced pressure. The residue was purified by flash chromatography on silica gel eluting with methanol/dichloromethane (1/10) to afford 2-[[8-chloro-7-fluoro-6-(4-methyl-3-pyridyl)-3-isoquinolyl]amino]-6-methyl-5,8-dihydropyrazolo[1,5-d][1,4]diazepine-4,7-dione (70 mg, 0.15 mmol) as a yellow solid. LC/MS (ESI) [M+H]$^+$=465

Step 3: 2-(8-chloro-7-fluoro-6-(4-methylpyridin-3-yl)isoquinolin-3-ylamino)-4-hydroxy-4,6-dimethyl-5,6-dihydro-4H-pyrazolo[1,5-g][1,4]diazepin-7(8H)-one

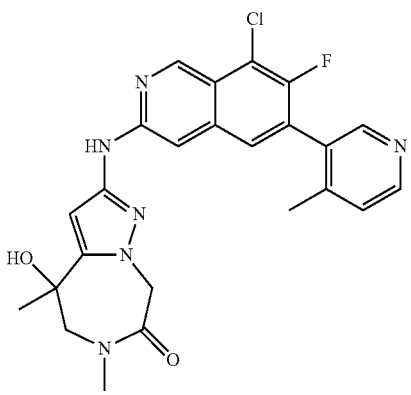 [SMILES: Cc1ccncc1-c1cc2cc(Nc3cc4n(n3)CC(=O)N(C)CC4(C)O)ncc2c(Cl)c1F]

To a mixture of 2-[[8-chloro-7-fluoro-6-(4-methyl-3-pyridyl)-3-isoquinolyl]amino]-6-methyl-5,8-dihydropyrazolo[1,5-d][1,4]diazepine-4,7-dione (100 mg, 0.22 mmol) in THF (10 mL) was added methylmagnesium iodide (0.43 mL, 1.29 mmol) in tetrahydrofuran at −78° C. The resulting solution was stirred for 2 hours at −65° C. The reaction was quenched with water. The resulting mixture was extracted with ethyl acetate, dried with anhydrous sodium sulfate. After filtration, the filtrate was concentrated under vacuum. The residue was purified by flash chromatography on silica gel eluting with methanol/dichloromethane (1/10) to afford 2-[[8-chloro-7-fluoro-6-(4-methyl-3-pyridyl)-3-isoquinolyl]amino]-4-hydroxy-4,6-dimethyl-5,8-dihydropyrazolo[1,5-d][1,4]diazepin-7-one (40 mg, 0.083 mmol) as a yellow solid. LC/MS (ESI): [M+H]$^+$=481

Step 4: tert-butyl 7-fluoro-3-(4-hydroxy-4,6-dimethyl-7-oxo-5,6,7,8-tetrahydro-4H-pyrazolo[1,5-g][1,4]diazepin-2-ylamino)-6-(4-methylpyridin-3-yl)isoquinolin-8-ylcarbamate

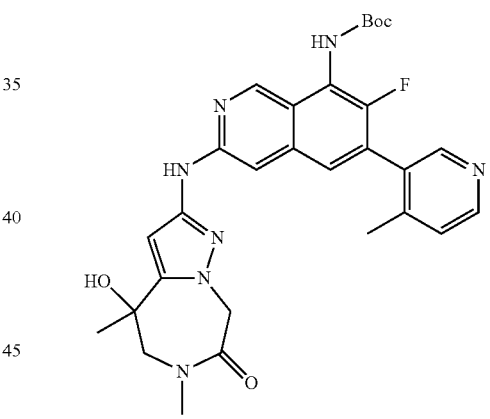

A mixture of 2-[[8-chloro-7-fluoro-6-(4-methyl-3-pyridyl)-3-isoquinolyl]amino]-4-hydroxy-4,6-dimethyl-5,8-dihydropyrazolo[1,5-d][1,4]diazepin-7-one (70 mg, 0.15 mmol), Boc-NH$_2$ (510.9 mg, 4.37 mmol), tris(dibenzylideneacetone)dipalladium-chloroformadduct (30.13 mg, 0.0300 mmol), Brettphos (15.63 mg, 0.030 mmol), cesium carbonate (189.8 mg, 0.58 mmol) in 1,4-dioxane (5 mL) was stirred for 2 hours at 90° C. After filtration, the filtrate was concentrated under reduced pressure. The residue was purified by flash chromatography on silica gel eluting with methanol/dichloromethane (1/10) to afford tert-butyl N-[7-fluoro-3-[(4-hydroxy-4,6-dimethyl-7-oxo-5,8-dihydropyrazolo[1,5-d][1,4]diazepin-2-yl)amino]-6-(4-methyl-3-pyridyl)-8-isoquinolyl]carbamate (40 mg, 0.071 mmol) as a yellow solid. LCMS (ESI) [M+H]$^+$=562.

Step 5: 2-(8-amino-7-fluoro-6-(4-methylpyridin-3-yl)isoquinolin-3-ylamino)-4-hydroxy-4,6-dimethyl-5,6-dihydro-4H-pyrazolo[1,5-g][1,4]diazepin-7(8H)-one

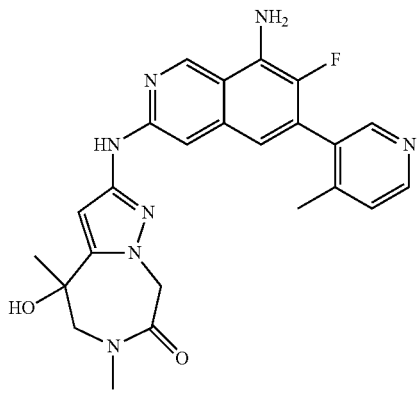 [SMILES: Cc1ccncc1-c1cc2cc(Nc3cc4n(n3)CC(=O)N(C)CC4(C)O)ncc2c(N)c1F]

A mixture of tert-butyl N-[7-fluoro-3-[(4-hydroxy-4,6-dimethyl-7-oxo-5,8-dihydropyrazolo[1,5-d][1,4]diazepin-2-yl)amino]-6-(4-methyl-3-pyridyl)-8-isoquinolyl]carbamate (30 mg, 0.050 mmol) in dichloromethane (2 mL) and 2,2,2-trifluoroacetic acid (5 mL) was stirred at 25° C. for 2 hours. The mixture was concentrated under vacuum. The crude product was purified by Prep-HPLC (Atlantis HILIC OBD, 19×150 mm 5 um; water (10 mmol/L): CH$_3$CN=15%-40% B in 7 min) to afford 2-(8-amino-7-fluoro-6-(4-methylpyridin-3-yl)isoquinolin-3-ylamino)-4-hydroxy-4,6-dimethyl-5,6-dihydro-4H-pyrazolo[1,5-g][1,4]diazepin-7(8H)-one (4.3 mg, 0.0093 mmol) as a yellow solid. LCMS (ESI) [M+H]$^+$=462.3; $^1$H NMR (300 MHz, Methanol-d$_4$) δ 9.16 (s, 1H), 8.50-8.37 (m, 2H), 7.67 (s, 1H), 7.42 (d, J=5.2 Hz, 1H), 6.86 (d, J=6.2 Hz, 1H), 6.35 (s, 1H), 5.16 (d, J=15.2 Hz, 1H), 4.96-4.89 (m, 2H), 4.11 (d, J=15.6 Hz, 1H), 3.64 (d, J=15.5 Hz, 1H), 3.15 (s, 3H), 2.32 (s, 3H), 1.61 (s, 3H).

Example 195

2-((8-amino-6-(5-amino-4-methylpyridin-3-yl)-7-fluoroisoquinolin-3-yl)amino)-6-(2,2-difluoroethyl)-5,6-dihydro-4H-pyrazolo[1,5-d][1,4]diazepin-7(8H)-one (Compound 312)

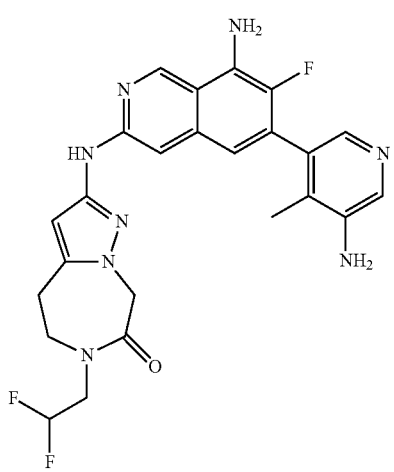 [SMILES: Cc1c(N)cncc1-c1cc2cc(Nc3cc4n(n3)CC(=O)N(CC(F)F)CC4)ncc2c(N)c1F]

Step 1: 2-Bromo-6-(2,2-difluoroethyl)-5,8-dihydro-4H-pyrazolo[1,5-d][1,4]diazepin-7-one

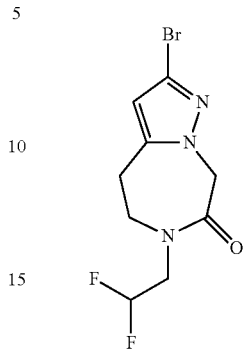

To a mixture of 2-bromo-4,5,6,8-tetrahydropyrazolo[1,5-d][1,4]diazepin-7-one (900 mg, 3.91 mmol) in N,N-dimethylformamide (50 mL) was added sodium hydride (281.67 mg, 11.74 mmol) at 0° C. The reaction was then stirred for 0.5 hours. 2-iodo-1,1-difluoroethane (3.75 g, 19.56 mmol) in N,N-dimethylformamide (5 mL) was added and stirred at 20° C. for 3 hours. The residue was purified directly by a reversed-phase HPLC with MeOH/0.5% sodium bicarbonate in water (5% to 65% in 30 min) to afford 2-bromo-6-(2,2-difluoroethyl)-5,8-dihydro-4H-pyrazolo[1,5-d][1,4]diazepin-7-one (380 mg, 33% yield) as a white solid. LCMS (ESI) [M+H]$^+$=294.1.

Step 2: Tert-butyl N-tert-butoxycarbonyl-N-[5-[8-chloro-3-[[6-(2,2-difluoroethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate

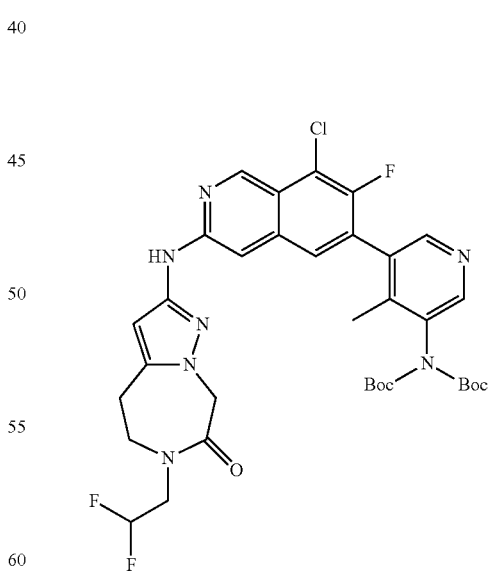

A mixture of tert-butyl N-[5-(3-amino-8-chloro-7-fluoro-6-isoquinolyl)-4-methyl-3-pyridyl]-N-tert-butoxycarbonyl-carbamate (350 mg, 0.70 mmol), 2-bromo-6-(2,2-difluoroethyl)-5,8-dihydro-4H-pyrazolo[1,5-d][1,4]diazepin-7-one (307 mg, 1.04 mmol), tris(dibenzylideneacetone)dipalladium-chloroformadduct (144 mg, 0.14 mmol), 4,5-bis(diphenylphosphino)-9,9-dimethylxanthene (160 mg, 0.28 mmol) and cesium carbonate (680 mg, 2.09 mmol) in 1,4-dioxane (35 mL) was stirred at 100° C. for 3 hours. After filtration, the filtrate was concentrated under reduced pressure. The residue was purified by a reversed-phase HPLC with MeOH/0.5% sodium bicarbonate in water (5% to 75% in 30 min) to afford tert-butyl N-tert-butoxycarbonyl-N-[5-[8-chloro-3-[[6-(2,2-difluoroethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate (180 mg, 36.1% yield) as a yellow solid. LCMS (ESI) [M+H]⁺=716.4.

Step 3: Tert-butyl N-tert-butoxycarbonyl-N-[5-[8-(tert-butoxycarbonylamino)-3-[[6-(2,2-difluoroethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate

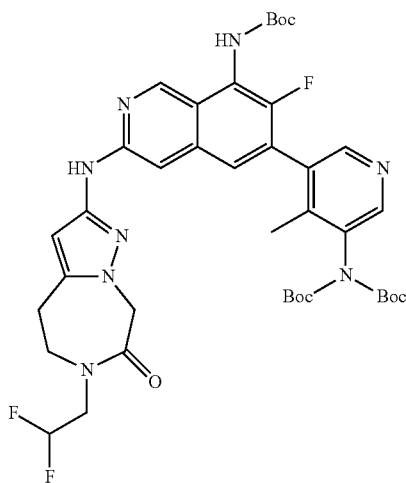 [SMILES: Cc1c(-c2cc3cc(Nc4cc5n(n4)CC(=O)N(CC(F)F)CC5)ncc3c(NC(=O)OC(C)(C)C)c2F)cncc1N(C(=O)OC(C)(C)C)C(=O)OC(C)(C)C]

A mixture of tert-butyl N-tert-butoxycarbonyl-N-[5-[8-chloro-3-[[6-(2,2-difluoroethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate (180 mg, 0.25 mmol), tert-butyl carbamate (736 mg, 6.28 mmol), tris(dibenzylideneacetone)dipalladium-chloroform adduct (39 mg, 0.04 mmol), BrettPhos (27 mg, 0.05 mmol) and cesium carbonate (410 mg, 1.26 mmol) in 1,4-dioxane (20 mL) was stirred at 90° C. for 2 hours. After filtration, the filtrate was concentrated under reduced pressure. The residue was purified by a reversed-phase HPLC with ACN/0.5% sodium bicarbonate in water (5% to 65% in 30 min) to afford tert-butyl N-tert-butoxycarbonyl-N-[5-[8-(tert-butoxycarbonylamino)-3-[[6-(2,2-difluoroethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate (100 mg, 49.9% yield) as a yellow solid. LCMS (ESI) [M+H]⁺=797.5.

Step 4: 2-[[8-Amino-6-(5-amino-4-methyl-3-pyridyl)-7-fluoro-3-isoquinolyl]amino]-6-(2,2-difluoroethyl)-5,8-dihydro-4H-pyrazolo[1,5-d][1,4]diazepin-7-one

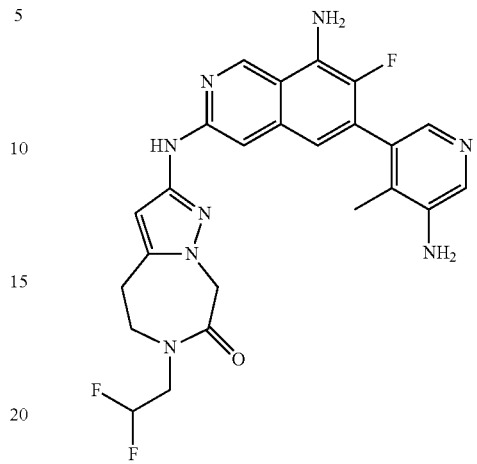

A solution of tert-butyl N-tert-butoxycarbonyl-N-[5-[8-(tert-butoxycarbonylamino)-3-[[6-(2,2-difluoroethyl)-7-oxo-5,8-dihydro-4H-pyrazolo[1,5-d][1,4]diazepin-2-yl]amino]-7-fluoro-6-isoquinolyl]-4-methyl-3-pyridyl]carbamate (500 mg, 0.63 mmol) and TFA (10 mL) in DCM (5 mL) was stirred at 20° C. for 1.5 hours. The mixture was concentrated under vacuum. The reaction mixture was adjusted to pH 10 with NH₃ in MeOH (7 M). After concentrated under vacuum, the crude product was purified by Prep-HPLC (XBridge Prep C18 OBD Column19*15 mm Sum; 10 mmol sodium bicarbonate in water: ACN (20%41% in 7 min)) to afford 2-[[8-amino-6-(5-amino-4-methyl-3-pyridyl)-7-fluoro-3-isoquinolyl]amino]-6-(2,2-difluoroethyl)-5,8-dihydro-4H-pyrazolo[1,5-d][1,4]diazepin-7-one (156 mg, 50.3% yield) as a yellow solid. LCMS (ESI) [M+H]⁺=497.3; ¹HNMR (300 MHz, DMSO) δ 9.24 (s, 1H), 9.08 (s, 1H), 7.98 (s, 1H), 7.71 (s, 1H), 7.66 (s, 1H), 6.71 (s, 1H), 6.37-5.98 (m, 4H), 5.22 (s, 2H), 5.04 (s, 2H), 3.96-3.79 (m, 4H), 3.07-3.03 (m, 2H), 1.92 (s, 3H).

Example 196

2-((8-amino-7-fluoro-6-(4-methylpyridin-3-yl)isoquinolin-3-yl)amino)-4-hydroxy-4-(methoxymethyl)-6-methyl-5,6-dihydro-4H-pyrazolo[1,5-d][1,4]diazepin-7(8H)-one (Compound 313)

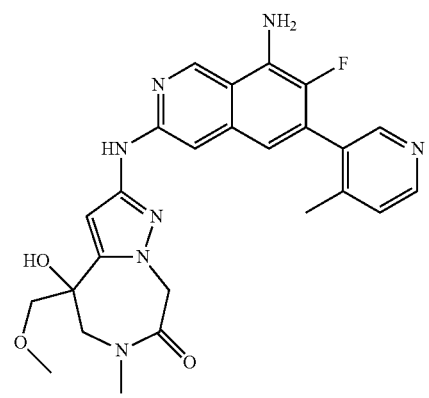 [SMILES: COCC1(O)CN(C)C(=O)Cn2nc(Nc3cc4cc(-c5cnccc5C)c(F)c(N)c4cn3)cc21]

Step 1: 2'-bromo-6'-methyl-5',6'-dihydrospiro[oxirane-2,4'-pyrazolo[1,5-d][1,4]diazepin]-7'(8'H)-one

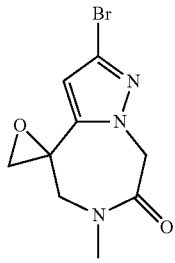

A mixture of 2-bromo-6-methyl-4-methylene-5,6-dihydro-4H-pyrazolo[1,5-d][1,4]diazepin-7(8H)-one (1.0 g, 3.91 mmol) and m-CPBA (2.03 g, 11.73 mmol) in dichloromethane (20 mL) was stirred at 25° C. for 12 hours. The reaction was quenched with aqueous $Na_2S_2O_3$ and $NaHCO_3$. The resulting mixture was extracted with dichloromethane, dried over anhydrous sodium sulfate. After filtration, the filtrate was concentrated under vacuum. The residue was purified by flash chromatography on silica gel eluting with dichloromethane/methanol (10/1) to afford 2'-bromo-6'-methyl-5',6'-dihydrospiro[oxirane-2,4'-pyrazolo[1,5-d][1,4]diazepin]-7'(8'H)-one (300 mg, 1.10 mmol) as a light yellow solid. LCMS (ESI) [M+H]$^+$=272.

Step 2: 2-bromo-4-hydroxy-4-(methoxymethyl)-6-methyl-5,6-dihydro-4H-pyrazolo[1,5-d][1,4]diazepin-7(8H)-one

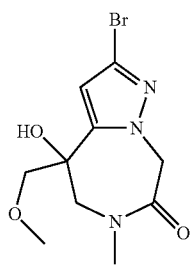 [SMILES: COCC1(O)CN(C)C(=O)Cn2nc(Br)cc21]

A solution of 2'-bromo-6'-methyl-5',6'-dihydrospiro[oxirane-2,4'-pyrazolo[1,5-d][1,4]diazepin]-7'(8'H)-one (300 mg, 1.10 mmol) and sodium methoxide (178 mg, 3.30 mmol) in methanol (5 mL) was stirred for 12 hour at room temperature. The residue was purified by flash chromatography on silica gel eluting with dichloromethane/methanol (10/1) to afford 2-bromo-4-hydroxy-4-(methoxymethyl)-6-methyl-5,6-dihydro-4H-pyrazolo[1,5-d][1,4]diazepin-7(8H)-one (170 mg, 0.56 mmol) a light yellow solid. LCMS (ESI) [M+H]$^+$=304.

Step 3: 2-[[8-chloro-7-fluoro-6-(4-methyl-3-pyridyl)-3-isoquinolyl]amino]-4-hydroxy-4-(methoxymethyl)-6-methyl-5,8-dihydropyrazolo[1,5-d][1,4]diazepin-7-one

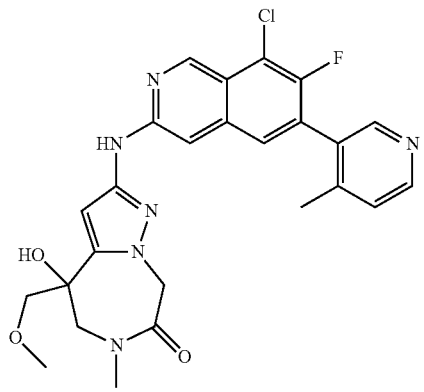 [SMILES: COCC1(O)CN(C)C(=O)Cn2nc(Nc3cc4cc(-c5cnccc5C)c(F)c(Cl)c4cn3)cc21]

A mixture of 8-chloro-7-fluoro-6-(4-methyl-3-pyridyl)isoquinolin-3-amine (75.68 mg, 0.26 mmol), 2-bromo-4-hydroxy-4-(methoxymethyl)-6-methyl-5,8-dihydropyrazolo[1,5-d][1,4]diazepin-7-one (80 mg, 0.26 mmol), t-BuBrettphos Pd G3 (89.85 mg, 0.11 mmol), t-BuBrettphos (63.65 mg, 0.13 mmol) and cesium carbonate (257.25 mg, 0.79 mmol) in 1,4-dioxane (4 mL) was stirred at 130° C. for 1 hour. The mixture was concentrated under vacuum.

The residue was purified by flash chromatography on silica gel eluting with Dichloromethane/methanol (10/1) to afford 2-[[8-chloro-7-fluoro-6-(4-methyl-3-pyridyl)-3-isoquinolyl]amino]-4-hydroxy-4-(methoxymethyl)-6-methyl-5,8-dihydropyrazolo[1,5-d][1,4]diazepin-7-one (47 mg, 0.092 mmol) as a light yellow solid. LCMS (ESI) [M+H]$^+$=511.

Step 4: tert-butyl N-[7-fluoro-3-[[4-hydroxy-4-(methoxymethyl)-6-methyl-7-oxo-5,8-dihydropyrazolo[1,5-d][1,4]diazepin-2-yl]amino]-6-(4-methyl-3-pyridyl)-8-isoquinolyl]carbamate

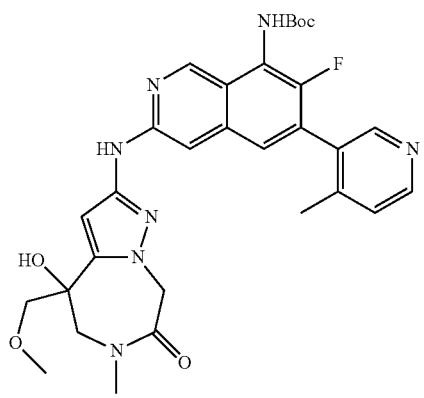 [SMILES: COCC1(O)CN(C)C(=O)Cn2nc(Nc3cc4cc(-c5cnccc5C)c(F)c(NC(=O)OC(C)(C)C)c4cn3)cc21]

A mixture of 2-[[8-chloro-7-fluoro-6-(4-methyl-3-pyridyl)-3-isoquinolyl]amino]-4-hydroxy-4-(methoxymethyl)-6-methyl-5,8-dihydropyrazolo[1,5-d][1,4]diazepin-7-one (100 mg, 0.20 mmol), tert-butyl carbamate (573.2 mg, 4.89 mmol), tris(dibenzylideneacetone)dipalladium-chloroformadduct (40.51 mg, 0.04 mmol), Brettphos (31.47 mg, 0.06 mmol) and cesium carbonate (191.41 mg, 0.59 mmol) in 1,4-dioxane (5 mL) was stirred at 90° C. for 3 hours. The mixture was concentrated under vacuum. The residue was purified by flash chromatography on silica gel eluting with dichloromethane/methanol (10/1) to afford tert-butyl N-[7-fluoro-3-[[4-hydroxy-4-(methoxymethyl)-6-methyl-7-oxo-5,8-dihydropyrazolo[1,5-d][1,4]diazepin-2-yl]amino]-6-(4-methyl-3-pyridyl)-8-isoquinolyl]carbamate (50 mg, 0.085 mmol) as a light yellow solid. LCMS (ESI) [M+H]$^+$=592.

Step 5: 2-[[8-amino-7-fluoro-6-(4-methyl-3-pyridyl)-3-isoquinolyl]amino]-4-hydroxy-4-(methoxymethyl)-6-methyl-5,8-dihydropyrazolo[1,5-d][1,4]diazepin-7-one

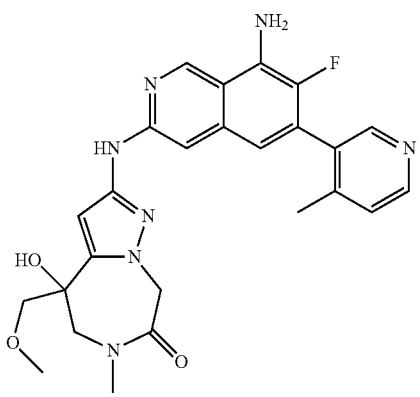 [SMILES: COCC1(O)CN(C)C(=O)Cn2nc(Nc3cc4cc(-c5cnccc5C)c(F)c(N)c4cn3)cc21]

A mixture of [tert-butyl N-[7-fluoro-3-[[4-hydroxy-4-(methoxymethyl)-6-methyl-7-oxo-5,8-dihydropyrazolo[1,5-d][1,4]diazepin-2-yl]amino]-6-(4-methyl-3-pyridyl)-8-isoquinolyl]carbamate (80 mg, 0.14 mmol) and 2,2,2-trifluoroacetic acid (0.5 mL) in dichloromethane (3 mL) was stirred at room temperature for 1 hour. The mixture was concentrated under vacuum. The residue was adjusted to pH 8 with ammonia in methanol (7 mol/L). The crude product was purified by Prep-HPLC (XBridge Prep C18 OBD Column19×150 mm; water (10 mmol/L sodium bicarbonate): CAN=30%-45% in 7 min) to afford 2-[[8-amino-7-fluoro-6-(4-methyl-3-pyridyl)-3-isoquinolyl]amino]-4-hydroxy-4-(methoxymethyl)-6-methyl-5,8-dihydropyrazolo[1,5-d][1,4]diazepin-7-one (11.5 mg, 0.023 mmol) as a yellow solid. LCMS (ESI) [M+H]$^+$=492. $^1$HNMR (400 MHz, DMSO) δ 9.29 (s, 1H), 9.19 (s, 1H), 8.50 (d, J=6.0 Hz, 1H), 8.43 (s, 1H), 7.72 (s, 1H), 7.39 (d, J=6.0 Hz, 1H), 6.79 (d, J=6.0 Hz, 1H), 6.26 (s, 1H), 6.13 (s, 2H), 5.85 (s, 1H), 5.07-4.84 (m, 2H), 4.07-3.65 (m, 2H), 3.55-3.43 (m, 2H), 3.32 (s, 3H), 2.97 (s, 3H), 2.23 (s, 3H).

Example 197

2'-((8-amino-7-fluoro-6-(1,3,5-trimethyl-1H-pyrazol-4-yl)isoquinolin-3-yl)amino)-6'-methyl-5',6'-dihydrospiro[cyclopropane-1,4'-pyrazolo[1,5-d][1,4]diazepin]-7'(8'H)-one (Compound 314)

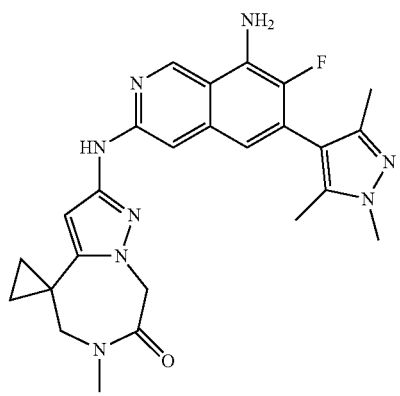

Step 1: 8-chloro-7-fluoro-6-(1,3,5-trimethylpyrazol-4-yl)isoquinolin-3-amine

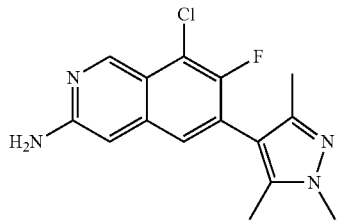 [SMILES: Cc1nn(C)c(C)c1-c1cc2cc(N)ncc2c(Cl)c1F]

A mixture of 8-chloro-7-fluoro-6-iodo-isoquinolin-3-amine (500 mg, 1.55 mmol), 1,3,5-trimethyl-4-(4,4,5,5-tetramethyl-1,3,2-dioxaborolan-2-yl)-1h-pyrazole (500 mg, 2.12 mmol), [1,1'-bis(diphenylphosphino)ferrocene]dichloropalladium(II) (113 mg, 0.15 mmol) and potassium carbonate (536 mg, 3.88 mmol) in 1,4-dioxane (15 mL) and water (1.5 mL) was stirred at 90° C. for 3 hours. The mixture was concentrated under vacuum. The residue was purified by flash chromatography on silica gel eluting with dichloromethane/methanol (96/4) to afford 8-chloro-7-fluoro-6-(1,3,5-trimethylpyrazol-4-yl)isoquinolin-3-amine (517 mg, 1.69 mmol) as a yellow solid. LCMS (ESI) [M+H]$^+$=305.

Step 2: 2-[[8-chloro-7-fluoro-6-(1,3,5-trimethylpyrazol-4-yl)-3-isoquinolyl]amino]-6-methyl-spiro[5,8-dihydropyrazolo[1,5-d1,4]diazepine-41'-cyclopropane1-7-one

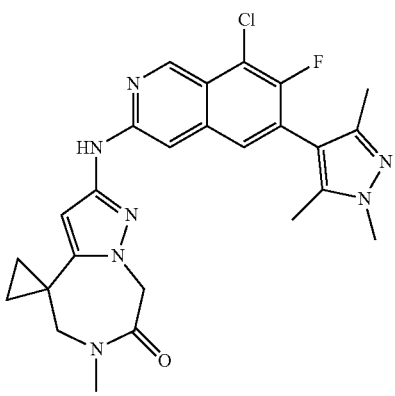 [SMILES: Cc1nn(C)c(C)c1-c1cc2cc(Nc3cc4n(n3)CC(=O)N(C)CC43CC3)ncc2c(Cl)c1F]

A mixture of 2-bromo-6-methyl-spiro[5,8-dihydropyrazolo[1,5-d][1,4]diazepine-4,1'-cyclopropane]-7-one (50 mg, 0.19 mmol), 8-chloro-7-fluoro-6-(1,3,5-trimethylpyrazol-4-yl)isoquinolin-3-amine (56.41 mg, 0.19 mmol), t-BuBrettphos Pd G3 (63.23 mg, 0.07 mmol), t-Bubrettphos (44.79 mg, 0.09 mmol) and cesium carbonate (181.02 mg, 0.56 mmol) in 1,4-dioxane (5 mL) was stirred at 130° C. for 1 hour. The mixture was concentrated under vacuum.

The residue was purified by flash chromatography on silica gel eluting with dichloromethane/methanol (94/6) to afford 2-[[8-chloro-7-fluoro-6-(1,3,5-trimethylpyrazol-4-yl)-3-isoquinolyl]amino]-6-methyl-spiro[5,8-dihydropyrazolo[1,5-d][1,4]diazepine-4,1'-cyclopropane]-7-one (27 mg, 0.055 mmol) as a yellow solid. LCMS (ESI) [M+H]$^+$=494.

Step 3: tert-butyl N-[7-fluoro-3-[(6-methyl-7-oxo-spiro[5,8-dihydropyrazolo[1,5-d][1,4]diazepine-4,1'-cyclopropane]-2-yl)amino]-6-(1,3,5-trimethylpyrazol-4-yl)-8-isoquinolyl]carbamate

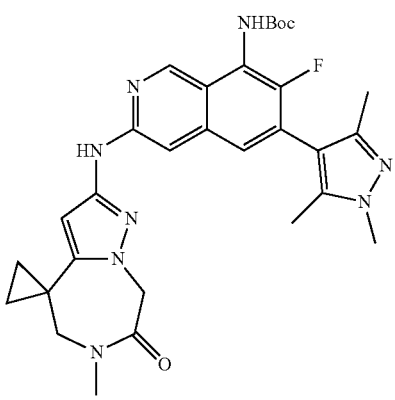 [SMILES: Cc1nn(C)c(C)c1-c1cc2cc(Nc3cc4n(n3)CC(=O)N(C)CC43CC3)ncc2c(NC(=O)OC(C)(C)C)c1F]

A mixture of 2-[[8-chloro-7-fluoro-6-(1,3,5-trimethylpyrazol-4-yl)-3-isoquinolyl]amino]-6-methyl-spiro[5,8-dihydropyrazolo[1,5-d][1,4]diazepine-4,1'-cyclopropane]-7-one (136.0 mg, 0.28 mmol), tert-butyl carbamate (806.36 mg, 6.88 mmol), Tris(dibenzylideneacetone)dipalladium-chloroformadduct (56.99 mg, 0.06 mmol), Brettphos (44.27 mg, 0.08 mmol) and cesium carbonate (269.27 mg, 0.83 mmol) in 1,4-dioxane (5 mL) was stirred at 90° C. for 3 hours. The mixture was concentrated under vacuum. The residue was purified by flash chromatography on silica gel eluting with dichloromethane/methanol (10/1) to afford tert-butyl N-[7-fluoro-3-[(6-methyl-7-oxo-spiro[5,8-dihydropyrazolo[1,5-d][1,4]diazepine-4,1'-cyclopropane]-2-yl)amino]-6-(1,3,5-trimethylpyrazol-4-yl)-8-isoquinolyl]carbamate (65 mg, 0.11 mmol) as a light yellow solid. LCMS (ESI) [M+H]$^+$=575.

Step 4: 2-[[8-amino-7-fluoro-6-(1,3,5-trimethylpyrazol-4-yl)-3-isoquinolyl]amino]-6-methyl-spiro[5,8-dihydropyrazolo[1,5-d][1,4]diazepine-4,1'-cyclopropane]-7-one

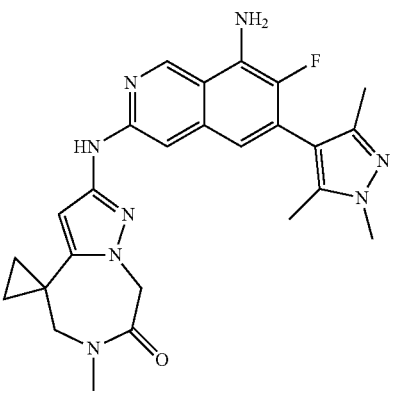

A mixture of tert-butyl N-[7-fluoro-3-[(6-methyl-7-oxo-spiro[5,8-dihydropyrazolo[1,5-d][1,4]diazepine-4,1'-cyclopropane]-2-yl)amino]-6-(1,3,5-trimethylpyrazol-4-yl)-8-isoquinolyl]carbamate (87.42 mg, 0.15 mmol) and 2,2,2-trifluoroacetic acid (1.0 mL) in dichloromethane (3 mL) was stirred at rt for 1 hour. The mixture was concentrated under vacuum.

The reaction mixture was adjusted to pH 8 with ammonia in methanol (7 mol/L). The crude product was purified by Prep-HPLC (XBridge Prep C18 OBD Column19×150 mm; water (10 mmol/L sodium bicarbonate) and ACN (30%-50%) in 7 min) to afford 2-[[8-amino-7-fluoro-6-(1,3,5-trimethylpyrazol-4-yl)-3-isoquinolyl]amino]-6-methyl-spiro[5,8-dihydropyrazolo[1,5-d][1,4]diazepine-4,1'-cyclopropane]-7-one (33 mg, 0.07 mmol) as a yellow solid. LCMS (ESI) [M+H]$^+$=475; $^1$HNMR (400 MHz, DMSO) δ 9.20 (s, 1H), 8.95 (s, 1H), 7.58 (s, 1H), 6.65 (d, J=6.0 Hz, 1H), 5.96 (s, 2H), 5.61 (s, 1H), 5.06 (s, 2H), 3.73-3.70 (m, 5H), 2.99 (s, 3H), 2.18 (s, 3H), 2.08 (s, 3H), 1.18-1.16 (m, 2H), 0.95-0.92 (m, 2H).

Example 198

2-((8-amino-6-(5-amino-4-methylpyridin-3-yl)-7-fluoroisoquinolin-3-yl)amino)-6-isopropyl-5,6-dihydro-4H-pyrazolo[1,5-d][1,4]diazepin-7(8H)-one (Compound 315)

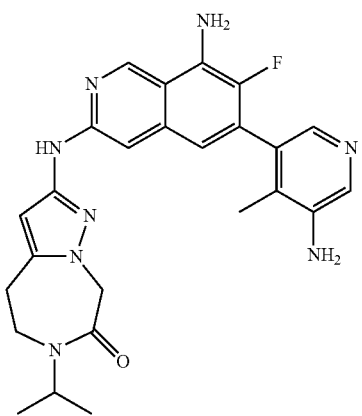

Step 1: tert-butyl N-tert-butoxycarbonyl-N-[5-[8-chloro-7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate

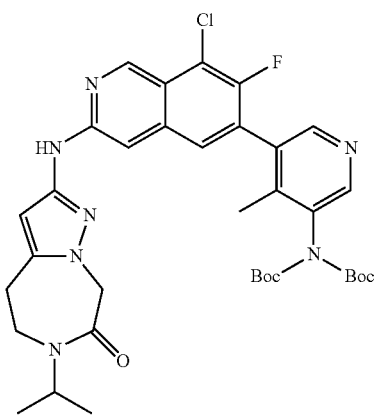 [SMILES: Cc1c(-c2cc3cc(Nc4cc5n(n4)CC(=O)N(C(C)C)CC5)ncc3c(Cl)c2F)cncc1N(C(=O)OC(C)(C)C)C(=O)OC(C)(C)C]

A mixture of tert-butyl N-[5-(3-amino-8-chloro-7-fluoro-6-isoquinolyl)-4-methyl-3-pyridyl]-N-tert-butoxycarbonyl-carbamate (518 mg, 1.03 mmol), 2-bromo-6-isopropyl-5,8-dihydro-4H-pyrazolo[1,5-d][1,4]diazepin-7-one (280.27 mg, 1.03 mmol), tris(dibenzylideneacetone)dipalladium (213.19 mg, 0.21 mmol), 4,5-bis(diphenylphosphino)-9,9-dimethylxanthene (238.11 mg, 0.41 mmol) and cesium carbonate (1.01 g, 3.09 mmol) in 1,4-dioxane (28 mL) was stirred at 100° C. for 15 hours. The reaction was cooled to room temperature and then concentrated under vacuum. The residue was purified by flash chromatography on silica gel eluting with dichloromethane/methanol (20/1) to afford tert-butyl N-tert-butoxycarbonyl-N-[5-[8-chloro-7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (280 mg, 0.40 mmol) as a yellow solid. LCMS (ESI) [M+H]$^+$=694.

Step 2: tert-butyl N-tert-butoxycarbonyl-N-[5-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate

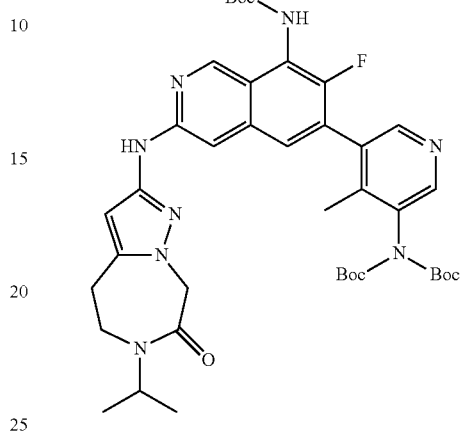

A mixture of tert-butyl N-tert-butoxycarbonyl-N-[5-[8-chloro-7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (270 mg, 0.39 mmol), tert-butyl carbamate (1.14 g, 9.72 mmol), tris(dibenzylideneacetone)dipalladium (80.51 mg, 0.08 mmol), Brettphos (83.39 mg, 0.16 mmol) and cesium carbonate (633.97 mg, 1.94 mmol) in 1,4-dioxane (40 mL) was stirred at 90° C. for 2 hours. The reaction was cooled to room temperature and then concentrated under vacuum. The residue was purified by flash chromatography on silica gel eluting with dichloromethane/methanol (20/1) to afford tert-butyl N-tert-butoxycarbonyl-N-[5-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (150 mg, 0.19 mmol) as a brown solid. LCMS (ESI) [M+H]$^+$=775.

Step 3: 2-[[8-amino-6-(5-amino-4-methyl-3-pyridyl)-7-fluoro-3-isoquinolyl]amino]-6-isopropyl-5,8-dihydro-4H-pyrazolo[1,5-d][1,4]diazepin-7-one

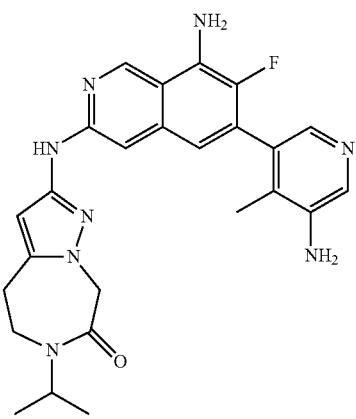 [SMILES: Cc1c(N)cncc1-c1cc2cc(Nc3cc4n(n3)CC(=O)N(C(C)C)CC4)ncc2c(N)c1F]

A solution of tert-butyl N-tert-butoxycarbonyl-N-[5-[8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]-4-methyl-3-pyridyl]carbamate (140 mg, 0.18 mmol) and 2,2,2-trifluoroacetic acid (5 mL, 0.18 mmol) in dichloromethane (5 mL) was stirred at 20° C. for 1 hours. The crude product was purified by Prep-HPLC (XBridge Shield RP18 OBD Column, 5 m, 19*150 mm; Water (10 mmol/L sodium bicarbonate)=25% B to 45% B in 7 min; 25 mL/min) to afford 2-[[8-amino-6-(5-amino-4-methyl-3-pyridyl)-7-fluoro-3-isoquinolyl]amino]-6-isopropyl-5,8-dihydro-4H-pyrazolo[1,5-d][1,4]diazepin-7-one (36.5 mg, 0.077 mmol) as a yellow solid. LCMS (ESI) [M+H]⁺=475.3. ¹H NMR (300 MHz, DMSO-d₆) δ 9.26 (s, 1H), 9.07 (s, 1H), 7.99 (s, 1H), 7.69 (d, J=8.9 Hz, 2H), 6.72 (d, J=6.1 Hz, 1H), 6.05 (s, 2H), 5.96 (s, 1H), 5.23 (s, 2H), 4.97 (s, 2H), 4.61-4.57 (m, 1H), 3.79-3.75 (m, 2H), 2.99-2.96 (m, 2H), 1.94 (s, 3H), 1.13 (d, J=6.8 Hz, 6H).

Example 199

2'-((8-amino-6-(5-amino-4-methylpyridin-3-yl)-7-fluoroisoquinolin-3-yl)amino)-6'-methyl-5',6'-dihydrospiro[cyclopropane-1,4'-pyrazolo[1,5-d][1,4]diazepin]-7'(8'H)-one (Compound 316)

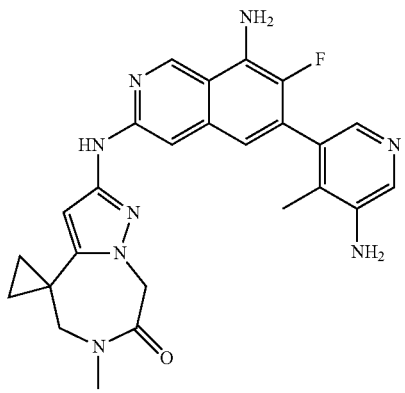 [SMILES: Cc1c(N)cncc1-c1cc2cc(Nc3cc4n(n3)CC(=O)N(C)CC43CC3)ncc2c(N)c1F]

Step 1: tert-butyl N-[(tert-butoxy)carbonyl]-N-[5-[8-chloro-7-fluoro-3-([3'-methyl-4'-oxo-2',3',4',5'-tetrahydrospiro[cyclopropane-1,1'-pyrazolo[1,5-d][1,4]diazepine]-8'-yl]amino)isoquinolin-6-yl]-4-methylpyridin-3-yl]carbamate

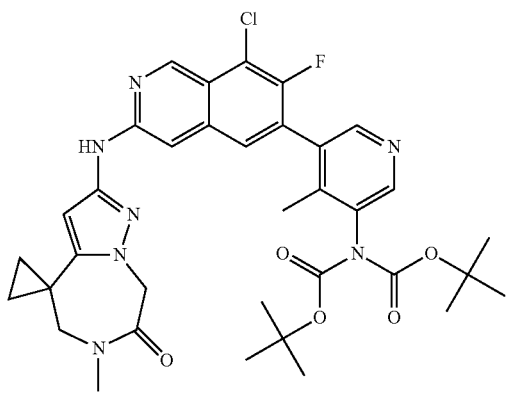 [SMILES: Cc1c(-c2cc3cc(Nc4cc5n(n4)CC(=O)N(C)CC54CC4)ncc3c(Cl)c2F)cncc1N(C(=O)OC(C)(C)C)C(=O)OC(C)(C)C]

A mixture of tert-butyl N-[5-(3-amino-8-chloro-7-fluoro-6-isoquinolyl)-4-methyl-3-pyridyl]-N-tert-butoxycarbonyl-carbamate (200 mg, 0.40 mmol), 2-bromo-6-methyl-spiro[5,8-dihydropyrazolo[1,5-d][1,4]diazepine-4,1'-cyclopropane]-7-one (129 mg, 0.48 mmol), t-BuBrettphos Pd G3 (137 mg, 0.16 mmol), t-Bubrettphos (97 mg, 0.2 mmol), cesium carbonate (391 mg, 1.2 mmol) in 1,4-dioxane was stirred at 130° C. for 1 hours. The mixture was concentrated under vacuum. The residue was purified by flash chromatography on silica gel eluting with dichloromethane/methanol (96/4) to afford tert-butyl N-[(tert-butoxy)carbonyl]-N-[5-[8-chloro-7-fluoro-3-([3'-methyl-4'-oxo-2',3',4',5'-tetrahydrospiro[cyclopropane-1,1'-pyrazolo[1,5-d][1,4]diazepine]-8'-yl]amino)isoquinolin-6-yl]-4-methylpyridin-3-yl]carbamate (69 mg, 25% yield) as a yellow solid. LCMS(ESI) [M+H]⁺=692.

Step 2: tert-butyl (tert-butoxycarbonyl)(5-(8-((tert-butoxycarbonyl)amino)-7-fluoro-3-((6'-methyl-7'-oxo-5',6',7',8'-tetrahydrospiro[cyclopropane-1,4'-pyrazolo[1,5-d][1,4]diazepin]-2'-yl)amino)isoquinolin-6-yl)-4-methylpyridin-3-yl)carbamate

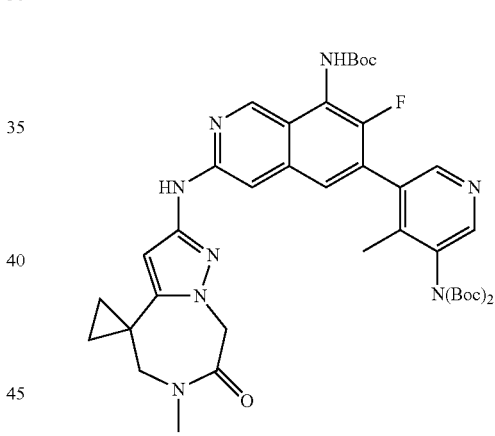

A mixture of tert-butyl N-[(tert-butoxy)carbonyl]-N-[5-[8-chloro-7-fluoro-3-([3'-methyl-4'-oxo-2',3',4',5'-tetrahydrospiro[cyclopropane-1,1'-pyrazolo[1,5-d][1,4]diazepine]-8'-yl]amino)isoquinolin-6-yl]-4-methylpyridin-3-yl] carbamate (69 mg, 0.1 mmol), tert-butyl carbamate (293 mg, 2.5 mmol), tris(dibenzylideneacetone)dipalladium-chloroformadduct (21 mg, 0.02 mmol), cesium carbonate (98 mg, 0.3 mmol), BrettPhos (22 mg, 0.04 mmol) in 1,4-dioxane (5 mL) was stirred for 2 h at 90° C. The resulting mixture was concentrated under vacuum. The residue was purified by flash chromatography on silica gel eluting with dichloromethane/methanol (10/1) to afford tert-butyl (tert-butoxycarbonyl)(5-(8-((tert-butoxycarbonyl)amino)-7-fluoro-3-((6'-methyl-7'-oxo-5',6',7',8'-tetrahydrospiro[cyclopropane-1,4'-pyrazolo[1,5-d][1,4]diazepin]-2'-yl)amino)isoquinolin-6-yl)-4-methylpyridin-3-yl)carbamate (39 mg, 50%) as a light yellow solid. LCMS (ESI) [M+H]⁺=773.

Step 3: 2-[[8-amino-6-(5-amino-4-methyl-3-pyridyl)-7-fluoro-3-isoquinolyl]amino]-6-methyl-spiro[5,8-dihydropyrazolo[1,5-d][1,4]diazepine-4,1'-cyclopropane]-7-one

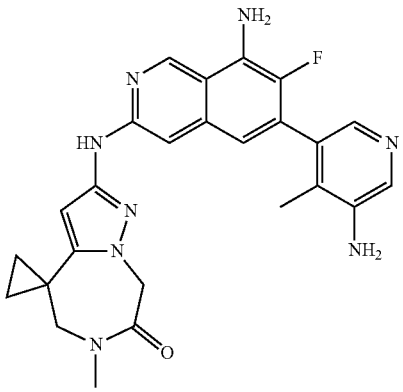 [SMILES: Cc1c(N)cncc1-c1cc2cc(Nc3cc4n(n3)CC(=O)N(C)CC43CC3)ncc2c(N)c1F]

A mixture of tert-butyl N-tert-butoxycarbonyl-N-[5-[8-(tert-butoxycarbonylamino)-7-fluoro-3-[(6-methyl-7-oxo-spiro[5,8-dihydropyrazolo[1,5-d][1,4]diazepine-4,1'-cyclopropane]-2-yl)amino]-6-isoquinolyl]-4-methyl-3-pyridyl] carbamate (50 mg, 0.06 mmol) and 2,2,2-trifluoroacetic acid (1.0 mL) in dichloromethane was stirred at rt for 1 hour. The mixture was concentrated under vacuum. The mixture was adjusted to pH 8 with a solution of NH$_3$ in methanol. After filtration, the filtrate was concentrated under reduced pressure. The crude product was purified by Prep-HPLC (Atlantis HILIC OBD Column 19 mm×150 um; CH$_3$CN: H$_2$O (sodium bicarbonate 10 mmol/L)=28-43% in 8 min) to afford 2-[[8-amino-6-(5-amino-4-methyl-3-pyridyl)-7-fluoro-3-isoquinolyl]amino]-6-methyl-spiro[5,8-dihydropyrazolo[1,5-d][1,4]diazepine-4,1'-cyclopropane]-7-one (8.2 mg, 0.017 mmol) as a yellow solid. LCMS (ESI [M+H]$^+$=473; $^1$HNMR (400 MHz, DMSO-d$_6$) δ 9.24 (s, 1H), 8.99 (s, 1H), 7.98 (s, 1H), 7.67 (s, 1H), 7.64 (s, 1H), 6.72 (d, J=6 Hz, 1H), 6.05 (s, 2H), 5.61 (s, 1H), 5.22 (s, 2H), 5.06 (s, 2H), 3.73 (s, 2H), 2.99 (s, 3H), 1.93 (s, 3H), 1.24-1.16 (m, 2H), 0.96-0.92 (m, 2H).

Example 200

2-((8-amino-7-fluoro-6-(4-methylpyridin-3-yl)isoquinolin-3-yl)amino)-6-methyl-4-methylene-5,6-dihydro-4H-pyrazolo[1,5-d][1,4]diazepin-7(8H)-one (Compound 317)

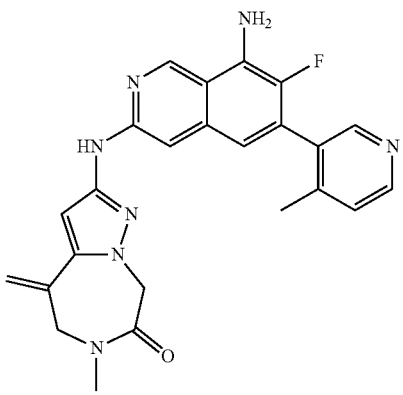 [SMILES: C=C1CN(C)C(=O)Cn2nc(Nc3cc4cc(-c5cnccc5C)c(F)c(N)c4cn3)cc21]

A mixture of tert-butyl N-[7-fluoro-3-([6-methyl-4-methylidene-7-oxo-4H,5H,6H,7H,8H-pyrazolo[1,5-d][1,4]diazepin-2-yl]amino)-6-(4-methylpyridin-3-yl)isoquinolin-8-yl] carbamate (20 mg, 0.03 mmol) in HCl in dioxane (2 mL, 4 mol/L) was stirred for 2 h at room temperature. The resulting mixture was concentrated under vacuum. The residue was purified by Prep-HPLC (Atlantis HILIC OBD Column 19*150 mm*5 um; Water (0.1% sodium bicarbonate):CH$_3$CN=25%-41% in 7 min) to afford 2-[[8-amino-7-fluoro-6-(4-methylpyridin-3-yl)isoquinolin-3-yl]amino]-6-methyl-4-methylidene-4H,5H,6H,7H,8H-pyrazolo[1,5-d][1,4]diazepin-7-one (2.8 mg, 0.006 mmol) as a yellow solid. LCMS (ESI) [M+H]$^+$=444; $^1$HNMR (400 MHz, DMSO-d$_6$) δ 9.29 (s, 1H), 9.17 (s, 1H), 8.50 (d, J=4.0 Hz, 1H), 8.42 (s, 1H), 7.65 (s, 1H), 7.38 (d, J=4.0 Hz, 1H), 6.80 (d, J=8.0 Hz, 1H), 6.51 (s, 1H), 6.11 (s, 2H), 5.63 (s, 1H), 5.33 (s, 1H), 5.08 (s, 2H), 4.41 (s, 2H), 2.91 (s, 3H), 2.21 (s, 3H).

Example 201

2-((8-amino-7-fluoro-6-(4-methyl-6-(oxazol-2-yl)pyridin-3-yl)isoquinolin-3-yl)amino)-4,6-dimethyl-5,6-dihydro-4H-pyrazolo[1,5-d][1,4]diazepin-7(8H)-one (Compound 318)

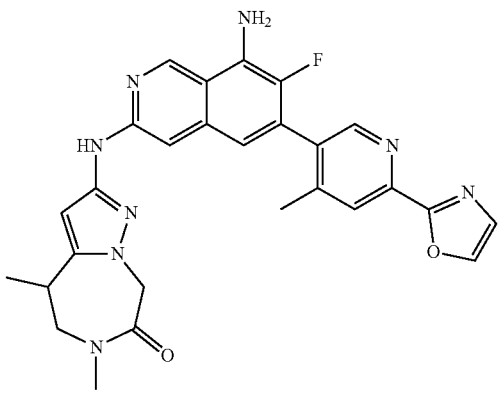 [SMILES: Cc1cc(-c2ncco2)ncc1-c1cc2cc(Nc3cc4n(n3)CC(=O)N(C)CC4C)ncc2c(N)c1F]

Step 1: 3,5-dibromo-1H-pyrazole

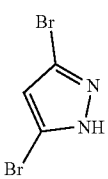

To a solution of 3,4,5-tribromo-1H-pyrazole (50 g, 164.1 mmol) in THF (750 mL) was added a solution of n-BuLi (2.5 M) in hexane (150 mL) at −65° C. The resulting solution was stirred for 1 h at −65° C. in a dry ice bath. The reaction was then quenched by water. The resulting mixture was concentrated under vacuum. The residue was purified by flash chromatography on silica gel eluting with dichloromethane/methanol (50/1) to afford 3,5-dibromo-1H-pyrazole (20 g, 54%) as a white solid. LCMS (ESI) [M+H]$^+$=226.9.

Step 2: Tert-butyl 2-(3,5-dibromo-1H-pyrazol-1-yl)acetate

To a solution of 3,5-dibromo-1H-pyrazole (20 g, 88.55 mmol) in N,N-dimethylformamide (400 mL) was added potassium carbonate (20 g, 144.7 mmol), TBAI (1.6 g, 4.33 mmol) and tert-butyl 2-chloroacetate (20 g, 132.8 mmol). The resulting solution was stirred for 12 h at room temperature. After filtration, the filtrate was concentrated under vacuum. The residue was purified on a silica gel column eluted with dichloromethane/methanol (100/1) to afford tert-butyl 2-(3,5-dibromo-1H-pyrazol-1-yl)acetate (18 g, 60%) as a colorless oil. LCMS (ESI) [M+H]$^+$=341.0.

Step 3: 2-(3,5-dibromo-1H-pyrazol-1-yl)acetic Acid

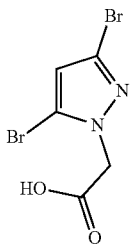

A solution of tert-butyl 2-(3,5-dibromo-1H-pyrazol-1-yl) acetate (18 g, 52.94 mmol) in dichloromethane (10 mL) and 2,2,2-trifluoroacetic acid (100 mL) was stirred for 2 h at 80° C. The resulting mixture was concentrated under vacuum to afford 2-(3,5-dibromo-1H-pyrazol-1-yl)acetic acid (15 g, crude) as a white solid. LCMS (ESI) [M+H]$^+$=284.9.

Step 4: 2-(3,5-Dibromo-1H-pyrazol-1-yl)-N-methyl-N-(prop-2-en-1-yl)acetamide

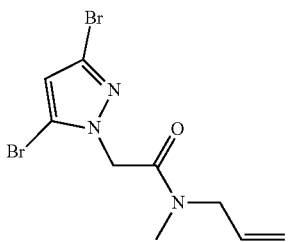

A solution of 2-(3,5-dibromo-1H-pyrazol-1-yl)acetic acid (15 g, 52.84 mmol), methyl(prop-2-en-1-yl)amine (5.7 g, 80.15 mmol), N,N-diisopropylethylamine (27 g, 208.9 mmol) and HATU (30 g, 78.9 mmol) in N,N-dimethylformamide (500 mL) was stirred for 16 hours at room temperature. The resulting mixture was diluted with ethyl acetate and then washed with sodium chloride solution. The organic phase was dried with anhydrous sodium sulfate. After filtration, the filtrate was concentrated under vacuum. The residue was purified by flash chromatography on silica gel eluting with ethyl acetate/petroleum ether (2/3) to afford 2-(3,5-dibromo-1H-pyrazol-1-yl)-N-methyl-N-(prop-2-en-1-yl)acetamide (16.3 g, 92%) as a yellow oil. LCMS (ESI) [M+H]$^+$=338.0.

Step 5: 2-Bromo-6-methyl-4-methylidene-4H,5H,6H,7H,8H-pyrazolo[1,5-d][1,4]diazepin-7-one

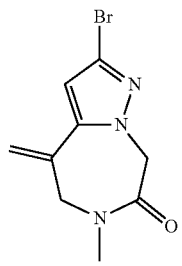

A mixture of 2-(3,5-dibromo-1H-pyrazol-1-yl)-N-methyl-N-(prop-2-en-1-yl)acetamide (5 g, 14.84 mmol), palladium acetate (166 mg, 0.74 mmol), triphenylphosphine (388 mg, 1.48 mmol), TBAB (4.8 g, 14.890 mmol) and potassium acetate (4.2 g, 42.80 mmol) in N,N-dimethylformamide (100 mL) was stirred for 10 h at 80° C. After filtration, the filtrate was concentrated under vacuum. The residue was purified on a silica gel column eluted with ethyl acetate/petroleum ether (2/1) to afford 2-bromo-6-methyl-4-methylidene-4H,5H,6H,7H,8H-pyrazolo[1,5-d][1,4]diazepin-7-one (3.2 g, 84%) as a brown oil. LCMS (ESI) [M+H]$^+$=258.1.

Step 6: 5-Bromo-4-methyl-2-(1,3-oxazol-2-yl)pyridine

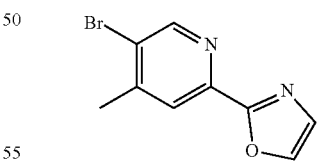

A mixture of 2,5-dibromo-4-methylpyridine (1.2 g, 4.78 mmol), 2-(tributylstannyl)-1,3-oxazole (2.06 g, 5.75 mmol) and tetrakis(triphenylphosphine)palladium (552 mg, 0.48 mmol) in 1,4-dioxane (30 mL) was stirred for 16 hours at 90° C. After filtration, the filtrate was concentrated under vacuum. The residue was purified on a silica gel column eluted with ethyl acetate/petroleum ether (1/2) to afford 5-bromo-4-methyl-2-(1,3-oxazol-2-yl)pyridine (380 mg, 33%) as a light yellow solid. LCMS (ESI) [M+H$^+$=241.1.

Step 7: 4-Methyl-2-(1,3-oxazol-2-yl)-5-(tetramethyl-1,3,2-dioxaborolan-2-yl)pyridine

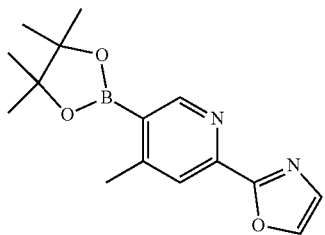 [SMILES: Cc1cc(-c2ncco2)ncc1B1OC(C)(C)C(C)(C)O1]

A mixture of 5-bromo-4-methyl-2-(1,3-oxazol-2-yl)pyridine (800 mg, 3.35 mmol), 4,4,5,5-tetramethyl-2-(tetramethyl-1,3,2-dioxaborolan-2-yl)-1,3,2-dioxaborolane (8.4 g, 33.08 mmol), [1,1'-bis(diphenylphosphino)ferrocene]dichloropalladium(II) (244 mg, 0.33 mmol) and potassium acetate (820 mg, 8.36 mmol) in 1,4-dioxane (30 mL) was stirred for 16 hours at 90° C. After filtration, the filtrate was concentrated under vacuum. The residue was purified on a silica gel column eluted with ethyl acetate/petroleum ether (1/1) to afford 4-methyl-2-(1,3-oxazol-2-yl)-5-(tetramethyl-1,3,2-dioxaborolan-2-yl)pyridine (1.2 g, crude) as a light yellow solid. LCMS (ESI) [M+H]$^+$=287.1.

Step 8: 8-Chloro-7-fluoro-6-[4-methyl-6-(1,3-oxazol-2-yl)pyridin-3-yl]isoquinolin-3-amine

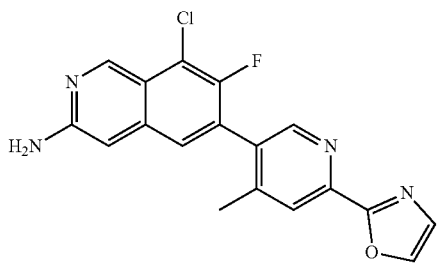 [SMILES: Cc1cc(-c2ncco2)ncc1-c1cc2cc(N)ncc2c(Cl)c1F]

A mixture of 8-chloro-7-fluoro-6-iodoisoquinolin-3-amine (550 mg, 1.71 mmol), 4-methyl-2-(1,3-oxazol-2-yl)-5-(tetramethyl-1,3,2-dioxaborolan-2-yl)pyridine (1.2 g, 4.19 mmol), potassium carbonate (825 mg, 5.97 mmol) and [1,1'-bis(diphenylphosphino)ferrocene]dichloropalladium (II) (125 mg, 0.17 mmol) in 1,4-dioxane (25 mL) and water (5 mL) was stirred for 2 h at 90° C. After filtration, the filtrate was concentrated under vacuum. The residue was purified on a silica gel column eluted with dichloromethane/methanol (10/1) to afford 8-chloro-7-fluoro-6-[4-methyl-6-(1,3-oxazol-2-yl)pyridin-3-yl]isoquinolin-3-amine (580 mg 95%) as a brown solid. LCMS (ESI) [M+H]$^+$=355.1.

Step 9: 2-([8-Chloro-7-fluoro-6-[4-methyl-6-(1,3-oxazol-2-yl)pyridin-3-yl]isoquinolin-3-yl]amino)-6-methyl-4-methylidene-4H,5H,6H,7H,8H-pyrazolo[1,5-d][1,4]diazepin-7-one

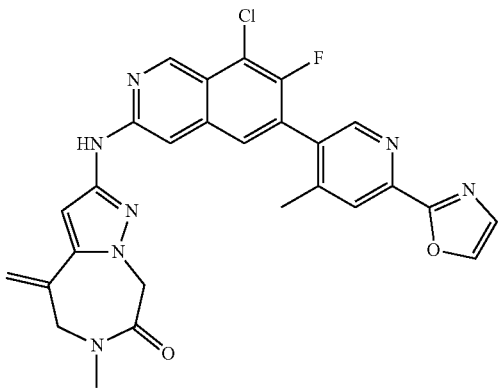

A mixture of 8-chloro-7-fluoro-6-[4-methyl-6-(1,3-oxazol-2-yl)pyridin-3-yl]isoquinolin-3-amine (700 mg, 1.97 mmol), 2-bromo-6-methyl-4-methylidene-4H,5H,6H,7H,8H-pyrazolo[1,5-d][1,4]diazepin-7-one (1.2 g, 4.69 mmol), 3rd generation t-BuBrettPhos precatalyst (675 mg, 0.79 mmol), t-BuBrettPhos (403 mg, 0.83 mmol) and cesium carbonate (3.2 g, 9.82 mmol) in 1,4-dioxane (80 mL) was stirred for 1.5 h at 110° C. The mixture was then filtered. The filtrate was concentrated. After concentrated under vacuum, the residue was purified on a silica gel column eluted with dichloromethane/methanol (15:1) to afford 2-([8-chloro-7-fluoro-6-[4-methyl-6-(1,3-oxazol-2-yl)pyridin-3-yl]isoquinolin-3-yl]amino)-6-methyl-4-methylidene-4H,5H,6H,7H,8H-pyrazolo[1,5-d][1,4]diazepin-7-one (300 mg, 29%) as a yellow solid. LCMS (ESI) [M+H]$^+$=530.3.

Step 10: 2-([8-Chloro-7-fluoro-6-[4-methyl-6-(1,3-oxazol-2-yl)pyridin-3-yl]isoquinolin-3-yl]amino)-4,6-dimethyl-4H,5H,6H,7H,8H-pyrazolo[1,5-d][1,4]diazepin-7-one

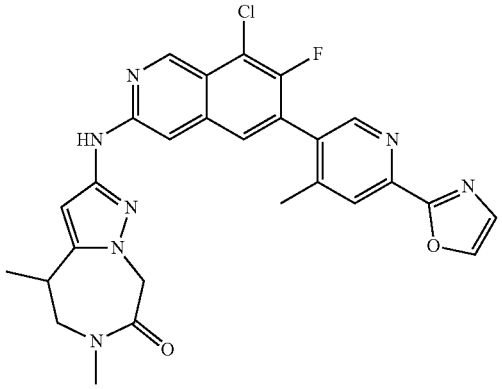 [SMILES: C=C1CN(C)C(=O)Cn2nc(Nc3cc4cc(-c5cnc(-c6ncco6)cc5C)c(F)c(Cl)c4cn3)cc21]

To a mixture of 2-([8-chloro-7-fluoro-6-[4-methyl-6-(1,3-oxazol-2-yl)pyridin-3-yl]isoquinolin-3-yl]amino)-6-methyl-4-methylidene-4H,5H,6H,7H,8H-pyrazolo[1,5-d][1,4]diazepin-7-one (300 mg, 0.57 mmol) in methanol (90 mL) and dichloromethane (10 mL) was added palladium on carbon (30.12 mg, 0.28 mmol). The reaction was stirred under hydrogen (2 atom) for 2 h at room temperature and then filtered. The filtrate was concentrated under vacuum to afford 2-([8-chloro-7-fluoro-6-[4-methyl-6-(1,3-oxazol-2-yl)pyridin-3-yl]isoquinolin-3-yl]amino)-4,6-dimethyl-4H, 5H,6H,7H,8H-pyrazolo[1,5-d][1,4]diazepin-7-one (130 mg, 43%) as a yellow solid. LCMS (ESI) [M+H]+=532.3.

Step 11: Tert-butyl N-[3-([4,6-dimethyl-7-oxo-4H, 5H,6H,7H,8H-pyrazolo[1,5-d][1,4]diazepin-2-yl] amino)-7-fluoro-6-[4-methyl-6-(1,3-oxazol-2-yl) pyridin-3-yl]isoquinolin-8-yl]carbamate

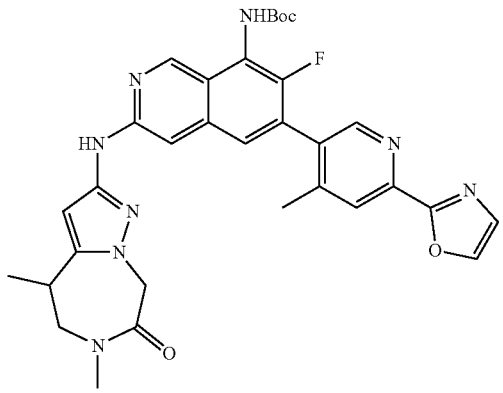 [SMILES: Cc1cc(-c2ncco2)ncc1-c1cc2cc(Nc3cc4n(n3)CC(=O)N(C)CC4C)ncc2c(NC(=O)OC(C)(C)C)c1F]

A mixture of 2-([8-chloro-7-fluoro-6-[4-methyl-6-(1,3-oxazol-2-yl)pyridin-3-yl]isoquinolin-3-yl]amino)-4,6-dimethyl-4H,5H,6H,7H,8H-pyrazolo[1,5-d][1,4]diazepin-7-one (100 mg, 0.19 mmol), tert-butyl carbamate (550 mg, 4.70 mmol), tris(dibenzylideneacetone)dipalladium-chloroform adduct (30 mg, 0.03 mmol), BrettPhos (20 mg, 0.04 mmol) and cesium carbonate (300 mg, 0.92 mmol) in 1,4-dioxane (10 mL) was stirred for 2 h at 90° C. and then filtered. After concentrated under vacuum, the residue was purified on a silica gel column eluted with dichloromethane/methanol (10:1) to afford tert-butyl N-[3-([4,6-dimethyl-7-oxo-4H, 5H,6H,7H,8H-pyrazolo[1,5-d][1,4]diazepin-2-yl]amino)-7-fluoro-6-[4-methyl-6-(1,3-oxazol-2-yl)pyridin-3-yl]isoquinolin-8-yl]carbamate (100 mg, 87%) as a brown oil. LCMS (ESI) [M+H]+=613.4.

Step 12: 2-([8-Amino-7-fluoro-6-[4-methyl-6-(1,3-oxazol-2-yl)pyridin-3-yl]isoquinolin-3-yl]amino)-4, 6-dimethyl-4H,5H,6H,7H,8H-pyrazolo[1,5-d][1,4] diazepin-7-one

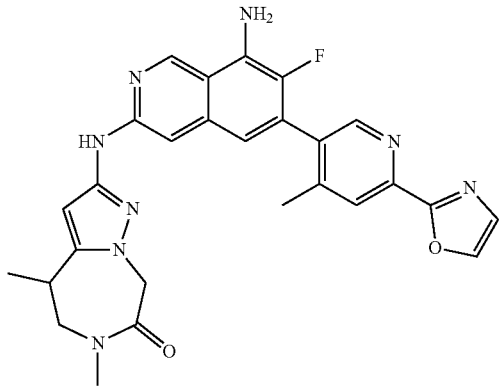 [SMILES: Cc1cc(-c2ncco2)ncc1-c1cc2cc(Nc3cc4n(n3)CC(=O)N(C)CC4C)ncc2c(N)c1F]

A mixture of tert-butyl N-[3-([4,6-dimethyl-7-oxo-4H, 5H,6H,7H,8H-pyrazolo[1,5-d][1,4]diazepin-2-yl]amino)-7-fluoro-6-[4-methyl-6-(1,3-oxazol-2-yl)pyridin-3-yl]isoquinolin-8-yl]carbamate (100 mg, 0.16 mmol) in DCM (5 mL) and TFA (5 mL) was stirred for 1.5 h at room temperature. The resulting mixture was concentrated under vacuum. The pH value of the solution was adjusted to 10 with NH₃ in methanol (7 M). The crude product was purified directly by Prep-HPLC (XBridge Prep C18 OBD Column19*15 mm Sum; 10 mmol sodium bicarbonate in water: ACN (50%~77%) in 8 min) to afford 2-([8-amino-7-fluoro-6-[4-methyl-6-(1,3-oxazol-2-yl)pyridin-3-yl]isoquinolin-3-yl]amino)-4,6-dimethyl-4H,5H,6H,7H,8H-pyrazolo[1,5-d][1, 4]diazepin-7-one (22.5 mg, 27%) as a yellow solid. LCMS (ESI) [M+H]+=513.3. ¹HNMR (400 MHz, DMSO) δ 9.29 (s, 1H), 9.13 (s, 1H), 8.57 (s, 1H), 8.35 (s, 1H), 8.12 (s, 1H), 7.74 (s, 1H), 7.50 (s, 1H), 6.86-6.84 (m, 1H), 6.17 (s, 2H), 6.04 (s, 1H), 5.13-4.81 (m, 2H), 3.84-3.77 (m, 1H), 3.68-3.63 (m, 1H), 3.30-3.26 (m, 1H), 2.97 (s, 3H), 2.33 (s, 3H), 1.26 (d, J=7.2 Hz, 3H).

Example 202

(1S,2S,3S)—N-(8-amino-7-fluoro-6-(4-methylpyridin-3-yl)isoquinolin-3-yl)-2-(1H-imidazol-5-yl)-3-methylcyclopropane-1-carboxamide (Compound 322)

(1S,2S,3R)—N-(8-amino-7-fluoro-6-(4-methylpyridin-3-yl)isoquinolin-3-yl)-2-(1H-imidazol-5-yl)-3-methylcyclopropane-1-carboxamide (Compound 321)

(1R,2R,3R)—N-(8-amino-7-fluoro-6-(4-methylpyridin-3-yl)isoquinolin-3-yl)-2-(1H-imidazol-5-yl)-3-methylcyclopropane-1-carboxamide (Compound 320) and (1R,2R,3S)—N-(8-amino-7-fluoro-6-(4-methylpyridin-3-yl)isoquinolin-3-yl)-2-(1H-imidazol-5-yl)-3-methylcyclopropane-1-carboxamide (Compound 319)

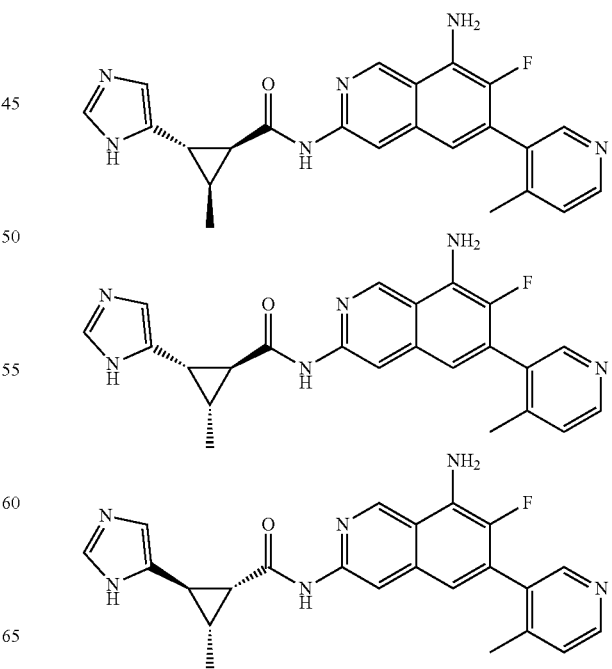

-continued

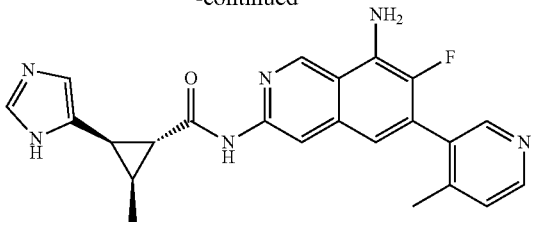

Step 1: methyl (2E)-3-[1-(triphenylmethyl)-1H-imidazol-5-yl]prop-2-enoate

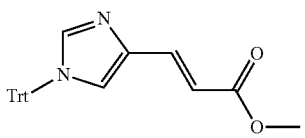

A mixture of 1-(triphenylmethyl)-1H-imidazole-5-carbaldehyde (10 g, 29.55 mmol) and methyl 2-(triphenyl-lambda5-phosphanylidene)acetate (9.88 g, 29.55 mmol) in tetrahydrofuran (150 mL) was stirred for 3 h at 70° C. The resulting mixture was concentrated under vacuum. The residue was purified by flash chromatography on silica gel eluting with ethyl acetate/petroleum ether (1/10) to afford methyl (2E)-3-[1-(triphenylmethyl)-1H-imidazol-5-yl]prop-2-enoate (10 g, 25.38 mmol) as a white solid. LCMS (ESI) [M+H]$^+$=395

Step 2: trans-methyl 2-methyl-3-[1-(triphenylmethyl)-1H-imidazol-4-yl]cyclopropane-1-carboxylate

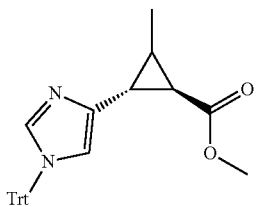

To a mixture of ethyldiphenylsulfanium; trifluoro(lambda2-fluoranidyl)boranuide (15 g, 49.64 mmol) in ethylene glycol dimethyl ether (100 mL) and dichloromethane (10 mL) was added lithium diisopropylamide (25 mL, 466.75 mmol) at −78° C. under nitrogen. The reaction was stirred for 30 mins at −78° C. Methyl (2E)-3-[1-(triphenylmethyl)-1H-imidazol-4-yl]prop-2-enoate (6.8 g, 17.23 mmol) was added. The reaction was stirred for 5 h at −78° C. The reaction was quenched with ice water. The resulting mixture was extracted with ethyl acetate and dried with anhydrous sodium sulfate. After filtration, the filtrate was concentrated under vacuum. The residue was purified by silica gel flash chromatography eluting with dichloromethane/methanol (10/1) to afford trans-methyl 2-methyl-3-[1-(triphenylmethyl)-1H-imidazol-4-yl]cyclopropane-1-carboxylate (3 g, 7.10 mmol) as a white solid. LCMS (ESI) [M+H]$^+$=423

Step 3: trans-2-methyl-3-[1-(triphenylmethyl)-1H-imidazol-4-yl]cyclopropane-1-carboxylic Acid

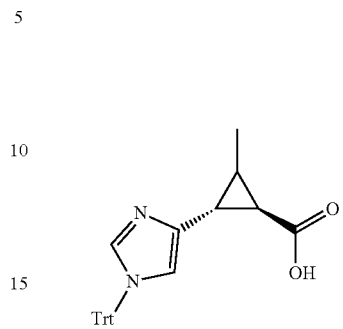

A mixture of trans-methyl 2-methyl-3-[1-(triphenylmethyl)-1H-imidazol-4-yl]cyclopropane-1-carboxylate (3 g, 7.10 mmol) and LiOH (853 mg, 35.61 mmol) in methanol (20 mL) and water (20 mL) was stirred for 12 h at room temperature. The reaction mixture was adjusted to pH 5 with hydrogen chloride. The resulting solution was extracted with of ethyl acetate and the organic layers combined and concentrated under vacuum to afford trans-2-methyl-3-[1-(triphenylmethyl)-1H-imidazol-4-yl]cyclopropane-1-carboxylic acid (1.26 g, 3.08 mmol) as a white solid. LCMS (ESI) [M+H]$^+$=409.

Step 4: trans-N-[8-chloro-7-fluoro-6-(4-methylpyridin-3-yl)isoquinolin-3-yl]-2-methyl-3-[1-(triphenylmethyl)-1H-imidazol-4-yl]cyclopropane-1-carboxamide

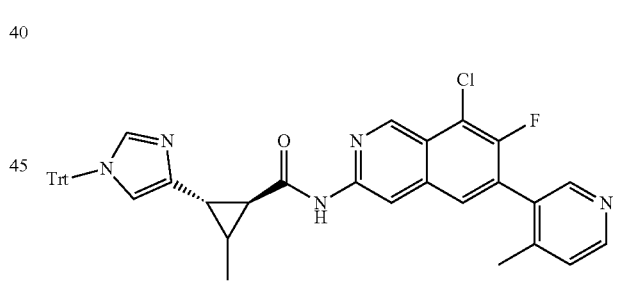

A mixture of 8-chloro-7-fluoro-6-(4-methylpyridin-3-yl)isoquinolin-3-amine (886 mg, 3.07 mmol), trans-2-methyl-3-[1-(triphenylmethyl)-1H-imidazol-4-yl]cyclopropane-1-carboxylic acid (1.26 g, 3.08 mmol) and Pyridine (5 mL, 62.118 mmol) in dichloromethane (50 mL) was added phosphorus oxychloride (1.4 g, 9.13 mmol) at 0° C. and then was stirred for 30 min at 0° C. The reaction was then quenched with water. The resulting mixture was washed with water. The organic phase was dried with anhydrous sodium sulfate. After filtration, the filtrate was concentrated under vacuum. The residue was purified by silica gel column with dichloromethane/methanol (10/1) to afford trans-N-[8-chloro-7-fluoro-6-(4-methylpyridin-3-yl)isoquinolin-3-yl]-2-methyl-3-[1-(triphenylmethyl)-1H-imidazol-4-yl]cyclopropane-1-carboxamide (500 mg, 0.73 mmol) as a white solid. LCMS (ESI) [M+H]$^+$=678.

Step 5: trans-tert-butyl N-(7-fluoro-3-[[2-methyl-3-[1-(triphenylmethyl)-1H-imidazol-4-yl]cyclopropane]amido]-6-(4-methylpyridin-3-yl)isoquinolin-8-yl)carbamate

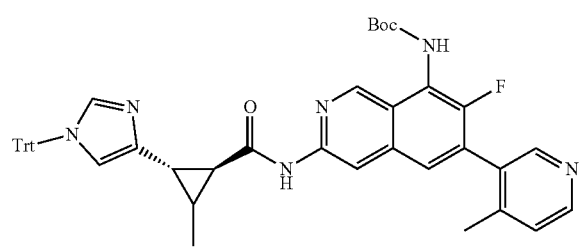

A mixture of tert-butyl carbamate (5.2 g, 44.38 mmol), trans-N-[8-chloro-7-fluoro-6-(4-methylpyridin-3-yl)isoquinolin-3-yl]-2-methyl-3-[1-(triphenylmethyl)-1H-imidazol-4-yl]cyclopropane-1-carboxamide (1.5 g, 2.21 mmol), tris(dibenzylideneacetone)dipalladium-chloroform adduct (460 mg, 0.44 mmol), BrettPhos (478 mg, 0.89 mmol) and cesium carbonate (2.89 g, 8.87 mmol) in dioxane (30 mL) was stirred for 3 h at 90° C. under nitrogen. After filtration, the filtrate was concentrated under vacuum. The residue was purified by silica gel flash chromatography eluting with dichloromethane/methanol (9/1) to afford tert-butyl N-(7-fluoro-3-[[(1S,3S)-2-methyl-3-[1-(triphenylmethyl)-1H-imidazol-4-yl]cyclopropane]amido]-6-(4-methylpyridin-3-yl)isoquinolin-8-yl)carbamate (1 g, 1.32 mmol) as a white solid. LCMS (ESI) [M+H]$^+$=759.

Step 6: (1S,2S,3S)—N-[8-amino-7-fluoro-6-(4-methylpyridin-3-yl)isoquinolin-3-yl]-2-(1H-imidazol-5-yl)-3-methylcyclopropane-1-carboxamide, (1R,2R,3R)—N-[8-amino-7-fluoro-6-(4-methylpyridin-3-yl)isoquinolin-3-yl]-2-(1H-imidazol-5-yl)-3-methylcyclopropane-1-carboxamide, (1S,2S,3R)—N-[8-amino-7-fluoro-6-(4-methylpyridin-3-yl)isoquinolin-3-yl]-2-(1H-imidazol-5-yl)-3-methylcyclopropane-1-carboxamide and (1R,2R,3S)—N-[8-amino-7-fluoro-6-(4-methylpyridin-3-yl)isoquinolin-3-yl]-2-(1H-imidazol-5-yl)-3-methylcyclopropane-1-carboxamide

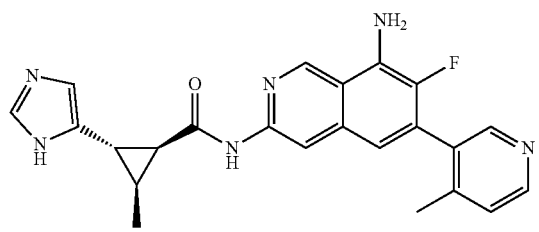

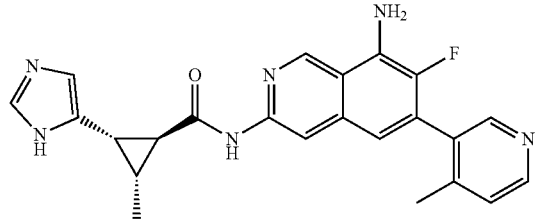

-continued

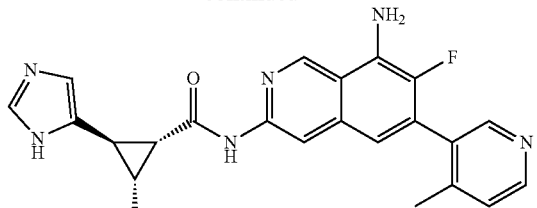

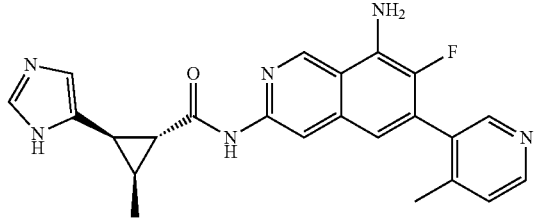

A mixture of trans-tert-butyl N-(7-fluoro-3-[[2-methyl-3-[1-(triphenylmethyl)-1H-imidazol-4-yl]cyclopropane]amido]-6-(4-methylpyridin-3-yl)isoquinolin-8-yl)carbamate (1 g, 1.31 mmol) in trifluoroacetic acid (10 mL) was stirred for 1 h at room temperature. The resulting mixture was concentrated under vacuum. The residue was purified by reverse phase chromatography (acetonitrile 0-50/0.1% sodium bicarbonate in water) to afford the mixture (500 mg, 1.20 mmol) as a yellow solid. The mixture was separated by Prep-SFC to afford four isomers (Cyclopropane stereochemistry for the isomers: imidazole trans to amide; methyl relative stereochemistry arbitrarily assigned; All absolute stereochemistry arbitrarily assigned): Compound 321: (84.9 mg, 0.20 mmol) as a yellow solid, Retention time:1.25 min (CHIRALPAK IC, 3.0*100 mm, 3[m; MeOH (0.1% DEA); 2 ml/min); LCMS (ESI) [M+H]$^+$=417; $^1$HNMR (400 MHz, DMSO) δ 11.76 (s, 1H), 10.68 (s, 1H), 9.40 (s, 1H), 8.51 (d, J=4.0 Hz, 1H), 8.42 (s, 1H), 8.34 (s, 1H), 7.48 (s, 1H), 7.40-7.38 (m, 1H), 6.95-6.93 (m, 2H), 6.27 (s, 2H), 2.39-2.32 (m, 1H), 2.29-2.27 (m, 1H), 2.19 (s, 3H), 1.75-1.70 (m, 1H), 1.29-1.27 (m, 3H). Compound 322: (123.9 mg, 0.29 mmol) as a yellow solid, Retention time:1.47 min (CHIRALPAK IC, 3.0*100 mm, 3 μm; MeOH (0.1% DEA); 2 ml/min); LCMS (ESI) [M+H]$^+$=417; $^1$HNMR (400 MHz, DMSO) δ 11.76 (s, 1H), 10.68 (s, 1H), 9.40 (s, 1H), 8.51 (d, J=4.0 Hz, 1H), 8.42 (s, 1H), 8.34 (s, 1H), 7.48 (s, 1H), 7.40-7.38 (m, 1H), 6.95-6.93 (m, 2H), 6.27 (s, 2H), 2.39-2.32 (m, 1H), 2.29-2.27 (m, 1H), 2.19 (s, 3H), 1.75-1.70 (m, 1H), 1.29-1.27 (m, 3H). Compound 320: (110.2 mg, 0.26 mmol) as a yellow solid. Retention time: 1.63 min (CHIRALPAK IC, 3.0*100 mm, 3 μm; MeOH (0.1% DEA); 2 ml/min); LCMS (ESI) [M+H]$^+$=417; $^1$HNMR (400 MHz, DMSO) δ 11.76 (s, 1H), 10.68 (s, 1H), 9.40 (s, 1H), 8.51-8.50 (d, J=4.0 Hz, 1H), 8.42 (s, 1H), 8.34 (s, 1H), 7.48 (s, 1H), 7.40-7.38 (m, 1H), 6.95-6.93 (m, 2H), 6.27 (s, 2H), 2.39-2.32 (m, 1H), 2.29-2.27 (m, 1H), 2.19 (s, 3H), 1.75-1.70 (m, 1H), 1.29-1.27 (m, 3H). Compound 319: (168.9 mg, 0.40 mmol) as a yellow solid. Retention time:2.20 min (CHIRALPAK IC, 3.0*100 mm, 3 μm; MeOH (0.1% DEA); 2 ml/min); LCMS (ESI) [M+H]$^+$=417; $^1$HNMR (400 MHz, DMSO) δ 11.76 (s, 1H), 10.68 (s, 1H), 9.40 (s, 1H), 8.51-8.50 (d, J=4.0 Hz, 1H), 8.42 (s, 1H), 8.34 (s, 1H), 7.48 (s, 1H), 7.40-7.38 (m, 1H), 6.95-6.93 (m, 2H), 6.27 (s, 2H), 2.39-2.32 (m, 1H), 2.29-2.27 (m, 1H), 2.19 (s, 3H), 1.75-1.70 (m, 1H), 1.29-1.27 (m, 3H).

Example 203

(±)-N-(8-amino-7-fluoro-6-(4-methylpyridin-3-yl)isoquinolin-3-yl)-2-(hydroxymethyl)-3-(1-methyl-1H-pyrazol-4-yl)cyclopropane-1-carboxamide (Compound 328)

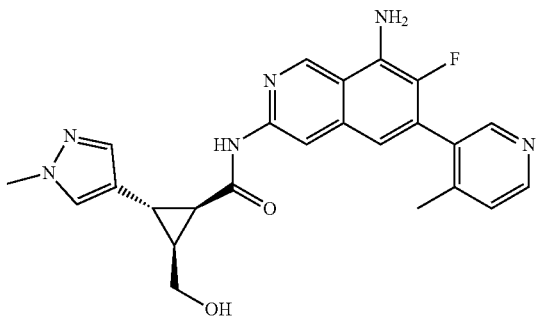

Step 1: 6-(1-methyl-1H-pyrazol-4-yl)-3-oxabicyclo[3.1.0]hexan-2-one

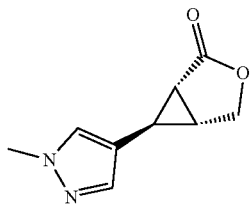

A solution of (2E)-3-(1-methyl-1H-pyrazol-4-yl)prop-2-en-1-yl 2-diazoacetate (100 mg, 0.48 mmol) and tert-butyl [(tert-butyldimethylsilyl)cuprio]dimethylsilane (7.1 mg, 0.024 mmol) in toluene (3 mL) was stirred for 2 hours at reflux. The resulting solution was concentrated under vacuum. The residue was purified by flash chromatography on silica gel eluting with petroleum ether/ethyl acetate (2/1) to afford 6-(1-methyl-H-pyrazol-4-yl)-3-oxabicyclo[3.1.0]hexan-2-one (25 mg, 0.14 mmol) as a yellow oil. LCMS (ESI) [M+H]$^+$=179.1.

Step 2: N-[8-chloro-7-fluoro-6-(4-methylpyridin-3-yl)isoquinolin-3-yl]-2-(hydroxymethyl)-3-(1-methyl-1H-pyrazol-4-yl)cyclopropane-1-carboxamide

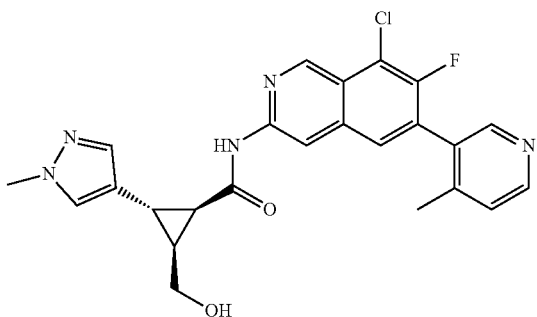 [SMILES: Cc1ccncc1-c1cc2cc(NC(=O)[C@H]3[C@@H](CO)[C@@H]3c3cnn(C)c3)ncc2c(Cl)c1F]

To a solution 6-(1-methyl-1H-pyrazol-4-yl)-3-oxabicyclo[3.1.0]hexan-2-one (200 mg, 1.12 mmol) in THF (5 mL) was added LiHMDS (1.35 mL, 8.07 mmol) at 0° C. The mixture was then stirred at 0° C. for 30 min. Then 8-chloro-7-fluoro-6-(4-methylpyridin-3-yl)isoquinolin-3-amine (287 mg, 0.99 mmol) was added. The mixture was stirred for 2 h at room temperature.

The reaction was then quenched by water. The resulting mixture was extracted with ethyl acetate, dried with anhydrous sodium sulfate. After filtration, the filtrate was concentrated under vacuum. The residue was purified by flash chromatography on silica gel eluting with ethyl acetate/petroleum ether (1/1) to afford N-[8-chloro-7-fluoro-6-(4-methylpyridin-3-yl)isoquinolin-3-yl]-2-(hydroxymethyl)-3-(1-methyl-1H-pyrazol-4-yl)cyclopropane-1-carboxamide (150 mg, 29%) as a yellow solid.

Step 3: N-[8-chloro-7-fluoro-6-(4-methylpyridin-3-yl)isoquinolin-3-yl]-2-(1-methyl-1H-pyrazol-4-yl)-3-[(oxan-2-yloxy)methyl]cyclopropane-1-carboxamide

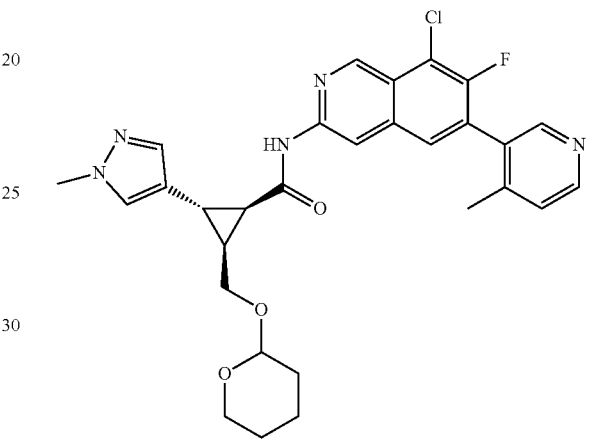

A mixture of N-[8-chloro-7-fluoro-6-(4-methylpyridin-3-yl)isoquinolin-3-yl]-2-(hydroxymethyl)-3-(1-methyl-1H-pyrazol-4-yl)cyclopropane-1-carboxamide (150 mg, 0.32 mmol), 3,4-dihydro-2H-pyran (140 mg, 1.66 mmol), TsOH (10 mg, 0.058 mmol) in tetrahydrofuran (5 mL) was stirred for 12 h at room temperature. The resulting solution was concentrated under vacuum. The residue was purified by flash chromatography on silica gel eluting with dichloromethane/methanol (20/1) to afford N-[8-chloro-7-fluoro-6-(4-methylpyridin-3-yl)isoquinolin-3-yl]-2-(1-methyl-1H-pyrazol-4-yl)-3-[(oxan-2-yloxy)methyl]cyclopropane-1-carboxamide (95 mg, 54%) as a yellow solid.

Step 4: tert-butyl N-(7-fluoro-3-[[2-(1-methyl-H-pyrazol-4-yl)-3-[(oxan-2-yloxy)methyl]cyclopropane]amido]-6-(4-methylpyridin-3-yl)isoquinolin-8-yl)carbamate

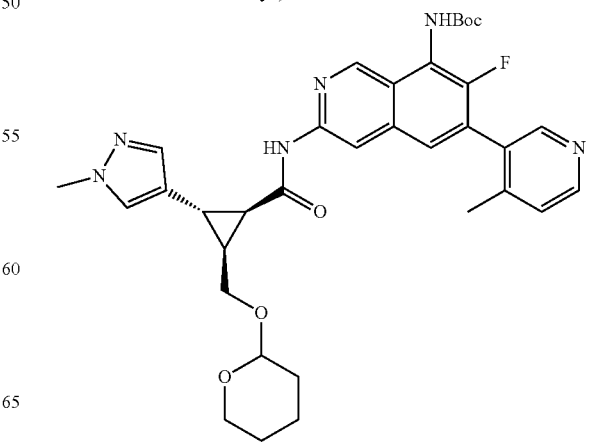

883

A mixture of N-[8-chloro-7-fluoro-6-(4-methylpyridin-3-yl)isoquinolin-3-yl]-2-(1-methyl-1H-pyrazol-4-yl)-3-[(oxan-2-yloxy)methyl]cyclopropane-1-carboxamide (95 mg, 0.17 mmol), Pd$_2$(dba)$_3$ (30 mg, 0.033 mmol), tert-butyl carbamate (510 mg, 4.35 mmol), BrettPhos (30 mg, 0.056 mmol), cesium carbonate (280 mg, 0.86 mmol), 1,4-dioxane (3 mL) was stirred for 2 h at 90° C. The resulting mixture was concentrated under vacuum. The residue was purified by flash chromatography on silica gel eluting with dichloromethane/methanol (20/1) to afford tert-butyl N-(7-fluoro-3-[[2-(1-methyl-1H-pyrazol-4-yl)-3-[(oxan-2-yloxy)methyl]cyclopropane]amido]-6-(4-methylpyridin-3-yl)isoquinolin-8-yl)carbamate (60 mg, 55%) as a yellow solid.

Step 5: N-[8-amino-7-fluoro-6-(4-methylpyridin-3-yl)isoquinolin-3-yl]-2-(hydroxymethyl)-3-(1-methyl-H-pyrazol-4-yl)cyclopropane-1-carboxamide

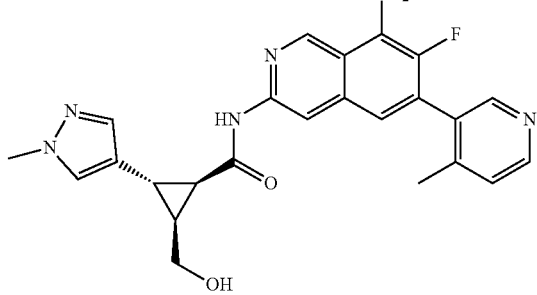

To a solution of tert-butyl N-(7-fluoro-3-[[2-(1-methyl-H-pyrazol-4-yl)-3-[(oxan-2-yloxy)methyl]cyclopropane]amido]-6-(4-methylpyridin-3-yl)isoquinolin-8-yl)carbamate (60 mg, 0.095 mmol) and trifluoroacetic acid (2 mL) in dichloromethane (2 mL) was stirred for 2 h at room temperature. The resulting mixture was concentrated under vacuum. The residue was purified by Prep-HPLC to afford N-[8-amino-7-fluoro-6-(4-methylpyridin-3-yl)isoquinolin-3-yl]-2-(hydroxymethyl)-3-(1-methyl-1H-pyrazol-4-yl)cyclopropane-1-carboxamide (7.1 mg, 17%) as a yellow solid. LCMS (ESI) [M+H]$^+$=447.3, 2.187 mins, K; $^1$HNMR (300 MHz, CD$_3$OD) δ 9.303 (s, 1H), 8.47 (d, J=5.1 Hz, 1H), 8.42 (s, 1H), 8.36 (s, 1H), 7.51 (s, 1H), 7.44 (s, J=5.1 Hz, 1H), 7.38 (s, 1H), 7.00 (d, J=6.0 Hz, 1H), 3.99-3.88 (m, 2H), 3.86 (s, 3H), 2.32-2.24 (m, 1H), 2.32 (s, 3H), 2.28-2.24 (m, 1H), 1.93-1.84 (m, 1H).

Example 204 and Example 205

(1R,2S)—N-(8-amino-7-fluoro-6-(4-methylpyridin-3-yl)isoquinolin-3-yl)-2-(hydroxymethyl)cyclopropane-1-carboxamide (Compound 327) and (1S,2R)—N-(8-amino-7-fluoro-6-(4-methylpyridin-3-yl)isoquinolin-3-yl)-2-(hydroxymethyl)cyclopropane-1-carboxamide (Compound 326)

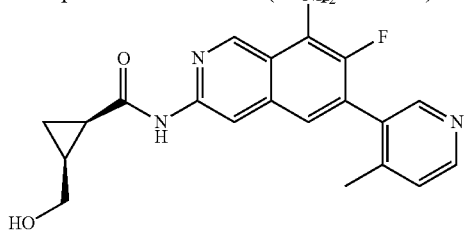

884

-continued

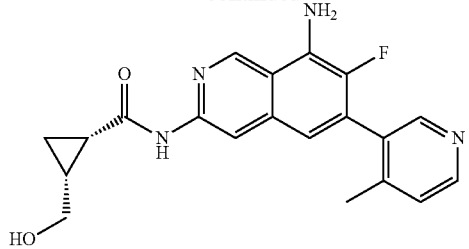

Step 1: 3-[8-chloro-7-fluoro-6-(4-methylpyridin-3-yl)isoquinolin-3-yl]-3-azabicyclo[3.1.0]hexane-2,4-dione

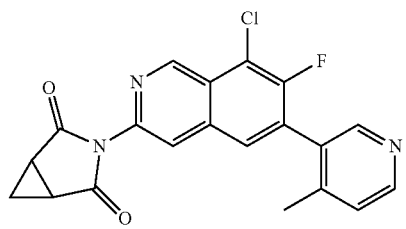 [SMILES: Cc1ccncc1-c1cc2cc(N3C(=O)C4CC4C3=O)ncc2c(Cl)c1F]

A mixture of 3-oxabicyclo[3.1.0]hexane-2,4-dione (390 mg, 3.48 mmol), 8-chloro-7-fluoro-6-(4-methylpyridin-3-yl)isoquinolin-3-amine (500 mg, 1.73 mmol), 4-dimethylaminopyridine (425 mg, 3.47 mmol) in dioxane (10 mL) was stirred for 12 h at 120° C. The resulting mixture was concentrated under vacuum. The residue was purified by silica gel column with dichloromethane/methanol (10/1) to afford 3-[8-chloro-7-fluoro-6-(4-methylpyridin-3-yl)isoquinolin-3-yl]-3-azabicyclo[3.1.0]hexane-2,4-dione (450 mg, 1.18 mmol) as a white solid. LCMS (ESI) [M+H]$^+$=382.

Step 2: tert-butyl N-(3-[2,4-dioxo-3-azabicyclo[3.1.0]hexan-3-yl]-7-fluoro-6-(4-methylpyridin-3-yl)isoquinolin-8-yl)carbamate

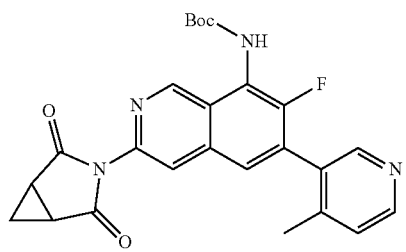 [SMILES: Cc1ccncc1-c1cc2cc(N3C(=O)C4CC4C3=O)ncc2c(NC(=O)OC(C)(C)C)c1F]

A mixture of tert-butyl carbamate (1.22 g, 10.41 mmol), 3-[8-chloro-7-fluoro-6-(4-methylpyridin-3-yl)isoquinolin-3-yl]-3-azabicyclo[3.1.0]hexane-2,4-dione (200 mg, 0.52 mmol), tris(dibenzylideneacetone)dipalladium-chloroform adduct (108 mg, 0.10 mmol), BrettPhos (112 mg, 0.20 mmol), cesium carbonate (682 mg, 2.09 mmol) in dioxane (20 mL) was stirred for 2 h at 90° C. After filtration, the filtrate was concentrated under vacuum. The residue was purified by flash chromatography on silica gel eluting with dichloromethane/methanol (10/1) to afford tert-butyl N-(3-[2,4-dioxo-3-azabicyclo[3.1.0]hexan-3-yl]-7-fluoro-6-(4- methylpyridin-3-yl)isoquinolin-8-yl)carbamate (150 mg, 0.32 mmol) as a brown solid. LCMS (ESI) [M+H]⁺=463

Step 3: Cis-tert-butyl N-(7-fluoro-3-[[2-(hydroxymethyl)cyclopropane]amido]-6-(4-methylpyridin-3-yl)isoquinolin-8-yl)carbamate

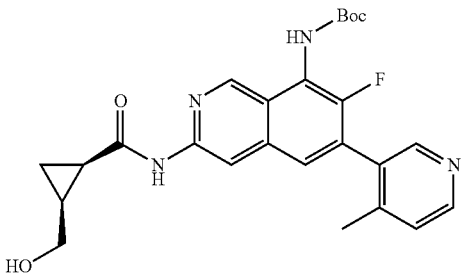 [SMILES: Cc1ccncc1-c1cc2cc(NC(=O)[C@@H]3C[C@@H]3CO)ncc2c(NC(=O)OC(C)(C)C)c1F]

To a mixture of tert-butyl N-(3-[2,4-dioxo-3-azabicyclo[3.1.0]hexan-3-yl]-7-fluoro-6-(4-methylpyridin-3-yl)isoquinolin-8-yl)carbamate (460 mg, 0.99 mmol) in methanol (30 mL) was added sodium borohydride (190 mg, 5.02 mmol). The mixture was stirred for 2 h at room temperature. The reaction was quenched with water. The resulting solution was extracted with ethyl acetate dried with anhydrous sodium sulfate. After filtration, the filtrate was concentrated under vacuum. The residue was purified by silica gel column with dichloromethane/methanol (10/1) to afford cis-tert-butyl N-(7-fluoro-3-[[2-(hydroxymethyl)cyclopropane]amido]-6-(4-methylpyridin-3-yl)isoquinolin-8-yl)carbamate (200 mg, 0.42 mmol) as a white solid. LCMS (ESI) [M+H]⁺=467.

Step 4: (1R,2S)—N-[8-amino-7-fluoro-6-(4-methylpyridin-3-yl)isoquinolin-3-yl]-2-(hydroxymethyl)cyclopropane-1-carboxamide and (1S,2R)—N-[8-amino-7-fluoro-6-(4-methylpyridin-3-yl)isoquinolin-3-yl]-2-(hydroxymethyl)cyclopropane-1-carboxamide

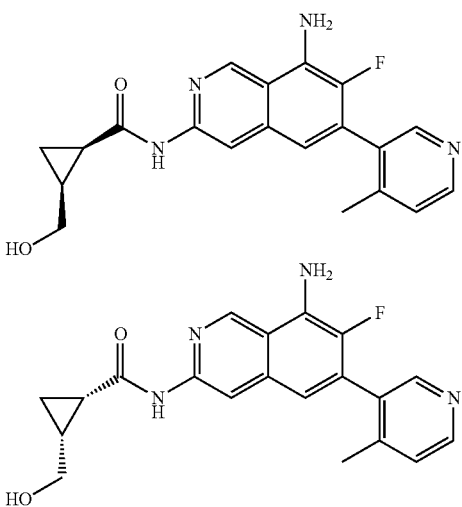

A mixture of cis-tert-butyl N-(7-fluoro-3-[[2-(hydroxymethyl)cyclopropane]amido]-6-(4-methylpyridin-3-yl)isoquinolin-8-yl)carbamate (200 mg, 0.42 mmol) in trifluoroacetic acid (5 mL) was stirred for 1 h at room temperature. The resulting mixture was concentrated under vacuum. The residue was purified by reverse phase chromatography (acetonitrile 0-50/0.1% sodium bicarbonate in water) to afford the racemic product (50 mg, 0.13 mmol) as a white solid. The racemate product was separated by Chiral-HPLC to afford two trans-isomers: Compound 327: Retention time: 3.04 min(Repaired Chiral IC, 0.46*10 cm; 5 µm; Hex (0.1% DEA):EtOH=50:50; 1 ml/min); LCMS (ESI) [M+H]⁺=367; ¹HNMR (400 MHz, CD₃OD) δ 9.28 (s, 1H), 8.45-8.44 (d, J=4.0 Hz, 1H), 8.39 (s, 1H), 8.31 (s, 1H), 7.42-7.41 (d, J=4.0 Hz, 1H), 6.98-6.96 (d, J=8.0 Hz, 1H), 3.86-3.82 (m, 1H), 3.75-3.70 (m, 1H), 2.29 (s, 3H), 2.08-2.02 (m, 1H), 1.64-1.59 (m, 1H), 1.15-1.10 (m, 2H). Compound 326: Retention time: 3.86 min (Repaired Chiral IC, 0.46*10 cm; 5 µm; Hex (0.1% DEA):EtOH=50:50; 1 ml/min); LCMS (ESI) [M+H]⁺=367; ¹HNMR (400 MHz, CD₃OD) δ 9.28 (s, 1H), 8.45-8.44 (d, J=4.0 Hz, 1H), 8.39 (s, 1H), 8.31 (s, 1H), 7.42-7.41 (d, J=4.0 Hz, 1H), 6.98-6.96 (d, J=8.0 Hz, 1H), 3.86-3.82 (m, 1H), 3.75-3.70 (m, 1H), 2.29 (s, 3H), 2.08-2.02 (m, 1H), 1.64-1.59 (m, 1H), 1.15-1.10 (m, 2H).

Example 206

2-((8-amino-7-fluoro-6-(4-methylpyridin-3-yl)isoquinolin-3-yl)amino)-6-(2,2,2-trifluoroethyl)-5,6-dihydro-4H-pyrazolo[1,5-d][1,4]diazepin-7(8H)-one (Compound 387)

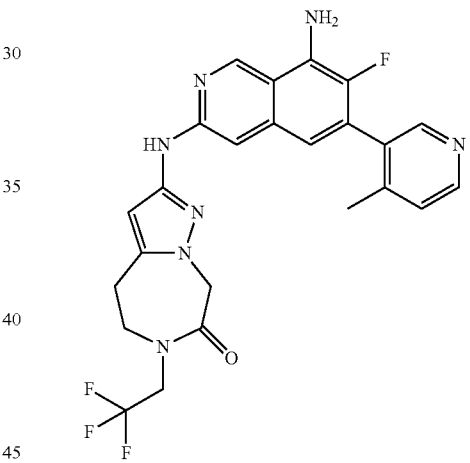

Step 1: 2-Bromo-6-(2,2,2-trifluoroethyl)-4H,5H,6H,7H,8H-pyrazolo[1,5-d][1,4]diazepin-7-one

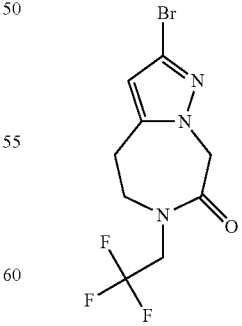

To a solution of 2-bromo-4H,5H,6H,7H,8H-pyrazolo[1,5-d][1,4]diazepin-7-one (1 g, 4.35 mmol) in THF/DMF (40 mL/4 mL) was added t-BuOK (1.5 g, 13.4 mmol) and 2,2,2-trifluoroethyl trifluoromethanesulfonate (5 g, 21.5 mmol). The resulting solution was stirred for 16 hours at room temperature. The crude product was purified by reversed-phase HPLC (C18 silica gel; 0.5% sodium bicarbonate in water: MeOH (5%70% in 50 min) to afford 2-bromo-6-(2,2,2-trifluoroethyl)-4H,5H,6H,7H,8H-pyrazolo[1,5-d][1,4]diazepin-7-one (300 mg, 22%) as a colorless oil. LCMS (ESI) [M+H]⁺=312.0.

Step 2: 2-[[8-Chloro-7-fluoro-6-(4-methylpyridin-3-yl)isoquinolin-3-yl]amino]-6-(2,2,2-trifluoroethyl)-4H,5H,6H,7H,8H-pyrazolo[1,5-d][1,4]diazepin-7-one

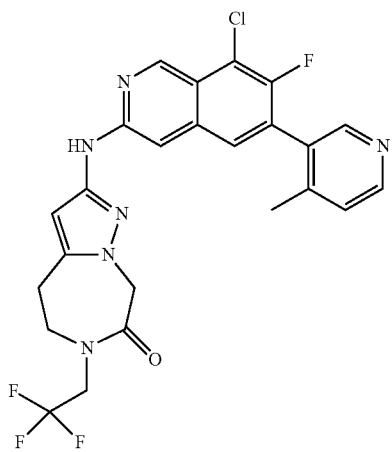 [SMILES: Cc1ccncc1-c1cc2cc(Nc3cc4n(n3)CC(=O)N(CC(F)(F)F)CC4)ncc2c(Cl)c1F]

A mixture of 8-chloro-7-fluoro-6-(4-methylpyridin-3-yl)isoquinolin-3-amine (100 mg, 0.35 mmol), 2-bromo-6-(2,2,2-trifluoroethyl)-4H,5H,6H,7H,8H-pyrazolo[1,5-d][1,4]diazepin-7-one (110 mg, 0.35 mmol), 3rd generation t-BuBrettPhos precatalyst (120 mg, 0.14 mmol), t-BuBrettPhos (75 mg, 0.16 mmol), cesium carbonate (570 mg, 1.75 mmol) and 1,4-dioxane (12 mL) was stirred for 1 h at 110° C. After filtration, the filtrate was concentrated under vacuum.

The residue was purified on a silica gel column eluted with dichloromethane/methanol (15/1) to afford 2-[[8-chloro-7-fluoro-6-(4-methylpyridin-3-yl)isoquinolin-3-yl]amino]-6-(2,2,2-trifluoroethyl)-4H,5H,6H,7H,8H-pyrazolo[1,5-d][1,4]diazepin-7-one (35 mg, 19%) as a yellow solid. LCMS (ESI) [M+H]⁺=519.2.

Step 3: Tert-butyl N-[7-fluoro-6-(4-methylpyridin-3-yl)-3-[[7-oxo-6-(2,2,2-trifluoroethyl)-4H,5H,6H,7H,8H-pyrazolo[1,5-d][1,4]diazepin-2-yl]amino]isoquinolin-8-yl]carbamate

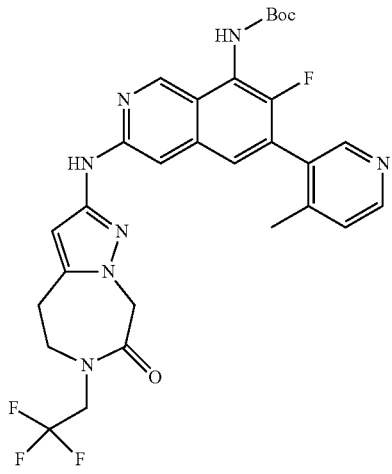 [SMILES: Cc1ccncc1-c1cc2cc(Nc3cc4n(n3)CC(=O)N(CC(F)(F)F)CC4)ncc2c(NC(=O)OC(C)(C)C)c1F]

A mixture of 2-[[8-chloro-7-fluoro-6-(4-methylpyridin-3-yl)isoquinolin-3-yl]amino]-6-(2,2,2-trifluoroethyl)-4H,5H,6H,7H,8H-pyrazolo[1,5-d][1,4]diazepin-7-one (150 mg, 0.29 mmol), tert-butyl carbamate (850 mg, 7.26 mmol), tris(dibenzylideneacetone)dipalladium-chloroformadduct (45 mg, 0.043 mmol), BrettPhos (30 mg, 0.056 mmol), cesium carbonate (472 mg, 1.45 mmol) in 1,4-dioxane (12 mL) was stirred for 2 h at 90° C. After filtration, the filtrate was concentrated under vacuum. The residue was purified on a silica gel column eluted with dichloromethane/methanol (10/1) to afford tert-butyl N-[7-fluoro-6-(4-methylpyridin-3-yl)-3-[[7-oxo-6-(2,2,2-trifluoroethyl)-4H,5H,6H,7H,8H-pyrazolo[1,5-d][1,4]diazepin-2-yl]amino]isoquinolin-8-yl]carbamate (40 mg, 23%) as a yellow solid. LCMS (ESI) [M+H]⁺=600.4.

Step 4: 2-[[8-Amino-7-fluoro-6-(4-methylpyridin-3-yl)isoquinolin-3-yl]amino]-6-(2,2,2-trifluoroethyl)-4H,5H,6H,7H,8H-pyrazolo[1,5-d][1,4]diazepin-7-one

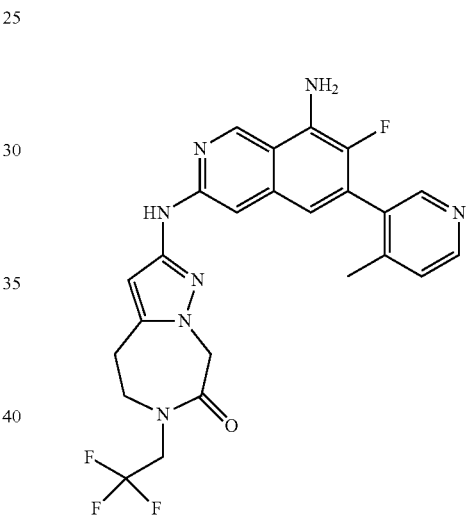

A solution of tert-butyl N-[7-fluoro-6-(4-methylpyridin-3-yl)-3-[[7-oxo-6-(2,2,2-trifluoroethyl)-4H,5H,6H,7H,8H-pyrazolo[1,5-d][1,4]diazepin-2-yl]amino]isoquinolin-8-yl]carbamate (40 mg, 0.067 mmol) in dichloromethane (2 mL) and trifluoroacetic acid (5 mL) was stirred for 2.5 h at room temperature. The resulting mixture was concentrated under vacuum.

The pH value of the solution was adjusted to 10 with NH₃ in methanol (7 M). The crude product was purified directly by Prep-HPLC (XBridge Prep C18 OBD Column19*15 mm 5 um; 10 mmol sodium bicarbonate in water: ACN (50%77%) in 8 min) to afford 2-[[8-amino-7-fluoro-6-(4-methylpyridin-3-yl)isoquinolin-3-yl]amino]-6-(2,2,2-trifluoroethyl)-4H,5H,6H,7H,8H-pyrazolo[1,5-d][1,4]diazepin-7-one (6.0 mg, 18%) as a yellow solid. LCMS (ESI) [M+H]⁺=500.1; ¹HNMR (300 MHz, MeOD) δ 9.14 (s, 1H), 8.44 (d, J=5.7 Hz, 1H), 8.39 (s, 1H), 7.64 (s, 1H), 7.41 (d, J=5.7 Hz, 1H), 6.85 (d, J=6.0 Hz, 1H), 6.06 (s, 1H), 5.11 (s, 2H), 4.25-4.22 (m, 2H), 4.07-4.03 (m, 2H), 3.19-3.17 (m, 2H), 2.30 (s, 3H).

Example 207

(1S,3R)—N-(8-amino-7-fluoro-6-(4-methylpyridin-3-yl)isoquinolin-3-yl)-2-(1H-imidazol-4-yl)-3-(1-methyl-1H-pyrazol-4-yl)cyclopropane-1-carboxamide (Compound 369) and (1R,3S)—N-(8-amino-7-fluoro-6-(4-methylpyridin-3-yl)isoquinolin-3-yl)-2-(1H-imidazol-4-yl)-3-(1-methyl-1H-pyrazol-4-yl)cyclopropane-1-carboxamide (Compound 370)

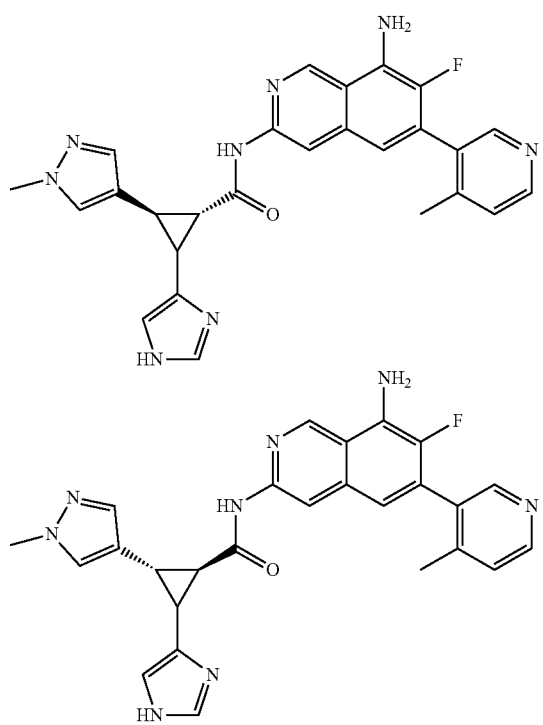

Step 1: 4-methyl-N'-[(1E)-[1-(triphenylmethyl)-1H-imidazol-4-yl]methylidene]benzene-1-sulfonohydrazide

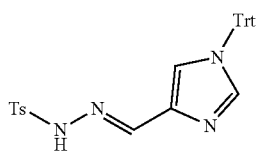

A mixture of 1-(triphenylmethyl)-1H-imidazole-4-carbaldehyde (10 g, 29.55 mmol), 4-methylbenzene-1-sulfonohydrazide (11 g, 59.06 mmol) in methanol (200 mL) and AcOH (0.5 mL) was stirred for 12 h at room temperature. After filtration, the solids were collected and washed by methanol (50 mL) to afford 4-methyl-N-[(1E)-[1-(triphenylmethyl)-1H-imidazol-4-yl]methylidene]benzene-1-sulfonohydrazide (10 g, 19.76 mmol) as a white solid. LCMS (ESI) [M+H]$^+$=507

Step 2: 2-(1-methyl-1H-pyrazol-4-yl)-3-[1-(triphenylmethyl)-1H-imidazol-4-yl]cyclopropane-1-carboxylate

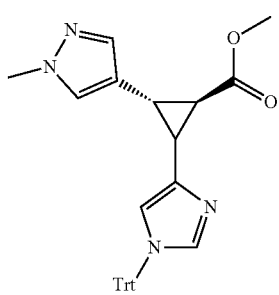

A mixture methyl (2E)-3-(1-methyl-1H-pyrazol-4-yl)prop-2-enoate (5 g, 30.08 mmol), 4-methyl-N-[(1E)-[1-(triphenylmethyl)-1H-imidazol-4-yl]methylidene]benzene-1-sulfonohydrazide (18.2 g, 35.92 mmol) in xylene (200 mL) was stirred for 4 h at 150° C. The resulting mixture was concentrated under vacuum. The residue was purified by flash chromatography on silica gel eluting with ethyl acetate to afford methyl 2-(1-methyl-1H-pyrazol-4-yl)-3-[1-(triphenylmethyl)-1H-imidazol-4-yl]cyclopropane-1-carboxylate (1.8 g, 3.68 mmol) as a brown solid. LCMS (ESI) [M+H]$^+$=489

Step 3: 2-(1-methyl-1H-pyrazol-4-yl)-3-[1-(triphenylmethyl)-1H-imidazol-4-yl]cyclopropane-1-carboxylic Acid

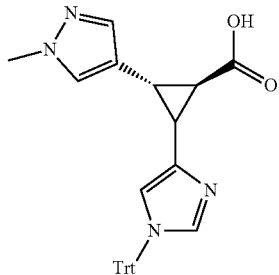

A mixture of methyl 2-(1-methyl-1H-pyrazol-4-yl)-3-[1-(triphenylmethyl)-1H-imidazol-4-yl]cyclopropane-1-carboxylate (700 mg, 1.43 mmol) and LiOH (172 mg, 7.18 mmol) in water (15 mL) and methanol (15 mL) was stirred for 12 h at room temperature. The reaction mixture was adjusted to pH 5 with hydrogen chloride (1N). The resulting mixture was extracted with ethyl acetate and dried with anhydrous sodium sulfate to afford 2-(1-methyl-1H-pyrazol-4-yl)-3-[1-(triphenylmethyl)-1H-imidazol-4-yl]cyclopropane-1-carboxylic acid (500 mg, 1.05 mmol) as a white solid. LCMS (ESI) [M+H]$^+$=475

Step 4: N-[8-chloro-7-fluoro-6-(4-methylpyridin-3-yl)isoquinolin-3-yl]-2-(1-methyl-1H-pyrazol-4-yl)-3-[1-(triphenylmethyl)-1H-imidazol-4-yl]cyclopropane-1-carboxamide

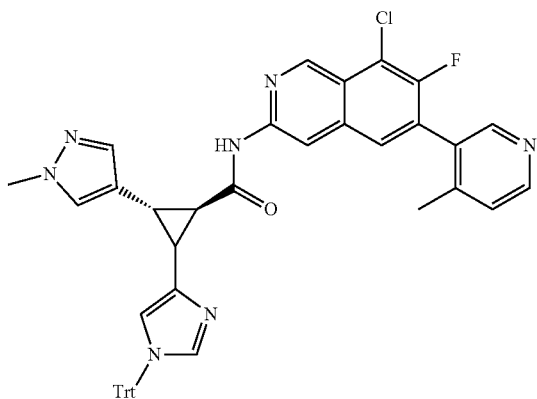

A mixture of 2-(1-methyl-1H-pyrazol-4-yl)-3-[1-(triphenylmethyl)-1H-imidazol-4-yl]cyclopropane-1-carboxylic acid (500 mg, 1.05 mmol), 8-chloro-7-fluoro-6-(4-methylpyridin-3-yl)isoquinolin-3-amine (302 mg, 1.05 mmol) and pyridine (4 mL) in dichloromethane (20 mL) was added phosphorus oxychloride (480 mg, 3.13 mmol) at 0° C. The resulting solution was stirred for 30 min at 0° C. The reaction was concentrated under vacuum. The residue was purified by silica gel column with dichloromethane/methanol (10/1) to afford trans-N-[8-chloro-7-fluoro-6-(4-methylpyridin-3-yl)isoquinolin-3-yl]-2-(1-methyl-1H-pyrazol-4-yl)-3-[1-(triphenylmethyl)-1H-imidazol-4-yl]cyclopropane-1-carboxamide (350 mg, 0.47 mmol) as a white solid. LCMS (ESI) [M+H]$^+$=744.

Step 5: tert-butyl N-(7-fluoro-3-[[2-(1-methyl-1H-pyrazol-4-yl)-3-[1-(triphenylmethyl)-1H-imidazol-4-yl]cyclopropane]amido]-6-(4-methylpyridin-3-yl)isoquinolin-8-yl)carbamate

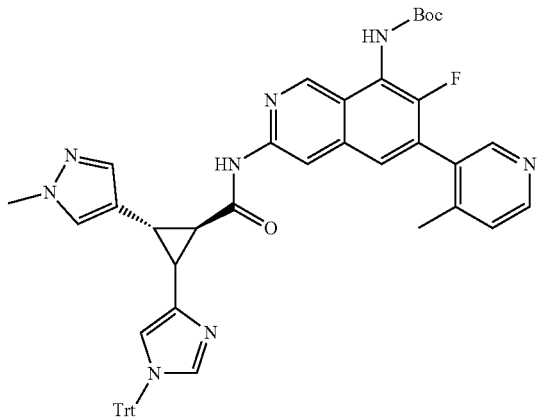

A mixture of N-[8-chloro-7-fluoro-6-(4-methylpyridin-3-yl)isoquinolin-3-yl]-2-(1-methyl-1H-pyrazol-4-yl)-3-[1-(triphenylmethyl)-1H-imidazol-4-yl]cyclopropane-1-carboxamide (250 mg, 0.33 mmol), tert-butyl carbamate (787 mg, 6.71 mmol), tris(dibenzylideneacetone)dipalladium-chloroform adduct (70 mg, 0.06 mmol), BrettPhos (72 mg, 0.13 mmol) and cesium carbonate (438 mg, 1.34 mmol) in dioxane (20 mL) was stirred for 3 h at 90° C. After filtration, the filtrate was concentrated under vacuum. The residue was purified by flash chromatography on silica gel eluting with dichloromethane/methanol (10/1) to afford tert-butyl N-(7-fluoro-3-[[2-(1-methyl-1H-pyrazol-4-yl)-3-[1-(triphenylmethyl)-1H-imidazol-4-yl]cyclopropane]amido]-6-(4-methylpyridin-3-yl)isoquinolin-8-yl)carbamate (120 mg, 0.14 mmol) as a white solid. LCMS (ESI) [M+H]$^+$=825.

Step 6: (1R,3S)—N-[8-amino-7-fluoro-6-(4-methylpyridin-3-yl)isoquinolin-3-yl]-2-(1H-imidazol-4-yl)-3-(1-methyl-1H-pyrazol-4-yl)cyclopropane-1-carboxamide and (1S,3R)—N-[8-amino-7-fluoro-6-(4-methylpyridin-3-yl)isoquinolin-3-yl]-2-(1H-imidazol-4-yl)-3-(1-methyl-1H-pyrazol-4-yl)cyclopropane-1-carboxamide

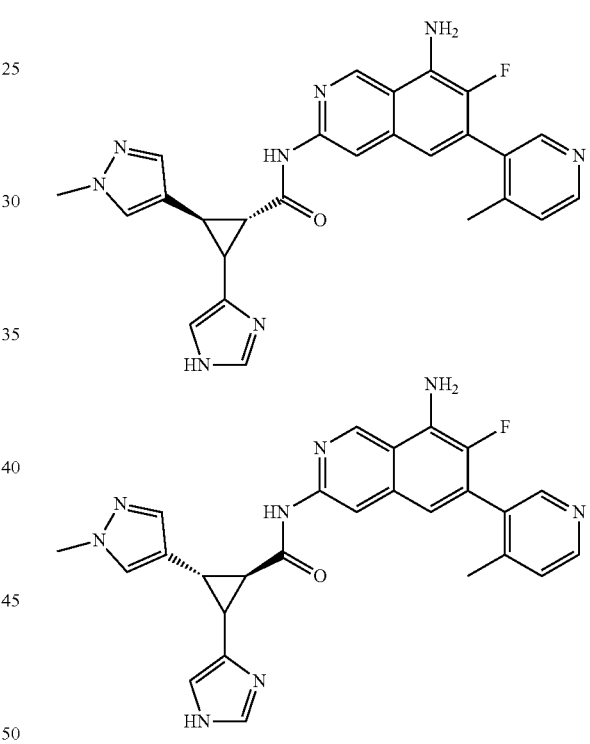

A mixture of tert-butyl N-(7-fluoro-3-[[2-(1-methyl-1H-pyrazol-4-yl)-3-[1-(triphenylmethyl)-1H-imidazol-4-yl]cyclopropane]amido]-6-(4-methylpyridin-3-yl)isoquinolin-8-yl)carbamate (100 mg, 0.12 mmol) in trifluoroacetic acid (5 mL) was stirred for 1 h at room temperature. The resulting mixture was concentrated under vacuum. The residue was purified by reverse phase chromatography (acetonitrile 0-50/0.1% FA in water) to afford the racemic product (20 mg, 0.04 mmol) as a yellow solid. The racemic product was separated by Chiral-HPLC to afford two isomers: (Cyclopropane stereochemistry for the isomers: pyrazole trans to amide; imidazole relative stereochemistry unknown; All absolute stereochemistry arbitrarily assigned) Compound 370: Retention time:4.99 min (CHIRALPAK ID-3, 0.46*10 cm; 3 μm; MtBE (0.1% DEA):EtOH=50:50; 1 ml/min); LCMS (ESI) [M+H]$^+$=483; $^1$HNMR (400 MHz, CD$_3$OD) δ 9.33 (s, 1H), 8.48 (d, J=4.0 Hz, 1H), 8.42-8.40 (m, 2H), 7.56 (s, 1H), 7.45 (d, J=4.0 Hz, 1H), 7.27 (s, 1H), 7.12 (s, 1H), 7.03 (s, 1H), 6.77 (s, 1H), 3.73 (s, 3H), 2.90-2.86 (m, 1H), 2.79-2.76 (m, 1H), 2.71-2.69 (m, 1H), 2.32 (s, 3H); Compound 369: Retention time: 5.98 min (CHIRALPAK ID-3, 0.46*10 cm; 3 μm; MtBE (0.1% DEA):EtOH=50:50; 1 ml/min); LCMS (ESI) [M+H]$^+$=483; $^1$HNMR (400 MHz, CD$_3$OD) δ 9.33 (s, 1H), 8.48 (d, J=4.0 Hz, 1H), 8.42-8.40 (m, 2H), 7.56 (s, 1H), 7.45 (d, J=4.0 Hz, 1H), 7.27 (s, 1H), 7.12 (s, 1H), 7.03 (s, 1H), 6.77 (s, 1H), 3.73 (s, 3H), 2.90-2.86 (m, 1H), 2.79-2.76 (m, 1H), 2.71-2.69 (m, 1H), 2.32 (s, 3H)

Example 208 and Example 209

(±)-(1R,2S,3S)—N-(8-amino-7-fluoro-6-(4-methylpyridin-3-yl)isoquinolin-3-yl)-2-(cyanomethyl)-3-((dimethylamino)methyl)cyclopropane-1-carboxamide (Compound 343)

(1R,2S,3S)—N-(8-amino-7-fluoro-6-(4-methylpyridin-3-yl)isoquinolin-3-yl)-2-(cyanomethyl)-3-((dimethylamino)methyl)cyclopropane-1-carboxamide (Compound 344) and (1S,2R,3R)—N-(8-amino-7-fluoro-6-(4-methylpyridin-3-yl)isoquinolin-3-yl)-2-(cyanomethyl)-3-((dimethylamino)methyl)cyclopropane-1-carboxamide (Compound 345)

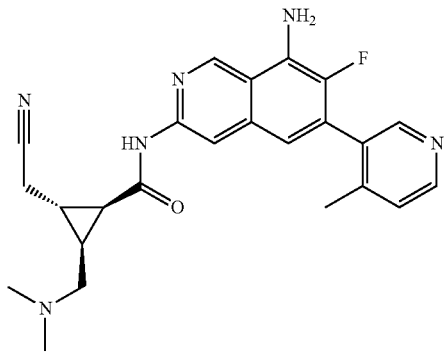

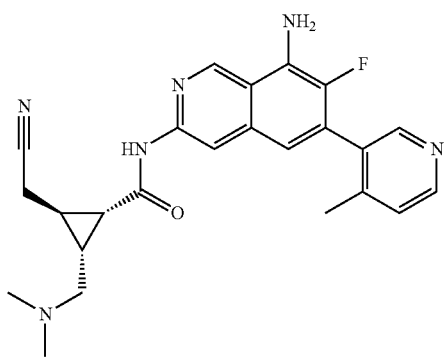

Step 1: ethyl 2-oxo-3-oxabicyclo[3.1.0]hexane-6-carboxylate

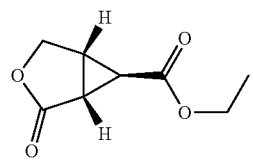

To a solution of (2-ethoxy-2-oxoethyl)dimethylsulfanium bromide (60 g, 261.85 mmol) and cesium carbonate (101 g, 309.98 mmol) in N,N-dimethylformamide (300 mL) was stirred for 20 min at 20° C. 2,5-dihydrofuran-2-one (20 g, 237.88 mmol) was added and the mixture was stirred for an additional 15 hours at 20° C. The reaction was quenched by water. The resulting solution was extracted with ethyl acetate, dried with anhydrous sodium sulfate. After filtration, the filtrate was concentrated under vacuum. The residue was purified by flash chromatography on silica gel eluting with ethyl acetate/petroleum ether (3/7) to afford ethyl 2-oxo-3-oxabicyclo[3.1.0]hexane-6-carboxylate (3 g, 7%) as a white solid. LCMS (ESI) [M+H]$^+$=171.

Step 2: ethyl 2-[[8-chloro-7-fluoro-6-(4-methylpyridin-3-yl)isoquinolin-3-yl]carbamoyl]-3-(hydroxymethyl)cyclopropane-1-carboxylate

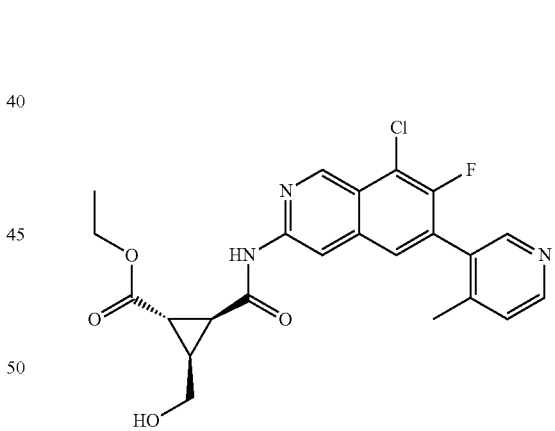

To a solution of 8-chloro-7-fluoro-6-(4-methylpyridin-3-yl)isoquinolin-3-amine (6.1 g, 21.20 mmol) in tetrahydrofuran (150 mL) was added LiHMDS (18 mL, 107.57 mmol) and then stirred for 1 hour at −78° C. Ethyl 2-oxo-3-oxabicyclo[3.1.0]hexane-6-carboxylate (4.5 g, 26.45 mmol) was added and the mixture was stirred for another 15 hours at 20° C. The resulting mixture was concentrated under vacuum. The residue was purified by flash chromatography on silica gel eluting with dichloromethane/methanol (49/1) to afford ethyl 2-[[8-chloro-7-fluoro-6-(4-methylpyridin-3-yl)isoquinolin-3-yl]carbamoyl]-3-(hydroxymethyl)cyclopropane-1-carboxylate (3.1 g, 26%) as a yellow solid. LCMS (ESI) [M+H]$^+$=458.

Step 3: ethyl 2-[[8-chloro-7-fluoro-6-(4-methylpyridin-3-yl)isoquinolin-3-yl]carbamoyl]-3-[(methanesulfonyloxy)methyl]cyclopropane-1-carboxylate

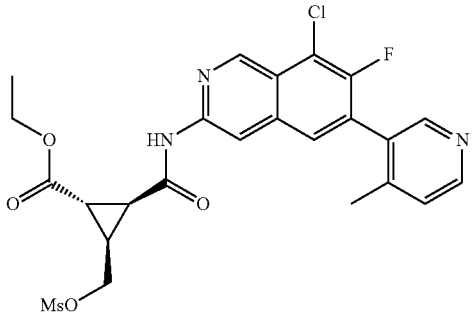 [SMILES: CCOC(=O)[C@H]1[C@H](COS(C)(=O)=O)[C@@H]1C(=O)Nc1cc2cc(-c3cnccc3C)c(F)c(Cl)c2cn1]

To a solution of ethyl 2-[[8-chloro-7-fluoro-6-(4-methylpyridin-3-yl)isoquinolin-3-yl]carbamoyl]-3-(hydroxymethyl)cyclopropane-1-carboxylate (1.4 g, 3.06 mmol) in dichloromethane (20 mL) was added triethylamine (927 mg, 9.161 mmol) and methanesulfonyl chloride (703 mg, 6.14 mmol) and then stirred for 15 min at 0° C. The resulting solution was concentrated under vacuum to afford ethyl 2-[[8-chloro-7-fluoro-6-(4-methylpyridin-3-yl)isoquinolin-3-yl]carbamoyl]-3-[(methanesulfonyloxy)methyl]cyclopropane-1-carboxylate (2 g, crude) as a brown solid. LCMS (ESI) [M+H]$^+$=536.

Step 4: ethyl 2-[[8-chloro-7-fluoro-6-(4-methylpyridin-3-yl)isoquinolin-3-yl]carbamoyl]-3-[(dimethylamino)methyl]cyclopropane-1-carboxylate

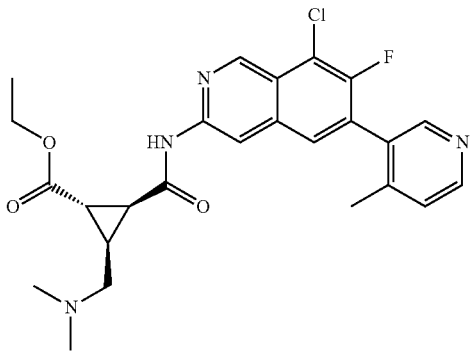 [SMILES: CCOC(=O)[C@H]1[C@H](CN(C)C)[C@@H]1C(=O)Nc1cc2cc(-c3cnccc3C)c(F)c(Cl)c2cn1]

To a solution of ethyl 2-[[8-chloro-7-fluoro-6-(4-methylpyridin-3-yl)isoquinolin-3-yl]carbamoyl]-3-[(methanesulfonyloxy)methyl]cyclopropane-1-carboxylate (3.6 g, 6.72 mmol) and dimethylamine in methanol (160 mL) was stirred for 36 h at 20° C. The resulting mixture was concentrated under vacuum. The residue was purified by flash chromatography on silica gel eluting with dichloromethane/methanol (24/1) to afford ethyl 2-[[8-chloro-7-fluoro-6-(4-methylpyridin-3-yl)isoquinolin-3-yl]carbamoyl]-3-[(dimethylamino)methyl]cyclopropane-1-carboxylate (1.85 g, 57%) as a yellow solid. LCMS (ESI) [M+H]$^+$=485.

Step 5: ethyl 2-[(8-[[(tert-butoxy)carbonyl]amino]-7-fluoro-6-(4-methylpyridin-3-yl)isoquinolin-3-yl)carbamoyl]-3-[(dimethylamino)methyl]cyclopropane-1-carboxylate

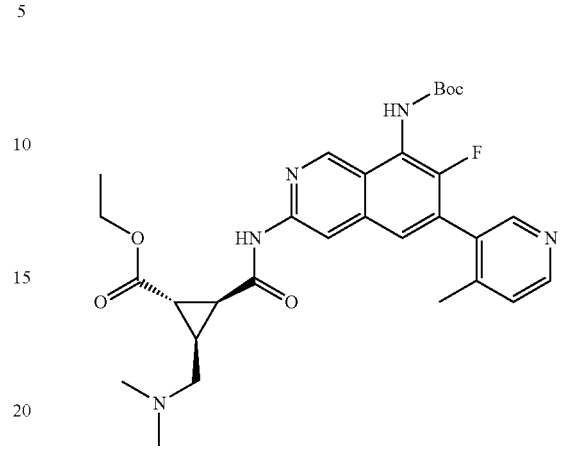

A mixture of ethyl 2-[[8-chloro-7-fluoro-6-(4-methylpyridin-3-yl)isoquinolin-3-yl]carbamoyl]-3-[(dimethylamino)methyl]cyclopropane-1-carboxylate (592 mg, 1.22 mmol), tert-butyl carbamate (3.57 g, 30.475 mmol), tris(dibenzylideneacetone)dipalladium-chloroform adduct (253 mg, 0.244 mmol), BrettPhos (262 mg, 0.49 mmol), cesium carbonate (1.99 g, 6.11 mmol) in 1,4-dioxane (20 mL) was stirred for 15 h at 90° C. The mixture was then filtered. The filtrate was concentrated under vacuum. The residue was purified by flash chromatography on silica gel eluting with dichloromethane/methanol (20/1) to afford ethyl 2-[(8-[[(tert-butoxy)carbonyl]amino]-7-fluoro-6-(4-methylpyridin-3-yl)isoquinolin-3-yl)carbamoyl]-3-[(dimethylamino)methyl]cyclopropane-1-carboxylate (280 mg, 41%) as a brown solid. LCMS (ESI) [M+H]$^+$=566.

Step 6: tert-butyl N-(3-[[2-[(dimethylamino)methyl]-3-(hydroxymethyl)cyclopropane]amido]-7-fluoro-6-(4-methylpyridin-3-yl)isoquinolin-8-yl)carbamate

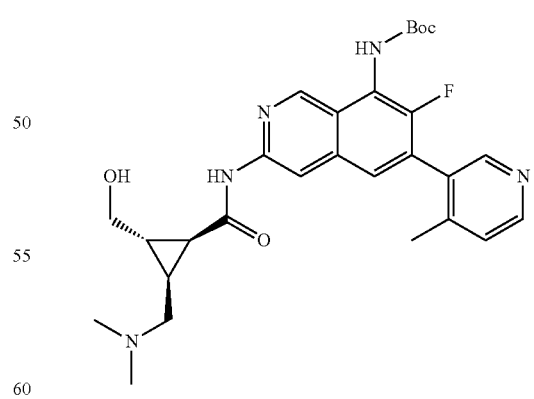

To a solution of ethyl 2-[(8-[[(tert-butoxy)carbonyl]amino]-7-fluoro-6-(4-methylpyridin-3-yl)isoquinolin-3-yl)carbamoyl]-3-[(dimethylamino)methyl]cyclopropane-1-carboxylate (280 mg, 0.49 mmol) in dichloromethane (5 mL) was added DIBAl-H (1.98 mL, 11.81 mmol). The mixture was stirred for 1 hour at −78° C. The reaction was quenched by methanol. The resulting mixture was concentrated under vacuum. The residue was purified by flash chromatography on silica gel eluting with dichloromethane/methanol (7/3) to afford tert-butyl N-(3-[[2-[(dimethylamino)methyl]-3-(hydroxymethyl)cyclopropane]amido]-7-fluoro-6-(4-methylpyridin-3-yl)isoquinolin-8-yl)carbamate (80 mg, 31%) as a brown solid. LCMS (ESI) [M+H]$^+$=524.

Step 7: tert-butyl N-(3-[[2-[(dimethylamino)methyl]-3-[(methanesulfonyloxy)methyl]cyclopropane]amido]-7-fluoro-6-(4-methylpyridin-3-yl)isoquinolin-8-yl)carbamate

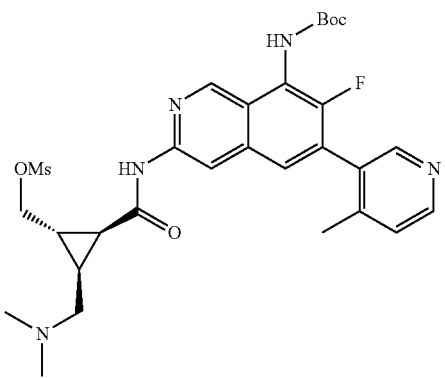 [SMILES: Cc1ccncc1-c1cc2cc(NC(=O)[C@@H]3[C@@H](COS(C)(=O)=O)[C@@H]3CN(C)C)ncc2c(NC(=O)OC(C)(C)C)c1F]

To a solution of tert-butyl N-(3-[[2-[(dimethylamino)methyl]-3-(hydroxymethyl)cyclopropane]amido]-7-fluoro-6-(4-methylpyridin-3-yl)isoquinolin-8-yl)carbamate (70 mg, 0.13 mmol) in dichloromethane (5 mL) was added triethylamine (42 mg, 0.42 mmol), methanesulfonyl chloride (31 mg, 0.27 mmol). The resulting solution was stirred for 15 min at 0° C. The resulting solution was concentrated under vacuum to afford tert-butyl N-(3-[[2-[(dimethylamino)methyl]-3-[(methanesulfonyloxy)methyl]cyclopropane]amido]-7-fluoro-6-(4-methylpyridin-3-yl)isoquinolin-8-yl)carbamate (90 mg, crude) as a brown solid. LCMS (ESI) [M+H]$^+$=602.

Step 8: tert-butyl N-(3-[[2-(cyanomethyl)-3-[(dimethylamino)methyl]cyclopropane]amido]-7-fluoro-6-(4-methylpyridin-3-yl)isoquinolin-8-yl)carbamate

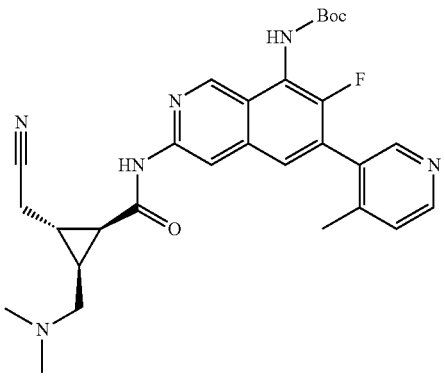 [SMILES: Cc1ccncc1-c1cc2cc(NC(=O)[C@@H]3[C@@H](CC#N)[C@@H]3CN(C)C)ncc2c(NC(=O)OC(C)(C)C)c1F]

To a mixture of tert-butyl N-(3-[[2-[(dimethylamino)methyl]-3-[(methanesulfonyloxy)methyl]cyclopropane]amido]-7-fluoro-6-(4-methylpyridin-3-yl)isoquinolin-8-yl)carbamate (90 mg, 0.150 mmol) and NaCN (15 mg, 0.31 mmol) in DMSO (5 mL) was stirred for 1 h at 50° C. The reaction was quenched by water. The resulting solution was extracted with ethyl acetate, dried with anhydrous sodium sulfate. After filtration, the filtrate was concentrated under vacuum to afford ert-butyl N-(3-[[2-(cyanomethyl)-3-[(dimethylamino)methyl]cyclopropane]amido]-7-fluoro-6-(4-methylpyridin-3-yl)isoquinolin-8-yl)carbamate (50 mg, 63%) as a brown solid. LCMS (ESI) [M+H]$^+$=533.

Step 9: (1R,2S,3S)—N-(8-amino-7-fluoro-6-(4-methylpyridin-3-yl)isoquinolin-3-yl)-2-(cyanomethyl)-3-((dimethylamino)methyl)cyclopropane-1-carboxamide and (1S,2R,3R)—N-(8-amino-7-fluoro-6-(4-methylpyridin-3-yl)isoquinolin-3-yl)-2-(cyanomethyl)-3-((dimethylamino)methyl)cyclopropane-1-carboxamide

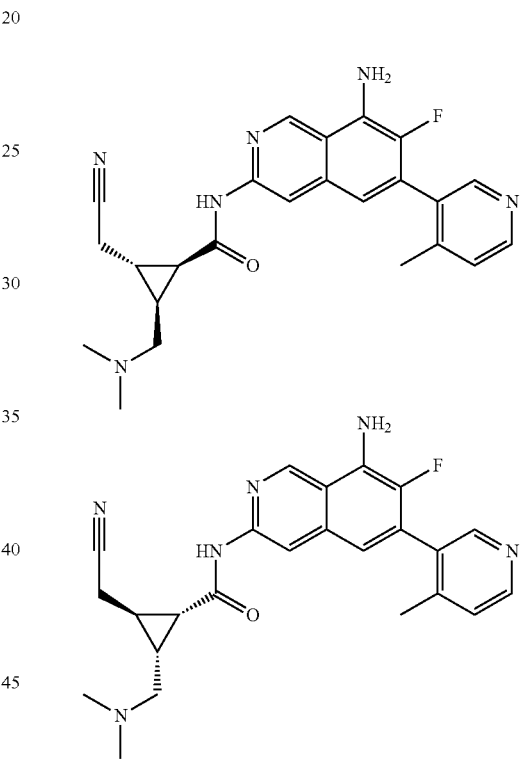

To a solution of tert-butyl N-(3-[[(1R,2S,3S)-2-(cyanomethyl)-3-[(dimethylamino)methyl]cyclopropane]amido]-7-fluoro-6-(4-methylpyridin-3-yl)isoquinolin-8-yl)carbamate (48 mg, 0.090 mmol) and trifluoroacetic acid (5 mL) in dichloromethane (5 mL) was stirred for 1 h at 20° C. The resulting mixture was concentrated under vacuum. The residue was purified by Prep-HPLC with the following conditions (Kinetex EVO C18 Column, 30*150.5 um; Water (10 mmol/L sodium bicarbonate) and ACN (15% to 35%) in 10 min) to afford (±)-(1R,2S,3S)—N-[8-amino-7-fluoro-6-(4-methylpyridin-3-yl)isoquinolin-3-yl]-2-(cyanomethyl)-3-[(dimethylamino)methyl]cyclopropane-1-carboxamide (2.4 mg, 6%) as a yellow solid. LCMS (ESI) [M+H]$^+$=433.2; $^1$HNMR (300 MHz, DMSO-d$_6$) δ 10.84 (s, 1H), 9.41 (s, 1H), 8.50 (d, J=5.0 Hz, 1H), 8.42 (s, 1H), 8.29 (s, 1H), 7.39 (d, J=5.1 Hz, 1H), 6.94 (d, J=6.2 Hz, 1H), 6.29 (s, 2H), 2.84-2.72 (m, 2H), 2.46 (d, J=6.7 Hz, 2H), 2.21 (s, 3H), 2.13 (s, 7H), 1.60 (dd, J=6.5, 5.0 Hz, 1H), 1.51-1.40 (m, 1H). The racemic product was separated by SFC to afford two isomers. Compound 344 (5.1 mg, 34%) as a yellow solid. Retention time: 3.652 min (CHIRALPAK IF, 2*25 cm, 5 μm; MTBE and 20.0% ethanol (8 mmol/L NH$_3$.H$_2$O) in 23 min); LCMS (ESI) [M+H]$^+$=433.2; $^1$HNMR (300 MHz, DMSO-d$_6$) δ 10.84 (s, 1H), 9.41 (s, 1H), 8.50 (d, J=5.0 Hz, 1H), 8.42 (s, 1H), 8.29 (s, 1H), 7.39 (d, J=5.1 Hz, 1H), 6.94 (d, J=6.2 Hz, 1H), 6.29 (s, 2H), 2.84-2.72 (m, 2H), 2.46 (d, J=6.7 Hz, 2H), 2.21 (s, 3H), 2.13 (s, 7H), 1.60 (dd, J=6.5, 5.0 Hz, 1H), 1.51-1.40 (m, 1H). Compound 345: (5.4 mg, 36%) as a yellow solid. Retention time: 4.805 min (CHIRALPAK IF, 2*25 cm, 5 μm; MTBE and 20.0% ethanol (8 mmol/L NH$_3$.H$_2$O) in 23 min); LCMS (ESI) [M+H]$^+$=433.2; $^1$HNMR (300 MHz, DMSO-d$_6$) δ 10.84 (s, 1H), 9.41 (s, 1H), 8.50 (d, J=5.0 Hz, 1H), 8.42 (s, 1H), 8.29 (s, 1H), 7.39 (d, J=5.1 Hz, 1H), 6.94 (d, J=6.2 Hz, 1H), 6.29 (s, 2H), 2.84-2.72 (m, 2H), 2.46 (d, J=6.7 Hz, 2H), 2.21 (s, 3H), 2.13 (s, 7H), 1.60 (dd, J=6.5, 5.0 Hz, 1H), 1.51-1.40 (m, 1H).

Example 210

(1S,2R,3R)—N-(8-amino-7-fluoro-6-(4-methylpyridin-3-yl)isoquinolin-3-yl)-2-(cyanomethyl)-3-(1H-imidazol-4-yl)cyclopropane-1-carboxamide (Compound 324) and (1R,2S,3S)—N-(8-amino-7-fluoro-6-(4-methylpyridin-3-yl)isoquinolin-3-yl)-2-(cyanomethyl)-3-(1H-imidazol-4-yl)cyclopropane-1-carboxamide (Compound 323)

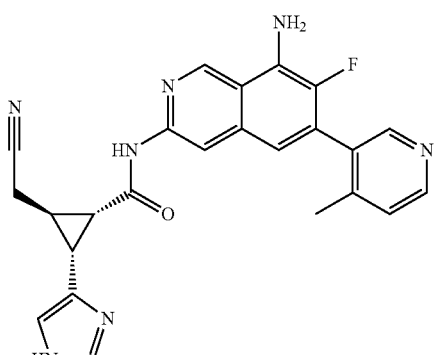

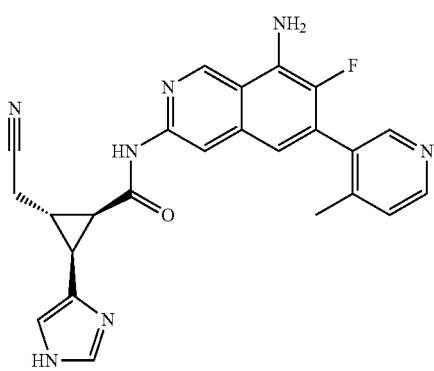

Step 1:dimethyl 3-(1-trityl-1H-imidazol-4-yl)cyclopropane-1,2-dicarboxylate

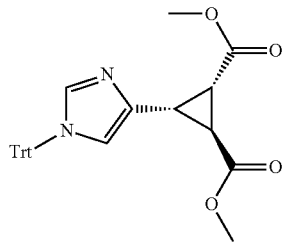

A mixture of 1,4-dimethyl (2E)-but-2-enedioate (10 g, 69.38 mmol), 4-methyl-N'-[(1E)-[1-(triphenylmethyl)-1H-imidazol-4-yl]methylidene]benzene-1-sulfonohydrazide (2.85 g, 5.63 mmol) and potassium carbonate (4.09 g, 29.59 mmol) in xylene (150 mL) was stirred for 1 h at 150° C. The mixture was then filtered and concentrated under vacuum. The residue was purified by flash chromatography on silica gel eluting with dichloromethane/methanol (10/1) to afford (±)-dimethyl (1S,2S)-3-(1-trityl-1H-imidazol-4-yl)cyclopropane-1,2-dicarboxylate (4 g, 24%) as a light yellow solid. LCMS (ESI) [M+H]$^+$=467.

Step 2: 2-(methoxycarbonyl)-3-[1-(triphenylmethyl)-1H-imidazol-4-yl]cyclopropane-1-carboxylic Acid

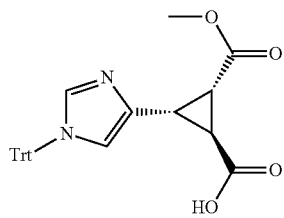

A mixture of 1,2-dimethyl 3-[1-(triphenylmethyl)-1H-imidazol-4-yl]cyclopropane-1,2-dicarboxylate (3.2 g, 6.85 mmol) and LiOH.H$_2$O (288 mg, 6.86 mmol) in tetrahydrofuran (30 mL) and methanol (10 mL) was stirred for 2 h at room temperature. The mixture was concentrated under vacuum. The residue was diluted with water and the pH value of the solution was adjusted to 4 with hydrogen chloride (1.0 mol/L). The resulting mixture was extracted with 3×100 mL of dichloromethane. The organic layers combined and dried over anhydrous sodium sulfate and filtered. The resulting mixture was concentrated under vacuum to afford 2-(methoxycarbonyl)-3-[1-(triphenylmethyl)-1H-imidazol-4-yl]cyclopropane-1-carboxylic acid (1.2 g, 39%) as a white solid. LCMS (ESI) [M+H]$^+$=453.

Step 3: methyl 2-(hydroxymethyl)-3-[1-(triphenylmethyl)-1H-imidazol-4-yl]cyclopropane-1-carboxylate

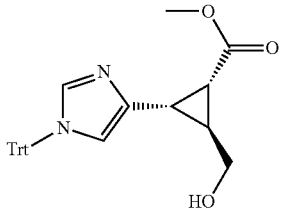

To a solution of 2-(methoxycarbonyl)-3-[1-(triphenylmethyl)-1H-imidazol-4-yl]cyclopropane-1-carboxylic acid (3.0 g, 6.63 mmol) in dichloromethane (40 mL) was added BH$_3$-Me$_2$S (2 mL, 21.09 mmol). The solution was stirred for 2 h at room temperature. The reaction was then quenched by methanol. The mixture was concentrated under vacuum. The residue was purified by flash chromatography on silica gel eluting with dichloromethane/methanol (10/1) to afford methyl 2-(hydroxymethyl)-3-[1-(triphenylmethyl)-1H-imidazol-4-yl]cyclopropane-1-carboxylate (1.5 g, 52%) as a white solid. LCMS (ESI) [M+H]$^+$=439.

Step 4: methyl 2-[(methanesulfonyloxy)methyl]-3-[1-(triphenylmethyl)-1H-imidazol-4-yl]cyclopropane-1-carboxylate

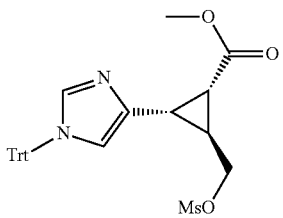

To a solution of methyl 2-(hydroxymethyl)-3-[1-(triphenylmethyl)-1H-imidazol-4-yl]cyclopropane-1-carboxylate (537 mg, 1.23 mmol) and triethylamine (371 mg, 3.67 mmol) in dichloromethane (10 mL) was added methanesulfonyl chloride (281 mg, 2.45 mmol) at 0° C. The solution was stirred for 15 min at 0° C. The reaction was then quenched by water. The resulting solution was extracted with dichloromethane. The organic layers were dried over anhydrous sodium sulfate. After filtration, the filtrate was concentrated under vacuum to afford methyl 2-[(methanesulfonyloxy)methyl]-3-[1-(triphenylmethyl)-1H-imidazol-4-yl]cyclopropane-1-carboxylate (500 mg, 79%) as light yellow oil. LCMS (ESI) [M+H]$^+$=517.

Step 5: methyl (2-(cyanomethyl)-3-[1-(triphenylmethyl)-1H-imidazol-4-yl]cyclopropane-1-carboxylate

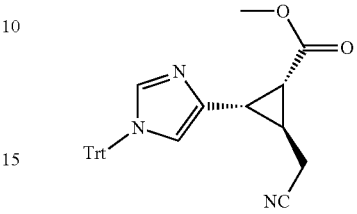

A mixture of methyl 2-[(methanesulfonyloxy)methyl]-3-[1-(triphenylmethyl)-1H-imidazol-4-yl]cyclopropane-1-carboxylate (620 mg, 1.20 mmol) and NaCN (118 mg, 2.41 mmol) in dimethyl sulphoxide (10 mL) was stirred for 1 h at 50° C. The reaction was diluted with ethyl acetate. The resulting mixture was washed with water. The organic phase was dried with anhydrous sodium sulfate. After filtration, the filtrate was concentrated under vacuum. The residue was purified by flash chromatography on silica gel eluting with dichloromethane/methanol (95/5) to afford methyl 2-(cyanomethyl)-3-[1-(triphenylmethyl)-1H-imidazol-4-yl]cyclopropane-1-carboxylate (440 mg, 82%) as a light yellow solid. LCMS (ESI) [M+H]$^+$=448.

Step 6: (1R,2S,3S)-2-(cyanomethyl)-3-[1-(triphenylmethyl)-1H-imidazol-4-yl]cyclopropane-1-carboxylic Acid

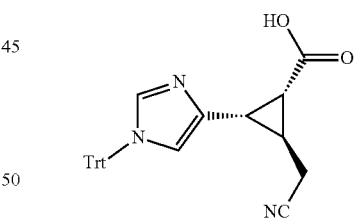

A mixture of methyl 2-(cyanomethyl)-3-[1-(triphenylmethyl)-1H-imidazol-4-yl]cyclopropane-1-carboxylate (400 mg, 0.89 mmol) and sodium hydroxide (107 mg, 2.68 mmol) in ethanol (10 mL), tetrahydrofuran (10 mL) and water (10 mL) was stirred for 12 h at room temperature. The mixture was concentrated under vacuum. The resulting solution was diluted with water. The pH value of the solution was adjusted to 4 with hydrogen chloride (1.0 mol/L). The solution was extracted with dichloromethane. The organic layers were dried over anhydrous sodium sulfate. After filtration, the filtrate was concentrated under vacuum to afford 2-(cyanomethyl)-3-[1-(triphenylmethyl)-1H-imidazol-4-yl]cyclopropane-1-carboxylic acid (320 mg, 83%) as a light yellow solid. LCMS (ESI) [M+H]$^+$=434.

903

Step 7: tert-butyl N-(3-[[(2-(cyanomethyl)-3-[1-(triphenylmethyl)-1H-imidazol-4-yl]cyclopropane]amido]-7-fluoro-6-(4-methylpyridin-3-yl)isoquinolin-8-yl)carbamate

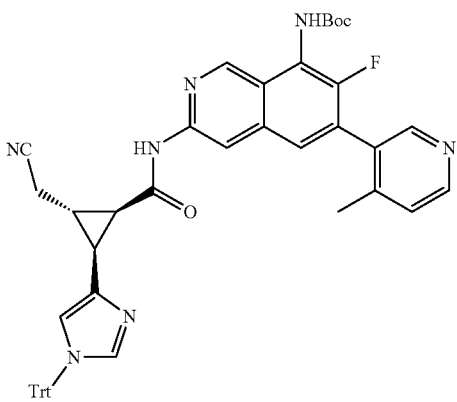

To a solution of 2-(cyanomethyl)-3-[1-(triphenylmethyl)-1H-imidazol-4-yl]cyclopropane-1-carboxylic acid (377 mg, 0.87 mmol), tert-butyl N-[3-amino-7-fluoro-6-(4-methylpyridin-3-yl)isoquinolin-8-yl]carbamate (320 mg, 0.87 mmol) and pyridine (1 mL) in dichloromethane (10 mL) was added POCl$_3$ (405 mg, 2.64 mmol). The mixture was stirred for 30 min at 0° C. The reaction was then quenched by water and then extracted with ethyl acetate. The organic layers were dried with anhydrous sodium sulfate. After filtration, the filtrate was concentrated under vacuum. The residue was purified by flash chromatography on silica gel eluting with dichloromethane/methanol (10/1) to afford tert-butyl N-(3-[[2-(cyanomethyl)-3-[1-(triphenylmethyl)-1H-imidazol-4-yl]cyclopropane]amido]-7-fluoro-6-(4-methylpyridin-3-yl)isoquinolin-8-yl)carbamateb (500 mg, 73%) as yellow oil. LCMS (ESI) [M+H]$^+$=784.

Step 8: (1R,2S,3S)—N-[8-amino-7-fluoro-6-(4-methylpyridin-3-yl)isoquinolin-3-yl]-2-(cyanomethyl)-3-(1H-imidazol-4-yl)cyclopropane-1-carboxamide and (1S,2R,3R)—N-[8-amino-7-fluoro-6-(4-methylpyridin-3-yl)isoquinolin-3-yl]-2-(cyanomethyl)-3-(1H-imidazol-4-yl)cyclopropane-1-carboxamide

904

-continued

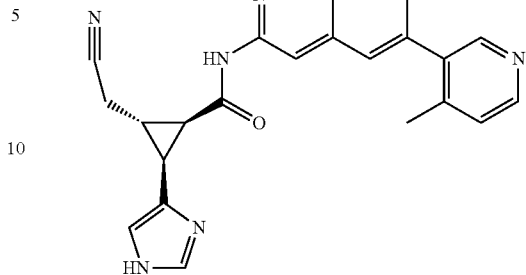

A mixture of tert-butyl N-(3-[[2-(cyanomethyl)-3-[1-(triphenylmethyl)-1H-imidazol-4-yl]cyclopropane]amido]-7-fluoro-6-(4-methylpyridin-3-yl)isoquinolin-8-yl)carbamate (600 mg, 0.77 mmol) in dichloromethane (5 mL) and 2,2,2-trifluoroacetic acid (5 mL) was stirred for 1 h at room temperature. The mixture was concentrated under vacuum and then diluted with dichloromethane. The pH value of the solution was adjusted to 8 with ammonia in methanol (7 mol/L). The crude product was purified by Prep-HPLC (Kinetex EVO C18 Column, 30*150, 5 μm; Water (10 mmol/L sodium bicarbonate) and ACN (20% ACN up to 35% in 7 min) to afford the racemic product. The racemic product was purified by Chiral-HPLC to afford two enantiomers. Compound 323: (16.7 mg, 5%) as a light yellow solid. LCMS (ESI) [M+H]$^+$=784. $^1$HNMR (400 MHz, DMSO) δ 11.86 (s, 1H), 10.77 (s, 1H), 9.39 (s, 1H), 8.50 (d, J=6.0 Hz, 1H), 8.41 (s, 1H), 8.17 (s, 1H), 7.47 (s, 1H), 7.39 (d, J=6.0 Hz, 1H), 6.89 (d, J=6.0 Hz, 1H), 6.80 (s, 1H), 6.29 (s, 2H), 2.97-2.82 (m, 2H), 2.47-2.41 (m, 2H), 2.38-2.20 (m, 4H). Compound 324: (13.8 mg, 4%) as alight yellow solid. LCMS (ESI) [M+H]$^+$=784. $^1$HNMR (400 MHz, DMSO) δ 11.86 (s, 1H), 10.77 (s, 1H), 9.39 (s, 1H), 8.50 (d, J=6.0 Hz, 1H), 8.41 (s, 1H), 8.17 (s, 1H), 7.47 (s, 1H), 7.39 (d, J=6.0 Hz, 1H), 6.89 (d, J=6.0 Hz, 1H), 6.80 (s, 1H), 6.29 (s, 2H), 2.97-2.82 (m, 2H), 2.47-2.41 (m, 2H), 2.38-2.20 (m, 4H).

Example 211

2-((8-amino-6-(5-amino-4-methylpyridin-3-yl)-7-fluoroisoquinolin-3-yl)amino)-6-methyl-5,6-dihydro-4H-pyrazolo[1,5-d][1,4]diazepin-7(8H)-one (Compound 229)

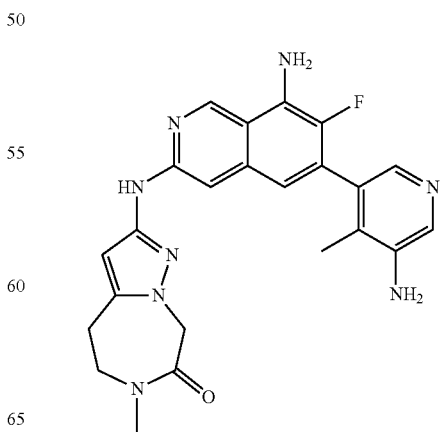

905

Step 1: tert-butyl N-[(tert-butoxy)carbonyl]-N-[5-[8-chloro-7-fluoro-3-([6-methyl-7-oxo-4H,5H,6H,7H,8H-pyrazolo[1,5-d][1,4]diazepin-2-yl]amino)isoquinolin-6-yl]-4-methylpyridin-3-yl]carbamate

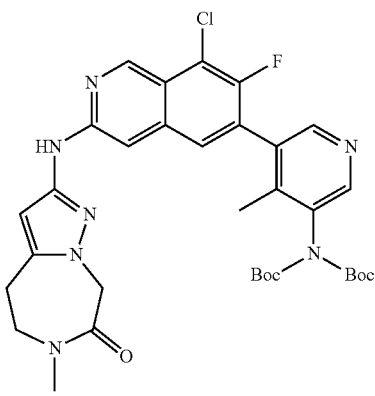 [SMILES: Cc1c(-c2cc3cc(Nc4cc5n(n4)CC(=O)N(C)CC5)ncc3c(Cl)c2F)cncc1N(C(=O)OC(C)(C)C)C(=O)OC(C)(C)C]

A mixture of 2-bromo-6-methyl-4H,5H,6H,7H,8H-pyrazolo[1,5-d][1,4]diazepin-7-one (25 mg, 0.10 mmol), tert-butyl N-[5-(3-amino-8-chloro-7-fluoroisoquinolin-6-yl)-4-methylpyridin-3-yl]-N-[(tert-butoxy)carbonyl]carbamate (50 mg, 0.099 mmol), tris(dibenzylideneacetone)dipalladium-chloroform adduct (21 mg, 0.020 mmol), XantPhos (23 mg, 0.040 mmol), cesium carbonate (81 mg, 0.25 mmol) in 1,4-dioxane (4 mL) was stirred for 15 h at 100° C. The reaction solution was cooled to room temperature and then filtrated. The filtrate was concentrated under vacuum. The residue was purified by flash chromatography on silica gel eluting with petroleum ether/ethyl acetate (1/1) to afford tert-butyl N-[(tert-butoxy)carbonyl]-N-[5-[8-chloro-7-fluoro-3-([6-methyl-7-oxo-4H,5H,6H,7H,8H-pyrazolo[1,5-d][1,4]diazepin-2-yl]amino)isoquinolin-6-yl]-4-methylpyridin-3-yl]carbamate (20 mg, 0.030 mmol) as a yellow solid. LCMS (ESI) [M+H]$^+$=666.

Step 2: tert-butyl (tert-butoxycarbonyl)(5-(8-((tert-butoxycarbonyl)amino)-7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)carbamate

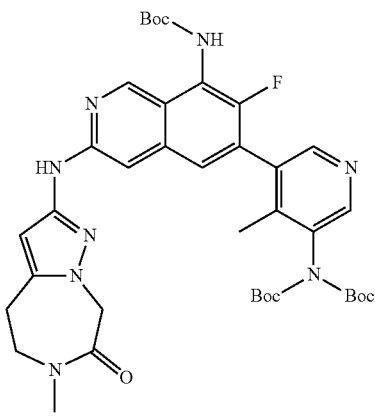 [SMILES: Cc1c(-c2cc3cc(Nc4cc5n(n4)CC(=O)N(C)CC5)ncc3c(NC(=O)OC(C)(C)C)c2F)cncc1N(C(=O)OC(C)(C)C)C(=O)OC(C)(C)C]

906

A mixture of tert-butyl N-[(tert-butoxy)carbonyl]-N-[5-[8-chloro-7-fluoro-3-([6-methyl-7-oxo-4H,5H,6H,7H,8H-pyrazolo[1,5-d][1,4]diazepin-2-yl]amino)isoquinolin-6-yl]-4-methylpyridin-3-yl]carbamate (60 mg, 0.090 mmol), tert-butyl carbamate (264 mg, 2.25 mmol), tris(dibenzylideneacetone)dipalladium-chloroformadduct (19 mg, 0.018 mmol), BrettPhos (20 mg, 0.037 mmol), cesium carbonate (147 mg, 0.45 mmol) in 1,4-dioxane (15 mL) was stirred for 2 h at 90° C. The reaction solution was cooled to room temperature and then filtrated. The filtrate was concentrated under vacuum. The residue was purified by flash chromatography on silica gel eluting with petroleum ether/ethyl acetate (1/1) to afford tert-butyl (tert-butoxycarbonyl)(5-(8-((tert-butoxycarbonyl)amino)-7-fluoro-3-((6-methyl-7-oxo-5,6,7,8-tetrahydro-4H-pyrazolo[1,5-d][1,4]diazepin-2-yl)amino)isoquinolin-6-yl)-4-methylpyridin-3-yl)carbamate (50 mg, 0.067 mmol) as a yellow solid. LCMS (ESI) [M+H]$^+$=747.

Step 3: 2-[[8-amino-6-(5-amino-4-methylpyridin-3-yl)-7-fluoroisoquinolin-3-yl]amino]-6-methyl-4H,5H,6H,7H,8H-pyrazolo[1,5-d][1,4]diazepin-7-one

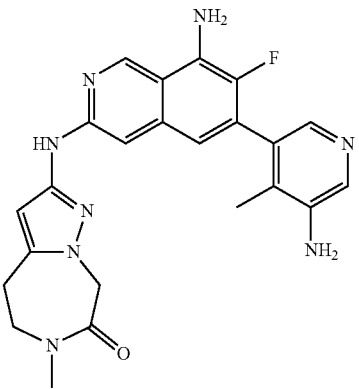 [SMILES: Cc1c(N)cncc1-c1cc2cc(Nc3cc4n(n3)CC(=O)N(C)CC4)ncc2c(N)c1F]

A solution of tert-butyl N-[6-(5-[bis[(tert-butoxy)carbonyl]amino]-4-methylpyridin-3-yl)-7-fluoro-3-([6-methyl-7-oxo-4H,5H,6H,7H,8H-pyrazolo[1,5-d][1,4]diazepin-2-yl]amino)isoquinolin-8-yl]carbamate (290 mg, 0.39 mmol) and trifluoroacetic acid (10 mL) in dichloromethane (3 mL) was stirred for 1 h at 20° C. The resulting mixture was concentrated under vacuum. The pH value of the solution was adjusted to 11 with ammonia in methanol (7 mol/L). The crude product was purified by Prep-HPLC with the following conditions (XBridge Shield RP18 OBD Column, 30*150 mm, 5 um; water (10 mmol/L sodium bicarbonate) and ACN (10% ACN up to 30% in 10 min) to afford 2-[[8-amino-6-(5-amino-4-methylpyridin-3-yl)-7-fluoroisoquinolin-3-yl]amino]-6-methyl-4H,5H,6H,7H,8H-pyrazolo[1,5-d][1,4]diazepin-7-one (34.1 mg, 20%) as a yellow solid. LCMS (ESI) [M+H]$^+$=447.2; $^1$H NMR (300 MHz, DMSO-$d_6$) δ 9.26 (s, 1H), 9.07 (s, 1H), 7.99 (s, 1H), 7.69 (s, 1H), 7.66 (s, 1H), 6.72 (d, J=6.1 Hz, 1H), 6.07 (s, 2H), 5.99 (s, 1H), 5.23 (s, 2H), 4.98 (s, 2H), 3.84 (t, J=5.7 Hz, 2H), 3.05 (t, J=5.6 Hz, 2H), 2.96 (s, 3H), 1.94 (d, J=1.5 Hz, 3H).

Example 212

(1R,2R,3R)—N-(8-amino-7-fluoro-6-(4-methylpyridin-3-yl)isoquinolin-3-yl)-2-methyl-3-(1H-pyrazol-5-yl)cyclopropane-1-carboxamide (Compound 332)

(1S,2R,3S)—N-(8-amino-7-fluoro-6-(4-methylpyridin-3-yl)isoquinolin-3yl)-2-methyl-3-(1H-pyrazol-5-yl)cyclopropane-1-carboxamide (Compound 331)

(1S,2S,3S)—N-(8-amino-7-fluoro-6-(4 methylpyridin-3-yl)isoquinolin-3-yl)-2-methyl-3-(1H-pyrazol-5-yl)cyclopropane-1-carboxamide (Compound 330) and (1R,2S,3R)—N-(8-amino-7-fluoro-6-(4-methylpyridin-3-yl)isoquinolin-3-yl)-2-methyl-3-(1H-pyrazol-5 yl)cyclopropane-1-carboxamide (assumed) (Compound 329)

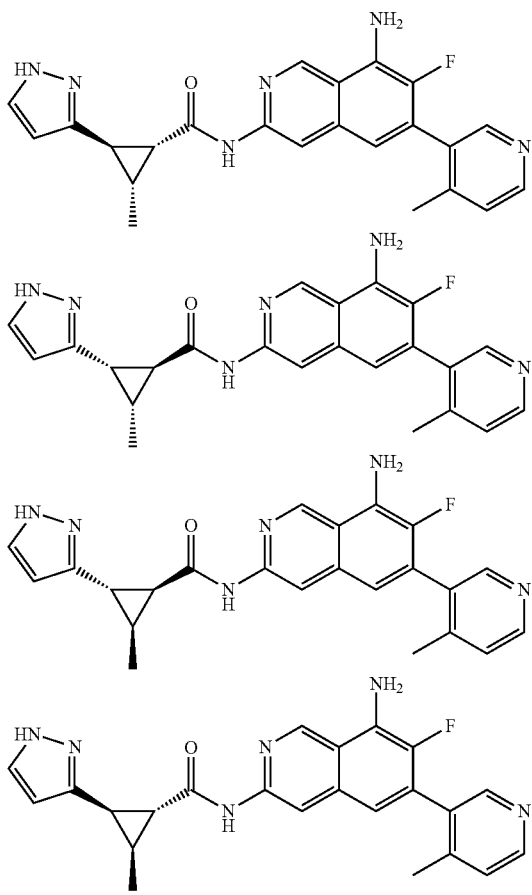

Step 1: 3-iodo-1-(tetrahydro-2H-pyran-2-yl)-1H-pyrazole

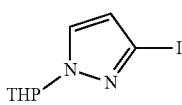

A mixture of 5-iodo-1H-pyrazole (10 g, 51.55 mmol), 3,4-dihydro-2H-pyran (13 g, 154.55 mmol), TsOH (443 mg, 2.57 mmol) in ethyl acetate (200 mL) was stirred for 3 h at 80° C. The resulting mixture was washed with water. The organic phase was dried with anhydrous sodium sulfate. After filtration, the filtrate was concentrated under vacuum. The residue was purified by flash chromatography on silica gel eluting with dichloromethane/petroleum ether (3/7) to afford 3-iodo-1-(oxan-2-yl)-1H-pyrazole (7.0 g, 25.18 mmol) as a white solid. LCMS (ESI) [M+H]$^+$=279.

Step 2: (E)-methyl 3-(1-(tetrahydro-2H-pyran-2-yl)-1H-pyrazol-3-yl)acrylate

A mixture of 3-iodo-1-(oxan-2-yl)-1H-pyrazole (5 g, 17.98 mmol), methyl prop-2-enoate (4.64 g, 53.90 mmol), palladium acetate (604 mg, 2.69 mmol), tri-o-tolyl phopine (1.09 g, 3.58 mmol), triethylamine (2.725 g, 26.93 mmol) in N,N-dimethylformamide (100 mL) was stirred for 12 h at 110° C. The resulting solution was diluted with ethyl acetate and then washed with water. The organic phase was dried with anhydrous sodium sulfate. After filtration, the filtrate was concentrated under vacuum. The residue was purified by flash chromatography on silica gel eluting with ethyl acetate/petroleum ether (15/85) to afford methyl (2E)-3-[1-(oxan-2-yl)-1H-pyrazol-3-yl]prop-2-enoate (2.7 g, 11.44 mmol) as a yellow solid. LCMS (ESI) [M+H]$^+$=237.

Step 3: methyl 2-methyl-3-(1-(tetrahydro-2H-pyran-2-yl)-1H-pyrazol-3-yl)cyclopropanecarboxylate A mixture of methyl (2E)-3-[1-(oxan-2-yl)-1H-pyrazol-3-yl]prop-2-enoate (2.7 g, 11.43 mmol), ethyldiphenylsulfanium trifluoroborane fluoride (10.37 g, 34.31 mmol), lithium diisopropylamide (20 mL, 373.40 mmol) in dichloromethane (30 mL) and ethylene glycol dimethyl ether (150 mL) was stirred for 5 hours at room temperature. The reaction was then quenched by water. The resulting solution was extracted with ethyl acetate, dried with anhydrous sodium sulfate. After filtration, the filtrate was concentrated under vacuum. The residue was purified by flash chromatography on silica gel eluting with ethyl acetate/petroleum ether (4/6) to afford methyl 2-methyl-3-[1-(oxan-2-yl)-1H-pyrazol-3-yl]cyclopropane-1-carboxylate (1.5 g, 5.66 mmol) as yellow oil. LC/MS (ESI) [M+H]$^+$=265

Step 4: 2-methyl-3-(1-(tetrahydro-2H-pyran-2-yl)-1H-pyrazol-3-yl)cyclopropanecarboxylic Acid

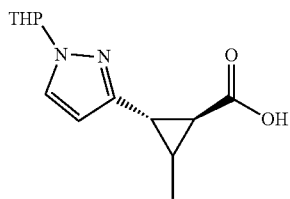

A mixture of methyl 2-methyl-3-[1-(oxan-2-yl)-1H-pyrazol-3-yl]cyclopropane-1-carboxylate (1.45 g, 5.49 mmol), LiOH (659 mg, 27.52 mmol) in tetrahydrofuran (15 mL) and water (15 mL) was stirred for 12 hours at room temperature. The resulting mixture was washed with ethyl acetate. The water phase was adjusted to pH 3 with hydrogen chloride (1 mol/L). The resulting solution was extracted with ethyl acetate, dried with anhydrous sodium sulfate. After filtration, the filtrate was concentrated under vacuum to afford 2-methyl-3-[1-(oxan-2-yl)-1H-pyrazol-3-yl]cyclopropane-1-carboxylic acid (1.3 g, 5.18 mmol) as a yellow solid. LCMS (ESI) [M+H]$^+$=251

Step 5: N-(8-chloro-7-fluoro-6-(4-methylpyridin-3-yl)isoquinolin-3-yl)-2-methyl-3-(1-(tetrahydro-2H-pyran-2-yl)-1H-pyrazol-3-yl)cyclopropanecarboxamide

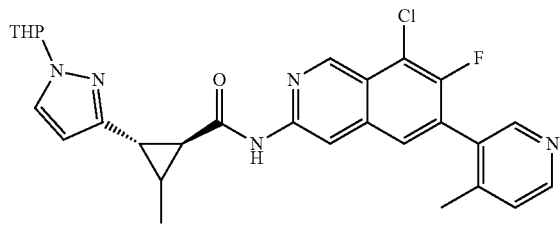

A mixture of 8-chloro-7-fluoro-6-(4-methylpyridin-3-yl)isoquinolin-3-amine (1.5 g, 5.21 mmol), 2-methyl-3-[1-(oxan-2-yl)-1H-pyrazol-3-yl]cyclopropane-1-carboxylic acid (1.3 g, 5.19 mmol), POCl$_3$ (1.6 g, 10.44 mmol), pyridine (5 mL, 62.12 mmol) in dichloromethane (30 mL) was stirred for 30 minutes at room temperature. The reaction was then quenched by water. The resulting solution was extracted with dichloromethane, dried with anhydrous sodium sulfate. After filtration, the filtrate was concentrated under vacuum. The residue was purified by flash chromatography on silica gel eluting with ethyl acetate/petroleum ether (2/1) to afford (1S,3S)—N-[8-chloro-7-fluoro-6-(4-methylpyridin-3-yl)isoquinolin-3-yl]-2-methyl-3-[1-(oxan-2-yl)-1H-pyrazol-3-yl]cyclopropane-1-carboxamide (1.26 g, 2.42 mmol) as a yellow solid. LCMS (ESI) [M+H]$^+$=520.

Step 6: tert-butyl 7-fluoro-3-(2-methyl-3-(1-(tetrahydro-2H-pyran-2-yl)-1H-pyrazol-3 yl)cyclopropanecarboxamido)-6-(4-methylpyridin-3-yl)isoquinolin-8-ylcarbamate

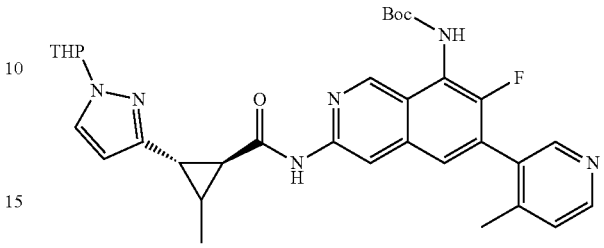

A mixture of N-[8-chloro-7-fluoro-6-(4-methylpyridin-3-yl)isoquinolin-3-yl]-2-methyl-3-[1-(oxan-2-yl)-1H-pyrazol-3-yl]cyclopropane-1-carboxamide (1.3 g, 2.50 mmol), tert-butyl carbamate (8.79 g, 75.05 mmol), BrettPhos (269 mg, 0.50 mmol), tris(dibenzylideneacetone)dipalladium-chloroformadduct (518 mg, 0.50 mmol, Cesium carbonate (3.27 g, 10.02 mmol) in 1,4-dioxane (160 mL) was stirred for 2 hours at 90° C. After filtration, the filtrate was concentrated under vacuum. The residue was purified by flash chromatography on silica gel eluting with ethyl acetate/petroleum ether (9/1) to afford tert-butyl N-(7-fluoro-3-[[2-methyl-3-[1-(oxan-2-yl)-1H-pyrazol-3-yl]cyclopropane]amido]-6-(4-methylpyridin-3-yl)isoquinolin-8-yl)carbamate (480 mg, 0.80 mmol) as a yellow solid. LC/MS (ESI) [M+H]$^+$=601.

Step 7: (1R,2R,3R)—N-(8-amino-7-fluoro-6-(4-methylpyridin-3-yl)isoquinolin-3-yl)-2-methyl-3-(1H-pyrazol-5-yl)cyclopropanecarboxamide (assumed), (1S,2R,3S)—N-(8-amino-7-fluoro-6-(4-methylpyridin-3-yl)isoquinolin-3-yl)-2-methyl-3-(1H-pyrazol-5-yl)cyclopropanecarboxamide (assumed), (1S,2S,3S)—N-(8-amino-7-fluoro-6-(4-methylpyridin-3-yl)isoquinolin-3-yl)-2-methyl-3-(1H-pyrazol-5-yl)cyclopropanecarboxamide (assumed) and (1R,2S,3R)—N-(8-amino-7-fluoro-6-(4-methylpyridin-3-yl)isoquinolin-3-yl)-2-methyl-3-(1H-pyrazol-5-yl)cyclopropanecarboxamide (Assumed)

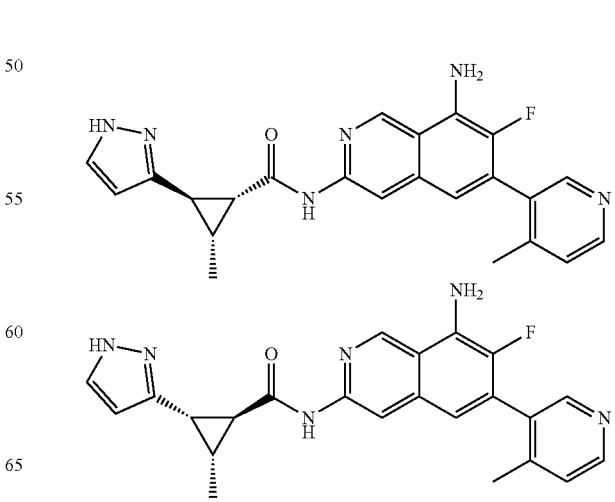

-continued

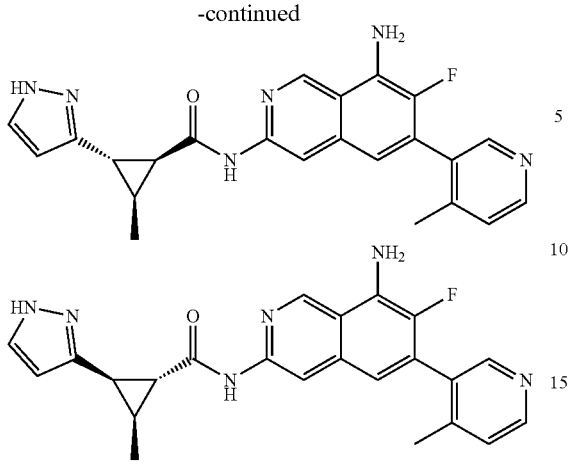

A mixture of tert-butyl N-(7-fluoro-3-[[2-methyl-3-[1-(oxan-2-yl)-1H-pyrazol-3-yl]cyclopropane]amido]-6-(4-methylpyridin-3-yl)isoquinolin-8-yl)carbamate (480 mg, 0.80 mmol), methanol (2 mL, 49.40 mmol) in HCl/dioxane (8 mL) was stirred for 10 h at room temperature. The resulting solution was concentrated uncer vacuum. The crude product was purified by Prep-HPLC (C18 silica gel; 0.5% sodium bicarbonate in water:ACN=30%-40% in 7 min) to afford the mixture (150 mg, 0.36 mmol). The mixture was separated by Chiral-HPLC to afford four isomers (Cyclopropane stereochemistry for each isomer: pyrazole trans to amide; methyl relative stereochemistry arbitrarily assigned; All absolute stereochemistry arbitrarily assigned): Compound 332: (16.7 mg, 0.040 mmol) as a yellow solid. Retention time: 2.289 min (Repaired Chiral IC. 0.46*10 cm; 5 μm; MtBE (0.1% DEA):IPA=70:30; 1.0 ml/min); LCMS (ESI) [M+H]$^+$=417.3; $^1$H NMR (400 MHz, DMSO-d$_6$) δ 12.73-12.49 (m, 1H), 10.82-10.77 (m, 1H), 9.42 (s, 1H), 8.52 (d, J=5.0 Hz, 1H), 8.44 (s, 1H), 8.35 (s, 1H), 7.61-7.35 (m, 2H), 6.96 (d, J=6.1 Hz, 1H), 6.32 (s, 2H), 6.06-5.97 (m, 1H), 2.42-2.29 (m, 2H), 2.22 (s, 3H), 1.73 (s, 1H), 1.29 (d, J=6.1 Hz, 3H). Compound 331: (36.7 mg, 0.088 mmol) as a yellow solid. Retention time: 2.917 min (Repaired Chiral IC. 0.46*10 cm; 5 μm; MtBE (0.1% DEA):IPA=70:30; 1.0 ml/min); LCMS (ESI) [M+H]$^+$=417.2; $^1$H NMR (400 MHz, DMSO-d$_6$) δ 12.77-12.59 (m, 1H), 10.82 (s, 1H), 9.43 (s, 1H), 8.51 (d, J=5.0 Hz, 1H), 8.44 (s, 1H), 8.33 (s, 1H), 7.66-7.40 (m, 2H), 6.94 (d, J=6.0 Hz, 1H), 6.32 (s, 2H), 6.14-6.01 (m, 1H), 2.49-2.24 (m, 3H), 2.22 (s, 2H), 1.70-1.64 (m, 1H), 1.1-0.9 (m, 3H). Compound 330: (17.8 mg, 0.043 mmol) as a yellow solid. Retention time: 3.720 min (Repaired Chiral IC. 0.46*10 cm; 5 μm; MtBE (0.1% DEA):IPA=70:30; 1.0 ml/min); LCMS (ESI) [M+H]$^+$=417.2; $^1$H NMR (400 MHz, DMSO-d$_6$) δ 12.73-12.49 (m, 1H), 10.82-10.77 (m, 1H), 9.42 (s, 1H), 8.52 (d, J=5.0 Hz, 1H), 8.44 (s, 1H), 8.36 (s, 1H), 7.61-7.35 (m, 2H), 7.09-6.82 (m, 1H), 6.32 (s, 2H), 6.15-5.72 (m, 1H), 2.43-2.32 (m, 2H), 2.22 (s, 3H), 1.77-1.69 (m, 1H), 1.28 (d, J=6.0 Hz, 3H). Compound 329: (37.4 mg, 0.090 mmol) as a yellow solid.
Retention time: 6.054 min (Repaired Chiral IC. 0.46*10 cm; 5 μm; MtBE (0.1% DEA):IPA=70:30; 1.0 ml/min); LCMS (ESI) [M+H]$^+$=417.2; $^1$H NMR (400 MHz, DMSO-d$_6$) δ 12.77-12.58 (m, 1H), 10.82 (s, 1H), 9.43 (s, 1H), 8.51 (d, J=5.0 Hz, 1H), 8.44 (s, 1H), 8.33 (s, 1H), 7.65-7.37 (m, 2H), 6.94 (d, J=6.1 Hz, 1H), 6.32-6.02 (m, 3H), 2.48-2.30 (s, 2H), 2.22 (s, 3H), 1.66 (s, 1H), 1.02 (d, J=6.5 Hz, 3H).

Example 213

(1S,2S)—N-(8-amino-7-fluoro-6-(4-methylpyridin-3-yl)isoquinolin-3-yl)-2-(1H-imidazol-5-yl)cyclopropane-1-carboxamide (Compound 335) and (1R,2R)—N-(8-amino-7-fluoro-6-(4-methylpyridin-3-yl)isoquinolin-3-yl)-2-(1H-imidazol-5-yl)cyclopropane-1-carboxamide (Compound 334)

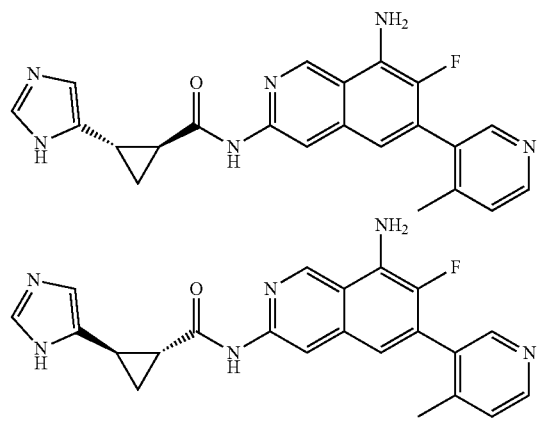

Step 1: ethyl (2E)-3-[1-(triphenylmethyl)-1H-imidazol-4-yl]prop-2-enoate

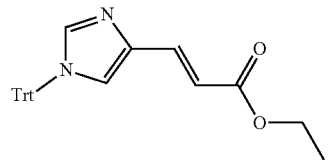

A mixture of 4-iodo-1-(triphenylmethyl)-1H-imidazole (7.41 g, 16.98 mmol), ethyl (2E)-3-(tetramethyl-1,3,2-dioxaborolan-2-yl)prop-2-enoate (9.60 g, 42.46 mmol), tetrakis(triphenylphosphine)palladium (1.96 g, 1.69 mmol), potassium phosphate (10.82 g, 50.97 mmol) in 1,4-dioxane (100 mL) and water (20 mL) was stirred for 6 h at 100° C. The reaction was concentrated under vacuum. The residue was purified by silica gel column with ethyl acetate/petroleum ether (20/80) to afford ethyl (2E)-3-[1-(triphenylmethyl)-1H-imidazol-4-yl]prop-2-enoate (2 g, 4.90 mmol) as a light yellow solid. LCMS (ESI) [M+H]$^+$=409.

Step 2: ethyl trans-2-[1-(triphenylmethyl)-1H-imidazol-4-yl]cyclopropane-1-carboxylate

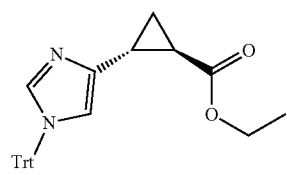

A mixture of S,S-dimethylmethanesulfinyl iodide (3.02 g, 13.72 mmol) and t-BuOK (1.54 g, 13.72 mmol) in dimethyl sulphoxide (20 mL) was stirred for 30 min at 25° C. Ethyl (2E)-3-[1-(triphenylmethyl)-1H-imidazol-4-yl]prop-2-enoate (1.4 g, 3.42 mmol) was added. The resulting solution was stirring for 15 h at 25° C. The resulting mixture was diluted with water and then extracted with ethyl acetate. The organic layers combined and dried with anhydrous sodium sulfate. After filtration, the filtrate was concentrated under vacuum. The residue was purified by silica gel column with dichloromethane/methanol (20/1) to afford ethyl trans-2-[1-(triphenylmethyl)-1H-imidazol-4-yl]cyclopropane-1-carboxylate (360 mg, 0.85 mmol) as yellow oil. LCMS (ESI) [M+H]$^+$=423.

Step 3: Trans-2-[1-(triphenylmethyl)-1H-imidazol-4-yl]cyclopropane-1-carboxylic Acid

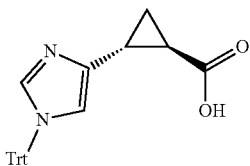

A mixture of ethyl trans-2-[1-(triphenylmethyl)-1H-imidazol-4-yl]cyclopropane-1-carboxylate (600 mg, 1.42 mmol) and LiOH (170 mg, 7.09 mmol) in tetrahydrofuran (10 mL) and water (10 mL) was stirred for 12 h at room temperature. The reaction mixture was adjusted to pH 4-5 with hydrogen chloride. The resulting solution was extracted with dichloromethane and dried with anhydrous sodium sulfate. After filtration, the filtrate was concentrated under vacuum to afford trans-2-[1-(triphenylmethyl)-1H-imidazol-4-yl]cyclopropane-1-carboxylic acid (460 mg, 1.17 mmol) as a white solid. LCMS (ESI) [M+H]$^+$=395.

Step 4: trans-N-[8-chloro-7-fluoro-6-(4-methylpyridin-3-yl)isoquinolin-3-yl]-2-[1-(triphenylmethyl)-1H-imidazol-4-yl]cyclopropane-1-carboxamide

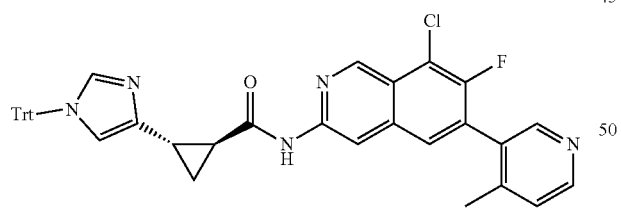

To a solution of 8-chloro-7-fluoro-6-(4-methylpyridin-3-yl)isoquinolin-3-amine (364 mg, 1.26 mmol), trans-2-[1-(triphenylmethyl)-1H-imidazol-4-yl]cyclopropane-1-carboxylic acid (500 mg, 1.26 mmol) in dichloromethane (20 mL) and pyridine (3 mL) was added phosphorus oxychloride (290 mg, 1.89 mmol) at 0° C. The mixture was stirred for 30 min at 0° C. The reaction was concentrated under vacuum. The residue was purified by silica gel column with dichloromethane/methanol (10/1) to afford trans-N-[8-chloro-7-fluoro-6-(4-methylpyridin-3-yl)isoquinolin-3-yl]-2-[1-(triphenylmethyl)-1H-imidazol-4-yl]cyclopropane-1-carboxamide (300 mg, 0.45 mmol) as a white solid. LCMS (ESI) [M+H]$^+$=664.

Step 5: trans-tert-butyl N-[7-fluoro-6-(4-methylpyridin-3-yl)-3-[[2-[1-(triphenylmethyl)-1H-imidazol-4-yl]cyclopropane]amido]isoquinolin-8-yl]carbamate

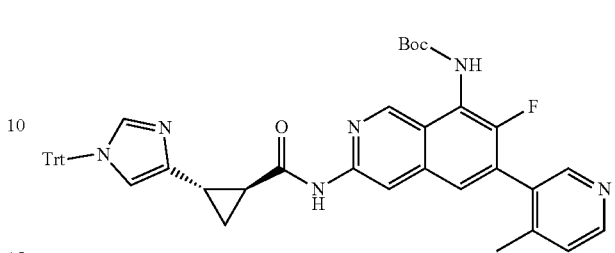

A mixture of trans-N-[8-chloro-7-fluoro-6-(4-methylpyridin-3-yl)isoquinolin-3-yl]-2-[1-(triphenylmethyl)-1H-imidazol-4-yl]cyclopropane-1-carboxamide (600 mg, 0.90 mmol), tert-butyl carbamate (2.1 g, 17.92 mmol), tris(dibenzylideneacetone)dipalladium (187 mg, 0.18 mmol), BrettPhos (193 mg, 0.36 mmol), and cesium carbonate (1.17 g, 3.59 mmol) in 1,4-dioxane (20 mL) was stirred for 5 h at 90° C. After filtration, the filtrate was concentrated under vacuum. The residue was purified by flash chromatography on silica gel eluting with dichloromethane/methanol (10/1) to afford trans-tert-butyl N-[7-fluoro-6-(4-methylpyridin-3-yl)-3-[[2-[1-(triphenylmethyl)-1H-imidazol-4-yl]cyclopropane]amido]isoquinolin-8-yl]carbamate (300 mg, 0.40 mmol) as a white solid. LCMS (ESI) [M+H]$^+$=745.

Step 6: (1S,2S)—N-[8-amino-7-fluoro-6-(4-methylpyridin-3-yl)isoquinolin-3-yl]-2-(1H-imidazol-5-yl)cyclopropane-1-carboxamide and (1R,2R)—N-[8-amino-7-fluoro-6-(4-methylpyridin-3-yl)isoquinolin-3-yl]-2-(1H-imidazol-5-yl)cyclopropane-1-carboxamide

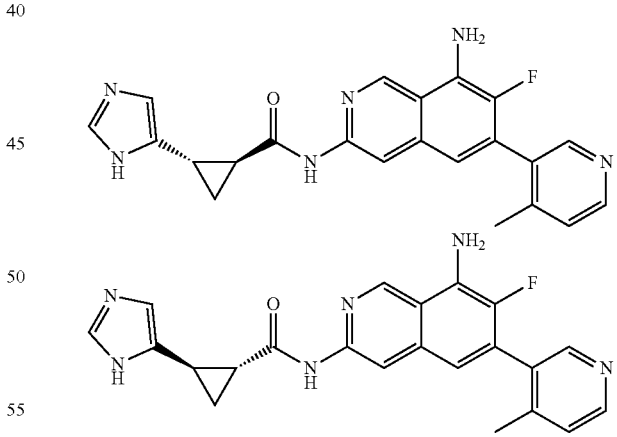

A solution of trans-tert-butyl N-[7-fluoro-6-(4-methylpyridin-3-yl)-3-[[2-[1-(triphenylmethyl)-1H-imidazol-4-yl]cyclopropane]amido]isoquinolin-8-yl]carbamate (200 mg, 0.26 mmol) in trifluoroacetic acid (5 mL) was stirred for 12 h at room temperature. The resulting mixture was concentrated under vacuum. The residue was purified by reverse phase chromatography (acetonitrile 0-50/0.1% sodium bicarbonate in water) to afford the racemic product (40 mg, 0.09 mmol) as a yellow solid. The racemate was separated by Chiral-HPLC to afford two isomers: (Cyclopropane stereochemistry for each isomers: imidazole trans to amide; All absolute stereochemistry arbitrarily assigned) Compound 335: Retention time:3.38 min (CHIRALPAK ID-3, 0.46*10 cm; 3 μm; MtBE (0.1% DEA):EtOH=70:30; 1 ml/min); LCMS (ESI) [M+H]⁺=403; ¹HNMR (400 MHz, CD₃OD) δ 9.27 (s, 1H), 8.45 (d, J=4.0 Hz, 1H), 8.39 (s, 1H), 8.32 (s, 1H), 7.57 (s, 1H), 7.42 (d, J=4.0 Hz, 1H), 6.98 (d, J=4.0 Hz, 1H), 6.92 (s, 1H), 2.51-2.46 (m, 1H), 2.29 (s, 3H), 2.19-2.18 (m, 1H), 1.57-1.52 (m, 1H), 1.41-1.38 (m, 1H). Compound 334: Retention time:5.68 min (CHIRALPAK ID-3, 0.46*10 cm; 3 μm;

MtBE (0.1% DEA):EtOH=70:30; 1 ml/min); LCMS (ESI) [M+H]⁺=403; ¹HNMR (400 MHz, CD₃OD) δ 9.27 (s, 1H), 8.45 (d, J=4.0 Hz, 1H), 8.39 (s, 1H), 8.32 (s, 1H), 7.57 (s, 1H), 7.42 (d, J=4.0 Hz, 1H), 6.98 (d, J=4.0 Hz, 1H), 6.92 (s, 1H), 2.51-2.46 (m, 1H), 2.29 (s, 3H), 2.19-2.18 (m, 1H), 1.57-1.52 (m, 1H), 1.41-1.38 (m, 1H)

Example 214

(1S,2S,3S)—N-(8-amino-7-fluoro-6-(4-methylpyridin-3-yl)isoquinolin-3-yl)-2-(1-(2,2-difluoroethyl)-1H-pyrazol-4-yl)-3-methylcyclopropane-1-carboxamide (Compound 340)

(1S,2S,3R)—N-(8-amino-7-fluoro-6-(4-methylpyridin-3-yl)isoquinolin-3-yl)-2-(1-(2,2-difluoroethyl)-1H-pyrazol-4-yl)-3-methylcyclopropane-1-carboxamide (Compound 339)

(1R,2R,3S)—N-(8-amino-7-fluoro-6-(4-methylpyridin-3-yl)isoquinolin-3-yl)-2-(1-(2,2-difluoroethyl)-1H-pyrazol-4-yl)-3-methylcyclopropane-1-carboxamide (Compound 338) and (1R,2R,3R)—N-(8-amino-7-fluoro-6-(4-methylpyridin-3-yl)isoquinolin-3-yl)-2-(1-(2,2-difluoroethyl)-1H-pyrazol-4-yl)-3-methylcyclopropane-1-carboxamide (Compound 337)

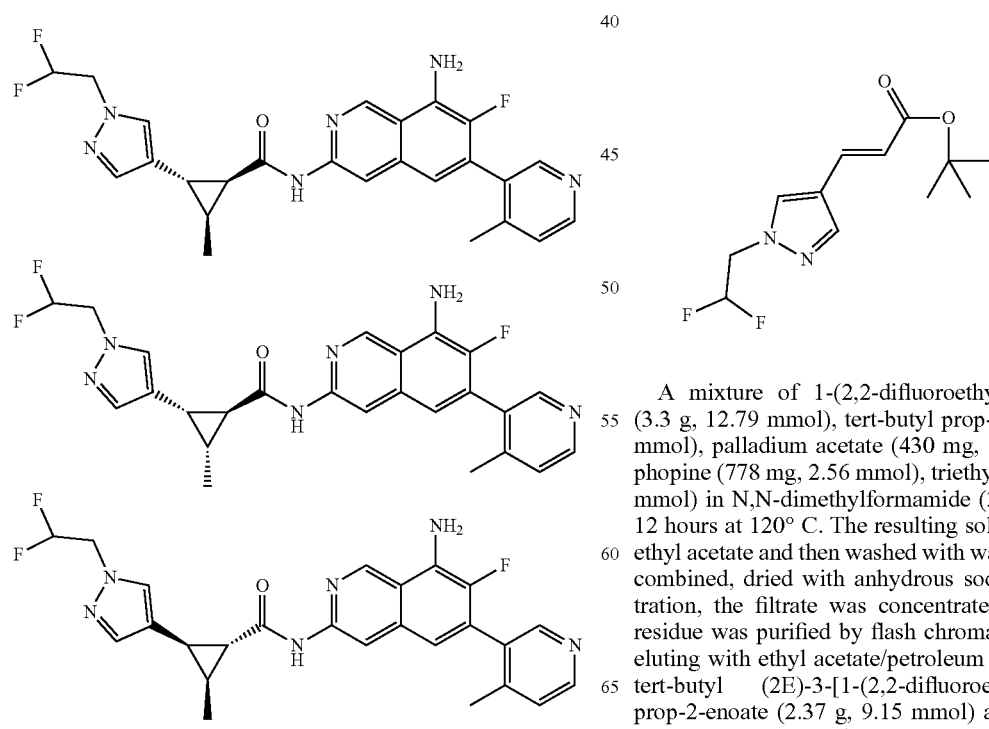

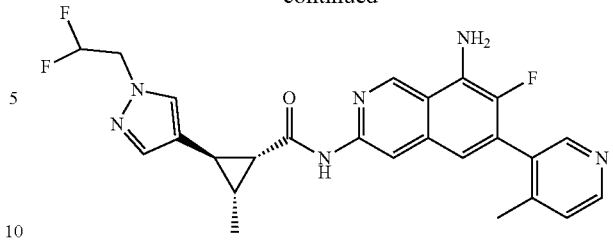

-continued

Step 1: 1-(2,2-difluoroethyl)-4-iodo-1H-pyrazole

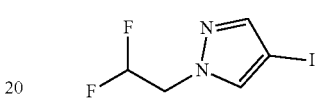

A mixture of 4-iodo-1H-pyrazole (3 g, 15.47 mmol), 2-bromo-1,1-difluoroethane (2.7 g, 18.63 mmol), potassium carbonate (4.3 g, 31.11 mmol) in N,N-dimethylformamide (30 mL) was stirred for 12 hours at room temperature. The resulting mixture was concentrated under vacuum. The residue was applied onto a silica gel column with ethyl acetate/petroleum ether (20/80) to afford 1-(2,2-difluoroethyl)-4-iodo-1H-pyrazole (3.3 g, 12.74 mmol) as colorless oil. LCMS (ESI) [M+H]⁺=259.

Step 2: (E)-tert-butyl 3-(1-(2,2-difluoroethyl)-1H-pyrazol-4-yl)acrylate

A mixture of 1-(2,2-difluoroethyl)-4-iodo-1H-pyrazole (3.3 g, 12.79 mmol), tert-butyl prop-2-enoate (4.9 g, 38.23 mmol), palladium acetate (430 mg, 1.92 mmol), tri-o-tolyl phopine (778 mg, 2.56 mmol), triethylamine (1.94 g, 19.172 mmol) in N,N-dimethylformamide (30 mL) was stirred for 12 hours at 120° C. The resulting solution was diluted with ethyl acetate and then washed with water. The organic layers combined, dried with anhydrous sodium sulfate. After filtration, the filtrate was concentrated under vacuum. The residue was purified by flash chromatography on silica gel eluting with ethyl acetate/petroleum ether (60/40) to afford tert-butyl (2E)-3-[1-(2,2-difluoroethyl)-1H-pyrazol-4-yl] prop-2-enoate (2.37 g, 9.15 mmol) as a light yellow solid. LC/MS (ESI) [M+H]⁺=259.

Step 3: tert-butyl 2-(1-(2,2-difluoroethyl)-1H-pyrazol-4-yl)-3-methylcyclopropanecarboxylate

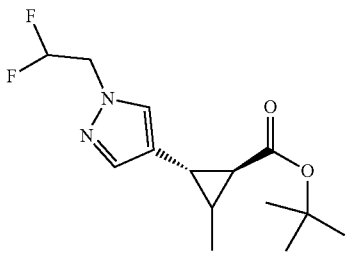 [SMILES: CC1[C@H](C(=O)OC(C)(C)C)[C@H]1c1cnn(CC(F)F)c1]

A mixture of tert-butyl (2E)-3-[1-(2,2-difluoroethyl)-1H-pyrazol-4-yl]prop-2-enoate (2.9 g, 11.23 mmol), thylene glycol dimethyl ether (150 mL, 1.55 mol), lithium diisopropylamide (19.6 mL, 365.93 mmol and eethyldiphenylsulfanium trifluoroborane fluoride (10.2 g, 33.76 mmol) in dichloromethane (20 mL) was stirred for 5 hours at room temperature. The reaction was then quenched by water. The resulting solution was extracted with dichloromethane, dried with anhydrous sodium sulfate. After filtration, the filtrate was concentrated under vacuum. The residue was purified by flash chromatography on silica gel eluting with ethyl acetate/petroleum ether (7/3) to afford tert-butyl 2-[1-(2,2-difluoroethyl)-1H-pyrazol-4-yl]-3-methylcyclopropane-1-carboxylate (1.9 g, 6.62 mmol) as yellow oil. LCMS (ESI) $[M+H]^+=287$

Step 4: 2-(1-(2,2-difluoroethyl)-1H-pyrazol-4-yl)-3-methylcyclopropanecarboxylic Acid

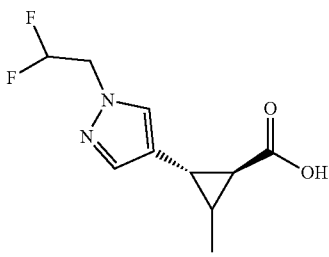 [SMILES: CC1[C@H](C(=O)O)[C@H]1c1cnn(CC(F)F)c1]

A mixture of tert-butyl 2-[1-(2,2-difluoroethyl)-1H-pyrazol-4-yl]-3-methylcyclopropane-1-carboxylate (1.9 g, 6.64 mmol) in trifluoroacetic acid (10 mL) and dichloromethane (20 mL) was stirred for 3 hours at room temperature. The resulting mixture was concentrated under vacuum. The crude product was purified by Prep-HPLC with the following conditions (C18 silica gel; $CH_3CN/H_2O=5\%/95\%$ increasing to $CH_3CN/H_2O=40\%/60\%$ in 30 min) to afford 2-[1-(2,2-difluoroethyl)-1H-pyrazol-4-yl]-3-methylcyclopropane-1-carboxylic acid (1.13 g, 4.89 mmol) as purple oil. LCMS (ESI) $[M+H]^+=231$.

Step 5: N-(8-chloro-7-fluoro-6-(4-methylpyridin-3-yl)isoquinolin-3-yl)-2-(1-(2,2-difluoroethyl)-1H-pyrazol-4-yl)-3-methylcyclopropanecarboxamide


A mixture of 2-[1-(2,2-difluoroethyl)-1H-pyrazol-4-yl]-3-methylcyclopropane-1-carboxylic acid (1.1 g, 4.78 mmol), 8-chloro-7-fluoro-6-(4-methylpyridin-3-yl)isoquinolin-3-amine (1.4 g, 4.87 mmol), phosphorus oxychloride (1.5 g, 9.78 mmol), pyridine (5 mL, 62.118 mmol) in dichloromethane (50 mL) was stirred for 30 minutes at room temperature. The reaction was then quenched by water. The resulting solution was extracted with ethyl acetate, dried with anhydrous sodium sulfate. After filtration, the filtrate was concentrated under vacuum. The residue was purified by flash chromatography on silica gel eluting with ethyl acetate/petroleum ether (8/2) to afford N-[8-chloro-7-fluoro-6-(4-methylpyridin-3-yl)isoquinolin-3-yl]-2-[1-(2,2-difluoroethyl)-1H-pyrazol-4-yl]-3-methylcyclopropane-1-carboxamide (1.48 g, 2.96 mmol) as a white solid. LCMS (ESI) $[M+H]^+=500$.

Step 6: tert-butyl 3-(2-(1-(2,2-difluoroethyl)-1H-pyrazol-4-yl)-3-methylcyclopropanecarboxamido)-7-fluoro-6-(4-methylpyridin-3-yl)isoquinolin-8-ylcarbamate

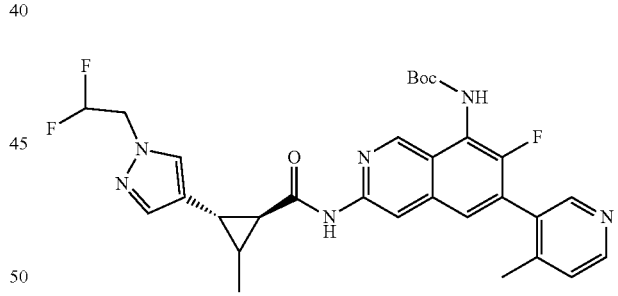

A mixture of N-[8-chloro-7-fluoro-6-(4-methylpyridin-3-yl)isoquinolin-3-yl]-2-[1-(2,2-difluoroethyl)-1H-pyrazol-4-yl]-3-methylcyclopropane-1-carboxamide (1.4 g, 2.80 mmol), tert-butyl carbamate (9.85 g, 84.08 mmol), BrettPhos (302 mg, 0.56 mmol), tris(dibenzylideneacetone)dipalladium-chloroformadduct (581 mg, 0.56 mmol), Cesium carbonate (3.66 g, 11.23 mmol) in 1,4-dioxane (120 mL) was stirred for 3 hours at 90° C. After filtration, the filtrate was concentrated under vacuum. The residue was purified by flash chromatography on silica gel eluting with dichloromethane/methanol (8/2) to afford tert-butyl N-(3-[[2-[1-(2,2-difluoroethyl)-1H-pyrazol-4-yl]-3-methylcyclopropane]amido]-7-fluoro-6-(4-methylpyridin-3-yl)isoquinolin-8-yl)carbamate (1.44 g, 2.48 mmol) as a yellow solid. LCMS (ESI) $[M+H]^+=581$ Step 7: (1S,2S,3S)—N-(8-amino-7-fluoro-6-(4-methylpyridin-3-yl)isoquinolin-3-yl)-2-(1-(2,2-difluoroethyl)-1H-pyrazol-4-yl)-3-methylcyclopropanecarboxamide, (1S,2S,3R)—N-(8-amino-7-fluoro-6-(4-methylpyridin-3-yl)isoquinolin-3-yl)-2-(1-(2,2-difluoroethyl)-1H-pyrazol-4-yl)-3-methylcyclopropanecarboxamide, (1R,2R,3S)—N-(8-amino-7-fluoro-6-(4-methylpyridin-3-yl)isoquinolin-3-yl)-2-(1-(2,2-difluoroethyl)-1H-pyrazol-4-yl)-3-methylcyclopropanecarboxamide and (1R,2R,3R)—N-(8-amino-7-fluoro-6-(4-methylpyridin-3-yl)isoquinolin-3-yl)-2-(1-(2,2-difluoroethyl)-1H-pyrazol-4-yl)-3-methylcyclopropanecarboxamide

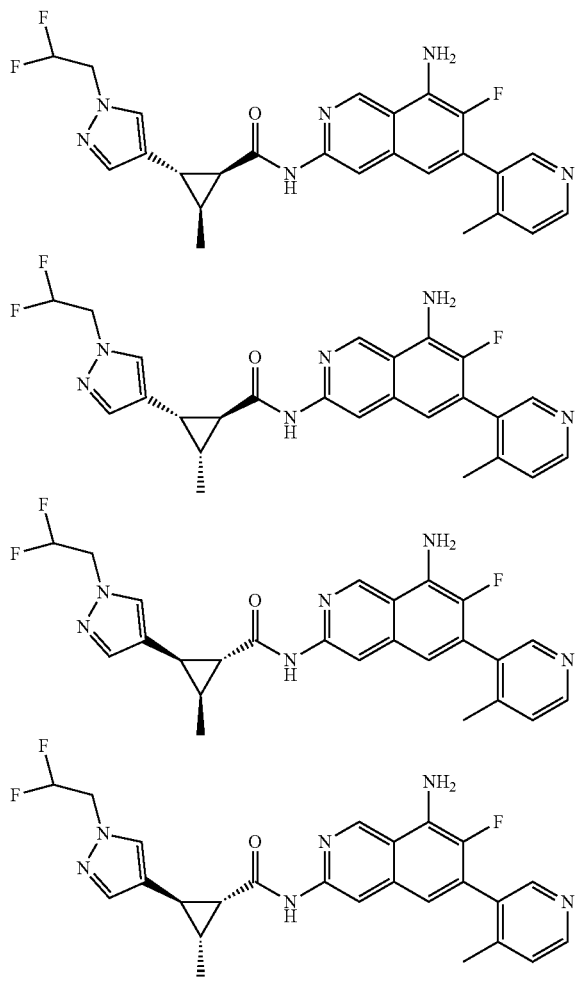

A mixture of tert-butyl N-(3-[[2-[1-(2,2-difluoroethyl)-1H-pyrazol-4-yl]-3-methylcyclopropane]amido]-7-fluoro-6-(4-methylpyridin-3-yl)isoquinolin-8-yl)carbamate (1.4 g, 2.41 mmol), HCl/dioxane (30 mL, 354.12 mmol) in methanol (10 mL) was stirred for 1 hour at 25° C. The mixture was concentrated under vacuum. The crude product was purified by Prep-HPLC (C18 silica gel; 0.5% sodium bicarbonate in water:ACN=37%-45% in 7 min) to afford the mixture (550 mg, 1.15 mmol). The mixture was separated by Chiral-HPLC to afford four isomers (Cyclopropane stereochemistry for each isomer: pyrazole trans to amide; methyl relative stereochemistry arbitrarily assigned; All absolute stereochemistry arbitrarily assigned): Compound 340: (46.5 mg, 0.097 mmol) as a yellow solid. Retention time: 1.65 min (Lux 5u Cellulose-3. 4.6*250 mm, 5 μm; MeOH (0.1% DEA); 4.0 ml/min); LCMS (ESI) [M+H]$^+$=481.2; $^1$HNMR (300 VMHz, DMO-d$_6$) δ 10.72 (s, 1H), 9.42 (s, 1H), 8.52 (d, J=5.0 Hz, 1H), 8.44 (s, 1H), 8.35 (s, 1H), 7.63 (s, 1H), 7.45-7.34 (m, 2H), 6.95 (d, J=6.1 Hz, 1H), 6.50-6.13 (m, 3H), 4.55 (td, J=15.1, 3.8 Hz, 2H), 2.31-2.22 (m, 5H), 1.66-1.51 (m, 1H), 1.28 (d, J=6.2 Hz, 3H). Compound 339: (163.3 mg, 0.34 mmol) as a yellow solid. Retention time: 1.86 min (Lux 5u Cellulose-3. 4.6*250 mm, 5 μm; MeOH (0.1% DEA); 4.0 ml/min); LCMS (ESI) [M+H]$^+$=481.3; H NMR (300 MHz, DMSO-d$_6$) δ 10.77 (s, 1H), 9.43 (s, 1H), 8.51 (d, J=5.0 Hz, 1H), 8.44 (s, 1H), 8.32 (s, 1H), 7.64 (s, 1H), 7.46-7.36 (m, 2H), 6.93 (d, J=6.1 Hz, 1H), 6.52-6.16 (m, 3H), 4.60 (td, J=15.2, 3.8 Hz, 2H), 2.37-2.30 (m, 1H), 2.22 (s, 3H), 2.15 (t, J=4.7 Hz, 1H) 1.70-1.55 (m, 1H), 0.96 (d, J=6.3 Hz, 3H). Compound 338: (173.9 mg, 0.36 mmol) as a yellow solid. Retention time: 2.23 min (Lux 5u Cellulose-3. 4.6*250 mm, 5 μm; MeOH (0.1% DEA); 4.0 ml/min); LCMS (ESI) [M+H]$^+$=481.3; $^1$H NMR (300 MHz, DMSO-d$_6$) δ 10.77 (s, 1H), 9.43 (s, 1H), 8.51 (d, J=5.0 Hz, 1H), 8.44 (s, 1H), 8.32 (s, 1H), 7.64 (s, 1H), 7.46-7.36 (m, 2H), 6.93 (d, J=6.1 Hz, 1H), 6.52-6.16 (m, 3H), 4.60 (td, J=15.2, 3.8 Hz, 2H), 2.37-2.30 (m, 1H), 2.22 (s, 3H), 2.15 (t, J=4.7 Hz, 1H) 1.69-1.56 (m, 1H), 0.96 (d, J=6.3 Hz, 3H). Compound 337: (66.3 mg, 0.14 mmol) as a yellow solid. Retention time: 2.91 min (Lux 5u Cellulose-3. 4.6*250 mm, 5 μm; MeOH (0.1% DEA); 4.0 ml/min); LCMS (ESI) [M+H]$^+$=481.3; $^1$H NMR (300 MHz, DMSO-d$_6$) δ 10.71 (s, 1H), 9.42 (s, 1H), 8.52 (d, J=5.0 Hz, 1H), 8.44 (s, 1H), 8.35 (s, 1H), 7.63 (s, 1H), 7.45-7.34 (m, 2H), 6.95 (d, J=6.1 Hz, 1H), 6.51-6.13 (m, 3H), 4.55 (td, J=15.2, 3.8 Hz, 2H), 2.31-2.15 (m, 5H), 1.66-1.52 (m, 1H), 1.28 (d, J=6.2 Hz, 3H).

Example 215

(1R,2S)—N-(8-amino-7-fluoro-6-(4-methylpyridin-3-yl)isoquinolin-3-yl)-2-((dimethylamino)methyl)cyclopropane-1-carboxamide (Compound 342) and (1S,2R)—N-(8-amino-7-fluoro-6-(4-methylpyridin-3-yl)isoquinolin-3-yl)-2-((dimethylamino)methyl)cyclopropane-1-carboxamide (Compound 341)

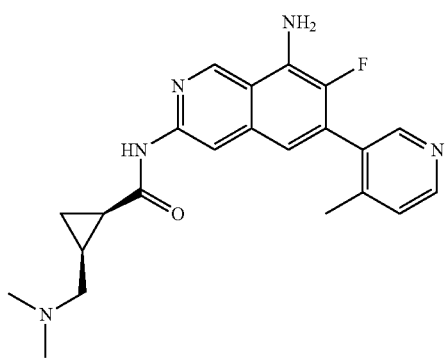

-continued-

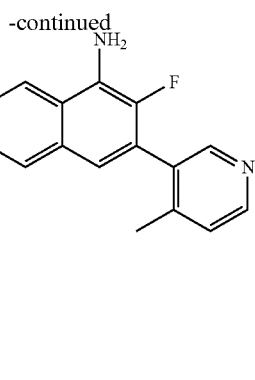

Step 1: 3-[8-chloro-7-fluoro-6-(4-methylpyridin-3-yl)isoquinolin-3-yl]-3-azabicyclo[3.1.0]hexane-2,4-dione

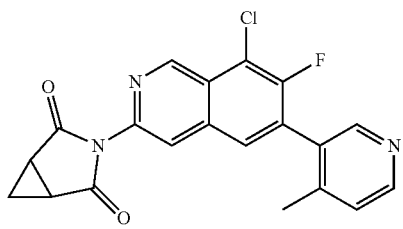 [SMILES: Cc1ccncc1-c1cc2cc(N3C(=O)C4CC4C3=O)ncc2c(Cl)c1F]

A mixture of 3-oxabicyclo[3.1.0]hexane-2,4-dione (390 mg, 3.48 mmol), 8-chloro-7-fluoro-6-(4-methylpyridin-3-yl)isoquinolin-3-amine (500 mg, 1.73 mmol), 4-dimethylaminopyridine (425 mg, 3.47 mmol) in dioxane (10 mL) was stirred for 12 h at 120° C. The resulting mixture was concentrated under vacuum. The residue was purified by silica gel column with dichloromethane/methanol (10/1) to afford 3-[8-chloro-7-fluoro-6-(4-methylpyridin-3-yl)isoquinolin-3-yl]-3-azabicyclo[3.1.0]hexane-2,4-dione (450 mg, 1.18 mmol) as a white solid. LCMS (ESI) [M+H]$^+$=382.

Step 2: Cis-N-[8-chloro-7-fluoro-6-(4-methylpyridin-3-yl)isoquinolin-3-yl]-2-(hydroxymethyl)cyclopropane-1-carboxamide

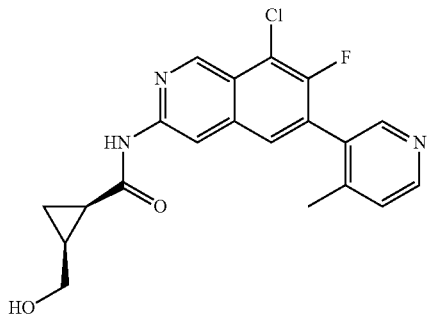 [SMILES: Cc1ccncc1-c1cc2cc(NC(=O)[C@@H]3C[C@@H]3CO)ncc2c(Cl)c1F]

To a solution of 3-[8-chloro-7-fluoro-6-(4-methylpyridin-3-yl)isoquinolin-3-yl]-3-azabicyclo[3.1.0]hexane-2,4-dione (450 mg, 1.17 mmol) in IPA (20 mL) and water (2 mL) was added NaBH$_4$ (224 mg, 5.92 mmol). The mixture was stirred for 1 h at room temperature. The resulting solution was extracted with ethyl acetate and the organic layers combined and concentrated under vacuum. The residue was purified by silica gel column with dichloromethane/methanol (10/1) to afford cis-N-[8-chloro-7-fluoro-6-(4-methylpyridin-3-yl)isoquinolin-3-yl]-2-(hydroxymethyl)cyclopropane-1-carboxamide (300 mg, 0.78 mmol) as a white solid. LCMS (ESI) [M+H]$^+$=386.

Step 3: Cis-[2-[[8-chloro-7-fluoro-6-(4-methylpyridin-3-yl)isoquinolin-3-yl]carbamoyl]cyclopropyl]methyl methanesulfonate

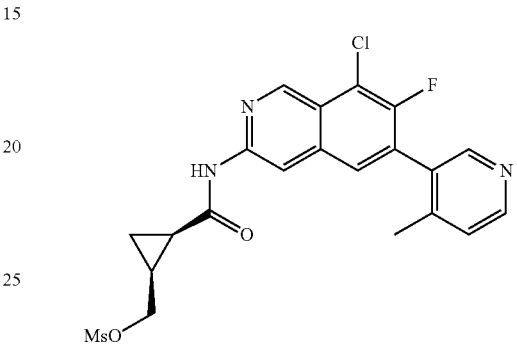

To a solution of cis-N-[8-chloro-7-fluoro-6-(4-methylpyridin-3-yl)isoquinolin-3-yl]-2-(hydroxymethyl)cyclopropane-1-carboxamide (300 mg, 0.77 mmol), triethylamine (236 mg, 2.33 mmol) in dichloromethane (20 mL) was added methanesulfonyl chloride (177 mg, 1.54 mmol) at 0° C. The mixture was then stirred for 1 h at room temperature. The resulting mixture was washed with water. The resulting solution was concentrated under vacuum to afford cis-[2-[[8-chloro-7-fluoro-6-(4-methylpyridin-3-yl)isoquinolin-3-yl]carbamoyl]cyclopropyl]methyl methanesulfonate (300 mg, 0.64 mmol) as a white solid. LCMS (ESI) [M+H]$^+$=464.

Step 4: Cis-N-[8-chloro-7-fluoro-6-(4-methylpyridin-3-yl)isoquinolin-3-yl]-2-[(dimethylamino)methyl]cyclopropane-1-carboxamide

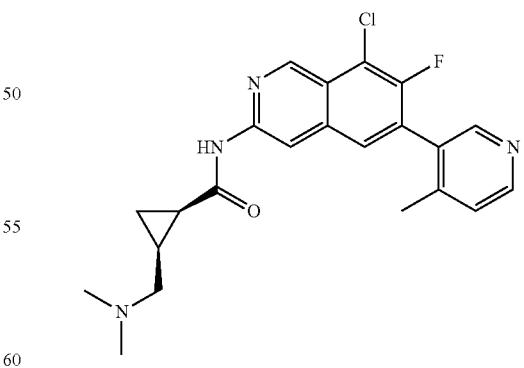

A mixture of cis-[2-[[8-chloro-7-fluoro-6-(4-methylpyridin-3-yl)isoquinolin-3-yl]carbamoyl]cyclopropyl]methyl methanesulfonate (300 mg, 0.64 mmol), dimethylamine (292 mg, 6.47 mmol) in tetrahydrofuran (5 mL) was stirred for 12 h at room temperature. The resulting mixture was concentrated under vacuum. The residue was purified by silica gel column with dichloromethane/methanol (3/1) to afford cis-N-[8-chloro-7-fluoro-6-(4-methylpyridin-3-yl)isoquinolin-3-yl]-2-[(dimethylamino)methyl]cyclopropane-1-carboxamide (250 mg, 0.60 mmol) as a white solid. LCMS (ESI) [M+H]$^+$=413.

Step 5: Cis-tert-butyl N-(3-[[2-[(dimethylamino)methyl]cyclopropane]amido]-7-fluoro-6-(4-methylpyridin-3-yl)isoquinolin-8-yl)carbamate

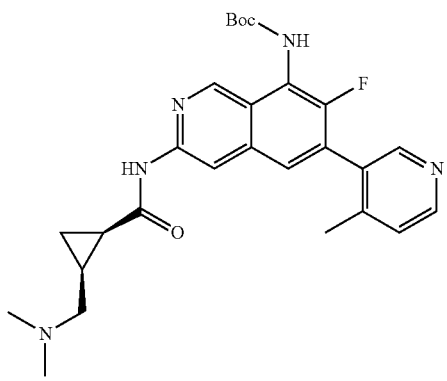 [SMILES: Cc1ccncc1-c1cc2cc(NC(=O)[C@@H]3C[C@@H]3CN(C)C)ncc2c(NC(=O)OC(C)(C)C)c1F]

The title compound was prepared in a fashion analogous to that described for Example 135 (Compound 36) using cis-N-[8-chloro-7-fluoro-6-(4-methylpyridin-3-yl)isoquinolin-3-yl]-2-[(dimethylamino)methyl]cyclopropane-1-carboxamide. LCMS (ESI) [M+H]$^+$=494.

Step 6: (1R,2S)—N-[8-amino-7-fluoro-6-(4-methylpyridin-3-yl)isoquinolin-3-yl]-2-[(dimethylamino)methyl]cyclopropane-1-carboxamide and (1S,2R)—N-[8-amino-7-fluoro-6-(4-methylpyridin-3-yl)isoquinolin-3-yl]-2-[(dimethylamino)methyl]cyclopropane-1-carboxamide

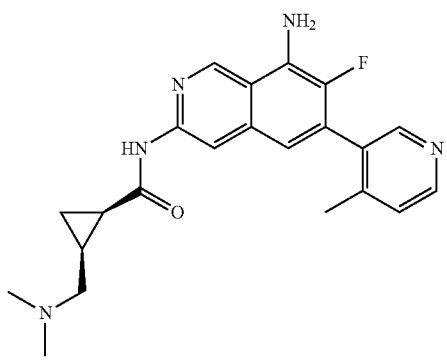

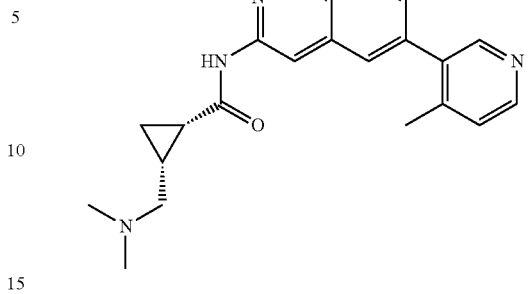

The title compound (racemic) was prepared in a fashion analogous to that described for Example 135 (Compound 36) using cis-tert-butyl N-(3-[[2-[(dimethylamino)methyl]cyclopropane]amido]-7-fluoro-6-(4-methylpyridin-3-yl)isoquinolin-8-yl)carbamate. The racemate was separated by Chiral-HPLC to afford two isomers (Cyclopropane stereochemistry for each isomer: dimethylaminomethyl trans to amide; Absolute stereochemistry arbitrarily assigned): Compound 342: Retention time:1.44 min(Lux Cellulose-4, 0.46*5 cm; 3 μm; Hex (8 mMNH3):EtOH=50:50; 1 ml/min); LCMS (ESI) [M+H]$^+$=394; $^1$HNMR (400 MHz, CD$_3$OD) δ 9.31 (s, 1H), 8.48 (d, J=4.0 Hz, 1H), 8.41 (s, 1H), 8.34 (s, 1H), 7.45 (d, J=4.0 Hz, 1H), 7.00 (d, J=8.0 Hz, 1H), 3.05-3.03 (m, 2H), 2.57 (s, 6H), 2.31 (s, 3H), 2.21-2.15 (m, 1H), 1.62-1.56 (m, 1H), 1.30-1.25 (m, 1H), 1.18-1.10 (m, 1H). Compound 341: Retention time:2.87 min (Lux Cellulose-4, 0.46*5 cm; 3 μm; Hex (8 mMNH3):EtOH=50:50; 1 ml/min); LCMS (ESI) [M+H]$^+$=394; $^1$HNMR (400 MHz, CD$_3$OD) δ 9.31 (s, 1H), 8.48 (d, J=4.0 Hz, 1H), 8.41 (s, 1H), 8.34 (s, 1H), 7.45 (d, J=4.0 Hz, 1H), 7.00 (d, J=8.0 Hz, 1H), 3.05-3.03 (m, 2H), 2.57 (s, 6H), 2.31 (s, 3H), 2.21-2.15 (m, 1H), 1.62-1.56 (m, 1H), 1.30-1.25 (m, 1H), 1.18-1.10 (m, 1H).

Example 216

(1S,2S,3S)—N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropanecarboxamide (Compound 381), (1R,2R,3R)—N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropanecarboxamide (Compound 380), (1S,2S,3R)—N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropanecarboxamide (Compound 379) and (1R,2R,3S)—N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropanecarboxamide (Compound 382)

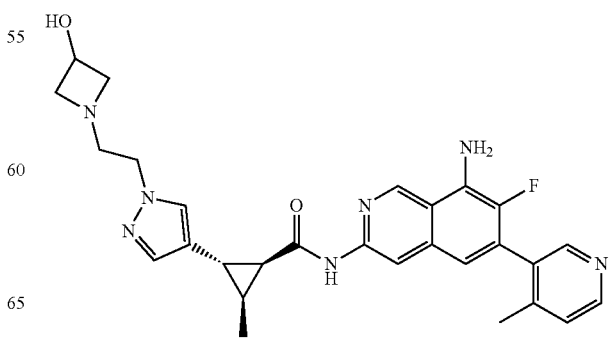

925
-continued

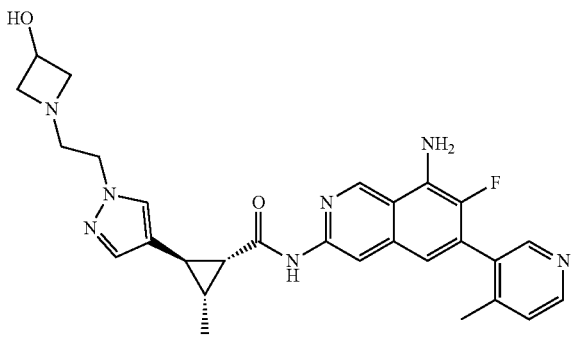

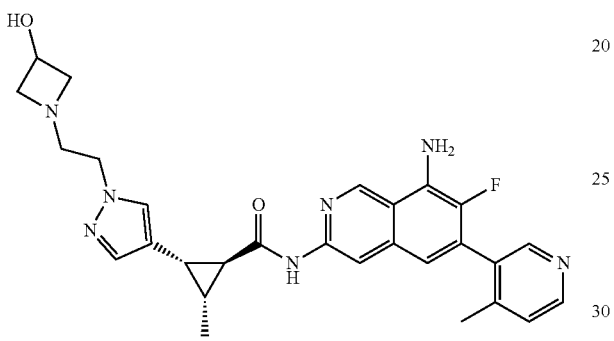

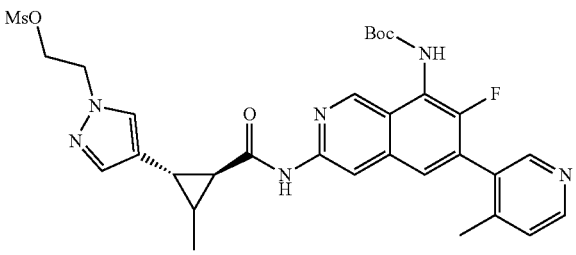 [SMILES: Cc1ccncc1-c1cc2cc(NC(=O)[C@H]3C(C)[C@@H]3c3cnn(CCOS(C)(=O)=O)c3)ncc2c(NC(=O)OC(C)(C)C)c1F]

Step 1: 2-(4-(2-(8-(tert-butoxycarbonylamino)-7-fluoro-6-(4-methylpyridin-3-yl)isoquinolin-3-ylcarbamoyl)-3-methylcyclopropyl)-1H-pyrazol-1-yl) ethyl methanesulfonate

926

A mixture of tert-butyl N-(7-fluoro-3-[[2-[1-(2-hydroxyethyl)-1H-pyrazol-4-yl]-3-methylcyclopropane]amido]-6-(4-methylpyridin-3-yl)isoquinolin-8-yl)carbamate (670 mg, 1.20 mmol), triethylamine (604 mg, 5.97 mmol), methanesulfonyl chloride (273 mg, 2.38 mmol) in dichloromethane (10 mL) was stirred for 1 hour at room temperature. The resulting solution was diluted with dichloromethane. The resulting mixture was washed with water. The organic phase was dried with anhydrous sodium sulfate. After filtration, the filtrate was concentrated under vacuum to afford 2-(4-((2-(8-(tert-butoxycarbonylamino)-7-fluoro-6-(4-methylpyridin-3-yl)isoquinolin-3-ylcarbamoyl)-3-methylcyclopropyl)-1H-pyrazol-1-yl)ethyl methanesulfonate (800 mg, 1.25 mmol) as a yellow solid. LCMS (ESI) [M+H]⁺=639.

Step 2: tert-butyl 7-fluoro-3-(2-(1-(2-(3-hydroxyazetidin-1-yl)ethyl)-1H-pyrazol-4-yl)-3-methylcyclopropanecarboxamido)-6-(4-methylpyridin-3-yl)isoquinolin-8-ylcarbamate

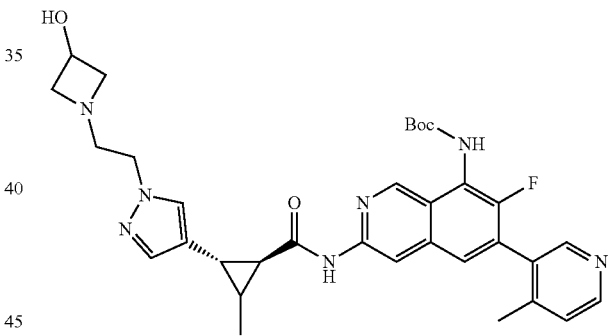

A mixture of 2-(4-(2-(8-(tert-butoxycarbonylamino)-7-fluoro-6-(4-methylpyridin-3-yl)isoquinolin-3-ylcarbamoyl)-3-methylcyclopropyl)-1H-pyrazol-1-yl)ethyl methanesulfonate (700 mg, 1.10 mmol), azetidin-3-ol (320 mg, 4.38 mmol), triethylamine (332 mg, 3.28 mmol) in N,N-dimethylformamide (10 mL) was stirred for 12 hours at 60° C. The resulting solution was diluted with ethyl acetate and then washed with water. The organic phase was dried with anhydrous sodium sulfate. After filtration, the filtrate was concentrated under vacuum. The residue was purified by flash chromatography on silica gel eluting with dichloromethane/methanol (4/1) to afford tert-butyl 7-fluoro-3-(2-(1-(2-(3-hydroxyazetidin-1-yl)ethyl)-1H-pyrazol-4-yl)-3-methylcyclopropanecarboxamido)-6-(4-methylpyridin-3-yl)isoquinolin-8-ylcarbamate (180 mg, 0.29 mmol) as a white solid. LCMS (ESI) [M+H]=616.

Step 3: (1S,2S,3S)—N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropanecarboxamide, (1R,2R,3R)—N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropanecarboxamide, (1S,2S,3R)—N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropanecarboxamide and (1R,2R,3S)—N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl-3-methylcyclopropanecarboxamide

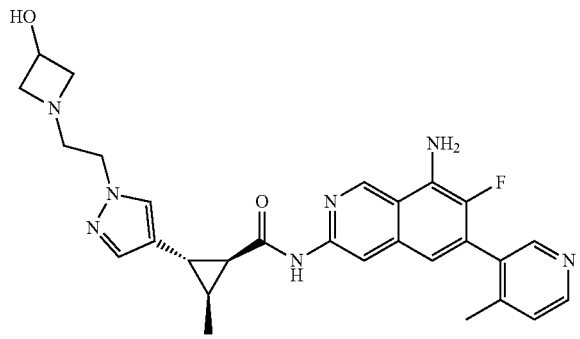

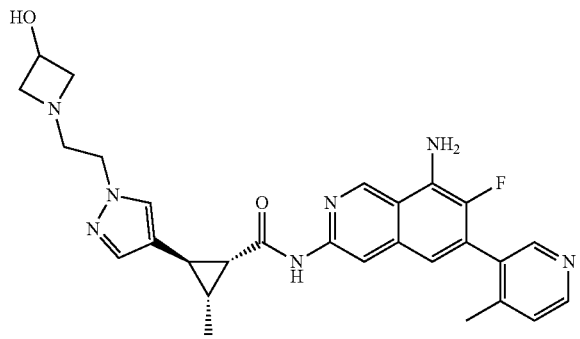

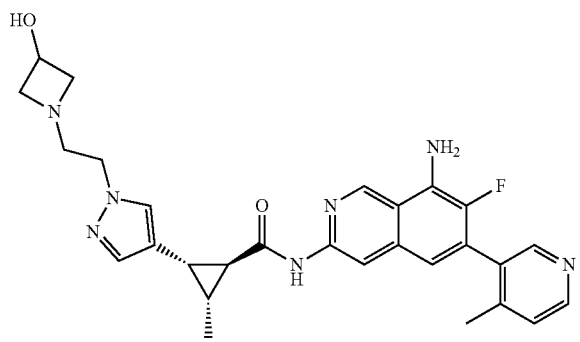 [SMILES: Cc1ccncc1-c1cc2cc(NC(=O)[C@H]3C(C)[C@@H]3c3cnn(CCN4CC(O)C4)c3)ncc2c(NC(=O)OC(C)(C)C)c1F]

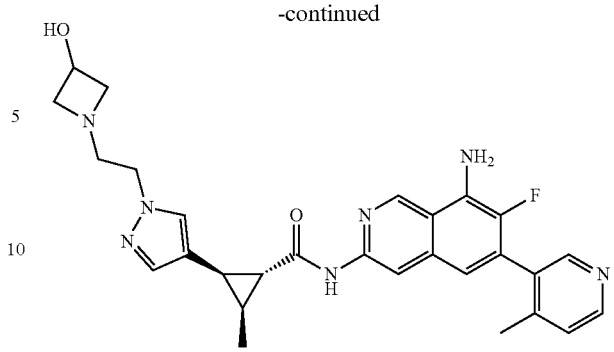

-continued

A mixture of tert-butyl N-(7-fluoro-3-[[2-[1-[2-(3-hydroxyazetidin-1-yl)ethyl]-1H-pyrazol-4-yl]-3-methylcyclopropane]amido]-6-(4-methylpyridin-3-yl)isoquinolin-8-yl) carbamate (180 mg, 0.29 mmol) in methanol (3 mL) and HCl/dioxane (10 mL, 6 mol/L) was stirred for 2 hours at room temperature. The mixture was concentrated under vacuum. The crude product was purified by Prep-HPLC (C18 silica gel; 0.5% NH$_4$HCO$_3$ in water: ACN=2%-50% in 8 min) to afford the mixture. The mixture was separated by Chiral-HPLC to afford four isomers (Cyclopropane stereochemistry for each isomer: pyrazole trans to amide; methyl relative stereochemistry arbitrarily assigned; All Absolute stereochemistry arbitrarily assigned): Compound 381: (11.1 mg, 0.022 mmol) as a yellow solid. Retention time: 2.342 min (CHIRALPAK IC-3. 0.46*10 cm; 3 μm; MtBE (0.1% DEA):EtOH=80:20; 1.0 ml/min); LCMS (ESI) [M+H]$^+$=516.4; $^1$H NMR (400 MHz, DMSO-d$_6$) δ 10.71 (s, 1H), 9.42 (s, 1H), 8.51 (d, J=5.0 Hz, 1H), 8.44 (s, 1H), 8.35 (s, 1H), 7.54 (s, 1H), 7.40 (d, J=5.1 Hz, 1H), 7.24 (s, 1H), 6.95 (d, J=6.1 Hz, 1H), 6.30 (s, 2H), 5.24 (d, J=6.6 Hz, 1H), 4.21-4.05 (m, 1H), 4.01-3.83 (m, 2H), 3.51-3.38 (m, 2H), 2.78-2.69 (m, 2H), 2.68-2.60 (m, 2H), 2.28-2.19 (m, 4H), 2.18-2.09 (m, 1H), 1.67-1.51 (m, 1H), 1.28 (d, J=6.2 Hz, 3H). Compound 380: (11.7 mg, 0.023 mmol) as a yellow solid. Retention time: 3.412 min (CHIRALPAK IC-3. 0.46*10 cm; 3 μm;

MtBE (0.1% DEA):EtOH=80:20; 1.0 ml/min); LCMS (ESI) [M+H]$^+$=516.4; $^1$H NMR (400 MHz, DMSO-d$_6$) δ 10.71 (s, 1H), 9.42 (s, 1H), 8.51 (d, J=5.0 Hz, 1H), 8.44 (s, 1H), 8.35 (s, 1H), 7.54 (s, 1H), 7.40 (d, J=5.0 Hz, 1H), 7.24 (s, 1H), 6.95 (d, J=6.2 Hz, 1H), 6.30 (s, 2H), 5.31-5.11 (m, 1H), 4.19-4.01 (m, 1H), 3.95 (t, J=6.2 Hz, 2H), 3.50-3.39 (m, 2H), 2.76-2.61 (m, 4H), 2.22 (s, 4H), 2.19-2.12 (m, 1H), 1.67-1.51 (m, 1H), 1.28 (d, J=6.2 Hz, 3H). Compound 379: (22.0 mg, 0.043 mmol) as a yellow solid. Retention time: 9.180 min (CHIRALPAK IE-3. 0.46*10 cm; 3 μm; MtBE (0.1% DEA):EtOH=75:25; 1.0 ml/min); LCMS (ESI) [M+H]$^+$=516.4; $^1$H NMR (400 MHz, DMSO-d$_6$) δ 10.76 (s, 1H), 9.44 (s, 1H), 8.51 (d, J=5.0 Hz, 1H), 8.44 (s, 1H), 8.32 (s, 1H), 7.55 (s, 1H), 7.40 (d, J=5.0 Hz, 1H), 7.30 (s, 1H), 6.93 (d, J=6.1 Hz, 1H), 6.31 (s, 2H), 5.23 (d, J=6.6 Hz, 1H), 4.19-4.08 (m, 1H), 4.01 (t, J=6.2 Hz, 2H), 3.49-3.37 (m, 2H), 2.74 (t, J=6.2 Hz, 2H), 2.69-2.61 (m, 2H), 2.37-2.24 (m, 1H), 2.22 (s, 3H), 2.12 (t, J=4.7 Hz, 1H), 1.67-1.53 (m, 1H), 0.96 (d, J=6.3 Hz, 3H). Compound 382: (18.5 mg, 0.036 mmol) as a yellow solid. Retention time: 11.776 min (CHIRALPAK IE-3. 0.46*10 cm; 3 μm;

MtBE (0.1% DEA):EtOH=75:25; 1.0 ml/min); LCMS (ESI) [M+H]$^+$=516.3; $^1$H NMR (400 MHz, DMSO-d$_6$) δ 10.75 (s, 1H), 9.43 (s, 1H), 8.51 (d, J=5.0 Hz, 1H), 8.44 (s, 1H), 8.32 (s, 1H), 7.55 (s, 1H), 7.40 (d, J=5.1 Hz, 1H), 7.30 (s, 1H), 6.93 (d, J=6.1 Hz, 1H), 6.31 (s, 2H), 5.23 (d, J=6.6

Hz, 1H), 4.19-4.08 (m, 1H), 4.01 (t, J=6.2 Hz, 2H), 3.46-3.37 (m, 2H), 2.75 (t, J=6.2 Hz, 2H), 2.69-2.61 (m, 2H), 2.34-2.27 (m, 1H), 2.22 (s, 3H), 2.12 (t, J=4.7 Hz, 1H), 1.67-1.53 (m, 1H), 0.96 (d, J=6.3 Hz, 3H).

Example 217

2-((8-amino-7-fluoro-6-(4-methylpyridin-3-yl)isoquinolin-3-yl)amino)-6-methyl-5,6-dihydro-4H-pyrazolo[1,5-d][1,4]diazepin-7(8H)-one (Compound 230)

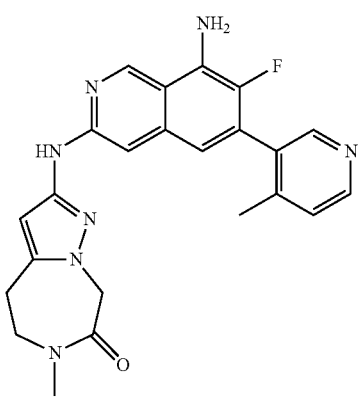 [SMILES: Cc1ccncc1-c1cc2cc(Nc3cc4n(n3)CC(=O)N(C)CC4)ncc2c(N)c1F]

Step 1: 2-[[8-Chloro-7-fluoro-6-(4-methylpyridin-3-yl)isoquinolin-3-yl]amino]-6-methyl-4H,5H,6H,7H,8H-pyrazolo[1,5-d][1,4]diazepin-7-one

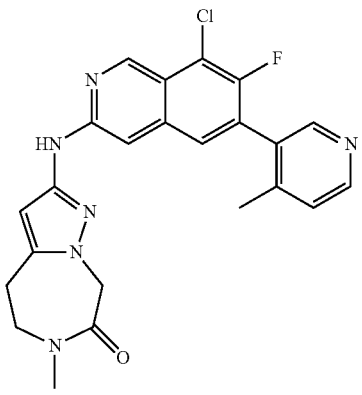

To a solution of 8-chloro-7-fluoro-6-(4-methylpyridin-3-yl)isoquinolin-3-amine (100 mg, 0.35 mmol) in 1,4-dioxane (10 mL) was added 2-bromo-6-methyl-4H,5H,6H,7H,8H-pyrazolo[1,5-d][1,4]diazepin-7-one (110 mg, 0.45 mmol), Pd₂(dba)₃.CHCl₃ (72 mg, 0.07 mmol), XantPhos (80 mg, 0.14 mmol) and cesium carbonate (290 mg, 0.89 mmol). The resulting mixture was stirred for 2 h at 110° C. After filtration, the filtrate was concentrated under vacuum. The residue was purified by flash chromatography on silica gel eluting with dichloromethane/methanol (15/1) to afford 2-[[8-chloro-7-fluoro-6-(4-methylpyridin-3-yl)isoquinolin-3-yl]amino]-6-methyl-4H,5H,6H,7H,8H-pyrazolo[1,5-d][1,4]diazepin-7-one (45 mg, 29%) as a yellow solid. LCMS (ESI) [M+H]⁺=451.2.

Step 2: Tert-butyl N-[7-fluoro-3-([6-methyl-7-oxo-4H,5H,6H,7H,8H-pyrazolo[1,5-d][1,4]diazepin-2-yl]amino)-6-(4-methylpyridin-3-yl)isoquinolin-8-yl]carbamate

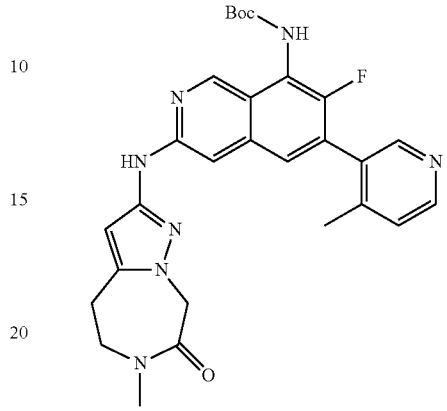

To a mixture of 2-[[8-chloro-7-fluoro-6-(4-methylpyridin-3-yl)isoquinolin-3-yl]amino]-6-methyl-4H,5H,6H,7H,8H-pyrazolo[1,5-d][1,4]diazepin-7-one (500 mg, 1.11 mmol) in 1,4-dioxane (45 mL) was added tert-butyl carbamate (3.25 g, 27.74 mmol), Pd₂(dba)₃.CHCl₃ (175 mg, 0.17 mmol), BrettPhos (125 mg, 0.23 mmol) and cesium carbonate (1.8 g, 5.525 mmol). The resulting mixture was stirred for 2 h at 90° C. After filtration, the filtrate was concentrated under vacuum. The residue was purified by flash chromatography on silica gel eluting with dichloromethane/methanol (10/1) to afford tert-butyl N-[7-fluoro-3-([6-methyl-7-oxo-4H,5H,6H,7H,8H-pyrazolo[1,5-d][1,4]diazepin-2-yl]amino)-6-(4-methylpyridin-3-yl)isoquinolin-8-yl]carbamate (350 mg, 59%) as a yellow solid. LCMS45 (ESI) [M+H]⁺=532.3.

Step 3: 2-[[8-Amino-7-fluoro-6-(4-methylpyridin-3-yl)isoquinolin-3-yl]amino]-6-methyl-4H,5H,6H,7H,8H-pyrazolo[1,5-d][1,4]diazepin-7-one

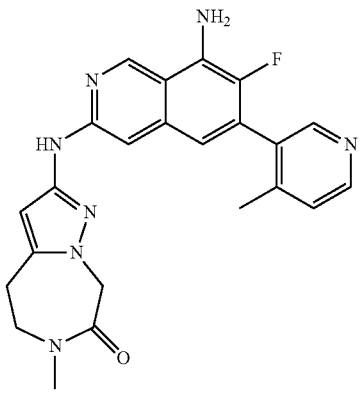 [SMILES: Cc1ccncc1-c1cc2cc(Nc3cc4n(n3)CC(=O)N(C)CC4)ncc2c(Cl)c1F]

A solution of tert-butyl N-[7-fluoro-3-([6-methyl-7-oxo-4H,5H,6H,7H,8H-pyrazolo[1,5-d][1,4]diazepin-2-yl]amino)-6-(4-methylpyridin-3-yl)isoquinolin-8-yl]carbamate (350 mg, 0.66 mmol) and dichloromethane (5 mL) in trifluoroacetic acid (10 mL) was stirred for 1.5 h at room

931 temperature. The resulting mixture was concentrated under vacuum. The pH value of the solution was adjusted to 10 with NH3 in methanol (7 M). The crude product was purified directly by Prep-HPLC (XBridge Prep C18 OBD Column19*15 mm Sum; 10 mmol NH$_4$HCO$_3$ in water: ACN (20%40% in 8 min)) to afford 2-[[8-amino-7-fluoro-6-(4-methylpyridin-3-yl)isoquinolin-3-yl]amino]-6-methyl-4H,5H,6H,7H,8H-pyrazolo[1,5-d][1,4]diazepin-7-one (90 mg, 32%) as a yellow solid. LCMS (ESI) [M+H]$^+$=432.3; $^1$H NMR (400 MHz, DMSO-d$_6$) δ 9.27 (s, 1H), 9.11 (s, 1H), 8.51 (s, 1H), 8.43 (s, 1H), 7.74 (s, 1H), 7.39 (d, J=7.2 Hz, 1H), 6.78 (d, J=7.2 Hz, 1H), 6.13 (s, 2H), 5.98 (s, 1H), 4.97 (s, 2H), 3.84-3.81 (m, 2H), 3.05-3.03 (m, 2H), 2.95 (s, 3H), 2.22 (s, 3H).

Example 218

N-(8-amino-7-fluoro-6-(4-methylpyridin-3-yl)isoquinolin-3-yl)-2-azabicyclo[2.1.1]hexane-2-carboxamide (Compound 336)

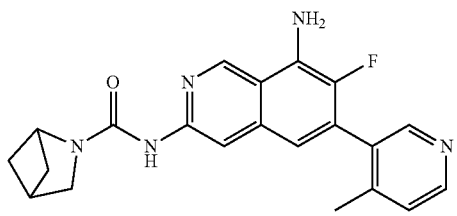

Step 1: 4-nitrophenyl 8-chloro-7-fluoro-6-(4-methylpyridin-3-yl)isoquinolin-3-ylcarbamate

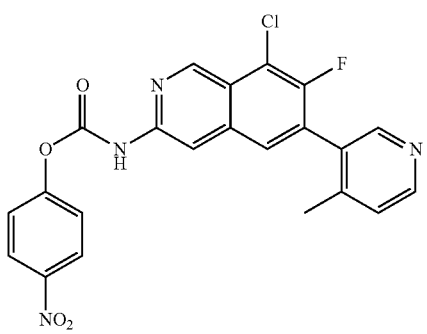 [SMILES: Cc1ccncc1-c1cc2cc(NC(=O)Oc3ccc([N+](=O)[O-])cc3)ncc2c(Cl)c1F]

A mixture of 8-chloro-7-fluoro-6-(4-methylpyridin-3-yl)isoquinolin-3-amine (500 mg, 1.74 mmol), pyridine (1 mL, 12.424 mmol), 4-nitrophenyl chloroformate (1.05 g, 5.21 mmol) in dichloromethane (10 mL) was stirred for 2 hours at room temperature. The solids were collected by filtration to afford 4-nitrophenyl N-[8-chloro-7-fluoro-6-(4-methylpyridin-3-yl)isoquinolin-3-yl]carbamate (800 mg, 1.77 mmol) as a white solid. LCMS (ESI) [M+H]$^+$=453.

932

Step 2: N-(8-chloro-7-fluoro-6-(4-methylpyridin-3-yl)isoquinolin-3-yl)-2-aza-bicyclo[2.1.1]hexane-2-carboxamide

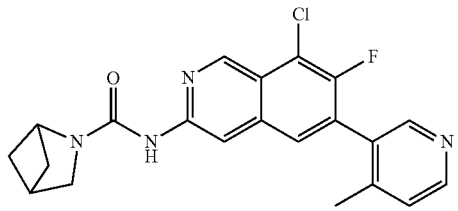 [SMILES: Cc1ccncc1-c1cc2cc(NC(=O)N3CC4CC3C4)ncc2c(Cl)c1F]

A mixture of 2-azabicyclo[2.1.1]hexane (658 mg, 7.92 mmol), pyridine (2 mL), 4-nitrophenyl N-[8-chloro-7-fluoro-6-(4-methylpyridin-3-yl)isoquinolin-3-yl]carbamate (500 mg, 1.10 mmol) in 1-methyl-2-pyrrolidinone (10 mL) was stirred for 1 hour at 30° C. The resulting solution was diluted with ethyl acetate and then washed with water. The organic phase was dried with anhydrous sodium sulfate. After filtration, the filtrate was concentrated under vacuum. The residue was purified by silica gel column eluting with dichloromethane/methanol (10/1) to afford N-[8-chloro-7-fluoro-6-(4-methylpyridin-3-yl)isoquinolin-3-yl]-2-azabicyclo[2.1.1]hexane-2-carboxamide (400 mg, 1.01 mmol) of as a white solid. LCMS (ESI) [M+H]$^+$=397

Step 3: tert-butyl 3-(2-aza-bicyclo[2.1.1]hexane-2-carboxamido)-7-fluoro-6-(4-methylpyridin-3-yl)isoquinolin-8-ylcarbamate

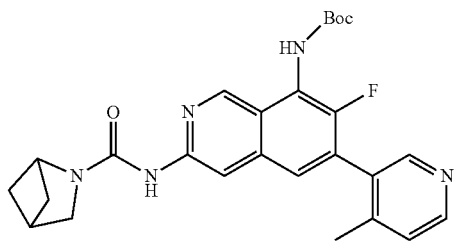 [SMILES: Cc1ccncc1-c1cc2cc(NC(=O)N3CC4CC3C4)ncc2c(NC(=O)OC(C)(C)C)c1F]

A mixture of N-[8-chloro-7-fluoro-6-(4-methylpyridin-3-yl)isoquinolin-3-yl]-2-azabicyclo[2.1.1]hexane-2-carboxamide (900 mg, 2.27 mmol), tert-butyl carbamate (7.98 g, 68.12 mmol), BrettPhos (244 mg, 0.46 mmol), Pd$_2$(dba)$_3$.CHCl$_3$ (470 mg, 0.45 mmol) and cesium carbonate (2.96 g, 9.09 mmol) in 1,4-dioxane (100 mL) was stirred for 3 hours at 90° C. After filtration, the filtrate was concentrated under vacuum. The residue was purified by silica gel column eluting with dichloromethane/methanol (9/1) to afford tert-butyl N-[3-[([2-azabicyclo[2.1.1]hexan-2-yl]carbonyl)amino]-7-fluoro-6-(4-methylpyridin-3-yl)isoquinolin-8-yl]carbamate (110 mg, 0.23 mmol) of as a purple solid. LCMS (ESI) [M+H]$^+$=478.

933

Step 4: N-(8-amino-7-fluoro-6-(4-methylpyridin-3-yl)isoquinolin-3-yl)-2-aza-bicyclo[2.1.1]hexane-2-carboxamide

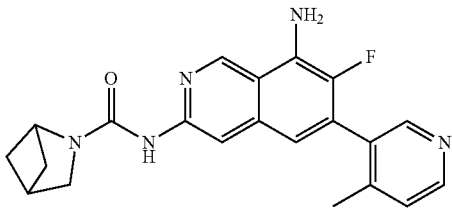 [SMILES: Cc1ccncc1-c1cc2cc(NC(=O)N3CC4CC3C4)ncc2c(N)c1F]

A mixture of tert-butyl N-[3-[([2-azabicyclo[2.1.1]hexan-2-yl]carbonyl)amino]-7-fluoro-6-(4-methylpyridin-3-yl)isoquinolin-8-yl]carbamate (100 mg, 0.21 mmol) in methanol (2 mL) and HCl/dioxane (10 mL, 6 mol/L) was stirred for 3 hours at room temperature. The mixture was concentrated under vacuum. The crude product was purified by Prep-HPLC (Atlantis HILIC OBD, 19×150 mm 5 um; water (10 mmol/L NH$_4$HCO$_3$): CH$_3$CN=0%-45% B in 14 min) to afford N-[8-amino-7-fluoro-6-(4-methylpyridin-3-yl)isoquinolin-3-yl]-2-azabicyclo[2.1.1]hexane-2-carboxamide (45.9 mg, 0.12 mmol) as a yellow solid. LCMS (ESI) [M+H]$^+$=378.2; $^1$H NMR (300 MHz, DMSO-d$_6$) δ 9.39 (s, 1H), 9.01 (s, 1H), 8.53 (d, J=5.3 Hz, 1H), 8.46 (s, 1H), 8.13 (s, 1H), 7.43 (d, J=4.7 Hz, 1H), 6.88 (d, J=6.4 Hz, 1H), 6.26 (s, 2H), 4.65 (d, J=7.0 Hz, 1H), 3.46-3.39 (m, 2H), 2.88 (s, 1H), 2.24 (s, 3H), 1.94 (s, 2H), 1.37-1.28 (m, 2H).

Example 219

(1S,2S,3S)—N-(8-amino-7-fluoro-6-(4-methylpyridin-3-yl)isoquinolin-3-yl)-2-methyl-3-(1-(2-morpholinoethyl)-1H-pyrazol-4-yl)cyclopropane-1-carboxamide (Compound 349)

(1S,2R,3S)—N-(8-amino-7-fluoro-6-(4-methylpyridin-3-yl)isoquinolin-3-yl)-2-methyl-3-(1-(2-morpholinoethyl)-1H-pyrazol-4-yl)cyclopropane-1-carboxamide (Compound 348)

(1R,2R,3R)—N-(8-amino-7-fluoro-6-(4-methylpyridin-3-yl)isoquinolin-3-yl)-2-methyl-3-(1-(2-morpholinoethyl)-1H-pyrazol-4-yl)cyclopropane-1-carboxamide (Compound 347) and (1R,2S,3R)—N-(8-amino-7-fluoro-6-(4-methylpyridin-3-yl)isoquinolin-3-yl)-2-methyl-3-(1-(2-morpholinoethyl)-1H-pyrazol-4-yl)cyclopropane-1-carboxamide (Compound 346)

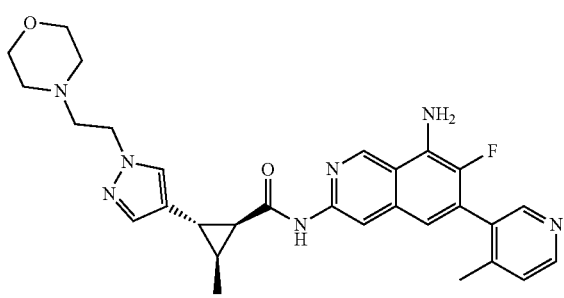

934

-continued

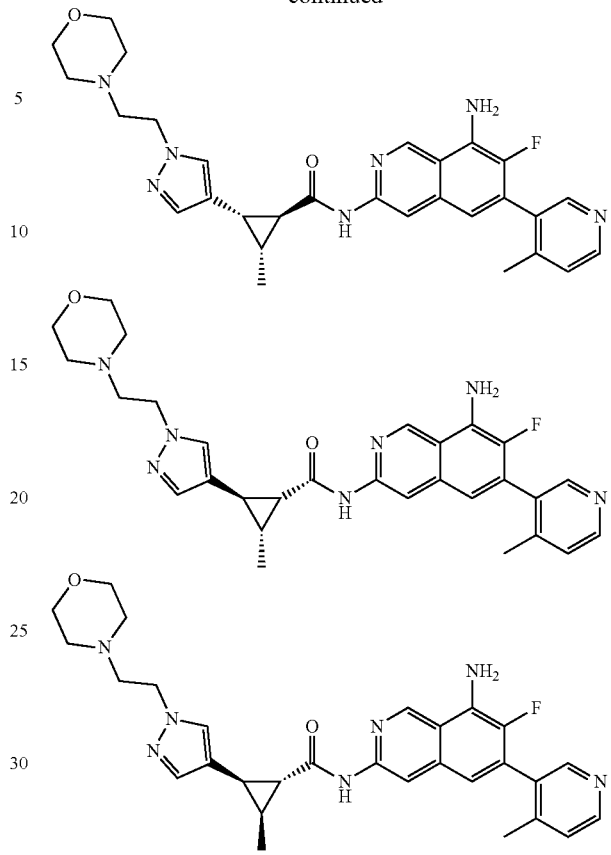

Step 1: 2-(4-(2-(8-(tert-butoxycarbonylamino)-7-fluoro-6-(4-methylpyridin-3-yl)isoquinolin-3-ylcarbamoyl)-3-methylcyclopropyl)-1H-pyrazol-1-yl)ethylmethanesulfonate

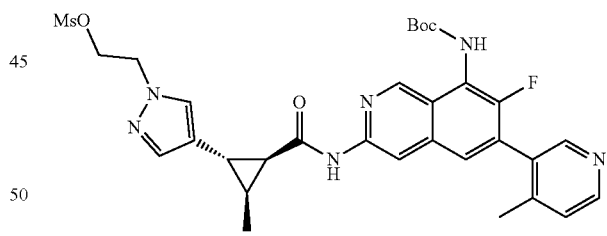

A mixture of tert-butyl N-(7-fluoro-3-[[2-[1-(2-hydroxyethyl)-1H-pyrazol-4-yl]-3-methylcyclopropane]amido]-6-(4-methylpyridin-3-yl)isoquinolin-8-yl)carbamate (200 mg, 0.36 mmol), triethylamine (72 mg, 0.71 mmol), methanesulfonyl chloride (61 mg, 0.53 mmol) in dichloromethane (5 mL) was stirred for 30 minutes at room temperature. The resulting mixture was diluted with dichloromethane and then washed with water. The organic phase was dried with anhydrous sodium sulfate. After filtration, the filtrate was concentrated under vacuum to afford tert-butyl N-(7-fluoro-3-[[2-[1-[2-(methanesulfonyloxy)ethyl]-1H-pyrazol-4-yl]-3-methylcyclopropane]amido]-6-(4-methylpyridin-3-yl)isoquinolin-8-yl)carbamate (240 mg, 0.38 mmol) as a yellow solid. LCMS (ESI) [M+H]$^+$=639.

Step 2: tert-butyl 7-fluoro-3-(2-methyl-3-(1-(2-morpholinoethyl)-1H-pyrazol-4-yl)cyclopropanecarboxamido)-6-(4-methylpyridin-3-yl)isoquinolin-8-ylcarbamate

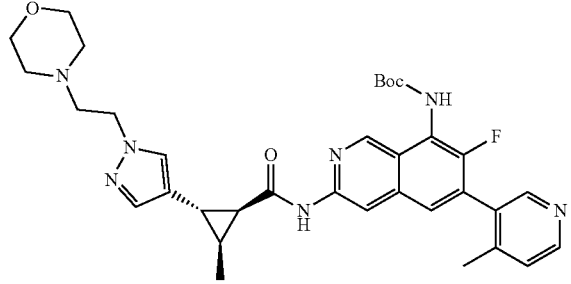 [SMILES: Cc1ccncc1-c1cc2cc(NC(=O)[C@H]3[C@@H](C)[C@@H]3c3cnn(CCN4CCOCC4)c3)ncc2c(NC(=O)OC(C)(C)C)c1F]

A mixture of tert-butyl N-(7-fluoro-3-[[2-[1-[2-(methanesulfonyloxy)ethyl]-1H-pyrazol-4-yl]-3-methylcyclopropane]amido]-6-(4-methylpyridin-3-yl)isoquinolin-8-yl)carbamate (600 mg, 0.94 mmol), morpholine (409 mg, 4.70 mmol) and potassium carbonate (260 mg, 1.88 mmol) in N,N-dimethylformamide (6 mL) was stirred for 12 hours at 70° C. The resulting solution was diluted with water and then extracted with ethyl acetate. The organic phase was dried with anhydrous sodium sulfate. After filtration, the filtrate was concentrated under vacuum. The residue was purified by silica gel column eluting with dichloromethane/methanol (9/1) to afford tert-butyl N-(7-fluoro-3-[[2-methyl-3-[1-[2-(morpholin-4-yl)ethyl]-1H-pyrazol-4-yl]cyclopropane]amido]-6-(4-methylpyridin-3-yl)isoquinolin-8-yl)carbamate (288 mg, 0.46 mmol) as a yellow solid. LCMS (ESI) [M+H]$^+$=630.

Step 3: (1S,2S,3S)—N-(8-amino-7-fluoro-6-(4-methylpyridin-3-yl)isoquinolin-3-yl)-2-methyl-3-(1-(2-morpholinoethyl)-1H-pyrazol-4-yl)cyclopropanecarboxamide, (1S,2R,3S)—N-(8-amino-7-fluoro-6-(4-methylpyridin-3-yl)isoquinolin-3-yl)-2-methyl-3-(1-(2-morpholinoethyl)-1H-pyrazol-4-yl)cyclopropanecarboxamide, (1R,2R,3R)—N-(8-amino-7-fluoro-6-(4-methylpyridin-3-yl)isoquinolin-3-yl)-2-methyl-3-(1-(2-morpholinoethyl)-1H-pyrazol-4-yl)cyclopropanecarboxamide and (1R,2S,3R)—N-(8-amino-7-fluoro-6-(4-methylpyridin-3-yl)isoquinolin-3-yl)-2-methyl-3-(1-(2-morpholinoethyl)-1H-pyrazol-4-yl)cyclopropanecarboxamide

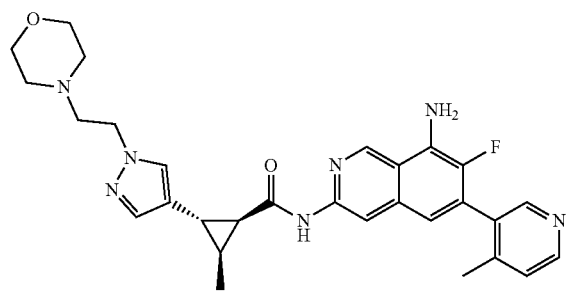

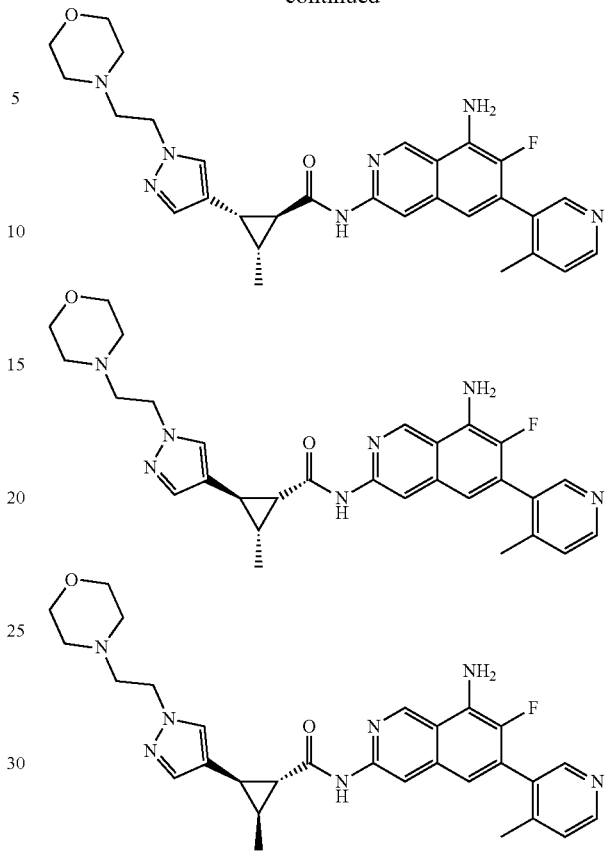

A mixture of tert-butyl N-(7-fluoro-3-[[2-methyl-3-[1-[2-(morpholin-4-yl)ethyl]-1H-pyrazol-4-yl]cyclopropane]amido]-6-(4-methylpyridin-3-yl)isoquinolin-8-yl)carbamate (280 mg, 0.45 mmol), methanol (4 mL) and HCl/1,4-dioxane (10 mL, 6 mol/L) was stirred for 2 hours at room temperature. The mixture was concentrated under vacuum. The crude product was purified by Prep-HPLC (C18 silica gel; 0.5% NH$_4$HCO$_3$ in water: ACN=30%-58% in 8 min) to afford the mixture. The mixture was separated by Chiral-HPLC to afford four isomers (Cyclopropane stereochemistry for isomers: pyrazole trans to amide; methyl relative stereochemistry arbitrarily assigned; All absolute stereochemistry arbitrarily assigned): Compound 349: (19.1 mg, 0.036 mmol) as a yellow solid. Retention time: 3.550 min (CHIRALPAK IE-3. 0.46*10 cm; 3 μm;
MtBE (0.1% DEA):EtOH=50:50; 1.0 ml/min); LCMS (ESI) [M+H]$^+$=530.4; $^1$H NMR (400 MHz, DMSO-d$_6$) δ 10.71 (s, 1H), 9.42 (s, 1H), 8.51 (d, J=5.0 Hz, 1H), 8.44 (s, 1H), 8.35 (s, 1H), 7.59 (s, 1H), 7.40 (d, J=5.0 Hz, 1H), 7.26 (s, 1H), 6.95 (d, J=6.2 Hz, 1H), 6.30 (s, 2H), 4.14 (t, J=6.7 Hz, 2H), 3.56 (t, J=4.6 Hz, 4H), 2.66 (t, J=4.0 Hz, 2H), 2.39 (s, 4H), 2.27-2.14 (m, 5H), 1.64-1.48 (m, 1H), 1.28 (d, J=6.1 Hz, 3H). Compound 348: (29.2 mg, 0.055 mmol) as a yellow solid. Retention time: 2.801 min (CHIRALPAK IC-3. 0.46*10 cm; 3 μm;
MtBE (0.1% DEA):EtOH=80:20; 1.0 ml/min); LCMS (ESI) [M+H]$^+$=530.4; $^1$H NMR (400 MHz, DMSO-d$_6$) δ 10.76 (s, 1H), 9.44 (s, 1H), 8.51 (d, J=5.0 Hz, 1H), 8.44 (s, 1H), 8.32 (s, 1H), 7.59 (s, 1H), 7.40 (d, J=5.1 Hz, 1H), 7.31 (s, 1H), 6.93 (d, J=6.1 Hz, 1H), 6.30 (s, 2H), 4.18 (t, J=6.6 Hz, 2H), 3.55 (t, J=4.6 Hz, 4H), 2.68 (t, J=6.6 Hz, 2H), 2.41-2.36 (m, 4H), 2.35-2.29 (m, 1H), 2.22 (s, 3H), 2.12 (t, J=4.7 Hz, 1H), 1.69-2.51 (m, 1H), 0.96 (d, J=6.3 Hz, 3H). Compound 347: (16.7 mg, 0.032 mmol) as a yellow solid. Retention time: 3.608 min (CHIRALPAK IC-3. 0.46*10 cm; 3 μm; MtBE (0.1% DEA):EtOH=80:20; 1.0 ml/min); LCMS (ESI) [M+H]$^+$=530.4; $^1$H NMR (400 MHz, DMSO-d$_6$) δ 10.71 (s, 1H), 9.42 (s, 1H), 8.51 (d, J=5.0 Hz, 1H), 8.44 (s, 1H), 8.35 (s, 1H), 7.59 (s, 1H), 7.44-7.37 (m, 1H), 7.26 (d, J=0.8 Hz, 1H), 6.95 (d, J=6.1 Hz, 1H), 6.30 (s, 2H), 4.14 (t, J=6.7 Hz, 2H), 3.56 (t, J=4.6 Hz, 4H), 2.66 (t, J=6.6 Hz, 2H), 2.43-2.36 (m, 4H), 2.27-2.13 (m, 5H), 1.66-1.48 (m, 1H), 1.28 (d, J=6.1 Hz, 3H). Compound 346: (33.1 mg, 0.063 mmol) as a yellow solid. Retention time: 6.022 min (CHIRALPAK IE-3. 0.46*10 cm; 3 μm; MtBE (0.1% DEA): EtOH=50:50; 1.0 ml/min); LCMS (ESI) [M+H]$^+$=530.4; $^1$H NMR (400 MHz, DMSO-d$_6$) δ 10.76 (s, 1H), 9.43 (s, 1H), 8.51 (d, J=5.0 Hz, 1H), 8.44 (s, 1H), 8.32 (s, 1H), 7.59 (s, 1H), 7.40 (d, J=5.1 Hz, 1H), 7.31 (s, 1H), 6.93 (d, J=6.1 Hz, 1H), 6.31 (s, 2H), 4.19 (t, J=6.6 Hz, 2H), 3.55 (t, J=4.5 Hz, 4H), 2.68 (s, 2H), 2.38 (s, 4H), 2.34-2.28 (m, 1H), 2.22 (s, 3H), 2.12 (t, J=4.7 Hz, 1H), 1.67-1.53 (m, 1H), 0.96 (d, J=6.3 Hz, 3H).

Example 220

(1S,2R,3S)—N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide (Compound 351)

(1R,2R,3R)—N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide (Compound 353), (1S,2S,3S)—N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide (Compound 352) and (1R,2S,3R)—N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide (Compound 350)

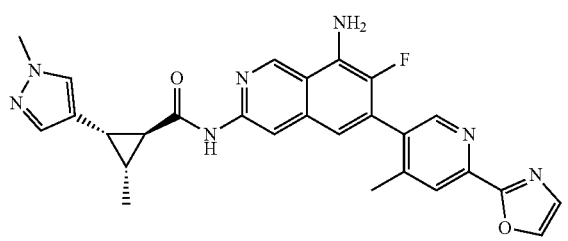

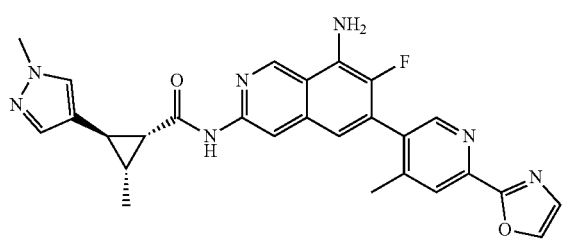

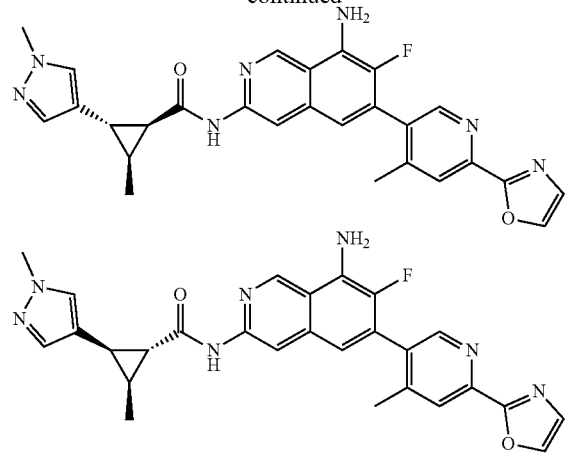

Step 1:
5-bromo-4-methyl-2-(1,3-oxazol-2-yl)pyridine

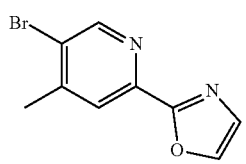

To a solution of 2,5-dibromo-4-methylpyridine (584 mg, 2.32 mmol) in 1,4-dioxane (15 mL) was added 2-(tributylstannyl)-1,3-oxazole (1.00 g, 2.79 mmol) and tetrakis(triphenylphosphine)palladium (268.95 mg, 0.23 mmol). The reaction was stirred for 16 hours 90° C. After filtration, the filtrate was concentrated under vacuum. The residue was purified by flash chromatography on silica gel eluting with ethyl acetate/petroleum ether (1/1) to afford 5-bromo-4-methyl-2-(1,3-oxazol-2-yl)pyridine (470 mg, 84%) as a yellow solid. LCMS (ESI) [M+H]$^+$=439.1.

Step 2: 4-methyl-2-(1,3-oxazol-2-yl)-5-(tetramethyl-1,3,2-dioxaborolan-2-yl)pyridine

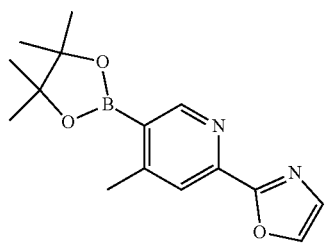 [SMILES: Cc1cc(-c2ncco2)ncc1B1OC(C)(C)C(C)(C)O1]

To a solution of 5-bromo-4-methyl-2-(1,3-oxazol-2-yl)pyridine (470 mg, 1.96 mmol) in 1,4-dioxane (15 mL) was added 4,4,5,5-tetramethyl-2-(tetramethyl-1,3,2-dioxaborolan-2-yl)-1,3,2-dioxaborolane (4.99 g, 19.65 mmol), [1,1'-bis(diphenylphosphino)ferrocene]dichloropalladium(II) (143.85 mg, 0.19 mmol) and potassium acetate (482.36 mg, 4.91 mmol). The reaction was stirred for 16 hours at 90° C. After filtration, the filtrate was concentrated under vacuum.

The residue was purified by flash chromatography on silica gel eluting with ethyl acetate/petroleum ether (1/4) to afford 4-methyl-2-(1,3-oxazol-2-yl)-5-(tetramethyl-1,3,2-dioxaborolan-2-yl)pyridine (330 mg, 59%) as yellow oil. LCMS (ESI) [M+H]$^+$=287.1.

Step 3: N-(8-chloro-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide

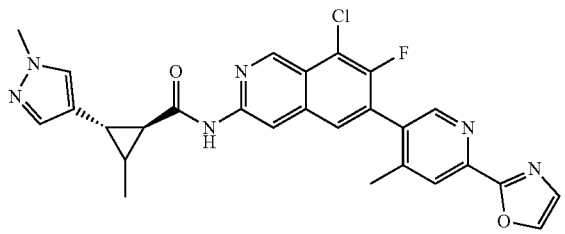 [SMILES: Cc1cc(-c2ncco2)ncc1-c1cc2cc(NC(=O)[C@H]3C(C)[C@@H]3c3cnn(C)c3)ncc2c(Cl)c1F]

To a solution of N-(8-chloro-7-fluoro-6-iodoisoquinolin-3-yl)-2-methyl-3-(1-methyl-1H-pyrazol-4-yl)cyclopropane-1-carboxamide (380 mg, 0.78 mmol) in 1,4-dioxane (16 mL) was added 4-methyl-2-(1,3-oxazol-2-yl)-5-(tetramethyl-1,3,2-dioxaborolan-2-yl)pyridine (448.66 mg, 1.56 mmol), potassium carbonate (325.06 mg, 2.35 mmol), X-Phos (37.37 mg, 0.07 mmol), XPhos-PdCl-2nd G (59.57 mg, 0.07 mmol) and water (3.2 mL). The reaction was stirred for 2 h at 90° C. After filtration, the filtrate was concentrated under vacuum. The residue was purified by flash chromatography on silica gel eluting with dichloromethane/methanol (25/1) to afford trans-N-(8-chloro-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide (210 mg, 52%) as orange oil. LCMS (ESI): [M+H]$^+$=517.2.

Step 4: tert-butyl(7-fluoro-3-(2-methyl-3-(1-methyl-1H-pyrazol-4-yl)cyclopropane-1-carboxamido)-6-(4-methyl-6-(oxazol-2-yl)pyridin-3-yl)isoquinolin-8-yl)carbamate

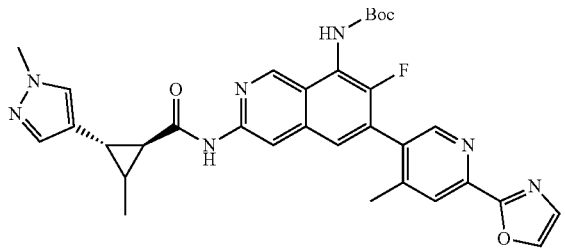 [SMILES: Cc1cc(-c2ncco2)ncc1-c1cc2cc(NC(=O)[C@H]3C(C)[C@@H]3c3cnn(C)c3)ncc2c(NC(=O)OC(C)(C)C)c1F]

To a solution of N-(8-chloro-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide (210 mg, 0.40 mmol) in 1,4-dioxane (10 mL) was added tert-butyl carbamate (1.19 g, 10.15 mmol), Pd$_2$(dba)$_3$·CHCl$_3$ (63.07 mg, 0.06 mmol), BrettPhos (43.61 mg, 0.08 mmol) and cesium carbonate (661.78 mg, 2.03 mmol). The resulting mixture was stirred for 2 h at 90° C. After filtration, the filtrate was concentrated under vacuum. The residue was purified by flash chromatography on silica gel eluting with dichloromethane/methanol (25/1) to afford trans-tert-butyl (7-fluoro-3-(2-methyl-3-(1-methyl-1H-pyrazol-4-yl)cyclopropane-1-carboxamido)-6-(4-methyl-6-(oxazol-2-yl)pyridin-3-yl)isoquinolin-8-yl)carbamate (140 mg, 58%) as orange oil. LCMS (ESI) [M+H]$^+$=598.3.

Step 5: (1S,2R,3S)—N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide, (1R,2R,3R)—N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide, (1S,2S,3S)—N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide and (1R,2S,3R)—N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide

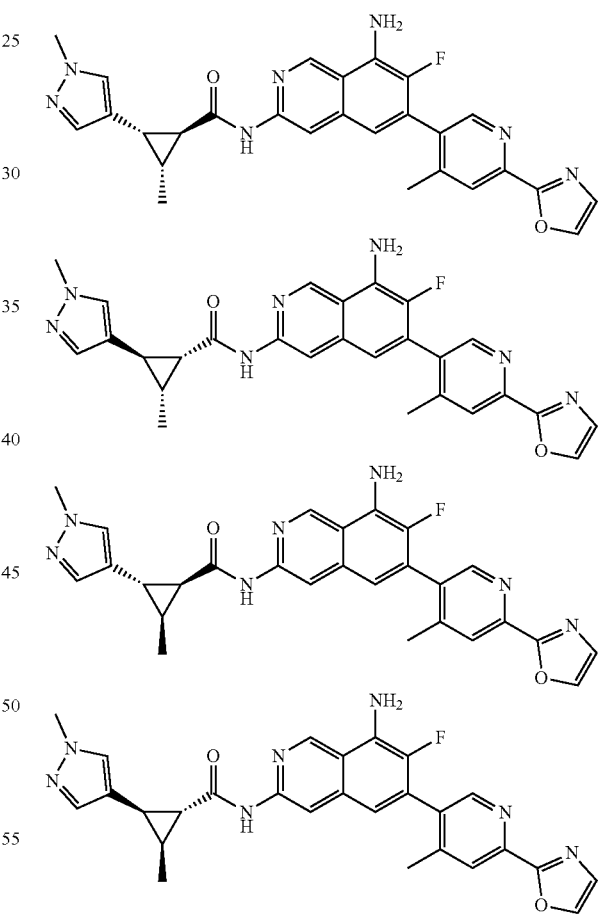

To a solution of trans-tert-butyl (7-fluoro-3-(2-methyl-3-(1-methyl-1H-pyrazol-4-yl)cyclopropane-1-carboxamido)-6-(4-methyl-6-(oxazol-2-yl)pyridin-3-yl)isoquinolin-8-yl)carbamate (310 mg, 0.51 mmol) in dichloromethane (15 mL) was added trifluoroacetic acid (15 mL). The resulting solution was stirred for 1 h at room temperature. The pH value of the solution was adjusted to 8 with ammonia in methanol (7 mol/L). After filtration, the filtrate was concentrated under vacuum. The residue was purified by Prep-HPLC to afford the mixture (120 mg, 46%) as a yellow solid. The mixture was isolated by Chiral-HPLC to afford four isomers (Cyclopropane stereochemistry for each isomer: pyrazole trans to amide; methyl relative stereochemistry arbitrarily assigned; All absolute stereochemistry arbitrarily assigned): Compound 351: (5.7 mg, 5%) as a yellow solid. Retention time: 2.261 (XBridge Shield RP18 OBD Column, 5 μm, 19*150 mm; Water (0.05% $NH_3H_2O$) and ACN (25.0% ACN up to 50.0% in 7 min); LCMS (ESI) $[M+H]^+=498.3$; $^1$HNMR (400 MHz, DMSO-$d_6$) δ 10.73 (s, 1H), 9.44 (s, 1H), 8.58 (s, 1H), 8.40-8.30 (m, 2H), 8.14 (s, 1H), 7.55-7.45 (m, 2H), 7.25 (d, J=0.9 Hz, 1H), 7.02 (d, J=6.0 Hz, 1H), 6.35 (s, 2H), 3.77 (s, 3H), 2.33 (s, 3H), 2.22 (dd, J=8.9, 4.8 Hz, 1H), 2.17-2.11 (m, 1H), 1.57 (dt, J=8.9, 6.3 Hz, 1H), 1.28 (d, J=6.1 Hz, 3H). Compound 353: (5.1 mg, 4%) as a yellow solid. Retention time: 2.691 (XBridge Shield RP18 OBD Column, 5 μm, 19*150 mm; Water (0.05% $NH_3H_2O$) and ACN (25.0% ACN up to 50.0% in 7 min); LCMS (ESI) $[M+H]^+=498.3$; $^1$HNMR (400 MHz, DMSO-$d_6$) δ 10.73 (s, 1H), 9.44 (s, 1H), 8.58 (s, 1H), 8.40-8.30 (m, 2H), 8.14 (s, 1H), 7.58-7.47 (m, 2H), 7.25 (d, J=0.8 Hz, 1H), 7.02 (d, J=6.1 Hz, 1H), 6.36 (s, 2H), 3.77 (s, 3H), 2.33 (s, 3H), 2.22 (dd, J=8.9, 4.8 Hz, 1H), 2.18-2.09 (m, 1H), 1.57 (dp, J=8.7, 6.2 Hz, 1H), 1.28 (d, J=6.1 Hz, 3H). Compound 352: (26.5 mg, 22%) as a yellow solid. Retention time: 7.975 (XBridge Shield RP18 OBD Column, 5 μm, 19*150 mm; Water (0.05% $NH_3H_2O$) and ACN (25.0% ACN up to 50.0% in 7 min); LCMS (ESI) $[M+H]^+=498.3$; $^1$HNMR (400 MHz, DMSO-$d_6$) δ 10.77 (s, 1H), 9.45 (s, 1H), 8.58 (s, 1H), 8.39-8.30 (m, 2H), 8.14 (s, 1H), 7.58-7.47 (m, 2H), 7.30 (s, 1H), 7.00 (d, J=6.1 Hz, 1H), 6.36 (s, 2H), 3.81 (s, 3H), 2.32 (s, 3H), 2.32-2.28 (m, 1H), 2.12 (t, J=4.7 Hz, 1H), 1.60 (ddd, J=9.1, 6.4, 4.8 Hz, 1H), 0.96 (d, J=6.2 Hz, 3H). Compound 350: (22.9 mg, 19%) as a yellow solid. Retention time: 9.196 (XBridge Shield RP18 OBD Column, 5 μm, 19*150 mm; Water (0.05% $NH_3H_2O$) and ACN (25.0% ACN up to 50.0% in 7 min); LCMS (ESI) $[M+H]^+=498.3$; $^1$H NMR (400 MHz, DMSO-$d_6$) δ 10.78 (s, 1H), 9.45 (s, 1H), 8.58 (s, 1H), 8.39-8.31 (m, 2H), 8.14 (s, 1H), 7.59-7.47 (m, 2H), 7.30 (s, 1H), 7.00 (d, J=6.1 Hz, 1H), 6.36 (s, 2H), 3.81 (s, 3H), 2.32 (s, 3H), 2.30 (d, J=4.6 Hz, 1H), 2.12 (t, J=4.7 Hz, 1H), 1.66-1.54 (m, 1H), 0.96 (d, J=6.2 Hz, 3H).

Example 221

2'-((8-amino-7-fluoro-6-(4-methylpyridin-3-yl)isoquinolin-3-yl)amino)-6'-methyl-5',6'-dihydrospiro[cyclopropane-1,4'-pyrazolo[1,5-d][1,4]diazepin]-7'(8'H)-one (Compound 228)

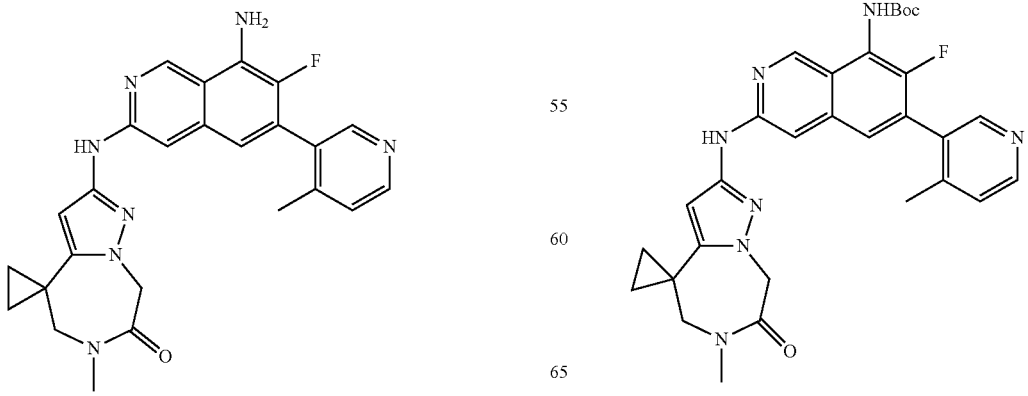

Step 1: 8'-[[6-(4-aminopyridin-3-yl)-8-chloro-7-fluoroisoquinolin-3-yl]amino]-3'-methyl-2',3',4',5'-tetrahydrospiro[cyclopropane-1,1'-pyrazolo[1,5-d][1,4]diazepine]-4'-one

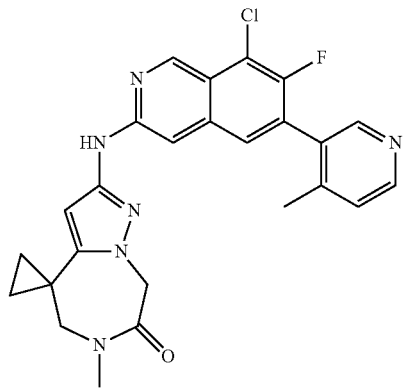 [SMILES: Cc1ccncc1-c1cc2cc(Nc3cc4n(n3)CC(=O)N(C)CC43CC3)ncc2c(Cl)c1F]

A mixture of 8'-bromo-3'-methyl-2',3',4',5'-tetrahydrospiro[cyclopropane-1,1'-pyrazolo[1,5-d][1,4]diazepine]-4'-one (200 mg, 0.74 mmol), 8-chloro-7-fluoro-6-(4-methylpyridin-3-yl)isoquinolin-3-amine (225 mg, 0.78 mmol), 3rd generation t-BuBrettPhos precatalyst (266 mg, 0.31 mmol), t-BuBrettPhos (151 mg, 0.32 mmol), cesium carbonate (1.27 g, 3.89 mmol) in 1,4-dioxane (12 mL). The resulting mixture was stirred for 2 h at 120° C. The resulting mixture was concentrated under vacuum. The residue was purified by flash chromatography on silica gel eluting with dichloromethane/methanol (10/1) to afford 8'-[[6-(4-aminopyridin-3-yl)-8-chloro-7-fluoroisoquinolin-3-yl]amino]-3'-methyl-2',3',4',5'-tetrahydrospiro[cyclopropane-1,1'-pyrazolo[1,5-d][1,4]diazepine]-4'-one (110 mg, 31%) as a light yellow solid. LCMS (ESI) $[M+H]^+=477$.

Step 2: tert-butyl N-[7-fluoro-3-([3'-methyl-4'-oxo-2',3',4',5'-tetrahydrospiro[cyclopropane-1,1'-pyrazolo[1,5-d][1,4]diazepine]-8'-yl]amino)-6-(4-methylpyridin-3-yl)isoquinolin-8-yl]carbamate

943

A mixture of 8'-[[8-chloro-7-fluoro-6-(4-methylpyridin-3-yl)isoquinolin-3-yl]amino]-3'-methyl-2',3',4',5'-tetrahydrospiro[cyclopropane-1,1'-pyrazolo[1,5-d][1,4]diazepine]-4'-one (110 mg, 0.23 mmol), tert-butyl carbamate (668 mg, 5.70 mmol), Pd$_2$(dba)$_3$·CHCl$_3$ (48 mg, 0.046 mmol), cesium carbonate (375 mg, 1.15 mmol), BrettPhos (37 mg, 0.069 mmol) in 1,4-dioxane (5 mL) was stirred for 12 h at 90° C. The mixture was filtered and the resulting mixture was concentrated under vacuum. The residue was purified by flash chromatography on silica gel eluting with dichloromethane/methanol (10/1) to afford tert-butyl N-[7-fluoro-3-([3'-methyl-4'-oxo-2',3',4',5'-tetrahydrospiro[cyclopropane-1,1'-pyrazolo[1,5-d][1,4]diazepine]-8'-yl]amino)-6-(4-methylpyridin-3-yl)isoquinolin-8-yl]carbamate (80 mg, 62%) as a light yellow solid. LCMS (ESI) [M+H]$^+$=558.

Step 3: 8'-[[8-amino-7-fluoro-6-(4-methylpyridin-3-yl)isoquinolin-3-yl]amino]-3'-methyl-2',3',4',5'-tetrahydrospiro[cyclopropane-1,1'-pyrazolo[1,5-d][1,4]diazepine]-4'-one

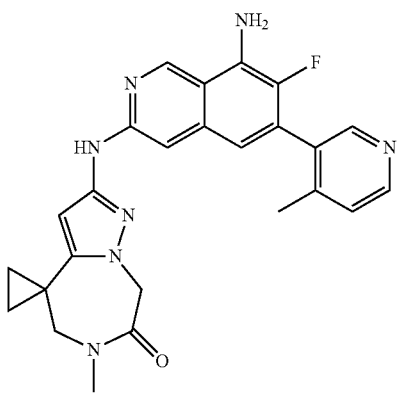 [SMILES: Cc1ccncc1-c1cc2cc(Nc3cc4n(n3)CC(=O)N(C)CC43CC3)ncc2c(N)c1F]

A mixture of tert-butyl N-[7-fluoro-3-([3'-methyl-4'-oxo-2',3',4',5'-tetrahydrospiro[cyclopropane-1,1'-pyrazolo[1,5-d][1,4]diazepine]-8'-yl]amino)-6-(4-methylpyridin-3-yl)isoquinolin-8-yl]carbamate (60 mg, 0.11 mmol), hydrogen chloride (2 mL) in dichloromethane (2 mL) and methanol (2 mL) was stirred for 1 h at room temperature. The resulting mixture was concentrated under vacuum. The residue was purified by Prep-HPLC (Kinetex EVO C18 Column, 30*150, 5um; Water (10 mmol/L NH$_4$HCO$_3$) and ACN (10% to 70% in 4.5 min)) to afford 8'-[[8-amino-7-fluoro-6-(4-methylpyridin-3-yl)isoquinolin-3-yl]amino]-3'-methyl-2',3',4',5'-tetrahydrospiro[cyclopropane-1,1'-pyrazolo[1,5-d][1,4]diazepine]-4'-one (2.9 mg, 6%) as a yellow solid. LCMS (ESI) [M+H]$^+$=458; $^1$H NMR (400 MHz, DMSO-d$_6$) δ 9.27 (s, 1H), 9.02 (s, 1H), 8.51 (d, J=6.0 Hz, 1H), 8.43 (s, 1H), 7.68 (s, 1H), 7.39 (d, J=6.0 Hz, 1H), 6.79 (d, J=6.0 Hz, 1H), 6.11 (s, 2H), 5.61 (s, 1H), 5.06 (s, 2H), 3.73 (s, 2H), 2.99 (s, 3H), 2.22 (s, 3H), 1.24-1.18 (m, 2H), 0.96-094 (m, 2H).

944

Example 222

(1R,2R,3R)—N-(8-amino-6-(5-amino-4-methylpyridin-3-yl)-7-fluoroisoquinolin-3-yl)-2-methyl-3-(1-methyl-1H-pyrazol-4-yl)cyclopropane-1-carboxamide (Compound 357)

(1S,2S,3S)—N-(8-amino-6-(5-amino-4-methylpyridin-3-yl)-7-fluoroisoquinolin-3-yl)-2-methyl-3-(1-methyl-1H-pyrazol-4-yl)cyclopropane-1-carboxamide (Compound 358)

(1S,2R,3S)—N-(8-amino-6-(5-amino-4-methylpyridin-3-yl)-7-fluoroisoquinolin-3-yl)-2-methyl-3-(1-methyl-1H-pyrazol-4-yl)cyclopropane-1-carboxamide (Compound 359) and (1R,2S,3R)—N-(8-amino-6-(5-amino-4-methylpyridin-3-yl)-7-fluoroisoquinolin-3-yl)-2-methyl-3-(1-methyl-1H-pyrazol-4-yl)cyclopropane-1-carboxamide (Compound 360)

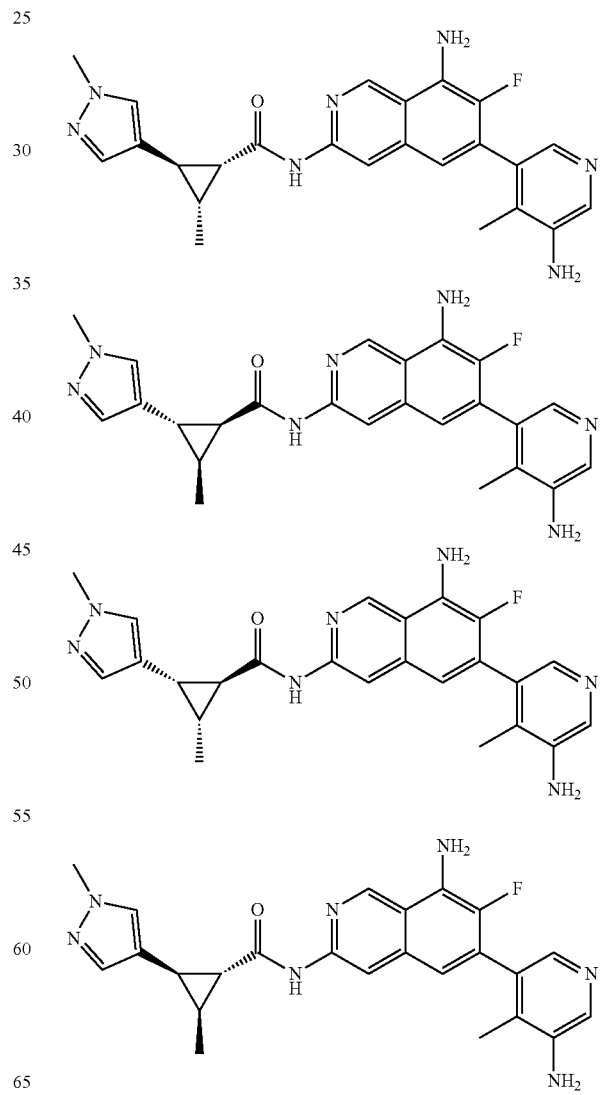

Step 1: N-(8-chloro-7-fluoro-6-iodoisoquinolin-3-yl)-2-methyl-3-(1-methyl-1H-pyrazol-4-yl)cyclopropanecarboxamide

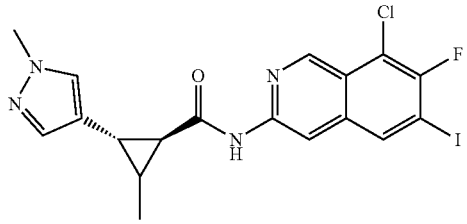 [SMILES: CC1[C@H](C(=O)Nc2cc3cc(I)c(F)c(Cl)c3cn2)[C@H]1c1cnn(C)c1]

A mixture of 8-chloro-7-fluoro-6-iodoisoquinolin-3-amine (280.6 mg, 0.87 mmol), 2-methyl-3-(1-methyl-1H-pyrazol-4-yl)cyclopropane-1-carboxylic acid (420 mg, 2.33 mmol), phosphorus oxychloride (298.4 mg, 1.95 mmol), pyridine (5 mL), dichloromethane (15 mL) was stirred for 5 minutes at 0° C. The resulting solution was stirred for 30 minute at room temperature. The reaction was quenched by water. The resulting solution was extracted with dichloromethane dried, dried with anhydrous sodium sulfate. After filtration, the filtrate was concentrated under vacuum. The residue was purified by silica gel column eluting with petroleum ether/ethyl acetate (4/6) to afford (1S,3S)—N-(8-chloro-7-fluoro-6-iodoisoquinolin-3-yl)-2-methyl-3-(1-methyl-1H-pyrazol-4-yl)cyclopropanecarboxamide (1.1 g, 2.27 mmol) as a yellow solid. LCMS (ESI) [M+H]$^+$=485.

Step 2: tert-butyl N-[(tert-butoxy)carbonyl]-N-[5-(8-chloro-7-fluoro-3-[[(1S,2R,3S)-2-methyl-3-(1-methyl-1H-pyrazol-4-yl)cyclopropane]amido]isoquinolin-6-yl)-4-methylpyridin-3-yl]carbamate

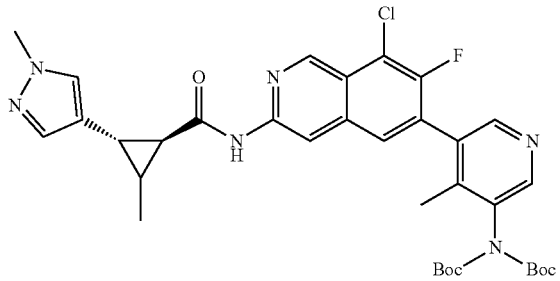 [SMILES: Cc1c(-c2cc3cc(NC(=O)[C@H]4C(C)[C@@H]4c4cnn(C)c4)ncc3c(Cl)c2F)cncc1N(C(=O)OC(C)(C)C)C(=O)OC(C)(C)C]

A mixture of N-(8-chloro-7-fluoro-6-iodoisoquinolin-3-yl)-2-methyl-3-(1-methyl-1H-pyrazol-4-yl)cyclopropane-1-carboxamide (400 mg, 0.83 mmol), tert-butyl N-[(tert-butoxy)carbonyl]-N-[4-methyl-5-(tetramethyl-1,3,2-dioxaborolan-2-yl)pyridin-3-yl]carbamate (720 mg, 1.66 mmol), terakis(triphenylphosphine)palladium (190 mg, 0.16 mmol), potassium phosphate (520 mg, 2.45 mmol) and water (1 mL) in 1,4-dioxane (5 mL) was stirred for 6 hours at 100° C. The reaction was cooled to room temperature, filtered and concentrated under vacuum. The residue was purified by silica gel column eluting with petroleum ether/ethyl acetate (1/9) to afford tert-butyl N-[(tert-butoxy)carbonyl]-N-[5-(8-chloro-7-fluoro-3-[[2-methyl-3-(1-methyl-1H-pyrazol-4-yl)cyclopropane]amido]isoquinolin-6-yl)-4-methylpyridin-3-yl]carbamate (545 mg, 0.82 mmol) as a yellow solid. LCMS (ESI) [M+H]$^+$=665.

Step 3: tert-butyl N-[6-(5-[bis[(tert-butoxy)carbonyl]amino]-4-methylpyridin-3-yl)-7-fluoro-3-[[(1S,2R,3S)-2-methyl-3-(1-methyl-1H-pyrazol-4-yl)cyclopropane]amido]isoquinolin-8-yl]carbamate

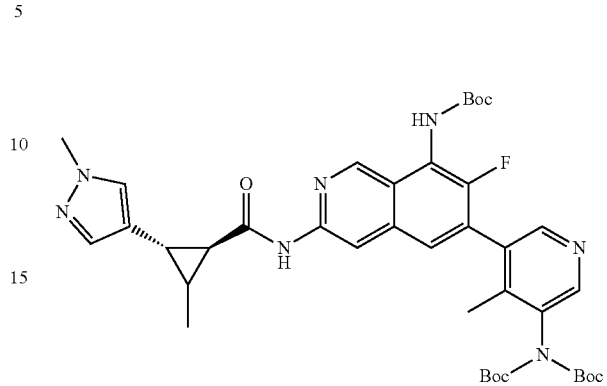

A mixture of tert-butyl N-[(tert-butoxy)carbonyl]-N-[5-(8-chloro-7-fluoro-3-[[2-methyl-3-(1-methyl-1H-pyrazol-4-yl)cyclopropane]amido]isoquinolin-6-yl)-4-methylpyridin-3-yl]carbamate (1.15 g, 1.73 mmol), tert-butyl carbamate (5.06 g, 43.19 mmol), Pd$_2$(dba)$_3$·CHCl$_3$ (356.5 mg, 0.34 mmol), Brettphos (373.8 mg, 0.70 mmol) and cesium carbonate (2.25 g, 6.91 mmol) in 1,4-dioxane (30 mL) was stirred for 3 hours at 110° C. After filtration, the filtrate was concentrated under vacuum. The residue was purified by silica gel column eluting with dichloromethane/methanol (30/1) to afford tert-butyl N-[6-(5-[bis[(tert-butoxy)carbonyl]amino]-4-methylpyridin-3-yl)-7-fluoro-3-[[2-methyl-3-(1-methyl-1H-pyrazol-4-yl)cyclopropane]amido]isoquinolin-8-yl]carbamate (1.0 g, 1.34 mmol) as a yellow solid. LCMS (ESI) [M+H]$^+$=746.

Step 4: (1R,2R,3R)—N-(8-amino-6-(5-amino-4-methylpyridin-3-yl)-7-fluoroisoquinolin-3-yl)-2-methyl-3-(1-methyl-1H-pyrazol-4-yl)cyclopropanecarboxamide, (1S,2S,3S)—N-(8-amino-6-(5-amino-4-methylpyridin-3-yl)-7-fluoroisoquinolin-3-yl)-2-methyl-3-(1-methyl-1H-pyrazol-4-yl)cyclopropanecarboxamide, (1S,2R,3S)—N-(8-amino-6-(5-amino-4-methylpyridin-3-yl)-7-fluoroisoquinolin-3-yl)-2-methyl-3-(1-methyl-1H-pyrazol-4-yl)cyclopropanecarboxamide and (1R,2S,3R)—N-(8-amino-6-(5-amino-4-methylpyridin-3-yl)-7-fluoroisoquinolin-3-yl)-2-methyl-3-(1-methyl-1H-pyrazol-4-yl)cyclopropanecarboxamide

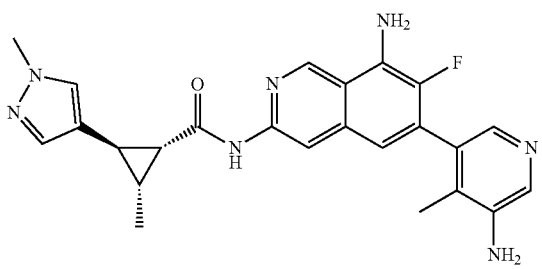

-continued

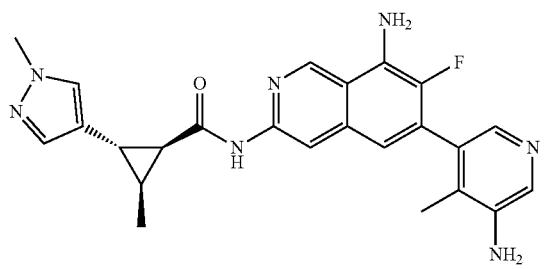

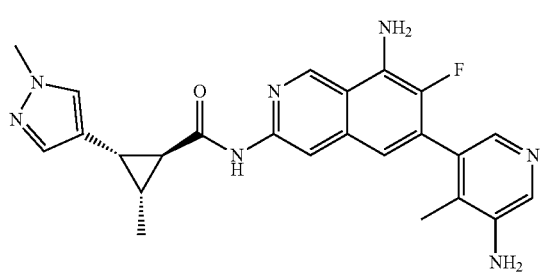

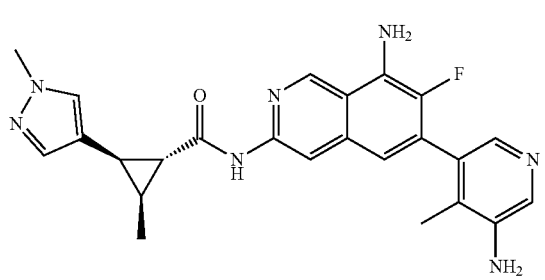

A mixture of N-[8-amino-6-(5-amino-4-methylpyridin-3-yl)-7-fluoroisoquinolin-3-yl]-2-methyl-3-(1-methyl-1H-pyrazol-4-yl)cyclopropane-1-carboxamide (400 mg, 0.90 mmol) in 4M HCl in 1,4-dioxane (50 mL) was stirred for 2 hours at room temperature. The mixture was concentrated under vacuum. The crude product was purified by Prep-HPLC (C18 silica gel; 0.5% NH₄HCO₃ in water:ACN=5%-50% in 9 min) to afford the mixture of isomers. The mixture was separated by Chiral-HPLC to afford four isomers (Cyclopropane stereochemistry for isomer: pyrazole trans to amide; methyl relative stereochemistry arbitrarily assigned; All absolute stereochemistry arbitrarily assigned): Compound 357: (11.4 mg, 0.026 mmol) as a yellow solid. Retention time: 2.794 min (Lux 3[Cellulose-3. 100*4.6 mm; MeOH (20 mMNH₃); 4.0 ml/min); LCMS (ESI) [M+H]⁺=446.3; ¹H NMR (300 MHz, Methanol-d₄) δ 9.30 (s, 1H), 8.35 (s, 1H), 8.03 (s, 1H), 7.78 (s, 1H), 7.48 (s, 1H), 7.35 (s, 1H), 6.99 (d, J=6.1 Hz, 1H), 3.86 (s, 3H), 2.34 (t, J=5.7 Hz, 1H), 2.23-2.1 (m, 1H), 2.08 (s, 3H), 1.77-1.52 (m, 1H), 1.37 (d, J=6.2 Hz, 3H). Compound 358: (101.8 mg, 0.23 mmol) as a yellow solid. Retention time: 3.089 min (Lux 3p Cellulose-3. 100*4.6 mm; MeOH (20 mMNH₃); 4.0 ml/min); LCMS (ESI) [M+H]⁺=446.3; ¹H NMR (400 MHz, DMSO-d₆) δ 10.74 (s, 1H), 9.41 (s, 1H), 8.29 (s, 1H), 7.99 (s, 1H), 7.66 (s, 1H), 7.54 (s, 1H), 7.29 (s, 1H), 6.85 (d, J=6.1 Hz, 1H), 6.26 (s, 2H), 5.26 (s, 2H), 3.81 (s, 3H), 2.33-2.25 (m, 1H), 2.11 (t, J=4.7 Hz, 1H), 1.92 (d, J=1.5 Hz, 3H), 1.66-1.53 (m, 1H), 0.96 (d, J=6.3 Hz, 3H). Compound 359: (91.3 mg, 0.21 mmol) as a yellow solid. Retention time: 2.505 min (CHIRALPAK IC-3. 100*3 mm, 3 μm; MeOH:ACN=1:1 (10 mMNH₃); 2.0 ml/min); LCMS (ESI) [M+H]⁺=446.3; ¹H NMR (400 MHz, DMSO-d₆) δ 10.74 (s, 1H), 9.41 (s, 1H), 8.29 (s, 1H), 7.99 (s, 1H), 7.66 (s, 1H), 7.54 (s, 1H), 7.29 (s, 1H), 6.85 (d, J=6.1 Hz, 1H), 6.25 (s, 2H), 5.26 (s, 2H), 3.81 (s, 3H), 2.33-2.25 (m, 1H), 2.11 (t, J=4.7 Hz, 1H), 1.92 (d, J=1.6 Hz, 3H), 1.66-1.53 (m, 1H), 0.96 (d, J=6.3 Hz, 3H). Compound 360: (17.2 mg, 0.039 mmol) as a yellow solid. Retention time: 2.084 min (CHIRALPAK IC-3. 100*3 mm, 3 μm; MeOH:ACN=1:1 (10 mMNH₃); 2.0 ml/min); LCMS (ESI) [M+H]⁺=446.3; ¹H NMR (300 MHz, Methanol-d₄) δ 9.30 (s, 1H), 8.35 (s, 1H), 8.03 (s, 1H), 7.77 (s, 1H), 7.48 (s, 1H), 7.35 (s, 1H), 6.99 (d, J=6.2 Hz, 1H), 3.86 (s, 3H), 2.34 (t, J=5.6 Hz, 1H), 2.21-2.12 (m, 1H), 2.08 (d, J=1.5 Hz, 3H), 1.71-1.52 (m, 1H), 1.37 (d, J=6.2 Hz, 3H).

Example 223

(S)-2-((8-amino-7-fluoro-6-(4-methylpyridin-3-yl)isoquinolin-3-yl)amino)-4,6-dimethyl-5,6-dihydro-4H-pyrazolo[1,5-d][1,4]diazepin-7(8H)-one (Compound 361) and (R)-2-((8-amino-7-fluoro-6-(4-methylpyridin-3-yl)isoquinolin-3-yl)amino)-4,6-dimethyl-5,6-dihydro-4H-pyrazolo[1,5-d][1,4]diazepin-7(8H)-one (Compound 362)

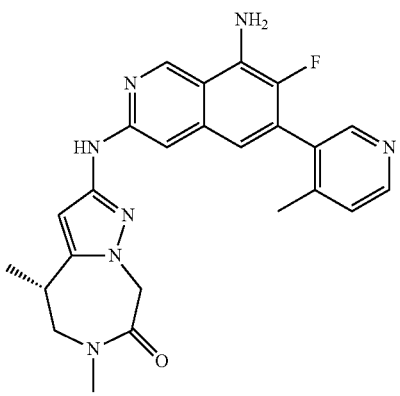

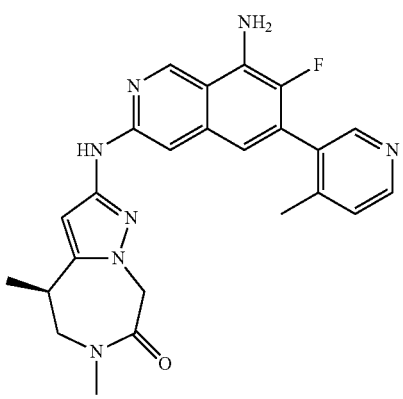

Step 1: 2-[[8-chloro-7-fluoro-6-(4-methylpyridin-3-yl)isoquinolin-3-yl]amino]-6-methyl-4-methylidene-4H,5H,6H,7H,8H-pyrazolo[1,5-d][1,4]diazepin-7-one

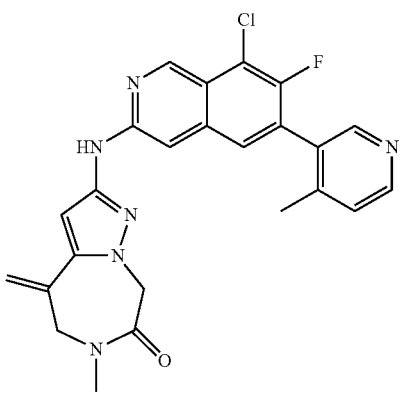 [SMILES: C=C1CN(C)C(=O)Cn2nc(Nc3cc4cc(-c5cnccc5C)c(F)c(Cl)c4cn3)cc21]

A solution of 2-bromo-6-methyl-4-methylidene-4H,5H,6H,7H,8H-pyrazolo[1,5-d][1,4]diazepin-7-one (250 mg, 0.98 mmol), 8-chloro-7-fluoro-6-(4-methylpyridin-3-yl)isoquinolin-3-amine (282 mg, 0.98 mmol), 3rd generation t-BuBrettPhos precatalyst (335 mg, 0.39 mmol), t-BuBrettPhos (189 mg, 0.39 mmol), cesium carbonate (1.6 g, 4.91 mmol) in 1,4-dioxane (15 mL) was stirred for 2 h at 130° C. The mixture was concentrated under vacuum. The residue was purified by flash chromatography on silica gel eluting with dichloromethane/methanol (10/1) to afford 2-[[8-chloro-7-fluoro-6-(4-methylpyridin-3-yl)isoquinolin-3-yl]amino]-6-methyl-4-methylidene-4H,5H,6H,7H,8H-pyrazolo[1,5-d][1,4]diazepin-7-one (200 mg, 44%) as a light yellow solid. LCMS (ESI) [M+H]$^+$=463.

Step 2: tert-butyl N-[7-fluoro-3-([6-methyl-4-methylidene-7-oxo-4H,5H,6H,7H,8H-pyrazolo[1,5-d][1,4]diazepin-2-yl]amino)-6-(4-methylpyridin-3-yl)isoquinolin-8-yl]carbamate

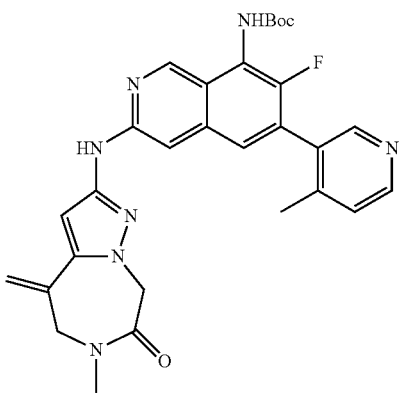 [SMILES: C=C1CN(C)C(=O)Cn2nc(Nc3cc4cc(-c5cnccc5C)c(F)c(NC(=O)OC(C)(C)C)c4cn3)cc21]

A mixture of 2-[[8-chloro-7-fluoro-6-(4-methylpyridin-3-yl)isoquinolin-3-yl]amino]-6-methyl-4-methylidene-4H,5H,6H,7H,8H-pyrazolo[1,5-d][1,4]diazepin-7-one (180 mg, 0.39 mmol), tert-butyl carbamate (1.14 g, 9.73 mmol), Pd$_2$(dba)$_3$·CHCl$_3$ (81 mg, 0.078 mmol), cesium carbonate (636 mg, 1.95 mmol), BrettPhos (63 mg, 0.12 mmol) in 1,4-dioxane (5 mL) was stirred for 3 h at 90° C. After filtration, the filtrate was concentrated under vacuum. The residue was purified by flash chromatography on silica gel eluting with dichloromethane/methanol (10/1) to afford tert-butyl N-[7-fluoro-3-([6-methyl-4-methylidene-7-oxo-4H,5H,6H,7H,8H-pyrazolo[1,5-d][1,4]diazepin-2-yl]amino)-6-(4-methylpyridin-3-yl)isoquinolin-8-yl]carbamate (160 mg, 76%) as a light yellow solid. LCMS (ESI) [M+H]$^+$=544.

Step 3: tert-butyl N-[3-([4,6-dimethyl-7-oxo-4H,5H,6H,7H,8H-pyrazolo[1,5-d][1,4]diazepin-2-yl]amino)-7-fluoro-6-(4-methylpyridin-3-yl)isoquinolin-8-yl]carbamate

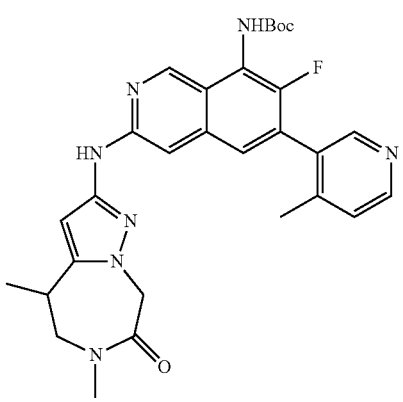 [SMILES: Cc1ccncc1-c1cc2cc(Nc3cc4n(n3)CC(=O)N(C)CC4C)ncc2c(NC(=O)OC(C)(C)C)c1F]

A mixture of tert-butyl N-[7-fluoro-3-([6-methyl-4-methylidene-7-oxo-4H,5H,6H,7H,8H-pyrazolo[1,5-d][1,4]diazepin-2-yl]amino)-6-(4-methylpyridin-3-yl)isoquinolin-8-yl]carbamate (140 mg, 0.26 mmol), palladium on carbon (200 mg) in methanol (10 mL) was stirred under hydrogen for 1 h at room temperature. After filtration, the filtrate was concentrated under vacuum to afford tert-butyl N-[3-([4,6-dimethyl-7-oxo-4H,5H,6H,7H,8H-pyrazolo[1,5-d][1,4]diazepin-2-yl]amino)-7-fluoro-6-(4-methylpyridin-3-yl)isoquinolin-8-yl]carbamate (134 mg, 95%) as a light yellow solid. LCMS (ESI) [M+H]$^+$=546.

Step 4: (S)-2-((8-amino-7-fluoro-6-(4-methylpyridin-3-yl)isoquinolin-3-yl)amino)-4,6-dimethyl-5,6-dihydro-4H-pyrazolo[1,5-d][1,4]diazepin-7(8H)-one and (R)-2-((8-amino-7-fluoro-6-(4-methylpyridin-3-yl)isoquinolin-3-yl)amino)-4,6-dimethyl-5,6-dihydro-4H-pyrazolo[1,5-d][1,4]diazepin-7(8H)-one

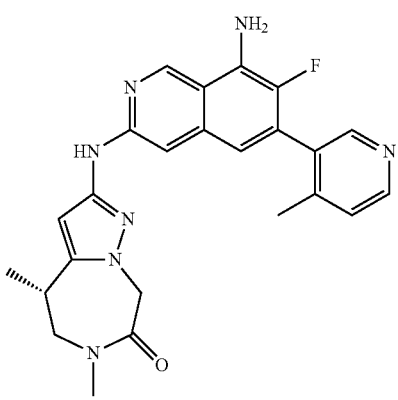

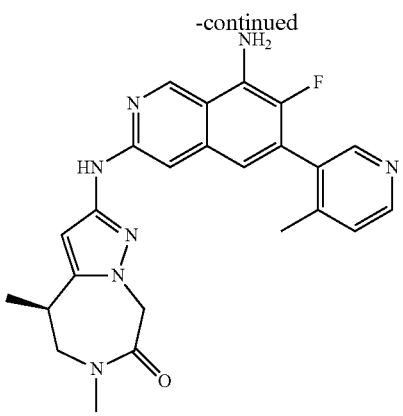

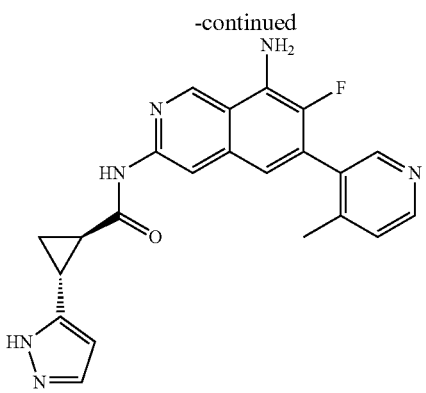

A solution of tert-butyl N-[3-([4,6-dimethyl-7-oxo-4H,5H,6H,7H,8H-pyrazolo[1,5-d][1,4]diazepin-2-yl]amino)-7-fluoro-6-(4-methylpyridin-3-yl)isoquinolin-8-yl]carbamate (150 mg, 0.28 mmol), hydrogen chloride (2 mL) in dichloromethane (2 mL) was stirred for 1 h at room temperature. The resulting solution was concentrated under vacuum. The crude product was purified by Prep-HPLC [Kinetex EVO C18 Column, 30*150, 5 um; Water (10 MMOL/L NH$_4$HCO$_3$) and ACN (25% to 42% in 7 min)] to afford the racemic product (50 mg, 41%) as a yellow solid. The racemic product was purified by Prep-SFC to afford the single enantiomers: Compound 362: (5.7 mg, 11%) as a yellow solid. Retention time: 0.867 min, CHIRALCEL OJ-3, 4.6*50 mm, 3 μm; CO$_2$/methanol=(50%)/(0.1% DEA, 50%); LCMS (ESI) [M+H]$^+$=446; $^1$HNMR (400 MHz, DMSO-d$_6$) δ 9.28 (s, 1H), 9.09 (s, 1H), 8.50 (d, J=6.0 Hz, 1H), 8.43 (s, 1H), 7.72 (s, 1H), 7.39 (d, J=6.0 Hz, 1H), 6.78 (d, J=6.0 Hz, 1H), 6.11 (s, 2H), 6.04 (s, 1H), 5.13-4.81 (m, 2H), 3.99-3.51 (m, 2H), 3.32-3.35 (m, 1H) 2.97 (s, 3H), 2.22 (s, 3H), 1.26 (d, J=7.0 Hz, 3H). Compound 361: (5.8 mg, 12%) as a yellow solid. Retention time: 1.268 min, CHIRALCEL OJ-3, 4.6*50 mm, 3 μm; CO$_2$/methanol=(50%)/(0.1% DEA, 50%); LCMS (ESI) [M+H]$^+$=446. $^1$HNMR (400 MHz, DMSO-d$_6$) δ 9.28 (s, 1H), 9.09 (s, 1H), 8.50 (d, J=6.0 Hz, 1H), 8.43 (s, 1H), 7.72 (s, 1H), 7.39 (d, J=6.0 Hz, 1H), 6.78 (d, J=6.0 Hz, 1H), 6.11 (s, 2H), 6.04 (s, 1H), 5.13-4.81 (m, 2H), 3.99-3.51 (m, 2H), 3.32-3.35 (m, 1H) 2.97 (s, 3H), 2.22 (s, 3H), 1.26 (d, J=7.0 Hz, 3H).

Example 224

(1S,2S)—N-(8-amino-7-fluoro-6-(4-methylpyridin-3-yl)isoquinolin-3-yl)-2-(1H-pyrazol-5-yl)cyclopropane-1-carboxamide (Compound 363) and (1R,2R)—N-(8-amino-7-fluoro-6-(4-methylpyridin-3-yl)isoquinolin-3-yl)-2-(1H-pyrazol-5-yl)cyclopropane-1-carboxamide (Compound 364)

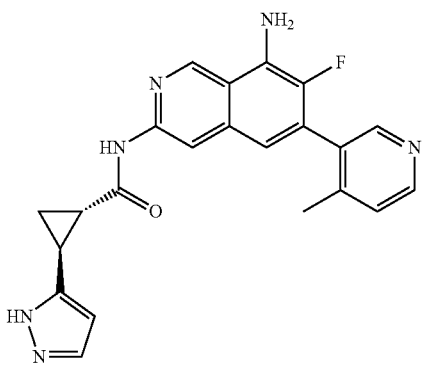

Step 1: ethyl (2Z)-3-(1H-pyrazol-5-yl)prop-2-enoate

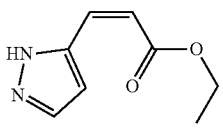

A mixture of ethyl 2-[bis(2,2,2-trifluoroethoxy)phosphoryl]acetate (3.04 g, 9.15 mmol), sodium hydride (400 mg, 16.66 mmol), 1H-pyrazole-5-carbaldehyde (800 mg, 8.32 mmol) in tetrahydrofuran (100 mL) was stirred for 2 h at room temperature. The reaction was quenched with water. The resulting mixture was extracted with ethyl acetate and the organic layers combined and concentrated under vacuum. The residue was purified by flash chromatography on a silica gel column eluted with ethyl acetate/petroleum ether (1/3) to afford ethyl (2Z)-3-(1H-pyrazol-5-yl)prop-2-enoate (500 mg, 2.99 mmol) as a white solid. LCMS (ESI) [M+H]$^+$=167.

Step 2: ethyl (2Z)-3-[1-(oxan-2-yl)-1H-pyrazol-5-yl]prop-2-enoate

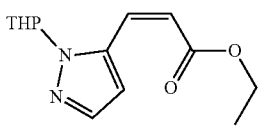

A mixture of ethyl (2Z)-3-(1H-pyrazol-5-yl)prop-2-enoate (530 mg, 3.18 mmol), 3,4-dihydro-2H-pyran (536 mg, 6.37 mmol), TsOH (27 mg, 0.15 mmol) in ethyl acetate (20 mL) was stirred for 2 h at 80° C. The resulting mixture was concentrated under vacuum. The residue was purified by flash chromatography on a silica gel column eluted with ethyl acetate/petroleum ether (1/10) to afford ethyl (2Z)-3-[1-(oxan-2-yl)-1H-pyrazol-5-yl]prop-2-enoate (600 mg, 2.39 mmol) as colorless oil. LCMS (ESI) [M+H]$^+$=251

Step 3: ethyl trans-2-[1-(oxan-2-yl)-1H-pyrazol-5-yl]cyclopropane-1-carboxylate

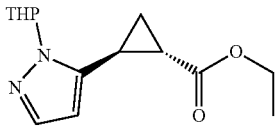

A mixture of trimethyl(oxo)-1^[6]-sulfanylium iodide (3.52 g, 15.99 mmol), t-BuOK (1.792 g, 15.97 mmol), ethyl (2Z)-3-[1-(oxan-2-yl)-1H-pyrazol-5-yl]prop-2-enoate (2 g, 7.99 mmol) in DMSO (20 mL) was stirred for 2 h at room temperature. The resulting solution was diluted with water. The resulting solution was extracted with ethyl acetate and the organic layers combined and concentrated under vacuum. The residue was purified by flash chromatography on a silica gel column eluted with ethyl acetate/petroleum ether (1/10) to afford trans ethyl-2-[1-(oxan-2-yl)-1H-pyrazol-5-yl]cyclopropane-1-carboxylate (400 mg, 1.52 mmol) as colorless oil. LCMS (ESI) [M+H]$^+$=265

Step 4: trans-2-[1-(oxan-2-yl)-1H-pyrazol-5-yl]cyclopropane-1-carboxylic Acid

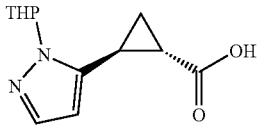

A mixture of trans ethyl-2-[1-(oxan-2-yl)-1H-pyrazol-5-yl]cyclopropane-1-carboxylate (400 mg, 1.51 mmol), lithium hydroxide (180 mg, 7.51 mmol) in tetrahydrofuran (10 mL) and water (10 mL) was stirred for 5 h at room temperature. The reaction mixture was adjusted to pH 4 with hydrogen chloride. The resulting solution was extracted with ethyl acetate and the organic layers combined and concentrated under vacuum to afford trans-2-[1-(oxan-2-yl)-1H-pyrazol-5-yl]cyclopropane-1-carboxylic acid (300 mg, 1.27 mmol) as a white solid. LCMS (ESI) [M+H]$^+$=237.

Step 5: trans-N-[8-chloro-7-fluoro-6-(4-methylpyridin-3-yl)isoquinolin-3-yl]-2-[1-(oxan-2-yl)-1H-pyrazol-5-yl]cyclopropane-1-carboxamide

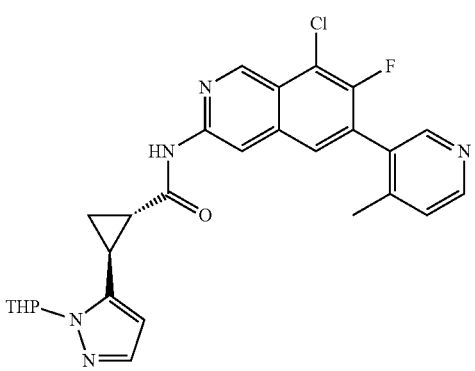

A mixture of trans-2-[1-(oxan-2-yl)-1H-pyrazol-5-yl]cyclopropane-1-carboxylic acid (350 mg, 1.48 mmol), 8-chloro-7-fluoro-6-(4-methylpyridin-3-yl)isoquinolin-3-amine (426 mg, 1.48 mmol) in Pyridine (1 mL) and dichloromethane (10 mL) was added phosphorus oxychloride (450 mg, 2.93 mmol). The resulting solution was stirred for 2 h at room temperature. The resulting mixture was concentrated under vacuum. The residue was purified by flash chromatography on a silica gel column eluted with dichloromethane/methanol (95/5) to afford trans-N-[8-chloro-7-fluoro-6-(4-methylpyridin-3-yl)isoquinolin-3-yl]-2-[1-(oxan-2-yl)-1H-pyrazol-5-yl]cyclopropane-1-carboxamide (300 mg, 0.59 mmol) as a yellow solid. LCMS (ESI) [M+H]$^+$=506

Step 5: trans-tert-butyl N-[7-fluoro-6-(4-methylpyridin-3-yl)-3-[[2-[1-(oxan-2-yl)-1H-pyrazol-5-yl]cyclopropane]amido]isoquinolin-8-yl]carbamate

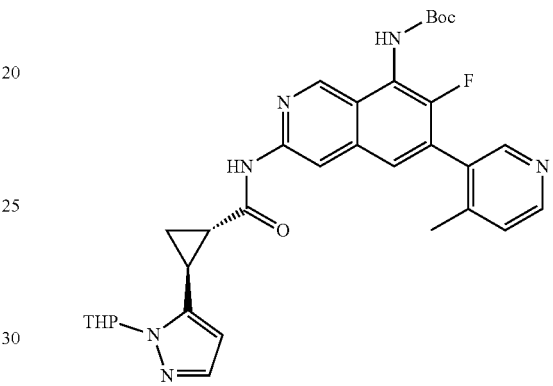

A mixture of tert-butyl carbamate (1.67 g, 14.25 mmol), trans-N-[8-chloro-7-fluoro-6-(4-methylpyridin-3-yl)isoquinolin-3-yl]-2-[1-(oxan-2-yl)-1H-pyrazol-5-yl]cyclopropane-1-carboxamide (360 mg, 0.71 mmol), Pd$_2$(dba)$_3$.CHCl$_3$ (150 mg, 0.14 mmol), BrettPhos (153 mg, 0.28 mmol), cesium carbonate (930 mg, 2.85 mmol) in dioxane (10 mL) was stirred for 12 h at 90° C. under nitrogen. The solids were filtered out. The resulting mixture was concentrated under vacuum. The residue was applied onto a silica gel column with dichloromethane/methanol (10/1) to afford trans-tert-butyl N-[7-fluoro-6-(4-methylpyridin-3-yl)-3-[[-2-[1-(oxan-2-yl)-1H-pyrazol-5-yl]cyclopropane]amido]isoquinolin-8-yl]carbamate (200 mg, 0.34 mmol) as a white solid. LCMS (ESI) [M+H]$^+$=587

Step 6: (1S,2S)—N-(8-amino-7-fluoro-6-(4-methylpyridin-3-yl)isoquinolin-3-yl)-2-(1H-pyrazol-5-yl)cyclopropane-1-carboxamide and (1R,2R)—N-(8-amino-7-fluoro-6-(4-methylpyridin-3-yl)isoquinolin-3-yl)-2-(1H-pyrazol-5-yl)cyclopropane-1-carboxamide

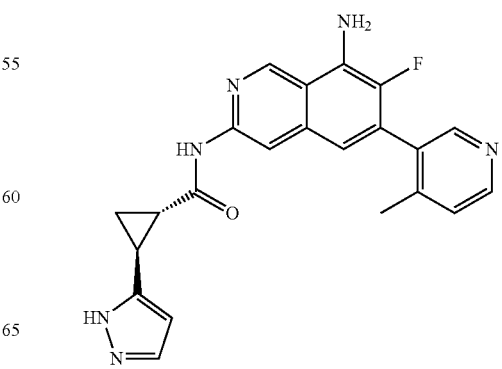

-continued

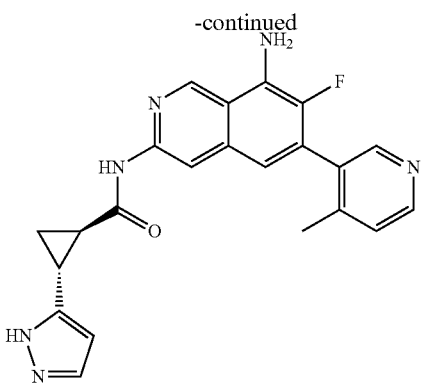

A mixture of trans-tert-butyl N-[7-fluoro-6-(4-methylpyridin-3-yl)-3-[[-2-[1-(oxan-2-yl)-1H-pyrazol-5-yl]cyclopropane]amido]isoquinolin-8-yl]carbamate (200 mg, 0.34 mmol) in trifluoroacetic acid (5 mL) was stirred for 1 h at room temperature. The resulting mixture was concentrated under vacuum. The residue was purified by reverse phase chromatography (acetonitrile 0-50/0.1% NH$_4$HCO$_3$ in water) to afford the racemic product (70 mg, 0.17 mmol) as a white solid. The racemate product was separated by Chiral-HPLC to afford two isomers (Cyclopropane stereochemistry: pyrazole trans to amide): Compound 364: Retention time:1.69 min (Lux Cellulose-4, 0.46*5 cm; 3 µm; Hex (0.1% DEA):EtOH=50:50; 1 ml/min); LCMS (ESI) [M+H]$^+$=402; $^1$HNMR (400 MHz, CD$_3$OD) δ 9.29 (s, 1H), 8.47 (d, J=5.2 Hz, 1H), 8.42 (s, 1H), 8.35 (s, 1H), 7.58-7.56 (m, 1H), 7.44 (d, J=5.2 Hz, 1H), 7.00 (d, J=6 Hz, 1H), 6.18-6.16 (m, 1H), 2.60-2.59 (m, 1H), 2.31 (s, 3H), 2.29-2.25 (m, 1H), 1.64-1.61 (m, 1H), 1.44-1.42 (m, 1H); Compound 363: Retention time: 3.07 min (Lux Cellulose-4, 0.46*5 cm; 3 µm; Hex (0.1% DEA):EtOH=50:50; 1 ml/min); LCMS (ESI) [M+H]$^+$=402; $^1$HNMR (400 MHz, CD$_3$OD) δ 9.29 (s, 1H), 8.47 (d, J=5.2 Hz, 1H), 8.42 (s, 1H), 8.35 (s, 1H), 7.58-7.56 (m, 1H), 7.44 (d, J=5.2 Hz, 1H), 7.00 (d, J=6 Hz, 1H), 6.18-6.16 (m, 1H), 2.60-2.59 (m, 1H), 2.31 (s, 3H), 2.29-2.25 (m, 1H), 1.64-1.61 (m, 1H), 1.44-1.42 (m, 1H).

Example 225

(1S,2S,3S)—N-(8-amino-7-fluoro-6-(4-methylpyridin-3-yl)isoquinolin-3-yl)-2-(1-(2-hydroxyethyl)-1H-pyrazol-4-yl)-3-methylcyclopropane-1-carboxamide (Compound 368)

(1S,2S,3R)—N-(8-amino-7-fluoro-6-(4-methylpyridin-3-yl)isoquinolin-3-yl)-2-(1-(2-hydroxyethyl)-1H-pyrazol-4-yl)-3-methylcyclopropane-1-carboxamide (Compound 367)

(1R,2R,3R)—N-(8-amino-7-fluoro-6-(4-methylpyridin-3-yl)isoquinolin-3-yl)-2-(1-(2-hydroxyethyl)-1H-pyrazol-4-yl)-3-methylcyclopropane-1-carboxamide (Compound 366) and (1R,2R,3S)—N-(8-amino-7-fluoro-6-(4-methylpyridin-3-yl)isoquinolin-3-yl)-2-(1-(2-hydroxyethyl)-1H-pyrazol-4-yl)-3-methylcyclopropane-1-carboxamide (Compound 365)

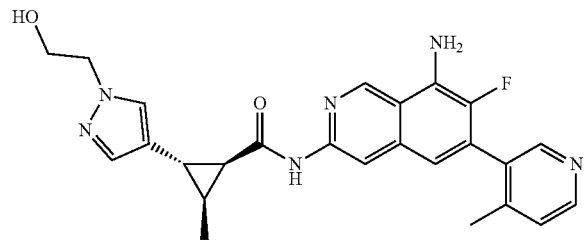

-continued

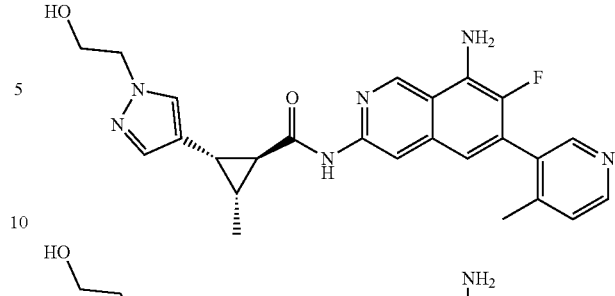

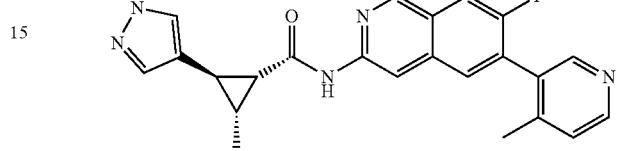

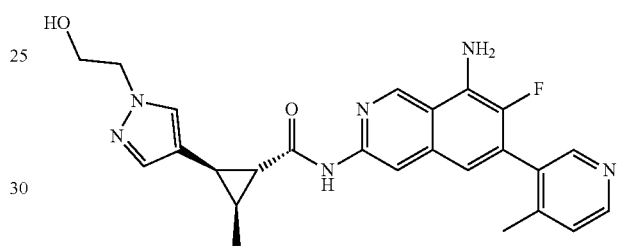

Step 1: 1-(2-(benzyloxy)ethyl)-4-iodo-1H-pyrazole

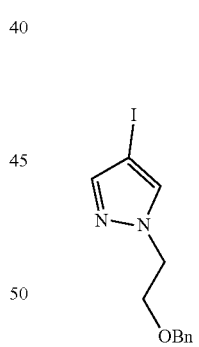

A mixture of 4-iodo-1H-pyrazole (10 g, 51.55 mmol), (2-bromoethoxy)methyl]benzene (13.24 g, 61.54 mmol), potassium carbonate (14.23 g, 102.94 mmol) in N,N-dimethylformamide (25 mL) was stirred for 2 hours at room temperature. The resulting solution was diluted with ethyl acetate. The resulting mixture was washed with water. The organic phase was dried with anhydrous sodium sulfate. After filtration, the filtrate was concentrated under vacuum. The residue was purified by silica gel column eluting with ethyl acetate/petroleum ether (1/1) to afford 1-[2-(benzyloxy)ethyl]-4-iodo-1H-pyrazole (20 g, 60.79 mmol) as yellow oil. LCMS (ESI) [M+H]$^+$=329.

957

Step 2: (E)-tert-butyl 3-(1-(2-(benzyloxy)ethyl)-1H-pyrazol-4-yl)acrylate

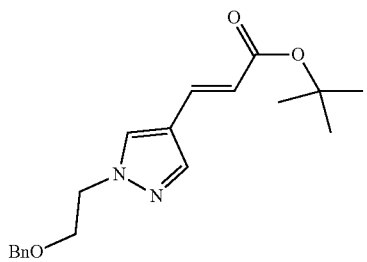 [SMILES: CC(C)(C)OC(=O)/C=C/c1cnn(CCOCc2ccccc2)c1]

A mixture of 1-[2-(benzyloxy)ethyl]-4-iodo-1H-pyrazole (22 g, 67.04 mmol), tert-butyl prop-2-enoate (25.76 g, 200.95 mmol), palladium acetate (2.25 g, 10.04 mmol), tri-o-tolyl phopine (12.23 g, 40.18 mmol) and triethylamine (10.16 g, 100.43 mmol) in N,N-dimethylformamide (150 mL) was stirred for 12 hours at 110° C. The resulting solution was diluted with ethyl acetate and then washed with water and concentrated. The residue was purified by silica gel column eluting with ethyl acetate/petroleum ether (4/6) to afford tert-butyl (2E)-3-[1-[2-(benzyloxy)ethyl]-1H-pyrazol-4-yl]prop-2-enoate (13.8 g, 41.95 mmol) as yellow oil. LCMS (ESI) [M+H]$^+$=329.

Step 3: (1S,2S)-tert-butyl 2-(1-(2-(benzyloxy)ethyl)-1H-pyrazol-4-yl)-3-methylcyclopropanecarboxylate

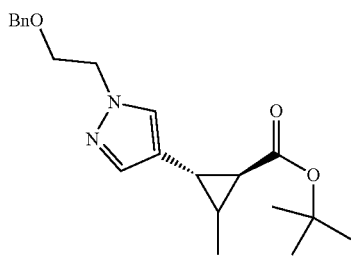 [SMILES: CC1[C@H](C(=O)OC(C)(C)C)[C@H]1c1cnn(CCOCc2ccccc2)c1]

LDA (19 mL, 45.67 mmol) was added to a mixture of tert-butyl (2E)-3-[1-[2-(benzyloxy)ethyl]-1H-pyrazol-4-yl]prop-2-enoate (5 g, 15.23 mmol) and ethylene glycol dimethyl ether (100 mL) at −78° C. The solution was stirred for 1 hour at this temperature. Then ethyldiphenylsulfanium trifluoroborane fluoride (13.8 g, 45.67 mmol) was added at −78° C. and then stirred for 5 hours at room temperature. The reaction was then quenched by the addition water. The resulting mixture was extracted with dichloromethane. The organic layers were dried with anhydrous sodium sulfate. After filtration, the filtrate was concentrated under vacuum. The residue was purified by silica gel column eluting with ethyl acetate/petroleum ether (7/3) to afford tert-butyl 2-[1-[2-(benzyloxy)ethyl]-1H-pyrazol-4-yl]-3-methylcyclopropane-1-carboxylate (4 g, 11.20 mmol) as red oil. LCMS (ESI) [M+H]$^+$=357.

958

Step 4: 2-(1-(2-(benzyloxy)ethyl)-1H-pyrazol-4-yl)-3-methylcyclopropanecarboxylic Acid

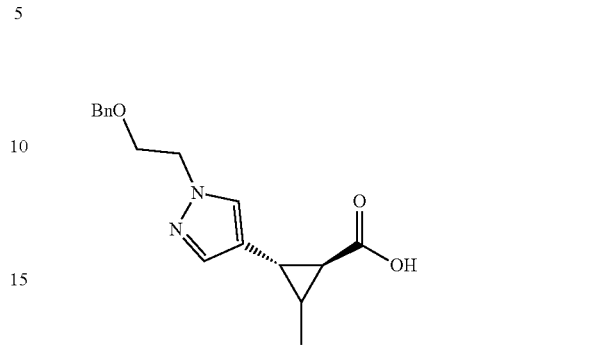

A mixture of tert-butyl 2-[1-[2-(benzyloxy)ethyl]-1H-pyrazol-4-yl]-3-methylcyclopropane-1-carboxylate (3.9 g, 10.94 mmol), trifluoroacetic acid (10 mL) in dichloromethane (50 mL). The resulting solution was stirred for 3 hours at room temperature. The resulting mixture was concentrated under vacuum to afford 2-[1-[2-(benzyloxy)ethyl]-1H-pyrazol-4-yl]-3-methylcyclopropane-1-carboxylic acid (5 g, crude) as purple oil. LCMS (ESI) [M+H]$^+$=301.

Step 5: 2-(1-(2-(benzyloxy)ethyl)-1H-pyrazol-4-yl)-N-(8-chloro-7-fluoro-6-(4-methylpyridin-3-yl)isoquinolin-3-yl)-3-methylcyclopropanecarboxamide

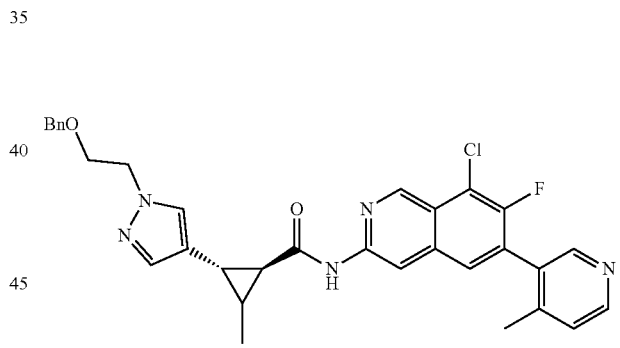

A mixture of 2-[1-[2-(benzyloxy)ethyl]-1H-pyrazol-4-yl]-3-methylcyclopropane-1-carboxylic acid (5.6 g, 18.65 mmol), 8-chloro-7-fluoro-6-(4-methylpyridin-3-yl)isoquinolin-3-amine (5.36 g, 18.62 mmol), pyridine (20 mL) and phosphorus oxychloride (5.71 g, 37.25 mmol) in dichloromethane (100 mL, 1.57 mol) was stirred for 30 minutes at room temperature. The reaction was then quenched by water. The resulting solution was extracted with dichloromethane. The organic layers were dried with anhydrous sodium sulfate. After filtration, the filtrate was concentrated under vacuum. The residue was purified by silica gel column eluting with ethyl acetate/petroleum ether (7/3) to afford 2-[1-[2-(benzyloxy)ethyl]-1H-pyrazol-4-yl]-N-[8-chloro-7-fluoro-6-(4-methylpyridin-3-yl)isoquinolin-3-yl]-3-methylcyclopropane-1-carboxamide (6.1 g, 10.70 mmol) as a yellow solid. LCMS (ESI) [M+H]$^+$=570.

Step 6: tert-butyl 3-((1S,2S)-2-(1-(2-(benzyloxy)ethyl)-1H-pyrazol-4-yl)-3-methylcyclopropanecarboxamido)-7-fluoro-6-(4-methylpyridin-3-yl)isoquinolin-8-ylcarbamate

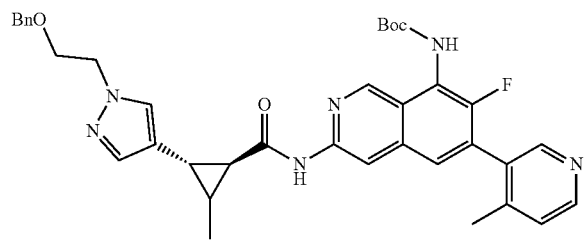 [SMILES: Cc1ccncc1-c1cc2cc(NC(=O)[C@H]3C(C)[C@@H]3c3cnn(CCOCc4ccccc4)c3)ncc2c(NC(=O)OC(C)(C)C)c1F]

A mixture of 2-[1-[2-(benzyloxy)ethyl]-1H-pyrazol-4-yl]-N-[8-chloro-7-fluoro-6-(4-methylpyridin-3-yl)isoquinolin-3-yl]-3-methylcyclopropane-1-carboxamide (6.1 g, 10.70 mmol), tert-butyl carbamate (37.63 g, 321.21 mmol), Pd$_2$(dba)$_3$·CHCl$_3$ (2.22 g, 2.14 mmol), BrettPhos (1.15 g, 2.14 mmol) and cesium carbonate (13.98 g, 42.91 mmol) in 1,4-dioxane (100 mL) was stirred for 5 hours at 90° C. The solids were filtered out. The residue was purified by silica gel column eluting with dichloromethane/methanol (4/1) to tert-butyl N-(3-[[2-[1-[2-(benzyloxy)ethyl]-1H-pyrazol-4-yl]-3-methylcyclopropane]amido]-7-fluoro-6-(4-methylpyridin-3-yl)isoquinolin-8-yl)carbamate (6.8 g, 10.45 mmol) as a purple solid. LCMS (ESI) [M+H]$^+$=651.

Step 7: tert-butyl 7-fluoro-3-(2-(1-(2-hydroxyethyl)-1H-pyrazol-4-yl)-3-methylcyclopropanecarboxamido)-6-(4-methylpyridin-3-yl)isoquinolin-8-ylcarbamate

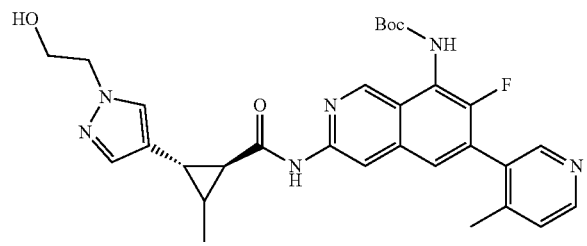 [SMILES: Cc1ccncc1-c1cc2cc(NC(=O)[C@H]3C(C)[C@@H]3c3cnn(CCO)c3)ncc2c(NC(=O)OC(C)(C)C)c1F]

A mixture of tert-butyl N-(3-[[(1S,2S)-2-[1-[2-(benzyloxy)ethyl]-1H-pyrazol-4-yl]-3-methylcyclopropane]amido]-7-fluoro-6-(4-methylpyridin-3-yl)isoquinolin-8-yl)carbamate (1.5 g, 2.31 mmol), Pd(OH)$_2$/C (646 mg, 4.60 mmol) and methanol (50 mL) was bubbled through with hydrogen gas for 20 min. The resulting solution was stirred for 12 hours under hydrogen (balloon) at 50° C. The mixture was filtered and concentrated. The residue was purified by silica gel column eluting with dichloromethane/methanol (96/4) to afford tert-butyl N-(7-fluoro-3-[[2-[1-(2-hydroxyethyl)-1H-pyrazol-4-yl]-3-methylcyclopropane]amido]-6-(4-methylpyridin-3-yl)isoquinolin-8-yl)carbamate (250 mg, 0.45 mmol) as a yellow solid. LCMS (ESI) [M+H]=561.

Step 8: (1S,2S,3S)—N-(8-amino-7-fluoro-6-(4-methylpyridin-3-yl)isoquinolin-3-yl)-2-(1-(2-hydroxyethyl)-1H-pyrazol-4-yl)-3-methylcyclopropanecarboxamide, (1S,2S,3R)—N-(8-amino-7-fluoro-6-(4-methylpyridin-3-yl)isoquinolin-3-yl)-2-(1-(2-hydroxyethyl)-1H-pyrazol-4-yl)-3-methylcyclopropanecarboxamide, (1R,2R,3R)—N-(8-amino-7-fluoro-6-(4-methylpyridin-3-yl)isoquinolin-3-yl)-2-(1-(2-hydroxyethyl)-1H-pyrazol-4-yl)-3-methylcyclopropanecarboxamide and (1R,2R,3S)—N-(8-amino-7-fluoro-6-(4-methylpyridin-3-yl)isoquinolin-3-yl)-2-(1-(2-hydroxyethyl)-1H-pyrazol-4-yl)-3-methylcyclopropanecarboxamide

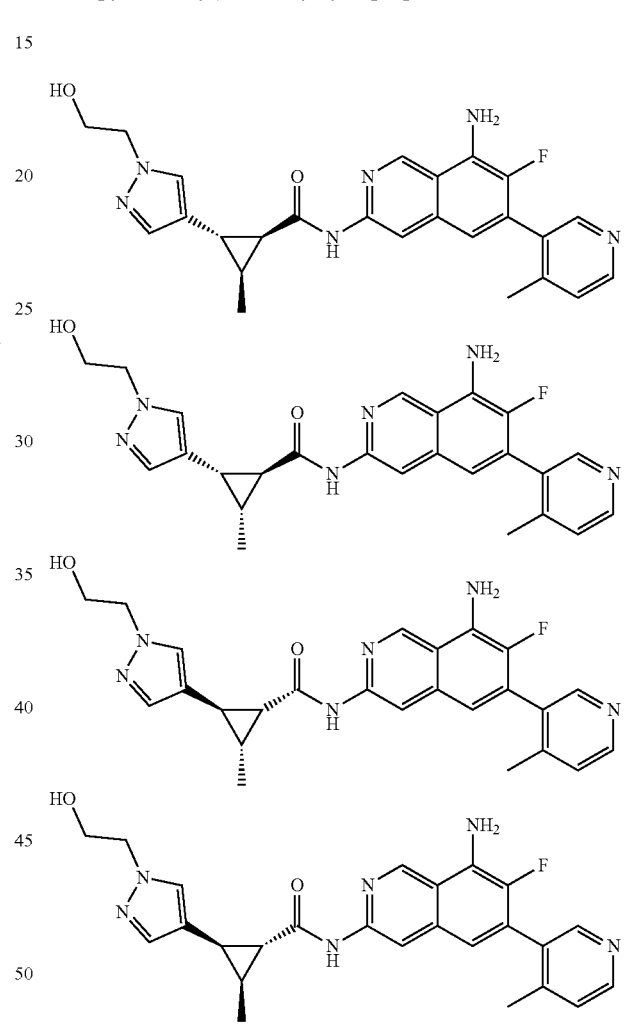

A mixture of tert-butyl N-(7-fluoro-3-[[2-[1-(2-hydroxyethyl)-1H-pyrazol-4-yl]-3-methylcyclopropane]amido]-6-(4-methylpyridin-3-yl)isoquinolin-8-yl)carbamate (200 mg, 0.36 mmol) in HCl/1,4-dioxane (10 mL) was stirred for 1 hour at room temperature. The mixture was concentrated under vacuum. The crude product was purified by Prep-HPLC (C18 silica gel; 0.5% NH$_4$HCO$_3$ in water: ACN=20%-50% in 7 min) to afford the mixture of 4 isomers. The mixture was separated by Chiral-HPLC to afford four isomers (Cyclopropane stereochemistry for each isomer: pyrazole trans to amide; methyl relative stereochemistry arbitrarily assigned; All absolute stereochemistry arbitrarily assigned): Compound 368: (12.1 mg, 0.026 mmol) as a yellow solid. Retention time: 4.112 min (Chiral IA.0.46*15 cm; 5 µm; MeOH (0.1% DEA): dichloromethane=80:20; 1.0 ml/min); LCMS (ESI) [M+H]⁺=461.3; ¹H NMR (400 MHz, DMSO-d₆) δ 10.72 (s, 1H), 9.42 (s, 1H), 8.52 (d, J=5.0 Hz, 1H), 8.45 (s, 1H), 8.35 (s, 1H), 7.55 (s, 1H), 7.41 (d, J=5.1 Hz, 1H), 7.27 (d, J=0.8 Hz, 1H), 6.95 (d, J=6.1 Hz, 1H), 6.31 (s, 2H), 4.87 (s, 1H), 4.06 (t, J=5.7 Hz, 2H), 3.69 (t, J=5.7 Hz, 2H), 2.22 (s, 3H), 2.28-2.13 (m, 2H), 1.62-1.49 (m, 1H), 1.28 (d, J=6.2 Hz, 3H).Compound 367: (20.5 mg, 0.045 mmol) as a yellow solid. Retention time: 2.172 min (Lux Cellulose-4. 0.46*5 cm; 3 µm;

Hex (8 mMNH₃):EtOH=60:40; 1.0 ml/min); LCMS (ESI) [M+H]⁺=461.3; ¹H NMR (400 MHz, DMSO-d₆) δ 10.76 (s, 1H), 9.43 (s, 1H), 8.51 (d, J=5.0 Hz, 1H), 8.43 (s, 1H), 8.32 (s, 1H), 7.57 (s, 1H), 7.40 (d, J=5.1 Hz, 1H), 7.32 (s, 1H), 6.93 (d, J=6.1 Hz, 1H), 6.30 (s, 2H), 4.89 (t, J=5.3 Hz, 1H), 4.10 (t, J=5.7 Hz, 2H), 3.80-3.63 (m, 2H), 2.33-2.27 (m, 1H), 2.22 (s, 3H), 2.13 (t, J=4.7 Hz, 1H), 1.67-1.54 (m, 1H), 0.97 (d, J=6.3 Hz, 3H). Compound 366: (10.2 mg, 0.022 mmol) as a yellow solid. Retention time: 3.118 min (Lux Cellulose-4. 0.46*5 cm; 3 µm; Hex (8 mMNH₃):EtOH=60: 40; 1.0 ml/min); LCMS (ESI) [M+H]⁺=461.3; ¹H NMR (400 MHz, DMSO-d₆) δ 10.71 (s, 1H), 9.42 (s, 1H), 8.51 (d, J=5.0 Hz, 1H), 8.44 (s, 1H), 8.35 (s, 1H), 7.55 (s, 1H), 7.40 (d, J=5.0 Hz, 1H), 7.27 (s, 1H), 6.95 (d, J=6.1 Hz, 1H), 6.30 (s, 2H), 4.86 (t, J=5.3 Hz, 1H), 4.06 (t, J=5.7 Hz, 2H), 3.80-3.59 (m, 2H), 2.22 (s, 3H), 2.28-2.13 (m, 2H), 1.62-1.50 (m, 1H), 1.28 (d, J=6.2 Hz, 3H). Compound 365: (25.4 mg, 0.055 mmol) as a yellow solid. Retention time: 7.392 min (Chiral IA. 0.46*15 cm; 5 µm;

MeOH (0.1% DEA):dichloromethane=80:20; 1.0 ml/min); LCMS (ESI) [M+H]⁺=461.2; ¹H NMR (400 MHz, DMSO-d₆) δ 10.76 (s, 1H), 9.43 (s, 1H), 8.53 (d, J=5.0 Hz, 1H), 8.45 (s, 1H), 8.32 (s, 1H), 7.57 (s, 1H), 7.43 (d, J=5.1 Hz, 1H), 7.32 (s, 1H), 6.93 (d, J=6.1 Hz, 1H), 6.31 (s, 2H), 4.89 (s, 1H), 4.10 (t, J=5.7 Hz, 2H), 3.71 (t, J=5.7 Hz, 2H), 2.39-2.30 (m, 1H), 2.23 (s, 3H), 2.13 (t, J=4.7 Hz, 1H), 1.67-1.54 (m, 1H), 0.97 (d, J=6.2 Hz, 3H).

Example 226

(1R,2R)—N-(8-amino-7-fluoro-6-(4-methylpyridin-3-yl)isoquinolin-3-yl)-2-(1-methyl-1H-1,2,3-triazol-4-yl)cyclopropane-1-carboxamide (Compound 356) and (1S,2S)—N-(8-amino-7-fluoro-6-(4-methylpyridin-3-yl)isoquinolin-3-yl)-2-(1-methyl-1H-1,2,3-triazol-4-yl)cyclopropane-1-carboxamide (Compound 355)

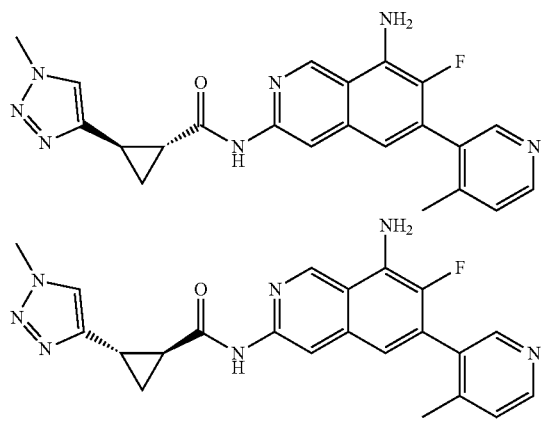

Step 1: tert-butyl(2E)-3-(1-methyl-1H-1,2,3-triazol-4-yl)prop-2-enoate

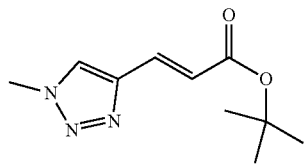

A solution of 4-bromo-1-methyl-1H-1,2,3-triazole (5 g, 30.87 mmol), tert-butyl prop-2-enoate (11.9 g, 92.85 mmol), palladium acetate (1.1 g, 4.90 mmol), tri-o-tolylphosphane (1.9 g, 6.24 mmol) and triethylamine (4.7 g, 46.45 mmol) in N,N-dimethylformamide (50 mL, 646.09 mmol) was stirred for 12 h at 110° C. The resulting mixture was cooled to room temperature and then diluted with water. The resulting solution was extracted with ethyl acetate, dried with anhydrous sodium sulfate. After filtration, the filtrate was concentrated under vacuum. The residue was purified by flash chromatography on a silica eluted with ethyl acetate/petroleum ether (3/2) to afford tert-butyl (2E)-3-(1-methyl-1H-1,2,3-triazol-4-yl)prop-2-enoate (3.6 g, 17.23 mmol) as a yellow solid. LCMS (ESI) [M+H]⁺=210.

Step 2: trans-tert-butyl-2-(1-methyl-1H-1,2,3-triazol-4-yl)cyclopropane-1-carboxylate

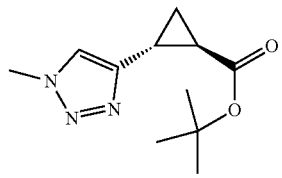 [SMILES: Cn1cc([C@@H]2C[C@H]2C(=O)OC(C)(C)C)nn1]

To a solution of trimethyl(oxo)-[6]-sulfanylium iodide (7.6 g, 34.53 mmol) and potassium tert-butoxide (3.9 g, 34.76 mmol) in dimethyl sulphoxide (80 mL) was added tert-butyl (2E)-3-(1-methyl-1H-1,2,3-triazol-4-yl)prop-2-enoate (3.6 g, 17.21 mmol) at room temperature for 12 hours. The resulting solution was diluted with water. The resulting solution was extracted with ethyl acetate, dried with anhydrous sodium sulfate. After filtration, the filtrate was concentrated under vacuum to afford trans-tert-butyl-2-(1-methyl-1H-1,2,3-triazol-4-yl)cyclopropane-1-carboxylate (1.3 g, crude) as a yellow oil. LCMS (ESI) [M+H]⁺=224.

Step 3: trans-2-(1-methyl-1H-1,2,3-triazol-4-yl)cyclopropane-1-carboxylic Acid

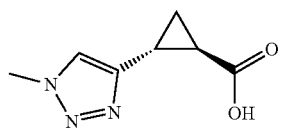

To a solution of trans-tert-butyl-2-(1-methyl-1H-1,2,3-triazol-4-yl)cyclopropane-1-carboxylate (1.3 g, 5.82 mmol)

in dichloromethane (10 mL) was added trifluoroacetic acid (2 mL, 26.93 mmol) at room temperature for 2 hours. The resulting mixture was concentrated under vacuum, the residue was purified by a reversed-phase column chromatography (0.5% NH4HCO₃ in water/CH₃CN=5%-50% in 25 min) to afford trans-2-(1-methyl-1H-1,2,3-triazol-4-yl)cyclopropane-1-carboxylic acid (223 mg, 1.34 mmol) as a yellow solid. LCMS (ESI) [M+H]⁺=168.

Step 4: trans-N-[8-chloro-7-fluoro-6-(4-methylpyridin-3-yl)isoquinolin-3-yl]-2-(1-methyl-1H-1,2,3-triazol-4-yl)cyclopropane-1-carboxamide

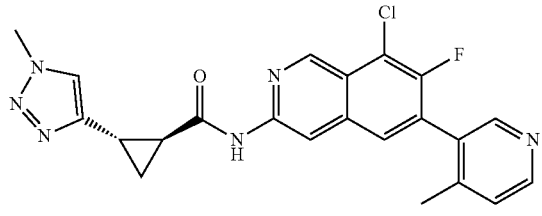 [SMILES: Cc1ccncc1-c1cc2cc(NC(=O)[C@H]3C[C@@H]3c3cn(C)nn3)ncc2c(Cl)c1F]

To a solution of trans-2-(1-methyl-1H-1,2,3-triazol-4-yl)cyclopropane-1-carboxylic acid (223 mg, 1.33 mmol), 8-chloro-7-fluoro-6-(4-methylpyridin-3-yl)isoquinolin-3-amine (320 mg, 1.11 mmol) and pyridine (0.5 mL, 6.21 mmol) in dichloromethane (5 mL, 78.65 mmol) was added phosphorus oxychloride (258 mg, 1.68 mmol) at 0° C. The resulting solution was stirred at room temperature for 30 min. The reaction was quenched by water and then extracted with dichloromethane. The organic layers was dried over with anhydrous sodium sulfate, filtered and concentrated under vacuum to afford trans-N-[8-chloro-7-fluoro-6-(4-methylpyridin-3-yl)isoquinolin-3-yl]-2-(1-methyl-1H-1,2,3-triazol-4-yl)cyclopropane-1-carboxamide (262 mg, 0.60 mmol) as a yellow solid. LCMS (ESI) [M+H]⁺=437.

Step 5: trans-tert-butyl N-(7-fluoro-3-[[2-(1-methyl-1H-1,2,3-triazol-4-yl)cyclopropane]amido]-6-(4-methylpyridin-3-yl)isoquinolin-8-yl)carbamate

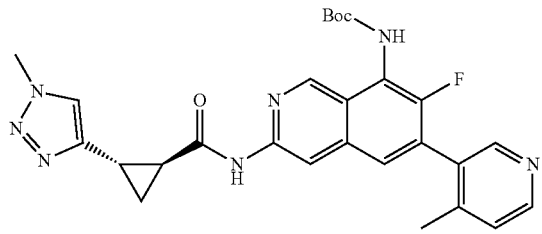 [SMILES: Cc1ccncc1-c1cc2cc(NC(=O)[C@H]3C[C@@H]3c3cn(C)nn3)ncc2c(NC(=O)OC(C)(C)C)c1F]

A mixture of trans-N-[8-chloro-7-fluoro-6-(4-methylpyridin-3-yl)isoquinolin-3-yl]-2-(1-methyl-1H-1,2,3-triazol-4-yl)cyclopropane-1-carboxamide (242 mg, 0.55 mmol), tert-butyl carbamate (1.95 g, 16.65 mmol), tris(dibenzylideneacetone)dipalladium (115 mg, 0.11 mmol), Brettphos (60 mg, 0.11 mmol) and cesium carbonate (724 mg, 2.22 mmol) in 1,4-dioxane (12 mL) was stirred at 100° C. for 2 h. After filtration, the filtrate was concentrated under vacuum.

The residue was purified by flash chromatography on silica eluted with dichloromethane/methanol (92/8) to afford trans-tert-butyl N-(7-fluoro-3-[[2-(1-methyl-1H-1,2,3-triazol-4-yl)cyclopropane]amido]-6-(4-methylpyridin-3-yl)isoquinolin-8-yl)carbamate (120 mg, 0.23 mmol) as a red solid. LCMS (ESI) [M+H]⁺=518.

Step 6: (1R,2R)—N-(8-amino-7-fluoro-6-(4-methylpyridin-3-yl)isoquinolin-3-yl)-2-(1-methyl-1H-1,2,3-triazol-4-yl)cyclopropane-1-carboxamide and (1S,2S)—N-(8-amino-7-fluoro-6-(4-methylpyridin-3-yl)isoquinolin-3-yl)-2-(1-methyl-1H-1,2,3-triazol-4-yl)cyclopropane-1-carboxamide

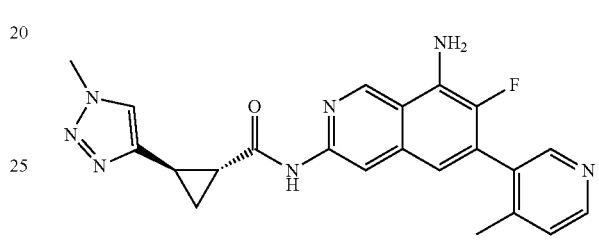

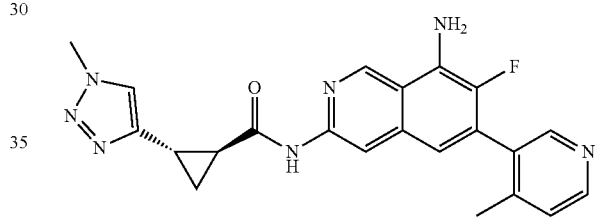

A solution of trans-tert-butyl N-(7-fluoro-3-[[2-(1-methyl-1H-1,2,3-triazol-4-yl)cyclopropane]amido]-6-(4-methylpyridin-3-yl)isoquinolin-8-yl)carbamate (100 mg, 0.19 mmol) in 1,4-dioxane (2.5 mL, 29.510 mmol) and hydrogen chloride (2.5 mL, 82.280 mmol) was stirred at room temperature for 3 h. After concentrated under vacuum the residue was purified by Prep-HPLC (XBridge Prep C18 OBD 19*150 mm*5 um; 10 mmol NH₄HCO₃ in water: CH₃CN=10%-50% in 7 min) to afford the racemic product. The racemic product was separated by Prep-Chiral-HPLC to afford two isomers (Cyclopropane stereochemistry the two isomers: triazole trans to amide, All absolute stereochemistry arbitrarily assigned): Compound 355: (8.7 mg, 0.021 mmol) as a yellow solid. Retention time; 1.977 mins ((CHIRALPAK IC2*25 cm, 5 μm; MeOH (0.1% DEA):DICHLOROMETHANE=70:30); LCMS (ESI) [M+H]⁺=418; ¹HNMR (400 MHz, DMSO-d6) δ 10.89 (s, 1H), 9.43 (s, 1H), 8.52 (d, J=5.0 Hz, 1H), 8.44 (s, 1H), 8.33 (s, 1H), 7.93 (s, 1H), 7.44-7.37 (m, 1H), 6.94 (d, J=6.1 Hz, 1H), 6.32 (s, 2H), 4.00 (s, 3H), 2.49-2.40 (m, 2H), 2.22 (s, 3H), 1.50-1.35 (m, 2H). Compound 356: (10.3 mg, 0.025 mmol) as a yellow solid. Retention time: 2.424 mins, ((CHIRALPAK IC2*25 cm, 5 μm; MeOH (0.1% DEA):DICHLOROMETHANE=70:30); LCMS (ESI) [M+H]⁺=418; ¹HNMR (400 MHz, DMSO-d6) δ 10.89 (s, 1H), 9.43 (s, 1H), 8.52 (d, J=5.0 Hz, 1H), 8.44 (s, 1H), 8.33 (s, 1H), 7.93 (s, 1H), 7.44-7.37 (m, 1H), 6.94 (d, J=6.1 Hz, 1H), 6.32 (s, 2H), 4.00 (s, 3H), 2.49-2.40 (m, 2H), 2.22 (s, 3H), 1.50-1.35 (m, 2H).

Example 227

(±)-(1S,2R,6R,7S)—N-(8-amino-7-fluoro-6-(4-methylpyridin-3-yl)isoquinolin-3-yl)-2-hydroxybicyclo[4.1.0]heptane-7-carboxamide (Compound 373 and Compound 374) and (±)-(1S,2S,6R,7S)—N-(8-amino-7-fluoro-6-(4-methylpyridin-3-yl)isoquinolin-3-yl)-2-hydroxybicyclo[4.1.0]heptane-7-carboxamide (racemic) (Compound 371 and Compound 372)

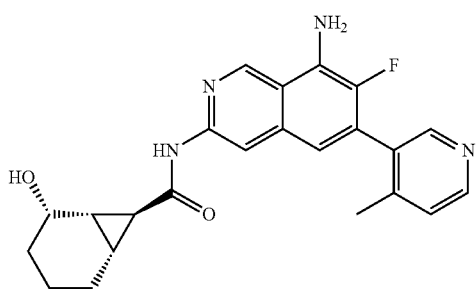

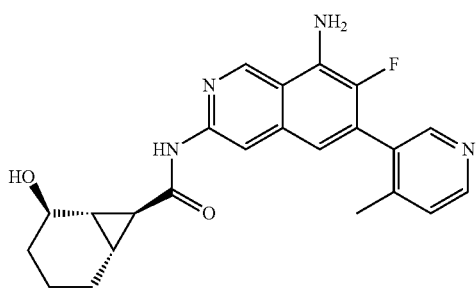

Step 1: exo-ethyl 2-oxobicyclo[4.1.0]heptane-7-carboxylate

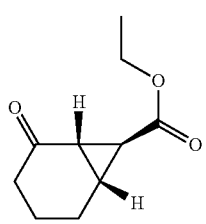

A mixture of cyclohex-2-en-1-one (4 g, 41.61 mmol), Ru$_2$(OAc)$_4$ (0.91 g, 2.05 mmol) in dichloromethane (40 mL) was added dropwised ethyl 2-(lambda4,-diazynyl)acetate (7.86 g, 68.28 mmol) at 0° C. The reaction was stirred for 2 h at 25° C. The reaction was then quenched with water, extracted with dichloromethane. The organic layers dried with anhydrous sodium sulfate. After filtration, the filtrate was concentrated under vacuum. The residue was purified by flash chromatography on silica gel eluting with ethyl acetate/petroleum ether (1:4) to afford exo-ethyl 2-oxobicyclo[4.1.0]heptane-7-carboxylate was obtained (2 g, 0.011 mol) as yellow oil. LCMS (ESI) [M+H]$^+$=183.2.

Step 2: exo-2-oxobicyclo[4.1.0]heptane-7-carboxylic Acid

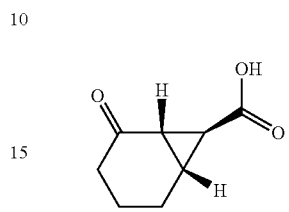

To a mixture of exo-ethyl 2-oxobicyclo[4.1.0]heptane-7-carboxylate (2 g, 10.97 mmol) in tetrahydrofuran (20 mL) was added LiOH (1.05 g, 43.84 mmol) in water (5 mL) was stirred for 3 h at 25° C. The pH value of the solution was adjusted to 5 with citric acid and then extracted with dichloromethane. The organic layers dried with anhydrous sodium sulfate. After filtration, the filtrate was concentrated under vacuum to afford exo-2-oxobicyclo[4.1.0]heptane-7-carboxylic acid (1.26 g, 74%) as a brown solid. LCMS (ESI) [M+H]$^+$=155.2.

Step 3: exo-N-(8-chloro-7-fluoro-6-(4-methylpyridin-3-yl)isoquinolin-3-yl)-2-oxobicyclo[4.1.0]heptane-7-carboxamide

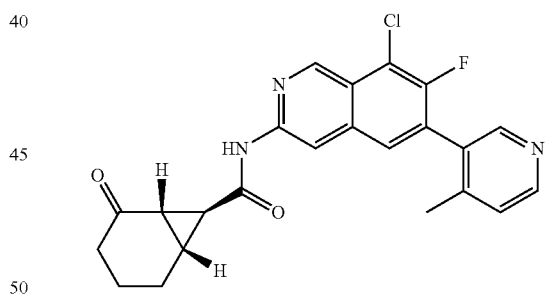

To a solution of 8-chloro-7-fluoro-6-(4-methylpyridin-3-yl)isoquinolin-3-amine (2.2 g, 7.64 mmol), exo-2-oxobicyclo[4.1.0]heptane-7-carboxylic acid (1.18 g, 7.654 mmol), pyridine (12 mL, 206.32 mmol) in dichloromethane (68 mL) was added dropwise phosphorus oxychloride (2.36 g, 15.39 mmol) at 5° C. The reaction was stirred for 30 min at 5° C. The reaction was then quenched with water, extracted with dichloromethane. The organic layers dried with anhydrous sodium sulfate. After filtration, the filtrate was concentrated under vacuum. The residue was purified by flash chromatography on silica gel eluting with dichloromethane/methanol (10/1) to afford exo-N-(8-chloro-7-fluoro-6-(4-methylpyridin-3-yl)isoquinolin-3-yl)-2-oxobicyclo[4.1.0]heptane-7-carboxamide (2.5 g, 77%) as a yellow solid. LCMS (ESI) [M+H]$^+$=424.2.

Step 4: exo-tert-butyl (7-fluoro-6-(4-methylpyridin-3-yl)-3-(2-oxobicyclo[4.1.0]heptane-7-carboxamido)isoquinolin-8-yl)carbamate

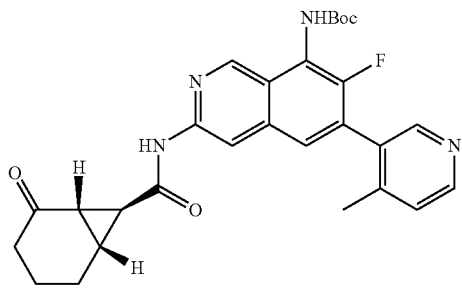 [SMILES: Cc1ccncc1-c1cc2cc(NC(=O)[C@H]3[C@@H]4CCCC(=O)[C@@H]43)ncc2c(NC(=O)OC(C)(C)C)c1F]

A mixture of exo-N-[8-chloro-7-fluoro-6-(4-methylpyridin-3-yl)isoquinolin-3-yl]-2-oxobicyclo[4.1.0]heptane-7-carboxamide (1.1 g, 2.59 mmol), tert-butyl carbamate (7.6 g, 64.87 mmol), Pd$_2$(dba)$_3$·CHCl$_3$ (540 mg, 0.52 mmol), Brettphos (560 mg, 1.04 mmol), cesium carbonate (3.4 g, 10.43 mmol) in 1,4-dioxane (40 mL) was stirred for 2 h at 90° C. The mixture was filtered and concentrated under vacuum. The residue was purified by flash chromatography on silica gel eluting with dichloromethane/methanol (10/1) to afford tert-butyl 7-fluoro-6-(4-methylpyridin-3-yl)-3-(2-oxobicyclo[4.1.0]heptane-7-carboxamido)isoquinolin-8-ylcarbamate (800 mg, 1.59 mmol) as a brown solid. LCMS (ESI) [M+H]$^+$=505.3.

Step 5: exo-tert-butyl (7-fluoro-3-(2-hydroxybicyclo[4.1.0]heptane-7-carboxamido)-6-(4-methylpyridin-3-yl)isoquinolin-8-yl)carbamate

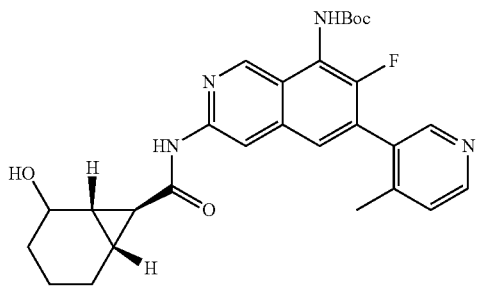 [SMILES: Cc1ccncc1-c1cc2cc(NC(=O)[C@H]3[C@@H]4CCCC(O)[C@@H]43)ncc2c(NC(=O)OC(C)(C)C)c1F]

A mixture of tert-butyl N-[7-fluoro-6-(4-methylpyridin-3-yl)-3-[(7S)-2-oxobicyclo[4.1.0]heptane-7-amido]isoquinolin-8-yl]carbamate (800 mg, 1.58 mmol) and NaBH$_4$ (362 mg, 9.56 mmol) in methanol (20 mL) was stirred for 90 min at 0° C. The reaction was then quenched by water, extracted with dichloromethane. The organic layers were dried with anhydrous sodium sulfate. After filtration, the filtrate was concentrated under vacuum. The residue was purified by flash chromatography on silica gel eluting with dichloromethane/methanol (10/1) to afford exo-tert-butyl 7-fluoro-3-(2-hydroxybicyclo[4.1.0]heptane-7-carboxamido)-6-(4-methylpyridin-3-yl)isoquinolin-8-ylcarbamate (370 mg, 46%) as a yellow solid.

Step 6: (1S,2R,6R,7S)—N-(8-amino-7-fluoro-6-(4-methylpyridin-3-yl)isoquinolin-3-yl)-2-hydroxybicyclo[4.1.0]heptane-7-carboxamide (racemic) and (1S,2S,6R,7S)—N-(8-amino-7-fluoro-6-(4-methylpyridin-3-yl)isoquinolin-3-yl)-2-hydroxybicyclo[4.1.0]heptane-7-carboxamide (Racemic)

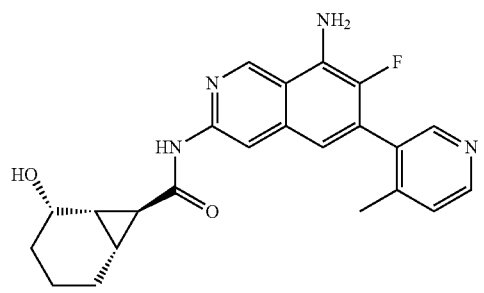

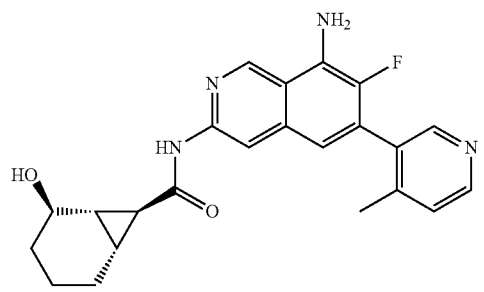

A solution of exo-tert-butyl N-[7-fluoro-3-(2-hydroxybicyclo[4.1.0]heptane-7-amido)-6-(4-methylpyridin-3-yl)isoquinolin-8-yl]carbamate (200 mg, 0.39 mmol) in N,N-dimethylformamide (1 mL) was added HCl(g)/dioxane (10 mL, 4 M). The reaction was stirred for 2 h at 20° C. The resulting mixture was concentrated under vacuum. The residue was purified by flash chromatography on silica gel eluting with dichloromethane/methanol (10/1) to afford two isomers. The mixtures were further separated on chiral HPLC to afford 4 singler stereoisomers. The relative stereochemistry is as drawn in Table 1; but the absolute stereochemistry has been assigned arbitrarily). Compound 371: Retention time; 2.74 mins ((CHIRALPAK OJ-3 4.6×50 mm; MeOH (0.1% DEA); LCMS (ESI) [M+H]$^+$=407. Compound 372: Retention time; 1.56 mins ((CHIRALPAK OJ-3 4.6×50 mm; MeOH (0.1% DEA); LCMS (ESI) [M+H]$^+$=407. Compound 373: Retention time; 1.25 mins ((Cellulose-4, 4.6×50 mm; MeOH (0.1% DEA); LCMS (ESI) [M+H]$^+$=407. Compound 374: Retention time; 3.03 mins ((Chiralcel OJ-3, 4.6×50 mm; MeOH (0.1% DEA); LCMS (ESI) [M+H]$^+$=407.

Example 228

(±)-N-(8-amino-6-(4-methylpyridin-3-yl)isoquinolin-3-yl)-2-(cyanomethyl)-3-methylcyclopropane-1-carboxamide (Compound 192) and (±)-(8-amino-6-(4-methylpyridin-3-yl)isoquinolin-3-yl)-2-(cyanomethyl)-3-methylcyclopropane-1-carboxamide (Compound 191)

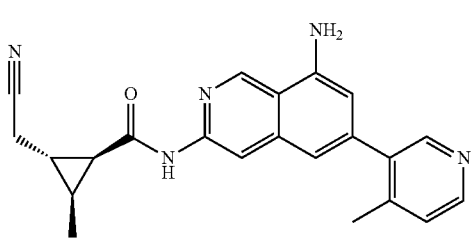

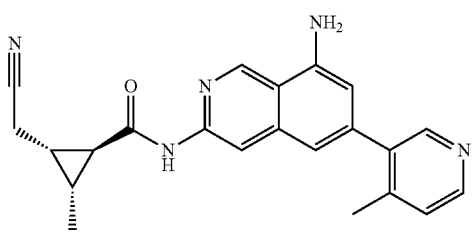

Step 1: tert-butyl N-(3-[[2-[(benzyloxy)methyl]-3-methylcyclopropane]amido]-6-(4-methylpyridin-3-yl)isoquinolin-8-yl)carbamate

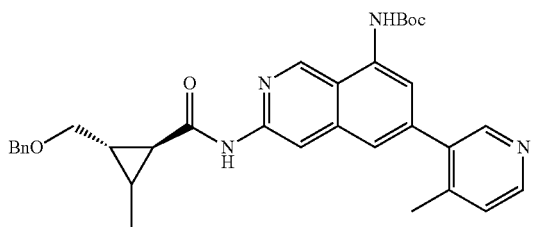 [SMILES: Cc1ccncc1-c1cc(NC(=O)OC(C)(C)C)c2cnc(NC(=O)[C@H]3C(C)[C@@H]3COCc3ccccc3)cc2c1]

A mixture of 2-[(benzyloxy)methyl]-N-[8-chloro-6-(4-methylpyridin-3-yl)isoquinolin-3-yl]-3-methylcyclopropane-1-carboxamide (420 mg, 0.89 mmol), tert-butyl carbamate (2.61 g 22.2 mmol), Pd$_2$(dba)$_3$·CHCl$_3$ (184 mg, 0.178 mmol), Brettphos (191 mg, 0.36 mmol), cesium carbonate (1.16 g, 3.566 mmol) in dioxane (10 mL, 118.041 mmol) was stirred for 1.5 h at 120° C. The resulting mixture was concentrated under vacuum. The residue was purified by flash chromatography on silica gel eluting with ethyl acetate/petroleum ether (4/1) to afford tert-butyl N-(3-[[2-[(benzyloxy)methyl]-3-methylcyclopropane]amido]-6-(4-methylpyridin-3-yl)isoquinolin-8-yl)carbamate (450 mg, 92%) as a yellow solid. LCMS (ESI) [M+H]$^+$=472.2.

Step 2: tert-butyl N-(3-[[2-(hydroxymethyl)-3-methylcyclopropane]amido]-6-(4-methylpyridin-3-yl)isoquinolin-8-yl)carbamate

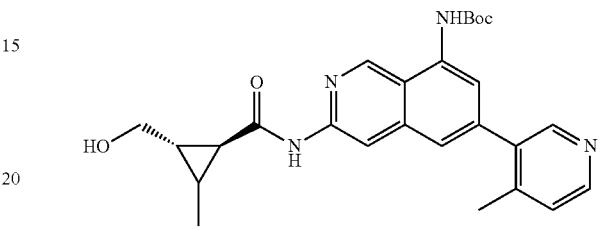

To a solution of tert-butyl N-(3-[[(1S,2S)-2-[(benzyloxy)methyl]-3-methylcyclopropane]amido]-6-(4-methylpyridin-3-yl)isoquinolin-8-yl)carbamate (350 mg, 0.63 mmol) in methanol (30 mL) was added Pd(OH)$_2$/C (2.5 g, 17.80 mmol). The resulting solution was stirred under hydrogen for 30 min at 25° C. After filtration, the resulting mixture was concentrated under vacuum to afford tert-butyl N-(3-[2-(hydroxymethyl)-3-methylcyclopropane]amido]-6-(4-methylpyridin-3-yl)isoquinolin-8-yl)carbamate (200 mg, 68%) as a light green solid. LCMS (ESI) [M+H]$^+$=463.3

Step 3: (2-((8-((tert-butoxycarbonyl)amino)-6-(4-methylpyridin-3-yl)isoquinolin-3-yl)carbamoyl)-3-methylcyclopropyl)methyl Methanesulfonate

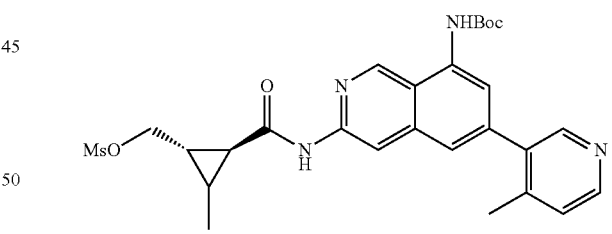

To a solution of tert-butyl N-(3-[[2-(hydroxymethyl)-3-methylcyclopropane]amido]-6-(4-methylpyridin-3-yl)isoquinolin-8-yl)carbamate (140 mg, 0.30 mmol), triethylamine (183 mg, 1.81 mmol) in dichloromethane (3 mL, 47.19 mmol) was dropwised MsCl (138 mg, 1.21 mmol). The resulting solution was stirred for 30 min at 25° C. The reaction was then quenched by water. The resulting mixture was extracted with dichloromethane dried with anhydrous sodium sulfate. After filtration, the filtrate was concentrated under vacuum to afford ((1S,2S)-2-((8-((tert-butoxycarbonyl)amino)-6-(4-methylpyridin-3-yl)isoquinolin-3-yl)carbamoyl)-3-methylcyclopropyl)methyl methanesulfonate (100 mg, 0.19 mmol) as yellow oil. LCMS (ESI) [M+H]$^+$=541.3.

Step 4: tert-butyl N-(3-[[(1S,2S)-2-(cyanomethyl)-3-methylcyclopropane]amido]-6-(4-methylpyridin-3-yl)isoquinolin-8-yl)carbamate

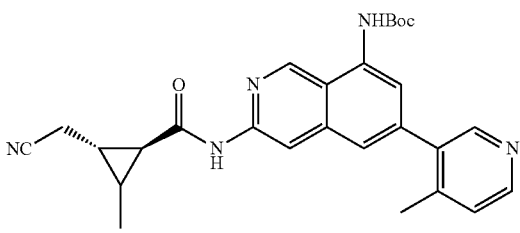 [SMILES: Cc1ccncc1-c1cc(NC(=O)OC(C)(C)C)c2cnc(NC(=O)[C@H]3C(C)[C@@H]3CC#N)cc2c1]

To a solution of tert-butyl N-(3-[[2-(methanesulfonylmethyl)-3-methylcyclopropane]amido]-6-(4-methylpyridin-3-yl)isoquinolin-8-yl)carbamate (100 mg, 0.19 mmol) in DMSO (3 mL, 42.24 mmol) was added KCN (99.29 mg, 1.53 mmol). The resulting solution was stirred for 2 h at 50° C. The resulting solution was diluted with water. The resulting solution was extracted with dichloromethane dried with anhydrous sodium sulfate. After filtration, the filtrate was concentrated under vacuum. The residue was purified by flash chromatography on silica gel eluting with dichloromethane/methanol (10/1) to afford tert-butyl N-(3-[[(1S,2S)-2-(cyanomethyl)-3-methylcyclopropane]amido]-6-(4-methylpyridin-3-yl)isoquinolin-8-yl)carbamate (70 mg, 78%) as a brown solid. LCMS (ESI) [M+H]$^+$=472.3

Step 5: (±)-(1S,2S)—N-(8-amino-6-(4-methylpyridin-3-yl)isoquinolin-3-yl)-2-(cyanomethyl)-3-methylcyclopropane-1-carboxamide and (±)-(1S,2S)—N-(8-amino-6-(4-methylpyridin-3-yl)isoquinolin-3-yl)-2-(cyanomethyl)-3-methylcyclopropane-1-carboxamide

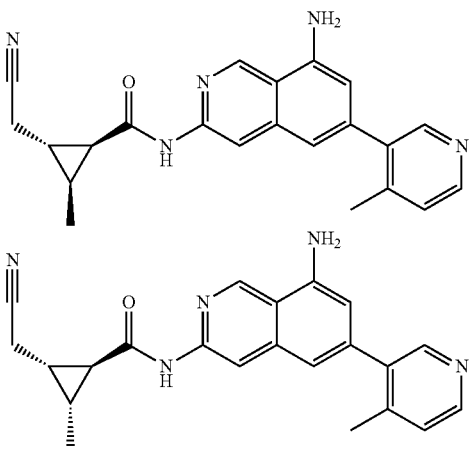

To a solution of tert-butyl N-(3-[[2-(cyanomethyl)-3-methylcyclopropane]amido]-6-(4-methylpyridin-3-yl)isoquinolin-8-yl)carbamate (70 mg, 0.15 mmol) in dichloromethane (1 mL, 15.73 mmol) and trifluoroacetic acid (1 mL) was stirred for 30 min at 25° C. The resulting solution was concentrated under vacuum. The crude product was purified by Prep-HPLC (XBridge Prep Amide OBD Column, 19×150 mm 5um; water (0.05% NH$_3$H$_2$O): ACN (20%-55% in 6 min) to afford two pairs of enantiomers (Cyclopropane stereochemistry: cyanomethyl trans to amide; All absolute stereochemistry arbitrarily assigned): Compound 191: as a yellow solid (2.8 mg, 5%). LCMS (ESI) [M+H]$^+$=372.2; $^1$HNMR (400 MHz, DMSO-d$_6$) δ 10.80 (s, 1H), 9.32 (s, 1H), 8.67-8.39 (m, 2H), 8.26 (s, 1H), 7.45 (d, J=5.1 Hz, 1H), 6.81 (s, 1H), 6.55 (d, J=1.5 Hz, 1H), 6.37 (s, 2H), 2.81 (dd, J=17.6, 7.3 Hz, 1H), 2.69 (dd, J=17.7, 7.7 Hz, 1H), 2.33 (s, 3H), 1.79 (t, J=4.5 Hz, 1H), 1.71-1.57 (m, 1H), 1.52-1.37 (m, 1H), 1.17 (d, J=6.3 Hz, 3H). Compound 192: as an off-white solid. LCMS (ESI) [M+H]$^+$=372.2; $^1$HNMR (400 MHz, DMSO) δ 10.79 (s, 1H), 9.32 (s, 1H), 8.48-8.36 (m, 2H), 8.28 (s, 1H), 7.35 (d, J=5.0 Hz, 1H), 6.92 (s, 1H), 6.55 (d, J=1.5 Hz, 1H), 6.34 (s, 2H), 2.83-2.61 (m, 2H), 2.30 (s, 3H), 2.15-2.03 (m, 1H), 1.58-1.45 (m, 1H), 1.36 (dt, J=9.1, 6.1 Hz, 1H), 1.17 (d, J=6.1 Hz, 3H).

Example 229

(±)-cis-N-(8-amino-6-(2,6-dichlorophenyl)-7-fluoroisoquinolin-3-yl)-2-fluorocyclopropane-1-carboxamide (Compound 152)

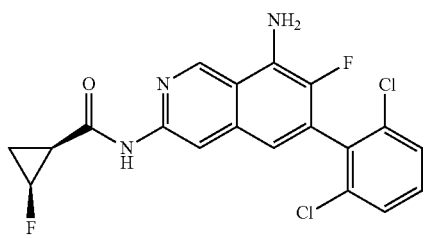 [SMILES: Nc1c(F)c(-c2c(Cl)cccc2Cl)cc2cc(NC(=O)[C@@H]3C[C@@H]3F)ncc12]

Step 1: 8-chloro-6-(2,6-dichlorophenyl)-7-fluoroisoquinolin-3-amine

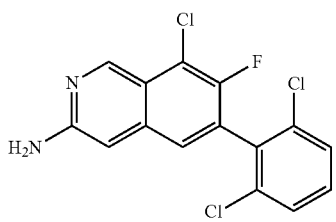 [SMILES: Nc1cc2cc(-c3c(Cl)cccc3Cl)c(F)c(Cl)c2cn1]

A mixture of 8-chloro-7-fluoro-6-iodoisoquinolin-3-amine (800 mg, 2.48 mmol), (2,6-dichlorophenyl)boronic acid (1.42 g, 7.42 mmol), bis(tri-tert-butylphosphine)palladium(0) (127 mg, 0.25 mmol) and cesium fluoride (1.13 g, 7.44 mmol) in dioxane (10 mL) and water (1 mL) was stirred at 100° C. for 12 hours. The resulting solution was concentrated under vacuum. The residue was purified by flash chromatography on silica gel eluted with ethyl acetate/petroleum ether (1/3) to afford 8-chloro-6-(2,6-dichlorophenyl)-7-fluoroisoquinolin-3-amine (820 mg, 2.412 mmol) as a white solid. LCMS (ESI) [M+H]$^+$=341.

Step 2: (±)-cis-N-[8-chloro-6-(2,6-dichlorophenyl)-7-fluoroisoquinolin-3-yl]-2-fluorocyclopropane-1-carboxamide

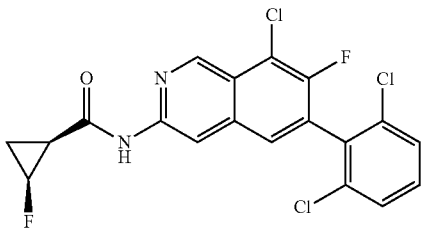 [SMILES: O=C(Nc1cc2cc(-c3c(Cl)cccc3Cl)c(F)c(Cl)c2cn1)[C@@H]1C[C@@H]1F]

To a solution of 8-chloro-6-(2,6-dichlorophenyl)-7-fluoroisoquinolin-3-amine (794 mg, 2.32 mmol), cis-2-fluorocyclopropane-1-carboxylic acid (320 mg, 3.075 mmol) and pyridine (1 mL, 12.42 mmol) in dichloromethane (10 mL) was added dropwise phosphorus oxychloride (560 mg, 3.65 mmol) at 0° C. The reaction mixture was stirred for 30 min at room temperature. The reaction was then quenched by water and then extracted with dichloromethane. The organic phase was dried over anhydrous sodium, filtered and concentrated under vacuum. The residue was purified by flash chromatography on silica eluted with ethyl acetate/petroleum ether (1:1) to afford cis-N-[8-chloro-6-(2,6-dichlorophenyl)-7-fluoroisoquinolin-3-yl]-2-fluorocyclopropane-1-carboxamide (763 mg, 1.79 mmol) as a yellow solid. LCMS (ESI) [M+H]$^+$=427.

Step 3: (±)-trans-tert-butyl (6-(2,6-dichlorophenyl)-7-fluoro-3-(2-fluorocyclopropane-1-carboxamido)isoquinolin-8-yl)carbamate

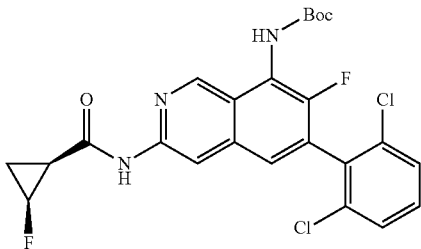 [SMILES: CC(C)(C)OC(=O)Nc1c(F)c(-c2c(Cl)cccc2Cl)cc2cc(NC(=O)[C@@H]3C[C@@H]3F)ncc12]

A solution of cis-N-[8-chloro-6-(2,6-dichlorophenyl)-7-fluoroisoquinolin-3-yl]-2-fluorocyclopropane-1-carboxamide (300 mg, 0.70 mmol), tert-butyl carbamate (2.5 g, 21.34 mmol), tris(dibenzylideneacetone)dipalladium (150 mg, 0.15 mmol), BrettPhos (75 mg, 0.14 mmol), and cesium carbonate (930 mg, 2.85 mmol) in 1,4-dioxane (15 mL) was stirred for 2 h at 90° C. The resulting mixture was cooled to room temperature and then filtered. The filtrate was concentrated under vacuum. The residue was purified by flash chromatography on silica eluted with ethyl acetate/petroleum ether (3/2) to afford cis-tert-butyl (6-(2,6-dichlorophenyl)-7-fluoro-3-(2-fluorocyclopropane-1-carboxamido)isoquinolin-8-yl)carbamate (190 mg, 0.375 mmol) as a yellow solid. LCMS (ESI) [M+H]$^+$=508.

Step 4: (±)-cis-N-[8-amino-6-(2,6-dichlorophenyl)-7-fluoroisoquinolin-3-yl]-2-fluorocyclopropane-1-carboxamide

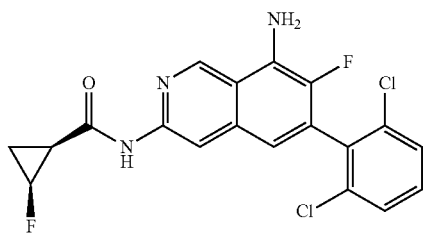 [SMILES: Nc1c(F)c(-c2c(Cl)cccc2Cl)cc2cc(NC(=O)[C@@H]3C[C@@H]3F)ncc12]

To a solution of cis-tert-butyl N-[6-(2,6-dichlorophenyl)-7-fluoro-3-[[2-fluorocyclopropane]amido]isoquinolin-8-yl]carbamate (170 mg, 0.33 mmol) and trifluoroacetic acid (1.6 mL, 21.541 mmol) in dichloromethane (8 mL) was stirred for 1 h at 25° C. The resulting mixture was concentrated under vacuum. The residue was purified by Prep-HPLC (Atlantis HILIC OBD, 19×150 mm 5 um; water (0.1% FA): CH$_3$CN (5%-23%) in 7 min) to afford (1)-cis-N-[8-amino-6-(2,6-dichlorophenyl)-7-fluoroisoquinolin-3-yl]-2-fluorocyclopropane-1-carboxamide (21.6 mg, 0.053 mmol) as a yellow solid. LCMS (ESI) [M+H]$^+$=408; $^1$HNMR (400 MHz, DMSO-d6) δ 10.86 (s, 1H), 9.44 (s, 1H), 8.30 (s, 1H), 7.65 (d, J=8.1 Hz, 2H), 7.54-7.49 (m, 1H), 6.93 (d, J=5.9 Hz, 1H), 6.32 (s, 2H), 5.04-4.83 (m, 1H), 2.31-2.19 (m, 1H), 1.68-1.66 (m, 1H), 1.19-1.17 (m, 1H).

Example 230

2-((6-(1-acetyl-1,2,3,6-tetrahydropyridin-4-yl)-8-amino-7-fluoroisoquinolin-3-yl)amino)-6-isopropyl-5,6-dihydro-4H-pyrazolo[1,5-d][1,4]diazepin-7(8H)-one (Compound 232)

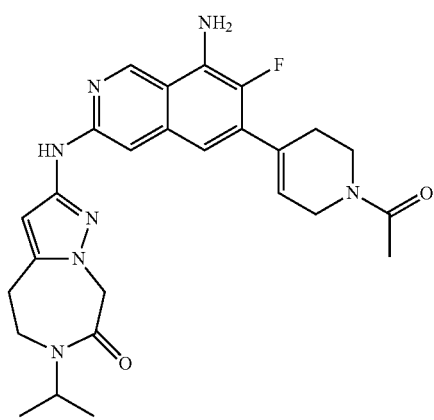 [SMILES: CC(=O)N1CC=C(c2cc3cc(Nc4cc5n(n4)CC(=O)N(C(C)C)CC5)ncc3c(N)c2F)CC1]

Step 1: 1-[4-(3-amino-7-chloro-6-isoquinolyl)-3,6-dihydro-2H-pyridin-1-yl]ethanone

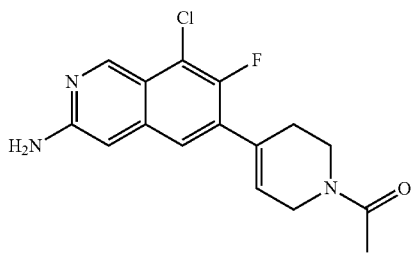 [SMILES: CC(=O)N1CC=C(c2cc3cc(N)ncc3c(Cl)c2F)CC1]

To a solution of 6-bromo-7-chloro-isoquinolin-3-amine (200 mg, 0.78 mmol) in 1,4-dioxane (2 mL) was added 1-[4-(4,4,5,5-tetramethyl-1,3,2-dioxaborolan-2-yl)-3,6-dihydro-2H-pyridin-1-yl]ethanone (234.1 mg, 0.93 mmol), potassium carbonate (321.5 mg, 2.33 mmol) and [1,1'-bis(diphenylphosphino)ferrocene]dichloropalladium(II) (56.85 mg, 0.08 mmol). The resulting suspension was stirred at 90° C. for 2 hours. After filtration, the filtrate was concentrated under vacuum. The residue was purified by flash chromatography on silica gel eluting with dichloromethane/methanol (10/1) to afford 1-[4-(3-amino-7-chloro-6-isoquinolyl)-3,6-dihydro-2H-pyridin-1-yl]ethanone (210 mg, 0.69 mmol) as a yellow solid. LCMS (ESI) [M+H]$^+$=319.0.

Step 2: 2-[[6-(1-acetyl-3,6-dihydro-2H-pyridin-4-yl)-8-chloro-7-fluoro-3-isoquinolyl]amino]-6-isopropyl-5,8-dihydro-4H-pyrazolo[1,5-d][1,4]diazepin-7-one

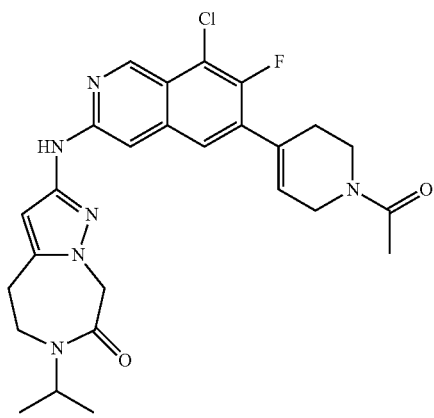 [SMILES: CC(=O)N1CC=C(c2cc3cc(Nc4cc5n(n4)CC(=O)N(C(C)C)CC5)ncc3c(Cl)c2F)CC1]

A mixture of 1-[4-(3-amino-8-chloro-7-fluoro-6-isoquinolyl)-3,6-dihydro-2H-pyridin-1-yl]ethanone (200 mg, 0.66 mmol), 2-bromo-6-isopropyl-5,8-dihydro-4H-pyrazolo[1,5-d][1,4]diazepin-7-one (265 mg, 0.99 mmol), t-BuBrettphos G3 (171 mg, 0.20 mmol), t-BuBrettphos (195 mg, 0.40 mmol), cesium carbonate (645 mg, 1.98 mmol) in 1,4-dioxane (20 mL) was stirred at 100° C. for 8 hours. The suspension was filtered through a pad of Celite. The mixture was concentrated under vacuum. The residue was purified by flash chromatography on silica gel eluting with dichloromethane/methanol (10/1) to afford 2-[[6-(1-acetyl-3,6-dihydro-2H-pyridin-4-yl)-8-chloro-7-fluoro-3-isoquinolyl]amino]-6-isopropyl-5,8-dihydro-4H-pyrazolo[1,5-d][1,4]diazepin-7-one (110 mg, 0.019 mmol) as a yellow solid. LCMS (ESI) [M+H]$^+$=510.

Step 3: 2-[[6-(1-acetyl-3,6-dihydro-2H-pyridin-4-yl)-8-chloro-7-fluoro-3-isoquinolyl]amino]-6-isopropyl-5,8-dihydro-4H-pyrazolo[1,5-d][1,4]diazepin-7-one

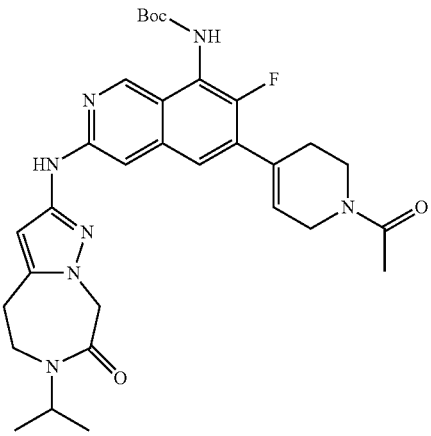 [SMILES: CC(=O)N1CC=C(c2cc3cc(Nc4cc5n(n4)CC(=O)N(C(C)C)CC5)ncc3c(NC(=O)OC(C)(C)C)c2F)CC1]

A mixture of 2-[[6-(1-acetyl-3,6-dihydro-2H-pyridin-4-yl)-8-chloro-7-fluoro-3-isoquinolyl]amino]-6-isopropyl-5,8-dihydro-4H-pyrazolo[1,5-d][1,4]diazepin-7-one (100 mg, 0.20 mmol) and tert-butyl carbamate (340 mg, 2.93 mmol), tris(dibenzylideneacetone)dipalladium-chloroform adduct (30 mg, 0.04 mmol), Brettphos (40.0 mg, 0.07 mmol), cesium carbonate (180 mg, 0.55 mmol) in 1,4-dioxane (10 mL) was stirred at 90° C. for 1 hours. After filtration, the filtrate was concentrated under vacuum. The residue was purified by flash chromatography on silica gel eluting with dichloromethane/methanol (10/1) to afford 2-[[6-(1-acetyl-3,6-dihydro-2H-pyridin-4-yl)-8-chloro-7-fluoro-3-isoquinolyl]amino]-6-isopropyl-5,8-dihydro-4H-pyrazolo[1,5-d][1,4]diazepin-7-one (100 mg, 0.20 mmol) as a yellow solid. LCMS (ESI) [M+H]$^+$=591.

Step 4: 2-[[6-(1-acetyl-3,6-dihydro-2H-pyridin-4-yl)-8-amino-7-fluoro-3-isoquinolyl]amino]-6-isopropyl-5,8-dihydro-4H-pyrazolo[1,5-d][1,4]diazepin-7-one

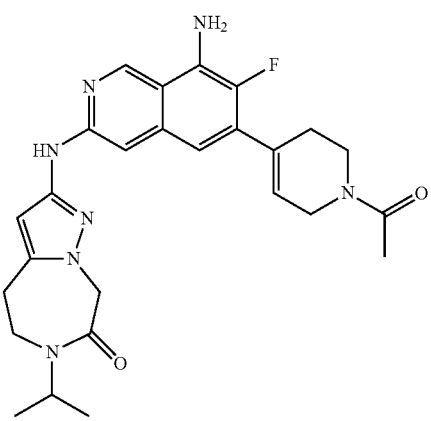 [SMILES: CC(=O)N1CC=C(c2cc3cc(Nc4cc5n(n4)CC(=O)N(C(C)C)CC5)ncc3c(N)c2F)CC1]

A solution of tert-butyl N-[6-(1-acetyl-3,6-dihydro-2H-pyridin-4-yl)-7-fluoro-3-[(6-isopropyl-7-oxo-5,8-dihydro-4H-pyrazolo[1,5-d][1,4]diazepin-2-yl)amino]-8-isoquinolyl]carbamate (105 mg, 0.18 mmol) in TFA (1 mL, 0.18 mmol) in dichloromethane (5 mL) was stirred at 15° C. for 2 hours. The resulting solution was concentrated under vacuum. The residue was purified by Prep-HPLC to provide 2-[[6-(1-acetyl-3,6-dihydro-2H-pyridin-4-yl)-8-amino-7-fluoro-3-isoquinolyl]amino]-6-isopropyl-5,8-dihydro-4H-pyrazolo[1,5-d][1,4]diazepin-7-one (27.8 mg, 0.057 mmol) as a yellow solid. LCMS (ESI) [M+H]$^+$=492.2; $^1$HNMR (400 MHz, DMSO-d$_6$) δ 9.16 (s, 1H), 9.02 (s, 1H), 7.68 (s, 1H), 6.79-6.76 (m, 1H), 6.09 (s, 1H), 5.94 (s, 3H), 4.97 (s, 2H), 4.64-4.55 (m, 1H), 4.17-4.10 (m, 2H), 3.80-3.78 (m, 2H), 3.66-3.61 (m, 2H), 3.00-2.96 (m, 2H), 2.56 (s, 1H), 2.51-2.50 (m, 1H), 2.07 (d, J=9.2 Hz, 3H), 1.12 (d, J=9.2 Hz, 6H).

Example 231

2-((8-amino-6-(3-amino-1,4-dimethyl-1H-pyrazol-5-yl)-7-fluoroisoquinolin-3-yl)amino)-6-isopropyl-5,6-dihydro-4H-pyrazolo[1,5-d][1,4]diazepin-7(8H)-one (Compound 251)

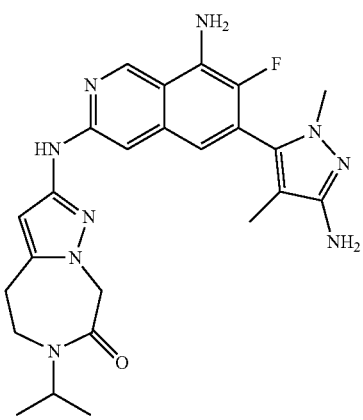 [SMILES: Cc1c(N)nn(C)c1-c1cc2cc(Nc3cc4n(n3)CC(=O)N(C(C)C)CC4)ncc2c(N)c1F]

Step 1: 1,4-dimethyl-3-nitro-pyrazole

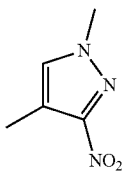

A solution of 4-methyl-3-nitro-1H-pyrazole (500 mg, 3.93 mmol), iodomethane (837.9 mg, 5.9 mmol) and potassium tert-butoxide (484.6 mg, 4.33 mmol) in tetrahydrofuran (20 mL) was stirred at 25° C. for 1 hour. The solvent was concentrated under vacuum. The residue was purified by flash chromatography on silica gel eluting with dichloromethane/methanol (10/1) to afford 1,4-dimethyl-3-nitro-pyrazole (450 mg, 3.18 mmol) as a white solid. LCMS (ESI) [M+H]+=142.

Step 2: 1,4-dimethylpyrazol-3-amine

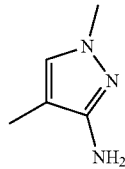

A solution of 1,4-dimethyl-3-nitro-pyrazole (530 mg, 3.76 mmol) and palladium carbon (10%) (50 mg, 3.76 mmol) in methanol (20 mL) was stirred at 20° C. for 1 hour. After filtration, the filtrate was concentrated under reduced pressure to afford 1,4-dimethylpyrazol-3-amine (400 mg, 3.59 mmol) as light yellow oil. LCMS (ESI) [M+H]$^+$=112.

Step 3: 3-(2,5-dimethylpyrrol-1-yl)-1,4-dimethyl-pyrazole

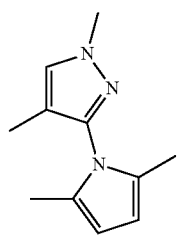

A solution of 1,4-dimethylpyrazol-3-amine (1.53 g, 13.77 mmol), 2,5-hexanedione (3.14 g, 27.53 mmol) and p-toluenesulfonic acid (0.24 g, 1.38 mmol) in toluene (60 mL) was stirred at 110° C. for 3 hours. The solvent was concentrated under vacuum. The residue was purified by flash chromatography on silica gel eluting with petroleum ether/ethyl acetate (80/20) to afford 3-(2,5-dimethylpyrrol-1-yl)-1,4-dimethyl-pyrazole (1.5 g, 7.92 mmol) as a gray solid. LCMS (ESI) [M+H]$^+$=190.

Step 4: 3-(2,5-dimethylpyrrol-1-yl)-5-iodo-1,4-dimethyl-pyrazole

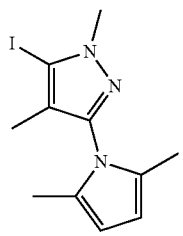

A solution of 3-(2,5-dimethylpyrrol-1-yl)-1,4-dimethyl-pyrazole (500 mg, 2.64 mmol) in tetrahydrofuran (20 mL) was added n-Butyllithium (1.27 mL, 3.17 mmol) at −78° C. The resulting solution was stirred for 1 hour at −78° C. Then iodine (671.03 mg, 2.64 mmol) was added and stirred at −78° C. for 10 minutes. The mixture was stirred at room temperature for 1 hour. The reaction was quenched with saturated sodium thiosulfate aqueous. The resulting solution was extracted with ethyl acetate, dried with anhydrous sodium sulfate. After filtration, the filtrate was concentrated under vacuum. The residue was purified by flash chromatography on silica gel eluting with petroleum ether/ethyl acetate (3/1) to afford 3-(2,5-dimethylpyrrol-1-yl)-5-iodo-1,4-dimethyl-pyrazole (385 mg, 1.22 mmol) as a light yellow oil. LCMS (ESI) [M+H]$^+$=316.

Step 5: 5-iodo-1,4-dimethyl-pyrazol-3-amine

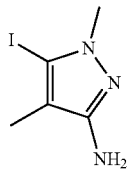

A solution of 3-(2,5-dimethylpyrrol-1-yl)-5-iodo-1,4-dimethyl-pyrazole (500 mg, 1.59 mmol), potassium hydroxide (444.23 mg, 7.93 mmol), hydroxylamine hydrochloride (1.09 g, 15.87 mmol) in ethanol (20 mL) and water (20 mL) was stirred at 90° C. for 12 hours. The solvent was concentrated under vacuum. The residue was purified by flash chromatography on silica gel eluting with dichloromethane/methanol (96/4) to afford 5-iodo-1,4-dimethyl-pyrazol-3-amine (281 mg, 1.18 mmol) as a white solid. LCMS (ESI) [M+H]$^+$=238.

Step 6: tert-butyl N-[6-(5-amino-2,4-dimethyl-pyrazol-3-yl)-7-fluoro-3-[(6-isopropyl-7-oxo-5,8-dihydro-4H-pyrazolo[1,5-d][1,4]diazepin-2-yl)amino]-8-isoquinolyl]carbamate

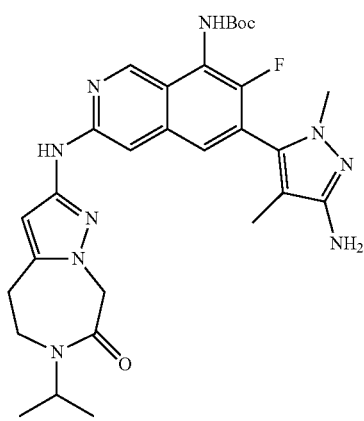 [SMILES: Cc1c(N)nn(C)c1-c1cc2cc(Nc3cc4n(n3)CC(=O)N(C(C)C)CC4)ncc2c(NC(=O)OC(C)(C)C)c1F]

A solution of 5-iodo-1,4-dimethyl-pyrazol-3-amine (31.0 mg, 0.13 mmol), [8-(tert-butoxycarbonylamino)-7-fluoro-3-[(6-isopropyl-7-oxo-5,8-dihydro-4H-pyrazolo[1,5-d][1,4]diazepin-2-yl)amino]-6-isoquinolyl]boronic acid (67 mg, 0.13 mmol), terakis(triphenylphosphine)palladium (27.59 mg, 0.03 mmol) and potassium carbonate (54.14 mg, 0.39 mmol) in 1,4-dioxane (3 mL) and water (0.3 mL) was stirred at 90° C. for 1 hour. The solvent was concentrated under vacuum to afford tert-butyl N-[6-(5-amino-2,4-dimethyl-pyrazol-3-yl)-7-fluoro-3-[(6-isopropyl-7-oxo-5,8-dihydro-4H-pyrazolo[1,5-d][1,4]diazepin-2-yl)amino]-8-isoquinolyl]carbamate (50 mg, crude) as a brown solid. LCMS (ESI) [M+H]$^+$=578.

Step 7: 2-[[8-amino-6-(5-amino-2,4-dimethyl-pyrazol-3-yl)-7-fluoro-3-isoquinolyl]amino]-6-isopropyl-5,8-dihydro-4H-pyrazolo[1,5-d][1,4]diazepin-7-one

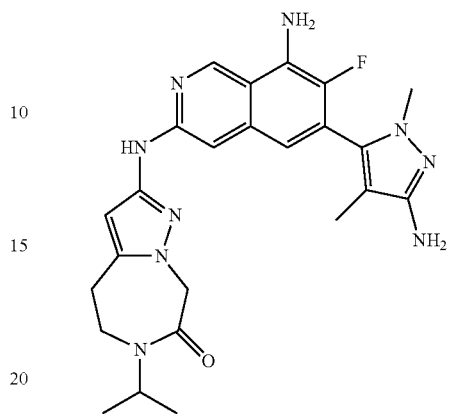

A solution of tert-butyl N-[6-(5-amino-2,4-dimethyl-pyrazol-3-yl)-7-fluoro-3-[(6-isopropyl-7-oxo-5,8-dihydro-4H-pyrazolo[1,5-d][1,4]diazepin-2-yl)amino]-8-isoquinolyl]carbamate (50.0 mg, 0.09 mmol) and 2,2,2-trifluoroacetic acid (1.0 mL) in dichloromethane (4 mL) was stirred at 25° C. for 1 hour. The resulting solution was concentrated under vacuum. The crude product was purified by Prep-HPLC [Atlantis HILIC OBD Column19×150 nm×50 um; water (10 mmol/L sodium bicarbonate and ACN (20%-50%) in 7 min] to afford 2-[[8-amino-6-(5-amino-2,4-dimethyl-pyrazol-3-yl)-7-fluoro-3-isoquinolyl]amino]-6-isopropyl-5,8-dihydro-4H-pyrazolo[1,5-d][1,4]diazepin-7-one (9.1 mg, 0.019 mmol) as a yellow solid. LCMS (ESI) [M+H]$^+$=478; $^1$HNMR (400 MHz, DMSO-d$_6$) δ 9.26 (s, 1H), 9.09 (s, 1H), 7.69 (s, 1H), 6.75 (d, J=6.0 Hz, 1H), 6.13 (s, 2H), 5.98 (s, 1H), 4.98 (s, 2H), 4.65-4.55 (m, 1H), 4.48 (s, 2H), 3.78 (t, J=6.0 Hz, 2H), 3.45 (s, 3H), 2.98 (t, J=6.0 Hz, 2H), 1.77 (s, 3H), 1.12 (d, J=6.0 Hz, 6H).

Example 232

(1S,2S,3R)—N-(8-amino-7-fluoro-6-(4-methylpyridin-3-yl)isoquinolin-3-yl)-2-(cyanomethyl)-3-methylcyclopropane-1-carboxamide (Compound 383),
(1R,2R,3S)—N-(8-amino-7-fluoro-6-(4-methylpyridin-3-yl)isoquinolin-3-yl)-2-(cyanomethyl)-3-methylcyclopropane-1-carboxamide (Compound 384),
(1S,2S,3S)—N-(8-amino-7-fluoro-6-(4-methylpyridin-3-yl)isoquinolin-3-yl)-2-(cyanomethyl)-3-methylcyclopropane-1-carboxamide (Compound 385),
(1R,2R,3R)—N-(8-amino-7-fluoro-6-(4-methylpyridin-3-yl)isoquinolin-3-yl)-2-(cyanomethyl)-3-methylcyclopropane-1-carboxamide (Compound 386)

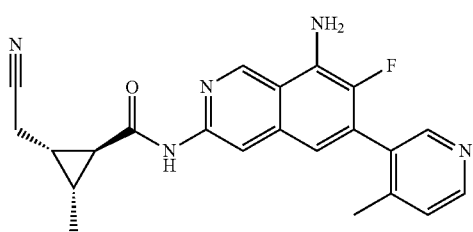

-continued

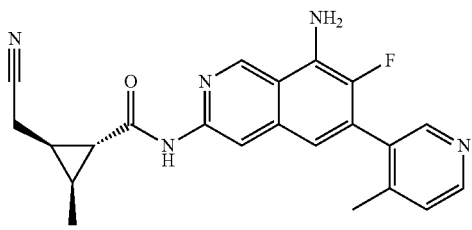

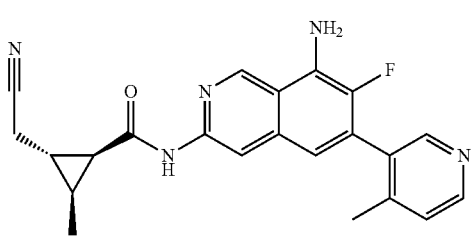

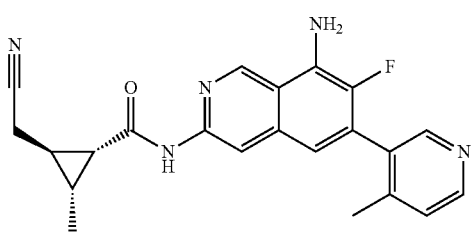

Step 1: 2-[(benzyloxy)methyl]-N-[8-chloro-7-fluoro-6-(4-methylpyridin-3-yl)isoquinolin-3-yl]-3-methylcyclopropane-1-carboxamide

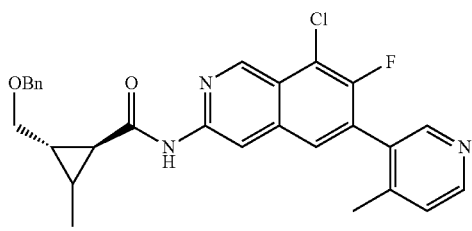 [SMILES: Cc1ccncc1-c1cc2cc(NC(=O)[C@H]3C(C)[C@@H]3COCc3ccccc3)ncc2c(Cl)c1F]

A solution of 8-chloro-7-fluoro-6-(4-methylpyridin-3-yl)isoquinolin-3-amine (1 g, 3.48 mmol), (1S,2S)-2-[(benzyloxy)methyl]-3-methylcyclopropane-1-carboxylic acid (1.15 g, 5.22 mmol), pyridine (2 mL, 24.847 mmol) in dichloromethane (20 mL) was added phosphorus oxychloride (1.06 g, 6.90 mmol) at 0° C. The resulting solution was stirred for 30 min at 0° C. and then quenched by water. The resulting solution was extracted with dichloromethane, dried with anhydrous sodium sulfate. After filtration, the filtrate was concentrated under vacuum. The residue was purified by flash chromatography on silica gel eluting with ethyl acetate/petroleum ether (10/1) to afford (1S,2S)-2-[(benzyloxy)methyl]-N-[8-chloro-7-fluoro-6-(4-methylpyridin-3-yl)isoquinolin-3-yl]-3-methylcyclopropane-1-carboxamide (0.9 g, 53%) as a yellow solid.

Step 2: tert-butyl N-(3-[[(2-[(benzyloxy)methyl]-3-methylcyclopropane]amido]-7-fluoro-6-(4-methylpyridin-3-yl)isoquinolin-8-yl)carbamate

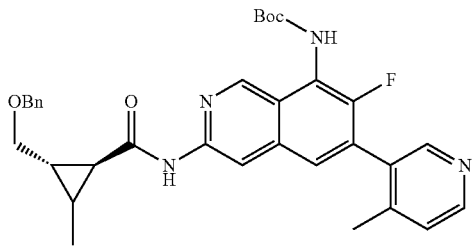 [SMILES: Cc1ccncc1-c1cc2cc(NC(=O)[C@H]3C(C)[C@@H]3COCc3ccccc3)ncc2c(NC(=O)OC(C)(C)C)c1F]

To a solution of 2-[(benzyloxy)methyl]-N-[8-chloro-7-fluoro-6-(4-methylpyridin-3-yl)isoquinolin-3-yl]-3-methyl-cyclopropane-1-carboxamide (900 mg, 1.84 mmol), tert-butyl N-methylcarbamate (4.3 g, 32.78 mmol), $Pd_2(dba)_3 \cdot CHCl_3$ (380 mg, 0.37 mmol), BrettPhos (395 mg, 0.74 mmol), cesium carbonate (2.4 g, 7.37 mmol) in 1,4-dioxane (30 mL) was stirred for 5 h at 100° C. The solids were filtered out. The resulting mixture was concentrated under vacuum. The residue was purified by flash chromatography on silica gel eluting with ethyl acetate/petroleum ether (10/1) to afford tert-butyl N-(3-[[2-[(benzyloxy)methyl]-3-methylcyclopropane]amido]-7-fluoro-6-(4-methylpyridin-3-yl)isoquinolin-8-yl)carbamate (500 mg, 48%) as a yellow solid. LCMS (ESI) $[M+H]^+=571$.

Step 3: tert-butyl N-(7-fluoro-3-[[2-(hydroxymethyl)-3-methylcyclopropane]amido]-6-(4-methylpyridin-3-yl)isoquinolin-8-yl)carbamate

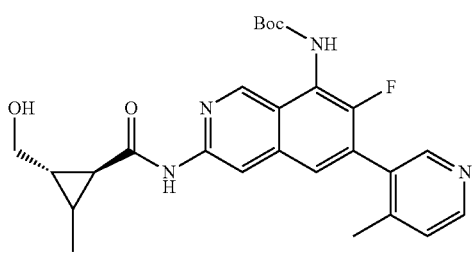 [SMILES: Cc1ccncc1-c1cc2cc(NC(=O)[C@H]3C(C)[C@@H]3CO)ncc2c(NC(=O)OC(C)(C)C)c1F]

To a solution of tert-butyl N-(3-[[2-[(benzyloxy)methyl]-3-methylcyclopropane]amido]-7-fluoro-6-(4-methylpyridin-3-yl)isoquinolin-8-yl)carbamate (500 mg, 0.88 mmol) in methanol (20 mL) was added $Pd(OH)_2/C$ (100 mg). The resulting solution was stirred for 12 h at room temperature under $H_2$ (1 atm). The reaction was filtered and concentrated under vacuum to afford tert-butyl N-(7-fluoro-3-[[2-(hydroxymethyl)-3-methylcyclopropane]amido]-6-(4-methylpyridin-3-yl)isoquinolin-8-yl)carbamate (220 mg, 52%) as a white solid. LCMS (ESI) $[M+H]^+=481$.

Step 4: tert-butyl N-(7-fluoro-3-[[2-[(methanesulfonyloxy)methyl]-3-methylcyclopropane]amido]-6-(4-methylpyridin-3-yl)isoquinolin-8-yl)carbamate

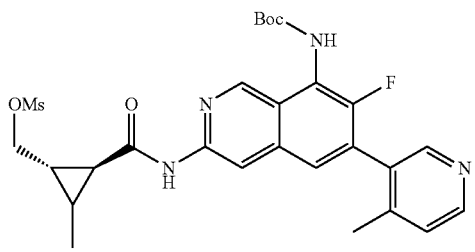 [SMILES: Cc1ccncc1-c1cc2cc(NC(=O)[C@H]3C(C)[C@@H]3COS(C)(=O)=O)ncc2c(NC(=O)OC(C)(C)C)c1F]

To a solution of tert-butyl N-(7-fluoro-3-[[(1S,2S)-2-(hydroxymethyl)-3-methylcyclopropane]amido]-6-(4-methylpyridin-3-yl)isoquinolin-8-yl)carbamate (200 mg, 0.42 mmol) in dichloromethane (10 mL) was added triethylamine (70 mg, 0.69 mmol) and methanesulfonyl chloride (60 mg, 0.52 mmol) at 0° C. The resulting solution was stirred for 15 min at room temperature and then concentrated under vacuum to afford tert-butyl N-(7-fluoro-3-[[2-[(methanesulfonyloxy)methyl]-3-methylcyclopropane]amido]-6-(4-methylpyridin-3-yl)isoquinolin-8-yl)carbamate (200 mg, crude) as a white solid. LCMS (ESI) [M+H]⁺=559.

Step 5: tert-butyl N-(3-[[2-(cyanomethyl)-3-methylcyclopropane]amido]-7-fluoro-6-(4-methylpyridin-3-yl)isoquinolin-8-yl)carbamate

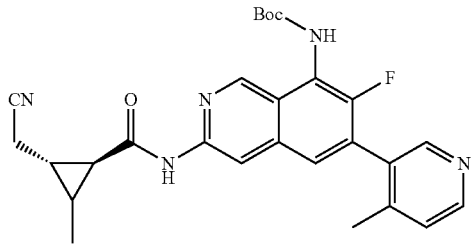 [SMILES: Cc1ccncc1-c1cc2cc(NC(=O)[C@H]3C(C)[C@@H]3CC#N)ncc2c(NC(=O)OC(C)(C)C)c1F]

To a solution of tert-butyl N-(7-fluoro-3-[[2-[(methanesulfonyloxy)methyl]-3-methylcyclopropane]amido]-6-(4-methylpyridin-3-yl)isoquinolin-8-yl)carbamate (200 mg, 0.36 mmol) in dimethyl sulphoxide (10 mL) was added potassium cyanide (46 mg, 0.71 mmol). The resulting solution was stirred for 3 h at 60° C. The resulting solution was diluted with water and then extracted with ethyl acetate. The organic layers dried with anhydrous sodium sulfate. After filtration, the filtrate was concentrated under vacuum to afford tert-butyl N-(3-[[2-(cyanomethyl)-3-methylcyclopropane]amido]-7-fluoro-6-(4-methylpyridin-3-yl)isoquinolin-8-yl)carbamate (210 mg, crude) as a white solid. LCMS (ESI) [M+H]⁺=490.

Step 6: (1S,2S,3R)—N-(8-amino-7-fluoro-6-(4-methylpyridin-3-yl)isoquinolin-3-yl)-2-(cyanomethyl)-3-methylcyclopropane-1-carboxamide, (1R,2R,3S)—N-(8-amino-7-fluoro-6-(4-methylpyridin-3-yl)isoquinolin-3-yl)-2-(cyanomethyl)-3-methylcyclopropane-1-carboxamide, (1S,2S,3S)—N-(8-amino-7-fluoro-6-(4-methylpyridin-3-yl)isoquinolin-3-yl)-2-(cyanomethyl)-3-methylcyclopropane-1-carboxamide, (1R,2R,3R)—N-(8-amino-7-fluoro-6-(4-methylpyridin-3-yl)isoquinolin-3-yl)-2-(cyanomethyl)-3-methylcyclopropane-1-carboxamide

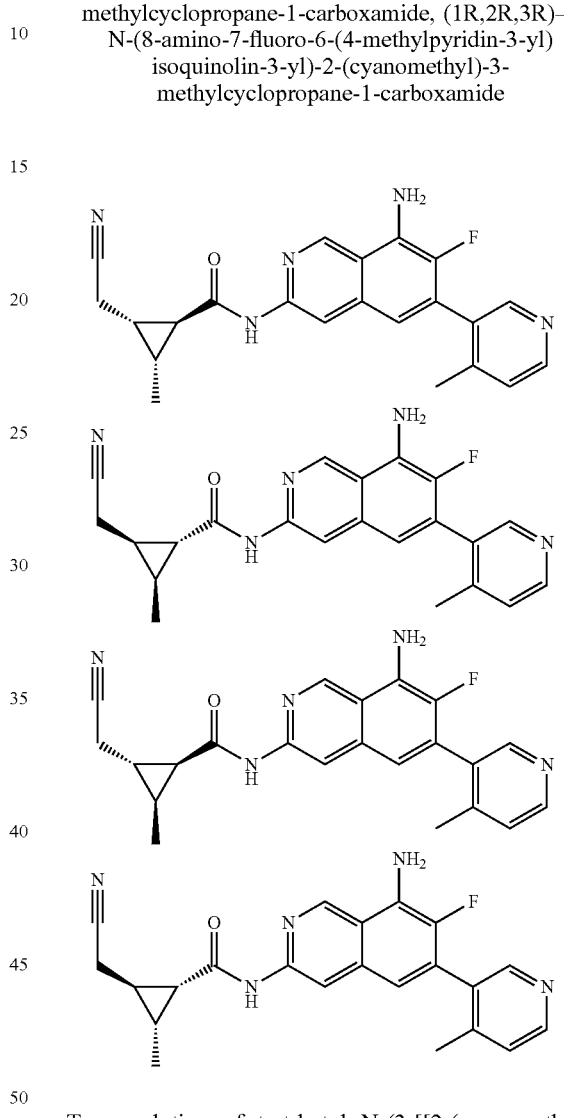

To a solution of tert-butyl N-(3-[[2-(cyanomethyl)-3-methylcyclopropane]amido]-7-fluoro-6-(4-methylpyridin-3-yl)isoquinolin-8-yl)carbamate (100 mg, 0.20 mmol) and TFA (3 ml) in 1,4-dioxane (5 mL) was stirred for 2 h at room temperature. The resulting mixture was concentrated under vacuum. The residue was purified by Prep-HPLC (XBridge Shield RP18 OBD Column, 5 m, 19*150 mm; Water (0.05% NH₃H₂O) and ACN (15% ACN up to 40% in 15 min)) to afford the mixture. The mixture was isolated by SFC to afford four isomers (Cyclopropane stereochemistry: cyanomethyl trans to amide; methyl relative stereochemistry arbitrarily assigned; All absolute stereochemistry arbitrarily assigned): Compound 383: (2.4 mg, 3%) as a yellow solid. Retention time: 3.83 min. (CHIRALPAK ID-30.46*10 cm; 3 μm; MtBE (0.1% DEA):EtOH=70:30; 1.0 ml/min); LCMS (ESI) [M+H]⁺=390; ¹HNMR (300 MHz, CD₃OD) δ 9.31 (s, 1H), 8.48-8.41 (m, 2H), 8.31 (s, 1H), 7.45-7.43 (d, J=5.1 Hz, 1H), 7.00-6.98 (d, J=6 Hz, 1H), 2.79-2.60 (m, 2H), 2.31 (s, 3H), 1.88-1.85 (m, 1H), 1.83-1.69 (m, 2H), 1.34-1.20 (m, 3H). Compound 384: (2.4 mg, 3%) as a yellow solid. Retention time: 5.64 min (CHIRALPAK ID-30.46*10 cm; 3 μm; MtBE (0.1% DEA):EtOH=70:30; 1.0 ml/min); LCMS (ESI) [M+H]$^+$=390; $^1$HNMR (300 MHz, CD$_3$OD) δ 9.31 (s, 1H), 8.48-8.41 (m, 2H), 8.31 (s, 1H), 7.45-7.43 (d, J=5.1 Hz, 1H), 7.00-6.98 (d, J=6 Hz, 1H), 2.79-2.60 (m, 2H), 2.31 (s, 3H), 1.88-1.85 (m, 1H), 1.83-1.69 (m, 2H), 1.34-1.20 (m, 3H). Compound 385: (3.4 mg, 4%) as a yellow solid. Retention time: 4.636 min (CHIRALPAK IA-30.46*5 cm; 3 μm;

Hex (0.1% DEA):EtOH=50:50; 1.0 ml/min); LCMS(ESI) [M+H]$^+$=390; $^1$HNMR (300 MHz, CD$_3$OD) δ 9.31 (s, 1H), 8.48-8.41 (m, 2H), 8.31 (s, 1H), 7.45-7.43 (d, J=5.1 Hz, 1H), 7.00-6.98 (d, J=6 Hz, 1H), 2.79-2.60 (m, 2H), 2.31 (s, 3H), 1.88-1.85 (m, 1H), 1.83-1.69 (m, 2H), 1.34-1.20 (m, 3H). Compound 386: (2.7 mg, 3%) as a yellow solid. Retention time: 6.686 min (CHIRALPAK IA-30.46*5 cm; 3 μm; Hex (0.1% DEA):EtOH=50:50; 1.0 ml/min); LCMS(ESI) [M+H]$^+$=390; $^1$HNMR (300 MHz, CD$_3$OD) δ 9.31 (s, 1H), 8.48-8.41 (m, 2H), 8.31 (s, 1H), 7.45-7.43 (d, J=5.1 Hz, 1H), 7.00-6.98 (d, J=6 Hz, 1H), 2.79-2.60 (m, 2H), 2.31 (s, 3H), 1.88-1.85 (m, 1H), 1.83-1.69 (m, 2H), 1.34-1.2 (m, 3H). Compound Characterization: Chemical

Example 233

Exemplary compounds of Formula I or Ia were prepared and characterized. The data are shown in Table A-1.

TABLE A-1

| Cmpd No. | Structure/Name | LCMS R$_T$ (min); M + H$^+$; Method | $^1$H NMR (ppm) |
|---|---|---|---|
| 1 | (±)-trans-N-[8-amino-6-(4-cyano-2-methyl-phenyl)-3-isoquinolyl]-2-cyano-cyclopropanecarboxamide | 1.842<br>368.1<br>C | $^1$H NMR (400 MHz, DMSO-d$_6$) δ: 11.12 (s, 1H), 9.35 (s, 1H), 8.24 (s, 1H), 7.81 (s, 1H), 7.73 (d, J = 8.0 Hz, 1H), 7.44 (d, J = 8.0 Hz, 1H), 6.88 (s, 1H), 6.54 (d, J = 1.2 Hz, 1H), 6.39 (s, 2H), 2.78-2.73 (m, 1H), 2.29 (s, 3H), 2.16-2.11 (m, 1H), 1.62-1.57 (m, 1H), 1.45-1.44 (m, 1H). |
| 2 | N-(8-amino-6-(4-methylpyridin-3-yl)isoquinolin-3-yl)cyclopropanecarboxamide | 1.781<br>319.2<br>C | $^1$H NMR (400 MHz, DMSO-d$_6$) δ: 10.78 (s, 1H), 9.31(s, 1H), 8.44 (d, J = 4.8 Hz, 1H), 8.40 (s, 1H), 8.26 (s, 1H), 7.34 (d, J = 4.8 Hz, 1H), 6.88 (s, 1H), 6.54 (s, 1H), 6.33 (s, 2H), 2.29 (s, 3H), 2.07-2.04 (m, 1H), 0.83-0.80 (m, 4H). |
| 3 | (±)-cis-N-[8-amino-6-[4-(hydroxymethyl)-3-pyridyl]-3-isoquinolyl]-2-fluoro-cyclopropanecarboxamide | 1.216<br>353.1<br>A | $^1$H NMR (400 MHz, CD$_3$OD) δ: 9.25 (s, 1H), 8.57 (d, J = 5.2 Hz, 1H), 8.43 (s, 1H), 8.33 (s, 1H), 7.74 (d, J = 5.2 Hz, 1H), 7.02 (s, 1H), 6.67 (d, J = 1.6 Hz, 1H), 4.99-4.95 (m, 0.5 H), 4.83-4.79 (m, 0.5 H), 4.67 (s, 2H), 2.18-2.13 (m, 1H), 1.88-1.77 (m, 1H), 1.27-1.18 (m, 1H). |

TABLE A-1-continued

| Cmpd No. | Structure/Name | LCMS $R_T$ (min); M + H+; Method | $^1$H NMR (ppm) |
|---|---|---|---|
| 4 | 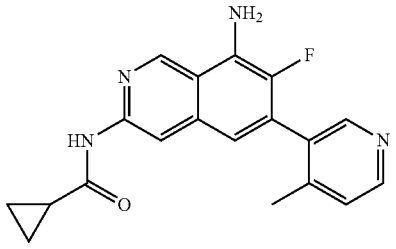 [SMILES: Cc1ccncc1-c1cc2cc(NC(=O)C3CC3)ncc2c(N)c1F]<br>N-(8-amino-7-fluoro-6-(4-methylpyridin-3-yl)isoquinolin-3-yl)cyclopropanecarboxamide | 1.819<br>337.0<br>C | $^1$H NMR (400 MHz, CDCl$_3$) δ: 9.05 (s, 1H), 8.54 (d, J = 4.8 Hz, 1H), 8.48 (s, 2H), 8.26 (s, 1H), 7.26 (d, J = 7.2 Hz, 1H), 7.06 (d, J = 6.4 Hz, 1H), 4.45 (bs, 2H), 2.26 (s, 3H), 1.63-1.60 (m, 1H), 1.16-1.14 (m, 2H), 0.94-0.92 (m, 2H). |
| 5 | 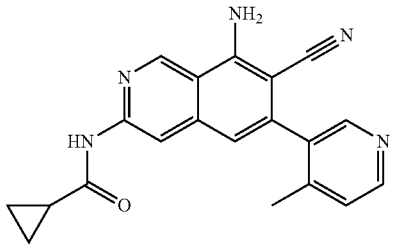 [SMILES: Cc1ccncc1-c1cc2cc(NC(=O)C3CC3)ncc2c(N)c1C#N]<br>N-(8-amino-7-cyano-6-(4-methylpyridin-3-yl)isoquinolin-3-yl)cyclopropanecarboxamide | 1.668<br>344.1<br>F | $^1$H NMR (400 MHz, CDCl$_3$) δ: 9.04 (s, 1H), 8.55 (d, J = 5.2 Hz, 1H), 8.47 (s, 1H), 8.46 (s, 1H), 8.25 (s, 1H), 7.27 (d, J = 5.2 Hz, 1H), 6.99 (s, 1H), 5.43 (bs, 2H), 2.28 (s, 3H), 1.60-1.57 (m, 1H), 1.17-1.15 (m, 2H), 0.97-0.96 (m, 2H). lU NMR (400 MHz, CD3OD) 5: 9.27 (s, 1H), 8.28 (s, 1H), 8.18 (s, 1H), 8.00 (s, 1H), 7.12 (s, 1H), 4.00 (s, 3H), 1.33 - 1.32 (m,lH), 1.04-1.03 (m, 2H), 0.95- 0.92 (m, 2H). |
| 6 | 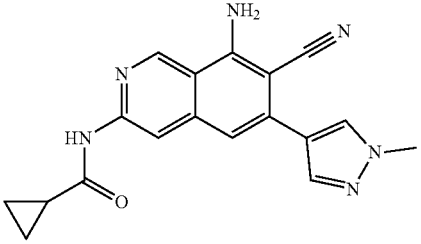 [SMILES: Cn1cc(-c2cc3cc(NC(=O)C4CC4)ncc3c(N)c2C#N)cn1]<br>N-(8-amino-7-cyano-6-(1-methyl-1H-pyrazol-4-yl)isoquinolin-3-yl)cyclopropanecarboxamide | 1.724<br>333.1<br>H | $^1$H NMR (400 MHz, CD$_3$OD) δ: 9.27 (s, 1H), 8.28 (s, 1H), 8.18 (s, 1H), 8.00 (s, 1H), 7.12 (s, 1H), 4.00 (s, 3H), 1.33-1.32 (m, 1H), 1.04-1.03 (m, 2H), 0.95-0.92 (m, 2H). |
| 7 | 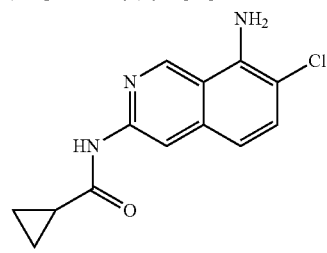<br>N-(8-amino-7-chloroisoquinolin-3-yl)cyclopropanecarboxamide | 1.760<br>262.0<br>F | $^1$H NMR (400 MHz, DMSO-d$_6$) δ: 10.84(s, 1H), 9.39(s, 1H), 8.26(s, 1H), 7.45(d, J = 8.4 Hz, 1H), 6.97(d, J = 8.4 Hz, 1H), 6.37(s, 2H), 2.02-2.06(m, 1H), 0.80-0.83(m, 4H). |
| 8 | 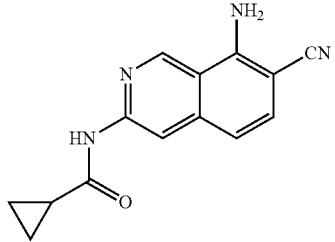 [SMILES: N#Cc1ccc2cc(NC(=O)C3CC3)ncc2c1N]<br>N-(8-amino-7-cyanoisoquinolin-3-yl)cyclopropanecarboxamide | 1.661<br>253.0<br>F | $^1$H NMR (400 MHz, CD$_3$OD) δ: 9.30 (s, 1H), 8.30 (s, 1H), 7.44 (d, J = 8.8 Hz, 1H), 7.00 (d, J = 8.4 Hz, 1H), 1.93-1.97 (m, 1H), 1.01-1.05 (m, 2H), 0.91-0.95 (m, 2H). |

TABLE A-1-continued

| Cmpd No. | Structure/Name | LCMS R_T (min); M + H+; Method | ¹H NMR (ppm) |
|---|---|---|---|
| 13 | (±)-5-[8-amino-3-[(cis-2-fluorocyclopropanecarbonyl)amino]-6-isoquinolyl]-N,4-dimethyl-pyrimidine-2-carboxamide | 1.493 395.1 E | ¹H NMR (400 MHz, CD$_3$OD) δ: 9.27 (s, 1H), 8.77 (s, 1H), 8.52 (brs, 1H), 8.36 (s, 1H), 7.09 (s, 1H), 6.72 (s, 1H), 4.99-4.79 (m, 1H), 3.04 (s, 3H), 2.65 (s, 3H), 2.18-2.13 (m, 1H), 1.88-1.78 (m, 1H), 1.27-1.19 (m, 1H). |
| 14 | (±)-cis-N-(8-amino-6-(6-methyl-1H-benzo[d]imidazol-5-yl)isoquinolin-3-yl)-2-fluorocyclopropanecarboxamide | 1.335 376.1 C | ¹H NMR (400 MHz, CD$_3$OD) δ: 9.23 (s, 1H), 8.30 (s, 1H), 8.16 (s, 1H), 7.59-7.47 (m, 2H), 7.03 (s, 1H), 6.76 (s, 1H), 4.99-4.78 (m, 1H), 2.40 (s, 3H), 2.20-2.12 (m, 1H), 1.87-1.76 (m, 1H), 1.27-1.17 (m, 1H). |
| 15 | (±)-cis-N-(8-amino-6-(5-cyclopropylpyridazin-4-yl)isoquinolin-3-yl)-2-fluorocyclopropanecarboxamide | 1.566 364.1 C | ¹H NMR (400 MHz, CD$_3$OD) δ: 9.28 (s, 1H), 9.00 (s, 1H), 8.78 (s, 1H), 8.37 (s, 1H), 7.18 (s, 1H), 6.80 (s, 1H), 4.99-4.95-4.78 (m, 1H), 2.21-2.08 (m, 2 H), 1.88-1.76 (m, 1H), 1.27-1.17 (m, 3H), 1.12-1.06 (m, 2H). |
| 16 | (±)-cis-N-(8-amino-6-(7-methyl-3H-imidazo [4, 5-b] pyridin-6-yl) isoquinolin-3-yl)-2-fluorocyclopropanecarboxamide | 1.42 377.2 E | ¹HNMR (400 MHz, CD$_3$OD) δ: 9.25 (s, 1H), 8.43 (s, 1H), 8.33 (s, 2H),7.06 (s, 1H), 6.76 (d, J = 1.6 Hz, 1H), 4.99-4.79 (m, 1H), 2.65 (s, 3H), 2.18-2.13 (m, 1H), 1.88-1.77 (m, 1H), 1.27-1.18 (m, 1H). |

TABLE A-1-continued

| Cmpd No. | Structure/Name | LCMS R$_T$ (min); M + H$^+$; Method | $^1$H NMR (ppm) |
|---|---|---|---|
| 17 | 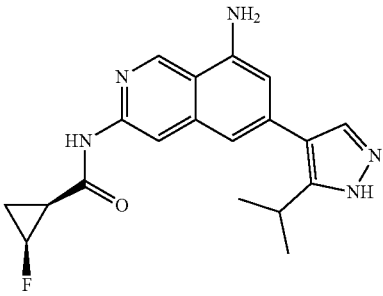 [SMILES: CC(C)c1[nH]ncc1-c1cc(N)c2cnc(NC(=O)[C@@H]3C[C@@H]3F)cc2c1]<br>(±)-cis-N-(8-amino-6-(5-isopropyl-1H-pyrazol-4-yl) isoquinolin-3-yl)-2-fluorocyclopropanecarboxamide | 1.57<br>354.1<br>E | $^1$H NMR (400 MHz, CD$_3$OD) δ: 9.17(s, 1H), 8.26 (s, 1H), 7.69 (s, 1H), 7.07 (s, 1H), 6.83 (d, J = 0.9 Hz, 1H), 4.99-4.92 (m, 0.5 H), 4.83-4.79 (m, 0.5 H), 3.45-3.44 (m, 1H), 2.17-2.13 (m, 1H), 1.87-1.79 (m, 1H), 1.37-1.35 (d, J = 6.8 Hz, 6H), 1.27-1.18 (m, 1H). |
| 18 | 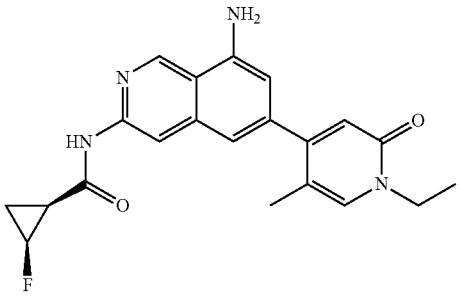<br>(±)-cis-N-(8-amino-6-(1-ethyl-5-methyl-2-oxo-1,2-dihydropyridin-4-yl)isoquinolin-3-yl)-2-fluorocyclopropanecarboxamide | 1.44<br>381.1<br>A | $^1$H NMR (400 MHz, CD$_3$OD) δ: 9.24 (s, 1H), 8.32 (s, 1H), 7.58 (s, 1H), 6.96 (s, 1H), 6.63 (d, J = 0.8 Hz, 1H), 6.49 (s, 1H), 4.97-4.80 (m, 1H), 4.108(q, J = 7.2 Hz, 2H), 2.17-2.14(m, 1H), 2.05 (s, 3H), 1.86-1.79 (m, 1H), 1.39 (t, J = 7.2 Hz, 3H), 1.25-1.20 (m, 1H). |
| 19 | 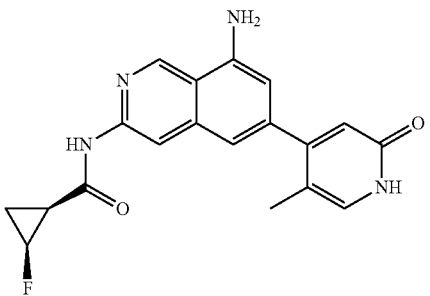 [SMILES: Cc1c[nH]c(=O)cc1-c1cc(N)c2cnc(NC(=O)[C@@H]3C[C@@H]3F)cc2c1]<br>(±)-cis-N-(8-amino-6-(5-methyl-2-oxo-1,2-dihydropyridin-4-yl)isoquinolin-3-yl)-2-fluorocyclopropanecarboxamide | 1.45<br>353.1<br>B | $^1$H NMR (400 MHz, DMSO-d$_6$) δ: 11.53-11.49 (m, 1H), 10.81 (s, 1H), 9.32 (s, 1H), 8.27 (s, 1H), 7.28 (s, 1H), 6.85 (s, 1H), 6.49 (s, 1H), 6.34 (s, 1H), 6.19 (s, 1H), 5.03-4.83 (m, 1H), 2.28-2.22 (m, 1H), 1.91 (s, 3H), 1.71-1.63 (m, 1H), 1.21-1.14 (m, 1H). |
| 20 | 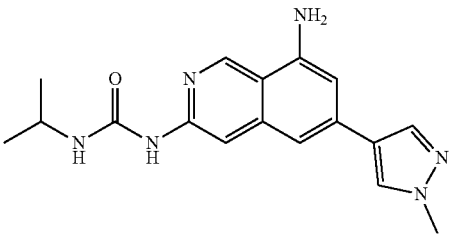 [SMILES: CC(C)NC(=O)Nc1cc2cc(-c3cnn(C)c3)cc(N)c2cn1]<br>1-(8-amino-6-(1-methyl-1H-pyrazol-4-yl)isoquinolin-3-yl)-3-isopropylurea | 1.167<br>325.2<br>B | $^1$H NMR (400 MHz, CD$_3$OD) δ: 8.94 (s, 1H), 7.92 (s, 1H), 7.78 (s, 1H), 7.35 (s, 1H), 7.06 (s, 1H), 6.76 (d, J = 1.6 Hz, 1H), 3.92-3.85 (m, 1H), 3.85 (s, 3H), 1.15 (d, J = 6.4 Hz, 6H). |

TABLE A-1-continued

| Cmpd No. | Structure/Name | LCMS R_T (min); M + H+; Method | 1H NMR (ppm) |
|---|---|---|---|
| 21 | (±)-trans-N-[8-amino-6-(1-methylpyrrolo[2,3-b]pyridin-4-yl)-3-isoquinolyl]-2-cyano-cyclopropanecarboxamide | 1.479 383.1 A | 1H NMR (400 MHz, DMSO-d6) δ: 11.13 (s, 1H), 9.37 (s, 1H), 8.36 (d, J = 4.8 Hz, 1H), 8.32 (s, 1H), 7.62 (d, J = 3.2 Hz, 1H), 7.28 (s, 1H), 7.27 (d, J = 4.8 Hz, 1H), 7.04 (d, J = 1.2 Hz, 1H), 6.69 (d, J = 3.2 Hz, 1H), 6.44 (s, 2H), 3.88 (s, 3H), 2.80-2.75 (m, 1H), 2.18-2.13 (m, 1H), 1.63-1.58 (m, 1H), 1.47-1.42 (m, 1H). |
| 22 | (±)-trans-N-[8-amino-6-(1H-pyrrolo[2,3-b]pyridin-4-yl)-3-isoquinolyl]-2-cyano-cyclopropanecarboxamide | 1.392 369.1 A | 1H NMR (400 MHz, DMSO-d6) δ: 11.80 (s, 1H), 11.11(s, 1H), 9.36 (s, 1H), 8.31 (s, 1H), 8.30 (d, J = 5.2 Hz, 1H), 7.56 (t, J = 2.8 Hz, 1H), 7.28 (s, 1H), 7.23 (d, J = 4.8 Hz, 1H), 7.04 (d, J = 1.2 Hz, 1H), 6.67 (q, J = 1.7 Hz, 1H), 6.42 (s, 2H), 2.79-2.75 (m, 1H), 2.17-2.12 (m, 1H), 1.62-1.57 (m, 1H), 1.47-1.42 (m, 1H). |
| 23 | (±)-trans-N-[8-amino-6-(3-ethyl-1-methyl-6-oxo-2-pyridyl)-3-isoquinolyl]-2-cyano-cyclopropanecarboxamide | 1.528 388.1 A | 1H NMR (400 MHz, CD3OD) δ: 9.30 (s, 1H), 8.32 (s, 1H), 7.58 (d, J = 9.2 Hz, 1H), 6.96 (s, 1H), 6.64 (d, J = 9.2 Hz, 1H), 6.56 (s, 1H), 3.30 (s, 3H), 2.67-2.62 (m, 1H), 2.22-2.10 (m, 3H), 1.62-1.53 (m, 2H), 1.3 (t, J = 7.6 Hz, 3H). |
| 24 | (±)-cis-N-[8-amino-6-(1,4-dimethyl-2-oxo-3-pyridyl)-3-isoquinolyl]-2-fluoro-cyclopropanecarboxamide | 1.543 367.1 C | 1H NMR (400 MHz, CD3OD) δ: 9.21 (s, 1H), 8.28 (s, 1H), 7.58(d, J = 6.8 Hz, 1H), 6.91 (s, 1H), 6.58 (s, 1H), 6.40 (d, J = 6.8 Hz, 1H), 4.98-4.78 (m, 1H), 3.59 (s, 3H), 2.17-2.13 (m, 1H), 2.01 (s, 3H), 1.87-1.76 (m, 1H), 1.26-1.17 (m, 1H). |

TABLE A-1-continued

| Cmpd No. | Structure/Name | LCMS R_T (min); M + H+; Method | 1H NMR (ppm) |
|---|---|---|---|
| 25 | (±)-trans-N-[8-amino-6-(1,4-dimethyl-2-oxo-3-pyridyl)-3-isoquinolyl]-2-fluoro-cyclopropanecarboxamide | 1.524 367.1 B | 1H NMR (400 MHz, CD3OD) δ: 9.21 (s, 1H), 8.21 (s, 1H), 7.58 (d, J = 6.8 Hz, 1H), 6.89 (s, 1H), 6.58 (s, 1H), 6.40 (d, J = 6.8 Hz, 1H), 4.97-4.78 (m, 1H), 3.59 (s, 3H), 2.49-2.39 (m, 1H), 2.01 (s, 3H), 1.55-1.47 (m, 1H), 1.41-1.36 (m, 1H). |
| 26 | (±)-cis-N-(8-amino-6-(6-methoxy-2-methylpyridin-3-yl)isoquinolin-3-yl)-2-fluorocyclopropanecarboxamide | 1.738 367.0 G | 1HNMR(400 MHz, CD3OD) δ 9.22 (s, 1H), 8.29 (s, 1H), 7.59 (d, J = 8.4 Hz, 1H), 6.98 (s, 1H), 6.71(d, J = 8.0 Hz, 1H), 6.69(d, J = 1.6 Hz, 1H), 4.99-4.80 (m, 1H), 3.96 (s, 3H), 2.44 (s, 3H), 2.18-2.14 (m, 1H), 1.86-1.79 (m, 1H), 1.25-1.22 (m, 1H). |
| 27 | (±)-cis-N-(8-amino-6-(2-methyl-6-oxo-1,6-dihydropyridin-3-yl)isoquinolin-3-yl)-2-fluorocyclopropanecarboxamide | 1.348 353.0 G | 1H NMR(400 MHz, CD3OD) δ: 9.20(s, 1H), 8.29(s, 1H), 7.62(d, J = 9.2 Hz, 1H), 6.97(s, 1H), 6.65 (d, J = 1.2 Hz, 1H), 6.48(d, J = 9.2 Hz, 1H), 4.98-4.80 (m, 1H), 2.35(s, 3H), 2.18-2.113 (m, 1H), 1.86-1.79 (m, 1H), 1.24-1.20 (m, 1H). |
| 28 | (±)-cis-N-(8-amino-6-(5-methyl-1H-pyrazol-4-yl)isoquinolin-3-yl)-2-fluorocyclopropanecarboxamide | 1.417 326.7 G | 1H NMR(400 MHz, CD3OD) δ: 9.14 (s, 1H), 8.27 (s, 1H), 7.81(s, 1H), 7.14 (s, 1H), 6.90 (d, J = 1.6 Hz, 1H), 4.99-4.79 (m, 1H), 2.52 (s, 3H), 2.19-2.12 (m, 1H), 1.87-1.79 (m, 1H), 1.25-1.20 (m, 1H). |

TABLE A-1-continued

| Cmpd No. | Structure/Name | LCMS $R_T$ (min); M + H+; Method | 1H NMR (ppm) |
|---|---|---|---|
| 30 | (1S,2S)-N-(8-amino-6-(5-oxopyrrolidin-3-yl)isoquinolin-3-yl)-2-fluorocyclopropanecarboxamide | 1.401 329.7 C | 1H NMR(400 MHz, CD3OD) δ 9.14 (s, 1H), 8.24 (s, 1H), 6.99 (s, 1H), 6.69 (s, 1H), 4.99-4.78 (m, 1H), 3.86-3.76 (m, 2H), 3.51-3.47 (m, 1H), 2.81-2.74 (m, 1H), 2.59-2.53 (m, 1H), 2.14-2.11 (m, 1H), 1.79-1.73 (m, 1H), 1.22-1.20 (m, 1H). |
| 31 | (±)-cis-N-(8-amino-6-(4-ethyl-6-(hydroxymethyl)pyridin-3-yl)isoquinolin-3-yl)-2-fluorocyclopropanecarboxamide | 1.565 381.7 C | 1HNMR(400 MHz, CD3OD) δ: 9.25 (s, 1H), 8.31(s, 1H), 8.30 (s, 1H) 7.56 (s, 1H), 6.99 (s, 1H), 6.67(d, J = 1.6 Hz, 1H), 4.98-4.75 (m, 1H), 4.75 (s, 2H), 2.74 (q, J = 7.2 Hz, 2H), 2.18-2.15 (m, 1H), 1.88-1.85 (m, 1H), 1.23-1.20 (m, 1H), 1.18 (t, J = 7.2 Hz, 3H). |
| 32 | (±)-trans-N-(8-amino-6-(4-methylpyridin-3-yl)isoquinolin-3-yl)-2-cyanocyclopropanecarboxamide | 1.381 344.1 B | 1H NMR (400 MHz, DMSO-d6) δ: 11.16 (s, 1H), 9.34 (s, 1H), 8.44 (d, J = 5.2 Hz, 1H), 8.40 (s, 1H), 8.24 (s, 1H), 7.34 (d, J = 4.8 Hz, 1H), 6.91 (s, 1H), 6.57 (d, J = 1.6 Hz, 1H), 6.38 (s, 2H), 2.76-2.74 (m, 1H), 2.29 (s, 3H), 2.15-2.11 (m, 1H), 1.60-1.44 (m, 1H), 1.43-1.41 (m, 1H). |
| 37 | (1S,2S)-N-(8-amino-6-(4-methyl-2-oxooxazolidin-3-yl)isoquinolin-3-yl)-2-fluorocyclopropane carboxamide | 1.540 345.1 C | 1H NMR (400 MHz, DMSO-d6) δ: 10.74 (s, 1H), 9.19 (s, 1H), 8.19 (s, 1H), 7.00 (d, J = 2.0 Hz, 1H), 6.92 (d, J = 1.6 Hz, 1H), 6.32 (s, 2H), 5.01-4.83 (m, 1H), 4.71-4.68 (m, 1H), 4.58-4.54 (m, 1H), 4.06-4.03 (m, 1H), 2.28-2.21 (m, 1H), 1.71-1.61 (m, 1H), 1.29 (d, J = 6.0 Hz, 3H), 1.19-1.12 (m, 1H). |

TABLE A-1-continued

| Cmpd No. | Structure/Name | LCMS R_T (min); M + H+; Method | 1H NMR (ppm) |
|---|---|---|---|
| 38 | (±)-trans-N-(8-amino-6-(quinolin-4-yl)isoquinolin-3-yl)-2-cyanocyclopropanecarboxamide | 1.573 380.1 B | 1H NMR (400 MHz, DMSO-d6) δ: 11.15 (s, 1H), 9.41 (s, 1H), 8.96 (d, J = 4.4 Hz, 1H), 8.28 (s, 1H), 8.12 (d, J = 8.0 Hz, 1H), 7.95 (d, J = 8.4 Hz, 1H), 7.82-7.78 (m, 1H), 7.62-7.58 (m, 1H), 7.51 (d, J = 4.4 Hz, 1H), 7.07 (s, 1H), 6.73 (d, J = 1.6 Hz, 1H), 6.49 (s, 2H), 2.77-2.72 (m, 1H), 2.15-2.11 (m, 1H), 1.60-1.58 (m, 1H), 1.45-1.40 (m, 1H). |
| 39 | (±)-cis-N-(8-amino-6-(5-amino-4-ethylpyridin-3-yl)isoquinolin-3-yl)-2-fluorocyclopropanecarboxamide | 1.540 366.2 F | 1H NMR (400 MHz, DMSO-d6) δ: 10.80 (s, 1H), 9.30 (s, 1H), 8.24 (s, 1H), 7.94 (s, 1H), 7.57 (s, 1H), 6.79 (s, 1H), 6.48 (s, 1H), 6.31 (s, 2H), 5.21 (s, 2H), 5.02-4.84 (m, 1H), 2.46-2.41 (m, 2H), 2.27-2.24 (m, 1H), 1.69-1.62 (m, 1H), 1.18-1.14 (m, 1H), 0.98 (t, J = 7.6 Hz, 3H). |
| 40 | 3-amino-N-(8-amino-6-(4-methylpyridin-3-yl)isoquinolin-3-yl)propanamide | 1.450 322.2 F | 1H NMR (400 MHz, CD3OD) δ: 9.23 (s, 1H), 8.40 (d, J = 5.2 Hz, 1H), 8.39 (s, 1H), 8.33 (s, 1H), 7.39 (d, J = 5.2 Hz, 1H), 6.99 (s, 1H), 6.68 (d, J = 1.2 Hz, 1H), 3.05 (t, J = 6.8 Hz, 2H), 2.66 (t, J = 6.8 Hz, 2H), 2.37 (s, 3H). |
| 41 | (±)-cis-N-(8-amino-6-(5-isopropyl-1H-pyrazol-4-yl) isoquinolin-3-yl)-2-fluoro cyclopropanecarboxamide | 1.530 354.2 B | 1H NMR (400 MHz, CD3OD) δ: 9.43 (s, 1H), 8.39 (s, 1H), 7.70 (s, 1H), 7.29 (s, 1H), 7.03 (s, 1H), 5.10-5.06 (m, 1H), 3.62-3.57 (m, 1H), 2.20-2.17 (m, 1H), 1.99-1.89 (m, 1H), 1.42 (d, J = 6.8 Hz, 6H), 1.39-1.30 (m, 1H). |

TABLE A-1-continued

| Cmpd No. | Structure/Name | LCMS R_T (min); M + H+; Method | ¹H NMR (ppm) |
|---|---|---|---|
| 42 | (±)-trans-N-(8-amino-6-(5-isopropyl-1H-pyrazol-4-yl) isoquinolin-3-yl)-2-fluoro cyclopropanecarboxamide | 1.590 354.2 B | ¹H NMR (400 MHz, CD$_3$OD) δ: 9.41 (s, 1H), 8.37 (s, 1H), 7.68 (s, 1H), 7.30 (s, 1H), 7.03 (s, 1H), 5.08-5.05 (m, 1H), 3.62-3.58 (m, 1H), 2.46-2.38 (m, 1H), 1.75-1.65 (m, 1H), 1.58-1.50 (m, 1H), 1.42 (d, J = 6.8 Hz, 6H). |
| 43 | (±)-cis-N-(8-amino-6-(1-methyl-6-oxo-1,6-dihydropyridin-2-yl)isoquinolin-3-yl)-2-fluorocyclopropane carboxamide | 1.385 353.1 A | 1H NMR(400 MHz, CD$_3$OD) δ: 9.27 (s, 1H), 8.36 (s, 1H), 7.59 (dd, J = 6.8, 9.2 Hz, 1H), 7.09 (s, 1H), 6.67 (d, J = 1.6 Hz, 1H), 6.62(dd, J = 1.2, 9.2 Hz, 1H), 6.42 (dd, J = 1.2, 6.8 Hz, 1H), 4.99-4.79 (m, 1H), 3.46 (s, 3H), 2.19-2.13 (m, 1H), 1.87-1.78 (m, 1H), 1.27-1.18 (m, 1H). |
| 44 | (±)-trans-N-[8-amino-6-(6-methyl-1H-indazol-5-yl)-3-isoquinolyl]-2-cyano-cyclopropanecarboxamide | 1.513 383.1 A | ¹H NMR (400 MHz, CD$_3$OD) δ: 9.24 (s, 1H), 8.27 (s, 1H), 8.03 (s, 1H), 7.65 (s, 1H), 7.45 (s, 1H), 7.00 (s, 1H), 6.76 (d, J = 1.2 Hz, 1H), 2.65-2.64 (m, 1H), 2.39 (s, 3H), 2.14-2.09 (m, 1H), 1.62-1.55 (m, 2H). |
| 45 | (±)-trans-N1-[8-amino-6-(6-methyl-1H-indazol-5-yl)-3-isoquinolyl] cyclopropane-1,2-dicarboxamide | 1.372 401.1 A | ¹H NMR (400 MHz, CD$_3$OD) δ: 9.23 (s, 1H), 8.25 (s, 1H), 8.03 (s, 1H), 7.65 (s, 1H), 7.45 (s, 1H), 7.00 (s, 1H), 6.75 (s, 1H), 2.42-2.38 (m, 4H), 2.25-2.20 (m, 1H), 1.44-1.40 (m, 2H). |

TABLE A-1-continued

| Cmpd No. | Structure/Name | LCMS R_T (min); M + H+; Method | 1H NMR (ppm) |
|---|---|---|---|
| 46 | 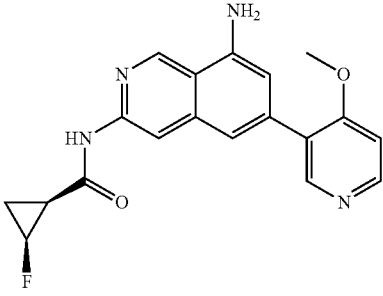 [SMILES: COc1ccncc1-c1cc(N)c2cnc(NC(=O)[C@@H]3C[C@@H]3F)cc2c1]<br>(±)-cis-N-(8-amino-6-(4-methoxypyridin-3-yl)isoquinolin-3-yl)-2-fluorocyclopropanecarboxamide | 1.253<br>353.1<br>A | 1H NMR (400 MHz, CD3OD) δ: 9.22 (s, 1H), 8.44 (d, J = 6.0 Hz, 1H), 8.41 (s, 1H), 8.31 (s, 1H), 7.21 (d, J = 6.0 Hz, 1H), 7.19 (s, 1H), 6.88 (d, J = 1.6 Hz, 1H), 4.98-4.80 (m, 1H), 3.96 (s, 3H), 2.19-2.14 (m, 1H), 1.88-1.78 (m, 1H), 1.27-1.18 (m, 1H). |
| 47 | 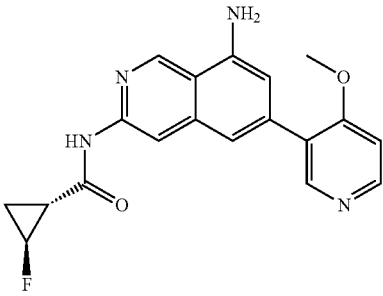<br>(±)-trans-N-(8-amino-6-(4-methoxypyridin-3-yl)isoquinolin-3-yl)-2-fluorocyclopropanecarboxamide | 1.295<br>353.1<br>A | 1H NMR (400 MHz, CD3OD) δ: 9.22 (s, 1H), 8.44 (d, J = 6.0 Hz, 1H), 8.40 (s, 1H), 8.25 (s, 1H), 7.21 (d, J = 6.0 Hz, 1H), 7.17 (s, 1H), 6.88 (d, J = 0.8 Hz, 1H), 4.99-4.78 (m, 1H), 3.96 (s, 3H), 2.50-2.40 (m, 1H), 1.55-1.49 (m, 1H), 1.42-1.37 (m, 1H). |
| 48 | 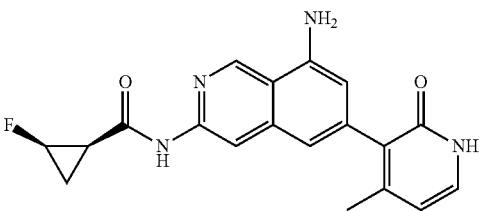 [SMILES: Cc1cc[nH]c(=O)c1-c1cc(N)c2cnc(NC(=O)[C@H]3C[C@H]3F)cc2c1]<br>(±)-cis-N-[8-amino-6-(2-hydroxy-4-methyl-3-pyridyl)-3-isoquinolyl]-2-fluoro-cyclopropanecarboxamide | 1.625<br>353.1<br>I | 1H NMR (400 MHz, DMSO-d6) δ: 11.26 (s, 1H), 10.47(s, 1H), 9.25 (s, 1H), 8.17 (s, 1H), 7.23 (d, J = 8.8 Hz, 1H), 6.74 (s, 1H), 6.47 (s, 1H), 6.13 (d, J = 8.8 Hz, 1H), 5.91 (s, 2H), 5.00-4.76 (m, 1H), 2.27-2.23 (m, 1H), 2.00 (s, 3H), 1.74-1.61 (m, 1H), 1.18-1.12 (m, 1H). |
| 49 | 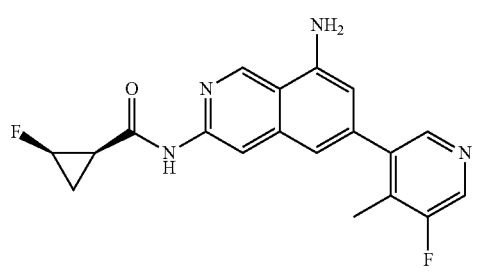 [SMILES: Cc1c(F)cncc1-c1cc(N)c2cnc(NC(=O)[C@H]3C[C@H]3F)cc2c1]<br>(±)-cis-N-[8-amino-6-(5-fluoro-4-methyl-3-pyridyl)-3-isoquinolyl]-2-fluoro-cyclopropanecarboxamide | 1.422<br>355.1<br>D | 1H NMR (400 MHz, CD3OD) δ: 9.25 (s, 1H), 8.39 (d, J = 1.2 Hz, 1H), 8.34 (s, 1H), 8.30 (s, 1H), 7.01 (s, 1H), 6.68 (d, J = 1.6 Hz, 1H), 4.99-4.78 (m, 1H), 2.31 (d, J = 2.0 Hz, 3H), 2.18-2.13 (m, 1H), 1.87-1.77 (m, 1H), 1.26-1.21 (m, 1H). |

TABLE A-1-continued

| Cmpd No. | Structure/Name | LCMS R$_T$ (min); M + H$^+$; Method | $^1$H NMR (ppm) |
|---|---|---|---|
| 50 | (±)-cis-N-[8-amino-6-(3-pyridyl)-3-isoquinolyl]-2-fluoro-cyclopropanecarboxamide | 1.273 323.0 A | $^1$H NMR (400 MHz, CD$_3$OD) δ: 9.23 (s, 1H), 8.89 (d, J = 1.6 Hz, 1H), 8.56 (dd, J = 1.6, 4.8 Hz, 1H), 8.37 (s, 1H), 8.21-8.18 (m, 1H), 7.56 (dd, J = 4.8, 8.0 Hz, 1H), 7.34 (s, 1H), 7.01(d, J = 1.2 Hz, 1H), 4.99-4.79 (m, 1H), 2.20-2.13 (m, 1H), 1.88-1.78 (m, 1H), 1.27-1.19(m, 1H). |
| 51 | (±)-trans-N-[8-amino-6-(3-methyl-4-pyridyl)-3-isoquinolyl]-2-cyano-cyclopropanecarboxamide | 1.338 344.2 D | $^1$H NMR (400 MHz, CD$_3$OD) δ: 9.26 (s, 1H), 8.47 (s, 1H), 8.41(d, J = 5.2 Hz, 1H), 8.30 (s, 1H), 7.35 (d, J = 5.2 Hz, 1H), 7.00 (s, 1H), 6.69 (d, J = 1.2 Hz, 1H), 2.64-2.63(m, 1H), 2.34 (s, 3H), 2.12-2.10(m, 1H), 1.60-1.53(m, 2H). |
| 52 | (±)-trans-N-[8-amino-7-fluoro-6-(4-methyl-3-pyridyl)-3-isoquinolyl]-2-cyano-cyclopropanecarboxamide | 1.330 362.1 A | $^1$H NMR (400 MHz, CD$_3$OD) δ: 9.32 (s, 1H), 8.47 (d, J = 5.2 Hz, 1H), 8.41(s, 1H), 8.33 (s, 1H), 7.42 (d, J = 5.2 Hz, 1H), 6.99 (d, J = 6.4 Hz, 1H), 2.65- 2.61 (m, 1H), 2.30 (s, 3H), 2.14-2.09 (m, 1H), 1.61-1.52 (m, 2H). |
| 54 | (±)-trans-N-(8-amino-6-(5-methyl-2-oxo-2,3-dihydrobenzo[d]oxazol-6-yl)isoquinolin-3-yl)-2-cyanocyclopropanecarboxamide | 1.669 400.1 B | $^1$H NMR (400 MHz, DMSO-d$_6$) δ: 11.14(s, 1H), 9.36 (s, 1H), 8.26 (s, 1H), 7.18 (s, 1H), 7.06 (s, 1H), 6.89 (s, 1H), 6.61(s, 1H), 6.35 (s, 2H), 2.83-2.78 (m, 1H), 2.30 (s, 3H), 2.21-2.16 (m, 1H), 1.66-1.62 (m, 1H), 1.51-1.46 (m, 1H). |

TABLE A-1-continued

| Cmpd No. | Structure/Name | LCMS R_T (min); M + H+; Method | 1H NMR (ppm) |
|---|---|---|---|
| 55 | (±)-cis-N-(8-amino-6-(2-ethyl-5-oxopyrrolidin-1-yl)isoquinolin-3-yl)-2-fluorocyclopropane carboxamide | 1.652 356.7 C | $^1$H NMR (400 MHz, CD$_3$OD) δ: 9.15 (s, 1H), 8.26 (s, 1H), 7.07-7.04 (m, 1H), 6.85-6.84 (m, 1H), 5.00-4.78 (m, 1H), 4.43-4.35 (m, 1H), 2.67-2.54 (m, 2H), 2.43-2.34 (m, 1H), 2.20-2.10 (m, 1H), 1.97-1.69 (m, 3H), 1.55-1.47 (m, 1H), 1.26-1.17 (m, 1H), 0.91 (t, J = 7.2 Hz, 3H) |
| 56 | (±)-trans-N-(8-amino-6-(4-ethylpyridin-3-yl)-2,7-naphthyridin-3-yl)-2-cyanocyclopropane carboxamide | 1.956 402.2 C | $^1$H NMR (400 MHz, CD$_3$OD) δ: 9.24 (s, 1H), 8.26 (s, 1H), 7.94 (s, 1H), 6.95 (s, 1H), 6.76 (s, 1H), 6.67 (d, J = 1.6 Hz, 1H), 4.35(q, J = 6.8 Hz, 2H), 2.69-2.63 (m, 3H), 2.14-2.09 (m, 1H), 1.61-1.53 (m, 2H), 1.42 (t, J = 7.2 Hz, 3H), 1.12 (t, J = 7.6 Hz, 3H) |
| 57 | (±)-trans-N-(8-amino-6-(1,2-dimethyl-1H-imidazol-5-yl)isoquinolin-3-yl)-2-cyanocyclopropanecarboxamide | 1.532 346.8 H | $^1$H NMR (400 MHz, CD$_3$OD) δ: 9.19 (s, 1H), 8.27 (s, 1H), 7.06 (s, 1H), 6.98 (s, 1H), 7.76 (d, J = 1.6 Hz, 1H), 3.66 (s, 3H), 2.67-2.60 (m, 1H), 2.45 (s, 3H), 2.13-2.04 (m, 1H), 1.63-1.50 (m, 2H). |
| 59 | (±)-cis-N-[8-amino-6-(3-methyl-4-pyridyl)-3-isoquinolyl]-2-fluoro-cyclopropanecarboxamide | 1.605 337.1 C | $^1$H NMR (400 MHz, CD$_3$OD) δ: 9.25 (s, 1H), 8.48 (s, 1H), 8.43 (d, J = 4.8 Hz, 1H), 8.33 (s, 1H), 7.36 (d, J = 4.8 Hz, 1H), 7.02 (s, 1H), 6.69 (d, J = 1.2 Hz, 1H), 4.99-4.79 (m, 1H), 2.35 (s, 3H), 2.20-2.12 (m, 1H), 1.87-1.77 (m, 1H), 1.27-1.18 (m, 1H). |

TABLE A-1-continued

| Cmpd No. | Structure/Name | LCMS R_T (min); M + H+; Method | $^1$H NMR (ppm) |
|---|---|---|---|
| 60 | (±)-trans-N-(8-amino-6-(4-(1,1-difluoroethyl)pyridin-3-yl)isoquinolin-3-yl)-2-cyanocyclopropanecarboxamide | 1.75 394.2 B | $^1$H NMR (400 MHz, DMSO-d$_6$) δ: 11.13 (s, 1H), 9.35 (s, 1H), 8.75 (d, J = 5.2 Hz, 1H), 8.51 (s, 1H), 8.21 (s, 1H), 7.64 (d, J = 5.6 Hz, 1H), 6.87 (s, 1H), 6.53 (s, 1H), 6.41 (s, 2H), 2.77-2.50 (m, 1H), 2.14-2.10 (m, 1H), 1.77 (t, J = 19.2 Hz, 1H), 1.61-1.58 (m, 1H), 1.44-1.43 (m, 1H). |
| 61 | (±)-N-(8-amino-6-(4-methylpyridin-3-yl)isoquinolin-3-yl)-2-(morpholin-3-yl)acetamide | 1.490 378.2 C | $^1$H NMR (400 MHz, DMSO-d$_6$) δ: 10.62 (s, 1H), 9.30 (s, 1H), 8.45 (d, J = 4.8 Hz, 1H), 8.41 (s, 1H), 8.29 (s, 1H), 7.35 (d, J = 4.8 Hz, 1H), 6.92 (s, 1H), 6.56 (s, 1H), 6.33(s, 2H), 3.71-3.63 (m, 2H), 3.22-3.20 (m, 1H), 3.12-3.10 (m, 2H), 2.78-2.75 (m, 2H), 2.41-2.40 (m, 2H), 2.30 (s, 3H). |
| 62 | (±)-trans-N-(8-amino-6-(4-methylisothiazol-5-yl)isoquinolin-3-yl)-2-cyanocyclopropanecarboxamide | 1.759 350.1 C | $^1$H NMR (400 MHz, DMSO-d$_6$) δ: 9.34 (s, 1H), 8.47 (s, 1H), 8.28 (s, 1H), 7.09 (s, 1H), 6.74 (d, J = 1.6 Hz, 1H), 6.52 (s, 2H), 6.08 (d, J = 1.6 Hz, 1H). 2.78-2.74 (m, 1H), 2.40 (s, 3H), 2.17-2.12 (m, 1H), 1.62-1.60 (m, 1H), 1.46-1.42 (m, 1H) |
| 63 | (±)-trans-N-[8-amino-6-[6-(difluoromethoxy)-4-ethyl-3-pyridyl]-3-isoquinolyl]-2-cyano-cyclopropanecarboxamide | 1.950 424.2 F | $^1$H NMR (400 MHz, CD$_3$OD) δ: 9.26 (s, 1H), 8.28 (s, 1H), 8.06 (s, 1H), 7.58 (t, J = 73.2 Hz, 1H), 6.97 (s, 2H), 6.67 (s, 1H), 2.71 (q, J = 7.6 Hz, 2H), 2.68-2.65 (m, 1H), 2.14-2.09 (m, 1H), 1.63-1.52 (m, 2H), 1.15 (t, J = 7.6 Hz, 3H). |

TABLE A-1-continued

| Cmpd No. | Structure/Name | LCMS $R_T$ (min); M + H+; Method | ¹H NMR (ppm) |
|---|---|---|---|
| 65 | (±)-trans-N-[8-amino-6-[4-(2-hydroxyethyl)-3-pyridyl]-3-isoquinolyl]-2-cyano-cyclopropane carboxamide | 1.409 374.2 G | ¹H NMR (400 MHz, CD₃OD) δ: 9.26 (s, 1H), 8.47 (d, J = 5.2 Hz, 1H), 8.40 (s, 1H), 8.30 (s, 1H), 7.49 (d, J = 5.2 Hz, 1H), 7.01 (s, 1H), 6.70 (d, J = 1.2 Hz, 1H), 3.70 (t, J = 6.8 Hz, 2H), 2.94 (t, J = 6.8 Hz, 2H), 2.70-2.61 (m, 1H), 2.17-2.06 (m, 1H), 1.66-1.49 (m, 2H). |
| 66 | (1S,2S)-N-(8-amino-6-(4-ethylpyridin-3-yl)isoquinolin-3-yl)-2-fluorocyclopropane-1-carboxamide | 2.808 351.1 J | ¹H NMR (400 MHz, DMSO) δ 10.80 (s, 1H), 9.32 (s, 1H), 8.49 (d, J = 5.1 Hz, 1H), 8.39-8.35 (m, 1H), 8.27 (s, 1H), 7.38 (d, J = 5.2 Hz, 1H), 6.88 (s, 1H), 6.53 (d, J = 1.5 Hz, 1H), 6.34 (s, 2H), 5.04-4.81 (m, 1H), 2.62 (q, J = 7.6 Hz, 2H), 2.26 (dq, J = 14.1, 7.1 Hz, 1H), 1.73-1.59 (m, 1H), 1.17 (ddt, J = 13.1, 9.8, 6.7 Hz, 1H), 1.13-1.06 (m, 3H). |
| 67 | (±)-trans-N-(8-amino-6-(4-ethylpyridin-3-yl)isoquinolin-3-yl)-2-cyanocyclopropane-1-carboxamide | 2.999 358.1 J | ¹H NMR (400 MHz, DMSO) δ 11.10 (s, 1H), 9.34 (s, 1H), 8.49 (d, J = 5.1 Hz, 1H), 8.40-8.34 (m, 1H), 8.23 (s, 1H), 7.41-7.35 (m, 1H), 6.88 (s, 1H), 6.55 (d, J = 1.5 Hz, 1H), 6.38 (s, 2H), 2.80-2.72 (m, 1H), 2.61 (q, J = 7.5 Hz, 2H), 2.13 (ddd, J = 9.3, 6.1, 4.3 Hz, 1H), 1.59 (ddd, J = 8.6, 6.0, 4.4 Hz, 1H), 1.43 (ddd, J = 9.3, 5.9, 4.4 Hz, 1H), 1.09 (t, J = 7.6 Hz, 3H). |

TABLE A-1-continued

| Cmpd No. | Structure/Name | LCMS R_T (min); M + H+; Method | 1H NMR (ppm) |
|---|---|---|---|
| 68 | 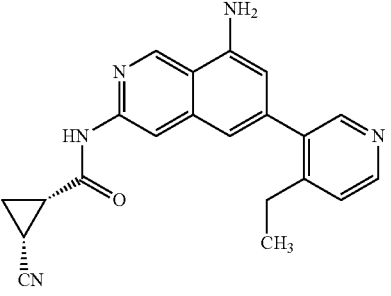 [SMILES: CCc1ccncc1-c1cc(N)c2cnc(NC(=O)[C@H]3C[C@H]3C#N)cc2c1]<br>(±)-cis-N-(8-amino-6-(4-ethylpyridin-3-yl)isoquinolin-3-yl)-2-cyanocyclopropane-1-carboxamide | 2.745<br>358.2<br>J | 1H NMR (400 MHz, DMSO) δ 11.06 (d, J = 20.0 Hz, 1H), 9.34 (s, 1H), 8.49 (d, J = 5.1 Hz, 1H), 8.37 (d, J = 0.5 Hz, 1H), 8.30 (s, 1H), 7.38 (dt, J = 9.0, 4.5 Hz, 1H), 6.92 (s, 1H), 6.55 (d, J = 1.5 Hz, 1H), 6.37 (s, 2H), 2.62 (dt, J = 15.0, 7.5 Hz, 3H), 2.30-2.22 (m, 1H), 1.51-1.40 (m, 2H), 1.09 (t, J = 7.6 Hz, 3H). |
| 69 | 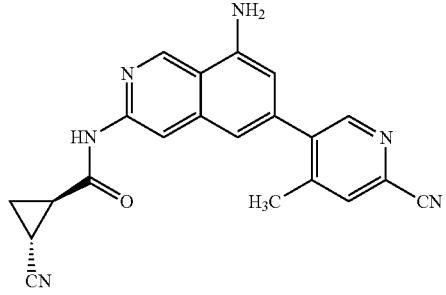 [SMILES: Cc1cc(C#N)ncc1-c1cc(N)c2cnc(NC(=O)[C@@H]3C[C@H]3C#N)cc2c1]<br>(±)-trans-N-(8-amino-6-(6-cyano-4-methylpyridin-3-yl)isoquinolin-3-yl)-2-cyanocyclopropane-1-carboxamide | 4.401<br>369.1<br>J | 1H NMR (400 MHz, DMSO) δ 11.13 (s, 1H), 9.36 (s, 1H), 8.59 (s, 1H), 8.26 (s, 1H), 8.06 (d, J = 0.7 Hz, 1H), 6.97 (d, J = 0.6 Hz, 1H), 6.57 (d, J = 1.5 Hz, 1H), 6.44 (s, 2H), 2.81-2.71 (m, 1H), 2.36 (s, 3H), 2.13 (ddd, J = 9.3, 6.1, 4.3 Hz, 1H), 1.59 (ddd, J = 8.6, 6.0, 4.4 Hz, 1H), 1.43 (ddd, J = 9.3, 5.9, 4.4 Hz, 1H). |
| 70 | 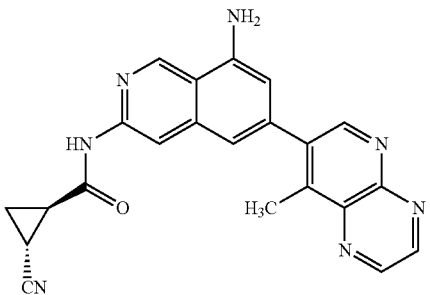 [SMILES: Cc1c(-c2cc(N)c3cnc(NC(=O)[C@@H]4C[C@H]4C#N)cc3c2)cnc2nccnc12]<br>(±)-trans-N-(8-amino-6-(8-methylpyrido[2,3-b]pyrazin-7-yl)isoquinolin-3-yl)-2-cyanocyclopropane-1-carboxamide | 3.847<br>396.1<br>J | 1H NMR (400 MHz, DMSO) δ 11.14 (s, 1H), 9.40 (s, 1H), 9.17 (t, J = 1.5 Hz, 1H), 9.14 (d, J = 1.8 Hz, 1H), 9.07 (s, 1H), 8.29 (s, 1H), 7.08 (s, 1H), 6.71 (d, J = 1.5 Hz, 1H), 6.47 (s, 2H), 2.82-2.73 (m, 4H), 2.14 (ddd, J = 9.3, 6.1, 4.3 Hz, 1H), 1.59 (ddd, J = 8.6, 6.0, 4.5 Hz, 1H), 1.43 (ddd, J = 9.2, 5.9, 4.4 Hz, 1H). |

Additional exemplary compounds of Formula I or Ia were prepared (Tables A-2, A-3 and A-4); and the binding data are shown in Tables B1-1 and B1-2.

TABLE A-2

| Compound No. | Structure | LCMS $R_T$ (min); $M + H^+$; Method |
|---|---|---|
| 71 trans enantiomer 1 | trans-N-(8-amino-6-(4-ethylpyridin-3-yl)isoquinolin-3-yl)-2-cyanocyclopropane-1-carboxamide | 2.999 358.1 N |
| 72 trans enantiomer 2 | trans-N-(8-amino-6-(4-ethylpyridin-3-yl)isoquinolin-3-yl)-2-cyanocyclopropane-1-carboxamide | 2.999 358.1 N |

TABLE A-2-continued

| Compound No. | Structure | LCMS R$_T$ (min); M + H$^+$; Method |
|---|---|---|
| 73 trans enantiomer 1 | *trans*-N-(8-amino-6-(4-methylpyridin-3-yl)isoquinolin-3-yl)-2-cyanocyclopropane-1-carboxamide | 1.38 344.1 E |
| 74 trans enantiomer 2 | *trans*-N-(8-amino-6-(4-methylpyridin-3-yl)isoquinolin-3-yl)-2-cyanocyclopropane-1-carboxamide | 1.38 344.1 E |

TABLE A-2-continued

| Compound No. | Structure | LCMS R_T (min); M + H+; Method |
|---|---|---|
| 75 trans racemic | | 2.76 383.1 N |
| | (±)-trans-N-(8-amino-6-(1-methyl-1H-pyrrolo[2,3-c]pyridin-4-yl)isoquinolin-3-yl)-2-cyanocyclopropane-1-carboxamide | |
| 76 trans racemic | 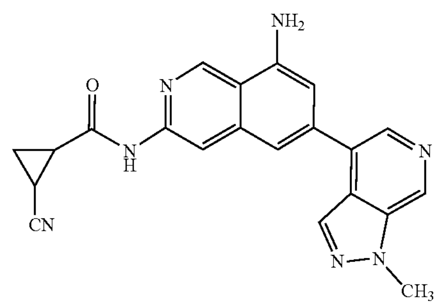 [SMILES: Cn1ncc2c(-c3cc(N)c4cnc(NC(=O)C5CC5C#N)cc4c3)cncc21] | 3.09 384.1 N |
| | (±)-trans-N-(8-amino-6-(1-methyl-1H-pyrazolo[3,4-c]pyridin-4-yl)isoquinolin-3-yl)-2-cyanocyclopropane-1-carboxamide | |
| 77 | 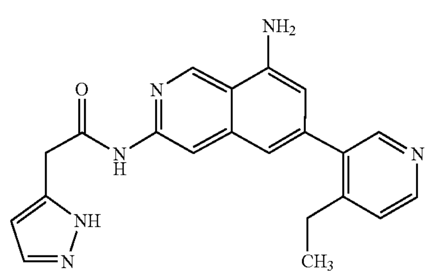 [SMILES: CCc1ccncc1-c1cc(N)c2cnc(NC(=O)Cc3ccn[nH]3)cc2c1] | |

TABLE A-2-continued
| Compound No. | Structure | LCMS R$_T$ (min); M + H$^+$; Method |
|---|---|---|
| 78 Trans racemic | 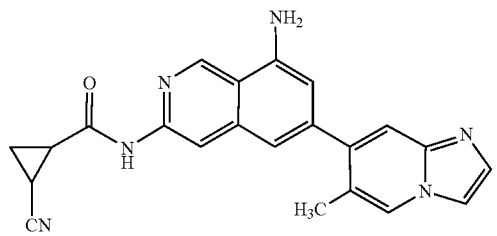 [SMILES: Cc1cn2ccnc2cc1-c1cc(N)c2cnc(NC(=O)C3CC3C#N)cc2c1] 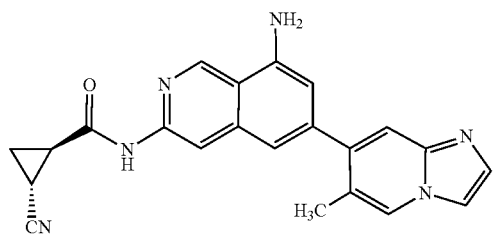 [SMILES: Cc1cn2ccnc2cc1-c1cc(N)c2cnc(NC(=O)[C@@H]3C[C@H]3C#N)cc2c1] (±)-trans-N-(8-amino-6-(6-methylimidazo[1,2-a]pyridin-7-yl)isoquinolin-3-yl)-2-cyanocyclopropane-1-carboxamide | n/a |
| 79 Trans racemic | 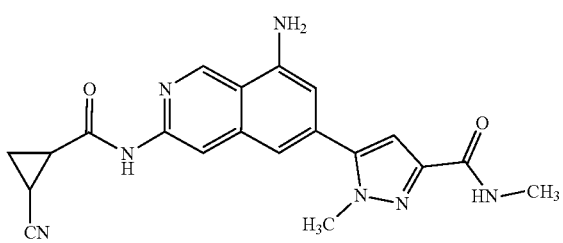 [SMILES: CNC(=O)c1cc(-c2cc(N)c3cnc(NC(=O)C4CC4C#N)cc3c2)n(C)n1] 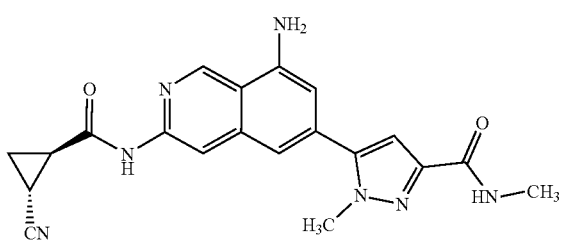 [SMILES: CNC(=O)c1cc(-c2cc(N)c3cnc(NC(=O)[C@@H]4C[C@H]4C#N)cc3c2)n(C)n1] (±)-5-(8-amino-3-((trans)-2-cyanocyclopropane-1-carboxamido)isoquinolin-6-yl)-N,1-dimethyl-1H-pyrazole-3-carboxamide | n/a |

TABLE A-2-continued

| Compound No. | Structure | LCMS $R_T$ (min); M + H[+]; Method |
|---|---|---|
| 80 Trans Racemic | | 1.65 369.1 C |

(±)-trans-N-(8-amino-7-cyano-6-(4-methylpyridin-3-yl)isoquinolin-3-yl)-2-cyanocyclopropane-1-carboxamide

| 81 Trans Racemic | | n/a |

(±)-trans-N-(8-amino-6-(3-(trifluoromethyl)-1H-pyrazol-4-yl)isoquinolin-3-yl)-2-cyanocyclopropane-1-carboxamide TABLE A-2-continued

| Compound No. | Structure | LCMS R_T (min); M + H+; Method |
|---|---|---|
| 82 Trans racemic | (±)-trans-N-(8-amino-6-(1H-pyrazol-4-yl)isoquinolin-3-yl)-2-cyanocyclopropane-1-carboxamide | n/a |
| 85 Trans racemic | (±)-trans-N-(8-amino-6-(4-methylpyridin-3-yl)isoquinolin-3-yl)-2-(hydroxymethyl)cyclopropane-1-carboxamide | 2.32 349.1 N |

TABLE A-2-continued

| Compound No. | Structure | LCMS R$_T$ (min); M + H$^+$; Method |
|---|---|---|
| 86 Trans racemic | (±)-trans-N-(8-amino-6-(2-methyl-2H-pyrazolo[3,4-c]pyridin-4-yl)isoquinolin-3-yl)-2-cyanocyclopropane-1-carboxamide | 2.70 384.1 N |
| 87 Trans racemic | (±)-trans-N-(8-amino-6-(1-methyl-4-oxo-1,4-dihydropyridin-2-yl)isoquinolin-3-yl)-2-cyanocyclopropane-1-carboxamide | 1.31 360.1 C |

TABLE A-2-continued

| Compound No. | Structure | LCMS R$_T$ (min); M + H$^+$; Method |
|---|---|---|
| 88 Trans racemic | (±)-trans-N-(8-amino-7-methyl-6-(4-methylpyridin-3-yl)isoquinolin-3-yl)-2-cyanocyclopropane-1-carboxamide | 1.31 358.1 C |
| 89 Trans racemic | (±)-trans-N-(8-amino-7-chloro-6-(4-methylpyridin-3-yl)isoquinolin-3-yl)-2-cyanocyclopropane-1-carboxamide | 1.67 378.1 C |

TABLE A-2-continued

| Compound No. | Structure | LCMS R$_T$ (min); M + H$^+$; Method |
|---|---|---|
| 90 Trans racemic | (±)-trans-N-(8-amino-6-(4-(dimethylamino)pyridin-3-yl)isoquinolin-3-yl)-2-cyanocyclopropane-1-carboxamide | 1.64 373.2 C |
| 91 Trans racemic | (±)-4-(8-amino-3-((trans)-2-cyanocyclopropane-1-carboxamido)isoquinolin-6-yl)-3-methyl-N-(2,2,2-trifluoroethyl)benzamide | 1.80 468.1 C |

TABLE A-2-continued

| Compound No. | Structure | LCMS R$_T$ (min); M + H$^+$; Method |
|---|---|---|
| 92 Trans Enantiomer 1 | | 1.67 400.1 E |
| | trans-N-(8-amino-6-(5-methyl-2-oxo-2,3-dihydrobenzo[d]oxazol-6-yl)isoquinolin-3-yl)-2-cyanocyclopropane-1-carboxamide | |
| 93 Trans Enantiomer 2 | 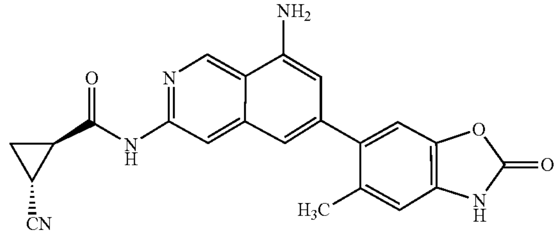 [SMILES: Cc1cc2[nH]c(=O)oc2cc1-c1cc(N)c2cnc(NC(=O)[C@@H]3C[C@H]3C#N)cc2c1] | 1.66 400.1 E |
| | trans-N-(8-amino-6-(5-methyl-2-oxo-2,3-dihydrobenzo[d]oxazol-6-yl)isoquinolin-3-yl)-2-cyanocyclopropane-1-carboxamide | |

TABLE A-2-continued

| Compound No. | Structure | LCMS R$_T$ (min); M + H$^+$; Method |
|---|---|---|
| 94 Trans Enantiomer 1 | trans-N-(8-amino-6-(4-(2-hydroxyethyl)pyridin-3-yl)isoquinolin-3-yl)-2-cyanocyclopropane-1-carboxamide | n/a |
| 95 Trans Enantiomer 2 | trans-N-(8-amino-6-(4-(2-hydroxyethyl)pyridin-3-yl)isoquinolin-3-yl)-2-cyanocyclopropane-1-carboxamide | 1.41 374.2 C |
| 96 | (±)-trans-N-(8-amino-6-(4-methylpyridin-3-yl)isoquinolin-3-yl)-2-(hydroxymethyl)cyclopropane-1-carboxamide | 1.30 349.2 C |

TABLE A-2-continued

| Compound No. | Structure | LCMS R$_T$ (min); M + H$^+$; Method |
|---|---|---|
| 97 trans racemic | | 1.65 369.1 E |

(±)-trans-N-(8-amino-7-cyano-6-(4-methylpyridin-3-yl)isoquinolin-3-yl)-2-cyanocyclopropane-1-carboxamide

| 98 | | n/a |
|---|---|---|

| 99 trans racemic | | 1.67 400.2 C |
|---|---|---|

(±)-3-(8-amino-3-((trans)-2-cyanocyclopropane-1-carboxamido)isoquinolin-6-yl)-N,4-dimethylbenzamide TABLE A-2-continued
| Compound No. | Structure | LCMS R_T (min); M + H+; Method |
|---|---|---|
| 100 trans racemic cyclopropyl | 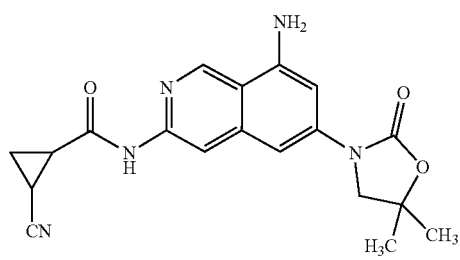 [SMILES: CC1(C)CN(c2cc(N)c3cnc(NC(=O)C4CC4C#N)cc3c2)C(=O)O1]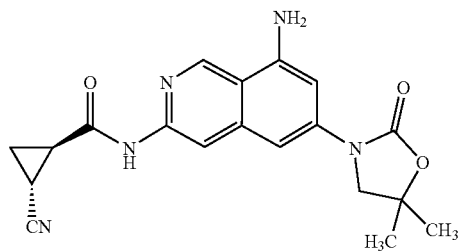 [SMILES: CC1(C)CN(c2cc(N)c3cnc(NC(=O)[C@@H]4C[C@H]4C#N)cc3c2)C(=O)O1] (±)-trans-N-(8-amino-6-(5,5-dimethyl-2-oxooxazolidin-3-yl)isoquinolin-3-yl)-2-cyanocyclopropane-1-carboxamide | 3.58 366.1 N |
| 101 trans racemic cyclopropyl; S-enantiomer at isopropyl center | 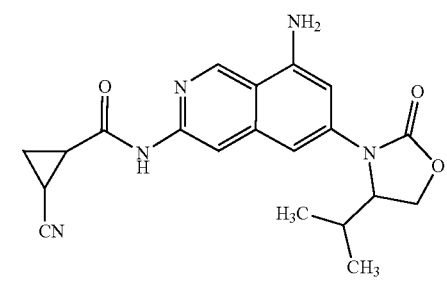 [SMILES: CC(C)C1COC(=O)N1c1cc(N)c2cnc(NC(=O)C3CC3C#N)cc2c1]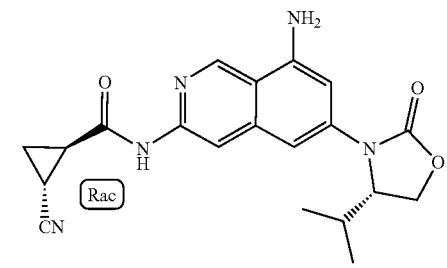 [SMILES: CC(C)[C@H]1COC(=O)N1c1cc(N)c2cnc(NC(=O)[C@@H]3C[C@H]3C#N)cc2c1] (±)-trans-N-(8-amino-6-((S)-4-isopropyl-2-oxooxazolidin-3-yl)isoquinolin-3-yl)-2-cyanocyclopropane-1-carboxamide | 3.89 380.1 N |

TABLE A-2-continued

| Compound No. | Structure | LCMS R_T (min); M + H+; Method |
|---|---|---|
| 102 trans racemic | | 2.53 377.1 N |

(±)-trans-N-(8-amino-7-fluoro-6-(4-methylpyridin-3-yl)isoquinolin-3-yl)-2-cyanocyclopropane-1-carboxamide

| 103 trans racemic cyclopropyl; R-enantiomer at isopropyl center | | 3.31 352.1 N |

(±)-trans-N-(8-amino-6-((R)-4-methyl-2-oxooxazolidin-3-yl)isoquinolin-3-yl)-2-cyanocyclopropane-1-carboxamide TABLE A-2-continued
| Compound No. | Structure | LCMS R$_T$ (min); M + H$^+$; Method |
|---|---|---|
| 104 | Removed | |
| 105 trans racemic | 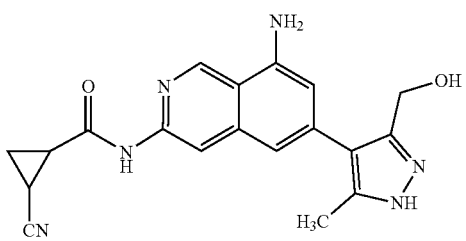 [SMILES: Cc1[nH]nc(CO)c1-c1cc(N)c2cnc(NC(=O)C3CC3C#N)cc2c1] 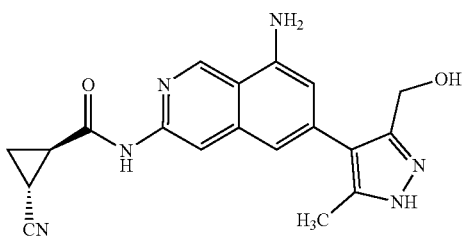 [SMILES: Cc1[nH]nc(CO)c1-c1cc(N)c2cnc(NC(=O)[C@@H]3C[C@H]3C#N)cc2c1] (±)-trans-N-(8-amino-6-(3-(hydroxymethyl)-5-methyl-1H-pyrazol-4-ypisoquinolin-3-yl)-2-cyanocyclopropane-1-carboxamide | 1.27 363.1 E |
| 106 trans racemic | 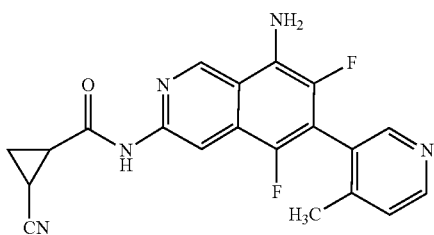 [SMILES: Cc1ccncc1-c1c(F)c(N)c2cnc(NC(=O)C3CC3C#N)cc2c1F] 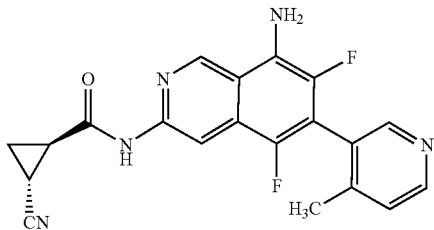 [SMILES: Cc1ccncc1-c1c(F)c(N)c2cnc(NC(=O)[C@@H]3C[C@H]3C#N)cc2c1F] (±)-trans-N-(8-amino-5,7-difluoro-6-(4-methylpyridin-3-yl)isoquinolin-3-yl)-2-cyanocyclopropane-1-carboxamide | n/a |

TABLE A-2-continued
| Compound No. | Structure | LCMS R_T (min); M + H+; Method |
|---|---|---|
| 107 trans racemic | 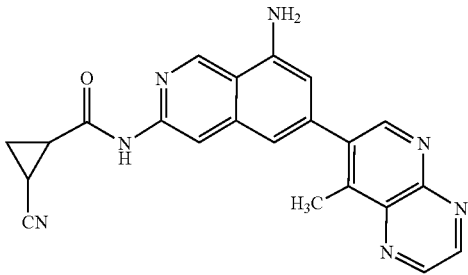 [SMILES: Cc1c(-c2cc(N)c3cnc(NC(=O)C4CC4C#N)cc3c2)cnc2nccnc12] 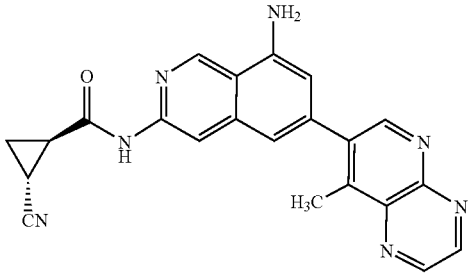 [SMILES: Cc1c(-c2cc(N)c3cnc(NC(=O)[C@@H]4C[C@H]4C#N)cc3c2)cnc2nccnc12]<br>(±)-trans-N-(8-amino-6-(8-methylpyrido[2,3-b]pyrazin-7-yl)isoquinolin-3-yl)-2-cyanocyclopropane-1-carboxamide | 3.847 396.1 J |
| 108 S,S-Cis-F-cyclopropyl; racemic at methyl center | 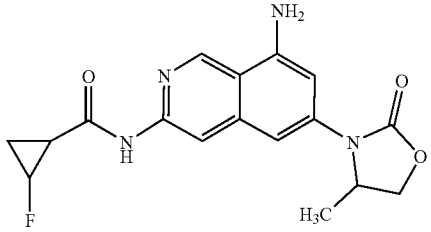 [SMILES: CC1COC(=O)N1c1cc(N)c2cnc(NC(=O)C3CC3F)cc2c1] 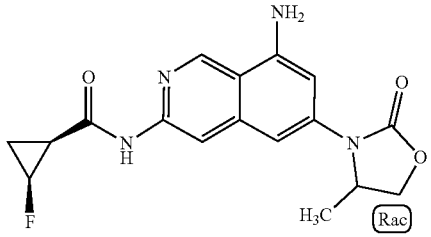 [SMILES: CC1COC(=O)N1c1cc(N)c2cnc(NC(=O)[C@@H]3C[C@@H]3F)cc2c1]<br>cis-N-(8-amino-6-(4-methyl-2-oxooxazolidin-3-yl)isoquinolin-3-yl)-2-fluorocyclopropane-1-carboxamide | 1.538 345.1 E |

TABLE A-3

| Compound No. | Structure/Name | LCMS R_T (min), M + H+, method | $^1$H NMR (ppm) |
|---|---|---|---|
| 109 | (±)-trans-N-(8-amino-6-(6-methylimidazo[1,2-a]pyridin-7-yl)isoquinolin-3-yl)-2-cyanocyclopropanecarboxamide | 1.646<br>383.7<br>C | $^1$H NMR (400 MHz, CD$_3$OD) δ 9.26 (s, 1H), 8.37 (s, 1H), 8.30 (s, 1H), 7.82 (s, 1H), 7.59 (s, 1H), 7.45 (s, 1H), 7.04 (s, 1H), 6.74 (s,1H), 2.66-2.64 (m, 1H), 2.27 (s, 3H), 2.15-2.10 (m, 1H), 1.61-1.57 (m, 2H). |
| 110 | (±)-trans-5-(8-amino-3-(trans-2-cyanocyclopropanecarboxamido)isoquinolin-6-yl)-N,1-dimethyl-1H-pyrazole-3-carboxamide | 1.543<br>390.7<br>C | $^1$H NMR (400 MHz, CD$_3$OD) δ 9.25 (s, 1H), 8.32 (s, 1H), 7.15 (s,1H), 6.84 (s, 1H), 6.80 (d, J = 1.2 Hz, 1H), 3.99 (s, 3H), 2.93 (s, 3H), 2.65-2.62 (m, 1H), 2.15-2.10 (m, 1H), 1.62-1.48 (m, 2H). |
| 113 | (±)-trans-N-[8-amino-7-cyano-6-(4-methyl-3-pyridyl)-3-isoquinolyl]-2-cyano-cyclopropanecarboxamide | 1.593<br>369.1<br>G<br>(racemate) | Enantiomer #1: $^1$H NMR (400 MHz, DMSO-d$_6$) δ 11.32 (s, 1H), 9.55 (s, 1H), 8.52 (d, J = 5.2 Hz, 1H), 8.41 (s, 1H), 8.27 (s, 1H), 7.44 (s, 2H), 7.40 (d, J = 5.2 Hz, 1H), 6.93 (s, 1H), 2.78-2.75 (m, 1H), 2.22 (s, 3H), 2.19-2.13 (m, 1H), 1.64-1.60 (m, 1H), 1.46-1.42 (m, 1H). Enantiomer #2: $^1$H NMR (400 MHz, DMSO-d$_6$) δ 11.32 (s, 1H), 9.55 (s, 1H), 8.52 (d, J = 5.2 Hz, 1H), 8.41 (s, 1H), 8.26 (s, 1H), 7.42 (s, 2H), 7.40 (d, J = 5.2 Hz, 1H), 6.93 (s, 1H), 2.78-2.75 (m, 1H), 2.22 (s, 3H), 2.19-2.13 (m, 1H), 1.64-1.60 (m, 1H), 1.46-1.42 (m, 1H). |
| 115 | (±)-trans-N-[8-amino-7-methyl-6-(4-methyl-3-pyridyl)-3-isoquinolyl]-2-cyano-cyclopropanecarboxamide | 1.70<br>358.1<br>C | $^1$H NMR (400 MHz, CD$_3$OD) δ 9.31 (s, 1H), 8.45 (d, J = 5.2 Hz, 1H), 8.28 (s, 1H), 8.22 (s, 1H), 7.42 (d, J = 5.2 Hz, 1H), 6.90 (s, 1H), 2.66-2.62 (m, 1H), 2.16 (s, 3H), 2.13-2.08 (m, 1H), 1.98 (s, 3H), 1.61-1.52 (m, 2H). |

TABLE A-3-continued

| Compound No. | Structure/Name | LCMS R$_T$ (min), M + H$^+$, method | $^1$H NMR (ppm) |
|---|---|---|---|
| 116 | (±)-trans-N-[8-amino-6-[4-(dimethylamino)-3-pyridyl]-3-isoquinolyl]-2-cyano-cyclopropanecarboxamide | 1.64 373.2 C | $^1$H NMR (400 MHz, CD$_3$OD) δ 9.21 (s, 1H), 8.26 (s, 1H), 8.17 (d, J = 6.0 Hz, 1H), 8.11 (s, 1H), 7.07 (s, 1H), 6.93 (d, J = 6.0 Hz, 1H), 6.80 (d, J = 1.2 Hz, 1H), 2.77 (s, 6H), 2.65-2.62 (m, 1H), 2.14-2.09 (m, 1H), 1.62-1.52 (m, 2H). |
| 117 | (±)-trans-N-(8-amino-6-(1-methyl-4-oxo-1,4-dihydropyridin-2-yl)isoquinolin-3-yl)-2-cyanocyclopropanecarboxamide | 1.310 360.1 G | $^1$H NMR (400 MHz, DMSO-d$_6$) δ 11.15 (s, 1H), 9.37 (s, 1H), 8.27 (s, 1H), 7.74 (d, J = 7.6 Hz, 1H), 6.99 (s, 1H), 6.54-6.51 (m, 3H), 6.14 (dd, J = 2.8, 7.6 Hz, 1H), 6.02 (d, J = 2.8 Hz, 1H), 3.41 (s, 3H), 2.77-2.73 (m, 1H), 2.17-2.12 (m, 1H), 1.62-1.57 (m, 1H), 1.45-1.41 (m, 1H). |
| 118 | (±)-trans-N-(8-amino-6-(3-(hydroxymethyl)-5-methyl-1H-pyrazol-4-yl)isoquinolin-3-yl)-2-cyanocyclopropanecarboxamide | 1.268 363.1 A | $^1$HNMR (400 MHz, CD$_3$OD) δ 9.19 (s, 1H), 8.26 (s, 1H), 7.12 (s, 1H), 6.85 (s, 1H), 4.63 (s, 2H), 2.67-2.62 (m, 1H), 2.38 (s, 3H), 2.14-2.09 (m, 1H), 1.61-1.53 (m, 2H). |
| 119 | (±)-trans-N-(8-amino-6-(4-methylpyridin-3-yl)isoquinolin-3-yl)-2-(hydroxymethyl)cyclopropanecarboxamide | 1.302 349.2 B (racemate) | Enantiomer #1: $^1$H NMR (400 MHz, DMSO) δ : 10.70 (s, 1H), 9.30 (s, 1H), 8.44 (m, 1H), 8.43 (s, 1H), 8.25 (s, 1H), 7.43 (m, 1H), 6.88 (s, 1H), 6.54 (s, 1H), 6.31 (s, 2H), 4.66 (m, 1H), 2.29 (s, 3H), 1.97 (m, 1H), 1.50 (m, 1H), 1.01 (m, 1H), 0.79 (m, 1H). Enantiomer #2: $^1$H NMR (400 MHz, DMSO) δ : 10.66 (s, 1H), 9.30 (s, 1H), 8.48 (m, 1H), 8.40 (s, 1H), 8.26 (s, 1H), 7.35 (m, 1H), 6.88 (s, 1H), 6.54 (s, 1H), 6.31 (s, 2H), 4.66 (m, 1H), 2.30 (s, 3H), 1.97 (m, 1H), 1.49 (m, 1H), 1.01 (m, 1H), 0.79 (m, 1H). |

TABLE A-3-continued

| Compound No. | Structure/Name | LCMS R_T (min), M + H+, method | 1H NMR (ppm) |
|---|---|---|---|
| 122 | 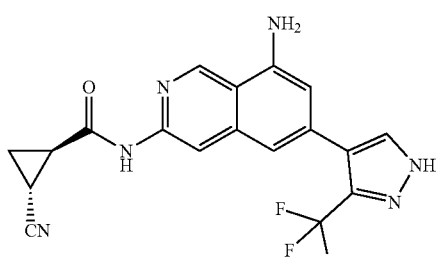<br>(±)-trans-N-[8-amino-6-[3-(trifluoromethyl)-1H-pyrazol-4-yl]-3-isoquinolyl]-2-cyano-cyclopropanecarboxamide | 1.69<br>387.1<br>B | 1H NMR (400 MHz, CD3OD) δ 9.27 (s, 1H), 8.07 (s, 1H), 8.04 (s, 1H), 7.19 (s, 1H), 6.92 (s, 1H), 2.63-2.61 (m, 1H), 2.20-2.15 (m, 1H), 1.65-1.59 (m, 2H). |
| 123 | 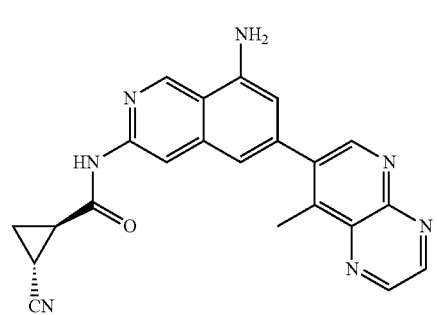<br>(±)-trans-N-(8-amino-6-(8-methylpyrido[3,2-b]pyrazin-7-yl)isoquinolin-3-yl)-2-cyanocyclopropane carboxamide | 1.65<br>396.2<br>B | 1H NMR (400 MHz, DMSO-d6) δ 11.15 (s, 1H), 9.40 (s, 1H), 9.17 (d, J = 1.6 Hz, 1H), 9.13 (d, J = 1.6 Hz, 1H), 9.06 (s, 1H), 8.29 (s, 1H), 7.08 (s, 1H), 6.71 (s, 1H), 6.48 (s, 2H), 2.79-2.75 (m, 3H), 2.15-2.11 (m, 1H), 1.61-1.59 (m, 1H), 1.44-1.42 (m, 1H). |
| 124 | 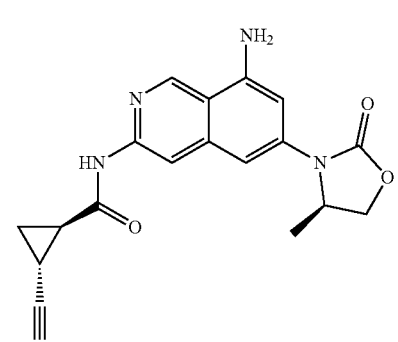<br>trans-N-(8-amino-6-((R)-4-methyl-2-oxooxazolidin-3-yl)isoquinolin-3-yl)-2-cyanocyclopropane-1-carboxamide | 1.56<br>352.2<br>B | 1H NMR (400 MHz, DMSO-d6) δ 11.04 (s, 1H), 9.21 (s, 1H), 8.15 (s, 1H), 7.00 (d, J = 1.6 Hz, 1H), 6.94 (d, J = 1.6 Hz, 1H), 6.35 (s, 2H), 4.70-4.67 (m, 1H), 4.57-4.53 (m, 1H), 4.06-4.03 (m, 1H), 2.75-2.73 (m, 1H), 2.14-2.10 (m, 1H), 1.60-1.58 (m, 1H), 1.42-1.38 (m, 1H), 1.28 (d, J = 6.0 Hz, 3H). |

| Compound No. | Structure/Name | LCMS R_T (min), M + H+, method | $^1$H NMR (ppm) |
|---|---|---|---|
| 125 | 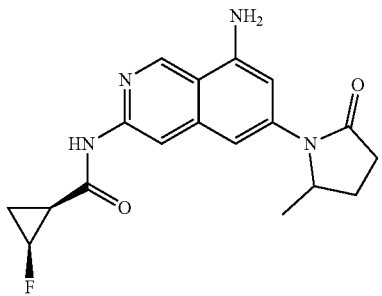<br>(1S,2S)-N-(8-amino-6-(2-methyl-5-oxopyrrolidin-1-yl)isoquinolin-3-yl)-2-fluorocyclopropanecarboxamide | 1.52<br>343.1<br>B | $^1$HNMR (400 MHz, CD$_3$OD) δ 9.14 (s, 1H), 8.11 (s, 1H), 7.09 (s, 1H), 6.92 (s, 1H), 4.98 (d, J = 3.6 Hz, 0.5H), 4.82-4.81 (m, 0.5H), 4.51 (d, J = 6.4 Hz, 1H), 2.72-2.61 (m, 1H), 2.59-2.53 (m, 1H), 2.48-2.41 (m, 1H), 2.16-2.14 (m, 1H), 1.88-1.78 (m, 2H), 1.28-1.21 (m, 4H). |
| 126 | 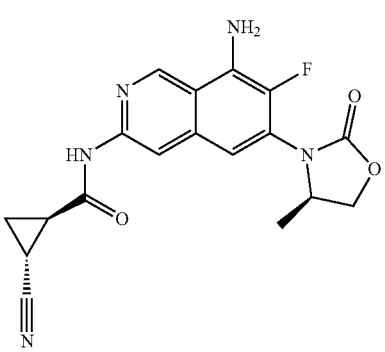<br>trans-N-(8-amino-7-fluoro-6-((R)-4-methyl-2-oxooxazolidin-3-yl)isoquinolin-3-yl)-2-cyanocyclopropanecarboxamide | 1.65<br>370.2<br>B | 1.65, [M + H]+ = 370.2, method = B. $^1$HNMR (400 MHz, DMSO-d$_6$) δ 11.14 (s, 1H), 9.39 (s, 1H), 8.22 (s, 1H), 7.05 (d, J = 6.4 Hz, 1H), 6.37 (s, 2H), 4.67 (t, J = 8.4 Hz, 1H), 4.54-4.52 (m, 1H), 4.06 (t, J = 8.0 Hz, 1H), 2.77-2.76 (m, 1H), 2.14-2.12 (m, 1H), 1.60-1.56 (m, 1H), 1.44-1.42 (m, 1H), 1.15 (d, J = 6.0 Hz, 3H). |
| 127 | 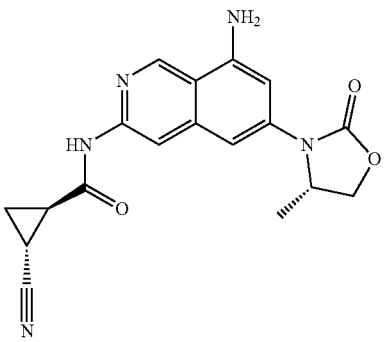<br>trans-N-(8-amino-6-((S)-4-methyl-2-oxooxazolidin-3-yl)isoquinolin-3-yl)-2-cyanocyclopropanecarboxamide | 1.52<br>352.1<br>B | 1.52, [M + H]+ = 352.1, method = B. $^1$HNMR (400 MHz, DMSO-d$_6$) δ 11.03 (s, 1H), 9.20 (s, 1H), 8.15 (s, 1H), 7.00 (d, J = 1.6 Hz, 1H), 6.94 (d, J = 1.6 Hz, 1H), 6.35 (s, 2H), 4.70-4.67 (m, 1H), 4.57-5.54 (m, 1H), 4.06-4.03 (m, 1H), 2.75-2.72 (m, 1H), 2.14-2.10 (m, 1H), 1.60-1.55 (m, 1H), 1.44-1.40 (m, 1H), 1.28 (d, J = 6.4 Hz, 3H). |

TABLE A-3-continued

| Compound No. | Structure/Name | LCMS $R_T$ (min), $M + H^+$, method | $^1$H NMR (ppm) |
|---|---|---|---|
| 128 | 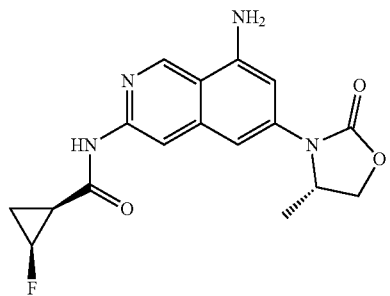<br>(1S,2S)-N-(8-amino-6-((S)-4-methyl-2-oxooxazolidin-3-yl)isoquinolin-3-yl)-2-fluorocyclopropanecarboxamide | 1.47<br>345.1<br>B | $^1$HNMR (400 MHz, DMSO-d$_6$) δ 10.75 (s, 1H), 9.19 (s, 1H), 8.19 (s, 1H), 7.00 (d, J = 2.0 Hz, 1H), 6.93 (s, 1H), 6.32 (s, 2H), 5.02-5.00 (m, 0.5H), 4.84-4.83 (m, 0.5H), 4.72-4.67 (m, 1H), 4.58-4.54 (m, 1H), 4.06-4.03 (m, 1H), 2.26-2.23 (m, 1H), 1.69-1.63 (m, 1H), 1.28 (d, J = 6.4 Hz, 3H), 1.17-1.13 (m, 1H). |
| 130 | 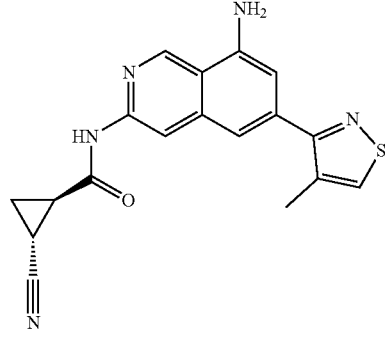<br>(±)-trans-N-(8-amino-6-(4-methylisothiazol-3-yl)isoquinolin-3-yl)-2-cyanocyclopropane carboxamide | 1.698<br>350.1<br>C | $^1$H NMR (400 MHz, DMSO-d$_6$) δ 11.12 (s, 1H), 9.33 (s, 1H), 8.81 (d, J = 0.4 Hz, 1H), 8.29 (s, 1H), 7.20 (s, 1H), 6.97 (d, J = 1.2 Hz, 1H), 6.37 (s, 2H), 2.78-2.73 (m, 1H), 2.42 (s, 3H), 2.16-2.12 (m, 1H), 1.62-1.57 (m,1H), 1.46-1.41 (m, 1H). |
| 131 | 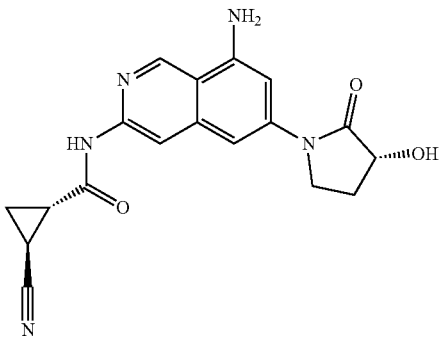<br>trans-N-(8-amino-6-((R)-3-hydroxy-2-oxopyrrolidin-1-yl)isoquinolin-3-yl)-2-cyanocyclopropanecarboxamide | 1.396<br>352.1<br>C | $^1$H NMR (400 MHz, DMSO-d$_6$) δ 11.02 (s, 1H), 9.20 (s, 1H), 8.14 (s, 1H), 7.28 (d, J = 1.6 Hz, 1H), 7.05 (d, J = 1.6 Hz, 1H), 6.315 (s, 2H), 5.78-5.77 (m, 1H), 4.34-4.28 (m, 1H), 3.82-3.71 (m, 1H), 2.77-2.72 (m, 1H), 2.44-2.33 (m, 1H), 2.15-2.10 (m, 1H), 1.87-1.82 (m, 1H), 1.60-1.56 (m, 1H), 1.44-1.40 (m, 1H). |

TABLE A-3-continued

| Compound No. | Structure/Name | LCMS R$_T$ (min), M + H$^+$, method | $^1$H NMR (ppm) |
|---|---|---|---|
| 132 | 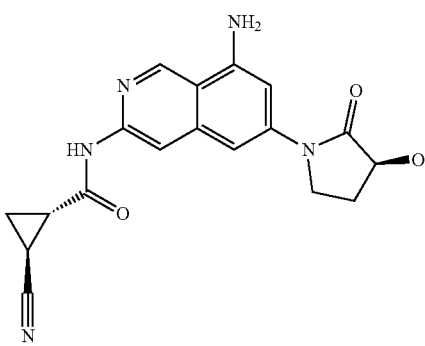<br>trans-N-(8-amino-6-((S)-3-hydroxy-2-oxopyrrolidin-1-yl)isoquinolin-3-yl)-2-cyanocyclopropanecarboxamide | 1.394<br>352.1<br>C | $^1$H NMR (400 MHz, DMSO-d$_6$) δ 11.04 (s, 1H), 9.20 (s, 1H), 8.14 (s, 1H), 7.28 (d, J = 1.6 Hz, 1H), 7.05 (d, J = 1.6 Hz, 1H), 6.33 (s, 2H), 5.79-5.78 (m, 1H), 4.34-4.28 (m, 1H), 3.79-3.71 (m, 1H), 2.75-2.73 (m, 1H), 2.42-2.39 (m, 1H), 2.13-2.10 (m, 1H), 1.87-1.82 (m, 1H), 1.61-1.56 (m, 1H), 1.44-1.41 (m, 1H). |
| 133 | 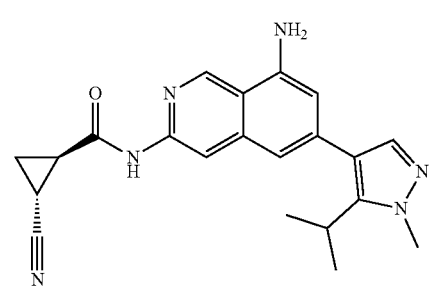<br>(±)-trans-N-[8-amino-6-(5-isopropyl-1-methyl-pyrazol-4-yl)-3-isoquinolyl]-2-cyano-cyclopropanecarboxamide | 1.72<br>375.2<br>F | $^1$HNMR (400 MHz, CD$_3$OD) δ 9.19 (s, 1H), 8.23 (s, 1H), 7.45 (s, 1H), 6.96 (s, 1H), 6.73 (d, J = 1.6 Hz, 1H), 3.95 (s, 3H), 3.47-3.40 (m, 1H), 2.67-2.62 (m, 1H), 2.15-2.10 (m, 1H), 1.62-1.52 (m, 2H), 1.36 (d, J = 6.8 Hz, 6H). |
| 134 | 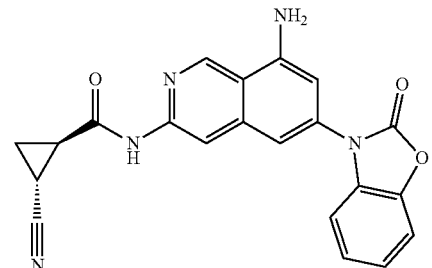<br>(±)-trans-N-[8-amino-6-(2-oxo-1,3-benzoxazol-3-yl)-3-isoquinolyl]-2-cyano-cyclopropane carboxamide | 1.83<br>386.1<br>B | $^1$H NMR (400 MHz, DMSO-d$_6$) δ 11.18 (s, 1H), 9.38 (s, 1H), 8.28 (s, 1H), 7.46 (s, 1H), 7.25-7.22 (m, 3H), 7.16 (s, 1H), 6.82 (d, J = 1.2 Hz, 1H), 6.65-6.64 (m, 2H), 2.78-2.76 (m, 1H), 2.17-2.12 (m, 1H), 1.62-1.58 (m, 1H), 1.46-1.41 (m, 1H). |
| 135 | 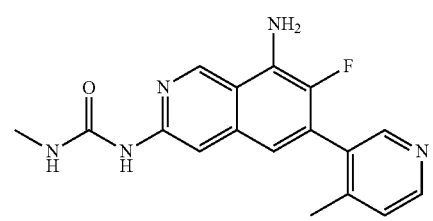<br>1-[8-amino-7-fluoro-6-(4-methyl-3-pyridyl)-3-isoquinolyl]-3-methyl-urea | 1.40<br>326.1<br>E | $^1$H NMR (400 MHz, CD$_3$OD) δ 9.25 (s, 1H), 8.47 (d, J = 5.6 Hz, 1H), 8.41 (s, 1H), 7.53 (s, 1H), 7.40 (d, J = 5.2 Hz, 1H), 6.91 (d, J = 6.0 Hz, 1H), 2.91 (s, 3H), 2.31 (s, 3H). |

TABLE A-3-continued

| Compound No. | Structure/Name | LCMS R_T (min), M + H+, method | 1H NMR (ppm) |
|---|---|---|---|
| 136 | 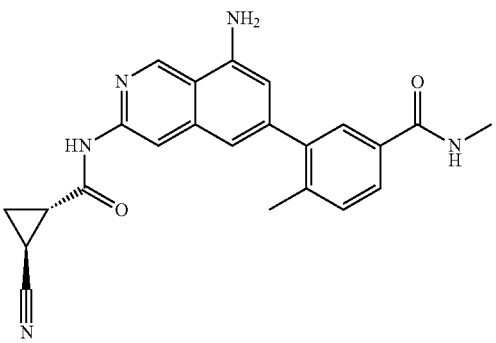<br>(±)-trans-3-(8-amino-3-(2-cyanocyclopropanecarboxamido)isoquinolin-6-yl)-N,4-dimethylbenzamide | 1.67<br>400.1<br>C | 1H NMR (400 MHz, CD3OD): δ 9.24 (s, 1H), 8.27 (s, 1H), 7.75-7.73 (m, 2H), 7.40-7.38 (m, 1H), 6.97 (s, 1H), 6.71 (s, 1H), 2.92 (s, 3H), 2.67-2.62 (m, 1H), 2.34 (s, 3H), 2.14-2.09 (m, 1H), 1.62-1.52 (m, 2H). |
| 138 | 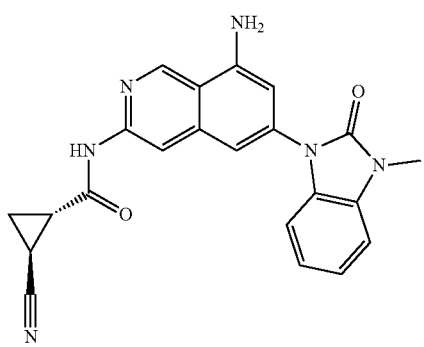<br>(±)-trans-N-(8-amino-6-(3-methyl-2-oxo-2,3-dihydro-1H-benzo[d]imidazol-1-yl)isoquinolin-3-yl)-2-cyanocyclopropanecarboxamide | 1.77<br>399.1<br>C | 1H NMR (400 MHz, DMSO-d6): δ 11.15 (s, 1H), 9.35 (s, 1H), 8.26 (s, 1H), 7.27-7.08 (m, 5H), 6.78 (s, 1H), 6.54 (s, 2H), 3.17 (s, 3H), 2.77-2.74 (m, 1H), 2.17-2.12 (m, 1H), 1.62-1.57 (m, 1H), 1.46-1.41 (m, 1H). |
| 139 | 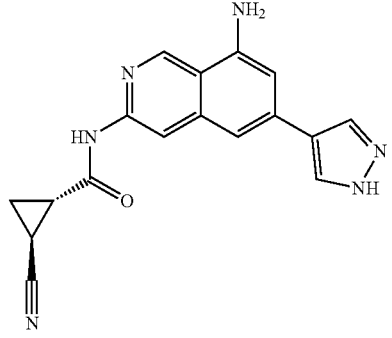<br>(±)-trans-N-(8-amino-6-(1H-pyrazol-4-yl)isoquinolin-3-yl)-2-cyanocyclopropanecarboxamide | 1.47<br>319.7<br>C | 1HNMR (400 MHz, DMSO-d6): δ 13.01 (s, 1H), 11.02 (s, 1H), 9.21 (s, 1H), 8.21 (s, 1H), 8.17 (s, 1H), 7.94 (s, 1H), 7.19 (s, 1H), 6.86 (s, 1H), 6.17 (s, 2H), 2.77-2.74 (m, 1H), 2.15-2.11 (m, 1H), 1.61-1.56 (m, 1H), 1.46-1.41 (m, 1H). |

TABLE A-3-continued

| Compound No. | Structure/Name | LCMS R$_T$ (min), M + H$^+$, method | $^1$H NMR (ppm) |
|---|---|---|---|
| 140 | 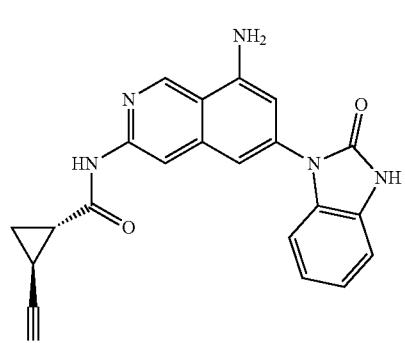<br>(±)-trans-N-(8-amino-6-(2-oxo-2,3-dihydro-1H-benzo[d]imidazol-1-yl)isoquinolin-3-yl)-2-cyanocyclopropanecarboxamide | 1.64<br>385.1<br>C | $^1$HNMR (400 MHz, DMSO-d$_6$): δ 11.13 (s, 1H), 9.34 (s, 1H), 8.25 (s, 1H), 7.15-7.00 (m, 6H), 6.79 (s, 1H), 6.51 (s, 2H), 2.78-2.74 (m, 1H), 2.17-2.12 (m, 1H), 1.61-1.57 (m, 1H), 1.46-1.41 (m, 1H). |
| 143 | 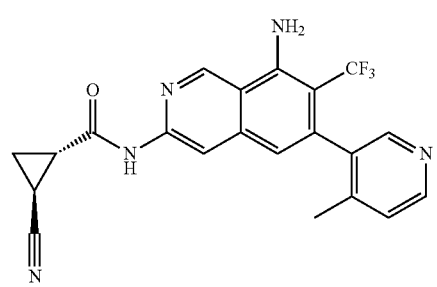<br>(±)-trans-N-(8-amino-6-(4-methylpyridin-3-yl)-7-(trifluoromethyl)isoquinolin-3-yl)-2-cyanocyclopropanecarboxamide | 1.864<br>421.1<br>C | 1.864, [M + H]$^+$ = 421.1, Method = C; $^1$HNMR (400 MHz, CD$_3$OD): δ 9.41 (s, 1H), 8.39 (s, 1H), 8.25-8.23 (m, 2H), 7.35 (s, 1H), 6.74 (s, 1H), 2.64-2.26 (m, 1H), 2.16 (s, 3H), 2.09-2.05 (m, 1H), 1.57-1.47 (m, 2H). |
| 144 | 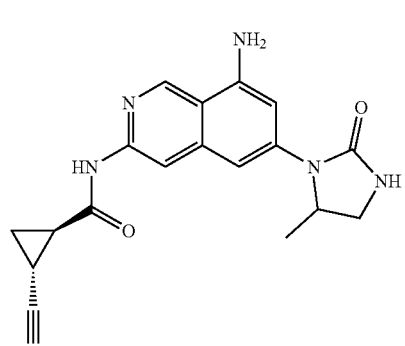<br>(±)-trans-N-(8-amino-6-(5-methyl-2-oxoimidazolidin-1-yl)isoquinolin-3-yl)-2-cyanocyclopropanecarboxamide | 1.332<br>351.2<br>A | $^1$HNMR (400 MHz, DMSO-d$_6$): δ 10.96 (s, 1H), 9.11 (s, 1H), 8.08 (s, 1H), 7.36 (s, 1H), 7.25 (s, 1H), 6.71 (s, 1H), 6.18 (s, 2H), 4.12-3.97 (m, 2H), 3.81-3.75 (m, 1H), 2.76-2.67 (m, 1H), 2.14-2.08 (m, 1H), 1.58-1.50 (m, 1H), 1.42-1.40 (m, 1H), 1.20 (d, J = 6.0 Hz, 3H). |

TABLE A-3-continued

| Compound No. | Structure/Name | LCMS $R_T$ (min), M + H$^+$, method | $^1$H NMR (ppm) |
|---|---|---|---|
| 145 | 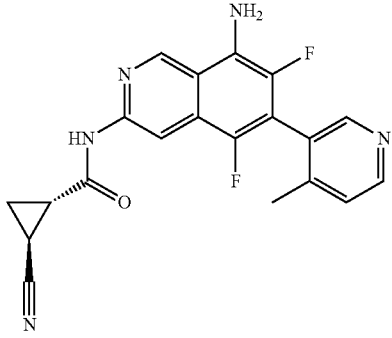<br>(±)-trans-N-(8-amino-5,7-difluoro-6-(4-methylpyridin-3-yl)isoquinolin-3-yl)-2-cyanocyclopropanecarboxamide | 1.625<br>380.2<br>G | $^1$H NMR (400 MHz, DMSO-d6) δ 11.32 (s, 1H), 9.53 (s, 1H), 8.55 (d, J = 5.2 Hz, 1H), 8.48 (s, 1H), 8.42 (s, 1H), 7.48 (d, J = 5.2 Hz, 1H), 6.20 (s, 2H), 2.62-2.75 (m, 1H), 2.11-2.25 (m, 4H), 1.60-1.68 (m, 1H), 1.40-1.48 (m, 1H). |
| 146 | 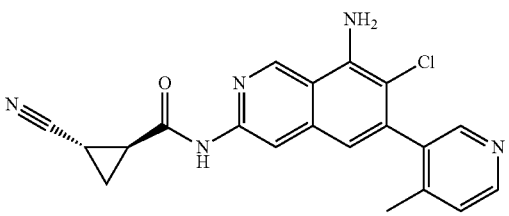<br>(±)-trans-N-(8-amino-7-chloro-6-(4-methylpyridin-3-yl)isoquinolin-3-yl)-2-cyanocyclopropanecarboxamide | 1.667<br>378.1<br>G | $^1$H NMR (400 MHz, DMSO-d$_6$) δ 9.49 (s, 1H), 8.48 (d, J = 5.2 Hz, 1H), 8.32 (s, 1H), 8.24 (s, 1H), 7.36 (d, J = 5.2 Hz, 1H), 6.96 (s, 1H), 6.61 (s, 1H), 6.03 (br, 2H), 2.79-2.71 (m, 1H), 2.17-2.10 (m, 1H), 2.11 (s, 3H), 1.63-1.55 (m, 1H), 1.46-1.40 (m, 1H). |
| 147 | 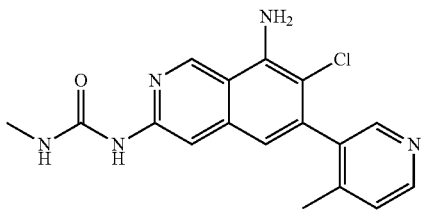<br>1-(8-amino-7-chloro-6-(4-methylpyridin-3-yl)isoquinolin-3-yl)-3-methylurea & 1-(8-amino-5-chloro-6-(4-methylpyridin-3-yl)isoquinolin-3-yl)-3-methylurea | 1.533<br>342.2<br>G | $^1$H NMR (400 MHz, DMSO-d$_6$) δ 9.35 (s, 1H), 9.12 (s, 1H), 8.48 (d, J = 5.2 Hz, 1H), 8.31 (s, 1H), 7.82 (s, 1H), 7.36 (d, J = 5.2 Hz, 1H), 7.04 (q, J = 4.8 Hz, 1H), 6.85 (s, 1H), 6.52 (s, 2H), 2.71 (d, J = 4.8 Hz, 3H), 2.12 (s, 3H). |
| 148 | 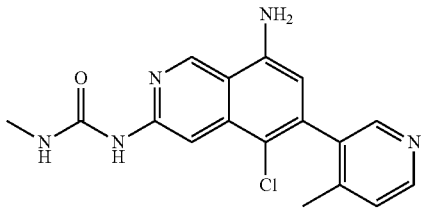<br>1-(8-amino-5-chloro-6-(4-methylpyridin-3-yl)isoquinolin-3-yl)-3-methylurea | 1.499<br>342.1<br>G | 1.499, [M + H]$^+$ = 342.1, method = G;<br>$^1$H NMR (400 MHz, DMSO-d6) δ 9.28 (s, 1H), 9.23 (s, 1H), 8.48 (d, J = 5.2 Hz, 1H), 8.32 (s, 1H), 8.22 (s, 1H), 7.37 (d, J = 5.2 Hz, 1H), 7.06 (q, J = 4.8 Hz, 1H), 6.49 (s, 2H), 6.36 (s, 1H), 2.72 (d, J = 4.8 Hz, 3H), 2.12 (s, 3H). |

| Compound No. | Structure/Name | LCMS $R_T$ (min), M + H+, method | 1H NMR (ppm) |
|---|---|---|---|
| 149 | 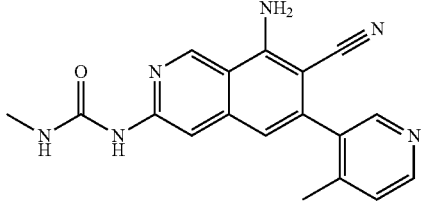<br>1-(8-amino-5-cyano-6-(4-methylpyridin-3-yl)isoquinolin-3-yl)-3-methylurea | 1.512<br>333.1<br>C | 1H NMR (400 MHz, DMSO-d6) δ 9.41 (s, 1H), 9.32 (s, 1H), 8.51 (d, J = 5.2 Hz, 1H), 8.39 (s, 1H), 7.86 (s, 1H), 7.39 (d, J = 5.2 Hz, 1H), 7.35 (s, 2H), 7.07 (q, J = 4.4 Hz, 1H), 6.80 (s, 1H), 2.71 (d, J = 4.4 Hz, 3H), 2.22 (s, 3H). |
| 150 | 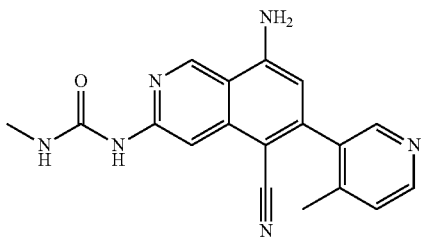<br>1-(8-amino-7-cyano-6-(4-methylpyridin-3-yl)isoquinolin-3-yl)-3-methylurea | 1.428<br>333.2<br>G | 1H NMR (400 MHz, DMSO-d6) δ 9.37 (s, 1H), 9.34 (s, 1H), 8.54 (d, J = 5.2 Hz, 1H), 8.43 (s, 1H), 8.18 (s, 1H), 7.50 (s, 2H), 7.43 (d, J = 5.2 Hz, 1H), 7.00 (q, J = 4.4 Hz, 1H), 6.41 (s, 1H), 2.73 (d, J = 4.4 Hz, 3H), 2.22 (s, 3H). |
| 151 | 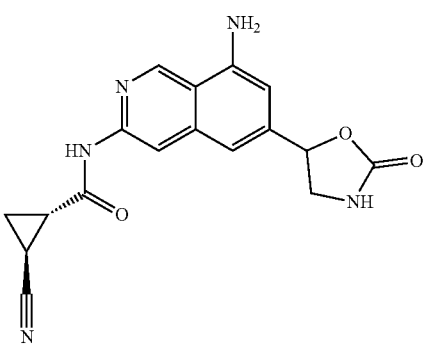<br>trans-N-[8-amino-6-(2-oxooxazolidin-5-yl)-3-isoquinolyl]-2-cyano-cyclopropane carboxamide | 1.398<br>338.0<br>C | 1H NMR (400 MHz, CD3OD) δ 9.20 (s, 1H), 8.27 (s, 1H), 7.06 (s, 1H), 6.74 (s, 1H), 5.72-5.68 (m, 1H), 4.07-4.02 (m, 1H), 3.53-3.49 (m, 1H), 2.65-2.62 (m, 1H), 2.13-2.11 (m, 1H), 1.61-1.53 (m, 1H). |
| 153 | 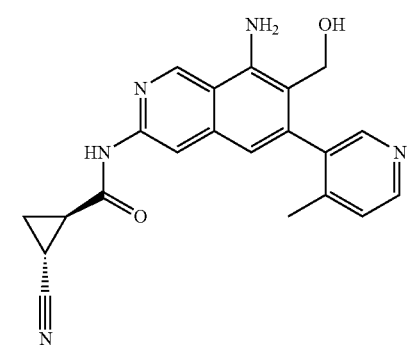<br>(±)-trans-N-[8-amino-7-(hydroxymethyl)-6-(4-methyl-3-pyridyl)-3-isoquinolyl]-2-cyano-cyclopropanecarboxamide | 1.852<br>374.1<br>C | 1H NMR (400 MHz, DMSO-d6) δ 11.12 (s, 1H), 9.46 (s, 1H), 8.46 (d, J = 4.8 Hz, 1H), 8.32 (d, J = 1.2 Hz, 1H), 8.19 (s, 1H), 7.34 (d, J = 4.8 Hz, 1H), 6.75 (s, 1H), 6.32 (s, 2H), 4.95 (s, 1H), 4.29 (d, J = 12.4 Hz, 1H), 4.18 (d, J = 12.0 Hz, 1H), 2.78-2.75 (m, 1H), 2.17-2.11 (m, 1H), 2.08 (s, 3H), 1.61-1.56 (m, 1H), 1.46-1.40 (m, 1H). |

TABLE A-3-continued

| Compound No. | Structure/Name | LCMS R$_T$ (min), M + H$^+$, method | $^1$H NMR (ppm) |
|---|---|---|---|
| 154 | 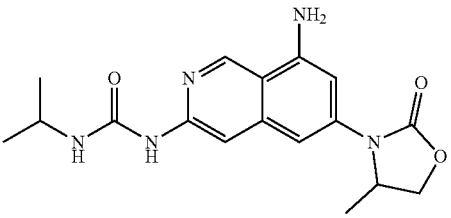<br>(±)-1-[8-amino-6-(4-methyl-2-oxo-oxazolidin-3-yl)-3-isoquinolyl]-3-isopropyl-urea | 1.399<br>344.2<br>A | $^1$H NMR (400 MHz, DMSO-d$_6$) δ 9.09 (s, 1H), 8.80 (s, 1H), 7.67 (s, 1H), 7.21 (d, J = 6.8 Hz, 1H), 6.87 (d, J = 1.2 Hz, 1H), 6.84 (s, 1H), 6.25 (s, 2H), 4.71-4.68 (m, 1H), 4.55 (t, J = 8.2 Hz, 1H), 4.04 (q, J = 4.4 Hz, 1H), 3.84-3.78 (m, 1H), 1.28 (d, J = 6.4 Hz, 3H), 1.13 (d, J = 6.8 Hz, 6H). |
| 155 | 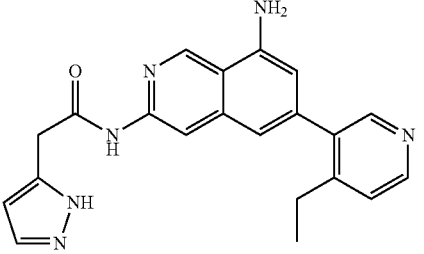<br>N-(8-amino-6-(4-ethylpyridin-3-yl)isoquinolin-3-yl)-2-(1H-pyrazol-5-yl)acetamide | 1.59<br>373.1<br>C | $^1$H NMR (400 MHz, DMSO-d$_6$): 12.62 (s, 1H), 10.52 (s, 1H), 9.31 (s, 1H), 8.49 (d, J = 5.2 Hz, 1H), 8.37 (s, 1H), 8.25 (s, 1H), 7.65 (s, 1H), 7.39 (d, J = 5.2 Hz, 1H), 6.88 (s, 1H), 6.35 (d, J = 6.8 Hz, 1H), 6.34 (s, 2H), 6.22 (d, J = 6.8 Hz, 1H), 3.83 (s, 2H), 2.64 (q, J = 7.6 Hz, 2H), 1.11 (t, J = 7.6 Hz, 3H). |
| 156 | 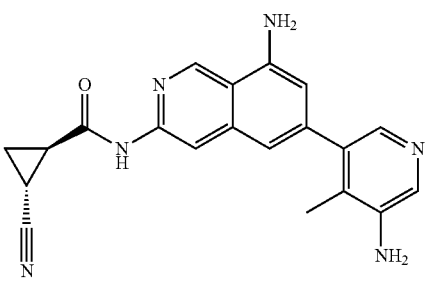<br>(±)-trans-N-(8-amino-6-(5-amino-4-methylpyridin-3-yl)isoquinolin-3-yl)-2-cyanocyclopropanecarboxamide | 1.49<br>359.1<br>C | $^1$H NMR (400 MHz, CD$_3$OD): 9.25 (s, 1H), 8.28 (s, 2H), 7.97 (s, 1H), 7.74 (s, 1H), 6.96 (s, 1H), 6.68 (s,1H), 2.66-2.64 (m, 1H), 2.14 (s, 3H), 2.14-2.11 (m, 1H), 1.62-1.54 (m, 2H). |
| 157 | 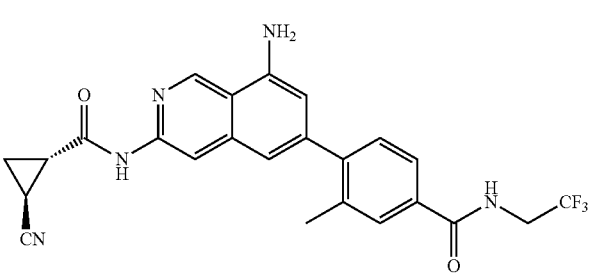<br>(±)-4-(8-amino-3-((trans)-2-cyanocyclopropanecarboxamido)isoquinolin-6-yl)-3-methyl-N-(2,2,2-trifluoroethyl)benzamide | 1.80<br>468.1<br>C | $^1$H NMR (400 MHz, CD$_3$OD): 9.25 (s, 1H), 8.28 (s, 1H), 7.82 (s, 1H), 7.76 (d, J = 7.6 Hz, 1H), 7.40 (d, J = 7.6 Hz, 1H), 6.97 (s, 1H), 4.17-4.10 (m, 2H), 2.67-2.62 (m, 1H), 2.36 (s, 3H), 2.14-2.09 (m, 1H), 1.62-1.52 (m, 2H). |

TABLE A-3-continued

| Compound No. | Structure/Name | LCMS $R_T$ (min), M + H⁺, method | ¹H NMR (ppm) |
|---|---|---|---|
| 159 | 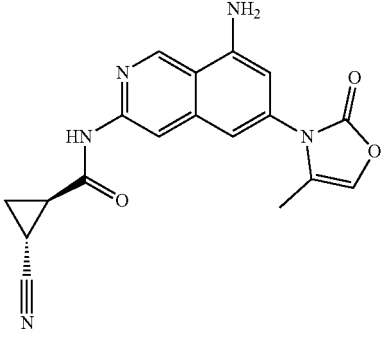<br>(±)-trans-N-(8-amino-6-(4-methyl-2-oxooxazol-3(2H)-yl)isoquinolin-3-yl)-2-cyanocyclopropanecarboxamide | 1.572<br>350.1<br>C | ¹H NMR (400 MHz, CD₃OD): δ 9.26 (s, 1H), 8.33 (s, 1H), 7.02 (s, 1H), 6.65 (s, 1H), 4.65 (s, 1H), 2.67-2.62 (m, 1H), 2.15-2.09 (m, 1H), 2.01 (s, 3H), 1.62-1.52 (m, 2H). |
| 160 | 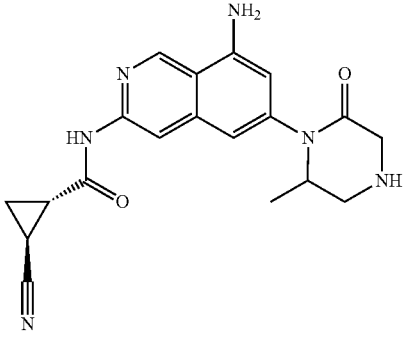<br>(±)-trans-N-(8-amino-6-(2-methyl-6-oxopiperazin-1-yl)isoquinolin-3-yl)-2-cyanocyclopropanecarboxamide | 1.35<br>365.1<br>C | ¹HNMR (400 MHz, DMSO-d₆): δ 11.09 (s, 1H), 9.27 (s, 1H), 8.16 (s, 1H), 6.79 (s, 1H), 6.44 (s, 1H), 6.30 (s, 2H), 4.05-3.92 (m, 2H), 3.17-3.12 (m, 2H), 2.78-2.74 (m, 3H), 2.17-2.11 (m, 1H), 1.61-1.56 (m, 1H), 1.45-1.42 (m, 1H), 1.01 (d, J = 6.4 Hz, 3H). |
| 161 | 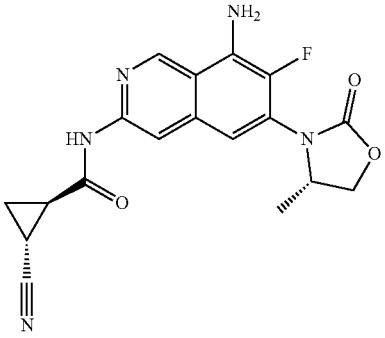<br>trans-N-(8-amino-7-fluoro-6-((S)-4-methyl-2-oxooxazolidin-3-yl)isoquinolin-3-yl)-2-cyanocyclopropanecarboxamide | 1.65<br>370.1<br>B | ¹HNMR (400 MHz, DMSO-d6) δ 11.14 (s, 1H), 9.39 (s, 1H), 8.22 (s, 1H), 7.06 (d, J = 6.4 Hz, 1H), 6.39 (s, 2H), 4.67 (t, J = 8.0 Hz, 1H), 4.53 (d, J = 7.2 Hz, 1H), 4.06 (t, J = 8.0 Hz, 1H), 2.75-2.71 (m, 1H), 2.15-2.12 (m, 1H), 1.61-1.57 (m, 1H), 1.42-1.40 (m, 1H), 1.15 (d, J = 6.0 Hz, 3H). |

TABLE A-3-continued

| Compound No. | Structure/Name | LCMS R$_T$ (min), M + H$^+$, method | $^1$H NMR (ppm) |
|---|---|---|---|
| 162 | 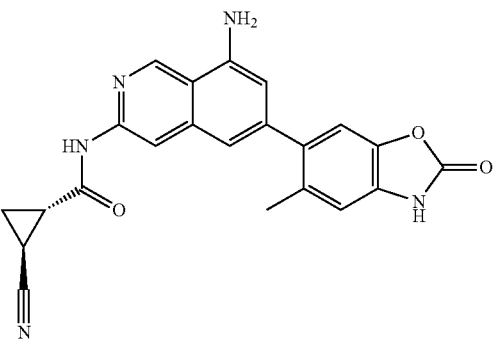<br>(1S,2S)-N-(8-amino-6-(5-methyl-2-oxo-2,3-dihydrobenzo[d]oxazol-6-yl)isoquinolin-3-yl)-2-cyanocyclopropane-1-carboxamide | 3.83<br>400.1<br>J | n/a |
| 163 | 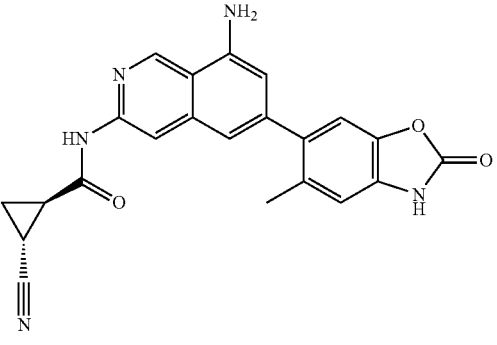<br>(1R,2R)-N-(8-amino-6-(5-methyl-2-oxo-2,3-dihydrobenzo[d]oxazol-6-yl)isoquinolin-3-yl)-2-cyanocyclopropane-1-carboxamide | 3.83<br>400.1<br>J | n/a |
| 164 | 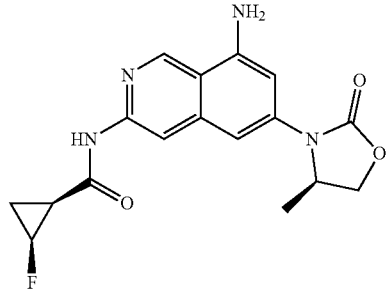<br>(1S,2S)-N-(8-amino-6-((R)-4-methyl-2-oxooxazolidin-3-yl)isoquinolin-3-yl)-2-fluorocyclopropane-1-carboxamide | 1.50<br>345.2<br>B | $^1$HNMR (400 MHz, DMSO-d6) δ 10.7 (s, 1H), 9.19 (s, 1H), 8.19 (s, 1H), 7.0 (s, 1H), 6.93 (s, 1H), 4.84-5.02 (m, 1H), 4.58-4.72 (m, 1H), 4.56 (t, 1H), 4.04-4.07 (m, 1H), 2.23-2.51 (m, 1H), 1.63-1.70 (m, 1H), 1.14-1.3 (m, 4H) |

TABLE A-3-continued

| Compound No. | Structure/Name | LCMS R_T (min), M + H+, method | 1H NMR (ppm) |
|---|---|---|---|
| 165 | 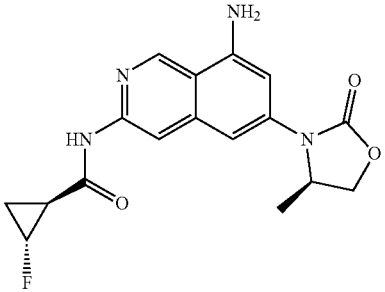<br>(1S,2R)-N-(8-amino-6-((R)-4-methyl-2-oxooxazolidin-3-yl)isoquinolin-3-yl)-2-fluorocyclopropane-1-carboxamide | 1.52<br>345.2<br>B | n/a |
| 166 | 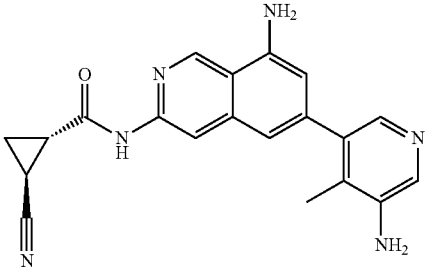<br>(1S,2S)-N-(8-amino-6-(5-amino-4-methylpyridin-3-yl)isoquinolin-3-yl)-2-cyanocyclopropane-1-carboxamide | 2.48<br>359.1<br>J | 1H NMR (400 MHz, DMSO-d6) δ 11.08 (s, 1H), 9.32 (s, 1H), 8.21 (s, 1H), 7.94 (s, 1H), 7.64 (s, 1H), 6.82 (s, 1H), 6.53 (s, 1H), 6.31 (s, 2H), 5.18 (s, 1H), 2.73-2.77 (m, 1H), 2.12-2.14 (m, 1H), 1.59-1.61 (m, 1H), 1.40-1.57 (m, 1H) |
| 167 | 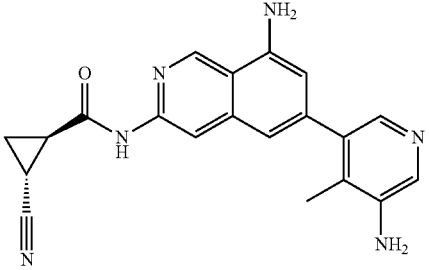<br>(1R,2R)-N-(8-amino-6-(5-amino-4-methylpyridin-3-yl)isoquinolin-3-yl)-2-cyanocyclopropane-1-carboxamide | 2.48<br>359.1<br>J | 1H NMR (400 MHz, DMSO-d6) δ 11.08 (s, 1H), 9.31 (s, 1H), 8.21 (s, 1H), 7.93 (s, 1H), 7.64 (s, 1H), 6.82 (s, 1H), 6.53 (s, 1H), 6.31 (s, 2H), 5.18 (s, 1H), 2.73-2.77 (m, 1H), 2.12-2.14 (m, 1H), 1.59-1.61 (m, 1H), 1.40-1.57 (m, 1H) |
| 168 | 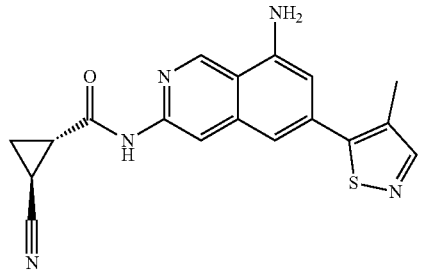<br>(1S,2S)-N-(8-amino-6-(4-methylisothiazol-5-yl)isoquinolin-3-yl)-2-cyanocyclopropane-1-carboxamide | 4.66<br>350.1<br>J | 1H NMR (400 MHz, DMSO-d6) δ 11.18 (s, 1H), 3.34 (s, 1H), 8.48 (s, H), 8.29 (s, 1H), 7.09 (s, 1H), 6.73 (s, 1H), 6.55 (s, 2H), 2.74-2.76 (m, 1H), 2.40 (s, 3H), 2.08-2.17 (m, 1H), 1.62-1.63 (m, 1H), 1.40-1.45 (m, 1H) |

TABLE A-3-continued

| Compound No. | Structure/Name | LCMS R_T (min), M + H+, method | $^1$H NMR (ppm) |
|---|---|---|---|
| 169 | (1R,2R)-N-(8-amino-6-(4-methylisothiazol-5-yl)isoquinolin-3-yl)-2-cyanocyclopropane-1-carboxamide | 4.66 350.1 J | $^1$H NMR (400 MHz, DMSO-d6) δ 11.18 (s, 1H), 3.34 (s, 1H), 8.48 (s, H), 8.29 (s, 1H), 7.09 (s, 1H), 6.73 (s, 1H), 6.55 (s, 2H), 2.74-2.76 (m, 1H), 2.40 (s, 3H), 2.08-2.17 (m, 1H), 1.62-1.58 (m, 1H), 1.40-1.45 (m, 1H) |
| 170 | (±)-trans-N-(8-amino-6-(1-methyl-1H-pyrrolo[2,3-c]pyridin-4-yl)isoquinolin-3-yl)-2-cyanocyclopropane-1-carboxamide | 2.76 383.1 J | 1H NMR (400 MHz, DMSO) δ 11.09 (s, 1H), 9.34 (s, 1H), 8.86 (s, 1H), 8.29 (d, J = 9.8 Hz, 2H), 7.66 (d, J = 3.1 Hz, 1H), 7.22 (s, 1H), 7.00 (d, J = 1.5 Hz, 1H), 6.68 (dd, J = 3.0, 0.8 Hz, 1H), 6.37 (s, 2H), 3.97 (s, 3H), 2.80-2.73 (m, 1H), 2.17-2.11 (m, 1H), 1.63-1.55 (m, 1H), 1.48-1.40 (m, 1H) |
| 171 | (±)-trans-N-(8-amino-6-(1-methyl-1H-pyrazolo[3,4-c]pyridin-4-yl)isoquinolin-3-yl)-2-cyanocyclopropane-1-carboxamide | 3.09 384.1 J | 1H NMR (400 MHz, DMSO) δ 11.11 (s, 1H), 9.36 (s, 1H), 9.20 (s, 1H), 8.47 (s, 1H), 8.40-8.29 (m, 2H), 7.34 (s, 1H), 7.06 (d, J = 1.5 Hz, 1H), 6.44 (s, 2H), 4.24 (s, 3H), 2.77 (dd, J = 10.8, 8.0 Hz, 1H), 2.19-2.09 (m, 1H), 1.65-1.56 (m, 1H), 1.49-1.39 (m, 1H) |

TABLE A-3-continued

| Compound No. | Structure/Name | LCMS R$_T$ (min), M + H$^+$, method | $^1$H NMR (ppm) |
|---|---|---|---|
| 172 | 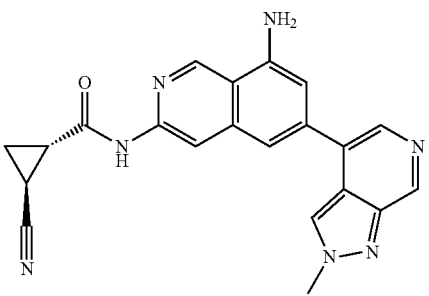<br>(±)-trans-N-(8-amino-6-(2-methyl-2H-pyrazolo[3,4-c]pyridin-4-yl)isoquinolin-3-yl)-2-cyanocyclopropane-1-carboxamide | 2.70<br>384.1<br>J | 1H NMR (400 MHz, DMSO) δ 11.11 (s, 1H), 9.35 (s, 1H), 9.15 (s, 1H), 8.76 (s, 1H), 8.32 (d, J = 14.3 Hz, 2H), 7.33 (s, 1H), 7.02 (d, J = 1.5 Hz, 1H), 6.39 (s, 2H), 4.30 (s, 3H), 2.75 (d, J = 5.9 Hz, 1H), 2.19-2.09 (m, 1H), 1.64-1.55 (m, 1H), 1.49-1.39 (m, 1H). |
| 173 | 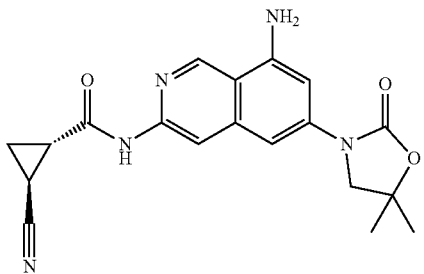<br>(±)-trans-N-(8-amino-6-(5,5-dimethyl-2-oxooxazolidin-3-yl)isoquinolin-3-yl)-2-cyanocyclopropane-1-carboxamide | 3.58<br>366.1<br>J | 1H NMR (400 MHz, DMSO) δ 11.01 (s, 1H), 9.19 (s, 1H), 8.12 (s, 1H), 7.21 (d, J = 2.1 Hz, 1H), 6.81 (d, J = 1.8 Hz, 1H), 6.34 (s, 2H), 3.89 (s, 2H), 2.74 (dd, J = 11.4, 7.2 Hz, 1H), 2.18-2.09 (m, 1H), 1.60-1.55 (m, 1H), 1.48 (s, 6H), 1.42 (dt, J = 10.2, 5.1 Hz, 1H). |
| 174 | 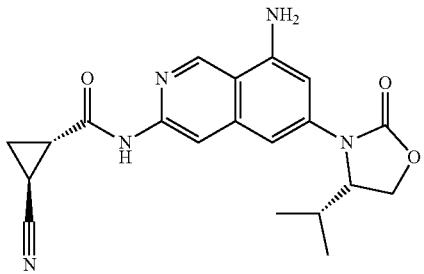<br>trans-N-(8-amino-6-((S)-4-isopropyl-2-oxooxazolidin-3-yl)isoquinolin-3-yl)-2-cyanocyclopropane-1-carboxamide | 3.89<br>380.1<br>J | 1H NMR (400 MHz, DMSO) δ 11.03 (s, 1H), 9.21 (s, 1H), 8.15 (s, 1H), 7.00 (s, 2H), 6.35 (s, 2H), 4.63 (dd, J = 8.4, 4.1 Hz, 1H), 4.42 (t, J = 8.9 Hz, 1H), 4.29 (dd, J = 9.0, 4.0 Hz, 1H), 2.73 (d, J = 12.9 Hz, 1H), 2.16-2.07 (m, 2H), 1.61-1.55 (m, 1H), 1.42 (dt, J = 9.3, 4.7 Hz, 1H), 0.88 (d, J = 7.0 Hz, 3H), 0.75 (d, J = 6.8 Hz, 3H). |
| 175 | 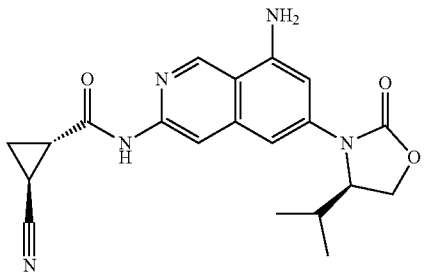<br>trans-N-(8-amino-6-((R)-4-isopropyl-2-oxooxazolidin-3-yl)isoquinolin-3-yl)-2-cyanocyclopropane-1-carboxamide | 3.98<br>380.2<br>J | 1H NMR (400 MHz, DMSO) δ 11.03 (s, 1H), 9.21 (s, 1H), 8.15 (s, 1H), 7.00 (s, 2H), 6.35 (s, 2H), 4.69-4.59 (m, 1H), 4.42 (t, J = 8.9 Hz, 1H), 4.30 (dd, J = 8.9, 4.0 Hz, 1H), 2.79-2.69 (m, 1H), 2.18-2.06 (m, 2H), 1.64-1.54 (m, 1H), 1.46-1.37 (m, 1H), 0.88 (d, J = 7.0 Hz, 3H), 0.75 (d, J = 6.8 Hz, 3H). |

TABLE A-3-continued

| Compound No. | Structure/Name | LCMS R_T (min), M + H+, method | ¹H NMR (ppm) |
|---|---|---|---|
| 176 | 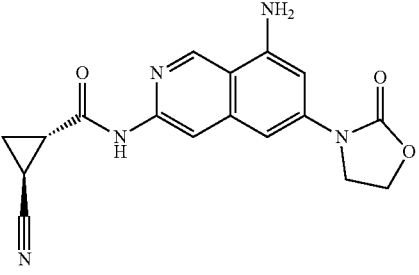<br>(±)-trans-N-(8-amino-6-(2-oxooxazolidin-3-yl)isoquinolin-3-yl)-2-cyanocyclopropane-1-carboxamide | 3.02<br>338.1<br>J | 1H NMR (400 MHz, DMSO) δ 11.01 (s, 1H), 9.19 (s, 1H), 8.14 (s, 1H), 7.20 (d, J = 2.0 Hz, 1H), 6.86 (d, J = 1.8 Hz, 1H), 6.35 (s, 2H), 4.47-4.40 (m, 2H), 4.13-4.06 (m, 2H), 2.78-2.71 (m, 1H), 2.17-2.08 (m, 1H), 1.6-1.54 (m, 1H), 1.46-1.38 (m, 1H). |
| 177 | 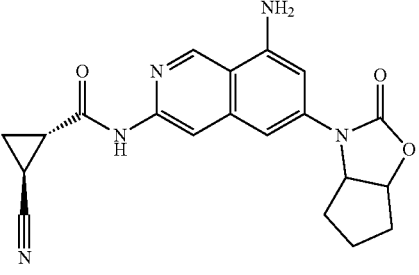<br>(±)-trans-N-(8-amino-6-(2-oxotetrahydro-2H-cyclopenta[d]oxazol-3(3aH)-yl)isoquinolin-3-yl)-2-cyanocyclopropane-1-carboxamide | 3.73<br>378.1<br>J | 1H NMR (400 MHz, DMSO) δ 11.02 (s, 1H), 9.19 (s, 1H), 8.14 (s, 1H), 7.16 (d, J = 2.0 Hz, 1H), 6.93 (d, J = 1.8 Hz, 1H), 6.35 2H), 5.14-5.04 1H), 4.89 (s, 1H), 2.73 (d, J = 5.3 Hz, 1H), 2.16-2.08 (m, 1H), 2.01-1.93 (m, 1H), 1.86-1.76 (m, 3H), 1.68 (s, 1H), 1.63-1.52 (m, 2H), 1.42 (d, J = 4.3 Hz, 1H). |
| 178 | 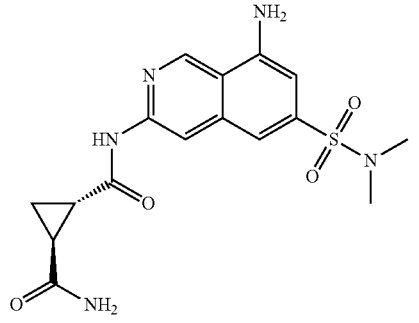<br>(±)-trans-N-(8-amino-6-(N,N-dimethylsulfamoyl)isoquinolin-3-yl)cyclopropane-1,2-dicarboxamide | 3.32<br>378.1<br>N* | |

TABLE A-3-continued

| Compound No. | Structure/Name | LCMS $R_T$ (min), M + H⁺, method | ¹H NMR (ppm) |
|---|---|---|---|
| 179 | (±)-trans-N-(8-amino-6-(N,N-dimethylsulfamoyl)isoquinolin-3-yl)-2-cyanocyclopropane-1-carboxamide | 3.39 360.1 N* | |
| 180 | (1S,2S)-N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropanecarboxamide | 1.23 479 K | ¹HNMR (400 MHz, CD₃OD) δ 9.17 (s, 1H), 8.56 (d, J = 5.1 Hz, 1H), 8.20 (s, 1H), 7.49 (d, J = 5.7 Hz, 2H), 7.37 (s, 1H), 7.20 (d, J = 2.0 Hz, 1H), 6.82 (s, 1H), 6.47 (d, J = 1.3 Hz, 1H), 5.99 (d, J = 2.0 Hz, 1H), 3.86 (s, 3H), 3.81 (s, 3H), 2.38-2.33 (m,1H), 2.29 (s, 3H), 2.12-2.04 (m, 1H), 1.57-1.53 (m, 1H), 1.30-1.18 (m, 1H). |
| 181 | (1R,2R)-N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropanecarboxamide | 1.22 479 K | ¹H NMR (400 MHz, CD₃OD) δ 9.17 (s, 1H), 8.56 (d, J = 5.1 Hz, 1H), 8.20 (s, 1H), 7.49 (d, J = 5.7 Hz, 2H), 7.37 (s, 1H), 7.20 (d, J = 2.0 Hz, 1H), 6.82 (s, 1H), 6.47 (d, J = 1.3 Hz, 1H), 5.99 (d, J = 2.0 Hz, 1H), 3.86 (s, 3H), 3.81 (s, 3H), 2.38-2.33 (m, 1H), 2.29 (s, 3H), 2.12-2.04 (m, 1H), 1.57-1.53 (m, 1H), 1.30-1.18 (m, 1H). |

TABLE A-3-continued

| Compound No. | Structure/Name | LCMS R_T (min), M + H+, method | $^1$H NMR (ppm) |
|---|---|---|---|
| 182 | (1R,2R)-N-(8-amino-6-(4-methyl-2-phenylpyridin-3-yl)isoquinolin-3-yl)-2-(1-methyl-1H-pyrazol-4-yl)cyclopropanecarboxamide | 1.13 474 K | $^1$HNMR (300 MHz, CD$_3$OD) δ 9.14 (s, 1H), 8.47 (s, 1H), 8.13 (s, 1H), 7.50 (s, 1H), 7.44-7.26 (m, 4H), 7.22-7.11 (m, 3H), 6.78 (s, 1H), 6.50 (d, J = 1.3 Hz, 1H), 3.85 (d, J = 0.6 Hz, 3H), 2.41-2.31 (m, 1H), 2.27 (s, 3H), 2.13-2.04 (m, 1H), 1.56-1.53 (m, 1H), 1.32-1.17 (m, 1H). |
| 183 | (1S,2S)-N-(8-amino-6-(4-methyl-2-phenylpyridin-3-yl)isoquinolin-3-yl)-2-(1-methyl-1H-pyrazol-4-yl)cyclopropanecarboxamide | 1.13 474, K | $^1$HNMR (300 MHz, CD$_3$OD) δ 9.14 (s, 1H), 8.47 (s, 1H), 8.13 (s, 1H), 7.50 (s, 1H), 7.44-7.26 (m, 4H), 7.22-7.11 (m, 3H), 6.78 (s, 1H), 6.50 (d, J = 1.3 Hz, 1H), 3.85 (s, 3H), 2.41-2.31 (m, 1H), 2.27 (s, 3H), 2.13-2.04 (m, 1H), 1.56-1.53 (m, 1H), 1.32-1.17 (m, 1H). |
| 184 | (±)-trans-N-(8-amino-6-(4-methyl-2-(piperidin-1-yl)pyridin-3-yl)isoquinolin-3-yl)-2-(1-methyl-1H-pyrazol-4-yl)cyclopropanecarboxamide | 2.02 482.3, K | $^1$HNMR (400 MHz, DMSO-d$_6$) δ 10.75 (s, 1H), 9.27 (s, 1H), 8.24 (s, 1H), 8.06 (d, J = 5.0 Hz, 1H), 7.56 (s, 1H), 7.29 (d, J = 0.8 Hz, 1H), 6.94-6.80 (m, 2H), 6.53 (d, J = 1.4 Hz, 1H), 6.20 (s, 2H), 3.78 (s, 3H), 2.96 (s, 4H), 2.19 (t, J = 7.1 Hz, 2H), 2.07 (s, 3H), 1.36 (qd, J = 7.0, 6.2, 4.3 Hz, 3H), 1.25 (d, J = 8.3 Hz, 4H), 1.20-1.10 (m, 1H). |
| 185 | (±)-trans-N-(8-amino-6-(2-amino-3-methylpyridin-4-yl)isoquinolin-3-yl)-2-(1-methyl-1H-pyrazol-4-yl)cyclopropanecarboxamide | 1.05 414.1 K | $^1$HNMR (300 MHz, DMSO-d$_6$) δ 10.75 (s, 1H), 9.30 (s, 1H), 8.27 (s, 1H), 7.83 (d, J = 5.1 Hz, 1H), 7.57 (d, J = 0.9 Hz, 1H), 7.30 (d, J = 0.8 Hz, 1H), 6.81 (d, J = 1.3 Hz, 1H), 6.53-6.41 (m, 2H), 6.31 (s, 2H), 5.78 (s, 2H), 3.78 (s, 3H), 2.20-2.16 (m, 2H), 1.98 (s, 3H), 1.44-1.32 (m, 1H), 1.17-1.14 (m, 1H). |

TABLE A-3-continued

| Compound No. | Structure/Name | LCMS R_T (min), M + H+, method | $^1$H NMR (ppm) |
|---|---|---|---|
| 186 | 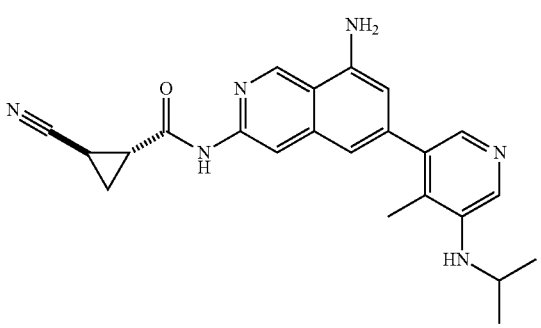<br>(±)-trans-N-(8-amino-6-[4-methyl-5-[(propan-2-yl)amino]pyridin-3-yl]isoquinolin-3-yl)-2-cyanocyclopropane-1-carboxamide | 1.03<br>401.1<br>K | $^1$HNMR (300 MHz, CD$_3$OD) δ 9.26 (s, 1H), 8.29 (s, 1H), 7.91 (s, 1H), 7.76 (s, 1H), 6.97 (s, 1H), 6.68 (d, J = 1.4 Hz, 1H), 3.83-3.80 (m, 1H), 2.71-2.60 (m, 1H), 2.18-2.03 (m, 4H), 1.58-1.54 (m, 2H), 1.33 (d, J = 12 Hz, 6H) |
| 187 | 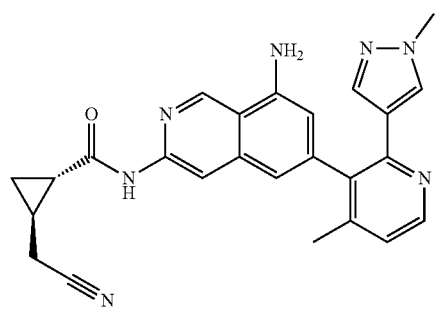<br>(±)-trans-(1S,2R)-N-(8-amino-6-(4-methyl-2-(1-methyl-1H-pyrazol-4-yl)pyridin-3-yl)isoquinolin-3-yl)-2-(cyanomethyl)cyclopropanecarboxamide | 1.207<br>438.2<br>K | $^1$H NMR (300 MHz, CD$_3$OD) δ 9.28 (s, 1H), 8.41 (d, J = 5.1 Hz, 1H), 8.23 (s, 1H), 7.35 (s, 1H), 7.26 (d, J = 5.1 Hz, 1H), 7.15 (s, 1H), 6.88 (s, 1H), 6.53 (s, 1H), 3.71 (s, 3H), 2.83-2.59 (m, 2H), 2.18 (t, J = 0.7 Hz, 3H), 2.01 (dt, J = 8.7, 4.5 Hz, 1H), 1.85-1.58 (m, 1H), 1.33 (dt, J = 9.0, 4.7 Hz, 1H), 1.07-1.00 (m, 1H). |
| 188 | 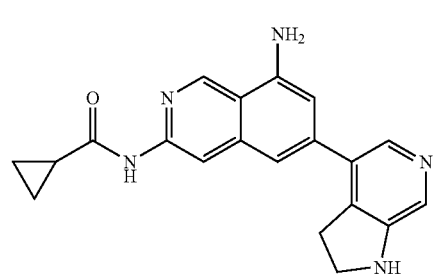<br>N-(8-amino-6-(2,3-dihydro-1H-pyrrolo[2,3-c]pyridin-4-yl)isoquinolin-3-yl)cyclopropanecarboxamide | 1.193<br>346.1<br>K | $^1$HNMR (300 MHz, DMSO-d$_6$) δ 10.80 (s, 1H), 9.32 (s, 1H), 8.31 (s, 1H), 7.99 (s, 1H), 7.83 (s, 1H), 7.11-7.02 (m, 1H), 6.73 (d, J = 1.5 Hz, 1H), 6.36 (s, 2H), 6.18 (s, 1H), 3.55-3.50 (m, 2H), 3.20-3.15 (m, 2H), 2.06-2.01 (m, 1H), 0.84-0.80 (m, 4H). |

| Compound No. | Structure/Name | LCMS R_T (min), M + H+, method | $^1$H NMR (ppm) |
|---|---|---|---|
| 189 | 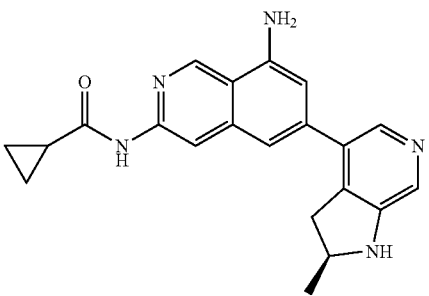<br>(S)-N-(8-amino-6-(2-methyl-2,3-dihydro-1H-pyrrolo[2,3-c]pyridin-4-yl)isoquinolin-3-yl)cyclopropanecarboxamide<br>(Absolute stereochemistry arbitrarily assigned) | 1.09<br>360.3<br>K | $^1$H NMR (300 MHz, CD$_3$OD) δ 9.21 (s, 1H), 8.28 (s, 1H), 7.94 (s, 1H), 7.78 (s, 1H), 7.11 (s, 1H), 6.83 (s, 1H), 4.18-3.91 (m, 1H), 3.34-3.31 (m, 1H), 2.81 (dd, J = 16.8 Hz, 7.7 Hz, 1H), 1.98-1.90 (m, 1H), 1.29 (d, J = 6.2 Hz, 3H), 1.05-0.99 (m, 2H), 0.98-0.85 (m, 2H). |
| 190 | 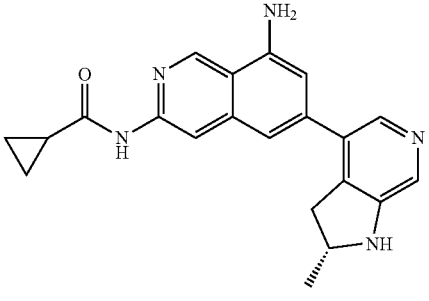<br>(R)-N-(8-amino-6-(2-methyl-2,3-dihydro-1H-pyrrolo[2,3-c]pyridin-4-yl)isoquinolin-3-yl)cyclopropanecarboxamide<br>(Absolute stereochemistry arbitrarily assigned) | 1.09<br>360.3<br>K | $^1$HNMR (300 MHz, CD$_3$OD) δ 9.21 (s, 1H), 8.28 (s, 1H), 7.94 (s, 1H), 7.78 (s, 1H), 7.11 (s, 1H), 6.83 (s, 1H), 4.18-3.91 (m, 1H), 3.34-3.31 (m, 1H), 2.81 (dd, J = 16.8, 7.7 Hz, 1H), 1.98-1.90 (m, 1H), 1.29 (d, J = 6.2 Hz, 3H), 1.05-0.99 (m, 2H), 0.98-0.85 (m, 2H). |
| 191 | 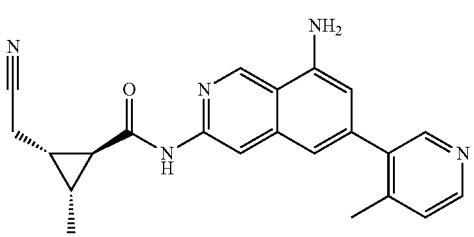<br>(±)-(1S*,2S*,3R*)-N-(8-amino-6-(4-methylpyridin-3-yl)isoquinolin-3-yl)-2-(cyanomethyl)-3-methylcyclopropanecarboxamide<br>(Absolute stereochemistry arbitrarily assigned) | 1.153<br>372.2<br>K | $^1$HNMR (400 MHz, DMSO-d$_6$) 10.80 (s, 1H), 9.32 (s, 1H), 8.67-8.39 (m, 2H), 8.26 (s, 1H), 7.45 (d, J = 5.1 Hz, 1H), 6.97-6.81 (m, 1H), 6.55 (d, J = 1.5 Hz, 1H), 6.37 (s, 2H), 2.81 (dd, J = 17.6, 7.3 Hz, 1H), 2.69 (dd, J = 17.7, 7.7 Hz, 1H), 2.33 (s, 3H), 1.79 (t, J = 4.5 Hz, 1H), 1.71-1.57 (m, 1H), 1.52-1.37 (m, 1H), 1.17 (d, J = 6.3 Hz, 3H). |

| Compound No. | Structure/Name | LCMS $R_T$ (min), $M+H^+$, method | $^1$H NMR (ppm) |
|---|---|---|---|
| 192 | 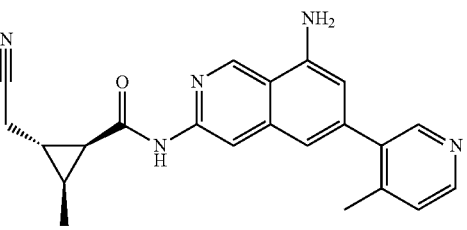<br>(±)-(1S*,2S*,3S*)-N-(8-amino-6-(4-methylpyridin-3-yl)isoquinolin-3-yl)-2-(cyanomethyl)-3-methylcyclopropanecarboxamide<br>(Absolute stereochemistry arbitrarily assigned) | 1.924<br>372.2<br>K | $^1$HNMR (400 MHz, DMSO-$d_6$) 10.79 (s, 1H), 9.32 (s, 1H), 8.48-8.36 (m, 2H), 8.28 (s, 1H), 7.35 (d, J = 5.0 Hz, 1H), 6.99-6.86 (m, 1H), 6.55 (d, J = 1.5 Hz, 1H), 6.34 (s, 2H), 2.83-2.61 (m, 2H), 2.30 (s, 3H), 2.15-2.03 (m, 1H), 1.58-1.45 (m, 1H), 1.36 (dt, J = 9.1, 6.1 Hz, 1H), 1.17 (d, J = 6.1 Hz, 3H). |
| 193 | 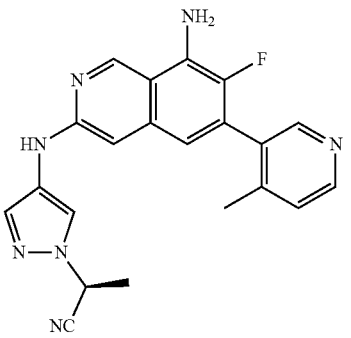<br>(2S)-2-(4-(8-amino-7-fluoro-6-(4-methylpyridin-3-yl)isoquinolin-3-ylamino)-1H-pyrazol-1-yl)propanenitrile<br>(Absolute stereochemistry arbitrarily assigned) | 1.08<br>388.2<br>K | $^1$HNMR (300 MHz, CD$_3$OD) δ 9.29 (s, 1H), 8.76 (s,1H), 8.49 (d, J = 5.0 Hz, 1H), 8.41 (s, 1H), 8.09 (d, J = 0.8 Hz, 1H), 7.62 (d, J = 0.8 Hz, 1H), 7.39-7.34 (m, 1H), 6.83 (s, 1H), 6.76 (d, J = 6.1 Hz, 1H), 6.13 (s, 2H), 5.82 (q, J = 7.1 Hz, 1H), 2.22 (s, 3H), 1.80 (d, J = 7.1 Hz, 3H). |
| 194 | 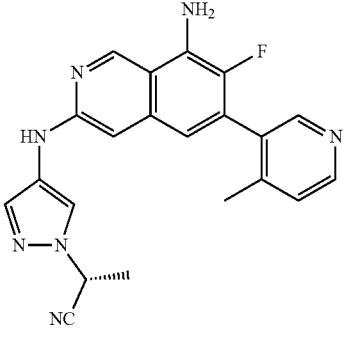<br>(2R)-2-(4-(8-amino-7-fluoro-6-(4-methylpyridin-3-yl)isoquinolin-3-ylamino)-1H-pyrazol-1-yl)propanenitrile<br>(Absolute stereochemistry arbitrarily assigned) | 1.08<br>388.2<br>K | $^1$HNMR (300 MHz, CD$_3$OD) δ 9.29 (s, 1H), 8.76 (s, 1H), 8.49 (d, J = 5.0 Hz, 1H), 8.41 (s, 1H), 8.09 (d, J = 0.8 Hz, 1H), 7.62 (d, J = 0.8 Hz, 1H), 7.39-7.34 (m, 1H), 6.83 (s, 1H), 6.76 (d, J = 6.1 Hz, 1H), 6.13 (s, 2H), 5.82 (q, J = 7.1 Hz, 1H), 2.22 (s, 3H), 1.80 (d, J = 7.1 Hz, 3H). |

TABLE A-3-continued

| Compound No. | Structure/Name | LCMS R_T (min), M + H⁺, method | ¹H NMR (ppm) |
|---|---|---|---|
| 195 | 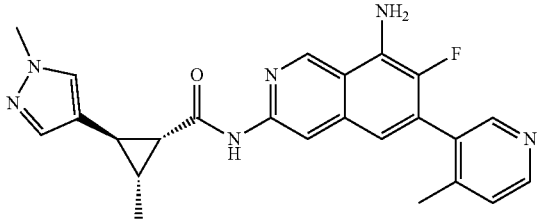<br>(1R,2R,3R)-N-(8-amino-7-fluoro-6-(4-methylpyridin-3-yl)isoquinolin-3-yl)-2-methyl-3-(1-methyl-1H-pyrazol-4-yl)cyclopropanecarboxamide<br>(Absolute stereochemistry arbitrarily assigned) | 1.14<br>461.3<br>K | ¹HNMR (400 MHz, CD$_3$OD) δ 9.30 (s, 1H), 8.47 (d, J = 5.2 Hz, 1H), 8.42 (s, 1H), 8.36 (s, 1H), 7.45 (t, J = 6.2 Hz, 2H), 7.34 (s, 1H), 7.00 (d, J = 8.0 Hz, 1H), 3.85 (s, 3H), 2.34-2.32 (m, 4H), 2.17-2.14 (m, 1H), 1.62-1.48 (m, 1H), 1.35 (d, J = 6.4 Hz, 3H). |
| 196 | 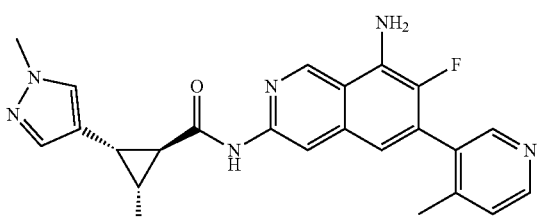<br>(1S,2R,3S)-N-(8-amino-7-fluoro-6-(4-methylpyridin-3-yl)isoquinolin-3-yl)-2-methyl-3-(1-methyl-1H-pyrazol-4-yl)cyclopropanecarboxamide<br>(Absolute stereochemistry arbitrarily assigned) | 1.15<br>461.3<br>K | ¹HNMR (400 MHz, CD$_3$OD) δ 9.31 (s, 1H), 8.46 (d, J=5.2 Hz, 1H), 8.41 (s, 1H), 8.34 (s, 1H), 7.51 (s, 1H), 7.42 (d, J = 5.2 Hz, 1H), 7.39 (s, 1H), 6.98 (d, J = 6.0 Hz, 1H), 3.88 (s, 3H), 2.52-2.49 (m, 1H), 2.30 (s, 3H), 1.99-1.97 (m, 1H), 1.79-1.72 (m, 1H), 1.17 (d, J = 6.4 Hz, 3H). |
| 197 | 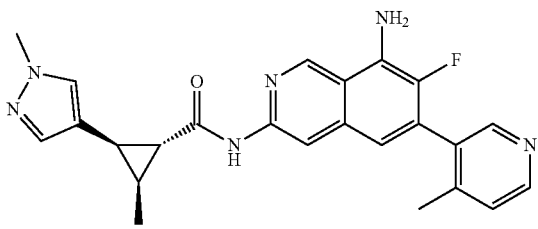<br>(1R,2S,3R)-N-(8-amino-7-fluoro-6-(4-methylpyridin-3-yl)isoquinolin-3-yl)-2-methyl-3-(1-methyl-1H-pyrazol-4-yl)cyclopropanecarboxamide<br>(Absolute stereochemistry arbitrarily assigned) | 1.15<br>461.3<br>K | ¹HNMR (400 MHz, CD$_3$OD) δ 9.31 (s, 1H), 8.46 (d, J = 5.2 Hz, 1H), 8.41 (s, 1H), 8.34 (s, 1H), 7.51 (s, 1H), 7.43 (d, J = 5.2 Hz, 1H), 7.39 (s, 1H), 6.98 (d, J = 6.0 Hz, 1H), 3.88 (s, 3H), 2.53-2.49 (m, 1H), 2.31 (s, 3H), 1.99-1.97 (m, 1H), 1.77-1.72 (m, 1H), 1.17 (d, J = 6.4 Hz, 3H). |
| 198 | 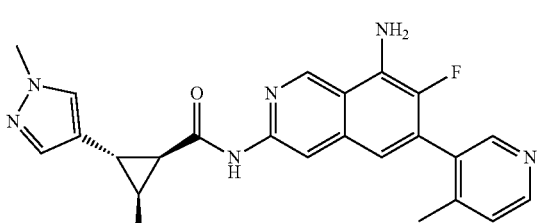<br>(1S,2S,3S)-N-(8-amino-7-fluoro-6-(4-methylpyridin-3-yl)isoquinolin-3-yl)-2-methyl-3-(1-methyl-1H-pyrazol-4-yl)cyclopropanecarboxamide<br>(Absolute stereochemistry arbitrarily assigned) | 1.14<br>461.3<br>K | ¹H NMR (400 MHz, CD$_3$OD) δ 9.30 (s, 1H), 8.47 (d, J = 5.2 Hz, 1H), 8.42 (s, 1H), 8.36 (s, 1H), 7.45 (t, J = 6.2 Hz, 2H), 7.34 (s, 1H), 7.00 (d, J = 8.0 Hz, 1H), 3.85 (s, 3H), 2.34-2.32 (m, 4H), 2.17-2.14 (m, 1H), 1.67-1.61 (m, 1H), 1.35 (d, J = 6.4 Hz, 3H). |

TABLE A-3-continued

| Compound No. | Structure/Name | LCMS R_T (min), M + H+, method | $^1$H NMR (ppm) |
|---|---|---|---|
| 199 | 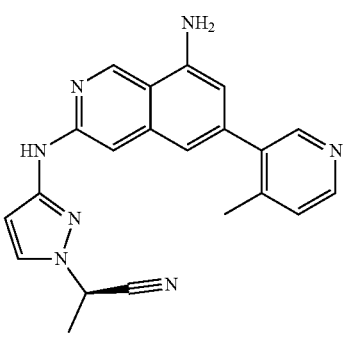<br>(R)-2-(3-(8-amino-6-(4-methylpyridin-3-yl)isoquinolin-3-ylamino)-1H-pyrazol-1-yl)propanenitrile<br>(Absolute stereochemistry arbitrarily assigned) | 0.99<br>461.3<br>K | $^1$H NMR (400 MHz, CD$_3$OD) δ 9.14 (s, 1H), 8.39 (d, J = 4.4 Hz, 2H), 7.80 (s, 1H), 7.67 (d, J = 2.4 Hz, 1H), 7.40 (d, J = 5.2 Hz, 1H), 6.89 (s, 1H), 6.52 (s, 1H), 6.25 (d, J = 2.4 Hz, 1H), 5.59-5.54 (m, 1H), 2.39 (s, 3H), 1.91 (d, J = 6.8 Hz, 3H). |
| 200 | 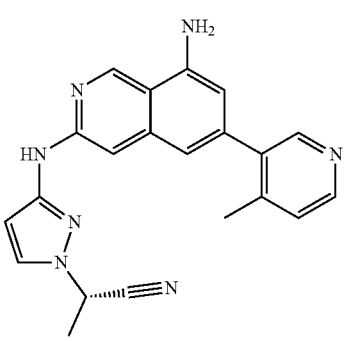<br>(S)-2-(3-(8-amino-6-(4-methylpyridin-3-yl)isoquinolin-3-ylamino)-1H-pyrazol-1-yl)propanenitrile<br>(Absolute stereochemistry arbitrarily assigned) | 0.99<br>461.3<br>K | $^1$HNMR (400 MHz, CD$_3$OD) δ 9.14 (s, 1H), 8.39 (d, J = 4.4 Hz, 2H), 7.80 (s, 1H), 7.67 (d, J = 2.4 Hz, 1H), 7.40 (d, J = 5.2 Hz, 1H), 6.89 (s, 1H), 6.52 (s, 1H), 6.25 (d, J = 2.4 Hz, 1H), 5.59-5.54 (m, 1H), 2.39 (s, 3H), 1.91 (d, J = 6.8 Hz, 3H). |
| 201 | 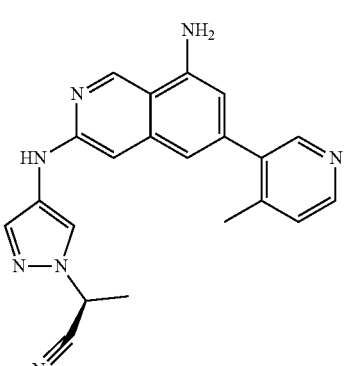<br>(S)-2-(4-(8-amino-6-(4-methylpyridin-3-yl)isoquinolin-3-ylamino)-1H-pyrazol-1-yl)propanenitrile<br>(Absolute stereochemistry arbitrarily assigned) | 1.585<br>370.2<br>K | $^1$HNMR (300 MHz, CD$_3$OD) δ 9.12 (s, 1H), 8.39-8.37 (m, 2H), 8.06 (s, 1H), 7.67 (s, 1H), 7.37 (d, J = 5.1 Hz, 1H), 6.82 (d, J = 5.1 Hz, 2H), 6.45 (s, 1H), 5.62 (q, J = 7.2 Hz, 1H), 2.37 (s, 3H), 1.90 (d, J = 7.2 Hz, 3H) |

| Compound No. | Structure/Name | LCMS R_T (min), M + H+, method | $^1$H NMR (ppm) |
|---|---|---|---|
| 202 | 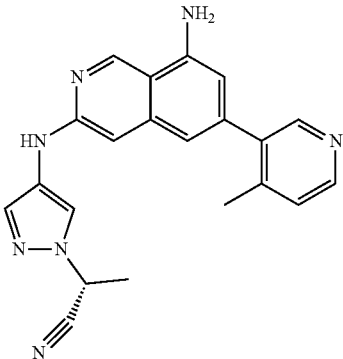<br>(R)-2-(4-(8-amino-6-(4-methylpyridin-3-yl)isoquinolin-3-ylamino)-1H-pyrazol-1-yl)propanenitrile (Absolute stereochemistry arbitrarily assigned) | 0.946<br>370.2<br>K | $^1$HNMR (300 MHz, CD$_3$OD) δ 9.12 (s, 1H), 8.39-8.37 (m, 2H), 8.06 (s, 1H), 7.67 (s, 1H), 7.37 (d, J = 5.1 Hz, 1H), 6.82 (d, J = 5.1 Hz, 2H), 6.45 (s, 1H), 5.62 (q, J = 7.2 Hz, 1H), 2.37 (s, 3H), 1.90 (d, J = 7.2 Hz, 3H) |
| 203 | 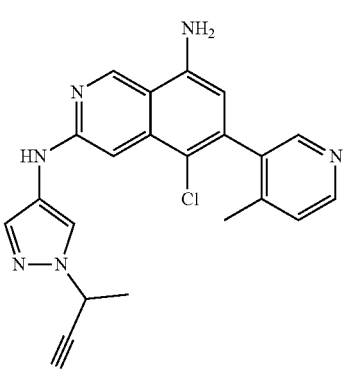<br>2-(4-(8-amino-5-chloro-6-(4-methylpyridin-3-yl)isoquinolin-3-ylamino)-1H-pyrazol-1-yl)propanenitrile | 1.118<br>404.3<br>K | $^1$HNMR (300 MHz, CD$_3$OD) δ 9.17 (s, 1H), 8.42 (d, J = 5.1 Hz, 1H), 8.27 (s, 1H), 8.10 (s, 1H), 7.69 (s, 1H), 7.40 (d, J = 5.1 Hz, 1H), 7.15 (s, 1H), 6.32 (s, 1H), 5.63 (q, J = 7.2 Hz, 1H), 2.22 (s, 3H), 1.89 (d, J = 7.2, 3H) |
| 204 | 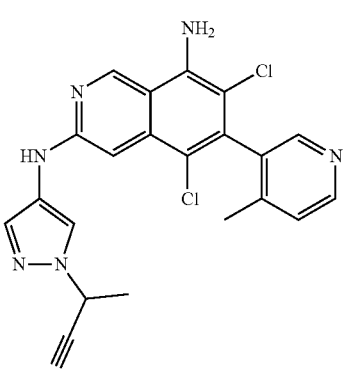<br>2-(4-(8-amino-5,7-dichloro-6-(4-methylpyridin-3-yl)isoquinolin-3-ylamino)-1H-pyrazol-1-yl)propanenitrile | 2.202<br>438.1<br>K | $^1$HNMR (300 MHz, CD$_3$OD) δ 9.26 (s, 1H), 8.48 (d, J = 5.1 Hz, 1H), 8.29 (s, 1H), 8.14 (1H, s), 7.70 (s, 1H), 7.46 (d, J = 5.1 Hz, 1H), 7.16 (s, 1H), 5.65 (q, J = 7.2 Hz, 1H), 2.17 (s, 3H), 1.90 (d, J = 7.2 Hz, 3H) |

TABLE A-3-continued

| Compound No. | Structure/Name | LCMS $R_T$ (min), M + H+, method | 1H NMR (ppm) |
|---|---|---|---|
| 205 | 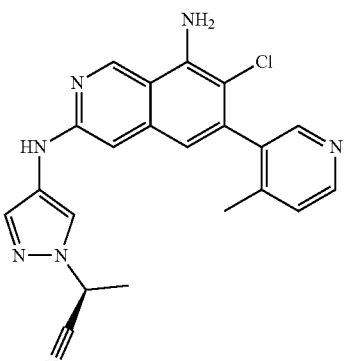<br>(2S)-2-(4-(8-amino-7-chloro-6-(4-methylpyridin-3-yl)isoquinolin-3-ylamino)-1H-pyrazol-1-yl)propanenitrile<br>(Absolute stereochemistry arbitrarily assigned) | 1.775<br>404.2<br>K | 1HNMR (300 MHz, CD3OD) δ 9.17 (s, 1H), 8.42 (d, J = 5.1 Hz, 1H), 8.27 (s, 1H), 8.07 (s, 1H), 7.66 (s, 1H), 7.39 (d, J = 5.1 Hz, 1H), 6.80 (s, 2H), 5.61 (q, J = 7.2 Hz, 1H), 2.22 (s, 3H), 1.89 (d, J = 7.2 Hz, 3H) |
| 206 | 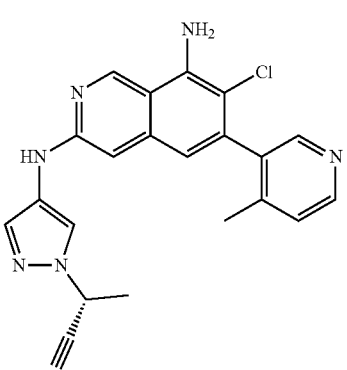<br>(2R)-2-(4-(8-amino-7-chloro-6-(4-methylpyridin-3-yl)isoquinolin-3-ylamino)-1H-pyrazol-1-yl)propanenitrile<br>(Absolute stereochemistry arbitrarily assigned) | 1.777<br>404.2<br>K | 1HNMR (300 MHz, CD3OD) δ 9.17 (s, 1H), 8.42 (d, J = 5.1 Hz, 1H), 8.27 (s, 1H), 8.07 (s, 1H), 7.66 (s, 1H), 7.39 (d, J = 5.1 Hz, 1H), 6.80 (s, 2H),<br>5.61 (q, J = 7.2 Hz, 1H), 2.22 (s, 3H), 1.89 (d, J = 7.2 Hz, 3H) |
| 207 | 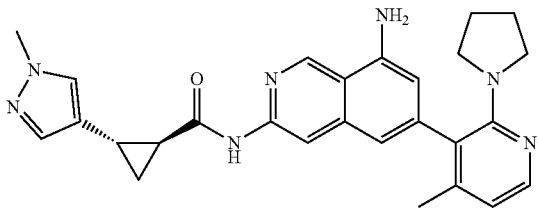<br>(1S,2S)-N-(8-amino-6-(4-methyl-2-(pyrrolidin-1-yl)pyridin-3-yl)isoquinolin-3-yl)-2-(1-methyl-1H-pyrazol-4-yl)cyclopropanecarboxamide<br>(Absolute stereochemistry arbitrarily assigned) | 1.14<br>467.0<br>K | 1HNMR (400 MHz, CD3OD) δ 9.22 (s, 1H), 8.24 (s, 1H), 7.93 (d, J = 5.2 Hz, 1H), 7.51 (s, 1H), 7.38 (s, 1H), 6.91 (s, 1H), 6.67-6.60 (m, 2H), 3.86 (s, 3H), 3.15-3.07 (m, 4H), 2.42-2.32 (m, 1H), 2.15-2.04 (m, 4H), 1.75-1.67 (m, 4H), 1.57 (dt, J = 9.1, 4.5 Hz, 1H), 1.33-1.20 (m, 1H). |

TABLE A-3-continued

| Compound No. | Structure/Name | LCMS R$_T$ (min), M + H$^+$, method | $^1$H NMR (ppm) |
|---|---|---|---|
| 208 | 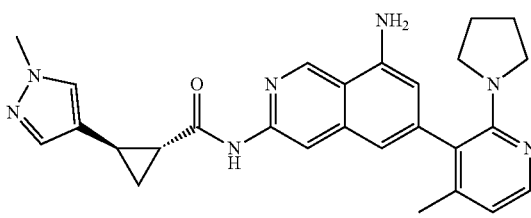<br>(1R,2R)-N-(8-amino-6-(4-methyl-2-(pyrrolidin-1-yl)pyridin-3-yl)isoquinolin-3-yl)-2-(1-methyl-1H-pyrazol-4-yl)cyclopropanecarboxamide (Absolute stereochemistry arbitrarily assigned) | 1.38<br>467.0<br>K | $^1$HNMR (400 MHz, CD$_3$OD) δ 9.22 (s, 1H), 8.24 (s, 1H), 7.93 (d, J = 5.3 Hz, 1H), 7.51 1H), 7.38 1H), 6.91 1H), 6.67-6.60 (m, 2H), 3.86 (s, 3H), 3.15-3.07 (m, 4H), 2.37 (dt, J = 9.7, 4.4 Hz, 1H), 2.14-2.04 (m, 4H), 1.75-1.67 (m, 4H), 1.57 (dt, J = 9.3, 4.6 Hz, 1H), 1.33-1.20 (m, 1H). |
| 209 | 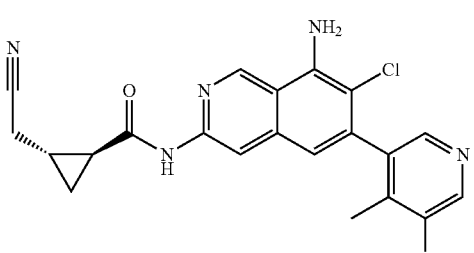<br>(±)-trans-N-(8-amino-6-(5-amino-4-methylpyridin-3-yl)-7-chloroisoquinolin-3-yl)-2-(cyanomethyl)cyclopropanecarboxamide (Absolute stereochemistry arbitrarily assigned) | 1.21<br>407.0<br>M | $^1$HNMR (400 MHz, DMSO-d$_6$) δ 10.95 (s, 1H), 9.45 (s, 1H), 8.24 (s, 1H), 7.97 (s, 1H), 7.56 (s, 1H), 6.88 (s, 1H), 6.54 (s, 2H), 5.22 (s, 2H), 2.77-2.70 (m, 2H), 2.11-2.07 (m, 1H), 1.82 (s, 3H), 1.58-1.55 (m, 1H), 1.15-1.08 (m, 1H), 0.99-0.92 (m, 1H). |
| 210 | 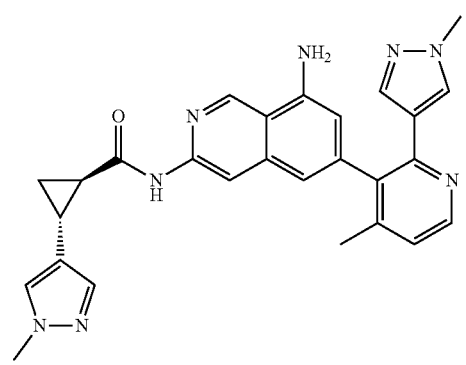<br>(1R,2R)-N-(8-amino-6-(4-methyl-2-(1-methyl-1H-pyrazol-4-yl)pyridin-3-yl)isoquinolin-3-yl)-2-(1-methyl-1H-pyrazol-4-yl)cyclopropanecarboxamide (Absolute stereochemistry arbitrarily assigned) | 1.09<br>479.3<br>K | $^1$HNMR (400 MHz, CD$_3$OD) δ 9.28 (s, 1H), 8.41 (d, J = 5.1 Hz, 1H), 8.26 (s, 1H), 7.51 (s, 1H), 7.37 (d, J = 8.0 Hz, 2H), 7.27 (d, J = 5.1 Hz, 1H), 7.16 (s, 1H), 6.89 (s, 1H), 6.53 (d, J = 1.4 Hz, 1H), 3.86 (s, 3H), 3.71 (s, 3H), 2.36 (ddd, J = 9.6, 6.3, 4.0 Hz, 1H), 2.18 (s, 3H), 2.14-2.05 (m, 1H), 1.56 (dt, J = 9.1, 4.6 Hz, 1H), 1.27-1.20 (m, 1H). |

TABLE A-3-continued

| Compound No. | Structure/Name | LCMS R_T (min), M + H+, method | 1H NMR (ppm) |
|---|---|---|---|
| 211 | 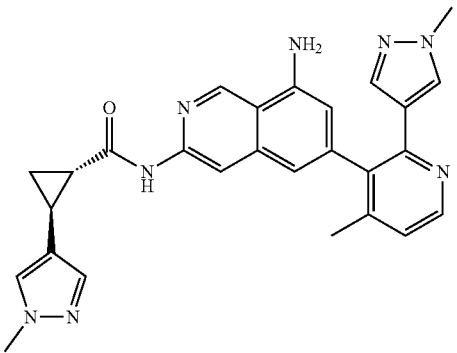<br>(1S,2S)-N-(8-amino-6-(4-methyl-2-(1-methyl-1H-pyrazol-4-yl)pyridin-3-yl)isoquinolin-3-yl)-2-(1-methyl-1H-pyrazol-4-yl)cyclopropanecarboxamide (Absolute stereochemistry arbitrarily assigned) | 1.09<br>479.3<br>K | $^1$HNMR (400 MHz, CD$_3$OD) δ 9.28 (s, 1H), 8.41 (d, J = 5.1 Hz, 1H), 8.26 (s, 1H), 7.51 (s, 1H), 7.37 (d, J = 8.0 Hz, 2H), 7.27 (d, J = 5.1 Hz, 1H), 7.16 (s, 1H), 6.89 (s, 1H), 6.53 (d, J = 1.4 Hz, 1H), 3.86 (s, 3H), 3.71 (s, 3H), 2.36 (ddd, J = 9.8, 6.4, 4.0 Hz, 1H), 2.18 (s, 3H), 2.14-2.07 (m, 1H), 1.56 (dt, J = 9.2, 4.6 Hz, 1H), 1.28-1.19 (m, 1H) |
| 212 | 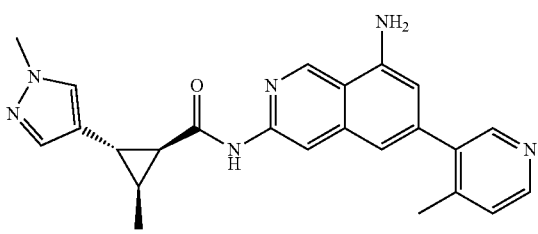<br>(1S,2S,3S)-N-(8-amino-6-(4-methylpyridin-3-yl)isoquinolin-3-yl)-2-methyl-3-(1-methyl-1H-pyrazol-4-yl)cyclopropanecarboxamide (Absolute stereochemistry arbitrarily assigned) | 0.95<br>413.4<br>M | $^1$HNMR (300 MHz, CD$_3$OD) δ 9.26 (s, 1H), 8.45-8.43 (m, 2H), 8.34 (s, 1H), 7.48 (s, 1H), 7.45 (d, J = 6.0 Hz 1H), 7.35 (s, 1H), 7.03 (s, 1H), 6.70 (d, J = 3.0 Hz, 1H), 3.86 (s, 3H), 2.41 (s, 3H), 2.34 (dd, J = 6.5, 4.8 Hz, 1H), 2.17 (dd, J = 9.1, 4.9 Hz, 1H), 1.66 (dt, J = 8.9, 6.2 Hz, 1H), 1.37 (d, J = 6.2 Hz, 3H). |
| 213 | 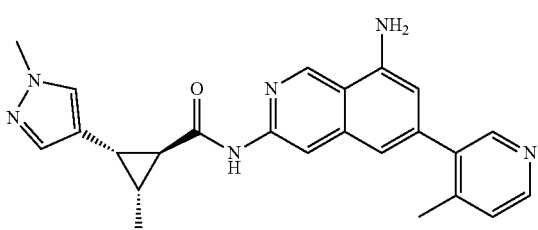<br>(1S,2R,3S)-N-(8-amino-6-(4-methylpyridin-3-yl)isoquinolin-3-yl)-2-methyl-3-(1-methyl-1H-pyrazol-4-yl)cyclopropanecarboxamide (Absolute stereochemistry arbitrarily assigned) | 0.75<br>413.2<br>K | $^1$HNMR (400 MHz, CD$_3$OD) δ 9.26 (s, 1H), 8.46-8.37 (m, 2H), 8.32 (s, 1H), 7.52 (s, 1H), 7.41 (d, J = 4.8 Hz, 2H), 7.04 (s, 1H), 6.69 (d, J = 3.0 Hz, 1H), 3.89 (s, 3H), 2.52 (dd, J = 9.3, 4.7 Hz, 1H), 2.39 (s, 3H), 1.99 (t, J = 4.7 Hz, 1H), 1.82-1.72 (m, 1H), 1.07 (d, J = 6.3 Hz, 3H). |

TABLE A-3-continued

| Compound No. | Structure/Name | LCMS R_T (min), M + H+, method | ¹H NMR (ppm) |
|---|---|---|---|
| 214 | (1R,2S,3R)-N-(8-amino-6-(4-methylpyridin-3-yl)isoquinolin-3-yl)-2-methyl-3-(1-methyl-1H-pyrazol-4-yl)cyclopropanecarboxamide (Absolute stereochemistry arbitrarily assigned) | 0.75 413.3 K | ¹HNMR (300 MHz, CD$_3$OD) δ 9.24 (s, 1H), 8.42 (d, J = 5.4 Hz, 2H), 8.33 (s, 1H), 7.53 (s, 1H), 7.41 (t, J = 2.6 Hz, 2H), 7.01 (s, 1H), 6.70 (d, J = 3.0 Hz, 1H), 3.90 (s, 3H), 2.53 (dd, J = 9.2, 4.7 Hz, 1H), 2.39 (s, 3H), 2.00 (t, J = 4.7 Hz, 1H), 1.77 (ddd, J = 9.4, 6.1, 4.7 Hz, 1H), 1.07 (d, J = 6.2 Hz, 3H). |
| 215 | (1R,2R,3R)-N-(8-amino-6-(4-methylpyridin-3-yl)isoquinolin-3-yl)-2-methyl-3-(1-methyl-1H-pyrazol-4-yl)cyclopropanecarboxamide (Absolute stereochemistry arbitrarily assigned) | 0.95 413.3 N | ¹HNMR (300 MHz, CD$_3$OD) δ 9.31 (s, 1H), 8.49-8.39 (m, 2H), 8.34 (s, 1H), 7.55-7.41 (m, 2H), 7.35 (s, 1H), 7.03 (s, 1H), 6.70 (d, J = 3.0 Hz, 1H), 3.86 (s, 3H), 2.41 (s, 3H), 2.34 (dd, J = 6.5, 4.9 Hz, 1H), 2.17 (dd, J = 9.1, 4.9 Hz, 1H), 1.66 (dt, J = 9.0, 6.3 Hz, 1H), 1.37 (d, J = 6.2 Hz, 3H). |
| 216 | (1R,2R)-N-(8-amino-6-(2,6-dichlorophenyl)isoquinolin-3-yl)-2-(1-methyl-1H-pyrazol-4-yl)cyclopropanecarboxamide (Absolute stereochemistry arbitrarily assigned) | 1.30 452.1 K | ¹HNMR (400 MHz, DMSO-d$_6$) δ 10.78 (s, 1H), 9.32 (s, 1H), 8.26 (s, 1H), 7.63-7.55 (m, 3H), 7.48-7.41 (m, 1H), 7.29 (s, 1H), 6.79 (s, 1H), 6.40 (s, 1H), 6.35 (s, 2H), 3.77 (s, 3H), 2.21-2.16 (m, 2H), 1.39-1.35 (m, 1H), 1.19-1.14 (m, 1H). |
| 217 | (1S,2S)-N-(8-amino-6-(2,6-dichlorophenyl)isoquinolin-3-yl)-2-(1-methyl-1H-pyrazol-4-yl)cyclopropanecarboxamide (Absolute stereochemistry arbitrarily assigned) | 1.31 452.2 K | ¹HNMR (400 MHz, DMSO-d$_6$) δ 10.78 (s, 1H), 9.32 (s, 1H), 8.26 (s, 1H), 7.65-7.51 (m, 3H), 7.46 (dd, J = 8.7, 7.5 Hz, 1H), 7.30 (s, 1H), 6.79 (s, 1H), 6.40 (s, 1H), 6.35 (s, 2H), 3.78 (s, 3H), 2.23-2.13 (m, 2H), 1.42-1.33 (m, 1H), 1.21-1.12 (m, 1H). |

TABLE A-3-continued

| Compound No. | Structure/Name | LCMS R$_T$ (min), M + H$^+$, method | $^1$H NMR (ppm) |
|---|---|---|---|
| 218 | 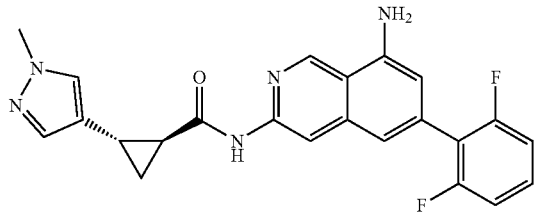<br>(1S,2S)-N-(8-amino-6-(2,6-difluorophenyl)isoquinolin-3-yl)-2-(1-methyl-1H-pyrazol-4-yl)cyclopropanecarboxamide<br>(Absolute stereochemistry arbitrarily assigned) | 1.49<br>420.2<br>K | $^1$HNMR (400 MHz, CD$_3$OD) δ 9.24 (s, 1H), 8.30 (s, 1H), 7.51 (s, 1H), 7.44 (ddd, J = 8.5, 6.3, 2.1 Hz, 1H), 7.38 (s, 1H), 7.10 (t, J = 8.0 Hz, 3H), 6.78 (s, 1H), 3.86 (s, 3H), 2.37 (td, J = 6.1, 3.2 Hz, 1H), 2.11 (dt, J = 8.7, 4.7 Hz, 1H), 1.57 (ddd, J = 9.2, 5.1, 4.1 Hz, 1H), 1.26 (ddd, J = 8.2, 6.4, 4.1 Hz, 1H). |
| 219 | 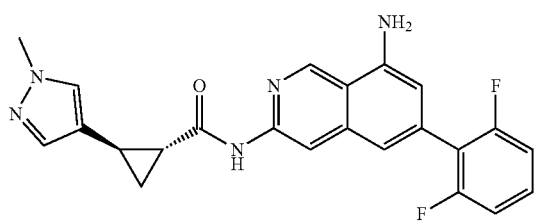<br>(1R,2R)-N-(8-amino-6-(2,6-difluorophenyl)isoquinolin-3-yl)-2-(1-methyl-1H-pyrazol-4-yl)cyclopropanecarboxamide<br>(Absolute stereochemistry arbitrarily assigned) | 1.49<br>420.2<br>K | $^1$HNMR (400 MHz, CD$_3$OD) δ 9.24 (s, 1H), 8.30 (s, 1H), 7.51 (s, 1H), 7.44 (ddd, J =8.5, 6.3, 2.1 Hz, 1H), 7.38 (s, 1H), 7.10 (t, J = 8.0 Hz, 3H), 6.78 (s, 1H), 3.86 (s, 3H), 2.37 (td, J = 6.1, 3.2 Hz, 1H), 2.11 (dt, J = 8.7, 4.7 Hz, 1H), 1.57 (ddd, J = 9.2, 5.1, 4.1 Hz, 1H), 1.26 (ddd, J = 8.2, 6.4, 4.1 Hz, 1H). |
| 220 | 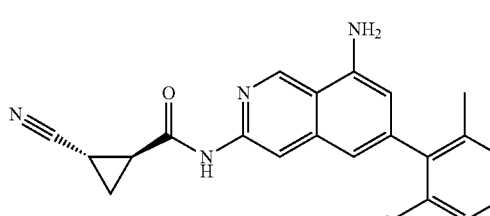<br>(1S,2S)-N-(8-amino-6-(2-cyano-6-methylphenyl)isoquinolin-3-yl)-2-cyanocyclopropanecarboxamide<br>(Absolute stereochemistry arbitrarily assigned) | 1.55<br>368.2<br>M | $^1$H NMR (300 MHz, DMSO-d$_6$) δ 11.14 (s, 1H), 9.37 (s, 1H), 8.24 (s, 1H), 7.76 (d, J = 5.5 Hz, 1H), 7.66 (d, J = 5.5 Hz, 1H), 7.50 (t, J = 5.8 Hz, 1H), 6.86 (s, 1H), 6.46 (d, J = 7.2 Hz, 3H), 2.78-2.72 (m, 1H), 2.16-2.10 (m, 4H), 1.62-1.57 (m, 1H), 1.45-1.43 (m, 1H). |
| 221 | 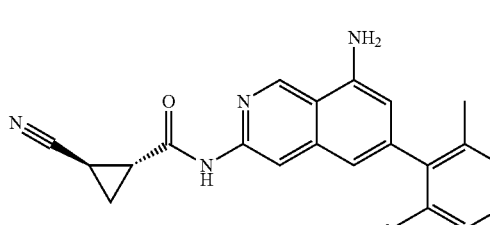<br>(1R,2R)-N-(8-amino-6-(2-cyano-6-methylphenyl)isoquinolin-3-yl)-2-cyanocyclopropanecarboxamide<br>(Absolute stereochemistry arbitrarily assigned) | 1.55<br>368.2<br>M | $^1$H NMR (300 MHz, DMSO-d$_6$) δ 11.14 (s, 1H), 9.37 (s, 1H), 8.24 (s, 1H), 7.76 (d, J = 5.5 Hz, 1H), 7.66 (d, J =5.5 Hz, 1H), 7.50 (t, J = 5.8 Hz, 1H), 6.86 (s, 1H), 6.46 (d, J = 7.2 Hz, 3H), 2.78-2.72 (m, 1H), 2.16-2.10 (m, 4H), 1.62-1.57 (m, 1H), 1.45-1.43 (m, 1H). |

TABLE A-3-continued

| Compound No. | Structure/Name | LCMS R$_T$ (min), M + H$^+$, method | $^1$H NMR (ppm) |
|---|---|---|---|
| 222 | 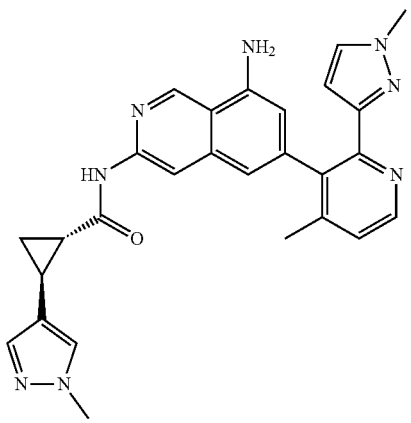<br>(1S,2S)-N-(8-amino-6-(4-methyl-2-(1-methyl-1H-pyrazol-3-yl)pyridin-3-yl)isoquinolin-3-yl)-2-(1-methyl-1H-pyrazol-4-yl)cyclopropanecarboxamide (Absolute stereochemistry arbitrarily assigned) | 1.10 479.3 K | $^1$HNMR (400 MHz, DMSO-d$_6$) 10.74 (s, 1H), 9.27 (s, 1H), 8.48 (d, J = 6.0 Hz, 1H), 8.19 (s, 1H), 7.56 (s, 1H), 7.38-7.29 (m, 3H), 6.71 (s, 1H), 6.33 (s, 1H), 6.20 (s, 2H), 5.77 (s, 1H), 3.77 (s, 3H), 3.68 (s, 3H), 2.18 (t, J = 6.0 Hz, 2H), 2.09 (s, 3H), 1.35-1.34 (m, 1H), 1.17-1.15 (m, 1H). |
| 223 | 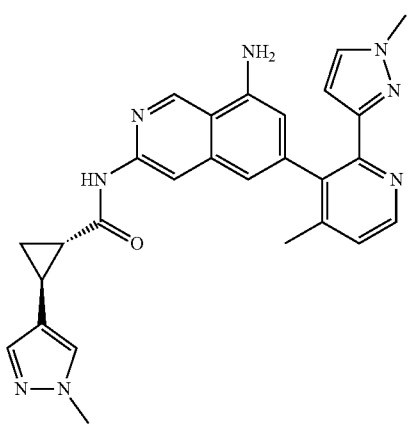<br>(1S,2S)-N-(8-amino-6-(4-methyl-2-(1-methyl-1H-pyrazol-3-yl)pyridin-3-yl)isoquinolin-3-yl)-2-(1-methyl-1H-pyrazol-4-yl)cyclopropanecarboxamide (Absolute stereochemistry arbitrarily assigned) | 1.10 479.3 K | $^1$HNMR (400 MHz, DMSO-d$_6$) 10.74 (s, 1H), 9.27 (s, 1H), 8.48 (d, J = 6.0 Hz, 1H), 8.19 (s, 1H), 7.56 (s, 1H), 7.38-7.29 (m, 3H), 6.71 (s, 1H), 6.33 (s, 1H), 6.20 (s, 2H), 5.77 (s, 1H), 3.77 (s, 3H), 3.68 (s, 3H), 2.18 (t, J = 6.0 Hz, 2H), 2.09 (s, 3H), 1.35-1.34 (m, 1H), 1.17-1.15 (m, 1H). |
| 224 | Exo for C3-Pr, unknown for OH<br>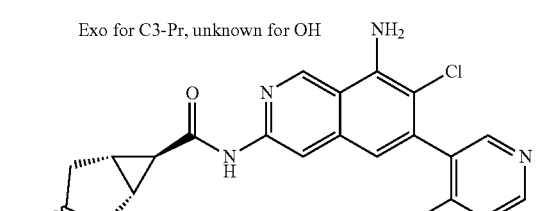<br>(1R,5S,6r)-N-(8-amino-7-chloro-6-(4-methylpyridin-3-yl)isoquinolin-3-yl)-3-hydroxybicyclo[3.1.0]hexane-6-carboxamide | 2.236 409.1 K | $^1$HNMR (300 MHz, DMSO-d$_6$) 10.59 (s, 1H), 9.44 (s, 1H), 8.49 (d, J = 6.0 Hz, 1H), 8.32 (s, 1H), 8.23 (s, 1H), 7.37 (d, J = 6.0 Hz, 1H), 6.91 (s, 1H), 6.57 (s, 2H), 4.70 (d, J = 6.0 Hz, 1H), 3.85-3.78 (m, 1H), 2.11 (s, 3H), 2.09-2.04 (m, 2H), 1.89-1.87 (m, 1H), 1.73-1.71 (m, 2H), 1.69-1.61 (m, 2H). |

TABLE A-3-continued

| Compound No. | Structure/Name | LCMS R_T (min), M + H+, method | $^1$H NMR (ppm) |
|---|---|---|---|
| 225 | Exo for C3-Pr, unknown for OH 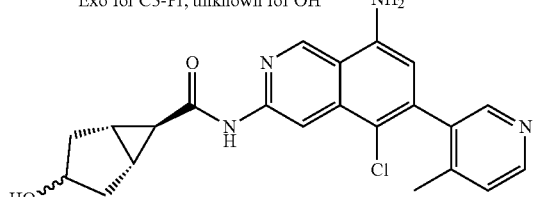<br>(1R,5S,6r)-N-(8-amino-5-chloro-6-(4-methylpyridin-3-yl)isoquinolin-3-yl)-3-hydroxybicyclo[3.1.0]hexane-6-carboxamide | 1.029<br>409.2<br>K | $^1$HNMR (300 MHz, DMSO-d$_6$) 10.70 (s, 1H), 9.37 (s, 1H), 8.62 (s, 1H), 8.49 (d, J = 6.0 Hz, 1H), 8.32 (s, 1H), 7.38 (d, J = 6.0 Hz, 1H), 6.54 (s, 2H), 6.44 (s, 1H), 4.71 (d, J = 6.0 Hz, 1H), 3.83-3.78 (m, 1H), 2.12 (s, 3H), 2.09-2.05 (m, 2H), 1.92-1.90 (m, 1H), 1.76-1.74 (m, 2H), 1.69-1.62 (m, 2H). |
| 226 | 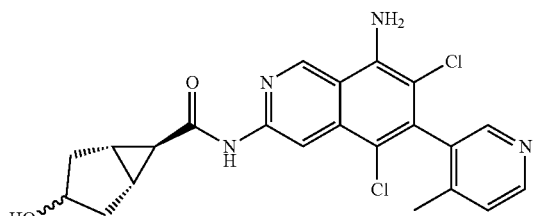<br>(1R,5S,6r)-N-(8-amino-5,7-dichloro-6-(4-methylpyridin-3-yl)isoquinolin-3-yl)-3-hydroxybicyclo[3.1.0]hexane-6-carboxamide | 1.205<br>443.1<br>L | $^1$HNMR (300 MHz, DMSO-d$_6$) 10.79 (s, 1H), 9.53 (s, 1H), 8.64 (s, 1H), 8.53 (d, J = 6.0 Hz, 1H), 8.29 (s, 1H), 7.43 (d, J = 6.0 Hz, 1H), 6.77 (s, 2H), 4.71 (d, J = 6.0 Hz, 1H), 3.85-3.79 (m, 1H), 2.12-2.08 (m, 2H), 2.05 (s, 3H), 1.92-1.90 (m, 1H), 1.75-1.74 (m, 2H), 1.69-1.62 (m, 2H). |
| 227 | 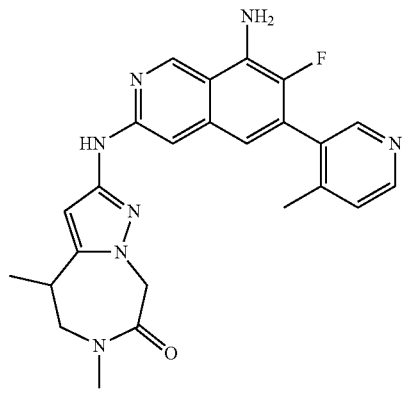 | 1.006<br>446.3<br>L | n/a |
| 228 | 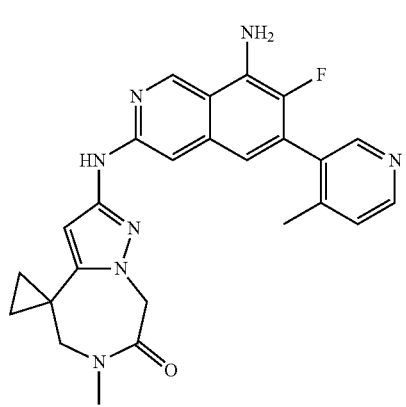 [SMILES: Cc1ccncc1-c1cc2cc(Nc3cc4n(n3)CC(=O)N(C)CC43CC3)ncc2c(N)c1F] | 458.3 | $^1$H NMR (400 MHz, DMSO-d$_6$) δ 9.27 (s, 1H), 9.02 (s, 1H), 8.51 (d, J = 6.0 Hz, 1H), 8.43 (s, 1H), 7.68 (s, 1H), 7.39 (d, J = 6.0 Hz, 1H), 6.79 (d, J = 6.0 Hz, 1H), 6.11 (s, 2H), 5.61 (s, 1H), 5.06 (s, 2H), 3.73 (s, 2H), 2.99 (s, 3H), 2.22 (s, 3H), 1.24-1.18 (m, 2H), 0.96-094 (m, 2H). |

TABLE A-3-continued

| Compound No. | Structure/Name | LCMS $R_T$ (min), $M + H^+$, method | $^1$H NMR (ppm) |
|---|---|---|---|
| 229 | | 0.942<br>447.2<br>L | $^1$H NMR (300 MHz, DMSO-$d_6$) δ 9.26 (s, 1H), 9.07 (s, 1H), 7.99 (s, 1H), 7.69 (s, 1H), 7.66 (s, 1H), 6.72 (d, J = 6.1 Hz, 1H), 6.07 (s, 2H), 5.99 (s, 1H), 5.23 (s, 2H), 4.98 (s, 2H), 3.84 (t, J = 5.7 Hz, 2H), 3.05 (t, J = 5.6 Hz, 2H), 2.96 (s, 3H), 1.94 (d, J = 1.5 Hz, 3H). |
| 230 | | 0.957<br>432.3<br>L | $^1$H NMR (400 MHz, DMSO-$d_6$) δ 9.27 (s, 1H), 9.11 (s, 1H), 8.51 (s, 1H), 8.43 (s, 1H), 7.74 (s, 1H), 7.39 (d, J = 7.2 Hz, 1H), 6.78 (d, J = 7.2 Hz, 1H), 6.13 (s, 2H), 5.98 (s, 1H), 4.97 (s, 2H), 3.84-3.81 (m, 2H), 3.05-3.03 (m, 2H), 2.95 (s, 3H), 2.22 (s, 3H). |

TABLE A-4

| Cmpd No. | Structure/Name | LCMS $R_T$ (min); $M + H^+$; Method |
|---|---|---|
| 9 | 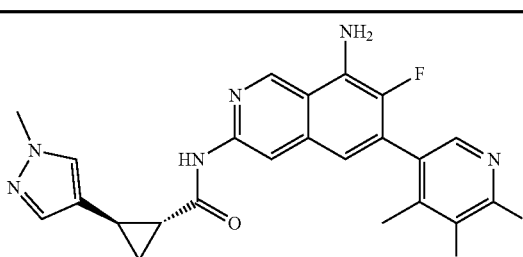<br>(1R,2S,3R)-N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide<br>(Pyrazole trans to amide; ethyl relative stereochemistry arbitrarily assigned; All absolute stereochemistry arbitrarily assigned) | See Example 134 |

TABLE A-4-continued

| Cmpd No. | Structure/Name | LCMS $R_T$ (min); M + H⁺; Method |
|---|---|---|
| 10 | 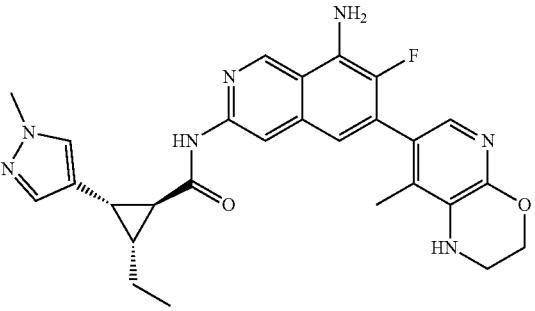 [SMILES: CC[C@H]1[C@H](C(=O)Nc2cc3cc(-c4cnc5c(c4C)NCCO5)c(F)c(N)c3cn2)[C@H]1c1cnn(C)c1]<br>(1S,2R,3S)-N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide<br>(Pyrazole trans to amide; ethyl relative stereochemistry arbitrarily assigned; All absolute stereochemistry arbitrarily assigned) | See Example 134 |
| 11 | 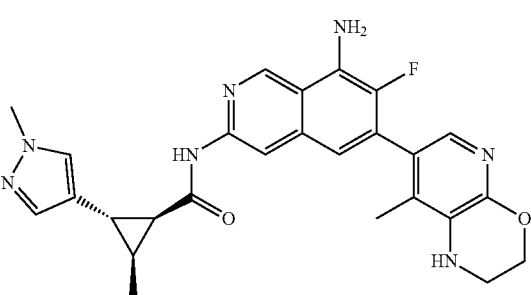<br>(1S,2S,3S)-N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide<br>(Pyrazole trans to amide; ethyl relative stereochemistry arbitrarily assigned; All absolute stereochemistry arbitrarily assigned) | See Example 134 |
| 12 | 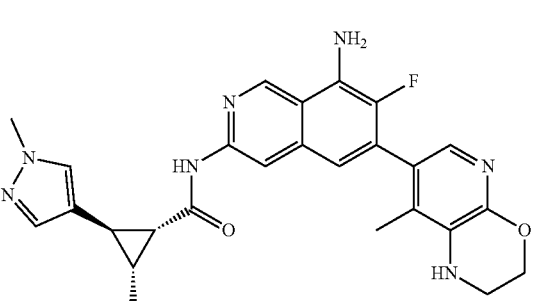<br>(1R,2R,3R)-N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide<br>(Pyrazole trans to amide; ethyl relative stereochemistry arbitrarily assigned; All absolute stereochemistry arbitrarily assigned) | See Example 134 |

TABLE A-4-continued

| Cmpd No. | Structure/Name | LCMS $R_T$ (min); M + H+; Method |
|---|---|---|
| 29 | 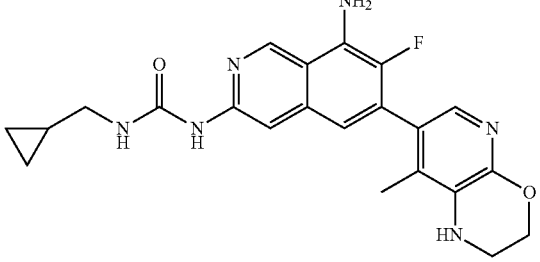<br>1-(8-amino-7-fluoro-6-(8-methyl-2,3-dihydro-1H-pyrido[2,3-b][1,4]oxazin-7-yl)isoquinolin-3-yl)-3-(cyclopropylmethyl)urea | See Example 133 |
| 33 | 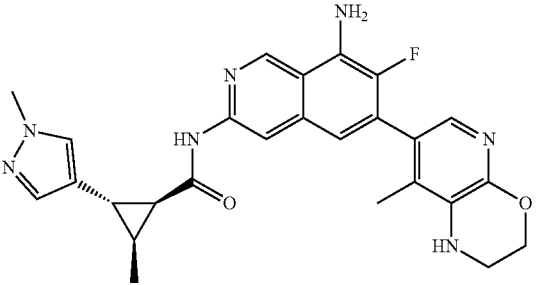<br>(1S,2S,3S)-N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide<br>(Pyrazole trans to amide; methyl relative stereochemistry arbitrarily assigned; All absolute stereochemistry arbitrarily assigned) | See Example 135 |
| 34 | 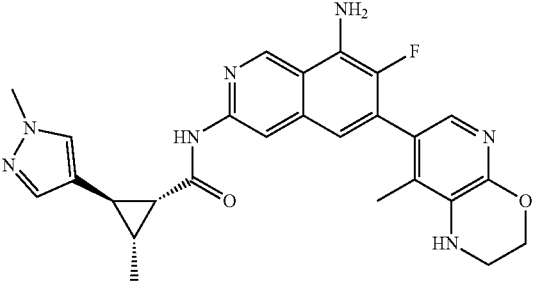 [SMILES: Cc1c(-c2cc3cc(NC(=O)[C@@H]4[C@H](C)[C@H]4c4cnn(C)c4)ncc3c(N)c2F)cnc2c1NCCO2]<br>(1R,2R,3R)-N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide<br>(Pyrazole trans to amide; methyl relative stereochemistry arbitrarily assigned; All absolute stereochemistry arbitrarily assigned) | See Example 135 |
| 35 | 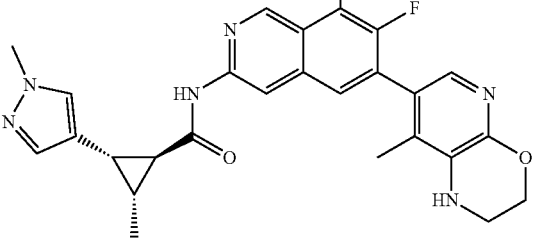<br>(1S,2R,3S)-N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide<br>(Pyrazole trans to amide; methyl relative stereochemistry arbitrarily assigned; All absolute stereochemistry arbitrarily assigned) | See Example 135 |

US 11,566,003 B2

TABLE A-4-continued

| Cmpd No. | Structure/Name | LCMS R$_T$ (min); M + H$^+$; Method |
|---|---|---|
| 36 | 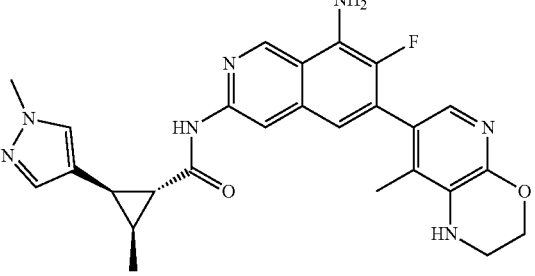<br>(1R,2S,3R)-N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide<br>(Pyrazole trans to amide; methyl relative stereochemistry arbitrarily assigned; All absolute stereochemistry arbitrarily assigned) | See Example 135 |
| 53 | 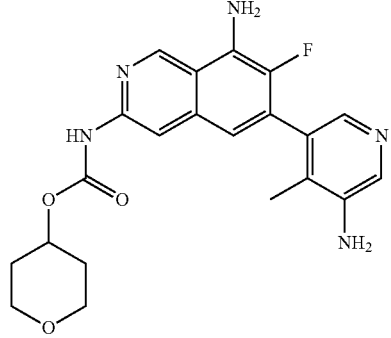 [SMILES: Cc1c(N)cncc1-c1cc2cc(NC(=O)OC3CCOCC3)ncc2c(N)c1F]<br>tetrahydro-2H-pyran-4-yl (8-amino-6-(5-amino-4-methylpyridin-3-yl)-7-fluoroisoquinolin-3-yl)carbamate | 2.71 412.1 N |
| 58 | 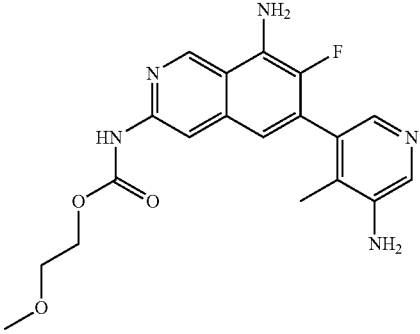 [SMILES: COCCOC(=O)Nc1cc2cc(-c3cncc(N)c3C)c(F)c(N)c2cn1]<br>2-methoxyethyl (8-amino-6-(5-amino-4-methylpyridin-3-yl)-7-fluoroisoquinolin-3-yl)carbamate | 2.54 386.1 N |
| 64 | 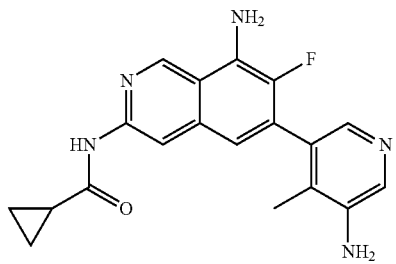 [SMILES: Cc1c(N)cncc1-c1cc2cc(NC(=O)C3CC3)ncc2c(N)c1F]<br>N-(8-amino-6-(5-amino-4-methylpyridin-3-yl)-7-fluoroisoquinolin-3-yl)cyclopropanecarboxamide | 2.50 352.1 N |

TABLE A-4-continued

| Cmpd No. | Structure/Name | LCMS $R_T$ (min); M + H$^+$; Method |
|---|---|---|
| 83 | 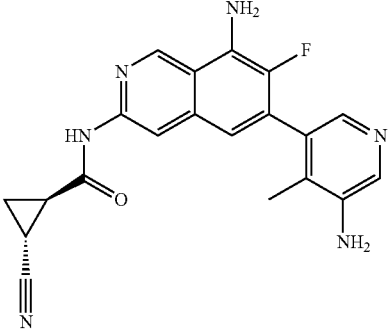<br>(1R,2R)-N-(8-amino-6-(5-amino-4-methylpyridin-3-yl)-7-fluoroisoquinolin-3-yl)-2-cyanocyclopropane-1-carboxamide<br>(Nitrile trans to amide; Absolute stereochemistry arbitrarily assigned) | 2.53<br>377.1<br>N |
| 84 | 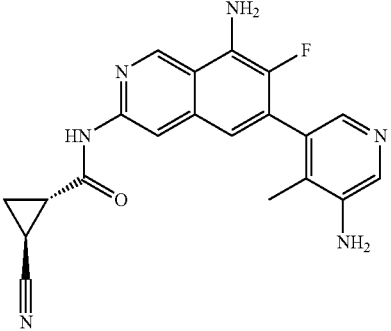<br>(1S,2S)-N-(8-amino-6-(5-amino-4-methylpyridin-3-yl)-7-fluoroisoquinolin-3-yl)-2-cyanocyclopropane-1-carboxamide<br>(Nitrile trans to amide; Absolute stereochemistry arbitrarily assigned) | 2.53<br>377.1<br>N |
| 96 | 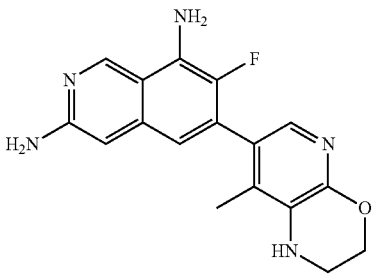 [SMILES: Cc1c(-c2cc3cc(N)ncc3c(N)c2F)cnc2c1NCCO2]<br>7-fluoro-6-(8-methyl-2,3-dihydro-1H-pyrido[2,3-b][1,4]oxazin-7-yl)isoquinoline-3,8-diamine | 1.39<br>326.12<br>K |
| 97 | 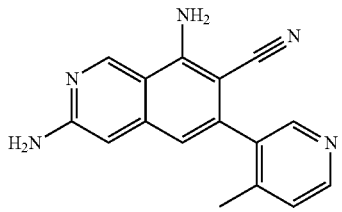<br>3,8-diamino-6-(4-methylpyridin-3-yl)isoquinoline-7-carbonitrile | 1.45<br>2.76.1<br>E |

TABLE A-4-continued

| Cmpd No. | Structure/Name | LCMS $R_T$ (min); M + H$^+$; Method |
|---|---|---|
| 111 | 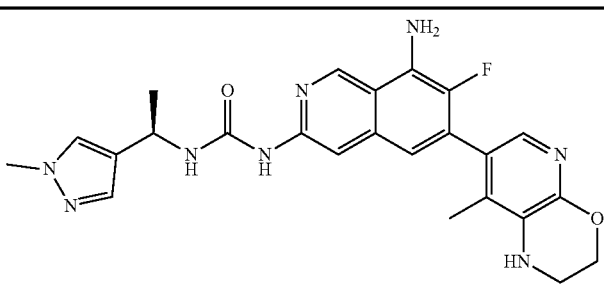<br>(R)-1-(8-amino-7-fluoro-6-(8-methyl-2,3-dihydro-1H-pyrido[2,3-b][1,4]oxazin-7-yl)isoquinolin-3-yl)-3-(1-(1-methyl-1H-pyrazol-4-yl)ethyl)urea<br>(Absolute stereochemistry arbitrarily assigned) | See Example 137 |
| 112 | 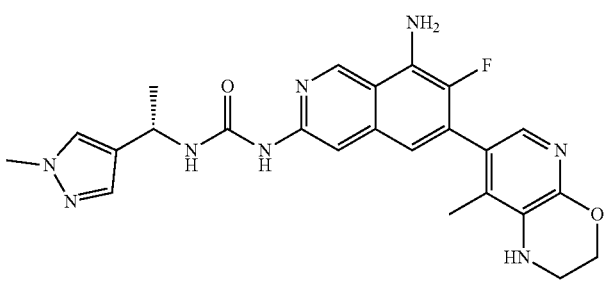 [SMILES: Cc1c(-c2cc3cc(NC(=O)N[C@@H](C)c4cnn(C)c4)ncc3c(N)c2F)cnc2c1NCCO2]<br>(S)-1-(8-amino-7-fluoro-6-(8-methyl-2,3-dihydro-1H-pyrido[2,3-b][1,4]oxazin-7-yl)isoquinolin-3-yl)-3-(1-(1-methyl-1H-pyrazol-4-yl)ethyl)urea<br>(Absolute stereochemistry arbitrarily assigned) | See Example 137 |
| 114 | 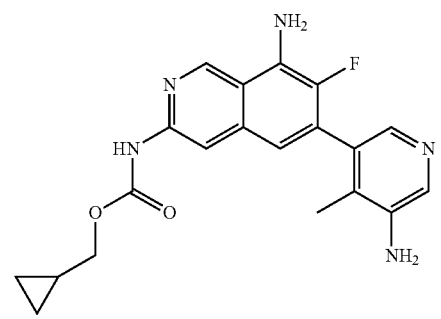 [SMILES: Cc1c(N)cncc1-c1cc2cc(NC(=O)OCC3CC3)ncc2c(N)c1F]<br>cyclopropylmethyl (8-amino-6-(5-amino-4-methylpyridin-3-yl)-7-fluoroisoquinolin-3-yl)carbamate | 3.05<br>382.1<br>N |
| 120 | 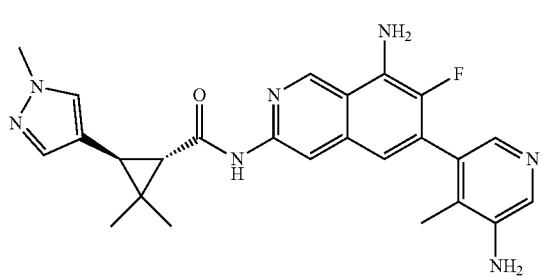<br>(1S,3S)-N-(8-amino-6-(5-amino-4-methylpyridin-3-yl)-7-fluoroisoquinolin-3-yl)-2,2-dimethyl-3-(1-methyl-1H-pyrazol-4-yl)cyclopropane-1-carboxamide<br>(Pyrazole1 trans to amide; Absolute stereochemistry arbitrarily assigned) | See Example 173 |

TABLE A-4-continued

| Cmpd No. | Structure/Name | LCMS R$_T$ (min); M + H$^+$; Method |
|---|---|---|
| 121 | (1R,3R)-N-(8-amino-6-(5-amino-4-methylpyridin-3-yl)-7-fluoroisoquinolin-3-yl)-2,2-dimethyl-3-(1-methyl-1H-pyrazol-4-yl)cyclopropane-1-carboxamide (Pyrazole1 trans to amide; Absolute stereochemistry arbitrarily assigned) | See Example 173 |
| 129 | isopropyl (8-amino-6-(5-amino-4-methylpyridin-3-yl)-7-fluoroisoquinolin-3-yl)carbamate | 2.91 370.1 N |
| 137 | 1-(8-amino-7-fluoro-6-(4-methylpyridin-3-yl)isoquinolin-3-yl)-3-(1-cyanopropan-2-yl)urea | 2.78 379.1 N |
| 141 | (+/−)-7-fluoro-6-(4-methylpyridin-3-yl)-N3-(3-(morpholin-3-yl)phenyl)isoquinoline-3,8-diamine | 2.42 430.1 N |

TABLE A-4-continued

| Cmpd No. | Structure/Name | LCMS R_T (min); M + H+; Method |
|---|---|---|
| 142 | (S)-7-fluoro-6-(4-methylpyridin-3-yl)-N3-(3-(morpholin-3-yl)phenyl)isoquinoline-3,8-diamine | 2.42 430.1 N |
| 152 | (+/−)-cis-N-(8-amino-6-(2,6-dichlorophenyl)-7-fluoroisoquinolin-3-yl)-2-fluorocyclopropane-1-carboxamide | See Example 229 |
| 158 | (1R,5S,6r)-N-(8-amino-6-(5-amino-4-methylpyridin-3-yl)-7-fluoroisoquinolin-3-yl)-3-oxabicyclo[3.1.0]hexane-6-carboxamide | 2.53 394.1 N |
| 231 | 2-((8-amino-7-fluoro-6-(4-methylpyridin-3-yl)isoquinolin-3-yl)amino)-6-(methyl-d3)-5,6-dihydro-4H-pyrazolo[1,5-d][1,4]diazepin-7(8H)-one | See Example 191 |

TABLE A-4-continued

| Cmpd No. | Structure/Name | LCMS $R_T$ (min); M + H$^+$; Method |
|---|---|---|
| 232 | 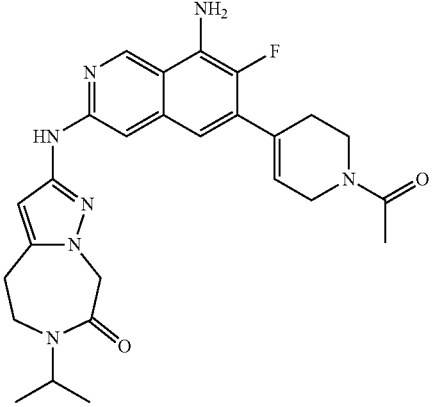 [SMILES: CC(=O)N1CC=C(c2cc3cc(Nc4cc5n(n4)CC(=O)N(C(C)C)CC5)ncc3c(N)c2F)CC1]<br>2-((6-(1-acetyl-1,2,3,6-tetrahydropyridin-4-yl)-8-amino-7-fluoroisoquinolin-3-yl)amino)-6-isopropyl-5,6-dihydro-4H-pyrazolo[1,5-d][1,4]diazepin-7(8H)-one | See Example 230 |
| 233 | 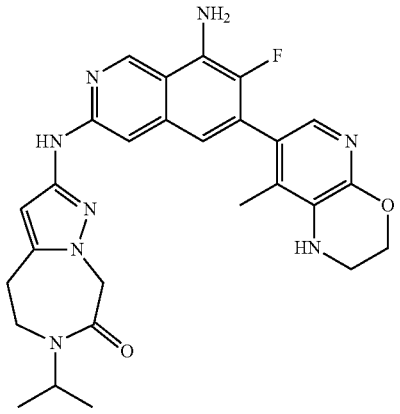 [SMILES: Cc1c(-c2cc3cc(Nc4cc5n(n4)CC(=O)N(C(C)C)CC5)ncc3c(N)c2F)cnc2c1NCCO2]<br>2-((8-amino-7-fluoro-6-(8-methyl-2,3-dihydro-1H-pyrido[2,3-b][1,4]oxazin-7-yl)isoquinolin-3-yl)amino)-6-isopropyl-5,6-dihydro-4H-pyrazolo[1,5-d][1,4]diazepin-7(8H)-one | See Example 136 |
| 234 | 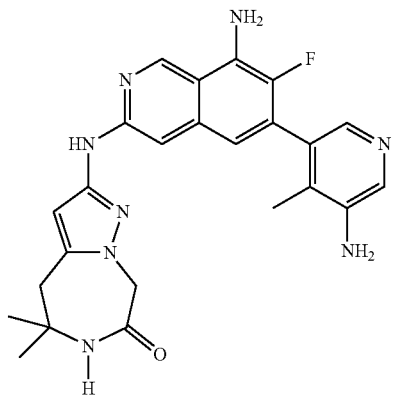 [SMILES: Cc1c(N)cncc1-c1cc2cc(Nc3cc4n(n3)CC(=O)NC(C)(C)C4)ncc2c(N)c1F]<br>2-((8-amino-6-(5-amino-4-methylpyridin-3-yl)-7-fluoroisoquinolin-3-yl)amino)-5,5-dimethyl-5,6-dihydro-4H-pyrazolo[1,5-d][1,4]diazepin-7(8H)-one | See Example 138 |

TABLE A-4-continued

| Cmpd No. | Structure/Name | LCMS R$_T$ (min); M + H$^+$; Method |
|---|---|---|
| 235 | 2-((8-amino-6-(5-amino-4-methylpyridin-3-yl)-7-fluoroisoquinolin-3-yl)amino)-5,5,6-trimethyl-5,6-dihydro-4H-pyrazolo[1,5-d][1,4]diazepin-7(8H)-one | See Example 139 |
| 236 | (1S,2S,3S)-N-(8-amino-6-(5-amino-4-methylpyridin-3-yl)-7-fluoroisoquinolin-3-yl)-2-(cyanomethyl)-3-methylcyclopropane-1-carboxamide (Cyanomethyl trans to amide; methyl relative stereochemistry arbitrarily assigned; All absolute stereochemistry arbitrarily assigned) | See Example 140 |
| 237 | (1R,2R,3R)-N-(8-amino-6-(5-amino-4-methylpyridin-3-yl)-7-fluoroisoquinolin-3-yl)-2-(cyanomethyl)-3-methylcyclopropane-1-carboxamide (Cyanomethyl trans to amide; methyl relative stereochemistry arbitrarily assigned; All absolute stereochemistry arbitrarily assigned) | See Example 140 |

TABLE A-4-continued

| Cmpd No. | Structure/Name | LCMS R_T (min); M + H+; Method |
|---|---|---|
| 238 | 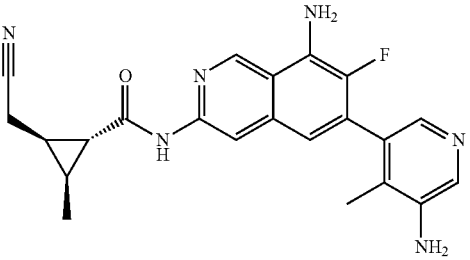<br>(1R,2R,3S)-N-(8-amino-6-(5-amino-4-methylpyridin-3-yl)-7-fluoroisoquinolin-3-yl)-2-(cyanomethyl)-3-methylcyclopropane-1-carboxamide<br>(Cyanomethyl trans to amide; methyl relative stereochemistry arbitrarily assigned; All absolute stereochemistry arbitrarily assigned) | See Example 140 |
| 239 | 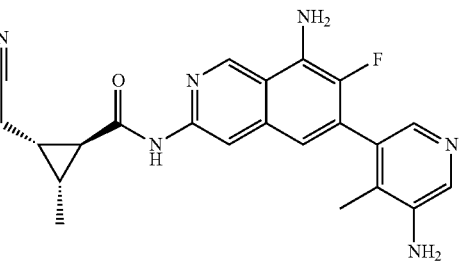<br>(1S,2S,3R)-N-(8-amino-6-(5-amino-4-methylpyridin-3-yl)-7-fluoroisoquinolin-3-yl)-2-(cyanomethyl)-3-methylcyclopropane-1-carboxamide<br>(Cyanomethyl trans to amide; methyl relative stereochemistry arbitrarily assigned; All absolute stereochemistry arbitrarily assigned) | See Example 140 |
| 240 | 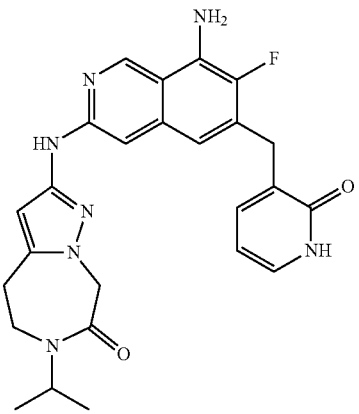 [SMILES: CC(C)N1CCc2cc(Nc3cc4cc(Cc5ccc[nH]c5=O)c(F)c(N)c4cn3)nn2CC1=O]<br>2-((8-amino-7-fluoro-6-((2-oxo-1,2-dihydropyridin-3-yl)methyl)isoquinolin-3-yl)amino)-6-isopropyl-5,6-dihydro-4H-pyrazolo[1,5-d][1,4]diazepin-7(8H)-one | See Example 141 |

TABLE A-4-continued

| Cmpd No. | Structure/Name | LCMS R_T (min); M + H+; Method |
|---|---|---|
| 241 | N-(8-amino-3-((6-isopropyl-7-oxo-5,6,7,8-tetrahydro-4H-pyrazolo[1,5-d][1,4]diazepin-2-yl)amino)isoquinolin-6-yl)ethanesulfonamide | See Example 142 |
| 242 | 5-(8-amino-7-fluoro-3-((6-isopropyl-7-oxo-5,6,7,8-tetrahydro-4H-pyrazolo[1,5-d][1,4]diazepin-2-yl)amino)isoquinolin-6-yl)-4-ethyloxazol-2(3H)-one | See Example 143 |
| 243 | 2-((8-amino-6-(5-amino-4-chloropyridin-3-yl)-7-fluoroisoquinolin-3-yl)amino)-6-isopropyl-5,6-dihydro-4H-pyrazolo[1,5-d][1,4]diazepin-7(8H)-one | See Example 144 |

TABLE A-4-continued

| Cmpd No. | Structure/Name | LCMS $R_T$ (min); M + H⁺; Method |
|---|---|---|
| 244 | 2-((8-amino-7-fluoro-6-((4-methyl-2-oxopiperazin-1-yl)methyl)isoquinolin-3-yl)amino)-6-isopropyl-5,6-dihydro-4H-pyrazolo[1,5-d][1,4]diazepin-7(8H)-one | See Example 145 |
| 245 | 5-(8-amino-7-fluoro-3-((6-isopropyl-7-oxo-5,6,7,8-tetrahydro-4H-pyrazolo[1,5-d][1,4]diazepin-2-yl)amino)isoquinolin-6-yl)-N,N,4-trimethylpyrimidine-2-carboxamide | See Example 146 |
| 246 | 2-((8-amino-6-(5-amino-4-methoxypyridin-3-yl)-7-fluoroisoquinolin-3-yl)amino)-6-isopropyl-5,6-dihydro-4H-pyrazolo[1,5-d][1,4]diazepin-7(8H)-one | See Example 147 |

TABLE A-4-continued

| Cmpd No. | Structure/Name | LCMS $R_T$ (min); M + H+; Method |
|---|---|---|
| 247 | 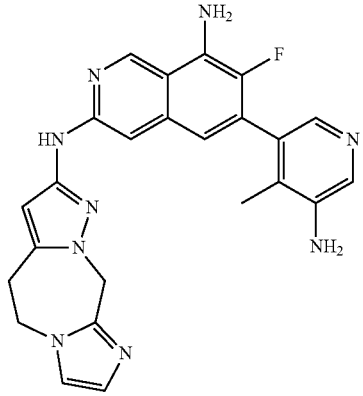 [SMILES: Cc1c(N)cncc1-c1cc2cc(Nc3cc4n(n3)Cc3nccn3CC4)ncc2c(N)c1F]<br>6-(5-amino-4-methylpyridin-3-yl)-N3-(5,6-dihydro-11H-imidazo[1,2-a]pyrazolo[1,5-d][1,4]diazepin-8-yl)-7-fluoroisoquinoline-3,8-diamine | See Example 148 |
| 248 | 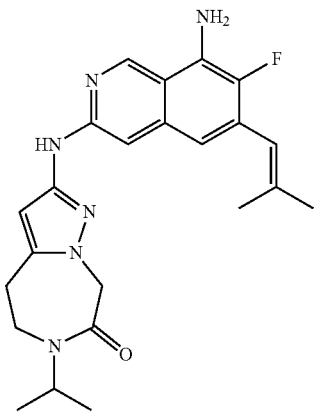 [SMILES: CC(C)=Cc1cc2cc(Nc3cc4n(n3)CC(=O)N(C(C)C)CC4)ncc2c(N)c1F]<br>2-((8-amino-7-fluoro-6-(2-methylprop-1-en-1-yl)isoquinolin-3-yl)amino)-6-isopropyl-5,6-dihydro-4H-pyrazolo[1,5-d][1,4]diazepin-7(8H)-one | 4.13 423.2 N |
| 249 | 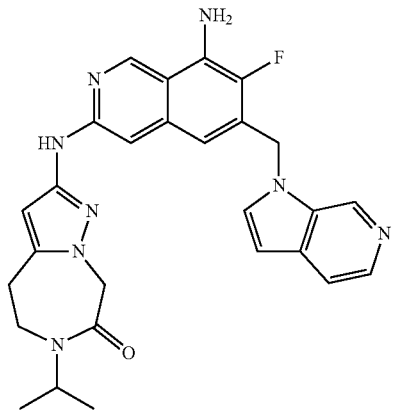 [SMILES: CC(C)N1CCc2cc(Nc3cc4cc(Cn5ccc6ccncc65)c(F)c(N)c4cn3)nn2CC1=O]<br>2-((6-((1H-pyrrolo[2,3-c]pyridin-1-yl)methyl)-8-amino-7-fluoroisoquinolin-3-yl)amino)-6-isopropyl-5,6-dihydro-4H-pyrazolo[1,5-d][1,4]diazepin-7(8H)-one | See Example 149 |

TABLE A-4-continued

| Cmpd No. | Structure/Name | LCMS $R_T$ (min); M + H⁺; Method |
|---|---|---|
| 250 | 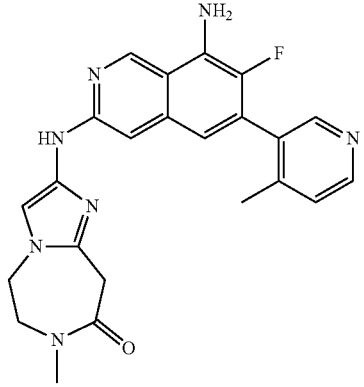 [SMILES: Cc1ccncc1-c1cc2cc(Nc3cn4c(n3)CC(=O)N(C)CC4)ncc2c(N)c1F]  2-((8-amino-7-fluoro-6-(4-methylpyridin-3-yl)isoquinolin-3-yl)amino)-7-methyl-6,7-dihydro-5H-imidazo[1,2-d][1,4]diazepin-8(9H)-one | See Example 150 |
| 251 | 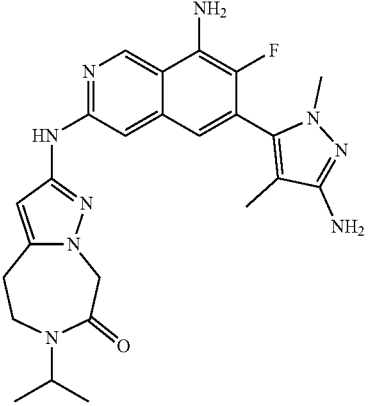 [SMILES: Cc1c(N)nn(C)c1-c1cc2cc(Nc3cc4n(n3)CC(=O)N(C(C)C)CC4)ncc2c(N)c1F]  2-((8-amino-6-(3-amino-1,4-dimethyl-1H-pyrazol-5-yl)-7-fluoroisoquinolin-3-yl)amino)-6-isopropyl-5,6-dihydro-4H-pyrazolo[1,5-d][1,4]diazepin-7(8H)-one | See Example 231 |
| 252 | 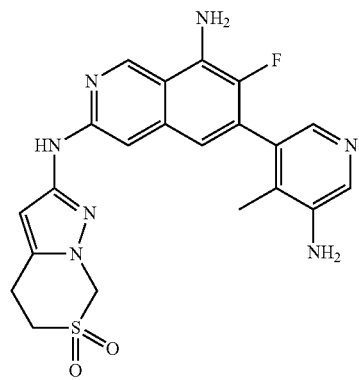 [SMILES: Cc1c(N)cncc1-c1cc2cc(Nc3cc4n(n3)CS(=O)(=O)CC4)ncc2c(N)c1F]  2-((8-amino-6-(5-amino-4-methylpyridin-3-yl)-7-fluoroisoquinolin-3-yl)amino)-4,5-dihydro-7H-pyrazolo[1,5-c][1,3]thiazine 6,6-dioxide | See Example 151 |

TABLE A-4-continued

| Cmpd No. | Structure/Name | LCMS $R_T$ (min); M + H+; Method |
|---|---|---|
| 253 | 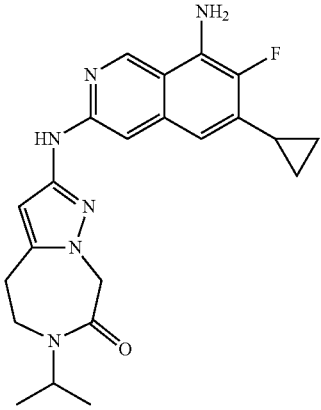 [SMILES: CC(C)N1CCc2cc(Nc3cc4cc(C5CC5)c(F)c(N)c4cn3)nn2CC1=O]

2-((8-amino-6-cyclopropyl-7-fluoroisoquinolin-3-yl)amino)-6-isopropyl-5,6-dihydro-4H-pyrazolo[1,5-d][1,4]diazepin-7(8H)-one | See Example 152 |
| 254 | 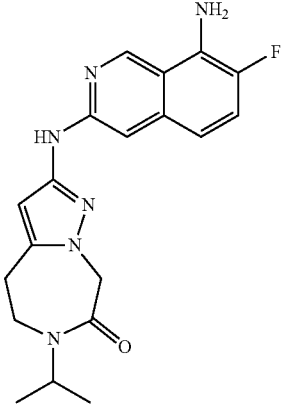 [SMILES: CC(C)N1CCc2cc(Nc3cc4ccc(F)c(N)c4cn3)nn2CC1=O]

2-((8-amino-7-fluoroisoquinolin-3-yl)amino)-6-isopropyl-5,6-dihydro-4H-pyrazolo[1,5-d][1,4]diazepin-7(8H)-one | See Example 153 |
| 255 | 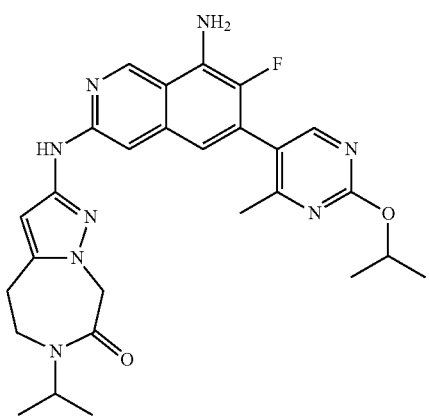 [SMILES: Cc1nc(OC(C)C)ncc1-c1cc2cc(Nc3cc4n(n3)CC(=O)N(C(C)C)CC4)ncc2c(N)c1F]

2-((8-amino-7-fluoro-6-(2-isopropoxy-4-methylpyrimidin-5-yl)isoquinolin-3-yl)amino)-6-isopropyl-5,6-dihydro-4H-pyrazolo[1,5-d][1,4]diazepin-7(8H)-one | See Example 154 |

TABLE A-4-continued

| Cmpd No. | Structure/Name | LCMS R$_T$ (min); M + H$^+$; Method |
|---|---|---|
| 256 | 2-((8-amino-6-(5-amino-4-methylpyridin-3-yl)-7-fluoroisoquinolin-3-yl)amino)-5-isopropyl-4,5-dihydro-7H-pyrazolo[5,1-d][1,2,5]thiadiazine 6,6-dioxide | See Example 155 |
| 257 | 2-((8-amino-6-(benzyloxy)-7-fluoroisoquinolin-3-yl)amino)-6-isopropyl-5,6-dihydro-4H-pyrazolo[1,5-d][1,4]diazepin-7(8H)-one | See Example 156 |
| 258 | 2-((8-amino-7-fluoro-6-methylisoquinolin-3-yl)amino)-6-isopropyl-5,6-dihydro-4H-pyrazolo[1,5-d][1,4]diazepin-7(8H)-one | See Example 157 |

TABLE A-4-continued

| Cmpd No. | Structure/Name | LCMS R_T (min); M + H+; Method |
|---|---|---|
| 259 | 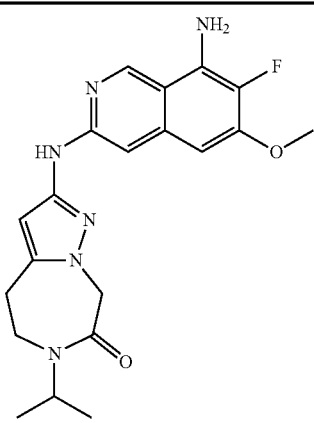<br>2-((8-amino-7-fluoro-6-methoxyisoquinolin-3-yl)amino)-6-isopropyl-5,6-dihydro-4H-pyrazolo[1,5-d][1,4]diazepin-7(8H)-one | See Example 158 |
| 260 | 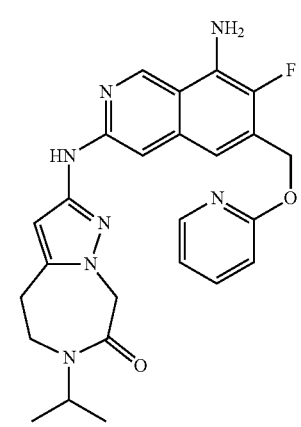 [SMILES: CC(C)N1CCc2cc(Nc3cc4cc(COc5ccccn5)c(F)c(N)c4cn3)nn2CC1=O]<br>2-((8-amino-7-fluoro-6-((pyridin-2-yloxy)methyl)isoquinolin-3-yl)amino)-6-isopropyl-5,6-dihydro-4H-pyrazolo[1,5-d][1,4]diazepin-7(8H)-one | See Example 159 |
| 261 | 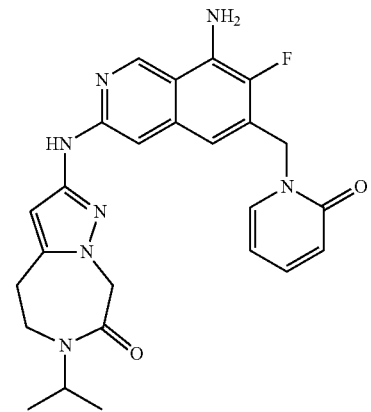 [SMILES: CC(C)N1CCc2cc(Nc3cc4cc(Cn5ccccc5=O)c(F)c(N)c4cn3)nn2CC1=O]<br>2-((8-amino-7-fluoro-6-((2-oxopyridin-1(2H)-yl)methyl)isoquinolin-3-yl)amino)-6-isopropyl-5,6-dihydro-4H-pyrazolo[1,5-d][1,4]diazepin-7(8H)-one | See Example 160 |

TABLE A-4-continued

| Cmpd No. | Structure/Name | LCMS $R_T$ (min); $M + H^+$; Method |
|---|---|---|
| 262 | 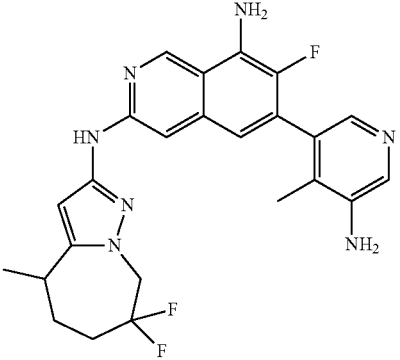 [SMILES: Cc1c(N)cncc1-c1cc2cc(Nc3cc4n(n3)CC(F)(F)CCC4C)ncc2c(N)c1F](+/−)-6-(5-amino-4-methylpyridin-3-yl)-N3-(7,7-difluoro-4-methyl-5,6,7,8-tetrahydro-4H-pyrazolo[1,5-a]azepin-2-yl)-7-fluoroisoquinoline-3,8-diamine | See Example 161 |
| 263 | 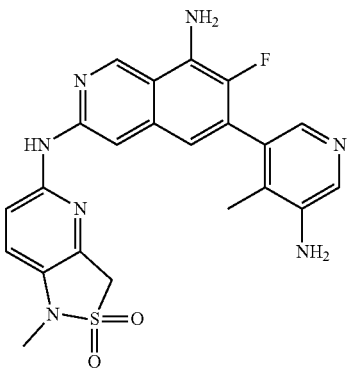 [SMILES: Cc1c(N)cncc1-c1cc2cc(Nc3ccc4c(n3)CS(=O)(=O)N4C)ncc2c(N)c1F]5-((8-amino-6-(5-amino-4-methylpyridin-3-yl)-7-fluoroisoquinolin-3-yl)amino)-1-methyl-1,3-dihydroisothiazolo[4,3-b]pyridine 2,2-dioxide | See Example 162 |
| 264 | 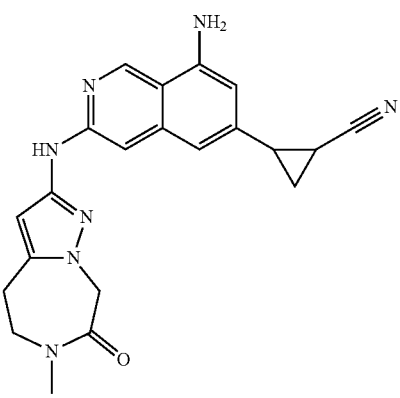 [SMILES: CN1CCc2cc(Nc3cc4cc(C5CC5C#N)cc(N)c4cn3)nn2CC1=O]2-(8-amino-3-((6-methyl-7-oxo-5,6,7,8-tetrahydro-4H-pyrazolo[1,5-d][1,4]diazepin-2-yl)amino)isoquinolin-6-yl)cyclopropane-1-carbonitrile | 2.88 388.2 N |

TABLE A-4-continued

| Cmpd No. | Structure/Name | LCMS $R_T$ (min); M + H⁺; Method |
|---|---|---|
| 265 | 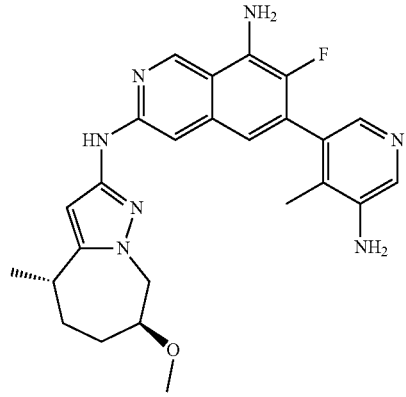 [SMILES: CO[C@H]1CC[C@H](C)c2cc(Nc3cc4cc(-c5cncc(N)c5C)c(F)c(N)c4cn3)nn2C1]<br>6-(5-amino-4-methylpyridin-3-yl)-7-fluoro-N3-((4S,7S)-7-methoxy-4-methyl-5,6,7,8-tetrahydro-4H-pyrazolo[1,5-a]azepin-2-yl)isoquinoline-3,8-diamine<br>(Stereochemistry arbitrarily assigned) | See Example 163 |
| 266 | 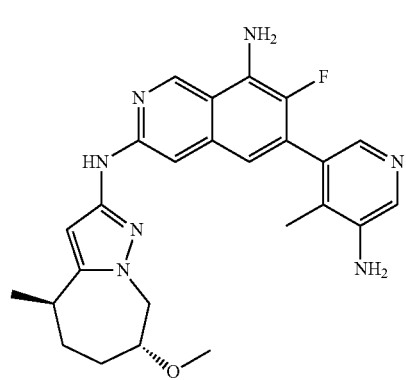 [SMILES: CO[C@@H]1CC[C@@H](C)c2cc(Nc3cc4cc(-c5cncc(N)c5C)c(F)c(N)c4cn3)nn2C1]<br>6-(5-amino-4-methylpyridin-3-yl)-7-fluoro-N3-((4R,7R)-7-methoxy-4-methyl-5,6,7,8-tetrahydro-4H-pyrazolo[1,5-a]azepin-2-yl)isoquinoline-3,8-diamine<br>(Stereochemistry arbitrarily assigned) | See Example 163 |
| 267 | 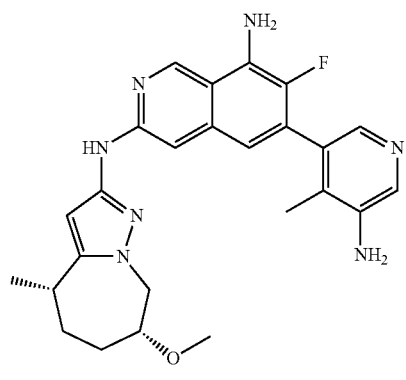 [SMILES: CO[C@@H]1CC[C@H](C)c2cc(Nc3cc4cc(-c5cncc(N)c5C)c(F)c(N)c4cn3)nn2C1]<br>6-(5-amino-4-methylpyridin-3-yl)-7-fluoro-N3-((4S,7R)-7-methoxy-4-methyl-5,6,7,8-tetrahydro-4H-pyrazolo[1,5-a]azepin-2-yl)isoquinoline-3,8-diamine<br>(Stereochemistry arbitrarily assigned) | See Example 163 |

TABLE A-4-continued

| Cmpd No. | Structure/Name | LCMS R_T (min); M + H+; Method |
|---|---|---|
| 268 | 6-(5-amino-4-methylpyridin-3-yl)-7-fluoro-N3-((4R,7S)-7-methoxy-4-methyl-5,6,7,8-tetrahydro-4H-pyrazolo[1,5-a]azepin-2-yl)isoquinoline-3,8-diamine (Stereochemistry arbitrarily assigned) | See Example 163 |
| 269 | 5-(8-amino-7-fluoro-3-((6-isopropyl-7-oxo-5,6,7,8-tetrahydro-4H-pyrazolo[1,5-d][1,4]diazepin-2-yl)amino)isoquinolin-6-yl)-1-ethyl-1H-pyrazole-3-carbonitrile | See Example 164 |
| 270 | 2-((8-amino-7-fluoro-6-(5,6,7,8-tetrahydroimidazo[1,2-a]pyrazin-3-yl)isoquinolin-3-yl)amino)-6-isopropyl-5,6-dihydro-4H-pyrazolo[1,5-d][1,4]diazepin-7(8H)-one | See Example 165 |

TABLE A-4-continued

| Cmpd No. | Structure/Name | LCMS R$_T$ (min); M + H$^+$; Method |
|---|---|---|
| 271 | 2-((8-amino-6-(5-amino-4-methylpyridin-3-yl)-7-fluoroisoquinolin-3-yl)amino)-5,6-dihydro-4H,8H-pyrazolo[1,5-c][1,3]thiazepine 7,7-dioxide | See Example 166 |
| 272 | 2-((8-amino-7-fluoro-6-(5-methyl-2-oxo-1,2-dihydropyridin-4-yl)isoquinolin-3-yl)amino)-6-isopropyl-5,6-dihydro-4H-pyrazolo[1,5-d][1,4]diazepin-7(8H)-one | See Example 167 |
| 273 | .2-((8-amino-7-fluoro-6-(4-methylpyridin-3-yl)isoquinolin-3-yl)amino)-6-(2-hydroxy-2-methylpropyl)-5,6-dihydro-4H-pyrazolo[1,5-d][1,4]diazepin-7(8H)-one | See Example 168 |

TABLE A-4-continued

| Cmpd No. | Structure/Name | LCMS R$_T$ (min); M + H$^+$; Method |
|---|---|---|
| 274 | 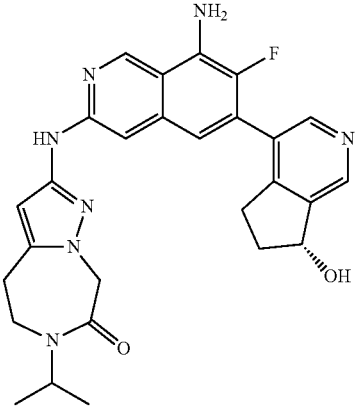 [SMILES: CC(C)N1CCc2cc(Nc3cc4cc(-c5cncc6c5CC[C@H]6O)c(F)c(N)c4cn3)nn2CC1=O]<br>(R)-2-((8-amino-7-fluoro-6-(7-hydroxy-6,7-dihydro-5H-cyclopenta[c]pyridin-4-yl)isoquinolin-3-yl)amino)-6-isopropyl-5,6-dihydro-4H-pyrazolo[1,5-d][1,4]diazepin-7(8H)-one<br>(Absolute stereochemistry arbitrarily assigned) | See Example 169 |
| 275 | 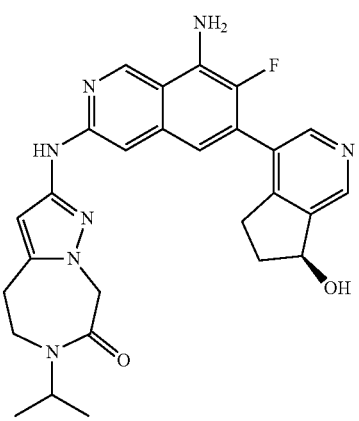 [SMILES: CC(C)N1CCc2cc(Nc3cc4cc(-c5cncc6c5CC[C@@H]6O)c(F)c(N)c4cn3)nn2CC1=O]<br>(S)-2-((8-amino-7-fluoro-6-(7-hydroxy-6,7-dihydro-5H-cyclopenta[c]pyridin-4-yl)isoquinolin-3-yl)amino)-6-isopropyl-5,6-dihydro-4H-pyrazolo[1,5-d][1,4]diazepin-7(8H)-one<br>(Absolute stereochemistry arbitrarily assigned) | See Example 169 |
| 276 | 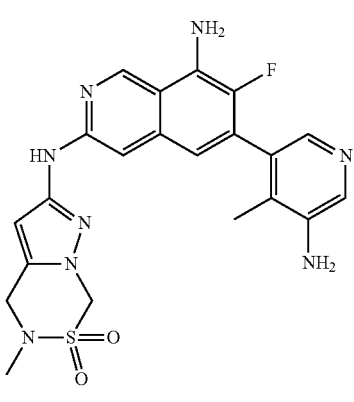 [SMILES: Cc1c(N)cncc1-c1cc2cc(Nc3cc4n(n3)CS(=O)(=O)N(C)C4)ncc2c(N)c1F]<br>2-((8-amino-6-(5-amino-4-methylpyridin-3-yl)-7-fluoroisoquinolin-3-yl)amino)-5-methyl-4,5-dihydro-7H-pyrazolo[5,1-d][1,2,5]thiadiazine 6,6-dioxide | See Example 170 |

TABLE A-4-continued

| Cmpd No. | Structure/Name | LCMS R$_T$ (min); M + H⁺; Method |
|---|---|---|
| 277 | 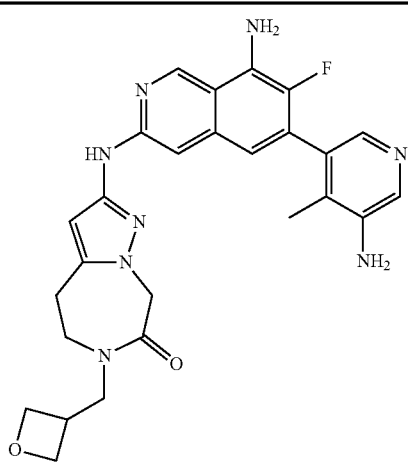<br>2-((8-amino-6-(5-amino-4-methylpyridin-3-yl)-7-fluoroisoquinolin-3-yl)amino)-6-(oxetan-3-ylmethyl)-5,6-dihydro-4H-pyrazolo[1,5-d][1,4]diazepin-7(8H)-one | See Example 171 |
| 278 | 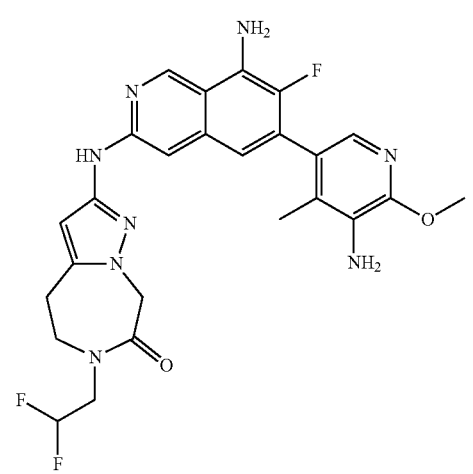 [SMILES: COc1ncc(-c2cc3cc(Nc4cc5n(n4)CC(=O)N(CC(F)F)CC5)ncc3c(N)c2F)c(C)c1N]<br>2-((8-amino-6-(5-amino-6-methoxy-4-methylpyridin-3-yl)-7-fluoroisoquinolin-3-yl)amino)-6-(2,2-difluoroethyl)-5,6-dihydro-4H-pyrazolo[1,5-d][1,4]diazepin-7(8H)-one | See Example 172 |
| 279 | 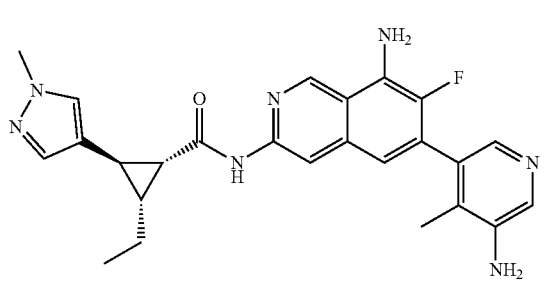<br>(1R,2R,3R)-N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide<br>(Pyrazolel trans to amide; Ethyl relative stereochemistry arbitrarily assigned; Absolute stereochemistry arbitrarily assigned) | See Example 173 |

TABLE A-4-continued

| Cmpd No. | Structure/Name | LCMS R_T (min); M + H+; Method |
|---|---|---|
| 280 | 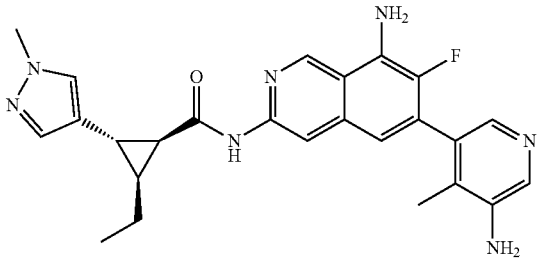<br>(1S,2S,3S)-N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide<br>(Pyrazolel trans to amide; Ethyl relative stereochemistry arbitrarily assigned; Absolute stereochemistry arbitrarily assigned) | See Example 173 |
| 281 | 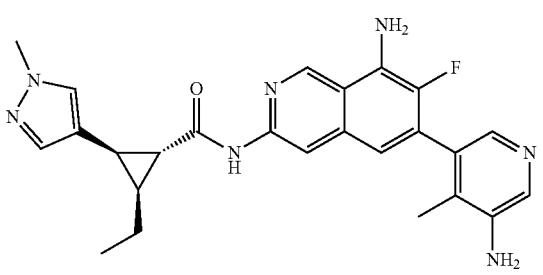<br>(1R,2S,3R)-N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide<br>(Pyrazolel trans to amide; Ethyl relative stereochemistry arbitrarily assigned; Absolute stereochemistry arbitrarily assigned) | See Example 173 |
| 282 | 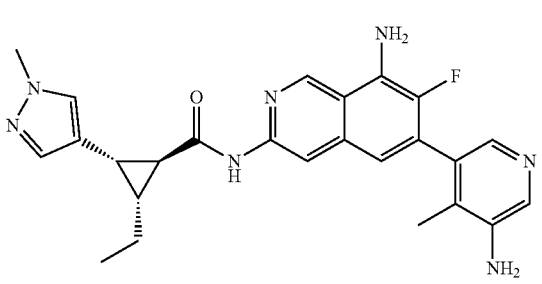<br>(1S,2R,3S)-N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide<br>(Pyrazolel trans to amide; Ethyl relative stereochemistry arbitrarily assigned; Absolute stereochemistry arbitrarily assigned) | See Example 173 |

TABLE A-4-continued

| Cmpd No. | Structure/Name | LCMS R_T (min); M + H+; Method |
|---|---|---|
| 283 | 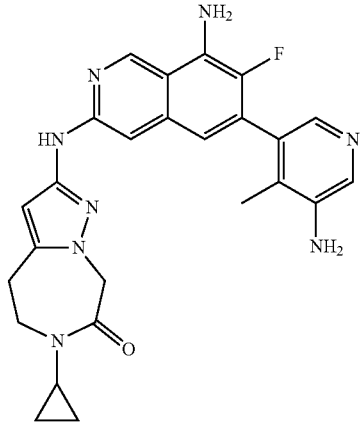 [SMILES: Cc1c(N)cncc1-c1cc2cc(Nc3cc4n(n3)CC(=O)N(C3CC3)CC4)ncc2c(N)c1F]  2-((8-amino-6-(5-amino-4-methylpyridin-3-yl)-7-fluoroisoquinolin-3-yl)amino)-6-cyclopropyl-5,6-dihydro-4H-pyrazolo[1,5-d][1,4]diazepin-7(8H)-one | See Example 174 |
| 284 | 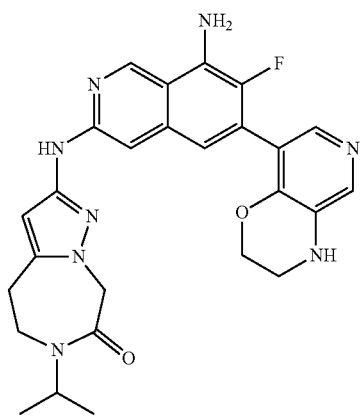 [SMILES: CC(C)N1CCc2cc(Nc3cc4cc(-c5cncc6c5OCCN6)c(F)c(N)c4cn3)nn2CC1=O]  2-((8-amino-6-(3,4-dihydro-2H-pyrido[4,3-b][1,4]oxazin-8-yl)-7-fluoroisoquinolin-3-yl)amino)-6-isopropyl-5,6-dihydro-4H-pyrazolo[1,5-d][1,4]diazepin-7(8H)-one | See Example 175 |
| 285 | 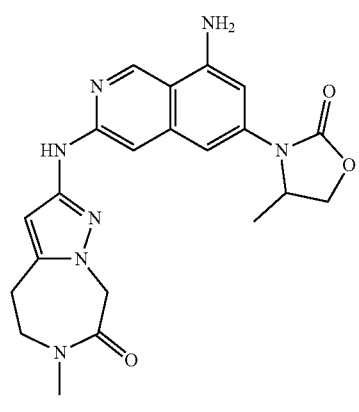 [SMILES: CC1COC(=O)N1c1cc(N)c2cnc(Nc3cc4n(n3)CC(=O)N(C)CC4)cc2c1]  (+/−)-3-(8-amino-3-((6-methyl-7-oxo-5,6,7,8-tetrahydro-4H-pyrazolo[1,5-d][1,4]diazepin-2-yl)amino)isoquinolin-6-yl)-4-methyloxazolidin-2-one | 2.78 422.2 N |

TABLE A-4-continued

| Cmpd No. | Structure/Name | LCMS $R_T$ (min); M + H⁺; Method |
|---|---|---|
| 286 | 2-((8-amino-6-(5-amino-4-ethylpyridin-3-yl)-7-fluoroisoquinolin-3-yl)amino)-6-isopropyl-5,6-dihydro-4H-pyrazolo[1,5-d][1,4]diazepin-7(8H)-one | See Example 176 |
| 287 | (+/−)-2-((8-amino-6-(5-amino-4-methylpyridin-3-yl)-7-fluoroisoquinolin-3-yl)amino)-4-ethyl-4H,6H-pyrazolo[1,5-c]thiazole 5,5-dioxide | See Example 177 |
| 288 | 2-((8-amino-6-(5-amino-4-methylpyridin-3-yl)-7-fluoroisoquinolin-3-yl)amino)-6-(cyclopropylmethyl)-5,6-dihydro-4H-pyrazolo[1,5-d][1,4]diazepin-7(8H)-one | See Example 178 |

TABLE A-4-continued

| Cmpd No. | Structure/Name | LCMS $R_T$ (min); M + H$^+$; Method |
|---|---|---|
| 289 | 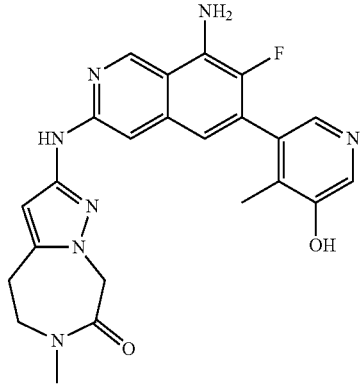<br>2-((8-amino-7-fluoro-6-(5-hydroxy-4-methylpyridin-3-yl)isoquinolin-3-yl)amino)-6-methyl-5,6-dihydro-4H-pyrazolo[1,5-d][1,4]diazepin-7(8H)-one | See Example 179 |
| 290 | 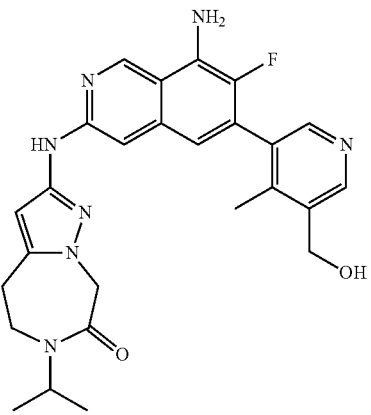 [SMILES: Cc1c(CO)cncc1-c1cc2cc(Nc3cc4n(n3)CC(=O)N(C(C)C)CC4)ncc2c(N)c1F]<br>2-((8-amino-7-fluoro-6-(5-(hydroxymethyl)-4-methylpyridin-3-yl)isoquinolin-3-yl)amino)-6-isopropyl-5,6-dihydro-4H-pyrazolo[1,5-d][1,4]diazepin-7(8H)-one | See Example 180 |
| 291 | 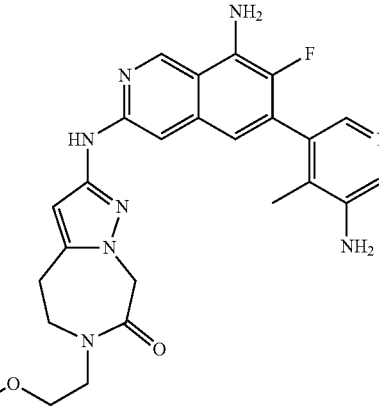<br>2-((8-amino-6-(5-amino-4-methylpyridin-3-yl)-7-fluoroisoquinolin-3-yl)amino)-6-(2-methoxyethyl)-5,6-dihydro-4H-pyrazolo[1,5-d][1,4]diazepin-7(8H)-one | See Example 181 |

TABLE A-4-continued

| Cmpd No. | Structure/Name | LCMS $R_T$ (min); M + H⁺; Method |
|---|---|---|
| 292 | 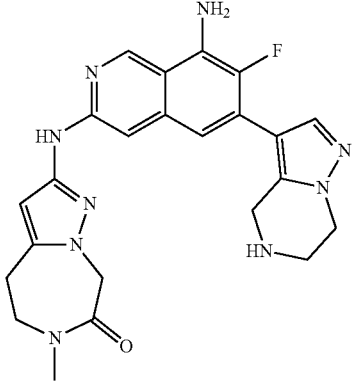 [SMILES: CN1CCc2cc(Nc3cc4cc(-c5cnn6c5CNCC6)c(F)c(N)c4cn3)nn2CC1=O]<br>2-((8-amino-7-fluoro-6-(4,5,6,7-tetrahydropyrazolo[1,5-a]pyrazin-3-yl)isoquinolin-3-yl)amino)-6-methyl-5,6-dihydro-4H-pyrazolo[1,5-d][1,4]diazepin-7(8H)-one | See Example 182 |
| 293 | 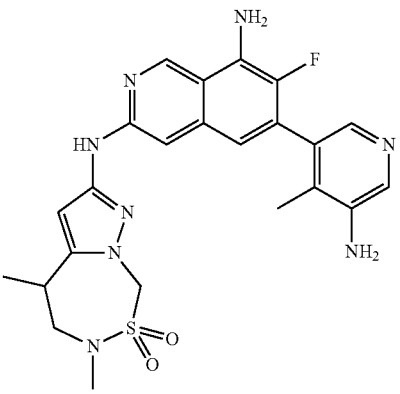 [SMILES: Cc1c(N)cncc1-c1cc2cc(Nc3cc4n(n3)CS(=O)(=O)N(C)CC4C)ncc2c(N)c1F]<br>(+/−)-2-((8-amino-6-(5-amino-4-methylpyridin-3-yl)-7-fluoroisoquinolin-3-yl)amino)-4,6-dimethyl-5,6-dihydro-4H,8H-pyrazolo[5,1-e][1,2,6]thiadiazepine 7,7-dioxide | See Example 183 |
| 294 | 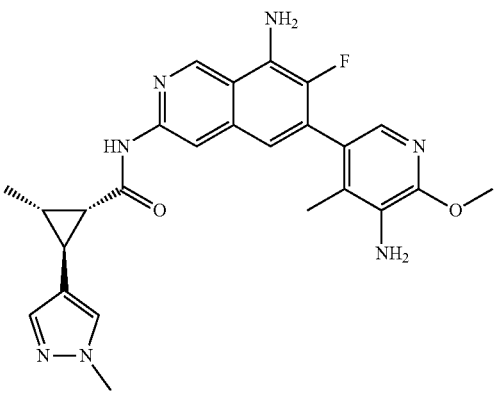<br>(1S,2S,3S)-N-(8-amino-6-(5-amino-6-methoxy-4-methylpyridin-3-yl)-7-fluoroisoquinolin-3-yl)-2-methyl-3-(1-methyl-1H-pyrazol-4-yl)cyclopropane-1-carboxamide<br>(Pyrazolel trans to amide; Methyl relative stereochemistry arbitrarily assigned; Absolute stereochemistry arbitrarily assigned) | 4.25 476.2 N |

TABLE A-4-continued

| Cmpd No. | Structure/Name | LCMS R_T (min); M + H+; Method |
|---|---|---|
| 295 | 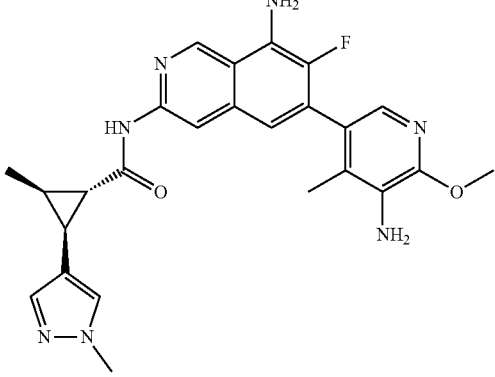<br>(1S,2R,3S)-N-(8-amino-6-(5-amino-6-methoxy-4-methylpyridin-3-yl)-7-fluoroisoquinolin-3-yl)-2-methyl-3-(1-methyl-1H-pyrazol-4-yl)cyclopropane-1-carboxamide<br>(Pyrazolel trans to amide; Methyl relative stereochemistry arbitrarily assigned; Absolute stereochemistry arbitrarily assigned) | 4.27<br>476.2<br>N |
| 296 | 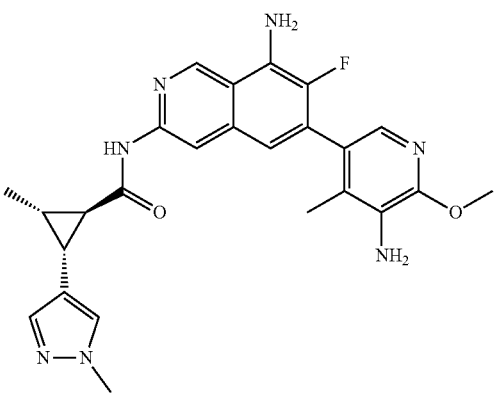<br>(1R,2S,3R)-N-(8-amino-6-(5-amino-6-methoxy-4-methylpyridin-3-yl)-7-fluoroisoquinolin-3-yl)-2-methyl-3-(1-methyl-1H-pyrazol-4-yl)cyclopropane-1-carboxamide<br>(Pyrazolel trans to amide; Methyl relative stereochemistry arbitrarily assigned; Absolute stereochemistry arbitrarily assigned) | 4.27<br>476.2<br>N |
| 297 | 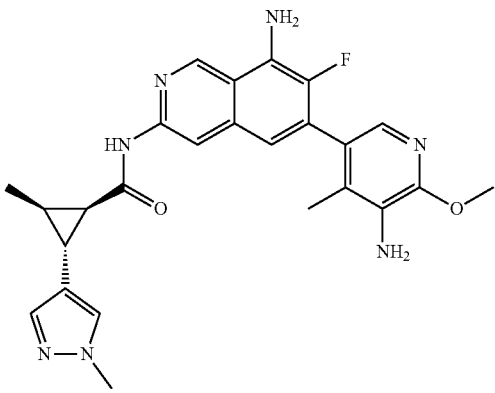<br>(1R,2R,3R)-N-(8-amino-6-(5-amino-6-methoxy-4-methylpyridin-3-yl)-7-fluoroisoquinolin-3-yl)-2-methyl-3-(1-methyl-1H-pyrazol-4-yl)cyclopropane-1-carboxamide<br>(Pyrazolel trans to amide; Methyl relative stereochemistry arbitrarily assigned; Absolute stereochemistry arbitrarily assigned) | 4.25<br>476.2<br>N |

TABLE A-4-continued

| Cmpd No. | Structure/Name | LCMS R$_T$ (min); M + H$^+$; Method |
|---|---|---|
| 298 | 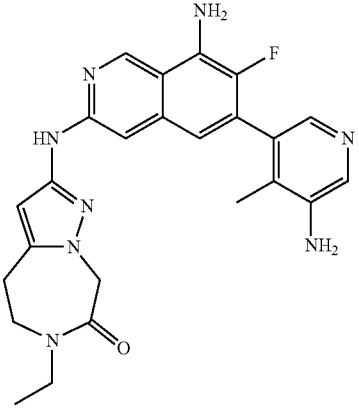 [SMILES: CCN1CCc2cc(Nc3cc4cc(-c5cncc(N)c5C)c(F)c(N)c4cn3)nn2CC1=O]<br>2-((8-amino-6-(5-amino-4-methylpyridin-3-yl)-7-fluoroisoquinolin-3-yl)amino)-6-ethyl-5,6-dihydro-4H-pyrazolo[1,5-d][1,4]diazepin-7(8H)-one | See Example 184 |
| 299 | 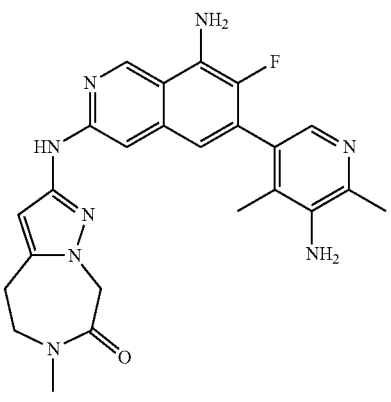 [SMILES: Cc1ncc(-c2cc3cc(Nc4cc5n(n4)CC(=O)N(C)CC5)ncc3c(N)c2F)c(C)c1N]<br>2-((8-amino-6-(5-amino-4,6-dimethylpyridin-3-yl)-7-fluoroisoquinolin-3-yl)amino)-6-methyl-5,6-dihydro-4H-pyrazolo[1,5-d][1,4]diazepin-7(8H)-one | See Example 185 |
| 300 | 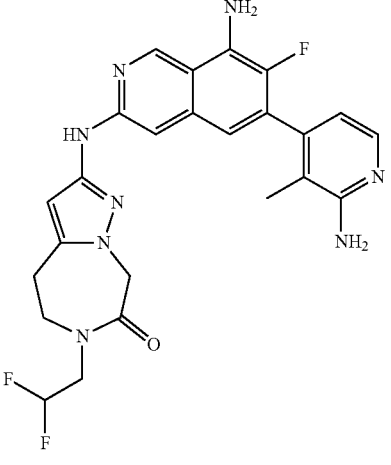 [SMILES: Cc1c(-c2cc3cc(Nc4cc5n(n4)CC(=O)N(CC(F)F)CC5)ncc3c(N)c2F)ccnc1N]<br>2-((8-amino-6-(2-amino-3-methylpyridin-4-yl)-7-fluoroisoquinolin-3-yl)amino)-6-(2,2-difluoroethyl)-5,6-dihydro-4H-pyrazolo[1,5-d][1,4]diazepin-7(8H)-one | See Example 186; |

TABLE A-4-continued

| Cmpd No. | Structure/Name | LCMS $R_T$ (min); M + H⁺; Method |
|---|---|---|
| 301 | 2-((8-amino-7-fluoro-6-(5-methyl-1H-pyrazol-4-yl)isoquinolin-3-yl)amino)-6-methyl-5,6-dihydro-4H-pyrazolo[1,5-d][1,4]diazepin-7(8H)-one | 2.82 421.2 N |
| 302 | 2-((8-amino-6-(5-amino-4-methylpyridin-3-yl)-7-fluoroisoquinolin-3-yl)amino)-5-methyl-4,5-dihydropyrazolo[1,5-a]pyrazin-6(7H)-one | See Example 187 |
| 303 | (E)-2-((8-amino-7-fluoro-6-(4-methylpyridin-3-yl)isoquinolin-3-yl)amino)-6-methyl-4-((1-methyl-1H-pyrazol-4-yl)methylene)-5,6-dihydro-4H-pyrazolo[1,5-d][1,4]diazepin-7(8H)-one | See Example 188 |

TABLE A-4-continued

| Cmpd No. | Structure/Name | LCMS $R_T$ (min); M + H⁺; Method |
|---|---|---|
| 304 | 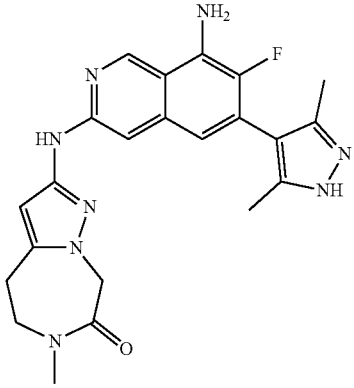 [SMILES: Cc1n[nH]c(C)c1-c1cc2cc(Nc3cc4n(n3)CC(=O)N(C)CC4)ncc2c(N)c1F]
2-((8-amino-6-(3,5-dimethyl-1H-pyrazol-4-yl)-7-fluoroisoquinolin-3-yl)amino)-6-methyl-5,6-dihydro-4H-pyrazolo[1,5-d][1,4]diazepin-7(8H)-one | 2.82 421.2 N |
| 305 | 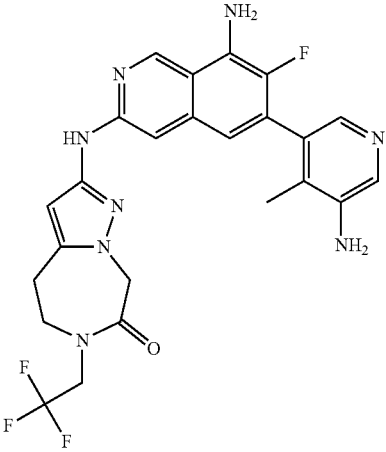 [SMILES: Cc1c(N)cncc1-c1cc2cc(Nc3cc4n(n3)CC(=O)N(CC(F)(F)F)CC4)ncc2c(N)c1F]
2-((8-amino-6-(5-amino-4-methylpyridin-3-yl)-7-fluoroisoquinolin-3-yl)amino)-6-(2,2,2-trifluoroethyl)-5,6-dihydro-4H-pyrazolo[1,5-d][1,4]diazepin-7(8H)-one | See Example 189 |
| 306 | 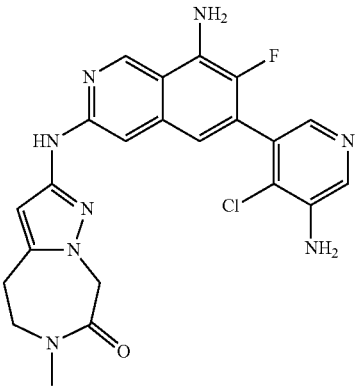 [SMILES: CN1CCc2cc(Nc3cc4cc(-c5cncc(N)c5Cl)c(F)c(N)c4cn3)nn2CC1=O]
2-((8-amino-6-(5-amino-4-chloropyridin-3-yl)-7-fluoroisoquinolin-3-yl)amino)-6-methyl-5,6-dihydro-4H-pyrazolo[1,5-d][1,4]diazepin-7(8H)-one | See Example 190 |

TABLE A-4-continued

| Cmpd No. | Structure/Name | LCMS $R_T$ (min); M + H+; Method |
|---|---|---|
| 307 | 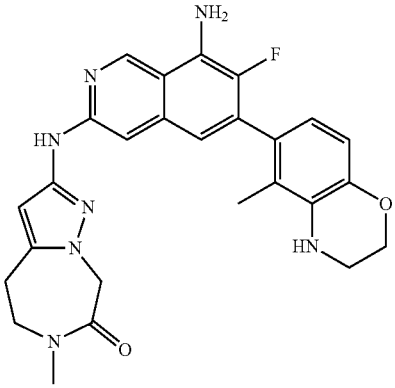 [SMILES: Cc1c(-c2cc3cc(Nc4cc5n(n4)CC(=O)N(C)CC5)ncc3c(N)c2F)ccc2c1NCCO2]  2-((8-amino-7-fluoro-6-(5-methyl-3,4-dihydro-2H-benzo[b][1,4]oxazin-6-yl)isoquinolin-3-yl)amino)-6-methyl-5,6-dihydro-4H-pyrazolo[1,5-d][1,4]diazepin-7(8H)-one | 2.41 488.2 K |
| 308 | 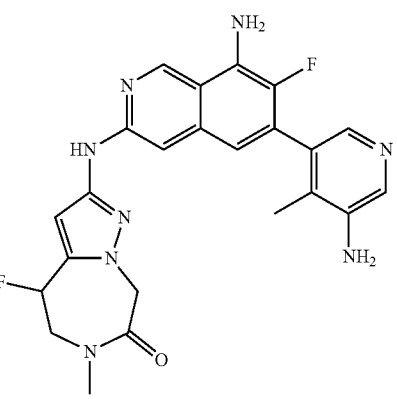  (±)-2-((8-amino-6-(5-amino-4-methylpyridin-3-yl)-7-fluoroisoquinolin-3-yl)amino)-4-fluoro-6-methyl-5,6-dihydro-4H-pyrazolo[1,5-d][1,4]diazepin-7(8H)-one | See Examples 192 and 193 |
| 309 | 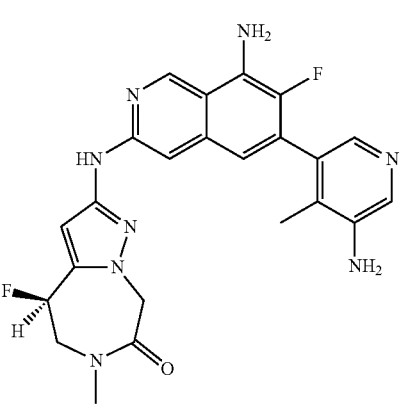 [SMILES: Cc1c(N)cncc1-c1cc2cc(Nc3cc4n(n3)CC(=O)N(C)C[C@H]4F)ncc2c(N)c1F]  (R)-2-((8-amino-6-(5-amino-4-methylpyridin-3-yl)-7-fluoroisoquinolin-3-yl)amino)-4-fluoro-6-methyl-5,6-dihydro-4H-pyrazolo[1,5-d][1,4]diazepin-7(8H)-one (Absolute stereochemistry arbitrarily assigned) | See Example 192 |

TABLE A-4-continued

| Cmpd No. | Structure/Name | LCMS R$_T$ (min); M + H$^+$; Method |
|---|---|---|
| 310 | 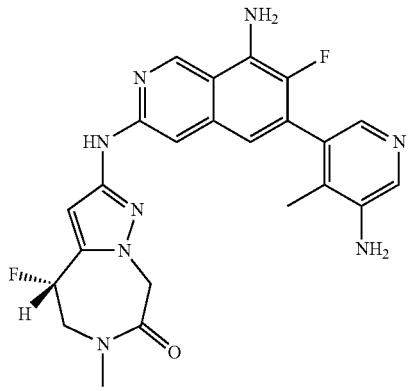 [SMILES: Cc1c(N)cncc1-c1cc2cc(Nc3cc4n(n3)CC(=O)N(C)C[C@@H]4F)ncc2c(N)c1F]<br>(S)-2-((8-amino-6-(5-amino-4-methylpyridin-3-yl)-7-fluoroisoquinolin-3-yl)amino)-4-fluoro-6-methyl-5,6-dihydro-4H-pyrazolo[1,5-d][1,4]diazepin-7(8H)-one<br>(Absolute stereochemistry arbitrarily assigned) | See Example 193 |
| 311 | 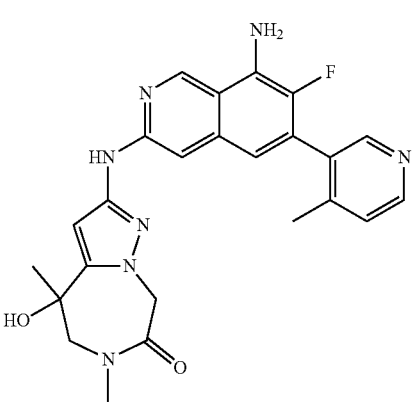 [SMILES: Cc1ccncc1-c1cc2cc(Nc3cc4n(n3)CC(=O)N(C)CC4(C)O)ncc2c(N)c1F]<br>(+/−)-2-((8-amino-7-fluoro-6-(4-methylpyridin-3-yl)isoquinolin-3-yl)amino)-4-hydroxy-4,6-dimethyl-5,6-dihydro-4H-pyrazolo[1,5-d][1,4]diazepin-7(8H)-one | See Example 194 |
| 312 | 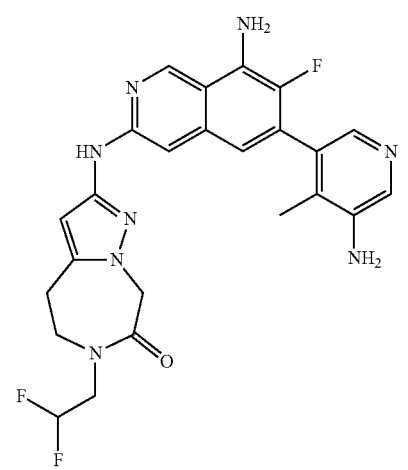 [SMILES: Cc1c(N)cncc1-c1cc2cc(Nc3cc4n(n3)CC(=O)N(CC(F)F)CC4)ncc2c(N)c1F]<br>2-((8-amino-6-(5-amino-4-methylpyridin-3-yl)-7-fluoroisoquinolin-3-yl)amino)-6-(2,2-difluoroethyl)-5,6-dihydro-4H-pyrazolo[1,5-d][1,4]diazepin-7(8H)-one | See Example 195 |

TABLE A-4-continued

| Cmpd No. | Structure/Name | LCMS $R_T$ (min); M + H⁺; Method |
|---|---|---|
| 313 | (+/−)-2-((8-amino-7-fluoro-6-(4-methylpyridin-3-yl)isoquinolin-3-yl)amino)-4-hydroxy-4-(methoxymethyl)-6-methyl-5,6-dihydro-4H-pyrazolo[1,5-d][1,4]diazepin-7(8H)-one | See Example 196 |
| 314 | 2'-((8-amino-7-fluoro-6-(1,3,5-trimethyl-1H-pyrazol-4-yl)isoquinolin-3-yl)amino)-6'-methyl-5',6'-dihydrospiro[cyclopropane-1,4'-pyrazolo[1,5-d][1,4]diazepin]-7'(8'H)-one | See Example 197 |
| 315 | 2-((8-amino-6-(5-amino-4-methylpyridin-3-yl)-7-fluoroisoquinolin-3-yl)amino)-6-isopropyl-5,6-dihydro-4H-pyrazolo[1,5-d][1,4]diazepin-7(8H)-one | See Example 198 |

TABLE A-4-continued

| Cmpd No. | Structure/Name | LCMS R_T (min); M + H+; Method |
|---|---|---|
| 316 | 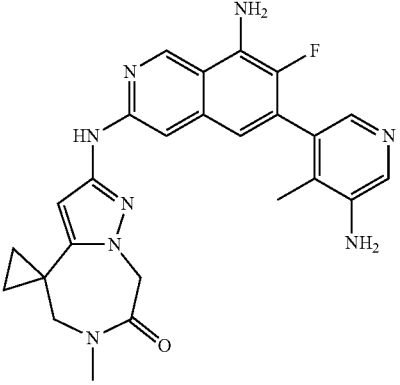 [SMILES: Cc1c(N)cncc1-c1cc2cc(Nc3cc4n(n3)CC(=O)N(C)CC43CC3)ncc2c(N)c1F]<br>2'-((8-amino-6-(5-amino-4-methylpyridin-3-yl)-7-fluoroisoquinolin-3-yl)amino)-6'-methyl-5',6'-dihydrospiro[cyclopropane-1,4'-pyrazolo[1,5-d][1,4]diazepin]-7'(8'H)-one | See Example 199 |
| 317 | 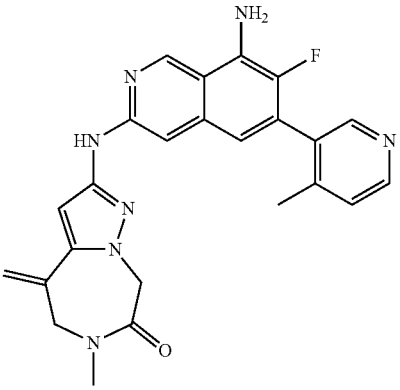 [SMILES: C=C1CN(C)C(=O)Cn2nc(Nc3cc4cc(-c5cnccc5C)c(F)c(N)c4cn3)cc21]<br>2-((8-amino-7-fluoro-6-(4-methylpyridin-3-yl)isoquinolin-3-yl)amino)-6-methyl-4-methylene-5,6-dihydro-4H-pyrazolo[1,5-d][1,4]diazepin-7(8H)-one | See Example 200 |
| 318 | 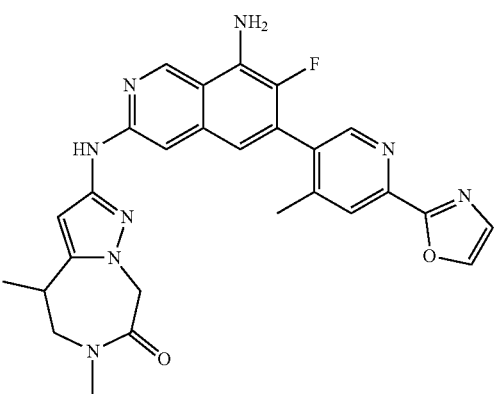 [SMILES: Cc1cc(-c2ncco2)ncc1-c1cc2cc(Nc3cc4n(n3)CC(=O)N(C)CC4C)ncc2c(N)c1F]<br>(+/−)-2-((8-amino-7-fluoro-6-(4-methyl-6-(oxazol-2-yl)pyridin-3-yl)isoquinolin-3-yl)amino)-4,6-dimethyl-5,6-dihydro-4H-pyrazolo[1,5-d][1,4]diazepin-7(8H)-one | See Example 201 |

TABLE A-4-continued

| Cmpd No. | Structure/Name | LCMS R_T (min); M + H+; Method |
|---|---|---|
| 319 | 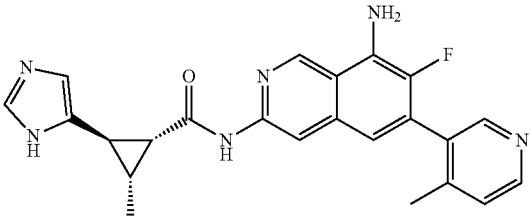<br>(1R,2R,3S)-N-(8-amino-7-fluoro-6-(4-methylpyridin-3-yl)isoquinolin-3-yl)-2-(1H-imidazol-5-yl)-3-methylcyclopropane-1-carboxamide<br>(Imidazole trans to amide; methyl relative stereochemistry arbitrarily assigned; Absolute stereochemistry arbitrarily assigned) | See Example 202 |
| 320 | 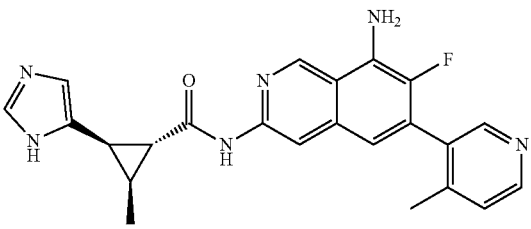<br>(1R,2R,3S)-N-(8-amino-7-fluoro-6-(4-methylpyridin-3-yl)isoquinolin-3-yl)-2-(1H-imidazol-5-yl)-3-methylcyclopropane-1-carboxamide<br>(Imidazole trans to amide; methyl relative stereochemistry arbitrarily assigned; Absolute stereochemistry arbitrarily assigned) | See Example 202 |
| 321 | 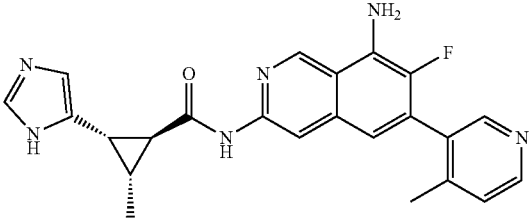 [SMILES: Cc1ccncc1-c1cc2cc(NC(=O)[C@H]3[C@H](C)[C@@H]3c3cnc[nH]3)ncc2c(N)c1F]<br>(1S,2S,3R)-N-(8-amino-7-fluoro-6-(4-methylpyridin-3-yl)isoquinolin-3-yl)-2-(1H-imidazol-5-yl)-3-methylcyclopropane-1-carboxamide<br>(Imidazole trans to amide; methyl relative stereochemistry arbitrarily assigned; Absolute stereochemistry arbitrarily assigned) | See Example 202 |
| 322 | 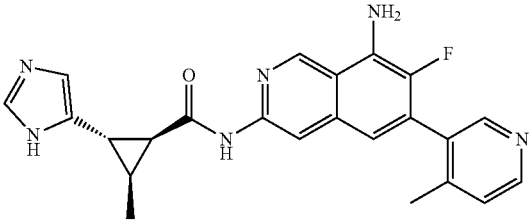 [SMILES: Cc1ccncc1-c1cc2cc(NC(=O)[C@H]3[C@@H](C)[C@@H]3c3cnc[nH]3)ncc2c(N)c1F]<br>(1S,2S,3S)-N-(8-amino-7-fluoro-6-(4-methylpyridin-3-yl)isoquinolin-3-yl)-2-(1H-imidazol-5-yl)-3-methylcyclopropane-1-carboxamide<br>(Imidazole trans to amide; methyl relative stereochemistry arbitrarily assigned; Absolute stereochemistry arbitrarily assigned) | See Example 202 |

TABLE A-4-continued

| Cmpd No. | Structure/Name | LCMS $R_T$ (min); M + H$^+$; Method |
|---|---|---|
| 323 | 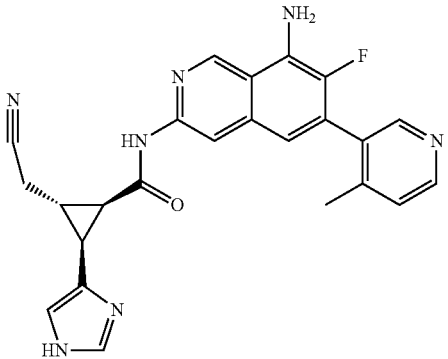 [SMILES: Cc1ccncc1-c1cc2cc(NC(=O)[C@@H]3[C@@H](CC#N)[C@@H]3c3c[nH]cn3)ncc2c(N)c1F]<br>(1R,2S,3S)-N-(8-amino-7-fluoro-6-(4-methylpyridin-3-yl)isoquinolin-3-yl)-2-(cyanomethyl)-3-(1H-imidazol-4-yl)cyclopropane-1-carboxamide<br>(Relative stereochemistry as drawn; Absolute stereochemistry arbitrarily assigned) | See Example 210 |
| 324 | 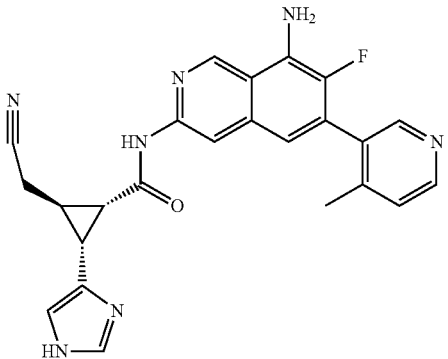 [SMILES: Cc1ccncc1-c1cc2cc(NC(=O)[C@H]3[C@H](CC#N)[C@H]3c3c[nH]cn3)ncc2c(N)c1F]<br>(1S,2R,3R)-N-(8-amino-7-fluoro-6-(4-methylpyridin-3-yl)isoquinolin-3-yl)-2-(cyanomethyl)-3-(1H-imidazol-4-yl)cyclopropane-1-carboxamide<br>(Relative stereochemistry as drawn; Absolute stereochemistry arbitrarily assigned) | See Example 210 |
| 325 | 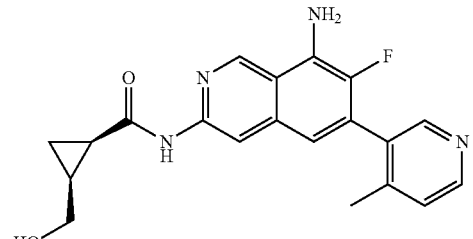<br>(±)-cis-N-(8-amino-7-fluoro-6-(4-methylpyridin-3-yl)isoquinolin-3-yl)-2-(hydroxymethyl)cyclopropane-1-carboxamide | 2.0 367.2 K |

TABLE A-4-continued

| Cmpd No. | Structure/Name | LCMS R_T (min); M + H+; Method |
|---|---|---|
| 326 | 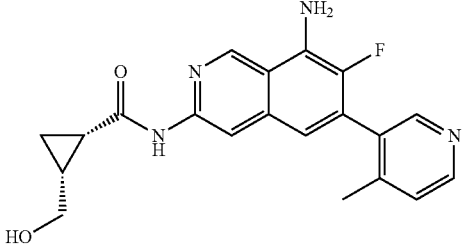 [SMILES: Cc1ccncc1-c1cc2cc(NC(=O)[C@H]3C[C@H]3CO)ncc2c(N)c1F]<br>(1S,2R)-N-(8-amino-7-fluoro-6-(4-methylpyridin-3-yl)isoquinolin-3-yl)-2-(hydroxymethyl)cyclopropane-1-carboxamide<br>(Hydroxymethyl trans to amide; Absolute stereochemistry arbitrarily assigned) | See Example 205 |
| 327 | 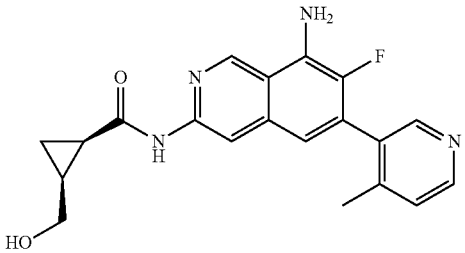 [SMILES: Cc1ccncc1-c1cc2cc(NC(=O)[C@@H]3C[C@@H]3CO)ncc2c(N)c1F]<br>(1R,2S)-N-(8-amino-7-fluoro-6-(4-methylpyridin-3-yl)isoquinolin-3-yl)-2-(hydroxymethyl)cyclopropane-1-carboxamide<br>(Hydroxymethyl trans to amide; Absolute stereochemistry arbitrarily assigned) | See Example 204 |
| 328 | 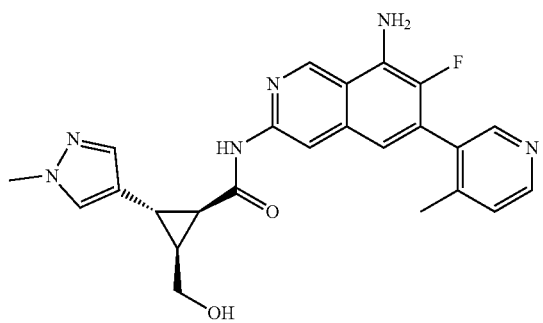 [SMILES: Cc1ccncc1-c1cc2cc(NC(=O)[C@H]3[C@@H](CO)[C@@H]3c3cnn(C)c3)ncc2c(N)c1F]<br>(±)-(1R,2S,3S)-N-(8-amino-7-fluoro-6-(4-methylpyridin-3-yl)isoquinolin-3-yl)-2-(hydroxymethyl)-3-(1-methyl-1H-pyrazol-4-yl)cyclopropane-1-carboxamide | See Example 203 |
| 329 | 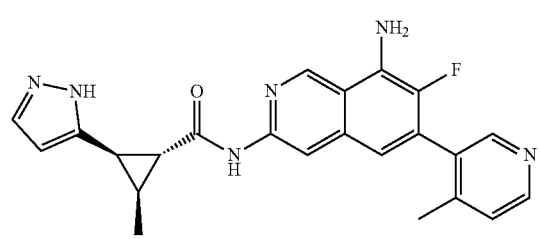 [SMILES: Cc1ccncc1-c1cc2cc(NC(=O)[C@@H]3[C@@H](C)[C@H]3c3ccn[nH]3)ncc2c(N)c1F]<br>(1R,2S,3R)-N-(8-amino-7-fluoro-6-(4-methylpyridin-3-yl)isoquinolin-3-yl)-2-methyl-3-(1H-pyrazol-5-yl)cyclopropane-1-carboxamide<br>(Pyrazole trans to amide; methyl relative stereochemistry arbitrarily assigned; Absolute stereochemistry arbitrarily assigned) | See Example 212 |

TABLE A-4-continued

| Cmpd No. | Structure/Name | LCMS R$_T$ (min); M + H$^+$; Method |
|---|---|---|
| 330 | (1S,2S,3S)-N-(8-amino-7-fluoro-6-(4-methylpyridin-3-yl)isoquinolin-3-yl)-2-methyl-3-(1H-pyrazol-5-yl)cyclopropane-1-carboxamide (Pyrazole trans to amide; methyl relative stereochemistry arbitrarily assigned; Absolute stereochemistry arbitrarily assigned) | See Example 212 |
| 331 | (1S,2R,3S)-N-(8-amino-7-fluoro-6-(4-methylpyridin-3-yl)isoquinolin-3-yl)-2-methyl-3-(1H-pyrazol-5-yl)cyclopropane-1-carboxamide (Pyrazole trans to amide; methyl relative stereochemistry arbitrarily assigned; Absolute stereochemistry arbitrarily assigned) | See Example 212 |
| 332 | (1R,2R,3R)-N-(8-amino-7-fluoro-6-(4-methylpyridin-3-yl)isoquinolin-3-yl)-2-methyl-3-(1H-pyrazol-5-yl)cyclopropane-1-carboxamide (Pyrazole trans to amide; methyl relative stereochemistry arbitrarily assigned; Absolute stereochemistry arbitrarily assigned) | See Example 212 |
| 333 | (±)-N-(8-amino-7-fluoro-6-(4-methylpyridin-3-yl)isoquinolin-3-yl)-2-(1H-imidazol-5-yl)cyclopropane-1-carboxamide | 1.30 403.2 K |

TABLE A-4-continued

| Cmpd No. | Structure/Name | LCMS R$_T$ (min); M + H$^+$; Method |
|---|---|---|
| 334 | (1R,2R)-N-(8-amino-7-fluoro-6-(4-methylpyridin-3-yl)isoquinolin-3-yl)-2-(1H-imidazol-5-yl)cyclopropane-1-carboxamide (Relative stereochemistry as drawn; Absolute stereochemistry arbitrarily assigned) | See Example 213 |
| 335 | (1S,2S)-N-(8-amino-7-fluoro-6-(4-methylpyridin-3-yl)isoquinolin-3-yl)-2-(1H-imidazol-5-yl)cyclopropane-1-carboxamide (Relative stereochemistry as drawn; Absolute stereochemistry arbitrarily assigned) | See Example 213 |
| 336 | N-(8-amino-7-fluoro-6-(4-methylpyridin-3-yl)isoquinolin-3-yl)-2-azabicyclo[2.1.1]hexane-2-carboxamide | See Example 218 |
| 337 | (1R,2R,3R)-N-(8-amino-7-fluoro-6-(4-methylpyridin-3-yl)isoquinolin-3-yl)-2-(1-(2,2-difluoroethyl)-1H-pyrazol-4-yl)-3-methylcyclopropane-1-carboxamide (Pyrazole trans to amide; methyl relative stereochemistry arbitrarily assigned; Absolute stereochemistry arbitrarily assigned) | See Example 214 |

TABLE A-4-continued

| Cmpd No. | Structure/Name | LCMS $R_T$ (min); M + H+; Method |
|---|---|---|
| 338 | 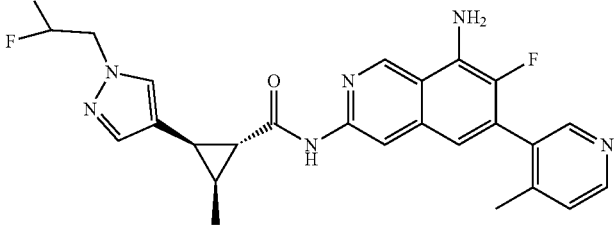<br>(1R,2R,3S)-N-(8-amino-7-fluoro-6-(4-methylpyridin-3-yl)isoquinolin-3-yl)-2-(1-(2,2-difluoroethyl)-1H-pyrazol-4-yl)-3-methylcyclopropane-1-carboxamide<br>(Pyrazole trans to amide; methyl relative stereochemistry arbitrarily assigned; Absolute stereochemistry arbitrarily assigned) | See Example 214 |
| 339 | 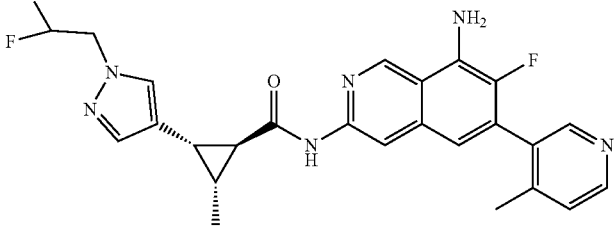<br>(1S,2S,3R)-N-(8-amino-7-fluoro-6-(4-methylpyridin-3-yl)isoquinolin-3-yl)-2-(1-(2,2-difluoroethyl)-1H-pyrazol-4-yl)-3-methylcyclopropane-1-carboxamide<br>(Pyrazole trans to amide; methyl relative stereochemistry arbitrarily assigned; Absolute stereochemistry arbitrarily assigned) | See Example 214 |
| 340 | 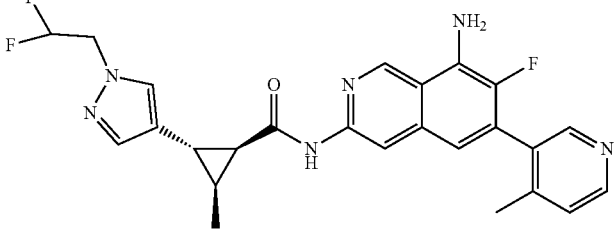<br>(1S,2S,3S)-N-(8-amino-7-fluoro-6-(4-methylpyridin-3-yl)isoquinolin-3-yl)-2-(1-(2,2-difluoroethyl)-1H-pyrazol-4-yl)-3-methylcyclopropane-1-carboxamide<br>(Pyrazole trans to amide; methyl relative stereochemistry arbitrarily assigned; Absolute stereochemistry arbitrarily assigned) | See Example 214 |
| 341 | 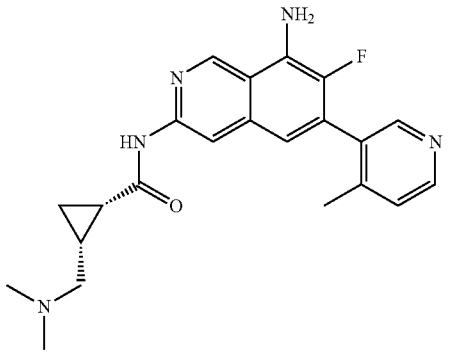 [SMILES: Cc1ccncc1-c1cc2cc(NC(=O)[C@H]3C[C@H]3CN(C)C)ncc2c(N)c1F]<br>(1S,2R)-N-(8-amino-7-fluoro-6-(4-methylpyridin-3-yl)isoquinolin-3-yl)-2-((dimethylamino)methyl)cyclopropane-1-carboxamide<br>(Relative stereochemistry as drawn; Absolute stereochemistry arbitrarily assigned) | See Example 215 |

TABLE A-4-continued

| Cmpd No. | Structure/Name | LCMS $R_T$ (min); M + H⁺; Method |
|---|---|---|
| 342 | 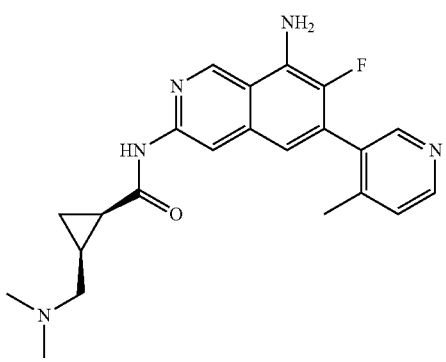 [SMILES: Cc1ccncc1-c1cc2cc(NC(=O)[C@@H]3C[C@@H]3CN(C)C)ncc2c(N)c1F]<br>(1R,2S)-N-(8-amino-7-fluoro-6-(4-methylpyridin-3-yl)isoquinolin-3-yl)-2-((dimethylamino)methyl)cyclopropane-1-carboxamide<br>(Relative stereochemistry as drawn; Absolute stereochemistry arbitrarily assigned) | See Example 215 |
| 343 | 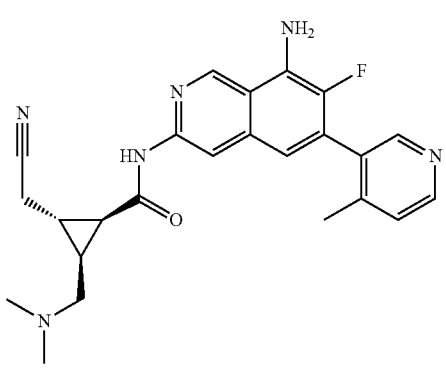 [SMILES: Cc1ccncc1-c1cc2cc(NC(=O)[C@@H]3[C@@H](CC#N)[C@@H]3CN(C)C)ncc2c(N)c1F]<br>(±)-(1R,2S,3S)-N-(8-amino-7-fluoro-6-(4-methylpyridin-3-yl)isoquinolin-3-yl)-2-(cyanomethyl)-3-((dimethylamino)methyl)cyclopropane-1-carboxamide<br>(Mixture of two enantiomers with relative stereochemistry as drawn) | See Examples 208 and 209 |
| 344 | 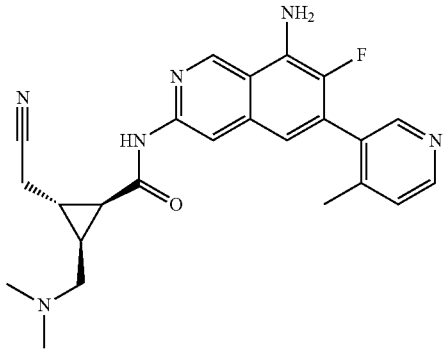 [SMILES: Cc1ccncc1-c1cc2cc(NC(=O)[C@@H]3[C@@H](CC#N)[C@@H]3CN(C)C)ncc2c(N)c1F]<br>(1R,2S,3S)-N-(8-amino-7-fluoro-6-(4-methylpyridin-3-yl)isoquinolin-3-yl)-2-(cyanomethyl)-3-((dimethylamino)methyl)cyclopropane-1-carboxamide<br>(Single enantiomer with relative stereochemistry as drawn; Absolute stereochemistry arbitrarily assigned) | See Example 208 |

TABLE A-4-continued

| Cmpd No. | Structure/Name | LCMS $R_T$ (min); M + H+; Method |
|---|---|---|
| 345 | 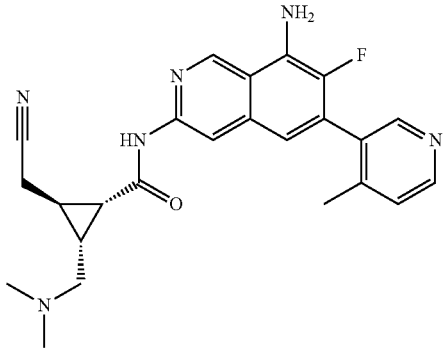 [SMILES: Cc1ccncc1-c1cc2cc(NC(=O)[C@H]3[C@H](CC#N)[C@H]3CN(C)C)ncc2c(N)c1F]<br>(1S,2R,3R)-N-(8-amino-7-fluoro-6-(4-methylpyridin-3-yl)isoquinolin-3-yl)-2-(cyanomethyl)-3-((dimethylamino)methyl)cyclopropane-1-carboxamide<br>(Single enantiomer with relative stereochemistry as drawn; Absolute stereochemistry arbitrarily assigned) | See Example 209 |
| 346 | 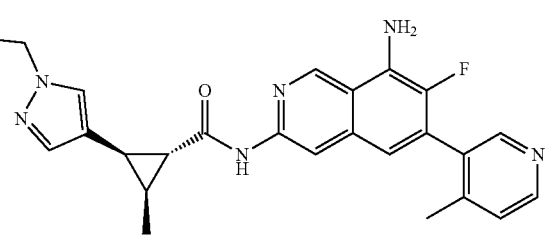<br>(1R,2S,3R)-N-(8-amino-7-fluoro-6-(4-methylpyridin-3-yl)isoquinolin-3-yl)-2-methyl-3-(1-(2-morpholinoethyl)-1H-pyrazol-4-yl)cyclopropane-1-carboxamide<br>(Pyrazole trans to amide; methyl relative stereochemistry arbitrarily assigned; Absolute stereochemistry arbitrarily assigned) | See Example 219 |
| 347 | 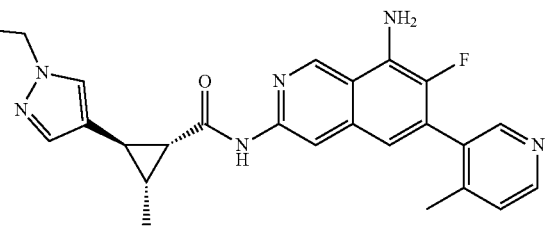<br>(1R,2R,3R)-N-(8-amino-7-fluoro-6-(4-methylpyridin-3-yl)isoquinolin-3-yl)-2-methyl-3-(1-(2-morpholinoethyl)-1H-pyrazol-4-yl)cyclopropane-1-carboxamide<br>(Pyrazole trans to amide; methyl relative stereochemistry arbitrarily assigned; Absolute stereochemistry arbitrarily assigned) | See Example 219 |

TABLE A-4-continued

| Cmpd No. | Structure/Name | LCMS $R_T$ (min); M + H⁺; Method |
|---|---|---|
| 348 | 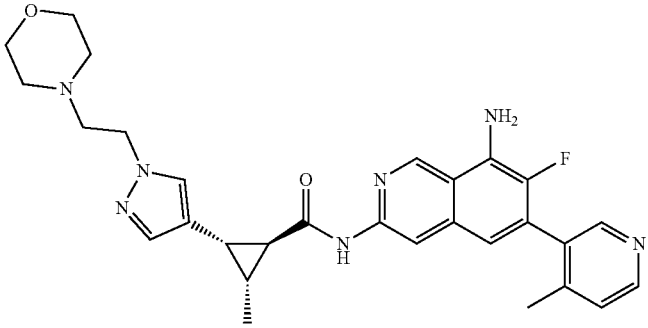 [SMILES: Cc1ccncc1-c1cc2cc(NC(=O)[C@H]3[C@H](C)[C@@H]3c3cnn(CCN4CCOCC4)c3)ncc2c(N)c1F]<br>(1S,2R,3S)-N-(8-amino-7-fluoro-6-(4-methylpyridin-3-yl)isoquinolin-3-yl)-2-methyl-3-(1-(2-morpholinoethyl)-1H-pyrazol-4-yl)cyclopropane-1-carboxamide<br>(Pyrazole trans to amide; methyl relative stereochemistry arbitrarily assigned; Absolute stereochemistry arbitrarily assigned) | See Example 219 |
| 349 | 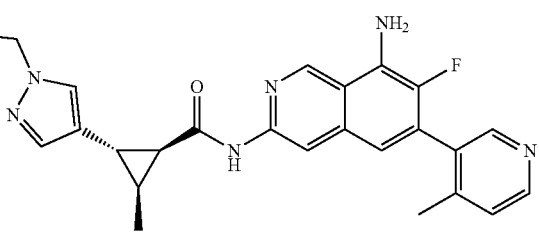<br>(1S,2S,3S)-N-(8-amino-7-fluoro-6-(4-methylpyridin-3-yl)isoquinolin-3-yl)-2-methyl-3-(1-(2-morpholinoethyl)-1H-pyrazol-4-yl)cyclopropane-1-carboxamide<br>(Pyrazole trans to amide; methyl relative stereochemistry arbitrarily assigned; Absolute stereochemistry arbitrarily assigned) | See Example 219 |
| 350 | 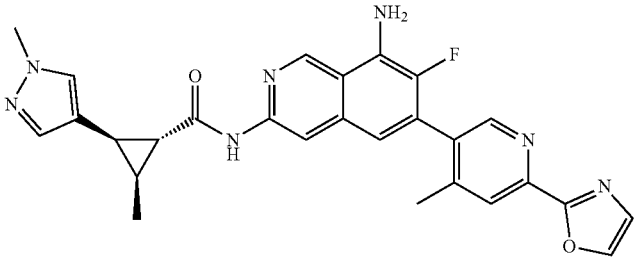 [SMILES: Cc1cc(-c2ncco2)ncc1-c1cc2cc(NC(=O)[C@@H]3[C@@H](C)[C@H]3c3cnn(C)c3)ncc2c(N)c1F]<br>(1R,2S,3R)-N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide<br>(Pyrazole trans to amide; methyl relative stereochemistry arbitrarily assigned; Absolute stereochemistry arbitrarily assigned) | See Example 220 |

TABLE A-4-continued

| Cmpd No. | Structure/Name | LCMS R_T (min); M + H+; Method |
|---|---|---|
| 351 | (1S,2R,3S)-N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide (Pyrazole trans to amide; methyl relative stereochemistry arbitrarily assigned; Absolute stereochemistry arbitrarily assigned) | See Example 220 |
| 352 | (1S,2S,3S)-N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide (Pyrazole trans to amide; methyl relative stereochemistry arbitrarily assigned; Absolute stereochemistry arbitrarily assigned) | See Example 220 |
| 353 | (1R,2R,3R)-N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide (Pyrazole trans to amide; methyl relative stereochemistry arbitrarily assigned; Absolute stereochemistry arbitrarily assigned) | See Example 220 |
| 354 | (1S,2S)-N-(8-amino-7-fluoro-6-(4-methylpyridin-3-yl)isoquinolin-3-yl)-2-(1-methyl-1H-1,2,3-triazol-4-yl)cyclopropane-1-carboxamide (Relative stereochemistry as drawn; Absolute stereochemistry arbitrarily assigned) | 1.74 418.3 K |

TABLE A-4-continued

| Cmpd No. | Structure/Name | LCMS $R_T$ (min); M + H+; Method |
|---|---|---|
| 355 | (1S,2S)-N-(8-amino-7-fluoro-6-(4-methylpyridin-3-yl)isoquinolin-3-yl)-2-(1-methyl-1H-1,2,3-triazol-4-yl)cyclopropane-1-carboxamide (Relative stereochemistry as drawn; Absolute stereochemistry arbitrarily assigned) | See Example 226 |
| 356 | (1R,2R)-N-(8-amino-7-fluoro-6-(4-methylpyridin-3-yl)isoquinolin-3-yl)-2-(1-methyl-1H-1,2,3-triazol-4-yl)cyclopropane-1-carboxamide (Relative stereochemistry as drawn; Absolute stereochemistry arbitrarily assigned) | See Example 226 |
| 357 | (1R,2R,3R)-N-(8-amino-6-(5-amino-4-methylpyridin-3-yl)-7-fluoroisoquinolin-3-yl)-2-methyl-3-(1-methyl-1H-pyrazol-4-yl)cyclopropane-1-carboxamide (Pyrazole trans to amide; methyl relative stereochemistry arbitrarily assigned; Absolute stereochemistry arbitrarily assigned) | See Example 222 |
| 358 | (1S,2S,3S)-N-(8-amino-6-(5-amino-4-methylpyridin-3-yl)-7-fluoroisoquinolin-3-yl)-2-methyl-3-(1-methyl-1H-pyrazol-4-yl)cyclopropane-1-carboxamide (Pyrazole trans to amide; methyl relative stereochemistry arbitrarily assigned; Absolute stereochemistry arbitrarily assigned) | See Example 222 |

TABLE A-4-continued

| Cmpd No. | Structure/Name | LCMS R_T (min); M + H+; Method |
|---|---|---|
| 359 | 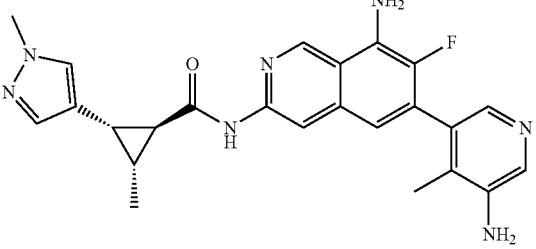<br>(1S,2R,3S)-N-(8-amino-6-(5-amino-4-methylpyridin-3-yl)-7-fluoroisoquinolin-3-yl)-2-methyl-3-(1-methyl-1H-pyrazol-4-yl)cyclopropane-1-carboxamide<br>(Pyrazole trans to amide; methyl relative stereochemistry arbitrarily assigned; Absolute stereochemistry arbitrarily assigned) | See Example 222 |
| 360 | 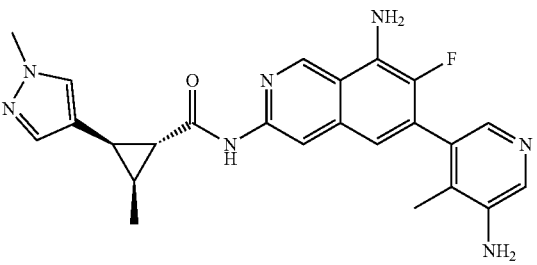 [SMILES: Cc1c(N)cncc1-c1cc2cc(NC(=O)[C@@H]3[C@@H](C)[C@H]3c3cnn(C)c3)ncc2c(N)c1F]<br>(1R,2S,3R)-N-(8-amino-6-(5-amino-4-methylpyridin-3-yl)-7-fluoroisoquinolin-3-yl)-2-methyl-3-(1-methyl-1H-pyrazol-4-yl)cyclopropane-1-carboxamide<br>(Pyrazole trans to amide; methyl relative stereochemistry arbitrarily assigned; Absolute stereochemistry arbitrarily assigned) | See Example 222 |
| 361 | 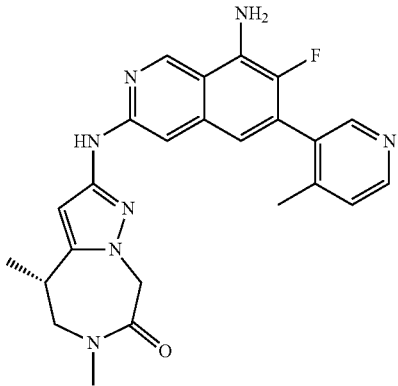 [SMILES: Cc1ccncc1-c1cc2cc(Nc3cc4n(n3)CC(=O)N(C)C[C@@H]4C)ncc2c(N)c1F]<br>(S)-2-((8-amino-7-fluoro-6-(4-methylpyridin-3-yl)isoquinolin-3-yl)amino)-4,6-dimethyl-5,6-dihydro-4H-pyrazolo[1,5-d][1,4]diazepin-7(8H)-one<br>(Absolute stereochemistry arbitrarily assigned) | See Example 223 |

TABLE A-4-continued

| Cmpd No. | Structure/Name | LCMS R_T (min); M + H+; Method |
|---|---|---|
| 362 | (R)-2-((8-amino-7-fluoro-6-(4-methylpyridin-3-yl)isoquinolin-3-yl)amino)-4,6-dimethyl-5,6-dihydro-4H-pyrazolo[1,5-d][1,4]diazepin-7(8H)-one (Absolute stereochemistry arbitrarily assigned) | See Example 223 |
| 363 | (1S,2S)-N-(8-amino-7-fluoro-6-(4-methylpyridin-3-yl)isoquinolin-3-yl)-2-(1H-pyrazol-5-yl)cyclopropane-1-carboxamide (Relative stereochemistry as drawn; Absolute stereochemistry arbitrarily assigned) | See Example 224 |
| 364 | (1R,2R)-N-(8-amino-7-fluoro-6-(4-methylpyridin-3-yl)isoquinolin-3-yl)-2-(1H-pyrazol-5-yl)cyclopropane-1-carboxamide (Relative stereochemistry as drawn; Absolute stereochemistry arbitrarily assigned) | See Example 224 |

TABLE A-4-continued

| Cmpd No. | Structure/Name | LCMS $R_T$ (min); M + H+; Method |
|---|---|---|
| 365 | (1R,2R,3S)-N-(8-amino-7-fluoro-6-(4-methylpyridin-3-yl)isoquinolin-3-yl)-2-(1-(2-hydroxyethyl)-1H-pyrazol-4-yl)-3-methylcyclopropane-1-carboxamide<br>(Pyrazole trans to amide; methyl relative stereochemistry arbitrarily assigned; Absolute stereochemistry arbitrarily assigned) | See Example 225 |
| 366 | (1R,2R,3R)-N-(8-amino-7-fluoro-6-(4-methylpyridin-3-yl)isoquinolin-3-yl)-2-(1-(2-hydroxyethyl)-1H-pyrazol-4-yl)-3-methylcyclopropane-1-carboxamide<br>(Pyrazole trans to amide; methyl relative stereochemistry arbitrarily assigned; Absolute stereochemistry arbitrarily assigned) | See Example 225 |
| 367 | (1S,2S,3R)-N-(8-amino-7-fluoro-6-(4-methylpyridin-3-yl)isoquinolin-3-yl)-2-(1-(2-hydroxyethyl)-1H-pyrazol-4-yl)-3-methylcyclopropane-1-carboxamide<br>(Pyrazole trans to amide; methyl relative stereochemistry arbitrarily assigned; Absolute stereochemistry arbitrarily assigned) | See Example 225 |
| 368 | (1S,2S,3S)-N-(8-amino-7-fluoro-6-(4-methylpyridin-3-yl)isoquinolin-3-yl)-2-(1-(2-hydroxyethyl)-1H-pyrazol-4-yl)-3-methylcyclopropane-1-carboxamide<br>(Pyrazole trans to amide; methyl relative stereochemistry arbitrarily assigned; Absolute stereochemistry arbitrarily assigned) | See Example 225 |

TABLE A-4-continued

| Cmpd No. | Structure/Name | LCMS R$_T$ (min); M + H$^+$; Method |
|---|---|---|
| 369 | (1S,3R)-N-(8-amino-7-fluoro-6-(4-methylpyridin-3-yl)isoquinolin-3-yl)-2-(1H-imidazol-4-yl)-3-(1-methyl-1H-pyrazol-4-yl)cyclopropane-1-carboxamide (Pyrazole trans to amide; Absolute stereochemistry arbitrarily assigned) | See Example 207 |
| 370 | (1R,3S)-N-(8-amino-7-fluoro-6-(4-methylpyridin-3-yl)isoquinolin-3-yl)-2-(1H-imidazol-4-yl)-3-(1-methyl-1H-pyrazol-4-yl)cyclopropane-1-carboxamide (Pyrazole trans to amide; Absolute stereochemistry arbitrarily assigned) | See Example 207 |
| 371 | (1S,2R,6R,7S)-N-(8-amino-7-fluoro-6-(4-methylpyridin-3-yl)isoquinolin-3-yl)-2-hydroxybicyclo[4.1.0]heptane-7-carboxamide | See Example 227 |

TABLE A-4-continued

| Cmpd No. | Structure/Name | LCMS R$_T$ (min); M + H$^+$; Method |
|---|---|---|
| 372 | (1R,2R,6S,7R)-N-(8-amino-7-fluoro-6-(4-methylpyridin-3-yl)isoquinolin-3-yl)-2-hydroxybicyclo[4.1.0]heptane-7-carboxamide (Relative stereochemistry as drawn; All absolute stereochemistry arbitrarily assigned) | See Example 227 |
| 373 | (1S,2R,6R,7S)-N-(8-amino-7-fluoro-6-(4-methylpyridin-3-yl)isoquinolin-3-yl)-2-hydroxybicyclo[4.1.0]heptane-7-carboxamide (Relative stereochemistry as drawn; All absolute stereochemistry arbitrarily assigned) | See Example 227 |
| 374 | (1R,2S,6S,7R)-N-(8-amino-7-fluoro-6-(4-methylpyridin-3-yl)isoquinolin-3-yl)-2-hydroxybicyclo[4.1.0]heptane-7-carboxamide (Relative stereochemistry as drawn; All absolute stereochemistry arbitrarily assigned) | See Example 227 |
| 375 | (1R,2S,3R)-N-(8-amino-6-(5-amino-4-methylpyridin-3-yl)-7-fluoroisoquinolin-3-yl)-2-ethyl-3-(1-methyl-1H-imidazol-5-yl)cyclopropane-1-carboxamide (Imidazole trans to amide; ethyl relative stereochemistry arbitrarily assigned; All absolute stereochemistry arbitrarily assigned) | 1.76, 460.2 K |

TABLE A-4-continued

| Cmpd No. | Structure/Name | LCMS $R_T$ (min); M + H+; Method |
|---|---|---|
| 376 | 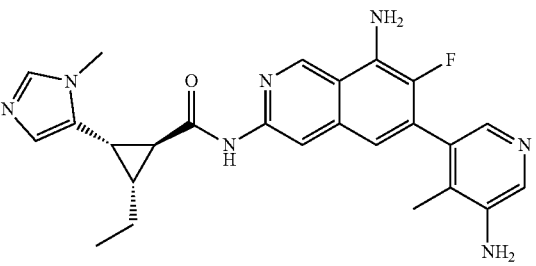 [SMILES: CC[C@H]1[C@H](C(=O)Nc2cc3cc(-c4cncc(N)c4C)c(F)c(N)c3cn2)[C@H]1c1cncn1C]<br>(1S,2R,3S)-N-(8-amino-6-(5-amino-4-methylpyridin-3-yl)-7-fluoroisoquinolin-3-yl)-2-ethyl-3-(1-methyl-1H-imidazol-5-yl)cyclopropane-1-carboxamide<br>(Imidazole trans to amide; ethyl relative stereochemistry arbitrarily assigned; All absolute stereochemistry arbitrarily assigned) | —<br>460.2<br>— |
| 377 | 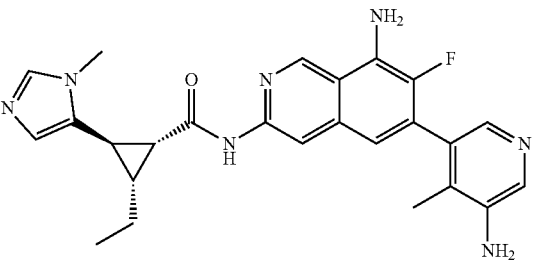 [SMILES: CC[C@H]1[C@@H](C(=O)Nc2cc3cc(-c4cncc(N)c4C)c(F)c(N)c3cn2)[C@@H]1c1cncn1C]<br>(1R,2R,3R)-N-(8-amino-6-(5-amino-4-methylpyridin-3-yl)-7-fluoroisoquinolin-3-yl)-2-ethyl-3-(1-methyl-1H-imidazol-5-yl)cyclopropane-1-carboxamide<br>(Imidazole trans to amide; ethyl relative stereochemistry arbitrarily assigned; All absolute stereochemistry arbitrarily assigned) | —<br>460.2<br>— |
| 378 | 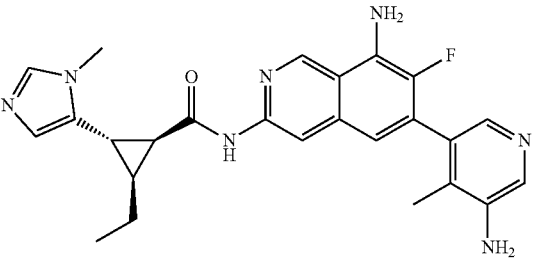 [SMILES: CC[C@@H]1[C@H](C(=O)Nc2cc3cc(-c4cncc(N)c4C)c(F)c(N)c3cn2)[C@H]1c1cncn1C]<br>(1S,2S,3S)-N-(8-amino-6-(5-amino-4-methylpyridin-3-yl)-7-fluoroisoquinolin-3-yl)-2-ethyl-3-(1-methyl-1H-imidazol-5-yl)cyclopropane-1-carboxamide<br>(Imidazole trans to amide; ethyl relative stereochemistry arbitrarily assigned; All absolute stereochemistry arbitrarily assigned) | —<br>460.2<br>— |

TABLE A-4-continued

| Cmpd No. | Structure/Name | LCMS R$_T$ (min); M + H$^+$; Method |
|---|---|---|
| 379 | (1S,2S,3R)-N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropane-1-carboxamide (Pyrazole trans to amide; methyl relative stereochemistry arbitrarily assigned; All absolute stereochemistry arbitrarily assigned) | See Example 216 |
| 380 | (1R,2R,3R)-N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropane-1-carboxamide (Pyrazole trans to amide; methyl relative stereochemistry arbitrarily assigned; All absolute stereochemistry arbitrarily assigned) | See Example 216 |
| 381 | (1S,2S,3S)-N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropane-1-carboxamide (Pyrazole trans to amide; methyl relative stereochemistry arbitrarily assigned; All absolute stereochemistry arbitrarily assigned) | See Example 216 |

TABLE A-4-continued

| Cmpd No. | Structure/Name | LCMS $R_T$ (min); M + H⁺; Method |
|---|---|---|
| 382 | (1R,2R,3S)-N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropane-1-carboxamide<br>(Pyrazole trans to amide; methyl relative stereochemistry arbitrarily assigned; All absolute stereochemistry arbitrarily assigned) | See Example 216 |
| 383 | (1S,2S,3R)-N-(8-amino-7-fluoro-6-(4-methylpyridin-3-yl)isoquinolin-3-yl)-2-(cyanomethyl)-3-methylcyclopropane-1-carboxamide<br>(Cyanomethyl trans to amide; methyl relative stereochemistry arbitrarily assigned; All absolute stereochemistry arbitrarily assigned) | See Example 232 |
| 384 | (1R,2R,3S)-N-(8-amino-7-fluoro-6-(4-methylpyridin-3-yl)isoquinolin-3-yl)-2-(cyanomethyl)-3-methylcyclopropane-1-carboxamide<br>(Cyanomethyl trans to amide; methyl relative stereochemistry arbitrarily assigned; All absolute stereochemistry arbitrarily assigned) | See Example 232 |
| 385 | (1S,2S,3S)-N-(8-amino-7-fluoro-6-(4-methylpyridin-3-yl)isoquinolin-3-yl)-2-(cyanomethyl)-3-methylcyclopropane-1-carboxamide<br>(Cyanomethyl trans to amide; methyl relative stereochemistry arbitrarily assigned; All absolute stereochemistry arbitrarily assigned) | See Example 232 |

TABLE A-4-continued

| Cmpd No. | Structure/Name | LCMS $R_T$ (min); M + H+; Method |
|---|---|---|
| 386 | 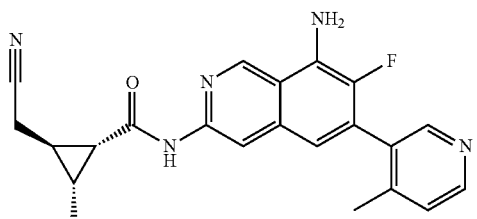<br>(1R,2R,3R)-N-(8-amino-7-fluoro-6-(4-methylpyridin-3-yl)isoquinolin-3-yl)-2-(cyanomethyl)-3-methylcyclopropane-1-carboxamide (Cyanomethyl trans to amide; methyl relative stereochemistry arbitrarily assigned; Absolute stereochemistry arbitrarily assigned) | See Example 232 |
| 387 | 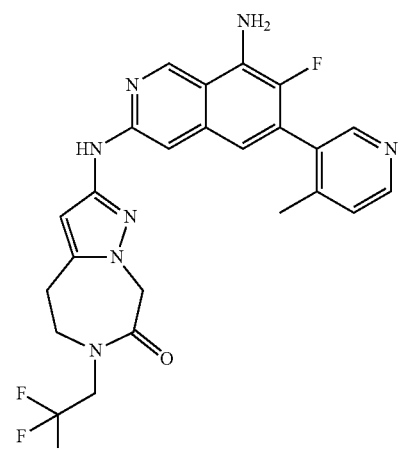<br>2-((8-amino-7-fluoro-6-(4-methylpyridin-3-yl)isoquinolin-3-yl)amino)-6-(2,2,2-trifluoroethyl)-5,6-dihydro-4H-pyrazolo[1,5-d][1,4]diazepin-7(8H)-one | See Example 206 |
| 388 | 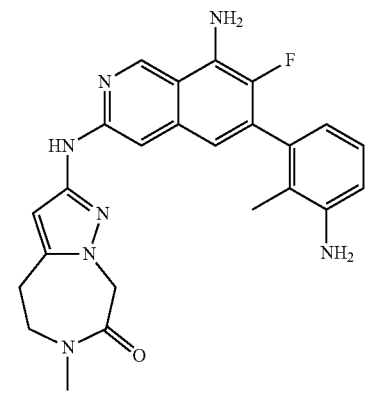 [SMILES: Cc1c(N)cccc1-c1cc2cc(Nc3cc4n(n3)CC(=O)N(C)CC4)ncc2c(N)c1F]<br>2-((8-amino-6-(3-amino-2-methylphenyl)-7-fluoroisoquinolin-3-yl)amino)-6-methyl-5,6-dihydro-4H-pyrazolo[1,5-d][1,4]diazepin-7(8H)-one | 1.76 446.1 K |

TABLE A-4-continued

| Cmpd No. | Structure/Name | LCMS $R_T$ (min); M + H+; Method |
|---|---|---|
| 389 | 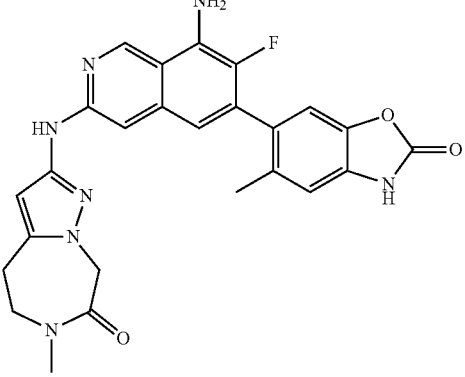<br>6-(8-amino-7-fluoro-3-((6-methyl-7-oxo-5,6,7,8-tetrahydro-4H-pyrazolo[1,5-d][1,4]diazepin-2-yl)amino)isoquinolin-6-yl)-5-methylbenzo[d]oxazol-2(3H)-one | 2.04<br>488.2<br>K |
| 390 | 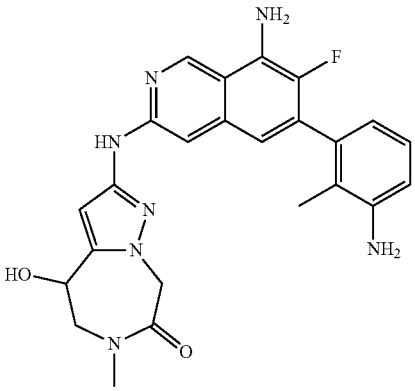 [SMILES: Cc1c(N)cccc1-c1cc2cc(Nc3cc4n(n3)CC(=O)N(C)CC4O)ncc2c(N)c1F]<br>2-((8-amino-6-(3-amino-2-methylphenyl)-7-fluoroisoquinolin-3-yl)amino)-4-hydroxy-6-methyl-5,6-dihydro-4H-pyrazolo[1,5-d][1,4]diazepin-7(8H)-one | 0.999<br>462.2<br>K |

Biological Evaluation

Exemplary compounds of Formula I or Ia were tested to assess compound inhibition of HPK-1. The $K_i$ for each exemplary compound was determined

Example B1: HPK1 Ki Determination

Example B1A: HPK1-FL HTRF Enzymatic Assay ("HTRF")

Assay Principle:

HPK-FL enzyme phosphorylates Biotin-SLP-76 substrate in the presence of ATP at 1 mM and varying concentrations of test compound. Product is detected by FRET using Eu-anti-pSLP76 Ab and SA-XL665. Also see www.cisbio.com/HTRF for additional HTRF technology information.

Instrumentation:
Echo555 compound dispenser
Agilent Bravo
Perkin Elmer Envision
Final Assay Conditions:
HPK full length, T165E S171E: 0.125 nM
Biotin-SLP76: 100 nM
ATP: 1 mM (ATP Km=20 μM)
Eu-anti-p SLP76: 2 nM
SA-XL665: 8.3 nM
Preincubation time: 30 min
Kinase reaction time: 60 min
Temperature: ambient
Total volume: 12 μl
$ATP^{app}$ Km: 17.7 μM
Materials:
Assay plate: White ProxiPlate 384 F (PerkinElmer cat #6008289)
Kinase: HPK full length double mutant
Substrate: Biotin-SLP76
ATP: 100 mM ATP
BSG: 2% BSG
DMSO: DMSO (Sigma cat #34869-100ML)
Reaction Buffer: $H_2O$/50 mM HEPES, pH 7.5/10 mM $MgCl_2$/2 mM TCEP/0.01% Brij-35/0.01% BSG
Detection mix:Eu-anti-pSLP76/SA-XL665 (Cisbio, #610SAXAC)

Assay Procedure Ki Determination:

To a 384 well Proxiplate with 80 nL compound or DMSO spotted on was added 4 μl/well kinase mix. The mixture was preincubated for 30 minutes and then 4 μl/well substrate mix was added. The solution was incubated for 60 min and then 4 μl/well detection mix was added. The solution was incubated for another 60 min. The plates were then loaded onto a Perkin Elmer Envision and the TR-FRET signal was measured at 615 and 665 nm. A ratio of 665/620 was used to calculate the % activity at each concentration of compound.

Example B1B: HPK1 Lantha Binding Assay ("Lanth")

Materials:

| Reagent | Vender-Cat# |
|---|---|
| white ProxiPlate 384 F(assay plate) | PerkinElmer-6008289 |
| 384-well Microplate(compound plate) | Labcyte-LP-0200 |
| HPK1 enzyme | Signalchem-M23-11G |
| Tracer-222 | Invitrogen-PV6121 |
| Eu-Anti-GST Ab | Invitrogen-PV5594 |
| Assay Buffer | 2 mM DTT(Sigma-43815), 0.01% BRIJ-35(Sigma-B4184), 10 mM MgCl$_2$, 50 mM HEPES(Invitrogen-15630130) |

Procedure:

I. Compound Dilution:

The compounds to be tested were diluted by preparing 12.5 uL/well of 5 mM compound (100×) in columns 2 and 13 and 10 ul/well of DMSO in columns 3-12, 14-23, and wells A1-H1 and I24-P24 of the compound plate using a Bravo liquid handling platform. For the reference compound, the top concentration was 1 mM. To the plate was added 10 ul 2 mM staurosporine in wells J1-P1 and A24-H24. A 11 point 5-fold compound serial dilution was performed using the Bravo liquid handling platform. From the plate were transferred 2.5 ul of the solutions from column 2 and column 13 to the 10 ul of DMSO in columns 3 and 14 & so on. The compound plate was centrifuged at 2500 rpm for 1 min. From the compound plate was transferred 80 nl of the compounds into an assay plate using the Echo liquid handler system. One compound plate makes two assay plates. Each assay plate is sealed and stored in an N$_2$ cabinet.

II. Assay Condition:

The following assay concentrations and times were used: 2 nM HPK1, 2 nM Eu-Anti-GST Ab, and 15 nM Tracer222, with 60 min incubation time.

III. HPK Lantha Binding Assay:

For the binding assay, 4 ul 2×HPK1 and Eu-anti-GST antibody were added to each well of the assay plate using a Multidrop reagent dispenser. The solutions were incubated in a 23 C incubator for 1 h. To each well of the assay plate was added 4 ul 2× Tracer-222 using a Multidrop reagent dispenser. The solutions were again incubated in a 23 C incubator for 1 h. The results of the assay were read using an Envision plate reader with the following parameters: TR_FRET, 340ex/615 and 665em; 100 usec Delay; and 200 usec integration.

IV. Analysis:

Compound Ki was analyzed using Morrison ki fit model in XL-fit a. fit=$(1-((((E+x)+(Ki*(1+(S/Kd))))-(((((E+x)+(Ki*(1+(S/Kd))))^2)-((4*E)*x))^0.5))/(2*E)))$ res=(y-fit)

b. Parameters:

E=enzyme concentration

S=Tracer222 concentration, Kd=Tracer222 Kd

All measurements reported using the same units (uM)

Exemplary compounds of Formula I or Ia were tested in the binding assays. The Ki values determined are listed in Tables B1-1 and B1-2.

TABLE B1-1

| Compound No. | HPK1 K$_i$ (μm), (Lanth) |
|---|---|
| 1 | 0.0575 |
| 2 | 0.000391 |
| 3 | 0.0158 |
| 4 | 0.000333 |
| 5 | 0.000209 |
| 6 | 0.00654 |
| 7 | 0.0925 |
| 8 | 0.0196 |
| 13 | 0.0815 |
| 14 | 0.012 |
| 15 | 0.0195 |
| 16 | 0.00166 |
| 17 | 0.000366 |
| 18 | 0.0273 |
| 19 | 0.00541 |
| 20 | 0.027 |
| 21 | 0.61 |
| 22 | 0.024 |
| 23 | 0.083 |
| 24 | 1.16 |
| 25 | 1.61 |
| 26 | 0.199 |
| 27 | 0.0864 |
| 28 | 0.00194 |
| 30 | 0.0757 |
| 31 | 0.00527 |
| 32 | 0.0012 |
| 37 | 0.000351 |
| 38 | 0.249 |
| 39 | 0.000167 |
| 40 | 0.0219 |
| 41 | 0.00037 |
| 42 | 0.000627 |
| 43 | 0.129 |
| 44 | 0.0153 |
| 45 | 0.0138 |
| 46 | 0.00719 |
| 47 | 0.00251 |
| 48 | 0.919 |
| 49 | 0.0146 |
| 50 | 0.00671 |
| 51 | 0.0158 |
| 52 | 0.000533 |
| 54 | 0.000624 |
| 55 | 0.0435 |
| 56 | 0.0134 |
| 57 | 0.0338 |
| 59 | 0.0084 |
| 60 | 0.0115 |
| 61 | 0.0837 |
| 62 | 0.00167 |
| 63 | 0.0457 |
| 65 | 0.00345 |
| 66 | 0.00104 |
| 67 | 0.000823 |
| 68 | 0.0016 |
| 69 | 0.0167 |
| 70 | 0.00567 |
| 71 | 0.00354 |
| 72 | 0.000447 |

TABLE B1-1-continued

| Compound No. | HPK1 $K_i$ (μm), (Lanth) |
|---|---|
| 73 | 0.00496 |
| 74 | 0.000622 |
| 75 | 0.0232 |
| 76 | 0.0472 |
| 77 | 0.0129 |
| 78 | 0.0463 |
| 79 | 0.0241 |
| 80 | 0.00139 |
| 81 | 0.00316 |
| 82 | 0.00553 |
| 85 | 0.00103 |
| 86 | 0.00882 |
| 87 | 0.0653 |
| 88 | 0.015 |
| 89 | 0.00253 |
| 90 | 0.0439 |
| 91 | 0.019 |
| 92 | 0.000205 |
| 93 | 0.00253 |
| 94 | 0.0118 |
| 95 | 0.000738 |
| 98 | 0.00432 |
| 99 | 0.0453 |
| 100 | 0.0148 |
| 101 | 0.000204 |
| 102 | 0.000333 |
| 103 | 0.0137 |
| 104 | 0.00037 |
| 105 | 0.0028 |
| 106 | 0.00581 |
| 107 | 0.00567 |
| 108 | 0.000191 |
| 109 | 0.046 |
| 110 | 0.024 |
| 113 | 0.000273 (Ent-1), 0.0047 (Ent-2) |
| 115 | 0.015 |
| 116 | 0.044 |
| 117 | 0.065 |
| 118 | 0.0028 |
| 119 | 0.00252(Ent-1), 0.00103 (Ent-2) |
| 122 | 0.0032 |
| 123 | 0.0057 |
| 124 | 0.014 |
| 125 | 0.016 |
| 126 | 0.086 |
| 127 | 0.000052 |
| 128 | 0.00025 |
| 130 | 0.0028 |
| 131 | 0.091 |
| 132 | 0.024 |
| 133 | 0.0012 |
| 134 | 0.075 |
| 135 | 0.0032 |
| 136 | 0.045 |
| 138 | 2.3 |
| 139 | 0.0055 |
| 140 | 0.22 |
| 143 | 0.007 |
| 144 | 0.013 |
| 145 | 0.0058 |
| 146 | 0.0025 |
| 147 | 0.0048 |
| 148 | 0.0038 |
| 149 | 0.00119 |
| 150 | 0.0038 |
| 151 | 0.034 |
| 153 | 0.1 |
| 154 | 0.00026 |
| 155 | 0.013 |
| 156 | 0.00037 |
| 157 | 0.019 |
| 159 | 0.014 |
| 160 | 0.41 |
| 161 | 0.0017 |
| 162 | 0.00035 |
| 163 | 0.0032 |
| 164 | 0.0105 |
| 165 | 0.0148 |
| 166 | 0.0000816 |
| 167 | 0.00068 |
| 168 | 0.000082 |
| 169 | 0.00183 |
| 170 | 0.023 |
| 171 | 0.0472 |
| 172 | 0.0102 |
| 173 | 0.0148 |
| 174 | 0.000204 |
| 175 | 0.00104 |
| 176 | 0.00271 |
| 177 | 0.00896 |
| 178 | 0.0685 |
| 179 | 0.0101 |
| 180 | 0.0161 |
| 181 | 0.0571 |
| 182 | 0.000584 |
| 183 | 0.000137 |
| 184 | 0.0256 |
| 185 | 0.000541 |
| 186 | 0.00696 |
| 187 | 0.0497 |
| 188 | 0.000312 |
| 189 | 0.00544 |
| 190 | 0.00105 |
| 191 | 0.000187 |
| 192 | 0.0022 |
| 193 | 0.000148 |
| 194 | 0.00079 |
| 195 | 0.000273 |
| 196 | 0.00021 |
| 197 | 0.00223 |
| 198 | 0.0046 |
| 199 | 0.00117 |
| 200 | 0.00212 |
| 201 | 0.000299 |
| 202 | 0.000253 |
| 203 | 0.000363 |
| 204 | 0.000668 |
| 205 | 0.00102 |
| 206 | 0.000485 |
| 207 | 0.0815 |
| 208 | 0.747 |
| 209 | 0.0000405 |
| 210 | 0.104 |
| 211 | 0.0235 |
| 212 | 0.00376 |
| 213 | 0.000939 |
| 214 | 0.0000564 |
| 215 | 0.000101 |
| 216 | 0.0118 |
| 217 | 0.00145 |
| 218 | 0.000844 |
| 219 | 0.0185 |
| 220 | 0.00326 |
| 221 | 0.0238 |
| 222 | 0.00326 |
| 223 | 0.00202 |
| 224 | 0.00129 |
| 225 | 0.000583 |
| 226 | 0.00227 |
| 227 | 0.000079 |
| 228 | 0.000015 |
| 229 | 0.000013 |
| 230 | 0.00015 |

TABLE B1-2

| Compound No. | HPK1 Ki (nM) L = Lanth; H = HTRF |
|---|---|
| 9 | 0.016 nM, H |
| 10 | 0.228 nM, H |
| 11 | 0.016 nM, H |

TABLE B1-2-continued

| Compound No. | HPK1 Ki (nM) L = Lanth; H = HTRF |
|---|---|
| 12 | 0.054 nM, H |
| 29 | 0.014 nM, H |
| 33 | 0.013 nM, H |
| 34 | 0.025 nM, H |
| 35 | 0.013 nM, H |
| 36 | 0.014 nM, H |
| 53 | 0.020 nM, H |
| 58 | 5.5 nM, H |
| 64 | 0.13 nM, H |
| 83 | 0.26 nM, H |
| 84 | 1.4 nM, H |
| 96 | 4.1 nm, H |
| 97 | 15 nm, L |
| 111 | 0.013 nM, H |
| 112 | 0.168 nM, H |
| 114 | 0.79 nM, H |
| 120 | 27 nM, H |
| 121 | 8.7 nM, H |
| 129 | 1.33 nM, H |
| 141 | 5.6 nM, H |
| 142 | 789 nM, H |
| 152 | 2.1 nM, L |
| 158 | 0.78 nM, H |
| 191 | 0.19 nM, L |
| 192 | 2.2 nM, L |
| 227 | 0.078 nM, L |
| 228 | 0.015 nM, H |
| 229 | 0.013 nM, H |
| 230 | 0.15 nM, H |
| 231 | 0.128 nM, H |
| 232 | 70 nM, H |
| 233 | 0.018 nM, H |
| 234 | 0.021 nM, H |
| 235 | 0.024 nM, H |
| 236 | 1.49 nM, H |
| 237 | 1.66 nM, H |
| 238 | 0.10 nM, H |
| 239 | 0.11 nM, H |
| 240 | 9 nM, H |
| 241 | 30.6 nM, H |
| 242 | 0.22 nM, H |
| 243 | 0.016 nM, H |
| 244 | 1234 nM, H |
| 245 | 16.6 nM, H |
| 246 | 0.035 nM, H |
| 247 | 0.13 nM, H |
| 248 | 86 nM, H |
| 249 | 382 nM, H |
| 250 | 16 nM, H |
| 251 | 1.6 nM, H |
| 252 | 0.20 nM, H |
| 253 | 284 nM, H |
| 254 | 224 nM, H |
| 255 | 0.796 nM, H |
| 256 | 0.51 nM, H |
| 257 | 628 nM, H |
| 258 | 150 nM, H |
| 259 | 265 nM, H |
| 260 | 514 nM, H |
| 261 | 211 nM, H |
| 262 | 0.31 nM, H |
| 263 | 1.43 nM, H |
| 264 | 390 nM, H |
| 265 | 2.2 nM, H |
| 266 | 2.6 nM, H |
| 267 | 9.9 nM, H |
| 268 | 5.8 nM, H |
| 269 | 8.8 nM, H |
| 270 | 22 nM, H |
| 271 | 0.17 nM, H |
| 272 | 1.9 nM, H |
| 273 | 0.14 nM, H |
| 274 | 5.1 nM, H |
| 275 | 0.15 nM, H |
| 276 | 0.21 nM, H |
| 277 | 0.013 nM, H |
| 278 | 0.96 nM, H |
| 279 | 0.026 nM, H |
| 280 | 1.8 nM, H |
| 281 | 8.5 nM, H |
| 282 | 0.91 nM, H |
| 283 | 0.013 nM, H |
| 284 | 1.1 nM, H |
| 285 | 2.0 nM, H |
| 286 | 0.013 nM, H |
| 287 | 0.27 nM, H |
| 288 | 0.013 nM, H |
| 289 | 0.24 nM, H |
| 290 | 0.13 nM, H |
| 291 | 0.013 nM, H |
| 292 | 15 nM, H |
| 293 | 0.20 nM, H |
| 294 | 23 nM, H |
| 295 | 722 nM, H |
| 296 | 135 nM, H |
| 297 | 255 nM, H |
| 298 | 0.017 nM, H |
| 299 | 0.017 nM, H |
| 300 | 0.87 nM, H |
| 301 | 2.8 nM, H |
| 302 | 0.365 nM, H |
| 303 | 0.024 nM, H |
| 304 | 2.1 nM, H |
| 305 | 0.019 nM, H |
| 306 | 0.013 nM, H |
| 307 | 0.084 nM, H |
| 308 | 0.013 nM, H |
| 309 | 0.017 nM, H |
| 310 | 0.013 nM, H |
| 311 | 0.154 nM, H |
| 312 | 0.015 nM, H |
| 313 | 0.15 nM, H |
| 314 | 0.39 nM, H |
| 315 | 0.013 nM, H |
| 316 | 0.013 nM, H |
| 317 | 0.043 nM, H |
| 318 | 0.013 nM, H |
| 319 | 10.4 nM, H |
| 320 | 42 nM, H |
| 321 | 0.99 nM, H |
| 322 | 0.86 nM, H |
| 323 | 163.5 nM, H |
| 324 | 975 nM, H |
| 325 | 70 nM, H |
| 326 | n/a |
| 327 | 122 nM, H |
| 328 | 7.5 nM, H |
| 329 | 37.9 nM, H |
| 330 | 50.12 nM, H |
| 331 | 1.3 nM, H |
| 332 | 4.6 nM, H |
| 333 | 0.83 nM, H |
| 334 | 9.4 nM, H |
| 335 | 0.22 nM, H |
| 336 | 18 nM, L |
| 337 | 2.8 nM, L |
| 338 | 0.58 nM, H |
| 339 | 0.02 nM, H |
| 340 | 0.02 nM, H |
| 341 | 5 nM, L |
| 342 | 2.1 nM, H |
| 343 | 110 nM, H |
| 344 | 82 nM, H |
| 345 | 383.7 nM, H |
| 346 | 2.9 nM, L |
| 347 | 7.2 nM, L |
| 348 | 0.22 nM, L |
| 349 | 0.32 nM, L |
| 350 | 2.4 nM, L |
| 351 | 1.6 nM, L |
| 352 | 0.72 nM, L |
| 353 | 16 nM, L |
| 354 | 0.84 nM, L |
| 355 | 1.3 nM, H |
| 356 | 2.2 nM, L |
| 357 | 0.026 nM, L |

TABLE B1-2-continued

| Compound No. | HPK1 Ki (nM) L = Lanth; H = HTRF |
|---|---|
| 358 | 0.026 nM, L |
| 359 | 0.21 nM, L |
| 360 | 1.2 nM, L |
| 361 | 0.033 nM, L |
| 362 | 0.034 nM, L |
| 363 | 0.13 nM, L |
| 364 | 5.9 nM, L |
| 365 | 0.73 nM, L |
| 366 | 3.6 nM, L |
| 367 | 0.12 nM, L |
| 368 | 0.082 nM, L |
| 369 | 25.6 nM, H |
| 370 | n/a |
| 371 | 0.87 nM, L |
| 372 | 95 nM, L |
| 373 | 5.5 nM, L |
| 374 | 0.95 nM, L |
| 375 | 0.33 nM, H |
| 376 | 0.39 nM, H |
| 377 | 12 nM, H |
| 378 | 22 nM, H |
| 379 | 0.21 nM, L |
| 380 | 5.8 nM, L |
| 381 | 0.15 nM, L |
| 382 | 2.7 nM, L |
| 383 | 0.55 nM, L |
| 384 | 0.17 nM, L |
| 385 | 8.3 nM, L |
| 386 | 3.7 nM, L |
| 387 | 0.168 nM, H |
| 388 | 0.50 nM, H |
| 389 | 0.038 nM, H |
| 390 | 1.4 nM, H |

Example B2: Human T-cell IL2 Induction Assay

Assay Principle:

Anti-CD3 and anti-CD28 activates TCR signaling in primary human pan T cells leading to IL-2 promoter induction. Secreted IL-2 in cell culture supernatant is detected by electrochemiluminescence using a capture antibody against IL-2 and an anti-IL-2 antibody labeled with SULFO-tag.

Literature:

See www.mesoscale.com for additional electrochemiluminescence technology information.

Assay Procedure:

Incubate primary human pan T cells with varying concentrations of test compounds for 30 minutes in a humidified incubator at 37° C. and 5% $CO_2$. Transfer cells to a plate pre-coated with a fixed concentration of anti-human CD3 (determined separately for each donor lot) and add soluble anti-human CD28 (final concentration=1 g/ml). Stimulate cells in a humidified incubator at 37° C. and 5% $CO_2$ for 4 hours. Transfer 25 µl of supernatant to a MSD single spot plate pre-coated with an anti-human IL-2 antibody. Incubate MSD plate overnight at 4° C. with gentle shaking. Wash MSD plate 4× with wash buffer. Add SULFO-tagged detection antibody at a 1:50 dilution and incubate at room temperature shaking for 2 hours. Wash MSD plate 4× with wash buffer and add 150 µl 2×MSD read buffer. Read on an MSD instrument. Normalize data to stimulated/untreated controls to calculate % activity at each concentration of compound.

Materials:

Frozen Primary Human Pan-T Cells (StemCell Technologies #70024)

anti-human CD3 (OKT3 clone) (eBioscience #16-0037-81)

anti-human CD28 (CD28.2 clone) (BD #555725)

96-well Human IL-2 tissue culture kit (MSD #K151AHB-4)

Instrumentation:

Biomek FX for liquid handling (Beckman Coulter)

MSD SECTOR S 600 (Meso Scale Discovery)

Exemplary compounds of Formula I or Ia were tested in the human T-cell L-2 induction assays. The % increase measured for IL-2 in cells treated by the test compounds relative to untreated cells are provided in Table B2 for certain compounds.

TABLE B2

| Compound No. | % IL-2 increase relative to untreated cells | Assayed concentration (µM) |
|---|---|---|
| 135 | 800% | 8.3 |
| 158 | 343% | 0.93 |
| 161 | 243% | 2.8 |
| 162 | 73% | 0.93 |
| 168 | 323% | 0.31 |
| 233 | 521% | 0.034 |
| 266 | 438% | 0.93 |
| 276 | 1157% | 0.31 |
| 279 | 333% | 0.10 |
| 284 | 529% | 0.93 |
| 302 | 732% | 2.8 |
| 315 | 480% | 0.31 |
| 327 | 331% | 25 |

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments 50%, in some embodiments 20%, in some embodiments±10%, in some embodiments 5%, in some embodiments 1%, in some embodiments 0.5%, and in some embodiments 0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed within the invention. The upper and lower limits of these small ranges which may independently be included in the smaller rangers is also encompassed within the invention, subject to any specifically excluded limit in the stated range. Where the stated range includes one or both of the limits, ranges excluding either or both of those included limits are also included in the invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Further Embodiments

Embodiment 1. A compound of Formula I:

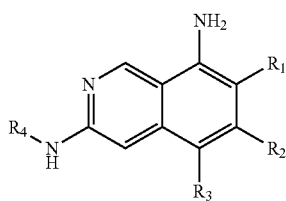

(I)

wherein, $R_1$ is hydrogen, halogen, methyl, $CF_3$, $CHF_2$, $CH_2OH$, or cyano;

$R_2$ is:

a 5-10 member heteroaryl or 5-10 member heterocyclyl, having 1-4 heteroatoms selected from O, S, and N; and optionally substituted with one, two, three or four substituents, $R_6$, $R_7$, $R_8$ and $R_{8'}$, each of which is independently selected from the group consisting of:
  i. branched or linear $C_{1-6}$ alkyl, $C_{1-6}$ alkenyl, or $C_{1-6}$ alkenylene, wherein said alkyl, alkenyl and alkenylene can be optionally substituted with one to four hydroxyl, halogen, nitrile, amino, mono($C_{1-6}$)alkylamino-, di($C_{1-6}$)alkylamino-, —$SO_2R^y$, $SONR^y$, —(CO)$NR^yR^z$ or —$NR^y$(CO)$R^z$, wherein $R^y$ and $R^z$, in each instance, is independently hydrogen or $C_{1-6}$ alkyl, wherein said alkyl can optionally be substituted with one to four hydroxyl or halogen;
  ii. $NR^yR^z$—C(O)—, wherein R and $R^z$ are each independently hydrogen or $C_{1-6}$ alkyl, wherein said alkyl can optionally be substituted with one to four hydroxyl or halogen;
  iii. hydroxy($C_{1-6}$)alkyl;
  iv. $C_{1-6}$ alkoxy, wherein said alkoxy can be optionally substituted with one to four hydroxyl or halogen;
  v. $C_{3-9}$ cycloalkyl, substituted or unsubstituted $C_6$ aryl, substituted or unsubstituted 5-member heteroaryl, or $C_{2-9}$ heterocyclyl;
  vi. halogen;
  vii. amino;
  viii. cyano;
  ix. —$NR^y$(CO)$R^z$, wherein R and $R^z$ are each independently hydrogen or $C_{1-6}$ alkyl, wherein said alkyl can optionally be substituted with one to four hydroxyl or halogen;
  x. —$SO_2R'$, wherein R' is H or $C_{1-6}$ alkyl;
  xi. —$SO_2NR'R''$, wherein R' and R'' are independently H or $C_{1-6}$ alkyl; and
  xii. wherein a carbon embedded in said heterocyclyl taken together with an oxygen to which it is bound can form a carbonyl; or $R_2$ is $C_{6-10}$ aryl having one, two, three or four substituents selected from the group consisting of branched or linear $C_{1-6}$ alkyl, $C_{1-6}$ alkenyl, $C_{1-6}$ alkenylene, $C_{3-4}$ cycloalkyl, wherein said alkyl, alkenyl, alkenylene and cycloalkyl can be substituted with amino, hydroxyl, cyano, halogen, amide, mono($C_{1-6}$)alkylamino-, di($C_{1-6}$)alkylamino-, —$SO_2R^c$, $SONR^d$, —(CO)$NR^cR^d$ and —$NR^c$(CO)$R^d$,
  wherein $R^c$ and $R^d$ are each independently selected from the group consisting of hydrogen and $C_{1-6}$ alkyl, wherein said alkyl can be optionally substituted with one to four hydroxyl or halogen; or $R_2$ is hydrogen or —$SO_2NH_2$;

$R_3$ is C1.6 alkyl, hydrogen, cyano, or halogen; and $R_4$ is A-C(O)—, wherein, A is:
  i. $C_{3-7}$ cycloalkyl, $C_{2-9}$ heteroaryl, or $C_{2-9}$ heterocyclyl, wherein said cycloalkyl, heteroaryl, or heterocyclyl can be optionally substituted with one, two, three or four of $R_5$, wherein $R_5$ is selected from the group consisting of hydrogen, branched or linear $C_{1-6}$ alkyl, $C_{3-7}$ cycloalkyl, $C_{1-6}$ alkenyl, $C_{1-6}$ alkenylene, wherein said alkyl, alkenyl and alkenylene can be substituted with amino, $C_{1-6}$ alkoxy, hydroxyl, halogen, —$SO_2R^e$ and amide; halogen, hydroxy($C_{1-6}$)alkyl, halo($C_{1-6}$)alkyl, cyano, cyano($C_{1-6}$)alkyl, hydroxyl, $C_{1-6}$ alkoxy, amino, $C_{2-9}$ heteroaryl, —$SO_2R^e$, and NR'$R^f$—C(O)—, wherein $R^e$ and $R^f$ are independently selected from the group consisting of hydrogen and branched or linear $C_{1-6}$ alkyl;
    or, said cycloalkyl or heterocyclyl together with two of $R_5$ form a bicyclic or spiro ring, wherein two of $R_5$ attached to different atoms are taken together with the carbon to which each is attached to form a bicyclic, or two of $R_5$ attached to the same carbon are taken together with the carbon to which each is attached to form a spiro ring; and
  ii. —$NHR^9$, wherein $R^9$ is selected from the group consisting of:
    a. branched or linear $C_{1-6}$ alkyl, $C_{3-5}$ cycloalkyl $C_{1-6}$ alkenyl, $C_{1-6}$ alkenylene, $C_{2-9}$ heterocyclyl, and $C_{3-7}$ cycloalkyl, wherein said alkyl, alkenyl, alkenylene, heterocyclyl and cycloalkyl can be optionally substituted with hydroxyl, halogen, —$CF_2$, —$CF_3$, amino, di($C_{1-6}$)alkylamino, mono($C_{1-6}$)alkylamino, cyano, $C_{3-7}$ cycloalkyl, $C_{1-6}$ alkoxy, —$SO_2R'$, —$SO_2NR'R''$, —(CO)$NR'R''$, or —$NR'$(CO)$R''$, wherein R' and R'' are independently H or $C_{1-6}$ alkyl; and
    b. $C_{2-9}$ heteroaryl or $C_{6-10}$ aryl, wherein said heteroaryl has 1-4 heteroatoms selected from O, S and N; and wherein said aryl and heteroaryl can be optionally substituted with one, two, three or four substituents selected from the group consisting of branched or linear $C_{1-6}$ alkyl, $C_{1-6}$ alkenyl, $C_{1-6}$ alkenylene, $C_{2-9}$ heterocyclyl, $C_{3-7}$ cycloalkyl, hydroxyl, halogen, —$CF_2$, —$CF_3$, amino, di($C_{1-6}$)alkylamino, mono($C_{1-6}$)alkylamino, cyano, C3-7 cycloalkyl, $C_{1-6}$ alkoxy, —$SO_2R'$, —$SO_2NR'R''$, —(CO)$NR'R''$, and —$NR'$(CO)$R''$, wherein R' and R'' are independently H or $C_{1-6}$ alkyl;

or, $R_4$ is D, wherein D is:
a 5-10 member heteroaryl, having 1-4 heteroatoms selected from 0, S, and N; and optionally substituted with one, two, three or four substituents.

Embodiment 2. The compound of embodiment 1, wherein $R_3$ is hydrogen.

Embodiment 3. The compound of embodiment 2, wherein $R_1$ is hydrogen, fluoro or cyano.

Embodiment 4. The compound of embodiment 3, wherein $R_5$ is other than hydrogen.

Embodiment 5. The compound of embodiment 4, wherein $R_4$ is A-C(O)—, wherein, A is:

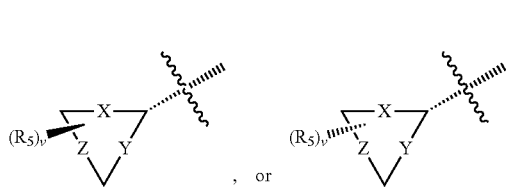, or wherein, v is zero, one, two, three or four; X, Y and Z are each independently absent or —CH$_2$—, and wherein, if present, zero, one or two of H on each of X, Y and Z can be $R_5$.

Embodiment 6. The compound of embodiment 4, wherein $R_4$ is A-C(O)—, wherein, A is:

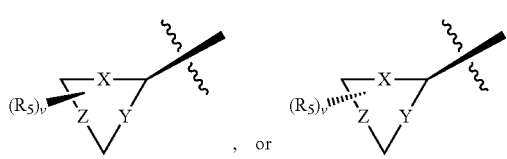, or wherein, v is zero, one, two, three or four; X, Y and Z are each independently absent or —CH$_2$—, and wherein, if present, zero, one or two of H on each of X, Y and Z can be $R_5$.

Embodiment 7. The compound of embodiment 2, wherein $R_4$ is A-C(O)—, wherein, A is:

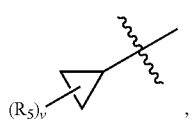, wherein, v is zero, one or two.

Embodiment 8. The compound of embodiment 7, wherein A is:

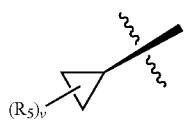, wherein, v is zero, one or two.

Embodiment 9. The compound of embodiment 8, wherein $R_5$ is other than hydrogen and A is:

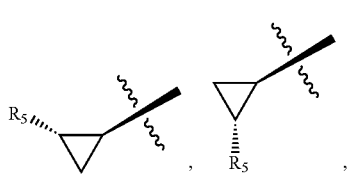,

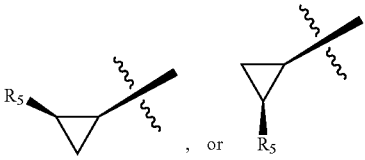, or

Embodiment 10. The compound of embodiment 7, wherein A is:

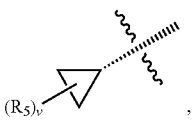, wherein, v is zero, one or two.

Embodiment 11. The compound of embodiment 10, wherein $R_5$ is other than hydrogen and A is:

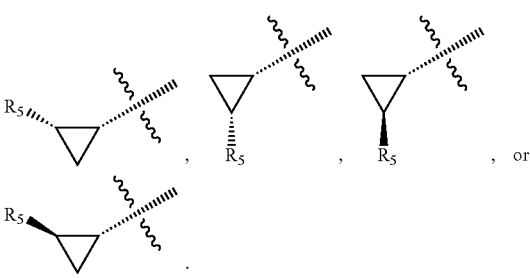.

Embodiment 12. The compound of embodiment 2, wherein $R_5$ is selected from the group consisting of hydrogen, fluorine, cyano, NH$_2$—C(O)—, C$_{2-9}$ heteroaryl, cyano(C$_{1-6}$)alkyl, and hydroxy(C$_{1-6}$)alkyl.

Embodiment 13. The compound of embodiment 12, wherein $R_5$ is fluoro or cyano.

Embodiment 14. The compound of embodiment 13, having one of the following structures:

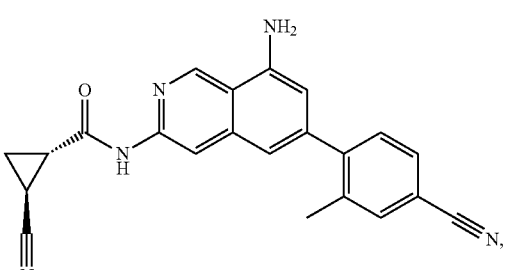

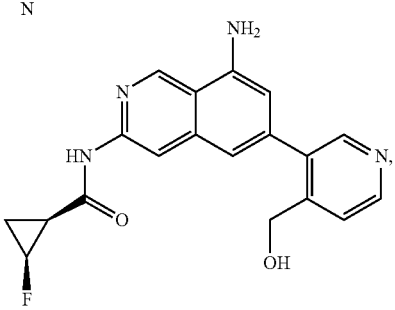

1241
-continued
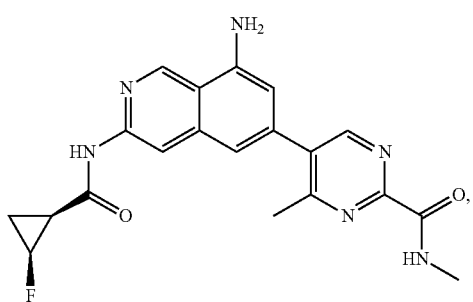
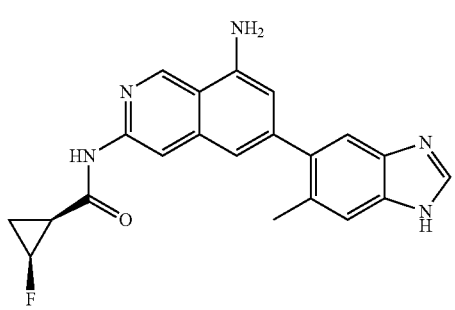
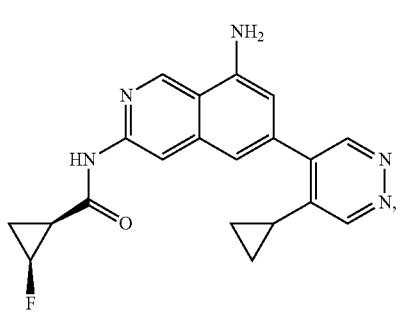
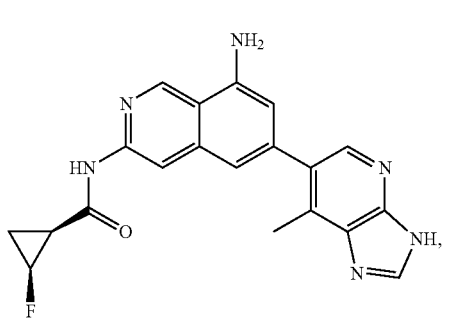
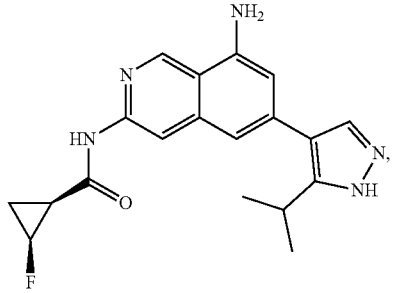
1242
-continued
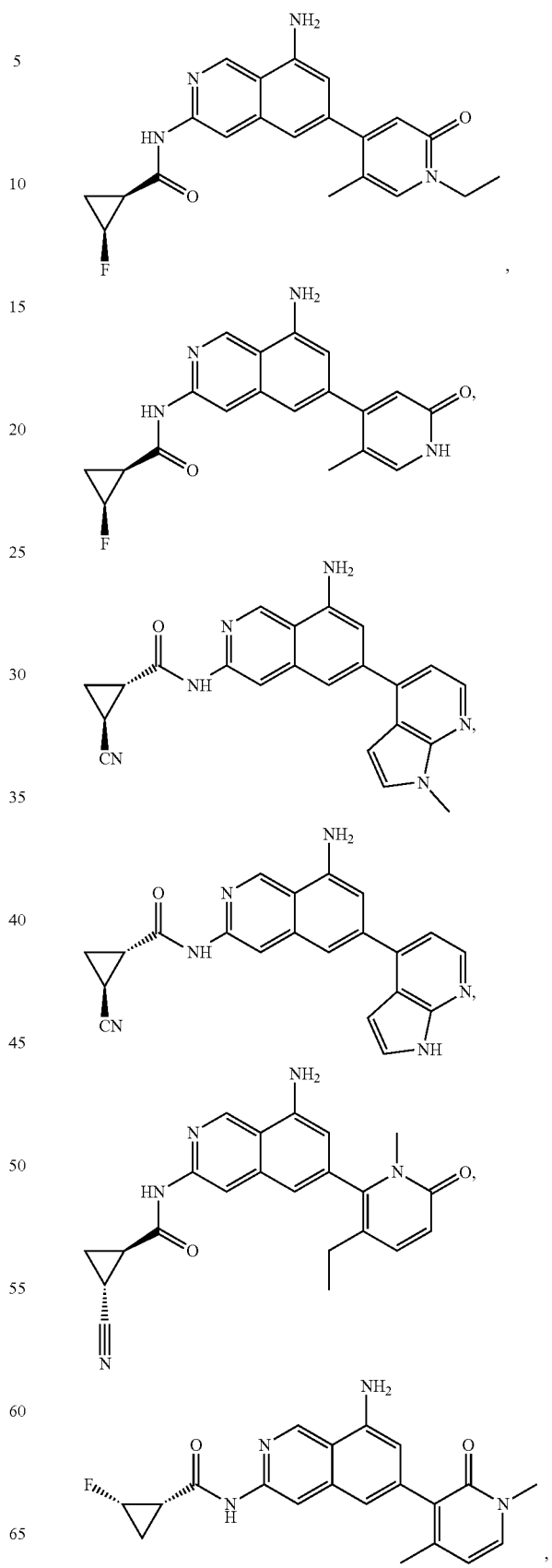

1243
-continued
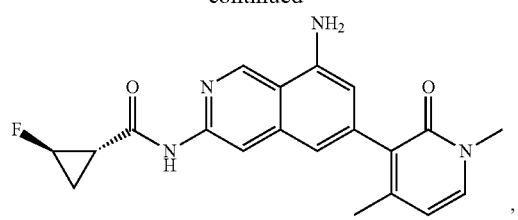
,
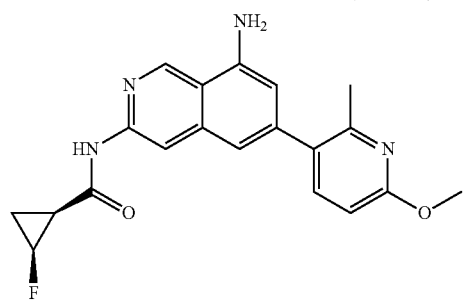
,
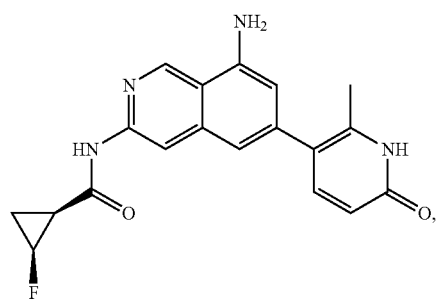
,
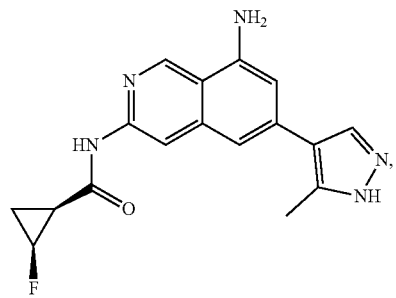
,
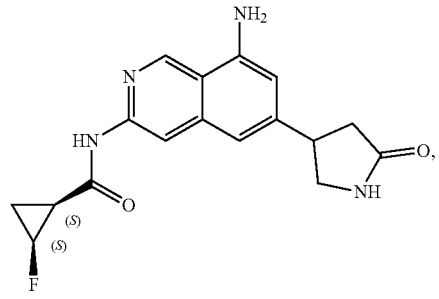
,
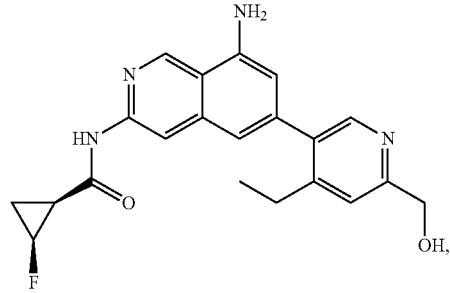
,
1244
-continued
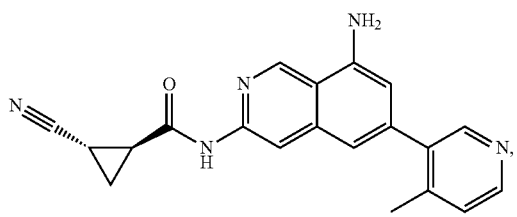
,
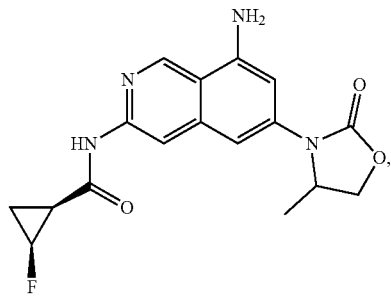
,
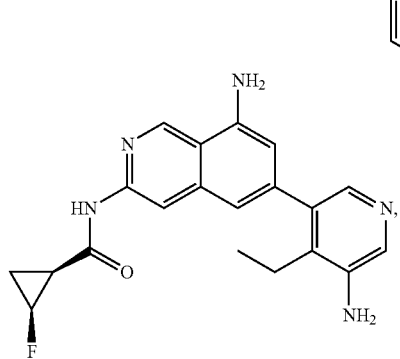
,
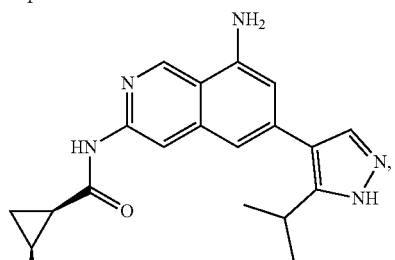
,
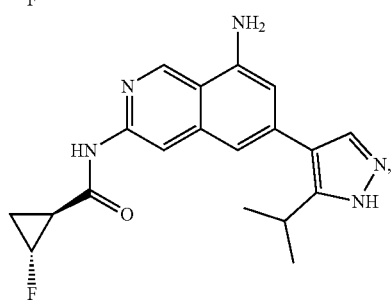
,

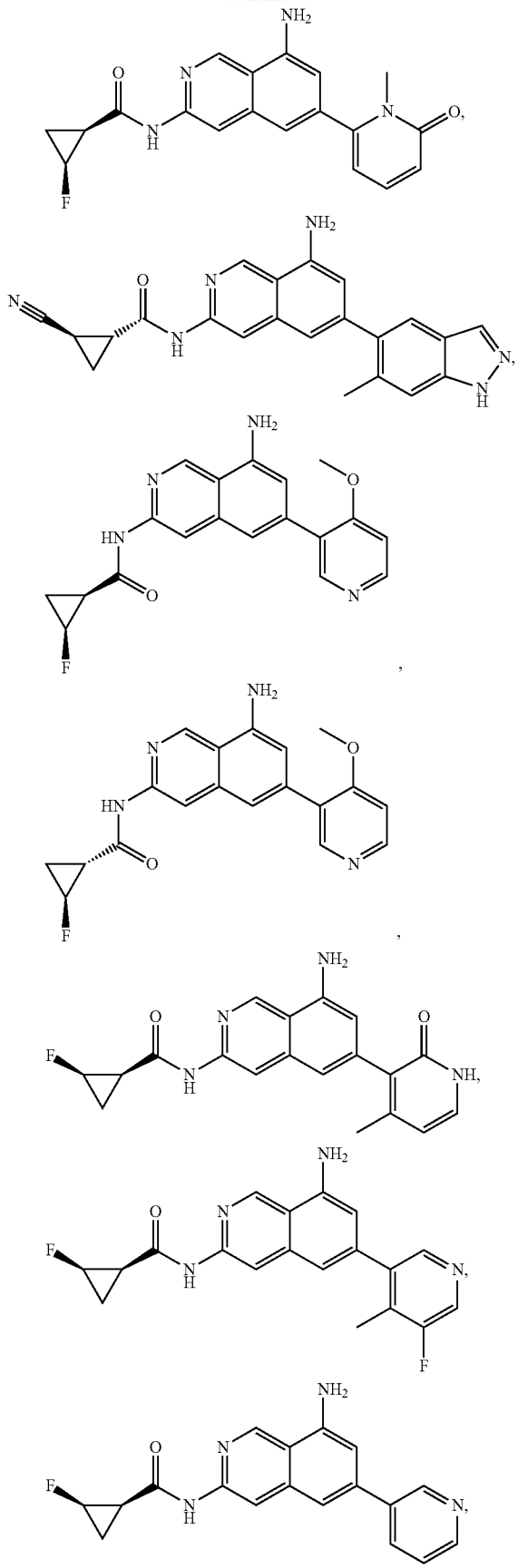
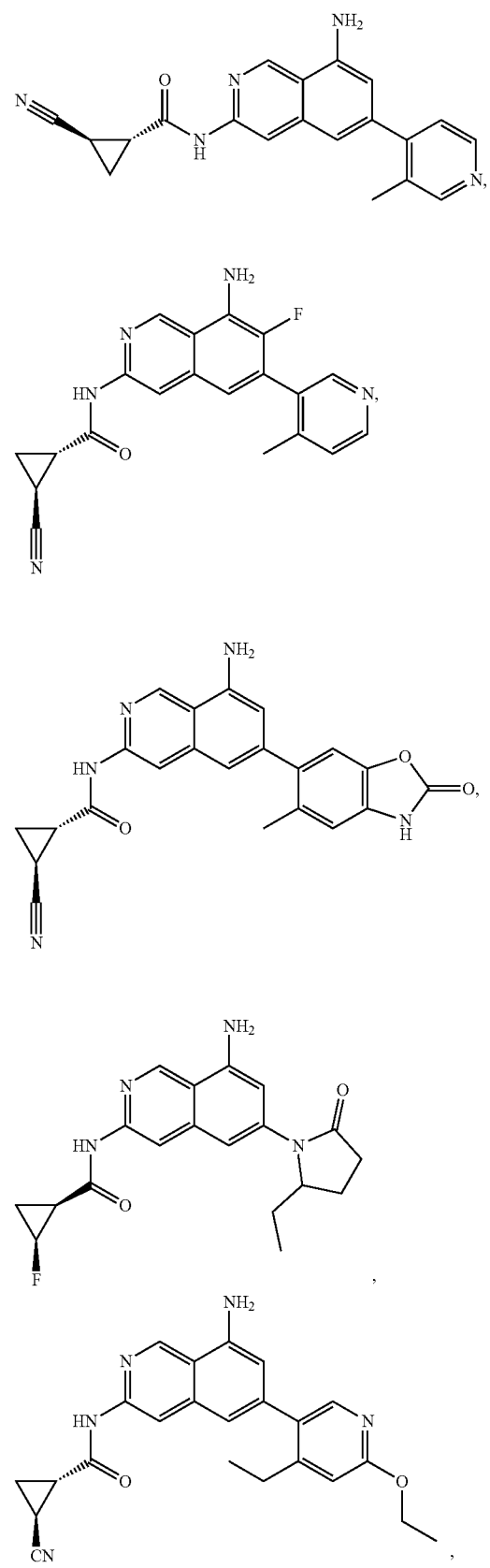

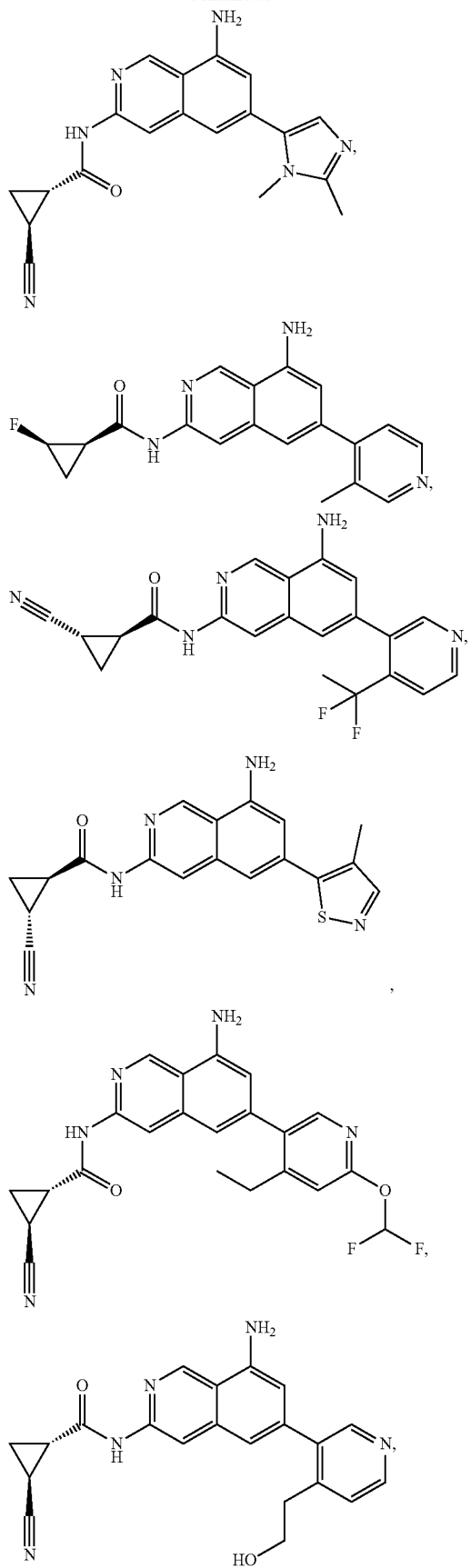

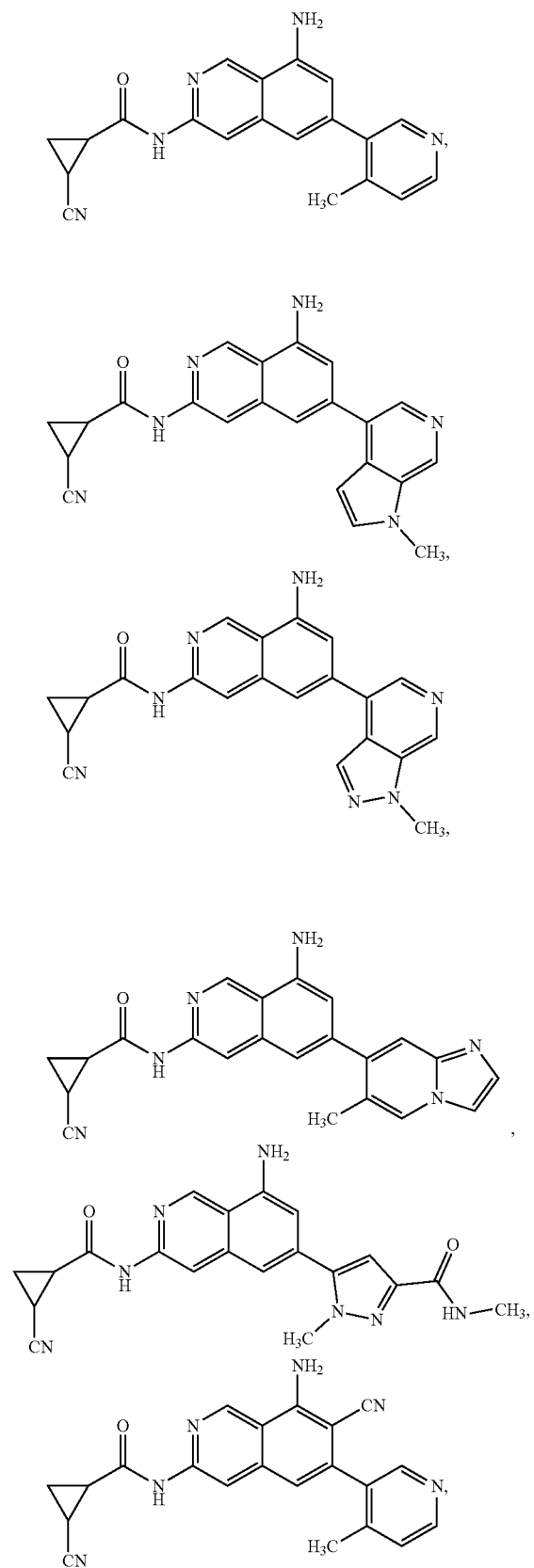
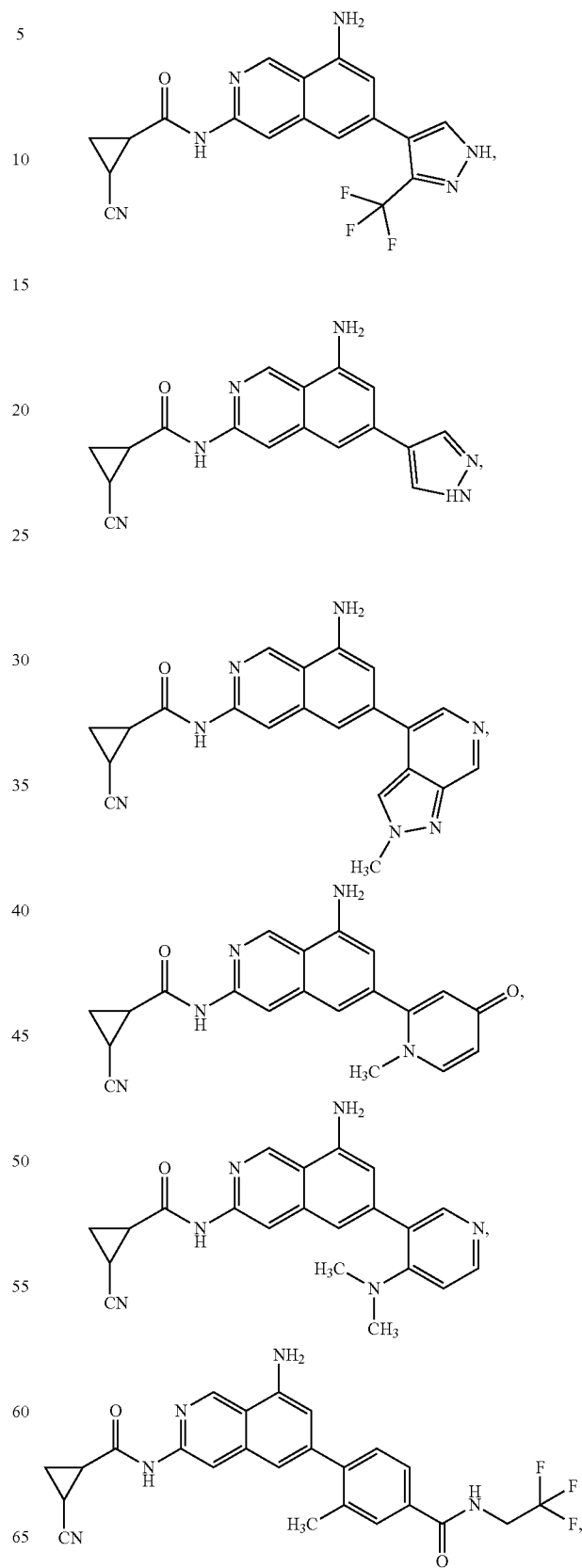

-continued
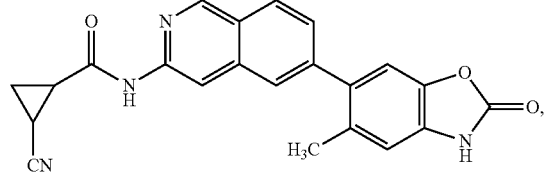
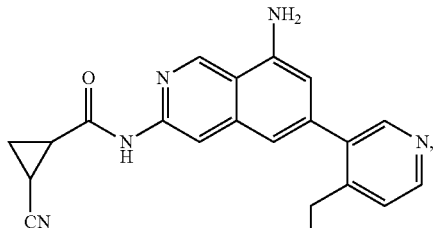
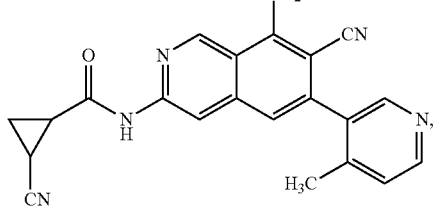
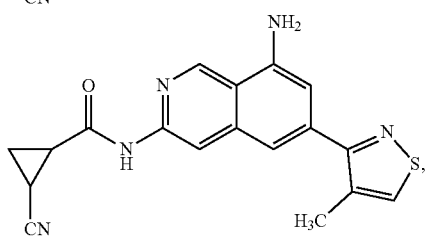
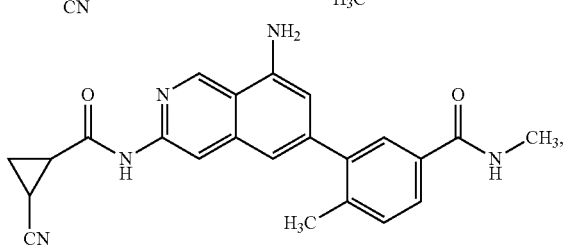
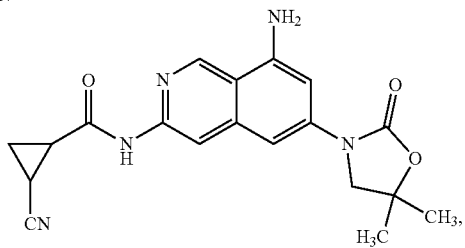
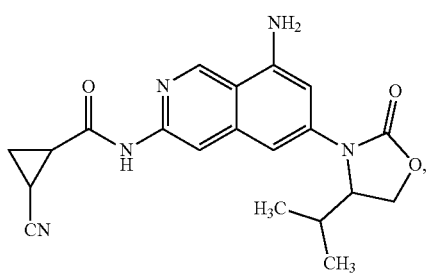
-continued
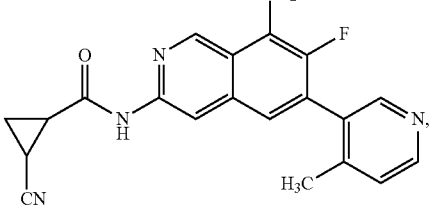
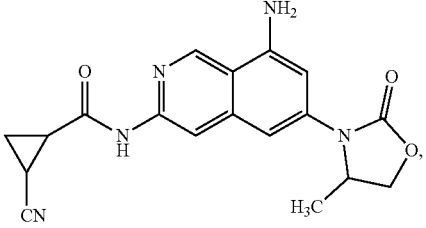
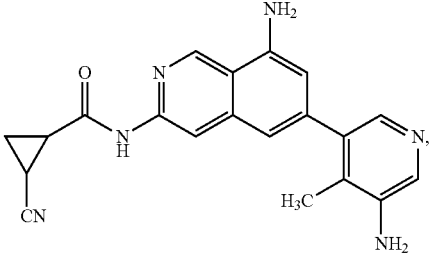
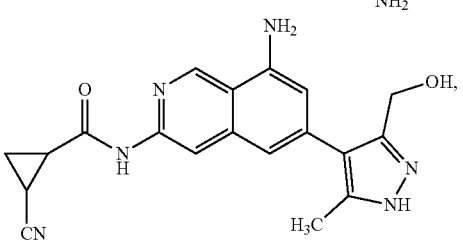
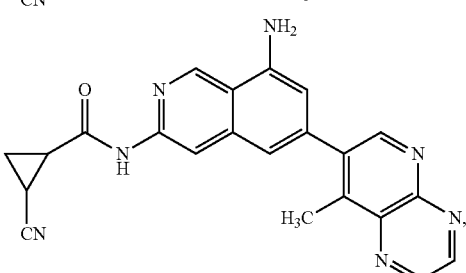
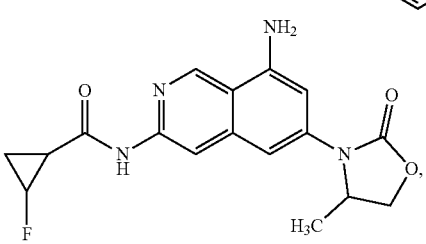
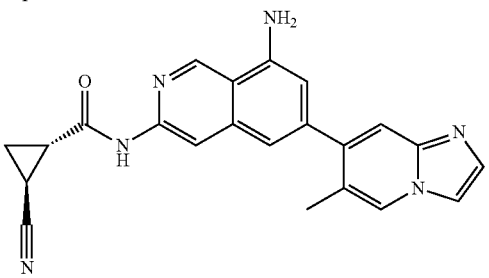

1253
-continued
1254
-continued
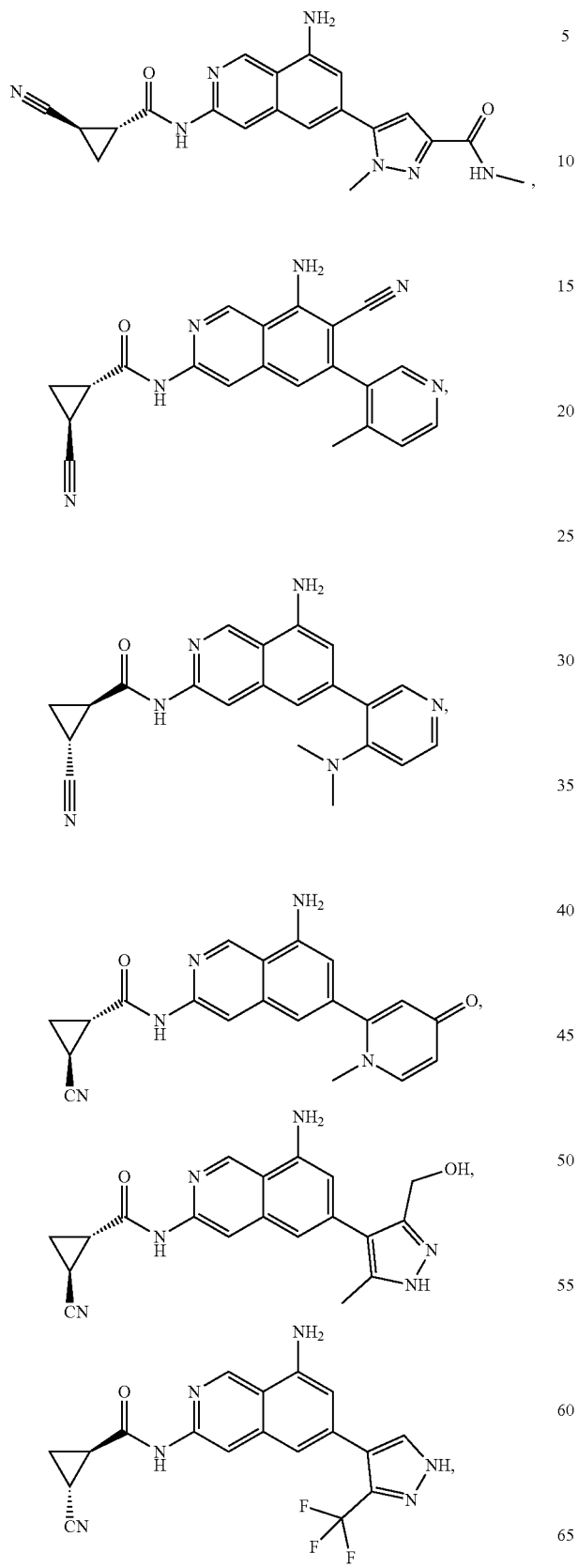
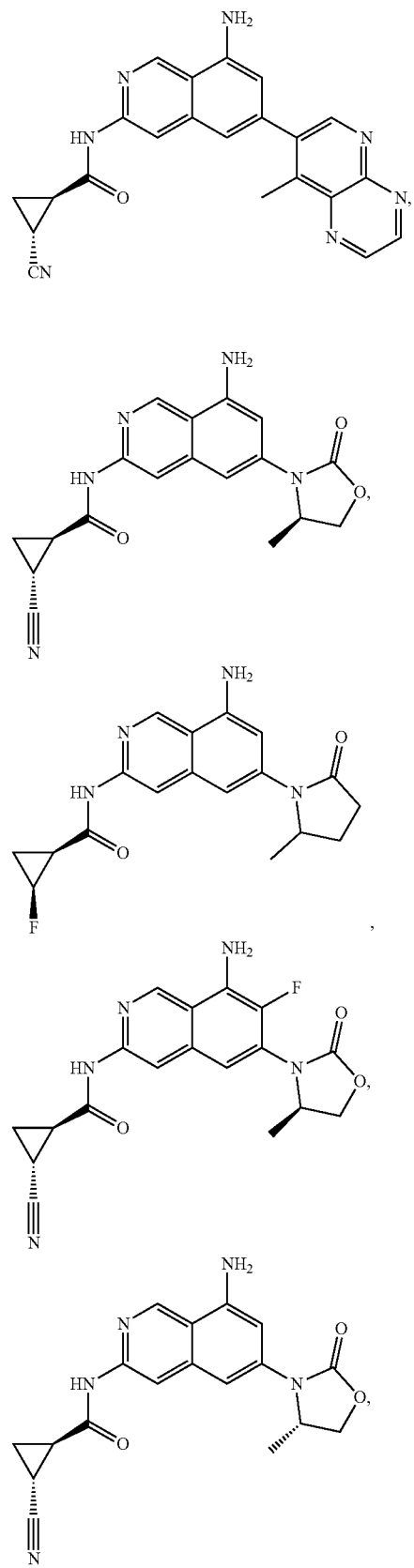

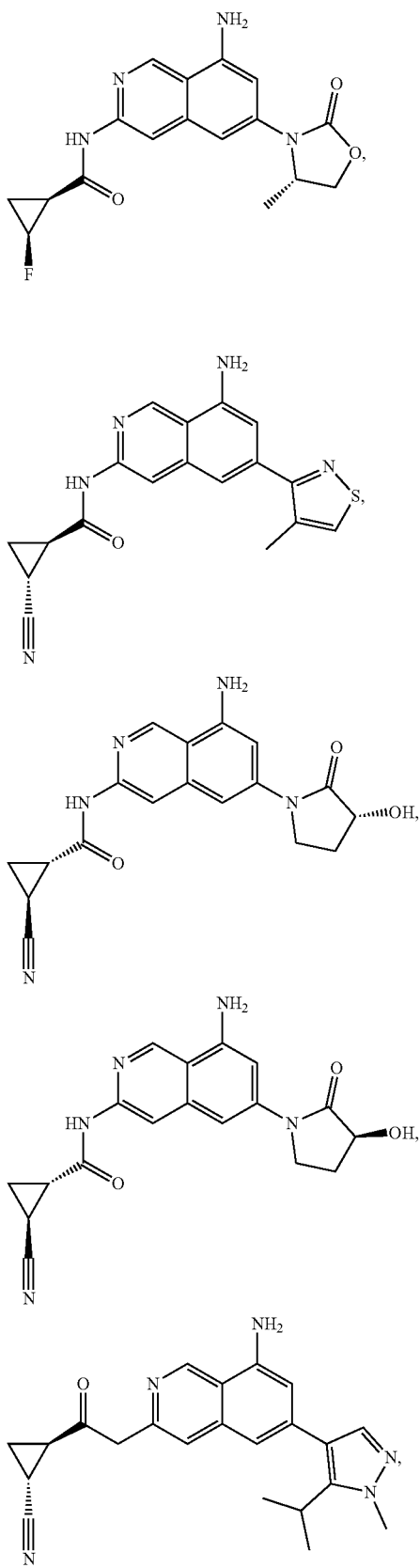
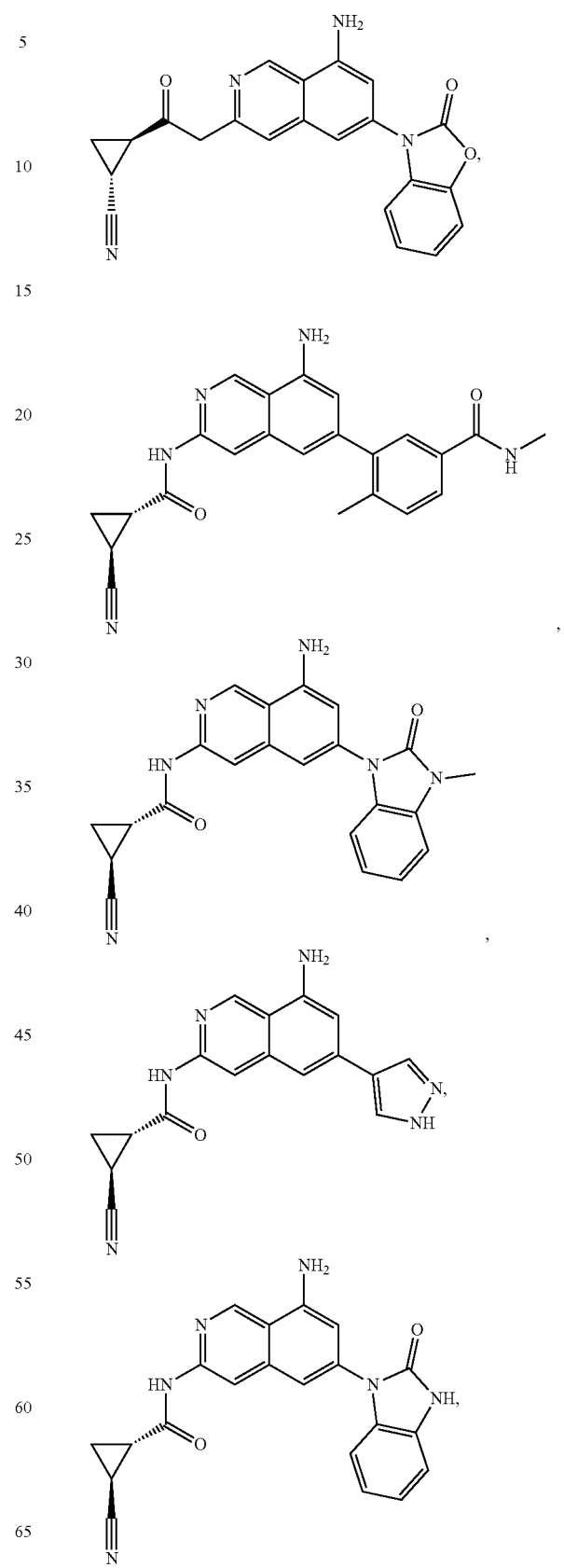

1257
-continued
1258
-continued
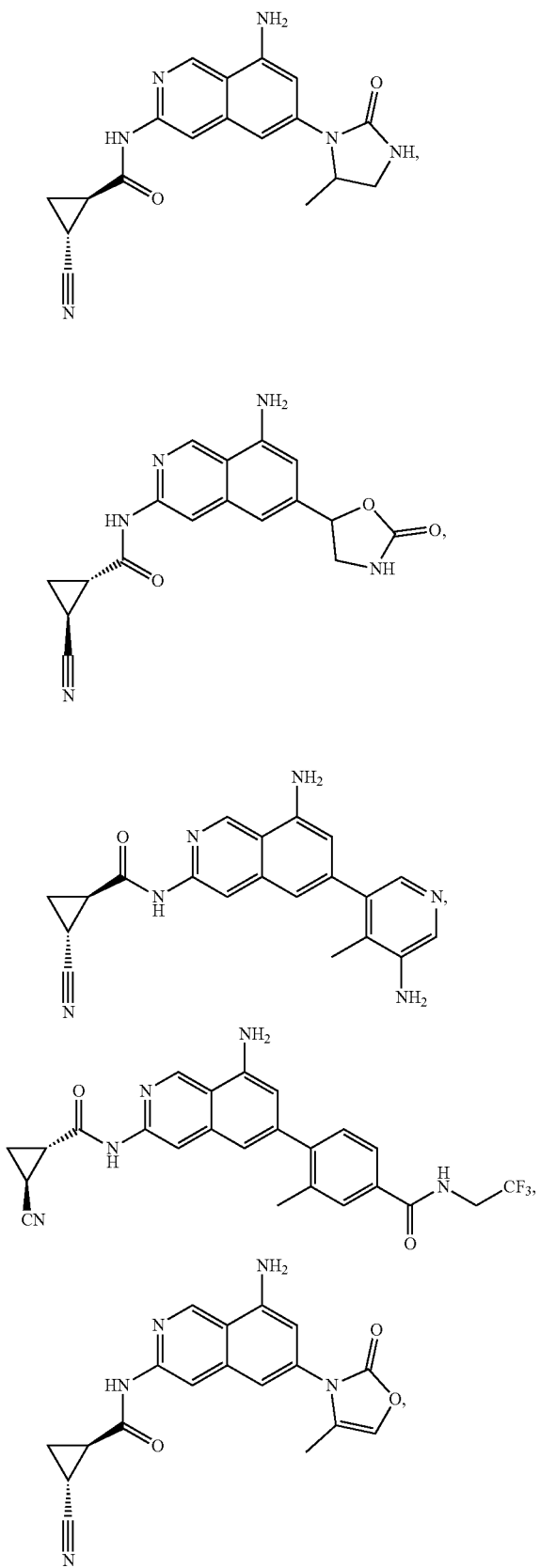
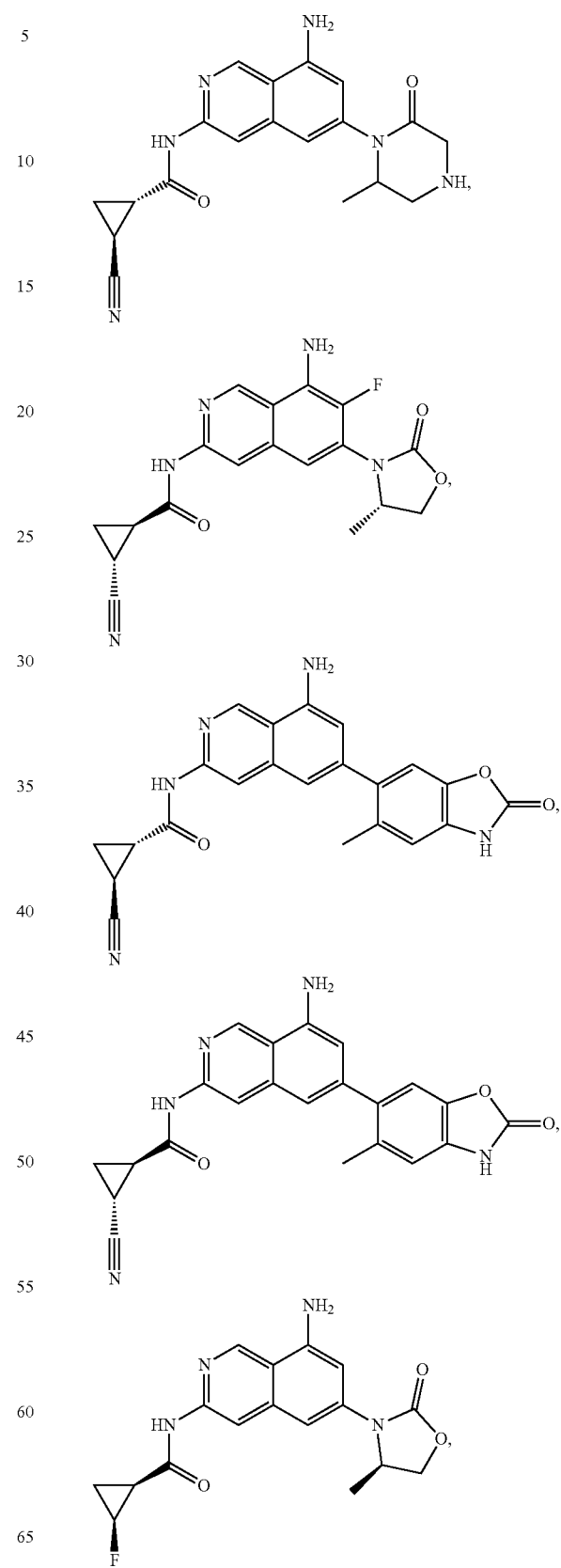

1259
-continued
1260
-continued
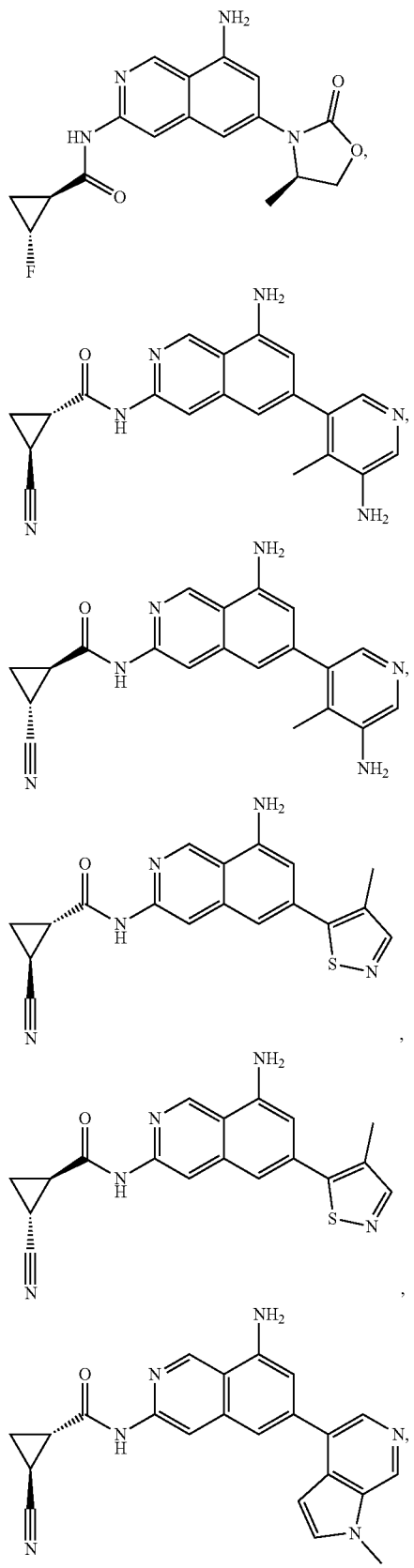
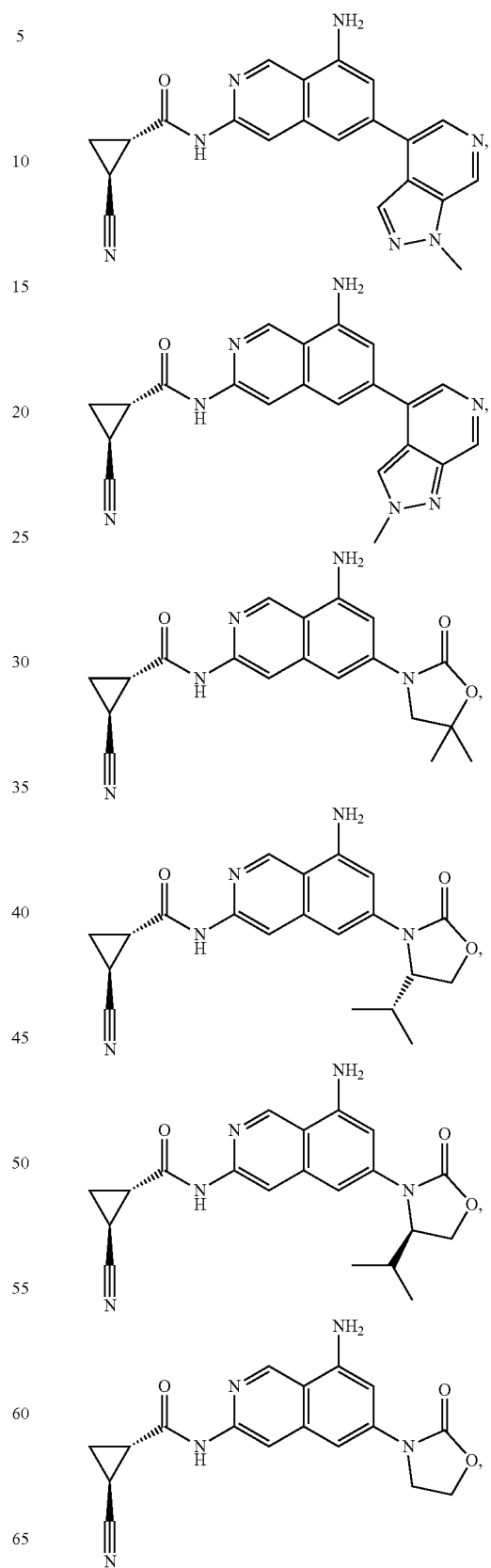

-continued

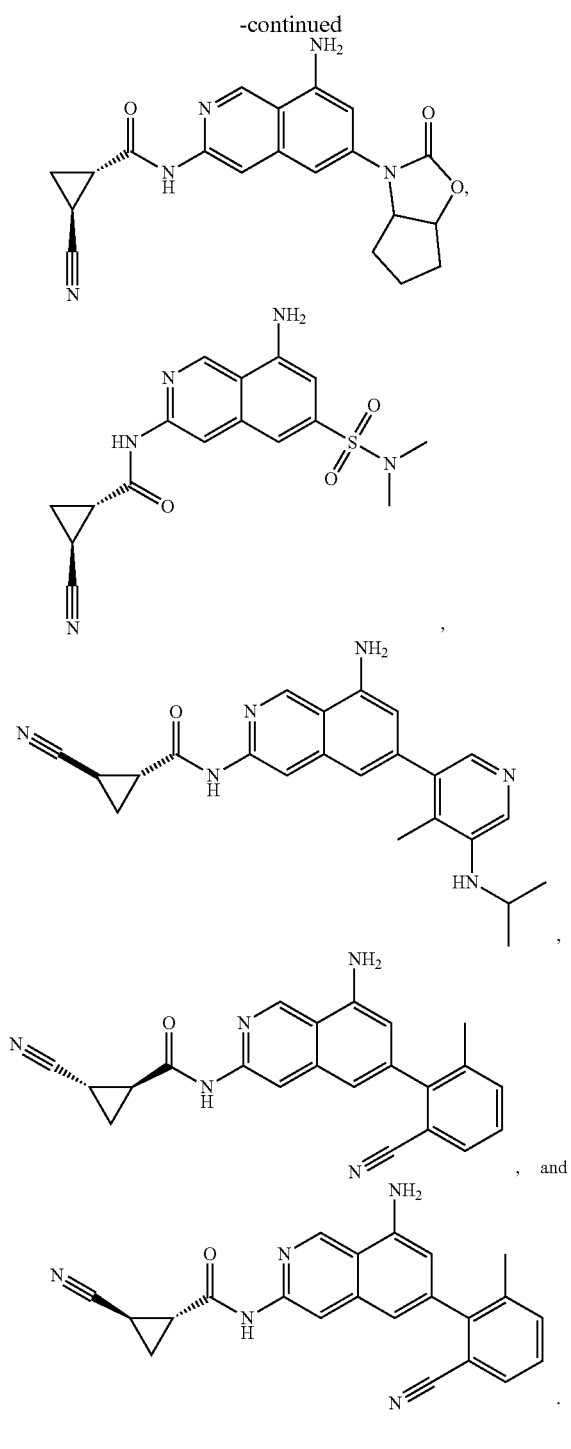

Embodiment 15. The compound of embodiment 12, wherein $R_5$ is $C_{2-9}$ heteroaryl.

Embodiment 16. The compound of embodiment 15, wherein said $C_{2-9}$ heteroaryl is an optionally substituted heteroaryl containing at least one nitrogen.

Embodiment 17. The compound of embodiment 16, wherein said heteroaryl is an optionally substituted 5-member heteroaryl containing 1 or 2 nitrogen atoms.

Embodiment 18. The compound of embodiment 17, wherein said 5-member heteroaryl is an optionally substituted pyrazole.

Embodiment 19. The compound of embodiment 18, having one of the following structures.

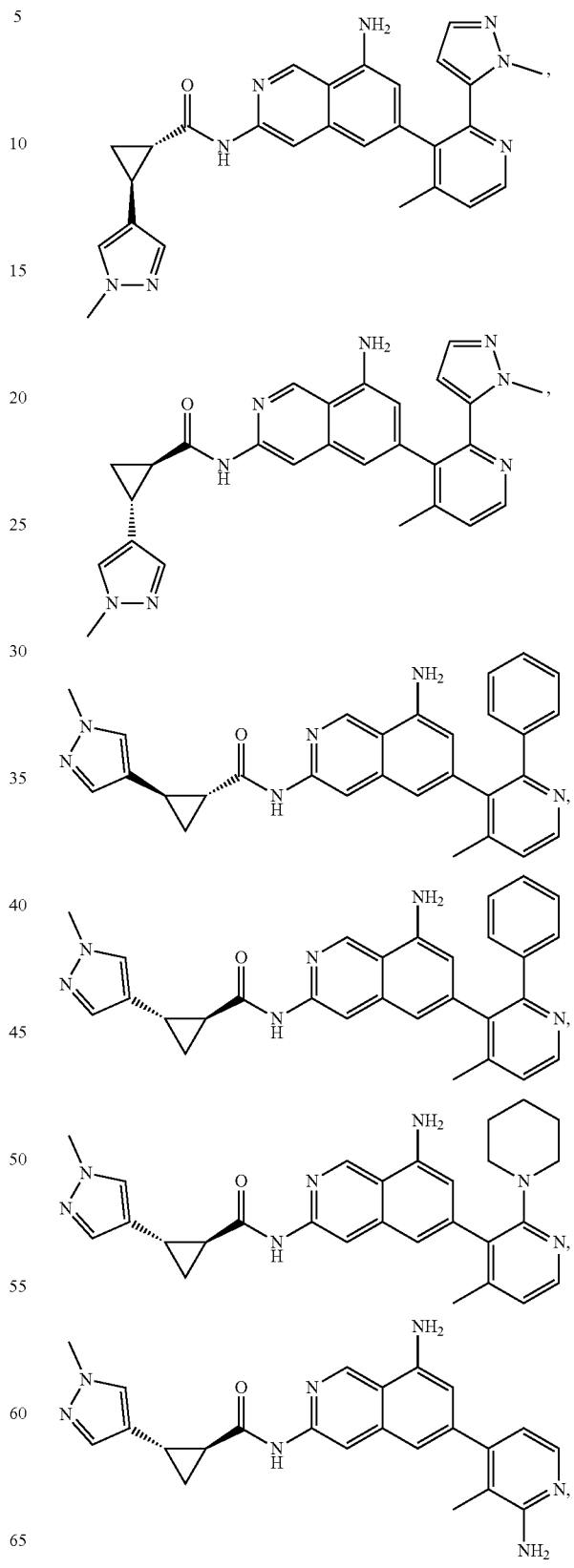

1263
-continued
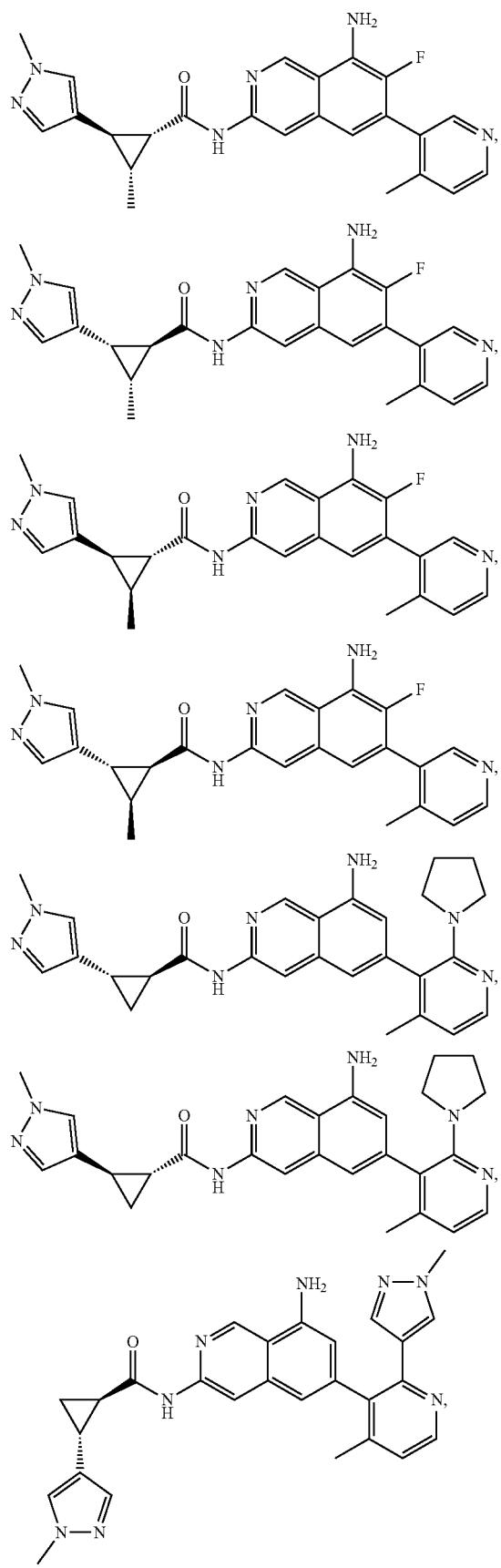
1264
-continued
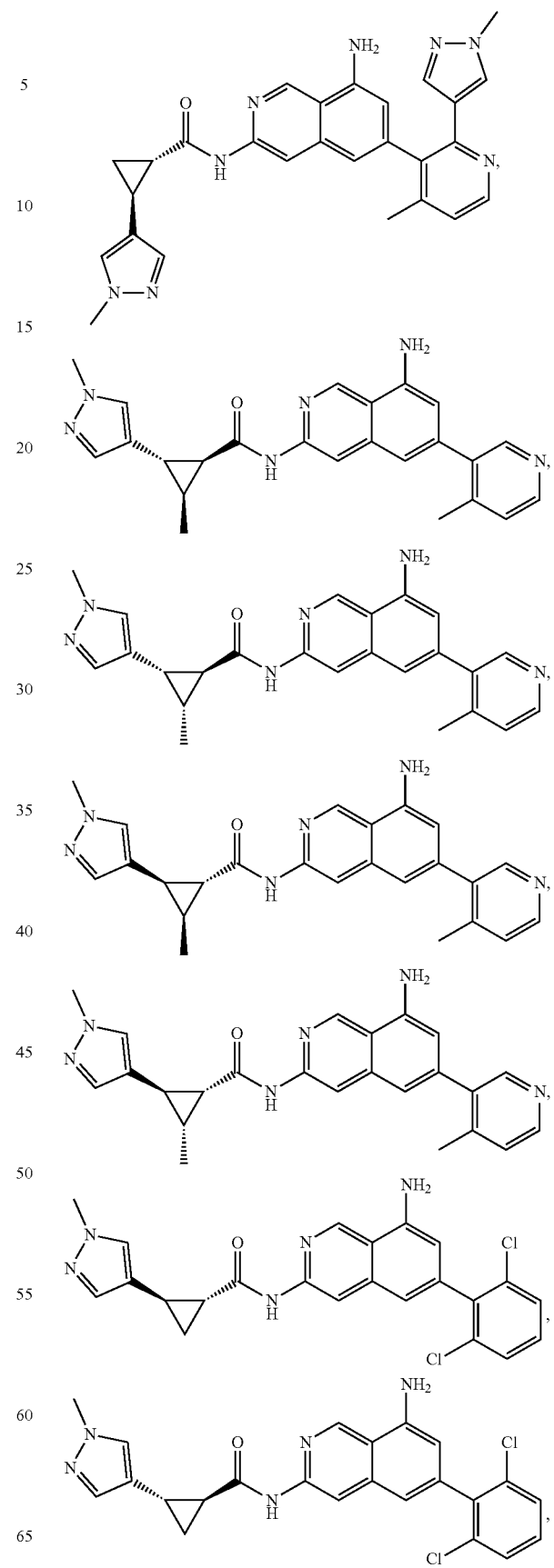

-continued

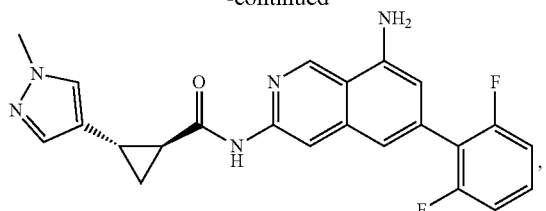

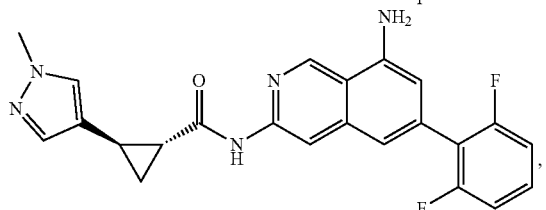

, and

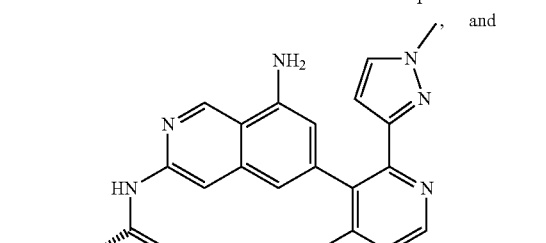

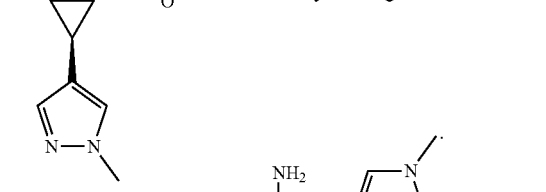

Embodiment 20. The compound of embodiment 12, wherein at least one $R_5$ is cyano($C_{1-6}$)alkyl.

Embodiment 21. The compound of embodiment 20, wherein at least one $R_5$ is cyano-$CH_2$—.

Embodiment 22. The compound of embodiment 21, having one of the following structures:

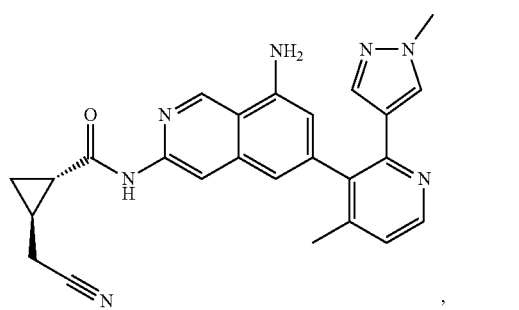

-continued

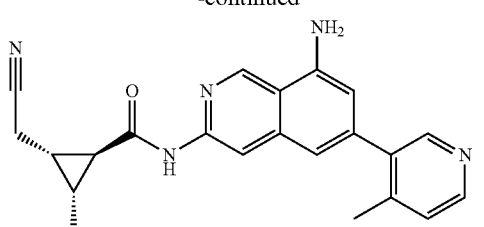

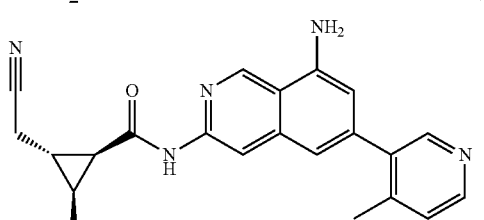

, and

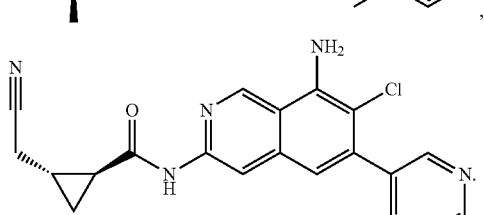

Embodiment 23. The compound of embodiment 12, wherein $R_5$ is hydrogen.

Embodiment 24. The compound of embodiment 23, having one of the following structures:

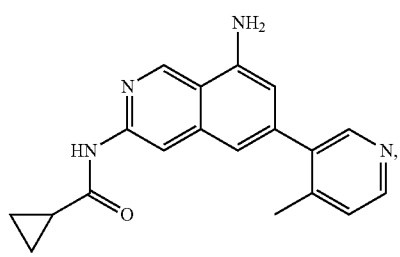

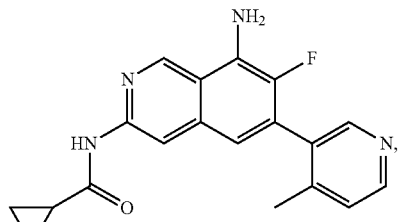

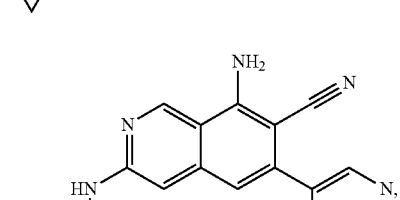

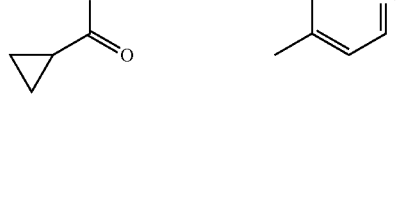

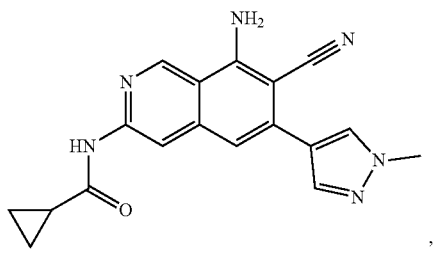

,

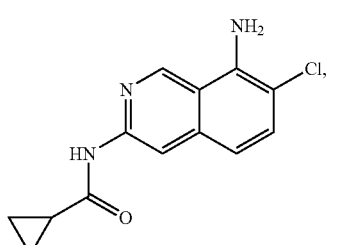

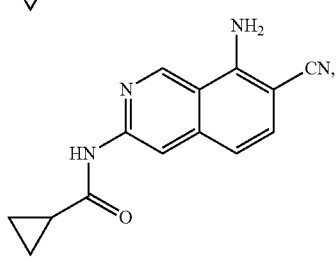

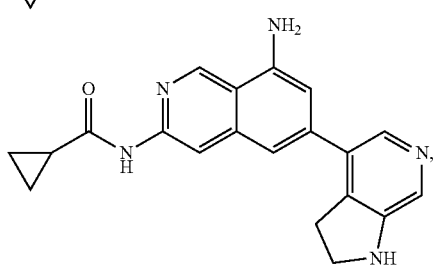

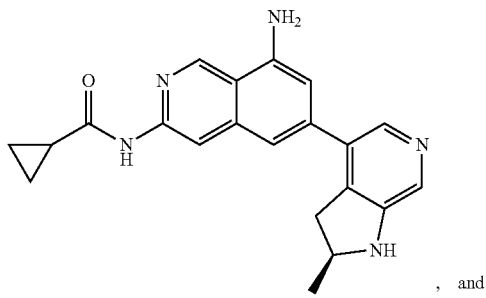

, and

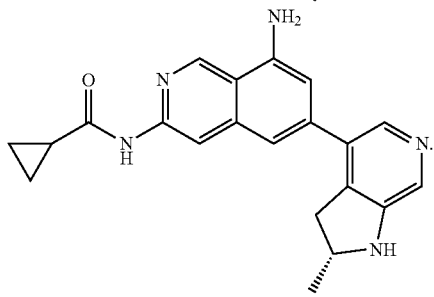

Embodiment 25. The compound of embodiment 1, wherein $R_4$ is D, and wherein D is an optionally substituted heteroaryl containing at least one nitrogen.

Embodiment 26. The compound of embodiment 25, wherein said heteroaryl is an optionally substituted 5-member heteroaryl containing 1 or 2 nitrogen atoms.

Embodiment 27. The compound of embodiment 26, wherein said 5-member heteroaryl is an optionally substituted pyrazole.

Embodiment 28. The compound of embodiment 27, wherein said optionally substituted pyrazole is

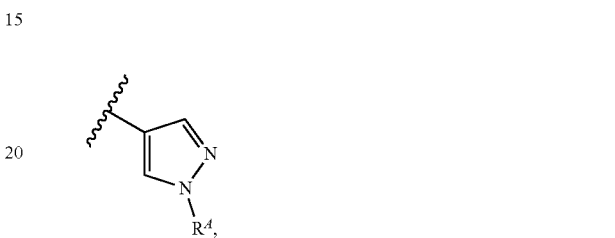

wherein the wavy line denotes the point of attachment to the N; and wherein $R^A$ is branched or linear $C_{1-6}$ alkyl, wherein said alkyl can be optionally substituted with one to four hydroxyl, halogen, nitrile, amino, mono($C_{1-6}$)alkylamino-, di($C_{1-6}$)alkylamino-, or $NR^y(CO)R^z$, wherein R and $R^z$, in each instance, is independently hydrogen or $C_{1-6}$ alkyl.

Embodiment 29. The compound of embodiment 28, wherein $R^A$ is linear $C_{1-6}$ alkyl substituted with hydroxyl, halogen, nitrile, or amino.

Embodiment 30. The compound of embodiment 29, wherein said linear $C_{1-6}$ alkyl is ethyl substituted with nitrile.

Embodiment 31. The compound of embodiment 30, wherein $R^A$ is

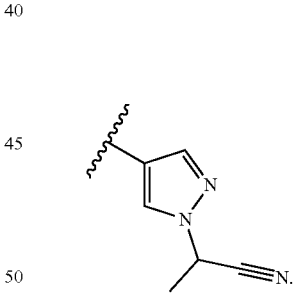

Embodiment 32. The compound of embodiment 31, wherein $R^A$ is

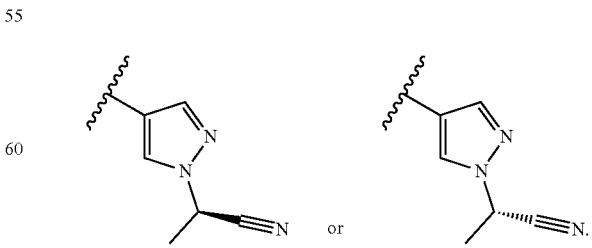

Embodiment 33. The compound of embodiment 31, having one of the following structures:

1269
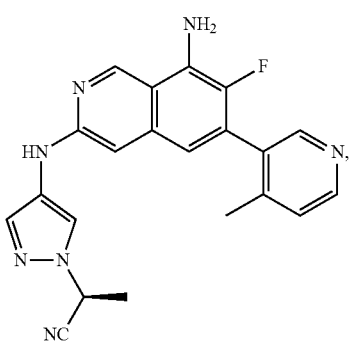
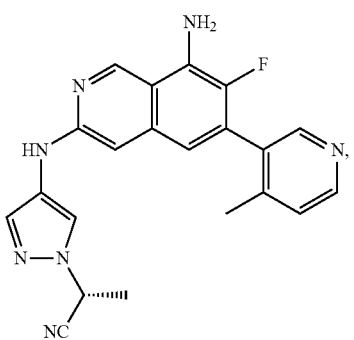
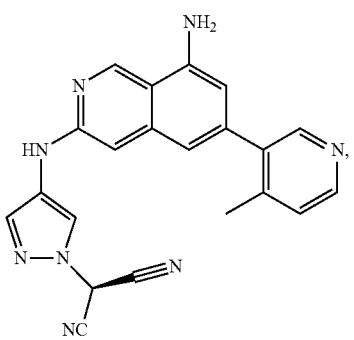
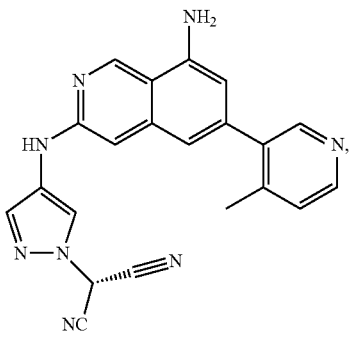
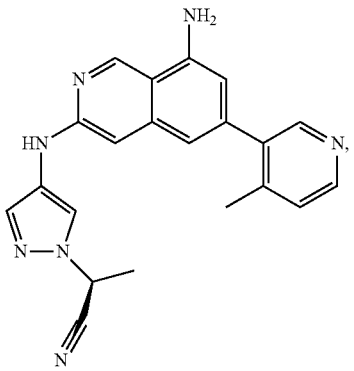
1270
-continued
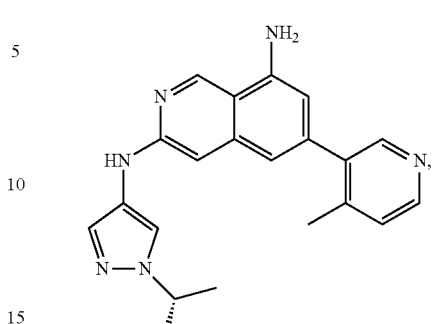
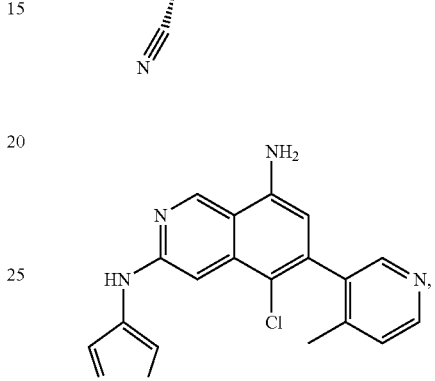
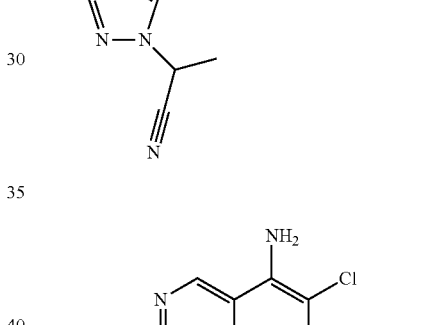
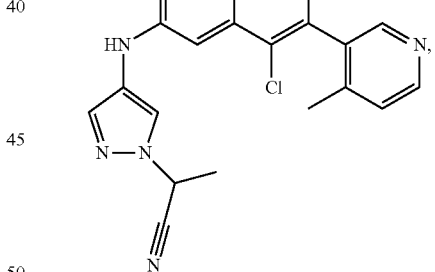
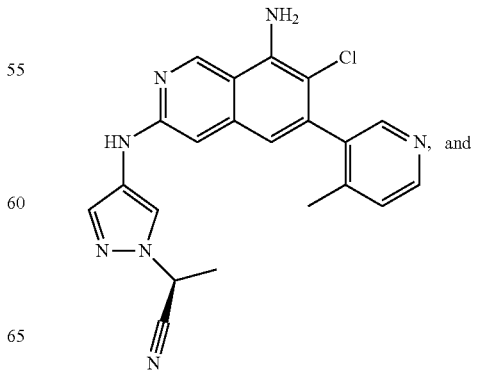
and

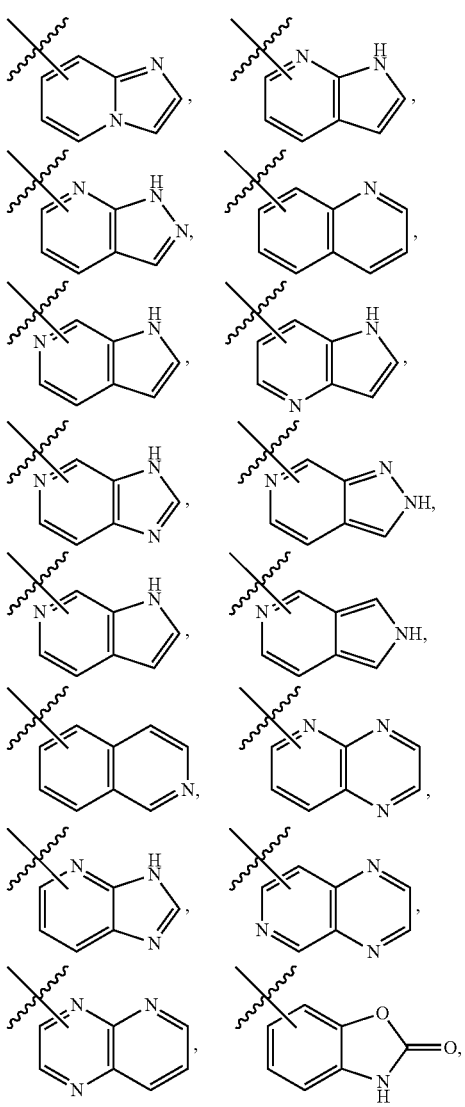

Embodiment 34. The compound of embodiment 1, wherein $R_2$ is an optionally substituted 5-10 member heteroaryl or an optionally substituted 5-10 member heterocyclyl.

Embodiment 35. The compound of embodiment 34, wherein $R_2$ is selected from the group consisting of:

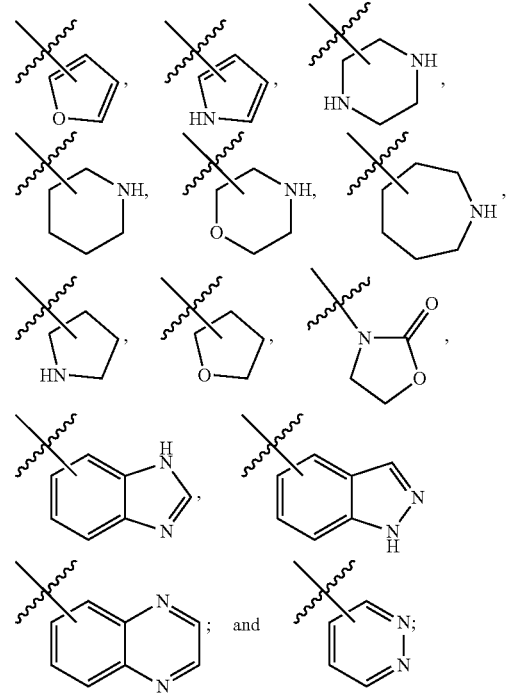

each of which can be optionally substituted at with one, two or three substituents, $R_6$, $R_7$ and $R_5$.

Embodiment 36. The compound of embodiment 35, wherein $R_2$ is:

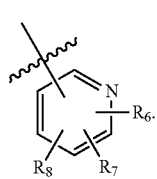

Embodiment 37. The compound of embodiment 36, wherein $R_2$ is:

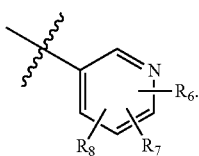
Embodiment 38. The compound of embodiment 37, wherein R₂ is:
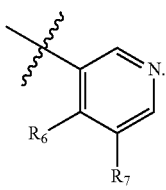
Embodiment 39. The compound of embodiment 38, wherein R₂ is:
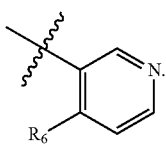
Embodiment 40. The compound of embodiment 39, wherein R₆ is C₁₋₆ alkyl or hydroxy(C₁₋₆)alkyl.
Embodiment 41. The compound of embodiment 40, wherein R₆ is methyl.
Embodiment 42. The compound of embodiment 41, having one of the following structures:
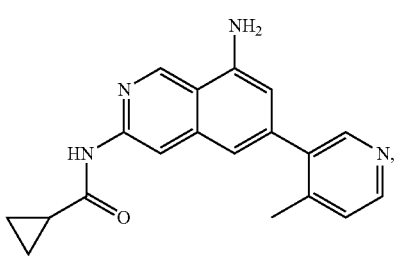
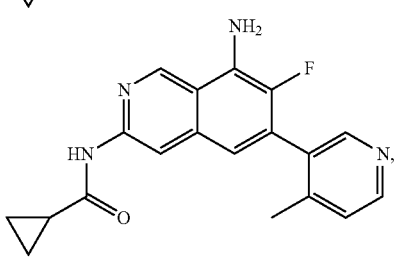
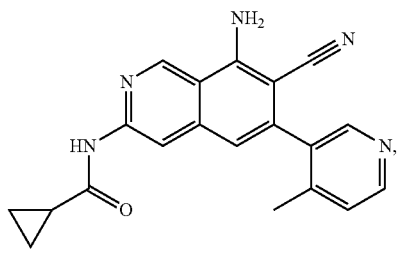
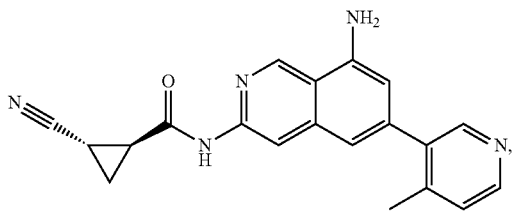
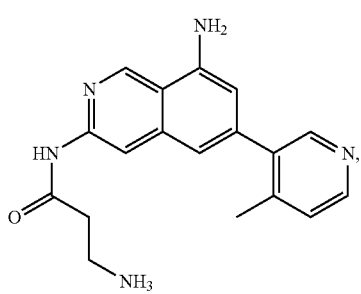
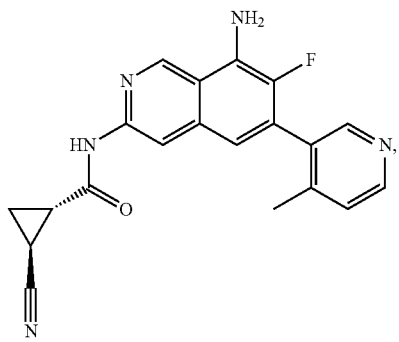
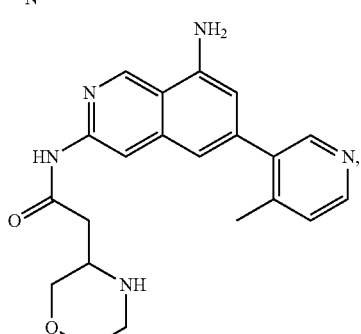
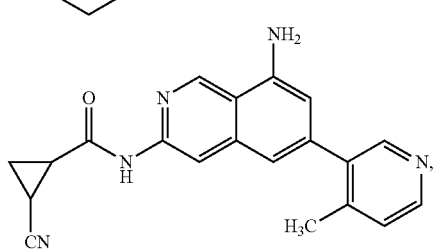

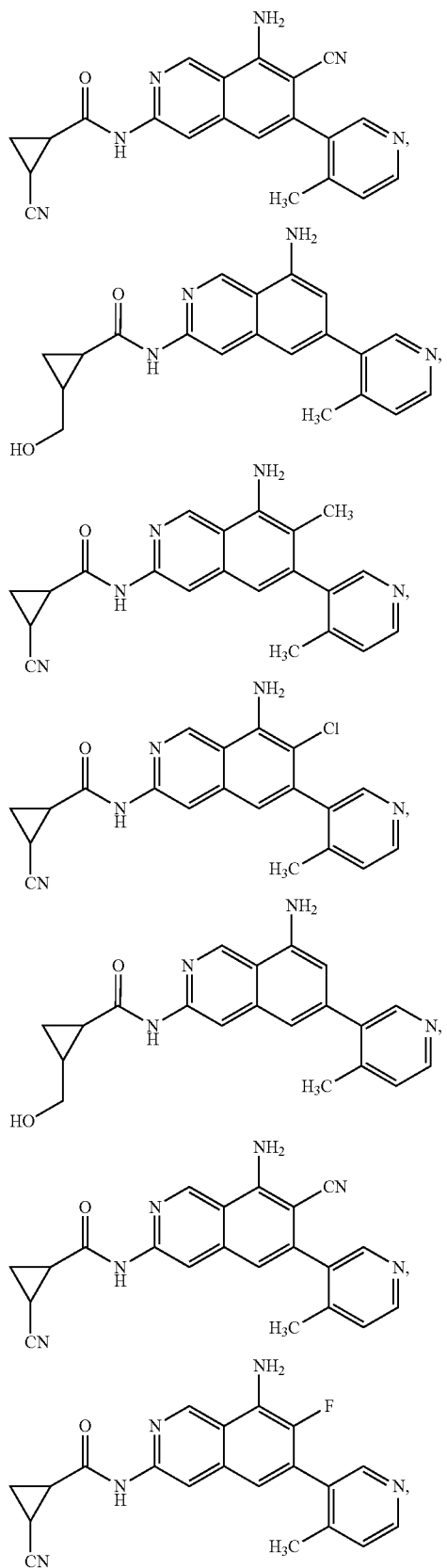
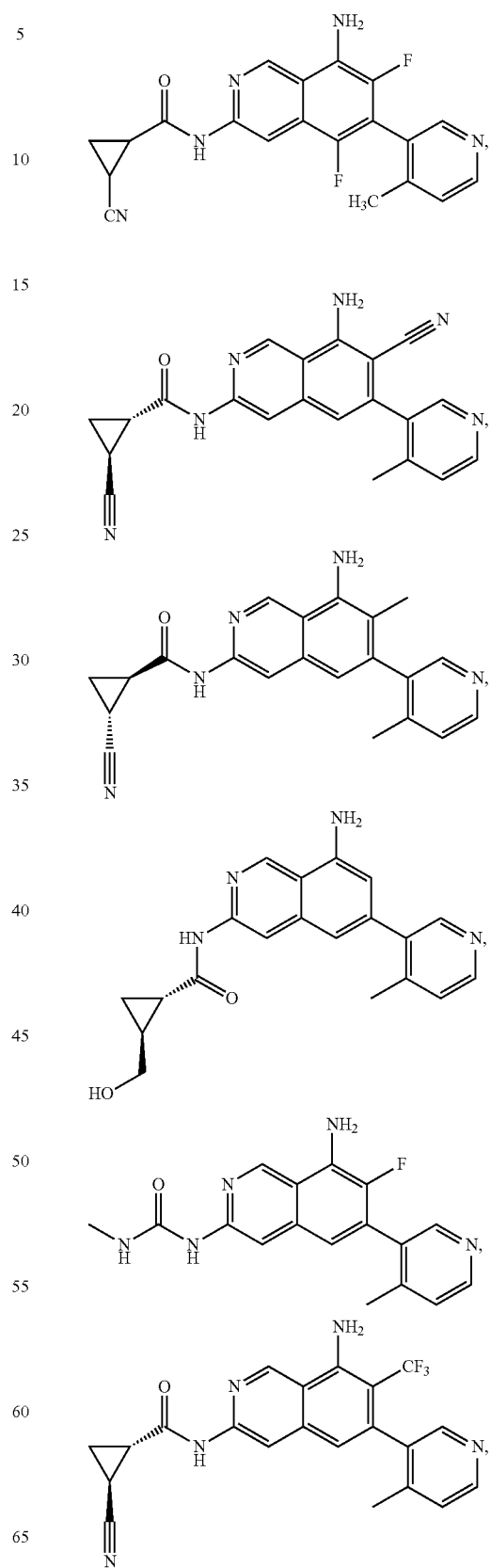

1277
-continued
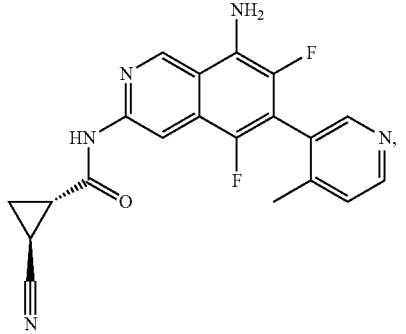
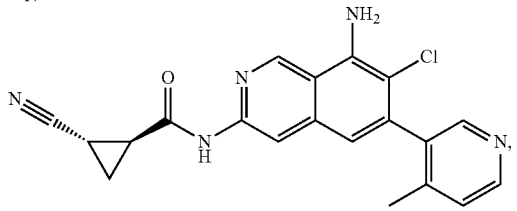
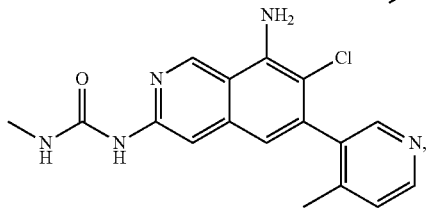
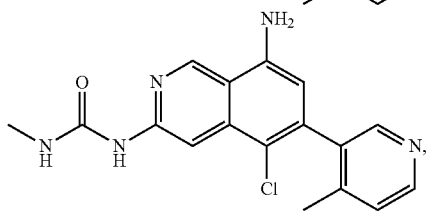
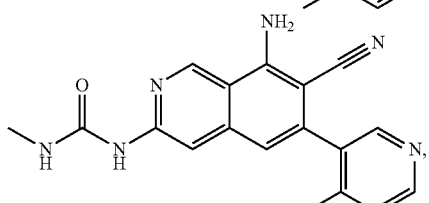
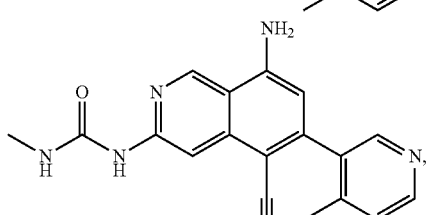
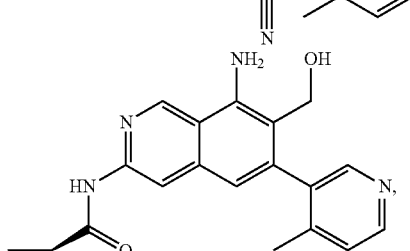
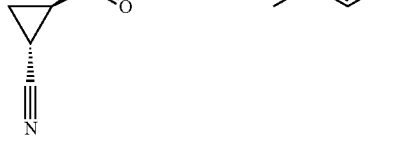
1278
-continued
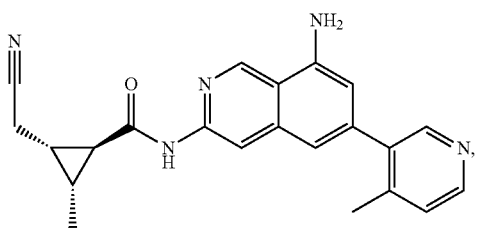
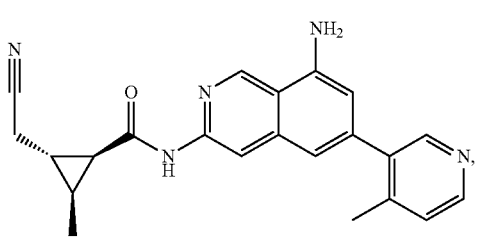
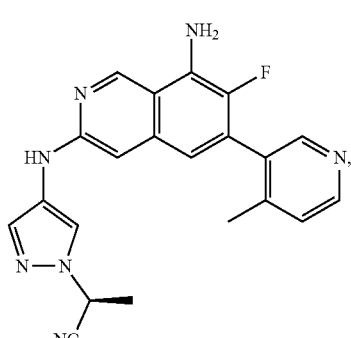
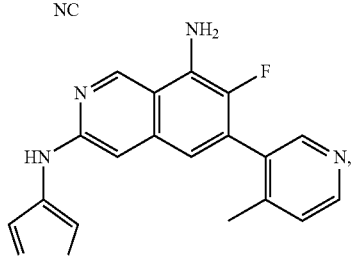
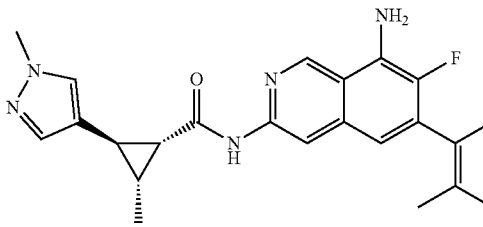
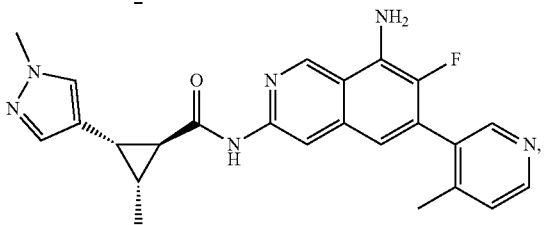

1279
-continued
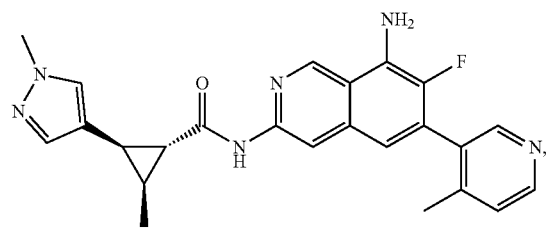
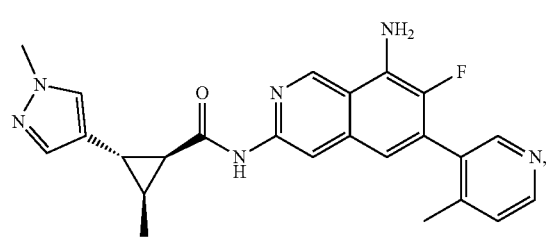
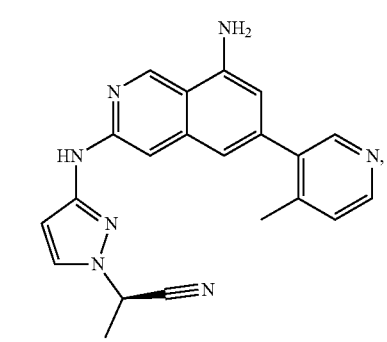
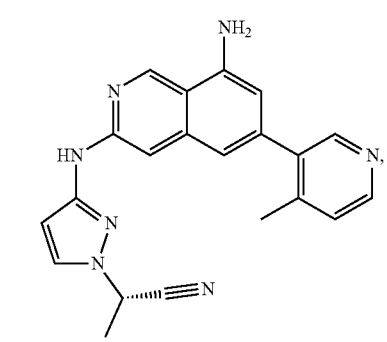
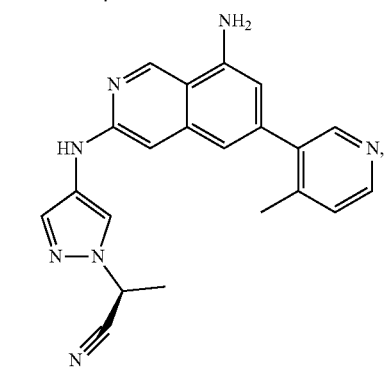
1280
-continued
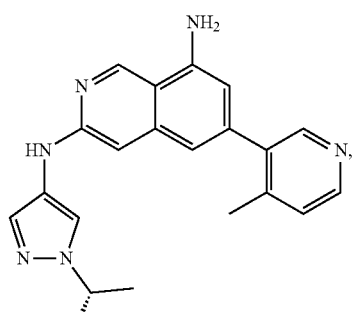
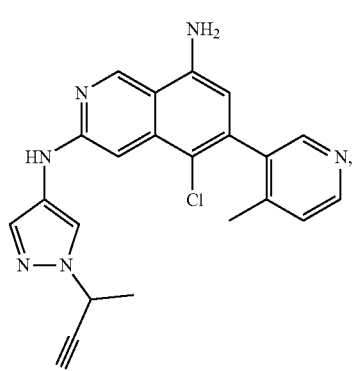
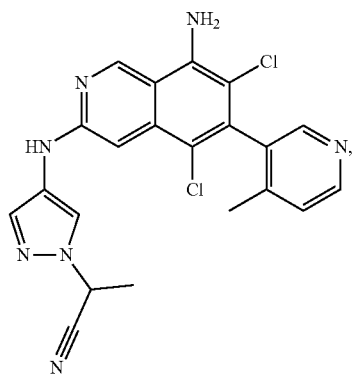
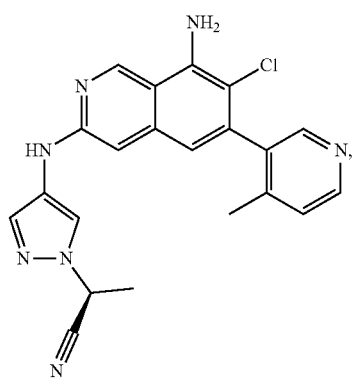

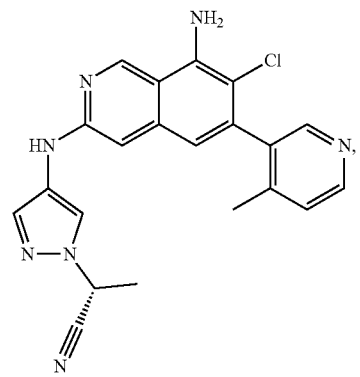

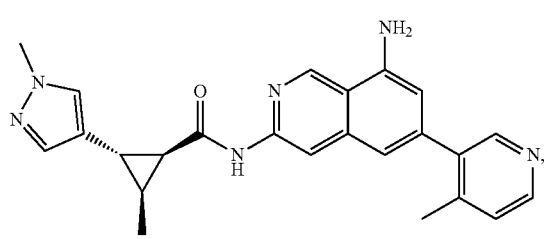

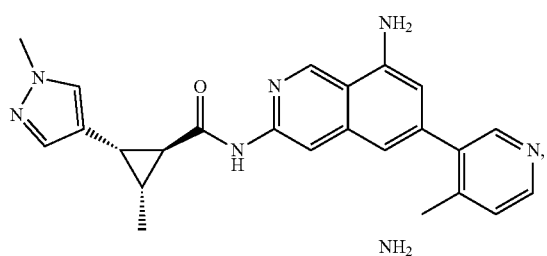

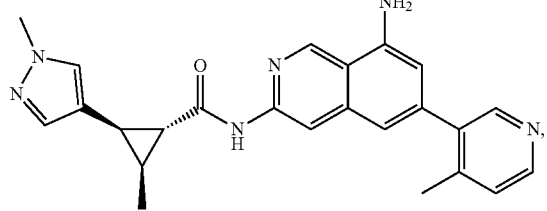

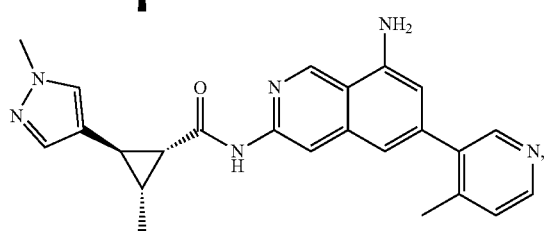

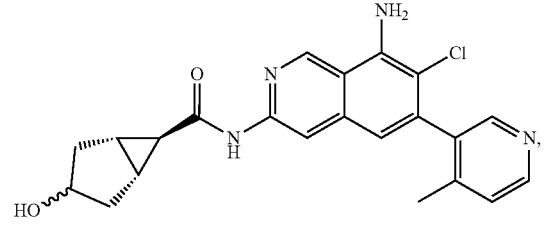

Exo for C3-Pr, unknown for OH

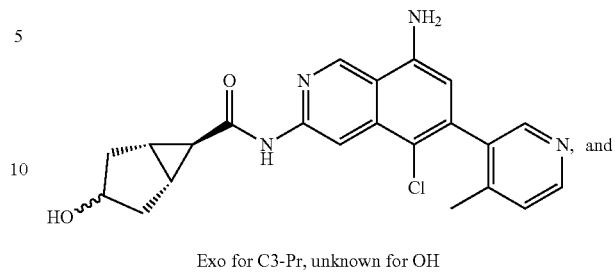

Exo for C3-Pr, unknown for OH

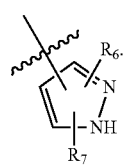

Embodiment 43. The compound of embodiment 35, wherein $R_2$ is:

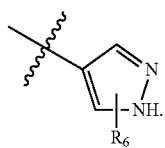

Embodiment 44. The compound of embodiment 43, wherein $R_2$ is:

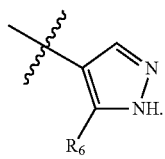

Embodiment 45. The compound of embodiment 44, wherein $R_2$ is:

Embodiment 46. The compound of embodiment 45, wherein $R_6$ is branched or linear $C_{1-6}$ alkyl, wherein said alkyl can be optionally substituted with one to four hydroxyl or halogen.

Embodiment 47. The compound of embodiment 46, wherein $R_2$ is:

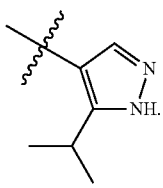 [SMILES: *c1cn[nH]c1C(C)C]

Embodiment 48. The compound of embodiment 47, having one of the following structures:

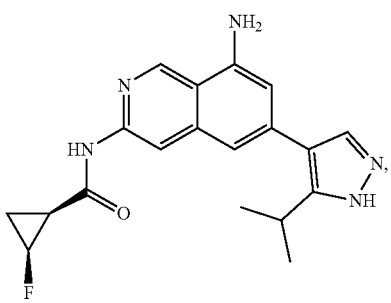

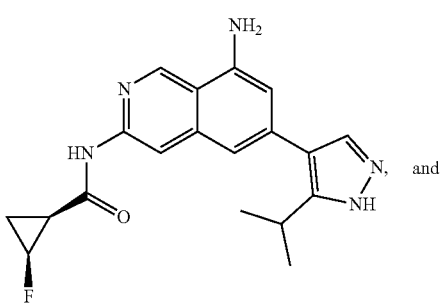

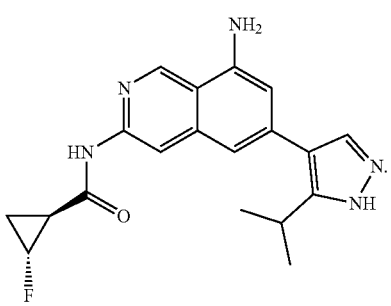

Embodiment 49. The compound of embodiment 35, wherein $R_2$ is:

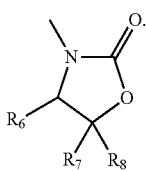

Embodiment 50. The compound of embodiment 49, wherein $R_2$ is:

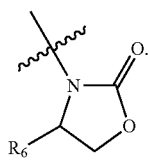

Embodiment 51. The compound of embodiment 50, wherein $R_6$ is branched or linear $C_{1-6}$ alkyl.

Embodiment 52. The compound of embodiment 51, wherein $R_6$ is methyl, ethyl or isopropyl.

Embodiment 53. The compound of embodiment 52, having one of the following structures:

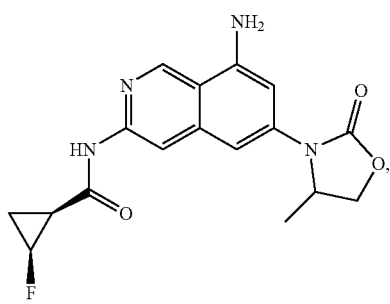

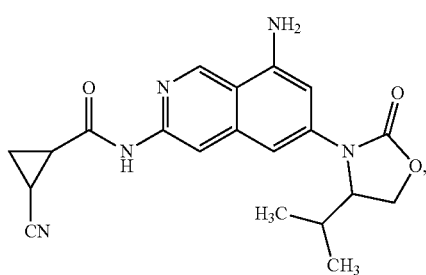

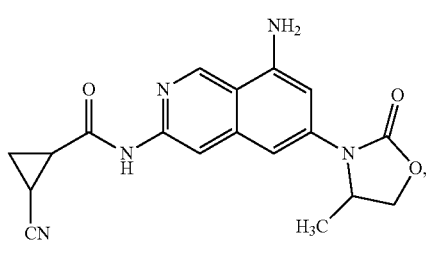

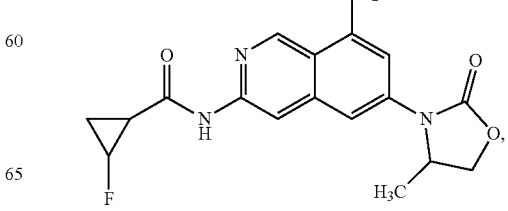

1285
-continued
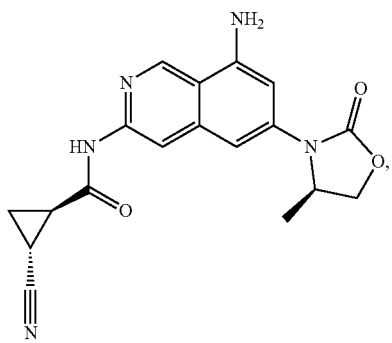
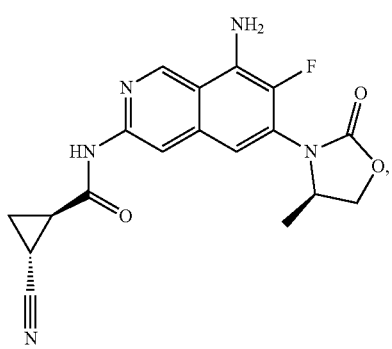
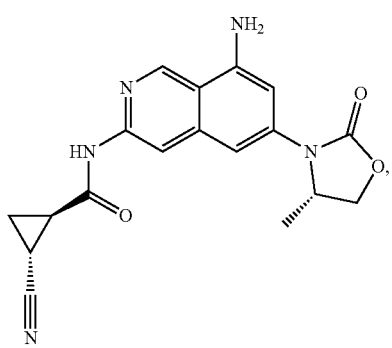
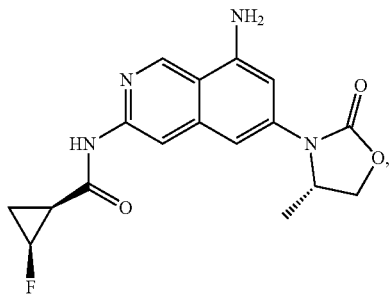
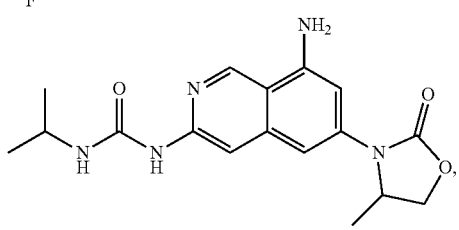
1286
-continued
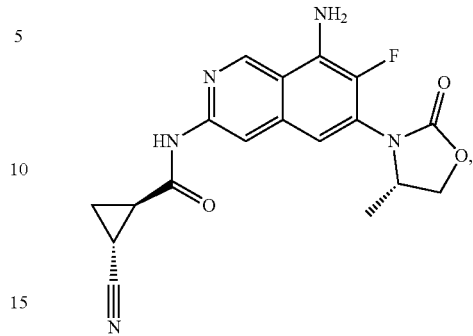
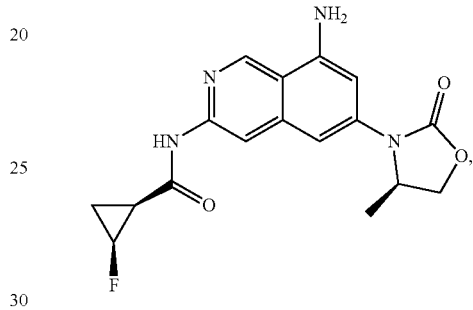
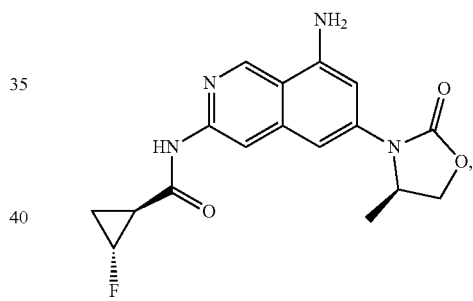
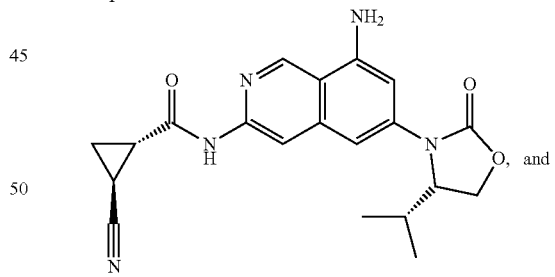, and
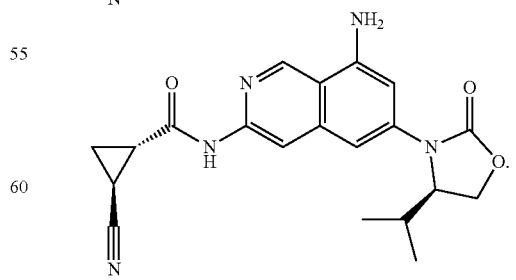
Embodiment 54. The compound of embodiment 35, wherein $R_2$ is:

1287

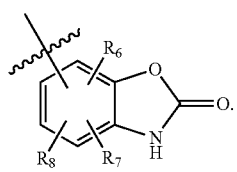

Embodiment 55. The compound of embodiment 54, wherein R₂ is:

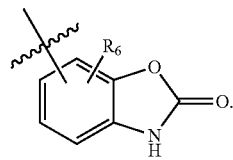

Embodiment 56. The compound of embodiment 55, wherein R₂ is:

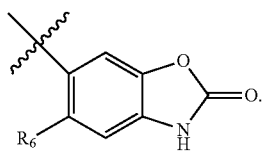

Embodiment 57. The compound of embodiment 56, wherein R₆ is branched or linear C₁₋₆ alkyl.

Embodiment 58. The compound of embodiment 57, wherein R₆ is methyl.

Embodiment 59. The compound of embodiment 58, having one of the following structures:

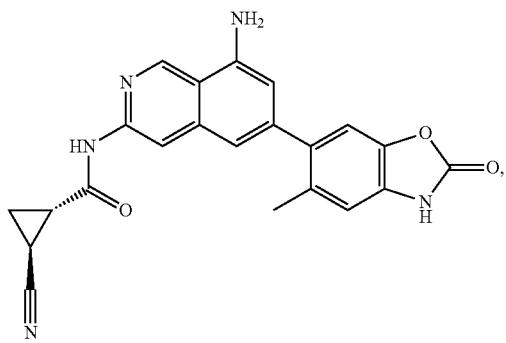

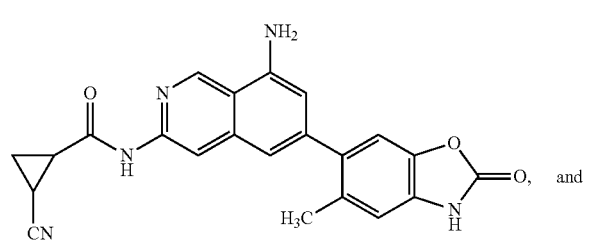

1288

-continued

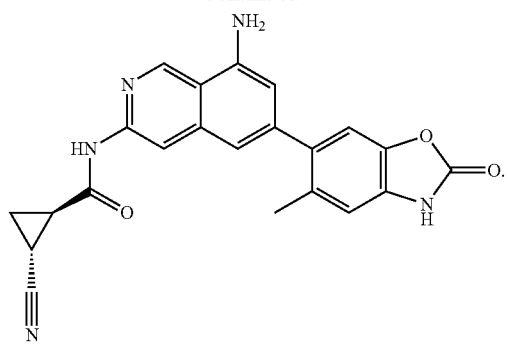

Embodiment 60. The compound of embodiment 35, wherein R₂ is:

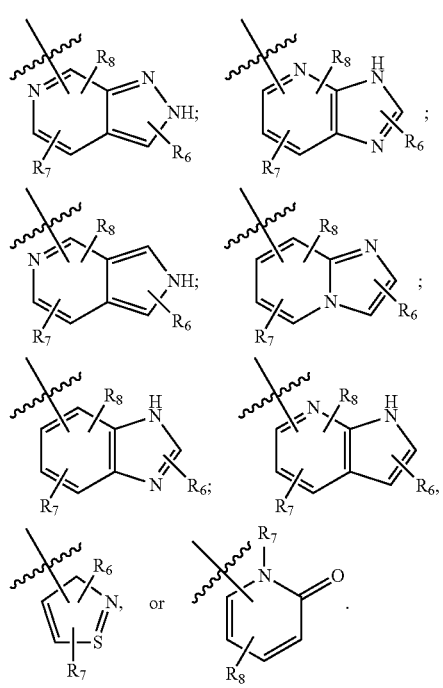

Embodiment 61. The compound of embodiment 35, wherein one of R₆, R₇ and R₈ is O and together with the carbon to which it is attached forms a carbonyl.

Embodiment 62. The compound of embodiment 61, wherein R₂ is

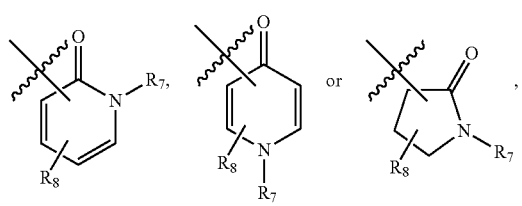

wherein R₇ is hydrogen or C₁₋₆ alkyl.

Embodiment 63. The compound of embodiment 62, having one of the following structures:

1289
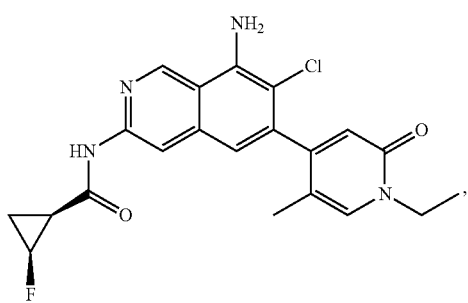
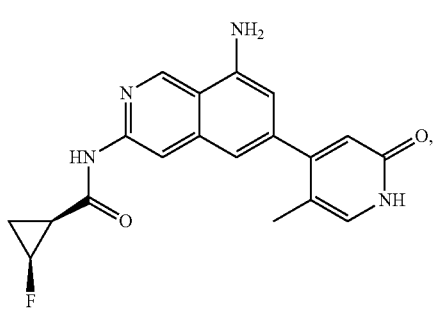
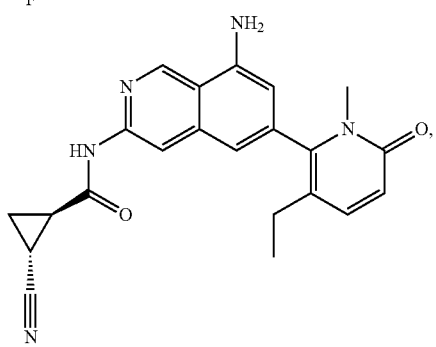
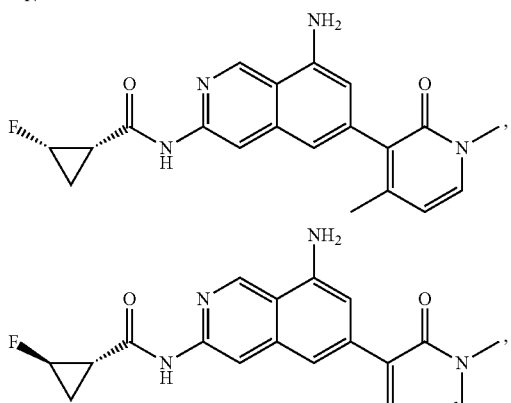
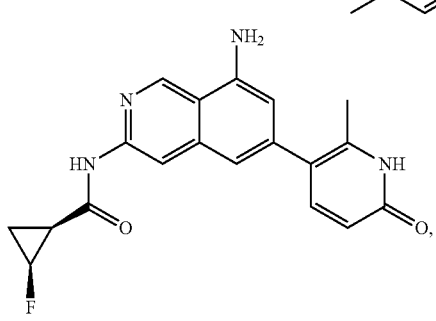
1290
-continued
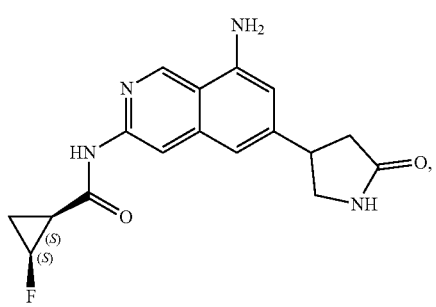
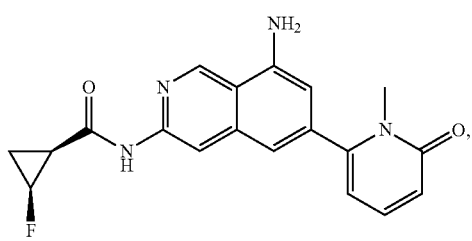
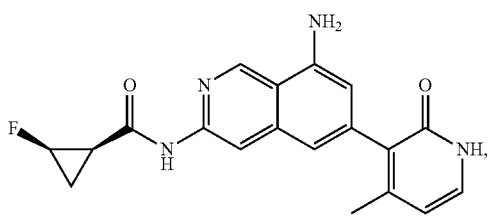
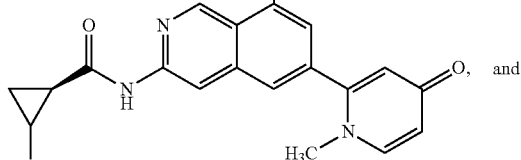
Embodiment 64. The compound of embodiment 1, having one of the following structures:
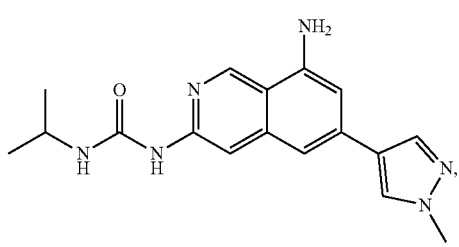

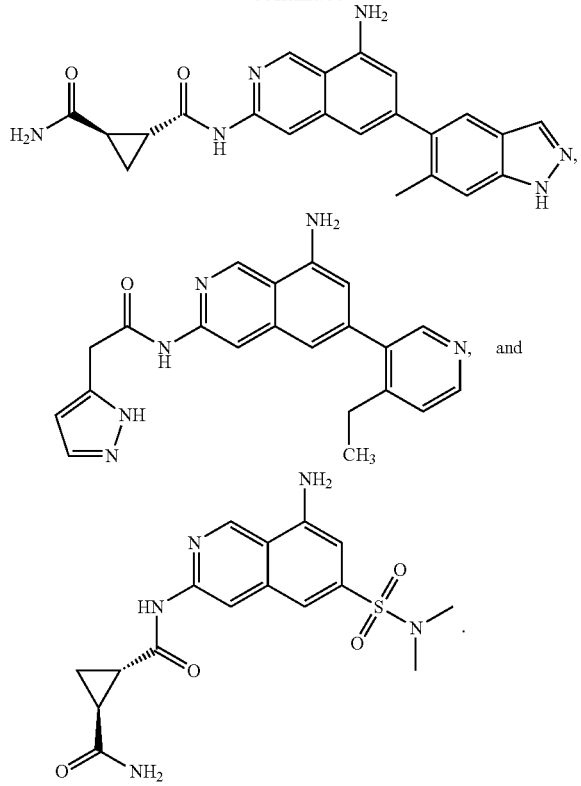

Embodiment 65. A pharmaceutical composition comprising a compound of any one of embodiments 1-64 and a pharmaceutically acceptable carrier.

Embodiment 66. The pharmaceutical composition of embodiment 65, wherein said composition further comprises a chemotherapeutic agent.

Embodiment 67. The pharmaceutical composition of embodiment 66, wherein said chemotherapeutic agent is an immunotherapeutic agent.

Embodiment 68. A method of inhibiting HPK1, said method comprising contacting HPK1 with an effective amount of a compound of any one of embodiments 1-64 or a pharmaceutical composition of any one of embodiments 65-67.

Embodiment 69. A method for enhancing an immune response in a subject in need thereof, wherein the method comprises administering to said subject an effective amount of a compound of any one of embodiments 1-64 or a pharmaceutical composition of any one of embodiments 65-67.

Embodiment 70. The method of embodiment 69, wherein T cells in the subject have at least one of enhanced priming, enhanced activation, enhanced migration, enhanced proliferation, enhanced survival, and enhanced cytolytic activity relative to prior to the administration of the compound or pharmaceutical composition.

Embodiment 71. The method of embodiment 70, wherein the T cell activation is characterized by an elevated frequency of $\gamma$-IFN$^+$ CD8 T cells or enhanced levels of IL-2 or granzyme B production by T cells relative to prior to administration of the compound or pharmaceutical composition.

Embodiment 72. The method of embodiment 71, wherein the number of T cells is elevated relative to prior to administration of the compound or pharmaceutical composition.

Embodiment 73. The method of any one of embodiments 70-72, wherein the T cell is an antigen-specific CD8 T cell.

Embodiment 74. The method of embodiment 73, wherein the antigen presenting cells in the subject have enhanced maturation and activation relative prior to the administration of the compound or pharmaceutical composition.

Embodiment 75. The method of embodiment 74, wherein the antigen presenting cells are dendritic cells.

Embodiment 76. The method of embodiment 74, wherein the maturation of the antigen presenting cells is characterized by increased frequency of CD83$^+$ dendritic cells.

Embodiment 77. The method of embodiment 74, wherein the activation of the antigen presenting cells is characterized by elevated expression of CD80 and CD86 on dendritic cells.

Embodiment 78. The method of any one of embodiments 68-77, wherein said subject has cancer.

Embodiment 79. A method for treating a HPK1-dependent disorder, said method comprising administering to a subject in need thereof an effective amount of a compound of any one of embodiments 1-64 or a pharmaceutical composition of any one of embodiments 65-67.

Embodiment 80. The method of embodiment 79, wherein said HPK1-dependent disorder is a cancer.

Embodiment 81. The method of embodiment 78 or 80, wherein the cancer comprises at least one cancer selected from the group consisting of colorectal cancer, melanoma, non-small cell lung cancer, ovarian cancer, breast cancer, pancreatic cancer, a hematological malignancy, and a renal cell carcinoma.

Embodiment 82. The method of any one of embodiments 78, 80, or 81, wherein the cancer has elevated levels of T-cell infiltration.

Embodiment 83. The method of any one of embodiments 78, 80, 81, or 82, wherein the cancer cells in the subject selectively have elevated expression of MHC class I antigen expression relative to prior to the administration of the compound or composition.

Embodiment 84. The method of any one of embodiments 78, 80, 81, 82, or 83, wherein said method further comprises administering a chemotherapeutic agent to said subject.

Embodiment 85. The method of embodiment 84, wherein said chemotherapeutic agent is administered to said subject simultaneously with said compound or said composition.

Embodiment 86. The method of embodiment 84, wherein said chemotherapeutic agent is administered to said subject prior to administration of said compound or said composition.

Embodiment 87. The method of embodiment 84, wherein said chemotherapeutic agent is administered to said subject after administration of said compound or said composition.

The invention claimed is:

1. A compound of Formula I:

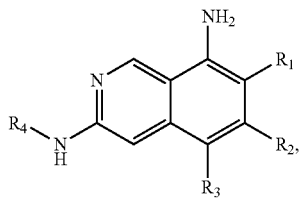

(I)

or a pharmaceutically acceptable salt thereof, wherein, $R_1$ is hydrogen, halogen, cyano, $C_{1-6}$ alkyl, $C_{3-7}$ cycloalkyl, $C_{1-6}$ haloalkyl, $C_{1-6}$ hydroxyalkyl, hydroxyl, $C_{1-6}$ alkoxyl, optionally substituted amino, or optionally substituted acylamino;

$R_2$ is (a), (b), (c), or (d), wherein:
 (a) is a 5-10 membered heteroaryl having 1-4 heteroatoms selected from O, S, and N or a 5-10 membered heterocyclyl having 1-4 heteroatoms selected from O, S, and N, wherein the 5-10 membered heteroaryl and the 5-10 membered heterocyclyl are optionally substituted with one, two, three, four or five substituents;
 (b) is a $C_{6-10}$ aryl optionally substituted with one, two, three, four or five substituents;
 (c) is a $C_{3-8}$ cycloalkyl optionally substituted with one, two, three, four or five substituents;
 (d) is a 5-10 membered heteroaryl fused with a ring selected from the group consisting of 5- or 6-membered heteroaryl, 5-10 membered heterocyclyl, $C_{6-10}$ aryl and $C_{3-7}$ cycloalkyl, wherein the 5-10 membered heteroaryl of $R_2$ and the fused ring are optionally substituted with one, two, three, or four substituents;

$R_3$ is hydrogen, cyano, halogen, optionally substituted $C_{1-6}$ alkyl, optionally substituted $C_{2-9}$ heterocyclyl, or optionally substituted $C_{1-6}$ alkoxy;

$R_4$ is A-C(O)—;

A is $C_{1-6}$ alkyl, $C_{3-7}$ cycloalkyl, $C_{2-9}$ heteroaryl, $C_{2-9}$ heterocyclyl, or —NHR$^g$; wherein the $C_{1-6}$ alkyl, $C_{3-7}$ cycloalkyl, $C_{2-9}$ heteroaryl and $C_{2-9}$ heterocyclyl of A are each optionally substituted independently with one, two, three, four or five substituents; and R$^g$ is $C_{1-6}$ alkyl, $C_{2-6}$ alkenyl, $C_{3-7}$ cycloalkyl, $C_{6-10}$ aryl, $C_{2-9}$ heteroaryl, or $C_{2-9}$ heterocyclyl; wherein the $C_{1-6}$ alkyl, $C_{2-6}$ alkenyl, $C_{3-7}$ cycloalkyl, $C_{6-10}$ aryl, $C_{2-9}$ heteroaryl and $C_{2-9}$ heterocyclyl of R$^g$ are each optionally substituted independently with one, two, three, four or five substituents.

2. The compound of claim 1, or a pharmaceutically acceptable salt thereof, wherein $R_2$ is a 5-10 membered heteroaryl having 1-4 heteroatoms selected from O, S, and N or a 5-10 membered heterocyclyl having 1-4 heteroatoms selected from O, S, and N, wherein the 5-10 membered heteroaryl and the 5-10 membered heterocyclyl are optionally substituted with one, two, three, four or five substituents.

3. The compound of claim 1, or a pharmaceutically acceptable salt thereof, wherein $R_2$ is selected from the group consisting of:

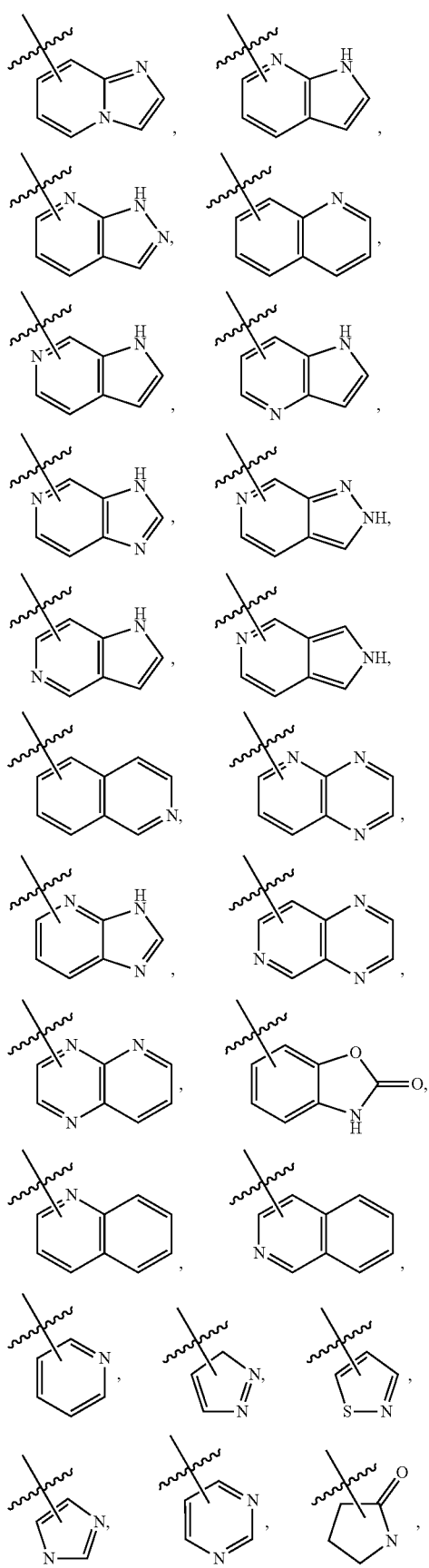
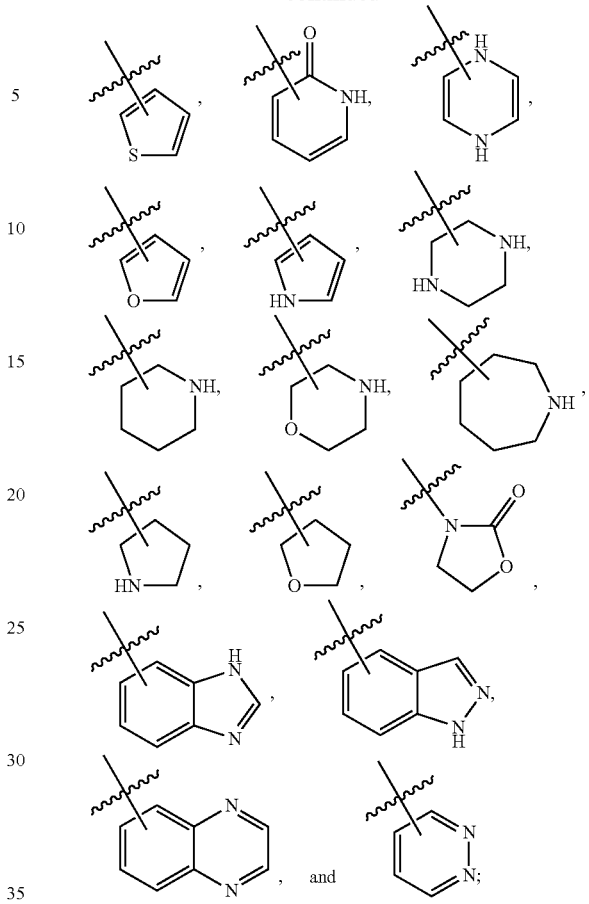
each of which can be optionally substituted with one, two, three, four or five substituents.
4. The compound of claim 1, or a pharmaceutically acceptable salt thereof, wherein $R_2$ is selected from the group consisting of:
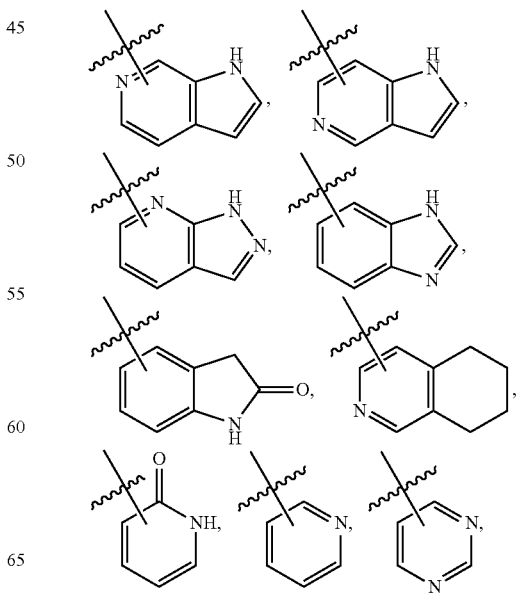

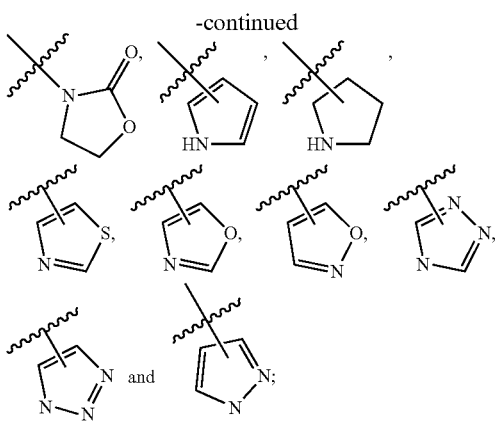

each of which is optionally substituted with one, two, three, four or five substituents.

5. The compound of claim 1, or a pharmaceutically acceptable salt thereof, wherein $R_2$ is:

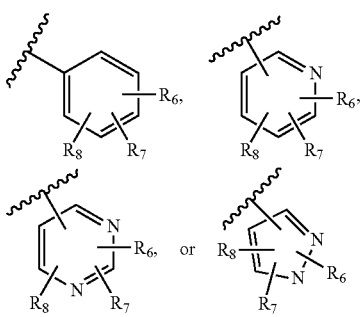

wherein $R_6$, $R_7$, and $R_8$ are each independently selected from the group consisting of:
  i. branched or linear $C_{1-6}$ alkyl or $C_{1-6}$ alkenyl, wherein said alkyl and alkenyl can each be optionally substituted with one, two, three, or four substituents independently selected from the group consisting of hydroxyl, halogen, nitrile, amino, mono($C_{1-6}$ alkyl)amino-, di($C_{1-6}$ alkyl)amino-, —$SO_2R^y$, —$S(O)NR^y$, —(CO)$NR^yR^z$ and —$NR^y(CO)R^z$, wherein $R^y$ and $R^z$, in each instance, is independently hydrogen or $C_{1-6}$ alkyl, wherein each alkyl can optionally be substituted with one, two, three, or four substituents independently selected from the group consisting of hydroxyl and halogen;
  ii. $NR^yR^z$—C(O)—, wherein $R^y$ and $R^z$ are each independently hydrogen or $C_{1-6}$ alkyl, wherein each alkyl can optionally be substituted with one, two, three, or four substituents independently selected from the group consisting of hydroxyl and halogen;
  iii. hydroxy($C_{1-6}$ alkyl);
  iv. $C_{1-6}$ alkoxy, wherein said alkoxy can be optionally substituted with one, two, three, or four substituents independently selected from the group consisting of hydroxyl and halogen;
  v. $C_{3-9}$ cycloalkyl, optionally substituted $C_6$ aryl, optionally substituted 5-membered heteroaryl, or $C_{2-9}$ heterocyclyl;
  vi. halogen;
  vii. amino;
  viii. cyano;
  ix. —$NR^yC(O)R^z$, wherein $R^y$ and $R^z$ are each independently hydrogen or $C_{1-6}$ alkyl, wherein each alkyl can optionally be substituted with one, two, three, or four substituents independently selected from the group consisting of hydroxyl and halogen;
  x. —$SO_2R'$, wherein $R'$ is H or $C_{1-6}$ alkyl;
  xi. —$SO_2NR'R''$, wherein $R'$ and $R''$ are independently H or $C_{1-6}$ alkyl; and
  xii. —$NR'C(O)OR''$, —$NR'SO_2NR''$ or —$NR'S(O)R''$, wherein each $R'$ is independently H or $C_{1-6}$ alkyl and each $R''$ is independently $C_{1-6}$ alkyl, halo($C_{1-6}$ alkyl) or $C_{6-10}$ aryl optionally substituted with $C_{1-6}$ alkyl.

6. The compound of claim 5, or a pharmaceutically acceptable salt thereof, wherein $R_2$ is:

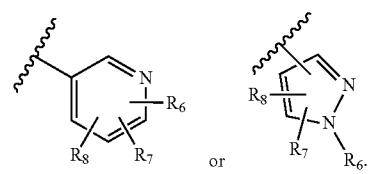

7. The compound of claim 6, or a pharmaceutically acceptable salt thereof, wherein $R_2$ is:

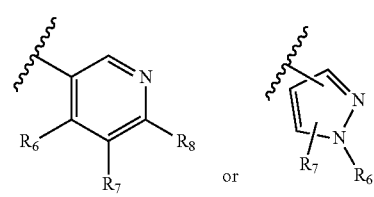

8. The compound of claim 1, or a pharmaceutically acceptable salt thereof, wherein $R_2$ is:

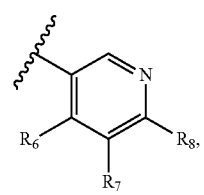

wherein $R_6$, $R_7$, and $R_8$ are each independently selected from the group consisting of hydrogen, hydroxyl, amino, $C_{1-6}$ alkyl, $C_{1-6}$ alkoxy, and mono($C_{1-6}$ alkyl)amino.

9. The compound of claim 8, or a pharmaceutically acceptable salt thereof, wherein $R_6$ is $C_{1-6}$ alkyl; $R_7$ is hydrogen, amino, or mono($C_{1-6}$ alkyl)amino; and $R_8$ is hydrogen, hydroxyl, or $C_{1-6}$ alkoxy.

10. The compound of claim 9, or a pharmaceutically acceptable salt thereof, wherein $R_6$ is methyl.

11. The compound of claim 10, or a pharmaceutically acceptable salt thereof, wherein $R_7$ is amino.

12. The compound of claim 1, or a pharmaceutically acceptable salt thereof, wherein $R_2$ is

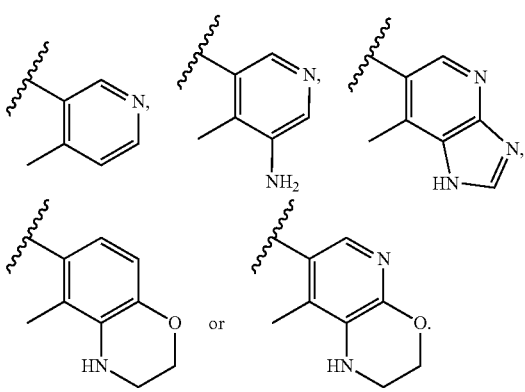

13. The compound of claim 1, or a pharmaceutically acceptable salt thereof, wherein A is:

i. $C_{3-7}$ cycloalkyl, $C_{2-9}$ heteroaryl, or $C_{2-9}$ heterocyclyl, wherein said cycloalkyl, heteroaryl, or heterocyclyl can each be optionally substituted with one, two, three or four of $R_5$, wherein each $R_5$ is independently selected from the group consisting of $C_{1-6}$ alkyl, $C_{3-7}$ cycloalkyl, $C_{2-6}$ alkenyl, halogen, cyano, hydroxyl, $C_{1-6}$ alkoxy, optionally substituted $C_{2-9}$ heteroaryl, —SO$_2$R$^e$, —NR$^e$C(O)R$^f$, —NR$^e$SO$_2$R$^f$ and NR$^e$R$^f$—C(O)—; wherein the $C_{1-6}$ alkyl, $C_{3-7}$ cycloalkyl, and $C_{2-6}$ alkenyl of $R_5$ can each be optionally substituted with one, two, three, or four substituents independently selected from the group consisting of $C_{1-6}$ alkoxy, hydroxyl, halogen, cyano, —SO$_2$R$^e$, —NR$^e$R$^f$, —NR$^e$C(O)R$^f$ and —C(O)NR$^e$R$^f$, wherein R$^e$ and R$^f$ in each occurrence are independently selected from the group consisting of hydrogen, branched or linear $C_{1-6}$ alkyl and $C_{3-7}$ cycloalkyl;

or, said cycloalkyl or heterocyclyl together with two of $R_5$ form a bicyclic or spiro ring system, wherein two of $R_5$ attached to different atoms are taken together with the carbon to which each is attached to form a bicyclic ring system, or two of $R_5$ attached to the same carbon are taken together with the carbon to which each is attached to form a spiro ring system;

ii. —NHR$^g$, wherein R$^g$ is selected from the group consisting of:

a. branched or linear $C_{1-6}$ alkyl, $C_{2-6}$ alkenyl, $C_{2-9}$ heterocyclyl, or $C_{3-7}$ cycloalkyl, wherein each alkyl, alkenyl, heterocyclyl and cycloalkyl can be optionally substituted with one, two, three, or four substituents independently selected from the group consisting of hydroxyl, halogen, —CHF$_2$, —CF$_3$, amino, di($C_{1-6}$ alkyl)amino, mono($C_{1-6}$ alkyl)amino, cyano, $C_{3-7}$ cycloalkyl, $C_{1-6}$ alkoxy, —SO$_2$R', —SO$_2$NR'R", —C(O)NR'R", —NR'C(O)R", —NR'C(O)OR", —NR'C(O)NR"R'", —NR'SO$_2$NR"R'" and —NR'S(O)R", wherein each R' and R'" is independently H or $C_{1-6}$ alkyl and each R" is independently $C_{1-6}$ alkyl, halo($C_{1-6}$ alkyl) or $C_{6-10}$ aryl optionally substituted with $C_{1-6}$ alkyl; or R" and R'" are taken together with the nitrogen to which they are attached to form an optionally substituted heterocyclyl; and b. $C_{2-9}$ heteroaryl or $C_{6-10}$ aryl wherein said heteroaryl has 1-4 heteroatoms selected from O, S and N; and wherein each aryl and heteroaryl can be optionally substituted with one, two, three or four substituents independently selected from the group consisting of branched or linear $C_{1-6}$ alkyl, $C_{1-6}$ alkenyl, $C_{2-9}$ heterocyclyl, $C_{3-7}$ cycloalkyl, hydroxyl, halogen, —CHF$_2$, —CF$_3$, amino, di($C_{1-6}$ alkyl)amino, mono ($C_{1-6}$ alkyl)amino, cyano, $C_{3-7}$ cycloalkyl, $C_{1-6}$ alkoxy, —SO$_2$R',—SO$_2$NR'R", —C(O)NR'R", and —NR'C(O)R", wherein each R' and R" is independently H or $C_{1-6}$ alkyl; or iii. $C_{1-6}$ alkyl optionally substituted with one, two, three, or four substituents independently selected from the group consisting of hydroxyl, halogen, cyano, $C_{1-6}$ alkoxy, amino, mono($C_{1-6}$ alkyl)amino, di($C_{1-6}$ alkyl) amino, $C_{3-7}$ cycloalkyl, $C_{6-10}$ aryl, 5-10 membered heteroaryl, 5-10 membered heterocyclyl, —SO$_2$R', —SO$_2$NR'R", —C(O)NR'R", —NR'C(O)R", —NR'C(O)OR", —NR'C(O)NR"R'", —NR'SO$_2$NR"R'" and —NR'S(O)R";

wherein each R' and R'" is independently H or $C_{1-6}$ alkyl and each R" is independently $C_{1-6}$ alkyl, halo ($C_{1-6}$ alkyl) or $C_{6-10}$ aryl optionally substituted with $C_{1-6}$ alkyl; or R" and R'" are taken together with the nitrogen to which they are attached to form an optionally substituted $C_{3-7}$ heterocyclyl.

14. The compound of claim 13, or a pharmaceutically acceptable salt thereof, wherein A is $C_{3-7}$ cycloalkyl optionally substituted with one, two, three or four of $R_5$.

15. The compound of claim 14, or a pharmaceutically acceptable salt thereof, wherein $R_4$ is:

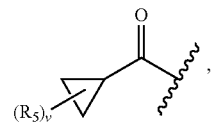

wherein, v is 0, 1, 2 or 3; and each $R_5$ is independently selected from the group consisting of $C_{1-6}$ alkyl, $C_{3-7}$ cycloalkyl, $C_{2-6}$ alkenyl, halogen, cyano, hydroxyl, $C_{1-6}$ alkoxy, optionally substituted $C_{2-9}$ heteroaryl, —SO$_2$R$^e$, —NR$^e$R$^f$, —NR$^e$C(O)R$^f$, —NR$^e$SO$_2$R$^f$ and NR$^e$R$^f$—C(O)—; wherein the $C_{1-6}$ alkyl, $C_{3-7}$ cycloalkyl, and $C_{2-6}$ alkenyl, of $R_5$ can each be optionally substituted with one, two, three, or four substituents independently selected from the group consisting of $C_{1-6}$ alkoxy, hydroxyl, halogen, cyano, -SO$_2$R$^e$, —NR$^e$R$^f$, —NR$^e$C(O)R$^f$ and —C(O)NR$^e$R$^f$, wherein R$^e$ and R$^f$ in each occurrence are independently selected from the group consisting of hydrogen, branched or linear $C_{1-6}$ alkyl and $C_{3-7}$ cycloalkyl.

16. The compound of claim 15, or a pharmaceutically acceptable salt thereof, wherein each $R_5$ is independently selected from the group consisting of $C_{1-6}$ alkyl, $C_{3-7}$ cycloalkyl, halogen, cyano, hydroxyl, $C_{1-6}$ alkoxy, and $C_{2-9}$ heteroaryl, wherein each alkyl, cycloalkyl, and heteroaryl is optionally substituted.

17. The compound of claim 16, or a pharmaceutically acceptable salt thereof, wherein at least one $R_5$ is $C_{1-6}$ alkyl.

18. The compound of claim 17, or a pharmaceutically acceptable salt thereof, wherein said $C_{1-6}$ alkyl is methyl or ethyl.

19. The compound of claim 16, or a pharmaceutically acceptable salt thereof, wherein one of $R_5$ is optionally substituted $C_{2-9}$ heteroaryl.

20. The compound of claim 19, or a pharmaceutically acceptable salt thereof, wherein said optionally substituted $C_{2-9}$ heteroaryl is an optionally substituted $C_3$ heteroaryl.

21. The compound of claim 20, or a pharmaceutically acceptable salt thereof, wherein said optionally substituted $C_3$ heteroaryl is an optionally substituted pyrazole.

22. The compound of claim 21, or a pharmaceutically acceptable salt thereof, wherein said optionally substituted pyrazole is

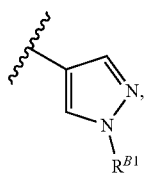

wherein the wavy line denotes the point of attachment to the cyclopropyl ring; and wherein $R^{B1}$ is $C_{1-6}$ alkyl.

23. The compound of claim 16, or a pharmaceutically acceptable salt thereof, wherein $R_4$ is:

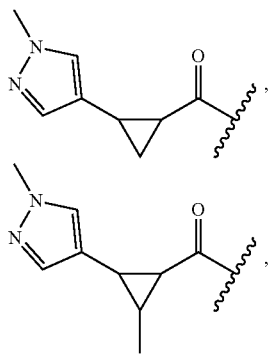

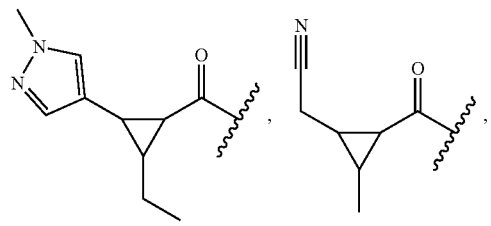

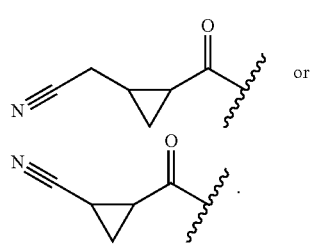

24. The compound of claim 1, or a pharmaceutically acceptable salt thereof, wherein $R_1$ is hydrogen, halogen, or methyl.

25. The compound of claim 24, or a pharmaceutically acceptable salt thereof, wherein $R_1$ is fluoro.

26. The compound of claim 1, or a pharmaceutically acceptable salt thereof, wherein $R_3$ is hydrogen.

27. The compound of claim 1, or a pharmaceutically acceptable salt thereof, wherein the compound is selected from the group consisting of:

| No. | Structure | Name |
|---|---|---|
| 1 | 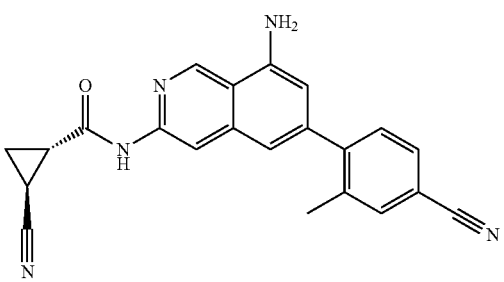 [SMILES: Cc1cc(C#N)ccc1-c1cc(N)c2cnc(NC(=O)[C@H]3C[C@@H]3C#N)cc2c1] | trans-N-[8-amino-6-(4-cyano-2-methyl-phenyl)-3-isoquinolyl]-2-cyano-cyclopropane-1-carboxamide; |
|  | 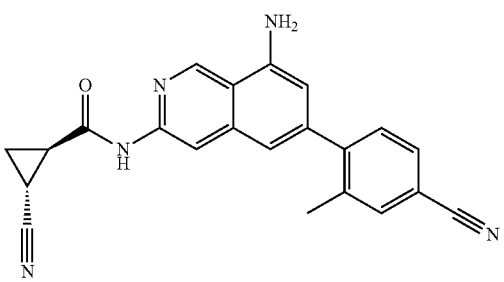 [SMILES: Cc1cc(C#N)ccc1-c1cc(N)c2cnc(NC(=O)[C@@H]3C[C@H]3C#N)cc2c1] |  |

-continued

| No. | Structure | Name |
|---|---|---|
| 2 | 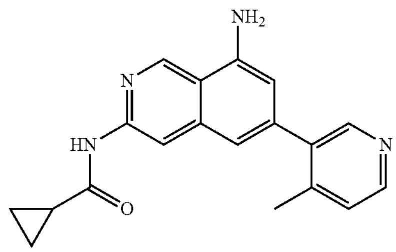 [SMILES: Cc1ccncc1-c1cc(N)c2cnc(NC(=O)C3CC3)cc2c1] | N-(8-amino-6-(4-methylpyridin-3-yl)isoquinolin-3-yl)cyclopropanecarboxamide; |
| 3 | | cis-N-[8-amino-6-[4-(hydroxymethyl)-3-pyridyl]-3-isoquinolyl]-2-fluoro-cyclopropane-1-carboxamide; |
| | | |
| 4 | 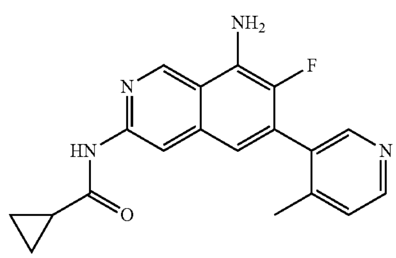 [SMILES: Cc1ccncc1-c1cc2cc(NC(=O)C3CC3)ncc2c(N)c1F] | N-(8-amino-7-fluoro-6-(4-methylpyridin-3-yl)isoquinolin-3-yl)cyclopropanecarboxamide; |
| 5 | 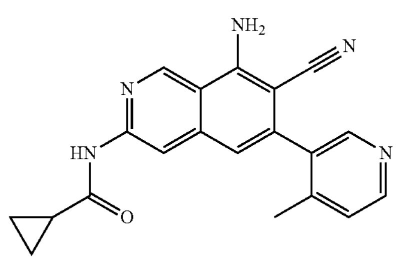 [SMILES: Cc1ccncc1-c1cc2cc(NC(=O)C3CC3)ncc2c(N)c1C#N] | N-(8-amino-7-cyano-6-(4-methylpyridin-3-yl)isoquinolin-3-yl)cyclopropanecarboxamide; |
| 6 | 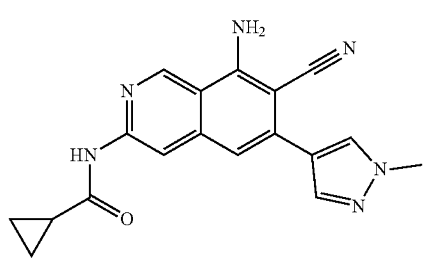 [SMILES: Cn1cc(-c2cc3cc(NC(=O)C4CC4)ncc3c(N)c2C#N)cn1] | N-(8-amino-7-cyano-6-(1-methyl-1H-pyrazol-4-yl)isoquinolin-3-yl)cyclopropanecarboxamide; |

-continued
| No. | Structure | Name |
|---|---|---|
| 13 | 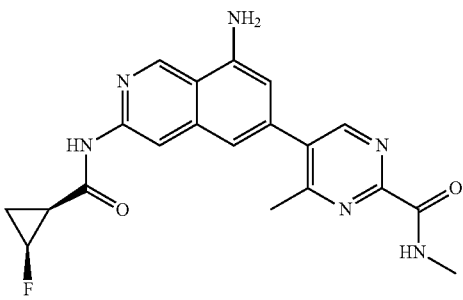 | 5-[8-amino-3-[(cis-2-fluorocyclopropanecarbonyl)amino]-6-isoquinolyl]-N,4-dimethyl-pyrimidine-2-carboxamide; |
| 14 | 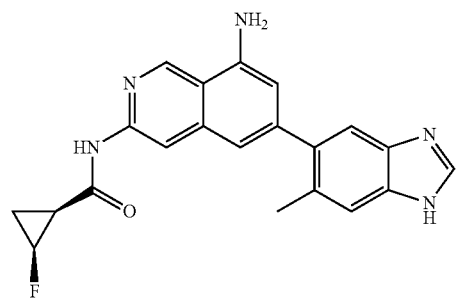 [SMILES: Cc1cc2[nH]cnc2cc1-c1cc(N)c2cnc(NC(=O)[C@@H]3C[C@@H]3F)cc2c1] | cis-N-(8-amino-6-(6-methyl-1H-benzo[d]imidazol-5-yl)isoquinolin-3-yl)-2-fluorocyclopropane-1-carboxamide; |
| 15 | 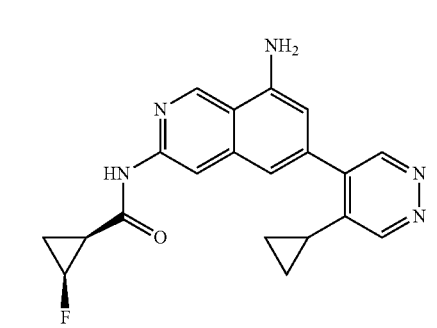 [SMILES: Nc1cc(-c2cnncc2C2CC2)cc2cc(NC(=O)[C@@H]3C[C@@H]3F)ncc12] | cis-N-(8-amino-6-(5-cyclopropylpyridazin-4-yl)isoquinolin-3-yl)-2-fluorocyclopropane-1-carboxamide; |

| No. | Structure | Name |
|---|---|---|
| | 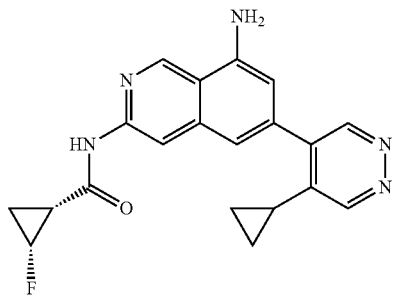 [SMILES: Nc1cc(-c2cnncc2C2CC2)cc2cc(NC(=O)[C@H]3C[C@H]3F)ncc12] | |
| 16 | 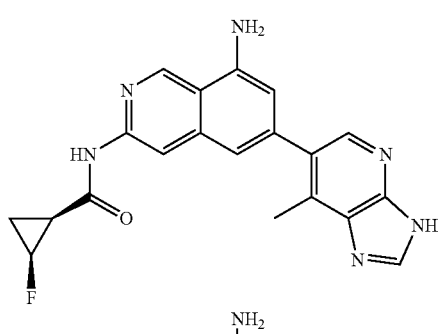 | cis-N-(8-amino-6-(7-methyl-3H-imidazo[4,5-b]pyridin-6-yl)isoquinolin-3-yl)-2-fluorocyclopropane-1-carboxamide; |
| | 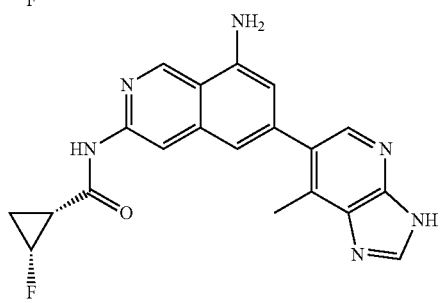 | |
| 17 | 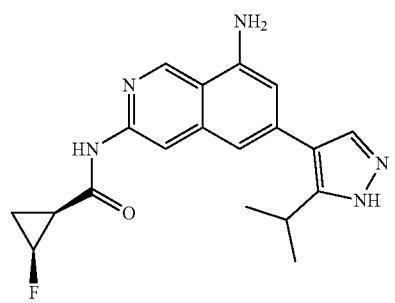 [SMILES: CC(C)c1[nH]ncc1-c1cc(N)c2cnc(NC(=O)[C@@H]3C[C@@H]3F)cc2c1] | cis-N-(8-amino-6-(5-isopropyl-1H-pyrazol-4-yl)isoquinolin-3-yl)-2-fluorocyclopropane-1-carboxamide; |
| | 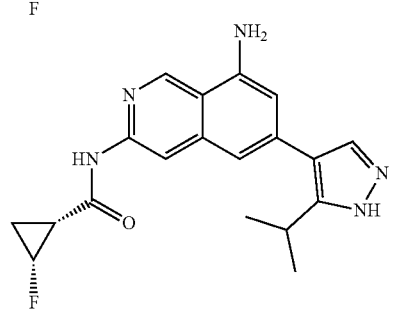 | |

-continued

| No. | Structure | Name |
|---|---|---|
| 18 | 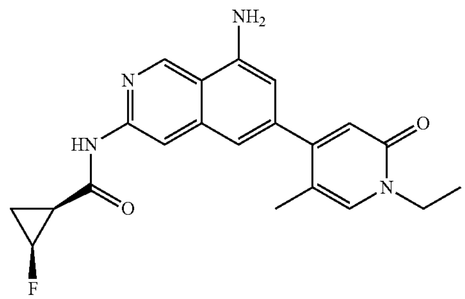 [SMILES: CCn1cc(C)c(-c2cc(N)c3cnc(NC(=O)[C@@H]4C[C@@H]4F)cc3c2)cc1=O] | cis-N-(8-amino-6-(1-ethyl-5-methyl-2-oxo-1,2-dihydropyridin-4-yl)isoquinolin-3-yl)-2-fluorocyclopropane-1-carboxamide; |
| | | |
| 19 | 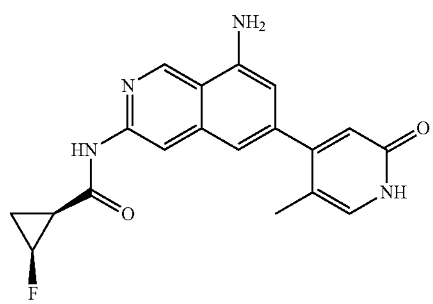 [SMILES: Cc1c[nH]c(=O)cc1-c1cc(N)c2cnc(NC(=O)[C@@H]3C[C@@H]3F)cc2c1] | cis-N-(8-amino-6-(5-methyl-2-oxo-1,2-dihydropyridin-4-yl)isoquinolin-3-yl)-2-fluorocyclopropane-1-carboxamide; |
| | | |
| 20 | 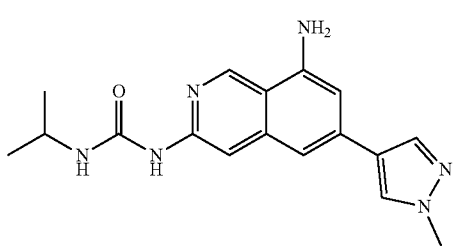 [SMILES: CC(C)NC(=O)Nc1cc2cc(-c3cnn(C)c3)cc(N)c2cn1] | 1-(8-amino-6-(1-methyl-1H-pyrazol-4-yl)isoquinolin-3-yl)-3-isopropylurea; |

| No. | Structure | Name |
|-----|-----------|------|
| 21 | | trans--N-[8-amino-6-(1-methylpyrrolo[2,3-b]pyridin-4-yl)-3-isoquinolyl]-2-cyano-cyclopropane-1-carboxamide; |
| | | |
| 22 | | trans-N-[8-amino-6-(1H-pyrrolo[2,3-b]pyridin-4-yl)-3-isoquinolyl]-2-cyano-cyclopropane-1-carboxamide; |
| | | |
| 23 | 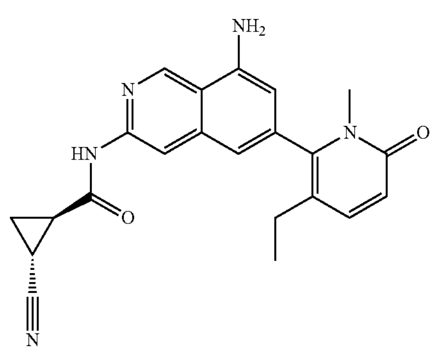 | trans-N-[8-amino-6-(3-ethyl-1-methyl-6-oxo-2-pyridyl)-3-isoquinolyl]-2-cyano-cyclopropane-1-carboxamide; |

| No. | Structure | Name |
|---|---|---|
| | 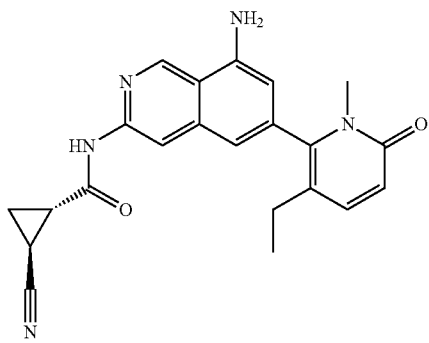 [SMILES: CCc1ccc(=O)n(C)c1-c1cc(N)c2cnc(NC(=O)[C@H]3C[C@@H]3C#N)cc2c1] | |
| 24 | 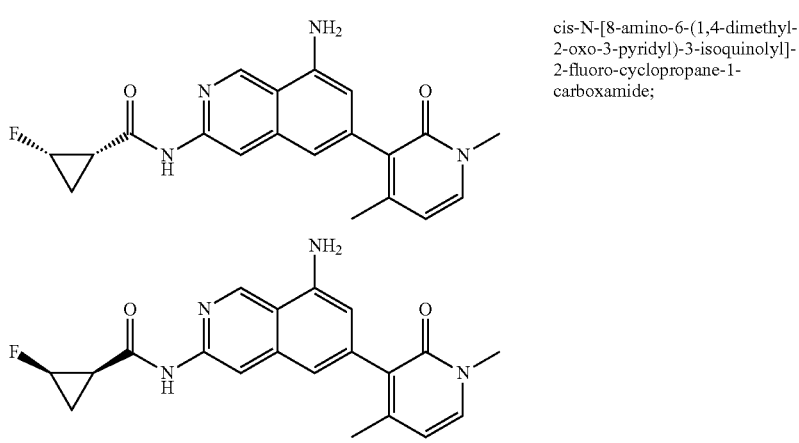 | cis-N-[8-amino-6-(1,4-dimethyl-2-oxo-3-pyridyl)-3-isoquinolyl]-2-fluoro-cyclopropane-1-carboxamide; |
| 25 | 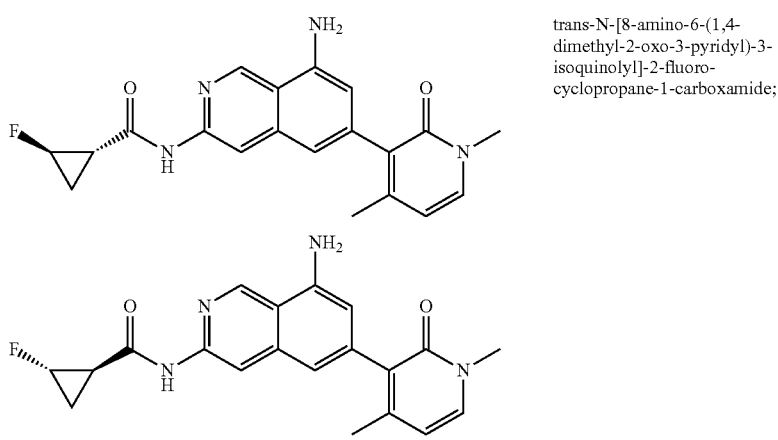 | trans-N-[8-amino-6-(1,4-dimethyl-2-oxo-3-pyridyl)-3-isoquinolyl]-2-fluoro-cyclopropane-1-carboxamide; |
| 26 | 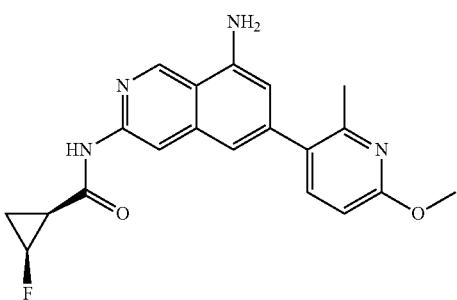 [SMILES: COc1ccc(-c2cc(N)c3cnc(NC(=O)[C@@H]4C[C@@H]4F)cc3c2)c(C)n1] | cis-N-(8-amino-6-(6-methoxy-2-methylpyridin-3-yl)isoquinolin-3-yl)-2-fluorocyclopropane-1-carboxamide; |

-continued
| No. | Structure | Name |
|---|---|---|
| | 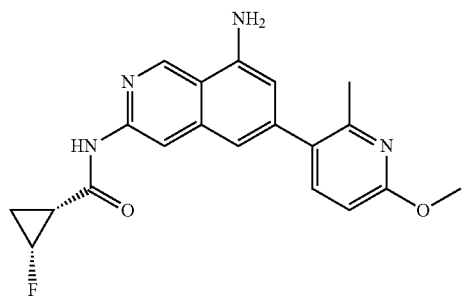 [SMILES: COc1ccc(-c2cc(N)c3cnc(NC(=O)[C@H]4C[C@H]4F)cc3c2)c(C)n1] | |
| 27 | 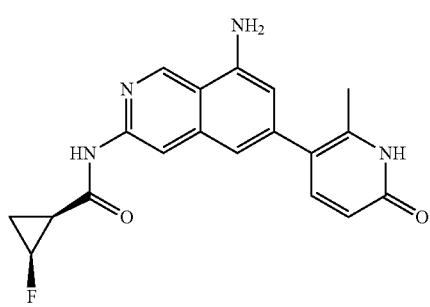 [SMILES: Cc1[nH]c(=O)ccc1-c1cc(N)c2cnc(NC(=O)[C@@H]3C[C@@H]3F)cc2c1] | cis-N-(8-amino-6-(2-methyl-6-oxo-1,6-dihydropyridin-3-yl)isoquinolin-3-yl)-2-fluorocyclopropane-1-carboxamide; |
| | 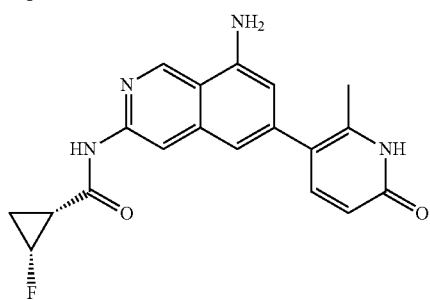 | |
| 28 | 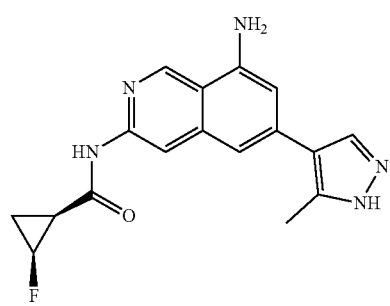 [SMILES: Cc1[nH]ncc1-c1cc(N)c2cnc(NC(=O)[C@@H]3C[C@@H]3F)cc2c1] | cis-N-(8-amino-6-(5-methyl-1H-pyrazol-4-yl)isoquinolin-3-yl)-2-fluorocyclopropane-1-carboxamide; |
| | 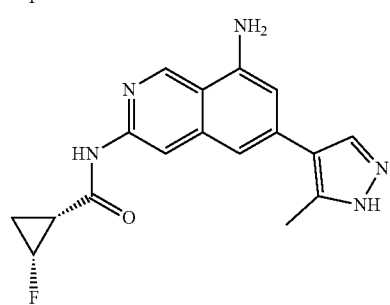 | |

-continued

| No. | Structure | Name |
|---|---|---|
| 30 | 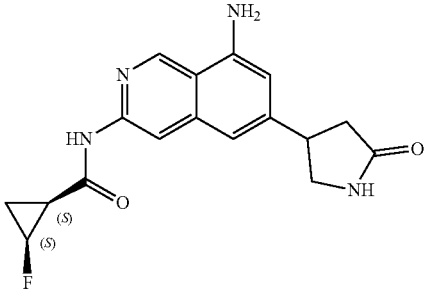 | (1S,2S)-N-(8-amino-6-(5-oxopyrrolidin-3-yl)isoquinolin-3-yl)-2-fluorocyclopropane-1-carboxamide; |
| 31 | 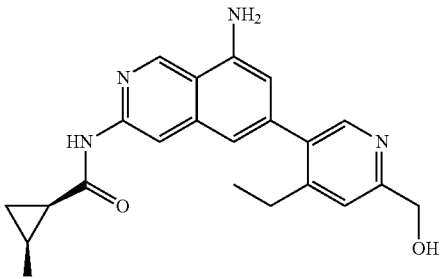 | cis-N-(8-amino-6-(4-ethyl-6-(hydroxymethyl)pyridin-3-yl)isoquinolin-3-yl)-2-fluorocyclopropane-1-carboxamide; |
| 32 | 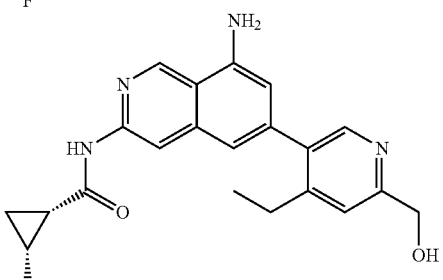 | trans-N-(8-amino-6-(4-methylpyridin-3-yl)isoquinolin-3-yl)-2-cyanocyclopropane-1-carboxamide; |
| 37, 108 | 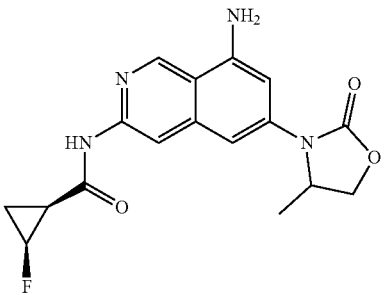 [SMILES: CC1COC(=O)N1c1cc(N)c2cnc(NC(=O)[C@@H]3C[C@@H]3F)cc2c1] | (1S,2S)-N-(8-amino-6-(4-methyl-2-oxooxazolidin-3-yl)isoquinolin-3-yl)-2-fluorocyclopropane-1-carboxamide; |

| No. | Structure | Name |
|---|---|---|
| 38 | 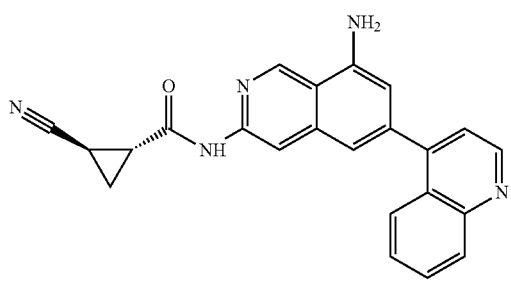 [SMILES: N#C[C@@H]1C[C@H]1C(=O)Nc1cc2cc(-c3ccnc4ccccc34)cc(N)c2cn1] | trans-N-(8-amino-6-(quinolin-4-yl)isoquinolin-3-yl)-2-cyanocyclopropane-1-carboxamide; |
| 39 | 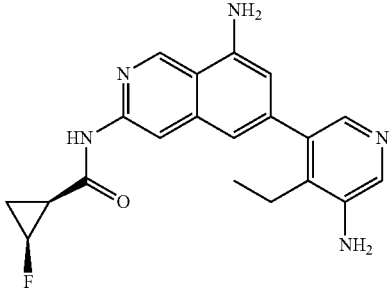 [SMILES: CCc1c(N)cncc1-c1cc(N)c2cnc(NC(=O)[C@@H]3C[C@@H]3F)cc2c1] | cis-N-(8-amino-6-(5-amino-4-ethylpyridin-3-yl)isoquinolin-3-yl)-2-fluorocyclopropane-1-carboxamide; |
|  | 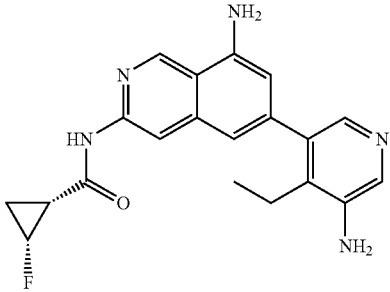 [SMILES: CCc1c(N)cncc1-c1cc(N)c2cnc(NC(=O)[C@H]3C[C@H]3F)cc2c1] |  |
| 40 | 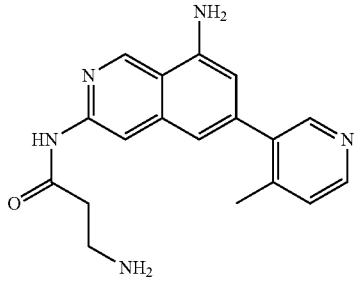 [SMILES: Cc1ccncc1-c1cc(N)c2cnc(NC(=O)CCN)cc2c1] | 3-amino-N-(8-amino-6-(4-methylpyridin-3-yl)isoquinolin-3-yl)propanamide; |

| No. | Structure | Name |
|---|---|---|
| 41 | | cis-N-(8-amino-6-(5-isopropyl-1H-pyrazol-4-yl)isoquinolin-3-yl)-2-fluoro-cyclopropane-1-carboxamide; |
| 42 | | trans-N-(8-amino-6-(5-isopropyl-1H-pyrazol-4-yl)isoquinolin-3-yl)-2-fluorocyclopropane-1-carboxamide; |
| 43 | 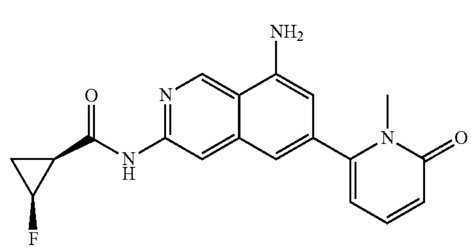 [SMILES: Cn1c(-c2cc(N)c3cnc(NC(=O)[C@@H]4C[C@@H]4F)cc3c2)cccc1=O] | cis-N-(8-amino-6-(1-methyl-6-oxo-1,6-dihydropyridin-2-yl)isoquinolin-3-yl)-2-fluorocyclopropane-1-carboxamide; |

| No. | Structure | Name |
|---|---|---|
| | 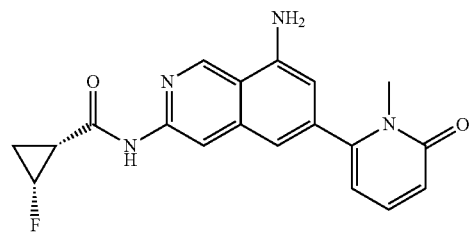 [SMILES: Cn1c(-c2cc(N)c3cnc(NC(=O)[C@H]4C[C@H]4F)cc3c2)cccc1=O] | |
| 44 | 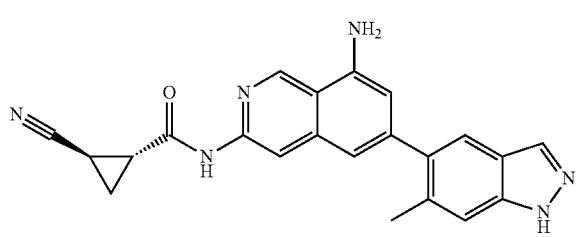 [SMILES: Cc1cc2[nH]ncc2cc1-c1cc(N)c2cnc(NC(=O)[C@@H]3C[C@H]3C#N)cc2c1] | trans-N-[8-amino-6-(6-methyl-1H-indazol-5-yl)-3-isoquinolyl]-2-cyano-cyclopropane-1-carboxamide; |
| | 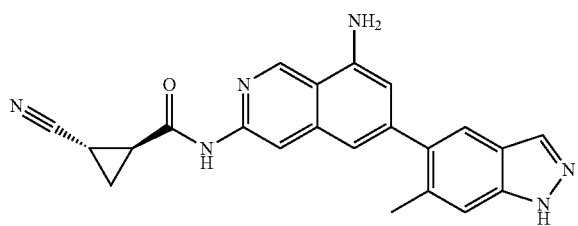 [SMILES: Cc1cc2[nH]ncc2cc1-c1cc(N)c2cnc(NC(=O)[C@H]3C[C@@H]3C#N)cc2c1] | |
| 45 | 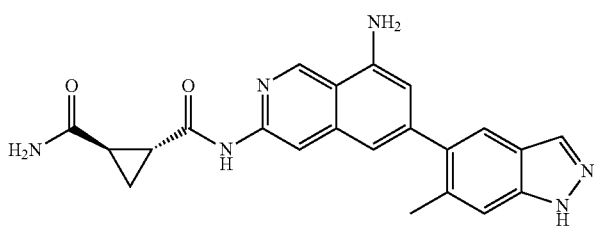 | trans-N1-[8-amino-6-(6-methyl-1H-indazol-5-yl)-3-isoquinolyl]cyclopropane-1,2-dicarboxamide; |
| | 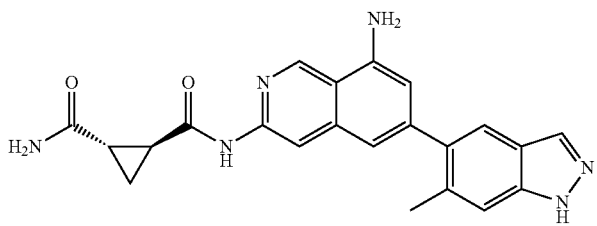 [SMILES: Cc1cc2[nH]ncc2cc1-c1cc(N)c2cnc(NC(=O)[C@H]3C[C@@H]3C(N)=O)cc2c1] | |
| 46 | 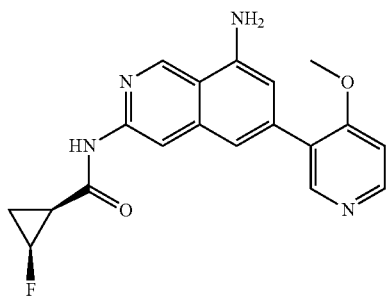 [SMILES: COc1ccncc1-c1cc(N)c2cnc(NC(=O)[C@@H]3C[C@@H]3F)cc2c1] | cis-N-(8-amino-6-(4-methoxypyridin-3-yl)isoquinolin-3-yl)-2-fluorocyclopropane-1-carboxamide; |

| No. | Structure | Name |
|---|---|---|
| | (structure) | |
| 47 | (structure) | trans-N-(8-amino-6-(4-methoxypyridin-3-yl)isoquinolin-3-yl)-2-fluorocyclopropane-1-carboxamide; |
| | (structure) | |
| 48 | (structure) | cis-N-[8-amino-6-(2-hydroxy-4-methyl-3-pyridyl)-3-isoquinolyl]-2-fluoro-cyclopropane-1-carboxamide; |
| | (structure) | |
| 49 | (structure) | cis-N-[8-amino-6-(5-fluoro-4-methyl-3-pyridyl)-3-isoquinolyl]-2-fluoro-cyclopropane-1-carboxamide; |

| No. | Structure | Name |
|---|---|---|
| | 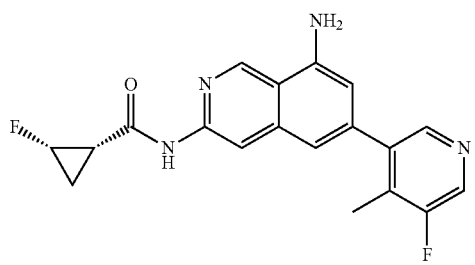 [SMILES: Cc1c(F)cncc1-c1cc(N)c2cnc(NC(=O)[C@@H]3C[C@@H]3F)cc2c1] | |
| 50 | 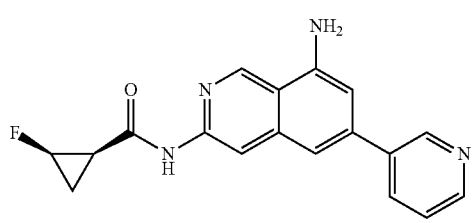 [SMILES: Nc1cc(-c2cccnc2)cc2cc(NC(=O)[C@H]3C[C@H]3F)ncc12] | cis-N-[8-amino-6-(3-pyridyl)-3-isoquinolyl]-2-fluoro-cyclopropane-1-carboxamide; |
| 51 | 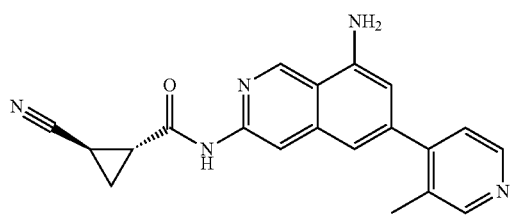 [SMILES: Cc1cnccc1-c1cc(N)c2cnc(NC(=O)[C@@H]3C[C@H]3C#N)cc2c1] | trans-N-[8-amino-6-(3-methyl-4-pyridyl)-3-isoquinolyl]-2-cyano-cyclopropane-1-carboxamide; |
| 52, 102 | 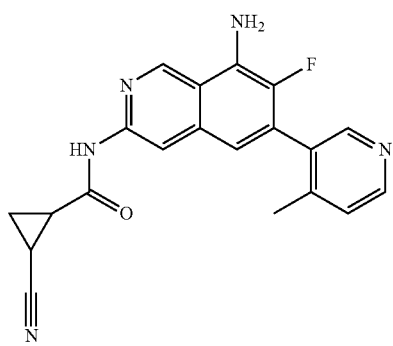 [SMILES: Cc1ccncc1-c1cc2cc(NC(=O)C3CC3C#N)ncc2c(N)c1F] | trans-N-[8-amino-7-fluoro-6-(4-methyl-3-pyridyl)-3-isoquinolyl]-2-cyano-cyclopropane-1-carboxamide; |

| No. | Structure | Name |
|---|---|---|
| | 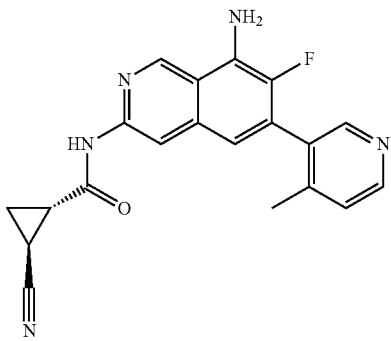 [SMILES: Cc1ccncc1-c1cc2cc(NC(=O)[C@H]3C[C@@H]3C#N)ncc2c(N)c1F] | |
| | 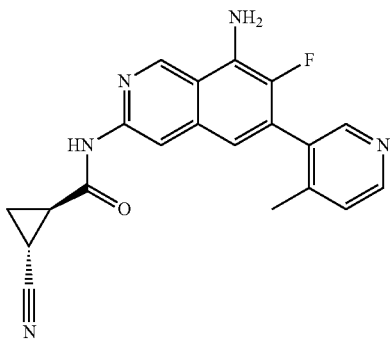 | |
| 54, 92, 93 | 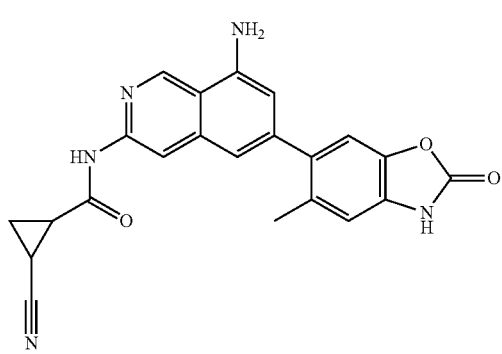 [SMILES: Cc1cc2[nH]c(=O)oc2cc1-c1cc(N)c2cnc(NC(=O)C3CC3C#N)cc2c1] | trans-N-(8-amino-6-(5-methyl-2-oxo-2,3-dihydrobenzo[d]oxazol-6-yl)isoquinolin-3-yl)-2-cyanocyclopropane-1-carboxamide; |
| | 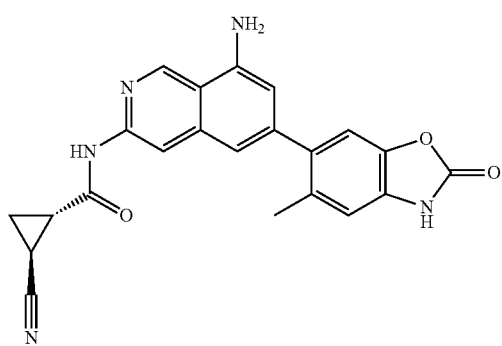 | |

| No. | Structure | Name |
|---|---|---|
| | | |
| 55 | | cis-N-(8-amino-6-(2-ethyl-5-oxopyrrolidin-1-yl)isoquinolin-3-yl)-2-fluorocyclopropane-1-carboxamide; |
| 56 | | trans-N-(8-amino-6-(4-ethylpyridin-3-yl)-2,7-naphthyridin-3-yl)-2-cyanocyclopropane-1-carboxamide; |

| No. | Structure | Name |
|---|---|---|
| 57 | 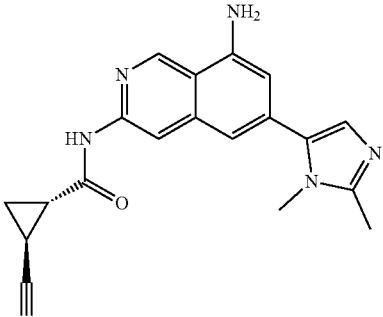 | trans-N-(8-amino-6-(1,2-dimethyl-1H-imidazol-5-yl)isoquinolin-3-yl)-2-cyanocyclopropane-1-carboxamide; |
| | 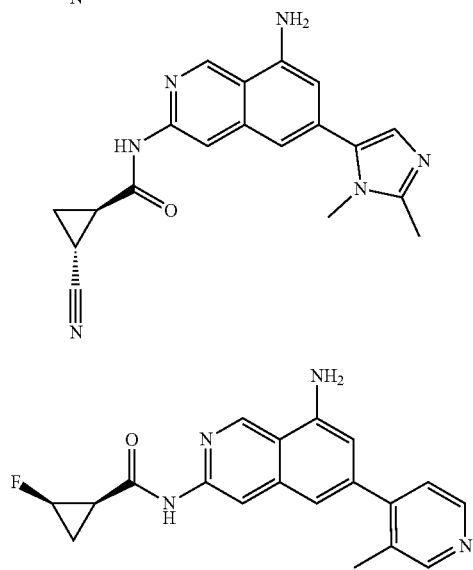 | |
| 59 | 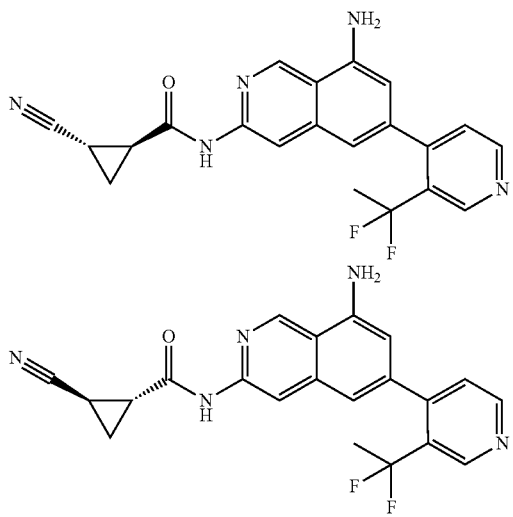 | cis-N-[8-amino-6-(3-methyl-4-pyridyl)-3-isoquinolyl]-2-fluoro-cyclopropane-1-carboxamide; |
| 60 | 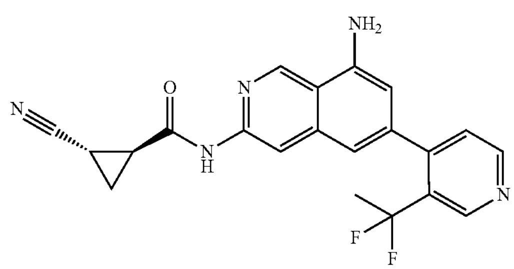 [SMILES: CC(F)(F)c1cnccc1-c1cc(N)c2cnc(NC(=O)[C@H]3C[C@@H]3C#N)cc2c1] | trans-N-(8-amino-6-(4-(1,1-difluoroethyl)pyridin-3-yl)isoquinolin-3-yl)-2-cyanocyclopropane-1-carboxamide; |

| No. | Structure | Name |
|---|---|---|
| 61 | 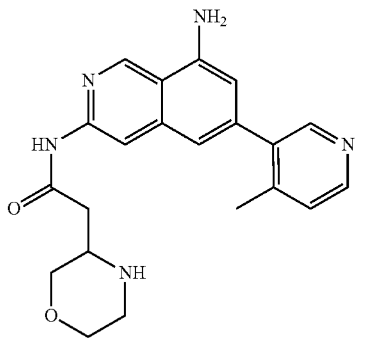 [SMILES: Cc1ccncc1-c1cc(N)c2cnc(NC(=O)CC3COCCN3)cc2c1] | N-(8-amino-6-(4-methylpyridin-3-yl)isoquinolin-3-yl)-2-(morpholin-3-yl)acetamide; |
| 62 | | trans-N-(8-amino-6-(4-methylisothiazol-5-yl)isoquinolin-3-yl)-2-cyanocyclopropane-1-carboxamide; |
| 63 | 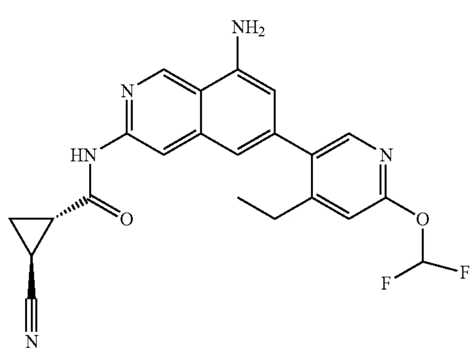 [SMILES: CCc1cc(OC(F)F)ncc1-c1cc(N)c2cnc(NC(=O)[C@H]3C[C@@H]3C#N)cc2c1] | trans-N-[8-amino-6-[6-(difluoromethoxy)-4-ethyl-3-pyridyl]-3-isoquinolyl]-2-cyanocyclopropane-1-carboxamide; |

-continued
| No. | Structure | Name |
|---|---|---|
| | 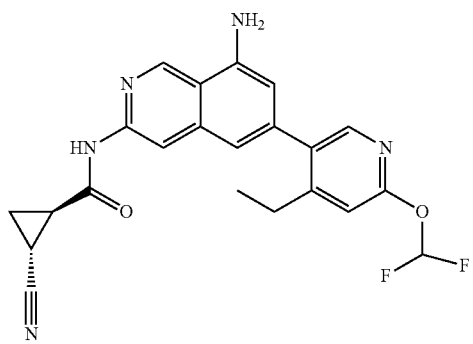 [SMILES: CCc1cc(OC(F)F)ncc1-c1cc(N)c2cnc(NC(=O)[C@@H]3C[C@H]3C#N)cc2c1] | |
| 65, 94, 95 | 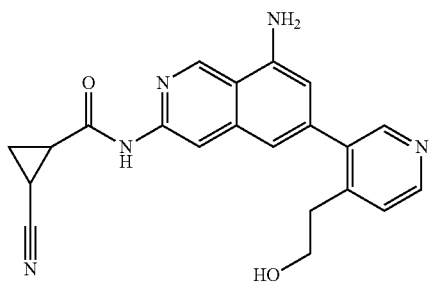 [SMILES: N#CC1CC1C(=O)Nc1cc2cc(-c3cnccc3CCO)cc(N)c2cn1] | trans-N-[8-amino-6-[4-(2-hydroxyethyl)-3-pyridyl]-3-isoquinolyl]-2-cyanocyclopropane-1-carboxamide; |
| | 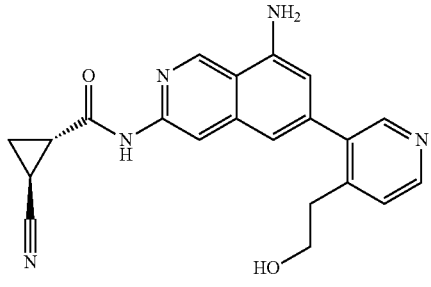 [SMILES: N#C[C@H]1C[C@@H]1C(=O)Nc1cc2cc(-c3cnccc3CCO)cc(N)c2cn1] | |
| | 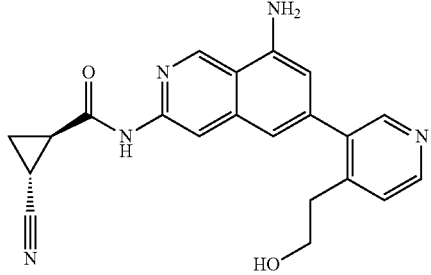 [SMILES: N#C[C@@H]1C[C@H]1C(=O)Nc1cc2cc(-c3cnccc3CCO)cc(N)c2cn1] | |
| 66 | 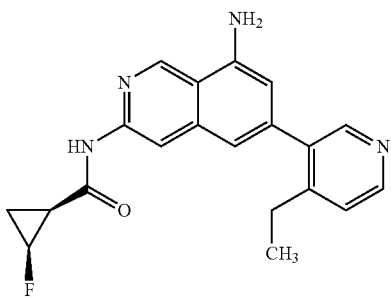 | (1S,2S)-N-(8-amino-6-(4-ethylpyridin-3-yl)isoquinolin-3-yl)-2-fluorocyclopropane-1-carboxamide; |

| No. | Structure | Name |
|---|---|---|
| 67, 71, 72 | 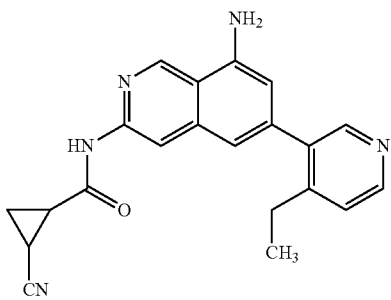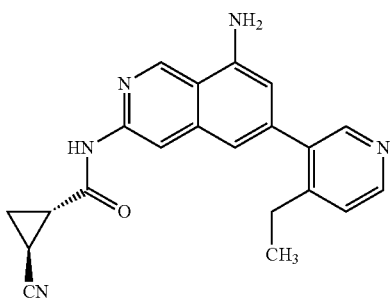 [SMILES: CCc1ccncc1-c1cc(N)c2cnc(NC(=O)[C@H]3C[C@@H]3C#N)cc2c1]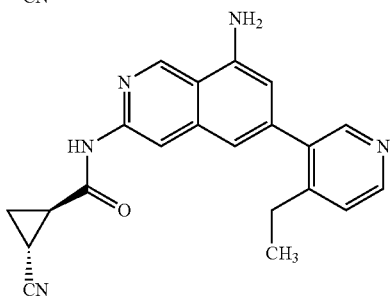 | trans-N-(8-amino-6-(4-ethylpyridin-3-yl)isoquinolin-3-yl)-2-cyanocyclopropane-1-carboxamide; |
| 68 | 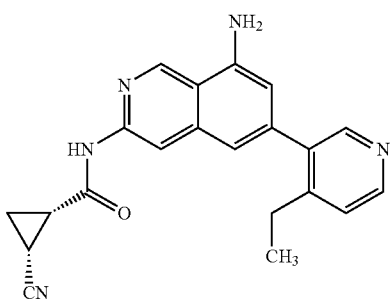 [SMILES: CCc1ccncc1-c1cc(N)c2cnc(NC(=O)[C@H]3C[C@H]3C#N)cc2c1]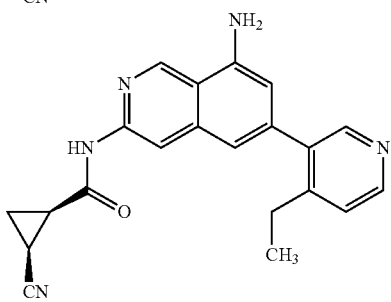 | cis-N-(8-amino-6-(4-ethylpyridin-3-yl)isoquinolin-3-yl)-2-cyanocyclopropane-1-carboxamide; |

| No. | Structure | Name |
|---|---|---|
| 69 | 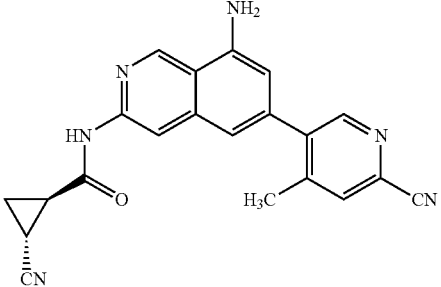 [SMILES: Cc1cc(C#N)ncc1-c1cc(N)c2cnc(NC(=O)[C@@H]3C[C@H]3C#N)cc2c1] | trans-N-(8-amino-6-(6-cyano-4-methylpyridin-3-yl)isoquinolin-3-yl)-2-cyanocyclopropane-1-carboxamide; |
| | 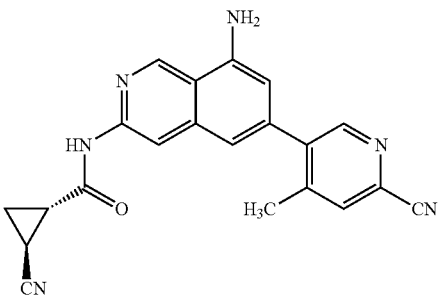 [SMILES: Cc1cc(C#N)ncc1-c1cc(N)c2cnc(NC(=O)[C@H]3C[C@@H]3C#N)cc2c1] | |
| 70, 107, 123 | 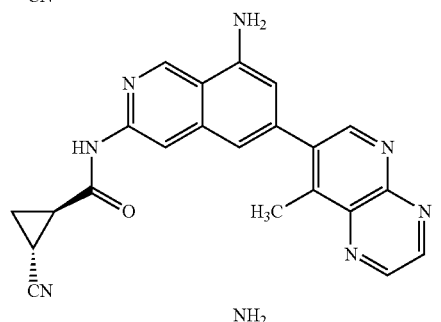 | trans-N-(8-amino-6-(8-methylpyrido[2,3-b]pyrazin-7-yl)isoquinolin-3-yl)-2-cyanocyclopropane-1-carboxamide; |
| | 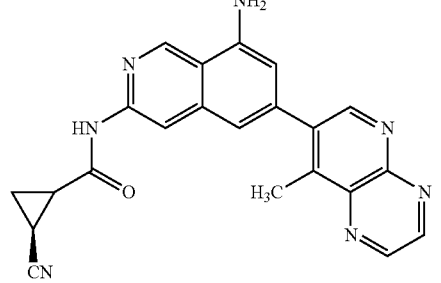 | |

| No. | Structure | Name |
|---|---|---|
| 73, 74 | 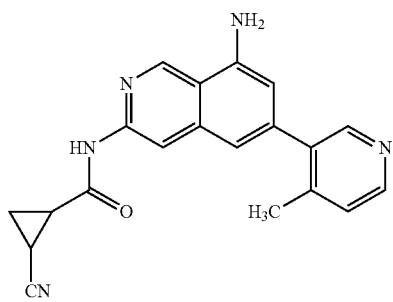 [SMILES: Cc1ccncc1-c1cc(N)c2cnc(NC(=O)C3CC3C#N)cc2c1] 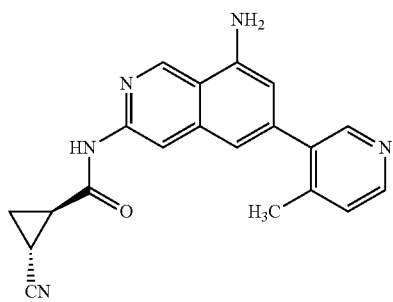 [SMILES: Cc1ccncc1-c1cc(N)c2cnc(NC(=O)[C@@H]3C[C@H]3C#N)cc2c1] 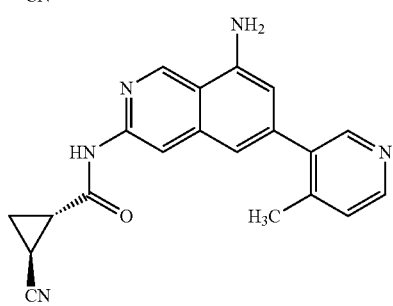 | trans-N-(8-amino-6-(4-methylpyridin-3-yl)isoquinolin-3-yl)-2-cyanocyclopropane-1-carboxamide; |
| 75, 170 | 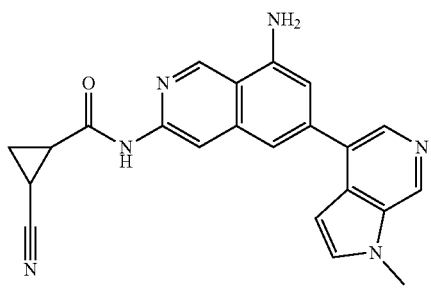 [SMILES: Cn1ccc2c(-c3cc(N)c4cnc(NC(=O)C5CC5C#N)cc4c3)cncc21] 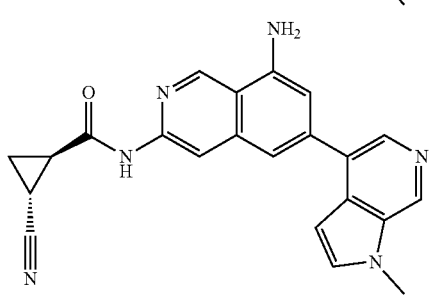 | trans-N-(8-amino-6-(1-methyl-1H-pyrrolo[2,3-c]pyridin-4-yl)isoquinolin-3-yl)-2-cyanocyclopropane-1-carboxamide; |

| No. | Structure | Name |
|---|---|---|
| 76, 171 | 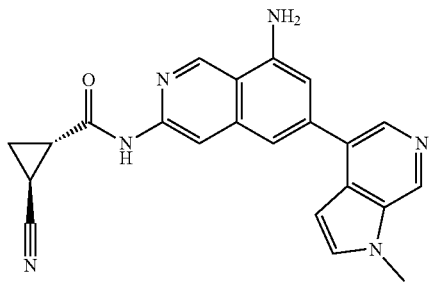 [SMILES: Cn1ccc2c(-c3cc(N)c4cnc(NC(=O)[C@H]5C[C@@H]5C#N)cc4c3)cncc21]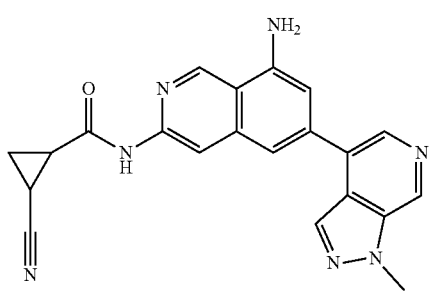 [SMILES: Cn1ncc2c(-c3cc(N)c4cnc(NC(=O)C5CC5C#N)cc4c3)cncc21]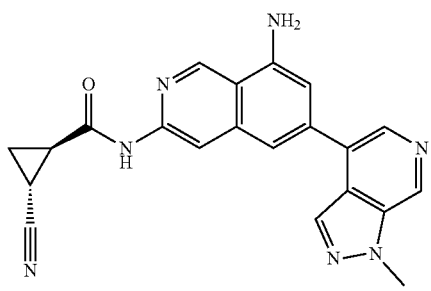 [SMILES: Cn1ncc2c(-c3cc(N)c4cnc(NC(=O)[C@@H]5C[C@H]5C#N)cc4c3)cncc21]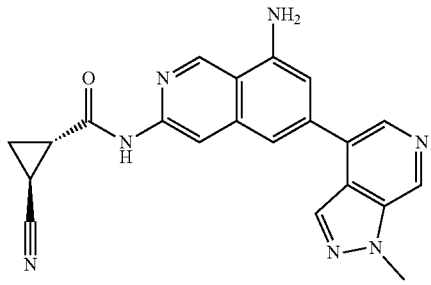 [SMILES: Cn1ncc2c(-c3cc(N)c4cnc(NC(=O)[C@H]5C[C@@H]5C#N)cc4c3)cncc21] | trans-N-(8-amino-6-(1-methyl-1H-pyrazolo[3,4-c]pyridin-4-yl)isoquinolin-3-yl)-2-cyanocyclopropane-1-carboxamide; |
| 77 | 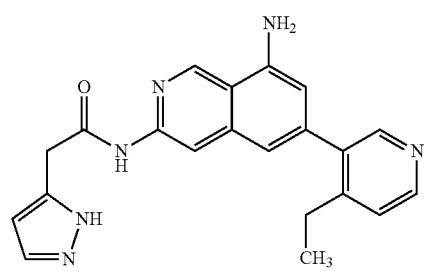 | N-(8-amino-6-(4-ethylpyridin-3-yl)isoquinolin-3-yl)-2-(1H-pyrazol-5-yl)acetamide; |

| No. | Structure | Name |
|---|---|---|
| 78, 109 | | trans-N-(8-amino-6-(6-methylimidazo[1,2-a]pyridin-7-yl)isoquinolin-3-yl)-2-cyanocyclopropane-1-carboxamide; |
| 79, 110 | | 5-(8-amino-3-(trans-2-cyanocyclopropane-1-carboxamido)isoquinolin-6-yl)-N,1-dimethyl-1H-pyrazole-3-carboxamide; |

-continued
| No. | Structure | Name |
|---|---|---|
| 80, 113 | 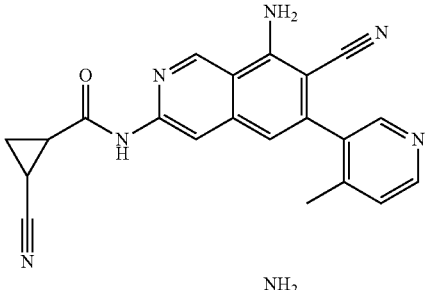 | trans-N-[8-amino-7-cyano-6-(4-methyl-3-pyridyl)-3-isoquinolyl]-2-cyanocyclopropane-1-carboxamide; |
| | 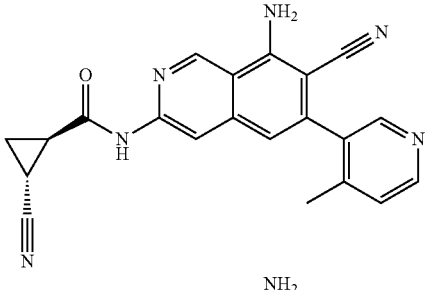 | |
| | 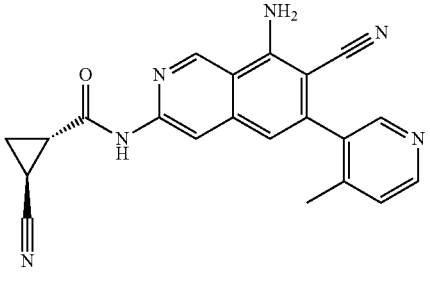 [SMILES: Cc1ccncc1-c1cc2cc(NC(=O)[C@H]3C[C@@H]3C#N)ncc2c(N)c1C#N] | |
| 81, 122 | 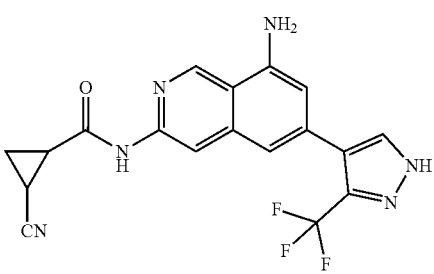 [SMILES: N#CC1CC1C(=O)Nc1cc2cc(-c3c[nH]nc3C(F)(F)F)cc(N)c2cn1] | trans-N-(8-amino-6-(3-(trifluoromethyl)-1H-pyrazol-4-yl)isoquinolin-3-yl)-2-cyanocyclopropane-1-carboxamide; |
| | 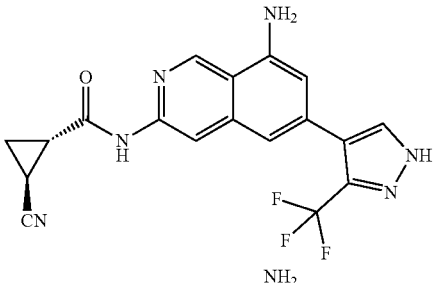 | |
| | 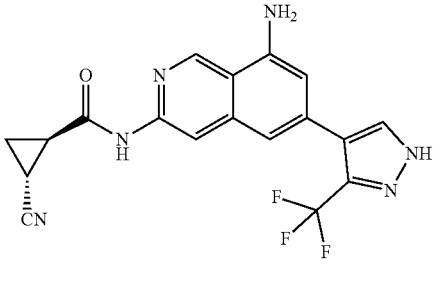 [SMILES: N#C[C@@H]1C[C@H]1C(=O)Nc1cc2cc(-c3c[nH]nc3C(F)(F)F)cc(N)c2cn1] | |

| No. | Structure | Name |
|---|---|---|
| 82, 139 | 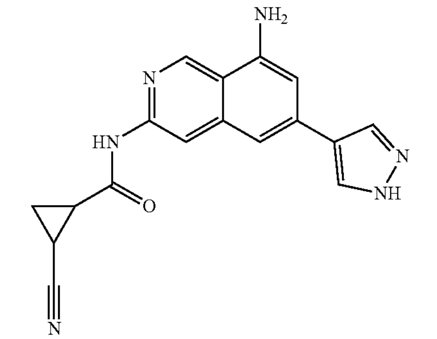 [SMILES: N#CC1CC1C(=O)Nc1cc2cc(-c3cn[nH]c3)cc(N)c2cn1] | trans-N-(8-amino-6-(1H-pyrazol-4-yl)isoquinolin-3-yl)-2-cyanocyclopropane-1-carboxamide; |
| | | |
| | | |
| 85, 119 | 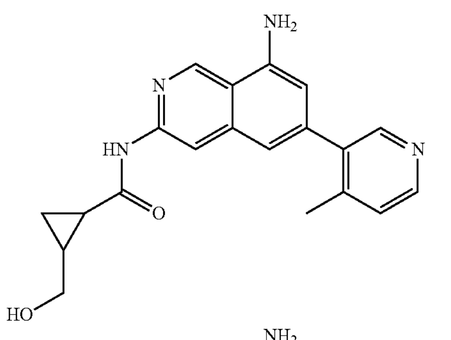 | trans-N-(8-amino-6-(4-methylpyridin-3-yl)isoquinolin-3-yl)-2-(hydroxymethyl)cyclopropane-1-carboxamide; |
| | | |

| No. | Structure | Name |
|---|---|---|
| 86, 172 | 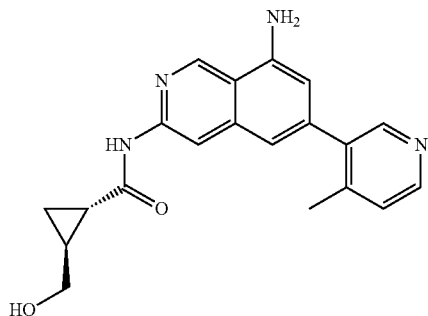 [SMILES: Cc1ccncc1-c1cc(N)c2cnc(NC(=O)[C@H]3C[C@@H]3CO)cc2c1]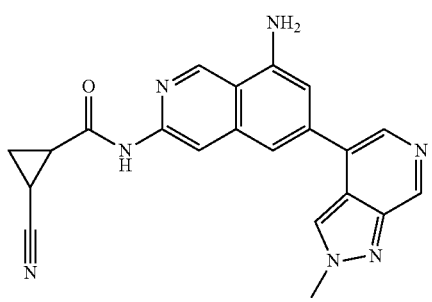 [SMILES: Cn1cc2c(-c3cc(N)c4cnc(NC(=O)C5CC5C#N)cc4c3)cncc2n1]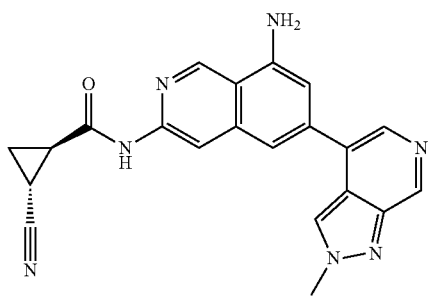 [SMILES: Cn1cc2c(-c3cc(N)c4cnc(NC(=O)[C@@H]5C[C@H]5C#N)cc4c3)cncc2n1]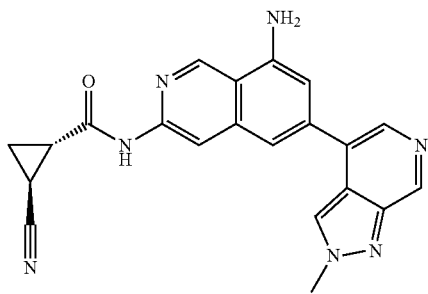 [SMILES: Cn1cc2c(-c3cc(N)c4cnc(NC(=O)[C@H]5C[C@@H]5C#N)cc4c3)cncc2n1] | trans-N-(8-amino-6-(2-methyl-2H-pyrazolo[3,4-c]pyridin-4-yl)isoquinolin-3-yl)-2-cyanocyclopropane-1-carboxamide; |
| 87, 117 | 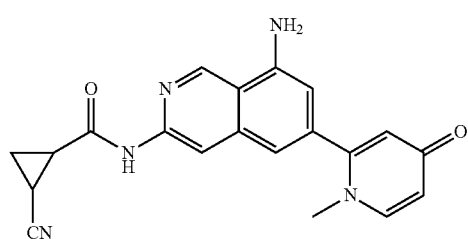 [SMILES: Cn1ccc(=O)cc1-c1cc(N)c2cnc(NC(=O)C3CC3C#N)cc2c1] | trans-N-(8-amino-6-(1-methyl-4-oxo-1,4-dihydropyridin-2-yl)isoquinolin-3-yl)-2-cyanocyclopropane-1-carboxamide; |

| No. | Structure | Name |
|---|---|---|
| | 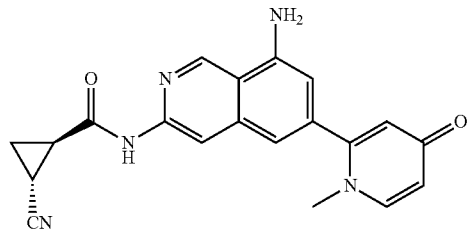 [SMILES: Cn1ccc(=O)cc1-c1cc(N)c2cnc(NC(=O)[C@@H]3C[C@H]3C#N)cc2c1] | |
| | 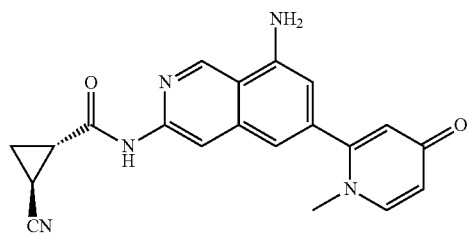 [SMILES: Cn1ccc(=O)cc1-c1cc(N)c2cnc(NC(=O)[C@H]3C[C@@H]3C#N)cc2c1] | |
| 88, 115 | 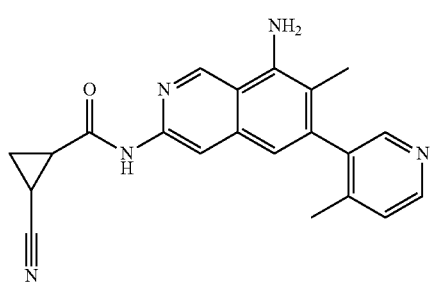 [SMILES: Cc1ccncc1-c1cc2cc(NC(=O)C3CC3C#N)ncc2c(N)c1C] | trans-N-(8-amino-7-methyl-6-(4-methylpyridin-3-yl)isoquinolin-3-yl)-2-cyanocyclopropane-1-carboxamide; |
| | 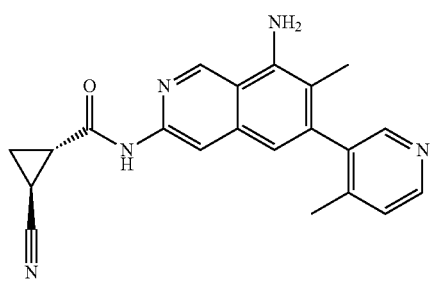 | |
| | 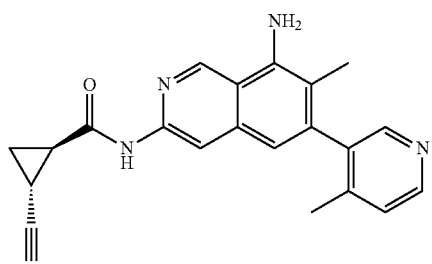 | |
| 89, 146 | 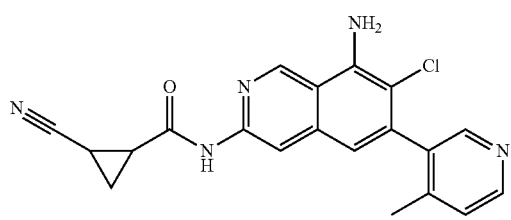 [SMILES: Cc1ccncc1-c1cc2cc(NC(=O)C3CC3C#N)ncc2c(N)c1Cl] | trans-N-(8-amino-7-chloro-6-(4-methylpyridin-3-yl)isoquinolin-3-yl)-2-cyanocyclopropane-1-carboxamide; |

| No. | Structure | Name |
|---|---|---|
| | 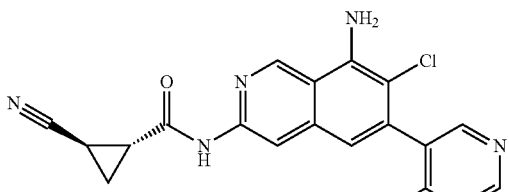 | |
| | 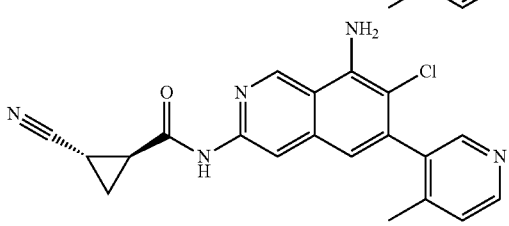 | |
| 90, 116 | 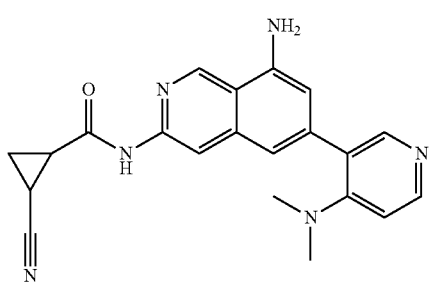 [SMILES: CN(C)c1ccncc1-c1cc(N)c2cnc(NC(=O)C3CC3C#N)cc2c1] | trans-N-(8-amino-6-(4-(dimethylamino)pyridin-3-yl)isoquinolin-3-yl)-2-cyanocyclopropane-1-carboxamide; |
| | 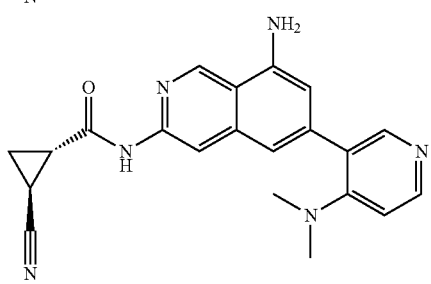 | |
| | 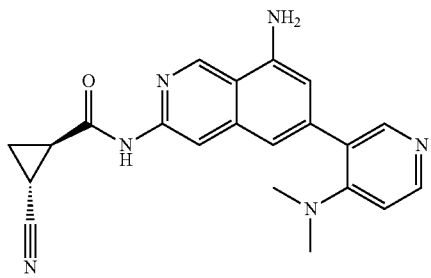 | |
| 91, 157 | 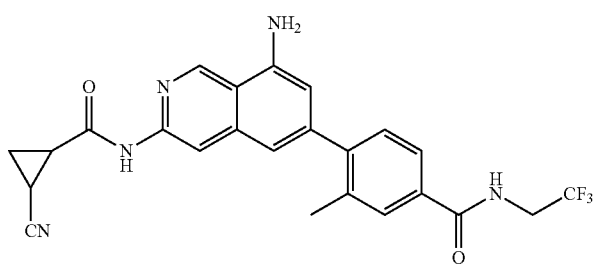 [SMILES: Cc1cc(C(=O)NCC(F)(F)F)ccc1-c1cc(N)c2cnc(NC(=O)C3CC3C#N)cc2c1] | 4-(8-amino-3-(trans-2-cyanocyclopropane-1-carboxamido)isoquinolin-6-yl)-3-methyl-N-(2,2,2-trifluoroethyl)benzamide; |

| No. | Structure | Name |
|---|---|---|
| | 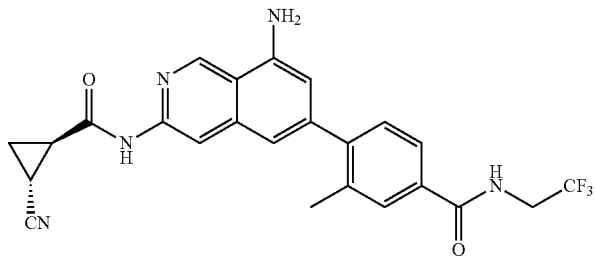 [SMILES: Cc1cc(C(=O)NCC(F)(F)F)ccc1-c1cc(N)c2cnc(NC(=O)[C@@H]3C[C@H]3C#N)cc2c1] | |
| | 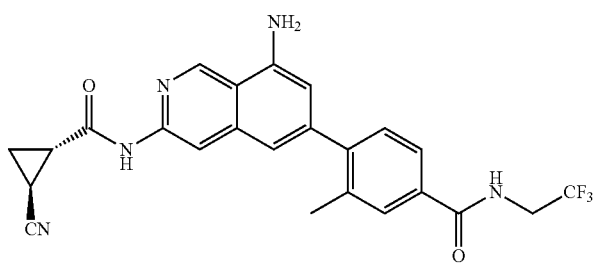 [SMILES: Cc1cc(C(=O)NCC(F)(F)F)ccc1-c1cc(N)c2cnc(NC(=O)[C@H]3C[C@@H]3C#N)cc2c1] | |
| 98 | 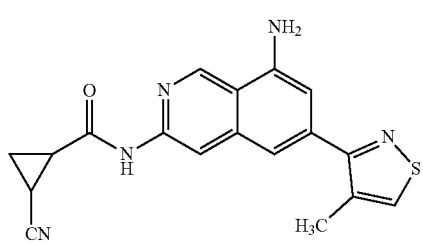 [SMILES: Cc1csnc1-c1cc(N)c2cnc(NC(=O)C3CC3C#N)cc2c1] | N-(8-amino-6-(4-methylisothiazol-3-yl)isoquinolin-3-yl)-2-cyanocyclopropane-1-carboxamide; |
| 99, 136 | 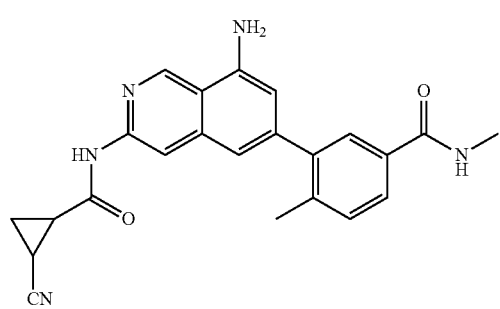 [SMILES: CNC(=O)c1ccc(C)c(-c2cc(N)c3cnc(NC(=O)C4CC4C#N)cc3c2)c1] | 3-(8-amino-3-(trans-2-cyanocyclopropane-1-carboxamido)isoquinolin-6-yl)-N,4-dimethylbenzamide; |
| | 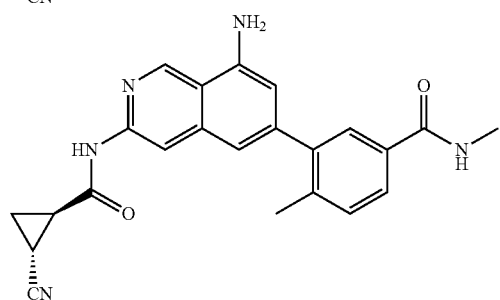 | |

| No. | Structure | Name |
|---|---|---|
| 100, 173 | 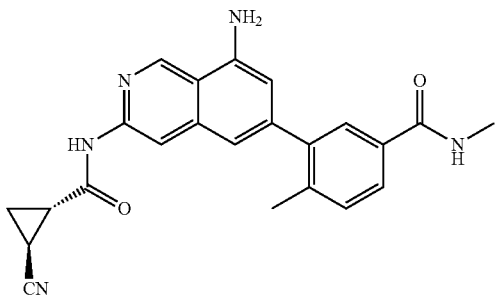 [SMILES: CNC(=O)c1ccc(C)c(-c2cc(N)c3cnc(NC(=O)[C@H]4C[C@@H]4C#N)cc3c2)c1]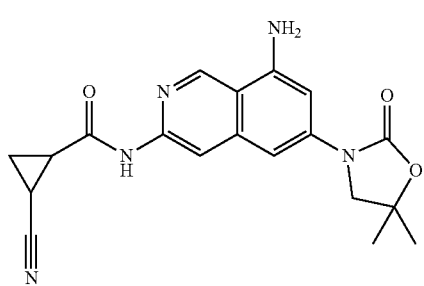 [SMILES: CC1(C)CN(c2cc(N)c3cnc(NC(=O)C4CC4C#N)cc3c2)C(=O)O1] | trans-N-(8-amino-6-(5,5-dimethyl-2-oxooxazolidin-3-yl)isoquinolin-3-yl)-2-cyanocyclopropane-1-carboxamide; |
| | 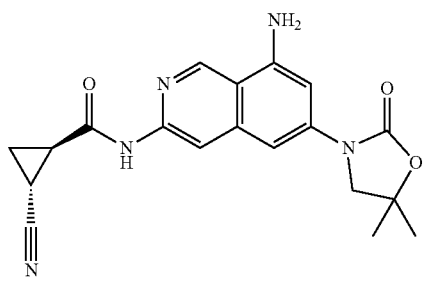 [SMILES: CC1(C)CN(c2cc(N)c3cnc(NC(=O)[C@@H]4C[C@H]4C#N)cc3c2)C(=O)O1]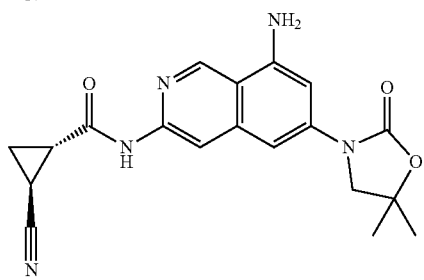 [SMILES: CC1(C)CN(c2cc(N)c3cnc(NC(=O)[C@H]4C[C@@H]4C#N)cc3c2)C(=O)O1] | |
| 101, 174 | 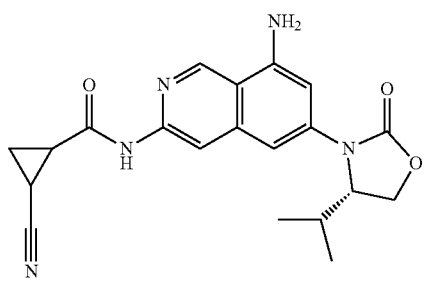 [SMILES: CC(C)[C@H]1COC(=O)N1c1cc(N)c2cnc(NC(=O)C3CC3C#N)cc2c1] | trans-N-(8-amino-6-((S)-4-isopropyl-2-oxooxazolidin-3-yl)isoquinolin-3-yl)-2-cyanocyclopropane-1-carboxamide; |

| No. | Structure | Name |
|---|---|---|
| 103, 124 | 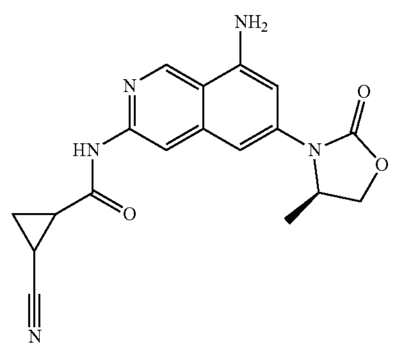 [SMILES: C[C@@H]1COC(=O)N1c1cc(N)c2cnc(NC(=O)C3CC3C#N)cc2c1] | trans-N-(8-amino-6-((R)-4-methyl-2-oxooxazolidin-3-yl)isoquinolin-3-yl)-2-cyanocyclopropane-1-carboxamide; |

| No. | Structure | Name |
|---|---|---|
| 104 | 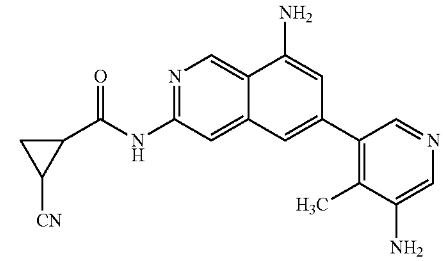 [SMILES: Cc1c(N)cncc1-c1cc(N)c2cnc(NC(=O)C3CC3C#N)cc2c1] | |
| 105, 118 | | trans-N-(8-amino-6-(3-(hydroxymethyl)-5-methyl-1H-pyrazol-4-yl)isoquinolin-3-yl)-2-cyanocyclopropane-1-carboxamide; |
| 106, 145 | | trans-N-(8-amino-5,7-difluoro-6-(4-methylpyridin-3-yl)isoquinolin-3-yl)-2-cyanocyclopropane-1-carboxamide; |

| No. | Structure | Name |
|---|---|---|
| | 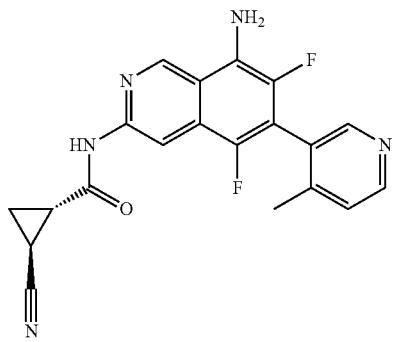 [SMILES: Cc1ccncc1-c1c(F)c(N)c2cnc(NC(=O)[C@H]3C[C@@H]3C#N)cc2c1F] | |
| 125 | 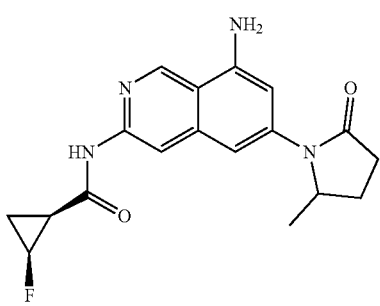 [SMILES: CC1CCC(=O)N1c1cc(N)c2cnc(NC(=O)[C@@H]3C[C@@H]3F)cc2c1] | (1S,2S)-N-(8-amino-6-(2-methyl-5-oxopyrrolidin-1-yl)isoquinolin-3-yl)-2-fluorocyclopropanecarboxamide; |
| 126 | 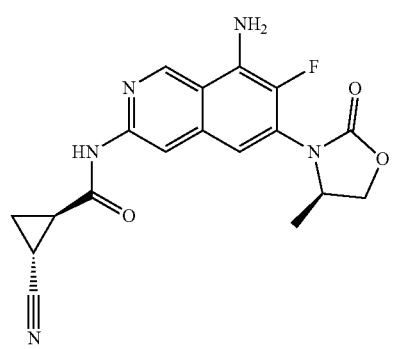 [SMILES: C[C@@H]1COC(=O)N1c1cc2cc(NC(=O)[C@@H]3C[C@H]3C#N)ncc2c(N)c1F] | trans-N-(8-amino-7-fluoro-6-((R)-4-methyl-2-oxooxazolidin-3-yl)isoquinolin-3-yl)-2-cyanocyclopropane-1-carboxamide; |
| | 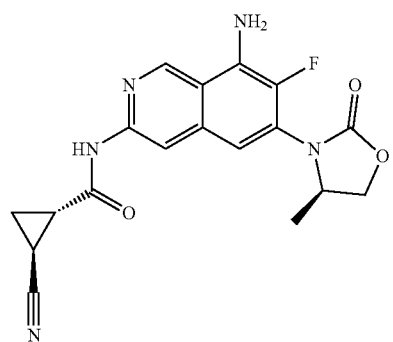 [SMILES: C[C@@H]1COC(=O)N1c1cc2cc(NC(=O)[C@H]3C[C@@H]3C#N)ncc2c(N)c1F] | |

-continued

| No. | Structure | Name |
|---|---|---|
| 127 | 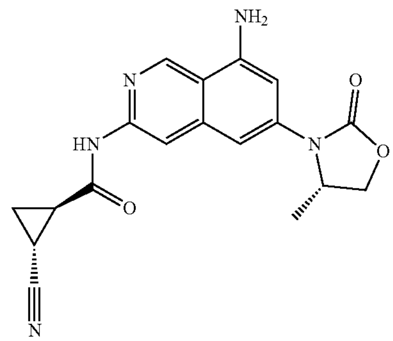 [SMILES: C[C@H]1COC(=O)N1c1cc(N)c2cnc(NC(=O)[C@@H]3C[C@H]3C#N)cc2c1] | trans-N-(8-amino-6-((S)-4-methyl-2-oxooxazolidin-3-yl)isoquinolin-3-yl)-2-cyanocyclopropane-1-carboxamide; |
| 128 | 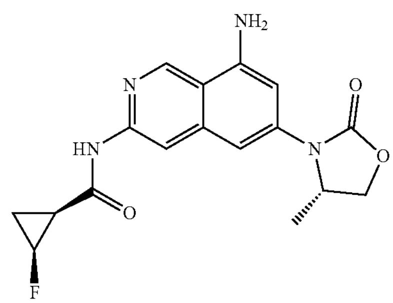 [SMILES: C[C@H]1COC(=O)N1c1cc(N)c2cnc(NC(=O)[C@@H]3C[C@@H]3F)cc2c1] | (1S,2S)-N-(8-amino-6-((S)-4-methyl-2-oxooxazolidin-3-yl)isoquinolin-3-yl)-2-fluorocyclopropane-1-carboxamide; |
| 130 | 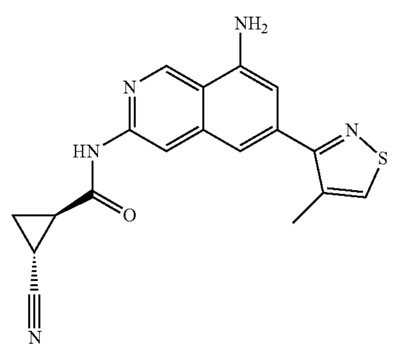 [SMILES: Cc1csnc1-c1cc(N)c2cnc(NC(=O)[C@@H]3C[C@H]3C#N)cc2c1] | trans-N-(8-amino-6-(4-methylisothiazol-3-yl)isoquinolin-3-yl)-2-cyanocyclopropane-1-carboxamide; |

| No. | Structure | Name |
|---|---|---|
| 131 | 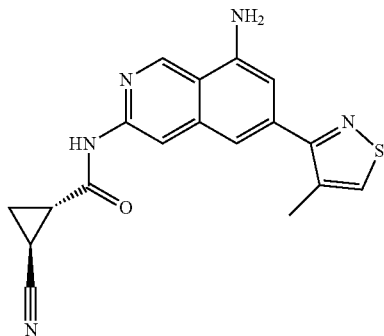 [SMILES: Cc1csnc1-c1cc(N)c2cnc(NC(=O)[C@H]3C[C@@H]3C#N)cc2c1]<br>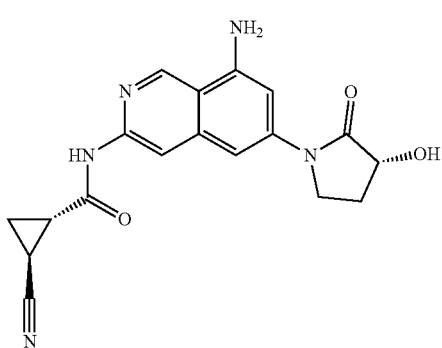 [SMILES: N#C[C@H]1C[C@@H]1C(=O)Nc1cc2cc(N3CC[C@@H](O)C3=O)cc(N)c2cn1] | trans-N-(8-amino-6-((R)-3-hydroxy-2-oxopyrrolidin-1-yl)isoquinolin-3-yl)-2-cyanocyclopropane-1-carboxamide; |
| 132 | 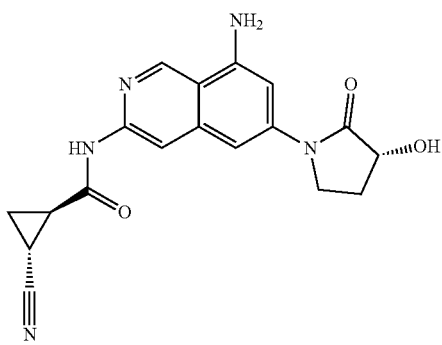 [SMILES: N#C[C@@H]1C[C@H]1C(=O)Nc1cc2cc(N3CC[C@@H](O)C3=O)cc(N)c2cn1]<br>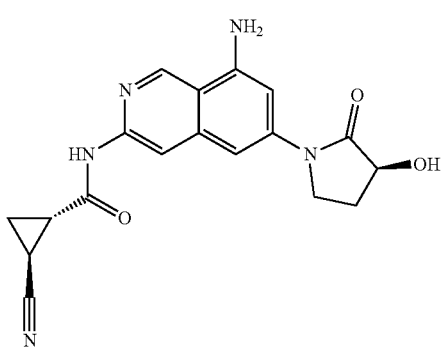 [SMILES: N#C[C@H]1C[C@@H]1C(=O)Nc1cc2cc(N3CC[C@H](O)C3=O)cc(N)c2cn1] | trans-N-(8-amino-6-((S)-3-hydroxy-2-oxopyrrolidin-1-yl)isoquinolin-3-yl)-2-cyanocyclopropane-1-carboxamide; |

| No. | Structure | Name |
|---|---|---|
| | 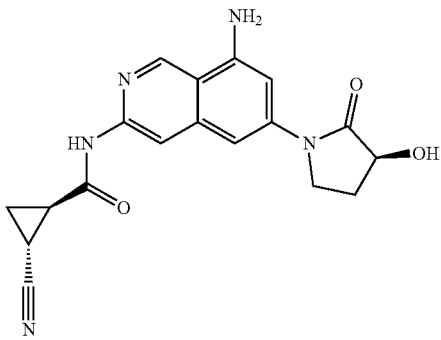 [SMILES: N#C[C@@H]1C[C@H]1C(=O)Nc1cc2cc(N3CC[C@H](O)C3=O)cc(N)c2cn1] | |
| 133 | 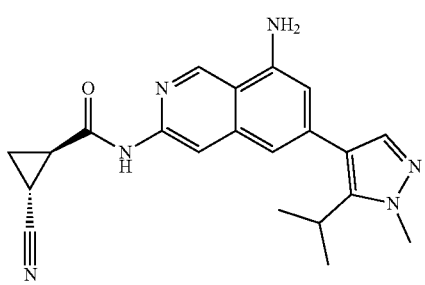 [SMILES: CC(C)c1c(-c2cc(N)c3cnc(NC(=O)[C@@H]4C[C@H]4C#N)cc3c2)cnn1C] | trans-N-[8-amino-6-(5-isopropyl-1-methyl-pyrazol-4-yl)-3-isoquinolyl]-2-cyano-cyclopropane-1-carboxamide; |
| | 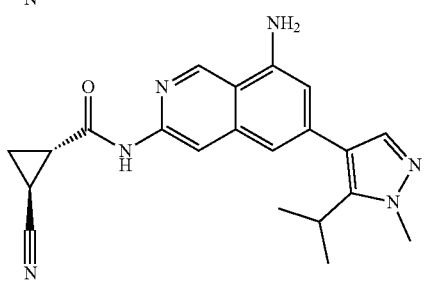 | |
| 134 | 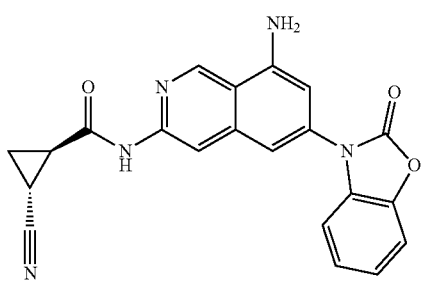 [SMILES: N#C[C@@H]1C[C@H]1C(=O)Nc1cc2cc(-n3c(=O)oc4ccccc43)cc(N)c2cn1] | trans-N-[8-amino-6-(2-oxo-1,3-benzoxazol-3-yl)-3-isoquinolyl]-2-cyano-cyclopropane-1-carboxamide; |
| | 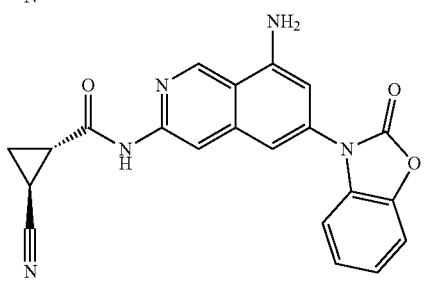 | |

| No. | Structure | Name |
|---|---|---|
| 135 | 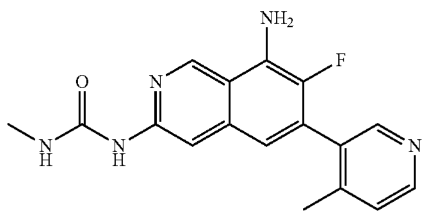 | 1-[8-amino-7-fluoro-6-(4-methyl-3-pyridyl)-3-isoquinolyl]-3-methylurea; |
| 138 | | trans-N-(8-amino-6-(3-methyl-2-oxo-2,3-dihydro-1H-benzo[d]imidazol-1-yl)isoquinolin-3-yl)-2-cyanocyclopropane-1-carboxamide; |
| | | |
| 140 | | trans-N-(8-amino-6-(2-oxo-2,3-dihydro-1H-benzo[d]imidazol-1-yl)isoquinolin-3-yl)-2-cyanocyclopropane-1-carboxamide; |

-continued

| No. | Structure | Name |
|---|---|---|
| 143 | 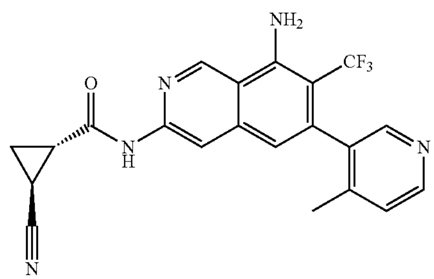 [SMILES: Cc1ccncc1-c1cc2cc(NC(=O)[C@H]3C[C@@H]3C#N)ncc2c(N)c1C(F)(F)F] | trans-N-(8-amino-6-(4-methylpyridin-3-yl)-7-(trifluoromethyl)isoquinolin-3-yl)-2-cyanocyclopropane-1-carboxamide; |
| 144 | 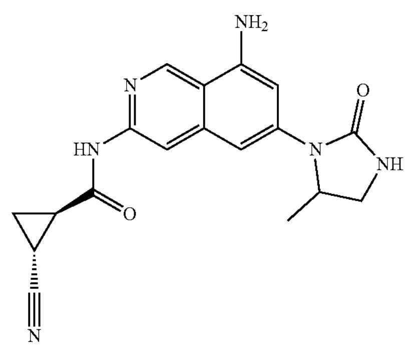 [SMILES: CC1CNC(=O)N1c1cc(N)c2cnc(NC(=O)[C@@H]3C[C@H]3C#N)cc2c1] | trans-N-(8-amino-6-(5-methyl-2-oxoimidazolidin-1-yl)isoquinolin-3-yl)-2-cyanocyclopropane-1-carboxamide; |
| 147 | 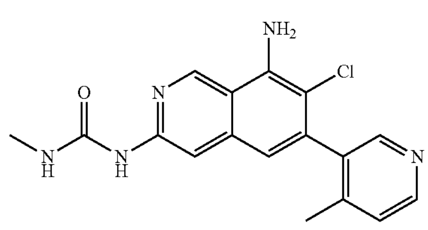 | 1-(8-amino-7-chloro-6-(4-methylpyridin-3-yl)isoquinolin-3-yl)-3-methylurea; |

| No. | Structure | Name |
| --- | --- | --- |
| 148 | 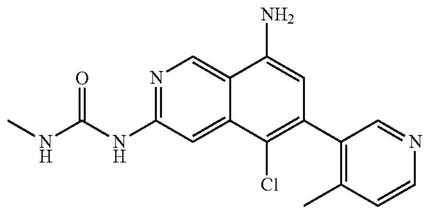 [SMILES: CNC(=O)Nc1cc2c(Cl)c(-c3cnccc3C)cc(N)c2cn1] | 1-(8-amino-5-chloro-6-(4-methylpyridin-3-yl)isoquinolin-3-yl)-3-methylurea; |
| 149 | 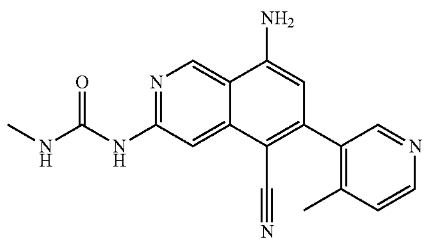 [SMILES: CNC(=O)Nc1cc2c(C#N)c(-c3cnccc3C)cc(N)c2cn1] | 1-(8-amino-5-cyano-6-(4-methylpyridin-3-yl)isoquinolin-3-yl)-3-methylurea; |
| 150 | 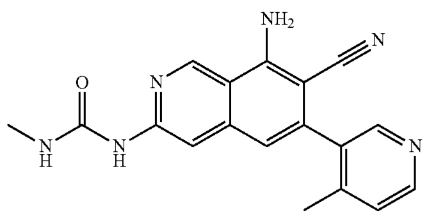 [SMILES: CNC(=O)Nc1cc2cc(-c3cnccc3C)c(C#N)c(N)c2cn1] | 1-(8-amino-7-cyano-6-(4-methylpyridin-3-yl)isoquinolin-3-yl)-3-methylurea; |
| 151 | | trans-N-[8-amino-6-(2-oxooxazolidin-5-yl)-3-isoquinolyl]-2-cyano-cyclopropane-1-carboxamide; |

| No. | Structure | Name |
|---|---|---|
| 153 | 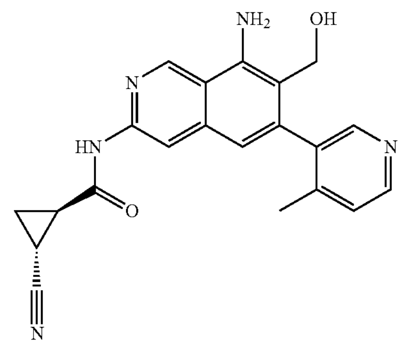 [SMILES: Cc1ccncc1-c1cc2cc(NC(=O)[C@@H]3C[C@H]3C#N)ncc2c(N)c1CO] | trans-N-[8-amino-7-(hydroxymethyl)-6-(4-methyl-3-pyridyl)-3-isoquinolyl]-2-cyano-cyclopropane-1-carboxamide; |
| | | |
| 154 | 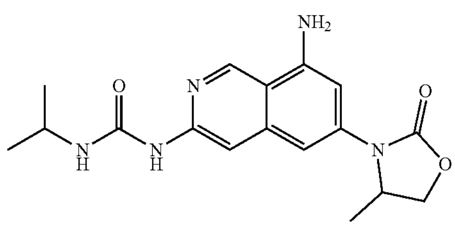 [SMILES: CC(C)NC(=O)Nc1cc2cc(N3C(=O)OCC3C)cc(N)c2cn1] | 1-[8-amino-6-(4-methyl-2-oxo-oxazolidin-3-yl)-3-isoquinolyl]-3-isopropylurea; |
| 155 | 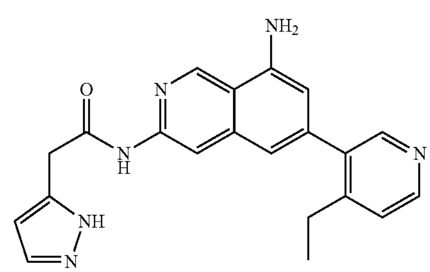 [SMILES: CCc1ccncc1-c1cc(N)c2cnc(NC(=O)Cc3ccn[nH]3)cc2c1] | N-(8-amino-6-(4-ethylpyridin-3-yl)isoquinolin-3-yl)-2-(1H-pyrazol-5-yl)acetamide; |
| 156 | 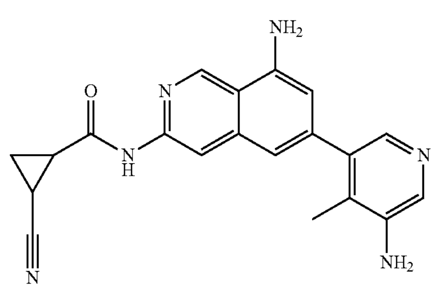 [SMILES: Cc1c(N)cncc1-c1cc(N)c2cnc(NC(=O)C3CC3C#N)cc2c1] | trans-N-(8-amino-6-(5-amino-4-methylpyridin-3-yl)isoquinolin-3-yl)-2-cyanocyclopropane-1-carboxamide; |

| No. | Structure | Name |
|---|---|---|
| 159 | 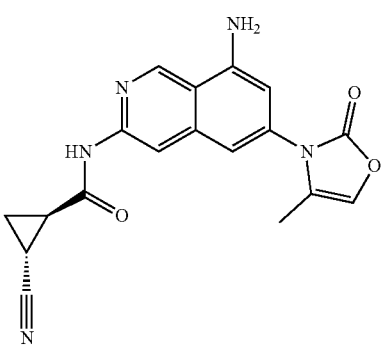 [SMILES: Cc1coc(=O)n1-c1cc(N)c2cnc(NC(=O)[C@@H]3C[C@H]3C#N)cc2c1]<br>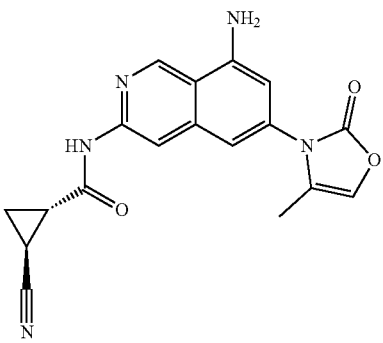 [SMILES: Cc1coc(=O)n1-c1cc(N)c2cnc(NC(=O)[C@H]3C[C@@H]3C#N)cc2c1] | trans-N-(8-amino-6-(4-methyl-2-oxooxazol-3(2H)-yl)isoquinolin-3-yl)-2-cyanocyclopropane-1-carboxamide; |
| 160 | 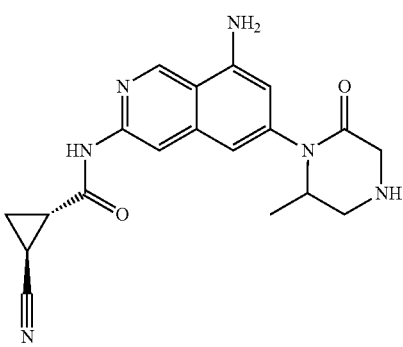 [SMILES: CC1CNCC(=O)N1c1cc(N)c2cnc(NC(=O)[C@H]3C[C@@H]3C#N)cc2c1]<br>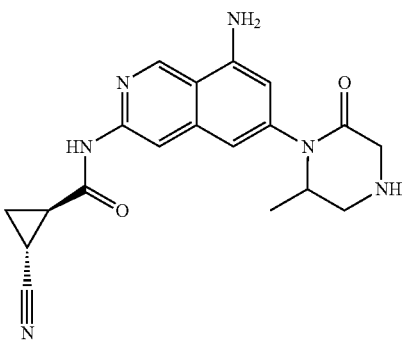 [SMILES: CC1CNCC(=O)N1c1cc(N)c2cnc(NC(=O)[C@@H]3C[C@H]3C#N)cc2c1] | trans-N-(8-amino-6-(2-methyl-6-oxopiperazin-1-yl)isoquinolin-3-yl)-2-cyanocyclopropane-1-carboxamide; |

-continued

| No. | Structure | Name |
|---|---|---|
| 161 | 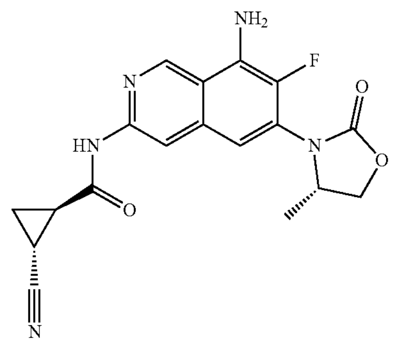 [SMILES: C[C@H]1COC(=O)N1c1cc2cc(NC(=O)[C@@H]3C[C@H]3C#N)ncc2c(N)c1F] | trans-N-(8-amino-7-fluoro-6-((S)-4-methyl-2-oxooxazolidin-3-yl)isoquinolin-3-yl)-2-cyanocyclopropane-1-carboxamide; |
| 162 | 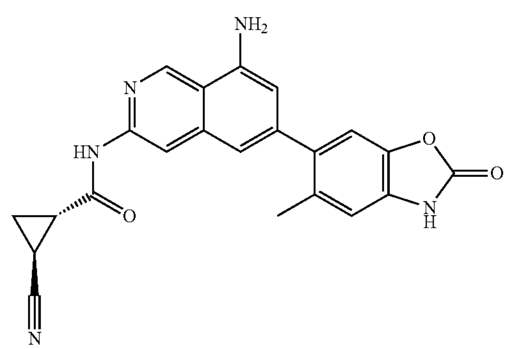 [SMILES: Cc1cc2[nH]c(=O)oc2cc1-c1cc(N)c2cnc(NC(=O)[C@H]3C[C@@H]3C#N)cc2c1] | (1S,2S)-N-(8-amino-6-(5-methyl-2-oxo-2,3-dihydrobenzo[d]oxazol-6-yl)isoquinolin-3-yl)-2-cyanocyclopropane-1-carboxamide; |
| 163 | 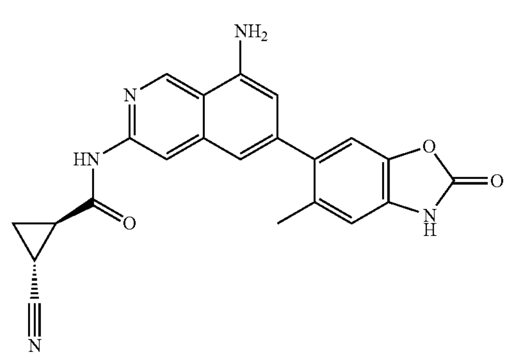 [SMILES: Cc1cc2[nH]c(=O)oc2cc1-c1cc(N)c2cnc(NC(=O)[C@@H]3C[C@H]3C#N)cc2c1] | (1R,2R)-N-(8-amino-6-(5-methyl-2-oxo-2,3-dihydrobenzo[d]oxazol-6-yl)isoquinolin-3-yl)-2-cyanocyclopropane-1-carboxamide; |

-continued

| No. | Structure | Name |
|---|---|---|
| 164 | 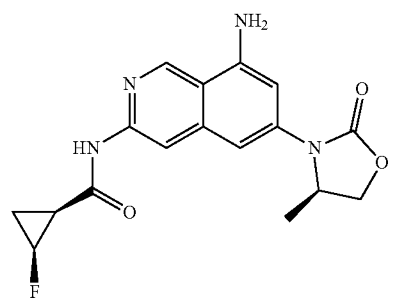 [SMILES: C[C@@H]1COC(=O)N1c1cc(N)c2cnc(NC(=O)[C@@H]3C[C@@H]3F)cc2c1] | (1S,2S)-N-(8-amino-6-((R)-4-methyl-2-oxooxazolidin-3-yl)isoquinolin-3-yl)-2-fluorocyclopropane-1-carboxamide; |
| 165 | 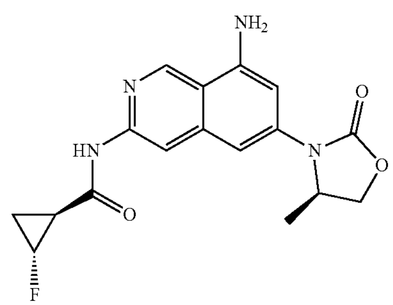 [SMILES: C[C@@H]1COC(=O)N1c1cc(N)c2cnc(NC(=O)[C@@H]3C[C@H]3F)cc2c1] | (1S,2R)-N-(8-amino-6-((R)-4-methyl-2-oxooxazolidin-3-yl)isoquinolin-3-yl)-2-fluorocyclopropane-1-carboxamide; |
| 166 | 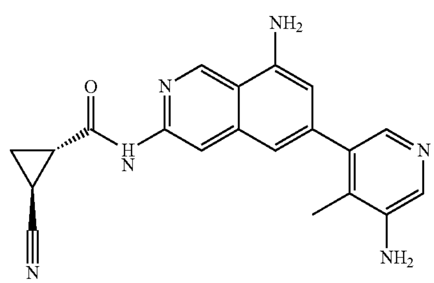 [SMILES: Cc1c(N)cncc1-c1cc(N)c2cnc(NC(=O)[C@H]3C[C@@H]3C#N)cc2c1] | (1S,2S)-N-(8-amino-6-(5-amino-4-methylpyridin-3-yl)isoquinolin-3-yl)-2-cyanocyclopropane-1-carboxamide; |
| 167 | 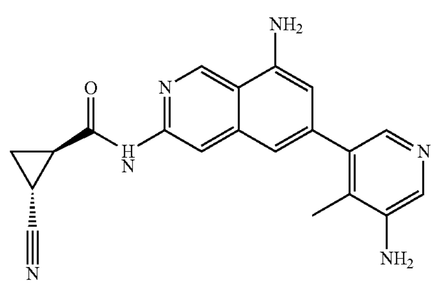 [SMILES: Cc1c(N)cncc1-c1cc(N)c2cnc(NC(=O)[C@@H]3C[C@H]3C#N)cc2c1] | (1R,2R)-N-(8-amino-6-(5-amino-4-methylpyridin-3-yl)isoquinolin-3-yl)-2-cyanocyclopropane-1-carboxamide; |
| 168, 169 | 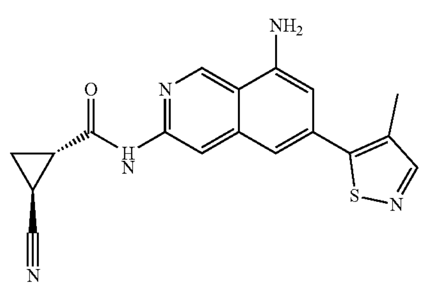 [SMILES: Cc1cnsc1-c1cc(N)c2cnc(NC(=O)[C@H]3C[C@@H]3C#N)cc2c1] | trans-N-(8-amino-6-(4-methylisothiazol-5-yl)isoquinolin-3-yl)-2-cyanocyclopropane-1-carboxamide; |

| No. | Structure | Name |
|---|---|---|
| | 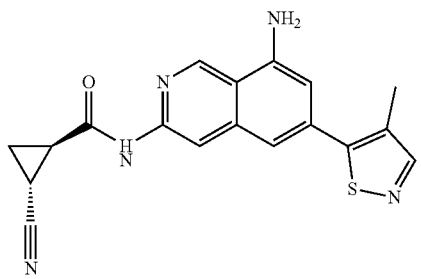 [SMILES: Cc1cnsc1-c1cc(N)c2cnc(NC(=O)[C@@H]3C[C@H]3C#N)cc2c1] | |
| 175 | 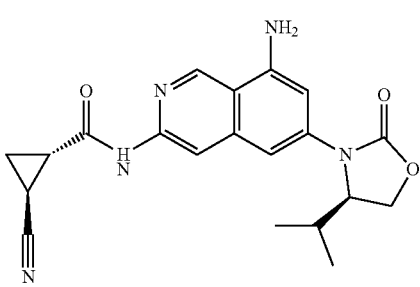 [SMILES: CC(C)[C@@H]1COC(=O)N1c1cc(N)c2cnc(NC(=O)[C@H]3C[C@@H]3C#N)cc2c1] | trans-N-(8-amino-6-((R)-4-isopropyl-2-oxooxazolidin-3-yl)isoquinolin-3-yl)-2-cyanocyclopropane-1-carboxamide; |
| | 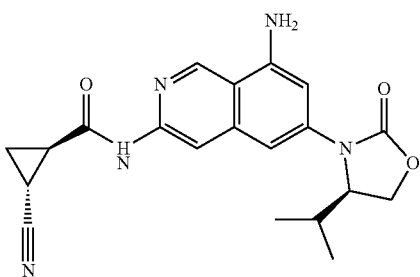 [SMILES: CC(C)[C@@H]1COC(=O)N1c1cc(N)c2cnc(NC(=O)[C@@H]3C[C@H]3C#N)cc2c1] | |
| 176 | 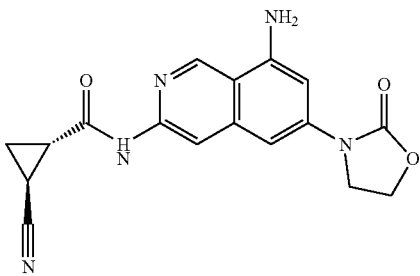 [SMILES: N#C[C@H]1C[C@@H]1C(=O)Nc1cc2cc(N3CCOC3=O)cc(N)c2cn1] | trans-N-(8-amino-6-(2-oxooxazolidin-3-yl)isoquinolin-3-yl)-2-cyanocyclopropane-1-carboxamide; |
| | 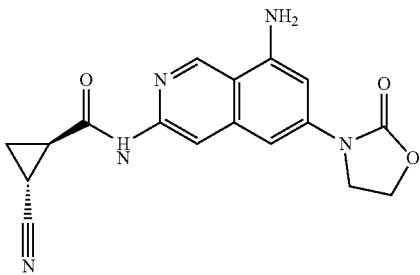 [SMILES: N#C[C@@H]1C[C@H]1C(=O)Nc1cc2cc(N3CCOC3=O)cc(N)c2cn1] | |

| No. | Structure | Name |
|---|---|---|
| 177 | 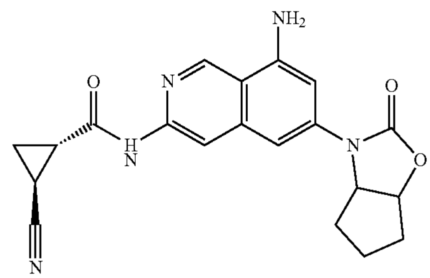 [SMILES: N#C[C@H]1C[C@@H]1C(=O)Nc1cc2cc(N3C(=O)OC4CCCC43)cc(N)c2cn1] | trans-N-(8-amino-6-(2-oxotetrahydro-2H-cyclopenta[d]oxazol-3(3aH)-yl)isoquinolin-3-yl)-2-cyanocyclopropane-1-carboxamide; |
| | | |
| 180 | 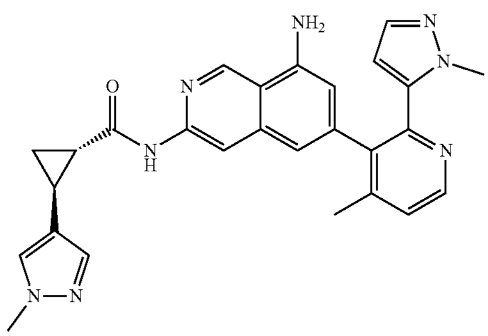 | (1S,2S)-N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropane-1-carboxamide; |
| 181 | 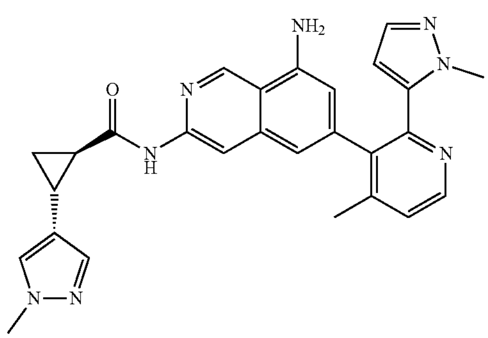 | (1R,2R)-N-(8-amino-6-(4-methyl-2-(1-methyl-1H-pyrazol-5-yl)pyridin-3-yl)isoquinolin-3-yl)-2-(1-methyl-1H-pyrazol-4-yl)cyclopropane-1-carboxamide; |
| 182 | 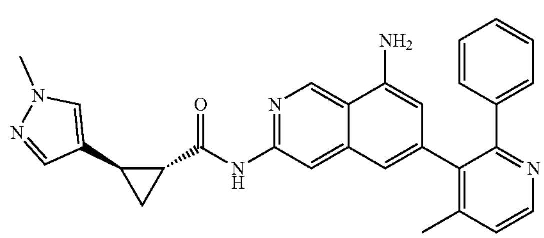 [SMILES: Cc1ccnc(-c2ccccc2)c1-c1cc(N)c2cnc(NC(=O)[C@@H]3C[C@H]3c3cnn(C)c3)cc2c1] | (1R,2R)-N-(8-amino-6-(4-methyl-2-phenylpyridin-3-yl)isoquinolin-3-yl)-2-(1-methyl-1H-pyrazol-4-yl)cyclopropane-1-carboxamide; |

-continued

| No. | Structure | Name |
|---|---|---|
| 183 | 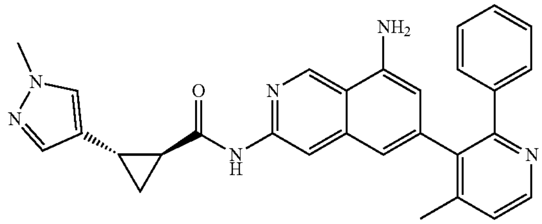 [SMILES: Cc1ccnc(-c2ccccc2)c1-c1cc(N)c2cnc(NC(=O)[C@H]3C[C@@H]3c3cnn(C)c3)cc2c1] | (1S,2S)-N-(8-amino-6-(4-methyl-2-phenylpyridin-3-yl)isoquinolin-3-yl)-2-(1-methyl-1H-pyrazol-4-yl)cyclopropane-1-carboxamide; |
| 184 | | trans-N-(8-amino-6-(4-methyl-2-(piperidin-1-yl)pyridin-3-yl)isoquinolin-3-yl)-2-(1-methyl-1H-pyrazol-4-yl)cyclopropane-1-carboxamide; |
| | | |
| 185 | | trans-N-(8-amino-6-(2-amino-3-methylpyridin-4-yl)isoquinolin-3-yl)-2-(1-methyl-1H-pyrazol-4-yl)cyclopropane-1-carboxamide; |
| | | |
| 186 | 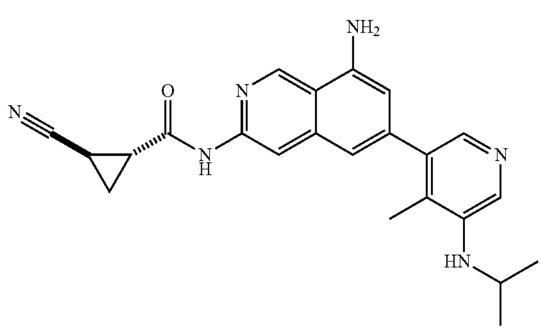 | trans-N-(8-amino-6-[4-methyl-5-[(propan-2-yl)amino]pyridin-3-yl]isoquinolin-3-yl)-2-cyanocyclopropane-1-carboxamide; |

| No. | Structure | Name |
|---|---|---|
| | 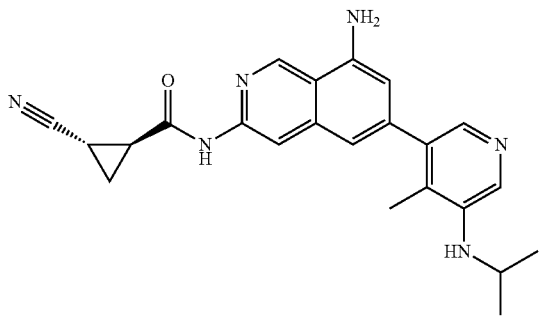 [SMILES: Cc1c(NC(C)C)cncc1-c1cc(N)c2cnc(NC(=O)[C@H]3C[C@@H]3C#N)cc2c1] | |
| 187 | 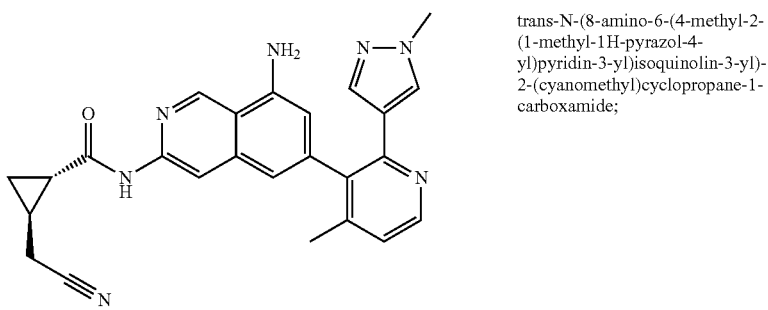 | trans-N-(8-amino-6-(4-methyl-2-(1-methyl-1H-pyrazol-4-yl)pyridin-3-yl)isoquinolin-3-yl)-2-(cyanomethyl)cyclopropane-1-carboxamide; |
| | 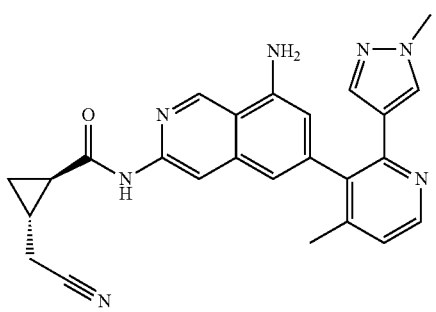 [SMILES: Cc1ccnc(-c2cnn(C)c2)c1-c1cc(N)c2cnc(NC(=O)[C@@H]3C[C@H]3CC#N)cc2c1] | |
| 188 | 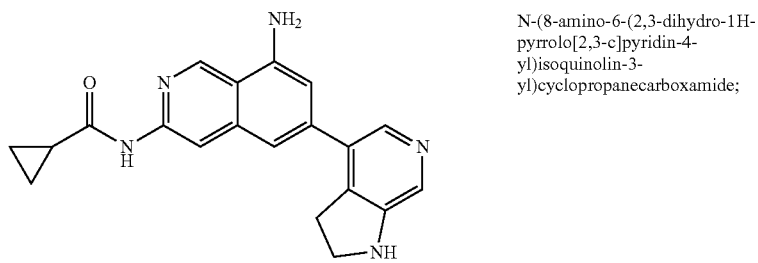 | N-(8-amino-6-(2,3-dihydro-1H-pyrrolo[2,3-c]pyridin-4-yl)isoquinolin-3-yl)cyclopropanecarboxamide; |
| 189, 190 | 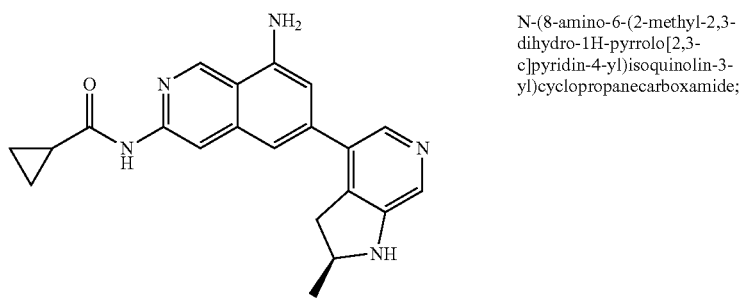 | N-(8-amino-6-(2-methyl-2,3-dihydro-1H-pyrrolo[2,3-c]pyridin-4-yl)isoquinolin-3-yl)cyclopropanecarboxamide; |

| No. | Structure | Name |
|---|---|---|
| | | |
| 191, 192 | 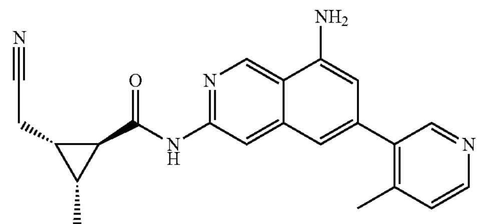 [SMILES: Cc1ccncc1-c1cc(N)c2cnc(NC(=O)[C@H]3[C@H](C)[C@@H]3CC#N)cc2c1] | (1,2)trans-N-(8-amino-6-(4-methylpyridin-3-yl)isoquinolin-3-yl)-2-(cyanomethyl)-3-methylcyclopropane-1-carboxamide; |
| | | |
| | | |
| | | |
| 195, 196, 197, 198 | 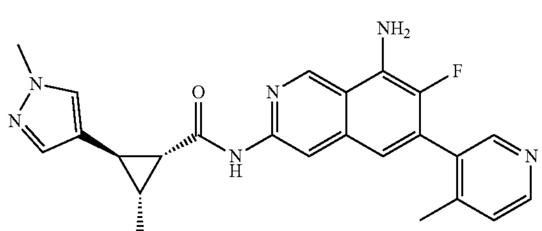 | (1,3)trans-N-(8-amino-7-fluoro-6-(4-methylpyridin-3-yl)isoquinolin-3-yl)-2-methyl-3-(1-methyl-1H-pyrazol-4-yl)cyclopropane-1-carboxamide; |
| | | |

| No. | Structure | Name |
|---|---|---|
| | 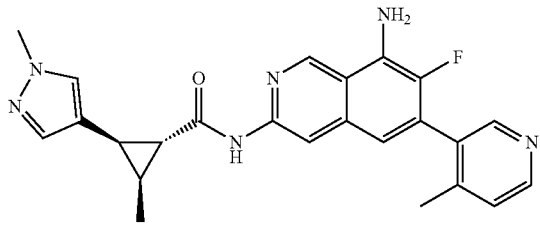 [SMILES: Cc1ccncc1-c1cc2cc(NC(=O)[C@@H]3[C@@H](C)[C@H]3c3cnn(C)c3)ncc2c(N)c1F]<br>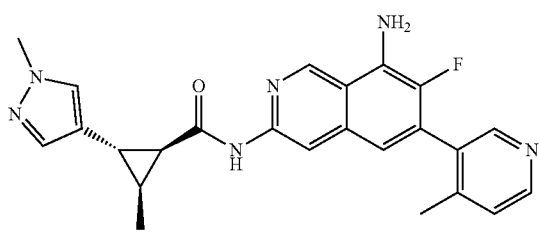 [SMILES: Cc1ccncc1-c1cc2cc(NC(=O)[C@H]3[C@@H](C)[C@@H]3c3cnn(C)c3)ncc2c(N)c1F] | |
| 207, 208 | 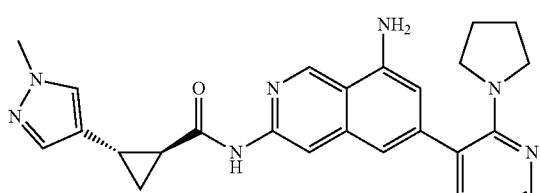<br>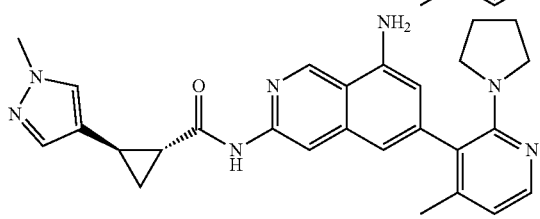 | trans-N-(8-amino-6-(4-methyl-2-(pyrrolidin-1-yl)pyridin-3-yl)isoquinolin-3-yl)-2-(1-methyl-1H-pyrazol-4-yl)cyclopropane-1-carboxamide; |
| 209 | 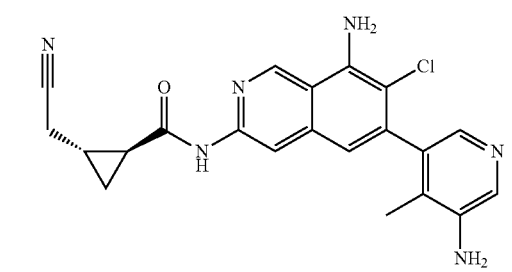 [SMILES: Cc1c(N)cncc1-c1cc2cc(NC(=O)[C@H]3C[C@@H]3CC#N)ncc2c(N)c1Cl]<br>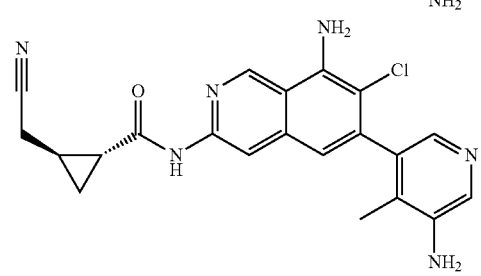 | trans-N-(8-amino-6-(5-amino-4-methylpyridin-3-yl)-7-chloroisoquinolin-3-yl)-2-(cyanomethyl)cyclopropane-1-carboxamide; |

| No. | Structure | Name |
|---|---|---|
| 210, 211 | | trans-N-(8-amino-6-(4-methyl-2-(1-methyl-1H-pyrazol-4-yl)pyridin-3-yl)isoquinolin-3-yl)-2-(1-methyl-1H-pyrazol-4-yl)cyclopropane-1-carboxamide; |
| 212, 213, 214, 215 | | (1,3)trans-N-(8-amino-6-(4-methylpyridin-3-yl)isoquinolin-3-yl)-2-methyl-3-(1-methyl-1H-pyrazol-4-yl)cyclopropane-1-carboxamide; |

-continued

| No. | Structure | Name |
|---|---|---|
| 216, 217 | | trans-N-(8-amino-6-(2,6-dichlorophenyl)isoquinolin-3-yl)-2-(1-methyl-1H-pyrazol-4-yl)cyclopropane-1-carboxamide; |
| 218, 219 | | trans-N-(8-amino-6-(2,6-difluorophenyl)isoquinolin-3-yl)-2-(1-methyl-1H-pyrazol-4-yl)cyclopropane-1-carboxamide; |
| 220, 221 | | trans-N-(8-amino-6-(2-cyano-6-methylphenyl)isoquinolin-3-yl)-2-cyanocyclopropane-1-carboxamide; |

-continued

| No. | Structure | Name |
|---|---|---|
| 222, 223 | | trans-N-(8-amino-6-(4-methyl-2-(1-methyl-1H-pyrazol-3-yl)pyridin-3-yl)isoquinolin-3-yl)-2-(1-methyl-1H-pyrazol-4-yl)cyclopropane-1-carboxamide; |
| | | |
| 224 | 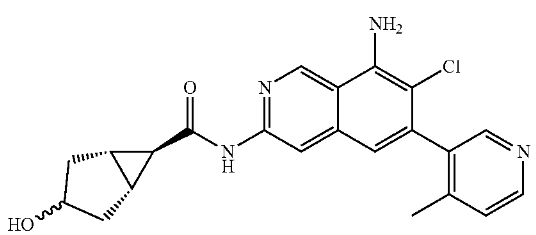 | (1R,5S,6r)-N-(8-amino-7-chloro-6-(4-methylpyridin-3-yl)isoquinolin-3-yl)-3-hydroxybicyclo[3.1.0]hexane-6-carboxamide; |
| 225 | 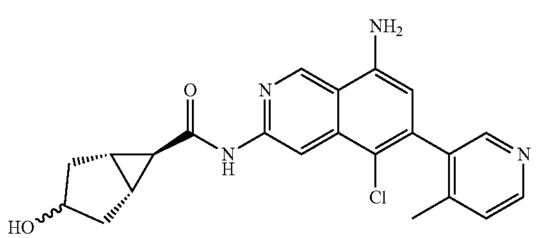 | (1R,5S,6r)-N-(8-amino-5-chloro-6-(4-methylpyridin-3-yl)isoquinolin-3-yl)-3-hydroxybicyclo[3.1.0]hexane-6-carboxamide; and |
| 226 | 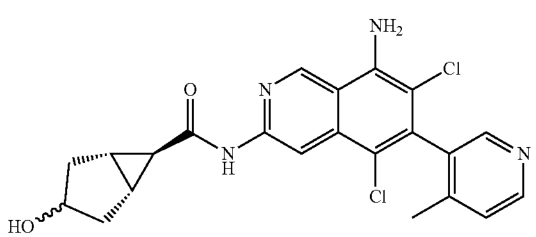 | (1R,5S,6r)-N-(8-amino-5,7-dichloro-6-(4-methylpyridin-3-yl)isoquinolin-3-yl)-3-hydroxybicyclo[3.1.0]hexane-6-carboxamide. |

28. The compound of claim 1, or a pharmaceutically acceptable salt thereof, wherein the compound is selected from the group consisting of:

| No. | Structure | Name |
|---|---|---|
| 9, 10, 11, 12 | | (1,3)trans-N-(8-amino-7-fluoro-6-(8-methyl-2,3-dihydro-1H-pyrido[2,3-b][1,4]oxazin-7-yl)isoquinolin-3-yl)-2-ethyl-3-(1-methyl-1H-pyrazol-4-yl)cyclopropane-1-carboxamide; |
| | | |
| | | |
| | | |
| 29 | 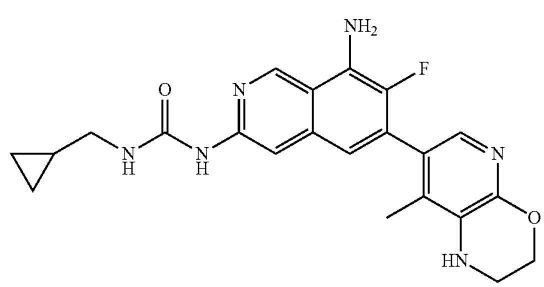 [SMILES: Cc1c(-c2cc3cc(NC(=O)NCC4CC4)ncc3c(N)c2F)cnc2c1NCCO2] | 1-(8-amino-7-fluoro-6-(8-methyl-2,3-dihydro-1H-pyrido[2,3-b][1,4]oxazin-7-yl)isoquinolin-3-yl)-3-(cyclopropylmethyl)urea; |

| No. | Structure | Name |
|---|---|---|
| 33, 34, 35, 36 | 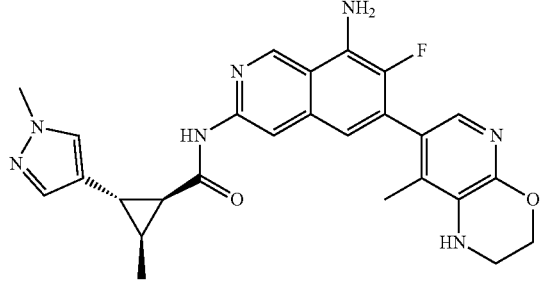 [SMILES: Cc1c(-c2cc3cc(NC(=O)[C@H]4[C@@H](C)[C@@H]4c4cnn(C)c4)ncc3c(N)c2F)cnc2c1NCCO2] | (1,3)trans-N-(8-amino-7-fluoro-6-(8-methyl-2,3-dihydro-1H-pyrido[2,3-b][1,4]oxazin-7-yl)isoquinolin-3-yl)-2-methyl-3-(1-methyl-1H-pyrazol-4-yl)cyclopropane-1-carboxamide; |
| | 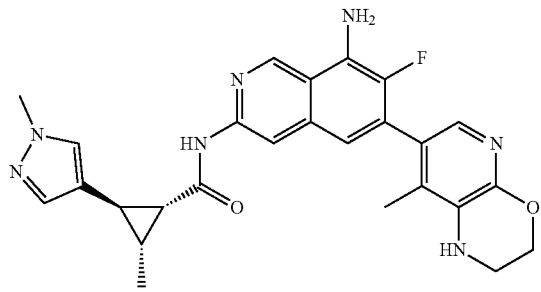 [SMILES: Cc1c(-c2cc3cc(NC(=O)[C@@H]4[C@H](C)[C@H]4c4cnn(C)c4)ncc3c(N)c2F)cnc2c1NCCO2] | |
| | 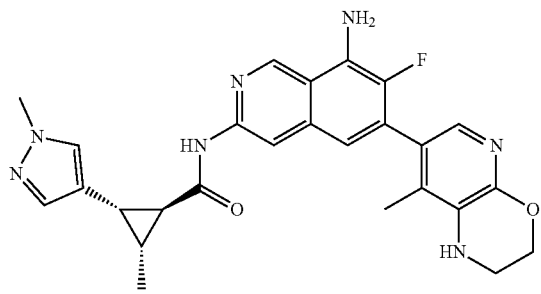 [SMILES: Cc1c(-c2cc3cc(NC(=O)[C@H]4[C@H](C)[C@@H]4c4cnn(C)c4)ncc3c(N)c2F)cnc2c1NCCO2] | |
| | 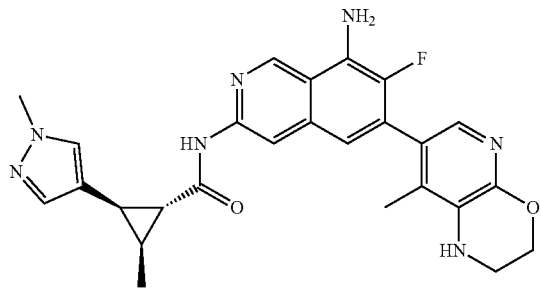 [SMILES: Cc1c(-c2cc3cc(NC(=O)[C@@H]4[C@@H](C)[C@H]4c4cnn(C)c4)ncc3c(N)c2F)cnc2c1NCCO2] | |
| 64 | 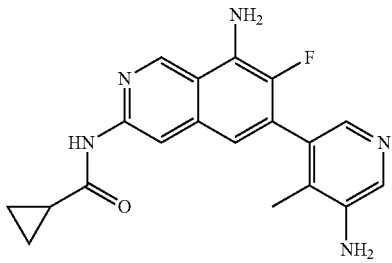 | N-(8-amino-6-(5-amino-4-methylpyridin-3-yl)-7-fluoroisoquinolin-3-yl)cyclopropanecarboxamide; |

-continued

| No. | Structure | Name |
|---|---|---|
| 83, 84 | | trans-N-(8-amino-6-(5-amino-4-methylpyridin-3-yl)-7-fluoroisoquinolin-3-yl)-2-cyanocyclopropane-1-carboxamide; |
| 111, 112 | | 1-(8-amino-7-fluoro-6-(8-methyl-2,3-dihydro-1H-pyrido[2,3-b][1,4]oxazin-7-yl)isoquinolin-3-yl)-3-(1-(1-methyl-1H-pyrazol-4-yl)ethyl)urea; |
| 120, 121 | 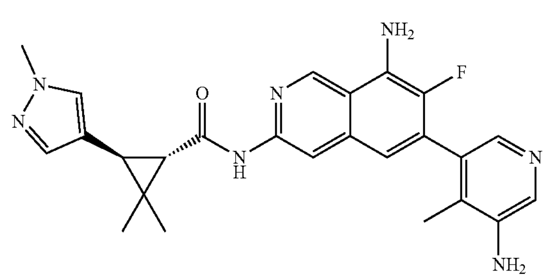 [SMILES: Cc1c(N)cncc1-c1cc2cc(NC(=O)[C@H]3[C@H](c4cnn(C)c4)C3(C)C)ncc2c(N)c1F] | trans-N-(8-amino-6-(5-amino-4-methylpyridin-3-yl)-7-fluoroisoquinolin-3-yl)-2,2-dimethyl-3-(1-methyl-1H-pyrazol-4-yl)cyclopropane-1-carboxamide; |

-continued

| No. | Structure | Name |
|---|---|---|
| | 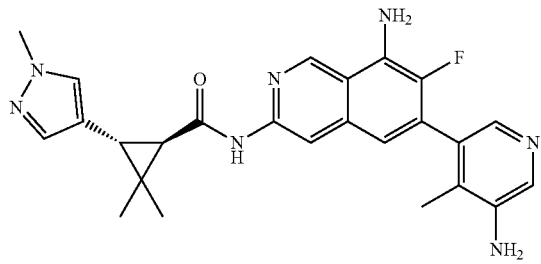 [SMILES: Cc1c(N)cncc1-c1cc2cc(NC(=O)[C@@H]3[C@@H](c4cnn(C)c4)C3(C)C)ncc2c(N)c1F] | |
| 137 | 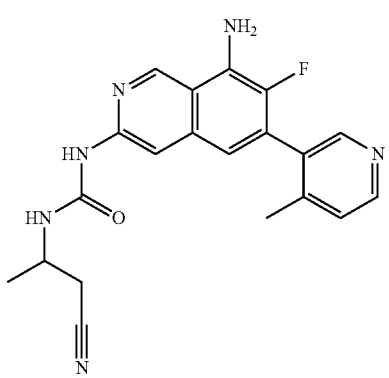 [SMILES: Cc1ccncc1-c1cc2cc(NC(=O)NC(C)CC#N)ncc2c(N)c1F] | 1-(8-amino-7-fluoro-6-(4-methylpyridin-3-yl)isoquinolin-3-yl)-3-(1-cyanopropan-2-yl)urea; |
| 152 | 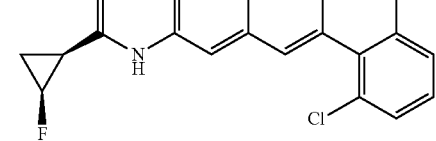 | cis-N-(8-amino-6-(2,6-dichlorophenyl)-7-fluoroisoquinolin-3-yl)-2-fluorocyclopropane-1-carboxamide; |
| 158 | 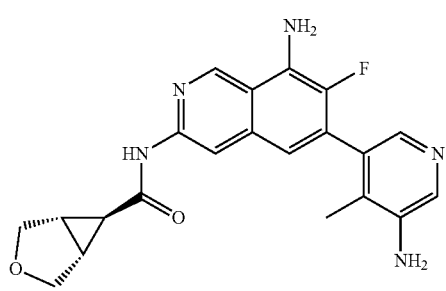 [SMILES: Cc1c(N)cncc1-c1cc2cc(NC(=O)[C@H]3[C@@H]4COC[C@@H]43)ncc2c(N)c1F] | (1R,5S,6r)-N-(8-amino-6-(5-amino-4-methylpyridin-3-yl)-7-fluoroisoquinolin-3-yl)-3-oxabicyclo[3.1.0]hexane-6-carboxamide; |
| 236, 237, 238, 239 | 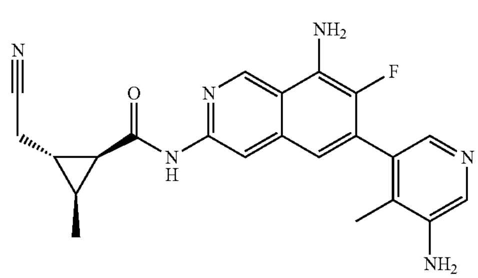 | (1,2)trans-N-(8-amino-6-(5-amino-4-methylpyridin-3-yl)-7-fluoroisoquinolin-3-yl)-2-(cyanomethyl)-3-methylcyclopropane-1-carboxamide; |

| No. | Structure | Name |
|---|---|---|
|  | 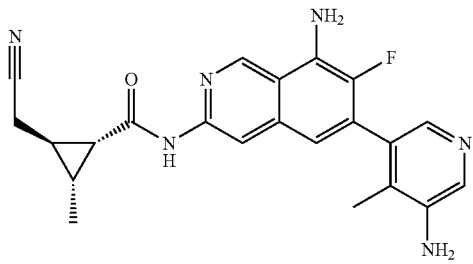 |  |
|  | 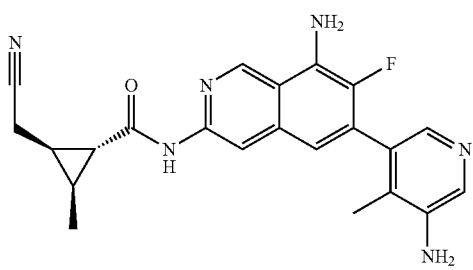 |  |
|  | 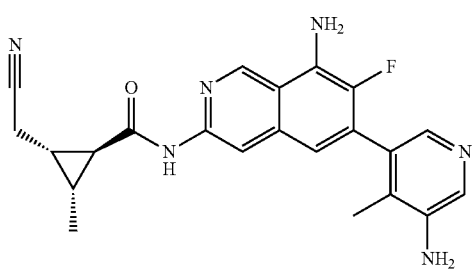 |  |
| 279, 280, 281, 282 | 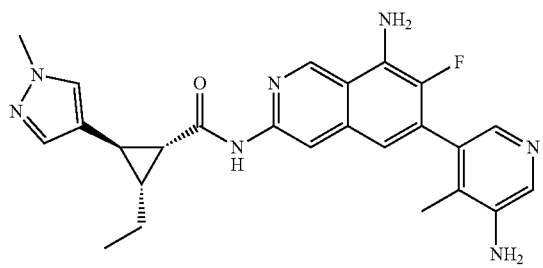 | (1,3)trans-N-(8-amino-6-(5-amino-4-methylpyridin-3-yl)-7-fluoroisoquinolin-3-yl)-2-ethyl-3-(1-methyl-1H-pyrazol-4-yl)cyclopropane-1-carboxamide; |
|  | 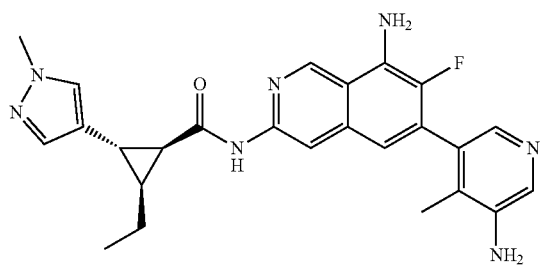 |  |
|  | 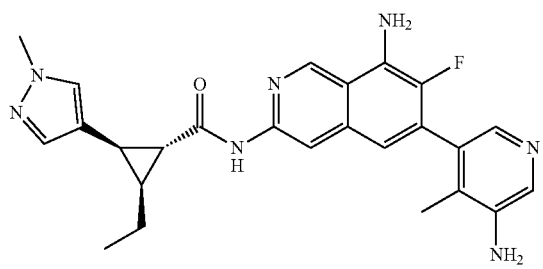 |  |

| No. | Structure | Name |
|---|---|---|
| 294, 295, 296, 297 | 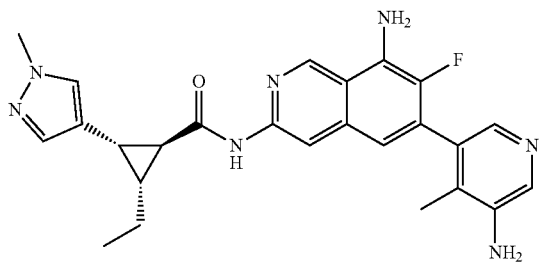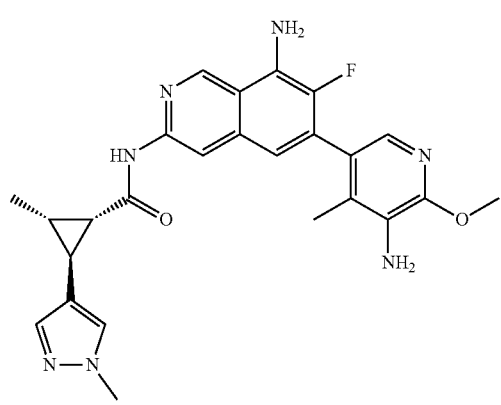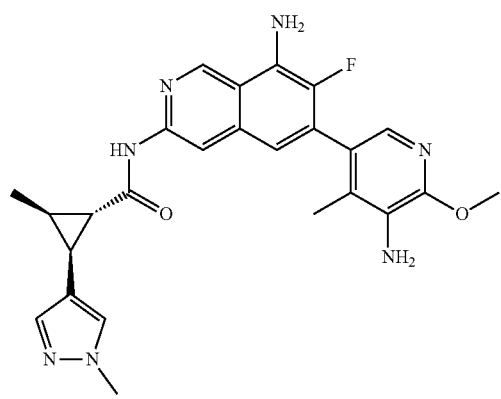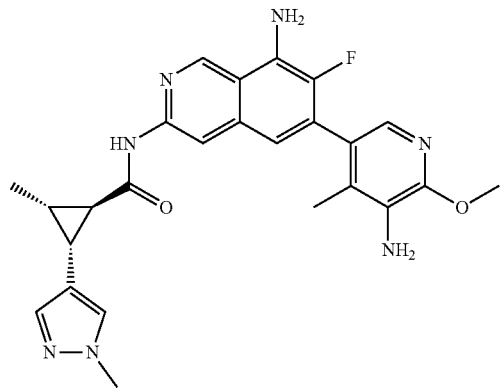 | (1,3)trans-N-(8-amino-6-(5-amino-6-methoxy-4-methylpyridin-3-yl)-7-fluoroisoquinolin-3-yl)-2-methyl-3-(1-methyl-1H-pyrazol-4-yl)cyclopropane-1-carboxamide; |

| No. | Structure | Name |
|---|---|---|
| 319, 320, 321, 322 | 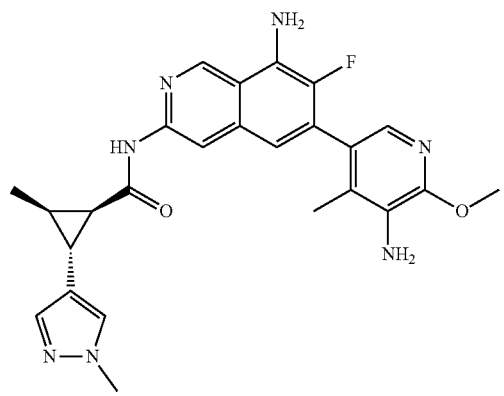 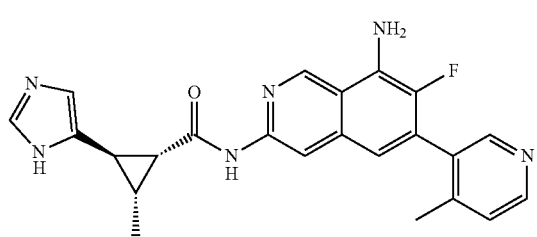 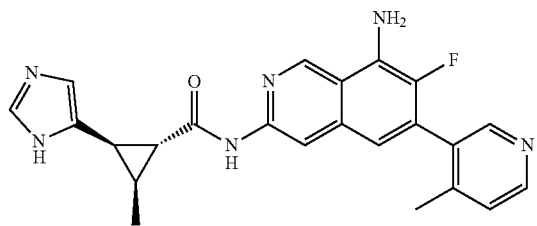 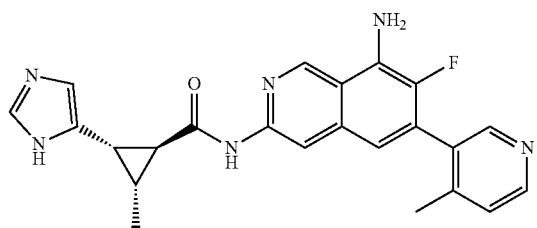 [SMILES: Cc1ccncc1-c1cc2cc(NC(=O)[C@H]3[C@H](C)[C@@H]3c3cnc[nH]3)ncc2c(N)c1F] 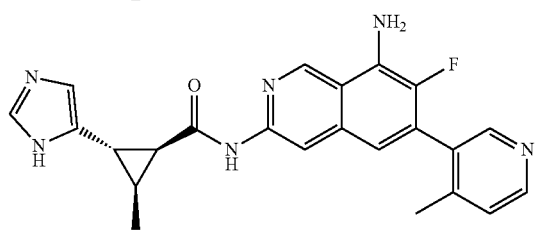 [SMILES: Cc1ccncc1-c1cc2cc(NC(=O)[C@H]3[C@@H](C)[C@@H]3c3cnc[nH]3)ncc2c(N)c1F] | (1,2)trans-N-(8-amino-7-fluoro-6-(4-methylpyridin-3-yl)isoquinolin-3-yl)-2-(1H-imidazol-5-yl)-3-methylcyclopropane-1-carboxamide; |

| No. | Structure | Name |
|---|---|---|
| 323, 324 | 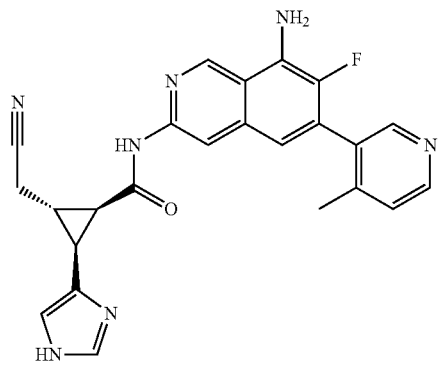 [SMILES: Cc1ccncc1-c1cc2cc(NC(=O)[C@@H]3[C@@H](CC#N)[C@@H]3c3c[nH]cn3)ncc2c(N)c1F] | N-(8-amino-7-fluoro-6-(4-methylpyridin-3-yl)isoquinolin-3-yl)-2-(cyanomethyl)-3-(1H-imidazol-4-yl)cyclopropane-1-carboxamide; |
|  | 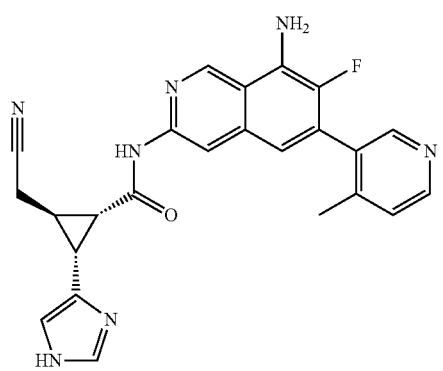 [SMILES: Cc1ccncc1-c1cc2cc(NC(=O)[C@H]3[C@H](CC#N)[C@H]3c3c[nH]cn3)ncc2c(N)c1F] |  |
| 325 | 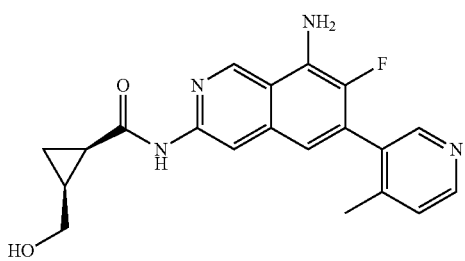 [SMILES: Cc1ccncc1-c1cc2cc(NC(=O)[C@@H]3C[C@@H]3CO)ncc2c(N)c1F] | cis-N-(8-amino-7-fluoro-6-(4-methylpyridin-3-yl)isoquinolin-3-yl)-2-(hydroxymethyl)cyclopropane-1-carboxamide; |
| 326 | 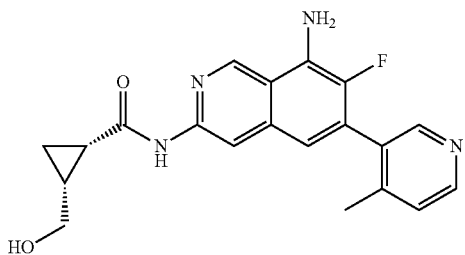 [SMILES: Cc1ccncc1-c1cc2cc(NC(=O)[C@H]3C[C@H]3CO)ncc2c(N)c1F] | (1R,2S)-N-(8-amino-7-fluoro-6-(4-methylpyridin-3-yl)isoquinolin-3-yl)-2-(hydroxymethyl)cyclopropane-1-carboxamide (Hydroxymethyl trans to amide; Absolute stereochemistry arbitrarily assigned); |
| 327 | 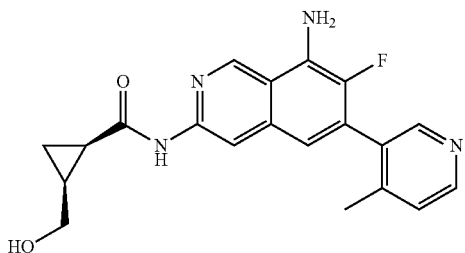 [SMILES: Cc1ccncc1-c1cc2cc(NC(=O)[C@@H]3C[C@@H]3CO)ncc2c(N)c1F] | (1R,2S)-N-(8-amino-7-fluoro-6-(4-methylpyridin-3-yl)isoquinolin-3-yl)-2-(hydroxymethyl)cyclopropane-1-carboxamide (Hydroxymethyl trans to amide; Absolute stereochemistry arbitrarily assigned); |

| No. | Structure | Name |
|---|---|---|
| 328 | 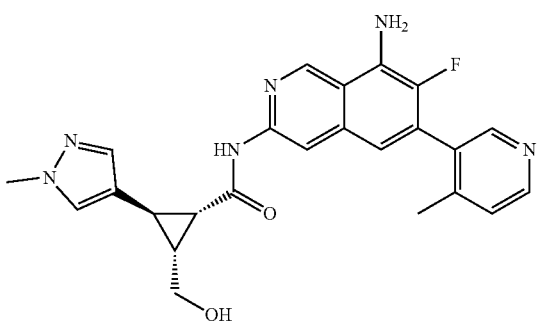 [SMILES: Cc1ccncc1-c1cc2cc(NC(=O)[C@@H]3[C@H](CO)[C@H]3c3cnn(C)c3)ncc2c(N)c1F] | N-(8-amino-7-fluoro-6-(4-methylpyridin-3-yl)isoquinolin-3-yl)-2-(hydroxymethyl)-3-(1-methyl-1H-pyrazol-4-yl)cyclopropane-1-carboxamide; |
|  | 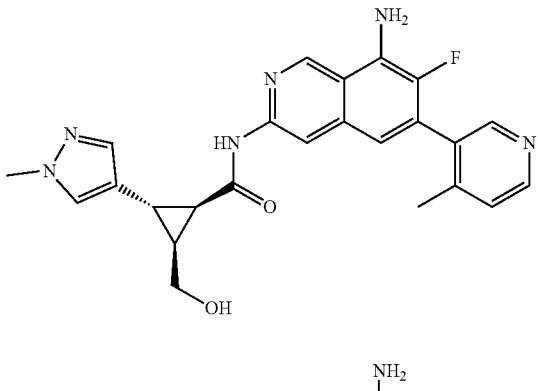 |  |
| 329, 330, 331, 332 | 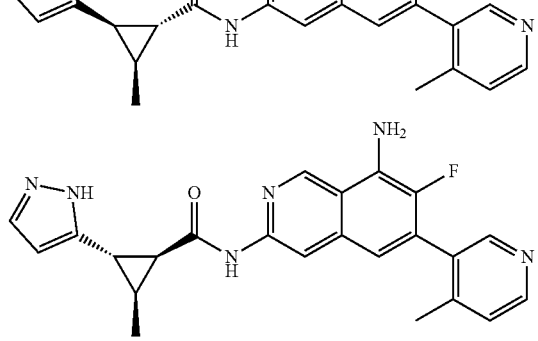 | (1,3)trans-N-(8-amino-7-fluoro-6-(4-methylpyridin-3-yl)isoquinolin-3-yl)-2-methyl-3-(1H-pyrazol-5-yl)cyclopropane-1-carboxamide; |

| No. | Structure | Name |
|---|---|---|
| 333 | 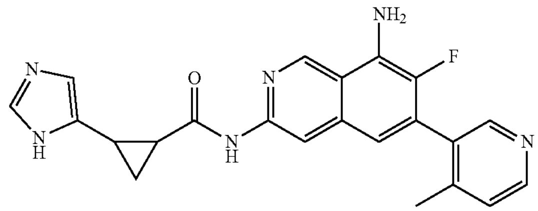 [SMILES: Cc1ccncc1-c1cc2cc(NC(=O)C3CC3c3cnc[nH]3)ncc2c(N)c1F] | trans-N-(8-amino-7-fluoro-6-(4-methylpyridin-3-yl)isoquinolin-3-yl)-2-(1H-imidazol-5-yl)cyclopropane-1-carboxamide; |
| 334 | 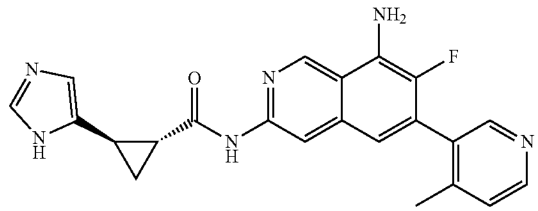 [SMILES: Cc1ccncc1-c1cc2cc(NC(=O)[C@@H]3C[C@H]3c3cnc[nH]3)ncc2c(N)c1F] | (1R,2R)-N-(8-amino-7-fluoro-6-(4-methylpyridin-3-yl)isoquinolin-3-yl)-2-(1H-imidazol-5-yl)cyclopropane-1-carboxamide; |
| 335 | 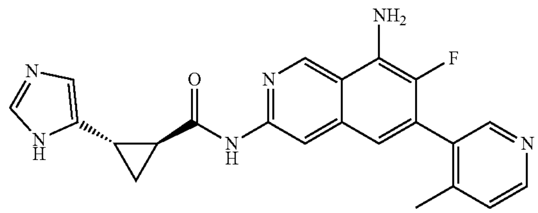 [SMILES: Cc1ccncc1-c1cc2cc(NC(=O)[C@H]3C[C@@H]3c3cnc[nH]3)ncc2c(N)c1F] | (1S,2S)-N-(8-amino-7-fluoro-6-(4-methylpyridin-3-yl)isoquinolin-3-yl)-2-(1H-imidazol-5-yl)cyclopropane-1-carboxamide; |
| 336 | 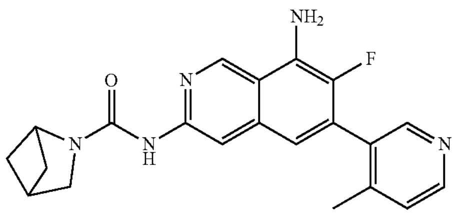 [SMILES: Cc1ccncc1-c1cc2cc(NC(=O)N3CC4CC3C4)ncc2c(N)c1F] | N-(8-amino-7-fluoro-6-(4-methylpyridin-3-yl)isoquinolin-3-yl)-2-azabicyclo[2.1.1]hexane-2-carboxamide; |
| 337, 338, 339, 340 | | (1,2)trans-N-(8-amino-7-fluoro-6-(4-methylpyridin-3-yl)isoquinolin-3-yl)-2-(1-(2,2-difluoroethyl)-1H-pyrazol-4-yl)-3-methylcyclopropane-1-carboxamide; |

| No. | Structure | Name |
|---|---|---|
| 341, 342 | 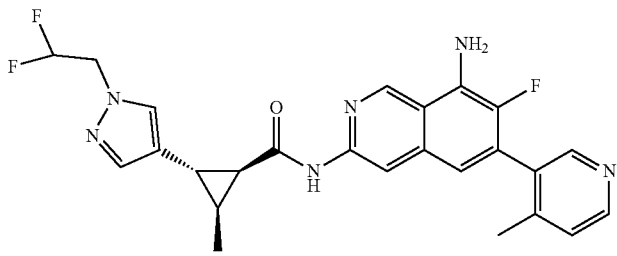 [SMILES: Cc1ccncc1-c1cc2cc(NC(=O)[C@H]3[C@@H](C)[C@@H]3c3cnn(CC(F)F)c3)ncc2c(N)c1F] | cis-N-(8-amino-7-fluoro-6-(4-methylpyridin-3-yl)isoquinolin-3-yl)-2-((dimethylamino)methyl)cyclopropane-1-carboxamide; |
| 343, 344, 345 | 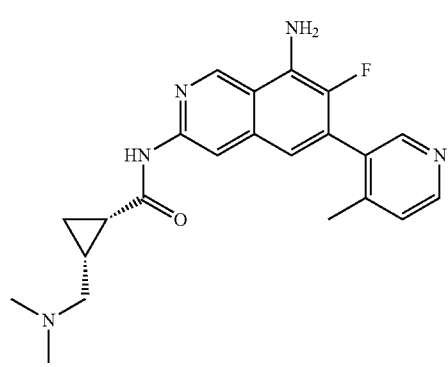 [SMILES: Cc1ccncc1-c1cc2cc(NC(=O)[C@H]3C[C@H]3CN(C)C)ncc2c(N)c1F]<br>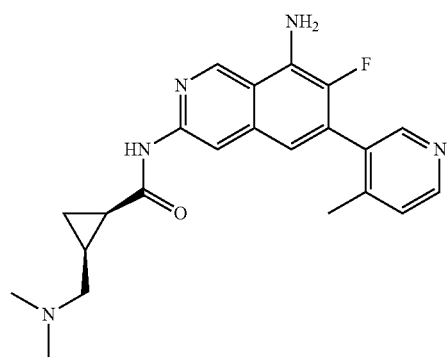 [SMILES: Cc1ccncc1-c1cc2cc(NC(=O)[C@@H]3C[C@@H]3CN(C)C)ncc2c(N)c1F] | N-(8-amino-7-fluoro-6-(4-methylpyridin-3-yl)isoquinolin-3-yl)-2-(cyanomethyl)-3-((dimethylamino)methyl)cyclopropane-1-carboxamide; |
| | 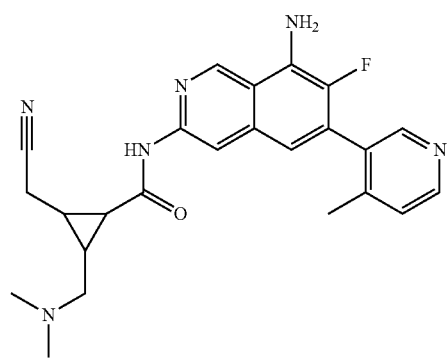 [SMILES: Cc1ccncc1-c1cc2cc(NC(=O)C3C(CC#N)C3CN(C)C)ncc2c(N)c1F] | |

| No. | Structure | Name |
|---|---|---|
| 346, 347, 348, 349 | 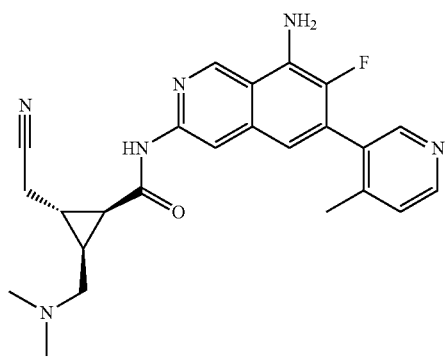 [SMILES: Cc1ccncc1-c1cc2cc(NC(=O)[C@@H]3[C@@H](CC#N)[C@@H]3CN(C)C)ncc2c(N)c1F]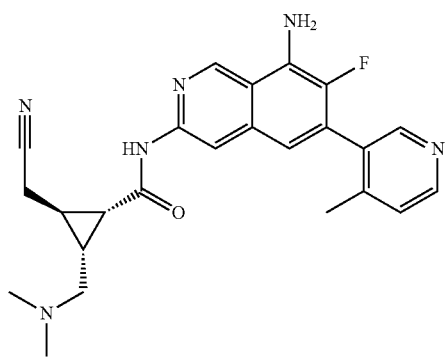 [SMILES: Cc1ccncc1-c1cc2cc(NC(=O)[C@H]3[C@H](CC#N)[C@H]3CN(C)C)ncc2c(N)c1F]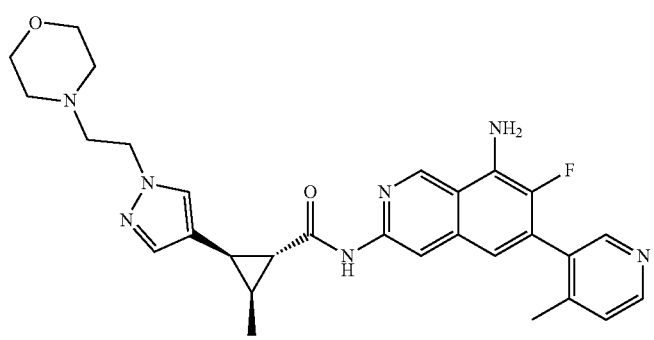 [SMILES: Cc1ccncc1-c1cc2cc(NC(=O)[C@@H]3[C@@H](C)[C@H]3c3cnn(CCN4CCOCC4)c3)ncc2c(N)c1F]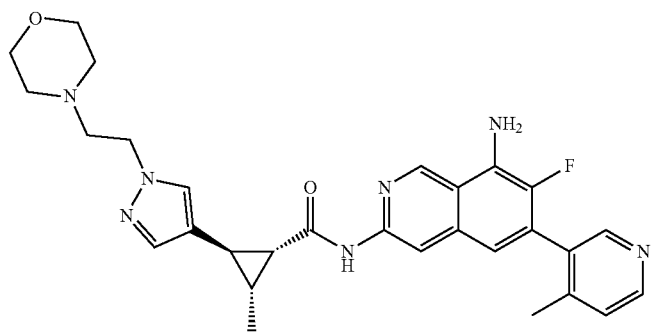 [SMILES: Cc1ccncc1-c1cc2cc(NC(=O)[C@@H]3[C@H](C)[C@H]3c3cnn(CCN4CCOCC4)c3)ncc2c(N)c1F] | (1,3)trans-N-(8-amino-7-fluoro-6-(4-methylpyridin-3-yl)isoquinolin-3-yl)-2-methyl-3-(1-(2-morpholinoethyl)-1H-pyrazol-4-yl)cyclopropane-1-carboxamide; |

| No. | Structure | Name |
|---|---|---|
| | 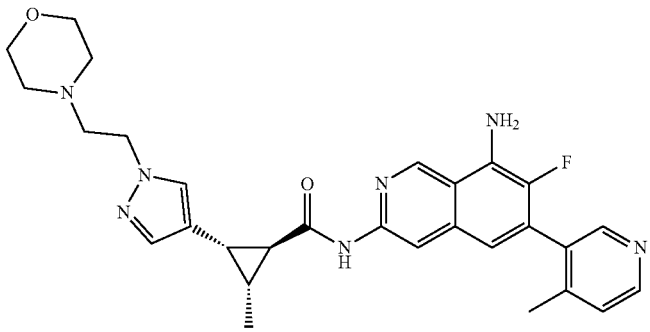 [SMILES: Cc1ccncc1-c1cc2cc(NC(=O)[C@H]3[C@H](C)[C@@H]3c3cnn(CCN4CCOCC4)c3)ncc2c(N)c1F] | |
| | 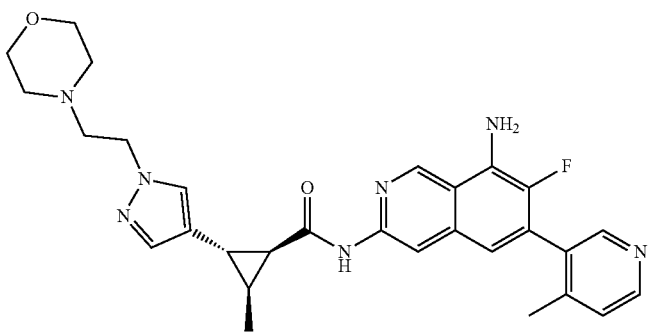 [SMILES: Cc1ccncc1-c1cc2cc(NC(=O)[C@H]3[C@@H](C)[C@@H]3c3cnn(CCN4CCOCC4)c3)ncc2c(N)c1F] | |
| 350, 351, 352, 353 | 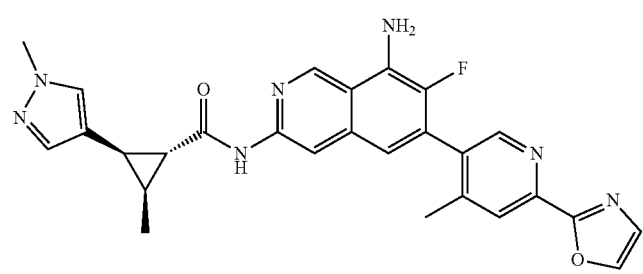 [SMILES: Cc1cc(-c2ncco2)ncc1-c1cc2cc(NC(=O)[C@@H]3[C@@H](C)[C@H]3c3cnn(C)c3)ncc2c(N)c1F]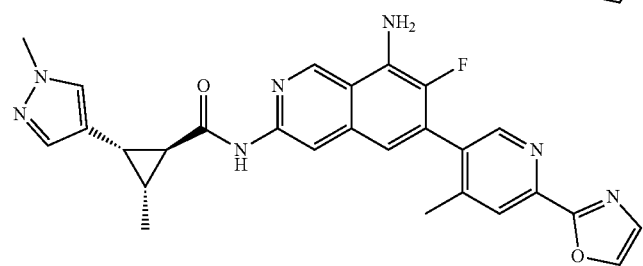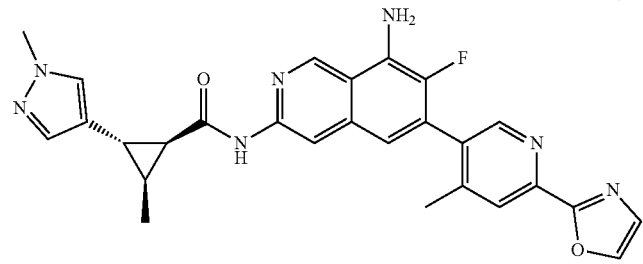 | (1,3)trans-N-(8-amino-7-fluoro-6-(4-methyl-6-(oxazol-2-yl)pyridin-3-yl)isoquinolin-3-yl)-2-methyl-3-(1-methyl-1H-pyrazol-4-yl)cyclopropane-1-carboxamide; |

| No. | Structure | Name |
|---|---|---|
| | 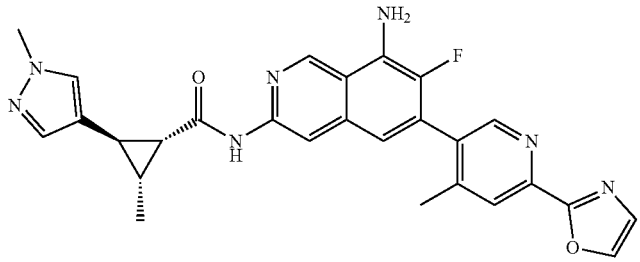 [SMILES: Cc1cc(-c2ncco2)ncc1-c1cc2cc(NC(=O)[C@@H]3[C@H](C)[C@H]3c3cnn(C)c3)ncc2c(N)c1F] | |
| 354 | 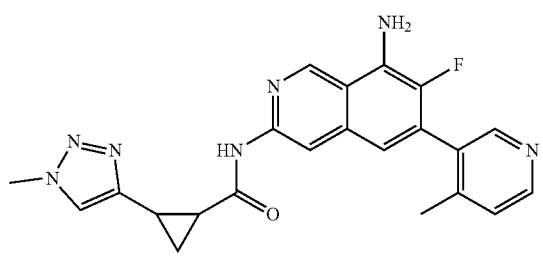 [SMILES: Cc1ccncc1-c1cc2cc(NC(=O)C3CC3c3cn(C)nn3)ncc2c(N)c1F] | N-(8-amino-7-fluoro-6-(4-methylpyridin-3-yl)isoquinolin-3-yl)-2-(1-methyl-1H-1,2,3-triazol-4-yl)cyclopropane-1-carboxamide; |
| 355 | 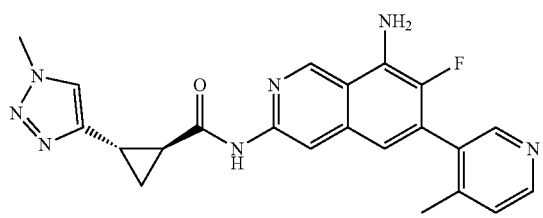 [SMILES: Cc1ccncc1-c1cc2cc(NC(=O)[C@H]3C[C@@H]3c3cn(C)nn3)ncc2c(N)c1F] | (1S,2S)-N-(8-amino-7-fluoro-6-(4-methylpyridin-3-yl)isoquinolin-3-yl)-2-(1-methyl-1H-1,2,3-triazol-4-yl)cyclopropane-1-carboxamide (Relative stereochemistry as drawn; Absolute stereochemistry arbitrarily assigned); |
| 356 | 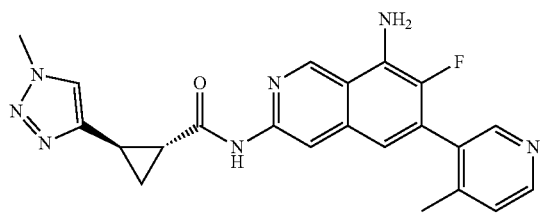 [SMILES: Cc1ccncc1-c1cc2cc(NC(=O)[C@@H]3C[C@H]3c3cn(C)nn3)ncc2c(N)c1F] | (1R,2R)-N-(8-amino-7-fluoro-6-(4-methylpyridin-3-yl)isoquinolin-3-yl)-2-(1-methyl-1H-1,2,3-triazol-4-yl)cyclopropane-1-carboxamide (Relative stereochemistry as drawn; Absolute stereochemistry arbitrarily assigned); |
| 357, 358, 359, 360 | 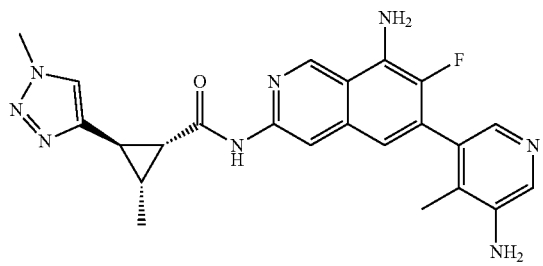 [SMILES: Cc1c(N)cncc1-c1cc2cc(NC(=O)[C@@H]3[C@H](C)[C@H]3c3cn(C)nn3)ncc2c(N)c1F]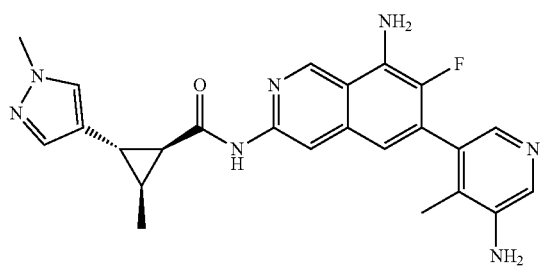 [SMILES: Cc1c(N)cncc1-c1cc2cc(NC(=O)[C@H]3[C@@H](C)[C@@H]3c3cnn(C)c3)ncc2c(N)c1F] | (1,3)trans-N-(8-amino-6-(5-amino-4-methylpyridin-3-yl)-7-fluoroisoquinolin-3-yl)-2-methyl-3-(1-methyl-1H-pyrazol-4-yl)cyclopropane-1-carboxamide; |

| No. | Structure | Name |
|---|---|---|
| | 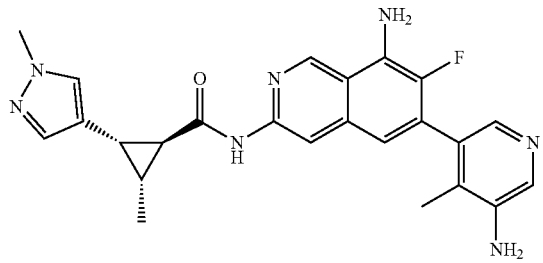 [SMILES: Cc1c(N)cncc1-c1cc2cc(NC(=O)[C@H]3[C@H](C)[C@@H]3c3cnn(C)c3)ncc2c(N)c1F] | |
| | 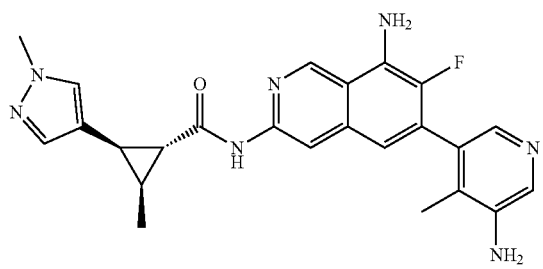 | |
| 363, 364 | 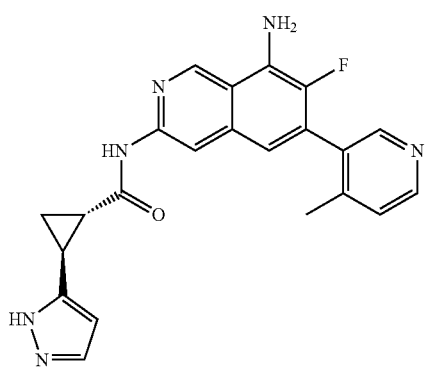 [SMILES: Cc1ccncc1-c1cc2cc(NC(=O)[C@H]3C[C@@H]3c3ccn[nH]3)ncc2c(N)c1F] | trans-N-(8-amino-7-fluoro-6-(4-methylpyridin-3-yl)isoquinolin-3-yl)-2-(1H-pyrazol-5-yl)cyclopropane-1-carboxamide; |
| | 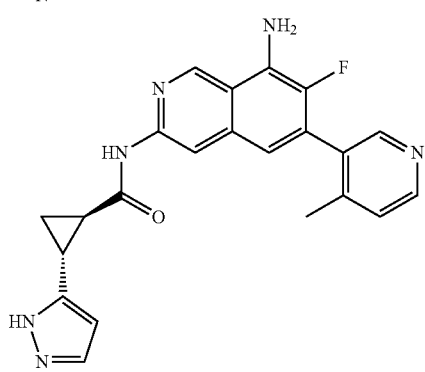 | |
| 365, 366, 367, 368 | 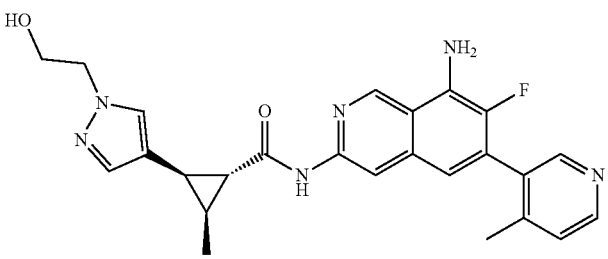 [SMILES: Cc1ccncc1-c1cc2cc(NC(=O)[C@@H]3[C@@H](C)[C@H]3c3cnn(CCO)c3)ncc2c(N)c1F] | (1,2)trans-N-(8-amino-7-fluoro-6-(4-methylpyridin-3-yl)isoquinolin-3-yl)-2-(1-(2-hydroxyethyl)-1H-pyrazol-4-yl)-3-methylcyclopropane-1-carboxamide; |

| No. | Structure | Name |
|---|---|---|
| | 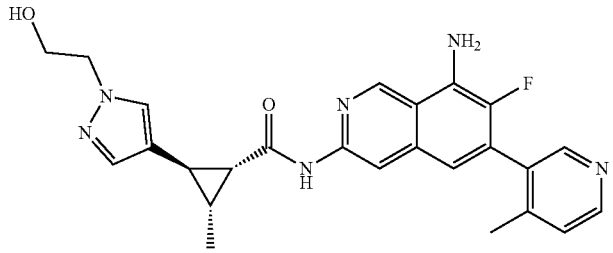 [SMILES: Cc1ccncc1-c1cc2cc(NC(=O)[C@@H]3[C@H](C)[C@H]3c3cnn(CCO)c3)ncc2c(N)c1F] | |
| | 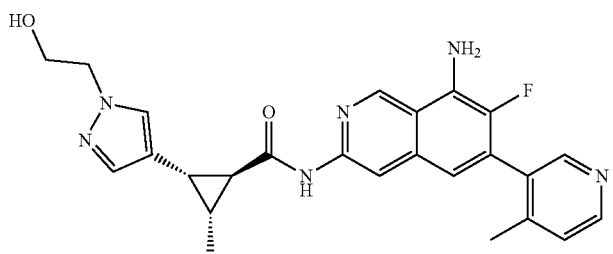 | |
| | 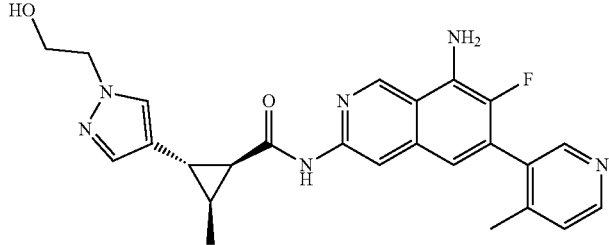 [SMILES: Cc1ccncc1-c1cc2cc(NC(=O)[C@H]3[C@@H](C)[C@@H]3c3cnn(CCO)c3)ncc2c(N)c1F] | |
| 369, 370 | 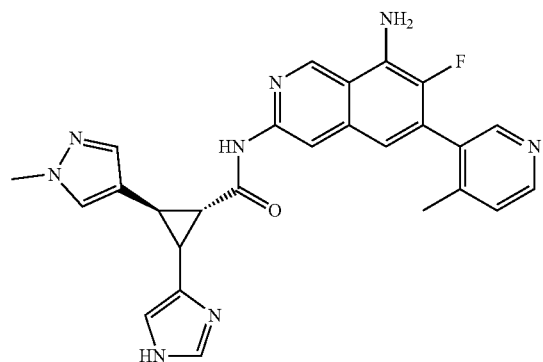 [SMILES: Cc1ccncc1-c1cc2cc(NC(=O)[C@@H]3C(c4c[nH]cn4)[C@H]3c3cnn(C)c3)ncc2c(N)c1F] | (1,3)trans-N-(8-amino-7-fluoro-6-(4-methylpyridin-3-yl)isoquinolin-3-yl)-2-(1H-imidazol-4-yl)-3-(1-methyl-1H-pyrazol-4-yl)cyclopropane-1-carboxamide; |
| | 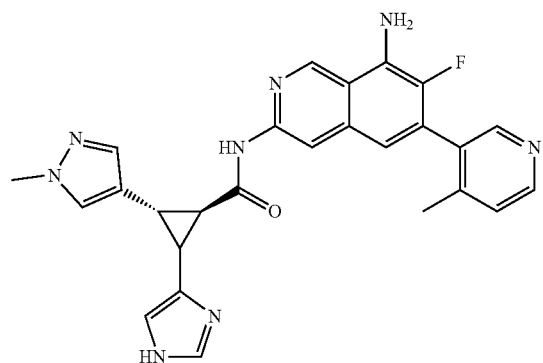 [SMILES: Cc1ccncc1-c1cc2cc(NC(=O)[C@H]3C(c4c[nH]cn4)[C@@H]3c3cnn(C)c3)ncc2c(N)c1F] | |

-continued
| No. | Structure | Name |
|---|---|---|
| 371, 372, 373, 374 | 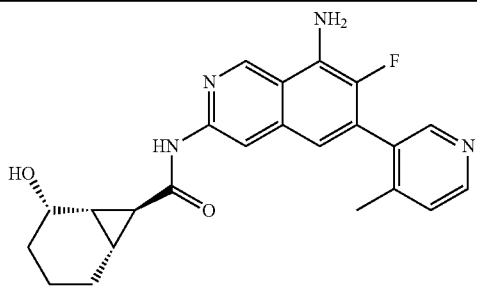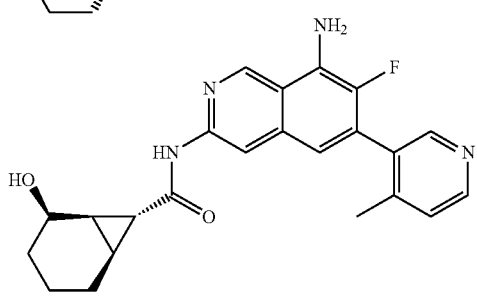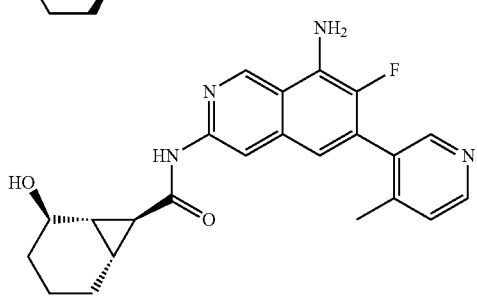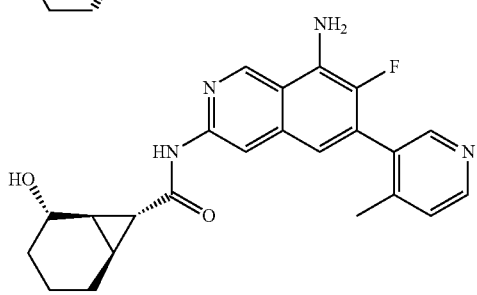 | exo-N-(8-amino-7-fluoro-6-(4-methylpyridin-3-yl)isoquinolin-3-yl)-2-hydroxybicyclo[4.1.0]heptane-7-carboxamide; |
| 375, 376, 377, 378 | 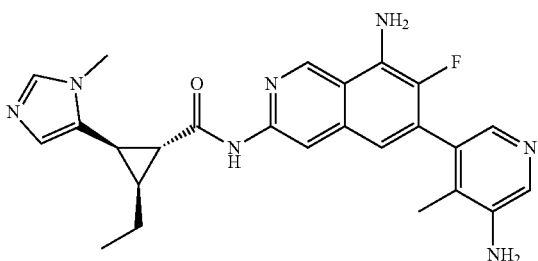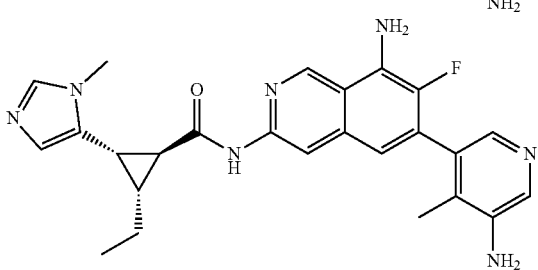 | (1,3)trans-N-(8-amino-6-(5-amino-4-methylpyridin-3-yl)-7-fluoroisoquinolin-3-yl)-2-ethyl-3-(1-methyl-1H-imidazol-5-yl)cyclopropane-1-carboxamide; |

| No. | Structure | Name |
|---|---|---|
| 379, 380, 381, 382 | 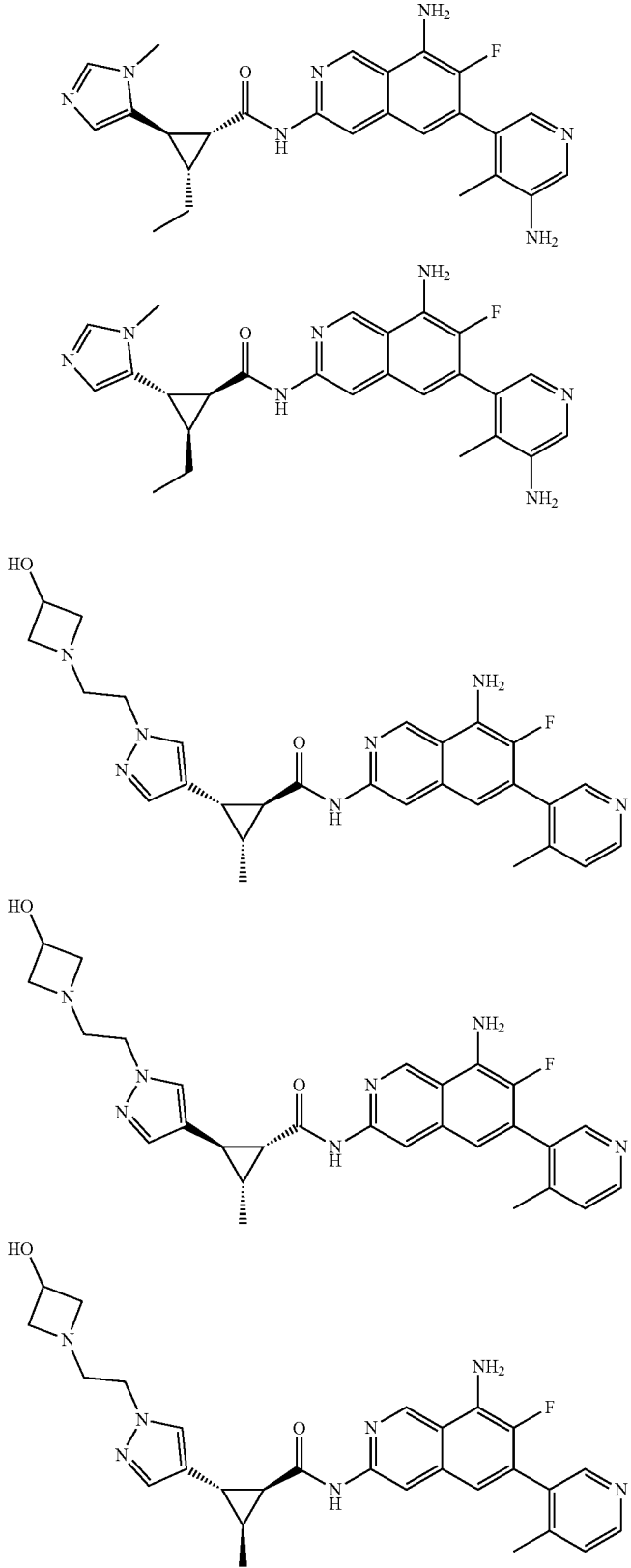 | (1,2)trans-N-(8-amino-7-fluoro-6-(4-methylpyridin-3-yl)isoquinolin-3-yl)-2-(1-(2-(3-hydroxyazetidin-1-yl)ethyl)-1H-pyrazol-4-yl)-3-methylcyclopropane-1-carboxamide; and |

| No. | Structure | Name |
|---|---|---|
| 383, 384, 385, 386 | 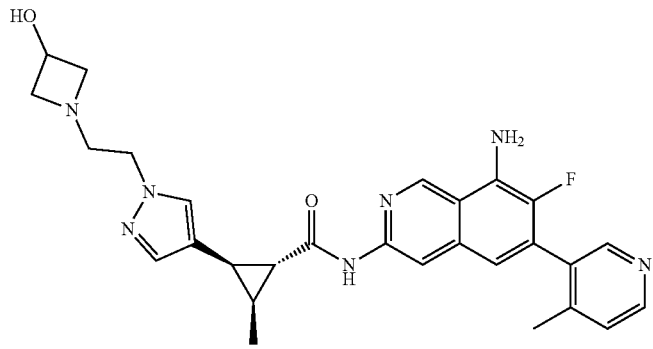 [SMILES: Cc1ccncc1-c1cc2cc(NC(=O)[C@@H]3[C@@H](C)[C@H]3c3cnn(CCN4CC(O)C4)c3)ncc2c(N)c1F]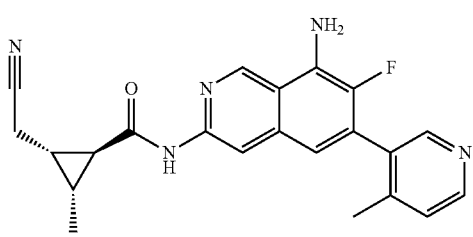 [SMILES: Cc1ccncc1-c1cc2cc(NC(=O)[C@H]3[C@H](C)[C@@H]3CC#N)ncc2c(N)c1F]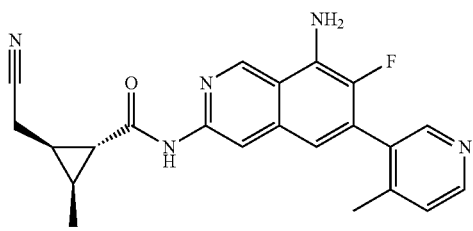 [SMILES: Cc1ccncc1-c1cc2cc(NC(=O)[C@@H]3[C@@H](C)[C@H]3CC#N)ncc2c(N)c1F]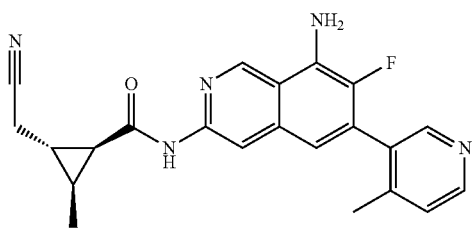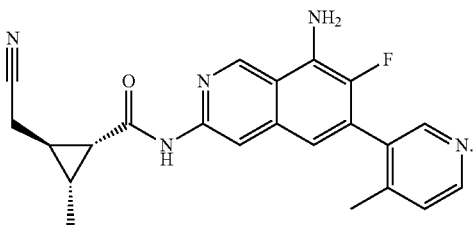 [SMILES: Cc1ccncc1-c1cc2cc(NC(=O)[C@@H]3[C@H](C)[C@H]3CC#N)ncc2c(N)c1F] | (1,2)trans-N-(8-amino-7-fluoro-6-(4-methylpyridin-3-yl)isoquinolin-3-yl)-2-(cyanomethyl)-3-methylcyclopropane-1-carboxamide |

29. The compound of claim 1, or a pharmaceutically acceptable salt thereof, wherein the compound is selected from the group consisting of:

| No. | Structure | Name |
|---|---|---|
| 391 | 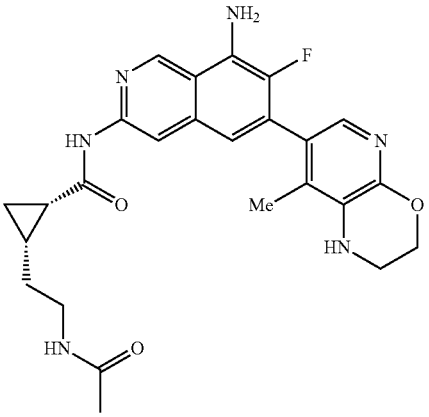 [SMILES: CC(=O)NCC[C@@H]1C[C@@H]1C(=O)Nc1cc2cc(-c3cnc4c(c3C)NCCO4)c(F)c(N)c2cn1] 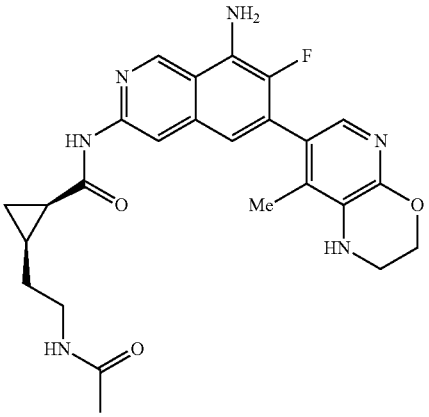 [SMILES: CC(=O)NCC[C@H]1C[C@H]1C(=O)Nc1cc2cc(-c3cnc4c(c3C)NCCO4)c(F)c(N)c2cn1] | cis-2-(2-acetamidoethyl)-N-(8-amino-7-fluoro-6-(8-methyl-2,3-dihydro-1H-pyrido[2,3-b][1,4]oxazin-7-yl)isoquinolin-3-yl)cyclopropane-1-carboxamide; |
| 392 | 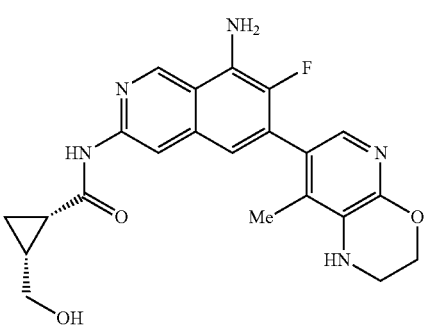 [SMILES: Cc1c(-c2cc3cc(NC(=O)[C@H]4C[C@H]4CO)ncc3c(N)c2F)cnc2c1NCCO2] 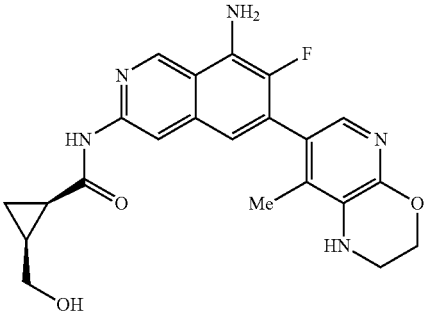 [SMILES: Cc1c(-c2cc3cc(NC(=O)[C@@H]4C[C@@H]4CO)ncc3c(N)c2F)cnc2c1NCCO2] | cis-N-(8-amino-7-fluoro-6-(8-methyl-2,3-dihydro-1H-pyrido[2,3-b][1,4]oxazin-7-yl)isoquinolin-3-yl)-2-(hydroxymethyl)cyclopropane-1-carboxamide; |

| No. | Structure | Name |
|---|---|---|
| 393 | 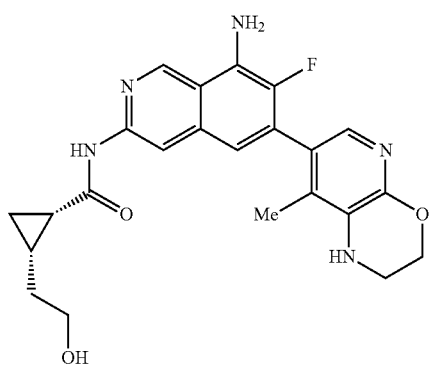 [SMILES: Cc1c(-c2cc3cc(NC(=O)[C@H]4C[C@H]4CCO)ncc3c(N)c2F)cnc2c1NCCO2] | cis-N-(8-amino-7-fluoro-6-(8-methyl-2,3-dihydro-1H-pyrido[2,3-b][1,4]oxazin-7-yl)isoquinolin-3-yl)-2-(2-hydroxyethyl)cyclopropane-1-carboxamide; |
|  | 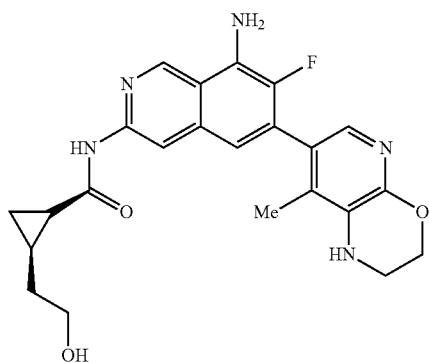 |  |
| 404 | 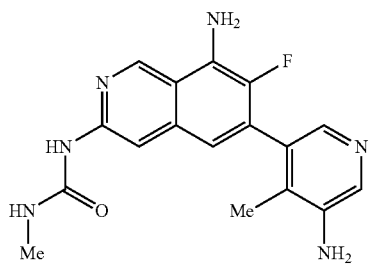 [SMILES: CNC(=O)Nc1cc2cc(-c3cncc(N)c3C)c(F)c(N)c2cn1] | 1-(8-amino-6-(5-amino-4-methylpyridin-3-yl)-7-fluoroisoquinolin-3-yl)-3-methylurea; |
| 405 | 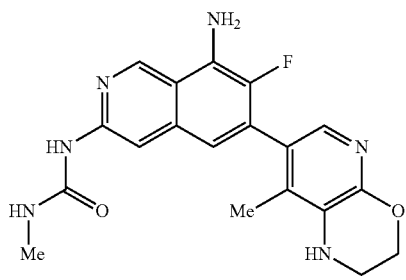 [SMILES: CNC(=O)Nc1cc2cc(-c3cnc4c(c3C)NCCO4)c(F)c(N)c2cn1] | 1-(8-amino-7-fluoro-6-(8-methyl-2,3-dihydro-1H-pyrido[2,3-b][1,4]oxazin-7-yl)isoquinolin-3-yl)-3-methylurea; |

| No. | Structure | Name |
|---|---|---|
| 519 | 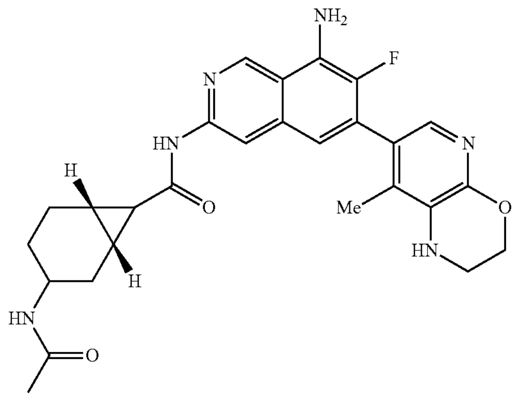 [SMILES: CC(=O)NC1CC[C@@H]2C(C(=O)Nc3cc4cc(-c5cnc6c(c5C)NCCO6)c(F)c(N)c4cn3)[C@@H]2C1] | (1R,6S)-3-acetamido-N-(8-amino-7-fluoro-6-(8-methyl-2,3-dihydro-1H-pyrido[2,3-b][1,4]oxazin-7-yl)isoquinolin-3-yl)bicyclo[4.1.0]heptane-7-carboxamide; and (1R,3R,6S,7S)-3-acetamido-N-(8-amino-7-fluoro-6-(8-methyl-2,3-dihydro-1H-pyrido[2,3-b][1,4]oxazin-7-yl)isoquinolin-3-yl)bicyclo[4.1.0]heptane-7-carboxamide |

30. A pharmaceutical composition comprising the compound of claim 1, or a pharmaceutically acceptable salt thereof; and a pharmaceutically acceptable carrier.

31. The pharmaceutical composition of claim 30, wherein said composition further comprises a chemotherapeutic agent.

* * * * *